US011225655B2

(12) United States Patent
Gouliaev et al.

(10) Patent No.: US 11,225,655 B2
(45) Date of Patent: Jan. 18, 2022

(54) BI-FUNCTIONAL COMPLEXES AND METHODS FOR MAKING AND USING SUCH COMPLEXES

(75) Inventors: Alex Haahr Gouliaev, Veksø Sjælland (DK); Thomas Franch, Snekkersten (DK); Michael Anders Godskesen, Vedbæk (DK); Kim Birkebæk Jensen, Rødovre (DK)

(73) Assignee: NUEVOLUTION A/S, Copenhagen (DK)

( * ) Notice: Subject to any disclaimer, the term of this patent is extended or adjusted under 35 U.S.C. 154(b) by 922 days.

(21) Appl. No.: 13/641,588

(22) PCT Filed: Apr. 16, 2011

(86) PCT No.: PCT/DK2011/000031
§ 371 (c)(1),
(2), (4) Date: Apr. 29, 2013

(87) PCT Pub. No.: WO2011/127933
PCT Pub. Date: Oct. 20, 2011

(65) Prior Publication Data
US 2013/0281324 A1   Oct. 24, 2013

Related U.S. Application Data

(60) Provisional application No. 61/325,160, filed on Apr. 16, 2010.

(30) Foreign Application Priority Data

Apr. 16, 2010  (DK) .......................... PA 2010 70149

(51) Int. Cl.
C12N 15/10   (2006.01)
(52) U.S. Cl.
CPC ..... C12N 15/1065 (2013.01); C12N 15/1068 (2013.01)
(58) Field of Classification Search
None
See application file for complete search history.

(56) References Cited

U.S. PATENT DOCUMENTS

| 4,822,731 A | 4/1989 | Watson et al. |
| 5,013,830 A | 5/1991 | Ohtsuka et al. |
| 5,047,519 A | 9/1991 | Hobbs et al. |
| 5,432,272 A | 7/1995 | Benner |
| 5,449,613 A | 9/1995 | Dordick et al. |
| 5,473,060 A | 12/1995 | Gryaznov et al. |
| 5,474,796 A | 12/1995 | Brennan |
| 5,476,930 A | 12/1995 | Letsinger et al. |
| 5,503,805 A | 4/1996 | Sugarman et al. |
| 5,571,677 A | 11/1996 | Gryaznov |
| 5,571,903 A | 11/1996 | Gryaznov |
| 5,573,905 A | 11/1996 | Lerner et al. |
| 5,604,097 A | 2/1997 | Brenner |
| 5,635,400 A | 6/1997 | Brenner |
| 5,639,603 A | 6/1997 | Dower et al. |
| 5,646,265 A | 7/1997 | McGee |
| 5,654,413 A | 8/1997 | Brenner |
| 5,656,739 A | 8/1997 | Cubicciotti |
| 5,663,046 A | 9/1997 | Baldwin et al. |
| 5,665,975 A | 9/1997 | Kedar |
| 5,670,633 A | 9/1997 | Cook et al. |
| 5,681,943 A | 10/1997 | Letsinger et al. |
| 5,684,169 A | 11/1997 | Hamada et al. |
| 5,686,243 A | 11/1997 | Royer et al. |
| 5,708,153 A | 1/1998 | Dower et al. |
| 5,723,320 A | 3/1998 | Dehlinger |
| 5,723,598 A | 3/1998 | Lerner et al. |
| 5,739,314 A | 4/1998 | Roy et al. |
| 5,739,386 A | 4/1998 | Holmes |
| 5,741,643 A | 4/1998 | Gryaznov et al. |
| 5,763,175 A | 6/1998 | Brenner |
| 5,763,263 A | 6/1998 | Dehlinger |
| 5,770,358 A | 6/1998 | Dower et al. |
| 5,770,455 A | 6/1998 | Cargilli et al. |
| 5,780,613 A | 7/1998 | Letsinger et al. |
| 5,789,162 A | 8/1998 | Dower et al. |
| 5,789,172 A | 8/1998 | Still et al. |

(Continued)

FOREIGN PATENT DOCUMENTS

| DE | 196 46 372 | 6/1997 |
| DE | 196 42 751 | 4/1998 |

(Continued)

OTHER PUBLICATIONS

Ocampo et al (Organic Letters 7:4349-52) (Year: 2005).*
Zhang et al (Chem. Commun. 2009 pp. 6795-6797) (Year: 2009).*
Zhang et al (Chem. Commun. 2009 pp. 6795-6797) supporting information (Year: 2009).*
Chevolot et al (Angew. Chem. Int. Ed. 46:2398-402) (Year: 2007).*
ISR International Search Report for International Application No. PCT/DK2006/000685 dated Jun. 14, 2007.
1st Office Action for European Application No. 06818144.5 dated Dec. 11, 2008.
Reply to 1st Office Action for European Application No. 06818144.5 dated Oct. 30, 2009.
Intent to Grant for European Application No. 06818144.5 dated Feb. 23, 2010.
Amendment after Grant for European Application No. 06818144.5 dated Oct. 7, 2010.

(Continued)

Primary Examiner — Christopher M Gross
(74) Attorney, Agent, or Firm — Merchant & Gould P.C.

(57) ABSTRACT

The present invention is directed to a method for the synthesis of a bi-functional complex comprising a molecule part and an identifier oligonucleotide part identifying the molecule part. A part of the synthesis method according to the present invention is preferably conducted in one or more organic solvents when a nascent bi-functional complex comprising an optionally protected tag or oligonucleotide identifier is linked to a solid support, and another part of the synthesis method is preferably conducted under conditions suitable for enzymatic addition of an oligonucleotide tag to a nascent bi-functional complex in solution.

20 Claims, 113 Drawing Sheets
Specification includes a Sequence Listing.

(56) References Cited

U.S. PATENT DOCUMENTS

| | | |
|---|---|---|
| 5,795,976 A | 8/1998 | Oefner et al. |
| 5,804,563 A | 9/1998 | Still et al. |
| 5,817,795 A | 10/1998 | Gryaznov et al. |
| 5,824,471 A | 10/1998 | Mashal et al. |
| 5,830,658 A | 11/1998 | Gryaznov |
| 5,837,860 A * | 11/1998 | Anderson ............... C07H 21/00 435/6.12 |
| 5,840,485 A | 11/1998 | Lebl et al. |
| 5,843,650 A | 12/1998 | Segev |
| 5,843,701 A | 12/1998 | Gold et al. |
| 5,846,719 A | 12/1998 | Brenner et al. |
| 5,880,972 A | 3/1999 | Horlbeck |
| 5,942,609 A | 8/1999 | Hunkapiller et al. |
| 5,948,648 A | 9/1999 | Khan et al. |
| 6,001,579 A | 12/1999 | Still et al. |
| 6,056,926 A | 5/2000 | Sugarman et al. |
| 6,060,596 A | 5/2000 | Lerner et al. |
| 6,087,112 A | 7/2000 | Dale |
| 6,090,912 A | 7/2000 | Lebl et al. |
| 6,096,875 A | 8/2000 | Khan et al. |
| 6,127,533 A | 10/2000 | Cook et al. |
| 6,132,970 A | 10/2000 | Stemmer |
| 6,140,489 A | 10/2000 | Brenner |
| 6,140,493 A | 10/2000 | Dower et al. |
| 6,143,497 A | 11/2000 | Dower et al. |
| 6,143,503 A | 11/2000 | Baskerville et al. |
| 6,150,516 A | 11/2000 | Brenner et al. |
| 6,165,717 A | 12/2000 | Dower et al. |
| 6,165,778 A | 12/2000 | Kedar et al. |
| 6,172,214 B1 | 1/2001 | Brenner |
| 6,194,550 B1 | 2/2001 | Gold et al. |
| 6,197,555 B1 | 3/2001 | Khan et al. |
| 6,207,446 B1 | 3/2001 | Szostak et al. |
| 6,210,900 B1 | 4/2001 | Yamashita et al. |
| 6,232,066 B1 | 5/2001 | Felder et al. |
| 6,235,475 B1 | 5/2001 | Brenner et al. |
| 6,235,889 B1 | 5/2001 | Ulanovsky |
| 6,248,568 B1 | 6/2001 | Khan et al. |
| 6,274,385 B1 | 8/2001 | Hochlowski et al. |
| 6,287,765 B1 | 9/2001 | Cubicciotti |
| 6,297,053 B1 | 10/2001 | Stemmer |
| 6,306,587 B1 | 10/2001 | Royer et al. |
| 6,352,828 B1 | 3/2002 | Brenner |
| 6,416,949 B1 | 7/2002 | Dower et al. |
| 6,429,300 B1 | 8/2002 | Kurz et al. |
| 6,479,264 B1 | 11/2002 | Louwrier |
| 6,503,759 B1 | 1/2003 | Still et al. |
| 6,514,736 B1 | 2/2003 | Erlich et al. |
| 6,537,776 B1 | 3/2003 | Short |
| 6,593,088 B1 | 7/2003 | Saito et al. |
| 6,613,508 B1 | 9/2003 | Ness et al. |
| 6,620,584 B1 | 9/2003 | Chee et al. |
| 6,620,587 B1 | 9/2003 | Taussig et al. |
| 6,780,981 B1 | 8/2004 | Southern et al. |
| 6,936,477 B2 | 8/2005 | Still et al. |
| 7,070,928 B2 | 7/2006 | Liu et al. |
| 7,223,545 B2 | 5/2007 | Liu et al. |
| 7,413,854 B2 | 8/2008 | Pedersen et al. |
| 7,442,160 B2 | 10/2008 | Liu et al. |
| 7,479,472 B1 | 1/2009 | Harbury et al. |
| 7,491,494 B2 | 2/2009 | Liu et al. |
| 7,557,068 B2 | 7/2009 | Liu et al. |
| 7,704,925 B2 | 4/2010 | Gouliaev et al. |
| 7,727,713 B2 | 6/2010 | Pedersen et al. |
| 7,771,935 B2 | 8/2010 | Liu et al. |
| 7,915,201 B2 | 3/2011 | Franch et al. |
| 7,998,904 B2 | 8/2011 | Liu et al. |
| 2002/0004876 A1 | 1/2002 | Timmer et al. |
| 2002/0005512 A1 | 1/2002 | Trill |
| 2002/0007288 A1 | 1/2002 | Endou |
| 2002/0008171 A1 | 1/2002 | Sumiyashiki et al. |
| 2002/0011506 A1 | 1/2002 | Shingu et al. |
| 2002/0012759 A1 | 1/2002 | Asayama et al. |
| 2002/0014233 A1 | 2/2002 | Gatly, Jr. et al. |
| 2003/0000412 A1 | 1/2003 | Haak et al. |
| 2003/0005045 A1 | 1/2003 | Tanimoto |
| 2003/0011373 A1 | 1/2003 | Steinlechner et al. |
| 2003/0018206 A1 | 1/2003 | Yamauchi |
| 2003/0018623 A1 | 1/2003 | Aggarwal et al. |
| 2003/0187240 A1 | 10/2003 | Cook et al. |
| 2004/0004900 A1 | 1/2004 | Dosaka |
| 2004/0011021 A1 | 1/2004 | Inoue et al. |
| 2004/0016174 A1 | 1/2004 | Connor et al. |
| 2004/0018548 A1 | 1/2004 | Yamashita |
| 2004/0019181 A1 | 1/2004 | Falla et al. |
| 2004/0019784 A1 | 1/2004 | Monsen et al. |
| 2004/0020928 A1 | 2/2004 | Lin |
| 2004/0197804 A1 | 10/2004 | Keefe et al. |
| 2005/0002576 A1 | 1/2005 | Nakaya |
| 2005/0004266 A1 | 1/2005 | Kayano et al. |
| 2005/0013017 A1 | 1/2005 | Amanai |
| 2005/0014258 A1 | 1/2005 | Collas et al. |
| 2005/0015876 A1 | 1/2005 | Clark |
| 2005/0017037 A1 | 1/2005 | Aftanas et al. |
| 2005/0158765 A1* | 7/2005 | Morgan ................ C07H 21/00 506/15 |
| 2006/0009959 A1 | 1/2006 | Fischer et al. |
| 2006/0012147 A1 | 1/2006 | Laffin |
| 2006/0023423 A1 | 2/2006 | Kuo et al. |
| 2006/0024645 A1 | 2/2006 | Nordin |
| 2006/0026992 A1 | 2/2006 | Chen |
| 2006/0029260 A1 | 2/2006 | Harrington et al. |
| 2007/0002639 A1 | 1/2007 | Ogawa et al. |
| 2007/0004240 A1 | 1/2007 | Dibene, II et al. |
| 2007/0022460 A1 | 1/2007 | Kim et al. |
| 2008/0019398 A1 | 1/2008 | Genossar et al. |
| 2008/0030595 A1 | 2/2008 | Murakami et al. |
| 2009/0003582 A1 | 1/2009 | Shen et al. |
| 2009/0014323 A1 | 1/2009 | Yendler et al. |
| 2009/0014934 A1 | 1/2009 | Seber |
| 2009/0023921 A1 | 1/2009 | Matthews et al. |
| 2009/0026430 A1 | 1/2009 | McDonald et al. |
| 2009/0209430 A1* | 8/2009 | Rasmussen ........ C12N 15/1068 506/4 |
| 2010/0001617 A9 | 1/2010 | Kanna |
| 2011/0023041 A1 | 1/2011 | Tsai |
| 2011/0245478 A1* | 10/2011 | Morvan ................ C07H 21/00 536/22.1 |
| 2012/0002881 A1 | 1/2012 | Maeda |

FOREIGN PATENT DOCUMENTS

| | | |
|---|---|---|
| EP | 0324616 | 7/1989 |
| EP | 0542770 | 5/1993 |
| EP | 0604552 | 7/1994 |
| EP | 0643778 | 3/1995 |
| EP | 0695305 | 2/1996 |
| EP | 0766826 | 4/1997 |
| EP | 0773227 | 5/1997 |
| EP | 0776330 | 6/1997 |
| EP | 0778280 | 6/1997 |
| EP | 0879219 | 11/1998 |
| EP | 0962527 | 12/1999 |
| EP | 1324045 | 7/2003 |
| EP | 1402024 | 3/2004 |
| EP | 1483585 | 12/2004 |
| EP | 1514938 | 3/2005 |
| EP | 1533385 | 5/2005 |
| EP | 1828381 | 9/2007 |
| EP | 1832567 | 9/2007 |
| EP | 2305808 | 4/2011 |
| JP | 05292967 | 11/1993 |
| JP | 08000268 | 1/1996 |
| WO | WO 1990/005785 | 5/1990 |
| WO | WO 1991/05058 | 4/1991 |
| WO | WO 1991/19818 | 12/1991 |
| WO | WO 1992/00091 | 1/1992 |
| WO | WO 1992/02536 | 2/1992 |
| WO | WO 1992/22875 | 12/1992 |
| WO | WO 1993/03172 | 2/1993 |
| WO | WO 1993/06121 | 4/1993 |
| WO | WO 1993/20242 | 10/1993 |
| WO | WO 1994/08051 | 4/1994 |
| WO | WO 1994/13623 | 6/1994 |

(56) References Cited

FOREIGN PATENT DOCUMENTS

| | | |
|---|---|---|
| WO | WO 1994/24143 | 10/1994 |
| WO | WO 1995/04160 | 2/1995 |
| WO | WO 1995/06293 | 3/1995 |
| WO | WO 1995/12608 | 5/1995 |
| WO | WO 1996/03418 | 2/1996 |
| WO | WO 1996/09316 | 3/1996 |
| WO | WO 1996/11878 | 4/1996 |
| WO | WO 1996/12014 | 4/1996 |
| WO | WO 1996/24061 | 8/1996 |
| WO | WO 1996/24847 | 8/1996 |
| WO | WO 1996/35699 | 11/1996 |
| WO | WO 1996/40201 | 12/1996 |
| WO | WO 1996/41011 | 12/1996 |
| WO | WO 1997/004131 | 2/1997 |
| WO | WO 1997/011958 | 4/1997 |
| WO | WO 1997/019039 | 5/1997 |
| WO | WO 1997/027317 | 7/1997 |
| WO | WO 1997/035198 | 9/1997 |
| WO | WO 1998/001562 | 1/1998 |
| WO | WO 1998/031700 | 7/1998 |
| WO | WO 1998/047613 | 10/1998 |
| WO | WO 1998/056904 | 12/1998 |
| WO | WO 1998/058256 | 12/1998 |
| WO | WO 1999/042605 | 8/1999 |
| WO | WO 1999/051546 | 10/1999 |
| WO | WO 1999/051773 | 10/1999 |
| WO | WO 1999/064378 | 12/1999 |
| WO | WO 2000/020639 | 4/2000 |
| WO | WO 2000/021909 | 4/2000 |
| WO | WO 2000/023456 | 4/2000 |
| WO | WO 2000/23458 | 4/2000 |
| WO | WO 2000/023458 | 4/2000 |
| WO | WO 2000/024882 | 5/2000 |
| WO | WO 2000/032823 | 6/2000 |
| WO | WO 2000/040695 | 7/2000 |
| WO | WO 2000/047775 | 8/2000 |
| WO | WO 2000/061775 | 10/2000 |
| WO | WO 2001/000876 | 1/2001 |
| WO | WO 2001/007657 | 2/2001 |
| WO | WO 2001/053539 | 7/2001 |
| WO | WO 2001/056955 | 8/2001 |
| WO | WO 2001/090414 | 11/2001 |
| WO | WO 2002/003067 | 1/2002 |
| WO | WO 2002/010186 | 2/2002 |
| WO | WO 2002/034948 | 5/2002 |
| WO | WO 2002/040664 | 5/2002 |
| WO | WO 2002/074929 | 9/2002 |
| WO | WO 2002/074978 | 9/2002 |
| WO | WO 2002/083951 | 10/2002 |
| WO | WO2002090581 | 11/2002 |
| WO | WO 2002/099078 | 12/2002 |
| WO | WO 2002/102820 | 12/2002 |
| WO | WO 2002/103008 | 12/2002 |
| WO | WO 2003/025567 | 3/2003 |
| WO | WO 2003/062417 | 7/2003 |
| WO | WO 2003/076943 | 9/2003 |
| WO | WO 2003/078050 | 9/2003 |
| WO | WO 2003/078445 | 9/2003 |
| WO | WO 2003/078446 | 9/2003 |
| WO | WO 2003/078625 | 9/2003 |
| WO | WO 2003/078626 | 9/2003 |
| WO | WO 2003/078627 | 9/2003 |
| WO | WO 2003/082901 | 10/2003 |
| WO | WO 2003/106679 | 12/2003 |
| WO | WO 2004/001042 | 12/2003 |
| WO | WO 2004/007529 | 1/2004 |
| WO | WO 2004/009814 | 1/2004 |
| WO | WO 2004/013070 | 2/2004 |
| WO | WO 2004/016767 | 2/2004 |
| WO | WO 2004/024929 | 3/2004 |
| WO | WO 2004/039825 | 5/2004 |
| WO | WO 2004/039962 | 5/2004 |
| WO | WO 2004/042019 | 5/2004 |
| WO | WO 2004/056994 | 7/2004 |
| WO | WO 2004/074429 | 9/2004 |
| WO | WO 2004/074501 | 9/2004 |
| WO | WO 2004/083427 | 9/2004 |
| WO | WO 2004/099441 | 11/2004 |
| WO | WO 2004/110964 | 12/2004 |
| WO | WO 2005/003778 | 1/2005 |
| WO | WO 2005/008240 | 1/2005 |
| WO | WO 2005/026387 | 3/2005 |
| WO | WO 2005/058479 | 6/2005 |
| WO | WO 2005/078122 | 8/2005 |
| WO | WO 2005/090566 | 9/2005 |
| WO | WO 2005/116213 | 12/2005 |
| WO | WO 2006/048025 | 5/2006 |
| WO | WO 2006/053571 | 5/2006 |
| WO | WO 2006/069063 | 6/2006 |
| WO | WO 2006/079061 | 7/2006 |
| WO | WO 2006/128138 | 11/2006 |
| WO | WO 2006/130669 | 12/2006 |
| WO | WO 2006/133312 | 12/2006 |
| WO | WO 2006/135654 | 12/2006 |
| WO | WO 2006/135786 | 12/2006 |
| WO | WO 2006/138560 | 12/2006 |
| WO | WO 2006/138666 | 12/2006 |
| WO | WO 2007/008276 | 1/2007 |
| WO | WO 2007/011722 | 1/2007 |
| WO | WO 2007/016488 | 2/2007 |
| WO | WO 2007/053358 | 5/2007 |
| WO | WO 2007/062664 | 6/2007 |
| WO | WO 2007/124758 | 11/2007 |
| WO | WO 2008/014238 | 1/2008 |
| WO | WO 2008/036273 | 3/2008 |
| WO | WO 2008/054600 | 5/2008 |
| WO | 2008/094599 | 8/2008 |
| WO | WO 2009/018003 | 2/2009 |
| WO | WO 2009/077173 | 6/2009 |
| WO | WO 2009/152824 | 12/2009 |
| WO | WO 2011/127933 | 10/2011 |

OTHER PUBLICATIONS

Decision to Grant European Application No. 06818144.5 dated Nov. 5, 2010.
EESR European Search Report for European Application No. 10 19 2716 dated May 24, 2011.
Office Action in European patent application No. 10192716.8 dated Jul. 30, 2012.
Office Action in European patent application No. 10192716.8 dated Jul. 3, 2013.
Invitation to Identify Subject Matter for European Application No. 10 192 717.6 dated Jun. 1, 2011.
Invitation to identify subject matter for search Response to Invitation dated Aug. 5, 2011.
Invitation to identify subject matter for search Comm, re partial ESR w. partial European Search Report dated Oct. 7, 2011.
Response to partial ESR dated Dec. 8, 2011.
ESR and Search Opinion dated Jan. 25, 2012.
Response to ESR dated Jan. 25, 2012 submitted Dec. 5, 2012.
Office Action dated Jul. 16, 2013 re European patent application No. 10192717.6.
ISR International Search Report for International Application No. PCT/DK2009/050129 dated Aug. 21, 2009.
R. 161/162 Communication pursuant to Rule 161(1) and 162 for European Application No. 09765460.2 dated Mar. 14, 2011.
Response to Rule 161(1) and 162 for European Application No. 09765460.2 dated Apr. 18, 2011.
European Office Action from EP 09765460.2 dated May 7, 2012.
Response to office action re 09765460.2 submitted Feb. 22, 2013.
International Search Report dated Aug. 23, 2011.
Communication pursuant to Rule 161(1) and 162 for European Application No. 11720372.9 dated Dec. 12, 2012.
File Wrapper for Australian Application No. 2003273792, 2003.
Third OA Examination Report for Australian Application No. 2003273792 dated May 6, 2011.
Notice of Acceptance for Australian Application No. 2003273792 dated Jun. 22, 2011.

(56) References Cited

OTHER PUBLICATIONS

Response to OA dated Mar. 26, 2012 re Canadian patent application No. 2,544,153.
Office action of Aug. 20, 2012 re Canadian patent application No. 2,544,153.
Office Action in Chinese patent application No. 200380104764.5 dated Feb. 29, 2012.
Notice of Allowance of Sep. 3, 2012 re Chinese patent application No. 200380104764.5.
Office Action in Israeli patent application No. 207672 dated Jan. 15, 2012.
Response to OA in Israeli patent application No. 207672 dated Jun. 14, 2012.
Office Action in Israeli patent application No. 207672 dated May 28, 2013.
Office Action in Israeli patent application No. 207673 dated Jan. 15, 2012.
Response to OA in Israeli patent application No. 207673 dated Jun. 14, 2012.
Office Action in Israeli patent application No. 207673 dated May 28, 2013.
Appeal filed for Indian patent application No. 178/MUMNP/2007 dated Nov. 15, 2011.
Office Action for Japanese Application No. 2005-501801 dated Apr. 6, 2010.
Office Action for Japanese Application No. 2005-501801 dated May 31, 2011.
Office Action of Jul. 10, 2012 re Japanese Application No. 2010-226107.
Office Action of Jan. 29, 2013 re Japanese patent application No. 2010-226107.
Decision of dismissal of amendment dated Aug. 20, 2013 re Japanese patent application No. 2010-226107.
Restriction Requirement dated Apr. 6, 2005 re U.S. Appl. No. 10/175,539.
Response to Restriction Requirement submitted May 6, 2005 re U.S. Appl. No. 10/175,539.
Non-final Rejection dated Oct. 13, 2005 re U.S. Appl. No. 10/175,539.
Response submitted Apr. 13, 2006 to Non-final Rejection re U.S. Appl. No. 10/175,539.
Final Rejection dated May 19, 2006 re U.S. Appl. No. 10/175,539.
Notice of Appeal filed Nov. 20, 2006 re U.S. Appl. No. 10/175,539.
RCE submitted Feb. 20, 2007 re U.S. Appl. No. 10/175,539.
Non-final rejection dated Mar. 30, 2009 re U.S. Appl. No. 10/593,868.
Response submitted Jul. 28, 2009 to Non-final rejection re U.S. Appl. No. 10/593,868.
Notice of Allowance dated Nov. 16, 2009 re U.S. Appl. No. 10/593,868.
Amendments after Notice of Allowance Feb. 16, 2010 re U.S. Appl. No. 10/593,868.
Issue Notification dated Apr. 7, 2010 re U.S. Appl. No. 10/593,868.
Restriction Requirement dated Apr. 7, 2011 re U.S. Appl. No. 10/589,551.
Response submitted Oct. 7, 2011 to Restriction Requirement re U.S. Appl. No. 10/589,551.
Non-final rejection dated Oct. 26, 2011 re U.S. Appl. No. 10/589,551.
1st Restriction requirement of Oct. 5, 2011 re U.S. Appl. No. 12/095,778.
Response dated Mar. 5, 2012 to 1st Restriction Requirement re U.S. Appl. No. 12/095,778.
2nd Restriction requirement dated Jun. 27, 2012 re U.S. Appl. No. 12/095,778.
Response submitted Dec. 27, 2012 to 2nd Restriction Requirement re U.S. Appl. No. 12/095,778.
Office Action dated Apr. 15, 2013 re U.S. Appl. No. 12/095,778.
Response dated May 15, 2013 to Restriction Requirement re U.S. Appl. No. 12/095,778.
Non-final rejection dated Oct. 8, 2013 re U.S. Appl. No. 12/095,778.

Adang, et al., "The Contribution of Combinatorial Chemistry to Lead Generation: An Interim Analysis", Current Medicinal Chemistry, 2001, 8, 985-998.
Affleck, "Solutions for library encoding to create collections of discrete compounds", Current Opinion in Chemical Biology, 2001, 5:257-263.
Bain, et al., "Biosynthetic site-specific incorporation of a non-natural amino acid into a polypeptide", J. Am. Chem. Soc., 1989, 8013-8014.
Barnes, et al., "Recent developments in the encoding and deconvolution of combinatorial libraries", Current Opinion in Chemical Biology, 2000, 4:346-350.
Chen, et al., "Total Synthesis of Naturally Occurring Prostaglandin F2α on a Non-Cross-Linked Polystyrene Support", Tetrahedron Letters, 39, (1998), 3943-3946.
Coe, et al., "Solution-phase combinatorial chemistry", Molecular Diversity, 4: 31-38, 1999.
Dolle, "Comprehensive Survey of Combinatorial Library Synthesis: 2000", Journal of Combinatorial Chemistry, 2001, vol. 3, No. 6, pp. 477-517.
Dolle, "Comprehensive Survey of Combinatorial Library Synthesis: 2001", Journal of Combinatorial Chemistry, 2002, vol. 4, No. 5, pp. 369-418.
Dolle, "Comprehensive Survey of Combinatorial Library Synthesis: 2002", Journal of Combinatorial Chemistry, 2003, vol. 5, No. 6, pp. 693-753.
Furka, et al., "General method for rapid synthesis of multicomponent peptide mixtures", Int. J. Peptide Protein Res., 37, 1991, 487-493.
Gallop, et al., "Applications of Combinatorial Technologies to Drug Discovery. 1. Background and Peptide Combinatorial Libraries", Journal of Medicinal Chemistry, 1994, vol. 37, No. 9, pp. 1233-1251.
Guillen Schlippe, et al.,"In Vitro Selection of Highly Modified Cyclic Peptides That Act as Tight Binding Inhibitors", J. Am. Chem. Soc., 2012, 134, 10469-10477.
Han, et al., "Liquid-phase combinatorial synthesis", Proc. Natl. Acad. Sci. USA, vol. 92, pp. 6419-6423, Jul. 1995.
www.wikipedia.org/wiki/DNA-encoded chemical library, Oct. 2, 2012, pp. 1-12.
http://www2.umt.edu/medchem/teaching/medchem/mclect14.htm, Thompson C. M., Medicinal Chemistry, lecture 14, Pharmaceutical Sciences 621 & Chemistry 569.
Li, et al., "Kinetics of RNA Degradation by specific base catalysis of transesterification involving the 2'-hydroxyl group", J. Am. Chem. Soc., 1999, 121, pp. 5364-5372.
Ma, et al., "In Vitro Selection of Unnatural Cyclic Peptide Libraries via mRNA Display", Book Ribosome Display and Related Technologies, ch. 21, pp. 367-390.
Maclean, et al., "Glossary of terms used in combinatorial chemistry", Pure Appl. Chem., vol. 71, No. 12, pp. 2349-2365, 1999.
Meier, et al, "Combinatorial Methods, Automated Synthesis and High-Throughput Screening in Polymer Research the Evolution Continues", Macromol. Rapid Commun. 2004, 25, 21-33.
Chorghade, "Drug discovery and development", 2006, ISBN-13: 978-0-471-39848-6, Published by John Wiley & Sons, Inc., Hoboken, New Jersey.
Needels, et al., "Generation and screening of an oligonucleotide-encoded synthetic peptide library", Proc. Natl. Acad. Sci. USA, vol. 90, pp. 10700-10704, Nov. 1993.
Ni, et al., "Versatile Approach to Encoding Combinatorial Organic Syntheses Using Chemically Robust Secondary Amine Tags", J. Med. Chem. 1996, 39, 1601-1608.
Nicolaou, et al., "Radiofrequency Encoded Combinatorial Chemistry", Angew. Chem. Int. Ed. Engl., 1995, 34, No. 20, pp. 2289-2291.
Noren, et al., "A general method for site-specific incorporation of unnatural aminoacids into protein", Science, vol. 244, 1989, pp. 182-188.
Starck, et al., "The puromycin route to assess stereo- and regiochemical constraints on peptide bond formation in eukaryotic ribosomes", J. Am. Chem. Soc., 2003, 125, 8090-8091.

(56) References Cited

OTHER PUBLICATIONS

Studer, et al., "Fluorous Synthesis: A Fluorous-Phase Strategy for Improving Separation Efficiency in Organic Synthesis", 1997, Science, 275, pp. 823-826.
Terrett, et al., "Combinatorial synthesis-The design of compound libraries and their application to drug discovery", Tetrahedron, 1995, vol. 51, No. 30., pp. 8135-8173.
Website: "Combinatorial chemistry", http://www.ukessays.co.uk/essays/chemistry/combinatorial-chemistry.php, Oct. 29, 2012, pp. 1-11.
Wermuth, et al., "Glossary of terms used in medical chemistry", Pure & Appl. Chem, 1998, vol. 70, No. 5, pp. 1129-1143.
Ymane, et al., "Discrimination between D- and L-Tyrosyl transfer ribonucleic acids in peptide chain elongation", Biochemistry, vol. 20, No. 25, Dec. 8, 1981, pp. 7059-7064.
Lipinski, et al., "Experimental and computational approaches to estimate solubility and permeability in drug discovery and development settings", Adv. Drug Deliv. Rev., vol. 46 (1-3), 2001, pp. 3-26.
Lipinski, "Lead- and drug-like compounds: the rule-of-five revolution", Drug Discovery Today: Technologies, vol. 1, No. 4, 2004, pp. 337-341.
Kleiner, et al., "Small-molecule discovery from DNA-encoded chemical libraries", Chem. Soc. Rev., 2011, 40, pp. 5707-5717.
http://en.wikipedia.org/wiki/Scaffold_protein.
Balkenhohl, et al., "Combinatorial synthesis of small organic molecules", Angew Chem Int. Ed Engl., 1996, 35, pp. 2288-2337.
Blondal et al., "Isolation and characterization of a thermostable RNA ligase 1 from a Thermus scotoductus bacteriophage TS2126 with good single-stranded DNA ligation properties", Nucl. Acids. Res. 2005, vol. 33, No. 1, pp. 135-142.
Brennan & Gumport, "T4 RNA ligase catalyzed synthesis of base analogue-containing oligodeoxyribonucleotides and a characterization of their thermal stabilities", Nucleic Acids Res., 1985, vol. 13, No. 24, pp. 8665-8684.
Cummins et al., "Characterization of fully 2'-modified oligoribonucleotide hetero- and homoduplex hybridization and nuclease sensitivity", Nucl. Acids Res. 1995, vol. 23, No. 11, pp. 2019-2024.
Inoue et al., "Synthesis and hybridization studies on two complementary nona(2'-O-methyl)ribonucleotides", Nucleic Acids Res. 1987, vol. 15, No. 15, pp. 6131-6148.
Lesnik et al., "Oligodeoxynucleotides containing 2'-O-modified adenosine: Synthesis and effects on stability of DNA RNA duplexes", Biochemistry, 1993, vol. 32, pp. 7832-7838.
Verma et al., "Functional tuning of nucleic acids by chemical modifications: tailored oligonucleotides as drugs, devices, and diagnostics", Chem Rec. 2003, 3(1), pp. 51-60.
Non final rejection dated Sep. 21, 2012 re U.S. Appl. No. 10/539,288.
Response after Non-final rejection submitted Feb. 28, 2013 re U.S. Appl. No. 10/539,288.
Non-final rejection dated Apr. 16, 2013 re U.S. Appl. No. 10/539,288.
Response to Non-final rejection submitted Sep. 16, 2013 re U.S. Appl. No. 10/539,288.
Restriction Requirement dated Jan. 4, 2008 re U.S. Appl. No. 10/518,056.
Response to Restriction Requirement submitted Jun. 2, 2008 re U.S. Appl. No. 10/518,056.
Non-final Rejection dated Oct. 8, 2008 re U.S. Appl. No. 10/518,056.
Response after Non-final Rejection submitted Feb. 17, 2009 re U.S. Appl. No. 10/518,056.
Final Rejection dated May 27, 2009 re U.S. Appl. No. 10/518,056.
Notice of Appeal filed Oct. 27, 2009 re U.S. Appl. No. 10/518,056.
Amendments after Notice of Appeal submitted Nov. 17, 2009 re U.S. Appl. No. 10/518,056.
Advisory Action dated Jan. 7, 2010 re U.S. Appl. No. 10/518,056.
RCE filed Mar. 22, 2010 re U.S. Appl. No. 10/518,056.
Non-final Rejection dated Mar. 31, 2008 re U.S. Appl. No. 10/545,795.
Response after Non-final Rejection submitted Sep. 30, 2008.
Final Rejection dated Jan. 27, 2009 re U.S. Appl. No. 10/545,795.
Notice of Appeal filed Jul. 27, 2009 re U.S. Appl. No. 10/545,795.
Amendments after Notice of Appeal submitted Sep. 28, 2009 re U.S. Appl. No. 10/545,795.
Advisory Action dated Sep. 29, 2009 re U.S. Appl. No. 10/545,795.
Second amendment after Notice of Appeal submitted Oct. 27, 2009 re U.S. Appl. No. 10/545,795.
Advisory Action dated Oct. 21, 2009 re U.S. Appl. No. 10/545,795.
RCE submitted Oct. 27, 2009 re U.S. Appl. No. 10/545,795.
Non-final Rejection dated Nov. 16, 2009 re U.S. Appl. No. 10/545,795.
Non-final Rejection dated Mar. 30, 2010 re U.S. Appl. No. 10/545,795.
Interview summary dated Jul. 15, 2010 re U.S. Appl. No. 10/545,795.
Interview summary dated Jul. 30, 2010 re U.S. Appl. No. 10/545,795.
Response after Non-final Rejection dated Aug. 30, 2010 re U.S. Appl. No. 10/545,795.
Final Rejection dated Feb. 1, 2011 re U.S. Appl. No. 10/545,795.
Notice of Appeal filed Jul. 27, 2011 re U.S. Appl. No. 10/545,795.
Restriction Requirement dated Jul. 31, 2008 re U.S. Appl. No. 10/546,538.
Response to Restriction Requirement filed Dec. 24, 2008 re U.S. Appl. No. 10/546,538.
Non-final Rejection dated Jun. 10, 2009 re U.S. Appl. No. 10/546,538.
Response after Non-final Rejection submitted Dec. 9, 2009 re U.S. Appl. No. 10/546,538.
Final Rejection dated Jun. 8, 2010 re U.S. Appl. No. 10/546,538.
Notice of Appeal filed Dec. 8, 2010 re U.S. Appl. No. 10/546,538.
Appeal dismissed dated Jul. 20, 2011 re U.S. Appl. No. 10/546,538.
Restriction requirement dated Apr. 24, 2012 re U.S. Appl. No. 13/179,283.
Response submitted Jul. 23, 2012 to restriction requirement re U.S. Appl. No. 13/179,283.
Non-final rejection dated Jul. 31, 2012 re U.S. Appl. No. 13/179,283.
Response dated Jan. 30, 2013 to Non final rejection re U.S. Appl. No. 13/179,283.
Final rejection dated Apr. 11, 2013 re U.S. Appl. No. 13/179,283.
Notice of Appeal filed Sep. 11, 2013 re U.S. Appl. No. 13/179,283.
Restriction Requirement dated Apr. 21, 2008 re U.S. Appl. No. 10/549,619.
Response filed Sep. 22, 2009 to Restriction Requirement re U.S. Appl. No. 10/549,619.
Non-final Rejection dated Apr. 28, 2009 re U.S. Appl. No. 10/549,619.
Response after Non-final Rejection submitted Oct. 26, 2009 re U.S. Appl. No. 10/549,619.
Interview summary dated Mar. 3, 2010 re U.S. Appl. No. 10/549,619.
Notice of Allowance re U.S. Appl. No. 10/549,619.
Amendments after Notice of Allowance dated Oct. 6, 2010 re U.S. Appl. No. 10/549,619.
Second amendment after Notice of Allowance dated Oct. 21, 2012 re U.S. Appl. No. 10/549,619.
Issue Notification dated Mar. 9, 2011 re U.S. Appl. No. 10/549,619.
First Restriction Requirement dated May 9, 2007 re U.S. Appl. No. 10/525,817.
Response submitted to First Restriction Requirement dated Sep. 10, 2007 re U.S. Appl. No. 10/525,817.
Second Restriction Requirement dated Nov. 28, 2007 re U.S. Appl. No. 10/525,817.
Response to second Restriction Requirement submitted Feb. 28, 2008 re U.S. Appl. No. 10/525,817.
Third Restriction Requirement dated Jul. 7, 2009 re U.S. Appl. No. 10/525,817.
Response to third Restriction Requirement submitted Oct. 5, 2009 re U.S. Appl. No. 10/525,817.
Non-final rejection dated Apr. 1, 2010 re U.S. Appl. No. 10/525,817.
Supplemental Non-final Action dated Apr. 5, 2010 re U.S. Appl. No. 10/525,817.
Response submitted Jul. 27, 2010 to Non-final Action Apr. 5, 2010 re U.S. Appl. No. 10/525,817.
Non-final rejection dated Jan. 5, 2011 re U.S. Appl. No. 10/525,817.
Interview Summary dated Jul. 1, 2011 re U.S. Appl. No. 10/525,817.
Response submitted Jul. 5, 2011 to Non-final Action re U.S. Appl. No. 10/525,817.
Examiner's amendment communication dated Dec. 12, 2011 re U.S. Appl. No. 10/525,817.
Notice of Allowance dated Oct. 14, 2011 re U.S. Appl. No. 10/525,817.

(56) References Cited

OTHER PUBLICATIONS

Notice of Allowance dated Jan. 19, 2012 re U.S. Appl. No. 10/525,817.
RCE dated Mar. 19, 2012 re U.S. Appl. No. 10/525,817.
Notice of Allowance dated Mar. 30, 2012 re U.S. Appl. No. 10/525,817.
Issue Notification dated Jun. 6, 2012 re U.S. Appl. No. 10/525,817.
Restriction Requirement dated Jun. 25, 2008 re U.S. Appl. No. 11/402,957.
Response submitted Aug. 25, 2008 to Restriction Requirement re U.S. Appl. No. 11/402,957.
Non-final Rejection dated Nov. 28, 2008 re U.S. Appl. No. 11/402,957.
Response submitted May 14, 2009 to Non-final Rejection re U.S. Appl. No. 11/402,957.
Non-final Rejection dated Jul. 6, 2009 re U.S. Appl. No. 11/402,957.
Response submitted Dec. 7, 2009 to Non-final Rejection re U.S. Appl. No. 11/402,957.
Final Rejection dated Feb. 16, 2010 re U.S. Appl. No. 11/402,957.
Response submitted Jul. 28, 2010 to Final Rejection re U.S. Appl. No. 11/402,957.
Notice of Appeal dated Aug. 16, 2010 re U.S. Appl. No. 11/402,957.
Notice of Allowance dated Sep. 2, 2010 re U.S. Appl. No. 11/402,957.
RCE dated Dec. 2, 2010 re U.S. Appl. No. 11/402,957.
Second Notice of Allowance dated Apr. 29, 2011 re U.S. Appl. No. 11/402,957.
RCE dated Jul. 28, 2011 re U.S. Appl. No. 11/402,957.
Third Notice of Allowance dated Oct. 31, 2011 re U.S. Appl. No. 11/402,957.
RCE dated Dec. 12, 2011 re U.S. Appl. No. 11/402,957.
Preliminary amendment Nov. 21, 2012 re U.S. Appl. No. 11/402,957.
Non-final Rejection dated May 22, 2013 re U.S. Appl. No. 11/402,957.
Response to Non-final rejection submitted Sep. 23, 2013 re U.S. Appl. No. 11/402,957.
Restriction Requirement dated May 14, 2013 re U.S. Appl. No. 13/455,223.
Response submitted Aug. 14, 2013 to Restriction Requirement re U.S. Appl. No. 13/455,223.
First Restriction Requirement dated Feb. 4, 2009 re U.S. Appl. No. 10/572,644.
Reponse submitted Jul. 29, 2009 to First Restriction Requirement re U.S. Appl. No. 10/572,644.
Non-final rejection dated Oct. 29, 2009 re U.S. Appl. No. 10/572,644.
Response submitted Apr. 28, 2010 to Non-final rejection re U.S. Appl. No. 10/572,644.
Second Restriction Requirement dated Jul. 21, 2010 re U.S. Appl. No. 10/572,644.
Response submitted Jan. 19, 2011 to Second Restriction Requirement re U.S. Appl. No. 10/572,644.
Non-final rejection dated Mar. 31, 2011 re U.S. Appl. No. 10/572,644.
Response submitted Sep. 30, 2011 to Non final rejection re U.S. Appl. No. 10/572,644.
Final rejection dated Jan. 9, 2012 re U.S. Appl. No. 10/572,644.
Notice of Appeal filed Jul. 6, 2012 re U.S. Appl. No. 10/572,644.
RCE of Sep. 6, 2012 re U.S. Appl. No. 10/572,644.
Whitesides, et al., "Enzymes as Catalysts in Organic Synthesis", Aldrichimica Acta., vol. 16, No. 2, pp. 27-39, 1983.
Winzeler et al., "Fluorescence-based expression monitoring using microarrays", Methods Enzymol., 1999; 306: 3-18.
Wong, et al., "Branch capture reactions: displacers derived from assymmetric PCR", 1991 Oxford University Press, Nucleic Acids Research, vol. 19; No. 9, pp. 2251-2259.
Xu, Y, et al., "A Novel 5'-Iodonucleoside Allows Efficient Nonenzymatic Ligation of Single-stranded and Duplex DNA", Abstract, Tetrahedron Letters (1997) 38:5595-5598.
Xu, Y., et al., "High sequence fidelity in a non-enzymatic DNA autoligation reaction", Nucleic Acids Research, 1999, vol. 27, No. 3; pp. 875-881.
Xu, Y., et al., "Nonenzymatic autoligation in direct three-color detection of RNA and DNA point mutations", Nat Biotechnol., vol. 19, pp. 148-152, Feb. 2001.
Xu, Y., et al., "Rapid and selective selenium-mediated autoligation of DNA strands", J. Am. Chem. Soc., vol. 122, pp. 9040-9041, 2000.
Zhan, ZJ, et al., "Chemical Amplification through template-directed synthesis", J. Am. Chem. Soc., vol. 119, pp. 12420-12421, 1997.
Zhu et al., "A Primer-dependent Polymerase Function of Pseudomonas aeruginosa ATP-dependent DNA ligase (LigD)", Journal of Biological Chemistry (2006) 280(1): 418-427.
Zuckerman, RN., et al., "Discovery of nanomolar ligands for 7-transmembrane G-protein-coupled receptors from a diverse N-(substituted) glycine peptoid library", J. Med. Chem., 1994, 37, 2678-2685.
ISR International Search Report from PCT No. PCT/DK02/00419 dated Jun. 25, 2003.
IPER International Preliminary Examination Report from PCT No. PCT/DK02/00419 dated Jan. 28, 2004.
First Office Action European Office Action from European Application No. EP 02740409.4 dated Sep. 1, 2005.
Reply to first Office Action RE: European Applicant No. 02740409.4 dated Jun. 16, 2006.
Intention to grant Intent to Grant from European Application No. EP 02740409.4 printed Oct. 13, 2006.
Decision to grant Decision to Grant from European Application No. EP 02740409.4 dated Jul. 26, 2007.
EESR Extended European Search Report from European Application No. 07114663.3 dated May 25, 2009.
1st Office Action in EP 07114663.3 dated Sep. 12, 2011.
Response to Office Action in EP 07114663.3 dated Jul. 4, 2012.
2nd Office Action in EP 07114663.3 dated Jul. 23, 2012.
Response to Office Action in EP 07114663.3 dated May 17, 2013.
3rd Office Action in European patent application No. 07114663.3 dated Jun. 3, 2013.
EESR Extended European Search Report from European Application No. 10 18 4311 dated Feb. 28, 2011.
EESR Response to ESR dated Feb. 6, 2012.
Office Action in EP 10184311.8 dated Mar. 19, 2012.
Response to 1st Office Action dated Mar. 19, 2012 in EP 10184311.8 submitted Jan. 18, 2013.
2nd Office action dated Feb. 6, 2013 in EP 10184311.8.
ISR International Search Report from PCT No. PCT/DK03/00172 dated Nov. 3, 2003.
First Office Action Office Action from European Application No. 03709676.5 dated Feb. 23, 2005.
Reply to first Office Action from European Application No. 30709676.5 dated Jun. 30, 2005.
Second Office Action 2nd Office Action from European Application No. 03709676.5 dated Aug. 26, 2005.
Reply to 2nd Office Action from European Application No. 03709676.5 dated Sep. 13, 2005.
Third Office Action from European Application No. 03709676.5 dated Sep. 30, 2005.
Reply to 3rd Office Action from European Application No. 03709676.5 dated May 19, 2006.
Intention to Grant from European Application No. 03709676.5 printed Dec. 17, 2004.
Amendment after Intention to Grant from European Application No. 03709676.5 dated Nov. 16, 2007.
Decision to Grant from European Application No. 03709676.5 dated Oct. 23, 2008.
ESR European Search Report from European Application No. 08 16 9346 dated Apr. 13, 2010.
Reply to ESR Response filed in European Application No. 08169346.7 dated Mar. 23, 2011.
1st Office Action from European Application No. 08169346.7 dated Apr. 19, 2011.
Response to Office Action filed Feb. 10, 2012.
2nd Office Action dated Feb. 24, 2012 with Annex.
Response to 2nd Office Action of Feb. 24, 2012 in EP 08169346.7 submitted Dec. 21, 2012.
3rd Office Action dated Jan. 29, 2013 in EP 08169346.7.
ISR International Search Report from PCT Application No. PCT/DK03/00516 dated Feb. 18, 2004.
1st Office Action from European Application No. 03766117.0 dated Mar. 24, 2009.

(56) References Cited

OTHER PUBLICATIONS

Reply to 1st Office Action from European Application No. 03766117.0 dated Jan. 8, 2010.
2nd Office Action from European Application No. 03766117.0 dated Feb. 16, 2010.
Reply to 2nd Office Action from European Application No. 03766117.0 dated Aug. 20, 2010.
3rd Office Action from European Application No. 03766117.0 dated Nov. 19, 2010.
Reply to 3rd Office Action from European Application No. 03766117.0 dated May 23, 2011.
4th Office Action from European Appllication No. 03766117.0 dated Jun. 9, 2011.
Response to 4th Office Action dated Jun. 9, 2011 in EP 03766117.0 submitted Mar. 14, 2012.
5th Office Action from European Appllication No. 03766117.0 dated May 31, 2012.
Office Action from European Application No. 03766117.0 dated Mar. 26, 2013.
ISR International Search Report for PCT Application No. PCT/DK03/00921 dated Jun. 22, 2004.
1st Office Action for European Application No. 03767480.1 dated May 7, 2007.
Reply to 1st Office Action for European Application No. 03767480.1 dated Mar. 19, 2008.
2nd Office Action for European Application No. 03767480.1 dated Jun. 18, 2008.
Reply to 2nd Office Action for European Application No. 03767480.1 dated Feb. 6, 2009.
Intent to Grant for European Application No. 03767480.1 dated Mar. 30, 2009.
Amendment after Intention to Grant for European Application No. 03767480.1 dated Jul. 22, 2009.
Decision to Grant for European Application No. 03767480.1 dated Nov. 5, 2009.
EESR European Search Report for European Application No. 09 17 7376 dated Feb. 24, 2011.
ISR International Search Report for PCT Application No. PCT/DK03/00417 dated Feb. 10, 2004.
1st Office Action for European Application No. 03729906.6 dated May 17, 2006.
Reply to 1st Office Action for European Application No. 03729906.6 dated Mar. 9, 2007.
P114EP00 Second Office Action 2nd Office Action for European Application No. 03729906.6 dated Sep. 22, 2009.
Reply to 2nd Office Action for European Application No. 03729906.6 dated May 6, 2010.
ISR International Search Report for PCT Application No. PCT/DK2004/000116 dated Aug. 23, 2004.
1st Office Action for European Application No. 04713515.7 dated Oct. 19, 2006.
Reply to 1st Office Action for European Application No. 04713515.7 dated Aug. 20, 2007.
2nd Office Action for European Application No. 04713515.7 dated Mar. 31, 2008.
Reply to 2nd Office Action for European Application No. 04713515.7 dated Dec. 5, 2008.
3rd Office Action for European Application No. 04713515.7 dated Sep. 6, 2010.
Reply to 3rd Office Action for European Application No. 04713515.7 dated Jun. 21, 2011.
ISR International Search Report for International Application No. PCT/DK2004/000117 dated Aug. 19, 2004.
1st Office Action for European Application No. 04713517.3 dated Dec. 22, 2006.
Reply to 1st Office Action for European Application No. 04713517.3 dated Oct. 19, 2007.
2nd Office Action for European Application No. 04713517.3 dated Sep. 23, 2008.
Reply to 2nd Office Action for European Application No. 04713517.3 dated Jul. 13, 2009.
3rd Office Action for European Application No. 04713517.3 dated Feb. 14, 2011.
ISR International Search Report for International Application No. PCT/2004/000195 dated Dec. 27, 2004.
1st Office Action for European Application No. 04722237.7 dated Mar. 2, 2006.
Reply to 1 st Office Action for European Application No. 04722237.7 dated Dec. 20, 2006.
2nd Office Action for European Application No. 04722237.7 dated Feb. 28, 2007.
Reply to 2nd Office Action for European Application No. 04722237.7 dated Oct. 19, 2007.
Intent to Grant for European Application No. 04722237.7 dated Jan. 18, 2008.
Amendments after intention to grant for European Application No. 04722237.7 dated Nov. 11, 2008.
Decision to Grant for European Applicaton No. 04722237.7 dated Feb. 5, 2009.
EESR European Search Report for European Applicaton No. 09154197 dated Sep. 15, 2010.
Response to Office Action filed Aug. 5, 2011.
Office Action dated Sep. 12, 2011.
Comm. 71(3) in European patent appliction No. 09154197.9 dated Aug. 7, 2012.
ISR International Search Report for International Application No. PCT/DK03/00739 dated Aug. 30, 2004.
Amendment after ESR for European Application No. 03757752.5 dated Feb. 14, 2006.
1st Office Action for European Application No. 03757752.5 dated Mar. 16, 2006.
Reply to 1st Office Action for European Application No. 03757752.5 dated Jan. 12, 2006.
2nd Office Action for European Application No. 03757752.5 dated Feb. 15, 2007.
Reply to 2nd Office Action for European Application No. 03757752.5 dated Aug. 15, 2007.
Bain, et al., "Regioselective Ligation of Oligoribonucleotides using DNA Splints", Nucl. Acids Res., vol. 20, No. 16, 4372, 1992.
Boger & Goldberg, "Chapter 10: Multi-step Solution Phase Combinatorial Synthesis" in Combinatorial Chemistry, ed. Hicham Fenniri, Oxford University Press (Oxford, England), 2000, pp. 303-326.
Cheng, et al., "Novel Solution Phase Strategy for the Synthesis of Chemical Libraries Containing Small Organic Molecules", J. Am. Chem. Soc., vol. 118, 2567-2573, 1996.
Clark, et al., "Design, Synthesis and Selection of DNA-encoded Small-molecule Libraries", Nat. Chem. Biol., vol. 5, No. 9, 647-654, 2009.
Curran, "Strategy-Level Separations in Organic Synthesis: From Planning to Practice", Angew. Chem. Int. Ed., vol. 37, 1174-1196, 1998.
Declaration by Dr. Dennis Benjamin (including curriculum vitae) Sep. 11, 2013.
Frutos, et al., "Enzymatic Ligation Reactions of DNA "Words" on Surfaces for DNA Computing", J. Am. Chem. Soc., 10277-10282, 1998.
Gait, "Chapter 1: An Introduction to Modern Methods of DNA Synthesis": Van Boom & Wreesman, "Chapter 7 Chemical Synthesis of Small Oligoribonucleotides in solution"; and Beckett & Uhlenbeck, "Chapter 8: Enzymatic Synthesis of Oligoribonucleotides", in Oligonucleotide Synthesis: A Practical Approach, ed. M.J. Gait, IRL Press (Oxford, England and Washington, DC), 1984, pp. 1-22, 153-183, and 185-197.
Gartner, et al., "Expanding the Reaction Scope of DNA-Templated Synthesis", Angew. Chem. Int. Ed., vol. 41, No. 10, 1796-1800, 2002.
Gartner, et al., "Multistep Small-Molecule Synthesis Programmed by DNA Templates", J. Am. Chem. Soc., vol. 124, 10304-10306, 2002 (including Supporting Information, pp. 1-4).
Glen Research Report, "Advances in RNA Synthesis and Structural Analysis", vol. 11, No. 2, (Dec. 1998).

(56) References Cited

OTHER PUBLICATIONS

Harrison, et al., "Synthesis and Hybridization Analysis of a Smal Library of Peptide-oligonucleotide Conjugates", Nucl. Acids Res., vol. 26, No. 13, 3136-3145, 1998.
Hausch, et al., "Libraries of Multifunctional RNA Conjugates for the Selection of New RNA Catalysts", Bioconjugate Chem., vol. 8, 885-890, 1997.
Hill, et al., "Diels-Alder Bioconjugation of Diene-Modified Oligonucleotides", J. Org. Chem., vol. 66, 5352-5358, 2001.
Itakura, et al., "Expression in *Escherichia coli* of a Chemically Synthesized Gene for the Hormone Somatostatin", Science, vol. 198, 1056-1063, 1977.
Janda, "Tagged Versus Untagged Libraries: Methods for the Generation and Screening of Combinatorial Chemical Libraries", PNAS USA, vol. 91, 10779-10785, 1994.
Kelemen, et al., "Hypersensitive Substrate for Ribonucleases", Nucl. Acids. Res., vol. 27, No. 18, 3696-3701, 1999.
Kempe, et al., "Chemical and Enzymatic Biotin-labeling of Oligodeoxyribonucleotides", Nucl. Acids Res., vol. 13, No. 1, 45-57, 1985.
Kinoshita, et al., "Enzymatic Synthesis of Sequencing Primers Based on a Library of Tetramers", Chem. Express, 149-152, 1992.
Kinoshita, et al., "Strand Ligation in a double-stranded DNA by T4 RNA Ligase", Chem. Lett., No. 9, 797-798, 1996.
Kitamura, et al., "Construction of Block-Shuffled Libraries of DNA for Evolutionary Protein Engineering: Y-Ligation-Based Block Shuffling", Prot. Engineering, vol. 15, No. 10, 843-853, 2002.
Kitamura, et al., "Development of Systemic in vitro Evolution and Its Application to Generation of Peptide-Aptamer-Based Inhibitors of Cathepsin E", J. Mol. Biol., vol. 387, 1186-1198, 2009.
Moore, et al., "Site-Specific Modification of Pre-mRNA: The 2'-hydroxyl Groups at the Splice Sites", Science, vol. 256, 992-997, 1992.
Nielsen, et al., "Synthetic Methods for the Implementation of Encoded Combinatorial Chemistry", J. Am. Chem. Soc., vol. 115, 9812-9813, 1993 with supplementary Materials (pp. 1-7).
Nielsen, et al., "Towards Chemical Implementation of Encoded Combinatorial Libraries", Methods: A Companion to Meth: In Enzymol., vol. 6, 361-371, 1994.
Roux, "Optimization and troubleshooting in PCR", PCR Methods Appl., S185-S194, 1995.
Schmitz, et al., "Solid-Phase Enzymatic Synthesis of Oligonucleotides", Org. Lett., vol. 1, 1729-1731, 1999.
Seelig, et al., "Site-Specific Modification of Enzymatically Synthesized RNA: Transcription Initiation and Diels-Alder Reaction," Tetrahed. Lett., vol. 38, 7729-7732, 1997.
Seo, et al., "Click Chemistry to Construct Fluorescent Oligonucelotides for DNA Sequencing", J. Org. Chem., vol. 68, 609-612, 2003.
Sherlin, et al., "Chemical and Enzymatic Synthesis of tRNAs for High-throughput Crystallization", RNA, vol. 7, 1671-1678, 2001.
Tabuchi, et al., "An Efficient Ligation Method in the Making of an in vitro Virus for in vitro Protein Evolution," Biol., Proced. Online, vol. 4, No. 1, 49-54, 2002.
Verma, et al., "Modified Oligonucleotides: Synthesis and Strategy for Users", Annu. Rev. Biochem., vol. 67, 99-134, 1998.
Woiwode, et al., "Synthetic Compound Libraries Displayed on the Surface of Encoded Bacteriophage", Chem. Biol., vol. 10, 847-858, (Sep. 2003).
Wojczewski, et al., "Fluorescent Oligonucleotides—Versatile Tools as Probes and Primers for DNA and RNA Analysis", Synlett, No. 10, 1667-1678, 1999.
Wong & Whitesided, "Enzymes in Synthetic Organic Chemistry", Tetrahedon Organic Chemistry Series vol. 12, Pergamon, Elsevier Science Lrd. (Oxford, England) 1994, pp. Xiii-xv, 1-40, and 329-334.
Zhang, et al., "Solution-Phase Preparation of a 560-Compound Library of Individual Pure Mappicine Analogous by Fluorous Mixture Synthesis", J. Am. Chem. Soc., vol. 124, 10443-10450, 2002.
Strachan, et al., "Human Molecular Genetics", 2nd edition, textbook published by Wiley-Liss, 1999.

Buskirk, et al., "Engineering a Ligand-Dependent RNA Transcriptional Activator", Chem. Biol. 11, 1157-1163 (2004), This work is featured in a Research Highlight in Nature Methods 1, 6-7 (2004).
Böhler, C., et al., "Template switching between PNA and RNA oligonucleotides", Nature 1995, 376, 578-581.
Calderone, C. T., et al., "Nucleic-Acid-Templated Synthesis as a Model System for Ancient Translation", Curr. Opin. Chem. Biol. 8, 645-653 (2004).
Calderone, CT., et al. "Directing otherwise incompatible reactions in a single solution by using DNA-templated organic synthesis". Angew Chem Int Ed, 2002, 41, No. 21. 4104-4108.
Canne et al., "Chemical Protein Synthesis by Solid Phase Ligation of Unprotected Peptide Segments", J. Am. Chem. Soc., 121, 8720-8727 (1999).
Chan, et al., "Intra-tRNA distance measurements for nucleocapsid protein-dependent tRNA unwinding during priming of HIV reverse transcription", PNAS, vol. 96, p. 459-464, Jan. 1999.
Chen, C.B., et al., "Template-directed synthesis on Oligodeoxycytidylate and Polydeoxycytidylate templates", J. Mol. Biol. 1985,181, 271-279.
Chen, et al., "Enzyme Engineering for Nonaqueous Solvents: Random Mutagenesis to Enchance Activity of SubtilisiM E in Polar Organic Media"; Bio/Technology 9, 1073-1077 (1991)—abstract.
Chen, et al., "Enzymes in Nonaqueous Solvents; Applications in Carbohydrate and Peptide Preparation", Methods in Biotechnology, vol. 15, 373-374 (2001).
Chu, et al., "Ligation of oligonucleotides to nucleic acids or proteins via disulfide bonds", vol. 16, No. 9, 1988; pp. 3671-3691.
Clark, et al., "Design, synthesis and selection of DNA-encoded small-molecule libraries", Nat Chem Biol, 5, 647-772. (2009).
Clark, "Selecting chemicals: the emerging utility of DNA-encoded libraries", Current Opinion in Chemical Biology (2010), 14, 396-403.
Colombo, R. et al., "Synthesis of leucin-enkephalin and methionineenkephalin . . .", Hoppe-Seyler'sZ.Physiol.Chem. vol. 362, pp. 1385-1391. (1981).
Constantino, et al., "Privileged structures as leads in medicinal chemistry", Curr Med Chem, 13, 65-85. (2006).
Cotton, et al. "Reactivity of cytosine and thymine in single-base-pair mismatches with hydroxylamine and osmium tetroxide and its application to the study of mutations", Proc Natl Acad Sci (US), 1988;85:4397-44401.
Cousins, GRL., et al., "Identification and isolation of a Receptor for N-Methyl Alkylammonium Salts: Molecular Amplification in a Pseudo-peptide Dynamic Combinatorial Library". Angew. Chem. Int. Ed., 2001, 40, No. 2, 423-427.
Czarnik, A. W., "Encoding strategies in combinatorial chemistry", Proc. Natl. Acad. Sci. USA, vol. 94, pp. 12738-12739, Nov. 1997 (B).
Czarnik, "Encoding methods for combinatorial chemistry", Current Opinion in Chemical Biology, Jun. 1997 (A), vol. 1, p. 60-66.
Czlapinski, et al., "Nucleic acid template-directed assembly of metallosalen-DNA conjugates", J. Am. Chem. Soc., vol. 123, pp. 8618-8619, Sep. 5, 2001, published on the web Aug. 10, 2001.
Degn, et al. "Enzyme Activity in Organic Solvent as a Function of Water Activity Determined by Membrane Inlet Mass Spectometry", Biotechnology Techniques vol. 6; No. 2; Mar./Apr. 1992; pp. 161-164-p. 161.
De Napoli, et al., "PEG-supported Synthesis of Cyclic Oligodeoxyribonucleotides", Nucleosides and Nucleotides, vol. 12, No. 1, pp. 21-30. 1993.
DeWitt, SH., et al., "Diversomers: an approach to nonpeptide, nonoligomeric chemical diversity". Proc. Natl. Acad. Sci. USA, vol. 90, pp. 6909-6913, Aug. 1993.
Dolinnaya, et al., "Chemical ligation as a method for the assembly of double-stranded nucleic acids: Modifications and local structure studies", Russian Chemical Bulletin, vol. 45, No. 8, pp. 1787-1809. 1996.
Dolinnaya, et al., "Structural and kinetic aspects of chemical reactions in DNA duplexes. Information on DNA local structure obtained from chemical ligation data", Nucleic Acids Research, vol. 19, No. 11, 3073-3080 (1991).

(56) References Cited

OTHER PUBLICATIONS

Douglas, et al., "Polymer-supported solution synthesis of oligosaccharides", J. Am. Chem. Soc., vol. 113, pp. 5095-5097, (1991).
Dower, WJ., et al., "In vitro selection as a powerful tool for the applied evolution of proteins and peptides". Current Opinion in Chemical Biology, 2002, 6:390-398.
Doyon, J.B et al., "Highly sensitive in vitro selections for DNA-linked synthetic small molecules with protein binding affinity and specificity", J. Am. Chem. Soc., 125, 12372-12373 (2003 A).
Doyon, J.B et al., "Highly sensitive in vitro selections for DNA-linked synthetic small molecules with protein binding affinity and specificity", J. Am. Chem. Soc., Sep. 16, 2003 B, S1-S8.
Drabovich, et al., "Selection of Smart Small-Molecule Ligands: The Proof of Principle", Analytical Chemistry, vol. 81, 490-494 (2009).
Drews, "Drug Discovery: A Historical Perspective", Science vol. 287, 2000, pp. 1960-1964.
Dreyer, et al., "Enzyme Catalysis in Nonaqueous Media: Past, Present and Future" in Patel (ed.), Biocatalysis in the Pharmaceutical and Biotechnology Industries, (2006).
Ecker, et al., "Rational screening of oligonucleotide combinatorial libraries for drug discovery", Nucleic Acids Research, 1993, vol. 21, No. 8, pp. 1853-1856.
Elghanian, R., et al., "Selective colorimetric detection of polynucleotides based on the distance-dependent optical properties of gold nanoparticles". Science, vol. 277, Aug. 22, 1997. pp. 1078-1081.
Ellman, J.A., et al., "Biosynthetic method for introducing Unnatural Amino acids site-specifically into proteins". Methods Enzymol. 202, 301-336 (1991).
Fack, et al. "Heteroduplex mobility assay (HMA) pre-screening: An improved strategy for the rapid identification of inserts selected from phage-displayed peptide libraries", Molecular diversity, vol. 5, 2000; pp. 7-12.
Fegan et al., "Rigid cyanine dye nucleic acid labels", Chem Commun 2008 2004-2006.
Ficht, Simon, et al., "As Fast and Selective as Enzymatic Ligations: Upaired Nucleobases Increase the Selectivity of DNA-Controlled Native Chemical PNA Ligation"; ChemBioChem: vol. 6 Issue 11 (2005), pp. 2098-2103.
Fredriksson, et al., "Protein detection using proximity-dependent DNA ligation assays", Nature Biotechnology, vol. 20, p. 473-477, May 2002.
Frutos, et al., "Demonstration of a word design strategy for DNA computing on surfaces", Nucleic Acids Research, 1997, vol. 25, No. 23, 4748-4757.
Fujimoto, et al., "Template directed photochemical synthesis of branched oligodeoxynucleotides via 5-carboxyvinyldeoxyuridine", Tetrahedron Letters, vol. 41, pp. 9437-9440, 2000 A.
Fujimoto, et al., "Template-directed photoreversible ligation of deoxyoligonucleotides via 5-Vinyldeoxyuridine", J. Am. Chem. Soc., vol. 122, pp. 5646-5647, 2000 B.
Fujimoto, et al., "Template-directed reversible photocircularization of DNA via 5-vinyldeoxycytidine," Tetrahedron Letters, vol. 41, pp. 6451-6454, 2000 C.
Furka, "Combinatorial Chemistry: 20 years on . . .", Drug discovery today vol. 7, No. 1, p. 1-4, 2002.
Furka, et al., "Combinatorial Libraries by Portioning and Mixing", Combinatorial Chemistry & High Throughput Screening, 1999, 2, 105-122.
Furlan, RLE., et al., "Molecular amplification in a dynamic combinatorial libray using non-covalent interactions". Chem. Commun., 2000, 1761-1762.
Gartner, et al., "Expanding the reaction scope of DNA-templated synthesis", Angew. Chem. Int. Ed., vol. 41, No. 10, pp. 1796-1800, 2002, published May 15, 2002 (B).
Gartner, et al., "The generality of DNA-templated synthesis as a basis for evolving non-natural small molecules", J. Am. Chem. Soc., vol. 123, pp. 6961-6963, 2001.
Gartner, et al., "DNA-Templated Organic Synthesis and Selection of a Library of Macrocycles", Science 305, 1601-1605 (2004).

Gartner, et al., "Multistep small-molecule synthesis programmed by DNA templates". J. Am. Chem. Soc. vol. 124, 2002 (A), 10304-10306.
Gartner, et al., "Two enabling architectures for DNA-templated organic synthesis". Angew. Chem Int. Ed. 2003, 42, No. 12, 1370-1375.
Kurz, M., et al., "Psoralen photo-crosslinked mRNA-puromycin conjugates: a novel template for the rapid and facile preparation of mRNA-protein fushions," Nucleic Acids Res., 2000 (B), 28(18):E83.
Ladner R.C., "Constrained peptides as binding entities", Trends in Biotechnology, vol. 13, 1995, pp. 426-430.
Lebl, "Parallel Personal Comments on "Classical" Papers in Combinatorial Chemistry", J. Comb. Chem. 1999, 1, pp. 3-24.
Lehman, I.R., "DNA ligase: Structure, Mechanism, and Function; The joining of DNA chains by DNA ligase is an essential component of DNA repair, replication, and recombination", Science vol. 186, 1974, pp. 790-797.
Leitzel, JC, et al., "Template-directed ligation: from DNA towards different versatile templates", The Japan chemical Journal Forum., vol. 1 (1), pp. 53-62, 2000.
Letsinger, RL, et al., "Chemical and photochemical ligation of oligonucleotide blocks", Nucleosides and Nucleotides, vol. 16 (5&6), pp. 643-652 (1997).
Lewis, RJ, et al., "Ligation of oligonucleotides by pyrimidine dimers—a missing 'link' in the origin of life?", Nature, vol. 298 (5872), pp. 393-396, Jul. 22, 1982.
Li, et al., "DNA-catalyzed polymerization", J. Am. Chem. Soc., vol. 124 (5), pp. 746-747, 2002.
Li, et al.,"Stereoselectivity in DNA-templated organic synthesis and its origins". J. Am. Chem. Soc. vol. 125, 2003, 10188-10189.
Li, et al., "DNA-Templated Organic Synthesis: Nature's Strategy for Controlling Chemical Ractivity Applied to Synthetic Molecules", Angew. Chem. Int. Ed., 43, 4848-4870 (2004 A).
Li, et al., "Translation of DNA into Synthetic N-Acyloxazolidines", J. Am. Chem. Soc., 126, 5090-5092 (2004 B).
Lim, Carols S. et al., "Syntehsis of DNA Dumbbells: Chemical vs. Enzymatic Ligation of Self-Complementary Oligonucleotides", Abstract only, Nucleosides and Nucleotieds and Nulio Acids; vol. 16, Issue 1 & 2, Jan. 1997.
Lindtröm, et al., "An orthogonal oligonucleotide protecting group strategy that enables assembly of repetitive or highly structured DNAs"; Nucleic Acids Research. Oct. 1, 2002; 30(19), e101; 2002 Oxford University Press.
Liu, D.R., "The Chemistry and Chemical Biology of molecular Evolution", Liu Group Research Summary from the website of Professor David R. Liu, obtained from the website in Feb. 2005.
Liu, D.R., "The Chemistry and Chemical Biology of Molecular Evolution", website of Dr. D. R. Liu, publicly available Mar. 1, 2001. www.web.archive.org/web/20010301175107/http://evolve.havard.edu.
Liu, D.R., "The Chemistry and Chemical Biology of Molecular Evolution", website of Dr. D. R. Liu, publicly available Oct. 15, 2003 (A). Www.web.archive.org/web/20031015114255/http://evolve.havard.edu.
Liu, D.R.,"The Chemistry and Chemical Biology of Molecular Evolution", website of Dr. D. R. Liu, publicly available Nov. 20, 2002. www.web.archive.org/web/20021120104204/http://evolve.havard.edu.
Liu, D.R., "The Chemistry of Molecular Evolution", website of Dr. D. R. Liu, publicly available Oct. 15, 2000 (B). www.web.archive.org/web/20001015144553/http://evolve.havard.edu.
Liu, DR., "The Development of Amplifiable and Evolvable Unnatural Molecules", Harvard Univ. Cambridge MA Dept of Chemistry and Chemical Biology, Report dated Aug. 4, 2003 (B) No. A104614, approved for public release.
Liu, DR., et al., "DNA-templated synthesis as a basis for the evolution of synthetic molecules.", Abstracts of Papers of the American Chemical Society 225:612-ORGN, Part 2, Mar. 2003 (C).
Liu, DR., et al., "Engineering a tRNA and aminoacyl-tRNA synthetase for the site-specific incorporation on unnatural amino acids into proteins in vivo". Proc Natl Acad Sci U S A. 1997, 10092-10097.

(56) References Cited

OTHER PUBLICATIONS

Liu, DR., et al., "Progress toward the evolution of an organism with an expanded genetic code". Proc Natl Acad Sci USA. 1999, 96(9):4780-4785.
Liu, DR.,"Translating DNA into Synthetic Molecules", PLoS Biology, Jul. 2004, vol. 2, Iss. 7, p. 905-906.
Liu, J, et al., "Template-directed photoligation of oligodeoxyribonucleotides via 4-thiothymidine", Nucleic Acids Res, vol. 26 (13), pp. 3300-3304,1998 (A).
Liu, R., et al., "Optimized synthesis of RNA-protein fusions for in vitro protein selection", Methods Enzymol. 2000 (A);318:268-295.
Liu, W, et al., "Denaturing high perfomance liquid chromatography (DHPLC) used in the detection of germline and somatic mutations", Nucleic Acids Research., 26:1396-1400, 1998 (B).
Lobanov. "Designing Cominatorial Libraries for Drug Discovery", Trends in biotechnology, vol. 20, No. 2, Feb. 2002, pp. 86-87.
Lockhart, et al., "Expression monitoring by hybridization to high-density oligonucleotide arrays", Nature Biotechnology, vol. 14, 1996, p. 1675-1680.
Loughlin, "Biotransformations in organic synthesis"; Bioresource Technology, 74 (2000); pp. 49-62.
Lowe, et al., "Combinatorial Libraries for Studying Molecule Recognition", URL: www.iupac.org/symposia/proceedings/phuket97/lowe.html, 7 pages, 1999.
Loweth, CJ., et al., "DNA-based assembly of gold nanocrystals", Angew. Chem. Int. Ed. ,1999, 38, No. 12. 1808-1812.
Luebke, et al., "Nonenzymatic ligation of double-helical DNA by alternate-strand triple helix formation", Nucleic Acids Research; vol. 20, No. 12; 1992; pp. 3005-3009.
Luo, P., et al., "Analysis of the structure and stability of a backbone-modified oligonucleotide: implications for avoiding product inhibition in catalytic template-directed synthesis", J. Am. Chem. Soc. 1998, 120, 3019-3031.
Luther, A., et al., "Surface-promoted replication and exponential amplification of DNA analogues". Nature, vol. 396, Nov. 19, 1998, 245-248.
Maclean, et al., "Encoded Combinatorial Chemistry: Synthesis and screening of a library of highly functionalized pyrrolidines", Proc. Natl. Acad. Sci. USA, vol. 94, pp. 2805-2810, Apr. 1997.
Magliery, et al. "Expanding the Genetic Code in vitro and in vivo", The Genetic Code and the Origin of Life, Ed. Ribas de Pouplana, L. Landes Bioscience, In Press (2004).
Makara, et al., "Improving Success rates for lead generation using affinity binding technologies", Current Opinion in Biotechnology 2005, 16:666-673.
Mannocci, L., "DNA-encoded affinity maturation libraries", 2nd International Symposium DNA Encoded Chemical Libraries, 2010.
Mannocci, "DNA-Encoded Chemical Libraries", Diss. ETH No. 18153, 2009.
Margulies, M. et al., "Genome sequencing in microfabricated high-density picolitre reactors", Nature, 437, 376-380. (2005).
Mashal, et al., "Detection of mutations by cleavage of DNA heteroduplexes with bacteriophage resolvases", Nature Genetics, 1995; 9:177-183.
Matsuda, et al., "Low Fidelity DNA Synthesis by Human DNA Polymerase-*", Nature, 404: 1011-1013, Apr. 27, 2000.
Matsuura, et al., "Construction of glyco-clusters by self-organization of site-specifically glycosylated oligonucleotides and their cooperative amplification of lectin-recognition", Journal of the American Chemical Society, vol. 123, pp. 357-358. (2001).
McCoy, et al., "T4 Ribonucleic Acid Ligase Joins Single-Strand Oligo(deoxyribonucleotides)", Biochemistry, 1980, vol. 19, No. 4, 635-642.
McGregor, et al., "Interaction-Dependent PGR: Identification of Ligand-Target Pairs from Libraries of Ligands and Libraries of Targets in a Single Solution-Phase Experiment", J. Am. Chem. Soc. 2010, 132, pp. 15522-15524.
Melkko, et al., "Lead discovery by DNA-encoded chemical libraries", Drug Discovery Today, vol. 12, Nos. 11/12, Jun. 2007, pp. 465-471.
Mendel, D., "Site-directed mutagenesis with an expanded genetic code", Annu. Rev. Biophys. Biomol. Struc., 1995. 24:435-462.
Miller, Scott J., "DNA as a template for reaction discovery", Nature Biotechnology, vol. 22, No. 11, pp. 1378-1379, Nov. 2004.
Millward; S.W. et al.; "A General Route for Post-Translational Cyclization of mRNA Display Libraries" Journal of the American Chemical Society, vol. 127, 2005, pp. 14142-14143.
Millward, et al., "Design of cyclic peptides that bind protein surfaces with antibody-like affinity" ACS Chemical Biology, vol. 2, No. 9; 2007, pp. 625-634.
Non-final Rejection dated May 14, 2007 re U.S. Appl. No. 10/175,539.
Response submitted Sep. 13, 2007 to Non-final Rejection to U.S. Appl. No. 10/175,539.
Quayle Action dated Nov. 27, 2007 re U.S. Appl. No. 10/175,539.
Response submitted Feb. 27, 2008 to Quayle Action re U.S. Appl. No. 10/175,539.
Notice of Allowance dated May 30, 2008 re U.S. Appl. No. 10/175,539.
Amendment after Notice of Allowance dated Oct. 16, 2008 re U.S. Appl. No. 10/175,539.
Amendment after Notice of Allowance dated May 13, 2009.
Issue Notification dated May 12, 2010 re U.S. Appl. No. 10/75,539.
Non-final Rejection dated Oct. 27, 2009 re U.S. Appl. No. 12/330,709.
Response submitted Apr. 21, 2010 to Non-final Rejection re U.S. Appl. No. 12/330,709.
Supplemental response submitted Jun. 2, 2010 re U.S. Appl. No. 12/330,709.
Ex parte Quyale Action dated Jul. 27, 2010 re U.S. Appl. No. 12/330,709.
Response of Jul. 27, 2010 Ex parte Quayle Action re U.S. Appl. No. 12/330,709.
Notice of Allowance dated Mar. 3, 2011 re U.S. Appl. No. 12/330,709.
RCE filed Jun. 2, 2011 re U.S. Appl. No. 12/330,709.
Office Action dated Sep. 17, 2012 re U.S. Appl. No. 12/330,709.
Response dated Feb. 18, 2013 to Office Action re U.S. Appl. No. 12/330,709.
Non-final rejection dated Mar. 27, 2013 re U.S. Appl. No. 12/330,709.
Response submitted Aug. 27, 2013 re U.S. Appl. No. 12/330,709.
Final rejection dated Oct. 28, 2013 re U.S. Appl. No. 12/330,709.
Non-final Rejection dated Feb. 8, 2007 re U.S. Appl. No. 10/507,121.
Response submitted Jun. 7, 2007 to Non-final Rejection re U.S. Appl. No. 10/507,121.
Final Rejection dated Sep. 7, 2007 re U.S. Appl. No. 10/507,121.
RCE filed Feb. 13, 2008 re U.S. Appl. No. 10/507,121.
Notice of Allowance dated Mar. 20, 2008 re U.S. Appl. No. 10/507,121.
Issue Notification for U.S. Appl. No. 10/507,121 dated Jul. 30, 2008.
Non-final Rejection dated Jan. 27, 2010 re U.S. Appl. No. 12/179,323.
Response submitted Jun. 24, 2010 to Non-final Rejection re U.S. Appl. No. 12/179,323.
Final Rejection dated Sep. 15, 2010 re U.S. Appl. No. 12/179,323.
Notice of Appeal submitted Mar. 15, 2011 re U.S. Appl. No. 12/179,323.
RCE submitted Oct. 17, 2011 re U.S. Appl. No. 12/179,323.
Non-final Rejection dated Jul. 3, 2013 re U.S. Appl. No. 12/179,323.
First Restriction Requirement dated Apr. 4, 2008 re U.S. Appl. No. 10/523,006.
Response to first Restriction Requirement submitted Oct. 1, 2008 re U.S. Appl. No. 10/523,006.
Second Restriction Requirement dated Dec. 9, 2009 re U.S. Appl. No. 10/523,006.
Response to second Restriction Requirement submitted May 5, 2010 re U.S. Appl. No. 10/523,006.
Third Restriction Requirement dated Aug. 3, 2010 re U.S. Appl. No. 10/523,006.
Response to third Restriction Requirement submitted Feb. 1, 2011 re U.S. Appl. No. 10/523,006.
Non-final Rejection dated Mar. 16, 2011 re U.S. Appl. No. 10/523,006.
Response submitted Sep. 16, 2011 to non-final rejection re U.S. Appl. No. 10/523,006.
Final rejection dated Feb. 6, 2012 re U.S. Appl. No. 10/523,006.
RCE submitted Aug. 6, 2012 re U.S. Appl. No. 10/523,006.

(56) References Cited

OTHER PUBLICATIONS

Response submitted Oct. 11, 2013 re U.S. Appl. No. 10/523,006.
Restriction Requirement dated Aug. 2, 2010 re U.S. Appl. No. 10/539,288.
Response to Restriction Requirement submitted Jan. 31, 2011 re U.S. Appl. No. 10/539,288.
Non-final Rejection dated Apr. 25, 2011 re U.S. Appl. No. 10/539,288.
Response after Non-final rejection submitted Oct. 25, 2011 re U.S. Appl. No. 10/539,288.
Final rejection dated Dec. 22, 2011 re U.S. Appl. No. 10/539,288.
Notice of Appeal filed Jun. 18, 2012 re U.S. Appl. No. 10/539,288.
RCE filed Aug. 20, 2012 re U.S. Appl. No. 10/539,288.
Geysen, et al., "Combinatorial Compound Libraries for Drug Discovery: An Ongoing Challenge", Nature Reviews, Drug Discovery, Mar. 2003, vol. 2, p. 222-230.
Giebel L.B.; et al., "Screening of cyclic peptide phage libraries identifies ligands that bind straptavidin with high affinities" Biochemistry, vol. 34, 1995; pp. 15430-15435.
Gordon, EM., et al., "Applications of combinatorial technologies to drug discovery. 2. Combinatorial organic synthesis, library screening strategies, and future directions", Medical Chemical Society, vol. 37, No. 10, May 13, 1994.
Gorin, et al., "Reactivity-Dependent PCR: Direct, Solution-Phase in Vitro Selection for Bond Formation", J. Am. Chem. Soc. 2009, 131, pp. 9189-9191.
Grange, et al., "Detection of point mutations in type I collagen by RNase digestion of RNA/RNA hybrids", Nucleic Acids Research, 1990,18:4227-4236.
Grubina, R., "DNA Templated Synthesis of a Synthetic Small Molecule Library", The Nucleus, vol. LXXXII, No. 5, p. 10-14, Jan. 2004.
Gruen, et al., "An In Vivo Selection System for Homing Endonuclease Activity", Nucleic Acids Research 30, e29 (2002).
Gryaznov SM, et al., "Template controlled coupling and recombination of oligonucleotide blocks containing thiophosphoryl groups", Nucleic Acids Res., vol. 21 (6), pp. 1403-1408, 1993 B.
Gryaznov, et al., "Chemical Ligation of oligonucleotides in the presence and absence of a template", J. Amer. Chem. Soc. , vol. 115, pp. 3808-3809, 1993 A.
Gryaznov, SM, et al., "Enhancement of selectivity in recognition of nucleic acids via chemical autoligation", Nucleic Acids Res., vol. 22(12), pp. 2366-2369, 1994.
Gumport, et al., "T4 RNA Ligase as a Nucleic Acids Synthesis and Modification Reagent", Elsevier North Holland, Inc., 314-345 (1981).
Guo, T. et al., "Preparation of Encoded Combinatorial Libraries for Drug Discovery", Methods in Molecular Biology, Combinatorial Library Methods and Protocols, vol. 201, pp. 23-39.
Halpin, et al., "DNA display I. Sequence-encoded routing of DNA populations," PLoS Biol. Jul. 2004;2(7):E173. 1015-1021, Epub 2004 (A) Jun. 22.
Halpin, et al., "DNA display II. Genetic manipulation of combinatorial chemistry libraries for small-molecule evolution," PLoS Biol. Jul. 2004;2(7):E174. Epub 2004 (B) Jun. 22, 1022-1030.
Halpin, et al., "DNA display III. Solid-phase organic synthesis on unprotected DNA," PLoS Biol. Jul. 2004;2(7):E175. Epub 2004 (C) Jun. 22, 1031-1038.
Hansen, M. et al., "A Yoctoliter-scale DNA reactor for small-molecule evolution", J Am Chem Soc, 131, 1322-1327. (2009).
Harada, et al., "In vitro selection of optimal DNA substrates for T4 RNA ligase", Proc. Natl. Acad. Sci. USA, vol. 90, pp. 1576-1579, Feb. 1993(A).
Harada, et al., "Unexpected substrate specificity of T4 DNA ligase revealed by in vitro selection", Nucleic Acids Research, vol. 21, No. 10, 2287-2291 (1993 B).
Harada, et al., "In vitro selection of optimal DNS substrates for ligation by a water-soluble carbodiimide", J Mol Evol., 38, 558-560 (1994).
Herpin, et al., "Synthesis of a 10 000 member 1,5-Benzodiazepine-2-one Library by the Directed Sorting Method", J. Comb. Chem., 2, 513-521 (2000).

Herrlein, MK, et al., "Selective chemical autoligation on a double-stranded DNA template", Nucleic Acids Res., vol. 22 (23), pp. 5076-5078, Nov. 25, 1994.
Higgins, et al., "Addition of Oligonucleotides to the 5'-Terminus of DNA by T4 RNA Ligase", Nucleic Acids Research, 6(3): 1013-1024, 1979 (A).
Higgins, et al., "DNA-joining Enzymes: A Review", Methods in Enzymology, vol. 68, pp. 50-71, 1979 (B).
Hinton, et al. "T4 RNA Ligase Joins 2'-Deoxyribonucleoside 3', 5'-Bisphosphates to Oligodeoxyribonucleotides", American Chemical Society,1978, pp. 5091-5097.
Holmes, CP., "Model Studies for New o-Nitrobenzyl Photolabile Linkers: Substituent Effects on the Rates of Photochemical Cleavage", J. Org. Chem. 1997, 62, 2370-2380.
Housby, et al., "Fidelity of DNA ligation: a novel experimental approach based on the polymerisation of libraries of oligonucleotides", Nucleic Acids Research, 1998, vol. 26, No. 18, pp. 4259-4266.
Hsu, et al., "Detection of DNA point mutations with DNA mismatch repair enzymes," carcinogenesis, 1994, 15:1657-1662.
Inoue, et al., "Oligomerization of (Guanosine 5'phosphor)-2-methylimidazolideon Poly(C)," J. Mol. Bio. (1982), 162, 201-217.
Inoue, T., et al., "A nonenzymatic RNA polymerase model", Science 1983, 219, p. 859-862.
Ito et al., "Tag-reporter and Resin Capture—Release Strategy in Oligosaccharide Synthesis," Chemistry A European Journal (2002) 8(14):3077-3084.
James, et al., "The Fidelity of Template-Directed Oligonucleotide Ligation and the Inevitability of Polymerase Function", Origins of Life and Evolution of the Biosphere, 29, 1999, pp. 375-390.
Janda, "Tagged versus untagged libraries: Methods for the generation and screening of combinatorial chemical Tibraries", Proc. Natl. Acad. Sci. USA, vol. 91, pp. 10779-10785, Nov. 1994.
Jones, et al., "Enzymes in organic synthesis 22. Effects of organic solvents on horse liver alcohol dehyrogense-catalyzed reduction"; Can. J. Chem. 60 1982; pp. 335-338.
Jäschke, et al., "Evolution of DNA and RNA as catalysts for chemical reactions"; Current Opinion in Chemical Biology 2000; 4; pp. 257-262.
Jäschke, et al. "Synthesis and properties of oligodeoxyribonucleotide—polyethylene glycol conjugates", Nucleic Acids Research, 1994, vol. 22, No. 22, pp. 4810-4817.
Kahn, Jason. "DNA-ligases": www.adnadn.umd.edu/biochem/kahn/molmachines/replication/DNA%20ligase.htm 4 pages, downloaded Dec. 10, 2009.
Kanagawa, "Bias and Artifacts in Multitemplate Polymerase Chain Reactions (PCR)," Journal of Bioscience and Bioengineering, vol. 96, No. 4, pp. 317-323, 2003.
Kanan, et al., "Reaction Discovery Enabled by DNA-Templated Synthesis and In Vitro Selection", Supplementary Information, pp. 1-20. 2004 (B).
Kanan, M.W et al., "Reaction discovery enabled by DNA-templated synthesis and in vitro selection", Nature, vol. 431, Sep. 30, 2004 (A), pp. 545-549.
Keiler, KC, et al., "Role of peptide tagging system in degradation of proteins synthesized from damaged messenger RNA", Science, vol. 271, pp. 990-993, Feb. 16, 1996.
Kerr, JM et al., "Encoded Combinatorial Peptide Libraries Containing Non-Natural Amino Acids", J. Am. Chem. Soc., USA. 115, 2529-2531, (1993).
Kinoshita, et al., "Enzymatic Synthesis of Code Regions for Encoded Combinatorial Chemistry (ECC)", Nucleic Acids Symposium Series, 34: 201-202, 1995.
Kinoshita, Y. et al., "Strand ligation in a double-stranded DNA by T4 RNA ligase", Department of Functional Materials Science, Saitama University, Urawa, Japan, Chemistry Letters (1996), 797-798.
Klekota, B., et al., "Selection of DNA-Binding Compounds via Multistage Molecular Evolution", Tetrahedron, 55, (1999) 11687-11697.
Klibanov, Alexander M., "Why are enzymes less active in organic solvent than water?", Trends in Biotechnology vol. 15, Issue 3, 97-101; Mar. 1, 1997, Abstract.

(56) References Cited

OTHER PUBLICATIONS

Koivunen E. et al., "Phage libraries displaying cyclic peptides with different ring sizes: Ligand Specificities of the RGD-directed Integrins" Bio/Technology, 1995, pp. 265-270.
Krishna, "Developments and trends in enzyme catalysis in nonconventional media", Biotechnology Advances; 2002 pp. 239-267 ,Abstract.
Krug, et al., "Reversal of T4 RNA Ligase", American Chemical Society, 1982, vol. 21, No. 8, pp. 1858-1864.
Kurz, M. et al., "cDNA—protein fusions: covalent protein—gene conjugates for the in vitro selection of peptides and proteins", Chembiochem, 2001, pp. 666-672.
Kurz, M., et al., "An efficient synthetic strategy for the preparation of nucleic acid-encoded peptide and protein libraries for in vitro evolution protocols". Fourth International Electron Conference on Synthetic Organic Chemistry (ECSOC-4), www.mdpi.org/ecsoc-4.htm, Sep. 1-30, 2000 (A).
Still, "Career-In-Review (CIR)", BJ Wright, Synthesis Literacy Group, Columbia University Chemistry, Mar. 30, 2007.
Storhoff, et al., "Programmed Materials Synthesis with DNA", Chem. Rev., vol. 99 (7), pp. 1849-1862, 1999.
Summerer, et al., "DNA-templated synthesis: more versatile than expected", Angew Chem Int Ed, vol. 41 (1), pp. 89-90, 2002.
Tabor, "DNA-ligases"; Current Protocols in Molecular Biology, (1987) 3.14.1-3.14.4.
Takemori, et al., "Stabilization of Enzyme Activity by an Organic Solvent", Abstract only, Nature 215, 417-419 (Jul. 22, 1967).
Tamura, et al., "Oligonucleotide-directed peptide synthesis in a ribosome- and ribozyme-free system", Proc Natl Acad Sci USA, vol. 98 (4), pp. 1393-1397, Feb. 13, 2001.
Tan et al., "Natural-product inhibitors of human DNA ligase I.", Biochemical Journal (1996) 314: 993-1000.
Tan, et al., "Ligand discovery using encoded combinatorial libraries", Current Opinion in Drug Discovery & Development, 3(4), p. 439-453, 2000.
Tanaka, et al., "Synthesis of a novel nucleoside for alternative DNA base pairing through metal complexation", J. Org. Chem. 1999, 64, 5002-5003.
Tessier, et al. "Ligation of Single-Stranded Oligodeoxyribonucleotides by T4 RNA Ligase", Analytical Biochemistry 158, 171-178 (1986).
Tse, et al., "Translation of DNA into a library of 13,000 synthetic small-molecule macrocycles suitable for in vitro selection", J Am Chem Soc, 130, 15611-15626, (2008).
Uhlenbeck, et al., "T4 RNA Ligase", The Enzymes, vol. XV, pp. 31-58, 1982.
Unknown, "Science & Technology: Concentrates", Chem. & Eng. News, (2004).
Vágner, et al., "Enzyme-mediated spatial segregation on individual polymeric support beads: Application to generation and screening of encoded combinatorial libraries", Proc. Natl. Acad. Sci. USA, vol. 93, pp. 8194-8199, Aug. 1996.
Vaisman, et al., "Human DNA polymerase, promiscuous mismatch extension", JBC 276: 30615-30622 (2001).
Visscher, et al., "Template-Directed Synthesis of Acyclic Oligonucleotide Analogues", Oligomerization Catalyzed by a Polynucleotide Analogu, Reports, 1989, 329-331.
Visscher, et al., "Oligomerization of deoxynucleoside-bisphosphate dimers: template and linkage specificity", Orig Life Evol Biosph, vol. 19, pp. 3-6, 1989 (A).
Visscher, J., et al., Template-directed Synthesis of Acyclic Oligonucleotied Analogues, J. Mol. Evol., 1988, 28:3-6.
Vratskikh, et al., "Solid-phase synthesis of oligoribonucleotides using T4 RNA Ligase and T4 polynucleotide kinase", Biochimie (1995), 77, 227-232.
Wagner, et al., "Mutation detection using immobilized mismatch binding protein (MutS)", Nucleic Acids Research 23, 3944-3948, 1995.
Walder, et al., "Complementary carrier peptide synthesis: general strategy and implications for prebiotic origin of peptide synthesis", Proc Natl Acad Sci USA, vol. 76 (1), pp. 51-55, 1979 (A).
Wang, et al., "A new functional suppressor tRNA/aminoacyl-tRNA synthetase pair for the in vivo incorporation of unnatural amino acids into proteins", J. Am. Chem. Soc. 2000, 122, 5010-5011, 2000.
Wang, et al., "Circular RNA oligonucleotides. Synthesis, nucleic acid binding properties, and a comparison with circular DNAs", Nucleic Acids Research, 1994, vol. 22, No. 12; 2326-2333.
Washington, et al., "Mismatch extension ability of yeast and human DNA polymerase •", JBC 276, 2263-2266 (2001).
Waybright, et al., "Oligonucleotide-directed assembly of materials: defined oligomers", J. Am Chem Soc., vol. 123, pp. 1828-1833, 2001.
Website of prof. David R. Liu, publicly available Apr. 19, 2001.
Website of prof. David R. Liu, publicly available Apr. 23, 2003.
Website of prof. David R. Liu, publicly available Aug. 1, 2003.
Website of prof. David R. Liu, publicly available Aug. 2, 2002.
Website of prof. David R. Liu, publicly available Dec. 16, 2003.
Website of prof. David R. Liu, publicly available Feb. 10, 2004.
Website of prof. David R. Liu, publicly available Feb. 15, 2001.
Website of prof. David R. Liu, publicly available Feb. 8, 2003.
Website of prof. David R. Liu, publicly available Jun. 4, 2002.
Website of prof. David R. Liu, publicly available Jun. 6, 2003.
Website of prof. David R. Liu, publicly available Mar. 1, 2001.
Website of prof. David R. Liu, publicly available Mar. 11, 2000.
Website of prof. David R. Liu, publicly available Mar. 27, 2003.
Website of prof. David R. Liu, publicly available Mar. 31, 2001.
Website of prof. David R. Liu, publicly available Nov. 20, 2002.
Website of prof. David R. Liu, publicly available Nov. 29, 2002.
Website of prof. David R. Liu, publicly available Nov. 30, 2001.
Website of prof. David R. Liu, publicly available Oct. 15, 2000.
Website of prof. David R. Liu, publicly available Oct. 15, 2003.
Website of prof. David R. Liu, publicly available Oct. 17, 2002.
Website of prof. David R. Liu, publicly available Sep. 23, 2001.
Website of prof. David R. Liu, publicly available Sep. 24, 2002.
Weiss, et al., "Enzymatic Breakage and Joining of Deoxyribonucleic Acid, I. Repair of Single-Strand Breaks in DNA by an Enzyme System From *Escherichia coli* Infected With T4 Bacteriophage", PNAS 1967, 57, (4): 1021-1028.
Weizman, et al., "2,2'-Bipyridine ligandoside: a novel building block for modifying DNA with intra-duplex metal complexes", J. Am. Chem. Soc., 2001, 123, 3375-3376.
Summons to attend Oral Proceedings for European Application No. 03757752.5 dated Aug. 5, 2008.
Letter for Oral Proceeding for European Application No. 03757752.5 dated Dec. 15, 2008.
Telephone Summary for European Application No. 03757752.5 dated Dec. 23, 2008.
Letter for Oral Proceedings 2 for European Application No. 03757752.5 dated Jan. 2, 2009.
Oral proceedings cancelled for European Application No. 03757752.5 dated Jan. 8, 2009.
3rd Office Action for European Application No. 03757752.5 dated Jan. 14, 2009.
Reply to 3rd Office Action for European Application No. 03757752.5 dated Jul. 17, 2009.
Intention to grant for European Application No. 03757752.5 dated Mar. 30, 2010.
Decision to Grant for European Application No. 03757752.5 dated May 19, 2011.
Request for Corrections for European Application No. 03757752.5 dated Nov. 9, 2010.
Decision to Grant dated Oct. 10, 2013 re European patent appliction No. 09154197.9.
Opposition against EP 1558744 filed by Strawman Limited on Mar. 15, 2012.
Opposition against EP 1558744 by HGF on Mar. 14, 2012.
Response to oppositions against EP 1558744 submitted Dec. 5, 2012.
Written submissions re EP 1558744 submitted Sep. 11, 2013 by proprietor.
Written submissions re EP 1558744 submitted Sep. 12, 2013 by opponent.
European Search Report dated Feb. 6, 2012 & Search Opinion.

(56) References Cited

OTHER PUBLICATIONS

Response to ESR dated Feb. 6, 2012 re European Patent Application No. 10183942.1 submitted Jan. 9, 2013.
1st Office Action for European Patent Application No. 10183942.1 dated Feb. 11, 2013.
Communication re Partial European Seach Report dated Feb. 10, 2012.
Partial European Search Report dated Feb. 3, 2012.
European Search Report dated Jun. 6, 2012 re EP 10184069.2.
Response dated Apr. 12, 2013 to European Search Report issued in European Patent Application No. 10184069.2.
1st Office Action for European Patent Application No. 10184069.2 dated Jul. 3, 2013.
ISR International Search Report for PCT/DK2004/000630 dated Feb. 14, 2005.
1st Office Action for European Application No. 04762850.8 dated Dec. 6, 2006.
Reply to 1st Office Action for European Application No. 04762850.8 dated Oct. 18, 2007.
2nd Office Action for European Application No. 04762850.8 dated Jan. 24, 2008.
Reply to second Office Action Reply to 2nd Office Action for European Application No. 04762850.8 dated Sep. 2, 2008.
Intent to Grant for European Applicaton No. 04762850.8 dated Dec. 10, 2008.
Amendment after Grant for European Application No. 04762850.8 dated Jul. 17, 2009.
Decision to Grant for European Application No. 04762850.8 dated Oct. 8, 2009.
ISR International Search Report for International Application No. PCT/DK2005/000199 dated Jan. 23, 2006.
1st Office Action for European Application No. 05715120.1 dated Apr. 12, 2007.
Reply to 1st Office Action for European Application No. 05715120.1 dated Feb. 1, 2008.
2nd Office Action for European Application No. 05715120.1 dated Mar. 25, 2008.
Reply to 2nd Office Action for European Application No. 05715120.1 dated Jan. 9, 2009.
Intent to Grant for European Application No. 05715120.1 dated May 7, 2009.
Amendment after Grant for European Application No. 05715120.1 dated Sep. 3, 2009.
Decision to Grant for European Application No. 05715120.1 dated Oct. 1, 2009.
ISR International Search Report for International Application No. PCT/DK2005/000106 dated Sep. 12, 2005.
1st Office Action for European Application No. 05700655.3 dated Jun. 19, 2007.
Reply to 1st Office Action for European Application No. 05700655.3 dated Apr. 11, 2008.
2nd Office Action for European Application No. 05700655.3 dated Sep. 12, 2008.
Reply to 2nd Office Action for European Application No. 05700655.3 dated Jul. 9, 2009.
3rd Office Action for European Application No. 05700655.3 dated Aug. 12, 2009.
Reply to 3rd Office Action for European Application No. 05700655.3 dated Feb. 9, 2010.
Intent to Grant for European Application No. 05700655.3 dated Mar. 31, 2010.
Amendment after Grant for European Application No. 05700655.3 dated Nov. 11, 2010.
Decision to Grant for European Application No. 05700655.3 dated Dec. 2, 2010.
Mirkin, "Programming the assembly of two- and three-dimensional architectures with DNA and nanoscale inorganic building blocks", Inorg Chem., vol. 39, pp. 2258-2272, 2000.

Mudrakovskaya, et al., "Solid-Phase Enzymatic Synthesis of Oligoribonucleotides", Bioorg Khim, vol. 17, No. 6, 1991, pp. 469-472.
Mutter, M. et al., "Functionalized polyethylene glycols and polypeptides in organic synthesis and catalysis", Reactive Polymers, vol. 6 (1987), pp. 99-107.
Myers, et al., "Detection of single base substitutions by ribonuclease cleavage at mismatches in RNA:DNA duplexes", Science, 1985, 230: 1242-1246.
Nazarenko, et al., "A closed tube format for amplification and detection of DNA based on energy transfer", Nucleic Acids Research, 1997, vol. 25, No. 12, p. 2516-2521.
Needels, et al., "Generation and screening of an oligonucleotide-encoded synthetic peptide library", Proc. Natl. Acad. Sci., USA, vol. 90, pp. 10700-10704. Nov. 1993, Chemistry.
Nemoto, et al. "In vitro virus: bonding of mRNA bearing puromycin at the 3-'terminal end to the C-terminal end of its encoded protein on the ribosome in vitro". FEBS Lett., 1997, 414, 405-408.
Nestler, et al., "A General Method for Molecular Tagging of Encoded Combinatorial Chemistry Libraries", J. Org. Chem., 1994, 59, 4723-4724.
Nielsen, et al., "Synthetic methods for the implementation of encoded combinatorial chemistry". J. Am. Chem. Soc., 1993, 115, 9812-9813.
Nielsen, "Combinatorial chemistry and automation", DDT, vol. 1, No. 11, pp. 458-460, Nov. 1996.
Nikolaiev, et al., "Peptide-Encoding for structure determination of nonsequenceable polymers within libraries synthesized and tested on solid-phase supports", Peptide Research, vol. 6, No. 3, 1993, pp. 161-170.
Nishigaki, et al., "Y-ligation: an efficient method for ligating single-tranded DNAs and RNAs with T4 RNA ligase", Molecular Diversity, 1998, 4, 187-190.
O'Donovan, et al.,"Blind analysis of denaturing high-perfomance liquid chromatography as a tool for mutation detection", Genomics. 52:44-49, 1998.
Ohlmeyer, et al., "Complex synthetic chemical libraries indexed with molecular tags". Proc. Natl. Acad. Sci. USA, vol. 90, pp. 10922-10926, Dec. 1993, Chemistry.
Otto, et al., "Recent developments in dynamic combinatorial chemistry", Current opinion in Chemical Biology, 2002, 6:321-327.
Pavia, "The Chemical generation of molecular diversity", www.netsci.org/science/combichem/feature01.html, 2004.
Persichetti, et al., "Cross-Linked Enzyme Crystals (CLECs) of Thermolysin in the Synthesis of Peptides", Journal of the American Chemical Society, 117: 2732-2737, 1995.
Piccirilli, "RNA seeks its maker", Nature vol. 376, Aug. 17, 1995, p. 548-549.
Pochet, et al., "Solid-Supported Ligation Primer", Nucleic Acids Research, 16(4): 1619, 1988.
Polsky-Cynkin et al., "Use of DNA immobilized on plastic and agarose supports to detect DNA by sandwich hybridization", Clin. Chem., 1985, 31(9), 1438-1443.
Porco, Jr., "Synthesis Undressed", Nature, 446, 383-385, 2007.
Purmal, et al., "A new affinity reagent for the site-specific, covalent attachment of DNA to active-site nucleophiles application to the EcoRI and Rsrl restriction and modification enzymes", Nucleic Acids Research, vol. 20, No. 14, 1992 Oxford University Press; pp. 3713-3719.
Ramström, et al., "In situ generation and screening of a dynamic combinatorial carbohydrate library against concanavalin A", ChemBioChem, 2000, 1, 41-48.
Rembold, H, et al., "Single-strand regions of poly(G) act as templates for oligo(C) synthesis", J. Mol. Evol., 1994, 38, 205-210.
Roberts, et al., "RNA-peptide fusions for the in vitro selection of peptides and proteins", Proc Natl Acad Sci USA, 1997, 94,12297-12302.
Roberts, et al., "Simultaneous selection, amplification and isolation of a pseudo-peptide receptor by an immobilised N-methyl ammonium ion template", Chem. Commun., 2002, 938-939.
Robertson, "Direct Evolution Process for Robust Enzyme Catalysis in Organic Solvents"; Report date: Sep. 1996, pp. 1-14.

(56) References Cited

OTHER PUBLICATIONS

Robinson, "A Synthesis of Tropinone", Journal of the Chemical Society Transactions, vol. 111, pp. 762-768, 1917.
Rodriguez, et al., "Template-directed extension of a guanosine 5'-phosphate covalently attached to an oligodeoxycytidylate template", J Mol Evol (1991) 33:477-482.
Romaniuk, et al., "Joining of RNA molecules with RNA ligase", Methods in Enzymology, vol. 100, pp. 52-59, 1983.
Rosenbaum, et al., "Efficient and sequence-specific DNA-templated polymerization of peptide nucleic acid aldehydes". J. Am. Chem. Soc., vol. 125, 2003,13924-13925.
Saiki, et al., "Genetic analysis of amplified DNA with immobilized sequence-specific oligonucleotide probes", PNAS, 86, 6230-6234,1989.
Sakurai, K., et al., "DNA-Templated Functional Group Transformations Enable Sequence-Programmed Synthesis Using Small-Molecule Reagents", J. Am.Chem. Soc., 127, 1660-1661 (2005).
Salas, et al., "Biosynthetic polydeoxynucleotides as direct templates for polypeptide synthesis", Journal of Biological Chemistry, vol. 243, No. 5, pp. 1012-1015, 1968.
Sarmento, et al., "Cardosins A and B, Two New Enzymes Available for Peptide Synthesis", Journal of Molecular Catalysis B: Enzymatic, 5: 327-330, 1998.
Scheuermann, et al., "DNA-encoded chemical libraries", Journal of Biotechnology, 126 (2006) 568-581.
Scheuermann, et al., "DNA-encoded chemical libraries: A tool for drug discovery and for chemical biology", ChemBioChem, 0000, 00, 1-8, 2010.
Schmidt, et al., "Information transfer from peptide nucleic acids to RNA by template-directed syntheses", Nucleic Acids Res., vol. 25 (23), pp. 4792-4796,1997 (A).
Schmidt, et al., "Information transfer from peptide nucleic acids to RNA by template-directed syntheses", Nucleic Acids Res., vol. 25 (23), pp. 4797-4802, 1997 (B).
Schmitz, et al., "Solid-Phase Enzymatic Synthesis of Oligonucleotides", Organic Letters, 1(11): 1729-1731, 1999.
Schoenleber, et al., "Photochemical release of amines by C,N-bond cleavage", Synlett, 2003, 501-504.
Schultz, et al., "The Combinatorial Library: A Multifunctional Ressource", Biotechnol. Prog., 1996, 12, 729-743.
Schwartz, et al., "Template-directed synthesis of novel, nucleic acid-like structures", Science 1985, 228, 585-587.
Shabarova, et al., "Chemical ligation of DNA: the first non-enzymatic assembly of a biologically active gene", Nucl. Acids Res., 19:4247-4251 (1991).
Sharifian, "Errors induced during PCR amplification", May 30, 2010.
Shchepinov, et al., "Trityl tags for encoding in combinatorial synthesis", Tetrahedron 56 (2000) 2713-2724.
Shuman, "DNA ligases: Progress and Prospects"; www.jbc.org/content/284/26/17365.full 7 pages, downloaded Feb. 10, 2009.
Smith, et al., "DNA-guided assembly of proteins as a pathway to an assembler", (wadsworth.org/albcon97/abstract/krummena.htm) The 1997 Albany Conference: Biomolecular Motors and Nanomachines.
Snyder, et al., "Ordered multistep synthesis in a single solution directed by DNA templates", Angew Chem Int Ed, 44, 7379-7382. (2005).
Sokolova, et al.,"Chemical reactions within DNA duplexes Cyanogen bromide as an effective oligodeoxyribonucleotide coupling agent", FEB, vol. 232, No. 1, pp. 153-155; May 1988.
Anonymous. "DCI—A Logical Alternative Aviator", Glen Research, vol. 10, No. 1, 1-12 (1997).
"DNA Phosphoramidites & CPG's"; www.qualitysystems.com.tw/proligo/dna%20phosphoamidites%20&%20cpg's.htm Dec. 2, 2010.
"Dokl Akad Nauk SSSR", vol. 258, 1242-1245, Krynetskya NF Tumanov YV (1981).
"Finding reactions in a haystack: Try'em all, see what works", Meeting American Chemical Society, Sep. 10, 2004, vol. 305, Science. p. 1558.
"Ligase", Answers.com: www.answers.com/topic/ligase, [acessed Dec. 10, 2009].
"Organic Chemistry", Wikipedia, [accessed Dec. 10, 2009]: www.wikipedia.org/wiki/organic_chemistry (10 pages).
"Orthogonal Protection Protecting Group", Wikipedia: www.wikipedia.org/wiki/protecting_group#Orthogonal_protection [accessed Apr. 15, 2010].
Abravaya, et al., "Detection of point mutations with a modified ligase chain reaction (Gap-LCR)", Nucleic Acids Research, vol. 23, No. 4, 675-682 (1995).
Acevedo, et al., "Template-directed oligonucleotide ligation on hydroxylapatite", Nature vol. 321, 19, Jun. 1986, 790-792.
Acevedo, O. L., et al., "Non-enzymatic transcription of an oligonucleotide 14 residues long", J. Mol. Biol. 1987, 197, 187-193.
Acinas, et al., "PCR-Induced Sequence Artifacts and Bias: Insights from Comparison of Two 16S rRNA Clone Libraries Constructed from the same Sample", Applied and Environmental Microbiology, vol. 71, No. 12, 8966-8969, (2005).
Agarwal, et al., "Total Synthesis of the gene for an alanine transfer ribonucleic acid from yeast", Nature, 227, 27-34 (1970).
Albagli, D, et al., "Chemical amplification (CHAMP) by a continuous, self-replicating oligonucleotide-based system", J. Am. Chem. Soc., vol. 121, pp. 6954-6955,1999, Pub. On the web Jul. 14, 1999.
Annex I: Vipergen Technology Paper—"The YoctoReactor drug discovery technology platform." 2 pages. No Date.
Annex II: Vipergen Technology Paper—"The YoctoReactor drug discovery technology platform." 2 pages. Aug. 2008.
Anonymous. "5,6-Dihydro-Pyrimidines, 2'-Phosphoramidites", Glen Research Report, vol. 10, 1997 (December issue), p. 11.
Anonymous. "Cytofectin GSV Transfection Protocol", Glen Research Report, vol. 10,1997 (December issue), p. 4-6.
Anonymous. "More Novel Monomers -4-Thio-dU, 5'-Amino-dT, 2'-F-Pyrimidines", Glen Research Report, vol. 10, 1997 (December issue), p. 10.
Anonymous. "New Fluorescent Reagents—Tamra CPG, Fluorescein-dt", Glen Research Report, vol. 10, 1997 (December issue), p. 7.
Anonymous. "Non-enzymatic Ligation of Single-Stranded and Duplex DNA", Glen Research Report, vol. 10, 1997 (December issue), p. 12.
Anonymous. "Preparing Oligonucleotides for Antisensen Experiments", Glen Research Report, vol. 10, 1997 (December issue), 2-3.
Anonymous. "Q-Supports Reduce Cleavage Time to 2 Minutes", Glen Research Report, vol. 10, 1997 (December issue), p. 9.
Anonymous. "Universal Support Replaces Individual Columns", Glen Research Report, vol. 10, 1997 (December issue), p. 8.
Australian Patents Act 1990—Section32 Regulation 3.6, (Request for a Determination of Dispute Between Applicants) dated Nov. 21, 2008.
Baldwin, "Design, Synthesis and use of binary encoded synthetic chemical libraries", Moleculat Diversity, 2, 81-88 (1996).
Baldwin, et al. "Synthesis of a Small Molecule Combinatorial Library Encoded with Molecular Tags", J. Am. Chem. Soc. 1995, 117, 5588-5589.
Baran et al., "Total Synthesis of Marine natural products without using protecting groups", Nature, vol. 446, 404-408 (2007).
Barany, "Genetic disease detection and DNA amplification using cloned thermostable ligase", Proc. Natl. Acad. Sci., vol. 88, 189-193 (1991).
Barany, F., "The ligase chain reaction in a PCR world", Genome Res. 1991 (B); 1:5-16.
Barany, F., "The Tagl "star" reaction: strand preferences reveal hydrogen-bond donor and acceptor sites in canonical sequence recognition", 1988, Gene vol. 65; pp. 149-165.
Battersby, et al. "Optical encoding of microbeads for gene screening: alternatives to microarrays". Drug Discovery Today, 2001, vol. 6, supp 1, p. 19-26.
Bayer, E. et al., "Liquid Phase Synthesis of Peptides", Nature, vol. 237, 1972.
Benner, SA., "Expanding the genetic lexicon: incorporating non-standard amino acids into proteins by ribosome-based synthesis". TIBTECH, May 1994;12:158-163.

(56) References Cited

OTHER PUBLICATIONS

Berger, M, et al., "Universal bases for hybridization, replication and chain termination", Nucleic Acids Research, Oxford University Press, vol. 28, No. 15, pp. 2911-2914, 2000.
Bittker, et al., "Nucleic Acid Evolution and Minimization by Non-homologous Random Recombination", Nature Biotechnology, 20, 1024-1029 (2002 A).
Bittker, et al., "Recent advances in the in vitro evolution of nucleic acids", Curr Opin Chem Biol, vol. 6, pp. 367-374, 2002, Review Pub. On the web Mar. 20, 2002 (B).
Bonora, et al., "Large Scale, PEG-Supported DNA Synthesis"; Nucleosides and Nucleotides, 10 (1-3), (1991).
Borman, "Combinatorial chemists focus on small molecules, molecular recognition, and automation", Chemical & Engineering News, Feb. 12, 1996.
Braun, E., et al., "DNA-templated assembly and electrode attachment of a conducting silver wire". Nature, vol. 391, Feb. 19, 1998, 775-778.
Brennan, et al., "Using T4 RNA Ligase with DNA Substrates", Methods in enzymology, vol. 100, pp. 28-52, 1983.
Brenner, et al., "Encoded Combinatorial Chemistry", Proc Natl. Acad. Sci. USA, vol. 89, pp. 5381-5383, Jun. 1992.
Broude, "Stem-loop oligonucleotides: a robust tool for molecule biology and biotechnology", Trends in Biotechnology, vol. 20, No. 6, Jun. 2002 pp. 249-256.
Bruick, et al., "A simple procedure for constructing 5' -amino terminated oligodeoxynucleotides in aqueous solution", Nucleic Acids Res., vol. 25 (6), pp. 1309-1310,1997.
Bruick, et al., "Template-Directed Ligation of Peptides to Oligonucleotides", Chemistry and Biology, 1996, vol. 3, 49-56.
Braasch, et al., "Locked nucleic acids (LNA): fine-tuning the recognition of DNA and RNA", Chemistry & Biology, 8, 1-7 (2001).
Buller, et al., "Drug Discovery with DNA-Encoded Chemical Libraries", Bioconjugate Chem., (2010).
Buller, et al., "Design and synthesis of a novel DNA-encoded chemical library using Diels-Alder cycloadditions", Bioorg. Med. Chem. Lett., 18, 5926-5931, (2008).
Buller, et al., "Discovery of TNF inhibitors from an DNA-encoded chemical library based on Diels-Alder cycloaddition", Chem. Biol., 16, 1075-1086. (2009).
Bunin, et al., "[26] Synthesis and Evaluation of 1,4-Benzodiazepine Libraries", Methods in Enzymology, vol. 267, pp. 448-465, 1996.
Bunin, et al., "The combinatorial synthesis and chemical and biological evaluation of a 1,4-benzodiazepine library", Proc. Natl. Acad. Sci. USA, vol. 91, pp. 4708-4712, May 1994.
Communication (office action) by the European Patent Office dated Mar. 24, 2016 in relation to European Patent No. 10741877.4.
Glen Research (Catalogue No. 10-1014-XX)—Mar. 8, 2005 + Material Safety Data Sheet on Catalogue No. 10-1014-xx—Sep. 11, 2004.
Glen Research (Catalogue No. 10-1054-XX)—Mar. 8, 2005 + Material Safety Data Sheet on Catalogue No. 10-1054-xx—Oct. 28, 2004.
Glen Research (Catalogue No. 10-1092-XX)—Apr. 28, 2005 + Material Safety Data Sheet on Catalogue No. 10-1092-xx—Oct. 28, 2004.
Glen Research (Catalogue No. 10-1590-XX)—Aug. 21, 2008 + Further Info on 10-1590-xx—Dec. 12, 2008.
Han et al., "Quantum-dot-tagged microbeads for multiplexed optical coding of biomolecules", Nature Biotechnology, 2001, vol. 19, pp. 631-635.
Korshun et al., "5-(1-Pyrenylethynyl)-2'-Deoxyuridine, A N Ovel Fluorescent Nucleosideanalog", Bioorganiceskaa himia, 22(12), 1996, pp. 923-925. (English abstract only).
Mullah et al., "Efficient synthesis of double dye-labeled oligodeoxyribonucleotide probes and their application in a real time PCR assay", Nucleic Acids Research, 1998, vol. 26, No. 4, pp. 1026-1031.
Thelwell, "Mode of action and application of Scorpion primers to mutation detection", Nucleic Acids Research, 2000, vol. 28, No. 19, pp. 3752-3761.
Third Party observation filed with the European Patent Office on Mar. 14, 2016 in relation to European Patent No. 10741877.4 (X-Chem Inc.).
Wagner, "Gene inhibition using antisense oligodeoxynucleotides", Nature, 1994, vol. 372, pp. 333-335.
Wagner, "Antisense gene inhibition by oligonucleotides containing C-5 propyne pyrimidines", Science, 1993, vol. 260, pp. 1510-1513.
Yamana et al., "Synthesis and Binding Properties of Oligonucleotides Containing an Azobenzene Linker", Nucleosides & Nucleotides, 1998, vol. 17, No. 1-3, pp. 233-242.
Zammatteo et al., "Amination of polystyrene microwells: Application to the covalent grafting of DNA probes for hybridization assays", Analytical Biochemistry, 236, pp. 85-94, 1996.

\* cited by examiner

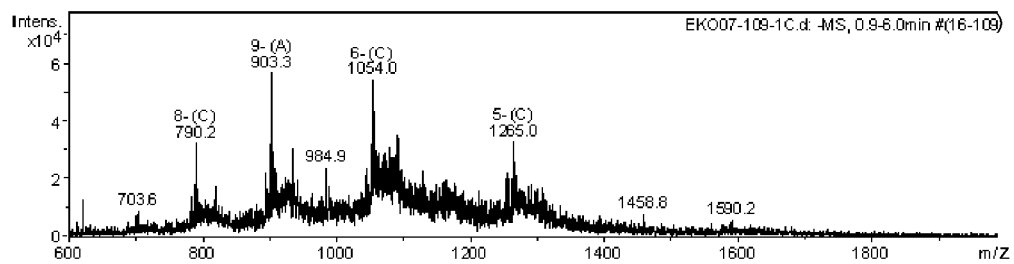
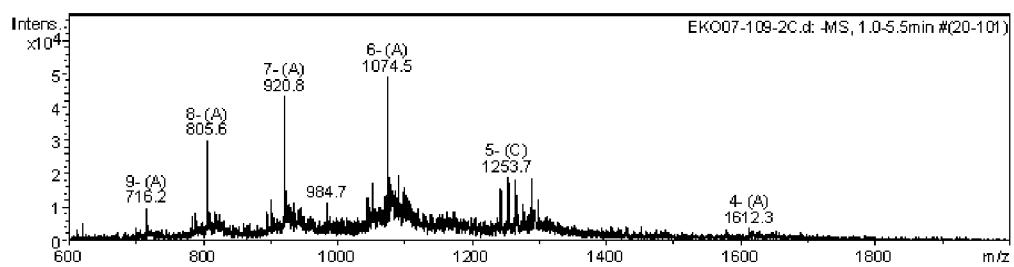
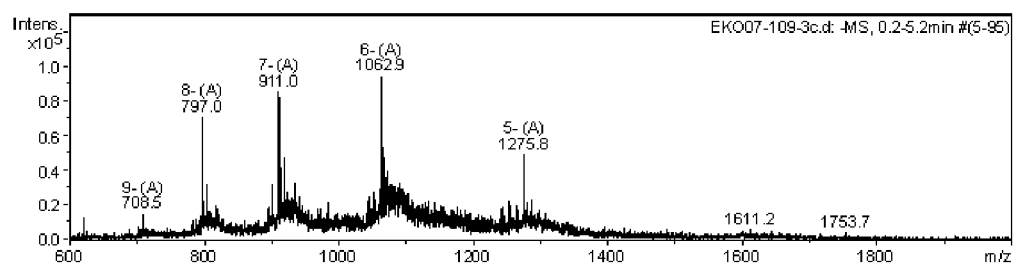
FIG 10 a) 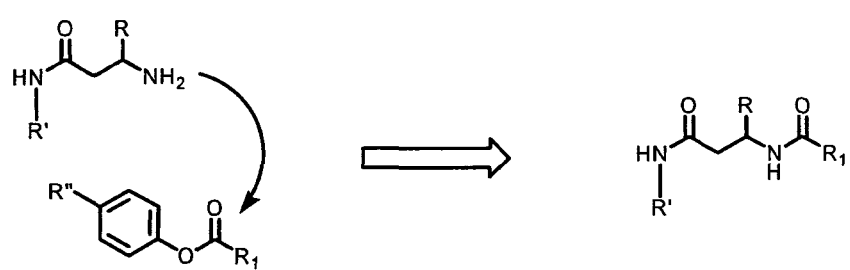
b) 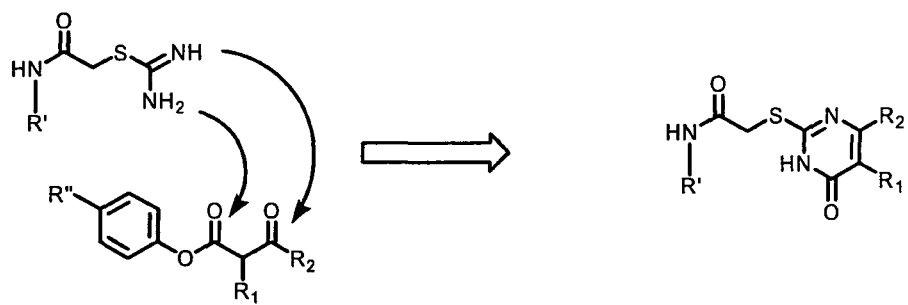
FIG 28

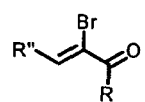
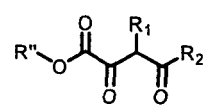
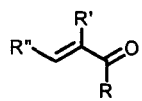
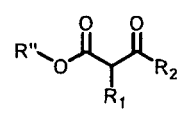
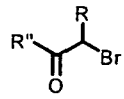
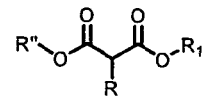
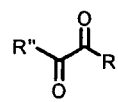
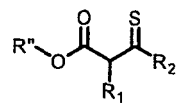
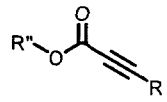
FIG 29

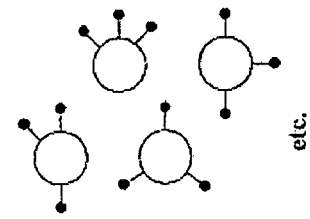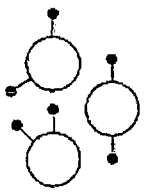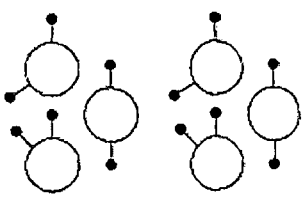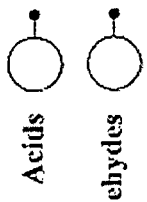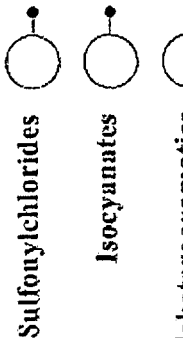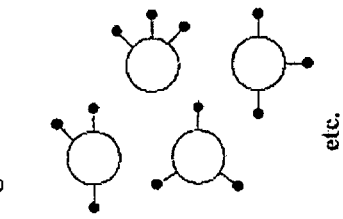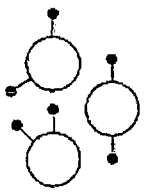
FIG 39

Library Mimic (general)

Purification handle

Step1: Add oligonucleotide complementary to a control mimic sequence. Purify using handle on complementary oligonucleotide, such as a biotin group, and a suitable method, such as interaction to SA-beads
Step2: Elute mimic and evaluate by analytical tool such as MALDI- or Electrospray MS

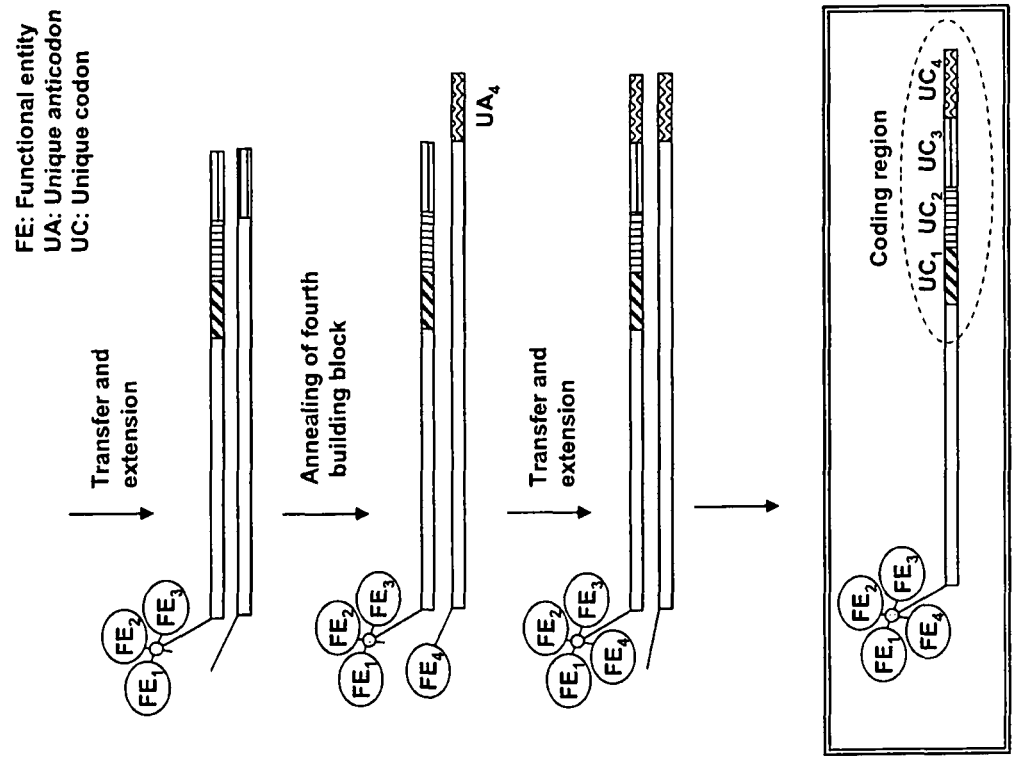
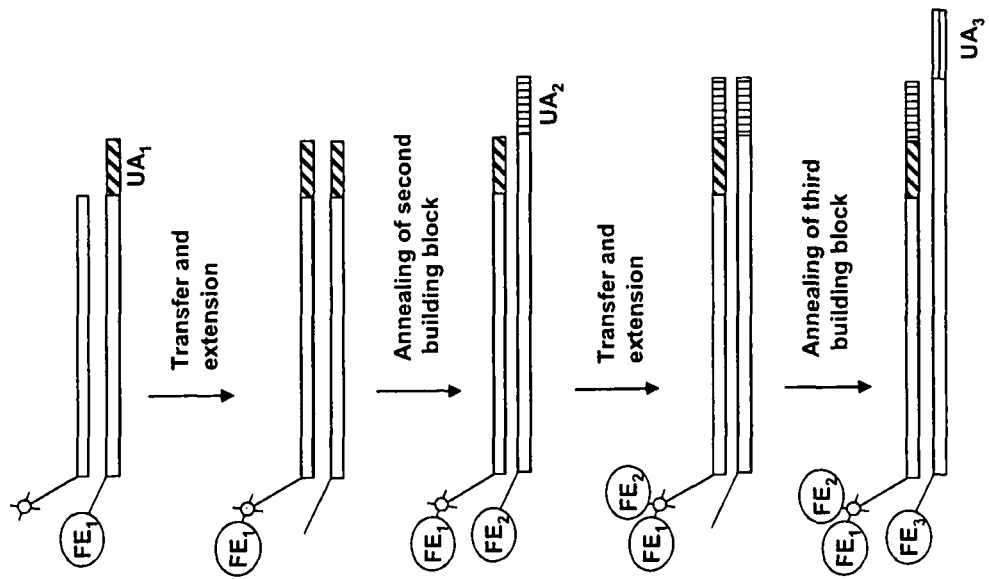
FIG 75

FE: Functional entity
UA: Unique anticodon
UC: Unique codon
IUC: Internal unique codon
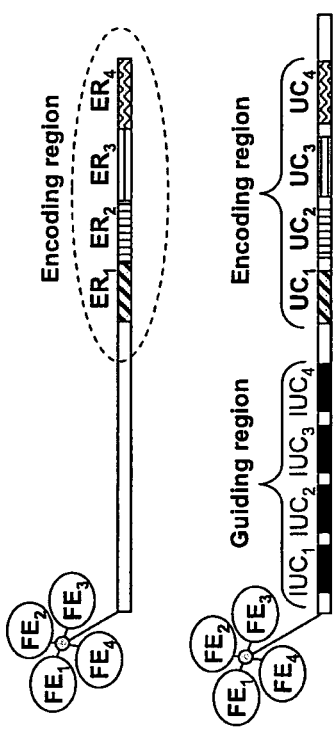
A
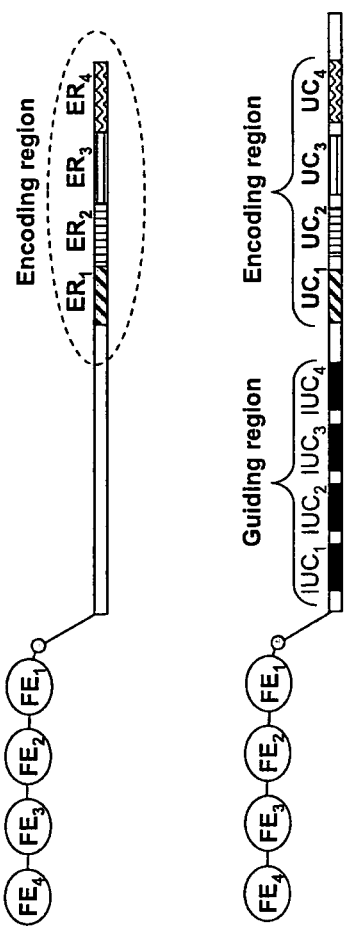
B
FIG 79

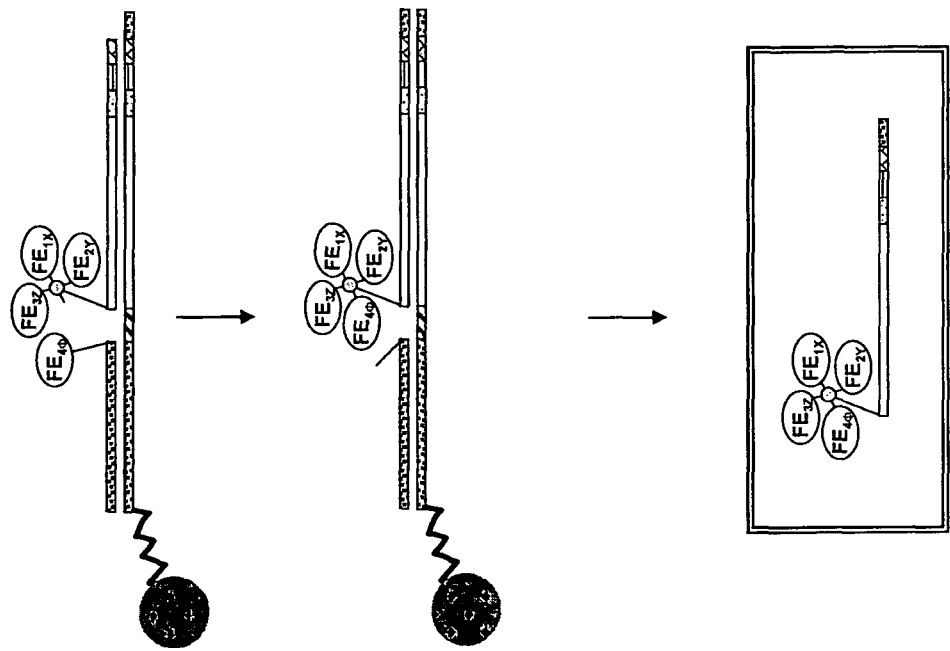
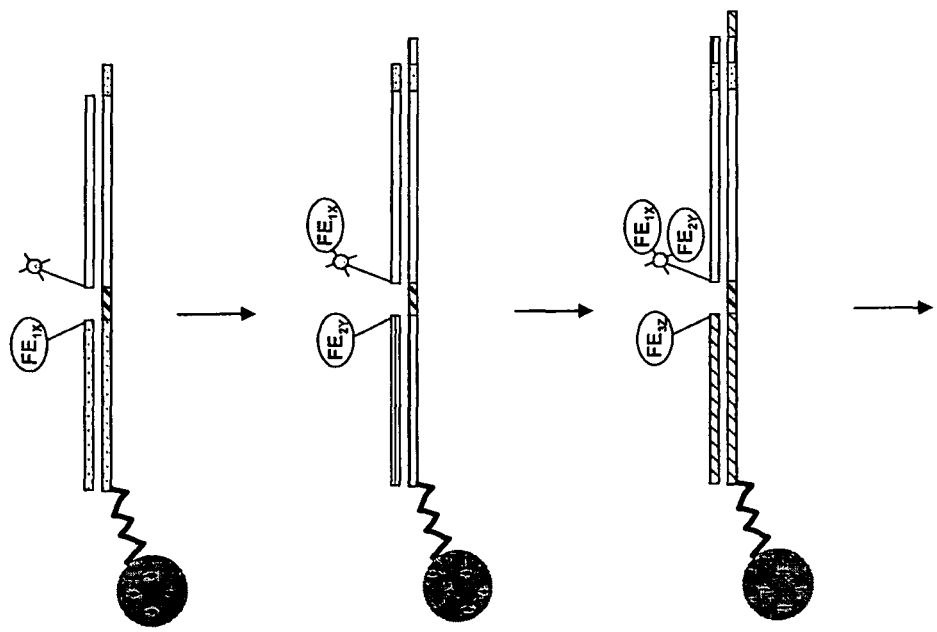
FIG 82

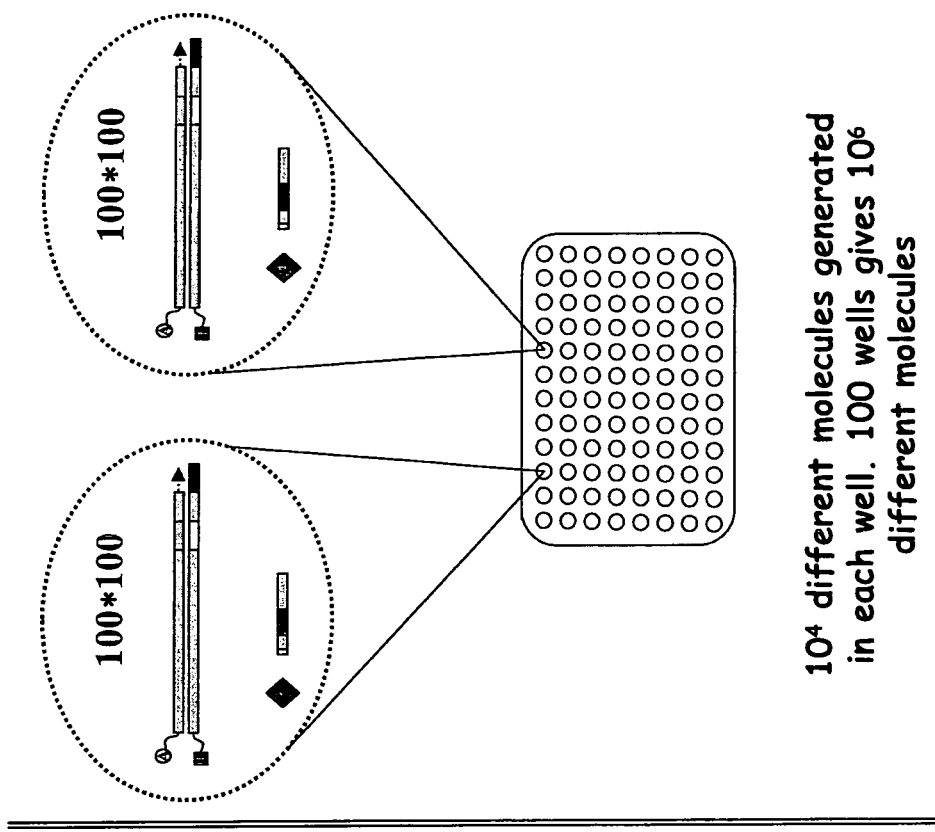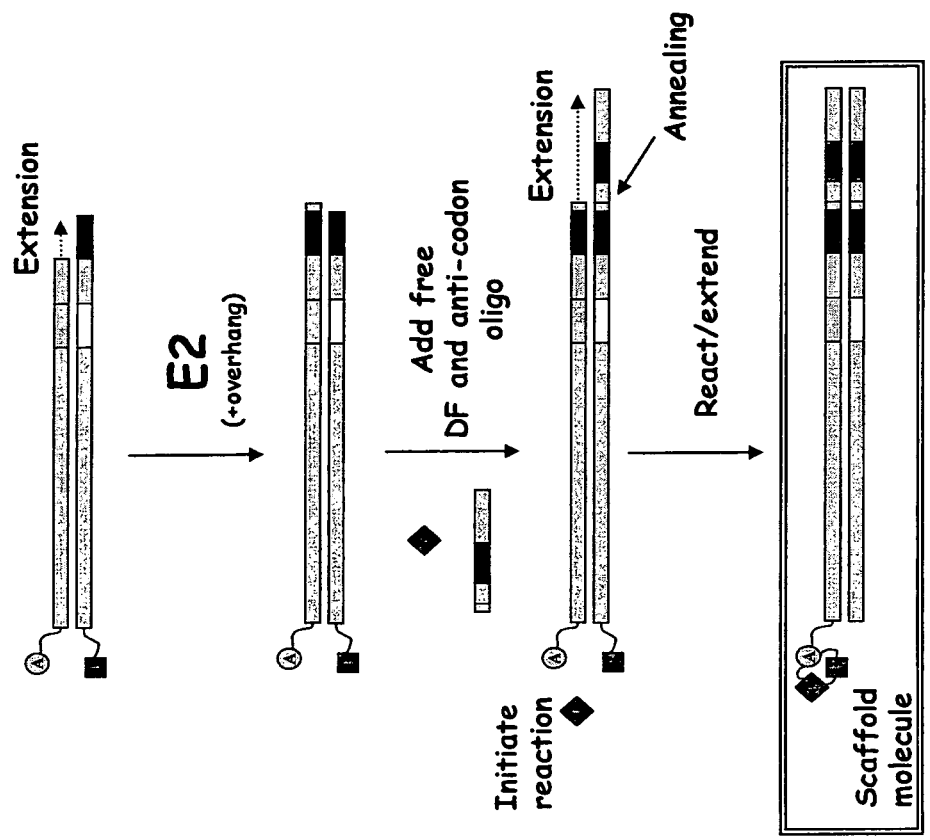
FIG 89

US 11,225,655 B2

BI-FUNCTIONAL COMPLEXES AND METHODS FOR MAKING AND USING SUCH COMPLEXES

This application is a National Stage Application of PCT/DK2011/000031, filed 16 Apr. 2011, which claims benefit of Ser. No. 61/325,160, filed 16 Apr. 2010 in the United States and Serial No. PA 2010 70149, filed 16 Apr. 2010 in Denmark and which applications are incorporated herein by reference. To the extent appropriate, a claim of priority is made to each of the above disclosed applications.

FIELD OF INVENTION

The present invention is directed to methods for organic synthesis of molecules and to molecules having been synthesised by the disclosed methods, as well as to methods for using such molecules.

BACKGROUND OF INVENTION

Libraries of bi-functional complexes can be produced by methods commonly known as split-and-mix methods, or by parallel, but separate synthesis of individual bi-functional complexes followed by mixing of such individually synthesized bi-functional complexes.

In a split-and-mix method, different synthesis reactions are performed in a plurality of different reaction compartments. The contents of the various reaction compartments are collected (mixed) and subsequently split into a number of different compartments for a new round of synthesis reactions. The sequential synthesis steps of a split-and-mix method are continued until the desired molecules have been synthesised.

It is often desirable to perform an encoded synthesis in order to be able to readily identify desirable molecules, for example after a selection step involving targeting a library of different bi-functional complexes to a molecular target. Encoded synthesis of biochemical molecules is disclosed by Lerner e.g. in U.S. Pat. Nos. 5,573,905, 5,723,598 and 6,060,596. One part of the bi-functional complexes is in the form of a molecule part and the other part is in the form of an identifier oligonucleotide comprising a plurality of oligonucleotide tags which encodes and identifies the building block residues which participated in the formation of the molecule and optionally the chemistries used for reacting the building block residues in the formation of the molecule. The oligonucleotide tags described by Lerner are added to each other exclusively by chemical ligation methods employing nucleotide-phosphoramidite chemistry.

The above-cited library synthesis principles require standard organic synthesis steps for both the sequential, chemical ligation of oligonucleotide tags and for the synthesis of the small molecule that is encoded by the resulting oligonucleotide identifier. It is an essential requirement, in the method described by Lerner, that the synthesis of the identifier oligonucleotide is completely orthogonal to the synthesis of the small molecule.

Facile organic synthesis of oligonucleotide tags used for the above-mentioned library synthesis principles employs nucleotide-phosphoramidite chemistry. This requires an efficient coupling of a trivalent phosphoramidite with the nucleophilic 5' OH-group of the growing nucleotide chain. Thus, any unprotected nucleophile present in the molecule part of the bi-functional complex may also react with tag phosphoramidite reactive groups in subsequent tag synthesis step and electrophilic groups present in the molecule part may also in some cases react with the nucleophilic 5' OH-group, which was intended to react with the phosphoramidite functional group of the incoming oligonucleotide tag.

Also, any protection groups used for protection of either the molecule, in its intermediate form, where such are used for controlling and directing its synthesis into the molecule or into a further intermediate of the molecule, and all protection groups used by the oligonucleotide tag must be compatible with the conditions applied, when the tag oligonucleotide is attached by use of chemical reaction based methods.

Furthermore, each round of nucleotide addition by phosphoramidite chemistry requires many steps, such as oxidation, capping of unreacted 5'-OH-groups, and DMT-deprotection using acidic conditions, all of which may challenge the integrity or reactivity of the small molecule part of the bi-functional complex.

As will be clear from the above, many prior art split-and-mix methods for performing an encoded synthesis are constrained in their application because of a lack of compatible chemistries between alternating synthesis procedures for adding to an intermediate bi-functional complex i) a reactive compound building block and ii) an oligonucleotide tag identifying said reactive compound building block and optionally the chemistry for said reaction, respectively.

It is a general problem that the reaction conditions and chemistries available for reacting reactive compound building blocks are far from always compatible with the phosphoramidite reaction conditions and chemistries required for performing the chemical ligation methods needed for adding an oligonucleotide tag to the identifier oligonucleotide of an intermediate bi-functional complex. Also, chemical synthesis methods exclusively employing on-bead combinatorial chemistry in the absence of any possibility for performing "in solution" reaction steps are constrained with respect to certain types of chemical reaction conditions typically used only in solution.

For several prior art split-and-mix methods, the problem of how to increase the sequential synthesis compatibility has been solved by including or even increasing the number of protection groups present on both the reactive compound building blocks and on the oligonucleotide tags identifying said reactive compound building block. The protection groups are added in a step-wise fashion as the alternating synthesis steps are performed. However, step-wise protection and deprotection reactions are cumbersome and have limited applicability when synthesising large libraries. This is due to a lack of available and compatible chemistries as well as the need to include a large number of different protection groups. This is being further complicated in split-and-mix synthesis methods, where many different molecules are in the process of being formed as a mixture, and all of these molecules in their intermediate form must be compatible with the conditions used for attaching the oligonucleotide tag.

Accordingly, many different protections groups will have to be employed in order to protect equally many different kinds of reactive groups in the molecules. In many cases, a library synthesis step can only be performed after several different protection reactions have taken place. Consequently, it is often regarded as undesirable, but necessary, to perform the number of protection and deprotection steps required for obtaining the needed degree of protection (and deprotection) of both reactive compound building blocks and oligonucleotide tags.

One cannot achieve sequential protection and deprotection of both reactive compound building blocks and oligonucleotide tag reactive groups without carrying out a certain number of protection group reactions. Accordingly, the requirement for orthogonality constitutes a major limitation of many prior art split-and-mix library synthesis methods and makes such methods cumbersome to use when synthesising large libraries.

Another approach for performing split-and-mix library synthesis methods is disclosed in WO 2004/039825 and WO 2007/062664. Unlike the above-cited library synthesis methods, WO 2004/039825 and WO 2007/062664 disclose methods wherein identifier oligonucleotide tags are ligated enzymatically. Enzymes are in general substrate specific and enzymatic ligation of identifier oligonucleotide tags is therefore unlikely to interfere with the synthesis of the molecule part of a bi-functional complex.

WO 00/23458 discloses yet another split-and-mix based approach, wherein molecule synthesis is both identified by and directed by oligonucleotide tags. A plurality of nucleic acid templates are used, each template having a chemical reaction site and a plurality of codons. The templates are partitioned by hybridisation of a first codon region to an immobilised probe and subsequently each of the strands of the template is reacted at the chemical reaction site(s) with specific building blocks. Subsequently, all the template strands are pooled and subjected to a second partitioning based on a second codon region. The split-and-mix method is conducted an appropriate number of times to produce a library of typically between $10^3$ and $10^6$ different compounds. This method has the disadvantage that a large number of nucleic acid templates must be provided. In the event a final library of $10^6$ different compounds is desired, a total of $10^6$ nucleic acid templates must be synthesised. The synthesis is generally cumbersome and expensive because the nucleic acid templates must be of a certain minimum length to secure sufficient hybridisation between codon regions and complementary probes.

WO 02/074929 and WO 02/103008 disclose templated methods for the synthesis of chemical compounds. The compounds are synthesised by initial contacting a transfer unit comprising an anti-codon and a reactive unit with a template under conditions allowing for hybridisation of the anti-codon to a codon of the template. Subsequently the reactive units of the transfer units are reacted. This method also suffers from the disadvantage that a large number of nucleic acid templates must be provided.

Generally, prior art methods using templates suffer from the disadvantage that molecule synthesis is dependent upon the recognition between the anti-codon and the template. Hybridisation between two oligonucleotides can occur provided there is a sufficient complementarity between them. Occasionally, the hybridisation will occur even though a complete match (i.e. complete complementarity) between the oligonucleotides is not present. The result is that sometimes a codon sequence of a template hybridises illegitimately to the anti-codon linked to a transfer unit. This impairs the subsequent de-coding of the synthesised molecules, wherefore only small libraries may be produced, and this in turn reduces the applicability of templated methods for the identification of drugable molecules.

SUMMARY OF INVENTION

There is a need for novel, encoded organic synthesis methods which optimize the use of protection groups in organic solvents by minimising the number of nucleic acid residues one needs to protect at any given reaction step—while at the same time facilitating reaction conditions compatible with molecule synthesis and/or tag additions in solution—i.e. in the absence of any linkage to a solid support.

Accordingly, part of the synthesis method according to the present invention is preferably conducted in one or more organic solvents when a nascent bi-functional complex comprising an optionally protected tag or oligonucleotide identifier is linked to a solid support, and another part of the synthesis method is preferably conducted under conditions suitable for enzymatic addition of an oligonucleotide tag to a nascent bi-functional complex in solution.

In one preferred embodiment, the optionally protected tag or oligonucleotide identifier linked to the solid support identifies some, but not all, of the reactive compound building blocks which have reacted with the chemical reaction site comprised by, or linked to, the optionally protected tag or oligonucleotide identifier, wherein said tag or identifier is in turn linked to a solid support.

The present invention thus relates to bi-functional complexes and combinatorial chemistry, organic synthesis methods used for synthesising and using such tagged complexes, wherein such bi-functional complexes comprises an identifier oligonucleotide comprising one or more tags, a linker and a natural or unnatural "molecule part" attached to the oligonucleotide via the linker, wherein such a natural or unnatural "molecule part" is not an oligonucleotide and wherein such "molecule part" is not a natural alpha-amino acid based peptide formed by ribosome catalyzed translation.

In another aspect the present invention is directed to split-and-mix methods for producing bi-functional complexes and libraries of different bi-functional complexes comprising an identifier oligonucleotide and a molecule identified by the identifier oligonucleotide, such as a chemical fragment or combination of fragments reacted to form a molecule. Such molecules may include but is not limited to scaffolded molecules, macrocyclic molecules or any compound suitable for binding a target.

Accordingly, the synthesis methods of the present invention preferably comprise one or more steps suitable for inclusion in a split-and mix combinatorial organic synthesis methods, or any other method for generating or providing one or more molecules attached to and/or encoded by one or more identifier oligonucleotide comprising one or more oligonucleotide tags.

In view of the above, there is also provided a bi-functional complex comprising a molecule and an oligonucleotide identifier, said molecule being linked by means of a linking moiety to the oligonucleotide identifier, wherein said oligonucleotide identifier comprises oligonucleotide tags identifying the reactive compound building blocks which have participated in the formation of the molecule.

In one embodiment, the above-cited bi-functional complex is linked to a solid support and/or comprises one or more protection groups protecting reactive groups of the oligonucleotide identifier.

There is also provided a library of different bi-functional complexes and a composition comprising a bi-functional complex and an enzyme capable of ligating oligonucleotide tags.

In yet another aspect of the present invention there is provided a synthesis method resulting in the synthesis of a library comprising different bi-functional complexes, wherein each bi-functional complex comprises a molecule part linked to an identifier oligonucleotide comprising a plurality of oligonucleotide tags identifying the reactive compound building blocks which participated in the synthesis of the molecule part of the bi-functional complex. Consequently, the methods of the present invention allow identification of at least part of the structure of the molecule part of the bi-functional complex.

Single compound bi-functional complexes or a library of different bi-functional complexes can be partitioned by contacting the one or more bi-functional complexes individually or as a mixture against a molecular target with the purpose of separating (partitioning) a mixture of bi-functional complexes according to their individual propensity to bind the molecular target or as individual compounds to determine the propensity of the molecular target to bind the compound, wherein such contacting may be performed in one or more iterative steps of a molecular target for which at least some of the bi-functional complexes have an affinity. Following selection of partitioned bi-functional complexes, desirable molecules can be at least partly identified by de-coding the identifier oligonucleotides linked to said molecules.

The "molecule part", hereinafter interchangeably denoted, or including, a "molecule", a "scaffolded molecule", a "compound", or a "small molecule", can be obtained by or be obtainable by the methods of the present invention. The molecule part can be a natural or an unnatural molecule, such as, but not limited to, small molecules, drugable molecules, such as small, scaffolded molecules, macrocyclic molecules, or lead compounds suitable for further optimization—for example by synthesis of intelligent libraries e.g. following one or more further partitioning and/or selection steps.

The terms "reactive compound building block" and "reactive compound building block" are used interchangeably in the present specification.

In a further aspect of the present invention there is provided an encoded, combinatorial chemistry synthesis method for synthesising a library of different molecules, said method comprising the steps of
a) providing a plurality of nascent bi-functional complexes each comprising one or more chemical reaction site(s) and one or more priming site(s) suitable for enzymatic or chemical addition of one or more oligonucleotide tag(s),
b) reacting the chemical reaction site(s) with one or more reactive compound building blocks, and
c) reacting the priming site enzymatically or chemically with one or more oligonucleotide tags identifying the one or more reactive compound building blocks,
wherein a reactive compound building block and the tag identifying the reactive compound building blocks are not linked prior to their reaction with the chemical reaction site and the priming site, respectively, of the nascent bi-functional complex.

The method in one preferred embodiment comprises at least two tag addition steps.

In one embodiment, a first oligonucleotide identifier tag identifying a first reactive compound building block is initially added to or synthesised on a solid support, such as a bead. The first oligonucleotide identifier tag can be unprotected or protected—wherein a protected tag is rendered inert and is unable to react e.g. with the reactive compound building block. Tag protection also enables use of certain organic solvents, as disclosed herein below, which cannot be used in the absence of a protection—by one or more protection group(s)—of reactive groups present in the oligonucleotide tag.

The oligonucleotide initially added to or synthesised on a solid support, such as a bead, can comprise more than one optionally protected oligonucleotide tag, such as 2 optionally protected oligonucleotide tags, for example 3 optionally protected oligonucleotide tags, such as 4 optionally protected oligonucleotide tags, for example 5 optionally protected oligonucleotide tags, wherein each tag identifies a reactive compound building block to be reacted at a later stage—either "on-bead" or "off-bead"—i.e. either while the nascent bi-functional complex is linked to the solid support, or after cleavage of at least one linker the cleavage of which releases the nascent bi-functional complex from the solid support.

During at least one of one or more reactive compound building block reactions, reactive groups of the identifier oligonucleotide of the nascent bi-functional complex is preferably protected by protection groups. The protected identifier oligonucleotide of the nascent bi-functional complex can comprise the tag identifying the reactive compound building block which is reacted. Alternatively, when the protected identifier oligonucleotide of the nascent bi-functional complex does not comprise the tag identifying the reactive compound building block which is reacted, the tag identifying the reactive compound building block which is reacted is added to the priming site by chemical or enzymatic means at a later stage or synthesis round which can be either "on-bead" or "off-bead", i.e. in solution.

In preferred embodiments, the oligonucleotide identifier comprises a double stranded part which is generated by at least one enzymatic linkage of at least one oligonucleotide tag, for example by an enzymatic nucleotide extension reaction and/or by an enzymatic nucleotide ligation reaction. At least one oligonucleotide tag, but not all oligonucleotide tags, can ligated by a chemical ligation step. At least some oligonucleotide tags are ligated enzymatically by a double stranded ligation reaction optionally involving a splint oligonucleotide hybridizing to the tags to be ligated. In one embodiment, at least some oligonucleotide tags are blunt end ligated. Preferably, oligonucleotide tags are added to the priming site of the nascent bi-functional complex by an enzymatic extension reaction involving a polymerase and/or added to the priming site by a ligation reaction involving a ligase enzyme.

In one embodiment, one or more reactive compound building blocks are reacted by using one or more reactions selected from the group of chemical reactions consisting of an acylation reaction, an alkylation reaction, a vinylation reaction, an alkenylidation reaction, a HWE reaction, a Wittig reaction, a transition metal catalyzed reaction, a transition metal catalyzed arylation reaction, a transition metal catalyzed hetarylation reaction, a transition metal catalyzed vinylation reaction, a palladium catalyzed reaction, a palladium catalyzed arylation reaction, a palladium catalyzed hetarylation reaction, a palladium catalyzed vinylation reaction, a reaction using boronic acid or boronic acid ester, a reaction using aryl iodide, a reaction using an enamine, a reaction using enolether, a Diels-Alder type reaction, a 1,3-dipolar cycloaddition reaction, a reaction using EDC, and a reaction using 4-(4,6-dimethoxy-1,3,5-thiazin-2-yl)-4-methylmorpholinium chloride (DMTMM), including combinations of the aforementioned reactions.

The oligonucleotide identifier preferably comprises deoxyribonucleotides (DNA) and does not contain ribonucleotides (RNA), wherein the priming site preferably comprises a 3'-OH group which is ligated to a phosphate group of a 5'-end located nucleotide of an incoming oligonucleotide tag, or wherein the priming site comprises a 5'-end phosphate group which is ligated to a 3-OH group of an incoming oligonucleotide tag.

The oligonucleotide identifiers according to the present invention can comprise an individual framing sequence and/or a flanking sequence identifying the respective oligonucleotide identifier. Also, individual tags of an oligonucleotide identifier can be separated by a spacer sequence optionally informative of synthesis history when reacting individual reactive compound building blocks, wherein preferably, the spacer sequence has from 1 to 20 nucleotides.

In one embodiment, one or more identifier tags identifies two or more reactive compound building blocks, and in at least some synthesis rounds, an identifier tag either identifies several different reactive compound building blocks, or several different identifier tags identifies or are used to identify the same reactive compound building block.

The linker separating the molecule and the identifier is preferably a flexible linker and more preferably, the linker comprises a PEG moiety or an alkane chain. Preferably, in one embodiment, the linker, such as the above-cited flexible linker is linking both strands of the double stranded identifier oligonucleotide.

Preferably, one or two reactive compound building blocks are reacted when the molecule is synthesised, and the molecule is preferably a small molecule having a molecular weight of less than 1000 Da, or a non-polymeric molecule having a molecular weight of more than 1000 Da, or a polymeric molecule having a molecular weight of more than 1000 Da.

When a library of different bi-functional complexes are synthesised by a split-and-mix organic combinatorial synthesis method, the method comprises the step(s) of reacting different reactive compound building blocks with the chemical reaction site, or with a nascent bi-functional complex synthesized in a previous synthesis round. The library preferably contains from $10^5$ to $10^6$ different bi-functional complexes, or from $10^5$ to $10^8$ different bi-functional complexes, or from $10^5$ to $10^{10}$ different bi-functional complexes, or from $10^5$ to $10^{14}$ different bi-functional complexes.

Following library synthesis, the library is partitioned and one or more bi-functional complexes are selected, wherein the selected molecules of said bi-functional complexes have an affinity for said target. The identifier oligonucleotide of synthesized or selected molecules can be amplified by using PCR, and the identifier oligonucleotides identifying selected and/or amplified molecules can be sequenced.

In one embodiment it may be beneficial to conduct the partitioning of bi-functional complexes using methods such as capillary electrophoresis (Drabovich A P, Berezovski M V, Musheev M U, Krylov S N. Anal Chem. 2009 Jan. 1; 81(1):490-4), affinity co-electrophoresis (Lim V A et al., Methods in Enzymology, 1991; 208:196-210, Cilley and Williamson, *RNA* 1997 3: 57-67), Gel-retardation (Sambrook and Russell, Cold Spring Harb Protoc; 2006; doi: 10.1101/pdb.prot3948) or other means of conducting partitioning of bound and unbound bi-functional molecules using electrophoresis-based methods. Screening libraries of tagged compounds against membrane-imbedded target proteins may provide a challenge. Membrane proteins are not soluble per se and may require specific and individual efforts before being amenable to screening. In some cases screening on whole-cells is possible if sufficient membrane target can be expressed on the cell surface. In other cases it may be desirable to solubilize the membrane protein using detergents, amphipols or fluorinated surfactants (Popot, J L, Annual Review of Biochemistry, 2010 Vol. 79: 737-775). This will allow the membrane protein to be manipulated outside its natural membrane environment to enable standard protocols useful for immobilisation and screening. In another embodiment it is desirable to immobilize membrane proteins in "nano-discs" which allows membrane proteins imbedded in a phospholipid bi-layer to be assembled into nano-disc of pre-specified size allowing solubility and manipulation of the desired membrane protein (Bayburt, T. H., Grinkova, Y. V., and Sligar, S. G. (2002) NanoLetters 2, 853-856. In another embodiment it may be desirable to screen libraries of bi-functional molecules against membrane proteins immobilized in lipoparticles (f.ex. lipoparticles from Integral Molecular, US).

Sequencing of a tag or an oligonucleotide identifier refers to the identification of the string of nucleotides attached to the chemical compound comprising the information necessary to deconvolute the complete or partial chemical composition of the compound. In one embodiment sequencing may require amplification of the tag by polymerases, ligases or other means before or during the sequencing process. In another embodiment sequencing may not require amplification of the tag for sequence identification. Several platforms methods exists for efficient mass sequencing such as that described by 454 (Roche), Illumina/Solexa, SOLID (Applied Biosystems), Ion Torrent (Life technologies), Pacific biosciences etc.

The reaction between the one or more reactive compound building blocks can occur subsequent to the addition of one or more tags, after the addition or synthesis of one or more tags, or simultaneous with the addition or synthesis of one or more tags. In one embodiment the one or more tags are synthesised directly on a solid support, such as a bead, whereas further tags are added in solution—i.e. off-bead. In one embodiment, a nascent bi-functional complex initially synthesised on a solid support is cleaved from said solid support in a form in which the identifier does not identify all of the reacted reactive compound building blocks. The one or more tags identifying previously reacted reactive compound building blocks are subsequently added in solution—i.e. off-bead—by either chemical and/or enzymatic means.

At least some reactive compound building block reactions take place in an organic solvent—either when the identifier oligonucleotide is linked to a solid support, or when the identifier oligonucleotide is not linked to a solid support, or both on-bead and off-bead—i.e. reactive compound building block reactions take place in an organic solvent both when the identifier oligonucleotide is linked to a solid support and before and/or after such a linkage of the identifier oligonucleotide to a solid support.

In one embodiment, an oligonucleotide identifier of a nascent bi-functional complex comprising one or more tags, such as 2 tags, for example 3 tags, such as 4 tags, is preferably synthesized on-bead—i.e. linked to a solid support—either by phosphoramidite chemistry, or by any other chemical means for performing oligonucleotide synthesis. In at least one reactive compound building block reaction, the oligonucleotide identifier is protected by one or more protection groups to prevent an interaction between the oligonucleotide identifier and the reactive compound building block reaction and/or to protect the identifier oligonucleotide from the solvent, such as an organic solvent, being used in the reaction of the reactive compound building block reaction.

In one embodiment, the oligonucleotide identifier can harbour one or more tags for yet un-reacted reactive compound building block(s)—which are to be reacted only in a later synthesis round, including a synthesis round taking place in solution after cleavage of the native bi-functional complex from a solid support.

In another embodiment, at least one of the employed oligonucleotide tags of a nascent bi-functional complex is preferably synthesized on-bead—i.e. linked to a solid support—either by phosphoramidite chemistry, or by any other chemical means for performing oligonucleotide synthesis. In at least one reactive compound building block reaction, the oligonucleotide tag is protected by one or more protection groups to prevent an interaction between the oligonucleotide tag and the reactive compound building block reaction and/or to protect the identifier oligonucleotide from the solvent, such as an organic solvent, being used in the reaction of the reactive compound building block reaction.

In certain embodiments of the present invention it is desirable to perform the synthesis of individual tag(s) using nucleotides with alternative protection groups for improved chemical stability. Certain reactive compound building block chemistries applied for the synthesis of a part or the molecule may require or benefit from the use of alternative protection groups on any part of the tag or linker.

In one example the use of methyl phosphoramidites may provide a suitable alternative to beta-cyanoethyl (CE) phosphoramidites using f.ex thiophenol as deprotection agent.

Similarly, suitable protection groups of the nucleobases may be changed to facilitate efficient orthogonal synthesis and deprotection strategy for small-molecule compound production. Benzyl, acetate, isobutyl, phenoxyacetate, isopropyl phenoxyacetate, dialkylmethylenes etc can be used as standard protection groups in DNA phosphoramidite chemistry (see f. ex Glen Research, US; www.glenresearch.com), but may be substituted for alternative protections scheme(s). Methods, tools and reagents for organic synthesis of oligonucleotides and linkers useful for the production of Bi-functional complexes according to this invention disclosed by Glen Research, US, are incorporated herein by reference.

In certain embodiments of the present invention it is desirable to perform the split-and-mix combinatorial synthesis steps in the absence of (i.e. detached from) a solid-support.

In general, a solid-support may offer an advantage in organic synthesis by providing a matrix of pre-specified chemical characteristics that allows control of matrix reactivity and easy purification of products from reactants and other additives. However, for any steps involving mix-and-split in the assembly of a combinatorial compound library, it may be desirable that the mix-and-split step is conducted with the nascent bi-functional complexes detached from the solid-support.

As acknowledged by a person skilled in the art, an even assembly (collection of beads), mixing and subsequent distribution of a population of beads into new reaction wells is cumbersome and non-trivial. Consequently, it may be envisioned that initial steps in the synthesis of an oligonucleotide tag and subsequent first reaction(s) prior to the mixing steps are conducted using solid-support synthesis.

Synthesis of oligonucleotide tags can preferably be done on either non-swelling beads, swelling beads or surfaces. The most known type of non-swelling beads is Controlled Pore Glass (CPG) but crystalline plastic materials mixed with materials with other physical and chemical properties, which gives the possibility to make an open structure can also be used. Swelling beads are often of the Poly Styrene (PS) type cross linked with Di Vinyle Benzene (DVB), but other cross linked polymers like Poly Amide (PA), Polystyrene-ethyleneglycol-acrylate (CLEPSER), Acr$_2$PEG, Tentagel, HypoGel, NovaGel, AcroGel, ChemMatrix, CLEAR Resin, SynPhase and others listed in "Linker Strategies in Solid-phase Organic Synthesis" by Peter J. H. Scott 2009 ISBN:978-0-470-51116-9) may work equally well and are incorporated herein by reference).

In one embodiment, following first round synthesis, the nascent, tagged compounds are cleaved off the solid support by cleaving a selectively cleavable linker moiety. The detached nascent bi-functional complexes, now in solution, can subsequently be collected and pooled before splitting the solution mixture into new reaction wells for the second round of synthesis and tagging. One example of such a bi-functional complex is described by the formula:

B-X-Y-D-L-C, in which B is a bead or matrix, X and Y are selectively cleavable linkers, D is an oligonucleotide tag with suitable protection groups connected to C, a nascent small molecule compound, via a linker, L. In one embodiment X and Y are distinctive orthogonal linkers capable of being selectively cleaved.

One example of a suitable linker pair is a photo-cleavable linker X and an ester-linkage Y such as the following:

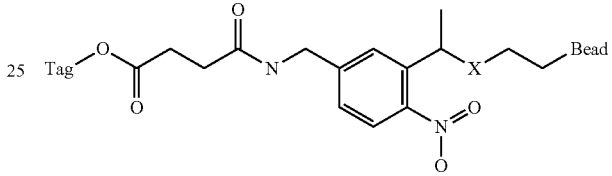

The photo-cleavable unit can be selectively cleaved using UV-light, usually in the range of 300-365 nm. The ester linker proximal to the tag can be selectively cleaved using f. ex basic aqueous conditions (ammonia, NaOH, methylamine, potassium carbonate etc. See also protocols from Glen Research, US, incorporated herein by reference). In the linker above, the x marks any atom although the atoms; oxygen, nitrogen or sulphur exhibit superior reactivity.

In another embodiment X and Y is a single cleavable unit f. ex an ester linkage or a phosphodiester linkage.

Following first round of synthesis and subsequent split to a second round of synthesis and tagging, the samples split into individual reaction wells may contain protection groups on nucleobases and phosphodiester backbone as well as a protection of the 3' OH group of the DNA-tag. The latter is optional and may depend on the actual chemistry involved in small-molecule library production.

The second round of synthesis is conducted by addition of second round fragments to the first round synthesis products. The protection groups on the functional groups of the DNA-tag may improve the scope of chemical reactions available to small-molecule synthesis. Following the chemical reactions of position 2 building blocks in each well, the DNA may be purified, preferably in a parallel format, and subsequently the DNA-tag is deprotected using standard conditions (f.ex deprotection using aqueous ammonia, 10 M/55° C./17 hours). Following evaporation of ammonia and optional purification of the tags, preferably in parallel format, the second encoding tag is enzymatically conjugated to the nascent bi-functional molecule in the well providing a unique encoding tag for each compound provided in the combinatorial library. The basics step(s) in the synthesis of a small compound library, as described above, is shown schematically in FIG. 104.

In certain embodiments of the present invention it may be desirable to perform multiple chemical reactions in the synthesis of a product(s) in each well. For example, multicomponent reactions may involve multiple reactants in one well producing one or more products to be encoded by a single position. An example of multiple reactions per encoding step is shown schematically in FIG. 105.

In one embodiment of the present invention it is possible to complete the synthesis of the compound library in the absence of water or aqueous media.

The steps performed using a solid support compared to the steps performed in solution is chosen arbitrarily and may ultimately depend on the actual chemistry steps to be performed. Consequently, under certain circumstances it may be desirable that all chemical steps are performed in solution. However, with present ease, quality and validation in solid-support oligonucleotide synthesis it is envisioned that at least the synthesis of the initial (first round) synthesis of n individual oligonucleotide tag sequences each comprising a unique sequence and reactive handle X should benefit from the synthesis using solid-support organic synthesis. It could be envisioned that library synthesis steps may benefit from high-throughput parallel synthesis formats to aid both tag synthesis and the chemical steps for compound synthesis.

Synthesis of oligonucleotide tags may be conducted on any solid-support or matrix suitable for organics synthesis of an oligonucleotide tag. Although, off-bead synthesis may also be envisioned and should be considered a viable option for the practice of the present invention, the on-bead solution is presently more appealing. CPG-beads for standard phosphoramidite chemistry are shown elsewhere in this application. Several solid-support options and strategies for organic synthesis of oligonucleotides exists such as those described by Glen Research, US and incorporated herein by reference. A few additional examples of solid-supports enabling DNA tag synthesis is described below (adopted from Glen research, US).

Universal support: Traditional procedures in oligonucleotide synthesis require that the solid support contains the first nucleoside which is destined to become the nucleoside at the 3'-terminus of the synthetic oligonucleotide. This situation therefore requires that an inventory of all four regular nucleoside supports must be maintained. At the same time, oligonucleotides with unusual nucleosides, available as phosphoramidites but not as supports, at the 3'-terminus can not be readily prepared. However, the most worrisome aspect of this situation is the potential for a mistake to be made in the selection of the column containing the 3'-nucleoside. This potential for error may be fairly low in regular column-type synthesizers, but it is especially significant in the new generation of parallel synthesizers where 96, 192 wells or even more may contain all four supports in a defined grid.

A universal support for preparing regular oligonucleotides must allow the elimination, during the cleavage and deprotection steps, of the terminal phosphodiester linkage along with the group originally attached to the support.

The key step in the use of any universal support in oligonucleotide synthesis is the dephosphorylation of the 3'-phosphate group to form the desired 3'-hydroxyl group. Amide groups may be considered to be weak N—H acids and can display basic properties in ammonium hydroxide or aqueous methylamine. (±)-3-Amino-1,2-propanediol was used to form a novel universal support. In the original US II support, a succinate linker attaches the 3-amino group to the support and the 2-OH is protected with a base-labile group to set up an amide-assisted elimination in mildly basic conditions. In this way, the dephosphorylation reaction would eliminate the desired 3'-OH oligonucleotide into solution and the product of any β-elimination competing side reaction would remain bound to the support.

A further improvement has been achieved by using a carbamate group to connect the universal linker to the support, now called Universal Support III. The structures of the two supports are shown below right. Using Universal Support II or III, an oligo yield of >80% can be achieved on CPG supports and >95% on polymeric supports, with purity equivalent to the same oligo prepared normally.

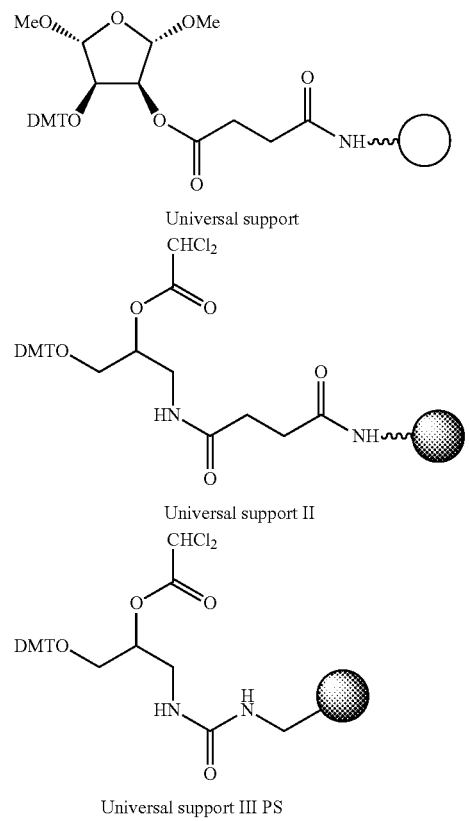

Universal support

Universal support II

Universal support III PS

Other examples such as the Q-support or the 5'-support for "reverse" oligonucleotide synthesis (5'- to 3'-end synthesis) are also viable choices for oligonucleotide tag synthesis.

As recognized by one skilled in the art the size and chemical characteristics of the beads used for any combinatorial chemistry library is important. It is generally appreciated that the total number of beads applied in library synthesis should be larger than the number of different compounds to be synthesized in the steps while compounds remain attached to the solid-support.

Further examples of useful linker and bead formats are shown in FIG. 106 Product purification and quality assessment can be done using LC/MS procedures comprising HPLC/UPLC separation and product detection using Electrospray-MS, MALDI-TOF or similar technique.

Another useful linker in accordance with the present invention is shown herein below in a de-protected synthesis mode. The linker can serve as an "encoding tag" for the synthesis of bi-functional complexes according to the present invention.

(SEQ ID NO 7)

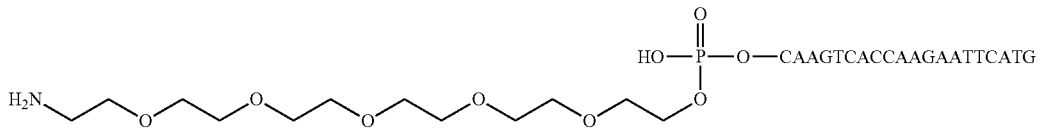

In certain embodiments it may be desirable to add a specific functionality of the nascent or final bi-functional molecules to facilitate rapid and efficient purification steps. One option for such functionality could be a poly-fluorinated hydrocarbon moiety (see f.ex Fluorous Inc.) shown in FIG. 108.

The polyfluorinated tag allows solution or column based extraction from most solvents using protocols specified by the manufacturer (Fluorous, Inc) and incorporated herein by reference. Diversity-oriented synthesis (Schreiber S L, 2000, Science 287:1964-1969, Burke M D, Schreiber S L, 2004, Angew Chem Int Ed 43:46-58,)

Although the methods of the invention in one embodiment employ the use of solid supports, such as beads, reactive compound building block reactions as well as oligonucleotide tag synthesis and/or addition to a nascent bi-functional complex can also take place in solution—i.e. the absence of a solid support.

In one embodiment, the methods of the invention employ at least two reactive compound building block reactions with a chemical reaction site of a bi-functional complex further comprising an identifier oligonucleotide comprising one or more covalently linked oligonucleotide tags, wherein at least one such reactive compound building block reaction takes place when reactive groups of the oligonucleotide tag or the entire oligonucleotide identifier is protected to prevent an undesirable contact between the oligonucleotide identifier or the tag and the reactive compound building block, or a contact between the reactive groups of the oligonucleotide tag and the solvent in which the reactive compound building block is reacted. The chemical reaction site of the bi-functional complex shall be understood to comprise both an initial chemical reaction site and the product formed by reaction of a chemical reaction site and a reactive compound building block in a previous synthesis round.

The use of protected oligonucleotide tags—or a protected oligonucleotide identifier as the case may be—in a reactive compound building block reaction enables use of certain organic solvents which would otherwise be more difficult to use for the synthesis of the molecules of the library. For example, reactive compound building block reactions under anhydrous conditions can be performed when reactive groups of an oligonucleotide tag or an oligonucleotide identifier is protected. Furthermore, it may be possible to solubilize a protected oligonucleotide identifier in an organic solvent in which the un-protected oligonucleotide identifier would not be soluble. For example, it is well known in the art that oligonucleotides are precipitated in many alcohols, including ethanol and butanol. Additionally, many organic solvents are likely to cause some form of degradation of oligonucleotides and such degradation can be reduced, minimized or even prevented in accordance with the methods of the present invention.

Furthermore, the use of protection groups for protecting an oligonucleotide tag or an oligonucleotide identifier increases the versatility of the chemical reagents one is able to employ for the library synthesis. For example, it may be possible to use reagents which are normally not compatible with protic solvents, such as protic solvents like $H_2O$, EtOH, MeOH, and the like.

Non-limiting examples of reactive groups in an oligonucleotide tag or an oligonucleotide identifier which can be protected according to the present invention includes —OH groups (3'-OH as well as —OH groups occurring in the backbone of the oligonucleotide); as well as —$NH_2$ groups on the nucleobases—i.e. N6 on Adenine, N2 on Guanine, and N4 on Cytidine).

While it is desirable to employ for some reactive compound building block reaction steps a tag or identifier oligonucleotide in protected form, it is very often undesirable to perform each and all such synthesis steps under such conditions. Hence, for some reactive compound building block reactions, or for some tag addition reactions, it is desirable to employ un-protected tags or identifier oligonucleotides.

Un-protected tags and oligonucleotides are advantageously used in e.g. enzymatic tag additions, such as enzymatic ligation of tags. Also, un-protected tags and oligonucleotides are often advantageously used in reactive compound building block reactions which take place in many aqueous solvents, including water. Also, bi-functional complexes comprising de-protected oligonucleotides are often more readily purified from organic solvents or reactive compound building blocks which are primarily present in organic solvents. Solvents for use in the methods of the present invention are disclosed in more detail herein below.

The term solvent (from the Latin solvere, "loosen") as used herein is a liquid or gas that dissolves another liquid or gaseous solute, resulting in a solution that is soluble in a certain volume of solvent at a specified temperature. Accordingly, when one substance is dissolved into another, a solution is formed.

Mixing of different solvents is generally referred to as miscibility, whereas the ability to dissolve one compound into another is known as solubility. However, in addition to mixing, substances, such as a reactive compound building blocks, in a solution can interact with each other as well as with the solvent in specific ways. Solvation describes these interactions.

When e.g. reactive compound building blocks are dissolved, molecules of the solvent may tend to arrange themselves around molecules of the solute. Heat may be involved and entropy is increased, often making the solution more thermodynamically stable than the solute alone. This arrangement is mediated by the respective chemical properties of the solvent and the one or more solute(s), chemical properties such as e.g. hydrogen bonding, dipole moment and polarizability.

Any type of solutions or solvations, including the ones mentioned herein above, can be used in one embodiment of this invention.

Solvents can be broadly classified into two categories: polar and non-polar. Generally, the dielectric constant of a solvent provides a rough measure of a solvent's polarity. The strong polarity of water is indicated, at 20° C., by a dielectric constant of 80.10.

Solvents with a dielectric constant of less than 15 are generally considered to be non-polar. Technically, the dielectric constant measures the solvent's ability to reduce the field strength of the electric field surrounding a charged particle immersed in it. This reduction is then compared to the field strength of the charged particle in a vacuum. In laymen's terms, dielectric constant of a solvent can be thought of as its ability to reduce the solute's internal charge.

Dielectric constants are not the only measure of polarity. Because solvents are used by chemists to carry out chemical reactions or observe chemical and biological phenomena, more specific measures of polarity are required.

The Grunwald Winstein mY scale measures polarity in terms of solvent influence on buildup of positive charge of a solute during a chemical reaction.

Kosower's Z scale measures polarity in terms of the influence of the solvent on uv absorption maxima of a salt, usually pyridinium iodide or the pyridinium zwitterion.

Donor number and donor acceptor scale measures polarity in terms of how a solvent interacts with specific substances, like a strong Lewis acid or a strong Lewis base.

The polarity, dipole moment, polarizability and hydrogen bonding of a solvent determines what type of compounds it is able to dissolve and with what other solvents or liquid compounds it is miscible. As a rule of thumb, polar solvents dissolve polar compounds best and non-polar solvents dissolve non-polar compounds best: "like dissolves like".

Strongly polar compounds like sugars (e.g. sucrose) or ionic compounds, like inorganic salts (e.g. table salt) dissolve only in very polar solvents like water, while strongly non-polar compounds like oils or waxes dissolve only in very non-polar organic solvents like hexane. Similarly, water and hexane (or vinegar and vegetable oil) are not miscible with each other and will quickly separate into two layers even after being shaken well.

Solvents with a relative static permittivity greater than 15 can be further divided into protic and aprotic. Protic solvents solvate anions (negatively charged solutes) via hydrogen bonding. Water is a protic solvent.

Aprotic solvents such as acetone or dichloromethane tend to have large dipole moments (separation of partial positive and partial negative charges within the same molecule) and solvate positively charged species via their negative dipole. In chemical reactions the use of polar protic solvents favors the $S_N 1$ reaction mechanism, while polar aprotic solvents favor the $S_N 2$ reaction mechanism.

Any type of solvent can be used in the present invention including solvents with the characteristics mentioned herein above.

Physical properties of solvents capable of being used in the methods of the present invention are disclosed herein below. Tables A and B herein below list solvents that are used in some preferred embodiments of the present invention.

The solvents can be grouped into non-polar, polar aprotic, and polar, protic solvents—and they can be ordered by increasing polarity. The polarity is given as the dielectric constant. The properties of solvents that exceed those of water are bolded.

TABLE A

| Solvent | Chemical formula | Boiling point | Dielectric constant | Density | Dipole moment |
|---|---|---|---|---|---|
| Non-polar solvents | | | | | |
| Pentane | $CH_3-CH_2-CH_2-CH_2-CH_3$ | 36° C. | 1.84 | 0.626 g/ml | 0.00 D |
| Cyclopentane | $C_5H_{10}$ | 40° C. | 1.97 | 0.751 g/ml | 0.00 D |
| Hexane | $CH_3-CH_2-CH_2-CH_2-CH_2-CH_3$ | 69° C. | 1.88 | 0.655 g/ml | 0.00 D |
| Cyclohexane | $C_6H_{12}$ | 81° C. | 2.02 | 0.779 g/ml | 0.00 D |
| Benzene | $C_6H_6$ | 80° C. | 2.3 | 0.879 g/ml | 0.00 D |
| Toluene | $C_6H_5-CH_3$ | 111° C. | 2.38 | 0.867 g/ml | 0.36 D |
| 1,4-Dioxane | $/-CH_2-CH_2-O-CH_2-CH_2-O-\backslash$ | 101° C. | 2.3 | 1.033 g/ml | 0.45 D |
| Chloroform | $CHCl_3$ | 61° C. | 4.81 | 1.498 g/ml | 1.04 D |
| Diethyl ether | $CH_3CH_2-O-CH_2-CH_3$ | 35° C. | 4.3 | 0.713 g/ml | 1.15 D |
| Polar aprotic solvents | | | | | |
| Dichloromethane (DCM) | $CH_2Cl_2$ | 40° C. | 9.1 | 1.3266 g/ml | 1.60 D |
| Tetrahydrofuran (THF) | $/-CH_2-CH_2-O-CH_2-CH_2-\backslash$ | 66° C. | 7.5 | 0.886 g/ml | 1.75 D |
| Ethyl acetate | $CH_3-C(=O)-O-CH_2-CH_3$ | 77° C. | 6.02 | 0.894 g/ml | 1.78 D |
| Acetone | $CH_3-C(=O)-CH_3$ | 56° C. | 21 | 0.786 g/ml | 2.88 D |
| Dimethylformamide (DMF) | $H-C(=O)N(CH_3)_2$ | 153° C. | 38 | 0.944 g/ml | 3.82 D |
| Acetonitrile (MeCN) | $CH_3-C\equiv N$ | 82° C. | 37.5 | 0.786 g/ml | 3.92 D |
| Dimethyl sulfoxide (DMSO) | $CH_3-S(=O)-CH_3$ | 189° C. | 46.7 | 1.092 g/ml | 3.96 D |
| Polar protic solvents | | | | | |
| Formic acid | $H-C(=O)OH$ | 101° C. | 58 | 1.21 g/ml | 1.41 D |
| n-Butanol | $CH_3-CH_2-CH_2-CH_2-OH$ | 118° C. | 18 | 0.810 g/ml | 1.63 D |
| Isopropanol (IPA) | $CH_3-CH(-OH)-CH_3$ | 82° C. | 18 | 0.785 g/ml | 1.66 D |
| n-Propanol | $CH_3-CH_2-CH_2-OH$ | 97° C. | 20 | 0.803 g/ml | 1.68 D |
| Ethanol | $CH_3-CH_2-OH$ | 79° C. | 24.55 | 0.789 g/ml | 1.69 D |
| Methanol | $CH_3-OH$ | 65° C. | 33 | 0.791 g/ml | 1.70 D |
| Acetic acid | $CH_3-C(=O)OH$ | 118° C. | 6.2 | 1.049 g/ml | 1.74 D |
| Water | $H-O-H$ | 100° C. | 80 | 1.000 g/ml | 1.85 D |

Further characterisation of solvents can be performed by knowing their Hansen solubility parameter values (HSPiP), which are based on δD=dispersion bonds, δP=polar bonds and δH=hydrogen bonds. In this way, one can obtain information about inter-molecular interactions with other solvents and also with types and classes of reactive compound building blocks.

Based on this information it is possible to optimize formulations and reaction conditions and to create rational reaction formulations or solvent compositions in which, for example, there is a good HSP match between a solvent and a particular class or group of reactive compound building blocks.

The following table shows that the intuitions from "non-polar", "polar aprotic" and "polar protic" are put numerically—the "polar" molecules have higher levels of δP and the protic solvents have higher levels of δH. Because numerical values are used, comparisons can be made rationally by comparing numbers. For example, acetonitrile is much more polar than acetone, but only slightly less hydrogen bonding.

In one embodiment the present invention relates, in one or more reactive compound building block reaction steps, to the use of a solvent with a dielectric constant selected from the group consisting of for example from 1 to 5, such as from 5 to 10, for example from 10 to 15, such as from 15 to 20, for example from 20 to 25, such as from 25 to 30, for example from 30 to 35, such as from 35 to 40, for example from 40 to 45, such as from 45 to 50, for example from 50 to 55, such as from 55 to 60, for example from 60 to 65, such as from 65 to 70, for example from 70 to 75, such as from 75 to 80, for example from 80 to 85, such as from 85 to 90, for example from 90 to 95, such as from 95 to 100 or higher than 100 or any combination of these intervals.

In one embodiment the present invention relates, in one or more reactive compound building block reaction steps, to use of a solvent with a density selected from the group consisting of for example from 0 to 0.1 g/ml, such as from 0.1 to 0.2 g/ml, for example from 0.2 to 0.3 g/ml, such as from 0.3 to 0.4 g/ml, for example from 0.4 to 0.5 g/ml, such as from 0.5 to 0.6 g/ml, for example from 0.6 to 0.7 g/ml, such as from 0.7 to 0.8 g/ml, for example from 0.8 to 0.9 g/ml, such as from 0.9 to 1.0 g/ml, for example from 1.0 to 1.1 g/ml, such as from 1.1 to 1.2 g/ml, for example from 1.2 to 1.3 g/ml, such as from 1.3 to 1.4 g/ml, for example from 1.4 to 1.5 g/ml, such as from 1.5 to 1.6 g/ml, for example from 1.6 to 1.7 g/ml, such as from 1.7 to 1.8 g/ml, for example from 1.8 to 1.9 g/ml, such as from 1.9 to 2.0 g/ml, for example from 2.0 to 2.1 g/ml, such as from 2.1 to 2.2 g/ml, for example from 2.2 to 2.3 g/ml, such as from 2.3 to 2.4 g/ml, for example from 2.4 to 2.5 g/ml, such as from 2.5 to 2.6 g/ml, for example from 2.6 to 2.7 g/ml, such as from 2.7 to 2.8 g/ml, for example from 2.8 to 2.9 g/ml, such as from 2.9 to 3.0 g/ml, for example from 3 to 4 g/ml, such as from 4 to 5 g/ml, or higher than 5 g/ml or any combination of these intervals.

In one embodiment the present invention relates, in one or more reactive compound building block reaction steps, to use of a solvent with a dipole moment selected from the group consisting of for example from 0 to 0.1 g/ml, such as from 0.1 to 0.2 g/ml, for example from 0.2 to 0.3 g/ml, such as from 0.3 to 0.4 g/ml, for example from 0.4 to 0.5 g/ml, such as from 0.5 to 0.6 g/ml, for example from 0.6 to 0.7 g/ml, such as from 0.7 to 0.8 g/ml, for example from 0.8 to 0.9 g/ml, such as from 0.9 to 1.0 g/ml, for example from 1.0 to 1.1 g/ml, such as from 1.1 to 1.2 g/ml, for example from 1.2 to 1.3 g/ml, such as from 1.3 to 1.4 g/ml, for example from 1.4 to 1.5 g/ml, such as from 1.5 to 1.6 g/ml, for example from 1.6 to 1.7 g/ml, such as from 1.7 to 1.8 g/ml, for example from 1.8 to 1.9 g/ml, such as from 1.9 to 2.0 g/ml, for example from 2.0 to 2.1 g/ml, such as from 2.1 to 2.2 g/ml, for example from 2.2 to 2.3 g/ml, such as from 2.3 to 2.4 g/ml, for example from 2.4 to 2.5 g/ml, such as from 2.5 to 2.6 g/ml, for example from 2.6 to 2.7 g/ml, such as from 2.7 to 2.8 g/ml, for example from 2.8 to 2.9 g/ml, such as from 2.9 to 3.0 g/ml, for example from 3.0 to 3.1 g/ml, such as from 3.1 to 3.2 g/ml, for example from 3.2 to 3.3 g/ml, such as from 3.3 to 3.4 g/ml, for example from 3.4 to 3.5 g/ml, such as from 3.5 to 3.6 g/ml, for example from 3.6 to 3.7 g/ml, such as from 3.7 to 3.8 g/ml, for example from 3.8 to 3.9 g/ml, such as from 3.9 to 4.0 g/ml, for example from 4.0 to 4.1 g/ml, such as from 4.1 to 4.2 g/ml, for example from 4.2 to 4.3 g/ml, such as from 4.3 to 4.4 g/ml, for example from 4.4 to 4.5 g/ml, such as from 4.5 to 4.6 g/ml, for example from 4.6 to 4.7 g/ml, such as from 4.7 to 4.8 g/ml, for example from 4.8 to 4.9 g/ml, such as from 4.9 to 5.0 g/ml, or higher than 5 g/ml or any combination of these intervals.

TABLE B

| Solvent | Chemical formula | δD Dispersion | δP Polar | δH Hydrogen bonding |
|---|---|---|---|---|
| Non-polar solvents | | | | |
| Hexane | $CH_3-CH_2-CH_2-CH_2-CH_2-CH_3$ | 14.9 | 0.0 | 0.0 |
| Benzene | $C_6H_6$ | 18.4 | 0.0 | 2.0 |
| Toluene | $C_6H_5-CH_3$ | 18.0 | 1.4 | 2.0 |
| Diethyl ether | $CH_3CH_2-O-CH_2-CH_3$ | 14.5 | 2.9 | 4.6 |
| Chloroform | $CHCl_3$ | 17.8 | 3.1 | 5.7 |
| 1,4-Dioxane | /—$CH_2$—$CH_2$—O—$CH_2$—$CH_2$—O—\ | 17.5 | 1.8 | 9.0 |
| Polar aprotic solvents | | | | |
| Ethyl acetate | $CH_3-C(=O)-O-CH_2-CH_3$ | 15.8 | 5.3 | 7.2 |
| Tetrahydrofuran (THF) | /—$CH_2$—$CH_2$—O—$CH_2$—$CH_2$—\ | 16.8 | 5.7 | 8.0 |
| Dichloromethane | $CH_2Cl_2$ | 17.0 | 7.3 | 7.1 |
| Acetone | $CH_3-C(=O)-CH_3$ | 15.5 | 10.4 | 7.0 |
| Acetonitrile (MeCN) | $CH_3-C\equiv N$ | 15.3 | 18.0 | 6.1 |
| Dimethylformamide (DMF) | $H-C(=O)N(CH_3)_2$ | 17.4 | 13.7 | 11.3 |
| Dimethyl sulfoxide (DMSO) | $CH_3-S(=O)-CH_3$ | 18.4 | 16.4 | 10.2 |

TABLE B-continued

| Solvent | Chemical formula | δD Dispersion | δP Polar | δH Hydrogen bonding |
|---|---|---|---|---|
| Polar protic solvents | | | | |
| Acetic acid | $CH_3-C(=O)OH$ | 14.5 | 8.0 | 13.5 |
| n-Butanol | $CH_3-CH_2-CH_2-CH_2-OH$ | 16.0 | 5.7 | 15.8 |
| Isopropanol | $CH_3-CH(-OH)-CH_3$ | 15.8 | 6.1 | 16.4 |
| n-Propanol | $CH_3-CH_2-CH_2-OH$ | 16.0 | 6.8 | 17.4 |
| Ethanol | $CH_3-CH_2-OH$ | 15.8 | 8.8 | 19.4 |
| Methanol | $CH_3-OH$ | 14.7 | 12.3 | 22.3 |
| Formic acid | $H-C(=O)OH$ | 14.6 | 10.0 | 14.0 |
| Water | $H-O-H$ | 15.5 | 16.0 | 42.3 |

In one embodiment of the present invention, one or more reactive compound building block reaction steps employs a solvent with a δD Dispersion of from 0 to 30, such as from 0 to 1, for example from 1 to 2, such as from 2 to 3, for example from 3 to 4, such as from 4 to 5, for example from 5 to 6, such as from 6 to 7, for example from 7 to 8, such as from 8 to 9, such as from 9 to 10, for example from 10 to 11, such as from 11 to 12, for example from 12 to 13, such as from 13 to 14, for example from 14 to 15, such as from 15 to 16, for example from 16 to 17, such as from 17 to 18, for example from 18 to 19, such as from 19 to 20, for example from 20 to 21, such as from 21 to 22, for example from 22 to 23, such as from 23 to 24, for example from 24 to 25, such as from 25 to 26, for example from 26 to 27, such as from 27 to 28, for example from 28 to 29, such as from 29 to 30, or more than 30 or any combination of these intervals.

In one embodiment of the present invention, one or more reactive compound building block reaction steps employs a solvent with a δD Polar from 0 to 30, such as from 0 to 1, for example from 1 to 2, such as from 2 to 3, for example from 3 to 4, such as from 4 to 5, for example from 5 to 6, such as from 6 to 7, for example from 7 to 8, such as from 8 to 9, such as from 9 to 10, for example from 10 to 11, such as from 11 to 12, for example from 12 to 13, such as from 13 to 14, for example from 14 to 15, such as from 15 to 16, for example from 16 to 17, such as from 17 to 18, for example from 18 to 19, such as from 19 to 20, for example from 20 to 21, such as from 21 to 22, for example from 22 to 23, such as from 23 to 24, for example from 24 to 25, such as from 25 to 26, for example from 26 to 27, such as from 27 to 28, for example from 28 to 29, such as from 29 to 30, or more than 30 or any combination of these intervals.

In one embodiment of the present invention, one or more reactive compound building block reaction steps employs a solvent with a δD Hydrogen bonding from 0 to 50, such as from 0 to 1, for example from 1 to 2, such as from 2 to 3, for example from 3 to 4, such as from 4 to 5, for example from 5 to 6, such as from 6 to 7, for example from 7 to 8, such as from 8 to 9, such as from 9 to 10, for example from 10 to 11, such as from 11 to 12, for example from 12 to 13, such as from 13 to 14, for example from 14 to 15, such as from 15 to 16, for example from 16 to 17, such as from 17 to 18, for example from 18 to 19, such as from 19 to 20, for example from 20 to 21, such as from 21 to 22, for example from 22 to 23, such as from 23 to 24, for example from 24 to 25, such as from 25 to 26, for example from 26 to 27, such as from 27 to 28, for example from 28 to 29, such as from 29 to 30, for example from 30 to 32, such as from 32 to 34, for example from 34 to 36, such as from 36 to 38, for example from 38 to 40, such as from 40 to 42, for example from 42 to 44, such as from 44 to 46, for example from 46 to 48, such as from 48 to 50, or more than 50 or any combination of these intervals.

Yet another way of characterizing a solvent is by the boiling point of said solvent. Table C herein below lists examples of suitable solvents and their boiling points.

TABLE C

| Solvent | Boiling point (° C.) |
|---|---|
| Ethylene dichloride | 83.48 |
| Pyridine | 115.25 |
| Methyl isobutyl ketone | 116.5 |
| Methylene chloride | 39.75 |
| Isooctane | 99.24 |
| Carbon disulfide | 46.3 |
| Carbon tetrachloride | 76.75 |
| O-xylene | 144.42 |

Accordingly, in one embodiment of the present invention comprise use of a solvent with a boiling point from 0° C. to 250° C., such as from 0° C. to 10° C., for example from 10° C. to 20° C., such as from 20° C. to 30° C., for example from 30° C. to 40° C., such as from 40° C. to 50° C., for example from 50° C. to 60° C., such as from 60° C. to 70° C., for example from 70° C. to 80° C., such as from 80° C. to 90° C., for example from 90° C. to 100° C., such as from 100° C. to 110° C., for example from 110° C. to 120° C., such as from 120° C. to 130° C., for example from 130° C. to 140° C., such as from 140° C. to 150° C., for example from 150° C. to 160° C., such as from 160° C. to 170° C., for example from 170° C. to 180° C., such as from 180° C. to 190° C., for example from 190° C. to 200° C., such as from 210° C. to 220° C., for example from 220° C. to 230° C., such as from 230° C. to 240° C., and for example from 240° C. to 250° C.

Most organic solvents have a lower density than water, which means they are lighter and will form a separate layer on top of water. An important exception is many halogenated solvents, like dichloromethane and chloroform. These solvents, when mixed with an aqueous solvent, will tend to sink to the bottom of a reaction container, leaving the aqueous layer as the top layer.

Often, specific gravity is cited in place of density. Specific gravity is defined as the density of the solvent divided by the density of water at the same temperature. As such, specific gravity is a unitless value. Specific gravity readily communicates whether a water-insoluble solvent will float (SG<1.0) or sink (SG>1.0) when mixed with water.

Examples of solvents and their specific gravity are listed in Table D herein below.

TABLE D

| Solvent | Specific gravity |
| --- | --- |
| Pentane | 0.626 |
| Petroleum ether | 0.656 |
| Hexane | 0.659 |
| Heptane | 0.684 |
| Diethyl amine | 0.707 |
| Diethyl ether | 0.713 |
| Triethyl amine | 0.728 |
| Tert-butyl methyl ether | 0.741 |
| Cyclohexane | 0.779 |
| Tert-butyl alcohol | 0.781 |
| Isopropanol | 0.785 |
| Acetonitrile | 0.786 |
| Ethanol | 0.789 |
| Acetone | 0.790 |
| Methanol | 0.791 |
| Methyl isobutyl ketone | 0.798 |
| Isobutyl alcohol | 0.802 |
| 1-Propanol | 0.803 |
| Methyl ethyl ketone | 0.805 |
| 2-Butanol | 0.808 |
| Isoamyl alcohol | 0.809 |
| 1-Butanol | 0.810 |
| Diethyl ketone | 0.814 |
| 1-Octanol | 0.826 |
| p-Xylene | 0.861 |
| m-Xylene | 0.864 |
| Toluene | 0.867 |
| Dimethoxyethane | 0.868 |
| Benzene | 0.879 |
| Butyl acetate | 0.882 |
| 1-Chlorobutane | 0.886 |
| Tetrahydrofuran | 0.889 |
| Ethyl acetate | 0.895 |
| o-Xylene | 0.897 |
| Hexamethylphosphorus triamide | 0.898 |
| 2-Ethoxyethyl ether | 0.909 |
| N,N-Dimethylacetamide | 0.937 |
| Diethylene glycol dimethyl ether | 0.943 |
| N,N-Dimethylformamide | 0.944 |
| 2-Methoxyethanol | 0.965 |
| Pyridine | 0.982 |
| Propanoic acid | 0.993 |
| Water | 1.000 |
| 2-Methoxyethyl acetate | 1.009 |
| Benzonitrile | 1.01 |
| 1-Methyl-2-pyrrolidinone | 1.028 |
| Hexamethylphosphoramide | 1.03 |
| 1,4-Dioxane | 1.033 |
| Acetic acid | 1.049 |
| Acetic anhydride | 1.08 |
| Dimethyl sulfoxide | 1.092 |
| Chlorobenzene | 1.1066 |
| Deuterium oxide | 1.107 |
| Ethylene glycol | 1.115 |
| Diethylene glycol | 1.118 |
| Propylene carbonate | 1.21 |
| Formic acid | 1.22 |
| 1,2-Dichloroethane | 1.245 |
| Glycerin | 1.261 |
| Carbon disulfide | 1.263 |
| 1,2-Dichlorobenzene | 1.306 |
| Methylene chloride | 1.326 |
| Nitromethane | 1.382 |
| 2,2,2-Trifluoroethanol | 1.393 |
| Chloroform | 1.498 |
| 1,1,2-Trichlorotrifluoroethane | 1.575 |
| Carbon tetrachloride | 1.594 |
| Tetrachloroethylene | 1.623 |

In one embodiment of the present invention, one or more reactive compound building block reaction steps employs a solvent having a specific gravity of from 0 to 5, such as for example from 0 to 0.1 g/ml, such as from 0.1 to 0.2 g/ml, for example from 0.2 to 0.3 g/ml, such as from 0.3 to 0.4 g/ml, for example from 0.4 to 0.5 g/ml, such as from 0.5 to 0.6 g/ml, for example from 0.6 to 0.7 g/ml, such as from 0.7 to 0.8 g/ml, for example from 0.8 to 0.9 g/ml, such as from 0.9 to 1.0 g/ml, for example from 1.0 to 1.1 g/ml, such as from 1.1 to 1.2 g/ml, for example from 1.2 to 1.3 g/ml, such as from 1.3 to 1.4 g/ml, for example from 1.4 to 1.5 g/ml, such as from 1.5 to 1.6 g/ml, for example from 1.6 to 1.7 g/ml, such as from 1.7 to 1.8 g/ml, for example from 1.8 to 1.9 g/ml, such as from 1.9 to 2.0 g/ml, for example from 2.0 to 2.1 g/ml, such as from 2.1 to 2.2 g/ml, for example from 2.2 to 2.3 g/ml, such as from 2.3 to 2.4 g/ml, for example from 2.4 to 2.5 g/ml, such as from 2.5 to 2.6 g/ml, for example from 2.6 to 2.7 g/ml, such as from 2.7 to 2.8 g/ml, for example from 2.8 to 2.9 g/ml, such as from 2.9 to 3.0 g/ml, for example from 3 to 4 g/ml, such as from 4 to 5 g/ml, or higher than 5 g/ml or any combination of these intervals.

In one embodiment of the present invention, one or more reactive compound building block reaction steps employs a solvent with a pH value from 0 to 14, such as from 1 to 2, for example from 2 to 3, such as from 3 to 4, for example from 4 to 5, such as from 5 to 6, for example from 6 to 7, such as from 7 to 8, for example from 8 to 9, such as from 10 to 11, for example from 11 to 12, such as from 12 to 13, for example from 13 to 14, including any combination of these intervals.

The organic solvent for use in one or more reactive compound building block reactions can in one embodiment be selected from the group consisting of volatile organic solvents, non-volatile organic solvents, aliphatic hydrocarbon solvents, acetone organic solvents, dmso organic solvents, ethanol organic solvents, ether organic solvents, halogenated organic solvents, methanol organic solvents, polar organic solvents, and non-polar organic solvents.

In one embodiment the solvent for use in one or more reactive compound building block reactions can be selected from the table herein below.

| Solvent | Formula | MW | Boiling point (° C.) | Melting point (° C.) | Density (g/mL) | Solubiliy in water (g/100 g) | Dielectric Constant | Flash point (° C.) |
| --- | --- | --- | --- | --- | --- | --- | --- | --- |
| acetic acid | $C_2H_4O_2$ | 60.05 | 118 | 16.6 | 1.049 | Miscible | 6.15 | 39 |
| acetone | $C_3H_6O$ | 58.08 | 56.2 | −94.3 | 0.786 | Miscible | 20.7(25) | −18 |
| acetonitrile | $C_2H_3N$ | 41.05 | 81.6 | −46 | 0.786 | Miscible | 37.5 | 6 |
| benzene | $C_6H_6$ | 78.11 | 80.1 | 5.5 | 0.879 | 0.18 | 2.28 | −11 |
| 1-butanol | $C_4H_{10}O$ | 74.12 | 117.6 | −89.5 | 0.81 | 6.3 | 17.8 | 35 |
| 2-butanol | $C_4H_{10}O$ | 74.12 | 98 | −115 | 0.808 | 15 | 15.8(25) | 26 |
| 2-butanone | $C_4H_8O$ | 72.11 | 79.6 | −86.3 | 0.805 | 25.6 | 18.5 | −7 |
| t-butyl alcohol | $C_4H_{10}O$ | 74.12 | 82.2 | 25.5 | 0.786 | Miscible | 12.5 | 11 |

-continued

| Solvent | Formula | MW | Boiling point (° C.) | Melting point (° C.) | Density (g/mL) | Solubility in water (g/100 g) | Dielectric Constant | Flash point (° C.) |
|---|---|---|---|---|---|---|---|---|
| carbon tetrachloride | CCl$_4$ | 153.82 | 76.7 | −22.4 | 1.594 | 0.08 | 2.24 | — |
| chlorobenzene | C$_6$H$_5$Cl | 112.56 | 131.7 | −45.6 | 1.1066 | 0.05 | 5.69 | 29 |
| chloroform | CHCl$_3$ | 119.38 | 61.7 | −63.7 | 1.498 | 0.795 | 4.81 | — |
| cyclohexane | C$_6$H$_{12}$ | 84.16 | 80.7 | 6.6 | 0.779 | <0.1 | 2.02 | −20 |
| 1,2-dichloroethane | C$_2$H$_4$Cl$_2$ | 98.96 | 83.5 | −35.3 | 1.245 | 0.861 | 10.42 | 13 |
| diethylether | C$_4$H$_{10}$O | 74.12 | 34.6 | −116.3 | 0.713 | 7.5 | 4.34 | −45 |
| diethylene glycol | C$_4$H$_{10}$O$_3$ | 106.12 | 245 | −10 | 1.118 | 10 | 31.7 | 143 |
| diglyme (diethylene glycol dimethyl ether) | C$_6$H$_{14}$O$_3$ | 134.17 | 162 | −68 | 0.943 | Miscible | 7.23 | 67 |
| 1,2-dimethoxyethane (glyme, DME) | C$_4$H$_{10}$O$_2$ | 90.12 | 85 | −58 | 0.868 | Miscible | 7.2 | −6 |
| dimethylether | C$_2$H$_6$O | 46.07 | −22 | −138.5 | NA | NA | NA | −41 |
| dimethylformamide (DMF) | C$_3$H$_7$NO | 73.09 | 153 | −61 | 0.944 | Miscible | 36.7 | 58 |
| dimethyl sulfoxide (DMSO) | C$_2$H$_6$OS | 78.13 | 189 | 18.4 | 1.092 | 25.3 | 47 | 95 |
| dioxane | C$_4$H$_8$O$_2$ | 88.11 | 101.1 | 11.8 | 1.033 | Miscible | 2.21(25) | 12 |
| ethanol | C$_2$H$_6$O | 46.07 | 78.5 | −114.1 | 0.789 | Miscible | 24.6 | 13 |
| ethyl | C$_4$H$_8$O$_2$ | 88.11 | 77 | −83.6 | 0.895 | 8.7 | 6(25) | −4 |
| ethylene glycol | C$_2$H$_6$O$_2$ | 62.07 | 195 | −13 | 1.115 | Miscible | 37.7 | 111 |
| glycerin | C$_3$H$_8$O$_3$ | 92.09 | 290 | 17.8 | 1.261 | Miscible | 42.5 | 160 |
| heptane | C$_7$H$_{16}$ | 100.20 | 98 | −90.6 | 0.684 | 0.01 | 1.92 | −4 |
| Hexamethylphosphoramide (HMPA) | C$_6$H$_{18}$N$_3$OP | 179.20 | 232.5 | 7.2 | 1.03 | Miscible | 31.3 | 105 |
| Hexamethylphosphorous triamide (HMPT) | C$_6$H$_{18}$N$_3$P | 163.20 | 150 | −44 | 0.898 | Miscible | ?? | 26 |
| hexane | C$_6$H$_{14}$ | 86.18 | 69 | −95 | 0.659 | 0.014 | 1.89 | −22 |
| methanol | CH$_4$O | 32.04 | 64.6 | −98 | 0.791 | Miscible | 32.6(25) | 12 |
| methyl t-butylether (MTBE) | C$_5$H$_{12}$O | 88.15 | 55.2 | −109 | 0.741 | 5.1 | ?? | −28 |
| methylene chloride | CH$_2$Cl$_2$ | 84.93 | 39.8 | −96.7 | 1.326 | 1.32 | 9.08 | 1.6 |
| N-methyl-2-pyrrolidinone (NMP) | C$_5$H$_9$NO | 99.13 | 202 | −24 | 1.033 | 10 | 32 | 91 |
| nitromethane | CH$_3$NO$_2$ | 61.04 | 101.2 | −29 | 1.382 | 9.50 | 35.9 | 35 |
| pentane | C$_5$H$_{12}$ | 72.15 | 36.1 | −129.7 | 0.626 | 0.04 | 1.84 | −49 |
| Petroleum ether (ligroine) | — | — | 30-60 | −40 | 0.656 | — | — | −30 |
| 1-propanol | C$_3$H$_8$O | 88.15 | 97 | −126 | 0.803 | Miscible | 20.1(25) | 15 |
| 2-propanol | C$_3$H$_8$O | 88.15 | 82.4 | −88.5 | 0.785 | Miscible | 18.3(25) | 12 |
| pyridine | C$_5$H$_5$N | 79.10 | 115.2 | −41.6 | 0.982 | Miscible | 12.3(25) | 17 |
| tetrahydrofuran (THF) | C$_4$H$_8$O | 72.11 | 66 | −108.4 | 0.886 | 30 | 7.6 | −21 |
| toluene | C$_7$H$_8$ | 92.14 | 110.6 | −93 | 0.867 | 0.05 | 2.38(25) | 4 |
| triethyl amine | C$_6$H$_{15}$N | 101.19 | 88.9 | −114.7 | 0.728 | 0.02 | 2.4 | −11 |

-continued

| Solvent | Formula | MW | Boiling point (° C.) | Melting point (° C.) | Density (g/mL) | Solubiliy in water (g/100 g) | Dielectric Constant | Flash point (° C.) |
|---|---|---|---|---|---|---|---|---|
| water | $H_2O$ | 18.02 | 100.00 | 0.00 | 0.998 | — | 78.54 | — |
| water, heavy | $D_2O$ | 20.03 | 101.3 | 4 | 1.107 | Miscible | ?? | — |
| o-xylene | $C_8H_{10}$ | 106.17 | 144 | −25.2 | 0.897 | Insoluble | 2.57 | 32 |
| m-xylene | $C_8H_{10}$ | 106.17 | 139.1 | −47.8 | 0.868 | Insoluble | 2.37 | 27 |
| p-xylene | $C_8H_{10}$ | 106.17 | 138.4 | 13.3 | 0.861 | Insoluble | 2.27 | 27 |

Accordingly, as will be clear from the above, the methods of the present employ a plurality of different reactive compound building block reactions capable of reacting with each other or with a chemical reaction site under various reaction conditions and in various solvents, wherein a tag or an identifier oligonucleotide is protected in at least one such reaction step, and wherein the same or a different tag, or the same or a different identifier oligonucleotide, is un-protected in at least one other reaction step taking place either prior to or after the afore-mentioned "protected" reactive compound building block reaction step.

Any combination of protection and de-protection of oligonucleotides can occur independently of whether the nascent bi-functional complex is linked to a solid support or not. The above-cited versatile reactive compound building block reactions allow both protic and aprotic solvents to be used, and the reactions can be carried out with reactive compound building blocks which are soluble in either water or an organic solvent.

Preferably, at least one enzymatic tag addition reaction is carried out using an un-protected tag addition site, or one or more un-protected tags, or an un-protected oligonucleotide tag identifier comprising two or more oligonucleotide tags each identifying a reactive compound building block which has reacted with a chemical reaction site, or is going to react with a chemical reaction site in a subsequent synthesis round. Further tag addition steps can be performed by enzymatic or by chemical means.

A common feature of many DNA-based catalysis approaches is that they inherently require an aqueous solvent as a reaction medium. While aqueous phase catalysis is an area of considerable interest due to the potential advantages of replacing organic solvents with water, and the special properties of water as part of a reaction medium, aqueous solvents represent in some instances an undesirable medium for performing certain reactive compound building block reactions. While water has been shown on the one hand to be beneficial for the rate and enantioselectivity of some catalyzed reactions, an obvious complication of using aqueous solvents is the limited solubility in such solvents of many organic substrates and reagents, including certain reactive compound building blocks with limited solubility in aqueous solvents. Accordingly, aqueous solvents may in one aspect of the present invention hamper or prevent certain certain reactive compound building block reactions to be performed. Accordingly, for many reactive compound building block reactions, organic co-solvents will be required to achieve chemical transformations at synthetically relevant scales.

One challenge associated with obtaining chemical transformations of certain reactive compound building blocks at synthetically relevant scales is represented by the presence of oligonucleotide tags, or identifier oligonucleotides, associated with a molecule part of the nascent bi-functional complexes according to the present invention. Such tags or oligonucleotide identifiers may e.g. precipitate and/or they may undergo a structural and/or physical change which render them unsuitable as identifiers of the final molecule.

In one embodiment, water-miscible organic co-solvents are used in certain reactive compound building block reactions in accordance with the present invention. Examples of co-solvents include MeCN, DMF, THF, EtOH, MeOH, DMSO, 1,4-Dioxane, and 2-Propanol.

Accordingly, in one embodiment of the invention there is provided a method for the synthesis of a bi-functional complex comprising a molecule part and an identifier oligonucleotide part identifying the molecule part, said method comprising the steps of i) optionally providing a solid support, ii) providing a first identifier oligonucleotide tag comprising a chemical reaction site capable of reacting with a first reactive compound building block and optionally capable of reacting with a further reactive compound building block, iii) providing a first reactive compound building block, wherein each first identifier oligonucleotide tag identifies the first reactive compound building block, iv) optionally linking, such as optionally covalently linking the first identifier oligonucleotide tag to the solid support, v) reacting the first reactive compound building block with the chemical reaction site of the first identifier oligonucleotide tag identifying the first reactive compound building block, wherein the first identifier oligonucleotide tag is optionally linked, such as optionally covalently linked to the solid support when the first reactive compound building block is reacted with the chemical reaction site of the first identifier oligonucleotide tag, wherein the reaction of the first reactive compound building block and the first identifier oligonucleotide tag generates a first intermediate, bi-functional complex comprising a first molecule part and a first identifier oligonucleotide tag optionally linked to the solid support, vi) reacting the first intermediate bi-functional complex obtained in step v) with a second reactive compound building block in the absence of a second identifier oligonucleotide tag identifying the second reactive compound building block, wherein the first intermediate bi-functional complex is optionally linked, such as optionally covalently linked to the solid support when the second reactive compound building block is reacted with the chemical reaction site and/or reacted with the first molecule part of the first intermediate bi-functional complex, wherein the reaction of the second reactive compound building block and the first intermediate bi-functional complex generates a second intermediate, bi-functional complex optionally linked to the solid support, vii) optionally cleaving the second intermediate bi-functional complex obtained in step vi) from the solid support, and viii) enzymatically adding, such as ligating, the first identifier oligonucleotide tag of said second intermediate bi-functional complex optionally cleaved from said solid support to a second identifier oligonucleotide tag identifying the second reactive compound building block, wherein the enzymatic ligation of the first and second identifier oligonucleotide tags generates a third intermediate bi-functional complex comprising a molecule part and an identifier oligonucleotide part identifying said molecule part.

In a further embodiment of the present invention there is provided a method for the synthesis of a bi-functional complex comprising a molecule part and an identifier oligonucleotide part identifying the molecule part, said method comprising the steps of i) providing a solid support, ii) providing, or synthesising directly on said solid support, a first identifier oligonucleotide tag comprising, or linked to, a chemical reaction site capable of reacting with a first reactive compound building block and, optionally, capable of reacting with a further reactive compound building block, iii) providing a first reactive compound building block, wherein each first identifier oligonucleotide tag identifies the first reactive compound building block, iv) linking, such as covalently linking, the first identifier oligonucleotide tag to the solid support, wherein the first identifier oligonucleotide tag can either be linked to the solid support via the initial nucleic acid residue employed in the synthesis of the first identifier oligonucleotide tag, or the first identifier oligonucleotide tag can be linked as a strand of covalently linked nucleotides, post-synthesis thereof to, to the solid support, v) reacting the first reactive compound building block with the chemical reaction site comprises by or linked to the first identifier oligonucleotide tag identifying the first reactive compound building block, wherein, optionally, said chemical reaction site may be the reaction product formed by the reaction of a chemical reaction site and one or more reactive compound building blocks in a previous synthesis round, wherein the first identifier oligonucleotide tag is linked, such as covalently linked, to the solid support when the first reactive compound building block is reacted with the chemical reaction site of the first identifier oligonucleotide tag, wherein the reaction of the first reactive compound building block and the first identifier oligonucleotide tag generates a first intermediate, bi-functional complex comprising a first molecule part and a first identifier oligonucleotide tag linked to the solid support, vi) reacting the first intermediate bi-functional complex obtained in step v) with a second reactive compound building block in the absence of a second identifier oligonucleotide tag identifying the second reactive compound building block, wherein the first intermediate bi-functional complex is linked, such as covalently linked, to the solid support when the second reactive compound building block is reacted with the chemical reaction site and/or reacted with the first molecule part of the first intermediate bi-functional complex, wherein the reaction of the second reactive compound building block and the first intermediate bi-functional complex generates a second intermediate, bi-functional complex linked to the solid support, vii) cleaving the second intermediate bi-functional complex obtained in step vi) from the solid support, and viii) enzymatically adding, such as ligating, the first identifier oligonucleotide tag of said second intermediate bi-functional complex optionally cleaved from said solid support to a second identifier oligonucleotide tag identifying the second reactive compound building block, wherein the enzymatic ligation of the first and second identifier oligonucleotide tags generates a third intermediate bi-functional complex comprising a molecule part and an identifier oligonucleotide part identifying said molecule part.

In one embodiment, at least one reactive compound building block reaction, such as a reaction of a reactive compound building block and the chemical reaction site comprised by, or linked to, the optionally protected first identifier oligonucleotide tag linked to the solid support, takes place in an organic solvent, optionally under anhydrous conditions, and at least one tag addition takes place when the nascent bi-functional complex is not bound to a solid support.

In a still further aspect of the present invention there is provided a method for the synthesis of a bi-functional complex comprising a molecule part and an identifier oligonucleotide part identifying the molecule part, said method comprising the steps of i) providing a first identifier oligonucleotide tag comprising a chemical reaction site capable of reacting with a first reactive compound building block, ii) providing a first reactive compound building block, wherein each first identifier oligonucleotide tag identifies the first reactive compound building block, iii) directly or indirectly reacting the first reactive compound building block with the first identifier oligonucleotide tag identifying the first reactive compound building block, wherein the reaction of the first reactive compound building block and the first identifier oligonucleotide tag generates a first intermediate, bi-functional complex comprising a first molecule part and a first identifier oligonucleotide, iv) reacting the first intermediate bi-functional complex obtained in step iii) with a second reactive compound building block in the absence of a second identifier oligonucleotide tag identifying the second reactive compound building block, wherein the reaction of the second reactive compound building block and the first intermediate bi-functional complex generates a second intermediate, bi-functional complex, v) enzymatically ligating the first identifier oligonucleotide tag of said second intermediate bi-functional complex to a second identifier oligonucleotide tag identifying the second reactive compound building block, wherein the enzymatic ligation of the first and second identifier oligonucleotide tags generates a third intermediate bi-functional complex comprising a molecule part and an identifier oligonucleotide part identifying said molecule part.

In an even further aspect of the present invention there is provided a method for the synthesis of a bi-functional complex comprising a molecule part and an identifier oligonucleotide part identifying the molecule part, said method comprising the steps of i) providing a solid support,
ii) providing a first identifier oligonucleotide tag comprising a chemical reaction site capable of reacting with a first reactive compound building block and optionally capable of reacting with a further reactive compound building block,
iii) providing a first reactive compound building block, wherein each first identifier oligonucleotide tag identifies the first reactive compound building block,
iv) covalently linking the first identifier oligonucleotide tag to the solid support,
v) reacting the first reactive compound building block with the chemical reaction site of the first identifier oligonucleotide tag identifying the first reactive compound building block,
wherein the first identifier oligonucleotide tag is covalently linked to the solid support when the first reactive compound building block is reacted with the chemical reaction site of the first identifier oligonucleotide tag, wherein the reaction of the first reactive compound building block and the first identifier oligonucleotide tag generates a first intermediate, bi-functional complex comprising a first molecule part and a first identifier oligonucleotide tag linked to the solid support,
vi) reacting the first intermediate bi-functional complex obtained in step v) with a second reactive compound building block in the absence of a second identifier oligonucleotide tag identifying the second reactive compound building block,
wherein the first intermediate bi-functional complex is covalently linked to the solid support when the second reactive compound building block is reacted with the chemical reaction site and/or with the first molecule part of the first intermediate bi-functional complex, wherein the reaction of the second reactive compound building block and the first intermediate bi-functional complex generates a second intermediate, bi-functional complex linked to the solid support,
vii) cleaving the second intermediate bi-functional complex obtained in step vi) from the solid support, and
viii) enzymatically ligating the first identifier oligonucleotide tag of said second intermediate bi-functional complex cleaved from said solid support to a second identifier oligonucleotide tag identifying the second reactive compound building block,
wherein the enzymatic ligation of the first and second identifier oligonucleotide tags generates a third intermediate bi-functional complex comprising a molecule part and an identifier oligonucleotide part identifying said molecule part.

The third intermediate bi-functional complex can be subjected to further reactive compound building block reactions and further oligonucleotide tag reactions as disclosed in more detail herein below.

In one embodiment, the first identifier oligonucleotide tag is synthesised directly on the solid support, e.g. by covalently linking a part of the first identifier oligonucleotide tag, such as a single nucleotide, to the solid support and synthesising the remaining part of the first identifier oligonucleotide tag by a solid phase nucleotide synthesis method comprising the steps of providing said remaining one or more nucleotide(s), optionally as sequentially provided, single nucleotides, and linking the remaining one or more nucleotide(s) to the part of the first identifier oligonucleotide tag covalently linked to the solid support.

In one embodiment, a reactive compound building block having reacted in a previous reaction round with one or more chemical reaction sites of an identifier oligonucleotide tag, or a reactive compound building block having previously reacted with a reactive compound building block which had in turn reacted in a previous round with said one or more chemical reaction sites, is to be regarded in one embodiment as a chemical reaction site capable of reacting with one or more reactive compound building blocks provided in a subsequent reaction round.

When a library of different bi-functional complexes are synthesised by split-and-mix methods according to the present invention, a composition of different nascent or intermediate bi-functional complexes obtained e.g. in step v) is split (divided) into a plurality of different compartments. In each different compartment, a different second reactive compound building block is provided, c.f. step vi) above.

Accordingly, the reaction of different reactive compound building blocks takes place in different compartments and this results in the synthesis in each different compartment of different nascent or intermediate bi-functional complexes comprising the result (reaction product in the form of a molecule part or a molecule precursor) of a reaction involving first and second reactive compound building blocks, wherein said reaction product of the nascent bi-functional product is linked to a corresponding identifier oligonucleotide comprising oligonucleotide tags identifying the molecule part and/or the reactive compound building blocks having participated in the synthesis of the molecule part. Consequently, different bi-functional complexes from a given round of synthesis are combined and split in order to initiate a new synthesis round.

In view of the above there is also provided, in yet another aspect of the invention, a method for the synthesis of a plurality of different bi-functional complexes each comprising a molecule and an oligonucleotide identifier identifying the molecule, said method comprising the steps of:

i) providing a plurality of solid supports,
ii) providing a plurality of different first identifier oligonucleotide tags each comprising a chemical reaction site capable of reacting with a first reactive compound building block and optionally capable of reacting with a further reactive compound building block,
iii) providing a plurality of different first reactive compound building blocks,
wherein each first identifier oligonucleotide tag identifies a first reactive compound building block,
iv) covalently linking different first identifier oligonucleotide tags to each of a plurality of solid supports,
v) reacting the plurality of different first reactive compound building blocks with the chemical reaction site of the different first identifier oligonucleotide tags each identifying a first reactive compound building block, wherein the first identifier oligonucleotide tags are each covalently linked to a solid support when the first reactive compound building blocks are reacted with the chemical reaction site of the first identifier oligonucleotide tags,
wherein the reactions of the different first reactive compound building blocks and the corresponding first identifier oligonucleotide tags generate a plurality of different first intermediate, bi-functional complexes each comprising a different first molecule part and a corresponding first identifier oligonucleotide tag linked to the solid support, vi) reacting the different first intermediate bi-functional complexes obtained in step v) with a plurality of different second reactive compound building blocks in the absence of second identifier oligonucleotide tags identifying the second reactive compound building blocks, wherein the different first intermediate bi-functional complexes are covalently linked to a solid support when the different second reactive compound building blocks are reacted with a chemical reaction site and/or with a first molecule part of the different first intermediate bi-functional complexes, wherein the reaction of the different second reactive compound building blocks and the first intermediate bi-functional complexes generate a plurality of different second intermediate, bi-functional complexes linked to a solid support, vii) cleaving different second intermediate bi-functional complexes obtained in step vi) from the solid support, and viii) enzymatically ligating each of a plurality of first identifier oligonucleotide tags of the second intermediate bi-functional complexes cleaved from a solid support to a second identifier oligonucleotide tag identifying a corresponding second reactive compound building block, wherein the enzymatic ligation of the first and second identifier oligonucleotide tags generates a plurality of different third intermediate bi-functional complexes each comprising a different molecule part and a corresponding identifier oligonucleotide part identifying said molecule part.

The different third intermediate bi-functional complexes can be subjected to further reactive compound building block reactions and further oligonucleotide tag reactions as disclosed in more detail herein below.

In one embodiment, the first identifier oligonucleotide tag is synthesised directly on the solid support, e.g. by covalently linking a part of the first identifier oligonucleotide tag, such as a single nucleotide, to the solid support and synthesising the remaining part of the first identifier oligonucleotide tag by a solid phase nucleotide synthesis method comprising the steps of providing said remaining one or more nucleotide(s), optionally as sequentially provided, single nucleotides, and linking the remaining one or more nucleotide(s) to the part of the first identifier oligonucleotide tag covalently linked to the solid support.

In the above-cited methods, the synthesised molecules are preferably not a natural or non-natural nucleotide, a natural or non-natural oligonucleotide, or a natural or non-natural polynucleotide.

Accordingly, while the identifier oligonucleotide comprises natural or non-natural nucleotides, the molecule part of a bi-functional complex does not consist of an entity selected from the group consisting of a natural or non-natural nucleotide, a natural or non-natural oligonucleotide, and a natural or non-natural polynucleotide Reactive groups present in an identifier oligonucleotide tag or an identifier oligonucleotide can optionally be protected by suitable protection groups. Such reactive groups include, but are not limited to, amines and phosphates present in individual nucleotides. This may be particularly relevant when an identifier oligonucleotide tag is linked to a solid support (cf. step iv) herein above), or when a reactive compound building block is reacted—e.g. with a chemical reaction site of the tag or with another reactive compound building block—(cf. steps v) and vi), respectively, herein above).

The devised reaction scheme according to the present invention allows use of organic solvents during the initial reaction steps—i.e. when the nascent bi-functional complex is linked to a solid support. Once cleaved from the solid support, remaining reactive compound building block reactions are carried out in solution and preferably in the absence of a covalent link between a nascent, bi-functional complex and a solid support. The reactions conditions for such remaining reactive compound building block reactions are typically those compatible with aqueous solution organic chemical synthesis schemes. Use of protection groups is optional for such reaction schemes indicating that for some reactions it may be desirable, but not necessary, to use protection groups for protecting either reactive compound building blocks and/or identifier oligonucleotide tags.

In one embodiment, either or both of a first reactive compound building block and a first identifier oligonucleotide tag is protected. In another embodiment, none or only one of a first reactive compound building block and a first identifier oligonucleotide tag is protected. Accordingly, a first reactive compound building block or a first identifier oligonucleotide tag can be protected.

While a first identifier oligonucleotide tag can be synthesised e.g. by phosphoamidite synthesis directly on the solid support, second and further identifier oligonucleotide tags preferably comprise natural or non-natural nucleotides capable of being enzymatically ligated. Preferably, all second and further identifier oligonucleotide tag additions are obtained by an enzymatic ligations step.

The identifier oligonucleotide tags can be single stranded or double stranded and they can comprise both single stranded and double stranded parts. Single stranded parts are preferably in the form of one or more overhang sequences. When on double stranded form, the two strands of an identifier oligonucleotide can be covalently linked or non-covalently linked. Suitable linker structures are disclosed herein below in more detail.

An identifier oligonucleotide tag in one embodiment preferably comprises a framing sequence part, a codon sequence part and an overhang sequence part. A framing sequence can serve various purposes, for example as a further annealing region for complementary anti-tags and/or as a sequence informative of the sequential synthesis history of the molecule part being synthesised, i.e. bearing evidence of the chronology of the synthesis history and the order in which different reactive compound building blocks have reacted.

In one embodiment, the framing sequence provides a binding site for PCR primers complementary thereto and PCR amplification of the oligonucleotide identifier.

In certain embodiments, an identifier oligonucleotide tag codes for several different reactive compound building blocks. In a subsequent identification step, the structure of the molecule can never-the-less be deduced by taking advantage of the knowledge of the different attachment chemistries, steric hindrance, deprotection of orthogonal protection groups, etc.

In another embodiment, the same identifier oligonucleotide tag can be used collectively for a group of reactive compound building blocks having a common functionality, such as e.g. a lipophilic nature, a similar molecular weight, or a certain attachment chemistry, etc.

In a still further embodiment, each identifier oligonucleotide tag is unique, i.e. an identical combination or sequence of nucleotides identifies only one reactive compound building block. The same or different synthesis methods can employ the same or different type of identifier oligonucleotide tags.

In some embodiments it can be advantageous to use several different tags for the same reactive compound building block. Accordingly, two or more tags identifying the same reactive compound building block can optionally carry further information relating to e.g. different reaction conditions.

The identifier oligonucleotide of the final bi-functional complex comprises all the identifier oligonucleotide tag necessary for identifying the corresponding molecule part—or the reactive compound building blocks having participated in the synthesis of the molecule part. All or part of the sequence of each identifier oligonucleotide tag is used to decipher the structure of the reactive compound building blocks that have participated in the formation of the molecule part.

The order of the tags can also be used to determine the order of incorporation of different reactive compound building blocks. Usually, to facilitate a decoding step, identifier oligonucleotide tags will further comprise a constant region, or a binding region, together with the identifier oligonucleotide tag sequence identifying a given reactive compound building block (a "codon sequence"). The constant region may contain information about the position of the reactive compound building block in a synthesis pathway resulting in the synthesis of the molecule.

The identifier oligonucleotide of the bi-functional complex is in a preferred aspect of the invention amplifiable. The capability of being amplified allows use of a small amount of bi-functional complex during a selection process.

In one embodiment an identifier oligonucleotide tag is a sequence of nucleotides which can be amplified using standard techniques like PCR. When two or more identifier oligonucleotide tags are present in a linear identifying oligonucleotide, said oligonucleotide generally comprises a backbone structure allowing an enzyme to recognise the identifier oligonucleotide as a substrate. As an example the back bone structure can be DNA or RNA.

Once the above-cited methods have been carried out—and an intermediate bi-functional complex has been synthesised—further method steps can be carried out as disclosed herein below in more detail. The further method steps employ as a starting material the end product(s)—i.e. final or intermediate bi-functional complexes obtained by performing the above-cited methods pertaining to preferred aspects of the present invention.

In one embodiment, the further method steps comprise the steps of
a) providing a nascent bi-functional complex comprising a chemical reaction site and a priming site for enzymatic addition of a tag in the form of a sequence of consecutive nucleotides,
b) reacting the chemical reaction site with one or more reactive compound building blocks, and
c) reacting the priming site enzymatically with one or more tags identifying the one or more reactive compound building blocks,
wherein a reactive compound building block and the tag identifying the reactive compound building block are not linked prior to their reaction with the chemical reaction site and the priming site, respectively, of the nascent bi-functional complex.

In another embodiment, the further method steps comprise the steps of
(a) providing a solution comprising m initiator compounds in the form of intermediate bi-functional complexes, wherein m is an integer of 1 or greater, where the initiator compounds consist of a functional moiety comprising n building blocks, where n is an integer of 1 or greater, which is operatively linked to an initial oligonucleotide which identifies the n building blocks;
(b) dividing the solution of step (a) into r reaction vessels, wherein r is an integer of 2 or greater, thereby producing r aliquots of the solution;
(c) reacting the initiator compounds in each reaction vessel with one of r building blocks, thereby producing r aliquots comprising compounds consisting of a functional moiety comprising n+1 building blocks operatively linked to the initial oligonucleotide; and
(d) reacting the initial oligonucleotide in each aliquot with one of a set of r distinct incoming oligonucleotides in the presence of an enzyme which catalyzes the ligation of the incoming oligonucleotide and the initial oligonucleotide, under conditions suitable for enzymatic ligation of the incoming oligonucleotide and the initial oligonucleotide; thereby producing r aliquots comprising molecules consisting of a functional moiety comprising n+1 building blocks operatively linked to an elongated oligonucleotide which encodes the n+1 building blocks.

In yet another embodiment, the further method steps comprise the steps of
(a) providing an initiator compound in the form of an intermediate bi-functional complex comprising an initial functional moiety comprising n building blocks, where n is an integer of 1 or greater, wherein the initial functional moiety comprises at least one reactive group, and is operatively linked to an initial oligonucleotide; wherein the initial functional moiety and the initial functional oligonucleotide are linked by a linking moiety and wherein the initial oligonucleotide is double-stranded and the linking moiety is covalent coupled to the initial functional moiety and to both strands of the initial oligonucleotide; wherein the linking moiety comprises a first functional group capable of forming a covalent bond with a building block, a second functional group capable of forming a bond with the 5'-end of one strand of the initial oligonucleotide, and a third functional group capable of forming a covalent bond with the 3'-end of the other strand of the initial oligonucleotide;
(b) reacting the initiator compound with a building block comprising at least one complementary reactive group, wherein the at least one complementary reactive group is complementary to the reactive group of step (a), under conditions suitable for reaction of the complementary reactive group to form a covalent bond;
(c) reacting the initial oligonucleotide with an incoming oligonucleotide corresponding to the building block of step (b) in the presence of an enzyme which catalyzes ligation of the initial oligonucleotide and the incoming oligonucleotide, under conditions suitable for ligation of the incoming oligonucleotide and the initial oligonucleotide to form an encoding oligonucleotide;
thereby producing a molecule which comprises a functional moiety comprising n+1 building blocks which is operatively linked to an encoding oligonucleotide which identifies the structure of the functional moiety.

In yet another embodiment, the further method steps comprise the steps of performing a method of synthesizing a molecule comprising a functional moiety which is operatively linked to an encoding oligonucleotide which identifies the structure of the functional moiety, wherein said method comprises the steps of:

(a) providing an intermediate bi-functional complex comprising an initiator compound comprising an initial functional moiety comprising n building blocks, where n is an integer of 1 or greater, wherein the initial functional moiety comprises at least one reactive group, and is operatively linked to an initial oligonucleotide; wherein the initial functional moiety and the initial oligonucleotide are linked by a linking moiety and wherein the initial oligonucleotide is double-stranded and the linking moiety is covalently coupled to the initial functional moiety and to both strands of the initial oligonucleotide; wherein the linking moiety comprises the structure

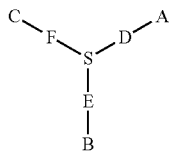

wherein
A is a first functional group capable of forming a covalent bond with the building block;
B is a second functional group capable of forming a covalent bond with the 5'-end of one strand of the initial oligonucleotide;
C is a third functional group capable of forming a covalent bond with the 3'-end of the other strand o the initial oligonucleotide;
S is an atom or a scaffold;
D is a chemical structure that connects A to S;
E is a chemical structure that connects B to S; and
F is a chemical structure that connects C to S;
wherein, preferably, D, E and F are each, independently, and alkylene group or an oligo(ethylene glycol) group;
(b) reacting the initiator compound with a building block comprising at least one complementary reactive group, wherein the at least one complementary reactive group is complementary to the reactive group of step (a), under conditions suitable for reaction of the complementary reactive group to form a covalent bond;
(c) reacting the initial oligonucleotide with an incoming oligonucleotide corresponding to the building block of step (b) in the presence of an enzyme which catalyzes ligation of the initial oligonucleotide and the incoming oligonucleotide, under conditions suitable for ligation of the incoming oligonucleotide and the initial oligonucleotide to form an encoding oligonucleotide;
thereby producing a molecule which comprises a functional moiety comprising n+1 building blocks which is operatively linked to an encoding oligonucleotide which identifies the structure of the functional moiety.

In yet another embodiment, the further method steps comprise the steps of performing a method of synthesizing a library of compounds in solution, wherein the compounds comprise a functional moiety comprising two or more building blocks which is operatively linked to an encoding oligonucleotide which identifies the structure of the functional moiety, said method comprises the further method steps of (a) providing a solution comprising m initiator compounds in the form of intermediate bi-functional complexes, wherein m is an integer of 1 or greater, where the initiator compounds comprise an initial functional moiety comprising n building blocks comprising at least one reactive group, where n is an integer of 1 or greater, which is operatively linked to an initial oligonucleotide corresponding to the n building blocks; wherein the initial functional moiety and the initial oligonucleotide are linked by a linking moiety and wherein the initial oligonucleotide is double-stranded and the linking moiety is covalent coupled to the initial functional moiety and to both strands of the initial oligonucleotide;
(b) dividing the solution of step (a) into r reaction vessels, wherein r is an integer of 2 or greater, thereby producing r aliquots of the solution;
(c) reacting the initiator compounds in each reaction vessel with one of r building blocks, said building blocks comprising at least one complementary reactive group, wherein the at least one complementary reactive group is complementary to the reactive group of step (a), under conditions suitable for reaction of the complementary reactive group to form a covalent bond, thereby producing r aliquots comprising compounds consisting of a functional moiety comprising n+1 building blocks operatively linked to the initial oligonucleotide; and
(d) reacting the initial oligonucleotide in each aliquot with one of a set of r distinct incoming oligonucleotides in the presence of an enzyme which catalyzes the ligation of the incoming oligonucleotide corresponding to the building block of step (c) and the initial oligonucleotide, under conditions suitable for enzymatic ligation of the incoming oligonucleotide and the initial oligonucleotide to form an encoding oligonucleotide, and wherein the last of said r distinct incoming oligonucleotides comprises a capping sequence, said capping sequence comprising a nucleotide sequence containing degenerate nucleotides;
thereby producing r aliquots comprising molecules consisting of a functional moiety comprising n+1 building blocks operatively linked to an encoding oligonucleotide which identifies the structure of the functional moiety comprising the n+1 building blocks.

In a still further embodiment, the further method steps comprise the steps of performing a method of synthesizing a library of compounds in solution, wherein the compounds comprise a functional moiety comprising two or more building blocks which is operatively linked to an encoding oligonucleotide which identifies the structure of the functional moiety, said method comprising the further steps of (a) providing a solution of intermediate bi-functional complexes comprising m initiator compounds, where m is an integer of 1 or greater, where the initiator compounds comprise an initial functional moiety comprising n building blocks comprising at least one reactive group, where n is an integer of 1 or greater, which is operatively linked to an initial oligonucleotide corresponding to the n building blocks; wherein the initial functional moiety and the initial oligonucleotide are linked by a linking moiety and wherein the initial oligonucleotide is double-stranded and the linking moiety is covalently coupled to the initial functional moiety and to both strands of the initial oligonucleotide; wherein the linking moiety comprises the structure

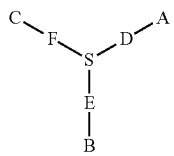

wherein
A is a functional group adapted to bond with the building block;
B is a functional group adapted to bond with the 5'-end of an initial oligonucleotide;
C is a functional group adapted to bond with the 3'-end of an initial oligonucleotide;
S is an atom or scaffold;
D is a chemical structure that connects A to S;
E is a chemical structure that connects B to S;
F is a chemical structure that connects C to S;
(b) dividing the solution of step (a) into r reaction vessels; wherein r is an integer of 2 or greater, thereby producing r aliquots of the solution;
(c) reacting the initiator compounds in each reaction vessel with one of r building blocks, said building blocks comprising at least one complementary reactive group, wherein the at least one complementary reactive group is complementary to the reactive group of step (a), under conditions suitable for reaction of the complementary reactive group to form a covalent bond, thereby producing r aliquots comprising compounds consisting of a functional moiety comprising n+1 building blocks operatively linked to the initial oligonucleotide; and
(d) reacting the initial oligonucleotide in each aliquot with one of a set of r distinct incoming oligonucleotides in the presence of an enzyme which catalyzes the ligation of the incoming oligonucleotide corresponding to the building block of step (c) and the initial oligonucleotide, under conditions suitable for enzymatic ligation of the incoming oligonucleotide and the initial oligonucleotide to form an encoding oligonucleotide, and wherein the last of said r distinct incoming oligonucleotides comprises a capping sequence, said capping sequence comprising a nucleotide sequence containing degenerate nucleotides;
thereby producing r aliquots comprising molecules consisting of a functional moiety comprising n+1 building blocks operatively linked to an encoding oligonucleotide which identifies the structure of the functional moiety comprising the n+1 building blocks.

In yet another embodiment, the further method steps comprise the steps of performing a method for identifying one or more compounds which bind to a biological target, said method comprising:
(A) synthesizing a library of bi-functional complexes comprising different compounds, wherein the compounds comprise a functional moiety comprising two or more building blocks which is operatively linked to an encoding oligonucleotide which identifies the structure of the functional moiety by:
  (i) providing a solution comprising m initiator compounds, wherein m is an integer of 1 or greater, where the initiator compounds consist of an initial functional moiety comprising n building blocks comprising at least one reactive group, where n is an integer of 1 or greater, which is operatively linked to an initial oligonucleotide which identifies the n building blocks; wherein the initial functional moiety and the initial oligonucleotide are linked by a linking moiety and wherein the initial oligonucleotide is double-stranded and the linking moiety is covalently coupled to the initial functional moiety an to both strands of the initial oligonucleotide;
  (ii) dividing the solution of step (A) (i) into r reaction vessels, wherein r is an integer of 2 or greater, thereby producing r aliquots of the solution;
  (iii) reacting the initiator compounds in each reaction vessel with one of r building blocks, said building blocks comprising at least one complementary reactive group, which complementary reactive group is complementary to the reactive group of step (A) (i), under conditions suitable for reaction of the complementary reactive group to form a covalent bond, thereby producing r aliquots comprising compounds consisting of a functional moiety comprising n+1 building blocks operatively linked to the initial oligonucleotide; and
  (iv) reacting the initial oligonucleotide in each aliquot with one of a set of r distinct incoming oligonucleotides corresponding to the building block of step (A) (iii) in the presence of an enzyme which catalyzes the ligation of the incoming oligonucleotide and the initial oligonucleotide, under conditions suitable for enzymatic ligation of the incoming oligonucleotide and the initial oligonucleotide to form an encoding oligonucleotide;
thereby producing r aliquots of molecules consisting of a functional moiety comprising n+1 building blocks operatively linked to an encoding oligonucleotide which identifies the structure of the functional moiety comprising the n+1 building blocks;
(B) contacting the biological target with the library of compounds, or a portion thereof, under conditions suitable for at least one member of the library of compounds to bind to the target;
(C) removing library members that do not bind to the target;
(D) sequencing the encoding oligonucleotides of the at least one member of the library of compounds which bind to the target, and
(E) using the sequence determined in step (D) to determine the structure of the functional moieties of the members of the library of compounds which bind to the biological target, thereby identifying one or more compounds which bind to the biological target.

In a still further embodiment, the further method steps comprise the steps of performing a method for identifying one or more compounds which bind to a biological target, said method comprising:
(A) synthesizing a library of bi-functional complexes comprising different compounds, wherein the compounds comprise a functional moiety comprising two or more building blocks which is operatively linked to an encoding oligonucleotide which identifies the structure of the functional moiety by:
  (i) providing a solution comprising m initiator compounds, wherein m is an integer of 1 or greater, wherein the initiator compounds consist of an initial functional moiety comprising n building blocks comprising at least one reactive group, where n is an integer of 1 or greater, which is operatively linked to an initial oligonucleotide which identifies the n building blocks; wherein the initial functional moiety and the initial oligonucleotide are linked by a linking moiety and wherein the initial oligonucleotide is double-stranded and the linking moiety is covalently coupled to the initial functional moiety an to both strands of the initial oligonucleotide;
  (ii) dividing the solution of step (A) (i) into r reaction vessels, wherein r is an integer of 2 or greater, thereby producing r aliquots of the solution;
  (iii) reacting the initiator compounds in each reaction vessel with one of r building blocks, said building blocks comprising at least one complementary reactive group, which complementary reactive group is complementary to the reactive group of step (A) (i), under conditions suitable for reaction of the complementary reactive group to form a covalent bond, thereby producing r aliquots comprising compounds consisting of a functional moiety comprising n+1 building blocks operatively linked to the initial oligonucleotide; and (iv) reacting the initial oligonucleotide in each aliquot with one of a set of r distinct incoming oligonucleotides corresponding to the building block of step (A) (iii) in the presence of an enzyme which catalyzes the ligation of the incoming oligonucleotide and the initial oligonucleotide, under conditions suitable for enzymatic ligation of the incoming oligonucleotide and the initial oligonucleotide; thereby producing r aliquots of molecules consisting of a functional moiety comprising n+1 building blocks operatively linked to an encoding oligonucleotide which identifies the structure of the functional moiety comprising the n+1 building blocks;

(B) contacting the biological target with the library of compounds, or a portion thereof, under conditions suitable for at least one member of the library of compounds to bind to the target;

(C) removing library members that do not bind to the target;

(D) sequencing the encoding oligonucleotides of the at least one member of the library of compounds which binds to the target, wherein said sequence comprises:

(i) annealing an effective amount of a sequence primer with a polymerase and a predetermined nucleotide triphosphate to yield a sequence product and, if the predetermined nucleotide thiphosphate is incorporated onto a 3' end of said sequence primer, a sequence reaction byproduct; and (ii) identifying the sequencing reaction byproduct, thereby determining the sequence of the encoding oligonucleotide; and (E) using the sequence of the encoding oligonucleotide determined in step (D) to determine the structure of the functional moieties of the members of the library of compounds which bind to the biological target, thereby identifying one or more compounds which bind to the biological target.

Yet more examples of further method steps in accordance with the present invention are disclosed in WO 2006/053571, the contents of which are hereby incorporated in their entirety. In particular, reference is made to the part of the specification presented on pages 36 to 42 under the heading of "Variations and specifications to the general scheme above for the generation of bi-functional molecules".

Further examples of further method steps are disclosed e.g. in US20050158765; US20090062147; US20070042401; and US20070224607, the contents of which are hereby incorporated by reference in their entirety.

Yet another example of further method steps is disclosed in WO 2010/094036, the contents of which are hereby incorporated by reference in their entirety.

A still further example of further method steps is disclosed in WO 2009/077173, the contents of which are hereby incorporated by reference in their entirety.

The contents of the following US patents directed to split-and-mix synthesis methods are hereby incorporated by reference in their entirety: U.S. Pat. Nos. 5,573,905; 5,723,598; and 6,060,596; 5,639,603; 5,665,975; 5,708,153; 5,770,358; 5,789,163; 6,056,926; 6,140,493; 6,143,497; 6,165,717; 6,165,778; and 6,416,949.

In a still further embodiment of the present invention there is provided a method comprising further steps for the synthesis of a bi-functional complex comprising a molecule and a single stranded oligonucleotide identifier attached to the molecule, said method comprising the further steps of i) providing a display oligonucleotide attached to
   a) one or more chemical reaction site(s) comprising one or more reactive groups, and
   b) one or more priming site(s) for enzymatic addition of a oligonucleotide tag,
   wherein said display oligonucleotide is further attached to a solid support, ii) providing a first reactive compound building block comprising one or more chemical entities and one or more reactive groups capable of reacting with
   c) the one or more chemical reaction site(s) of the display oligonucleotide, and/or
   d) one or more reactive groups of at least a first further reactive compound building block comprising one or more chemical entities, wherein said first further reactive compound building block is provided simultaneously or sequentially in any order with the first reactive compound building block, iii) providing a first oligonucleotide tag capable of hybridising to part of a first oligonucleotide anti-tag, wherein the first oligonucleotide tag identifies the first reactive compound building block and, optionally, the further first reactive compound building block, iv) providing a first oligonucleotide anti-tag capable of hybridising to at least part of the first oligonucleotide tag provided in step iii) and to at least part of the display oligonucleotide provided in step i), v) reacting the first reactive compound building block provided in step ii) with c) the one or more chemical reaction site(s) of the display oligonucleotide and/or with d) the one or more reactive groups of the first further reactive compound building block comprising one or more chemical entities,
   wherein the reaction of complementary reactive groups result in the formation of a covalent bond, and
   wherein one or more reactive group reactions of step v) result in the formation of one or more covalent bond(s) between the one or more chemical reaction site(s) of the display oligo and at least one chemical entity of at least one reactive compound building block selected from the group consisting of the first reactive compound building block and the further first reactive compound building block, vi) hybridising the oligonucleotide anti-tag to the display oligonucleotide and to the first oligonucleotide tag,
   wherein method steps v) and vi) are simultaneous or sequential in any order, vii) enzymatically ligating the display oligonucleotide and the first oligonucleotide tag, viii) providing a second reactive compound building block comprising one or more chemical entities and one or more reactive groups capable of reacting with
   c) the one or more chemical reaction site(s) of the display oligonucleotide, and/or
   d) one or more reactive groups of one or more reactive compound building block(s) having reacted in a previous synthesis round, and/or
   e) one or more reactive groups of a second further reactive compound building block comprising one or more chemical entities, wherein said second further reactive compound building block is provided simultaneously or sequentially in any order with the second reactive compound building block,
   wherein the second reactive compound building block is provided in step viii) and reacted in the following step ix) in the absence of a second oligonucleotide tag identifying the second reactive compound building block, ix) reacting the second reactive compound building block provided in step viii) with c) the one or more chemical reaction site(s) of the display oligonucleotide and/or d) one or more reactive groups of one or more reactive compound building block(s) having reacted in a previous synthesis round and/or e) one or more reactive groups of a further second reactive compound building block comprising one or more chemical entities,
wherein the reaction of complementary reactive groups result in the formation of a covalent bond, and
wherein one or more reactive group reactions of step ix) result in f) the formation of one or more covalent bond(s) between the one or more chemical reaction site(s) and at least one chemical entity of at least one reactive compound building block selected from the group consisting of the second reactive compound building block and the further second reactive compound building block, and/or g) the formation of one or more covalent bond(s) between a reactive compound building block having reacted in a previous synthesis round and at least one chemical entity of at least one reactive compound building block selected from the group consisting of the second reactive compound building block and the further second reactive compound building block,
wherein the reaction product is preferably in the form of a small, scaffolded molecule, or a precursor or intermediate small, scaffolded molecule to be further reacted in subsequent reaction cycles, x) cleaving the reaction product obtained in step ix), in the form of an intermediate bi-functional complex, from the solid support, xi) providing a second oligonucleotide tag capable of hybridising to part of a second oligonucleotide anti-tag, wherein the second oligonucleotide tag identifies the second reactive compound building block and, optionally, the further second reactive compound building block, xii) providing a second oligonucleotide anti-tag capable of hybridising to part of the first oligonucleotide tag provided in step iii) and to part of the second oligonucleotide tag provided in step xi),
wherein method step ix) is carried out prior to carrying out method step x),
wherein method step x) is carried out prior to carrying out method steps xi) and xii), xiii) hybridising the oligonucleotide anti-tag to the first oligonucleotide tag and the second oligonucleotide tag, xiv) enzymatically ligating the first and second oligonucleotide tags in the absence of ligation the first and second anti-tag oligonucleotides, and optionally xv) displacing unligated anti-tags from the bi-functional complex comprising a molecule and a single stranded oligonucleotide identifier comprising oligonucleotide tags identifying the reactive compound building blocks which participated in the synthesis of the molecule and converting the single stranded oligonucleotide identifier, by nucleotide extension(s) of a primer, to a double stranded oligonucleotide identifier.

In a still further aspect of the present invention there is provided a method for synthesising a library of different bi-functional complexes according to the present invention, wherein the lack of a covalent link between a reactive compound building block and an oligonucleotide tag during library synthesis means that the library can be produced by a split-and-mix strategy without using a pre-made template. In a first step a display oligonucleotide or a nascent bi-functional complex is dispensed in separate compartments and subsequently exposed to a different reactive compound building block in each or at least the majority of the compartments. The reactive compound building block reacts in each compartment with at least one reactive group of the chemical reaction site. Apart from the initial oligonucleotide tag which is chemically synthesised directly on the solid support, oligonucleotide tags identifying respective reactive compound building blocks are added by enzymatic action, such as enzymatic ligation, at the priming site.

There is also provided a method for partitioning a library or composition of different bi-functional complexes, said partitioning resulting in the selection of bi-functional complexes comprising molecules having one or more desirable characteristics. The partitioning of bi-functional complexes can occur as a result of the differential affinity of the molecule(s) of different bi-functional complexes for the same or different targets, such as the targets disclosed herein. Alternatively, and/or in combination with the above, partitioning of bi-functional complexes can occur based on oligonucleotide tag features, such as e.g. oligonucleotide tag nucleotide sequences and/or physical properties capable of distinguishing different oligonucleotide tags and/or identifier oligonucleotides from each other.

Whereas an initially generated library is often termed a "naïve library", the library obtained after partitioning is often termed an "intelligent" or "enriched" library. The partitioning can be carried out once or more than once using the same or different partitioning parameters, such as binding affinity to a target compound under predetermined assaying conditions.

In a further aspect there is provided a pharmaceutical composition comprising the molecule, or a variant of the molecule, of the bi-functional complex—wherein preferably the molecule is not linked to the identifier oligonucleotide of the bi-functional complex. The terms "molecule", "compound", "chemical compound", "reaction product", "bioactive agent" and "bioactive species" are used interchangeably herein when referring to a product obtained by the methods of the present invention, or a variant of such a product obtained e.g. when a "lead compound" or "drug lead" is being optimised for pharmaceutical uses. A "bioactive agent" or a "bioactive species" is typically a molecule which exerts a biologically relevant activity, such as e.g. a biologically relevant binding affinity for a target compound.

There is also provided the use of a bi-functional complex according to the invention in the manufacture of a medicament for the treatment of a clinical indication in an individual in need thereof.

Definitions

α-peptide: Peptide comprising or essentially consisting of at least two α-amino acids linked to one another by a linker including a peptide bond.

Amino acid: Entity comprising an amino terminal part ($NH_2$) and a carboxy terminal part (COOH) separated by a central part comprising a carbon atom, or a chain of carbon atoms, comprising at least one side chain or functional group. $NH_2$ refers to the amino group present at the amino terminal end of an amino acid or peptide, and COOH refers to the carboxy group present at the carboxy terminal end of an amino acid or peptide. The generic term amino acid comprises both natural and non-natural amino acids. Natural amino acids of standard nomenclature as listed in J. Biol. Chem., 243:3552-59 (1969) and adopted in 37 C.F.R., section 1.822(b) (2) belong to the group of amino acids listed herein below. Non-natural amino acids are those not listed in the below table. Examples of non-natural amino acids are those listed e.g. in 37 C.F.R. section 1.822(b) (4), all of which are incorporated herein by reference. Further examples of non-natural amino acids are listed herein below. Amino acid residues described herein can be in the "D" or "L" isomeric form.

| Symbols | | |
|---|---|---|
| 1-Letter | 3-Letter | Amino acid |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

Amino acid precursor: Moiety capable of generating an amino acid residue following incorporation of the precursor into a peptide.

Amplifying: Any process or combination of process steps that increases the number of copies of an identifier oligonucleotide. Amplification of identifier oligonucleotides can be carried out by any state of the art method including, but not limited to, a polymerase chain reaction to increase the copy number of each identifier oligonucleotide by using the identifier oligonucleotide(s) as template(s) for synthesising additional copies of the identifier oligonucleotides. Any amplification reaction or combination of such reactions known in the art can be used as appropriate as readily recognized by those skilled in the art. Accordingly, identifier oligonucleotides can be amplified using a polymerase chain reaction (PCR), a ligase chain reaction (LCR), by in vivo amplification of identifier oligonucleotides cloned in DNA chromosomal or extra-chromosomal elements including vectors and plasmids, and the like. The amplification method should preferably result in the proportions of the amplified mixture of identifier oligonucleotides being essentially representative of the proportions of identifier oligonucleotides of different sequences in a mixture prior to said amplification.

Base: Nitrogeneous base moiety of a natural or non-natural nucleotide, or a derivative of such a nucleotide comprising alternative sugar or phosphate moieties. Used interchangeably with nucleobase. Base moieties include any moiety that is different from a naturally occurring moiety and capable of complementing one or more bases of the opposite nucleotide strand of a double helix.

Bi-functional complex: Complex comprising an identifier oligonucleotide, one or more linker(s), and a molecule part synthesised by reacting a plurality of reactive compound building block(s). An "intermediate bi-functional complex" is a complex wherein the chemical reaction site(s) will undergo further reactions with reactive groups of reactive compound building blocks and/or with protective groups in order to synthesise a final bi-functional complex.

Binding region: Region on a string of consecutive nucleotides to which an enzyme can bind, e.g. when ligating different oligonucleotides (e.g. in case of a ligase) or prior to a fill-in reaction (e.g. in case of a polymerase).

Catalyst: Moiety acting on a starting compound or a set of starting compounds and speeding up chemical reactions involving such compound(s).

Chemical reaction site: Site of a intermediate bi-functional complex reacted with at least one reactive group or reactive compound building block during the synthesis of a molecule.

Cleavable linker: Residue or bond capable of being cleaved under predetermined conditions.

Cleaving: Breaking a chemical bond. The bond can be a covalent bond or a non-covalent bond.

Complementary binding partners: Binding partners capable of reacting with each other through complementary reactive groups.

Complementary reactive groups: Reactive groups capable of reacting with each other.

Contacting: Bringing, e.g. corresponding reactive groups or corresponding binding partners or hybridization partners, into reactive contact with each other. The reactive contact is evident from a reaction between the partners, or the formation of a bond, or hybridization, between the partners.

Cycle of reaction: The methods of the present invention employ split-n-mix strategies for molecule synthesis. A reaction cycle involves a reaction of a reactive group or reactive compound building block with another reactive group or reactive compound building block or with the chemical reaction site and the reaction of an oligonucleotide tag with another oligonucleotide tag or with the oligonucleotide tag addition site. In other words, a reaction cycle involves both a molecule specific reaction and an oligonucleotide tag specific reaction.

Enzyme: Any polypeptide capable of speeding up chemical reactions. Enzymes act as catalysts for a single reaction and convert a starting compound or a specific set of starting compounds into specific products. Examples are ligases and polymerases.

Hybridisation: The ability of complementary nucleotides to form an association through hydrogen bonding.

Identifier oligonucleotide: The identifier oligonucleotide can be single stranded or, in an initial state, at least partly hybridised to one or more discrete complementary tags. The oligonucleotide identifier(s) can be linear or branched. The nucleotides of the identifier oligonucleotide can be natural and/or non-natural nucleotides, including nucleotide derivatives. The length can vary as long as the identifier is long enough (i.e. contains a sufficient number of nucleotides) to identify the molecule part of the bi-functional complex to which the identifier oligonucleotide is linked, or the reactive compound building block having participated in the synthesis of the molecule. In one embodiment, the identifier oligonucleotide is double stranded and the individual strands are covalently linked to each other.

Interacting: Used interchangeably with contacting. Bringing species, e.g. corresponding binding partners, into reactive contact with each other. The reaction can be mediated by recognition groups forming corresponding binding partners by means of covalent or non-covalent bonds.

Library: A composition of different moieties, such as small molecules or bi-functional complexes comprising different small molecules each linked to a specific identifier oligonucleotide identifying the small molecule.

Linker: A residue or chemical bond separating at least two species. The species can be retained at an essentially fixed distance, or the linker can be flexible and allow the species some freedom of movement in relation to each other. The link can be a covalent bond or a non-covalent bond.

Molecule: A chemical reaction site, such as optionally a scaffold, which has reacted with one or more reactive groups. The molecule can form part of a bi-functional complex further comprising an identifier oligonucleotide capable of identifying the molecule or the reactive compound building blocks which have reacted in the method for synthesising the molecule. The molecule is also termed a "final reactive compound building block". The molecule part of the bi-functional complex can be linked covalently to the oligonucleotide tag addition site of the bi-functional complex and/or to a single stranded identifier oligonucleotide comprising a plurality of covalently linked oligonucleotide tags or via a linker. A "molecule" is any reactive compound building block, or part thereof, selected or designed to be part of a synthetic precursor to lead candidate or drug candidate or the final molecule following all reactions combining chemical building blocks. The molecule comprises one, two, or three or more chemical substituents, also called "reactive compound building blocks". A molecule preferably optionally exhibits properties of desirable lead compounds, including, for example, a low molecular complexity (low number of hydrogen bond donors and acceptors, low number of rotatable bonds, and low molecular weight), and low hydrophobicity. When a molecule is a small molecule, one of ordinary skill in the art may further develop or elaborate the small molecule into a lead or drug candidate by modifying the molecule, either at the reactive compound building blocks or at the core structure, to have desirable drug characteristics, including, for example, characteristics meeting the Lipinski rule of five. Preferred molecule properties optionally include lead-like properties and are known to those of ordinary skill in the art and are described in Teague, S. J., et al., Agnew. Chem. Int. Ed. 38:3743-3748, 1999; Oprea, T. I., et al., J. Chem. Inf. Comput. Sci. 41:1308-1315, 2001; and Hann, M. M. et al., J. Chem. Inf. Comput. Sci. 41:856-864, 2001. Desirable small molecules include, but are not limited to, for example, molecules having some or all of the following general properties: MW of preferably less than about 1000 Dalton, MW of preferably less than about 500, MW of preferably less than about 350, MW of preferably less than about 300, or MW of preferably less than about 250, a c log P of preferably about −1 to 5, preferably less than about 5 rings, and an Log P of preferably less than about 4 or of preferably less than about 3. Other general properties may include less than about 15, such as 12, for example 10 nonterminal single bonds, less than about 10, such as 8, for example 6 hydrogen bond donors, and less than about 10, such as 8, for example 6 hydrogen bond acceptors. Thus, molecules are optionally designed so that more complexity and weight can be added during development and building out of the compound into a lead candidate, while maintaining the general properties. Molecules may comprise scaffolds comprising cyclic or non-cyclic structures. Examples of non-cyclic scaffolds, include, but are not limited to, hypusine, putrescine, gamma-aminobutyric acid, and 2-hydroxyputresine. Generally, the scaffold portion of a molecule may comprise 1) a cyclic structure, including any of the cyclic structures described herein, with 2) one or more of the reactive compound building blocks disclosed herein.

Intermediate bi-functional complex: Also referred to as a growing complex; specifies an initial or intermediate complex to be processed according to the methods of the present invention. An intermediate complex designates an initial complex that has been subjected to one or more rounds of reactive compound building block reaction and oligonucleotide tag addition.

Natural nucleotide: Any of the four deoxyribonucleotides, dA, dG, dT, and dC (constituents of DNA) and the four ribonucleotides, A, G, U, and C (constituents of RNA) are natural nucleotides. Each natural nucleotide comprises a sugar moiety (ribose or deoxyribose), a phosphate moiety, and a natural/standard base moiety. Natural nucleotides bind to complementary nucleotides according to well-known base pairing rules, such as e.g. Watson & Crick type base pairing, where adenine (A) pairs with thymine (T) or uracil (U); and where guanine (G) pairs with cytosine (C), wherein corresponding base-pairs are part of complementary, anti-parallel nucleotide strands. The base pairing results in a specific hybridization between predetermined and complementary nucleotides. The base pairing is the basis by which enzymes are able to catalyze the synthesis of an oligonucleotide complementary to the template oligonucleotide. In this synthesis, building blocks (normally the triphosphates of ribo or deoxyribo derivatives of A, T, U, C, or G) are directed by a template oligonucleotide to form a complementary oligonucleotide with the correct, complementary sequence. The recognition of an oligonucleotide sequence by its complementary sequence is mediated by corresponding and interacting bases forming base pairs. In nature, the specific interactions leading to base pairing are governed by the size of the bases and the pattern of hydrogen bond donors and acceptors of the bases. A large purine base (A or G) pairs with a small pyrimidine base (T, U or C). Additionally, base pair recognition between bases is influenced by hydrogen bonds formed between the bases. In the geometry of the Watson-Crick base pair, a six membered ring (a pyrimidine in natural oligonucleotides) is juxtaposed to a ring system composed of a fused, six membered ring and a five membered ring (a purine in natural oligonucleotides), with a middle hydrogen bond linking two ring atoms, and hydrogen bonds on either side joining functional groups appended to each of the rings, with donor groups paired with acceptor groups.

Non-natural base pairing: Base pairing among non-natural nucleotides, or among a natural nucleotide and a non-natural nucleotide. Examples are described in U.S. Pat. No. 6,037,120, wherein eight non-standard nucleotides are described, and wherein the natural base has been replaced by a non-natural base. As is the case for natural nucleotides, the non-natural base pairs involve a monocyclic, six membered ring pairing with a fused, bicyclic heterocyclic ring system composed of a five member ring fused with a six membered ring. However, the patterns of hydrogen bonds through which the base pairing is established are different from those found in the natural AT, AU and GC base pairs. In this expanded set of base pairs obeying the Watson-Crick hydrogen-bonding rules, A pairs with T (or U), G pairs with C, iso-C pairs with iso-G, and K pairs with X, H pairs with J, and M pairs with N. Nucleobases capable of base pairing without obeying Watson-Crick hydrogen-bonding rules have also been described (Berger et al., 2000, Nucleic Acids Research, 28, pp. 2911-2914).

Non-natural nucleotide: Any nucleotide not falling within the above definition of a natural nucleotide.

Nucleotide: The term nucleotides as used herein refers to both natural nucleotides and non-natural nucleotides. Nucleotides can differ from natural nucleotides by having a different phosphate moiety and/or a different sugar moiety and/or a different base moiety from the natural nucleotide. Accordingly, nucleotides can form part of an identifier oligonucleotide when they are linked to each other by a natural bond in the form of a phosphodiester bond, or a non-natural bond, such as e.g. a peptide bond as in the case of PNA (peptide nucleic acids).

Nucleotide derivative: Nucleotide further comprising an appended molecular entity. The nucleotides can be derivatized on the bases and/or the ribose/deoxyribose unit and/or the phosphate. Preferred sites of derivatization on the bases include the 8-position of adenine, the 5-position of uracil, the 5- or 6-position of cytosine, and the 7-position of guanine. The nucleotide-analogs described below can be derivatized at the corresponding positions (Benner, U.S. Pat. No. 6,037,120). Other sites of derivatization can be used, as long as the derivatization does not disrupt base pairing specificity. Preferred sites of derivatization on the ribose or deoxyribose moieties are the 5', 4' or 2' positions. In certain cases it can be desirable to stabilize the nucleic acids towards degradation, and it can be advantageous to use 2'-modified nucleotides (U.S. Pat. No. 5,958,691). Again, other sites can be employed, as long as the base pairing specificity is not disrupted. Finally, the phosphates can be derivatized. Preferred derivatizations are phosphorothiote. Nucleotide analogs (as described below) can be derivatized similarly to nucleotides. It is clear that the various types of modifications mentioned herein above, including i) derivatization and ii) substitution of the natural bases or natural backbone structures with non-natural bases and alternative, non-natural backbone structures, respectively, can be applied once or more than once within the same nucleic acid molecule.

Oligonucleotide: The term oligonucleotide comprises oligonucleotides of both natural and/or non-natural nucleotides, including any combination thereof. The natural and/or non-natural nucleotides can be linked by natural phosphodiester bonds or by non-natural bonds. Oligonucleotides have at least 2 nucleotides, such as 3 or more nucleotides. Oligonucleotides can be comprised of either one or two strands.

Oligonucleotide tag: Part of an identifier oligonucleotide. The oligonucleotide tag can comprise 1 or several nucleotides in a highly specific arrangement or they may be arranged and selected randomly. The oligonucleotide tag also comprises 1 or several complete or partial codons, each codon being a triplet of three nucleotides. The nucleotide comprising the oligonucleotide tags may be synthesised either directly on the solid support or on its linker or attached to the solid support or on its linker as oligonucleotides. An oligonucleotide tag is a string of consecutive nucleotides capable of identifying a particular reactive group or reactive compound building block having reacted during the method of synthesising the intermediate complex to which the identifier oligonucleotide is linked. An oligonucleotide tag can be an element of an identifier, such as an identifier oligonucleotide, comprising one or more recognition group(s) capable of recognising one or more predetermined, complementary recognition group(s). The recognition can be generated by and/or result in the formation of a covalent bond or a non-covalent bond between corresponding pairs of recognition groups capable of interacting with one another. The recognition groups can be nucleobases in a strand of consecutive nucleotides, such as an oligonucleotide.

Oligomer: Molecule comprising three or more monomers that can be identical, of the same type, or different monomers. Oligomers can be homooligomers comprising a plurality of identical monomers, oligomers comprising different monomers of the same type, or herooligomers comprising different types of monomers, wherein each type of monomer can be identical or different.

Partitioning: Process whereby molecules, or complexes comprising such molecules linked to an identifier oligonucleotide, are preferentially bound to a target molecule and separated from molecules, or complexes comprising such molecules linked to an identifier oligonucleotide, that do not have an affinity for—and is consequently not bound to—such target molecules. Partitioning can be accomplished by various methods known in the art. The only requirement is a means for separating molecules bound to a target molecule from molecules not bound to target molecules under the same conditions. The choice of partitioning method will depend on properties of the target and of the synthesised molecule and can be made according to principles and properties known to those of ordinary skill in the art.

Peptide: Plurality of covalently linked amino acid residues defining a sequence and linked by amide bonds. The term is used analogously with oligopeptide and polypeptide. The amino acids can be both natural amino acids and non-natural amino acids, including any combination thereof. The natural and/or non-natural amino acids can be linked by peptide bonds or by non-peptide bonds. The term peptide also embraces post-translational modifications introduced by chemical or enzyme-catalyzed reactions, as are known in the art. Such post-translational modifications can be introduced prior to partitioning, if desired. Amino acids as specified herein will preferentially be in the L-stereoisomeric form. Amino acid analogs can be employed instead of the 20 naturally-occurring amino acids. Several such analogs are known, including fluorophenylalanine, norleucine, azetidine-2-carboxylic acid, S-aminoethyl cysteine, 4-methyl tryptophan and the like.

Plurality: At least two, for example from 2 to $10^{18}$, such as from 2 to 100, for example from 2 to 50, such as from 2 to 20, for example from 2 to 10, such as from 2 to 5.

Polymer: Molecules characterised by a sequence of covalently linked residues each comprising a functional group, including H. Polymers according to the invention comprise at least two residues.

Precursor entity: Reactive compound building block comprising a precursor moiety which is cleaved or modified when the reactive compound building block is reacted with another reactive compound building block.

Oligonucleotide tag addition site: Site on a third intermediate bi-functional complex or a intermediate bi-functional complex to which at least on an oligonucleotide tag is added chemically or enzymatically or otherwise during the synthesis of the molecule. At least one oligonucleotide tag is added enzymatically.

Protective group: Part of a molecule that discloses the feature of protecting any other selective reactive centre of any group comprised in solid support, linker, oligonucleotide tags, reactive group or reactive compound building block during addition of new reactive compound building blocks or nucleotides. Protective groups has the ability to be attached to any selective feature of the groups above and further be selectively detached when required from the specified group.

Reactive compound building block: Functional, chemical group which, when reacted, becomes covalently or non-covalently attached to a site of a bi-functional complex, such as a chemical reaction site, such as a scaffold. One or more reactive groups can be e.g. reacted, substituted or added. Reactive compound building blocks are generally involved in covalent bond forming reactions and the reaction of reactive compound building blocks results in the synthesis of the molecule part of a bi-functional complex through the reaction of different sets of complementary reactive groups. Reactive compound building blocks can be modified or substituted partly or completely by other reactive compound building blocks or derived substituents using one step or two step chemical processes. Protection and de-protection steps may also be required. In an embodiment of the methods of the invention, this modification can be done independently at each reactive compound building block, without the need to add protecting groups at the other reactive compound building blocks. Reactive compound building blocks may comprise substituents capable of anomalous scattering. The reactive compound building block can comprise or be linked to a reactive group capable of reacting with reactive groups of other reactive compound building blocks. Reactive compound building blocks that can be used in various embodiments of the present invention include, but are not limited to: H, benzyl halides, benzyl alcohols, allyl halides, allyl alcohols, carboxylic acids, aryl amines, heteroaryl amines, benzyl amines, aryl alkyl amines, alkyl aminos, phenols, aryl halides, heteroaryl halides, heteroaryl chlorides, aryl aldehydes, heteroaryl aldehydes, aryl alkyl aldehydes, alkyl aldehydes, aryls, heteroaryls, alkyls, aryl alkyls, ketones, arylthiols, heteroaryl thiols, ureas, imides, aryl boronic acids, esters, carbamates, tert-butyl carbamates, nitros, aryl methyls, heteroaryl methyls, vinyl methyls, 2- or 2,2-substituted vinyls, 2-substituted alkynes, acyl halides, aryl halides, alkyl halides, cycloalkyl halides, sulfonyl halides, carboxylic anhydrides, epoxides, and sulfonic acids. In other embodiments, the reactive compound building blocks can e.g. be benzyl bromides, benzyl alcohols, allyl bromides, allyl alcohols, carboxylic acids, aryl amines, heteroaryl amines, benzyl amines, aryl alkyl amines, phenols, aryl bromides, heteroaryl bromides, heteroaryl chlorides, aryl aldehydes, heteroaryl aldehydes, aryl alkyl aldehydes, ketones, arylthiols, heteroaryl thiols, ureas, imides, and aryl boronic acids. Halide includes iodide, bromide, fluoride, and chloride. Halide can give raise to anomalous scattering, such as, for example, bromide or iodide. By convention, a reactive compound building block can be considered either a "direct" reactive compound building block or a "latent" reactive compound building block, with some reactive compound building blocks having the capacity to function as either. A direct reactive compound building block is a functional group or moiety that can react directly with another functional group or moiety without prior modification or that can be rendered reactive by the addition of reagents and/or catalysts typically, but not necessarily, in a single-pot reaction. Examples of a direct reactive compound building block include, but are not limited to: the Br in a benzyl bromide, carboxylic acid, amine, phenol, the Br in an aryl bromide, aldehyde, thiol, boronic acid or ester, and the like. A latent reactive compound building block is a functional group or moiety that requires prior modification, either in a separate step after which it may or may not be isolated, or generated in situ to afford a more reactive species (i.e., obtaining a direct reactive compound building block). A latent reactive compound building block may also comprise a moiety that by virtue of its proximity or connectivity to a functional group or other moiety is rendered reactive. Examples of a latent reactive compound building block include, but are not limited to: nitro (which can be reduced to an amine), aryl methyl (which can be converted to aryl bromomethyl or to aryl carboxylic acid), olefin (which can undergo oxidative cleavage to afford an epoxide, an aldehyde or carboxylic acid), and the like. The adoption of the above convention serves to illustrate the scope of chemical moieties regarded as reactive compound building blocks within the present invention. Additional reactive compound building blocks are within the scope of this invention and are evident to those trained in the art and having access to the chemical literature.

Reactive group: Part of e.g. a reactive compound building block and linked to the reactive compound building block of the reactive compound building block. Tags also have reactive groups. Complementary reactive groups brought into reactive contact with each other are capable of forming a chemical bond linking two binding partners. Reaction of reactive compound building block comprising complementary reactive groups results in the formation of a chemical bond between the reactive groups or the reactive compound building blocks of each reactive compound building block.

Recognition group: Part of an oligonucleotide tag and involved in the recognition of complementary recognitions groups of e.g. a complementary oligonucleotide. Preferred recognition groups are natural and non-natural nitrogeneous bases of a natural or non-natural nucleotide.

Recombine: A recombination process recombines two or more sequences by a process, the product of which is a sequence comprising sequences from each of the two or more sequences. When involving nucleotides, the recombination involves an exchange of nucleotide sequences between two or more nucleotide molecules at sites of identical nucleotide sequences, or at sites of nucleotide sequences that are not identical, in which case the recombination can occur randomly. One type of recombination among nucleotide sequences is referred to in the art as gene shuffling.

Residue: A molecule comprises a plurality of linked residues, wherein each residue comprises a functional group. A polymer comprises a sequence of covalently linked residues, wherein each residue comprises a functional group.

Ribose derivative: Ribose moiety forming part of a nucleoside capable of being enzymatically incorporated into a template or complementing template. Examples include e.g. derivatives distinguishing the ribose derivative from the riboses of natural ribonucleosides, including adenosine (A), guanosine (G), uridine (U) and cytidine (C). Further examples of ribose derivatives are described in e.g. U.S. Pat. No. 5,786,461. The term covers derivatives of deoxyriboses, and analogously with the above-mentioned disclosure, derivatives in this case distinguishes the deoxyribose derivative from the deoxyriboses of natural deoxyribonucleosides, including deoxyadenosine (dA), deoxyguanosine (dG), deoxythymidine (dT) and deoxycytidine (dC).

Scaffold: Structural entity comprising one or more reactive groups, preferably more reactive groups, with which one or more reactive groups can react. A "scaffold" or "core scaffold" is a molecule that generally does not include reactive compound building blocks, as described herein, but may include internal reactive compound building blocks, such as atoms that are part of one of the central rings. A molecule comprises a scaffold and at least one reactive compound building block. Non-limiting examples of a scaffold include any cyclic or non-cyclic structure, such as, but not limited to, those disclosed herein. In some embodiments of the invention, a scaffold is the portion of a molecule lacking one or more reactive compound building blocks. Compounds of the invention include those comprising a scaffold and one or more reactive compound building blocks. A scaffold preferably exhibits properties of desirable lead compounds, including, for example, a low molecular complexity (low number of hydrogen bond donors and acceptors, low number of rotatable bonds, and low molecular weight), and low hydrophobicity. Because a scaffold is small, one of ordinary skill in the art may further develop or elaborate the core into a lead or drug candidate by modifying the core to have desirable drug characteristics, including, for example, by meeting the Lipinski rule of five. Preferred core properties include lead-like properties and are known to those of ordinary skill in the art and are described in Teague, S. J., et al., Agnew. Chem. Int. Ed. 38:3743-3748, 1999; Oprea, T. I., et al., J. Chem. Inf. Comput. Sci. 41:1308-1315, 2001; and Hann, M. M. et al., J. Chem. Inf. Comput. Sci. 41:856-864, 2001. Thus, scaffolds are designed so that more complexity and weight can be added during development and building out of the molecule into a lead candidate, while maintaining the general properties.

Selectively cleavable linker: Selectively cleavable linkers are not cleavable under conditions wherein cleavable linkers are cleaved.

Small molecule: a small molecule according to the present invention is a low molecular weight organic compound which is not an oligomer or a polymer, such as a natural or non-natural oligopeptide or polypeptide produced by ribosomal translation, or a nucleotide or nucleotide sequence.

Solid support: A solid support can be comprised of only the solid support or a solid support with a linker. The solid support, with and without linker, can be solid or semi-solid to which oligonucleotide tags or reactive compound building blocks can be attached. Examples of supports include planar surfaces including silicon wafers as well as beads or controlled poreglas (CPG) of various shape including spherical, tetragonal, cubic, octahedronal, dodecahedronal and icosahedronal just to mention a few.

Specific recognition: The specific interaction of e.g. a nucleotide of an oligonucleotide tag with preferably one predetermined nucleotide of an complementary tag constitutes a specific recognition. A specific recognition occurs when the affinity of an oligonucleotide tag nucleotide recognition group for an complementary tag nucleotide recognition group results in the formation of predominantly only one type of corresponding binding partners. Simple mismatch incorporation does not exclude a specific recognition of corresponding binding partners.

Subunit: Monomer of an oligonucleotide tag, such as e.g. a nucleotide.

Support: Solid or semi-solid member to which e.g. oligonucleotide tags can be attached. Examples of supports includes planar surfaces including silicon wafers as well as beads.

Target molecule: Any compound of interest for which a templated molecule in the form of a ligand is desired. A target molecule can be a protein, fusion protein, peptide, enzyme, nucleic acid, nucleic acid binding protein, carbohydrate, polysaccharide, glycoprotein, hormone, receptor, receptor ligand, cell membrane component, antigen, antibody, virus, virus component, substrate, metabolite, transition state analog, cofactor, inhibitor, drug, controlled substance, dye, nutrient, growth factor, toxin, lipid, glycolipid, etc., without limitation.

Variant: Molecule exhibiting a certain degree of identity or homology—either physically or functionally—to a predetermined molecule.

Chemical Definitions

The term "hydrido" denotes a single hydrogen atom (H). This hydrido radical may be attached, for example, to an oxygen atom to form a hydroxyl radical or two hydrido radicals may be attached to a carbon atom to form a methylene (—$CH_2$—) radical.

Where the term "alkyl" is used, either alone or within other terms such as "haloalkyl" and "alkylsulfonyl", it embraces linear or branched radicals having one to about twenty carbon atoms or, preferably, one to about twelve carbon atoms. Preferred alkyl radicals are "lower alkyl" radicals having one to about ten carbon atoms, such as lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. Branched chain isomers of straight chain alkyl groups, include, but are not limited to, the following which are provided by way of example: —$CH(CH_3)_2$, —$CH(CH_3)(CH_2CH_3)$, —$CH(CH_2CH_3)_2$, —$C(CH_3)_3$, —$C(CH_2CH_3)_3$, —$CH_2CH(CH_3)_2$, —$CH_2CH(CH_3)(CH_2CH_3)$, —$CH_2CH(CH_2CH_3)_2$, —$CH_2C(CH_3)_3$, —$CH_2C(CH_2CH_3)_3$, —$CH(CH_3)CH(CH_3)(CH_2CH_3)$, —$CH_2CH_2CH(CH_3)_2$, —$CH_2CH_2CH(CH_3)(CH_2CH_3)$, —$CH_2CH_2CH(CH_2CH_3)_2$, —$CH_2CH_2C(CH_3)_3$, —$CH_2CH_2C(CH_2CH_3)_3$, —$CH(CH_3)CH_2CH(CH_3)_2$, —$CH(CH_3)CH(CH_3)CH(CH_3)CH(CH_3)_2$, —$CH(CH_2CH_3)CH(CH_3)CH(CH_3)(CH_2CH_3)$, and others. When substituted, the "alkyl" or "lower alkyl" can comprise one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl.

The term "alkenyl" embraces linear or branched radicals having at least one carbon-carbon double bond of two to about twenty carbon atoms, such as from two to about twelve carbon atoms, for example from two to about eight carbon atoms. Preferred alkyl radicals are "lower alkenyl" radicals having two to about six carbon atoms. Examples of such radicals include ethenyl, n-propenyl, butenyl, and the like. When substituted, the "alkenyl" or "lower alkenyl" can comprise one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl.

The term "halo" means halogens such as fluorine, chlorine, bromine or iodine atoms. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" preferably embraces radicals having 1-6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The "haloalkyl" or "lower haloalkyl" can optionally be further substituted. When further substituted, the "haloalkyl" or "lower haloalkyl" can further comprise one or more radicals selected from the group of radicals consisting of hydroxy, primary amine, carboxy, acid chloride, sulfonyl chloride, sulphonate, nitro, cyano, isothiocyanate, phosphonyl, sulphonyl, sulfamyl, carbonyl, and thiolyl.

The term "hydroxyalkyl" embraces linear or branched alkyl radicals having from one to about ten carbon atoms any one of which may be substituted with one or more hydroxyl radicals. Hydroxyalkyl radicals can be "lower hydroxyalkyl" radicals preferably having one to six carbon atoms and one or more hydroxyl radicals. Examples of such radicals include hydroxymethyl, hydroxyethyl, hydroxypropyl, hydroxybutyl and hydroxyhexyl. The "hydroxyalkyl" or "lower hydroxyalkyl" can optionally be further substituted. When further substituted, the "hydroxyalkyl" or "lower hydroxyalkyl" can further comprise one or more radicals selected from the group of radicals consisting of primary amine, carboxy, acid chloride, sulfonyl chloride, sulphonate, nitro, cyano, isothiocyanate, halogen, phosphonyl, sulphonyl, sulfamyl, carbonyl, and thiolyl.

The terms "alkoxy" and "alkoxyalkyl" embrace linear or branched oxy-containing radicals each having alkyl portions of one to about ten carbon atoms, such as methoxy radical. Alkoxy radicals can be "lower alkoxy" radicals having one to six carbon atoms. Examples of such radicals include methoxy, ethoxy, propoxy, butoxy and tert-butoxy. The term "alkoxyalkyl" also embraces alkyl radicals having two or more alkoxy radicals attached to the alkyl radical, that is, to form monoalkoxyalkyl and dialkoxyalkyl radicals. Alkoxyalkyl radicals can be "lower alkoxyalkyl" radicals having one to six carbon atoms and one or two alkoxy radicals. Examples of such radicals include methoxymethyl, methoxyethyl, ethoxyethyl, methoxybutyl and metoxypropyl. The alkyl in said "alkoxyalkyl" can be substituted with one or more of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl. When e.g. the above "alkoxyl" or "alkoxyalkyl" radicals are substituted with one or more halo atoms, such as fluoro, chloro or bromo, "haloalkoxy" or "haloalkoxyalkyl" radicals are provided. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one, two or three rings wherein such rings may be attached together in a pendent manner or may be fused. When substituted, "aryl" can comprise one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl. Examples of "aryl" include aromatic radicals such as phenyl, pentafluorphenyl, naphthyl, tetrahydronaphthyl, indane and biphenyl.

The term "heterocyclic" embraces saturated, partially saturated and unsaturated heteroatom-containing ring-shaped radicals, where the heteroatoms may be selected from nitrogen, sulfur and oxygen. When substituted, "heterocyclic" can comprise one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl. Examples of saturated heterocyclic radicals include e.g. saturated 3 to 6-membered heteromonocylic group containing 1 to 4 nitrogen atoms [e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g. thiazolidinyl, etc.]. Examples of partially saturated heterocyclic radicals include dihydrothiophene, dihydropyran, dihydrofuran and dihydrothiazole.

The term "heteroaryl" embraces unsaturated heterocyclic radicals. When substituted, "heteroaryl" can comprise one or more radicals selected from the group of radicals consisting of hydroxy, primary amine, secondary amine, carboxy, acid chloride, sulfonyl chloride, sulphonate, nitro, cyano, isothiocyanate, halogen, phosphonyl, sulphonyl, sulfamyl, carbonyl, and thiolyl. Examples of unsaturated heterocyclic radicals, also termed "heteroaryl" radicals, include e.g. unsaturated 5 to 6 membered heteromonocyclic group containing 1 to 4 nitrogen atoms, for example, pyrrolyl, pyrrolinyl, imidazolyl, pyrazolyl 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl, etc.], etc.; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3, 4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term "heteroaryl" or "unsaturated heterocyclic radical" also embraces radicals where heterocyclic radicals are fused with aryl radicals. Examples of such fused bicyclic radicals include benzofuran, benzothiophene, and the like. Said "heterocyclic group" can be substituted with one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl, said substitution generating a substituted "heteroaryl", optionally a substituted "heteroaryl" fused with an "aryl" radical which can be substituted or un-substituted. When substituted, the "aryl" is substituted as described herein above. Preferred heterocyclic radicals include five to ten membered fused or unfused radicals. More preferred examples or heteroaryl radicals include benzofuryl, 2,3-dihydrobenzofuryl, benzotrienyl, indolyl, dihydroindolyl, chromanyl, benzopyran, thiochromanyl, benzothiopyran, benzodioxolyl, benzodioxanyl, pyridyl, thienyl, thiazolyl, oxazolyl, furyl, and pyrazinyl.

The term "sulfonyl", whether used alone or linked to other terms such as alkylsulfonyl, denotes respectively divalent radicals —$SO_2$—.

"Alkylsulfonyl" embraces alkyl radicals attached to a sulfonyl radical, where alkyl can be substituted is defined as above. Alkylsulfonyl radicals can be "lower alkylsulfonyl" radicals having one to six carbon atoms. Examples of such lower alkylsulfonyl radicals include methylsulfonyl, ethylsulfonyl and propylsulfonyl.

The term "arylsulfonyl" embraces aryl radicals as defined above, including substituted aryl radicals, attached to a sulfonyl radical. Examples of such radicals include phenylsulfonyl.

The terms "sulfamyl," "aminosulfonyl" and "sulfonamidyl," whether alone or used with terms such as "N-alkylaminosulfonyl", "N-arylaminosulfonyl", "N,N-dialkylaminosulfonyl" and "N-alkyl-N-arylaminosulfonyl", denotes a sulfonyl radical substituted with an amine radical, forming a sulfonamide (—SO$_2$NH$_2$).

The terms "N-alkylaminosulfonyl" and "N,N-dialkylaminosulfonyl" denote sulfamyl radicals substituted respectively, with one alkyl radical, or two alkyl radicals, optionally substituted alkyl radicals as described herein above. Alkylaminosulfonyl radicals can be "lower alkylaminosulfonyl" radicals having one to six carbon atoms. Examples of such lower alkylaminosulfonyl radicals include N-methylaminosulfonyl, N-ethylaminosulfonyl and N-methyl-N-ethylaminosulfonyl.

The terms "N-arylaminosulfonyl" and "N-alkyl-N-arylaminosulfonyl" denote sulfamyl radicals substituted, respectively, with one aryl radical, or one alkyl and one aryl radical, optionally substituted aryl and/or alkyl radicals as described herein above. N-alkyl-N-arylaminosulfonyl radicals can be "lower N-alkyl-N-arylsulfonyl" radicals having alkyl radicals of one to six carbon atoms. Examples of such lower N-alkyl-N-aryl aminosulfonyl radicals include N-methyl-phenylaminosulfonyl and N-ethyl-phenylaminosulfonyl.

The terms "carboxy" or "carboxyl", whether used alone or with other terms, such as "carboxyalkyl", denotes —CO$_2$H.

The term "carboxyalkyl" or "alkanoyl" embraces radicals having a carboxy radical as defined above, attached to an alkyl radical as described herein above. When substituted, the "alkyl" or "lower alkyl" can comprise one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl. Examples of "carboxyalkyl" radicals include formyl, acetyl, propionyl (propanoyl), butanoyl (butyryl), isobutanoyl (isobutyryl), valeryl (pentanoyl), isovaleryl, pivaloyl, hexanoyl or the like.

The term "carbonyl", whether used alone or with other terms, such as "alkylcarbonyl", denotes —(C=O)—.

The term "alkylcarbonyl" embraces radicals having a carbonyl radical substituted with an alkyl radical. Alkylcarbonyl radicals can be "lower alkylcarbonyl" radicals having from one to six carbon atoms. Examples of such radicals include methylcarbonyl and ethylcarbonyl. When substituted, the "alkyl" or "lower alkyl" of the "alkylcarbonyl" can comprise one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, and thiolyl.

The term "alkylcarbonylalkyl", denotes an alkyl radical substituted with an "alkylcarbonyl" radical as described herein above. Both the alkyl and the alkylcarbonyl can be substituted as described herein above.

The term "alkoxycarbonyl" means a radical containing an alkoxy radical, as defined above, attached via an oxygen atom to a carbonyl radical. "Lower alkoxycarbonyl" embraces alkoxy radicals preferably having from one to six carbon atoms. Examples of "lower alkoxycarbonyl" ester radicals include substituted or unsubstituted methoxycarbonyl, ethoxycarbonyl, propoxycarbonyl, butoxycarbonyl and hexyloxycarbonyl.

The term "alkoxycarbonylalkyl" embraces radicals having "alkoxycarbonyl", as defined above substituted to an optionally substituted alkyl radical. Alkoxycarbonylalkyl radicals can be "lower alkoxycarbonylalkyl" having lower alkoxycarbonyl radicals as defined above attached to one to six carbon atoms. Examples of such lower alkoxycarbonylalkyl radicals include methoxycarbonylmethyl, tert-butoxycarbonylethyl, and methoxycarbonylethyl.

The term "aminocarbonyl" when used by itself or with other terms such as "aminocarbonylalkyl", "N-alkylaminocarbonyl", "N-arylaminocarbonyl, "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula —C(=O)NH$_2$.

The terms "N-alkylaminocarbonyl" and "N,N-dialkylaminocarbonyl" denote aminocarbonyl radicals which have been substituted with one alkyl radical and with two alkyl radicals, respectively. The alkyl radicals can be substituted as described herein above. "Lower alkylaminocarbonyl" comprises lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical, wherein such radicals can be substituted as described herein above.

The term "aminocarbonylalkyl" embraces optionally substituted alkyl radicals substituted with aminocarbonyl radicals.

The term "N-cycloalkylaminocarbonyl" denotes aminocarbonyl radicals which have been substituted with at least one optionally substituted cycloalkyl radical. "Lower cycloalkylaminocarbonyl" comprises lower cycloalkyl radicals of three to seven carbon atoms, attached to an aminocarbonyl radical.

The term "aminoalkyl" embraces alkyl radicals substituted with one or more amino radicals. The alkyl radicals can be further substituted by one or more radicals selected from the group of radicals consisting of hydroxy, carboxy, acid chloride, sulfonyl chloride, sulphonate, nitro, cyano, isothiocyanate, halogen, phosphonyl, sulphonyl, sulfamyl, carbonyl, and thiolyl.

The term "alkylaminoalkyl" embraces aminoalkyl radicals having the nitrogen atom substituted with an optionally substituted alkyl radical.

The term "amidino" denotes an —C(=NH)—NH$_2$ radical.

The term "cyanoamidino" denotes an —C(=N—CN)—NH$_2$ radical.

The term "heterocyclicalkyl" embraces heterocyclic-substituted alkyl radicals. The alkyl radicals can themselves be substituted by one or more radicals selected from the group of radicals consisting of hydroxy, primary amino, carboxy, acid chloride, sulfonyl chloride, sulphonate, nitro, cyano, isothiocyanate, halogen, phosphonyl, sulphonyl, sulfamyl, carbonyl, and thiolyl. Heterocyclicalkyl radicals can be "lower heterocyclicalkyl" radicals preferably having from one to six carbon atoms and a heterocyclic radical. Examples include such radicals as pyrrolidinylmethyl, pyridylmethyl and thienylmethyl.

The term "aralkyl" embraces aryl-substituted alkyl radicals. The alkyl radicals can themselves be substituted by one or more radicals selected from the group of radicals consisting of hydroxy, primary amino, carboxy, acid chloride, sulfonyl chloride, sulphonate, nitro, cyano, isothiocyanate, halogen, phosphonyl, sulphonyl, sulfamyl, carbonyl, and thiolyl. Aralkyl radicals can be "lower aralkyl" radicals having aryl radicals attached to alkyl radicals having from one to six carbon atoms. Examples of such radicals include benzyl, diphenylmethyl, triphenylmethyl, phenylethyl and diphenylethyl. The aryl in said aralkyl may be additionally substituted with halo, alkyl, alkoxy, halkoalkyl and haloalkoxy. The terms benzyl and phenylmethyl are interchangeable.

The term "cycloalkyl" embraces radicals having three to ten carbon atoms. Cycloalkyl radicals can be "lower cycloalkyl" radicals having three to seven carbon atoms. Examples include radicals such as cyclopropyl, cyclobutyl, cyclopentyl, cyclohexyl and cycloheptyl. The "cycloalkyl" can optionally be substituted by one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl.

The term "cycloalkenyl" embraces unsaturated cyclic radicals having three to ten carbon atoms. The "cycloalkenyl" can optionally be substituted by one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl. Examples include cyclobutenyl, cyclopentenyl, cyclohexenyl and cycloheptenyl, which can optionally be substituted as described above.

The term "alkylthio" embraces radicals containing a linear or branched alkyl radical, of one to ten carbon atoms, attached to a divalent sulfur atom. An example of "alkylthio" is methylthio, ($CH_3$—S—). The alkyl radical can be substituted as described herein above.

The term "alkylsulfinyl" embraces radicals containing a linear or branched alkyl radical, of one to ten carbon atoms, attached to a divalent —S(=O)— atom. The alkyl radical can be substituted as described herein above.

The term "aminoalkyl" embraces alkyl radicals substituted with amino radicals. The alkyl radicals can be further substituted by one or more radicals selected from the group of radicals consisting of hydroxy, carboxy, acid chloride, sulfonyl chloride, sulphonate, nitro, cyano, isothiocyanate, halogen, phosphonyl, sulphonyl, sulfamyl, carbonyl, and thiolyl. Aminoalkyl radicals can be "lower aminoalkyl" having from one to six carbon atoms. Examples include aminomethyl, aminoethyl and aminobutyl which can optionally be further substituted as described above.

The term "alkylaminoalkyl" embraces aminoalkyl radicals having the nitrogen atom substituted with at least one alkyl radical. Alkylaminoalkyl radicals can be "lower alkylaminoalkyl" having one to six carbon atoms attached to a lower aminoalkyl radical as described above. The alkyl radical can be substituted as described herein above.

The terms "N-alkylamino" and "N,N-dialkylamino" denote amino groups which have been substituted with one alkyl radical and with two alkyl radicals, respectively. The alkyl radical can be substituted as described herein above. Alkylamino radicals can be "lower alkylamino" radicals having one or two alkyl radicals of one to six carbon atoms, attached to a nitrogen atom. Suitable "alkylamino" may be mono or dialkylamino such as N-methylamino, N-ethylamino, N,N-dimethylamino, N,N-diethylamino or the like.

The term "arylamino" denotes amino groups which have been substituted with one or two aryl radicals, such as N-phenylamino. The "arylamino" radicals may be further substituted on the aryl ring portion of the radical. Substitutions can include one or more of hydroxy, amino, carboxy, acid chloride, sulfonyl chloride, sulphonate, nitro, cyano, isothiocyanate, halogen, phosphonyl, sulphonyl, sulfamyl, carbonyl, and thiolyl.

The term "aralkylamino" denotes amino groups which have been substituted with one or two aralkyl radicals, such as N-benzylamino. The "aralkylamino" radicals may be further substituted on the aryl ring portion of the radical. Substitutions can include one or more of hydroxy, amino, carboxy, acid chloride, sulfonyl chloride, sulphonate, nitro, cyano, isothiocyanate, halogen, phosphonyl, sulphonyl, sulfamyl, carbonyl, and thiolyl.

The terms "N-alkyl-N-arylamino" and "N-aralkyl-N-alkylamino" denote amino groups which have been substituted with one aralkyl and one alkyl radical, or one aryl and one alkyl radical, respectively, to an amino group. The aralkyl and/or alkyl and/or aryl radicals can be substituted as described herein above.

The terms "N-arylaminoalkyl" and "N-aralkylaminoalkyl" denote amino groups which have been substituted with one aryl radicals or one aralkyl radical, respectively, and having the amino group attached to an alkyl radical. The aralkyl and/or alkyl and/or aryl radicals can be substituted as described herein above. Arylaminoalkyl radicals can be "lower arylaminoalkyl" having the arylamino radical attached to one to six carbon atoms. Examples of such radicals include N-phenylaminomethyl and N-phenyl-N-methylaminomethyl.

The terms "N-alkyl-N-arylaminoalkyl", and "N-aralkyl-N-alkylaminoalkyl" denote N-alkyl-N-arylamino and N-alkyl-N-aralkylamino groups, respectively, and having the amino group attached to alkyl radicals which can be substituted as described herein above.

The term "acyl", whether used alone, or within a term such as "acylamino", denotes a radical provided by the residue after removal of hydroxyl from an organic acid.

The term "acylamino" embraces an amino radical substituted with an acyl group. An examples of an "acylamino" radical is acetylamino or acetamido ($CH_3C(=O)$—NH—) where the amine may be further substituted with alkyl, aryl or aralkyl, wherein said alkyl, aryl or aralkyl can be substituted as described herein above.

The term "arylthio" embraces aryl radicals of six to ten carbon atoms, attached to a divalent sulfur atom. The aryl can be substituted as described herein above. An example of "arylthio" is phenylthio.

The term "aralkylthio" embraces aralkyl radicals as described above, attached to a divalent sulfur atom. The aralkyl radicals can be further substituted as described herein above. An example of "aralkylthio" is benzylthio.

The term "aryloxy" embraces aryl radicals, as defined above, attached to an oxygen atom. The aryl can be substituted as described herein above. Examples of such radicals include phenoxy.

The term "aralkoxy" embraces oxy-containing aralkyl radicals attached through an oxygen atom to other radicals. The aralkyl can be substituted as described herein above. Aralkoxy radicals can be "lower aralkoxy" radicals having phenyl radicals attached to lower alkoxy radical as described above.

The term "haloaralkyl" embraces aryl radicals as defined above attached to haloalkyl radicals. The aryl can be further substituted as described herein above.

The term "carboxyhaloalkyl" embraces carboxyalkyl radicals as defined above having halo radicals attached to the alkyl portion. The alkyl portion can be further substituted as described herein above.

The term "alkoxycarbonylhaloalkyl" embraces alkoxycarbonyl radicals as defined above substituted on a haloalkyl radical. The haloalkyl radical can be further substituted by one or more of hydroxy, amino, carboxy, acid chloride, sulfonyl chloride, sulphonate, nitro, cyano, isothiocyanate, phosphonyl, sulphonyl, sulfamyl, carbonyl, and thiolyl.

The term "aminocarbonylhaloalkyl" embraces aminocarbonyl radicals as defined above substituted on an optionally substituted haloalkyl radical wherein the alkyl is substituted by one or more of hydroxy, amino, carboxy, acid chloride, sulfonyl chloride, sulphonate, nitro, cyano, isothiocyanate, phosphonyl, sulphonyl, sulfamyl, carbonyl, and thiolyl.

The term "alkylaminocarbonylhaloalkyl" embraces alkylaminocarbonyl radicals as defined above substituted on an optionally substituted haloalkyl radical as described above.

The term "alkoxycarbonylcyanoalkenyl" embraces alkoxycarbonyl radicals as defined above, and a cyano radical, both substituted on an optionally substituted alkenyl radical.

The term "carboxyalkylaminocarbonyl" embraces aminocarbonyl radicals substituted with carboxyalkyl radicals, as defined above. The carboxyalkyl can be further substituted. Substitutions can include one or more of hydroxy, amino, acid chloride, sulfonyl chloride, sulphonate, nitro, cyano, isothiocyanate, halogen, phosphonyl, sulphonyl, sulfamyl, carbonyl, and thiolyl.

The term "aralkoxycarbonylalkylaminocarbonyl" embraces aminocarbonyl radicals substituted with aryl-substituted alkoxycarbonyl radicals, as defined above.

The term "cycloalkylalkyl" embraces cycloalkyl radicals having three to ten carbon atoms attached to an alkyl radical, as defined above. Cycloalkylalkyl radicals can be "lower cycloalkylalkyl" radicals having cycloalkyl radicals attached to lower alkyl radicals as defined above. Examples include radicals such as cyclopropylmethyl, cyclobutylmethyl, and cyclohexylethyl.

The term "aralkenyl" embraces optionally substituted aryl radicals attached to alkenyl radicals having two to ten carbon atoms, such as phenylbutenyl, and phenylethenyl or styryl. When substituted the aryl can be substituted with one or more of hydroxy, amino, carboxy, acid chloride, sulfonyl chloride, sulphonate, nitro, cyano, isothiocyanate, halogen, phosphonyl, sulphonyl, sulfamyl, carbonyl, and thiolyl.

DETAILED DESCRIPTION OF THE INVENTION

In one embodiment of the methods of the present invention, one or more oligonucleotide tags are provided and attached to a solid support. The attachment may be non-covalent or covalent. Preferably, the oligonucleotide tag(s) are attached to the solid-support that was used for synthesising the oligonucleotide(s) by means of solid phase organic synthesis methods. Each oligonucleotide may contain a common nucleotide sequence shared with other nucleotides, or a unique, "bar-code"-like oligonucleotide sequence, or a combination of such common and unique nucleotide sequences.

Each of the above-cited oligonucleotide tags can be attached to the solid-support (marked by a sphere in FIG. 1) through a selectively cleavable linker (SCL) which can be cleaved with all or only a subset of optionally present protection groups still intact. The underlined sequences are examples of common sequences shared between the oligonucleotides in the illustrated set of oligonucleotides. Such sequences may be useful e.g. for amplification by PCR of oligonucleotide-tag information.

Furthermore, the common sequences may be used to facilitate enzymatic coupling to one or more further oligonucleotide tags e.g. by double stranded or partly double stranded overhang ligations, ligations using a complementary "splint" oligonucleotide, or by ligation between single stranded oligonucleotides using enzymes such as e.g. T4 DNA ligase, *E. coli* ligase, various thermostable ligases, T4 RNA ligase, or similar performing enzymes, as well as polymerases and recombinases. A ligation can also be accomplished without using complementary sequences, by using e.g. blunt-end ligation, or by using a combination of chemical ligation methods and enzymatic ligation methods.

All of the employed oligonucleotides may contain a linker (L) that connects the oligonucleotide to one or more reactive sites marked by an X in FIG. 1. The reactive sites may be located at any position in the oligonucleotide, such as in the 3' end and/or the 5' end and/or at one or more internal positions in the oligonucleotide.

The reactive sites X may be different or identical—depending on the specific requirements for a chemical compound building block and a reactive site to react. Thus, it may be desirable to have different reactive groups, such as e.g. primary and secondary aliphatic- or cyclic amines, carboxylic acids, aliphatic- or aromatic aldehydes, aliphatic- or aromatic thiols- or alcohols, or any other reactive group useful as a chemical handle for the addition of a chemical fragment to the oligonucleotide. In another embodiment it may be preferred to have identical reactive handles. Further examples of suitable reactive handles have been described elsewhere in this application.

The linker (L) is introduced to distance the reactive site X from the oligonucleotide in order to facilitate display of chemical compounds attached to X to interaction with a molecular target entity, such as a target protein or protein complex. Thus, a molecular spacing by the linker (L) would act to improve presentation of the attached compounds for the purpose of applying a selection process, such as an in vitro affinity selection assay to retrieve compounds with desired interaction properties without interference from the oligonucleotide moiety in the selection process. Suitable linkers should preferably be inert and include but is not limited to polycarbons or polyethyleneglycols units of any number as described elsewhere in this application.

Each of the oligonucleotides listed above contain a unique "codon" sequence of 6 nucleotides enabling each oligonucleotide to encode a unique chemical fragment or fragment group reacted at the reactive site X. Similar to the procedures described elsewhere in this patent application, attachment of a number of different building blocks to individual oligonucleotide tags each having a unique codon sequence thus forms a library of bi-functional complexes comprising unique compounds covalently linked to a unique oligonucleotide tag that encodes said compound(s).

Such a library of bi-functional complexes may be subjected to a partitioning to enrich for compounds of desired properties, such as affinity to a target protein. The identity of enriched compounds is revealed by optionally amplifying the enriched oligonucleotide tags by PCR prior to the sequencing oligonucleotide tags. The relative abundance of individual oligonucleotide codons or codon combinations will identify the relative abundance and identity of chemical compounds retrieved in the selection step(s) as describe elsewhere herein.

The attachment of chemical fragments to the one or more reactive site(s) X on the oligonucleotide requires a chemical reaction between two reactive entities forming one or more covalent bond(s). Any number of reactions is feasible provided that the chemical reaction does not adversely affect its function as an information storage unit. Thus, any chemical reaction may be used—provided that it does not affect the quality, amplifiability and sequencing property of oligonucleotide tags present in the reaction mixture.

Many chemical reactions can be accomplished in the presence of DNA that does not carry protection groups on the functional groups of the nucleotides (nucleobases, sugar and phosphate-backbone moieties). However, for some reactions it will be expected that the optimal reaction conditions will damage unprotected oligonucleotides and the use of such reactions will be a trade-off between reaction turnover and how much DNA damage is tolerated.

In order to limit the dismissal of potentially interesting chemical reactions due to excessive DNA damage, or the suboptimal use of mild reaction conditions with insufficient turnover, it may be desirable to conduct some chemical transformations, such as e.g. organometallic catalysis reactions, alkylations with aliphatic halides, or acylations with fluoro/chloro-acids, etc., in the presence of oligonucleotides with suitable protection groups to avoid unwarranted side-reactions with the oligonucleotides.

An initial or naïve library of intermediate or final bi-functional complexes can be partitioned by selection against a target and desirable bi-functional complexes having affinity for the target can thus be obtained. Such partitioned, desirable bi-functional complexes can be decoded and the information obtained from decoding the identifier oligonucleotide can be used for the synthesis of intelligent libraries.

The methods of the present invention and their various components are further disclosed in more detail herein below.

Nucleotides

An oligonucleotide tag comprises recognition units, i.e. units which can be recognized by recognition groups. The recognition units making up an oligonucleotide tag possesses information so as to identify a reactive compound building block having participated in the synthesis of the molecule. Generally, it is preferred that the oligonucleotide tag comprises or consists of a sequence of nucleotides.

Individual oligonucleotide tags can be distinguished from each other e.g. by a difference in only a single nucleotide position, such as a deletion, an insertion or a mutation. However, to facilitate a subsequent decoding process it is in general desirable to have two or more differences in the nucleotide sequence of any two oligonucleotide tags.

In the event two or more reactive compound building blocks are reacted with the chemical reactive site, the oligonucleotide tags of the identifier oligonucleotide can be separated by a constant region or a binding region. One function of the binding region can be to establish a platform at which an enzyme, such as polymerase or ligase can recognise as a substrate. Depending on the molecule formed, the identifier oligonucleotide can comprise further oligonucleotide tags, such as 2, 3, 4, 5, or more oligonucleotide tags. Each of the further oligonucleotide tags can be separated by a suitable binding region.

All or at least a majority of the oligonucleotide tags of the identifier oligonucleotide can be separated from a neighbouring oligonucleotide tag by a binding sequence. The binding region may have any suitable number of nucleotides, e.g. 1 to 20. The binding region, if present, may serve various purposes besides serving as a substrate for an enzyme. In one setup of the invention, the binding region identifies the position of the oligonucleotide tag. Usually, the binding region either upstream or downstream of an oligonucleotide tag comprises information which allows determination of the position of the oligonucleotide tag. In another setup, the binding regions have alternating sequences, allowing for addition of reactive compound building blocks from two pools in the formation of the library. Moreover, the binding region may adjust the annealing temperature to a desired level.

A binding region with high affinity can be provided by one or more nucleobases forming three hydrogen bonds to a cognate nucleobase. Examples of nucleobases having this property are guanine and cytosine. Alternatively, or in addition, the binding region can be subjected to backbone modification. Several backbone modifications provides for higher affinity, such as 2'-O-methyl substitution of the ribose moiety, peptide nucleic acids (PNA), and 2'-4' O-methylene cyclisation of the ribose moiety, also referred to as LNA (Locked Nucleic Acid).

The identifier oligonucleotide can optionally further comprise flanking regions around the oligonucleotide tag. The flanking region can encompass a signal group, such as a fluorophor or a radio active group to allow for detection of the presence or absence of a complex or the flanking region may comprise a label that can be detected, such as biotin. When the identifier comprises a biotin moiety, the identifier may easily be recovered.

The flanking regions can also serve as oligonucleotide tag addition sites for amplification reactions, such as PCR. Usually, the last cycle in the formation of the bi-functional complex includes the incorporation of an oligonucleotide tag addition site. A region of the bi-functional complex close to the molecule, such as a nucleic acid sequence between the molecule and the oligonucleotide tag coding for the scaffold molecule, is usually used for another oligonucleotide tag addition site, thereby allowing for PCR amplification of the coding region of the bi-functional complex if necessary for decoding such as sequencing and subsequent deconvolution.

Apart from a combination of the nucleotides coding for the identity of the reactive compound building block, an oligonucleotide tag may comprise further nucleotides, such as a framing sequence. The framing sequence can serve various purposes, such as acting as a further annealing region for complementary tags and/or as a sequence informative of the point in time of the synthesis history of the molecule being synthesised.

In certain embodiments, an oligonucleotide tag codes for several different reactive compound building blocks. In a subsequent identification step, the structure of the molecule can never-the-less be deduced by taking advanoligonucleotide tage of the knowledge of the different attachment chemistries, steric hindrance, deprotection of orthogonal protection groups, etc. In another embodiment, the same oligonucleotide tag is used for a group of reactive compound building blocks having a common property, such as a lipophilic nature, molecular weight, or a certain attachment chemistry, etc. In a still further embodiment, each oligonucleotide tag is unique, i.e. a similar combination of nucleotides does not identify another reactive compound building block. The same of different synthesis methods can employ the same or different type of oligonucleotide tags as disclosed herein above.

In some embodiments it can be advantageous to use several different oligonucleotide tags for the same reactive compound building block. Accordingly, two or more oligonucleotide tags identifying the same reactive compound building block can optionally carry further information relating to e.g. different reaction conditions.

The identifier oligonucleotide of the final bi-functional complex comprises all the oligonucleotide tags necessary for identifying the corresponding molecule. All or part of the sequence of each oligonucleotide tag is used to decipher the structure of the reactive compound building blocks that have participated in the formation of the molecule, i.e. the reaction product.

The order of the oligonucleotide tags can also be used to determine the order of incorporation of the reactive compound building blocks. This can be of particular interest e.g. when a linear polymer is formed, because the exact sequence of the polymer can be determined by decoding the encoding sequence. Usually, to facilitate the decoding step, oligonucleotide tags will further comprise a constant region or a binding region together with the oligonucleotide tag sequence identifying a given reactive compound building block. The constant region may contain information about the position of the reactive compound building block in a synthesis pathway resulting in the synthesis of the molecule.

The identifier oligonucleotide of the bi-functional complex is in a preferred aspect of the invention amplifiable. The capability of being amplified allows for the use of a low amount of bi-functional complex during a selection process. In one embodiment the oligonucleotide tag is a sequence of nucleotides which can be amplified using standard techniques like PCR. When two or more oligonucleotide tags are present in a linear identifying oligonucleotide, said oligonucleotide generally comprises a certain backbone structure, so as to allow an enzyme to recognise the oligonucleotide as substrate. As an example the back bone structure can be DNA or RNA.

The oligonucleotide tag addition site of a nascent bi-functional complex is capable of receiving an oligonucleotide tag. When the oligonucleotide tag comprises a polynucleotide sequence, the oligonucleotide tag addition site generally comprises a 3'-OH or 5'-phosphate group, or functional derivatives of such groups. Enzymes which can be used for enzymatic addition of an oligonucleotide tag to the oligonucleotide tag addition site include an enzyme selected from polymerase, ligase, and recombinase, and a combination of these enzymes. In some embodiments, an enzyme comprising ligase activity is preferred.

All or some of the nucleotides of an oligonucleotide tag can be involved in the identification of a corresponding reactive compound building block. In other words, decoding of an identifier oligonucleotide can be performed by determining the sequence of all or only a part of the identifier oligonucleotide.

In some embodiments of the invention, each oligonucleotide tag and each complementary tag constitutes what is often referred to as a "codon" and an "anti-codon", respectively. These terms are often used in the prior art even though the methods employ split-and-mix technology and not templated reactions. In some embodiments, each oligonucleotide tag and each complementary tag comprises one or more "codon(s)" or anti-codon(s)", respectively, which identifies the corresponding reactive compound building block involved in the synthesis of a molecule.

The identifier oligonucleotide resulting from oligonucleotide tag ligation can include or exclude the third intermediate bi-functional complex and preferably has a length of from 6 to about 300 consecutive nucleotides, for example from 6 to about 250 consecutive nucleotides, such as from 6 to about 200 consecutive nucleotides, for example from 6 to about 150 consecutive nucleotides, such as from 6 to 100, for example from 6 to 80, such as from 6 to 60, such as from 6 to 40, for example from 6 to 30, such as from 6 to 20, such as from 6 to 15, for example from 6 to 10, such as from 6 to 8, such as 6, for example from 7 to 100, such as from 7 to 80, for example from 7 to 60, such as from 7 to 40, for example from 7 to 30, such as from 7 to 20, for example from 7 to 15, such as from 7 to 10, such as from 7 to 8, for example 7, for example from 8 to 100, such as from 8 to 80, for example from 8 to 60, such as from 8 to 40, for example from 8 to 30, such as from 8 to 20, for example from 8 to 15, such as from 8 to 10, such as 8, for example 9, for example from 10 to 100, such as from 10 to 80, for example from 10 to 60, such as from 10 to 40, for example from 10 to 30, such as from 10 to 20, for example from 10 to 15, such as from 10 to 12, such as 10, for example from 12 to 100, such as from 12 to 80, for example from 12 to 60, such as from 12 to 40, for example from 12 to 30, such as from 12 to 20, for example from 12 to 15, such as from 14 to 100, such as from 14 to 80, for example from 14 to 60, such as from 14 to 40, for example from 14 to 30, such as from 14 to 20, for example from 14 to 16, such as from 16 to 100, such as from 16 to 80, for example from 16 to 60, such as from 16 to 40, for example from 16 to 30, such as from 16 to 20, such as from 18 to 100, such as from 18 to 80, for example from 18 to 60, such as from 18 to 40, for example from 18 to 30, such as from 18 to 20, for example from 20 to 100, such as from 20 to 80, for example from 20 to 60, such as from 20 to 40, for example from 20 to 30, such as from 20 to 25, for example from 22 to 100, such as from 22 to 80, for example from 22 to 60, such as from 22 to 40, for example from 22 to 30, such as from 22 to 25, for example from 25 to 100, such as from 25 to 80, for example from 25 to 60, such as from 25 to 40, for example from 25 to 30, such as from 30 to 100, for example from 30 to 80, such as from 30 to 60, for example from 30 to 40, such as from 30 to 35, for example from 35 to 100, such as from 35 to 80, for example from 35 to 60, such as from 35 to 40, for example from 40 to 100, such as from 40 to 80, for example from 40 to 60, such as from 40 to 50, for example from 40 to 45, such as from 45 to 100, for example from 45 to 80, such as from 45 to 60, for example from 45 to 50, such as from 50 to 100, for example from 50 to 80, such as from 50 to 60, for example from 50 to 55, such as from 60 to 100, for example from 60 to 80, such as from 60 to 70, for example from 70 to 100, such as from 70 to 90, for example from 70 to 80, such as from 80 to 100, for example from 80 to 90, such as from 90 to 100 consecutive nucleotides.

The length of the identifier oligonucleotide will depend of the length of the individual oligonucleotide tags as well as on the number of oligonucleotide tags ligated. In some embodiments of the invention it is preferred that the identifier oligonucleotide is attached to a solid or semi-solid support.

The identifier oligonucleotide preferably comprises a string of consecutive nucleotides comprising from 2 to 10 oligonucleotide tags, for example from 3 to 10 oligonucleotide tags, such as from 4 to 10 oligonucleotide tags, for example from 5 to 10 oligonucleotide tags, such as from 6 to 10 oligonucleotide tags, for example from 7 to 10 oligonucleotide tags, such as from 8 to 10 oligonucleotide tags, for example from 2 to 9 oligonucleotide tags, such as from 2 to 8 oligonucleotide tags, for example from 2 to 7 oligonucleotide tags, such as from 2 to 6 oligonucleotide tags, for example from 2 to 5 oligonucleotide tags, such as from 2 to 4 oligonucleotide tags, for example 2 or 3 oligonucleotide tags, such as from 3 to 9 oligonucleotide tags, such as from 3 to 8 oligonucleotide tags, for example from 3 to 7 oligonucleotide tags, such as from 3 to 6 oligonucleotide tags, for example from 3 to 5 oligonucleotide tags, such as from 3 to 4 oligonucleotide tags, for example from 4 to 9 oligonucleotide tags, such as from 4 to 8 oligonucleotide tags, for example from 4 to 7 oligonucleotide tags, such as from 4 to 6 oligonucleotide tags, for example from 4 to 5 oligonucleotide tags, such as from 5 to 9 oligonucleotide tags, such as from 5 to 8 oligonucleotide tags, for example from 5 to 7 oligonucleotide tags, such as 5 or 6 oligonucleotide tags, for example 2, 3, 4 or 5 oligonucleotide tags, such as 6, 7 or 8 oligonucleotide tags, for example 9 or 10 oligonucleotide tags.

The third intermediate bi-functional complex and/or the oligonucleotide tags employed in the methods of the present invention in one embodiment preferably comprise or essentially consist of nucleotides selected from the group consisting of deoxyribonucleic acids (DNA), ribonucleic acids (RNA), peptide nucleic acids (PNA), locked nucleic acids (LNA), and morpholinos sequences, including any analog or derivative thereof.

In another embodiment, the third intermediate bi-functional complex and/or the oligonucleotide tags employed in the methods of the present invention preferably comprise or essentially consist of nucleotides selected from the group consisting of DNA, RNA, PNA, LNA and morpholinos sequence, including any analog or derivative thereof, and the complementary tags preferably comprise or essentially consist of nucleotides selected from the group consisting of DNA, RNA, PNA, LNA and morpholinos sequences, including any analog or derivative thereof.

The nucleic acids useful in connection with the present invention include, but is not limited to, nucleic acids which can be linked together in a sequence of nucleotides, i.e. an oligonucleotide. However, in one embodiment and in order to prevent ligation of complementary tags, c.f. step xiv) and xv), end-positioned nucleic acids of complementary tags do not contain a reactive group, such as a 5'-P or a 3'-OH reactive group, capable of being linked by e.g. an enzyme comprising ligase activity. The oligonucleotide tag addition site of the third intermediate bi-functional complex preferably comprises a 3'-OH or 5'-phosphate group, or functional derivatives of such groups, capable of being linked by an enzyme comprising ligase activity.

Each nucleotide monomer is normally composed of two parts, namely a nucleobase moiety, and a backbone. The back bone may in some cases be subdivided into a sugar moiety and an internucleoside linker. The nucleobase moiety can be selected among naturally occurring nucleobases as well as non-naturally occurring nucleobases. Thus, "nucleobase" includes not only known purine and pyrimidine hetero-cycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diamino-purine, 5-methylcytosine, 5-($C^3$-$C^6$)-alkynylcytosine, 5-fluorouracil, 5-bromouracil, pseudoisocytosine, 2-hydroxy-5-methyl-4-triazolopyridine, isocytosine, isoguanine, inosine and the "non-natural" nucleobases described in U.S. Pat. No. 5,432,272.

The term "nucleobase" is intended to cover these examples as well as analogues and tautomers thereof. Especially interesting nucleobases are adenine, guanine, thymine, cytosine, 5-methylcytosine, and uracil, which are considered as the naturally occurring nucleobases. Examples of suitable specific pairs of nucleobases are shown below:

Natural Base Pairs

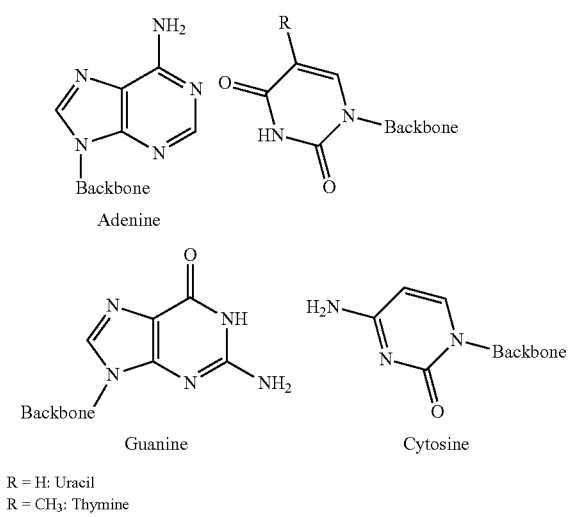

R = H: Uracil
R = $CH_3$: Thymine

Synthetic Base Pairs

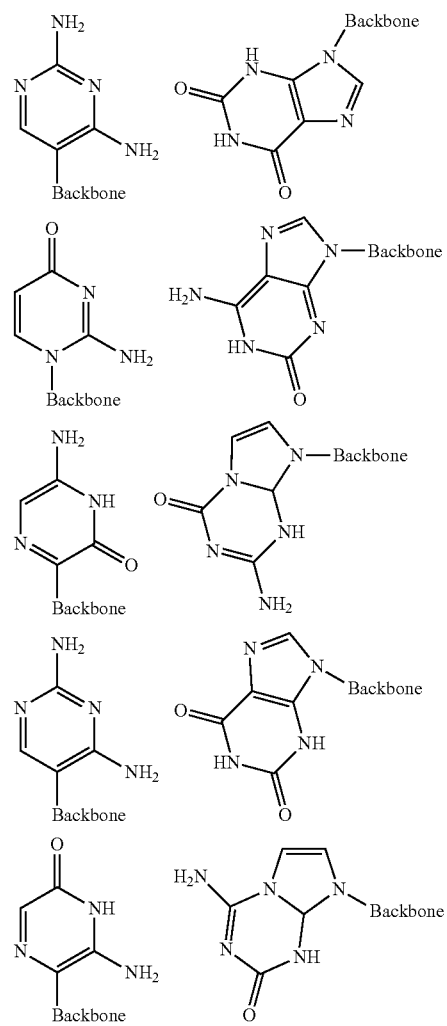

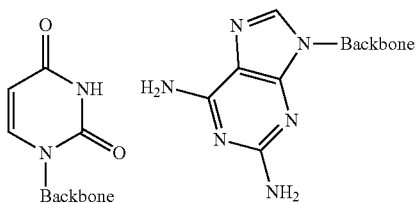
Synthetic Purine Bases Pairing with Natural Pyrimidines
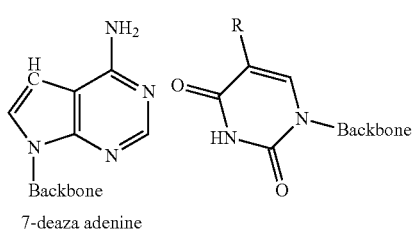
7-deaza adenine
7-deaza guanine       Cytosine
R = H: Uracil
R = CH₃: Thymine
Suitable examples of backbone units are shown below (B denotes a nucleobase):
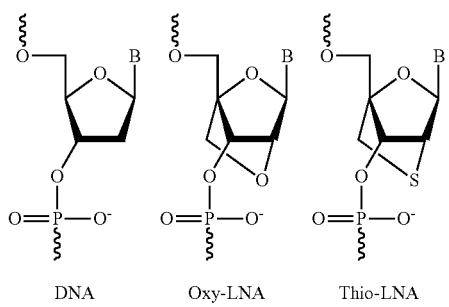
DNA        Oxy-LNA       Thio-LNA
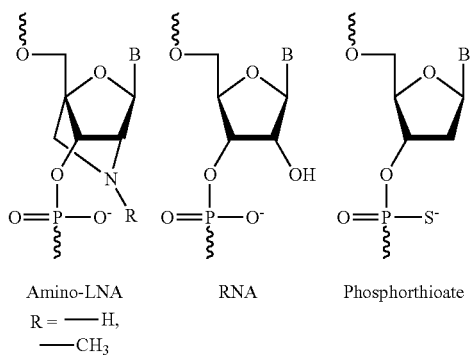
Amino-LNA     RNA      Phosphorthioate
R = ——H,
    ——CH₃
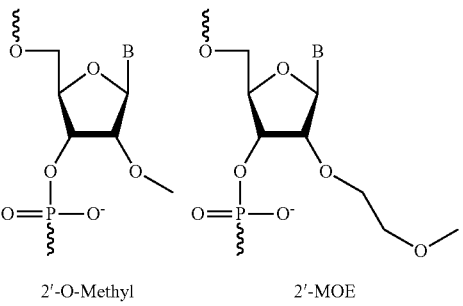
2'-O-Methyl       2'-MOE
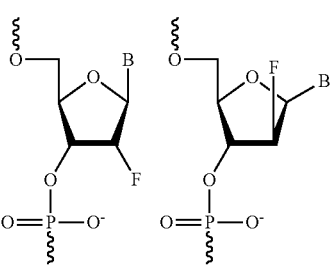
2'-Fluoro       2'-F-ANA
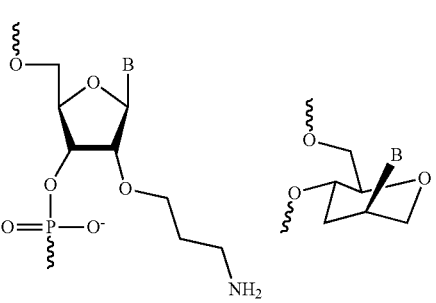
2'-AP            HNA
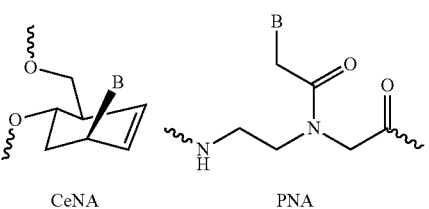
CeNA            PNA
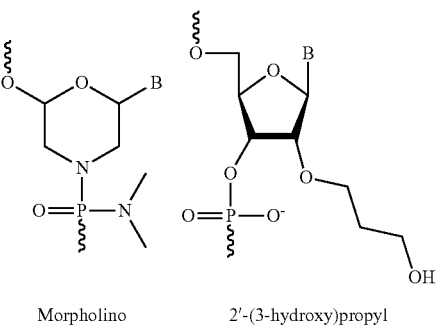
Morpholino     2'-(3-hydroxy)propyl

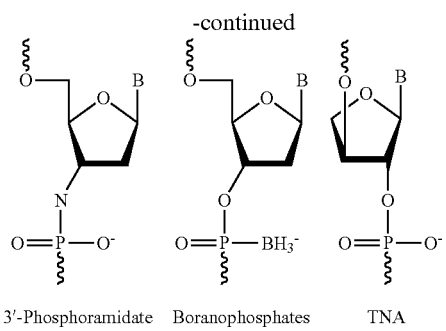

3'-Phosphoramidate    Boranophosphates    TNA

The sugar moiety of the backbone is suitably a pentose, but can be the appropriate part of an PNA or a six-member ring. Suitable examples of possible pentoses include ribose, 2'-deoxyribose, 2'-O-methyl-ribose, 2'-flour-ribose, and 2'-4'-O-methylene-ribose (LNA). Suitably the nucleobase is attached to the 1' position of the pentose entity.

An internucleoside linker connects the 3' end of preceding monomer to a 5' end of a succeeding monomer when the sugar moiety of the backbone is a pentose, like ribose or 2-deoxyribose. The internucleoside linkage can be the natural occurring phosphodiester linkage or a derivative thereof. Examples of such derivatives include phosphorothioate, methylphosphonate, phosphoramidate, phosphotriester, and phosphodithioate. Furthermore, the internucleoside linker can be any of a number of non-phosphorous-containing linkers known in the art.

Preferred nucleic acid monomers include naturally occurring nucleosides forming part of the DNA as well as the RNA family connected through phosphodiester linkages. The members of the DNA family include deoxyadenosine, deoxyguanosine, deoxythymidine, and deoxycytidine. The members of the RNA family include adenosine, guanosine, uridine, cytidine, and inosine.

It is within the capability of the skilled person in the art to construct the desired design of an oligonucleotide. When a specific annealing temperature is desired it is a standard procedure to suggest appropriate compositions of nucleic acid monomers and the length thereof. The construction of an appropriate design can be assisted by software, such as Vector NTI Suite or the public database at the internet address http://www.nwfsc.noaa.gov/protocols/oligoTMcalc.html. The conditions which allow hybridisation of two oligonucleotides are influenced by a number of factors including temperature, salt concentration, type of buffer, and acidity. It is within the capabilities of the person skilled in the art to select appropriate conditions to ensure that the contacting between two oligonucleotides is performed at hybridisation conditions. The temperature at which two single stranded oligonucleotides forms a duplex is referred to as the annealing temperature or the melting temperature. The melting curve is usually not sharp indicating that the annealing occurs over a temperature range.

Oligonucleotides in the form of oligonucleotide tags, complementary tags and third intermediate bi-functional complexes can be synthesized by a variety of chemistries as is well known. For synthesis of an oligonucleotide on a substrate in the direction of 3' to 5', a free hydroxy terminus is required that can be conveniently blocked and deblocked as needed. A preferred hydroxy terminus blocking group is a dimexothytrityl ether (DMT). DMT blocked termini are first deblocked, such as by treatment with 3% dichloroacetic acid in dichloromethane (DCM) as is well known for oligonucleotide synthesis, to form a free hydroxy terminus.

Nucleotides in precursor form for addition to a free hydroxy terminus in the direction of 3' to 5' require a phosphoramidate moiety having an aminodiisopropyl side chain at the 3' terminus of a nucleotide. In addition, the free hydroxy of the phosphoramidate is blocked with a cyanoethyl ester (OCNET), and the 5' terminus is blocked with a DMT ether. The addition of a 5' DMT-, 3' OCNET-blocked phosphoramidate nucleotide to a free hydroxyl requires tetrazole in acetonitrile followed by iodine oxidation and capping of unreacted hydroxyls with acetic anhydride, as is well known for oligonucleotide synthesis. The resulting product contains an added nucleotide residue with a DMT blocked 5' terminus, ready for deblocking and addition of a subsequent blocked nucleotide as before.

For synthesis of an oligonucleotide in the direction of 5' to 3', a free hydroxy terminus on the linker is required as before. However, the blocked nucleotide to be added has the blocking chemistries reversed on its 5' and 3' termini to facilitate addition in the opposite orientation. A nucleotide with a free 3' hydroxyl and 5' DMT ether is first blocked at the 3' hydroxy terminus by reaction with TBS-Cl in imidazole to form a TBS ester at the 3' terminus. Then the DMT-blocked 5' terminus is deblocked with DCA in DCM as before to form a free 5' hydroxy terminus. The reagent (N,N-diisopropylamino) (cyanoethyl) phosphonamidic chloride having an aminodiisopropyl group and an OCNET ester is reacted in tetrahydrofuran (THF) with the 5' deblocked nucleotide to form the aminodiisopropyl-, OCNET-blocked phosphonamidate group on the 5' terminus. Thereafter the 3' TBS ester is removed with tetrabutylammonium fluoride (TBAF) in DCM to form a nucleotide with the phosphonamidate-blocked 5' terminus and a free 3' hydroxy terminus. Reaction in base with DMT-Cl adds a DMT ether blocking group to the 3' hydroxy terminus.

The addition of the 3' DMT-, 5' OCNET-blocked phosphonamidated nucleotide to a linker substrate having a free hydroxy terminus then proceeds using the previous tetrazole reaction, as is well known for oligonucleotide polymerization. The resulting product contains an added nucleotide residue with a DMT-blocked 3' terminus, ready for deblocking with DCA in DCM and the addition of a subsequent blocked nucleotide as before.

The identifier oligonucleotide part of a bi-functional complex is formed by addition of an oligonucleotide tag or more than one oligonucleotide tag to an oligonucleotide tag addition site and/or to a previously added oligonucleotide tag using one or more enzymes such as enzymes possessing ligase activity. When one or more further oligonucleotide tag(s) are attached to an oligonucleotide tag which was added to a nascent bi-functional complex in a previous synthesis round, the addition can produce a linear or a branched identifier oligonucleotide. Preferably, at least one oligonucleotide tag of the identifier is attached to the oligonucleotide tag addition site and/or to another oligonucleotide tag by an enzymatically catalysed reaction, such as a ligation. Further oligonucleotide tag(s) can in principle be attached using chemical means or enzymatic means. In one embodiment, all oligonucleotide tags are attached using an enzymatically catalysed reaction.

The identifier oligonucleotide part of the bi-functional complex is preferably amplifiable. This means that the oligonucleotide tags form a sequence of nucleotides capable of being amplified e.g. using a polymerase chain reaction (PCR) techniques.

The oligonucleotide tags can be "unique" for a single predetermined reactive compound building block, or a given oligonucleotide tag can in principle code for several different reactive compound building blocks, in which case the structure of the synthesised molecule can optionally be deduced by taking into account factors such as different attachment chemistries, steric hindrance and deprotection of orthogonal protection groups. It is also possible to use the same or similar oligonucleotide tags for a group of reactive compound building blocks having at least one common property in common, such as e.g. lipophilic nature, molecular weight and attachment chemistry.

In one embodiment, two or more oligonucleotide tags identifying the same reactive compound building block comprise further information related to different reaction conditions used for reacting said reactive compound building block. Individual oligonucleotide tags can be distinguished from each other by only a single nucleotide, or by two or more nucleotides. For example, when the oligonucleotide tag or complementary tag length is 5 nucleotides, more than 100 nucleotide combinations exist in which two or more differences appear between any two oligonucleotide tags.

Multiple Encoding

In one embodiment, multiple encoding implies that two or more oligonucleotide tags are provided in the identifier prior to or subsequent to a reaction between the chemical reactive site and two or more reactive compound building blocks. Multiple encoding has various advanoligonucleotide tages, such as allowing a broader range of reactions possible, as many compounds can only be synthesis by a three (or more) component reaction because an intermediate between the first reactive compound building block and the chemical reactive site is not stable. Other advanoligonucleotide tages relates to the use of organic solvents and the availability of two or more reactive compound building blocks in certain embodiments.

Thus in a certain aspect of the invention, it relates to a method for obtaining a bi-functional complex comprising a molecule part and a identifier oligonucleotide, wherein the molecule is obtained by reaction of a chemical reactive site with two or more reactive compound building blocks and the identifier oligonucleotide comprises oligonucleotide tag(s) identifying the reactive compound building blocks.

In a certain aspect of the invention, a first reactive compound building block forms an intermediate product upon reaction with the chemical reactive site and a second reactive compound building block reacts with the intermediate product to obtain the molecule or a precursor thereof. In another aspect of the invention, two or more reactive compound building blocks react with each other to form an intermediate product and the chemical reactive site reacts with this intermediate product to obtain the molecule or a precursor thereof.

The intermediate product can be obtained by reacting the two or more reactive compound building blocks separately and then in a subsequent step reacting the intermediate product with the chemical reactive site. Reacting the reactive compound building blocks in a separate step provide for the possibility of using conditions the oligonucleotide tags would not withstand. Thus, in case the identifier oligonucleotide comprises nucleic acids, the reaction between the reactive compound building block can be conducted at conditions that otherwise would degrade the nucleic acid.

The reactions can be carried out in accordance with the scheme shown below. The scheme shows an example in which the identifying oligonucleotide tags for two reactive compound building blocks and the chemical reactive site (scaffold) attached to the chemical reaction site are provided in separate compartments. The compartments are arranged in an array, such as a microtiter plate, allowing for any combination of the different acylating agents and the different alkylating agents.

| Starting situation: | | | | |
|---|---|---|---|---|
| Acylating | Alkylating agents | | | |
| agents | A | B | C | ... |
| 1 | Oligonucleotide tagx11-X | Oligonucleotide tagx12-X | Oligonucleotide tagx13-X | ... |
| 2 | Oligonucleotide tagx21-X | Oligonucleotide tagx22-X | Oligonucleotide tagx23-X | ... |
| 3 | Oligonucleotide tagx31-X | Oligonucleotide tagx32-X | Oligonucleotide tagx33-X | ... |
| ... | ... | ... | ... | ... |

X denotes a chemical reaction site such as a scaffold.

The two reactive compound building blocks are either separately reacted with each other in any combination or subsequently added to each compartment in accordance with the oligonucleotide tags of the identifier oligonucleotide or the reactive compound building blocks can be added in any order to each compartment to allow for a direct reaction. The scheme below shows the result of the reaction.

| Plate of products | | | | |
|---|---|---|---|---|
| Acylating | Alkylating agents | | | |
| agents | A | B | C | ... |
| 1 | Oligonucleotide tagx11-XA1 | Oligonucleotide tagx12-XB1 | Oligonucleotide tagx13-XC1 | ... |
| 2 | Oligonucleotide tagx21-XA2 | Oligonucleotide tagx22-XB2 | Oligonucleotide tagx23-XC2 | ... |
| 3 | Oligonucleotide tagx31-XA3 | Oligonucleotide tagx32-XB3 | Oligonucleotide tagx33-XC3 | ... |
| ... | ... | ... | ... | ... |

As an example XA2 denotes molecule XA2 in its final state, i.e. fully assembled from fragments X, A and 2.

The identifier oligonucleotide comprising the two or more oligonucleotide tags identifying the reactive compound building blocks, can in principle be prepared in any suitable way either before or after the reaction. In one embodiment of the invention, each of the identifier oligonucleotides are synthesised by standard phosphoramidite chemistry. In another aspect the oligonucleotide tags are pre-prepared and assembled into the final identifier oligonucleotide by chemical or enzymatic ligation.

Various possibilities for chemical ligation exist. Suitable examples include that a) a first identifier oligonucleotide end comprises a 3'-OH group and the second identifier oligonucleotide end comprises a 5'-phosphor-2-imidazole group. When reacted a phosphodiester internucleoside linkage is formed, b) a first identifier oligonucleotide end comprising a phosphoimidazolide group and the 3'-end and a phosphoimidazolide group at the 5'-and. When reacted together a phosphodiester internucleoside linkage is formed, c) a first identifier oligonucleotide end comprising a 3'-phosphorothioate group and a second identifier oligonucleotide comprising a 5'-iodine. When the two groups are reacted a 3'-O—P(=O) (OH)—S-5' internucleoside linkage is formed, and d) a first identifier oligonucleotide end comprising a 3'-phosphorothioate group and a second identifier oligonucleotide comprising a 5'-tosylate. When reacted a 3'-O—P(=O)(OH)—S-5' internucleoside linkage is formed.

Enzymes

The identifier oligonucleotide of a nascent bi-functional complex involves the addition of at least one oligonucleotide tag to an oligonucleotide tag addition site using one or more enzymes. Further oligonucleotide tags can be attached to a previous oligonucleotide tag so as to produce a linear or branched identifier oligonucleotide. One or more enzymes are used for at least one reaction involving one or more identifier oligonucleotide tags. Enzymes are in general substrate specific, entailing that the enzymatic addition of an oligonucleotide tag to an oligonucleotide tag addition site, or to another oligonucleotide tag, is not likely to interfere with the synthesis of a molecule. Enzymes can be active in both aqueous and organic solvents.

As long as at least one oligonucleotide tag of the identifier is attached to the oligonucleotide tag addition site or to another oligonucleotide tag by an enzymatic reaction, further oligonucleotide tags can be added using either chemical means or the same or different enzymatic means. In one embodiment, all of the oligonucleotide tags are added to the oligonucleotide tag addition site and/or to each other using the same or different enzymatically catalysed reaction(s).

In one embodiment, addition of an oligonucleotide tag to the oligonucleotide tag addition site, or to an oligonucleotide tag having reacted with the oligonucleotide tag addition site or another oligonucleotide tag in a previous synthesis round, can involve an enzymatic extension reaction. The extension reaction can be performed by a polymerase or a ligase, or a combination thereof. The extension using a polymerase is suitably conducted using an oligonucleotide tag hybridised to an complementary tag oligonucleotide as template. The substrate is usually a blend of triphosphate nucleotides selected from the group comprising dATP, dGTP, dTTP, dCTP, rATP, rGTP, rTTP, rCTP, rUTP.

In a different embodiment, a ligase is used for the addition of an oligonucleotide tag using one or more oligonucleotides as substrates. The ligation can be performed in a single stranded or a double stranded state depending on the enzyme used. In general it is preferred to ligate oligonucleotide tags in a double stranded state, i.e. oligonucleotide tag oligonucleotides to be ligated together are kept together by a complementing oligonucleotide (complementary tag), which complements the ends of the two oligonucleotide tag oligonucleotides to be ligated.

Substrates for ligases are oligo- and polynucleotides, i.e. nucleic acids comprising two or more nucleotides. An enzymatic ligation can be performed in a single or double stranded fashion. When a single stranded ligation is performed, a 3' OH group of a first nucleic acid is ligated to a 5' phosphate group of a second nucleic acid. A double stranded ligation uses a third oligonucleotide complementing a part of the 3' end and 5' end of the first and second nucleic acid to assist in the ligation. Generally, it is preferred to perform a double stranded ligation. Only oligonucleotide tags are ligated. Complementary tags are not ligated as they do not, in one embodiment, comprise a reactive group, such as a 5'-P or a 3'-OH, or variants or derivatives thereof, enabling enzymatic ligation. In another embodiment, complementary tags do not abut to each other but are physically separated by hybridisation to parts of oligonucleotide tag oligonucleotides which are separated from each other. This is illustrated in FIG. 3.

In some embodiments of the invention, a combination of polymerase transcription and ligational coupling is used. As an example, a gap in an otherwise double stranded nucleic acid can be filled-in by a polymerase and a ligase can ligate the oligonucleotide tag portion of the extension product.

Examples of suitable polymerases include DNA polymerase, RNA polymerase, Reverse Transcriptase, DNA ligase, RNA ligase, Taq DNA polymerase, Pfu polymerase, Vent polymerase, HIV-1 Reverse Transcriptase, Klenow fragment, or any other enzyme that will catalyze the incorporation of complementing elements such as mono-, di- or polynucleotides. Other types of polymerases that allow mismatch extension could also be used, such for example DNA polymerase η (Washington et al., (2001) JBC 276: 2263-2266), DNA polymerase ι (Vaisman et al., (2001) JBC 276: 30615-30622), or any other enzyme that allow extension of mismatched annealed base pairs.

Suitable examples of ligases include Taq DNA ligase, T4 DNA ligase, T4 RNA ligase, T7 DNA ligase, and *E. coli* DNA ligase. The choice of the ligase depends, among other things, on the design of the ends to be joined together. Thus, if the ends are blunt, T4 RNA ligase can be preferred, while a Taq DNA ligase can be preferred for a sticky end ligation, i.e. a ligation in which an overhang on each end is a complement to each other.

Chemical Reaction Site, Reactive Compound Building Blocks and Reactive Groups

The synthesis of the molecule part of the bi-functional complexes according to the present invention involves reactions taking place between a chemical reaction site and one or more reactive compound building blocks and optionally also one or more reactions taking place between at least two reactive compound building blocks. The respective reactions are mediated by one or more reactive groups of the chemical reaction site and one or more groups of one or more reactive compound building blocks.

A reactive compound building block can participate in a reaction with the chemical reaction site and/or in a reaction with other reactive compound building blocks and contributes to the a chemical structure of the final molecule. The reaction between the chemical reaction site and the one or more reactive compound building blocks, or between individual reactive compound building blocks, can take place under any suitable condition that favours the reaction.

Generally, a molecule is formed by reacting several reactive compound building blocks with each other and/or with a chemical reaction site, such as a scaffold moiety comprising a plurality of reactive groups or sites. In one embodiment of the invention, a nascent bi-functional complex is reacted with one or more reactive compound building blocks and with the respective oligonucleotide tag(s) more than once preferably using a split-and-mix technique. The reactions can be repeated as often as necessary in order to obtain a molecule as one part of the bi-functional complex and an identifying oligonucleotide comprising the oligonucleotide tags identifying the reactive compound building blocks which participated in the formation of the molecule.

The synthesis of a molecule according to the methods of the present invention can proceed via particular type(s) of coupling reaction(s), such as, but not limited to, one or more of the reactive group reactions cited herein above. In some embodiments, combinations of two or more reactive group reactions will occur, such as combinations of two or more of the reactive group reactions discussed above, or combinations of the reactions disclosed in Table 1. For example, reactive compound building blocks can be joined by a combination of amide bond formation (amino and carboxylic acid complementary groups) and reductive amination (amino and aldehyde or ketone complementary groups).

The reaction of the reactive compound building block(s) with each other and/or with the chemical reaction site on the one hand and the reaction of oligonucleotide tag(s) with each other and/or with the oligonucleotide tag addition site on the other hand may occur sequentially in any order or simultaneously. The choice of order can be influenced by e.g. type of enzyme, reaction conditions used, and the type of reactive compound building block(s). The chemical reaction site can comprise a single or multiple reactive groups capable of reacting with one or more reactive compound building blocks. In a certain aspect the chemical reaction site comprises a scaffold having one or more reactive groups attached.

A round or cycle of reaction can imply that a) a single reactive compound building block is reacted with the chemical reaction site, such as a scaffold, or with one or more reactive compound building block(s) having reacted with the chemical reaction site during a previous reaction round, and b) that the respective oligonucleotide tag identifying the reactive compound building block is reacted with another oligonucleotide tag or with the oligonucleotide tag addition site. However, a round or cycle of reaction can also imply that a) multiple reactive compound building blocks are reacted with the chemical reaction site, such as a scaffold, or with one or more reactive compound building block(s) having reacted with the chemical reaction site during a previous reaction round, and b) that respective oligonucleotide tags identifying the reactive compound building blocks are reacted with each other and/or with another oligonucleotide tag and/or with the oligonucleotide tag addition site. At least one oligonucleotide tag reaction resulting in the oligonucleotide tag being attached to another oligonucleotide tag or to the oligonucleotide tag addition site involves one or more enzymes.

A reactive compound building block comprising one or more reactive compound building blocks and one or more reactive groups can have any chemical structure. At least one reactive group, or a precursor thereof, reacts with the chemical reaction site or one or more reactive group(s) of one or more other reactive compound building blocks. A "bridging molecule" can act to mediate a connection or form a bridge between two reactive compound building blocks or between a reactive compound building block and a chemical reaction site.

The invention can be performed by reacting a single reactive compound building block with the nascent bi-functional complex and add the corresponding oligonucleotide tag. However, it may be preferred to build a molecule comprising the reaction product of two of more reactive compound building blocks. Thus, in a certain aspect of the invention a method is devised for obtaining a bi-functional complex composed of a molecule part and a single stranded identifier oligonucleotide, said molecule part being the reaction product of reactive compound building blocks and the chemical reaction site of the initial complex.

In one embodiment of the invention, parallel syntheses are performed so that an oligonucleotide tag is enzymatical linked to a nascent bi-functional complex in parallel with a reaction between a chemical reaction site and a reactive compound building block. In each round the addition of the oligonucleotide tag is followed or preceded by a reaction between reactive compound building block and the chemical reaction site. In each subsequent round of parallel syntheses the reaction product of the previous reactions serves as the chemical reaction site and the last-incorporated oligonucleotide tag provides for an oligonucleotide tag addition site which allows for the enzymatical addition an oligonucleotide tag. In other aspects of the invention, two or more oligonucleotide tags are provided prior to or subsequent to reaction with the respective reactive compound building blocks.

The single stranded identifier oligonucleotide comprising covalently ligated oligonucleotide tags can be transformed to a double stranded form by an extension process in which a primer is annealed to the 3' end of the single stranded identifier oligonucleotide and extended using a suitable polymerase. The double strandness can be an advanoligonucleotide tage during subsequent selection processes.

Reactive compound building blocks can be synthesised e.g. as disclosed by Dolle et al. (Dolle, R. E. Mol. Div.; 3 (1998) 199-233; Dolle, R. E. Mol. Div.; 4 (1998) 233-256; Dolle, R. E.; Nelson, K. H., Jr. J. Comb. Chem.; 1 (1999) 235-282; Dolle, R. E. J. Comb. Chem.; 2 (2000) 383-433; Dolle, R. E. J. Comb. Chem.; 3 (2001) 477-517; Dolle, R. E. J. Comb. Chem.; 4 (2002) 369-418; Dolle, R. E. J. Comb. Chem.; 5 (2003) 693-753; Dolle, R. E. J. Comb. Chem.; 6 (2004) 623-679; Dolle, R. E. J. Comb. Chem.; 7 (2005) 739-798; Dolle, R. E.; Le Bourdonnec, B.; Morales, G. A.; Moriarty, K. J.; Salvino, J. M., J. Comb. Chem.; 8 (2006) 597-635 and references cited therein. (incorporated by reference herein in their entirety).

Reactive compound building blocks may furthermore be formed by use of solid phase synthesis or by in solution synthesis. Reactive compound building blocks may also be commercially available. Reactive compound building blocks may be produced by conventional organic synthesis, parallel synthesis or combinatorial chemistry methods.

The chemical reaction site can comprise a single reactive group or two or more reactive groups. In preferred embodiments, the chemical reaction site comprises 3 or more reactive groups. The plurality of reactive groups of a chemical reaction site can each react with one or more reactive compound building blocks each comprising one or more reactive groups linked to one or more reactive compound building blocks.

Reactive groups of the chemical reaction site are in principle no different from reactive groups of complementary reactive compound building blocks capable of reacting with each other under conditions allowing such a reaction to occur. Examples of reactive groups of chemical reaction sites and complementary reactive compound building blocks are listed in the detailed disclosure of the invention herein below.

Chemical reaction site reactive groups can be selected a variety of from well known reactive groups, such as e.g. hydroxyl groups, thiols, optionally substituted or activated carboxylic acids, isocyanates, amines, esters, thioesters, and the like. Further non-limiting examples of reactive group reactions are e.g. Suzuki coupling, Heck coupling, Sonogashira coupling, Wittig reaction, alkyl lithium-mediated condensations, halogenation, SN2 displacements (for example, N, O, S), ester formation, and amide formation, as well as other reactions and reactive groups that can be used to generate reactive compound building blocks, such as those presented herein.

In general, the chemical reaction site and reactive compound building blocks capable of reacting with the chemical reaction site, i.e. complementary reactive compound building blocks, can in principle be any chemical compounds which are complementary, that is the reactive groups of the entities in question must be able to react. Typically, a reactive compound building block can have a single reactive group or more than one reactive group, such as at least two reactive groups, although it is possible that some of the reactive compound building blocks used will have more than two reactive groups each. This will be the case when branched molecules are synthesised.

The number of reactive groups on present on a reactive compound building block and/or a chemical reaction site is suitably from 1 to 10, for example 1, such as 2, for example 3, such as 4, for example 5, such as 6, for example 7, such as 8, for example 9, such as from 2 to 4, for example from 4 to 6, such as from 6 to 8, for example from 8 to 10, such as from 2 to 6, for example from 6 to 10, such as from 3 to 6, for example from 6 to 9, such as from 4 to 6, for example from 6 to 10 reactive groups present on the chemical reaction site and/or a reactive compound building block capable of reacting with the chemical reaction site and/or with another reactive compound building block.

Reactive groups on two different reactive compound building blocks should be complementary, i.e., capable of reacting to form a covalent bond, optionally with the concomitant loss of a small molecular entity, such as water, HCl, HF, and so forth.

Two reactive groups are complementary if they are capable of reacting together to form a covalent bond. Complementary reactive groups of two reactive compound building blocks can react, for example, via nucleophilic substitution, to form a covalent bond. In one embodiment, one member of a pair of complementary reactive groups is an electrophilic group and the other member of the pair is a nucleophilic group. Examples of suitable electrophilic reactive groups include reactive carbonyl groups, such as acyl chloride groups, ester groups, including carbonylpentafluorophenyl esters and succinimide esters, ketone groups and aldehyde groups; reactive sulfonyl groups, such as sulfonyl chloride groups, and reactive phosphonyl groups. Other electrophilic reactive groups include terminal epoxide groups, isocyanate groups and alkyl halide groups. Suitable nucleophilic reactive groups include, but is not limited to, primary and secondary amino groups and hydroxyl groups and carboxyl groups.

Accordingly, complementary electrophilic and nucleophilic reactive groups include any two groups which react via nucleophilic substitution under suitable conditions to form a covalent bond. A variety of suitable bond-forming reactions are known in the art. See, for example, March, Advanced Organic Chemistry, fourth edition, New York: John Wiley and Sons (1992), Chapters 10 to 16; Carey and Sundberg, Advanced Organic Chemistry, Part B, Plenum (1990), Chapters 1-11; and Collman et al., Principles and Applications of Organotransition Metal Chemistry, University Science Books, Mill Valley, Calif. (1987), Chapters 13 to 20; each of which is incorporated herein by reference in its entirety.

Further suitable complementary reactive groups are set forth herein below. One of skill in the art can readily determine other reactive group pairs that can be used in the present method, such as, but not limited to, reactive groups capable of facilitating the reactions illustrated in Table 1.

In some embodiments, the reactive groups of the chemical reaction site and/or the reactive group(s) of one or more reactive compound building blocks reacting with each other and/or with the chemical reaction site are preferably selected from the group consisting of:

a) activated carboxyl groups, reactive sulfonyl groups and reactive phosphonyl groups, or a combination thereof, and complementary primary or secondary amino groups; the complementary reactive groups react under suitable conditions to form amide, sulfonamide and/or phosphonamidate bonds;

b) epoxide groups and complementary primary and/or secondary amino groups; a reactive compound building block comprising one or more epoxide reactive group(s) can react with one or more amine-group(s) of a complementary reactive compound building block under suitable conditions to form one or more carbon-nitrogen bond(s), resulting e.g. in a beta-amino alcohol;

c) aziridine groups and complementary primary or secondary amino groups; under suitable conditions, a reactive compound building block comprising one or more aziridine-group(s) can react with one or more amine-group(s) of a complementary reactive compound building block to form one or more carbon-nitrogen bond(s), resulting e.g. in a 1,2-diamine;

d) isocyanate groups and complementary primary or secondary amino groups, a reactive compound building block comprising one or more isocyanate-group(s) can react with one or more amino-group(s) of a complementary reactive compound building block under suitable conditions to form one or more carbon-nitrogen bond(s), resulting e.g. in a urea group;

e) isocyanate groups and complementary hydroxyl groups; a reactive compound building block comprising one or more isocyanate-group(s) can react with a complementary reactive compound building block comprising one or more hydroxyl-groups under suitable conditions to form one or more carbon-oxygen bond(s), resulting e.g. in a carbamate group.

f) amino groups and complementary carbonyl groups; a reactive compound building block comprising one or more amino groups can react with a complementary reactive compound building block comprising one or more carbonyl-group(s), such as aldehyde and/or a ketone group(s); the amines can react with such groups via reductive amination to form e.g. a carbon-nitrogen bond;

g) phosphorous ylide groups and complementary aldehyde and/or ketone groups; A reactive compound building block comprising a phosphorus-ylide-group can react with an aldehyde and/or a ketone-group of a complementary reactive compound building block under suitable conditions to form e.g. a carbon-carbon double bond, resulting e.g. in an alkene;

h) complementary reactive groups can react via cycloaddition to form a cyclic structure; an example of such complementary reactive groups are alkynes and organic azides, which can react under suitable conditions to form a triazole ring structure—suitable conditions for such reactions are known in the art and include those disclosed in WO 03/101972, the entire contents of which are incorporated by reference herein;

i) the complementary reactive groups are alkyl halide groups and one or more nucleophile group(s), such as, but not limited to, nucleophile groups selected from the group consisting of amino groups, hydroxyl groups and carboxyl group; such groups react under suitable conditions to form a carbon-nitrogen bond (alkyl halide plus amine) or carbon oxygen bond (alkyl halide plus hydroxyl or carboxyl group);

j) the complementary functional groups are halogenated heteroaromatic groups and one or more nucleophile group(s), the reactive compound building blocks are linked under suitable conditions via aromatic nucleophilic substitution; suitable halogenated heteroaromatic groups include chlorinated pyrimidines, triazines and purines, which react with nucleophiles, such as amines, under mild conditions in aqueous solution.

As will be clear from the above, a large variety of chemical reactions may be used for the formation of one or more covalent bonds between a reactive compound building block and one or more chemical reaction sites and a large variety of chemical reactions may be used for the formation of one or more covalent bonds between one or more reactive compound building blocks. It will be understood that some of these chemical reactions are preferably performed in solution while others are preferably performed while an optionally protected tag or identifier oligonucleotide linked to a chemical reaction site is further linked to a solid support, such as a bead.

Thus, reactions such as those listed in March's Advanced Organic Chemistry, Organic Reactions, Organic Syntheses, organic text books, journals such as Journal of the American Chemical Society, Journal of Organic Chemistry, Tetrahedron, etc., and Carruther's Some Modern Methods of Organic Chemistry can be used.

The chosen reaction conditions are preferably compatible with the presence in a nascent bi-functional complex of optionally protected nucleic acids and oligonucleotides, such as DNA or RNA, or the reaction conditions are compatible with optionally protected modified nucleic acids.

Reactions useful in molecule synthesis include, for example, substitution reactions, carbon-carbon bond forming reactions, elimination reactions, acylation reactions, and addition reactions. An illustrative but not exhaustive list of aliphatic nucleophilic substitution reactions useful in the present invention includes, for example, SN2 reactions, SNI reactions, SNi reactions, allylic rearrangements, nucleophilic substitution at an aliphatic trigonal carbon, and nucleophilic substitution at a vinylic carbon. Specific aliphatic nucleophilic substitution reactions with oxygen nucleophiles include, for example, hydrolysis of alkyl halides, hydrolysis of gen-dihalides, hydrolysis of 1,1,1-trihalides, hydrolysis of alkyl esters or inorganic acids, hydrolysis of diazo ketones, hydrolysis of acetal and enol ethers, hydrolysis of epoxides, hydrolysis of acyl halides, hydrolysis of anhydrides, hydrolysis of carboxylic esters, hydrolysis of amides, alkylation with alkyl halides (Williamson Reaction), epoxide formation, alkylation with inorganic esters, alkylation with diazo compounds, dehydration of alcohols, transetherification, alcoholysis of epoxides, alkylation with onium salts, hydroxylation of silanes, alcoholysis of acyl halides, alcoholysis of anhydrides, esterfication of carboxylic acids, alcoholysis of carboxylic esters (transesterfication), alcoholysis of amides, alkylation of carboxylic acid salts, cleavage of ether with acetic anhydride, alkylation of carboxylic acids with diazo compounds, acylation of carboxylic acids with acyl halides; acylation of carlpoxylic acids with carboxylic acids, formation of oxoniiim salts, preparation of peroxides arid hydroperoxides, preparation of inorganic esters (e.g., nitrites, nitrates, sulfonates), preparation of alcohols from amines, arid preparation of mixed organic-inorganic anhydrides.

Specific aliphatic nucleophilic substitution reactions with sulfur nucleophiles, which tend to be better nucleophiles than their oxygen analogs, include, for example, attack by SH at an alkyl carbon to form thiols, attack by S at an alkyl carbon to form thioethers, attack by SH or SR at an acyl carbon, formation of disulfides formation of Bunte salts, alkylation of sulfuric acid salts, and formation of alkyl thiocyanates.

Aliphatic nucleophilic substitution reactions with nitrogen nucleophiles include, for example, alkylation of amines, N-arylation of amines, replacement of a hydroxy by an amino group, transamination, transamidation, alkylation of amines with diazo compounds, animation of epoxides, amination of oxetanes, amination of aziridines, amination of alkanes, formation of isocyanides, acylation of amines by acyl halides, acylation of amines by anhydrides, acylation of amines by carboxylic acids, acylation of amines by carboxylic esters, acylation of amines by amides, acylation of amines by other acid derivatives, N-alkylation or N-arylation of amides and imides, N-acylation of amides and imides, formation of aziridines from epoxides, formation of nitro compounds, formation of azides, formation of isocyanates and isothiocyanates, and formation of azoxy compounds. Aliphatic nucleophilic substitution reactions with halogen nucleophiles include, for example, attack at an alkyl carbon, halide exchange, formation of alkyl halides from esters of sulfuric and sulfonic acids, formation of alkyl halides from alcohols, formation of alkyl halides from ethers, formation of halohydrins from epoxides, cleavage of carboxylic esters with lithium iodide, conversion of diazo ketones to alpha-halo ketones, conversion of amines to halides, conversion of tertiary amines to cyanamides (the von Braun reaction), formation of acyl halides from carboxylic acids, and formation of acyl halides from acid derivatives.

Aliphatic nucleophilic substitution reactions using hydrogen as a nucleophile include, for example, reduction of alkyl halides, reduction of tosylates, other sulfonates, and similar compounds, hydrogenolysis of alcohols, hydrogenolysis of esters (Barton-McCombie reaction), hydrogenolysis of nitriles, replacement of alkoxyl by hydrogen, reduction of epoxides, reductive cleavage of carboxylic esters, reduction of a C—N bond, desulfurization, reduction of acyl halides, reduction of carboxylic acids, esters, and anhydrides to aldehydes, and reduction of amides to aldehydes.

Although certain carbon nucleophiles may be too nucleophilic and/or basic to be used in certain embodiments of the invention, aliphatic nucleophilic substitution reactions using carbon nucleophiles include, for example, coupling with silanes, coupling of alkyl halides (the Wurtz reaction), the reaction of alkyl halides and sulfonate esters with Group I (I A), and II (II A) organometallic reagents, reaction of alkyl halides and sulfonate esters with organocuprates, reaction of alkyl halides and sulfonate esters with other organometallic reagents; allylic and propargylic coupling with a halide substrate, coupling of organometallic reagents with esters of sulfuric and sulfonic acids, sulfoxides, and sulfones, coupling involving alcohols, coupling of organometallic reagents with carboxylic esters, coupling of organometallic reagents with compounds containing an ester linkage, reaction of organometallic reagents with epoxides, reaction of organometallics with aziridine, alkylation at a carbon bearing an active hydrogen, alkylation of ketones, nitriles, and carboxylic esters, alkylation of carboxylic acid salts, alkylation at a position alpha to a heteroatom (alkylation of 1,3-dithianes), alkylation of dihydro-1,3-oxazine (the Meyers synthesis of aldehydes, ketones, and carboxylic acids), alkylation with trialkylboranes, alkylation at an alkynyl carbon, preparation of nitriles, direct conversion of alkyl halides to aldehydes and ketones, conversion of alkyl halides, alcohols, or alkanes to carboxylic acids and their derivatives, the conversion of acyl halides to ketones with organometallic compounds, the conversion of anhydrides, carboxylic esters, or amides to ketones with organometallic compounds, the coupling of acyl halides, acylation at a carbon bearing an active hydrogen, acylation of carboxylic esters by carboxylic esters (the Claisen and Dieckmann condensation), acylation of ketones and nitriles with carboxylic esters, acylation of carboxylic acid salts, preparation of acyl cyanides, and preparation of diazo ketones, ketonic decarboxylation. Reactions which involve nucleophilic attack at a sulfonyl sulfur atom may also be used in the present invention and include, for example, hydrolysis of sulfonic acid derivatives (attack by OH), formation of sulfonic esters (attack by OR), formation of sulfonamides (attack by nitrogen), formation of sulfonyl halides (attack by halides), reduction of sulfonyl chlorides (attack by hydrogen), and preparation of sulfones (attack by carbon).

Aromatic electrophilic substitution reactions may also be used in molecule synthesis schemes according to the present invention. Hydrogen exchange reactions are examples of aromatic electrophilic substitution reactions that use hydrogen as the electrophile. Aromatic electrophilic substitution, reactions which use nitrogen electrophiles include, for example, nitration and nitro-dehydrogenation, nitrosation of nitroso-de-hydrogenation, diazonium coupling, direct introduction of the diazonium group, and amination or amino-dehydrogenation. Reactions of this type with sulfur electrophiles include, for example, sulfonation, sulfo-dehydrogenation, halosulfonation, halosulfo-dehydrogenation, sulfurization, and sulfonylation. Reactions using halogen electrophiles include, for example, halogenation, and halo-dehydrogenation. Aromatic electrophilic substitution reactions with carbon electrophiles include, for example, Friedel-Crafts alkylation, alkylation, alkyl-dehydrogenation, Friedel-Crafts arylation (the Scholl reaction), Friedel-Crafts acylation, formylation with disubstituted formamides, formylation with zinc cyanide and HCl (the Gatterman reaction), formylation with chloroform (the Reimer-Tiemami reaction), other formylations, formyl-dehydrogenation, carboxylation with carbonyl halides, carboxylation with carbon dioxide (the Kolbe-Schmitt reaction), amidation with isocyanates, N-alkylcarbamoyl-dehydrogenation, hydroxyalkylation, hydroxyalkyl-dehydrogenation, cyclodehydration of aldehydes and ketones, haloalkylation, halo-dehydrogenation, aminoalkylation, amidoalkylation, dialkylaminoalkylation, dialkylamino-dehydrogenation, thioalkylation, acylation with nitriles (the Hoesch reaction), cyanation, and cyano-dehydrogenation. Reactions using oxygen electrophiles include, for example, hydroxylation and hydroxy-dehydrogenation.

Rearrangement reactions include, for example, the Fries rearrangement, migration of a nitro group, migration of a nitroso group (the Fischer-Hepp Rearrangement), migration of an arylazo group, migration of a halogen (the Orton rearrangement), migration of an alkyl group, etc. Other reaction on an aromatic ring include the reversal of a Friedel-Crafts alkylation, decarboxylation of aromatic aldehydes, decarboxylation of aromatic acids, the Jacobsen reaction, deoxygenation, desulfonation, hydro-desulfonation, dehalogenation, hydro-dehalogenation, and hydrolysis of organometallic compounds.

Aliphatic electrophilic substitution reactions are also useful. Reactions using the SE1, SE2 (front), SE2 (back), SEi, addition-elimination, and cyclic mechanisms can be used in the present invention. Reactions of this type with hydrogen as the leaving group include, for example, hydrogen exchange (deuterio-de-hydrogenation, deuteriation), migration of a double bond, and keto-enol tautomerization. Reactions with halogen electrophiles include, for example, halogenation of aldehydes and ketones, halogenation of carboxylic acids and acyl halides, and halogenation of sulfoxides and sulfones. Reactions with nitrogen electrophiles include, for example, aliphatic diazonium coupling, nitrosation at a carbon bearing an active hydrogen, direct formation of diazo compounds, conversion of amides to alpha-azido amides, direct amination at an activated position, and insertion by nitrenes. Reactions with sulfur or selenium electrophiles include, for example, sulfenylation, sulfonation, and selenylation of ketones and carboxylic esters. Reactions with carbon electrophiles include, for example, acylation at an aliphatic carbon, conversion of aldehydes to beta-keto esters or ketones, cyanation, cyano-de-hydrogenation, alkylation of alkanes, the Stork enamine reaction, and insertion by carbenes. Reactions with metal electrophiles include, for example, metalation with organometallic compounds, metalation with metals and strong bases, and conversion of enolates to silyl enol ethers. Aliphatic electrophilic substitution reactions with metals as leaving groups include, for example, replacement of metals by hydrogen, reactions between organometallic reagents and oxygen, reactions between organometallic reagents and peroxides, oxidation of trialkylboranes to borates, conversion of Grignard reagents to sulfur compounds, halo-demetalation, the conversion of organometallic compounds to amines, the conversion of organometallic compounds to ketones, aldehydes, carboxylic esters and amides, cyano-de-metalation, transmetalation with a metal, transmetalation with a metal halide, transmetalation with an organometallic compound, reduction of alkyl halides, metallo-de-halogenation, replacement of a halogen by a metal from an organometallic compound, decarboxylation of aliphatic acids, cleavage of aikoxides, replacement of a carboxyl group by an acyl group, basic cleavage of beta-keto esters and beta-diketones, haloform reaction, cleavage of non-enolizable ketones, the Haller-Bauer reaction, cleavage of alkanes, decyanation, and hydro-de-cyanation. Electrophilic substitution reactions at nitrogen include, for example, diazotization, conversion of hydrazines to azides, N-nitrosation, N-nitroso-de-hydrogenation, conversion of amines to azo compounds, N-halogenation, N-halo-dehydrogenation, reactions of amines with carbon monoxide, and reactions of amines with carbon dioxide. Aromatic nudeophilic substitution reactions may also be used in the present invention. Reactions proceeding via the SNAr mechanism, the SNI mechanism, the benzyne mechanism, the SRN1 mechanism, or other mechanism, for example, can be used. Aromatic nudeophilic substitution reactions with oxygen nucleophiles include, for example, hydroxy-de-halogenation, alkali fusion of sulfonate salts, and replacement of OR or OAr. Reactions with sulfur nucleophiles include, for example, replacement by SH or SR. Reactions using nitrogen nucleophiles include, for example, replacement by NH2, NHR, or NR2, and replacement of a hydroxy group by an amino group: Reactions with halogen nucleophiles include, for example, the introduction halogens. Aromatic nudeophilic substitution reactions with hydrogen as the nucleophile include, for example, reduction of phenols and phenolic esters and ethers, and reduction of halides and nitro compounds. Reactions with carbon nucleophiles include, for example, the Rosenmund-von Braun reaction, coupling of organometallic compounds with aryl halides, ethers, and carboxylic esters, arylation at a carbon containing an active hydrogen, conversions of aryl substrates to carboxylic acids, their derivatives, aldehydes, and ketones, and the Ullmann reaction. Reactions with hydrogen as the leaving group include, for example, alkylation, arylation, and amination of nitrogen heterocycles. Reactions with N2+ as the leaving group include, for example, hydroxy-de-diazoniation, replacement by sulfur-containing groups, iodo-de-diazoniation, and the Schiemann reaction. Rearrangement reactions include, for example, the von Richter rearrangement, the Sommelet-Hauser rearrangement, rearrangement of aryl hydroxylamines, and the Smiles rearrangement. Reactions involving free radicals can also be used, although the free radical reactions used in nucleotide-templated chemistry should be carefully chosen to avoid modification or cleavage of the nucleotide template. With that limitation, free radical substitution reactions can be used in the present invention. Particular free radical substitution reactions include, for example, substitution by halogen, halogenation at an alkyl carbon, allylic halogenation, benzylic halogenation, halogenation of aldehydes, hydroxylation at an aliphatic carbon, hydroxylation at an aromatic carbon, oxidation of aldehydes to carboxylic acids, formation of cyclic ethers, formation of hydroperoxides, formation of peroxides, acyloxylation, acyloxy-de-hydrogenation, chlorosulfonation, nitration of alkanes, direct conversion of aldehydes to amides, amidation and amination at an alkyl carbon, simple coupling at a susceptible position, coupling of alkynes, arylation of aromatic compounds by diazonium salts, arylation of activated alkenes by diazonium salts (the Meerwein arylation), arylation and alkylation of alkenes by organopalladium compounds (the Heck reaction), arylation and alkylation of alkenes by vinyltin compounds (the StHle reaction), alkylation and arylation of aromatic compounds by peroxides, photochemical arylation of aromatic compounds, alkylation, acylation, and carbalkoxylation of nitrogen heterocycles. Particular reactions in which N2+ is the leaving group include, for example, replacement of the diazonium group by hydrogen, replacement of the diazonium group by chlorine or bromine, nitro-de-diazonization, replacement of the diazonium group by sulfur-containing groups, aryl dimerization with diazonium salts, methylation of diazonium salts, vinylation of diazonium salts, arylation of diazonium salts, and conversion of diazonium salts to aldehydes, ketones, or carboxylic acids. Free radical substitution reactions with metals as leaving groups include, for example, coupling of Grignard reagents, coupling of boranes, and coupling of other organometallic reagents. Reaction with halogen as the leaving group are included. Other free radical substitution reactions with various leaving groups include, for example, desulfurization with Raney Nickel, conversion of sulfides to organolithium compounds, decarboxylase dimerization (the Kolbe reaction), the Hunsdiecker reaction, decarboxylative allylation, and decarbonylation of aldehydes and acyl halides.

Reactions involving additions to carbon-carbon multiple bonds are also used in the molecule synthesis schemes. Any mechanism may be used in the addition reaction including, for example, electrophilic addition, nucleophilic addition, free radical addition, and cyclic mechanisms. Reactions involving additions to conjugated systems can also be used. Addition to cyclopropane rings can also be utilized. Particular reactions include, for example, isomerization, addition of hydrogen halides, hydration of double bonds, hydration of triple bonds, addition of alcohols, addition of carboxylic acids, addition of $H_2S$ and thiols, addition of ammonia and amines, addition of amides, addition of hydrazoic acid, hydrogenation of double and triple bonds, other reduction of double and triple bonds, reduction of the double and triple bonds of conjugated systems, hydrogenation of aromatic rings, reductive cleavage of cyclopropanes, hydroboration, other hydrometalations, addition of alkanes, addition of alkenes and/or alkynes to alkenes and/or alkynes (e.g., pi-cation cyclization reactions, hydro-alkenyl-addition), ene reactions, the Michael reaction, addition of organometallics to double and triple bonds not conjugated to carbonyls, the addition of two alkyl groups to an alkyne, 1,4-addition of organometallic compounds to activated double bonds, addition of boranes to activated double bonds, addition of tin and mercury hydrides to activated double bonds, acylation of activated double bonds and of triple bonds, addition of alcohols, amines, carboxylic esters, aldehydes, etc., carbonylation of double and triple bonds, hydrocarboxylation, hydroformylation, addition of aldehydes, addition of HCN, addition of silanes, radical addition, radical cydization, halogenation of double and triple bonds (addition of halogen, halogen), halolactonization, halolactamization, addition of hypohalous acids and hypohalites (addition of halogen, oxygen), addition of sulfur compounds (addition of halogen, sulfur), addition of halogen and an amino group (addition of halogen, nitrogen), addition of NOX and $NO_2X$ (addition of halogen, nitrogen), addition of $XN_3$ (addition of halogen, nitrogen), addition of alkyl halides (addition of halogen, carbon), addition of acyl halides (addition of halogen, carbon), hydroxylation (addition of oxygen, oxygen) (e.g., asymmetric dihydroxylation reaction with $OSO_4$), dihydroxylation of aromatic rings, epoxidation (addition of oxygen, oxygen) (e.g., Sharpless asymmetric epoxidation), photooxidation of dienes (addition of oxygen, oxygen), hydroxysulfenylation (addition of oxygen, sulfur), oxyamination (addition of oxygen, nitrogen), diamination (addition of nitrogen, nitrogen), formation of aziridines (addition of nitrogen), aminosulferiylation (addition of nitrogen, sulfur), acylacyloxylation and acylamidation (addition of oxygen, carbon or nitrogen, carbon), 1,3-dipolar addition; (addition of oxygen, nitrogen, carbon), Diels-Alder reaction, heteroatom Diels-Alder reaction, all carbon 3+2 cycloadditions, dimerization of alkenes, the addition of carbenes and carbenoids to double and triple bonds, trimerization and tetramerization of alkynes, and other cycloaddition reactions.

In addition to reactions involving additions to carbon-carbon multiple bonds, addition reactions to carbon-hetero multiple bonds can be used in nucleotide-templated chemistry. Exemplary reactions include, for example, the addition of water to aldehydes and ketones (formation of hydrates), hydrolysis of carbon-nitrogen double bond, hydrolysis of aliphatic nitro compounds, hydrolysis of nitriles, addition of alcohols and thiols to aldehydes and ketones, reductive alkylation of alcohols, addition of alcohols to isocyanates, alcoholysis of nitriles, formation of xanthates, addition of H2S and thiols to carbonyl compounds, formation of bisulfite addition products, addition of amines to aldehydes and ketones, addition of amides to aldehydes, reductive alkylation of ammonia or amines, the Mannich reaction, the addition of amines to isocyanates, addition of ammonia or amines to nitriles, addition of amines to carbon disulfide and carbon dioxide, addition of hydrazine derivative to carbonyl compounds, formation of oximes, conversion of aldehydes to nitriles, formation of gem-dihalides from aldehydes and ketones, reduction of aldehydes and ketones to alcohols, reduction of the carbon-nitrogen double bond, reduction of nitriles to amines, reduction of nitriles to aldehydes, addition of Grignard reagents and organolithium reagents to aldehydes and ketones, addition of other organometallics to aldehydes and ketones, addition of trialkylallylsilanes to aldehydes and ketones, addition of conjugated alkenes to aldehydes (the Baylis-Billmah reaction), the Reformatsky reaction, the conversion of carboxylic acid salts to ketones with organometallic compounds, the addition of Grignard reagents to acid derivatives, the addition of Organometallic compounds to CO2 and CS2, addition of organometallic compounds to C=IM compounds, addition of carbenes and diazoalkanbs to C=N compounds, addition of Grignard reagents to nitriles and isocyanates, the Aldol reaction, Mukaiyama Aldol and related reactions, Aldol-type reactions between carboxylic esters or amides and aldehydes or ketones, the Knoevenagel reaction (e.g., the Nef reaction, the Favorskii reaction), the Peterson alkenylation reaction, the addition of active hydrogen compounds to CO2 and CS2, the Perkin reaction, Darzens glycidic ester condensation, the Tollens reaction, the Wittig reaction, the Tebbe alkenylation, the Petasis alkenylation, alternative alkenylations, the Thorpe reaction, the Thorpe-Ziegler reaction, addition of silanes, formation of cyanohydrins, addition of HCN to C=N and C—N bonds, the Prins reaction, the benzoin condensation, addition of radicals to C=O, C=S, C=N compounds, the Ritter reaction, acylation of aldehydes and ketones, addition of aldehydes to aldehydes, the addition of isocyanates to isocyanates (formation of carbodiimides), the conversion of carboxylic acid salts to nitriles, the formation of epoxides from aldehydes and ketones, the formation of episulfides and episulfones, the formation of beta-lactones and oxetanes (e.g., the Paterno-Buchi reaction), the formation of beta-lactams, etc. Reactions involving addition to isocyanides include the addition of water to isocyanides, the Passerini reaction, the Ug reaction, and the formation of metalated aldimines. Elimination reactions, including alpha, beta, and gamma eliminations, as well as extrusion reactions, can be performed using nucleotide-templated chemistry, although the strength of the reagents and conditions employed should be considered. Preferred elimination reactions include reactions that go by El, E2, ElcB, or E2C mechanisms. Exemplary reactions include, for example, reactions in which hydrogen is removed from one side (e.g., dehydration of alcohols, cleavage of ethers to alkenes, the Chugaev reaction, ester decomposition, cleavage of quarternary ammonium hydroxides, cleavage of quaternary ammonium salts with strong bases, cleavage of amine oxides, pyrolysis of keto-ylids, decomposition of toluene-p-sulfonylhydrazones, cleavage of sulfoxides, cleavage of selenoxides, cleavage of sulfornes, dehydrogalogenation of alkyl halides, dehydrohalogenation of acyl halides, dehydrohalogenation of sulfonyl halides, elimination of boranes, conversion of alkenes to alkynes, decarbonylation of acyl halides), reactions in which neither leaving atom is hydrogen (e.g., deoxygenation of vicinal diols, cleavage of cyclic thionocarbonates, conversion of epoxides to episulfides and alkenes, the Ramberg-Backlund reaction, conversion of aziridines to alkenes, dehalogenation of vicinal dihalides, dehalogenation of alpha-halo acyl halides, and elimination of a halogen and a hetero group), fragmentation reactions (i.e., reactions in which carbon is the positive leaving group or the electrofuge, such as, for example, fragmentation of gamma-amino and gamma-hydroxy halides, fragmentation of 1,3-diols, decarboxylation of beta-hydroxy carboxylic acids, decarboxylation of (3-lactones, fragmentation of alpha-beta-epoxy hydrazones, elimination of CO from bridged bicydic compounds, and elimination Of CO2 from bridged bicydic compounds), reactions in which C=N or C=N bonds are formed (e.g., dehydration of aldoximes or similar compounds, conversion of ketoximes to nitriles, dehydration of unsubstituted amides, and conversion of N-alkylformamides to isocyanides), reactions in which C=O bonds are formed (e.g., pyrolysis of beta-hydroxy alkenes), and reactions in which N=N bonds are formed (e.g., eliminations to give diazoalkenes). Extrusion reactions include, for example, extrusion of N2 from pyrazolines, extrusion of N2 from pyrazoles, extrusion of N2 from triazolines, extrusion of CO, extrusion Of CO2, extrusion Of SO2, the Story synthesis, and alkene synthesis by twofold extrusion.

Rearrangements, including, for example, nudeophilic rearrangements, electrophilic rearrangements, prototropic rearrangements, and free-radical rearrangements, can also be performed using molecule synthesis schemes. Both 1,2 rearrangements and non-1,2 rearrangements can be performed. Exemplary reactions include, for example, carbon-to-carbon migrations of R, H, and Ar (e.g., Wagner-Meerwein and related reactions, the Pinacol rearrangement, ring expansion reactions, ring contraction reactions, acid-catalyzed rearrangements of aldehydes and ketones, the dienone-phenol rearrangement, the Favorskii rearrangement, the Arndt-Eistert synthesis, homologation of aldehydes, and homologation of ketones), carbon-to-carbon migrations of other groups (e.g., migrations of halogen, hydroxyl, amino, etc.; migration of boron; and the Neber rearrangement), carbon-to-nitrogen migrations of R and Ar (e.g., the Hofmann rearrangement, the Curtius rearrangement, the Lossen rearrangement, the Schmidt reaction, the Beckman rearrangement, the Stieglits rearrangement, and related rearrangements), carbon-to-oxygen migrations of R and Ar (e.g., the Baeyer-Villiger rearrangement and rearrangement of hydroperoxides), nitrogen-to-carbon, oxygen-to-carbon, and sulfur-to-carbon migration (e.g., the Stevens rearrangement, and the Wittig rearrangement), boron-to-carbon migrations (e.g., conversion of boranes to alcohols (primary or otherwise), conversion of boranes to aldehydes, conversion of boranes to carboxylic acids, conversion of vinylic boranes to alkenes, formation of alkynes from boranes and acetylides, formation of alkenes from boranes and acetylides, and formation of ketones from boranes and acetylides), electrocyclic rearrangements (e.g., of cyclobutenes and 1,3-cyclohexadienes, or conversion of stilbenes to phenanthrenes), sigmatropic rearrangements (e.g., (1,j) sigmatropic migrations of hydrogen, (Ij) sigmatropic migrations of carbon, conversion of vinylcyclopropanes to cyclopentenes, the Cope rearrangement, the Claisen rearrangement, the Fischer indole synthesis, (2,3) sigmatropic rearrangements, and the benzidine rearrangement), other cyclic rearrangements (e.g., metathesis of alkenes, the di-n-methane and related rearrangements, and the Hofmann-Loffler and related reactions), and non-cyclic rearrangements (e.g., hydride shifts, the Chapman rearrangement, the Wallach rearrangement, and dybtropic rearrangements). Oxidative and reductive reactions may also be performed using molecule synthesis schemes. Exemplary reactions may involve, for example, direct electron transfer, hydride transfer, hydrogen-atom transfer, formation of ester intermediates, displacement mechanisms, or addition-elimination mechanisms. Exemplary oxidations include, for example, eliminations of hydrogen (e.g., aromatization of six-membered rings, dehydrogenations yielding carbon-carbon double bonds, oxidation or dehydrogenation of alcohols to aldehydes and ketones, oxidation of phenols and aromatic amines to quinones, oxidative cleavage of ketones, oxidative cleavage of aldehydes, oxidative cleavage of alcohols, ozonolysis, oxidative cleavage of double bonds and aromatic rings, oxidation of aromatic side chains, oxidative decarboxylation, and bisdecarboxylation), reactions involving replacement of hydrogen by oxygen (e.g., oxidation of methylene to carbonyl, oxidation of methylene to OH, CO2R, or OR, oxidation of arylmethanes, oxidation of ethers to carboxylic esters and related reactions, oxidation of aromatic hydrocarbons to quinones, oxidation of amines or nitro compounds to aldehydes, ketones, or dihalides, oxidation of primary alcohols to carboxylic acids or carboxylic esters, oxidation of alkenes to aldehydes or ketones, oxidation of amines to nitroso compounds and hydroxylamines, oxidation of primary amines, oximes, azides, isocyanates, or nitroso compounds, to nitro compounds, oxidation of thiols and other sulfur compounds to sulfonic acids), reactions in which oxygen is added to the substrate (e.g., oxidation of alkynes to alpha-diketones, oxidation of tertiary amines to amine oxides, oxidation of thioesters to sulfoxides and sulfones, and oxidation of carboxylic acids to peroxy acids, and oxidative coupling reactions (e.g., coupling involving carbanoins, dimerization of silyl enol ethers or of lithium enolates, and oxidation of thiols to disulfides).

Exemplary reductive reactions include, for example, reactions involving replacement of oxygen by hydrogen {e.g., reduction of carbonyl to methylene in aldehydes and ketones, reduction of carboxylic acids to alcohols, reduction of amides to amines, reduction of carboxylic esters to ethers, reduction of cyclic anhydrides to lactones and acid derivatives to alcohols, reduction of carboxylic esters to alcohols, reduction of carboxylic acids and esters to alkanes, complete reduction of epoxides, reduction of nitro compounds to amines, reduction of nitro compounds to hydroxylamines, reduction of nitroso compounds and hydroxylamines to amines, reduction of oximes to primary amines or aziridines, reduction of azides to primary amines, reduction of nitrogen compounds, and reduction of sulfonyl halides and sulfonic acids to thiols), removal of oxygen from the substrate {e.g., reduction of amine oxides and azoxy compounds, reduction of sulfoxides and sulfones, reduction of hydroperoxides and peroxides, and reduction of aliphatic nitro compounds to oximes or nitrites), reductions that include cleavage {e.g., de-alkylation of amines and amides, reduction of azo, azoxy, and hydrazo compounds to amines, and reduction of disulfides to thiols), reductive coupling reactions {e.g., bimolecular reduction of aldehydes and ketones to 1,2-diols, bimolecular reduction of aldehydes or ketones to alkenes, acyloin ester condensation, reduction of nitro to azoxy compounds, and reduction of nitro to azo compounds), and reductions in which an organic substrate is both oxidized and reduced {e.g., the Cannizzaro reaction, the Tishchenko reaction, the Pummerer rearrangement, and the Willgerodt reaction).

In one embodiment, a reactive group may comprise a nitrogen atom such as for example an amine, an isocyanate, an isocyanide, a hydroxylamine, a hydrazine, a nitrile, an amide, a lactam, an imine, an azo group, a nitro group, a nitroso group, an amidine group, a guanidine group, a carbamate, an azide, which may optionally be substituted by one or more substituents depending on the type of reactive group.

In one embodiment, a reactive group may comprise an oxygen atom such as for example a hydroxyl group, an ether, a ketone, an aldehyde, a hemiacetal, a hemiketal, an acetal, a ketal, a carboxylic acid, a carboxylic acid ester, an ortho ester, a carbonate, a carbamate, a lactam, a lactone, a hydroxylamine, which may optionally be substituted by one or more substituents depending on the type of reactive group.

In one embodiment, a reactive group may comprise a sulfur atom such as for example a thiol, a disulfide, a sulfide, a sulfoxide, a sulfin amide, a sulfonamide, a sulfone, a sultam, a sultone, a thioketone, a thioaldehyde, a dithioacetal, a carboxylic acid thioester, a thiocarbonate, a thiocarbamate, a isothiocyanate, which may optionally be substituted by one or more substituents depending on the type of reactive group.

In one embodiment, a reactive group may comprise a halogen such as for example fluorine, chlorine, bromine, iodine, for example alkylchloride, alkylbromide, alkyliodide, alkenylchloride, alkenylbromide, alkenyliodide, alkynylchloride, alkynylbromide, alkynyliodide, arylfluoride, arylchloride, arylbromide, aryliodide, hetarylfluoride, hetarylchloride, hetarylbromide, hetaryliodide, carbonylfluoride, carbonylchloride, carbonylbromide, carbonyliodide, sulfonylfluoride, sulfonylchloride, sulfonylbromide, sulfonyliodide, which may optionally be substituted by one or more substituents depending on the type of reactive group.

In one embodiment, a reactive group may comprise a carbon atom such as for example an alkene, an alpha,beta-unsaturated ketone, an alpha,beta-unsaturated aldehyde, an alpha,beta-unsaturated carboxylic acid ester, an alpha,beta-unsaturated carboxylic acid amide, an alpha,beta-unsaturated sulfoxide, an alpha,beta-unsaturated sulfone, an alpha,beta-unsaturated sulfonamide, an alpha,beta-unsaturated sulfonylchloride, a nitro alkene, such as a vinylogous nitro group (alpha,beta-unsaturated nitroalkene), an alkyne, an arene, a hetarene, a nitrile, an amide, a lactam, an imine, a nitroalkyl group, a nitroaryl group, an amidine group, a carbamate, a ketone, an aldehyde, a hemiacetal, a hemiketal, an acetal, a ketal, a carboxylic acid, a carboxylic acid ester, an ortho ester, a carbonate, a carbamate, a lactam, a lactone, a carbosulfone, a carbosultam, a carbosultone, a thioketone, a thioaldehyde, a dithioacetal, a carboxylic acid thioester, a thiocarbonate, a thiocarbamate, an alkylchloride, an alkylbromide, an alkyliodide, an alkenylchloride, an alkenylbromide, an alkenyliodide, an alkynylchloride, an alkynylbromide, an alkynyliodide, an arylfluoride, an arylchloride, an arylbromide, an aryliodide, an hetarylfluoride, an hetarylchloride, an hetarylbromide, an hetaryliodide, an carbonylfluoride, an carbonylchloride, an carbonylbromide, an carbonyliodide, an isocyanate, an isothiocyanate, an isocyanide, a alkylphosphonium group such as for example alkyltriphenylphosphonium chloride, for example alkyltriphenylphosphonium bromide, for example alkyltriphenylphosphonium iodide, which may optionally be substituted by one or more substituents depending on the type of reactive group.

Reactive groups may also comprising further functional groups as described in Comprehensive Organic Functional Group Transformations, Eds. A. R. Katritsky, O. Meth-Cohn, C. W. Rees, Pergamon, Elsevier 1995 Volumes 1-6, which are hereby incorporated by reference.

A chemical reactive site may comprise one or more reactive groups for example chemical reactive sites comprising 1-10 reactive groups, for example one reactive group, for example two reactive groups, for example three reactive groups, for example four reactive groups, for example five reactive groups.

A reactive compound building block may comprise one or more reactive groups for example reactive compound building blocks comprising 1-10 reactive groups, for example one reactive group, for example two reactive groups, for example three reactive groups, for example four reactive groups, for example five reactive groups.

In one embodiment, a reactive compound building block comprises two reactive groups, such as for example a diamine, an aminoketone, an aminoalcohol, an aminothiol, an aminoacid, such as for example an amino carboxylic acid, an aminoacid ester such as for example and amino carboxylic acid ester, an aminoacid amide such as for example an amino carboxylic acid amide, an amino chloroazine such as for example an amino chloropyridine, for example an amino chloropyrimidine, an amino chloropyridazine, an amino chloropyrazine, an amino fluoroazine such as for example an amino fluoropyridin, for example an amino fluoropyrimidine, an amino fluoropyridazine, an amino fluoro pyrazine, an Fmoc protected diamine, an Fmoc protected aminoketone, an Fmoc protected aminoalcohol, an Fmoc protected aminoacid such as for example an Fmoc protected amino carboxylic acid, an Fmoc protected aminoacid ester such as for example an Fmoc protected amino carboxylic acid ester, an Fmoc protected aminoacid amide such as for example an Fmoc protected amino carboxylic acid amide, an Fmoc protected aminoisocyanate, an Fmoc protected amino chloroazine such as for example an Fmoc protected amino chloropyridine, for example an Fmoc protected amino chloropyrimidine, an Fmoc protected amino chloropyridazine, an Fmoc protected amino chloropyrazine, an Fmoc protected amino fluoroazine such as for example an Fmoc protected amino fluoropyridin, for example an Fmoc protected amino fluoropyrimidine, an Fmoc protected amino fluoropyridazine, an Fmoc protected amino fluoro pyrazine, an Fmoc protected aminosulfonylchloride, an Fmoc protected aminoaldehyde, an Fmoc protected aminoisocyanate, an MSc protected diamine, an MSc protected aminoketone, an MSc protected aminoalcohol, an MSc protected aminoacid, an MSc protected aminoacid such as for example an MSc protected amino carboxylic acid, an MSc protected aminoacid ester such as for example an MSc protected amino carboxylic acid ester, an MSc protected aminoacid amide such as for example an MSc protected amino carboxylic acid amide, an MSc protected aminoisocyanate, an MSc protected amino chloroazine such as for example an MSc protected amino chloropyridine, for example an MSc protected amino chloropyrimidine, an MSc protected amino chloropyridazine, an MSc protected amino chloropyrazine, an MSc protected amino fluoroazine such as for example an MSc protected amino fluoropyridin, for example an MSc protected amino fluoropyrimidine, an MSc protected amino fluoropyridazine, an MSc protected amino fluoro pyrazine, an MSc protected aminosulfonylchloride, an MSc protected aminoaldehyde, an MSc protected aminoisocyanate, a 4-pentenoyl protected diamine, a 4-pentenoyl protected aminoketone, a 4-pentenoyl protected aminoalcohol, a 4-pentenoyl protected aminoacid such as for example a 4-pentenoyl protected amino carboxylic acid, a 4-pentenoyl protected aminoacid ester such as for example a 4-pentenoyl protected amino carboxylic acid ester, a 4-pentenoyl protected aminoacid amide such as for example a 4-pentenoyl protected amino carboxylic acid amide, a 4-pentenoyl protected aminoisocyanate, a 4-pentenoyl protected amino chloroazine such as for example a 4-pentenoyl protected amino chloropyridine, for example an 4-pentenoyl protected amino chloropyrimidine, a 4-pentenoyl protected amino chloropyridazine, a 4-pentenoyl protected amino chloropyrazine, a 4-pentenoyl protected amino fluoroazine such as for example a 4-pentenoyl protected amino fluoropyridin, for example a 4-pentenoyl protected amino fluoropyrimidine, a 4-pentenoyl protected amino fluoropyridazine, a 4-pentenoyl protected amino fluoro pyrazine, a 4-pentenoyl protected aminosulfonylchloride, a 4-pentenoyl protected aminoaldehyde, a 4-pentenoyl protected aminoisocyanate, a Boc protected diamine, a Boc protected aminoketone, a Boc protected aminoalcohol, a Boc protected aminoacid such as for example a Boc protected amino carboxylic acid, a Boc protected aminoacid ester such as for example a Boc protected amino carboxylic acid ester, a Boc protected aminoacid amide such as for example a Boc protected amino carboxylic acid amide, a Boc protected aminoisocyanate, a Boc protected amino chloroazine such as for example an Boc protected amino chloropyridine, for example a Boc protected amino chloropyrimidine, a Boc protected amino chloropyridazine, a Boc protected amino chloropyrazine, a Boc protected amino fluoroazine such as for example a Boc protected amino fluoropyridin, for example an Boc protected amino fluoropyrimidine, an Boc protected amino fluoropyridazine, an Boc protected amino fluoro pyrazine, a o-Ns protected diamine, a o-Ns protected aminoketone, a o-Ns protected aminoalcohol, a o-Ns protected aminoacid such as for example a o-Ns protected amino carboxylic acid, a o-Ns protected aminoacid ester such as for example a o-Ns protected amino carboxylic acid ester, a o-Ns protected aminoacid amide such as for example a o-Ns protected amino carboxylic acid amide, a o-Ns protected aminoisocyanate, a o-Ns protected amino chloroazine such as for example an o-Ns protected amino chloropyridine, for example a o-Ns protected amino chloropyrimidine, a o-Ns protected amino chloropyridazine, a o-Ns protected amino chloropyrazine, a o-Ns protected amino fluoroazine such as for example a o-Ns protected amino fluoropyridin, for example an o-Ns protected amino fluoropyrimidine, an o-Ns protected amino fluoropyridazine, an o-Ns protected amino fluoro pyrazine, a p-Ns protected diamine, a p-Ns protected aminoketone, a p-Ns protected aminoalcohol, a p-Ns protected aminoacid such as for example a p-Ns protected amino carboxylic acid, a p-Ns protected aminoacid ester such as for example a p-Ns protected amino carboxylic acid ester, a p-Ns protected aminoacid amide such as for example a p-Ns protected amino carboxylic acid amide, a p-Ns protected aminoisocyanate, a p-Ns protected amino chloroazine such as for example an p-Ns protected amino chloropyridine, for example a p-Ns protected amino chloropyrimidine, a p-Ns protected amino chloropyridazine, a p-Ns protected amino chloropyrazine, a p-Ns protected amino fluoroazine such as for example a p-Ns protected amino fluoropyridin, for example an p-Ns protected amino fluoropyrimidine, an p-Ns protected amino fluoropyridazine, an p-Ns protected amino fluoro pyrazine, a allyl carbamate protected diamine, a allyl carbamate protected aminoketone, a allyl carbamate protected aminoalcohol, a allyl carbamate protected aminoacid such as for example a allyl carbamate protected amino carboxylic acid, a allyl carbamate protected aminoacid ester such as for example a allyl carbamate protected amino carboxylic acid ester, a allyl carbamate protected aminoacid amide such as for example a allyl carbamate protected amino carboxylic acid amide, a allyl carbamate protected aminoisocyanate, a allyl carbamate protected amino chloroazine such as for example an allyl carbamate protected amino chloropyridine, for example a allyl carbamate protected amino chloropyrimidine, a allyl carbamate protected amino chloropyridazine, a allyl carbamate protected amino chloropyrazine, a allyl carbamate protected amino fluoroazine such as for example a allyl carbamate protected amino fluoropyridin, for example an allyl carbamate protected amino fluoropyrimidine, an allyl carbamate protected amino fluoropyridazine, an allyl carbamate protected amino fluoro pyrazine, a benzyl carbamate protected diamine, a benzyl carbamate protected aminoketone, a benzyl carbamate protected aminoalcohol, a benzyl carbamate protected aminoacid such as for example a benzyl carbamate protected amino carboxylic acid, a benzyl carbamate protected aminoacid ester such as for example a benzyl carbamate protected amino carboxylic acid ester, a benzyl carbamate protected aminoacid amide such as for example a benzyl carbamate protected amino carboxylic acid amide, a benzyl carbamate protected aminoisocyanate, a benzyl carbamate protected amino chloroazine such as for example an benzyl carbamate protected amino chloropyridine, for example a benzyl carbamate protected amino chloropyrimidine, a benzyl carbamate protected amino chloropyridazine, a benzyl carbamate protected amino chloropyrazine, a benzyl carbamate protected amino fluoroazine such as for example a benzyl carbamate protected amino fluoropyridin, for example an benzyl carbamate protected amino fluoropyrimidine, an benzyl carbamate protected amino fluoropyridazine, an benzyl carbamate protected amino fluoro pyrazine, a Fmoc protected aminofluorotriazine such as for example a Fmoc protected aminofluoro-1,2,3-triazine, for example a Fmoc protected aminofluoro-1,2,4-triazine, for example a Fmoc protected aminofluoro-1,3,5-triazine, a Fmoc protected aminochlorotriazine such as for example a Fmoc protected aminochloro-1,2,3-triazine, for example a Fmoc protected aminochloro-1,2,4-triazine, for example a Fmoc protected aminochloro-1,3,5-triazine, a MSc protected aminofluorotriazine such as for example a MSc protected aminofluoro-1,2,3-triazine, for example a MSc protected aminofluoro-1,2,4-triazine, for example a MSc protected aminofluoro-1,3,5-triazine, a MSc protected aminochlorotriazine such as for example a MSc protected aminochloro-1,2,3-triazine, for example a MSc protected aminochloro-1,2,4-triazine, for example a MSc protected aminochloro-1,3,5-triazine, a o-Ns protected aminofluorotriazine such as for example a o-Ns protected aminofluoro-1,2,3-triazine, for example a o-Ns protected aminofluoro-1,2,4-triazine, for example a o-Ns protected aminofluoro-1,3,5-triazine, a o-Ns protected aminochlorotriazine such as for example a o-Ns protected aminochloro-1,2,3-triazine, for example a o-Ns protected aminochloro-1,2,4-triazine, for example a o-Ns protected aminochloro-1,3,5-triazine, a p-Ns protected aminofluorotriazine such as for example a p-Ns protected aminofluoro-1,2,3-triazine, for example a p-Ns protected aminofluoro-1,2,4-triazine, for example a p-Ns protected aminofluoro-1,3,5-triazine, a p-Ns protected aminochlorotriazine such as for example a p-Ns protected aminochloro-1,2,3-triazine, for example a p-Ns protected aminochloro-1,2,4-triazine, for example a p-Ns protected aminochloro-1,3,5-triazine, a allyl carbamate protected aminofluorotriazine such as for example a allyl carbamate protected aminofluoro-1,2,3-triazine, for example a allyl carbamate protected aminofluoro-1,2,4-triazine, for example a allyl carbamate protected aminofluoro-1,3,5-triazine, a allyl carbamate protected aminochlorotriazine such as for example a allyl carbamate protected aminochloro-1,2,3-triazine, for example a allyl carbamate protected aminochloro-1,2,4-triazine, for example a allyl carbamate protected aminochloro-1,3,5-triazine, a benzyl carbamate protected aminofluorotriazine such as for example a benzyl carbamate protected aminofluoro-1,2,3-triazine, for example a benzyl carbamate protected aminofluoro-1,2,4-triazine, for example a benzyl carbamate protected aminofluoro-1,3,5-triazine, a benzyl carbamate protected aminochlorotriazine such as for example a benzyl carbamate protected aminochloro-1,2,3-triazine, for example a benzyl carbamate protected aminochloro-1,2,4-triazine, for example a benzyl carbamate protected aminochloro-1,3,5-triazine, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactive compound building blocks may optionally be substituted by one or more substituents.

In a further embodiment, a reactive compound building block comprises two reactive groups, such as for example a mercaptoaldehyde, a hydroxyaldehyde, a formylalkyl carboxylic acid, a formyl aryl carboxylic acid, a formyl hetaryl carboxylic acid, a formyl alkylaryl carboxylic acid, a formyl alkylhetaryl carboxylic acid, a formyl arylalkyl carboxylic acid, a formyl hetarylalkyl carboxylic acid, a formylalkyl carboxylic acid ester, a formyl aryl carboxylic acid ester, a formyl hetaryl carboxylic acid ester, a formyl alkylaryl carboxylic acid ester, a formyl alkylhetaryl carboxylic acid ester, a formyl arylalkyl carboxylic acid ester, a formyl hetarylalkyl carboxylic acid ester, a formylalkyl sulfonyl chloride, a formyl aryl sulfonyl chloride, a formyl hetaryl sulfonyl chloride, a formyl alkylaryl sulfonyl chloride, a formyl alkylhetaryl sulfonyl chloride, a formyl arylalkyl sulfonyl chloride, a formyl hetarylalkyl sulfonyl chloride, a formylalkyl isocyanate, a formyl aryl isocyanate, a formyl hetaryl isocyanate, a formyl alkylaryl isocyanate, a formyl alkylhetaryl isocyanate, a formyl arylalkyl isocyanate, a formyl hetarylalkyl isocyanate, a formylalkyl isocyanide, a formyl aryl isocyanide, a formyl hetaryl isocyanide, a formyl alkylaryl isocyanide, a formyl alkylhetaryl isocyanide, a formyl arylalkyl isocyanide, a formyl hetarylalkyl isocyanide, a formyl chloroazine such as for example a formyl chloropyridine, for example a formyl chloropyrimidine, a formyl chloropyridazine, a formyl chloropyrazine, a formyl fluoroazine such as for example a formyl fluoropyridin, for example a formyl fluoropyrimidine, a formyl fluoropyridazine, a formyl fluoro pyrazine, a formyl fluorotriazine, a formylchlorotriazine, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactive compound building blocks may optionally be substituted by one or more substituents.

In a further embodiment, a reactive compound building block comprises two reactive groups, such as for example a dicarboxylic acid, a alkoxycarbonylalkyl carboxylic acid, a alkoxycarbonyl aryl carboxylic acid, a alkoxycarbonyl hetaryl carboxylic acid, a alkoxycarbonyl alkylaryl carboxylic acid, a alkoxycarbonyl alkylhetaryl carboxylic acid, a alkoxycarbonyl arylalkyl carboxylic acid, a alkoxycarbonyl hetarylalkyl carboxylic acid, a carboxyalkyl sulfonyl chloride, a carboxy aryl sulfonyl chloride, a carboxy hetaryl sulfonyl chloride, a carboxy alkylaryl sulfonyl chloride, a carboxy alkylhetaryl sulfonyl chloride, a carboxy arylalkyl sulfonyl chloride, a carboxy hetarylalkyl sulfonyl chloride, a alkoxycarbonylalkyl sulfonyl chloride, a alkoxycarbonyl aryl sulfonyl chloride, a alkoxycarbonyl hetaryl sulfonyl chloride, a alkoxycarbonyl alkylaryl sulfonyl chloride, a alkoxycarbonyl alkylhetaryl sulfonyl chloride, a alkoxycarbonyl arylalkyl sulfonyl chloride, a alkoxycarbonyl hetarylalkyl sulfonyl chloride, a alkoxycarbonylalkyl isocyanate, a alkoxycarbonyl aryl isocyanate, a alkoxycarbonyl hetaryl isocyanate, a alkoxycarbonyl alkylaryl isocyanate, a alkoxycarbonyl alkylhetaryl isocyanate, a alkoxycarbonyl arylalkyl isocyanate, a alkoxycarbonyl hetarylalkyl isocyanate, a alkoxycarbonyl chloroazine such as for example a alkoxycarbonyl chloropyridine, for example a alkoxycarbonyl chloropyrimidine, a alkoxycarbonyl chloropyridazine, a alkoxycarbonyl chloropyrazine, a alkoxycarbonyl fluoroazine such as for example a alkoxycarbonyl fluoropyridin, for example a alkoxycarbonyl fluoropyrimidine, a alkoxycarbonyl fluoropyridazine, a alkoxycarbonyl fluoro pyrazine, a alkoxycarbonyl fluorotriazine, a alkoxycarbonylchlorotriazine, a carboxycarbonyl chloroazine such as for example a carboxycarbonyl chloropyridine, for example a carboxycarbonyl chloropyrimidine, a carboxycarbonyl chloropyridazine, a carboxycarbonyl chloropyrazine, a carboxycarbonyl fluoroazine such as for example a carboxycarbonyl fluoropyridin, for example a carboxycarbonyl fluoropyrimidine, a carboxycarbonyl fluoropyridazine, a carboxycarbonyl fluoro pyrazine, a carboxycarbonyl fluorotriazine, a carboxycarbonylchlorotriazine, a chlorosulfonyl chloroazine such as for example a chlorosulfonyl chloropyridine, for example a chlorosulfonyl chloropyrimidine, a chlorosulfonyl chloropyridazine, a chlorosulfonyl chloropyrazine, a chlorosulfonyl fluoroazine such as for example a chlorosulfonyl fluoropyridin, for example a chlorosulfonyl fluoropyrimidine, a chlorosulfonyl fluoropyridazine, a chlorosulfonyl fluoro pyrazine, a chlorosulfonyl fluorotriazine, a chlorosulfonylchlorotriazine, a dihaloazine such as for example a dihalopyridin, for example a dihalopyrimidine, a dihalopyridazine, a dihalo pyrazine, a dihalotriazine, a dihalotriazine such as for example a dihalo-1,2,3-triazine, for example a dihalo-1,2,4-triazine, for example a dihalo-1,3,5-triazine, a dichloroazine such as for example a dichloropyridin, for example a dichloropyrimidine, a dichloropyridazine, a dichloro pyrazine, a dichlorotriazine, a dichlorotriazine such as for example a dichloro-1,2,3-triazine, for example a dichloro-1,2,4-triazine, for example a dichloro-1,3,5-triazine, a difluoroazine such as for example a difluoropyridin, for example a difluoropyrimidine, a difluoropyridazine, a difluoro pyrazine, a difluorotriazine, a difluorotriazine such as for example a difluoro-1,2,3-triazine, for example a difluoro-1,2,4-triazine, for example a difluoro-1,3,5-triazine, a chlorofluoroazine such as for example a chlorofluoropyridin, for example a chlorofluoropyrimidine, a chlorofluoropyridazine, a chlorofluoro pyrazine, a chlorofluorotriazine, a chlorofluorotriazine such as for example a chlorofluoro-1,2,3-triazine, for example a chlorofluoro-1,2,4-triazine, for example a chlorofluoro-1,3,5-triazine, wherein such reactive groups may optionally be protected by further protection groups, for example carboxylic acid protection such as methyl ester, ethyl ester, t-butyl ester, 2,2,2-trichloroethyl ester, methylsulfonylethyl ester, benzyl ester, p-methoxy benzyl ester, o-nitrobenzyl ester, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactive compound building blocks may optionally be substituted by one or more substituents.

In a further embodiment, a reactive compound building block comprises two reactive groups, such as for example an alpha,beta-unsaturated aldehyde, an alpha,beta-unsaturated sulfonyl chloride, an alpha,beta-unsaturated carboxylic acid, an alpha,beta-unsaturated carboxylic acid ester, an alpha,beta-unsaturated isocyanate, an alpha,beta-unsaturated ketone, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactive compound building blocks may optionally be substituted by one or more substituents.

In a further embodiment, a reactive compound building block comprises three reactive groups, such as for example a triamine, a diamino carboxylic acid, an amino dicarboxylic acid, a tricarboxylic acid, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactive compound building blocks may optionally be substituted by one or more substituents.

In a further embodiment, a reactive compound building block comprises three reactive groups, such as for example trihalotriazine for example trichlorotriazine, trifluorotriazine, dichlorofluorotriazine, difluorochlorotriazine, such as for example formyl dihaloazines, carboxy dihaloazines, chlorosulfonyl dihaloazines, isocyanato dihaloazines, amino dihaloazines, trihaloazinylazine, dihaloazinylhaloazine, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactive compound building blocks may optionally be substituted by one or more substituents.

In a further embodiment, a reactive compound building block comprises three reactive groups, such as for example a diamino aldehyde, an amino dialdehyde, a trialdehyde, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactive compound building blocks may optionally be substituted by one or more substituents.

In a further embodiment, a reactive compound building block comprises three reactive groups, such as for example a diformyl carboxylic acid, a formyl dicarboxylic acid, a formyl amino carboxylic acid, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactive compound building blocks may optionally be substituted by one or more substituents.

In a further embodiment, a reactive compound building block comprises three reactive groups, such as for example an alpha,beta-unsaturated aminoaldehyde, an alpha,beta-unsaturated aminosulfonyl chloride, an alpha,beta-unsaturated aminocarboxylic acid, an alpha,beta-unsaturated aminocarboxylic acid ester, an alpha,beta-unsaturated aminoisocyanate, an alpha,beta-unsaturated aminoketone, an alpha,beta-unsaturated aminocarboxylic acid amide, an alpha,beta-unsaturated aminosulfoxide, an alpha,beta-unsaturated aminosulfone, an alpha,beta-unsaturated aminosulfonamide, an alpha,beta-unsaturated aminosulfonylchloride, a nitro aminoalkene, such as comprising a vinylogous nitro group (alpha,beta-unsaturated nitroaminoalkene), an alpha,beta-unsaturated formylaldehyde, an alpha,beta-unsaturated formylsulfonyl chloride, an alpha,beta-unsaturated formylcarboxylic acid, an alpha,beta-unsaturated formylcarboxylic acid ester, an alpha,beta-unsaturated formylisocyanate, an alpha,beta-unsaturated formylketone, an alpha,beta-unsaturated formylcarboxylic acid amide, an alpha,beta-unsaturated formylsulfoxide, an alpha,beta-unsaturated formylsulfone, an alpha,beta-unsaturated formylsulfonamide, an alpha,beta-unsaturated formylsulfonylchloride, a nitro formylalkene, such as comprising a vinylogous nitro group (alpha,beta-unsaturated nitroformylalkene), wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactive compound building blocks may optionally be substituted by one or more substituents.

In a further embodiment, a reactive compound building block comprises three reactive groups, such as for example an alpha,beta-unsaturated carboxyaldehyde, an alpha,beta-unsaturated carboxysulfonyl chloride, an alpha,beta-unsaturated carboxycarboxylic acid, an alpha,beta-unsaturated carboxycarboxylic acid ester, an alpha,beta-unsaturated carboxylsocyanate, an alpha,beta-unsaturated carboxyketone, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactive compound building blocks may optionally be substituted by one or more substituents.

In a further embodiment, a reactive compound building block comprises three reactive groups, such as for example an alpha,beta-unsaturated alkoxycarbonylaldehyde, an alpha,beta-unsaturated alkoxycarbonylsulfonyl chloride, an alpha,beta-unsaturated alkoxycarbonylcarboxylic acid, an alpha,beta-unsaturated alkoxycarbonylcarboxylic acid ester, an alpha,beta-unsaturated alkoxycarbonylisocyanate, an alpha,beta-unsaturated alkoxycarbonylketone, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactive compound building blocks may optionally be substituted by one or more substituents.

In a further embodiment, a reactive compound building block comprises three reactive groups, such as for example an alpha,beta-unsaturated formylaldehyde, an alpha,beta-unsaturated formylsulfonyl chloride, an alpha,beta-unsaturated formylcarboxylic acid, an alpha,beta-unsaturated formylcarboxylic acid ester, an alpha,beta-unsaturated formylisocyanate, an alpha,beta-unsaturated formylketone, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactive compound building blocks may optionally be substituted by one or more substituents.

Further reactive group reactions are illustrated herein below. The illustrations should not be construed as limiting the scope of the present invention in any way.

Nucleophilic Substitution Using Activation of Electrophiles
A. Acylating Monomer Building Blocks (Reactive Compound Building Blocks)—Principle

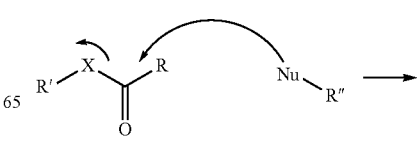

-continued

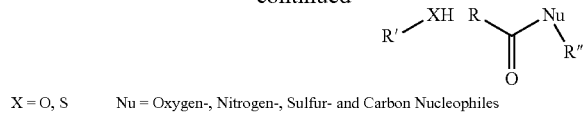

X = O, S    Nu = Oxygen-, Nitrogen-, Sulfur- and Carbon Nucleophiles

B. Acylation
Amide Formation by Reaction of Amines with Activated Esters

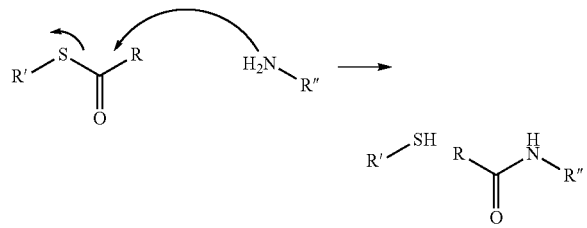

C. Acylation
Pyrazolone Formation by Reaction of Hydrazines with Alpha-Ketoesters

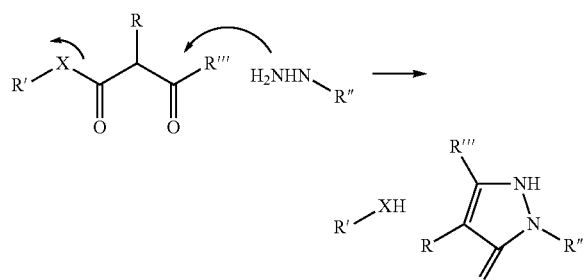

D. Acylation
Isoxazolone Formation by Reaction of Hydroxylamines with Alpha-Ketoesters

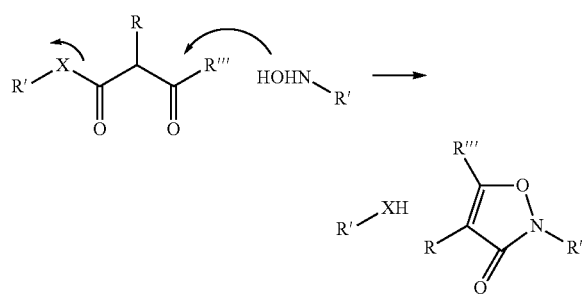

E. Acylation
Pyrimidine Formation by Reaction of Thioureas with Alpha-Ketoesters

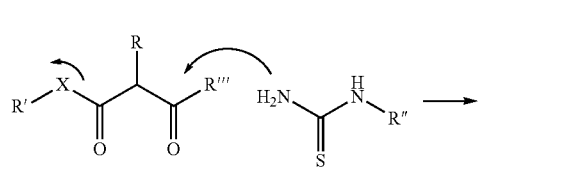

-continued

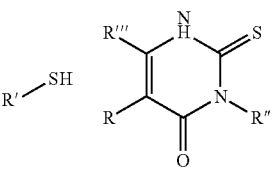

F. Acylation
Pyrimidine Formation by Reaction of Ureas with Malonates

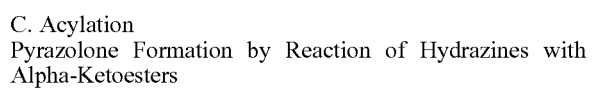

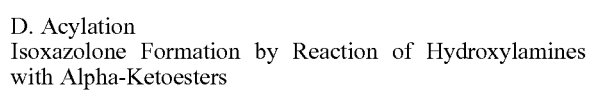

G. Acylation
Coumarine or Quinolinon Formation by a Heck Reaction Followed by a Nucleophilic Substitution

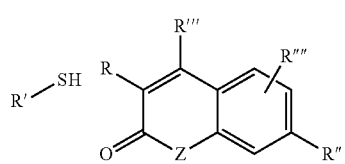

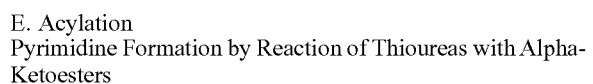

X = O, S
X' = Halogen, OTf, OMs
Z = O, NH

H. Acylation
Phthalhydrazide Formation by Reaction of Hydrazines and Phthalimides

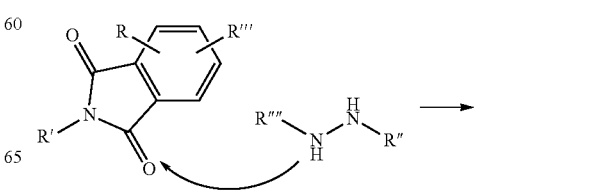

-continued

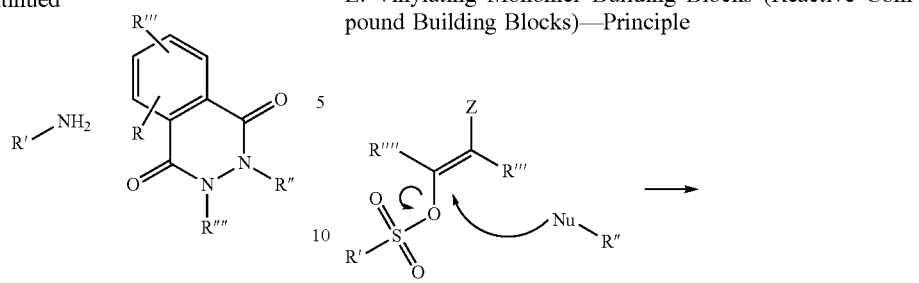

I. Acylation
Diketopiperazine Formation by Reaction of Amino Acid Esters

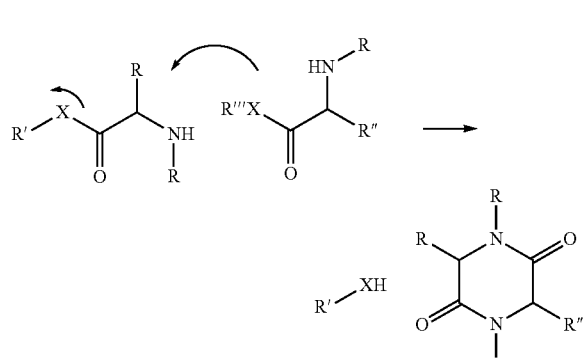

X = O, S
R' = H, R

J. Acylation
Hydantoin Formation by Reaction of Urea and α-Substituted Esters

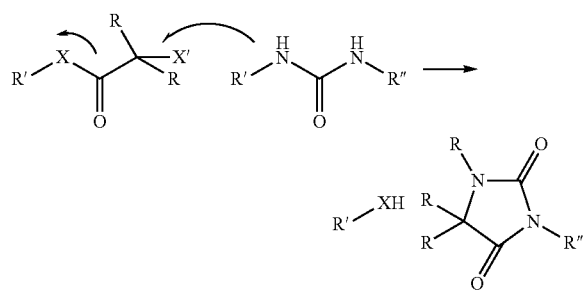

X = O, S
X' = Hal, OTos, OMs, etc.

K. Alkylating Monomer Building Blocks (Reactive Compound Building Blocks)—Principle
Alkylated Compounds by Reaction of Sulfonates with Nucleofiles

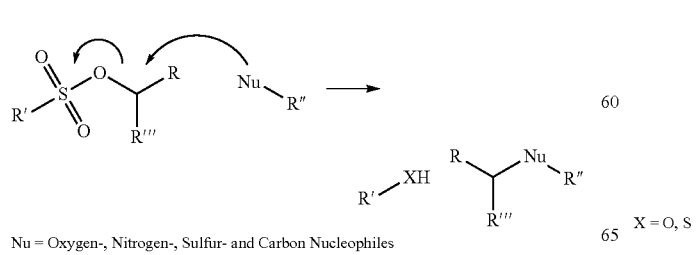

Nu = Oxygen-, Nitrogen-, Sulfur- and Carbon Nucleophiles

L. Vinylating Monomer Building Blocks (Reactive Compound Building Blocks)—Principle

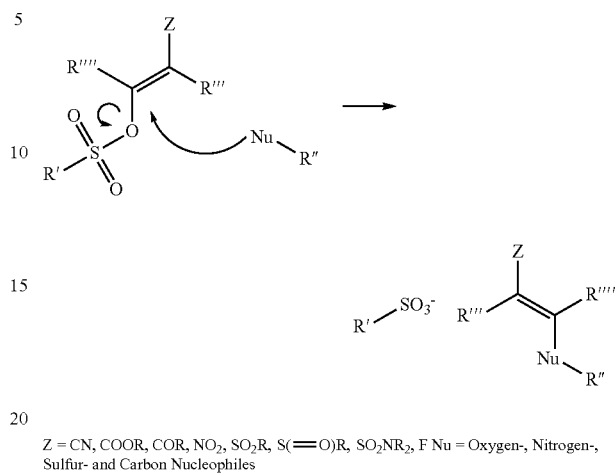

Z = CN, COOR, COR, $NO_2$, $SO_2R$, S(=O)R, $SO_2NR_2$, F   Nu = Oxygen-, Nitrogen-, Sulfur- and Carbon Nucleophiles

M. Heteroatom Electrophiles
Disulfide Formation by Reaction of Pyridyl Disulfide with Mercaptanes

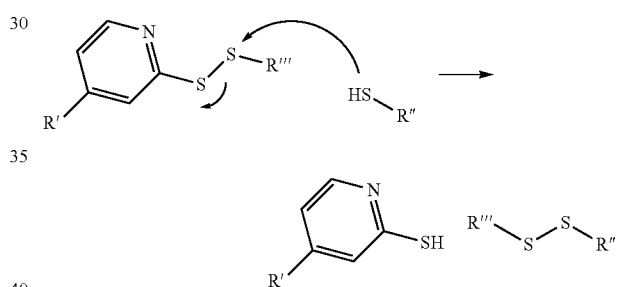

N. Acylation
Benzodiazepinone Formation by Reaction of Amino Acid Esters and Amino Ketones

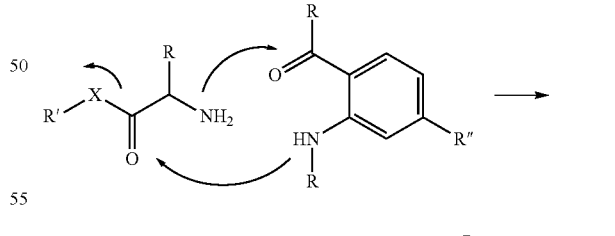

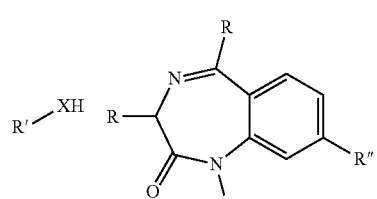

X = O, S

Addition to Carbon-Hetero Multiple Bonds:
O. Wittig/Horner-Wittig-Emmons Reagents
Substituted Alkene Formation by Reaction of Phosphonates with Aldehydes or Ketones

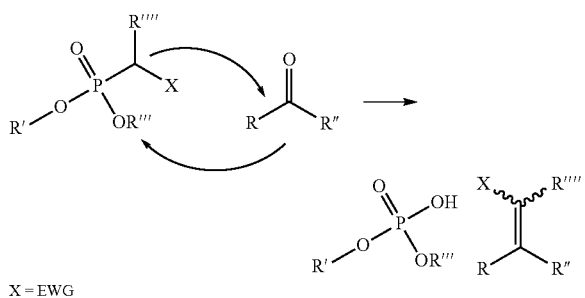

X = EWG

Transition Metal Catalysed Reactions
P. Arylation
Biaryl formation by the reaction of Boronates with Aryls or Heteroaryls

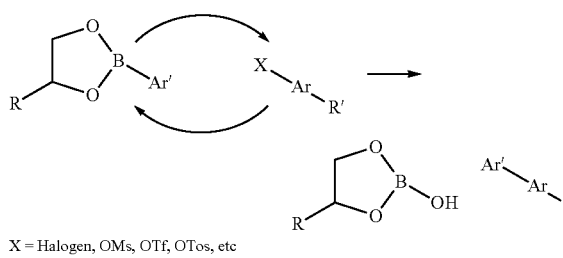

X = Halogen, OMs, OTf, OTos, etc

Q. Arylation
Biaryl Formation by the Reaction of Boronates with Aryls or Heteroaryls

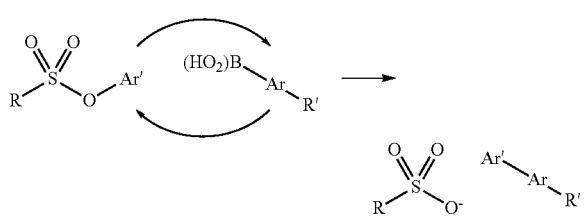

R. Arylation
Vinylarene Formation by the Reaction of Alkenes with Aryls or Heteroaryls

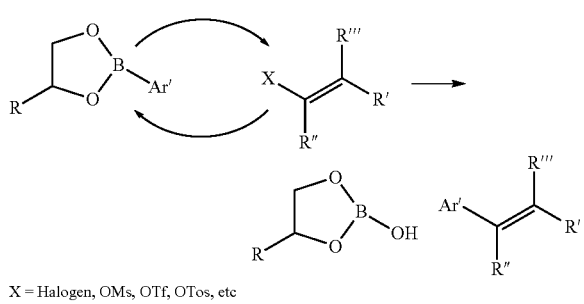

X = Halogen, OMs, OTf, OTos, etc

S. Alkylation
Alkylation of Arenes/Hetarens by the Reaction with Alkyl Boronates

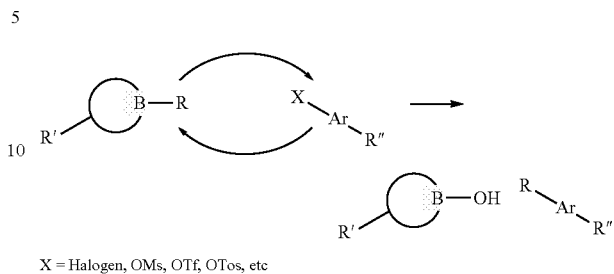

X = Halogen, OMs, OTf, OTos, etc

T. Alkylation
Alkylation of Arenas/Hetarenes by Reaction with Enolethers

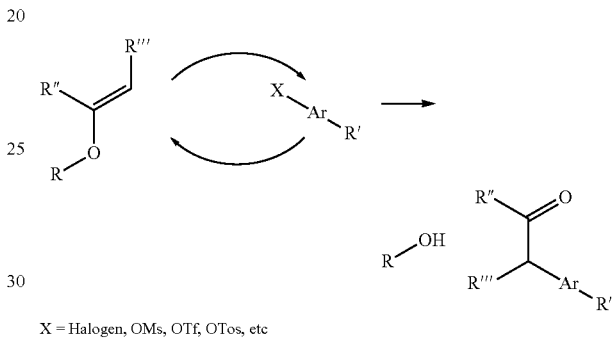

X = Halogen, OMs, OTf, OTos, etc

Nucleophilic Substitution Using Activation of Nucleophiles
U. Condensations
Alkylation of Aldehydes with Enolethers or Enamines

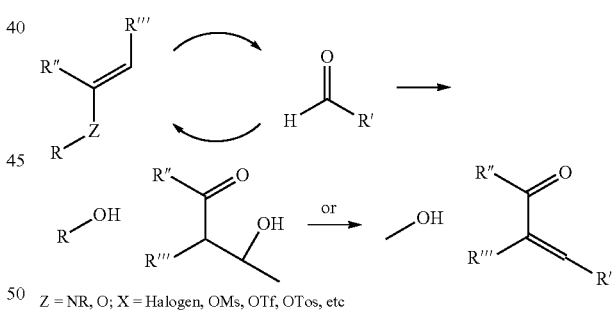

Z = NR, O; X = Halogen, OMs, OTf, OTos, etc

V. Alkylation
Alkylation of Aliphatic Halides or Tosylates with Enolethers or Enamines

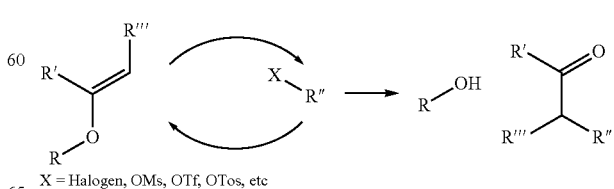

X = Halogen, OMs, OTf, OTos, etc

Cycloadditions

W. [2+4] Cycloadditions

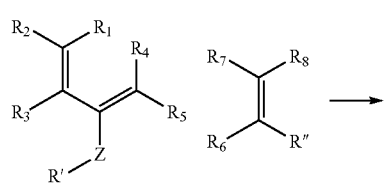

Z = O, NR

X. [2+4] Cycloadditions

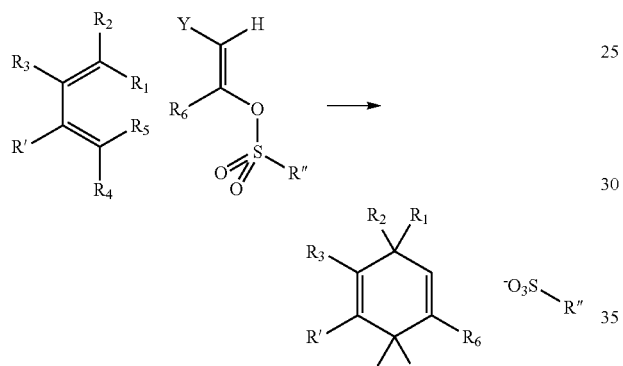

Y, CN, COOR, COR, NO₂, SO₂R, S(=O)R, SO₂NR₂, F

Y. [3+2] Cycloadditions

Y, CN, COOR, COR, NO₂, SO₂R, S(=O)R, SO₂NR₂, F

Z. [3+2] Cycloadditions

Y, CN, COOR, COR, NO₂, SO₂R, S(=O)R, SO₂NR₂, F

The synthesis of the molecule can involve one or more of the below illustrated reactions.

Examples of nucleophilic substitution reactions involved in one or more molecule synthesis steps.

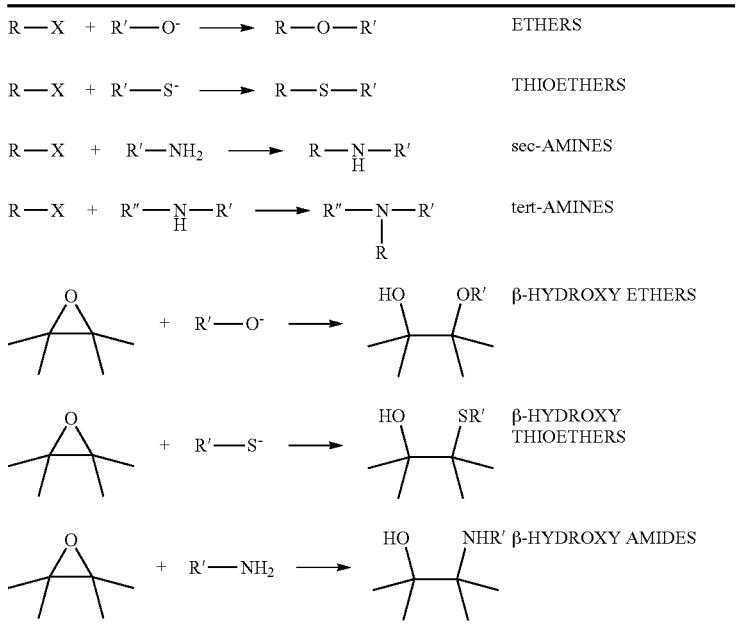

-continued
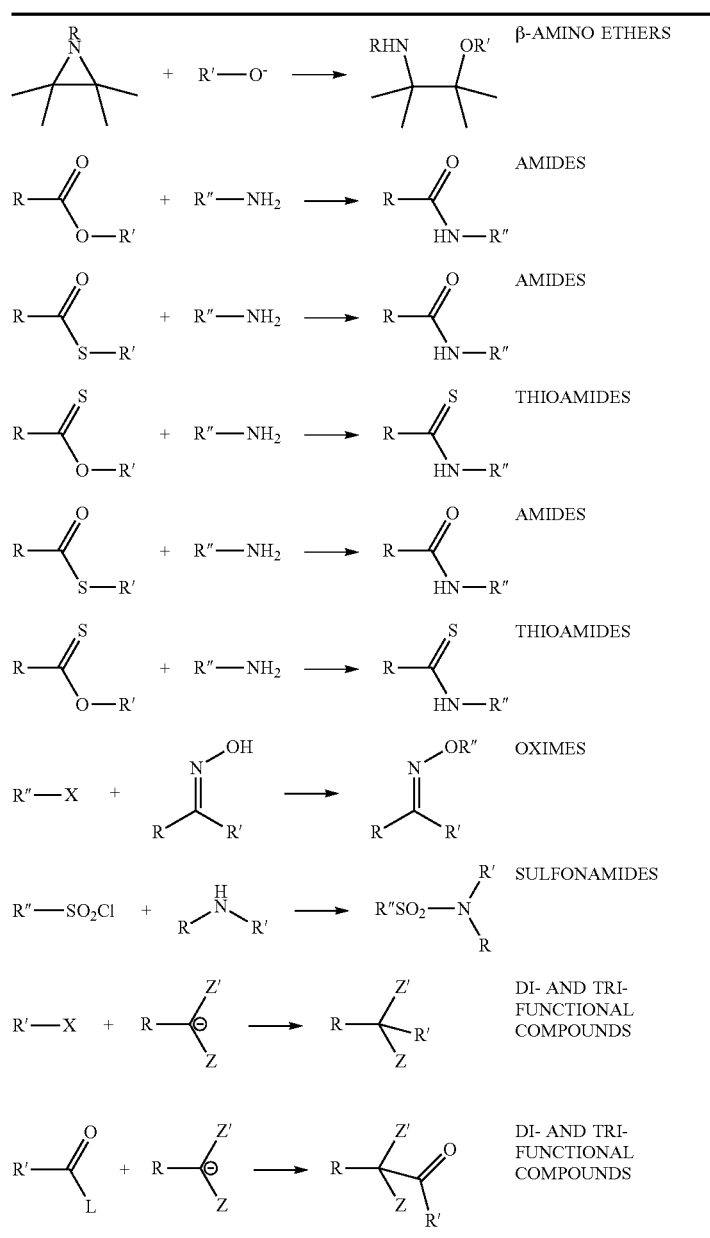
Z', Z = COOR, CHO, COR, CONR"$_2$, COO$^-$, NO$_2$, SOR, SO$_2$R, SO$_2$NR"$_2$, CN, ect.
Aromatic Nucleophilic Substitutions Transition Metal Catalysed reactions
SUBSTITUTED AROMATIC COMPOUNDS
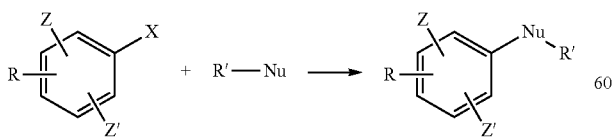
Nu = Oxygen-, Nitrogen-, Sulfur- and Carbon Nucleophiles
X = F, Cl, Br, I, OSO$_2$CH$_3$, OSO$_2$CF$_3$, OSO$_2$TOL . . . etc.
Z', Z = COOR, CHO, COR, CONR"$_2$, COO$^-$, CN, NO$_2$, SOR, SO$_2$R, SO$_2$NR"$_2$ . . . ect.

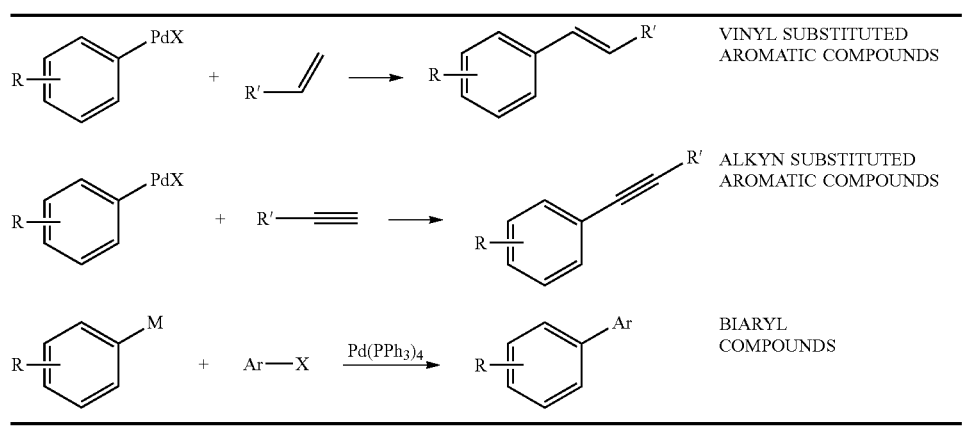
Addition to Carbon-Carbon Multiple Bonds
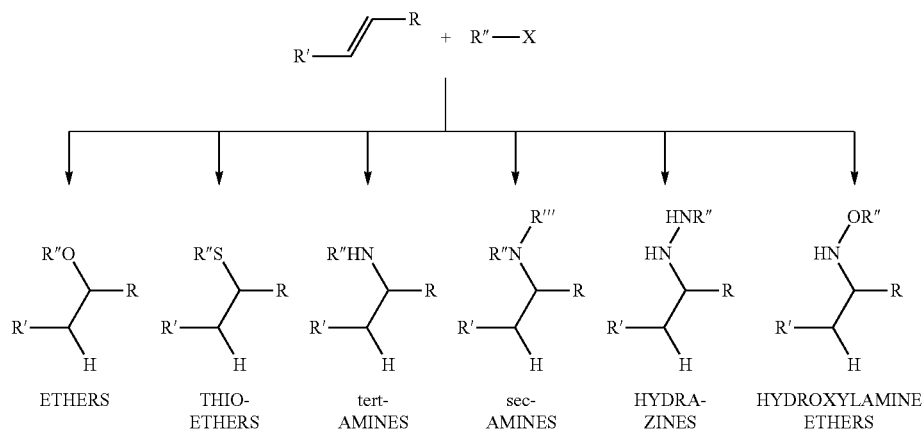
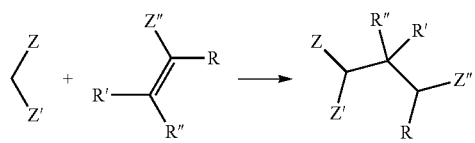
MULTI FUNCTIONAL COMPOUNDS
Z = H, Alkyl, Z', Ar
Z" = COOR, CHO, COR, CONR"$_2$, CN, NO$_2$, SOR, SO$_2$R, SO$_2$NR"$_2$, ect.
Z' = Z" R = R', = R", = Z
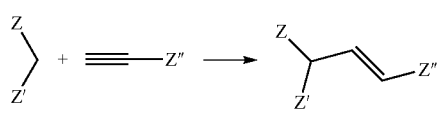
DI- AND TRI- FUNCTIONAL ALKENES
Z = H, Alkyl, Ar,
Z" = Z', Alkyl, Ar,
Z' = COOR, CHO, COR, CONR"$_2$, CN, NO$_2$, SOR, SO$_2$R, SO$_2$NR"$_2$, ect.

Cycloaddition to Multiple Bounds

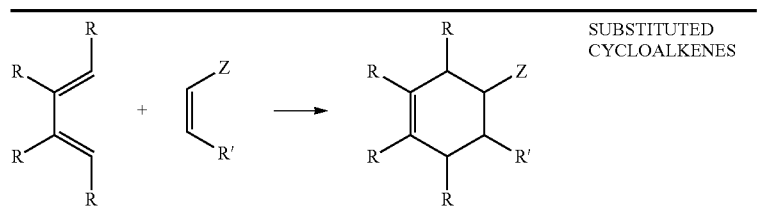

SUBSTITUTED CYCLOALKENES

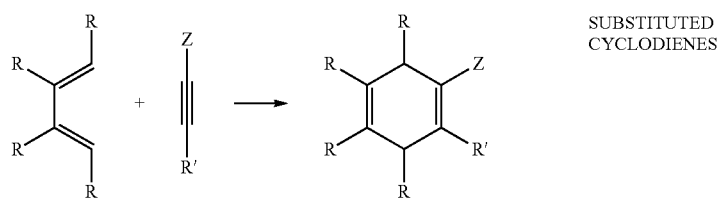

SUBSTITUTED CYCLODIENES

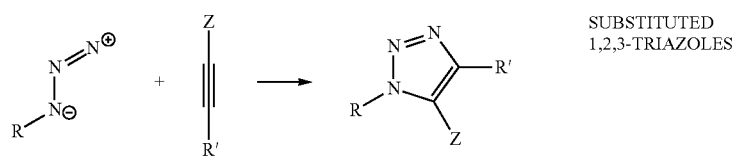

SUBSTITUTED 1,2,3-TRIAZOLES

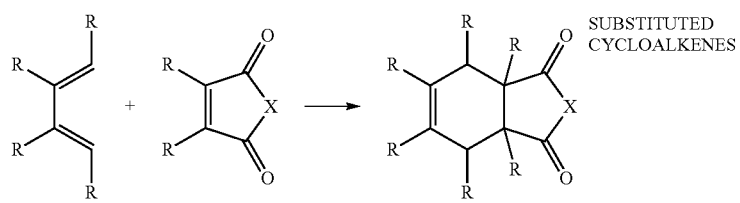

SUBSTITUTED CYCLOALKENES

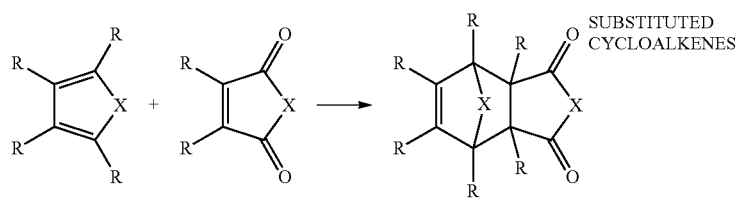

SUBSTITUTED CYCLOALKENES

Z = COOR, CHO, COR, COOH COAr CN, NO$_2$, Ar, CH$_2$OH, CH$_2$NH$_2$, CH$_2$CN, SOR, SO$_2$R etc.
R = H, Alkyl, Ar, Z
X = O, NR, CR$_2$, S.

Addition to Carbon-Hetero Multiple Bonds

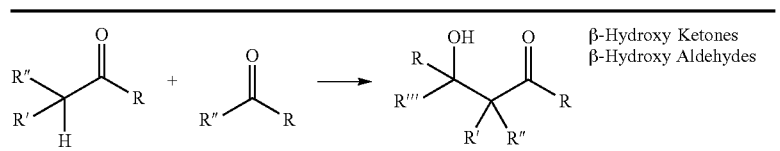

β-Hydroxy Ketones
β-Hydroxy Aldehydes

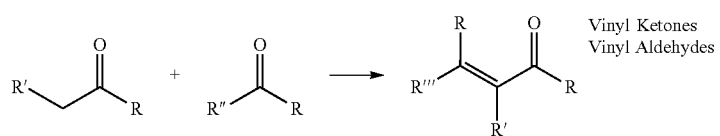

Vinyl Ketones
Vinyl Aldehydes

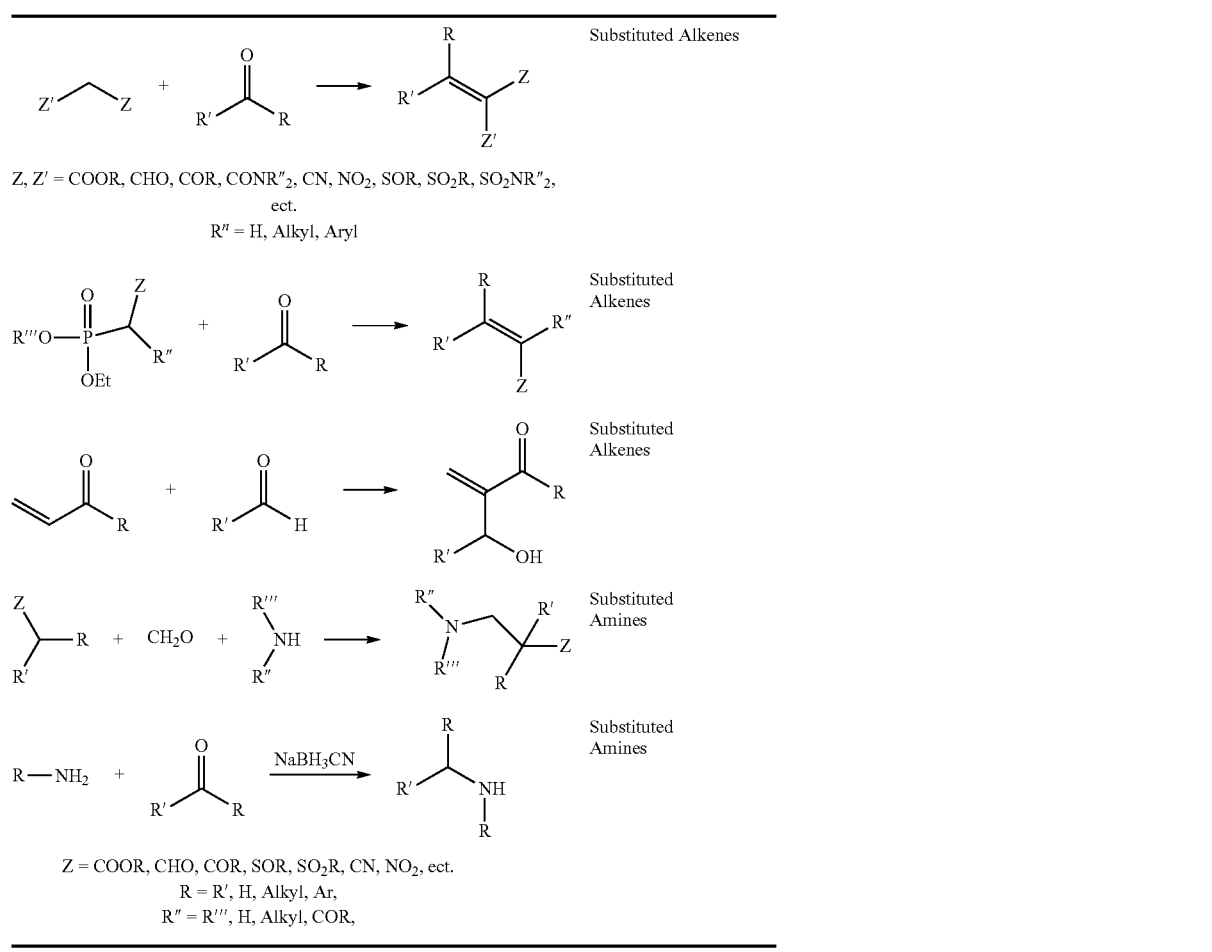

In the above illustrated chemical reactions, R, R', R", R"', R"", R1, R2, R3, R4, R5, R6, R7, R8, respectively, are selected independently from the group consisting of:
hydrido,
substituted and unsubstituted alkyl, substituted and unsubstituted haloalkyl, substituted and unsubstituted hydroxyalkyl, substituted and unsubstituted alkylsulfonyl,
substituted and unsubstituted alkenyl,
halo,
substituted and unsubstituted alkoxy, substituted and unsubstituted alkoxyalkyl, substituted and unsubstituted haloalkoxy, substituted and unsubstituted haloalkoxyalkyl,
substituted and unsubstituted aryl,
substituted and unsubstituted heterocyclic,
substituted and unsubstituted heteroaryl,
sulfonyl, substituted and unsubstituted alkylsulfonyl, substituted and unsubstituted arylsulfonyl, sulfamyl, sulfonamidyl, aminosulfonyl, substituted and unsubstituted N-alkylaminosulfonyl, substituted and unsubstituted N-arylaminosulfonyl, substituted and unsubstituted N,N-dialkylaminosulfonyl, substituted and unsubstituted N-alkyl-N-arylaminosulfonyl, substituted and unsubstituted N-alkylaminosulfonyl, substituted and unsubstituted N,N-dialkylaminosulfonyl, substituted and unsubstituted N-arylaminosulfonyl, substituted and unsubstituted N-alkyl-N-arylaminosulfonyl,
carboxy, substituted and unsubstituted carboxyalkyl,
carbonyl, substituted and unsubstituted alkylcarbonyl, substituted and unsubstituted alkylcarbonylalkyl,
substituted and unsubstituted alkoxycarbonyl, substituted and unsubstituted alkoxycarbonylalkyl,
aminocarbonyl, substituted and unsubstituted aminocarbonylalkyl, substituted and unsubstituted N-alkylaminocarbonyl, substituted and unsubstituted N-arylaminocarbonyl, substituted and unsubstituted N,N-dialkylaminocarbonyl, substituted and unsubstituted N-alkyl-N-arylaminocarbonyl, substituted and unsubstituted N-alkyl-N-hydroxyaminocarbonyl, substituted and unsubstituted N-alkyl-N-hydroxyaminocarbonylalkyl, substituted and unsubstituted N-alkylaminocarbonyl, substituted and unsubstituted N,N-dialkylaminocarbonyl, substituted and unsubstituted N-arylaminocarbonyl, substituted and unsubstituted N-alkyl-N-arylaminocarbonyl, substituted and unsubstituted aminocarbonylalkyl, substituted and unsubstituted N-cycloalkylaminocarbonyl,
substituted and unsubstituted aminoalkyl, substituted and unsubstituted alkylaminoalkyl,
amidino,
cyanoamidino,
substituted and unsubstituted heterocyclicalkyl,
substituted and unsubstituted aralkyl,
substituted and unsubstituted cycloalkyl,
substituted and unsubstituted cycloalkenyl,
substituted and unsubstituted alkylthio,
substituted and unsubstituted alkylsulfinyl,
substituted and unsubstituted N-alkylamino, substituted and unsubstituted N,N-dialkylamino, substituted and unsubstituted arylamino, substituted and unsubstituted aralkylamino, substituted and unsubstituted N-alkyl-N-arylamino, substituted and unsubstituted N-aralkyl-N-alkylamino, substituted and unsubstituted N-arylaminoalkyl, substituted and unsubstituted N-aralkylaminoalkyl, substituted and unsubstituted N-alkyl-N-arylaminoalkyl, substituted and unsubstituted N-aralkyl-N-alkylaminoalkyl, acyl, acylamino, substituted and unsubstituted arylthio, substituted and unsubstituted aralkylthio, substituted and unsubstituted aryloxy, substituted and unsubstituted aralkoxy, substituted and unsubstituted haloaralkyl, substituted and unsubstituted carboxyhaloalkyl, substituted and unsubstituted alkoxycarbonylhaloalkyl, substituted and unsubstituted aminocarbonylhaloalkyl, substituted and unsubstituted alkylaminocarbonylhaloalkyl, substituted and unsubstituted alkoxycarbonylcyanoalkenyl, substituted and unsubstituted carboxyalkylaminocarbonyl, substituted and unsubstituted aralkoxycarbonylalkylaminocarbonyl, substituted and unsubstituted cycloalkylalkyl, and substituted and unsubstituted aralkenyl.

Additional bond-forming reactions that can be used to join building blocks in the synthesis of the molecules and libraries of the invention include those shown below. The reactions shown below emphasize the reactive functional groups.

Various substituents can be present in the reactive compound building blocks, including those labeled R1, R2, R3 and R4. The possible positions which can be substituted include, but are not limited to, those indicated by R1, R2, R3 and R4. These substituents can include any suitable chemical moieties, such as the chemical moieties cited herein above, but they are preferably limited, in one embodiment, to those which will not interfere with or significantly inhibit the indicated reaction, and, unless otherwise specified, they can include, but are not limited to, hydrogen, alkyl, substituted alkyl, aryl, substituted aryl, heteroaryl, substituted heteroaryl, alkoxy, aryloxy, arylalkyl, substituted arylalkyl, amino, substituted amino and others as are known in the art. Suitable substituents on these groups include alkyl, aryl, heteroaryl, cyano, halogen, hydroxyl, nitro, amino, mercapto, carboxyl, and carboxamide. Where specified, suitable electron-withdrawing groups include nitro, carboxyl, haloalkyl, such as trifluoromethyl and others as are known in the art. Examples of suitable electron-donating groups include alkyl, alkoxy, hydroxyl, amino, halogen, acetamido and others as are known in the art.

Addition of a Primary Amine to an Alkene:

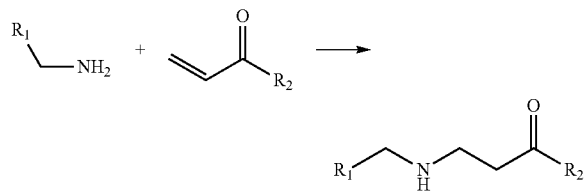

Nucleophilic Substitution:

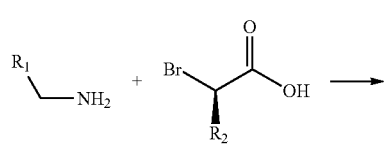

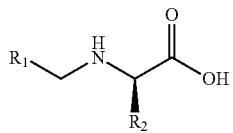

Reductive Alkylation of an Amine:

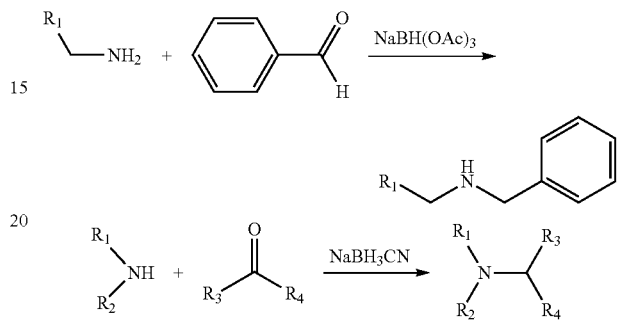

Palladium Catalyzed Carbon-Carbon Bond Forming Reactions:

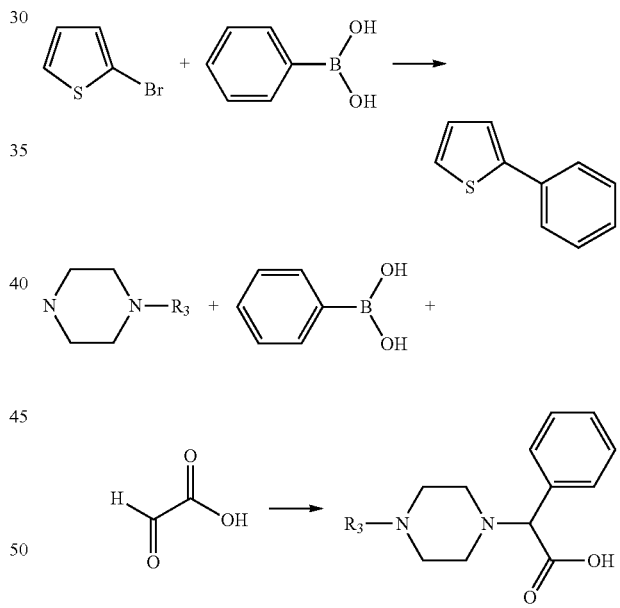

Ugi Condensation Reactions:

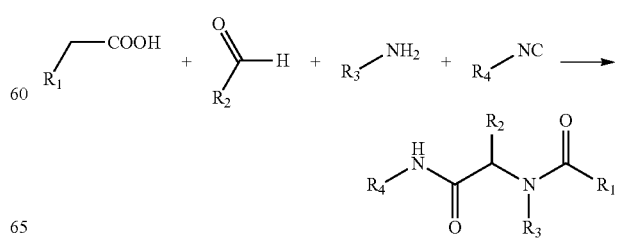

Electrophilic Aromatic Substitution Reactions:

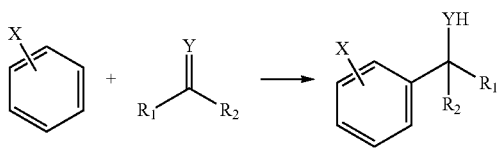

X is an Electron-Donating Group. Imine/Iminium/Enamine Forming Reactions:

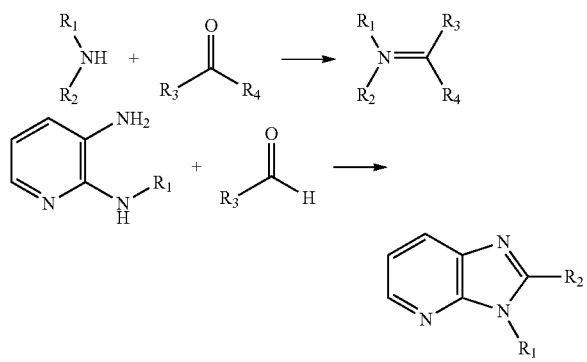

Cycloaddition Reactions:

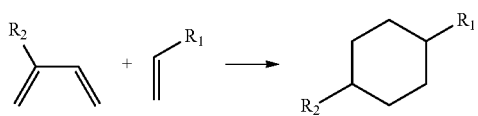

Diels-Alder Cycloaddition

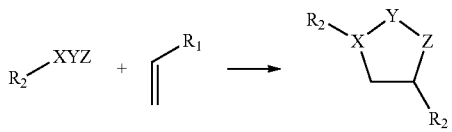

1,3-di[rho]olar Cycloaddition, X—Y—Z=C—N—O, C—N—S, N3, Nucleophilic Aromatic Substitution Reactions:

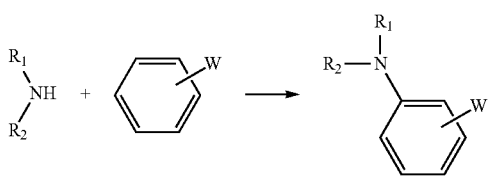

W is an Electron Withdrawing Group

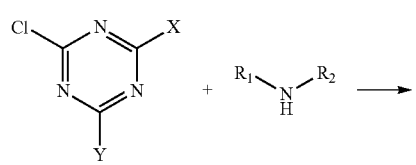

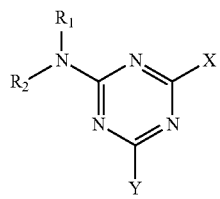

Examples of suitable substituents X and Y include substituted or unsubstituted amino, substituted or unsubstituted alkoxy, substituted or unsubstituted thioalkoxy, substituted or unsubstituted aryloxy and substituted and unsubstituted thioaryloxy.

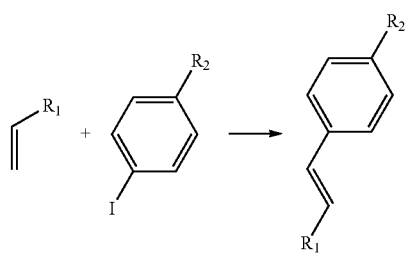

Heck Reaction:

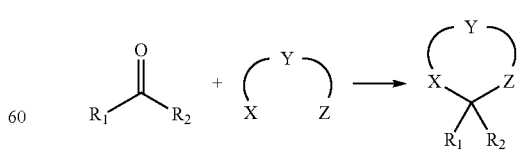

Acetal Formation:

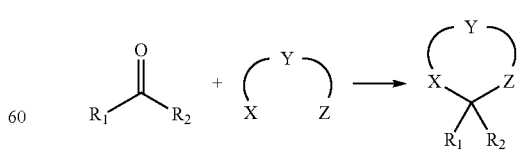

Examples of suitable substituents X and Y include substituted and unsubstituted amino, hydroxyl and sulfhydryl; Y is a linker that connects X and Y and is suitable for forming the ring structure found in the product of the reaction Aldol Reactions:

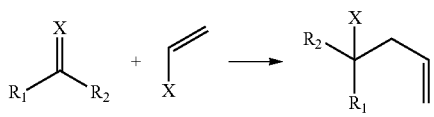

Examples of suitable substituents X include O, S and $NR_j$.

Yet further reaction schemes falling within the scope of the present invention are disclosed herein below.

A. Acylation Reactions

General route to the formation of acylating reactive compound building blocks and the use of these:

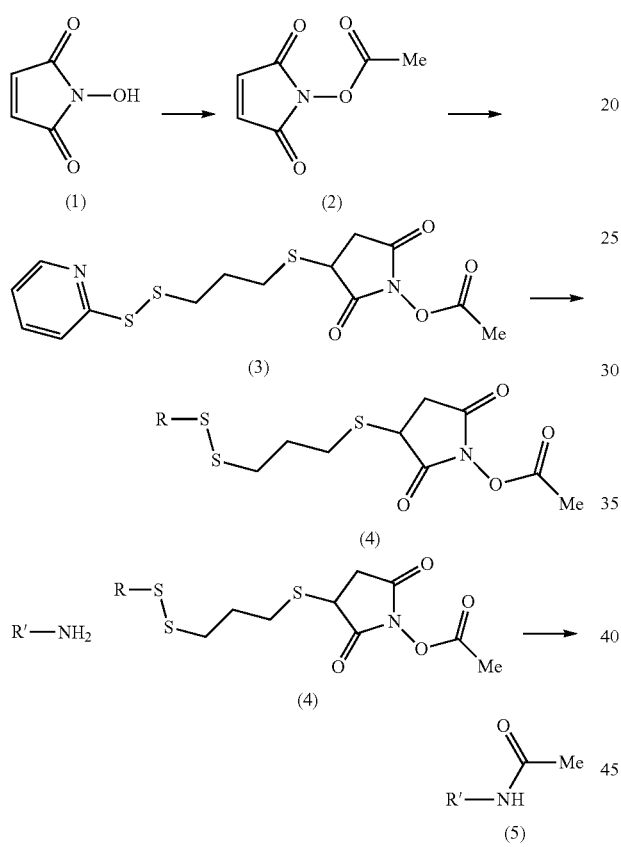

N-hydroxymaleimide (1) may be acylated by the use of an acylchloride e.g. acetylchloride or alternatively acylated in e.g. THF by the use of dicyclohexylcarbodiimide or diisopropylcarbodiimide and acid e.g. acetic acid. The intermediate may be subjected to Michael addition by the use of excess 1,3-propanedithiol, followed by reaction with either 4,4'-dipyridyl disulfide or 2,2'-dipyridyl disulfide. This intermediate (3) may then be loaded onto an oligonucleotide carrying a thiol handle to generate the reactive compound building block (4). Obviously, the intermediate (2) can be attached to the oligonucleotide using another linkage than the disulfide linkage, such as an amide linkage and the N-hydroxymaleimide can be distanced from the oligonucleotide using a variety of spacers.

The reactive compound building block (4) may be reacted with an identifier oligonucleotide comprising a recipient amine group e.g. by following the procedure:

The reactive compound building block (4) (1 nmol) is mixed with an amino-oligonucleotide (1 nmol) in hepes-buffer (20 μL of a 100 mM hepes and 1 M NaCl solution, pH=7.5) and water (39 uL). The oligonucleotides are annealed together by heating to 50° C. and cooling (2° C./second) to 30° C. The mixture is then left o/n at a fluctuating temperature (10° C. for 1 second then 35° C. for 1 second), to yield the product (5).

In more general terms, the reactive compound building blocks indicated below is capable of transferring a reactive compound building block (CE) to a recipient nucleophilic group, typically an amine group. The bold lower horizontal line illustrates the reactive compound building block and the vertical line illustrates a spacer. The 5-membered substituted N-hydroxysuccinimid (NHS) ring serves as an activator, i.e. a labile bond is formed between the oxygen atom connected to the NHS ring and the reactive compound building block. The labile bond may be cleaved by a nucleophilic group, e.g. positioned on a scaffold

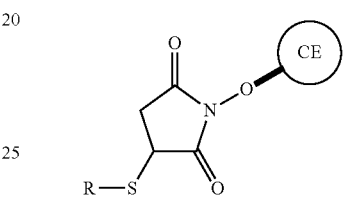

Another reactive compound building block which may form an amide bond is

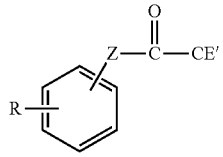

R may be absent or $NO_2$, $CF_3$, halogen, preferably Cl, Br, or I, and Z may be S or O. This type of reactive compound building block is disclosed in Danish patent application No. PA 2002 0951 and US provisional patent application filed 20 Dec. 2002 with the title "A reactive compound building block capable of transferring a functional entity to a recipient reactive group". The content of both patent application are incorporated herein in their entirety by reference.

A nucleophilic group can cleave the linkage between Z and the carbonyl group thereby transferring the reactive compound building block —(C=O)—CE' to said nucleophilic group.

CE and CE' are preferably selected from the group consisting of:

hydrido, substituted and unsubstituted alkyl, substituted and unsubstituted haloalkyl, substituted and unsubstituted hydroxyalkyl, substituted and unsubstituted alkylsulfonyl, substituted and unsubstituted alkenyl, halo, substituted and unsubstituted alkoxy, substituted and unsubstituted alkoxyalkyl, substituted and unsubstituted haloalkoxy, substituted and unsubstituted haloalkoxyalkyl, substituted and unsubstituted aryl, substituted and unsubstituted heterocyclic, substituted and unsubstituted heteroaryl, sulfonyl, substituted and unsubstituted alkylsulfonyl, substituted and unsubstituted arylsulfonyl, sulfamyl, sulfonamidyl, aminosulfonyl, substituted and unsubstituted N-alkylaminosulfonyl, substituted and unsubstituted N-arylaminosulfonyl, substituted and unsubstituted N,N-dialkylaminosulfonyl, substituted and unsubstituted N-alkyl-N-arylaminosulfonyl, substituted and unsubstituted N-alkylaminosulfonyl, substituted and unsubstituted N,N-dialkylaminosulfonyl, substituted and unsubstituted N-arylaminosulfonyl, substituted and unsubstituted N-alkyl-N-arylaminosulfonyl, carboxy, substituted and unsubstituted carboxyalkyl, carbonyl, substituted and unsubstituted alkylcarbonyl, substituted and unsubstituted alkylcarbonylalkyl, substituted and unsubstituted alkoxycarbonyl, substituted and unsubstituted alkoxycarbonylalkyl, aminocarbonyl, substituted and unsubstituted aminocarbonylalkyl, substituted and unsubstituted N-alkylaminocarbonyl, substituted and unsubstituted N-arylaminocarbonyl, substituted and unsubstituted N,N-dialkylaminocarbonyl, substituted and unsubstituted N-alkyl-N-arylaminocarbonyl, substituted and unsubstituted N-alkyl-N-hydroxyaminocarbonyl, substituted and unsubstituted N-alkyl-N-hydroxyaminocarbonylalkyl, substituted and unsubstituted N-alkylaminocarbonyl, substituted and unsubstituted N,N-dialkylaminocarbonyl, substituted and unsubstituted N-arylaminocarbonyl, substituted and unsubstituted N-alkyl-N-arylaminocarbonyl, substituted and unsubstituted aminocarbonylalkyl, substituted and unsubstituted N-cycloalkylaminocarbonyl, substituted and unsubstituted aminoalkyl, substituted and unsubstituted alkylaminoalkyl, amidino, cyanoamidino, substituted and unsubstituted heterocyclicalkyl, substituted and unsubstituted aralkyl, substituted and unsubstituted cycloalkyl, substituted and unsubstituted cycloalkenyl, substituted and unsubstituted alkylthio, substituted and unsubstituted alkylsulfinyl, substituted and unsubstituted N-alkylamino, substituted and unsubstituted N,N-dialkylamino, substituted and unsubstituted arylamino, substituted and unsubstituted aralkylamino, substituted and unsubstituted N-alkyl-N-arylamino, substituted and unsubstituted N-aralkyl-N-alkylamino, substituted and unsubstituted N-arylaminoalkyl, substituted and unsubstituted N-aralkylaminoalkyl, substituted and unsubstituted N-alkyl-N-arylaminoalkyl, substituted and unsubstituted N-aralkyl-N-alkylaminoalkyl, acyl, acylamino, substituted and unsubstituted arylthio, substituted and unsubstituted aralkylthio, substituted and unsubstituted aryloxy, substituted and unsubstituted aralkoxy, substituted and unsubstituted haloaralkyl, substituted and unsubstituted carboxyhaloalkyl, substituted and unsubstituted alkoxycarbonylhaloalkyl, substituted and unsubstituted aminocarbonylhaloalkyl, substituted and unsubstituted alkylaminocarbonylhaloalkyl, substituted and unsubstituted alkoxycarbonylcyanoalkenyl, substituted and unsubstituted carboxyalkylaminocarbonyl, substituted and unsubstituted aralkoxycarbonylalkylaminocarbonyl, substituted and unsubstituted cycloalkylalkyl, and substituted and unsubstituted aralkenyl.

B. Alkylation

General Route to the Formation of Alkylating/Vinylating Reactive Compound Building Blocks and Use of these:

Alkylating reactive compound building blocks may have the following general structure:

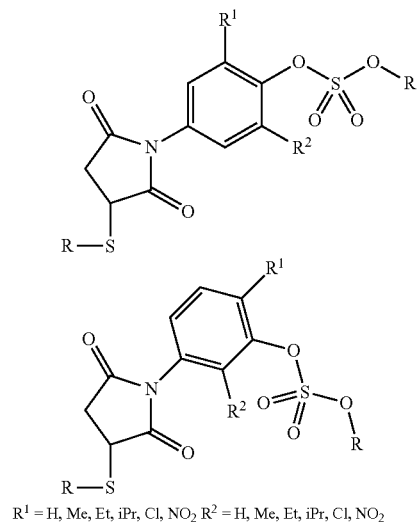

$R^1$ = H, Me, Et, iPr, Cl, $NO_2$ $R^2$ = H, Me, Et, iPr, Cl, $NO_2$ $R^1$ and $R^2$ may be used to tune the reactivity of the sulphate to allow appropriate reactivity. Chloro and nitro substitution will increase reactivity. Alkyl groups will decrease reactivity. Ortho substituents to the sulphate will due to steric reasons direct incoming nucleophiles to attack the R-group selectively and avoid attack on sulphur.

An example of the formation of an alkylating reactive compound building block and the transfer of a functional entity is depicted below:

3-Aminophenol (6) is treated with maleic anhydride, followed by treatment with an acid e.g. $H_2SO_4$ or $P_2O_5$ and heated to yield the maleimide (7). The ring closure to the maleimide may also be achieved when an acid stable O-protection group is used by treatment with $Ac_2O$, with or without heating, followed by O-deprotection. Alternatively reflux in $Ac_2O$, followed by O-deacetylation in hot water/dioxane to yield (7). Further treatment of (7) with $SO_2Cl_2$, with or without triethylamine or potassium carbonate in dichloromethane or a higher boiling solvent will yield the intermediate (8), which may be isolated or directly further transformed into the aryl alkyl sulphate by the quench with the appropriate alcohol, in this case MeOH, whereby (9) will be formed.

The organic moiety (9) may be connected to an oligonucleotide, as follows: A thiol carrying oligonucleotide in buffer 50 mM MOPS or hepes or phosphate pH 7.5 is treated with a 1-100 mM solution and preferably 7.5 mM solution of the organic reactive compound building block (9) in DMSO or alternatively DMF, such that the DMSO/DMF concentration is 5-50%, and preferably 10%. The mixture is left for 1-16 h and preferably 2-4 h at 25° C. to give the alkylating agent in this case a methylating reactive compound building block (10).

The reaction of the alkylating reactive compound building block (10) with an amine bearing nascent bi-functional complex may be conducted as follows: The bi-functional complex (1 nmol) is mixed the reactive compound building block (10) (1 nmol) in hepes-buffer (20 µL of a 100 mM hepes and 1 M NaCl solution, pH=7.5) and water (39 µL). The oligonucleotides are annealed to each other by heating to 50° C. and cooled (2° C./second) to 30° C. The mixture is then left o/n at a fluctuating temperature (10° C. for 1 second then 35° C. for 1 second), to yield the methylamine reaction product (11).

In more general terms, a reactive compound building block capable of transferring a reactive compound building block to a receiving reactive group forming a single bond is

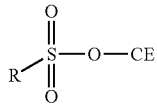

The receiving group may be a nucleophile, such as a group comprising a hetero atom, thereby forming a single bond between the reactive compound building block and the hetero atom, or the receiving group may be an electronegative carbon atom, thereby forming a C—C bond between the reactive compound building block and the scaffold.

CE is defined as herein above under section A (acylation reactions).

C. Vinylation Reactions

A vinylating reactive compound building block may be prepared and used similarly as described above for an alkylating reactive compound building block. Although instead of reacting the chlorosulphonate (8 above) with an alcohol, the intermediate chlorosulphate is isolated and treated with an enolate or O-trialkylsilylenolate with or without the presence of fluoride. E.g.

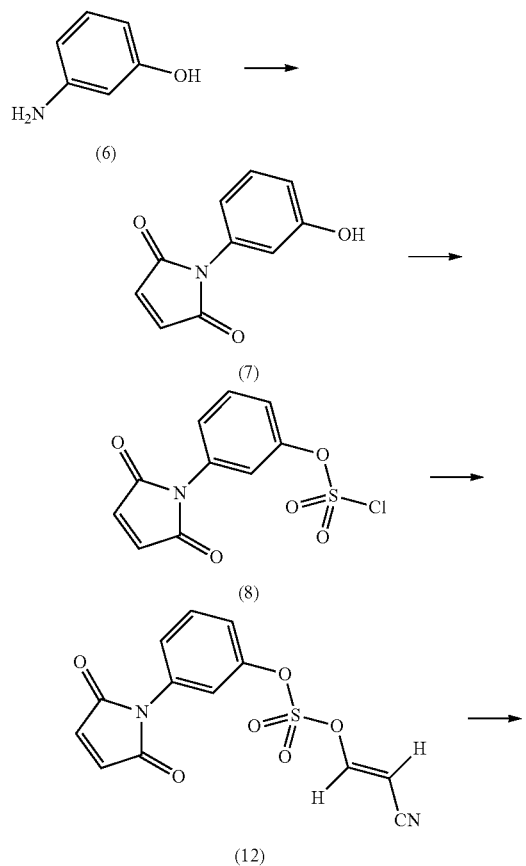

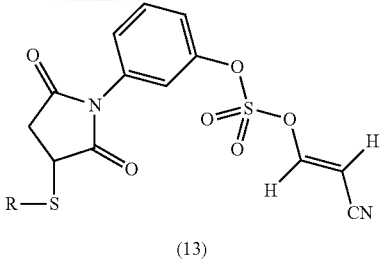

Formation of an exemplary vinylating reactive compound building block (13): The thiol carrying oligonucleotide in buffer 50 mM MOPS or hepes or phosphate pH 7.5 is treated with a 1-100 mM solution and preferably 7.5 mM solution of the organic moiety (12) in DMSO or alternatively DMF, such that the DMSO/DMF concentration is 5-50%, and preferably 10%. The mixture is left for 1-16 h and preferably 2-4 h at 25° C. to give the vinylating reactive compound building block (13).

The sulfonylenolate (13) may be used to react with amine carrying scaffold to give an enamine (14a and/or 14b) or e.g. react with a carbanion to yield (15a and/or 15b). E.g.

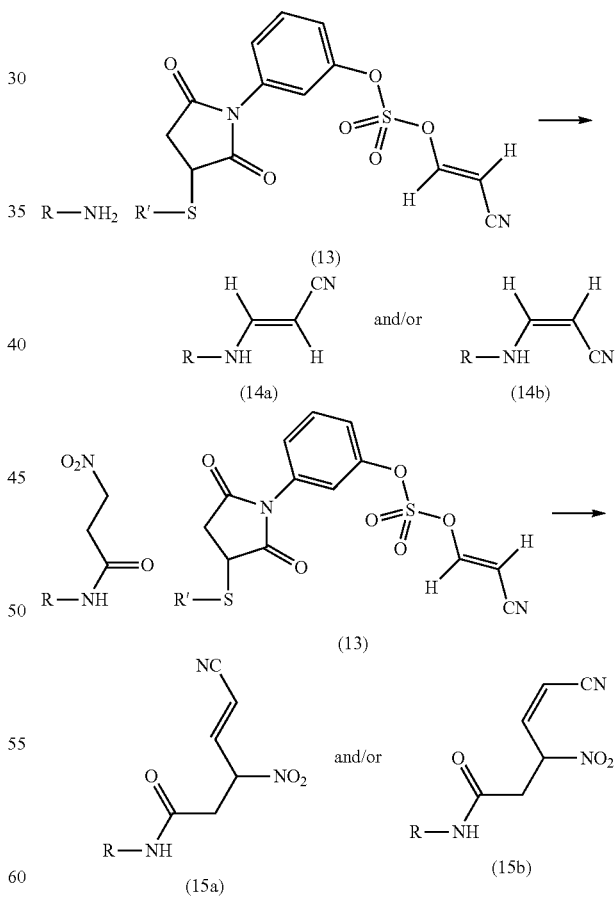

The reaction of the vinylating reactive compound building block (13) and an amine or nitroalkyl carrying identifier may be conducted as follows:

The amino-oligonucleotide (1 nmol) or nitroalkyl-oligonucleotide (1 nmol) identifier is mixed with the reactive compound building block (1 nmol) (13) in 0.1 M TAPS, phosphate or hepes-buffer and 300 mM NaCl solution, pH=7.5-8.5 and preferably pH=8.5. The oligonucleotides are annealed to the template by heating to 50° C. and cooled (2° C./second) to 30° C. The mixture is then left o/n at a fluctuating temperature (10° C. for 1 second then 35° C. for 1 second), to yield reaction product (14a/b or 15a/b). Alternative to the alkyl and vinyl sulphates described above may equally effective be sulphonates as e.g. (31) (however with R″ instead as alkyl or vinyl), described below, prepared from (28, with the phenyl group substituted by an alkyl group) and (29), and be used as alkylating and vinylating agents.

Another reactive compound building block capable of forming a double bond by the transfer of a reactive compound building block to a recipient aldehyde group is shown below. A double bond between the carbon of the aldehyde and the reactive compound building block is formed by the reaction.

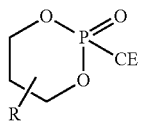

The above reactive compound building block is comprised by the Danish patent application No. DK PA 2002 01952 and the US provisional patent application filed 20 Dec. 2002 with the title "A reactive compound building block capable of transferring a functional entity to a recipient reactive group forming a C=C double bond". The content of both patent applications are incorporated herein in their entirety by reference.

CE is defined as herein above under section A (acylation reactions).

D. Alkenylidation Reactions

General Route to the Formation of Wittig and HWE Reactive Compound Building Blocks and Use of these:

Commercially available compound (16) may be transformed into the NHS ester (17) by standard means, i.e. DCC or DIC couplings. An amine carrying oligonucleotide in buffer 50 mM MOPS or hepes or phosphate pH 7.5 is treated with a 1-100 mM solution and preferably 7.5 mM solution of the organic compound in DMSO or alternatively DMF, such that the DMSO/DMF concentration is 5-50%, and preferably 10%. The mixture is left for 1-16 h and preferably 2-4 h at 25° C. to give the phosphine bound precursor reactive compound building block (18). This precursor reactive compound building block is further transformed by addition of the appropriate alkylhalide, e.g. N,N-dimethyl-2-iodoacetamide as a 1-100 mM and preferably 7.5 mM solution in DMSO or DMF such that the DMSO/DMF concentration is 5-50%, and preferably 10%. The mixture is left for 1-16 h and preferably 2-4 h at 25° C. to give the reactive compound building block (19). As an alternative to this, the organic compound (17) may be P-alkylated with an alkylhalide and then be coupled onto an amine carrying oligonucleotide to yield (19).

An aldehyde carrying identifier (20), may be formed by the reaction between the NHS ester of 4-formylbenzoic acid and an amine carrying oligonucleotide, using conditions similar to those described above. The identifier (20) reacts with (19) under slightly alkaline conditions to yield the alkene (21).

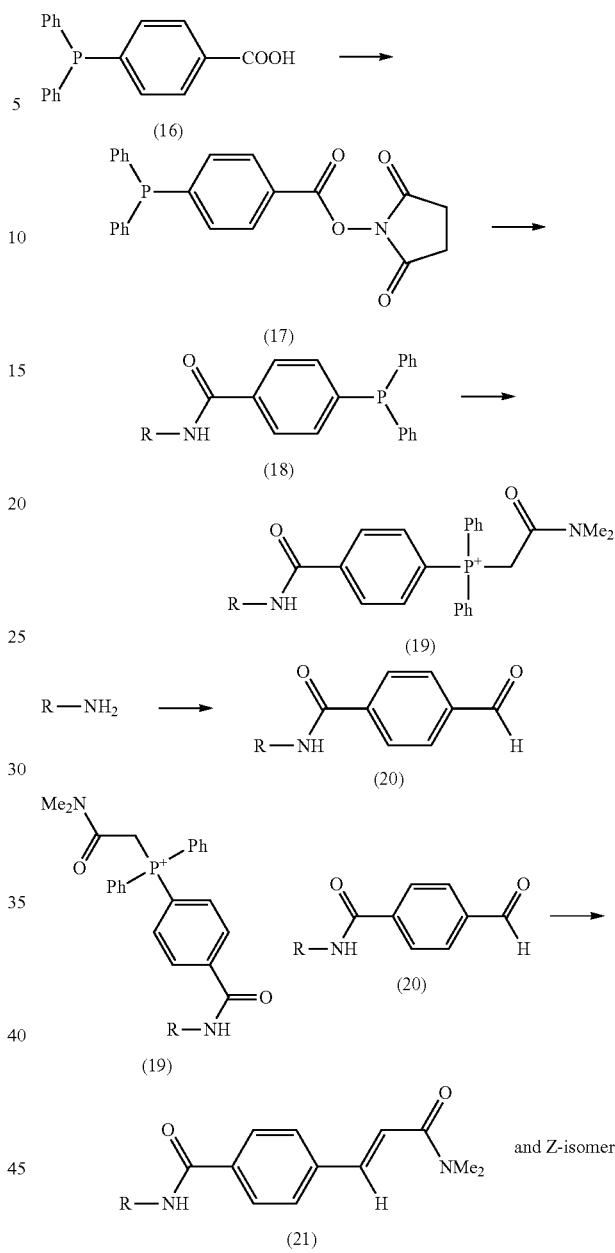

The reaction of monomer reactive compound building blocks (19) and identifier (20) may be conducted as follows: The identifier (20) (1 nmol) is mixed with reactive compound building block (19) (1 nmol) in 0.1 M TAPS, phosphate or hepes-buffer and 1 M NaCl solution, pH=7.5-8.5 and preferably pH=8.0. The reaction mixture is left at 35-65° C. preferably 58° C. over night to yield reaction product (21).

As an alternative to (17), phosphonates (24) may be used instead. They may be prepared by the reaction between diethylchlorophosphite (22) and the appropriate carboxy carrying alcohol. The carboxylic acid is then transformed into the NHS ester (24) and the process and alternatives described above may be applied. Although instead of a simple P-alkylation, the phosphite may undergo Arbuzov's reaction and generate the phosphonate. Reactive compound building block (25) benefits from the fact that it is more reactive than its phosphonium counterpart (19).

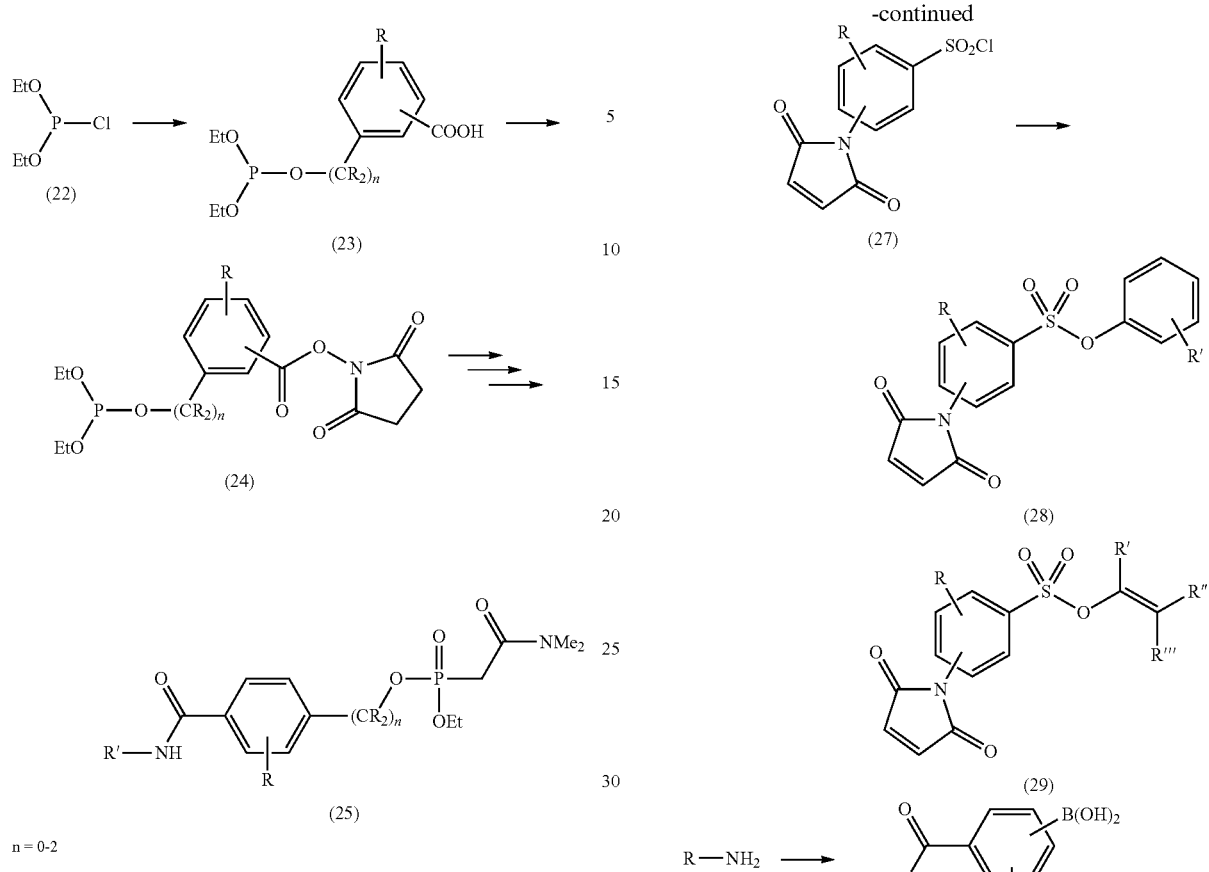

E. Transition Metal Catalyzed Arylation, Hetarylation and Vinylation Reactions Electrophilic reactive compound building blocks (31) capable of transferring an aryl, hetaryl or vinyl functionality may be prepared from organic compounds (28) and (29) by the use of coupling procedures for maleimide derivatives to SH-carrying oligonucleotides described above. Alternatively to the maleimide the NHS-ester derivatives may be prepared from e.g. carboxybenzensulfonic acid derivatives, be used by coupling of these to an amine carrying oligonucleotide. The R-group of (28) and (29) is used to tune the reactivity of the sulphonate to yield the appropriate reactivity.

The transition metal catalyzed cross coupling may be conducted as follows: A premix of 1.4 mM $Na_2PdCl_4$ and 2.8 mM $P(p\text{-}SO_3C_6H_4)_3$ in water left for 15 min was added to a mixture of the identifier (30) and reactive compound building block (31) (both 1 nmol) in 0.5 M NaOAc buffer at pH=5 and 75 mM NaCl (final [Pd]=0.3 mM). The mixture is then left o/n at 35-65° C. preferably 58° C., to yield reaction product (32).

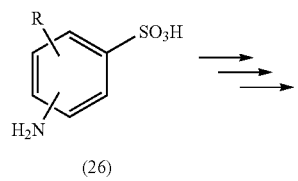

Corresponding nucleophilic monomer reactive compound building blocks capable of transferring an aryl, hetaryl or vinyl functionality may be prepared from organic compounds of the type (35). This is available by estrification of a boronic acid by a diol e.g. (33), followed by transformation into the NHS-ester derivative. The NHS-ester derivative may then be coupled to an oligonucleotide, by use of coupling procedures for NHS-ester derivatives to amine carrying oligonucleotides described above, to generate reactive compound building block type (37). Alternatively, maleimide derivatives may be prepared as described above and loaded onto SH-carrying oligonucleotides.

The transition metal catalyzed cross coupling is conducted as follows:

A premix of 1.4 mM $Na_2PdCl_4$ and 2.8 mM $P(p-SO_3C_6H_4)_3$ in water left for 15 min was added to a mixture of the identifier (36) and the reactive compound building block (37) (both 1 nmol) in 0.5 M NaOAc buffer at pH=5 and 75 mM NaCl (final [Pd]=0.3 mM). The mixture is then left o/n at 35-65° C. preferably 58° C., to yield template bound captoethanol is reacted with a dipyridyl disulfide, followed by O-tosylation (Z=OTs). The tosylate (40) may then be reacted directly with an enolate or in the presence of fluoride with a O-trialkylsilylenolate to generate the enolate (41).

The enamine or enolate (41) may then be coupled onto an SH-carrying oligonucleotide as described above to give the reactive compound building block (42).

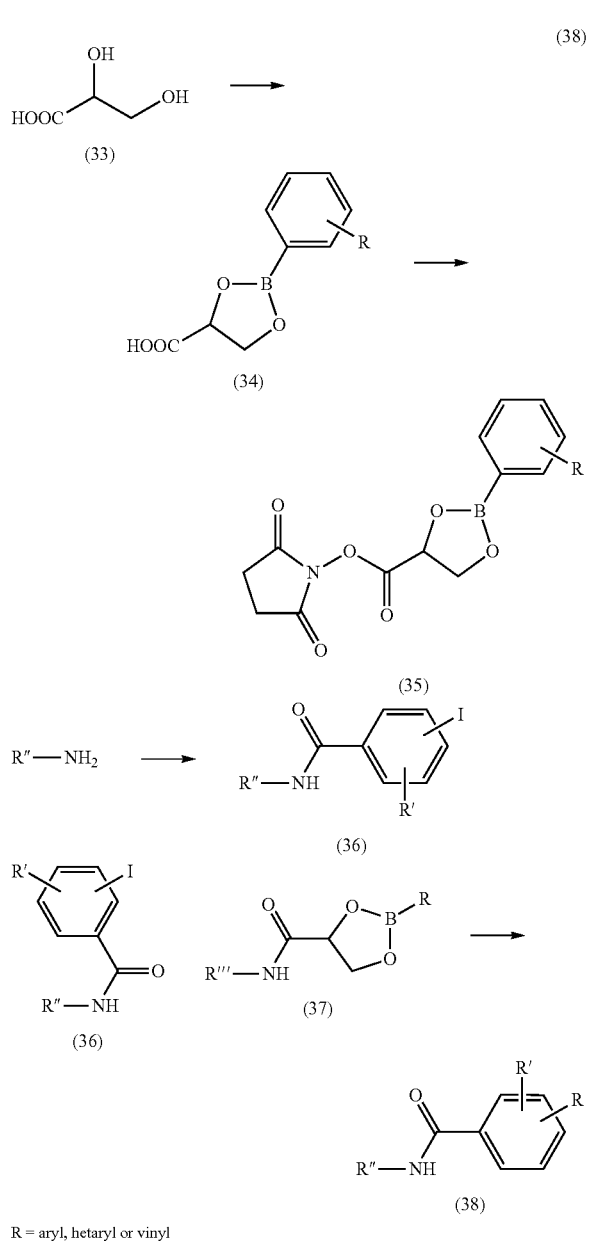

R = aryl, hetaryl or vinyl

F. Reactions of Enamine and Enolether Monomer Reactive Compound Building Blocks

Reactive compound building blocks loaded with enamines and enolethers may be prepared as follows:

For Z=NHR(R=H, alkyl, aryl, hetaryl), a 2-mercaptoethylamine may be reacted with a dipyridyl disulfide to generate the activated disulfide (40), which may then be condensed to a ketone or an aldehyde under dehydrating conditions to yield the enamine (41). For Z=OH, 2-mer-

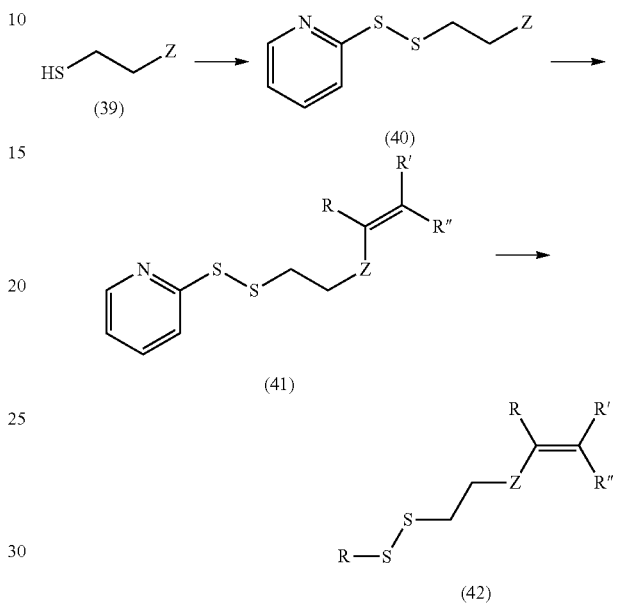

The reactive compound building block (42) may be reacted with a carbonyl carrying identifier oligonucleotide like (44) or alternatively an alkylhalide carrying oligonucleotide like (43) as follows:

The reactive compound building block (42) (1 nmol) is mixed with the identifier (43) (1 nmol) in 50 mM MOPS, phosphate or hepes-buffer buffer and 250 mM NaCl solution, pH=7.5-8.5 and preferably pH=7.5. The reaction mixture is left at 35-65° C. preferably 58° C. over night or alternatively at a fluctuating temperature (10° C. for 1 second then 35° C. for 1 second) to yield reaction product (46), where Z=O or NR. For compounds where Z=NR slightly acidic conditions may be applied to yield product (46) with Z=O.

The reactive compound building block (42) (1 nmol) is mixed with the identifier (44) (1 nmol) in 0.1 M TAPS, phosphate or hepes-buffer buffer and 300 mM NaCl solution, pH=7.5-8.5 and preferably pH=8.0. The reaction mixture is left at 35-65° C. preferably 58° C. over night or alternatively at a fluctuating temperature (10° C. for 1 second then 35° C. for 1 second) to yield reaction product (45), where Z=O or NR. For compounds where Z=NR slightly acidic conditions may be applied to yield product (45) with Z=O.

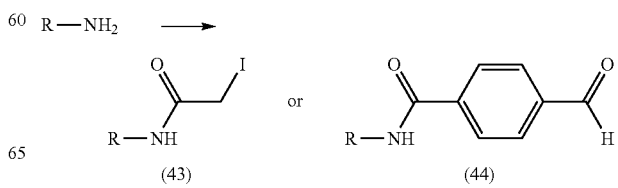

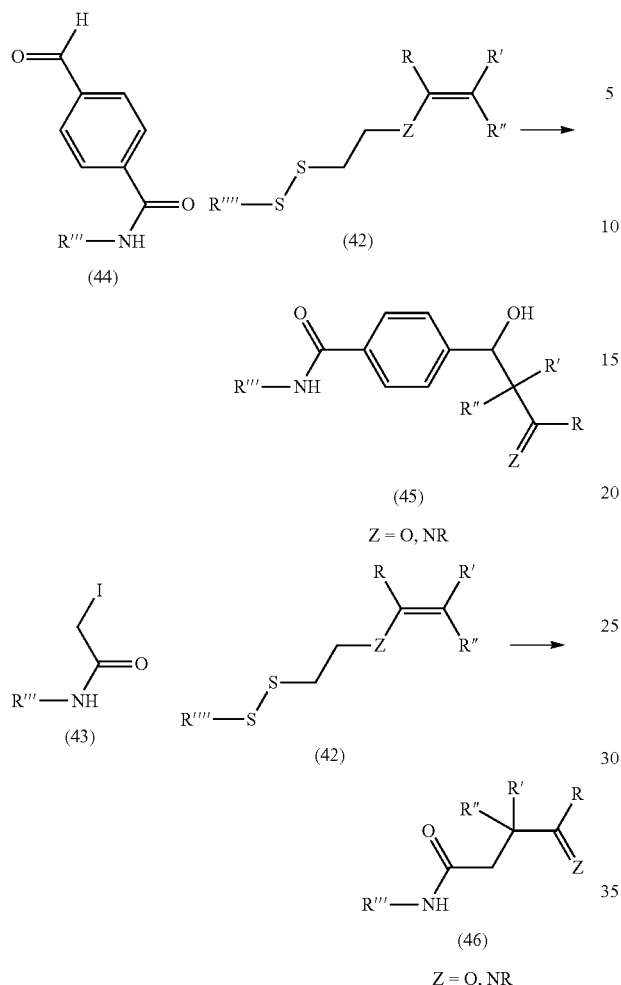

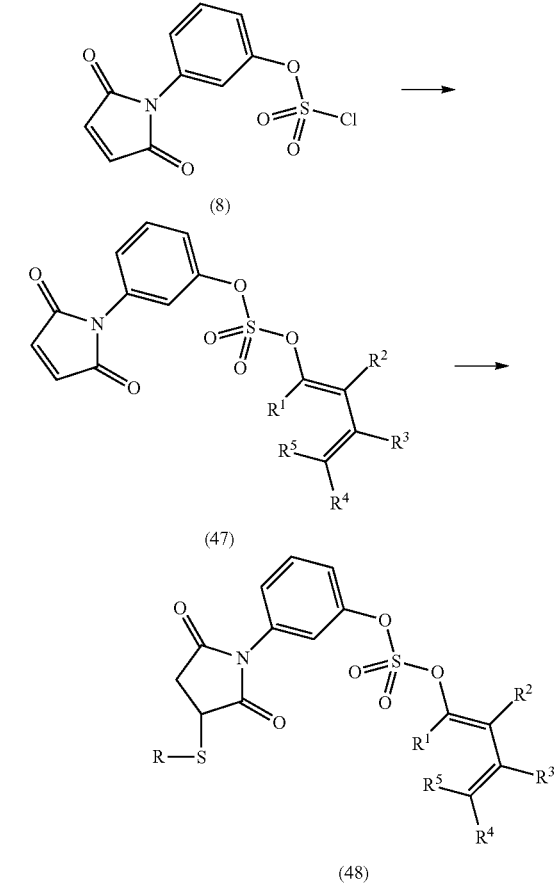

Enolethers type (13) may undergo cycloaddition with or without catalysis. Similarly, dienolethers may be prepared and used, e.g. by reaction of (8) with the enolate or trialkylsilylenolate (in the presence of fluoride) of an α,β-unsaturated ketone or aldehyde to generate (47), which may be loaded onto an SH-carrying oligonucleotide, to yield monomer reactive compound building block (48).

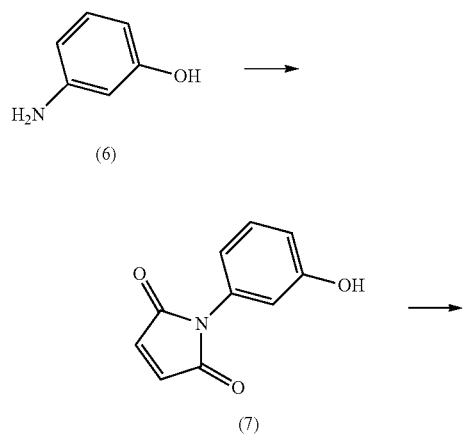

The diene (49), the ene (50) and the 1,3-dipole (51) may be formed by simple reaction between an amino carrying oligonucleotide and the NHS-ester of the corresponding organic compound. Reaction of (13) or alternatively (31, R"=vinyl) with dienes as e.g. (49) to yield (52) or e.g. 1,3-dipoles (51) to yield (53) and reaction of (48) or (31, R"=dienyl) with enes as e.g. (50) to yield (54) may be conducted as follows:

The reactive compound building block (13) or (48) (1 nmol) is mixed with the identifier (49) or (50) or (51) (1 nmol) in 50 mM MOPS, phosphate or hepes-buffer buffer and 2.8 M NaCl solution, pH=7.5-8.5 and preferably pH=7.5. The reaction mixture is left at 35-65° C. preferably 58° C. over night or alternatively at a fluctuating temperature (10° C. for 1 second then 35° C. for 1 second) to yield template bound (52), (53) or (54), respectively.

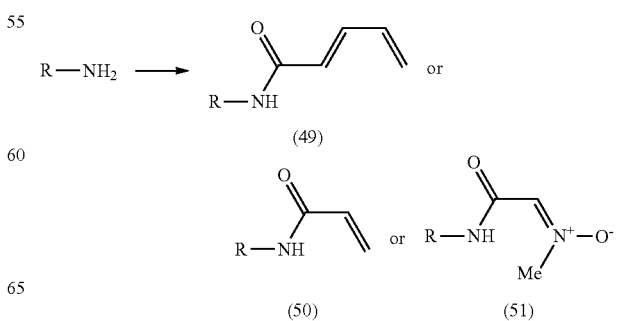

Cross-Link Cleavage Reactive Compound Building Blocks

It may be advantageous to split the transfer of a reactive compound building block to a recipient reactive group into two separate steps, namely a cross-linking step and a cleavage step because each step can be optimized. A suitable reactive compound building block for this two step process is illustrated below:

Initially, a reactive group appearing on the functional entity precursor (abbreviated FEP) reacts with a recipient reactive group, e.g. a reactive group appearing on a scaffold, thereby forming a cross-link. Subsequently, a cleavage is performed, usually by adding an aqueous oxidising agent such as $I_2$, $Br_2$, $Cl_2$, $H^+$, or a Lewis acid. The cleavage results in a transfer of the group HZ-FEP- to the recipient moiety, such as a scaffold.

In the above formula

Z is O, S, $NR^4$

Q is N, $CR^1$

P is a valence bond, O, S, $NR^4$, or a group $C_{5-7}$arylene, $C_{1-6}$alkylene, $C_{1-6}$O-alkylene, $C_{1-6}$S-alkylene, $NR^1$-alkylene, $C_{1-6}$alkylene-O, $C_{1-6}$alkylene-S option said group being substituted with 0-3 $R^4$, 0-3 $R^5$ and 0-3 $R^9$ or $C_1$-$C_3$ alkylene-$NR^4_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4_2$, $C_1$-$C_2$ alkylene-O—$NR^4C(O)R^8$, $C_1$-$C_2$ alkylene-O—$NR^4C(O)OR^5$ substituted with 0-3 $R^9$, B is a group comprising D-E-F, in which D is a valence bond or a group $C_{1-6}$alkylene, $C_{1-6}$alkenylene, $C_{1-6}$alkynylene, $C_{5-7}$arylene, or $C_{5-7}$heteroarylene, said group optionally being substituted with 1 to 4 group $R^{11}$, E is, when present, a valence bond, O, S, $NR^4$, or a group $C_{1-6}$alkylene, $C_{1-6}$alkenylene, $C_{1-6}$alkynylene, $C_{5-7}$arylene, or $C_{5-7}$heteroarylene, said group optionally being substituted with 1 to 4 group $R^{11}$, F is, when present, a valence bond, O, S, or $NR^4$, A is a spacing group distancing the chemical structure from the complementing element, which may be a nucleic acid, $R^1$, $R^2$, and $R^3$ are independent of each other selected among the group consisting of H, $C_1$-$C_6$ alkyl, $C_2$-$C_6$ alkenyl, $C_2$-$C_6$ alkynyl, $C_4$-$C_8$ alkadienyl, $C_3$-$C_7$ cycloalkyl, $C_3$-$C_7$ cycloheteroalkyl, aryl, and heteroaryl, said group being substituted with 0-3 $R^4$, 0-3 $R^5$ and 0-3 $R^9$ or $C_1$-$C_3$ alkylene-$NR^4{}_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4{}_2$, $C_1$-$C_2$ alkylene-O—$NR^4C(O)R^8$, $C_1$-$C_2$ alkylene-O—$NR^4C(O)OR^8$ substituted with 0-3 $R^9$, FEP is a group selected among the group consisting of H, $C_1$-$C_6$ alkyl, $C_2$-$C_6$ alkenyl, $C_2$-$C_6$ alkynyl, $C_4$-$C_8$ alkadienyl, $C_3$-$C_7$ cycloalkyl, $C_3$-$C_7$ cycloheteroalkyl, aryl, and heteroaryl, said group being substituted with 0-3 $R^4$, 0-3 $R^5$ and 0-3 $R^8$ or $C_1$-$C_3$ alkylene-$NR^4{}_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4{}_2$, $C_1$-$C_2$ alkylene-O—$NR^4C(O)R^8$, $C_1$-$C_2$ alkylene-O—$NR^4C(O)OR^8$ substituted with 0-3 $R^9$, where $R^4$ is H or selected independently among the group consisting of $C_1$-$C_6$ alkyl, $C_2$-$C_6$ alkenyl, $C_2$-$C_6$ alkynyl, $C_3$-$C_7$ cycloalkyl, $C_3$-$C_7$ cycloheteroalkyl, aryl, heteroaryl, said group being substituted with 0-3 $R^9$ and $R^5$ is selected independently from —$N_3$, —CNO, —C(NOH)$NH_2$, —NHOH, —NHN$HR^6$, —C(O)$R^6$, —Sn$R^6{}_3$, —B(O$R^6$)$_2$, —P(O) (O$R^6$)$_2$ or the group consisting of $C_2$-$C_6$ alkenyl, $C_2$-$C_6$ alkynyl, $C_4$-$C_8$ alkadienyl said group being substituted with 0-2 $R^7$, where $R^6$ is selected independently from H, $C_1$-$C_6$ alkyl, $C_3$.$C_7$ cycloalkyl, aryl or $C_1$-$C_6$ alkylene-aryl substituted with 0-5 halogen atoms selected from —F, —Cl, —Br, and —I; and $R^7$ is independently selected from —$NO_2$, —COO$R^6$, —COR$^E$, —CN, —OSi$R^6{}_3$, —O$R^6$ and —$NR^6{}_2$.

$R^8$ is H, $C_1$-$C_6$ alkyl, $C_2$-$C_6$ alkenyl, $C_2$-$C_6$ alkynyl, $C_3$-$C_7$ cycloalkyl, aryl or $C_1$-$C_6$ alkylene-aryl substituted with 0-3 substituents independently selected from —F, —Cl, —$NO_2$, —$R^3$, —O$R^3$, —Si$R^3{}_3$ $R^9$ is =O, —F, —Cl, —Br, —I, —CN, —$NO_2$, —O$R^6$, —$NR^6{}_2$, —$NR^6$—C(O)$R^8$, —$NR^6$—C(O)O$R^8$, —S$R^6$, —S(O)$R^6$, —S(O)$_2R^6$, —COO$R^6$, —C(O)$NR^6{}_2$ and —S(O)$_2NR^6{}_2$.

In a preferred embodiment Z is O or S, P is a valence bond, Q is CH, B is $CH_2$, and $R^1$, $R^2$, and $R^3$ is H. The bond between the carbonyl group and Z is cleavable with aqueous $I_2$.

Protection Groups

Reactive groups may optionally be protected using protection group chemistries as e.g. described by Green T. W. and Wuts P. G. M in Protection Groups in Organic Synthesis, Wiley, 1999, ISBN: 0-471-16019-9 which is hereby incorporated by reference.

In one embodiment amines may optionally be protected as carbamates, such as for example methyl carbamate, ethyl carbamate, t-butyl carbamate (Boc), 9-fluorenylmethyl carbamate (Fmoc), 2,2,2-trichlorethyl carbamate, 2-trimethylsilylethyl carbamate, vinyl carbamate, allyl carbamate, benzyl carbamate, p-methoxybenzyl carbamate, p-nitrobenzyl carbamate, m-nitrophenyl carbamate, 3,5-dimethoxybenzyl carbamate, alpha-methylnitropiperonyl carbamate, o-nitrophenyl carbamate, 3,4-dimethoxy-6-nitro carbamate, phenyl (o-nitrophenyl)methyl carbamate, 2-(2-nitrophenyl)ethyl carbamate, 6-nitroveratryl carbamate, 4-methoxyphenacyl carbamate, methylsulfonylethyl carbamate (MSc), which may optionally be deprotected as appropriate according to literature procedures as described by Green T. W. and Wuts P. G. M in *Protection Groups in Organic Synthesis*, Wiley, 1999.

In another embodiment amines may optionally be protected as amides, such as for example trifluoroacetamide, trichloroacetamide, 4-pentenoic acid amide, o-(benzoyloxymethyl)benzamide, 2-(acetoxymethyl)benzamide, N-phthalimide, N-tetrachlorophthalimide, a nosyl (Ns) protection group, such as for example an o-nitrophenylsulfonamide (o-Ns), for example an p-nitrophenylsulfonylsulfonamide (p-Ns), which may optionally be deprotected as appropriate according to literature procedures as described by Green T. W. and Wuts P. G. M in *Protection Groups in Organic Synthesis*, Wiley, 1999.

In a further embodiment amines may optionally be protected as triphenylmethyl amine (trityl, Trt), di(p-methoxyphenyl)phenylmethyl (DMT) amine, which may optionally be deprotected as appropriate according to literature procedures as described by Green T. W. and Wuts P. G. M in *Protection Groups in Organic Synthesis*, Wiley, 1999.

In one embodiment carboxylic acids may optionally be protected such as for example methyl ester, ethyl ester, t-butyl ester, benzyl ester, p-methoxy benzyl ester, 9-fluorenylmethyl ester, methoxy methyl ester, benzyloxy methyl ester, cyanomethyl ester, phenacyl ester, p-methoxy phenacyl ester, 2,2,2-trichloroethyl ester, vinyl ester, allyl ester, triethylsilyl ester, t-butyldimethylsilyl ester, phenyldimethylsilyl ester, triphenylmethyl ester, di(p-methoxyphenyl) phenylmethyl ester, methyl sulfonylethyl ester, which may optionally be deprotected as appropriate according to literature procedures as described by Green T. W. and Wuts P. G. M in *Protection Groups in Organic Synthesis*, Wiley, 1999.

In one embodiment hydroxyl groups may optionally be protected such as for example methyl ether, methoxymethyl ether, benzyloxymethyl ether, p-methoxybenzyloxymethyl ether, o-nitrobenzyloxymethyl ether, tetrahydropyranyl ether, tetrahydrofuranyl ether, ethoxyethyl ether, 2,2,2-trichloroethyl ether, allyl ether, vinyl ether, benzyl ether, p-methoxybenzyl ether, o-nitrobenzyl ether, triphenylmethyl ether, di(p-methoxyphenyl)phenylmethyl ether, which may optionally be deprotected as appropriate according to literature procedures as described by Green T. W. and Wuts P. G. M in *Protection Groups in Organic Synthesis*, Wiley, 1999.

In another embodiment hydroxyl groups may optionally be protected such as for example formic acid ester, acetic acid ester, trichloroacetic acid ester, trifluoroacetic acid ester, which may optionally be deprotected as appropriate according to literature procedures as described by Green T. W. and Wuts P. G. M in *Protection Groups in Organic Synthesis*, Wiley, 1999.

In a further embodiment hydroxyl groups may optionally be protected such as for example methyl carbonates, methoxymethyl carbonates, 9-fluorenylmethyl carbonates, ethyl carbonates, 2,2,2-trichloroethyl carbonates, allyl carbonates, vinyl carbonates, t-butyl carbonates, benzyl carbonates, p-methoxybenzyl carbonates, tosylate, which may optionally be deprotected as appropriate according to literature procedures as described by Green T. W. and Wuts P. G. M in *Protection Groups in Organic Synthesis*, Wiley, 1999.

In one embodiment carbonyl groups may optionally be protected such as for example dimethyl acetal and ketal, dibenzyl acetal and ketal, 1,3-dioxanes, 1,3-dioxolanes, 1,3-dithiane, 1,3-dithiolane, S,S'-dimethyl thioacetal and ketal, which may optionally be deprotected as appropriate according to literature procedures as described by Green T. W. and Wuts P. G. M in *Protection Groups in Organic Synthesis*, Wiley, 1999.

In another embodiment aldehydes may optionally be masked as 1,2-diols, which may optionally be demasked by use of periodate. For example:

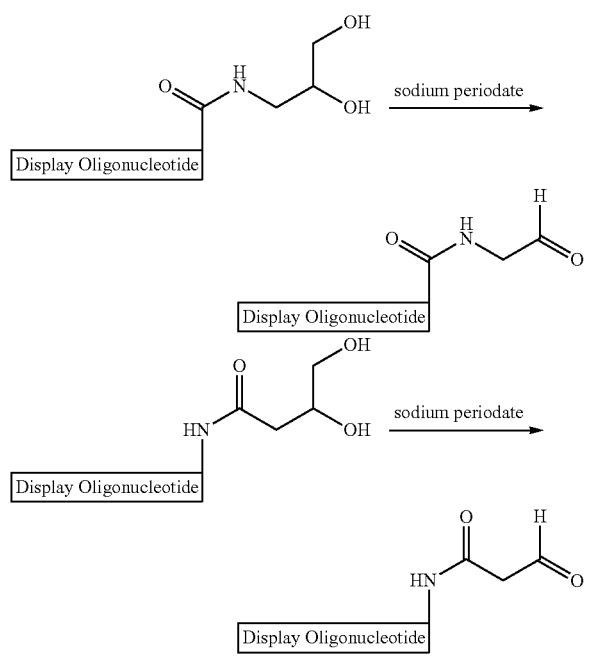

1. Dry down 1-20 nmol diol functionalised oligo
2. Add 25 μl NaIO$_4$ (50 mM in Sodium Acetate Buffer pH 4)
3. Shake at 25° C. for 30 min.
4. Add 25 μl 700 mM Phosphate buffer pH 6.7
5. Purify by P6 spin column
6. Dry down the aldehyde functionalized oligo (temperature max. 45° C.)

The following procedures may be applied for deprotection of protection groups. Other methods may also be applied as described in the literature and by Green T. W. and Wuts P. G. M in *Protection Groups in Organic Synthesis*, Wiley, 1999:

Procedure for tBu Ester and N-Boc Deprotection
  1. Dry down functionalised oligo in an PCR tube
  2. Add 20 μL 37.5 mM NaOAc and 5 μL 1M MgCl$_2$
  3. Incubate at 70° C. ON (Lid 100° C.). in PCR-machine
  4. Add 45 μL H$_2$O
  5. Purify by P6 spin column Procedure Fmoc Deprotection in Water
  1. Dry down oligo
  2. Add 6% piperidine/H$_2$O 10 μL
  3. Shake 30 min at 25° C.
  4. Add 40 μL H$_2$O
  5. Purify by P6 spin column Procedure Msc Deprotection in Water
  1. Dry down oligo
  2. Dissolve in 25 μL Sodium Borate Buffer (0.1 M, pH=10)
  3. Shake 3h at 40° C.
  4. Add 25 μL Water
  5. Purify by P6 spin column Deprotection of tBu, Me and Et Esters
  1. Dry down oligo in an PCR tube
  2. Add 20 μL 100 mM LiOH, seal tube
  3. Incubate at 80° C. in PCR machine for 30 minutes
  4. Add 40 μL 100 mM NaOAc buffer pH 5
  5. Purify by P6 spin column Procedure for Fmoc Deprotection on DEAE Sepharose
  1) 100 μL DEAE suspension is pipetted into a filtertube and drained by vacuum.
  2) Add water (200 μL) and drain.
  3) Bind solution (H$_2$O (200 μL)) is added. Shake 10 min 600 rpm, then drain.
  4) Bind solution (H$_2$O (100 μL) is added. No drain!
  5) Oligo dissolved in H$_2$O (max. 50 μL) is added. Shake 10 min 600 rpm, then drain.
  6) H$_2$O is added (200 μL). Drain.
  7) DMF is added (200 μL). Drain.
  8) Repeat step 11 twice.
  9) 10% piperidine/DMF (250 μL) is added. Shake 5 min 600 rpm. Spin 1000 g 1 min.
  10) Repeat step 13.
  11) DMF is added (200 μL). Drain.
  12) Repeat step 15 twice
  13) H$_2$O is added (200 μL). Drain.
  14) Repeat step 17
  15) Release solution is added (35 μL, 2M TEAB). Shake 10 min 600 rpm. Spin at 1000 g for 1 min, collect the solvent in an eppendorf tube.
  16) Repeat step 19.
  17) Combine the solvents from step 19 and 20, then spin column filtrate the sample.

Procedure for Ns Deprotection on DEAE Sepharose
  1) 100 μL DEAE suspension is pipetted into a filtertube and drained by vacuum.
  2) Add water (200 μL) and drain.
  3) Bind solution (H$_2$O (200 μL)) is added. Shake 10 min 600 rpm, then drain.
  4) Bind solution (H$_2$O (100 μL) is added. No drain!
  5) Oligo dissolved in H$_2$O (max. 50 μL) is added. Shake 10 min 600 rpm, then drain.
  6) H$_2$O is added (200 μL). Drain.
  7) DMF (dry) is added (200 μL). Drain.
  8) Repeat step 7 twice.
  9) 0.5M mercaptoanisol and 0.25M DIPEA in DMF (dry) (200 μL; freshly prepared) is added. Shake 24h at 25° C., 600 rpm. No drain!
  10) 0.3 M AcOH in DMF is added (200 μL). Shake 5 min 600 rpm, then drain.
  11) DMF is added (200 μL). Drain.
  12) Repeat step 11 twice
  13) H$_2$O is added (200 μL). Drain.
  14) Repeat step 13
  15) Release solution is added (35 μL, 2M TEAB). Shake 10 min 600 rpm. Spin at 1000 g for 1 min, collect the solvent in an eppendorf tube.
  16) Repeat step 15.
  17) Combine the solvents from step 14 and 15, then spin column filtrate the sample.

Procedure for Ns Deprotection on DEAE Sepharose (Parallel Format)
  1) 20 μL DEAE suspension is pipetted into each well and drained by vacuum. (The capacity of the DEAE suspension is 0.5 nmol/μL oligo use min 20 μL for >10 nmol oligo)
  2) Add water (100 μL per well) and drain.
  3) Bind solution (H$_2$O (100 μL per well)) is added. Shake 10 min 600 rpm, then drain.

4) Oligo dissolved in H$_2$O (max. 100 µL per well) is added. Shake 10 min 600 rpm, then drain.
5) H$_2$O is added (100 µL per well). Drain.
6) DMF (dry) is added (100 µL per well). Drain.
7) Repeat step 6 twice.
8) 0.5M mercaptoanisol and 0.25M DIPEA in DMF (dry) (100 µL per well; freshly prepared) is added. Shake 24h at 25° C., 600 rpm. No drain!
9) 0.3 M AcOH in DMF is added (100 µL per well). Shake 5 min 600 rpm, then drain.
10) DMF is added (100 µL per well). Drain.
11) Repeat step 10 twice
12) H$_2$O is added (100 µL per well). Drain.
13) Repeat step 12
14) Release solution is added (50 µL per well, 2M TEAB). Shake 10 min 600 rpm. Spin at 1000 g for 1 min, collect the solvent in a 96 well plate.
15) Repeat step 14.
16) Combine the solvents from step 14 and 15, then evaporate samples to ~50 µL per well and spin column filtrate the samples.

A reactive compound building block can include one or more functional groups in addition to the reactive group or groups employed to generate the molecule being synthesised by the methods of the present invention. One or more of the functional groups can be protected to prevent undesired reactions of these functional groups. Suitable protecting groups are known in the art for a variety of functional groups (see e.g. Greene and Wuts, Protective Groups in Organic Synthesis, second edition, New York: John Wiley and Sons (1991), incorporated herein by reference). Useful protecting groups include t-butyl esters and ethers, acetals, trityl ethers and amines, acetyl esters, trimethylsilyl ethers, trichloroethyl ethers and esters and carbamates.

The reactive groups of the reactive compound building blocks and/or the chemical reaction site can also be in a pro-form that has to be activated before a reaction with (another) reactive compound building block can take place. As an example, the reactive groups can be protected, c.f. above, with a suitable group, which needs to be removed before a reaction with the reactive compound building block can proceed. Accordingly, a reactive compound building block can comprise one or more reactive group(s) or precursors of such groups, wherein the precursors can be activated or processed to generate the reactive group. Also, the reactive compound building block itself can be a precursor for the structural entity which is going to be incorporated into the third intermediate bi-functional complex.

Examples of further protection groups include "N-protected amino" and refers to protecting groups protecting an amino group against undesirable reactions during synthetic procedures. Commonly used N-protecting groups are disclosed in Greene, "Protective Groups In Organic Synthesis," (John Wiley & Sons, New York (1981)). Preferred N-protecting groups are formyl, acetyl, benzoyl, pivaloyl, t-butylacetyl, phenylsulfonyl, benzyl, t-butyloxycarbonyl (Boc), and benzyloxycarbonyl (Cbz).

Also, the term "O-protected carboxy" refers to a carboxylic acid protecting ester or amide group typically employed to block or protect the carboxylic acid functionality while the reactions involving other functional sites of the compound are performed. Carboxy protecting groups are disclosed in Greene, "Protective Groups in Organic Synthesis" (1981). Additionally, a carboxy protecting group can be used as a prodrug whereby the carboxy protecting group can be readily cleaved in vivo, for example by enzymatic hydrolysis, to release the biologically active parent. Such carboxy protecting groups are well known to those skilled in the art, having been extensively used in the protection of carboxyl groups in the penicillin and cephalosporin fields as described in U.S. Pat. Nos. 3,840,556 and 3,719,667.

In some embodiments, the reaction between reactans or between a reactive compound building block and the chemical reaction site can involve a further reactive compound building block, such as a "bridging-molecule", mediating a connection between the reactive compound building block and the chemical reaction site.

Scaffolds and Small Molecules

In some embodiments, the chemical reaction site comprises one or more scaffolds each having one or more reactive groups attached thereto. The one or more reactive groups can e.g. be any of the groups cited herein above under the heading "Chemical reaction site and reactive groups".

Examples of scaffold structures are e.g. benzodiazepines, steroids, hydantiones, piperasines, diketopiperasines, morpholines, tropanes, cumarines, qinolines, indoles, furans, pyrroles, oxazoles, amino acid precursors, and thiazoles. Further examples are provided herein below.

When the synthesis methods employ scaffolds, a reactive compound building block comprising only one reactive group can be used in the end position of the scaffolded molecule being synthesised, whereas reactive compound building blocks comprising two or more reactive groups are suitably incorporated into the body part and/or a branching portion of a scaffolded molecule optionally capable of being reacted with further reactive compound building blocks. Two or more reactive groups can be present on a scaffold having a core structure on which the molecule is being synthesised. This create the basis for synthesising multiple variants of compounds of the same class or compounds sharing certain physical or functional traits. The variants can be formed e.g. through reaction of reactive groups of the scaffold with reactive groups of one or more reactive compound building blocks, optionally mediated by fill-in groups ("bridging molecules") and/or catalysts.

The small molecules of the compound libraries of the present invention can be linear, branched or cyclical, or comprise structural elements selected from a combination of the aforementioned structures. When comprising a ring system, the small molecules can comprise a single ring or a fused ring system. One or more heteroatoms can be present in either the single ring system or the fused ring system.

"Single ring" refers to a cycloalkyl, heterocycloalkyl, aryl, or heteroaryl ring having about three to about eight, or about four to about six ring atoms. A single ring is not fused by being directly bonded at more than one ring atom to another closed ring.

"Fused ring" refers to fused aryl or cyclyl ring. For example, about six or less, about five or less, about four or less, about three or less, or about two rings can be fused. Each ring can be independently selected from the group consisting of aryl, heteroaryl, cycloalkyl, heterocycloalkyl, cycloalkenyl, and heterocycloalkenyl rings, each of which ring may independently be substituted or unsubstituted, having about four to about ten, about four to about thirteen, or about four to about fourteen ring atoms.

The number of rings in a small molecule refers to the number of single or fused ring systems. Thus, for example a fused ring can be considered to be one ring. As non-limiting examples, a phenyl ring, naphthalene, and norbornane, for purposes of the present invention, are all considered to be one ring, whereas biphenyl, which is not fused, is considered to be two rings.

A "heteroatom" refers to N, O, S, or P. In some embodiments, heteroatom refers to N, O, or S, where indicated. Heteroatoms shall include any oxidized form of nitrogen, sulfur, and phosphorus and the quaternized form of any basic nitrogen.

Accordingly, examples of small molecule ring systems are:

"Aryl", used alone or as part of a larger moiety as in "aralkyl", refers to aromatic rings having six ring carbon atoms.

"Fused aryl," refers to fused about two to about three aromatic rings having about six to about ten, about six to about thirteen, or about six to about fourteen ring carbon atoms.

"Fused heteroaryl" refers to fused about two to about three heteroaryl rings wherein at least one of the rings is a heteroaryl, having about five to about ten, about five to about thirteen, or about five to about fourteen ring atoms.

"Fused cycloalkyl" refers to fused about two to about three cycloalkyl rings having about four to about ten, about four to about thirteen, or about four to about fourteen ring carbon atoms.

"Fused heterocycloalkyl" refers to fused about two to about three heterocycloalkyl rings, wherein at least one of the rings is a heterocycloalkyl, having about four to about ten, about four to about thirteen, or about four to about fourteen ring atoms.

"Heterocycloalkyl" refers to cycloalkyls comprising one or more heteroatoms in place of a ring carbon atom.

"Lower heterocycloalkyl" refers to cycloalkyl groups containing about three to six ring members.

"Heterocycloalkenyl" refers to cycloalkenyls comprising one or more heteroatoms in place of a ring carbon atom. "Lower heterocycloalkenyl" refers to cycloalkyl groups containing about three to about six ring members. The term "heterocycloalkenyl" does not refer to heteroaryls.

"Heteroaryl" refers to aromatic rings containing about three, about five, about six, about seven, or about eight ring atoms, comprising carbon and one or more heteroatoms.

"Lower heteroaryl" refers to heteroaryls containing about three, about five, or about six ring members.

Exemplary preferred scaffold structures can e.g. be selected from the group consisting of quinazoline, tricyclic quinazoline, purine, pyrimidine, phenylamine-pyrimidine, phthalazine, benzylidene malononitrile, amino acid, tertiary amine, peptide, lactam, sultam, lactone, pyrrole, pyrrolidine, pyrrolinone, oxazole, isoxazole, oxazoline, isoxazoline, oxazolinone, isoxazolinone, thiazole, thiozolidinone, hydantoin, pyrazole, pyrazoline, pyrazolone, imidazole, imidazolidine, imidazolone, triazole, thiadiazole, oxadiazole, benzofuran, isobenzofuran, dihydrobenzofuran, dihydroisobenzofuran, indole, indoline, benzoxazole, oxindole, indolizine, benzimidazole, benzimidazolone, pyridine, piperidine, piperidinone, pyrimidinone, piperazine, piperazinone, diketopiperazine, metathiazanone, morpholine, thiomorpholine, phenol, dihydropyran, quinoline, isoquinoline, quinolinone, isoquinolinone, quinolone, quinazolinone, quinoxalinone, benzopiperazinone, quinazolinedione, benzazepine and azepine.

Further exemplary scaffold structures linked to the third intermediate bi-functional complexes are selected from the group consisting of:
hydrido,
substituted and unsubstituted alkyl, substituted and unsubstituted haloalkyl, substituted and unsubstituted hydroxyalkyl, substituted and unsubstituted alkylsulfonyl,
substituted and unsubstituted alkenyl,
halo,
substituted and unsubstituted alkoxy, substituted and unsubstituted alkoxyalkyl, substituted and unsubstituted haloalkoxy, substituted and unsubstituted haloalkoxyalkyl,
substituted and unsubstituted aryl,
substituted and unsubstituted heterocyclic,
substituted and unsubstituted heteroaryl,
sulfonyl, substituted and unsubstituted alkylsulfonyl, substituted and unsubstituted arylsulfonyl, sulfamyl, sulfonamidyl, aminosulfonyl, substituted and unsubstituted N-alkylaminosulfonyl, substituted and unsubstituted N-arylaminosulfonyl, substituted and unsubstituted N,N-dialkylaminosulfonyl, substituted and unsubstituted N-alkyl-N-arylaminosulfonyl, substituted and unsubstituted N-alkylaminosulfonyl, substituted and unsubstituted N,N-dialkylaminosulfonyl, substituted and unsubstituted N-arylaminosulfonyl, substituted and unsubstituted N-alkyl-N-arylaminosulfonyl,
carboxy, substituted and unsubstituted carboxyalkyl,
carbonyl, substituted and unsubstituted alkylcarbonyl, substituted and unsubstituted alkylcarbonylalkyl,
substituted and unsubstituted alkoxycarbonyl, substituted and unsubstituted alkoxycarbonylalkyl,
aminocarbonyl, substituted and unsubstituted aminocarbonylalkyl, substituted and unsubstituted N-alkylaminocarbonyl, substituted and unsubstituted N-arylaminocarbonyl, substituted and unsubstituted N,N-dialkylaminocarbonyl, substituted and unsubstituted N-alkyl-N-arylaminocarbonyl, substituted and unsubstituted N-alkyl-N-hydroxyaminocarbonyl, substituted and unsubstituted N-alkyl-N-hydroxyaminocarbonylalkyl, substituted and unsubstituted N-alkylaminocarbonyl, substituted and unsubstituted N,N-dialkylaminocarbonyl, substituted and unsubstituted N-arylaminocarbonyl, substituted and unsubstituted N-alkyl-N-arylaminocarbonyl, substituted and unsubstituted aminocarbonylalkyl, substituted and unsubstituted N-cycloalkylaminocarbonyl,
substituted and unsubstituted aminoalkyl, substituted and unsubstituted alkylaminoalkyl,
amidino,
cyanoamidino,
substituted and unsubstituted heterocyclicalkyl,
substituted and unsubstituted aralkyl,
substituted and unsubstituted cycloalkyl,
substituted and unsubstituted cycloalkenyl,
substituted and unsubstituted alkylthio,
substituted and unsubstituted alkylsulfinyl,
substituted and unsubstituted N-alkylamino, substituted and unsubstituted N,N-dialkylamino,
substituted and unsubstituted arylamino, substituted and unsubstituted aralkylamino, substituted and unsubstituted N-alkyl-N-arylamino, substituted and unsubstituted N-aralkyl-N-alkylamino, substituted and unsubstituted N-arylaminoalkyl, substituted and unsubstituted N-aralkylaminoalkyl, substituted and unsubstituted N-alkyl-N-arylaminoalkyl, substituted and unsubstituted N-aralkyl-N-alkylaminoalkyl,
acyl, acylamino,
substituted and unsubstituted arylthio, substituted and unsubstituted aralkylthio,
substituted and unsubstituted aryloxy, substituted and unsubstituted aralkoxy,
substituted and unsubstituted haloaralkyl,
substituted and unsubstituted carboxyhaloalkyl,
substituted and unsubstituted alkoxycarbonylhaloalkyl, substituted and unsubstituted aminocarbonylhaloalkyl, substituted and unsubstituted alkylaminocarbonylhaloalkyl,
substituted and unsubstituted alkoxycarbonylcyanoalkenyl, substituted and unsubstituted carboxyalkylaminocarbonyl, substituted and unsubstituted aralkoxycarbonylalkylaminocarbonyl, substituted and unsubstituted cycloalkylalkyl, and substituted and unsubstituted aralkenyl.

The same or different scaffolds comprising a plurality of sites for functionalization react with one or more identical or different reactive compound building blocks in order to generate a compound library comprising different small molecules. As used herein, the term "scaffold reactive group" refers to a chemical moiety that is capable of reacting with the reactive group of a reactive compound building block or reactive compound building block during the synthesis if the small molecule. Preferred scaffold reactive groups include, but are not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, amino acid, aryl, cycloalkyl, heterocyclyl, heteroaryl, etc. One of skill in the art will be aware of other common functional groups that are encompassed by the present invention.

As used herein, the term "reactive compound building block reactive group" refers to a chemical moiety of a reactive compound building block capable of reacting with one or more scaffold reactive groups. Preferred reactive groups of a reactive compound building block include, but are not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, amino acid, aryl, cycloalkyl, heterocyclyl, heteroaryl, etc. One of skill in the art will be aware of other common functional groups that are encompassed by the present invention.

The small molecule compounds of the present invention can be prepared using a variety of synthetic reactions. Suitable reaction chemistries are preferably selected from the following group: Amine acylation, reductive alkylation, aromatic reduction, aromatic acylation, aromatic cyclization, aryl-aryl coupling, [3+2] cycloaddition, Mitsunobu reaction, nucleophilic aromatic substitution, sulfonylation, aromatic halide displacement, Michael addition, Wittig reaction, Knoevenagel condensation, reductive amination, Heck reaction, Stille reaction, Suzuki reaction, Aldol condensation, Claisen condensation, amino acid coupling, amide bond formation, acetal formation, Diels-Alder reaction, [2+2] cycloaddition, enamine formation, esterification, Friedel Crafts reaction, glycosylation, Grignard reaction, Homer-Emmons reaction, hydrolysis, imine formation, metathesis reaction, nucleophilic substitution, oxidation, Pictet-Spengler reaction, Sonogashira reaction, thiazolidine formation, thiourea formation and urea formation.

Accordingly, the reactive compound building blocks and scaffolds of the present invention are those that enable the reactions above to occur. These include, but are not limited to, nucleophiles, electrophiles, acylating agents, aldehydes, carboxylic acids, alcohols, nitro, amino, carboxyl, aryl, heteroaryl, heterocyclyl, boronic acids, phosphorous ylides, etc. One of skill in the art can envision other synthetic reactions and reactive components useful in the present invention.

Radicals R, $R_1$ and $R_2$ can be any of the above described groups, such as, for example, hydrogen, alkyl, cycloalkyl, heterocyclyl, aryl and heteroaryl, all optionally substituted as disclosed herein above. One of skill in the art will further understand that radical Ar is an aryl, which can be, for example, phenyl, naphthyl, pyridyl and thienyl. In addition, one of skill in the art will understand that radical X can be, for example, hydrogen, halogen alkyl, cycloalkyl, heterocyclyl, aryl and heteroaryl.

Contacting a scaffold with one or more reactive compound building blocks results in the conversion of the scaffold into a small molecule, or an intermediate scaffold structure to be further reacted or modified.

Accordingly, in one embodiment of the present invention, reactive compound building blocks comprising one or more reactive groups, react with one or more, preferably more, such as 2, 3, 4, 5, 6, 7, 8, 9, 10, or from 10 to 20, reactive groups of a scaffold comprising a plurality of such reactive groups, by one or more reactions selected from the group consisting of amine acylation, reductive alkylation, aromatic reduction, aromatic acylation, aromatic cyclization, aryl-aryl coupling, [3+2] cycloaddition, Mitsunobu reaction, nucleophilic aromatic substitution, sulfonylation, aromatic halide displacement, Michael addition, Wittig reaction, Knoevenagel condensation, reductive amination, Heck reaction, Stille reaction, Suzuki reaction, Aldol condensation, Claisen condensation, amino acid coupling, amide bond formation, acetal formation, Diels-Alder reaction, [2+2] cycloaddition, enamine formation, esterification, Friedel Crafts reaction, glycosylation, Grignard reaction, Homer-Emmons reaction, hydrolysis, imine formation, metathesis reaction, nucleophilic substitution, oxidation, Pictet-Spengler reaction, Sonogashira reaction, thiazolidine formation, thiourea formation and urea formation, wherein said scaffold preferably comprises a structural component selected from the group consisting of a cyclic or bicyclic hydrocarbon, a steroid, a sugar, a heterocyclic structure, a polycyclic aromatic molecule, an amine, an amino acid, a multi-functional small molecule, a peptide or a polymer having various substituents at defined positions.

Suitable scaffolds of the present invention include, but are not limited to, quinazoline, tricyclic quinazoline, purine, pyrimidine, phenylamine-pyrimidine, phthalazine, benzylidene malononitrile, amino acid, tertiary amine, peptide, polymer, aromatic compounds containing ortho-nitro fluoride(s), aromatic compounds containing para-nitro fluoride(s), aromatic compounds containing ortho-nitro chloromethyl, aromatic compounds containing ortho-nitro bromomethyl, lactam, sultam, lactone, pyrrole, pyrrolidine, pyrrolinone, oxazole, isoxazole, oxazoline, isoxazoline, oxazolinone, isoxazolinone, thiazole, thiozolidinone, hydantoin, pyrazole, pyrazoline, pyrazolone, imidazole, imidazolidine, imidazolone, triazole, thiadiazole, oxadiazole, benzofuran, isobenzofuran, dihydrobenzofuran, dihydroisobenzofuran, indole, indoline, benzoxazole, oxindole, indolizine, benzimidazole, benzimidazolone, pyridine, piperidine, piperidinone, pyrimidinone, piperazine, piperazinone, diketopiperazine, metathiazanone, morpholine, thiomorpholine, phenol, dihydropyran, quinoline, isoquinoline, quinolinone, isoquinolinone, quinolone, quinazolinone, quinoxalinone, benzopiperazinone, quinazolinedione, benzazepine and azepine, and wherein said scaffold preferably comprises at least two scaffold reactive groups selected from the group consisting of hydroxyl, carboxyl, amino, thiol, aldehyde, halogen, nitro, cyano, amido, urea, carbonate, carbamate, isocyanate, sulfone, sulfonate, sulfonamide, sulfoxide, etc., for reaction with said one or more reactive compound building blocks.

The compound libraries can be partitioned or enriched with the selection of possible "lead candidates" or "drug candidates" as a result. The identification of "lead candidates" or "drug candidates" typically result when an association is formed between a small molecule member of the compound library and a target compound.

A "library" is a collection of library compounds, such as a collection of different small molecules. The library can be virtual, in that it is an in silico or electronic collection of structures used for computational analysis as described herein. The library is preferably physical, in that the set of small molecules are synthesized, isolated, or purified.

A "lead candidate" is a library compound, such as a small molecule, that binds to a biological target molecule and is designed to modulate the activity of a target protein. A lead candidate can be used to develop a drug candidate, or a drug to be used to treat a disorder or disease in an animal, including, for example, by interacting with a protein of said animal, or with a bacterial, viral, fungal, or other organism that can be implicated in said animal disorder or disease, and that is selected for further testing either in cells, in animal models, or in the target organism. A lead candidate may also be used to develop compositions to modulate plant diseases or disorders, including, for example, by modulating plant protein activity, or by interacting with a bacterial, viral, fungal, or other organism implicated in said disease or disorder.

A "drug candidate" is a lead candidate that has biological activity against a biological target molecule and has ADMET (absorption, distribution, metabolism, excretion and toxicity) properties appropriate for it to be evaluated in an animal, including a human, clinical studies in a designated therapeutic application.

A "compound library" is a group comprising more than one compound, such as more than one different small molecule, used for drug discovery. The compounds in the library can be small molecules designed to be linked to other compounds or small molecules, or the compounds can be small molecules designed to be used without linkage to other small molecules.

A "plurality" is more than one of whatever noun "plurality" modifies in the sentence.

The term "obtain" refers to any method of obtaining, for example, a small molecule, a library of such different small molecules, or a target molecule. The method used to obtain such compounds, biological target molecules, or libraries, may comprise synthesis, purchase, or any means the compounds, biological target molecules, or libraries can be obtained.

By "activity against" is meant that a compound may have binding activity by binding to a biological target molecule, or it may have an effect on the enzymatic or other biological activity of a target, when present in a target activity assay. Biological activity and biochemical activity refer to any in vivo or in vitro activity of a target biological molecule. Non-limiting examples include the activity of a target molecule in an in vitro, cellular, or organism level assay. As a non-limiting example with an enzymatic protein as the target molecule, the activity includes at least the binding of the target molecule to one or more substrates, the release of a product or reactive compound building block by the target molecule, or the overall catalytic activity of the target molecule. These activities can be accessed directly or indirectly in an in vitro or cell based assay, or alternatively in a phenotypic assay based on the effect of the activity on an organism. As a further non-limiting example wherein the target molecule is a kinase, the activity includes at least the binding of the kinase to its target polypeptide and/or other substrate (such as ATP as a non-limiting example) as well as the actual activity of phosphorylating a target polypeptide.

Obtaining a crystal of a biological target molecule in association with or in interaction with a test small molecule includes any method of obtaining a compound in a crystal, in association or interaction with a target protein. This method includes soaking a crystal in a solution of one or more potential compounds, or ligands, or incubating a target protein in the presence of one or more potential compounds, or ligands.

By "or" is meant one, or another member of a group, or more than one member. For example, A, B, or C, may indicate any of the following: A alone; B alone; C alone; A and B; B and C; A and C; A, B, and C.

"Association" refers to the status of two or more molecules that are in close proximity to each other. The two molecules can be associated non-covalently, for example, by hydrogen-bonding, van der Waals, electrostatic or hydrophobic interactions, or covalently.

"Active Site" refers to a site in a target protein that associates with a substrate for target protein activity. This site may include, for example, residues involved in catalysis, as well as residues involved in binding a substrate. Inhibitors may bind to the residues of the active site.

"Binding site" refers to a region in a target protein, which, for example, associates with a ligand such as a natural substrate, non-natural substrate, inhibitor, substrate analog, agonist or anoligonucleotide tagonist, protein, co-factor or small molecule, as well as, optionally, in addition, various ions or water, and/or has an internal cavity sufficient to bind a small molecule and can be used as a target for binding drugs. The term includes the active site but is not limited thereby.

"Crystal" refers to a composition comprising a biological target molecule, including, for example, macromolecular drug receptor targets, including protein, including, for example, but not limited to, polypeptides, and nucleic acid targets, for example, but not limited to, DNA, RNA, and ribosomal subunits, and carbohydrate targets, for example, but not limited to, glycoproteins, crystalline form. The term "crystal" includes native crystals, and heavy-atom derivative crystals, as defined herein. The discussion below often uses a target protein as a exemplary, and non-limiting example. The discussion applies in an analogous manner to all possible target molecules.

"Alkyl" and "alkoxy" used alone or as part of a larger moiety refers to both straight and branched chains containing about one to about eight carbon atoms. "Lower alkyl" and "lower alkoxy" refer to alkyl or alkoxy groups containing about one to about four carbon atoms.

"Cyclyl", "cycloalkyl", or "cycloalkenyl" refer to cyclic alkyl or alkenyl groups containing from about three to about eight carbon atoms. "Lower cyclyl," "lower cycloalkyl." or "lower cycloalkenyl" refer to cyclic groups containing from about three to about six carbon atoms.

"Alkenyl" and "alkynyl" used alone or as part of a larger moiety shall include both straight and branched chains containing about two to about eight carbon atoms, with one or more unsaturated bonds between carbons. "Lower alkenyl" and "lower alkynyl" include alkenyl and alkynyl groups containing from about two to about five carbon atoms.

"Halogen" means F, Cl, Br, or I.

"Linker group" of a bi-functional complex means an organic moiety that connects two parts of the bi-functional complex, typically the small molecule and the oligonucleotide identifier. Linkers are typically comprised of an atom such as oxygen or sulfur, a unit such as —NH— or —CH$_2$—, or a chain of atoms, such as an alkylidene chain. The molecular mass of a linker is typically in the range of about 14 to about 200. Examples of linkers are known to those of ordinary skill in the art and include, but are not limited to, a saturated or unsaturated $C_{1-6}$ alkylidene chain which is optionally substituted, and wherein up to two saturated carbons of the chain are optionally replaced by —C(=O)—, —CONH—, CONHNH—, —CO$_2$—, —NHCO$_2$—, —O—, —NHCONH—, —O(C=O)—, —O(C=O)NH—, —NHNH—, —NHCO—, —S—, —SO—, —SO$_2$—, —NH—, —SO$_2$NH—, or NHSO$_2$—.

An Log P value can be, for example, a calculated Log P value, for example, one determined by a computer program for predicting Log P, the log of the octanol-water partition coefficient commonly used as an empirical descriptor for predicting bioavailability (e.g. Lipinski's Rule of 5; Lipinski, C. A.; Lombardo, F.; Dominy, B. W.; Feeney, P. J. (1997) Experimental and computational approaches to estimate solubility and permeability in drug discovery and development settings. Adv. Drug Delivery Rev. 23, 3-25). The calculated log P value may, for example, be the S log P value. S log P is implemented in the MOE software suite from Chemical Computing Group, www.chemcomp.com. S log P is based on an atomic contribution model (Wildman, S. A., Crippen, G. M.; Prediction of Physicochemical Parameters by Atomic Contributions; J. Chem. Inf. Comput. Sci., 39(5), 868-873 (1999)).

A molecule can be formed by the reaction of one or more reactive groups on one or more reactive compound building blocks or a molecule can be formed by the reaction of one or more reactive groups on one or more reactive compound building blocks and one or more chemical reaction sites.

A molecule can comprise one or more atoms and one or more bonds, wherein such bonds between atoms may optionally be single bonds, double bonds or triple bonds and a combination thereof, wherein such atoms may comprise carbon, silicon, nitrogen, phosphorous, oxygen, sulfur, selenium, fluorine, chlorine, bromine, iodine, borane, stannane, lithium, sodium, potassium, kalium, calcium, barium, strontium, including any combination thereof. In further embodiments, a molecule may comprise other atoms in the periodic system.

In one or more embodiments, a reactive group may comprise one or more atoms and one or more bonds, wherein such bonds between atoms may optionally be single bonds, double bonds or triple bonds and a combination thereof, wherein such atoms may comprise carbon, silicon, nitrogen, phosphorous, oxygen, sulfur, selenium, fluorine, chlorine, bromine, iodine, borane, stannane, lithium, sodium, potassium, kalium, calcium, barium, strontium. In further embodiments, a molecule may comprise other atoms in the periodic system.

In one or more embodiments, a chemical reaction site may comprise one or more atoms and one or more bonds, wherein such bonds between atoms may optionally be single bonds, double bonds or triple bonds and a combination thereof, wherein such atoms may comprise carbon, silicon, nitrogen, phosphorous, oxygen, sulfur, selenium, fluorine, chlorine, bromine, iodine, borane, stannane, lithium, sodium, potassium, kalium, calcium, barium, strontium. In further embodiments, a molecule may comprise other atoms in the periodic system.

In one or more embodiments, the molecule comprisings the molecule, which can be formed following the reaction of one or more reactive compound building blocks with one or more chemical reaction sites, where the molecule is linked through a linker to a third intermediate bi-functional complex optionally covalently linked to one or more oligonucleotide tags.

In one or more embodiments, the molecule comprisings the chemical motif formed by reaction of reactive groups comprising atoms participating in the reaction between one or more reactive groups on one or more reactive compound building blocks and one or more chemical reaction sites.

In one embodiment, the molecule comprisings a carboxamide. In another embodiment, the molecule comprisings a sulfonamide. In a further embodiment, the molecule comprisings a urea group. In further embodiments, the molecule comprisings an amine. In another embodiment, the molecule comprisings an ether. In a further embodiment, the molecule comprisings an ester for example an carboxylic acid ester. In a further embodiment, the molecule comprisings an alkene. In a further embodiment, the molecule comprisings an alkyne. In a further embodiment, the molecule comprisings an alkane. In a further embodiment, the molecule comprisings a thioether. In a further embodiment, the molecule comprisings a sulfone. In a further embodiment, the molecule comprisings a sulfoxide. In a further embodiment, the molecule comprisings a sulfonamide. In a further embodiment, the molecule comprisings a carbamate. In a further embodiment, the molecule comprisings a carbonate. In a further embodiment, the molecule comprisings a 1,2-diol. In a further embodiment, the molecule comprisings a 1,2-dioxoalkane. In a further embodiment, the molecule comprisings a ketone. In a further embodiment, the molecule comprisings an imine. In a further embodiment, the molecule comprisings a hydrazone. In a further embodiment, the molecule comprisings an oxime. In a further embodiment, the molecule comprisings an aminohetarene.

In one embodiment the molecule comprising a cyclic structure such as a 3-40 member ring, such as for example an 18-40 member ring, such as for example a 3-7 member ring, for example an 8-24 member ring, for example an 8-18 member ring, for example an 8-14 member ring, for example a 5-7 member ring, such as for example a 3 member ring, for example a 4 member ring, for example a 5 member ring, for example a 6 member ring, for example a 7 member ring, for example an 8 member ring, for example a 9 member ring, for example a 10 member ring, for example an 11 member ring, for example a 12 member ring, for example a 13 member ring, for example a 14 member ring, for example a 15 member ring, for example a 16 member ring, for example a 17 member ring, for example an 18 member ring.

In one embodiment the molecule comprisings a cyclic structure, for example an aliphatic ring, for example an aromatic ring, for example a partially unsaturated ring and a combination thereof.

In one embodiment the molecule comprising a 3 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 4 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 5 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 6 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 7 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising an 8 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 9 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 10 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising an 11 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 12 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 13 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 14 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 15 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 16 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 17 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising an 18 member ring comprising one or more carbon ring atoms and optionally one or more heteroatoms, for example one or more oxygen ring atoms, for example one or more nitrogen ring atoms, for example one or more sulfur ring atoms.

In one embodiment a molecule comprises for example a fully unsaturated ring structure, for example a fully saturated ring structure, for example a partly saturated ring structure, wherein such ring structure may comprise a pyrrole, a tetrahydrofuran, a tetrahydropyran, a furan, a thiophene, a pyrazole, an imidazole, a furazan, an oxazole, an isoxazole, a thiazole, an isothiazole, a 1,2,3-triazole, a 1,2,4-triazole, an 1,2,3-oxadiazole, 1,2,4-oxadiazole, 1,3,4-oxadiazole, a tetrazole, a pyridine, a pyridazine, a pyrimidine, a pyrazine, a piperidine, a piperazine, a morpholine, a thiomorpholine, an indole, an isoindole, an indazole, a purine, an indolizine, a purine, a quinoline, an isoquinoline, a quinazoline, a pteridine, a quinolizine, a carbazole, a phenazine, a phenothiazine, a phenanthridine, a chroman an oxolane, a dioxine, an aziridine, an oxirane, an azetidine, an azepine, which may optionally be substituted by one or more substituents.

In one embodiment a molecule comprises for example a fully unsaturated ring structure, for example a fully saturated ring structure, for example a partly saturated ring structure, wherein such ring structure may comprise a benzopyrrole, a benzotetrahydrofuran, a benzotetrahydropyran, a benzofuran, a benzothiophene, a benzopyrazole, an benzoimidazole, a benzofurazan, an benzooxazole, an benzoisoxazole, a benzothiazole, an benzoisothiazole, a benzo1,2,3-triazole, a benzopyridine, a benzopyridazine, a benzopyrimidine, a benzopyrazine, a benzopiperidine, a benzopiperazine, a benzomorpholine, a benzothiomorpholine, an benzoindole, an benzoisoindole, an benzoindazole, an benzoindolizine, a benzoquinoline, a benzoisoquinoline, a benzoquinazoline, a benzopteridine, a benzoquinolizine, a benzocarbazole, a benzophenazine, a benzophenothiazine, a benzophenanthridine, a benzochroman an benzooxolane, a benzodioxine, a benzoazetidine, a benzoazepine, which may optionally be substituted by one or more substituents.

In one embodiment a molecule comprises for example a fully unsaturated ring structure, for example a fully saturated ring structure, for example a partly saturated ring structure, wherein such ring structure may comprise a pyridopyrrole, a pyridotetrahydrofuran, a pyridotetrahydropyran, a pyridofuran, a pyridothiophene, a pyridopyrazole, an pyridoimidazole, a pyridofurazan, an pyridooxazole, an pyridoisoxazole, a pyridothiazole, an pyridoisothiazole, a pyrido1,2,3-triazole, a pyridopyridine, a pyridopyridazine, a pyridopyrimidine, a pyridopyrazine, a pyridopiperidine, a pyridopiperazine, a pyridomorpholine, a pyridothiomorpholine, an pyridoindole, an pyridoisoindole, an pyridoindazole, an pyridoindolizine, a pyridoquinoline, a pyridoisoquinoline, a pyridoquinazoline, a pyridopteridine, a pyridoquinolizine, a pyridocarbazole, a pyridophenazine, a pyridophenothiazine, a pyridophenanthridine, a pyridochroman an pyridooxolane, a pyridodioxine, a pyridoazetidine, a pyridoazepine, which may optionally be substituted by one or more substituents.

In one embodiment a molecule comprises for example a fully unsaturated ring structure, for example a fully saturated ring structure, for example a partly saturated ring structure, wherein such ring structure may comprise a pyrrolopyrrole, a pyrrolotetrahydrofuran, a pyrrolotetrahydropyran, a pyrrolofuran, a pyrrolothiophene, a pyrrolopyrazole, an pyrroloimidazole, a pyrrolofurazan, an pyrrolooxazole, an pyrroloisoxazole, a pyrrolothiazole, an pyrroloisothiazole, a pyrrolo1,2,3-triazole, a pyrrolopyridine, a pyrrolopyridazine, a pyrrolopyrimidine, a pyrrolopyrazine, a pyrrolopiperidine, a pyrrolopiperazine, a pyrrolomorpholine, a pyrrolothiomorpholine, an pyrroloindole, an pyrroloisoindole, an pyrroloindazole, an pyrroloindolizine, a pyrroloquinoline, a pyrroloisoquinoline, a pyrroloquinazoline, a pyrrolopteridine, a pyrroloquinolizine, a pyrrolocarbazole, a pyrrolophenazine, a pyrrolophenothiazine, a pyrrolo-phenanthridine, a pyrrolochroman an pyrrolooxolane, a pyrrolodioxine, a pyrroloazetidine, a pyrroloazepine, which may optionally be substituted by one or more substituents.

In one embodiment a molecule comprises for example a fully unsaturated ring structure, for example a fully saturated ring structure, for example a partly saturated ring structure, wherein such ring structure may comprise a furopyrrole, a furotetrahydrofuran, a furotetrahydropyran, a furofuran, a furothiophene, a furopyrazole, an furoimidazole, a furofurazan, an furooxazole, an furoisoxazole, a furothiazole, an furoisothiazole, a furo1,2,3-triazole, a furopyridine, a furopyridazine, a furopyrimidine, a furopyrazine, a furopiperidine, a furopiperazine, a furomorpholine, a furothiomorpholine, an furoindole, an furoisoindole, an furoindazole, an furoindolizine, a furoquinoline, a furoisoquinoline, a furoquinazoline, a furopteridine, a furoquinolizine, a furocarbazole, a furophenazine, a furophenothiazine, a furophenanthridine, a furochroman an furooxolane, a furodioxine, a furoazetidine, a furoazepine, which may optionally be substituted by one or more substituents.

In one embodiment a molecule comprises for example a fully unsaturated ring structure, for example a fully saturated ring structure, for example a partly saturated ring structure, wherein such ring structure may comprise a thienopyrrole, a thienotetrahydrofuran, a thienotetrahydropyran, a thienofuran, a thienothiophene, a thienopyrazole, an thienoimidazole, a thienofurazan, an thienooxazole, an thienoisoxazole, a thienothiazole, an thienoisothiazole, a thieno1,2,3-triazole, a thienopyridine, a thienopyridazine, a thienopyrimidine, a thienopyrazine, a thienopiperidine, a thienopiperazine, a thienomorpholine, a thienothiomorpholine, an thienoindole, an thienoisoindole, an thienoindazole, an thienoindolizine, a thienoquinoline, a thienoisoquinoline, a thienoquinazoline, a thienopteridine, a thienoquinolizine, a thienocarbazole, a thienophenazine, a thienophenothiazine, a thienophenanthridine, a thienochroman an thienooxolane, a thienodioxine, a thienoazetidine, a thienoazepine, which may optionally be substituted by one or more substituents.

In one embodiment a molecule comprises for example a fully unsaturated ring structure, for example a fully saturated ring structure, for example a partly saturated ring structure, wherein such ring structure may comprise a imidazopyrrole, a imidazotetrahydrofuran, a imidazotetrahydropyran, a imidazofuran, a imidazothiophene, a imidazopyrazole, an imidazoimidazole, a imidazofurazan, an imidazooxazole, an imidazoisoxazole, a imidazothiazole, an imidazoisothiazole, a imidazo1,2,3-triazole, a imidazopyridine, a imidazopyridazine, a imidazopyrimidine, a imidazopyrazine, a imidazopiperidine, a imidazopiperazine, a imidazomorpholine, a imidazothiomorpholine, an imidazoindole, an imidazoisoindole, an imidazoindazole, an imidazoindolizine, a imidazoquinoline, a imidazoisoquinoline, a imidazoquinazoline, a imidazopteridine, a imidazoquinolizine, a imidazocarbazole, a imidazophenazine, a imidazophenothiazine, a imidazophenanthridine, a imidazochroman an imidazooxolane, a imidazodioxine, a imidazoazetidine, a imidazoazepine, which may optionally be substituted by one or more substituents.

In one embodiment a molecule comprises for example a fully unsaturated ring structure, for example a fully saturated ring structure, for example a partly saturated ring structure, wherein such ring structure may comprise a pyrazolopyrrole, a pyrazolotetrahydrofuran, a pyrazolotetrahydropyran, a pyrazolofuran, a pyrazolothiophene, a pyrazolopyrazole, an pyrazoloimidazole, a pyrazolofurazan, an pyrazolooxazole, an pyrazoloisoxazole, a pyrazolothiazole, an pyrazoloisothiazole, a pyrazolo1,2,3-triazole, a pyrazolopyridine, a pyrazolopyridazine, a pyrazolopyrimidine, a pyrazolopyrazine, a pyrazolopiperidine, a pyrazolopiperazine, a pyrazolomorpholine, a pyrazolothiomorpholine, an pyrazoloindole, an pyrazoloisoindole, an pyrazoloindazole, an pyrazoloindolizine, a pyrazoloquinoline, a pyrazoloisoquinoline, a pyrazoloquinazoline, a pyrazolopteridine, a pyrazoloquinolizine, a pyrazolocarbazole, a pyrazolophenazine, a pyrazolophenothiazine, a pyrazolophenanthridine, a pyrazolochroman an pyrazolooxolane, a pyrazolodioxine, a pyrazoloazetidine, a pyrazoloazepine, which may optionally be substituted by one or more substituents.

In one embodiment a molecule comprises for example a fully unsaturated ring structure, for example a fully saturated ring structure, for example a partly saturated ring structure, wherein such ring structure may comprise a oxazolopyrrole, a oxazolotetrahydrofuran, a oxazolotetrahydropyran, a oxazolofuran, a oxazolothiophene, a oxazolopyrazole, an oxazoloimidazole, a oxazolofurazan, an oxazolooxazole, an oxazoloisoxazole, a oxazolothiazole, an oxazoloisothiazole, a oxazolo1,2,3-triazole, a oxazolopyridine, a oxazolopyridazine, a oxazolopyrimidine, a oxazolopyrazine, a oxazolopiperidine, a oxazolopiperazine, a oxazolomorpholine, a oxazolothiomorpholine, an oxazoloindole, an oxazoloisoindole, an oxazoloindazole, an oxazoloindolizine, a oxazoloquinoline, a oxazoloisoquinoline, a oxazoloquinazoline, a oxazolopteridine, a oxazoloquinolizine, a oxazolocarbazole, a oxazolophenazine, a oxazolophenothiazine, a oxazolophenanthridine, a oxazolochroman an oxazolooxolane, a oxazolodioxine, a oxazoloazetidine, a oxazoloazepine, which may optionally be substituted by one or more substituents.

In one embodiment a molecule comprises for example a fully unsaturated ring structure, for example a fully saturated ring structure, for example a partly saturated ring structure, wherein such ring structure may comprise a isoxazolopyrrole, a isoxazolotetrahydrofuran, a isoxazolotetrahydropyran, a isoxazolofuran, a isoxazolothiophene, a isoxazolopyrazole, an isoxazoloimidazole, a isoxazolofurazan, an isoxazolooxazole, an isoxazoloisoxazole, a isoxazolothiazole, an isoxazoloisothiazole, a isoxazolo1,2,3-triazole, a isoxazolopyridine, a isoxazolopyridazine, a isoxazolopyrimidine, a isoxazolopyrazine, a isoxazolopiperidine, a isoxazolopiperazine, a isoxazolomorpholine, a isoxazolothiomorpholine, an isoxazoloindole, an isoxazoloisoindole, an isoxazoloindazole, an isoxazoloindolizine, a isoxazoloquinoline, a isoxazoloisoquinoline, a isoxazoloquinazoline, a isoxazolopteridine, a isoxazoloquinolizine, a isoxazolocarbazole, a isoxazolophenazine, a isoxazolophenothiazine, a isoxazolophenanthridine, a isoxazolochroman an isoxazolooxolane, a isoxazolodioxine, a isoxazoloazetidine, a isoxazoloazepine, which may optionally be substituted by one or more substituents.

In one embodiment a molecule comprises for example a fully unsaturated ring structure, for example a fully saturated ring structure, for example a partly saturated ring structure, wherein such ring structure may comprise a thiaazolopyrrole, a thiaazolotetrahydrofuran, a thiaazolotetrahydropyran, a thiaazolofuran, a thiaazolothiophene, a thiaazolopyrazole, an thiaazoloimidazole, a thiaazolofurazan, an thiaazolooxazole, an thiaazoloisoxazole, a thiaazolothiazole, an thiaazoloisothiazole, a thiaazolo1,2,3-triazole, a thiaazolopyridine, a thiaazolopyridazine, a thiaazolopyrimidine, a thiaazolopyrazine, a thiaazolopiperidine, a thiaazolopiperazine, a thiaazolomorpholine, a thiaazolothiomorpholine, an thiaazoloindole, an thiaazoloisoindole, an thiaazoloindazole, an thiaazoloindolizine, a thiaazoloquinoline, a thiaazoloisoquinoline, a thiaazoloquinazoline, a thiaazolopteridine, a thiaazoloquinolizine, a thiaazolocarbazole, a thiaazolophenazine, a thiaazolophenothiazine, a thiaazolophenanthridine, a thiaazolochroman an thiaazolooxolane, a thiaazolodioxine, a thiaazoloazetidine, a thiaazoloazepine, which may optionally be substituted by one or more substituents.

In one embodiment a molecule comprises for example a fully unsaturated ring structure, for example a fully saturated ring structure, for example a partly saturated ring structure, wherein such ring structure may comprise a isothiaazolopyrrole, a isothiaazolotetrahydrofuran, a isothiaazolotetrahydropyran, a isothiaazolofuran, a isothiaazolothiophene, a isothiaazolopyrazole, an isothiaazoloimidazole, a isothiaazolofurazan, an isothiaazolooxazole, an isothiaazoloisoxazole, a isothiaazolothiazole, an isothiaazoloisothiazole, a isothiaazolo1,2,3-triazole, a isothiaazolopyridine, a isothiaazolopyridazine, a isothiaazolopyrimidine, a isothiaazolopyrazine, a isothiaazolopiperidine, a isothiaazolopiperazine, a isothiaazolomorpholine, a isothiaazolothiomorpholine, an isothiaazoloindole, an isothiaazoloisoindole, an isothiaazoloindazole, an isothiaazoloindolizine, a isothiaazoloquinoline, a isothiaazoloisoquinoline, a isothiaazoloquinazoline, a isothiaazolopteridine, a isothiaazoloquinolizine, a isothiaazolocarbazole, a isothiaazolophenazine, a isothiaazolophenothiazine, a isothiaazolophenanthridine, a isothiaazolochroman an isothiaazolooxolane, a isothiaazolodioxine, a isothiaazoloazetidine, a isothiaazoloazepine, which may optionally be substituted by one or more substituents.

In one embodiment a molecule comprises for example a fully unsaturated ring structure, for example a fully saturated ring structure, for example a partly saturated ring structure, wherein such ring structure may comprise a isothiaazolopyridine, a isothiaazolopyridazine, a isothiaazolopyrimidine, a isothiaazolopyrazine, a isothiazolotriazine, a pyrimidinopyridine, a pyrimidinopyridazine, a pyrimidinopyrimidine, a pyrimidinopyrazine, a pyrimidinotriazine, a pyrazinopyridine, a pyrazinopyridazine, a pyrazinopyrimidine, a pyrazinopyrazine, a pyrazinotriazine, a pyridazinopyridine, a pyridazinopyridazine, a pyridazinopyrimidine, a pyridazinopyrazine, a pyridazinotriazine, a triazinopyridine, a triazinopyridazine, a triazinopyrimidine, a triazinopyrazine, a triazinotriazine, which may optionally be substituted by one or more substituents.

In one embodiment the molecule may comprising a lactone, a lactam, a 2-hydroxy tetrahydrofuran, a 2-alkoxy tetrahydrofuran, a 2-hydroxy tetrahydropyran, a 2-alkoxy tetrahydropyran, a benzene, a naphthalene, a phenanthrene, an anthracene, a cyclopentane, a cyclopentene, a cyclohexane, a cyclohexene, a 1,3-cyclohexadiene, a 1,4-cyclohexadiene, a cyclopentadiene, which may optionally be substituted by one or more substituents.

In one embodiment the molecule may comprising a monocyclic system, a bicyclic system, a tricyclic system, a spirocyclic system, a fused bicyclic system, wherein such cyclic systems may optionally comprise carbon atoms, silicon atoms, nitrogen atoms, phosphorous atoms, oxygen atoms, sulfur atoms, wherein such cyclic systems may optionally be substituted by one or more substituents.

In a further embodiment, two or more cyclic structures may optionally be linked by one or more bonds comprising single bonds, double bonds, triple bonds and a combination thereof, wherein such cyclic systems may optionally comprise carbon atoms, silicon atoms, nitrogen atoms, phosphorous atoms, oxygen atoms, sulfur atoms, wherein such cyclic systems may optionally be substituted by one or more substituents.

Linker Moieties

The nascent bi-functional complex comprising a chemical reaction site and an oligonucleotide tag addition site for enzymatic addition of an oligonucleotide tag can also comprise a linking moiety connecting the chemical reaction site of the bi-functional complex and the oligonucleotide tag addition site.

In some embodiments it is preferable that the linker ensures that a reactive group or a building block (reactive compound building block) or a molecule is spaced away from the oligonucleotide tag or an oligonucleotide identifier. In some embodiments it is also preferable that the linker ensures that a reactive group, a building block (reactive compound building block) or the molecule part of the bi-functional complex can efficiently interact with another object such as a target used for screening/affinity selection.

The linker may be composed of one or more atoms. The linker may include monomer units such as a peptide, protein, carbohydrates and substituted carbohydrates, a nucleotide, or any unit synthesized using organic and/or inorganic chemistry such as ethylenglycol; 1,3-propylenglycol; 1,4-propylenglycol; 1,5-pentylenglycol. Any unit may be in substituted form, e.g., 1,3.propylenglycol hydroxyl-substituted at the 2 position (Propane-1,2,3-triol). The linker may also include a polymer such as an organic polymer, e.g. a polyethylenglycol, a polypeptide, or an oligonucleotide, polyvinyl, acetylene or polyacetylene, aryl/hetaryl and substituted aryl/hetaryl, ethers and polyethers such as e.g. polyethylenglycol and substituted polyethers, amines, polyamines and substituted polyamines, single- or double-stranded oligonucleotides, and polyamides and natural and unnatural polypeptides. The linker may contain any combination of monomeric and polymeric units. The linker may also contain branching units. The linker may be flexible or rigid and contain flexible and/or rigid parts. The linker may be attached to one or more reactive groups by one or more atoms. Moreover, the linker may contain one or more reactive groups. The linker may be attached to the oligonucleotide tag or identifier via one or more atoms, e.g. via a phosphate group.

The attachment point may be anywhere on the oligonucleotide tags or identifiers such as a 5' or 3' phosphate, a 5' or 3' OH, carbon, oxygen or nitrogen on one or more nucleotides. The linker may be attached to one or more oligonucleotide tags or identifiers such as both strands of a double stranded oligonucleotide tag. The linker may be attached to the oligonucleotide tag or identifier by one or more covalent bonds and/or one or more non-covalent bonds, e.g. the linker may include a biotin moiety which can bind non-covalently to a streptavidin molecule attached to the oligonucleotide tag. Preferably the length of the linker is in the range of 1-50 angstrom, more preferably 5-30 angstrom, most preferably 10-25 angstrom. Preferably, the linker separates the linker-oligonucleotide tag attachment point from a reactive group by 5-50 atomic bonds, more preferably, by 10-30 atomic bonds, most preferably by 15-25 atomic bonds. Preferably, the linker is prepared from Diisopropyl-phosphoramidous acid 2-cyano-ethyl ester 2-[2-(2-{2-[2-(2-{[(4-methoxyphenyl)-diphenyl-methyl]-amino}-ethoxy)-ethoxy]-ethoxy}-ethoxy)-ethoxy]-ethyl ester or similar compound. Preferably, the linker contains the structure 2-[2-(2-{2-[2-(2-Amino-ethoxy)-ethoxy]-ethoxy}-ethoxy)-ethoxy]-ethanol.

Cleavable linkers can be cleaved in any number of ways, e.g., by photolysis or increased temperature, or by the addition of acid, base, enzymes, ribozymes, other catalysts, or any other agents.

To maintain a physical link between the identifier and the molecule part of the bi-functional complex (in the case of oligonucleotide tags synthesis, the template and the encoded molecule), at least one non-cleavable linker is needed. The non-cleavable linker may of course be cleavable under certain conditions, but is non-cleavable under the conditions that lead to the bi-functional molecule employed in the screening. This non-cleavable linker is preferably flexible, enabling it to expose the encoded molecule in an optimal way.

Under certain conditions it may desirable to be able to cleave the linker before, during or after the screening of the library has been done, for example in order to perform a mass spectrometric analysis of the encoded molecule without the identifier attached, or to perform other types of assays on the free encoded molecule.

The linking moiety in one embodiment separates the oligonucleotide tag addition site from the chemical reaction site so as to allow an enzyme to perform the oligonucleotide tag addition and provide for a hybridisation region. The linking moiety can be a nucleic acid sequence, such as an oligonucleotide. The length of the oligonucleotide is preferably suitable for hybridisation with a complementing oligonucleotide, i.e. the number of nucleotides in the linking moiety is suitably 2 or more, such as 3 or more, for example 4 or above, such as 5 or more, for example 6 or more, such as 7 or more, for example 8 or more nucleotides.

In a certain embodiment, the linking moiety is attached to the chemical reaction site via a spacer comprising a selectively cleavable linker to enable release of the molecule from the identifier oligonucleotide in a step subsequent to the formation of the final bi-functional complex. The cleavable linker can be selectively cleavable, i.e. conditions can be selected that only cleave that particular linker.

When two chemical structures are linked together in such a way as to remain linked through the various manipulations they are expected to undergo they can be seen as being operatively linked. Typically the molecule part of the bi-functional complex and the oligonucleotide identifier are linked covalently via an appropriate linking group. The linking group is a bivalent moiety with a site of attachment for the oligonucleotide and a site of attachment for the molecule. For example, when the molecule is a polyamide compound, the polyamide compound can be attached to the linking group at its N-terminus, its C-terminus or via a functional group on one of the side chains. The linking group is sufficient to separate the polyamide compound and the oligonucleotide by at least one atom, and preferably, by more than one atom, such as at least two, at least three, at least four, at least five or at least six atoms.

Preferably, the linking group is sufficiently flexible to allow the polyamide compound to bind target molecules in a manner which is independent of the oligonucleotide identifier. In one embodiment, the linking group is attached to the N-terminus of the polyamide compound and the 5'-phosphate group of the oligonucleotide. For example, the linking group can be derived from a linking group precursor comprising an activated carboxyl group on one end and an activated ester on the other end. Reaction of the linking group precursor with the N-terminal nitrogen atom will form an amide bond connecting the linking group to the polyamide compound or N-terminal building block, while reaction of the linking group precursor with the 5'-hydroxy group of the oligonucleotide identifier will result in attachment of the oligonucleotide identifier to the linking group via an ester linkage. The linking group can comprise, for example, a polymethylene chain, such as a —$(CH_2)_n$— chain, or a poly(ethylene glycol) chain, such as a —$(CH_2CH_2O)_n$— chain, where in both cases n is an integer from 1 to about 20. Preferably, n is from 2 to about 12, more preferably from about 4 to about 10. In one embodiment, the linking group comprises a hexamethylene (—$(CH_2)_6$—) group.

In one embodiment, the oligonucleotide identifier is double-stranded and the two strands are covalently joined. The linking moiety can be any chemical structure which comprises a first functional group which is adapted to react with a building block, a second functional group which is adapted to react with the 3'-end of an oligonucleotide, and a third functional group which is adapted to react with the 5'-end of an oligonucleotide. Preferably, the second and third functional groups are oriented so as to position the two oligonucleotide strands in a relative orientation that permits hybridization of the two strands. For example, the linking moiety can have the general structure (I):

(I)

where A, is a functional group that can form a covalent bond with a building block, B is a functional group that can form a bond with the 5'-end of an oligonucleotide, and C is a functional group that can form a bond with the 3'-end of an oligonucleotide. D, F and E are chemical groups that link functional groups A, C and B to S, which is a core atom or scaffold. Preferably, D, E and F are each independently a chain of atoms, such as an alkylene chain or an oligo (ethylene glycol) chain, and D, E and F can be the same or different, and are preferably effective to allow hybridization of the two oligonucleotides and synthesis of the functional moiety. In one embodiment, the trivalent linker has the structure:

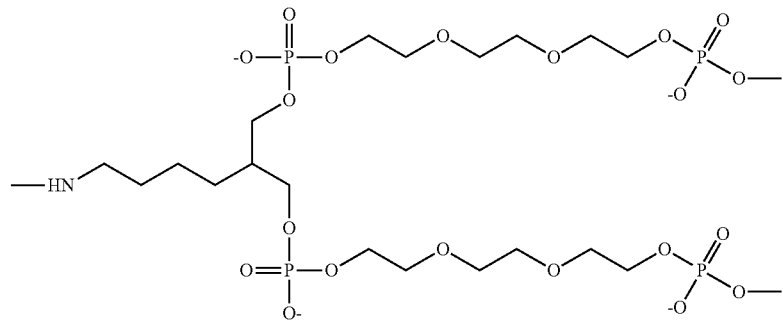

In this embodiment, the NH group is available for attachment to a building block, while the terminal phosphate groups are available for attachment to an oligonucleotide.

Cleavable linkers can be selected from a variety chemical structures. Examples of linkers includes, but are not limited to, linkers having an enzymatic cleavage site, linkers comprising a chemical degradable component, and linkers cleavable by electromagnetic radiation.

Examples of Linkers Cleavable by Electromagnetic Radiation (Light)
o-nitrobenzyl
p-alkoxy

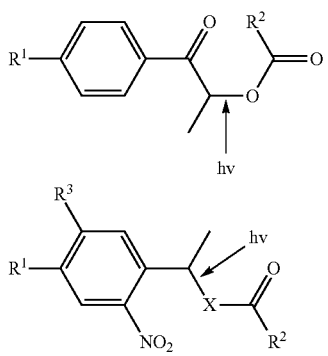

o-nitrobenzyl in exo position

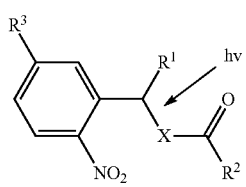

For more details see Holmes CP. J. Org. Chem. 1997, 62, 2370-2380
3-nitrophenyloxy

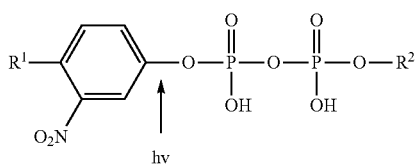

For more details see Rajasekharan Pillai, V. N. Synthesis. 1980, 1-26
Dansyl Derivatives:

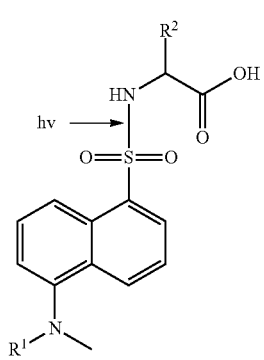

For more details see Rajasekharan Pillai, V. N. Synthesis. 1980, 1-26
Coumarin Derivatives

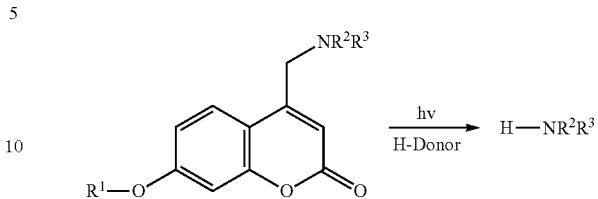

For more details see R. O, Schoenleber, B. Giese. Synlett 2003, 501-504

$R^1$ and $R^2$ can be any molecule or reactive compound building block (CE) such as those exemplified herein above under section A (acylation reactions), respectively. Moreover, $R^1$ and $R^2$ can be either the target or a solid support, respectively. $R^3$ can be e.g. H or $OCH_3$ independently of $R^1$ and $R^2$. If X is O then the product will be a carboxylic acid. If X is NH the product will be a carboxamide.

One specific example is the PC Spacer Phosphoramidite (Glen research catalog #10-4913-90) which can be introduced in an oligonucleotide during synthesis and cleaved by subjecting the sample in water to UV light (300-350 nm) for 30 seconds to 1 minute.

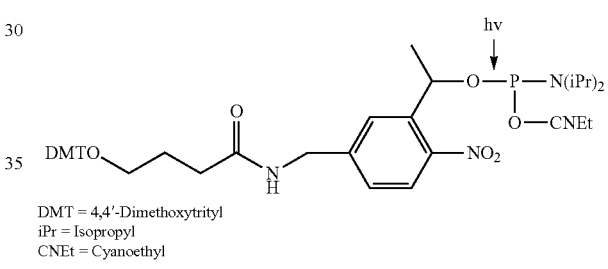

DMT = 4,4'-Dimethoxytrityl
iPr = Isopropyl
CNEt = Cyanoethyl

The above PC spacer phosphoamidite is suitable incorporated in a library of complexes at a position between the identifier and the potential drug candidate. The spacer can be cleaved according to the following reaction.

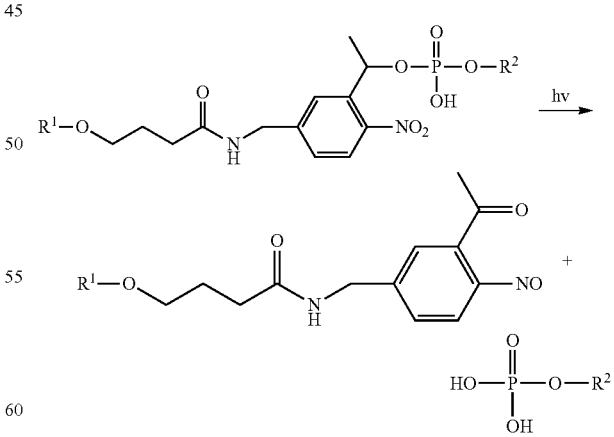

$R^1$ and $R^2$ can be any molecule or reactive compound building block (CE) such as those exemplified herein above under section A (acylation reactions). Moreover, $R^1$ and $R^2$ can be either the target or a solid support, respectively. In a preferred aspect $R^2$ is an oligonucleotide identifier and the $R^1$ is the molecule. When the linker is cleaved a phosphate group is generated allowing for further biological reactions. As an example, the phosphate group can be positioned in the 5' end of an oligonucleotide allowing for an enzymatic ligation process to take place.

Examples of Linkers Cleavable by Chemical Agents:

Ester linkers can be cleaved by nucleophilic attack using e.g. hydroxide ions. In practice this can be accomplished by subjecting the complex to a base for a short period.

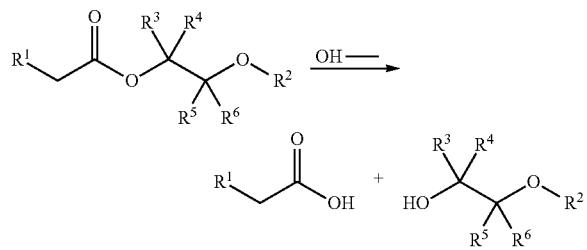

$R^1$ and $R^2$ can be the either of be the potential drug candidate or the identifier, respectively. $R^{4-6}$ can be any of the following: H, CN, F, $NO_2$, $SO_2NR_2$.

Disulfide linkers can efficiently be cleaved/reduced by Tris (2-carboxyethyl) phosphine (TCEP). TCEP selectively and completely reduces even the most stable water-soluble alkyl disulfides over a wide pH range. These reductions frequently required less than 5 minutes at room temperature. TCEP is a non-volatile and odorless reductant and unlike most other reducing agents, it is resistant to air oxidation. Trialkylphosphines such as TCEP are stable in aqueous solution, selectively reduce disulfide bonds, and are essentially unreactive toward other functional groups commonly found in proteins.

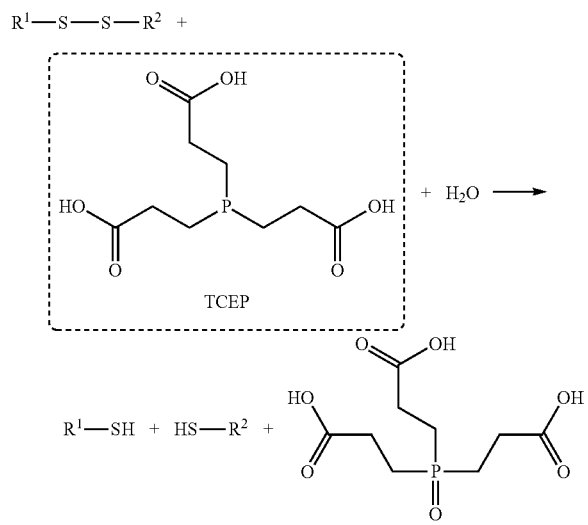

More details on the reduction of disulfide bonds can be found in Kirley, T. L. (1989), Reduction and fluorescent labeling of cyst(e)ine-containing proteins for subsequent structural analysis, *Anal. Biochem.* 180, 231 and Levison, M. E., et al. (1969), Reduction of biological substances by water-soluble phosphines: Gamma-globulin. *Experentia* 25, 126-127.

Linkers Cleavable by Enzymes

Linkers connecting the molecule part of the bi-functional complex with the identifier can include a peptide region that allows a specific cleavage using a protease. This is a well-known strategy in molecular biology. Site-specific proteases and their cognate target amino acid sequences are often used to remove the fusion protein oligonucleotide tags that facilitate enhanced expression, solubility, secretion or purification of the fusion protein.

Various proteases can be used to accomplish a specific cleavage. The specificity is especially important when the cleavage site is presented together with other sequences such as for example the fusion proteins. Various conditions have been optimized in order to enhance the cleavage efficiency and control the specificity. These conditions are available and know in the art.

Enterokinase is one example of an enzyme (serine protease) that cleaves a specific amino acid sequence. Enterokinase recognition site is Asp-Asp-Asp-Asp-Lys (DDDDK), and it cleaves C-terminally of Lys. Purified recombinant Enterokinase is commercially available and is highly active over wide ranges in pH (pH 4.5-9.5) and temperature (4-45° C.).

The nuclear inclusion protease from tobacco etch virus (TEV) is another commercially available and well-characterized protease that can be used to cut at a specific amino acid sequence. TEV protease cleaves the sequence Glu-Asn-Leu-Tyr-Phe-Gln-Gly/Ser (ENLYFQG/S) between Gln-Gly or Gln-Ser with high specificity.

Another well-known protease is thrombin that specifically cleaves the sequence Leu-Val-Pro-Arg-Gly-Ser (LVPAGS) between Arg-Gly. Thrombin has also been used for cleavage of recombinant fusion proteins. Other sequences can also be used for thrombin cleavage; these sequences are more or less specific and more or less efficiently cleaved by thrombin. Thrombin is a highly active protease and various reaction conditions are known to the public.

Activated coagulation factor FX (FXa) is also known to be a specific and useful protease. This enzyme cleaves C-terminal of Arg at the sequence Ile-Glu-Gly-Arg (IEGR). FXa is frequently used to cut between fusion proteins when producing proteins with recombinant technology. Other recognition sequences can also be used for FXa.

Other types of proteolytic enzymes can also be used that recognize specific amino acid sequences. Proteolytic enzymes that cleave amino acid sequences in an unspecific manner can also be used if the linker is the only part of the bi-functional complex which contains an amino acid sequence.

Other type of molecules such as ribozymes, catalytically active antibodies, or lipases can also be used to cleave linkers. The only prerequisite is that the catalytically active molecule can cleave the specific structure used as the linker, or as a part of the linker, that connects the encoding region (i.e the oligonucleotide tag or identifier) and the displayed molecule (i.e. the molecule part of the bi-functional complex) or, in the alternative the solid support and the target. Also, a variety of endonucleases are available that recognize and cleave a double stranded nucleic acid having a specific sequence of nucleotides.

Resynthesis of Bi-Functional Complexes

In some embodiments unique bi-functional complexes are resynthesized following synthesis and analysis of a library. The unique binfunctional complexes may be identified by unique codon sequences. It is then possible to mix the bi-functional complexes and then enrich certain bi-functional complexes according to e.g. affinity for a target, e.g. by performing an affinity selection. Such enriched bi-functional complexes can then be identified e.g. by quantitative PCR, hybridization or a similar method.

Also provided in the present invention is a method to obtain information on third intermediate bi-functional complexes in their free form, i.e. without an identifier oligonucleotide. A display molecule can be synthesized from an initial nascent bi-functional complex with a cleavable linker. The identifier or oligonucleotide tag of this complex may have any composition, e.g. it may be an oligonucleotide of any length or sequence, for example an oligo nucleotide of 10-40 nucleotides in length. During synthesis the nascent bi-functional complex can be purified by gel filtration (size exclusion) because the mass of the oligonucleotide tag employed, e.g. from 3000 to 12000 dalton allows separation of the nascent bi-functional complex from reactive compound building blocks, buffer components and other molecular entities of small mass, which typically have masses less than 1000 dalton. Furthermore, the use of an oligonucleotide tag allows the amount of material retained during synthesis of the bi-functional complex to be estimated by measuring e.g. the optical density (OD) of the DNA by measuring absorbance at 260 nm. Alternatively, an oligonucleotide tag with an easily measurable label such as phosphor-32 or fluorescent groups is used. Following synthesis and subsequent purification of the bi-functional complex, the cleavable linker is cleaved e.g. by electromagnetic radiation, whereby the third intermediate bi-functional complex is released. The oligonucleotide tag can then be removed from the solution containing the third intermediate bi-functional complex, e.g. by hybridizing the oligonucleotide tag to a complementary complementary tag oligonucleotide attached to a solid phase which can easily be removed from the solution. The third intermediate bi-functional complex can then be used in any assay determining some property of the third intermediate bi-functional complex such as Ki determination versus an enzyme, Kd determination versus a protein or other target, or determination of any in vitro or biological parameter such as the activated partial thromboplastin time (aPTT). Removal of the oligonucleotide tag is advantageous if the assay used to measure some property of the third intermediate bi-functional complex is sensitive to the presence of DNA. One advanoligonucleotide tage of the describe method is that the synthesis scale is on the order of nanomoles. Only a small amount of each building block (reactive compound building block) used to synthesize the bi-functional complex is therefore required. Also the building blocks (reactive compound building blocks) used to synthesize the third intermediate bi-functional complex may be labelled by any method e.g. by radioactive atoms; for example the third intermediate bi-functional complex may be synthesized using on or more building blocks (reactive compound building blocks) containing a hydrogen-3 or carbon-14 atom. In this way a released third intermediate bi-functional complex may be used in an assay which measures some property of the third intermediate bi-functional complex by measuring the amount of label present. For example, the third intermediate bi-functional complex may be applied on one side of a layer of confluent CaCo-2 cells. Following a period of incubation the presence of label (reflecting the presence of third intermediate bi-functional complex) may be measured at each side of the confluent cell layer. Said measurements can be informative of the bioavailability of the third intermediate bi-functional complex. In another example the third intermediate bi-functional complex is applied to plasma proteins, e.g. human plasma proteins and the fraction of third intermediate bi-functional complex bound to plasma protein can be determined.

In some cases it may be beneficial that the identifier oligonucleotide tag information that is amplified following the portioning step can be used to direct the re-synthesis of the first library for subsequent further partitioning and identification of desired molecules. Consequently, following an initial split-and-mix synthesis of a library of bi-functional complexes according to the present invention and as disclosed herein and a subsequent partitioning step and optionally amplification of the identifier oligonucleotide tags (identifier oligonucleotides) of selected molecules, the oligonucleotide tags or oligonucleotide tag amplification product(s) can be used as a template for the re-synthesis of the first library or a subset of the first library using any process that allows the information of the amplified identifier to direct a templated synthesis of the library.

Following templated synthesis, the generated second library can be partitioned and the template amplified for identification of desired molecules by e.g. sequencing of the isolated identifiers (templates). Alternatively the amplified template can be used to template the synthesis of a third library being identical to or a subset of the first or the second library using any process that allows the templated synthesis of a library of bi-functional molecules. The process of library resynthesis, partitioning and template amplification can be iterated any number of times such as 1 time, 2 times, 3 times, 4 times, 5 times, 6 times, 7 times, 8 times, 9 times, 10 times or more than 10 times.

Methods that can be used for templated library resynthesis includes but is not limited to (Rasmussen (2006) WO 06/053571A2, Liu et al. (2002), WO 02/074929 A2; Pedersen et al. (2002) WO 02/103008 A2; Pedersen et al. (2003) WO03/078625 A2; Harbury and Halpin, WO 00/23458, Hansen et al WO 06/048025. In the method disclosed by Harbury and Halpin, free reactive compound building blocks are loaded on the reactive site on the identifier in solution or attached to a solid-support. This method of reactive compound building block loading in free form is similar to the methods disclosed herein. Consequently, the building block reactive compound building blocks applied for a first library of bi-functional complexes is directly applicable to the templated process described by Halpin and Harbury for second library synthesis. Other methods for templated synthesis listed above (Rasmussen (2006) WO 06/053571A2, Liu et al. (2002), WO 02/074929 A2; Pedersen et al. (2002) WO 02/103008 A2; Pedersen et al. (2003) WO03/078625 A2; Hansen et al WO 06/048025 A1, requires the pre-attachment of reactive compound building blocks to oligonucleotides prior to the chemical reactions required for the templated synthesis of a second library. Thus, none of the building block reactive compound building blocks applied in a first library synthesis using the method disclosed herein is directly applicable to the synthesis of a second library without prior modification of the reactive compound building blocks and/or appendage to an oligonucleotide.

The following example is included to illustrate the principle of templated resynthesis of a library using templates that are amplified from a pool of identifiers isolated from the screening of a first library of bi-functional molecules.

Synthesis of a first library is conducted as described elsewhere in the claims and in example 1 producing a library consisting of app 65.000 different bi-functional molecules. The tetramer library consists of bi-functional complexes each comprising 4 DNA codon elements (oligonucleotide tags) covalently linked to the cognate chemical fragments.

Each 20 nt/bp codon is spaced by a 10 nt fixed region and the oligonucleotide tags A-D is flanked by fixed sequences useful for amplification by PCR.

The 65.000 member library was screened against thrombin and the isolated DNA was amplified as described in example 1 using proof-reading PCR and the forward and reverse primers 5'-CAAGTCACCAAGAATTCATG (SEQ ID NO 7) and 5'-AAGGAACATCATCATGGAT. The PCR product was used as template for large-scale 96 wells proof-reading PCR (Pwo Master- mix, Roche) using a similar primer pair except that the forward primer contained the $NH_2$-PEG unit described in example 1 and the reverse primer contained a 5'-biotin group. Following PCR, the content of all wells was pooled, extracted twice with phenol and once with chloroform before ethanol/acetate precipitation of the DNA. Following centrifugation the DNA pellet was washed twice using 70% ethanol, dried and redissolved in 100 ul of 25 mM $NH_4$-acetate pH 7.25. 100 ul SA-beads (Amersham) is washed 3 times with 25 mM $NH_4$-acetate buffer before mixing with the DNA sample and incubation for 10 min at RT. The sample is washed 3 times with ammonium-acetate buffer. The non-biotinylated topstrand comprising the 5' Amino-PEG unit was eluted by adding 200 ul of $H_2O$ at 90° C. for 30 seconds before immediate spin removal of the SA-beads using a SpinX column (Corning). The singlestranded template is incubated with another 100 ul of SA-beads and incubated for 10 min at RT before SA-bead removal using SpinX column. The unbound fraction is purified on a microspin 6 column (Bio-rad). This sample containing a singlestranded template with terminal Amino-PEG unit was used for the templated resynthesis of the second library essentially according to the method of Halpin and Harbury: DNA Display I. Sequence-Encoded Routing of DNA Populations, *PLoS Biol.* 2004 July; 2(7): e173. DNA Display II. Genetic Manipulation of Combinatorial Chemistry Libraries for Small-Molecule Evolution, *PLoS Biol.* 2004 July; 2(7): e174. DNA Display III. Solid-Phase Organic Synthesis on Unprotected DNA, *PLoS Biol.* 2004 July 2(7): e175.

In brief, the singlestranded template is allocated according to the codon sequence in position A into specific compartments by hybridization to a complementary complementary tag immobilised to a solid-support. Consequently, 16 different complementary tags each capable of hybridizing specifically to one A-codon oligonucleotide tag is immobilised on solid-support, placed in individual housings and connected in series. The template is pumped through the compartments in a circular system until the templates are allocated in their cognate compartments. Subsequently, each template is transferred to a DEAE column for chemical reaction with a codon specific building block (reactive compound building block) according to Table 1.4A. Following chemical transformation and deprotection, all templates are collected from the DEAE column, pooled and redistributed into specific codon B compartments in a process similar to that described above for position A. Consequently the allocation, chemical reaction, deprotection, pooling steps can be iterated for codon positions A to D ultimately producing a library a bi-functional complexes using the same building block/codon combinations as for the initial library enabling the resynthesis of this library based on the identifier/template bias created from the partitioning of the first library.

Templated Synthesis of a Library of Bi-Functional Complexes Using Identifier Allocation by Sequential Identifier Subtraction.

Several methods have been disclosed for the templated synthesis of a library of bi-functional complexes such as (Rasmussen (2006) WO 06/053571A2, Liu et al. (2002), WO 02/074929 A2; Pedersen et al. (2002) WO 02/103008 A2; Pedersen et al. (2003) WO03/078625 A2; Harbury and Halpin, WO 00/23458, Hansen et al WO 06/048025. All methods except for DNA-display (Harbury and Halpin) employ the pre-attachment of reactive compound building blocks to specific oligonucleotide sequences capable of hybridising to a specific codon on the template. This pre-attachment is time- and resource consuming and limits the number of commercially available reactive compound building blocks for library generation. In contrast, the chemical transformation using free-form reactive compound building blocks (Halpin and Harbury) dramatically increase building block access, number of chemical reactions available for library generation and reduce time and resources necessary for preparation of reactive compound building blocks. Consequently, the free-form reactive compound building block offers a clear advanoligonucleotide tage for the fast access to and diversity of chemical transformations. However, the method disclosed by Halpin and Harbury requires specific allocation of the identifier templates into discrete compartments. This allocation is conducted by passing the pool of identifier templates through a series of compartments comprising compartment specific complementary tags oligonucleotides attached to a solid-support. Such compartment specific allocation is difficult due to problems with unspecific template allocation resulting in a template being fortuitously trapped in compartments with a non-cognate complementary tag. Ultimately, this results in an illegal reactive compound building block/codon combination and a reduced fidelity in translation of the template. Furthermore, the single stranded form of DNA is energetically disfavoured and a complex ssDNA template will tend to take up secondary structure which may result in template loss during an allocation step due to lack of hybridisation to a cognate complementary tag. Also, the hybridisation between two complementary oligonucleotide sequences may be impeded to some extent by the covalent attachment of one oligonucleotide component (complementary tag) to a solid-support compared to a similar duplex formation performed in solution.

The issues above could be resolved by performing the hybridization between a specific complementary tag or a subset pool of complementary tags and the complementary identifier sequence(s) in solution. This allows the experimenter to remove secondary structures in the template f. ex by a heat denaturation step prior to complementary tag hybridization for improved hybridization kinetics. Subsequently, the complementary tag/identifier duplexes needs to be retracted from the remaining unbound fraction of identifiers in a first allocation step using a handle supplied on the complementary tag such as a biotin-group for specific isolation using SA(streptavidin)-beads. Following retraction of the first subset of identifiers the remaining pool of unbound identifiers is denatured before addition of the next specific complementary tag or subset of complementary tags and the process of identifier subset isolation is iterated until all identifiers are allocated on their sequence specific subset SA-beads. Obviously, an iterative process involving fishing out single specific codon identifier sequences may become unfeasible for large codon sets. Consequently, the entire pool of individual (single) complementary tag sequences complementary to the pool of codons at one position such as position A in the template, can be subdivided into a subset pool of complementary tags. The subset pools can then be used for sequential subtraction of identifier templates into discrete pools. Following elution of identifiers from each retracted sub-pool the single-stranded identifiers are hybridised to a smaller subset of complementary tags than used for initial round of allocation or using a single complementary tag from the corresponding first round subset. The sequential subtraction can be iterated until each identifier is allocated in separate compartments according to its unique first codon sequence.

The example below is included to illustrate the use of sequential subtraction. Initially, 10 subset pools a-j each comprising 10 complementary tag totaling 100 complementary tag sequences for codon position A is prepared carrying a purification handle (f. ex a biotin-group).

i) A singlestranded identifier with a reactive entity is provided.
ii) $1^{st}$ capture: combine complementary tags complementary to codon position A in different 10 different pools (a-j) each having 10 complementary tags:
(a)1-10, (b)11-20, (c)21-30, (d)31-40, (e)41-50, (t)51-60, (g)61-70, (h)71-80, (1)81-90, (j)91-100.
iii) Add pool a to identifier and hybridize complementary tags to the cognate subset of identifiers in solution or on solid support. The bound fraction is subtracted from the pool using the complementary tag handle.
iv) The fraction of unbound identifiers is hybridized to pool b and subtracted from the identifier pool as above
v) Continue the identifier subset subtraction using complementary tag pool a to j.
vi) Elute single-stranded identifier into pool a to j
vii) $2^{nd}$ capture: The subset capture method described above is used for each subset a to j applying single complementary tags. Consequently, from pool a, complementary tag 1 is used as a first hybridizing complementary tag allowing specific subtraction of identifiers with a codon 1 at position A. The unbound pool of identifiers is subsequently hybridized with complementary tag 2 for specific subtraction of identifiers with codon 2 at position A.
viii) Repeat identifier subset allocation using all 10 single complementary tag within specific subgroup allowing specific (single) allocation of identifiers in 100 subset groups.
ix) Chemical reaction using specific reactive compound building block/codon combinations and subsequent deprotection
x) Pool identifiers and repeat routing principle for codon position B In the example above, two branch allocations are conducted for each specific identifier (ie each codon sequence is subset allocated twice). In the first round each identifier is allocated as a subset pool followed by a second specific allocation for each unique codon. However, the experimenter may choose any number of branches, any number of subset pools at each branch and any number of complementary tags in each subset pool. Furthermore, the specific routing conducted for one position is custom-made for that codon position and, consequently, the experimenter can re-use the branch-profile from one position to any of the remaining positions or may apply a branch profile that is unique for a codon position.

Also, the experimenter may use any number of branches such as 1, 2, 3, 4, 5, 6, 7, 8, 9, 10 or more than 10 branches in the routing protocol. Furthermore, the experimenter can use any number of subset pools such as any number between 1 and 1.000 or more than 1.000. Also the experimenter can use any number of complementary tags in each subset pool such as any number between 1 and 1.000 or more than 1.000.

The use of multiple branches increase the specificity of the allocation step, because the level of unspecific allocation is reduced when conducting more than a single allocation round as described Halpin and Harbury WO 00/23458. In the example below, a principle for sub-allocation of 200 different codons at position for a pool of identifier templates is described using 3 branches. In the first branch 5 pools of complementary tags each comprising 40 unique complementary tags is used for the sequential subtraction of identifiers into their cognate sub-pools. Following elution of identifiers in each sub-pool, the second branch of allocation is conducted using a subset of 5 pools of 8 complementary tags each, for the specific retrieval of subsets within their respective $1^{st}$ branch subset producing a total of 25 sub-pools. Following identifier elution, the $3^{rd}$ branch of subset allocation is conducted using each unique complementary tag individually for identifier retrieval subtracted from their cognate subset pool from the $2^{nd}$ branch resulting in specific single allocation of identifiers containing a unique codon at position A. Subsequently, the identifiers can be eluted e.g. in H2O as described herein elsewhere and prepared for chemical transformation using a codon-specific reactive compound building block, reacted, optionally purified, optionally deprotected and pooled before re-allocation according to the next codon position of the identifier template. The process is iterated any number of times dependent on the number of chemical reactive compound building block that need to be reacted and the number of codon positions. Chemical reactions can be conducted by any means compatible with the presence of DNA including methods described herein and using methods referred in this document The method described here, make use of iterative steps of subtraction of specifically formed duplexes between the complementary tags supplied and the corresponding identifier codon sequences. The method relies on efficient retrieval of the duplexes which can be done using any means useful for isolation of DNA duplexes. Consequently, any entity capable of being linked to an complementary tag and useful as handle for purification purposes may be used for the allocation steps described herein. Specifically, the complementary tags may be supplied with a handle for purification of the duplexex, such as a biotin-group for interaction with streptavidine-beads or derivatives thereof, a dinitrophenol (DNP) for purification using DNP-specific antibodies (f.ex covalently attached to a solid-support) or having a reactive compound building block f. ex a thiol-group capable of reacting forming a covalent link with a solid-support such as 2-pyridin-activated thio-sepharose (Amersham Biosciences). In principle, the complementary tag or pool of complementary tags may be linked covalently, or non-covalently to a solid-support prior to hybridization of the identifier templates.

An example of a templated re-synthesis is disclosed herein below.

Step1: Construction of Complementary Tag Columns 16 different twenty-base capture oligonucleotides were synthesized using standard phosphoramidite chemistry, with the addition of a C12-methoxytritylamine modifier at the 5'-end (Glen Research #10-1912, DNA technology, Aarhus Denmark). The HPLC purified oligonucleotides were loaded on a DEAE column and reacted with Fmoc-amino-PEG24 carboxylic-acid (Quanta BioDesign, ltd) using DMT-MM as activating agent. Excess Fmoc-Amino-PEG linker was removed by collecting the oligonucleotide on a DEAE column followed by Fmoc deprotection by two 1-ml treatments with 20% piperidine in DMF, one for 3 min and one for 17 min. Following elution from DEAE, the oligonucleotides were purified by microspin column gelfiltration (biorad) and analysed on ES-MS. The oligonucleotides were covalently attached to a sepharose resin by incubation with one volume equivalent of drained NHS-activated Sepharose (Amersham Biosciences #17-0906-01). The suspension was rotated at 37° C. ON before addition of 1M Tris-HCl and incubation ON. The product resin was washed and could be stored at 4° C. or −20° C.

The derivatized resins were loaded into empty DNA synthesis column housings (#CL-1502-1; Biosearch Technologies, Novato, Calif., United States).

Step 2: ssDNA Template Hybridization.

Approximately 250 μl of DEAE Sepharose suspension was pipetted into an empty Glen Research column housing and washed with 20 ml of $H_2O$ followed by 12 ml of DEAE bind buffer (10 mM acetic acid and 0.005% Triton X-100) using a syringe or a syringe barrel, a male-male luer adapter, and a vacuum manifold. The template DNA was loaded onto the washed chemistry column in 1 ml of DEAE bind buffer at approximately 1 ml/min. Anticodon columns were connected in series to the DEAE column using male tapered luer couplers, capillary tubing, silicone tubing, and tubing connectors. Approximately 3 ml of hybridization buffer containing 1 nmol of each oligonucleotide complementary to the noncoding regions was cyclically pumped over the system at 0.5 ml/min for 1 h at 70° C., 10 min at 37° C., and 1 h in a 46° C. water bath within a 37° C. room. Hybridized DNA was transferred back to fresh individual DEAE columns for loading of the specific reactive compound building blocks, Step 3: Chemical Reactions at Position A Chemical reaction on the reactive amino-group on the template was carried out essentially as described in Halpin and Harbury (PLoS, 2004). To accomplish amino acid additions, columns were washed with 3 ml of DMF and subsequently incubated with 50 mM Fmoc protected-AA shown in table 1.4 and 50 mM DMT-MM in 100 ul of coupling mix containing 2% DEA in DIPEA/H2O (95:5) for 10 min. Excess reagent was washed away with 3 ml DMF, and the coupling procedure was repeated. The Fmoc-protecting group was then removed by two 1-ml treatments with 20% piperidine in DMF, one for 3 min and one for 17 min. Finally, the columns were washed with 3 ml of DMF followed by 3 ml of DEAE Bind Buffer (10 mM acetic acid, 0.005% Triton X-100). Identifier templates were eluted with 2 ml of Basic Elute Buffer (1.5 M NaCl, 10 mM NaOH, and 0.005% Triton X-100) heated to 80° C. The DNA was pooled, precipitated with ethanol/acetate, redissolved and reloaded on a fresh DEAE column.

Subsequent Re-Allocation According to Codon B, C and D.

Construction of complementary tag columns, ssDNA template allocation and transfer to specific DEAE columns for position B, C and D reactions was accomplished using the protocol described above for codon A.

Chemical Reaction at Position B

Building block reactive compound building blocks according to Table 1.4B was reacted using 50 mM of reactive compound building block, 50 mM DMT-MM in in 100 ul of coupling mix containing 2% DIPEA (N,N'-Diisopropyethylamin) in DMF/H2O (95:5) for 10 min. Excess reagent was washed away with 3 ml DMF, and the coupling procedure was repeated. The Msec protection group was removed by addition of 20% piperidine in H2O for 10 min. The process was repeated once.

Chemical Reactions at Position C

Building blocks (reactive compound building blocks) for position C is listed in Table1.4C i) Acylation reactions: Conducted as described above.

ii) Isocyanate addition: The DNA on DEAE was washed with 0.5 ml of a buffer containing 100 mM sodium borate and 100 mM sodium phosphate pH 8.0 and subsequently incubated with 50 mM of specific isocyanate reactive compound building block in CH3CN in the above buffer in a total volume of 100 ul. The reaction was incubated at 50° C. ON.

iii) Sulphonylation: The DNA on DEAE was washed using 100 mM Na-borate pH 9. Subsequently 10 ul of 100 mM of sulphonylation reactive compound building block in THF is mixed with 40 ul of 100 mM Na-borate buffer pH 9 and incubated at 30° C. ON.

Following transformations all resins are washed and the templated molecules are Ns deprotected by incubation in a solution of 0.25 M mercaptoanisol and 0.25 M DIPEA (N,N'-Diisopropylethylamine) in DMF and incubated ON at 25° C. in an eppendorph thermoshaker at 600 rpm. Then the material on DEAE was washed with 0.3M AcOH in DMF, then twice with DMF before elution.

Chemical Reactions at Position D

Building blocks (reactive compound building blocks) for position D are listed in Table 1.4D Acylation, isocyanate addition and sulphonylation was carried out as described above.

iv) Nucleophilic aromatic substitution: DNA on DEAE was washed once with 0.5 ml 100 mM Na-borate buffer pH 9.0. 25 ul of the reactive compound building block in (100 mM in DMSO) was mixed with 25 ul of 100 mM Na-borate pH 9.0 was added and the reaction incubated at 90° C. ON v) Reductive amination: DNA on the DEAE resin was washed with 0.5 ml of 200 Na-acetate buffer pH 5.0 in 90% DMF followed by incubation of 10 ul of 200 mM reactive compound building block in DMSO dissolved in 40 ul of 200 mM Na-acetate buffer pH 5.0 in 90% DMF and subsequent incubation at 30° C. for 1 hour. Subsequently 25 ul of freshly prepared 140 mM $NaCNBH_3$ in Na-acetate buffer pH 5.0 was added followed by incubation ON at 30° C.

Following the final chemical reactions, all samples are subjected to an Fmoc deprotection reaction using piperidine as described above (position A). The DNA is eluted from the DEAE columns, pooled and precipitated using ethanol/acetate. Following centrifugation the pellet is washed twice with 70% ethanol, dried and redissolved in $H_2O$.

Prior to iterating the affinity selections on trombin, the singlestranded library of bi-functional complexes is converted to a doublestranded form by polymerase extension as described in example 1.

Library Synthesis Methods

When a library of different bi-functional complexes are synthesised, split-and-mix synthesis methods are employed as disclosed herein above. Accordingly, a plurality of nascent bi-functional complexes obtained after a first synthesis round are divided ("split") into multiple fractions. In each fraction, the nascent bi-functional complex is reacted sequentially or simultaneously with a different reactive compound building block and a corresponding oligonucleotide tag which identifies each different reactive compound building block.

The molecules (linked to their respective identifier oligonucleotides) produced in each of the fractions as disclosed herein above and in the claims, are combined ("pooled") and then divided again into multiple fractions. Each of these fractions is then reacted with a further unique (fraction-specific) reactive compound building block and a further oligonucleotide tag identifying the reactive compound building block. The number of unique molecules present in the product library is a function of the number of different reactive compound building blocks used in each round of the synthesis and the number of times the pooling and dividing process is repeated.

When a library of different bi-functional complexes according to the present invention are synthesised, the method preferably comprises the steps of providing in separate compartments nascent bi-functional complexes, each comprising a chemical reaction site and an oligonucleotide tag addition site for enzymatic addition of an oligonucleotide tag, and performing in any order reaction in each compartment between the chemical reaction site and one or more reactive compound building blocks, and enzymatically adding to the oligonucleotide tag addition site one or more oligonucleotide tags identifying the one or more reactive compound building blocks having participated in the synthesis of a molecule or an intermediate thereof.

The nascent bi-functional complexes in each compartment can be identical or different. In the event the nascent bi-functional complex differs at the chemical reaction site, the nascent bi-functional complex suitably comprises an oligonucleotide tag identifying the structure of the chemical reaction site. Similar, the reactive compound building blocks applied in each compartment can be identical or different as the case may be. Also, the reaction conditions in each compartment can be similar or different.

Accordingly, the contents of any two or more compartments can be mixed and subsequently split into an array of compartments for a new round of reaction. Thus, in any round subsequent to the first round, the end product of a preceding round of reaction is used as the nascent bi-functional complex to obtain a library of bi-functional complexes, in which each member of the library comprises a reagent specific reaction product and respective oligonucleotide tags which codes for the identity of each of the reactive compound building blocks that have participated in the formation of the reaction product.

In some embodiments, it is preferred to add the oligonucleotide tag to the nascent bi-functional complex prior to the reaction, because it can be preferable to apply conditions for the reaction which are different form the conditions used by the enzyme. Generally, enzyme reactions are conducted in aqueous media, whereas the reaction between reactive compound building blocks or between reactive compound building blocks and the chemical reaction site—at least for certain types of reactions—is favoured by an organic solvent.

One approach for obtaining suitable condition for both reactions is to conduct the enzyme reaction in an aqueous media, lyophilize the mixture and subsequently dissolve or disperse the lyophilized mixture in a media suitable for the desired reaction to take place. In an alternative approach, the lyophilization step can be dispensed with as the appropriate reaction condition can be obtained by adding a solvent to the aqueous media. The solvent can be miscible with the aqueous media to produce a homogeneous reaction media or immiscible to produce a bi-phasic media.

A vast number of different libraries can be designed and synthesised by the methods of the present invention. The libraries may be designed using a number of approaches known to a person skilled in the art. Library design (i.e. the choice of reactive compound building blocks, linkers, and oligonucleotide tags which shall be used for the synthesis of a library) may consist of a number of steps including but not limited to:

I. Choosing the linker type, e.g., the linker may be chosen to have a single chemical reaction site, two chemical reaction sites or more. The chemical reaction site may be chosen to be an amine, an acid, an aldehyde or a C—X group where X is a halogen.
II. Choosing the number of reactive compound building blocks to be used at each cycle during library synthesis.
III. Choosing the type of reactive compound building blocks, such as, but not limited to
   a. reactive compound building blocks with a single reactive group such as a —COOH group, an amine, an isocyanate, a sulfonyl halogen, an aldehyde or a C—X group where X is a halogen, and/or
   b. reactive compound building blocks with two reactive groups chosen from the group of a —COOH group, an amine, an isocyanate, a sulfonyl halogen, an aldehyde or a C—X group where X is a halogen, and/or
   c. reactive compound building blocks with three reactive groups chosen from the group of a —COOH group, an amine, an isocyanate, a sulfonyl halogen, an aldehyde or a C—X group where X is a halogen.
   d. reactive compound building blocks with four reactive groups chosen from the group of a —COOH group, an amine, an isocyanate, a sulfonyl halogen, an aldehyde or a C—X group where X is a halogen.
   e. reactive compound building blocks with five reactive groups chosen from the group of a —COOH group, an amine, an isocyanate, a sulfonyl halogen, an aldehyde or a C—X group where X is a halogen.
   f. reactive compound building blocks with six reactive groups chosen from the group of a —COOH group, an amine, an isocyanate, a sulfonyl halogen, an aldehyde or a C—X group where X is a halogen.
   g. All or some of the reactive group may be appropriately protected using a protection group known to a person skilled in the art such as an fmoc group, a nosyl group, an msec group, a boc group or a tBu group (see general procedures for details).
IV. Choosing the number of each type of reactive compound building blocks to be used at each cycle during library synthesis.
V. Analyzing reactive compound building blocks with regards to properties such as molecular weight, octanol/water and water/gas log Ps, log S, log BB, overall CNS activity, Caco-2 and MDCK cell permeabilities, human oral absorption, log Khsa for human serum albumin binding, and log IC50 for HERG K+-channel blockage log D, the number of hydrogen bond donors or acceptors, rotational bonds, polar surface area, Lipinski Rule-of-Five violations, drug-likeness or lead-likeness etc. Said properties may be predicted e.g. using a computer program such as qikprop (www.schrodinger.com) or determined in an assay by a person skilled in the art.
VI. Comparing reactive compound building blocks with other reagents with regards to structural of functional similarity.
VII. Enumerating the library to be synthesized, i.e., virtually (e.g. using a computer) constructing all possible encoded molecules.
   a. Analyzing said molecules with regards to properties such as molecular weight, octanol/water and water/gas log Ps, log S, log BB, overall CNS activity, Caco-2 and MDCK cell permeabilities, human oral absorption, log Khsa for human serum albumin binding, and log IC50 for HERG K+-channel blockage log D, number of hydrogen bond donors or acceptors, rotational bonds, polar surface area, Lipinski Rule-of-Five violations, drug-likeness or lead-likeness etc. Said properties may be predicted e.g. using a computer program such as qikprop (www.schrodinger.com) or determined in an assay by a person skilled in the art.
b. Comparing said molecules with other molecules with regards to structural of functional similarity.

VIII. Testing the reaction efficiency of reactive compound building blocks before using them for library synthesis.

IX. Generating one or more encoded molecules using reactive compound building blocks from an initial list of reactive compound building blocks to be used for the synthesis of a specific library, subjecting said encoded molecule(s) to one or more assays, and adjusting said list of reactive compound building blocks (i.e. removing reactive compound building blocks from the list or adding reactive compound building blocks to the list) based on the results of said assays.

X. Choosing reactive compound building blocks based on prior information regarding a target or a related molecule on which a library is intended to be screened.
A related molecule may be one or more parts of a target, a molecule derived from a target e.g. by mutation, a molecule which is related to the target e.g. another member of the target family, a target homolog etc.
The prior information may be
a. structural information obtained by x-ray crystallography or NMR or another method
b. structural information obtained by x-ray crystallography or NMR or another method in the presence of ligand and/or cofactor
c. structural information obtained by x-ray crystallography or NMR or another method in the presence of a molecule or fragment such as a reactive compound building block or a reactive compound building block analog
d. information obtained by oligonucleotide mutagenesis followed by an assay which can be performed by a person skilled in the art.
e. structure-activity information obtained e.g. by synthesis of a series of molecules followed by testing of the molecules in an appropriate assay. Such information may suggest reactive compound building blocks which are identical or similar to parts of said tested molecules.

XI. Choosing reactive compound building blocks based on prior information obtained by synthesis of a library followed by screening of the library and analyses of the screening results. Said library being synthesized by the methods described by the current invention or related methods for synthesizing bi-functional molecules such but not limited to those described in Rasmussen (2006) WO 06/053571A2, Liu et al. (2002), WO 02/074929 A2; Pedersen et al. (2002) WO 02/103008 A2; Pedersen et al. (2003) WO03/078625 A2; Harbury and Halpin, WO 00/23458, and Hansen et al WO 06/048025.

In some embodiments it is preferred that each intermediate or final bi-functional complex has the same general structure. In other embodiments it is preferred that each intermediate or final bi-functional complex has a different general structure, e.g. is composed from a different number of reactive compound building blocks, such as e.g.:

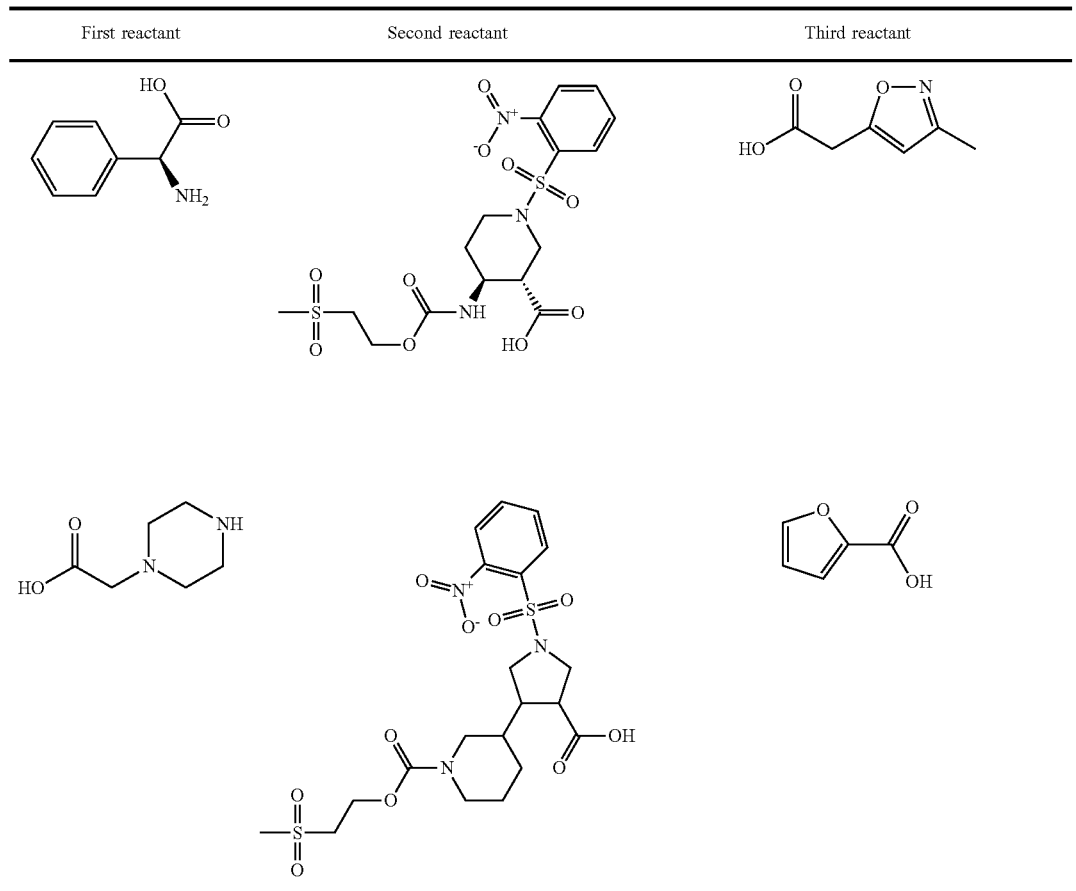

| Fourth reactant | Fifth reactant | Final product |
|---|---|---|

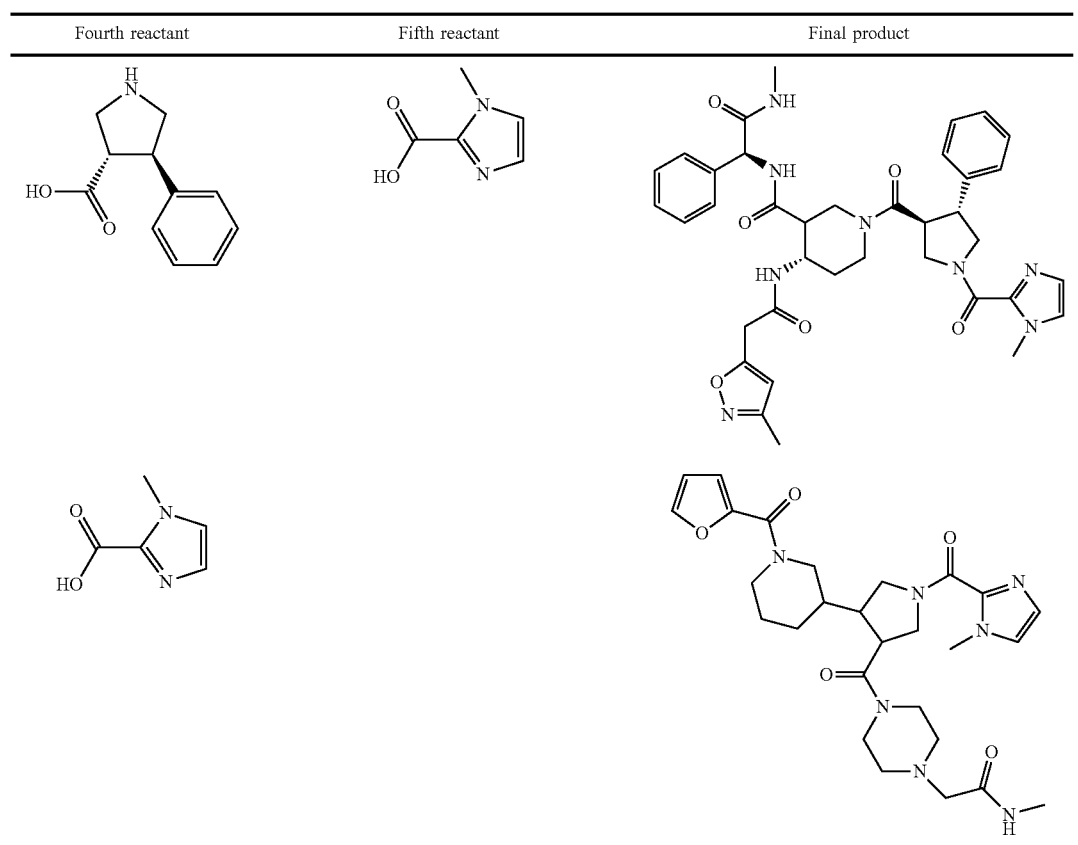

This can be achieved e.g. by subjecting the library to a final reactive compound building block reaction step. The reactive compound building block can only react with third intermediate bi-functional complexes that have a corresponding reactive group. Thus, the finalized library may contain third intermediate bi-functional complexes of different general structures, e.g., be composed of a different number of entities.

Libraries of the present invention can be virtual libraries, in that they are collections of computational or electronic representations of molecules. The libraries may also be "wet" or physical libraries, in that they are a collection of molecules that are actually obtained through, for example, synthesis or purification, or they can be a combination of wet and virtual, with some of the molecules having been obtained and others remaining virtual, or both.

Libraries of the present invention may, for example, comprise at least about 10, such as at least about 50, for example at least about 100, such as at least about 500, for example at least about 750, such as at least about 1,000, or for example at least about 2,500 molecules or compounds. Larger libraries of e.g. at least $10^4$ different molecules or compounds, such as least $10^5$ different molecules, for example least $10^6$ different molecules, such as least $10^7$ different molecules, for example at least $10^8$ different molecules are also contemplated.

Libraries of the present invention may also include subsets of larger libraries, i.e. enriched libraries comprising at least two members of a larger (naïve) library.

In various embodiments, at least about 40%, at least about 50%, at least about 75%, at least about 90%, or at least about 95% of the molecules of the libraries of the present invention have less than six, less than five, or, for example, less than four hydrogen bond acceptors.

In various embodiments, at least about 40%, at least about 50%, at least about 75%, at least about 90%, or at least about 95% of the molecules of the libraries of the present invention have less than six, less than five, or, for example, less than four hydrogen bond donors.

In various embodiments, at least about 40%, at least about 50%, at least about 75%, at least about 90%, or at least about 95% of the molecules or compounds of the libraries of the present invention have a calculated Log P value of less than six, less than five, or, for example, less than four.

In various embodiments, at least about 40%, at least about 50%, at least about 75%, at least about 90%, or at least about 95% of the molecules or compounds of the libraries of the present invention have a molecular weight of less than about 500, such as less than about 350, for example, less than about 300, such as less than about 250, for example less than about 200 Daltons, such as less than about 150 Daltons, for example less than about 100 Daltons.

Also included in the scope of the present invention are methods and computer processor executable instructions on one or more computer readable storage devices wherein the instructions cause representation and/or manipulation, via a computer output device, of a molecule library of the present invention. Also, methods for performing such representation and/or manipulation of a molecule library having been produced by the methods of the present invention are within the scope of the present invention.

For example, the processor executable instructions are provided on one or more computer readable storage devices wherein the instructions cause representation and/or manipulation, via a computer output device, of a library of the present invention, such as, for example, a library of scaffolded molecules, the library may comprise a plurality of molecules, wherein each molecule comprises a scaffolded part and one or more reactive compound building blocks.

The present invention also provides processor executable instructions on one or more computer readable storage devices wherein the instructions cause representation and/or manipulation, via a computer output device, of a combination of structures for analysis, wherein the combination comprises the structure of one or more members of a library of the present invention, and a biological target molecule.

In one embodiment of the invention the structure of the one or more members of the library can be represented or displayed as interacting with at least a portion of a substrate binding pocket structure of a biological target molecule. The processor executable instructions may optionally include one or more instructions directing the retrieval of data from a computer readable storage medium for the representation and/or manipulation of a structure or structures described herein.

In another aspect of the invention, combinations are provided. For example, provided in the present invention is a combination of structures for analysis, comprising a molecule library of the present invention, and a biological target molecule, wherein the structures comprise members of the library, the target molecule, and combinations thereof.

Also provided in the present invention is a combination of structures for analysis, comprising a member of a molecule library of the present invention and a biological target molecule, wherein the structures comprise the library member, the biological target molecule, and combinations thereof. The combination can be virtual, for example, computational representations, or actual or wet, for example, physical entities. In one example, at least one member of the library binds to a portion of a ligand binding site of the target molecule. In some aspects of the combination, the concentration ratio of library members to target molecules is in a ratio of, for example about 50,000, about 25,000, about 10,000, about 1,000, about 100, or about 10 mol/mol. In some aspects of the combination, the concentration of library members is close to, at, or beyond the solubility point of the solution.

The present invention also provides a mixture for analysis by x-ray crystallography, comprising a plurality of molecules or compounds selected from a library of the present invention and a biological target molecule. The biological target molecule, may, for example, be a protein, or a nucleic acid. The biological target molecule may, for example, be crystalline.

Methods of designing novel compounds or lead candidates are also provided in the present invention. For example, in one embodiment of the present invention, a method is provided of designing a lead candidate having activity against a biological target molecule, comprising obtaining a library of the present invention, determining the structures of one or more, and in some embodiments of the invention at least two, members of the library in association with the biological target molecule, and selecting information from the structures to design at least one lead candidate.

The methods of the present invention can further comprise the step of determining the structure of the lead candidate in association with the biological target molecule. In one embodiment, the method further comprises the step of designing at least one second library of compounds wherein each compound of the second library comprises a scaffold and two or more reactive compound building blocks; and each compound of the second library is different. In one embodiment of the invention, the scaffold of the compounds of the second library and the scaffold of the lead candidate is the same. In one embodiment, the method further comprises the steps of obtaining the second library; and determining the structures of one or more, and in some embodiments of the invention at least two, compounds of the second library in association with the biological target molecule. The biological target molecule can be, for example, a protein or, for example, a nucleic acid. The biological target molecule may, for example, be crystalline.

In one embodiment, the method of the present invention further comprises cross-linking one or more bi-functional complexes to a particular compound, to which the molecule part of the bi-functional complexes has affinity.

The crosslinking may be performed using any suitable means that ensures the formation of a covalent bond. Suitably, the crosslinking is performed employing compounds or reactive moieties selected from a group consisting of chemical crosslinkers. In a preferred embodiment the compounds are from the subgroup consisting of photoactivatable cross-linkers. The photoactivatable cross linkers can be incorporated in the bi-functional molecule prior to the library generation as a part of the spacer or attached to the spacer. In another example the photoactivatable crosslinkers can be incorporated into or as a part of the displayed molecule during the library generation.

The photoactivatable crosslinkers for coupling target and bi-functional molecules can be selected from a large plethora. Suitable examples include:

a) Azides

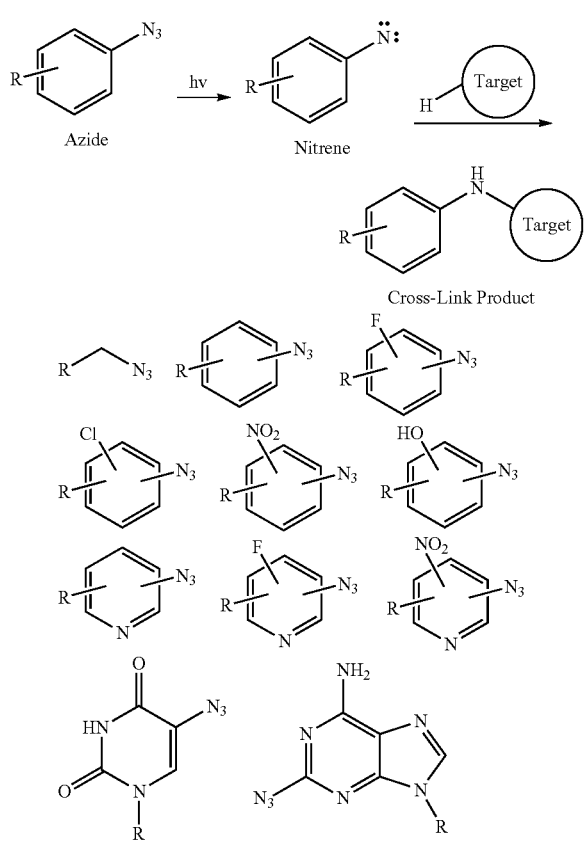

175
-continued
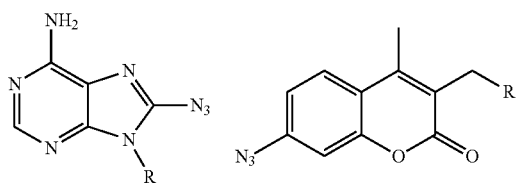
b) Diazirines
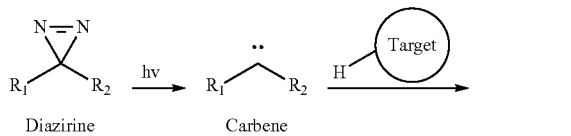
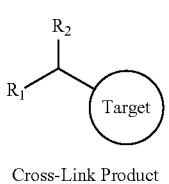
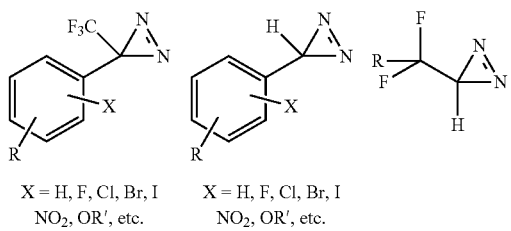
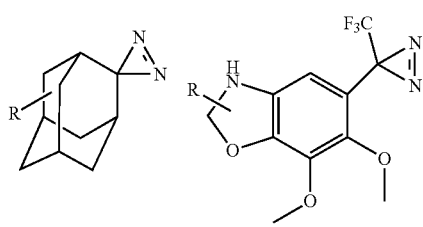
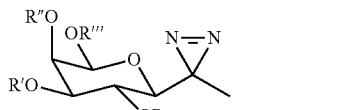
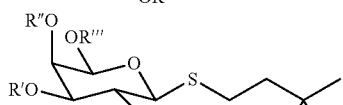
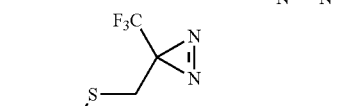
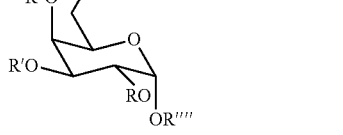
176
c) Halo-Aromatic/Halo-Heteroaromatic Compounds
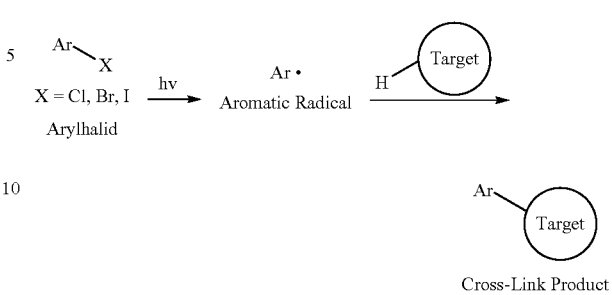
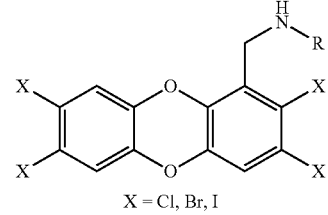
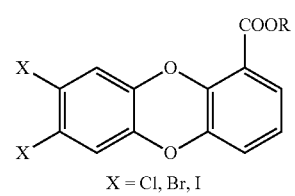
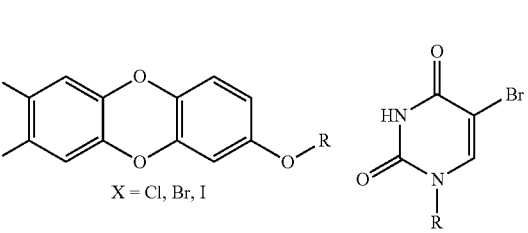
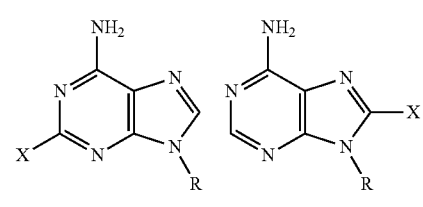
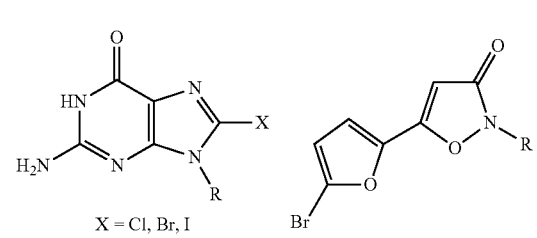
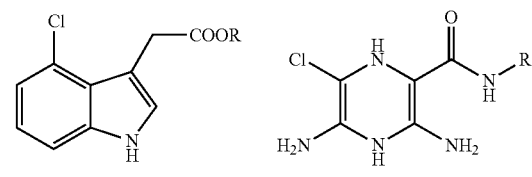

d) Aromatic Nitro Compounds
e) Benzophenones
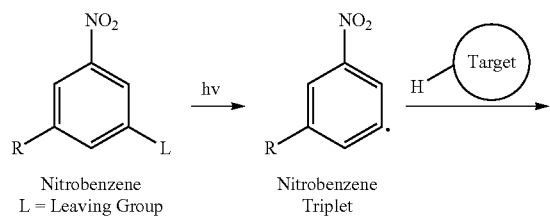
Nitrobenzene
L = Leaving Group
L = OR, F, Cl, Br, I
Nitrobenzene
Triplet
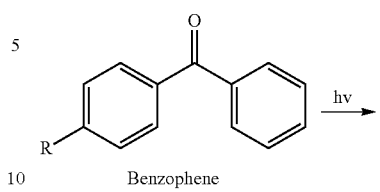
Benzophene
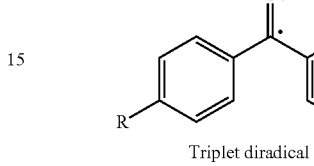
Cross-Link Product
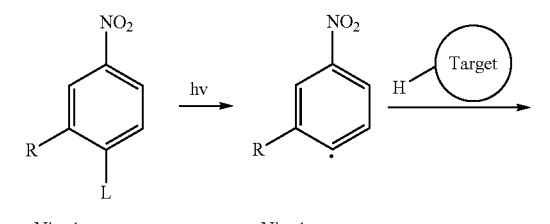
Nitrobenzene
L = Leaving Group
L = OR, F, Cl, Br, I
Nitrobenzene
Triplet
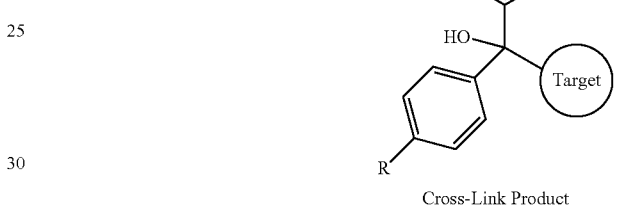
Triplet diradical
Cross-Link Product
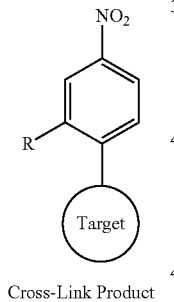
Cross-Link Product
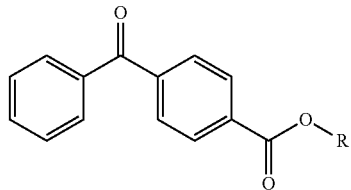
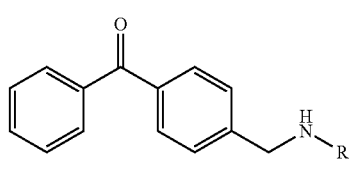
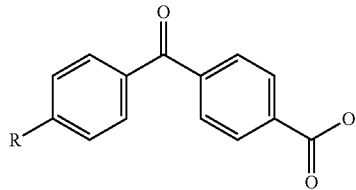
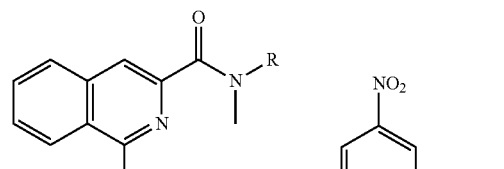
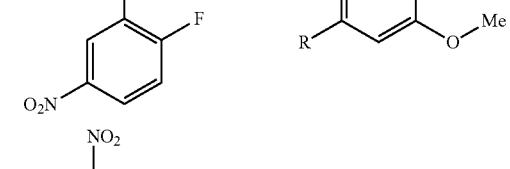

179
-continued
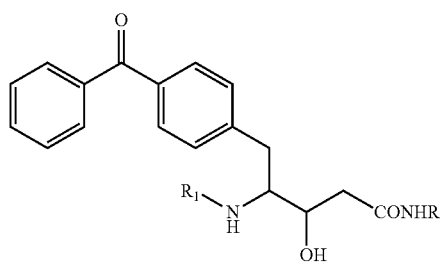
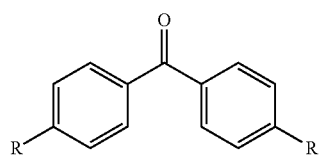
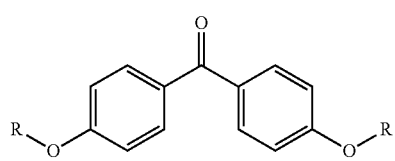
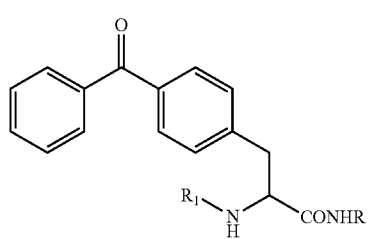
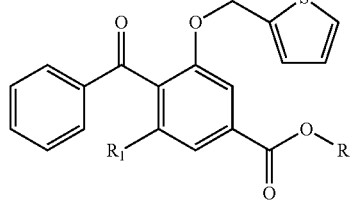
f) Enones
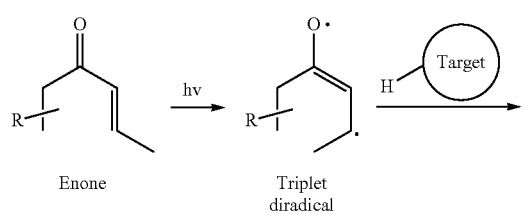
Enone → Triplet diradical
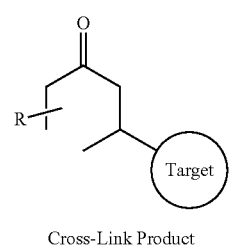
Cross-Link Product
180
-continued
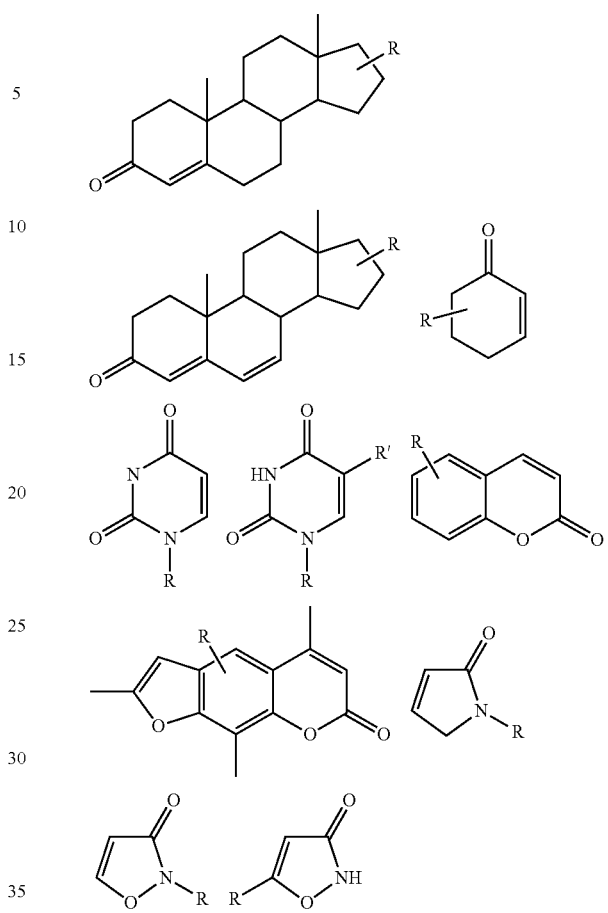
g) Thiobenzyl Compounds
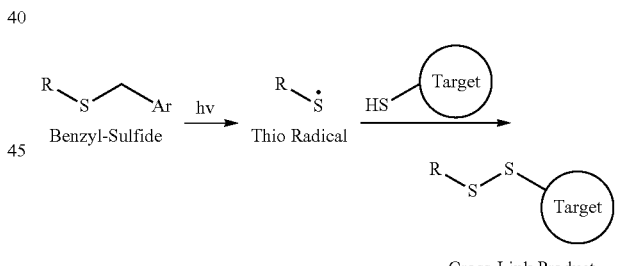
Benzyl-Sulfide → Thio Radical
Cross-Link Product
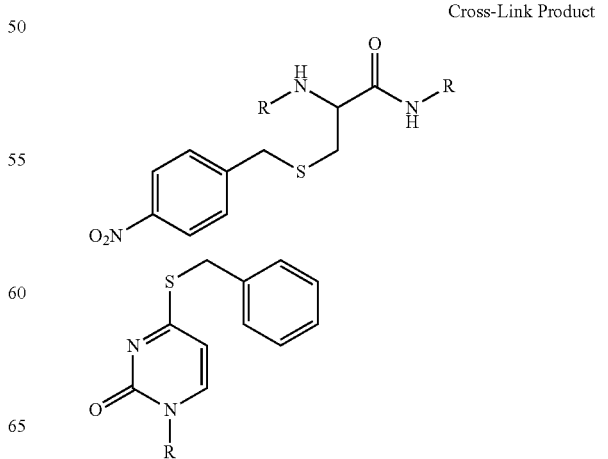

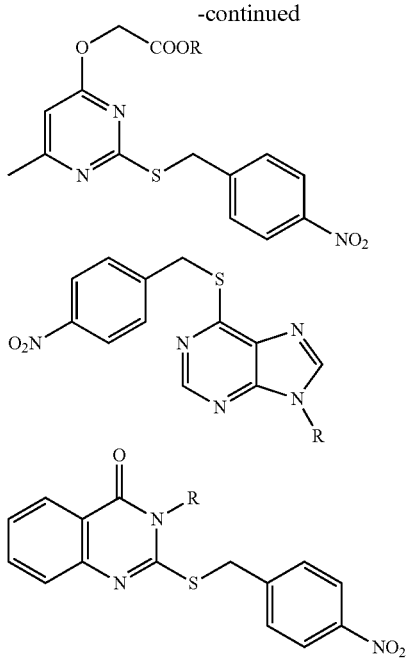

The method can, for example, comprise preparing a plurality of mixtures of the biological target molecule with at least one of the molecules. The methods of the present invention can also, for example, comprise preparing a mixture of the biological target molecule with a plurality of the molecules.

The method can, for example, further comprise the step of assaying the biological activity of one or more, and in some embodiments of the invention at least two, molecules against the biological target molecule. The assay may, for example, be a biochemical activity assay, or, for example, a biophysical assay, such as, for example, a binding assay, including, for example, but not limited to, an assay that comprises the use of mass spectroscopy. The biological activity assay may, for example, be conducted before, after, or simultaneously with obtaining the structure of the molecule in association with the biological target molecule.

In one example, a subset of the molecules or compounds assayed in the biological activity assay are selected for the structure determination step. In another example, a subset of the molecules or compounds used in the structure determination step are assayed in the biological activity assay. In one embodiment of the invention, the structure is determined using a method comprising X-ray crystallography. In one example, the methods of the present invention can further comprise the step of analyzing the binding of one or more, and in some embodiments of the invention at least two, molecules to the biological target molecule using a computational method.

In another example, the methods of the present invention can further comprise the steps of selecting or otherwise using information about the structures to design at least one second library, wherein the second library is derived from at least one molecule of the molecule library; and comprises compounds having modifications in at least one of the reactive compound building blocks of the scaffolded molecule. The method can, for example, further comprise the step of assaying the biological activity of one or more, and in some embodiments of the invention at least two, of the compounds against the biological target molecule.

The present invention also provides a method of designing a lead candidate having activity against a biological target molecule, comprising obtaining a library of bi-functional complexes of the present invention, determining the structures of at least one compound of the library in association with the biological target molecule, and selecting information from the structure to design at least one lead candidate.

The present invention also comprises methods where the molecule library can be screened against a first biological target molecule and eventually developed for activity against a second biological molecule. In some aspects of the invention, molecules or compounds found to have activity toward one biological target molecule can be screened against other biological target molecules where they may, for example, have the same or even enhanced activity. The second biological target molecule may, for example, be a related protein, and may, for example, be from the same protein family, for example, a protease, phosphatase, nuclear hormone receptor, or kinase family.

Thus, provided in the present invention is a method of designing a candidate compound having activity against a second biological target molecule, comprising obtaining a lead candidate of the present invention, determining the interaction of the lead candidate with a second biological target molecule; and designing at least one second library of compounds wherein each compound of the second library comprises a scaffold found in the lead candidate and modifications in at least one of the reactive compound building blocks on the scaffold.

In other methods of the invention, the molecule libraries are used in binding or biological activity assays before crystallization, and those molecules or compounds exhibiting a certain threshold of activity are selected for crystallization and structure determination. The binding or activity assay may also be performed at the same time as, or after, crystallization. Because of the ability to determine any complex structure, the threshold for determining whether a particular molecule is a hit can be set to be more inclusive than traditional high throughput screening assays, because obtaining a large number of false positives would not greatly negatively affect the process. For example, weak binders from a binding assay can be used in crystallization, and any false-positives easily weeded out. In other methods of the invention, the binding or biological activity assays can be performed after crystallization, and the information obtained, along with the structural data, used to determine the direction of the follow-up combinatorial library.

In one embodiment of the present invention, derivative compounds are selected from each library, wherein each such library comprises molecules with modifications at one reactive compound building block, resulting in a derived substituent, and for each library, the reactive compound building block that is modified is a different reactive compound building block, a new derivative compound is selected having the best-scoring reactive compound building blocks in one compound. This selected derivative compound can be used as the basis of a new round of library design and screening, or can be the basis of a more traditional combinatorial library. The selected derivative compound may also be subjected to computational elaboration, in that it may serve as the basis for the individual design of an improved compound for screening. The cycle continues until a new derivative compound is obtained that can be considered to be a lead compound, having a desired $IC_{50}$, and other desirable lead compound properties.

The present invention also provides methods for designing the molecule and compound libraries of the present invention. Provided in the present invention is a method of designing a molecule library for drug discovery, comprising screening or reviewing a list of synthetically accessible or commercially available molecules, and selecting molecules for the library wherein each of the molecules comprises: two or more reactive compound building blocks and preferably less than 25 non-hydrogen atoms. The molecules of the library may, for example, comprise, in their scaffold, at least one single or fused ring system. The molecules of the library may, for example, comprise in their scaffold at least one hetero atom on at least one ring system.

Also provided in the present invention is a method of screening for a molecule for use as a base molecule for library design, comprising obtaining a library of the present invention, screening the library for members having binding activity against a biological target molecule; and selecting a molecule of member(s) with binding activity to use as a base molecule for library design.

Also provided in the present invention are lead candidates and candidate compounds obtained by the methods of the present invention, libraries obtained by the methods of the present invention, and libraries comprising compounds with molecules selected by the methods of the present invention.

The present invention also provides a method of designing a lead candidate having biophysical or biochemical activity against a biological target molecule, comprising obtaining the structure of the biological target molecule bound to a molecule, wherein the molecule comprises a substituent having anomalous dispersion properties, synthesizing a lead candidate molecule comprising the step of replacing a reactive compound building block or derived substituent on the compound with a substituent comprising a functionalized carbon, nitrogen, oxygen, sulfur, or phosphorus atom, and assaying the lead candidate molecule for biophysical or biochemical activity against the biological target molecule.

The present invention also provides a method of designing a lead candidate having biophysical or biochemical activity against a biological target molecule, comprising combining a biological target molecule with a mixture comprising one or more, and in some embodiments of the invention at least two, molecules or compounds, wherein at least one of the molecules or compounds comprises a substituent having anomalous dispersion properties, identifying a molecule bound to the biological target molecule using the anomalous dispersion properties of the substituent, synthesizing a lead candidate molecule comprising the step of replacing the anomalous dispersion substituent with a substituent comprising a functionalized carbon or nitrogen atom, and assaying the lead candidate molecule for biophysical or biochemical activity against the biological target molecule.

Selection Steps and Further Down-Stream Processing Steps

Once a library of bi-functional complexes has been synthesised in accordance with the methods of the present invention, it is possible to select and/or screen and/or partition and/or purify the library in order to identify or isolate compounds with desirable features or properties from the library. The obtained compounds are in one embodiment small, scaffolded molecules.

The terms select and/or selection are used in the genetic sense; i.e. a biological process whereby a phenotypic characteristic is used to enrich a population for those organisms displaying the desired phenotype The selection or partitioning may be based on one or more features or properties of a molecule. Such a feature may be associated with or reside in a bi-functional molecule or a part of or a combination of parts of the encoded small molecule, the linker, or the identifier. Partitioning may be based on structural, chemical, or electronic features of a molecule. Partitioning may be based on a feature of a molecule or one or more parts of the molecule such as affinity for a target, hydrophobicity, hydrophilicity, charge distribution, size, mass, volume, conductivity, electric resistance, reactivity under certain conditions such as bond formation to a target, effect of the molecule such as induction of a signal in a system, e.g. a biochemical system, a biological system such as cell or a whole organism. The feature may be present in the molecule or it may be induced by the addition of a cofactor, e.g. a metal ion to the molecule.

A number of screening methods exist, for the identification of molecules, e.g. organic molecules such as the encoded molecule part of a bi-functional complex or the oligonucleotide tag part of a bi-functional complex, with desired characteristics. Different types of selection or screening protocols are described in (Rasmussen (2006) WO 06/053571A2, Liu et al. (2002), WO 02/074929 A2; Pedersen et al. (2002) WO 02/103008 A2; Pedersen et al. (2003) WO03/078625 A2; Lerner et al., EP 0643778 B1, Encoded combinatorial chemical libraries; Dower et al., EP 0604552 B1; Freskgard et al., WO 2004/039825 A2; Morgan et al., 2005, WO 2005/058479; Harbury and Halpin, WO 00/23458). For example, affinity selections may be performed according to the principles used in library-based selection methods such as phage display, polysome display, and mRNA-fusion protein displayed peptides. The template-directed synthesis of the invention permits selection procedures analogous to other display methods such as phage display (Smith (1985) SCIENCE 228: 1315-1317). Phage display selection has been used successfully on peptides (Wells et al. (1992) CURR. OP. STRUCT. BIOL. 2: 597-604), proteins (Marks et al. (1992) J. BIOL. CHEM. 267: 16007-16010) and antibodies (Winter et al. (1994) ANNU. REV. IMMUNOL. 12: 433-455). Similar selection procedures are also exploited for other types of display systems such as ribosome display Mattheakis et al. (1994) PROC. NATL. ACAD. Sci. 91: 9022-9026) and mRNA display (Roberts, et al. (1997) PROC. NATL. ACAD. Sci. 94: 12297-302).

The invention also relates to a method for identifying a molecule having a preselected property, comprising the steps of: subjecting the library produced according to the method indicated above to a condition, wherein a molecule or a subset of molecules having a predetermined property is partitioned from the remainder of the library, and identifying the molecule(s) having a preselected function by decoding the identifier oligonucleotide of the complex.

The above method, generally referred to as selection or screening, involves that a library is subjected to a condition in order to select molecules having a property which is responsive to this condition. The condition may involve the exposure of the library to a target e.g to identify ligands for a particular target. In the present context, a ligand is a substance that is able to bind to and form a complex with a biomolecule. The bi-functional complexes or ligands having an affinity towards this target can be partitioned form the remainder of the library by removing non-binding complexes and subsequent eluting under more stringent conditions the complexes that have bound to the target. Alternatively, the identifier oligonucleotide of the bi-functional complex can be cleaved from the molecule after the removal of non-binding complexes and the identifier oligonucleotide can be recovered and decoded to identify the molecule.

Specific screening methods employing bifunctional molecules for the identification of organic molecules with desired characteristics include but are not limited to:

i. Affinity selection on immobilised target molecules. In this approach the target molecules (e.g., DNA, RNA, protein, peptide, carbohydrate, organic or inorganic molecule, supramolecular structure or any other molecule, is immobilized covalently or non-covalently to a solid support such as beads, the bottom of a well of a microtiter plate, a reagent tube, a chromatographic column, or any other type of solid support. A library of bi-functional molecules are now incubated with the immobilized target molecule, excess non-bound bi-functional molecules are washed off by replacing the supernatant or column buffer with buffer not containing bi-functional molecules one or more times. After washing, the bound bi-functional molecules are released from solid support by addition of reagents, specific ligands or the like that results in the elution of the bi-functional molecule, or the pH is increased or decreased to release the bound bi-functional molecules, or the identifier of the bi-functional molecule, e.g., one or both strands of the identifier, is released from the encoded molecule with a reagent, pH change or light-induced cleavage. The recovered identifiers can now optionally be amplified by PCR, optionally cloned and sequenced to reveal the structure of the ligands encoded by the identifier. As an alternative, the identifiers or bi-functional molecules comprising identifiers, are not released from solid support, but rather the identifiers are optionally amplified by PCR and/or analyzed directly while still immobilised on solid support. Selection of binding molecules from a library can be performed in any format to identify optimal binding molecules. Binding selections typically involve immobilizing the desired target molecule, adding a library of potential binders, and removing non-binders by washing. When the molecules showing low affinity for an immobilized target are washed away, the molecules with a stronger affinity generally remain attached to the target. The enriched population remaining bound to the target after stringent washing is preferably eluted with, for example, acid, chaotropic salts, heat, competitive elution with a known ligand or by proteolytic release of the target and/or of template molecules. The eluted templates are suitable for PCR, leading to many orders of amplification, whereby essentially each selected template becomes available at a greatly increased copy number for cloning, sequencing, and/or further enrichment or diversification. In a binding assay, when the concentration of ligand is much less than that of the target (as it would be during the selection of a DNA-templated library), the fraction of ligand bound to target is determined by the effective concentration of the target protein. The fraction of ligand bound to target is a sigmoidal function of the concentration of target, with the midpoint (50% bound) at [target]=Kd of the ligand-target complex. This relationship indicates that the stringency of a specific selection—the minimum ligand affinity required to remain bound to the target during the selection—is determined by the target concentration. Therefore, selection stringency is controllable by varying the effective concentration of target. The target molecule (peptide, protein, DNA or other antigen) can be immobilized on a solid support, for example, a container wall, a wall of a microtiter plate well. The library preferably is dissolved in aqueous binding buffer in one pot and equilibrated in the presence of immobilized target molecule. Non-binders are washed away with buffer. Those molecules that may be binding to the target molecule through their attached DNA templates rather than through their synthetic moieties can be eliminated by washing the bound library with unfunctionalized templates lacking PCR primer binding sites. Remaining bound library members then can be eluted, for example, by denaturation. The target molecule can be immobilized on beads, particularly if there is doubt that the target molecule will adsorb sufficiently to a container wall, as may be the case for an unfolded target eluted from an SDS-PAGE gel. The derivatized beads can then be used to separate high-affinity library members from nonbinders by simply sedimenting the beads in a benchtop centrifuge. Alternatively, the beads clan be used to make an affinity column. In such cases, the library is passed through the column, one or more times to permit binding. The column is then washed to remove nonbinding library members. Magnetic beads are essentially a variant on the above; the target is attached to magnetic beads which are then used in the selection. There are many reactive matrices available for immobilizing the target molecule, including matrices bearing —NH2 groups or —SH groups. The target molecule can be immobilized by conjugation with NHS ester or maleimide groups covalently linked to Sepharose beads and the integrity of known properties of the target molecule can be verified. Activated beads are available with attachment sites for —NH2 or —COOH groups (which can be used for coupling). Alternatively, the target molecule is blotted onto nitrocellulose or PVDF. When using a blotting strategy, the blot should be blocked (e.g., with BSA or similar protein) after immobilization of the target to prevent nonspecific binding of library members to the blot.

ii. Affinity selection on target molecules in solution, followed by any means of isolation of the bi-functional molecules bound to the target, e.g. by immunoprecipitation of the target-bi-functional molecule complexes, capture of the complexes on nitrocellulose filter or by immobilisation of the target via a functionality on the target such as biotin or GST-oligonucleotide tag or Histidine-oligonucleotide tag or other useful means for immobilization as recognized by a person skilled in the art. A library of bi-functional molecules are incubated with target molecules (e.g. a protein). After complex formation of bi-functional molecules with target, the complex is isolated from non-complexes, for example by the addition of polyvalent antibodies against the target molecule and precipitation of antibody-target-bi-functional molecule complexes, or is precipitated by the addition of beads that bind the target molecules. The latter may for example be by addition of streptavidin-coated beads that bind to pre-biotinylated targets. The identifiers recovered by precipitation can now be characterised or amplified, e.g., by PCR, as described in (i). The sequence of the identifiers will reveal the identity of the encoded molecules that bind the target molecules.

iii. Affinity selection on target molecules in solution, followed by gel retardation, chromatographic separation e.g. size exclusion chromatography, or separation by centrifugation e.g. in a $CsCl_2$-gradient. A library of bi-functional molecules are incubated with target molecules (e.g. a protein). After complex formation of bi-functional molecules with target, the complex is isolated from non-complexes, for example by gel electrophoresis or size exclusion chromatography, or any other chromatographic or non-chromatographic method that separates the target-bi-functional molecule complexes from non-complexed bi-functional molecules, for example based on the difference in size and/or charge. The oligonucleotide tags of the bi-functional molecules of the column fraction or band on the gel that comprises target-bi-functional molecule complexes are now characterised or amplified, e.g., by PCR, as described above. The sequence of the oligonucleotide tags will reveal the identity of the encoded molecules that bind the target molecules.

iv. Affinity selection on surfaces. Particles, preferably small particles, of solid material, e.g., metal particles, metal oxide particles, grinded plastic, wood, preformed carbon nanotubes, clay, glas, silica, bacterial biofilm or biofilm of other microorganism, cement, solid paint particles, laminate, stone, marble, quartz, textile, paper, skin, hair, cell membranes, industrial membranes, epiderm, or the like, is added to a solution comprising a library of bi-functional molecules. After incubation, one or more washing steps are performed, to remove unbound bi-functional molecules. Then, the bi-functional molecules bound to the surface, or the identifiers of the bi-functional molecules bound to the surface, are released as described above, and the identifiers characterised and/or amplified as described above.

v. Selection for intracellularisation and transepithelial transport. To investigate intracellularisation of bi-functional molecules, the bi-functional molecules to be investigated are incubated with cells or micelles, or on one side of a lipid membrane, in order to allow the bi-functional molecule to pass or become immobilized in the membranes. Likewise, one can investigate the ability of bi-functional molecules to traverse cell monolayers (e.g. CaCo2 cell monolayer or other epithelial cell monolayers) by incubating bi-functional molecules on one side of an epithelial cell monolayer and selecting molecules that are able to pass the cell monolayer either by way of paracellular or transcellular transport. Paracellular transport refers to the transfer of molecules between cells of an epithelium and transcellular transport refers to when the molecules travel through the cell, passing through both the apical membrane and basolateral membrane. Then, a number of washing steps are performed in order to remove bi-functional molecules that have not become immobilized or have passed the membrane or cell monolayer. Identifiers from bi-functional molecules that have become immobilized or have passed the membrane or cell monolayer are now amplified and/or characterized as described above. The encoded molecule of bi-functional molecules that have either become immobilized in the membrane or have passed the membrane or cell monolayer, represent potential transporters for intracellularization and transcellular transport, i.e. by attaching these encoded molecules (without the oligonucleotide tag) to e.g. non-oral drugs, these may become orally available, because the transporter can mediate their transport across cell membranes and/or epithelia.

vi. Selection by phase partitioning. A two- or three phase system may be set up, wherein the bi-functional molecules will partition out according (at least in part) to the characteristics of the encoded molecules. Therefore, the principle allows the identification of encoded molecules that have particular preference for a certain kind of solvent. Again, the identifiers of the isolated bi-functional molecules can be amplified and/or characterised after the selection has occurred. It may be necessary to coat the nucleic acid component of the bi-functional molecule with e.g. DNA binding proteins, in order to ensure that the partitioning of the bi-functional molecule is significantly correlated with the characteristics of the encoded molecule of the bi-functional molecule.

vii. Selection for induced dimerisation of target molecules. In a preferred embodiment, encoded molecules are sought that induce the dimerization of target molecules. For example, small molecules with the potential to induce dimerization of protein receptors in the cell membrane may be applicable as therapeutics. Thus, a selection protocol for encoded molecules with the potential to induce dimerization of proteins A and B is as follows: A library of bi-functional molecules are incubated with proteins A and B. After incubation, and optional step of stabilising the protein dimer is performed e.g by cross-linking the proteins of the formed dimer. The solution is then applied to gel electrophoresis, ultracentrifugation (e.g. CsCl-centrifugation), size exclusion chromatography, or any other kind of separation that separates the protein A-protein B-bi-functional molecule-complex from un-complexed protein A and B, and other undesired complexes, such as protein A-protein B-complex. Bi-functional molecules from the band or fraction corresponding to the size and/or charge of the protein A-protein B-bi-functional molecule-complex are recovered, and template identifiers are then amplified and/or characterised as described above. In this case, the encoded molecule would be resynthesized, and tested in a protein dimerisation assay for its effect on the dimerisation of protein A and B.

viii. Selection by iterative rounds of binding and elution. This is a modification of the methods reported previously (Doyon et al. (2003), J. Am. Chem. Soc., 125, 12372-12373, the content of which is incorporated herein by reference in its entirety). Bi-functional molecules are incubated with e.g. immobilised target molecule, e.g. a biotinylated enzyme immobilised on streptavidin beads. After washing one or more times, the bound bi-functional molecules are released from solid support by a change in pH, addition of a detergent such as SDS, or by addition of an excess of ligand that binds the target molecule (the ligand can be e.g. a small molecule, peptide, DNA aptamer or protein that is known to bind the target molecule). Alternatively, the bi-functional molecules may be released by degradation of the immobilised target (e.g. by nuclease or protease), denaturation of target by methods such as heat or induced conformational changes in target structure or the like. The recovered bi-functional molecules are now re-applied to e.g. immobilised target molecule, optionally after removal or degradation of the ligand or reagent used for elution in the previous step. Again, washing is performed, and the bound bi-functional molecules eluted. The process of incubation and binding, washing and elution can be repeated many times, until eventually only bi-functional molecules of high affinity remains. Then the oligonucleotide tags of the bi-functional molecules are amplified and/or characterised. Using this kind of iterative binding and elution, enrichment factors higher than 1,000,000-fold can be obtained.

Targets may be immobilised on columns, on beads (batch selection), on the surface of a well, or target and ligands may interact in solution, followed by immunoprecipitation of the target (leading to immunoprecipitation of ligands bound to target). In one embodiment of iterative library pardoning step(s) the target concentration is kept constant at all selection steps. In another embodiment it may be desirable to change the target concentration between or during each or some partitioning steps. Consequently, the experimenter can choose the affinity thresholds for molecule recovery based on the molecules affinity for the target by altering the target concentration. E.g. a first selection step may employ a target concentration in the range of 1 to 50 uM (or even higher if practically allowed). Following selection and isolation of the library pool enriched for ligands the library pool is incubated with a target in reduced concentration such as in the range of 0.01 to 5 uM. A reduction in target concentration will enable the experimenter to increase the recovery of the best ligands in a library compared to molecules of lower affinity thereby achieving a better or more exact ranking of isolated ligands from the library pool based on ligand affinity (i.e the number of specific DNA-oligonucleotide tags isolated from the selection output correlate directly with molecule affinity for the target). In yet another embodiment, the ranking of ligands in a selection output is based on the off-rate of the target-molecule pair. Following the library incubation with immobilised target a specific ligand is added which saturate unbound target thus preventing rebinding of library molecules once released from it target binding site. This enables the experimenter to isolate library fractions eluted at different timepoints after target saturation resulting in primarily the isolation of molecules according to their off-rates (koff).

It is possible to perform a single or several rounds of selection against a specific target followed by subsequent amplification of the oligonucleotide tags of the selected bi-functional molecules. The obtained bi-functional molecules are then separately tested in a suitable assay. The selection condition can be stringent and specific to obtain high affinity binding molecules in a single selection round. It can be advantageous to perform the method using a single round of selection because the number and diversity of the potential binders are larger compared to procedures using further selections where potential binders can be lost. In another embodiment the selection procedure involves several rounds of selection using increasing stringency conditions. Between each selection an amplification of the selected complexes can be desirable.

x. Whole organism selection. A library of bi-functional molecules, optionally modified by e.g. coating proteins, is injected into a dead or living animal, for example a mouse. After incubation for a period of time (e.g two hours) in the animal, specific tissue or organs are recovered, and the bi-functional molecules associated with specific organs can be characterised, by e.g. PCR amplification and/or sequencing of the corresponding identifiers. As a specific example, a mouse carrying a tumor can be injected with a library of bi-functional molecules. After incubation, the tumor can be isolated from the animal. The bi-functional molecules associated with the tumor are potential therapeutics or diagnostics for that cancer.

The abovementioned target molecules may be of any supramolecular structure (e.g. nanoclusters, multiprotein complex, ribosomes), macromolecule (e.g. DNA, RNA, protein, polymers such as carbohydrates, thiophenes, fibrin), or low molecular weight compound (e.g. cAMP, small peptide hormones, chelates, morphine, drug). The target molecules may be biological or synthetic molecules as well as other organic and inorganic substances.

After having performed any of the selections above, the bi-functional molecules can taken through one more rounds of the same or another selection protocol. This process can be repeated until an appropriately small number of different bi-functional molecules are recovered. The appropriate number of bi-functional molecules to end up with after selection can be predetermined by the practitioner of the method.

The selection may be performed in the presence of one or more specific ligands for a particular site on a target. For example, if it is desired to avoid identification of ligands to a particular target site, known ligands to that site may be included during selection. The known ligand may then compete with bi-functional molecules for binding to the particular site thus reducing or eliminating binding of bi-functional molecules to the site. In this way, the bi-functional molecules will primarily be identified based on their affinity to other target sites and not the undesirable target site.

In another embodiment, the method of the present invention can be used to select bi-functional molecules that do not have a certain characteristic or feature. An example is to select bi-functional molecules that do not have affinity for certain targets, i.e. a selection for non-binders.

Once ligands are identified by any of the above-described processes, various levels of analysis can be applied to yield structure-activity relationship information and to guide further optimization of the affinity, specificity and bioactivity of the ligand. For ligands derived from the same scaffold, three-dimensional molecular modeling can be employed to identify significant structural features common to the ligands, thereby generating families of small-molecule ligands that presumably bind at a common site on the target biomolecule.

A variety of screening approaches can be used to obtain ligands that possess high affinity for one target but significantly weaker affinity for another closely related target. One screening strategy is to identify ligands for both biomolecules in parallel experiments and to subsequently eliminate common ligands by a cross-referencing comparison. In this method, ligands for each biomolecule can be separately identified as disclosed above. This method is compatible with both immobilized target biomolecules and target biomolecules free in solution. For immobilized target biomolecules, another strategy is to add a preselection step that eliminates all ligands that bind to the non-target biomolecule from the library. For example, a first biomolecule can be contacted with a library of bi-functional complexes as described above. Compounds which do not bind to the first biomolecule are then separated from any first biomolecule-ligand complexes which form. The second biomolecule is then contacted with the compounds which did not bind to the first biomolecule. Compounds which bind to the second biomolecule have significantly greater affinity for the second biomolecule than to the first biomolecule.

A ligand for a biomolecule of unknown function which is identified by the method disclosed above can also be used to determine the biological function of the biomolecule. This is advantageous because although new gene sequences continue to be identified, the functions of the proteins encoded by these sequences and the validity of these proteins as targets for new drug discovery and development are difficult to determine and represent perhaps the most significant obstacle to applying genomic information to the treatment of disease. Target-specific ligands obtained through the process described in this invention can be effectively employed in whole cell biological assays or in appropriate animal models to understand both the function of the target protein and the validity of the target protein for therapeutic intervention. This approach can also confirm that the target is specifically amenable to small molecule drug discovery. In one embodiment one or more compounds within a library of the invention are identified as ligands for a particular biomolecule. These compounds can then be assessed in an in vitro assay for the ability to bind to the biomolecule. Preferably, the molecules are synthesized without the oligonucleotide tag, or identifier or linker moiety, and these molecules are assessed for the ability to bind to the biomolecule.

The effect of the binding of the molecule without the associated oligonucleotide identifier to the biomolecule on the function of the biomolecule can also be assessed using in vitro cell-free or cell-based assays. For a biomolecule having a known function, the assay can include a comparison of the activity of the biomolecule in the presence and absence of the ligand, for example, by direct measurement of the activity, such as enzymatic activity, or by an indirect measure, such as a cellular function that is influenced by the biomolecule. If the biomolecule is of unknown function, a cell which expresses the biomolecule can be contacted with the ligand and the effect of the ligand on the viability, function, phenotype, and/or gene expression of the cell can be assessed. The in vitro assay can be, for example, a cell death assay, a cell proliferation assay or a viral replication assay. For example, if the biomolecule is a protein expressed by a virus, a cell infected with the virus can be contacted with a ligand for the viral protein. The affect of the binding of the ligand to the protein on viral viability can then be assessed.

A ligand identified by the method of the invention can also be assessed in an in vivo model or in a human. For example, the ligand can be evaluated in an animal or organism which produces the biomolecule. Any resulting change in the health status (e.g., disease progression) of the animal or organism can be determined.

For a biomolecule, such as a protein or a nucleic acid molecule, of unknown function, the effect of a ligand which binds to the biomolecule on a cell or organism which produces the biomolecule can provide information regarding the biological function of the biomolecule. For example, the observation that a particular cellular process is inhibited in the presence of the ligand indicates that the process depends, at least in part, on the function of the biomolecule. Ligands identified using the methods of the invention can also be used as affinity reagents for the biomolecule to which they bind. In one embodiment, such ligands are used to effect affinity purification of the biomolecule, for example, via chromatography of a solution comprising the biomolecule using a solid phase to which one or more such ligands are attached. In addition to the screening of encoded libraries as described herein, other traditional drug discovery methods, such as phage display, differential display (mRNA display), and aptamer/SELEX, could benefit from the methods of the invention which eliminate the introduction of amplification errors and biases. For example, multiple rounds of selection using phage display (described in, for example, PCT Publication Nos. WO91/18980, WO91/19818, and WO92/18619, and U.S. Pat. No. 5,223,409, the entire contents of each of which are incorporated herein by reference) can cause host toxicity and, consequently, loss or under-representation of desired library members (see, e.g., Daugherty, P. S., et al. (1999) Protein Engineering 12(7):613-621 and Holt, LJ., et al. (2000) Nucleic Acids Res. 28(15):E72). Moreover, methods such as Systematic Evolution of Ligands by Exponential enrichment (also known as SELEX which is described in, for example, U.S. Pat. Nos. 5,654,151, 5,503, 978, 5,567,588 and 5,270,163, as well as PCT Publication Nos. WO 96/38579 and WO9927133A1, the entire contents of each of which are incorporated herein by reference) introduce biases due to the need for multiple rounds of selection, i.e., partitioning unbound nucleic acids from those nucleic acids which have bound specifically to a target molecule, and multiple rounds of amplification of the nucleic acids that have bound to the target by reverse transcription and PCR. Similarly, methods of selection like differential display (described in, for example, U.S. Pat. Nos. 5,580,726 and 5,700,644, the entire contents of each of which are incorporated herein by reference) rely on multiple rounds of PCR amplification which also leads to unequal representation of the clones in the library. Thus, the foregoing multi-step selection processes may benefit from the methods described herein which employ massively parallel sequencing approaches (such as, for example, a pyrophosphate-based sequencing method or a single molecule sequencing by synthesis method) which leads to the accurate identification of a compound with a desired biological activity without the need for any nucleic acid amplification.

After having performed any of the selections or partitioning steps described above, the oligonucleotide identifier of the selected bi-functional complexes can be amplified by PCR or other means. Information about the chemical composition of the molecule can be obtained indirectly by analysing the composition of identifier.

Taq Amplification

In one embodiment of the invention, the library of compounds comprising encoding oligonucleotides are amplified to increase the copy number of encoding oligonucleotide molecules prior to sequencing. Encoding oligonucleotides may be amplified by any suitable method of DNA amplification including, for example, temperature cycling-polymerase chain reaction (PCR) (see, e.g., Saiki, et al. (1995) Science 230:1350-1354; Gingeras, et al. WO 88/10315; Davey, et al. European Patent Application Publication No. 329,822; Miller, et al. WO 89/06700), ligase chain reaction (see, e.g., Barany (1991) Proc. Natl. Acad. Sci. USA 88:189-193; Barringer, et al. (1990) Gene 89:117-122), transcription-based amplification (see, e.g., Kwoh, et al. (1989) Proc. Natl. Acad. Sd. USA 86:1173-1177) isothermal amplification systems—self-sustaining, sequence replication (see, e.g., Guatelli, et al. (1990) Proc. Natl. Acad. ScL USA 87:1874-1878); the Qp replicase system (see, e.g., Lizardi, et al. (1988) BioTechnology 6: 1197-1202); strand displacement amplification (Walker, et al. (1992) Nucleic Acids Res 20(7):1691-6; the methods described by Walker, et al. {Proc. Natl. Acad. Sci. USA (1992) I:89(I):392-6; the methods described by Kievits, et al. (J Virol Methods (1991) 35(3): 273-86; "race" (Frohman, In: PCR Protocols: A Guide to Methods and Applications, Academic Press, NY (1990)); "one-sided PCR" (Ohara, et al. (1989) Proc. Natl. Acad. Sci. U.S.A. 86.5673-5677); "di-oligonucleotide" amplification, isothermal amplification (Walker, et al. (1992) Proc. Natl. Acad. Sci. U.S.A. 89:392-396), and rolling circle amplification (reviewed in U.S. Pat. No. 5,714,320).

In one embodiment, the library of compounds comprising encoding oligonucleotides is amplified prior to sequence analysis in order to minimize any potential skew in the population distribution of DNA molecules present in the selected library mix. For example, only a small amount of library is recovered after a selection step and is typically amplified using PCR prior to sequence analysis. PCR has the potential to produce a skew in the population distribution of DNA molecules present in the selected library mix. This is especially problematic when the number of input molecules is small and the input molecules are poor PCR templates. PCR products produced at early cycles are more efficient templates than covalent duplex library, and therefore the frequency of these molecules in the final amplified population may be much higher than in original input template.

Accordingly, in order to minimize this potential PCR skew, in one embodiment of the invention, a population of single-stranded oligonucleotides corresponding to the individual library members is produced by, for example, using one primer in a reaction, followed by PCR amplification using two primers. By doing so, there is a linear accumulation of single-stranded primer-extension product prior to exponential amplification using PCR, and the diversity and distribution of molecules in the accumulated primer-extension product more accurately reflect the diversity and distribution of molecules present in the original input template, since the exponential phase of amplification occurs only after much of the original molecular diversity present is represented in the population of molecules produced during the primer-extension reaction. Preferably, DNA amplification is performed by PCR. PCR amplification methods are described in detail in U.S. Pat. Nos. 4,683,192, 4,683,202, 4,800,159, and 4,965,188, and at least in PCR Technology: Principles and Applications, for DNA Amplification, H. Erlich, ed., Stockton Press, New York (1989); and PCR Protocols: A Guide to Methods and Applications, Innis et ah, eds., Academic Press, San Diego, Calif. (1990). The contents of all the foregoing documents are incorporated herein by reference. In one embodiment of the invention, PCR amplification of the template is performed on an oligonucleotide tag bound to a bead, and encapsulated with a PCR solution comprising all the necessary reagents for a PCR reaction. In another embodiment of the invention, PCR amplification of the template is performed on a soluble oligonucleotide tag (i.e., not bound to a bead) which is encapsulated with a PCR solution comprising all the necessary reagents for a PCR reaction. PCR is subsequently performed by exposing the emulsion to any suitable thermocycling regimen known in the art. In one embodiment, between 30 and 50 cycles, preferably about 40 cycles, of amplification are performed. It is desirable, but not necessary, that following the amplification procedure there be one or more hybridization and extension cycles following the cycles of amplification. In a another embodiment, between 10 and 30 cycles, or about 25 cycles, of hybridization and extension are performed, hi one embodiment, the template DNA is amplified until about at least two million to fifty million copies or about ten million to thirty million copies of the template DNA are immobilized per bead.

Following amplification of the encoding oligonucleotide tag, the emulsion is "broken" (also referred to as "demulsification" in the art). There are many well known methods of breaking an emulsion (see, e.g., U.S. Pat. No. 5,989,892 and references cited therein) and one of skill in the art would be able to select the proper method. For example, the emulsion may be broken by adding additional oil to cause the emulsion to separate into two phases. The oil phase is then removed, and a suitable organic solvent (e.g., hexanes) is added. After mixing, the oil/organic solvent phase is removed. This step may be repeated several times. Finally, the aqueous layers is removed. If the encoding oligonucleotides are attached to beads, the beads are then washed with an organic solvent/annealing buffer mixture, and then washed again in annealing buffer. Suitable organic solvents include alcohols such as methanol, ethanol and the like.

The amplified encoding oligonucleotides may then be resuspended in aqueous solution for use, for example, in a sequencing reaction according to known technologies. (See, e.g., Sanger, F. et al. (1977) Proc. Natl. Acad. Sd. U.S.A. 75:5463-5467; Maxam & Gilbert (1977) Proc Natl Acad Sd USA 74:560-564; Ronaghi, et al. (1998) Science 281: 363, 365; Lysov, et al. (1988) DoklAkadNauk SSSR 303:1508-1511; Bains & Smith (1988) J TheorBiol 135:303-307; Drnanac, R. et al. (1989) Genomics 4:114-128; Khrapko, et al (1989) FEBS Lett 256:118-122; Pevzner (1989) J Biomol Struct Dyn 7:63-73; Southern, et al. (1992) Genomics 13:1008-1017).

If the encoding oligonucleotide attached to a bead is to be used in a pyrophosphate-based sequencing reaction (described, e.g., in U.S. Pat. Nos. 6,274,320, 6,258,568 and 6,210,891, and incorporated herein by reference), then it is necessary to remove the second strand of the BCR product and anneal a sequencing primer to the single stranded template that is bound to the bead.

Briefly, the second strand is melted away using any number of commonly known methods such as NaOH, low ionic {e.g., salt) strength, or heat processing. Following this melting step, the beads are pelleted and the supernatant is discarded. The beads are resuspended in an annealing buffer, the sequencing primer added, and annealed to the bead-attached single stranded template using a standard annealing cycle.

The amplified encoding oligonucleotide, optionally on a bead, may be sequenced either directly or in a different reaction vessel. In one embodiment of the present invention, the encoding oligonucleotide is sequenced directly on the bead by transferring the bead to a reaction vessel and subjecting the DNA to a sequencing reaction {e.g., pyrophosphate or Sanger sequencing). Alternatively, the beads may be isolated and the encoding oligonucleotide may be removed from each bead and sequenced. Nonetheless, the sequencing steps may be performed on each individual bead and/or the beads that contain no nucleic acid template may be removed prior to distribution to a reaction vessel by, for example, biotin-streptavidin magnetic beads. Other suitable methods to separate beads are described in, for example, Bauer, J. (1999) J. Chromatography B, 722:55-69 and in Brody et al. (1999) Applied Physics Lett. 74:144-146.

Once the encoding oligonucleotide tag has been amplified, the sequence of the tag, and ultimately the composition of the selected molecule, can be determined using nucleic acid sequence analysis, a well known procedure for determining the sequence of nucleotide sequences. Nucleic acid sequence analysis is approached by a combination of (a) physiochemical techniques, based on the hybridization or denaturation of a probe strand plus its complementary target, and (b) enzymatic reactions with polymerases.

The nucleotide sequence of the oligonucleotide tag comprised of polynucleotides that identify the building blocks that make up the functional moiety as described herein, may be determined by the use of any sequencing method known to one of skill in the art. Suitable methods are described in, for example, Sanger, F. et al. (1977) Proc. Natl. Acad. Sd. U.S.A. 75:5463-5467; Maxam & Gilbert (1977) Proc Natl Acad Sd USA 74:560-564; Ronaghi, et al. (1998) Science 281:363, 365; Lysov, et al. (1988) DoM Akad Nauk SSSR 303:1508-1511; Bains & Smith (1988) JTheorBiol 135:303-307; Drnanac, R. et al. (1989) Genomics 4:114-128; Khrapko, et al. (1989) FEBS Lett 256:118-122; Pevzner (1989) J Biomol Struct Dyn 7:63-73; Southern, et al. (1992) Genomics 13:1008-1017).

In a preferred embodiment, the oligonucleotide tags are sequenced using the apparati and methods described in PCT publications WO 2004/069849, WO2005/003375, WO 2005/073410, and WO 2005/054431, the entire contents of each of which are incorporated herein by this reference. In one embodiment, a region of the sequence product is determined by annealing a sequencing primer to a region of the template nucleic acid, and then contacting the sequencing primer with a DNA polymerase and a known nucleotide triphosphate, i.e., dATP, dCTP, dGTP, dTTP, or an analog of one of these nucleotides, such as, for example, [alpha]-thio-dATP. The sequence can be determined by detecting a sequence reaction byproduct, using methods known in the art. In some embodiments, the nucleotide is modified to contain a disulfide-derivative of a hapten, such as biotin. The addition of the modified nucleotide to the nascent primer annealed to an anchored substrate is analyzed by a suitable post-polymerization method. Such methods enable a nucleotide to be identified in a given target position, and the DNA to be sequenced simply and rapidly while avoiding the need for electrophoresis and the use of potentially dangerous radiolabels.

Examples of suitable haptens include, for example, biotin, digoxygenin, the fluorescent dye molecules cy3 and cy5, and fluorescein. The attachment of the hapten can occur through linkages via the sugar, the base, and/or via the phosphate moiety on the nucleotide. Exemplary means for signal amplification following polymerization and extension of the encoding oligonucleotide include fluorescent, electrochemical and enzymatic means. In one embodiment using enzymatic amplification, the enzyme is one for which light-generating substrates are known, such as, for example, alkaline phosphatase (AP), horse-radish peroxidase (HRP), beta-galactosidase, or luciferase, and the means for the detection of these light-generating (chemiluminescent) substrates can include a CCD camera.

A sequencing primer can be of any length or base composition, as long as it is capable of specifically annealing to a region of the nucleic acid template (i.e., the oligonucleotide tag). The oligonucleotide primers of the present invention may be synthesized by conventional technology, e.g., with a commercial oligonucleotide synthesizer and/or by ligating together subfragments that have been so synthesized. No particular structure for the sequencing primer is required so long as it is able to specifically prime a region on the template nucleic acid. The sequencing primer is extended with the DNA polymerase to form a sequence product. The extension is performed in the presence of one or more types of nucleotide triphosphates, and if desired, auxiliary binding proteins. Incorporation of the dNTP is determined by, for example, assaying for the presence of a sequencing byproduct.

In one embodiment, the nucleic acid sequence of the oligonucleotide tag is determined by the use of the polymerase chain reaction (PCR). Briefly, the oligonucleotide tag (optionally attached to a bead) is subjected to a PCR reaction as follows. The appropriate sample is contacted with a PCR primer pair, each member of the pair having a pre-selected nucleotide sequence. The PCR primer pair is capable of initiating primer extension reactions by hybridizing to a PCR primer binding site on the encoding oligonucleotide tag. The PCR reaction is performed by mixing the PCR primer pair, preferably a predetermined amount thereof, with the nucleic acids of the encoding oligonucleotide tag, preferably a predetermined amount thereof, in a PCR buffer to form a PCR reaction admixture. The admixture is thermocycled for a number of cycles, which is typically predetermined, sufficient for the formation of a PCR reaction product. A sufficient amount of product is one that can be isolated in a sufficient amount to allow for DNA sequence determination.

PCR is typically carried out by thermocycling i.e., repeatedly increasing and decreasing the temperature of a PCR reaction admixture within a temperature range whose lower limit is about 30° C. to about 55° C. and whose upper limit is about 90° C. to about 100° C. The increasing and decreasing can be continuous, but is preferably phasic with time periods of relative temperature stability at each of temperatures favoring polynucleotide synthesis, denaturation and hybridization.

The PCR reaction is performed using any suitable method. Generally it occurs in a buffered aqueous solution, i.e., a PCR buffer, preferably at a pH of from about 7 to about 9.

Preferably, a molar excess of the primer is present. A large molar excess is preferred to improve the efficiency of the process.

The PCR buffer also contains the deoxyribonucleotide triphosphates (polynucleotide synthesis substrates) dATP, dCTP, dGTP, and dTTP and a polymerase, typically thermostable, all in adequate amounts for primer extension (polynucleotide synthesis) reaction. The resulting solution (PCR admixture) is heated to about 90° C.-100° C. for about 1 to 10 minutes, preferably from 1 to 4 minutes. After this heating period the solution is allowed to cool to 54° C., which is preferable for primer hybridization. The synthesis reaction may occur at a temperature ranging from room temperature up to a temperature above which the polymerase (inducing agent) no longer functions efficiently. Thus, for example, if DNA polymerase is used, the temperature is generally no greater than about 40° C. The thermocycling is repeated until the desired amount of PCR product is produced. An exemplary PCR buffer comprises the following reagents: 50 mM KCl; 10 mM Tris-HCl at pH 8.3; 1.5 mM $MgCl_2$; 0.001% (wt/vol) gelatin, 200 µM dATP; 200 µM dTTP; 200 µM dCTP; 200 µM dGTP; and 2.5 units *Thermus aquaticus* (Taq) DNA polymerase I per 100 microliters of buffer.

Suitable enzymes for elongating the primer sequences include, for example, *E. coli* DNA polymerase I, Taq DNA polymerase, Klenow fragment of *E. coli* DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. The newly synthesized DNA strand and its complementary strand form a double-stranded molecule which can be used in the succeeding steps of the analysis process.

In one embodiment, the nucleotide sequence of the oligonucleotide tag is determined by measuring inorganic pyrophosphate (PPi) liberated from a nucleotide triphosphate (dNTP) as the dNMP is incorporated into an extended sequence primer. This method of sequencing, termed Pyrosequencing(TM) technology (PyroSequencing AB, Stockholm, Sweden) can be performed in solution (liquid phase) or as a solid phase technique. PPi-based sequencing methods are described in, e.g., U.S. Pat. Nos. 6,274,320, 6,258,568 and 6,210,891, WO9813523A1, Ronaghi, et al. (1996) Anal Biochem. 242:84-89, Ronaghi, et al. (1998) Science 281: 363-365, and USSN 2001/0024790. These disclosures of PPi sequencing are incorporated herein in their entirety, by reference. See also, e.g., U.S. Pat. Nos. 6,210,891 and 6,258,568, each of which are fully incorporated herein by this reference.

Pyrophosphate can be detected by a number of different methodologies, and various enzymatic methods have been previously described (see e.g., Reeves, et al. (1969) Anal Biochem. 28:282-287; Guillory, et al. (1971) Anal Biochem. 39:170-180; Johnson, et al. (1968) Anal Biochem. 15:273; Cook, et al. 1978. Anal Biochem. 91:557-565; and Drake, et al. (1919) Anal Biochem. 94: 117-120).

In one embodiment, PPi is detected enzymatically (e.g., by the generation of light). Such methods enable a nucleotide to be identified in a given target position, and the DNA to be sequenced simply and rapidly while avoiding the need for electrophoresis and the use of potentially dangerous radiolabels.

In one embodiment, the PPi and a coupled luciferase-luciferin reaction is used to generate light for detection, hi another embodiment, the PPi and a coupled sulfurylase/luciferase reaction is used to generate light for detection as described in U.S. Pat. No. 6,902,921, the contents of which are hereby expressly incorporated herein by reference. In one embodiment, the sulfurylase is thermostable. In some embodiments, either or both the sulfurylase and luciferase are immobilized on one or more mobile solid supports disposed at each reaction site. In another embodiment, the nucleotide sequence of the oligonucleotide tag may be determined according to the methods described in PCT Publication No. WO 01/23610, the contents of which are incorporated herein by reference. Briefly, a target nucleotide sequence can be determined by generating its complement using the polymerase reaction to extend a suitable primer, and characterizing the successive incorporation of bases that generate the complement sequence. The target sequence is, typically, immobilized on a solid support. Each of the different bases A, T, G," or C is then brought, by sequential addition, into contact with the target, and any incorporation events are detected via a suitable label attached to the base.

A labeled base is incorporated into the complementary sequence by the use of a polymerase, e.g., a polymerase with a 3' to 5' exonuclease activity (e.g., DNA polymerase I, the Klenow fragment, DNA polymerase III, T4 DNA polymerase, and T7 DNA polymerase). Following detection of the incorporated labeled base, the polymerase replaces the terminally labeled base with a corresponding unlabelled base, thus permitting further sequencing to occur.

In yet another embodiment, the nucleotide sequence of the oligonucleotide tag is determined by the use of single molecule sequencing by synthesis methods described in, for example, PCT Publication No. WO 2005/080605, the entire contents of which are expressly incorporated by reference. The benefit of using this technology is that it eliminates the need for DNA amplification prior to sequencing, thus, abolishing the introduction of amplification errors and bias. Briefly, the encoding oligonucleotide is hybridized to a universal primer immobilized on a solid surface. The oligonucleotide:primer duplexes are visualized by, e.g., illuminating the surface with a laser and imaging with a digital TV camera connected to a microscope, and the positions of all the duplexes on the surface are recorded. DNA polymerase and one type of fluorescently labeled nucleotide, e.g., A, is added to the surface and incorporated into the appropriate primer. Subsequently, the polymerase and the unincorporated nucleotides are washed from the surface and the incorporated nucleotide is visualized by, e.g., illuminating the surface with a laser and imaging with a camera as before to record the positions of the incorporated nucleotides. The fluorescent label is removed from each incorporated nucleotide and the process is repeated with the next nucleotide, e.g., G, stepping through A, C, G, T, until the desired read-length is achieved.

One group of fluorescent dyes suitable for this method of sequencing is fluorescence resonance energy transfer (FRET) dyes, including donor and acceptor energy fluorescent dyes and linkers such as, for example, Cy3 and Cy5. FRET is a phenomenon described in, for example, Selvin (1995) Methods in Enzym. 246:300. FRET can detect the incorporation of multiple nucleotides into a single oligonucleotide molecule and is, thus, useful for sequencing the encoding oligonucleotides of the invention. Sequencing methods using FRET are described in, for example, PCT Publication No. WO 2005/080605, the entire contents of which are expressly incorporated by reference. Alternatively, quantum dots can be used as a labeling moiety on the different types of nucleotides for use in sequencing reactions.

In one embodiment of the present invention, structural information about a molecule forming part of a bi-functional complex can be obtained by way of analysing the nucleotide sequence of the oligonucleotide identifier. Structural information about a molecule can be obtained by the method comprising the steps of i) providing
   (A) at least one encoding oligonucleotide, each encoding oligonucleotide being the oligonucleotide identifier associated with a particular molecule of a bi-functional complex in said library, or a sequence complementary to said oligonucleotide identifier, and
   (B) an array comprising a plurality of at least partially single stranded decoding oligonucleotides of predetermined sequence immobilized in discrete areas of a solid support, wherein a single stranded portion of each decoding oligonucleotide is capable of hybridizing to at least one tag of at least one encoding oligonucleotide(s), ii) adding the encoding oligonucleotide(s), to the array under conditions which allow for specific hybridization, iii) observing the discrete areas of the support in which a specific hybridization event has occurred, wherein each observed specific hybridization event is indicative of a specific hybridization between one or more encoding oligonucleotide tags and a single stranded portion of a decoding oligonucleotide, wherein the predetermined sequence of each single stranded portion of a decoding oligonucleotide hybridizing to said one or more encoding oligonucleotide tags allows the identification of said one or more encoding oligonucleotide tags, wherein the identification of said one or more encoding oligonucleotide tags in turn allows the identification of one or more building blocks which have reacted and participated in the synthesis of the molecule part of the bi-functional complex, by reliance on knowledge of which identifier oligonucleotide tag encoded each building block of said set of building blocks in said process of producing said library, wherein the identification of a participating building block in turn allows identification of a structural entity of said molecule which was derived, in the course of synthesis of the molecule part of the bi-functional complex, from said building block, whereby said structural information about the molecule part of the bi-functional complex that is obtained comprises the identity of at least one such structural entity. In one embodiment of the above method for obtaining structural information about the molecule part of the bi-functional complex the decoding oligonucleotide comprises a single stranded nucleic acid probe directly immobilized on the support and a single stranded adapter oligonucleotide, said adapter oligonucleotide having a first sequence complementing the probe as well as a second sequence complementing one or more identifier oligonucleotide tags of the encoding oligonucleotide, said probe and said adapter oligonucleotide hybridizing together to form a decoding oligonucleotide that is partially double stranded.

The method of the present invention can further comprise a step of generating a second enriched library comprising a plurality of bi-functional complexes, the further method steps comprising the steps of:

i) providing an initial library of bi-functional complexes comprising a plurality of different bi-functional complexes, each bi-functional complex comprising a molecule associated with an oligonucleotide identifier, said identifier comprising a plurality of enzymatically connected identifier oligonucleotide tags, each tag identifying a particular reactive compound building block which has participated in the synthesis of the molecule to which the oligonucleotide identifier is associated, wherein said identifier oligonucleotide tags do not form part of an oligonucleotide identifier which has been synthesised prior to the synthesis of the molecule part of the bi-functional complex,
   ii) partitioning the initial library of bi-functional complexes provided in step i) by subjecting the initial library to a partitioning condition resulting in the partitioning from the initial library of a first enriched library comprising bi-functional complexes comprising molecules comprising a predetermined property, thereby obtaining a first enriched library,
   iii) determining the sequence and the relative amounts of the identifier oligonucleotide tags of the oligonucleotide identifiers of the bi-functional complexes of the first, enriched library,
wherein each identifier oligonucleotide tag identifies a particular reactive compound building block having participated in the synthesis of a molecule part of a partitioned, bi-functional complex of the first, enriched library,
   iv) determining the identity and relative amounts of the reactive compound building blocks encoded by identifier oligonucleotide tags identified in step iii),
   v) generating a second, enriched library by a method comprising the step of reacting at least a part of the reactive compound building blocks, the identity of which were determined in step iv),
wherein the reactive compound building blocks are employed for the synthesis of the second, enriched library in amounts different from those determined in step iv), thereby obtaining a second, enriched library of bi-functional complexes,
   vi) determining the sequence and the relative amounts of the identifier oligonucleotide tags of the oligonucleotide identifiers of the bi-functional complexes of the second, enriched library,
wherein each identifier oligonucleotide tag identifies a particular reactive compound building block having participated in the synthesis of a molecule part of a bi-functional complex of the second enriched library,
   vii) determining the identity and relative amounts of the reactive compound building blocks encoded by the identifier oligonucleotide tags of oligonucleotide identifiers of the bi-functional complexes of the second, enriched library as identified in step vi), said reactive compound building blocks having participated in the synthesis of molecules of the second enriched library, and
optionally identifying molecules of the second, enriched library which have been synthesized as a result of the reaction of said reactive compound building blocks.

An example of employing the reactive compound building blocks in amounts different from the relative amounts determined in the bi-functional complexes of the first, enriched library would be to apply the reactive compound building blocks in equimolar amounts when synthesizing the second, enriched library. In some instances, only a fraction of the reactive compound building blocks used for the synthesis of the second, enriched library are employed in equimolar amounts.

In some instances, all of the reactive compound building blocks identified as being present in the first, enriched library are employed in the synthesis of the second, enriched library. In other instances, less than all of the reactive compound building blocks identified as being present in the first, enriched library are employed in the synthesis of the second, enriched library.

In yet another instance, the second, enriched library can be synthesized by employing reactive compound building blocks not present in the first, enriched library. The employment of building blocks not present in the preceding library is known as "spiking" and can e.g. be advantageous when it is desired to include building blocks in the synthesis of the second, enriched library with certain features or characteristics which were not selected for in the partitioning step.

Polyvalent Display and Other Means of Increasing the Likelihood of Identifying Encoded Molecules with Weak Characteristics Under certain conditions the requirements of an encoded molecule, in order to be isolated during the screening step, are too strong, and few or none of the encoded molecules of a library are expected to fulfil the requirements. Such requirements may be for example high affinity or high catalytic turn-over. The methods and success of multivalent display in affinity selections is evident from systems similar to that described here such as phage display as should be recognized by persons skilled in the art Thus, it may be desirable to employ a multivalent display mode, i.e., to generate libraries of multivalent encoded molecules (multiple encoded molecules attached to one oligonucleotide tag). During a selection step in which for example an encoded molecule interacts weakly with a target protein, a multivalent encoded molecule may interact with multiple protein targets through the multiple copies of encoded molecules that it contains, and as a result, may bind with higher affinity because of the avidity effect. Likewise, in a screening or selection step for catalytic efficiency, a multivalent encoded molecule may generate more product in a given time, and may be isolated because of this.

A preferred means of generating libraries of multivalent encoded molecules each containing multiple copies of the same encoded molecule, is as follows: The DNAn oligonucleotide tag-piece (denoted "Third intermediate bi-functional complex" or "single-stranded identifier") employed for chemical reaction can be synthesised with 1 or more reactive handles using standard phosphoramidite chemistry. One strategy for the introduction of multivalent display involves the incorporation of doublers or treblers (such as Glen Research catalog No10-1920-90 or 10-1922-90) one or more times forming dendrimer structures that can be capped by reactive handles f.ex amino-, acid-, Thiol- or aldehyde-group (or any reactive compound building block useful as starting point in a chemical reaction. This enables the formation of a single DNA sequence connected to any number of reactive handles such as 1, 2, 3, 4, 5, 6, 7, 8, 9, 10, 11, 12, 13, 14, 15, 16, 17, 18, 19, 20 or more reactive handles. It may be desirable to include spacing groups such as polyethylene glycol (PEG) units at any point in the synthesis process (chosen by the experimenter) for improved synthesis and display of the synthetic molecule.

The multivalent encoded molecules can now be used in various screening or selection processes. For example, the multivalent encoded molecules may be added to an affinity column, to which target protein has been immobilised with an appropriately high density, so that multivalent encoded molecules may interact with several immobilised targets simultaneously. This will lead to the isolation of bi-functional complexes that contain encoded molecules with affinity for the immobilised target protein. The use of multivalent encoded molecules may be particularly advantageous to use when selecting for affinity to a homodimeric target molecule, or any other target that contains two or more identical binding sites. Relevant targets include membrane proteins such as the Epo-receptor, p53, HER2, Insulin Receptor, many interleukins, palindromic DNA- or RNA-sequences, or fibrin. Divalent encoded molecules containing identical encoded molecules are also appropriate for affinity selection on target molecules with one binding site, where the binding site is partly or fully symmetrical, and therefore allows two identical encoded molecules to interact.

In another embodiment the addition of a helper element comprising a helper molecule known to interact with the target, is linked to an oligonucleotide capable of hybridizing to a region on the DNA portion of the bi-functional library molecules may aid the isolation of a bi-functional molecule e.g. by increasing the overall affinity of the helper molecule/bi-functional molecule complex for the target. Hybridization of a second primer followed by polymerase extention and ligation will produce dsDNA displaying both the encoded library molecule and the helper molecule Consequently, if a ligand is known for a binding site in a protein, this ligand may be coupled to the bi-functional molecule, in order to guide the encoded molecule to the target protein, and in order to increase the affinity of the bi-functional molecule (carrying the known ligand) for the target protein Similar approaches may be used for isolation of encoded molecules with affinity for a target binding site, where the binding site can be occupied by both the encoded molecule and the known ligand simultaneously. Finally, it may be desirable to increase the overall affinity of the bi-functional molecule for the target by linking a short oligonucleotide that is complementary to the oligonucleotide tag of the bi-functional molecule to the target. The short oligonucleotide will then function as a helper moiety that increases the affinity of the bi-functional molecule for the target, by hybridisation of the short oligonucleotide to the bi-functional molecule.

Selections employing such bi-functional complexes to which have been attached a helper moiety may be applied to affinity selection against all kinds of targets, including protein-heterodimers as well as protein-homodimers, and thus molecular targets include HER2, Insulin-receptor, VEGF, EGF, IL-4, IL-2, TNF-alpha, the TATA-box of eukaryotic promoter regions, and many others.

In another embodiment, a target and the bi-functional complexes may be modified to allow screening. For example, an —SH group may be introduced in a protein target by muoligonucleotide tagenesis of an amino acid to a cysteine. Correspondingly, a library of bi-functional complexes may be synthesized such that encoded molecules carry an —SH group. Alternatively, a library may following synthesis be reacted with a reactive compound building block that carries an —SH group. Screenings may then be performed under conditions that induce the formation of an S—S bond between the —SH of the target and the —SH of the encoded molecules of the library. In this way, the bi-functional complexes may be directed to a specific site on the target.

Dynamic combinatorial library of dimers or trimers of encoded molecules. The bi-functional complexes of a library may be designed in a way that leads to transient complex formation between 2, 3, or more bi-functional complexes during the screening process. This may be desirable, especially in cases where the libraries that have been generated are relatively small, or in cases where it is desirable to screen a large number of combinations of encoded molecules for synergistic effects. In order to generate transient complexes, the bi-functional complexes may be designed so as to comprise half of a transient interaction pair. For example, a short single stranded oligonucleotide region may be included in the design of the oligonucleotide tag of the bi-functional complexes; if some of the bi-functional complexes carry a molecular entity "A" and some other bi-functional complexes of the library carry another molecular entity "B" that interacts transiently, i.e. forms a short-lived complex with, "A", then the two sets of bi-functional complexes of the library will form transient dimers of bi-functional molecules. These transient dimers may then be exposed to a screening process, for example affinity selection, where the dimers are then examined for ability to bind to a certain target. As an example, for each of the species of bi-functional molecules, half of the generated bi-functional complexes carry the oligo sequence 3'-ATGC-5' in the proximity of the encoded molecule, and the other half of the generated bi-functional complexes carry the oligo sequence 3'-GCTA-5'. When all the generated bi-functional complexes are incubated at appropriately low temperature, different combinations of dimers will transiently form, and allow for a feature displayed by the combination of the corresponding two encoded molecules to be selected for. This feature could be the binding of the two encoded molecules of the dimer to bind simultaneously to a target molecule. If appropriately designed, trimers may be (transiently) formed, by formation of triplex DNA between three bi-functional molecules. In this way, all the possible dimers (or trimers) of a pool of bi-functional complexes may be screened for the desired feature.

Once the screening of a library of bi-functional complexes has been done, the isolated bi-functional complexes may be identified. This can be done without DNA amplification or more preferably by use of PCR or other means of DNA amplification. Next, the structure of the molecules isolated can be identified from the oligonucleotide tag sequence directly using techniques such as pyrosequencing described by Margulies, M. et al (Nature. 2005 Sep. 15; 437(7057): 376-80) and incorporated herein by reference or by a probing technique described in WO2005093094 or other means of direct sequencing without cloning. Alternatively the oligonucleotide tags can be cloned and sequenced by conventional means such as Sanger sequencing, mass spectrometry-based sequencing, single molecule sequencing, or sequencing by hybridisation to oligonucleotide arrays.

The characteristics of the encoded molecules thus identified may now be analyzed, either in its free form (after resynthesis by organic chemistry or after generation of the bi-functional molecule followed by cleavage of the linker that connects the encoded molecule and its identifier) or in its oligonucleotide-linked form (as a bi-functional molecule).

QC of Library Generation

It may be desirable to test reaction efficiencies for the entire set- or a subset of chemical reactions. A simple method for evaluation of transformations efficiency is the use of Mass spectroscopy for analysis of library transformations. Consequently, a small sample of all reaction wells, a subset or of single wells may be collected and analysed directly by any analytical tool available such as MALDI-TOF MS or Electrospray MS. Alternatively the sample may be subjected to a number of methods for the aid of the analysis. In one embodiment it may be desirably to purify the identifier from unwanted DNA, reactive compound building blocks, buffers etc using methods such as HPLC/FPLC, gelfiltration, Ion-chromatography, Gel-electrophoresis or using immobilisation on solid-support followed by elution of the library product. Subsequently, the identifier DNA can be analysed using spectroscopic methods including but not limited to MALDI-TOF or ES-MS.

In some embodiments it may be necessary to apply additional methods for the simplification of the analytical step. Since each bi-functional complexes generated by the library generation process contains both a DNA part and a chemical part, all samples following the first pool event comprises both a heterogeneous DNA part (due to the sequence differences) and heterogeneous chemical part due the differences in the chemical composition. Consequently, in order to analyze the chemical reactions it may be desirable to separate the DNA portion of the bi-functional molecule from the reactive compound building block. Thus, one method for separation is the use of a selectively cleavable linker connecting the DNA and the small molecule allowing cleavage and subsequent (optional) removal of the DNA allowing analysis of the remaining chemical fragment.

Selectively cleavable linkers have been described elsewhere and are incorporated herein by reference Pedersen (Pedersen et al. (2002) WO 02/103008 A2). One example is the use of a photo-cleavable linkers or the use of chemically labile linkers such as a linker comprising and S—S bond which can be selectively cleaved by reducing agents such as DTT or TCEP.

In an alternative approach, a fixed DNA sequence of the DNA-oligonucleotide tag that separates the reactive compound building block from the heterologous DNA encoding part may contain a restriction site recognized by a DNA restriction endonuclease. Consequently, DNA cleavage would produce a sample containing a small uniform DNA segment connected to a heterologous reactive compound building block. This fragment may be purified by several methods which include but is not restricted to gel-eletrophoresis, HPLC or hybridization to a biotinylated DNA-oligonucleotide complementary to the DNA segment comprising the pool of chemical fragments followed by binding to streptavidine beads (SA-beads) and subsequent elution of the DNA fragments.

The example described below is included to describe one principle for the evaluation of transformation efficiencies during the generation of a library of bi-functional molecules: The example is used to illustrate one principle for quality control on one or more single reactions, a subset pool of reactions or a sample pool collected from all reactions In a split and mix library generation procedure n chemical reactions are conducted producing n chemical fragments linked to N different oligonucleotide tags producing intermediates with a common structure.

The procedure can be conducted at each round of chemical reaction to monitor reaction efficiencies. If any reactions is not run satisfactorily, all or only a subset of reactions can be iterated and subject to another round of analysis. Such a process using chemical reactions followed by QC on the transformation rates can be repeated any number of time until sufficient chemical turn-over is achieved and verified. For some analysis it may be desirable to purify the sample by gel-electrophoresis or other means such as to harvest the ssDNA or dsDNA identifier comprising the reactive compound building block and purify this moiety from the remaining DNA in the sample such as unligated surplus oligonucleotide tags. Alternatively it may be desirable to purify a singlestranded form of the identifier f. ex by gel-electrophoresis on UREA-PAGE prior to step2 described above.

Another method for monitoring transformation efficiencies in library generation is to include one or more library mimics, a DNA molecule with a reactive entity, in the library synthesis step(s) containing a specific DNA sequence preferably unrelated to any sequence used for library oligonucleotide tagging. The one or more mimics can be included as tracers to monitor single-, a subset pool or the entire pool of reactions at any synthesis or deprotection step during library generation. The mimics will be chemically transformed similar to the reactive entity on the identifier in the library generation process and can be included at any specific reaction step or at multiple reaction steps. As each mimic contains a unique DNA sequence, one or more mimics can be specifically subtracted from the library at any step and analysed for chemical transformations. This allows the experimenter to continuously analyse the chemical reaction within the library synthesis by examination of the included control mimics. The methods for mimic isolation includes, but is not limited to, purification by UREA-PAGE, HPLC/FPLC or purification using binding to a complementary nucleic acids strand, PNA, LNA or molecule with equivalent specific hybridization function, that carries a handle, such as a biotin group, useful for purification such as on SA-beads as described above. Subsequently the mimics can be analysed by any suitable analytical tool such as MALDI- or Electrospray MS.

An alternative method for the purification of the control mimics in the library is to include a selective cleavable linker connecting a handle for purification and the reactive chemical unit. The reactive unit (site) is any suitable reactive groups for example but not limited to an amino, thiol, carboxylic-acid or aldehyd-group. The oligonucleotide moiety is optional but provides an excellent handle for molecular weight analysis using MS. The cleavable linker (optionally) is selectively cleavable by any means such as e.g. by enzymatic, chemical or photocleavable methods. The purification (optional) may be any unit capable of being selectively recovered.

Templated Synthesis:

In some embodiments it may be desirable to amplify, by PCR or other means, the oligonucleotide tags recovered from a selection step and use the amplified material as template for a subsequent synthesis of a library of bi-functional molecules. Methods for templated synthesis of bi-functional complexes include, but is not restricted to methods disclosed in (Rasmussen (2006) WO 06/053571A2, Liu et al. (2002), WO 02/074929 A2; Pedersen et al. (2002) WO 02/103008 A2; Pedersen et al. (2003) WO03/078625 A2; Harbury and Halpin, WO 00/23458, and further methods described herein. Alternatively the amplified oligonucleotide tags may be used for the partitioning of a library of bi-functional complexes prior to selection on a target. This step will enrich a subset of the library by hybridization with the matching oligonucleotide tag and the selection procedure(s) can be iterated with this library subset.

Such pre-selection partitioning of libraries of bi-functional complexes can be accomplished by various methods which include but is not restricted to techniques disclosed in Brenner and Lerner (1992, Proc, Natl. Acad. Sci. 89:5381-83 Lerner et al., EP 0643778 B1; EP 0604552 B1; WO2004099441)

The templated library re-synthesis or subset partitioning followed by selection and amplification (optional) step(s)

described above may be iterated any number of times. Preferably, the processes are iterated until sufficient sequence bias is achieved for easy identification of ligands form oligonucleotide tag sequencing.

The characteristics of the encoded molecules thus identified may now be analyzed, either in its free form (after resynthesis by organic chemistry or after generation of the bi-functional molecule followed by cleavage of the linker that connects the encoded molecule and its identifier) or in its oligonucleotide-linked form (as a bi-functional molecule).

Once the library has been formed in accordance with the methods disclosed herein, one must screen the library for chemical compounds having predetermined desirable characteristics. Predetermined desirable characteristics can include binding to a target, catalytically changing the target, chemically reacting with a target in a manner which alters/modifies the target or the functional activity of the target, and covalently attaching to the target as in a suicide inhibitor. In addition to bioactive species produced as disclosed herein above, bioactive species prepared in accordance with method A and B below, can be screened according to the present invention.

A. Molecules can be single compounds in their final "state", which are oligonucleotide tagged individually and separately. E.g. single compounds may individually be attached to a unique oligonucleotide tag. Each unique oligonucleotide tag holds information on that specific compound, such as e.g. structure, molecular mass etc.

B. A molecule can be a mixture of compounds, which can be considered to be in their final "state". These molecules are normally oligonucleotide tagged individually and separately, i.e. each single compound in a mixture of compounds can be attached to the same oligonucleotide tag. Another oligonucleotide tag can be used for another mixture of compounds. Each unique oligonucleotide tag holds information on that specific mixture, such as e.g. spatial position on a plate.

The target can be any compound of interest. The target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, cell, tissue, etc. without limitation. Particularly preferred targets include, but are not limited to, angiotensin converting enzyme, renin, cyclooxygenase, 5-lipoxygenase, IIL-1 0 converting enzyme, cytokine receptors, PDGF receptor, type II inosine monophosphate dehydrogenase, β-lactamases, and fungal cytochrome P-450. Targets can include, but are not limited to, bradykinin, neutrophil elastase, the HIV proteins, including tat, rev, gag, int, RT, nucleocapsid etc., VEGF, bFGF, TGFβ, KGF, PDGF, thrombin, theophylline, caffeine, substance P, IgE, sPLA2, red blood cells, glioblastomas, fibrin clots, PBMCs, hCG, lectins, selectins, cytokines, ICP4, complement proteins, etc. The target can also be for example, a surface (such as metal, plastic, composite, glass, ceramics, rubber, skin, or tissue); a polymer; a catalyst; or a target biomolecule such as a nucleic acid, a protein (including enzymes, receptors, antibodies, and glycoproteins), a signal molecule (such as cAMP, inositol triphosphate, peptides, or prosoligonucleotide taglandins), a carbohydrate, or a lipid. Binding assays can be advantageously combined with activity assays for the effect of a reaction product on a function of a target molecule.

The methods described herein may involve partitioning of molecules or bi-functional complexes according to their affinity for a target. Targets may be protein or non-protein molecules as discussed herein elsewhere.

In the case of protein targets a list of applicable targets may be obtained e.g. by accessing an public database such as a NCBI database (http://www.ncbi.nlm.nih.gov/entrez/query.fcgi?db=Protein).

In the case of human enzymes and receptors, targets may be retrieved from said database using e.g. "Human" and "Enzyme" or "Receptor" as query keywords. Moreover, a list of targets can be retrieved from the "Mode of Action" section of the Medtrack database (www.medtrack.com).

Further targets of interest for the present invention are listed herein below.

1:) (2'-5')oligo(A) synthetase (EC 2.7.7.-), splice form 8-2-human; (2:) [3-methyl-2-oxobutanoate dehydrogenase [lipoamide]] kinase, mitochondrial precursor (Branched-chain alpha-ketoaciddehydrogenase kinase) (BCKDHKIN) (BCKD-kinase); (3:) [Protein ADP-ribosylarginine] hydrolase (ADP-ribosylargininehydrolase) (ADP-ribose-L-arginine cleaving enzyme); (4:) 1,4-alpha-glucan branching enzyme; (5:) 11 beta-hydroxysteroid dehydrogenase type II; (6:) 11-beta-hydroxysteroid dehydrogenase 1 [*Homo sapiens*]; (7:) 130 kDa leucine-rich protein (LRP 130) (GP130) (Leucine-rich PPR motif-containing protein); (8:) 130 kDa phosphatidylinositol 4,5-biphosphate-dependent ARF1 GTPase-activating protein (PIP2-dependent ARF1 GAP) (ADP-ribosylation factor-directed GTPase-activating protein 1) (ARFGTPase-activating protein 1) (Development and differentiation-enhancing factor 1); (9:) 14-3-3 protein zeta/delta (Protein kinase C inhibitor protein 1) (KCIP-1); (10:) 15-hydroxyprostaglandin dehydrogenase [NAD+] (PGDH) (Prostaglandindehydrogenase 1); (11:) 17 beta hydroxysteroid dehydrogenase type 2; (12:) 17beta-hydroxysteroid dehydrogenase type 10/short chainL-3-hydroxyacyl-CoA dehydrogenase [*Homo sapiens*]; (13:) 17beta-hydroxysteroid dehydrogenase type 7 form 2 [*Homo sapiens*]; (14:) 1-acylglycerol-3-phosphate O-acyltransferase 1 [*Homo sapiens*]; (15:) 1-acylglycerol-3-phosphate O-acyltransferase 5 [*Homo sapiens*]; (16:) 1-aminocyclopropane-1-carboxylate synthase [*Homo sapiens*]; (17:) 1-phosphatidylinositol-4,5-bisphosphate phosphodiesterase gamma 2(Phosphoinositide phospholipase C) (PLC-gamma-2) (PhospholipaseC-gamma-2) (PLC-IV); (18:) 2,4-dienoyl CoA reductase 1 precursor [*Homo sapiens*]; (19:) 2,4-di-enoyl-CoA reductase, mitochondrial precursor (2,4-dienoyl-CoAreductase [NADPH]) (4-enoyl-CoA reductase [NADPH]); (20:) 2',5'-oligoadenylate synthetase 1 isoform 1 [*Homo sapiens*]; (21:) 2',5'-oligoadenylate synthetase 1 isoform 2 [*Homo sapiens*]; (22:) 2',5'-oligoadenylate synthetase 1 isoform 3 [*Homo sapiens*]; (23:) 2-5A-dependent ribonuclease (2-5A-dependent RNase) (Ribonuclease L) (RNase L) (Ribonuclease 4); (24:) 25-hydroxyvitamin D-1 alpha hydroxylase, mitochondrial precursor (Cytochrome P450 subfamily XXVIIB polypeptide 1) (Cytochrome p45027B1) (Calcidiol 1-monooxygenase) (25-OHD-1 alpha-hydroxylase) (25-hydroxyvitamin D(3) 1-alpha-hydroxylase) (VD3 1A hydroxylase) (P450C1 alpha) (P450VD1-alpha); (25:) 25-hydroxyvitamin D-1-alpha-hydroxylase [*Homo sapiens*]; (26:) 2'-5' oligoadenylate synthetase 3 [*Homo sapiens*]; (27:) 2'-5'-oligoadenylate synthetase-like isoform a [*Homo sapiens*]; (28:) 2',5'-oligoadenylate synthetase-like isoform b [*Homo sapiens*]; (29:) 26S proteasome non-ATPase regulatory subunit 2 (26S proteasome regulatory subunit RPN1) (26S proteasome regulatory subunit S2) (26S proteasome subunit p97) (Tumor necrosis factor type 1 receptor-associated protein 2) (55.11 protein); (30:) 26S proteasome non-ATPase regulatory subunit 7 (26S proteasome regulatory subunit rpn8) (26S proteasome regulatory subunit S12) (Proteasome subunit p40) (Mov34 protein homolog); (31:) 2-acylglycerol O-acyltransferase 2 (MonoacylglycerolO-acyltransferase 2) (Acyl CoA: monoacylglycerol acyltransferase 2) (MGAT2) (hMGAT2) (Diacylglycerol acyltransferase 2-like protein 5) (Diacylglycerol O-acyltransferase candidate 5) (hDC5); (32:) 2-acylglycerol O-acyltransferase 3 (MonoacylglycerolO-acyltransferase 3) (Acyl CoA: monoacylglycerol acyltransferase 3) (MGAT3) (Diacylglycerol acyltransferase 2-like protein 7) (Diacylglycerol O-acyltransferase candidate 7) (hDC7); (33:) 2-amino-3-carboxymuconate-6-semialdehyde decarboxylase; (34:) 2-amino-3-ketobutyrate coenzyme A ligase, mitochondrial precursor (AKB ligase) (Glycine acetyltransferase); (35:) 2-amino-3-ketobutyrate-CoA ligase [*Homo sapiens*]; (36:) 2-aminoadipic 6-semialdehyde dehydrogenase [*Homo sapiens*]; (37:) 2-enoyl-CoA hydratase, 3-hydroxyacyl-CoA dehydrogenase, 3-oxoacyl-CoA thiolase, TFE beta=trifunctional enzyme beta subunit{N-terminal} [human, liver, Peptide Mitochondrial Partial, 16 aa]; (38:) 2-hydroxyacyl-CoA lyase 1 [*Homo sapiens*]; (39:) 2-hydroxyacylsphingosine 1-beta-galactosyltransferase (EC 2.4.1.45)—human; (40:) 2-hydroxyphytanoyl-CoA lyase (2-HPCL); (41:) 2-hydroxyphytanoyl-CoA lyase [*Homo sapiens*]; (42:) 2-oxoglutarate dehydrogenase E1 component, mitochondrial precursor (Alpha-ketoglutarate dehydrogenase); (43:) 2-oxoglutarate receptor 1 (Alpha-ketoglutarate receptor 1) (G-protein coupled receptor 80) (G-protein coupled receptor 99) (P2Y purinoceptor 15) (P2Y-like nucleotide receptor) (P2Y-like GPCR); (44:) "3 beta-hydroxysteroid dehydrogenase/delta 5→4-isomerase type I(3Beta-HSD I) (Trophoblast antigen FDO161G) [Includes: 3-beta-hydroxy-delta(5)-steroid dehydrogenase (3-beta-hydroxy-5-enesteroid dehydrogenase) (Progesterone reductase); Steroid delta-isomerase (Delta-5-3-ketosteroid isomerase)]."; (45:) "3 beta-hydroxysteroid dehydrogenase/delta 5→4-isomerase type II(3Beta-HSD II) [Includes:) 3-beta-hydroxy-delta(5)-steroid dehydrogenase (3-beta-hydroxy-5-ene steroid dehydrogenase) (Progesterone reductase); Steroid delta-isomerase(Delta-5-3-ketosteroid isomerase)]."; (46:) 3' histone mRNA exonuclease 1 (3'-5' exonuclease ERI1) (Eri-1 homolog) (Histone mRNA 3' end-specific exoribonuclease) (Protein3' hExo) (HEXO); (47:) 3'(2'),5'-bisphosphate nucleotidase 1 (Bisphosphate 3'-nucleotidase)) (PAP-inositol-1,4-phosphatase) (PIP); (48:) 3,2-trans-enoyl-CoA isomerase, mitochondrial precursor (Dodecenoyl-CoA isomerase) (Delta(3),delta(2)-enoyl-CoA isomerase) (D3,D2-enoyl-CoA isomerase); (49:) 3',5'-cyclic nucleotide phosphodiesterase (EC 3.1.4.17) 8B1-human; (50:) 3-hydroxy-3-methylglutaryl coenzyme A reductase; (51:) "3-hydroxyacyl-CoA dehydrogenase; peroxisomal enoyl-CoA hydratase [*Homo sapiens*]."; (52:) 3-hydroxybutyrate dehydrogenase precursor [*Homo sapiens*]; (53:) 3-hydroxybutyrate dehydrogenase type 2 (R-beta-hydroxybutyrate dehydrogenase) (Dehydrogenase/reductase SDR family member 6) (Oxidoreductase UCPA); (54:) 3-hydroxybutyrate dehydrogenase, type 2 [*Homo sapiens*]; (55:) 3-hydroxyisobutyrate dehydrogenase [*Homo sapiens*]; (56:) 3-hydroxymethyl-3-methylglutaryl-Coenzyme A lyase(hydroxymethylglutaricaciduria) [*Homo sapiens*]; (57:) 3-keto-steroid reductase (Estradiol 17-beta-dehydrogenase 7) (17-beta-HSD 7) (17-beta-hydroxysteroid dehydrogenase 7); (58:) 3-mercaptopyruvate sulfurtransferase [*Homo sapiens*]; (59:) 3-methylcrotonyl-CoA carboxylase alpha subunit [*Homo sapiens*]; (60:) 3-methylcrotonyl-CoA carboxylase biotin-containing subunit [*Homo sapiens*]; (61:) 3-oxo-5 alpha-steroid 4-dehydrogenase 2 [*Homo sapiens*]; (62:) 3-oxo-5-beta-steroid 4-dehydrogenase (Delta(4)-3-ketosteroid5-beta-reductase) (Aldo-keto reductase family 1 member D1); (63:) 3-oxoacid CoA transferase 1 precursor [*Homo sapiens*]; (64:) 3-oxoacyl-[acyl-carrier-protein] synthase, mitochondrial precursor (Beta-ketoacyl synthase); (65:) 3'-phosphoadenosine 5'-phosphosulfate synthase 1 [*Homo sapiens*]; (66:) 3' phosphoadenosine 5'-phosphosulfate synthase 2b isoform [*Homo sapiens*]; (67:) 40 kDa peptidyl-prolyl cis-trans isomerase (PPIase) (Rotamase) (Cyclophilin-40) (CYP-40) (Cyclophilin-related protein); (68:) 4a-carbinolamine dehydratase; (69:) 4-alpha-glucanotransferase (EC 2.4.1.25)/amylo-1,6-glucosidase(EC 3.2.1.33)—human; (70:) 4-aminobutyrate aminotransferase precursor [*Homo sapiens*]; (71:) 4-trimethylaminobutyraldehyde dehydrogenase (TMABADH) (Aldehydedehydrogenase 9A1) (Aldehyde dehydrogenase E3 isozyme) (Gamma-aminobutyraldehyde dehydrogenase) (R-aminobutyraldehydedehydrogenase); (72:) 5' nucleotidase, ecto [*Homo sapiens*]; (73:) 5'(3')-deoxyribonucleotidase, cytosolic type (Cytosolic5',3'-pyrimidine nucleotidase) (Deoxy-5'-nucleotidase 1) (dNT-1); (74:) 5,10-methylenetetrahydrofolate reductase (NADPH) [*Homo sapiens*]; (75:) 5',3'-nucleotidase, cytosolic [*Homo sapiens*]; (76:) 5',3'-nucleotidase, mitochondrial precursor [*Homo sapiens*]; (77:) 52 kD Ro/SSA autoantigen [*Homo sapiens*]; (78:) 5-aminoimidazole-4-carboxamide ribonucleotide formyltransferase/IMP cyclohydrolase [*Homo sapiens*]; (79:) 5-aminolevulinate synthase, erythroid-specific, mitochondrial precursor (5-aminolevulinic acid synthase) (Delta-aminolevulinate synthase) (Delta-ALA synthetase) (ALAS-E); (80:) 5-aminolevulinate synthase, nonspecific, mitochondrial precursor (5-aminolevulinic acid synthase) (Delta-aminolevulinate synthase) (Delta-ALA synthetase) (ALAS-H); (81:) 5-beta steroid reductase [*Homo sapiens*]; (82:) 5-hydroxytryptamine 1A receptor (5-HT-1A) (Serotonin receptor 1A) (5-HT1A) (G-21); (83:) 5-hydroxytryptamine 1B receptor (5-HT-1B) (Serotonin receptor 1 B) (5-HT1B) (5-HT-1D-beta) (Serotonin 1D beta receptor) (S12); (84:) 5-hydroxytryptamine 1D receptor (5-HT-1D) (Serotonin receptor 1D) (5-HT-1D-alpha); (85:) 5-hydroxytryptamine 1E receptor (5-HT-1E) (Serotonin receptor 1E) (5-HT1E) (S31); (86:) 5-hydroxytryptamine 1F receptor (5-HT-1F) (Serotonin receptor 1F); (87:) 5-hydroxytryptamine 2A receptor (5-HT-2A) (Serotonin receptor 2A) (5-HT-2); (88:) 5-hydroxytryptamine 2B receptor (5-HT-2B) (Serotonin receptor 2B); (89:) 5-hydroxytryptamine 2C receptor (5-HT-2C) (Serotonin receptor 2C) (5-HT2C) (5-HTR2C) (5HT-1C); (90:) 5-hydroxytryptamine 3 receptor precursor (5-HT-3) (Serotonin-gated ion channel receptor) (5-HT3R); (91:) 5-hydroxytryptamine 4 receptor (5-HT-4) (Serotonin receptor 4) (5-HT4); (92:) 5-hydroxytryptamine 5A receptor (5-HT-5A) (Serotonin receptor 5A) (5-HT-5); (93:) 5-hydroxytryptamine 6 receptor (5-HT-6) (Serotonin receptor 6); (94:) 5-hydroxytryptamine 7 receptor (5-HT-7) (Serotonin receptor 7) (5-HT-X) (5HT7); (95:) 5-methyltetrahydrofolate-homocysteine methyltransferase [*Homo sapiens*]; (96:) 5'-methylthioadenosine phosphorylase [*Homo sapiens*]; (97:) 5'-nucleotidase, cytosolic II [*Homo sapiens*]; (98:) 5'-nucleotidase, cytosolic III isoform 1 [*Homo sapiens*]; (99:) 6-phosphofructo-2-kinase (EC 2.7.1.105)/ fructose-2,6-bisphosphate 2-phosphatase (EC 3.1.3.46)—human; (100:) "6-phosphofructo-2-kinase/fructose-2,6-biphosphatase 1(6PF-2-K/Fru-2,6-P2ASE liver isozyme) [Includes: 6-phosphofructo-2-kinase; Fructose-2,6-bisphosphatase]."; (101:) 6-phosphofructo-2-kinase/fructose-2,6-biphosphatase 2 isoform a [*Homo sapiens*]; (102:) 6-phosphofructo-2-kinase/fructose-2,6-biphosphatase 2 isoform b [*Homo sapiens*];

(103:) "6-phosphofructo-2-kinase/fructose-2,6-biphosphatase 2(6PF-2-K/Fru-2,6-P2ASE heart-type isozyme) (PFK-2/FBPase-2)[Includes:) 6-phosphofructo-2-kinase; Fructose-2,6-bisphosphatase]."; (104:) 6-phosphofructo-2-kinase/fructose-2,6-biphosphatase 4 [*Homo sapiens*]; (105:) 6-phosphofructo-2-kinase/fructose-2,6-biphosphatase 4 splice isoform 3 [*Homo sapiens*]; (106:) 6-phosphofructo-2-kinase/fructose-2,6-biphosphatase 4 splice isoform 4 [*Homo sapiens*]; (107:) 6-phosphofructo-2-kinase/fructose-2,6-biphosphatase 4 splice isoform 5 [*Homo sapiens*]; (108:) "6-phosphofructo-2-kinase/fructose-2,6-biphosphatase 4(6PF-2-K/Fru-2,6-P2ASE testis-type isozyme) [Includes: 6-phosphofructo-2-kinase; Fructose-2,6-bisphosphatase]."; (109:) 6-phosphofructo-2-kinase/fructose-2,6-biphosphatase-4 isoform 2 [*Homo sapiens*]; (110:) 6-phosphofructokinase (EC 2.7.1.11), hepatic-human; (111:) 6-phosphofructokinase type C (Phosphofructokinase 1) (Phosphohexokinase) (Phosphofructo-1-kinase isozyme C) (PFK-C) (6-phosphofructokinase, platelet type); (112:) 6-phosphofructokinase, liver type (Phosphofructokinase 1) (Phosphohexokinase) (Phosphofructo-1-kinase isozyme B) (PFK-B); (113:) 6-phosphofructokinase, muscle type (Phosphofructokinase 1) (Phosphohexokinase) (Phosphofructo-1-kinase isozyme A) (PFK-A) (Phosphofructokinase-M); (114:) 6-phosphogluconolactonase (6PGL); (115:) 6-pyruvoyl tetrahydrobiopterin synthase (PTPS) (PTP synthase); (116:) 6-pyruvoyltetrahydropterin synthase [*Homo sapiens*]; (117:) 7,8-dihydro-8-oxoguanine triphosphatase (8-oxo-dGTPase) (Nucleosidediphosphate-linked moiety X motif 1) (Nudix motif 1); (118:) 72 kDa type IV collagenase precursor (72 kDa gelatinase) (Matrixmetalloproteinase-2) (MMP-2) (Gelatinase A) (TBE-1); (119:) 85 kDa calcium-independent phospholipase A2 (iPLA2) (Cal-PLA2) (Group VI phospholipase A2) (GVI PLA2); (120:) 8-hydroxyguanine-DNA glycosylase [*Homo sapiens*]; (121:) 8-oxo-7,8-dihydroguanosine triphophatase—human; (122:) 8-oxo-dGTPase [*Homo sapiens*]; (123:) 8-oxoguanine DNA glycosylase 1 [*Homo sapiens*]; (124:) 8-oxoguanine DNA glycosylase homolog 1 [*Homo sapiens*]; (125:) 8-oxoguanine DNA glycosylase isoform 1a [*Homo sapiens*]; (126:) 8-oxoguanine DNA glycosylase isoform 1b [*Homo sapiens*]; (127:) 8-oxoguanine DNA glycosylase isoform 1c [*Homo sapiens*]; (128:) 8-oxoguanine DNA glycosylase isoform 2a [*Homo sapiens*]; (129:) 8-oxoguanine DNA glycosylase isoform 2b [*Homo sapiens*]; (130:) 8-oxoguanine DNA glycosylase isoform 2c [*Homo sapiens*]; (131:) 8-oxoguanine DNA glycosylase isoform 2d [*Homo sapiens*]; (132:) 8-oxoguanine DNA glycosylase isoform 2e [*Homo sapiens*]; (133:) 92-kDa type IV collagenase [*Homo sapiens*]; (134:) 9-cis-retinol specific dehydrogenase [*Homo sapiens*]; (135:) A Transferase [*Homo sapiens*]; (136:) A/G-specific adenine DNA glycosylase (MutY homolog) (hMYH); (137:) ACAD 10 [*Homo sapiens*]; (138:) Ac-CoA carboxylase; (139:) ACE2 [*Homo sapiens*]; (140:) ACE-related carboxypeptidase ACE2 [*Homo sapiens*]; (141:) Acetoacetyl-CoA synthetase [*Homo sapiens*]; (142:) Acetolactate synthase [*Homo sapiens*]; (143:) acetolactate synthase homolog; (144:) Acetylcholine receptor protein subunit alpha precursor; (145:) Acetylcholine receptor protein subunit beta precursor; (146:) Acetylcholine receptor protein subunit delta precursor; (147:) Acetylcholine receptor protein subunit epsilon precursor; (148:) Acetylcholine receptor protein subunit gamma precursor; (149:) Acetylcholinesterase collagenic tail peptide precursor (AChE Qsubunit) (Acetylcholinesterase-associated collagen); (150:) acetylcholinesterase collagen-like tail subunit [*Homo sapiens*]; (151:) acetylcholinesterase collagen-like tail subunit isoform I precursor [*Homo sapiens*]; (152:) acetylcholinesterase collagen-like tail subunit isoform II [*Homo sapiens*]; (153:) acetylcholinesterase collagen-like tail subunit isoform III [*Homo sapiens*]; (154:) acetylcholinesterase collagen-like tail subunit isoform III precursor [*Homo sapiens*]; (155:) acetylcholinesterase collagen-like tail subunit isoform IV [*Homo sapiens*]; (156:) acetylcholinesterase collagen-like tail subunit isoform IV precursor [*Homo sapiens*]; (157:) acetylcholinesterase collagen-like tail subunit isoform V [*Homo sapiens*]; (158:) acetylcholinesterase collagen-like tail subunit isoform V precursor [*Homo sapiens*]; (159:) acetylcholinesterase collagen-like tail subunit isoform VI [*Homo sapiens*]; (160:) acetylcholinesterase collagen-like tail subunit isoform VII [*Homo sapiens*]; (161:) acetylcholinesterase collagen-like tail subunit isoform VIII [*Homo sapiens*]; (162:) acetylcholinesterase collagen-like tail subunit isoform VIII precursor [*Homo sapiens*]; (163:) acetylcholinesterase collagen-like tail subunit isoform VII precursor [*Homo sapiens*]; (164:) acetylcholinesterase collagen-like tail subunit isoform VI precursor [*Homo sapiens*]; (165:) acetylcholinesterase isoform E4-E5 precursor [*Homo sapiens*]; (166:) acetyl-CoA carboxylase (EC 6.4.1.2)—human; (167:) Acetyl-CoA carboxylase 1 (ACC-alpha) [Includes:) Biotin carboxylase]; (168:) acetyl-CoA carboxylase 1 [*Homo sapiens*]; (169:) Acetyl-CoA carboxylase 2 (ACC-beta) [Includes:) Biotin carboxylase]; (170:) acetyl-CoA carboxylase 2 [*Homo sapiens*]; (171:) Acetyl-CoA carboxylase 2 variant [*Homo sapiens*]; (172:) acetyl-CoA carboxylase alpha [*Homo sapiens*]; (173:) acetyl-CoA synthetase [*Homo sapiens*]; (174:) acetyl-Coenzyme A acetyltransferase 1 precursor [*Homo sapiens*]; (175:) acetyl-Coenzyme A acetyltransferase 2 [*Homo sapiens*]; (176:) acetyl-Coenzyme A acyltransferase 1 [*Homo sapiens*]; (177:) acetyl-Coenzyme A carboxylase alpha isoform 1 [*Homo sapiens*]; (178:) acetyl-Coenzyme A carboxylase alpha isoform 2 [*Homo sapiens*]; (179:) acetyl-Coenzyme A carboxylase alpha isoform 3 [*Homo sapiens*]; (180:) acetyl-Coenzyme A carboxylase alpha isoform 4 [*Homo sapiens*]; (181:) acetyl-Coenzyme A carboxylase beta [*Homo sapiens*]; (182:) Acetyl-coenzyme A synthetase 2-like, mitochondrial precursor (Acetate-CoA ligase 2) (Acetyl-CoA synthetase 2) (Acyl-CoAsynthetase short-chain family member 1); (183:) Acetyl-coenzyme A synthetase, cytoplasmic (Acetate-CoA ligase) (Acyl-activating enzyme) (Acetyl-CoA synthetase) (ACS) (AceCS) (Acyl-CoA synthetase short-chain family member 2); (184:) acid alpha-glucosidase preproprotein [*Homo sapiens*]; (185:) acid phosphatase 1 isoform b [*Homo sapiens*]; (186:) acid phosphatase 1 isoform c [*Homo sapiens*]; (187:) acid phosphatase 1 isoform d [*Homo sapiens*]; (188:) acid phosphatase 6, lysophosphatidic [*Homo sapiens*]; (189:) acid phosphatase; (190:) aconitase 2 precursor [*Homo sapiens*]; (191:) Aconitate hydratase, mitochondrial precursor (Citrate hydro-lyase) (Aconitase); (192:) acrosin precursor [*Homo sapiens*]; (193:) ACSBG2 protein [*Homo sapiens*]; (194:) ACSL1 protein [*Homo sapiens*]; (195:) ACSL3 protein [*Homo sapiens*]; (196:) ACSL6 protein [*Homo sapiens*]; (197:) ACSM1 protein [*Homo sapiens*]; (198:) ACSS2 protein [*Homo sapiens*]; (199:) activating transcription factor 2 [*Homo sapiens*]; (200:) activation of Sentrin/SUMO protein AOS1 [*Homo sapiens*]; (201:) activation-induced cytidine deaminase [*Homo sapiens*]; (202:) activin A receptor, type IC [*Homo sapiens*]; (203:) activin A receptor, type IIA precursor [*Homo sapiens*]; (204:) activin A type IB receptor isoform a precursor [*Homo sapiens*]; (205:) activin A type IB receptor isoform b precursor [*Homo sapiens*]; (206:) activin A type IB receptor isoform c precursor [*Homo sapiens*]; (207:) activin A type IIB receptor precursor [*Homo sapiens* sapiens]; (208:) Activin receptor type 1B precursor (ACTR-IB) (Serine/threonine-protein kinase receptor R2) (SKR2) (Activin receptor-like kinase 4) (ALK-4); (209:) Activin receptor type 1C precursor (ACTR-IC) (Activin receptor-like kinase 7) (ALK-7); (210:) Activin receptor type 2A precursor (Activin receptor type IIA) (ACTR-IIA) (ACTRIIA); (211:) Activin receptor type 2B precursor (Activin receptor type IIB) (ACTR-IIB); (212:) Activin receptor type-1 precursor (Activin receptor type I) (ACTR-I) (Serine/threonine-protein kinase receptor R1) (SKR1) (Activin receptor-like kinase 2) (ALK-2) (TGF-B superfamily receptor type I) (TSR-I); (213:) acyl coenzyme A:cholesterol acyltransferase [Homo sapiens]; (214:) acyl coenzyme A:monoacylglycerol acyltransferase 3 [Homo sapiens]; (215:) acylamino acid-releasing enzyme [Homo sapiens]; (216:) Acylamino-acid-releasing enzyme (AARE) (Acyl-peptide hydrolase) (APH) (Acylaminoacyl-peptidase) (Oxidized protein hydrolase) (OPH) (DNF15S2 protein); (217:) Acyl-CoA dehydrogenase family member 8, mitochondrial precursor (ACAD-8) (Isobutyryl-CoA dehydrogenase) (Activator-recruited cofactor 42 kDa component) (ARC42); (218:) Acyl-CoA synthetase 3 [Homo sapiens]; (219:) acyl-CoA synthetase 4 [Homo sapiens]; (220:) Acyl-CoA synthetase bubblegum family member 2 [Homo sapiens]; (221:) acyl-CoA synthetase long-chain family member 1 [Homo sapiens]; (222:) acyl-CoA synthetase long-chain family member 1 isoform a [Homo sapiens]; (223:) acyl-CoA synthetase long-chain family member 1 isoform c [Homo sapiens]; (224:) acyl-CoA synthetase long-chain family member 3 [Homo sapiens]; (225:) Acyl-CoA synthetase long-chain family member 4 [Homo sapiens]; (226:) acyl-CoA synthetase long-chain family member 4 isoform 1 [Homo sapiens]; (227:) acyl-CoA synthetase long-chain family member 4 isoform 2 [Homo sapiens]; (228:) Acyl-CoA synthetase long-chain family member 5 [Homo sapiens]; (229:) acyl-CoA synthetase long-chain family member 5 isoform a [Homo sapiens]; (230:) acyl-CoA synthetase long-chain family member 5 isoform b [Homo sapiens]; (231:) acyl-CoA synthetase long-chain family member 6 isoform a [Homo sapiens]; (232:) acyl-CoA synthetase long-chain family member 6 isoform b [Homo sapiens]; (233:) acyl-CoA synthetase long-chain family member 6 isoform d [Homo sapiens]; (234:) acyl-CoA synthetase long-chain family member 6 isoform e [Homo sapiens]; (235:) Acyl-CoA synthetase medium-chain family member 3 [Homo sapiens]; (236:) Acyl-CoA synthetase short-chain family member 1 [Homo sapiens]; (237:) Acyl-CoA synthetase short-chain family member 2 [Homo sapiens]; (238:) acyl-CoA synthetase short-chain family member 2 isoform 1 [Homo sapiens]; (239:) acyl-CoA synthetase short-chain family member 2 isoform 2 [Homo sapiens]; (240:) acyl-CoA synthetase-like protein [Homo sapiens]; (241:) Acyl-CoA wax alcohol acyltransferase 1 (Long-chain-alcoholO-fatty-acyltransferase 1) (Diacylglycerol O-acyltransferase 2-like protein 3) (Diacyl-glycerol acyltransferase 2); (242:) Acyl-CoA wax alcohol acyltransferase 2 (Long-chain-alcoholO-fatty-acyltransferase 2) (Wax synthase) (hWS) (MultifunctionalO-acyltransferase) (Diacylglycerol O-acyltransferase 2-like protein4) (Diacylglycerol O-acyltransferase candidate 4) (hDC4); (243:) acyl-Coenzyme A dehydrogenase family, member 10 [Homo sapiens]; (244:) Acyl-Coenzyme A dehydrogenase family, member 11 [Homo sapiens]; (245:) acyl-Coenzyme A dehydrogenase family, member 8 [Homo sapiens]; (246:) acyl-Coenzyme A dehydrogenase, C-2 to C-3 short chain precursor [Homo sapiens]; (247:) acyl-Coenzyme A dehydrogenase, C-4 to C-12 straight chain [Homo sapiens]; (248:) acyl-Coenzyme A dehydrogenase, long chain precursor [Homo sapiens]; (249:) acyl-Coenzyme A dehydrogenase, short/branched chain precursor [Homo sapiens]; (250:) acyl-Coenzyme A oxidase 2, branched chain [Homo sapiens]; (251:) acyl-Coenzyme A oxidase 3, pristanoyl [Homo sapiens]; (252:) acyl-Coenzyme A oxidase isoform a [Homo sapiens]; (253:) acyl-Coenzyme A oxidase isoform b [Homo sapiens]; (254:) Acyl-coenzyme A thioesterase 8 (Acyl-CoA thioesterase 8) (Peroxisomal acyl-coenzyme A thioester hydrolase 1) (PTE-1) (Peroxisomal long-chain acyl-coA thioesterase 1) (HIV-Nef-associated acyl coA thioesterase) (Thioesterase II) (hTE) (hACTEIII) (hACTE-III) (PTE-2); (255:) acyl-malonyl condensing enzyme [Homo sapiens]; (256:) acyl-malonyl condensing enzyme 1 [Homo sapiens]; (257:) acyloxyacyl hydrolase precursor [Homo sapiens]; (258:) acyloxyacyl hydrolase; (259:) ADAM 10 precursor (A disintegrin and metalloproteinase domain 10) (Mammalian disintegrin-metalloprotease) (Kuzbanian protein homolog) (CDw156c antigen); (260:) ADAM 17 precursor (A disintegrin and metalloproteinase domain 17) (TNF-alpha-converting enzyme) (TNF-alpha convertase) (Snakevenom-like protease) (CD156b antigen); (261:) ADAM metallopeptidase domain 10 [Homo sapiens]; (262:) ADAM metallopeptidase domain 12 isoform 1 preproprotein [Homo sapiens]; (263:) ADAM metallopeptidase domain 12 isoform 2 preproprotein [Homo sapiens]; (264:) ADAM metallopeptidase domain 17 preproprotein [Homo sapiens]; (265:) ADAM metallopeptidase domain 19 isoform 1 preproprotein [Homo sapiens]; (266:) ADAM metallopeptidase domain 19 isoform 2 preproprotein [Homo sapiens]; (267:) ADAM metallopeptidase domain 33 isoform alpha preproprotein [Homo sapiens]; (268:) ADAM metallopeptidase domain 33 isoform beta preproprotein [Homo sapiens]; (269:) ADAM metallopeptidase with thrombospondin type 1 motif, 12preproprotein [Homo sapiens]; (270:) ADAM metallopeptidase with thrombospondin type 1 motif, 13 isoform1 preproprotein [Homo sapiens]; (271:) ADAM metallopeptidase with thrombospondin type 1 motif, 13 isoform2 preproprotein [Homo sapiens]; (272:) ADAM metallopeptidase with thrombospondin type 1 motif, 13 isoform3 preproprotein [Homo sapiens]; (273:) ADAM metallopeptidase with thrombospondin type 1 motif, 1preproprotein [Homo sapiens]; (274:) ADAM metallopeptidase with thrombospondin type 1 motif, 2 isoform 1preproprotein [Homo sapiens]; (275:) ADAM metallopeptidase with thrombospondin type 1 motif, 2 isoform 2 [Homo sapiens]; (276:) ADAM metallopeptidase with thrombospondin type 1 motif, 3proprotein [Homo sapiens]; (277:) ADAM metallopeptidase with thrombospondin type 1 motif, 4preproprotein [Homo sapiens]; (278:) ADAM metallopeptidase with thrombospondin type 1 motif, 5preproprotein [Homo sapiens]; (279:) ADAM metallopeptidase with thrombospondin type 1 motif, 8preproprotein [Homo sapiens]; (280:) ADAM10 [Homo sapiens]; (281:) ADAMTS-13 precursor (A disintegrin and metalloproteinase with thrombospondin motifs 13) (ADAM-TS13) (ADAM-TS13) (von Willebrand factor-cleaving protease) (vWF-cleaving protease) (vWF-CP); (282:) ADAMTS-14 precursor (A disintegrin and metalloproteinase with thrombospondin motifs 14) (ADAM-TS14) (ADAM-TS14); (283:) ADAMTS-2 precursor (A disintegrin and metalloproteinase with thrombospondin motifs 2) (ADAM-TS 2) (ADAM-TS2) (Procollagen I/II amino propeptide-processing enzyme) (Procollagen I N-proteinase) (PC I-NP) (Procollagen N-endopeptidase) (pNPI); (284:) ADAMTS-3 precursor (A disintegrin and metalloproteinase with thrombospondin motifs 3) (ADAM-TS 3) (ADAM-TS3) (Procollagen II amino propeptide-processing enzyme)

(Procollagen II N-proteinase) (PC II-NP); (285:) adaptor-related protein complex 2, alpha 1 subunit isoform 1 [*Homo sapiens*]; (286:) adaptor-related protein complex 2, alpha 1 subunit isoform 2 [*Homo sapiens*]; (287:) Adenine phosphoribosyltransferase (APRT); (288:) adenine phosphoribosyltransferase isoform a [*Homo sapiens*]; (289:) adenine phosphoribosyltransferase isoform b [*Homo sapiens*]; (290:) Adenosine A1 receptor; (291:) Adenosine A2a receptor; (292:) Adenosine A2b receptor; (293:) Adenosine A3 receptor, (294:) adenosine deaminase [*Homo sapiens*]; (295:) adenosine deaminase variant [*Homo sapiens*]; (296:) adenosine deaminase, RNA-specific isoform a [*Homo sapiens*]; (297:) adenosine deaminase, RNA-specific isoform b [*Homo sapiens*]; (298:) adenosine deaminase, RNA-specific isoform c [*Homo sapiens*]; (299:) adenosine deaminase, RNA-specific isoform d [*Homo sapiens*]; (300:) adenosine kinase isoform a [*Homo sapiens*]; (301:) adenosine kinase isoform b [*Homo sapiens*]; (302:) adenosine monophosphate deaminase 1 (isoform M) [*Homo sapiens*]; (303:) adenylate cyclase (EC 4.6.1.1)—human (fragment); (304:) adenylate cyclase 2 [*Homo sapiens*]; (305:) adenylate cyclase 3 [*Homo sapiens*]; (306:) adenylate cyclase 5 [*Homo sapiens*]; (307:) adenylate cyclase 6 isoform a [*Homo sapiens*]; (308:) adenylate cyclase 6 isoform b [*Homo sapiens*]; (309:) adenylate cyclase 7 [*Homo sapiens*]; (310:) adenylate cyclase 8 [*Homo sapiens*]; (311:) adenylate cyclase 9 [*Homo sapiens*]; (312:) adenylate cyclase activating polypeptide 1 (pituitary) receptor type I precursor [*Homo sapiens*]; (313:) Adenylate cyclase type 1 (Adenylate cyclase type I) (ATP pyrophosphate-lyase 1) (Ca(2+)/calmodulin-activated adenylyl cyclase); (314:) Adenylate cyclase type 2 (Adenylate cyclase type II) (ATP pyrophosphate-lyase 2) (Adenylyl cyclase 2); (315:) Adenylate cyclase type 3 (Adenylate cyclase type III) (Adenylate cyclase, olfactive type) (ATP pyrophosphate-lyase 3) (Adenylyl cyclase 3) (AC-III) (AC3); (316:) Adenylate cyclase type 4 (Adenylate cyclase type IV) (ATP pyrophosphate-lyase 4) (Adenylyl cyclase 4); (317:) Adenylate cyclase type 5 (Adenylate cyclase type V) (ATP pyrophosphate-lyase 5) (Adenylyl cyclase 5); (318:) Adenylate cyclase type 6 (Adenylate cyclase type VI) (ATP pyrophosphate-lyase 6) (Ca(2+)-inhibitable adenylyl cyclase); (319:) Adenylate cyclase type 8 (Adenylate cyclase type VIII) (ATP pyrophosphate-lyase 8) (Ca(2+)/calmodulin-activated adenylyl cyclase); (320:) Adenylate cyclase type 9 (Adenylate cyclase type IX) (ATP pyrophosphate-lyase 9) (Adenylyl cyclase 9); (321:) adenylate kinase 1 [*Homo sapiens*]; (322:) adenylate kinase 2 isoform a [*Homo sapiens*]; (323:) adenylate kinase 2 isoform b [*Homo sapiens*]; (324:) Adenylate kinase isoenzyme 1 (ATP-AMP transphosphorylase) (AK1) (Myokinase); (325:) Adenylate kinase isoenzyme 2, mitochondrial (ATP-AMP transphosphorylase); (326:) Adenylate kinase isoenzyme 5 (ATP-AMP transphosphorylase); (327:) Adenylate kinase isoenzyme 6 (ATP-AMP transphosphorylase 6); (328:) Adenylosuccinate lyase (Adenylosuccinase) (ASL) (ASASE); (329:) adenylosuccinate lyase [*Homo sapiens*]; (330:) adenylosuccinate synthase [*Homo sapiens*]; (331:) adhesion regulating molecule 1 precursor [*Homo sapiens*]; (332:) adiponectin precursor [*Homo sapiens*]; (333:) Adiponectin receptor protein 1 (Progestin and adipoQ receptor family member I); (334:) Adiponectin receptor protein 2 (Progestin and adipoQ receptor family member II); (335:) "Adiponutrin (iPLA2-epsilon) (Calcium-independent phospholipase A2-epsilon) (Patatin-like phospholipase domain-containing protein3) [Includes:) Triacylglycerol lipase; AcylglycerolO-acyltransferase]."; (336:) ADP-ribosyl cyclase 1 (Cyclic ADP-ribose hydrolase 1) (cADPrhydrolase 1) (Lymphocyte differentiation antigen CD38) (T10) (Acutelymphoblastic leukemia cells antigen CD38); (337:) ADP-ribosylarginine hydrolase [*Homo sapiens*]; (338:) ADP-ribosylation factor binding protein 2 [*Homo sapiens*]; (339:) ADP-ribosyltransferase 5 precursor [*Homo sapiens*]; (340:) adrenal gland protein AD-004 [*Homo sapiens*]; (341:) Adrenocorticotropic hormone receptor (ACTH receptor) (ACTH-R) (Melanocortin receptor 2) (MC2-R) (Adrenocorticotropin receptor); (342:) Adrenomedullin receptor (AM-R); (343:) advanced glycosylation end product-specific receptor isoform 1precursor [*Homo sapiens*]; (344:) advanced glycosylation end product-specific receptor isoform 2precursor [*Homo sapiens*]; (345:) aggrecanase 1 [*Homo sapiens*]; (346:) AHCYL1 protein [*Homo sapiens*]; (347:) AICAR formyltransferase/IMP cyclohydrolase bi-functional enzyme; (348:) AK001663 hypothetical protein [*Homo sapiens*]; (349:) A-kinase anchor protein 10 precursor [*Homo sapiens*]; (350:) A-kinase anchor protein 5 (A-kinase anchor protein 79 kDa) (AKAP79) (cAMP-dependent protein kinase regulatory subunit II high affinity-binding protein) (H21); (351:) A-kinase anchor protein 7 isoform alpha [*Homo sapiens*]; (352:) A-kinase anchor protein 7 isoform beta [*Homo sapiens*]; (353:) A-kinase anchor protein 7 isoform gamma [*Homo sapiens*]; (354:) A-kinase anchor protein 8 [*Homo sapiens*]; (355:) alanyl-tRNA synthetase [*Homo sapiens*]; (356:) albumin precursor [*Homo sapiens*]; (357:) Alcohol dehydrogenase [NADP+] (Aldehyde reductase) (Aldo-ketoreductase family 1 member A1); (358:) Alcohol dehydrogenase 1B (Alcohol dehydrogenase beta subunit); (359:) alcohol dehydrogenase 1B (class I), beta polypeptide [*Homo sapiens*]; (360:) Alcohol dehydrogenase 4 (Alcohol dehydrogenase class II pi chain); (361:) Alcohol dehydrogenase class 4 mu/sigma chain (Alcohol dehydrogenase class IV mu/sigma chain) (Retinol dehydrogenase) (Gastric alcohol dehydrogenase); (362:) alcohol dehydrogenase pi subunit; (363:) alcohol dehydrogenase, iron containing, 1 isoform 1 [*Homo sapiens*]; (364:) alcohol dehydrogenase, iron containing, 1 isoform 2 [*Homo sapiens*]; (365:) "alcohol sulfotransferase; hydroxysteroid sulfotransferase [*Homo sapiens*]."; (366:) aldehyde dehydrogenase (NAD+) [*Homo sapiens*]; (367:) aldehyde dehydrogenase 1 (EC 1.2.1.3); (368:) aldehyde dehydrogenase 1 family, member L1 [*Homo sapiens*]; (369:) aldehyde dehydrogenase 1A1 [*Homo sapiens*]; (370:) aldehyde dehydrogenase 1A2 isoform 1 [*Homo sapiens*]; (371:) aldehyde dehydrogenase 1A2 isoform 2 [*Homo sapiens*]; (372:) aldehyde dehydrogenase 1A2 isoform 3 [*Homo sapiens*]; (373:) Aldehyde dehydrogenase 1A3 (Aldehyde dehydrogenase 6) (Retinaldehyde dehydrogenase 3) (RALDH-3); (374:) aldehyde dehydrogenase 1B1 precursor [*Homo sapiens*]; (375:) aldehyde dehydrogenase 2 (EC 1.2.1.3); (376:) aldehyde dehydrogenase 3 family, member A1 [*Homo sapiens*]; (377:) aldehyde dehydrogenase 4A1 precursor [*Homo sapiens*]; (378:) aldehyde dehydrogenase 5A1 precursor, isoform 1 [*Homo sapiens*]; (379:) aldehyde dehydrogenase 5A1 precursor, isoform 2 [*Homo sapiens*]; (380:) aldehyde dehydrogenase 6A1 precursor [*Homo sapiens*]; (381:) aldehyde dehydrogenase 8A1 isoform 1 [*Homo sapiens*]; (382:) aldehyde dehydrogenase 8A1 isoform 2 [*Homo sapiens*]; (383:) aldehyde dehydrogenase 9A1 [*Homo sapiens*]; (384:) Aldehyde dehydrogenase, dimeric NADP-preferring (ALDH class 3) (ALDHIII); (385:) Aldehyde dehydrogenase, mitochondrial precursor (ALDH class 2) (ALDHI) (ALDH-E2); (386:) Aldehyde Reductase; (387:) Aldo-keto reductase family 1 member C3(Trans-1,2-dihydrobenzene-1,2-diol dehydrogenase) (3-alpha-hydroxysteroid dehydrogenase type 2) (3-alpha-HSD type 2) (3-alpha-HSD type II, brain) (Prostaglandin F synthase) (PGFS) (Estradiol 17-beta-dehydrogenase) (17-beta-hydroxysteroiddehydrogenase type 5) (17-beta-HSD 5) (Chlordecone reductase homolog HAKRb) (HA1753) (Dihydrodiol dehydrogenase type I) (Dihydrodiol dehydrogenase 3) (DD3) (DD-3); (388:) aldo-keto reductase family 1, member A4 [Homo sapiens]; (389:) aldo-keto reductase family 1, member B1 [Homo sapiens]; (390:) aldo-keto reductase family 1, member C1 [Homo sapiens]; (391:) aldo-keto reductase family 1, member C2 [Homo sapiens]; (392:) aldo-keto reductase family 1, member C3 [Homo sapiens]; (393:) aldo-keto reductase family 1, member C4 [Homo sapiens]; (394:) aldo-keto reductase family 1, member D1 [Homo sapiens]; (395:) aldolase A [Homo sapiens]; (396:) aldolase B [Homo sapiens]; (397:) Aldose reductase (AR) (Aldehyde reductase); (398:) Aldose Reductase (E.C.1.1.1.21) Mutant With Cys 298 Replaced By Ser(C298s) Complex With Nadph; (399:) Aldose Reductase (E.C.1.1.1.21) Mutant With Tyr 48 Replaced By His(Y48h) Complexed With Nadp+ And Citrate; (400:) ALK tyrosine kinase receptor precursor (Anaplastic lymphoma kinase) (CD246 antigen); (401:) Alkaline ceramidase 1 (Alkaline CDase-1) (AlkCDase 1) (Acylsphingosine deacylase 3) (N-acylsphingosine amidohydrolase 3); (402:) Alkaline phosphatase, placental type precursor (PLAP-1) (Reganisozyme); (403:) Alkaline phosphatase, tissue-nonspecific isozyme precursor (AP-TNAP) (Liver/bone/kidney isozyme) (TNSALP); (404:) Alkaline phytoceramidase (aPHC) (Alkaline ceramidase) (Alkalinedihydroceramidase SB89); (405:) alkaline phytoceramidase [Homo sapiens]; (406:) alkyldihydroxyacetone phosphate synthase precursor [Homo sapiens]; (407:) Alkyldihydroxyacetonephosphate synthase, peroxisomal precursor (Alkyl-DHAP synthase) (Alkylglycerone-phosphate synthase) (Aging-associated protein 5); (408:) alpha (1, 2) fucosyltransferase [Homo sapiens]; (409:) alpha 1 type I collagen preproprotein [Homo sapiens]; (410:) alpha 1 type II collagen isoform 1 precursor [Homo sapiens]; (411:) alpha 1 type II collagen isoform 2 precursor [Homo sapiens]; (412:) alpha 1,2-mannosidase [Homo sapiens]; (413:) alpha 1,4-galactosyltransferase [Homo sapiens]; (414:) alpha 2,3-sialyltransferase III isoform A7 [Homo sapiens]; (415:) alpha 2,3-sialyltransferase III isoform A8 [Homo sapiens]; (416:) alpha 2,3-sialyltransferase III type D2+26 [Homo sapiens]; (417:) alpha galactosidase A; (418:) alpha isoform of regulatory subunit A, protein phosphatase 2 [Homo sapiens]; (419:) alpha isoform of regulatory subunit B55, protein phosphatase 2 [Homo sapiens]; (420:) alpha mannosidase II; (421:) Alpha platelet-derived growth factor receptor precursor (PDGF-R-alpha) (CD140a antigen); (422:) alpha(1,2)fucosyltransferase [Homo sapiens]; (423:) Alpha-(1,3)-fucosyltransferase (Galactoside 3-L-fucosyltransferase) (Fucosyltransferase 6) (FUCT-VI); (424:) alpha/beta hydrolase domain containing protein 1 [Homo sapiens]; (425:) alpha-1 antitrypsin [Homo sapiens]; (426:) alpha-1 antitrypsin variant [Homo sapiens]; (427:) alpha-1,3(6)-mannosylglycoproteinbeta-1,6-N-acetyl-glucosaminyltransferase [Homo sapiens]; (428:) Alpha-1,4-N-acetylglucosaminyltransferase (Alpha4GnT); (429:) Alpha-1A adrenergic receptor (Alpha 1A-adrenoceptor) (Alpha1A-adrenoreceptor) (Alpha-1C adrenergic receptor) (Alpha adrenergic receptor 1c); (430:) Alpha-1-antichymotrypsin precursor (ACT) [Contains: Alpha-1-antichymotrypsin His-Pro-less]; (431:) Alpha-1B adrenergic receptor (Alpha 1B-adrenoceptor) (Alpha1B-adrenoreceptor); (432:) Alpha-1D adrenergic receptor (Alpha 1D-adrenoceptor) (Alpha1D-adrenoreceptor) (Alpha-1A adrenergic receptor) (Alpha adrenergic receptor 1a); (433:) Alpha-2A adrenergic receptor (Alpha-2A adrenoceptor) (Alpha-2A adrenoreceptor) (Alpha-2AAR) (Alpha-2 adrenergic receptor subtype C10); (434:) Alpha-2B adrenergic receptor (Alpha-2B adrenoceptor) (Alpha-2B adrenoreceptor) (Alpha-2 adrenergic receptor subtype C2); (435:) Alpha-2C adrenergic receptor (Alpha-2C adrenoceptor) (Alpha-2C adrenoreceptor) (Alpha-2 adrenergic receptor subtype C4); (436:) Alpha-2-macroglobulin precursor (Alpha-2-M); (437:) alpha-2-macroglobulin precursor [Homo sapiens]; (438:) alpha-2-plasmin inhibitor [Homo sapiens]; (439:) alpha2-subunit of soluble guanylyl cyclase [Homo sapiens]; (440:) alpha-aminoadipate semialdehyde synthase [Homo sapiens]; (441:) "Alpha-aminoadipic semialdehyde synthase, mitochondrial precursor (LKR/SDH) [Includes:) Lysine ketoglutarate reductase (LOR) (LKR); Saccharopine dehydrogenase (SDH)]."; (442:) Alpha-enolase (2-phospho-D-glycerate hydro-lyase) (Non-neuralenolase) (NNE) (Enolase 1) (Phosphopyruvate hydratase) (C-mycpromoter-binding protein) (MBP-1) (MPB-1) (Plasminogen-binding protein); (443:) alpha-galactosidase A [Homo sapiens]; (444:) alpha-galactosidase A precursor (EC 3.2.1.22); (445:) Alpha-galactosidase A precursor (Melibiase) (Alpha-D-galactoside-galactohydrolase) (Alpha-D-galactosidase A) (Agalsidase alfa); (446:) alpha-galactosidase; (447:) alpha-keto acid dehydrogenase precursor; (448:) "alpha-ketoglutarate dehydrogenase complex dihydrolipoylsuccinyltransferase; KGDHC E2k component [Homo sapiens]."; (449:) alpha-KG-E2 [Homo sapiens]; (450:) Alpha-lactalbumin precursor (Lactose synthase B protein); (451:) alpha-L-iduronidase precursor [Homo sapiens]; (452:) Alpha-L-iduronidase precursor; (453:) alpha-methylacyl-CoA racemase isoform 1 [Homo sapiens]; (454:) alpha-methylacyl-CoA racemase isoform 2 [Homo sapiens]; (455:) alpha-N-acetylgalactosaminidase precursor [Homo sapiens]; (456:) alpha-N-acetylglucosaminidase precursor [Homo sapiens]; (457:) alpha-N-acetylglucosaminidase; (458:) Alpha-N-acetyl-neuraminide alpha-2,8-sialyltransferase (Ganglioside GD3 synthase) (Ganglioside GT3 synthase) (Alpha-2,8-sialyltransferase 8A) (ST8Sia I); (459:) alpha-synuclein isoform NACP112 [Homo sapiens]; (460:) alpha-synuclein isoform NACP140 [Homo sapiens]; (461:) amiloride binding protein [Homo sapiens]; (462:) Amiloride binding protein 1 (amine oxidase (copper-containing)) [Homo sapiens]; (463:) amiloride binding protein 1 precursor [Homo sapiens]; (464:) amiloride-binding protein 1 (amine oxidase (copper-containing)) [Homo sapiens]; (465:) amiloride-binding protein; (466:) Amiloride-sensitive amine oxidase [copper-containing] precursor (Diamine oxidase) (DAO) (Amiloride-binding protein) (ABP) (Histaminase) (Kidney amine oxidase) (KAO); (467:) amine oxidase (flavin containing) domain 2 isoform b [Homo sapiens]; (468:) amine oxidase (flavin-containing) [Homo sapiens]; (469:) Amine oxidase [flavin-containing] A (Monoamine oxidase type A) (MAO-A); (470:) amine oxidase, copper containing 2 (retina-specific) [Homo sapiens]; (471:) amine oxidase, copper containing 2 isoform a [Homo sapiens]; (472:) amine oxidase, copper containing 2 isoform b [Homo sapiens]; (473:) Amine oxidase, copper containing 3 (vascular adhesion protein 1) [Homo sapiens]; (474:) amine oxidase, copper containing 3 precursor [Homo sapiens]; (475:) amino-acid N-acetyltransferase (EC 2.3.1.1)-human; (476:) aminoacylase 1 [Homo sapiens]; (477:) aminoadipate-semialdehyde dehydrogenase-phosphopantetheinyltransferase [Homo sapiens]; (478:) aminoadipate-semialdehyde synthase [Homo sapiens]; (479:) aminocarboxymuconate semialdehyde decarboxylase [Homo sapiens]; (480:) aminolevulinate delta-synthase 1 [Homo sapiens]; (481:) aminolevulinate, delta, synthase 1 [Homo sapiens]; (482:) Aminolevulinate, delta-, synthase 1 [Homo sapiens]; (483:) aminolevulinate, delta-, synthase 2 isoform a [Homo sapiens]; (484:) aminolevulinate, delta-, synthase 2 isoform b [Homo sapiens]; (485:) aminolevulinate, delta-, synthase 2 isoform c [Homo sapiens]; (486:) aminolevulinate, delta-, synthase 2 isoform d [Homo sapiens]; (487:) aminomethyltransferase (glycine cleavage system protein T) [Homo sapiens]; (488:) Aminopeptidase N (hAPN) (Alanyl aminopeptidase) (Microsomalaminopeptidase) (Aminopeptidase M) (gp150) (Myeloid plasma membrane glycoprotein CD13) (CD13 antigen); (489:) Aminopeptidase O (AP-O); (490:) aminopeptidase puromycin sensitive [Homo sapiens]; (491:) AMP deaminase 3 (AMP deaminase isoform E) (Erythrocyte AMPdeaminase); (492:) AMP-activated protein kinase alpha 2 catalytic subunit [Homo sapiens]; (493:) AMP-activated protein kinase beta 1 non-catalytic subunit [Homo sapiens]; (494:) AMP-activated protein kinase beta 2 non-catalytic subunit [Homo sapiens]; (495:) AMP-activated protein kinase gamma2 subunit isoform a [Homo sapiens]; (496:) AMP-activated protein kinase gamma2 subunit isoform b [Homo sapiens]; (497:) AMP-activated protein kinase gamma2 subunit isoform c [Homo sapiens]; (498:) AMP-activated protein kinase, noncatalytic gamma-1 subunit isoform1 [Homo sapiens]; (499:) AMP-activated protein kinase, noncatalytic gamma-1 subunit isoform2 [Homo sapiens]; (500:) AMP-activated protein kinase, non-catalytic gamma-3 subunit [Homo sapiens]; (501:) AMP-binding enzyme, 33217 [Homo sapiens]; (502:) amphiregulin preproprotein [Homo sapiens]; (503:) "amylase, alpha 1A; salivary precursor [Homo sapiens]."; (504:) Amylo-1,6-glucosidase, 4-alpha-glucanotransferase (glycogen debranching enzyme, glycogen storage disease type III) [Homo sapiens]; (505:) amylo-1,6-glucosidase, 4-alpha-glucanotransferase isoform 1 [Homo sapiens]; (506:) amylo-1,6-glucosidase, 4-alpha-glucanotransferase isoform 2 [Homo sapiens]; (507:) amylo-1,6-glucosidase, 4-alpha-glucanotransferase isoform 3 [Homo sapiens]; (508:) "Amyloid beta A4 protein precursor (APP) (ABPP) (Alzheimer disease amyloid protein) (Cerebral vascular amyloid peptide) (CVAP) (Protease nexin-II) (PN-II) (APPI) (PreA4) [Contains:) Soluble APP-alpha (S-APP-alpha); Soluble APP-beta (S-APP-beta); C99;Beta-amyloid protein 42 (Beta-APP42); Beta-amyloid protein 40(Beta-APP40); C83; P3(42); P3(40); Gamma-CTF(59) (Gamma-secretase C-terminal fragment 59) (Amyloid intracellular domain 59) (AID(59)); Gamma-CTF(57) (Gamma-secretase C-terminal fragment 57) (Amyloid intracellular domain 57) (AID(57)); Gamma-CTF(50) (Gamma-secretase C-terminal fragment 50) (Amyloid intracellular domain 50) (AID(50)); C31]."; (509:) amyloid beta A4 protein precursor, isoform a [Homo sapiens]; (510:) amyloid beta A4 protein precursor, isoform b [Homo sapiens]; (511:) amyloid beta A4 protein precursor, isoform c [Homo sapiens]; (512:) Amyloid beta precursor protein binding protein 1 [Homo sapiens]; (513:) amyloid beta precursor protein-binding protein 1 isoform a [Homo sapiens]; (514:) amyloid beta precursor protein-binding protein 1 isoform b [Homo sapiens]; (515:) amyloid beta precursor protein-binding protein 1 isoform c [Homo sapiens]; (516:) amyloid precursor protein-binding protein 1 (APP-B1) [Homo sapiens]; (517:) amyloid precursor protein-binding protein 1; (518:) anaphase promoting complex subunit 1 [Homo sapiens]; (519:) anaphase promoting complex subunit 10 [Homo sapiens]; (520:) Anaphase-promoting complex subunit 11 (APC11) (Cyclosome subunit11) (Hepatocellular carcinoma-associated RING finger protein); (521:) anaphase-promoting complex subunit 2 [Homo sapiens]; (522:) anaphase-promoting complex subunit 4 [Homo sapiens]; (523:) anaphase-promoting complex subunit 5 [Homo sapiens]; (524:) anaphase-promoting complex subunit 7 [Homo sapiens]; (525:) Androgen receptor (Dihydrotestosterone receptor); (526:) androgen receptor isoform 1 [Homo sapiens]; (527:) androgen receptor isoform 2 [Homo sapiens]; (528:) androgen-regulated short-chain dehydrogenase/reductase 1 [Homo sapiens]; (529:) Angiogenin precursor (Ribonuclease 5) (RNase 5); (530:) Angiopoietin-1 receptor precursor (Tyrosine-protein kinase receptor TIE-2) (hTIE2) (Tyrosine-protein kinase receptor TEK) (p140 TEK) (Tunica interna endothelial cell kinase) (CD202b antigen); (531:) angiotensin converting enzyme (EC 3.4.15.1); (532:) angiotensin converting enzyme 2 [Homo sapiens]; (533:) angiotensin converting enzyme precursor (EC 3.4.15.1); (534:) angiotensin converting enzyme-like protein [Homo sapiens]; (535:) angiotensin I converting enzyme (peptidyl-dipeptidase A) 1 [Homo sapiens]; (536:) Angiotensin I converting enzyme (peptidyl-dipeptidase A) 2 [Homo sapiens]; (537:) angiotensin I converting enzyme [Homo sapiens]; (538:) angiotensin I converting enzyme 2 precursor [Homo sapiens]; (539:) angiotensin I converting enzyme isoform 1 precursor [Homo sapiens]; (540:) angiotensin I converting enzyme isoform 1 precursor variant [Homo sapiens]; (541:) angiotensin I converting enzyme isoform 2 precursor [Homo sapiens]; (542:) angiotensin I converting enzyme isoform 3 precursor [Homo sapiens]; (543:) "angiotensin I converting enzyme precursor; dipeptidylcarboxypeptidase 1 [Homo sapiens]."; (544:) "angiotensin I converting enzyme precursor; dipeptidylcarboxypeptidase 1; kininase II [Homo sapiens]."; (545:) angiotensin I-converting enzyme [Homo sapiens]; (546:) angiotensin I-converting enzyme precursor (EC 3.4.15.1); (547:) angiotensin II receptor type-1 (clone HATR1GH)—human (fragment); (548:) angiotensin II receptor, type 1 [Homo sapiens]; (549:) angiotensin II receptor, type 2 [Homo sapiens]; (550:) angiotensin-converting enzyme [Homo sapiens]; (551:) angiotensin-converting enzyme 2 [Homo sapiens]; (552:) Angiotensin-converting enzyme 2 precursor (ACE-related carboxypeptidase) (Angiotensin-converting enzyme homolog) (ACEH); (553:) Angiotensin-converting enzyme, somatic isoform precursor (Dipeptidyl carboxypeptidase I) (Kininase II) (CD143 antigen)[Contains:) Angiotensin-converting enzyme, somatic isoform, soluble form]; (554:) Angiotensin-converting enzyme, testis-specific isoform precursor (ACE-T) (Dipeptidyl carboxypeptidase I) (Kininase II) [Contains: Angiotensin-converting enzyme, testis-specific isoform, soluble form]; (555:) "Angiotensinogen precursor [Contains:) Angiotensin-1 (Angiotensin I) (Ang I); Angiotensin-2 (Angiotensin II) (Ang II); Angiotensin-3(Angiotensin III) (Ang III) (Des-Asp[1]-angiotensin II)]."; (556:) angiotensinogen preproprotein [Homo sapiens]; (557:) Annexin A4 (Annexin IV) (Lipocortin IV) (Endonexin I) (Chromobindin-4) (Protein II) (P32.5) (Placental anticoagulant protein II) (PAP-II) (PP4-X) (35-beta calcimedin) (Carbohydrate-binding protein P33/P41) (P33/41); (558:) Annexin A5 (Annexin V) (Lipocortin V) (Endonexin II) (CalphobindinI) (CBP-I) (Placental anticoagulant protein I) (PAP-I) (PP4) (Thromboplastin inhibitor) (Vascular anticoagulant-alpha) (VAC-alpha) (Anchorin CII); (559:) anthracycline-associated resistance ARX [Homo sapiens]; (560:) Anthrax toxin receptor 1 precursor (Tumor endothelial marker 8); (561:) Anthrax toxin receptor 2 precursor (Capillary morphogenesis gene 2protein) (CMG-2); (562:) Anti-Muellerian hormone type-2 receptor precursor (Anti-Muellerian hormone type II receptor) (AMH type II receptor) (MIS type II receptor) (MISRII) (MRII); (563:) antioxidant enzyme AOE37-2 [Homo sapiens]; (564:) antioxidant enzyme B166 [Homo sapiens]; (565:) AP2-associated protein kinase 1 (Adaptor-associated kinase 1); (566:) APC11 anaphase promoting complex subunit 11 isoform 1 [Homo sapiens]; (567:) APC11 anaphase promoting complex subunit 11 isoform 2 [Homo sapiens]; (568:) Apelin receptor (G-protein coupled receptor APJ) (Angiotensin receptor-like 1) (HG11); (569:) APEX nuclease (multifunctional DNA repair enzyme) [Homo sapiens]; (570:) APEX nuclease (multifunctional DNA repair enzyme) 1 [Homo sapiens]; (571:) APG10 autophagy 10-like [Homo sapiens]; (572:) APG12 autophagy 12-like [Homo sapiens]; (573:) Apg3p [Homo sapiens]; (574:) APG4 autophagy 4 homolog B isoform a [Homo sapiens]; (575:) APG4 autophagy 4 homolog B isoform b [Homo sapiens]; (576:) APG5 autophagy 5-like [Homo sapiens]; (577:) APG7 autophagy 7-like [Homo sapiens]; (578:) APOBEC1 complementation factor (APOBEC1-stimulating protein); (579:) apobec-1 complementation factor isoform 1 [Homo sapiens]; (580:) apobec-1 complementation factor isoform 2 [Homo sapiens]; (581:) apobec-1 complementation factor isoform 3 [Homo sapiens]; (582:) APOBEC-1 stimulating protein [Homo sapiens]; (583:) Apolipoprotein A-I precursor (Apo-AI) (ApoA-I) [Contains: Apolipoprotein A-I(1-242)]; (584:) apolipoprotein A-II preproprotein [Homo sapiens]; (585:) apolipoprotein B mRNA editing enzyme [Homo sapiens]; (586:) apolipoprotein B mRNA editing enzyme catalytic polypeptide-like 3G [Homo sapiens]; (587:) apolipoprotein B mRNA editing enzyme complex-1 [Homo sapiens]; (588:) apolipoprotein B mRNA editing enzyme, catalytic polypeptide 1; (589:) apolipoprotein B mRNA editing enzyme, catalytic polypeptide-like 2 [Homo sapiens]; (590:) apolipoprotein B mRNA editing enzyme, catalytic polypeptide-like 2variant [Homo sapiens]; (591:) Apolipoprotein B mRNA editing enzyme, catalytic polypeptide-like 3A [Homo sapiens]; (592:) apolipoprotein B mRNA editing enzyme, catalytic polypeptide-like 3B [Homo sapiens]; (593:) apolipoprotein B mRNA editing enzyme, catalytic polypeptide-like 3C [Homo sapiens]; (594:) apolipoprotein B mRNA editing enzyme, catalytic polypeptide-like 3C variant [Homo sapiens]; (595:) apolipoprotein B mRNA editing enzyme, catalytic polypeptide-like 3D [Homo sapiens]; (596:) Apolipoprotein B mRNA editing enzyme, catalytic polypeptide-like 3F [Homo sapiens]; (597:) apolipoprotein B mRNA editing enzyme, catalytic polypeptide-like 3F isoform a [Homo sapiens]; (598:) apolipoprotein B mRNA editing enzyme, catalytic polypeptide-like 3F isoform b [Homo sapiens]; (599:) apolipoprotein B mRNA editing enzyme, catalytic polypeptide-like 3G [Homo sapiens]; (600:) Apolipoprotein B mRNA editing enzyme, catalytic polypeptide-like 3H [Homo sapiens]; (601:) apolipoprotein B mRNA editing enzyme, catalytic polypeptide-like 4(putative) [Homo sapiens]; (602:) apolipoprotein B precursor [Homo sapiens]; (603:) apolipoprotein C-II precursor [Homo sapiens]; (604:) apolipoprotein D precursor [Homo sapiens]; (605:) apolipoprotein E precursor [Homo sapiens]; (606:) apoptotic caspase Mch5-beta [Homo sapiens]; (607:) apoptotic cysteine protease Mch5 isoform alpha; (608:) apoptotic cysteine protease proMch4; (609:) aprataxin isoform a [Homo sapiens]; (610:) aprataxin isoform b [Homo sapiens]; (611:) aprataxin isoform c [Homo sapiens]; (612:) aprataxin isoform d [Homo sapiens]; (613:) apurinic/apyrimidinic endonuclease; (614:) aquaporin 12A [Homo sapiens]; (615:) arachidonate 12-lipoxygenase [Homo sapiens]; (616:) arachidonate 15-lipoxygenase [Homo sapiens]; (617:) arachidonate 5-lipoxygenase [Homo sapiens]; (618:) arachidonate 5-lipoxygenase-activating protein [Homo sapiens]; (619:) Archaemetzincin-1 (Archeobacterial metalloproteinase-like protein1); (620:) Archaemetzincin-2 (Archeobacterial metalloproteinase-like protein2); (621:) arginase, type I [Homo sapiens]; (622:) Arginine decarboxylase (ARGDC) (ADC) (Ornithine decarboxylase-likeprotein) (ODC-paralogue) (ODC-p); (623:) arginine decarboxylase [Homo sapiens]; (624:) arginine methyltransferase 6 [Homo sapiens]; (625:) argininosuccinate lyase isoform 1 [Homo sapiens]; (626:) argininosuccinate lyase isoform 2 [Homo sapiens]; (627:) argininosuccinate lyase isoform 3 [Homo sapiens]; (628:) arginyl aminopeptidase (aminopeptidase B) [Homo sapiens]; (629:) arginyltransferase 1 isoform 1 [Homo sapiens]; (630:) arginyltransferase 1 isoform 2 [Homo sapiens]; (631:) Ariadne homolog, ubiquitin-conjugating enzyme E2 binding protein, I (Drosophila) [Homo sapiens]; (632:) ariadne ubiquitin-conjugating enzyme E2 binding protein homolog 1 [Homo sapiens]; (633:) aromatase cytochrome P-450; (634:) aromatic decarboxylase [Homo sapiens]; (635:) Aromatic-L-amino-acid decarboxylase (AADC) (DOPA decarboxylase) (DDC); (636:) Arsenite methyltransferase (S-adenosyl-L-methionine:arsenic(III)methyltransferase) (Methylarsonite methyltransferase); (637:) Aryl hydrocarbon receptor precursor (Ah receptor) (AhR); (638:) Arylacetamide deacetylase (AADAC); (639:) arylalkylamine N-acetyltransferase [Homo sapiens]; (640:) arylamide acetylase 2 [Homo sapiens]; (641:) Arylamine N-acetyltransferase 1 (Arylamide acetylase 1) (Monomorphic arylamine N-acetyltransferase) (MNAT) (N-acetyltransferase type 1) (NAT-1); (642:) "Arylsulfatase A precursor (ASA) (Cerebroside-sulfatase) [Contains: Arylsulfatase A component B; Arylsulfatase A component C]."; (643:) arylsulfatase A precursor [Homo sapiens]; (644:) arylsulfatase B isoform 1 precursor [Homo sapiens]; (645:) arylsulfatase B isoform 2 precursor [Homo sapiens]; (646:) Arylsulfatase B precursor (ASB) (N-acetylgalactosamine-4-sulfatase) (G4S); (647:) Arylsulfatase E precursor (ASE); (648:) Arylsulfatase F precursor (ASF); (649:) Asialoglycoprotein receptor 1 (ASGPR 1) (ASGP-R 1) (Hepatic lectin H1); (650:) Asialoglycoprotein receptor 2 (ASGP-R 2) (ASGPR 2) (Hepatic lectin H2); (651:) asparagine-linked glycosylation 12 [Homo sapiens]; (652:) aspartate aminotransferase 1 [Homo sapiens]; (653:) aspartate aminotransferase 2 precursor [Homo sapiens]; (654:) aspartoacylase [Homo sapiens]; (655:) aspartylglucosaminidase precursor [Homo sapiens]; (656:) aspartyl-tRNA synthetase [Homo sapiens]; (657:) Astacin-like metalloendopeptidase precursor (Oocyte astacin) (Ovastacin); (658:) ataxin 3 isoform 1 [Homo sapiens]; (659:) ataxin 3 isoform 2 [Homo sapiens]; (660:) ataxin 3 isoform 3 [Homo sapiens]; (661:) Ataxin-3 (Machado-Joseph disease protein 1) (Spinocerebellar ataxia type 3 protein); (662:) ATP citrate lyase isoform 1 [Homo sapiens]; (663:) ATP citrate lyase isoform 2 [Homo sapiens]; (664:) ATP specific succinyl CoA synthetase beta subunit precursor [Homo sapiens]; (665:) ATP sulfurylase/APS kinase [Homo sapiens]; (666:) ATP sulfurylase/APS kinase isoform SK2 [Homo sapiens]; (667:) ATP synthase mitochondrial F1 complex assembly factor 1 isoform 1 precursor [Homo sapiens]; (668:) ATP synthase mitochondrial F1 complex assembly factor 1 isoform 2 precursor [Homo sapiens]; (669:) ATP synthase mitochondrial F1 complex assembly factor 2 [Homo sapiens]; (670:) ATPase, Ca++ transporting, cardiac muscle, slow twitch 2 isoform 1 [Homo sapiens]; (671:) ATPase, Ca++ transporting, cardiac muscle, slow twitch 2 isoform 2 [Homo sapiens]; (672:) ATPase, Ca++ transporting, fast twitch 1 isoform a [Homo sapiens]; (673:) ATPase, Ca++ transporting, fast twitch 1 isoform b [Homo sapiens]; (674:) ATPase, Cu++ transporting, alpha polypeptide [Homo sapiens]; (675:) ATPase, Cu++ transporting, beta polypeptide isoform a [*Homo sapiens*]; (676:) ATPase, Cu++ transporting, beta polypeptide isoform b [*Homo sapiens*]; (677:) ATPase, H+ transporting, lysosomal 14 kD, V1 subunit F [*Homo sapiens*]; (678:) ATPase, H+ transporting, lysosomal 21 kDa, V0 subunit b isoform 1 [*Homo sapiens*]; (679:) ATPase, H+ transporting, lysosomal 21 kDa, V0 subunit b isoform 2 [*Homo sapiens*]; (680:) ATPase, H+ transporting, lysosomal 42 kDa, V1 subunit C1 isoform A [*Homo sapiens*]; (681:) ATPase, H+ transporting, lysosomal 42 kDa, V1 subunit C1 isoform B [*Homo sapiens*]; (682:) ATPase, H+ transporting, lysosomal 50/57 kDa, V1 subunit H [*Homo sapiens*]; (683:) ATPase, H+ transporting, lysosomal 50/57 kDa, V1 subunit H isoform 1 [*Homo sapiens*]; (684:) ATPase, H+ transporting, lysosomal 50/57 kDa, V1 subunit H isoform 2 [*Homo sapiens*]; (685:) ATPase, H+ transporting, lysosomal 56/58 kDa, V1 subunit B1 [*Homo sapiens*]; (686:) ATPase, H+ transporting, lysosomal 70 kD, V1 subunit A, isoform 1 [*Homo sapiens*]; (687:) ATPase, H+ transporting, lysosomal 9 kDa, V0 subunit e1 [*Homo sapiens*]; (688:) ATPase, H+ transporting, lysosomal accessory protein 1 precursor [*Homo sapiens*]; (689:) ATPase, H+ transporting, lysosomal V0 subunit a isoform 1 [*Homo sapiens*]; (690:) ATPase, H+ transporting, lysosomal V0 subunit a4 [*Homo sapiens*]; (691:) ATPase, H+ transporting, lysosomal, V0 subunit c [*Homo sapiens*]; (692:) ATPase, H+ transporting, lysosomal, V0 subunit d1 [*Homo sapiens*]; (693:) ATPase, H+ transporting, lysosomal, V1 subunit G2 isoform a [*Homo sapiens*]; (694:) ATPase, H+ transporting, lysosomal, V1 subunit G2 isoform b [*Homo sapiens*]; (695:) ATPase, H+ transporting, lysosomal, V1 subunit G3 isoform a [*Homo sapiens*]; (696:) ATPase, H+ transporting, lysosomal, V1 subunit G3 isoform b [*Homo sapiens*]; (697:) ATPase, H+/K+ exchanging, alpha polypeptide [*Homo sapiens*]; (698:) ATPase, H+/K+ exchanging, beta polypeptide [*Homo sapiens*]; (699:) ATP-binding cassette sub-family B member 1 [*Homo sapiens*]; (700:) ATP-binding cassette transporter sub-family C member 8(Sulfonylurea receptor 1); (701:) ATP-binding cassette transporter sub-family C member 9(Sulfonylurea receptor 2); (702:) ATP-citrate synthase (ATP-citrate (pro-S-)-lyase) (Citrate cleavage enzyme); (703:) ATP-dependent DNA helicase 2 subunit 1 (ATP-dependent DNA helicaseII 70 kDa subunit) (Lupus Ku autoantigen protein p70) (Ku70) (70 kDa subunit of Ku antigen) (Thyroid-lupus autoantigen) (TLAA) (CTCbox-binding factor 75 kDa subunit) (CTCBF) (CTC75) (DNA-repair protein XRCC6); (704:) ATP-dependent DNA helicase 2 subunit 2 (ATP-dependent DNA helicaseII 80 kDa subunit) (Lupus Ku autoantigen protein p86) (Ku86) (Ku80) (86 kDa subunit of Ku antigen) (Thyroid-lupus autoantigen) (TLAA) (CTC box-binding factor 85 kDa subunit) (CTCBF) (CTC85) (Nuclear factor IV) (DNA-repair protein XRCC5); (705:) ATP-dependent DNA helicase II [*Homo sapiens*]; (706:) ATP-dependent DNA helicase II, 70 kDa subunit [*Homo sapiens*]; (707:) Atrial natriuretic peptide clearance receptor precursor (ANP-C) (ANPRC) (NPR-C) (Atrial natriuretic peptide C-type receptor); (708:) Atrial natriuretic peptide receptor A precursor (ANP-A) (ANPRA) (GC-A) (Guanylate cyclase) (NPR-A) (Atrial natriuretic peptide A-type receptor); (709:) Atrial natriuretic peptide receptor B precursor (ANP-B) (ANPRB) (GC-B) (Guanylate cyclase B) (NPR-B) (Atrial natriuretic peptide B-type receptor); (710:) Atrial natriuteric peptide-converting enzyme (pro-ANP-converting enzyme) (Corin) (Heart-specific serine proteinase ATC2) (Transmembrane protease, serine 10); (711:) Attractin precursor (Mahogany homolog) (DPPT-L); (712:) AU RNA-binding protein/ enoyl-Coenzyme A hydratase precursor [*Homo sapiens*]; (713:) Autocrine motility factor receptor precursor, isoform 1 (AMF receptor); (714:) Autocrine motility factor receptor, isoform 2 (AMF receptor) (gp78); (715:) autoimmune regulator AIRE isoform 1 [*Homo sapiens*]; (716:) autoimmune regulator AIRE isoform 2 [*Homo sapiens*]; (717:) Autophagy-related protein 10 (APG10-like); (718:) Autophagy-related protein 3 (APG3-like) (hApg3) (Protein PC3-96); (719:) Autophagy-related protein 7 (APG7-like) (Ubiquitin-activating enzyme E1-like protein) (hAGP7); (720:) autotaxin isoform 1 preproprotein [*Homo sapiens*]; (721:) autotaxin isoform 2 preproprotein [*Homo sapiens*]; (722:) Azurocidin precursor (Cationic antimicrobial protein CAP37) (Heparin-binding protein) (HBP); (723:) azurocidin, PUP=elastase homlog [human, Peptide Partial, 21 aa]; (724:) B- and T-lymphocyte attenuator precursor (B- and T-lymphocyte-associated protein) (CD272 antigen); (725:) B1 bradykinin receptor (BK-1 receptor) (B1R); (726:) B2 bradykinin receptor (BK-2 receptor) (B2R); (727:) B3GAT1 [*Homo sapiens*]; (728:) B3GAT2 [*Homo sapiens*]; (729:) B3GAT2 protein [*Homo sapiens*]; (730:) B3GAT3 protein [*Homo sapiens*]; (731:) baculoviral IAP repeat-containing 6 [*Homo sapiens*]; (732:) Baculoviral IAP repeat-containing protein 6 (Ubiquitin-conjugating BIR-domain enzyme apollon); (733:) Basic fibroblast growth factor receptor 1 precursor (FGFR-1) (bFGF-R) (Fms-like tyrosine kinase 2) (c-fgr) (CD331 antigen); (734:) BDNF/NT-3 growth factors receptor precursor (Neurotrophic tyrosine kinase receptor type 2) (TrkB tyrosine kinase) (GP145-TrkB) (Trk-B); (735:) beclin 1 [*Homo sapiens*]; (736:) beta adrenergic receptor kinase 1 [*Homo sapiens*]; (737:) beta adrenergic receptor kinase 2 [*Homo sapiens*]; (738:) beta amyloid cleaving enzyme 2 [*Homo sapiens*]; (739:) beta isoform of regulatory subunit A, protein phosphatase 2 isoforma [*Homo sapiens*]; (740:) beta isoform of regulatory subunit A, protein phosphatase 2 isoformb [*Homo sapiens*]; (741:) beta isoform of regulatory subunit B55, protein phosphatase 2 isoform a [*Homo sapiens*]; (742:) beta isoform of regulatory subunit B55, protein phosphatase 2 isoform b [*Homo sapiens*]; (743:) beta isoform of regulatory subunit B55, protein phosphatase 2 isoform c [*Homo sapiens*]; (744:) beta isoform of regulatory subunit B55, protein phosphatase 2 isoform d [*Homo sapiens*]; (745:) beta isoform of regulatory subunit B56, protein phosphatase 2A [*Homo sapiens*]; (746:) Beta klotho (BetaKlotho) (Klotho beta-like protein); (747:) Beta platelet-derived growth factor receptor precursor (PDGF-R-beta) (CD140b antigen); (748:) beta(1,6)-N-acetylglucosaminyltransferase V isoform 1 [*Homo sapiens*]; (749:) beta(1,6)-N-acetylglucosaminyltransferase V isoform 2 [*Homo sapiens*]; (750:) Beta,beta-carotene 9',10'-dioxygenase (Beta-carotene dioxygenase 2) (B-diox-II); (751:) Beta-1 adrenergic receptor (Beta-1 adrenoceptor) (Beta-1adrenoreceptor); (752:) beta-1,3 galactosyltransferase-V [*Homo sapiens*]; (753:) Beta-1,3-galactosyl-O-glycosyl-glycoproteinbeta-1,6-N-acetylglucosaminyltransferase (Core 2 branching enzyme) (Core2-GlcNAc-transferase) (C2GNT) (Core 2 GNT); (754:) beta-1,3-galactosyl-O-glycosyl-glycoproteinbeta-1,6-N-acetylglucosaminyltransferase [*Homo sapiens*]; (755:) beta1,3-galactosyltransferase [*Homo sapiens*]; (756:) Beta-1,3-galactosyltransferase 5 (Beta-1,3-GalTase 5) (Beta3Gal-T5) (b3Gal-T5) (UDP-galactose: beta-N-acetylglucosaminebeta-1,3-galactosyltransferase 5) (UDP-Gal:beta-GlcNAcbeta-1,3-galactosyltransferase 5) (Beta-3-Gx-T5); (757:) Beta-1,3-glucosyltransferase (Beta3Glc-T) (Beta-3-glycosyltransferase-like); (758:) Beta-1,3-glucuronyltransferase 1 (glucuronosyltransferase P) [*Homo sapiens*]; (759:) beta-1,3-glucuronyltransferase 1 [*Homo sapiens*]; (760:) Beta-1,3-glucuronyltransferase 3

(glucuronosyltransferase I) [Homo sapiens]; (761:) beta-1,3-glucuronyltransferase 3 [Homo sapiens]; (762:) beta-1,3-N-acetylglucosaminyltransferase 5 [Homo sapiens]; (763:) beta-1,3-N-acetylglucosaminyltransferase 6 [Homo sapiens]; (764:) "Beta-1,4-galactosyltransferase 1 (Beta-1,4-GalTase 1) (Beta4Gal-T1) (b4Gal-T1) (UDP-galactose:beta-N-acetylglucosaminebeta-1,4-galactosyltransferase 1) (UDP-Gal:beta-GlcNAcbeta-1,4-galactosyltransferase 1) [Includes:) Lactose synthase A protein; N-acetyllactosamine synthase (NaI synthetase); Beta-N-acetylglucosaminylglycopeptidebeta-1,4-galactosyltransferase; Beta-N-acetylglucosaminyl-glycolipid beta-1,4-galactosyltransferase]."; (765:) Beta-1,4-galactosyltransferase 6 (Beta-1,4-GalTase 6) (Beta4Gal-T6) (b4Gal-T6) (UDP-galactose: beta-N-acetylglucosaminebeta-1,4-galactosyltransferase 6) (UDP-Gal:beta-GlcNAcbeta-1,4-galactosyltransferase 6) [Includes:) Lactosylceramidesynthase (LacCer synthase) (UDP-Gal:glucosylceramidebeta-1,4-galactosyltransferase)]; (766:) beta-1,4-N-acethylgalactosaminyltransferase [Homo sapiens]; (767:) beta-1,4-N-acetyl-galactosaminyl transferase 1 [Homo sapiens]; (768:) beta-1,6-N-acetylglucosaminyltransferase [Homo sapiens]; (769:) beta-1,6-N-acetylglucosaminyltransferase 2 [Homo sapiens]; (770:) beta-1,6-N-acetylglucosaminyltransferase 3 [Homo sapiens]; (771:) beta-1,6-N-acetylglucosaminyltransferase; (772:) Beta-2 adrenergic receptor (Beta-2 adrenoceptor) (Beta-2adrenoreceptor); (773:) Beta-3 adrenergic receptor (Beta-3 adrenoceptor) (Beta-3adrenoreceptor); (774:) beta-adrenergic-receptor kinase (EC 2.7.1.126) 2—human; (775:) Beta-Ala-His dipeptidase precursor (Carnosine dipeptidase 1) (CNDPdipeptidase 1) (Serum carnosinase) (Glutamate carboxypeptidase-likeprotein 2); (776:) beta-carotene 15,15'-monooxygenase 1 [Homo sapiens]; (777:) beta-carotene dioxygenase 2 isoform a [Homo sapiens]; (778:) beta-carotene dioxygenase 2 isoform b [Homo sapiens]; (779:) beta-D-galactosidase precursor (EC 3.2.1.23); (780:) Beta-galactosidase precursor (Lactase) (Acid beta-galactosidase); (781:) beta-galactosidase related protein precursor; (782:) Beta-galactosidase-related protein precursor (Beta-galactosidase-like protein) (S-Gal) (Elastin-binding protein) (EBP); (783:) Beta-hexosaminidase alpha chain precursor (N-acetyl-beta-glucosaminidase) (Beta-N-acetyl-hexosaminidase) (Hexosaminidase A); (784:) "Beta-hexosaminidase beta chain precursor (N-acetyl-beta-glu-cosaminidase) (Beta-N-acetylhexosaminidase) (Hexosaminidase B) (Cervical cancer proto-oncogene 7) (HCC-7)[Contains:) Beta-hexosaminidase beta-B chain; Beta-hexosaminidasebeta-A chain]."; (785:) beta-hexosaminidase beta-chain {R to Q substitution at residue 505,internal fragment} {EC 3.2.1.53} [human, skin fibroblasts, PeptidePartial Mutant, 23 aa]; (786:) betaine-homocysteine methyltransferase [Homo sapiens]; (787:) beta-mannosidase [Homo sapiens]; (788:) beta-polymerase; (789:) Beta-secretase 1 precursor (Beta-site APP cleaving enzyme 1) (Beta-site amyloid precursor protein cleaving enzyme 1) (Membrane-associated aspartic protease 2) (Memapsin-2) (Aspartylprotease 2) (Asp 2) (ASP2); (790:) Beta-secretase 2 precursor (Beta-site APP-cleaving enzyme 2) (Aspartyl protease 1) (Asp 1) (ASP1) (Membrane-associated asparticprotease 1) (Memapsin-1) (Down region aspartic protease); (791:) beta-site APP cleaving enzyme [Homo sapiens]; (792:) beta-site APP cleaving enzyme I-432 [Homo sapiens]; (793:) beta-site APP cleaving enzyme I-457 [Homo sapiens]; (794:) beta-site APP cleaving enzyme I-476 [Homo sapiens]; (795:) beta-site APP cleaving enzyme isoform I-127 [Homo sapiens]; (796:) beta-site APP cleaving enzyme type B [Homo sapiens]; (797:) beta-site APP cleaving enzyme type C [Homo sapiens]; (798:) beta-site APP-cleaving enzyme [Homo sapiens]; (799:) Beta-site APP-cleaving enzyme 1 [Homo sapiens]; (800:) beta-site APP-cleaving enzyme 1 isoform A preproprotein [Homo sapiens]; (801:) beta-site APP-cleaving enzyme 1 isoform B preproprotein [Homo sapiens]; (802:) beta-site APP-cleaving enzyme 1 isoform C preproprotein [Homo sapiens]; (803:) beta-site APP-cleaving enzyme 1 isoform D preproprotein [Homo sapiens]; (804:) Beta-site APP-cleaving enzyme 2 [Homo sapiens]; (805:) beta-site APP-cleaving enzyme 2 isoform A preproprotein [Homo sapiens]; (806:) beta-site APP-cleaving enzyme 2 isoform B preproprotein [Homo sapiens]; (807:) beta-site APP-cleaving enzyme 2 isoform C preproprotein [Homo sapiens]; (808:) beta-site APP-cleaving enzyme 2, EC 3.4.23. [Homo sapiens]; (809:) beta-synuclein [Homo sapiens]; (810:) Beta-ureidopropionase (Beta-alanine synthase) (N-carbamoyl-beta-alanine amidohydrolase) (BUP-1); (811:) "Bi-functional 3'-phosphoadenosine 5'-phosphosulfate synthetase 1(PAPS synthetase 1) (PAPSS 1) (Sulfurylase kinase 1) (SK1) (SK 1)[Includes) Sulfate adenylyltransferase (Sulfate adenylatetransferase) (SAT) (ATP-sulfurylase); Adenylyl-sulfate kinase(Adenylylsulfate 3'-phosphotransferase) (APS kinase) (Adenosine-5'-phosphosulfate 3'-phosphotransferase) (3'-phosphoadenosine-5'-phosphosulfate synthetase)]."; (812:) "Bi-functional 3'-phosphoadenosine 5'-phosphosulfate synthetase 2(PAPS synthetase 2) (PAPSS 2) (Sulfurylase kinase 2) (SK2) (SK 2)[Includes) Sulfate adenylyltransferase (Sulfate adenylatetransferase) (SAT) (ATP-sulfurylase); Adenylyl-sulfate kinase(Adenylylsulfate 3'-phosphotransferase) (APS kinase) (Adenosine-5'-phosphosulfate 3'-phosphotransferase) (3'-phosphoadenosine-5'-phosphosulfate synthetase)]."; (813:) bi-functional ATP sulfurylase/adenosine 5'-phosphosulfate kinase [Homo sapiens]; (814:) "Bi-functional coenzyme A synthase (CoA synthase) (NBP) (POV-2)[Includes) Phosphopantetheine adenylyltransferase(Pantetheine-phosphate adenylyltransferase) (PPAT) (Dephospho-CoApyrophosphorylase); Dephospho-CoA kinase (DPCK) (DephosphocoenzymeA kinase) (DPCOAK)]."; (815:) "Bi-functional heparan sulfate N-deacetylase/N-sulfotransferase 1(Glucosaminyl N-deacetylase/N-sulfotransferase 1) (NDST-1) ([Heparan sulfate]-glucosamine N-sulfotransferase 1) (HSNST 1) (N-heparan sulfate sulfotransferase 1) (N-HSST 1) [Includes: Heparan sulfate N-deacetylase 1; Heparan sulfate N-sulfotransferase 1]."; (816:) "Bi-functional heparan sulfate N-deacetylase/N-sulfotransferase 2(Glucosaminyl N-deacetylase/N-sulfotransferase 2) (NDST-2) (N-heparan sulfate sulfotransferase 2) (N-HSST 2) [Includes: Heparan sulfate N-deacetylase 2; Heparan sulfate N-sulfotransferase 2]."; (817:) "Bi-functional heparan sulfate N-deacetylase/N-sulfotransferase 3(Glucosaminyl N-deacetylase/N-sulfotransferase 3) (NDST-3) (hNDST-3) (N-heparan sulfate sulfotransferase 3) (N-HSST 3)[Includes) Heparan sulfate N-deacetylase 3; Heparan sulfate N-sulfotransferase 3]."; (818:) "Bi-functional heparan sulfate N-deacetylase/N-sulfotransferase 4(Glucosaminyl N-deacetylase/N-sulfotransferase 4) (NDST-4) (N-heparan sulfate sulfotransferase 4) (N-HSST 4) [Includes: Heparan sulfate N-deacetylase 4; Heparan sulfate N-sulfotransferase 4]."; (819:) "Bi-functional methylenetetrahydrofolate dehydrogenase/cyclohydrolase, mitochondrial precursor [Includes: NAD-dependent methylenetetrahydrofolate dehydrogenase; Methenyltetrahydrofolate cyclohydrolase]."; (820:) bi-functional phosphopantetheine adenylyl transferase/dephosphoCoA kinase [Homo sapiens]; (821:) "Bi-functional protein NCOAT (Nuclear cytoplasmic O-GlcNAcase and acetyltransferase)

(Meningioma-expressed antigen 5) [Includes: Beta-hexosaminidase (N-acetyl-beta-glucosaminidase) (Beta-N-acetylhexosaminidase) (Hexosaminidase C) (N-acetyl-beta-D-glucosaminidase) (O-GlcNAcase); Histoneacetyltransferase (HAT)]."; (822:) "Bi-functional UDP-N-acetylglucosamine-2-epimerase/N-acetylmannosamine kinase(UDP-GlcNAc-2-epimerase/ManAc kinase) [Includes: UDP-N-acetylglucosamine 2-epimerase (Uridinediphosphate-N-acetylglucosamine-2-epimerase) (UDP-GlcNAc-2-epimerase); N-acetylmannosamine kinase (ManAckinase)]."; (823:) bile acid beta-glucosidase [*Homo sapiens*]; (824:) bile acid CoA:) Amino acid N-acyltransferase; (825:) Bile acid CoA:amino acid N-acyltransferase (BAT) (BACAT) (GlycineN-choloyltransferase) (Long-chain fatty-acyl-CoA hydrolase); (826:) bile acid Coenzyme A:) amino acid N-acyltransferase [*Homo sapiens*]; (827:) Bile acid receptor (Farnesoid X-activated receptor) (Farnesolreceptor HRR-1) (Retinoid X receptor-interacting protein 14) (RXR-interacting protein 14); (828:) Bile acyl-CoA synthetase (BACS) (Bile acid CoA ligase) (BA-CoAligase) (BAL) (Cholate-CoA ligase) (Very long-chain acyl-CoAsynthetase homolog 2) (VLCSH2) (VLCS-H2) (Very long chain acyl-CoAsynthetase-related protein) (VLACS-related) (VLACSR) (Fatty-acid-coenzyme A ligase, very long-chain 3) (Fatty acid transport protein 5) (FATP-5) (Solute carrier family 27 member 5); (829:) Bile salt sulfotransferase (Hydroxysteroid Sulfotransferase) (HST) (Dehydroepiandrosterone sulfotransferase) (DHEA-ST) (ST2) (ST2A3); (830:) Bile salt-activated lipase precursor (BAL) (Bile salt-stimulated lipase) (BSSL) (Carboxyl ester lipase) (Sterol esterase) (Cholesterol esterase) (Pancreatic lysophospholipase); (831:) biliverdin reductase B (flavin reductase (NADPH)) [*Homo sapiens*]; (832:) biphenyl hydrolase-like [*Homo sapiens*]; (833:) Bis(5'-adenosyl)-triphosphatase (Diadenosine-5',5''''-P1,P3-triphosphate hydrolase) (Dinucleosidetriphosphatase) (AP3A hydrolase) (AP3AASE) (Fragile histidine triad protein); (834:) BK158_1 (OTTHUMP00000040718) variant [*Homo sapiens*]; (835:) BK158_1 [*Homo sapiens*]; (836:) bleomycin hydrolase [*Homo sapiens*]; (837:) Blue-sensitive opsin (BOP) (Blue cone photoreceptor pigment); (838:) Bombesin receptor subtype-3 (BRS-3); (839:) bone morphogenetic protein 1 isoform 1, precursor [*Homo sapiens*]; (840:) bone morphogenetic protein 1 isoform 2, precursor [*Homo sapiens*]; (841:) bone morphogenetic protein 1 isoform 3, precursor [*Homo sapiens*]; (842:) Bone morphogenetic protein 1 precursor (BMP-1) (Procollagen C-proteinase) (PCP) (Mammalian tolloid protein) (mTld); (843:) Bone morphogenetic protein receptor type IA precursor (Serine/threonine-protein kinase receptor R5) (SKR5) (Activin receptor-like kinase 3) (ALK-3) (CD292 antigen); (844:) Bone morphogenetic protein receptor type IB precursor (CDw293antigen); (845:) Bone morphogenetic protein receptor type-2 precursor (Bonemorphogenetic protein receptor type II) (BMP type II receptor) (BMPR-II); (846:) bradykinin receptor B1 [*Homo sapiens*]; (847:) bradykinin receptor B2 [*Homo sapiens*]; (848:) brain creatine kinase [*Homo sapiens*]; (849:) brain glycogen phosphorylase [*Homo sapiens*]; (850:) brain-derived neurotrophic factor isoform a preproprotein [*Homo sapiens*]; (851:) brain-derived neurotrophic factor isoform b preproprotein [*Homo sapiens*]; (852:) brain-derived neurotrophic factor isoform c preproprotein [*Homo sapiens*]; (853:) Brain-specific angiogenesis inhibitor 1 precursor; (854:) Brain-specific angiogenesis inhibitor 2 precursor; (855:) Brain-specific angiogenesis inhibitor 3 precursor; (856:) branched chain acyltransferase precursor; (857:) branched chain aminotransferase 1, cytosolic [*Homo sapiens*]; (858:) branched chain aminotransferase 2, mitochondrial [*Homo sapiens*]; (859:) branched chain keto acid dehydrogenase E1, alpha polypeptide [*Homo sapiens*]; (860:) branching-enzyme interacting dual-specificity protein phosphatase BEDP [*Homo sapiens*]; (861:) Breast cancer type 1 susceptibility protein (RING finger protein53); (862:) Brefeldin A-inhibited guanine nucleotide-exchange protein 1(Brefeldin A-inhibited GEP 1) (p200 ARF-GEP1) (p200 ARF guanine nucleotide exchange factor); (863:) Brefeldin A-inhibited guanine nucleotide-exchange protein 2(Brefeldin A-inhibited GEP 2); (864:) bubblegum related protein [*Homo sapiens*]; (865:) butyrylcholinesterase precursor [*Homo sapiens*]; (866:) C→U-editing enzyme APOBEC-1 (Apolipoprotein B mRNA-editing enzyme1) (HEPR); (867:) C1 esterase inhibitor [*Homo sapiens*]; (868:) C10orf129 protein [*Homo sapiens*]; (869:) C1GALT1-specific chaperone 1 [*Homo sapiens*]; (870:) C1-tetrahydrofolate synthase [*Homo sapiens*]; (871:) "C-1-tetrahydrofolate synthase, cytoplasmic (C1-THF synthase)[Includes:) Methylenetetrahydrofolate dehydrogenase; Methenyltetrahydrofolate cyclohydrolase; Formyltetrahydrofolatesynthetase]."; (872:) C3a anaphylatoxin chemotactic receptor (C3a-R) (C3AR); (873:) C5a anaphylatoxin chemotactic receptor (C5a-R) (C5aR) (CD88antigen); (874:) C5a anaphylatoxin chemotactic receptor C5L2 (G-protein coupled receptor 77); (875:) C9orf3 protein [*Homo sapiens*]; (876:) C9orf95 protein [*Homo sapiens*]; (877:) Ca2+/calmodulin-dependent protein kinase (EC 2.7.1.123) II gammachain, splice form B—human; (878:) Ca2+/calmodulin-dependent protein kinase kinase beta-3 [*Homo sapiens*]; (879:) CAD protein [*Homo sapiens*]; (880:) cadherin 1, type 1 preproprotein [*Homo sapiens*]; (881:) Cadherin EGF LAG seven-pass G-type receptor 1 precursor (Flamingo homolog 2) (hFmi2); (882:) Cadherin EGF LAG seven-pass G-type receptor 2 precursor (Epidermal growth factor-like 2) (Multiple epidermal growth factor-like domains 3) (Flamingo 1); (883:) Cadherin EGF LAG seven-pass G-type receptor 3 precursor (Flamingo homolog 1) (hFmi1) (Multiple epidermal growth factor-like domains2) (Epidermal growth factor-like 1); (884:) Calcitonin gene-related peptide type 1 receptor precursor (CGRP type 1 receptor) (Calcitonin receptor-like receptor); (885:) calcitonin gene-related peptide-receptor component protein isoform a [*Homo sapiens*]; (886:) calcitonin gene-related peptide-receptor component protein isoform b [*Homo sapiens*]; (887:) calcitonin gene-related peptide-receptor component protein isoform c [*Homo sapiens*]; (888:) Calcitonin receptor precursor (CT-R); (889:) calcium activated nucleotidase 1 [*Homo sapiens*]; (890:) calcium receptor (clone phPCa-4.0)—human; (891:) calcium receptor (clone phPCaR-5.2)—human; (892:) Calcium/calmodulin-dependent 3',5'-cyclic nucleotidephosphodiesterase 1A (Cam-PDE 1A) (61 kDa Cam-PDE) (hCam-1); (893:) Calcium/calmodulin-dependent 3',5'-cyclic nucleotidephosphodiesterase 1B (Cam-PDE 1B) (63 kDa Cam-PDE); (894:) Calcium/calmodulin-dependent 3',5'-cyclic nucleotidephosphodiesterase 1C (Cam-PDE 1C) (hCam-3); (895:) calcium/calmodulin-dependent protein kinase I [*Homo sapiens*]; (896:) calcium/calmodulin-dependent protein kinase II delta isoform 1 [*Homo sapiens*]; (897:) calcium/calmodulin-dependent protein kinase II delta isoform 2 [*Homo sapiens*]; (898:) calcium/calmodulin-dependent protein kinase II delta isoform 3 [*Homo sapiens*]; (899:) calcium/calmodulin-dependent protein kinase II gamma isoform 1 [*Homo sapiens*]; (900:) calcium/calmodulin-dependent protein kinase II gamma isoform 2 [*Homo sapiens*]; (901:) calcium/calmodulin-dependent protein kinase II gamma isoform 3 [*Homo* sapiens]; (902:) calcium/calmodulin-dependent protein kinase II gamma isoform 4 [Homo sapiens]; (903:) calcium/calmodulin-dependent protein kinase II gamma isoform 5 [Homo sapiens]; (904:) calcium/calmodulin-dependent protein kinase II gamma isoform 6 [Homo sapiens]; (905:) calcium/calmodulin-dependent protein kinase IIA isoform 1 [Homo sapiens]; (906:) calcium/calmodulin-dependent protein kinase IIA isoform 2 [Homo sapiens]; (907:) calcium/calmodulin-dependent protein kinase IIB isoform 1 [Homo sapiens]; (908:) calcium/calmodulin-dependent protein kinase IIB isoform 2 [Homo sapiens]; (909:) calcium/calmodulin-dependent protein kinase IIB isoform 3 [Homo sapiens]; (910:) calcium/calmodulin-dependent protein kinase IIB isoform 4 [Homo sapiens]; (911:) calcium/calmodulin-dependent protein kinase IIB isoform 5 [Homo sapiens]; (912:) calcium/calmodulin-dependent protein kinase IIB isoform 6 [Homo sapiens]; (913:) calcium/calmodulin-dependent protein kinase IIB isoform 7 [Homo sapiens]; (914:) calcium/calmodulin-dependent protein kinase IIB isoform 8 [Homo sapiens]; (915:) calcium/calmodulin-dependent protein kinase IV [Homo sapiens]; (916:) Calcium/calmodulin-dependent protein kinase kinase 1(Calcium/calmodulin-dependent protein kinase kinase alpha) (CaM-kinase kinase alpha) (CaM-KK alpha) (CaMKK alpha) (CaMKK I) (CaM-kinase IV kinase); (917:) Calcium/calmodulin-dependent protein kinase kinase 2(Calcium/calmodulin-dependent protein kinase kinase beta) (CaM-kinase kinase beta) (CaM-KK beta) (CaMKK beta); (918:) Calcium/calmodulin-dependent protein kinase type 1 (CaM kinase I) (CaM-KI) (CaM kinase I alpha) (CaMKI-alpha); (919:) Calcium/calmodulin-dependent protein kinase type 1B (CaM kinase IB) (CaM kinase I beta) (CaMKI-beta) (CaM-KI beta) (Pregnancy up-regulated non-ubiquitously expressed CaM kinase); (920:) Calcium/calmodulin-dependent protein kinase type 1D (CaM kinase ID) (CaM kinase I delta) (CaMKI-delta) (CaM-KI delta) (CaMKI delta) (Camk1D) (CamKI-like protein kinase) (CKLiK); (921:) Calcium/calmodulin-dependent protein kinase type 1G (CaM kinase IG) (CaM kinase I gamma) (CaMKI gamma) (CaMKI-gamma) (CaM-KI gamma) (CaMKIG) (CaMK-like CREB kinase III) (CLICK III); (922:) Calcium/calmodulin-dependent protein kinase type II alpha chain(CaM-kinase II alpha chain) (CaM kinase II alpha subunit) (CaMK-II subunit alpha); (923:) Calcium/calmodulin-dependent protein kinase type II beta chain (CaM-kinase II beta chain) (CaM kinase II subunit beta) (CaMK-II subunit beta); (924:) Calcium/calmodulin-dependent protein kinase type II delta chain(CaM-kinase II delta chain) (CaM kinase II subunit delta) (CaMK-II subunit delta); (925:) Calcium/calmodulin-dependent protein kinase type II gamma chain(CaM-kinase II gamma chain) (CaM kinase II gamma subunit) (CaMK-II subunit gamma); (926:) Calcium/calmodulin-dependent protein kinase type IV (CAM kinase-GR) (CaMK IV); (927:) Calcium-dependent phospholipase A2 precursor (Phosphatidylcholine-2-acylhydrolase) (PLA2-10) (Group V phospholipase A2); (928:) calcium-independent phospholipase A2 [Homo sapiens]; (929:) calcium-sensing receptor [Homo sapiens]; (930:) calcium-transporting ATPase 2C1 isoform 1a [Homo sapiens]; (931:) calcium-transporting ATPase 2C1 isoform 1b [Homo sapiens]; (932:) calcium-transporting ATPase 2C1 isoform 1c [Homo sapiens]; (933:) calcium-transporting ATPase 2C1 isoform 1d [Homo sapiens]; (934:) Calcium-transporting ATPase type 2C member 1 (ATPase 2C1) (ATP-dependent Ca(2+) pump PMR1); (935:) Calmodulin (Vertebrate); (936:) calmodulin-like skin protein [Homo sapiens]; (937:) calnexin precursor [Homo sapiens]; (938:) calpain [Homo sapiens]; (939:) calpain 1, large subunit [Homo sapiens]; (940:) calpain 2, large subunit [Homo sapiens]; (941:) calpain 3 isoform a [Homo sapiens]; (942:) calpain 3 isoform b [Homo sapiens]; (943:) calpain 3 isoform c [Homo sapiens]; (944:) calpain 3 isoform d [Homo sapiens]; (945:) calpain 3 isoform e [Homo sapiens]; (946:) calpain 3 isoform f [Homo sapiens]; (947:) calpain 3 isoform g [Homo sapiens]; (948:) calpain 3 isoform h [Homo sapiens]; (949:) Calpain-1 catalytic subunit (Calpain-1 large subunit) (Calcium-activated neutral proteinase 1) (CANP 1) (Calpain mu-type) (muCANP) (Micromolar-calpain); (950:) Calpain-2 catalytic subunit precursor (Calpain-2 large subunit) (Calcium-activated neutral proteinase 2) (CANP 2) (Calpain M-type) (M-calpain) (Millimolar-calpain) (Calpain large polypeptide L2); (951:) Calpain-3 (Calpain L3) (Calpain p94) (Calcium-activated neutral proteinase 3) (CANP 3) (Muscle-specific calcium-activated neutral protease 3) (nCL-1); (952:) C-alpha-formyglycine-generating enzyme [Homo sapiens]; (953:) cAMP and cAMP-inhibited cGMP 3',5'-cyclic phosphodiesterase 10A; (954:) cAMP responsive element binding protein 3 [Homo sapiens]; (955:) cAMP-dependent protein kinase catalytic subunit alpha isoform 1 [Homo sapiens]; (956:) cAMP-dependent protein kinase catalytic subunit alpha isoform 2 [Homo sapiens]; (957:) cAMP-dependent protein kinase inhibitor alpha (PKI-alpha) (cAMP-dependent protein kinase inhibitor, muscle/brain isoform); (958:) cAMP-dependent protein kinase inhibitor beta (PKI-beta); (959:) cAMP-dependent protein kinase inhibitor gamma (PKI-gamma); (960:) cAMP-dependent protein kinase type I-alpha regulatory subunit(Tissue-specific extinguisher 1) (TSE1); (961:) cAMP-dependent protein kinase type I-beta regulatory subunit; (962:) cAMP-dependent protein kinase type II-alpha regulatory subunit; (963:) cAMP-dependent protein kinase type II-beta regulatory subunit; (964:) cAMP-dependent protein kinase, alpha-catalytic subunit (PKAC-alpha); (965:) cAMP-dependent protein kinase, beta-catalytic subunit (PKA C-beta); (966:) cAMP-dependent protein kinase, gamma-catalytic subunit (PKAC-gamma); (967:) cAMP-specific 3',5'-cyclic phosphodiesterase 4A (DPDE2) (PDE46); (968:) cAMP-specific 3',5'-cyclic phosphodiesterase 4B (DPDE4) (PDE32); (969:) cAMP-specific 3',5'-cyclic phosphodiesterase 4C (DPDE1) (PDE21); (970:) cAMP-specific 3',5'-cyclic phosphodiesterase 4D (DPDE3) (PDE43); (971:) cAMP-specific 3',5'-cyclic phosphodiesterase 7B; (972:) cAMP-specific phosphodiesterase 4D [Homo sapiens]; (973:) Cannabinoid receptor 1 (CB1) (CB-R) (CANN6); (974:) Cannabinoid receptor 2 (CB2) (CB-2) (CX5); (975:) CAP10-like 46 kDa protein precursor (Myelodysplastic syndromes relative protein); (976:) capping enzyme 1 [Homo sapiens]; (977:) capping enzyme 1A [Homo sapiens]; (978:) capping enzyme 1B [Homo sapiens]; (979:) Carbamoyl-phosphate synthase [ammonia], mitochondrial precursor (Carbamoyl-phosphate synthetase I) (CPSase I); (980:) carbamoyl-phosphate synthetase 1, mitochondrial [Homo sapiens]; (981:) Carbamoyl-phosphate synthetase 2, aspartate transcarbamylase, and dihydroorotase [Homo sapiens]; (982:) carbamoylphosphate synthetase 2/aspartate transcarbamylase/dihydroorotase [Homo sapiens]; (983:) carbohydrate (N-acetylglucosamine 6-O) sulfotransferase 6 [Homo sapiens]; (984:) carbohydrate (N-acetylglucosamine 6-O) sulfotransferase 7 [Homo sapiens]; (985:) carbohydrate (N-acetylglucosamine-6-O) sulfotransferase 2 [Homo sapiens]; (986:) Carbohydrate sulfotransferase 10 (HNK-1 sulfotransferase) (HNK1ST) (HNK-1ST) (huHNK-1ST); (987:) Carbohydrate sulfotransferase 11 (Chondroitin 4-O-sulfotransferase1) (Chondroitin 4-sulfotransferase 1) (C4ST) (C4ST-1) (C4S-1); (988:) Carbohydrate sulfotransferase 12 (Chondroitin 4-O-sulfotransferase2) (Chondroitin 4-sulfotransferase 2) (C4ST-2) (Sulfotransferase Hlo); (989:) Carbohydrate sulfotransferase 13 (Chondroitin 4-O-sulfotransferase3) (Chondroitin 4-sulfotransferase 3) (C4ST3) (C4ST-3); (990:) Carbohydrate sulfotransferase 2 (N-acetylglucosamine-6-O-sulfotransferase 1) (GlcNAc6ST-1) (Gn6ST) (Galactose/N-acetylglucosamine/N-acetylglucosamine-6-O-sulfotransferase 2) (GST-2); (991:) Carbohydrate sulfotransferase 3 (Chondroitin 6-sulfotransferase) (Chondroitin 6-O-sulfotransferase 1) (C6ST-1) (C6ST) (Galactose/N-acetylglucosamine/N-acetylglucosamine-6-O-sulfotransferase 0) (GST-0); (992:) Carbohydrate sulfotransferase 4 (N-acetylglucosamine-6-O-sulfotransferase 2) (GlcNAc6ST-2) (High endothelial cellsN-acetylglucosamine 6-O-sulfotransferase) (HEC-GlcNAc6ST) (L-selectin ligand sulfotransferase) (LSST) (Galactose/N-acetylglucosamine/N-acetylglucosamine-6-O-sulfotransferase 3) (GST-3); (993:) Carbohydrate sulfotransferase 7 (Chondroitin 6-sulfotransferase 2) (C6ST-2) (N-acetylglucosamine 6-O-sulfotransferase 1) (GlcNAc6ST-4) (Galactose/N-acetylglucosamine/N-acetylglucosamine-6-O-sulfotransferase 5) (GST-5); (994:) Carbohydrate sulfotransferase 8(N-acetylgalactosamine-4-O-sulfotransferase 1) (GalNAc-4-O-sulfotransferase 1) (GalNAc-4-ST1) (GalNAc4ST-1); (995:) Carbohydrate sulfotransferase 9(N-acetylgalactosamine-4-O-sulfotransferase 2) (GalNAc-4-O-sulfotransferase 2) (GalNAc-4-ST2); (996:) Carbohydrate sulfotransferase D4ST1 (Dermatan 4-sulfotransferase 1) (D4ST-1) (hD4ST); (997:) Carbonic anhydrase 12 precursor (Carbonic anhydrase XII) (Carbonatedehydratase XII) (CA-XII) (Tumor antigen HOM-RCC-3.1.3); (998:) Carbonic anhydrase 4 precursor (Carbonic anhydrase IV) (Carbonatedehydratase IV) (CA-IV); (999:) Carbonic Anhydrase I (E.C.4.2.1.1) Complexed With Bicarbonate; (1000:) carbonic anhydrase I [*Homo sapiens*]; (1001:) carbonic anhydrase II [*Homo sapiens*]; (1002:) carbonic anhydrase IV precursor [*Homo sapiens*]; (1003:) carbonic anhydrase IX precursor [*Homo sapiens*]; (1004:) carbonic anhydrase VIII [*Homo sapiens*]; (1005:) carbonyl reductase 1 [*Homo sapiens*]; (1006:) carbonyl reductase 3 [*Homo sapiens*]; (1007:) carboxyl ester lipase precursor [*Homo sapiens*]; (1008:) carboxylesterase 1 isoform a precursor [*Homo sapiens*]; (1009:) carboxylesterase 1 isoform b precursor [*Homo sapiens*]; (1010:) carboxylesterase 1 isoform c precursor [*Homo sapiens*]; (1011:) carboxylesterase 2 isoform 1 [*Homo sapiens*]; (1012:) carboxylesterase 2 isoform 2 [*Homo sapiens*]; (1013:) carboxylesterase; (1014:) carboxypeptidase A2 (pancreatic) [*Homo sapiens*]; (1015:) carboxypeptidase A4 preproprotein [*Homo sapiens*]; (1016:) carboxypeptidase A5 [*Homo sapiens*]; (1017:) carboxypeptidase B precursor [*Homo sapiens*]; (1018:) Carboxypeptidase D precursor (Metallocarboxypeptidase D) (gp180); (1019:) carboxypeptidase E precursor [*Homo sapiens*]; (1020:) Carboxypeptidase M precursor (CPM); (1021:) carboxypeptidase N, polypeptide 1, 50 kD precursor [*Homo sapiens*]; (1022:) carboxypeptidase Z isoform 1 [*Homo sapiens*]; (1023:) carboxypeptidase Z isoform 2 precursor [*Homo sapiens*]; (1024:) carboxypeptidase Z isoform 3 [*Homo sapiens*]; (1025:) Carboxypeptidase Z precursor (CPZ); (1026:) carnitine acetyltransferase isoform 1 precursor [*Homo sapiens*]; (1027:) carnitine acetyltransferase isoform 2 [*Homo sapiens*]; (1028:) carnitine acetyltransferase isoform 3 precursor [*Homo sapiens*]; (1029:) Carnitine O-acetyltransferase (Carnitine acetylase) (CAT) (Carnitine acetyltransferase) (CrAT); (1030:) carnitine O-octanoyltransferase [*Homo sapiens*]; (1031:) Carnitine O-palmitoyltransferase I, liver isoform (CPT I) (CPTI-L) (Carnitine palmitoyltransferase 1A); (1032:) carnitine palmitoyltransferase 1A isoform 1 [*Homo sapiens*]; (1033:) carnitine palmitoyltransferase 1A isoform 2 [*Homo sapiens*]; (1034:) carnitine palmitoyltransferase 1B isoform a [*Homo sapiens*]; (1035:) carnitine palmitoyltransferase 1B isoform b [*Homo sapiens*]; (1036:) "Cartilage intermediate layer protein 1 precursor (CILP-1) (Cartilage intermediate-layer protein) [Contains:] Cartilage intermediate layer protein 1 C1; Cartilage intermediate layer protein 1 C2]."; (1037:) Cas-Br-M (murine) ecotropic retroviral transforming sequence [*Homo sapiens*]; (1038:) casein alpha s1 isoform 1 [*Homo sapiens*]; (1039:) casein alpha s1 isoform 2 [*Homo sapiens*]; (1040:) casein beta [*Homo sapiens*]; (1041:) casein kinase 1, gamma 1 [*Homo sapiens*]; (1042:) casein kinase 1, gamma 1 isoform L [*Homo sapiens*]; (1043:) casein kinase 2, alpha prime polypeptide [*Homo sapiens*]; (1044:) casein kinase 2, beta polypeptide [*Homo sapiens*]; (1045:) Casein kinase I isoform delta (CKI-delta) (CKId); (1046:) casein kinase II alpha 1 subunit isoform a [*Homo sapiens*]; (1047:) casein kinase II alpha 1 subunit isoform b [*Homo sapiens*]; (1048:) CASH alpha protein [*Homo sapiens*]; (1049:) CASP1 protein [*Homo sapiens*]; (1050:) CASP10 protein [*Homo sapiens*]; (1051:) CASP12P1 [*Homo sapiens*]; (1052:) CASP2 [*Homo sapiens*]; (1053:) CASP8 and FADD-like apoptosis regulator [*Homo sapiens*]; (1054:) "CASP8 and FADD-like apoptosis regulator precursor (Cellular FLICE-like inhibitory protein) (c-FLIP) (Caspase-eight-related protein) (Casper) (Caspase-like apoptosis regulatory protein) (CLARP) (MACH-related inducer of toxicity) (MRIT) (Caspase homolog) (CASH) (Inhibitor of FLICE) (I-FLICE) (FADD-like antiapoptotic molecule 1) (FLAME-1) (Usurpin) [Contains:] CASP8 and FADD-like apoptosis regulator subunit p43; CASP8 and FADD-like apoptosis regulator subunit p12]."; (1055:) CASP8 protein [*Homo sapiens*]; (1056:) caspase 1 isoform alpha precursor [*Homo sapiens*]; (1057:) caspase 1 isoform alpha precursor variant [*Homo sapiens*]; (1058:) caspase 1 isoform beta precursor [*Homo sapiens*]; (1059:) caspase 1 isoform delta [*Homo sapiens*]; (1060:) caspase 1 isoform epsilon [*Homo sapiens*]; (1061:) caspase 1 isoform gamma precursor [*Homo sapiens*]; (1062:) Caspase 1, apoptosis-related cysteine peptidase (interleukin 1,beta, convertase) [*Homo sapiens*]; (1063:) caspase 10 [*Homo sapiens*]; (1064:) caspase 10 isoform a preproprotein [*Homo sapiens*]; (1065:) caspase 10 isoform b preproprotein [*Homo sapiens*]; (1066:) caspase 10 isoform d preproprotein [*Homo sapiens*]; (1067:) caspase 10, apoptosis-related cysteine peptidase [*Homo sapiens*]; (1068:) caspase 14 precursor [*Homo sapiens*]; (1069:) Caspase 14, apoptosis-related cysteine peptidase [*Homo sapiens*]; (1070:) caspase 2 isoform 1 preproprotein [*Homo sapiens*]; (1071:) caspase 2 isoform 2 precursor variant [*Homo sapiens*]; (1072:) caspase 2 isoform 3 [*Homo sapiens*]; (1073:) Caspase 2, apoptosis-related cysteine peptidase (neural precursor cell expressed, developmentally down-regulated 2) [*Homo sapiens*]; (1074:) caspase 2, apoptosis-related cysteine protease (neural precursor cell expressed, developmentally down-regulated 2) [*Homo sapiens*]; (1075:) caspase 3 preproprotein [*Homo sapiens*]; (1076:) Caspase 3, apoptosis-related cysteine peptidase [*Homo sapiens*]; (1077:) caspase 3, apoptosis-related cysteine protease [*Homo sapiens*]; (1078:) caspase 4 isoform alpha precursor [*Homo sapiens*]; (1079:) caspase 4 isoform delta [*Homo sapiens*]; (1080:) caspase 4 isoform gamma precursor [*Homo sapiens*]; (1081:) Caspase 4, apoptosis-related cysteine peptidase [*Homo sapiens*]; (1082:) caspase 5 precursor [*Homo sapiens*]; (1083:) Caspase 5, apoptosis-related cysteine peptidase [*Homo sapiens*]; (1084:) caspase 6 isoform alpha preproprotein [*Homo*

*sapiens*]; (1085:) caspase 6 isoform beta [*Homo sapiens*]; (1086:) Caspase 6, apoptosis-related cysteine peptidase [*Homo sapiens*]; (1087:) caspase 6, apoptosis-related cysteine protease [*Homo sapiens*]; (1088:) caspase 7 isoform alpha [*Homo sapiens*]; (1089:) caspase 7 isoform alpha precursor [*Homo sapiens*]; (1090:) caspase 7 isoform beta [*Homo sapiens*]; (1091:) caspase 7 isoform delta [*Homo sapiens*]; (1092:) Caspase 7, apoptosis-related cysteine peptidase [*Homo sapiens*]; (1093:) caspase 7, apoptosis-related cysteine protease [*Homo sapiens*]; (1094:) caspase 8 isoform A [*Homo sapiens*]; (1095:) caspase 8 isoform B precursor [*Homo sapiens*]; (1096:) caspase 8 isoform C [*Homo sapiens*]; (1097:) caspase 8 isoform E [*Homo sapiens*]; (1098:) caspase 8, apoptosis-related cysteine peptidase [*Homo sapiens*]; (1099:) caspase 9 isoform alpha preproprotein [*Homo sapiens*]; (1100:) caspase 9 isoform alpha preproprotein variant [*Homo sapiens*]; (1101:) caspase 9 isoform beta preproprotein [*Homo sapiens*]; (1102:) caspase 9 short isoform [*Homo sapiens*]; (1103:) Caspase 9, apoptosis-related cysteine peptidase [*Homo sapiens*]; (1104:) caspase 9, apoptosis-related cysteine protease [*Homo sapiens*]; (1105:) caspase-1 dominant-negative inhibitor pseudo-ICE isoform 1 [*Homo sapiens*]; (1106:) caspase-1 dominant-negative inhibitor pseudo-ICE isoform 2 [*Homo sapiens*]; (1107:) caspase-1 isoform zeta precursor [*Homo sapiens*]; (1108:) "Caspase-1 precursor (CASP-1) (Interleukin-1 beta convertase) (IL-1BC) (IL-1 beta-converting enzyme) (ICE) (Interleukin-1beta-converting enzyme) (p45) [Contains:) Caspase-1 p20 subunit; Caspase-1 p10 subunit]."; (1109:) "Caspase-10 precursor (CASP-10) (ICE-like apoptotic protease 4) (Apoptotic protease Mch-4) (FAS-associated death domain proteininter leukin-1 B-converting enzyme 2) (FLICE2) [Contains:) Caspase-10subunit p23/17; Caspase-10 subunit p12]."; (1110:) caspase-10/d [*Homo sapiens*]; (1111:) caspase-10a [*Homo sapiens*]; (1112:) caspase-10b [*Homo sapiens*]; (1113:) "Caspase-14 precursor (CASP-14) [Contains:) Caspase-14 subunit 1;Caspase-14 subunit 2]."; (1114:) "Caspase-2 precursor (CASP-2) (ICH-1 protease) (ICH-1L/1S)[Contains:) Caspase-2 subunit p18; Caspase-2 subunit p13; Caspase-2subunit p12]."; (1115:) caspase-3 [*Homo sapiens*]; (1116:) "Caspase-3 precursor (CASP-3) (Apopain) (Cysteine protease CPP32) (Yama protein) (CPP-32) (SREBP cleavage activity 1) (SCA-1)[Contains:) Caspase-3 p17 subunit; Caspase-3 p12 subunit]."; (1117:) "Caspase-4 precursor (CASP-4) (ICH-2 protease) (TX protease) (ICE(rel)-II) [Contains:) Caspase-4 subunit 1; Caspase-4 subunit 2]."; (1118:) "Caspase-5 precursor (CASP-5) (ICH-3 protease) (TY protease) (ICE(rel)-III) [Contains:) Caspase-5 subunit p20; Caspase-5 subunit p10]."; (1119:) caspase-5/b [*Homo sapiens*]; (1120:) caspase-5/f [*Homo sapiens*]; (1121:) "Caspase-6 precursor (CASP-6) (Apoptotic protease Mch-2) [Contains: Caspase-6 subunit p18; Caspase-6 subunit p11]."; (1122:) "Caspase-7 precursor (CASP-7) (ICE-like apoptotic protease 3) (ICE-LAP3) (Apoptotic protease Mch-3) (CMH-1) [Contains:) Caspase-7subunit p20; Caspase-7 subunit p11]."; (1123:) caspase-8 [*Homo sapiens*]; (1124:) "Caspase-8 precursor (CASP-8) (ICE-like apoptotic protease 5) (MORT1-associated CED-3 homolog) (MACH) (FADD-homologous ICE/CED-3-like protease) (FADD-like ICE) (FLICE) (Apoptotic cysteine protease) (Apoptotic protease Mch-5) (CAP4) [Contains: Caspase-8 subunit p18; Caspase-8 subunit p10]."; (1125:) caspase-8L [*Homo sapiens*]; (1126:) Caspase-9 [*Homo sapiens*]; (1127:) caspase-9 beta [*Homo sapiens*]; (1128:) "Caspase-9 precursor (CASP-9) (ICE-like apoptotic protease 6) (ICE-LAP6) (Apoptotic protease Mch-6) (Apoptotic protease-activating factor 3) (APAF-3) [Contains:) Caspase-9 subunit p35; Caspase-9 subunit p10]."; (1129:) caspase-9S precursor [*Homo sapiens*]; (1130:) caspase-like apoptosis regulatory protein [*Homo sapiens*]; (1131:) Casper [*Homo sapiens*]; (1132:) catalase [*Homo sapiens*]; (1133:) Catechol O-methyltransferase; (1134:) catechol-O-methyltransferase isoform MB-COMT [*Homo sapiens*]; (1135:) catechol-O-methyltransferase isoform S-COMT [*Homo sapiens*]; (1136:) catenin (cadherin-associated protein), beta 1, 88 kDa [*Homo sapiens*]; (1137:) cathepsin B preproprotein [*Homo sapiens*]; (1138:) cathepsin C isoform a preproprotein [*Homo sapiens*]; (1139:) cathepsin C isoform b precursor [*Homo sapiens*]; (1140:) cathepsin D preproprotein [*Homo sapiens*]; (1141:) Cathepsin E precursor; (1142:) Cathepsin F precursor (CATSF); (1143:) cathepsin G preproprotein [*Homo sapiens*]; (1144:) cathepsin H isoform a preproprotein [*Homo sapiens*]; (1145:) cathepsin H isoform b precursor [*Homo sapiens*]; (1146:) cathepsin K preproprotein [*Homo sapiens*]; (1147:) cathepsin L preproprotein [*Homo sapiens*]; (1148:) Cathepsin L2 precursor (Cathepsin V) (Cathepsin U); (1149:) cathepsin O [*Homo sapiens*]; (1150:) Cathepsin O precursor; (1151:) cathepsin O preproprotein [*Homo sapiens*]; (1152:) cathepsin S [*Homo sapiens*]; (1153:) cathepsin S preproprotein [*Homo sapiens*]; (1154:) Cation-dependent mannose-6-phosphate receptor precursor (CD Man-6-Preceptor) (CD-MPR) (46 kDa mannose 6-phosphate receptor) (MPR 46); (1155:) cation-dependent mannose-6-phosphate receptor precursor [*Homo sapiens*]; (1156:) Cation-independent mannose-6-phosphate receptor precursor (CIMan-6-P receptor) (CI-MPR) (M6PR) (Insulin-like growth factor 2receptor) (Insulin-like growth factor II receptor) (IGF-II receptor) (M6P/IGF2 receptor) (M6P/IGF2R) (300 kDa mannose6-phosphate receptor) (MPR 300) (MPR300) (CD222 antigen); (1157:) caveolin 1 [*Homo sapiens*]; (1158:) CBS protein [*Homo sapiens*]; (1159:) C-C chemokine receptor type 1 (C-C CKR-1) (CC-CKR-1) (CCR-1) (CCR1) (Macrophage inflammatory protein 1-alpha receptor) (MIP-1alpha-R) (RANTES-R) (HM145) (LD78 receptor) (CD191 antigen); (1160:) C-C chemokine receptor type 10 (C-C CKR-10) (CC-CKR-10) (CCR-10) (G-protein coupled receptor 2); (1161:) C-C chemokine receptor type 11 (C-C CKR-11) (CC-CKR-11) (CCR-11) (CC chemokine receptor-like 1) (CCRL1) (CCX CKR); (1162:) C-C chemokine receptor type 2 (C-C CKR-2) (CC-CKR-2) (CCR-2) (CCR2) (Monocyte chemoattractant protein 1 receptor) (MCP-1-R) (CD192antigen); (1163:) C-C chemokine receptor type 3 (C-C CKR-3) (CC-CKR-3) (CCR-3) (CCR3) (CKR3) (Eosinophil eotaxin receptor) (CD193 antigen); (1164:) C-C chemokine receptor type 4 (C-C CKR-4) (CC-CKR-4) (CCR-4) (CCR4) (K5-5); (1165:) C-C chemokine receptor type 5 (C-C CKR-5) (CC-CKR-5) (CCR-5) (CCR5) (HIV-1 fusion coreceptor) (CHEMRI3) (CD195 antigen); (1166:) C-C chemokine receptor type 6 (C-C CKR-6) (CC-CKR-6) (CCR-6) (LARC receptor) (GPR-CY4) (GPRCY4) (Chemokine receptor-like 3) (CKR-L3) (DRY6) (G-protein coupled receptor 29) (CD196 antigen); (1167:) C-C chemokine receptor type 7 precursor (C-C CKR-7) (CC-CKR-7) (CCR-7) (MIP-3 beta receptor) (EBV-induced G-protein coupled receptor 1) (EBI1) (BLR2) (CD197 antigen) (CDw197); (1168:) C-C chemokine receptor type 8 (C-C CKR-8) (CC-CKR-8) (CCR-8) (GPR-CY6) (GPRCY6) (Chemokine receptor-like 1) (CKR-L1) (TER1) (CMKBRL2) (CC-chemokine receptor CHEMR1) (CDw198 antigen); (1169:) C-C chemokine receptor type 9 (C-C CKR-9) (CC-CKR-9) (CCR-9) (GPR-9-6) (G-protein coupled receptor 28) (CDw199 antigen); (1170:) C-C chemokine receptor-like 2 (Putative MCP-1 chemokine receptor) (Chemokine receptor CCR11)

(Chemokine receptor X); (1171:) CCR4-NOT transcription complex, subunit 4 isoform a [*Homo sapiens*]; (1172:) CCR4-NOT transcription complex, subunit 4 isoform b [*Homo sapiens*]; (1173:) CD160 antigen precursor (Natural killer cell receptor BY55); (1174:) CD180 antigen precursor (Lymphocyte antigen 64) (Radioprotective 105 kDa protein); (1175:) CD200 antigen isoform a precursor [*Homo sapiens*]; (1176:) CD200 antigen isoform b [*Homo sapiens*]; (1177:) CD209 antigen (Dendritic cell-specific ICAM-3-grabbing nonintegrin1) (DC-SIGN1) (DC-SIGN) (C-type lectin domain family 4 member L); (1178:) CD226 antigen precursor (DNAX accessory molecule 1) (DNAM-1); (1179:) CD2-associated protein (Cas ligand with multiple SH3 domains) (Adapter protein CMS); (1180:) CD38 antigen [*Homo sapiens*]; (1181:) CD40 antigen isoform 1 precursor [*Homo sapiens*]; (1182:) CD40 antigen isoform 2 precursor [*Homo sapiens*]; (1183:) CD44 antigen precursor (Phagocytic glycoprotein I) (PGP-1) (HUTCH-I) (Extracellular matrix receptor-III) (ECMR-III) (GP90lymphocyte homing/adhesion receptor) (Hermes antigen) (Hyaluronate receptor) (Heparan sulfate proteoglycan) (Epican) (CDw44); (1184:) CD53 antigen [*Homo sapiens*]; (1185:) CD63 antigen isoform A [*Homo sapiens*]; (1186:) CD63 antigen isoform B [*Homo sapiens*]; (1187:) CD97 antigen precursor (Leukocyte antigen CD97); (1188:) CDC16 homolog [*Homo sapiens*]; (1189:) CDC26 subunit of anaphase promoting complex [*Homo sapiens*]; (1190:) Cdc34 [*Homo sapiens*]; (1191:) Cdk5 and Abl enzyme substrate 1 [*Homo sapiens*]; (1192:) Cdk5 and Abl enzyme substrate 2 [*Homo sapiens*]; (1193:) CDK5 and ABL1 enzyme substrate 1 (Interactor with CDK3 1) (Ik3-1); (1194:) CDK5 and ABL1 enzyme substrate 2 (Interactor with CDK3 2) (Ik3-2); (1195:) CDP-diacylglycerol-inositol 3-phosphatidyltransferase (Phosphatidylinositol synthase) (Ptdlns synthase) (PI synthase); (1196:) Cell division control protein 2 homolog (p34 protein kinase) (Cyclin-dependent kinase 1) (CDK1); (1197:) Cell division control protein 42 homolog precursor (G25KGTP-binding protein); (1198:) cell division cycle 2 protein isoform 1 [*Homo sapiens*]; (1199:) cell division cycle 2 protein isoform 2 [*Homo sapiens*]; (1200:) cell division cycle 2-like 1 (PITSLRE proteins) isoform 1 [*Homo sapiens*]; (1201:) cell division cycle 2-like 1 (PITSLRE proteins) isoform 2 [*Homo sapiens*]; (1202:) cell division cycle 2-like 1 (PITSLRE proteins) isoform 3 [*Homo sapiens*]; (1203:) cell division cycle 2-like 1 (PITSLRE proteins) isoform 4 [*Homo sapiens*]; (1204:) cell division cycle 2-like 1 (PITSLRE proteins) isoform 5 [*Homo sapiens*]; (1205:) cell division cycle 2-like 1 (PITSLRE proteins) isoform 6 [*Homo sapiens*]; (1206:) cell division cycle 2-like 1 (PITSLRE proteins) isoform 8 [*Homo sapiens*]; (1207:) cell division cycle 2-like 1 (PITSLRE proteins) isoform 9 [*Homo sapiens*]; (1208:) Cell division cycle 34 [*Homo sapiens*]; (1209:) Cell division cycle 34 homolog (*S. cerevisiae*) [*Homo sapiens*]; (1210:) cell division cycle protein 23 [*Homo sapiens*]; (1211:) cell division cycle protein 27 [*Homo sapiens*]; (1212:) Cell division protein kinase 2 (p33 protein kinase); (1213:) Cell division protein kinase 4 (Cyclin-dependent kinase 4) (PSK-J3); (1214:) Cell division protein kinase 7 (CDK-activating kinase) (CAK) (TFIIH-basal transcription factor complex kinase subunit) (39 kDa proteinkinase) (P39 Mo15) (STK1) (CAK1); (1215:) Cell surface glycoprotein OX2 receptor precursor (CD200 cell surface glycoprotein receptor); (1216:) Centaurin-gamma 1 (ARF-GAP with GTP-binding protein-like, ankyrin repeat and pleckstrin homology domains 2) (AGAP-2) (Phosphatidylinositol-3-kinase enhancer) (PIKE) (GTP-binding and GTPase-activating protein 2) (GGAP2); (1217:) Centaurin-gamma 2 (ARF-GAP with GTP-binding protein-like, ankyrin repeat and pleckstrin homology domains 1) (AGAP-1) (GTP-binding and GTPase-activating protein 1) (GGAP1); (1218:) Centaurin-gamma 3 (ARF-GAP with GTP-binding protein-like, ankyrin repeat and pleckstrin homology domains 3) (AGAP-3) (MR1-interacting protein) (MRIP-1) (CRAM-associated GTPase) (CRAG); (1219:) CGI-02 protein [*Homo sapiens*]; (1220:) CGI-11 protein [*Homo sapiens*]; (1221:) CGI-76 protein [*Homo sapiens*]; (1222:) cGMP-dependent protein kinase 1, alpha isozyme (CGK 1 alpha) (cGKI-alpha); (1223:) cGMP-dependent protein kinase 1, beta isozyme (cGK 1 beta) (cGKI-beta); (1224:) cGMP-dependent protein kinase 2 (CGK 2) (cGKII) (Type IIc GMP-dependent protein kinase); (1225:) cGMP-inhibited 3',5'-cyclic phosphodiesterase A (Cyclic GMP-inhibited phosphodiesterase A) (CGI-PDE A); (1226:) cGMP-inhibited 3',5'-cyclic phosphodiesterase B (Cyclic GMP-inhibited phosphodiesterase B) (CGI-PDE B) (CGIPDE1) (CGIP1); (1227:) cGMP-specific 3',5'-cyclic phosphodiesterase (CGB-PDE) (cGMP-binding cGMP-specific phosphodiesterase); (1228:) CHCHD2 protein [*Homo sapiens*]; (1229:) CHCHD4 protein [*Homo sapiens*]; (1230:) chemokine (C-C motif) ligand 14 isoform 1 precursor [*Homo sapiens*]; (1231:) chemokine (C-C motif) ligand 14 isoform 2 precursor [*Homo sapiens*]; (1232:) chemokine (C-C motif) ligand 7 precursor [*Homo sapiens*]; (1233:) chemokine (C-C motif) receptor 2 isoform A [*Homo sapiens*]; (1234:) chemokine (C-C motif) receptor 2 isoform B [*Homo sapiens*]; (1235:) chemokine (C-X3-C motif) ligand 1 [*Homo sapiens*]; (1236:) chemokine (C-X-C motif) ligand 12 (stromal cell-derived factor 1)isoform alpha [*Homo sapiens*]; (1237:) chemokine (C-X-C motif) ligand 12 (stromal cell-derived factor 1)isoform beta [*Homo sapiens*]; (1238:) chemokine (C-X-C motif) ligand 12 (stromal cell-derived factor 1)isoform gamma [*Homo sapiens*]; (1239:) Chemokine receptor-like 1 (G-protein coupled receptor DEZ) (G-protein coupled receptor ChemR23); (1240:) Chemokine receptor-like 2 (G-protein coupled receptor 30) (IL8-related receptor DRY12) (Flow-induced endothelial G-protein coupled receptor) (FEG-1) (GPCR-BR); (1241:) Chemokine XC receptor 1 (XC chemokine receptor 1) (Lymphotactin receptor) (G-protein coupled receptor 5); (1242:) Chemokine-binding protein 2 (Chemokine-binding protein D6) (C-Cchemokine receptor D6) (Chemokine receptor CCR-9) (Chemokine receptor CCR-10); (1243:) chitotriosidase [*Homo sapiens*]; (1244:) chitotriosidase precursor [*Homo sapiens*]; (1245:) Chitotriosidase-1 precursor (Chitinase-1); (1246:) chloride channel 6 isoform CIC-6a [*Homo sapiens*]; (1247:) chloride channel 6 isoform CIC-6b [*Homo sapiens*]; (1248:) chloride channel 6 isoform CIC-6c [*Homo sapiens*]; (1249:) chloride channel 6 isoform CIC-6d [*Homo sapiens*]; (1250:) cholecystokinin A receptor [*Homo sapiens*]; (1251:) cholecystokinin preproprotein [*Homo sapiens*]; (1252:) Cholecystokinin type A receptor (CCK-A receptor) (CCK-AR) (Cholecystokinin-1 receptor) (CCK1-R); (1253:) cholesterol 25-hydroxylase [*Homo sapiens*]; (1254:) cholesterol side-chain cleavage enzyme P450scc (EC 1.14.15.67); (1255:) choline acetyltransferase [*Homo sapiens*]; (1256:) choline acetyltransferase isoform 1 [*Homo sapiens*]; (1257:) choline acetyltransferase isoform 2 [*Homo sapiens*]; (1258:) choline kinase alpha isoform a [*Homo sapiens*]; (1259:) choline kinase alpha isoform b [*Homo sapiens*]; (1260:) Choline O-acetyltransferase (CHOACTase) (Choline acetylase) (ChAT); (1261:) choline phosphotransferase 1 [*Homo sapiens*]; (1262:) choline/ethanolamine kinase isoform a [*Homo sapiens*]; (1263:) choline/ethanolamine kinase isoform b [*Homo sapiens*]; (1264:) Choline-phosphate cytidylyltransferase A (Phosphorylcholine transferase A) (CTP: phosphocholine cytidylyltransferase A) (CT A) (CCT A) (CCT-alpha); (1265:) cholinephosphotransferase [*Homo sapiens*]; (1266:) cholinergic receptor, nicotinic, alpha 4 subunit precursor [*Homo sapiens*]; (1267:) Cholinesterase precursor (Acylcholine acylhydrolase) (Cholineesterase II) (Butyrylcholine esterase) (Pseudocholinesterase); (1268:) chondroitin beta-1,4 N-acetylgalactosaminyltransferase [*Homo sapiens*]; (1269:) chondroitin beta-1,4 N-acetylgalactosaminyltransferase 2 [*Homo sapiens*]; (1270:) Chondroitin beta-1,4-N-acetylgalactosaminyltransferase 1(beta4GalNAcT-1); (1271:) Chondroitin beta-1,4-N-acetylgalactosaminyltransferase 2(GalNAcT-2) (beta4GalNAcT-2); (1272:) chondroitin sulfate proteoglycan 2 (versican) [*Homo sapiens*]; (1273:) chondroitin sulfate synthase 3 [*Homo sapiens*]; (1274:) chromatin-specific transcription elongation factor large subunit [*Homo sapiens*]; (1275:) chymase 1, mast cell preproprotein [*Homo sapiens*]; (1276:) Chymase precursor (Mast cell protease I); (1277:) chymotrypsin-like [*Homo sapiens*]; (1278:) Chymotrypsin-like serine proteinase (LCLP); (1279:) Ciliary neurotrophic factor receptor alpha precursor (CNTFR alpha); (1280:) citrate synthase precursor, isoform a [*Homo sapiens*]; (1281:) citrate synthase precursor, isoform b [*Homo sapiens*]; (1282:) Class B basic helix-loop-helix protein 2 (bHLHB2) (Differentially expressed in chondrocytes protein 1) (DEC1) (Enhancer-of-split and hairy-related protein 2) (SHARP-2) (Stimulated with retinoic acid13); (1283:) class I alcohol dehydrogenase, alpha subunit [*Homo sapiens*]; (1284:) class I alcohol dehydrogenase, gamma subunit [*Homo sapiens*]; (1285:) class II alcohol dehydrogenase 4 pi subunit [*Homo sapiens*]; (1286:) class III alcohol dehydrogenase 5 chi subunit [*Homo sapiens*]; (1287:) class IV alcohol dehydrogenase 7 mu or sigma subunit [*Homo sapiens*]; (1288:) class IV alcohol dehydrogenase, sigma sigma-ADH; (1289:) clathrin heavy chain 1 [*Homo sapiens*]; (1290:) CLCN6 [*Homo sapiens*]; (1291:) CMH-1; (1292:) CMP-N-acetylneuraminate-beta-galactosamide-alpha-2,6-sialyltransferase (Beta-galactoside alpha-2,6-sialyltransferase) (Alpha 2,6-ST) (Sialyltransferase 1) (ST6Gal I) (B-cell antigen CD75); (1293:) CMRF35-H antigen precursor (CMRF35-H9) (CMRF-35-H9) (CD300a antigen) (Inhibitory receptor protein 60) (IRp60) (IRC1/IRC2) (NK inhibitory receptor); (1294:) CMRF35-like-molecule 1 precursor (CLM-1) (Immune receptor expressed on myeloid cells protein 1) (IREM-1) (Immunoglobulin superfamily member 13) (NK inhibitory receptor) (CD300 antigen like family member F) (IgSF13); (1295:) c-myc binding protein [*Homo sapiens*]; (1296:) coactivator-associated arginine methyltransferase 1 [*Homo sapiens*]; (1297:) coactosin-like 1 [*Homo sapiens*]; (1298:) coagulation factor II (thrombin) receptor-like 1 precursor [*Homo sapiens*]; (1299:) coagulation factor II precursor [*Homo sapiens*]; (1300:) coagulation factor III precursor [*Homo sapiens*]; (1301:) coagulation factor IX [*Homo sapiens*]; (1302:) coagulation factor V precursor [*Homo sapiens*]; (1303:) coagulation factor VII isoform a precursor [*Homo sapiens*]; (1304:) coagulation factor VII isoform b precursor [*Homo sapiens*]; (1305:) coagulation factor VIII isoform a precursor [*Homo sapiens*]; (1306:) coagulation factor VIII isoform b precursor [*Homo sapiens*]; (1307:) coagulation factor X preproprotein [*Homo sapiens*]; (1308:) coagulation factor XIII A1 subunit precursor [*Homo sapiens*]; (1309:) coagulation factor XIII B subunit precursor [*Homo sapiens*]; (1310:) COASY protein [*Homo sapiens*]; (1311:) Coenzyme A synthase [*Homo sapiens*]; (1312:) coenzyme A synthase isoform a [*Homo sapiens*]; (1313:) coenzyme A synthase isoform b [*Homo sapiens*]; (1314:) Cofactor required for Sp1 transcriptional activation subunit 9(Transcriptional coactivator CRSP33) (RNA polymerase transcriptional regulation mediator subunit 7 homolog) (hMED7) (Activator-recruited cofactor 34 kDa component) (ARC34); (1315:) coilin-interacting nuclear ATPase protein [*Homo sapiens*]; (1316:) coilin-interacting nulcear ATPase protein [*Homo sapiens*]; (1317:) Colipase precursor; (1318:) colony stimulating factor 3 isoform a precursor [*Homo sapiens*]; (1319:) colony stimulating factor 3 isoform b precursor [*Homo sapiens*]; (1320:) colony stimulating factor 3 isoform c [*Homo sapiens*]; (1321:) colony-stimulating factor; (1322:) complement C1r activated form; (1323:) "Complement C1r subcomponent precursor (Complement component 1, rsubcomponent) [Contains:) Complement C1r subcomponent heavy chain; Complement C1r subcomponent light chain]."; (1324:) complement component 1, s subcomponent [*Homo sapiens*]; (1325:) complement component 3 precursor [*Homo sapiens*]; (1326:) Complement component 6 precursor [*Homo sapiens*]; (1327:) Complement component C1q receptor precursor (Complement component 1q subcomponent receptor 1) (C1qR) (C1qRp) (C1 qR(p)) (C1q/MBL/SPA receptor) (CD93 antigen) (CDw93); (1328:) complement factor D preproprotein [*Homo sapiens*]; (1329:) Complement receptor type 1 precursor (C3b/C4b receptor) (CD35antigen); (1330:) Complement receptor type 2 precursor (Cr2) (Complement C3d receptor) (Epstein-Barr virus receptor) (EBV receptor) (CD21antigen); (1331:) copper monamine oxidase; (1332:) coproporphyrinogen oxidase [*Homo sapiens*]; (1333:) core 2 beta-1,6-N-acetylglucosaminyltransferase 3 [*Homo sapiens*]; (1334:) corin [*Homo sapiens*]; (1335:) Corticosteroid 11-beta-dehydrogenase isozyme 1 (11-DH) (11-beta-hydroxysteroid dehydrogenase 1) (11-beta-HSD1); (1336:) Corticosteroid 11-beta-dehydrogenase isozyme 2 (11-DH2) (11-beta-hydroxysteroid dehydrogenase type 2) (11-beta-HSD2) (NAD-dependent 11-beta-hydroxysteroid dehydrogenase); (1337:) Corticotropin-releasing factor receptor 1 precursor (CRF-R) (CRF1) (Corticotropin-releasing hormone receptor 1) (CRH-R1); (1338:) Corticotropin-releasing factor receptor 2 precursor (CRF-R 2) (CRF2) (Corticotropin-releasing hormone receptor 2) (CRH-R 2); (1339:) COUP transcription factor 1 (COUP-TF1) (COUP-TF I) (V-ERBA-related protein EAR-3); (1340:) COUP transcription factor 2 (COUP-TF2) (COUP-TF II) (ApolipoproteinAI regulatory protein 1) (ARP-1); (1341:) COX11 homolog [*Homo sapiens*]; (1342:) Coxsackievirus and adenovirus receptor precursor (Coxsackievirus B-adenovirus receptor) (hCAR) (CVB3-binding protein) (HCVADR); (1343:) CPA4 protein [*Homo sapiens*]; (1344:) C-reactive protein, pentraxin-related [*Homo sapiens*]; (1345:) CREB binding protein [*Homo sapiens*]; (1346:) CRSP complex subunit 2 (Cofactor required for Sp1 transcriptional activation subunit 2) (Transcriptional coactivator CRSP150) (Vitamin D3 receptor-interacting protein complex 150 kDa component) (DRIP150) (Thyroid hormone receptor-associated protein complex 170 kDa component) (Trap170) (Activator-recruited cofactor 150 kDa component) (ARC150); (1347:) CRSP complex subunit 3 (Cofactor required for Sp1 transcriptional activation subunit 3) (Transcriptional coactivator CRSP130) (Vitamin D3 receptor-interacting protein complex 130 kDa component) (DRIP130) (Activator-recruited cofactor 130 kDa component) (ARC130); (1348:) CRSP complex subunit 6 (Cofactor required for Sp1 transcriptional activation subunit 6) (Transcriptional coactivator CRSP77) (Vitamin D3 receptor-interacting protein complex 80 kDa component) (DRIP80) (Thyroid hormone receptor-associated protein complex 80 kDa component) (Trap80) (Activator-recruited cofactor 77 kDa component) (ARC77); (1349:) CRSP complex subunit 7 (Cofactor required for Sp1 transcriptional activation subunit 7) (Transcriptional coactivator CRSP70) (Activator-recruited cofactor 70 kDa component) (ARC70); (1350:) crystallin, alpha A [Homo sapiens]; (1351:) crystallin, alpha B [Homo sapiens]; (1352:) crystallin, beta A2 [Homo sapiens]; (1353:) crystallin, beta A3 [Homo sapiens]; (1354:) crystallin, beta A4 [Homo sapiens]; (1355:) crystallin, beta B1 [Homo sapiens]; (1356:) crystallin, beta B2 [Homo sapiens]; (1357:) crystallin, beta B3 [Homo sapiens]; (1358:) crystallin, gamma A [Homo sapiens]; (1359:) crystallin, gamma B [Homo sapiens]; (1360:) crystallin, gamma C [Homo sapiens]; (1361:) crystallin, gamma D [Homo sapiens]; (1362:) crystallin, gamma S [Homo sapiens]; (1363:) crystallin, mu isoform 1 [Homo sapiens]; (1364:) crystallin, mu isoform 2 [Homo sapiens]; (1365:) crystallin, zeta [Homo sapiens]; (1366:) c-src tyrosine kinase [Homo sapiens]; (1367:) CTP synthase [Homo sapiens]; (1368:) CTP synthase 1 (UTP—ammonia ligase 1) (CTP synthetase 1); (1369:) CTP synthase 2 (UTP—ammonia ligase 2) (CTP synthetase 2); (1370:) C-type lectin domain family 4 member F (C-type lectin superfamily member 13) (C-type lectin 13); (1371:) C-type lectin domain family 4 member M (CD209 antigen-like protein1) (Dendritic cell-specific ICAM-3-grabbing nonintegrin 2) (DC-SIGN2) (DC-SIGN-related protein) (DC-SIGNR) (Liver/lymph node-specific ICAM-3-grabbing nonintegrin) (L-SIGN) (CD299antigen); (1372:) C-type lectin domain family 9 member A; (1373:) Cubilin precursor (Intrinsic factor-cobalamin receptor) (Intrinsic factor-vitamin B12 receptor) (460 kDa receptor) (Intestinal intrinsic factor receptor); (1374:) Cullin-1 (CUL-1); (1375:) Cullin-2 (CUL-2); (1376:) Cullin-5 (CUL-5) (Vasopressin-activated calcium-mobilizing receptor) (VACM-1); (1377:) CX3C chemokine receptor 1 (C-X3-C CKR-1) (CX3CR1) (Fractalkine receptor) (G-protein coupled receptor 13) (V28) (Beta chemokine receptor-like 1) (CMK-BRL-1) (CMK-BLR1); (1378:) C-X-C chemokine receptor type 3 (CXC-R3) (CXCR-3) (Interferon-inducible protein 10 receptor) (IP-10 receptor) (CKR-L2) (CD183 antigen) (G protein-coupled receptor 9); (1379:) C-X-C chemokine receptor type 4 (CXC-R4) (CXCR-4) (Stromal cell-derived factor 1 receptor) (SDF-1 receptor) (Fusin) (Leukocyte-derived seven transmembrane domain receptor) (LESTR) (LCR1) (FB22) (NPYRL) (HM89) (CD184 antigen); (1380:) C-X-C chemokine receptor type 5 (CXC-R5) (CXCR-5) (Burkitt lymphoma receptor 1) (Monocyte-derived receptor 15) (MDR-15) (CD185antigen); (1381:) C-X-C chemokine receptor type 6 (CXC-R6) (CXCR-6) (G-protein coupled receptor bonzo) (G-protein coupled receptor STRL33) (CD186antigen) (CDw186); (1382:) C-X-C chemokine receptor type 7 (CXC-R7) (CXCR-7) (G-protein coupled receptor RDC1 homolog) (RDC-1) (Chemokine orphan receptor1) (G-protein coupled receptor 159); (1383:) cyclin D1 [Homo sapiens]; (1384:) cyclin-dependent kinase 2 isoform 1 [Homo sapiens]; (1385:) cyclin-dependent kinase 2 isoform 2 [Homo sapiens]; (1386:) cyclin-dependent kinase inhibitor 1B [Homo sapiens]; (1387:) cyclin-dependent kinase inhibitor 2A isoform 1 [Homo sapiens]; (1388:) cyclin-dependent kinase inhibitor 2A isoform 3 [Homo sapiens]; (1389:) cyclin-dependent kinase inhibitor 2A isoform 4 [Homo sapiens]; (1390:) Cyclin-dependent kinase inhibitor 2A, isoform 4 (p14ARF) (p19ARF); (1391:) Cyclin-dependent kinase-like 5 (Serine/threonine-protein kinase 9); (1392:) cyclin-selective ubiquitin carrier protein [Homo sapiens]; (1393:) Cystathionase (cystathionine gamma-lyase) [Homo sapiens]; (1394:) cystathionase isoform 1 [Homo sapiens]; (1395:) cystathionase isoform 1 variant [Homo sapiens]; (1396:) cystathionase isoform 2 [Homo sapiens]; (1397:) cystathionine B synthase [Homo sapiens]; (1398:) Cystathionine beta-synthase (Serine sulfhydrase) (Beta-thionase); (1399:) cystathionine beta-synthase major isoform [Homo sapiens]; (1400:) cystathionine beta-synthase; (1401:) Cystathionine gamma-lyase (Gamma-cystathionase); (1402:) "cystathionine gamma-lyase; cystathionase [Homo sapiens]."; (1403:) cystathionine-beta-synthase [Homo sapiens]; (1404:) Cystatin C precursor (Neuroendocrine basic polypeptide) (Gamma-trace) (Post-gamma-globulin); (1405:) "cysteine conjugate-beta lyase; cytoplasmic (glutamine transaminaseK, kyneurenine aminotransferase) [Homo sapiens]."; (1406:) cysteine desulfurase [Homo sapiens]; (1407:) Cysteine desulfurase, mitochondrial precursor; (1408:) cysteine dioxygenase [Homo sapiens]; (1409:) Cysteine protease ATG4A (Autophagy-related protein 4 homolog A) (hAPG4A) (Autophagin-2) (Autophagy-related cysteine endopeptidase2) (AUT-like 2 cysteine endopeptidase); (1410:) Cysteine protease ATG4B (Autophagy-related protein 4 homolog B) (hAPG4B) (Autophagin-1) (Autophagy-related cysteine endopeptidase 1) (AUT-like 1 cysteine endopeptidase); (1411:) Cysteine protease ATG4C (Autophagy-related protein 4 homolog C) (Autophagin-3) (Autophagy-related cysteine endopeptidase 3) (AUT-like 3 cysteine endopeptidase); (1412:) Cysteine protease ATG4D (Autophagy-related protein 4 homolog D) (Autophagin-4) (Autophagy-related cysteine endopeptidase 4) (AUT-like 4 cysteine endopeptidase); (1413:) cysteine protease CPP32 isoform alpha; (1414:) cysteine protease CPP32 isoform beta; (1415:) cysteine protease Mch2 isoform alpha; (1416:) cysteine protease Mch2 isoform beta; (1417:) cysteine protease; (1418:) cysteine-rich, angiogenic inducer, 61 [Homo sapiens]; (1419:) Cysteinyl leukotriene receptor 1 (CysLTR1) (Cysteinyl leukotrieneD4 receptor) (LTD4 receptor) (HG55) (HMTMF81); (1420:) Cysteinyl leukotriene receptor 2 (CysLTR2) (HG57) (HPN321) (hGPCR21); (1421:) cytidine 5'-monophosphate N-acetylneuraminic acid synthetase [Homo sapiens]; (1422:) Cytidine deaminase (Cytidine aminohydrolase); (1423:) cytidine deaminase [Homo sapiens]; (1424:) Cytidine monophosphate-N-acetylneuraminic acid hydroxylase-like protein (CMP-NeuAc hydroxylase-like protein); (1425:) cytidine triphosphate synthase II [Homo sapiens]; (1426:) cytidylate kinase [Homo sapiens]; (1427:) cytochrome b [Homo sapiens]; (1428:) cytochrome b, alpha polypeptide [Homo sapiens]; (1429:) Cytochrome b; (1430:) cytochrome b5 reductase b5R.2 [Homo sapiens]; (1431:) cytochrome b5 reductase isoform 1 [Homo sapiens]; (1432:) cytochrome b5 reductase isoform 2 [Homo sapiens]; (1433:) cytochrome c [Homo sapiens]; (1434:) Cytochrome c oxidase subunit 1 (Cytochrome c oxidase polypeptideI); (1435:) Cytochrome c oxidase subunit 2 (Cytochrome c oxidase polypeptideII); (1436:) Cytochrome c oxidase subunit 3 (Cytochrome c oxidase polypeptideIII); (1437:) cytochrome c oxidase subunit 8A [Homo sapiens]; (1438:) cytochrome c oxidase subunit IV isoform 1 precursor [Homo sapiens]; (1439:) cytochrome c oxidase subunit IV isoform 2 [Homo sapiens]; (1440:) cytochrome c oxidase subunit IV precursor [Homo sapiens]; (1441:) cytochrome c oxidase subunit Va precursor [Homo sapiens]; (1442:) cytochrome c oxidase subunit Vb precursor [Homo sapiens]; (1443:) cytochrome c oxidase subunit VIa polypeptide 1 precursor [Homo sapiens]; (1444:) cytochrome c oxidase subunit VIa polypeptide 2 precursor [Homo sapiens]; (1445:) cytochrome c oxidase subunit VIb [Homo sapiens]; (1446:) cytochrome c oxidase subunit VIc proprotein [*Homo sapiens*]; (1447:) cytochrome c-1 [*Homo sapiens*]; (1448:) cytochrome P450 [*Homo sapiens*]; (1449:) Cytochrome P450 11A1, mitochondrial precursor (CYPXIA1) (P450(scc)) (Cholesterol side-chain cleavage enzyme) (Cholesterol desmolase); (1450:) Cytochrome P450 11B2, mitochondrial precursor (CYPXIB2) (P-450Aldo) (Aldosterone synthase) (ALDOS) (Aldosterone-synthesizing enzyme) (Steroid 18-hydroxylase) (P-450C18); (1451:) Cytochrome P450 17A1 (CYPXVII) (P450-C17) (P450c17) (Steroid17-alpha-monooxygenase) (Steroid 17-alpha-hydroxylase/17,20 lyase); (1452:) Cytochrome P450 19A1 (Aromatase) (CYPXIX) (Estrogen synthetase) (P-450AROM); (1453:) Cytochrome P450 1A1 (CYPIA1) (P450-P1) (P450 form 6) (P450-C); (1454:) cytochrome P450 1A1 variant [*Homo sapiens*]; (1455:) Cytochrome P450 1A2 (CYPIA2) (P450-P3) (P(3)450) (P450 4); (1456:) Cytochrome P450 1B1 (CYPIB1); (1457:) Cytochrome P450 21 (Cytochrome P450 XXI) (Steroid 21-hydroxylase) (21-OHase) (P450-C21) (P-450c21) (P450-C21B); (1458:) Cytochrome P450 26A1 (Retinoic acid-metabolizing cytochrome) (P450retinoic acid-inactivating 1) (P450RAI) (hP450RAI) (Retinoic acid4-hydroxylase); (1459:) Cytochrome P450 26B1 (P450 26A2) (P450 retinoic acid-inactivating2) (P450RAI-2) (Retinoic acid-metabolizing cytochrome); (1460:) Cytochrome P450 27, mitochondrial precursor (CytochromeP-450C27/25) (Sterol 26-hydroxylase) (Sterol 27-hydroxylase) (Vitamin D(3) 25-hydroxylase) (5-beta-cholestane-3-alpha,7-alpha,12-alpha-triol 27-hydroxylase); (1461:) cytochrome P450 2A3, hepatic—human (fragment); (1462:) Cytochrome P450 2A7 (CYPIIA7) (P450-IIA4); (1463:) Cytochrome P450 2B6 (CYPIIB6) (P450 IIB1); (1464:) Cytochrome P450 2C18 (CYPIIC18) (P450-6B/29C); (1465:) Cytochrome P450 2C8 (CYPIIC8) (P450 form 1) (P450MP-12/MP-20) (P450 IIC2) (S-mephenyloin 4-hydroxylase); (1466:) Cytochrome P450 2C9 ((R)-limonene 6-monooxygenase) ((S)-limonene6-monooxygenase) ((S)-limonene 7-monooxygenase) (CYPIIC9) (P450PB-1) (P450MP-4/MP-8) (S-mephenyloin 4-hydroxylase) (P-450 MP); (1467:) Cytochrome P450 2E1 (CYPIIE1) (P450-J); (1468:) Cytochrome P450 2J2 (CYPIIJ2) (Arachidonic acid epoxygenase); (1469:) Cytochrome P450 2R1 (Vitamin D 25-hydroxylase); (1470:) Cytochrome P450 3A3 (CYPIIIA3) (HLp); (1471:) Cytochrome P450 3A4 (Quinine 3-monooxygenase) (CYPIIIA4) (Nifedipine oxidase) (Taurochenodeoxycholate 6-alpha-hydroxylase) (NF-25) (P450-PCN1); (1472:) Cytochrome P450 3A5 (CYPIIIA5) (P450-PCN3) (HLp2); (1473:) Cytochrome P450 3A7 (CYPIIIA7) (P450-HFLA); (1474:) Cytochrome P450 4A11 precursor (CYPIVA11) (Fatty acidomega-hydroxylase) (P-450 HK omega) (Lauric acid omega-hydroxylase) (CYP4AII) (P450-HL-omega); (1475:) Cytochrome P450 4B1 (CYPIVB1) (P450-HP); (1476:) Cytochrome P450 4F2 (CYPIVF2) (Leukotriene-B(4) omega-hydroxylase) (Leukotriene-B(4) 20-monooxygenase) (Cytochrome P450-LTB-omega); (1477:) Cytochrome P450 4F3 (CYPIVF3) (Leukotriene-B(4) omega-hydroxylase) (Leukotriene-B(4) 20-monooxygenase) (Cytochrome P450-LTB-omega); (1478:) cytochrome P450 family 1 subfamily A polypeptide 1 [*Homo sapiens*]; (1479:) cytochrome P450 family 3 subfamily A polypeptide 4 [*Homo sapiens*]; (1480:) cytochrome P450 reductase [*Homo sapiens*]; (1481:) cytochrome P450, family 1, subfamily A, polypeptide 1 [*Homo sapiens*]; (1482:) cytochrome P450, family 1, subfamily A, polypeptide 2 [*Homo sapiens*]; (1483:) cytochrome P450, family 1, subfamily B, polypeptide 1 [*Homo sapiens*]; (1484:) cytochrome P450, family 11, subfamily B, polypeptide 1 isoform 1precursor [*Homo sapiens*]; (1485:) cytochrome P450, family 11, subfamily B, polypeptide 1 isoform 2precursor [*Homo sapiens*]; (1486:) cytochrome P450, family 17 [*Homo sapiens*]; (1487:) cytochrome P450, family 19 [*Homo sapiens*]; (1488:) cytochrome P450, family 2, subfamily A, polypeptide 6 [*Homo sapiens*]; (1489:) cytochrome P450, family 2, subfamily B, polypeptide 6 [*Homo sapiens*]; (1490:) cytochrome P450, family 2, subfamily C, polypeptide 18 [*Homo sapiens*]; (1491:) cytochrome P450, family 2, subfamily C, polypeptide 19 [*Homo sapiens*]; (1492:) cytochrome P450, family 2, subfamily C, polypeptide 8 [*Homo sapiens*]; (1493:) cytochrome P450, family 2, subfamily C, polypeptide 9 [*Homo sapiens*]; (1494:) cytochrome P450, family 2, subfamily D, polypeptide 6 isoform 1 [*Homo sapiens*]; (1495:) cytochrome P450, family 2, subfamily D, polypeptide 6 isoform 2 [*Homo sapiens*]; (1496:) cytochrome P450, family 2, subfamily E, polypeptide 1 [*Homo sapiens*]; (1497:) cytochrome P450, family 2, subfamily J, polypeptide 2 [*Homo sapiens*]; (1498:) cytochrome P450, family 2, subfamily R, polypeptide 1 [*Homo sapiens*]; (1499:) cytochrome P450, family 2, subfamily U, polypeptide 1 [*Homo sapiens*]; (1500:) cytochrome P450, family 2, subfamily W, polypeptide 1 [*Homo sapiens*]; (1501:) cytochrome P450, family 21, subfamily A, polypeptide 2 [*Homo sapiens*]; (1502:) cytochrome P450, family 24 precursor [*Homo sapiens*]; (1503:) cytochrome P450, family 26, subfamily A, polypeptide 1 isoform 1 [*Homo sapiens*]; (1504:) cytochrome P450, family 26, subfamily A, polypeptide 1 isoform 2 [*Homo sapiens*]; (1505:) cytochrome P450, family 26, subfamily b, polypeptide 1 [*Homo sapiens*]; (1506:) cytochrome P450, family 26, subfamily C, polypeptide 1 [*Homo sapiens*]; (1507:) cytochrome P450, family 27, subfamily A, polypeptide 1 precursor [*Homo sapiens*]; (1508:) cytochrome P450, family 27, subfamily B, polypeptide 1 [*Homo sapiens*]; (1509:) cytochrome P450, family 3, subfamily A, polypeptide 43 isoform 1 [*Homo sapiens*]; (1510:) cytochrome P450, family 3, subfamily A, polypeptide 43 isoform 2 [*Homo sapiens*]; (1511:) cytochrome P450, family 3, subfamily A, polypeptide 43 isoform 3 [*Homo sapiens*]; (1512:) cytochrome P450, family 3, subfamily A, polypeptide 5 [*Homo sapiens*]; (1513:) cytochrome P450, family 3, subfamily A, polypeptide 7 [*Homo sapiens*]; (1514:) cytochrome P450, family 4, subfamily A, polypeptide 11 [*Homo sapiens*]; (1515:) cytochrome P450, family 4, subfamily F, polypeptide 12 [*Homo sapiens*]; (1516:) cytochrome P450, family 4, subfamily F, polypeptide 2 [*Homo sapiens*]; (1517:) cytochrome P450, family 4, subfamily F, polypeptide 3 [*Homo sapiens*]; (1518:) cytochrome P450, family 46 [*Homo sapiens*]; (1519:) cytochrome P450, family 7, subfamily A, polypeptide 1 [*Homo sapiens*]; (1520:) cytochrome P450, family 7, subfamily B, polypeptide 1 [*Homo sapiens*]; (1521:) cytochrome P450, subfamily 111A, polypeptide 4 [*Homo sapiens*]; (1522:) cytochrome P450, subfamily XIA precursor [*Homo sapiens*]; (1523:) cytochrome P450, subfamily XIB polypeptide 2 precursor [*Homo sapiens*]; (1524:) cytochrome P450; (1525:) cytochrome P450j; (1526:) Cytokine receptor common beta chain precursor (GM-CSF/IL-3/IL-5receptor common beta-chain) (CD131 antigen) (CDw131); (1527:) Cytokine receptor common gamma chain precursor (Gamma-C) (Interleukin-2 receptor gamma chain) (IL-2R gamma chain) (p64) (CD132 antigen); (1528:) Cytokine receptor-like factor 1 precursor (Cytokine-like factor 1) (CLF-1) (ZcytoR5); (1529:) Cytokine receptor-like factor 2 precursor (Cytokine receptor-like2) (CRL2) (IL-XR) (Thymic stromal lymphopoietin protein receptor) (TSLPR); (1530:) cytoplasmic cysteine conjugate-beta lyase [Homo sapiens]; (1531:) Cytoplasmic dynein 1 light intermediate chain 1 (Dynein light intermediate chain 1, cytosolic) (Dynein light chain A) (DLC-A); (1532:) Cytosol aminopeptidase (Leucine aminopeptidase) (LAP) (Leucylaminopeptidase) (Proline aminopeptidase) (Prolyl aminopeptidase) (Peptidase S); (1533:) Cytosolic 5'-nucleotidase 1A (Cytosolic 5'-nucleotidase IA) (cN1A) (cN-IA) (cN-I); (1534:) Cytosolic 5'-nucleotidase 1B (Cytosolic 5'-nucleotidase IB) (cN1B) (cN-IB) (Autoimmune infertility-related protein); (1535:) cytosolic acetyl-CoA hydrolase [Homo sapiens]; (1536:) cytosolic aminopeptidase P [Homo sapiens]; (1537:) Cytosolic beta-glucosidase (Cytosolic beta-glucosidase-like protein1); (1538:) cytosolic beta-glucosidase [Homo sapiens]; (1539:) cytosolic inhibitor of NRF2 [Homo sapiens]; (1540:) cytosolic leucyl-tRNA synthetase [Homo sapiens]; (1541:) cytosolic malic enzyme 1 [Homo sapiens]; (1542:) cytosolic malic enzyme 1 variant [Homo sapiens]; (1543:) cytosolic malic enzyme; (1544:) cytosolic NADP(+)-dependent malic enzyme; (1545:) cytosolic ovarian carcinoma antigen 1 isoform a [Homo sapiens]; (1546:) cytosolic ovarian carcinoma antigen 1 isoform b [Homo sapiens]; (1547:) cytosolic phosphoenolpyruvate carboxykinase 1 [Homo sapiens]; (1548:) "Cytosolic phospholipase A2 (cPLA2) (Phospholipase A2 group IVA)[Includes) Phospholipase A2 (Phosphatidylcholine 2-acylhydrolase);Lysophospholipase]."; (1549:) Cytosolic phospholipase A2 beta (cPLA2-beta) (Phospholipase A2group IVB); (1550:) Cytosolic phospholipase A2 delta (cPLA2-delta) (Phospholipase A2group IVD); (1551:) Cytosolic phospholipase A2 epsilon (cPLA2-epsilon) (PhospholipaseA2 group IVE); (1552:) Cytosolic phospholipase A2 gamma precursor (cPLA2-gamma) (Phospholipase A2 group IVC); (1553:) Cytosolic phospholipase A2 zeta (cPLA2-zeta) (Phospholipase A2group IVF); (1554:) cytosolic phospholipase A2, group IVA [Homo sapiens]; (1555:) Cytosolic purine 5'-nucleotidase (5'-nucleotidase cytosolic II); (1556:) cytosolic thyroid hormone-binding protein (EC 2.7.1.40); (1557:) CAAX prenyl protease 1 homolog (Prenyl protein-specific endoprotease 1) (Farnesylated proteins-converting enzyme 1) (FACE-1) (Zinc metalloproteinase Step 24 homolog); (1558:) CAAX prenyl protease 2 (Prenyl protein-specific endoprotease 2) (Farnesylated proteins-converting enzyme 2) (FACE-2) (hRCE1); (1559:) D(1A) dopamine receptor; (1560:) D(1B) dopamine receptor (D(5) dopamine receptor) (D1beta dopamine receptor); (1561:) D(2) dopamine receptor (Dopamine D2 receptor); (1562:) D(3) dopamine receptor; (1563:) D(4) dopamine receptor (Dopamine D4 receptor) (D(2C) dopamine receptor); (1564:) D-2-hydroxyglutarate dehydrogenase, mitochondrial precursor; (1565:) dachshund homolog 1 isoform a [Homo sapiens]; (1566:) dachshund homolog 1 isoform b [Homo sapiens]; (1567:) dachshund homolog 1 isoform c [Homo sapiens]; (1568:) D-amino-acid oxidase [Homo sapiens]; (1569:) D-aspartate oxidase isoform a [Homo sapiens]; (1570:) D-aspartate oxidase isoform b [Homo sapiens]; (1571:) D-beta-hydroxybutyrate dehydrogenase, mitochondrial precursor (BDH) (3-hydroxybutyrate dehydrogenase); (1572:) DCP1 decapping enzyme homolog A [Homo sapiens]; (1573:) DCP1 decapping enzyme homolog B (S. cerevisiae) [Homo sapiens]; (1574:) DCP2 decapping enzyme [Homo sapiens]; (1575:) D-dopachrome decarboxylase (D-dopachrome tautomerase) (Phenylpyruvate tautomerase II); (1576:) D-dopachrome tautomerase [Homo sapiens]; (1577:) DEAD/H (Asp-Glu-Ala-Asp/His) box polypeptide 11 isoform 1 [Homo sapiens]; (1578:) DEAD/H (Asp-Glu-Ala-Asp/His) box polypeptide 11 isoform 2 [Homo sapiens]; (1579:) deaminase, adenosine; (1580:) Death-associated protein kinase 1 (DAP kinase 1); (1581:) Death-associated protein kinase 2 (DAP kinase 2) (DAP-kinase-related protein 1) (DRP-1); (1582:) Debranching enzyme homolog 1 (S. cerevisiae) [Homo sapiens]; (1583:) debranching enzyme homolog 1 [Homo sapiens]; (1584:) decapping enzyme Dcp1b [Homo sapiens]; (1585:) decapping enzyme hDcp1a [Homo sapiens]; (1586:) decapping enzyme hDcp1b [Homo sapiens]; (1587:) decapping enzyme hDcp2 [Homo sapiens]; (1588:) Decapping enzyme, scavenger [Homo sapiens]; (1589:) defender against cell death 1 [Homo sapiens]; (1590:) defensin, alpha 5 preproprotein [Homo sapiens]; (1591:) Dehydrogenase/reductase SDR family member 8 precursor (17-beta-hydroxysteroid dehydrogenase 11) (17-beta-HSD 11) (17-beta-HSD XI) (17betaHSDXI) (17bHSD11) (17betaHSD11) (Retinal short-chain dehydrogenase/reductase 2) (retSDR2) (Cutaneous T-cellymphoma-associated antigen HD-CL-03) (CTCL tumor antigenHD-CL-03); (1592:) deiodinase, iodothyronine, type I isoform a [Homo sapiens]; (1593:) deiodinase, iodothyronine, type I isoform b [Homo sapiens]; (1594:) deiodinase, iodothyronine, type I isoform c [Homo sapiens]; (1595:) deiodinase, iodothyronine, type I isoform d [Homo sapiens]; (1596:) deiodinase, iodothyronine, type II isoform a [Homo sapiens]; (1597:) deiodinase, iodothyronine, type II isoform b [Homo sapiens]; (1598:) deiodinase, iodothyronine, type III [Homo sapiens]; (1599:) "Delta 1-pyrroline-5-carboxylate synthetase (P5CS) (Aldehydedehydrogenase 18 family member A1) [Includes:) Glutamate 5-kinase (Gamma-glutamyl kinase) (GK); Gamma-glutamyl phosphate reductase(GPR) (Glutamate-5-semialdehyde dehydrogenase) (Glutamyl-gamma-semialdehyde dehydrogenase)]."; (1600:) delta 4-3-oxosteroid 5 beta-reductase [Homo sapiens]; (1601:) delta-aminolevulinate synthase (housekeeping) [Homo sapiens]; (1602:) Delta and Notch-like epidermal growth factor-related receptor precursor; (1603:) delta isoform of regulatory subunit B56, protein phosphatase 2A isoform 1 [Homo sapiens]; (1604:) delta isoform of regulatory subunit B56, protein phosphatase 2A isoform 2 [Homo sapiens]; (1605:) delta isoform of regulatory subunit B56, protein phosphatase 2A isoform 3 [Homo sapiens]; (1606:) Delta-1-pyrroline-5-carboxylate dehydrogenase, mitochondrial precursor (P5C dehydrogenase) (Aldehyde dehydrogenase 4A1); (1607:) delta3, delta2-enoyl-CoA isomerase; (1608:) Delta-4-3-oxosteroid 5beta reductase; (1609:) Delta-aminolevulinic acid dehydratase (Porphobilinogen synthase) (ALADH); (1610:) delta-aminolevulinic acid dehydratase isoform a [Homo sapiens]; (1611:) delta-aminolevulinic acid dehydratase isoform b [Homo sapiens]; (1612:) Delta-type opioid receptor (DOR-1); (1613:) deoxy-5'-nucleotidase [Homo sapiens]; (1614:) deoxycytidine kinase [Homo sapiens]; (1615:) Deoxycytidylate deaminase (dCMP deaminase); (1616:) deoxycytidylate deaminase; (1617:) deoxyguanosine kinase isoform a precursor [Homo sapiens]; (1618:) deoxyguanosine kinase isoform b precursor [Homo sapiens]; (1619:) Deoxyhypusine hydroxylase (Deoxyhypusine monooxygenase) (hDOHH) (HEAT-like repeat-containing protein 1); (1620:) Deoxyhypusine synthase (DHS); (1621:) deoxyhypusine synthase isoform a [Homo sapiens]; (1622:) deoxyhypusine synthase isoform b [Homo sapiens]; (1623:) deoxyhypusine synthase isoform c [Homo sapiens]; (1624:) deoxyhypusine synthase; (1625:) Deoxyribonuclease gamma precursor (DNase gamma) (DeoxyribonucleaseI-like 3) (DNase I homolog protein DHP2) (Liver and spleen DNase) (LS-DNase) (LSD); (1626:) deoxyribonuclease I precursor [Homo sapiens]; (1627:) deoxyribonuclease II, lysosomal precursor [Homo sapiens]; (1628:) deoxyribonuclease III (DNase III) [*Homo sapiens*]; (1629:) Deoxyribonuclease-2-alpha precursor (Deoxyribonuclease II alpha) (DNase II alpha) (Acid DNase) (Lysosomal DNase II) (R31240_2); (1630:) Deoxyuridine 5'-triphosphate nucleotidohydrolase, mitochondrial precursor (dUTPase) (dUTP pyrophosphatase); (1631:) de-ubiquitinase [*Homo sapiens*]; (1632:) deubiquitinating enzyme [*Homo sapiens*]; (1633:) deubiquitinating enzyme 1 [*Homo sapiens*]; (1634:) deubiquitinating enzyme 3 [*Homo sapiens*]; (1635:) deubiquitinating enzyme DUB1 [*Homo sapiens*]; (1636:) deubiquitinating enzyme DUB2 [*Homo sapiens*]; (1637:) deubiquitinating enzyme DUB4 [*Homo sapiens*]; (1638:) Deubiquitinating Enzyme Uch-L3 (Human) At 1.8 Angstrom Resolution; (1639:) Deubiquitinating protein VCIP135 (Valosin-containing protein p97/p47 complex-interacting protein p135) (Valosin-containing protein p97/p47 complex-interacting protein 1); (1640:) D-glucuronyl C5-epimerase [*Homo sapiens*]; (1641:) Diacylglycerol kinase alpha (Diglyceride kinase alpha) (DGK-alpha) (DAG kinase alpha) (80 kDa diacylglycerol kinase); (1642:) Diacylglycerol kinase beta (Diglyceride kinase beta) (DGK-beta) (DAG kinase beta) (90 kDa diacylglycerol kinase); (1643:) Diacylglycerol kinase delta (Diglyceride kinase delta) (DGK-delta) (DAG kinase delta) (130 kDa diacylglycerol kinase); (1644:) Diacylglycerol kinase gamma (Diglyceride kinase gamma) (DGK-gamma) (DAG kinase gamma); (1645:) diacylglycerol kinase gamma [*Homo sapiens*]; (1646:) Diacylglycerol kinase kappa (Diglyceride kinase kappa) (DGK-kappa) (DAG kinase kappa) (142 kDa diacylglycerol kinase); (1647:) diacylglycerol kinase, beta isoform 1 [*Homo sapiens*]; (1648:) diacylglycerol kinase, beta isoform 2 [*Homo sapiens*]; (1649:) diacylglycerol kinase, delta 130 kDa isoform 1 [*Homo sapiens*]; (1650:) diacylglycerol kinase, delta 130 kDa isoform 2 [*Homo sapiens*]; (1651:) diacylglycerol kinase, eta isoform 1 [*Homo sapiens*]; (1652:) diacylglycerol kinase, eta isoform 2 [*Homo sapiens*]; (1653:) diacylglycerol kinase, gamma 90 kDa [*Homo sapiens*]; (1654:) diacylglycerol kinase, iota [*Homo sapiens*]; (1655:) diacylglycerol O-acyltransferase 1 [*Homo sapiens*]; (1656:) Diacylglycerol O-acyltransferase 2 (Diglyceride acyltransferase 2); (1657:) diacylglycerol O-acyltransferase 2-like 4 [*Homo sapiens*]; (1658:) Diamine acetyltransferase 1 (Spermidine/spermine N(1)-acetyltransferase 1) (SSAT) (SSAT-1) (Putrescineacetyltransferase) (Polyamine N-acetyltransferase 1); (1659:) Diamine acetyltransferase 2 (Spermidine/spermineN(1)-acetyltransferase 2) (Polyamine N-acetyltransferase 2); (1660:) diamine oxidase, copper/topa quinone containing; (1661:) diamine oxidase; (1662:) dicarbonyl/L-xylulose reductase [*Homo sapiens*]; (1663:) dicer1 [*Homo sapiens*]; (1664:) dihydrofolate reductase [*Homo sapiens*]; (1665:) Dihydrofolate reductase; (1666:) dihydrolipoamide acetyltransferase; (1667:) "dihydrolipoamide branched chain transacylase (E2 component of branched chain keto acid dehydrogenase complex; maple syrup urine disease) [*Homo sapiens*]."; (1668:) Dihydrolipoamide branched chain transacylase E2 [*Homo sapiens*]; (1669:) dihydrolipoamide branched chain transacylase precursor [*Homo sapiens*]; (1670:) dihydrolipoamide dehydrogenase precursor [*Homo sapiens*]; (1671:) dihydrolipoamide dehydrogenase-binding protein [*Homo sapiens*]; (1672:) dihydrolipoamide S-acetyltransferase (E2 component of pyruvatedehydrogenase complex) [*Homo sapiens*]; (1673:) dihydrolipoamide S-acetyltransferase (E2 component of pyruvatedehydrogenase complex) variant [*Homo sapiens*]; (1674:) dihydrolipoamide S-succinyltransferase (E2 component of 2-oxo-glutarate complex) [*Homo sapiens*]; (1675:) dihydrolipoamide S-succinyltransferase (EC 2.3.1.61)-human; (1676:) dihydrolipoamide succinyltransferase [*Homo sapiens*]; (1677:) dihydrolipoamide succinyltransferase; (1678:) Dihydrolipoyl dehydrogenase, mitochondrial precursor (Dihydrolipoamide dehydrogenase) (Glycine cleavage system Lprotein); (1679:) dihydrolipoyl transacylase; (1680:) Dihydrolipoyllysine-residue acetyltransferase component of pyruvatedehydrogenase complex, mitochondrial precursor (Pyruvatedehydrogenase complex E2 subunit) (PDCE2) (E2) (DihydrolipoamideS-acetyltransferase component of pyruvate dehydrogenase complex) (PDC-E2) (70 kDa mitochondrial autoantigen of primary biliarycirrhosis) (PBC) (M2 antigen complex 70 kDa subunit); (1681:) Dihydrolipoyllysine-residue succinyltransferase component of 2-oxoglutarate dehydrogenase complex, mitochondrial precursor (Dihydrolipoamide succinyltransferase component of 2-oxoglutaratedehydrogenase complex) (E2) (E2K); (1682:) dihydroorotate dehydrogenase isoform 1 precursor [*Homo sapiens*]; (1683:) dihydroorotate dehydrogenase isoform 2 precursor [*Homo sapiens*]; (1684:) Dihydroorotate dehydrogenase, mitochondrial precursor (Dihydroorotate oxidase) (DHOdehase); (1685:) Dihydropteridine reductase (HDHPR) (Quinoid dihydropteridinereductase); (1686:) dihydropyrimidine dehydrogenase [*Homo sapiens*]; (1687:) Dihydropyrimidine dehydrogenase [NADP+] precursor (DPD) (DHPDHase) (Dihydrouracil dehydrogenase) (Dihydrothymine dehydrogenase); (1688:) dihydropyrimidine dehydrogenase; (1689:) dimerization cofactor of hepatocyte nuclear factor 1 (HNF1) from muscle [*Homo sapiens*]; (1690:) dimethylaniline monooxygenase (N-oxide-forming) (EC 1.14.13.8),hepatic 2—human; (1691:) Dimethylaniline monooxygenase [N-oxide-forming] 5 (Hepaticflavin-containing monooxygenase 5) (FMO 5) (Dimethylaniline oxidase5); (1692:) dimethylarginine dimethylaminohydrolase 1 [*Homo sapiens*]; (1693:) dimethylarginine dimethylaminohydrolase 2 [*Homo sapiens*]; (1694:) dimethylglycine dehydrogenase precursor [*Homo sapiens*]; (1695:) DIP2 disco-interacting protein 2 homolog B [*Homo sapiens*]; (1696:) DIP2 disco-interacting protein 2 homolog C (*Drosophila*) [*Homo sapiens*]; (1697:) DIP2 disco-interacting protein 2 homolog C [*Homo sapiens*]; (1698:) DIP2B protein [*Homo sapiens*]; (1699:) DIP2C protein [*Homo sapiens*]; (1700:) DIP2-like protein isoform a [*Homo sapiens*]; (1701:) dipeptidase 1 (renal) [*Homo sapiens*]; (1702:) Dipeptidase 1 precursor (Microsomal dipeptidase) (Renaldipeptidase) (hRDP) (Dehydropeptidase-I); (1703:) Dipeptidase 2 precursor; (1704:) Dipeptidase 3 precursor; (1705:) dipeptidyl peptidase 7 preproprotein [*Homo sapiens*]; (1706:) Dipeptidyl peptidase 8 (Dipeptidyl peptidase VIII) (DP8) (Prolyldipeptidase DPP8) (Dipeptidyl peptidase IV-related protein 1) (DPRP-1); (1707:) dipeptidyl peptidase 8 [*Homo sapiens*]; (1708:) dipeptidyl peptidase 8 isoform 1 [*Homo sapiens*]; (1709:) dipeptidyl peptidase 8 isoform 2 [*Homo sapiens*]; (1710:) dipeptidyl peptidase 8 isoform 3 [*Homo sapiens*]; (1711:) dipeptidyl peptidase 8 isoform 4 [*Homo sapiens*]; (1712:) Dipeptidyl peptidase 9 (Dipeptidyl peptidase IX) (DP9) (Dipeptidylpeptidase-like protein 9) (DPLP9) (Dipeptidyl peptidase IV-related protein 2) (DPRP-2); (1713:) dipeptidyl peptidase III [*Homo sapiens*]; (1714:) dipeptidylpeptidase 9 [*Homo sapiens*]; (1715:) dipeptidylpeptidase IV [*Homo sapiens*]; (1716:) Diphosphoinositol polyphosphate phosphohydrolase 1 (DIPP-1) (Diadenosine 5',5'''-P1,P6-hexaphosphate hydrolase 1) (Nucleosidediphosphate-linked moiety X motif 3) (Nudix motif 3); (1717:) Diphosphoinositol polyphosphate phosphohydrolase 2 (DIPP-2) (Diadenosine 5',5'''-P1,P6-hexaphosphate hydrolase 2) (Nucleosidediphosphate-linked moiety X motif 4) (Nudix motif 4); (1718:) Diphosphoinositol polyphosphate phosphohydrolase 3 alpha (DIPP-3alpha) (DIPP3 alpha) (hDIPP3alpha) (Diadenosine-5',5'''-P1,P6-hexaphosphate hydrolase 3 alpha) (Nucleosidediphosphate-linked moiety X motif 10) (Nudix motif 10) (hAps2); (1719:) Diphosphoinositol polyphosphate phosphohydrolase 3 beta (DIPP-3beta) (DIPP3 beta) (hDIPP3beta) (Diadenosine-5', 5'''-P1,P6-hexaphosphate hydrolase 3 beta) (Nucleosidediphosphate-linked moiety X motif 11) (Nudix motif 11) (hAps1); (1720:) diphosphomevalonate decarboxylase [Homo sapiens]; (1721:) Discoidin domain-containing receptor 2 precursor (Discoidin domain receptor 2) (Receptor protein-tyrosine kinase TKT) (Tyrosine-protein kinase TYRO 10) (Neurotrophic tyrosine kinase, receptor-related 3) (CD167b antigen); (1722:) Disco-interacting protein 2 homolog A; (1723:) Disco-interacting protein 2 homolog C; (1724:) DLST [Homo sapiens]; (1725:) DNA (cytosine-5-)-methyltransferase 1 [Homo sapiens]; (1726:) DNA cytosine methyltransferase 3 alpha isoform a [Homo sapiens]; (1727:) DNA cytosine methyltransferase 3 alpha isoform b [Homo sapiens]; (1728:) DNA cytosine methyltransferase 3 alpha isoform c [Homo sapiens]; (1729:) DNA cytosine-5 methyltransferase 3 beta isoform 1 [Homo sapiens]; (1730:) DNA cytosine-5 methyltransferase 3 beta isoform 2 [Homo sapiens]; (1731:) DNA cytosine-5 methyltransferase 3 beta isoform 3 [Homo sapiens]; (1732:) DNA cytosine-5 methyltransferase 3 beta isoform 6 [Homo sapiens]; (1733:) DNA dC→dU-editing enzyme APOBEC-3F (Apolipoprotein B mRNA-editing enzyme catalytic polypeptide-like 3F); (1734:) DNA dC→dU-editing enzyme APOBEC-3G (APOBEC-related cytidinedeaminase) (ARCD) (APOBEC-related protein) (ARP-9) (CEM15) (CEM-15); (1735:) DNA directed RNA polymerase II polypeptide A [Homo sapiens]; (1736:) DNA directed RNA polymerase II polypeptide B [Homo sapiens]; (1737:) DNA fragmentation factor subunit beta (DNA fragmentation factor 40 kDa subunit) (DFF-40) (Caspase-activated deoxyribonuclease) (Caspase-activated DNase) (CAD) (Caspase-activated nuclease) (CPAN); (1738:) DNA helicase II, HDH II=ATP-dependent DNA unwinding enzyme/Kuautoantigen large subunit {N-terminal} [human, HeLa cells, PeptidePartial, 19 aa]; (1739:) DNA ligase 3 (DNA ligase III) (Polydeoxyribonucleotide synthase[ATP] 3); (1740:) DNA ligase 4 (DNA ligase IV) (Polydeoxyribonucleotide synthase[ATP]-4); (1741:) DNA ligase I [Homo sapiens]; (1742:) DNA ligase III [Homo sapiens]; (1743:) DNA ligase IV [Homo sapiens]; (1744:) DNA mismatch repair protein [Homo sapiens]; (1745:) DNA mismatch repair protein homolog [Homo sapiens]; (1746:) DNA mismatch repair protein Mlh1 (MutL protein homolog 1); (1747:) DNA mismatch repair protein Mlh3 (MutL protein homolog 3); (1748:) DNA mismatch repair protein MLH3 [Homo sapiens]; (1749:) DNA mismatch repair protein; (1750:) DNA nucleotidylexotransferase (Terminal addition enzyme) (Terminaldeoxynucleotidyltransferase) (Terminal transferase); (1751:) DNA polymerase beta; (1752:) DNA polymerase beta2 [Homo sapiens]; (1753:) DNA polymerase epsilon, catalytic subunit A (DNA polymerase IIsubunit A); (1754:) DNA polymerase lambda (Pol Lambda) (DNA polymerase kappa) (DNApolymerase beta-2) (Pol beta2); (1755:) DNA polymerase subunit alpha B (DNA polymerase alpha 70 kDa subunit); (1756:) DNA polymerase subunit gamma 2, mitochondrial precursor (Mitochondrial DNA polymerase accessory subunit) (PolG-beta) (MtPolB) (DNA polymerase gamma accessory 55 kDa subunit) (p55); (1757:) DNA polymerase theta [Homo sapiens]; (1758:) DNA primase large subunit, 58 kDa [Homo sapiens]; (1759:) DNA primase small subunit, 49 kDa [Homo sapiens]; (1760:) DNA repair enzyme; (1761:) DNA replication licensing factor MCM6 (p105MCM); (1762:) DNA topoisomerase 1 (DNA topoisomerase I); (1763:) DNA topoisomerase 2-alpha (DNA topoisomerase II, alpha isozyme); (1764:) DNA topoisomerase I [Homo sapiens]; (1765:) DNA topoisomerase I, mitochondrial precursor (TOP1mt); (1766:) DNA topoisomerase II [Homo sapiens]; (1767:) DNA topoisomerase II, alpha isozyme [Homo sapiens]; (1768:) DNA topoisomerase II, beta isozyme [Homo sapiens]; (1769:) DNA-(apurinic or apyrimidinic site) lyase (AP endonuclease 1) (APEXnuclease) (APEN) (REF-1 protein); (1770:) DNA-3-methyladenine glycosylase (3-methyladenine DNA glycosidase) (ADPG) (3-alkyladenine DNA glycosylase) (N-methylpurine-DNAglycosylase); (1771:) DNA-binding protein [Homo sapiens]; (1772:) DNA-dependent protein kinase catalytic subunit (DNA-PK catalytic subunit) (DNA-PKcs) (DNPK1) (p460); (1773:) DNA-directed RNA polymerase II 19 kDa polypeptide (RPB7); (1774:) DNA-directed RNA polymerase III largest subunit (RPC155) (RPC1); (1775:) DNA-directed RNA polymerase III subunit C (DNA-directed III 62 kDa polypeptide) (RNA polymerase III C62 subunit) (RPC3); (1776:) DnaJ (Hsp40) homolog, subfamily B, member 6 isoform a [Homo sapiens]; (1777:) DnaJ (Hsp40) homolog, subfamily B, member 6 isoform b [Homo sapiens]; (1778:) docking protein 1 [Homo sapiens]; (1779:) dodecenoyl-CoA delta-isomerase [Homo sapiens]; (1780:) dodecenoyl-Coenzyme A delta isomerase precursor [Homo sapiens]; (1781:) dolichol monophosphate mannose synthase [Homo sapiens]; (1782:) Dolichol-phosphate mannosyltransferase (Dolichol-phosphate mannosesynthase) (Dolichyl-phosphate beta-D-mannosyltransferase) (Mannose-P-dolichol synthase) (MPD synthase) (DPM synthase); (1783:) Dolichyl-diphosphooligosaccharide-protein glycosyltransferase 48 kDa subunit precursor (Oligosaccharyl transferase 48 kDa subunit) (DDOST 48 kDa subunit); (1784:) Dolichyl-diphosphooligosaccharideprotein glycosyltransferase 63 kDa subunit precursor (Ribophorin II) (RPN-II) (RIBIIR); (1785:) Dolichyl-diphosphooligosaccharide-protein glycosyltransferase 67 kDa subunit precursor (Ribophorin I) (RPN-I); (1786:) Dolichyl-diphosphooligosaccharide-protein glycosyltransferase subunit DAD1 (Oligosaccharyl transferase subunit DAD1) (Defender against cell death 1) (DAD-1); (1787:) Dolichyl-diphosphooligosaccharide-protein glycosyltransferase subunit STT3A (Oligosaccharyl transferase subunit STT3A) (STT3-A) (B5) (Integral membrane protein 1) (TMC); (1788:) Dolichyl-diphosphooligosaccharide-protein glycosyltransferase subunit STT3B (Oligosaccharyl transferase subunit STT3B) (STT3-B) (Source of immunodominant MHC-associated peptides homolog); (1789:) dolichyl-phosphate mannosyltransferase polypeptide 1 [Homo sapiens]; (1790:) dolichyl-phosphate mannosyltransferase polypeptide 2, regulatory subunit [Homo sapiens]; (1791:) dolichyl-phosphate mannosyltransferase polypeptide 3 isoform 1 [Homo sapiens]; (1792:) dolichyl-phosphate mannosyltransferase polypeptide 3 isoform 2 [Homo sapiens]; (1793:) DOLPP1 protein [Homo sapiens]; (1794:) dopa decarboxylase (aromatic L-amino acid decarboxylase) [Homo sapiens]; (1795:) dopachrome tautomerase (dopachrome delta-isomerase, tyrosine-related protein 2) [Homo sapiens]; (1796:) Dopamine beta-hydroxylase precursor (Dopamine beta-monooxygenase); (1797:) dopamine beta-hydroxylase precursor [Homo sapiens]; (1798:) double-stranded RNA adenosine deaminase; (1799:) Double-stranded RNA-specific adenosine deaminase (DRADA) (136 kDa double-stranded RNA-binding protein) (P136) (K88DSRBP) (Interferon-inducible protein 4) (IFI-4 protein); (1800:) Double-stranded RNA-specific editase 1

(dsRNA adenosine deaminase) (RNA-editing deaminase 1) (RNA-editing enzyme 1); (1801:) Double-stranded RNA-specific editase B2 (dsRNA adenosine deaminaseB2) (RNA-dependent adenosine deaminase 3) (RNA-editing deaminase 2) (RNA-editing enzyme 2); (1802:) Drug-Protein Interactions:) Structure Of Sulfonamide Drug Complexed With Human Carbonic Anhydrase I; (1803:) dsRNA adenosine deaminase DRADA2a [*Homo sapiens*]; (1804:) dsRNA adenosine deaminase DRADA2b [*Homo sapiens*]; (1805:) dsRNA adenosine deaminase DRADA2c [*Homo sapiens*]; (1806:) Dual 3',5'-cyclic-AMP and -GMP phosphodiesterase 11A (cAMP and cGMPphosphodiesterase 11A); (1807:) Dual oxidase 1 precursor (NADPH thyroid oxidase 1) (Thyroid oxidase1) (Large NOX 1) (Long NOX 1); (1808:) Dual oxidase 2 precursor (NADPH oxidase/peroxidase DUOX2) (NADPHthyroid oxidase 2) (Thyroid oxidase 2) (NADH/NADPH thyroid oxidasep138-tox) (p138 thyroid oxidase) (Large NOX 2) (Long NOX 2); (1809:) Dual specificity mitogen-activated protein kinase kinase 1 (MAP-kinase kinase 1) (MAPKK 1) (ERK activator kinase 1) (MAPK/ERKkinase 1) (MEK1); (1810:) Dual specificity mitogen-activated protein kinase kinase 3 (MAPkinase kinase 3) (MAPKK 3) (MAPK/ERK kinase 3); (1811:) Dual specificity mitogen-activated protein kinase kinase 6 (MAP-kinase kinase 6) (MAPKK 6) (MAPK/ERK kinase 6)/(SAPKK3); (1812:) Dual specificity protein phosphatase 18 (Low molecular weight dual specificity phosphatase 20); (1813:) Dual specificity protein phosphatase 23 (Low molecular mass dual specificity phosphatase 3) (LDP-3) (VH1-like phosphatase Z); (1814:) Dual specificity testis-specific protein kinase 1 (Testicular protein kinase 1); (1815:) Dual specificity testis-specific protein kinase 2 (Testicular protein kinase 2); (1816:) Dual specificity tyrosine-phosphorylation-regulated kinase 1A(Protein kinase minibrain homolog) (MNBH) (HP86) (Dual specificity YAK1-related kinase); (1817:) Dual specificity tyrosine-phosphorylation-regulated kinase 1B (Mirk protein kinase) (Minibrain-related kinase); (1818:) Dual specificity tyrosine-phosphorylation-regulated kinase 2; (1819:) Duffy antigen/chemokine receptor (Fy glycoprotein) (GpFy) (Glycoprotein D) (*Plasmodium vivax* receptor) (CD234 antigen); (1820:) dUTP pyrophosphatase isoform 1 precursor [*Homo sapiens*]; (1821:) dUTP pyrophosphatase isoform 2 [*Homo sapiens*]; (1822:) dUTP pyrophosphatase isoform 3 [*Homo sapiens*]; (1823:) dUTP pyrophosphatase; (1824:) dynamin 1 isoform 1 [*Homo sapiens*]; (1825:) dynamin 1 isoform 2 [*Homo sapiens*]; (1826:) Dynamin-1-like protein (Dynamin-like protein) (Dnm1p/Vps1p-likeprotein) (DVLP) (Dynamin family member proline-rich carboxyl-terminal domain less) (Dymple) (Dynamin-related protein 1) (Dynamin-like protein 4) (Dynamin-like protein IV) (HdynIV); (1827:) dynein light chain 1 [*Homo sapiens*]; (1828:) dystonin isoform 1 [*Homo sapiens*]; (1829:) dystonin isoform 1e precursor [*Homo sapiens*]; (1830:) dystonin isoform 1eA precursor [*Homo sapiens*]; (1831:) dystonin isoform 1eB precursor [*Homo sapiens*]; (1832:) E-1 enzyme [*Homo sapiens*]; (1833:) E1A binding protein p300 [*Homo sapiens*]; (1834:) E1A-associated protein p300; (1835:) E2 protein [*Homo sapiens*]; (1836:) E2 ubiquitin-conjugating enzyme [*Homo sapiens*]; (1837:) E2F transcription factor 2 [*Homo sapiens*]; (1838:) E3 ubiquitin ligase IBRDC2 (IBR domain-containing protein 2) (p53-inducible RING finger protein); (1839:) E3 ubiquitin ligase TRIAD3 (Ubiquitin-conjugating enzyme7-interacting protein 1) (Zinc finger protein inhibiting NF-kappa-B) (Triad domain-containing protein 3); (1840:) E3 ubiquitin protein ligase TRAF7 (TNF receptor-associated factor7) (RING finger and WD repeat domain protein 1) (RING finger protein 119); (1841:) E3 ubiquitin-protein ligase CBL (Signal transduction protein CBL) (Proto-oncogene c-CBL) (Casitas B-lineage lymphoma proto-oncogene) (RING finger protein 55); (1842:) E3 ubiquitin-protein ligase CBL-B (Signal transduction protein CBL-B) (SH3-binding protein CBL-B) (Casitas B-lineage lymphomaproto-oncogene b) (RING finger protein 56); (1843:) E3 ubiquitin-protein ligase HECTD1 (HECT domain-containing protein1) (E3 ligase for inhibin receptor) (EULIR); (1844:) E3 ubiquitin-protein ligase NEDD4; (1845:) E3 ubiquitin-protein ligase NEDD4-like protein (Nedd-4-2) (NEDD4.2); (1846:) early growth response 1 [*Homo sapiens*]; (1847:) EBV-induced G-protein coupled receptor 2 (EBI2); (1848:) ECE-1 [*Homo sapiens*]; (1849:) ectonucleoside triphosphate diphosphohydrolase 2 isoform 1 [*Homo sapiens*]; (1850:) ectonucleoside triphosphate diphosphohydrolase 2 isoform 2 [*Homo sapiens*]; (1851:) "Ectonucleotide pyrophosphatase/phosphodiesterase 1 (E-NPP 1) (Phosphodiesterase I/nucleotide pyrophosphatase 1) (Plasma-cell membrane glycoprotein PC-1) [Includes:) Alkaline phosphodiesterase I; Nucleotide pyrophosphatase (NPPase)]."; (1852:) Ectonucleotide pyrophosphatase/phosphodiesterase 6 precursor (E-NPP6) (NPP-6) [Contains:) Ectonucleotidepyrophosphatase/phosphodiesterase 6 soluble form]; (1853:) ectonucleotide pyrophosphatase/ phosphodiesterase 7 [*Homo sapiens*]; (1854:) Ectonucleotide pyrophosphatase/phosphodiesterase 7 precursor (E-NPP7) (NPP-7) (Alkaline sphingomyelin phosphodiesterase) (Intestinal alkaline sphingomyelinase) (Alk-SMase); (1855:) EGF, latrophilin and seven transmembrane domain-containing protein1 precursor (EGF-TM7-latrophilin-related protein) (ETL protein); (1856:) EGF-like module-containing mucin-like hormone receptor-like 1 precursor (Cell surface glycoprotein EMR1) (EMR1 hormone receptor); (1857:) EGF-like module-containing mucin-like hormone receptor-like 2precursor (EGF-like module EMR2) (CD312 antigen); (1858:) EGF-like module-containing mucin-like hormone receptor-like 3precursor (EGF-like module-containing mucin-like receptor EMR3); (1859:) EGF-like module-containing mucin-like hormone receptor-like 4precursor (G-protein coupled receptor 127); (1860:) EGL nine (*C. elegans*) homolog 2 isoform 1 [*Homo sapiens*]; (1861:) EGL nine (*C. elegans*) homolog 2 isoform 2 [*Homo sapiens*]; (1862:) EGL nine (*C. elegans*) homolog 2 isoform 3 [*Homo sapiens*]; (1863:) Egl nine homolog 1 (Hypoxia-inducible factor prolyl hydroxylase 2) (HIF-prolyl hydroxylase 2) (HIF-PH2) (HPH-2) (Prolyl hydroxylasedomain-containing protein 2) (PHD2) (SM-20); (1864:) Egl nine homolog 3 (Hypoxia-inducible factor prolyl hydroxylase 3) (HIF-prolyl hydroxylase 3) (HIF-PH3) (HPH-1) (Prolyl hydroxylasedomain-containing protein 3) (PHD3); (1865:) elastase 1, pancreatic [*Homo sapiens*]; (1866:) elastase 2, neutrophil preproprotein [*Homo sapiens*]; (1867:) elastase isozyme 4, HSE 1-4 [human, sputum, Peptide Partial, 21aa]; (1868:) ELAV-like 1 [*Homo sapiens*]; (1869:) Electrogenic sodium bicarbonate cotransporter 1 (Sodium bicarbonatecotransporter) (Na(+)/HCO3(−) cotransporter) (Solute carrier family4 member 4) (kNBC1); (1870:) Elongation factor 2 kinase (eEF-2 kinase) (eEF-2K) (Calcium/calmodulin-dependent eukaryotic elongation factor 2kinase); (1871:) elongin B [*Homo sapiens*]; (1872:) elongin B isoform a [*Homo sapiens*]; (1873:) elongin B isoform b [*Homo sapiens*]; (1874:) elongin C [*Homo sapiens*]; (1875:) endo-beta-N-acetylglucosaminidase [*Homo sapiens*]; (1876:) endonuclease III [*Homo sapiens*]; (1877:) Endonuclease III-like protein 1; (1878:) Endonuclease VIII-like 2 (Nei-like 2) (DNA glycosylase/AP lyaseNei2) (DNA- (apurinic or apyrimidinic site) lyase Neil2) (NEH2); (1879:) endopeptidase La homolog (EC 3.4.21.-) precursor, mitochondrial(version 2)—human; (1880:) endoplasmic reticulum alpha-mannosidase I [Homo sapiens]; (1881:) Endoplasmic reticulum mannosyl-oligosaccharide-1,2-alpha-mannosidase (ER alpha-1,2-mannosidase) (Mannosidase alphaclass 1B member 1) (Man9GlcNAc2-specific-processing alpha-mannosidase); (1882:) endothelial cell growth factor 1 (platelet-derived) [Homo sapiens]; (1883:) Endothelial cells scavenger receptor precursor (Acetyl LDL receptor) (Scavenger receptor class F member 1); (1884:) Endothelial lipase precursor (Endothelial cell-derived lipase) (EDL) (EL); (1885:) Endothelial protein C receptor precursor (Endothelial cell proteinC receptor) (Activated protein C receptor) (APC receptor) (CD201antigen); (1886:) endothelin 1 [Homo sapiens]; (1887:) endothelin 3 isoform 1 preproprotein [Homo sapiens]; (1888:) endothelin 3 isoform 2 preproprotein [Homo sapiens]; (1889:) endothelin 3 isoform 3 preproprotein [Homo sapiens]; (1890:) Endothelin B receptor precursor (ET-B) (Endothelin receptor Nonselective type); (1891:) Endothelin B receptor-like protein 2 precursor (ETBR-LP-2) (G-protein coupled receptor 37-like 1); (1892:) endothelin converting enzyme [Homo sapiens]; (1893:) endothelin converting enzyme 1 [Homo sapiens]; (1894:) endothelin converting enzyme 1 isoform 1c [Homo sapiens]; (1895:) endothelin converting enzyme 2 isoform A [Homo sapiens]; (1896:) endothelin converting enzyme 2 isoform B [Homo sapiens]; (1897:) endothelin converting enzyme-1 [Homo sapiens]; (1898:) endothelin converting enzyme-2A [Homo sapiens]; (1899:) endothelin converting enzyme-2B [Homo sapiens]; (1900:) endothelin converting enzyme-like 1 [Homo sapiens]; (1901:) endothelin receptor type A [Homo sapiens]; (1902:) endothelin receptor type B isoform 1 [Homo sapiens]; (1903:) endothelin receptor type B isoform 2 [Homo sapiens]; (1904:) Endothelin-1 receptor precursor (Endothelin A receptor) (ET-A) (hET-AR) (ETA-R); (1905:) endothelin-converting enzyme [Homo sapiens]; (1906:) Endothelin-converting enzyme 1 (ECE-1); (1907:) Endothelin-converting enzyme 2 (ECE-2); (1908:) endothelin-converting enzyme 2B [Homo sapiens]; (1909:) endothelin-converting enzyme, isoform ECE-1a [Homo sapiens]; (1910:) endothelin-converting enzyme, isoform ECE-1b [Homo sapiens]; (1911:) endothelin-converting enzyme; (1912:) endothelin-converting enzyme-1c [Homo sapiens]; (1913:) endothelin-converting enzyme-2C [Homo sapiens]; (1914:) Endothelin-converting enzyme-like 1 (Xce protein); (1915:) endothelin-converting-enzyme 1 [Homo sapiens]; (1916:) endotheline-converting enzyme ECEL1 [Homo sapiens]; (1917:) enolase 1 [Homo sapiens]; (1918:) enolase 2 [Homo sapiens]; (1919:) enolase 3 [Homo sapiens]; (1920:) enoyl-CoA hydratase:) 3-hydroxyacyl-CoA dehydrogenase; (1921:) enoyl-Coenzyme A, hydratase/3-hydroxyacyl Coenzyme A dehydrogenase [Homo sapiens]; (1922:) enterocyte differentiation associated factor EDAF-1 [Homo sapiens]; (1923:) enterokinase precursor [Homo sapiens]; (1924:) enyol-CoA:) hydratase/3-hydroxyacyl-CoA dehydrogenase; (1925:) eosinophil serine protease [Homo sapiens]; (1926:) eosinophil serine protease 1 splicing variant [Homo sapiens]; (1927:) ephrin receptor EphB2 isoform 1 precursor [Homo sapiens]; (1928:) ephrin receptor EphB2 isoform 2 precursor [Homo sapiens]; (1929:) Ephrin type-A receptor 1 precursor (Tyrosine-protein kinasereceptor EPH); (1930:) Ephrin type-A receptor 10 precursor; (1931:) Ephrin type-A receptor 2 precursor (Tyrosine-protein kinasereceptor ECK) (Epithelial cell kinase); (1932:) Ephrin type-A receptor 3 precursor (Tyrosine-protein kinasereceptor ETK1) (HEK) (HEK4); (1933:) Ephrin type-A receptor 4 precursor (Tyrosine-protein kinasereceptor SEK) (Receptor protein-tyrosine kinase HEK8); (1934:) Ephrin type-A receptor 5 precursor (Tyrosine-protein kinasereceptor EHK-1) (EPH homology kinase 1) (Receptor protein-tyrosinekinase HEK7); (1935:) Ephrin type-A receptor 6 precursor (Tyrosine-protein kinasereceptor EHK-2) (EPH homology kinase 2); (1936:) Ephrin type-A receptor 7 precursor (Tyrosine-protein kinasereceptor EHK-3) (EPH homology kinase 3) (Receptor protein-tyrosinekinase HEK11); (1937:) Ephrin type-A receptor 8 precursor (Tyrosine-protein kinasereceptor EEK) (EPH- and ELK-related kinase) (HEK3); (1938:) Ephrin type-B receptor 1 precursor (Tyrosine-protein kinasereceptor EPH-2) (NET) (HEK6) (ELK); (1939:) Ephrin type-B receptor 2 precursor (Tyrosine-protein kinasereceptor EPH-3) (DRT) (Receptor protein-tyrosine kinase HEK5) (ERK) (NY-REN-47 antigen); (1940:) Ephrin type-B receptor 3 precursor (Tyrosine-protein kinasereceptor HEK-2); (1941:) Ephrin type-B receptor 4 precursor (Tyrosine-protein kinasereceptor HTK); (1942:) Ephrin type-B receptor 6 precursor (Tyrosine-proteinkinase-defective receptor EPH-6) (HEP); (1943:) epidermal growth factor (beta-urogastrone) [Homo sapiens]; (1944:) epidermal growth factor receptor isoform a [Homo sapiens]; (1945:) epidermal growth factor receptor isoform b [Homo sapiens]; (1946:) epidermal growth factor receptor isoform c [Homo sapiens]; (1947:) epidermal growth factor receptor isoform d [Homo sapiens]; (1948:) epidermal growth factor receptor pathway substrate 15 [Homo sapiens]; (1949:) Epidermal growth factor receptor precursor (Receptortyrosine-protein kinase ErbB-1); (1950:) Epithelial discoidin domain-containing receptor 1 precursor (Epithelial discoidin domain receptor 1) (Tyrosine kinase DDR) (Discoidin receptor tyrosine kinase) (Tyrosine-protein kinase CAK) (Cell adhesion kinase) (TRK E) (Protein-tyrosine kinase RTK 6) (HGK2) (CD167a antigen); (1951:) Epoxide hydrolase 1 (Microsomal epoxide hydrolase) (Epoxidehydratase); (1952:) Epoxide hydrolase 2 (Soluble epoxide hydrolase) (SEH) (Epoxidehydratase) (Cytosolic epoxide hydrolase) (CEH); (1953:) epoxide hydrolase 2, cytoplasmic [Homo sapiens]; (1954:) epsilon isoform of regulatory subunit B56, protein phosphatase 2A [Homo sapiens]; (1955:) epsilon-trimethyllysine 2-oxoglutarate dioxygenase [Homo sapiens]; (1956:) ER lumen protein retaining receptor 1 (KDEL receptor 1) (KDELendoplasmic reticulum protein retention receptor 1) (PutativeMAPK-activating protein PM23); (1957:) ER lumen protein retaining receptor 2 (KDEL receptor 2) (KDELendoplasmic reticulum protein retention receptor 2) (ERD2-likeprotein 1) (ELP-1); (1958:) ER lumen protein retaining receptor 3 (KDEL receptor 3) (KDELendoplasmic reticulum protein retention receptor 3); (1959:) ERO1-like protein alpha precursor (ERO1-Lalpha) (Oxidoreductin-1-Lalpha) (Endoplasmic oxidoreductin-1-like protein) (ERO1-L); (1960:) ERO1-like protein beta precursor (ERO1-Lbeta) (Oxidoreductin-1-Lbeta) (Endoplasmic oxidoreductin-1-like proteinB); (1961:) erythrocyte acylphosphatase 1 isoform a [Homo sapiens]; (1962:) erythrocyte acylphosphatase 1 isoform b [Homo sapiens]; (1963:) erythrocyte adenosine monophosphate deaminase isoform 1A [Homo sapiens]; (1964:) erythrocyte adenosine monophosphate deaminase isoform 1B [Homo sapiens]; (1965:) erythrocyte adenosine monophosphate deaminase isoform 1C [Homo sapiens]; (1966:) Erythropoietin receptor precursor (EPO-R); (1967:) estradiol 17 beta-dehydrogenase 8 [Homo sapiens]; (1968:) Estradiol 17-beta-dehydrogenase 1 (17-beta-hydroxysteroiddehydrogenase type 1) (17-beta-HSD 1) (Placental17-beta-hydroxysteroid dehydrogenase) (20 alpha-hydroxysteroiddehydrogenase) (20-alpha-HSD)

(E2DH); (1969:) Estradiol 17-beta-dehydrogenase 12 (17-beta-HSD 12) (17-beta-hydroxysteroid dehydrogenase 12) (3-ketoacyl-CoAreductase) (KAR); (1970:) Estradiol 17-beta-dehydrogenase 2 (17-beta-HSD 2) (Microsomal17-beta-hydroxysteroid dehydrogenase) (20 alpha-hydroxysteroiddehydrogenase) (20-alpha-HSD) (E2DH); (1971:) Estrogen receptor (ER) (Estradiol receptor) (ER-alpha); (1972:) Estrogen receptor beta (ER-beta); (1973:) estrogen-related receptor alpha [Homo sapiens]; (1974:) Estrogen-related receptor gamma (Estrogen receptor-related protein3) (ERR gamma-2); (1975:) ethanolamine kinase 1 isoform A [Homo sapiens]; (1976:) ethanolamine kinase 1 isoform B [Homo sapiens]; (1977:) ets variant gene 6 [Homo sapiens]; (1978:) Eukaryotic translation initiation factor 2-alpha kinase 1(Heme-regulated eukaryotic initiation factor eIF-2-alpha kinase) (Heme-regulated inhibitor) (Heme-controlled repressor) (HCR) (Hemin-sensitive initiation factor 2-alpha kinase); (1979:) eukaryotic translation initiation factor 2-alpha kinase 2 [Homo sapiens]; (1980:) Eukaryotic translation initiation factor 2-alpha kinase 3 precursor (PRKR-like endoplasmic reticulum kinase) (Pancreatic eIF2-alphakinase) (HsPEK); (1981:) Eukaryotic translation initiation factor 4 gamma 2 (eIF-4-gamma 2) (eIF-4G 2) (eIF4G 2) (p97) (Death-associated protein 5) (DAP-5); (1982:) evolutionarily related interleukin-1 beta converting enzyme [Homo sapiens]; (1983:) Exostosin-like 2 (Glucuronyl-galactosyl-proteoglycan-4-alpha-N-acetylglucosaminyltransferase) (Alpha-1,4-N-acetylhexosaminyltransferase EXTL2) (Alpha-GalNAcTEXTL2) (EXT-related protein 2); (1984:) Extracellular calcium-sensing receptor precursor (CaSR) (Parathyroid Cell calcium-sensing receptor); (1985:) FAD synthetase isoform 1 [Homo sapiens]; (1986:) FAD1 flavin adenine dinucleotide synthetase homolog (S. cerevisiae) [Homo sapiens]; (1987:) FADD-homologous ICE/CED-3-like protease [Homo sapiens]; (1988:) FAD-synthetase (PP591) [Homo sapiens]; (1989:) FAD-synthetase [Homo sapiens]; (1990:) FAM80B protein [Homo sapiens]; (1991:) Family with sequence similarity 80, member A [Homo sapiens]; (1992:) Family with sequence similarity 80, member B [Homo sapiens]; (1993:) Fanconi anemia complementation group D2 isoform a [Homo sapiens]; (1994:) Fanconi anemia complementation group D2 isoform b [Homo sapiens]; (1995:) Fanconi anemia group D2 protein (Protein FACD2); (1996:) Fanconi anemia, complementation group G [Homo sapiens]; (1997:) Far upstream element-binding protein 2 (FUSE-binding protein 2) (KHtype-splicing regulatory protein) (KSRP) (p75); (1998:) farnesyl diphosphate synthase [Homo sapiens]; (1999:) farnesylated-proteins converting enzyme 1 [Homo sapiens]; (2000:) farnesylated-proteins converting enzyme 2 [Homo sapiens]; (2001:) farnesyl-diphosphate farnesyltransferase 1 [Homo sapiens]; (2002:) Fas-associated death domain protein interleukin-1b-converting enzyme 2 [Homo sapiens]; (2003:) Fas-associated via death domain [Homo sapiens]; (2004:) fatty acid amide hydrolase [Homo sapiens]; (2005:) fatty acid CoA ligase-like AMP-binding enzyme [Homo sapiens]; (2006:) fatty acid coenzyme A ligase 5 [Homo sapiens]; (2007:) fatty acid desaturase 2 [Homo sapiens]; (2008:) fatty acid omega-hydroxylase (cytochrome P450 4A); (2009:) fatty acid synthase [Homo sapiens]; (2010:) fatty-acid-Coenzyme A ligase, long-chain 5 [Homo sapiens]; (2011:) FBP2 [Homo sapiens]; (2012:) Fc receptor-like protein 2 precursor (SH2 domain-containing phosphatase anchor protein 1) (Fc receptor homolog 2) (FcRH2) (Immunoglobulin receptor translocation-associated 4 protein); (2013:) Fc receptor-like protein 5 precursor (Immunoglobulin receptor translocation-associated gene 2 protein) (BXMAS1) (CD307 antigen); (2014:) Feline leukemia virus subgroup C receptor-related protein 1 (Felineleukemia virus subgroup C receptor) (hFLVCR); (2015:) ferredoxin 1 precursor [Homo sapiens]; (2016:) ferredoxin reductase isoform 1 precursor [Homo sapiens]; (2017:) ferredoxin reductase isoform 2 precursor [Homo sapiens]; (2018:) Ferrochelatase (protoporphyria) [Homo sapiens]; (2019:) ferrochelatase [Homo sapiens]; (2020:) ferrochelatase isoform a precursor [Homo sapiens]; (2021:) ferrochelatase isoform b precursor [Homo sapiens]; (2022:) ferrochelatase precursor [Homo sapiens]; (2023:) Ferrochelatase, mitochondrial precursor (Protoheme ferro-lyase) (Heme synthetase); (2024:) fibrinogen, alpha polypeptide isoform alpha preproprotein [Homo sapiens]; (2025:) fibrinogen, alpha polypeptide isoform alpha-E preproprotein [Homo sapiens]; (2026:) fibroblast activation protein, alpha subunit [Homo sapiens]; (2027:) fibroblast growth factor 23 precursor [Homo sapiens]; (2028:) Fibroblast growth factor receptor 2 precursor (FGFR-2) (Keratinocyte growth factor receptor 2) (CD332 antigen); (2029:) Fibroblast growth factor receptor 3 precursor (FGFR-3) (CD333antigen); (2030:) Fibroblast growth factor receptor 4 precursor (FGFR-4) (CD334antigen); (2031:) Fibroblast growth factor receptor-like 1 precursor (FGFreceptor-like protein 1) (Fibroblast growth factor receptor 5) (FGFR-like protein) (FGF homologous factor receptor); (2032:) fibronectin 1 isoform 1 preproprotein [Homo sapiens]; (2033:) fibronectin 1 isoform 2 preproprotein [Homo sapiens]; (2034:) fibronectin 1 isoform 3 preproprotein [Homo sapiens]; (2035:) fibronectin 1 isoform 4 preproprotein [Homo sapiens]; (2036:) fibronectin 1 isoform 5 preproprotein [Homo sapiens]; (2037:) fibronectin 1 isoform 6 preproprotein [Homo sapiens]; (2038:) fibronectin 1 isoform 7 preproprotein [Homo sapiens]; (2039:) Fk506 And Rapamycin-Binding Protein (Fkbp12) (Nmr, 20 Structures); (2040:) Fk506 And Rapamycin-Binding Protein (Fkbp12) (Nmr, Minimized Average Structure Excluding Electrostatic Interactions); (2041:) Fk506 And Rapamycin-Binding Protein (Fkbp12) (Nmr, Minimized Average Structure); (2042:) FK506 binding protein 12-rapamycin associated protein 1 [Homo sapiens]; (2043:) FK506 binding protein 5 [Homo sapiens]; (2044:) FK506-binding protein 10 precursor (Peptidyl-prolyl cis-transisomerase) (PPlase) (Rotamase) (65 kDa FK506-binding protein) (FKBP65) (Immunophilin FKBP65); (2045:) FK506-binding protein 1A (Peptidyl-prolyl cis-trans isomerase) (PPlase) (Rotamase) (12 kDa FKBP) (FKBP-12) (Immunophilin FKBP12); (2046:) FK506-binding protein 1A [Homo sapiens]; (2047:) FK506-binding protein 1B (Peptidyl-prolyl cis-trans isomerase 1B) (PPlase 1B) (Rotamase 1B) (12.6 kDa FKBP) (FKBP-12.6) (ImmunophilinFKBP12.6) (h-FKBP-12); (2048:) FK506-binding protein 1B isoform a [Homo sapiens]; (2049:) FK506-binding protein 1B isoform b [Homo sapiens]; (2050:) FK506-binding protein 2 precursor (Peptidyl-prolyl cis-transisomerase) (PPlase) (Rotamase) (13 kDa FKBP) (FKBP-13); (2051:) FK506-binding protein 3 (Peptidyl-prolyl cis-trans isomerase) (PPlase) (Rotamase) (25 kDa FKBP) (FKBP-25) (Rapamycin-selective 25 kDa immunophilin); (2052:) FK506-binding protein 4 [Homo sapiens]; (2053:) FK506-binding protein 5 (Peptidyl-prolyl cis-trans isomerase) (PPlase) (Rotamase) (51 kDa FK506-binding protein) (FKBP-51) (54 kDa progesterone receptor-associated immunophilin) (FKBP54) (P54) (FF1 antigen) (HSP90-binding immunophilin) (Androgen-regulated protein 6); (2054:) FK506-binding protein 6 [Homo sapiens]; (2055:) FK506-binding protein 9 precursor (Peptidyl-prolyl cis-transisomerase) (PPlase) (Rotamase); (2056:) FL cytokine receptor precursor (Tyrosine-protein kinase receptor FLT3)

(Stem cell tyrosine kinase 1) (STK-1) (CD135 antigen); (2057:) FLAD1 protein [Homo sapiens]; (2058:) FLAME-1 [Homo sapiens]; (2059:) FLAME-1-beta [Homo sapiens]; (2060:) FLAME-1-delta [Homo sapiens]; (2061:) FLAME-1-gamma [Homo sapiens]; (2062:) flap structure-specific endonuclease 1 [Homo sapiens]; (2063:) flavin adenine dinucleotide synthetase isoform 1 [Homo sapiens]; (2064:) flavin adenine dinucleotide synthetase isoform 2 [Homo sapiens]; (2065:) flavin containing monooxygenase 1 [Homo sapiens]; (2066:) flavin containing monooxygenase 2 (non-functional) [Homo sapiens]; (2067:) flavin containing monooxygenase 4 [Homo sapiens]; (2068:) flavin containing monooxygenase 5 [Homo sapiens]; (2069:) Flavin reductase (FR) (NADPH-dependent diaphorase) (NADPH-flavinreductase) (FLR) (Biliverdin reductase B) (BVR-B) (Biliverdin-IXbeta-reductase) (Green heme-binding protein) (GHBP); (2070:) FLICE-like inhibitory protein long form [Homo sapiens]; (2071:) FLJ00013 protein [Homo sapiens]; (2072:) FLJ00207 protein [Homo sapiens]; (2073:) FLJ00405 protein [Homo sapiens]; (2074:) FLJ11011 [Homo sapiens]; (2075:) FLJ12389 protein [Homo sapiens]; (2076:) FLJ13855 [Homo sapiens]; (2077:) FLJ20581 protein [Homo sapiens]; (2078:) FLJ21963 protein [Homo sapiens]; (2079:) fMet-Leu-Phe receptor (fMLP receptor) (N-formyl peptide receptor) (FPR) (N-formylpeptide chemoattractant receptor); (2080:) FMLP-related receptor I (FMLP-R-I) (Lipoxin A4 receptor) (LXA4receptor) (Formyl peptide receptor-like 1) (RFP) (HM63); (2081:) FMLP-related receptor II (FMLP-R-II) (Formylpeptide receptor-like2); (2082:) fms-related tyrosine kinase 1 (vascular endothelial growth factor/vascular permeability factor receptor) [Homo sapiens]; (2083:) folate hydrolase 1 isoform 1 [Homo sapiens]; (2084:) folate hydrolase 1 isoform 2 [Homo sapiens]; (2085:) Folate receptor alpha precursor (FR-alpha) (Folate receptor 1) (Folate receptor, adult) (Adult folate-binding protein) (FBP) (Ovarian tumor-associated antigen MOv18) (KB cells FBP); (2086:) Folate receptor beta precursor (FR-beta) (Folate receptor 2) (Folate receptor, fetal/placental) (Placental folate-binding protein) (FBP); (2087:) Folate receptor gamma precursor (FR-gamma) (Folate receptor 3); (2088:) Follicle-stimulating hormone receptor precursor (FSH-R) (Follitropin receptor); (2089:) folylpolyglutamate synthase isoform a precursor [Homo sapiens]; (2090:) folylpolyglutamate synthase isoform b [Homo sapiens]; (2091:) Folylpolyglutamate synthase, mitochondrial precursor (Folylpoly-gamma-glutamate synthetase) (FPGS) (Tetrahydrofolatesynthase) (Tetrahydrofolylpolyglutamate synthase); (2092:) "Formimidoyltransferase-cyclodeaminase(Formiminotransferase-cyclodeaminase) (FTCD) (LCHCl) [Includes: Glutamate formimidoyltransferase (Glutamate formiminotransferase) (Glutamate fomyltransferase); Formimidoyltetrahydrofolatecyclodeaminase (Formiminotetrahydrofolate cyclodeaminase)]."; (2093:) formiminotransferase cyclodeaminase [Homo sapiens]; (2094:) fragile histidine triad gene [Homo sapiens]; (2095:) frataxin isoform 1 preproprotein [Homo sapiens]; (2096:) frataxin isoform 2 preproprotein [Homo sapiens]; (2097:) Free fatty acid receptor 1 (G-protein coupled receptor 40); (2098:) Free fatty acid receptor 2 (G-protein coupled receptor 43); (2099:) Free fatty acid receptor 3 (G-protein coupled receptor 41); (2100:) Frizzled-1 precursor (Fz-1) (hFz1) (FzE1); (2101:) Frizzled-10 precursor (Fz-10) (hFz10) (FzE7); (2102:) Frizzled-2 precursor (Fz-2) (hFz2) (FzE2); (2103:) Frizzled-3 precursor (Fz-3) (hFz3); (2104:) Frizzled-4 precursor (Fz-4) (hFz4) (FzE4); (2105:) Frizzled-5 precursor (Fz-5) (hFz5) (FzE5); (2106:) Frizzled-6 precursor (Fz-6) (hFz6); (2107:) Frizzled-7 precursor (Fz-7) (hFz7) (FzE3); (2108:) Frizzled-8 precursor (Fz-8) (hFz8); (2109:) Frizzled-9 precursor (Fz-9) (hFz9) (FzE6) (CD349 antigen); (2110:) fructosamine 3 kinase [Homo sapiens]; (2111:) fructosamine-3-kinase-related protein [Homo sapiens]; (2112:) fructose-1,6-bisphosphatase [Homo sapiens]; (2113:) Fructose-1,6-bisphosphatase 1 (D-fructose-1,6-bisphosphate1-phosphohydrolase 1) (FBPase 1); (2114:) fructose-1,6-bisphosphatase 1 [Homo sapiens]; (2115:) fructose-1,6-bisphosphatase 1 variant [Homo sapiens]; (2116:) fructose-1,6-bisphosphatase 2 [Homo sapiens]; (2117:) Fructose-1,6-bisphosphatase isozyme 2 (D-fructose-1,6-bisphosphate1-phosphohydrolase 2) (FBPase 2); (2118:) fructose-1,6-bisphosphatase; (2119:) fructose-6-phosphate,2-kinase/fructose-2,6-bisphosphatase [Homo sapiens]; (2120:) Fructose-bisphosphate aldolase A (Muscle-type aldolase) (Lung cancer antigen NY-LU-1); (2121:) Fructose-bisphosphate aldolase B (Liver-type aldolase); (2122:) Fructose-bisphosphate aldolase C (Brain-type aldolase); (2123:) fructose-bisphosphate aldolase C [Homo sapiens]; (2124:) fucokinase [Homo sapiens]; (2125:) fucose-1-phosphate guanyltransferase [Homo sapiens]; (2126:) Fucose-1-phosphate guanylyltransferase (GDP-L-fucosepyrophosphorylase) (GDP-L-fucose diphosphorylase); (2127:) fucosidase, alpha-L-1, tissue [Homo sapiens]; (2128:) fucosidase, alpha-L-2, plasma [Homo sapiens]; (2129:) fucosyltransferase 1 [Homo sapiens]; (2130:) fucosyltransferase 2 (secretor status included) [Homo sapiens]; (2131:) fucosyltransferase 3 (galactoside 3(4)-L-fucosyltransferase, Lewisblood group included) [Homo sapiens]; (2132:) fucosyltransferase 5 [Homo sapiens]; (2133:) fucosyltransferase 8 isoform a [Homo sapiens]; (2134:) fucosyltransferase 8 isoform b [Homo sapiens]; (2135:) fucosyltransferase 8 isoform c [Homo sapiens]; (2136:) fukutin-related protein [Homo sapiens]; (2137:) fumarate hydratase precursor [Homo sapiens]; (2138:) Fumarylacetoacetase (Fumarylacetoacetate hydrolase) (Beta-diketonase) (FAA); (2139:) fumarylacetoacetate hydrolase (fumarylacetoacetase) [Homo sapiens]; (2140:) Furin (paired basic amino acid cleaving enzyme) [Homo sapiens]; (2141:) Furin precursor (Paired basic amino acid residue cleaving enzyme) (PACE) (Dibasic-processing enzyme); (2142:) furin preproprotein [Homo sapiens]; (2143:) Fused toes protein homolog (Ft1); (2144:) FXYD domain containing ion transport regulator 3 isoform 1precursor [Homo sapiens]; (2145:) FXYD domain containing ion transport regulator 3 isoform 2precursor [Homo sapiens]; (2146:) FXYD domain-containing ion transport regulator 2 isoform 1 [Homo sapiens]; (2147:) FXYD domain-containing ion transport regulator 2 isoform 2 [Homo sapiens]; (2148:) FXYD domain-containing ion transport regulator 5 [Homo sapiens]; (2149:) FXYD domain-containing ion transport regulator 6 [Homo sapiens]; (2150:) FXYD domain-containing ion transport regulator 7 [Homo sapiens]; (2151:) G protein-coupled bile acid receptor 1 [Homo sapiens]; (2152:) G protein-coupled receptor kinase-interactor 2 isoform 1 [Homo sapiens]; (2153:) G protein-coupled receptor kinase-interactor 2 isoform 2 [Homo sapiens]; (2154:) G protein-coupled receptor kinase-interactor 2 isoform 3 [Homo sapiens]; (2155:) G protein-coupled receptor kinase-interactor 2 isoform 4 [Homo sapiens]; (2156:) G/T mismatch-specific thymine DNA glycosylase; (2157:) G6b protein precursor; (2158:) GA binding protein transcription factor, alpha subunit (60 kD) [Homo sapiens]; (2159:) GABA(A) receptor-associated protein [Homo sapiens]; (2160:) Galactocerebrosidase precursor (GALCERase) (Galactosylceramidase) (Galactosylceramide beta-galactosidase) (Galactocerebrosidebeta-galactosidase); (2161:) Galactokinase (Galactose kinase); (2162:) galactokinase 1 [Homo sapiens]; (2163:) galactose mutarotase (aldose 1-epimerase) [Homo sapiens]; (2164:) galactose-1-phosphate uridyl transferase [Homo sapiens]; (2165:) galactose-1-phosphate uridyl transferase; (2166:) Galactose-1-phosphate uridylyltransferase (Gal-1-Puridylyltransferase) (UDP-glucosehexose-1-phosphateuridylyltransferase); (2167:) galactose-1-phosphate uridylyltransferase [Homo sapiens]; (2168:) galactose-3-O-sulfotransferase [Homo sapiens]; (2169:) Galactose-3-O-sulfotransferase 2 (Gal3ST-2) (Galbeta1-3GalNAc3'-sulfotransferase 2) (Beta-galactose-3-O-sulfotransferase 2) (Glycoprotein beta-Gal 3'-sulfotransferase 2); (2170:) galactose-3-O-sulfotransferase 2 [Homo sapiens]; (2171:) galactosidase, alpha [Homo sapiens]; (2172:) galactosidase, beta 1 [Homo sapiens]; (2173:) Galactoside 2-alpha-L-fucosyltransferase 1(GDP-L-fucose:beta-D-galactoside 2-alpha-L-fucosyltransferase 1) (Alpha(1,2)FT 1) (Fucosyltransferase 1) (Blood group H alpha2-fucosyltransferase); (2174:) Galactoside 2-alpha-L-fucosyltransferase 2(GDP-L-fucose:beta-D-galactoside 2-alpha-L-fucosyltransferase 2) (Alpha(1,2)FT 2) (Fucosyltransferase 2) (Secretor blood group alpha-2-fucosyltransferase) (Secretor factor) (Se) (SE2); (2175:) Galactoside 3(4)-L-fucosyltransferase (Blood group Lewis alpha-4-fucosyltransferase) (Lewis FT) (Fucosyltransferase 3) (FUCT-III); (2176:) galactosyl transferase-associated protein [Homo sapiens]; (2177:) galactosylceramidase (EC 3.2.1.46) precursor—human; (2178:) galactosylceramidase isoform a precursor [Homo sapiens]; (2179:) galactosylceramidase isoform b precursor [Homo sapiens]; (2180:) Galactosylgalactosylxylosylprotein 3-beta-glucuronosyltransferase 1(Beta-1,3-glucuronyltransferase 1) (Glucuronosyltransferase-P) (GlcAT-P) (UDP-GlcUA:glycoprotein beta-1,3-glucuronyltransferase) (GlcUAT-P); (2181:) Galactosylgalactosylxylosylprotein 3-beta-glucuronosyltransferase 2(Beta-1,3-glucuronyltransferase 2) (Glucuronosyltransferase-S) (GlcAT-S) (UDP-glucuronosyltransferase-S) (GlcAT-D); (2182:) galactosylgalactosylxylosyl protein 3-beta-glucuronosyltransferase 2 [Homo sapiens]; (2183:) Galactosylgalactosylxylosyl protein 3-beta-glucuronosyltransferase 3(Beta-1,3-glucuronyltransferase 3) (Glucuronosyltransferase-I) (GlcAT-I) (UDP-GlcUA:Gal beta-1,3-Gal-R glucuronyltransferase) (GlcUAT-I); (2184:) Galanin receptor type 1 (GAL1-R) (GALR1); (2185:) Galanin receptor type 2 (GAL2-R) (GALR2); (2186:) Galanin receptor type 3 (GAL3-R) (GALR3); (2187:) galctocerebrosidase; (2188:) galectin 3 [Homo sapiens]; (2189:) GalNAc 4-sulfotransferase [Homo sapiens]; (2190:) gamma isoform of regulatory subunit B55, protein phosphatase 2 isoform a [Homo sapiens]; (2191:) gamma isoform of regulatory subunit B55, protein phosphatase 2 isoform b [Homo sapiens]; (2192:) gamma isoform of regulatory subunit B56, protein phosphatase 2A isoform a [Homo sapiens]; (2193:) gamma isoform of regulatory subunit B56, protein phosphatase 2A isoform b [Homo sapiens]; (2194:) gamma isoform of regulatory subunit B56, protein phosphatase 2A isoform c [Homo sapiens]; (2195:) gamma isoform of regulatory subunit B56, protein phosphatase 2A isoform d [Homo sapiens]; (2196:) Gamma-aminobutyric acid type B receptor, subunit 1 precursor (GABA-B receptor 1) (GABA-B-R1) (Gb1); (2197:) Gamma-aminobutyric acid type B receptor, subunit 2 precursor (GABA-B receptor 2) (GABA-B-R2) (Gb2) (GABABR2) (G-protein coupled receptor 51) (HG20); (2198:) gamma-butyrobetaine dioxygenase [Homo sapiens]; (2199:) gamma-catenin [Homo sapiens]; (2200:) gamma-glutamyl carboxylase [Homo sapiens]; (2201:) gamma-glutamyl hydrolase (EC 3.4.19.9)-human; (2202:) Gamma-glutamyl hydrolase precursor (Gamma-Glu-X carboxypeptidase) (Conjugase) (GH); (2203:) gamma-glutamyl hydrolase precursor [Homo sapiens]; (2204:) gamma-glutamyltransferase 1 precursor [Homo sapiens]; (2205:) "Gamma-glutamyltransferase 5 precursor (Gamma-glutamyltranspeptidase5) (Gamma-glutamyltransferase-like activity 1) (GGT-rel) [Contains: Gamma-glutamyltransferase 5 heavy chain; Gamma-glutamyltransferase5 light chain]."; (2206:) gamma-glutamyltransferase-like activity 1 [Homo sapiens]; (2207:) gamma-glutamyltransferase-like activity 4 [Homo sapiens]; (2208:) "Gamma-glutamyltranspeptidase 1 precursor (Gamma-glutamyltransferase1) (GGT 1) (CD224 antigen) [Contains:) Gamma-glutamyltranspeptidase1 heavy chain; Gamma-glutamyltranspeptidase 1 light chain]."; (2209:) gamma-glutmyl transpeptidase-related protein; (2210:) Gamma-secretase subunit APH-1A (APH-1a) (Aph-1 alpha) (Presenilin-stabilization factor); (2211:) Gamma-secretase subunit PEN-2 (Presenilin enhancer protein 2); (2212:) ganglioside-specific alpha-2,8-polysialyltransferase; (2213:) gastric inhibitory polypeptide preproprotein [Homo sapiens]; (2214:) Gastric inhibitory polypeptide receptor precursor (GIP-R) (Glucose-dependent insulinotropic polypeptide receptor); (2215:) gastric lipase precursor [Homo sapiens]; (2216:) Gastric triacylglycerol lipase precursor (Gastric lipase) (GL); (2217:) Gastrin/cholecystokinin type B receptor (CCK-B receptor) (CCK-BR) (Cholecystokinin-2 receptor) (CCK2-R); (2218:) gastrin-releasing peptide isoform 1 preproprotein [Homo sapiens]; (2219:) gastrin-releasing peptide isoform 2 preproprotein [Homo sapiens]; (2220:) gastrin-releasing peptide isoform 3 preproprotein [Homo sapiens]; (2221:) Gastrin-releasing peptide receptor (GRP-R) (GRP-preferring bombesin receptor); (2222:) GCNT2 [Homo sapiens]; (2223:) GCNT3 protein [Homo sapiens]; (2224:) GDNF family receptor alpha-1 precursor (GFR-alpha-1) (GDNF receptor alpha) (GDNFR-alpha) (TGF-beta-related neurotrophic factor receptor1) (RET ligand 1); (2225:) GDNF family receptor alpha-2 precursor (GFR-alpha-2) (Neurturin receptor alpha) (NTNR-alpha) (NRTNR-alpha) (TGF-beta-related neurotrophic factor receptor 2) (GDNF receptor beta) (GDNFR-beta) (RET ligand 2); (2226:) GDNF family receptor alpha-3 precursor (GFR-alpha-3); (2227:) GDNF family receptor alpha-4 precursor (GFR-alpha-4) (Persephin receptor); (2228:) GDNF family receptor alpha-like precursor; (2229:) GDP-D-mannose-4,6-dehydratase [Homo sapiens]; (2230:) GDP-L-fucose pyrophosphorylase [Homo sapiens]; (2231:) GDP-mannose 4,6-dehydratase [Homo sapiens]; (2232:) GDP-mannose pyrophosphorylase A [Homo sapiens]; (2233:) GDP-mannose pyrophosphorylase B isoform 1 [Homo sapiens]; (2234:) GDP-mannose pyrophosphorylase B isoform 2 [Homo sapiens]; (2235:) gelatinase, type IV collagenase {N-terminal} [human, neutrophils, Peptide Partial, 19 aa]; (2236:) Gephyrin [Homo sapiens]; (2237:) gephyrin isoform 1 [Homo sapiens]; (2238:) gephyrin isoform 2 [Homo sapiens]; (2239:) geranylgeranyl diphosphate synthase 1 isoform A [Homo sapiens]; (2240:) geranylgeranyl diphosphate synthase 1 isoform B [Homo sapiens]; (2241:) geranylgeranyl transferase II [Homo sapiens]; (2242:) Geranylgeranyl transferase type-2 alpha subunit (Geranylgeranyltransferase type II alpha subunit) (Rab geranylgeranyltransferasealpha subunit) (Rab geranyl-geranyltransferase alpha subunit) (RabGG transferase alpha) (Rab GGTase alpha); (2243:) Geranylgeranyl transferase type-2 subunit beta (Geranylgeranyltransferase type II subunit beta) (Rab geranylgeranyltransferasesubunit beta) (Rab geranyl-geranyltransferase subunit beta) (Rab GGtransferase beta) (Rab GGTase beta); (2244:) ghrelin precursor [Homo sapiens]; (2245:) GlcNac-1-P transferase [Homo sapiens]; (2246:) GlcNAc-phosphotransferase precursor [Homo sapiens]; (2247:) Globoside alpha-1,3-N-acetylgalactosaminyltransferase 1 (Forssmanglycolipid synthetase-like protein); (2248:) glomulin [Homo sapiens]; (2249:) Glucagon receptor precursor (GL-R); (2250:) Glucagon-like peptide 1 receptor precursor (GLP-1 receptor) (GLP-1-R) (GLP-1R); (2251:) Glucagon-like peptide 2 receptor precursor (GLP-2 receptor) (GLP-2-R) (GLP-2R); (2252:) glucan (1,4-alpha-), branching enzyme 1 (glycogen branching enzyme) [Homo sapiens]; (2253:) Glucan, branching enzyme 1 variant [Homo sapiens]; (2254:) glucocerebrosidase precursor [Homo sapiens]; (2255:) Glucocorticoid receptor (GR); (2256:) Glucokinase (Hexokinase-4) (Hexokinase type IV) (HK IV) (HK4) (Hexokinase-D); (2257:) glucokinase isoform 1 [Homo sapiens]; (2258:) glucokinase isoform 2 [Homo sapiens]; (2259:) glucokinase isoform 3 [Homo sapiens]; (2260:) Glucokinase regulatory protein (Glucokinase regulator); (2261:) glucokinase regulatory protein [Homo sapiens]; (2262:) glucosamine (N-acetyl)-6-sulfatase precursor [Homo sapiens]; (2263:) glucosamine-fructose-6-phosphate aminotransferase [Homo sapiens]; (2264:) Glucosaminyl (N-acetyl) transferase 1, core 2(beta-1,6-N-acetylglucosaminyltransferase) [Homo sapiens]; (2265:) Glucosaminyl (N-acetyl) transferase 2, I-branching enzyme (I bloodgroup) [Homo sapiens]; (2266:) glucosaminyl (N-acetyl) transferase 2, I-branching enzyme isoform A [Homo sapiens]; (2267:) glucosaminyl (N-acetyl) transferase 2, I-branching enzyme isoform B [Homo sapiens]; (2268:) glucosaminyl (N-acetyl) transferase 2, I-branching enzyme isoform C [Homo sapiens]; (2269:) Glucosaminyl (N-acetyl) transferase 2, I-branching enzyme, isoformB [Homo sapiens]; (2270:) glucosaminyl (N-acetyl) transferase 3, mucin type [Homo sapiens]; (2271:) glucose phosphate isomerase [Homo sapiens]; (2272:) glucose transporter 4 [Homo sapiens]; (2273:) Glucose-6-phosphatase (G6Pase) (G-6-Pase); (2274:) glucose-6-phosphatase, catalytic subunit [Homo sapiens]; (2275:) Glucose-6-phosphate 1-dehydrogenase (G6PD); (2276:) glucose-6-phosphate dehydrogenase isoform a [Homo sapiens]; (2277:) glucose-6-phosphate dehydrogenase isoform b [Homo sapiens]; (2278:) "glucosidase, alpha; neutral C [Homo sapiens]."; (2279:) glucuronidase, beta [Homo sapiens]; (2280:) glucuronyltransferase [Homo sapiens]; (2281:) glucuronyltransferase I [Homo sapiens]; (2282:) Glutamate [NMDA] receptor subunit 3A precursor (N-methyl-D-aspartate receptor subtype NR3A) (NMDAR-L); (2283:) Glutamate [NMDA] receptor subunit 3B precursor (N-methyl-D-aspartate receptor subtype NR3B) (NR3B) (NMDAR3B); (2284:) Glutamate [NMDA] receptor subunit epsilon 1 precursor (N-methylD-aspartate receptor subtype 2A) (NR2A) (NMDAR2A) (hNR2A); (2285:) Glutamate [NMDA] receptor subunit epsilon 2 precursor (N-methylD-aspartate receptor subtype 2B) (NR2B) (NMDAR2B) (N-methyl-D-aspartate receptor subunit 3) (NR3) (hNR3); (2286:) Glutamate [NMDA] receptor subunit epsilon 3 precursor (N-methylD-aspartate receptor subtype 2C) (NR2C) (NMDAR2C); (2287:) Glutamate [NMDA] receptor subunit epsilon 4 precursor (N-methylD-aspartate receptor subtype 2D) (NR2D) (NMDAR2D) (EB11); (2288:) Glutamate [NMDA] receptor subunit zeta 1 precursor (N-methyl-D-aspartate receptor subunit NR1); (2289:) Glutamate carboxypeptidase 2 (Glutamate carboxypeptidase II) (Membrane glutamate carboxypeptidase) (mGCP) (N-acetylated-alpha-linked acidic dipeptidase I) (NAALADase I) (Pteroylpoly-gamma-glutamate carboxypeptidase) (Folylpoly-gamma-glutamate carboxypeptidase) (FGCP) (Folatehydrolase 1) (Prostate-specific membrane antigen) (PSMA) (PSM); (2290:) Glutamate decarboxylase 1 (Glutamate decarboxylase 67 kDa isoform) (GAD-67) (67 kDa glutamic acid decarboxylase); (2291:) glutamate decarboxylase 1 isoform GAD25 [Homo sapiens]; (2292:) glutamate decarboxylase 1 isoform GAD67 [Homo sapiens]; (2293:) glutamate decarboxylase 2 [Homo sapiens]; (2294:) glutamate dehydrogenase 1 [Homo sapiens]; (2295:) Glutamate dehydrogenase 1, mitochondrial precursor (GDH); (2296:) glutamate dehydrogenase 2 [Homo sapiens]; (2297:) Glutamate receptor 1 precursor (GluR-1) (GluR-A) (GluR-K1) (Glutamate receptor ionotropic, AMPA 1) (AMPA-selective glutamatereceptor 1); (2298:) Glutamate receptor 2 precursor (GluR-2) (GluR-B) (GluR-K2) (Glutamate receptor ionotropic, AMPA 2) (AMPA-selective glutamatereceptor 2); (2299:) Glutamate receptor 3 precursor (GluR-3) (GluR-C) (GluR-K3) (Glutamate receptor ionotropic, AMPA 3) (AMPA-selective glutamatereceptor 3); (2300:) Glutamate receptor 4 precursor (GluR-4) (GluR4) (GluR-D) (Glutamatereceptor ionotropic, AMPA 4) (AMPA-selective glutamate receptor 4); (2301:) Glutamate receptor delta-1 subunit precursor (GluR delta-1); (2302:) Glutamate receptor delta-2 subunit precursor (GluR delta-2); (2303:) Glutamate receptor, ionotropic kainate 1 precursor (Glutamatereceptor 5) (GluR-5) (GluR5) (Excitatory amino acid receptor 3) (EAA3); (2304:) Glutamate receptor, ionotropic kainate 2 precursor (Glutamatereceptor 6) (GluR-6) (GluR6) (Excitatory amino acid receptor 4) (EAA4); (2305:) Glutamate receptor, ionotropic kainate 3 precursor (Glutamatereceptor 7) (GluR-7) (GluR7) (Excitatory amino acid receptor 5) (EAA5); (2306:) Glutamate receptor, ionotropic kainate 4 precursor (Glutamatereceptor KA-1) (KA1) (Excitatory amino acid receptor 1) (EAA1); (2307:) Glutamate receptor, ionotropic kainate 5 precursor (Glutamatereceptor KA-2) (KA2) (Excitatory amino acid receptor 2) (EAA2); (2308:) glutamate-5-semialdehyde dehydrogenase (EC 1.2.1.41)-human(fragments); (2309:) Glutamatecysteine ligase catalytic subunit(Gamma-glutamylcysteine synthetase) (Gamma-ECS) (GCS heavy chain); (2310:) glutamate-cysteine ligase regulatory protein [Homo sapiens]; (2311:) glutamate-cysteine ligase, catalytic subunit [Homo sapiens]; (2312:) glutamic gamma-semialdehyde dehydrogenase; (2313:) glutaminase 2 [Homo sapiens]; (2314:) glutaminase C [Homo sapiens]; (2315:) glutamine synthetase [Homo sapiens]; (2316:) glutaminyl-peptide cyclotransferase precursor [Homo sapiens]; (2317:) Glutaminyl-tRNA synthetase (Glutamine-tRNA ligase) (GlnRS); (2318:) glutaminyl-tRNA synthetase [Homo sapiens]; (2319:) Glutaredoxin-2, mitochondrial precursor; (2320:) glutaryl-CoA dehydrogenase [Homo sapiens]; (2321:) Glutaryl-CoA dehydrogenase, mitochondrial precursor (GCD); (2322:) glutaryl-Coenzyme A dehydrogenase isoform a precursor [Homo sapiens]; (2323:) glutaryl-Coenzyme A dehydrogenase isoform b precursor [Homo sapiens]; (2324:) glutathione peroxidase [Homo sapiens]; (2325:) glutathione peroxidase 1 isoform 1 [Homo sapiens]; (2326:) glutathione peroxidase 1 isoform 2 [Homo sapiens]; (2327:) glutathione peroxidase 4 isoform A precursor [Homo sapiens]; (2328:) glutathione peroxidase 4 isoform B precursor [Homo sapiens]; (2329:) glutathione peroxidase 4 isoform C precursor [Homo sapiens]; (2330:) Glutathione Reductase (E.C.1.6.4.2) (Oxidized) Complex With Glutathione Disulfide And Nadp+; (2331:) Glutathione Reductase (E.C.1.6.4.2) Carboxymethylated At Cys 58Complex With Phosphate; (2332:) Glutathione Reductase (E.C.1.6.4.2) Complex With Covalently Bound Glutathione And Phosphate; (2333:) Glutathione Reductase (E.C.1.6.4.2) Modified By Bcnu(1,3-Bis(2-Chloroethyl)-1-Nitrosourea) At Cys 58 Complexed With Phosphate; (2334:) Glutathione Reductase (E.C.1.6.4.2) Modified By Hecnu(1-(2-Chloroethyl)-3-(2-Hydroxyethyl)-1-Nitrosourea) At Cys 58Complexed With Phosphate; (2335:) glutathione reductase [*Homo sapiens*]; (2336:) Glutathione reductase, mitochondrial precursor (GR) (GRase); (2337:) glutathione S-transferase A1 [*Homo sapiens*]; (2338:) glutathione S-transferase A3 [*Homo sapiens*]; (2339:) Glutathione S-transferase A4 (Glutathione S-transferase A4-4) (GSTclass-alpha member 4); (2340:) glutathione S-transferase A4 [*Homo sapiens*]; (2341:) glutathione S-transferase M1 isoform 1 [*Homo sapiens*]; (2342:) glutathione S-transferase M1 isoform 2 [*Homo sapiens*]; (2343:) glutathione S-transferase M3 [*Homo sapiens*]; (2344:) Glutathione S-transferase Mu 1 (GSTM1-1) (GST class-mu 1) (GSTM1a-1a) (GSTM1b-1b) (HB subunit 4) (GTH4); (2345:) glutathione S-transferase theta 1 [*Homo sapiens*]; (2346:) Glutathione S-transferase theta-1 (GST class-theta-1) (Glutathionetransferase T1-1); (2347:) glutathione transferase [*Homo sapiens*]; (2348:) glutathione transferase A4-4 [*Homo sapiens*]; (2349:) glutathione transferase kappa 1 [*Homo sapiens*]; (2350:) glutathione transferase T1-1 [*Homo sapiens*]; (2351:) glutathione transferase zeta 1 isoform 1 [*Homo sapiens*]; (2352:) glutathione transferase zeta 1 isoform 2 [*Homo sapiens*]; (2353:) glutathione transferase zeta 1 isoform 3 [*Homo sapiens*]; (2354:) glutathione transferase; (2355:) glyceraldehyde-3-phosphate dehydrogenase [*Homo sapiens*]; (2356:) Glycerol kinase (ATP:glycerol 3-phosphotransferase) (Glycerokinase) (GK); (2357:) Glycerol kinase, testis specific 1 (ATP:glycerol3-phosphotransferase) (Glycerokinase) (GK); (2358:) Glycerol kinase, testis specific 2 (ATP: glycerol3-phosphotransferase) (Glycerokinase) (GK); (2359:) glycerol-3-phosphate dehydrogenase 2 (mitochondrial) [*Homo sapiens*]; (2360:) Glycerol-3-phosphate dehydrogenase, mitochondrial precursor (GPD-M) (GPDH-M) (mtGPD); (2361:) glycine amidinotransferase (L-arginine: glycine amidinotransferase) [*Homo sapiens*]; (2362:) Glycine amidinotransferase, mitochondrial precursor (L-arginine:glycine amidinotransferase) (Transamidinase) (AT); (2363:) Glycine C-acetyltransferase (2-amino-3-ketobutyrate coenzyme Aligase) [*Homo sapiens*]; (2364:) glycine C-acetyltransferase precursor [*Homo sapiens*]; (2365:) Glycine cleavage system H protein, mitochondrial precursor; (2366:) glycine cleavage system protein H (aminomethyl carrier) [*Homo sapiens*]; (2367:) glycine dehydrogenase (decarboxylating) [*Homo sapiens*]; (2368:) glycine N-methyltransferase [*Homo sapiens*]; (2369:) Glycine receptor subunit alpha-1 precursor (Glycine receptor 48 kDa subunit) (Glycine receptor strychnine-binding subunit); (2370:) Glycine receptor subunit alpha-2 precursor; (2371:) Glycine receptor subunit alpha-3 precursor; (2372:) Glycine receptor subunit beta precursor (Glycine receptor 58 kDa subunit); (2373:) glycine-N-acyltransferase isoform a [*Homo sapiens*]; (2374:) glycine-N-acyltransferase isoform b [*Homo sapiens*]; (2375:) glycoasparaginase; (2376:) Glycogen [starch] synthase, liver; (2377:) Glycogen [starch] synthase, muscle; (2378:) "Glycogen debranching enzyme (Glycogen debrancher) [Includes: 4-alpha-glucanotransferase (Oligo-1, 4-1,4-glucantransferase);Amylo-alpha-1,6-glucosidase (A-mylo-1,6-glucosidase) (Dextrin6-alpha-D-glucosidase)]."; (2379:) glycogen debranching enzyme [*Homo sapiens*]; (2380:) glycogen debranching enzyme isoform 1 [*Homo sapiens*]; (2381:) glycogen debranching enzyme isoform 2 [*Homo sapiens*]; (2382:) glycogen debranching enzyme isoform 3 [*Homo sapiens*]; (2383:) glycogen debranching enzyme isoform 4 [*Homo sapiens*]; (2384) glycogen debranching enzyme isoform 6 [*Homo sapiens*]; (2385:) glycogen phosphorylase [*Homo sapiens*]; (2386:) Glycogen phosphorylase, brain form; (2387:) Glycogen phosphorylase, liver form; (2388:) Glycogen phosphorylase, muscle form (Myophosphorylase); (2389:) glycogen synthase kinase 3 beta [*Homo sapiens*]; (2390:) Glycogen synthase kinase-3 beta (GSK-3 beta); (2391:) glycogen-debranching enzyme [*Homo sapiens*]; (2392:) glycophorin A precursor [*Homo sapiens*]; (2393:) glycoprotein V (platelet) [*Homo sapiens*]; (2394:) glycoprotein-fucosylgalactosidealpha-N-acetylgalactosaminyltransferase (EC 2.4.1.40) A1 allele[validated]—human; (2395:) glycosylphosphatidylinositol specific phospholipase D1 isoform 1precursor [*Homo sapiens*]; (2396:) glycosylphosphatidylinositol specific phospholipase D1 isoform 2precursor [*Homo sapiens*]; (2397:) Glycylpeptide N-tetradecanoyltransferase 1 (PeptideN-myristoyltransferase 1) (Myristoyl-CoA: proteinN-myristoyltransferase 1) (NMT 1) (Type I N-myristoyltransferase); (2398:) glycyl-tRNA synthetase [*Homo sapiens*]; (2399:) glyoxalase I [*Homo sapiens*]; (2400:) glyoxylate reductase/hydroxypyruvate reductase [*Homo sapiens*]; (2401:) Glyoxylate reductase/hydroxypyruvate reductase; (2402:) GM2 ganglioside activator precursor [*Homo sapiens*]; (2403:) Golgi autoantigen, golgin subfamily a, 2 [*Homo sapiens*]; (2404:) golgi autoantigen, golgin subfamily b, macrogolgin (with transmembrane signal), 1 [*Homo sapiens*]; (2405:) Golgi reassembly stacking protein 1 [*Homo sapiens*]; (2406:) Golgi-specific brefeldin A-resistance guanine nucleotide exchange factor 1 (BFA-resistant GEF 1); (2407:) Golli-mbp isoform 1 [*Homo sapiens*]; (2408:) Golli-mbp isoform 2 [*Homo sapiens*]; (2409:) Gonadotropin-releasing hormone II receptor (Type II GnRH receptor) (GnRH-II-R); (2410:) Gonadotropin-releasing hormone receptor (GnRH receptor) (GnRH-R); (2411:) gp180-carboxypeptidase D-like enzyme [*Homo sapiens*]; (2412:) GPI mannosyltransferase 1 (GPI mannosyltransferase I) (GPI-MT-I) (Phosphatidylinositol-glycan biosynthesis class M protein) (PIG-M); (2413:) GPI mannosyltransferase 2 (GPI mannosyltransferase II) (GPI-MT-II) (Phosphatidylinositol-glycan biosynthesis class V protein) (PIG-V); (2414:) GPI transamidase component PIG-T precursor (Phosphatidylinositol-glycan biosynthesis class T protein); (2415:) GPI-anchor transamidase precursor (GPI transamidase) (Phosphatidylinositol-glycan biosynthesis class K protein) (PIG-K) (hGPI8); (2416:) G-protein coupled bile acid receptor 1 (Membrane-type receptor for bile acids) (M-BAR) (hGPCR19) (BG37) (hBG37); (2417:) G-protein coupled receptor 120 (G-protein coupled receptor PGR4) (G-protein coupled receptor GT01) (G-protein coupled receptor 129); (2418:) G-protein coupled receptor 143 (Ocular albinism type 1 protein); (2419:) G-protein coupled receptor 15 (BOB); (2420:) G-protein coupled receptor 56 precursor (TM7XN1 protein); (2421:) G-protein coupled receptor 64 precursor (Epididymis-specific protein 6) (He6 receptor); (2422:) G-protein coupled receptor 98 precursor (Monogenic audiogenic seizure susceptibility protein 1 homolog) (Very large G-protein coupled receptor 1) (Usher syndrome type-2C protein); (2423:) G-protein coupled receptor family C group 5 member B precursor (Retinoic acid-induced gene 2 protein) (RAIG-2) (A-69G12.1); (2424:) G-protein coupled receptor family C group 5 member C precursor (Retinoic acid-induced gene 3 protein) (RAIG-3); (2425:) G-protein coupled receptor family C group 5 member D; (2426:) G-protein coupled receptor family C group 6 member A precursor (hGPRC6A) (G-protein coupled receptor 33) (hGPCR33); (2427:) Grainyhead-like protein 1 homolog (Transcription factor CP2-like 2) (Transcription factor LBP-32) (NH32) (Mammalian grainyhead); (2428:) Granulocyte colony-stimulating factor receptor precursor (G-CSF-R) (CD114 antigen); (2429:) Granulocyte-macrophage colony-stimulating factor receptor alphachain precursor (GM-CSF-R-alpha) (GMR) (CD116 antigen) (CDw116); (2430:) Granzyme A precursor (Cytotoxic T-lymphocyte proteinase 1) (Hanukkah factor) (H factor) (HF) (Granzyme-1) (CTL tryptase); (2431:) Granzyme B precursor (T-cell serine protease 1-3E) (CytotoxicT-lymphocyte proteinase 2) (Lymphocyte protease) (SECT) (Granzyme-2) (Cathepsin G-like 1) (CTSGL1) (CTLA-1) (Humanlymphocyte protein) (HLP) (C11); (2432:) granzyme B precursor [Homo sapiens]; (2433:) Granzyme H precursor (Cytotoxic T-lymphocyte proteinase) (CathepsinG-like 2) (CTSGL2) (CCP-X) (Cytotoxic serine protease C) (CSP-C); (2434:) granzyme M precursor [Homo sapiens]; (2435:) Green-sensitive opsin (Green cone photoreceptor pigment); (2436:) Group 3 secretory phospholipase A2 precursor (Group III secretoryphospholipase A2) (Phosphatidylcholine 2-acylhydrolase GIII) (GIIIsPLA2); (2437:) group III secreted phospholipase A2 [Homo sapiens]; (2438:) growth factor receptor-bound protein 2 isoform 1 [Homo sapiens]; (2439:) growth factor receptor-bound protein 2 isoform 2 [Homo sapiens]; (2440:) growth hormone 1 isoform 1 [Homo sapiens]; (2441:) growth hormone 1 isoform 2 [Homo sapiens]; (2442:) growth hormone 1 isoform 3 [Homo sapiens]; (2443:) growth hormone 1 isoform 4 [Homo sapiens]; (2444:) growth hormone 1 isoform 5 [Homo sapiens]; (2445:) Growth hormone receptor precursor (GH receptor) (Somatotropin receptor) [Contains:) Growth hormone-binding protein (GH-binding protein) (GHBP) (Serum-binding protein)]; (2446:) Growth hormone secretagogue receptor type 1 (GHS-R) (GH-releasing peptide receptor) (GHRP) (Ghrelin receptor); (2447:) Growth hormone-releasing hormone receptor precursor (GHRH receptor) (GRF receptor) (GRFR); (2448:) growth-inhibiting protein 17 [Homo sapiens]; (2449:) G-T3 synthase; (2450:) GTP cyclohydrase I [Homo sapiens]; (2451:) GTP cyclohydrolase 1 isoform 1 [Homo sapiens]; (2452:) GTP cyclohydrolase 1 isoform 2 [Homo sapiens]; (2453:) GTP cyclohydrolase 1 isoform 3 [Homo sapiens]; (2454:) GTP cyclohydrolase I (GTP-CH-1); (2455:) GTP cyclohydrolase I [Homo sapiens]; (2456:) GTPase activating Rap/RanGAP domain-like 1 isoform 1 [Homo sapiens]; (2457:) GTPase activating Rap/RanGAP domain-like 1 isoform 2 [Homo sapiens]; (2458:) GTPase ERas precursor (E-Ras) (Embryonic stem cell-expressed Ras); (2459:) GTPase HRas precursor (Transforming protein p21) (p21ras) (H-Ras-1) (c-H-ras); (2460:) GTPase KRas (K-Ras 2) (Ki-Ras) (c-K-ras) (c-Ki-ras); (2461:) GTPase NRas precursor (Transforming protein N-Ras); (2462:) GTP-binding protein Rit1 (Ras-like protein expressed in many tissues) (Ras-like without CAAX protein 1); (2463:) guanine deaminase [Homo sapiens]; (2464:) guanine nucleotide exchange factor p532 [Homo sapiens]; (2465:) guanosine monophosphate reductase [Homo sapiens]; (2466:) guanylate cyclase 1, soluble, alpha 2 [Homo sapiens]; (2467:) guanylate cyclase activator 1A (retina) [Homo sapiens]; (2468:) "Guanylate cyclase activator 2B precursor [Contains:) Guanylatecyclase C-activating peptide 2 (Guanylate cyclase C-activating peptide II) (GCAP-II); Uroguanylin (UGN)]."; (2469:) Guanylate cyclase soluble subunit alpha-2 (GCS-alpha-2); (2470:) Guanylate cyclase soluble subunit alpha-3 (GCS-alpha-3) (Soluble guanylate cyclase large subunit) (GCS-alpha-1); (2471:) Guanylate cyclase soluble subunit beta-1 (GCS-beta-1) (Soluble guanylate cyclase small subunit) (GCS-beta-3); (2472:) Guanylate cyclase soluble subunit beta-2 (GCS-beta-2); (2473:) guanylate cyclase: SUBUNIT=alpha2; (2474:) "Guanylin precursor (Guanylate cyclase activator 2A) (Guanylatecyclase-activating protein 1) (Gap-I) [Contains:) HMW-guanylin;Guanylin]."; (2475:) H(+)-transporting two-sector ATPase [Homo sapiens]; (2476:) H+-exporting ATPase (EC 3.6.3.6) chain D, vacuolar—human; (2477:) H2A histone family, member O [Homo sapiens]; (2478:) HACL1 protein [Homo sapiens]; (2479:) head and neck tumor and metastasis related protein [Homo sapiens]; (2480:) heat shock 27 kDa protein 1 [Homo sapiens]; (2481:) heat shock 27 kDa protein 2 [Homo sapiens]; (2482:) heat shock 70 kDa protein 5 [Homo sapiens]; (2483:) heat shock-like protein 1 [Homo sapiens]; (2484:) HEAT-like (PBS lyase) repeat containing 1 [Homo sapiens]; (2485:) Heat-stable enterotoxin receptor precursor (GC-C) (Intestinalguanylate cyclase) (STA receptor) (hSTAR); (2486:) hect domain and RLD 5 [Homo sapiens]; (2487:) hedgehog acyltransferase [Homo sapiens]; (2488:) heme oxygenase (decyclizing) 1 [Homo sapiens]; (2489:) heme oxygenase (decyclizing) 2 [Homo sapiens]; (2490:) heparan sulfate (glucosamine) 3-O-sulfotransferase 5 [Homo sapiens]; (2491:) heparan sulfate (glucosamine) 3-O-sulfotransferase 6 [Homo sapiens]; (2492:) heparan sulfate 2-O-sulfotransferase 1 [Homo sapiens]; (2493:) heparan sulfate 3-O-sulfotransferase-1 precursor [Homo sapiens]; (2494:) heparan sulfate 6-O-sulfotransferase [Homo sapiens]; (2495:) heparan sulfate 6-O-sulfotransferase 3 [Homo sapiens]; (2496:) heparan sulfate D-glucosaminyl 3-O-sulfotransferase 2 [Homo sapiens]; (2497:) heparan sulfate D-glucosaminyl 3-O-sulfotransferase 1 precursor [Homo sapiens]; (2498:) heparan sulfate D-glucosaminyl 3-O-sulfotransferase 3A1 [Homo sapiens]; (2499:) heparan sulfate D-glucosaminyl 3-O-sulfotransferase 3B1 [Homo sapiens]; (2500:) heparan sulfate D-glucosaminyl 3-O-sulfotransferase 4 [Homo sapiens]; (2501:) Heparan sulfate glucosamine 3-O-sulfotransferase 1 precursor (Heparan sulfate D-glucosaminyl 3-O-sulfotransferase 1) (Heparansulfate 3-O-sulfotransferase 1) (h3-OST-1); (2502:) Heparan sulfate glucosamine 3-O-sulfotransferase 3A1 (Heparansulfate D-glucosaminyl 3-O-sulfotransferase 3A1) (Heparan sulfate3-O-sulfotransferase 3A1) (h3-OST-3A); (2503:) Heparan sulfate glucosamine 3-O-sulfotransferase 3B1 (Heparansulfate D-glucosaminyl 3-O-sulfotransferase 3B1) (Heparan sulfate3-O-sulfotransferase 3B1) (h3-OST-3B); (2504:) Heparan sulfate glucosamine 3-O-sulfotransferase 5 (Heparan sulfateD-glucosaminyl 3-O-sulfotransferase 5) (Heparan sulfate3-O-sulfotransferase 5) (h3-OST-5); (2505:) Heparan sulfate glucosamine 3-O-sulfotransferase 6 (Heparan sulfateD-glucosaminyl 3-O-sulfotransferase 6) (Heparan sulfate3-O-sulfotransferase 6) (h3-OST-6); (2506:) heparanase [Homo sapiens]; (2507:) "Heparanase precursor (Heparanase-1) (Hpa1) (Endo-glucoronidase) [Contains:) Heparanase 8 kDa subunit; Heparanase 50 kDa subunit]."; (2508:) heparanase precursor [Homo sapiens]; (2509:) Heparanase-2 (Hpa2); (2510:) Heparan-sulfate 6-O-sulfotransferase 1 (HS6ST-1); (2511:) Heparan-sulfate 6-O-sulfotransferase 2 (HS6ST-2); (2512:) Heparan-sulfate 6-O-sulfotransferase 3 (HS6ST-3); (2513:) Heparin-binding EGF-like growth factor precursor (HB-EGF) (HBEGF) (Diphtheria toxin receptor) (DT-R); (2514:) Hepatic triacylglycerol lipase precursor (Hepatic lipase) (HL); (2515:) Hepatitis A virus cellular receptor 1 precursor (HAVcr-1) (T cell immunoglobulin and mucin domain-containing protein 1) (TIMD-1) (Tcell membrane protein 1) (TIM-1) (TIM); (2516:) Hepatocyte growth factor receptor precursor (HGF receptor) (Scatterfactor receptor) (SF receptor) (HGF/SF receptor) (Metproto-oncogene tyrosine kinase) (c-Met); (2517:) Hepatocyte nuclear factor 4-alpha (HNF-4-alpha) (Transcriptionfactor HNF-4) (Transcription factor 14);

(2518:) Hepatocyte nuclear factor 4-gamma (HNF-4-gamma); (2519:) herpesvirus associated ubiquitin-specific protease (HAUSP) [*Homo sapiens*]; (2520:) "HERV-K_3q27.3 provirus ancestral Pol protein [Includes:) Reversetranscriptase (RT); Ribonuclease H(RNase H); Integrase (IN)]."; (2521:) HERV-K_5q33.3 provirus ancestral Pro protein (HERV-K10 Pro protein) (HERV-K107 Pro protein) (Protease) (Proteinase) (PR); (2522:) "HERV-K_7p22.1 provirus ancestral Pol protein (HERV-K(HML-2.HOM) Polprotein) (HERV-K108 Pol protein) (HERV-K(C7) Pol protein) [Includes:) Reverse transcriptase (RT); Ribonuclease H(RNase H);Integrase (IN)]."; (2523:) heterogeneous nuclear ribonucleoprotein AB isoform a [*Homo sapiens*]; (2524:) heterogeneous nuclear ribonucleoprotein AB isoform b [*Homo sapiens*]; (2525:) hexokinase 1 [*Homo sapiens*]; (2526:) hexokinase 1 isoform HKI [*Homo sapiens*]; (2527:) hexokinase 1 isoform HKI-R [*Homo sapiens*]; (2528:) hexokinase 1 isoform HKI-ta/tb [*Homo sapiens*]; (2529:) hexokinase 1 isoform HKI-td [*Homo sapiens*]; (2530:) hexokinase 2 [*Homo sapiens*]; (2531:) hexokinase 3 [*Homo sapiens*]; (2532:) Hexokinase-1 (Hexokinase type I) (HK I) (Brain form hexokinase); (2533:) Hexokinase-2 (Hexokinase type II) (HK II) (Muscle form hexokinase); (2534:) Hexokinase-3 (Hexokinase type III) (HK III); (2535:) hexosaminidase A preproprotein [*Homo sapiens*]; (2536:) hexosaminidase B preproprotein [*Homo sapiens*]; (2537:) hexose-6-phosphate dehydrogenase precursor [*Homo sapiens*]; (2538:) HGD protein [*Homo sapiens*]; (2539:) "HHR6A (Human homologue of yeast RAD 6); putative."; (2540:) "HHR6B (Human homologue of yeast RAD 6); putative."; (2541:) High affinity immunoglobulin epsilon receptor alpha-subunit precursor (FcERI) (IgE Fc receptor, alpha-subunit) (Fc-epsilonRI-alpha); (2542:) High affinity immunoglobulin epsilon receptor gamma-subunit-precursor (FceRI gamma) (IgE Fc receptor gamma-subunit) (Fc-epsilonRl-gamma); (2543:) High affinity immunoglobulin epsilon receptor subunit beta (FcERI) (IgE Fc receptor, subunit beta) (Fc epsilon receptor 1 beta-chain); (2544:) High affinity immunoglobulin gamma Fc receptor I precursor (Fc-gamma RI) (FcRI) (IgG Fc receptor I) (CD64 antigen); (2545:) High affinity interleukin-8 receptor A (IL-8R A) (IL-8 receptor type 1) (CXCR-1) (CD181 antigen) (CDw128a); (2546:) High affinity interleukin-8 receptor B (IL-8R B) (CXCR-2) (GRO/MGSA receptor) (IL-8 receptor type 2) (CD182 antigen) (CDw128b); (2547:) High affinity nerve growth factor receptor precursor (Neurotrophictyrosine kinase receptor type 1) (TRK1 transforming tyrosine kinase protein) (p140-TrkA) (Trk-A); (2548:) High-affinity cAMP-specific 3',5'-cyclic phosphodiesterase 7A (HCP1) (TM22); (2549:) High-affinity cAMP-specific and IBMX-insensitive 3',5'-cyclicphosphodiesterase 8A; (2550:) High-affinity cAMP-specific and IBMX-insensitive 3',5'-cyclicphosphodiesterase 8B (HSPDE8B); (2551:) High-affinity cationic amino acid transporter 1 (CAT-1) (CAT1) (System Y+basic amino acid transporter) (Ecotropic retroviralleukemia receptor homolog) (ERR) (Ecotropic retrovirus receptorhomolog); (2552:) High-affinity cGMP-specific 3',5'-cyclic phosphodiesterase 9A; (2553:) Histamine H1 receptor; (2554:) H1stamine H2 receptor (H2R) (Gastric receptor I); (2555:) Histamine H3 receptor (HH3R) (G-protein coupled receptor 97); (2556:) Histamine H4 receptor (HH4R) (GPRv53) (G-protein coupled receptor105) (GPCR105) (SP9144) (AXOR35); (2557:) Histamine N-methyltransferase (HMT); (2558:) histamine N-methyltransferase [*Homo sapiens*]; (2559:) histamine N-methyltransferase isoform 1 [*Homo sapiens*]; (2560:) histamine N-methyltransferase isoform 2 [*Homo sapiens*]; (2561:) histamine N-methyltransferase isoform 3 [*Homo sapiens*]; (2562:) histamine N-methyltransferase variant 1 [*Homo sapiens*]; (2563:) histamine N-methyltransferase variant 2 [*Homo sapiens*]; (2564:) histamine N-methyltransferase variant 3 [*Homo sapiens*]; (2565:) histamine N-methyltransferase; (2566:) Histidine acid phosphatase domain containing 1 [*Homo sapiens*]; (2567:) Histidine acid phosphatase domain containing 2A isoform 4 [*Homo sapiens*]; (2568:) histidine ammonia-lyase [*Homo sapiens*]; (2569:) histidine decarboxylase [*Homo sapiens*]; (2570:) histidine triad nucleotide binding protein 1 [*Homo sapiens*]; (2571:) histidine triad protein member 5 [*Homo sapiens*]; (2572:) histidyl-tRNA synthetase [*Homo sapiens*]; (2573:) histidyl-tRNA synthetase-like [*Homo sapiens*]; (2574:) Histone acetyltransferase HTATIP (60 kDa Tat interactive protein) (Tip60) (HIV-1 Tat interactive protein) (cPLA(2)-interacting protein); (2575:) Histone acetyltransferase MYST3 (MYST protein 3) (MOZ, YBF2/SAS3,SAS2 and TIP60 protein 3) (Runt-related transcription factor-binding protein 2) (Monocytic leukemia zinc finger protein) (Zinc finger protein 220); (2576:) Histone acetyltransferase MYST4 (MYST protein 4) (MOZ, YBF2/SAS3,SAS2 and TIP60 protein 4) (Histone acetyltransferase MOZ2) (Monocytic leukemia zinc finger protein-related factor) (Histoneacetyltransferase MORF); (2577:) Histone acetyltransferase PCAF (P300/CBP-associated factor) (P/CAF) (Histone acetylase PCAF); (2578:) histone deacetylase 2 [*Homo sapiens*]; (2579:) histone stem-loop binding protein [*Homo sapiens*]; (2580:) Histone-lysine N-methyltransferase, H3 lysine-79 specific (HistoneH3-K79 methyltransferase) (H3-K79-HMTase) (DOT1-like protein); (2581:) Histone-lysine N-methyltransferase, H3 lysine-9 specific 1 (HistoneH3-K9 methyltransferase 1) (H3-K9-HMTase 1) (Suppressor of variegation 3-9 homolog 1) (Su(var)3-9 homolog 1); (2582:) Histone-lysine N-methyltransferase, H3 lysine-9 specific 3 (HistoneH3-K9 methyltransferase 3) (H3-K9-HMTase 3) (Euchromatichistone-lysine N-methyltransferase 2) (HLA-B-associated transcript8) (Protein G9a); (2583:) Histone-lysine N-methyltransferase, H3 lysine-9 specific 5 (HistoneH3-K9 methyltransferase 5) (H3-K9-HMTase 5) (Euchromatichistone-lysine N-methyltransferase 1) (Eu-HMTase1) (G9a-likeprotein 1) (GLP1); (2584:) HIV-1 Tat interactive protein, 60 kDa isoform 1 [*Homo sapiens*]; (2585:) HIV-1 Tat interactive protein, 60 kDa isoform 2 [*Homo sapiens*]; (2586:) HIV-1 Tat interactive protein, 60 kDa isoform 3 [*Homo sapiens*]; (2587:) HLA class II histocompatibility antigen, DP alpha chain precursor (HLA-SB alpha chain) (MHC class II DP3-alpha) (DP(W3)) (DP(W4)); (2588:) HLA-B associated transcript 8 isoform a [*Homo sapiens*]; (2589:) HLA-B associated transcript 8 isoform b [*Homo sapiens*]; (2590:) hla-dcalpha alpha 2 domain (partial) [*Homo sapiens*]; (2591:) hla-dralpha related alpha 2 domain [*Homo sapiens*]; (2592:) HMC chymase I [*Homo sapiens*]; (2593:) HMGCR protein [*Homo sapiens*]; (2594:) hMLH1 gene product; (2595:) HMT1 hnRNP methyltransferase-like 6 [*Homo sapiens*]; (2596:) hMYHalpha1 [*Homo sapiens*]; (2597:) hMYHalpha2 [*Homo sapiens*]; (2598:) hMYHalpha3 [*Homo sapiens*]; (2599:) hMYHalpha4 [*Homo sapiens*]; (2600:) hMYHbetal [*Homo sapiens*]; (2601:) hMYHbeta3 [*Homo sapiens*]; (2602:) hMYHbeta5 [*Homo sapiens*]; (2603:) hMYHgamma2 [*Homo sapiens*]; (2604:) hMYHgamma3 [*Homo sapiens*]; (2605:) hMYHgamma4 [*Homo sapiens*]; (2606:) HNF1-alpha dimerization cofactor [*Homo sapiens*]; (2607:) homogentisate 1,2-dioxygenase [*Homo sapiens*]; (2608:) "homogentisate 1,2-dioxygenase; HGO [*Homo sapiens*]."; (2609:) homogentisate dioxygenase [*Homo sapiens*]; (2610:) homolgue of yeast DNA repair and recombination enzyme (RAD52)gene; (2611:) homolog of yeast long chain polyunsaturated fatty acid elongation [*Homo sapiens*]; (2612:) homolog of yeast mutL gene; (2613:) Hormone-sensitive lipase (HSL); (2614:) hormone-sensitive lipase [*Homo sapiens*]; (2615:) HOYS7 [*Homo sapiens*]; (2616:) hPMS7 [*Homo sapiens*]; (2617:) H-protein; (2618:) HSPC015 [*Homo sapiens*]; (2619:) HSPC140 [*Homo sapiens*]; (2620:) HSPC150 [*Homo sapiens*]; (2621:) HSPC153 [*Homo sapiens*]; (2622:) HSPC279 [*Homo sapiens*]; (2623:) HtrA serine peptidase 1 [*Homo sapiens*]; (2624:) human 26S proteasome subunit p97 [*Homo sapiens*]; (2625:) Human Arylsulfatase A; (2626:) human endothelin-converting enzyme-1d isoform [*Homo sapiens*]; (2627:) human gamma-glutamyl hydrolase [*Homo sapiens*]; (2628:) Human Glutathione Reductase A34e, R37w Mutant, Mixed Disulfide Between Trypanothione And The Enzyme; (2629:) Human Glutathione Reductase A34e, R37w Mutant, Oxidized Glutathione Complex; (2630:) Human Glutathione Reductase A34e, R37w Mutant, Oxidized Trypanothione Complex; (2631:) Human Glutathione Reductase A34e, R37w Mutant, Glutathionyl spermidine Complex; (2632:) Human Glutathione Reductase A34eR37W MUTANT; (2633:) Human Glutathione Reductase Modified By Dinitrosoglutathione; (2634:) Human Glutathione Reductase Modified ByDiglutathione-Dinitroso-Iron; (2635:) human homolog of *E. coli* mutL gene product, Swiss-Prot Accession Number P23367; (2636:) human mammary dihydrolipoamide acetyltransferase, mature sequence [*Homo sapiens*]; (2637:) Human Ubc9; (2638:) human ubiquitin conjugating enzyme G2 EC 6.3.2.19. [*Homo sapiens*]; (2639:) huntingtin [*Homo sapiens*]; (2640:) huntingtin interacting protein 2 [*Homo sapiens*]; (2641:) huntingtin interacting protein; (2642:) hyaluronan synthase (EC 2.4.1.-)—human; (2643:) hyaluronan synthase 3 [*Homo sapiens*]; (2644:) Hyaluronidase-2 precursor (Hyal-2) (Hyaluronoglucosaminidase-2) (LUCA-2); (2645:) hyaluronoglucosaminidase 1 isoform 1 [*Homo sapiens*]; (2646:) hyaluronoglucosaminidase 1 isoform 2 [*Homo sapiens*]; (2647:) hyaluronoglucosaminidase 1 isoform 3 [*Homo sapiens*]; (2648:) hyaluronoglucosaminidase 1 isoform 4 [*Homo sapiens*]; (2649:) hyaluronoglucosaminidase 1 isoform 5 [*Homo sapiens*]; (2650:) hyaluronoglucosaminidase 1 isoform 6 [*Homo sapiens*]; (2651:) hydroxyacyl glutathione hydrolase isoform 1 [*Homo sapiens*]; (2652:) hydroxyacyl glutathione hydrolase isoform 2 [*Homo sapiens*]; (2653:) hydroxyacyl-Coenzyme A dehydrogenase, type II isoform 1 [*Homo sapiens*]; (2654:) hydroxyacyl-Coenzyme A dehydrogenase, type II isoform 2 [*Homo sapiens*]; (2655:) hydroxy-delta-5-steroid dehydrogenase, 3 beta- and steroiddelta-isomerase 1 [*Homo sapiens*]; (2656:) hydroxy-delta-5-steroid dehydrogenase, 3 beta- and steroiddelta-isomerase 2 [*Homo sapiens*]; (2657:) Hydroxymethylbilane synthase [*Homo sapiens*]; (2658:) hydroxymethylbilane synthase isoform 1 [*Homo sapiens*]; (2659:) hydroxymethylbilane synthase isoform 2 [*Homo sapiens*]; (2660:) hydroxymethylbilane synthase; (2661:) Hydroxymethylglutaryl-CoA synthase, cytoplasmic (HMG-CoA synthase) (3-hydroxy-3-methylglutaryl coenzyme A synthase); (2662:) Hydroxymethylglutaryl-CoA synthase, mitochondrial precursor (HMG-CoA synthase) (3-hydroxy-3-methylglutaryl coenzyme Asynthase); (2663:) hydroxyprostaglandin dehydrogenase 15-(NAD) [*Homo sapiens*]; (2664:) hydroxysteroid (11-beta) dehydrogenase 2 [*Homo sapiens*]; (2665:) hydroxysteroid (17-beta) dehydrogenase 1 [*Homo sapiens*]; (2666:) hydroxysteroid (17-beta) dehydrogenase 2 [*Homo sapiens*]; (2667:) hydroxysteroid (17-beta) dehydrogenase 4 [*Homo sapiens*]; (2668:) hydroxysteroid (17-beta) dehydrogenase 7 [*Homo sapiens*]; (2669:) hypoxanthine phosphoribosyltransferase [*Homo sapiens*]; (2670:) hypoxanthine phosphoribosyltransferase 1 [*Homo sapiens*]; (2671:) Hypoxanthine-guanine phosphoribosyltransferase (HGPRT) (HGPRTase); (2672:) Hypoxia-inducible factor 1 alpha (HIF-1 alpha) (HIF1 alpha) (ARNT-interacting protein) (Member of PAS protein 1) (MOP1); (2673:) Hypoxia-inducible factor 1 alpha inhibitor (Hypoxia-inducible factor asparagine hydroxylase) (Factor inhibiting HIF-1) (FIH-1); (2674:) hypoxia-inducible factor 1, alpha subunit inhibitor [*Homo sapiens*]; (2675:) hypoxia-inducible factor 1, alpha subunit isoform 1 [*Homo sapiens*]; (2676:) hypoxia-inducible factor 1, alpha subunit isoform 2 [*Homo sapiens*]; (2677:) I beta 1-6 N-acetylglucosaminyltransferase; (2678:) I beta-1,6-N-acetylglucosaminyltransferase A form [*Homo sapiens*]; (2679:) I beta-1,6-N-acetylglucosaminyltransferase B form [*Homo sapiens*]; (2680:) I beta-1,6-N-acetylglucosaminyltransferase C form [*Homo sapiens*]; (2681:) IARS2 protein [*Homo sapiens*]; (2682:) "i-beta-1,3-N-acetylglucosaminyltransferase;poly-N-acetyllactosamine extension enzyme i-antigen; iGnT [*Homo sapiens*]."; (2683:) I-branching beta-1,6-acetylglucosaminyltransferase family polypeptide 1 [*Homo sapiens*]; (2684:) I-branching beta-1,6-acetylglucosaminyltransferase family polypeptide 2 [*Homo sapiens*]; (2685:) I-branching beta-1,6-acetylglucosaminyltransferase family polypeptide 3 [*Homo sapiens*]; (2686:) I-branching enzyme [*Homo sapiens*]; (2687:) ICE-LAP6—human; (2688:) ICE-LAP6; (2689:) ICH-1L; (2690:)1CH-1S; (2691:) Ich-2; (2692:) "Iduronate 2-sulfatase precursor (Alpha-L-iduronate sulfatesulfatase) (Idursulfase) [Contains:) Iduronate 2-sulfatase 42 kDa chain; Iduronate 2-sulfatase 14 kDa chain]."; (2693:) iduronate 2-sulfatase; (2694:) I-FLICE [*Homo sapiens*]; (2695:) I-FLICE isoform 2 [*Homo sapiens*]; (2696:) I-FLICE isoform 3 [*Homo sapiens*]; (2697:) I-FLICE isoform 4 [*Homo sapiens*]; (2698:) I-FLICE isoform 5 [*Homo sapiens*]; (2699:) IgG receptor FcRn large subunit p51 precursor (FcRn) (Neonatal Fcreceptor) (IgG Fc fragment receptor transporter, alpha chain); (2700:) IKK-related kinase epsilon [*Homo sapiens*]; (2701:) IlvB (bacterial acetolactate synthase)-like [*Homo sapiens*]; (2702:) IlvB (bacterial acetolactate synthase)-like isoform 1 [*Homo sapiens*]; (2703:) IlvB (bacterial acetolactate synthase)-like isoform 1 variant [*Homo sapiens*]; (2704:) IlvB (bacterial acetolactate synthase)-like isoform 2 [*Homo sapiens*]; (2705:) immunodeficiency virus type 1, HIV-1 gp120—human (fragments); (2706:) Immunoglobulin alpha Fc receptor precursor (IgA Fc receptor) (CD89antigen); (2707:) Immunoglobulin-like domain-containing receptor 1 precursor; (2708:) Importin-11 (Imp11) (Ran-binding protein 11) (RanBP11); (2709:) Inactive ubiquitin carboxyl-terminal hydrolase 50 (Inactive ubiquitin-specific peptidase 50); (2710:) indoleamine-pyrrole 2,3 dioxygenase [*Homo sapiens*]; (2711:) indolethylamine N-methyltransferase [*Homo sapiens*]; (2712:) inducible nitric oxide synthase; (2713:) inhibin alpha subunit precursor [*Homo sapiens*]; (2714:) inhibin beta A precursor [*Homo sapiens*]; (2715:) inhibin beta B subunit precursor [*Homo sapiens*]; (2716:) inhibitor of kappa light polypeptide gene enhancer in B-cells, kinase beta [*Homo sapiens*]; (2717:) inhibitor of kappa light polypeptide gene enhancer in B-cells, kinase gamma [*Homo sapiens*]; (2718:) Inhibitor of nuclear factor kappa-B kinase alpha subunit (I kappa-B kinase alpha) (IkBKA) (IKK-alpha) (IKK-A) (IkappaB kinase) (I-kappa-B kinase 1) (IKK1) (Conserved helix-loop-helix ubiquitouskinase) (Nuclear factor NF-kappa-B inhibitor kinase alpha) (NFKBIKA); (2719:) Inner Lipoyl Domain From Human Pyruvate Dehydrogenase (Pdh)Complex, Nmr, 1 Structure; (2720:) Inorganic pyrophosphatase (Pyrophosphate phospho-hydrolase) (PPase); (2721:) Inorganic pyrophosphatase 2, mitochondrial precursor (PPase 2) (Pyrophosphatase SIDE-306); (2722:) inosine monophosphate dehydrogenase 2 [*Homo sapiens*]; (2723:) Inosine triphosphate pyrophosphatase (ITPase) (Inosinetriphosphatase) (Putative oncogene protein hIc14-06-p); (2724:) Inosine-5'-monophosphate dehydrogenase 1 (IMP dehydrogenase 1) (IMPDH-1) (IMPD 1); (2725:) Inosine-5'-monophosphate dehydrogenase 2 (IMP dehydrogenase 2) (IMPDH-II) (IMPD 2); (2726:) inositol 1,3,4,5,6-pentakisphosphate 2-kinase [*Homo sapiens*]; (2727:) inositol 1,3,4-triphosphate 5/6 kinase [*Homo sapiens*]; (2728:) inositol 1,3,4-trisphosphate 5/6-kinase; (2729:) inositol 1,4,5-triphosphate receptor, type 3 [*Homo sapiens*]; (2730:) inositol 1,4,5-trisphosphate 3-kinase B—human; (2731:) Inositol 1,4,5-trisphosphate receptor type 1 (Type 1 inositol1,4,5-trisphosphate receptor) (Type 1 InsP3 receptor) (IP3 receptor isoform 1) (InsP3R1) (IP3R); (2732:) Inositol 1,4,5-trisphosphate receptor type 2 (Type 2 inositol1,4,5-trisphosphate receptor) (Type 2 InsP3 receptor) (IP3 receptor isoform 2) (InsP3R2); (2733:) Inositol 1,4,5-trisphosphate receptor type 3 (Type 3 inositol1,4,5-trisphosphate receptor) (Type 3 InsP3 receptor) (IP3 receptorisoform 3) (InsP3R3); (2734:) Inositol Monophosphatase (E.C.3.1.3.25) (Apoenzyme); (2735:) Inositol monophosphatase (IMPase) (IMP) (Inositol-1(or 4)-monophosphatase) (Lithium-sensitive myo-inositol monophosphataseA1); (2736:) Inositol monophosphatase 2 (IMPase 2) (IMP 2) (Inositol-1(or 4)-monophosphatase 2) (Myo-inositol monophosphatase A2); (2737:) Inositol polyphosphate 1-phosphatase (IPPase) (IPP); (2738:) inositol polyphosphate-1-phosphatase [*Homo sapiens*]; (2739:) inositol polyphosphate-4-phosphatase, type 1 isoform a [*Homo sapiens*]; (2740:) inositol polyphosphate-4-phosphatase, type 1 isoform b [*Homo sapiens*]; (2741:) inositol polyphosphate-4-phosphatase, type II, 105 kD [*Homo sapiens*]; (2742:) inositol(myo)-1(or 4)-monophosphatase 1 [*Homo sapiens*]; (2743:) Inositol-pentakisphosphate 2-kinase(Inositol-1,3,4,5,6-pentakisphosphate 2-kinase) (Ins(1,3,4,5,6)P52-kinase) (InsP5 2-kinase) (IPK1 homolog); (2744:) Inositol-tetrakisphosphate 1-kinase (Inositol-triphosphate5/6-kinase) (Inositol 1,3,4-trisphosphate 5/6-kinase); (2745:) Inositol-trisphosphate 3-kinase A (Inositol 1,4,5-trisphosphate3-kinase A) (IP3K A) (IP3 3-kinase A); (2746:) Inositol-trisphosphate 3-kinase B (Inositol 1,4,5-trisphosphate3-kinase B) (IP3K B) (IP3 3-kinase B) (IP3K-B); (2747:) Inositol-trisphosphate 3-kinase C (Inositol 1,4,5-trisphosphate3-kinase C) (InsP 3-kinase C) (IP3K-C); (2748:) insulin receptor [*Homo sapiens*]; (2749:) "Insulin receptor precursor (IR) (CD220 antigen) [Contains:) Insulin receptor subunit alpha; Insulin receptor subunit beta]."; (2750:) insulin receptor substrate 1 [*Homo sapiens*]; (2751:) "Insulin receptor-related protein precursor (IRR) (IR-related receptor) [Contains:) Insulin receptor-related protein alpha chain; Insulin receptor-related protein beta chain]."; (2752:) insulin receptor-related receptor—human (fragment); (2753:) Insulin-degrading enzyme (Insulysin) (Insulinase) (Insulin protease); (2754:) Insulin-degrading enzyme [*Homo sapiens*]; (2755:) insulin-like growth factor 1 (somatomedin C) [*Homo sapiens*]; (2756:) "Insulin-like growth factor 1 receptor precursor (Insulin-like growth factor I receptor) (IGF-I receptor) (CD221 antigen)[Contains:) Insulin-like growth factor 1 receptor alpha chain; Insulin-like growth factor 1 receptor beta chain]."; (2757:) insulin-like growth factor 2 [*Homo sapiens*]; (2758:) insulin-like growth factor 2 receptor [*Homo sapiens*]; (2759:) insulysin [*Homo sapiens*]; (2760:) Integral membrane protein 2B (Transmembrane protein BRI) [Contains: ABri/ADan amyloid peptide]; (2761:) Integral membrane protein 2C (Transmembrane protein BRI3) (Cerebralprotein 14) [Contains:) CT-BRI3]; (2762:) integral membrane protein 2C isoform 1 [*Homo sapiens*]; (2763:) integral membrane protein 2C isoform 2 [*Homo sapiens*]; (2764:) integral membrane protein 2C isoform 3 [*Homo sapiens*]; (2765:) Integral membrane protein DGCR2/IDD precursor; (2766:) integrin alpha chain, alpha 6 [*Homo sapiens*]; (2767:) Integrin alpha-1 (Laminin and collagen receptor) (VLA-1) (CD49a antigen); (2768:) Integrin alpha-10 precursor; (2769:) Integrin alpha-11 precursor; (2770:) Integrin alpha-2 precursor (Platelet membrane glycoprotein Ia) (GPIa) (Collagen receptor) (VLA-2 alpha chain) (CD49b antigen); (2771:) "Integrin alpha-3 precursor (Galactoprotein B3) (GAPB3) (VLA-3 alpha-chain) (FRP-2) (CD49c antigen) [Contains:) Integrin alpha-3 heavy chain; Integrin alpha-3 light chain]."; (2772:) Integrin alpha-4 precursor (Integrin alpha-IV) (VLA-4) (CD49d antigen); (2773:) "Integrin alpha-5 precursor (Fibronectin receptor subunit alpha) (Integrin alpha-F) (VLA-5) (CD49e antigen) [Contains:) Integrin alpha-5 heavy chain; Integrin alpha-5 light chain]."; (2774:) "Integrin alpha-6 precursor (VLA-6) (CD49f antigen) [Contains: Integrin alpha-6 heavy chain; Integrin alpha-6 light chain]."; (2775:) "Integrin alpha-7 precursor [Contains:) Integrin alpha-7 heavy chain; Integrin alpha-7 light chain]."; (2776:) "Integrin alpha-8 precursor [Contains:) Integrin alpha-8 heavy chain; Integrin alpha-8 light chain]."; (2777:) Integrin alpha-9 precursor (Integrin alpha-RLC); (2778:) Integrin alpha-D precursor (Leukointegrin alpha D) (ADB2) (CD11d antigen); (2779:) "Integrin alpha-E precursor (Mucosal lymphocyte 1 antigen) (HML-1 antigen) (Integrin alpha-IEL) (CD103 antigen) [Contains:) Integrinalpha-E light chain; Integrin alpha-E heavy chain]."; (2780:) "Integrin alpha-IIb precursor (Platelet membrane glycoprotein IIb) (GPalpha IIb) (GPIIb) (CD41 antigen) [Contains:) Integrin alpha-IIb heavy chain; Integrin alpha-IIb light chain]."; (2781:) Integrin alpha-L precursor (Leukocyte adhesion glycoprotein LFA-1 alpha chain) (LFA-1 A) (Leukocyte function-associated molecule 1 alpha chain) (CD11a antigen); (2782:) Integrin alpha-M precursor (Cell surface glycoprotein MAC-1 alphasubunit) (CR-3 alpha chain) (Leukocyte adhesion receptor MO1) (Neutrophil adherence receptor) (CD11b antigen); (2783:) "Integrin alpha-V precursor (Vitronectin receptor subunit alpha) (CD51 antigen) [Contains:) Integrin alpha-V heavy chain; Integrin alpha-V light chain]."; (2784:) Integrin alpha-X precursor (Leukocyte adhesion glycoprotein p150,95alpha chain) (Leukocyte adhesion receptor p150,95) (Leu M5) (CD11c antigen); (2785:) Integrin beta 1 binding protein 3 [*Homo sapiens*]; (2786:) integrin beta 1 binding protein 3 isoform 2 [Homo sapiens]; (2787:) Integrin beta-1 precursor (Fibronectin receptor subunit beta) (Integrin VLA-4 subunit beta) (CD29 antigen); (2788:) Integrin beta-2 precursor (Cell surface adhesion glycoproteins LFA-1/CR3/p150,95 subunit beta) (Complement receptor C3 subunit beta) (CD18 antigen); (2789:) Integrin beta-3 precursor (Platelet membrane glycoprotein IIIa) (GPIIIa) (CD61 antigen); (2790:) Integrin beta-4 precursor (GP150) (CD104 antigen); (2791:) Integrin beta-5 precursor; (2792:) Integrin beta-6 precursor; (2793:) Integrin beta-7 precursor; (2794:) Integrin beta-8 precursor; (2795:) integrin-linked kinase [*Homo sapiens*]; (2796:) Integrin-linked protein kinase 1 (ILK-1) (59 kDa serine/threonine-protein kinase) (p591LK); (2797:) inter-alpha globulin inhibitor H2 polypeptide [*Homo sapiens*]; (2798:) intercellular adhesion molecule 1 precursor [*Homo sapiens*];

(2799:) interferon, gamma [Homo sapiens]; (2800:) interferon, gamma-inducible protein 30 preproprotein [Homo sapiens]; (2801:) Interferon-alpha/beta receptor alpha chain precursor (IFN-alpha-REC); (2802:) Interferon-alpha/beta receptor beta chain precursor (IFN-alpha-REC) (Type I interferon receptor) (IFN-R) (Interferon alpha/betareceptor 2); (2803:) Interferon-gamma receptor alpha chain precursor (1FN-gamma-R1) (CD119 antigen) (CDw119); (2804:) Interferon-gamma receptor beta chain precursor (Interferon-gammareceptor accessory factor 1) (AF-1) (Interferon-gamma transducer1); (2805:) Interferon-induced 17 kDa protein precursor [Contains:) Ubiquitin cross-reactive protein (hUCRP) (Interferon-induced 15 kDa protein)]; (2806:) Interferon-induced, double-stranded RNA-activated protein kinase(Interferon-inducible RNA-dependent protein kinase) (Protein kinase RNA-activated) (PKR) (p68 kinase) (P1/eIF-2A protein kinase); (2807:) Interferon-stimulated gene 20 kDa protein (Promyelocytic leukemia nuclear body-associated protein ISG20) (Estrogen-regulated transcript 45 protein); (2808:) interleukin 1 receptor antagonist isoform 1 precursor [Homo sapiens]; (2809:) interleukin 1 receptor antagonist isoform 2 [Homo sapiens]; (2810:) interleukin 1 receptor antagonist isoform 3 [Homo sapiens]; (2811:) interleukin 1 receptor antagonist isoform 4 [Homo sapiens]; (2812:) interleukin 1, beta proprotein [Homo sapiens]; (2813:) interleukin 18 proprotein [Homo sapiens]; (2814:) interleukin 1-beta convertase [Homo sapiens]; (2815:) interleukin 1-beta convertase; (2816:) Interleukin 1-beta converting enzyme isoform beta; (2817:) Interleukin 1-beta converting enzyme isoform delta; (2818:) Interleukin 1-beta converting enzyme isoform epsilon; (2819:) interleukin 1-beta converting enzyme isoform gamma; (2820:) interleukin 1beta-converting enzyme; (2821:) interleukin 6 receptor isoform 1 precursor [Homo sapiens]; (2822:) interleukin 6 receptor isoform 2 precursor [Homo sapiens]; (2823:) interleukin 8 precursor [Homo sapiens]; (2824:) interleukin 8 receptor beta [Homo sapiens]; (2825:) interleukin-1 beta converting enzyme {N-terminal} [human, PeptidePartial, 23 aa]; (2826:) Interleukin-1 receptor accessory protein precursor (IL-1 receptor accessory protein) (IL-1RAcP); (2827:) Interleukin-1 receptor type I precursor (IL-1R-1) (IL-1RT1) (IL-1R-alpha) (p80) (CD121a antigen); (2828:) Interleukin-1 receptor type II precursor (1L-1R-2) (IL-1R-beta) (CD121b antigen) (CDw121b); (2829:) Interleukin-1 receptor-associated kinase 1 (IRAK-1); (2830:) Interleukin-1 receptor-associated kinase-like 2 (IRAK-2); (2831:) Interleukin-1 receptor-like 1 precursor (ST2 protein); (2832:) Interleukin-1 receptor-like 2 precursor (IL-1 Rrp2) (Interleukin-1receptor-related protein 2) (IL1R-rp2); (2833:) Interleukin-10 receptor alpha chain precursor (IL-10R-A) (IL-10R1) (CDw210a antigen); (2834:) Interleukin-10 receptor beta chain precursor (IL-10R-B) (IL-10R2) (Cytokine receptor family 2 member 4) (Cytokine receptor class-II member 4) (CRF2-4) (CDw210b antigen); (2835:) Interleukin-11 receptor alpha chain precursor (IL-11R-alpha) (IL-11RA); (2836:) Interleukin-12 receptor beta-1 chain precursor (IL-12R-beta1) (Interleukin-12 receptor beta) (IL-12 receptor beta component) (IL-12RB1) (CD212 antigen); (2837:) Interleukin-12 receptor beta-2 chain precursor (IL-12 receptorbeta-2) (IL-12R-beta2); (2838:) Interleukin-13 receptor alpha-1 chain precursor (IL-13R-alpha-1) (IL-13RA-1) (CD213a1 antigen); (2839:) Interleukin-13 receptor alpha-2 chain precursor (Interleukin-13-binding protein) (CD213a2 antigen); (2840:) Interleukin-15 receptor alpha chain precursor (IL-15R-alpha) (IL-15RA); (2841:) Interleukin-17 receptor A precursor (IL-17 receptor) (CD217antigen) (CDw217); (2842:) Interleukin-17 receptor B precursor (IL-17 receptor B) (IL-17RB) (Interleukin-17B receptor) (IL-17B receptor) (IL-17 receptorhomolog 1) (IL-17Rh1) (IL17Rh1) (Cytokine receptor CRL4); (2843:) Interleukin-17 receptor C precursor (IL-17 receptor C) (IL-17RC) (Interleukin-17 receptor-like protein) (IL-17RL) (Interleukin-17receptor homolog) (IL17Rhom); (2844:) Interleukin-17 receptor D precursor (IL-17 receptor D) (IL-17RD) (Interleukin-17D receptor) (IL-17D receptor) (IL17Rhom) (Interleukin-17 receptor-like protein) (Sef homolog) (hSef); (2845:) Interleukin-18 receptor 1 precursor (IL1 receptor-related protein) (IL-1Rrp) (CDw218a antigen); (2846:) Interleukin-18 receptor accessory protein precursor (IL-18 receptor accessory protein) (IL-18RAcP) (Interleukin-18 receptor accessory protein-like) (IL-18Rbeta) (IL-1R accessory protein-like) (IL-1RAcPL) (Accessory protein-like) (AcPL) (IL-1R7) (CDw218b antigen); (2847:) interleukin-1B converting enzyme [Homo sapiens]; (2848:) Interleukin-2 receptor alpha chain precursor (IL-2 receptor alpha subunit) (IL-2-RA) (IL2-RA) (p55) (TAC antigen) (CD25 antigen); (2849:) Interleukin-2 receptor subunit beta precursor (IL-2 receptor) (P70-75) (p75) (High affinity IL-2 receptor subunit beta) (CD122antigen); (2850:) Interleukin-20 receptor alpha chain precursor (IL-20R-alpha) (IL-20R1) (Cytokine receptor family 2 member 8) (Cytokine receptor class-II member 8) (CRF2-8) (ZcytoR7); (2851:) Interleukin-20 receptor beta chain precursor (IL-20R-beta) (IL-20R2); (2852:) Interleukin-21 receptor precursor (IL-21R) (Novel interleukin receptor); (2853:) Interleukin-22 receptor alpha-2 chain precursor (IL-22R-alpha-2) (Interleukin 22-binding protein) (IL22BP) (Cytokine receptor family class II member 10) (CRF2-10) (Cytokine receptor family type 2,soluble 1) (CRF2-S1); (2854:) Interleukin-27 receptor alpha chain precursor (IL-27R-alpha) (WSX-1) (Type 1T-cell cytokine receptor) (TCCR) (Protein CRL1); (2855:) Interleukin-28 receptor alpha chain precursor (IL-28R-alpha) (IL-28RA) (Cytokine receptor family 2 member 12) (Cytokine receptor class-II member 12) (CRF2-12) (Interferon lambda receptor 1) (IFN-lambda R1) (Likely interleukin or cytokine receptor 2); (2856:) Interleukin-3 receptor alpha chain precursor (IL-3R-alpha) (CD123antigen); (2857:) Interleukin-4 receptor alpha chain precursor (IL-4R-alpha) (CD124antigen) [Contains:) Soluble interleukin-4 receptor alpha chain(sIL4Ralpha/prot) (IL-4-binding protein) (IL4-BP)]; (2858:)Interleukin-5 receptor alpha chain precursor (IL-5R-alpha) (CD125antigen) (CDw125); (2859:) Interleukin-6 receptor alpha chain precursor (IL-6R-alpha) (IL-6R1) (Membrane glycoprotein 80) (gp80) (CD126 antigen); (2860:) Interleukin-6 receptor subunit beta precursor (IL-6R-beta) (Interleukin-6 signal transducer) (Membrane glycoprotein 130) (gp130) (Oncostatin-M receptor alpha subunit) (CD130 antigen) (CDw130); (2861:) Interleukin-7 receptor alpha chain precursor (IL-7R-alpha) (CD127antigen) (CDw127); (2862:) Interleukin-9 receptor precursor (IL-9R) (CD129 antigen); (2863:) Interphotoreceptor matrix proteoglycan 1 precursor (Interphotoreceptor matrix proteoglycan of 150 kDa) (IPM-150) (Sialoprotein associated with cones and rods); (2864:) "Interstitial collagenase precursor (Matrix metalloproteinase-1) (MMP-1) (Fibroblast collagenase) [Contains:) 22 kDa interstitial collagenase; 27 kDa interstitial collagenase]."; (2865:) intestinal alkaline phosphatase precursor [Homo sapiens]; (2866:) intestinal alkaline sphingomyelinase [Homo sapiens]; (2867:) iron-sulfur cluster assembly enzyme isoform ISCU1 [Homo sapiens]; (2868:) iron-sulfur cluster assembly enzyme isoform ISCU2 precursor [Homo sapiens]; (2869:) islet amyloid polypeptide precursor [Homo sapiens]; (2870:) Isocitrate dehydrogenase

[NAD] subunit gamma, mitochondrial precursor (Isocitric dehydrogenase) (NAD(+)-specific ICDH); (2871:) Isocitrate dehydrogenase [NADP] cytoplasmic (CytosolicNADP-isocitrate dehydrogenase) (Oxalosuccinate decarboxylase) (IDH) (NADP(+)-specific ICDH) (IDP); (2872:) isocitrate dehydrogenase 1 (NADP+), soluble [Homo sapiens]; (2873:) isocitrate dehydrogenase 3 (NAD+) alpha precursor [Homo sapiens]; (2874:) isopentenyl-diphosphate delta isomerase [Homo sapiens]; (2875:) isopeptidase T; (2876:) isopeptidase T-3 [Homo sapiens]; (2877:) isoprenylcysteine carboxyl methyltransferase [Homo sapiens]; (2878:) isovaleryl Coenzyme A dehydrogenase [Homo sapiens]; (2879:) Itchy homolog E3 ubiquitin protein ligase (Itch) (Atrophin-1-interacting protein 4) (AIP4) (NFE2-associated polypeptide 1) (NAPP1); (2880:) Janus kinase 3 [Homo sapiens]; (2881:) JmjC domain-containing histone demethylation protein 1B([Histone-H3]-lysine-36 demethylase 1B) (F-box/LRR-repeat protein10) (F-box and leucine-rich repeat protein 10) (F-box protein FBL10) (Protein JEMMA) (Jumonji domain-containing EMSY-interactor methyltransferase motif protein) (CXXC-type zinc finger protein 2) (Protein-containing CXXC domain 2); (2882:) JmjC domain-containing histone demethylation protein 2B (Jumonjidomain-containing protein 1B) (Nuclear protein 5qNCA); (2883:) JmjC domain-containing histone demethylation protein 3B (Jumonjidomain-containing protein 2B); (2884:) JmjC domain-containing histone demethylation protein 3C (Jumonjidomain-containing protein 2C) (Gene amplified in squamous cell carcinoma 1 protein) (GASC-1 protein); (2885:) JmjC domain-containing histone demethylation protein 3D (Jumonjidomain-containing protein 2D); (2886:) JRK protein [Homo sapiens]; (2887:) jub, ajuba homolog isoform 1 [Homo sapiens]; (2888:) jub, ajuba homolog isoform 2 [Homo sapiens]; (2889:) jun oncogene [Homo sapiens]; (2890:) junction plakoglobin [Homo sapiens]; (2891:) JUP protein [Homo sapiens]; (2892:) kalirin, RhoGEF kinase isoform 1 [Homo sapiens]; (2893:) kalirin, RhoGEF kinase isoform 2 [Homo sapiens]; (2894:) kalirin, RhoGEF kinase isoform 3 [Homo sapiens]; (2895:) kallikrein 8 isoform 1 preproprotein [Homo sapiens]; (2896:) kallikrein 8 isoform 2 [Homo sapiens]; (2897:) kallikrein 8 isoform 3 [Homo sapiens]; (2898:) kallikrein 8 isoform 4 [Homo sapiens]; (2899:) Kallikrein-5 precursor (Stratum corneum tryptic enzyme) (Kallikrein-like protein 2) (KLK-L2); (2900:) Kallikrein-6 precursor (Protease M) (Neurosin) (Zyme) (SP59); (2901:) Kallikrein-7 precursor (hK7) (Stratum corneum chymotryptic enzyme) (hSCCE); (2902:) kallikrein-related peptidase 4 preproprotein [Homo sapiens]; (2903:) kallikrein-related peptidase 5 preproprotein [Homo sapiens]; (2904:) kallikrein-related peptidase 6 isoform A preproprotein [Homo sapiens]; (2905:) kallikrein-related peptidase 6 isoform B [Homo sapiens]; (2906:) Kallistatin precursor (Serpin A4) (Kallikrein inhibitor) (Protease inhibitor 4); (2907:) Kappa-type opioid receptor (KOR-1); (2908:) KAT3 protein [Homo sapiens]; (2909:) Katanin p60 ATPase-containing subunit A1 (Katanin p60 subunit A1) (p60 katanin); (2910:) katanin p60 subunit A 1 [Homo sapiens]; (2911:) katanin p80 subunit B 1 [Homo sapiens]; (2912:) KDEL (Lys-Asp-Glu-Leu) containing 1 [Homo sapiens]; (2913:) KDEL (Lys-Asp-Glu-Leu) containing 2 [Homo sapiens]; (2914:) KDEL motif-containing protein 1 precursor; (2915:) KDEL motif-containing protein 2 precursor; (2916:) Kelch-like ECH-associated protein 1 (Cytosolic inhibitor of Nrf2) (Kelch-like protein 19); (2917:) Kell blood group, metallo-endopeptidase [Homo sapiens]; (2918:) keratan sulfate Gal-6-sulfotransferase [Homo sapiens]; (2919:) Ketohexokinase (Hepatic fructokinase); (2920:) Ketosamine-3-kinase (Fructosamine-3-kinase-related protein); (2921:) KH-type splicing regulatory protein (FUSE binding protein 2) [Homo sapiens]; (2922:) kidney and liver proline oxidase 1 [Homo sapiens]; (2923:) Killer cell immunoglobulin-like receptor 2DL1 precursor (MHC classI NK cell receptor) (Natural killer-associated transcript 1) (NKAT-1) (p58 natural killer cell receptor clones CL-42/47.11) (p58NK receptor) (p58.1 MHC class-1-specific NK receptor) (CD158a antigen); (2924:) Killer cell immunoglobulin-like receptor 2DL2 precursor (MHC classI NK cell receptor) (Natural killer-associated transcript 6) (NKAT-6) (p58 natural killer cell receptor clone CL-43) (p58 NK receptor); (2925:) Killer cell immunoglobulin-like receptor 2DL3 precursor (MHC classI NK cell receptor) (Natural killer-associated transcript 2) (NKAT-2) (NKAT2a) (NKAT2b) (p58 natural killer cell receptor clone CL-6) (p58 NK receptor) (p58.2 MHC class-1-specific NK receptor) (Killer inhibitory receptor cl 2-3) (KIR-023 GB) (CD158b antigen); (2926:) Killer cell immunoglobulin-like receptor 2DL4 precursor (MHC classI NK cell receptor KIR103AS) (Killer cell inhibitory receptor103AS) (KIR-103AS) (G9P) (CD158d antigen); (2927:) Killer cell immunoglobulin-like receptor 2DS1 precursor (MHC classI NK cell receptor Eb6 ActI) (CD158h antigen); (2928:) Killer cell immunoglobulin-like receptor 2DS2 precursor (MHC classI NK cell receptor) (Natural killer-associated transcript 5) (NKAT-5) (p58 natural killer cell receptor clone CL-49) (p58 NK receptor) (NK receptor 183 ActI) (CD158j antigen); (2929:) Killer cell immunoglobulin-like receptor 2DS3 precursor (MHC classI NK cell receptor) (Natural killer-associated transcript 7) (NKAT-7); (2930:) Killer cell immunoglobulin-like receptor 2DS4 precursor (MHC classI NK cell receptor) (Natural killer-associated transcript 8) (NKAT-8) (P58 natural killer cell receptor clone CL-39) (p58 NK receptor) (CL-17) (CD158i antigen); (2931:) Killer cell immunoglobulin-like receptor 2DS5 precursor (MHC classI NK cell receptor) (Natural killer-associated transcript 9) (NKAT-9) (CD158g antigen); (2932:) Killer cell immunoglobulin-like receptor 3DL1 precursor (MHC classI NK cell receptor) (Natural killer-associated transcript 3) (NKAT-3) (p70 natural killer cell receptor clones CL-2/CL-11) (HLA-BW4-specific inhibitory NK cell receptor); (2933:) Killer cell immunoglobulin-like receptor 3DL2 precursor (MHC classI NK cell receptor) (Natural killer-associated transcript 4) (NKAT-4) (p70 natural killer cell receptor clone CL-5) (CD158k antigen); (2934:) Killer cell immunoglobulin-like receptor 3DL3 precursor (Killer cell inhibitory receptor 1) (CD158z antigen); (2935:) Killer cell immunoglobulin-like receptor 3DS1 precursor (MHC classI NK cell receptor) (Natural killer-associated transcript 10) (NKAT-10); (2936:) Killer cell lectin-like receptor subfamily F member 1 (Lectin-like receptor F1) (Activating coreceptor NKp80); (2937:) kinase insert domain receptor (a type III receptor tyrosine kinase) [Homo sapiens]; (2938:) kinase interacting stathmin [Homo sapiens]; (2939:) kinase related protein, telokin isoform 7 [Homo sapiens]; (2940:) kinase related protein, telokin isoform 8 [Homo sapiens]; (2941:) kinase, phosphoglycerate; (2942:) kinesin family member 23 isoform 1 [Homo sapiens]; (2943:) kinesin family member 23 isoform 2 [Homo sapiens]; (2944:) Kinesin-like protein KIF23 (Mitotic kinesin-like protein 1) (Kinesin-like protein 5); (2945:) Kinesin-like protein KIFC1 (Kinesin-like protein 2) (Kinesin-related protein HSET); (2946:) KiSS-1 receptor (KiSS-1R) (Kisspeptins receptor) (Metastin receptor) (G-protein coupled receptor 54) (Hypogonadotropin-1) (hOT7T175); (2947:) KIAA0184 [Homo sapiens]; (2948:) KIAA0184 protein [Homo sapiens]; (2949:) KIAA0377 splice variant 4 [Homo sapiens]; (2950:) KIAA0398 [Homo sapiens]; (2951:) KIAA0433 [Homo sapiens]; (2952:) KIAA0837 protein [Homo sapiens]; (2953:) KIAA0934 protein [Homo sapiens]; (2954:) KIAA1238 protein [Homo sapiens]; (2955:) KIAA1289 protein [Homo sapiens]; (2956:) KIAA1385 protein [Homo sapiens]; (2957:) KIAA1463 protein [Homo sapiens]; (2958:) KIAA1516 protein [Homo sapiens]; (2959:) KIAA1734 protein [Homo sapiens]; (2960:) KIAA1846 protein [Homo sapiens]; (2961:) KIAA1963 protein [Homo sapiens]; (2962:) KIAA1992 protein [Homo sapiens]; (2963:) Kruppel-like factor 4 (gut) [Homo sapiens]; (2964:) kynureninase (L-kynurenine hydrolase) isoform a [Homo sapiens]; (2965:) kynureninase (L-kynurenine hydrolase) isoform b [Homo sapiens]; (2966:) Kynureninase (L-kynurenine hydrolase); (2967:) Kynurenine 3-monooxygenase (Kynurenine 3-hydroxylase); (2968:) kynurenine aminotransferase III [Homo sapiens]; (2969:) kynurenine aminotransferase III isoform 1 [Homo sapiens]; (2970:) kynurenine aminotransferase III isoform 2 [Homo sapiens]; (2971:) L-3-hydroxyacyl-Coenzyme A dehydrogenase precursor [Homo sapiens]; (2972:) "Lactase-phlorizin hydrolase precursor (Lactase-glycosylceramidase)[Includes:) Lactase; Phlorizin hydrolase]."; (2973:) lactase-phlorizin hydrolase preproprotein [Homo sapiens]; (2974:) lactate dehydrogenase A [Homo sapiens]; (2975:) Lactosylceramide 4-alpha-galactosyltransferase(Alpha-1,4-galactosyltransferase) (UDP-galactose:beta-D-galactosyl-beta1-R4-alpha-D-galactosyltransferase) (Alpha-1,4-N-acetylglucosaminyltransferase) (Alpha4Gal-T1) (Globotriaosylceramide synthase) (Gb3 synthase) (CD77 synthase) (P1/Pk synthase); (2976:) Lactoylglutathione lyase (Methylglyoxalase) (Aldoketomutase) (Glyoxalase I) (Glx I) (Ketone-aldehyde mutase) (S-D-lactoylglutathione methylglyoxal lyase); (2977:) laeverin [Homo sapiens]; (2978:) lambda-crystallin [Homo sapiens]; (2979:) Lambda-crystallin homolog; (2980:) Lamin-B receptor (Integral nuclear envelope inner membrane protein) (LMN2R); (2981:) laminin alpha 3 subunit isoform 1 [Homo sapiens]; (2982:) laminin alpha 3 subunit isoform 2 [Homo sapiens]; (2983:) laminin subunit beta 3 precursor [Homo sapiens]; (2984:) laminin, gamma 2 isoform a precursor [Homo sapiens]; (2985:) laminin, gamma 2 isoform b precursor [Homo sapiens]; (2986:) LANCL2 protein [Homo sapiens]; (2987:) lanthionine synthetase C-like protein 1 [Homo sapiens]; (2988:) Lariat debranching enzyme; (2989:) Latrophilin-1 precursor (Calcium-independent alpha-latrotoxin receptor 1) (Lectomedin-2); (2990:) Latrophilin-2 precursor (Calcium-independent alpha-latrotoxin receptor 2) (Latrophilin homolog 1) (Lectomedin-1); (2991:) Latrophilin-3 precursor (Calcium-independent alpha-latrotoxinreceptor 3) (Lectomedin-3); (2992:) LBP-32 [Homo sapiens]; (2993:) LBP-9 [Homo sapiens]; (2994:) LCFA CoA ligase [Homo sapiens]; (2995:) leader-binding protein 32 isoform 1 [Homo sapiens]; (2996:) leader-binding protein 32 isoform 2 [Homo sapiens]; (2997:) Lecithin retinol acyltransferase (Phosphatidylcholine-retinolO-acyltransferase); (2998:) lecithin retinol acyltransferase [Homo sapiens]; (2999:) lecithin-cholesterol acyltransferase precursor [Homo sapiens]; (3000:) legumain preproprotein [Homo sapiens]; (3001:) legumaturain [Homo sapiens]; (3002:) leprecan-like 1 [Homo sapiens]; (3003:) leprecan-like 2 [Homo sapiens]; (3004:) Leptin receptor precursor (LEP-R) (OB receptor) (OB-R) (HuB219) (CD295 antigen); (3005:) leucine aminopeptidase 3 [Homo sapiens]; (3006:) leucine proline-enriched proteoglycan (leprecan) 1 [Homo sapiens]; (3007:) leucine-rich alpha-2-glycoprotein 1 [Homo sapiens]; (3008:) Leucine-rich repeat serine/threonine-protein kinase 1; (3009:) Leucine-rich repeat-containing G-protein coupled receptor 4precursor (G-protein coupled receptor 48); (3010:) Leucine-rich repeat-containing G-protein coupled receptor 5precursor (Orphan G-protein coupled receptor HG38) (G-protein coupled receptor 49) (G-protein coupled receptor 67); (3011:) Leucine-rich repeat-containing G-protein coupled receptor 6(VTS20631); (3012:) leucyl aminopeptidase (EC 3.4.11.1)/prolyl aminopeptidase (EC3.4.11.5)—human (fragment); (3013:) Leucyl-cystinyl aminopeptidase (Cystinyl aminopeptidase) (Oxytocinase) (OTase) (Insulin-regulated membrane aminopeptidase) (Insulin-responsive aminopeptidase) (IRAP) (Placental leucineaminopeptidase) (P-LAP); (3014:) Leukemia inhibitory factor receptor precursor (LIF receptor) (LIF-R) (CD118 antigen); (3015:) Leukocyte elastase precursor (Elastase-2) (Neutrophil elastase) (PMN elastase) (Bone marrow serine protease) (Medullasin) (Humanleukocyte elastase) (HLE); (3016:) Leukocyte immunoglobulin-like receptor subfamily A member 1 precursor (Leukocyte immunoglobulin-like receptor 6) (LIR-6) (CD85i antigen); (3017:) Leukocyte immunoglobulin-like receptor subfamily A member 2precursor (Leukocyte immunoglobulin-like receptor 7) (LIR-7) (Immunoglobulin-like transcript 1) (ILT-1) (CD85h antigen); (3018:) Leukocyte immunoglobulin-like receptor subfamily A member 3precursor (Leukocyte immunoglobulin-like receptor 4) (LIR-4) (Immunoglobulin-like transcript 6) (ILT-6) (Monocyte inhibitory receptor HM43/HM31) (CD85e antigen); (3019:) Leukocyte immunoglobulin-like receptor subfamily A member 4precursor (Immunoglobulin-like transcript 7) (ILT-7) (CD85g antigen); (3020:) Leukocyte immunoglobulin-like receptor subfamily B member 1precursor (Leukocyte immunoglobulin-like receptor 1) (LIR-1) (Immunoglobulin-like transcript 2) (ILT-2) (Monocyte/macrophage immunoglobulin-like receptor 7) (MIR-7) (CD85j antigen); (3021:) Leukocyte immunoglobulin-like receptor subfamily B member 2precursor (Leukocyte immunoglobulin-like receptor 2) (LIR-2) (Immunoglobulin-like transcript 4) (ILT-4) (Monocyte/macrophage immunoglobulin-like receptor 10) (MIR-10) (CD85d antigen); (3022:) Leukocyte immunoglobulin-like receptor subfamily B member 3precursor (Leukocyte immunoglobulin-like receptor 3) (LIR-3) (Immunoglobulin-like transcript 5) (ILT-5) (Monocyte inhibitory receptor HL9) (CD85a antigen); (3023:) Leukocyte immunoglobulin-like receptor subfamily B member 4precursor (Leukocyte immunoglobulin-like receptor 5) (LIR-5) (Immunoglobulin-like transcript 3) (ILT-3) (Monocyte inhibitory receptor HM18) (CD85k antigen); (3024:) Leukocyte immunoglobulin-like receptor subfamily B member 5precursor (Leukocyte immunoglobulin-like receptor 8) (LIR-8) (CD85c antigen); (3025:) Leukocyte tyrosine kinase receptor precursor (Protein tyrosinekinase 1); (3026:) Leukocyte-associated immunoglobulin-like receptor 1 precursor (LAIR-1) (hLAIR1) (CD305 antigen); (3027:) Leukocyte-associated immunoglobulin-like receptor 2 precursor (LAIR-2) (CD306 antigen); (3028:) Leukotriene A-4 hydrolase (LTA-4 hydrolase) (Leukotriene A(4)hydrolase); (3029:) leukotriene A4 hydrolase [Homo sapiens]; (3030:) leukotriene A-4 hydrolase precursor; (3031:) Leukotriene A4 hydrolase, LTA4 hydrolase [human, B-lymphocytic cell line Raji, Peptide Partial, 21 aa]; (3032:) leukotriene A4 hydrolase; (3033:) leukotriene B4 receptor [Homo sapiens]; (3034:) Leukotriene B4 receptor 1 (LTB4-R 1) (P2Y purinoceptor 7) (P2Y7) (Chemoattractant receptor-like 1) (G-protein coupled receptor 16); (3035:) Leukotriene B4 receptor 2 (LTB4-R2) (Seven transmembrane receptor BLTR2) (Leukotriene B4 receptor BLT2) (LTB4 receptor JULF2); (3036:) leukotriene C4 synthase (EC 6.-.-.-)— human; (3037:) leukotriene C4 synthase [*Homo sapiens*]; (3038:) Lice2 alpha [*Homo sapiens*]; (3039:) Lice2 beta cysteine protease [*Homo sapiens*]; (3040:) Lice2 gamma cysteine protease [*Homo sapiens*]; (3041:) ligase III, DNA, ATP-dependent isoform alpha precursor [*Homo sapiens*]; (3042:) ligase III, DNA, ATP-dependent isoform beta precursor [*Homo sapiens*]; (3043:) Limb region 1 protein homolog (Differentiation-related gene 14protein); (3044:) lipase A precursor [*Homo sapiens*]; (3045:) lipase C precursor [*Homo sapiens*]; (3046:) Lipase member I precursor (Membrane-associated phosphatidic acid-selective phospholipase A1-beta) (mPA-PLA1 beta) (LPD lipase); (3047:) lipase, gastric [*Homo sapiens*]; (3048:) Lipid phosphate phosphohydrolase 1 (Phosphatidic acid phosphatase2a) (Phosphatidate phosphohydrolase type 2a) (PAP2a) (PAP-2a) (PAP2-alpha); (3049:) Lipid phosphate phosphohydrolase 2 (Phosphatidic acid phosphatase2c) (Phosphatidate phosphohydrolase type 2c) (PAP2c) (PAP-2c) (PAP2-gamma) (PAP2-G); (3050:) Lipid phosphate phosphohydrolase 3 (Phosphatidic acid phosphatase2b) (Phosphatidate phosphohydrolase type 2b) (PAP2b) (PAP-2b) (PAP2-beta) (Vascular endothelial growth factor and type (collagen-inducible protein) (VCIP); (3051:) lipin 1 [*Homo sapiens*]; (3052:) Lipoamide acyltransferase component of branched-chain alpha-ketoacid dehydrogenase complex, mitochondrial precursor (Dihydrolipoyllysine-residue (2-methylpropanoyl)transferase) (E2) (Dihydrolipoamide branched chain transacylase) (BCKAD E2 subunit); (3053:) lipocalin 2 [*Homo sapiens*]; (3054:) Lipolysis-stimulated lipoprotein receptor; (3055:) Lipoprotein lipase precursor (LPL); (3056:) lipoprotein lipase precursor [*Homo sapiens*]; (3057:) lipoprotein Lp(a) precursor [*Homo sapiens*]; (3058:) lipoyl-containing component X [*Homo sapiens*]; (3059:) lipoyltransferase [*Homo sapiens*]; (3060:) lipoyltransferase 1 [*Homo sapiens*]; (3061:) Lipoyltransferase 1, mitochondrial precursor (Lipoate-proteinligase) (Lipoate biosynthesis protein) (Lipoyl ligase); (3062:) Liver carboxylesterase 1 precursor (Acyl coenzyme A: cholesterolacyltransferase) (ACAT) (Monocyte/macrophage serine esterase) (HMSE) (Serine esterase 1) (Brain carboxylesterase hBr1) (Triacylglycerol hydrolase) (TGH) (Egasyn); (3063:) liver phosphofructokinase isoform a [*Homo sapiens*]; (3064:) liver phosphofructokinase isoform a variant [*Homo sapiens*]; (3065:) liver phosphofructokinase isoform b [*Homo sapiens*]; (3066:) liver-type 1-phosphofructokinase [*Homo sapiens*]; (3067:) long chain fatty acyl CoA synthetase 2 [*Homo sapiens*]; (3068:) long chain polyunsaturated fatty acid elongation enzyme [*Homo sapiens*]; (3069:) long-chain acyl-CoA synthetase [*Homo sapiens*]; (3070:) long-chain acyl-CoA synthetase 5 [*Homo sapiens*]; (3071:) long-chain acyl-CoA synthetase; (3072:) Long-chain fatty acid transport protein 1 (Fatty acid transportprotein 1) (FATP-1) (Solute carrier family 27 member 1); (3073:) Long-chain fatty acid transport protein 3 (Fatty acid transportprotein 3) (FATP-3) (Very long-chain acyl-CoA synthetase homolog 3) (VLCS-3) (Solute carrier family 27 member 3); (3074:) Long-chain fatty acid transport protein 4 (Fatty acid transportprotein 4) (FATP-4) (Solute carrier family 27 member 4); (3075:) Long-chain fatty acid transport protein 6 (Fatty acid transportprotein 6) (FATP-6) (Very long-chain acyl-CoA synthetase homolog 1) (VLCSH1) (hVLCS-H1) (Fatty-acid-coenzyme A ligase, very long-chain2) (Solute carrier family 27 member 6); (3076:) Long-chain-fatty-acidCoA ligase 1 (Long-chain acyl-CoA synthetase1) (LACS 1) (Palmitoyl-CoA ligase 1) (Long-chain fatty acid CoAligase 2) (Long-chain acyl-CoA synthetase 2) (LACS 2) (Acyl-CoAsynthetase 1) (ACS1) (Palmitoyl-CoA ligase 2); (3077:) Long-chain-fatty-acid—CoA ligase 3 (Long-chain acyl-CoA synthetase3) (LACS 3); (3078:) Long-chain-fatty-acidCoA ligase 4 (Long-chain acyl-CoA synthetase4) (LACS 4); (3079:) Long-chain-fatty-acid—CoA ligase 5 (Long-chain acyl-CoA synthetase5) (LACS 5); (3080:) Long-chain-fatty-acid—CoA ligase 6 (Long-chain acyl-CoA synthetase6) (LACS 6); (3081:) "Low affinity immunoglobulin epsilon Fc receptor (Lymphocyte IgE receptor) (Fc-epsilon-RII) (BLAST-2) (Immunoglobulin E-binding factor) (CD23 antigen) [Contains:) Low affinity immunoglobulin epsilon Fc receptor membrane-bound form; Low affinity immunoglobulin epsilon Fc receptor soluble form]."; (3082:) Low affinity immunoglobulin gamma Fc region receptor II-a precursor (Fc-gamma RH-a) (FcRII-a) (IgG Fc receptor II-a) (Fc-gamma-RIIa) (CD32 antigen) (CDw32); (3083:) Low affinity immunoglobulin gamma Fc region receptor II-b precursor (Fc-gamma RII-b) (FcRII-b) (IgG Fc receptor II-b) (Fc-gamma-RIIb) (CD32 antigen) (CDw32); (3084:) Low affinity immunoglobulin gamma Fc region receptor II-c precursor (Fc-gamma RII-c) (FcRII-c) (IgG Fc receptor II-c) (Fc-gamma-RIIc) (CD32 antigen) (CDw32); (3085:) Low affinity immunoglobulin gamma Fc region receptor III-A precursor (IgG Fc receptor III-2) (Fc-gamma RIII-alpha) (Fc-gammaRIIIa) (FcRIIIa) (Fc-gamma RIII) (FcRIII) (FcR-10) (CD16a antigen); (3086:) Low affinity immunoglobulin gamma Fc region receptor III-Bprecursor (IgG Fc receptor III-1) (Fc-gamma RIII-beta) (Fc-gammaRIIIb) (FcRIIIb) (Fc-gamma RIII) (FcRIII) (FcR-10) (CD16b antigen); (3087:) low density lipoprotein receptor precursor [*Homo sapiens*]; (3088:) low density lipoprotein-related protein 1 [*Homo sapiens*]; (3089:) Low molecular weight phosphotyrosine protein phosphatase (LMW-PTP) (Low molecular weight cytosolic acid phosphatase) (Red cell acid phosphatase 1) (PTPase) (Adipocyte acid phosphatase); (3090:) Low-density lipoprotein receptor precursor (LDL receptor); (3091:) Low-density lipoprotein receptor-related protein 1 precursor (LRP) (Alpha-2-macroglobulin receptor) (A2MR) (Apolipoprotein E receptor) (APOER) (CD91 antigen); (3092:) Low-density lipoprotein receptor-related protein 10 precursor; (3093:) Low-density lipoprotein receptor-related protein 11 precursor; (3094:) Low-density lipoprotein receptor-related protein 12 precursor (Suppressor of tumorigenicity protein 7); (3095:) Low-density lipoprotein receptor-related protein 1B precursor (Low-density lipoprotein receptor-related protein-deleted in tumor) (LRP-DIT); (3096:) Low-density lipoprotein receptor-related protein 2 precursor (Megalin) (Glycoprotein 330) (gp330); (3097:) Low-density lipoprotein receptor-related protein 3 precursor (hLRp105); (3098:) Low-density lipoprotein receptor-related protein 4 precursor (Multiple epidermal growth factor-like domains 7); (3099:) Low-density lipoprotein receptor-related protein 5 precursor; (3100:) Low-density lipoprotein receptor-related protein 6 precursor; (3101:) Low-density lipoprotein receptor-related protein 8 precursor (Apolipoprotein E receptor 2); (3102:) L-pipecolic acid oxidase [*Homo sapiens*]; (3103:) LRAP protein [Homo sapiens]; (3104:) L-serine dehydratase (L-serine deaminase); (3105:) L-UBC [*Homo sapiens*]; (3106:) luteinizing hormone/choriogonadotropin receptor precursor [*Homo sapiens*]; (3107:) Lutheran blood group glycoprotein precursor (B-CAM cell surface glycoprotein) (Auberger B antigen) (F8/G253 antigen) (CD239antigen); (3108:) Lutropin-choriogonadotropic hormone receptor precursor (LH/CG-R) (LSH-R) (Luteinizing hormone receptor) (LHR); (3109:) L-xylulose reductase (XR) (Dicarbonyl/L-xylulose reductase) (Kidneydicarbonyl reductase) (kiDCR) (Carbonyl reductase II) (Sperm surface protein P34H); (3110:)

Lymphatic vessel endothelial hyaluronic acid receptor 1 precursor (LYVE-1) (Cell surface retention sequence-binding protein 1) (CRSBP-1) (Hyaluronic acid receptor) (Extracellular link domain-containing protein 1); (3111:) Lymphocyte antigen 75 precursor (DEC-205) (gp200-MR6) (CD205antigen); (3112:) Lysine-specific histone demethylase 1 (Flavin-containing amineoxidase domain-containing protein 2) (BRAF35-HDAC complex protein BHC110); (3113:) Lysophosphatidic acid receptor 4 (LPA receptor 4) (LPA-4) (P2Y purinoceptor 9) (P2Y9) (Purinergic receptor 9) (G-protein coupled receptor 23) (P2Y5-like receptor); (3114:) Lysophosphatidic acid receptor Edg-2 (LPA receptor 1) (LPA-1); (3115:) Lysophosphatidic acid receptor Edg-4 (LPA receptor 2) (LPA-2); (3116:) Lysophosphatidic acid receptor Edg-7 (LPA receptor 3) (LPA-3); (3117:) lysophospholipase 3 (lysosomal phospholipase A2) [Homo sapiens]; (3118:) "Lysosomal alpha-glucosidase precursor (Acid maltase) (Aglucosidasealfa) [Contains:) 76 kDa lysosomal alpha-glucosidase; 70 kDa lysosomal alpha-glucosidase]."; (3119:) "Lysosomal alpha-mannosidase precursor (Mannosidase, alpha B) (Lysosomal acid alpha-mannosidase) (Laman) (Mannosidase alpha class2B member 1) [Contains:) Lysosomal alpha-mannosidase A peptide; Lysosomal alpha-mannosidase B peptide; Lysosomal alpha-mannosidaseC peptide; Lysosomal alpha-mannosidase D peptide; Lysosomalalpha-mannosidase E peptide]."; (3120:) lysosomal enzyme beta-N-acetylhexosaminidase A [Homo sapiens]; (3121:) lysosomal glucocerebrosidase precursor [Homo sapiens]; (3122:) lysosomal neuraminidase precursor [Homo sapiens]; (3123:) "Lysosomal protective protein precursor (Cathepsin A) (Carboxypeptidase C) (Protective protein for beta-galactosidase)[Contains:) Lysosomal protective protein 32 kDa chain; Lysosomal protective protein 20 kDa chain]."; (3124:) Lysosomal thioesterase PPT2 precursor (PPT-2) (S-thioesterase G14); (3125:) Lysosome membrane protein 2 (Lysosome membrane protein II) (LIMPII) (Scavenger receptor class B member 2) (85 kDa lysosomal membrane sialoglycoprotein) (LGP85) (CD36 antigen-like 2); (3126:) Lysozyme-like protein 4 precursor; (3127:) lysyl hydroxylase precursor [Homo sapiens]; (3128:) lysyl oxidase preproprotein [Homo sapiens]; (3129:) lysyl oxidase-like 2 precursor [Homo sapiens]; (3130:) lysyl oxidase-like 3 precursor [Homo sapiens]; (3131:) lysyl-tRNA synthetase [Homo sapiens]; (3132:) M2-type pyruvate kinase; (3133:) MACH-alpha-1 [Homo sapiens]; (3134:) MACH-alpha-2 [Homo sapiens]; (3135:) MACH-alpha-3 [Homo sapiens]; (3136:) MACH-beta-3 [Homo sapiens]; (3137:) MACH-beta-4 [Homo sapiens]; (3138:) Macrophage colony-stimulating factor 1 receptor precursor (CSF-1-R) (Fms proto-oncogene) (c-fms) (CD115 antigen); (3139:) Macrophage mannose receptor 1 precursor (MMR) (CD206 antigen); (3140:) Macrophage mannose receptor 2 precursor (Urokinase receptor-associated protein) (Endocytic receptor 180) (CD280antigen); (3141:) Macrophage receptor MARCO (Macrophage receptor with collagenous structure) (Scavenger receptor class A member 2); (3142:) Macrophage scavenger receptor types I and II (Macrophage acetylated LDL receptor I and II) (Scavenger receptor class A member 1) (CD204antigen); (3143:) "Macrophage-stimulating protein receptor precursor (MSP receptor) (p185-Ron) (CD136 antigen) (CDw136) [Contains: Macrophage-stimulating protein receptor alpha chain; Macrophage-stimulating protein receptor beta chain]."; (3144:) Magnesium-dependent phosphatase 1 (MDP-1); (3145:) major histocompatibility complex, class II, DP alpha 1 precursor [Homo sapiens]; (3146:) major histocompatibility complex, class II, DQ alpha 2 [Homo sapiens]; (3147:) malate dehydrogenase (oxaloacetate decarboxylating) (NADP+) [Homo sapiens]; (3148:) male sterility domain containing 1 [Homo sapiens]; (3149:) male sterility domain containing 2 [Homo sapiens]; (3150:) Maleylacetoacetate isomerase (MAAI) (Glutathione S-transferase zeta1) (GSTZ1-1); (3151:) Malic enzyme 1, NADP(+)-dependent, cytosolic [Homo sapiens]; (3152:) malic enzyme 2 [Homo sapiens]; (3153:) malic enzyme 2, NAD(+)-dependent, mitochondrial [Homo sapiens]; (3154:) malic enzyme 3, NADP(+)-dependent, mitochondrial [Homo sapiens]; (3155:) Malonyl CoA-acyl carrier protein transacylase, mitochondrial precursor (MCT) (Mitochondrial malonyltransferase); (3156:) maltase-glucoamylase [Homo sapiens]; (3157:) manganese superoxide dismutase isoform A precursor [Homo sapiens]; (3158:) manganese superoxide dismutase isoform B precursor [Homo sapiens]; (3159:) mannan-binding lectin serine protease 2 isoform 1 precursor [Homo sapiens]; (3160:) mannan-binding lectin serine protease 2 isoform 2 precursor [Homo sapiens]; (3161:) "Mannan-binding lectin serine protease 2 precursor (Mannose-binding protein-associated serine protease 2) (MASP-2) (MBL-associated serine protease 2) [Contains:) Mannan-binding lectin serine protease2 A chain; Mannan-binding lectin serine protease 2 B chain]."; (3162:) mannosidase, alpha, class 1A, member 1 [Homo sapiens]; (3163:) mannosidase, alpha, class 2A, member 1 [Homo sapiens]; (3164:) mannosidase, alpha, class 2B, member 1 precursor [Homo sapiens]; (3165:) mannosidase, alpha, class 2C, member 1 [Homo sapiens]; (3166:) mannosidase, endo-alpha [Homo sapiens]; (3167:) mannosyl (alpha-1,3-)-glycoproteinbeta-1,2-N-acetylglucosaminyltransferase [Homo sapiens]; (3168:) mannosyl (alpha-1,6-)-glycoproteinbeta-1,2-N-acetylglucosaminyltransferase [Homo sapiens]; (3169:) mannosyl (beta-1,4-)-glycoproteinbeta-1,4-N-acetylglucosaminyltransferase [Homo sapiens]; (3170:) Mannosyl-oligosaccharide 1,2-alpha-mannosidase IA (Processingalpha-1,2-mannosidase IA) (Alpha-1,2-mannosidase IA) (Mannosidasealpha class 1A member 1) (Man(9)-alpha-mannosidase) (Man9-mannosidase); (3171:) Mannosyl-oligosaccharide 1,2-alpha-mannosidase IB (Processingalpha-1,2-mannosidase IB) (Alpha-1,2-mannosidase IB) (Mannosidasealpha class 1A member 2); (3172:) Mannosyl-oligosaccharide 1,2-alpha-mannosidase IC (Processingalpha-1,2-mannosidase IC) (Alpha-1,2-mannosidase IC) (Mannosidasealpha class 1C member 1) (HMIC); (3173:) mannosyl-oligosaccharide glucosidase [Homo sapiens]; (3174:) MAP kinase-activated protein kinase 2 (MAPK-activated proteinkinase 2) (MAPKAP kinase 2) (MAPKAPK-2) (MK2); (3175:) MAP kinase-activated protein kinase 5 (MAPK-activated proteinkinase 5) (MAPKAP kinase 5) (p38-regulated/activated proteinkinase); (3176:) MAP kinase-interacting serine/threonine-protein kinase 1 (MAPkinase signal-integrating kinase 1) (Mnk1); (3177:) MAPK/MAK/MRK overlapping kinase (MOK protein kinase) (Renal tumor antigen 1) (RAGE-1); (3178:) marapsin [Homo sapiens]; (3179:) MAS proto-oncogene; (3180:) masA [Homo sapiens]; (3181:) Mas-related G-protein coupled receptor member D (Beta-alanine receptor) (G-protein coupled receptor TGR7); (3182:) Mas-related G-protein coupled receptor member E (G-protein coupled receptor 167); (3183:) Mas-related G-protein coupled receptor member F (Mas-related gene F protein) (G-protein coupled receptor 168); (3184:) Mas-related G-protein coupled receptor member G (G-protein coupled receptor 169); (3185:) Mas-related G-protein coupled receptor member X1 (Sensory neuron-specific G-protein coupled receptor 3/4); (3186:) Mas-related G-protein coupled receptor member X2; (3187:) Mas-related G-protein coupled receptor member X3 (Sensory neuron-specific G-protein coupled receptor 1/2); (3188:) Mas-related G-protein coupled receptor member X4 (Sensoryneuron-specific G-protein coupled receptor 5/6); (3189:) Mas-related G-protein coupled receptor MRG (MAS-R) (MAS1-like); (3190:) mast cell function-associated antigen [Homo sapiens]; (3191:) Mast/stem cell growth factor receptor precursor (SCFR) (Proto-oncogene tyrosine-protein kinase Kit) (c-kit) (CD117antigen); (3192:) matrix metalloproteinase 1 preproprotein [Homo sapiens]; (3193:) matrix metalloproteinase 10 preproprotein [Homo sapiens]; (3194:) matrix metalloproteinase 11 preproprotein [Homo sapiens]; (3195:) matrix metalloproteinase 12 preproprotein [Homo sapiens]; (3196:) matrix metalloproteinase 13 preproprotein [Homo sapiens]; (3197:) matrix metalloproteinase 14 preproprotein [Homo sapiens]; (3198:) matrix metalloproteinase 15 preproprotein [Homo sapiens]; (3199:) matrix metalloproteinase 16 isoform 1 preproprotein [Homo sapiens]; (3200:) matrix metalloproteinase 16 isoform 2 preproprotein [Homo sapiens]; (3201:) matrix metalloproteinase 17 preproprotein [Homo sapiens]; (3202:) matrix metalloproteinase 19 isoform 2 precursor [Homo sapiens]; (3203:) matrix metalloproteinase 19 isoform rasi-1 preproprotein [Homo sapiens]; (3204:) matrix metalloproteinase 2 preproprotein [Homo sapiens]; (3205:) matrix metalloproteinase 20 preproprotein [Homo sapiens]; (3206:) matrix metalloproteinase 23B precursor [Homo sapiens]; (3207:) matrix metalloproteinase 26 preproprotein [Homo sapiens]; (3208:) matrix metalloproteinase 28 isoform 1 preproprotein [Homo sapiens]; (3209:) matrix metalloproteinase 28 isoform 3 [Homo sapiens]; (3210:) matrix metalloproteinase 3 preproprotein [Homo sapiens]; (3211:) matrix metalloproteinase 7 preproprotein [Homo sapiens]; (3212:) matrix metalloproteinase 8 preproprotein [Homo sapiens]; (3213:) matrix metalloproteinase 9 preproprotein [Homo sapiens]; (3214:) Matrix metalloproteinase-16 precursor (MMP-16) (Membrane-typematrix metalloproteinase 3) (MT-MMP 3) (MTMMP3) (Membrane-type-3matrix metalloproteinase) (MT3-MMP) (MT3MMP) (MMP-X2); (3215:) Matrix metalloproteinase-19 precursor (MMP-19) (Matrixmetalloproteinase RASI) (MMP-18); (3216:) "Matrix metalloproteinase-9 precursor (MMP-9) (92 kDa type IV collagenase) (92 kDa gelatinase) (Gelatinase B) (GELB) [Contains:67 kDa matrix metalloproteinase-9; 82 kDa matrixmetalloproteinase-9]."; (3217:) matrix, extracellular phosphoglycoprotein with ASARM motif (bone) [Homo sapiens]; (3218:) Mch3 isoform alpha; (3219:) Mch3 isoform beta; (3220:) "MDMCSF (EC 1.5.1.5; EC 3.5.4.9; EC 6.3.4.3)."; (3221:) MDS010 [Homo sapiens]; (3222:) ME2 protein [Homo sapiens]; (3223:) Mediator complex subunit 4 (Mediator of RNA polymerase IItranscription subunit 4) (Vitamin D3 receptor-interacting proteincomplex 36 kDa component) (DRIP36) (Activator-recruited cofactor 36 kDa component) (ARC36) (TRAP/SMCC/PC2 subunit p36 subunit); (3224:) Mediator of RNA polymerase II transcription subunit 12 (Thyroid hormone receptor-associated protein complex 230 kDa component) (Trap230) (Activator-recruited cofactor 240 kDa component) (ARC240) (CAG repeat protein 45) (OPA-containing protein) (Trinucleotide repeat-containing gene 11 protein); (3225:) Mediator of RNA polymerase II transcription subunit 8 homolog(Activator-recruited cofactor 32 kDa component) (ARC32); (3226:) mediator of RNA polymerase II transcription subunit MED8 isoform 1 [Homo sapiens]; (3227:) mediator of RNA polymerase II transcription subunit MED8 isoform 2 [Homo sapiens]; (3228:) mediator of RNA polymerase II transcription subunit MED8 isoform 3 [Homo sapiens]; (3229:) mediator of RNA polymerase II transcription subunit MED8 isoform 4 [Homo sapiens]; (3230:) medium-chain acyl-CoA dehydrogenase (EC 1.3.99.3); (3231:) medium-chain acyl-CoA dehydrogenase; (3232:) Medium-chain specific acyl-CoA dehydrogenase, mitochondrial precursor (MCAD); (3233:) Meis1 homolog [Homo sapiens]; (3234:) Melanin-concentrating hormone receptor 1 (MCH receptor 1) (MCHR-1) (MCH-R1) (MCH1R) (MCH-1R) (MCHR) (G-protein coupled receptor 24) (Somatostatin receptor-like protein) (SLC-1); (3235:) Melanin-concentrating hormone receptor 2 (MCH receptor 2) (MCHR-2) (MCH-R2) (MCH2R) (MCH-2R) (MCH2) (G-protein coupled receptor 145) (GPRv17); (3236:) Melanocortin receptor 3 (MC3-R); (3237:) Melanocortin receptor 4 (MC4-R); (3238:) Melanocortin receptor 5 (MC5-R) (MC-2); (3239:) Melanocyte protein Pmel 17 precursor (Melanocyte lineage-specific antigen GP100) (Melanoma-associated ME20 antigen) (ME20M/ME20S) (ME20-M/ME20-S) (95 kDa melanocyte-specific secreted glycoprotein); (3240:) Melanocyte-stimulating hormone receptor (MSH-R) (Melanotropin receptor) (Melanocortin receptor 1) (MC1-R); (3241:) Melanopsin (Opsin-4); (3242:) Melatonin receptor type 1A (Mel-1A-R) (Melia melatonin receptor); (3243:) Melatonin receptor type 1B (Mel-1B-R) (Mel1b melatonin receptor); (3244:) Melatonin-related receptor (G protein-coupled receptor 50) (H9); (3245:) membrane alanine aminopeptidase precursor [Homo sapiens]; (3246:) membrane associated guanylate kinase, WW and PDZ domain containing 2 [Homo sapiens]; (3247:) Membrane copper amine oxidase (Semicarbazide-sensitive amineoxidase) (SSAO) (Vascular adhesion protein 1) (VAP-1) (HPAO); (3248:) membrane metallo-endopeptidase [Homo sapiens]; (3249:) Membrane metallo-endopeptidase-like 1 (Membranemetallo-endopeptidase-like 2) (Neprilysin-2) (Neprilysin II) (NL2) (NEPII) (NEP2(m)) [Contains:) Membrane metallo-endopeptidase-like 1,soluble form (Neprilysin-2 secreted) (NEP2(s))]; (3250:) Membrane progestin receptor alpha (mPR alpha) (Progestin and adipoQreceptor family member VII); (3251:) Membrane progestin receptor beta (mPR beta) (Progestin and adipoQreceptor family member VIII) (Lysosomal membrane protein in brain-1); (3252:) Membrane progestin receptor gamma (mPR gamma) (Progestin and adipoQreceptor family member V); (3253:) Membrane-associated progesterone receptor component 1 (mPR); (3254:) Membrane-associated progesterone receptor component 2 (Progesterone membrane-binding protein) (Steroid receptor protein DG6); (3255:) membrane-associated prostaglandin E synthase (EC 5.3.99.3)-2-human; (3256:) Membrane-associated tyrosine- and threonine-specific cdc2-inhibitory kinase (Myt1 kinase); (3257:) Membrane-bound transcription factor site 1 protease precursor (S1P endopeptidase) (Site-1 protease) (Subtilisin/kexin-isozyme 1) (SKI-1); (3258) Membrane-spanning 4-domains subfamily A member 10; (3259:) Membrane-spanning 4-domains subfamily A member 12; (3260:) Membrane-spanning 4-domains subfamily A member 3(Hematopoietic-specific transmembrane 4 protein) (HTm4) (CD20antigen-like protein); (3261:) Membrane-spanning 4-domains subfamily A member 4A (Four-span transmembrane protein 1) (CD20 antigen-like 1); (3262:) Membrane-spanning 4-domains subfamily A member 4E; (3263:) Membrane-spanning 4-domains subfamily A member 5 (Testis-expressed transmembrane 4 protein) (CD20 antigen-like 2); (3264:) Membrane-spanning 4-domains subfamily A member 6A (Four-span transmembrane protein 3) (CD20 antigen-like 3); (3265:) Membrane-spanning 4-domains subfamily A member 6E; (3266:) Membrane-spanning 4-domains subfamily A member 7(CD20/FC-epsilon-R1-beta family member 4) (Four-span transmembrane protein 2)

(CD20 antigen-like 4); (3267:) Membrane-spanning 4-domains subfamily A member 8B (Four-spantrans membrane protein 4); (3268:) membrane-type mosaic serine protease [*Homo sapiens*]; (3269:) menage a trois 1 (CAK assembly factor) [*Homo sapiens*]; (3270:) meningioma expressed antigen 5 (hyaluronidase) [*Homo sapiens*]; (3271:) meprin A, alpha (PABA peptide hydrolase) [*Homo sapiens*]; (3272:) meprin A, beta [*Homo sapiens*]; (3273:) mercaptopyruvate sulfurtransferase variant [*Homo sapiens*]; (3274:) mesotrypsin preproprotein [*Homo sapiens*]; (3275:) mesotrypsinogen [*Homo sapiens*]; (3276:) Metabotropic glutamate receptor 1 precursor (mGluR1); (3277:) Metabotropic glutamate receptor 2 precursor (mGluR2); (3278:) Metabotropic glutamate receptor 3 precursor (mGluR3); (3279:) Metabotropic glutamate receptor 4 precursor (mGluR4); (3280:) metabotropic glutamate receptor 5 A—human; (3281:) metabotropic glutamate receptor 5 B—human; (3282:) Metabotropic glutamate receptor 5 precursor (mGluR5); (3283:) Metabotropic glutamate receptor 6 precursor (mGluR6); (3284:) Metabotropic glutamate receptor 7 precursor (mGluR7); (3285:) Metabotropic glutamate receptor 8 precursor (mGluR8); (3286:) metallopeptidase [*Homo sapiens*]; (3287:) metallothionein 1A [*Homo sapiens*]; (3288:) methionine sulfoxide reductase A [*Homo sapiens*]; (3289:) methionine synthase reductase isoform 1 [*Homo sapiens*]; (3290:) methionine synthase reductase isoform 2 [*Homo sapiens*]; (3291:) methionyl aminopeptidase 2 [*Homo sapiens*]; (3292:) Methionyl-tRNA synthetase, mitochondrial precursor (Methionine—tRNA ligase 2) (Mitochondrial methioninetRNA ligase) (MtMetRS); (3293:) methyl sterol oxidase; (3294:) Methylated-DNAprotein-cysteine methyltransferase(6-O-methylguanine-DNA methyltransferase) (MGMT) (O-6-methylguanine-DNA-alkyltransferase); (3295:) Methylcrotonoyl-CoA carboxylase subunit alpha, mitochondrial precursor (3-methylcrotonyl-CoA carboxylase 1) (MCCase subunit alpha) (3-methylcrotonyl-CoA:carbon dioxide ligase subunit alpha) (3-methylcrotonyl-CoA carboxylase biotin-containing subunit); (3296:) methylcrotonoyl-Coenzyme A carboxylase 1 (alpha) [*Homo sapiens*]; (3297:) methylcrotonoyl-Coenzyme A carboxylase 1 (alpha) variant [*Homo sapiens*]; (3298:) methylcrotonoyl-Coenzyme A carboxylase 2 (beta) [*Homo sapiens*]; (3299:) methylene tetrahydrofolate dehydrogenase 2 isoform A precursor [*Homo sapiens*]; (3300:) methylene tetrahydrofolate dehydrogenase 2 isoform B [*Homo sapiens*]; (3301:) methylenetetrahydrofolate dehydrogenase (NADP+ dependent) 1-like [*Homo sapiens*]; (3302:) methylenetetrahydrofolate dehydrogenase 1 [*Homo sapiens*]; (3303:) methylenetetrahydrofolate reductase [*Homo sapiens*]; (3304:) methylenetetrahydrofolate reductase intermediate form [*Homo sapiens*]; (3305:) methylenetetrahydrofolate reductase long isoform [*Homo sapiens*]; (3306:) methylenetetrahydrofolate reductase short isoform [*Homo sapiens*]; (3307:) Methylenetetrahydrofolate reductase; (3308:) methylmalonyl Coenzyme A mutase precursor [*Homo sapiens*]; (3309:) Methylmalonyl-CoA mutase, mitochondrial precursor (MCM) (Methylmalonyl-CoA isomerase); (3310:) methylthioadenosine phosphorylase [*Homo sapiens*]; (3311:) methyltransferase like 3 [*Homo sapiens*]; (3312:) Mevalonate kinase (MK); (3313:) mevalonate kinase [*Homo sapiens*]; (3314:) mevalonate pyrophosphate decarboxylase; (3315:) MGC42638 protein [*Homo sapiens*]; (3316:) microphthalmia-associated transcription factor isoform 1 [*Homo sapiens*]; (3317:) microphthalmia-associated transcription factor isoform 2 [*Homo sapiens*]; (3318:) microphthalmia-associated transcription factor isoform 3 [*Homo sapiens*]; (3319:) microphthalmia-associated transcription factor isoform 4 [*Homo sapiens*]; (3320:) microphthalmia-associated transcription factor isoform 5 [*Homo sapiens*]; (3321:) microphthalmia-associated transcription factor isoform 6 [*Homo sapiens*]; (3322:) Microsomal glutathione S-transferase 1 (Microsomal GST-1) (Microsomal GST-I); (3323:) microsomal glutathione S-transferase 2 [*Homo sapiens*]; (3324:) Microsomal glutathione S-transferase 3 (Microsomal GST-3) (Microsomal GST-III); (3325:) microsomal glutathione S-transferase 3 [*Homo sapiens*]; (3326:) microtubule-associated protein tau isoform 1 [*Homo sapiens*]; (3327:) microtubule-associated protein tau isoform 2 [*Homo sapiens*]; (3328:) microtubule-associated protein tau isoform 3 [*Homo sapiens*]; (3329:) microtubule-associated protein tau isoform 4 [*Homo sapiens*]; (3330:) microtubule-associated proteins 1A/1B light chain 3 [*Homo sapiens*]; (3331:) migration-inducing gene 10 protein [*Homo sapiens*]; (3332:) migration-inducing protein 4 [*Homo sapiens*]; (3333:) Mih1fTX isoform beta [*Homo sapiens*]; (3334:) Mih1fTX isoform delta [*Homo sapiens*]; (3335:) Mih1/TX isoform gamma [*Homo sapiens*]; (3336:) Mineralocorticoid receptor (MR); (3337:) minichromosome maintenance protein 4 [*Homo sapiens*]; (3338:) minichromosome maintenance protein 6 [*Homo sapiens*]; (3339:) minichromosome maintenance protein 7 isoform 1 [*Homo sapiens*]; (3340:) minichromosome maintenance protein 7 isoform 2 [*Homo sapiens*]; (3341:) mitochondrial aldehyde dehydrogenase 2 precursor [*Homo sapiens*]; (3342:) mitochondrial C1-tetrahydrofolate synthetase—human; (3343:) mitochondrial dihydrolipoamide succinyltransferase [*Homo sapiens*]; (3344:) mitochondrial DNA polymerase accessory subunit precursor [*Homo sapiens*]; (3345:) mitochondrial glycine cleavage system H-protein precursor [*Homo sapiens*]; (3346:) Mitochondrial import receptor subunit TOM22 homolog (Translocase of outer membrane 22 kDa subunit homolog) (hTom22) (1C9-2); (3347:) Mitochondrial intermediate peptidase, mitochondrial precursor (MIP); (3348:) mitochondrial malate dehydrogenase precursor [*Homo sapiens*]; (3349:) mitochondrial MTO1-3 [*Homo sapiens*]; (3350:) mitochondrial NAD(P)+-dependent malic enzyme; (3351:) mitochondrial NADP(+)-dependent malic enzyme 3 [*Homo sapiens*]; (3352:) mitochondrial phosphoenolpyruvate carboxykinase 2 isoform 1 precursor [*Homo sapiens*]; (3353:) mitochondrial phosphoenolpyruvate carboxykinase 2 isoform 2precursor [*Homo sapiens*]; (3354:) mitochondrial short-chain enoyl-coenzyme A hydratase 1 precursor [*Homo sapiens*]; (3355:) mitochondrial topoisomerase I [*Homo sapiens*]; (3356:) Mitochondrial translation optimization 1 homolog (*S. cerevisiae*) [*Homo sapiens*]; (3357:) mitochondrial translation optimization 1 homolog isoform a [*Homo sapiens*]; (3358:) mitochondrial translation optimization 1 homolog isoform b [*Homo sapiens*]; (3359:) mitochondrial trifunctional protein, alpha subunit precursor [*Homo sapiens*]; (3360:) mitochondrial trifunctional protein, beta subunit precursor [*Homo sapiens*]; (3361:) Mitogen-activated protein kinase 1 (Extracellular signal-regulated kinase 2) (ERK-2) (Mitogen-activated protein kinase 2) (MAP kinase2) (MAPK 2) (p42-MAPK) (ERT1); (3362:) mitogen-activated protein kinase 1 [*Homo sapiens*]; (3363:) Mitogen-activated protein kinase 10 (Stress-activated proteinkinase JNK3) (c-Jun N-terminal kinase 3) (MAP kinase p49 3F12); (3364:) Mitogen-activated protein kinase 11 (Mitogen-activated proteinkinase p38 beta) (MAP kinase p38 beta) (p38b) (p38-2) (Stress-activated protein kinase 2); (3365:) Mitogen-activated protein kinase 12 (Extracellular signal-regulated kinase 6) (ERK-6) (Stress-activated protein kinase 3) (Mitogen-activated protein kinase p38 gamma) (MAP kinase p38gamma); (3366:) Mitogen-activated protein kinase 13 (Stress-activated proteinkinase 4) (Mitogen-activated protein kinase p38 delta) (MAP kinasep38 delta); (3367:) Mitogen-activated protein kinase 14 (Mitogen-activated proteinkinase p38 alpha) (MAP kinase p38 alpha) (Cytokine suppressive anti-inflammatory drug-binding protein) (CSAID-binding protein) (CSBP) (MAX-interacting protein 2) (MAP kinase MXI2) (SAPK2A); (3368:) Mitogen-activated protein kinase 15 (Extracellular signal-regulated kinase 8); (3369:) Mitogen-activated protein kinase 3 (Extracellular signal-regulated kinase 1) (ERK-1) (Insulin-stimulated MAP2 kinase) (MAP kinase 1) (MAPK 1) (p44-ERK1) (ERT2) (p44-MAPK) (Microtubule-associated protein 2 kinase); (3370:) mitogen-activated protein kinase 3 isoform 1 [*Homo sapiens*]; (3371:) mitogen-activated protein kinase 3 isoform 2 [*Homo sapiens*]; (3372:) Mitogen-activated protein kinase 7 (Extracellular signal-regulated kinase 5) (ERK-5) (ERK4) (BMK1 kinase); (3373:) Mitogen-activated protein kinase 8 (Stress-activated protein kinase JNK1) (c-Jun N-terminal kinase 1) (JNK-46); (3374:) mitogen-activated protein kinase 8 isoform JNK1 alpha1 [*Homo sapiens*]; (3375:) mitogen-activated protein kinase 8 isoform JNK1 alpha2 [*Homo sapiens*]; (3376:) mitogen-activated protein kinase 8 isoform JNK1 beta1 [*Homo sapiens*]; (3377:) mitogen-activated protein kinase 8 isoform JNK1 beta2 [*Homo sapiens*]; (3378:) Mitogen-activated protein kinase 9 (Stress-activated protein kinase JNK2) (c-Jun N-terminal kinase 2) (JNK-55); (3379:) mitogen-activated protein kinase kinase 1 [*Homo sapiens*]; (3380:) Mitogen-activated protein kinase kinase kinase (Mixed lineage kinase 4); (3381:) Mitogen-activated protein kinase kinase kinase 1 (MAPK/ERK kinase kinase 1) (MEK kinase 1) (MEKK 1); (3382:) Mitogen-activated protein kinase kinase kinase 10 (Mixed lineage kinase 2) (Protein kinase MST); (3383:) Mitogen-activated protein kinase kinase kinase 11 (Mixed lineage kinase 3) (Src-homology 3 domain-containing proline-rich kinase); (3384:) mitogen-activated protein kinase kinase kinase 12 [*Homo sapiens*]; (3385:) Mitogen-activated protein kinase kinase kinase 13 (Mixed lineage kinase) (MLK) (Leucine zipper-bearing kinase); (3386:) Mitogen-activated protein kinase kinase kinase 15 (MAPK/ERK kinase kinase 15) (MEK kinase 15) (MEKK 15); (3387:) Mitogen-activated protein kinase kinase kinase 2 (MAPK/ERK kinase kinase 2) (MEK kinase 2) (MEKK 2); (3388:) Mitogen-activated protein kinase kinase kinase 3 (MAPK/ERK kinase kinase 3) (MEK kinase 3) (MEKK 3); (3389:) Mitogen-activated protein kinase kinase kinase 4 (MAPK/ERK kinase kinase 4) (MEK kinase 4) (MEKK 4) (MAP three kinase 1); (3390:) Mitogen-activated protein kinase kinase kinase 5 (MAPK/ERK kinase kinase 5) (MEK kinase 5) (MEKK 5) (Apoptosis signal-regulating kinase 1) (ASK-1); (3391:) mitogen-activated protein kinase kinase kinase 5 [*Homo sapiens*]; (3392:) Mitogen-activated protein kinase kinase kinase 6; (3393:) Mitogen-activated protein kinase kinase kinase 9 (Mixed lineage kinase 1); (3394:) Mitogen-activated protein kinase kinase kinase MLT (MLK-like mitogen-activated protein triple kinase) (Leucine zipper- and sterile alpha motif-containing kinase) (Sterile alpha motif- and leucine zipper-containing kinase AZK) (Mixed lineage kinase-related kinase) (MLK-related kinase) (MRK) (Cervical cancer suppressor gene4 protein); (3395:) mitogen-activated protein kinase-activated protein kinase 2 isoform1 [*Homo sapiens*]; (3396:) mitogen-activated protein kinase-activated protein kinase 2 isoform2 [*Homo sapiens*]; (3397:) Mitotic checkpoint serine/threonine-protein kinase BUB1 (hBUB1) (BUB1A); (3398:) mitotic kinase-like protein-1 [*Homo sapiens*]; (3399:) Mitotic Kinesin Eg5; (3400:) MLH1+ ins1a isoform [*Homo sapiens*]; (3401:) MLH1-Ex6 isoform [*Homo sapiens*]; (3402:) MLH3 protein [*Homo sapiens*]; (3403:) MMS2 [*Homo sapiens*]; (3404:) MOCS1 [*Homo sapiens*]; (3405:) MOCS1 protein [*Homo sapiens*]; (3406:) MOCS1A enzyme [*Homo sapiens*]; (3407:) MOCS1A protein [*Homo sapiens*]; (3408:) Molybdenum cofactor biosynthesis protein 1 A (MOCS1A); (3409:) Molybdenum cofactor biosynthesis protein 1 B (MOCS1B) (Molybdenum cofactor synthesis-step 1 protein A-B) (Molybdenum cofactor biosynthesis protein C); (3410:) molybdenum cofactor biosynthesis protein A [*Homo sapiens*]; (3411:) molybdenum cofactor synthesis-step 1 protein isoform 1 [*Homo sapiens*]; (3412:) molybdenum cofactor synthesis-step 1 protein isoform 2 [*Homo sapiens*]; (3413:) molybdenum cofactor synthesis-step 1 protein isoform 3 [*Homo sapiens*]; (3414:) molybdenum cofactor synthesis-step 1 protein isoform 4 [*Homo sapiens*]; (3415:) molybdopterin synthase large subunit MOCS2B [*Homo sapiens*]; (3416:) molybdopterin synthase small subunit MOCS2A [*Homo sapiens*]; (3417:) monoacylglycerol O-acyltransferase 3 [*Homo sapiens*]; (3418:) Monoamine Oxidase A (MAO-A); (3419:) monoamine oxidase A [*Homo sapiens*]; (3420:) Monoamine Oxidase B (MAO-B); (3421:) Monocyte Chemoattractant Protein 1 (MCP-1) Receptor; (3422:) Monocyte to macrophage differentiation factor 2 (Progestin and adipoQ receptor family member X); (3423:) Monocyte to macrophage differentiation protein (Progestin and adipoQ receptor family member XI); (3424:) MOP-4 [*Homo sapiens*]; (3425:) mosaic serine protease [*Homo sapiens*]; (3426:) Motilin Receptor; (3427:) Motilin receptor (G-protein coupled receptor 38); (3428:) M-phase inducer phosphatase 1 (Dual specificity phosphatase Cdc25A); (3429:) M-phase inducer phosphatase 2 (Dual specificity phosphatase Cdc25B); (3430:) MRIT-alpha-1 [*Homo sapiens*]; (3431:) mRNA (guanine-7-)methyltransferase [*Homo sapiens*]; (3432:) mRNA 5' cap guanine-N-7 methyltransferase [*Homo sapiens*]; (3433:) mRNA cap guanine-N7 methyltransferase (mRNA(guanine-N(7)-)-methyltransferase) (RG7MT1) (mRNA capmethyltransferase) (hcmlp) (hCMT1) (hMet); (3434:) "mRNA capping enzyme (HCE) (HCAP1) [Includes:) Polynucleotide5'-triphosphatase (mRNA 5'-triphosphatase) (TPase); mRNAguanylyltransferase (GTP-RNA guanylyltransferase) (GTase)]."; (3435:) mRNA capping enzyme [*Homo sapiens*]; (3436:) mRNA decapping enzyme [*Homo sapiens*]; (3437:) mRNA decapping enzyme 1A (Transcription factor SMIF) (Smad-4-interacting transcriptional co-activator); (3438:) mRNA decapping enzyme 1 B; (3439:) mRNA decapping enzyme 2 (hDpc) (Nucleoside diphosphate-linked moiety X motif 20) (Nudix motif 20); (3440:) mRNA decapping enzyme variant [*Homo sapiens*]; (3441:) mRNA-decapping enzyme [*Homo sapiens*]; (3442:) MSTP042 [*Homo sapiens*]; (3443:) MTO1 isoform 1 [*Homo sapiens*]; (3444:) MTO1 isoform 2 [*Homo sapiens*]; (3445:) MTO1 protein [*Homo sapiens*]; (3446:) MTO1 protein isoform III [*Homo sapiens*]; (3447:) MTO1 protein isoform IV [*Homo sapiens*]; (3448:) MTO1-like protein [*Homo sapiens*]; (3449:) mucin 1 isoform 1 precursor [*Homo sapiens*]; (3450:) mucin 1 isoform 2 precursor [*Homo sapiens*]; (3451:) mucin 1 isoform 3 precursor [*Homo sapiens*]; (3452:) mucin 1 isoform 5 precursor [*Homo sapiens*]; (3453:) mucin 1 isoform 6 precursor [*Homo sapiens*]; (3454:) mucin 1 isoform 7 precursor [*Homo sapiens*]; (3455:) mucin 1 isoform 8 precursor [*Homo sapiens*]; (3456:) Mucin-1 (MUC1) Glycoprotein; (3457:) mu-crystallin [*Homo sapiens*]; (3458:) Mu-crystallin homolog (NADP-regulated thyroid-hormone-binding protein); (3459:) Multidrug Resistance-Associated Protein 1 (MRP1);

(3460:) Multidrug resistance-associated protein 7 (ATP-binding cassette sub-family C member 10); (3461:) multifunctional protein CAD [Homo sapiens]; (3462:) multiple exostoses-like 2 [Homo sapiens]; (3463:) Mu-Opioid Receptor; (3464:) Muscarinic acetylcholine receptor M1; (3465:) Muscarinic acetylcholine receptor M2; (3466:) Muscarinic acetylcholine receptor M3; (3467:) Muscarinic acetylcholine receptor M4; (3468:) Muscarinic acetylcholine receptor M5; (3469:) Muscarinic M1 Receptor; (3470:) Muscarinic M2 Receptor; (3471:) Muscarinic M3 Receptor; (3472:) Muscarinic M4 Receptor; (3473:) muscle beta 1 intergrin cytoplasmic domain binding protein MIBP [Homo sapiens]; (3474:) muscle creatine kinase [Homo sapiens]; (3475:) Muscle, skeletal receptor tyrosine protein kinase precursor (Muscle-specific tyrosine protein kinase receptor) (Muscle-specific kinase receptor) (MuSK); (3476:) mutant arylamine N-acetyltransferase [Homo sapiens]; (3477:) mutant 1 beta-1,6-N-acetylglucosaminyltransferase C form [Homo sapiens]; (3478:) mutL 3 homolog (E. coli) [Homo sapiens]; (3479:) MutL homolog 1, colon cancer, nonpolyposis type 2 (E. coli) [Homo sapiens]; (3480:) MutL homolog 3 (E. coli) [Homo sapiens]; (3481:) mutL homolog 3 isoform 1 [Homo sapiens]; (3482:) mutL homolog 3 isoform 2 [Homo sapiens]; (3483:) MutL protein homolog 1 [Homo sapiens]; (3484:) MutL protein homolog 1 variant [Homo sapiens]; (3485:) mutS homolog 2 [Homo sapiens]; (3486:) mutS homolog 6 [Homo sapiens]; (3487:) mutY homolog isoform 1 [Homo sapiens]; (3488:) mutY homolog isoform 2 [Homo sapiens]; (3489:) mutY homolog isoform 3 [Homo sapiens]; (3490:) mutY homolog isoform 4 [Homo sapiens]; (3491:) Mu-type opioid receptor (MOR-1); (3492:) Mycobacterial Arabinosyltransferases; (3493:) Mycobacterial Fatty Acid Synthetase I (FAS-I); (3494:) Mycobacterial Translocase I; (3495:) Mycobacterium Tuberculosis Adenosine Triphosphate (ATP) Synthase; (3496:) Mycobacterium Tuberculosis Enoyl-Acyl Carrier Protein Reductase (InhA); (3497:) Mycobacterium Tuberculosis Isocitrate Lyase (Id); (3498:) myelin basic protein isoform 1 [Homo sapiens]; (3499:) myelin basic protein isoform 2 [Homo sapiens]; (3500:) myelin basic protein isoform 3 [Homo sapiens]; (3501:) myelin basic protein isoform 4 [Homo sapiens]; (3502:) myelin basic protein isoform 5 [Homo sapiens]; (3503:) myelin basic protein isoform 6 [Homo sapiens]; (3504:) Myelin Basic Protein Stimulator; (3505:) Myeloblastin precursor (Leukocyte proteinase 3) (PR-3) (PR3) (AGP7) (Wegener autoantigen) (P29) (C-ANCA antigen) (Neutrophil proteinase4) (NP-4); (3506:) myelodysplastic syndromes relative [Homo sapiens]; (3507:) myeloperoxidase [Homo sapiens]; (3508:) myofibrillogenesis regulator 1 isoform 1 [Homo sapiens]; (3509:) myofibrillogenesis regulator 1 isoform 2 [Homo sapiens]; (3510:) myofibrillogenesis regulator 1 isoform 3 [Homo sapiens]; (3511:) myo-inositol oxygenase [Homo sapiens]; (3512:) myo-inositol-1(or 4)-monophosphatase [Homo sapiens]; (3513:) Myosin heavy chain, cardiac muscle beta isoform (MyHC-beta); (3514:) myosin light chain kinase isoform 1 [Homo sapiens]; (3515:) myosin light chain kinase isoform 2 [Homo sapiens]; (3516:) myosin light chain kinase isoform 3A [Homo sapiens]; (3517:) myosin light chain kinase isoform 3B [Homo sapiens]; (3518:) Myosin light chain kinase, smooth muscle (MLCK) (Telokin) (Kinase-related protein) (KRP); (3519:) Myosin regulatory light chain 2, nonsarcomeric (Myosin RLC); (3520:) Myosin regulatory light chain 2, smooth muscle isoform (Myosin RLC) (Myosin regulatory light chain 9) (LC20); (3521:) Myostatin; (3522:) myotonic dystrophy protein kinase [Homo sapiens]; (3523:) Myotonin-protein kinase (Myotonic dystrophy protein kinase) (MDPK) (DM-kinase) (DMK) (DMPK) (MT-PK); (3524:) myristoyl CoA: protein N-myristoyltransferase [Homo sapiens]; (3525:) Myristoylated Alanine-Rich C-Kinase Substrate (MARCKS); (3526:) myristoylated alanine-rich protein kinase C substrate [Homo sapiens]; (3527:) myristoyl-CoA: protein N-myristoyltransferase [Homo sapiens]; (3528:) Na+/K+-ATPase alpha 1 subunit isoform a proprotein [Homo sapiens]; (3529:) Na+/K+-ATPase alpha 1 subunit isoform b proprotein [Homo sapiens]; (3530:) Na+/K+-ATPase alpha 2 subunit proprotein [Homo sapiens]; (3531:) Na+/K+-ATPase alpha 3 subunit [Homo sapiens]; (3532:) Na+/K+-ATPase alpha 4 subunit isoform 1 [Homo sapiens]; (3533:) Na+/K+-ATPase alpha 4 subunit isoform 2 [Homo sapiens]; (3534:) Na+/K+-ATPase beta 1 subunit isoform a [Homo sapiens]; (3535:) Na+/K+-ATPase beta 1 subunit isoform b [Homo sapiens]; (3536:) Na+/K+-ATPase beta 2 subunit [Homo sapiens]; (3537:) Na+/K+-ATPase beta 3 subunit [Homo sapiens]; (3538:) N-acetylated-alpha-linked acidic dipeptidase 2(N-acetylated-alpha-linked acidic dipeptidase II) (NAALADase II); (3539:) N-acetylated-alpha-linked-acidic dipeptidase (NAALADase); (3540:) N-acetylgalactosamine 4-sulfate 6-O-sulfotransferase (GalNAc4S-6ST) (B-cell RAG-associated gene protein) (hBRAG); (3541:) N-acetylgalactosamine 6-sulfate sulfatase [Homo sapiens]; (3542:) N-acetylgalactosamine-6-sulfatase precursor [Homo sapiens]; (3543:) N-acetylgalactosaminyltransferase 7 (Protein-UDPacetylgalactosaminyltransferase 7) (UDP-GalNAc: polypeptide N-acetylgalactosaminyltransferase 7) (Polypeptide GalNActransferase 7) (GalNAc-T7) (pp-GaNTase 7); (3544:) N-Acetylglucosamine kinase [Homo sapiens]; (3545:) N-acetylglucosamine-1-phosphate transferase [Homo sapiens]; (3546:) N-acetylglucosamine-1-phosphodiester alpha-N-acetylglucosaminidase precursor (Phosphodiester alpha-GlcNAcase) (Mannose6-phosphate-uncovering enzyme); (3547:) N-acetylglucosamine-1-phosphodiester alpha-N-acetylglucosaminidase precursor [Homo sapiens]; (3548:) N-acetylglucosamine-1-phosphotransferase subunit gamma precursor (GlcNAc-1-phosphotransferase subunit gamma) (UDP-N-acetylglucosamine-1-phosphotransferase, subunit gamma); (3549:) "N-acetylglucosamine-1-phosphotransferase subunits alpha/beta precursor (GlcNAc-1-phosphotransferase alpha/beta subunits) (UDP-N-acetylglucosamine-1-phosphotransferase alpha/beta subunits) (Stealth protein GNPTAB) [Contains: N-acetylglucosamine-1-phosphotransferase subunit alpha; N-acetylglucosamine-1-phosphotransferase subunit beta]."; (3550:) N-acetylglucosamine-1-phosphotransferase, gamma subunit [Homo sapiens]; (3551:) N-acetylglucosamine-6-O-sulfotransferase (GlcNAc6ST) [Homo sapiens]; (3552:) N-acetylglutamate synthase [Homo sapiens]; (3553:) "N-acetylglutamate synthase, mitochondrial precursor (Amino-acidacetyltransferase) [Contains:) N-acetylglutamate synthase long form; N-acetylglutamate synthase short form; N-acetylglutamate synthase conserved domain form]."; (3554:) N-acetyllactosaminide beta-1,3-N-acetylglucosaminyltransferase(Poly-N-acetyllactosamine extension enzyme) (1-beta-1,3-N-acetylglucosaminyltransferase) (iGnT) (UDP-GlcNAc:betaGal beta-1,3-N-acetylglucosaminyltransferase 6); (3555:) N-acetyllactosaminide beta-1,6-N-acetylglucosaminyl-transferase(N-acetylglucosaminyltransferase) (I-branching enzyme) (IGNT); (3556:) N-acetyllactosaminide beta-1,6-N-acetylglucosaminyltransferase [Homo sapiens]; (3557:) N-acetylneuraminate pyruvate lyase [Homo sapiens]; (3558:) N-acetylneuraminic acid phosphate synthase [Homo sapiens]; (3559:) N-acetyltransferase 1 [Homo sapiens]; (3560:)

N-acetyltransferase 2 [*Homo sapiens*]; (3561:) N-acetyltransferase ESCO1 (Establishment of cohesion 1 homolog 1) (ECO1 homolog 1) (ESO1 homolog 1) (Establishment factor-likeprotein 1) (EFO1p) (hEFO1) (CTF7 homolog 1); (3562:) N-acylaminoacyl-peptide hydrolase [*Homo sapiens*]; (3563:) N-acylethanolamine-hydrolyzing acid amidase precursor (N-acylsphingosine amidohydrolase-like) (ASAH-like protein) (Acidceramidase-like protein); (3564:) N-acylglucosamine 2-epimerase (GlcNAc 2-epimerase) (N-acetyl-D-glucosamine 2-epimerase) (AGE) (Renin-binding protein) (RnBP); (3565:) N-acylneuraminate cytidylyltransferase (CMP-N-acetylneuraminic acidsynthetase) (CMP-NeuNAc synthetase); (3566:) N-acylneuraminate-9-phosphatase (Neu5Ac-9-Pase) (Haloaciddehalogenase-like hydrolase domain-containing protein 4); (3567:) N-acylsphingosine amidohydrolase (acid ceramidase) 1 isoform b [*Homo sapiens*]; (3568:) N-acylsphingosine amidohydrolase (acid ceramidase) 1 preproprotein isoform a [*Homo sapiens*]; (3569:) N-acylsphingosine amidohydrolase 3 [*Homo sapiens*]; (3570:) N-acylsphingosine amidohydrolase-like protein isoform 1 precursor [*Homo sapiens*]; (3571:) N-acylsphingosine amidohydrolase-like protein isoform 2 precursor [*Homo sapiens*]; (3572:) NAD kinase (Poly(P)/ATP NAD kinase); (3573:) NAD(P) dependent steroid dehydrogenase-like [*Homo sapiens*]; (3574:) NAD(P)H dehydrogenase [quinone] 1 (Quinone reductase 1) (NAD(P)H:quinone oxidoreductase 1) (QR1) (DT-diaphorase) (DTD) (Azoreductase) (Phylloquinone reductase) (Menadione reductase); (3575:) NAD(P)H menadione oxidoreductase 1, dioxin-inducible isoform a [*Homo sapiens*]; (3576:) NAD(P)H menadione oxidoreductase 1, dioxin-inducible isoform b [*Homo sapiens*]; (3577:) NAD(P)H menadione oxidoreductase 1, dioxin-inducible isoform c [*Homo sapiens*]; (3578:) NAD+ADP-ribosyltransferase; (3579:) NAD-dependent deacetylase sirtuin-1 (hSIRT1) (hSIR2) (SIR2-likeprotein 1); (3580:) NAD-dependent deacetylase sirtuin-2 (SIR2-like) (SIR2-like protein2); (3581:) NAD-dependent deacetylase sirtuin-3, mitochondrial precursor (SIR2-like protein 3) (hSIRT3); (3582:) NAD-dependent malic enzyme, mitochondrial precursor (NAD-ME) (Malicenzyme 2); (3583:) NADH dehydrogenase (ubiquinone) 1 alpha subcomplex, 10, 42 kDa precursor [*Homo sapiens*]; (3584:) NADH dehydrogenase (ubiquinone) 1 alpha subcomplex, 4, 9 kDa [*Homo sapiens*]; (3585:) NADH dehydrogenase (ubiquinone) 1 alpha subcomplex, 5 [*Homo sapiens*]; (3586:) NADH dehydrogenase (ubiquinone) 1 alpha subcomplex, 8, 19 kDa [*Homo sapiens*]; (3587:) NADH dehydrogenase (ubiquinone) 1 beta subcomplex, 2, 8 kDa precursor [*Homo sapiens*]; (3588:) NADH dehydrogenase (ubiquinone) 1 beta subcomplex, 3, 12 kDa [*Homo sapiens*]; (3589:) NADH dehydrogenase (ubiquinone) 1 beta subcomplex, 4, 15 kDa [*Homo sapiens*]; (3590:) NADH dehydrogenase (ubiquinone) 1 beta subcomplex, 5, 16 kDa precursor [*Homo sapiens*]; (3591:) NADH dehydrogenase (ubiquinone) 1 beta subcomplex, 6, 17 kDa isoform1 [*Homo sapiens*]; (3592:) NADH dehydrogenase (ubiquinone) 1 beta subcomplex, 6, 17 kDa isoform2 [*Homo sapiens*]; (3593:) NADH dehydrogenase (ubiquinone) 1 beta subcomplex, 7, 18 kDa [*Homo sapiens*]; (3594:) NADH dehydrogenase (ubiquinone) Fe-S protein 1, 75 kDa precursor [*Homo sapiens*]; (3595:) NADH dehydrogenase (ubiquinone) Fe-S protein 3, 30 kDa(NADH-coenzyme Q reductase) [*Homo sapiens*]; (3596:) NADH dehydrogenase (ubiquinone) Fe-S protein 4, 18 kDa(NADH-coenzyme Q reductase) [*Homo sapiens*]; (3597:) NADH dehydrogenase (ubiquinone) Fe-S protein 6, 13 kDa(NADH-coenzyme Q reductase) [*Homo sapiens*]; (3598:) NADH dehydrogenase [ubiquinone] 1 alpha subcomplex subunit 1(NADH-ubiquinone oxidoreductase MWFE subunit) (Complex I-MWFE) (CI-MWFE); (3599:) NADH dehydrogenase [ubiquinone] 1 alpha subcomplex subunit 10,mitochondrial precursor (NADH-ubiquinone oxidoreductase 42 kDa subunit) (Complex I-42 kD) (CI-42 kD); (3600:) NADH dehydrogenase [ubiquinone] 1 alpha subcomplex subunit 11(NADH-ubiquinone oxidoreductase subunit B14.7) (Complex I-B14.7) (CI-B14.7); (3601:) NADH dehydrogenase [ubiquinone] 1 alpha subcomplex subunit 12(NADH-ubiquinone oxidoreductase subunit 817.2) (Complex I-B17.2) (CI-B17.2) (CIB17.2) (13 kDa differentiation-associated protein); (3602:) NADH dehydrogenase [ubiquinone] 1 alpha subcomplex subunit 13(NADH-ubiquinone oxidoreductase 816.6 subunit) (Complex I-B16.6) (CI-B16.6) (Gene associated with retinoic-interferon-induced mortality 19 protein) (GRIM-19) (Cell death-regulatory protein GRIM-19); (3603:) NADH dehydrogenase [ubiquinone] 1 alpha subcomplex subunit 2(NADH-ubiquinone oxidoreductase B8 subunit) (Complex I-B8) (CI-B8); (3604:) NADH dehydrogenase [ubiquinone] 1 alpha subcomplex subunit 3(NADH-ubiquinone oxidoreductase B9 subunit) (Complex I-B9) (CI-B9); (3605:) NADH dehydrogenase [ubiquinone] 1 alpha subcomplex subunit 4(NADH-ubiquinone oxidoreductase MLRQ subunit) (Complex I-MLRQ) (CI-MLRQ); (3606:) NADH dehydrogenase [ubiquinone] 1 alpha subcomplex subunit 5(NADH-ubiquinone oxidoreductase 13 kDa-B subunit) (Complexi-13 kD-B) (CI-13 kD-B) (Complex I subunit B13); (3607:) NADH dehydrogenase [ubiquinone] 1 alpha subcomplex subunit 6(NADH-ubiquinone oxidoreductase B14 subunit) (Complex I-B14) (CI-B14); (3608:) NADH dehydrogenase [ubiquinone] 1 alpha subcomplex subunit 7(NADH-ubiquinone oxidoreductase subunit B14.5a) (Complex I-B14.5a) (CI-B14.5a); (3609:) NADH dehydrogenase [ubiquinone] 1 alpha subcomplex subunit 8(NADH-ubiquinone oxidoreductase 19 kDa subunit) (Complex I-19 kD) (CI-19 kD) (Complex I-PGIV) (CI-PGIV); (3610:) NADH dehydrogenase [ubiquinone] 1 alpha subcomplex subunit 9,mitochondrial precursor (NADH-ubiquinone oxidoreductase 39 kDa subunit) (Complex I-39 kD) (CI-39 kD); (3611:) NADH dehydrogenase [ubiquinone] 1 beta subcomplex subunit 1(NADH-ubiquinone oxidoreductase MNLL subunit) (Complex I-MNLL) (CI-MNLL); (3612:) NADH dehydrogenase [ubiquinone] 1 beta subcomplex subunit 10(NADH-ubiquinone oxidoreductase PDSW subunit) (Complex I-PDSW) (CI-PDSW); (3613:) NADH dehydrogenase [ubiquinone] 1 beta subcomplex subunit 11,mitochondrial precursor (NADH-ubiquinone oxidoreductase ESSS subunit) (Complex I-ESSS) (CI-ESSS) (Neuronal protein 17.3) (p17.3) (Np17.3); (3614:) NADH dehydrogenase [ubiquinone] 1 beta subcomplex subunit 2,mitochondrial precursor (NADH-ubiquinone oxidoreductase AGGG subunit) (Complex I-AGGG) (CI-AGGG); (3615:) NADH dehydrogenase [ubiquinone] 1 beta subcomplex subunit 3(NADH-ubiquinone oxidoreductase B12 subunit) (Complex I-B12) (CI-B12); (3616:) NADH dehydrogenase [ubiquinone] 1 beta subcomplex subunit 4(NADH-ubiquinone oxidoreductase B15 subunit) (Complex I-B15) (CI-B15); (3617:) NADH dehydrogenase [ubiquinone] 1 beta subcomplex subunit 5,mitochondrial precursor (NADH-ubiquinone oxidoreductase SGDH subunit) (Complex I-SGDH) (CI-SGDH); (3618:) NADH dehydrogenase [ubiquinone] 1 beta subcomplex subunit 6(NADH-ubiquinone oxidoreductase B17 subunit) (Complex I-B17) (CI-B17); (3619:) NADH dehydrogenase [ubiquinone] 1 beta subcomplex subunit 7(NADH-ubiquinone oxidoreductase B18 subunit) (Complex I-B18) (CI-B18) (Cell adhesion protein SQM1); (3620:) NADH dehydrogenase [ubiquinone] 1 beta subcomplex subunit 8,mitochondrial precursor (NADH-ubiquinone oxidoreductase ASHi subunit) (Complex I-ASHI) (CI-ASHI); (3621:) NADH dehydrogenase [ubiquinone] 1 beta subcomplex subunit 9(NADH-ubiquinone oxidoreductase B22 subunit) (Complex I-B22) (CI-B22); (3622:) NADH dehydrogenase [ubiquinone] 1 subunit C1, mitochondrial precursor (NADH-ubiquinone oxidoreductase KFYI subunit) (ComplexI-KFYI) (CI-KFYI); (3623:) NADH dehydrogenase [ubiquinone] 1 subunit C2 (NADH-ubiquinoneoxidoreductase subunit B14.5b) (Complex I-B14.5b) (CI-B14.5b); (3624:) NADH dehydrogenase [ubiquinone] flavoprotein 1, mitochondrial precursor (NADH-ubiquinone oxidoreductase 51 kDa subunit) (ComplexI-51 kD) (CI-51 kD) (NADH dehydrogenase flavoprotein 1); (3625:) NADH dehydrogenase [ubiquinone] flavoprotein 2, mitochondrial precursor (NADH-ubiquinone oxidoreductase 24 kDa subunit); (3626:) NADH dehydrogenase [ubiquinone] flavoprotein 3, mitochondrial precursor (NADH-ubiquinone oxidoreductase 9 kDa subunit) (ComplexI-9 kD) (CI-9 kD) (NY-REN-4 antigen); (3627:) NADH dehydrogenase [ubiquinone] iron-sulfur protein 2,mitochondrial precursor (NADH-ubiquinone oxidoreductase 49 kDa subunit) (ComplexI-49 kD) (CI-49 kD); (3628:) NADH dehydrogenase [ubiquinone] iron-sulfur protein 3,mitochondrial precursor (NADH-ubiquinone oxidoreductase 30 kDa subunit) (Complex I-30 kD) (CI-30 kD); (3629:) NADH dehydrogenase [ubiquinone] iron-sulfur protein 4,mitochondrial precursor (NADH-ubiquinone oxidoreductase 18 kDa subunit) (Complex I-18 kDa) (CI-18 kDa) (Complex I-AQDQ) (CI-AQDQ); (3630:) NADH dehydrogenase [ubiquinone] iron-sulfur protein 5(NADH-ubiquinone oxidoreductase 15 kDa subunit) (Complex I-15 kDa) (CI-15 kDa); (3631:) NADH dehydrogenase [ubiquinone] iron-sulfur protein 6,mitochondrial precursor (NADH-ubiquinone oxidoreductase 13 kDa-A subunit) (Complex I-13 kD-A) (CI-13 kD-A); (3632:) NADH dehydrogenase [ubiquinone] iron-sulfur protein 7,mitochondrial precursor (NADH-ubiquinone oxidoreductase 20 kDa subunit) (Complex I-20 kD) (CI-20 kD) (PSST subunit); (3633:) "NADH-cytochrome b5 reductase (B5R) (Diaphorase-1) (Cytochrome b5reductase 3) [Contains:) NADH-cytochrome b5 reductase membrane-bound form; NADH-cytochrome b5 reductase soluble form]."; (3634:) NADH-cytochrome b5 reductase [*Homo sapiens*]; (3635:) "NADH-cytochrome b5 reductase; b5R [*Homo sapiens*]."; (3636:) NADH-ubiquinone oxidoreductase 75 kDa subunit, mitochondrial precursor (Complex I-75 kD) (CI-75 kD); (3637:) NADP(+)-dependent malic enzyme—human (fragments); (3638:) "NADP+-dependent malic enzyme; malate dehydrogenase (oxaloacetate decarboxylating) (NADP+) [*Homo sapiens*]."; (3639:) NADP-dependent isocitrate dehydrogenase [*Homo sapiens*]; (3640:) NADP-dependent malic enzyme (NADP-ME) (Malic enzyme 1); (3641:) NADP-dependent malic enzyme, mitochondrial precursor (NADP-ME) (Malic enzyme 3); (3642:) NADP-dependent malic enzyme; (3643:) NADPH oxidase 1 isoform long [*Homo sapiens*]; (3644:) NADPH oxidase 1 isoform long variant [*Homo sapiens*]; (3645:) NADPH oxidase 1 isoform short [*Homo sapiens*]; (3646:) NADPH oxidase 3 (gp91phox homolog 3) (GP91-3) (Mitogenic oxidase2); (3647:) NADPH oxidase 3 [*Homo sapiens*]; (3648:) NADPH oxidase 4 (Kidney superoxide-producing NADPH oxidase) (KOX-1) (Renal NAD(P)H-oxidase); (3649:) NADPH oxidase 5; (3650:) NADPH oxidase homolog 1 (NOX-1) (NOH-1) (NADH/NADPH mitogenicoxidase subunit P65-MOX) (Mitogenic oxidase 1) (MOX1); (3651:) NADPH oxidase, EF hand calcium-binding domain 5 [*Homo sapiens*]; (3652:) NADPH—cytochrome P450 reductase (CPR) (P450R); (3653:) nardilysin (N-arginine dibasic convertase) [*Homo sapiens*]; (3654:) Nardilysin precursor (N-arginine dibasic convertase) (NRD-convertase) (NRD-C); (3655:) N-arginine dibasic convertase [*Homo sapiens*]; (3656:) natriuretic peptide precursor A [*Homo sapiens*]; (3657:) natriuretic peptide precursor B preprotein [*Homo sapiens*]; (3658:) Natriuretic Peptide Receptor A (NPR-A); (3659:) natriuretic peptide receptor A/guanylate cyclase A (atrionatriuretic peptide receptor A) [*Homo sapiens*]; (3660:) natriuretic peptide receptor B precursor [*Homo sapiens*]; (3661:) Natural cytotoxicity triggering receptor 1 precursor (Natural killer cell p46-related protein) (NKp46) (hNKp46) (NK-p46) (NKcell-activating receptor) (Lymphocyte antigen 94 homolog) (CD335antigen); (3662:) Natural cytotoxicity triggering receptor 2 precursor (Natural killer cell p44-related protein) (NKp44) (NK-p44) (NKcell-activating receptor) (Lymphocyte antigen 95 homolog) (CD336antigen); (3663:) Natural cytotoxicity triggering receptor 3 precursor (Natural killer cell p30-related protein) (NKp30) (NK-p30) (CD337 antigen); (3664:) Natural killer cell receptor 2B4 precursor (NKR2B4) (NK cell type (receptor protein 2B4) (h2B4) (CD244 antigen) (NK cell activation-inducing ligand) (NAIL); (3665:) Natural killer cells antigen CD94 (NK cell receptor) (Killer cellectin-like receptor subfamily D member 1) (KP43); (3666:) N-Cadherin; (3667:) NCUBE1 [*Homo sapiens*]; (3668:) N-deacetylase/N-sulfotransferase (heparan glucosaminyl) 2 [*Homo sapiens*]; (3669:) NDUFS1 protein [*Homo sapiens*]; (3670:) NEDD4-like E3 ubiquitin-protein ligase WWP1 (WW domain-containing protein 1) (Atropin-1-interacting protein 5) (AIP5); (3671:) NEDD4-like E3 ubiquitin-protein ligase WWP2 (WW domain-containingprotein 2) (Atrophin-1-interacting protein 2) (AIP2); (3672:) NEDD8 precursor (Ubiquitin-like protein Nedd8) (Neddylin); (3673:) NEDD8-activating enzyme E1 catalytic subunit (Ubiquitin-activating enzyme 3) (NEDD8-activating enzyme E1 C) (Ubiquitin-activating enzyme E1C); (3674:) NEDD8-activating enzyme E1 regulatory subunit (Amyloid protein-binding protein 1) (Amyloid beta precursor protein-binding protein 1, 59 kDa) (APP-BP1) (Proto-oncogene protein 1) (HPP1); (3675:) Nedd8-activating enzyme hUba3 [*Homo sapiens*]; (3676:) NEDD8-conjugating enzyme [*Homo sapiens*]; (3677:) Nedd8-conjugating enzyme hUbc12 [*Homo sapiens*]; (3678:) NEDD8-conjugating enzyme NCE2 [*Homo sapiens*]; (3679:) NEDD8-conjugating enzyme Ubc12 (Ubiquitin-conjugating enzyme E2 M) (NEDD8 protein ligase) (NEDD8 carrier protein); (3680:) Nef associated protein 1 [*Homo sapiens*]; (3681:) nei endonuclease VIII-like 1 [*Homo sapiens*]; (3682:) nei-like 2 [*Homo sapiens*]; (3683:) Nematode Nicotinic Acetylcholine Receptor (nAChR); (3684:) neo-poly(A) polymerase [*Homo sapiens*]; (3685:) nephrin [*Homo sapiens*]; (3686:) Nerve Growth Factor (NGF); (3687:) Netrin receptor DCC precursor (Tumor suppressor protein DCC) (Colorectal cancer suppressor); (3688:) Netrin receptor UNC5A precursor (Unc-5 homolog A) (Unc-5 homolog1); (3689:) Netrin receptor UNC5B precursor (Unc-5 homolog B) (Unc-5 homolog 2) (p53-regulated receptor for death and life protein 1); (3690:) Netrin receptor UNC5C precursor (Unc-5 homolog C) (Unc-5 homolog3); (3691:) Netrin receptor UNC5D precursor (Unc-5 homolog D) (Unc-5 homolog4); (3692:) neural stem cell-derived dendritic regulator [*Homo sapiens*]; (3693:) Neural Thread Protein (NTP); (3694:) Neuralized-like protein 2; (3695:) Neuraminidase; (3696:) neuraminidase precursor [*Homo sapiens*]; (3697:)

neuroblastoma apoptosis-related protease [*Homo sapiens*]; (3698:) Neuroendocrine convertase 1 precursor (NEC 1) (PC1) (Prohormoneconvertase 1) (Proprotein convertase 1); (3699:) Neuroendocrine convertase 2 precursor (NEC 2) (PC2) (Prohormoneconvertase 2) (Proprotein convertase 2) (KEX2-like endoprotease 2); (3700:) Neurofibromin (Neurofibromatosis-related protein NF-1) [Contains: Neurofibromin truncated]; (3701:) neurofibromin isoform 1 [*Homo sapiens*]; (3702:) neurofibromin isoform 2 [*Homo sapiens*]; (3703:) neurofilament, light polypeptide 68 kDa [*Homo sapiens*]; (3704:) "Neurogenic locus notch homolog protein 1 precursor (Notch 1) (hN1) (Translocation-associated notch protein TAN-1) [Contains:) Notch 1extracellular truncation; Notch 1 intracellular domain]."; (3705:) "Neurogenic locus notch homolog protein 2 precursor (Notch 2) (hN2)[Contains:) Notch 2 extracellular truncation; Notch 2 intracellulardomain]."; (3706:) "Neurogenic locus notch homolog protein 3 precursor (Notch 3)[Contains:) Notch 3 extracellular truncation; Notch 3 intracellulardomain]."; (3707:) "Neurogenic locus notch homolog protein 4 precursor (Notch 4) (hNotch4) [Contains:) Notch 4 extracellular truncation; Notch 4intracellular domain]."; (3708:) Neurokinin NK1 Receptor; (3709:) Neurokinin NK2 Receptor; (3710:) Neurokinin NK3 Receptor; (3711:) Neuromedin K receptor (NKR) (Neurokinin B receptor) (NK-3 receptor) (NK-3R) (Tachykinin receptor 3); (3712:) Neuromedin U receptor 1 (NMU-R1) (G-protein coupled receptor 66) (G-protein coupled receptor FM-3); (3713:) Neuromedin U receptor 2 (NMU-R2) (G-protein coupled receptor TGR-1) (G-protein coupled receptor FM-4); (3714:) Neuromedin-B receptor (NMB-R) (Neuromedin-B-preferring bombesin receptor); (3715:) Neuronal acetylcholine receptor protein subunit alpha-10 precursor (Nicotinic acetylcholine receptor subunit alpha 10) (NACHR alpha10); (3716:) Neuronal acetylcholine receptor protein subunit alpha-3 precursor; (3717:) Neuronal acetylcholine receptor protein subunit alpha-5 precursor; (3718:) Neuronal acetylcholine receptor protein subunit alpha-6 precursor; (3719:) Neuronal acetylcholine receptor protein subunit alpha-9 precursor (Nicotinic acetylcholine receptor subunit alpha 9) (NACHR alpha 9); (3720:) Neuronal Nicotinic Acetylcholine Receptor (nAChR); (3721:) Neuronal pentraxin receptor; (3722:) neuronal tryptophan hydroxylase [*Homo sapiens*]; (3723:) neuron-derived receptor NOR-1—human; (3724:) Neuropeptide FF receptor 1 (G-protein coupled receptor 147) (RFamide-related peptide receptor OT7T022); (3725:) Neuropeptide FF receptor 2 (Neuropeptide G-protein coupled receptor) (G-protein coupled receptor 74) (G-protein coupled receptor HLWAR77); (3726:) Neuropeptide S receptor (G-protein coupled receptor 154) (G-protein coupled receptor for asthma susceptibility) (G-protein coupled receptor PGR14); (3727:) Neuropeptide Y receptor type 1 (NPY1-R); (3728:) Neuropeptide Y receptor type 2 (NPY2-R) (NPY-Y2 receptor); (3729:) Neuropeptide Y receptor type 4 (NPY4-R) (Pancreatic polypeptide receptor 1) (PP1); (3730:) Neuropeptide Y receptor type 5 (NPY5-R) (NPY-Y5 receptor) (Y5receptor) (NPYY5); (3731:) Neuropeptide Y Y1 Receptor (NPY Y1R); (3732:) Neuropeptide Y Y2 Receptor (NPY Y2R); (3733:) Neuropeptide Y Y4 Receptor (NPY Y4R); (3734:) Neuropeptide Y Y5 Receptor (NPY Y5R); (3735:) Neuropeptides B/W receptor type 1 (G-protein coupled receptor 7); (3736:) Neuropeptides B/W receptor type 2 (G-protein coupled receptor 8); (3737:) Neuropilin and tolloid-like protein 1 precursor (Brain-specific transmembrane protein containing 2 CUB and 1 LDL-receptor class A domains protein 1); (3738:) Neuropilin and tolloid-like protein 2 precursor (Brain-specific transmembrane protein containing 2 CUB and 1 LDL-receptor class A domains protein 2); (3739:) Neuropilin-1 precursor (Vascular endothelial cell growth factor 165receptor) (CD304 antigen); (3740:) Neuropilin-2 precursor (Vascular endothelial cell growth factor 165receptor 2); (3741:) Neurotensin Receptor; (3742:) Neurotensin receptor type 1 (NT-R-1) (High-affinity levocabastine-insensitive neurotensin receptor) (NTRH); (3743:) Neurotensin receptor type 2 (NT-R-2) (Levocabastine-sensitive neurotensin receptor) (NTR2 receptor); (3744:) neurotensin/neuromedin N preproprotein [*Homo sapiens*]; (3745:) Neurotrophic factor production accelerator; (3746:) Neurotrophic Tyrosine Kinase Receptor 1 (NTRK1); (3747:) Neurotrophic Tyrosine K1nase Receptor 2 (NTRK2); (3748:) neurotrophin 5 preproprotein [*Homo sapiens*]; (3749:) neurotrypsin precursor [*Homo sapiens*]; (3750:) Neutral alpha-glucosidase AB precursor (Glucosidase II subunitalpha); (3751:) Neutral amino acid transporter B(0) (ATB(0)) (Sodium-dependent neutral amino acid transporter type 2) (RD114/simian type Dretrovirus receptor) (Baboon M7 virus receptor); (3752:) Neutral ceramidase (NCDase) (N-CDase) (Acylsphingosine deacylase 2) (N-acylsphingosine amidohydrolase 2) (BCDase) (LCDase) (hCD)[Contains:) Neutral ceramidase soluble form]; (3753:) Neutral Endopeptidase (NEP); (3754:) Neutral Sphingomyelinase (nSMase); (3755:) Neutrophil Cathepsin G; (3756:) Neutrophil collagenase precursor (Matrix metalloproteinase-8) (MMP-8) (PMNL collagenase) (PMNL-CL); (3757:) Neutrophil cytosol factor 4 (NCF-4) (Neutrophil NADPH oxidase factor 4) (p40-phox) (p40phox); (3758:) neutrophil cytosolic factor 1 [*Homo sapiens*]; (3759:) neutrophil cytosolic factor 4 (40 kD) isoform 1 [*Homo sapiens*]; (3760:) neutrophil cytosolic factor 4 (40 kD) isoform 2 [*Homo sapiens*]; (3761:) Neutrophil Elastase; (3762:) NFS1 nitrogen fixation 1 [*Homo sapiens*]; (3763:) "N-glycosylase/DNA lyase [Includes:) 8-oxoguanine DNA glycosylase; DNA-(apurinic or apyrimidinic site) lyase (Alyase)]."; (3764:) Niacin Receptor; (3765:) Nicastrin precursor; (3766:) NICE-5 protein [*Homo sapiens*]; (3767:) Nicotinamide Adenine Dinucleotide synthetase (NADs); (3768:) nicotinamide mononucleotide adenylyl transferase [*Homo sapiens*]; (3769:) Nicotinamide mononucleotide adenylyltransferase 1 (NMNadenylyltransferase 1); (3770:) nicotinamide mononucleotide adenylyltransferase 2 isoform 1 [*Homo sapiens*]; (3771:) nicotinamide mononucleotide adenylyltransferase 2 isoform 2 [*Homo sapiens*]; (3772:) nicotinamide nucleotide adenylyltransferase 1 [*Homo sapiens*]; (3773:) nicotinamide nucleotide adenylyltransferase 3 [*Homo sapiens*]; (3774:) nicotinamide riboside kinase 1 [*Homo sapiens*]; (3775:) Nicotinamide riboside kinase 2 (Integrin beta-1-binding protein 3) (Muscle integrin-binding protein) (MIBP); (3776:) nicotinamide riboside kinase 2 [*Homo sapiens*]; (3777:) Nicotinic acid receptor 1 (G-protein coupled receptor 109A) (G-protein coupled receptor HM74A); (3778:) Nicotinic acid receptor 2 (G-protein coupled receptor 109B) (G-protein coupled receptor HM74) (G-protein coupled receptor HM74B); (3779:) Nicotinic Receptor; (3780:) NifU-like N-terminal domain-containing protein, mitochondrial precursor (NifU-like protein) (Iron-sulfur cluster assembly enzyme ISCU); (3781:) Nitric Oxide Neutralizer; (3782:) Nitric Oxide Synthase (NOS); (3783:) nitric oxide synthase 1 (neuronal) [*Homo sapiens*]; (3784:) nitric oxide synthase 2A isoform 1 [*Homo sapiens*]; (3785:) nitric oxide synthase 2A isoform 2 [*Homo sapiens*]; (3786:) nitric oxide synthase 3 (endothelial cell) [*Homo sapiens*]; (3787:) nitric oxide synthase trafficking isoform 1 [*Homo sapiens*]; (3788:) nitric oxide synthase trafficking isoform 2 [*Homo sapiens*]; (3789:) Nitric oxide synthase, inducible (NOS type II) (Inducible NOsynthase) (Inducible NOS) (iNOS) (Hepatocyte NOS) (HEP-NOS); (3790:) nitric oxide synthase; (3791:) Nitric-oxide synthase IIC(NOS type II C) (NOSIIc); (3792:) Nitric-oxide synthase, brain (NOS type I) (Neuronal NOS) (N—NOS) (nNOS) (Constitutive NOS) (NC-NOS) (bNOS); (3793:) Nitric-oxide synthase, endothelial (EC-NOS) (NOS type III) (NOSIII) (Endothelial NOS) (eNOS) (Constitutive NOS) (cNOS); (3794:) NKG2-A/NKG2-B type II integral membrane protein(NKG2-NB-activating NK receptor) (NK cell receptor A) (CD159a antigen); (3795:) NKG2-C type II integral membrane protein (NKG2-C-activating NK receptor) (NK cell receptor C) (CD159c antigen); (3796:) NKG2-D type II integral membrane protein (NKG2-D-activating NK receptor) (NK cell receptor D) (Killer cell lectin-like receptor subfamily K member 1) (CD314 antigen); (3797:) NKG2-E type II integral membrane protein (NKG2-E-activating NK receptor) (NK cell receptor E); (3798:) NKG2-F type II integral membrane protein (NKG2-F-activating NK receptor) (NK cell receptor F); (3799:) N-kinase; (3800:) NME1-NME2 protein [Homo sapiens]; (3801:) N-methyl purine DNA-glycosylase [Homo sapiens]; (3802:) N-Methyl-D-Aspartate (NMDA) Receptor; (3803:) N-methylpurine-DNA glycosylase isoform a [Homo sapiens]; (3804:) N-methylpurine-DNA glycosylase isoform b [Homo sapiens]; (3805:) N-methylpurine-DNA glycosylase isoform c [Homo sapiens]; (3806:) N-myristoyltransferase 1 [Homo sapiens]; (3807:) Nociceptin receptor (Orphanin FQ receptor) (Kappa-type 3 opioid receptor) (KOR-3); (3808:) NOD2 (CARD15) Receptor; (3809:) Non-Canonical UBiquitin Conjugating Enzyme 1 (NCUBEI) [Homo sapiens]; (3810:) nonfunctional alpha(1,2)-fucosyltransferase [Homo sapiens]; (3811:) non-metastatic cells 1, protein (NM23A) expressed in isoform a [Homo sapiens]; (3812:) non-metastatic cells 1, protein (NM23A) expressed in isoform b [Homo sapiens]; (3813:) non-metastatic cells 2, protein (NM23B) expressed in [Homo sapiens]; (3814:) Norepinephrine Reuptake; (3815:) Notch-1 Protein; (3816:) nov precursor [Homo sapiens]; (3817:) novel AMP-binding enzyme [Homo sapiens]; (3818:) novel protein [Homo sapiens]; (3819:) N-sulfoglucosamine sulfohydrolase (sulfamidase) [Homo sapiens]; (3820:) N-sulphoglucosamine sulphohydrolase [Homo sapiens]; (3821:) N-sulphoglucosamine sulphohydrolase precursor (Sulfoglucosaminesulfamidase) (Sulphamidase); (3822:) NT-3 growth factor receptor precursor (Neurotrophic tyrosine kinasereceptor type 3) (TrkC tyrosine kinase) (GP145-TrkC) (Trk-C); (3823:) N-terminal Asn amidase [Homo sapiens]; (3824:) nth endonuclease III-like 1 [Homo sapiens]; (3825:) N-Type Calcium Channel Blocker (NCCB); (3826:) NUAK family SNF1-like kinase 1 (AMPK-related protein kinase 5); (3827:) NUAK family SNF1-like kinase 2 (SNF1/AMP kinase-related kinase) (SNARK); (3828:) nuclear factor (erythroid-derived 2)-like 2 [Homo sapiens]; (3829:) nuclear factor kappa-B, subunit 1 [Homo sapiens]; (3830:) Nuclear Factor-Kappa B (NF-kB); (3831:) Nuclear receptor 0B1 (Nuclear receptor DAX-1) (DSS-AHC critical region on the X chromosome protein 1); (3832:) Nuclear receptor 0B2 (Orphan nuclear receptor SHP) (Small heterodimer partner); (3833:) Nuclear receptor coactivator 3 (NCoA-3) (Thyroid hormone receptor activator molecule 1) (TRAM-1) (ACTR) (Receptor-associated coactivator 3) (RAC-3) (Amplified in breast cancer-1 protein) (AIB-1) (Steroid receptor coactivator protein 3) (SRC-3) (CBP-interacting protein) (pCIP); (3834:) nuclear receptor interacting protein 1 [Homo sapiens]; (3835:) Nuclear receptor ROR-alpha (Nuclear receptor RZR-alpha); (3836:) Nuclear receptor ROR-beta (Nuclear receptor RZR-beta); (3837:) Nuclear receptor ROR-gamma (Nuclear receptor RZR-gamma); (3838:) nuclear receptor subfamily 1, group H, member 4 [Homo sapiens]; (3839:) nuclear receptor subfamily 3, group C, member 1 isoform alpha [Homo sapiens]; (3840:) nuclear receptor subfamily 3, group C, member 1 isoform beta [Homo sapiens]; (3841:) nuclear receptor subfamily 3, group C, member 1 isoform gamma [Homo sapiens]; (3842:) nuclear receptor subfamily 5, group A, member 1 [Homo sapiens]; (3843:) nuclear receptor subfamily 5, group A, member 2 isoform 1 [Homo sapiens]; (3844:) nuclear receptor subfamily 5, group A, member 2 isoform 2 [Homo sapiens]; (3845:) nucleolar protein GU2 [Homo sapiens]; (3846:) Nucleolin; (3847:) Nucleoside diphosphate kinase A (NDK A) (NDP kinase A) (Tumormetastatic process-associated protein) (Metastasis inhibition factor nm23) (nm23-H1) (Granzyme A-activated DNase) (GAAD); (3848:) Nucleoside diphosphate kinase B (NDK B) (NDP kinase B) (nm23-H2) (C-myc purine-binding transcription factor PUF); (3849:) Nucleoside Reverse Transcriptase (NRTI); (3850:) "nucleotide binding protein; NBP [Homo sapiens]."; (3851:) nudix-type motif 14 [Homo sapiens]; (3852:) nudix-type motif 1 isoform p18 [Homo sapiens]; (3853:) nudix-type motif 1 isoform p22 [Homo sapiens]; (3854) nudix-type motif 2 [Homo sapiens]; (3855:) O6-Alkylguanine-DNA Alkyltransferase (AGT); (3856:) O-6-methylguanine-DNA methyltransferase; (3857:) OB-Cadherin; (3858:) Olfactory receptor 10A1 (Olfactory receptor 11-403) (OR11-403); (3859:) Olfactory receptor 10A3 (HTPCRX12); (3860:) Olfactory receptor 10A4 (HP2) (Olfactory receptor-like protein JCG5); (3861:) Olfactory receptor 10A5 (HP3) (Olfactory receptor-like protein JCG6); (3862:) Olfactory receptor 10A6; (3863:) Olfactory receptor 10A7; (3864:) Olfactory receptor 10AD1; (3865:) Olfactory receptor 10AG1 (Olfactory receptor OR11-160); (3866:) Olfactory receptor 10C1 (Hs6M1-17); (3867:) Olfactory receptor 10D4; (3868:) Olfactory receptor 10G2; (3869:) Olfactory receptor 10G3 (Olfactory receptor OR14-40); (3870:) Olfactory receptor 10G4 (Olfactory receptor OR11-278); (3871:) Olfactory receptor 10G6 (Olfactory receptor OR11-280); (3872:) Olfactory receptor 10G7; (3873:) Olfactory receptor 10G8 (Olfactory receptor OR11-282); (3874:) Olfactory receptor 10G9; (3875:) Olfactory receptor 10H1; (3876:) Olfactory receptor 10H2; (3877:) Olfactory receptor 10H3; (3878:) Olfactory receptor 10H4; (3879:) Olfactory receptor 10H5; (3880:) Olfactory receptor 10J1 (Olfactory receptor-like protein HGMP07J) (Olfactory receptor OR1-26); (3881:) Olfactory receptor 10J3; (3882:) Olfactory receptor 10J5; (3883:) Olfactory receptor 10J6; (3884:) Olfactory receptor 10K1; (3885:) Olfactory receptor 10K2 (Olfactory receptor OR1-4); (3886:) Olfactory receptor 10P1 (Olfactory receptor OR12-7); (3887:) Olfactory receptor 10Q1; (3888:) Olfactory receptor 10R2; (3889:) Olfactory receptor 10S1; (3890:) Olfactory receptor 10T2 (Olfactory receptor OR1-3); (3891:) Olfactory receptor 10V1; (3892:) Olfactory receptor 10W1 (Olfactory receptor OR11-236); (3893:) Olfactory receptor 10X1 (Olfactory receptor OR1-14); (3894:) Olfactory receptor 10Z1; (3895:) Olfactory receptor 11A1 (Hs6M1-18); (3896:) Olfactory receptor 11G2; (3897:) Olfactory receptor 11H1 (Olfactory receptor 22-1) (OR22-1); (3898:) Olfactory receptor 11H4 (Olfactory receptor OR14-36); (3899:) Olfactory receptor 11H6 (Olfactory receptor OR14-35); (3900:) Olfactory receptor 11L1; (3901:) Olfactory receptor 12D2 (Hs6M1-20); (3902:) Olfactory receptor 12D3 (Hs6M1-27); (3903:) Olfactory receptor 13A1 (Olfactory receptor OR10-3); (3904:) Olfactory receptor 13C2; (3905:) Olfactory receptor 13C3;

(3906:) Olfactory receptor 13C4; (3907:) Olfactory receptor 13C5; (3908:) Olfactory receptor 13C8; (3909:) Olfactory receptor 13C9; (3910:) Olfactory receptor 13D1; (3911:) Olfactory receptor 13F1; (3912:) Olfactory receptor 13G1; (3913:) Olfactory receptor 13H1; (3914:) Olfactory receptor 13J1; (3915:) Olfactory receptor 1A1 (Olfactory receptor 17-7) (OR17-7) (Olfactory receptor OR17-11); (3916:) Olfactory receptor 1A2 (Olfactory receptor 17-6) (OR17-6) (Olfactory receptor OR17-10); (3917:) Olfactory receptor 1B1 (Olfactory receptor 9-B) (OR9-B) (Olfactory receptor OR9-26); (3918:) Olfactory receptor 1C1 (Olfactory receptor TPCR27) (Olfactory receptor OR1-42); (3919:) Olfactory receptor 1D2 (Olfactory receptor-like protein HGMP07E) (Olfactory receptor 17-4) (OR17-4); (3920:) Olfactory receptor 1D4 (Olfactory receptor 17-30) (OR17-30); (3921:) Olfactory receptor 1D5 (Olfactory receptor 17-31) (OR17-31); (3922:) Olfactory receptor 1E1 (Olfactory receptor-like protein HGMP07I) (Olfactory receptor 17-2/17-32) (OR17-2) (OR17-32) (Olfactory receptor 13-66) (OR13-66) (Olfactory receptor 5-85) (OR5-85); (3923:) Olfactory receptor 1E2 (Olfactory receptor 17-93/17-135/17-136) (OR17-93) (OR17-135) (OR17-136); (3924:) Olfactory receptor 1F1 (Olfactory receptor 16-35) (OR16-35) (Olfactory receptor OR16-4); (3925:) Olfactory receptor 1F10 (Olfactory receptor 3-145) (OR3-145); (3926:) Olfactory receptor 1F12 (Hs6M1-35P); (3927:) Olfactory receptor 1F2 (OLFmf2); (3928:) Olfactory receptor 1G1 (Olfactory receptor 17-209) (OR17-209); (3929:) Olfactory receptor 1I1 (Olfactory receptor 19-20) (OR19-20); (3930:) Olfactory receptor 1J1 (Olfactory receptor OR9-18); (3931:) Olfactory receptor 1J2 (OST044) (HSA5) (HTPCRX15) (Olfactory receptor OR9-19); (3932:) Olfactory receptor 1J4 (HTPCRX01) (Olfactory receptor OR9-21); (3933:) Olfactory receptor 1K1; (3934:) Olfactory receptor 1L1 (Olfactory receptor 9-C) (OR9-C); (3935:) Olfactory receptor 1L3 (Olfactory receptor 9-D) (OR9-D) (Olfactory receptor OR9-28); (3936:) Olfactory receptor 1L4 (Olfactory receptor 9-E) (OR9-E) (OST046); (3937:) Olfactory receptor 1L6; (3938:) Olfactory receptor 1L8 (Olfactory receptor OR9-24); (3939:) Olfactory receptor 1M1 (Olfactory receptor 19-6) (OR19-6); (3940:) Olfactory receptor 1N1 (Olfactory receptor 1-26) (OR1-26) (Olfactory receptor 1N3) (Olfactory receptor OR9-22); (3941:) Olfactory receptor 1N2; (3942:) Olfactory receptor 1Q1 (Olfactory receptor TPCR106) (Olfactory receptor 9-A) (OR9-A) (OST226) (Olfactory receptor OR9-25); (3943:) Olfactory receptor 1S1; (3944:) Olfactory receptor 1S2; (3945:) Olfactory receptor 2A12; (3946:) Olfactory receptor 2A14 (OST182); (3947:) Olfactory receptor 2A2 (Olfactory receptor OR7-11); (3948:) Olfactory receptor 2A4 (Olfactory receptor OR6-37); (3949:) Olfactory receptor 2A42; (3950:) Olfactory receptor 2A5 (Olfactory receptor 7-138/7-141) (OR7-138) (OR7-141); (3951:) Olfactory receptor 2A7; (3952:) Olfactory receptor 2AE1; (3953:) Olfactory receptor 2AG1 (HT3); (3954:) Olfactory receptor 2AJ1; (3955:) Olfactory receptor 2AK2 (Olfactory receptor OR1-47); (3956:) Olfactory receptor 2AP1 (Olfactory receptor OR12-9); (3957:) Olfactory receptor 2B11; (3958:) Olfactory receptor 2B2 (Olfactory receptor 6-1) (OR6-1) (Hs6M1-10); (3959:) Olfactory receptor 2B3 (Olfactory receptor 6-4) (OR6-4) (Olfactory receptor OR6-14) (Hs6M1-1); (3960:) Olfactory receptor 2B6 (Olfactory receptor 6-31) (OR6-31) (Olfactory receptor 5-40) (OR5-40) (Hs6M1-32); (3961:) Olfactory receptor 2B8 (Hs6M1-29P); (3962:) Olfactory receptor 2C1 (OLFmf3); (3963:) Olfactory receptor 2C3; (3964:) Olfactory receptor 2D2 (Olfactory receptor 11-610) (OR11-610) (HB2) (Olfactory receptor OR11-88); (3965:) Olfactory receptor 2D3; (3966:) Olfactory receptor 2F1 (Olfactory receptor-like protein OLF3); (3967:) Olfactory receptor 2F2 (Olfactory receptor 7-1) (OR7-1) (Olfactory receptor OR7-6); (3968:) Olfactory receptor 2G2 (Olfactory receptor OR1-32); (3969:) Olfactory receptor 2G3 (Olfactory receptor OR1-33); (3970:) Olfactory receptor 2G6; (3971:) Olfactory receptor 2H1 (Hs6M1-16) (Olfactory receptor 6-2) (OR6-2) (OLFR42A-9004.14/9026.2); (3972:) Olfactory receptor 2H2 (Hs6M1-12) (Olfactory receptor-like protein FAT11); (3973:) Olfactory receptor 2H7 (OLFR42B-9079.6); (3974:) Olfactory receptor 2I1; (3975:) Olfactory receptor 2J1 (Olfactory receptor 6-5) (OR6-5) (Hs6M1-4); (3976:) Olfactory receptor 2J2 (Olfactory receptor 6-8) (OR6-8) (Hs6M1-6); (3977:) Olfactory receptor 2J3 (Olfactory receptor 6-6) (OR6-6) (Hs6M1-3); (3978:) Olfactory receptor 2K2 (HTPCRH06); (3979:) Olfactory receptor 2L13; (3980:) Olfactory receptor 2L2 (HTPCRH07); (3981:) Olfactory receptor 2L3; (3982:) Olfactory receptor 2L5 (Olfactory receptor OR1-53); (3983:) Olfactory receptor 2L8 (Olfactory receptor OR1-46); (3984:) Olfactory receptor 2M1 (Olfactory receptor-like protein JCG10) (OST037); (3985:) Olfactory receptor 2M2 (OST423); (3986:) Olfactory receptor 2M3 (Olfactory receptor OR1-54); (3987:) Olfactory receptor 2M4 (Olfactory receptor TPCR100) (OST710) (HTPCRX18) (Olfactory receptor OR1-55); (3988:) Olfactory receptor 2M7 (Olfactory receptor OR1-58); (3989:) Olfactory receptor 2S2 (Olfactory receptor OR9-3); (3990:) Olfactory receptor 2T1 (Olfactory receptor 1-25) (OR1-25) (Olfactory receptor OR1-61); (3991:) Olfactory receptor 2T10 (Olfactory receptor OR1-64); (3992:) Olfactory receptor 2T11 (Olfactory receptor OR1-65); (3993:) Olfactory receptor 2T12 (Olfactory receptor OR1-57); (3994:) Olfactory receptor 2T2 (Olfactory receptor OR1-43); (3995:) Olfactory receptor 2T27 (Olfactory receptor OR1-67); (3996:) Olfactory receptor 2T29; (3997:) Olfactory receptor 2T3; (3998:) Olfactory receptor 2T33 (Olfactory receptor OR1-56); (3999:) Olfactory receptor 2T34 (Olfactory receptor OR1-63); (4000:) Olfactory receptor 2T35 (Olfactory receptor OR1-66); (4001:) Olfactory receptor 2T4 (Olfactory receptor OR1-60); (4002:) Olfactory receptor 2T5 (Olfactory receptor OR1-62); (4003:) Olfactory receptor 2T6 (OST703); (4004:) Olfactory receptor 2V2 (Olfactory receptor OR5-3); (4005:) Olfactory receptor 2W1 (Hs6M1-15); (4006:) Olfactory receptor 2W3 (Olfactory receptor OR1-49); (4007:) Olfactory receptor 2Y1 (Olfactory receptor OR5-2); (4008:) Olfactory receptor 2Z1 (Olfactory receptor OR19-4); (4009:) Olfactory receptor 3A1 (Olfactory receptor 17-40) (OR17-40); (4010:) Olfactory receptor 3A2 (Olfactory receptor 17-228) (OR17-228); (4011:) Olfactory receptor 3A3 (Olfactory receptor 17-201) (OR17-201); (4012:) Olfactory receptor 3A4 (Olfactory receptor 17-24) (OR17-24); (4013:) Olfactory receptor 4A15 (Olfactory receptor OR11-118); (4014:) Olfactory receptor 4A16 (Olfactory receptor OR11-117); (4015:) Olfactory receptor 4A4 (Olfactory receptor OR11-107); (4016:) Olfactory receptor 4A47 (Olfactory receptor OR11-113); (4017:) Olfactory receptor 4A5 (Olfactory receptor OR11-111); (4018:) Olfactory receptor 4B1 (OST208) (Olfactory receptor OR11-106); (4019:) Olfactory receptor 4C11 (Olfactory receptor OR11-136); (4020:) Olfactory receptor 4C12 (Olfactory receptor OR11-259); (4021:) Olfactory receptor 4C13 (Olfactory receptor OR11-260); (4022:) Olfactory receptor 4C15 (Olfactory receptor OR11-127) (Olfactory receptor OR11-134); (4023:) Olfactory receptor 4C16 (Olfactory receptor OR11-135); (4024:) Olfactory receptor 4C3 (Olfactory receptor OR11-98); (4025:) Olfactory receptor 4C5 (Olfactory receptor OR11-99); (4026:) Olfactory receptor 4C6 (Olfactory receptor OR11-138); (4027:) Olfactory receptor 4D1 (Olfactory receptor TPCR16); (4028:) Olfactory receptor 4D10 (Olfactory receptor OR11-251); (4029:) Olfactory receptor 4D11; (4030:) Olfactory receptor 4D2 (Olfactory receptor OR17-24) (B-lymphocytemembrane protein BC2009); (4031:) Olfactory receptor 4D5 (Olfactory receptor OR11-276); (4032:) Olfactory receptor 4D6 (Olfactory receptor OR11-250); (4033:) Olfactory receptor 4D9 (Olfactory receptor OR11-253); (4034:) Olfactory receptor 4E2 (Olfactory receptor OR14-42); (4035:) Olfactory receptor 4F14; (4036:) Olfactory receptor 4F15; (4037:) Olfactory receptor 4F17; (4038:) Olfactory receptor 4F29 (Olfactory receptor OR1-1); (4039:) Olfactory receptor 4F3; (4040:) Olfactory receptor 4F4 (HS14a-1-A) (Olfactory receptor OR19-3); (4041:) Olfactory receptor 4F5; (4042:) Olfactory receptor 4F6; (4043:) Olfactory receptor 4H12; (4044:) Olfactory receptor 4K1; (4045:) Olfactory receptor 4K13 (Olfactory receptor OR14-27); (4046:) Olfactory receptor 4K14 (Olfactory receptor OR14-22); (4047:) Olfactory receptor 4K15; (4048:) Olfactory receptor 4K17; (4049:) Olfactory receptor 4K2; (4050:) Olfactory receptor 4K3; (4051:) Olfactory receptor 4K5; (4052:) Olfactory receptor 4L1 (Olfactory receptor OR14-28); (4053:) Olfactory receptor 4M1; (4054:) Olfactory receptor 4M2; (4055:) Olfactory receptor 4N2 (Olfactory receptor OR14-8); (4056:) Olfactory receptor 4N4; (4057:) Olfactory receptor 4N5 (Olfactory receptor OR14-33); (4058:) Olfactory receptor 4P4; (4059:) Olfactory receptor 4Q3 (Olfactory receptor OR14-3); (4060:) Olfactory receptor 4S1; (4061:) Olfactory receptor 4S2; (4062:) Olfactory receptor 4X1; (4063:) Olfactory receptor 4X2; (4064:) Olfactory receptor 51A2; (4065:) Olfactory receptor 51A4; (4066:) Olfactory receptor 51A7; (4067:) Olfactory receptor 51B2 (Odorant receptor HOR5'beta3); (4068:) Olfactory receptor 51B4 (Odorant receptor HOR5'beta1); (4069:) Olfactory receptor 51B5 (Odorant receptor HOR5'beta5) (Olfactory receptor OR11-37); (4070:) Olfactory receptor 51B5 (Odorant receptor HOR5'beta6); (4071:) Olfactory receptor 51D1 (Olfactory receptor OR11-14); (4072:) Olfactory receptor 51E1; (4073:) Olfactory receptor 51E2 (Prostate-specific G-protein coupled receptor) (HPRAJ); (4074:) Olfactory receptor 51F2; (4075:) Olfactory receptor 51G1; (4076:) Olfactory receptor 51G2; (4077:) Olfactory receptor 51H1; (4078:) Olfactory receptor 51I1 (Odorant receptor HOR5'beta11) (Olfactory receptor OR11-39); (4079:) Olfactory receptor 51I2 (Odorant receptor HOR5'beta12) (Olfactory receptor OR11-38); (4080:) Olfactory receptor 51L1; (4081:) Olfactory receptor 51M1 (Odorant receptor HOR5'beta7) (Olfactory receptor OR11-40); (4082:) Olfactory receptor 51Q1; (4083:) Olfactory receptor 51S1; (4084:) Olfactory receptor 51T1; (4085:) Olfactory receptor 51V1 (Odorant receptor HOR3'beta1) (Olfactory receptor OR11-36); (4086:) Olfactory receptor 52A1 (HPFH1OR) (Odorant receptor HOR3'beta4); (4087:) Olfactory receptor 52A5 (Odorant receptor HOR3'beta5) (Olfactory receptor OR11-33); (4088:) Olfactory receptor 52B2; (4089:) Olfactory receptor 52B4 (Olfactory receptor OR11-3); (4090:) Olfactory receptor 52B6; (4091:) Olfactory receptor 52D1 (Odorant receptor HOR5'beta14) (Olfactory receptor OR11-43); (4092:) Olfactory receptor 52E1; (4093:) Olfactory receptor 52E2; (4094:) Olfactory receptor 52E4; (4095:) Olfactory receptor 52E5; (4096:) Olfactory receptor 52E6; (4097:) Olfactory receptor 52E8 (Olfactory receptor OR11-54); (4098:) Olfactory receptor 52H1; (4099:) Olfactory receptor 52I1; (4100:) Olfactory receptor 52I2; (4101:) Olfactory receptor 52J2; (4102:) Olfactory receptor 52K1; (4103:) Olfactory receptor 52K2; (4104:) Olfactory receptor 52L1; (4105:) Olfactory receptor 52L2; (4106:) Olfactory receptor 52M1 (Olfactory receptor OR11-11); (4107:) Olfactory receptor 52N1; (4108:) Olfactory receptor 52N2; (4109:) Olfactory receptor 52N4; (4110:) Olfactory receptor 52N5; (4111:) Olfactory receptor 52P1; (4112:) Olfactory receptor 52R1; (4113:) Olfactory receptor 52W1 (Olfactory receptor OR11-71); (4114:) Olfactory receptor 56A1; (4115:) Olfactory receptor 56A3; (4116:) Olfactory receptor 56A4; (4117:) Olfactory receptor 56B1 (Olfactory receptor OR11-65); (4118:) Olfactory receptor 56B2; (4119:) Olfactory receptor 56B4; (4120:) Olfactory receptor 5A1 (OST181); (4121:) Olfactory receptor 5A2; (4122:) Olfactory receptor 5AC2 (HSA1); (4123:) Olfactory receptor 5AK2; (4124:) Olfactory receptor 5AK3; (4125:) Olfactory receptor 5AN1 (Olfactory receptor OR11-244); (4126:) Olfactory receptor 5AP2; (4127:) Olfactory receptor 5AR1; (4128:) Olfactory receptor 5AS1; (4129:) Olfactory receptor 5AT1; (4130:) Olfactory receptor 5AU1; (4131:) Olfactory receptor 5AV1; (4132:) Olfactory receptor 5AY1; (4133:) Olfactory receptor 5B12 (Olfactory receptor OR11-241); (4134:) Olfactory receptor 5B17 (Olfactory receptor OR11-237); (4135:) Olfactory receptor 5B2 (OST073) (Olfactory receptor OR11-240); (4136:) Olfactory receptor 5B3 (Olfactory receptor OR11-239); (4137:) Olfactory receptor 5BF1; (4138:) Olfactory receptor 5C1 (Olfactory receptor 9-F) (OR9-F); (4139:) Olfactory receptor 5D13; (4140:) Olfactory receptor 5D14; (4141:) Olfactory receptor 5D16; (4142:) Olfactory receptor 5D18; (4143:) Olfactory receptor 5F1 (Olfactory receptor 11-10) (OR11-10); (4144:) Olfactory receptor 5H2; (4145:) Olfactory receptor 5H6; (4146:) Olfactory receptor 5I1 (Olfactory receptor-like protein OLF1) (Olfactory receptor OR11-159); (4147:) Olfactory receptor 5J2 (Olfactory receptor OR11-266); (4148:) Olfactory receptor 5K1 (HTPCRX10); (4149:) Olfactory receptor 5K2 (Olfactory receptor OR3-9); (4150:) Olfactory receptor 5L1 (OST262); (4151:) Olfactory receptor 5L2 (HTPCRX16); (4152:) Olfactory receptor 5M1 (OST050); (4153:) Olfactory receptor 5M10 (Olfactory receptor OR11-207); (4154:) Olfactory receptor 5M11; (4155:) Olfactory receptor 5M3 (Olfactory receptor OR11-191); (4156:) Olfactory receptor 5M8 (Olfactory receptor OR11-194); (4157:) Olfactory receptor 5M9 (Olfactory receptor OR11-190); (4158:) Olfactory receptor 5P2 (Olfactory receptor-like protein JCG3); (4159:) Olfactory receptor 5P3 (Olfactory receptor-like protein JCG1); (4160:) Olfactory receptor 5R1 (Olfactory receptor OR11-185); (4161:) Olfactory receptor 5T1 (Olfactory receptor OR11-179); (4162:) Olfactory receptor 5T2; (4163:) Olfactory receptor 5T3; (4164:) Olfactory receptor 5U1 (Olfactory receptor OR6-25) (Hs6M1-28); (4165:) Olfactory receptor 5V1 (Hs6M1-21); (4166:) Olfactory receptor 5W2 (Olfactory receptor OR11-155); (4167:) Olfactory receptor 6A2 (Olfactory receptor 11-55) (OR11-55) (hP2olfactory receptor); (4168:) Olfactory receptor 6B1 (Olfactory receptor 7-3) (OR7-3); (4169:) Olfactory receptor 6B2 (Olfactory receptor OR2-1); (4170:) Olfactory receptor 6B3 (Olfactory receptor OR2-2); (4171:) Olfactory receptor 6C1 (OST267); (4172:) Olfactory receptor 6C2 (HSA3); (4173:) Olfactory receptor 6C3 (HSA8); (4174:) Olfactory receptor 6C4; (4175:) Olfactory receptor 6F1 (Olfactory receptor OR1-38); (4176:) Olfactory receptor 6J1; (4177:) Olfactory receptor 6K2; (4178:) Olfactory receptor 6K3; (4179:) Olfactory receptor 6K6; (4180:) Olfactory receptor 6M1 (Olfactory receptor OR11-271); (4181:) Olfactory receptor 6N1; (4182:) Olfactory receptor 6N2; (4183:) Olfactory receptor 6P1 (Olfactory receptor OR1-12); (4184:) Olfactory receptor 6Q1; (4185:) Olfactory receptor 6S1; (4186:) Olfactory receptor 6T1; (4187:) Olfactory receptor 6V1; (4188:) Olfactory receptor 6W1 (Olfactory receptor sdolf); (4189:) Olfactory receptor 6X1 (Olfactory receptor OR11-270); (4190:) Olfactory receptor 6Y1 (Olfactory receptor OR1-11); (4191:) Olfactory receptor 7A10 (OST027) (Olfactory receptor OR19-18); (4192:) Olfactory receptor 7A17; (4193:) Olfactory receptor 7A2; (4194:) Olfactory receptor 7A5 (Olfactory receptor TPCR92); (4195:) Olfactory receptor 7C1 (Olfactory receptor TPCR86); (4196:) Olfactory receptor 7C2 (Olfactory receptor 19-18) (OR19-18); (4197:) Olfactory receptor 7D2 (Olfactory receptor 19-4) (OR19-4) (HTPCRH03); (4198:) Olfactory receptor 7D4 (Olfactory receptor OR19-7); (4199:) Olfactory receptor 7G1 (Olfactory receptor 19-15) (OR19-15); (4200:) Olfactory receptor 7G2 (Olfactory receptor 19-13) (OR19-13) (OST260); (4201:) Olfactory receptor 7G3 (OST085); (4202:) Olfactory receptor 8A1 (OST025); (4203:) Olfactory receptor 8B12 (Olfactory receptor OR11-317); (4204:) Olfactory receptor 8B2; (4205:) Olfactory receptor 8B3; (4206:) Olfactory receptor 8B4; (4207:) Olfactory receptor 8B8 (Olfactory receptor TPCR85) (Olfactory-like receptor JCG8); (4208:) Olfactory receptor 8D1 (Olfactory receptor-like protein JCG9) (OST004) (Olfactory receptor OR11-301); (4209:) Olfactory receptor 8D2 (Olfactory receptor-like protein JCG2); (4210:) Olfactory receptor 8D4; (4211:) Olfactory receptor 8G1 (Olfactory receptor TPCR25) (Olfactory receptor OR11-281); (4212:) Olfactory receptor 8G2 (Olfactory receptor TPCR120) (Olfactory receptor OR11-297); (4213:) Olfactory receptor 8G5 (Olfactory receptor OR11-298); (4214:) Olfactory receptor 8H1; (4215:) Olfactory receptor 8H2; (4216:) Olfactory receptor 8H3; (4217:) Olfactory receptor 8I2; (4218:) Olfactory receptor 8J1; (4219:) Olfactory receptor 8J3; (4220:) Olfactory receptor 8K1; (4221:) Olfactory receptor 8K3; (4222:) Olfactory receptor 8K5; (4223:) Olfactory receptor 8S1; (4224:) Olfactory receptor 8U1; (4225:) Olfactory receptor 9A2; (4226:) Olfactory receptor 9A4; (4227:) Olfactory receptor 9G1; (4228:) Olfactory receptor 9G4; (4229:) Olfactory receptor 9G5 (Olfactory receptor OR11-114); (4230:) Olfactory receptor 9I1; (4231:) Olfactory receptor 9K2; (4232:) Olfactory receptor 9Q1; (4233:) Olfactory receptor 9Q2; (4234:) olfactory receptor, family 4, subfamily F, member 6 [*Homo sapiens*]; (4235:) oligoadenylate synthetase; (4236:) O-linked GlcNAc transferase isoform 1 [*Homo sapiens*]; (4237:) O-linked GlcNAc transferase isoform 2 [*Homo sapiens*]; (4238:) Oncomodulin (OM) (Parvalbumin beta); (4239:) Opa-interacting protein OIP3 [*Homo sapiens*]; (4240:) Opioid Growth Factor Receptor (OGFr); (4241:) Opioid growth factor receptor (OGFr) (Zeta-type opioid receptor) (7-60 protein); (4242:) Opioid Receptor; (4243:) opioid receptor, mu 1 isoform MOR-1 [*Homo sapiens*]; (4244:) opioid receptor, mu 1 isoform MOR-1A [*Homo sapiens*]; (4245:) opioid receptor, mu 1 isoform MOR-10 [*Homo sapiens*]; (4246:) opioid receptor, mu 1 isoform MOR-1X [*Homo sapiens*]; (4247:) Opioid Receptor-Like1 (ORL1) Receptor; (4248:) Opsin-3 (Encephalopsin) (Panopsin); (4249:) Opsin-5 (Neuropsin) (G-protein coupled receptor 136) (G-protein coupled receptor PGR12) (Transmembrane protein 13); (4250:) Orexigenic neuropeptide QRFP receptor (G-protein coupled receptor103) (SP9155) (AQ27); (4251:) Orexin Receptor; (4252:) Orexin receptor type 1 (Ox1r) (Hypocretin receptor type 1); (4253:) Orexin receptor type 2 (Ox2r) (Hypocretin receptor type 2); (4254:) Organic Anion Transporter 3 (OAT3); (4255:) Organic cation/carnitine transporter 1 (Solute carrier family 22member 4) (Ergothioneine transporter) (ET transporter); (4256:) ornithine aminotransferase precursor [*Homo sapiens*]; (4257:) ornithine carbamoyltransferase precursor [*Homo sapiens*]; (4258:) Ornithine carbamoyltransferase, mitochondrial precursor (OTCase) (Ornithine transcarbamylase); (4259:) Ornithine Decarboxylase; (4260:) ornithine decarboxylase 1 [*Homo sapiens*]; (4261:) ornithine decarboxylase-like protein [*Homo sapiens*]; (4262:) Orphan nuclear receptor EAR-2 (V-erbA-related protein EAR-2); (4263:) Orphan nuclear receptor NR1D1 (V-erbA-related protein EAR-1) (Rev-erbA-alpha); (4264:) Orphan nuclear receptor NR1D2 (Rev-erb-beta) (EAR-1R) (Orphannuclear hormone receptor BD73); (4265:) Orphan nuclear receptor NR1I3 (Constitutive androstane receptor) (CAR) (Constitutive activator of retinoid response) (Constitutive active response) (Orphan nuclear receptor MB67); (4266:) Orphan nuclear receptor NR2E1 (Nuclear receptor TLX) (Tailless-homolog) (TII) (hTII); (4267:) Orphan nuclear receptor NR4A1 (Orphan nuclear receptor HMR) (Early response protein NAK1) (TR3 orphan receptor) (ST-59); (4268:) Orphan nuclear receptor NR4A2 (Orphan nuclear receptor NURR1) (Immediate-early response protein NOT) (Transcriptionally-inducible nuclear receptor); (4269:) Orphan nuclear receptor NR4A3 (Nuclear hormone receptor NOR-1) (Neuron-derived orphan receptor 1) (Mitogen-induced nuclear orphan receptor); (4270:) Orphan nuclear receptor NR5A2 (Alpha-1-fetoprotein transcription factor) (Hepatocytic transcription factor) (B1-binding factor) (hB1F) (CYP7A promoter-binding factor) (Liver receptor homolog 1) (LRH-1); (4271:) Orphan nuclear receptor NR6A1 (Germ cell nuclear factor) (GCNF) (Retinoid receptor-related testis-specific receptor) (RTR); (4272:) Orphan nuclear receptor PXR (Pregnane X receptor) (Orphan nuclear receptor PAR1) (Steroid and xenobiotic receptor) (SXR); (4273:) orphan nuclear receptor steroidogenic factor 1, SF-1 (long terminal repeat-binding protein, ELP) [human, Peptide, 205 aa]; (4274:) Orphan nuclear receptor TR2 (Testicular receptor 2); (4275:) Orphan nuclear receptor TR4 (Orphan nuclear receptor TAK1); (4276:) orphan UDP-glucuronosyltransferase (EC 2.4.-.-)—human; (4277:) OTU domain-containing protein 7B (Zinc finger protein Cezanne) (Zinc finger A20 domain-containing protein 1) (Cellular zinc finger anti-NF-kappa B protein); (4278:) oxidised low density lipoprotein (lectin-like) receptor 1 [*Homo sapiens*]; (4279:) Oxidized low-density lipoprotein receptor 1 (Ox-LDL receptor 1) (Lectin-type oxidized LDL receptor 1) (Lectin-like oxidized LDL receptor 1) (Lectin-like oxLDL receptor 1) (LOX-1) (hLOX-1)[Contains:) Oxidized low-density lipoprotein receptor 1, soluble form]; (4280:) Oxidosqualene Cyclase (OSC); (4281:) Oxoeicosanoid receptor 1 (G-protein coupled receptor TG1019) (5-oxo-ETE G-protein coupled receptor) (G-protein coupled receptor170) (G-protein coupled receptor R527); (4282:) Oxysterols receptor LXR-alpha (Liver X receptor alpha) (Nuclearorphan receptor LXR-alpha); (4283:) Oxysterols receptor LXR-beta (Liver X receptor beta) (Nuclearorphan receptor LXR-beta) (Ubiquitously-expressed nuclear receptor) (Nuclear receptor NER); (4284:) Oxytocin Receptor (OTR); (4285:) oxytocin-neurophysin I preproprotein [*Homo sapiens*]; (4286:) P/Q-Type Calcium Channel Blocker; (4287:) p136 [*Homo sapiens*]; (4288:) P2 purinergic Receptor; (4289:) p21-activated kinase 2 [*Homo sapiens*]; (4290:) P2X purinoceptor 1 (ATP receptor) (P2X1) (Purinergic receptor); (4291:) P2X purinoceptor 2 (ATP receptor) (P2X2) (Purinergic receptor); (4292:) P2X purinoceptor 3 (ATP receptor) (P2X3) (Purinergic receptor); (4293:) P2X purinoceptor 4 (ATP receptor) (P2X4) (Purinergic receptor); (4294:) P2X purinoceptor 5 (ATP receptor) (P2X5) (Purinergic receptor);

(4295:) P2X purinoceptor 6 (ATP receptor) (P2X6) (Purinergic receptor) (P2XM) (Purinergic receptor P2X-like 1); (4296:) P2X purinoceptor 7 (ATP receptor) (P2X7) (Purinergic receptor) (P2Z receptor); (4297:) P2X3 Purinergic Receptor; (4298:) P2X7 Purinergic Receptor; (4299:) P2Y purinoceptor 1 (ATP receptor) (P2Y1) (Purinergic receptor); (4300:) P2Y purinoceptor 11 (P2Y11); (4301:) P2Y purinoceptor 12 (P2Y12) (P2Y12 platelet ADP receptor) (P2Y (ADP)) (ADP-glucose receptor) (ADPG-R) (P2Y(AC)) (P2Y(cyc)) (P2T(AC)) (SP1999); (4302:) P2Y purinoceptor 13 (P2Y13) (G-protein coupled receptor 86) (G-protein coupled receptor 94); (4303:) P2Y purinoceptor 14 (P2Y14) (UDP-glucose receptor) (G-protein coupled receptor 105); (4304:) P2Y purinoceptor 2 (P2Y2) (P2U purinoceptor 1) (P2U1) (ATP receptor) (Purinergic receptor); (4305:) P2Y purinoceptor 4 (P2Y4) (Uridine nucleotide receptor) (UNR) (P2P); (4306:) P2Y purinoceptor 5 (P2Y5) (Purinergic receptor 5) (RB intron encoded G-protein coupled receptor); (4307:) P2Y purinoceptor 6 (P2Y6); (4308:) P2Y purinoceptor 8 (P2Y8); (4309:) P2Y12 Purinergic Receptor; (4310:) P2Y2 Purinergic Receptor; (4311:) p300/CBP-associated factor [*Homo sapiens*]; (4312:) p38 Mitogen-Activated Protein (MAP) Kinase; (4313:) p38 mitogen-activated protein (MAP) kinase activator; (4314:) p53 Activator; (4315:) p65 Protein; (4316:) p70 Ribosomal Protein S6 Kinase (S6K); (4317:) p85 beta subunit of phosphatidyl-inositol-3-kinase [*Homo sapiens*]; (4318:) Paired Box Gene 4 (Pax4) Functional; (4319:) Paired immunoglobulin-like type 2 receptor alpha precursor (Inhibitory receptor PILR-alpha) (Cell surface receptor FDF03); (4320:) Paired immunoglobulin-like type 2 receptor beta precursor (Activating receptor PILR-beta) (Cell surface receptor FDFACT); (4321:) palmitoyl-protein thioesterase [*Homo sapiens*]; (4322:) palmitoyl-protein thioesterase 1 (ceroid-lipofuscinosis, neuronal1, infantile) [*Homo sapiens*]; (4323:) Palmitoyl-protein thioesterase 1 precursor (PPT-1) (Palmitoyl-protein hydrolase 1); (4324:) PAN2 [*Homo sapiens*]; (4325:) pancreas-enriched phospholipase C [*Homo sapiens*]; (4326:) pancreatic ribonuclease precursor [*Homo sapiens*]; (4327:) Pantothenate kinase 1 (Pantothenic acid kinase 1) (hPanK1) (hPanK); (4328:) pantothenate kinase 1 isoform alpha [*Homo sapiens*]; (4329:) pantothenate kinase 1 isoform beta [*Homo sapiens*]; (4330:) pantothenate kinase 1 isoform gamma [*Homo sapiens*]; (4331:) pantothenate kinase 2 isoform 1 preproprotein [*Homo sapiens*]; (4332:) pantothenate kinase 2 isoform 2 [*Homo sapiens*]; (4333:) Pantothenate kinase 2, mitochondrial precursor (Pantothenic acid kinase 2) (hPANK2); (4334:) Pantothenate kinase 3 (Pantothenic acid kinase 3) (hPanK3); (4335:) pantothenate kinase 3 [*Homo sapiens*]; (4336:) Pantothenate kinase 4 (Pantothenic acid kinase 4) (hPanK4); (4337:) pantothenate kinase 4 [*Homo sapiens*]; (4338:) Pappalysin-1 precursor (Pregnancy-associated plasma protein-A) (PAPP-A) (Insulin-like growth factor-dependent IGF-binding protein4 protease) (IGF-dependent IGFBP-4 protease) (IGFBP-4-ase); (4339:) PAPSS1 protein [*Homo sapiens*]; (4340:) paraoxanase-3 [*Homo sapiens*]; (4341:) paraoxonase 1 [*Homo sapiens*]; (4342:) paraoxonase 2 isoform 1 [*Homo sapiens*]; (4343:) paraoxonase 2 isoform 2 [*Homo sapiens*]; (4344:) paraoxonase 3 [*Homo sapiens*]; (4345:) Parathyroid Hormone (PTH); (4346:) Parathyroid hormone receptor precursor (PTH2 receptor); (4347:) Parathyroid hormone/parathyroid hormone-related peptide receptor precursor (PTH/PTHr receptor) (PTH/PTHrP type I receptor); (4348:) parkin isoform 1 [*Homo sapiens*]; (4349:) parkin isoform 2 [*Homo sapiens*]; (4350:) parkin isoform 3 [*Homo sapiens*]; (4351:) PAS domain-containing serine/threonine-protein kinase (PAS-kinase) (PASKIN) (hPASK); (4352:) patatin-like phospholipase domain containing 1 isoform 2 [*Homo sapiens*]; (4353:) patatin-like phospholipase domain containing 1 [*Homo sapiens*]; (4354:) PC Cell-Derived Growth Factor (PCDGF); (4355:) PC1/PC3 [*Homo sapiens*]; (4356:) PC8 precursor; (4357:) PCBD [*Homo sapiens*]; (4358:) PCK1 [*Homo sapiens*]; (4359:) PCK2 [*Homo sapiens*]; (4360:) PCTAIRE protein kinase 1 [*Homo sapiens*]; (4361:) PDC-E2 precursor (AA −54 to 561) [*Homo sapiens*]; (4362:) Pepsin; (4363:) Peptide Deformylase (PDF); (4364:) Peptide methionine sulfoxide reductase (Protein-methionine-S-oxidereductase) (PMSR) (Peptide Met(O) reductase); (4365:) Peptide-N(4)-(N-acetyl-beta-glucosaminyl)asparagine amidase(PNGase) (hPNGase) (Peptide:N-glycanase) (N-glycanase 1); (4366:) peptidyl arginine deiminase, type IV [*Homo sapiens*]; (4367:) peptidyl dipeptidase I [*Homo sapiens*]; (4368:) peptidylarginine deiminase type III [*Homo sapiens*]; (4369:) peptidylglycine alpha-amidating monooxygenase COOH-terminal interactor [*Homo sapiens*]; (4370:) peptidylglycine alpha-amidating monooxygenase isoform a, preproprotein [*Homo sapiens*]; (4371:) peptidylglycine alpha-amidating monooxygenase isoform b, preproprotein [*Homo sapiens*]; (4372:) peptidylglycine alpha-amidating monooxygenase isoform c,preproprotein [*Homo sapiens*]; (4373:) peptidylglycine alpha-amidating monooxygenase isoform d, preproprotein [*Homo sapiens*]; (4374:) "Peptidyl-glycine alpha-amidating monooxygenase precursor (PAM) [Includes] Peptidylglycine alpha-hydroxylating monooxygenase (PHM); Peptidyl-alpha-hydroxyglycine alpha-amidating lyase(Peptidylamidoglycolate lyase) (PAL)]."; (4375:) Peptidylprolyl Cis-Trans Isomerase (PPlase); (4376:) Peptidyl-prolyl cis-trans isomerase A (PPlase A) (Rotamase A) (Cyclophilin A) (Cyclosporin A-binding protein); (4377:) Peptidyl-prolyl cis-trans isomerase B precursor (PPlase) (Rotamase) (Cyclophilin B) (S-cyclophilin) (SCYLP) (CYP-S1); (4378:) Peptidyl-prolyl cis-trans isomerase C(PPlase) (Rotamase) (Cyclophilin C); (4379:) Peptidyl-prolyl cis-trans isomerase G (Peptidyl-prolyl isomerase G) (PPlase G) (Rotamase G) (Cyclophilin G) (Clk-associating RS-cyclophilin) (CARS-cyclophilin) (CARS-Cyp) (SR-cyclophilin) (SRcyp) (SR-cyp) (CASP10); (4380:) Peptidyl-prolyl cis-trans isomerase-like 1 (PPlase) (Rotamase); (4381:) peptidylprolyl isomerase A [*Homo sapiens*]; (4382:) Peptidyl-tRNA hydrolase 2, mitochondrial precursor (PTH 2) (Bcl-2 inhibitor of transcription 1); (4383:) Peripheral Chemoreceptor; (4384:) Peripheral-type benzodiazepine receptor (PBR) (PKBS) (Mitochondrialbenzodiazepine receptor); (4385:) peroxiredoxin 2 isoform a [*Homo sapiens*]; (4386:) peroxiredoxin 2 isoform c [*Homo sapiens*]; (4387:) peroxiredoxin 5 precursor, isoform a [*Homo sapiens*]; (4388:) peroxiredoxin 5 precursor, isoform b [*Homo sapiens*]; (4389:) peroxiredoxin 5 precursor, isoform c [*Homo sapiens*]; (4390:) peroxiredoxin 6 [*Homo sapiens*]; (4391:) Peroxiredoxin-1 (Thioredoxin peroxidase 2) (Thioredoxin-dependent peroxide reductase 2) (Proliferation-associated protein PAG) (Natural killer cell-enhancing factor A) (NKEF-A); (4392:) Peroxiredoxin-2 (Thioredoxin peroxidase 1) (Thioredoxin-dependentperoxide reductase 1) (Thiol-specific antioxidant protein) (TSA) (PRP) (Natural killer cell-enhancing factor B) (NKEF-B); (4393:) Peroxiredoxin-4 (Prx-IV) (Thioredoxin peroxidase AO372) (Thioredoxin-dependent peroxide reductase AO372) (Antioxidantenzyme AOE372) (A0E37-2); (4394:) Peroxiredoxin-5, mitochondrial precursor (Prx-V) (Peroxisomalantioxidant enzyme) (PLP) (Thioredoxin reductase) (Thioredoxinperoxidase PMP20) (Antioxidant enzyme B166) (AOEB166) (TPx type VI) (Liver tissue 2D-page spot 71B) (Alu corepressor 1); (4395:) Peroxiredoxin-6 (Antioxidant protein 2) (1-Cys peroxiredoxin) (1-Cys PRX) (Acidic calcium-independent phospholipase A2) (aiPLA2) (Non-selenium glutathione peroxidase) (NSGPx) (24 kDa protein) (Liver 2D page spot 40) (Red blood cells page spot 12); (4396:) Peroxisomal 2,4-dienoyl-CoA reductase (2,4-dienoyl-CoA reductase 2) (pDCR); (4397:) peroxisomal acyl-CoA thioesterase 1 isoform a [Homo sapiens]; (4398:) peroxisomal acyl-CoA thioesterase 1 isoform c [Homo sapiens]; (4399:) "Peroxisomal bi-functional enzyme (PBE) (PBFE) [Includes:] Enoyl-CoAhydratase; 3,2-trans-enoyl-CoA isomerase; 3-hydroxyacyl-CoAdehydrogenase J."; (4400:) Peroxisomal coenzyme A diphosphatase NUDT7 (Nucleosidediphosphate-linked moiety X motif 7) (Nudix motif 7); (4401:) peroxisomal D3,D2-enoyl-CoA isomerase isoform 1 [Homo sapiens]; (4402:) peroxisomal D3,D2-enoyl-CoA isomerase isoform 2 [Homo sapiens]; (4403:) peroxisomal enoyl-coenzyme A hydratase-like protein [Homo sapiens]; (4404:) Peroxisomal multifunctional enzyme type 2 (MFE-2) (D-bi-functional protein) (DBP) (17-beta-hydroxysteroid dehydrogenase 4) (17-beta-HSD 4) (D-3-hydroxyacyl-CoA dehydratase) (3-alpha,7-alpha,12-alpha-trihydroxy-5-beta-cholest-24-enoyl-CoAhydratase) (3-hydroxyacyl-CoA dehydrogenase); (4405:) Peroxisomal NADH pyrophosphatase NUDT12 (Nucleosidediphosphate-linked moiety X motif 12) (Nudix motif 12); (4406:) Peroxisomal sarcosine oxidase (PSO) (L-pipecolate oxidase) (L-pipecolic acid oxidase); (4407:) Peroxisomal trans-2-enoyl-CoA reductase (TERP) (HPDHase) (pVI-ARL) (2,4-dienoyl-CoA reductase-related protein) (DCR-RP); (4408:) peroxisome proliferative activated receptor gamma isoform 1 [Homo sapiens]; (4409:) peroxisome proliferative activated receptor gamma isoform 2 [Homo sapiens]; (4410:) Peroxisome proliferator-activated receptor alpha (PPAR-alpha); (4411:) Peroxisome proliferator-activated receptor delta (PPAR-delta) (PPAR-beta) (Nuclear hormone receptor 1) (NUC1) (NUCI); (4412:) Peroxisome proliferator-activated receptor gamma (PPAR-gamma); (4413:) peroxisome proliferator-activated receptor gamma, coactivator 1 alpha [Homo sapiens]; (4414:) peroxisome proliferator-activated receptor gamma-2—human; (4415:) Peroxisome Proliferator-Activated Receptor-Alpha (PPAR-Alpha); (4416:) Peroxisome Proliferator-Activated Receptor-Delta (PPAR-Delta); (4417:) Peroxisome proliferator-activated receptor-gamma (PPAR-gamma) Partial; (4418:) PFKL protein [Homo sapiens]; (4419:) PFKM [Homo sapiens]; (4420:) PFKM protein [Homo sapiens]; (4421:) PFKP protein [Homo sapiens]; (4422:) PGK1 [Homo sapiens]; (4423:) P-Glycoprotein (P-gp); (4424:) PH domain leucine-rich repeat-containing protein phosphatase (PHdomain leucine-rich repeat protein phosphatase) (Pleckstrin homology domain-containing family E protein 1) (Suprachiasmatic nucleus circadian oscillatory protein) (hSCOP); (4425:) phenylalanine hydroxylase [Homo sapiens]; (4426:) phenylalanine hydroxylase-stimulating protein, pterin-4-alpha-carbinolamine dehydratase, PHS, PCD [human, liver, Peptide,103 aa]; (4427:) Phenylalanine-4-hydroxylase (PAH) (Phe-4-monooxygenase); (4428:) Phenylethanolamine N-methyltransferase (PNMTase) (Noradrenaline N-methyltransferase); (4429:) phenylethanolamine N-methyltransferase [Homo sapiens]; (4430:) phenylethanolamine N-methyltransferase; (4431:) phosphate cytidylyltransferase 1, choline, alpha isoform [Homo sapiens]; (4432:) phosphatidate cytidylyltransferase 1 [Homo sapiens]; (4433:) phosphatidate cytidylyltransferase 2 [Homo sapiens]; (4434:) phosphatidic acid phosphatase type 2 domain containing 2 [Homo sapiens]; (4435:) phosphatidic acid phosphatase type 2A isoform 1 [Homo sapiens]; (4436:) phosphatidic acid phosphatase type 2A isoform 2 [Homo sapiens]; (4437:) Phosphatidylcholine (PtdCho) Synthesis; (4438:) Phosphatidylcholine:ceramide cholinephosphotransferase I (Transmembrane protein 23) (Sphingomyelin synthase 1) (Mobprotein); (4439:) Phosphatidylcholine:ceramide cholinephosphotransferase 2(Sphingomyelin synthase 2); (4440:) Phosphatidylcholine-sterol acyltransferase precursor (Lecithin-cholesterol acyltransferase) (Phospholipid-cholesterolacyltransferase); (4441:) Phosphatidylethanolamine N-methyltransferase (PEAMT) (PEMT) (PEMT2); (4442:) phosphatidylethanolamine N-methyltransferase isoform 1 [Homo sapiens]; (4443:) phosphatidylethanolamine N-methyltransferase isoform 2 [Homo sapiens]; (4444:) Phosphatidylinositol 3-Kinase (PI3K); (4445:) Phosphatidylinositol 3-kinase catalytic subunit type 3(PtdIns-3-kinase type 3) (PI3-kinase type 3) (PI3K type 3) (Phosphoinositide-3-kinase class 3) (Phosphatidylinositol 3-kinasep100 subunit); (4446:) Phosphatidylinositol 3-kinase regulatory subunit beta (PI3-kinasep85-subunit beta) (PtdIns-3-kinase p85-beta); (4447:) Phosphatidylinositol 4-kinase alpha (PI4-kinase alpha) (PtdIns-4-kinase alpha) (P14K-alpha); (4448:) Phosphatidylinositol 4-kinase beta (PtdIns 4-kinase beta) (PI4 Kbeta) (PI4K-beta) (NPIK) (PI4K92); (4449:) phosphatidylinositol 4-kinase type II [Homo sapiens]; (4450:) phosphatidylinositol 4-kinase type-II beta [Homo sapiens]; (4451:) phosphatidylinositol 4-kinase, catalytic, alpha polypeptide isoform1 [Homo sapiens]; (4452:) phosphatidylinositol 4-kinase, catalytic, alpha polypeptide isoform2 [Homo sapiens]; (4453:) phosphatidylinositol 4-kinase, catalytic, beta polypeptide [Homo sapiens]; (4454:) phosphatidylinositol glycan anchor biosynthesis, class K precursor [Homo sapiens]; (4455:) phosphatidylinositol glycan anchor biosynthesis, class L [Homo sapiens]; (4456:) phosphatidylinositol glycan anchor biosynthesis, class P isoform 1 [Homo sapiens]; (4457:) phosphatidylinositol glycan anchor biosynthesis, class P isoform 2 [Homo sapiens]; (4458:) phosphatidylinositol glycan anchor biosynthesis, class Q isoform 1 [Homo sapiens]; (4459:) phosphatidylinositol glycan anchor biosynthesis, class Q isoform 2 [Homo sapiens]; (4460:) phosphatidylinositol glycan anchor biosynthesis, class S [Homo sapiens]; (4461:) phosphatidylinositol glycan anchor biosynthesis, class T precursor [Homo sapiens]; (4462:) phosphatidylinositol glycan anchor biosynthesis, class Y isoform 1 [Homo sapiens]; (4463:) phosphatidylinositol glycan anchor biosynthesis, class Y isoform 2 [Homo sapiens]; (4464:) phosphatidylinositol glycan class Y [Homo sapiens]; (4465:) phosphatidylinositol glycan, class C [Homo sapiens]; (4466:) Phosphatidylinositol N-acetylglucosaminyltransferase subunit A(GlcNAc-PI synthesis protein) (Phosphatidylinositol-glycanbiosynthesis class A protein) (PIG-A); (4467:) phosphatidylinositol N-acetylglucosaminyltransferase subunit A isoform 1 [Homo sapiens]; (4468:) phosphatidylinositol N-acetylglucosaminyltransferase subunit Aisoform 3 [Homo sapiens]; (4469:) Phosphatidylinositol N-acetylglucosaminyltransferase subunit P(Phosphatidylinositol-glycan biosynthesis class P protein) (PIG-P) (Down syndrome critical region protein 5) (Down syndrome critical region protein C); (4470:) Phosphatidylinositol N-acetylglucosaminyltransferase subunit Q(Phosphatidylinositol-glycan biosynthesis class Q protein) (PIG-Q) (N-acetylglucosamyl transferase component GPI1); (4471:) Phosphatidylinositol N-acetylglucosaminyltransferase subunit Y(Phosphatidylinositol-glycan biosynthesis class Y protein) (PIG-Y); (4472:) phosphatidylinositol polyphosphate 5-phosphatase isoform a [Homo sapiens]; (4473:) phosphatidylinositol polyphosphate 5-phosphatase isoform b [*Homo sapiens*]; (4474:) Phosphatidylinositol-4,5-bisphosphate 3-kinase catalytic subunit gamma isoform (PI3-kinase p110 subunit gamma) (PtdIns-3-kinase subunit p110) (PI3K) (PI3 Kgamma) (p120-PI3K); (4475:) Phosphatidylinositol-4-phosphate 3-kinase C2 domain-containing beta polypeptide (Phosphoinositide 3-Kinase-C2-beta) (PtdIns-3-kinase C2beta) (PI3K-C2beta) (C2-PI3K); (4476:) Phosphatidylinositol-4-phosphate 3-kinase C2 domain-containing alpha polypeptide (Phosphoinositide 3-Kinase-C2-alpha) (PtdIns-3-kinase C2 alpha) (PI3K-C2alpha); (4477:) phosphatidylinositol-4-phosphate 5-kinase type II alpha [*Homo sapiens*]; (4478:) Phosphatidylinositol-4-phosphate 5-kinase type-1 gamma (Phosphatidylinositol-4-phosphate 5-kinase type I gamma) (PtdIns(4)P-5-kinase gamma) (PtdInsPKIgamma) (PIP5KIgamma); (4479:) phosphatidylinositol-4-phosphate 5-kinase, type I, alpha [*Homo sapiens*]; (4480:) phosphatidylinositol-4-phosphate 5-kinase, type 1, gamma [*Homo sapiens*]; (4481:) Phosphatidylserine Receptor (PTDSR); (4482:) Phosphatidylserine synthase 1 (PtdSer synthase 1) (PSS-1) (Serine-exchange enzyme I); (4483:) Phosphatidylserine synthase 2 (PtdSer synthase 2) (PSS-2) (Serine-exchange enzyme II); (4484:) Phosphodiesterase (PDE); (4485:) phosphodiesterase 5A isoform 1 [*Homo sapiens*]; (4486:) phosphodiesterase 5A isoform 2 [*Homo sapiens*]; (4487:) phosphodiesterase 5A isoform 3 [*Homo sapiens*]; (4488:) phosphodiesterase 6B, cGMP-specific, rod, beta [*Homo sapiens*]; (4489:) phosphodiesterase 8A isoform 1 [*Homo sapiens*]; (4490:) phosphodiesterase 8A isoform 2 [*Homo sapiens*]; (4491:) phosphodiesterase 8A isoform 3 [*Homo sapiens*]; (4492:) phosphodiesterase 8A isoform 4 [*Homo sapiens*]; (4493:) phosphodiesterase I/nucleotide pyrophosphatase beta [*Homo sapiens*]; (4494:) Phosphodiesterase-1 (PDE-1); (4495:) Phosphodiesterase-10A (PDE-10A); (4496:) Phosphodiesterase-2 (PDE-2); (4497:) Phosphodiesterase-3 (PDE-3); (4498:) Phosphodiesterase-4 (PDE-4); (4499:) Phosphodiesterase-5 (PDE-5); (4500:) Phosphodiesterase-5 (PDE-5); (4501:) phosphoenolpyruvate carboxykinase (GTP) [*Homo sapiens*]; (4502:) Phosphoenolpyruvate carboxykinase [GTP], mitochondrial precursor (Phosphoenolpyruvate carboxylase) (PEPCK-M); (4503:) Phosphoenolpyruvate carboxykinase 1 (soluble) [*Homo sapiens*]; (4504:) Phosphoenolpyruvate carboxykinase 2 (mitochondrial) [*Homo sapiens*]; (4505:) Phosphoenolpyruvate carboxykinase, cytosolic [GTP](Phosphoenolpyruvate carboxylase) (PEPCK-C); (4506:) phosphoenolpyruvate carboxykinase; (4507:) Phosphoethanolamine/phosphocholine phosphatase; (4508:) phosphofructokinase [*Homo sapiens*]; (4509:) Phosphofructokinase, liver [*Homo sapiens*]; (4510:) phosphofructokinase, muscle [*Homo sapiens*]; (4511:) phosphofructokinase, platelet [*Homo sapiens*]; (4512:) phosphofructokinase; (4513:) phosphofructokinase-M; (4514:) phosphofructokinase-P [*Homo sapiens*]; (4515:) phosphoglucomutase 1 [*Homo sapiens*]; (4516:) Phosphoglucomutase-1 (Glucose phosphomutase 1) (PGM 1); (4517:) Phosphoglucomutase-2 (Glucose phosphomutase 2) (PGM 2); (4518:) phosphogluconate dehydrogenase [*Homo sapiens*]; (4519:) phosphoglycerate dehydrogenase [*Homo sapiens*]; (4520:) phosphoglycerate kinase [*Homo sapiens*]; (4521:) Phosphoglycerate kinase 1 (Primer recognition protein 2) (PRP 2); (4522:) phosphoglycerate kinase 1 [*Homo sapiens*]; (4523:) Phosphoglycerate kinase 2 [Homo sapiens]; (4524:) Phosphoglycerate kinase, testis specific; (4525:) phosphoglycerete kinase 1 [*Homo sapiens*]; (4526:) phosphoinositide 3-kinase (EC 2.7.-.-) T105—human (fragment); (4527:) phosphoinositide 3-kinase (EC 2.7.-.-) T14—human (fragment); (4528:) Phosphoinositide 3-kinase regulatory subunit 5 (PI3-kinase-regulatory subunit 5) (PI3-kinase p101 subunit) (PtdIns-3-kinasep101) (p101-PI3K) (Phosphatidylinositol-4,5-bisphosphate 3-kinaseregulatory subunit) (PtdIns-3-kinase regulatory subunit) (ProteinFOAP-2); (4529:) phosphoinositide-3-kinase, catalytic, alpha polypeptide [*Homo sapiens*]; (4530:) phosphoinositide-3-kinase, catalytic, beta polypeptide [*Homo sapiens*]; (4531:) phosphoinositide-3-kinase, catalytic, gamma polypeptide [*Homo sapiens*]; (4532:) phosphoinositide-3-kinase, class 2, beta polypeptide [*Homo sapiens*]; (4533:) phosphoinositide-3-kinase, class 3 [*Homo sapiens*]; (4534:) phosphoinositide-3-kinase, regulatory subunit 2 (p85 beta) [*Homo sapiens*]; (4535:) phosphoinositide-3-kinase, regulatory subunit, polypeptide 1 isoform 1 [*Homo sapiens*]; (4536:) phosphoinositide-3-kinase, regulatory subunit, polypeptide 1 isoform 2 [*Homo sapiens*]; (4537:) phosphoinositide-3-kinase, regulatory subunit, polypeptide 1isoform 3 [*Homo sapiens*]; (4538:) phosphoinositide-specific phospholipase C PLC-epsilon [*Homo sapiens*]; (4539:) phospholemman precursor [*Homo sapiens*]; (4540:) Phospholipase A2 (PLA2); (4541:) Phospholipase A2 precursor (Phosphatidylcholine 2-acylhydrolase) (Group IB phospholipase A2); (4542:) phospholipase A2, group IIA [*Homo sapiens*]; (4543:) phospholipase A2, group IIE [*Homo sapiens*]; (4544:) phospholipase A2, group III precursor [*Homo sapiens*]; (4545:) phospholipase A2, group V precursor [*Homo sapiens*]; (4546:) phospholipase A2, group VI isoform a [*Homo sapiens*]; (4547:) phospholipase A2, group VI isoform b [*Homo sapiens*]; (4548:) phospholipase A2, group VII [*Homo sapiens*]; (4549:) Phospholipase A2, membrane associated precursor (Phosphatidylcholine 2-acylhydrolase) (Group IIA phospholipase A2) (GIIC sPLA2) (Non-pancreatic secretory phospholipase A2) (NPS-PLA2); (4550:) phospholipase A2; (4551:) phospholipase C delta 3 [*Homo sapiens*]; (4552:) phospholipase C epsilon [*Homo sapiens*]; (4553:) phospholipase C epsilon 1 [*Homo sapiens*]; (4554:) phospholipase C gamma 1 isoform a [*Homo sapiens*]; (4555:) phospholipase C gamma 1 isoform b [*Homo sapiens*]; (4556:) phospholipase C, delta 1 [*Homo sapiens*]; (4557:) phospholipase C, delta 4 [*Homo sapiens*]; (4558:) phospholipase C, epsilon 1 [*Homo sapiens*]; (4559:) phospholipase C-eta2 [*Homo sapiens*]; (4560:) Phospholipase D1 (PLD 1) (Choline phosphatase 1) (Phosphatidylcholine-hydrolyzing phospholipase D1) (hPLD1); (4561:) Phospholipase D2 (PLD 2) (Choline phosphatase 2) (Phosphatidylcholine-hydrolyzing phospholipase D2) (PLD1C) (hPLD2); (4562:) phospholipid scramblase 1 [*Homo sapiens*]; (4563:) phospholipid transfer protein isoform a precursor [*Homo sapiens*]; (4564:) phospholipid transfer protein isoform b precursor [*Homo sapiens*]; (4565:) phospholysine phosphohistidine inorganic pyrophosphate phosphatase(EC 3.6.1.1)-Human; (4566:) phosphomevalonate kinase [*Homo sapiens*]; (4567:) phosphopantetheine adenylyltransferase/dephosphcoenzyme A kinase [*Homo sapiens*]; (4568:) Phosphopantothenatecysteine ligase (Phosphopantothenoylcysteinesynthetase) (PPC synthetase); (4569:) phosphoprotein phosphatase (EC 3.1.3.16) 2A BR gamma regulatorychain—human; (4570:) phosphoribosyl pyrophosphate amidotransferase proprotein [*Homo sapiens*]; (4571:) phosphoribosyl pyrophosphate synthetase-associated protein 2 [*Homo sapiens*]; (4572:) phosphoribosylformylglycinamidine synthase [*Homo sapiens*]; (4573:) phosphoribosylglycinamide formyltransferase,phosphoribosylglycinamide synthetase, phosphoribosylaminoimidazolesynthetase isoform 1 [*Homo sapiens*]; (4574:) phosphoribosylglycinamide formyltransferase,phosphoribosylglycinamide synthetase, phosphoribosylaminoimidazolesynthetase isoform 2 [Homo sapiens]; (4575:) phosphoribosylpyrophosphate synthetase subunit III; (4576:) Phosphorylase b kinase regulatory subunit alpha, liver isoform (Phosphorylase kinase alpha L subunit); (4577:) Phosphorylase b kinase regulatory subunit alpha, skeletal muscleisoform (Phosphorylase kinase alpha M subunit); (4578:) Phosphorylase b kinase regulatory subunit beta (Phosphorylasekinase subunit beta); (4579:) phosphorylase kinase gamma subunit 1 [Homo sapiens]; (4580:) phosphorylase kinase, alpha 1 (muscle) [Homo sapiens]; (4581:) phosphoserine aminotransferase isoform 1 [Homo sapiens]; (4582:) phosphoserine aminotransferase isoform 2 [Homo sapiens]; (4583:) Phosphoserine phosphatase (PSP) (O-phosphoserine phosphohydrolase) (PSPase) (L-3-phosphoserine phosphatase); (4584:) phosphoserine phosphatase [Homo sapiens]; (4585:) photoreceptor outer segment all-trans retinol dehydrogenase [Homo sapiens]; (4586:) Photoreceptor-specific nuclear receptor (Retina-specific nuclear receptor); (4587:) phytanoil-CoA alpha hydroxylase [Homo sapiens]; (4588:) phytanoyl-CoA 2-hydroxylase isoform a precursor [Homo sapiens]; (4589:) phytanoyl-CoA 2-hydroxylase isoform b precursor [Homo sapiens]; (4590:) Phytanoyl-CoA dioxygenase, peroxisomal precursor (Phytanoyl-CoAalpha-hydroxylase) (PhyH) (Phytanic acid oxidase); (4591:) phytoceramidase, alkaline [Homo sapiens]; (4592:) PI-3 kinase [Homo sapiens]; (4593:) PIG50 [Homo sapiens]; (4594:) pim-1 oncogene [Homo sapiens]; (4595:) Pim-1 Receptor Tyrosine Kinase; (4596:) PITSLRE serine/threonine-protein kinase CDC2L1(Galactosyltransferase-associated protein kinase p58/GTA) (Celldivision cycle 2-like protein kinase 1) (CLK-1) (CDK11) (p58CLK-1); (4597:) PITSLRE serine/threonine-protein kinase CDC2L2(Galactosyltransferase-associated protein kinase p58/GTA) (Celldivision cycle 2-like protein kinase 2) (CDK11); (4598:) Pituitary Adenylate Cyclase Activating Peptide Receptor 3 (PACAP R3); (4599:) pituitary adenylate cyclase activating peptide receptor type Iprecursor—human; (4600:) Pituitary adenylate cyclase-activating polypeptide type I receptor precursor (PACAP type I receptor) (PACAP-R-1); (4601:) PKM2 protein [Homo sapiens]; (4602:) placenta copper monamine oxidase [Homo sapiens]; (4603:) Placental Alkaline Phosphatase (PALP); (4604:) placental alkaline phosphatase preproprotein [Homo sapiens]; (4605:) placental lactogen hormone precursor [Homo sapiens]; (4606:) placental lactogen; (4607:) placental-like alkaline phosphatase preproprotein [Homo sapiens]; (4608:) plakoglobin [Homo sapiens]; (4609:) plasma carboxypeptidase B2 isoform a preproprotein [Homo sapiens]; (4610:) plasma carboxypeptidase B2 isoform b [Homo sapiens]; (4611:) plasma glutathione peroxidase 3 precursor [Homo sapiens]; (4612:) plasma kallikrein B1 precursor [Homo sapiens]; (4613:) "Plasma kallikrein precursor (Plasma prekallikrein) (Kininogenin) (Fletcher factor) [Contains:] Plasma kallikrein heavy chain; Plasmakallikrein light chain]."; (4614:) Plasma membrane calcium-transporting ATPase 1 (PMCA1) (Plasmamembrane calcium pump isoform 1) (Plasma membrane calcium ATPase isoform 1); (4615:) Plasma membrane calcium-transporting ATPase 2 (PMCA2) (Plasmamembrane calcium pump isoform 2) (Plasma membrane calcium ATPaseisoform 2); (4616:) Plasma membrane calcium-transporting ATPase 3 (PMCA3) (Plasmamembrane calcium pump isoform 3) (Plasma membrane calcium ATPaseisoform 3); (4617:) Plasma membrane calcium-transporting ATPase 4 (PMCA4) (Plasmamembrane calcium pump isoform 4) (Plasma membrane calcium ATPaseisoform 4); (4618:) plasminogen [Homo sapiens]; (4619:) Plasminogen activator (PAI); (4620:) Plasminogen activator-1 (PAI-1); (4621:) plasminogen activator, tissue type isoform 1 preproprotein [Homo sapiens]; (4622:) plasminogen activator, tissue type isoform 2 precursor [Homo sapiens]; (4623:) plasminogen activator, tissue type isoform 3 precursor [Homo sapiens]; (4624:) plasminogen activator, urokinase receptor isoform 1 precursor [Homo sapiens]; (4625:) plasminogen activator, urokinase receptor isoform 2 precursor [Homo sapiens]; (4626:) plasminogen activator, urokinase receptor isoform 3 precursor [Homo sapiens]; (4627:) "Plasminogen precursor [Contains:] Plasmin heavy chain A; Activation-peptide; Angiostatin; Plasmin heavy chain A, short form; Plasminlight chain B]."; (4628:) Plasmodium Falciparum Calcium-Dependent ATPase (PfATP6); (4629:) platelet coagulation factor XI isoform b [Homo sapiens]; (4630:) platelet coagulation factor XI precursor [Homo sapiens]; (4631:) Platelet Derived Growth Factor Receptor-Alpha (PDGFR-Alpha); (4632:) Platelet Derived Growth Factor Receptor-Beta (PDGFR-Beta); (4633:) platelet factor 4 (chemokine (C-X-C motif) ligand 4) [Homo sapiens]; (4634:) Platelet glycoprotein 4 (Platelet glycoprotein IV) (GPIV) (Glycoprotein IIIb) (GPIIIB) (Leukocyte differentiation antigenCD36) (CD36 antigen) (PAS IV) (PAS-4 protein) (Platelet collagen receptor) (Fatty acid translocase) (FAT) (Thrombospondin receptor); (4635:) Platelet glycoprotein VI precursor; (4636:) Platelet receptor Gi24 precursor; (4637:) Platelet-Activating Factor (PAF); (4638:) platelet-activating factor acetylhydrolase 2 [Homo sapiens]; (4639:) Platelet-activating factor acetylhydrolase 2, cytoplasmic(Serine-dependent phospholipase A2) (HSD-PLA2); (4640:) Platelet-activating factor acetylhydrolase IB subunit alpha (PAFacetylhydrolase 45 kDa subunit) (PAF-AH 45 kDa subunit) (PAF-AHalpha) (PAFAH alpha) (Lissencephaly-1 protein) (LIS-1); (4641:) Platelet-activating factor acetylhydrolase IB subunit beta (PAFacetylhydrolase 30 kDa subunit) (PAF-AH 30 kDa subunit) (PAF-AH subunit beta) (PAFAH subunit beta); (4642:) Platelet-activating factor acetylhydrolase IB subunit gamma (PAFacetylhydrolase 29 kDa subunit) (PAF-AH 29 kDa subunit) (PAF-AHsubunit gamma) (PAFAH subunit gamma); (4643:) platelet-activating factor acetylhydrolase, isoform Ib, alphasubunit (45 kD) [Homo sapiens]; (4644:) Platelet-activating factor receptor (PAF-R); (4645:) Platelet-Derived Growth Factor Receptor (PDGFR); (4646:) platelet-derived growth factor receptor beta precursor [Homo sapiens]; (4647:) Platelet-derived growth factor-D (PDGF-D); (4648:) platelet-type phosphofructokinase [Homo sapiens]; (4649:) Plexin-A3 precursor (Plexin-4) (Semaphorin receptor SEX); (4650:) Plexin-A4 precursor; (4651:) Plexin-B1 precursor (Semaphorin receptor SEP); (4652:) Plexin-B2 precursor (MM1); (4653:) Plexin-B3 precursor; (4654:) Plexin-D1 precursor; (4655:) PMS1 nirs variant 1 [Homo sapiens]; (4656:) PMS1 nirs variant 2 [Homo sapiens]; (4657:) PMS1 nirs variant 3 [Homo sapiens]; (4658:) PMS1 nirs variant 5 [Homo sapiens]; (4659:) PMS1 nirs variant 6 [Homo sapiens]; (4660:) PMS1 nirs variant 7 [Homo sapiens]; (4661:) PMS1 nirs variant 8 [Homo sapiens]; (4662:) PMS1 nirs variant 9 [Homo sapiens]; (4663:) PMS1 postmeiotic segregation increased 1 (S. cerevisiae) [Homo sapiens]; (4664:) PMS1 protein [Homo sapiens]; (4665:) PMS1 protein homolog 1 (DNA mismatch repair protein PMS1); (4666:) PMS1 protein homolog 2 (DNA mismatch repair protein PMS2); (4667:) PMS2 gene; (4668:) PMS2 postmeiotic segregation increased 2 (S. cerevisiae) [Homo sapiens]; (4669:) PMS2 postmeiotic segregation increased 2 isoform a [Homo sapiens]; (4670:) PMS2 protein [Homo sapiens]; (4671:) PMS2-C terminal-like [Homo sapiens]; (4672:) PMS2CL protein [Homo sapiens]; (4673:) PMS2L14 [Homo sapiens];

(4674:) PMS2L15 [Homo sapiens]; (4675:) PMS2L16 [Homo sapiens]; (4676:) PMS2L5 protein [Homo sapiens]; (4677:) PMS7 [Homo sapiens]; (4678:) Poliovirus receptor precursor (Nectin-like protein 5) (Necl-5) (CD155 antigen); (4679:) poliovirus receptor-related 4 [Homo sapiens]; (4680:) Poliovirus receptor-related protein 1 precursor (Herpes virus entrymediator C) (HveC) (Nectin-1) (Herpesvirus Ig-like receptor) (HIgR) (CD111 antigen); (4681:) Poliovirus receptor-related protein 2 precursor (Herpes virus entrymediator B) (HveB) (Nectin-2) (CD112 antigen); (4682:) Polo-Like Kinase (Plk); (4683:) polo-like kinase [Homo sapiens]; (4684:) Polo-Like Kinase 1 (Plk1); (4685:) POLS protein [Homo sapiens]; (4686:) poly (ADP-ribose) glycohydrolase [Homo sapiens]; (4687:) poly (ADP-ribose) polymerase family, member 1 [Homo sapiens]; (4688:) poly (ADP-ribose) polymerase family, member 10 [Homo sapiens]; (4689:) Poly [ADP-ribose] polymerase 1 (PARP-1) (ADPRT) (NAD(+)ADP-ribosyltransferase 1) (Poly[ADP-ribose] synthetase 1); (4690:) Poly(A) polymerase gamma (PAP gamma) (Polynucleotideadenylyltransferase gamma) (SRP RNA 3' adenylating enzyme) (Neo-poly(A) polymerase) (Neo-PAP); (4691:) poly(A) polymerase gamma [Homo sapiens]; (4692:) Poly(A)-specific ribonuclease PARN (Polyadenylate-specific ribonuclease) (Deadenylating nuclease) (Deadenylation nuclease); (4693:) Poly(ADP-Ribose) Glycohydrolase (PARG); (4694:) Poly(ADP-ribose) polymerase (PARP); (4695:) Poly(ADP-ribose) polymerase-1 (PARP-1); (4696:) Poly(ADP-ribose) polymerase-2 (PARP-2); (4697:) poly(rC) binding protein 1 [Homo sapiens]; (4698:) polyamine oxidase isoform 1 [Homo sapiens]; (4699:) polyamine oxidase isoform 2 [Homo sapiens]; (4700:) polyamine oxidase isoform 3 [Homo sapiens]; (4701:) polyamine oxidase isoform 4 [Homo sapiens]; (4702:) Polycystic kidney and hepatic disease 1 precursor (Fibrocystin) (Polyductin) (Tigmin); (4703:) polymerase (DNA directed) kappa [Homo sapiens]; (4704:) polymerase (DNA directed), beta [Homo sapiens]; (4705:) polymerase (DNA directed), delta 2, regulatory subunit [Homo sapiens]; (4706:) polymerase (DNA directed), eta [Homo sapiens]; (4707:) polymerase (DNA directed), gamma 2, accessory subunit [Homo sapiens]; (4708:) polymerase (DNA directed), lambda [Homo sapiens]; (4709:) polymerase (DNA-directed), alpha [Homo sapiens]; (4710:) polymerase (RNA) III (DNA directed) polypeptide A, 155 kDa [Homo sapiens]; (4711:) polymerase (RNA) III (DNA directed) polypeptide C (62 kD) [Homo sapiens]; (4712:) polynucleotide kinase 3'-phosphatase [Homo sapiens]; (4713:) Polypeptide N-acetylgalactosaminyltransferase 1 (Protein-UDPacetylgalactosaminyltransferase 1) (UDP-GalNAc:polypeptideN-acetylgalactosaminyltransferase 1) (Polypeptide GalNActransferase 1) (GalNAc-T1) (pp-GaNTase 1) [Contains:) PolypeptideN-acetylgalactosaminyltransferase 1 soluble form]; (4714:) Polypeptide N-acetylgalactosaminyltransferase 10 (Protein-UDPacetylgalactosaminyltransferase 10) (UDP-GalNAc:polypeptideN-acetylgalactosaminyltransferase 10) (Polypeptide GalNActransferase 10) (GalNAc-T10) (pp-GaNTase 10); (4715:) Polypeptide N-acetylgalactosaminyltransferase 11 (Protein-UDPacetylgalactosaminyltransferase 11) (UDP-GalNAc:polypeptideN-acetylgalactosaminyltransferase 11) (Polypeptide GalNActransferase 11) (GalNAc-T11) (pp-GaNTase 11); (4716:) Polypeptide N-acetylgalactosaminyltransferase 12 (Protein-UDPacetylgalactosaminyltransferase 12) (UDP-GalNAc:polypeptideN-acetylgalactosaminyltransferase 12) (Polypeptide GalNActransferase 12) (GalNAc-T12) (pp-GaNTase 12); (4717:) Polypeptide N-acetylgalactosaminyltransferase 13 (Protein-UDPacetylgalactosaminyltransferase 13) (UDP-GalNAc:polypeptideN-acetylgalactosaminyltransferase 13) (Polypeptide GalNActransferase 13) (GalNAc-T13) (pp-GaNTase 13); (4718:) Polypeptide N-acetylgalactosaminyltransferase 14 (Protein-UDPacetylgalactosaminyltransferase 14) (UDP-GalNAc:polypeptideN-acetylgalactosaminyltransferase 14) (Polypeptide GalNActransferase 14) (GalNAc-T14) (pp-GaNTase 14); (4719:) Polypeptide N-acetylgalactosaminyltransferase 2 (Protein-UDPacetylgalactosaminyltransferase 2) (UDP-GalNAc:polypeptideN-acetylgalactosaminyltransferase 2) (Polypeptide GalNActransferase 2) (GalNAc-T2) (pp-GaNTase 2) [Contains:) PolypeptideN-acetylgalactosaminyltransferase 2 soluble form]; (4720:) polypeptide N-acetylgalactosaminyltransferase 2 [Homo sapiens]; (4721:) Polypeptide N-acetylgalactosaminyltransferase 3 (Protein-UDPacetylgalactosaminyltransferase 3) (UDP-GalNAc:polypeptideN-acetylgalactosaminyltransferase 3) (Polypeptide GalNActransferase 3) (GalNAc-T3) (pp-GaNTase 3); (4722:) Polypeptide N-acetylgalactosaminyltransferase 4 (Protein-UDPacetylgalactosaminyltransferase 4) (UDP-GalNAc:polypeptideN-acetylgalactosaminyltransferase 4) (Polypeptide GalNActransferase 4) (GalNAc-T4) (pp-GaNTase 4); (4723:) Polypeptide N-acetylgalactosaminyltransferase 6 (Protein-UDPacetylgalactosaminyltransferase 6) (UDP-GalNAc:polypeptideN-acetylgalactosaminyltransferase 6) (Polypeptide GalNActransferase 6) (GalNAc-T6) (pp-GaNTase 6); (4724:) polypeptide N-acetylgalactosaminyltransferase 7 [Homo sapiens]; (4725:) polypeptide N-acetylgalactosaminyltransferase 8 [Homo sapiens]; (4726:) Polypeptide N-acetylgalactosaminyltransferase 9 (Protein-UDPacetylgalactosaminyltransferase 9) (UDP-GalNAc:polypeptideN-acetylgalactosaminyltransferase 9) (Polypeptide GalNActransferase 9) (GalNAc-T9) (pp-GaNTase 9); (4727:) Polypeptide N-acetylgalactosaminyltransferase-like protein 2(Protein-UDP acetylgalactosaminyltransferase-like protein 2) (UDP-GalNAc: polypeptide N-acetylgalactosaminyltransferase-like protein 2) (Polypeptide GalNAc transferase-like protein 2) (GalNAc-T-like protein 2) (pp-GaNTase-like protein 2); (4728:) polyserase-2 [Homo sapiens]; (4729:) Polyserase-2 precursor (Polyserine protease 2) (Protease serine-36); (4730:) Porcine endogenous retrovirus A receptor 1 precursor (PERV-Areceptor 1) (Protein GPR172A); (4731:) Porcine endogenous retrovirus A receptor 2 precursor (PERV-Areceptor 2) (Protein GPR172B); (4732:) Porimin precursor (Transmembrane protein 123) (Pro-oncosis receptor inducing membrane injury) (Keratinocytes-associated transmembraneprotein 3) (KCT-3); (4733:) Porphobilinogen deaminase (Hydroxymethylbilane synthase) (HMBS) (Preuroporphyrinogen synthase) (PBG-D); (4734:) "porphobilinogen deaminase; PBGD [Homo sapiens]."; (4735:) postmeiotic segregation 1 [Homo sapiens]; (4736:) postmeiotic segregation increased 2 nirs variant 2 [Homo sapiens]; (4737:) postmeiotic segregation increased 2 nirs variant 5 [Homo sapiens]; (4738:) postmeiotic segregation increased 2-like 5 [Homo sapiens]; (4739:) postreplication repair protein hRAD18p [Homo sapiens]; (4740:) PP3895 [Homo sapiens]; (4741:) PPP2R5E protein [Homo sapiens]; (4742:) prenyl diphosphate synthase, subunit 1 [Homo sapiens]; (4743:) prenyl protein peptidase RCE1 isoform 1 [Homo sapiens]; (4744:) prenyl protein peptidase RCE1 isoform 2 [Homo sapiens]; (4745:) prenylcysteine lyase [Homo sapiens]; (4746:) prenylcysteine oxidase 1 [Homo sapiens]; (4747:) presenilin 1 [Homo sapiens]; (4748:) presenilin 2 isoform 1 [Homo sapiens]; (4749:) presenilin 2 isoform 2 [Homo sapiens]; (4750:) "Presenilin-1 (PS-1)

(Protein S182) [Contains:) Presenilin-1 NTF subunit; Presenilin-1 CTF subunit; Presenilin-1 CTF12 (PS1-CTF12)]."; (4751:) Presequence protease, mitochondrial precursor (hPreP) (Pitrilysinmetalloproteinase 1) (Metalloprotease 1) (hMP1); (4752:) Presqualene diphosphate phosphatase (Phosphatidic acid phosphatasetype 2 domain-containing protein 2); (4753:) prion protein preproprotein [*Homo sapiens*]; (4754:) pristanoyl-CoA oxidase [*Homo sapiens*]; (4755:) Pro oligopeptidase; (4756:) Probable allantoicase (Allantoate amidinohydrolase); (4757:) Probable C→U-editing enzyme APOBEC-2; (4758:) Probable calcium-transporting ATPase KIAA0703; (4759:) Probable DNA dC→dU-editing enzyme APOBEC-3A (Phorbolin-1); (4760:) Probable DNA dC→dU-editing enzyme APOBEC-3B (Phorbolin-1-related protein) (Phorbolin-2/3); (4761:) Probable DNA dC→dU-editing enzyme APOBEC-3C (APOBEC1-like) (Phorbolin I protein); (4762:) Probable DNA dC→dU-editing enzyme APOBEC-3D; (4763:) Probable E3 ubiquitin-protein ligase HECTD2 (HECT domain-containing protein 2); (4764:) Probable E3 ubiquitin-protein ligase HECTD3 (HECT domain-containingprotein 3); (4765:) Probable G-protein coupled receptor 1; (4766:) Probable G-protein coupled receptor 101; (4767:) Probable G-protein coupled receptor 110 precursor (G-protein coupled receptor PGR19) (G-protein coupled receptor KPG_012); (4768:) Probable G-protein coupled receptor 111 (G-protein coupled receptor PGR20); (4769:) Probable G-protein coupled receptor 112; (4770:) Probable G-protein coupled receptor 113 precursor (G-protein coupled receptor PGR23); (4771:) Probable G-protein coupled receptor 114 precursor (G-protein coupled receptor PGR27); (4772:) Probable G-protein coupled receptor 115 (G-protein coupled receptor PGR18); (4773:) Probable G-protein coupled receptor 116 precursor; (4774:) Probable G-protein coupled receptor 119; (4775:) Probable G-protein coupled receptor 12; (4776:) Probable G-protein coupled receptor 123; (4777:) Probable G-protein coupled receptor 124 precursor (Tumor endothelial marker 5); (4778:) Probable G-protein coupled receptor 125 precursor; (4779:) Probable G-protein coupled receptor 126 precursor; (4780:) Probable G-protein coupled receptor 128 precursor; (4781:) Probable G-protein coupled receptor 132 (G2 accumulation protein); (4782:) Probable G-protein coupled receptor 133 precursor (G-protein coupled receptor PGR25); (4783:) Probable G-protein coupled receptor 135; (4784:) Probable G-protein coupled receptor 139 (G(q)-coupled orphan receptor GPRg1) (G-protein-coupled receptor PGR3); (4785:) Probable G-protein coupled receptor 141 (G-protein coupled receptor PGR13); (4786:) Probable G-protein coupled receptor 142 (G-protein coupled receptor PGR2); (4787:) Probable G-protein coupled receptor 144 (G-protein coupled receptor PGR24); (4788:) Probable G-protein coupled receptor 148 (G-protein coupled receptor PGR6) (Brain and testis restricted GPCR); (4789:) Probable G-protein coupled receptor 149 (G-protein coupled receptor PGR10); (4790:) Probable G-protein coupled receptor 150; (4791:) Probable G-protein coupled receptor 151 (G-protein coupled receptor PGR7) (GPCR-2037); (4792:) Probable G-protein coupled receptor 152 (G-protein coupled receptor PGR5); (4793:) Probable G-protein coupled receptor 153 (G-protein coupled receptor PGR1); (4794:) Probable G-protein coupled receptor 156 (GABAB-related G-protein coupled receptor) (G-protein coupled receptor PGR28); (4795:) Probable G-protein coupled receptor 157; (4796:) Probable G-protein coupled receptor 158 precursor; (4797:) Probable G-protein coupled receptor 160; (4798:) Probable G-protein coupled receptor 161 (G-protein coupled receptor RE2); (4799:) Probable G-protein coupled receptor 162 (Gene-rich cluster gene A protein); (4800:) Probable G-protein coupled receptor 171 (G-protein coupled receptor H963); (4801:) Probable G-protein coupled receptor 173 (Super conserved receptor expressed in brain 3); (4802:) Probable G-protein coupled receptor 174; (4803:) Probable G-protein coupled receptor 176 (HB-954); (4804:) Probable G-protein coupled receptor 179 precursor (Probable G-protein coupled receptor 158-like 1); (4805:) Probable G-protein coupled receptor 18; (4806:) Probable G-protein coupled receptor 19 (GPR-NGA); (4807:) Probable G-protein coupled receptor 20; (4808:) Probable G-protein coupled receptor 21; (4809:) Probable G-protein coupled receptor 22; (4810:) Probable G-protein coupled receptor 25; (4811:) Probable G-protein coupled receptor 26; (4812:) Probable G-protein coupled receptor 27 (Super conserved receptor expressed in brain 1); (4813:) Probable G-protein coupled receptor 3 (ACCA orphan receptor); (4814:) Probable G-protein coupled receptor 31; (4815:) Probable G-protein coupled receptor 32; (4816:) Probable G-protein coupled receptor 33; (4817:) Probable G-protein coupled receptor 34; (4818:) Probable G-protein coupled receptor 35; (4819:) Probable G-protein coupled receptor 37 precursor (Endothelin B receptor-like protein 1) (ETBR-LP-1) (Parkin-associated endothelin receptor-like receptor) (PAELR); (4820:) Probable G-protein coupled receptor 39; (4821:) Probable G-protein coupled receptor 4 (G-protein coupled receptor19); (4822:) Probable G-protein coupled receptor 45 (PSP24-alpha) (PSP24-1); (4823:) Probable G-protein coupled receptor 52; (4824:) Probable G-protein coupled receptor 55; (4825:) Probable G-protein coupled receptor 61 (Biogenic amine receptor-like G-protein coupled receptor); (4826:) Probable G-protein coupled receptor 62 (hGPCR8); (4827:) Probable G-protein coupled receptor 63 (PSP24-beta) (PSP24-2); (4828:) Probable G-protein coupled receptor 75; (4829:) Probable G-protein coupled receptor 78; (4830:) Probable G-protein coupled receptor 81 (G-protein coupled receptor104); (4831:) Probable G-protein coupled receptor 82; (4832:) Probable G-protein coupled receptor 83 precursor (G-protein coupled receptor 72); (4833:) Probable G-protein coupled receptor 84 (Inflammation- related G-protein coupled receptor EX33); (4834:) Probable G-protein coupled receptor 85 (Super conserved receptor expressed in brain 2); (4835:) Probable G-protein coupled receptor 87 (G-protein coupled receptor95); (4836:) Probable G-protein coupled receptor 88 (Striatum-specific G-protein coupled receptor); (4837:) Probable G-protein coupled receptor 92; (4838:) Probable G-protein coupled receptor 97 precursor (G-protein coupled receptor PGR26); (4839:) Probable G-protein-coupled receptor 146 (G-protein coupled receptor PGR8); (4840:) Probable P2Y purinoceptor GPR17 (G protein-coupled receptor 17) (P2Y-like receptor) (R12); (4841:) Probable ubiquitin carboxyl-terminal hydrolase CYLD (Ubiquitinthioesterase CYLD) (Ubiquitin-specific-processing protease CYLD) (Deubiquitinating enzyme CYLD); (4842:) Probable ubiquitin carboxyl-terminal hydrolase FAF-X (Ubiquitinthioesterase FAF-X) (Ubiquitin-specific-processing protease FAF-X) (Deubiquitinating enzyme FAF-X) (Fat facets protein-related, X-linked) (Ubiquitin-specific protease 9, X chromosome); (4843:) Probable ubiquitin carboxyl-terminal hydrolase FAF-Y (Ubiquitinthioesterase FAF-Y) (Ubiquitin-specific-processing protease FAF-Y) (Deubiquitinating enzyme FAF-Y) (Fat facets protein-related, Y-linked) (Ubiquitin-specific protease 9, Y chromosome); (4844:) Probable ubiquitin-conjugating enzyme E2 W (Ubiquitin-proteinligase W) (Ubiquitin carrier protein W); (4845:) procaspase-8 [*Homo sapiens*];

(4846:) procaspase-8L [*Homo sapiens*]; (4847:) procollagen-lysine, 2-oxoglutarate 5-dioxygenase 2 isoform a precursor [*Homo sapiens*]; (4848:) procollagen-lysine, 2-oxoglutarate 5-dioxygenase 2 isoform b precursor [*Homo sapiens*]; (4849:) procollagen-lysine, 2-oxoglutarate 5-dioxygenase 3 precursor [*Homo sapiens*]; (4850:) Procollagen-lysine, 2-oxoglutarate 5-dioxygenase 1 precursor (Lysylhydroxylase 1) (LH1); (4851:) Procollagen-lysine,2-oxoglutarate 5-dioxygenase 2 precursor (Lysylhydroxylase 2) (LH2); (4852:) Progesterone Receptor (PR); (4853:) Progesterone-induced-blocking factor 1; (4854:) Progestin and adipoQ receptor family member 3 (Progestin and adipoQreceptor family member III); (4855:) Progestin and adipoQ receptor family member 4 (Progestin and adipoQreceptor family member IV); (4856:) Progestin and adipoQ receptor family member 6 (Progestin and adipoQreceptor family member VI); (4857:) Progestin and adipoQ receptor family member 9 (Progestin and adipoQreceptor family member IX); (4858:) Programmed Cell Death 1 (PDCD1) Receptor; (4859:) Programmed cell death 1 ligand 1 precursor (Programmed death ligand1) (PD-L1) (PDCD1 ligand 1) (B7 homolog 1) (B7-H1) (CD274 antigen); (4860:) Programmed cell death 1 ligand 2 precursor (Programmed death ligand2) (PD-L2) (PD-1-ligand 2) (PDCD1 ligand 2) (Butyrophilin B7-DC) (B7-DC) (CD273 antigen); (4861:) Prohibitin-2 (B-cell receptor-associated protein BAP37) (Repressor of estrogen receptor activity) (D-prohibitin); (4862:) prohormone convertase 2 [*Homo sapiens*]; (4863:) prohormone convertase 2, PC2 [human, Peptide, 638 aa]; (4864:) prohormone convertase; (4865:) proinsulin precursor [*Homo sapiens*]; (4866:) Prokineticin 2 (PK2) Receptor; (4867:) Prokineticin receptor 1 (PK-R1) (G-protein coupled receptor 73) (GPR73a) (G-protein coupled receptor ZAQ); (4868:) Prokineticin receptor 2 (PK-R2) (G-protein coupled receptor 73-like1) (GPR73b) (GPRg2); (4869:) Prolactin receptor precursor (PRL-R); (4870:) Prolactin-releasing peptide receptor (PrRP receptor) (PrRPR) (G-protein coupled receptor 10) (hGR3); (4871:) proliferating cell nuclear antigen [*Homo sapiens*]; (4872:) Prolyl 4-Hydroxylase; (4873:) prolyl 4-hydroxylase alpha (II) subunit [*Homo sapiens*]; (4874:) Prolyl 4-hydroxylase alpha-2 subunit precursor (4-PH alpha-2) (Procollagen-proline, 2-oxoglutarate-4-dioxygenase alpha-2 subunit); (4875:) prolyl 4-hydroxylase, alpha I subunit isoform 1 precursor [*Homo sapiens*]; (4876:) prolyl 4-hydroxylase, alpha I subunit isoform 2 precursor [*Homo sapiens*]; (4877:) prolyl 4-hydroxylase, alpha II subunit isoform 1 precursor [*Homo sapiens*]; (4878:) prolyl 4-hydroxylase, alpha II subunit isoform 2 precursor [*Homo sapiens*]; (4879:) prolyl 4-hydroxylase, alpha III subunit precursor [*Homo sapiens*]; (4880:) prolyl 4-hydroxylase, beta subunit [*Homo sapiens*]; (4881:) Prolyl Endopeptidase (PEP); (4882:) prolyl endopeptidase [*Homo sapiens*]; (4883:) prolylcarboxypeptidase isoform 1 preproprotein [*Homo sapiens*]; (4884:) prolylcarboxypeptidase isoform 2 preproprotein [*Homo sapiens*]; (4885:) prolylcarboxypeptidase; (4886:) pro-matrix metalloproteinase-3—human (fragment); (4887:) proMch6; (4888:) Promyelocytic Leukemia/Retinoic Acid Receptor Alpha (PMURAR) Protein; (4889:) Properdin precursor (Factor P); (4890:) "propionyl CoA carboxylase alpha subunit; PCCA [*Homo sapiens*]."; (4891:) propionyl Coenzyme A carboxylase, alpha polypeptide [*Homo sapiens*]; (4892:) propionyl-CoA carboxylase [*Homo sapiens*]; (4893:) Propionyl-CoA carboxylase alpha chain, mitochondrial precursor (PCCase subunit alpha) (Propanoyl-CoA:carbon dioxide ligase subunitalpha); (4894:) propionyl-CoA carboxylase alpha polypeptide precursor [*Homo sapiens*]; (4895:) propionyl-CoA carboxylase alpha subunit [*Homo sapiens*]; (4896:) Propionyl-CoA carboxylase beta chain, mitochondrial precursor (PCCase subunit beta) (Propanoyl-CoA:carbon dioxide ligase subunitbeta); (4897:) propionyl-CoA carboxylase; (4898:) propionyl-Coenzyme A carboxylase, alpha polypeptide precursor [*Homo sapiens*]; (4899:) proprotein convertase subtilisin/kexin type 1 preproprotein [*Homo sapiens*]; (4900:) proprotein convertase subtilisin/kexin type 2 [*Homo sapiens*]; (4901:) proprotein convertase subtilisin/kexin type 5 preproprotein [*Homo sapiens*]; (4902:) Proprotein convertase subtilisin/kexin type 6 precursor (Paired basic amino acid cleaving enzyme 4) (Subtilisin/kexin-like protease PACE4) (Subtilisin-like proprotein convertase 4) (SPC4); (4903:) Proprotein convertase subtilisin/kexin type 7 precursor (Proprotein convertase PC7) (Subtilisin/kexin-like protease PC7) (Prohormoneconvertase PC7) (PC8) (hPC8) (Lymphoma proprotein convertase); (4904:) proprotein convertase subtilisin/kexin type 7 preproprotein [*Homo sapiens*]; (4905:) Proprotein convertase subtilisin/kexin type 9 precursor (Proprotein convertase PC9) (Subtilisin/kexin-like protease PC9) (Neuralapoptosis-regulated convertase 1) (NARC-1); (4906:) prosaposin isoform a preproprotein [*Homo sapiens*]; (4907:) prosaposin isoform b preproprotein [*Homo sapiens*]; (4908:) prosaposin isoform c preproprotein [*Homo sapiens*]; (4909:) Prostacyclin receptor (Prostanoid IP receptor) (PGI receptor) (Prostaglandin I2 receptor); (4910:) Prostaglandin D2 (PGD2) Receptor; (4911:) Prostaglandin D2 receptor (Prostanoid DP receptor) (PGD receptor); (4912:) Prostaglandin E synthase (Microsomal glutathione S-transferase)-like 1) (MGST1-L1) (p53-induced apoptosis protein 12); (4913:) prostaglandin E synthase [*Homo sapiens*]; (4914:) Prostaglandin E synthase 2 (Microsomal prostaglandin E synthase 2) (mPGES-2) [Contains:) Prostaglandin E synthase 2 truncated form]; (4915:) Prostaglandin E1 (PGE1) Receptor; (4916:) prostaglandin E2 receptor EP3-chain—human; (4917:) Prostaglandin E2 receptor, EP1 subtype (Prostanoid EP1 receptor) (PGE receptor, EP1 subtype); (4918:) Prostaglandin E2 receptor, EP2 subtype (Prostanoid EP2 receptor) (PGE receptor, EP2 subtype); (4919:) Prostaglandin E2 receptor, EP3 subtype (Prostanoid EP3 receptor) (PGE receptor, EP3 subtype) (PGE2-R); (4920:) Prostaglandin E2 receptor, EP4 subtype (Prostanoid EP4 receptor) (PGE receptor, EP4 subtype); (4921:) Prostaglandin F2 alpha (PGF2 alpha) Receptor; (4922:) Prostaglandin F2-alpha receptor (Prostanoid FP receptor) (PGFreceptor) (PGF2 alpha receptor); (4923:) Prostaglandin G/H synthase 1 precursor (Cyclooxygenase-1) (COX-1) (Prostaglandin-endoperoxide synthase 1) (Prostaglandin H2 synthase1) (PGH synthase 1) (PGHS-1) (PHS1); (4924:) Prostaglandin G/H synthase 2 precursor (Cyclooxygenase-2) (COX-2) (Prostaglandin-endoperoxide synthase 2) (Prostaglandin H2 synthase2) (PGH synthase 2) (PGHS-2) (PHS II); (4925:) Prostaglandin I2 (PGI2) Receptor; (4926:) prostaglandin I2 (prostacyclin) synthase [*Homo sapiens*]; (4927:) prostaglandin-D synthase [*Homo sapiens*]; (4928:) prostaglandin-endoperoxide synthase 1 isoform 1 precursor [*Homo sapiens*]; (4929:) prostaglandin-endoperoxide synthase 1 isoform 2 precursor [*Homo sapiens*]; (4930:) prostaglandin-endoperoxide synthase 2 precursor [*Homo sapiens*]; (4931:) prostaglandin-endoperoxide synthase-1 [*Homo sapiens*]; (4932:) Prostasin; (4933:) prostasin preproprotein [*Homo sapiens*]; (4934:) Prostate-Specific Membrane Antigen (PSMA); (4935:) prostatic acid phosphatase precursor [*Homo sapiens*]; (4936:) protease, serine, 1 preproprotein [*Homo sapiens*]; (4937:) protease, serine, 2 preproprotein [*Homo sapiens*]; (4938:) protease, serine, 22 [*Homo sapiens*]; (4939:) protease, serine, 36 [*Homo sapi-* ens]; (4940:) Protease-Activated Receptor 1 (PAR1); (4941:) Proteasome; (4942:) proteasome 26S ATPase subunit 1 [Homo sapiens]; (4943:) proteasome 26S ATPase subunit 2 [Homo sapiens]; (4944:) proteasome 26S ATPase subunit 3 [Homo sapiens]; (4945:) proteasome 26S ATPase subunit 4 isoform 1 [Homo sapiens]; (4946:) proteasome 26S ATPase subunit 4 isoform 2 [Homo sapiens]; (4947:) proteasome 26S ATPase subunit 5 [Homo sapiens]; (4948:) proteasome 26S ATPase subunit 6 [Homo sapiens]; (4949:) proteasome 26S non-ATPase subunit 1 [Homo sapiens]; (4950:) proteasome 26S non-ATPase subunit 10 isform 2 [Homo sapiens]; (4951:) proteasome 26S non-ATPase subunit 10 isoform 1 [Homo sapiens]; (4952:) proteasome 26S non-ATPase subunit 11 [Homo sapiens]; (4953:) proteasome 26S non-ATPase subunit 12 [Homo sapiens]; (4954:) proteasome 26S non-ATPase subunit 13 isoform 1 [Homo sapiens]; (4955:) proteasome 26S non-ATPase subunit 13 isoform 2 [Homo sapiens]; (4956:) proteasome 26S non-ATPase subunit 2 [Homo sapiens]; (4957:) proteasome 26S non-ATPase subunit 3 [Homo sapiens]; (4958:) proteasome 26S non-ATPase subunit 4 isoform 1 [Homo sapiens]; (4959:) proteasome 26S non-ATPase subunit 4 isoform 2 [Homo sapiens]; (4960:) proteasome 26S non-ATPase subunit 5 [Homo sapiens]; (4961:) proteasome 26S non-ATPase subunit 7 [Homo sapiens]; (4962:) proteasome 26S non-ATPase subunit 8 [Homo sapiens]; (4963:) proteasome 26S non-ATPase subunit 9 [Homo sapiens]; (4964:) proteasome activator hPA28 suunit beta [Homo sapiens]; (4965:) proteasome activator subunit 1 isoform 1 [Homo sapiens]; (4966:) proteasome activator subunit 1 isoform 2 [Homo sapiens]; (4967:) proteasome activator subunit 2 [Homo sapiens]; (4968:) proteasome activator subunit 3 isoform 1 [Homo sapiens]; (4969:) proteasome activator subunit 3 isoform 2 [Homo sapiens]; (4970:) proteasome alpha 1 subunit isoform 1 [Homo sapiens]; (4971:) proteasome alpha 1 subunit isoform 2 [Homo sapiens]; (4972:) proteasome alpha 2 subunit [Homo sapiens]; (4973:) proteasome alpha 3 subunit isoform 1 [Homo sapiens]; (4974:) proteasome alpha 3 subunit isoform 2 [Homo sapiens]; (4975:) proteasome alpha 4 subunit [Homo sapiens]; (4976:) proteasome alpha 5 subunit [Homo sapiens]; (4977:) proteasome alpha 6 subunit [Homo sapiens]; (4978:) proteasome alpha 7 subunit [Homo sapiens]; (4979:) proteasome beta 1 subunit [Homo sapiens]; (4980:) proteasome beta 10 subunit proprotein [Homo sapiens]; (4981:) proteasome beta 2 subunit [Homo sapiens]; (4982:) proteasome beta 3 subunit [Homo sapiens]; (4983:) proteasome beta 4 subunit [Homo sapiens]; (4984:) proteasome beta 5 subunit [Homo sapiens]; (4985:) proteasome beta 6 subunit [Homo sapiens]; (4986:) proteasome beta 7 subunit proprotein [Homo sapiens]; (4987:) proteasome beta 8 subunit isoform E1 proprotein [Homo sapiens]; (4988:) proteasome beta 8 subunit isoform E2 proprotein [Homo sapiens]; (4989:) proteasome beta 9 subunit isoform 1 proprotein [Homo sapiens]; (4990:) proteasome beta 9 subunit isoform 2 proprotein [Homo sapiens]; (4991:) proteasome inhibitor subunit 1 isoform 1 [Homo sapiens]; (4992:) proteasome inhibitor subunit 1 isoform 2 [Homo sapiens]; (4993:) Proteasome subunit alpha type 1 (Proteasome component C2) (Macropain subunit C2) (Multicatalytic endopeptidase complex subunit C2) (Proteasome nu chain) (30 kDa prosomal protein) (PROS-30); (4994:) Proteasome subunit alpha type 2 (Proteasome component C3) (Macropain subunit C3) (Multicatalytic endopeptidase complex subunit C3); (4995:) Proteasome subunit alpha type 3 (Proteasome component C8) (Macropain subunit C8) (Multicatalytic endopeptidase complex subunit C8); (4996:) Proteasome subunit alpha type 4 (Proteasome component C9) (Macropain subunit C9) (Multicatalytic endopeptidase complex subunit C9) (Proteasome subunit L); (4997:) Proteasome subunit beta type 1 (Proteasome component C5) (Macropain subunit C5) (Multicatalytic endopeptidase complex subunit C5) (Proteasome gamma chain); (4998:) Proteasome subunit beta type 2 (Proteasome component C7-I) (Macropain subunit C7-I) (Multicatalytic endopeptidase complex subunit C7-I); (4999:) Proteasome subunit beta type 3 (Proteasome theta chain) (Proteasome chain 13) (Proteasome component C10-II); (5000:) Proteasome subunit beta type 4 precursor (Proteasome beta chain) (Macropain beta chain) (Multicatalytic endopeptidase complex beta chain) (Proteasome chain 3) (HSN3) (HsBPROS26); (5001:) proteasome subunit C2 [Homo sapiens]; (5002:) proteasome subunit C3 [Homo sapiens]; (5003:) proteasome subunit C5 [Homo sapiens]; (5004:) proteasome subunit C8 [Homo sapiens]; (5005:) proteasome subunit C9 [Homo sapiens]; (5006:) proteasome subunit HsC10-11 [Homo sapiens]; (5007:) proteasome subunit HsC7-I [Homo sapiens]; (5008:) proteasome subunit HsN3 [Homo sapiens]; (5009:) proteasome subunit p40/Mov34 protein [Homo sapiens]; (5010:) proteasome subunit X [Homo sapiens]; (5011:) proteasome subunit Y [Homo sapiens]; (5012:) proteasome: SUBUNIT=HsC10-11; (5013:) proteasome: SUBUNIT=HsC7-I; (5014:) proteasome: SUBUNIT=HsN3; (5015:) protective protein for beta-galactosidase [Homo sapiens]; (5016:) Protein arginine N-methyltransferase 1 (Interferon receptor 1-bound protein 4); (5017:) Protein arginine N-methyltransferase 3 (Heterogeneous nuclear ribonucleoprotein methyltransferase-like protein 3); (5018:) Protein arginine N-methyltransferase 6 (Heterogeneous nuclear ribonucleoprotein methyltransferase-like protein 6); (5019:) Protein ariadne-1 homolog (ARI-1) (Ubiquitin-conjugating enzyme E2-binding protein 1) (UbCH7-binding protein) (UbcM4-interacting protein) (HHAR1) (H7-AP2) (MOP-6); (5020:) protein disulfide isomerase-associated 3 precursor [Homo sapiens]; (5021:) protein disulfide isomerase-associated 4 [Homo sapiens]; (5022:) protein disulfide isomerase-related protein; (5023:) Protein disulfide-isomerase A4 precursor (Protein ERp-72) (ERp72); (5024:) Protein disulfide-isomerase TXNDC10 precursor (Thioredoxindomain-containing protein 10) (Thioredoxin-related transmembraneprotein 3); (5025:) Protein FAM125A (CIN85/CD2AP family-binding protein); (5026:) protein kinase (EC 2.7.1.37), cAMP-dependent, type 1-betaregulatory chain—human; (5027:) Protein Kinase A (PKA); (5028:) Protein Kinase B (PKB); (5029:) Protein Kinase B (PKB); (5030:) protein kinase C (EC 2.7.1.-) beta-1—human; (5031:) Protein Kinase C (PKC); (5032:) Protein kinase C alpha type (PKC-alpha) (PKC-A); (5033:) Protein kinase C beta type (PKC-beta) (PKC-B); (5034:) Protein kinase C delta type (nPKC-delta); (5035:) Protein kinase C epsilon type (nPKC-epsilon); (5036:) Protein kinase C eta type (nPKC-eta) (PKC-L); (5037:) Protein kinase C gamma type (PKC-gamma); (5038:) Protein kinase C iota type (nPKC-iota) (Atypical protein kinaseC-lambdanota) (aPKC-lambdahota) (PRKC-lambda/iota); (5039:) protein kinase C substrate 80K-H isoform 1 [Homo sapiens]; (5040:) protein kinase C substrate 80K-H isoform 2 [Homo sapiens]; (5041:) Protein kinase C theta type (nPKC-theta); (5042:) Protein kinase C zeta type (nPKC-zeta); (5043:) protein kinase C, alpha [Homo sapiens]; (5044:) protein kinase C, delta [Homo sapiens]; (5045:) protein kinase C, epsilon [Homo sapiens]; (5046:) protein kinase C, gamma [Homo sapiens]; (5047:) Protein Kinase C-alpha (PKC-alpha); (5048:) Protein Kinase C-beta (PKC-beta); (5049:) Protein Kinase C-delta (PKC-delta); (5050:)

protein kinase CHK2 isoform a [*Homo sapiens*]; (5051:) protein kinase CHK2 isoform b [*Homo sapiens*]; (5052:) protein kinase CHK2 isoform c [*Homo sapiens*]; (5053:) protein kinase, cGMP-dependent, type I [*Homo sapiens*]; (5054:) protein kinase, DNA-activated, catalytic polypeptide [*Homo sapiens*]; (5055:) Protein Kinase-C Like 2 (PRKCL2); (5056:) Protein LMBR1L (Lipocalin-1-interacting membrane receptor) (Lipocalin-interacting membrane receptor) (Limb region 1 protein homolog-like); (5057:) Protein MTO1 homolog, mitochondrial precursor; (5058:) Protein N-terminal asparagine amidohydrolase (Protein NH2-terminalasparagine deamidase) (N-terminal Asn amidase) (NTN-amidase) (PNAD) (Protein NH2-terminal asparagine amidohydrolase) (PNAA); (5059:) protein O-fucosyltransferase 1 isoform 1 precursor [*Homo sapiens*]; (5060:) protein O-fucosyltransferase 1 isoform 2 precursor [*Homo sapiens*]; (5061:) Protein O-mannosyl-transferase 1(Dolichyl-phosphate-mannose—protein mannosyltransferase 1); (5062:) Protein O-mannosyl-transferase 2(Dolichyl-phosphate-mannoseprotein mannosyltransferase 2); (5063:) Protein patched homolog 1 (PTC1) (PTC); (5064:) Protein patched homolog 2 (PTC2); (5065:) protein phosphatase 1, catalytic subunit, alpha isoform 1 [*Homo sapiens*]; (5066:) protein phosphatase 1, catalytic subunit, alpha isoform 2 [*Homo sapiens*]; (5067:) protein phosphatase 1, catalytic subunit, alpha isoform 3 [*Homo sapiens*]; (5068:) protein phosphatase 1, catalytic subunit, gamma isoform [*Homo sapiens*]; (5069:) protein phosphatase 1G [*Homo sapiens*]; (5070:) protein phosphatase 1J (PP2C domain containing) [*Homo sapiens*]; (5071:) protein phosphatase 2, catalytic subunit, alpha isoform [*Homo sapiens*]; (5072:) protein phosphatase 2, catalytic subunit, beta isoform [*Homo sapiens*]; (5073:) protein phosphatase 2, regulatory subunit B (B56), alpha isoform [*Homo sapiens*]; (5074:) protein phosphatase 2, regulatory subunit B", alpha isoform 1 [*Homo sapiens*]; (5075:) protein phosphatase 2, regulatory subunit B", alpha isoform 2 [*Homo sapiens*]; (5076:) protein phosphatase 2, regulatory subunit B", beta isoform 1 [*Homo sapiens*]; (5077:) protein phosphatase 2, regulatory subunit B", beta isoform 2 [*Homo sapiens*]; (5078:) protein phosphatase 2A, regulatory subunit B' isoform a [*Homo sapiens*]; (5079:) protein phosphatase 2A, regulatory subunit B' isoform b [*Homo sapiens*]; (5080:) protein phosphatase 2A, regulatory subunit B' isoform d [*Homo sapiens*]; (5081:) Protein phosphatase 2C isoform alpha (PP2C-alpha) (IA) (Proteinphosphatase 1A); (5082:) Protein phosphatase 2C isoform beta (PP2C-beta); (5083:) Protein preY, mitochondrial precursor; (5084:) Protein Tyrosine Phosphatase 1B (PTP1B); (5085:) Protein tyrosine phosphatase type IVA protein 1 (Protein-tyrosinephosphatase 4a1) (Protein-tyrosine phosphatase of regenerating liver 1) (PRL-1) (PTP (CAAXI)); (5086:) Protein tyrosine phosphatase type IVA protein 2 (Protein-tyrosinephosphatase 4a2) (Protein-tyrosine phosphatase of regeneratingliver 2) (PRL-2) (PTP (CAAXII)) (HU-PP-1) (OV-1); (5087:) Protein tyrosine phosphatase type IVA protein 3 (Protein-tyrosinephosphatase 4a3) (Protein-tyrosine phosphatase of regeneratingliver 3) (PRL-3) (PRL-R); (5088:) protein tyrosine phosphatase type IVA, member 1 [*Homo sapiens*]; (5089:) protein tyrosine phosphatase, non-receptor type 22 (lymphoid)isoform 1 [*Homo sapiens*]; (5090:) protein tyrosine phosphatase, non-receptor type 22 (lymphoid)isoform 2 [*Homo sapiens*]; (5091:) protein tyrosine phosphatase, receptor type, N precursor [*Homo sapiens*]; (5092:) protein X [*Homo sapiens*]; (5093:) protein Z; (5094:) Protein-arginine deiminase type-3 (Protein-arginine deiminase typeIII) (Peptidylarginine deiminase III); (5095:) Protein-arginine deiminase type-4 (Protein-arginine deiminase typeIV) (Peptidylarginine deiminase IV) (HL-60 PAD); (5096:) proteinase 3 (serine proteinase, neutrophil, Wegener granulomatosis autoantigen) [*Homo sapiens*]; (5097:) Proteinase Activated Receptor-2 (PAR-2); (5098:) Proteinase-activated receptor 1 precursor (PAR-1) (Thrombin receptor) (Coagulation factor II receptor); (5099:) Proteinase-activated receptor 2 precursor (PAR-2) (Thrombinreceptor-like 1) (Coagulation factor II receptor-like 1) (G-protein coupled receptor 11); (5100:) Proteinase-activated receptor 3 precursor (PAR-3) (Thrombinreceptor-like 2) (Coagulation factor II receptor-like 2); (5101:) Proteinase-activated receptor 4 precursor (PAR-4) (Thrombin receptor-like 3) (Coagulation factor II receptor-like 3); (5102:) Protein-glutamine gamma-glutamyltransferase 5 (Transglutaminase-5) (TGase 5) (Transglutaminase X) (TGase X) (TGX) (TG(X)); (5103:) "Protein-glutamine gamma-glutamyltransferase E precursor (TGase E) (TGE) (TG(E)) (Transglutaminase-3) [Contains:) Protein-glutaminegamma-glutamyltransferase E 50 kDa non-catalytic chain; Protein-glutamine gamma-glutamyltransferase E 27 kDa catalyticchain]."; (5104:) Protein-glutamine gamma-glutamyltransferase K (Transglutaminase K) (TGase K) (TGK) (TG(K)) (Transglutaminase-1) (Epidermal TGase); (5105:) protein-L-isoaspartate (D-aspartate) O-methyltransferase [*Homo sapiens*]; (5106:) protein-O-mannosyltransferase 1 isoform a [*Homo sapiens*]; (5107:) protein-O-mannosyltransferase 1 isoform b [*Homo sapiens*]; (5108:) protein-O-mannosyltransferase 1 isoform c [*Homo sapiens*]; (5109:) protein-tyrosine kinase (EC 2.7.1.112), receptor type tie precursor—human; (5110:) Protein-tyrosine sulfotransferase 1 (Tyrosylproteinsulfotransferase-1) (TPST-1); (5111:) protein-tyrosine-phosphatase (EC 3.1.3.48), receptor type Hprecursor—human; (5112:) protein-tyrosine-phosphatase (EC 3.1.3.48), receptor type Oprecursor—human; (5113:) "Prothrombin precursor (Coagulation factor II) [Contains:) Activationpeptide fragment 1; Activation peptide fragment 2; Thrombin lightchain; Thrombin heavy chain]."; (5114:) protooncogene protein 1 [*Homo sapiens*]; (5115:) Proto-oncogene tyrosine-protein kinase ABL1 (p150) (c-ABL) (Abelsonmurine leukemia viral oncogene homolog 1); (5116:) Proto-oncogene tyrosine-protein kinase MER precursor (C-mer) (Receptor tyrosine kinase MerTK); (5117:) Proto-oncogene tyrosine-protein kinase ROS precursor (c-ros-1); (5118:) Protoporphyrinogen oxidase (PPO); (5119:) PRTD-NY3 [*Homo sapiens*]; (5120:) P-Selectin Activator; (5121:) Psychosine receptor (G-protein coupled receptor 65) (T cell-death-associated protein 8); (5122:) pterin carbinolamine dehydratase [*Homo sapiens*]; (5123:) pterin-4 alpha-carbinolamine dehydratase precursor [*Homo sapiens*]; (5124:) Pterin-4 alpha-carbinolamine dehydratase/dimerization cofactor of hepatocyte nuclear factor 1 alpha (TCF1) [*Homo sapiens*]; (5125:) Pterin-4 alpha-carbinolamine dehydratase/ dimerization cofactor of hepatocyte nuclear factor 1 alpha (TCF1) 2 [*Homo sapiens*]; (5126:) pterin-4a-carbinolamine dehydratase; (5127:) Pterin-4-alpha-carbinolamine dehydratase (PHS) (4-alpha-hydroxy-tetrahydropterin dehydratase) (Phenylalaninehydroxylase-stimulating protein) (Pterin carbinolamine dehydratase) (PCD) (Dimerization cofactor of hepatocyte nuclear factor 1-alpha) (Dimerization cofactor of HNF1) (DCoH); (5128:) Pterin-4-alpha-carbinolamine dehydratase 2 (PHS 2) (4-alpha-hydroxy-tetrahydropterin dehydratase 2) (DcoH-like proteinDCoHm) (Dimerization cofactor of hepatocyte nuclear factor 1 from-muscle) (HNF1-alpha dimerization cofactor); (5129:) PTK2 protein tyrosine kinase 2 isoform a [*Homo sapiens*]; (5130:) PTK2 protein tyrosine kinase 2 isoform b [*Homo sapiens*];

(5131:) P-Type Calcium Channel Blocker; (5132:) Purine Nucleoside Phosphorylase (PNP); (5133:) purine nucleoside phosphorylase [Homo sapiens]; (5134:) putative 1-aminocyclopropane-1-carboxylate synthase [Homo sapiens]; (5135:) putative acyl-CoA dehydrogenase [Homo sapiens]; (5136:) putative b,b-carotene-9',10'-dioxygenase [Homo sapiens]; (5137:) Putative C→U-editing enzyme APOBEC-4 (Apolipoprotein BmRNA-editing enzyme catalytic polypeptide-like 4); (5138:) putative carotene dioxygenase [Homo sapiens]; (5139:) putative deubiquitinazing enzyme [Homo sapiens]; (5140:) Putative G-protein coupled receptor 42; (5141:) Putative G-protein coupled receptor 44 (Chemoattractant receptor-homologous molecule expressed on Th2 cells) (CD294antigen); (5142:) "putative non-ribosomal peptide synthetase NRPS1098; hNRPS1098 [Homo sapiens]."; (5143:) putative non-ribosomal peptide synthetase NRPS998 [Homo sapiens]; (5144:) Putative P2Y purinoceptor 10 (P2Y10) (P2Y-like receptor); (5145:) putative peroxisomal antioxidant enzyme [Homo sapiens]; (5146:) putative protein O-mannosyltransferase [Homo sapiens]; (5147:) putative pyroglutamyl-peptidase I [Homo sapiens]; (5148:) Putative Taste receptor type 2 member 12 (T2R12) (Taste receptor type 2 member 26) (T2R26); (5149:) putative ubiquitin-conjugating enzyme E2 variant [Homo sapiens]; (5150:) pVHL-interacting deubiquitinating enzyme 1 type I [Homo sapiens]; (5151:) pVHL-interacting deubiquitinating enzyme 1 type II [Homo sapiens]; (5152:) pVHL-interacting deubiquitinating enzyme 2 [Homo sapiens]; (5153:) Pyridoxal kinase (Pyridoxine kinase); (5154:) pyridoxal kinase [Homo sapiens]; (5155:) Pyridoxal phosphate phosphatase (PLP phosphatase); (5156:) Pyridoxal phosphate phosphatase PHOSPHO2; (5157:) pyridoxine 5'-phosphate oxidase [Homo sapiens]; (5158:) pyroglutamyl-peptidase I [Homo sapiens]; (5159:) pyrophosphatase 1 [Homo sapiens]; (5160:) pyrroline 5-carboxylate synthetase [Homo sapiens]; (5161:) pyrroline-5-carboxylate reductase 1 isoform 1 [Homo sapiens]; (5162:) pyrroline-5-carboxylate reductase 1 isoform 2 [Homo sapiens]; (5163:) pyrroline-5-carboxylate synthase [Homo sapiens]; (5164:) pyrroline-5-carboxylate synthase long form [Homo sapiens]; (5165:) pyrroline-5-carboxylate synthetase isoform 1 [Homo sapiens]; (5166:) pyrroline-5-carboxylate synthetase isoform 2 [Homo sapiens]; (5167:) Pyruvate carboxylase [Homo sapiens]; (5168:) pyruvate carboxylase precursor [Homo sapiens]; (5169:) pyruvate carboxylase precursor; (5170:) Pyruvate carboxylase, mitochondrial precursor (Pyruvic carboxylase) (PCB); (5171:) pyruvate carboxylase; (5172:) "pyruvate carboxylase; pyruvate:carbon dioxide ligase [Homo sapiens]."; (5173:) pyruvate dehydrogenase (lipoamide) alpha 1 [Homo sapiens]; (5174:) Pyruvate Dehydrogenase (PDH) Kinase; (5175:) pyruvate dehydrogenase complex protein X subunit precursor [Homo sapiens]; (5176:) pyruvate dehydrogenase complex, component X [Homo sapiens]; (5177:) Pyruvate dehydrogenase E1 component alpha subunit, somatic form, mitochondrial precursor (PDHE1-A type I); (5178:) Pyruvate dehydrogenase E1 component alpha subunit, testis-specific form, mitochondrial precursor (PDHE1-A type II); (5179:) Pyruvate dehydrogenase E1 component subunit beta, mitochondrial precursor (PDHE1-B); (5180:) Pyruvate Dehydrogenase Kinase 2 (PDHK2); (5181:) Pyruvate dehydrogenase protein X component, mitochondrial precursor (Dihydrolipoamide dehydrogenase-binding protein of pyruvatedehydrogenase complex) (Lipoyl-containing pyruvate dehydrogenase complex component X) (E3-binding protein) (E3BP) (proX); (5182:) pyruvate kinase (EC 2.7.1.40), muscle splice form M1—human; (5183:) pyruvate kinase [Homo sapiens]; (5184:) pyruvate kinase 3 isoform 1 [Homo sapiens]; (5185:) pyruvate kinase 3 isoform 1 variant [Homo sapiens]; (5186:) pyruvate kinase 3 isoform 2 [Homo sapiens]; (5187:) Pyruvate kinase isozymes M1/M2 (Pyruvate kinase muscle isozyme) (Pyruvate kinase 2/3) (Cytosolic thyroid hormone-binding protein) (CTHBP) (THBP1); (5188:) Pyruvate kinase isozymes R/L (R-type/L-type pyruvate kinase) (Redcell/liver pyruvate kinase) (Pyruvate kinase 1); (5189:) pyruvate kinase L [Homo sapiens]; (5190:) pyruvate kinase M2 [Homo sapiens]; (5191:) pyruvate kinase PK-L isoenzyme [Homo sapiens]; (5192:) pyruvate kinase PK-R isoenzyme [Homo sapiens]; (5193:) Pyruvate kinase, liver and RBC [Homo sapiens]; (5194:) pyruvate kinase, liver and RBC isoform 1 [Homo sapiens]; (5195:) pyruvate kinase, liver and RBC isoform 2 [Homo sapiens]; (5196:) Pyruvate kinase, muscle [Homo sapiens]; (5197:) pyruvate kinase; (5198:) carbon-dioxide ligase (ADP-forming); (5199:) Pyruvate:Ferredoxin Oxidoreductase (PFOR); (5200:) QTRT1 protein [Homo sapiens]; (5201:) QTRTD1 protein [Homo sapiens]; (5202:) Queuine tRNA-ribosyltransferase (tRNA-guanine transglycosylase) (Guanine insertion enzyme); (5203:) quinoid dihydropteridine reductase [Homo sapiens]; (5204:) quinolinate phosphoribosyltransferase [Homo sapiens]; (5205:) rabaptin, RAB GTPase binding effector protein 1 [Homo sapiens]; (5206:) Rac GTPase activating protein 1 [Homo sapiens]; (5207:) RAD18 [Homo sapiens]; (5208:) RAD51 homolog protein isoform 1 [Homo sapiens]; (5209:) RAD51 homolog protein isoform 2 [Homo sapiens]; (5210:) RAD6 homolog; (5211:) Raf Kinase (RKI); (5212:) ralA binding protein 1 [Homo sapiens]; (5213:) RALBP1 associated Eps domain containing 2 [Homo sapiens]; (5214:) Ran binding protein 11 [Homo sapiens]; (5215:) RAN binding protein 2 [Homo sapiens]; (5216:) RAN binding protein 9 [Homo sapiens]; (5217:) Ran GTPase activating protein 1 [Homo sapiens]; (5218:) Ran GTPase-activating protein 1; (5219:) Ran-binding protein 2 (RanBP2) (Nuclear pore complex proteinNup358) (Nucleoporin Nup358) (358 kDa nucleoporin) (P270); (5220:) Ran-binding protein 9 (RanBP9) (RanBP7) (Ran-binding protein M) (RanBPM) (BPM90) (BPM-L); (5221:) RanBP-type and C3HC4-type zinc finger containing 1 isoform 1 [Homo sapiens]; (5222:) RanBP-type and C3HC4-type zinc finger containing 1 isoform 2 [Homo sapiens]; (5223:) RanBP-type and C3HC4-type zinc finger-containing protein 1(Ubiquitin-conjugating enzyme 7-interacting protein 3) (Hepatitis Bvirus X-associated protein 4) (HBV-associated factor 4) (RINGfinger protein 54); (5224:) Ras-GTPase-activating protein SH3-domain-binding protein [Homo sapiens]; (5225:) Ras-related C3 botulinum toxin substrate 1 precursor (p21-Rac1) (Ras-like protein TC25); (5226:) Ras-related C3 botulinum toxin substrate 2 precursor (p21-Rac2) (Small G protein) (GX); (5227:) Ras-related protein Rab-5A; (5228:) Ras-related protein Rab-5B; (5229:) Ras-related protein Rap-1A precursor (GTP-binding protein smg-p21A) (Ras-related protein Krev-1) (C21KG) (G-22K); (5230:) Ras-related protein Rap-1b precursor (GTP-binding protein smgp21B); (5231:) Ras-related protein Rap-2a (RbBP-30); (5232:) rcUBE2S [Homo sapiens]; (5233:) Receptor activity-modifying protein 1 precursor (CRLR activity-modifying protein 1) (Calcitonin-receptor-like receptor activity-modifying protein 1); (5234:) Receptor activity-modifying protein 2 precursor (CRLRactivity-modifying protein 2) (Calcitonin-receptor-like receptor activity-modifying protein 2); (5235:) Receptor activity-modifying protein 3 precursor (CRLR activity-modifying protein 3) (Calcitonin-receptor-like receptor activity-modifying protein 3); (5236:) Receptor Gamma (RXR Gamma); (5237:) Receptor tyrosine-protein kinase erbB-2 precursor (p185erbB2) (C-erbB-2) (NEU proto-oncogene) (Tyrosine kinase-type cell surface receptor HER2) (MLN 19) (CD340 antigen); (5238:) Receptor tyrosine-protein kinase erbB-3 precursor (c-erbB3) (Tyrosine kinase-type cell surface receptor HER3); (5239:) Receptor tyrosine-protein kinase erbB-4 precursor (p180erbB4) (Tyrosine kinase-type cell surface receptor HER4); (5240:) Receptor-binding cancer antigen expressed on SiSo cells(Cancer-associated surface antigen RCAS1) (Estrogen receptor-binding fragment-associated gene 9 protein); (5241:) receptor-interacting serine-threonine kinase 2 [Homo sapiens]; (5242:) Receptor-type tyrosine-protein phosphatase delta precursor (Protein-tyrosine phosphatase delta) (R-PTP-delta); (5243:) Receptor-type tyrosine-protein phosphatase F precursor (LAR protein) (Leukocyte antigen related); (5244:) Receptor-type tyrosine-protein phosphatase kappa precursor (Protein-tyrosine phosphatase kappa) (R-PTP-kappa); (5245:) Receptor-type tyrosine-protein phosphatase mu precursor (Protein-tyrosine phosphatase mu) (R-PTP-mu); (5246:) Receptor-type tyrosine-protein phosphatase N2 precursor (R-PTP-N2) (Islet cell autoantigen-related protein) (ICAAR) (IAR) (Phogrin); (5247:) Receptor-type tyrosine-protein phosphatase O precursor (Glomerular epithelial protein 1) (Protein tyrosine phosphatase U2) (PTPase U2) (PTP-U2); (5248:) Receptor-type tyrosine-protein phosphatase R precursor (Protein-tyrosine phosphatase PCPTP1) (NC-PTPCOM1) (Ch-1PTPase); (5249:) Receptor-type tyrosine-protein phosphatase S precursor (R-PTP-S) (Protein-tyrosine phosphatase sigma) (R-PTP-sigma); (5250:) Receptor-type tyrosine-protein phosphatase T precursor (R-PTP-T) (RPTP-rho); (5251:) Receptor-type tyrosine-protein phosphatase U precursor (R-PTP-U) (Protein-tyrosine phosphatase J) (PTP-J) (Pancreatic carcinoma phosphatase 2) (PCP-2); (5252:) Receptor-type tyrosine-protein phosphatase-like N precursor (R-PTP-N) (PTP IA-2) (Islet cell antigen 512) (ICA 512) (Islet cell autoantigen 3); (5253:) RECK protein precursor [Homo sapiens]; (5254:) RecQ protein-like isoform 1 [Homo sapiens]; (5255:) redox active peptide; (5256:) Red-sensitive opsin (Red cone photoreceptor pigment); (5257:) reductase, dihydrofolate; (5258:) Ref-1 [Homo sapiens]; (5259:) regenerating islet-derived 1 alpha precursor [Homo sapiens]; (5260:) Relaxin receptor 1 (Relaxin family peptide receptor 1) (Leucine-rich repeat-containing G-protein coupled receptor 7); (5261:) Relaxin receptor 2 (Relaxin family peptide receptor 2) (Leucine-rich repeat-containing G-protein coupled receptor 8) (G-protein coupled receptor affecting testicular descent) (G-protein coupled receptor 106); (5262:) Relaxin-3 receptor 1 (RLN3 receptor 1) (Relaxin family peptide receptor 3) (Somatostatin- and angiotensin-like peptide receptor) (G protein-coupled receptor SALPR) (GPCR135); (5263:) Relaxin-3 receptor 2 (Relaxin family peptide receptor 4) (G-protein coupled receptor 100) (GPCR142); (5264:) Renin; (5265:) renin binding protein [Homo sapiens]; (5266:) Renin precursor (Angiotensinogenase); (5267:) Renin receptor precursor (Renin/prorenin receptor) (ATPaseH(+)-transporting lysosomal accessory protein 2) (ATPaseH(+)-transporting lysosomal-interacting protein 2) (Vacuolar ATPsynthase membrane sector-associated protein M8-9) (V-ATPase M8.9subunit) (ATP6M8-9) (N14F) (ER-localized type I transmembrane adaptor) (Embryonic liver differentiation factor 10); (5268:) resist in [Homo sapiens]; (5269:) Ret Receptor Tyrosine Kinase Stimulator; (5270:) Reticulon-4 receptor precursor (Nogo receptor) (NgR) (Nogo-66receptor); (5271:) Reticulon-4 receptor-like 1 precursor (Nogo-66 receptor homolog 2) (Nogo-66 receptor-related protein 3) (NgR3) (Nogo receptor-like 2); (5272:) Reticulon-4 receptor-like 2 precursor (Nogo-66 receptor homolog 1) (Nogo-66 receptor-related protein 2) (NgR2) (Nogo receptor-like 3); (5273:) retina copper-containing monoamine oxidase [Homo sapiens]; (5274:) Retinal dehydrogenase 1 (RaIDH1) (RALDH 1) (Aldehyde dehydrogenase family 1 member A1) (Aldehyde dehydrogenase, cytosolic) (ALHDII) (ALDH-E1); (5275:) Retinal guanylyl cyclase 1 precursor (Guanylate cyclase 2D,retinal) (RETGC-1) (Rod outer segment membrane guanylate cyclase) (ROS-GC); (5276:) Retinal guanylyl cyclase 2 precursor (Guanylate cyclase 2F,retinal) (RETGC-2) (Rod outer segment membrane guanylate cyclase 2) (ROS-GC2) (Guanylate cyclase F) (GC-F); (5277:) retinal pigment epithelium-specific protein 65 kDa [Homo sapiens]; (5278:) retina-specific amine oxidase [Homo sapiens]; (5279:) Retina-specific copper amine oxidase precursor (RAO) (Amine oxidase[copper-containing]); (5280:) retinoblastoma 1 [Homo sapiens]; (5281:) retinoblastoma-like 2 (p130) [Homo sapiens]; (5282:) retinoic acid hydroxylase [Homo sapiens]; (5283:) Retinoic acid receptor alpha (RAR-alpha); (5284:) Retinoic acid receptor beta (RAR-beta) (RAR-epsilon) (HBV-activated protein); (5285:) Retinoic acid receptor gamma-1 (RAR-gamma-1); (5286:) Retinoic acid receptor gamma-2 (RAR-gamma-2); (5287:) Retinoic acid receptor RXR-alpha (Retinoid X receptor alpha); (5288:) Retinoic acid receptor RXR-beta (Retinoid X receptor beta); (5289:) Retinoic acid receptor RXR-gamma (Retinoid X receptor gamma); (5290:) Retinoic Acid Receptor-Alpha (RAR Alpha); (5291:) Retinoic Acid Receptor-Beta (RAR Beta); (5292:) Retinoic Acid Receptor-Gamma (RAR Gamma); (5293:) Retinoic acid-induced protein 3 (G-protein coupled receptor family C group 5 member A) (Retinoic acid-induced gene 1 protein) (RAIG-1) (Orphan G-protein coupling receptor PEIG-1); (5294:) Retinoic X Receptor Alpha (RXR Alpha); (5295:) Retinoic X Receptor Beta (RXR Beta); (5296:) retinoid X receptor, alpha [Homo sapiens]; (5297:) Retinol Dehydrogenase; (5298:) Retinol dehydrogenase 12 (All-trans and 9-cis retinoldehydrogenase); (5299:) retinol dehydrogenase 12 (all-trans and 9-cis) [Homo sapiens]; (5300:) Retinol dehydrogenase 13; (5301:) retinol dehydrogenase 16 [Homo sapiens]; (5302:) retinol dehydrogenase 5 (11-cis and 9-cis) [Homo sapiens]; (5303:) retinol dehydrogenase 8 (all-trans) [Homo sapiens]; (5304:) rhabdomyosarcoma antigen MU-RMS-40.10E [Homo sapiens]; (5305:) Rho GTPase Protein; (5306:) Rho-associated protein kinase 1 (Rho-associated, coiled-coil-containing protein kinase 1) (p160 ROCK-1) (p160ROCK) (NY-REN-35 antigen); (5307:) Rho-associated protein kinase 2 (Rho-associated,coiled-coil-containing protein kinase 2) (p164 ROCK-2) (Rho kinase2); (5308:) Rho-associated, coiled-coil containing protein kinase 1 [Homo sapiens]; (5309:) Rhodopsin (Opsin-2); (5310:) Rho-Kinase; (5311:) Rho-related GTP-binding protein RhoQ (Ras-related GTP-binding protein TC10); (5312:) Ribonuclease 4 precursor (RNase 4); (5313:) Ribonuclease H1 (RNase H1) (Ribonuclease H type II); (5314:) ribonuclease H1 [Homo sapiens]; (5315:) Ribonuclease H2 subunit A (RNase H2 subunit A) (Ribonuclease H1 subunit A) (Ribonuclease HI large subunit) (RNase HI large subunit) (RNase H(35)) (Aicardi-Goutieres syndrome 4 protein) (AGS4); (5316:) ribonuclease HI, large subunit [Homo sapiens]; (5317:) ribonuclease III, nuclear [Homo sapiens]; (5318:) ribonuclease, RNase A family, 4 precursor [Homo sapiens]; (5319:) Ribonucleoside-diphosphate reductase large subunit(Ribonucleoside-diphosphate reductase M1 subunit) (Ribonucleotidereductase large chain); (5320:) ribonucleoside-diphosphate reductase M1 chain [Homo sapiens]; (5321:) Ribonucleotide Reductase (RR); (5322:)

Ribose-phosphate pyrophosphokinase I (Phosphoribosyl pyrophosphatesynthetase I) (PRS-I) (PPRibP); (5323:) Ribose-phosphate pyrophosphokinase II (Phosphoribosyl pyrophosphatesynthetase II) (PRS-II) (PPRibP); (5324:) Ribose-phosphate pyrophosphokinase III (Phosphoribosylpyrophosphate synthetase III) (PRS-III) (Phosphoribosylpyrophosphate synthetase 1-like 1); (5325:) Ribosomal protein S6 kinase alpha-1 (S6K-alpha 1) (90 kDa ribosomal protein S6 kinase 1) (p90-RSK 1) (Ribosomal S6 kinase 1) (RSK-1) (pp 90RSK1) (p90S6K) (MAP kinase-activated protein kinase 1a) (MAPKAPK1A); (5326:) Ribosomal protein S6 kinase alpha-2 (S6K-alpha 2) (90 kDa ribosomal-protein S6 kinase 2) (p90-RSK 2) (Ribosomal S6 kinase 3) (RSK-3) (pp 90RSK3) (MAP kinase-activated protein kinase 1c) (MAPKAPK1C); (5327:) Ribosomal protein S6 kinase alpha-3 (S6K-alpha 3) (90 kDa ribosomalprotein S6 kinase 3) (p90-RSK 3) (Ribosomal S6 kinase 2) (RSK-2) (pp 90RSK2) (Insulin-stimulated protein kinase 1) (ISPK-1) (MAPkinase-activated protein kinase 1b) (MAPKAPK1B); (5328:) Ribosomal protein S6 kinase alpha-4 (Nuclear mitogen- and stress-activated protein kinase 2) (90 kDa ribosomal protein S6kinase 4) (Ribosomal protein kinase B) (RSKB); (5329:) Ribosomal protein S6 kinase alpha-5 (Nuclear mitogen- and stress-activated protein kinase 1) (90 kDa ribosomal protein S6kinase 5) (RSK-like protein kinase) (RSKL); (5330:) Ribosomal protein S6 kinase alpha-6 (S6K-alpha 6) (90 kDa ribosomalprotein S6 kinase 6) (p90-RSK 6) (Ribosomal S6 kinase 4) (RSK-4) (pp 90RSK4); (5331:) Ribosomal protein S6 kinase beta-1 (Ribosomal protein S6 kinase I) (S6K) (S6K1) (70 kDa ribosomal protein S6 kinase 1) (p70 S6 kinasealpha) (p70(S6K)-alpha) (p70-S6K) (P70S6K) (p70-alpha); (5332:) Ribosyldihydronicotinamide dehydrogenase [quinone] (NRHdehydrogenase [quinone] 2) (Quinone reductase 2) (QR2) (NRH:quinoneoxidoreductase 2); (5333:) RING finger and WD repeat domain protein 2 (Ubiquitin-proteinligase COP1) (Constitutive photomorphogenesis protein 1 homolog) (hCOP1); (5334:) RING finger protein 125 (T-cell RING activation protein 1) (TRAC-1); (5335:) RING finger protein 139 (Translocation in renal carcinoma onchromosome 8); (5336:) ring finger protein 139 [*Homo sapiens*]; (5337:) ring finger protein 144 [*Homo sapiens*]; (5338:) ring finger protein 2 [*Homo sapiens*]; (5339:) ring finger protein 25 [*Homo sapiens*]; (5340:) RING finger protein 25; (5341:) RING finger protein 37 (Ubiquitin-conjugating enzyme 7-interacting protein 5) (U-box domain-containing protein 5); (5342:) ring finger protein 41 isoform 1 [*Homo sapiens*]; (5343:) ring finger protein 41 isoform 2 [*Homo sapiens*]; (5344:) ring finger protein 7 isoform 1 [*Homo sapiens*]; (5345:) ring finger protein 7 isoform 3 [*Homo sapiens*]; (5346:) RING-box protein 1 (Rbx1) (Regulator of cullins 1) (RING finger protein 75) (Protein ZYP); (5347:) RING-box protein 2 (Rbx2) (RING finger protein 7) (Regulator of cullins 2) (CKII beta-binding protein 1) (CKBBP1) (Sensitive toapoptosis gene protein); (5348:) RNA (guanine-7-) methyltransferase [*Homo sapiens*]; (5349:) RNA (guanine-N7-) methyltransferase [*Homo sapiens*]; (5350:) RNA 3'-terminal phosphate cyclase (RNA-3'-phosphate cyclase) (RNAcyclase); (5351:) RNA cyclase homolog [*Homo sapiens*]; (5352:) RNA guanylyltransferase and 5'-phosphatase [*Homo sapiens*]; (5353:) RNA lariat debranching enzyme [*Homo sapiens*]; (5354:) RNA polymerase I-associated factor PAF49 (Anti-sense to ERCC-1protein) (ASE-1) (CD3-epsilon-associated protein) (CD3E-associated protein) (CAST); (5355:) RNA polymerase II transcription factor SIII p18 subunit; (5356:) RNA polymerase III subunit RPC155-A [*Homo sapiens*]; (5357:) RNA polymerase III subunit RPC155-B [*Homo sapiens*]; (5358:) RNA polymerase III subunit RPC155-C [*Homo sapiens*]; (5359:) RNA polymerase III subunit RPC155-D [*Homo sapiens*]; (5360:) RNA polymerase III subunit RPC62 [*Homo sapiens*]; (5361:) RNA polymerase transcriptional regulation mediator, subunit 6homolog (Activator-recruited cofactor 33 kDa component) (ARC33) (NY-REN-28 antigen); (5362:) RNA-specific adenosine deaminase B1 isoform 1 [*Homo sapiens*]; (5363:) RNA-specific adenosine deaminase B1 isoform 2 [*Homo sapiens*]; (5364:) RNA-specific adenosine deaminase B1 isoform 3 [*Homo sapiens*]; (5365:) RNA-specific adenosine deaminase B1 isoform 4 [*Homo sapiens*]; (5366:) RNPEPL1 protein [*Homo sapiens*]; (5367:) Roundabout homolog 1 precursor (H-Robo-1) (Deleted in U twenty twenty); (5368:) Roundabout homolog 3 precursor (Roundabout-like protein 3); (5369:) Roundabout homolog 4 precursor (Magic roundabout); (5370:) RP11-235O14.2 [*Homo sapiens*]; (5371:) RPE-retinal G protein-coupled receptor; (5372:) "R-type pyruvate kinase; R-type PK [*Homo sapiens*]."; (5373:) Ryanodine Receptor 1 (RyR1); (5374:) Ryanodine receptor 1 (Skeletal muscle-type ryanodine receptor) (RyR1) (RyR-1) (Skeletal muscle calcium release channel); (5375:) Ryanodine receptor 2 (Cardiac muscle-type ryanodine receptor) (RyR2) (RyR-2) (Cardiac muscle ryanodine receptor-calcium release channel) (hRyR-2); (5376:) Ryanodine receptor 3 (Brain-type ryanodine receptor) (RyR3) (RyR-3) (Brain ryanodine receptor-calcium release channel); (5377:) S100 calcium-binding protein A8 [*Homo sapiens*]; (5378:) S100 calcium-binding protein A9 [*Homo sapiens*]; (5379:) SA [*Homo sapiens*]; (5380:) SA hypertension-associated homolog isoform 2 [*Homo sapiens*]; (5381:) S-adenosylhomocysteine hydrolase [*Homo sapiens*]; (5382:) S-adenosylmethionine decarboxylase (SAMDC); (5383:) S-adenosylmethionine decarboxylase 1 isoform 1 precursor [*Homo sapiens*]; (5384:) S-adenosylmethionine decarboxylase 1 isoform 2 [*Homo sapiens*]; (5385:) "S-adenosylmethionine decarboxylase proenzyme (AdoMetDC) (SamDC)[Contains:) S-adenosylmethionine decarboxylase alpha chain;S-adenosylmethionine decarboxylase beta chain]."; (5386:) Salivary alpha-amylase precursor (1,4-alpha-D-glucanglucanohydrolase); (5387:) sarco/endoplasmic reticulum Ca2+-ATPase isoform a [*Homo sapiens*]; (5388:) sarco/endoplasmic reticulum Ca2+-ATPase isoform b [*Homo sapiens*]; (5389:) sarco/endoplasmic reticulum Ca2+-ATPase isoform c [*Homo sapiens*]; (5390:) sarco/endoplasmic reticulum Ca2+-ATPase isoform d [*Homo sapiens*]; (5391:) sarco/endoplasmic reticulum Ca2+-ATPase isoform e [*Homo sapiens*]; (5392:) sarco/endoplasmic reticulum Ca2+-ATPase isoform f [*Homo sapiens*]; (5393:) Sarcoplasmic/endoplasmic reticulum calcium ATPase 1 (Calcium pump1) (SERCA1) (SR Ca(2+)-ATPase 1) (Calcium-transporting ATPasesarcoplasmic reticulum type, fast twitch skeletal muscle isoform) (Endoplasmic reticulum class 1/2 Ca(2+) ATPase); (5394:) Sarcoplasmic/endoplasmic reticulum calcium ATPase 2 (Calcium pump2) (SERCA2) (SR Ca(2+)-ATPase 2) (Calcium-transporting ATPasesarcoplasmic reticulum type, slow twitch skeletal muscle isoform) (Endoplasmic reticulum class 1/2 Ca(2+) ATPase); (5395:) Sarcoplasmic/endoplasmic reticulum calcium ATPase 3 (Calcium pump3) (SERCA3) (SR Ca(2+)-ATPase 3); (5396:) SARS Virus Protease; (5397:) scavenger mRNA decapping enzyme [*Homo sapiens*]; (5398:) Scavenger mRNA decapping enzyme DcpS (DCS-1) (Hint-related7meGMP-directed hydrolase) (Histidine triad protein member 5) (HINT-5); (5399:) Scavenger receptor class B member 1 (SRB1) (SR-BI) (CD36antigen-like 1) (CD36 and LIMPII analogous 1) (CLA-1) (Collagentype I receptor, thrombospondin receptor-like 1); (5400:) scavenger receptor class B, member 1 [*Homo sapiens*]; (5401:) Scavenger receptor class F member 2 precursor (Scavenger receptorexpressed by endothelial cells 2 protein) (SREC-II) (SRECRP-1); (5402:) SDS protein [*Homo sapiens*]; (5403:) SDSL protein [*Homo sapiens*]; (5404:) SEC14-like 2 [*Homo sapiens*]; (5405:) SECIS binding protein 2 [*Homo sapiens*]; (5406:) Secreted Apoptosis-Related Protein 2 (SARP2); (5407:) Secretin Receptor (SCTR); (5408:) Secretin receptor precursor (SCT-R); (5409:) Secretory Leukocyte Protease (SLPI); (5410:) Secretory Phospholipase A2 (sPLA2); (5411:) Secretory Protein Clusterin (sCLU); (5412:) selectin E precursor [*Homo sapiens*]; (5413:) selectin L precursor [*Homo sapiens*]; (5414:) selectin P ligand [*Homo sapiens*]; (5415:) selectin P precursor [*Homo sapiens*]; (5416:) selenocysteine lyase [*Homo sapiens*]; (5417:) selenophosphate synthetase [*Homo sapiens*]; (5418:) selenophosphate synthetase 2 [*Homo sapiens*]; (5419:) Semaphorin-4D precursor (Leukocyte activation antigen CD100) (BB18) (A8) (GR3); (5420:) Semicarbazide-Sensitive Amine Oxidase (SSAO); (5421:) Sentrin-specific protease 8 (Sentrin/SUMO-specific protease SENP8) (Protease, cysteine 2) (NEDD8-specific protease 1) (Deneddylase-1); (5422:) Separin (Separase) (Caspase-like protein ESPL1) (Extra spindlepoles-like 1 protein); (5423:) sepiapterin reductase (7,8-dihydrobiopterin:NADP+oxidoreductase) [*Homo sapiens*]; (5424:) Sepiapterin reductase (SPR); (5425:) sepiapterin reductase; (5426:) Serase-1B [*Homo sapiens*]; (5427:) serine (or cysteine) proteinase inhibitor, Glade A (alpha-1 antiproteinase, antitrypsin), member 1 [*Homo sapiens*]; (5428:) serine (or cysteine) proteinase inhibitor, Glade B (ovalbumin),member 2 [*Homo sapiens*]; (5429:) serine (or cysteine) proteinase inhibitor, Glade B (ovalbumin),member 9 [*Homo sapiens*]; (5430:) serine (or cysteine) proteinase inhibitor, clade I (neuroserpin),member 1 [*Homo sapiens*]; (5431:) serine dehydratase (EC 4.2.1.13); (5432:) serine dehydratase [*Homo sapiens*]; (5433:) serine dehydratase-2 [*Homo sapiens*]; (5434:) serine dehydratase-like [*Homo sapiens*]; (5435:) serine hydroxymethyltransferase 1 (soluble) isoform 1 [*Homo sapiens*]; (5436:) serine hydroxymethyltransferase 1 (soluble) isoform 2 [*Homo sapiens*]; (5437:) Serine hydroxymethyltransferase, cytosolic (Serine methylase) (Glycine hydroxymethyltransferase) (SHMT); (5438:) Serine hydroxymethyltransferase, mitochondrial precursor (Serinemethylase) (Glycine hydroxymethyltransferase) (SHMT); (5439:) serine palmitoyltransferase (SPT); (5440:) Serine palmitoyltransferase 1 (Long chain base biosynthesis protein1) (LCB 1) (Serine-palmitoyl-CoA transferase 1) (SPT 1) (SPT1); (5441:) Serine palmitoyltransferase 2 (Long chain base biosynthesis protein2) (LCB 2) (Serine-palmitoyl-CoA transferase 2) (SPT 2); (5442:) serine palmitoyltransferase subunit 1 isoform a [*Homo sapiens*]; (5443:) serine palmitoyltransferase subunit 1 isoform b [*Homo sapiens*]; (5444:) serine palmitoyltransferase, long chain base subunit 2 [*Homo sapiens*]; (5445:) serine palmitoyltransferase, subunit I [*Homo sapiens*]; (5446:) serine palmitoyltransferase, subunit II [*Homo sapiens*]; (5447:) serine protease inhibitor, Kazal type 1 [*Homo sapiens*]; (5448:) serine racemase [*Homo sapiens*]; (5449:) Serine racemase; (5450:) serine/threonine kinase 16 [*Homo sapiens*]; (5451:) Serine/threonine kinase NLK (Nemo-like kinase) (Protein LAK1); (5452:) Serine/threonine-protein kinase 25 (Sterile 20/oxidantstress-response kinase 1) (Step 20/oxidant stress response kinase 1) (SOK-1) (Step 20-like kinase); (5453:) Serine/threonine-protein kinase 3 (STE20-like kinase MST2) (MST-2) (Mammalian STE20-like protein kinase 2) (Serine/threonine-proteinkinase Krs-1); (5454:) Serine/threonine-protein kinase 36 (Fused homolog); (5455:) Serine/threonine-protein kinase 38 (NDR1 protein kinase) (NuclearDbf2-related kinase 1); (5456:) Serine/threonine-protein kinase 38-like (NDR2 protein kinase) (Nuclear Dbf2-related kinase 2); (5457:) Serine/threonine-protein kinase 4 (STE20-like kinase MST1) (MST-1) (Mammalian STE20-like protein kinase 1) (Serine/threonine-proteinkinase Krs-2); (5458:) Serine/threonine-protein kinase ATR (Ataxia telangiectasia and Rad3-related protein) (FRAP-related protein 1); (5459:) Serine/threonine-protein kinase Chk2 (Cds1); (5460:) Serine/threonine-protein kinase D1 (nPKC-D1) (Protein kinase D) (Protein kinase C mu type) (nPKC-mu); (5461:) Serine/threonine-protein kinase D2 (nPKC-D2); (5462:) Serine/threonine-protein kinase D3 (Protein kinase C nu type) (nPKC-nu) (Protein kinase EPK2); (5463:) Serine/threonine-protein kinase H1 (PSK-H1); (5464:) Serine/threonine-protein kinase ICK (Intestinal cell kinase) (hICK) (MAK-related kinase) (MRK) (Laryngeal cancer kinase 2) (LCK2); (5465:) Serine/threonine-protein kinase MARK1 (MAP/microtubule affinity-regulating kinase 1); (5466:) Serine/threonine-protein kinase MARK2 (MAP/microtubuleaffinity-regulating kinase 2) (ELKL motif kinase) (EMK1) (PAR1homolog); (5467:) Serine/threonine-protein kinase MRCK (CDC42-binding proteinkinase alpha) (Myotonic dystrophy kinase-related CDC42-binding kinase alpha) (Myotonic dystrophy protein kinase-like alpha) (MRCKalpha) (DMPK-like alpha); (5468:) Serine/threonine-protein kinase MRCK beta (CDC42-binding proteinkinase beta) (Myotonic dystrophy kinase-related CDC42-binding kinase beta) (Myotonic dystrophy protein kinase-like beta) (MRCKbeta) (DMPK-like beta); (5469:) Serine/threonine-protein kinase MRCK gamma (CDC42-binding proteinkinase gamma) (Myotonic dystrophy kinase-related CDC42-bindingkinase gamma) (Myotonic dystrophy protein kinase-like alpha) (MRCK-gamma) (DMPK-like gamma); (5470:) Serine/threonine-protein kinase MST4 (STE20-like kinase MST4) (MST-4) (Mammalian STE20-like protein kinase 4) (Serine/threonine-protein kinase MASK) (Mst3 and SOK1-related kinase); (5471:) Serine/threonine-protein kinase N1 (Protein kinase C-like 1) (Protein-kinase C-related kinase 1) (Protein kinase C-like PKN) (Serine-threonine protein kinase N) (Protein kinase PKN-alpha); (5472:) Serine/threonine-protein kinase N2 (Protein kinase C-like 2) (Protein-kinase C-related kinase 2); (5473:) Serine/threonine-protein kinase Nek11 (NimA-related protein kinase11) (Never in mitosis A-related kinase 11); (5474:) Serine/threonine-protein kinase Nek2 (NimA-related protein kinase2) (NimA-like protein kinase 1) (HSPK 21); (5475:) Serine/threonine-protein kinase Nek9 (NimA-related protein kinase9) (Never in mitosis A-related kinase 9) (Nercc1 kinase) (NIMA-related kinase 8) (Nek8); (5476:) Serine/threonine-protein kinase NIM1; (5477:) Serine/threonine-protein kinase OSR1 (Oxidative stress-responsive 1protein); (5478:) Serine/threonine-protein kinase PAK 1 (p21-activated kinase 1) (PAK-1) (P65-PAK) (Alpha-PAK); (5479:) Serine/threonine-protein kinase PAK 2 (p21-activated kinase 2) (PAK-2) (PAK65) (Gamma-PAK) (S6/H4 kinase); (5480:) Serine/threonine-protein kinase PAK 3 (p21-activated kinase 3) (PAK-3) (Beta-PAK) (Oligophrenin-3); (5481:) Serine/threonine-protein kinase receptor R3 precursor (SKR3) (Activin receptor-like kinase 1) (ALK-1) (TGF-B superfamily receptor type I) (TSR-I); (5482:) Serine/threonine-protein kinase SMG1 (SMG-1) (hSMG-1) (Lambda/iotaprotein kinase C-interacting protein) (Lambda-interacting protein) (61E3.4); (5483:) Serine/threonine-protein kinase SNF1-like kinase 1(Serine/threonine-protein kinase SNF1LK);

(5484:) Serine/threonine-protein kinase SNF1-like kinase 2 (Qin-induced kinase); (5485:) Serine/threonine-protein kinase SRPK1 (Serine/arginine-rich protein-specific kinase 1) (SR-protein-specific kinase 1) (SFRS protein kinase 1); (5486:) Serine/threonine-protein kinase SRPK2 (Serine/arginine-rich protein-specific kinase 2) (SR-protein-specific kinase 2) (SFR Sprotein kinase 2); (5487:) Serine/threonine-protein kinase TBK1 (TANK-binding kinase 1) (T2K) (NF-kappa-B-activating kinase); (5488:) Serine/threonine-protein kinase tousled-like 1 (Tousled-like kinase1) (PKU-beta); (5489:) Serine/threonine-protein kinase tousled-like 2 (Tousled-like kinase2) (PKU-alpha); (5490:) Serine/threonine-protein kinase VRK1 (Vaccinia-related kinase 1); (5491:) Serine/threonine-protein kinase WNK1 (Protein kinase with no lysine1) (Protein kinase, lysine-deficient 1) (Kinase deficient protein); (5492:) Serine/threonine-protein kinase WNK2 (Protein kinase with no lysine-2) (Protein kinase, lysine-deficient 2); (5493:) Serine/threonine-protein kinase WNK3 (Protein kinase with no lysine-3) (Protein kinase, lysine-deficient 3); (5494:) Serine/threonine-protein kinase WNK4 (Protein kinase with no lysine-4) (Protein kinase, lysine-deficient 4); (5495:) "Serine/threonine-protein kinase/endoribonuclease IRE1 precursor (Inositol-requiring protein 1) (hIRE1p) (IRE1a) (Ire1-alpha) (Endoplasmic reticulum-to-nucleus signaling 1) [Includes: Serine/threonine-protein kinase; Endoribonuclease]."; (5496:) "Serine/threonine-protein kinase/endoribonuclease IRE2 precursor (Inositol-requiring protein 2) (hIRE2p) (IRE1b) (Ire1-beta) (Endoplasmic reticulum-to-nucleus signaling 2) [Includes: Serine/threonine-protein kinase; Endoribonuclease]."; (5497:) Serine/threonine-protein phosphatase 2A 48 kDa regulatory subunit B(PP2A, subunit B, PR48 isoform); (5498:) Serine/threonine-protein phosphatase 2A 55 kDa regulatory subunit Balpha isoform (PP2A, subunit B, B-alpha isoform) (PP2A, subunit B,B55-alpha isoform) (PP2A, subunit B, PR55-alpha isoform) (PP2A,subunit B, R2-alpha isoform); (5499:) Serine/threonine-protein phosphatase 2A 55 kDa regulatory subunit Bbeta isoform (PP2A, subunit B, B-beta isoform) (PP2A, subunit B,B55-beta isoform) (PP2A, subunit B, PR55-beta isoform) (PP2A, subunit B, R2-beta isoform); (5500:) Serine/threonine-protein phosphatase 2A 55 kDa regulatory subunit Bdelta isoform (PP2A, subunit B, B-delta isoform) (PP2A, subunit B,B55-delta isoform) (PP2A, subunit B, PR55-delta isoform) (PP2A,subunit B, R2-delta isoform); (5501:) Serine/threonine-protein phosphatase 2A 55 kDa regulatory subunit Bgamma isoform (PP2A, subunit B, B-gamma isoform) (PP2A, subunit B,B55-gamma isoform) (PP2A, subunit B, PR55-gamma isoform) (PP2A,subunit B, R2-gamma isoform) (IMYPNO1); (5502:) Serine/threonine-protein phosphatase 2A 56 kDa regulatory subunitalpha isoform (PP2A, B subunit, B' alpha isoform) (PP2A, B subunit,B56 alpha isoform) (PP2A, B subunit, PR61 alpha isoform) (PP2A, Bsubunit, R5 alpha isoform); (5503:) Serine/threonine-protein phosphatase 2A 56 kDa regulatory subunitbeta isoform (PP2A, B subunit, B' beta isoform) (PP2A, B subunit,B56 beta isoform) (PP2A, B subunit, PR61 beta isoform) (PP2A, Bsubunit, R5 beta isoform); (5504:) Serine/threonine-protein phosphatase 2A 56 kDa regulatory subunit delta isoform (PP2A, B subunit, B' delta isoform) (PP2A, B subunit,B56 delta isoform) (PP2A, B subunit, PR61 delta isoform) (PP2A, Bsubunit, R5 delta isoform); (5505:) Serine/threonine-protein phosphatase 2A 56 kDa regulatory subunit epsilon isoform (PP2A, B subunit, B' epsilon isoform) (PP2A, Bsubunit, B56 epsilon isoform) (PP2A, B subunit, PR61 epsilon isoform) (PP2A, B subunit, R5 epsilon isoform); (5506:) Serine/threonine-protein phosphatase 2A 56 kDa regulatory subunit gamma isoform (PP2A, B subunit, B' gamma isoform) (PP2A, B subunit,B56 gamma isoform) (PP2A, B subunit, PR61 gamma isoform) (PP2A, Bsubunit, R5 gamma isoform) (NY-REN-29 antigen); (5507:) Serine/threonine-protein phosphatase 2A 65 kDa regulatory subunit Abeta isoform (PP2A, subunit A, PR65-beta isoform) (PP2A, subunit A,R1-beta isoform); (5508:) Serine/threonine-protein phosphatase 2A 65 kDa regulatory subunit Aalpha isoform (PP2A, subunit A, PR65-alpha isoform) (PP2A, subunitA, R1-alpha isoform) (Medium tumor antigen-associated 61 kDa protein); (5509:) Serine/threonine-protein phosphatase 2A 72/130 kDa regulatory subunit B (PP2A, subunit B, B"-PR72/PR130) (PP2A, subunit B,B72/B130 isoforms) (PP2A, subunit B, PR72/PR130 isoforms) (PP2A,subunit B, R3 isoform); (5510:) Serine/threonine-protein phosphatase 2A catalytic subunit alphaisoform (PP2A-alpha) (Replication protein C) (RP-C); (5511:) Serine/threonine-protein phosphatase 2A catalytic subunit betaisoform (PP2A-beta); (5512:) Serine/threonine-protein phosphatase 2A regulatory subunit B'(PP2A, subunit B', PR53 isoform) (Phosphotyrosyl phosphatase activator) (PTPA); (5513:) Serine/threonine-protein phosphatase with EF-hands 1 (PPEF-1) (Protein phosphatase with EF calcium-binding domain) (PPEF) (Serine/threonine-protein phosphatase 7) (PP7); (5514:) Serine/threonine-protein phosphatase with EF-hands 2 (PPEF-2); (5515:) Serine-protein kinase ATM (Ataxia telangiectasia mutated) (A-T, mutated); (5516:) serum albumin precursor [*Homo sapiens*]; (5517:) Serum paraoxonase/arylesterase 1 (PON 1) (Serumaryldialkylphosphatase 1) (A-esterase 1) (Aromatic esterase 1) (K-45); (5518:) serum/glucocorticoid regulated kinase [*Homo sapiens*]; (5519:) seryl-tRNA synthetase [*Homo sapiens*]; (5520:) SET and MYND domain-containing protein 3 (Zinc finger MYNDdomain-containing protein 1); (5521:) SET domain-containing protein 7 [*Homo sapiens*]; (5522:) SH3-containing GRB2-like protein 2 (Endophilin-1) (Endophilin-A1) (SH3 domain protein 2A) (EEN-B1); (5523:) SH3-domain kinase-binding protein 1 (Cbl-interacting protein of 85 kDa) (Human Src-family kinase-binding protein 1) (HSB-1) (CD2-binding protein 3) (CD2BP3); (5524:) short/branched chain acyl-CoA dehydrogenase [*Homo sapiens*]; (5525:) Short/branched chain specific acyl-CoA dehydrogenase, mitochondrial precursor (SBCAD) (2-methyl branched chain acyl-CoA dehydrogenase) (2-MEBCAD) (2-methylbutyryl-coenzyme A dehydrogenase) (2-methylbutyryl-CoA dehydrogenase); (5526:) sialidase 2 [*Homo sapiens*]; (5527:) sialidase 3 [*Homo sapiens*]; (5528:) sialidase 4 [*Homo sapiens*]; (5529:) Sialidase-1 precursor (Lysosomal sialidase) (N-acetyl-alpha-neuraminidase 1) (Acetylneuraminyl hydrolase) (G9sialidase); (5530:) sialyltransferase 1 isoform a [*Homo sapiens*]; (5531:) sialyltransferase 1 isoform b [*Homo sapiens*]; (5532:) sialyltransferase 6 isoform a [*Homo sapiens*]; (5533:) sialyltransferase 6 isoform b [*Homo sapiens*]; (5534:) sialyltransferase 6 isoform c [*Homo sapiens*]; (5535:) sialyltransferase 6 isoform d [*Homo sapiens*]; (5536:) sialyltransferase 6 isoform e [*Homo sapiens*]; (5537:) sialyltransferase 6 isoform f [*Homo sapiens*]; (5538:) sialyltransferase 6 isoform g [*Homo sapiens*]; (5539:) sialyltransferase 6 isoform h [*Homo sapiens*]; (5540:) sialyltransferase 6 isoform i [*Homo sapiens*]; (5541:) sialyltransferase 6 isoform j [*Homo sapiens*]; (5542:) Sigma Receptor; (5543:) Sigma1 Receptor; (5544:) Sigma2 Receptor; (5545:) signal peptide peptidase-like 2B isoform 2 [*Homo sapiens*]; (5546:) signal peptide peptidase-like 2B isoform 3 [*Homo sapiens*]; (5547:) Signal recognition particle receptor subunit alpha (SR-alpha) (Docking protein alpha) (DP-alpha); (5548:) Signal recognition particle receptor subunit beta (SR-beta) (Protein APMCF1); (5549:) Signal Transducer and Activator of Transcription 1 (STAT1); (5550:) Signal Transducer and Activator of Transcription 3 (STAT3); (5551:) Signal Transducer and Activator of Transcription 4 (STAT4); (5552:) Signal transducing adapter molecule 2 (STAM-2); (5553:) signal transducing adaptor molecule 1 [Homo sapiens]; (5554:) signal transducing adaptor molecule 2 [Homo sapiens]; (5555:) Signal transduction protein CBL-C(SH3-binding protein CBL-C) (CBL-3) (RING finger protein 57); (5556:) Signaling lymphocytic activation molecule precursor (IPO-3) (CD150antigen) (CDw150); (5557:) Single-strand selective monofunctional uracil DNA glycosylase; (5558:) Sirtunin 1 (SIRT1); (5559:) skeletal myosin light chain kinase [Homo sapiens]; (5560:) Skin Protease (SPI); (5561:) SLAM family member 5 precursor (Signaling lymphocytic activation molecule 5) (Leukocyte differentiation antigen CD84) (CD84 antigen) (Cell surface antigen MAX.3) (Hly9-beta); (5562:) SLAM family member 6 precursor (NK-T-B-antigen) (NTB-A) (Activating NK receptor); (5563:) SLAM family member 7 precursor (CD2-like receptor activating cytotoxic cells) (CRACC) (Protein 19A) (CD2 subset 1) (Novel Ly9) (Membrane protein FOAP-12) (CD319 antigen); (5564:) SLC27A1 protein [Homo sapiens]; (5565:) SLC27A3 protein [Homo sapiens]; (5566:) Smad ubiquitination regulatory factor 1 (Ubiquitin—protein ligase SMURF1) (Smad-specific E3 ubiquitin ligase 1) (hSMURF1); (5567:) Smad ubiquitination regulatory factor 2 (Ubiquitin—protein ligase SMURF2) (Smad-specific E3 ubiquitin ligase 2) (hSMURF2); (5568:) "Small inducible cytokine A14 precursor (CCL14) (ChemokineCC-1/CC-3) (HCC-1/HCC-3) (HCC-1(1-74)) (NCC-2) [Contains:HCC-1(3-74); HCC-1 (4-74); HCC-1(9-74)]."; (5569:) small inducible cytokine A2 precursor [Homo sapiens]; (5570:) "Small inducible cytokine AS precursor (CCL5) (T-cell-specific RANTES protein) (SIS-delta) (T cell-specific protein P228) (TCP228) [Contains:) RANTES(3-68); RANTES(4-68)]."; (5571:) small inducible cytokine B10 precursor [Homo sapiens]; (5572:) Small ubiquitin-related modifier 4 precursor (SUMO-4) (Small ubiquitin-like protein 4); (5573:) S-methyl-5-thioadenosine phosphorylase (5'-methylthioadenosinephosphorylase) (MTA phosphorylase) (MTAPase); (5574:) Smoothened homolog precursor (SMO) (Gx protein); (5575:) SMT3 suppressor of mif two 3 homolog 1 isoform a precursor [Homo sapiens]; (5576:) SMT3 suppressor of mif two 3 homolog 1 isoform b precursor [Homo sapiens]; (5577:) Sn1-specific diacylglycerol lipase alpha (DGL-alpha) (Neural stem cell-derived dendrite regulator); (5578:) Sn1-specific diacylglycerol lipase beta (DGL-beta) (KCCR13L); (5579:) snake venom-like protease [Homo sapiens]; (5580:) SNF-related serine/threonine-protein kinase (SNF1-related kinase); (5581:) Sodium bicarbonate cotransporter 3 (Sodium bicarbonatecotransporter 2) (Sodium bicarbonate cotransporter 2b) (Bicarbonate transporter) (Solute carrier family 4 member 7); (5582:) Sodium Hydrogen Exchange (NHE); (5583:) Sodium Hydrogen Exchange Isoform-1 (NHE-1); (5584:) Sodium Hydrogen Exchange Isoform-3 (NHE-3); (5585:) Sodium/calcium exchanger 1 precursor (Na(+)/Ca(2+)-exchange protein1); (5586:) Sodium/calcium exchanger 2 precursor (Na(+)/Ca (2+)-exchange protein2); (5587:) Sodium/calcium exchanger 3 precursor (Na(+)/Ca(2+)-exchange protein3); (5588:) Sodium/nucleoside cotransporter 2 (Na(+)/nucleoside cotransporter2) (Sodium-coupled nucleoside transporter 2) (Concentrative nucleoside transporter 2) (CNT 2) (hCNT2) (Sodium/purine nucleosideco-transporter) (SPNT); (5589:) Sodium/potassium-transporting ATPase alpha-1 chain precursor (Sodium pump 1) (Na+/K+ ATPase 1); (5590:) Sodium/potassium-transporting ATPase alpha-2 chain precursor (Sodium pump 2) (Na+/K+ ATPase 2); (5591:) Sodium/potassium-transporting ATPase alpha-3 chain (Sodium pump 3) (Na+/K+ ATPase 3) (Alpha(III)); (5592:) Sodium/potassium-transporting ATPase alpha-4 chain (Sodium pump 4) (Na+/K+ ATPase 4); (5593:) Sodium/potassium-transporting ATPase subunit beta-1(Sodium/potassium-dependent ATPase beta-1 subunit); (5594:) Sodium/potassium-transporting ATPase subunit beta-2(Sodium/potassium-dependent ATPase beta-2 subunit); (5595:) Sodium/potassium-transporting ATPase subunit beta-3(Sodium/potassium-dependent ATPase beta-3 subunit) (ATPB-3) (CD298antigen); (5596:) Sodium-Chloride Cotransporter (NCC); (5597:) Sodium-dependent phosphate transporter 1 (Solute carrier family 20member 1) (Phosphate transporter 1) (PiT-1) (Gibbon ape leukemiavirus receptor 1) (GLVR-1) (Leukemia virus receptor 1 homolog); (5598:) Sodium-Glucose Cotransporter (SGLT); (5599:) Sodium-Glucose Cotransporter Type 1 (SGLT1); (5600:) Sodium-Glucose Cotransporter Type 2 (SGLT2); (5601:) Sodium-Potassium ATPase; (5602:) Sodium-Potassium-Chloride Cotransporter; (5603:) Soluble calcium-activated nucleotidase 1 (SCAN-1) (Apyrase homolog) (Putative NF-kappa-B-activating protein 107) (PutativeMAPK-activating protein PM09); (5604:) soluble calcium-activated nucleotidase 1 [Homo sapiens]; (5605:) solute carrier family 2 (facilitated glucose transporter), member 1 [Homo sapiens]; (5606:) solute carrier family 27 (fatty acid transporter), member 2 [Homo sapiens]; (5607:) solute carrier family 7 (cationic amino acid transporter, y+system), member 1 [Homo sapiens]; (5608:) solute carrier family 7, member 2 isoform 1 [Homo sapiens]; (5609:) solute carrier family 7, member 2 isoform 2 [Homo sapiens]; (5610:) Somatostatin Receptor (SSTR); (5611:) Somatostatin Receptor 1 (SSTR1); (5612:) Somatostatin Receptor 2 (SSTR2); (5613:) Somatostatin Receptor 3 (SSTR3); (5614:) Somatostatin Receptor 5 (SSTR5); (5615:) Somatostatin receptor type 1 (SS1R) (SRIF-2); (5616:) Somatostatin receptor type 2 (SS2R) (SRIF-1); (5617:) Somatostatin receptor type 3 (SS3R) (SSR-28); (5618:) Somatostatin receptor type 4 (SS4R); (5619:) Somatostatin receptor type 5 (SS5R); (5620:) Sorbitol dehydrogenase (L-iditol 2-dehydrogenase); (5621:) sorbitol dehydrogenase [Homo sapiens]; (5622:) Sortilin precursor (Neurotensin receptor 3) (NTR3) (NT3) (Glycoprotein 95) (Gp95) (100 kDa NT receptor); (5623:) sortilin-related receptor containing LDLR class A repeats preproprotein [Homo sapiens]; (5624:) Sortilin-related receptor precursor (Sorting protein-related receptor containing LDLR class A repeats) (SorLA) (SorLA-1) (Low-density lipoprotein receptor relative with 11 ligand-binding repeats) (LDLR relative with 11 ligand-binding repeats) (LR11); (5625:) Sorting nexin-1; (5626:) Sorting nexin-2 (Transformation-related gene 9 protein) (TRG-9); (5627:) Sp1 transcription factor [Homo sapiens]; (5628:) spectrin, alpha, erythrocytic 1 [Homo sapiens]; (5629:) spen homolog, transcriptional regulator [Homo sapiens]; (5630:) sperm adhesion molecule 1 isoform 1 [Homo sapiens]; (5631:) sperm adhesion molecule 1 isoform 2 [Homo sapiens]; (5632:) Spermidine synthase (Putrescine aminopropyltransferase) (SPDSY); (5633:) spermidine synthase [Homo sapiens]; (5634:) Spermidine/Spermine N1-Acetyltransferase (SSAT); (5635:) spermidine/spermine N1-acetyltransferase [Homo sapiens]; (5636:) Spermine oxidase (Polyamine oxidase 1) (PAO-1) (PAOh1); (5637:) spermine synthase [Homo sapiens]; (5638:) S-phase kinase-associated protein 1A isoform a [Homo sapiens]; (5639:) S-phase kinase-associated protein 1A isoform b [Homo sapiens]; (5640:) S-phase kinase-associated protein 2 isoform 1 [Homo sapiens]; (5641:) S-phase kinase-associated protein 2 isoform 2 [Homo sapiens]; (5642:) sphingomyelin phosphodiesterase (EC 3.1.4.12)—human (fragments); (5643:) sphingomyelin phosphodiesterase [Homo sapiens]; (5644:) sphingomyelin phosphodiesterase 1, acid lysosomal isoform 1 precursor [Homo sapiens]; (5645:) sphingomyelin phosphodiesterase 1, acid lysosomal isoform 2precursor [Homo sapiens]; (5646:) Sphingomyelin phosphodiesterase 3 (Neutral sphingomyelinase 2) (Neutral sphingomyelinase II) (nSMase2) (nSMase-2); (5647:) Sphingomyelin phosphodiesterase precursor (Acid sphingomyelinase) (aSMase); (5648:) Sphingosine 1-Phosphate (SIP) Receptor; (5649:) Sphingosine 1-Phosphate Receptor 1 (S1P1); (5650:) Sphingosine 1-phosphate receptor Edg-1 (Sphingosine 1-phosphate receptor 1) (S1P1); (5651:) Sphingosine 1-phosphate receptor Edg-3 (S1P receptor Edg-3) (Endothelial differentiation G-protein coupled receptor 3) (Sphingosine 1-phosphate receptor 3) (S1P3); (5652:) Sphingosine 1-phosphate receptor Edg-5 (SIP receptor Edg-5) (Endothelial differentiation G-protein coupled receptor 5) (Sphingosine 1-phosphate receptor 2) (S1P2); (5653:) Sphingosine 1-phosphate receptor Edg-6 (SIP receptor Edg-6) (Endothelial differentiation G-protein coupled receptor 6) (Sphingosine 1-phosphate receptor 4) (S1P4); (5654:) Sphingosine 1-phosphate receptor Edg-8 (Endothelial differentiation sphingolipid G-protein-coupled receptor 8) (Sphingosine 1-phosphate receptor 5) (S1P5); (5655:) Sphingosine 1-phosphate receptor GPR6 (G-protein coupled receptor6); (5656:) sphingosine kinase 1 isoform 1 [Homo sapiens]; (5657:) sphingosine kinase 1 isoform 2 [Homo sapiens]; (5658:) Sphingosylphosphorylcholine receptor (Ovarian cancer G-protein coupled receptor 1) (OGR-1) (G-protein coupled receptor 68) (GPR12A); (5659:) Spleen Tyrosine Kinase (Syk); (5660:) Squalene Synthase; (5661:) Squalene synthetase (SQS) (SS) (Farnesyl-diphosphatefarnesyltransferase) (FPP:FPP farnesyltransferase); (5662:) Sqv-8-like protein [Homo sapiens]; (5663:) Src Homology-2-Containing Protein Tyrosine Phosphatase-1 (SHP-1); (5664:) Src Tyrosine Kinase (STK); (5665:) SRC/ABL Kinase; (5666:) SRP RNA 3' adenylating enzyme/pap2 [Homo sapiens]; (5667:) SRR [Homo sapiens]; (5668:) ST3 beta-galactoside alpha-2,3-sialyltransferase 5 isoform 1 [Homo sapiens]; (5669:) ST3 beta-galactoside alpha-2,3-sialyltransferase 5 isoform 2 [Homo sapiens]; (5670:) ST8 alpha-N-acetyl-neuraminide alpha-2,8-sialyltransferase 1 [Homo sapiens]; (5671:) Stabilin-1 precursor (FEEL-1 protein) (MS-1 antigen); (5672:) Stabilin-2 precursor (FEEL-2 protein) (Fasciclin EGF-like laminin-type EGF-like and link domain-containing scavenger receptor1) (FAS1 EGF-like and X-link domain-containing adhesion molecule 2) (Hyaluronan receptor for endocytosis) [Contains:) 190 kDa formstabilin-2 (190 kDa hyaluronan receptor for endocytosis)]; (5673:) STAM binding protein [Homo sapiens]; (5674:) STAM-binding protein (Associated molecule with the SH3 domain of STAM); (5675:) Staphylococcus aureus Methionyl-tRNA Synthetase (MetS); (5676:) stearoyl-CoA desaturase [Homo sapiens]; (5677:) stearoyl-CoA desaturase 4 isoform a [Homo sapiens]; (5678:) stearoyl-CoA desaturase 4 isoform b [Homo sapiens]; (5679:) steroid dehydrogenase homolog [Homo sapiens]; (5680:) Steroid hormone receptor ERR1 (Estrogen-related receptor, alpha) (ERR-alpha) (Estrogen receptor-like 1); (5681:) Steroid hormone receptor ERR2 (Estrogen-related receptor, beta) (ERR-beta) (Estrogen receptor-like 2) (ERR beta-2); (5682:) Steroid receptor RNA activator 1 (Steroid receptor RNA activator protein) (SRAP); (5683:) steroid sulfatase [Homo sapiens]; (5684:) Steroid X Receptor (SXR); (5685:) steroid-5-alpha-reductase 1 [Homo sapiens]; (5686:) Steroidogenic factor 1 (STF-1) (SF-1) (Adrenal 4-binding protein) (Steroid hormone receptor Ad4BP) (Fushi tarazu factor homolog 1); (5687:) sterol O-acyltransferase (acyl-Coenzyme A:) cholesterolacyltransferase) 1 [Homo sapiens]; (5688:) sterol-05-desaturase-like [Homo sapiens]; (5689:) steryl-sulfatase precursor [Homo sapiens]; (5690:) Stomach Acid Neutralizer; (5691:) Stratum Corneum Chymotryptic Enzyme (SCCE); (5692:) stratum corneum chymotryptic enzyme [Homo sapiens]; (5693:) stratum corneum chymotryptic enzyme preproprotein [Homo sapiens]; (5694:) stratum corneum chymotryptic enzyme; (5695:) stratum corneum tryptic enzyme [Homo sapiens]; (5696:) Stress-Associated Endoplasmic Reticulum Protein 1 (SERP1); (5697:) Substance-K receptor (SKR) (Neurokinin A receptor) (NK-2 receptor) (NK-2R) (Tachykinin receptor 2); (5698:) Substance-P receptor (SPR) (NK-1 receptor) (NK-1R) (Tachykinin receptor 1); (5699:) Substrate Binding And Catalysis By Glutathione Reductase As Derived From Refined Enzyme:) Substrate Crystal Structures At 2 Angstroms Resolution; (5700:) subtilisin-like proprotein convertase (EC 3.4.21.-) homolog—human; (5701:) succinate dehydrogenase complex, subunit A, flavoprotein precursor [Homo sapiens]; (5702:) succinate dehydrogenase complex, subunit B, iron sulfur (Ip) [Homo sapiens]; (5703:) succinate dehydrogenase complex, subunit C isoform 1 precursor [Homo sapiens]; (5704:) succinate dehydrogenase complex, subunit C isoform 2 precursor [Homo sapiens]; (5705:) succinate dehydrogenase complex, subunit C isoform 3 precursor [Homo sapiens]; (5706:) succinate dehydrogenase complex, subunit C isoform 4 precursor [Homo sapiens]; (5707:) succinate dehydrogenase complex, subunit D precursor [Homo sapiens]; (5708:) succinate dehydrogenase flavoprotein subunit; (5709:) Succinate receptor 1 (G-protein coupled receptor 91) (P2Y purinoceptor 1-like); (5710:) Succinate semialdehyde dehydrogenase, mitochondrial precursor (NAD(+)-dependent succinic semialdehyde dehydrogenase); (5711:) succinate-CoA ligase, ADP-forming, beta subunit [Homo sapiens]; (5712:) succinyl CoA:3-oxoacid CoA transferase precursor; (5713:) Succinyl-CoA ligase [ADP-forming] beta-chain, mitochondrial precursor (Succinyl-CoA synthetase, betaA chain) (SCS-betaA) (ATP-specific succinyl-CoA synthetase subunit beta) (NY-REN-39antigen); (5714:) Succinyl-CoA:3-ketoacid-coenzyme A transferase 1, mitochondrial precursor (Somatic-type succinyl CoA:3-oxoacid CoA-transferase) (Scot-S); (5715:) Succinyl-CoA:3-ketoacid-coenzyme A transferase 2, mitochondrial precursor (Testis-specific succinyl CoA:3-oxoacid CoA-transferase) (SCOT-t); (5716:) "Sucrase-isomaltase, intestinal [Contains:) Sucrase; Isomaltase]."; (5717:) Sulfatase; (5718:) sulfatase modifying factor 1 [Homo sapiens]; (5719:) sulfatase modifying factor 2 isoform a precursor [Homo sapiens]; (5720:) sulfatase modifying factor 2 isoform b precursor [Homo sapiens]; (5721:) sulfatase modifying factor 2 isoform c precursor [Homo sapiens]; (5722:) sulfatase modifying factor 2 isoform d precursor [Homo sapiens]; (5723:) Sulfatase-modifying factor 1 precursor (C-alpha-formyglycine-generating enzyme 1); (5724:) Sulfatase-modifying factor 2 precursor (C-alpha-formyglycine-generating enzyme 2); (5725:) sulfite oxidase [Homo sapiens]; (5726:) Sulfite oxidase, mitochondrial precursor; (5727:) Sulfonylurea Receptor 1 (SUR1); (5728:) Sulfotransferase 1A1 (Aryl sulfotransferase 1) (Phenolsulfotransferase 1) (Phenol-sulfating phenol sulfotransferase 1) (P-PST 1) (Thermostable phenol sulfotransferase) (Ts-PST)

(HAST1/HAST2) (ST1A3); (5729:) sulfotransferase family, cytosolic, 1A, phenol-preferring, member 1 isoform a [*Homo sapiens*]; (5730:) sulfotransferase family, cytosolic, 1A, phenol-preferring, member 1 isoform b [*Homo sapiens*]; (5731:) sulfotransferase family, cytosolic, 1A, phenol-preferring, member 2 [*Homo sapiens*]; (5732:) sulfotransferase family, cytosolic, 1A, phenol-preferring, member 3 [*Homo sapiens*]; (5733:) sulfotransferase family, cytosolic, 1A, phenol-preferring, member 4 [*Homo sapiens*]; (5734:) sulfotransferase family, cytosolic, 2A, dehydroepiandrosterone-preferring, member 1 [*Homo sapiens*]; (5735:) sulfotransferase family, cytosolic, 2B, member 1 isoform a [*Homo sapiens*]; (5736:) sulfotransferase family, cytosolic, 2B, member 1 isoform b [*Homo sapiens*]; (5737:) SUMO1 activating enzyme subunit 1 [*Homo sapiens*]; (5738:) SUMO-1 activating enzyme subunit 1 [*Homo sapiens*]; (5739:) SUMO1 activating enzyme subunit 2 [*Homo sapiens*]; (5740:) SUMO-1 activating enzyme subunit 2 [*Homo sapiens*]; (5741:) SUMO-1 activating enzyme subunit 2 variant [*Homo sapiens*]; (5742:) SUMO-1-activating enzyme E1 C subunit [*Homo sapiens*]; (5743:) SUMO-1-activating enzyme E1 N subunit [*Homo sapiens*]; (5744:) SUMO-1-conjugating enzyme UBC9 (SUMO-1-protein ligase) (Ubiquitin-conjugating enzyme E2 I) (Ubiquitin-protein ligase I) (Ubiquitin carrier protein I) (Ubiquitin carrier protein 9) (p18); (5745:) Superoxide Dismutase (SOD) Mimetic; (5746:) Superoxide dismutase [Cu—Zn]; (5747:) Superoxide Dismutase 1 (SOD1); (5748:) superoxide dismutase 1, soluble [*Homo sapiens*]; (5749:) suppressor of variegation 3-9 homolog 1 [*Homo sapiens*]; (5750:) SUR5 [*Homo sapiens*]; (5751:) Survivin; (5752:) SWI/SNF related, matrix associated, actin dependent regulator of chromatin, subfamily b, member 1 isoform a [*Homo sapiens*]; (5753:) SWI/SNF related, matrix associated, actin dependent regulator of chromatin, subfamily b, member 1 isoform b [*Homo sapiens*]; (5754:) SWI/SNF-related matrix-associated actin-dependent regulator ofchromatin a4 [*Homo sapiens*]; (5755:) SWI/SNF-related matrix-associated actin-dependent regulator ofchromatin a5 [*Homo sapiens*]; (5756:) synapsin I [*Homo sapiens*]; (5757:) synapsin I isoform Ia [*Homo sapiens*]; (5758:) synapsin I isoform Ib [*Homo sapiens*]; (5759:) Synapsin-1 (Synapsin I) (Brain protein 4.1); (5760:) synaptojanin 2 binding protein [*Homo sapiens*]; (5761:) synuclein alpha interacting protein [*Homo sapiens*]; (5762:) synuclein, gamma (breast cancer-specific protein 1) [*Homo sapiens*]; (5763:) T cell receptor delta chain [*Homo sapiens*]; (5764:) tachykinin receptor 1 isoform long [*Homo sapiens*]; (5765:) tachykinin receptor 1 isoform short [*Homo sapiens*]; (5766:) TAF2 protein [*Homo sapiens*]; (5767:) TAF9 RNA polymerase II isoform b [*Homo sapiens*]; (5768:) TAF9 RNA polymerase II isoform c [*Homo sapiens*]; (5769:) TAF9 RNA polymerase II, TATA box binding protein (TBP)-associated factor, 32 kDa [*Homo sapiens*]; (5770:) talin 1 [*Homo sapiens*]; (5771:) TANK-binding kinase 1 [*Homo sapiens*]; (5772:) tartrate resistant acid phosphatase 5 precursor [*Homo sapiens*]; (5773:) Taste receptor type 1 member 1 precursor (G-protein coupled receptor 70); (5774:) Taste receptor type 1 member 2 precursor (G-protein coupled receptor 71) (Sweet taste receptor T1R2); (5775:) Taste receptor type 1 member 3 precursor (Sweet taste receptor T1R3); (5776:) Taste receptor type 2 member 1 (T2R1) (Taste receptor family B member 7) (TRB7); (5777:) Taste receptor type 2 member 10 (T2R10) (Taste receptor family B member 2) (TRB2); (5778:) Taste receptor type 2 member 13 (T2R13) (Taste receptor family B member 3) (TRB3); (5779:) Taste receptor type 2 member 14 (T2R14) (Taste receptor family B member 1) (TRB1); (5780:) Taste receptor type 2 member 16 (T2R16); (5781:) Taste receptor type 2 member 3 (T2R3); (5782:) Taste receptor type 2 member 38 (T2R38) (T2R61) (PTC bitter taste receptor); (5783:) Taste receptor type 2 member 39 (T2R39) (T2R57); (5784:) Taste receptor type 2 member 4 (T2R4); (5785:) Taste receptor type 2 member 40 (T2R40) (T2R58) (G-protein coupled receptor 60); (5786:) Taste receptor type 2 member 41 (T2R41) (T2R59); (5787:) Taste receptor type 2 member 42 (T2R42) (T2R55); (5788:) Taste receptor type 2 member 43 (T2R43) (T2R52); (5789:) Taste receptor type 2 member 44 (T2R44) (T2R53); (5790:) Taste receptor type 2 member 45 (T2R45) (G-protein coupled receptor59); (5791:) Taste receptor type 2 member 46 (T2R46) (T2R54); (5792:) Taste receptor type 2 member 47 (T2R47); (5793:) Taste receptor type 2 member 48 (T2R48); (5794:) Taste receptor type 2 member 49 (T2R49) (T2R56); (5795:) Taste receptor type 2 member 5 (T2R5); (5796:) Taste receptor type 2 member 50 (T2R50) (T2R51); (5797:) Taste receptor type 2 member 60 (T2R60) (T2R56); (5798:) Taste receptor type 2 member 7 (T2R7) (Taste receptor family B member 4) (TRB4); (5799:) Taste receptor type 2 member 8 (T2R8) (Taste receptor family B member 5) (TRB5); (5800:) Taste receptor type 2 member 9 (T2R9) (Taste receptor family B member 6) (TRB6); (5801:) TBP-associated factor 1 isoform 1 [*Homo sapiens*]; (5802:) TBP-associated factor 1 isoform 2 [*Homo sapiens*]; (5803:) T-cell antigen CD7 precursor (GP40) (T-cell leukemia antigen) (TP41) (Leu-9); (5804:) T-cell receptor alpha chain (clone A21)—human (fragment); (5805:) T-cell receptor alpha chain (Mb11a) precursor—human (fragment); (5806:) T-cell receptor alpha chain C region; (5807:) T-cell receptor alpha chain V region CTL-L17 precursor; (5808:) T-cell receptor alpha chain V region HPB-MLT precursor; (5809:) T-cell receptor alpha chain V region PY14 precursor; (5810:) T-cell receptor beta chain C region; (5811:) T-cell receptor beta chain V region—human (fragment); (5812:) T-cell receptor beta chain V region CTL-L17 precursor; (5813:) T-cell receptor beta chain V region YT35 precursor; (5814:) T-cell receptor gamma chain C region PT-gamma-1/2; (5815:) T-cell receptor gamma chain V region PT-gamma-1/2 precursor; (5816:) T-cell receptor Vb CDR3, carrier PBL Vb 12a.sbt—human(fragment); (5817:) T-cell receptor Vb CDR3, carrier PBL Vb 12b.sbt—human(fragment); (5818:) T-cell receptor Vb CDR3, carrier PBL Vb 2.sbt—human (fragment); (5819:) T-cell receptor Vb CDR3, carrier PBL Vb 6.sbt—human (fragment); (5820:) T-cell receptor Vb CDR3, carrier PBL Vb 7.sbt—human (fragment); (5821:) T-cell receptor Vb CDR3, carrier Vb 17.sbt—human (fragment); (5822:) T-cell receptor Vb CDR3, Ctrl TCR Vb 12 CDR 3aa.sbt—human(fragment); (5823:) T-cell receptor Vb CDR3, Ctrl TCR Vb 7CDR 3aas.sbt—human (fragment); (5824:) T-cell receptor Vb CDR3, Ctrl TCR Vb8 CDR 3aas.sbt—human(fragment); (5825:) T-cell receptor Vb CDR3, Ctr2 TCR Vb12 CDR 3aa.sbt—human(fragment); (5826:) T-cell receptor Vb CDR3, HAM1TCR Vb12b CDR3a.sbt—human(fragment); (5827:) T-cell receptor Vb CDR3, HAM1TCR Vb14 CDR3a.sbt—human(fragment); (5828:) T-cell receptor Vb CDR3, HAM1TCR Vb5a CDR3a.sbt—human(fragment); (5829:) T-cell receptor Vb CDR3, HAM1TCR VbSb CDR3a.sbt—human(fragment); (5830:) T-cell receptor Vb CDR3, HAM1TCR Vb5C CDR 3aa.sbt—human(fragment); (5831:) T-cell receptor Vb CDR3, HAM1TCR Vb5d CDR3a.sbt—human(fragment); (5832:) T-cell receptor Vb CDR3, HAM1TCR Vb6b CDR3a.sbt—human(fragment); (5833:) T-cell receptor Vb CDR3, HAM1TCR Vb7a CDR3a.sbt—human(fragment); (5834:) T-cell receptor Vb CDR3, HAM1TCR Vb7b CDR3a.sbt—human(fragment); (5835:) T-cell receptor Vb CDR3, HAM1TCR Vb8a CDR3a.sbt—human(fragment); (5836:) T-cell receptor Vb CDR3, HAM1TCR Vb8b CDR3a.sbt—human(fragment); (5837:) T-cell receptor Vb CDR3, HAM2TCR Vb 19a.sbt—human (fragment); (5838:) T-cell receptor Vb CDR3, HAM2TCR Vb17 CDR3a.sbt—human(fragment); (5839:) T-cell receptor Vb CDR3, HAM2TCR Vb19b CDR3a.sbt—human(fragment); (5840:) T-cell receptor Vb CDR3, HAM2TCR Vb6a CDR3a.sbt—human(fragment); (5841:) T-cell receptor Vb CDR3, HAM2TCR Vb6b CDR3a.sbt—human(fragment); (5842:) T-cell receptor Vb CDR3, HAM2TCR Vb8a CDR3a.sbt—human(fragment); (5843:) T-cell receptor Vb CDR3, HAM2TCR Vb8c CDR3a.sbt—human(fragment); (5844:) T-cell receptor zeta chain isoform 1 precursor [Homo sapiens]; (5845:) T-cell receptor zeta chain isoform 2 precursor [Homo sapiens]; (5846:) T-cell surface glycoprotein CD3 delta chain precursor (T-cell receptor T3 delta chain); (5847:) T-cell surface glycoprotein CD3 epsilon chain precursor (T-cellsurface antigen T3/Leu-4 epsilon chain); (5848:) T-cell surface glycoprotein CD3 gamma chain precursor (T-cellreceptor T3 gamma chain); (5849:) T-cell surface glycoprotein CD3 zeta chain precursor (T-cellreceptor T3 zeta chain) (CD237 antigen); (5850:) T-cell, immune regulator 1 isoform a [Homo sapiens]; (5851:) T-cell, immune regulator 1 isoform b [Homo sapiens]; (5852:) TEA domain family member 3 [Homo sapiens]; (5853:) TEK Receptor Tyrosine Kinase Activator; (5854:) Telomerase; (5855:) Telomerase Activator; (5856:) Telomerase reverse transcriptase (Telomerase catalytic subunit) (HEST2) (Telomerase-associated protein 2) (TP2); (5857:) telomerase reverse transcriptase isoform 1 [Homo sapiens]; (5858:) telomerase reverse transcriptase isoform 2 [Homo sapiens]; (5859:) terminal deoxynucleotidyltransferase isoform 1 [Homo sapiens]; (5860:) terminal deoxynucleotidyltransferase isoform 2 [Homo sapiens]; (5861:) testicular ECA [Homo sapiens]; (5862:) testisin isoform 1 [Homo sapiens]; (5863:) testisin isoform 2 [Homo sapiens]; (5864:) testisin isoform 3 [Homo sapiens]; (5865:) Testisin precursor (Eosinophil serine protease 1) (ESP-1); (5866:) Testis-specific serine/threonine-protein kinase 1 (TSSK-1) (Testis-specific kinase 1) (TSK-1) (Serine/threonine-protein kinase22A); (5867:) Testis-specific serine/threonine-protein kinase 2 (TSSK-2) (Testis-specific kinase 2) (TSK-2) (Serine/threonine-protein kinase22B) (DiGeorge syndrome protein G); (5868:) Testis-specific serine/threonine-protein kinase 3 (TSSK-3) (Testis-specific kinase 3) (TSK-3) (Serine/threonine-protein kinase22C); (5869:) Testis-specific serine/threonine-protein kinase 4 (TSSK-4) (Testis-specific kinase 4) (TSK-4) (Serine/threonine-protein kinase22E); (5870:) TGF-beta receptor type III precursor (TGFR-3) (Transforming growth factor beta receptor III) (Betaglycan); (5871:) TGF-beta receptor type-1 precursor (TGF-beta receptor type I) (TGFR-1) (TGF-beta type I receptor) (Serine/threonine-proteinkinase receptor R4) (SKR4) (Activin receptor-like kinase 5) (ALK-5); (5872:) TGF-beta receptor type-2 precursor (TGF-beta receptor type II) (TGFR-2) (TGF-beta type II receptor) (Transforming growthfactor-beta receptor type II) (TbetaR-II); (5873:) The Solution Structure Of Reduced Monomeric Superoxide Dismutase,Nmr, 36 Structures; (5874:) thimet oligopeptidase 1 [Homo sapiens]; (5875:) thioesterase II [Homo sapiens]; (5876:) Thiopurine S-methyltransferase (Thiopurine methyltransferase); (5877:) thiopurine S-methyltransferase [Homo sapiens]; (5878:) thioredoxin [Homo sapiens]; (5879:) Thioredoxin domain-containing protein 2 (Spermatid-specific thioredoxin-1) (Sptrx-1); (5880:) Thioredoxin domain-containing protein 6 (Thioredoxin-like protein2) (Txl-2); (5881:) thioredoxin peroxidase [Homo sapiens]; (5882:) Thioredoxin Reductase (TrxR); (5883:) thioredoxin reductase [Homo sapiens]; (5884:) thioredoxin reductase 1 [Homo sapiens]; (5885:) thioredoxin reductase 2 precursor [Homo sapiens]; (5886:) Thioredoxin-1 (Trx-1); (5887:) Thioredoxin-dependent peroxide reductase, mitochondrial precursor (Peroxiredoxin-3) (PRX III) (Antioxidant protein 1) (AOP-1) (Protein MER5 homolog) (HBC189); (5888:) thiosulfate sulfurtransferase [Homo sapiens]; (5889:) Three prime repair exonuclease 1 (3'-5' exonuclease TREX1) (DNaseIII); (5890:) three prime repair exonuclease 1 isoform a [Homo sapiens]; (5891:) three prime repair exonuclease 1 isoform b [Homo sapiens]; (5892:) three prime repair exonuclease 1 isoform c [Homo sapiens]; (5893:) three prime repair exonuclease 1 isoform d [Homo sapiens]; (5894:) three prime repair exonuclease 2 [Homo sapiens]; (5895:) "Threonine aspartase 1 (Taspase-1) [Contains:) Threonine aspartase subunit alpha; Threonine aspartase subunit beta]."; (5896:) Threonine synthase-like 1 (bacterial) [Homo sapiens]; (5897:) threonine synthase-like 1 [Homo sapiens]; (5898:) Threonine synthase-like 1; (5899:) Thrombin; (5900:) Thrombin Receptor; (5901:) Thrombomodulin precursor (TM) (Fetomodulin) (CD141 antigen); (5902:) Thrombomodulin Receptor; (5903:) Thrombopoietin (TPO) Receptor; (5904:) Thrombopoietin receptor precursor (TPO-R) (Myeloproliferative leukemia protein) (C-mpl) (CD110 antigen); (5905:) Thrombospondin-1 (TSP-1); (5906:) Thromboxane (TX) Synthesis; (5907:) thromboxane A synthase 1 (platelet, cytochrome P450, family 5,subfamily A) isoform TXS-I [Homo sapiens]; (5908:) thromboxane A synthase 1 (platelet, cytochrome P450, family 5,subfamily A) isoform TXS-11 [Homo sapiens]; (5909:) Thromboxane A2 (TXA2) Receptor; (5910:) Thromboxane A2 receptor (TXA2-R) (Prostanoid TP receptor); (5911:) thymidine kinase 1, soluble [Homo sapiens]; (5912:) thymidine kinase 2 [Homo sapiens]; (5913:) thymidine kinase 2, mitochondrial [Homo sapiens]; (5914:) Thymidine kinase 2, mitochondrial precursor (Mt-TK); (5915:) Thymidine kinase, cytosolic; (5916:) Thymidine Phosphorylase (TP); (5917:) Thymidylate Synthase (TS); (5918:) thymidylate synthetase [Homo sapiens]; (5919:) thymine-DNA glycosylase [Homo sapiens]; (5920:) Thyroid Hormone Receptor (TR); (5921:) Thyroid hormone receptor alpha (C-erbA-alpha) (c-erbA-1) (EAR-7) (EAR7); (5922:) Thyroid hormone receptor beta-1; (5923:) Thyroid hormone receptor beta-2; (5924:) Thyroid hormone receptor-associated protein 2 (Thyroid hormone receptor-associated protein complex 240 kDa component-like); (5925:) Thyroid hormone receptor-associated protein 3 (Thyroid hormone receptor-associated protein complex 150 kDa component) (Trap150); (5926:) Thyroid hormone receptor-associated protein complex 240 kDa component (Trap240) (Thyroid hormone receptor-associated protein 1) (Vitamin D3 receptor-interacting protein complex component DRIP250) (DRIP 250) (Activator-recruited cofactor 250 kDa component) (ARC250); (5927:) Thyroid Hormone Receptor-Beta (TR Beta); (5928:) Thyroid Peroxidase; (5929:) thyroid peroxidase [Homo sapiens]; (5930:) thyroid peroxidase isoform a [Homo sapiens]; (5931:) thyroid peroxidase isoform b [Homo sapiens]; (5932:) thyroid peroxidase isoform c [Homo sapiens]; (5933:) thyroid peroxidase isoform d [Homo sapiens]; (5934:) thyroid peroxidase isoform e [Homo sapiens]; (5935:) Thyroid peroxidase precursor (TPO); (5936:) Thyroid receptor-interacting protein 12 (TRIP12); (5937:) Thyrotropin receptor precursor (TSH-R) (Thyroid-stimulating hormone receptor); (5938:) Thyrotropin-Releasing Hormone (TRH) Receptor; (5939:) thyrotropin-releasing hormone degrading enzyme [Homo sapiens]; (5940:) Thyrotropin-releasing hormone receptor (TRH-R) (Thyroliberin receptor); (5941:) Tie-1 Receptor Tyrosine Kinase; (5942:) TIGD5 protein [Homo sapiens]; (5943:) Tissue alpha-L-fucosidase precursor (Alpha-L-fucosidase I) (Alpha-L-fucoside fucohydrolase); (5944:) Tissue Factor; (5945:) tissue inhibitor of metalloproteinase 1 precursor [Homo sapiens]; (5946:) tissue inhibitor of metalloproteinase 2 precursor [Homo sapiens]; (5947:) tissue inhibitor of metalloproteinase 3 precursor [Homo sapiens]; (5948:) tissue inhibitor of metalloproteinase 4 precursor [Homo sapiens]; (5949:) tissue non-specific alkaline phosphatase precursor [Homo sapiens]; (5950:) Tissue Plasminogen Activator (tPA); (5951:) tissue plasminogen activator (t-PA) [Homo sapiens]; (5952:) "Tissue-type plasminogen activator precursor (tPA) (t-PA) (t-plasminogen activator) (Alteplase) (Reteplase) [Contains: Tissue-type plasminogen activator chain A; Tissue-type plasminogen activator chain B]."; (5953:) Titin (Connectin) (Rhabdomyosarcoma antigen MU-RMS-40.14); (5954:) TLL1 protein [Homo sapiens]; (5955:) TLL2 protein [Homo sapiens]; (5956:) T-lymphocyte activation antigen CD80 precursor (Activation B7-1antigen) (CTLA-4 counter-receptor B7.1) (B7) (BB1); (5957:) T-lymphocyte activation antigen CD86 precursor (Activation B7-2antigen) (CTLA-4 counter-receptor B7.2) (B70) (FUN-1) (BU63); (5958:) T-lymphokine-activated killer cell-originated protein kinase (T-LAK cell-originated protein kinase) (PDZ-binding kinase) (Spermatogenesis-related protein kinase) (SPK) (MAPKK-like proteinkinase) (Nori-3); (5959:) TNF receptor-associated factor 2 (Tumor necrosis factor type 2receptor-associated protein 3); (5960:) TNF receptor-associated factor 6 (Interleukin 1 signal transducer) (RING finger protein 85); (5961:) TNF receptor-associated factor 6 [Homo sapiens]; (5962:) TNF-alpha converting enzyme [Homo sapiens]; (5963:) TNF-alpha converting enzyme precursor [Homo sapiens]; (5964:) Toll-Like Receptor (TLR); (5965:) Toll-like receptor 1 precursor (Toll/interleukin-1 receptor-likeprotein) (TIL) (CD281 antigen); (5966:) Toll-like receptor 10 precursor (CD290 antigen); (5967:) Toll-like receptor 2 precursor (Toll/interleukin 1 receptor-likeprotein 4) (CD282 antigen); (5968:) Toll-Like Receptor 3 (TLR3); (5969:) Toll-like receptor 3 precursor (CD283 antigen); (5970:) Toll-Like Receptor 4 (TLR4); (5971:) Toll-like receptor 4 precursor (hToll) (CD284 antigen); (5972:) toll-like receptor 4 precursor [Homo sapiens]; (5973:) Toll-like receptor 5 precursor (Toll/interleukin-1 receptor-likeprotein 3); (5974:) Toll-like receptor 6 precursor; (5975:) Toll-Like Receptor 7 (TLR7); (5976:) Toll-like receptor 7 precursor; (5977:) Toll-like receptor 8 precursor (CD288 antigen); (5978:) Toll-Like Receptor 9 (TLR9); (5979:) Toll-like receptor 9 precursor (CD289 antigen); (5980:) topoisomerase (DNA) III alpha [Homo sapiens]; (5981:) topoisomerase (DNA) III beta [Homo sapiens]; (5982:) Topoisomerase I; (5983:) Topoisomerase II; (5984:) Topoisomerase IV; (5985:) topoisomerase-related function protein [Homo sapiens]; (5986:) TP53-induced glycolysis and apoptosis regulator [Homo sapiens]; (5987:) TPA:) ubiquitin-specific protease 17-like protein [Homo sapiens]; (5988:) TPA_exp:) cytosolic 5'(3')-deoxyribonucleotidase [Homo sapiens]; (5989:) TPK1 protein [Homo sapiens]; (5990:) Trace amine-associated receptor 1 (Trace amine receptor 1) (TaR-1); (5991:) Trace amine-associated receptor 2 (G-protein coupled receptor 58); (5992:) Trace amine-associated receptor 3 (G-protein coupled receptor 57); (5993:) Trace amine-associated receptor 5 (Putative neurotransmitter receptor); (5994:) Trace amine-associated receptor 6 (Trace amine receptor 4) (TaR-4); (5995:) Trace amine-associated receptor 8 (Trace amine receptor 5) (TaR-5) (G-protein coupled receptor 102); (5996:) Trace amine-associated receptor 9 (Trace amine receptor 3) (TaR-3); (5997:) TRAF6-regulated IKK activator 1 beta Uev1A [Homo sapiens]; (5998:) Trans-2-enoyl-CoA reductase, mitochondrial precursor (HsNrbf-1) (NRBF-1); (5999:) transacylase [Homo sapiens]; (6000:) transaldolase 1 [Homo sapiens]; (6001:) Transcription elongation factor B (SIII), polypeptide 2 (18 kDa,elongin B) [Homo sapiens]; (6002:) Transcription elongation factor B polypeptide 2 (RNA polymerase IItranscription factor SIII subunit B) (SIII p18) (Elongin B) (EloB) (Elongin 18 kDa subunit); (6003:) Transcription elongation factor SPT4 (hSPT4) (DRB sensitivity-inducing factor small subunit) (DSIF small subunit) (DSIF p14); (6004:) Transcription elongation factor SPT5 (hSPT5) (DRBsensitivity-inducing factor large subunit) (DSIF large subunit) (DSIF p160) (Tat-cotransactivator 1 protein) (Tat-CT1 protein); (6005:) transcription factor 1, hepatic [Homo sapiens]; (6006:) transcription factor AP-2 alpha isoform a [Homo sapiens]; (6007:) transcription factor AP-2 alpha isoform b [Homo sapiens]; (6008:) transcription factor AP-2 alpha isoform c [Homo sapiens]; (6009:) transcription factor AP-2 beta (activating enhancer binding protein2 beta) [Homo sapiens]; (6010:) transcription factor AP-2 gamma [Homo sapiens]; (6011:) Transcription factor CP2-like protein 1 (CP2-related transcriptional repressor 1) (CRTR-1) (Transcription factor LBP-9); (6012:) transcription factor LBP-1b [Homo sapiens]; (6013:) transcription factor LBP-9 [Homo sapiens]; (6014:) Transcription factor p65 (Nuclear factor NF-kappa-B p65 subunit); (6015:) transcription factor-like protein 4 isoform alpha [Homo sapiens]; (6016:) transcription factor-like protein 4 isoform beta [Homo sapiens]; (6017:) transcription factor-like protein 4 isoform gamma [Homo sapiens]; (6018:) Transcription initiation factor IIF alpha subunit (TFIIF-alpha) (Transcription initiation factor RAP74) (General transcription factor IIF polypeptide 174 kDa subunit protein); (6019:) Transcription initiation factor TFIID subunit 1 (Transcription initiation factor TFIID 250 kDa subunit) (TAF(II)250) (TAFII-250) (TAFII250) (TBP-associated factor 250 kDa) (p250) (Cell cycle gene1 protein); (6020:) Transcriptional repressor NF-X1 (Nuclear transcription factor, Xbox-binding, 1); (6021:) transferrin [Homo sapiens]; (6022:) Transferrin Receptor (Tf-R); (6023:) Transferrin receptor protein 1 (TfR1) (TR) (TfR) (Trfr) (CD71 antigen) (T9) (p90); (6024:) Transferrin receptor protein 2 (TfR2); (6025:) Transforming growth factor-beta (TGF-beta); (6026:) Transforming growth factor-beta 1 (TGF-beta 1); (6027:) Transforming growth factor-beta 2 (TGF-beta 2); (6028:) Transforming growth factor alpha (TGF-alpha); (6029:) transforming growth factor, alpha [Homo sapiens]; (6030:) transforming growth factor, beta 1 [Homo sapiens]; (6031:) transforming growth factor, beta receptor II isoform A precursor [Homo sapiens]; (6032:) transforming growth factor, beta receptor II isoform B precursor [Homo sapiens]; (6033:) Transforming Growth Factor-Beta3 (TGF-Beta3) Receptor; (6034:) Transglutaminase (TGase); (6035:) transglutaminase 1 [Homo sapiens]; (6036:) transglutaminase 2 isoform a [Homo sapiens]; (6037:) transglutaminase 2 isoform b [Homo sapiens]; (6038:) transglutaminase 3 precursor [Homo sapiens]; (6039:) transglutaminase K enzyme; (6040:) Transient receptor potential cation channel subfamily M member 2(Long transient receptor potential channel 2) (LTrpC2) (LTrpC-2); (6041:) Transient receptor potential channel 7 (TrpC7) (Estrogen-responsive element-associated gene 1 protein); (6041:) Transketolase (TK); (6042:) transketolase-like 1 [Homo sapiens]; (6043:) translation repressor NAT1

[*Homo sapiens*]; (6044:) transmembrane 4 superfamily member 15 [*Homo sapiens*]; (6045:) transmembrane aspartic proteinase Asp 1 [*Homo sapiens*]; (6046:) transmembrane aspartic proteinase Asp 2 [*Homo sapiens*]; (6047:) Transmembrane glycoprotein NMB precursor (Transmembrane glycoprotein HGFIN); (6048:) transmembrane protease, serine 11D [*Homo sapiens*]; (6049:) "Transmembrane protease, serine 11D precursor (Airway trypsin-like protease) [Contains:) Transmembrane protease, serine 11D non-catalytic chain; Transmembrane protease, serine 11D catalyticchain]."; (6050:) Transmembrane protease, serine 13 (Mosaic serine protease) (Membrane-type mosaic serine protease); (6051:) transmembrane protease, serine 13 [*Homo sapiens*]; (6052:) "Transmembrane protease, serine 9 (Polyserase-1) (Polyserase-I) (Polyserine protease 1) [Contains:) Serase-1; Serase-2; Serase-3]."; (6053:) trehalase [*Homo sapiens*]; (6054:) Trem-like transcript 1 protein precursor (TLT-1) (Triggering receptor expressed on myeloid cells-like protein 1); (6055:) Trem-like transcript 2 protein precursor (TLT-2) (Triggering receptor expressed on myeloid cells-like protein 2); (6056:) TRIAD3 protein isoform a [*Homo sapiens*]; (6057:) TRIAD3 protein isoform b [*Homo sapiens*]; (6058:) "Trifunctional enzyme subunit alpha, mitochondrial precursor (TP-alpha) (78 kDa gastrin-binding protein) [Includes:) Long-chain enoyl-CoA hydratase; Long chain 3-hydroxyacyl-CoA dehydrogenase]."; (6059:) Trifunctional enzyme subunit beta, mitochondrial precursor (TP-beta) [Includes:) 3-ketoacyl-CoA thiolase (Acetyl-CoA acyltransferase) (Beta-ketothiolase)]; (6060:) Triggering receptor expressed on myeloid cells 1 precursor (TREM-1) (Triggering receptor expressed on monocytes 1); (6061:) Triggering receptor expressed on myeloid cells 2 precursor (Triggering receptor expressed on monocytes 2) (TREM-2); (6062:) Triggering Receptor Expressed on Myeloid Cells-1 (TREM-1) Receptor; (6063:) Trimethyllysine dioxygenase, mitochondrial precursor (Epsilon-trimethyllysine 2-oxoglutarate dioxygenase) (TML-alpha-ketoglutarate dioxygenase) (TML hydroxylase) (TMLdioxygenase) (TMLD); (6064:) trimethyllysine hydroxylase, epsilon [*Homo sapiens*]; (6065:) Triosephosphate isomerase (TIM) (Triose-phosphate isomerase); (6066:) triosephosphate isomerase 1 [*Homo sapiens*]; (6067:) tripeptidyl peptidase II [*Homo sapiens*]; (6068:) tripeptidyl peptidase II; (6069:) Tripeptidyl-peptidase 2 (Tripeptidyl-peptidase II) (TPP-II) (Tripeptidyl aminopeptidase); (6070:) tripeptidyl-peptidase I precursor [*Homo sapiens*]; (6071:) tRNA 5-methylaminomethyl-2-thiouridylate methyltransferase 1 [*Homo sapiens*]; (6072:) tRNA isopentenyl transferase [*Homo sapiens*]; (6073:) tRNA isopentenyltransferase 1 [*Homo sapiens*]; (6074:) tRNA isopentenyltransferase, mitochondrial precursor (Isopentenyl-diphosphate:tRNA isopentenyltransferase) (IPPtransferase) (IPTase) (IPPT) (hGRO1); (6075:) tRNA nucleotidyl transferase, CCA-adding, 1 isoform 1 [*Homo sapiens*]; (6076:) tRNA nucleotidyl transferase, CCA-adding, 1 isoform 2 [*Homo sapiens*]; (6077:) tRNA-guanine transglycosylase [*Homo sapiens*]; (6078:) tRNA-nucleotidyltransferase [*Homo sapiens*]; (6079:) tRNA-nucleotidyltransferase 1, mitochondrial precursor (Mitochondrial tRNA nucleotidyl transferase, CCA-adding) (mt tRNAadenylyltransferase) (mt tRNA CCA-pyrophosphorylase) (mt tRNACCA-diphosphorylase) (mt CCA-adding enzyme); (6080:) truncated mercaptopyruvate sulfurtransferase variant [*Homo sapiens*]; (6081:) *Trypanosoma cruzi* Trypanothione Reductase; (6082:) Trypsin; (6083:) Tryptase; (6084:) Tryptase Beta; (6085:) Tryptase delta precursor (Delta tryptase) (Mast cell mMCP-7-like) (Tryptase-3) (HmMCP-3-like tryptase III); (6086:) tryptophan hydroxylase 1 [*Homo sapiens*]; (6087:) tryptophanyl-tRNA synthetase isoform a [*Homo sapiens*]; (6088:) tryptophanyl-tRNA synthetase isoform b [*Homo sapiens*]; (6089:) TTLL3 protein [*Homo sapiens*]; (6090:) T-Type Calcium Channel (CaV3.1d) Blocker; (6091:) Tubulin; (6092:) Tubulin Polymerase; (6093:) tubulin tyrosine ligase [*Homo sapiens*]; (6094:) Tumor Necrosis Apoptosis Inducing Ligand Receptor 1 (TRAIL-R1); (6095:) Tumor Necrosis Apoptosis Inducing Ligand Receptor 2 (TRAIL-R2); (6096:) Tumor Necrosis Factor (TNF) Release; (6097:) tumor necrosis factor alpha [*Homo sapiens*]; (6098:) "Tumor necrosis factor ligand superfamily member 11 (Receptoractivator of nuclear factor kappa B ligand) (RANKL) (TNF-related activation-induced cytokine) (TRANCE) (Osteoprotegerin ligand) (OPGL) (Osteoclast differentiation factor) (ODF) (CD254 antigen)[Contains:) Tumor necrosis factor ligand superfamily member 11,membrane form; Tumor necrosis factor ligand superfamily member 11,soluble form]."; (6099:) tumor necrosis factor ligand superfamily, member 11 isoform 1 [*Homo sapiens*]; (6100:) tumor necrosis factor ligand superfamily, member 11 isoform 2 [*Homo sapiens*]; (6101:) Tumor Necrosis Factor Receptor 1 (TNFR1); (6102:) tumor necrosis factor receptor 1 precursor [*Homo sapiens*]; (6103:) Tumor necrosis factor receptor superfamily member 10A precursor (Death receptor 4) (TNF-related apoptosis-inducing ligand receptor1) (TRAIL receptor 1) (TRAIL-R1) (CD261 antigen); (6104:) Tumor necrosis factor receptor superfamily member 10B precursor (Death receptor 5) (TNF-related apoptosis-inducing ligand receptor2) (TRAIL receptor 2) (TRAIL-R2) (CD262 antigen); (6105:) Tumor necrosis factor receptor superfamily member 10C precursor (Decoy receptor 1) (DcR1) (Decoy TRAIL receptor without death domain) (TNF-related apoptosis-inducing ligand receptor 3) (TRAIL receptor 3) (TRAIL-R3) (Trail receptor without an intracellulardomain) (Lymphocyte inhibitor of TRAIL) (Antagonist decoy receptor for TRAIL/Apo-2L) (CD263 antigen); (6106:) Tumor necrosis factor receptor superfamily member 10D precursor (Decoy receptor 2) (DcR2) (TNF-related apoptosis-inducing ligand receptor 4) (TRAIL receptor 4) (TRAIL-R4) (TRAIL receptor with a truncated death domain) (CD264 antigen); (6107:) Tumor necrosis factor receptor superfamily member 11A precursor (Receptor activator of NF-KB) (Osteoclast differentiation factor receptor) (ODFR) (CD265 antigen); (6108:) Tumor necrosis factor receptor superfamily member 11B precursor (Osteoprotegerin) (Osteoclastogenesis inhibitory factor); (6109:) Tumor necrosis factor receptor superfamily member 12A precursor (Fibroblast growth factor-inducible immediate-early response protein 14) (FGF-inducible 14) (Tweak-receptor) (TweakR) (CD266antigen); (6110:) Tumor necrosis factor receptor superfamily member 13B(Transmembrane activator and CAML interactor) (CD267 antigen); (6111:) Tumor necrosis factor receptor superfamily member 13C (Bcell-activating factor receptor) (BAFF receptor) (BAFF-R) (BLysreceptor 3) (CD268 antigen); (6112:) Tumor necrosis factor receptor superfamily member 14 precursor (Herpesvirus entry mediator A) (Tumor necrosis factor receptor-like2) (TR2); (6113:) Tumor necrosis factor receptor superfamily member 16 precursor (Low-affinity nerve growth factor receptor) (NGF receptor) (Gp80-LNGFR) (p75 ICD) (Low affinity neurotrophin receptor p75NTR) (CD271 antigen); (6114:) Tumor necrosis factor receptor superfamily member 17 (B-cell maturation protein) (CD269 antigen); (6115:) Tumor necrosis factor receptor superfamily member 18 precursor (Glucocorticoid-induced TNFR-related protein) (Activation-inducible TNFR family receptor); (6116:)

Tumor necrosis factor receptor superfamily member 19 precursor (Toxicity and JNK inducer) (TRADE); (6117:) Tumor necrosis factor receptor superfamily member 19L precursor (Receptor expressed in lymphoid tissues); (6118:) "Tumor necrosis factor receptor superfamily member 1A precursor (p60) (TNF-R1) (TNF-RI) (TNFR-I) (p55) (CD120a antigen) [Contains: Tumor necrosis factor receptor superfamily member 1A, membrane form; Tumor necrosis factor-binding protein 1 (TBPI)]."; (6119:) "Tumor necrosis factor receptor superfamily member 1B precursor (Tumor necrosis factor receptor 2) (TNF-R2) (Tumor necrosis factor receptor type II) (p75) (p80 TNF-alpha receptor) (CD120b antigen) (Etanercept) [Contains:) Tumor necrosis factor receptor superfamily member 1b, membrane form; Tumor necrosis factor-binding protein 2(TBPII) (TBP-2)]."; (6120:) Tumor necrosis factor receptor superfamily member 21 precursor (TNFR-related death receptor 6) (Death receptor 6); (6121:) Tumor necrosis factor receptor superfamily member 25 precursor (WSL-1 protein) (Apoptosis-mediating receptor DR3) (Apoptosis-mediating receptor TRAMP) (Death domain receptor 3) (WSL protein) (Apoptosis-inducing receptor AIR) (Apo-3) (Lymphocyte-associated receptor of death) (LARD); (6122:) Tumor necrosis factor receptor superfamily member 27 (X-linked ectodysplasin-A2 receptor) (EDA-A2 receptor); (6123:) Tumor necrosis factor receptor superfamily member 3 precursor (Lymphotoxin-beta receptor) (Tumor necrosis factor receptor2-related protein) (Tumor necrosis factor C receptor); (6124:) Tumor necrosis factor receptor superfamily member 4 precursor (OX40L receptor) (ACT35 antigen) (TAX transcriptionally-activated glycoprotein 1 receptor) (CD134 antigen); (6125:) Tumor necrosis factor receptor superfamily member 5 precursor (CD40L receptor) (B-cell surface antigen CD40) (CDw40) (Bp50); (6126:) Tumor necrosis factor receptor superfamily member 6 precursor (FASLG receptor) (Apoptosis-mediating surface antigen FAS) (Apo-1 antigen) (CD95 antigen); (6127:) Tumor necrosis factor receptor superfamily member 6B precursor (Decoy receptor for Fas ligand) (Decoy receptor 3) (DcR3) (M68); (6128:) Tumor necrosis factor receptor superfamily member 7 precursor (CD27L receptor) (T-cell activation antigen CD27) (T14); (6129:) Tumor necrosis factor receptor superfamily member 8 precursor (CD30L receptor) (Lymphocyte activation antigen CD30) (KI-1 antigen); (6130:) Tumor necrosis factor receptor superfamily member 9 precursor (4-1BB ligand receptor) (T-cell antigen 4-1BB homolog) (T-cell antigen ILA) (CD137 antigen) (CDw137); (6131:) Tumor necrosis factor receptor superfamily member EDAR precursor (Anhidrotic ectodysplasin receptor 1) (Ectodysplasin-A receptor) (EDA-A1 receptor) (Ectodermal dysplasia receptor) (Downless homolog); (6132:) tumor necrosis factor receptor superfamily, member 6 isoform 1precursor [*Homo sapiens*]; (6133:) tumor necrosis factor receptor superfamily, member 6 isoform 2precursor [*Homo sapiens*]; (6134:) tumor necrosis factor receptor superfamily, member 6 isoform 3precursor [*Homo sapiens*]; (6135:) tumor necrosis factor receptor superfamily, member 6 isoform 4precursor [*Homo sapiens*]; (6136:) tumor necrosis factor receptor superfamily, member 6 isoform 5precursor [*Homo sapiens*]; (6137:) tumor necrosis factor receptor superfamily, member 6 isoform 6precursor [*Homo sapiens*]; (6138:) tumor necrosis factor receptor superfamily, member 6 isoform 7precursor [*Homo sapiens*]; (6139:) tumor necrosis factor receptor superfamily, member 8 isoform 1precursor [*Homo sapiens*]; (6140:) tumor necrosis factor receptor superfamily, member 8 isoform 2 [*Homo sapiens*]; (6141:) tumor necrosis factor, alpha-induced protein 8 isoform a [*Homo sapiens*]; (6142:) tumor necrosis factor, alpha-induced protein 8 isoform b [*Homo sapiens*]; (6143:) Tumor Necrosis Factor-Alpha (TNF-Alpha) Synthesis; (6144:) Tumor Necrosis Factor-Alpha Converting Enzyme (TACE); (6145:) tumor protein p53 [*Homo sapiens*]; (6146:) tumor stroma and activated macrophage protein DLM-1 [*Homo sapiens*]; (6147:) Tumor susceptibility gene 101 protein; (6148:) "Tumor-associated hydroquinone oxidase (tNOX) (Cytosolic ovarian carcinoma antigen 1) (APK1 antigen) [Includes:) Hydroquinone [NADH]oxidase; Protein disulfide-thiol oxidoreductase]."; (6149:) Tumour Cell Survival Phosphatase-1 (TCSP-1); (6150:) TX protease precursor [*Homo sapiens*]; (6151:) TY protease [*Homo sapiens*]; (6152:) Type II inositol-3,4-bisphosphate 4-phosphatase (Inositolpolyphosphate 4-phosphatase type II); (6153:) Type-1 angiotensin II receptor (AT1) (AT1AR) (AT1BR); (6154:) Type-2 angiotensin II receptor (AT2); (6155:) Tyrosinase; (6156:) Tyrosinase precursor (Monophenol monooxygenase) (Tumor rejection antigen AB) (SK29-AB) (LB24-AB); (6157:) tyrosinase precursor [*Homo sapiens*]; (6158:) tyrosine 3/tryptophan 5-monooxygenase activation protein, thetapolypeptide [*Homo sapiens*]; (6159:) tyrosine 3/tryptophan 5-monooxygenase activation protein, zetapolypeptide [*Homo sapiens*]; (6160:) Tyrosine 3-monooxygenase (Tyrosine 3-hydroxylase) (TH); (6161:) tyrosine hydroxylase isoform a [*Homo sapiens*]; (6162:) tyrosine hydroxylase isoform b [*Homo sapiens*]; (6163:) tyrosine hydroxylase isoform c [*Homo sapiens*]; (6164:) Tyrosine Kinase; (6165:) Tyrosine-protein kinase 6 (Breast tumor kinase) (Tyrosine-proteinkinase BRK); (6166:) Tyrosine-protein kinase receptor Tie-1 precursor; (6167:) Tyrosine-protein kinase receptor TYRO3 precursor (Tyrosine-proteinkinase RSE) (Tyrosine-protein kinase SKY) (Tyrosine-protein kinase DTK) (Protein-tyrosine kinase byk); (6168:) Tyrosine-protein kinase receptor UFO precursor (AXL oncogene); (6169:) Tyrosine-protein kinase RYK precursor; (6170:) Tyrosine-protein kinase transmembrane receptor ROR1 precursor (Neurotrophic tyrosine kinase, receptor-related 1); (6171:) Tyrosine-protein kinase transmembrane receptor ROR2 precursor (Neurotrophic tyrosine kinase, receptor-related 2); (6172:) Tyrosine-protein kinase-like 7 precursor (Colon carcinoma kinase 4) (CCK-4); (6173:) Tyrosine-protein phosphatase non-receptor type 11 (Protein-tyrosinephosphatase 2C) (PTP-2C) (PTP-1D) (SH-PTP3) (SH-PTP2) (SHP-2) (Shp2); (6174:) Tyrosyl-DNA phosphodiesterase 1 (Tyr-DNA phosphodiesterase 1); (6175:) tyrosyl-DNA phosphodiesterase 1 [*Homo sapiens*]; (6176:) tyrosyl protein sulfotransferase 1 [*Homo sapiens*]; (6177:) tyrosyl protein sulfotransferase-1 [*Homo sapiens*]; (6178:) tyrosyl protein sulfotransferase-2 [*Homo sapiens*]; (6179:) "tyrosyl protein sulfotransferase-2; TPST-2 [*Homo sapiens*]."; (6180:) tyrosyl-tRNA synthetase [*Homo sapiens*]; (6181:) UBA2 [*Homo sapiens*]; (6182:) UBA3 [*Homo sapiens*]; (6183:) UBC13/UEV-interacting ring finger protein [*Homo sapiens*]; (6184:) Ubc6p homolog [*Homo sapiens*]; (6185:) UbCH5B; (6186:) UbCH5C; (6187:) UbcM2 [*Homo sapiens*]; (6188:) UBE1C [*Homo sapiens*]; (6189:) UBE1L protein [*Homo sapiens*]; (6190:) UBE1L2 protein [*Homo sapiens*]; (6191:) UBE21 [*Homo sapiens*]; (6192:) UBE2B [*Homo sapiens*]; (6193:) UBE2C [*Homo sapiens*]; (6194:) UBE2D3 [*Homo sapiens*]; (6195:) UBE2G1 protein [*Homo sapiens*]; (6196:) UBE2H protein [*Homo sapiens*]; (6197:) UBE2I protein [*Homo sapiens*]; (6198:) UBE2L3 [*Homo sapiens*]; (6199:) UBE2L6 [*Homo sapiens*]; (6200:) UBE2O protein [*Homo sapiens*]; (6201:) UBE2Q [*Homo sapiens*]; (6202:) UBE2Q1 protein [*Homo sapiens*]; (6203:) UBE2Q2 protein [*Homo sapiens*]; (6204:) UBE2R2 [*Homo sapiens*]; (6205:) UBE2S protein [*Homo sapiens*]; (6206:)

UBE2V1 protein [*Homo sapiens*]; (6207:) UBE2V2 [*Homo sapiens*]; (6208:) UBE2W protein [*Homo sapiens*]; (6209:) UBE2Z protein [*Homo sapiens*]; (6210:) ubenimex (Bestatin)-sensitive aminopeptidase B-like enzyme (EC3.4.11.-)—human (fragments); (6211:) ubiquinol-cytochrome-c reductase (EC 1.10.2.2) cytochrome b—human mitochondrion; (6212:) Ubiquitin activating enzyme [*Homo sapiens*]; (6213:) ubiquitin activating enzyme E1 [*Homo sapiens*]; (6214:) ubiquitin associated protein 2 [*Homo sapiens*]; (6215:) ubiquitin B precursor [*Homo sapiens*]; (6216:) ubiquitin carboxyl-terminal esterase L1 (ubiquitin thiolesterase) [*Homo sapiens*]; (6217:) ubiquitin carboxyl-terminal esterase L3 [*Homo sapiens*]; (6218:) Ubiquitin carboxyl-terminal hydrolase 1 (Ubiquitin thioesterase 1) (Ubiquitin-specific-processing protease 1) (Deubiquitinating enzyme1) (hUBP); (6219:) Ubiquitin carboxyl-terminal hydrolase 10 (Ubiquitin thioesterase 10) (Ubiquitin-specific-processing protease 10) (Deubiquitinating enzyme 10); (6220:) Ubiquitin carboxyl-terminal hydrolase 11 (Ubiquitin thioesterase11) (Ubiquitin-specific-processing protease 11) (Deubiquitinatingenzyme 11); (6221:) Ubiquitin carboxyl-terminal hydrolase 12 (Ubiquitin thioesterase12) (Ubiquitin-specific-processing protease 12) (Deubiquitinatingenzyme 12) (Ubiquitin-hydrolyzing enzyme 1); (6222:) Ubiquitin carboxyl-terminal hydrolase 13 (Ubiquitin thioesterase13) (Ubiquitin-specific-processing protease 13) (Deubiquitinatingenzyme 13) (Isopeptidase T-3) (ISOT-3); (6223:) Ubiquitin carboxyl-terminal hydrolase 14 (Ubiquitin thioesterase 14) (Ubiquitin-specific-processing protease 14) (Deubiquitinatingenzyme 14); (6224:) Ubiquitin carboxyl-terminal hydrolase 15 (Ubiquitin thioesterase15) (Ubiquitin-specific-processing protease 15) (Deubiquitinatingenzyme 15) (Unph-2) (Unph4); (6225:) Ubiquitin carboxyl-terminal hydrolase 16 (Ubiquitin thioesterase 16) (Ubiquitin-specific-processing protease 16) (Deubiquitinatingenzyme 16) (Ubiquitin-processing protease UBP-M); (6226:) Ubiquitin carboxyl-terminal hydrolase 17-like protein (Ubiquitinthioesterase 17-like) (Ubiquitin-specific-processing protease17-like) (Deubiquitinating enzyme 17-like); (6227:) Ubiquitin carboxyl-terminal hydrolase 19 (Ubiquitin thioesterase 19) (Ubiquitin-specific-processing protease 19) (Deubiquitinatingenzyme 19) (Zinc finger MYND domain-containing protein 9); (6228:) Ubiquitin carboxyl-terminal hydrolase 2 (Ubiquitin thioesterase 2) (Ubiquitin-specific-processing protease 2) (Deubiquitinating enzyme2) (41 kDa ubiquitin-specific protease); (6229:) Ubiquitin carboxyl-terminal hydrolase 20 (Ubiquitin thioesterase20) (Ubiquitin-specific-processing protease 20) (Deubiquitinatingenzyme 20); (6230:) Ubiquitin carboxyl-terminal hydrolase 21 (Ubiquitin thioesterase21) (Ubiquitin-specific-processing protease 21) (Deubiquitinatingenzyme 21) (NEDD8-specific protease); (6231:) Ubiquitin carboxyl-terminal hydrolase 22 (Ubiquitin thioesterase22) (Ubiquitin-specific-processing protease 22) (Deubiquitinatingenzyme 22); (6232:) Ubiquitin carboxyl-terminal hydrolase 24 (Ubiquitin thioesterase24) (Ubiquitin-specific-processing protease 24) (Deubiquitinatingenzyme 24); (6233:) Ubiquitin carboxyl-terminal hydrolase 25 (Ubiquitin thioesterase25) (Ubiquitin-specific-processing protease 25) (Deubiquitinatingenzyme 25) (USP on chromosome 21); (6234:) Ubiquitin carboxyl-terminal hydrolase 26 (Ubiquitin thioesterase26) (Ubiquitin-specific-processing protease 26) (Deubiquitinatingenzyme 26); (6235:) Ubiquitin carboxyl-terminal hydrolase 28 (Ubiquitin thioesterase28) (Ubiquitin-specific-processing protease 28) (Deubiquitinatingenzyme 28); (6236:) Ubiquitin carboxyl-terminal hydrolase 29 (Ubiquitin thioesterase29) (Ubiquitin-specific-processing protease 29) (Deubiquitinatingenzyme 29); (6237:) Ubiquitin carboxyl-terminal hydrolase 3 (Ubiquitin thioesterase 3) (Ubiquitin-specific-processing protease 3) (Deubiquitinating enzyme3); (6238:) Ubiquitin carboxyl-terminal hydrolase 30 (Ubiquitin thioesterase30) (Ubiquitin-specific-processing protease 30) (Deubiquitinatingenzyme 30); (6239:) Ubiquitin carboxyl-terminal hydrolase 31 (Ubiquitin thioesterase31) (Ubiquitin-specific-processing protease 31) (Deubiquitinatingenzyme 31); (6240:) Ubiquitin carboxyl-terminal hydrolase 32 (Ubiquitin thioesterase32) (Ubiquitin-specific-processing protease 32) (Deubiquitinatingenzyme 32) (NY-REN-60 antigen); (6241:) Ubiquitin carboxyl-terminal hydrolase 33 (Ubiquitin thioesterase33) (Ubiquitin-specific-processing protease 33) (Deubiquitinatingenzyme 33) (VHL-interacting deubiquitinating enzyme 1); (6242:) Ubiquitin carboxyl-terminal hydrolase 34 (Ubiquitin thioesterase34) (Ubiquitin-specific-processing protease 34) (Deubiquitinatingenzyme 34); (6243:) Ubiquitin carboxyl-terminal hydrolase 35 (Ubiquitin thioesterase35) (Ubiquitin-specific-processing protease 35) (Deubiquitinatingenzyme 35); (6244:) Ubiquitin carboxyl-terminal hydrolase 36 (Ubiquitin thioesterase36) (Ubiquitin-specific-processing protease 36) (Deubiquitinatingenzyme 36); (6245:) Ubiquitin carboxyl-terminal hydrolase 37 (Ubiquitin thioesterase37) (Ubiquitin-specific-processing protease 37) (Deubiquitinatingenzyme 37); (6246:) Ubiquitin carboxyl-terminal hydrolase 38 (Ubiquitin thioesterase38) (Ubiquitin-specific-processing protease 38) (Deubiquitinatingenzyme 38) (HP43.8 KD); (6247:) Ubiquitin carboxyl-terminal hydrolase 4 (Ubiquitin thioesterase 4) (Ubiquitin-specific-processing protease 4) (Deubiquitinating enzyme4) (Ubiquitous nuclear protein homolog); (6248:) Ubiquitin carboxyl-terminal hydrolase 40 (Ubiquitin thioesterase40) (Ubiquitin-specific-processing protease 40) (Deubiquitinatingenzyme 40); (6249:) Ubiquitin carboxyl-terminal hydrolase 42 (Ubiquitin thioesterase42) (Ubiquitin-specific-processing protease 42) (Deubiquitinatingenzyme 42); (6250:) Ubiquitin carboxyl-terminal hydrolase 43 (Ubiquitin thioesterase43) (Ubiquitin-specific-processing protease 43) (Deubiquitinatingenzyme 43); (6251:) Ubiquitin carboxyl-terminal hydrolase 44 (Ubiquitin thioesterase44) (Ubiquitin-specific-processing protease 44) (Deubiquitinatingenzyme 44); (6252:) Ubiquitin carboxyl-terminal hydrolase 46 (Ubiquitin thioesterase46) (Ubiquitin-specific-processing protease 46) (Deubiquitinatingenzyme 46); (6253:) Ubiquitin carboxyl-terminal hydrolase 47 (Ubiquitin thioesterase47) (Ubiquitin-specific-processing protease 47) (Deubiquitinatingenzyme 47); (6254:) Ubiquitin carboxyl-terminal hydrolase 48 (Ubiquitin thioesterase48) (Ubiquitin-specific-processing protease 48) (Deubiquitinatingenzyme 48); (6255:) Ubiquitin carboxyl-terminal hydrolase 49 (Ubiquitin thioesterase49) (Ubiquitin-specific-processing protease 49) (Deubiquitinatingenzyme 49); (6256:) Ubiquitin carboxyl-terminal hydrolase 5 (Ubiquitin thioesterase 5) (Ubiquitin-specific-processing protease 5) (Deubiquitinating enzyme5) (Isopeptidase T); (6257:) Ubiquitin carboxyl-terminal hydrolase 51 (Ubiquitin thioesterase51) (Ubiquitin-specific-processing protease 51) (Deubiquitinatingenzyme 51); (6258:) Ubiquitin carboxyl-terminal hydrolase 6 (Ubiquitin thioesterase 6) (Ubiquitin-specific-processing protease 6) (Deubiquitinating enzyme6) (Proto-oncogene TRE-2); (6259:) Ubiquitin carboxyl-terminal hydrolase 7 (Ubiquitin thioesterase 7) (Ubiquitin-specific-processing protease 7) (Deubiquitinating enzyme7) (Herpesvirus-associated ubiquitin-specific protease); (6260:) Ubiquitin carboxyl-terminal hydrolase 8 (Ubiquitin thioesterase 8) (Ubiquitin-specific-processing protease 8) (Deubiquitinating enzyme8)

(hUBPy); (6261:) Ubiquitin carboxyl-terminal hydrolase BAP1 (BRCA1-associated protein 1) (Cerebral protein 6); (6262:) ubiquitin carboxyl-terminal hydrolase CYLD isoform 1 [*Homo sapiens*]; (6263:) ubiquitin carboxyl-terminal hydrolase CYLD isoform 2 [*Homo sapiens*]; (6264:) Ubiquitin carboxyl-terminal hydrolase isozyme L1 (UCH-L1) (Ubiquitin thioesterase L1) (Neuron cytoplasmic protein 9.5) (PGP9.5) (PGP9.5); (6265:) Ubiquitin carboxyl-terminal hydrolase isozyme L3 (UCH-L3) (Ubiquitin thioesterase L3); (6266:) Ubiquitin carboxyl-terminal hydrolase isozyme L5 (UCH-L5) (Ubiquitin thioesterase L5) (Ubiquitin C-terminal hydrolase UCH37); (6267:) ubiquitin carrier protein [*Homo sapiens*]; (6268:) ubiquitin carrier protein E2-human; (6269:) ubiquitin carrier protein; (6270:) ubiquitin conjugating enzyme—human (fragment); (6271:) ubiquitin conjugating enzyme [*Homo sapiens*]; (6272:) ubiquitin conjugating enzyme 12 [*Homo sapiens*]; (6273:) ubiquitin conjugating enzyme 6 [*Homo sapiens*]; (6274:) ubiquitin conjugating enzyme 7 interacting protein 5 isoform a variant [*Homo sapiens*]; (6275:) ubiquitin conjugating enzyme 7 interacting protein 5 isoform b variant [*Homo sapiens*]; (6276:) ubiquitin conjugating enzyme 9 [*Homo sapiens*]; (6277:) ubiquitin conjugating enzyme 9; (6278:) ubiquitin conjugating enzyme E2 [*Homo sapiens*]; (6279:) ubiquitin conjugating enzyme E2, J2 isoform 1 [*Homo sapiens*]; (6280:) ubiquitin conjugating enzyme E2, J2 isoform 2 [*Homo sapiens*]; (6281:) ubiquitin conjugating enzyme E2, J2 isoform 3 [*Homo sapiens*]; (6282:) ubiquitin conjugating enzyme G2 [*Homo sapiens*]; (6283:) ubiquitin conjugating enzyme homolog; (6284:) ubiquitin conjugating enzyme; (6285:) ubiquitin C-terminal hydrolase UCH37 [*Homo sapiens*]; (6286:) ubiquitin hydrolyzing enzyme 1 [*Homo sapiens*]; (6287:) ubiquitin hydrolyzing enzyme I [*Homo sapiens*]; (6288:) Ubiquitin isopeptidase T [*Homo sapiens*]; (6289:) Ubiquitin Ligase; (6290:) ubiquitin ligase E3A isoform 1 [*Homo sapiens*]; (6291:) Ubiquitin ligase LNX (Numb-binding protein 1) (Ligand of Numb-protein X 1); (6292:) Ubiquitin ligase protein DZIP3 (DAZ-interacting protein 3) (RNA-binding ubiquitin ligase of 138 kDa) (hRUL138); (6293:) Ubiquitin ligase protein RING2 (RING finger protein 2) (RING finger protein 1B) (RING1b) (RING finger protein BAP-1) (DinG protein) (Huntingtin-interacting protein 2-interacting protein 3) (HIP2-interacting protein 3); (6294:) Ubiquitin ligase SIAH1 (Seven in absentia homolog 1) (Siah-1) (Siah-1a); (6295:) Ubiquitin ligase SIAH2 (Seven in absentia homolog 2) (Siah-2) (hSiah2); (6296:) ubiquitin processing protease [*Homo sapiens*]; (6297:) ubiquitin protein ligase E3A isoform 1 [*Homo sapiens*]; (6298:) ubiquitin protein ligase E3A isoform 2 [*Homo sapiens*]; (6299:) ubiquitin protein ligase E3A isoform 3 [*Homo sapiens*]; (6300:) ubiquitin protein ligase E3B [*Homo sapiens*]; (6301:) ubiquitin protein ligase E3C [*Homo sapiens*]; (6302:) Ubiquitin protein ligase Prajal (RING finger protein 70); (6303:) ubiquitin specific protease 1 [*Homo sapiens*]; (6304:) ubiquitin specific protease 11 [*Homo sapiens*]; (6305:) ubiquitin specific protease 14 isoform a [*Homo sapiens*]; (6306:) ubiquitin specific protease 14 isoform b [*Homo sapiens*]; (6307:) ubiquitin specific protease 15 [*Homo sapiens*]; (6308:) ubiquitin specific protease 16 isoform a [*Homo sapiens*]; (6309:) ubiquitin specific protease 16 isoform b [*Homo sapiens*]; (6310:) ubiquitin specific protease 2 isoform b [*Homo sapiens*]; (6311:) ubiquitin specific protease 20 [*Homo sapiens*]; (6312:) ubiquitin specific protease 25 [*Homo sapiens*]; (6313:) ubiquitin specific protease 28 [*Homo sapiens*]; (6314:) ubiquitin specific protease 29 [*Homo sapiens*]; (6315:) ubiquitin specific protease 2b [*Homo sapiens*]; (6316:) ubiquitin specific protease 31 [*Homo sapiens*]; (6317:) ubiquitin specific protease 33 isoform 1 [*Homo sapiens*]; (6318:) ubiquitin specific protease 33 isoform 2 [*Homo sapiens*]; (6319:) ubiquitin specific protease 33 isoform 3 [*Homo sapiens*]; (6320:) ubiquitin specific protease 36 [*Homo sapiens*]; (6321:) ubiquitin specific protease 42 [*Homo sapiens*]; (6322:) ubiquitin specific protease 48 [*Homo sapiens*]; (6323:) ubiquitin specific protease 48 isoform a [*Homo sapiens*]; (6324:) ubiquitin specific protease 51 [*Homo sapiens*]; (6325:) ubiquitin specific protease 7 (herpes virus-associated) [*Homo sapiens*]; (6326:) ubiquitin specific protease 8 [*Homo sapiens*]; (6327:) ubiquitin specific protease 9, X-linked isoform 3 [*Homo sapiens*]; (6328:) ubiquitin specific protease 9, X-linked isoform 4 [*Homo sapiens*]; (6329:) ubiquitin specific protease 9, Y-linked [*Homo sapiens*]; (6330:) ubiquitin specific protease, proto-oncogene isoform a [*Homo sapiens*]; (6331:) ubiquitin specific protease, proto-oncogene isoform b [*Homo sapiens*]; (6332:) Ubiquitin thioesterase protein OTUB1 (Otubain-1) (OTUdomain-containing ubiquitin aldehyde-binding protein 1) (Ubiquitin-specific-processing protease OTUB1) (Deubiquitinatingenzyme OTUB1); (6333:) Ubiquitin thioesterase protein OTUB2 (Otubain-2) (OTUdomain-containing ubiquitin aldehyde-binding protein 2) (Ubiquitin-specific-processing protease OTUB2) (Deubiquitinatingenzyme OTUB2); (6334:) Ubiquitin; (6335:) Ubiquitin-activating enzyme E1 (A1S9 protein); (6336:) Ubiquitin-activating enzyme E1 (A1S9T and BN75 temperature sensitivity complementing) [*Homo sapiens*]; (6337:) ubiquitin-activating enzyme E1 [*Homo sapiens*]; (6338:) Ubiquitin-activating enzyme E1 domain-containing protein 1(UFM1-activating enzyme) (Ubiquitin-activating enzyme 5) (ThiFP1); (6339:) Ubiquitin-activating enzyme E1 homolog (D8); (6340:) Ubiquitin-activating enzyme E1C (UBA3 homolog, yeast) [*Homo sapiens*]; (6341:) ubiquitin-activating enzyme E1C isoform 1 [*Homo sapiens*]; (6342:) ubiquitin-activating enzyme E1C isoform 2 [*Homo sapiens*]; (6343:) ubiquitin-activating enzyme E1C isoform 3 [*Homo sapiens*]; (6344:) Ubiquitin-activating enzyme E1-domain containing 1 [*Homo sapiens*]; (6345:) ubiquitin-activating enzyme E1-domain containing 1 isoform 1 [*Homo sapiens*]; (6346:) ubiquitin-activating enzyme E1-domain containing 1 isoform 2 [*Homo sapiens*]; (6347:) ubiquitin-activating enzyme E1-like [*Homo sapiens*]; (6348:) Ubiquitin-activating enzyme E1-like 2 [*Homo sapiens*]; (6349:) ubiquitin-activating enzyme E1-related protein; (6350:) ubiquitination factor E4A [*Homo sapiens*]; (6351:) ubiquitin-conjugating enzyme [*Homo sapiens*]; (6352:) ubiquitin-conjugating BIR-domain enzyme APOLLON [*Homo sapiens*]; (6353:) ubiquitin-conjugating enzyme [*Homo sapiens*]; (6354:) ubiquitin-conjugating enzyme 1 isoform [*Homo sapiens*]; (6355:) ubiquitin-conjugating enzyme 16 [*Homo sapiens*]; (6356:) Ubiquitin-conjugating enzyme 7-interacting protein 4(UbcM4-interacting protein 4) (RING finger protein 144); (6357:) ubiquitin-conjugating enzyme 9 (UBC9); (6358:) ubiquitin-conjugating enzyme E2 [*Homo sapiens*]; (6359:) Ubiquitin-conjugating enzyme E2 A (Ubiquitin-protein ligase A) (Ubiquitin carrier protein A) (HR6A) (hHR6A); (6360:) Ubiquitin-conjugating enzyme E2 B (Ubiquitin-protein ligase B) (Ubiquitin carrier protein B) (HR6B) (hHR6B) (E2-17 kDa); (6361:) Ubiquitin-conjugating enzyme E2 C (Ubiquitin-protein ligase C) (Ubiquitin carrier protein C) (UbCH10); (6362:) Ubiquitin-conjugating enzyme E2 D1 (Ubiquitin-protein ligase D1) (Ubiquitin carrier protein D1) (UbCH5) (Ubiquitin-conjugating enzyme E2-17 kDa 1) (E2(17)KB 1); (6363:) Ubiquitin-conjugating enzyme E2 D2 (Ubiquitin-protein ligase D2) (Ubiquitin carrier protein D2) (Ubiquitin-conjugating enzyme E2-17 kDa 2) (E2(17) KB 2); (6364:) ubiquitin-conjugating enzyme E2 D2 transcript variant 1 [*Homo sapiens*]; (6365:) Ubiquitin-conjugating enzyme E2 D3 (Ubiquitin-protein ligase D3) (Ubiquitin carrier protein D3) (Ubiquitin-conjugating enzyme E2-17 kDa 3) (E2(17)KB 3); (6366:) Ubiquitin-conjugating enzyme E2 E1 (Ubiquitin-protein ligase E1) (Ubiquitin carrier protein E1) (UbCH6); (6367:) Ubiquitin-conjugating enzyme E2 E2 (Ubiquitin-protein ligase E2) (Ubiquitin carrier protein E2) (UbCH8); (6368:) Ubiquitin-conjugating enzyme E2 E3 (Ubiquitin-protein ligase E3) (Ubiquitin carrier protein E3) (Ubiquitin-conjugating enzyme E2-23 kDa) (UbCH9) (UbcM2); (6369:) Ubiquitin-conjugating enzyme E2 G1 (Ubiquitin-protein ligase G1) (Ubiquitin carrier protein G1) (E217K) (UBC7); (6370:) Ubiquitin-conjugating enzyme E2 G2 (Ubiquitin-protein ligase G2) (Ubiquitin carrier protein G2); (6371:) Ubiquitin-conjugating enzyme E2 H (Ubiquitin-protein ligase H) (Ubiquitin carrier protein H) (UbCH2) (E2-20K); (6372:) Ubiquitin-conjugating enzyme E2 J1 (Non-canonical ubiquitin-conjugating enzyme 1) (NCUBE1) (Yeast ubiquitin-conjugating enzyme UBC6 homolog E) (HSUBC6e); (6373:) Ubiquitin-conjugating enzyme E2 J2 (Non-canonicalubiquitin-conjugating enzyme 2) (NCUBE2); (6374:) ubiquitin-conjugating enzyme E2 Kua-UEV isoform 1 [*Homo sapiens*]; (6375:) ubiquitin-conjugating enzyme E2 Kua-UEV isoform 2 [*Homo sapiens*]; (6376:) Ubiquitin-conjugating enzyme E2 L3 (Ubiquitin-protein ligase L3) (Ubiquitin carrier protein L3) (UbCH7) (E2-F1) (L-UBC); (6377:) Ubiquitin-conjugating enzyme E2 L6 (Ubiquitin-protein ligase L6) (Ubiquitin carrier protein L6) (UbCH8) (Retinoic acid-induced geneB protein) (RIG-B); (6378:) Ubiquitin-conjugating enzyme E2 N (Ubiquitin-protein ligase N) (Ubiquitin carrier protein N) (Ubc13) (Bendless-like ubiquitin-conjugating enzyme); (6379:) Ubiquitin-conjugating enzyme E2 Q1 (Ubiquitin-protein ligase Q1) (Ubiquitin carrier protein Q1) (Protein NICE-5); (6380:) Ubiquitin-conjugating enzyme E2 Q2 (Ubiquitin-protein ligase Q2) (Ubiquitin carrier protein Q2); (6381:) Ubiquitin-conjugating enzyme E2 S (Ubiquitin-protein ligase S) (Ubiquitin carrier protein S) (Ubiquitin-conjugating enzyme E2-24 kDa) (E2-EPF5); (6382:) Ubiquitin-conjugating enzyme E2 T (Ubiquitin-protein ligase T) (Ubiquitin carrier protein T); (6383:) Ubiquitin-conjugating enzyme E2 U (Ubiquitin-protein ligase U) (Ubiquitin carrier protein U); (6384:) ubiquitin-conjugating enzyme E2 UbcH-ben [*Homo sapiens*]; (6385:) Ubiquitin-conjugating enzyme E2 variant 1 (UEV-1) (CROC-1) (Ubiquitin-conjugating enzyme variant Kua) (TRAF6-regulated IKK activator 1 beta Uev1A); (6386:) Ubiquitin-conjugating enzyme E2 variant 1 [*Homo sapiens*]; (6387:) ubiquitin-conjugating enzyme E2 variant 1 isoform a [*Homo sapiens*]; (6388:) ubiquitin-conjugating enzyme E2 variant 1 isoform c [*Homo sapiens*]; (6389:) ubiquitin-conjugating enzyme E2 variant 1 isoform d [*Homo sapiens*]; (6390:) Ubiquitin-conjugating enzyme E2 variant 2 (MMS2) (Enterocyte differentiation-associated factor EDAF-1) (Enterocytedifferentiation-promoting factor) (EDPF-1) (Vitamin D3-inducible protein) (DDVit 1); (6391:) ubiquitin-conjugating enzyme E2 variant 2 [*Homo sapiens*]; (6392:) Ubiquitin-conjugating enzyme E2, J1 (UBC6 homolog, yeast) [*Homo sapiens*]; (6393:) ubiquitin-conjugating enzyme E2, J1 [*Homo sapiens*]; (6394:) ubiquitin-conjugating enzyme E2, J1 variant [*Homo sapiens*]; (6395:) Ubiquitin-conjugating enzyme E2, J2 (UBC6 homolog, yeast) [*Homo sapiens*]; (6396:) ubiquitin-conjugating enzyme E2-17 kDa [*Homo sapiens*]; (6397:) Ubiquitin-conjugating enzyme E2-25 kDa (Ubiquitin-protein ligase) (Ubiquitin carrier protein) (E2(25K)) (Huntingtin-interacting protein 2) (HIP-2); (6398:) Ubiquitin-conjugating enzyme E2-32 kDa complementing(Ubiquitin-protein ligase) (Ubiquitin carrier protein) (E2-CDC34); (6399:) Ubiquitin-conjugating enzyme E2A (RAD6 homolog) [*Homo sapiens*]; (6400:) ubiquitin-conjugating enzyme E2A isoform 1 [*Homo sapiens*]; (6401:) ubiquitin-conjugating enzyme E2A isoform 1 variant [*Homo sapiens*]; (6402:) ubiquitin-conjugating enzyme E2A isoform 2 [*Homo sapiens*]; (6403:) ubiquitin-conjugating enzyme E2A isoform 3 [*Homo sapiens*]; (6404:) Ubiquitin-conjugating enzyme E2B (RAD6 homolog) [*Homo sapiens*]; (6405:) ubiquitin-conjugating enzyme E2B [*Homo sapiens*]; (6406:) Ubiquitin-conjugating enzyme E2C [*Homo sapiens*]; (6407:) ubiquitin-conjugating enzyme E2C isoform 1 [*Homo sapiens*]; (6408:) ubiquitin-conjugating enzyme E2C isoform 2 [*Homo sapiens*]; (6409:) ubiquitin-conjugating enzyme E2C isoform 3 [*Homo sapiens*]; (6410:) ubiquitin-conjugating enzyme E2C isoform 4 [*Homo sapiens*]; (6411:) ubiquitin-conjugating enzyme E2C isoform 5 [*Homo sapiens*]; (6412:) Ubiquitin-conjugating enzyme E2D 1 (UBC4/5 homolog, yeast) [*Homo sapiens*]; (6413:) ubiquitin-conjugating enzyme E2D 1 [*Homo sapiens*]; (6414:) Ubiquitin-conjugating enzyme E2D 2 (UBC4/5 homolog, yeast) [*Homo sapiens*]; (6415:) ubiquitin-conjugating enzyme E2D 2 isoform 1 [*Homo sapiens*]; (6416:) ubiquitin-conjugating enzyme E2D 2 isoform 2 [*Homo sapiens*]; (6417:) Ubiquitin-conjugating enzyme E2D 3 (UBC4/5 homolog, yeast) [*Homo sapiens*]; (6418:) ubiquitin-conjugating enzyme E2D 3 [*Homo sapiens*]; (6419:) ubiquitin-conjugating enzyme E2D 3 isoform 1 [*Homo sapiens*]; (6420:) ubiquitin-conjugating enzyme E2D 3 isoform 2 [*Homo sapiens*]; (6421:) ubiquitin-conjugating enzyme E2D 3 isoform 3 [*Homo sapiens*]; (6422:) ubiquitin-conjugating enzyme E2D 4 (putative) [*Homo sapiens*]; (6423:) Ubiquitin-conjugating enzyme E2E 1 (UBC4/5 homolog, yeast) [*Homo sapiens*]; (6424:) ubiquitin-conjugating enzyme E2E 1 isoform 1 [*Homo sapiens*]; (6425:) ubiquitin-conjugating enzyme E2E 1 isoform 2 [*Homo sapiens*]; (6426:) ubiquitin-conjugating enzyme E2E 2 (UBC4/5 homolog, yeast) [*Homo sapiens*]; (6427:) Ubiquitin-conjugating enzyme E2E 3 (UBC4/5 homolog, yeast) [*Homo sapiens*]; (6428:) ubiquitin-conjugating enzyme E2E 3 [*Homo sapiens*]; (6429:) Ubiquitin-conjugating enzyme E2F (putative) [*Homo sapiens*]; (6430:) ubiquitin-conjugating enzyme E2G 1 (UBC7 homolog, C. elegans) [*Homo sapiens*]; (6431:) Ubiquitin-conjugating enzyme E2G 1 (UBC7 homolog, yeast) [*Homo sapiens*]; (6432:) ubiquitin-conjugating enzyme E2G 1 [*Homo sapiens*]; (6433:) Ubiquitin-conjugating enzyme E2G 2 (UBC7 homolog, yeast) [*Homo sapiens*]; (6434:) ubiquitin-conjugating enzyme E2G 2 isoform 1 [*Homo sapiens*]; (6435:) ubiquitin-conjugating enzyme E2G 2 isoform 2 [*Homo sapiens*]; (6436:) ubiquitin-conjugating enzyme E2H (UBC8 homolog, yeast) [*Homo sapiens*]; (6437:) ubiquitin-conjugating enzyme E2H isoform 1 [*Homo sapiens*]; (6438:) ubiquitin-conjugating enzyme E2H isoform 2 [*Homo sapiens*]; (6439:) Ubiquitin-conjugating enzyme E2I (UBC9 homolog, yeast) [*Homo sapiens*]; (6440:) ubiquitin-conjugating enzyme E2I [*Homo sapiens*]; (6441:) ubiquitin-conjugating enzyme E2I variant [*Homo sapiens*]; (6442:) Ubiquitin-conjugating enzyme E2L 3 [*Homo sapiens*]; (6443:) ubiquitin-conjugating enzyme E2L 3 isoform 1 [*Homo sapiens*]; (6444:) ubiquitin-conjugating enzyme E2L 3 isoform 2 [*Homo sapiens*]; (6445:) Ubiquitin-conjugating enzyme E2L 6 [*Homo sapiens*]; (6446:) ubiquitin-conjugating enzyme E2L 6 isoform 1 [*Homo sapiens*]; (6447:) ubiquitin-conjugating enzyme E2L 6 isoform 2 [*Homo sapiens*];

(6448:) ubiquitin-conjugating enzyme E2-like isoform a [*Homo sapiens*]; (6449:) ubiquitin-conjugating enzyme E2-like isoform b [*Homo sapiens*]; (6450:) Ubiquitin-conjugating enzyme E2M (UBC12 homolog, yeast) [*Homo sapiens*]; (6451:) ubiquitin-conjugating enzyme E2M [*Homo sapiens*]; (6452:) Ubiquitin-conjugating enzyme E2N (UBC13 homolog, yeast) [*Homo sapiens*]; (6453:) ubiquitin-conjugating enzyme E2N [*Homo sapiens*]; (6454:) ubiquitin-conjugating enzyme E2N-like [*Homo sapiens*]; (6455:) ubiquitin-conjugating enzyme E2O [*Homo sapiens*]; (6456:) ubiquitin-conjugating enzyme E2Q (putative) [*Homo sapiens*]; (6457:) ubiquitin-conjugating enzyme E2Q (putative) 2 [*Homo sapiens*]; (6458:) ubiquitin-conjugating enzyme E2Q [*Homo sapiens*]; (6459:) Ubiquitin-conjugating enzyme E2R 2 [*Homo sapiens*]; (6460:) ubiquitin-conjugating enzyme E2S [*Homo sapiens*]; (6461:) ubiquitin-conjugating enzyme E2T (putative) [*Homo sapiens*]; (6462:) ubiquitin-conjugating enzyme E2U (putative) [*Homo sapiens*]; (6463:) Ubiquitin-conjugating enzyme E2W (putative) [*Homo sapiens*]; (6464:) ubiquitin-conjugating enzyme E2W (putative) isoform 1 [*Homo sapiens*]; (6465:) ubiquitin-conjugating enzyme E2W (putative) isoform 2 [*Homo sapiens*]; (6466:) ubiquitin-conjugating enzyme E2W (putative) isoform 3 [*Homo sapiens*]; (6467:) ubiquitin-conjugating enzyme E2Z (putative) [*Homo sapiens*]; (6468:) ubiquitin-conjugating enzyme HBUCE1 [*Homo sapiens*]; (6469:) ubiquitin-conjugating enzyme isolog [*Homo sapiens*]; (6470:) ubiquitin-conjugating enzyme RIG-B [*Homo sapiens*]; (6471:) ubiquitin-conjugating enzyme UBC3B [*Homo sapiens*]; (6472:) ubiquitin-conjugating enzyme UbCH2 [*Homo sapiens*]; (6473:) ubiquitin-conjugating enzyme UbCH6 [*Homo sapiens*]; (6474:) ubiquitin-conjugating enzyme UbCH7 [*Homo sapiens*]; (6475:) ubiquitin-conjugating enzyme UbcM2 [*Homo sapiens*]; (6476:) ubiquitin-conjugating enzyme variant Kua [*Homo sapiens*]; (6477:) ubiquitin-conjugating enzyme, UBC9 [*Homo sapiens*]; (6478:) ubiquitin-conjugating enzyme; (6479:) ubiquitin-conjugating enzyme E2 [*Homo sapiens*]; (6480:) Ubiquitin-fold modifier conjugating enzyme 1 [*Homo sapiens*]; (6481:) Ubiquitin-like 1-activating enzyme E1A (SUMO-1-activating enzyme subunit 1); (6482:) Ubiquitin-like 1-activating enzyme E1B (SUMO-1-activating enzyme subunit 2) (Anthracycline-associated resistance ARX); (6483:) Ubiquitin-like PHD and RING finger domain-containing protein 2(Ubiquitin-like-containing PHD and RING finger domains protein 2) (Np95/ICBP90-like RING finger protein) (Np95-like RING finger protein) (Nuclear zinc finger protein Np97) (RING finger protein107); (6484:) "ubiquitin-like protein activating enzyme; sentrin activating enzyme [*Homo sapiens*]."; (6485:) Ubiquitin-protein E3 ligase Topors (SUMO1-protein E3 ligase Topors) (Topoisomerase I-binding RING finger protein) (Topoisomerase1-binding arginine/serine-rich protein) (Tumor suppressor p53-binding protein 3) (p53-binding protein 3) (p53BP3); (6486:) Ubiquitin-protein ligase BRE1A (BRE1-A) (hBRE1) (RING finger protein 20); (6487:) Ubiquitin-protein ligase BRE1B (BRE1-B) (RING finger protein 40) (95 kDa retinoblastoma-associated protein) (RBP95); (6488:) ubiquitin-protein ligase E1 homolog—human; (6489:) Ubiquitin-protein ligase E3A (E6AP ubiquitin-protein ligase) (Oncogenic protein-associated protein E6-AP) (Human papillomavirus E6-associated protein) (NY-REN-54 antigen); (6490:) Ubiquitin-protein ligase E3C; (6491:) Ubiquitin-protein ligase EDD1 (Hyperplastic discs protein homolog) (hHYD) (Progestin-induced protein); (6492:) ubiquitin-specific processing protease [*Homo sapiens*]; (6493:) ubiquitin-specific protease 12-like 1 [*Homo sapiens*]; (6494:) ubiquitin-specific protease 21 [*Homo sapiens*]; (6495:) ubiquitin-specific protease 26 [*Homo sapiens*]; (6496:) ubiquitin-specific protease 3 [*Homo sapiens*]; (6497:) ubiquitin-specific protease 31 [*Homo sapiens*]; (6498:) ubiquitin-specific protease 7 isoform [*Homo sapiens*]; (6499:) U-box domain containing 5 isoform a [*Homo sapiens*]; (6500:) U-box domain containing 5 isoform b [*Homo sapiens*]; (6501:) UDP glucuronosyltransferase (EC 2.4.1.-) 1A10 precursor—human; (6502:) UDP glycosyltransferase 1 family, polypeptide A1 precursor [*Homo sapiens*]; (6503:) UDP glycosyltransferase 1 family, polypeptide A10 precursor [*Homo sapiens*]; (6504:) UDP glycosyltransferase 1 family, polypeptide A3 precursor [*Homo sapiens*]; (6505:) UDP glycosyltransferase 1 family, polypeptide A4 precursor [*Homo sapiens*]; (6506:) UDP glycosyltransferase 1 family, polypeptide A5 precursor [*Homo sapiens*]; (6507:) UDP glycosyltransferase 1 family, polypeptide A6 isoform 1precursor [*Homo sapiens*]; (6508:) UDP glycosyltransferase 1 family, polypeptide A6 isoform 2 [*Homo sapiens*]; (6509:) UDP glycosyltransferase 1 family, polypeptide A7 precursor [*Homo sapiens*]; (6510:) UDP glycosyltransferase 1 family, polypeptide A8 precursor [*Homo sapiens*]; (6511:) UDP glycosyltransferase 1 family, polypeptide A9 precursor [*Homo sapiens*]; (6512:) UDP glycosyltransferase 2 family, polypeptide B15 [*Homo sapiens*]; (6513:) UDP glycosyltransferase 2 family, polypeptide B4 [*Homo sapiens*]; (6514:) UDP glycosyltransferase 8 (UDP-galactose ceramidegalactosyltransferase) [*Homo sapiens*]; (6515:) UDP-Gal:betaGlcNAc beta 1,3-galactosyltransferase 5 [*Homo sapiens*]; (6516:) UDP-Gal:betaGlcNAc beta 1,4-galactosyltransferase 1,membrane-bound form [*Homo sapiens*]; (6517:) UDP-Gal:betaGlcNAc beta 1,4-galactosyltransferase 2 [*Homo sapiens*]; (6518:) UDP-Gal:betaGlcNAc beta 1,4-galactosyltransferase 3 [*Homo sapiens*]; (6519:) UDP-Gal:betaGlcNAc beta 1,4-galactosyltransferase 4 [*Homo sapiens*]; (6520:) UDP-Gal:betaGlcNAc beta 1,4-galactosyltransferase 5 [*Homo sapiens*]; (6521:) UDP-Gal:betaGlcNAc beta 1,4-galactosyltransferase 6 [*Homo sapiens*]; (6522:) UDP-galactose-4-epimerase [*Homo sapiens*]; (6523:) UDP-GlcNAc:betaGal beta-1,3-N-acetylglucosaminyltransferase 1 [*Homo sapiens*]; (6524:) UDP-GlcNAc:betaGal beta-1,3-N-acetylglucosaminyltransferase 2 [*Homo sapiens*]; (6525:) UDP-GlcNAc:betaGal beta-1,3-N-acetylglucosaminyltransferase 3 [*Homo sapiens*]; (6526:) UDP-GlcNAc:betaGal beta-1,3-N-acetylglucosaminyltransferase 4 [*Homo sapiens*]; (6527:) UDP-GlcNAc:betaGal beta-1,3-N-acetylglucosaminyltransferase 5 [*Homo sapiens*]; (6528:) UDP-GlcNAc:betaGal beta-1,3-N-acetylglucosaminyltransferase 6 [*Homo sapiens*]; (6529:) UDP-glucose 4-epimerase (Galactowaldenase) (UDP-galactose-4-epimerase); (6530:) UDP-glucose pyrophosphorylase 2 isoform a [*Homo sapiens*]; (6531:) UDP-glucose pyrophosphorylase 2 isoform b [*Homo sapiens*]; (6532:) UDP-glucuronate decarboxylase 1 [*Homo sapiens*]; (6533:) UDP-glucuronosyltransferase 1-1 precursor (UDP-glucuronosyltransferase 1A1) (UDPGT) (UGT1*1) (UGT1-01) (UGT1.1) (UGT-1A) (UGT1A) (Bilirubin-specific UDPGT isozyme 1) (HUG-BR1); (6534:) UDP-glucuronosyltransferase 1-6 precursor (UDP-glucuronosyltransferase 1A6) (UDPGT) (UGT1*6) (UGT1-06) (UGT1.6) (UGT-1F) (UGT1F) (Phenol-metabolizing UDP-glucuronosyltransferase); (6535:) UDP-glucuronosyltransferase 2B15 precursor (UDPGT) (UDPGTh-3) (HLUG4); (6536:) UDP-glucuronosyltransferase 2B17 precursor (UDPGT) (C19-steroid-specific UDP-glucuronosyltransferase); (6537:) UDP-glucuronosyltransferase 2B4 precursor (UDPGT) (Hyodeoxycholic acid) (HLUG25) (UDPGTh-1); (6538:) UDP-glucuronyltransferase-S [*Homo sapiens*]; (6539:)

UDP-N-acetylglucosamine-2-epimerase/N-acetylmannosamine kinase [Homo sapiens]; (6540:) UDP-N-acetylglucosamine-2-epimerase [Homo sapiens]; (6541:) UDP-N-acetylglucosamine-2-epimerase/N-acetylmannosamine kinase [Homo sapiens]; (6542:) UDP-N-acetylglucosaminedolichyl-phosphateN-acetylglucosaminephosphotransferase (GPT) (G1PT) (N-acetylglucosamine-1-phosphate transferase) (GlcNAc-1-P transferase); (6543:) UDP-N-acetylglucosamine-dolichyl-phosphateN-acetylglucosaminephosphotransferase isoform a [Homo sapiens]; (6544:) UDP-N-acetylglucosamine-dolichyl-phosphateN-acetylglucosaminephosphotransferase isoform b [Homo sapiens]; (6545:) "UDP-N-acetylhexosamine pyrophosphorylase (Antigen X) (AGX) (Sperm-associated antigen 2) [Includes:) UDP-N-acetylgalactosaminepyrophosphorylase (AGX-1); UDP-N-acetylglucosaminepyrophosphorylase (AGX-2)]."; (6546:) UDP-N-acteylglucosamine pyrophosphorylase 1 [Homo sapiens]; (6547:) UEV-1 [Homo sapiens]; (6548:) UEV1As [Homo sapiens]; (6549:) UEV1Bs [Homo sapiens]; (6550:) Ufm1-conjugating enzyme 1 (Ubiquitin-fold modifier-conjugating enzyme 1); (6551:) Ufm1-conjugating enzyme 1 [Homo sapiens]; (6552:) UGA suppressor tRNA-associated protein (tRNA(Ser/Sec)-associated antigenic protein) (SLA/LP autoantigen) (Soluble liver antigen) (SLA) (Liver-pancreas antigen) (LP) (SLA-p35); (6553:) UMP synthase [Homo sapiens]; (6554:) UMP-CMP kinase (Cytidylate kinase) (Deoxycytidylate kinase) (Cytidine monophosphate kinase) (Uridine monophosphate/cytidinemonophosphate kinase) (UMP/CMP kinase) (UMP/CMPK) (Uridinemonophosphate kinase); (6555:) UMP-CMP kinase [Homo sapiens]; (6556:) UnpEL [Homo sapiens]; (6557:) UnpES [Homo sapiens]; (6558:) u-plasminogen activator receptor form 1 precursor—human; (6559:) upstream binding protein 1 (LBP-1a) [Homo sapiens]; (6560:) Upstream-binding protein 1 (LBP-1); (6561:) Uracil-DNA glycosylase (UDG); (6562:) uracil-DNA glycosylase isoform UNG1 precursor [Homo sapiens]; (6563:) uracil-DNA glycosylase isoform UNG2 [Homo sapiens]; (6564:) Urate Transporter 1 (URAT1); (6565:) Urease; (6566:) Uridine diphosphate glucose pyrophosphatase (UDPG pyrophosphatase) (UGPPase) (Nucleoside diphosphate-linked moiety X motif 14) (Nudixmotif 14); (6567:) uridine diphosphate glucose pyrophosphatase [Homo sapiens]; (6568:) uridine phosphorylase (EC 2.4.2.3)-2—human; (6569:) Uridine Phosphorylase (Urd-Pase); (6570:) uridine-cytidine kinase 2 [Homo sapiens]; (6571:) UROD [Homo sapiens]; (6572:) urokinase plasminogen activator preproprotein [Homo sapiens]; (6573:) Urokinase plasminogen activator surface receptor precursor (uPAR) (U-PAR) (Monocyte activation antigen Mo3) (CD87 antigen); (6574:) Urokinase-type plasminogen activator (uPA); (6575:) Urokinase-type plasminogen activator receptor (uPAR); (6576:) Uronyl 2-sulfotransferase; (6577:) uroporphyrinogen decarboxylase (EC 4.1.1.37); (6578:) Uroporphyrinogen decarboxylase (URO-D) (UPD); (6579:) uroporphyrinogen decarboxylase [Homo sapiens]; (6580:) uroporphyrinogen decarboxylase; (6581:) Urotensin II (UT-II) Receptor; (6582:) Urotensin II receptor (UR-II-R) (G-protein coupled receptor 14); (6583:) USP48 protein [Homo sapiens]; (6584:) usurpin beta [Homo sapiens]; (6585:) Usurpin-alpha [Homo sapiens]; (6586:) Usurpin-beta [Homo sapiens]; (6587:) Usurpin-gamma [Homo sapiens]; (6588:) UTP-hexose-1-phosphate uridylyltransferase (EC 2.7.7.10)—human; (6589:) UURF2 ubiquitin ligase [Homo sapiens]; (6590:) Vacuolar ATP synthase 16 kDa proteolipid subunit; (6591:) Vacuolar ATP synthase catalytic subunit A, osteoclast isoform(V-ATPase subunit A 2) (Vacuolar proton pump alpha subunit 2) (V-ATPase 69 kDa subunit 2) (Isoform HO68); (6592:) Vacuolar ATP synthase catalytic subunit A, ubiquitous isoform(V-ATPase subunit A 1) (Vacuolar proton pump alpha subunit 1) (V-ATPase 69 kDa subunit 1) (Isoform VA68); (6593:) Vacuolar ATP synthase subunit B, brain isoform (V-ATPase B2subunit) (Vacuolar proton pump B isoform 2) (Endomembrane protonpump 58 kDa subunit) (HO57); (6594:) Vacuolar ATP synthase subunit B, kidney isoform (V-ATPase B1 subunit) (Vacuolar proton pump B isoform 1) (Endomembrane protonpump 58 kDa subunit); (6595:) Vacuolar ATP synthase subunit C (V-ATPase C subunit) (Vacuolarproton pump C subunit); (6596:) Vacuolar ATP synthase subunit D (V-ATPase D subunit) (Vacuolarproton pump D subunit) (V-ATPase 28 kDa accessory protein); (6597:) Vacuolar ATP synthase subunit d (V-ATPase d subunit) (Vacuolarproton pump subunit d) (V-ATPase AC39 subunit) (V-ATPase 40 kDa accessory protein) (P39) (32 kDa accessory protein); (6598:) Vacuolar ATP synthase subunit E (V-ATPase E subunit) (Vacuolarproton pump E subunit) (V-ATPase 31 kDa subunit) (P31); (6599:) Vacuolar ATP synthase subunit F (V-ATPase F subunit) (Vacuolarproton pump F subunit) (V-ATPase 14 kDa subunit); (6600:) Vacuolar ATP synthase subunit G 1 (V-ATPase G subunit 1) (Vacuolarproton pump G subunit 1) (V-ATPase 13 kDa subunit 1) (Vacuolar ATPsynthase subunit M16); (6601:) Vacuolar ATP synthase subunit G 2 (V-ATPase G subunit 2) (Vacuolarproton pump G subunit 2) (V-ATPase 13 kDa subunit 2); (6602:) Vacuolar ATP synthase subunit G 3 (V-ATPase G subunit 3) (Vacuolarproton pump G subunit 3) (V-ATPase 13 kDa subunit 3); (6603:) Vacuolar ATP synthase subunit H (V-ATPase H subunit) (Vacuolarproton pump subunit H) (V-ATPase 50/57 kDa subunits) (Vacuolarproton pump subunit SFD) (VMA13) (Nef-binding protein 1) (NBP1); (6604:) vacuolar ATPase subunit H [Homo sapiens]; (6605:) vacuolar H+ ATPase C2 isoform a [Homo sapiens]; (6606:) vacuolar H+ ATPase C2 isoform b [Homo sapiens]; (6607:) vacuolar H+ ATPase E1 isoform a [Homo sapiens]; (6608:) vacuolar H+ ATPase E1 isoform b [Homo sapiens]; (6609:) vacuolar H+ ATPase E1 isoform c [Homo sapiens]; (6610:) vacuolar H+ ATPase G1 [Homo sapiens]; (6611:) vacuolar H+ ATPase B2 [Homo sapiens]; (6612:) Vacuolar Hydrogen Transporting ATPase (V-ATPase); (6613:) Vacuolar protein sorting-associated protein 26A (Vesicle protein sorting 26A) (hVPS26); (6614:) Vacuolar protein sorting-associated protein 26B (Vesicle protein sorting 26B); (6615:) Vacuolar protein sorting-associated protein 29 (Vesicle protein sorting 29) (hVPS29) (PEP11); (6616:) Vacuolar protein sorting-associated protein 35 (Vesicle protein sorting 35) (hVPS35) (Maternal-embryonic 3); (6617:) vacuolar proton pump subunit SFD alpha isoform [Homo sapiens]; (6618:) Vacuolar proton translocating ATPase 116 kDa subunit a isoform 1(V-ATPase 116 kDa isoform a1) (Clathrin-coated vesicle/synaptic vesicle proton pump 116 kDa subunit) (Vacuolar proton pump subunit1) (Vacuolar adenosine triphosphatase subunit Ac116); (6619:) Vacuolar proton translocating ATPase 116 kDa subunit a isoform 2(V-ATPase 116 kDa isoform a2) (TJ6); (6620:) Vacuolar proton translocating ATPase 116 kDa subunit a isoform 3(V-ATPase 116 kDa isoform a3) (Osteoclastic proton pump 116 kDa subunit) (OC-116 kDa) (OC116) (T-cell immune regulator 1) (T cellimmune response cDNA7 protein) (TIRC7); (6621:) Vacuolar proton translocating ATPase 116 kDa subunit a isoform 4(V-ATPase 116 kDa isoform a4) (Vacuolar proton translocating ATPase116 kDa subunit a kidney isoform); (6622:) v-akt murine thymoma viral oncogene homolog 1 [Homo sapiens]; (6623:) v-akt murine thymoma viral oncogene homolog 2 [*Homo sapiens*]; (6624:) Valacyclovir hydrolase precursor (VACVase) (Biphenyl hydrolase-likeprotein) (Biphenyl hydrolase-related protein) (Bph-rp) (Breast epithelial mucin-associated antigen) (MCNAA); (6625:) valosin containing protein (p97)/p47 complex interacting protein 1 [*Homo sapiens*]; (6626:) Valyl-tRNA synthetase (Valine—tRNA ligase) (ValRS) (Protein G7a); (6627:) Vanilloid Receptor 1 (VR1); (6628:) Vascular Adhesion Protein-1 (VAP-1) Receptor; (6629:) vascular adhesion protein-1 [*Homo sapiens*]; (6630:) Vascular Adhesion Protein-1/Semicarbazide-Sensitive Amine Oxidase (VAP-1/SSAO); (6631:) "vascular adhesion protein-1; semicarbazide sensitive amine oxidase; copper-containing amine oxidase homolog [*Homo sapiens*]."; (6632:) Vascular Cell Adhesion Molecule-1 (VCAM-1) Expression; (6633:) Vascular Endothelial Growth Factor (VEGF); (6634:) Vascular Endothelial Growth Factor (VEGF) Receptor; (6635:) Vascular Endothelial Growth Factor 121 (VEGF121); (6636:) Vascular Endothelial Growth Factor 145 (VEGF145); (6637:) Vascular Endothelial Growth Factor 165 (VEGF165); (6638:) Vascular Endothelial Growth Factor 165 (VEGF165) Receptor; (6639:) vascular endothelial growth factor A isoform a precursor [*Homo sapiens*]; (6640:) vascular endothelial growth factor A isoform b precursor [*Homo sapiens*]; (6641:) vascular endothelial growth factor A isoform c precursor [*Homo sapiens*]; (6642:) vascular endothelial growth factor A isoform d precursor [*Homo sapiens*]; (6643:) vascular endothelial growth factor A isoform e precursor [*Homo sapiens*]; (6644:) vascular endothelial growth factor A isoform f precursor [*Homo sapiens*]; (6645:) vascular endothelial growth factor A isoform g precursor [*Homo sapiens*]; (6646:) Vascular Endothelial Growth Factor Receptor 1 (VEGFR-1); (6647:) Vascular endothelial growth factor receptor 1 precursor (VEGFR-1) (Vascular permeability factor receptor) (Tyrosine-protein kinasereceptor FLT) (Flt-1) (Tyrosine-protein kinase FRT) (Fms-like tyrosine kinase 1); (6648:) Vascular Endothelial Growth Factor Receptor 2 (VEGFR-2); (6649:) Vascular endothelial growth factor receptor 2 precursor (VEGFR-2) (Kinase insert domain receptor) (Protein-tyrosine kinase receptor Flk-1) (CD309 antigen); (6650:) Vascular endothelial growth factor receptor 3 precursor (VEGFR-3) (Tyrosine-protein kinase receptor FLT4); (6651:) Vascular Endothelial Growth Factor Receptor1-Tyrosine Kinase (VEGFR1-TK); (6652:) Vascular Endothelial Growth Factor Receptor2-Tyrosine Kinase (VEGFR2-TK); (6653:) Vascular Endothelial Growth Factor Receptor-Tyrosine Kinase (VEGFR-TK); (6654:) Vascular Endothelial-Cadherin (VE-Cadherin); (6655:) Vasoactive Intestinal Peptide Receptor 1 (VPAC1); (6656:) vasoactive intestinal peptide receptor-related protein precursor (clone hIVR5)—human; (6657:) Vasoactive intestinal polypeptide receptor 1 precursor (VIP-R-1) (Pituitary adenylate cyclase-activating polypeptide type II receptor) (PACAP type II receptor) (PACAP-R-2); (6658:) Vasoactive intestinal polypeptide receptor 2 precursor (VIP-R-2) (Pituitary adenylate cyclase-activating polypeptide type III receptor) (PACAP type III receptor) (PACAP-R-3) (Helodermin-preferring VIP receptor); (6659:) Vasopressin Via receptor (V1aR) (Vascular/hepatic-type argininevasopressin receptor) (Antidiuretic hormone receptor 1a) (AVPRV1a); (6660:) Vasopressin V1b receptor (V1bR) (AVPR V1b) (Vasopressin V3receptor) (AVPR V3) (Antidiuretic hormone receptor 1b); (6661:) Vasopressin V2 receptor (Renal-type arginine vasopressin receptor) (Antidiuretic hormone receptor) (AVPR V2); (6662:) VELF1904 [*Homo sapiens*]; (6663:) Very low-density lipoprotein receptor precursor (VLDL receptor) (VLDL-R); (6664:) Very-long-chain acyl-CoA synthetase (VLCS) (Very-long-chain-fatty-acid-CoA ligase) (VLACS) (THCA-CoA ligase) (Fatty-acid-coenzyme A ligase, very long-chain 1) (Long-chain-fatty-acid—CoA ligase) (Fatty acid transport protein2) (FATP-2) (Solute carrier family 27 member 2); (6665:) vesicle docking protein p115 [*Homo sapiens*]; (6666:) Vesicle-associated membrane protein 8 (VAMP-8) (Endobrevin) (EDB); (6667:) v-ets erythroblastosis virus E26 oncogene homolog 1 [*Homo sapiens*]; (6668:) visfatin precursor [*Homo sapiens*]; (6669:) Visual pigment-like receptor peropsin; (6670:) vitamin D (1,25-dihydroxyvitamin D3) receptor [*Homo sapiens*]; (6671:) vitamin D inducible protein [*Homo sapiens*]; (6672:) Vitamin D Receptor (VDR); (6673:) Vitamin D3 receptor (VDR) (1,25-dihydroxyvitamin D3 receptor); (6674:) Vitamin K; (6675:) Vitamin K epoxide reductase complex subunit 1 (Vitamin K12,3-epoxide reductase subunit 1); (6676:) vitamin K epoxide reductase complex, subunit 1 isoform 1 [*Homo sapiens*]; (6677:) vitamin K epoxide reductase complex, subunit 1 isoform 2 [*Homo sapiens*]; (6678:) "Vitamin K-dependent protein C precursor (Autoprothrombin IIA) (Anticoagulant protein C) (Blood coagulation factor XIV) [Contains: Vitamin K-dependent protein C light chain; Vitamin K-dependent protein C heavy chain; Activation peptide] ."; (6679:) Vitamin K-dependent protein Z precursor; (6680:) v-kit Hardy-Zuckerman 4 feline sarcoma viral oncogene homolog precursor [*Homo sapiens*]; (6681:) v-maf musculoaponeurotic fibrosarcoma oncogene homolog G [*Homo sapiens*]; (6682:) v-maf musculoaponeurotic fibrosarcoma oncogene homolog isoform a [*Homo sapiens*]; (6683:) v-maf musculoaponeurotic fibrosarcoma oncogene homolog isoform b [*Homo sapiens*]; (6684:) Vomeronasal type-1 receptor 1 (V1r-like receptor 1) (Vomeronasalolfactory receptor chromosome 19 subtype I member 1) (V3r-related gene) (hGPCR24); (6685:) Vomeronasal type-1 receptor 2 (V1r-like receptor 2) (hGPCR25); (6686:) Vomeronasal type-1 receptor 3 (V1r-like receptor 3); (6687:) Vomeronasal type-1 receptor 4 (V1r-like receptor 4) (hGPCR27); (6688:) Vomeronasal type-1 receptor 5 (V1r-like receptor 5) (hGPCR26); (6689:) Von Hippel-Lindau disease tumor suppressor (pVHL) (G7 protein); (6690:) von Hippel-Lindau tumor suppressor isoform 1 [*Homo sapiens*]; (6691:) von Hippel-Lindau tumor suppressor isoform 2 [*Homo sapiens*]; (6692:) von Willebrand Factor (vWF) Receptor; (6693:) von Willebrand factor preproprotein [*Homo sapiens*]; (6694:) v-raf murine sarcoma 3611 viral oncogene homolog [*Homo sapiens*]; (6695:) v-raf murine sarcoma viral oncogene homolog B1 [*Homo sapiens*]; (6696:) v-raf-1 murine leukemia viral oncogene homolog 1 [*Homo sapiens*]; (6697:) v-rel reticuloendotheliosis viral oncogene homolog A, nuclear factor of kappa light polypeptide gene enhancer in B-cells 3, p65 [*Homo sapiens*]; (6698:) wax synthase [*Homo sapiens*]; (6699:) Wee1-like protein kinase (Wee1A kinase) (WEE1hu); (6700:) Werner syndrome protein [*Homo sapiens*]; (6701:) Wiskott-Aldrich syndrome protein [*Homo sapiens*]; (6702:) Wnt; (6703:) WW, C2 and coiled-coil domain containing 1 [*Homo sapiens*]; (6704:) xanthine dehydrogenase [*Homo sapiens*]; (6705:) "Xanthine dehydrogenase/oxidase [Includes:) Xanthine dehydrogenase(XD); Xanthine oxidase (XO) (Xanthine oxidoreductase)]."; (6706:) Xanthine Oxidase (XO); (6707:) X-Linked inhibitor of Apoptosis Protein (XIAP); (6708:) X-linked interleukin-1 receptor accessory protein-like 1 precursor (IL1RAPL-1) (Oligophrenin-4) (Three immunoglobulindomain-containing IL-1 receptor-related 2) (TIGIRR-2); (6709:) X-linked interleukin-1 receptor accessory protein-like 2 precursor (IL1RAPL-2-related protein)

(Interleukin-1 receptor 9) (IL-1R9) (IL-1 receptor accessory protein-like 2) (Three immunoglobulindomain-containing IL-1 receptor-related 1) (TIGIRR-1); (6710:) X-linked phosphate regulating endopeptidase homolog [*Homo sapiens*]; (6711:) X-prolyl aminopeptidase (aminopeptidase P) 1, soluble [*Homo sapiens*]; (6712:) X-prolyl aminopeptidase 2, membrane-bound [*Homo sapiens*]; (6713:) xylosylprotein beta 1,4-galactosyltransferase 7 [*Homo sapiens*]; (6714:) Xylosyltransferase 1 (Xylosyltransferase I) (XyIT-1) (XT-I) (Peptide O-xylosyltransferase 1); (6715:) Xylosyltransferase 2 (Xylosyltransferase II) (xyIT-II) (XT-II) (Peptide O-xylosyltransferase 1); (6716:) xylosyltransferase I [*Homo sapiens*]; (6717:) xylosyltransferase II [*Homo sapiens*]; (6718:) Xaa-Pro aminopeptidase 1 (X-Pro aminopeptidase 1) (X-prolylaminopeptidase 1, soluble) (Cytosolic aminopeptidase P) (Solubleaminopeptidase P) (sAmp) (Aminoacylproline aminopeptidase); (6719:) Xaa-Pro dipeptidase (X-Pro dipeptidase) (Proline dipeptidase) (Prolidase) (Imidodipeptidase); (6720:) Xaa-Pro dipeptidase [*Homo sapiens*]; (6721:) Yama protein; (6722:) Ymer protein long isoform [*Homo sapiens*]; (6723:) Ymer protein short isoform [*Homo sapiens*]; (6724:) YOD1 OTU deubiquinating enzyme 1 homolog [*Homo sapiens*]; (6725:) Zinc finger FYVE domain-containing protein 9 (Mothers against decapentaplegic homolog-interacting protein) (Madh-interacting protein) (Smad anchor for receptor activation) (Receptor activation anchor) (hSARA) (Novel serine protease) (NSP); (6726:) zinc finger protein 146 [*Homo sapiens*]; (6727:) zinc finger protein Cezanne [*Homo sapiens*]; (6728:) Zinc finger protein OZF (Only zinc finger protein) (Zinc finger protein 146); (6729:) zinc metalloproteinase STE24 homolog [*Homo sapiens*]; (6730:) Zinc phosphodiesterase ELAC protein 1 (Ribonuclease Z 1) (RNase Z1) (tRNase Z 1) (tRNA 3 endonuclease 1) (ElaC homolog protein 1) (Deleted in Ma29); (6731:) Zinc phosphodiesterase ELAC protein 2 (Ribonuclease Z 2) (RNase Z2) (tRNase Z 2) (tRNA 3 endonuclease 2) (ElaC homolog protein 2) (Heredity prostate cancer protein 2); (6732:) Zona pellucida sperm-binding protein 2 precursor (Zona pellucidaglycoprotein ZP2) (Zona pellucida protein A)

Methods for Isolating "Lead Compounds"

The present invention in one embodiment is also directed to a method for isolating novel "drug leads" or "lead compounds" from libraries of different molecules synthesised by the methods of the invention. A "drug lead" or "lead compound" is a compound which may not in itself be suitable as a drug, but which exhibits a number of characteristics which are interesting when viewed from the point of view of medical therapy.

The reasons why such "lead compounds" are often unsuitable could be toxicity, unsuitable pharmacokinetic or pharmacodynamic properties, difficulties relating to preparation and purification etc. In such cases, the "lead compound" is used as a model for de novo synthesis of other chemical compounds which are designed so as to be related to the active part of the lead compound in 3D structure and distribution of charged, polar and non-polar groups.

This approach can be refined by initially identifying the members of the library by methods of structure-based or nonstructure based computer drug-modelling. Suitable nonstructure based methods are disclosed in e.g. U.S. Pat. Nos. 5,307,287 and 5,025,388 (a method known as CoMFA). An alternative is HASL (Hypothetical Active Site Lattice; Hypothesis Software). Both these methods are based on 3D-QSAR. A feasible structure-based approach is e.g. disclosed in WO 95/06293.

In view of the above, the present invention also pertains to a method for the preparation of a medicinal product, the method comprising the steps of a) selecting a chemical compound by the methods of the invention described above, b) performing pre-clinical tests with the chemical compound in order to assess the suitability thereof as a medicinal product, c) entering, if the chemical compound is deemed suitable in step (b), clinical trials using the chemical compound in order to obtain market authorization for a medicinal product including the chemical compound as a pharmaceutically active substance, and d) upon grant of a market authorization, admixing the chemical compound with a pharmaceutically acceptable carrier excipient or diluent and marketing the thus obtained medicinal product.

The above-outlined methods should take into consideration all necessary requirements in order to meet GCP and GMP standards.

Additional preferred uses and embodiments of the present invention is disclosed herein below. A number of assays which can be used to verify or identify an effect or property of a molecule identified by one or more methods of the present invention can be performed by a person skilled in the art.

In embodiments of the present invention, the bioactive species encoding it is used to identify pharmaceutically relevant target molecules, i.e. the molecules with which the bioactive species can form an interaction. As will be appreciated by those in the art, there can be primary target molecules to which the bioactive species binds or acts upon directly and there can be secondary target molecules, which are part of a signalling pathway affected by the bioactive species; the latter might be termed "validated targets".

In one embodiment, the present methods are useful in cancer applications. The ability to rapidly and specifically kill tumor cells is a cornerstone of cancer chemotherapy. In general, using the methods of the present invention, bioactive species can be identified which, when introduced into any tumor cell (primary or cultured), induce apoptosis, cell death loss of cell division or decreased cell growth. This can be done de novo, or by biased randomization toward known cancer agents, such as angiostatin, which inhibits blood vessel wall growth. According to one embodiment of the present invention, the methods for synthesising a molecule linked to a single stranded identifier oligonucleotide is targeted to a target compound known to be involved in induction of apoptosis, cell death loss of cell division or decreased cell growth.

Targets can include e.g. known proteins such as Abl, Src, Ras, and others, which lead to abnormal cell growth in certain cells or the development of micro-metastases. Thus, in one embodiment, bioactive species obtainable by the methods of the invention are introduced into cancer cells to select for bioactive species which reverse or correct a cancer condition. One of the signal features of oncogene activity in cells is the loss of contact inhibition and the ability to grow in soft-agar. When e.g. Abl, Src, or Ras are expressed 3T3 cells and subjected to puromycin selection, all of the 3T3 cells hyper-transform and detach from the plate. The cells can be removed by washing with fresh medium. This can serve as the basis of a screen, since cells which express a bioactive species having anti-cancer activity will remain attached to the plate and form colonies.

Similarly, the growth and/or spread of certain tumor types is enhanced by stimulatory responses from growth factors and cytokines (PDGF, EGF, Heregulin, and others) which bind to receptors on the surfaces of specific tumors. In one embodiment, the bioactive species obtainable by the methods of the invention are used to inhibit or stop tumor growth and/or spread selecting bioactive species capable of blocking the ability of the growth factor or cytokine to stimulate the tumor cell. The introduction of bioactive species obtainable by the methods of the present invention into specific tumor cells with the addition of the growth factor or cytokine, followed by selection of bioactive species which block the binding, signaling, phenotypic and/or functional responses of these tumor cells to the growth factor or cytokine in question, represent one embodiment of the present invention.

Similarly, the spread of cancer cells (invasion and metastasis) is a significant problem limiting the success of cancer therapies. The ability to inhibit the invasion and/or migration of specific tumor cells would be a significant advance in the therapy of cancer. Tumor cells known to have a high metastatic potential (for example, melanoma, lung cell carcinoma, breast and ovarian carcinoma) can have bioactive species obtainable by the methods of the present invention introduced into them, and bioactive species selected which in a migration or invasion assay, inhibit the migration and/or invasion of specific tumor cells. Particular applications for inhibition of the metastatic phenotype, which could allow a more specific inhibition of metastasis, include the polypeptide encoded by the metastasis suppressor gene NM23, which codes for a dinucleoside diphosphate kinase. Thus, bioactive species acting as activators of this gene could block metastasis. Many oncogene products also enhance metastasis.

Bioactive species which inactivate or counteract gene products encoded by mutated RAS oncogenes, v-MOS, v-RAF, A-RAF, v-SRC, v-FES, and v-FMS would also act as anti-metastatics. Bioactive species obtainable by the invention which act intracellularly to block the release of combinations of proteases required for invasion, such as the matrix metalloproteases and urokinase, could also be effective antimetastatics.

In one embodiment, the bioactive species obtainable by the methods of the present invention are introduced into tumor cells known to have inactivated tumor suppressors, and successful reversal e.g. by compensation of suppression of the suppressor can be screened for e.g. by restoration of a normal phenotype. A major example is the reversal of p53-inactivating mutations, which are present in 50% or more of all cancers. Since p53's actions are complex and involve its action as a transcription factor, there are probably numerous potential ways a small molecule bioactive species could reverse the mutation. One example could be e.g. to increase the activity of the cyclin-dependent kinase p21CIP1NVAF1. To be useful such reversal would have to work for many of the different known p53 mutations. It is possible to screen for one or more small molecules possessing the above-cited activities.

In another embodiment, the methods of the present invention for synthesising and selecting small molecule bioactive species are useful in various cardiovascular applications. In one embodiment, cardiomyocytes can be screened for the prevention of cell damage or death in the presence of normally injurious conditions, including, but not limited to, the presence of toxic drugs (particularly chemo-therapeutic drugs), for example, to prevent heart failure following treatment with adriamycin; anoxia, for example in the setting of coronary artery occlusion; and autoimmune cellular damage by attack from activated lymphoid cells (for example as seen in post viral myocarditis and lupus). Candidate bioactive species are inserted into cardiomyocytes, the cells are subjected to the insult. It is possible to screen for bioactive species are selected that prevent any or all of: apoptosis; membrane depolarization (i.e. decrease arrythmogenic potential of insult); cell swelling; or leakage of specific intracellular ions, second messengers and activating molecules (for example, arachidonic acid and/or lysophosphatidic acid).

In yet another embodiment, the bioactive species obtainable by the methods of the present invention are used to screen for diminished arrhythmia potential in cardiomyocytes. The screens comprise the introduction of the candidate bioactive species, followed by the application of arrythmogenic insults, with screening for bioactive species that block specific depolarization of cell membrane. This can be detected using patch clamps, or via fluorescence techniques). Similarly, channel activity (for example, potassium and chloride channels) in cardiomyocytes could be regulated using the bioactive species obtainable by the methods of the present invention in order to enhance contractility and prevent or diminish arrhythmias.

In yet another embodiment, the bioactive species obtainable by the methods of the present invention are used to screen for enhanced contractile properties of cardiomyocytes and diminish heart failure potential. The introduction of the bioactive species obtainable by the methods of the present invention followed by measuring the rate of change of myosin polymerization/depolymerization using fluorescent techniques can be done. It is possible to screen for bioactive species which increase the rate of change of this phenomenon can result in a greater contractile response of the entire myocardium, similar to the effect seen with digitalis.

In a still further embodiment, selected bioactive species obtainable by the methods of the present invention can be useful for identifying agents involved in the regulation of intracellular and sarcolemmal calcium cycling in cardiomyocytes in order to prevent arrhythmias. It is possible to screen for bioactive species which regulate sodium-calcium exchange, sodium proton pump function, and regulation of calcium-ATPase activity in human or animal cells.

In one embodiment, the bioactive species obtainable by the methods of the present invention are useful for identifying agents that diminish embolic phenomena in arteries and arterioles leading to strokes (and other occlusive events leading to kidney failure and limb ischemia) and angina precipitating a myocardial infarct are selected. For example, it is possible to screen for bioactive species which will diminish the adhesion of platelets and leukocytes, and thus diminish the occlusion events.

Adhesion in this setting can be inhibited by the bioactive species obtainable by the methods of the present invention once such bioactive species are inserted into endothelial cells (quiescent cells, or activated by cytokines, i.e. IL-1, and growth factors, i.e. PDGF I EGF) and then screened for either: 1) downregulation of adhesion molecule expression on the surface of the endothelial cells (binding assay); 2) blocking of adhesion molecule activation on the surface of these cells (signaling assay); or 3) releasing in an autocrine manner biological molecules including peptides that block receptor binding to the cognate receptor on the adhering cell.

Embolic phenomena can also be addressed by activating proteolytic enzymes on the cell surfaces of endothelial cells, and thus releasing active enzyme which can digest blood clots. Thus, the bioactive species obtainable by the methods of the present invention can be introduced into endothelial cells, followed by standard fluorogenic assays, which will allow monitoring of proteolytic activity on the cell surface towards a known substrate. Bioactive species can then be selected which activate specific enzymes towards specific substrates.

In one embodiment, arterial inflammation in the setting of vasculitis and post-infarction can be regulated by decreasing the chemotactic responses of leukocytes and mononuclear leukocytes. This can be accomplished by blocking chemotactic receptors and their responding pathways on these cells. Candidate bioactive species can thus be inserted into these cells, and one can screen for inhibition of the chemotactic response to diverse chemokines (for example, to the IL-8 family of chemokines, RANTES) in cell migration assays.

In yet another embodiment, arterial restenosis following coronary angioplasty can be controlled by regulating the proliferation of vascular intimal cells and capillary and/or arterial endothelial cells. Candidate bioactive species can be inserted into these cell types and their proliferation in response to specific stimuli can be monitored. It is possible to screen for bioactive species which are capable of blocking the expression or function of c-myc and other oncogene products in smooth muscle cells to stop their proliferation. It would also be possible to introduce the bioactive species obtainable by the methods of the present invention into vascular smooth muscle cells and to screen for bioactive species which can selectively induce apoptosis.

Application of small molecule bioactive species may require targeted drug delivery; this is available e.g. with stents, hydrogel coatings, and infusion-based catheter systems. Bioactive species which down regulate endothelin-1A receptors or which block the release of the potent vasoconstrictor and vascular smooth muscle cell mitogen endothelin-I may also be candidates for therapeutics. Accordingly, it is possible to screen for bioactive species which can inhibit growth of these cells, or which prevent the adhesion of other cells in the circulation known to release autocrine growth factors, such as platelets (PDGF) and mononuclear leukocytes.

The control of capillary and blood vessel growth is an important goal in order to promote increased blood flow to ischemic areas (growth), or to cut-off the blood supply (angiogenesis inhibition) of tumors. Candidate bioactive species can be inserted into capillary endothelial cells and the growth of such cells can be monitored. Stimuli such as low oxygen tension and varying degrees of angiogenic factors can regulate the responses, and one can screen for bioactive species which can produce the appropriate phenotype. Screening for bioactive species capable of acting as antagonisms of vascular endothelial cell growth factor, important in angiogenesis, would also be useful.

In one embodiment, the bioactive species obtainable by the methods of the present invention are useful in screening for decreases in atherosclerosis producing mechanisms to find biological molecules that regulate LDL and HDL metabolism. Candidate bioactive species can be inserted into the appropriate cells (including hepatocytes, mononuclear leukocytes, endothelial cells) and one can screen for bioactive species which lead to a decreased release of LDL or diminished synthesis of LDL, or conversely to an increased release of HDL or enhanced synthesis of HDL. It is also possible to screen for bioactive species which decreases the production of oxidized LDL, which has been implicated in atherosclerosis and isolated from atherosclerotic lesions. This could occur e.g. by activating reducing systems or enzymes, or blocking the activity or production of enzymes implicated in production of oxidized LDL, such as 1 5-lipoxygenase in macrophages.

In one embodiment, the bioactive species obtainable by the methods of the present invention are used in screens to regulate obesity via the control of food intake mechanisms or diminishing the responses of receptor signaling pathways that regulate metabolism. One can screen for bioactive species that regulate or inhibit the responses of neuropeptide Y (NPY), cholecystokinin and galanin receptors. Candidate bioactive species can be inserted into cells that have these receptors cloned into them, and one can screen for bioactive species which block the signaling responses to galanin and NPY. In a similar manner, one can screen for bioactive species which regulate the leptin receptor.

In a still further embodiment, bioactive species obtainable by the methods of the present invention can be used in screens in neurobiology applications. Candidate bioactive species can be used for screening for anti-apoptotics for preservation of neuronal function and prevention of neuronal death. Initial screens would be done in cell culture. One application would include prevention of neuronal death, by apoptosis, in cerebral ischemia resulting from stroke. Apoptosis is known to be blocked by neuronal apoptosis inhibitory polypeptide (NAIP); screens for its upregulation, or effecting any coupled step could yield bioactive species which selectively block neuronal apoptosis. Other applications include neurodegenerative diseases such as Alzheimer's disease and Huntington's disease.

In another embodiment, bioactive species obtainable by the methods of the present invention can be used in screens in bone biology applications. Osteoclasts are known to play a key role in bone remodeling by breaking down "old" bone, so that osteoblasts can lay down "new" bone. In osteoporosis one has an imbalance of this process. A screen for osteoclast overactivity can be set up by introducing candidate bioactive species to these cells, and then screening for bioactive species that produce: 1) a diminished processing of collagen by these cells; 2) decreased pit formation on bone chips; and 3) decreased release of calcium from bone fragments.

The bioactive species obtainable by the methods of the present invention can also be used in screens for agonists of bone morphogenic biological molecules and hormone mimetics to stimulate, regulate, or enhance new bone formation (in a manner similar to parathyroid hormone and calcitonin, for example). These have use in osteoporosis, for poorly healing fractures, and to accelerate the rate of healing of new fractures. Furthermore, cell lines of connective tissue origin can be treated with candidate bioactive species and screened for their growth, proliferation, collagen stimulating activity, and/or proline incorporating ability on the target osteoblasts. Alternatively, candidate bioactive species can be screened for their ability to increase production of collagen or bone.

In one embodiment, bioactive species obtainable by the methods of the present invention can be screened for activities which are useful in various skin biology applications. Keratinocyte responses to a variety of stimuli may result in psoriasis, a proliferative change in these cells. Candidate bioactive species can be inserted into cells removed from active psoriatic plaques, and one can screen for bioactive species which decrease the rate of growth of these cells.

In one embodiment, the bioactive species obtainable by the methods of the present invention can be screened for activities which are useful in the regulation or inhibition of keloid formation (i.e. excessive scarring). Candidate bioactive species can be introduced into skin connective tissue cells isolated from individuals with this condition, and one can screen for bioactive species that decrease proliferation, collagen formation, or proline incorporation. Results from this work can be extended to treat the excessive scarring that also occurs in burn patients. If a common bioactive species motif is found in the context of the keloid work, then it can be tested if this motif can be used widely in a topical manner to diminish scarring post burn.

Similarly, wound healing for diabetic ulcers and other chronic "failure to heal" conditions in the skin and extremities can be regulated by providing additional growth signals to cells which populate the skin and dermal layers. Growth factor mimetics may in fact be very useful for this condition. Candidate bioactive species can be inserted into skin connective tissue cells, and one can screen for bioactive species which promote the growth of these cells under "harsh" conditions, such as low oxygen tension, low pH, and the presence of inflammatory mediators.

Cosmeceutical applications of the present invention include the control of melanin production in skin melanocytes. A naturally occurring peptide, arbutin, is a tyrosine hydroxylase inhibitor, a key enzyme in the synthesis of melanin. Candidate bioactive species can be introduced into melanocytes and known stimuli that increase the synthesis of melanin applied to the cells. One can screen for bioactive species which inhibit the synthesis of melanin under these conditions.

In one embodiment, one can screen for activities of bioactive species obtainable by the methods of the present invention which are useful in endocrinology applications. The methods of the present invention and the bioactive species thus obtained can be applied broadly to any endocrine, growth factor, cytokine or chemokine network which involves a signaling peptide or polypeptide that acts in either an endocrine, paracrine or autocrine manner that binds or dimerizes a receptor and activates a signaling cascade that results in a known phenotypic or functional outcome. One can screen for bioactive species which either mimics a desired hormone (i.e., insulin, leptin, calcitonin, PDGF, EGF, EPO, GMCSF, IL1-17, mimetics) or inhibits its action by either blocking the release of the hormone, blocking its binding to a specific receptor or carrier polypeptide (for example, CRF binding polypeptide), or inhibiting the intracellular responses of the specific target cells to that hormone. It is also possible to screen for bioactive species which increase the expression or release of hormones from cells which normally produce them. This would have broad applications in conditions of hormonal deficiency.

In one embodiment, one can screen for activities of bioactive species obtainable by the methods of the present invention which are useful in infectious disease applications. Viral latency (herpes viruses such as CMV, EBV, HBV, and other viruses such as HIV) and their reactivation are a significant problem, particularly in immunosuppressed patients (patients with AIDS and transplant patients). The ability to block the reactivation and spread of these viruses is an important goal. Cell lines known to harbor or be susceptible to latent viral infection can be infected with the specific virus, and then stimuli applied to these cells which have been shown to lead to reactivation and viral replication. This can be followed by measuring viral titers in the medium and scoring cells for phenotypic changes. Candidate bioactive species can then be introduced into these cells under the above conditions, and one can screen for bioactive species which block or diminish the growth and/or release of the virus. As with chemotherapeutics, these experiments can also be done in combination with drugs which are only partially effective towards this outcome, and one can screen for bioactive species which enhance the virucidal effect of these drugs.

One example of many is the ability to block HIV-1 infection. HIV-1 requires CD4 and a co-receptor which can be one of several seven transmembrane G-polypeptide coupled receptors. In the case of the infection of macrophages, CCR-5 is the required coreceptor, and there is strong evidence that a block on CCR-5 will result in resistance to HIV-1 infection. There are two lines of evidence for this statement. First, it is known that the natural ligands for CCR-5, the CC chemokines RANTES, MIPIa and MIPIb are responsible for CD8+ mediated resistance to HIV. Second, individuals homozygous for a mutant allele of CCR-5 are completely resistant to HIV infection. Accordingly, one can screen for activities of bioactive species obtainable by the methods of the present invention which are inhibitory for CCR-5/HIV interaction.

Viruses are known to enter cells using specific receptors to bind to cells (for example, HIV uses CD4, coronavirus uses CD13, murine leukemia virus uses transport polypeptide, and measles virus uses CD44) and to fuse with cells (HIV uses chemokine receptor). Candidate bioactive species can be introduced into target cells known to be permissive to these viruses, and one can screen for bioactive species which block the ability of these viruses to bind to and fuse with specific target cells.

In one embodiment, one can screen for activities of bioactive species obtainable by the methods of the present invention which have applications in the area of infectious organisms. Intracellular organisms such as mycobacteria, *listeria, salmonella, pneumocystis, yersinia, leishmania, T. cruzi*, can persist and replicate within cells, and become active in immunosuppressed patients. There are currently drugs on the market and in development which are either only partially effective or ineffective against these organisms. Candidate bioactive species can be inserted into specific cells infected with these organisms (pre- or post-infection), and one can screen for bioactive species which promote the intracellular destruction of these organisms in a manner analogous to intracellular "antibiotic bioactive species" similar to magainins. In addition, one can screen for bioactive species which enhance the cidal properties of drugs already under investigation which have insufficient potency by themselves, but, when combined with one or more bioactive species obtainable by the methods of the present invention, are dramatically more potent through a synergistic mechanism or otherwise. One can screen for bioactive species which alter the metabolism of these intracellular organisms, in such a way as to terminate their intracellular life cycle by inhibiting a key organismal event.

Antibiotic drugs that are widely used have certain dose dependent, tissue specific toxicities. For example renal toxicity is seen with the use of gentamicin, tobramycin, and amphotericin; hepatotoxicity is seen with the use of INH and rifampin; bone marrow toxicity is seen with chloramphenicol; and platelet toxicity is seen with ticarcillin, etc. These toxicities limit their use. One can introduce candidate bioactive species into the specific cell types where specific changes leading to cellular damage or apoptosis by the antibiotics are produced, and one can screen for bioactive species which confer protection, when these cells are treated with these specific antibiotics.

Furthermore, the present invention finds use in screening for bioactive species that block antibiotic transport mechanisms. The rapid secretion from the blood stream of certain antibiotics limits their usefulness. For example penicillins are rapidly secreted by certain transport mechanisms in the kidney and choroid plexus in the brain. Probenecid is known to block this transport and increase serum and tissue levels. Candidate agents can be introduced into specific cells derived from kidney cells and cells of the choroid plexus known to have active transport mechanisms for antibiotics. One can then screen for bioactive species which block the active transport of specific antibiotics and thus extend the serum halflife of these drugs.

In one embodiment bioactive species obtainable by the methods of the present invention are useful in drug toxicities and drug resistance applications. Drug toxicity is a significant clinical problem. This may manifest itself as specific tissue or cell damage with the result that the drug's effectiveness is limited. Examples include myeloablation in high dose cancer chemotherapy, damage to epithelial cells lining the airway and gut, and hair loss.

Specific examples include adriamycin induced cardiomyocyte death, cisplatinin-induced kidney toxicity, vincristine-induced gut motility disorders, and cyclosporin-induced kidney damage. Candidate bioactive species can be introduced into specific cell types with characteristic drug-induced phenotypic or functional responses, in the presence of the drugs, and one can screen for bioactive agents which reverse or protect the specific cell type against the toxic changes when exposed to the drug. These effects may manifest as blocking the drug induced apoptosis of the cell of interest, thus initial screens will be for survival of the cells in the presence of high levels of drugs or combinations of drugs used in combination chemotherapy.

Drug toxicity can be due to a specific metabolite produced in the liver or kidney which is highly toxic to specific cells, or due to drug interactions in the liver which block or enhance the metabolism of an administered drug. Candidate bioactive species can be introduced into liver or kidney cells following the exposure of these cells to the drug known to produce the toxic metabolite. One can screen for bioactive species which alter how the liver or kidney cells metabolize the drug, and for bioactive species which prevent the generation of a specific toxic metabolite. The generation of the metabolite can be followed by mass spectrometry, and phenotypic changes can be assessed by microscopy. Such a screen can also be done in cultured hepatocytes, cocultured with readout cells which are specifically sensitive to the toxic metabolite. Applications include reversible (to limit toxicity) inhibitors of enzymes involved in drug metabolism.

Multiple drug resistance, and hence tumor cell selection, outgrowth, and relapse, leads to morbidity and mortality in cancer patients. Candidate bioactive species can be introduced into tumor cell lines (primary and cultured) that have demonstrated specific or multiple drug resistance. One can then screen for bioactive species which confer drug sensitivity when the cells are exposed to the drug of interest, or to drugs used in combination chemotherapy. The readout can be the onset of apoptosis in these cells, membrane permeability changes, the release of intracellular ions and fluorescent markers. The cells in which multidrug resistance involves membrane transporters can be preloaded with fluorescent transporter substrates, and selection carried out for bioactive species which block the normal efflux of fluorescent drug from these cells. Candidate bioactive species are particularly suited to screening for bioactive species which reverse poorly characterized or recently discovered intracellular mechanisms of resistance or mechanisms for which few or no chemosensitizers currently exist, such as mechanisms involving LRP (lung resistance polypeptide). This polypeptide has been implicated in multidrug resistance in ovarian carcinoma, metastatic malignant melanoma, and acute myeloid leukemia. Particularly interesting examples include screening for agents which reverse more than one important resistance mechanism in a single cell, which occurs in a subset of the most drug resistant cells, which are also important targets. Applications would include screening for inhibitors of both MRP (multidrug resistance related polypeptide) and LRP for treatment of resistant cells in metastatic melanoma, for inhibitors of both p-glycopolypeptide and LRP in acute myeloid leukemia, and for inhibition (by any mechanism) of all three polybioactive species for treating pan-resistant cells.

In one embodiment, the bioactive species obtainable by the methods of the present invention are useful in improving the performance of existing or developmental drugs. First pass metabolism of orally administered drugs limits their oral bioavailability, and can result in diminished efficacy as well as the need to administer more drug for a desired effect. Reversible inhibitors of enzymes involved in first pass metabolism may thus be a useful adjunct enhancing the efficacy of these drugs. First pass metabolism occurs in the liver, thus inhibitors of the corresponding catabolic enzymes may enhance the effect of the cognate drugs.

Reversible inhibitors would be delivered at the same time as, or slightly before, the drug of interest. Screening of candidate bioactive species in hepatocytes for inhibitors (by any mechanism, such as polypeptide down regulation as well as a direct inhibition of activity) of particularly problematical isozymes would be of interest. These include the CYP3A4 isozymes of cytochrome P450, which are involved in the first pass metabolism of the anti-HIV drugs saquinavir and indinavir. Other applications could include reversible inhibitors of UDP-glucuronyltransferases, sulfotransferases, N-acetyltransferases, epoxide hydrolases, and glutathione 5-transferases, depending on the drug. Screens would be done in cultured hepatocytes or liver microsomes, and could involve antibodies recognizing the specific modification performed in the liver, or cocultured readout cells, if the metabolite had a different bioactivity than the untransformed drug.

The enzymes modifying the drug would not necessarily have to be known, if screening was for lack of alteration of the drug.

In one embodiment, the bioactive species obtainable by the methods of the present invention are useful in immunobiology, inflammation, and allergic response applications. Selective regulation of T lymphocyte responses is a desired goal in order to modulate immune-mediated diseases in a specific manner. Candidate bioactive species can be introduced into specific T cell subsets (TH1, TH2, CD4+, CD8+, and others) and the responses which characterize those subsets (cytokine generation, cytotoxicity, proliferation in response to antigen being presented by a mononuclear leukocyte, and others) modified by members of the library. One can screen for activities of bioactive species obtainable by the methods of the present invention which increase or diminish the known T cell subset physiologic response. This approach will be useful in any number of conditions, including: 1) autoimmune diseases where one wants to induce a tolerant state (select a peptide that inhibits T cell subset from recognizing a self-antigen bearing cell); 2) allergic diseases where one wants to decrease the stimulation of IgE producing cells (select peptide which blocks release from T cell subsets of specific Cell stimulating cytokines which induce switch to IgE production); 3) in transplant patients where one wants to induce selective immunosuppression (select peptide that diminishes proliferative responses of host T cells to foreign antigens); 4) in lymphoproliferative states where one wants to inhibit the growth or sensitize a specific T cell tumor to chemotherapy and/or radiation; 5) in tumor surveillance where one wants to inhibit the killing of cytotoxic T cells by Fas ligand bearing tumor cells; and 5) in T cell mediated inflammatory diseases such as Rheumatoid arthritis, Connective tissue diseases (SLE), Multiple sclerosis, and inflammatory bowel disease, where one wants to inhibit the proliferation of disease-causing T cells (promote their selective apoptosis) and the resulting selective destruction of target tissues (cartilage, connective tissue, oligodendrocytes, gut endothelial cells, respectively).

Regulation of B cell responses will permit a more selective modulation of the type and amount of immunoglobulin made and secreted by specific B cell subsets. Candidate bioactive species can be introduced into B cells and one can screen for activities of bioactive species which inhibit the release and synthesis of a specific immunoglobulin. This can be useful in autoimmune diseases characterized by the overproduction of auto antibodies and the production of allergy causing antibodies, such as IgE. One can also screen for bioactive species which inhibit or enhance the binding of a specific immunoglobulin subclass to a specific antigen either foreign of self. Finally, one can screen for bioactive species which inhibit the binding of a specific immunoglobulin subclass to its receptor on specific cell types.

Similarly, one can screen for bioactive agents which affect cytokine production, generally by using two cell systems. For example, cytokine production from macrophages, monocytes, etc. can be evaluated. Similarly, one can screen for bioactive species which mimic cytokines, for example erythropoetin and IL1-17, or for bioactive species that bind cytokines such as TNF-alpha, before they bind their receptor.

Antigen processing by mononuclear leukocytes (ML) is an important early step in the immune system's ability to recognize and eliminate foreign polybioactive species. Candidate bioactive species can be introduced into ML cell lines and one can screen for bioactive species which alter the intracellular processing of foreign bioactive species and sequence of the foreign peptide that is presented to T cells by MLs on their cell surface in the context of Class II MHC. One can look for members of a library of bioactive species which enhance immune responses of a particular T cell subset (for example, the peptide would in fact work as a vaccine), or look for a bioactive species library member that binds more tightly to MHC, thus displacing naturally occurring bioactive species, but nonetheless the bioactive species would be less immunogenic (less stimulatory to a specific T cell clone). Such bioactive species would in fact induce immune tolerance and/or diminish immune responses to foreign agents, such as polypeptides. This approach could be used in transplantation, autoimmune diseases, and allergic diseases.

The release of inflammatory mediators (cytokines, leukotrienes, prostaglandins, platelet activating factor, histamine, neurobioactive species, and other peptide and lipid mediators) is a key element in maintaining and amplifying aberrant immune responses. Candidate bioactive species can be introduced into MLs, mast cells, eosinophils, and other cells participating in a specific inflammatory response, and one can screen for bioactive species which inhibit the synthesis, release and binding to the cognate receptor of each of these types of mediators.

In one embodiment, the bioactive species obtainable by the methods of the present invention are useful in biotechnology applications. Random bioactive species displayed on the surface of circulating cells can be used as tools to identify organ, tissue, and cell specific targeting sequences. Any cell introduced into the bloodstream of an animal expressing a library targeted to the cell surface can be selected for specific organ and tissue targeting. The bioactive species identified in this way can then be coupled to an antibody, enzyme, drug, imaging agent or substance for which organ targeting is desired.

Other bioactive species for which screens can be set up include: 1) bioactive species which block e.g. the activity of transcription factors, using cell lines with reporter genes; 2) bioactive species which block the interaction of two known biological molecules in cells, using the absence of normal cellular functions, the mammalian two-hybrid system or fluorescence resonance energy transfer mechanisms for detection.

Enrichment

The present invention also relates to a method for determining the identity of a chemical entity having a preselected property, comprising the steps of:
i) generating a tagged library of chemical entities by appending unique identifier tags to chemical entities,
ii) subjecting the library to a condition, wherein a chemical entity or a subset of chemical entities having a predetermined property is partitioned from the remainder of the library,
iii) recovering an anti-tag from the partitioned library, said anti-tag being capable of interacting with the unique identifier tag in a specific manner, and
iv) identifying the chemical entity/ies having a preselected function by decoding the anti-tag.

The tag is appended the chemical entity by a suitable process. Notably, each chemical entity is appended a tag by a reaction involving a chemical reaction between a reactive group of the chemical entity and a reactive group of the tag, such as method A and B of the selection section. The attachment of the chemical entity can be directly or through a bridging molecule part. The molecule part can be any suitable chemical structure able to connect the chemical entity to the tag.

The anti-tag has the ability to interact with the unique identifier tag in a specific manner. The chemical structure of the anti-tag is to a large extent dependent on the choice of unique tag. As an example, if the unique tag is chosen as an antibody, the anti-tag is selected as the epitope able to associate with the antibody. In general, it is preferred to use an anti-tag comprising a sequence of nucleotides complementary to a unique identifier tag.

The method can be performed without amplification in certain embodiments. However, when larger bioactive species are intended, it is in general preferred to use an anti-tag which is amplifiable. Anti-tags comprising a sequence of nucleotides can be amplified using standard techniques like PCR.

In the event the tag as well as the anti-tag is a sequence of nucleic acids, a tag:anti-tag hybrid can be formed prior to the subjecting the library to partitioning conditions or subsequent to the partitioning step. In some embodiments of the invention it is preferred to form the tag:anti-tag hybrid prior to the partition step in order to make the appended nucleotide sequence inert relative to the system as it is well known that certain sequences of nucleotides can bind to a target or catalyse a chemical reaction.

The oligonucleotide anti-tag can be formed in a variety of ways. In one embodiment of the invention, the anti-tag is formed as an enzymatic extension reaction. The extension comprises the initial annealing of a primer to the unique identifier tag and subsequent extension of the primer using a polymerase and dNTPs. Other types of extension reactions may also be contemplated. As an example ligases can be used to create the primer starting from di- or trinucleotide substrates and the extension can be performed using a suitable polymerase.

It can be desirable to recover the anti-tag at various steps during the process. To this end it is preferred in some aspects of the invention to provide the primer provided with a chemical entity capable of binding to a suitable affinity partner. An arsenal of different chemical entities and affinity partners are available to the skilled person in the art. The most widely used chemical entity is biotin, which in general are also preferred according to the present invention. Biotin binds to the affinity partner streptavidin or avidin. A standard technique in the laboratory is to recover a biochemical entity having attached a biotin using a solid phase covered with streptavidin. Suitably, the solid phase is a bead which can be separated from the liquid after the binding action by rotation or a magnetic field in case the solid bead comprises magnetic particles.

In other aspects of the present invention, the anti-tag is provided as a separate oligonucleotide. The separate oligonucleotide can be produced using standard amidite synthesis strategies or can be provided using other useful methods. It is in general preferred to provide the oligonucleotide by synthesis, at least in part, because the biotin amidite is easily incorporated in a nascent oligonucleotide strand. Following the addition of an oligonucleotide anti-tag to a liquid comprising chemical entities tagged with complementing oligonucleotide tags a double stranded library is formed as a hybridisation product between the unique identifier tag and the anti-tag oligonucleotide.

As mentioned above, the anti-tag oligonucleotide can be provided with a chemical entity, such as biotin, capable of binding to an affinity partner, such as streptavidin or avidin.

Following the addition of the anti-tag oligonucleotides to the tagged chemical entities, some of the oligonucleotides present in the media may not find a partner. In one embodiment of the invention it is preferred that oligonucleotides not hybridised to a cognate unique identifier and/or anti-tag are transformed into a double helix. In other aspects of the invention single stranded oligonucleotides are degraded prior to step ii) to avoid unintended interference.

The chemical entity can be used to purify the library prior to or subsequent to the partitioning step. In some embodiments of the invention, the purification step is performed prior to the partitioning step to reduce the noise of the system. In another aspect the chemical entity is used to purify the partitioned library subsequent to step ii) in order to recover a double stranded product which can be amplified.

The library is subjected to a condition in order to select chemical entities having a property which is responsive to this condition. The condition may involve the exposure of the library to a target and partitioning the chemical entities having an affinity towards this target. Another condition could be subjecting the library to a substrate and partitioning chemical entities having a catalytical activity relative to this substrate.

The anti-tag can be formed subsequent to the partitioning step. In an aspect of the invention, the single stranded nucleotide serving as a tag is made double stranded while the chemical entity is attached to the target of an affinity partitioning. Optionally, in a repeated temperature cycle, a plurality of anti-tags can be formed as extension products using the tag as template. In another aspect of the invention, the chemical entity bearing the single stranded oligonucleotide is detached from the target and a complementing anti-tag is subsequently prepared.

In the event the anti-tag comprises a chemical entity, this chemical entity can be used to purify the partitioned library. The recovery of the anti-tag is then performed by melting off said anti-tag from a partitioned double stranded library. Optionally, the amount of anti-tags can be multiplied by conventional amplification techniques, such as PCR.

The method according to the invention can be performed using a single partitioning step. Usually, it is preferred, however, to use more than one partitioning step in order to select the candidate having the desired properties from a large library. Thus, the recovered anti-tags can be mixed with the initial library or a subset thereof and the steps of partitioning (step ii)) and recovery (step iii)) may is repeated a desired number of times. Optionally, single stranded moieties in the mixture can be degraded or removed or made inert as described above.

Generally, the partitioned library obtained in step ii) is subjected to one or more further contacting steps using increasing stringency conditions. The stringency conditions can be increased by increasing the temperature, salt concentration, acidity, alkalinity, etc.

In one embodiment of the invention, the partitioned library is not subjected to intermediate process steps prior to a repeated contacting step. Especially, the partitioned library is not subjected to intermediate amplification of the anti-tag. This embodiment can be of advantage when relatively small bioactive species are used.

The method of the invention terminates with a decoding step, that is a step in which the identity of the chemical entity or entities are deciphered by an analysis of the anti-tag. When the anti-tag is an oligonucleotide, the decoding step iv) can be performed by sequencing an anti-tag nucleotide. Various methods for sequencing are apparent for the skilled person, including the use of cloning and exposure to a microarray. The tags contain recognizing groups such as e.g. nucleotide sequence(s), epitope(s) a.o. The tags carries information of the entity to which it is attached, such as e.g. entity structure, mass, spatial position (plate information) etc. The tags can be composed of monoclonal antibodies, bioactive species, proteins, oligonucleotides, DNA, RNA, LNA, PNA, natural bioactive species, unnatural bioactive species, polymeric or oligomeric hydrazino aryl and alkyl carboxylic acids, polymeric or oligomeric aminoxy aryl and alkyl carboxylic acids, peptoids, other natural polymers or oligomers, unnatural polymers (molecular weight >1000 Da) or oligomers (molecular weight <1000 Da), small non-polymeric molecules (molecular weight <1000 Da) or large non-polymeric molecules (molecular weight >1000 Da).

In one embodiment, entities consist of small non-polymeric molecules (molecular weight <1000 Da). Small molecules are generally the compounds of interest in the quest for drug oral candidates. Especially, small molecules not occurring in Nature are of interest in the drug discovery process and in one embodiment of the present invention the method are designed to select a oral drug candidate. A variety of drug candidate bioactive species are available on the market. The drug candidates of the library usually comprise a reactive group or a group which can be altered into a reactive group. In one preferred aspect of the present invention each of the members of the drug candidate library is appended a nucleic acid tag via said reactive group of the library member and a reactive group on the nucleic acid. Preferably, the nucleic acid is an oligonucleotide.

In another aspect of the invention, entities consist of large non-polymeric molecules (molecular weight >1000 Da). In still another embodiment, entities consist of polymeric molecules.

The tags and anti-tags can be composed of RNA linked to monoclonal antibodies, proteins, LNA, PNA, natural polybioactive species, unnatural polybioactive species, polymeric or oligomeric hydrazino aryl or alkyl carboxylic acids, polymeric or oligomeric aminoxy aryl or alkyl carboxylic acids, other natural polymers or oligomers, unnatural polymers (molecular weight >1000 Da) or oligomers (molecular weight <1000 Da), small non-polymeric molecules (molecular weight <1000 Da) or large non-polymeric molecules (molecular weight >1000 Da).

Alternatively, anti-tags can be composed of DNA linked to monoclonal antibodies, proteins, LNA, PNA, natural polybioactive species, unnatural polybioactive species, polymeric or oligomeric hydrazino aryl or alkyl carboxylic acids, polymeric or oligomeric aminoxy aryl or alkyl carboxylic acids, other natural polymers or oligomers, unnatural polymers (molecular weight >1000 Da) or oligomers (molecular weight <1000 Da), small non-polymeric molecules (molecular weight <1000 Da) or large non-polymeric molecules (molecular weight >1000 Da). Alternatively, anti-tags are just composed of oligonucleotides, DNA or RNA. In a embodiment, anti-tags are composed of DNA. In another embodiment anti-tags are composed of RNA.

Anti-tags which are linked to DNA or RNA are also encoded by the DNA/RNA linked to them, e.g. phage displayed or polysome displayed antibodies, bioactive species or proteins, and via DNA-templated synthesis of anti-tags, where the DNA encode the synthesis of the anti-tag, which is linked to its DNA during its synthesis.

Each chemical compound or group of compounds can be associated with a tag through formation of a covalent or non-covalent bond. For covalent bond formation, tagging may involve, but is not limited to, the formation of a cycloaddition product, an alkylation product, an arylation product, an acylation product, an amide bond, a carboxylic ester bond, a sulfonamide bond, a disulfide bond, an S-alkyl bond, an NR-alkyl bond, an O-alkyl bond, an aryl-vinyl bond, an alkyne-vinyl bond, an oxime bond, an imine bond, a bicyclic product, a trizole, a hexene, a 7-Oxa-bicyclo[2.2.1]hept-2-ene derivative, a 7-Aza-bicyclo[2.2.1]hept-2-ene derivative or a 7-Methyl-7-aza-bicyclo[2.2.1]hept-2-ene. Non-covalent bonds may involve, but are not limited to, attachment via e.g. hydrogen bonding, van der Waals interactions, pi-stacking or through hybridization. Hybridization can be between complementary strands of DNA, RNA, PNA or LNA or mixtures thereof. In such case both the tag and the chemical compound carries such a strand complementary to each other. The tagged entity, compound or mixture of compounds can be transformed into a new tagged entity, e.g. by transformation of the entity or by transformation of the tag. The transformation can be caused by either chemical or physical transformations such e.g. addition of reagents (e.g. oxidizing or reducing agents, pH adjustment a.o.) or subjection to UV-irradiation or heat.

The complex between tags and anti-tags can be formed on individually tagged entities immediately after tagging. Alternatively, after mixing individually tagged entities, either before or after the optionally use of library purification, or either before or after library enrichment for specific properties.

When tags and anti-tags are composed of nucleotides the complex consists of a double stranded nucleotide, e.g. duplex DNA or hybrids DNA/RNA.

The purification chemical entity (denoted "@") can be connected to the anti-tag. The purification chemical entity contains a recognizing group(s) such as e.g. nucleotide sequence(s), epitopes, reactive groups, high affine ligands a.o. The purification chemical entities can be composed of monoclonal antibodies, bioactive species, proteins, DNA, RNA, LNA, PNA, natural bioactive species, unnatural bioactive species, polymeric or oligomeric hydrazine aryl or alkyl carboxylic acids, polymeric or oligomeric aminoxy aryl or alkyl carboxylic acids, other natural polymers or oligomers, unnatural polymers (molecular weight >1000 Da) or oligomers (molecular weight <1000 Da), small non-polymeric molecules (molecular weight <1000 Da) or large non-polymeric molecules (molecular weight >1000 Da). Purification chemical entities may e.g. be a nucleotide sequence, biotin, streptavidin, avidin, "his-tags", mercapto groups or disulfide/activated disulfide groups. The purification chemical entity can be part of the anti-tag, e.g. in the case the anti-tag is nucleotide based or e.g. antibodies where part of the antibody may serve as epitope for another antibody (e.g. immobilized antibody which serve as purification filter).

Purification filters contains components which associate, interact or react with purification chemical entities whereby a complex is formed. This complex allows separation of non-complexed tagged entities and complexed tagged entities. The purification filter contains a recognizing group(s) such as e.g. nucleotide sequence(s), epitopes, reactive groups, high affine ligands a.o. The purification filter can be composed of monoclonal antibodies, bioactive species, proteins, DNA, RNA, LNA, PNA, natural bioactive species, unnatural bioactive species, polymeric or oligomeric hydrazino aryl or alkyl carboxylic acids, polymeric or oligomeric aminoxy aryl or alkyl carboxylic acids, other natural polymers or oligomers, unnatural polymers (molecular weight >1000 Da) or oligomers (molecular weight <1000 Da), small non-polymeric molecules (molecular weight <1000 Da) or large non-polymeric molecules (molecular weight >1000 Da). Purification filters may e.g. be a nucleotide sequence, biotin, strepdavidin, avidin, "his-tags", mercapto groups or disulfide/activated disulfide groups.

The library is probed and enriched for properties. Properties can be affinity, catalytic activity or membrane penetrating capability a.o.

Amplification may use PCR or RTPCR techniques. Anti-tags are amplifiable in some aspects of the invention. Anti-tags can be separated from tags by use of physical or chemical means, such as e.g. UV-irradiation, heat, pH-adjustment, use of salt solutions a.o.

Isolated tagged entities can be identified either trough their tag or anti-tag. Identification can be accomplished by cloning of anti-tags and sequencing their DNA/RNA or through mass analysis of either tagged entities or anti-tags or complexes of anti-tags/tagged entities.

The library of tagged entities may involve $10\text{-}10^{20}$ or $10\text{-}10^{14}$ or $10\text{-}10^{2}$ or $10\text{-}10^{3}$ or $10^{2}\text{-}10^{3}$ or $10^{2}\text{-}10^{4}$ or $10^{3}\text{-}10^{6}$ or $10^{3}\text{-}10^{8}$ or $10^{3}\text{-}10^{10}$ or $10^{3}\text{-}10^{14}$ or $10^{5}\text{-}10^{6}$ or $10^{5}\text{-}10^{8}$ or $10^{5}\text{-}10^{10}$ or $10^{5}\text{-}10^{14}$ or $10^{8}\text{-}10^{14}$ or $10^{14}\text{-}10^{20}$ entities.

Library complexes of tagged entities and anti-tags can be enriched for properties prior to purification by use of purification chemical entity and purification filter or after purification.

The term unique, when used together with sequences of nucleotides, implies that at least one of the nucleobases and/or backbone entities of the sequence does not appear together with different chemical entities. Preferably, a specific sequence is unique due to fact that no other chemical entities are associated with the same sequence of nucleobases.

Once the library has been formed, one must screen the library for chemical compounds having predetermined desirable characteristics. Predetermined desirable characteristics can include binding to a target, catalytically changing the target, chemically reacting with a target in a manner which alters/modifies the target or the functional activity of the target, and covalently attaching to the target as in a suicide inhibitor.

The target can be any compound of interest. The target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, cell, tissue, etc. without limitation. Particularly preferred targets include, but are not limited to, angiotensin converting enzyme, renin, cyclooxygenase, 5-lipoxygenase, IIL-1 0 converting enzyme, cytokine receptors, PDGF receptor, type II inosine monophosphate dehydrogenase, β-lactamases, and fungal cytochrome P-450. Targets can include, but are not limited to, bradykinin, neutrophil elastase, the HIV proteins, including tat, rev, gag, int, RT, nucleocapsid etc., VEGF, bFGF, TGFβ, KGF, PDGF, thrombin, theophylline, caffeine, substance P, IgE, sPLA2, red blood cells, glioblastomas, fibrin clots, PBMCs, hCG, lectins, selectins, cytokines, ICP4, complement proteins, etc.

The stringency conditions under which the library are screened are normally limited to such condition that maintain the hybridisation between the identifier tag and the anti-tag. High stringency conditions can be applied, however, followed by a renewed synthesis or attachment of the anti-tag. Screening conditions are known to one of ordinary skill in the art.

Chemical compounds having predetermined desirable characteristics can be partitioned away from the rest of the library while still attached to a nucleic acid identifier tag by various methods known to one of ordinary skill in the art. In one embodiment of the invention the desirable products are partitioned away from the entire library without chemical degradation of the attached nucleic acid such that the identifier nucleic acids are amplifiable. The identifier tag may then be amplified, either still attached to the desirable chemical compound or after separation from the desirable chemical compound.

In the most embodiment, the desirable chemical compound acts on the target without any interaction between the tag attached to the desirable chemical compound and the target. In one embodiment, the desirable chemical compounds bind to the target and the bound tag-desirable chemical compound-target complex can be partitioned from unbound products by a number of methods. The methods include nitrocellulose filter binding, column chromatography, filtration, affinity chromatography, centrifugation, and other well known methods.

Briefly, the library is subjected to the partitioning step, which may include contact between the library and a column onto which the target is bound. All tags which have not formed hybridisation products with a chemical entity-tag aggregate or those tags associated with undesirable chemical entities will pass through the column. Additional undesirable chemical entities (e.g., entities which cross-react with other targets) can be removed by counter-selection methods. Desirable complexes are bound to the column and can be eluted by changing the conditions of the column (e.g., salt, etc.) or the tag associated with the desirable chemical compound can be cleaved off and eluted directly.

Additionally, chemical compounds which react with a target can be separated from those products that do not react with the target. In one example, a chemical compound which covalently attaches to the target (such as a suicide inhibitor) can be washed under very stringent conditions. The resulting complex can then be treated with proteinase, DNAse or other suitable reagents to cleave a linker and liberate the nucleic acids which are associated with the desirable chemical compound. The liberated nucleic acids can be amplified.

In another example, the predetermined desirable characteristic of the desirable product is the ability of the product to transfer a chemical group (such as acyl transfer) to the target and thereby inactivate the target. One could have a product library where all of the products have a thioester chemical group. Upon contact with the target, the desirable products will transfer the chemical group to the target concomitantly changing the desirable product from a thioester to a thiol. Therefore, a partitioning method which would identify products that are now thiols (rather than thioesters) will enable the selection of the desirable products and amplification of the nucleic acid associated therewith.

There are other partitioning and screening processes which are compatible with this invention that are known to one of ordinary skill in the art. In one embodiment, the products can be fractionated by a number of common methods and then each fraction is then assayed for activity. The fractionization methods can include size, pH, hydrophobicity, etc.

Inherent in the present method is the selection of chemical entities on the basis of a desired function; this can be extended to the selection of small molecules with a desired function and specificity. Specificity can be required during the selection process by first extracting identifier sequences of chemical compounds which are capable of interacting with a non-desired "target" (negative selection, or counter-selection), followed by positive selection with the desired target. As an example, inhibitors of fungal cytochrome P-450 are known to cross-react to some extent with mammalian cytochrome P-450 (resulting in serious side effects). Highly specific inhibitors of the fungal cytochrome could be selected from a library by first removing those products capable of interacting with the mammalian cytochrome, followed by retention of the remaining products which are capable of interacting with the fungal cytochrome.

Following the selection procedure, anti-tags are recovered. The recovery can be performed by subjecting the selected complexes to stringency conditions which will detach the anti-tag sequences from the identifier tag. In the event the tag and the anti-tag are nucleic acids, the stringency conditions can be increased by increasing the temperature gradually until the two strands of the double helix are melted apart. Further copies of anti-tag sequences can be provided by extension of the identifier sequences using a suitable primer and a polymerase. In the alternative, the recovered anti-tag sequence and/or the identifier sequence tag can be subjected to PCR to form a double stranded product. The strands comprising the sequence that complements at least a part of a unique identifier sequence are subsequently isolated.

The selected chemical entity can be attached to the target during the extension or amplification or can be detached from the target. In one embodiment of the invention, it is preferred that the target is immobilised and the chemical compound remain attached to the target during the extension or amplification, to allow for easy recovery of the extension or amplification product by simple elution. In another aspect the selected chemical entities are separated from the unique identifier sequences, prior to, simultaneous with or subsequent to the recovery of the enrichment sequences.

In order to recover the desired anti-tag sequences, it can be appropriate to provide the native as well as the amplified, if present, anti-tag sequences with one part of a molecular affinity pair. The one part of a molecular affinity pair is also referred to herein as a chemical entity. The anti-tags may then be recovered by using the other part of the molecular affinity pair attached to a solid phase, which is possible to isolate. The essential property of the molecular affinity pair is that the two parts are capable of interacting in order to assemble the molecular affinity pair. In the biotechnological field a variety of interacting molecular parts are known which can be used as the molecular affinity pair. Examples include, but are not restricted to protein-protein interactions, protein-polysaccharide interactions, RNA-protein interactions, DNA-DNA interactions, DNA-RNA interactions, RNA-RNA interactions, biotin-streptavidin interactions, enzyme-ligand interactions, antibody-ligand interaction, protein-ligand interaction, etc.

A suitable molecular affinity pair is biotin-streptavidin. The anti-tag sequences can be provided with biotin, e.g. by using a primer attached to a biotin moiety in the amplification or extension step and contacting the biotin tagged anti-tag sequence with beads coated with streptavidin.

After the recovery of the anti-tag sequences, these are contacted with the initial library or a fraction thereof and an enriched library is allowed to be formed by the hybridisation of the anti-tag sequences to the cognate sequence of the unique identifier tag.

The method according to the invention can be repeated one or more times. In a second round of the method, the part of the single stranded library not recognized by an anti-tag sequence can be cleared from the reaction media or the remaining part of the single stranded library may remain in admixture with the enrich library. In general, it is not necessary to separate the remaining part of the single stranded library from the media before the enriched double stranded library is subjected to a second contact with the target because conditions for the preselected function usually are more stringent than the first round, wherefore the members of the single stranded library presumably will not bind to the target. However, to reduce the noise of the system, it can be useful at some events to withdraw from the media the members of the single stranded initial library not mated with an anti-tag sequence. If the anti-tag sequences are provided with one part of a molecular affinity pair, like biotin, the chemical compounds of interest can be extracted from the media by treatment with immobilized streptavidin, e.g beads coated with streptavidin.

As mentioned above, the conditions for performing the second or further selection step is generally more stringent than in the first or preceding step. The increasing stringency conditions in sequential selection rounds provide for the formation of a sub-library of chemical compounds which is narrowed with respect to the number but enriched with respect to the desired property.

In the present description with claims, the terms nucleic acid, oligonucleotide, oligo, and nucleotides are used frequently. The terms nucleotide, nucleotide monomer, or mononucleotides are used to denote a compound normally composed of two parts, namely a nucleobase moiety, and a backbone. The back bone may in some cases be subdivided into a sugar moiety and an internucleoside linker. Mononucleotides can be linked to each other to form a oligonucleotide. Usually, the mononucleotides are linked through an internucleoside linkage. The term nucleic acid covers mononucleotides as well as oligonucleotides. Usually, however, the term denotes an oligonucleotide having from 2 to 30 mononucleotides linked together through internucleoside linkers.

Determining the Identifier Oligonucleotide of the Bi-Functional Complex

The identifier oligonucleotide of the identifier sequence present in the isolated bi-functional molecules or the separated identifier oligonucleotides is determined to identify the chemical entities that participated in the formation of the molecule. The synthesis method of the molecule can be established if information on the functional entities as well as the point in time they have been incorporated in the molecule can be deduced from the identifier oligonucleotide. It can be sufficient to get information on the chemical structure of the various chemical entities that have participated in the molecule to deduce the full molecule due to structural constraints during the formation. As an example, the use of different kinds of attachment chemistries may ensure that a chemical entity on a reactive compound building block can only be transferred to a single position on a scaffold. Another kind of chemical constrains can be present due to steric hindrance on the scaffold molecule or the functional entity to be transferred. In general however, it is preferred that information can be inferred from the identifier sequence that enable the identification of each of the chemical entities that have participated in the formation of the molecule along with the point in time in the synthesis history the chemical entities have been incorporated in the (nascent) molecule.

Although conventional DNA sequencing methods are readily available and useful for this determination, the amount and quality of isolated bi-functional molecule may require additional manipulations prior to a sequencing reaction.

Where the amount is low, it is preferred to increase the amount of the identifier sequence by polymerase chain reaction (PCR) using PCR primers directed to primer binding sites present in the identifier sequence.

In addition, the quality of the isolated bi-functional molecule can be such that multiple species of bi-functional molecules are co-isolated by virtue of similar capacities for binding to the target. In cases where more than one species of bi-functional molecule are isolated, the different isolated species must be separated prior to sequencing of the identifier oligonucleotide.

Thus in one embodiment, the different identifier sequences of the isolated bi-functional complexes are cloned into separate sequencing vectors prior to determining their sequence by DNA sequencing methods. This is typically accomplished by amplifying all of the different identifier sequences by PCR as described herein, and then using a unique restriction endonuclease sites on the amplified product to directionally clone the amplified fragments into sequencing vectors. The cloning and sequencing of the amplified fragments then is a routine procedure that can be carried out by any of a number of molecular biological methods known in the art.

Alternatively, the bi-functional complex or the PCR amplified identifier sequence can be analysed in a microarray. The array can be designed to analyse the presence of a single tag or multiple tags in an identifier sequence.

The libraries of the present invention can contain molecules that could potentially bind to any known or unknown target, such as e.g. the targets disclosed herein above. The binding region of a target molecule could include a catalytic site of an enzyme, a binding pocket on a receptor (for example, a G-protein coupled receptor), a protein surface area involved in a protein-protein or protein-nucleic acid interaction (preferably a hot-spot region), or a specific site on DNA (such as the major groove). The natural function of the target could be stimulated (agonized), reduced (anoligonucleotide tagonized), unaffected, or completely changed by the binding of the reaction product. This will depend on the precise binding mode and the particular binding site the reaction product occupies on the target Functional sites (such as protein-protein interaction or catalytic sites) on proteins often are more prone to bind molecules than are, other more neutral surface areas on a protein. In addition, these functional sites normally contain, a smaller region that seems to be primarily responsible for the binding energy: the so-called, hot-spot regions (Wells, et al. (1993) RECENT, PROG. HORMONE RES. 48: 253-262). This phenomenon facilitates selection for molecules affecting the biological function of a certain target The linkage between the template molecule and reaction product allows rapid identification of binding molecules using various selection strategies. This invention broadly permits identifying binding molecules for any known target molecule. In addition, novel unknown targets can be discovered by isolating binding molecules against unknown antigens (epitopes) and using these binding molecules for identification and validation. In another preferred embodiment, the target molecule is designed to mimic a transition state of a chemical reaction; one or more reaction products resulting from the selection may stabilize the transition state and catalyze the chemical reaction.

The upper limit for the strength of the stringency conditions is the disintegration of the complex comprising the displayed molecule and the encoding region. Screening conditions are known to one of ordinary skill in the art.

Complexes having predetermined desirable characteristics can be partitioned away from the rest of the library while still attached to a nucleic acid identifier oligonucleotide tag by various methods known to one of ordinary skill in the art. In one embodiment of the invention the desirable products are partitioned away from the entire library without chemical degradation of the attached nucleic acid such that the identifier nucleic acids are amplifiable. The part of the identifier comprising the oligonucleotide tags may then be amplified, either still attached to the desirable chemical compound or after separation from the desirable chemical compound.

Library members that bind a target molecule can be released by denaturation, acid, or chaotropic salts. Alternatively, elution conditions can be more specific to reduce background or to select for a desired specificity. Elution can be accomplished using proteolysis to cleave a linker between the target molecule and the immobilizing surface or between the reaction product and the template. Also, elution can be accomplished by competition with a known competitive ligand for the target molecule. Alternatively, a PCR reaction can be performed directly in the presence of the washed target molecules at the end of the selection procedure. Thus, the binding molecules need not be elutable from the target to be selectable since only the template is needed for further amplification or cloning, not the reaction product itself. Indeed, some target molecules bind the most avid ligands so tightly that elution would be difficult.

In a certain embodiment, the desirable molecule acts on the target without any interaction between the coding sequences attached to the desirable display compound and the target. In one embodiment, the desirable chemical compounds bind to the target followed by a partition of the complex from unbound products by a number of methods. The methods include plastic binding, nitrocellulose filter binding, column chromatography, filtration, affinity chromatography, centrifugation, and other well known methods for immobilizing targets.

Briefly, the library is subjected to the partitioning step, which may include contact between the library and a column onto which the target is bound. All identifier sequences which do not encode for a reaction product having an activity towards the target will pass through the column. Additional undesirable reactive compound building blocks (e.g., entities which cross-react with other targets) can be removed by counter-selection methods. Desirable complexes are bound to the column and can be eluted by changing the conditions of the column (e.g., salt, etc.) or the identifier sequence associated with the desirable chemical compound can be cleaved off and eluted directly.

In a certain embodiment, the basic steps involve mixing the library of complexes with the immobilized target of interest. The target can be attached to a column matrix or microtitre wells with direct immobilization or by means of antibody binding or other high-affinity interactions. In another embodiment, the target and displayed molecules interact without immobilisation of the target. Displayed molecules that bind to the target will be retained on this surface, while nonbinding displayed molecules will be removed during a single or a series of wash steps. The identifiers of complexes bound to the target can then be separated by cleaving the physical connection to the synthetic molecule. It can be considered advantageously to perform a chromatography step after of (or) instead of the washing step. After the cleavage of the physical link between the synthetic molecule and the identifier, the identifier can be recovered from the media and optionally amplified before the decoding step.

In traditional elution protocols, false positives due to suboptimal binding and washing conditions are difficult to circumvent and may require elaborate adjustments of experimental conditions. However, an enrichment of more than 100 to 1000 is rarely obtained. The selection process used in example 7 herein alleviates the problem with false positive being obtained because the non-specific binding complexes to a large extent remain in the reaction chamber. The experiments reported herein suggest that an enrichment of more than $10^7$ can be obtained.

Additionally, chemical compounds which react with a target can be separated from those products that do not react with the target. In one example, a chemical compound which covalently attaches to the target (such as a suicide inhibitor) can be washed under very stringent conditions. The resulting complex can then be treated with proteinase, DNAse or other suitable reagents to cleave a linker and liberate the nucleic acids which are associated with the desirable chemical compound. The liberated nucleic acids can be amplified.

In another example, the predetermined desirable characteristic of the desirable product is the ability of the product to transfer a chemical group (such as acyl transfer) to the target and thereby inactivate the target. One could have a product library where all of the products have a thioester chemical group, or similar activated chemical group. Upon contact with the target, the desirable products will transfer the chemical group to the target concomitantly changing the desirable product from a thioester to a thiol. Therefore, a partitioning method which would identify products that are now thiols (rather than thioesters) will enable the selection of the desirable products and amplification of the nucleic acid associated therewith.

There are other partitioning and screening processes which are compatible with this invention that are known to one of ordinary skill in the art. In one embodiment, the products can be fractionated by a number of common methods and then each fraction is then assayed for activity. The fractionization methods can include size, pH, hydrophobicity, etc.

To select for a molecule that binds a protein expressible on a cell surface, such as an ion channel or a transmembrane receptor, the cells themselves can be used as the selection agent. The library preferably is first exposed to cells not expressing the target molecule on their surfaces to remove library members that bind specifically or non specifically to other cell surface epitopes. Alternatively, cells lacking the target molecule are present in large excess in the selection process and separable (by fluorescence-activated cell sorting (FACS), for example) from cells bearing the target molecule. In either method, cells bearing the target molecule then are used to isolate library members bearing the target molecule (e.g., by sedimenting the cells or. by FACS sorting). For example, a recombinant DNA encoding the target molecule can be introduced into a cell line; library members that bind the transformed cells but not the untransformed cells are enriched for target molecule binders. This approach is also called subtraction, selection and has been used for phage display on antibody libraries (Hoogenboom et al. (1998) IMMUNOTECH 4: 20).

A selection procedure can also involve selection for binding to cell surface receptors that are internalized so that the. receptor together with the selected binding molecule passes into the cytoplasm, nucleus, or other cellular compartment, such as the Golgi or lysosomes. Depending on the dissociation rate constant for specific selected binding molecules, these molecules may localize primarily within the intracellular compartments. Internalized library members can be distinguished from molecules attached to the cell surface by washing the cells, preferably with a denaturant. More preferably, standard subcellular fractionation techniques are used to isolate the selected library members in a desired subcellular compartment.

An alternative selection protocol also includes a known, weak ligand affixed to each member of the library. The known ligand guides the selection by interacting with a defined part of the target molecule and focuses the selection on molecules that bind to the same region, providing a cooperative effect. This can be particularly useful for increasing the affinity of a ligand with a desired biological function but with too low a potency.

Other methods for selection or partitioning are also available for use with the present invention. These include, for example: immunoprecipitation (direct or indirect) where the target molecule is captured together with library members; mobility shift assays in agarose or polyacrylamide gels, where the selected library members migrate with the target molecule in a gel; cesium chloride gradient centrifugation to isolate the target molecule with library members; mass spectroscopy to identify target molecules labeled with library members. In general, any method where the library member/target molecule complex can be separated from library members not bound to the target is useful.

The selection process is well suited for optimizations, where the selection steps are made in series, starting with the selection of binding molecules and ending with an optimized binding molecule. The procedures in each step can be automated using various robotic systems.

Thus, the invention permits supplying a suitable library and target molecule to a fully automatic system which finally generates an optimized binding molecule. Under ideal conditions, this process should run without any requirement for external work outside the robotic system during the entire procedure.

The selection methods of the present invention can be combined with secondary selection or screening identify reaction products capable of modifying target molecule function upon binding. Thus, the methods, described herein can be employed to isolate or produce binding molecules that bind to and modify the function of any protein or, nucleic acid.

For example, nucleic acid-templated chemistry can be used to identify, isolate, or produce binding molecules (1) affecting catalytic activity of target enzymes by inhibiting catalysis or, modifying substrate binding; (2) affecting the functionality of protein receptors, by inhibiting binding to receptors. or by modifying the specificity of binding to receptors; (3) affecting the formation of protein multimers by disrupting the quaternary structure of protein subunits; or (4) modifying transport properties of a protein by disrupting transport of small molecules or ions.

Functional assays can be included in the selection process. For example after selecting for binding activity, selected library members can be directly tested for a desired functional effect, such as an effect on cell signaling. This can, for example, be performed via FACS methodologies.

The binding molecules of the invention can be selected for other properties in addition to binding. For example, to select for stability of binding interactions in a desired working environment. If stability in the presence of a certain protease is desired, that protease can be part of the buffer medium used during selection. Similarly, the selection can be performed in serum or cell extracts or in any type of medium, aqueous or organic. Conditions that disrupt or degrade the template should however be avoided to allow subsequent amplification.

Selections for other desired properties, such as catalytic or other functional activities, can also be performed. Generally, the selection should be designed such that library members with the desired activity are isolatable on that basis from other library members. For example, library members can be screened for the ability to fold or otherwise significantly change conformation in the presence of a target molecule, such as a metal ion, or under particular pH or salinity conditions. The folded library members can be isolated by performing non-denaturing gel electrophoresis under the conditions of interest. The folded library members migrate to a different position in the gel and can subsequently be extracted from the gel and isolated.

Selection for catalytic activity may be performed by affinity selections on transition-state analog affinity columns (Baca et al. (1997) PROC. NATL. ACAD. Sci. USA 94 (19): 10063-8) or by function-based selection schemes (Pedersen et al. (1998) PROC. NATL. ACAD. Sci. USA 95 (18): 10523-8).

Similarly, reaction products that fluoresce in the presence of specific ligands may be selected by FACS based sorting of translated polymers linked through their DNA templates to beads. Those beads that fluoresce in the presence, but not in the absence, of the target ligand are' isolated and, characterized. Useful beads with a homogenous population of nucleic acid-templates-on any bead can be prepared using, the split-ppol synthesis technique on the bead, such that each bead is exposed to only a single nucleotide sequence. Alternatively, a different anti-" template (each complementary to only a single, different template) can by synthesized on beads using a split-pool'technique, and then can anneal to capture a solution-phase library.

Biotin-terminated biopolymers can be selected for the actual catalysis of bond-. breaking reactions by passing these biopolymers over a resin linked through a substrate to avidin. Those biopolymers that catalyze substrate cleavage self-elute from a column charged with this resin. Similarly, biotin-terminated biopolymers can be selected for the catalysis of bond-forming reactions. One substrate is linked to resin and the second substrate is linked to avidin. Biopolymers that catalyze bond formation between the substrates are selected by their ability to react the substrates together, resulting in attachment of the biopolymer to the resin.

Library members can also be selected for their catalytic effects on synthesis of a polymer to which the template is or becomes attached. For example, the library member may influence the selection of monomer units to be polymerized as well as how the polymerization reaction takes place (e.g., stereochemistry, tacticity, activity). The synthesized polymers can be selected for specific properties, such as, molecular weight, density, hydrophobicity, tacticity, stereoselectivity, using standard techniques, such as, electrophoresis, gel filtration, centrifugal sedimentation, or partitioning into solvents of different hydrophobicities. The attached template that directed the synthesis of the polymer can then be identified.

Library members that catalyze virtually any reaction causing bond formation between two substrate molecules or resulting in bond breakage into two product molecules can be selected. To select for bond forming catalysts (for example, hetero Diels-Alder, Heck coupling, aldol reaction, or olefin metathesis catalysts), library members are covalently linked to one substrate through their 5'. amino or thiol termini. The other substrate of the reaction is synthesized as a derivative linked to biotin. When dilute solutions of library-substrate conjugate are combined with the substrate-biotin conjugate, those library members that catalyze bond formation cause the biotin group to become covalently attached to themselves. Active bond forming catalysts can then be separated from inactive library members by capturing the former with immobilized streptavidin and washing away inactive library members. In an analogous manner, library members that catalyze bond cleavage reactions such as retro-aldol reactions, amide hydrolysis, elimination reactions, or olefin dihydroxylation followed by periodate cleavage can be selected. In this case, library members are covalently linked to biotinylated substrates such that the bond breakage reaction causes the disconnection of the biotin moiety from the library members. Upon incubation under reaction conditions, active catalysts, but not inactive library members, induce the loss of their biotin groups. Streptavidin-linked beads can then be used to capture inactive polymers, while active catalysts are able to be eluted from the beads. Related bond formation and bond cleavage selections have been used successfully in catalytic RNA and DNA evolution (Jaschke et al.(2000) CURR. OPIN. CHEM. BIOL. 4: 257-62) Although these selections do not explicitly select for multiple turnover catalysis, RNAs and DNAs selected in this manner have in general proven to be multiple turnover catalysts when separated from their substrate moieties (Jaschke et al. (2000) CURR. OPIN. CHEM. BIOL. 4: 257-62; Jaeger et al. (1999) PROC. NATL. ACAD. Sci. USA 96: 14712-7; Bartel et al. (1993) SCIENCE 261: 1411-8; Sen et al. (1998) CURR. OPIN. CHEM. BIOL. 2:680-7).

In addition to simply evolving active catalysts, the in vitro selections described above are used to evolve non-natural polymer libraries in powerful directions difficult to achieve using other catalyst discovery approaches. Substrate specificity among catalysts can be selected by selecting for active catalysts in the presence of the desired substrate and then selecting for inactive catalysts in the presence of one or more undesired substrates. If the desired and undesired substrates differ by their configuration at one or more stereocenters, enantioselective or diastereoselective catalysts can emerge from rounds of selection. Similarly, metal selectivity can be evolved by selecting for active catalysts in the presence of desired metals and selecting for inactive catalysts in the presence of undesired metals. Conversely, catalysts with broad substrate tolerance can be evolved by varying substrate structures between successive rounds of iteration.

Alternatively, following PCR amplification of DNA templates encoding selected synthetic molecules, additional rounds of translation, selection, and amplification can be conducted to enrich the library for high affinity binders. The stringency of the selection is gradually increased by increasing the salt concentration of the binding and washing buffers, decreasing the duration of binding, elevating the binding and washing temperatures, and increasing the concentration of washing additives such as template DNA or unrelated proteins.

Importantly, in vitro selections can also select for specificity in addition to binding affinity. Library screening methods for binding specificity typically require duplicating the entire screen for each target or non-target of interest. In contrast, selections for specificity can be performed in a single experiment by selecting for target binding as well as for the inability to bind one or more non-targets. Thus, the library can be pre-depleted by removing library members that bind to a non-target. Alternatively, or in addition, selection for binding to the target molecule can be performed in the presence of an excess of one or more non-targets. To maximize specificity, the non-target can be a homologous molecule. If the target molecule is a protein, appropriate non-target proteins include, for example, a generally promiscuous protein such as an albumin. If the binding assay is designed to target only a specific portion of a target molecule, the non-target can be a variation on the molecule in which that portion has been changed or removed.

Ultimately, a binding molecule identified using the present invention may be useful as a therapeutic and/or diagnostic agent. Once the selection is complete, the selected templates optionally can be amplified and sequenced. The selected reaction products, if present in sufficient quantity, can be separated from the templates, purified (e.g., by HPLC, column chromatography, or other chromatographic method), and further characterized.

Inherent in the present method is the selection of reactive compound building blocks on the basis of a desired function; this can be extended to the selection of small molecules with a desired function and specificity. Specificity can be required during the selection process by first extracting identifiers sequences of chemical compounds which are capable of interacting with a non-desired "target" (negative selection, or counter-selection), followed by positive selection with the desired target. As an example, inhibitors of fungal cytochrome P-450 are known to cross-react to some extent with mammalian cytochrome P-450 (resulting in serious side effects). Highly specific inhibitors of the fungal cytochrome could be selected from a library by first removing those products capable of interacting with the mammalian cytochrome, followed by retention of the remaining products which are capable of interacting with the fungal cytochrome.

Amplification of Identifier Oligonucleotides

PCR amplification methods are described in detail in U.S. Pat. Nos. 4,683,192, 4,683,202, 4,800,159, and 4,965,188, and at least in PCR Technology: Principles and Applications for DNA Amplification, H. Erlich, ed., Stockton Press, New York (1989); and PCR Protocols: A Guide to Methods and Applications, Innis et al., eds., Academic Press, San Diego, Calif. (1990). The contents of all the foregoing documents are incorporated herein by reference.

The identifier oligonucleotide can be amplified using PCR with primers generating two unique cut-sites. These cut-sites can be used for multimerization of the coding region by cloning into a suitable vector for sequencing. This approach will allow simultaneously sequencing of many encoding regions. Alternatively, the PCR product is directly cloned into a suitable vector using for example TA cloning. In still another approach the identity of the molecule is established by applying the PCR product to a suitable microarray.

It is preferred that the oligonucleotide parts of the bi-functional complexes of the libraries of the invention have a common terminal sequence which can serve as a primer for PCR, as is known in the art. Such a common terminal sequence can be incorporated as the terminal end of an oligonucleotide tag added in the final cycle of the library synthesis, or it can be added following library synthesis, for example, using the enzymatic ligation methods disclosed herein.

In embodiments in which PCR is to be used to amplify the identifier oligonucleotides of selected bi-functional complexes, the identifier oligonucleotides preferably include PCR primer sequences. For example, a PCR primer sequence can be included in the third intermediate bi-functional complex and/or it can be included with the first identifier oligonucleotide tag oligonucleotide. The identifier oligonucleotide can also include a capping PCR primer sequence that follows the oligonucleotide tag sequences. The capping sequence can be ligated to the identifier oligonucleotide following the final cycle of library synthesis or it can be included in the oligonucleotide tag oligonucleotide of the final cycle. In cases in which the PCR primer sequences are included in an oligonucleotide tag oligonucleotide, these oligonucleotide tag oligonucleotides will be longer than the oligonucleotide tag oligonucleotides added in the other cycles, because they will include both an oligonucleotide tag sequence and a PCR primer sequence.

In cases in which the capping sequence is added after the addition of the final reactive compound building block and the final oligonucleotide tag oligonucleotide, the synthesis of a library as set forth herein will include the step of ligating the capping sequence to the identifier oligonucleotide, such that the oligonucleotide portion of substantially all of the library members terminates in a sequence that includes a PCR primer sequence.

PCR primer sequences suitable for use in the libraries of the invention are known in the art; suitable primers and methods are set forth, for example, in Innis et al., eds., PCR Protocols: A Guide to Methods and Applications, San Diego: Academic Press (1990), the contents of which are incorporated herein by reference in their entirety. Preferably, the capping sequence is added by ligation to the pooled fractions which are products of the final synthesis round. The capping sequence can be added using the enzymatic process used in the construction of the library.

As indicated above, the nucleotide sequence of the oligonucleotide tag as part of the methods of this invention, may be determined by the use of the polymerase chain reaction (PCR).

The nucleic acid sequence of an oligonucleotide tag can be determined by subjecting the oligonucleotide tag to a PCR reaction as follows. The appropriate sample is contacted with a PCR primer pair, each member of the pair having a preselected nucleotide sequence. The PCR primer pair is capable of initiating primer extension reactions by hybridizing to a PCR primer binding site on the identifier oligonucleotide tag. The PCR primer binding site is preferably designed into the identifier oligonucleotide tag. For example, a PCR primer binding site may be incorporated into the initial (display) oligonucleotide tag and the second PCR primer binding site may be in the final oligonucleotide tag. Alternatively, the second PCR primer binding site may be incorporated into the capping sequence as described herein. In preferred embodiments, the PCR primer binding site is at least about 5,7,10,13, 15, 17, 20, 22, or 25 nucleotides in length.

The PCR reaction can be performed by mixing the PCR primer pair, preferably a predetermined amount thereof, with the identifier oligonucleotide, preferably a predetermined amount thereof, in a PCR buffer to form a PCR reaction admixture. The admixture is thermocycled for a number of cycles, which is typically predetermined, sufficient for the formation of a PCR reaction product. A sufficient amount of product is one that can be isolated in a sufficient amount to allow for DNA sequence determination.

PCR is typically carried out by thermocycling i.e. repeatedly increasing and decreasing the temperature of a PCR reaction admixture within a temperature range whose lower limit is about 30° C. to about 55° C. and whose upper limit is about 90° C. to about 100° C. The increasing and decreasing steps can be continuous, but is preferably phasic with time periods of relative temperature stability at each of temperatures favoring polynucleotide synthesis, denaturation and hybridization.

The PCR reaction can be performed using any suitable method. Generally it occurs in a buffered aqueous solution, i.e. a PCR buffer, preferably at a pH of 7-9. Preferably, a molar excess of the primer is present. A large molar excess is preferred to improve the efficiency of the process.

The PCR buffer also contains the deoxyribonucleotide triphosphates (polynucleotide synthesis substrates) dATP, dCTP, dGTP and dTTP and a polymerase, typically thermostable, all in adequate amounts for primer extension (polynucleotide synthesis) reaction. The resulting solution (PCR mixture) is-heated to about 90° C.-100° C. for about 1 to 10 minutes, preferably from 1 to 4 minutes. After this heating period the solution is allowed to cool to 54° C., which is preferable for primer hybridization.

The synthesis reaction may occur at a temperature ranging from room temperature up to a temperature above which the polymerase no longer functions efficiently. Suitable enzymes for elongating the primer sequences include, for example, *E. coli* DNA polymerase I, Taq DNA polymerase, Klenow fragment of *E. coli* DNA polymerasel, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. The newly synthesized DNA strand and its complementary strand form a double-stranded molecule which can be used in the succeeding steps of the analysis process.

Ultra High-Throughput Methods

Oligonucleotide tags and/or identifiers may be analyzed by an ultra high throughput method, such as ultra high throughput sequencing as described herein below. Often following a screen or affinity assay using encoded molecules e.g. phage display, DNA display, mRNA display, or other types of oligonucleotide tagged compounds, the results of screening may be analyzed by sampling a limited number of oligonucleotide tags, e.g. 1-100 oligonucleotide tags. Oligonucleotide tags may be analyzed by cloning individual oligonucleotide tags e.g. by cloning in E. coli followed by preparation of plasmids or "colony PCR" and then sequencing using any method known in the art. However, it is often desirable to analyse a significantly larger number of oligonucleotide tags to obtain more information from the screening which makes these traditional methods of cloning and sequencing cumbersome. For example, a single type of sequence corresponding to a specific combination of codons may dominate a small oligonucleotide tag sample e.g. 40 of 100 oligonucleotide tags may correspond to a single codon combination and the remaining oligonucleotide tags may be different. If instead 1000 or 10000 oligonucleotide tags are analysed it is expected that about 400 and 4000 sequences respectively correspond to the oligonucleotide tag observed 40 of 100 times in the small sample. However the remaining 600 and 6000 sequences respectively may reveal several sequences that are observed more than once thus indicating that they have been preferentially enriched during the screening. Thus a potential wealth of information exists which is very cumbersome to access using traditional methods, e.g. e.g. by cloning in E. coli followed by preparation of plasmids or "colony PCR" and then sequencing. Several methods can be applied to analyze oligonucleotide tags in an ultra high-throughput fashion. For example identifiers may be analyzed by an ultra high-throughput method similar to that described in patent WO0120039 and Margulies M et al (Genome sequencing in microfabricated high-density picolitre reactors, Nature 2005). This method involves capture of individual PCR-derived fragments on their own beads and, within the droplets of an emulsion, clonally amplifying the individual fragment. Unlike in current sequencing technology, this approach does not require subcloning in bacteria or the handling of individual clones; the templates are handled in bulk within the emulsions. Sequencing can be done by synthesis simultaneously in open wells of a fibre-optic slide using a modified pyrosequencing protocol that is designed to take advanoligonucleotide tage of the small scale of the wells. The fibreoptic slides are manufactured by slicing of a fibre-optic block that is obtained by repeated drawing and fusing of optic fibres. At each iteration, the diameters of the individual fibres decrease as they are hexagonally packed into bundles of increasing cross-sectional sizes. Each fibre-optic core is 44 µm in diameter and surrounded by 2-3 µm of cladding; etching of each core creates reaction wells approximately 55 µm in depth with a centre-to-centre distance of 50 µm, resulting in a calculated well size of 75 pl (picoliters). The slide, containing approximately 1.6 million wells, is loaded with beads and mounted in a flow chamber designed to create a 300-mm high channel, above the well openings, through which the sequencing reagents flow The unetched base of the slide is in optical contact with a second fibre optic imaging bundle bonded to a charge-coupled device (CCD) sensor, allowing the capture of emitted photons from the bottom of each individual well. The combination of picolitre-sized wells, enzyme loading uniformity allowed by the small beads and enhanced solid support chemistry enables a method that extends the useful read length of sequencing-by-synthesis to more than 100 bases.

Identifiers may also be analyzed by an ultra high-throughput method similar to that described in WO/2005/093094. This method relates to "high-density fingerprinting", in which a panel of nucleic acid probes is annealed to nucleic acid information is desired, e.g. an identifier, with determination of the presence or absence of sequence complementary to a panel of probes, thus providing sequence information. The method involves hybridization of a panel of probes, each probe comprising one or more oligonucleotide molecules, in sequential steps determining for each probe if it hybridizes to the template or not, thus forming the "hybridization fingerprint" of the target. Preferably, the panel of probes and the length of the template strand are adjusted to ensure dense coverage of any given template strand with indicative probes' (probes which hybridize exactly once to the template strand). Probes may be 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides long. Probes may contain any natural or unnatural nucleotide or analog. The obtained hybridization spectrum can then be compared with a reference database containing all expected identifier sequences. Before probing, identifiers or derived products may be immobilized in an array format. Then identifiers may be amplified e.g. using rolling-circle amplification or a related method. Thus individual identifier sequences are placed apart and amplified avoiding the need for traditional cumbersome cloning e.g. in E. coli.

Identifiers may also be analyzed by an ultra high-throughput method similar to that described in WO/2001/057248. By this method identifiers or amplified or modified identifiers may be immobilized in an array format. Primers may be annealed to the identifiers and the sequence of the identifiers may be determined by sequencing. Sequencing in an array format can be done by various methods recognized by those skilled in the art. For example, incorporation of fluorescently-labeled, 3'-blocked nucleotides can be done in the presence of a DNA polymerase. Nucleotide may be any natural or unnatural nucleotide or any nucleotide analog. The polymerase incorporates a base complementary to the target polynucleotide, but is prevented from further addition by the 3'-blocking group. The label of the incorporated base can then be determined and the blocking group removed by chemical cleavage to allow further polymerisation to occur. The fluorescent group can also be removed thus allowing detection of a new nucleotide incorporation at a specific array position. Prior to immobilization, a hairpin adaptor may be ligated to the identifier sequence such that a primer becomes covalently linked to the identifier.

The information carried by oligonucleotide tags may be analyzed using a computer application, e.g. a word or text processing application, a spreadsheet application, Preferably, the oligonucleotide tag information may be analyzed using a computer application which can translate the oligonucleotide tag information into e.g. encoded structures. A computer application may preferably be used to analyze such encoded structures include quantitative and qualitative structure-activity relationship (SAR) analyses e.g. such as analyzing and/or clustering structural fingerprints common to enriched encoded structures.

A simple but efficient method is to look for oligonucleotide tag combinations which have been enriched by the screening process.

It may be found that only specific reactive compound building blocks or dimers formed by reactive compound building blocks, e.g., dimers formed by the first and the second reactive compound building block or the first and the third reactive compound building block are enriched by a screening process. Such a result may indicate that the screening process has not been optimized and steps can be taken to improve the screening process. If a large number of molecules with e.g. same or very similar target affinity exist in a library of bi-functional complexes it may be difficult or impossible to optimize the screening process so that it can discriminate sufficiently between them. The oligonucleotide tag analysis may then identify a common reactive compound building block combination shared by the oligonucleotide tags whereas one reactive compound building block position may be "undefined" i.e. it is not possible to determine which reactive compound building block is preferred at this position, e.g. the "C" position in the following list of oligonucleotide tag combinations, where identifiers are composed of three oligonucleotide tags (A-B-C): A2-B17-C13, A1-B1-C2, A1-B1-C14, A1-B1-C23, A1-B1-C17, A5-B278-C11. In this case is preferable to obtain significantly more oligonucleotide tag sequences as this may enable discrimination of different but similar reactive compound building block combinations. This can be achieved by using ultra high-throughput oligonucleotide tag sequencing methods as described.

Following screening or analyses of identifiers the pool of identifiers may be subjected to further methods which may aid analyses of the identifiers. Such methods may include partitioning the identifiers based on specific features of the identifiers such as a nucleotide sequence. For example a subset of identifiers may contain too many variants of an oligonucleotide tag combination or it may contains too much noise, e.g. identifiers which are deemed uninteresting. In such cases nested PCR may be used to amplify only identifiers which contain specific oligonucleotide tags. The resulting amplification product may then be processed e.g. sequencing, optionally in an ultra high-throughput fashion, to identify a common oligonucleotide tag at an otherwise unresolved position. Alternatively, oligonucleotide tag combinations may be enriched by partitioning single-stranded identifier oligonucleotides e.g. sequentially with anticodons corresponding to specific oligonucleotide tags essentially performing an affinity selection/screening of the identifiers with or without encoded molecules. In this way it is possible to partition specific identifiers or identifier subsets.

Figure 1:
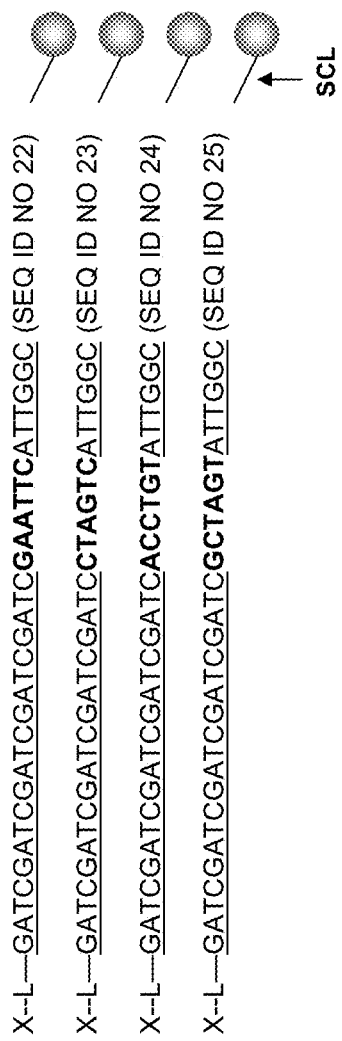
FIG. 1. Each oligonucleotide sequence may contain a common nucleotide sequence shared with other nucleotides, a unique oligonucleotide sequence or a combination of common and unique sequences. Each of the oligonucleotides above is attached to the solid-support (marked by a sphere) through a selectively cleavable linker (SCL) (can be cleaved with all or a subset of protection groups still intact). The underlined sequences are examples of common sequences shared between the oligonucleotides in the set of oligonucleotides. Such sequences may be useful for amplification of oligonucleotide-tag information by for example PCR. Furthermore, the common sequences may be used to facilitate enzymatic coupling to one or more oligonucleotide tags by f.ex doublestranded or partly doublestranded overhang ligation, ligation using a splint or by ligation between singlestranded oligonucleotides using enzymes such as T4 DNA ligase, E. coli ligase, thermostable ligases, T4 RNA ligase or similar performing ligation enzymes, polymerases or recombinases. X is a chemical reaction site and L is a linker.

In example (A), one or more building blocks is first reacted separately on one or more reactive sites X, before synthesis of one or more oligonucleotide tags by organic synthesis comprising one or more unique codons that encode the building block reacted on X. Following oligonucleotide synthesis, the bi-functional molecules are stripped of some or all of their protection groups and cleaved off the solid-support in either single or multiple reactions in any order or simultaneously. The term bi-functional molecule is used interchangeably with the term bi-functional complex. These steps provide a library of bi-functional molecules each comprising a unique chemical entity linked to a unique encoding oligonucleotide tag. The library of bi-functional molecules may be further developed by subjected the pool to one or more further rounds of chemical reaction with any number of building blocks and concomitant enzymatic addition of oligonucleotide tags that encode the individual building blocks (Note that the order of events for reaction and tagging are arbitrary). Furthermore, in one embodiment of the present invention the continuous split-and-mix cycle of building block addition and addition of oligonucleotide tags may by-pass step 3 described above, hence the bi-functional molecule is not cleaved from the solid support. In this case the split-and-mix protocol is adopted on protected or partially protected oligonucleotides still attached to a solid-support and the subsequent reaction of building blocks and enzymatic addition of encoding tags may be conducted on solid-support using preformed oligonucleotide tags and enzymes such as ligases, polymerases and recombinases. For the further enzymatic addition of tags it may be suitable to provide the oligonucleotides with a 3'H-group, 5' OH'-group or 5'-end phosphate for enzymatic reactivity.

In example (B) the end result is similar to (A) except that oligonucleotide tag synthesis precedes addition of the building block or fragment to the reactive site X.

In Example (C) the oligonucleotide tag synthesis precedes the loading of a building block to the reactive site X. However, in contrast to (B), X is located distal to the solid-support. This may offer an advantage in terms of reaction efficiency due to better solvation of X and thus better transformation turnover. The reactive site X may be positioned anywhere suitable along the oligonucleotide and may also be exposed using modified nucleobases such as amino-modifier on cytidine and thymidine bases (f.ex Glenn Research catalog #10-1019-90 or 10-1039-90) or similar. F. ex the method of (A) may have certain advantages compared to (B) and (C) in that no nucleotides are yet synthesized at the time of chemical reaction of the building block to X arguably increasing the potential scope of reaction diversity. Each oligonucleotide strand may contain any number of reactive sites X such as one or more dependent on the desired fragment valency (i.e the number of displayed molecules on a single oligonucleotide tag. Consequently, the fragment can be displayed once, twice, 3 times, ×4, ×5, ×6, ×7, ×8, ×9, ×10 or more than 10 times on an oligonucleotide strand.

For (A), (B) and (C) above, the selectively cleavable linker should preferably not be cleaved until one round of building block addition and oligonucleotide synthesis has been completed. Furthermore, the directionality of oligonucleotide synthesis is arbitrary and may proceed in the 5' to 3' direction or the more conventional 3' to 5' end direction.

Figure 2:
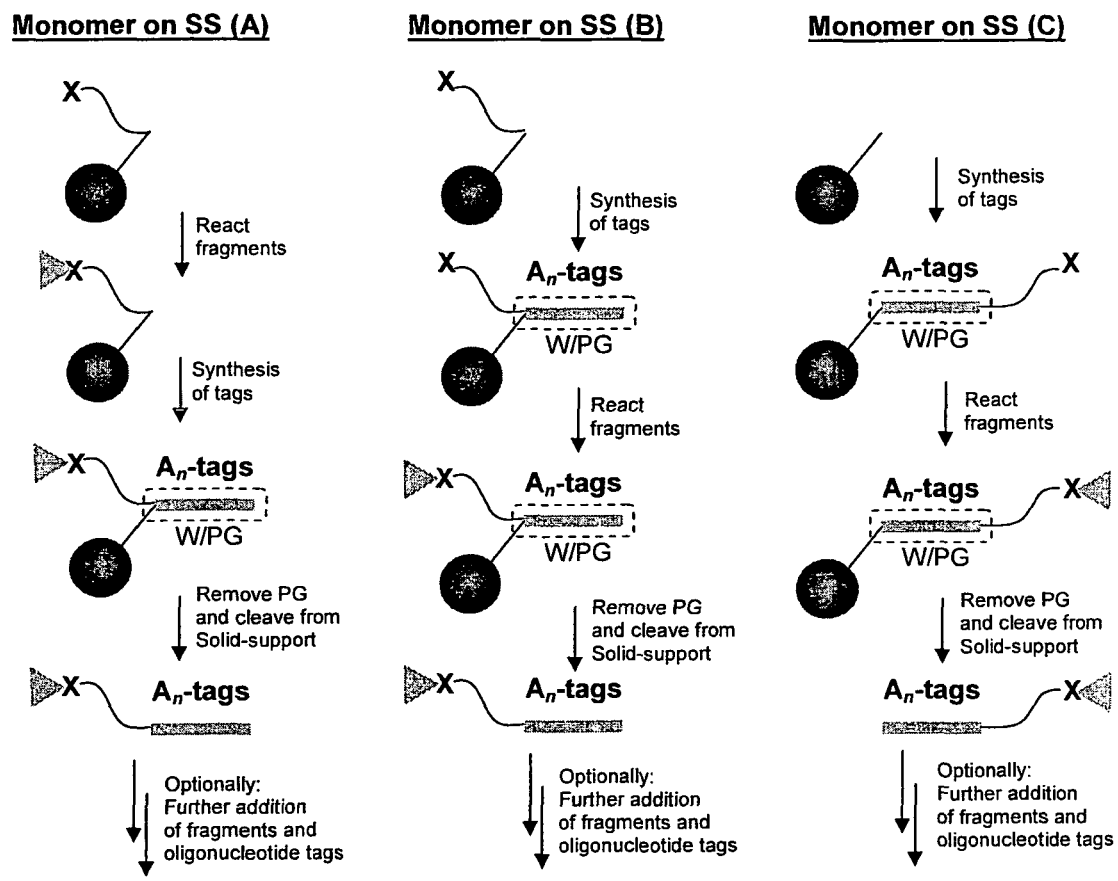
FIG. 2. The set of reactive compound building blocks, in the figure referred to as fragments is illustrated by grey triangles and reacted with the chemical reaction site or handle X of a set of unique oligonucleotide tags (grey bar) coupled to a solid-support (grey sphere). The terms "reaction site" and "handle" are used interchangeably throughout the application. Hairlines represent linkers. The dashed line illustrates oligonucleotide protection groups (W/PG).
Figure 3:
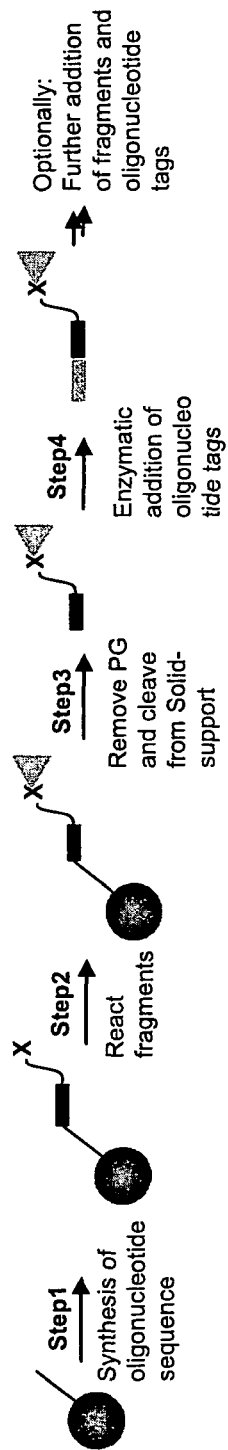

FIG. 3. A further example using any method of FIGS. 2 (A), (B) and (C) described above for the synthesis of a library of building blocks or fragments attached to a reactive site X and an oligonucleotide that does not contain a unique codon sequence may be envisioned. In this embodiment, the chemical reaction of a building block with a reactive site X occurs on an oligonucleotide that does not contain a unique sequence. Instead, the product will be subject to enzymatic addition of a unique codon tag as shown in the figure. The addition of the unique tag can be conducted after step 3 in solution or after step 2 when the bi-functional complex is still attached to the solid-support. For the latter option, it may be desirable that all or a subset of oligonucleotide protection groups have been removed. Note that the order of step 1 and 2 as well as the position and number of reactive sites X are chosen arbitrarily and the setup describing enzymatic addition of oligonucleotide tags could be incorporated with any of the procedures described elsewhere.

Figure 4:
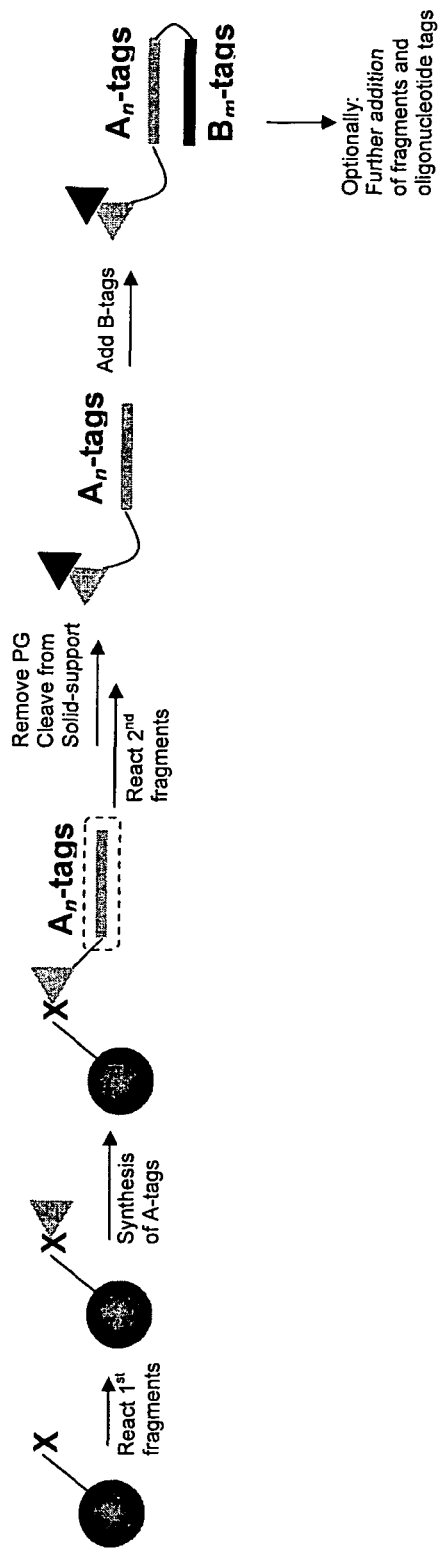

FIG. 4. In one embodiment shown schematically in FIG. 4, the first building block is a spacer between the solid-support and the oligonucleotide tag.

Figure 5:
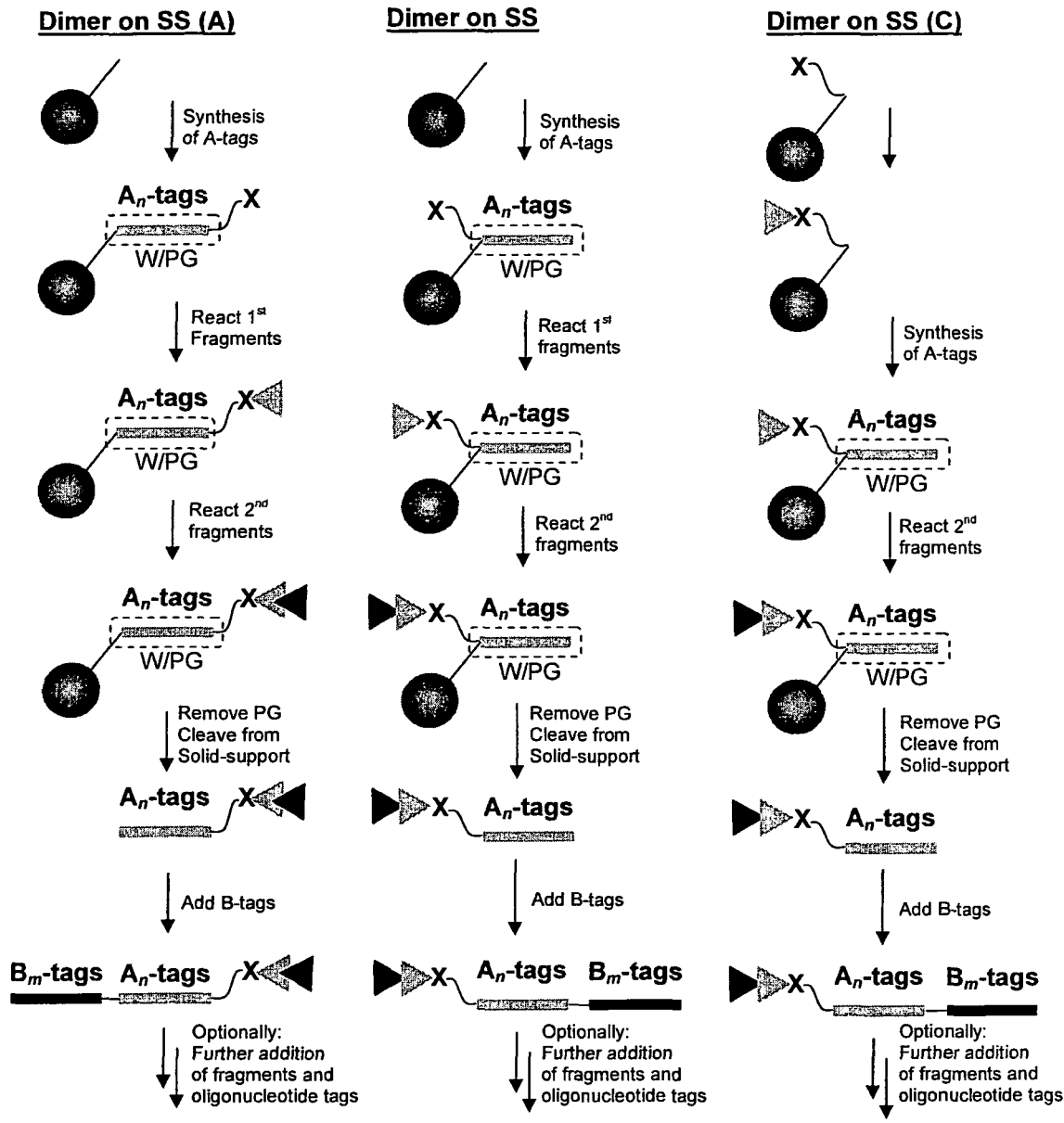

FIG. 5. The figure outlines at least two possible procedures (A) and (B) for combinatorial synthesis of small molecules each composed of two or more fragments without intervening tag-addition. The use of sequential reactions with no intervening oligonucleotide tagging events such as shown schematically in scheme (A) and (B) enable the experimenter to connect two building blocks using any chemistry suitable without the restriction of maintaining orthogonality to the tagging step such as steps involving organic synthesis of oligonucleotide sequences. The order of events for building block and tag addition is arbitrary and tag-addition may be conducted without intervening building block reaction and conversely sequential building block addition may be feasible without intervening addition of tags. The tag-bars indicate a single-chain DNA-tag but may also contain a double stranded region at any point during the reaction scheme when an enzymatic tagging step is necessary. For simplicity, the use of building block and some nucleotide protection and deprotection steps has been omitted from the figure but is inferred as an integral part of any synthesis strategy. Furthermore, the figures depict the parallel processes and have for simplicity omitted the mixing steps. In a further example (C) the reaction of the first building block precedes tag addition and allows chemical reactions without potential limitations from the presence of protected oligonucleotides.

Figure 6:
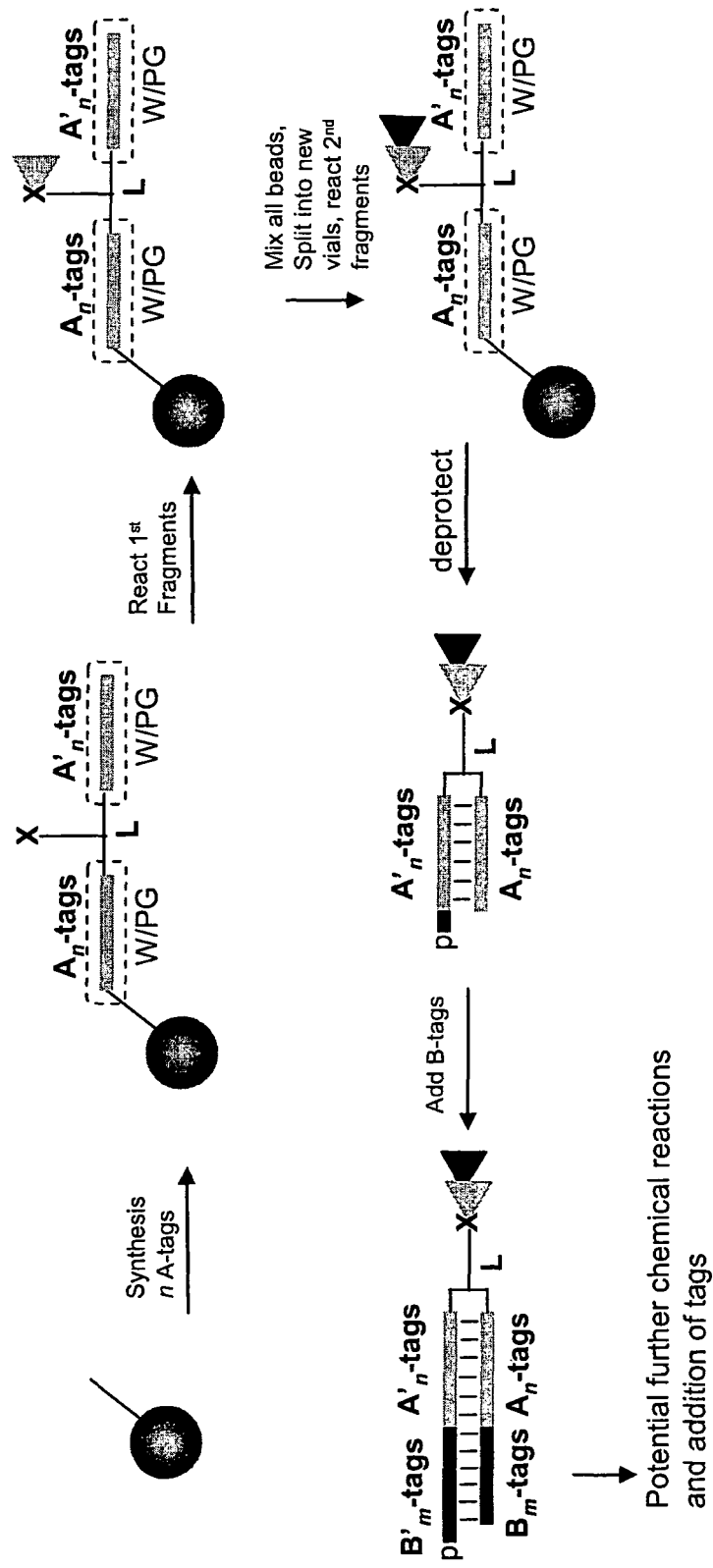

FIG. 6. An example of solid-phase synthesis of a self-complementary tag with a reactive site is shown. The synthesis starts with an oligonucleotide containing a split-region separating the self-complementary or partially self-complementary sequences which allows for intramolecular hybridization once protection groups have been removed. The grey and black bars indicate oligonucleotide tags and hairlines between the bars indicate the possibilities for basepairing. The oligonucleotide tags are preferably DNA tags. L is a linker. The reactive site X is selectively deprotected allowing chemical reaction. The reactive site on this chemical entity may comprise an amine, carboxylic acid, thiol, alcohol, aldehyde, reactive scaffold or any other chemical entity or entities capable of reacting with fragments without damaging the protected or partially protected DNA tags (although, unprotected DNA attached to a solid support may prove feasible and incorporated in this invention—however the practical aspect makes this embodiment less convenient). The composition of the A-tags may comprise both a fixed sequence common to all A-tags or a subset of A-tags (f.ex for PCR-amplification purposes) and a unique sequence encoding one or more specific fragments. In one embodiment several tags may encode only one fragment or a subset of fragments. The 5'-end of the A-tags should comprise a phosphor-group (shown as p in the figure) for subsequent ligation to a B-tag. Although a 5'-end phosphor may be introduced by enzymatic means it is most desirable that the 5'-end phosphate is incorporated during oligonucleotide solid-phase synthesis. Furthermore, it could be envisioned that both of the split-regions of the tag does not need to encode the specific tag sequence specifying the chemical fragment. In this case, the segment complementary to the encoding A-tag sequence could be ligated following the DNA deprotection step. The linker (L) is any useful linker capable of connecting the split codon segments. Preferably, the linker could be a poly-carbon or poly-ethyleneglycol (PEG) based linker of any useful dimensions provided that the linker can connect complementary oligonucleotide tag sequences and display a chemical reaction site. Preferably, the linker forms a 3-way junction such as shown in this figure. If polyvalent display is desired the linker may contain two or more reactive sites such as 3, 4, 5, 6, 7, 8, 9, 10 or more than 10 reactive handles. The triangles represent chemical fragments reacting on the reactive site X or a structure or sub-structure of the reactive site or a part of a previously reacted fragment. The terms "fragments" and "building blocks" are used interchangeably. Chemical deprotection steps have been omitted for simplicity but are assumed as part as any chemical synthesis strategy. Note that the final molecule comprises two DNA strands covalently linked through the connecting linker.

Figure 7:
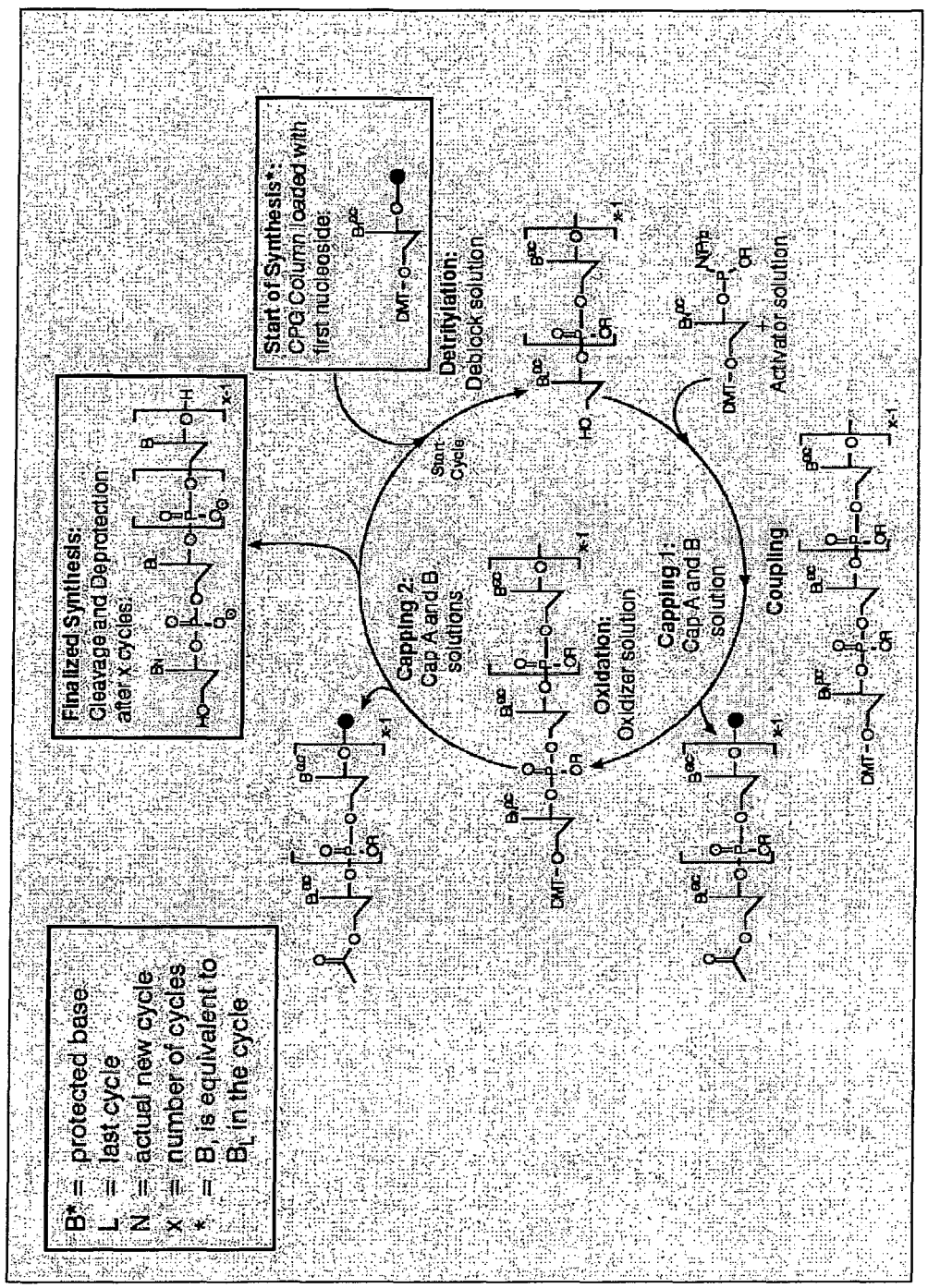

FIG. 7. General synthesis cycle (adopted from Sigma/ProOligo)

Figure 8:

FIG. 8. The figure depicts five different oligonucleotide tags attached to a solid support. The sequence of 6 underlined nucleotides indicate the sequence unique to each of the oligonucleotide tags. X is the reactive amino-group with optional protection group, L is a polyethyleneglycol linker of 6 units, G, A, T, C are deoxynucleotide bases with suitable protection groups on base and backbone functional groups. The oligonucleotide entities are linked with f. ex and ester-linkage to a solid-support resin (grey sphere) suitable for oligonucleotide synthesis.

Figure 9:
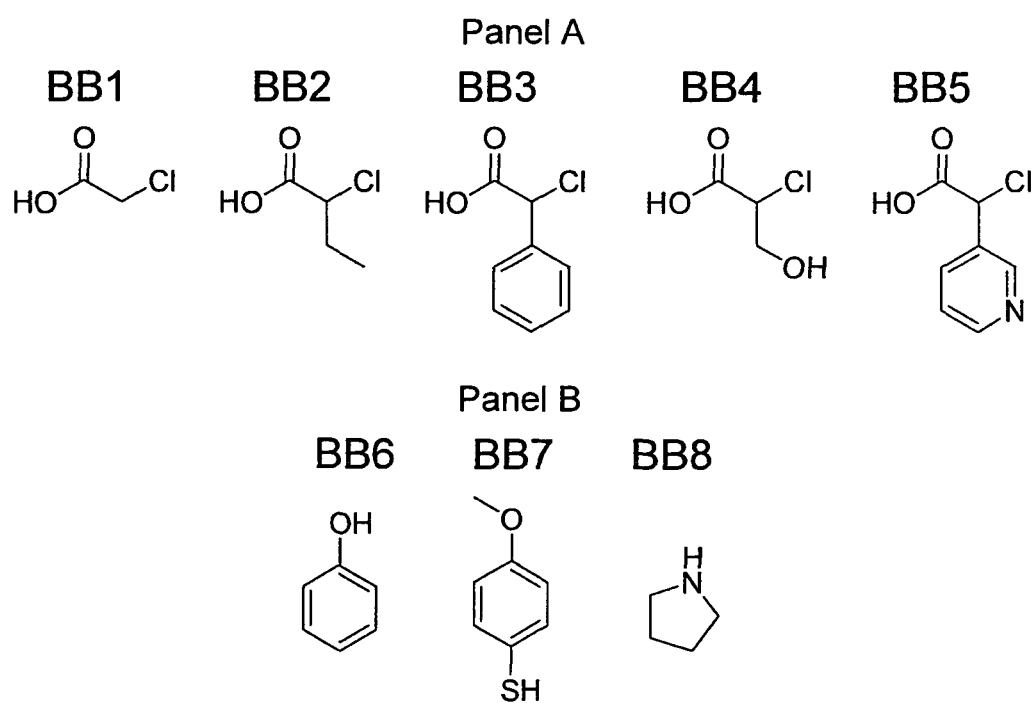

FIG. 9. Panel A: Building blocks BB1, BB2, BB3, BB4 and BB5.

Panel B: Building blocks BB 6, BB7 and BB 8.

FIG. 10. The figure depicts the results of mass spectroscopy analyses by ES-MS.

Panel A: Dimer A: BB1-BB6. Correct mass: 6406 Da. Starting material 6350. No product is apparent.

Panel B: Dimer B: BB1-BB7. Correct mass: 6453 Da. Estimated loading efficiency >80%.

Panel C: Dimer C: BB1-BB8. Correct mass: 6384 Da. Estimated loading efficiency >80%.

Figure 11:
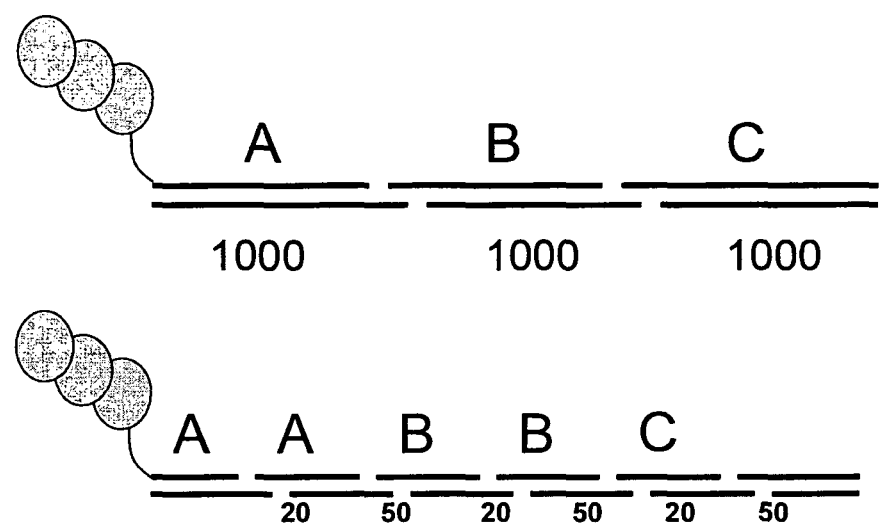

FIG. 11. The figure shows the DNA encoding setup for the generation of a billion trimeric molecules encoded without subcodon combination and with subcodon combinations, respectively. A theoretical synthetic combinatorial library of DNA-tagged molecules consisting of a billion compounds of trimers can be synthesized from a combination of 1000×1000×1000 fragments molecules. Assuming a one-to-one relationship between a fragment and a unique codon it would require 3000 unique codons which in case of double-stranded codons would result in 6000 oligonucleotides. However, if each unique codon could be produced from two or more subsets of codons linked by enzymatic ligation, a reduced number of codons are required. In the example above, the 1000 codons in each position could be produced from 20×50 subcodons or 33×34 subcodons. Consequently, the encoding of a billion member trimer library above could be accomplished by 20×50×20×50×20×50 codons totalling only 210 codon or 420 oligonucleotides. Such codon combinations dramatically decrease time and resources necessary for codon maintenance and logistics although at the expense of a modest decrease in library yield due to an increased number of ligation reactions.

Figure 12:
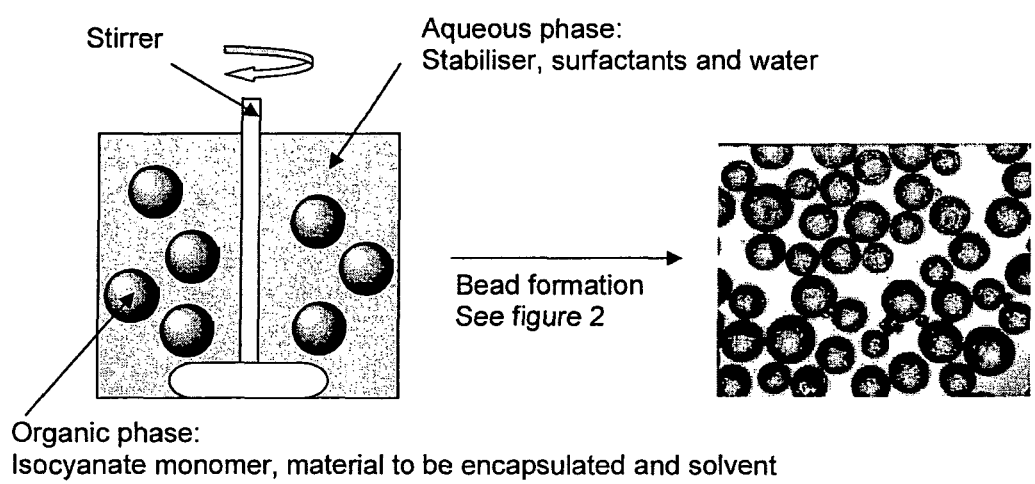

FIG. 12. In certain embodiments it may be desirable to conduct chemical reactions using reagents potentially harmful to the stability of DNA. To avoid detrimental DNA damage, encaging or encapsulation of chemical constituents may be able to sustain chemical reactivity of a chemical entity connected to DNA-tags while shielding DNA-tags from direct contact with the harmful reagents such as transition metals. The following examples illustrate some strategies for reagent encapsulation and for DNA proximity enhancement of encapsulated reagents by introduction of surface charges for attraction of DNA-tags to the beads. An oil-in-water emulsion is formed when stirring the organic and aqueous phase very rapidly. The beads with the encapsulated material are formed in the inter phase between the water and the organic medium.

Figure 13:
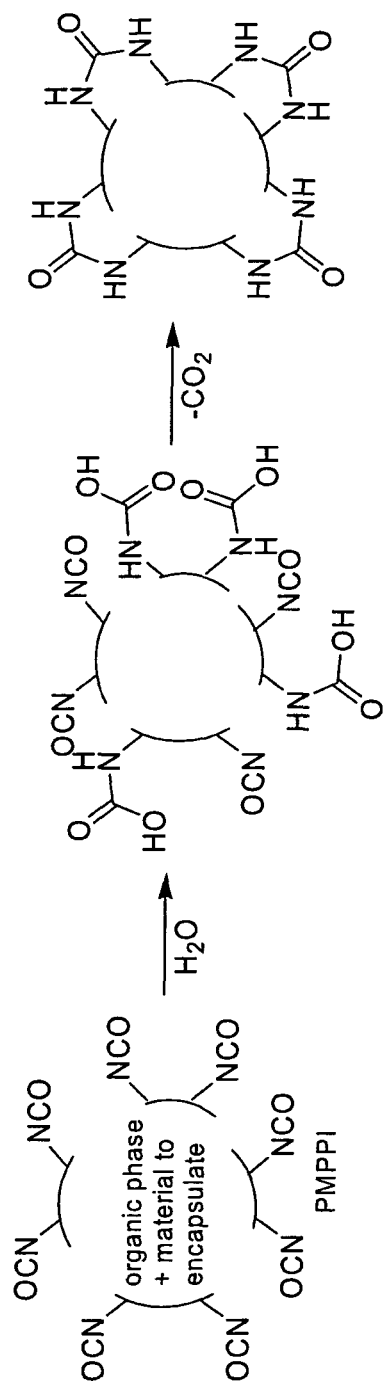

FIG. 13. The beads are formed when isocyanate on e.g. polymethylene polyphenylene di-isocyanate (PMPPI) is partly hydrolysed to amine with evolution of carbodioxide. The amine reacts further with a proximal isocyanate moiety.

Figure 14:
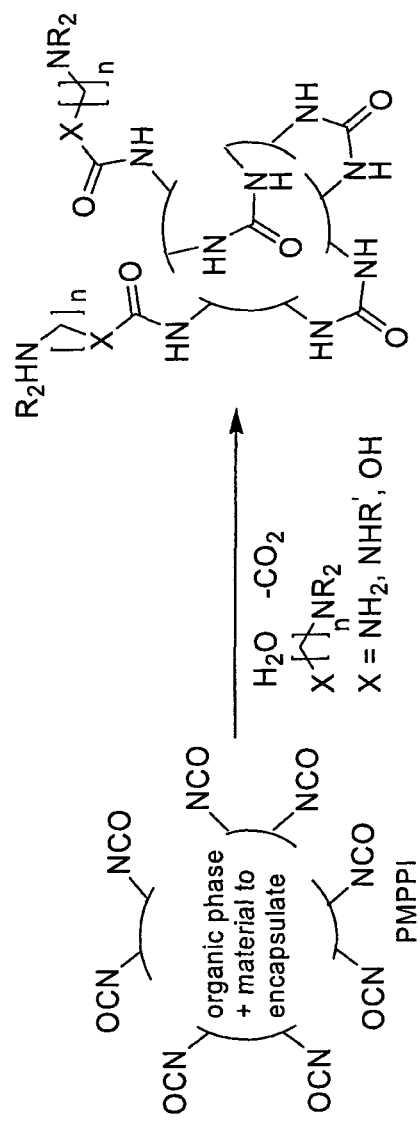

FIG. 14. An example of how the surface of the beads can be modified with covalently bound tertiary amine. R and R' can be any small aliphatic chain such as methyl and ethyl and n=1 to 8.

Figure 15:
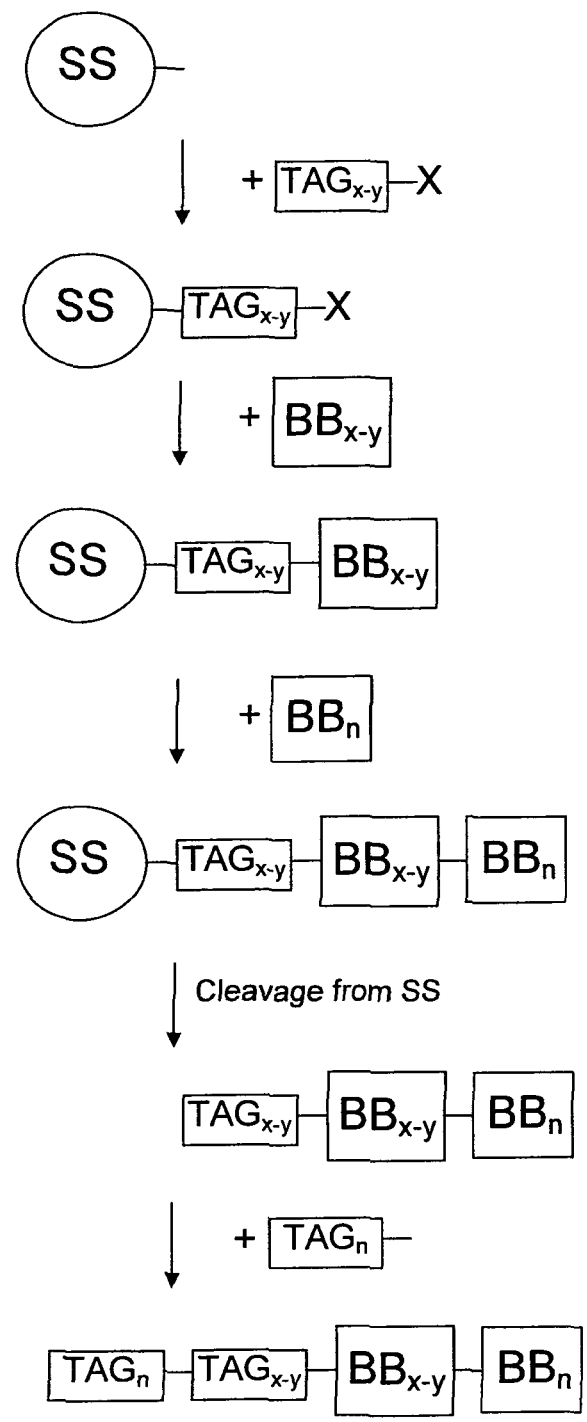

FIG. 15. The figure shows how a library of bi-functional complexes can be synthesised according to the present invention. A plurality of solid supports (SS) are reacted with a plurality of different (x-y) first identifier oligonucleotide tags ($TAG_{x-y}$) comprising a chemical reaction site X. Alternatively, the first identifier oligonucleotide tags are synthesised in a step-by-step fashion directly on the solid support. A building block ($BB_{x-y}$), which is identified by the first identifier oligonucleotide tag ($TAG_{x-y}$), is then reacted with the chemical reaction site X, thereby generating a plurality of different first intermediate, bi-functional complexes. A second building block ($BB_n$) is reacted with the different first intermediate, bi-functional complexes in the absence of a tag identifying it, thereby generating a plurality of different second intermediate, bi-functional complexes, where after the second intermediate, bi-functional complexes are cleaved from the solid supports. Finally a tag ($TAG_n$) identifying $BB_n$ is attached to the second intermediate, bi-functional complexes via enzymatic ligation to generate a plurality of different third intermediate bi-functional complexes. n can be any number between 10 and 10.000.

Figure 16:
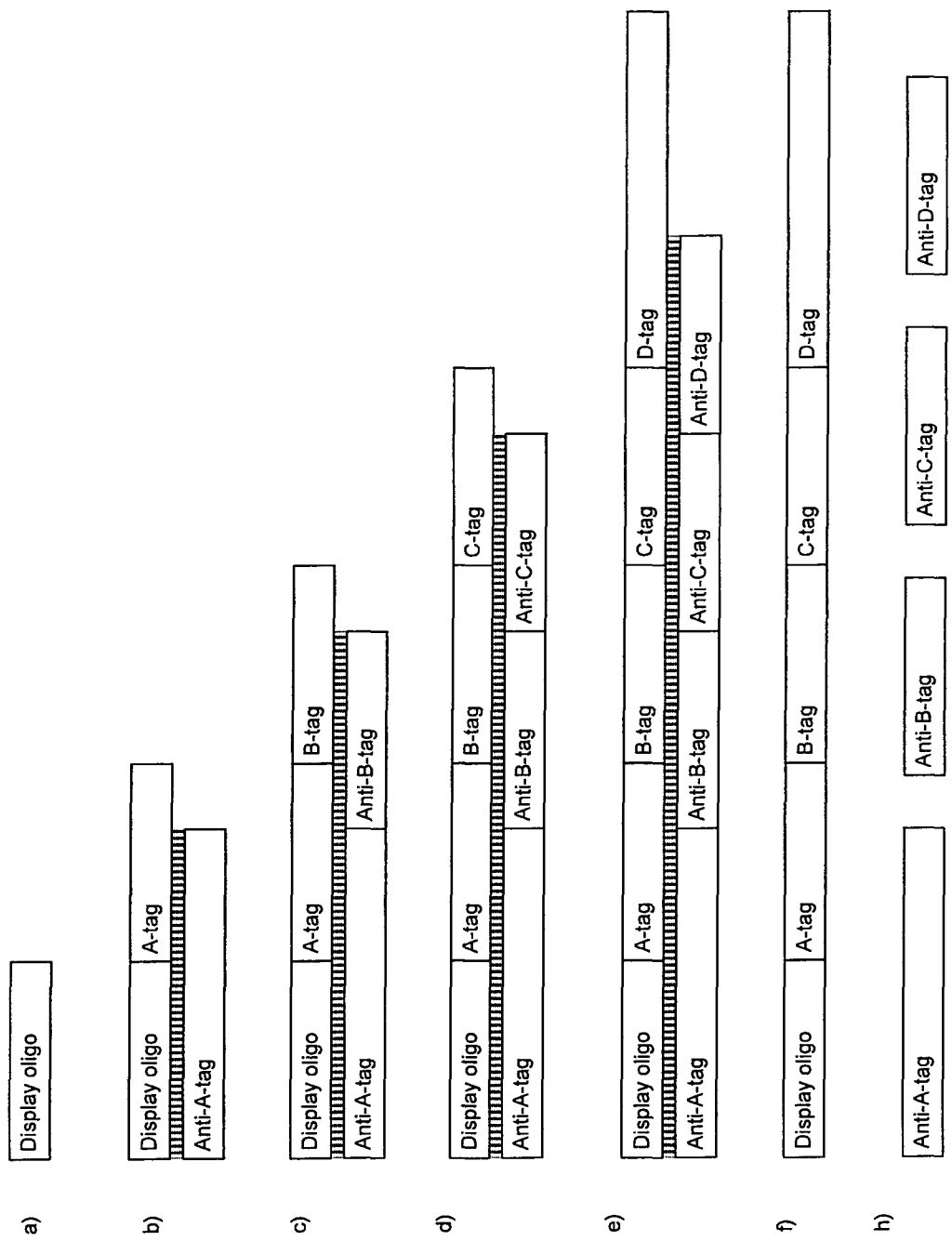
Figure 103:
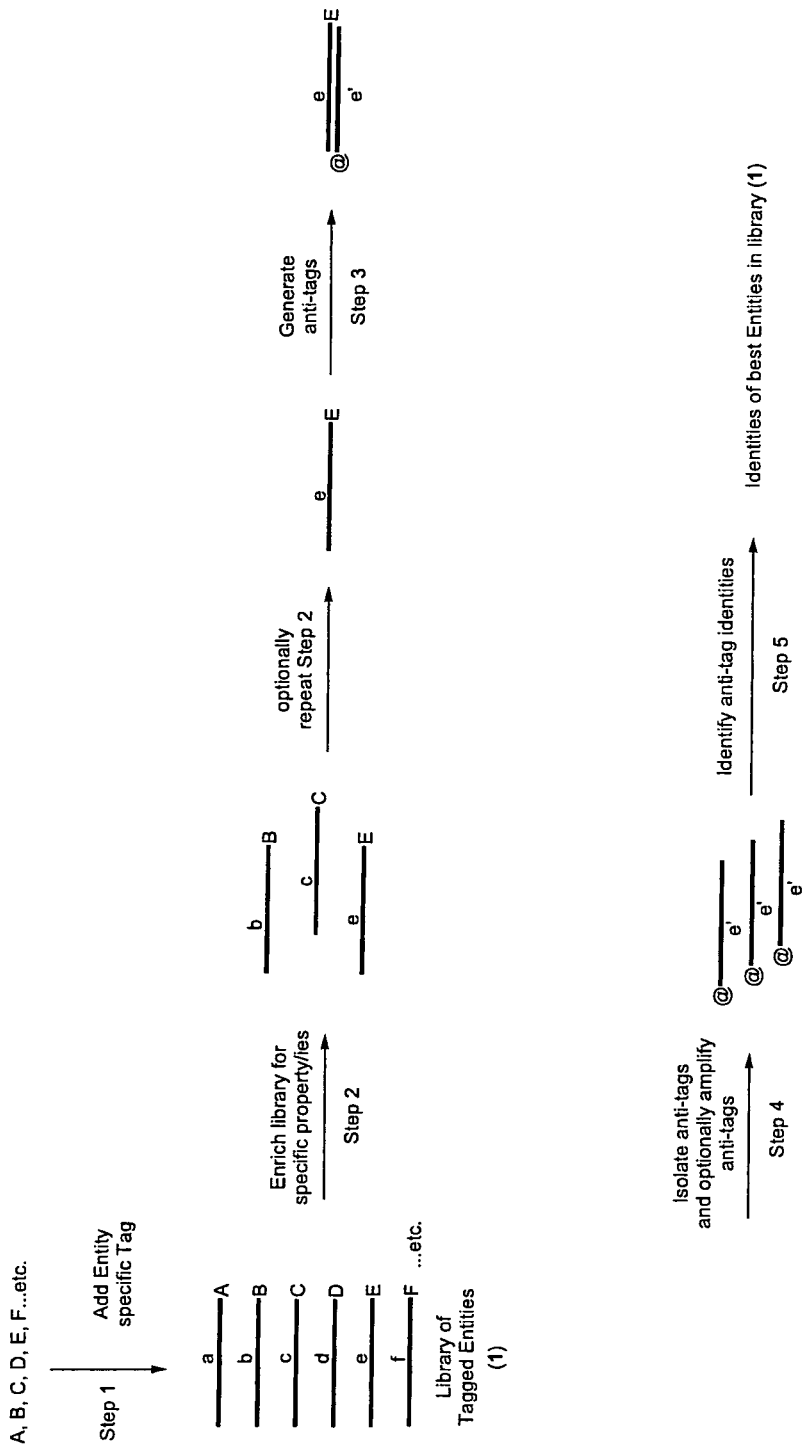

The methods of the present invention comprises in one or more further embodiments the further steps described in FIGS. 16-103.

FIG. 16. A tag addition process employing linkage of top strand tags only. (a) The initial bi-functional complex. (b-e) Addition of tags A to D. (f) The top strand containing tags A to D. (h) The individual anti-tags Ax to Dx. The polarity of overhangs is such that B, C, and D tags contact their cognant anti-tag and the anti-tag cognate to the following tag, e.g. a B-tag contacts an anti-B-tag and an anti-C-tag.

Figure 17:
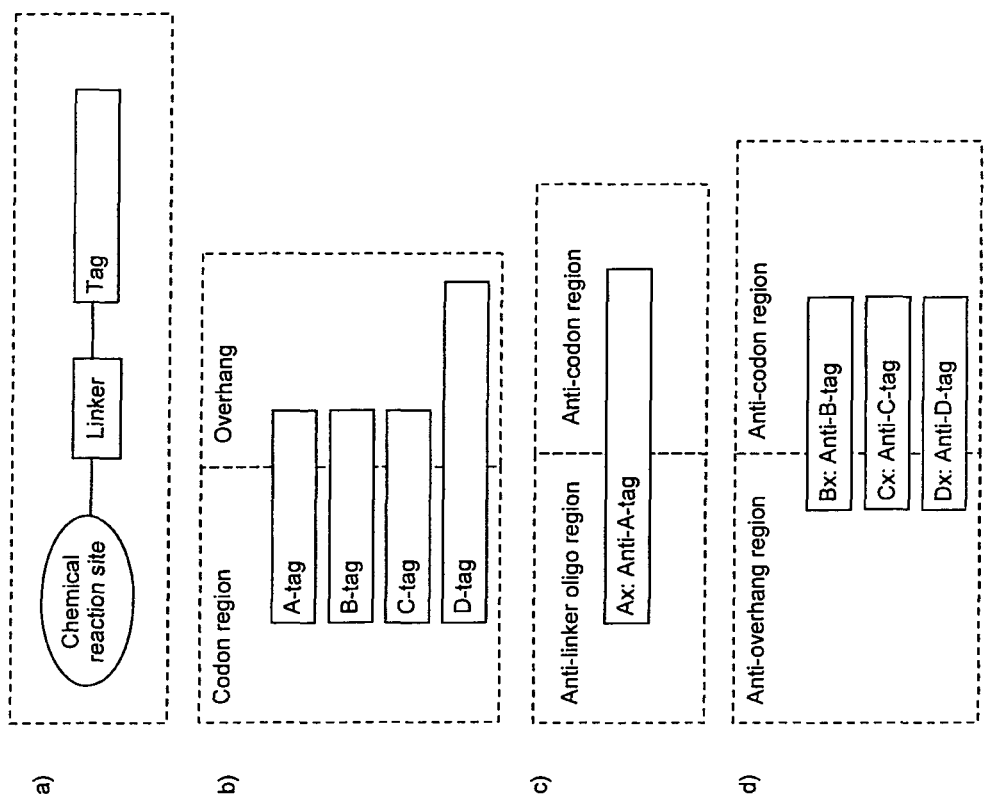

FIG. 17. One possible type of tag layout. (a) The initial bi-functional complex containing a chemical reaction site, a linker moiety, and a tag region (linker tag). (b) Tags A, B, C, and D containing a tag region and an overhang region. (c) The anti-A-tag containing an anti-linker tag region and an anti-A-tag region. (d) Anti-tags Ax, Bx, Cx, and Dx containing an anti-overhang region and an anti-tag region.

Figure 18:
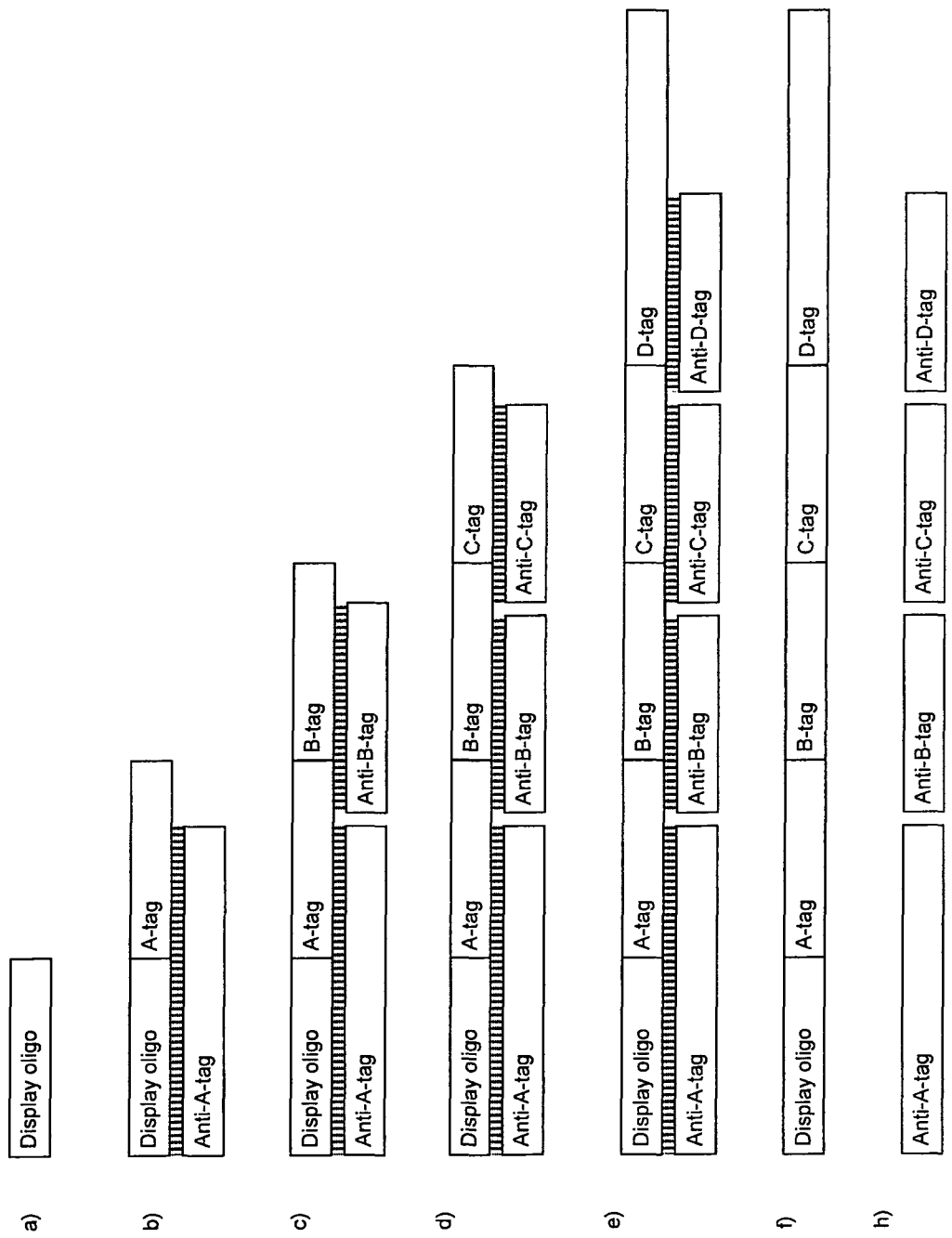

FIG. 18. A tag addition process employing linkage of top strand tags only and using non-abutting anti-tags, i.e., the anti-tags are separated from each other. (a) The initial binfunctional complex. (b-e) Addition of tags A to D. (f) The top strand containing tags A to D. (h) The individual anti-tags Ax to Dx. The polarity of overhangs is such that B, C, and D tags contact their cognant anti-tag and the anti-tag cognate to the following tag, e.g. a B-tag contacts an anti-B-tag and an anti-C-tag.

Figure 19:
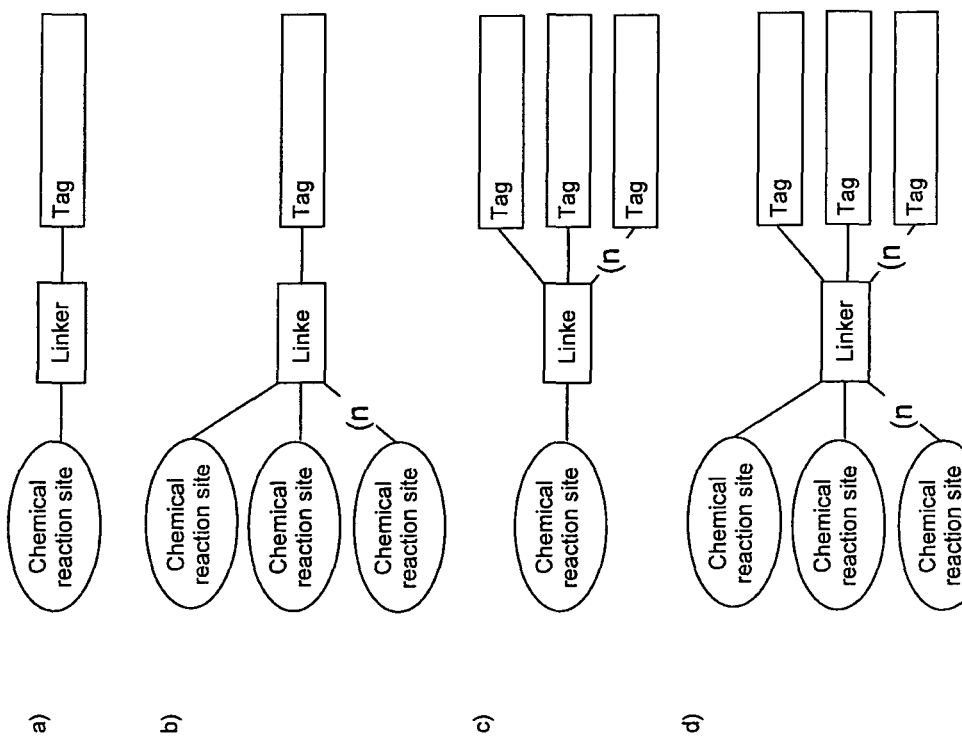

FIG. 19. Different possible designs of the initial bi-functional complex. (a) a single chemical reaction site is attached to a single linker tag via a non-branched linker. (b) A number (n) of chemical reaction sites are attached to a single linker tag via a branched linker. (c) A single chemical reaction site is attached to a number (n) of linker tags via a branched linker. (d) A number (n) of chemical reaction sites are attached to a number (n) of linker tags via a branched linker.

Figure 20:
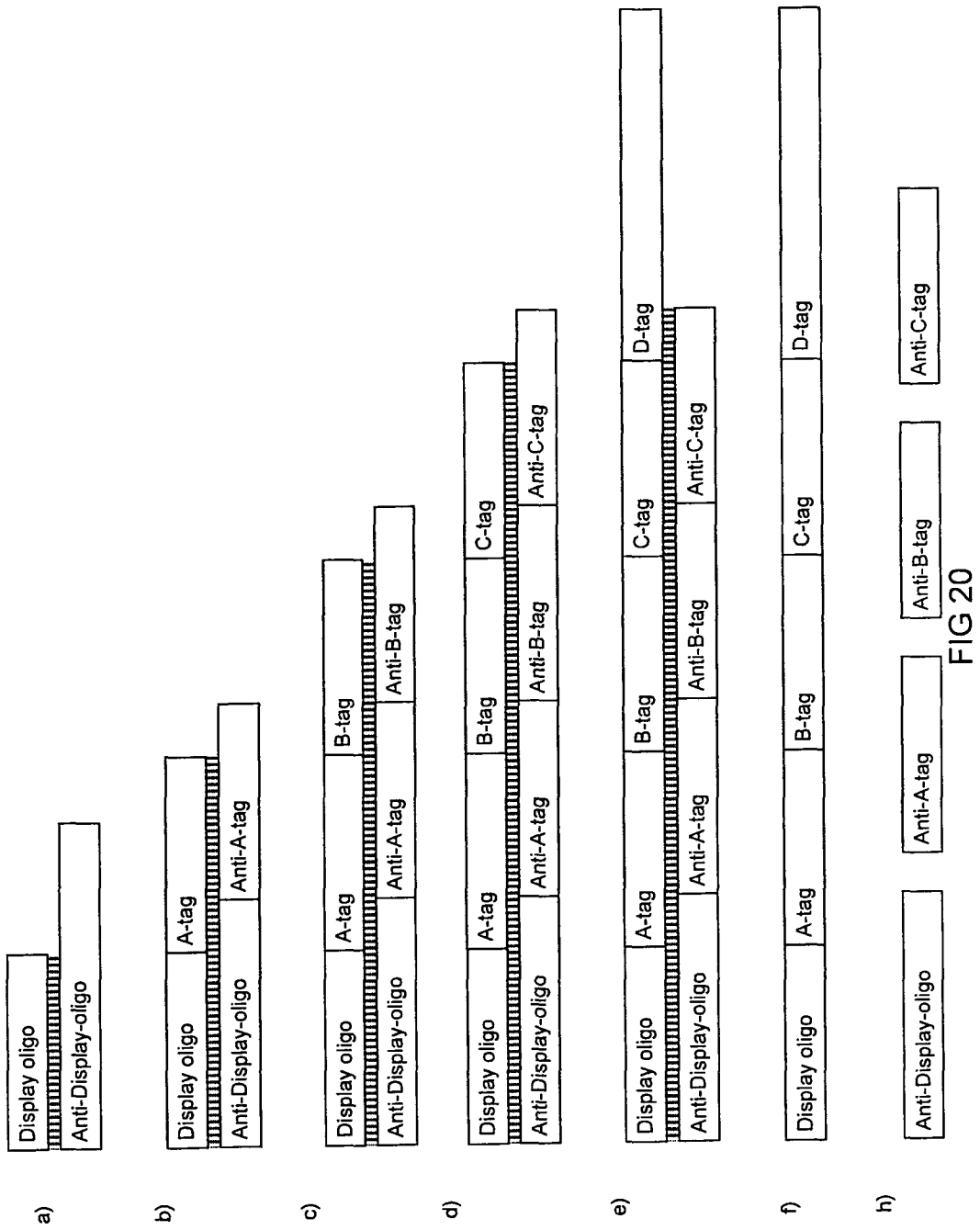

FIG. 20. A tag addition process employing linkage of top strand tags only. (a) The initial binfunctional complex. (b-e) Addition of tags A to D. (f) The top strand containing tags A to D. (h) The individual anti-tags Ax to Dx. The polarity of overhangs is such that B, C, and D tags contact their cognant anti-tag and the anti-tag cognate to the previous tag (compare with FIG. 1), e.g. a B-tag contacts an anti-B-tag and an anti-A-tag.

Figure 21:
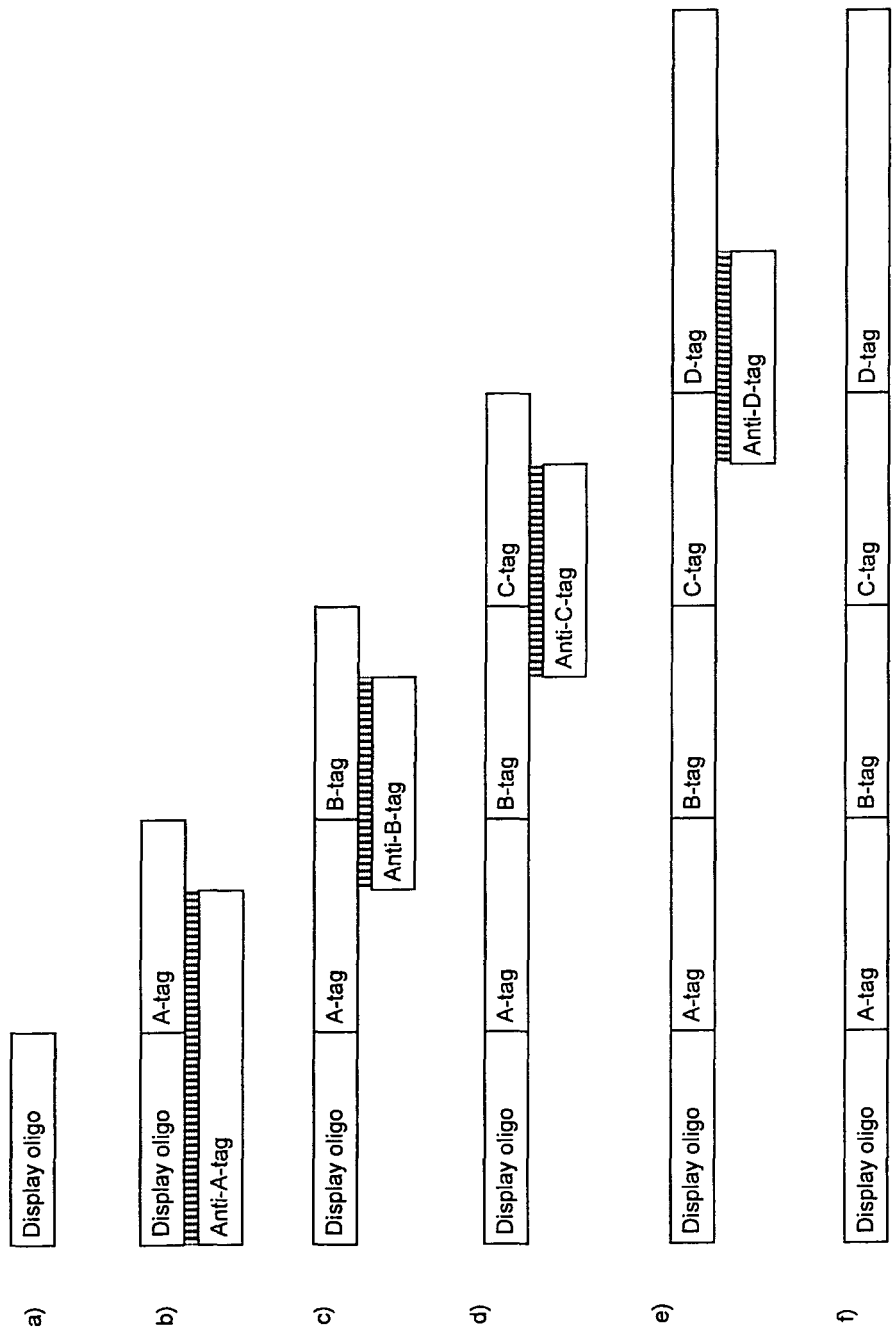

FIG. 21. A tag addition process employing linkage of top strand tags only and removal of anti-tags after each cycle of tag addition. (a) The initial binfunctional complex. (b-e) Addition of tags A to D. (f) The top strand containing tags A to D. The polarity of overhangs is such that B, C, and D tags contact their cognant anti-tag and the anti-tag cognate to the following tag, e.g. a B-tag contacts an anti-B-tag and an anti-C-tag.

Figure 22:
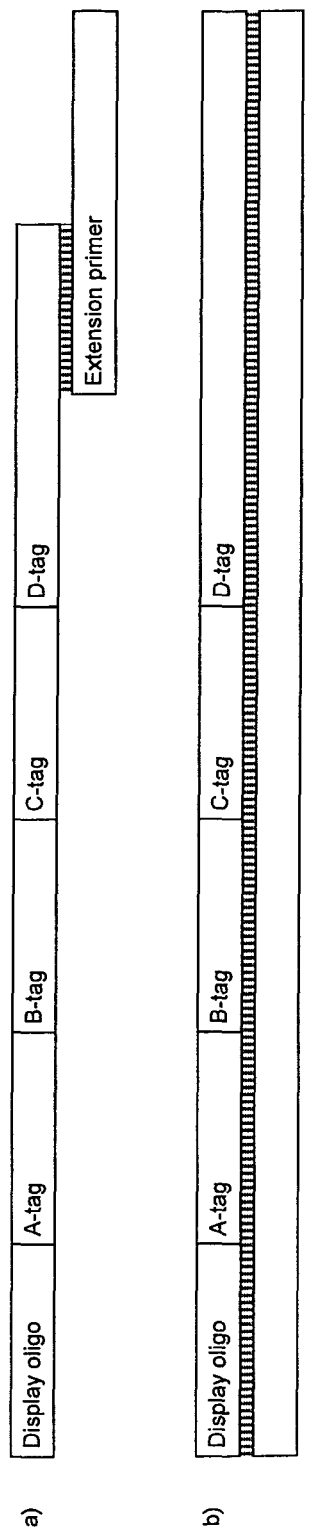

FIG. 22. The primer extension process. (a) An extension primer is annealed to the single tag strand containing tags. (b) Extension of the primer results in a double-stranded tag.

Figure 23:
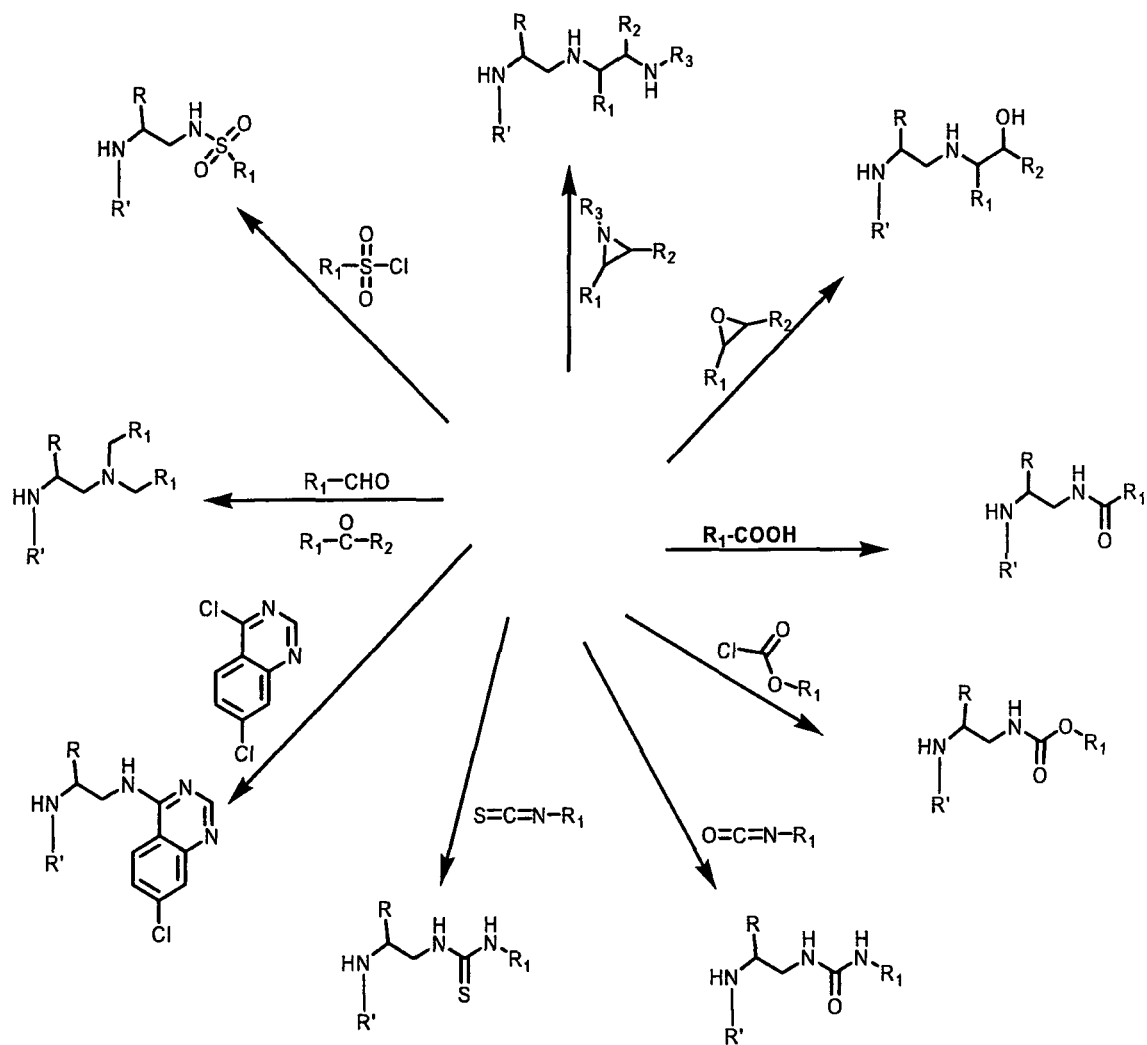

FIG. 23. Examples of chemical reactions using an amine as a chemical reaction site.

Figure 24:
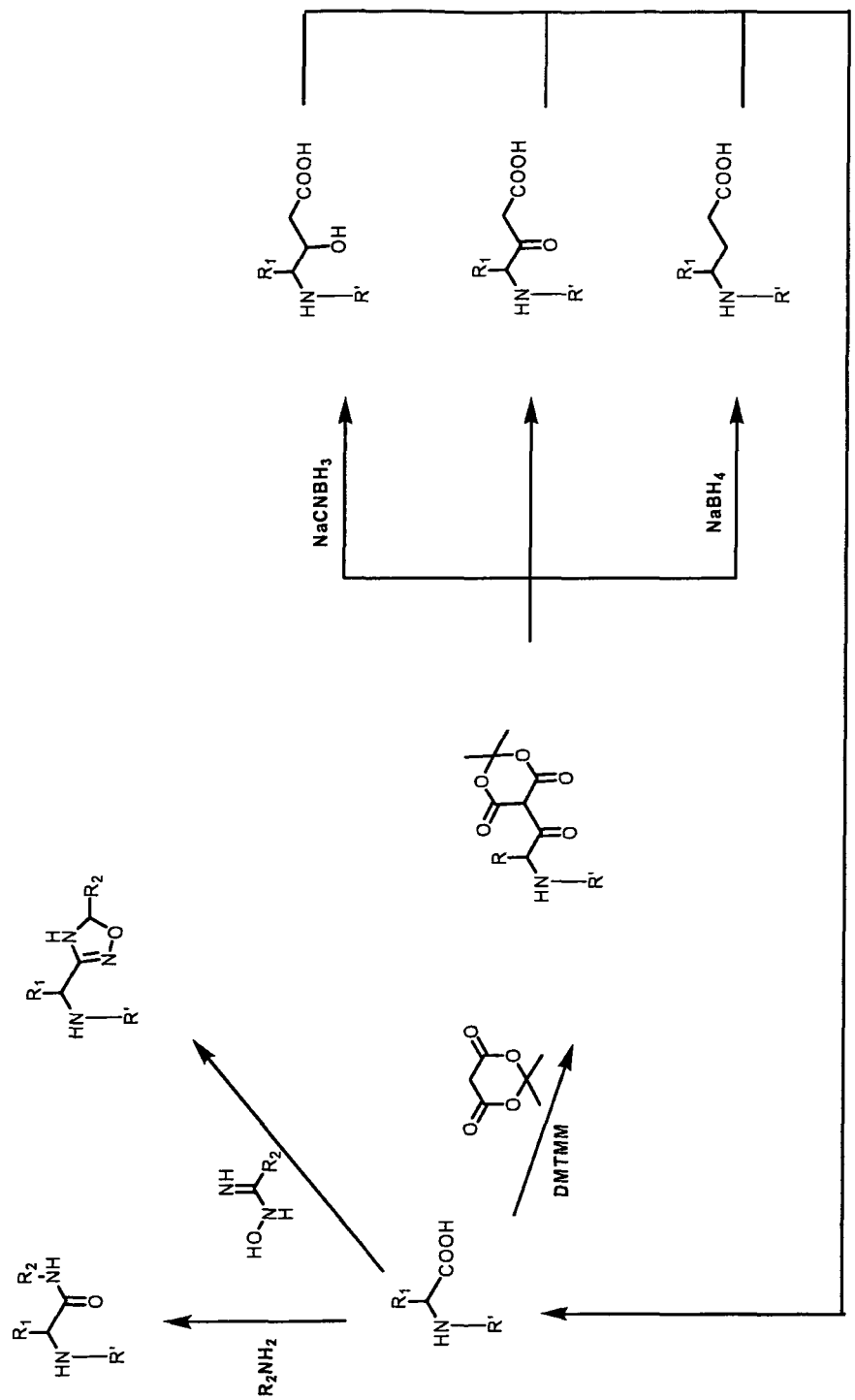

FIG. 24. Examples of chemical reactions using an acid as a chemical reaction site.

Figure 25:
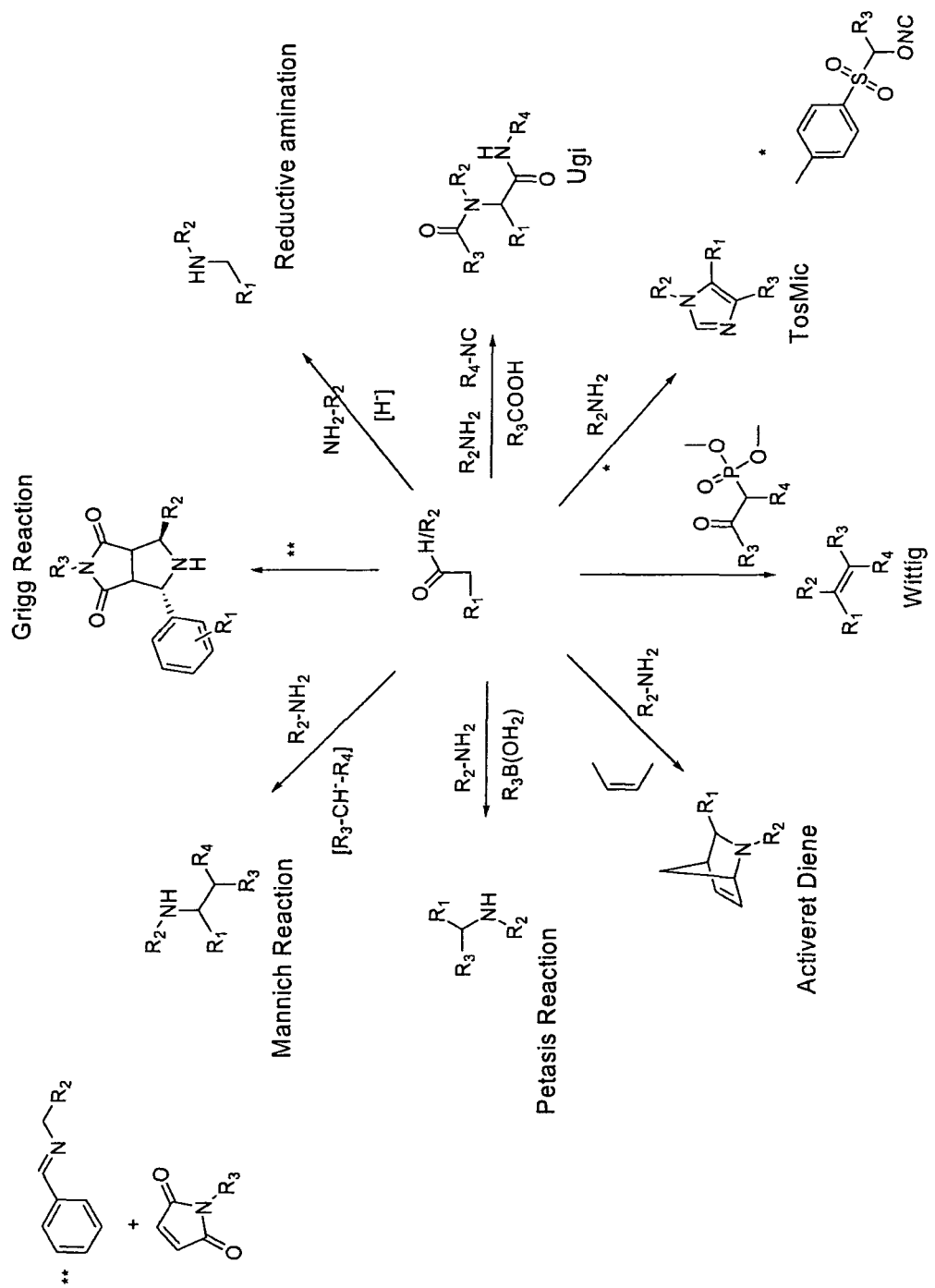

FIG. 25. Examples of chemical reactions using an aldehyde or a ketone as a chemical reaction site.

Figure 26:
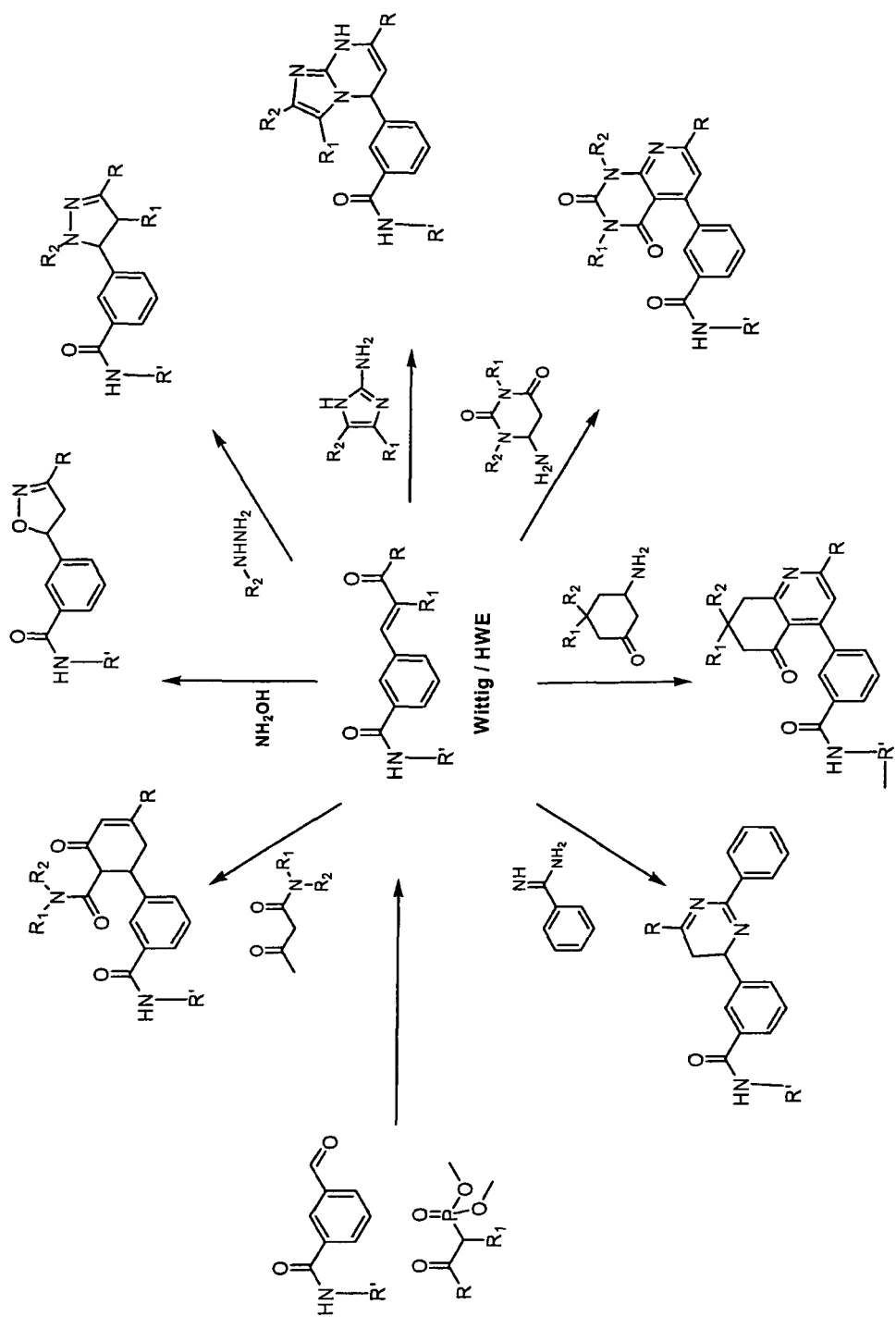

FIG. 26. Examples of chemical reactions using Wittig or Horner-Wadsworth-Emmons reaction substrates.

Figure 27:
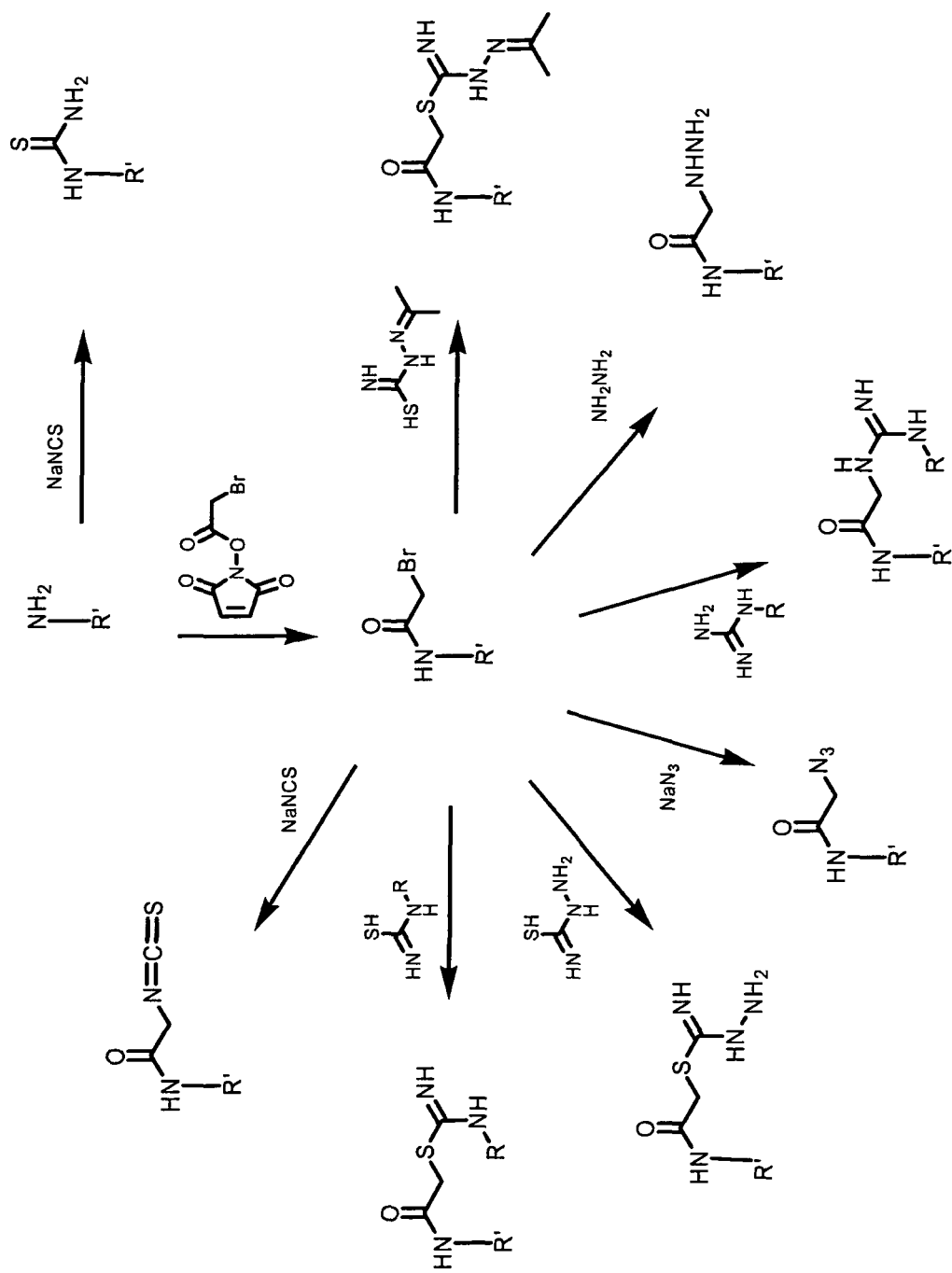

FIG. 27. Examples of chemical reactions generating a dinucleophile.

FIG. 28. Examples of monofunctional versus multifunctional reactions. (a) monofunctional reaction. (b) bi-functional reaction generating a heterocyclic molecule.

FIG. 29. Examples of bi-functional electrophiles.

Figure 30:
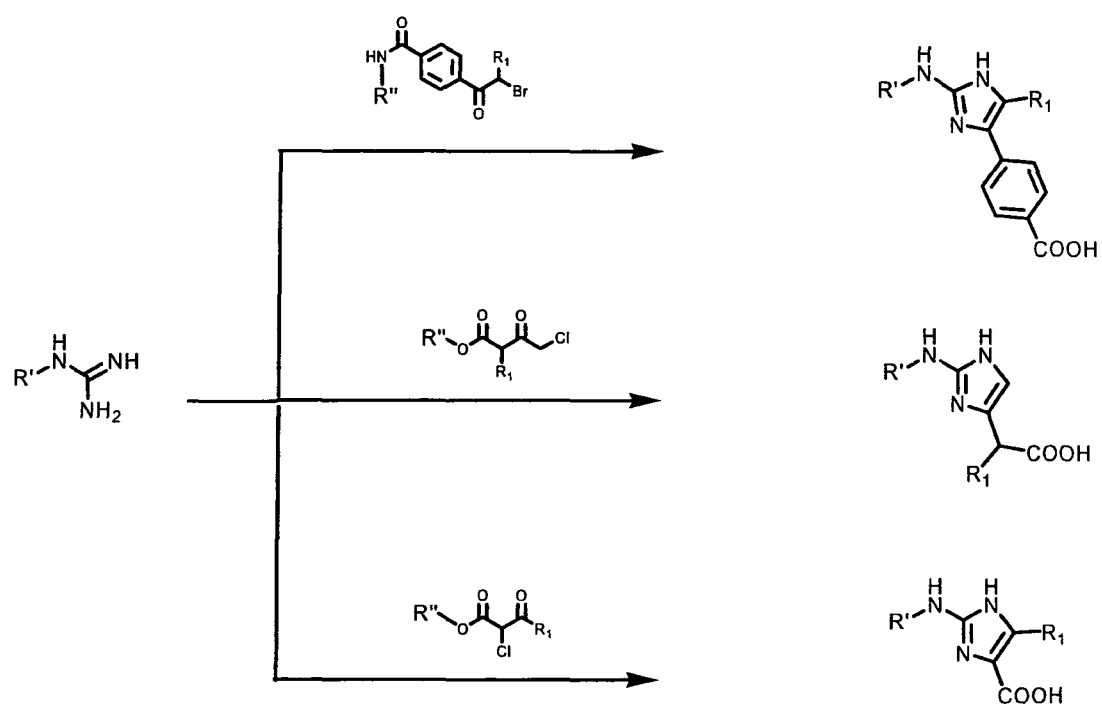

FIG. 30. Examples of chemical reactions of 1,2-dielectrophiles.

Figure 31:
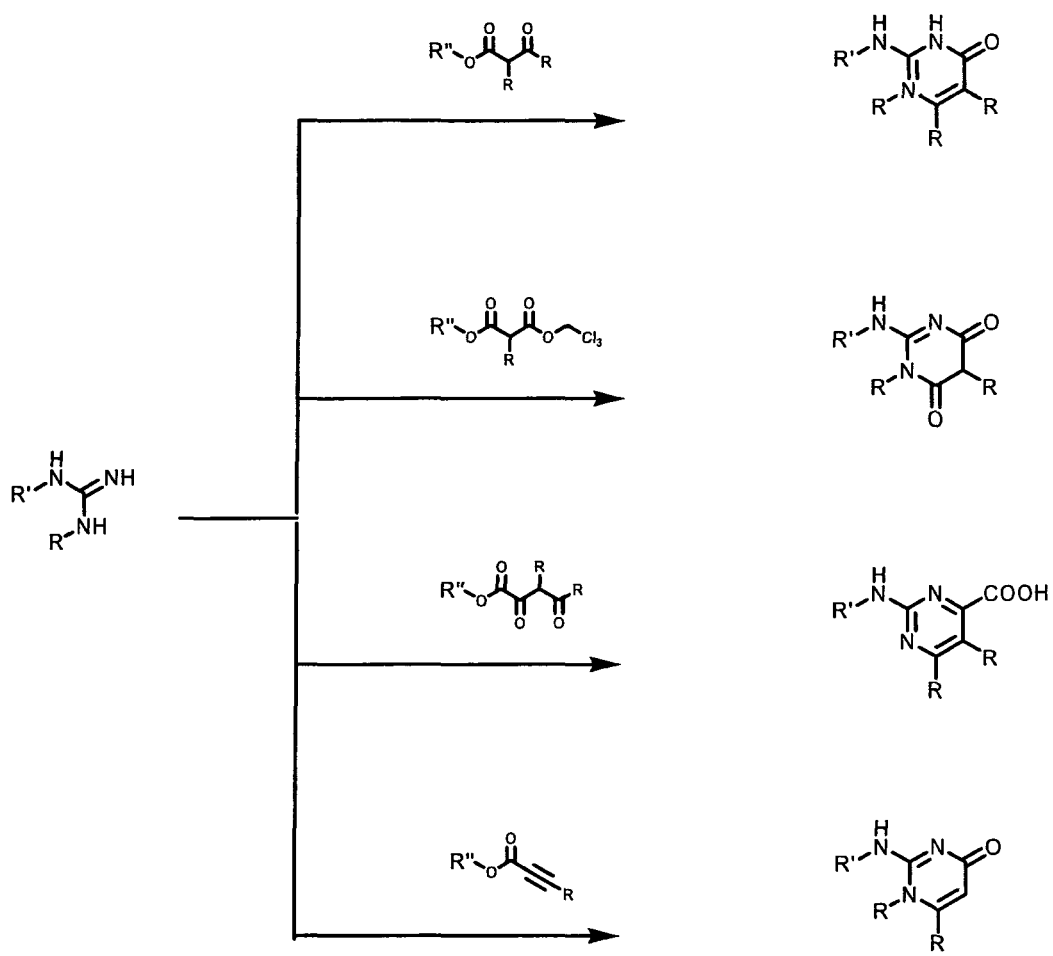

FIG. 31. Examples of chemical reactions of 1,3-dielectrophiles.

Figure 32:
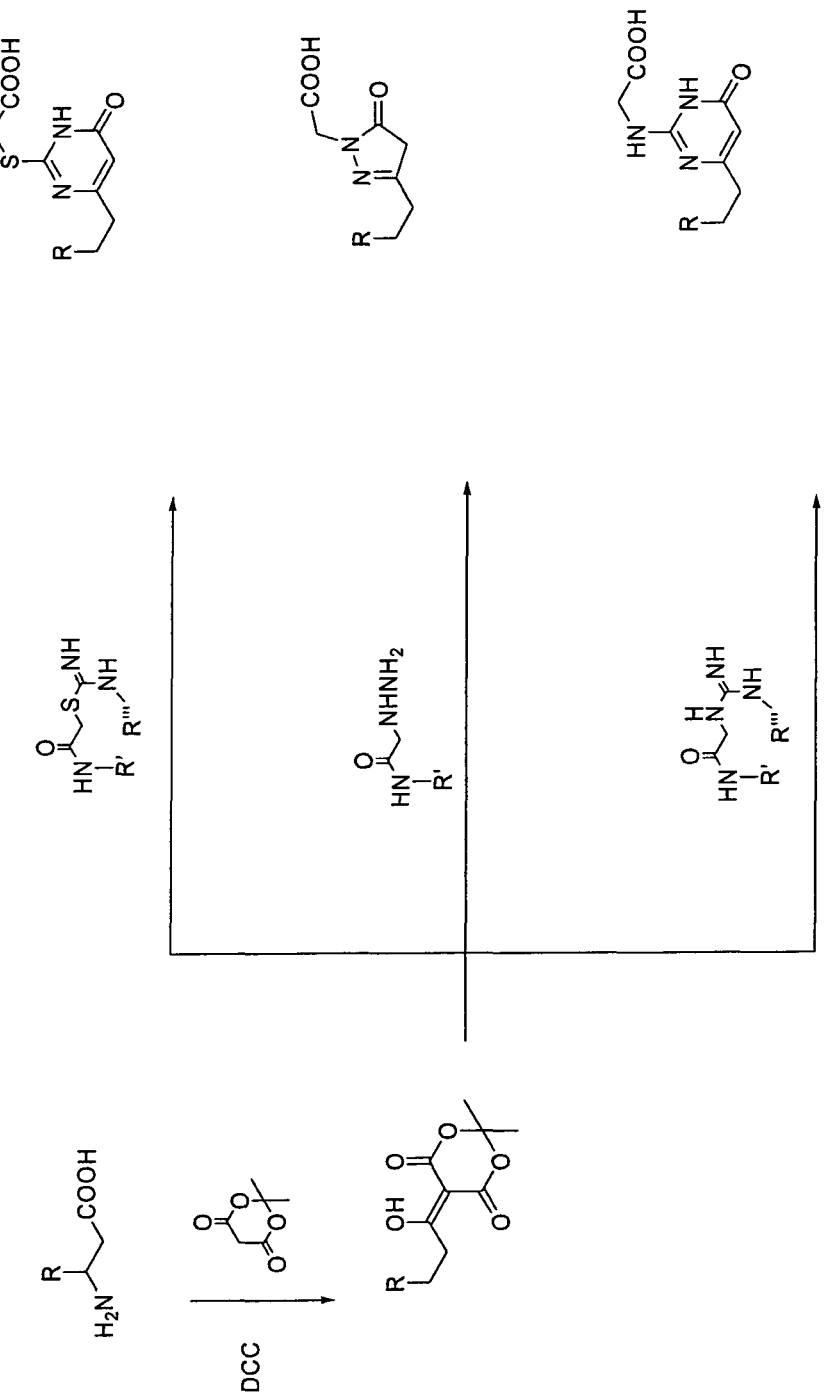

FIG. 32. Examples of transformations of building blocks (reactive compound building blocks) into heterocycles.

Figure 33:
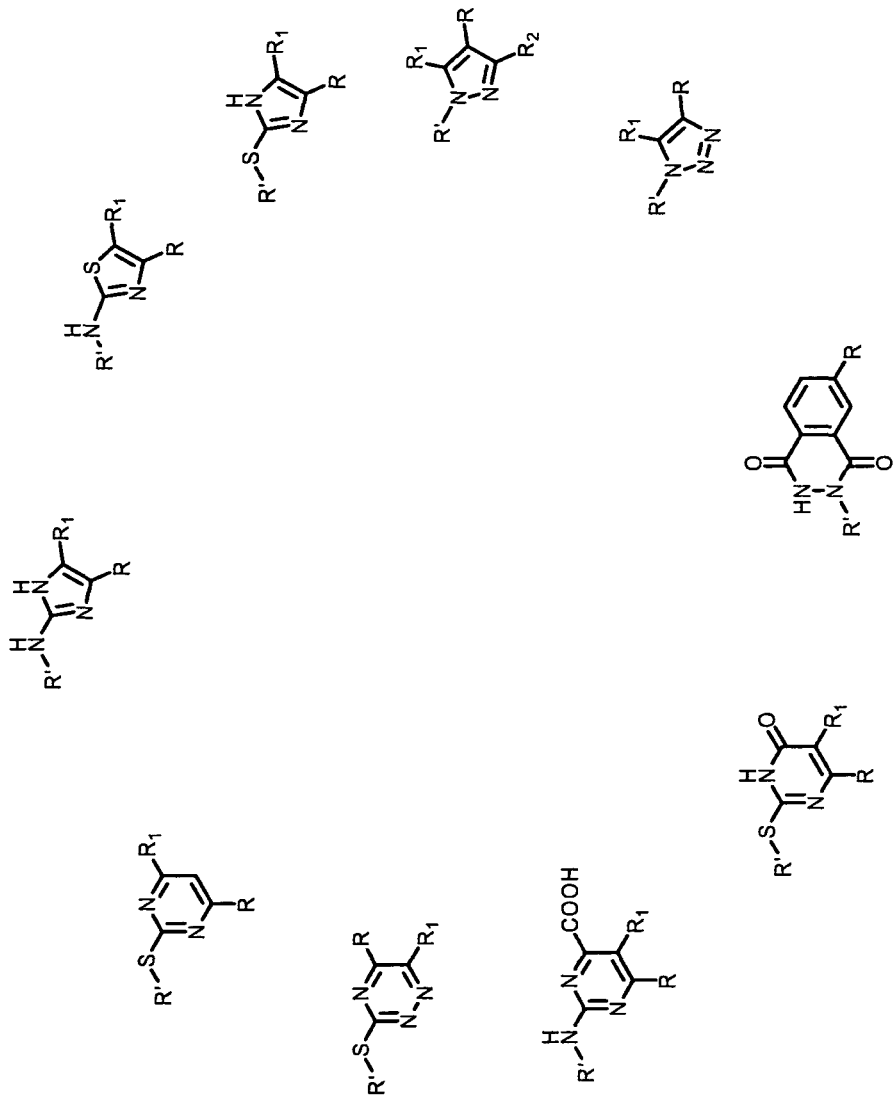

FIG. 33. Examples of heterocyclic structures generated using bi-functional reactions.

Figure 34:
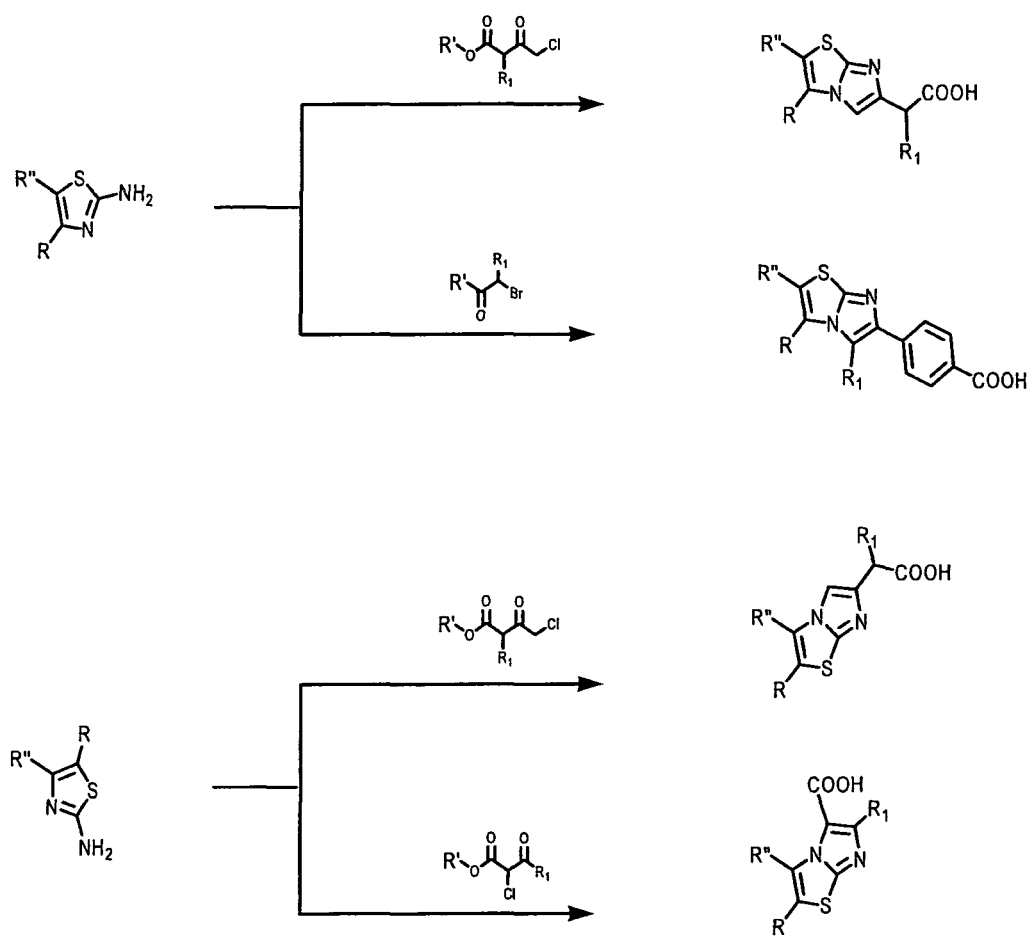

FIG. 34. Examples of chemical reactions generating bicyclic structures (I).

Figure 35:
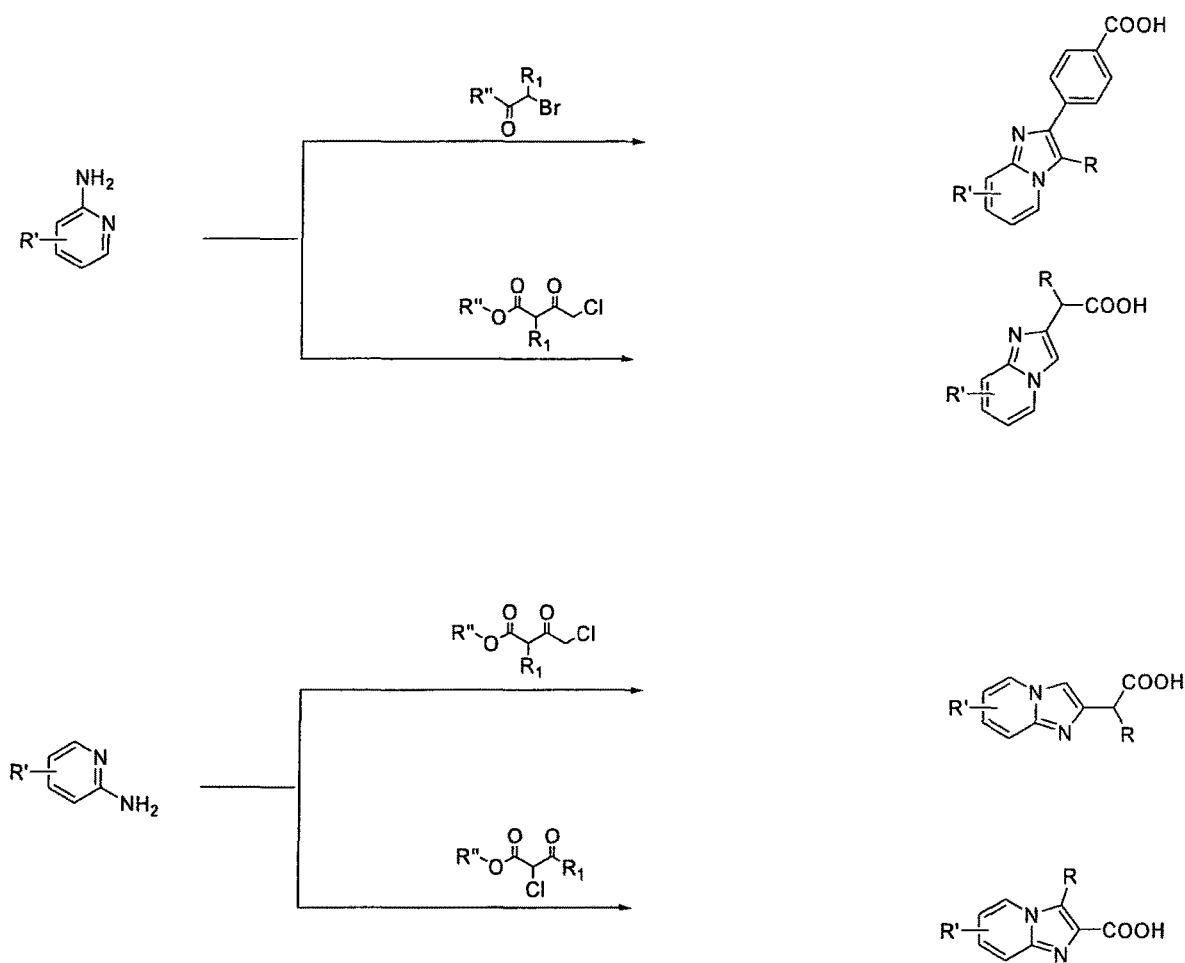

FIG. 35. Examples of chemical reactions generating bicyclic structures (II).

Figure 36:
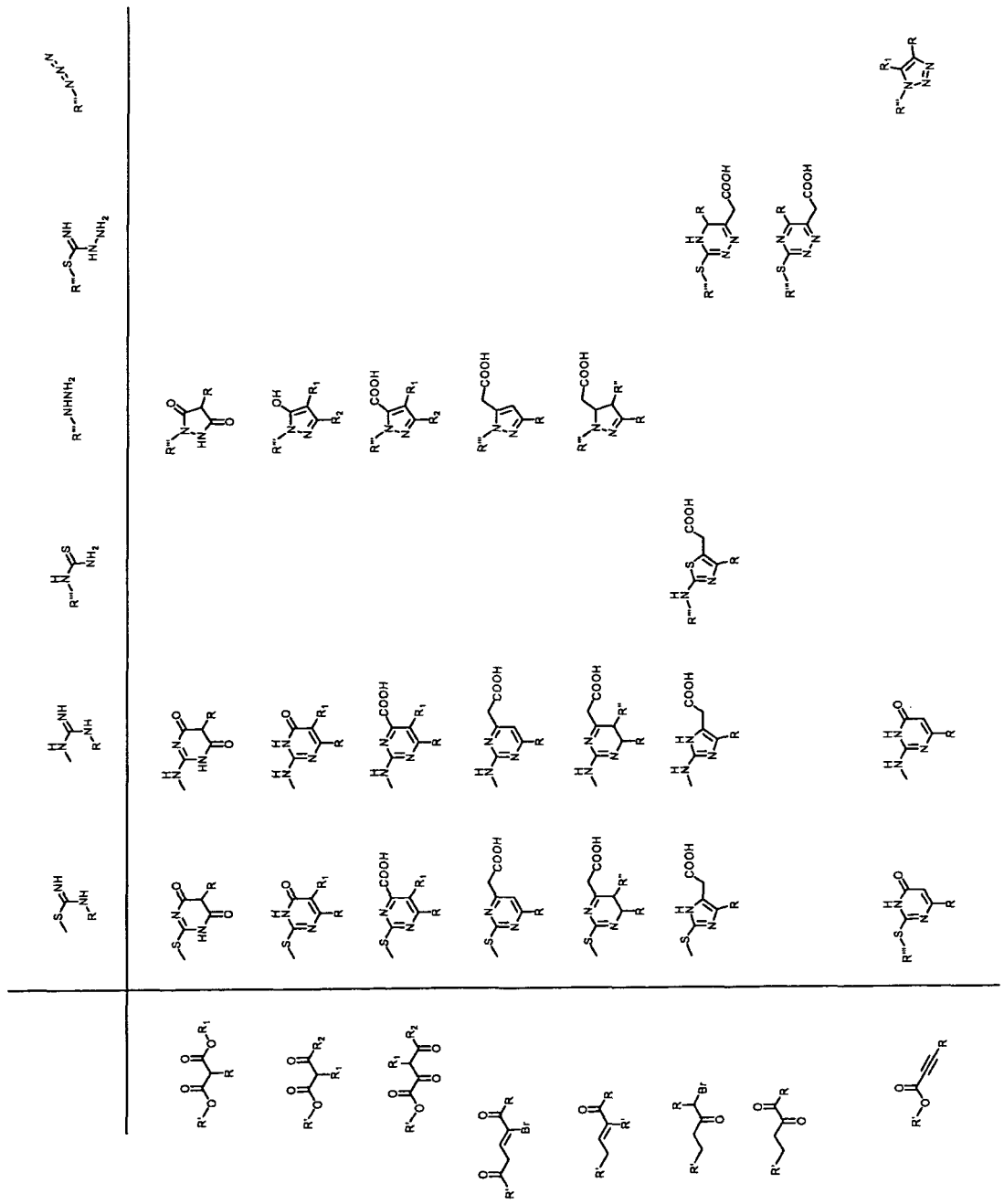

FIG. 36. Examples of chemical reaction matrix illustrating how building blocks (reactive compound building blocks) (rows and columns) can be combined to form cyclic structures.

Figure 37:
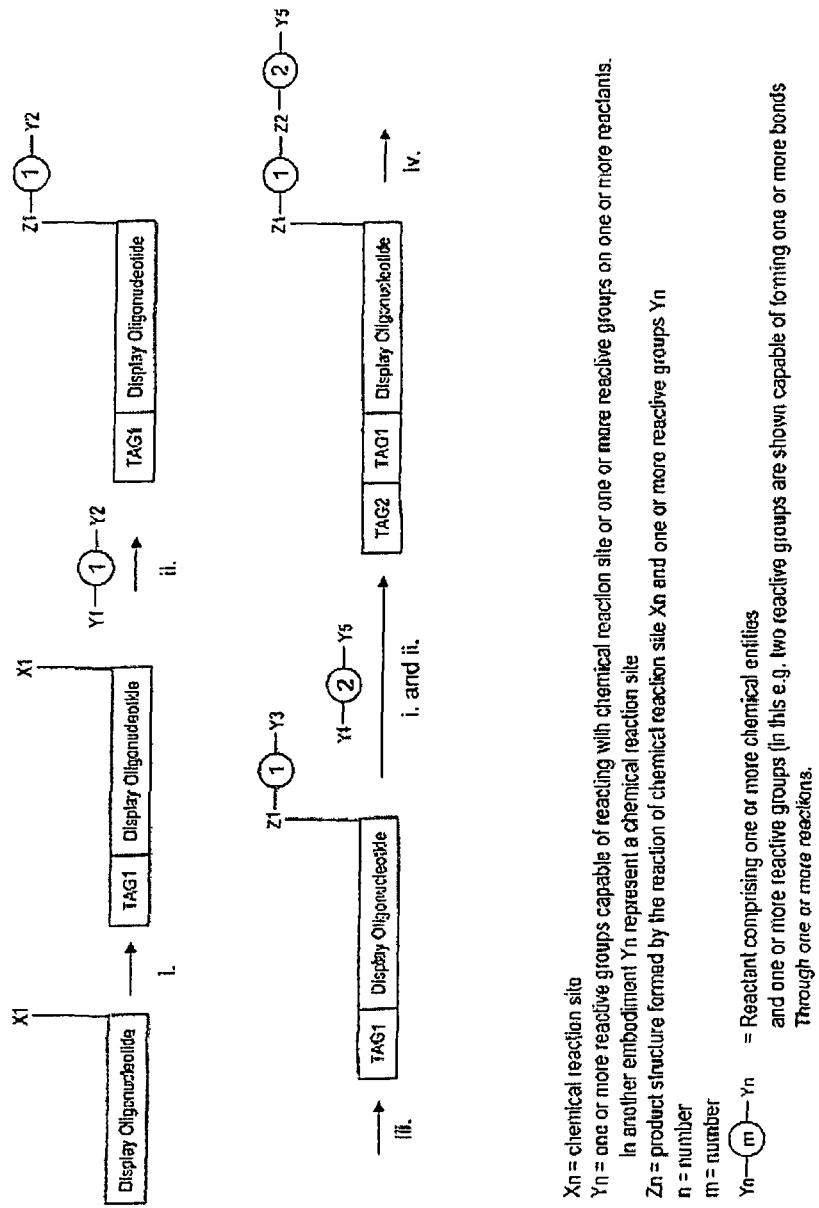
Figure 38:
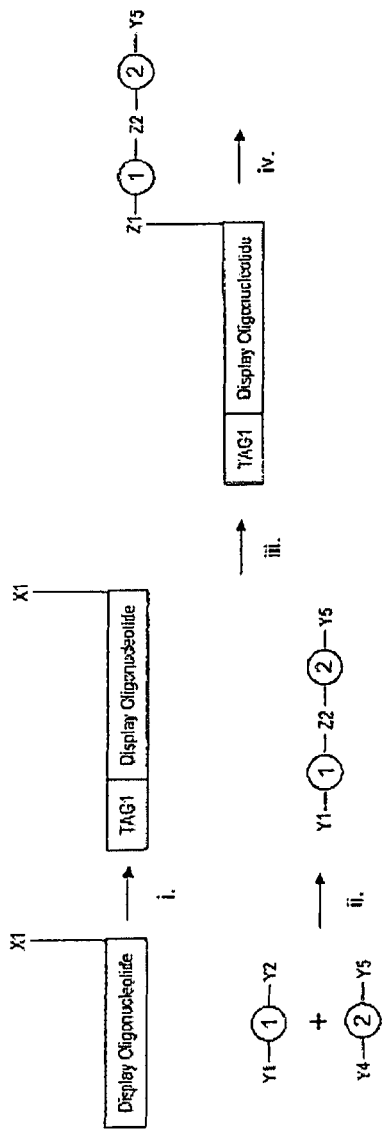
Figure 40:
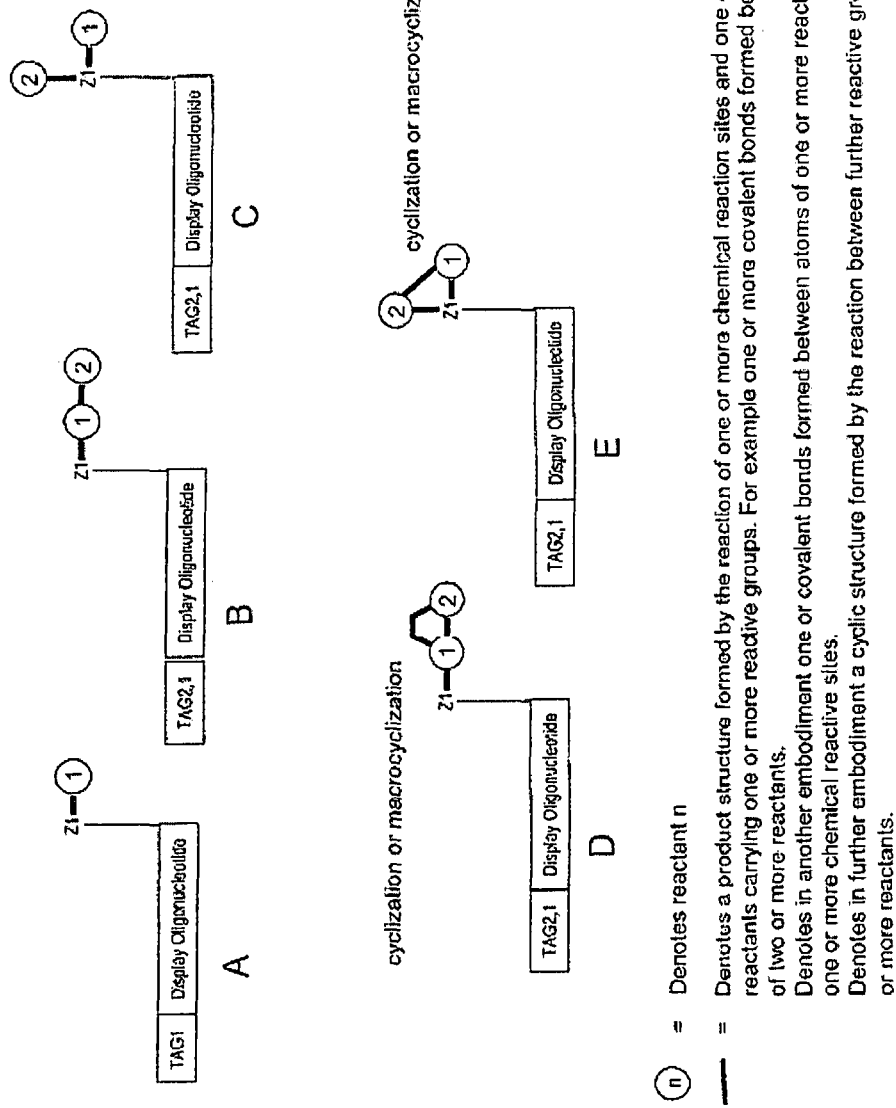
Figure 41:
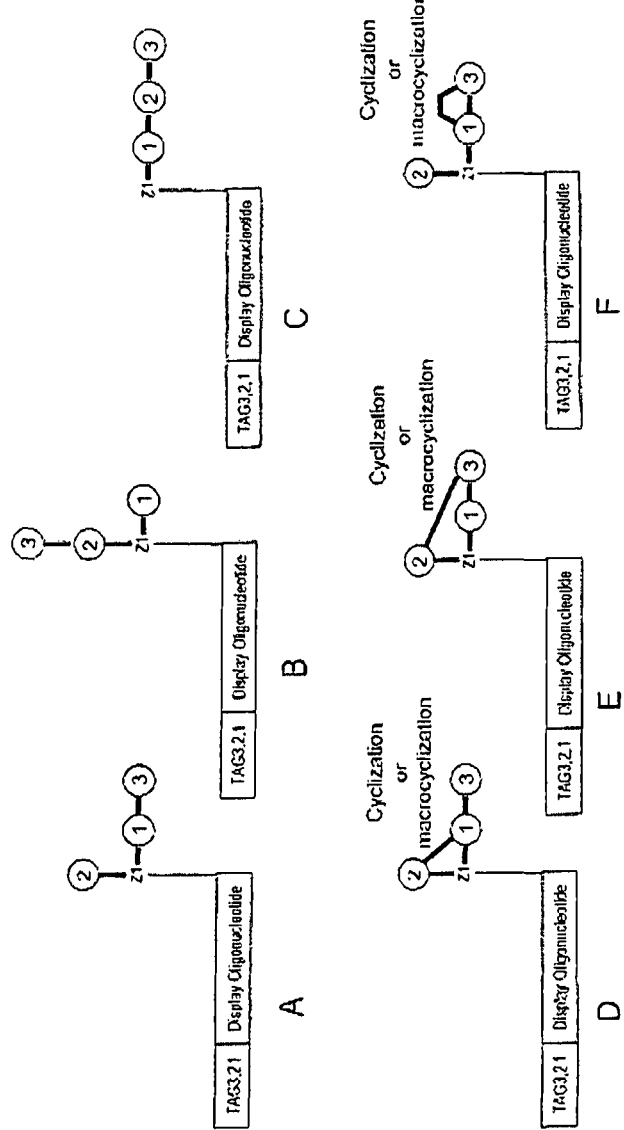
Figure 42:
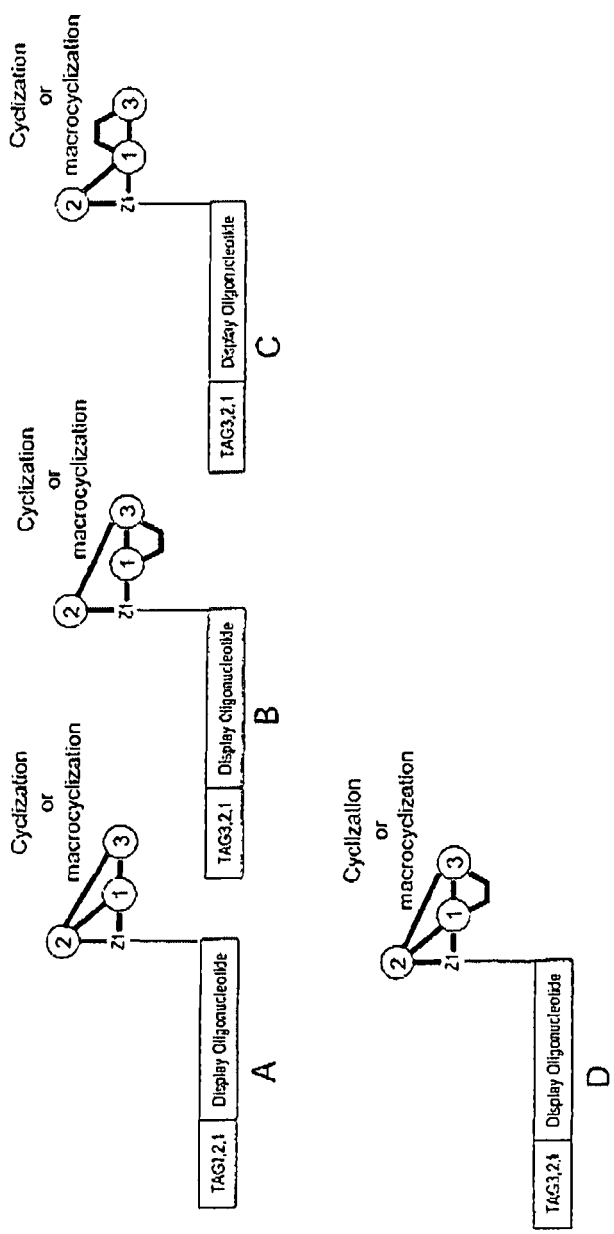
Figure 43:
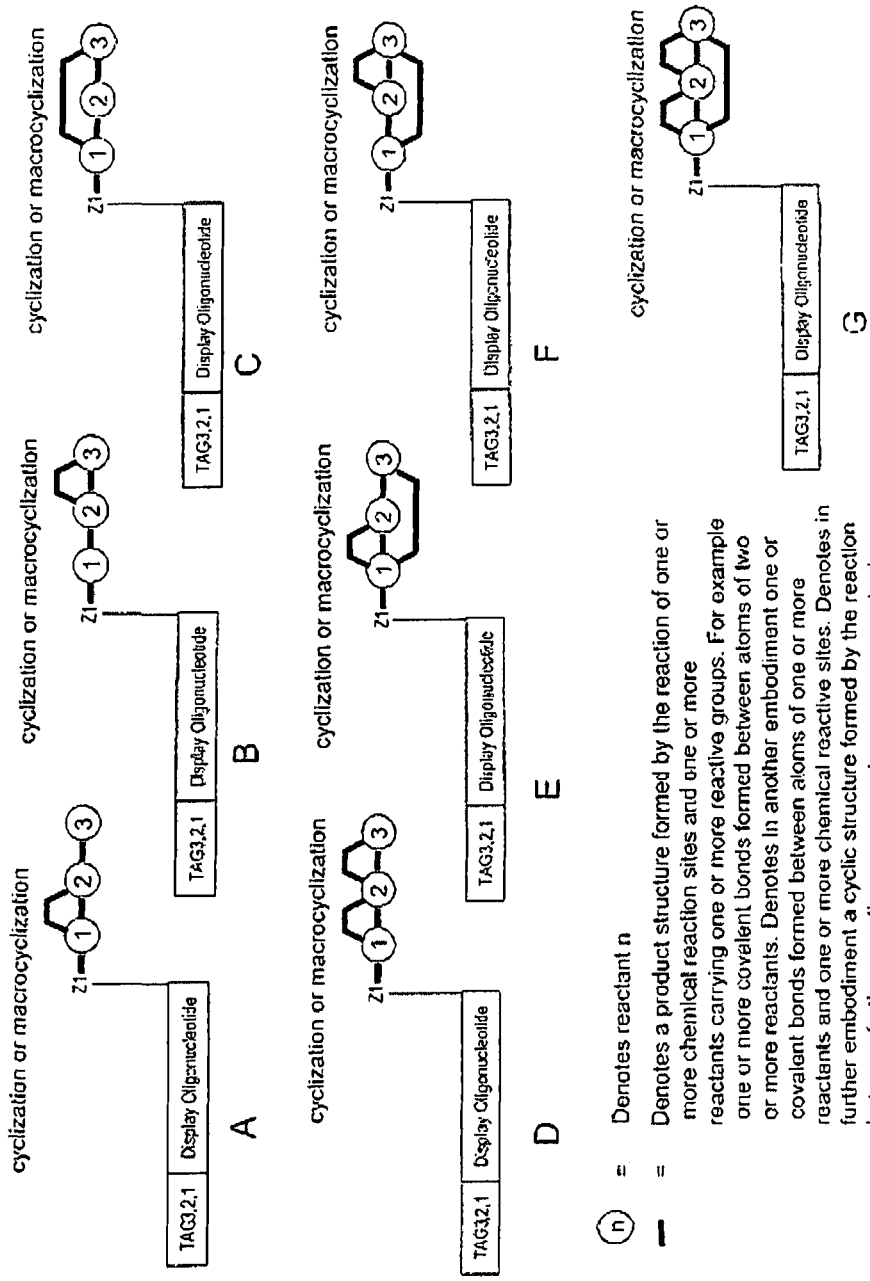
Figure 44:
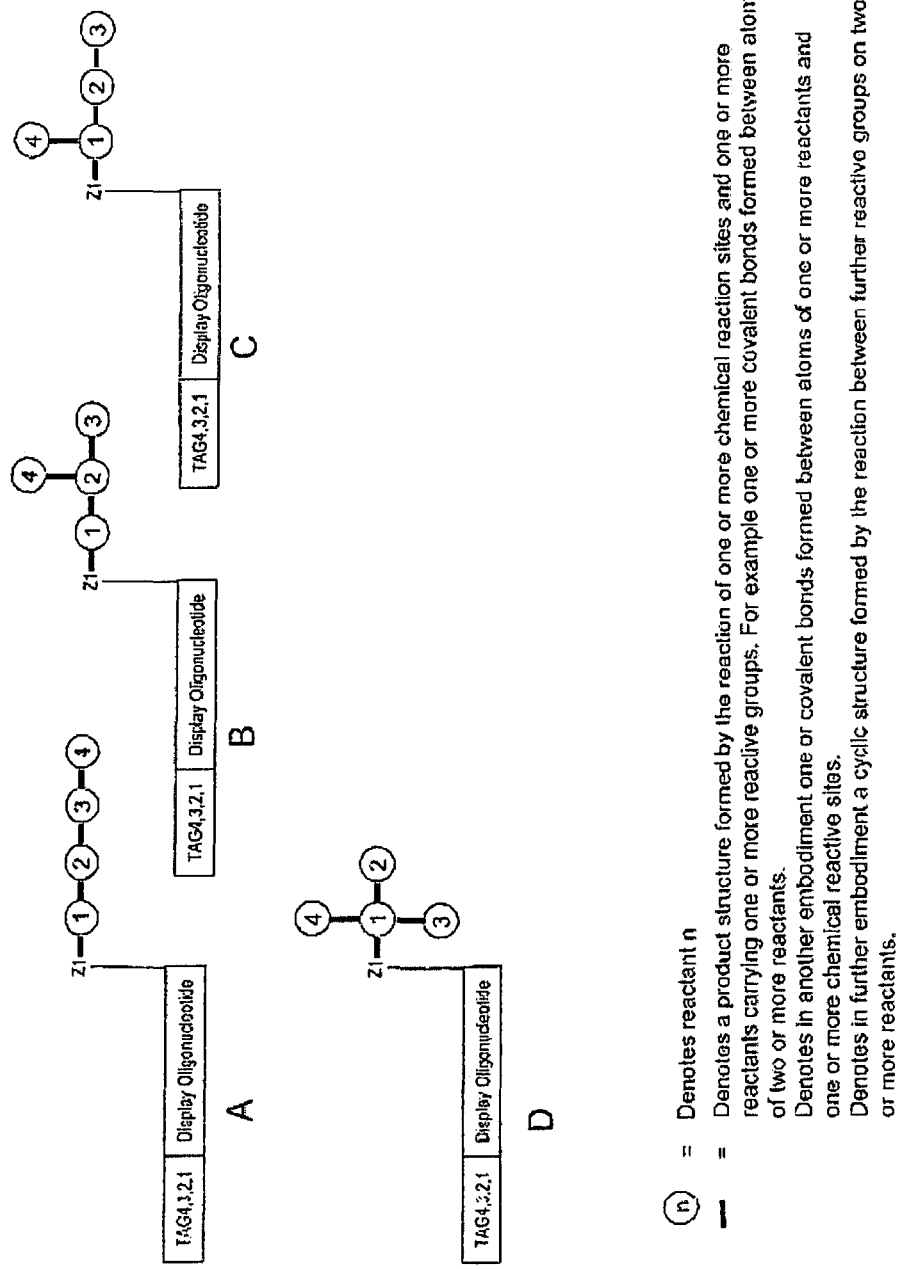
Figure 45:
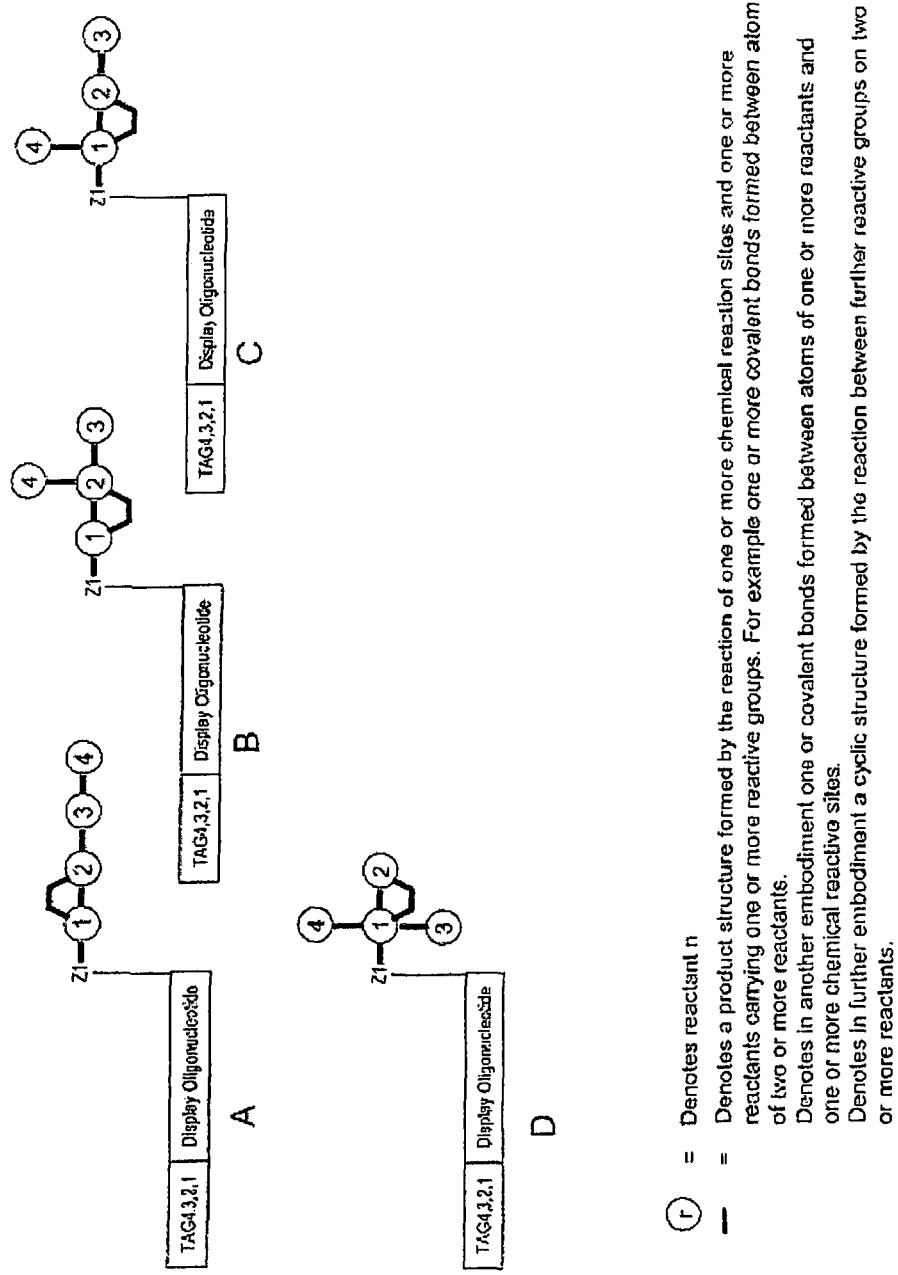
Figure 46:
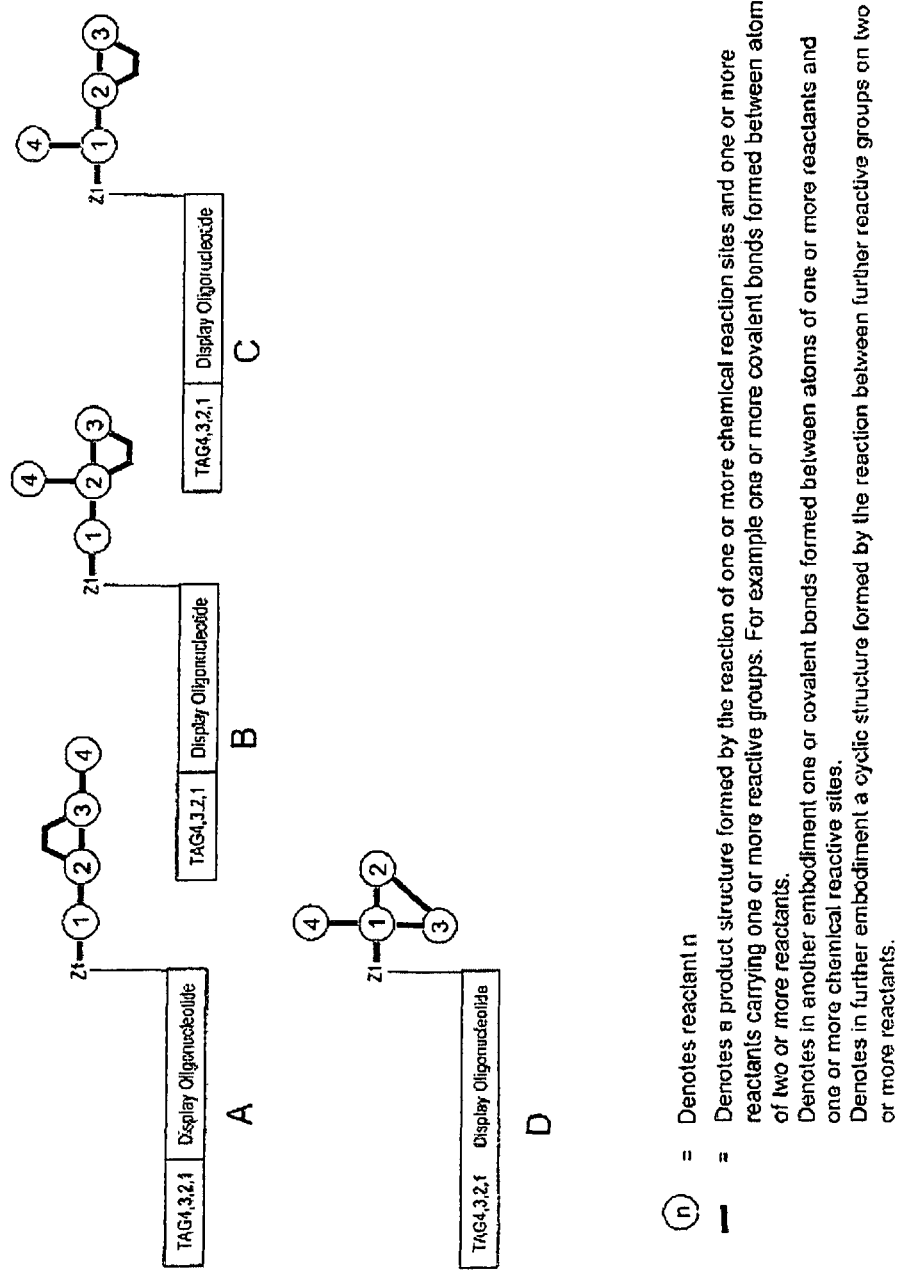
Figure 47:
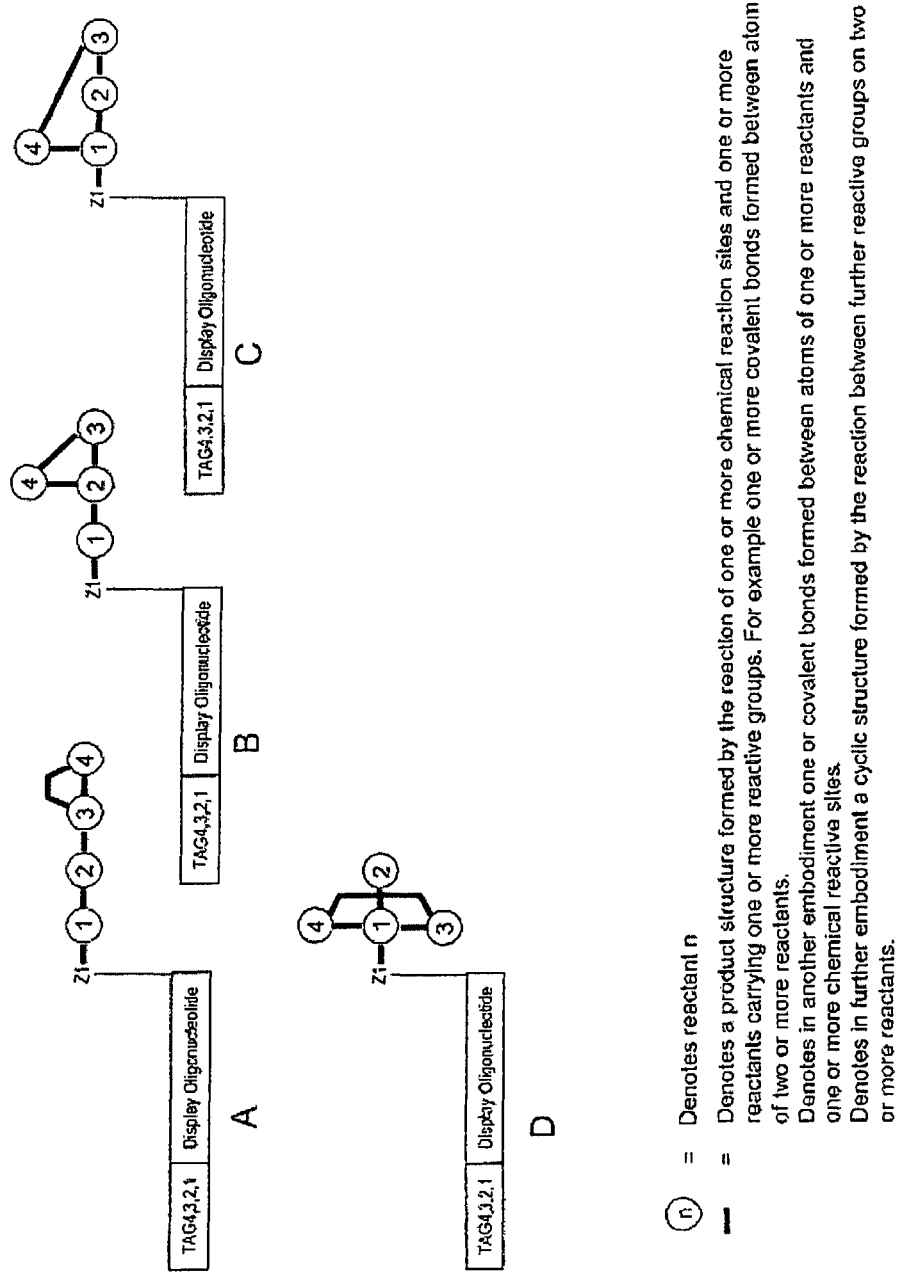
Figure 48:
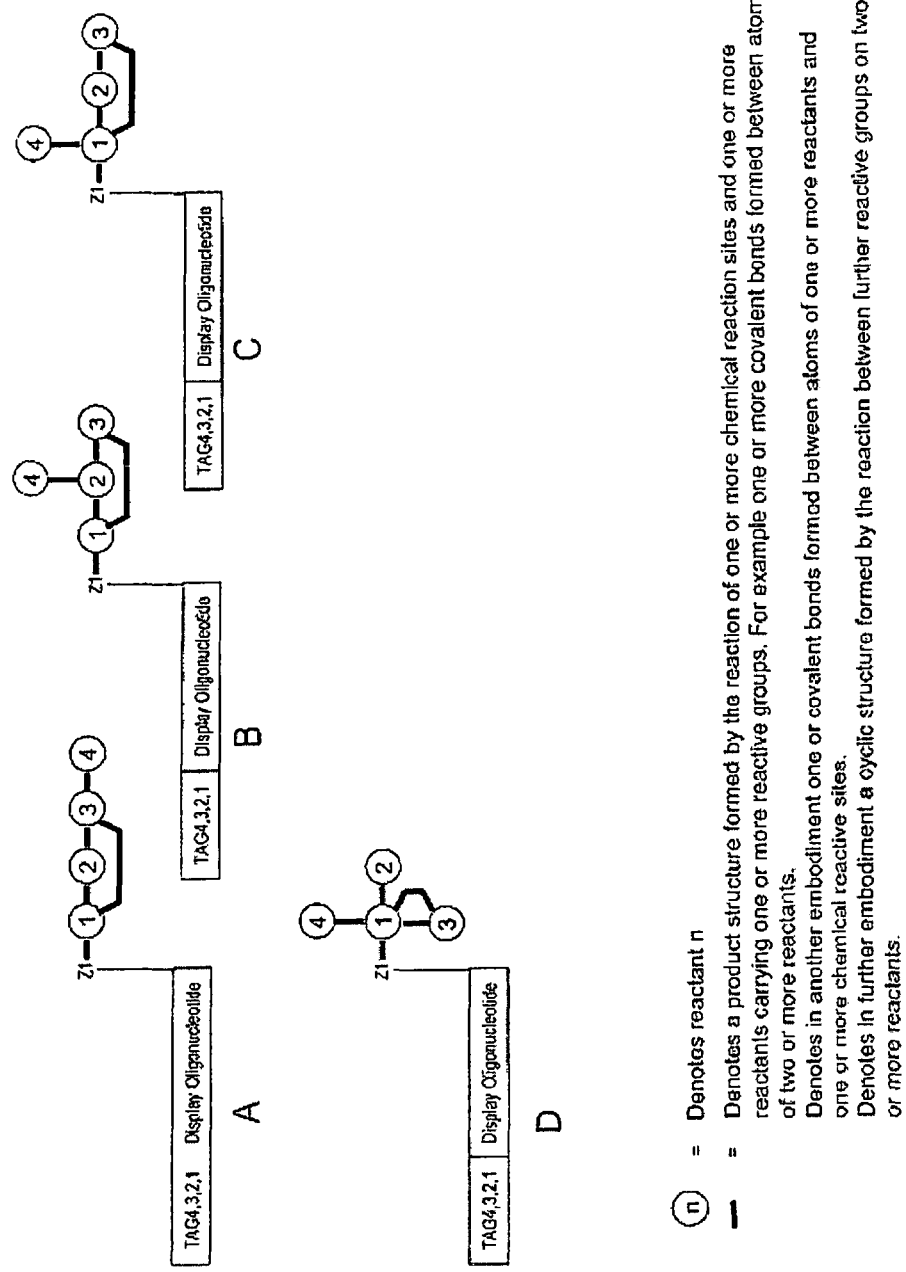
Figure 49:
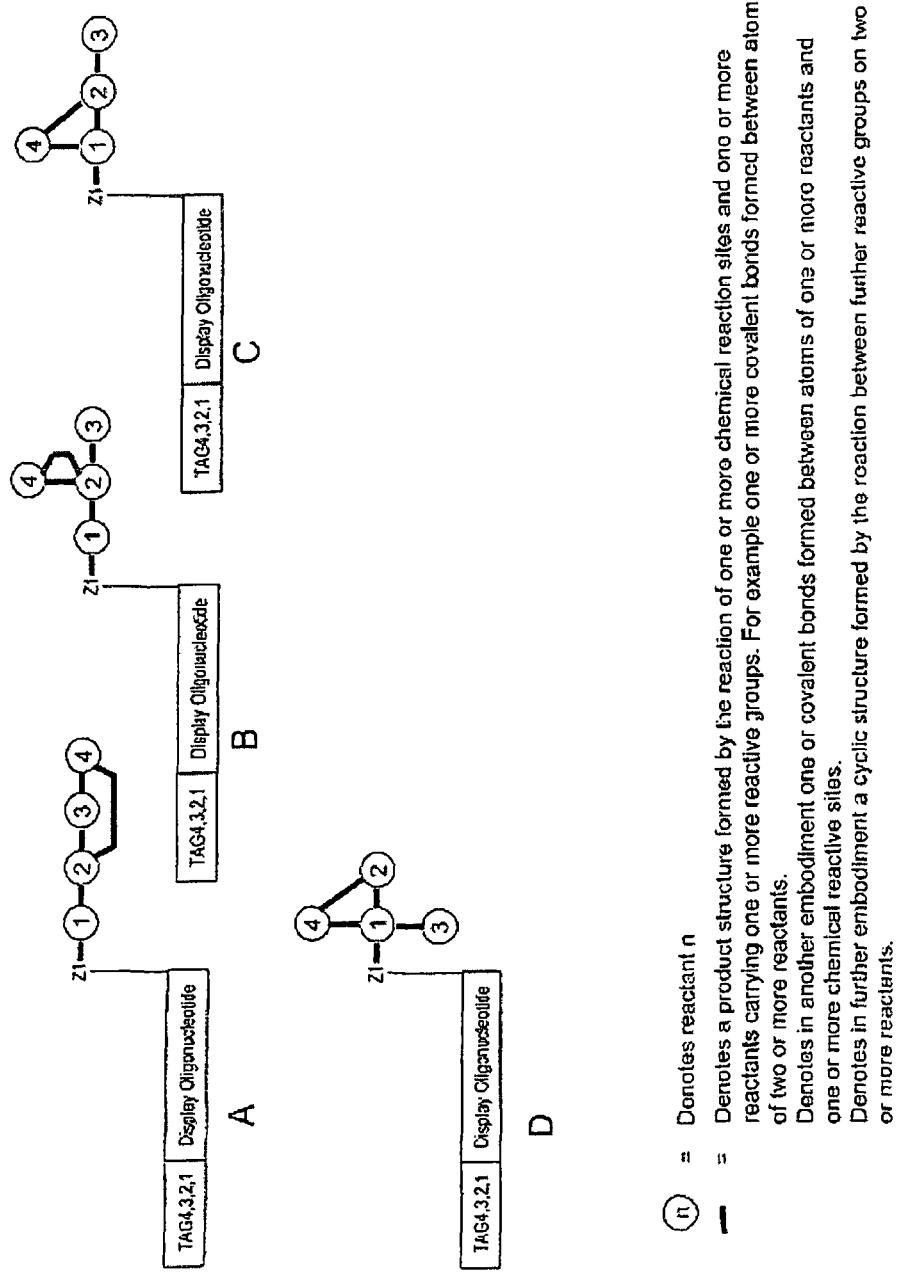
Figure 50:
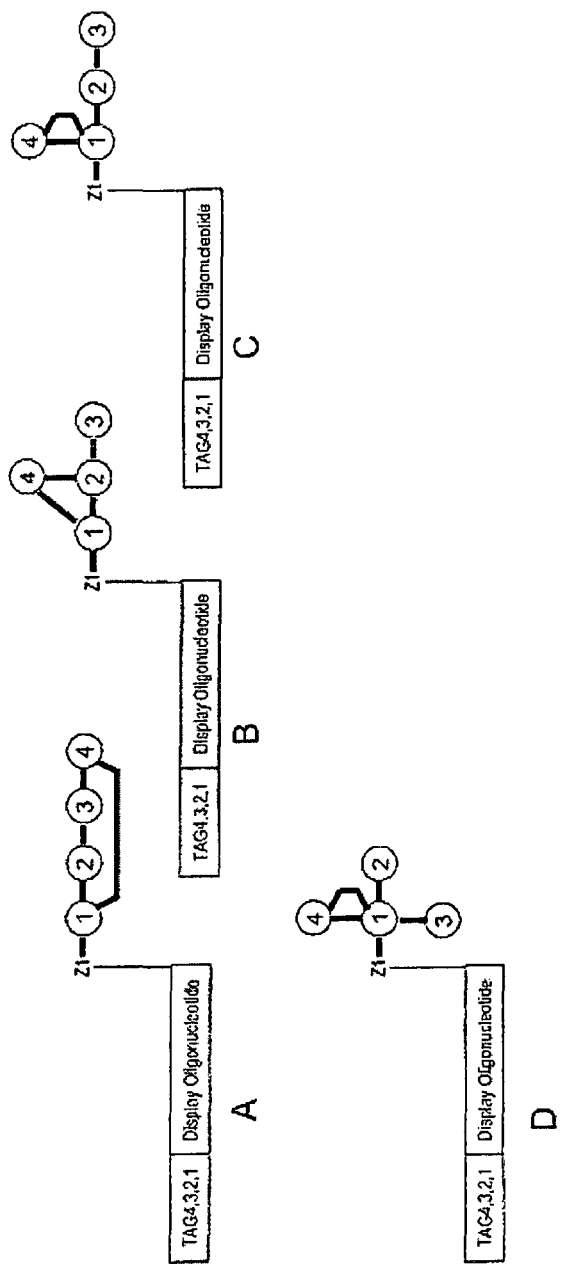
Figure 51:
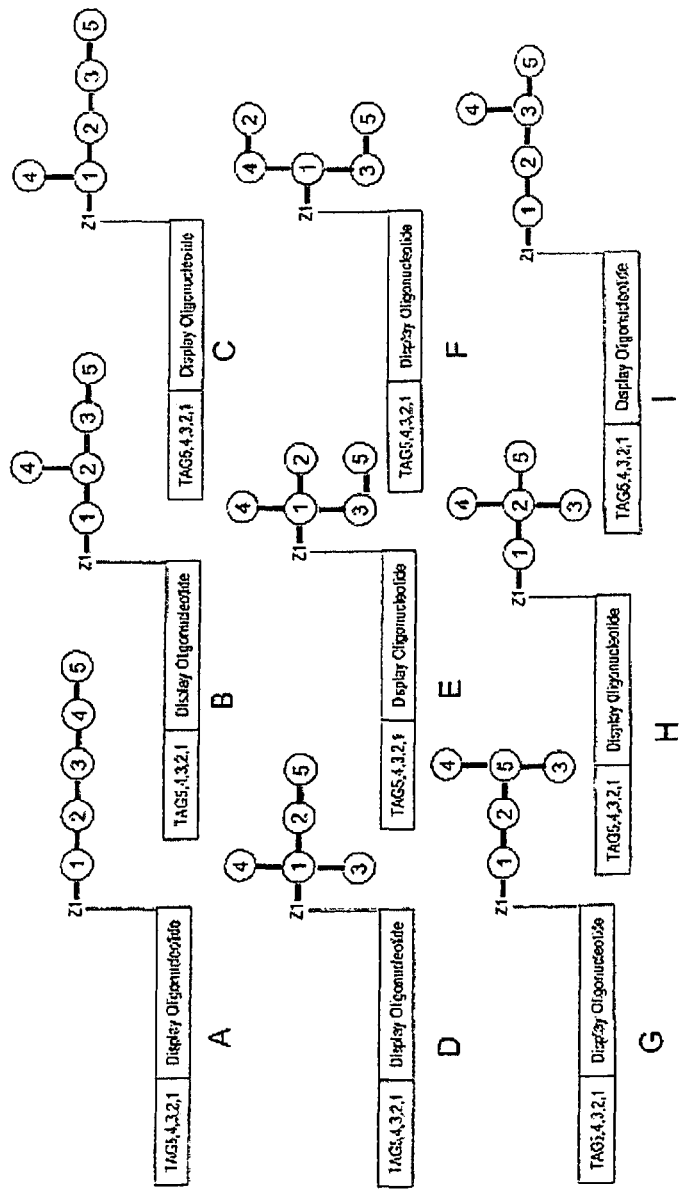

FIGS. 37-38. The figures serve to illustrate the formation of molecules/product structures formed by the process.

The figures represent examples, which are not meant to limit the scope of the invention. In FIG. 37, the following steps are illustrated:

Step i.: E.g. enzymatical ligation of one oligonucleotide tag to the display oligonucleotide.

Step ii.: E.g. Reacting one reactive compound building block with the chemical reaction site in the formation of one or more covalent bonds.

Step iii.: Reactive groups may optionally be transformed into other reactive groups, such as for example but not limited to the deprotection of one reactive group into another reactive group, for example deprotection of a amino protection group, whereby a reactive amine will be formed, for example deprotection of an ester, whereby a reactive carboxylic acid will be formed, for example oxidation of a 1,2-diol using periodate, whereby a reactive aldehyde will be formed.

Step iv.: Optionally repeat step iii., optionally repeat step i. and ii. Optionally, conduct further repetition of step iv. and other steps in accordance with and as described and claimed by this invention.

FIG. 38. Reactive compound building blocks may be reacted prior to (step ii) reactions with the chemical reaction site (step iii).

FIG. 39. The figure serves to illustrate example reactive compound building blocks comprising one or more chemical entities and one or more reactive groups. The invention is not limited to the use of the reactive compound building blocks shown.

Reactive compound building blocks may furthermore be protected by use of one or more protection groups.

Reactive compound building blocks within a group comprising one or more identical reactive groups may comprise different chemical entities, which may be focused around specific core structures or which may be diverse (different) or the group may comprise a combination of focused and diverse chemical entities.

Reactive compound building blocks in different groups of reactive groups may be focused around specific core structures or may be diverse (different) or the groups may comprise a combination of focused and diverse chemical entities.

FIGS. 40-51. Circles with a number inside, denotes reactive compound building blocks. The figures serve to illustrate various product structures formed by the use of reactive compound building blocks in various ways.

Emphasized (thick) lines denotes a product structure formed by the reaction of one or more reactive groups on one or more reactive compound building blocks and a product structure formed by the reaction of one or more reactive groups on one or more reactive compound building blocks and one or more chemical reaction sites. The product structure does not need to comprise atoms (direct covalent linkage of two reactive compound building blocks). The product structure may also comprise one or more bonds and one or more atoms. The product structure may be cyclic or linear or branched or combinations thereof. The product structure may for example also comprise product structure examples as described elsewhere by this invention. Product structures represented by thick lines may be the same or different.

FIGS. 52-65. In some figures a pyrimidine product structure is used as an example for a heteroaromatic chemical structure e.g. an azine, such as for example a pyridine, a pyrimidine, a pyrazine, a pyridazine, a purine and for example benzo and azolo variants thereof. Azine product structure examples are also exemplified elsewhere in this invention.

Definitions Used:
CRS: Chemical reactive site
Chemical entities are denoted/illustrated by R groups, which may have numbers such as R1, R2, R3, R4, R5, R6, R7, R8, R9, R10. Chemical entities may also be shown as a circle with an R group inside. Such circles may optionally represent a cyclic structure, e.g. R1 may be a cyclic structure such as e.g. a cyclic diamino acid, for example but not limited to the product following the use of piperidine 2-carboxylic acid as reactive compound building block, whereby two amino groups may react with similar or different electrophiles, such as for example reaction with aldehydes under reductive amination conditions to form an alkylated amine, for example reaction with a sulfonyl chloride to form sulfonamides, for example acylation by reaction with carboxylic acids under for example EDC/NHS or DMTMM coupling conditions to form carboxamides, for example reaction with haloazines to form aminoazines, and the carboxylic acid of the diaminoacid may undergo an acylation reaction to form an amide. Although illustrated by circles, the back bone/core/scaffolded structure may in fact be either cyclic or non-cyclic, including branched, linear, cyclic structures or a combination thereof. Amino groups may be primary amines, secondary amines, tertiary amines. Amide groups may be primary, secondary, tertiary amides. When the circle represents a cyclic structure, amines may be endocyclic or exocyclic.

Het: means a heterocyclic product structure for example an azine, an azole, a purine, and other heterocyclic systems as defined elsewhere in the invention.

Aromatic rings with an N inside the ring are by definition equivalent to Het. Pyrimidine structures are also equivalent to the definition of Het and the pyrimidine structure is only used to illustrate the example and not to limit the scope of this invention.

Figure 52:
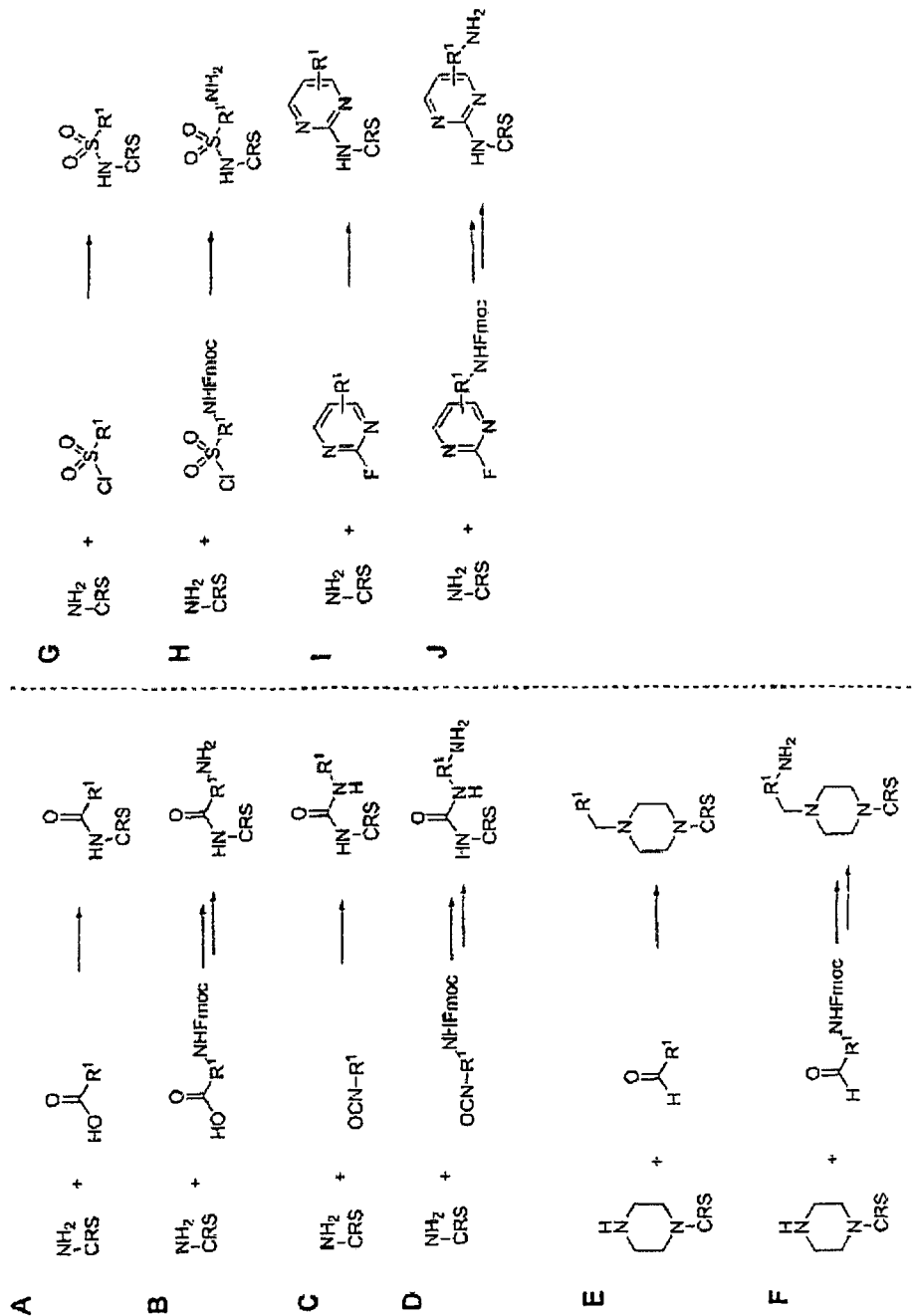
Figure 53:
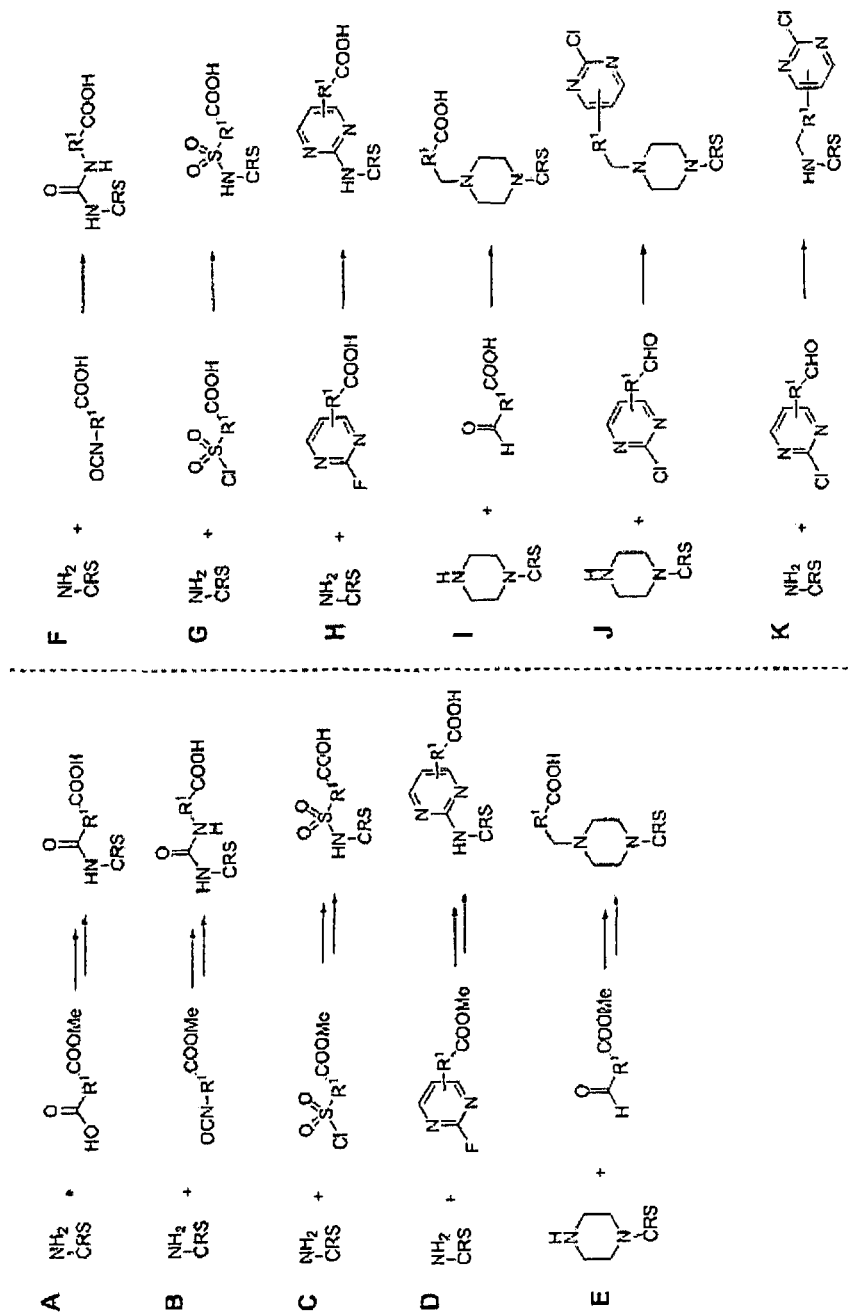
Figure 54:
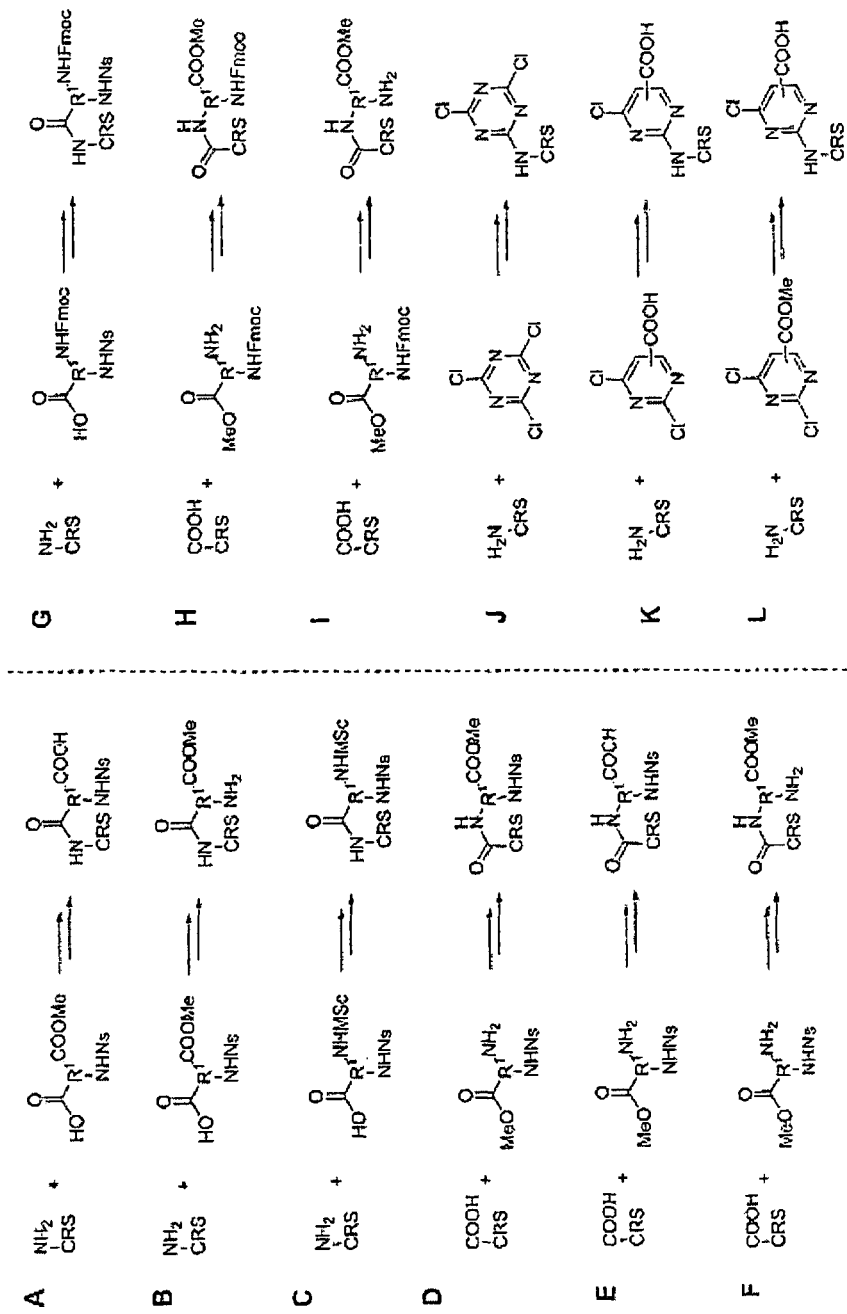
Figure 55:
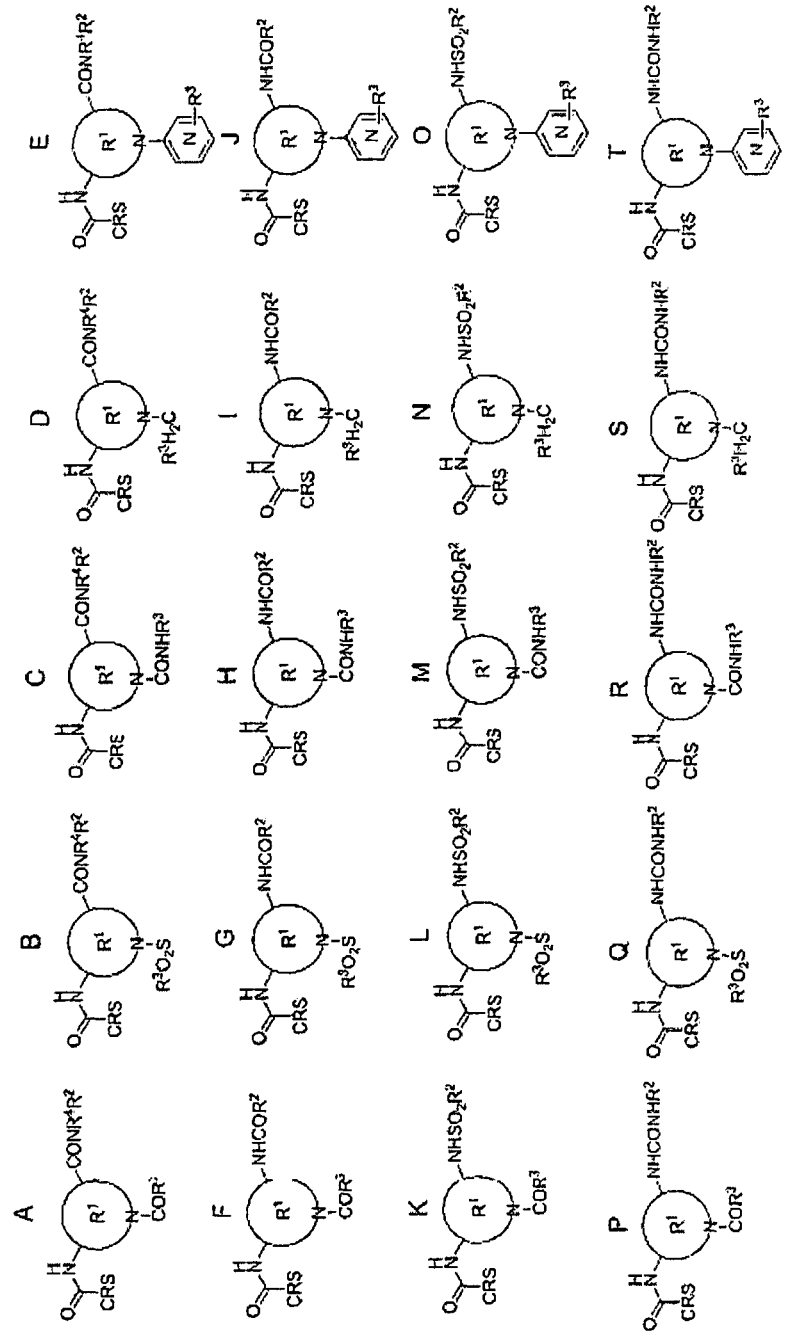
Figure 56:
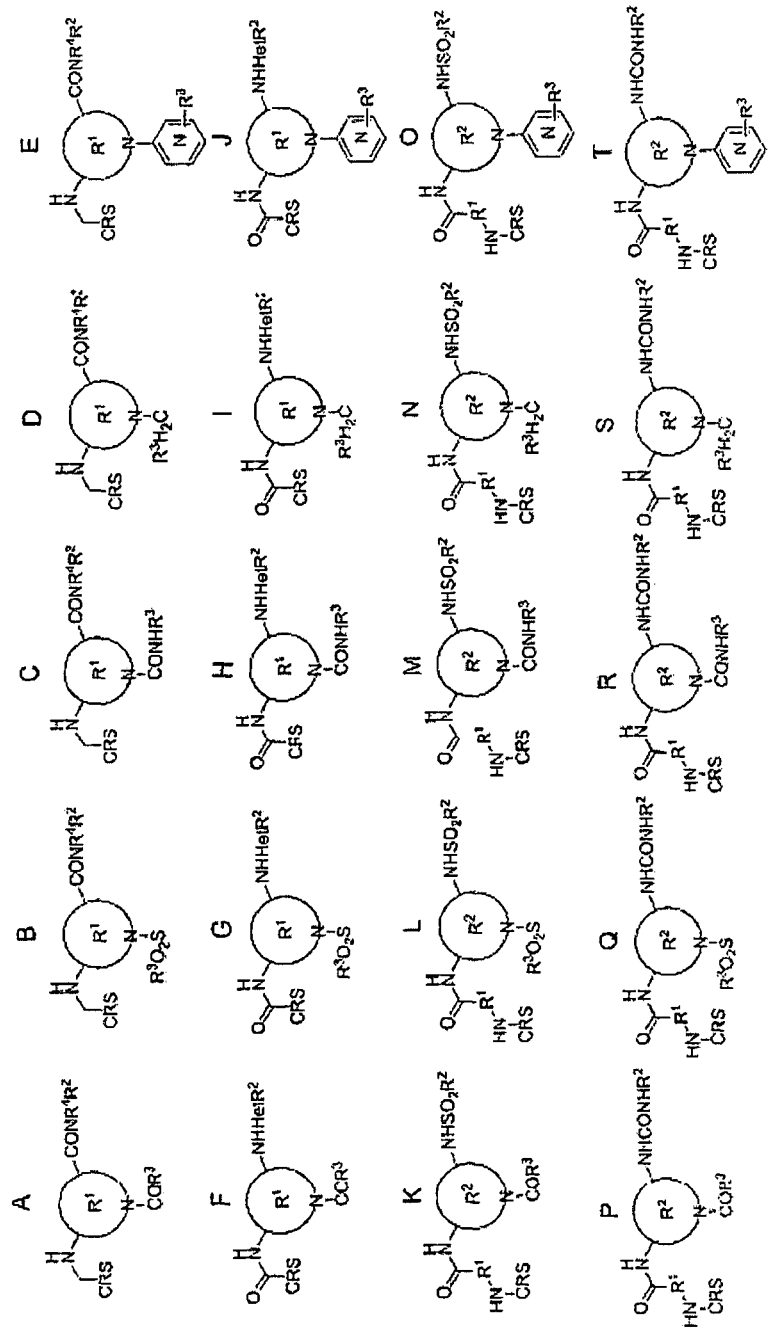
Figure 57:
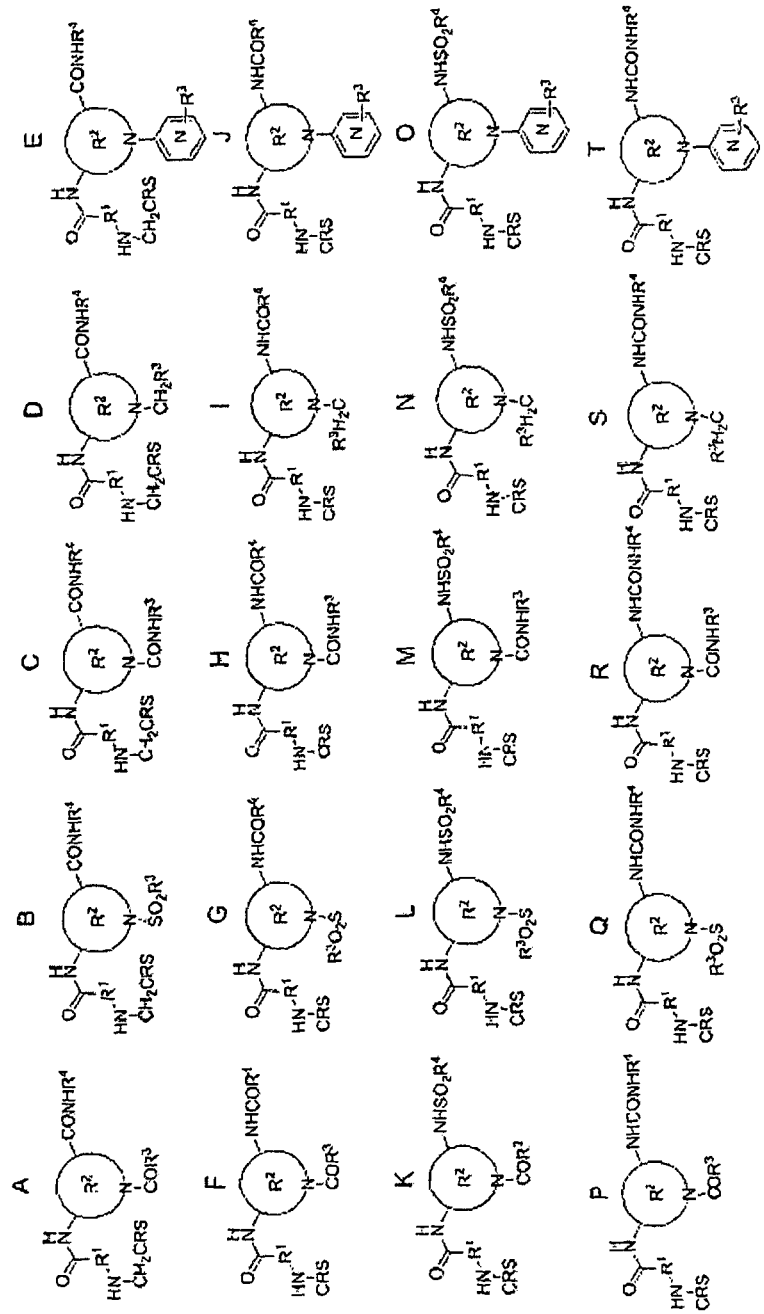
Figure 58:
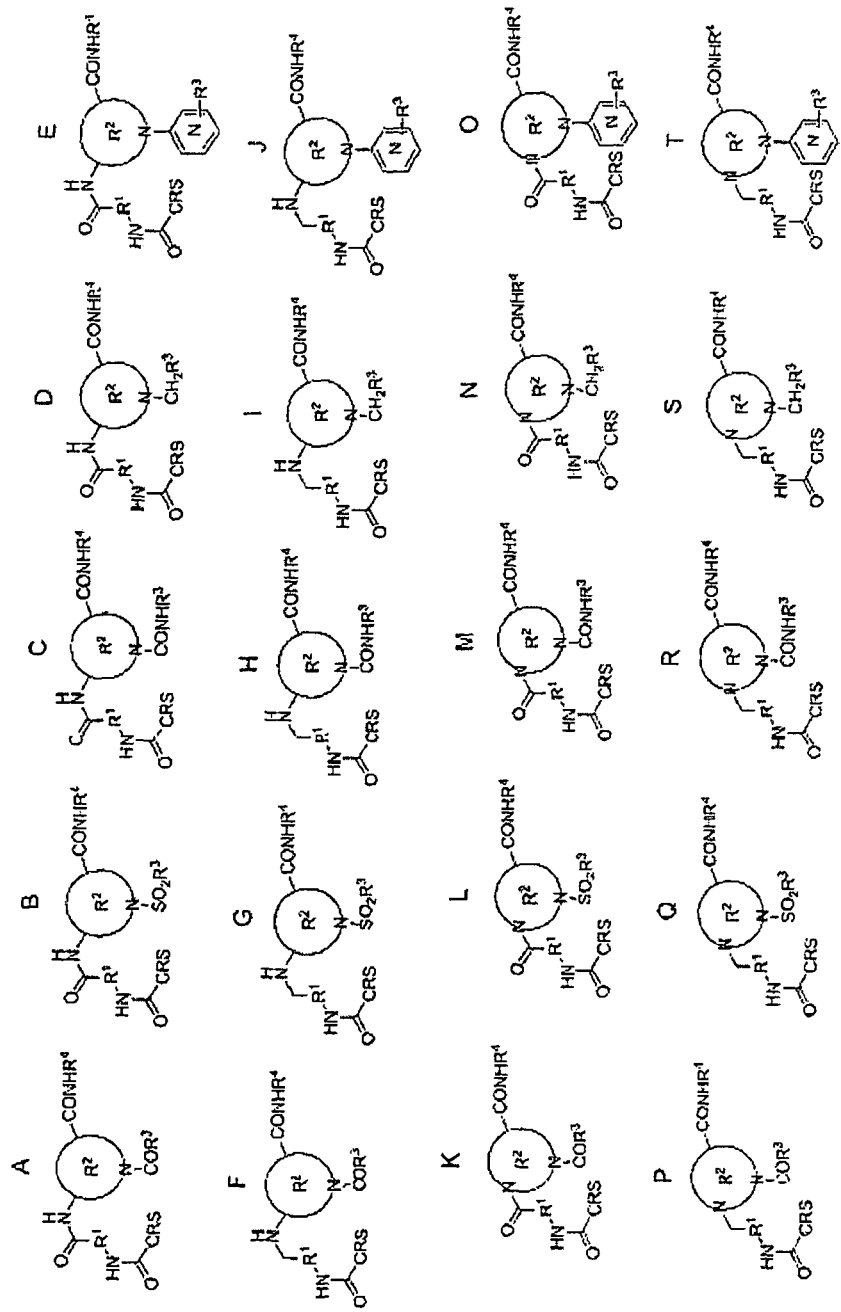
Figure 59:
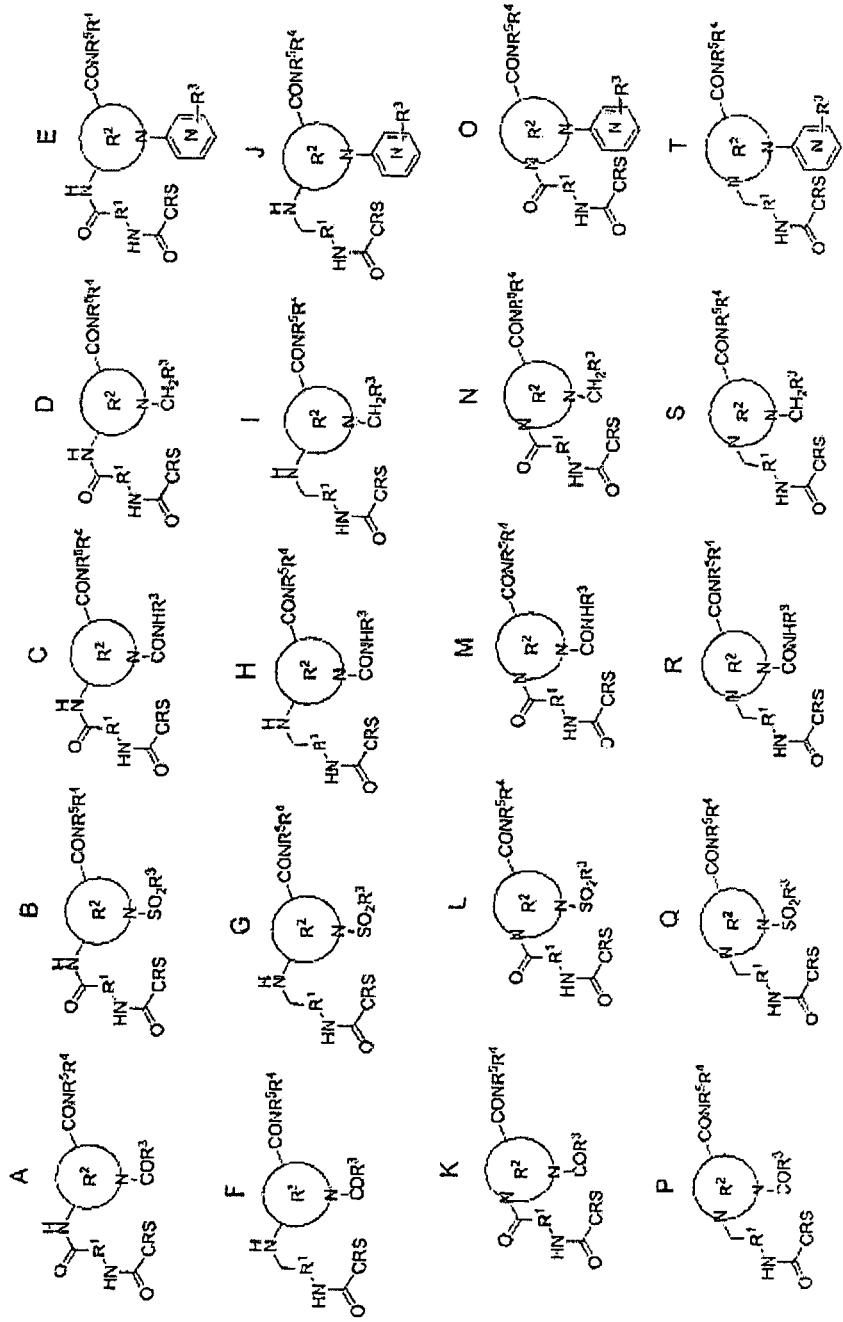
Figure 60:
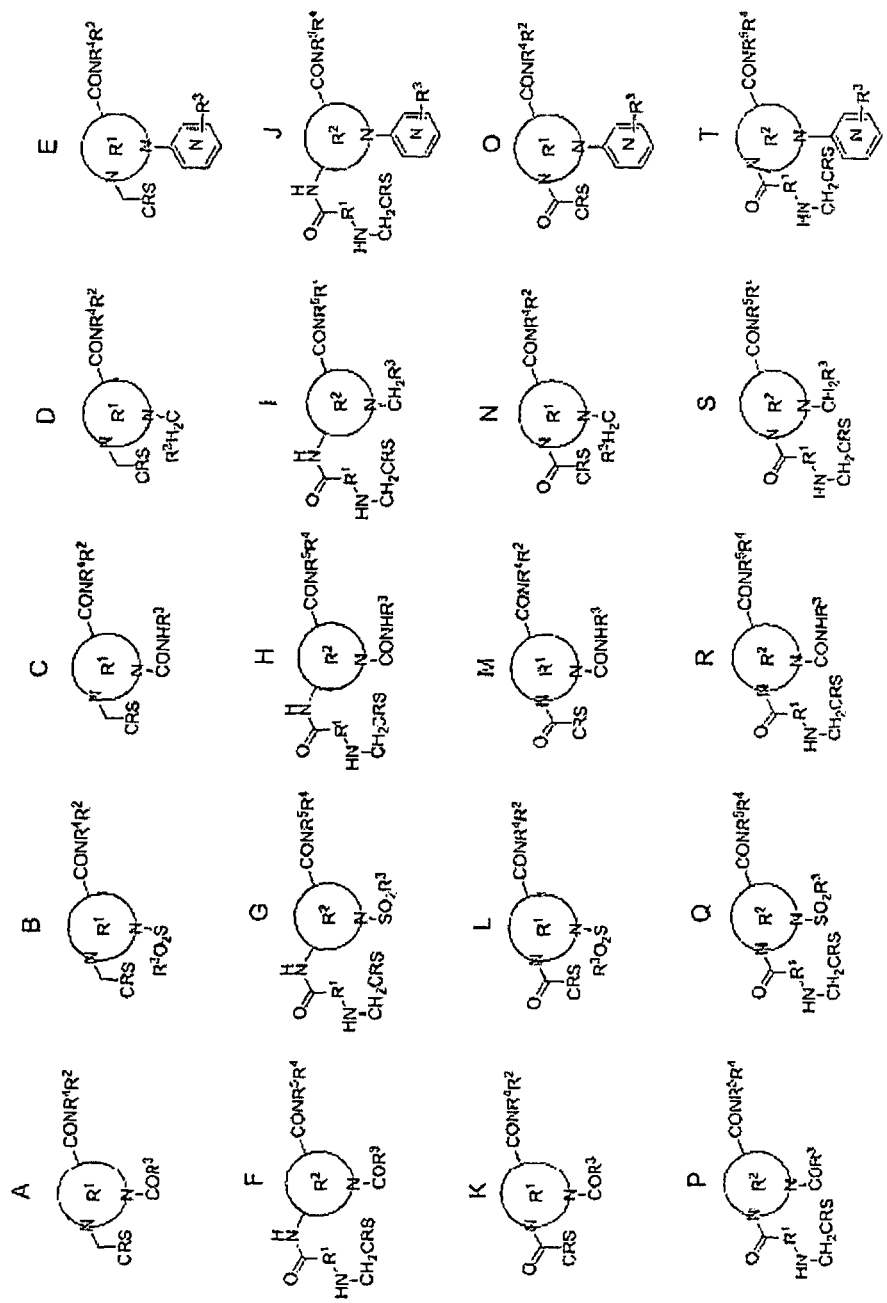
Figure 61:
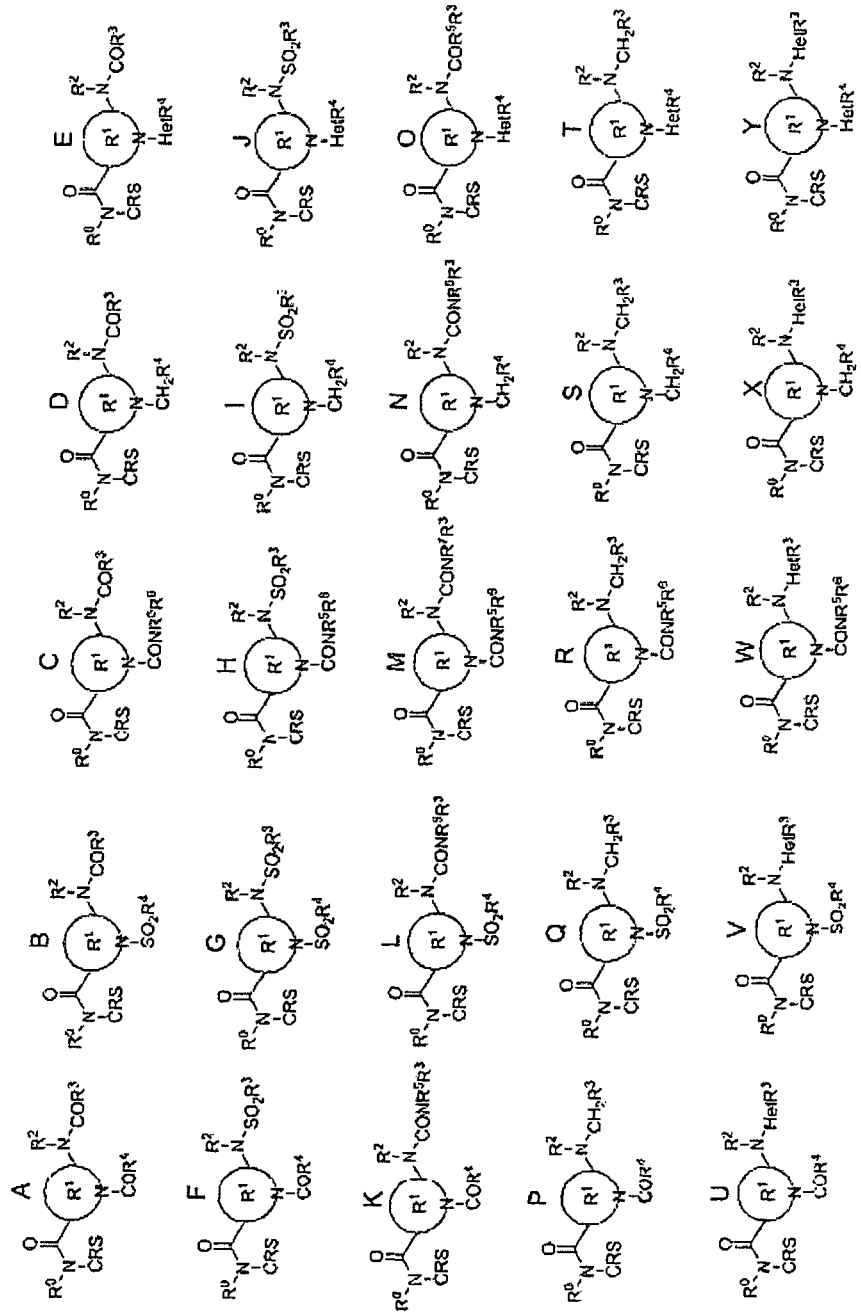
Figure 62:
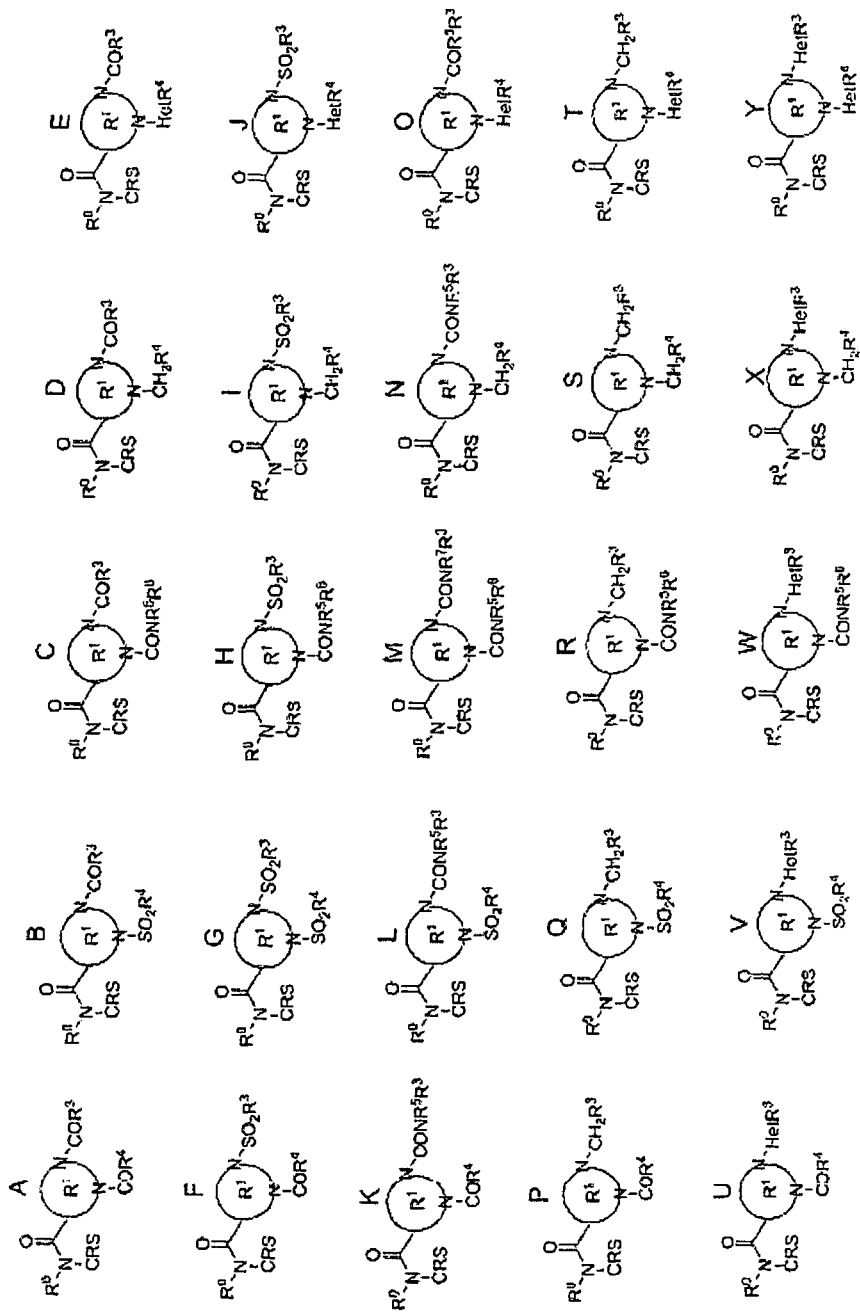
Figure 63:
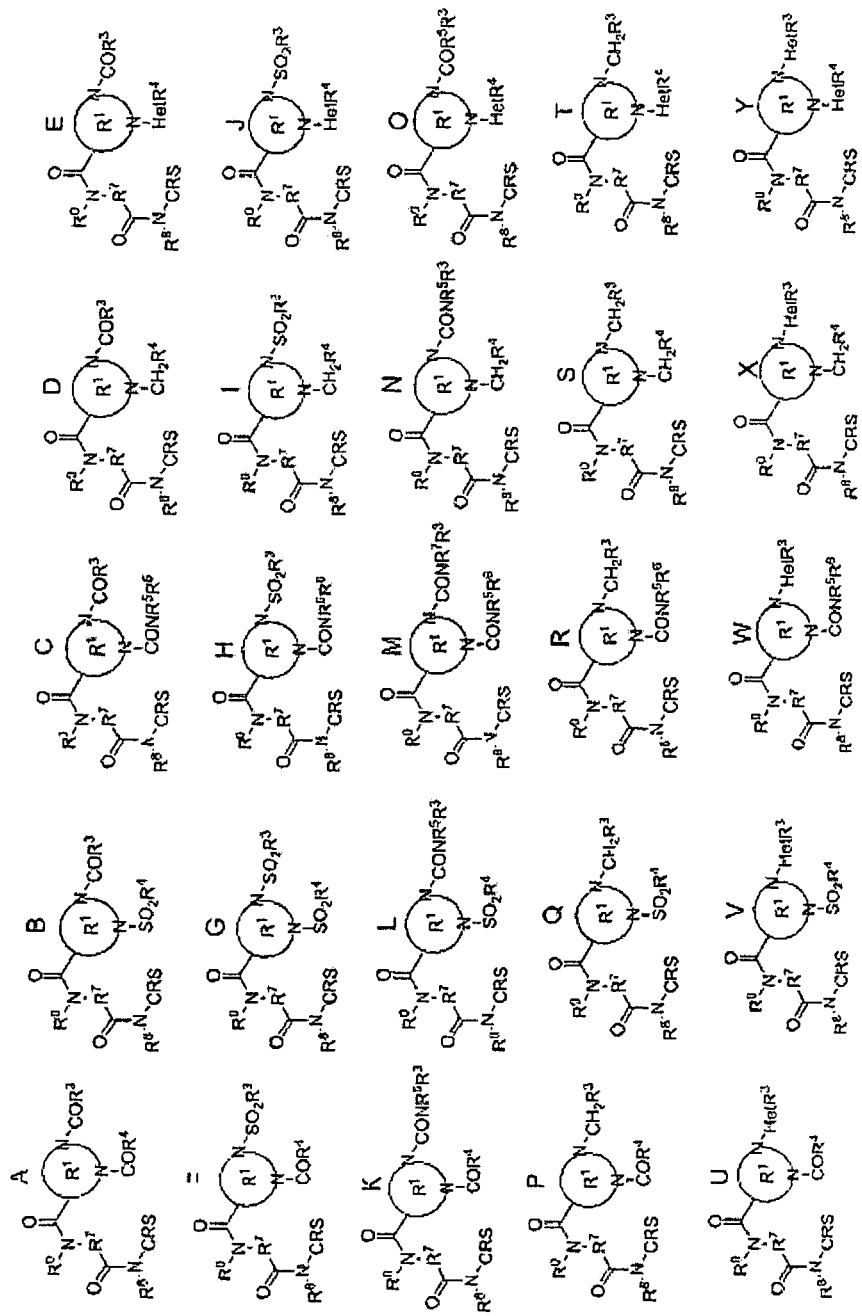
Figure 64:
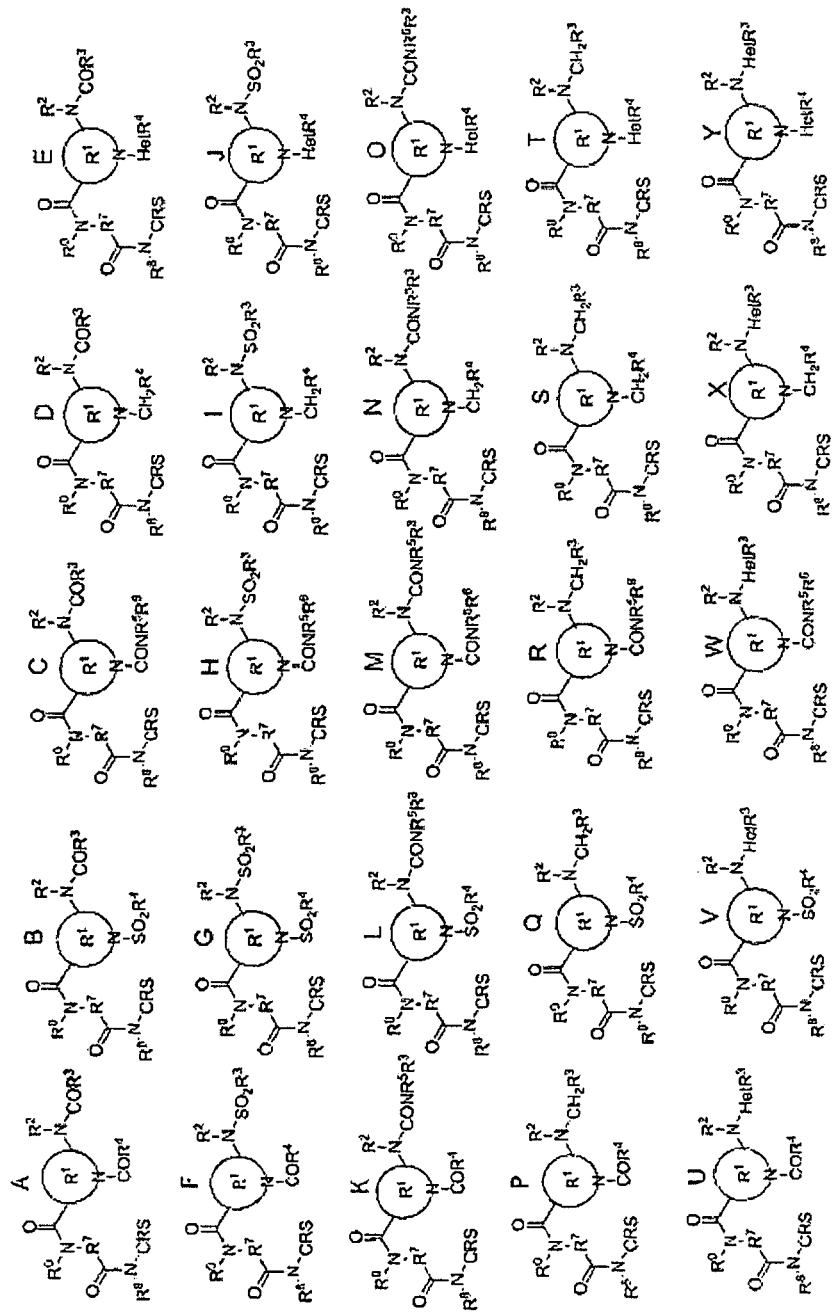
Figure 65:
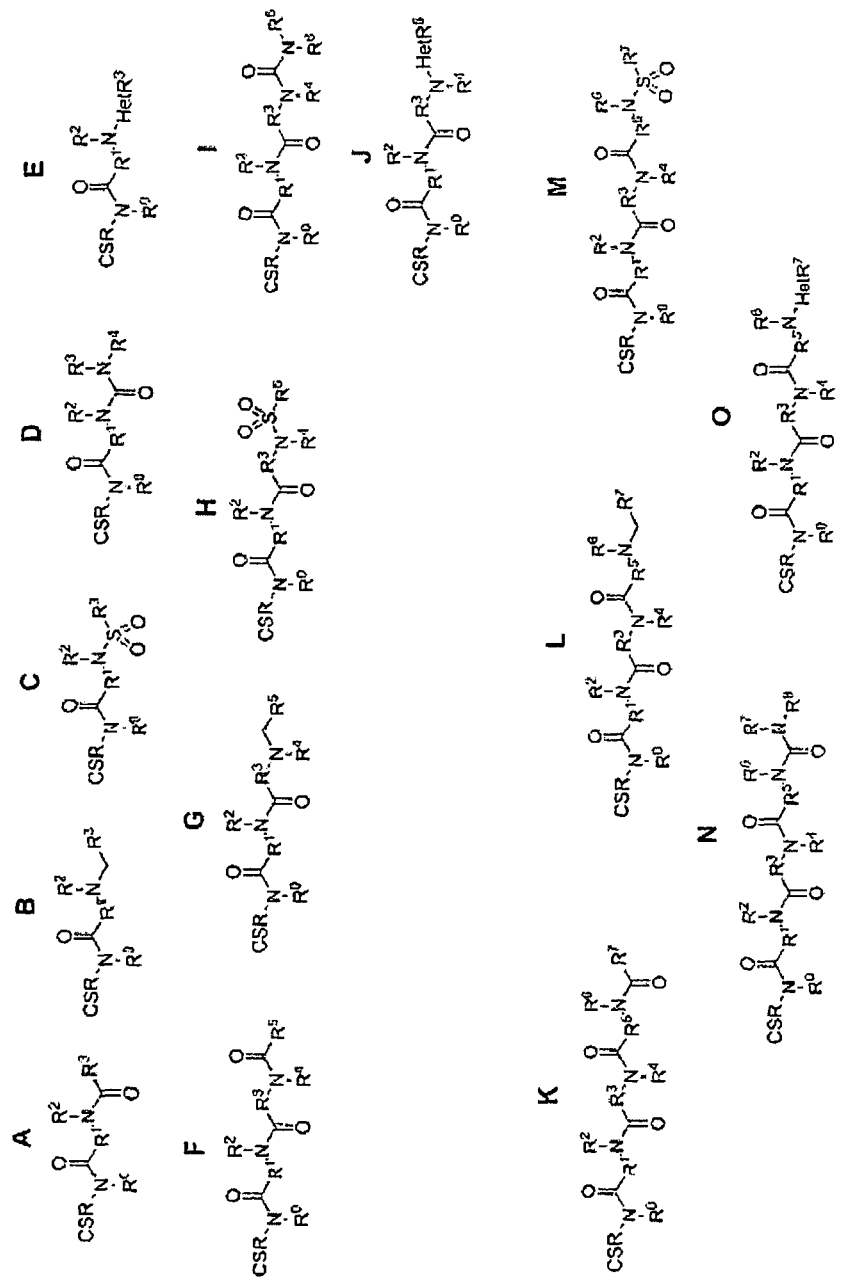

FIGS. 52-54. The figure describes various example product structures formed by use of at least one reactive compound building block. In some examples reactive compound building blocks comprising further reactive groups may react with further reactive compound building blocks to form linear, branched, cyclic, macrocyclic structures or a combination thereof or undergo intramolecular cyclization through the reaction with further reactive groups on R1, including reactive groups not shown but comprised by R1.

FIGS. 55-65. The figure describes various product structures formed by use of 1-5 reactive compound building blocks, for example one reactive compound building block, for example 2 reactive compound building blocks, for example 3 reactive compound building blocks, for example 4 reactive compound building blocks, for example 5 reactive compound building blocks. In some examples reactive compound building blocks comprising further reactive groups may react with further reactive compound building blocks to form linear, branched, cyclic or macrocyclic structures or undergo intramolecular cyclization through the reaction with further reactive groups on Rn-groups, including reactive groups not shown but comprised by Rn-groups (where n is an integer).

The invention may also use more than five reactive compound building blocks, such as six reactive compound building blocks, for example seven reactive compound building blocks, for example eight reactive compound building blocks, for example nine reactive compound building blocks, for example ten reactive compound building blocks. In another embodiment, 11-20 reactive compound building blocks are used, such as 11-15 reactive compound building blocks, for example 16-20 reactive compound building blocks.

Figure 66:
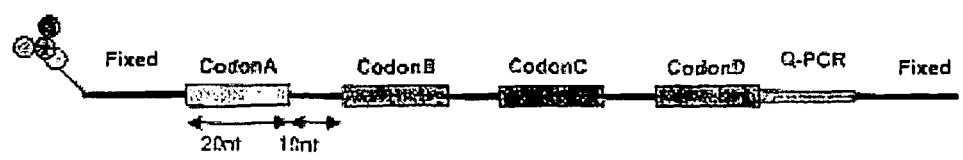

FIG. 66. The figure illustrates a member of a tetramer library consisting of bi-functional molecules each comprising 4 DNA codon elements (tags) covalently linked to the cognate chemical fragments. The overall structure of the bi-functional molecules is shown. Each 20 nt/bp codon is spaced by a 10 nt fixed region and the tags A-D is flanked by fixed sequences useful for amplification by PCR.

Figure 67:
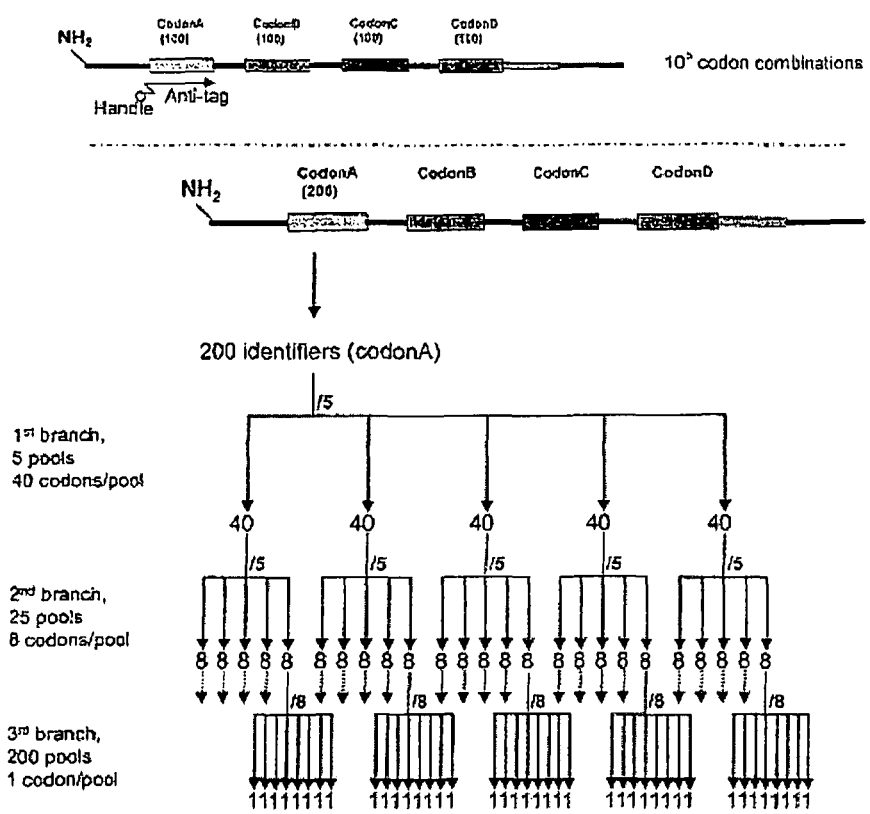

FIG. 67. Panel A illustrates a single stranded identifier oligonucleotide linked to a reactive entity (chemical reaction site). Panel B illustrates iterative steps of subtraction of specifically formed duplexes between the anti-tags supplied and the corresponding identifier codon sequences.

Figure 68:
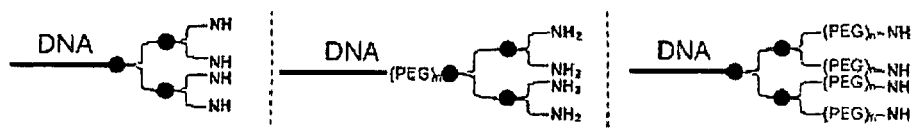

FIG. 68. Illustration of a simple quadruple amino-DNA tag enabling synthesis and display of the same encoded molecule attached to a single encoding tag. It may be desirable to include spacing groups such as polyethylene glycol (PEG) units at any point in the synthesis process (chosen by the experimenter) for improved synthesis and display of the synthetic molecule.

Figure 69:
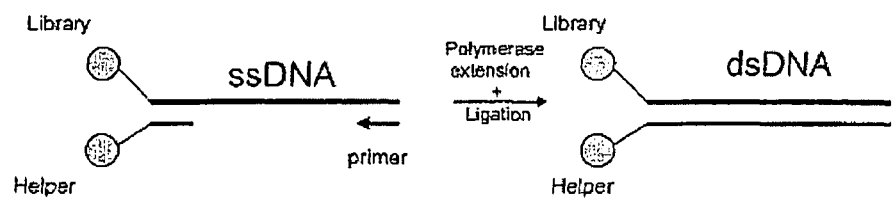

FIG. 69. The figure depicts a scheme for the addition, by hybridization, of a helper molecule covalently linked to a DNA sequence complementary to the region of DNA of the bi-functional library molecule that is proximal to the displayed molecule. Hybridization of a second primer followed by polymerase extention and ligation will produce dsDNA displaying both the encoded library molecule and the helper molecule.

Figure 70:
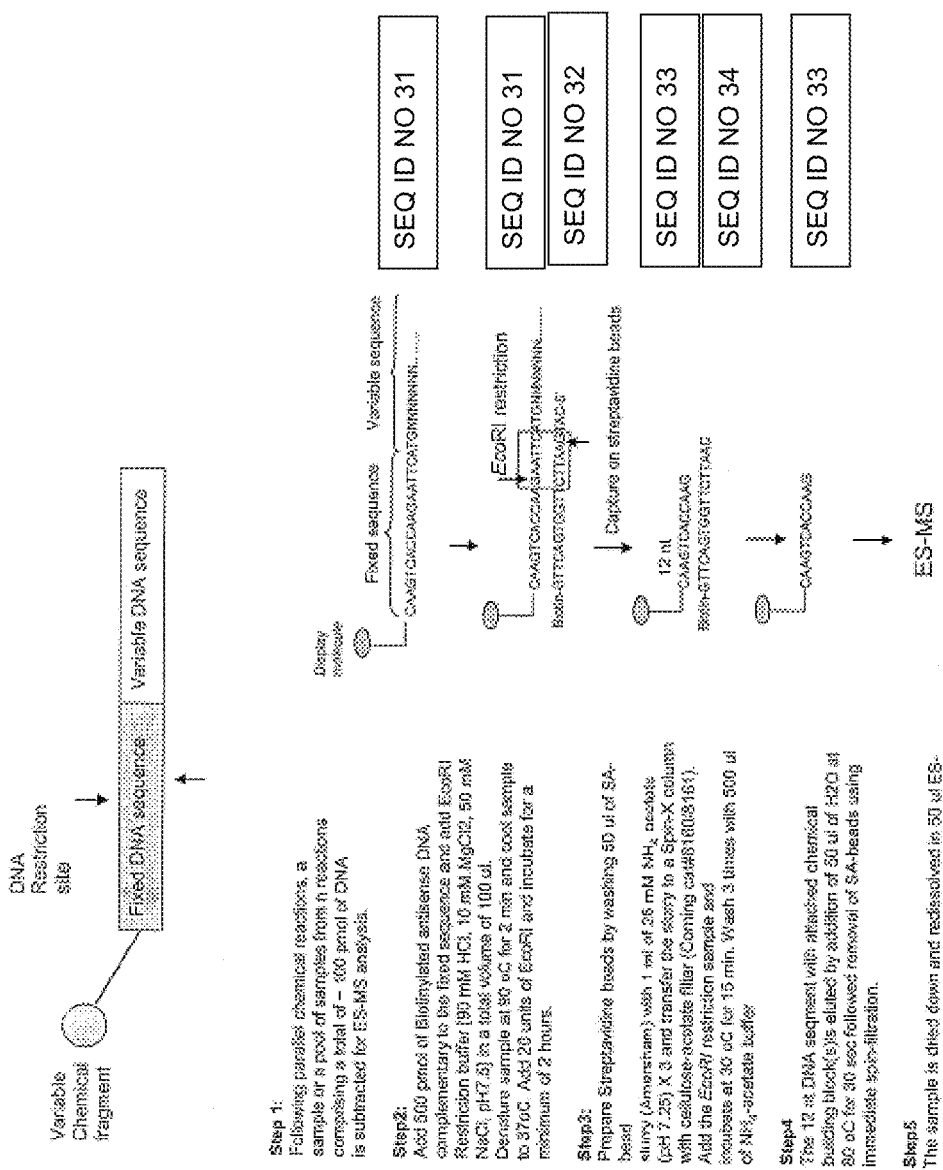

FIG. 70. In a split and mix library generation procedure n chemical reactions are conducted producing n chemical fragments linked to N different tags producing intermediates with a common structure.

Figure 71:
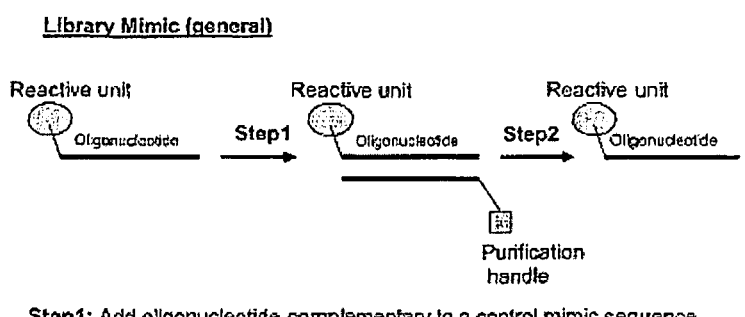

FIG. 71. The figure illustrates an alternative method for the purification of the control mimics in the library is to include a selective cleavable linker connecting a handle for purification and the reactive chemical unit.

Figure 72:
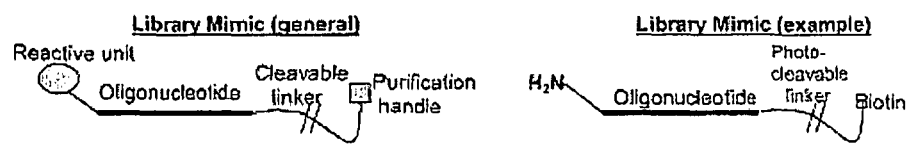

FIG. 72. The figure illustrates an alternative method for the purification of the control mimics in a library. A selectively cleavable linker connecting a handle for purification and the reactive chemical unit is included. The reactive unit (site) is any suitable reactive groups, for example, but not limited to, an amino, thiol, carboxylic-acid or aldehyd-group. The oligonucleotide moiety is optional but provides an excellent handle for molecular weight analysis using MS. The cleavable linker (optionally) is selectively cleavable by any means such as e.g. by enzymatic, chemical or photo-cleavable methods. The purification (optional) may be any unit capable of being selectively recovered.

Figure 73:
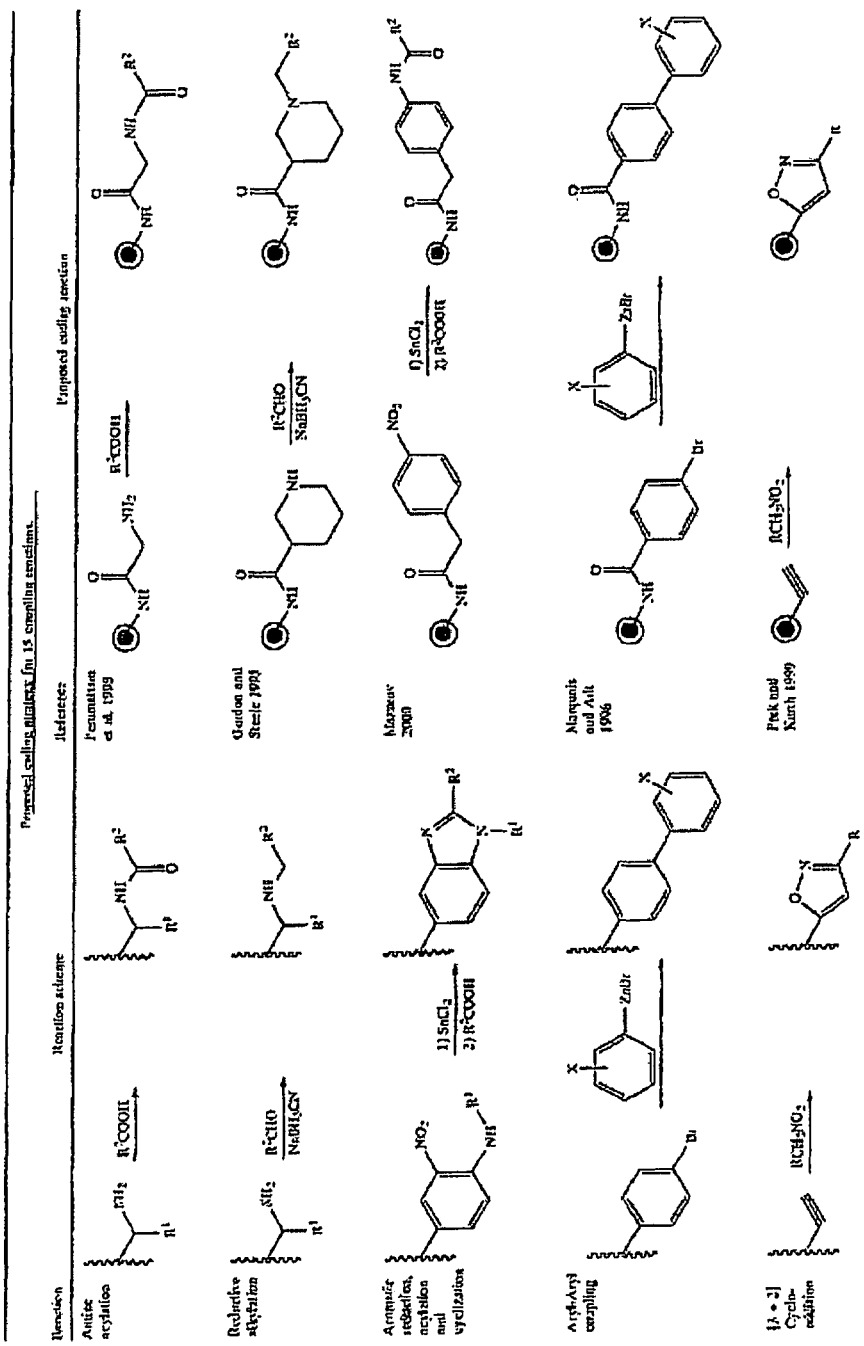
Figure 73:
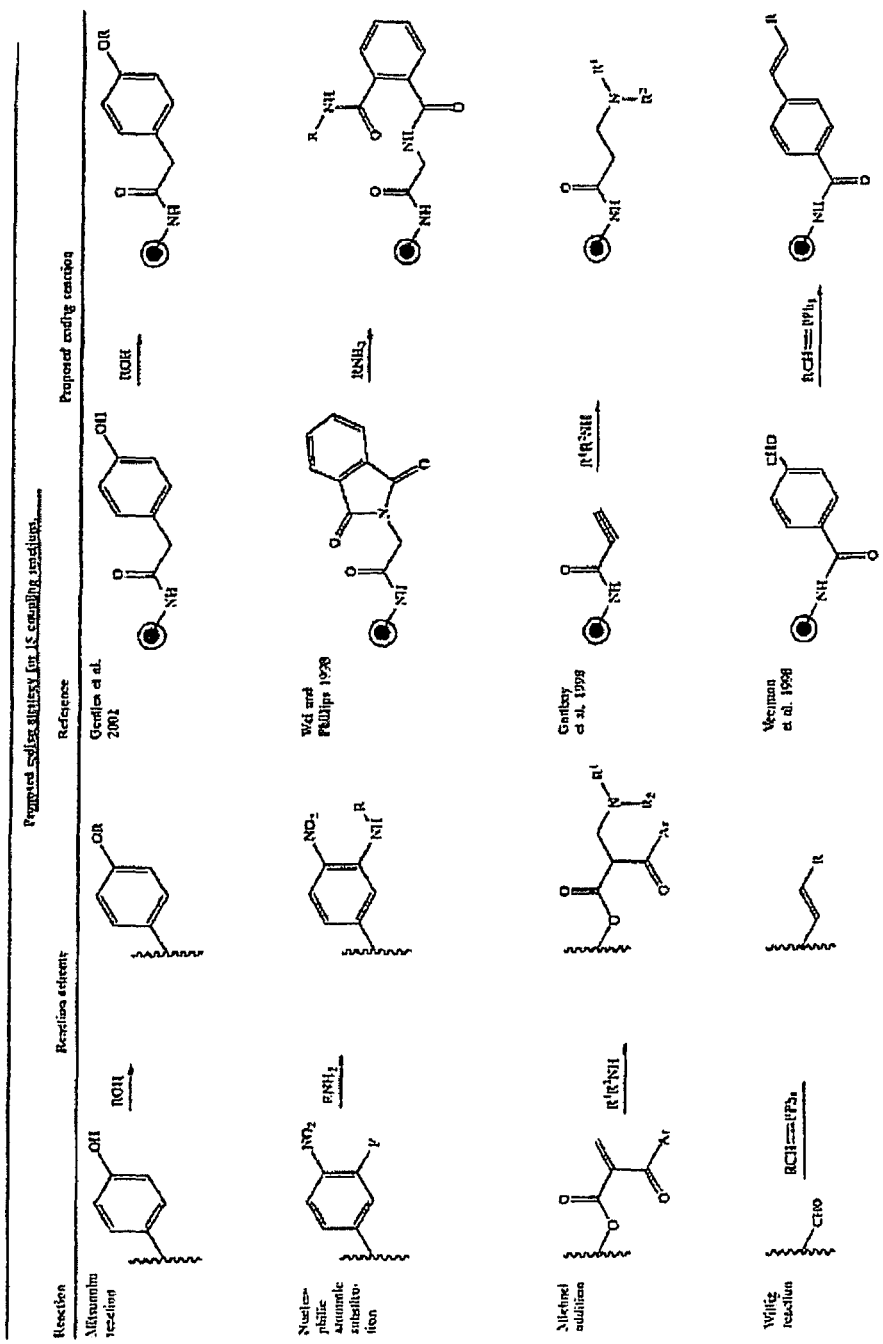
Figure 73:
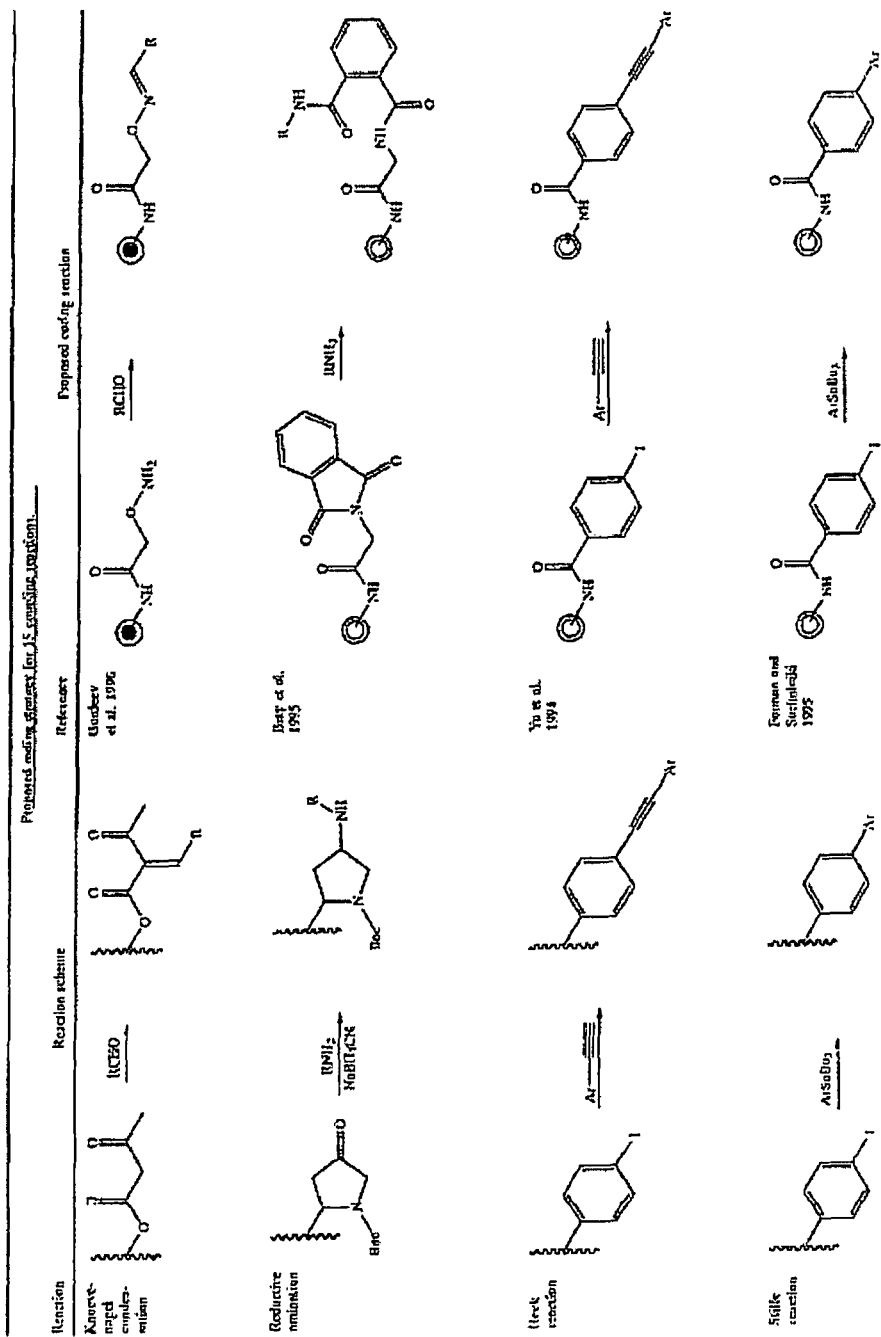
Figure 73:
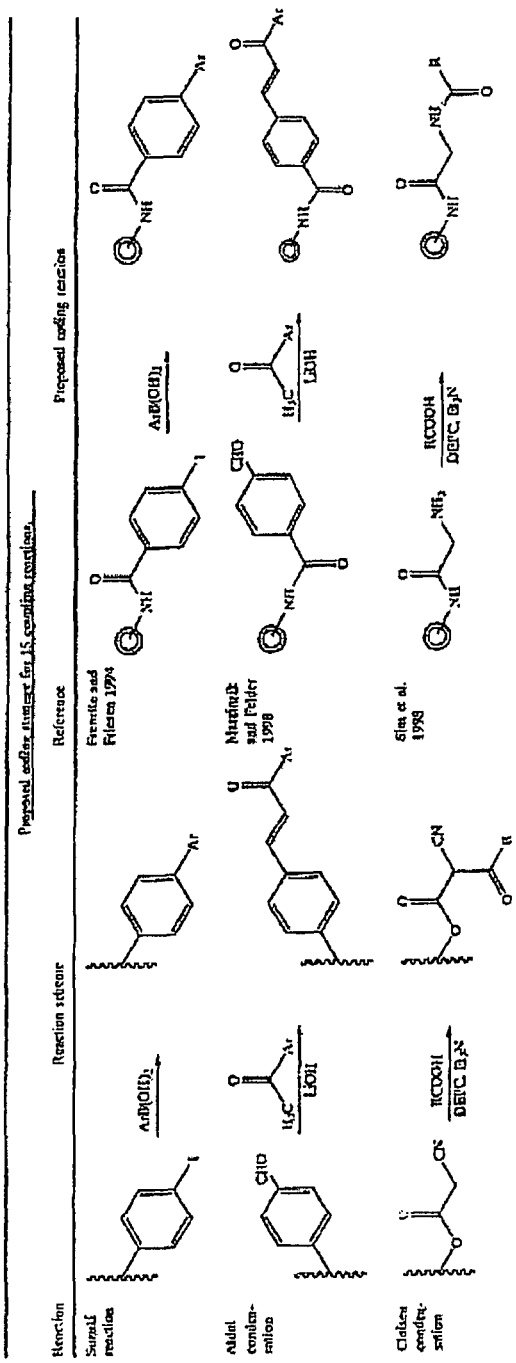

FIG. 73. The figure illustrates exemplary reaction chemistries applicable to the present invention.

Figure 74:
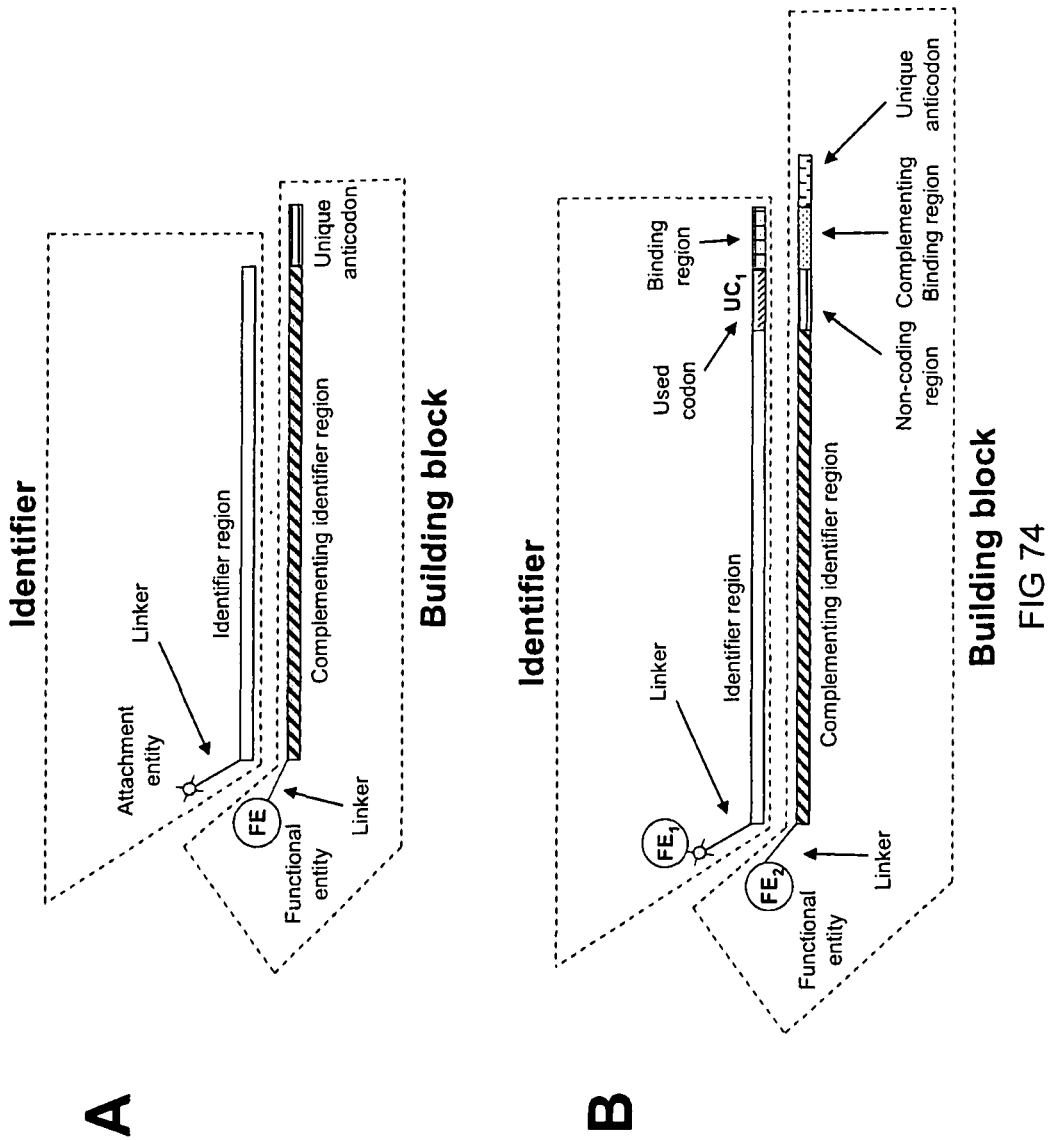

FIG. 74 discloses in panel A a hybridisation product between a nascent bi-functional complex and a building block. The nascent bi-functional complex, for short the Identifier, comprises an attachment entity connected to an oligonucleotide identifier region by a linker moiety. The attachment entity may be a single recipient reactive group having been adapted to receive a functional entity or may be a scaffold structure comprising one or more recipient reactive groups. In panel A the attachment entity is indicated as a scaffold having four reactive groups capable of receiving functional entities.

The building block comprises a functional entity attached to an oligonucleotide which is sufficiently complementary to the identifier region to allow for a hybridisation product to be formed. The functional entity is able to be transferred to the attachment entity through a chemical reaction. The complementing identifier region further comprises a unique codon at the 3' or 5' end thereof. The unique codon identifies the functional entity in an unequivocal way.

Following the formation of the hybridisation product between the identifier and the building block, the functional entity and the unique anti-codon are transferred to the identifier. In an aspect of the invention, the linker connecting the functional entity and the complementing identifier region is cleaved simultaneously with the reaction with the attachment entity resulting in a transfer of the functional entity to the attachment entity. Prior to, simultaneously with or subsequent to the transfer, the transcription of the codon occurs. The transcription is performed by an enzyme capable of polymerisation or oligomerisation of oligonucleotides using a template oligonucleotide to form a complementary stand. Usually a polymerase, such as the Pfu polymerase is used together with suitable dNTPs, i.e. a mixture of ATP, CTP, GTP, and UP, to form the unique codon as an extension of the identifier strand using the unique anti-codon of the building block as template.

FIG. 74, panel B illustrates a typical setup for a second transfer of functional entity. The identifier has been provided with a first functional entity and has been extended by a codon. Furthermore, the codon also comprises a binding region as an extension of the codon. The binding region is usually a constant region transferred to the identifier in the first transfer cycle by the first building block. The identifier forms a hybridisation product with a second building block. The second building block comprises a second functional entity connected to an oligonucleotide sufficient complementary to the identifier region of the identifier to allow for a hybridisation. A part of the complementing identifier region comprises a non-coding region and a region complementing the binding region. The non-coding region opposes the codon transferred in the first cycle and the complementing binding region is complementary to the binding region to allow for a hybridisation which is sufficiently strong for an enzyme to bind to the helix. A second unique anti-codon is attached to the complementary binding region and identifies the second functional entity. The second codon is transferred to the identifier using the second anti-codon as template in the same manner as described above for the first codon.

FIG. 75 illustrates four cycles of functional entity and codon transfer. In the first cycle, a hybridisation product is formed between the identifier and building block. The hybridisation product ensures that the functional entity and the scaffold are brought into close spatial proximity, thus increasing the probability that a reaction will take place. The formation of a duplex between the two oligonucleotides also provides a binding region for a polymerase. In the presence of a polymerase, a mixture of dNTPs and a suitable puffer such as an aqueous solution containing 20 mM HEPES- KOH, 40 mM KCl and 8 mM MgCl$_2$ and a pH adjusted to 7,4, the unique anti-codon (UA$_1$) is transferred to the identifier as a codon.

After the transfer of functional entity and codon, respectively, the spent building block is separated from the identifier by increasing the stringency. Usually, the stringency is increased by a increasing the temperature, changing the pH or by increasing the ionic strength. After the rupture of the duple helix structure, the identifier is recovered. In one aspect of the invention the identifier is immobilized to ease the separation from the spent building block. In another aspect the spent building block is degraded chemically or enzymatically. Following the recovery of the identifier a new cycle can be initiated by contacting the identifier with a further building block.

The final product after four cycles of transfer is a bi-functional complex, which comprises a reaction product at one end and an encoding region at the other. The reaction product comprises constituents from the transferred functional entities and the initial scaffold. The encoding region comprises a genetic code for which entities that have been transferred in which order. Thus, the synthetic history may be decoded from the encoding region.

Figure 76:
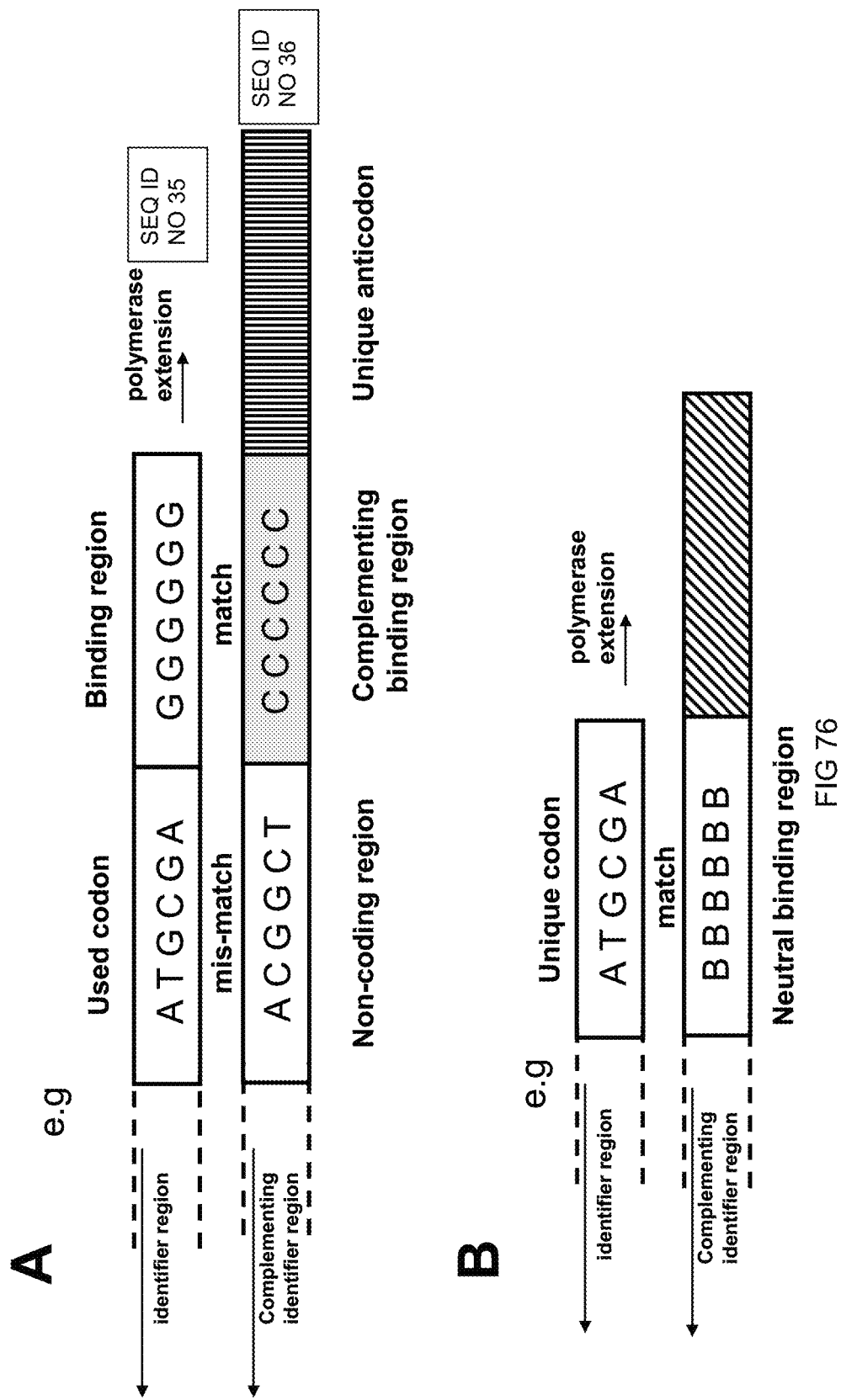

FIG. 76 shows examples of the design of the coding area. Panel A, depicts a detailed view of an example of a design according to FIG. 1, panel B. The unique codon transferred in a first cycle is opposed by a partly mis-matching region. To compensate for the decrease in affinity a binding region is following the codon. The binding region is opposed by a matching complementary binding region of the building block.

In FIG. 76, panel B the unique codon incorporated in a first cycle is opposed by a second building block having incorporated in the complementing identifier region a neutral binding region. The neutral binding region is not capable of discriminating between varieties of unique codons, but is able to show some kind of affinity towards the each of the codons. Usually, the neutral binding region comprises one or more universal bases and more preferred the neutral binding region comprises a sequence of universal bases opposing at least a part of the codon region on the identifier.

Figure 77:
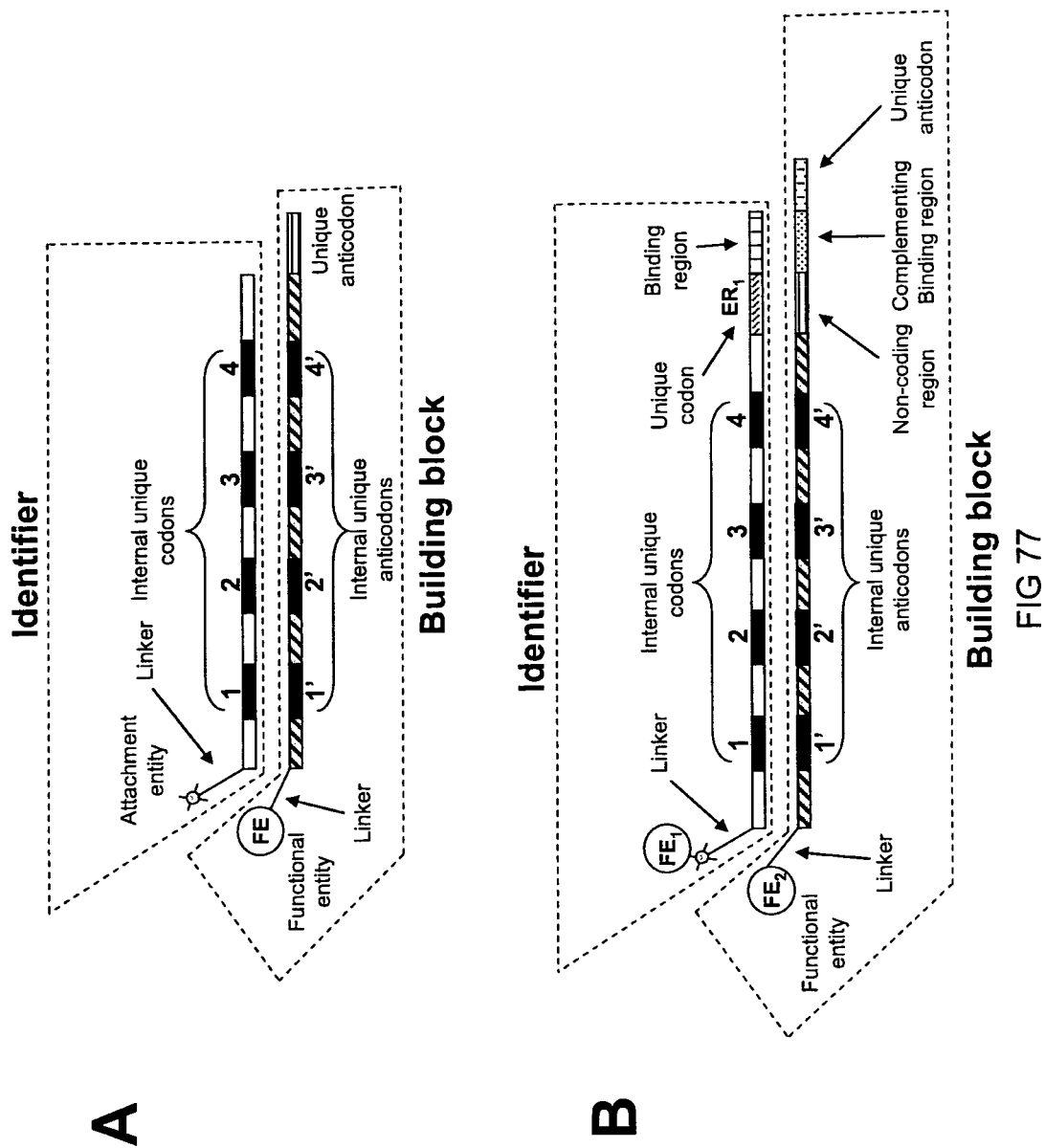

FIG. 77 shows a hybridisation product between an identifier and a building block wherein the identifier has internal codons and the building block has corresponding anti-codons. The identifier region and the complementing identifier region can also contain specific unique codons and anti-codons, respectively.

The use of internal codons is of particular importance when several rounds of selection are anticipated, especially when the encoded molecule is formed from a PCR product of a previous round. The internal anti-codons in the building block may completely or partly match the identifier sequence or may comprise one or more universal bases to provide for affinity but not for specificity. The role of the internal unique codons is only to guide the annealing between the identifier molecule and the building block molecule. The correct encoding is taken care of by the unique codons which are created in the extension process. These unique codons are passed on to the next generation of molecules and used to decode the synthetic history of the displayed molecules. This system will not be totally dependent on an accurate encoding function by the internal unique codons in order to pass the correct genotype to the next generation of identifier molecules.

In panel A the hybridisation product provides for a spatial proximity between the functional entity and the attachment entity, thus increasing the probability that a reaction occurs. The unique codon templates the codon on the identifier sequence by an enzymatic extension reaction. In panel B a binding region is introduced between each unique coding sequence to provide for affinity of the two strands to each other even though one or more mis-matching bases appear in the codon:non-coding domain of a previously used codon.

Figure 78:
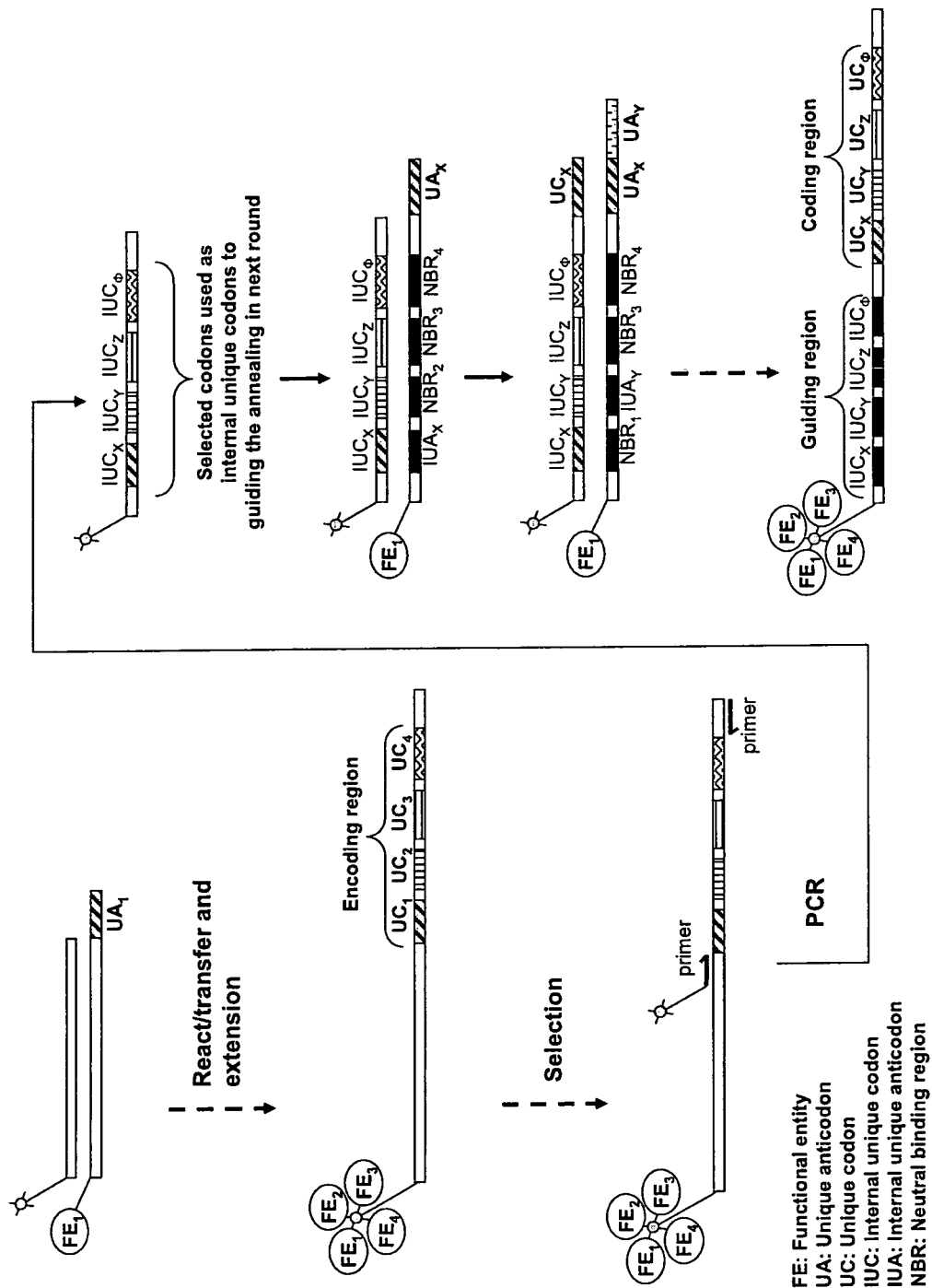

FIG. 78 shows an embodiment useful when an amplification step is involved between selections. Initially, a library of complexes is produced as depicted in FIG. 75. The library of the complexes may be subjected to a selection process. The selection process may involve presenting the molecule on the complex to a target and subsequent selecting the molecules which shows a desired interaction with the target. It may be advantageously to use relatively mild conditions during the selection process, to obtain a sub-library. The sub-library may be decoded to obtain information on the synthetic history for the entire sub-library. However, it is usually preferred to reduce the sub-library further before a decoding is performed.

The sub-library may be reduced by subjecting it to the target again and use more stringent conditions. However, to obtain a higher number of each of the members of the sub-library before a second selection, it is generally preferred to amplify the complex. Thus, a primer which is loaded with a scaffold is initially annealed to a primer site at one end of the encoding region. Subsequently a transcript is formed. A reverse primer is preferably present to obtain a duple stranded PCR product having a scaffold attached thereto.

This PCR is the basis for the generation of en amplification of the sub-library. The identifier sequence is segregated into a number of internal unique codons, abbreviated IUC in the drawing. The number of the IUCs corresponds to the number of functional entities participating in the formation of the molecule. The sequence of the IUCs expresses the identity of the individual functional entities and the order of the IUCs indicates the order of reaction of the functional entities. Preferably, a primer region is presented adjacent to the sequence of IUCs to allow for a later amplification of the nucleic acid sequence.

The sub-library is contacted with a plurality of building blocks comprising a transferable functional entity and an internal unique anti-codon (IUA) complementary to at least one of the IUCs. The complementing identifier region is provided with sufficient complementarity to provide for a hybridisation with the oligonucleotide identifier region. In a preferred embodiment the IUCs not identifying a functional entity to be transferred is opposed in the complementary identifier region with a neutral binding region. As mentioned above the neutral binding region may comprise universal bases, i.e. bases that have the ability to be paired with two or more of the naturally occurring nucleobases. Adjacent to the region comprising specific base-pairing sequences and non-specific base-pairing sequences, i.e. the complementary identifier region is a unique anticodon (UA). The UA comprises the same information as the IUA of the complementing identifier region, typically the UA and the IUA has the same sequence on nucleotides.

The transfer step and the reaction step are conducted in several cycles as described above to form a bi-functional complex. In FIG. 78 four cycles are performed, however, it will be appreciated that less than cycles, such as 3 or 2 cycles can be performed to produce a reaction product comprising constituent from 3 or 2 functional entities respectively. Also more, than four cycles may be performed, such as 5 to 20 to form a more diverse library of molecules. The complexes resulting form the cycles are a reaction product between the functional entities and the scaffold, and an oligonucleotide. The oligonucleotide can be divided into a guiding region, that is, the region that guided the annealing of the individual building blocks, and an encoding region, which comprises the unique codons which have been transferred from the building blocks to the identifier.

Using the above encoding method, allows for the amplification of more and more focused sub-libraries to obtain a sufficient amount of material to allow decoding.

The encoding method shown in FIG. 79 can create both monomer and polymer encoded molecules. Panel A: Complex reaction products can be created using an attachment entity which has reacted with multiple functional entities. Panel B: Polymers can be created using one attachment entity with one reactive group allowing attachment with a functional entity having at least two reactive groups.

Figure 80:
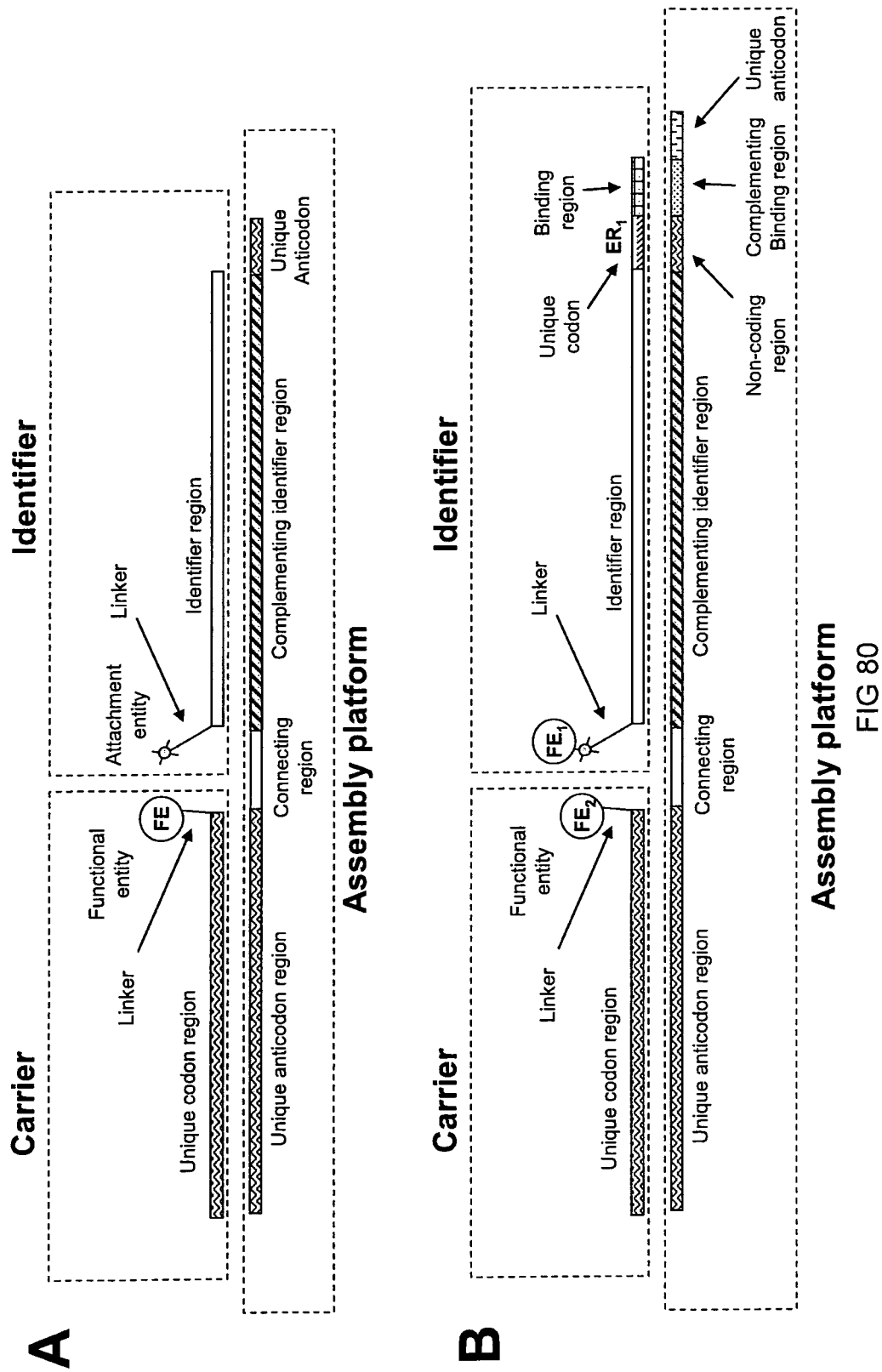

FIG. 80 illustrates a three strand assembly procedure for the encoding by extension principle. A: The identifier and building block can be assembled on an assembly platform. This assembly platform contains a unique anticodon region and a unique anticodon where these two elements are directly linked through their sequences. There may be a connecting region linking the unique anticodon region together with the complementing identifier region. B: Describes all the components of the identifier, building block and the assembly platform used in the consecutive reaction, where the identifier also contain a unique codon and a binding region and the assembly platform also contains a non-coding region and a complementing binding region.

Figure 81:
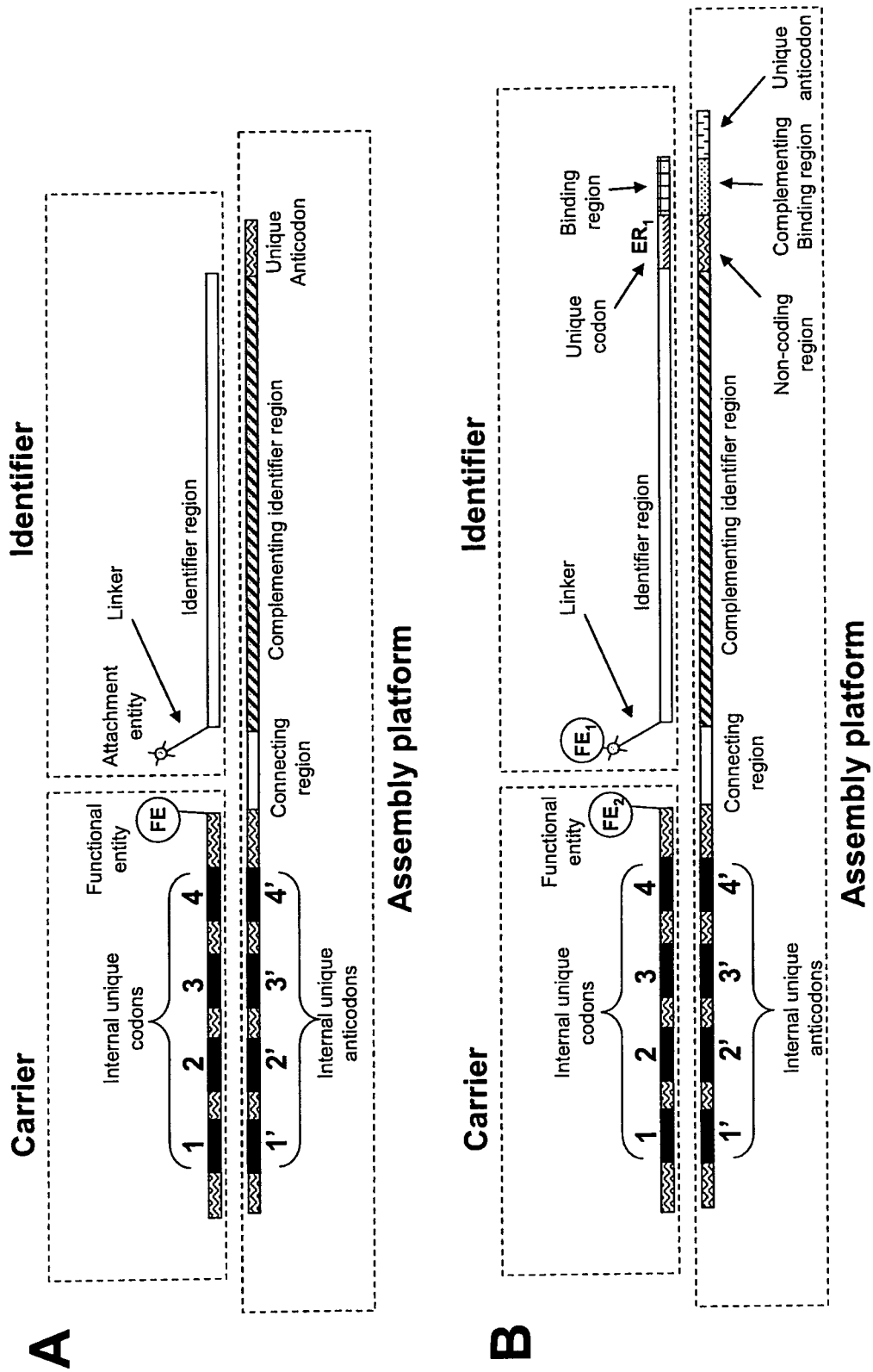

In FIG. 81 it is shown that internal codons can also be used for the three-strand assembly principle. This will be useful when selection will be performed in multiple rounds with intermediate amplification steps.

FIG. 82 shows a solid-phase three-strand displayed-molecule synthesis. The assembly platform molecule is attached to a solid support to allow sequential attachment of building blocks to the attachment entity. Different libraries of assembly platform molecules, which is extended with suitable non-coding regions and complementing binding regions, can be used in each step in separate vials. This will allow the use of identical building block and identifier molecules in each step.

Figure 83:
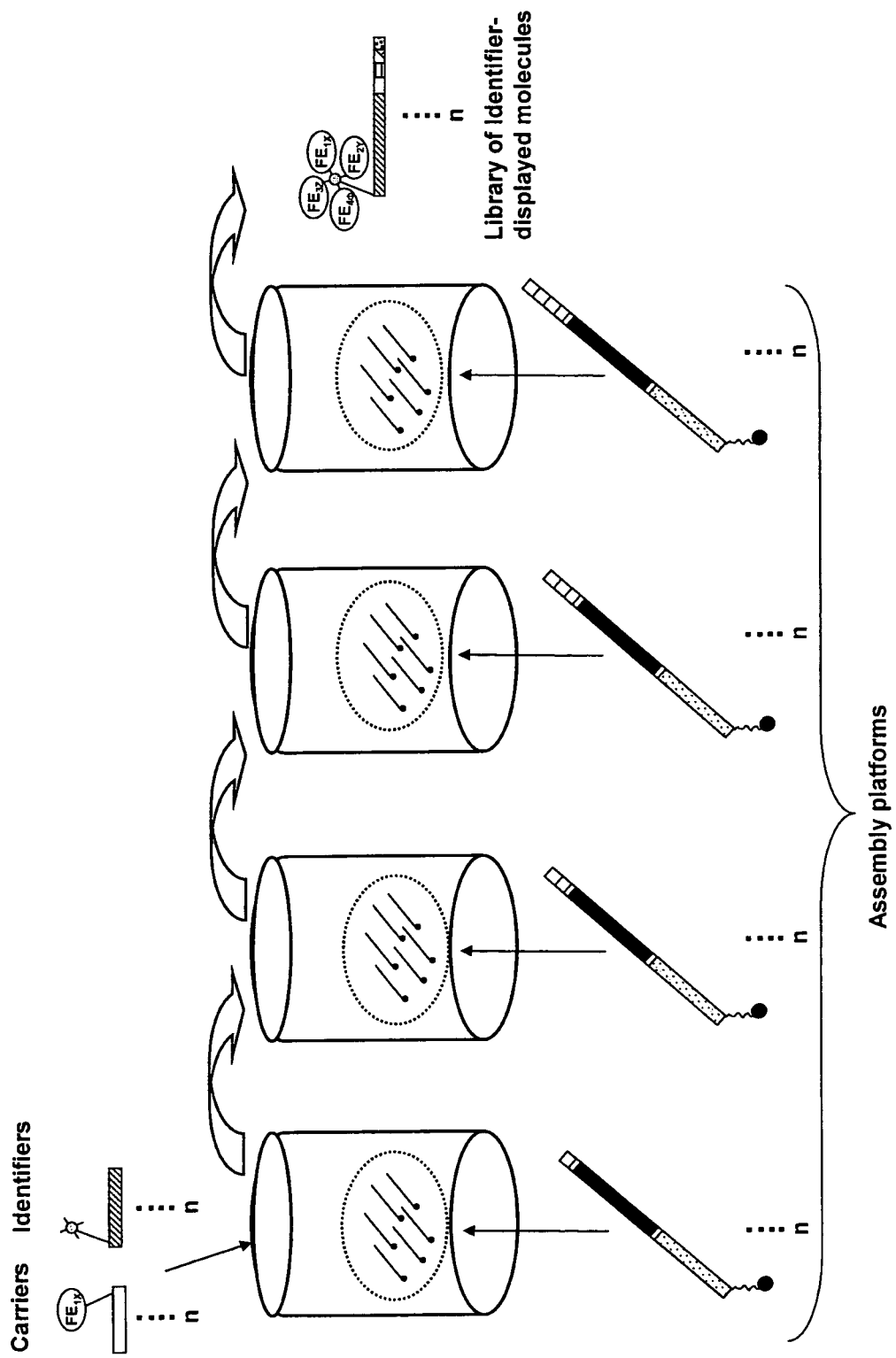

FIG. 83 shows the sequential transfer/extension using the assembly platform principle. Each well contains a library of platform molecules. The platform molecule is extended with one unique anticodon in the subsequent wells. A library of identifier and building block molecule is added to the first well which allows specific annealing and transfer of functional entities. The reaction mixture is the transferred to the next wells which finally generates the identifier-displayed library.

Figure 84:
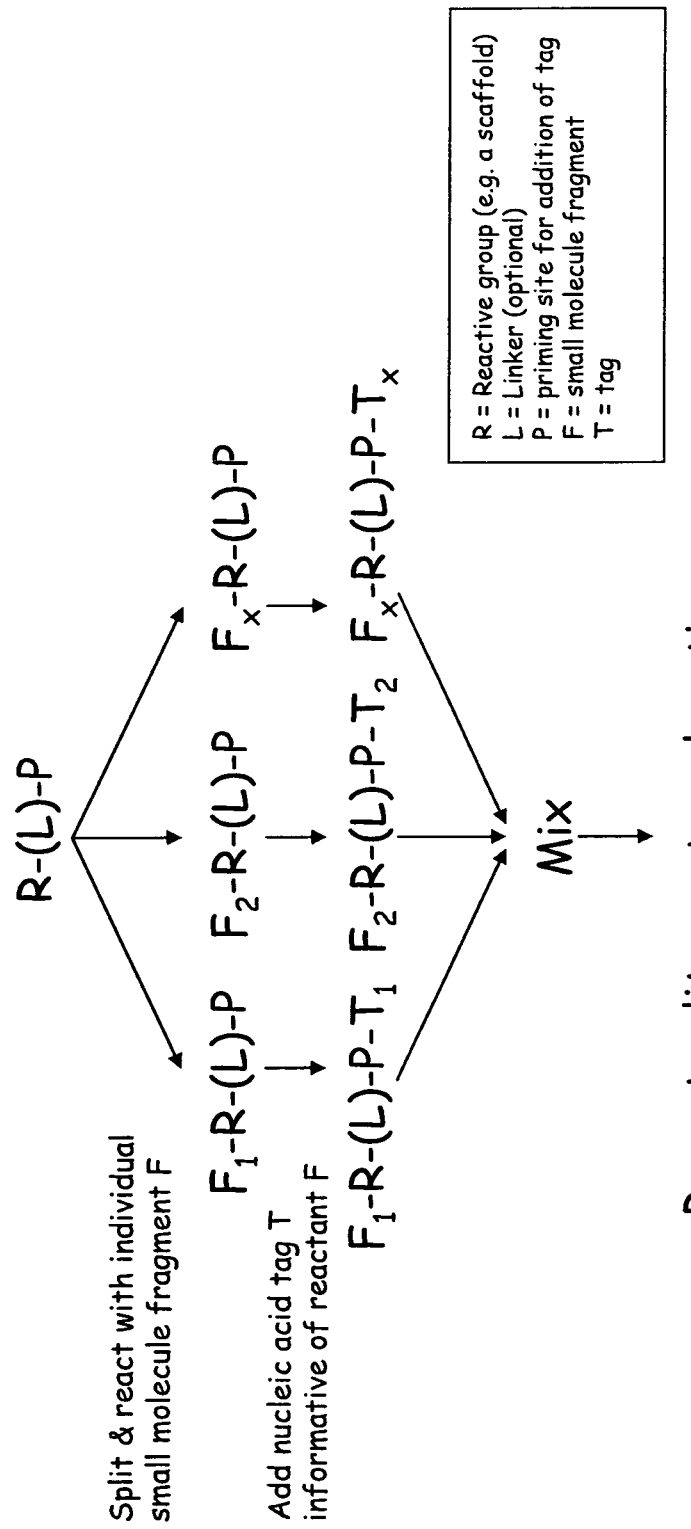

FIG. 84 discloses a general scheme for alternating parallel synthesis of combinatorial libraries. In a first step a nascent bi-functional molecule is provided. The nascent bi-functional molecule comprises as one part of the molecule a reactive group, which may appear on a chemical scaffold, and some times referred to herein as a chemical reactive site. Another part of the bi-functional molecule comprises a priming site for addition of a tag. The priming site may be a 3'-OH group or a 5'-phosphate group of a nucleotide in case the tag is a nucleotide. The chemical reactive site and the priming site may optionally be spaced by a linking group. In the event that the linking group is resent it may be a nucleotide or a sequence of nucleotides. The spacing entity may further comprise a hydrophilic linker, such as a polyethylene or polypropylene, to distance the chemical reactive site from the nucleotide. Also comprised in the linking moiety may be a selective cleavable linker that allows the experimenter to separate the molecule from the coding part.

The nascent bi-functional molecule is divided into a plurality of compartments, usually wells of a microtiter plate or similar equipment that allow easy handling of multiple spatially separated containers. Each of the compartments is reacted with a specific small molecule fragment, also referred to herein as a reactive compound building block. Thus, in a first compartment, the nascent bi-functional molecule is reacted with a first small molecule fragment ($F_1$), in a second compartment; the nascent bi-functional molecule is reacted with a second small molecule fragment ($F_2$), etc. The number of compartments may in principle be indefinite, however, for practical reasons; the number is usually between 5 and 5000, such as 10 and 500. In each of the compartments the small molecule fragments may be identical or different as the case may be. In each compartment, one, two, or more reactive compound building blocks may participate in the reaction. After the reaction between the drug fragment and the nascent bi-functional molecule has occurred in each compartment, a tag is added, said tag identifying the small molecule fragment. In certain aspects of the invention, the tag is a nucleic acid. Thus, in the first compartment, a first nucleic acid tag ($T_1$) is added to the priming site of the reaction product, in the second compartment, a second nucleic acid tag ($T_2$) is added to the priming site of the second reaction product, etc. Various methods for enzymatic encoding are contemplated and discussed herein. Following the enzymatic addition of the tags in each of the compartments, the contents of the compartments are collected.

In a second round the mixture of bi-functional molecules is split into compartments again. The number of compartments of the second round need not be the same as the number of compartments in the first round. In each compartment the products of the previous round serves as the nascent bi-functional molecule. Thus, a reactive group appearing on the reaction product between the scaffold and the small molecule fragment of the first round is reacted with one or more small molecule fragments of the second round. Thus, in a first compartment, the mixed reaction products of the first round are reacted with a first small molecule fragment ($F_1$), in a second compartment, the mixed reaction products of the first round are reacted with a second small molecule fragment ($F_2$), etc. The small molecule fragments $F_1$, $F_2$, . . . $F_X$ of the second round may be identical or different from the small molecule fragments used in the first round.

After the reactions have been allowed to occur, a tag specifying the small molecule fragment is added. The tag added in the first round usually comprises a priming site that can be used for addition of the tag in the second round so as to produce a linear identifier comprising the tags. In the first compartment, the reacted product is added a first tag which identifies the reactive compound building block of the second round that has reacted with the reactive reaction site of the nascent bi-functional molecule; in a second compartment, the product reacted with the second small molecule fragment of the second round is added the tag identifying said reactive compound building block, etc. Following the addition of the tags in each compartment, the content of the compartments are mixed in a common pool. The split-reaction-combining cycle can be repeated an appropriate number of times to obtain a library of bi-functional molecules comprising a molecule part and a coding part. The library may be used in a selection process disclosed elsewhere herein.

Above, the general principle for split-and-mix is disclosed, in which the reaction of the small molecule fragment and the chemical reaction site occurs prior to the encoding step. Obviously, the events can occur in the reverse order or simultaneously.

Figure 85:
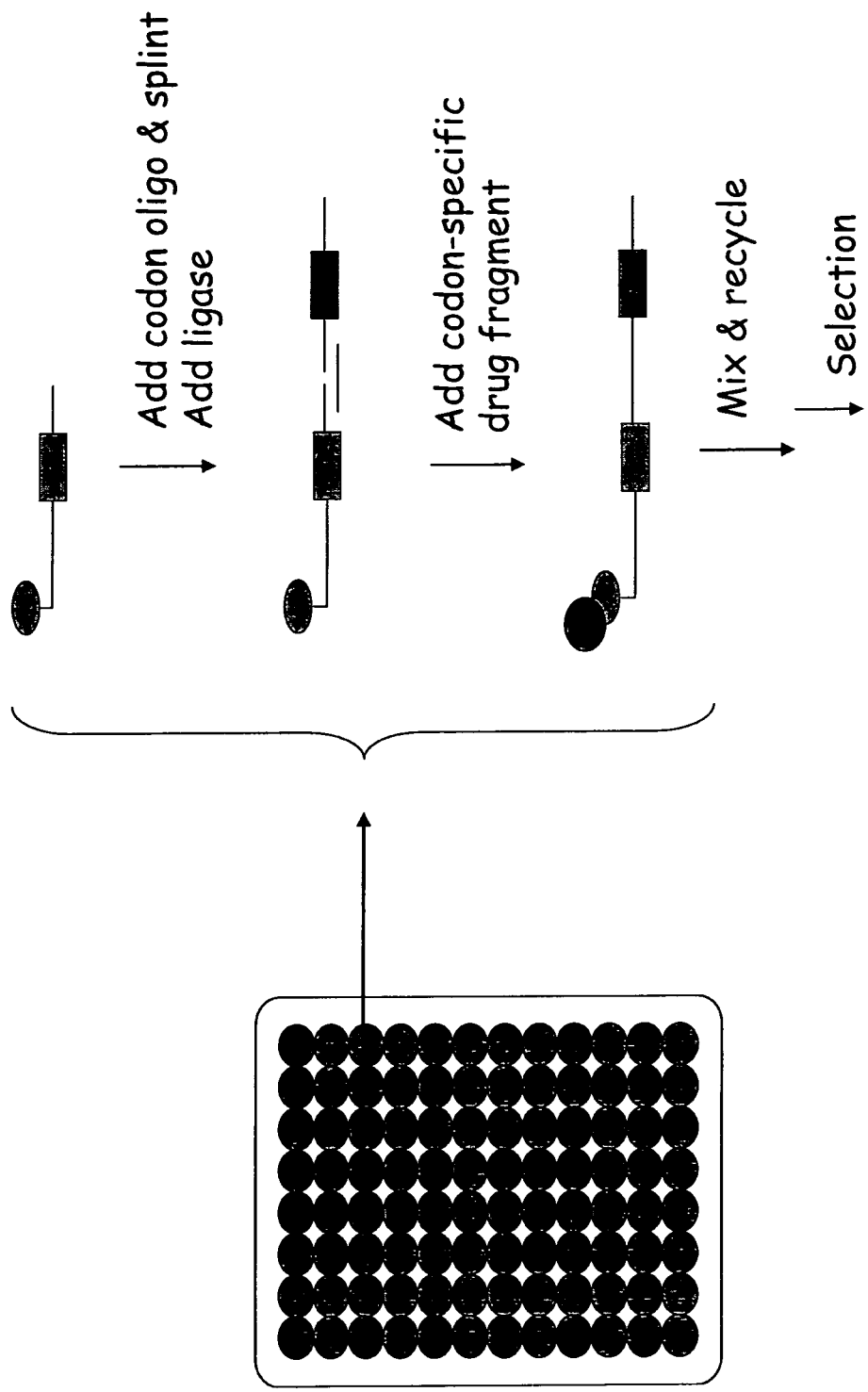

FIG. 85 schematically shows a 96 well microtiter plate to the left. In each well or in a selected number of wells, the process to the right occurs. Initially, a bi-functional molecule is provided. The bi-functional molecule comprise a chemical reaction site (oval) attached to a codon (rectangle) through a linker (line). To the left of the codon a binding region is provided. Next, a codon oligonucleotide and a splint oligonucleotide are added. The codon oligonucleotide is provided with a codon and flanking binding regions. The splint is designed with sequences complementing the binding region of the nascent bi-functional molecule and a binding region of the codon oligonucleotide such that the ends abut each other under hybridisation conditions. The nascent bi-functional complex, the splint and the codon oligonucleotide forms a hybridisation product under appropriate conditions. A ligase is added to couple the codon oligo to the nascent bi-functional complex. In a second step, a drug fragment, i.e. a reactive compound building block, is added and conditions providing for a reaction with the chemical reaction site is instituted.

Then the content of each well is combined and, optionally, divided into a range of wells again for a second round of reaction and encoding. In final step, the combined contents of the wells are used in a selection or partition step, as disclosed herein.

Figure 86:
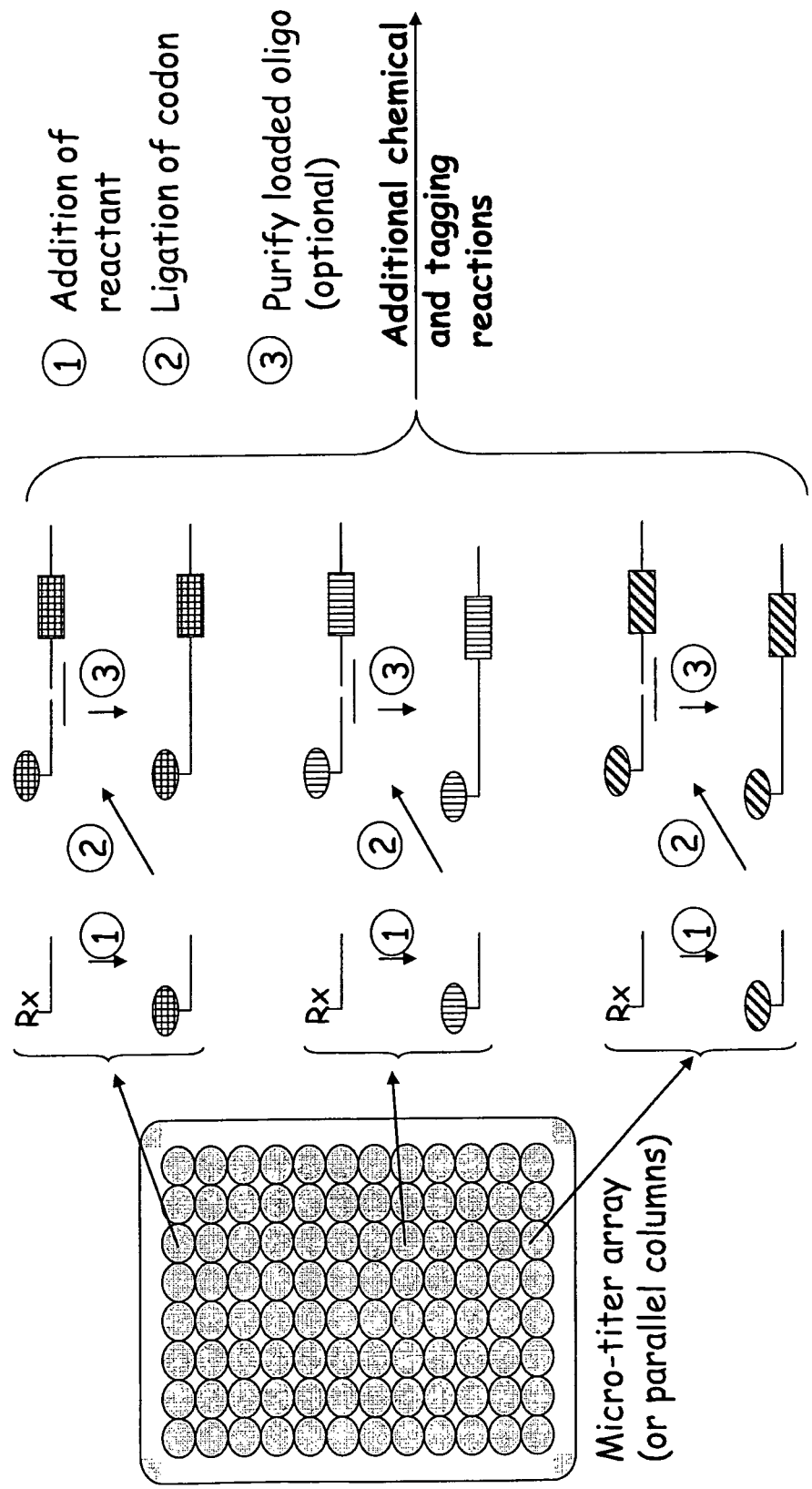

FIG. 86 outlines an embodiment with the encoding and reaction step reversed compared to the embodiment shown in FIG. 12. In a variety of wells a nascent bi-functional complex having a reactive group (Rx) attached to an oligonucleotide (horizontal line) is dispensed. In a first step, the reactive group in each compartment is reacted with a reactive compound building block, in a second step a codon oligonucleotide and a splint is added together with a ligase to ligate covalently the codon oligonucleotide to the reacted nascent bi-functional complex, and in a third step the ligation product is recovered. The content of the wells may subsequently be combined and used as a library of bi-functional complexes or recycled for another round of reaction and addition of tag.

Figure 87:
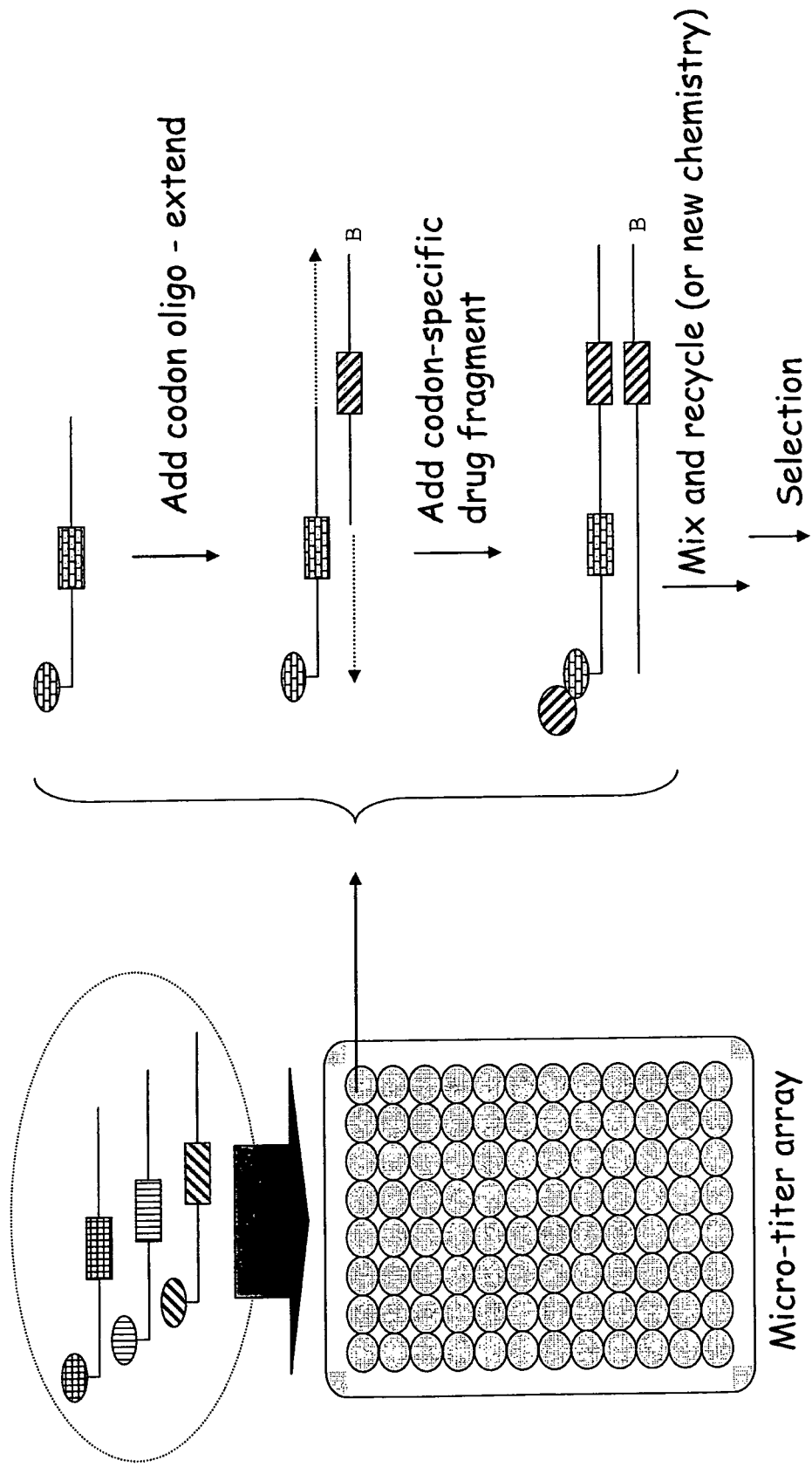

FIG. 87 discloses the use of the library produced in accordance FIG. 86, or any other library having a coding part and molecule part, in a further round. Initially, the combined contents of the wells from the embodiment of FIG. 86 are dispensed in separate wells. Then an anti-codon oligonucleotide having a binding region which is complementary to the binding region of the nascent bi-functional molecule is added under hybridisation conditions, i.e. conditions which favour the assembly of the hybridisation product between the nascent bi-functional complex and the anti-codon oligonucleotide. Subsequently, or simultaneously with the addition of the anti-codon oligonucleotide, a polymerase, a collection of dNTP (usually, dATP, dGTP, dCTP, and dTTP), and appropriate salts and buffer are added to provide for an extension to occur. The extension (dotted arrow) transcribe the anti-codon to the identifier, thus attaching a tag that encodes the identity of the reactive compound building block subsequently reacted at the chemical reaction site. The anti-codon oligonucleotide is connected to a biotin (B) to allow for removal of the oligonucleotide.

Figure 88:
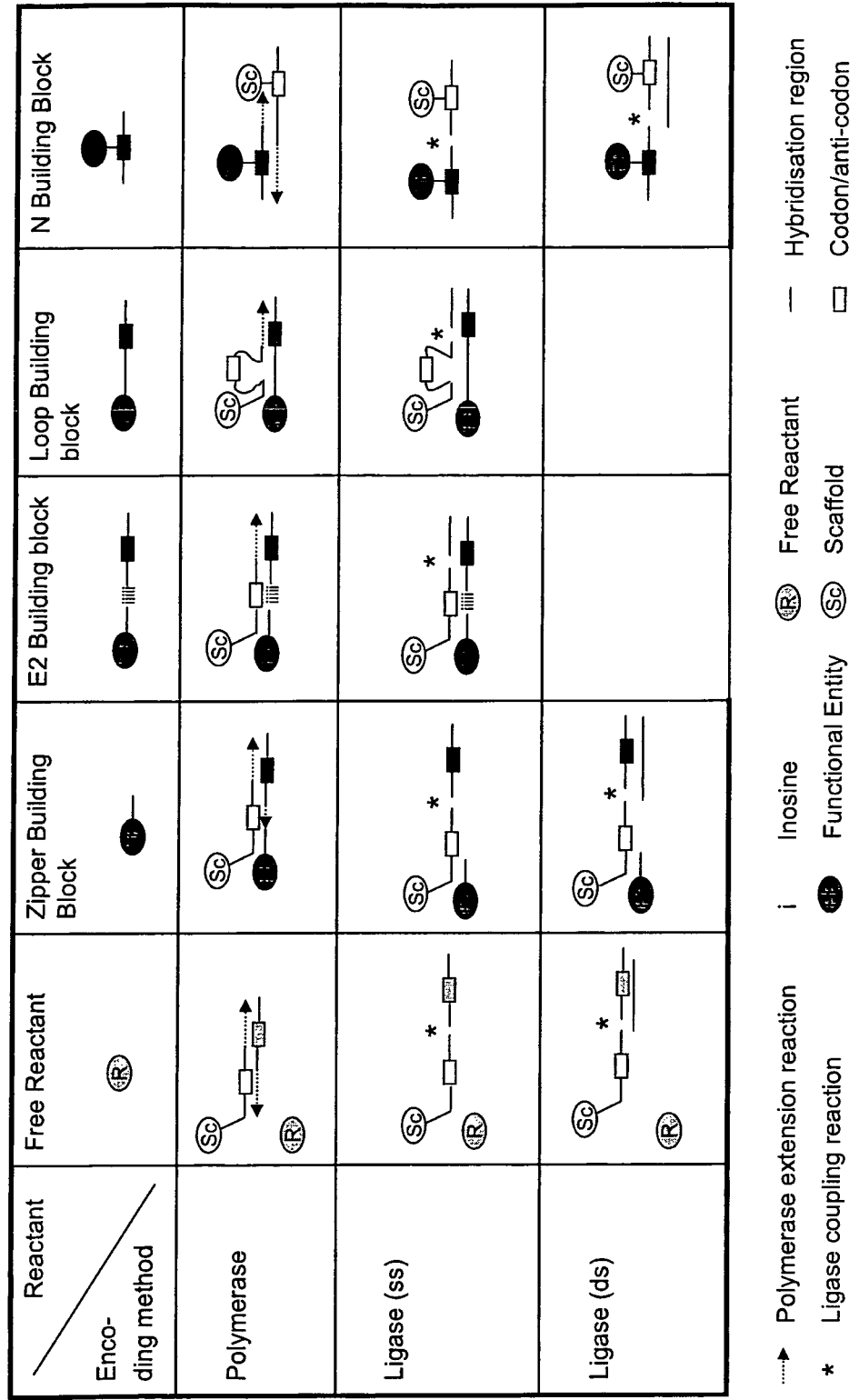

FIG. 88 discloses a scheme of various encoding methods combined with a collection of reactive compound building blocks. All the combinations are in according the invention.

Free Reactive Compound Building Block/Polymerase Encoding:

A nascent bi-functional complex comprises a scaffold (=chemical reaction site) comprising a reactive group and an oligonucleotide part comprising a codon identifying the scaffold. The codon is associated with an oligonucleotide binding region capable of forming a hybridisation product with a complementing binding region of an anti-codon oligonucleotide. The hybridisation product is subjected to an extension reaction, in which the scaffold oligonucleotide is extended over the anti-codon, thereby providing the scaffold oligonucleotide with a codon. Subsequent, simultaneously with or prior to the extension reaction, a free reactive compound building block coded for by the anti-codon is reacted with the scaffold.

Zipper Building Block/Polymerase:

A nascent bi-functional complex comprises a scaffold (=chemical reaction site) comprising a reactive group and an oligonucleotide part comprising a codon identifying the scaffold. The codon is associated with two oligonucleotide binding region capable of forming a hybridisation product with a complementing binding region of an anti-codon oligonucleotide and a complementing binding region of the reactive compound building block. The hybridisation product is subjected to an extension reaction, in which the scaffold oligonucleotide is extended over the anti-codon, thereby providing the scaffold oligonucleotide with a codon. Subsequent, simultaneously with or prior to the extension reaction, a functional entity coded for by the anti-codon is reacted with the scaffold. The selection of polymerase may determine the order of reaction and encoding as some polymerase, such as Sequenase, displaces the binding region attached to the functional entity, while other polymerases, like Taq polymerase, do not perform the displacement of the binding region. When a zipper building block is used a close proximity between the scaffold and the functional entity is obtained thereby promoting a reaction to take place.

E2 Building Block/Polymerase Encoding:

A nascent bi-functional complex comprises a chemical scaffold and an oligonucleotide part comprising the codon identifying the scaffold. The oligonucleotide part comprises two binding region on each sides of the codon. An E2 building block anneals to the scaffold oligonucleotide such that the functional entity comes in close proximity as to the scaffold and a double helix is formed just before the anti-codon, thus enable a polymerase to recognize the double helix as a binding area. Applying appropriate conditions and substrates enable the extension of the identifier oligonucleotide over the anti-codon, thus transcribing the genetic information of the function entity to the identifier. Opposing the scaffold codon is a stretch of universal binding nucleotides, such as inosine. Use of an E2 building block allows for one-pot synthesis of a library.

Loop Building Block/Polymerase Encoding:

A nascent bi-functional complex comprises a chemical scaffold and an oligonucleotide part comprising the codon identifying the scaffold. The oligonucleotide part comprises two binding region on each sides of the codon. A loop building block anneals to the scaffold oligonucleotide such that the functional entity comes in close proximity as to the scaffold and a double helix is formed just before the anti-codon, thus enable a polymerase to recognize the double helix as a binding area. Applying appropriate conditions and substrates enable the extension of the identifier oligonucleotide over the anti-codon, thus transcribing the genetic information of the function entity to the identifier. As no sequence on the building block complements the scaffold codon sequence, this codon sequence loops out. Use of a loop building block allows for one-pot synthesis of a library.

N Building Block/Polymerase Encoding:

A nascent bi-functional complex comprises a chemical scaffold attached to a scaffold codon through a linker. On one or each side of the codon a binding region is present. An N building block comprises a binding region which is complementary to the scaffold binding region and an anti-codon. A functional entity is attached to the codon or a binding region. Under hybridisation conditions the complementary binding regions hybridise and a polymerase extends in both directions, thereby transferring the genetic information of the anti-codon to the oligonucleotide covalently connected to the scaffold. Before, after or simultaneously with the extension reaction, the reaction between the functional entity and the scaffold may take place. Usually, the functional entity is attached to the anti-codon oligonucleotide via a cleavable linker so as to allow for transfer of the functional entity to the scaffold structure.

Free Reactive Compound Building Block/Ligase:

A scaffold entity is attached to an oligonucleotide comprising a codon. The scaffold oligonucleotide further comprises a priming site to which a codon oligonucleotide is ligated. The ligation is performed by a ligase. The ligation can take place in a single stranded or double stranded form. In the single stranded form, a 3' OH (or 5'-phosphate) of the scaffold oligonucleotide is ligated to a 5'-phosphate (or 3'-OH) of the codon oligonucleotide. In the double stranded form, an oligonucleotide complementing the ends of the scaffold and codon oligonucleotides, respectively, is used and designed so that the ends abuts each other. Optionally, the ligation occurs between two double stranded oligonucleotides, i.e. a double stranded scaffold oligonucleotide with an over hang ("sticky end") is ligated to a double stranded codon oligonucleotide provided with a complementing overhang. The type of ligation depends on the selected enzyme. Usually, the double stranded ligation is preferred because the reaction is faster due to the guiding effect of the oligonucleotide complementing the ends. The complementing oligonucleotide is also referred to herein as the splint oligonucleotide. Following, preceding, or simultaneously with the ligation of the codon oligonucleotide to the scaffold oligonucleotide a reaction between the free reactive compound building block and the scaffold takes place.

Zipper Building Block/Ligase:

A scaffold entity is attached to an oligonucleotide comprising a codon and binding region between the scaffold and the codon. The scaffold oligonucleotide further comprises a priming site to which a codon oligonucleotide is ligated. The ligation is performed by a ligase. The ligation can take place in a single stranded or double stranded form. In the single stranded form, a 3' OH (or 5'-phosphate) of the scaffold oligonucleotide is ligated to a 5'-phosphate (or 3'-OH) of the codon oligonucleotide. In the double stranded form, an oligonucleotide complementing the ends of the scaffold and codon oligonucleotides, respectively, is used and designed so that the ends abuts each other. Optionally, the ligation occurs between two double stranded oligonucleotides, i.e. a double stranded scaffold oligonucleotide with an over hang ("sticky end") is ligated to a double stranded codon oligonucleotide provided with a complementing overhang. The type of ligation depends on the selected enzyme. Usually, the double stranded ligation is preferred because the reaction is faster due to the guiding effect of the oligonucleotide complementing the ends. The complementing oligonucleotide is also referred to herein as the splint oligonucleotide. A zipper building block is a functional entity attached to a binding oligonucleotide. The binding oligonucleotide is complementing the binding region of the scaffold oligonucleotide, thus forming a hybridisation product under hybridisation conditions. Following, preceding, or simultaneously with the ligation of the codon oligonucleotide to the scaffold oligonucleotide a reaction between the functional entity and the scaffold takes place. The use of the binding region on the reactive compound building block ensures a close proximity between the functional entity and the scaffold.

E2 Building Block/Ligational Encoding:

Initially is provided a nascent bi-functional complex comprising a scaffold attached to an oligonucleotide, said oligonucleotide comprising a codon and a binding region between the scaffold codon and the scaffold codon. The scaffold oligonucleotide also comprises a priming site to which a codon oligonucleotide can be ligated. The scaffold oligonucleotide is hybridised to an E2 building block which carries a double stranded part. The oligonucleotide complementing the anticodon as ligated to the scaffold oligonucleotide using the E2 building block as a template. Before, after or simultaneously with the ligation a reaction takes place between the functional entity and the scaffold.

Loop Building Block/Ligational Encoding:

A bi-functional complex is provided comprising a scaffold attached to an oligonucleotide, wherein the scaffold oligonucleotide comprises a codon flanked by two binding regions. A loop building block is provided which has binding regions complementing the binding regions of the scaffold oligonucleotide. Upon hybridisation, the codon part of the scaffold oligonucleotide loops out. The loop building block also comprises a double stranded codon part. The oligonucleotide complementing the anti-codon part of the loop building block is ligated to the free binding region of the scaffold oligonucleotide. Before, after or simultaneously with the ligation a reaction takes place between the functional entity and the scaffold.

N Building Block/Ligational Encoding:

A nascent bi-functional complex is initially provided in which a scaffold via a suitable linker is attached the codon identifying said scaffold or attached to a binding region connect to the codon. A building block having a functional entity connected to a codon is the ligated to the scaffold oligonucleotide to connect the scaffold oligonucleotide with functional entity oligonucleotide. The ligation may be performed in a single stranded or in a double stranded state, depending on the particular enzyme selected for the ligation. Subsequently, the functional entity is reacted with the scaffold. In the alternative, the functional entity and the scaffold are reacted prior to ligation of the respective oligonucleotides.

When a round, i.e. a reaction with and a tagging of the nascent bi-functional complex, has been completed in accordance with any of the above encoding methods, a new round maybe in initialized according to any of the above reaction/encoding methods. Thus, the encoding and reaction in a first round may be the same or different in a subsequent second or further round. A single bi-functional complex or a library of complexes may be generated. When a library is contemplated, one-pot-synthesis can be conducted with the building blocks in which a covalent link between the functional entity and the codon/anti-codon is used, i.e. the columns of E2 building block, loop building block, and N building block. Split and mix synthesis can be performed, when no covalent link between the functional entity/reactive compound building block and the codon/anti-codon is present, i.e. in the columns indicating the free reactive compound building block and the zipper building block.

FIG. 89 shows a double encoding method, i.e. a method for encoding two or more reactive compound building blocks in one go. In certain embodiments, the multiple encoding methods allow for multi reaction between reactive compound building blocks and scaffold. Initially, a scaffold connected to an oligonucleotide comprising a hybridisation region, a scaffold codon and a binding region is annealed to an E2 building block. Subsequently, an extension is performed in which the anti-codon of the building block is transferred to the identifier. Several polymerases form an overhang of one or more single stranded nucleotides. This overhang is used in the present invention to attach an anti-codon oligo and allow the polymerase to further extent the identifier oligonucleotide over the anti-codon region of the anti-codon oligonucleotide. The transfer of the information of the anti-codon oligonucleotide allows for encoding a third free reactive compound building block C. The annealing between the oligonucleotide carrying A and the oligonucleotide carrying B provide for a close proximity between A and B and thus a high local concentration. Thus, when the free reactive compound building block C is added a reaction between the three components is favoured. One advantage of double encoding is that it is possible to exchange solvent, such that the reaction not necessarily must take place in the same solvent as the extension occurs.

To the right is illustrated an example, in which the above method is applied on 100 different scaffold oligonucleotides and 100 building blocks. The hybridisation product between the scaffold oligonucleotides and the building block oligonucleotides is divided into 100 different wells. In each of the wells the extension, addition of anti-codon oligonucleotide and reaction with specific free reactive compound building block is allowed. In total $10^6$ different bi-functional molecules are generated.

Figure 90:
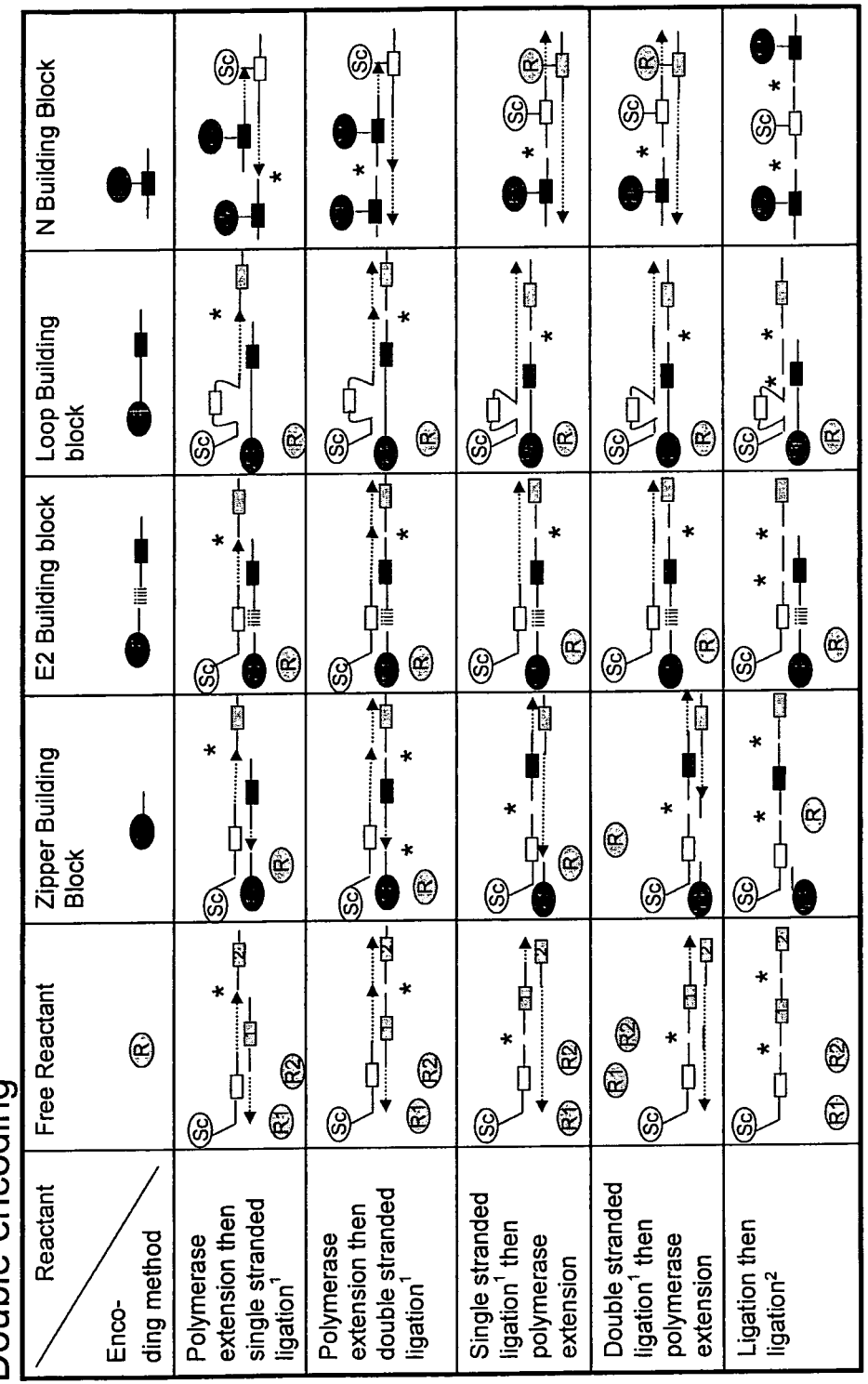

FIG. 90 discloses various methods for performing double encoding. In all the examples, the encoding is shown to occur prior to reaction, but it will be within the ambit of the skilled person to perform the reaction first and then the encoding. When a library is contemplated, it is possible to conduct the reaction in a single container (one-pot synthesis) using the N building blocks in combination with any of the encoding methods. For the remaining reactive compound building blocks it is necessary to conduct one or more split-and-mix step. In the combination of the zipper building block, E2 building block, and the loop building block with any of the encoding methods a single split-and-mix step is necessary, whereas two split-and-mix steps are necessary for the free reactive compound building block in combination with any encoding method. The scheme makes it possible for the skilled person to select a reaction/encoding method which is useful for a specific reaction. If triple-, quadro-, or multi encoding is contemplated, it is possible to perform such encoding using an embodiment of the double encoding scheme in combination with an embodiment of the single encoding scheme of FIG. 88 one or more times to arrive at an encoding/reaction method that suits the need for a specific chemical reaction.

Figure 91:
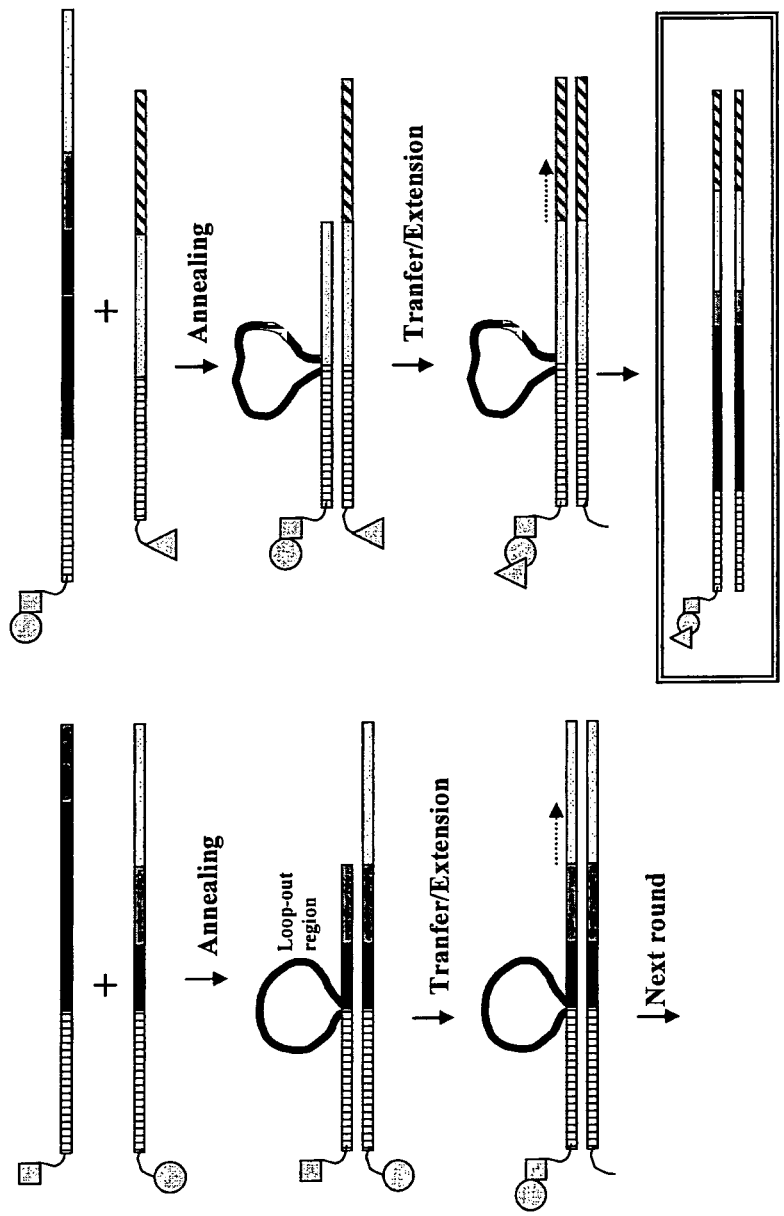

FIG. 91 discloses encoding using an loop building block.

Figure 92:
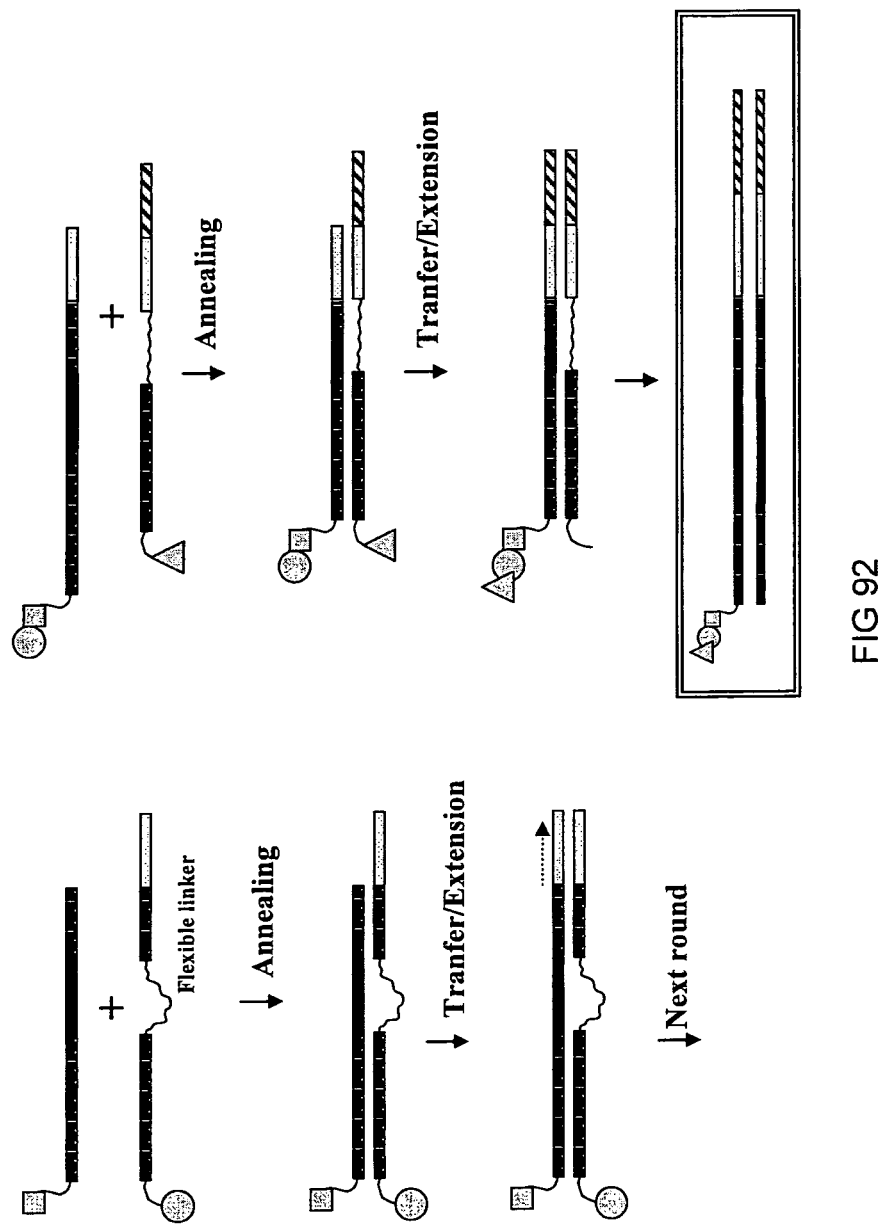

FIG. 92 discloses a method in which a flexible linker is used in the building block.

Figure 93:
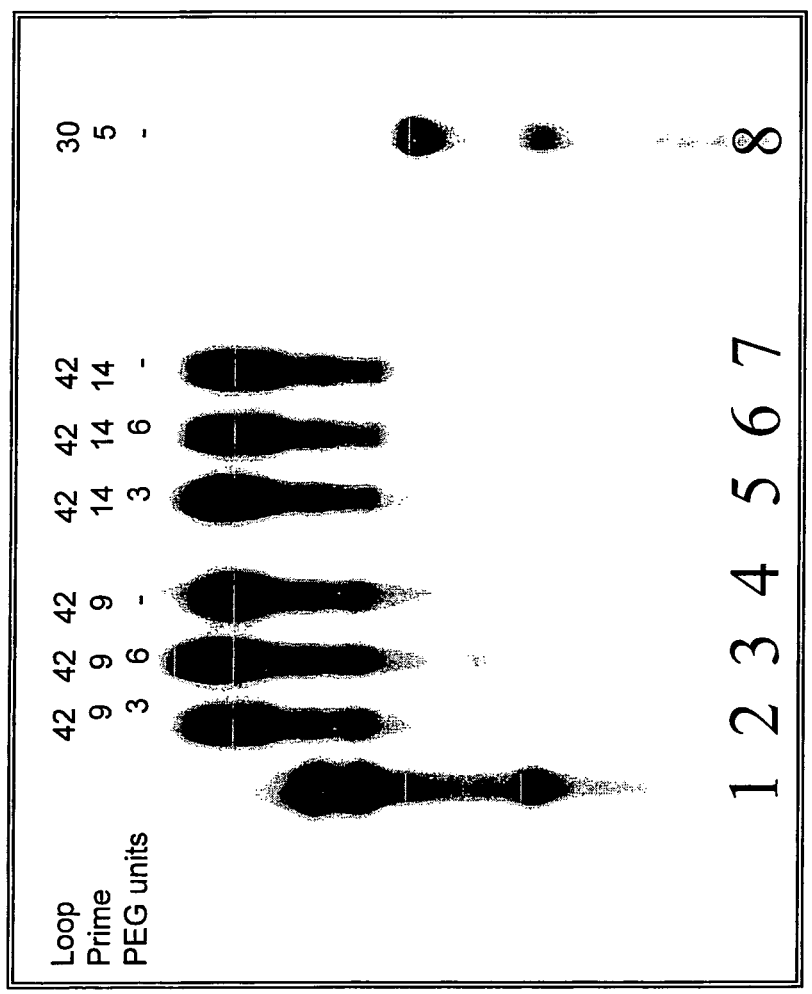

FIG. 93 discloses a gel showing the result of an experiment according to example 6.

Figure 94:
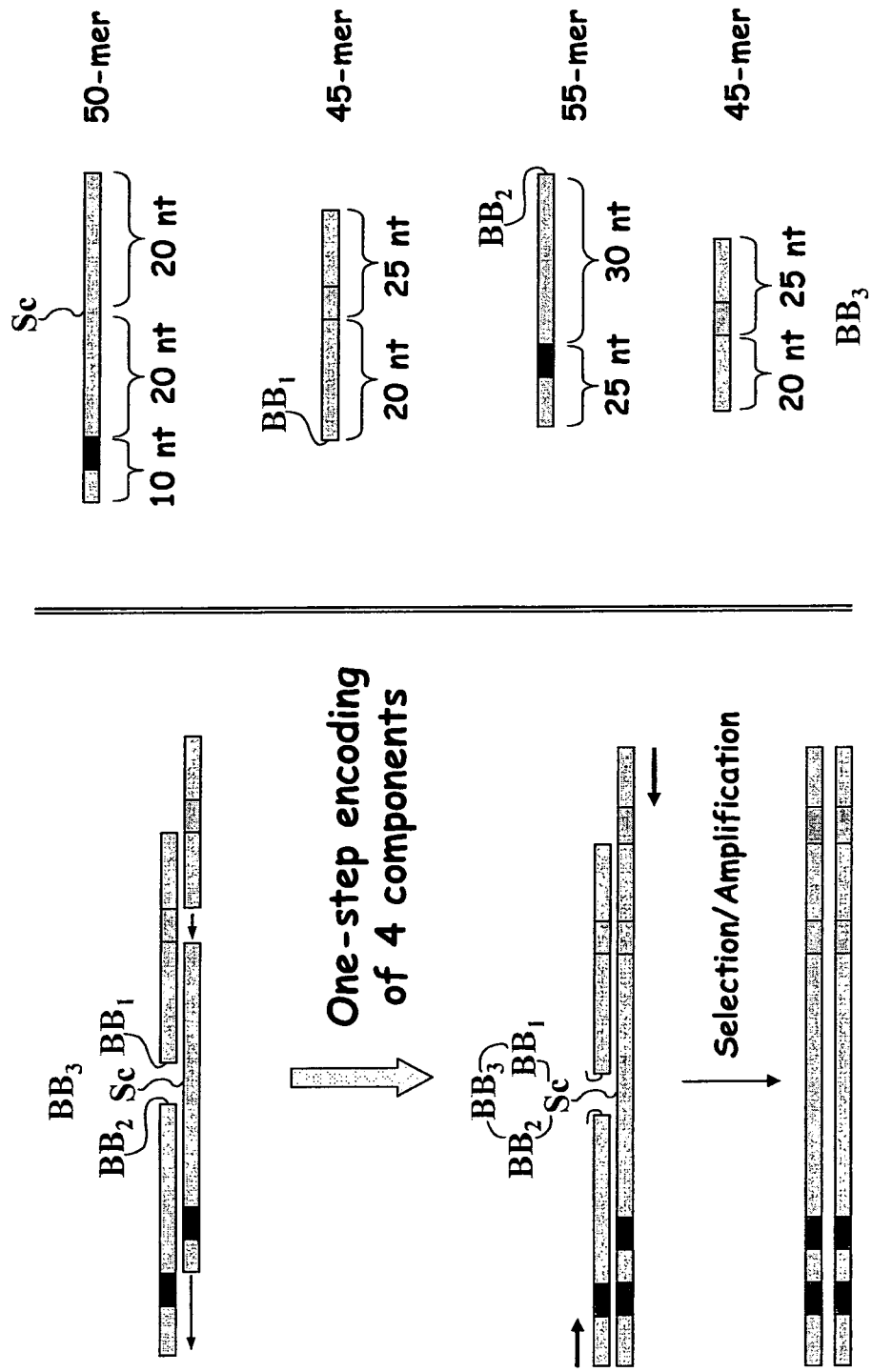

FIG. 94. discloses a triple encoding method. Initially, a scaffold attached to a scaffold oligonucleotide is provided. The scaffold is attached to a binding region the scaffold oligonucleotide, and the scaffold oligonucleotide is further provided with a codon. The two building blocks of the E2 type is annealed to the scaffold oligonucleotide, thereby bringing the functional entities BB1 and BB2 into close proximity with the scaffold. Simultaneously, prior or subsequent to the addition the building blocks a codon oligonucleotide coding for a third reactive compound building block (BB3) is provided which comprises a part complementing a nucleotide sequence of the first building block. The components of the system are allowed to hybridise to each other and a polymerase and a ligase is provided. The polymerase performs an extension where possible and the ligase couples the extended oligonucleotides together so as to form a double stranded product. Following the encoding process, the third reactive compound building block is added and conditions are provided which promote a reaction between the scaffold and the reactive compound building blocks. Finally, a selection is used to select reaction products that perform a certain function towards a target. The identifying oligonucleotides of the selected bi-functional complexes are amplified by PCR and identified.

To the right a particular embodiment for carrying out the present invention is indicated. Accordingly, each codon is 5 nucleotides in length and the binding regions flanking the scaffold are 20 nucleotides each. The building blocks designed to hybridise to the binding regions of the scaffold comprises a 20 nucleotide complementing sequence as well as a 5 nucleotide codon.

Figure 95:
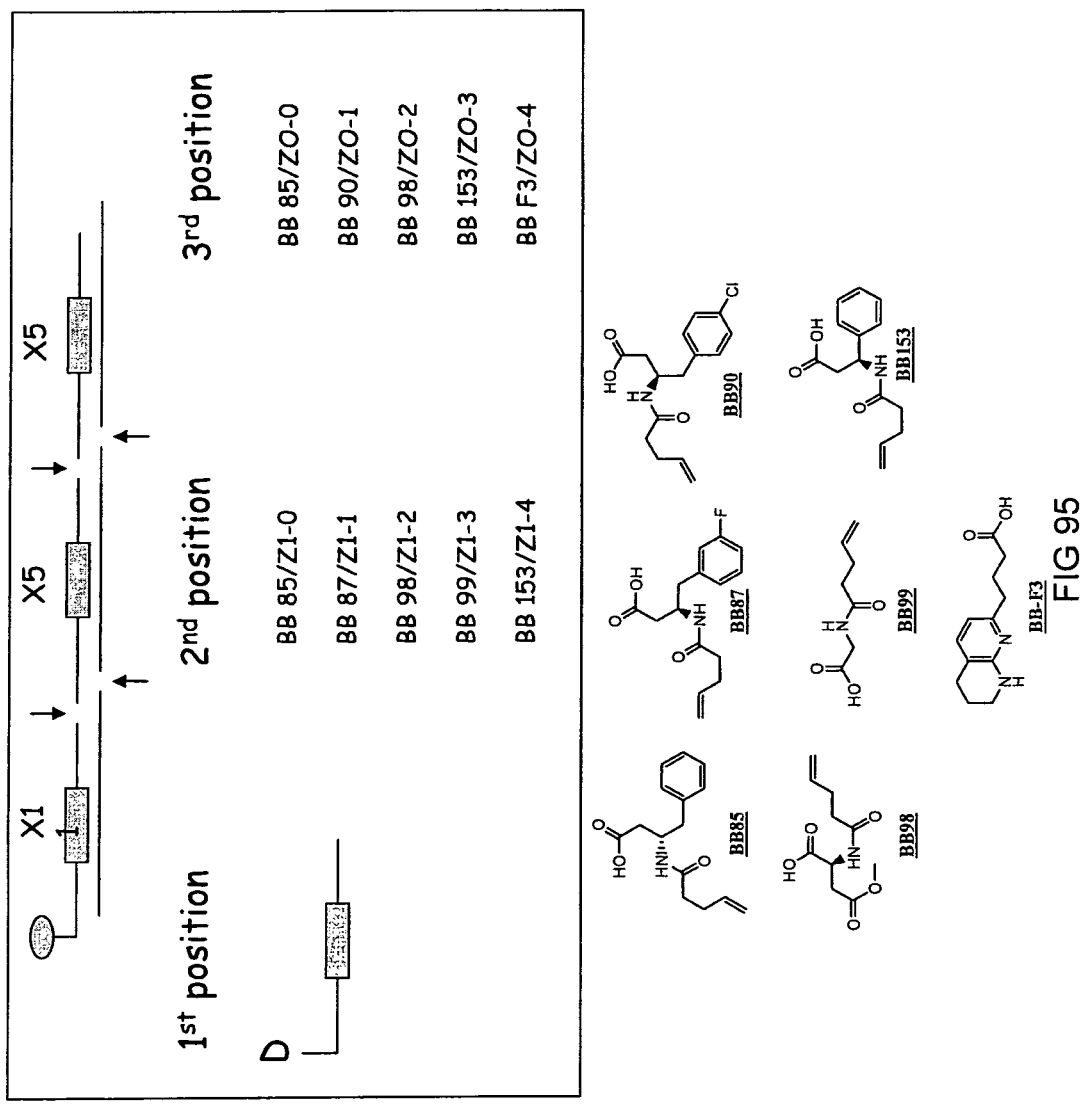
Figure 96:
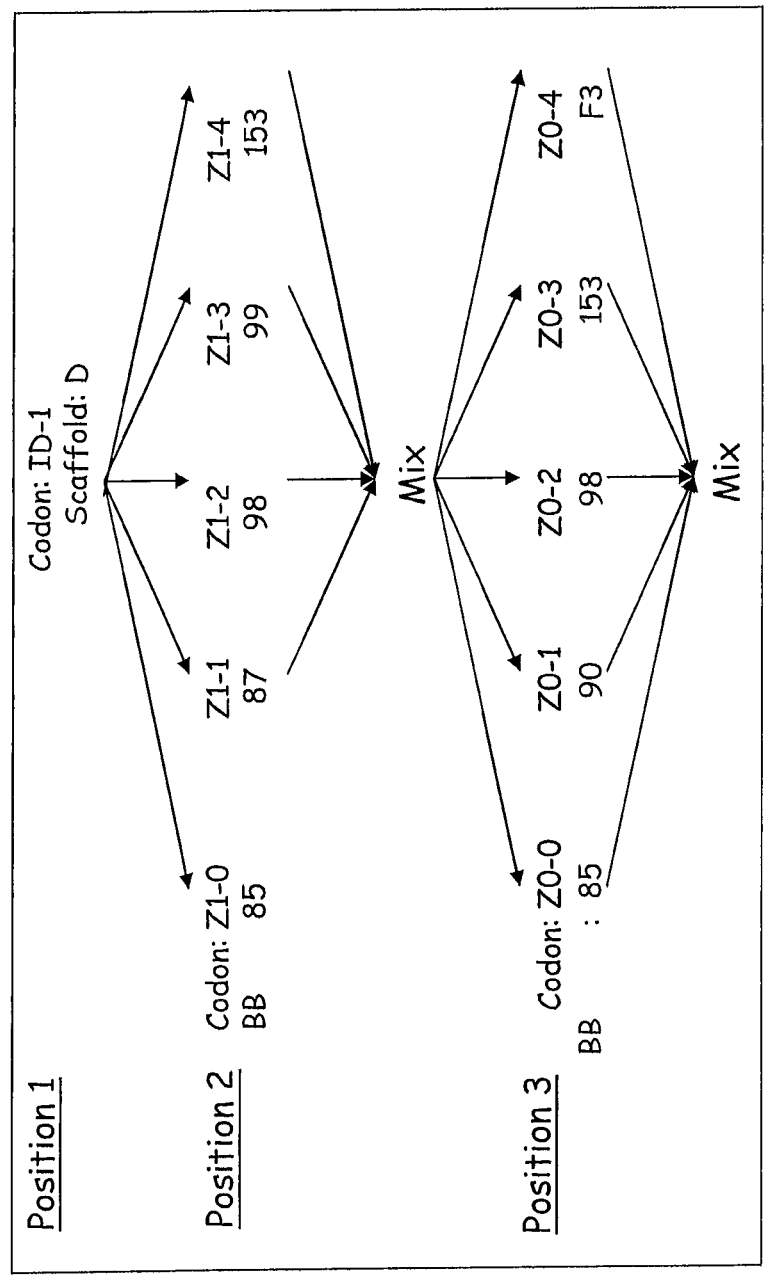

FIGS. 95-96 show schemes for the synthesis of a library.

Figure 97:
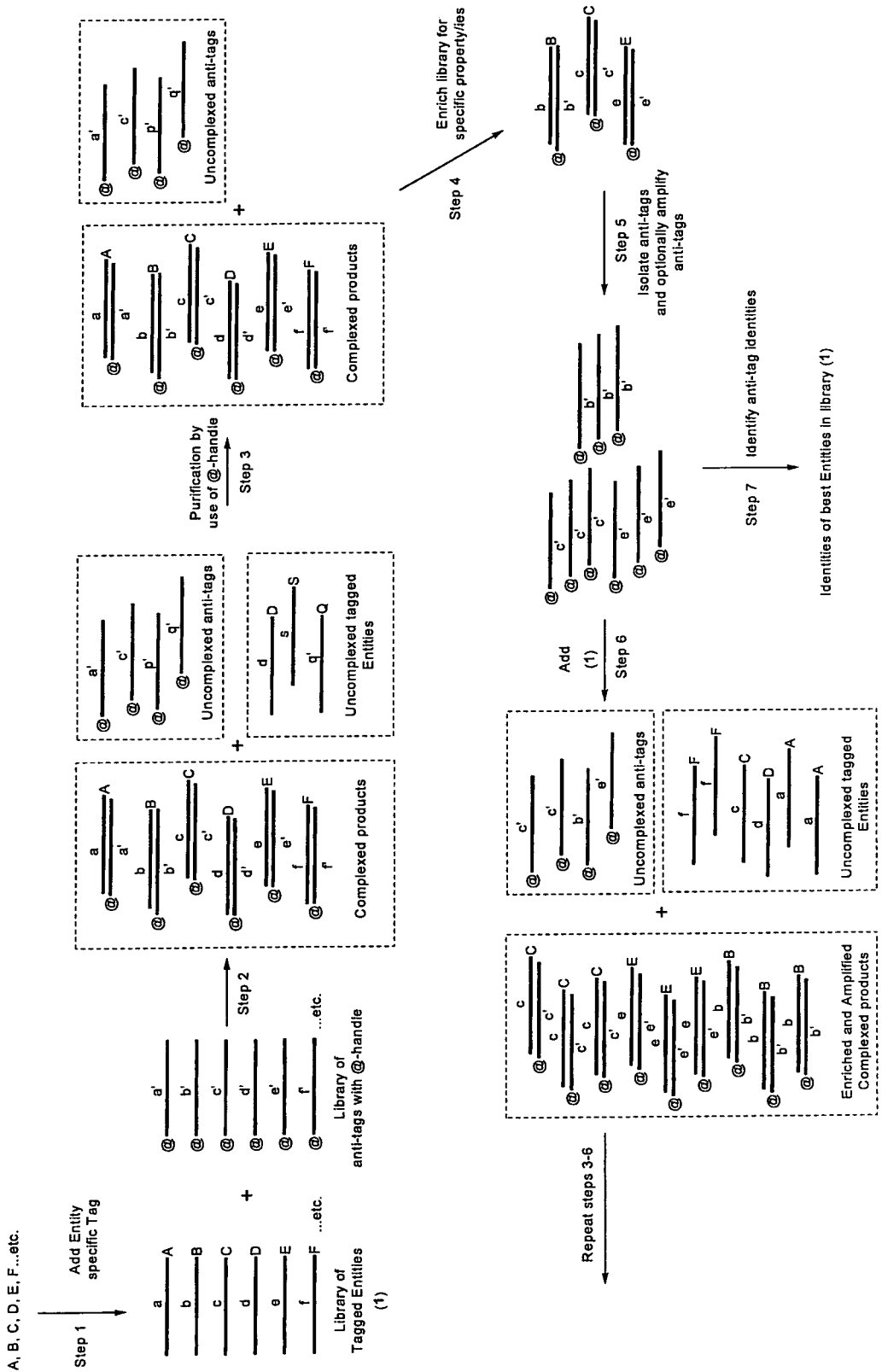

An embodiment of the enrichment method of the present invention is shown on FIG. 97. Initially, each chemical entity (denoted by letters A, B, C, . . . ) in a library is attached to a unique identifier tag (denoted a, b, c, . . . ). The identifier tag comprises information about that particular compound or group of compounds with respect to e.g. structure, mass, composition, spatial position, etc. In a second step, tagged chemical compounds are combined with a set of anti-tag sequences (denoted a', b', c', . . . ). Each anti-tag sequence carries a handle, like biotin, for purification purposes. The anti-tag sequences comprise a segment which is complementary to a sequence of the identifier sequence. The combination of anti-tag sequences and identifier sequences are allowed to form hybridisation products. Optionally, there may be tagged chemical entities present which have not been recognized by an anti-tag. In a third step, the sequences carrying a handle are removed, i.e. the tagged chemical compounds are left in the media while the matter comprising a handle is transferred to a second media. In the event, the handle is biotin it may be transferred to a second media using immobilized streptavidin.

Figure 98:
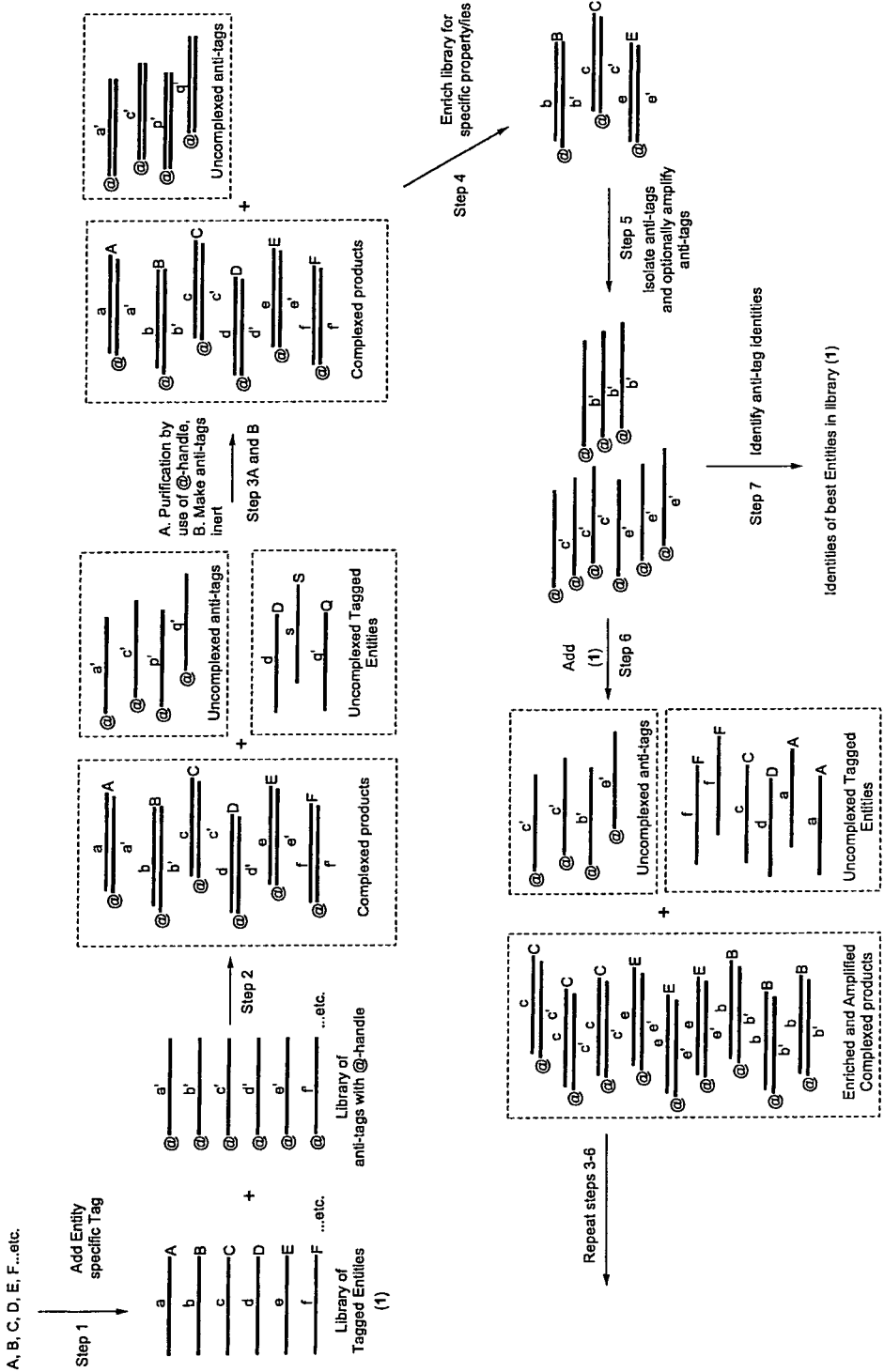

The purified matter may comprise anti-tag sequences not hybridised to a cognate sequence. As these anti-tag sequences are not coupled to a chemical compound to be selected for, the enrichment sequences may remain in the media. However, in some applications it may be preferably to make the excess anti-tag sequences double stranded, as illustrated in FIG. 98, because the double helix normally is inert relative to the selection procedure. The excess anti-tag sequences may be transformed into the double helix state by the use of a primer together with a suitable polymerase and nucleotide triphosphates.

The purified fraction is in step 4 is subjected to a selection process. The selection comprises probing for a set of properties, e.g. but not limited to affinity for a specific protein. In such a case, entities which do not bind to the specific protein will be eliminated. Anti-tags complexed to entities binding to the specific protein may be recovered/be isolated through e.g. the use of its purification handle.

In step 5 isolated anti-tags are optionally amplified through the use of PCR or RTPCR.

In step 6, the initial library of tagged entities produced in step 1, may undergo further rounds of complexation and screening, i.e. the anti-tags from step 5 may be added the library of tagged entities of step 1 and then be submitted to step 3, step 4 and step 5. Step 6 may be repeated.

In step 7, the isolated anti-tags of step 5 may be cloned and their identity be revealed. E.g. in the case of DNA, sequencing may be applied whereby the identity of specific entities with selected properties in the library of tagged entities will be revealed.

Figure 99:
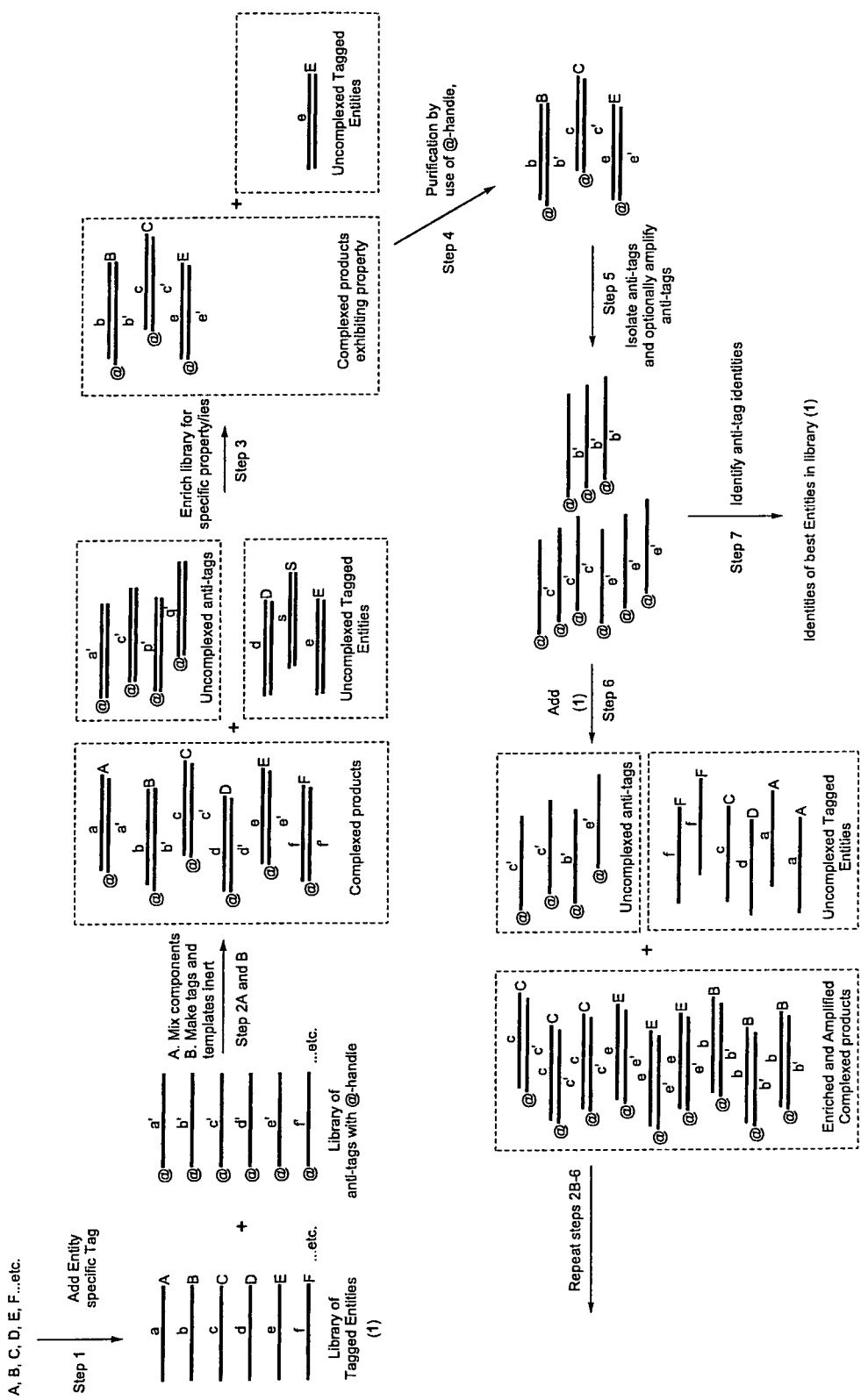

The embodiment shown in FIG. 99 resembles that of FIG. 97 except that the non-complexed components are rendered inert, e.g. if the tags and/or anti-tags are composed of single stranded DNA or RNA, they may be transformed into double stranded DNA, RNA or a hybrid thereof. This may be accomplished by use of a primer, nucleotide triphosphates and a polymerase or transcriptase. Furthermore, the sequence of purification (by use of the purification handle on anti-tags) and probing for properties is changed compared to the method of FIG. 97.

Figure 100:
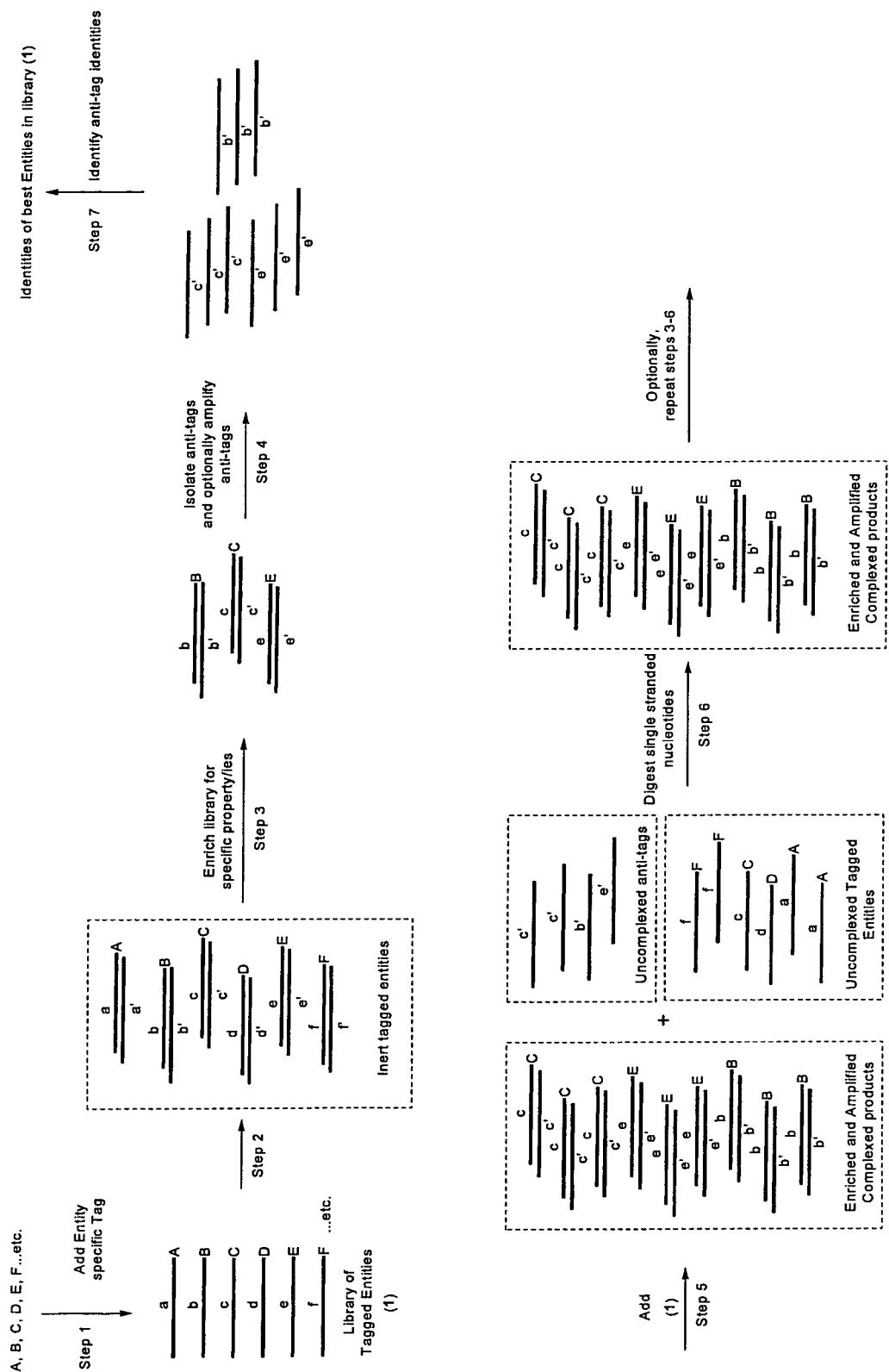

In FIG. 100, step 1, a number of entities (denoted by letters A, B, C . . . ), being it mixtures or single compounds are attached to a unique tag more specifically a DNA or RNA sequence or a derivative thereof, holding information on that compound or mixture, such as e.g. structure, mass, composition, spatial information etc.

In step 2, all tags of tagged entities are made double stranded by use of a primer (optionally carrying a @-handle such as e.g. biotin), nucleotide triphosphates and a polymerase or transcriptase. Remaining single stranded DNA or RNA may optionally be digested by use of nucleases.

The mixture, is probed for a set of properties in step 3, e.g. but not limited to affinity for a specific protein. In such a case, entities which do not bind to the specific protein will be eliminated. Anti-tags complexed to entities binding to the specific protein may be recovered/be isolated through e.g. the use of its @-handle.

Isolated anti-tags may optionally be amplified in step 4 through the use of PCR or RTPCR.

In step 5, the library of tagged entities of step 1, may undergo complexation to the isolated and optionally amplified anti-tags of step 3 and 4.

Single stranded components are being digested in step 6 by use of e.g. nucleases. The remaining double stranded subset of the library is optionally subjected to a renewed enrichment of the library according to step 3-6. Steps 3-6 may be repeated as sufficient number of times to obtain an appropriate chemical entity having the desired property.

In step 7, the isolated anti-tags of step 4 can be cloned and their identity be revealed, e.g. in the case of DNA, sequencing may be applied, whereby the identity of specific entities in the library of tagged entities is revealed.

Figure 101:
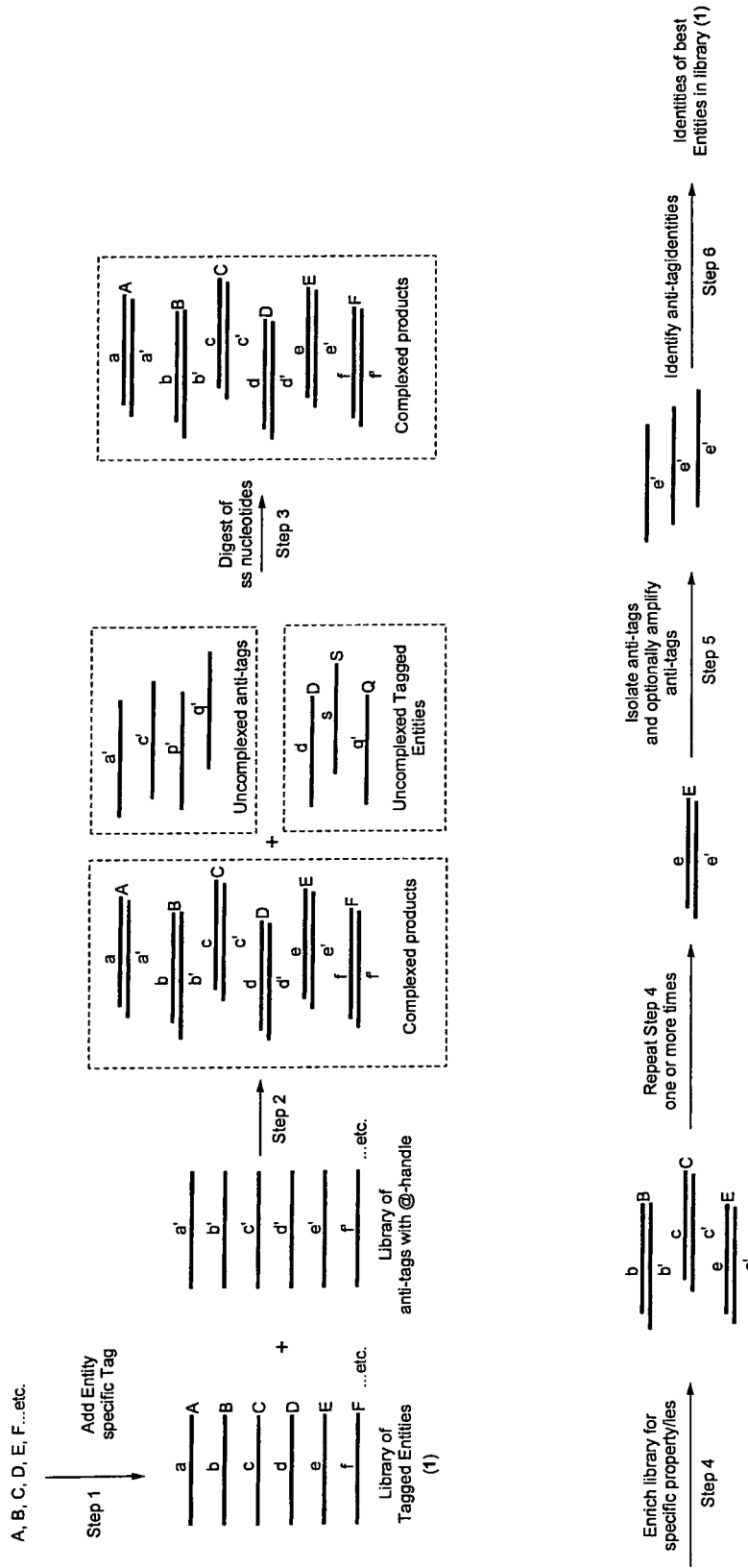

FIG. 101 relates to a method involving a digestion of single stranded oligonucleotides. In a first step a number of entities (denoted by letters A,B,C . . . ), being it mixtures or single compounds, are attached to a unique tag, holding information on that compound or mixture, such as e.g. structure, mass, composition, spatial information etc.

In step 2, mixtures of tagged entities are combined with a set of complementary anti-tags. Anti-tags may be, but is not limited to nucleotide derivatives. Anti-tags may optionally carry a @-handle. The tag and the anti-tags are allowed to form a complex. The complexation may be, but is not limited to hybridization. Some anti-tags will not form a complex with a tagged entity and some tagged entities will not form a complex with an anti-tag.

Non-complexed components is digested in step 3 using e.g. nucleases when the tags and/or anti-tags are composed of DNA or RNA or hybrids thereof.

The mixture of step 3, is probed for a set of properties in step 4, e.g. but not limited to affinity for a specific protein. In such a case, entities which do not bind to the specific protein will be eliminated. Anti-tags complexed to entities binding to the specific protein may be recovered/be isolated through e.g. the use of its @handle. Step 4 may be repeated one or more times.

Isolated anti-tags may optionally be amplified through the use of PCR or RTPCR as illustrated in step 5. Anti-tags may then also be used as described in FIGS. 24-27.

The isolated anti-tags may be cloned and their identity be revealed in step 6, e.g. in the case of DNA, sequencing may be applied, whereby the identity of specific entities in the library of tagged entities will be revealed.

Figure 102:
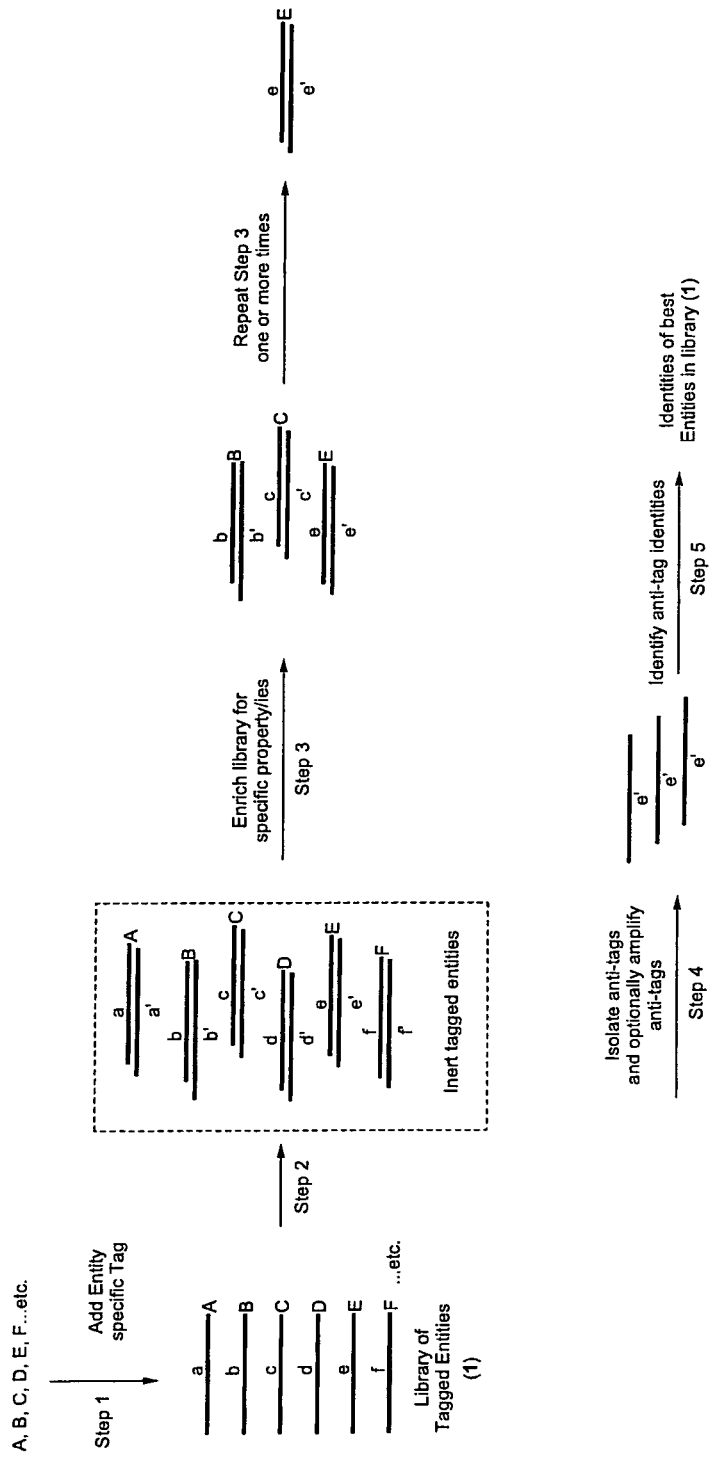

According to FIG. 102, step 1, a number of entities (denoted by letters A,B,C . . . ), being it mixtures or single compounds, are attached to a unique tag more specifically a DNA or RNA sequence or a derivative thereof, holding information on that compound or mixture, such as e.g. structure, mass, composition, spatial information etc.

All tags of tagged entities are made double stranded in step 2 by use of a primer (optionally carrying a @-handle such as e.g. biotin), nucleotide triphosphates and a polymerase or transcriptase. Remaining single stranded DNA or RNA may optionally be digested by use of e.g. nucleases.

In step 3, the mixture is probed for a set of properties, e.g. but not limited to affinity for a specific protein. In such a case, entities which do not bind to the specific protein will be eliminated. Anti-tags complexed to tags having appended entities binding to the specific protein may be recovered/be isolated through e.g. the use of its @-handle. Step 3 may be repeated one or more times.

According to step 4, isolated anti-tags may optionally be amplified through the use of PCR or RTPCR. Anti-tags may then also be used as described in FIGS. 97-100.

The isolated anti-tags may be cloned in step 5 and their identity be revealed, e.g. in the case of DNA, sequencing may be applied. Whereby, the identity of specific entities in the library of tagged entities will be revealed.

FIG. 103, step 1, produces a number of entities (denoted by letters A,B,C . . . ), being it mixtures or single compounds which are attached to a unique tag more specifically a DNA or RNA sequence or a derivative thereof, holding information on that compound or mixture, such as e.g. structure, mass, composition, spatial information etc.

In step 2, the mixture is probed for a set of properties, e.g. but not limited to affinity for a specific protein. In such a case, entities which do not bind to the specific protein will be eliminated. Step 2 may be repeated.

All tags of tagged entities are made double stranded in step 3 by use of a primer (optionally carrying a @-handle such as e.g. biotin), nucleotide triphosphates and a polymerase or transcriptase. Remaining single stranded DNA or RNA may optionally be digested by use of e.g. nucleases.

Anti-tags complexed to tags of entities binding to the specific protein may be recovered/be isolated in step 4 through e.g. the use of its @-handle. Anti-tags may optionally be amplified through the use of PCR or RTPCR. Anti-tags may then also be used as described in FIGS. 97-100.

The isolated anti-tags may be cloned in step 5 and their identity be revealed, e.g. in the case of DNA, sequencing may be applied, whereby, the identity of specific entities in the library of tagged entities is revealed.

Figure 104:
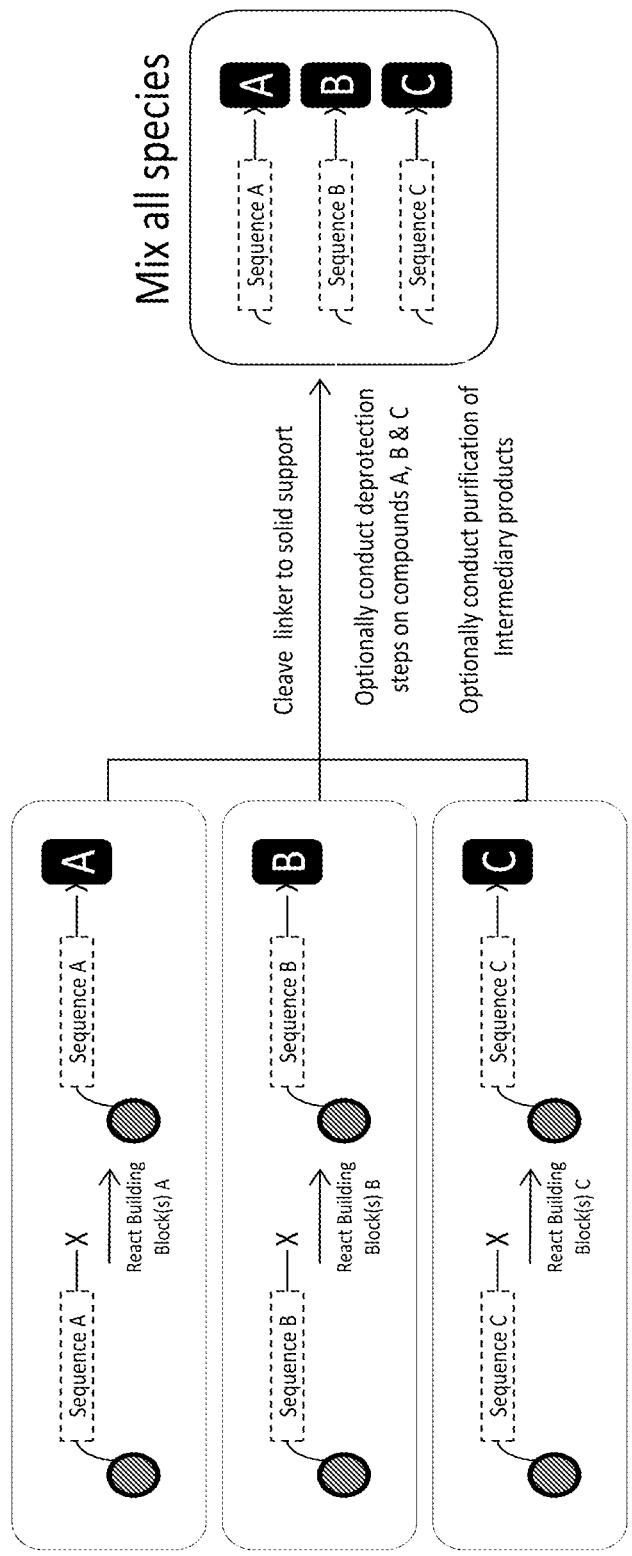
Figure 104:
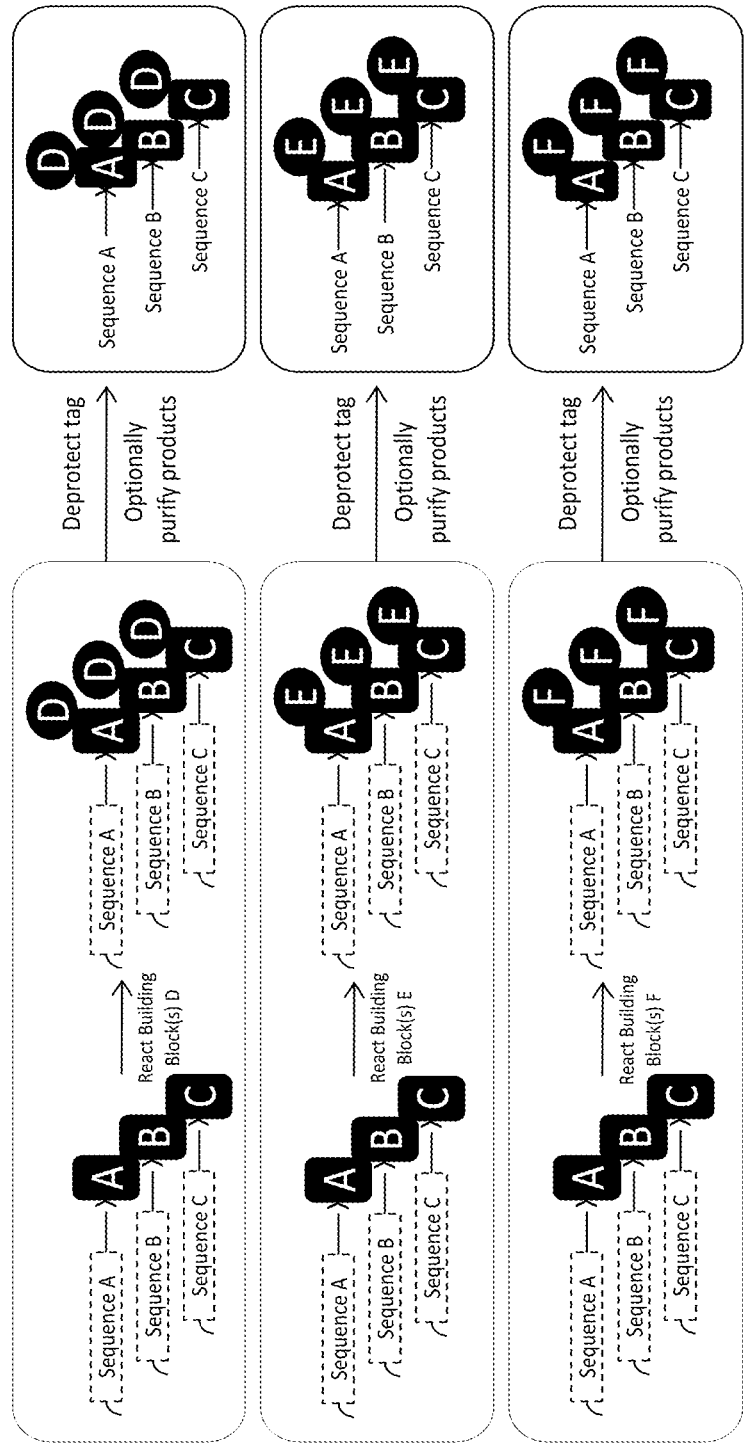
Figure 104:
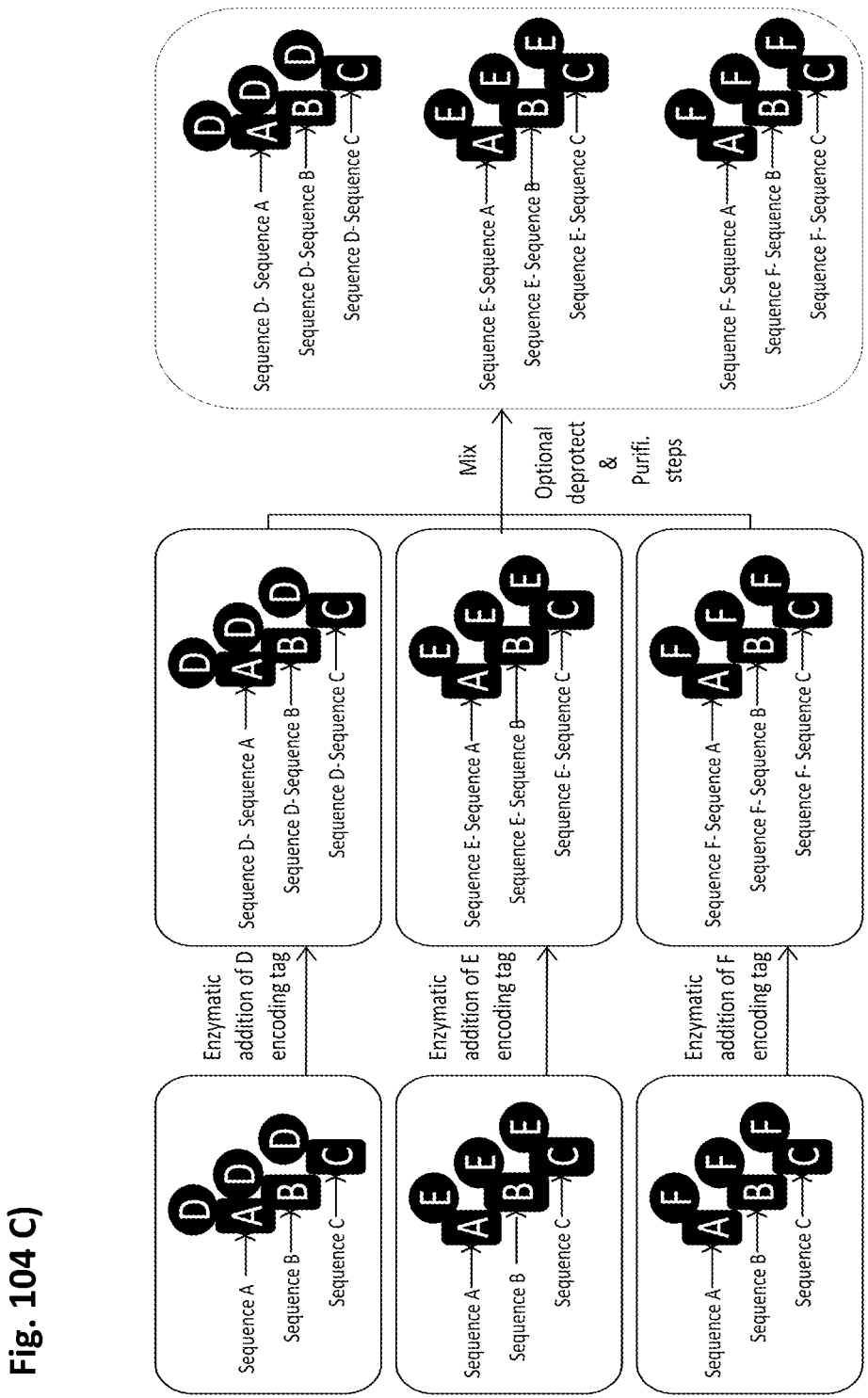

FIG. 104 depicts one setup and its synthetic steps involved in the synthesis of a library of bi-functional molecules.

A) Initially, individual unique oligonucleotide tag sequences (sequence A-C) are produced in separate wells and maintained connected to the solid support through a selectively cleavable linker (hairline) connecting the sequence and the solid-support (grey sphere). The oligonucleotide tag is connected to the reactive site X for the synthesis and display of the compound structure to be encoded by the oligonucleotide tag sequence(s). The oligonucleotide tags contain suitable protection groups on any potentially vulnerable functionalities such as the phosphodiester backbone and nucleo-base functionalities showed by a dashed box surrounding the sequences allowing for initial organic synthesis of the protected oligonucleotide tag as well as further chemical reactions on the reactive site X. The protections groups provide the oligonucleotide sequence tags with apolar characteristics which favor the use of organic solvents, media and reagents for any synthesis steps or manipulations to be conducted. The reactive site X may be suitably protected by a selectively cleavable protection group such as f. ex DMT/MMT (dimethoxytrityl/monomethoxytrityl). In each of the wells, shown boxed, a unique building block(s) A-C, is reacted with the reactive site X, producing a nascent bifunctional complex in which the building block is covalently conjugated to a unique oligonucleotide encoding said building block. Following, optional washing and deprotection steps, preferably in a parallel format, the linker of nascent bi-functional complexes are cleaved from the solid-support. The solution now containing the detached nascent bi-functional complex may optionally be subjected to further purification before mixing the samples from the individual wells providing a mixture of the content of the wells. The dangling end shown attached to the oligonucleotide tag sequences illustrate the possible protection group remaining on the tag, f.ex. on the 3'OH-group that may be used at a later stage for enzymatic addition of further tag(s).

B) The mixture in A) is split into a number of new wells and reacted with a unique building block, D-F, in each well. Following optional purification, preferably in a parallel format, the oligonucleotide tags are deprotected and optionally purified in a parallel format. The deprotection converts the tag of the bi-functional complex to unprotected and thus polar moiety suitable for handling in aqueous media or buffer or in mixtures of aqueous media and organic solvents for further manipulations. The transition from apolar to polar nature of the nascent bi-functional molecules allows for the enzymatic addition of a unique second tag encoding the second building block C) Enzymatic addition of the second tag encoding the second building block. Notice that the second tag may be combined from a combination of tags (see also FIG. 11). Following the ligation step the bi-functional products may be purified individually or collectively and optionally deprotected. The mixture produced may be prepared and used for library screening or may be developed further involving addition of more building blocks and cognate encoding tags.

The overall steps shown are:
Bead→Bead-Tag1→Bead-Tag1-BB1→Tag1-BB1→Tag1-BB1-BB2→Tag2-Tag 1-BB1-BB2.

A person skilled in the art will acknowledge that the order of events shown are arbitrary and may be interchanged for the purpose of improving a chemical synthesis process.

It should be further stated that this setup could be combined with other features in the present invention. Fx the use of a head-piece shown in FIG. 6 containing the reactive site X bridging two, fully or partly, self-complementary oligonucleotide sequences could be implemented allowing for self-hybridization useful for providing a suitable self-organized overhang to facilitate enzymatic addition of encoding tag sequences in C).

Figure 105:
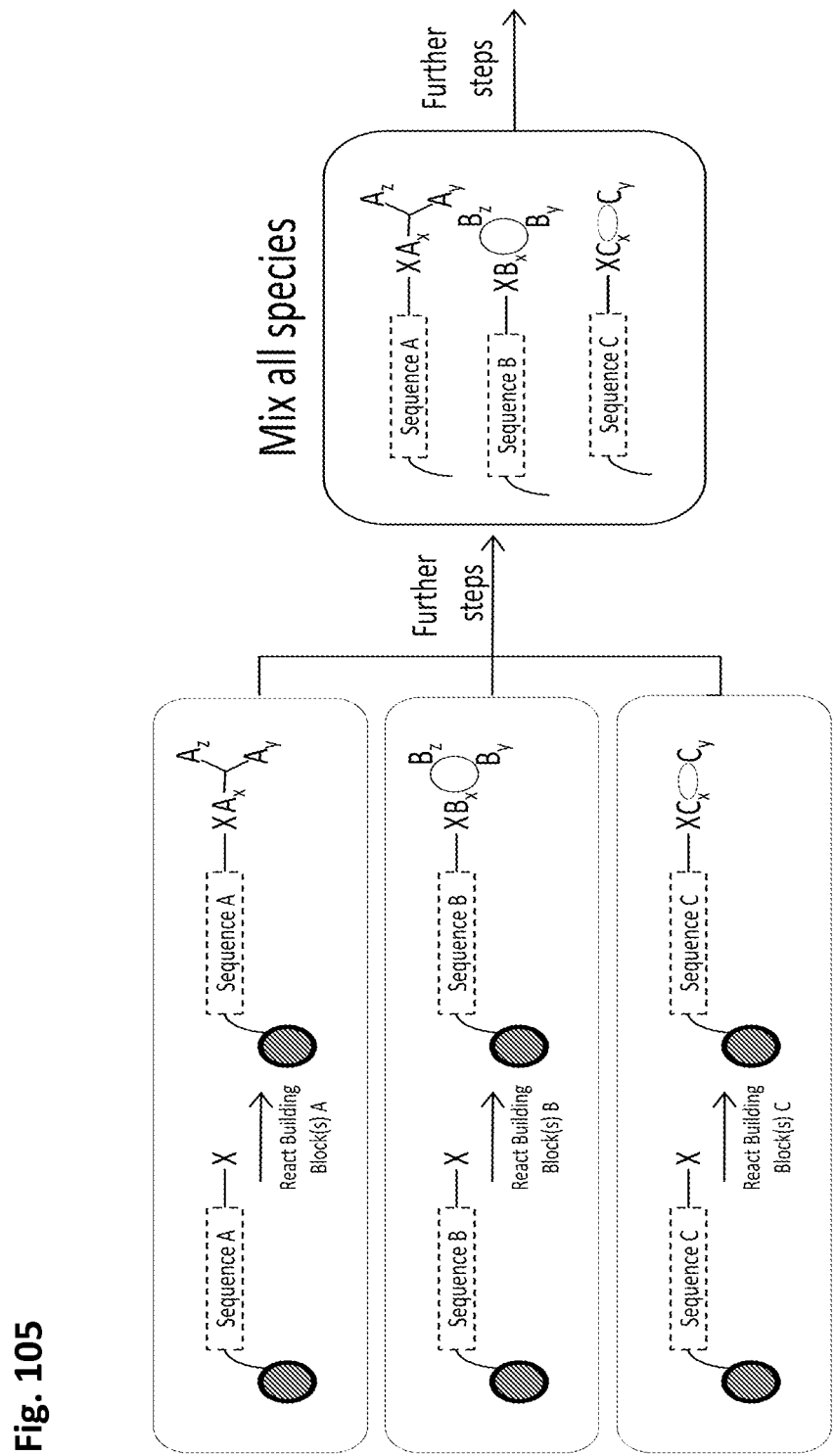

FIG. 105 depicts the synthesis of first intermediate bi-functional complexes similar to step A) in FIG. 104. However, the number of building blocks used and the order of their reaction with the reactive site X are arbitrary. Consequently, a number of different chemical reactions in different reaction wells may provide suitable products useful for being mixed and split to new reaction wells for addition of a second building block(s)

Figure 106:
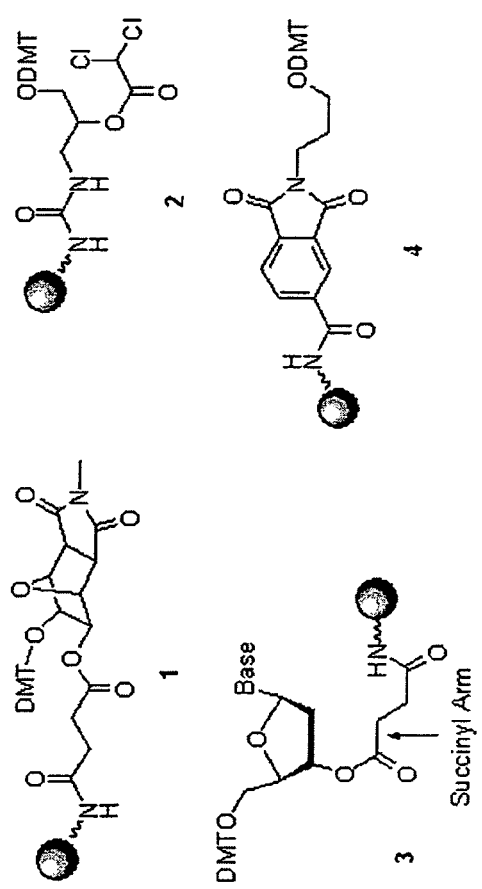

FIG. 106 depicts different common solid support linker for conventional organic synthesis of oligonucleotides using preferably phosphoramidite chemistry. The grey spheres represent CPG (Controlled Glass-Pore) solid supports or equivalent and a DMT-protected linker. Entity 1 and 2 are both universal linkers suitable for reaction after deprotection with a suitable phosphoramidite as described by Glen Research, US (Glen Research catalog 2010 or www.glenresearch.com) or elsewhere in this application. The linker formed between the 3'-phosphate group of the oligonucleotide is labile upon addition of aqueous base such as concentrated ammonia forming a hydrolytic cyclization reaction cleaving the 3-phosphate group leaving a 3'OH group on the oligonucleotide. Linker entity 3 is a standard succinimidyl-ester based linker that is hydrolyzed by aqueous base such as concentrated ammonia to leave a 3'-OH group on the oligonucleotide.

Figure 107:
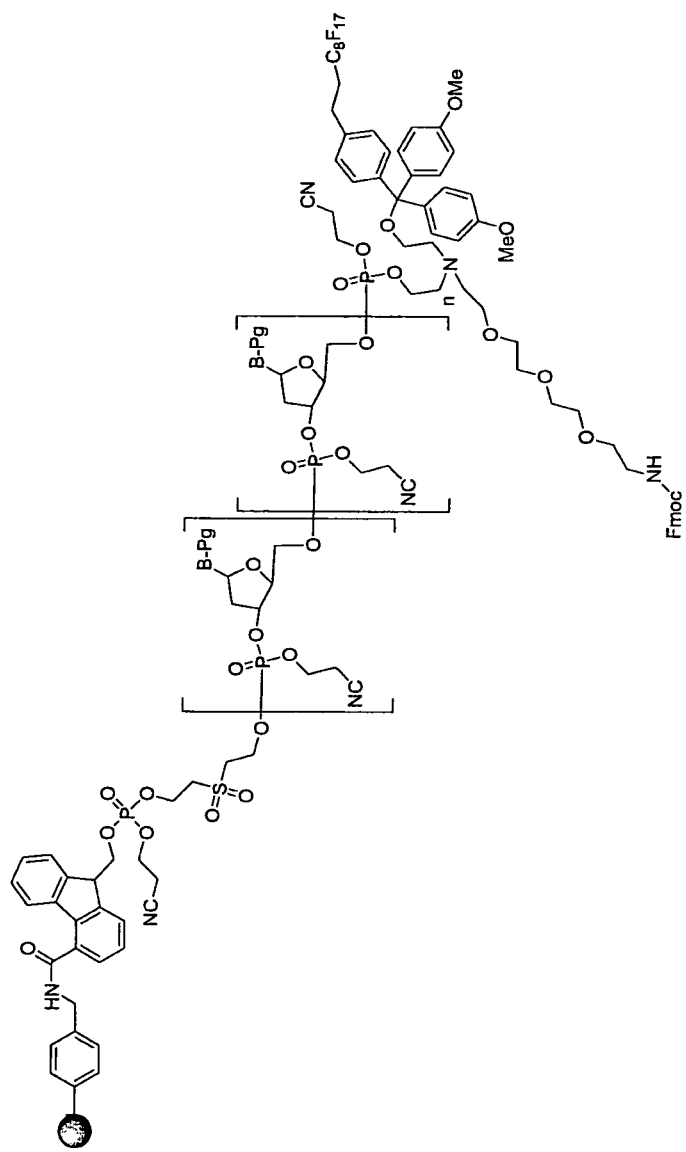

FIG. 107 is an example of an oligonucleotide tag having useful features suitable for the production of bi-functional complexes. The oligonucleotide is conjugated to a solid-support through a selectively cleavable sulphonic linker cleavable at high pH (via beta-elimination). The 5' end of the protected oligonucleotide tag contains a polyethylene-glycol linker with a terminal amine protected with Fmoc (selectively cleavable using piperidine, Chan & White, 2000, ISBN0199637253, methods incorporated herein by reference) and a polyfluorinated carbon tag useful for fast, efficient and versatile purification using methods described by Fluorous, Inc, US. The polyfluorinated carbon entity is shown linked via a DMT-group. For a person skilled in the art it is obvious that the exact structure shown can be modified to suit similar purposes of providing selectively cleavable units/protection groups, a reactive handle for compound synthesis and a purification tag or any subset of these. In one alternative example it should be envisioned that the sulphonic linker is connected directly to the 3' oxygen-group of the oligonucleotide tag eliminating the 3'-phosphate group.

Figure 108:
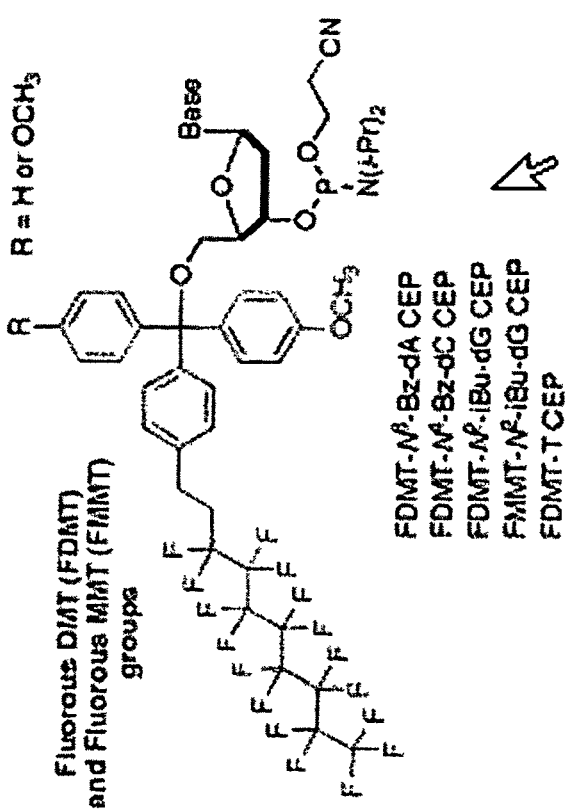

FIG. 108 is an example of a useful phosphoramidite entity comprising a C8F17 polyfluorinated tag for further modification and/or incorporation into oligonucleotide tag sequences.

EXAMPLES OF PREFERRED LIBRARY SYNTHESIS STRATEGIES

The following example describes generically the loading of single building block on nascent oligonucleotide tags or oligonucleotides in their final form on a solid-support.

The set of building block fragments is illustrated by grey or black triangles and reacted with the handle X of a set of unique oligonucleotide tags (grey bar) coupled to a solid-support (grey sphere). Hairlines represent linkers. The dashed line illustrates oligonucleotide protection groups (W/PG).

In example (A) one or more building blocks is first reacted separately on one or more reactive handles X, before synthesis of one or more oligonucleotide tags by organic synthesis comprising one or more unique codons that encode the building reacted on X. Following oligonucleotide synthesis, the bi-functional molecules are removed of some or all of their protection groups and cleaved off the solid-support in either single or multiple reactions in any order or simultaneously.

These steps provide a library of bi-functional complexes each comprising a unique chemical entity linked to a unique encoding oligonucleotide tag. The library of bi-functional complexes may be further developed by subjected the pool to one or more further rounds of chemical reaction with any number of building blocks and concomitant enzymatic addition of oligonucleotide tags that encode the individual building blocks (Note that the order of events for reaction and tagging are arbitrary).

Furthermore, in one embodiment of the present invention the continuous split-and-mix cycle of building block addition and addition of codon tags may by-pass step 3 described above. In this case the split-and-mix protocol is adopted on protected or partially protected oligonucleotides still allocated to a solid-support and the subsequent reaction of building blocks and enzymatic addition of encoding tags may be conducted on solid-support using preformed oligonucleotide codon tags and enzymes such as ligases, polymerases and recombinases.

For the further enzymatic addition of tags it may be suitable to provide the oligonucleotides with a 3'OH-group, 5' OH'-group or 5'-end phosphate for enzymatic reactivity.

In example (B) the ultimate result is similar to (A) except that oligonucleotide tag synthesis precedes addition of the building to the reactive site X. In Example (C) the oligonucleotide tag synthesis precedes the loading of building to the reactive handle X. However, in contrast to (B), X is located distal to the solid-support. This may offer an advantage in terms of reaction efficiency due to better solvation of X and thus better transformation turnover. The reactive handle X may be positioned anywhere suitable along the oligonucleotide and may also be exposed using modified nucleobases such as amino-modifier on cytidine and thymidine bases (f.ex Glenn Research catalog #10-1019-90 or 10-1039-90) or similar.

The method of (A) may have certain advantages compared to (B) and (C) in that no nucleotides are yet synthesized at the time of chemical reaction of the building block to X arguably increasing the potential scope of reaction diversity. Each oligonucleotide strand may contain any number of reactive handles X such as 1 or more dependent on the desired fragment valency (i.e the number of displayed molecules on a single oligonucleotide tag. Consequently, the fragment can be displayed once, twice, 3 times, ×4, ×5, ×6, ×7, ×8, ×9, ×10 or more than 10 times on an oligonucleotide strand.

For examples (A), (B) and (C) above, the selectively cleavable linker should preferably not be cleaved until one round of building block addition and oligonucleotide synthesis has been completed. Furthermore, the directionality of oligonucleotide synthesis is arbitrary and may proceed in the 5' to 3' direction or the more conventional 3' to 5' end direction.

A further example using any method of (A), (B) and (C) described above for the synthesis of a library of chemical fragments attached to a reactive handle and an oligonucleotide that does not contain a unique codon sequence may be envisioned. In this embodiment, the chemical reaction of a building block with a reactive handle X on an oligonucleotide that does not contain a unique sequence. Instead, the product will be subject to enzymatic addition of a unique codon tag as shown in FIG. 3 (c.f. FIG. 3). The addition of the tag can be conducted after step3 in solution or after step 2 when the bi-functional complex is still attached to the solid-support. For the latter option it may be desirable that all or a subset of oligonucleotide protection groups have been removed. Note that the order of step 1 and 2 as well as the position and number of reactive handles X are chosen arbitrarily and the setup below describing enzymatic addition of could be incorporated with any of the procedures depicted in FIG. 2 (c.f. FIG. 2).

In one embodiment shown schematically in FIG. 4 (c.f. FIG. 4) the first building block is a spacer between the solid-support and the oligonucleotide tag.

FIG. 5 (c.f. FIG. 5) outlines at least 2 possible procedures for combinatorial synthesis of small molecules each composed of 2 or more fragments without intervening tag-addition. In a further example (C) the reaction of the first building precedes tag addition and allows chemical reactions without potential limitations from the presence of protected oligo-nucleotides. The use of sequential reactions with no intervening oligo-nucleotide tagging events such as shown schematically in scheme (A) and (B) above enable the experimenter to connect 2 building blocks using any chemistry suitable without the restriction of maintaining orthogonality to the tagging step such as steps involving organic synthesis of oligonucleotide sequences.

The order of events for building block and tag addition is arbitrary and tag-addition may be conducted without intervening building reaction and conversely sequential building block addition may be feasible without intervening addition of tags. The tag-bars indicate a single-chain DNA-tag but may also contain a double stranded region at any point during the reaction scheme when an enzymatic tagging step is necessary. For simplicity the use of building block and some nucleotide protection and deprotection steps has been omitted but is inferred as an integral part of any synthesis strategy. Furthermore, the figures depict the parallel processes and have for simplicity omitted the mixing steps.

An example of solid-phase synthesis of self-complementary tag with a reactive handle is shown in FIG. 6 (c.f. FIG. 6). The synthesis of starting oligonucleotide containing a split-region separating the self-complementary or partially self-complementary sequences allows for intramolecular hybridization once protection groups have been removed. The grey and black bars indicate DNA-tags and hairline between the bars indicate the possibilities for base-pairing. The reactive handle X is selectively deprotected allowing chemical reaction on this chemical entity such as an amine, carboxylic acid, thiol, alcohol, aldehyde, reactive scaffold or any other chemical entity or entities capable of reacting with fragments without damaging the protected or partially protected DNA tags (although, unprotected DNA attached to a solid may prove feasible and incorporated in this invention—the practical aspect makes this embodiment less convenient).

The composition of the A-tags may comprise both a fixed sequence common to all A-tags or a subset of A-tags (f.ex for PCR-amplification purposes) and a unique sequence encoding one or more specific fragments. In on embodiment several tags may encode only one fragment or a subset of fragments. The 5'-end of the A-tags should comprise a phosphor-group (shown as p in the figure) for subsequent ligation to a B-tag. Although a 5'-end phosphor may be introduced by enzymatic means it is most desirable that the 5'-end phosphate is incorporated during oligonucleotide solid-phase synthesis. Furthermore, it could be envisioned that both of the split-regions of the tag does not need to encode the specific tag sequence specifying the chemical fragment. In this case, the segment complementary to the encoding A-tag sequence could be ligated following the DNA deprotection step.

The linker (L) is any useful linker capable of connecting the split codon segments. Preferably, the linker could be a poly-carbon or poly-ethyleneglycol (PEG) based linker of any useful dimensions provided that the Linker can connect complementary tag-sequences and display a reactive handle. Preferably, the linker forms a 3-way junction such as shown in this figure. If polyvalent display is desired the linker may contain 2 or more reactive handles such as 3, 4, 5, 6, 7, 8, 9, 10 or more than 10 reactive handles. The triangles represent chemical fragments reacting on the reactive site X or a structure or sub-structure of the reactive site or a part of a previously reacted fragment. Chemical deprotection steps have been omitted but is assumed as part of a chemical synthesis strategy.

Note that the final molecule comprises 2 (two) DNA strands covalently linked through the connecting linker.

Examples of Sequencing Input Library Material and of the Selection Output.

Following library affinity selection on a target of relevance, the small compounds having pre-disposed affinity for the target are identified by sequencing of the DNA tags. Any number of tags may be sequenced from any suitable selection step. Maximising the information content from the selection steps is essential for reliable hit identification. Consequently, it is desirable to obtain as much sequence information as possible. Several sequencing methods allows for the mass-sequencing of DNA. Fluorescent labeling techniques such as the Solexa principle (Illumina inc) using reversible terminators, SOLID™ sequencing by ligation (Applied Biosystems) and reversible terminator sequencing by Helicos. These sequencing technologies and further in development all describe mass-sequencing protocols useful or potentially useful for the sequencing and subsequent decoding of the DNA-tags produced in the exercise of the present invention. Furthermore, the pyrosequencing (Margulis et al., 2006) by 454 (Roche) is also feasible for sequencing DNA-tags. All useful techniques for mass sequencing and DNA-tag identification is incorporated herein by reference including but not limited to the mass-sequencing technologies described above.

Example of Synthesis of a Library Containing Bi-Functional Molecules.

Conventional organic synthesis of oligonucleotides employs solid-phase for efficient synthesis using f. ex phosphoamidites as building blocks carrying suitable protection groups. Other methods such as those listed in *Current protocols in Nucleic acid Chemistry*, Edit, Beucage et al. publ. Wiley, 2001 are equally feasible and incorporated herein by reference.

Example of Oligonucleotide Synthesis on a Solid Support Comprising a Reactive Amino Group Synthesis is conducted ABI 3900 synthesizer. Starting column material is 1 µmol Polystyrene $dG^{DMF}$ from Applied Biosystems and the following reagents:

LH 193 Phosphoramidite (see below) 100 mg/ml in acetonitrile.
0.05 M Benzoyl-dA Phosphoramidite in acetonitrile.
0.05 M DMF-dG Phosphoramidite in acetonitrile.
0.05 M Benzoyl-dC Phosphoramidite in acetonitrile.
0.05 M dT Phosphoramidite in acetonitrile.
Activator: 0.1 M 5-(Bis-3,5-trifluoromethylphenyl)-1H-tetrazole (Activator 42 fra Sigma/PrOligo) in acetonitrile.
Capping: A) 10% acetic anhydride in Tetrahydrofuran (THF) B) 16% N-methylimidazole i THF/pyridine
Oxidation: 0,02 M Iodine in THF/pyridine.
Deblock: 3% Trichloroacetic acid (TCA) in Dichloromethane General synthesis cycle (adopted from Sigma/PrOligo) (c.f. FIG. 7).

Deblock solution, containing trichloracetic acid (TCA) or dichloroacetic acid (DCA) in dichloromethane, removes the dimethoxytrityl (DMT) protecting group from the 5' hydroxyl moiety of nucleotides already incorporated into the growing nucleic acid, prior to the addition of the next phosphoramidite. Removal of the dimethoxytrityl (DMT) allows the unprotected 5' hydroxyl moiety to react with a new phosphoramidite in a subsequent extension reaction.

Wash solution, containing anhydrous acetonitrile (water content 5 30 ppm), is used as the overall wash solvent following each step in the synthesis cycle.

Activator solution, containing powerful activators like 4,5-dicyanoimidazole (DCI) or 5-(3,5-bis(trifluoromethyl)phenyl)-1H-tetrazole in acetonitrile, are mixed with solutions of phosphoramidites during the extension step. The activator reacts with the amidite group to form a highly reactive intermediate. The intermediate then forms an internucleotide bond with the detritylated 5'-hydroxyl group of the growing oligonucleotide chain Cap A solution, containing acetic anhydride and tetrahydrofuran (THF), is used after the phosphoramidite reaction/coupling step. This solution aborts chains bearing unreacted 5' hydroxyl groups due to failure of reaction with activated phosphoramidite (typically, 1 to 2% of growing oligonucleotide chains in each synthesis cycle). These unreacted 5' hydroxyl groups are capped with an acetyl group and thus rendered unreactive for subsequent synthesis steps. For certain syntheses with Proligo Reagents'® TAC-protected phosphoramidites, Fast Deprotection CAP A solution must be employed instead of Cap A solution.

Fast Deprotection Cap A solution, must be used for synthesis with Proligo Reagents'® TAC-protected phosphoramidites. Fast Deprotection Cap A solution, containing tertbutylphenoxyacetyl acetic anhydride (tac2O) in tetrahydrofuran, is used in place of Cap A solution to ensure that the displacement of tert-butylphenoxyacetyl (TAC) on guanine bases of the TAC-protected RNA phosphoramidites does not occur.

Cap B solution, containing tetrahydrofuran (THF), pyridine and N-methylimidazole (NMI), is mixed in-situ with Cap A solution during the capping (acetylation) reaction. Pyridine is applied as a mild base while NMI provides a powerful acylation catalyst.

Oxidizer solution, containing tetrahydrofuran (THF), pyridine, iodine and water, is applied to oxidise the chemically unstable trivalent phosphorous triester linkage formed in the coupling reaction to a stable pentavalent phosphate triester. Iodine functions as a mild oxidant and water functions as an oxygen donor.

Phosphoramidite LH193

The phosphoramidite LH193, which is described elsewhere in this application, or any suitable phosphoramidite containing an optionally protected group capable of optionally being deprotected and acting as a chemical handle or multiple chemical handles for attachment of chemical fragment(s) in the synthesis of small molecule libraries. Said phosphoramidites can be attached as internal or terminal entities in standard oligonucleotide synthesis as recognised by a person skilled in the art.

Example of Library Synthesis 5 different oligonucleotide tags, A1-A5 were synthesized using the protocol above, maintained on solid-support and deprotected on the terminal amine using the following protocol Deprotect Protected oligonucleotides A1-A5 maintained on solid-support
  To each column add 1 ml Dichloromethane (DCM).
  Incubate at RT for 15'
  Add 0.5 ml 2% DCA in Dimethylformamide (DMF. Incubate 1' min and drain
  Add 0.5 ml 2% DCA in DMF. Incubate 5' min and drain (turn yellow)
  Add 0.5 ml 2% DCA in DMF. Incubate 5' min and drain (turn yellow)
  Repeat until no color development
  Wash ×1 with 0.5 ml 2% DCA in DMF.
  Wash ×3 with 0.5 ml DCM and inc. 5'.

Each of the tags A1-A5 on solid support was reacted with a unique building block (BB1-BB5) shown below.

The 5 different oligonucleotide tags shown in FIG. 8 (c.f. FIG. 8) where X is the reactive amino-group with optional protection group, L is a polyethyleneglycol linker of 6 units, G, A, T, C are deoxynucleotide bases with suitable protection groups on base and backbone functional groups. The oligonucleotide entities are linked with f. ex and ester-linkage to a solid-support resin (grey sphere) suitable for oligonucleotide synthesis. The 6 nucleotides underlined depict the sequence unique to each of the oligonucleotide tags.

Acylation Reaction of Position 1 Building Blocks

All solutions are freshly prepared using dry solvent

Load Conditions:
  To each column is added:
  25 µl of specific building block BB1-5 shown in FIG. 9, panel A (c.f. FIG. 9) (0.1M in DMF)
  20 µl EDC (1-(3-[dimethylamino]propyl)-3-ethylcarbodiimide hydrochloride (0.1 M in DMF)
  5 µl HOAt (1-hydroxy-7-azabenzotriazol) (50 mM in MeOH)
  Inc. 1 h RT
  Wash 2×100 µl DMF (Dry)
  Repeat Load
  Wash 3×500 µl DMF
  Wash 3×500 µl DCM Following reaction, the solid support material is removed from all 5 columns and pooled. The material is split into 3 different samples and loaded on filtertips (MG) for reaction with position 3 different position 2 building blocks.

Alkylation Reaction of Position 2 Building Blocks (BB6-8)
  Add 0.1 ml DMF_dry to each resin. Incubate 5' and drain. Repeat
  Add: 25 µl BB 6-8 shown in FIG. 9, panel B (c.f. FIG. 9) (0.1M in DMF)
  5 µl DIPEA[0.5M] in DMF 87 µl DEA+913 ul DMF
  Incubate at 50° C. ON
  Wash 3×500 µl DMF, 3×500 µl water, 3×500 ul MeOH, 3×500 ul DMF, 3×500 ul DCM
  Pull out filter and resin to eppendorph tube Following reaction of the position 2 building blocks, the column material is treated with concentrated ammonia to remove oligonucleotide protection groups and cleave the covalent bond connecting the oligonucleotide with the solid support.

To each column is added:
50 µl of 10 M $NH_4$ in Acetonitril (AcCN)
Incubate at RT ON
Following brief centrifugation, the supernatant is transferred to new tubes. The resin material is washed ×2 with 50 ul of 10 M $NH_4$ in AcCN and the individual washes are transferred to the respective supernatant samples above.

The 3 individual samples are dried by lyophilization.

Each sample is dissolved in 50 µl of $H_2O$ and the samples are purified by P-6 spin-column Gelfiltration (Bio-rad). The amount of recovered and purified DNA material is estimated using optical density at 260 or 254 nm.

Ligation of Position 2 Codons.

1 nmol of DNA sample is transferred to new vials.

To each vial is added 5 µl of 10× ligase buffer [300 mM Hepes-buffer, pH 7.8, 100 mM $MgCl_2$, 100 mM DTT, 10 mM ATP]

To each of the 3 samples is added 1 nmol of a unique (pre-annealed) partially double stranded codon (standard oligonucleotides with no protection groups):
  Codon B1 (encoding BB6) pCTGATCGCTAAATGT-CAATCGGACTT (top strand) (SEQ ID NO 1)/AAGTCC-GATTGACATTTAGCGATCAGGCCAAT (bottom strand) (SEQ ID NO 2)
  Codon B2 (encoding BB7) pGATCCAGCTAAATGT-CAATCGGACTT (top strand) (SEQ ID NO 3)/AAGTCC-GATTGACATTTAGCTGGATCGCCAAT (Bottom strand) (SEQ ID NO 4)
  Codon B3 (encoding BB8) pGTAGTTGCTAAATGT-CAATCGGACTT (top strand) (SEQ ID NO 5)/AAGTCC-GATTGACATTTAGCAACTACGCCAAT (bottom strand) (SEQ ID NO 6)

The p on the top strand denotes a 5' end phosphor-group to facilitate enzymatic ligation.

$H_2O$ is added to each sample to a final volume of 45 µl.
To each sample is added 5 µl mixture containing 20 units of T4 DNA ligase (Promega) in 1× ligase buffer.

Samples are ligated at RT ON. and the ligase is inactivated by incubation at 80° C. for 10 min.

Following ligation and enzyme inactivation, each sample is purified in parallel using P-6 spin-column gelfiltration (Bio-rad). The samples are pooled and subsequently the library material is purified using HPLC, denaturing PAGE or equivalent techniques.

The amount of DNA library material is estimated from OD260.

Prior to selection on a relevant target protein, a library sample is converted to a double-stranded form by primer extension as described elsewhere in this application.

Example of Chemical Transformation in Library Synthesis.

In the library generation described above a first acylation reaction is followed by an alkylation producing a di-mer molecule on an oligonucleotide carrying a reactive amino handle, protection groups on the DNA-bases and attached to solid support resin.

A 21 nt oligonucleotide containing a 5'-terminal LH193 was synthesized using phosphoamidite chemistry. The oligonucleotide was deprotected at the terminal amino-group of LH193 unit using the protocol described above and maintained on the resin. Here, BB1 is loaded on the terminal amine as described above and the resulting product is split into 3 fractions for the subsequent load of BB6, BB7 and BB8 as shown above yielding dimmer A, B and C.

Following alkylation, the oligonucleotides are washed, deprotected and purified according to the above protocol and the resulting oligonucleotide products are subjected to mass spectroscopy by ES-MS on a Bruker-Esquire.

Dimer A: BB1-BB6 shown in FIG. 10, panel A (c.f. FIG. 10). Correct mass: 6406 Da. Starting material 6350. No product is apparent.

Dimer B: BB1-BB7 shown in FIG. 10, panel B (c.f. FIG. 10). Correct mass: 6453 Da. Estimated loading efficiency >80%.

Dimer C: BB1-BB8 shown in FIG. 10, panel C (c.f. FIG. 10). Correct mass: 6384 Da. Estimated loading efficiency >80%.

Example of Codon Combinations for Specifying a Single Building Block or a Combination of Building Blocks In certain aspects of the present invention it is desirable to reduce the time and resources spend on the purchasing, quality assurance by MS, stoichiometric pre-hybridisation, storage and user logistics of double-stranded codon oligonucleotides for library generation. Consequently, it may be desirable to reduce the number of codons to be prepared for library synthesis.

A theoretical synthetic combinatorial library of DNA-tagged molecules consisting of a billion compounds of trimers can be synthesized from a combination of 1000× 1000×1000 fragments molecules. Assuming a one-to-one relationship between a fragment and a unique codon it would require 3000 unique codons which in case of double-stranded codons would result in 6000 oligonucleotides. However, if each unique codon could be produced from two or more subsets of codons linked by enzymatic ligation, a reduced number of codons are required. In the example above, the 1000 codons in each position could be produced from 20×50 subcodons or 33×34 subcodons.

Consequently, the encoding of a billion member trimer library above could be accomplished by 20×50×20×50×20× 50 codons totalling only 210 codon or 420 oligonucleotides. Such codon combinations dramatically decrease time and resources necessary for codon maintenance and logistics although at the expense of a modest decrease in library yield due to an increased number of ligation reactions. FIG. 11 (c.f. FIG. 11) show the DNA encoding setup for the generation of a billion trimeric molecules encoded without subcodon combination and with subcodon combinations, respectively.

The use of subcodon combination reduces cost and resources and allows leeway and flexibility in the library encoding as dictated by library chemistry. F. ex., if a skewed di-mer library is desired with the fragment combination of 500×50.000 the subcodon setup shown above could encode the library using $A_1 \times A_2$ to encode position 1 and $B_1 \times B_2 \times C_1 \times C_2$ encoding position 2 building blocks. In a reverse with 50.000 fragments in position and only 500 fragments in position 2, $A_1 \times A_2 \times B_1 \times B_2$ could encode position 1 building blocks and $C_1 \times C_2$ could encode position 2 building blocks. In yet another skewed library composed of trimers, with the composition of 500×20×10.000, position 1 building blocks could be encoded by $A_1 \times A_2$, position 2 building blocks by $B_1$ and position 3 building blocks by $B_2 \times A_1 \times A_2$. Thus, the use of combinations of subcodons for encoding allows maximum freedom in encoding setup for multiple diverse libraries at much reduced cost and maintenance efforts. The number of subcodons shown in the example above is meant to illustrate the purpose and not to assume that 6 subcodons are in anyway preferred. Thus, any number of subcodons can be chosen as desired such as 1, 2, 3, 4, 5, 6, 7, 8, 9, 10 or more than 10 subcodons as chosen by the experimenter.

Example of Subset Encoding of Pre-Classified Building Blocks or a Combination of Building Blocks In certain aspect of the present technologies and any related technologies using DNA-tags for the encoding of chemical compounds, it may be desirable to enhance or reduce specific features within a selection output. The sequencing or otherwise deification of enriched molecules from a selection output may be dominated by DNA-tags encoding chemical fragments or full-size molecules with features that are less desirable for an optimised ligand for the target. It could be envisioned that the final molecules are too heavy, too polar, too charged, too lipophilic, too flexible etc. Consequently, if such molecules dominate the selection output it may be desirable that one or more subsets with desired characteristics within the encoded library can be specifically addressed and/or enhanced in the selection output.

In one example, building blocks entering a library at position 1 can be pre-categorised and grouped according to their molecular weight. F. ex using 4 groups A-D: A) MW<150 Da; B) MW 150-180 Da; C) MW 180-210 Da; D) MW>210 Da The 4 different building blocks groups are encoded by a first codon containing a group-specific sequence. The group-specific sequence can be used for selective amplification by PCR allowing selective read-out and sequencing of only the desired one or more subsets.

Furthermore, the group-specific sequence could constitute sites for DNA restriction enzymes, useful for the selective removal of undesired sub-groups by cleavage of the selection input or output material using relevant endonucleases Example of Designed Sub-Codons are Shown Below for a First Encoding Position The Display sequence: 5'-CAAGTCACCAAGAATT-CATG-3' (SEQ ID NO 7) in the sequences below represent a fixed 5'-end sequence common to all encoding tags. The fixed sequence is useful for the undiscriminative amplication of tags regardless of subsets at the first encoding position.

Consequently, a PCR reaction conducted with said primer sequence will not discriminate between encoding tags at the first encoding position and thus sustain the amplification of all position 1 subsets. A codon set marked Aset-0001/Axset-0001 represent one set of a codon series with a top and bottom DNA strand. The Aset-0001 contains a 5'-end phosphate marked p for ligation to the Display sequence carrying a 5'-end polyethyleneglycol-linker with a terminal amino-handle for chemical reaction. Aset-0001 is divided into 4 different encoding segments A-D.

A) 5'-TAGCAC-3' is a subcodon identifier sequence,
B) 5'-GATGCTTCCT-3' (SEQ ID NO 8) is a 10 nt codon sequence,
C) 5'-3' is a 6 nt degenerated sequence (Barcode) for detection of artifacts arising from events such as uneven amplification by PCR of library tags or sequencing bias introduced by the sequencing technology or tag recombination events.

D) 5'-CCTAGGACCA-3' (SEQ ID NO 9) is a fixed sequence for hybridization to neighbouring tags.

The Aset-0017 tag carries the same C+D sequence elements as Aset-0001 but a unique A) element with the sequence 5'-TAGTCT-3' and a unique B) element 10 nt codon sequence 5'-GTGCAACTTT-3'(SEQ ID NO 10). The third subset Aset-0033 contains the same C+D elements as Aset-0001 and Aset-0017 but a separate A) element with the sequence 5'-GTAACC-3' a unique B) codon element 5'-GACGAAGCAC-3' (SEQ ID NO 11). All A sequence elements are sub-group specific codons of 3 nt each allowing specific amplification of the desired subset.

F.ex a PCR reaction using the forward primer SetF_1-32_MDL280907 with the sequence 5'-CAAGTCAC-CAAGAATTCATGTAG (SEQ ID NO 12) will allow amplification of tags containing subcodons of the Aset-0001 series and Aset-0017 series but not the Aset-0033 subset. A PCR reaction using a forward primer SetF_1-16_MDL280907 with the sequence 5'-CAAGTCACCAAGAATT-CATGTAGCAC (SEQ ID NO 13) will only allow amplification of the Aset-0001 and not the Aset-0017 and Aset-0033 subcodon set. A PCR reaction with the primer SetF_17-32_MDL280907 with the sequence 5'-CAAGT-CACCAAGAATTCATGTAGTCT-3' (SEQ ID NO 14) will allow amplification of the Aset-0017 but not the Aset-0001 and Aset-0033 subcodons.

Finally, amplification using SetF_33-48_MDL280907 with the sequence 5'-CAAGTCACCAAGAATT-CATGGTAACC-'3 (SEQ ID NO 15) will allow amplification of the Aset-0033 subset but not the Aset-0001 and Aset-0017 subsets. A similar subset encoding may be envisioned for the second and/or third, and/or fourth and/or fifth and/or sixth and/or seventh and/or eighth and/or ninth and/or tenth and/or more than ten encoding positions.

The subset encoding may be used at single position or in more than one positions as suitable. In some embodiments of the present invention it may be desirable to use subset codons containing sequences for the selective cleavage of one or more restriction endonucleases. If the A elements described above was composed of restriction sites each subset tag could be selective cleaved to remove the tags from the pool of library tags by preventing subsequent tag identification by sequencing.

Consequently, a library could be cleaved with one or more nucleases prior to selection, during selection, immediately following selection or following selection and PCR amplification to remove a subset of the tag output before sequence identification. Any use of, and method for, subset encoding and the selective retrieval or removal of a subset of library tags of value for maximum information of library molecules and selected ligands are incorporated herein.

SetF_1-32_MDL280907
(SEQ ID NO 12)
CAAGTCACCAA*GAATTC*ATGTAG

SetF_1-16_MDL280907
(SEQ ID NO 13)
CAAGTCACCAAGAATTCATGTAGCAC

Aset-0001
(SEQ ID NO 16)
pTAGCACGATGCTTCCTNNNNNNNCCTAGGACCA

Axset-0001
(SEQ ID NO 17)
3'GTTCAGTGGTT*CTTAAG*TACATCGTGCTACGAAGGA

SetF_17-32_MDL280907
(SEQ ID NO 14)
CAAGTCACCAA*GAATTC*ATGTAGTCT

Aset-0017
(SEQ ID NO 18)
pTAGTCTGTGCAACTTTNNNNNNNCCTAGGACCA

AxSet-0017
(SEQ ID NO 19)
3'GTTCAGTGGTT*CTTAAG*TACATCAGACACGTTGAAA

SetF_33-48_MDL280907
(SEQ ID NO 15)
CAAGTCACCAA*GAATTC*ATGGTAACC

Aset-0033
(SEQ ID NO 20)
pGTAACCGACGAAGCACNNNNNNNCCTAGGACCA

AxSet-0033
(SEQ ID NO 21)
3'GTTCAGTGGTT*CTTAAG*TACCATTGG

Example of Using DNA-Damaging Chemical Reactions for DNA-Encoded Chemical Libraries Much chemistry using transition metals as catalyst is not compatible with the presence of intact DNA. Transition metals such as palladium and copper has adverse effects on DNA stability but are useful catalyst in many chemical reactions such as Suzuki, Heck, Buchwald-Hartwig, Sonogashira, aldol couplings etc (KBJ fyld pa). Consequently, any method for reducing DNA damage such as by shielding the DNA while conducting efficient chemical transformation on a DNA-tethered reactive handle using transition metals or other reagents harmful to the DNA, is well appreciated and incorporated herein.

In one embodiment DNA phase-transfer reagents such as CTAB (cetyltrimethylammoniumbromide) may be added to the DNA prior to the reaction with chemical reagents harmful to the DNA. CTAB can bind the polyanion backbone of DNA to protect the DNA from adverse reactions or alternatively the CTAB may form micelles to separate the DNA from harmful chemical entities.

Example of Suzuki reaction conditions:

1) 10 nmol of DNA with a reactive Iodo-aromate handle is supplied in 10 µl of $H_2O$.
2) 1 µl of 10 mM of CTAB is added and the sample is lyophilized.
3) Add 45 µl 100 mM $Na_2CO_3$ (pH 11.5)
4) Add 2 mg PdOAc/Phosphine
5) Add 5 µl of 500 mM Boronic acid building block in Isopropanol
6) Incubate at 80° C. ON
7) Add 20 µL $H_2O$
8) Purify by P6 gel-filtration column.

CTAB is removed by addition of 2 M ammonium acetate followed by ethanol precipitation.

Other DNA binding polymers such as glycogen, chitin, poly-amines and poly-imidazoles can bind the DNA in the major and/or minor groove of duplex DNA to increase stability during chemical reactions.

Example of Suzuki reaction conditions 1) 10 nmol of dsDNA with one reactive Iodo-aromate handle is supplied in 10 µl of $H_2O$.
2) 1 µl of 500 mM of spermidine is added and the sample is lyophilized.
3) Add 45 µl 100 mM $Na_2CO_3$ (pH 11.5)
4) Add 2 PdOAc/Phosphine 5) Add 5 µl of 500 mM Boronic acid building block in Isopropanol
6) Incubate at 80° C. ON
7) Add 20 µL H$_2$O
8) Purify by P6 gel-filtration column.

In another embodiment, water-in-oil emulsion can act to separate DNA from the reactive species. Alternative, addition of detergents or vigorous vortexing of non-mixable solvents can create "small-particle in solution" mixtures capable of reactions while separating DNA and any harmful reagents.

In yet another embodiment the chemical reaction occurs with DNA in solution while the DNA-damaging reagents are encapsulated/caged. For example, transitions metals or chemical reagents can be encapsulated in a polymer matrix (such as Reaxas PdEncat product)

Example of Suzuki reaction conditions:
1) 10 nmol of Iodo-aromat containing DNA oligonucleotide is lyophilized
2) Add 45 µl 100 mM Na$_2$CO$_3$ (pH 11.5)
3) Add 2 mg PdEnCat (Sigma/Aldrich cat #644706)
4) Add 5 µl 500 mM boronic acid building blocks in isopropanol
5) Incubate at 80° C. ON in PCR machine
6) Add 20 µL H2O
7) Purify by P6 spin column In yet another embodiment the DNA can be temporarily fixed covalently or noncovalently to a solid-support for the purpose of shielding the DNA from harmful reactive chemical entities. In one example DNA is bound non-covalently to a diethylaminoethyl-sepharose beads (DEAE sepharose, GE healthcare #).

Example of Suzuki reaction conditions
1) 10 nmol of Iodo-aromat DNA-oligonucleotide is provided in 10 µl of H2O
2) 25 µl of DEAE-sepharose prewashed with H2O is added to 1) and Incubated for 10 min.
3) Excess H2O is removed
4) Add 45 µl 100 mM Na$_2$CO$_3$ (pH 11.5)
5) Add PdOAc/Phosphine)
6) Add 5 µl 500 mM boronic acid building blocks in isopropanol
7) Incubate at 80° C. ON in PCR machine
8) Add 20 µL H2O
9) Purify by P6 spin column
Example of Encapsulation of Reagents In certain embodiments it may be desirable to conduct chemical reactions using reagents potentially harmful to the stability of DNA. To avoid detrimental DNA damage, encaging or encapsulation of chemical constituents may be able to sustain chemical reactivity of a chemical entity connected to DNA-tags while shielding DNA-tags from direct contact with the harmful reagents such as transition metals. The following examples illustrate some strategies for reagent encapsulation and for DNA proximity enhancement of encapsulated reagents by introduction of surface charges for attraction of DNA-tags to the beads.

An oil-in-water emulsion shown in FIG. 12 (c.f. FIG. 12) is formed when stirring the organic and aqueous phase very rapidly. The beads with the encapsulated material are formed in the inter phase between the water and the organic medium.

The beads shown in FIG. 13 (c.f. FIG. 13) are formed when isocyanate on e.g. polymethylene polyphenylene di-isocyanate (PMPPI) is partly hydrolysed to amine with evolution of carbodioxide. The amine reacts further with a proximal isocyanate moiety.

Shown in FIG. 13 (c.f. FIG. 13) is an example of how the surface of the beads can be modified with covalently bound tertiary amine. R and R' can be any small aliphatic chain such as methyl and ethyl and n=1 to 8.

FURTHER EXAMPLES AND PREPARATIONS

The invention is further illustrated by the following examples. The use of the catalysts of the invention for catalysis of typical reactions is illustrated but the invention is not limited to the use of the catalysts for any specific reaction.

In the following examples GOSHENOL is polyvinyl alcohol, SOLVESSO 200 is just a high boiling (230-257° C.) mixture of aromatics (mainly naphthalenes), TERGITOL XD is the polyoxypropylene polyoxyethylene ether of butyl alcohol, REAX 100M is sodium lignosulfonate. REAX, TERGITOL and GOSHENOL are added as colloid stabilisers and detergents.

Preparation of Catalyst Example
1—Microencapsulated Pd(OAc), with Co-Encapsulated PPh$_3$ Due to air-sensitive nature of the ligand, the oil phase is prepared in a glove box. Pd(OAc)$_2$ (3.34 g, 98%) is dissolved in chloroform (46.82 g) and the solution stirred for 10 minutes. Triphenylphosphine (3.92 g, 99%, 1:1 molar ratio Pd/PPh$_3$) is then added and the solution stirred for a further 30 minutes. To this mixture, polymethylene polyphenylene di-isocyanate (PMPPI) (17.59 g) is added and the contents stirred for a further 60 minutes. The mixture is then added to a cooled (4° C.) aqueous mixture under inert atmosphere (N$_2$) containing 40% REAX 100 M solution (5.73 g), 20% TERGITOL XD solution (1.43 g) and 25% Poly Vinyl Alcohol (PVOH) solution (2.87 g) in deionised water (120 ml) while shearing (using a FISHER 4-blade retrieve-curve stirrer) at 500 rpm for 8 minutes. The shear rate is then reduced to 250 rpm and after being maintained at 4° C. for 90 minutes, the temperature of the batch is gradually allowed to warm to room temperature. At the onset of polymerisation (12° C.) a few drops of de-foamer (DrewPLus S-4382) are added. The suspension thus obtained is stirred at room temperature for 24 hours. The microcapsules are then filtered though a polyethylene frit (20 micron porosity) and the capsules washed on a filter bed according to the sequence: deionised water (5×100 ml), ethanol (3×100 ml), hexane (3×100 ml), and dried in a vacuum oven at 50° C.

Preparation of Catalyst Example 2—Microencapsulated Pd(OAc)$_2$ with Co-Encapsulated 2-dicyclohexylphosphino-2',4',6'-triisopropyl-1,1'-biphenyl Due to air-sensitive nature of ligand the organic phase is prepared under a nitrogen atmosphere. The organic phase is formed from Pd(OAc)$_2$ (0.94 g, 98%) dissolved in chloroform (27 g) and then stirred for 10 minutes followed by addition of 2-dicyclohexylphosphino-2', 4',6'-triisopropyl-1, 1'-biphenyl (2.0 g, 98%, 1:1 Pd:P). To this mixture is added polymethylene polyphenylene di-isocyanate (PMPPI) (10.0 g) and the contents stirred for a further 120 minutes. This organic phase mixture is then added to an aqueous phase, cooled to 1° C., containing 40% REAX 100 M solution (7.99 g), 20% TERGITOL XD solution (3.99 g) and 25% Poly Vinyl Alcohol (PVOH) solution (6.39 g) in deionised water (67.10 ml) while shearing (using a FISHER 4-blade retreatcurve stirrer) at 500 rpm for 8 minutes. The reaction was maintained under inert atmosphere ($N_2$) throughout. After 8 minutes the shear rate was reduced to 160 rpm and few drops of de-foamer (DrewPLus S-4382) were added during the onset of polymerisation (detected by carbon dioxide evolution). The suspension thus obtained was stirred at 1° C. for a further 30 minutes, then maintained at 5° C. for 18 hours, warmed to 45° C. and maintained at this temperature for a further 2 hours. The microcapsules were then filtered though a polyethylene frit (20 micron porosity) and the capsules washed on a filter bed according to the following sequence: deionised water (5×100 ml), DMF (2×50 ml), ethanol (2×50 ml), toluene (2×50 ml), hexane (2×50 ml), and finally dried in a vacuum oven at 50° C.

Example of Library Synthesis Utilizing Multicomponent Reactions 96 different oligonucleotide tags, A1-A96 were synthesized using the protocol above, maintained on solid-support and deprotected on the terminal amine using the following protocol (in this example 96 different oligonucleotides are used).

However, the protocol is not fixed and can easily be scaled to any number between 1 and 10.000 or beyond 10.000 in a high-throughput format at any desired scale suitable for the experimenter.

Deprotection

Protected oligonucleotides A1-A96 maintained on solid-support

To each column add 0.3 ml Dichloromethane (DCM).
Incubate at RT for 15 min
Add 0.3 ml 2% DCA in DCM Incubate 1 min and drain
Add 0.3 ml 2% DCA in DMF. Incubate 5 min and drain (turn yellow)
Repeat until no color development
Wash ×3 with 0.3 ml DCM and inc. 5 min.

Each of the tags A1-A96 on solid support was reacted with a unique building block (BBa1-a96) using an acylation reaction as shown elsewhere in the examples. Building blocks were selected as suitably protected NH—R—COOH, NR'—R—COOH, NH—CH(R)—COOH, NR'—CH(R)—COOH, NR'—R—COOH or NH—R'—NR—CH$_2$—COOH reactants where R or R' can be any chemical entity f.ex a chemical entity listed elsewhere in this application.

The protection group used in this example is preferable Fmoc, which was removed using standard conditions chosen from Greene, "Protective Groups In Organic Synthesis," (John Wiley & Sons, New York (1999). Orthogonal protection groups on R-groups are present whenever relevant for the feasibility of the overall library chemistry.

Multicomponent Reactions for Generation of Position 2 Building Blocks (BBb1-b96)

Multicomponent Reactions (MCRs) are convergent reactions, in which three or more starting materials react to form a product, where basically all or most of the atoms contribute to the newly formed product (A. Dömling, I. Ugi, *Angew. Chem. Intl. Ed.* 2000, 39, 3168).

In an MCR, a product is assembled according to a cascade of elementary chemical reactions. Thus, there is a network of reaction equilibria, which all finally flow into an irreversible step yielding the product. The challenge is to conduct an MCR in such a way that the network of pre-equilibrated reactions channel into the main product and do not yield side products.

The result is clearly dependent on the reaction conditions: solvent, temperature, catalyst, concentration, the kind of starting materials and functional groups. (A. Dömling in: *Multicomponent Reactions* (J. Zhu, H. Bienayme) Wiley-VCH, Weinheim 2005, p. 76).

More than 500 different scaffolds have been described in the literature so far, where 18 of these scaffolds are shown herein below. Many of these reactions are base catalyzed which works well in combination with DNA.

Other MCR's requires acidic catalysis which is known to be troublesome in combination with DNA. In these cases a mild lewis catalysis like $NH_4Cl$, LiBr in aprotic solvents, should be used.

Some of the procedures described below require an alternative protection strategy for the phosphate backbone or the nucleobases. The phosphate groups in the DNA backbone are usually protected with cyanoethyl group, but alternative protection groups for the phosphates like the methyl and other more stable groups are known from the literature.

Multicomponent reaction can be combined with a reaction where suitable R groups react and thus forms a ring structure. One example of this is ring closure metathesis (*Chem. Commun.* 2003 596) where 2 of the R groups contain an alkene functionality.

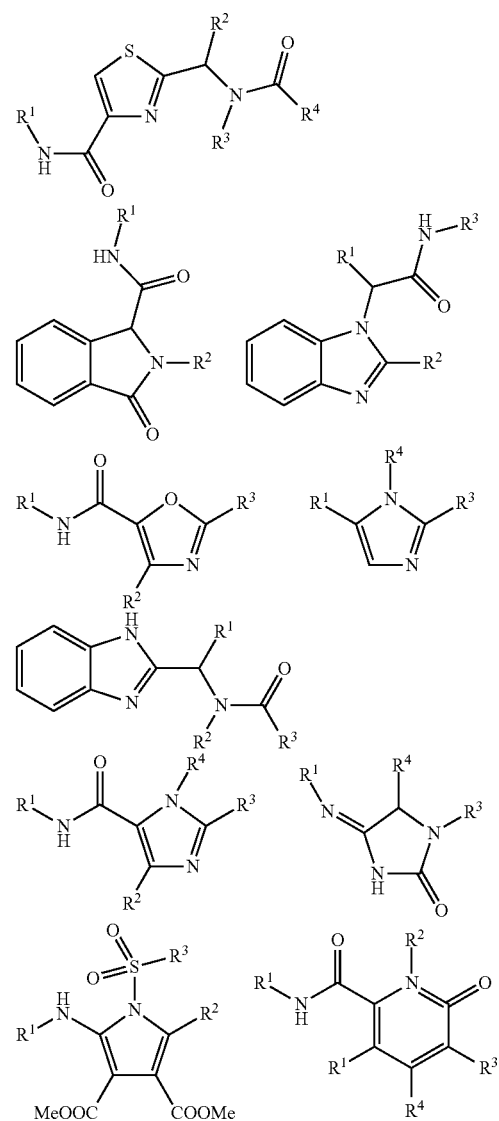

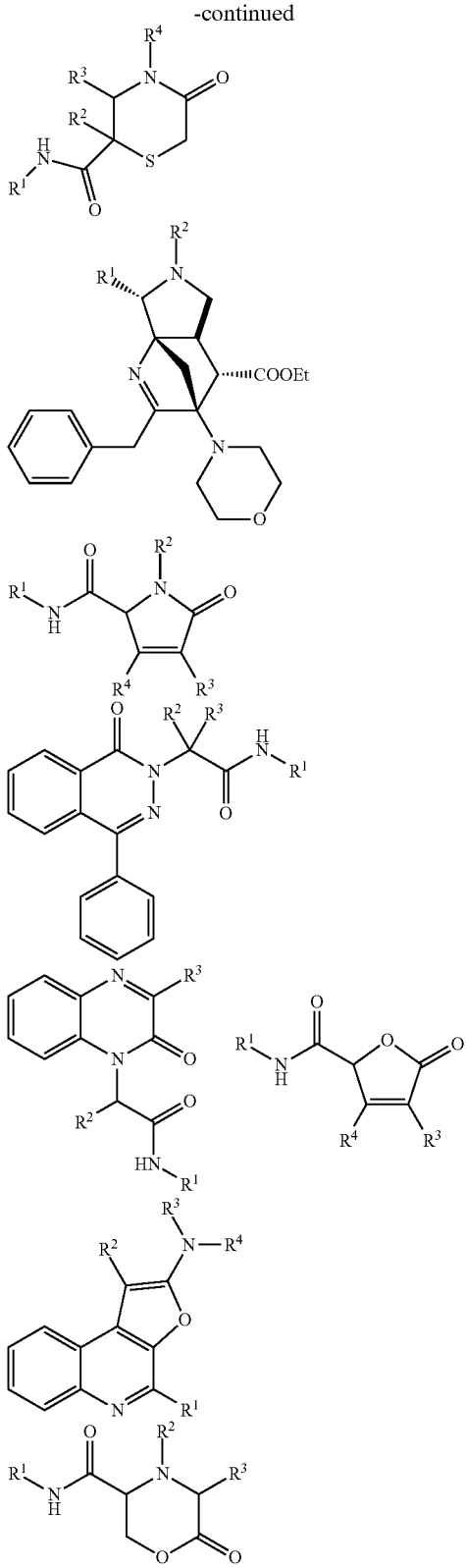

The above formulas are illustrative of 18 examples of scaffolds generated by multicomponent reactions.

Uqi 4 component reaction used for generation of position 2 building blocks (BBb1-b96): After a mix and a split step into 96 different positions of the oligonucleotides (A1-A96)-(BBa1-96) complexes, an array of 3 isonitrils and 4 aldehydes were mixed with 8 acids, each mixture transferred to one individual oligonucleotide and allowed to react at ambient temperature ranging from 20-150° C. giving rise to 9216 formed compounds as a combination of position 1 and position 2.

Add the acid 25 µl 0.5 M in DCM, add isonitrile 25 µl 0.5M in DCM, add aldehyde 25 µl 0.5 M in DCM and add 25 µl alcohol (methanol, ethanol, isopropanol, trifluoroethanol, hexaisofluoroisopropanol or the likes). Heated in a sealed multiposition plate in the microwave oven for 15 min or allowed to react at ambient temperature for 24-48 hours.

Aldehydes selected from the list of: aldehydes list No. 2
Acids selected from the list of: Acids list No. 4
Isonitriles selected from the list of: isonitrile (methyl ester) list No. 1

Protection groups was removed using standard conditions chosen from Greene, "Protective Groups In Organic Synthesis," (John Wiley & Sons, New York (1999). Washed with 3×DMF, 3×DCM.

Deprotect oligonucleotide and cleave from resin using standard methods for the selected protection and attachment strategy ("Protective Groups In Organic Synthesis," (John Wiley & Sons, New York (1999)) followed by purification on either a spin column or by reverse phase chromatography described elsewhere in this patent application and 96 different oligonucleotide tags, B1-B96 are enzymatically attached using the protocol described elsewhere in this application.

TOSMIC van Leusen 3 Component Reaction Used for Generation of Position 2 Building Blocks (BBb1-b96):

After a mix and a split step into 96 different positions of the oligonucleotides (A1-A96)-(BBa1-96) complexes, an array of 8 isonitriles and 12 aldehydes were created, each mixture transferred to one individual oligonucleotide and allowed to react at ambient temperature ranging from 20-150° C. giving rise to 9216 formed compounds as a combination of position 1 and position 2. (M. van Leusen, J. Wildeman, O. H. Oldenziel, J. Org. Chem. 1977, 42, 1153. A. M. van Leusen, Heterocycl. Chem. 1980, 5, S-111)

Add the aldehyde 25 µl 0.5 M in DMF incubate for 30 minutes, add isonitrile (TOSMIC reagent) 25 µl 0.5M in DCM and add triethylamine, diisopropylethylamine or morpholine 25 µl 2 M in DCM. Heated in a sealed multiposition plate in the microwave oven for 15 min or allowed to react at ambient temperature for 24-48 hours.

Aldehydes selected from the list of: aldehydes list No. 2
Isonitrile selected from the list of: isonitrile(tosmic) list No. 1

Protection groups was removed using standard conditions chosen from Greene, "Protective Groups In Organic Synthesis," (John Wiley & Sons, New York (1999). Washed with 3×DMF, 3×DCM.

Deprotect oligonucleotide and cleave from resin using standard methods for the selected protection and attachment strategy ("Protective Groups In Organic Synthesis," (John Wiley & Sons, New York (1999)) followed by purification on either a spin column or by reverse phase chromatography described elsewhere in this patent application and 96 different oligonucleotide tags, B1-B96 are enzymatically attached using the protocol described elsewhere in this application.

Petasis 3 Component Reaction Used for Generation of Position 2 Building Blocks (BBb1-b96):

After a mix and a split step into 96 different positions of the oligonucleotides (A1-A96)-(BBa1-96) complexes, an array of 8 aldehydes and 12 boronic acids were created and allowed to react at ambient temperature ranging from 20-150° C. giving rise to 9216 formed compounds as a combination of position 1 and position 2.

Add the aldehyde 25 µl 0.5 M in DCM incubate for 10 minutes mix with boronic acid 25 µl 1 M in DCM. Heated in a sealed multiposition plate in the microwave oven for 15 min or allowed to react at ambient temperature for 24-48 hours.

Aldehydes selected from the list of: aldehydes list No. 2

Boronic acids selected from the list of: Boronic acids list No. 3

Protection groups was removed using standard conditions chosen from Greene, "Protective Groups In Organic Synthesis," (John Wiley & Sons, New York (1999). Washed with 3×DMF, 3×DCM.

Deprotect oligonucleotide and cleave from resin using standard methods for the selected protection and attachment strategy ("Protective Groups In Organic Synthesis," (John Wiley & Sons, New York (1999)) followed by purification on either a spin column or by reverse phase chromatography described elsewhere in this patent application and 96 different oligonucleotide tags, B1-B96 are enzymatically attached using the protocol described elsewhere in this application.

Example of Library Synthesis Utilizing Organocatalytic Reactions 96 different oligonucleotide tags, A1-A96 were synthesized using the protocol above, maintained on solid-support and deprotected on the terminal amine using the following protocol (in this example 96 different oligonucleotides are used). However, the protocol is not fixed and can easily be scaled to any number between 1 and 10.000 or beyond 10.000 in a high-throughput format at any desired scale suitable for the experimenter.

Deprotection

Protected oligonucleotides A1-A96 maintained on solid-support To each column add 0.3 ml Dichloromethane (DCM). Incubate at RT for 15 min Add 0.3 ml 2% DCA in DCM Incubate 1 min and drain Add 0.3 ml 2% DCA in DMF. Incubate 5 min and drain (turn yellow) Repeat until no color development Wash ×3 with 0.3 ml DCM and inc. 5 min. Each of the tags A1-A96 on solid support was reacted with a unique building block (BBa1-a96) using an acylation reaction as shown elsewhere in the examples. Building blocks were selected as suitably protected NH—R—COOH, NR'—R—COOK NH—CH(R)—COOH, NR'—CH(R)—COOH, NR'—R—COOH or NH—R'—NR—CH$_2$—COOH reactants where R or R' can be any chemical entity f.ex a chemical entity listed elsewhere in this application. The protection group used in this example is Fmoc, was removed using standard conditions chosen from Greene, "Protective Groups In Organic Synthesis," (John Wiley & Sons, New York (1999). Orthogonal protection groups on R-groups are present whenever relevant for the feasibility of the overall library chemistry.

Organocatalytic Reactions for Generation of Position 2 Building Blocks (BBb1-b96)

Organocatalytic reaction have in the past ten years received an increasingly interest. Iminium-, enamine- and recently SOMO catalysis open a wide range of chemical reactions performed in the presence of DNA since all three types of activation lowers the activation energy of the chemical reactions and conditions are mild compared to traditional activation like Lewis acid catalysis. If the catalyst responsible for the organocatalytic reactions are carefully selected these types of reaction all runs with high enantioselectivity or diastereoselectivity, if stereoselectivity in the reaction, is undesired an achiral catalyst is chosen.

1,4-Addition of Electron-Rich Benzenes to α,β-Unsaturated Aldehydes.

After a mix and a split step into 96 different positions of the oligonucleotides (A1-A96)-(BBa1-96) complexes, 12 different anilines were attached to the oligonucleotide complexes using an acylation reaction as shown elsewhere in the examples, each aniline added to 8 positions. An array of reactions are created by addition of 8 different croton aldehydes, preactivated with the catalyst, to each of the 12 anilines, attached to different oligonucleotides and allowed to react at ambient temperature ranging from +20-150° C. giving rise to 9216 formed compounds as a combination of position 1 and position2. J. Am. Chem. Soc. 2002, 7894.

Add the aniline 25 µl 0.1 M in DMF, add HATU (2-(7-Aza-1H-benzotriazole-1-yl)-1,1,3,3-tetramethyluronium hexafluorophosphate) and 24 µl 0.1 M, 25 µl 0.2 M Dipea (diisopropylamine) in DMF.

Incubate for 1 hour at 25° C.

Washed with 3×DMF, 3×DCM.

A mixture of the crotonaldehyde 25 µl 0.5 M in DCM, catalyst ((2S,5S)-5-benzyl-2-tert-butyl-3-methylimidazolidin-4-one) 25 µl 0.05M in DCM and 24 µl 0.05 M HCl (made from 4N HCl in dioxane, pH are carefully checked in a test mixture of catalyst and HCl). Incubate 30 min and transfer to oligonucleotide, allow to react at ambient temperature for 24 48 hours Anilines selected from the list of: anilines List No. 6

Crotonaldehydes selected from the list of: crotonaldehydes List No. 7

Protection groups was removed using standard conditions chosen from Greene, "Protective Groups In Organic Synthesis," (John Wiley & Sons, New York (1999). Washed with 3×DMF, 3×DCM.

Deprotect oligonucleotide and cleave from resin using standard methods for the selected protection and attachment strategy ("Protective Groups In Organic Synthesis," (John Wiley & Sons, New York (1999)) followed by purification on either a spin column or by reverse phase chromatography described elsewhere in this patent application and 96 different oligonucleotide tags, B1-B96 are enzymatically attached using the protocol described elsewhere in this application.

Organocatalytical Cyclopropanations of α,β-Unsaturated Aldehydes.

After a mix and a split step into 96 different positions of the oligonucleotides (A1-A96)-(BBa1-96) complexes, 12 different methylketones were attached to the oligonucleotide complexes using an acylation reaction as shown elsewhere in the examples, transformed into the corresponding dimethylsulfonylide as described below, each ylide is present in 8 positions. An array of reactions are created by addition of 8 different crotonaldehydes, preactivated with the catalyst, to each of the 12 ylides formed from the methylketones, attached to different oligonucleotides and allowed to react at ambient temperature ranging from +20-150° C. giving rise to 9216 formed compounds as a combination of position 1 and position 2. J. Am. Chem. Soc. 2005, 3240.

Add the methylketone 25 µl 0.1 M in DMF, add HATU (2-(7-Aza-1H-benzotriazole-1-yl)-1,1,3,3-tetramethyluronium hexafluorophosphate) and 24 µl 0.1 M, 25 µl 0.2 M Dipea (diisopropylamine) in DMF.

Incubate for 1 hour at 25° C.

Washed with 3×DMF, 3×DCM.

Methylketones are transformed into α-keto bromides or iodides by reaction with NBS (N-bromo-succinimide) or NIS (N-iodo-succinimide), respectively. Other reagents with similar reactivity is also possible.

Add 100 µl 0.1 M NBS in $CHCl_3$.
Incubate for 60 min at ambient temperature.
Washed with 3×DCM.
Add 100 µl 0.5 M dimethylsulfide in DCM.
Incubate for 60 min at ambient temperature.
Washed with 3×DCM.
A mixture of the crotonaldehyde 25 µl 0.5 M in $CHCl_3$ and catalyst ((S)-(-)-indoline-2-carboxylic acid) 25 µl 0.05M in DCM
Incubate 30 min and transfer to oligonucleotide, allow to react at ambient temperature for 24 48 hours.
Crotonaldehydes selected from the list of: crotonaldehydes List No. 7
Methylketones selected from the list of: Methylketones List No. 8
Washed with 3×DMF, 3×DCM.
Deprotect oligonucleotide and cleave from resin using standard methods for the selected protection and attachment strategy ("Protective Groups In Organic Synthesis," (John Wiley & Sons, New York (1999)) followed by purification on either a spin column or by reverse phase chromatography described elsewhere in this patent application and 96 different oligonucleotide tags, B1-B96 are enzymatically attached using the protocol described elsewhere in this application.

Cross-Aldol Reaction of Aldehydes.

After a mix and a split step into 96 different positions of the oligonucleotides (A1-A96)-(BBa1-96) complexes, 12 different carboxylic acid-aldehydes were attached to the oligonucleotide complexes using an acylation reaction as shown elsewhere in the examples, An array of reactions are created by addition of 8 different aldehydes, premixed with the catalyst, to each of the 12 aldehydes attached to different oligonucleotides and allowed to react at ambient temperature ranging from +20-150° C. giving rise to 9216 formed compounds as a combination of position 1 and position 2. J. Am. Chem. Soc. 2002, 6798.

Add the carboxylic acid—aldehyde 25 µl 0.1 M in DMF, add HATU (2-(7-Aza-1H-benzotriazole-1-yl)-1,1,3,3-tetramethyluronium hexafluorophosphate) and 24 µl 0.1 M, 25 µl 0.2 M Dipea (diisopropylamine) in DMF.
Incubate for 1 hour at 25° C.
Washed with 3×DMF, 3×DCM.
A mixture of the aldehyde 25 µl 0.5 M in DMF and catalyst ((S)-proline) 25 µl 0.05M in DMF.
Transfer to oligonucleotide, allow to react at ambient temperature for 24-48 hours
Aldehydes selected from the list of: aldehydes list No. 2
Carboxylic acid-aldehydes selected from the list of: Carboxylic acids—aldehydes List No. 5
Washed with 3×DMF, 3×DCM.
Deprotect oligonucleotide and cleave from resin using standard methods for the selected protection and attachment strategy ("Protective Groups In Organic Synthesis," (John Wiley & Sons, New York (1999)) followed by purification on either a spin column or by reverse phase chromatography described elsewhere in this patent application and 96 different oligonucleotide tags, B1-B96 are enzymatically attached using the protocol described elsewhere in this application.

Examples of Library Synthesis Utilizing Heterocycle Generating Reactions.

96 different oligonucleotide tags, A1-A96 were synthesized using the protocol above, maintained on solid-support and deprotected on the terminal amine using the following protocol (in this example 96 different oligonucleotides are used). However, the protocol is not fixed and can easily be scaled to any number between 1 and 10.000 or beyond 10.000 in a high-throughput format at any desired scale suitable for the experimenter.

Deprotection

Protected oligonucleotides A1-A96 maintained on solid-support To each column add 0.3 ml Dichloromethane (DCM). Incubate at RT for 15 min Add 0.3 ml 2% DCA in DCM Incubate 1 min and drain Add 0.3 ml 2% DCA in DMF. Incubate 5 min and drain (turn yellow) Repeat until no color development Wash ×3 with 0.3 ml DCM and inc. 5 min. Each of the tags A1-A96 on solid support was reacted with a unique building block (BBa1-a96) using an acylation reaction as shown elsewhere in the examples. Building blocks were selected as suitably protected NH—R—COOH, NR'—R—COOH, NH—CH(R)—COOH, NR'—CH(R)—COOH, NR'—R—COOH or NH—R'—NR—$CH_2$—COOH reactants where R or R' can be any chemical entity f.ex a chemical entity listed elsewhere in this application. The protection group used in this example is Fmoc, was removed using standard conditions chosen from Greene, "Protective Groups In Organic Synthesis," (John Wiley & Sons, New York (1999). Orthogonal protection groups on R-groups are present whenever relevant for the feasibility of the overall library chemistry.

Reactions Between Di-Nucleophiles and Di-Electrophiles for Generation of Position 2 Building Blocks (BBb1-b96)

Several reactions which generates heterocycles are known, most of these reactions can be used in connection with protected DNA when conditions are carefully selected. Obvious strong protic acid must be avoided, but mild Lewis acids like $NH_4Cl$, LiBr or similar can be used as alternatives when the right solvent and temperature is applied (Name Reactions in Heterocyclic Chemistry, Lie Jack Li, 2005

Knorr Pyrazole Synthesis.

After a mix and a split step into 96 different positions of the oligonucleotides (A1-A96)-(BBa1-96) complexes, 12 different carboxylic acid-aldehydes were attached to the oligonucleotide complexes using an acylation reaction as shown elsewhere in the examples, each aldehyde added to 8 positions. These aldehydes were transformed into the corresponding hydrazines by reductive amination using either trifluoroacetic acid hydrazide, Fmoc hydrazide (9-fluorenylmethyl carbazate) or hydrazine hydrochloride followed by subsequent deprotection. An array of reactions are created by addition of 8 different dicarbonyls or β-ketoesters, to each of the 12 hydrazines aldehydes attached to different oligonucleotides and allowed to react at ambient temperature ranging from 20-150° C., using standard heating or microwave heating, giving rise to 9216 formed compounds as a combination of position 1 and position2. Add the carboxylic acid-aldehydes 25 µl 0.1 M in DMF, add HATU (2-(7-Aza-1H-benzotriazole-1-yl)-1,1,3,3-tetramethyluronium hexafluorophosphate) and 24 µl 0.1 M, 25 µl 0.2 M Dipea (diisopropylamine) in DMF.

Incubate for 1 hour at 25° C.

Washed with 3×DMF, 3×DCM.

Add Fmoc hydrazide 25 µl 0.1 M in THF, and 25 µl trimethyl orthoformate, incubate for 1 h at rt., add sodiumcyanoborohydride 25 µl 0.1 M in DMF/MeOH 3:1 incubate for 16 h at rt.

Wash with 3×DMF

Add piperidine/DMF 1:4 wait 5 minutes drain and repeat treatment.

Washed with 3×Methanol, 3×DMF, 3×DCM.

Add a mixture of the dicarbonyl 25 µl 0.5 M in THF, catalyst Lithium bromide 25 µl 0.05M in THF to oligonucleotide, allow to react at ambient temperature for 24 48 hours Carboxylic acid-aldehydes selected from the list: Carboxylic acid-aldehydes List No. 5

Dicarbonyls selected from the list: dicarbonyls List No. 9

Washed with 3×THF, 3×DMF, 3×DCM.

Deprotect oligonucleotide and cleave from resin using standard methods for the selected protection and attachment strategy ("Protective Groups In Organic Synthesis," (John Wiley & Sons, New York (1999)) followed by purification on either a spin column or by reverse phase chromatography described elsewhere in this patent application and 96 different oligonucleotide tags, B1-B96 are enzymatically attached using the protocol described elsewhere in this application.

Bioinelli Reaction.

After a mix and a split step into 96 different positions of the oligonucleotides (A1-A96)-(BBa1-96) complexes, 12 different carboxylic acid-aldehydes were attached to the oligonucleotide complexes using an acylation reaction as shown elsewhere in the examples, each aldehyde added to 8 positions. An array of reactions are created by addition, of 8 different β-ketoesters or β-ketoamides mixed with either urea or thiourea, to each of the 12 aldehydes attached to different oligonucleotides and allowed to react at ambient temperature ranging from 20-150° C., using standard heating or microwave heating, giving rise to 9216 formed compounds as a combination of position 1 and position2.

Add the carboxylic acid-aldehydes 25 µl 0.1 M in DMF, add HATU (2-(7-Aza-1H-benzotriazole-1-yl)-1,1,3,3-tetramethyluronium hexafluorophosphate) and 24 µl 0.1 M, 25 µl 0.2 M Dipea (diisopropylamine) in DMF.

Incubate for 1 hour at 25° C.

Washed with 3×DMF, 3×DCM.

Add a mixture of urea 25 µl 0.5 M in THF, β-ketoester 25 µl 0.5 M in THF and catalyst Lithium bromide 25 µl 0.05M in THF to oligonucleotide, allow to react at ambient temperature for 24 48 hours.

Carboxylic acid-aldehydes selected from the list: Carboxylic acid-aldehydes List No. 5

Dicarbonyls selected from the list: dicarbonyls List No. 9

Washed with 3×THF, 3×DMF, 3×DCM.

Deprotect oligonucleotide and cleave from resin using standard methods for the selected protection and attachment strategy ("Protective Groups In Organic Synthesis," (John Wiley & Sons, New York (1999)) followed by purification on either a spin column or by reverse phase chromatography described elsewhere in this patent application and 96 different oligonucleotide tags, B1-B96 are enzymatically attached using the protocol described elsewhere in this application.

Reverse Phase Chromatography Purification of Oligonucleotides:

Deprotected Oligoes:

Each oligonucleotide are dissolved in 20 µl solvent A and placed in a sealed 96 well plate and placed in the Waters ACQUITY autosampler. All samples are run through the Waters ACQUITY UPLC System with SQD-MS, controlled by MassLynx 4.1 and collected according to their target mass. MaxEnt is used to deconvolute massspec and compare with target mass (oligo-small molecule complex).

Column: Acquity UPLC BEH C18 1.7 µm 2.1×50 mm (Waters part 186002350)

Method used:

Solvent A: 200 mM HFIP 8.4 mM TEA 5% MeOH in water

Solvent B: 200 mM HFIP 8.4 mM TEA 60% MeOH in water

|  | Time (min) | Flow (ml/min) | % A | % B |
|---|---|---|---|---|
| Gradient: | Initial | 0.9 | 90 | 10 |
|  | 0.70 | 0.9 | 90 | 10 |
|  | 4.50 | 0.9 | 0 | 100 |
|  | 5.00 | 0.9 | 0 | 100 |
|  | 5.10 | 0.9 | 90 | 10 |
|  | 6.00 | 0.9 | 90 | 10 |

Column Oven Temperature: 65° C.

UV Detection: 254 nm

MS Detection: ESi(−), 6 min, 550-1300 Da; Cone 35 V; Source Temp 130° C.

Use spilt flow between MS and Fraction Collector (1:9)

Fractions containing the target mass were evaporated furnishing pure oligonucleotide.

Protected Oligoes:

The method outlined above for the Waters ACQUITY equipment can also be used applying protected oligonucleotide. Preferable the buffer content are lowered in both solvent A and B with a factor 10 or simply changed to solvent A: water and solvent B: acetonitrile.

Alternatively:

Full or partial protected oligonucleotides can also be purified using reverse phase cartridges in a single column or a parallel format using one of the different commercial available products such as the Glen-Pack from Glen research or "Discovery DSC-18Lt SPE 96-well Plate" from supelco.

The protected oligonucleotide must be applied on the column dissolved in a solvent composition with a moderate organic solvent strength. Therefore the oligonucleotides needs to be concentrated in a vacuum evaporator if dissolved in pure organics.

Dissolve the protected oligonucleotide in a mixture of water and acetonitrile (preferable with a content of acetonitril below 20%) apply the solution to a preconditioned cartridge water/acetonitrile 9:1 and wash with more water/acetonitrile 9:1. The protected oligonucleotide is eluated with a higher content of acetonitrile in the solvent used. Preferable a stepwise gradient is used starting with water/acetonitril 90:10 up to 90:10, raising 10% per 100 µl, 100 µl solvent per 100 µl adsorbent used.

Examples above from the multicomponent, organocatalytic or heterocyclic generating reactions could be carried out using oligoes detached from the solid support if a photolabile linker is used as the support. Only difference is that the wash procedures must be substituted with the purification protocol above.

Through all following lists, protection groups are applied when necessary, selected from "Protection Groups" $3^{rd}$ edition 2004 Philip J. Kocienski).

List No. 1—Isonitriles:

Tosmic-isonitriles: (1-PHENYL-1-TOSYL)METHYL ISOCYANIDE; (2,4-DIMETHYLPHENYL)(ISOCYANO) METHYL 4-METHYLPHENYL SULFONE; (3-METHOXYPHENYL)[(4-METHYLPHENYL)SULFONYL]ACETONITRILE; (4-METHOXYPHENYL)[(4-METHYLPHENYL)SULFONYL]ACETONITRILE; [1-

(2-FLUOROPHENYL)-1-TOSYL]METHYL ISOCYANIDE; [1-(2-TRIFLUOROMETHYLPHENYL)-1-TOSYL]METHYL ISOCYANIDE; [1-(3-CHLOROPHENYL)-1-TOSYL]METHYL ISOCYANIDE; [1-(3-FLUOROPHENYL)-1-TOSYL]METHYL ISOCYANIDE; [1-(3-TRIFLUOROMETHYLPHENYL)-1-TOSYL]METHYL ISOCYANIDE; [1-(4-TRIFLUOROMETHYLPHENYL)-1-TOSYL]METHYL ISOCYANIDE; 1-(2,3-DICHLOROPHENYL)-1-TOSYLMETHYL ISOCYANIDE; 1-(2,3-DIMETHOXYPHENYL)-1-TOSYLMETHYL ISOCYANIDE; 1-(2,4-DIMETHOXYPHENYL)-1-TOSYLMETHYL ISOCYANIDE; 1-(2,5-DIBROMOPHENYL)-1-TOSYLMETHYL ISOCYANIDE; 1-(2,5-DICHLOROPHENYL)-1-TOSYLMETHYL ISOCYANIDE; 1-(2,5-DIMETHOXYPHENYL)-1-TOSYLMETHYL ISOCYANIDE; 1-(2,6-DICHLOROPHENYL)-1-TOSYLMETHYL ISOCYANIDE; 1-(2,6-DIMETHOXYPHENYL)-1-TOSYLMETHYL ISOCYANIDE; 1-(2-CYCLOPROPYL-1-ISOCYANOETHYLSULFONYL)-4-METHYLBENZENE; 1-(3,4-DIBROMOPHENYL)-1-TOSYLMETHYL ISOCYANIDE; 1-(3,4-DICHLOROPHENYL)-1-TOSYLMETHYL ISOCYANIDE; 1-(3,5-DIBROMOPHENYL)-1-TOSYLMETHYL ISOCYANIDE; 1-(4-DIMETHYLAMINOPHENYL)-1-TOSYLMETHYL ISOCYANIDE; 1,3-DICHLORO-5-[ISOCYANO-(TOLUENE-4-SULFONYL)-METHYL]-BENZENE; 1-[(1-ISOCYANO-3-METHYLBUTYL)SULFONYL]-4-METHYL-BENZENE; 1-[ISOCYANO-(TOLUENE-4-SULFONYL)-METHYL]-NAPHTHALENE; 1-ALLYL-1-TOSYLMETHYL ISOCYANIDE; 1-BENZYL-1-TOSYLMETHYL ISOCYANIDE; 1-CYCLOBUTYL-1-TOSYLMETHYL ISOCYANIDE; 1-CYCLOHEXYL-1-TOSYLMETHYL ISOCYANIDE; 1-CYCLOPENTYL-1-TOSYLMETHYL ISOCYANIDE; 1-CYCLOPROPYL-1-TOSYLMETHYL ISOCYANIDE; 1-ETHOXYCARBONYL-1-TOSYLMETHYL ISOCYANIDE; 1-ETHYL-1-TOSYLMETHYL ISOCYANIDE; 1-FURAN-2-YL-1-TOSYLMETHYL ISOCYANIDE; 1-ISOCYANO-2-PHENYL-1-TOSYLETHENE; 1-ISOPROPYL-1-TOSYLMETHYL ISOCYANIDE; 1-METHYL-1-TOSYLMETHYL ISOCYANIDE; 1-M-TOLYL-1-TOSYLMETHYL ISOCYANIDE; 1-N-BUTYL-1-TOSYLMETHYL ISOCYANIDE; 1-N-PENTYL-1-TOSYLMETHYL ISOCYANIDE; 1-N-PROPYL-1-TOSYLMETHYL ISOCYANIDE; 1-O-TOLYL-1-TOSYLMETHYL ISOCYANIDE; 1-P-TOLYL-1-TOSYLMETHYL ISOCYANIDE; 1-PYRIDIN-2-YL-1-TOSYLMETHYL ISOCYANIDE; 1-PYRIDIN-3-YL-1-TOSYLMETHYL ISOCYANIDE; 1-PYRIDIN-4-YL-1-TOSYLMETHYL ISOCYANIDE; 1-PYRROL-2-YL-1-TOSYLMETHYL ISOCYANIDE; 1-THIOPHEN-2-YL-1-TOSYLMETHYL ISOCYANIDE; 2,4-DICHLORO-1-[ISOCYANO-(TOLUENE-4-SULFONYL)-METHYL]-BENZENE; 2-[ISOCYANO-(TOLUENE-4-SULFONYL)-METHYL]-NAPHTHALENE; 2-CHLORO-1-[ISOCYANO-(TOLUENE-4-SULFONYL)-METHYL]-BENZENE; 2-CHLORO-4-FLUORO-1-[ISOCYANO-(TOLUENE-4-SULFONYL)-METHYL]-BENZENE; 3-[ISOCYANO-(TOLUENE-4-SULFONYL)-METHYL]-BENZOIC ACID METHYL ESTER; 3-BROMO-1-[ISOCYANO-(TOLUENE-4-SULFONYL)-METHYL]-BENZENE; 4-[ISOCYANO-(TOLUENE-4-SULFONYL)-METHYL]-1,2-DIMETHOXY-BENZENE; 4-[ISOCYANO(TOLUENE-4-SULPHONYL)METHYL]BIPHENYL; 4-BROMO-1-[ISOCYANO-(TOLUENE-4-SULFONYL)-METHYL]-BENZENE; 5-[ISOCYANO-(TOLUENE-4-SULFONYL)-METHYL]-1,2,3-TRIMETHOXY-BENZENE; 5-[ISOCYANO-(TOLUENE-4-SULFONYL)-METHYL]-BENZO[1,3]DIOXOLE; 6-[ISOCYANO-(TOLUENE-4-SULFONYL)-METHYL]-2,3-DIHYDRO-BENZO[1,4]DIOXINE; A-(P-TOLYLSULFONYL)-A-((THIEN-3-YL)METHYL)ISOCYANIDE; ALPHA-(P-TOLUENESULFONYL)-4-FLUOROBENZYLISONITRILE; A-TOSYL-(2,3-DIFLUOROBENZYL)ISOCYANIDE; A-TOSYL-(2,4-DIFLUOROBENZYL)ISOCYANIDE; A-TOSYL-(2,5-DIFLUOROBENZYL) ISOCYANIDE; A-TOSYL-(2,6-DIFLUOROBENZYL)ISOCYANIDE; A-TOSYL-(2-BROMOBENZYL) ISOCYANIDE; A-TOSYL-(2-NITROBENZYL) ISOCYANIDE; A-TOSYL-(3,4-DIFLUOROBENZYL) ISOCYANIDE; A-TOSYL-(3,5-DIFLUOROBENZYL) ISOCYANIDE; A-TOSYL-(3-IODOMETHYLBENZYL)ISOCYANIDE; A-TOSYL-(3-NITROBENZYL) ISOCYANIDE; A-TOSYL-(4-CHLOROBENZYL) ISOCYANIDE; A-TOSYL-(4-IODOMETHYLBENZYL)ISOCYANIDE; A-TOSYL-(4-NITROBENZYL) ISOCYANIDE; ISOCYANO(2-METHOXYPHENYL)METHYL-4-METHYLPHENYL SULFONE; ISOCYANO(2-TERT-BUTYLSULFANYLPHENYL)METHYL-4-METHYLPHENYL SULFONE; PHENYLSULFONYLMETHYL ISOCYANIDE; TERT-BUTYL-3-ISOCYANO-3-TOSYLPROPANOATE; TOSYL-(2-FLUORBENZYL)-METHYL-ISOCYANIDE; TOSYL-(3-BROMBENZYL)-METHYL-ISOCYANIDE; TOSYL-(3-CHLORBENZYL)-METHYL-ISOCYANIDE; TOSYL-(3-CYANOBENZYL)-METHYL-ISOCYANIDE; TOSYL-(3-FLUORBENZYL)-METHYL-ISOCYANIDE; TOSYL-(3-METHYLBENZYL)-METHYL-ISOCYANIDE; TOSYL-(3-TRIFLUORMETHYLBENZYL)-METHYLISOCYANIDE; TOSYL-(4-BROMBENZYL)-METHYL-ISOCYANIDE; TOSYL-(4-CHLORBENZYL)-METHYL-ISOCYANIDE; TOSYL-(4-CYANOBENZYL)-METHYL-ISOCYANIDE; TOSYL-(4-FLUORBENZYL)-METHYL-ISOCYANIDE; TOSYL-(4-METHYLBENZYL)-METHYL-ISOCYANIDE; TOSYL-(4-TRIFLUORMETHYLBENZYL)-METHYLISOCYANIDE; TOSYLMETHYL ISOCYANIDE

Methyl esters; METHYL ISOCYANOACETATE; 6-ISOCYANOHEXANOICACIDMETHYL-ESTER; 5-ISOCYANOVALERIC ACID METHYL ESTER; TRANS-4-(ISOCYANOMETHYL)CYCLOHEXANE CARBOXYLIC ACID METHYL ESTER; 11-ISOCYANOUNDECANOIC ACID METHYL ESTER; D,L-3-ISOCYANO-N-BUTYRIC ACID METHYL ESTER; 4-ISOCYANOBUTYRIC ACID METHYL ESTER; 2-ISOCYANO-2-(4-FLUOROPHENYL) ACETIC ACID METHYL ESTER; 2-ISOCYANO-2-(4-CHLOROPHENYL)PROPIONIC ACID METHYL ESTER; 2-ISOCYANO-4-BENZYLOXYCARBONYLBUTYRIC ACID METHYL ESTER; 2,6-DIISOCYANOHEPTANEDIOIC ACID DIMETHYL ESTER; 2-ISOCYANO-2-(4-FLUOROPHENYL)-PROPIONIC ACID METHYL ESTER; 2-ISOCYANO-(INDOL-3-YL)-ACETIC ACID METHYL ESTER; 2-ISOCYANO-4-METHYLPENTANOIC ACID METHYL ESTER; 2-ISOCYANOHEXANOIC ACID METHYL ESTER; 2-ISOCYANOADIPIC ACID DIMETHYL ESTER; 2,5-DIISOCYANOVALERIC ACID METHYL ESTER; 2-(1'-ISOCYANOCYCLOHEXYL) ACETIC ACID METHYL ESTER; METHYL 3-ISOCYANO-3-(3-NITROPHENYL) PROPIONATE; METHYL 3-ISOCYANO-3-(4-METHYLPHENYL)PROPIONATE; METHYL-3-ISOCYANO-3-(4-BENZYLOXYPHENYL)PROPIONATE;

2-ISOCYANOOCTANOIC ACID METHYL ESTER; 2-ISOCYANOSUCCINIC ACID DIMETHYL ESTER; 2-ISOCYANOVALERIC ACID METHYL ESTER; METHYL 3-ISOCYANO-3-(3-FLUOROPHENYL)PROPIONATE; METHYL 3-ISOCYANO-3-(4-FLUOROPHENYL)PROPIONATE; METHYL 3-ISOCYANO-3-(4-ISOPROPYLPHENYL)PROPIONATE; 2-ISOCYANO-3-(BENZYLTHIO)PROPIONIC ACID METHYL ESTER; 2-ISOCYANO-2,4-DIMETHYLPENTANOIC ACID METHYL ESTER; 2-ISOCYANO-4-(METHYLTHIO)BUTYRIC ACID METHYL ESTER; METHYL-2-ISOCYANO-3-(METHYLTHIO)-PROPIONATE; 2-ISOCYANO-3,3-DIMETHYLBUTYRIC ACID METHYL ESTER; METHYL 3-ISOCYANO-3-(2-FLUOROPHENYL)PROPIONATE; METHYL 3-ISOCYANO-3-(3,4-METHYLENEDIOXYPHENYL)PROPIONATE; 3-DIMETHYLAMINO-2-ISOCYANOACRYLIC ACID METHYL ESTER; 2-ISOCYANO-3-PHENYLPROPIONIC ACID METHYL ESTER; METHYL 3-ISOCYANO-3-(4-HEXYLOXYPHENYL)PROPIONATE; METHYL 3-ISOCYANO-3-(2,3-DICHLOROPHENYL)PROPIONATE; METHYL-3-ISOCYANO-3-(4-CYANOPHENYL)PROPIONATE; METHYL 3-ISOCYANO-3-(4-METHYLTHIOPHENYL)PROPIONATE; METHYL 3-ISOCYANO-3-PHENYLPROPIONATE; METHYL-3-ISOCYANO-3-(4-BENZALDEHYDEDIETHYLACETAL)PROPIONATE; METHYL-3-ISOCYANO-3-(4-BROMOPHENYL)PROPIONATE; 2-ISOCYANOGLUTARIC ACID METHYL ESTER; METHYL 2-ISOCYANO-3-METHYLPENTANOATE; METHYL 3-ISOCYANO-3-(4-TRIFLUOROMETHYLPHENYL)PROPIONATE; METHYL 3-ISOCYANO-3-(4-METHOXYPHENYL) PROPIONATE; METHYL-3-ISOCYANO-4-CHLOROBENZOATE; METHYL-3-ISOCYANO-2-METHYL-BENZOATE; METHYL 3-ISOCYANO-4-METHYLBENZOATE; METHYL-4-ISOCYANOBENZOATE; METHYL-1-ISOCYANOCYCLOHEXYL-CARBOXYLATE; METHYL 3-ISOCYANOPROPANOATE; METHYL-3-ISOCYANOBENZOATE; METHYL 2-ISOCYANOISOVALERATE; 2-ISOCYANOPROPIONIC ACID METHYL ESTER; METHYL-2-ISOCYANO-ISOBUTYRATE; (S,R)-METHYL-2-ISOCYANO-3-METHYL-3-PHENYLPROPIONATE; METHYL-3-ISOCYANO-(3-METHOXYPHENYL)PROPIONATE; 8-ISOCYANOOCTANOIC ACID METHYL ESTER; METHYL-4-ISOCYANO-5-CHLORO-2-METHOXYBENZOATE; METHYL-3,5-DIISOCYANOBENZOATE; METHYL-3-METHYLCARBOXYMETHYL-THIO-2-ISOCYANO-PROPIONATE; METHYL-2-ISOCYANO-5-CHLORO-BENZOATE; METHYL-2-ISOCYANO-3-METHYL-BENZOATE; METHYL-2-ISOCYANO-6-CHLORO-BENZOATE; METHYL-2-ISOCYANO-6-FLUOR-BENZOATE; METHYL-2-ISOCYANO-5-BROMO-BENZOATE; METHYL-2-ISOCYANO-4,5-DIMETHOXY-BENZOATE; METHYL-3-ISOCYANO-2-NAPHTHALINOATE; METHYL-4-(ISOCYANOMETHYL)-BENZOATE; METHYL-2-ISOCYANO-3,5-DICHLORO-BENZOATE; METHYL-2-ISOCYANO-5-METHYL-BENZOATE; METHYL-2-ISOCYANO-6-METHYL-BENZOATE; METHYL-2-ISOCYANO-5-NITRO-BENZOATE; METHYL-2-ISOCYANO-4-FLUOR-BENZOATE; METHYL-3-ISOCYANOHEXANOATE; METHYL-2-ISOCYANO-3-(4-IMIDAZOLYL)PROPIONATE; METHYL-1-ISOCYANO-1-CYCLOPENTAN-CARBOXYLATE; 2-ISOCYANO-4-(METHYLSELENO) BUTYRIC ACID METHYL ESTER; METHYL-2-ISOCYANOBENZOATE; DIMETHYL 2-ISOCYANOTEREPHTHALATE; METHYL-2-ISOCYANO-4-CHLORO-BENZOATE; SCHOLLKOPF ISOCYANIDE; METHYL-3-[3,5-BIS(TRIFLUOROMETHYL)-PHENYL]-2-ISOCYANO-PROPIONATE; METHYL-2-ISOCYANO-3-(4-CHLOROPHENYL)-PROPIONATE; METHYL 3-(1H-INDOL-3-YL)-2-ISOCYANOPROPANOATE; METHYL 2-ISOCYANO-3-(4-BENZYLOXY-PHENYL)-PROPIONATE; METHYL-2-ISOCYANO-3-(4-FLUORO-PHENYL)-PROPIONATE; METHYL-4-ISOCYANO-3-METHYL-BENZOATE; METHYL-(−1-ISOCYANOCYCLOPROPYL)-CARBOXYLATE; METHYL-3-ISOCYANO-4-METHOXY-BENZOATE; METHYL 4-ISOCYANOPHENYLACETATE; 2-ISOCYANO-3-ACETYL PROPIONIC ACID METHYL ESTER; METHYL-2-ISOCYANONAPHTHALENE CARBOXYLATE; 2-ISOCYANOPHENYL ACETIC ACID METHYL ESTER; METHYL (2R)-2-AMINO-3-(4,6-DIAMINO-3-ISOCYANO(2-PYRIDYL))PROPANOATE; METHYL (2S)-2-AMINO-3-(4,6-DIAMINO-3-ISOCYANO(2-PYRIDYL))PROPANOATE; METHYL-4-ISOCYANO-3-(TRIFLUOROMETHOXY)-BENZOATE; METHYL-2-ISOCYANO-3-(TRIFLUOROMETHYL)-BENZOATE; METHYL-3-ISOCYANO-5-(TRIFLUOROMETHYL)-BENZOATE; METHYL-2-ISOCYANO-6-(TRIFLUOROMETHYL)-BENZOATE; METHYL-2-HYDROXYMETHYL-ISOCYANO-ACETATE; METHYL-3-(4-T-BUTOXYPHENYL)-2-ISOCYANO-PROPIONATE; METHYL-3-(N—BOC-AMINO)-5-ISOCYANO-BENZOATE; CN-GLY-PRO-OME; METHYL-2-FLUORO-4-ISOCYANOBUTYRATE; METHYL-3-ISOCYANO-4-FLUOROBENZOATE; METHYL-2-ISOCYANO-5-FLUOROBENZOATE; METHYL-2-FLUORO-4-ISOCYANOBENZOATE; METHYL-3-FLUORO-4-ISOCYANOBENZOATE; METHYL-2-FLUORO-5-ISOCYANOBENZOATE; 2-ISOCYANO-BUTANOIC ACID METHYL ESTER

Without methyl ester functionality; TERT-BUTYL ISOCYANIDE; 1,1,3,3-TETRAMETHYLBUTYL ISOCYANIDE; BENZYL ISOCYANIDE; N-BUTYLISOCYANIDE; CYCLOHEXYL ISOCYANIDE; 1,6-DIISOCYANOHEXANE; 1,4-DIISOCYANOBENZENE; 2,6-DIMETHYLPHENYL ISOCYANIDE; I-PROPYLISOCYANIDE; 2-MORPHOLINOETHYL ISOCYANIDE; 3-ISCYANOPROPYLTOSYLATE; (ISOCYANOMETHYL)TRIMETHYLSILANE; DIETHYL ISOCYANOMETHYLPHOSPHONATE; 3-ISOCYANATOPROPYLTRIMETHOXYSILANE; HEXYL ISOCYANIDE; 1-(ISOCYANOMETHYL)-1H-BENZOTRIAZOLE; 4-ETHYLPHENYL ISOCYANIDE; TRIPHENYLMETHYLISOCYANIDE; XANTHOASCIN; XANTOCILLIN; XANTHOCILLIN X MONOMETHYL ETHER; ETHYL ISOCYANIDE; 6-OXABICYCLO(3.1.0)HEX-3-ENE-2-METHANOL, 2-HYDROXY-4-ISOCYANO-ALPHA-METHYL-, (1-ALPHA,2-BETA,2(R*),5-ALPHA)-(−)-; BIS-(4-ISOCYANOPHENYL)METHANE; 3,5-BIS(TRIFLUOROMETHYL)PHENYLISOCYANIDE; 4-CHLORO-2-ISOCYANO-1-METHOXY-BENZENE; 2-ISOCYANO-5-CHLORBENZOTRIFLUORIDE; 2,3-DICHLOROPHENYLISOCYANIDE; 1,3-DICHLORO-5-ISOCYANOBENZENE; 1-ISOCYANO-2,5-DIMETHOXY-4-NITRO-BENZENE; 2-METHOXY-5-NITRO-PHENYL-ISOCYANIDE; 4-NITROPHENYLISOCYANIDE; 2-METHOXY-4-NITROPHENYL ISOCYANIDE; 2-METHYL-5-NITROPHENYL ISOCYANIDE; 4-METHYL-3-NITRO-PHE- NYLISOCYANIDE; 3-NITROPHENYLISOCYANIDE; CARDIO-SPECT; 1-ADAMANTANEISOCYANIDE; 4-METHOXYBENZYL ISOCYANIDE; 1-ETHOXY-4-(ISOCYANOMETHYL)BENZENE; 3-FLUOROBENZYLISOCYANIDE; 3-CHLOROBENZYLISOCYANIDE; 3-METHOXYBENZYLISOCYANIDE; 2-CHLOROBENZYLISOCYANIDE; 2-METHOXYBENZYLISOCYANIDE; 2-TRIFLUOROMETHYLBENZYLISOCYANIDE; 1-(2-ISOCYANOETHYL)-4-METHOXYBENZENE; 2-METHYLBENZYLISOCYANIDE; 3-METHYLBENZYLISOCYANIDE; 1-(ISOCYANOMETHYL)-4-METHYLBENZENE; 3,4-DIMETHOXYBENZYL ISOCYANIDE; 1,3-BENZODIOXOL-5-YLMETHYL ISOCYANIDE; (1-ISOCYANOETHYL)BENZENE; 2-PHENOXYPHENYLISOCYANIDE; 3-PHENYLPROPYL ISOCYANIDE; (2-ISOCYANOETHYL)BENZENE; 1,3-DICHLORO-2-(2-ISOCYANOETHYL)BENZENE; 4-FLUOROPHENETHYLISOCYANIDE; BETA-METHYLPHENYLETHYLISOCYANIDE; 2-(4-CHLOROPHENYL)ETHYLISOCYANIDE; 1,2,3,4-TETRAHYDRONAPHTHALEN-1-YL ISOCYANIDE; ISOAMYLISOCYANIDE; 2-ISOCYANOMETHYLTETRAHYDRO-FURANE; OCTYL ISOCYANIDE; 3-TRIFLUOROMETHYLBENZYLISOCYANIDE; 2-FLUOROBENZYLISOCYANIDE; 2-METHOXYPHENYL ISOCYANIDE; 3-METHOXYPHENYL ISOCYANIDE; 1-BENZYL-4-ISOCYANOPIPERIDINE; 1-BENZYL-4-(ISOCYANOMETHYL)-4-PHENYLPIPERIDINE; 9-ETHYL-3-ISOCYANO-9H-CARBAZOLE; 2,2-DIPHENYLETHYLISOCYANIDE; 1-ISOCYANO-3,3-DIPHENYLPROPANE; 4-PHENYLBUT-1-YLISOCYANIDE; 2-PENTYL ISOCYANIDE; 2-ISOCYANOBUTANE; 1-PENTYL ISOCYANIDE; DIPHENYLMETHYL ISOCYANIDE; 3,4-DICHLOROPHENYLISOCYANIDE; 3-ISOCYANOBENZONITRILE; 2,2-DIMETHOXYETHYL ISOCYANIDE; CYCLOPENTYL ISOCYANIDE; 2-CYANOPHENYLISONITRILE; 4-ISOCYANOBENZONITRILE; 1-ISOCYANO-2-(TRIFLUOROMETHYL)BENZENE; 3-ISOCYANO-4-CHLOROBENZOTRIFLUORIDE; 3-ISOCYANOBENZOTRIFLUORIDE; 5-ISOCYANO-2-CHLOROBENZOTRIFLUORIDE; 3-(ISOCYANOMETHYL)PYRIDINE; 4-(ISOCYANOMETHYL)PYRIDINE; 5-METHYLHEX-2-YLISOCYANIDE; 2-(ISOCYANOMETHYL)PYRIDINE; 1-BENZOYL-4-(2-ISOCYANOETHYL)PIPERAZINE; 1-(2-ISOCYANOETHYL)-PIPERIDINE; 1-METHYL-3-PHENYLPROPYLISOCYANIDE; 2-BROMOBENZYLISOCYANIDE; 3-BROMOBENZYLISOCYANIDE; 4-METHOXYPHENYL ISOCYANIDE; 4-BENZYLOXYPHENYLISOCYANIDE; 2,4-DICHLOROPHENYL ISOCYANIDE; 1-CHLORO-2-ISOCYANOBENZENE; 2,5-DICHLOROPHENYL ISOCYANIDE; 2,6-DICHLOROPHENYL ISOCYANIDE; 3-CHLORO-4-FLUOROPHENYLISOCYANIDE; 4-CHLORO-2-FLUORO-1-ISOCYANOBENZENE; 5-CHLORO-2-METHYLPHENYL ISOCYANIDE; 3-CHLORO-4-METHYLPHENYLISOCYANIDE; 3-CHLORO-2-METHYL-PHENYL-ISOCYANIDE; 4-SEC-BUTYLPHENYL ISOCYANIDE; 4-TERT-BUTYLPHENYLISOCYANIDE; 2-SEC-BUTYLPHENYL ISOCYANIDE; 2-ISOPROPYL-PHENYLISOCYANIDE; 2-ETHYLPHENYL ISOCYANIDE; 4-ISOPROPYL-PHENYLISOCYANIDE; 4-(TRIFLUORMETHOXY)-PHENYL-ISOCYANIDE; 2,3-DIMETHYLPHENYLISOCYANIDE; 2,4-DIMETHYLPHENYL ISOCYANIDE; 2,5-DIMETHYLPHENYL ISOCYANIDE; 3,5-DIMETHYLPHENYL ISOCYANIDE; 3,4-DIMETHYLPHENYL ISOCYANIDE; N-(4-ISOCYANOPHENYL)-N,N-DIMETHYLAMINE; 1-ISOCYANONAPHTHALENE; CYCLOHEPTYL ISOCYANIDE; CYCLOCTYLISOCYANIDE; 2-CYCLOHEXEN-1-YL-ETHYLISOCYANIDE; 2-(3,4-DIMETHOXYPHENYL)ETHYLISOCYANIDE; 3,4-DIFLUORPHENYLISOCYANIDE; 2,4-DIFLUOROPHENYL ISOCYANIDE; 1,4-DIISOCYANOBUTANE; 1,3-DIISOCYANOPROPANE; N-(3-ISOCYANOPROPYL)-N,N-DIMETHYLAMINE; N,N-DIETHYL-N-(3-ISOCYANOPROPYL)AMINE; 2-ISOCYANO-N,N-DIMETHYLETHANAMINE; 4-(3-ISOCYANOPROPYL)MORPHOLINE; 3-METHOXYPROPYL ISOCYANIDE; 3-BUTOXYPROP-1-YLISOCYANIDE; 1-ISOCYANO-3-ISOPROPOXYPROPANE; 3-ISOCYANOOCTANE; TERT-AMYLISOCYANIDE; 2-ISOCYANOOCTANE; 5-ISOCYANOMETHYL-2-DIMETHYL-DIOXOLANE; 4-BROMOBENZYLISOCYANIDE; 4-FLUOROBENZYLISOCYANIDE; 4-CHLOROBENZYLISOCYANIDE; (S)-(−)-ALPHA-METHYLBENZYL ISOCYANIDE; ISONITRILOMETHYL PS RESIN; TUNGSTEN(0) PENTACARBONYL-N-PENTYLISONITRILE; 5-CHLORO-2-ISOCYANOPYRIDINE; 5-BROMO-2-ISOCYANOPYRIDINE; 1-ISOCYANO-4-PHENOXYBENZENE; 1-(3-ISOCYANOPHENYL)ETHANONE; 1-FLUORO-3-ISOCYANOBENZENE; 2,6-DIBROMO-4-FLUOROPHENYLISOCYANIDE; 3-BROMO-4-FLUOROBENZYLISOCYANIDE; 5-BROMO-2-FLUOROBENZYLISOCYANIDE; 1-(4-CHLOROPHENYL)ETHYL ISOCYANIDE; 2-CHLORO-6-FLUOROBENZYLISOCYANIDE; 3,4,5-TRIMETHOXYBENZYLISOCYANIDE; 3,5-BIS(TRIFLUOROMETHYL)BENZYLISOCYANIDE; 2,4-DIFLUOROBENZYLISOCYANIDE; 2,5-DIFLUOROBENZYLISOCYANIDE; 2,5-DIMETHYLBENZYLISOCYANIDE; D-(+)-ALPHA-METHYLBENZYLISOCYANIDE; 1-(4-BROMOPHENYL)ETHYLISOCYANIDE; 2-PHENYLPROP-2-YLISOCYANIDE; 4-(TRIFLUOROMETHOXY)BENZYLISOCYANIDE; 2,6-DIFLUORBENZYLISOCYANIDE; 3-(METHYLTHIO)PHENYLISOCYANIDE; 1-BROMO-4-ISOCYANOBENZENE; 3-NITROBENZYLISOCYANIDE; 4-ISOCYANOBENZOPHENONE; 4-ETHOXYPHENYLISOCYANIDE; 2-CHLORO-4-NITROPHENYLISOCYANIDE; 2-ETHOXYPHENYLISOCYANIDE; CYCLOPROPYL ISOCYANIDE; (S)-(+)-1-ISOCYANOINDANE; (R)-(−)-1-ISOCYANOINDANE; 4-BROMO-2-FLUOROBENZYLISOCYANIDE; 4-CHLORO-2-FLUOROBENZYLISOCYANIDE; 1-FLUORO-2-ISOCYANOBENZENE; 4-METHYLPHENYLISOCYANIDE; 4-ISOCYANO-3-NITROBENZOTRIFLUORIDE; 2-METHYLPHENYLISOCYANIDE; 2-METHYL-6-ISOPROPYLPHENYLISOCYANIDE; (S)-3,3-DIMETHYLBUTY-2-YLISOCYANIDE; 4-TERT-BUTYLBENZYLISOCYANIDE; 2,2-DIPHENYLPROPYLISOCYANIDE; 2,4-DIMETHOXYPHENYLISOCYANIDE; 2,5-DIMETHOXYPHENYLISOCYANIDE; 4-BROMO-2-FLUOROPHENYLISOCYANIDE; 3,3-DIMETHYLBUT-1-YLISOCYANIDE; (R)-3,3-DIMETHYLBUT-2-YLISOCYANIDE; 2,2-DIMETHYLPROPYLISOCYANIDE; CYCLODODECYLISOCYANIDE; 1-ISOCYANOINDANE; 2-(3-METHOXYPHENYL)ETHYL-ISOCYANIDE; 3,5-DIMETHYLBENZYLISOCYANIDE; 3-ISOCYANO-4-METHOXY-1,1'-BIPHENYL; 2-ISOCYANO- 5-CHLORO-2'-FLUOROBENZOPHENONE; 2-ISOCYANO-2'-FLUORO-5-BROMO-BENZOPHENONE; 2-BROMOPHENYLISOCYANIDE; 3,4-DIMETHOXYPHENYLISOCYANIDE; 3-ISOCYANO-PHENYLFORMAMIDE; 4-FLUOROPHENYL ISOCYANIDE; 4-ISOCYANOACETOPHENONE; 1-ISOCYANO-2-PHENYLBENZENE; 1-CYANO-4-ISOCYANONAPHTHALENE; 2-FLUOROPHENETHYLISOCYANIDE; 2-(3-BROMOPHENYL)ETHYLISOCYANIDE; 2-(4-BROMOPHENYL)ETHYLISOCYANIDE; 2-(2-CHLOROPHENYL)ETHYLISOCYANIDE; 3,4-DICHLOROBENZYLISOCYANIDE; 2,4-DICHLORBENZYLISOCYANIDE; 2-(4-ISOCYANOPHENYL)ETHYL-ISOCYANIDE; 3-METHYLPHENETHYLISOCYANIDE; 4-CHLORO-2-METHOXY-5-METHYLPHENYL ISOCYANIDE; 2,4-DIBROMO-6-METHYLPHENYL-ISOCYANIDE; 2-BROMO-4-METHYLPHENYLISOCYANIDE; 2,5-DIBROMOPHENYLISOCYANIDE; 2-FLUOR-5-NITROPHENYLISOCYANIDE; 2,4,6-TRICHLOROPHENYLISOCYANIDE; 4-BROMO-2-CHLOROPHENYLISOCYANIDE; 2-METHYLPHENETHYLISOCYANIDE; 3-FLUORO-PHENETHYLISOCYANIDE; 2,4-DICHLOROPHENETHYLISOCYANIDE; 2-(3-CHLORO-PHENYL)ETHYLISOCYANIDE; 3-CHLORO-2-METHOXYPHENYL-ISOCYANIDE; 1-ISOCYANO-4-(TRIFLUOROMETHYL)BENZENE; 3-BROMOPHENYLISOCYANIDE; 2,6-DIBROMO-4-NITROPHENYLISOCYANIDE; 2,6-DIBROMO-4-METHYLISOCYANIDE; 4-FLUORO-2-METHYLPHENYLISOCYANIDE; 2-METHOXY-5-METHYLPHENYL-ISOCYANIDE; 1-ISOCYANOBENZENE; 1-(2-ISOCYANOETHYL)-PYRROLIDINE; 1-(2-ISOCYANO-ETHYL)-4-METHYL-PIPERAZINE; (5-CHLORO-2-THIENYL)METHYLISOCYANIDE; 2-(THIEN-2-YL)ETHYLISOCYANIDE; 1-(2-ISOCYANOETHYL)-2,2-DIMETHYLPYRROLIDINE; 1-(3-CHLOROPHENYL)ETHYL ISOCYANIDE; 3-(1-ISOCYANO-ETHYL)-PYRIDINE; 4-(1-ISOCYANO-ETHYL)PYRIDINE; 4-BENZYL-1-(2-ISOCYANO-ETHYL)PIPERIDINE; 1-(2-ISOCYANO-ETHYL)-4-PYRIDIN-2-YL-PIPERAZINE; 1-CYCLOHEXYL-4-(2-ISOCYANO-ETHYL)-PIPERAZINE; 4-(TRIFLUOROMETHYL)BENZYL-ISOCYANIDE; 1-(2-CHLOROPHENYL)ETHYL ISOCYANIDE; 1-(1-ISOCYANO-ETHYL)-2-METHOXY-BENZENE; 1-(5-METHYL-2-THIENYL)ETHYL ISOCYANIDE; 1-(4-FLUOROPHENYL)ETHYLISOCYANIDE; 1-(2-ISOCYANO-ETHYL)-4-PHENYL-PIPERAZINE; 1-(2-ISOCYANOETHYL)-4-(2-PYRROLIDINOETHYL)-PIPERIDINE; N-2-ISOCYANOETHYL-2,3-DIHYDROINDOLE; 1-(2-ISOCYANOETHYL)-1,2,3,4-TETRAHYDROQUINOLINE; 1-(2-ISOCYANOETHYL)-6,7-DIEMTHOXY-1,2,3,4-TETRAHYDROQUINOLINE; 1-(2-ISOCYANO-ETHYL)-4-PHENYL-PIPERIDINE; 1-(3-CHLORO-PROPYL)-4-(2-ISOCYANO-ETHYL)-PIPERAZINE; 1-ALLYL-4-(2-ISOCYANO-ETHYL)-PIPERAZINE; 1-BUTYL-4-(2-ISOCYANOETHYL)PIPERAZINE; 1-(2-ISOCYANO-ETHYL)-4-ISOPROPYL-PIPERAZINE; 4-[4-(2-ISOCYANO-ETHYL)-PIPERAZIN-1-YL]-MORPHOLINE; 1-(2-ISOCYANO-ETHYL)-4-PYRROLIDIN-1-YL-PIPERAZINE; 1-(2-ISOCYANO-ETHYL)-4-(2-METHOXY-ETHYL)-PIPERAZINE; 1-(2-ISOCYANO-ETHYL)-4-(2-DIMETHYLAMINOETHYL)-PIPERAZINE; 1-(2-ISOCYANO-ETHYL)-4-(2-PYRIMIDINO)-PIPERAZINE; 1-(2-ISOCYANO-ETHYL)-4-(2-PYRAZINYL)-PIPERAZINE; 1-CHLORO-4-ISOCYANOBENZENE; 4-(DIETHYLAMINO)PHENYL ISOCYANIDE; 2-ISOCYANO-1-PHENYLETHANOLE; 1-(2-ISOCYANO-ETHYL)-4-PYRIDIN-4-YL-PIPERAZINE; 2-CHLORO-6-METHYLPHENYL ISOCYANIDE; METHYL ISOCYANIDE; 4-(2-DIMETHYLAMINO)-PIPERAZINO-ISOCYANO-ACETAMIDE; 4,4'-DIISOCYANO-BIPHENYL; 4-(ISOCYANOMETHYL)BENZYL-ISOCYANIDE; 1,4-BIS(3-ISOCYANOPROPYL)PIPERAZINE; 3-ISOCYANOPHENYLISOCYANIDE; 1,2-DIISOCYANOCYCLOHEXANE; 1,4-DIISOCYANOCYCLOHEXANE; 1,3-DIISOCYANO-2,2-DIMETHYL-PROPANE; 3-(2-ISOCYANOETHYL)-1H-INDOLE; 4-(3-CHLOROPROPYL)-PIPERAZINO-ISOCYANO-ACETAMIDE; 4-N-BUTYL-PIPERAZINO-ISOCYANO-ACETAMIDE; 4-(2-PYRIMIDINO)-PIPERAZINO-ISOCYANO-ACETAMIDE; 4-(2-PYRAZINYL)-PIPERAZINO-ISOCYANO-ACETAMIDE; 4-(2-PYRIDYL)-PIPERAZINO-ISOCYANO-ACETAMIDE; 4-(4-PYRIDYL)-PIPERAZINO-ISOCYANO-ACETAMIDE; N-METHYLPIPERAZINO-ISOCYANO-ACETAMIDE; 6-ISOCYANOQUINOLINE; 3-(ISOCYANOMETHYL)BENZYL-ISOCYANIDE; 1,2-DIISOCYANO-2-METHYLPROPANE; 1,5-DIISOCYANOPENTANE; 1,7-DIISOCYANOHEPTANE; 4,4'-DIISOCYANO-3,3'-DIMETHOXY-BIPHENYL; 1,2-BIS-(2-ISOCYANOETHOXY)-ETHANE; 1,3-BIS(ISOCYANOMETHYL)CYCLO-HEXANE; 4-ALLYL-PIPERAZINO-ISOCYANO-ACETAMIDE; 4-ISOPROPYL-PIPERAZINO-ISOCYANO-ACETAMIDE; 4-CYCLOHEXYL-PIPERAZINO-ISOCYANO-ACETAMIDE; 4-[((2-MORPHOLINO-4-YL)ETHYL)]-PIPERAZINO-ISOCYANO-ACETAMIDE; 4-(2-PYRROLIDINOETHYL)-PIPERAZINO-ISOCYANO-ACETAMIDE; 1,2-DIISOCYANOETHANE; 4-(2-METHOXYETHYL)-PIPERAZINO-ISOCYANO-ACETAMIDE; 4-CHLORO-2-METHYLPHENYL ISOCYANIDE; (S,S)-1,2-DIISOCYANOCYCLOHEXANE; 4-(2-PYRROLIDINOETHYL)-1-PIPERIDINO-2-ISOCYANOACETAMIDE; 1-PYRROLIDINO-2-ISOCYANOACETAMIDE; 4-(1-PYRROLIDINO)-PIPERIDINO-ISOCYANO-ACETAMIDE; 4-METHYL-PIPERIDINO-ISOCYANO-ACETAMIDE; 1-CYCLOHEXENYLISOCYANIDE; 1,10-DIISOCYANODECANE; 2-(2-ISOCYANOETHYL)PYRIDINE; N-MORPHOLINO-2-ISOCYANOACET-AMIDE; N-PIPERIDINO-2-ISOCYANOACETAMIDE; 4-BENZYL-PIPERIDINO-ISOCYANO-ACETAMIDE; 2,6-DIMETHYL-PIPERIDINO-ISOCYANO-ACETAMIDE; 4-PHENYL-PIPERIDINO-ISOCYANO-ACETAMIDE; (5-METHYL-2-FURYL)METHYL ISOCYANIDE; 1,3-DIMETHYLBUT-1-YLISOCYANIDE; 6-METHYLHEPT-2-YLISOCYANIDE; 2-NAPHTHYL ISOCYANIDE; 2-ISOCYANO-3-PHENYL-PROPIONIC-ACIDMORPHOLINAMIDE; 3,5-DIFLUORBENZYLISOCYANIDE; 4-FORMYLAMINOPHENYLISOCYANIDE; 2-(ISOCYANOMETHYL)FURAN; 2-ISOCYANOPYRIDINE; 2,3-DIHYDRO-6-ISOCYANO-1,4-BENZODIOXINE; 1-CHLORO-3-ISOCYANOBENZENE; 2-CHLORO-5-NITROPHENYLISOCYANIDE; 2,4-DIBROMPHENYLISOCYANIDE; 1-CHLORO-5-ISOCYANO-2,4-DIMETHOXYBENZENE; 3-PHENOXY-PHENYLISOCYANIDE; 3-CHLORO-2-FLUOROPHENYLISOCYANIDE; 1-ISOCYANO-2-METHOXYETHANE; 1-(3-ISOCYANOPROPYL)-1H-IMIDAZOLE; 3,4,5-

TRIMETHOXYPHENYLISOCYANIDE; 1-ISOCYANO-3,3-DIETHOXYPROPANE; 1,8-DIISOCYANOOCTANE; 2,2-DIETHOXY-1-ISOCYANOETHANE; 1-(2-ISOCYANOPHENYL)PYRROLE; (R)-(+)-ALPHA-(1-NAPHTHYL)-ETHYL-ISOCYANIDE; (S)-(−)-ALPHA-(1-NAPHTHYL)-ETHYL-ISOCYANIDE; 4-(4-ISOCYANOPHENYL)MORPHOLINE; 4-NITROPHENYLETHYLISOCYANIDE; 5-ISOCYANOMETHYLINDOLE; 3-ISOCYANOPROPYLTRIETHOXYSILANE; 1-(3-ISOCYANOPROPYL)-2-PYRROLIDINONE; 2-(2-ISOCYANOETHOXY)PROPANE; 1-(2-ISOCYANOETHOXY)PROPANE; 1-ETHOXY-2-ISOCYANOETHANE; 2-TERT-BUTOXYETHYL ISOCYANIDE; 1,3-BENZODIOXOL-5-YLISOCYANIDE; 2-ISOCYANO-1,3,5-TRIMETHYLBENZENE; 4-ISOCYANO-1,3,5-TRIMETHYL-1H-PYRAZOLE; 8-ISOCYANOQUINOLINE; (1-ISOCYANO-2-PHENYLETHYL)BENZENE; 1-(ISOCYANOMETHYL)NAPHTHALENE; 4-PHENYLCYCLOHEXENYLISOCYANIDE; 3-CHLORO-5-METHOXYPHENYLISOCYANIDE; 2-IODOPHENYL ISOCYANIDE; 3-CHLORO-4-METHOXYPHENYLISOCYANIDE; 2-(3,4-DIETHOXYPHENYL) ETHYL ISOCYANIDE; 2,4-DIMETHOXYBENZYL ISOCYANIDE; 3-METHYLPHENYL ISOCYANIDE; 2-CHLORO-5-(TRIFLUOROMETHYL)BENZYL-ISOCYANIDE; 1,3-DIETHYL-2-ISOCYANO-BENZENE; 2,3-DICHLOROBENZYLISOCYANIDE; 4-CHLORO-3-(TRIFLUOROMETHYL)BENZYL-ISOCYANIDE; 2,3-DIMETHYLBENZYLISOCYANIDE; 4-METHYL-3-CHLOROBENZYL-ISOCYANIDE; 2,4,6-TRIMETHYLBENZYLISOCYANIDE; 3-CHLORO-4-FLUOROBENZYLISOCYANIDE; 2,6-DICHLOROBENZYLISOCYANIDE; 4-PHENOXYBENZYLISOCYANIDE; 3-PHENOXYBENZYL ISOCYANIDE; 2-METHYL-3-NITROPHENYL ISOCYANIDE; 2-METHYL-4-NITROPHENYL ISOCYANIDE; ALLYLISOCYANIDE; CYCLOBUTYL ISOCYANIDE; 4-BROMO-2-METHYLPHENYL ISOCYANIDE; 1-ISOPROPYL-2-METHYLPROPYL ISOCYANIDE; 1,7,7-TRIMETHYLBICYCLO[2.2.1]HEPT-2-YL ISOCYANIDE; 4-(2-ISOCYANOETHYL)PYRIDINE; 2-NITROPHENYL ISOCYANIDE; 2-ISOCYANO-N,N-DIMETHYL-2-PYRIDIN-4-YLETHYLENAMINE; 1,2,3,4-TETRAHYDRO-CHINOLINO-1-ISOCYANOACETAMIDE; 4-(METHYLTHIO)PHENYLISOCYANIDE; 2-ISOCYANO-2-METHYLPROPANE HYDROCHLORIDE; 5-ISOCYANO-PYRIDINE-2,4-DIAMINE; 5-BROMO-2-ISOCYANO-1,3-DIMETHYLBENZENE; 2,5-DIFLUORO-PHENYLISOCYANIDE; 2,6-DIFLUORO-PHENYLISOCYANIDE; 2,4,6-TRIFLUOROPHENYLISOCYANIDE; 2-ETHYL-6-METHYL-PHENYLISOCYANIDE; 2-ISOCYANO-9-FLUORENONE; 2-(TRIFLUORMETHOXY)-PHENYLISOCYANIDE; 2-ISOCYANOBENZOPHENONE; 2-ISOCYANO-5-CHLORBENZO-PHENONE; 2-ISOCYANO-2',5-DICHLORBENZO-PHENONE; 2-NITRO-4-METHOXYPHENYL-ISOCYANIDE; 2-ISOPROPENYL-PHENYLISOCYANIDE; 2,3,4-TRIFLUORO-PHENYLISOCYANIDE; 2-CHLORO-4-FLUORO-5-METHYL-PHENYLISOCYANIDE; 4-BUTOXY-PHENYLISOCYANIDE; 4-METHOXY-2-METHYL-PHENYL-ISOCYANIDE; 2-METHOXYISOBUTYL ISOCYANIDE; PROPANE, 2-ISOCYANO-2-METHYL-, ZINC COMPLEX; 2-(4-ISOCYANOPHENYL)ACETONITRILE; 5-FLUORO-2-METHYL-PHENYL-ISOCYANIDE; 3,5-DIMETHOXY-PHENYLISOCYANIDE; 4-ISOCYANO-3-CHLOROBENZOTRI-FLUORIDE; 4-OCTYLOXY-PHENYLISOCYANIDE; 5-BROMO-2-METHYL-PHENYL-ISOCYANIDE; 2,4,5-TRIFLUOROPHENYLISOCYANIDE; 4-VINYL-PHENYLISOCYANIDE; 3,3-DIFLUORO-PHENYLISOCYANIDE; 3-ETHYL-PHENYLISOCYANIDE; 3-FLUORO-2-METHYL-PHENYL-ISOCYANIDE; 4-PROPYL-PHENYLISOCYANIDE; 2-BROMO-4-TRIFLUOROMETHOXY-PHENYLISOCYANIDE; 3-BROMO-4-METHYL-PHENYL-ISOCYANIDE; 1-ISOCYANO-3-(TRIFLUOROMETHOXY)BENZENE; 1,2-DIFLUORO-3-ISOCYANO-BENZENE; 4-HEXYL-PHENYLISOCYANIDE; 2-FLUORO-5-(TRIFLUOROMETHYL)-PHENYLISOCYANIDE; 2-METHOXY-5-(TRIFLUOROMETHYL)-PHENYLISOCYANIDE; 4-BROMO-5-(TRIFLUOROMETHYL)-PHENYLISOCYANIDE; (3-ISOCYANOPHENYL)(PHENYL)METHANONE; 2-TERT-BUTYL-PHENYLISOCYANIDE; 5-ISOCYANO-1H-INDOLE; 2-FLUORO-5-METHYL-PHENYLISOCYANIDE; 3-FLUORO-4-METHYL-PHENYLISOCYANIDE; 3-TRIFLUOROMETHYL-4-FLUORO-PHENYLISOCYANIDE; 2-METHOXYDIBENZO[B,D]FURAN-3-YL ISOCYANIDE; 1-(ISOCYANOMETHYL)-2,3-DIMETHOXYBENZENE; 6-ISOCYANO-1-METHYL-1H-INDOLE; 5-ISOCYANO-1-METHYL-1H-INDOLE; 6-BROMO-5-ISOCYANO-PYRIDINE-2,4-DIAMINE; 5-ISOCYANO-1H-INDAZOLE; 1-BENZYL-5-ISOCYANO-1H-INDAZOLE; 1-(ISOCYANOMETHYL)-3-(TRIFLUOROMETHOXY)BENZENE; 5-FLUORO-2-ISOCYANO-1,3-DIMETHYL-BENZENE; 1-(2,6-DICHLORO-4-(TRIFLUOROMETHYL)PHENYL)-3-ISOCYANO-1H-PYRAZOL-5-AMINE; 1-ISOCYANO-3,5-DIMETHYLADAMANTANE; 2,3-DIHYDRO-6-ISOCYANOBENZO[E][1,3]OXAZIN-4-ONE; N-(4-ISOCYANOPHENYL)ACETAMIDE; 3-((1S,3S)-3-AMINO-1,4-DIHYDROXYBUTYL)BENZENISOCYANIDE; 3-((1R,3R)-3-AMINO-1,4-DIHYDROXYBUTYL)BENZENISOCYANIDE; 4-((1S,3S)-3-AMINO-1,4-DIHYDROXYBUTYL)BENZENISOCYANIDE; 4-((1R,3R)-3-AMINO-1,4-DIHYDROXYBUTYL)BENZENISOCYANIDE; (R)-1-(4-ISOCYANOPHENYL)ETHANOL; (S)-1-(4-ISOCYANOPHENYL)ETHANOL; 3-((1R)-1-AMINO-2-HYDROXY-ISOPROPYL)BENZENISOCYANIDE; 3-((1S)-1-AMINO-2-HYDROXY-ISOPROPYL)BENZENISOCYANIDE; 4-((1R)-1-AMINO-2-HYDROXY-ISOPROPYL)BENZENISOCYANIDE; 4-((1S)-1-AMINO-2-HYDROXY-ISOPROPYL)BENZENISOCYANIDE; 4-((1S,3R)-3-AMINO-1,4-DIHYDROXYBUTYL)BENZENISOCYANIDE; 3-((3S,1R)-3-AMINO-1,4-DIHYDROXYBUTYL)BENZENISOCYANIDE; 3-((1S,3R)-3-AMINO-1,4-DIHYDROXYBUTYL)BENZENISOCYANIDE; 4-((3S,1R)-3-AMINO-1,4-DIHYDROXYBUTYL)BENZENISOCYANIDE; 2-ISOCYANO-1-METHOXY-3-METHYL-BENZENE; 1-(2-ISOCYANOETHYL)-3-TRIFLUOROMETHOXY-BENZENE; 4-PHENYL-PIPERAZINO-ISOCYANO-ACETAMIDE; 2-CHLORO-4-ISOCYANOMETHYL-PYRIDINE; 2,4'-DIISOCYANO-BIPHENYL; 2,4-DIBROMO-6-FLUORPHENYLISOCYANIDE; 2,6-DIBROMO-4-(TRIFLUOROMETHOXY)PHENYL-ISOCYANIDE; 2,4-DIBROMO-6-(TRIFLUOROMETHYL)-PHENYLISOCYANIDE; 2,6-DICHLORO-4-(TRIFLUOROMETHOXY)PHENYL-ISOCYANIDE; 2,6-DICHLORO-4-(TRIFLUOROMETHYL)PHENYL-ISOCYANIDE; 3-(DIFLUOROMETHOXY)

PHENYLISOCYANIDE; 1,5-BIS-ISOCYANOMETHYL-2,4-DIMETHYL-BENZENE; R-1-ISOCYANO-1,2,3,4-TETRA-HYDRONAPHTHALENE; 4-BROMO-3,5-DIFLUORO-PHENYLISOCYANIDE; 5-BROMO-2,4-DIFLUORO-PHENYLISOCYANIDE; 2-BROMO-4-FLUOROPHENYLISOCYANIDE; 2-BROMO-5-FLUOROPHENYLISOCYANIDE; 3-BROMO-4-FLUOROPHENYLISOCYANIDE; 4-BROMO-3-FLUOROPHENYLISOCYANIDE; 2-CHLORO-4,6-DIFLUORO-PHENYLISOCYANIDE; 2-CHLORO-4-FLUOROPHENYLISOCYANIDE; 2-CHLORO-5-FLUOROPHENYLISOCYANIDE; 2-CHLORO-6-FLUOROPHENYLISOCYANIDE; 4-CHLORO-3-FLUOROPHENYLISOCYANIDE; 5-CHLORO-2-FLUOROPHENYLISOCYANIDE; 2-CHLORO-5-FLUORO-4-NITROPHENYL-ISOCYANIDE; 4-(DIFLUOROMETHOXY)PHENYLISOCYANIDE; (1S,2R,5R)6,6-DIMETHYLBICYCLO-[3.1.1]HEPT-2-YLMETHYL-ISOCYANIDE; 3-FLUORO-4-(TRIFLUOROMETHYL)-PHENYLISOCYANIDE; 2-(2-METHOXYPHENOXY)-5-(TRIFLUOROMETHYL)-PHENYLISOCYANIDE; 3-TRIFLUOROMETHOXY-4-ISOCYANOBENZONITRIL; 2,4-BIS(TRIFLUOROMETHYL)PHENYLISOCYANIDE; 2,5-BIS(TRIFLUOROMETHYL)PHENYLISOCYANIDE; 3,5-BIS(TRIFLUOROMETHYL)-2-METHYL-PHENYLISOCYANIDE; 4-[3,5-DI(TRIFLUOROMETHYL)PHENOXY]-PHENYLISOCYANIDE; 2-BROMO-4-CHLORO-6-FLUOROPHENYLISOCYANIDE; 2-BROMO-5-CHLORO-4-FLUOROPHENYLISOCYANIDE; 2-BROMO-6-CHLORO-4-(TRIFLUOROMETHYL)-PHENYLISOCYANIDE; 2-BROMO-4,6-DIFLUORO-PHENYLISOCYANIDE; 4-BROMO-2,6-DIFLUORO-PHENYLISOCYANIDE; 5-BROMO-2-FLUOROPHENYLISOCYANIDE; 3-BROMO-4-(TRIFLUOROMETHOXY)-PHENYLISOCYANIDE; 4-BROMO-2-(TRIFLUOROMETHOXY)-PHENYLISOCYANIDE; 4-BROMO-3-(TRIFLUOROMETHOXY)-PHENYLISOCYANIDE; 5-CHLORO-4-FLUORO-2-NITROPHENYL-ISOCYANIDE; 2-CHLORO-4-TRIFLUOROMETHOXY-PHENYLISOCYANIDE; 3-CHLORO-4-TRIFLUOROMETHOXY-PHENYLISOCYANIDE; 3-ISOCYANO-4-(METHYLTHIO)BENZOTRIFLUORIDE; 2-ISOCYANO-5-NITRO-BENZOTRIFLUORIDE; 3-ISOCYANO-4-NITRO-BENZOTRIFLUORIDE; 5-ISOCYANO-2-NITRO-BENZOTRIFLUORIDE; 4-ISOCYANO-NONAFLUOROBIPHENYL; 3-(TRIFLUOROMETHYLTHIO)-PHENYLISOCYANIDE; 4-(TRIFLUOROMETHYLTHIO)PHENYLISOCYANIDE; 4-[(3-(TRIFLUOROMETHYL)PHENYL)SULFANYL]-PHENYLISOCYANIDE; 3-ISOCYANO-4-(4-MORPHOLINO)BENZOTRIFLUORIDE; 3-ISOCYANO-4-(1-PIPERIDINO)-BENZOTRIFLUORIDE; 1,5-DIISOCYANO-NAPHTHALENE; 2-ISOCYANO-9H-FLUORENE; 2-BROMO-4-(TRIFLUOROMETHYL)-6-NITROPHENYL-ISOCYANIDE; 3-CHLORO-4-(TRIFLUOROMETHYL)PHENYL-ISOCYANIDE; 2-ISOCYANO-4-(4-CHLORO-3,5-DIMETHYLPHENOXY)-BENZOTRIFLUORIDE; 2-ISOCYANO-4-CHLORO-2'-FLUOROBENZOPHENONE; 3-CHLORO-5-NITRO-4-(TRIFLUOROMETHYL)-PHENYL-ISOCYANIDE; 2-CHLORO-5-NITRO-4-(TRIFLUOROMETHYL)-PHENYLISOCYANIDE; 4-ISOCYANO-2-CYANO-3'-(TRIFLUOROMETHYL)DIPHENYL THIOETHER; 4-ISOCYANO-2,5-DIFLUOROBENZONITRILE; 2-ISOCYANO-5-(TRIFLUOROMETHYL)PYRIDINE; 2-ISOCYANO-6-(TRIFLUOROMETHYL)PYRIDINE; 3-ISOCYANO-4-(TRIFLUOROMETHYL)PYRIDINE; 3-ISOCYANO-6-(TRIFLUOROMETHYL)PYRIDINE; 4-BROMO-2-(TRIFLUORMETHYL)PHENYL-ISOCYANIDE; 2-BROMO-5-(TRIFLUORMETHYL)PHENYLISOCYANIDE; 3-BROM-5-(TRIFLUORMETHYL)PHENYL-ISOCYANIDE; 2,2'-DIISOCYANO-BIPHENYL; 2-BROMO-4-(TRIFLUOROMETHYL)PHENYL-ISOCYANIDE; 3-(4-ISOCYANOBENZYLTHIO)-BENZOTRIFLUORIDE; 3-CHLORO-2-FLUOROBENZYLISOCYANIDE; 5-CHLORO-2-FLUOROBENZYLISOCYANIDE; 6-CHLORO-2-FLUORO-3-METHYLBENZYLISOCYANIDE; 2,3-DIFLUORBENZYLISOCYANIDE; 3,4-DIFLUOROBENZYLISOCYANIDE; 2-(DIFLUOROMETHOXY)BENZYLISOCYANIDE; 1,4-DIISOCYANO-2-METHOXY-BENZENE; N-ALLYL-2-ISOCYANO-ACETAMIDE; N-ALLYL-2-ISOCYANO-N-METHYL-ACETAMIDE; N-ALLYL-2-BENZYL-2-ISOCYANO-ACETAMIDE; 2-ISOCYANO-4-METHYL-PENTANOIC ACID ALLYLAMIDE; 2-ISOCYANO-3-(5-IMIDAZO)-PROPIONIC ACID MORPHOLINAMIDE; N-PROPYLISOCYANIDE; 2-HYDROXY-CYCLOHEXYLISOCYANIDE; 3-(DIFLUOROMETHOXY)BENZYLISOCYANIDE; 3-ISOCYANO-2-(2-FLUOROPHENOXY)PYRIDINE; 5-FLUORO-2-ISOCYANOPYRIDINE; 2-ISOCYANO-4-(TRIFLUOROMETHYL)PYRIDINE; N-ALLYL-2-ISOCYANO-N-ETHYL-ACETAMIDE; 2-ISOCYANO-PROPIONIC ACID MORPHOLINAMIDE; PRIAXON 01648; 2-ISOCYANO-CYCLOHEXYLOXY-TRIMETHYLSILANE; 2-(TRIFLUOROMETHOXY)BENZYL-ISOCYANIDE; 5-ISOCYANO-2-CYANO-BENZO-TRIFLUORIDE; 1-ETHYL-2-ISOCYANO-3-METHOXY-BENZENE; 4-ISOCYANO-3-P-TOLYL-1H-PYRAZOLE; 1,6-DICHLORO-4-FLUOROPHENYL-ISOCYANIDE; 2-(METHYLTHIO)ETHYLISOCYANIDE; 4-ISOCYANOBIPHENYL; 2-(2-CHLORO-6-FLUOROBENZYLTHIO)ETHYL-ISOCYANIDE; 2-CHLORO-3,6-DIFLUOROBENZYLISOCYANIDE; 3-CHLORO-2,6-DIFLUOROBENZYLISOCYANIDE; 2-CHLORO-4-FLUOROBENZYLISOCYANIDE; DIETHYL-(4-ISOCYANO-PENTYL)-AMINE; 2,6-DINITRO-4-(TRIFLUOROMETHYL)PHENYL-ISOCYANIDE; 2-FLUORO-5-ISOCYANOBENZONITRILE; 2-FLUORO-3-(TRIFLUOROMETHYL)-PHENYLISOCYANIDE; 3-FLUORO-5-(TRIFLUOROMETHYL)-PHENYLISOCYANIDE; BUTYL-(3-ISOCYANO-PROPYL)-(1-ISOCYANO-PROPYL)-AMINE; 4-ISOCYANO-1-METHOXY-2-NITRO-BENZENE; 2-ISOCYANO-5-NITRO-1H-PYRROLE; 2-ISOCYANO-5-NITRO-PYRIDINE; 2-ISOCYANO-3-PHENYL-1-(PYRROLIDIN-1-YL)PROPAN-1-ONE; 2-ISOCYANO-3-PHENYL-1-(PIPERIDIN-1-YL)PROPAN-1-ONE; 1-AMINO-5-ISOCYANOINDOLE; 2-ISOCYANOETHYLTOSYLATE; (E)-3-CHLORO-4,4,4-TRIFLUORO-2-ISOCYANOBUT-2-ENENITRILE; 2-ISOCYANO-3-METHYL-PYRIDINE; 5-ISOCYANO-PYRIDIN-3-OL; 4-ISOCYANOBENZOIC ACID MORPHOLIDE; P-TOLYLTHIOMETHYL ISOCYANIDE; 1-(2-ISOCYANO-ETHYL)-1,2,3,4-TETRAHYDRO-NAPHTHALENE; 2-ISOCYANOETHYL O-TOLYLSULFAMATE; (E)-4,4,4-TRIFLUORO-2-ISOCYANO-3-METHOXY-BUT-2-ENENITRILE; 3-BROMO-5-ISOCYANOPYRIDIN-2-AMINE

List No. 2—aldehydes: including aldehydes from list no. 5; (−)-CITRONELLAL; (+)-CITRONELLAL;

(1-FORMYL-2-OXO-2-PHENYLETHYL)SODIUM; (1-METHYL-1H-IMIDAZOL-4-YL)-ACETALDEHYDE; (1-METHYLPIPERIDIN-4-YL)ACETALDEHYDE; (1R,3S,5S)-8-METHYL-8-AZABICYCLO[3.2.1]OCTANE-3-CARBALDEHYDE; (1R,4R)-METHYL 4-FORMYLCYCLOHEXANECARBOXYLATE; (1S)-1,3,4-TRIMETHYL-3-CYCLOHEXENE-1-CARBALDEHYDE; (1S,2S)-2-(TRIFLUOROMETHYL)CYCLOPROPANE-1-CARBALDEHYDE; (1S,4R)-BICYCLO[2.2.1]HEPTANE-2-CARBALDEHYDE; (2,2,3-TRIMETHYL-CYCLOPENT-3-ENYL)-ACETALDEHYDE; (2,3,6-TRIFLUOROPHENYL)ACETALDEHYDE; (2,3-DIFLUORO-4-METHYLPHENYL)ACETALDEHYDE; (2,3-DIFLUOROPHENYL)ACETALDEHYDE; (2,4-DIFLUOROPHENYL)ACETALDEHYDE; (2,5-DIFLUOROPHENYL)-ACETALDEHYDE; (2,6-DIFLUORO-3-METHYLPHENYL)ACETALDEHYDE; (2-CHLORO-5-FLUOROPHENYL)ACETALDEHYDE; (2-CYANO-5-FORMYLPHENYL)BORONIC ACID; (2-FLUORO-3-METHYLPHENYL)ACETALDEHYDE; (2-FORMYL-IMIDAZOL-1-YL)-ACETIC ACID METHYL ESTER; (2-FORMYLPHENOXY)ACETONITRILE; (2-FORMYLPHENYL)-ACETONITRILE; (2-HYDROXY-PHENYL)-ACETALDEHYDE; (2-METHOXYPHENYL)ACETALDEHYDE; (2-METHYLPHENYL)ACETALDEHYDE; (2-NITROPHENYL)ACETALDEHYDE; (3,4,5-TRIMETHYL-1H-PYRAZOL-1-YL)ACETALDEHYDE; (3,4-DIFLUOROPHENYL)ACETALDEHYDE; (3,5-DIMETHYL-1H-PYRAZOL-1-YL)ACETALDEHYDE; (3,5-DIMETHYL-1H-PYRAZOL-4-YL)ACETALDEHYDE COMPOUND WITH METHANOL (1:1); (3AR,3BS,4S,4AS,5AS)-2-OXOOCTAHYDROCYCLOPROPA[3,4]CYCLOPENTA[1,2-B]FURAN-4-CARBALDEHYDE; (3-CHLORO-4-METHYLPHENYL)ACETALDEHYDE; (3-CHLORO-5-FLUOROPHENYL)ACETALDEHYDE; (3-CHLORO-PHENYL)-ACETALDEHYDE; (3-FLUORO-4-METHOXYPHENYL)ACETALDEHYDE; (3-FLUORO-PHENYL)-ACETALDEHYDE; (3-HYDROXY-4-METHOXY-PHENYL)-ACETALDEHYDE; (3-HYDROXY-PHENYL)-ACETALDEHYDE; (3-METHYLPHENYL)ACETALDEHYDE; (3-NITRO-1H-PYRAZOL-1-YL)ACETALDEHYDE; (3-NITRO-PHENYL)-ACETALDEHYDE; (3S)-3-ISOPROPYL-6-OXOHEPTANAL; (4-CHLORO-2-FLUOROPHENYL)ACETALDEHYDE; (4-CHLORO-PHENYL)-ACETALDEHYDE; (4-CHLORO-PHENYL)-OXO-ACETALDEHYDE; (4-ETHYL-3,5-DIMETHYL-1H-PYRAZOL-1-YL)ACETALDEHYDE; (4-FLUORO-2-FORMYLPHENYL)BORONIC ACID; (4-FLUORO-3-METHYL-PHENYL)-OXO-ACETALDEHYDE; (4-FLUORO-PHENYL)-ACETALDEHYDE; (4-FLUORO-PHENYL)-OXO-ACETALDEHYDE; (4-FORMYL-3-METHOXYPHENOXYMETHYL)POLYSTYRENE; (4-ISOPROPYLPHENYL)ACETALDEHYDE; (4-METHOXY-PHENYL)-OXO-ACETALDEHYDE; (4-METHYLPHENYL)(OXO)ACETALDEHYDE; (4-METHYL-PIPERAZIN-1-YL)-ACETALDEHYDE; (4-METHYL-PYRAZOL-1-YL)-ACETALDEHYDE; (4-METHYLSULFANYLPHENYL)ACETALDEHYDE; (4-NITRO-1H-PYRAZOL-1-YL)ACETALDEHYDE; (4-NITRO-PHENYL)-ACETALDEHYDE; (4R,5S)-5-(HYDROXYMETHYL)-2,2-DIMETHYL-1,3-DIOXOLANE-4-CARBALDEHYDE; (4S)-2,2-DIMETHYL-1,3-DIOXOLANE-4-ACETALDEHYDE; (5-CHLORO-2-FLUOROPHENYL)ACETALDEHYDE; (5-CHLOROPYRIMIDIN-2-YL)ACETALDEHYDE; (5-FORMYLPYRIDIN-3-YL)BORONIC ACID; (5-METHYL-3-NITRO-PYRAZOL-1-YL)-ACETALDEHYDE; (5-PYRIMIDINYLOXY)-ACETALDEHYDE; (5S)-5,6-DIHYDRO-5-INDOLIZINECARBOXALDEHYDE; (8R)-5,6,7,8-TETRAHYDRO-8-INDOLIZINEACETALDEHYDE; (AR)-A-METHYL-2-FURANACETALDEHYDE; (AR)-A-METHYL-3-FURANACETALDEHYDE; (AS,BS)-A,B-DIMETHYL-1H-PYRROLE-1-PROPANAL; (BR)-A,B-DIMETHYL-1H-PYRROLE-1-PROPANAL; (BR)-B, 1-DIMETHYL-1H-PYRROLE-2-PROPANAL; (BR)-B-METHYL-2,5-DIOXO-1-PYRROLIDINEPROPANAL; (BS)-B,1-DIMETHYL-1H-PYRROLE-2-PROPANAL; (DIMETHYLHYDRAZONO)ACETALDEHYDE; (E)-2-ALLYL-2-ETHYLHEX-3-ENAL; (M-TOLYL)GLYOXAL HYDRATE; (PHENYLSULFANYL)ACETALDEHYDE; (R)-(−)-3-HYDROXYNONANAL; (R)-(+)-2,2-DIMETHYL-1,3-DIOXOLANE-4-CARBOXALDEHYDE; (R)-1,4-DIOXASPIRO[4,5]DECANE-2-CARBOXALDEHYDE; (R)-CYCLOHEX-3-ENECARBALDEHYDE; (S)-2-(1H-PYRROL-1-YL)PROPANAL; (S)-2-(2,5-DIMETHYL-1H-PYRROL-1-YL)PROPANAL; (S)-2-(BENZYLOXY)PROPIONAL; (S)-GLYCERALDEHYDE ACETONIDE; (S,E)-1-(BUT-1-ENYL)-5-OXOPYRROLIDINE-2-CARBALDEHYDE; (TERT-BUTYLDIMETHYLSILYLOXY)ACETALDEHYDE; (TETRAHYDROTHIOPYRAN-4-YL)-ACETALDEHYDE; [1,2,4]TRIAZINE-3-CARBALDEHYDE; [1,2,4]TRIAZOLO[4,3-A]PYRAZINE-3-CARBALDEHYDE; [1,3]DIOXOLO[4,5-B]PYRIDINE-6-CARBALDEHYDE; [1,3]DIOXOLO[4,5-B]PYRIDINE-7-CARBALDEHYDE; [1,6]NAPHTHYRIDINE-8-CARBALDEHYDE; [1,8]NAPHTHYRIDIN-2-YL-ACETALDEHYDE; [1,8]NAPHTHYRIDINE-2-CARBALDEHYDE; [1,8]NAPHTHYRIDINE-3-CARBALDEHYDE; [4-(2-OXO-ETHYL)-PHENYL]-ACETALDEHYDE; 1-([ETHYL(METHYL)AMINO]METHYL)CYCLOPENTANE-1-CARBALDEHYDE; 1-(1,1-DIMETHYLPROPYL)-2-FORMYLIMIDAZOLE; 1-(1,2-DIMETHYLPROPYL)-2-FORMYLIMIDAZOLE; 1-(1-ETHYLPROPYL)-2-FORMYLIMIDAZOLE; 1-(2,3-DIHYDROXY-PROPYL)-2-FORMYLIMIDAZOLE; 1-(2-CHLOROETHYL)-2-FORMYLIMIDAZOLE; 1-(2-FORMYLIMIDAZOL-1-YL)-PROPAN-2-OL; 1-(2-HYDROXY-1,1-DIMETHYLETHYL)-2-FORMYLIMIDAZOLE; 1-(2-HYDROXY-1-METHYL-ETHYL)-2-FORMYLIMIDAZOLE; 1-(2-HYDROXYETHYL)PIPERIDINE-2-CARBALDEHYDE; 1-(2-HYDROXYETHYL)PIPERIDINE-3-CARBALDEHYDE; 1-(2-HYDROXYETHYL)PIPERIDINE-4-CARBALDEHYDE; 1-(2-HYDROXYPROPYL)PIPERIDINE-2-CARBALDEHYDE; 1-(2-HYDROXYPROPYL)PIPERIDINE-3-CARBALDEHYDE; 1-(2-HYDROXYPROPYL)PIPERIDINE-4-CARBALDEHYDE; 1-(2-METHOXYETHYL)-1H-IMIDAZOLE-2-CARBALDEHYDE; 1-(2-METHOXYETHYL)PIPERIDINE-2-CARBALDEHYDE; 1-(2-METHOXYETHYL)PIPERIDINE-3-CARBALDEHYDE; 1-(2-METHOXYETHYL)PIPERIDINE-4-CARBALDEHYDE; 1-(2-METHYLPROP-2-EN-1-YL)PIPERIDINE-2-CARBALDEHYDE; 1-(2-METHYLPROP-2-EN-1-YL)PIPERIDINE-3-CARBALDEHYDE; 1-(2-METHYLPROP-2-EN-1-YL)PIPERIDINE-4-CARBALDEHYDE; 1-(2-METHYLPROPYL)PIPERIDINE-2-CARBALDEHYDE; 1-(2-METHYLPROPYL)PIPERIDINE-3-CARBALDEHYDE; 1-(2-METHYLPROPYL)PIPERIDINE-4-CARBALDEHYDE; 1-(3-CHLORO-PROPYL)-1H-IMIDAZOLE-2-CARBALDEHYDE; 1-(3-HYDROXYPROPYL)

PIPERIDINE-2-CARBALDEHYDE; 1-(3-HYDROXYPROPYL)PIPERIDINE-3-CARBALDEHYDE; 1-(3-HYDROXYPROPYL)PIPERIDINE-4-CARBALDEHYDE; 1-(3-METHOXYPROPYL)-2-FORMYL-1H-IMIDAZOLE; 1-(3-METHYLBUTYL)-1H-IMIDAZOLE-2-CARBALDEHYDE; 1-(BUT-2-YN-1-YL)PIPERIDINE-2-CARBALDEHYDE; 1-(BUT-2-YN-1-YL)PIPERIDINE-3-CARBALDEHYDE; 1-(BUT-2-YN-1-YL)PIPERIDINE-4-CARBALDEHYDE; 1-(BUT-3-EN-2-YL)PIPERIDINE-2-CARBALDEHYDE; 1-(BUT-3-EN-2-YL)PIPERIDINE-3-CARBALDEHYDE; 1-(BUT-3-EN-2-YL)PIPERIDINE-4-CARBALDEHYDE; 1-(BUT-3-YN-1-YL)PIPERIDINE-2-CARBALDEHYDE; 1-(BUT-3-YN-1-YL)PIPERIDINE-3-CARBALDEHYDE; 1-(BUT-3-YN-1-YL)PIPERIDINE-4-CARBALDEHYDE; 1-(BUTAN-2-YL)PIPERIDINE-2-CARBALDEHYDE; 1-(BUTAN-2-YL)PIPERIDINE-3-CARBALDEHYDE; 1-(BUTAN-2-YL)PIPERIDINE-4-CARBALDEHYDE; 1-(CYCLOPROPYLMETHYL)PIPERIDINE-2-CARBALDEHYDE; 1-(CYCLOPROPYLMETHYL)PIPERIDINE-3-CARBALDEHYDE; 1-(CYCLOPROPYLMETHYL)PIPERIDINE-4-CARBALDEHYDE; 1-(DIFLUOROMETHYL)-1H-IMIDAZOLE-2-CARBALDEHYDE; 1-(DIFLUOROMETHYL)PIPERIDINE-2-CARBALDEHYDE; 1-(DIFLUOROMETHYL)PIPERIDINE-3-CARBALDEHYDE; 1-(DIFLUOROMETHYL)PIPERIDINE-4-CARBALDEHYDE; 1-(DIMETHYLAMINOMETHYL)CYCLOPENTANECARBOXALDEHYDE; 1-(METHOXYMETHYL)-1H-PYRAZOLE-3-CARBALDEHYDE; 1-(PROP-2-EN-1-YL)PIPERIDINE-2-CARBALDEHYDE; 1-(PROP-2-EN-1-YL)PIPERIDINE-3-CARBALDEHYDE; 1-(PROP-2-EN-1-YL)PIPERIDINE-4-CARBALDEHYDE; 1-(PROP-2-YN-1-YL)PIPERIDINE-2-CARBALDEHYDE; 1-(PROP-2-YN-1-YL)PIPERIDINE-3-CARBALDEHYDE; 1-(PROP-2-YN-1-YL)PIPERIDINE-4-CARBALDEHYDE; 1-(PROPAN-2-YL)PIPERIDINE-2-CARBALDEHYDE; 1-(PROPAN-2-YL)PIPERIDINE-3-CARBALDEHYDE; 1-(PYRIDIN-2-YL)CYCLOBUTANECARBALDEHYDE; 1-(TETRAHYDROPYRANYLOXY)CYCLOPROPANECARBALDEHYDE; 1-(TRIFLUOROMETHYL)CYCLOPROPANECARBALDEHYDE; 1,1-DIOXO-HEXAHYDRO-1LAMBDA6-THIOPYRAN-4-CARBALDEHYDE; 1,2,3,4-TETRAHYDRONAPHTHALENE-1-CARBALDEHYDE; 1,2,3,4-TETRAHYDRO-NAPHTHALENE-2-CARBALDEHYDE; 1,2,3-BENZOTHIADIAZOLE-5-CARBOXALDEHYDE; 1,2,4-OXADIAZOLE-3-CARBOXALDEHYDE; 1,2,4-OXADIAZOLE-5-CARBOXALDEHYDE; 1,2,4-THIADIAZOLE-3-CARBOXALDEHYDE; 1,2,4-THIADIAZOLE-3-CARBOXALDEHYDE, 5-METHYL-; 1,2,4-THIADIAZOLE-5-CARBOXALDEHYDE; 1,2,4-THIADIAZOLE-5-CARBOXALDEHYDE, 3-METHYL-; 1,2,4-TRIAZOLO[4,3-A]PYRIDINE-3-CARBOXALDEHYDE; 1,2-BENZENEDICARBOXALDEHYDE, 3-FLUORO; 1,2-BENZISOXAZOLE-3-CARBOXALDEHYDE; 1,3,4-OXADIAZOLE-2-CARBALDEHYDE; 1,3,4-OXADIAZOLE-2-CARBOXALDEHYDE, 5-METHYL-; 1,3,4-THIADIAZOLE-2,5-DICARBOXALDEHYDE; 1,3,4-THIADIAZOLE-2-CARBOXALDEHYDE; 1,3,4-TRIMETHYL-3-CYCLOHEXEN-1-CARBOXALDEHYDE; 1,3,5-TRIAZINE-2-CARBALDEHYDE; 1,3-BENZENEDICARBOXALDEHYDE, 2-CHLORO-; 1,3-BENZENEDICARBOXALDEHYDE, 5-HYDROXY-; 1,3-BENZODIOXOLE-5-CARBOXALDEHYDE, 6-HYDROXY-; 1,3-BENZOTHIAZOLE-2-CARBALDEHYDE; 1,3-DIHYDRO-1-OXO-5-ISOBENZOFURANCARBOXALDEHYDE; 1,3-DIHYDRO-2,1,3-BENZOXADIAZOLE-5-CARBOXALDEHYDE; 1,3-DIHYDROFURO[3,4-C]PYRIDINE-6-CARBOXALDEHYDE; 1,3-DIMETHYLPIPERIDINE-4-CARBALDEHYDE; 1,3-DIOXOLANE-2,2-DIACETALDEHYDE; 1,3-DIOXOLANE-2-ACETALDEHYDE, 2-METHYL-; 1,3-DIOXOLANE-4-CARBOXALDEHYDE, 5-(HYDROXYMETHYL)-2,2-DIMETHYL-, (4R,5R)-; 1,3-OXAZOL-2-YLACETALDEHYDE; 1,3-THIAZOL-2-YLACETALDEHYDE; 1,4,5,6-TETRAHYDRO-CYCLOPENTAPYRAZOLE-3-CARBALDEHYDE; 1,4,5-TRIMETHYL-1H-IMIDAZOLE-2-CARBALDEHYDE; 1,4,6,7-TETRAHYDROPYRANO[4,3-C]PYRAZOLE-3-CARBALDEHYDE; 1,4,7-TRIOXASPIRO[4.4]NONANE-9-CARBALDEHYDE; 1,4-BENZODIOXAN-6-CARBOXALDEHYDE; 1,4-BENZODIOXIN-5-CARBOXALDEHYDE; 1,4-DIMETHYL-1H-IMIDAZOLE-2-CARBALDEHYDE; 1,4-DIMETHYL-5-NITRO-1H-IMIDAZOLE-2-CARBALDEHYDE; 1,4-DIMETHYLPIPERAZINE-2-CARBALDEHYDE; 1,4-DIMETHYLPIPERIDINE-4-CARBALDEHYDE; 1,4-DIOXANE-2-CARBOXALDEHYDE; 1,4-DIOXASPIRO[4.5]DECANE-8-CARBALDEHYDE; 1,5-DIMETHYL-1H-IMIDAZOLE-2-CARBALDEHYDE; 1,5-DIMETHYL-1H-PYRAZOLE-3-CARBALDEHYDE; 1,5-DIMETHYL-2-BENZIMIDAZOLECARBOXALDEHYDE; 1,5-NAPHTHYRIDINE-2-CARBOXALDEHYDE; 1,5-NAPHTHYRIDINE-3-CARBALDEHYDE; 1,5-NAPHTHYRIDINE-4-CARBOXALDEHYDE; 1,6-DIHYDRO-6-OXO-3-PYRIDAZINECARBOXALDEHYDE; 1,6-NAPHTHYRIDINE-2-CARBOXALDEHYDE; 1,6-NAPHTHYRIDINE-4-CARBOXALDEHYDE; 1,7-NAPHTHYRIDINE-3-CARBALDEHYDE; 1,8-NAPHTHYRIDINE-4-CARBOXALDEHYDE; 1,8-NAPHTHYRIDINE-4-CARBOXALDEHYDE, 3-HYDROXY-; 1-[(DIMETHYLAMINO)METHYL]CLOHEXANE-1-CARBALDEHYDE; 10-UNDECENAL; 1-ACETYL-2-PIPERIDINECARBOXALDEHYDE; 1-ACETYLAZETIDINE-3-CARBALDEHYDE; 1-ACETYLPIPERIDINE-3-CARBALDEHYDE; 1-ACETYLPIPERIDINE-4-CARBALDEHYDE; 1-ADAMANTANE CARBOXALDEHYDE; 1-ALLYL-1H-IMIDAZOLE-2-CARBALDEHYDE; 1-ALLYLCYCLOHEXANECARBALDEHYDE; 1-AZABICYCLO[2.2.2]OCTANE-2-CARBOXALDEHYDE; 1-AZA-BICYCLO[2.2.2]OCTANE-3-CARBALDEHYDE; 1-AZABICYCLO[2.2.2]OCTANE-4-CARBOXALDEHYDE; 1-BENZOFURAN-3-YLACETALDEHYDE; 1-BENZOFURAN-5-CARBALDEHYDE; 1-BENZOFURAN-6-CARBALDEHYDE; 1-BENZOTHIOPHENE-5-CARBALDEHYDE; 1-BUTYL-1H-IMIDAZOLE-2-CARBALDEHYDE; 1-BUTYLPIPERIDINE-2-CARBALDEHYDE; 1-BUTYLPIPERIDINE-3-CARBALDEHYDE; 1-BUTYLPIPERIDINE-4-CARBALDEHYDE; 1-CYCLOBUTYLMETHYL-1H-IMIDAZOLE-2-CARBALDEHYDE; 1-CYCLOPENTYL-1H-IMIDAZOLE-2-CARBALDEHYDE; 1-CYCLOPROPYL-1H-IMIDAZOLE-2-CARBALDEHYDE; 1-ETHYL-1H-1,2,4-TRIAZOLE-5-CARBALDEHYDE; 7; 1-ETHYL-1H-IMIDAZOLE-2-CARBALDEHYDE; 1-ETHYL-1H-INDOLE-4-CARBALDEHYDE; 1-ETHYL-1H-INDOLE-5-CARBALDEHYDE; 1-ETHYL-1H-INDOLE-6-CARBALDEHYDE; 1-ETHYL-1H-

PYRAZOLE-3-CARBALDEHYDE; 1-ETHYL-4-METHYL-1H-IMIDAZOLE-2-CARBALDEHYDE; 1-ETHYL-4-OXOCYCLOHEXANECARBALDEHYDE; 1-ETHYL-AZEPANE-4-CARBALDEHYDE; 1-ETHYLPIPERIDINE-2-CARBALDEHYDE; 1-ETHYLPIPERIDINE-3-CARBALDEHYDE; 1-ETHYLPIPERIDINE-4-CARBALDEHYDE; 1-FLUORONAPHTHALENE-2-CARBALDEHYDE; 1-FLUORONAPHTHALENE-3-CARBOXALDEHYDE; 1-FLUORONAPHTHALENE-7-CARBOXALDEHYDE; 1-FLUORONAPHTHALENE-8-CARBOXALDEHYDE; 1-FORMYL-2-(4-METHOXYPHENYL)-ETHYL; 1-FORMYL-CYCLOBUTANECARBOXYLIC ACID METHYL ESTER; 1-FORMYL-CYCLOHEXANECARBOXYLIC ACID METHYL ESTER; 1-FORMYL-CYCLOPENTANECARBOXYLIC ACID METHYL ESTER; 1-FORMYL-CYCLOPROPANECARBOXYLIC ACID METHYL ESTER; 1H-1,2,4-TRIAZOLE-3-CARBALDEHYDE; 1H-BENZIMIDAZOLE-1-ACETALDEHYDE; 1H-BENZO[D][1,2,3]TRIAZOLE-5-CARBALDEHYDE; 1H-INDAZOL-3-YLACETALDEHYDE; 1H-INDAZOLE-1-PROPANAL; 1H-INDAZOLE-3,4-DICARBOXALDEHYDE; 1H-INDAZOLE-3,5-DICARBOXALDEHYDE; 1H-INDAZOLE-3-CARBALDEHYDE; 1H-INDAZOLE-4-CARBALDEHYDE; 1H-INDAZOLE-5-CARBALDEHYDE; 1H-INDAZOLE-6-CARBALDEHYDE; 1H-INDAZOLE-7-CARBALDEHYDE; 1H-INDENE-1-CARBOXALDEHYDE, 2,3-DIHYDRO-; 1H-INDENE-2-CARBOXALDEHYDE,2,3-DIHYDRO-; 1H-INDOLE-1-PROPANAL; 1H-PYRAZOL-1-YLACETALDEHYDE; 1H-PYRAZOLE-3-CARBALDEHYDE; 1H-PYRAZOLE-3-CARBALDEHYDE, HYDROCHLORIDE; 1H-PYRAZOLE-3-CARBOXALDEHYDE, 1,4-DIMETHYL-; 1H-PYRAZOLO[3,4-B]PYRIDINE-3-CARBALDEHYDE; 1H-PYRAZOLO[3,4-B]PYRIDINE-5-CARBALDEHYDE; 1H-PYRAZOLO[3,4-C]PYRIDINE-4-CARBALDEHYDE; 1H-PYRAZOLO[3,4-C]PYRIDINE-5-CARBALDEHYDE; 1H-PYRAZOLO[3,4-C]PYRIDINE-7-CARBALDEHYDE; 1H-PYRAZOLO[4,3-B]PYRIDINE-5-CARBALDEHYDE; 1H-PYRAZOLO[4,3-B]PYRIDINE-6-CARBALDEHYDE; 1H-PYRAZOLO[4,3-B]PYRIDINE-7-CARBALDEHYDE; 1H-PYRAZOLO[4,3-C]PYRIDINE-4-CARBALDEHYDE; 1H-PYRROLE-1-BUTANAL; 1H-PYRROLE-1-PROPANAL; 1H-PYRROLO[2,3-B]PYRIDINE-1-PROPANAL; 1-HYDROXY-2-NAPHTHALDEHYDE; 1-ISOBUTYL-1H-IMIDAZOLE-2-CARBALDEHYDE; 1-ISOPROPYL-1H-IMIDAZOLE-2-CARBALDEHYDE; 1-ISOPROPYL-AZEPANE-4-CARBALDEHYDE; 1-ISOPROPYLPIPERIDINE-4-CARBALDEHYDE; 1-METHYL-1H-1,2,3-BENZOTRIAZOLE-5-CARBALDEHYDE; 1-METHYL-1H-BENZIMIDAZOLE-5-CARBOXALDEHYDE; 1-METHYL-1H-BENZO[D]IMIDAZOLE-6-CARBALDEHYDE; 1-METHYL-1H-IMIDAZO[4,5-B]PYRIDINE-2-CARBALDEHYDE; 1-METHYL-1H-IMIDAZO[4,5-C]PYRIDINE-2-CARBALDEHYDE; 1-METHYL-1H-IMIDAZOLE-2-CARBALDEHYDE; 1-METHYL-1H-INDAZOLE-3-CARBALDEHYDE; 1-METHYL-1H-INDAZOLE-4-CARBALDEHYDE; 1-METHYL-1H-INDAZOLE-5-CARBALDEHYDE; 1-METHYL-1H-INDAZOLE-6-CARBALDEHYDE; 1-METHYL-1H-INDAZOLE-7-CARBALDEHYDE; 1-METHYL-1H-INDOLE-3-ACETALDEHYDE; 1-METHYL-1H-INDOLE-4-CARBALDEHYDE; 1-METHYL-1H-INDOLE-5-ACETALDEHYDE; 1-METHYL-1H-INDOLE-5-CARBALDEHYDE; 1-METHYL-1H-INDOLE-6-CARBALDEHYDE; 1-METHYL-1H-INDOLE-7-CARBALDEHYDE; 1-METHYL-1H-PYRAZOLE-3-CARBALDEHYDE; 1-METHYL-1H-PYRAZOLO[3,4-C]PYRIDINE-4-CARBALDEHYDE; 1-METHYL-1H-PYRROLE-2-ACETALDEHYDE; 1-METHYL-1H-PYRROLE-2-PROPANAL; 1-METHYL-2,3-DIHYDRO-1H-PYRROLIZINE-2-CARBALDEHYDE; 1-METHYL-2-FORMYLBENZIMIDAZOLE; 1-METHYL-2-OXO-3-PIPERIDINEACETALDEHYDE; 1-METHYL-3,4-DIHYDROISOQUINOLINE-7-CARBALDEHYDE; 1-METHYL-3-CYCLOHEXENE-1-CARBOXALDEHYDE; 1-METHYL-3-PIPERIDINEACETALDEHYDE; 1-METHYL-4-OXOCYCLOHEXANECARBALDEHYDE; 1-METHYL-4-PIPERIDINECARBALDEHYDE HYDROCHLORIDE; 1-METHYL-5-NITRO-1H-IMIDAZOLE-2-CARBALDEHYDE; 1-METHYL-8-NAPHTHALDEHYDE; 1-METHYL-AZEPANE-4-CARBALDEHYDE; 1-METHYLBENZIMIDAZOLE-4-CARBOXALDEHYDE; 1-METHYLCYCLOHEXANE-1-CARBOXALDEHYDE; 1-METHYL-CYCLOPENTANECARBOXALDEHYDE; 1-METHYLINDOLINE-5-CARBALDEHYDE; 1-METHYLNAPHTHALENE-2-CARBOXALDEHYDE; 1-METHYLNAPHTHALENE-3-CARBOXALDEHYDE; 1-METHYLNAPHTHALENE-5-CARBOXALDEHYDE; 1-METHYLNAPHTHALENE-6-CARBOXALDEHYDE; 1-METHYLNAPHTHALENE-7-CARBOXALDEHYDE; 1-METHYLPIPERIDINE-2-CARBALDEHYDE; 1-METHYLPIPERIDINE-3-CARBALDEHYDE; 1-METHYLPIPERIDINE-4-CARBALDEHYDE; 1-NAPHTHALDEHYDE; 1-NAPHTHALENECARBOXALDEHYDE, 5,6,7,8-TETRAHYDRO; 1-OXO-1,2,3,4-TETRAHYDRONAPHTHALENE-2-CARBALDEHYDE; 1-PENTYL-1H-IMIDAZOLE-2-CARBALDEHYDE; 1-PHENYL-1H-IMIDAZOLE-2-CARBALDEHYDE; 1-PHENYLCYCLOPENTANECARBALDEHYDE; 1-PHENYLCYCLOPROPANECARBALDEHYDE; 1-PIPERIDINEPROPANAL; 1-PROPYL-1H-IMIDAZOLE-2-CARBALDEHYDE; 1-PROPYL-1H-PYRAZOLE-3-CARBALDEHYDE; 1-PROPYLPIPERIDINE-2-CARBALDEHYDE; 1-PROPYLPIPERIDINE-3-CARBALDEHYDE; 1-PROPYLPIPERIDINE-4-CARBALDEHYDE; 1-PYRIDIN-3-YL-1H-IMIDAZOLE-2-CARBALDEHYDE; 1-SEC-BUTYL-1H-IMIDAZOLE-2-CARBALDEHYDE; 1-TERT-BUTYL-1H-IMIDAZOLE-2-CARBALDEHYDE; 1-VINYL-1H-IMIDAZOLE-2-CARBALDEHYDE; 2-([(2-HYDROXYETHYL)(METHYL)AMINO]METHYL)-2-METHYLBUTANAL; 2-([2-(DIMETHYLAMINO)ETHYL](PROPYL)AMINO)ACETALDEHYDE; 2-([CYCLOPROPYL(METHYL)AMINO]METHYL)-2-METHYLBUTANAL; 2-([ETHYL(METHYL)AMINO]METHYL)-2-METHYLBUTANAL; 2-([ETHYL(METHYL)AMINO]METHYL)-2-METHYLPENTANAL; 2-(1-(2-OXOETHYL)-1H-PYRAZOL-4-YL)ACETONITRILE; 2-(1,2,4-OXADIAZOL-3-YL)BENZALDEHYDE; 2-(1,3,4-THIADIAZOL-2-YLSULFANYL)ACETALDEHYDE; 2-(1,3-DIOXOLAN-2-YL)ACETALDEHYDE; 2-(1,3-THIAZOL-2-YLSULFANYL)ACETALDEHYDE; OXAZEPAN-4-YL)ACETALDEHYDE; 2-(1-ACETYLAZETIDIN-2-YL)ACETALDEHYDE; 2-(1H-1,2,3-BENZOTRIAZOL-1-YL)ACETALDEHYDE; 2-(1H-1,2,4-TRIAZOL-1-YL)ACETALDEHYDE; 2-(1H-1,2,4-TRIAZOL-5-YLSULFANYL)ACETALDEHYDE; 2-(1H-IMIDAZOL-1-YL)PYRIMIDINE-5-CARBALDEHYDE; 2-(1H-INDOL-1-YL)ACETALDEHYDE; 2-(1H-PYRAZOL-1-YL)BENZALDEHYDE; 2-(1H-PYRAZOL-1-YL)PYRIMIDINE-5-CARBALDEHYDE; 2-(1H-PYRAZOL-

3-YL)BENZALDEHYDE; 2-(1H-PYRROL-1-YL)BENZALDEHYDE; 2-(1H-PYRROL-1-YL)PROPANAL; 2-(1-METHYL-1H-BENZO[D]IMIDAZOL-2-YL)ACETALDEHYDE; 2-(1-METHYL-2-OXOPYRROLIDIN-3-YL)ACETALDEHYDE; 2-(1-METHYLETHYL)-3-PYRIDINECARBOXALDEHYDE; 2-(1-METHYLETHYL)-4-PYRIDINECARBOXALDEHYDE; 2-(2-(3-OXOPROPYL)PHENYL)ACETONITRILE; 2-(2,2,2-TRIFLUOROETHOXY)ACETALDEHYDE; 2-(2,2,3,3-TETRAFLUOROPROPOXY)ACETALDEHYDE; 2-(2,2-DIMETHYLMORPHOLIN-4-YL)ACETALDEHYDE; 2-(2,2-DIMETHYLPYRROLIDIN-1-YL)ACETALDEHYDE; 2-(2,3,5-TRIFLUOROPHENYL)ACETALDEHYDE; 2-(2,3-DIFLUOROPHENOXY)ACETALDEHYDE; 2-(2,3-DIHYDRO-1H-INDOL-1-YL)ACETALDEHYDE; 2-(2,3-DIHYDRO-1H-ISOINDOL-2-YL)ACETALDEHYDE; 2-(2,3-DIHYDROBENZOFURAN-5-YL)ACETALDEHYDE; 2-(2,3-DIHYDROBENZOFURAN-6-YL)ACETALDEHYDE; 2-(2,3-DIMETHYLPHENOXY)ACETALDEHYDE; DIMETHYLPHENYL)ACETALDEHYDE; 2-(2,3-DIMETHYLPIPERIDIN-1-YL)ACETALDEHYDE; 2-(2,4,5-TRIFLUOROPHENYL)ACETALDEHYDE; 2-(2,4,6-TRIFLUOROPHENYL)ACETALDEHYDE; 2-(2,4-DIFLUOROPHENOXY)ACETALDEHYDE; 2-(2,4-DIFLUOROPHENYL)-2-OXOACETALDEHYDE; 2-(2,4-DIMETHYLPHENOXY)ACETALDEHYDE; 2-(2,4-DIMETHYLPHENYL)ACETALDEHYDE; 2-(2,4-DIMETHYLPIPERIDIN-1-YL)ACETALDEHYDE; 2-(2,4-DIOXO-1,3-THIAZOLIDIN-3-YL)ACETALDEHYDE; 2-(2,5-DIFLUOROPHENOXY)ACETALDEHYDE; 2-(2,5-DIMETHYLPHENOXY)ACETALDEHYDE; 2-(2,5-DIMETHYLPHENYL)ACETALDEHYDE; 2-(2,5-DIOXOPYRROLIDIN-1-YL)ACETALDEHYDE; 2-(2,6-DIFLUOROPHENYL)ACETALDEHYDE; 2-(2,6-DIMETHYLPHENOXY)ACETALDEHYDE; 2-(2,6-DIMETHYLPHENYL)ACETALDEHYDE; 2-(2,6-DIOXOPIPERIDIN-1-YL)ACETALDEHYDE; 2-(2,7-DIOXOAZEPAN-1-YL)ACETALDEHYDE; 2-(2-[(DIMETHYLAMINO)METHYL]PYRROLIDIN-1-YL)ACETALDEHYDE; 2-(2-AZABICYCLO[2.2.1]HEPTAN-2-YL)ACETALDEHYDE; 2-(2-BUTOXYETHOXY)ACETALDEHYDE; 2-(2-CHLORO-4-FLUOROPHENYL)ACETALDEHYDE; 2-(2-CHLORO-6-FLUOROPHENYL)ACETALDEHYDE; 2-(2-CHLOROPHENOXY)ACETALDEHYDE; 2-(2-CHLOROPHENYL)ACETALDEHYDE; 2-(2-ETHOXYETHOXY)ACETALDEHYDE; 2-(2-ETHOXYPHENYL)ACETALDEHYDE; 2-(2-ETHYL-1H-IMIDAZOL-1-YL)ACETALDEHYDE; 2-(2-ETHYLPHENOXY)ACETALDEHYDE; 2-(2-FLUORO-3-FORMYLPHENYL)ACETONITRILE; 2-(2-FLUORO-5-FORMYLPHENYL)ACETONITRILE; 2-(2-FLUORO-5-METHYLPHENYL)ACETALDEHYDE; 2-(2-FLUOROETHOXY)-BENZALDEHYDE; 2-(2-FLUOROPHENOXY)ACETALDEHYDE; 2-(2-FLUOROPHENYL)-3-OXOPROPANENITRILE; 2-(2-FLUOROPHENYL)ACETALDEHYDE; 2-(2-FORMYLIMIDAZOL-1-YL)-BUTAN-1-OL; 2-(2-FORMYLIMIDAZOL-1-YL)-PROPANE-1,3-DIOL; 2-(2-FORMYLPIPERIDIN-1-YL)ACETONITRILE; 2-(2-FORMYLPIPERIDIN-1-YL)PROPANENITRILE; 2-(2-FURYL)-2-OXO-ACETALDEHYDE; 2-(2-FURYL)-5-PYRIMIDINECARBALDEHYDE; 2-(2-HYDROXYETHOXY)ACETALDEHYDE; 2-(2-HYDROXYETHOXY)BENZALDEHYDE; 2-(2-METHOXY-5-METHYLPHENYL)ACETALDEHYDE; 2-(2-METHOXYETHOXY)ACETALDEHYDE; 2-(2-METHOXYETHYL)PYRIMIDINE-4-CARBALDEHYDE; 2-(2-METHOXYETHYL)PYRIMIDINE-5-CARBALDEHYDE; 2-(2-METHOXYPHENOXY)ACETALDEHYDE; 2-(2-METHYL-1,4-OXAZEPAN-4-YL)ACETALDEHYDE; 2-(2-METHYL-1H-IMIDAZOL-1-YL)ACETALDEHYDE; 2-(2-METHYL-1H-INDOL-1-YL)ACETALDEHYDE; 2-(2-METHYLFURAN-3-YL)ACETALDEHYDE; 2-(2-METHYLPHENOXY)ACETALDEHYDE; 2-(2-METHYLPHENYL)-3-OXOPROPANENITRILE; 2-(2-METHYLPROPOXY)ACETALDEHYDE; 2-(2-METHYLPROPYL)PYRIMIDINE-4-CARBALDEHYDE; 2-(2-METHYLPROPYL)PYRIMIDINE-5-CARBALDEHYDE; 2-(2-METHYLTHIAZOL-5-YL)ACETALDEHYDE; 2-(2-OXO-1,2-DIHYDROPYRIDIN-1-YL)ACETALDEHYDE; 2-(2-OXO-1,2-DIHYDROPYRIMIDIN-1-YL)ACETALDEHYDE; 2-(2-OXO-1,3-THIAZOLIDIN-3-YL)ACETALDEHYDE; 2-(2-OXO-2,3-DIHYDRO-1,3-THIAZOL-3-YL)ACETALDEHYDE; 2-(2-OXOAZEPAN-1-YL)ACETALDEHYDE; 2-(2-OXOAZOCAN-1-YL)ACETALDEHYDE; 2-(2-OXOETHOXY)BENZONITRILE; 2-(2-OXOPIPERIDIN-1-YL)ACETALDEHYDE; 2-(2-OXOPYRROLIDIN-1-YL)ACETALDEHYDE; 2-(2-PHENYLHYDRAZONO)ACETALDEHYDE; 2-(2-PROPYNYLOXY)BENZENECARBALDEHYDE; 2-(2-PYRAZINYL)MALONDIALDEHYDE; 2-(2-PYRIDINYLOXY)-ACETALDEHYDE; 2-(2-PYRIDYL)MALONDIALDEHYDE; 2-(3-(DIMETHYLAMINO)PHENYL)ACETALDEHYDE; 2-(3-(NITROMETHYL)OXETAN-3-YL)ACETALDEHYDE; 2-(3,3-DIMETHYLMORPHOLIN-4-YL)ACETALDEHYDE; 2-(3,4,5-TRIFLUOROPHENYL)ACETALDEHYDE; 2-(3,4-DIFLUOROPHENOXY)ACETALDEHYDE; 2-(3,4-DIMETHYLPHENOXY)ACETALDEHYDE; 2-(3,4-DIMETHYLPHENYL)-3-OXOPROPANENITRILE; 2-(3,4-DIMETHYLPHENYL)ACETALDEHYDE; 2-(3,5-DIFLUOROPHENOXY)ACETALDEHYDE; 2-(3,5-DIFLUOROPHENYL)ACETALDEHYDE; 2-(3,5-DIMETHYL-1H-1,2,4-TRIAZOL-1-YL)ACETALDEHYDE; 2-(3,5-DIMETHYLPHENOXY)ACETALDEHYDE; 2-(3,5-DIMETHYLPHENYL)ACETALDEHYDE; 2-(3,5-DIOXOMORPHOLIN-4-YL)ACETALDEHYDE; 2-(3,6-DIOXO-1,2,3,6-TETRAHYDROPYRIDAZIN-1-YL)ACETALDEHYDE; 2-(3-CHLORO-2-FLUOROPHENYL)ACETALDEHYDE; 2-(3-CHLORO-4-FLUOROPHENYL)ACETALDEHYDE; 2-(3-CHLOROPHENOXY)ACETALDEHYDE; 2-(3-ETHYLPHENOXY)ACETALDEHYDE; 2-(3-FLUORO-4-FORMYLPHENYL)ACETONITRILE; 2-(3-FLUORO-4-HYDROXYPHENYL)ACETALDEHYDE; 2-(3-FLUORO-4-METHYLPHENYL)ACETALDEHYDE; 2-(3-FLUORO-5-FORMYLPHENYL)ACETONITRILE; 2-(3-FLUORO-5-METHYLPHENYL)ACETALDEHYDE; 2-(3-FLUOROPHENOXY)ACETALDEHYDE; 2-(3-FLUOROPHENYL)-3-OXOPROPANENITRILE; 2-(3-FLUORO-PHENYL)-CYCLOPROPANECARBALDEHYDE; 2-(3-FLUORO-PHENYL)-MALONALDEHYDE; 2-(3-FORMYLPHENOXY)ACETONITRILE; 2-(3-FORMYLPHENYL)ACETONITRILE; 2-(3-FORMYLPIPERIDIN-1-YL)ACETONITRILE; 2-(3-FORMYLPIPERIDIN-1-YL)PROPANENITRILE; 2-(3-HYDROXYPYRROLIDIN-1-YL)ACETALDEHYDE; 2-(3-METHOXYPHENOXY)ACETALDEHYDE; 2-(3-METHOXYPHENYL)ACETALDEHYDE; 2-(3-METHOXYPROPOXY)ACETALDEHYDE; 2-(3-

METHYL-1H-INDOL-1-YL)ACETALDEHYDE; 2-(3-METHYL-2,4,5-TRIOXIOIMIDAZOLIDIN-1-YL)ACETALDEHYDE; 2-(3-METHYL-2,5-DIOXOIMIDAZOLIDIN-1-YL)ACETALDEHYDE; 2-(3-METHYL-2-OXO-1,2-DIHYDROPYRIDIN-1-YL)ACETALDEHYDE; 2-(3-METHYL-2-OXOIMIDAZOLIDIN-1-YL)ACETALDEHYDE; 2-(3-METHYLBUTOXY)ACETALDEHYDE; 2-(3-METHYLPHENYL)-3-OXOPROPANENITRILE; 2-(3-METHYLPHENYL)MALONDIALDEHYDE; 2-(3-NITRO-1H-1,2,4-TRIAZOL-1-YL)ACETALDEHYDE; 2-(3-OXOPROPANOYL)BENZONITRILE; 2-(4-(DIMETHYLAMINO)PHENYL)ACETALDEHYDE; 2-(4,4-DIMETHYLPIPERIDIN-1-YL)ACETALDEHYDE; 2-(4,5-DIMETHYL-2-OXO-2,3-DIHYDRO-1,3-THIAZOL-3-YL)ACETALDEHYDE; 2-(4,6-DIMETHYL-2-OXO-1,2-DIHYDROPYRIMIDIN-1-YL)ACETALDEHYDE; 2-(4-ACETYLPIPERAZIN-1-YL)ACETALDEHYDE; 2-(4-CHLORO-3-FLUOROPHENYL)ACETALDEHYDE; 2-(4-CHLOROPHENOXY)ACETALDEHYDE; 2-(4-CHLORO-PHENYL)-PROPIONALDEHYDE; 2-(4-CYCLOPROPYLPIPERAZIN-1-YL)ACETALDEHYDE; 2-(4-ETHOXYPHENYL)ACETALDEHYDE; 2-(4-ETHOXYPIPERIDIN-1-YL)ACETALDEHYDE; 2-(4-ETHYL-4-METHYLPIPERIDIN-1-YL)ACETALDEHYDE; 2-(4-ETHYLPHENOXY)ACETALDEHYDE; 2-(4-ETHYL-PHENYL)-3-OXO-PROPIONITRILE; 2-(4-ETHYLPHENYL)ACETALDEHYDE; 2-(4-ETHYLPIPERAZIN-1-YL)ACETALDEHYDE; 2-(4-ETHYLPIPERIDIN-1-YL)ACETALDEHYDE; 2-(4-FLUORO-2-METHYLPHENYL)ACETALDEHYDE; 2-(4-FLUORO-3-METHOXYPHENYL)ACETALDEHYDE; 2-(4-FLUORO-3-METHYLPHENYL)ACETALDEHYDE; 2-(4-FLUOROPHENOXY)ACETALDEHYDE; 2-(4-FLUOROPHENYL)-3-OXOPROPANENITRILE; 2-(4-FLUOROPHENYL)CYCLOPROPANECARBALDEHYDE; 2-(4-FLUOROPHENYL)MALONDIALDEHYDE; 2-(4-FORMYLPHENOXY)ACETONITRILE; 2-(4-FORMYLPHENYL)ACETONITRILE; 2-(4-FORMYLPIPERIDIN-1-YL)ACETONITRILE; 2-(4-FORMYLPIPERIDIN-1-YL)PROPANENITRILE; 2-(4-HYDROXY-3-METHOXYPHENYL)ACETALDEHYDE; 2-(4-HYDROXYPHENYL)ACETALDEHYDE; 2-(4-HYDROXYPIPERIDIN-1-YL)ACETALDEHYDE; 2-(4-METHOXY-2-METHYLPHENYL)ACETALDEHYDE; 2-(4-METHOXY-3-METHYLPHENYL)ACETALDEHYDE; 2-(4-METHOXYPHENOXY)ACETALDEHYDE; 2-(4-METHOXYPIPERIDIN-1-YL)ACETALDEHYDE; 2-(4-METHYL-1H-INDOL-1-YL)ACETALDEHYDE; 2-(4-METHYL-2,3-DIOXOPIPERAZIN-1-YL)ACETALDEHYDE; 2-(4-METHYL-2-OXO-2,3-DIHYDRO-1,3-THIAZOL-3-YL)ACETALDEHYDE; 2-(4-METHYL-2-OXOPYRROLIDIN-1-YL)ACETALDEHYDE; 2-(4-METHYL-6-OXO-1,6-DIHYDROPYRIMIDIN-1-YL)ACETALDEHYDE; 2-(4-METHYLPHENYL)-3-OXOPROPANENITRILE; 2-(4-METHYLPHENYL)MALONDIALDEHYDE; 2-(4-METHYLPIPERIDIN-1-YL)ACETALDEHYDE; 2-(4-NITRO-1H-IMIDAZOL-1-YL)ACETALDEHYDE; 2-(4-OXOCYCLOHEXYL)ACETALDEHYDE; 2-(4-OXOPIPERIDIN-1-YL)ACETALDEHYDE; 2-(4-PROPYLPHENYL)ACETALDEHYDE; 2-(4-PROPYLPIPERAZIN-1-YL)ACETALDEHYDE; 2-(4-PROPYLPIPERIDIN-1-YL)ACETALDEHYDE; 2-(4-PYRIDYL)MALONDIALDEHYDE; 2-(4-PYRIMIDYL)MALONDIALDEHYDE; DIMETHYL-1,3-DIOXAN-2-YL)ACETALDEHYDE; 2-(5-ETHYLPYRIDIN-2-YL)ACETALDEHYDE; 2-(5-FLUORO-2-METHYLPHENYL)ACETALDEHYDE; 2-(5-FLUOROPYRIDIN-3-YL)ACETALDEHYDE; 2-(5-METHYL-1H-INDOL-1-YL)ACETALDEHYDE; 2-(5-METHYL-2-OXO-1,2-DIHYDROPYRIMIDIN-1-YL)ACETALDEHYDE; 2-(5-METHYLFURAN-2-YL)-2-OXOACETALDEHYDE; 2-(5-NITROFURAN-2-YL)-2-OXOACETALDEHYDE; 2-(6-CHLOROPYRIDIN-3-YL)ACETALDEHYDE; 2-(6-METHYL-1H-INDOL-1-YL)ACETALDEHYDE; 2-(6-METHYL-2-OXO-1,2-DIHYDROPYRIDIN-1-YL)ACETALDEHYDE; 2-(6-METHYLPYRIDIN-3-YL)ACETALDEHYDE; 2-(7-METHYL-1H-INDAZOL-5-YL)ACETALDEHYDE; 2-(AZEPAN-1-YL)ACETALDEHYDE; 2-(AZOCAN-1-YL)ACETALDEHYDE; 2-(BENZO[D]OXAZOL-2-YL)ACETALDEHYDE; 2-(BENZOFURAN-5-YL)ACETALDEHYDE; 2-(BENZOFURAN-6-YL)ACETALDEHYDE; 2-(BENZYLSULFANYL)ACETALDEHYDE; 2-(BUT-2-YN-1-YLOXY)BENZALDEHYDE; 2-(BUT-3-EN-1-YLOXY)ACETALDEHYDE; 2-(BUT-3-YN-1-YLOXY)BENZALDEHYDE; 2-(BUTYLSULFANYL)ACETALDEHYDE; 2-(CHLOROMETHYL)NICOTINALDEHYDE; 2-(CHLOROMETHYL)PYRIMIDINE-4-CARBALDEHYDE; 2-(CHLOROMETHYL)PYRIMIDINE-5-CARBALDEHYDE; 2-(CYCLOHEPTYLOXY)ACETALDEHYDE; 2-(CYCLOHEXYLMETHOXY)ACETALDEHYDE; 2-(CYCLOHEXYLOXY)ACETALDEHYDE; 2-(CYCLOHEXYLSULFANYL)ACETALDEHYDE; 2-(CYCLOPENTYLOXY)ACETALDEHYDE; 2-(CYCLOPENTYLSULFANYL)ACETALDEHYDE; 2-(CYCLOPROPYLMETHOXY)ACETALDEHYDE; 2-(CYCLOPROPYLMETHYL)PYRIMIDINE-5-CARBALDEHYDE; 2-(DIBUTYLAMINO)ACETALDEHYDE; 2-(DIETHYLAMINO)ACETALDEHYDE; 2-(DIFLUOROMETHOXY)BENZALDEHYDE; 2-(DIFLUOROMETHOXY)PYRAZINE-6-CARBOXALDEHYDE; 2-(DIFLUOROMETHYL)-4-FLUOROBENZALDEHYDE; 2-(DIFLUOROMETHYL)BENZALDEHYDE; 2-(DIMETHYLAMINO)-3-HYDROXYBENZALDEHYDE; 2-(DIMETHYLAMINO)-4-HYDROXYBENZALDEHYDE; 2-(DIMETHYLAMINO)-5-FLUOROBENZALDEHYDE; 2-(DIMETHYLAMINO)-5-HYDROXYBENZALDEHYDE; 2-(DIMETHYLAMINO)-6-HYDROXYBENZALDEHYDE; 2-(DIMETHYLAMINO)-6-METHYLPYRIMIDINE-4-CARBALDEHYDE; 2-(DIMETHYLAMINO)ACETALDEHYDE; 2-(DIMETHYLAMINO)ISONICOTINALDEHYDE; 2-(DIMETHYLAMINO)NICOTINALDEHYDE; 2-(DIMETHYLAMINO)PYRIMIDINE-4-CARBOXALDEHYDE; 2-(DIPROPYLAMINO)ACETALDEHYDE; 2-(ETHYLSULFANYL)ACETALDEHYDE; 2-(FURAN-2-YL)-2-METHYLPROPANAL; 2-(FURAN-2-YL)-2-OXOACETALDEHYDE HYDRATE; 2-(FURAN-2-YL)ACETALDEHYDE; 2-(FURAN-2-YL)BUTANAL; 2-(FURAN-2-YL)PROPANAL; 2-(FURAN-2-YL)PYRIMIDINE-4-CARBALDEHYDE; 2-(FURAN-2-YLMETHOXY)ACETALDEHYDE; 2-(HEPTYLOXY)ACETALDEHYDE; 2-(HEXYLOXY)ACETALDEHYDE; 2-(HYDROXYMETHYL)-4-PYRIDINECARBOXALDEHYDE; 2-(HYDROXYMETHYL)-5-PYRIMIDINECARBOXALDEHYDE; 2-(HYDROXYMETHYL)-6-METHYLPYRIMIDINE-4-CARBALDEHYDE; 2-(HYDROXYMETHYL)PYRIMIDINE-4-CARBALDEHYDE; 2-(ISOQUINOLIN-5-YL)ACETALDEHYDE; 2-(ISOQUINOLIN-6-YL)ACETALDEHYDE; 2-(ISOQUI-

NOLIN-7-YL)ACETALDEHYDE; 2-(METHOXYMETHOXY)BENZALDEHYDE; 2-(METHOXYMETHYL)-5-PYRIMIDINECARBALDEHYDE; 2-(METHOXYMETHYL)-6-METHYLPYRIMIDINE-4-CARBALDEHYDE; 2-(METHOXYMETHYL) PYRIMIDINE-4-CARBALDEHYDE; 2-(METHYL[(1-METHYL-1H-PYRAZOL-4-YL)METHYL]AMINO) ACETALDEHYDE; 2-(METHYL[(1-METHYLPYRROLIDIN-3-YL)METHYL]AMINO) ACETALDEHYDE; 2-(METHYL[(2-METHYLFURAN-3-YL)METHYL]AMINO)ACETALDEHYDE; 2-(METHYL [(5-METHYLFURAN-2-YL)METHYL]AMINO) ACETALDEHYDE; 2-(METHYL[2-(PYRROLIDIN-1-YL)ETHYL]AMINO)ACETALDEHYDE; 2-(METHYLDITHIO)-ISOBUTYRALDEHYDE; 2-(METHYLTHIO)BENZALDEHYDE; 2-(METHYLTHIO)NICOTINALDEHYDE; 2-(METHYLTHIO)PYRIMIDINE-4-CARBALDEHYDE; 2-(METHYLTHIO)PYRIMIDINE-5-CARBALDEHYDE; 2-(N,N-DIMETHYLAMINO)BENZALDEHYDE; 2-(NAPHTHALEN-1-YL)ACETALDEHYDE; 2-(OXAN-4-YLMETHOXY)ACETALDEHYDE; 2-(OXAN-4-YLSULFANYL)ACETALDEHYDE; 2-(OXOLAN-3-YL) ACETALDEHYDE; 2-(OXOLAN-3-YLOXY) ACETALDEHYDE; 2-(PENTYLOXY) ACETALDEHYDE; 2-(PIPERIDIN-1-YL) ACETALDEHYDE; 2-(PIPERIDIN-1-YL)BUTANAL; 2-(PROP-2-EN-1-YLOXY)ACETALDEHYDE; 2-(PROPAN-2-YLOXY)ACETALDEHYDE; 2-(PROPAN-2-YLSULFANYL)ACETALDEHYDE; 2-(PROPYLSULFANYL)ACETALDEHYDE; 2-(PYRAZIN-2-YL) ACETALDEHYDE; 2-(PYRIDIN-2-YL) ACETALDEHYDE; 2-(PYRIDIN-2-YL) ACETALDEHYDE N-OXIDE; 2-(PYRIDIN-2-YLSULFANYL)ACETALDEHYDE; 2-(PYRIDIN-3-YL) ACETALDEHYDE; 2-(PYRIDIN-4-YL) ACETALDEHYDE; 2-(PYRIMIDIN-2-YL) ACETALDEHYDE; 2-(PYRIMIDIN-2-YLSULFANYL) ACETALDEHYDE; 2-(PYRIMIDIN-4-YL) ACETALDEHYDE; 2-(PYRIMIDIN-5-YL) ACETALDEHYDE; 2-(PYRROLIDIN-1-YL) ACETALDEHYDE; 2-(QUINOLIN-2-YL) ACETALDEHYDE; 2-(QUINOLIN-3-YL) ACETALDEHYDE; 2-(QUINOLIN-4-YL) ACETALDEHYDE; 2-(QUINOLIN-5-YL) ACETALDEHYDE; 2-(QUINOLIN-6-YL) ACETALDEHYDE; 2-(QUINOLIN-7-YL) ACETALDEHYDE; 2-(QUINOLIN-8-YL) ACETALDEHYDE; 2-(TERT-BUTOXY) ACETALDEHYDE; 2-(TERT-BUTYLSULFANYL) ACETALDEHYDE; 2-(TETRAHYDRO-2H-PYRAN-4-YL)-2-METHYLPROPANAL; 2-(TETRAHYDRO-2H-THIOPYRAN-4-YL)-2-METHYLPROPANAL; 2-(THIOMORPHOLIN-4-YL)ACETALDEHYDE; 2-(THIOPHEN-2-YL)ACETALDEHYDE; 2-(THIOPHEN-2-YLMETHOXY)ACETALDEHYDE; 2-(THIOPHEN-2-YLSULFANYL)ACETALDEHYDE; 2-(THIOPHEN-3-YL)ACETALDEHYDE; 2-(TRIFLUOROMETHYL) BENZALDEHYDE; 2-(TRIFLUOROMETHYL) PROPIONALDEHYDE; 2,2 DIMETHYL-4-CYANOBUTYRALDEHYDE; 2,2,3,3,3-PENTAFLUOROPROPANAL; 2,2,3-TRIMETHYLCYCLOPENT-3-ENE-1-CARBOXALDEHYDE; 2,2,4-TRIMETHYL-3-HYDROXYPENTANAL; 2,2,5-TRIMETHYLHEX-4-ENAL; 2,2,5-TRIMETHYLHEXANAL; 2,2,6,6-TETRAMETHYLTETRAHYDRO-2H-PYRAN-4-CARBALDEHYDE; 2,2-BIS(ETHYLTHIO) ACETALDEHYDE; 2,2-DICHLOROHEXANAL; 2,2-DICHLOROPENTANAL; 2,2-DIFLUOROACETALDEHYDE; 2,2-DIFLUOROCYCLOPROPANECARBALDEHYDE; 2,2-DIMETHYL-1,3-DIOXANE-5-CARBALDEHYDE; 2,2-DIMETHYL-1,3-DIOXOLANE-4-CARBOXALDEHYDE; 2,2-DIMETHYL-3-(2-METHYLPYRROLIDIN-1-YL) PROPANAL; 2,2-DIMETHYL-3-(3-METHYLPYRROLIDIN-1-YL)PROPANAL; 2,2-DIMETHYL-3,4-OCTADIENAL; 2,2-DIMETHYL-3-[METHYL(2-METHYLPROPYL)AMINO]PROPANAL; 2,2-DIMETHYL-3-[METHYL(PROPAN-2-YL)AMINO] PROPANAL; 2,2-DIMETHYL-3-[METHYL(PROPYL) AMINO]PROPANAL; 2,2-DIMETHYL-3-MORPHOLIN-4-YLPROPANAL; 2,2-DIMETHYL-3-OXOHEPT-6-ENAL; 2,2-DIMETHYL-3-OXOHEPTANAL; 2,2-DIMETHYL-3-OXOHEXANAL; 2,2-DIMETHYL-3-OXOCTANAL; 2,2-DIMETHYL-3-OXOPENTANAL; 2,2-DIMETHYL-3-PHENYLPROPIONALDEHYDE; 2,2-DIMETHYL-3-PIPERIDIN-1-YLPROPANAL; 2,2-DIMETHYL-3-PYRROLIDIN-1-YLPROPANAL; 2,2-DIMETHYL-4-HEXEN-1-ALDEHYDE; 2,2-DIMETHYL-4-PENTENAL; 2,2-DIMETHYL-5-VINYL-[1,3] DIOXOLANE-4-CARBALDEHYDE; 2,2-DIMETHYLBUTANAL; 2,2-DIMETHYLNONANAL; 2,2-DIMETHYL-SUCCINALDEHYDONITRILE; 2,2-DIMETHYL-TETRAHYDRO-PYRAN-4-CARBALDEHYDE; 2,2-DIMETHYL-TETRAHYDROTHIOPHENE-3-CARBOXALDEHYDE; 2,2'-OXYBISACETALDEHYDE; 2,3-(METHYLENEDIOXY)BENZALDEHYDE; 2,3,4,5-TETRAHYDROXY-PENTANAL; 2,3,4-TRIFLUOROBENZALDEHYDE; 2,3,4-TRIFLUOROBENZENEYL ACETALDEHYDE; 2,3,4-TRIHYDROXY-6-METHYL-BENZALDEHYDE; 2,3,4-TRIHYDROXYBENZALDEHYDE; 2,3,5,6-TETRAMETHYLBENZALDEHYDE; 2,3,5-TRIFLUORO-4-PYRIDINECARBOXALDEHYDE; 2,3,5-TRIFLUOROBENZALDEHYDE; 2,3,6-TRIFLUOROBENZALDEHYDE; 2,3,6-TRIFLUOROPYRIDINE-4-CARBOXALDEHYDE; 2,3,6-TRIMETHYLCYCLOHEXYLMETHANAL; 2,3-DICHLORO-2-METHYLPROPANAL; 2,3-DICHLOROPROPIONALDEHYDE; 2,3-DIFLUORO-4-HYDROXYBENZALDEHYDE; 2,3-DIFLUORO-4-METHOXYBENZALDEHYDE; 2,3-DIFLUORO-4-METHYLBENZALDEHYDE; 2,3-DIFLUORO-5-METHYLBENZALDEHYDE; 2,3-DIFLUORO-6-HYDROXYBENZALDEHYDE; 2,3-DIFLUORO-6-METHOXYBENZALDEHYDE; 2,3-DIFLUORO-6-METHYLBENZALDEHYDE; 2,3-DIFLUOROBENZALDEHYDE; 2,3-DIFLUOROBENZENEPROPANAL; 2,3-DIFLUOROISONICOTINALDEHYDE; 2,3-DIHYDRO-[1,4]DIOXINO[2,3-B]PYRIDINE-6-CARBALDEHYDE; 2,3-DIHYDRO-[1,4]DIOXINO[2,3-B]PYRIDINE-7-CARBALDEHYDE; 2,3-DIHYDRO-[1,4]DIOXINO[2,3-C] PYRIDINE-7-CARBALDEHYDE; 2,3-DIHYDRO-1,4-BENZODIOXINE-5-CARBALDEHYDE; 2,3-DIHYDRO-1-BENZOFURAN-2-CARBALDEHYDE; 2,3-DIHYDRO-1-BENZOFURAN-7-CARBALDEHYDE; 2,3-DIHYDRO-2,5-DIMETHYL-2-FORMYL-1,4-PYRAN; 2,3-DIHYDRO-2-OXO-3-FURANCARBOXALDEHYDE; 2,3-DIHYDRO-4-BENZOFURANCARBOXALDEHYDE; 2,3-DIHYDRO-BENZO[1,4]DIOXINE-2-CARBALDEHYDE; 2,3-DIHYDROBENZO[B]FURAN-5-CARBOXALDEHYDE; 2,3-DIHYDRO-BENZOFURAN-6-CARBALDEHYDE; 2,3-DIHYDROXY-4-

METHOXYBENZALDEHYDE; 2,3-DIHYDROXYBENZALDEHYDE; 2,3-DIMETHOXYBENZALDEHYDE; 2,3-DIMETHOXYISONICOTINALDEHYDE; 2,3-DIMETHYLANISALDEHYDE; 2,3-DIMETHYLBENZALDEHYDE; 2,3-DIMETHYL-BENZENEPROPANAL; 2,3-DIMETHYLISONICOTINALDEHYDE; 2,3-DIMETHYLPENTANAL; 2,3-EPOXYDECANAL; 2,3-EPOXYHEPTANAL; 2,3-EPOXYOCTANAL; 2,3-O-(3-PENTYLIDENE)-D-GLYCERALDEHYDE; 2,3-O-(3-PENTYLIDENE)-L-GLYCERALDEHYDE; 2,3-PYRIDINEDICARBOXALDEHYDE; 2,4,5-TRIFLUORO-3-METHYLBENZALDEHYDE; 2,4,5-TRIFLUOROBENZALDEHYDE; 2,4,5-TRIHYDROXYBENZALDEHYDE; 2,4,5-TRIMETHYLBENZALDEHYDE; 2,4,6-PYRIDINETRICARBOXALDEHYDE; 2,4,6-TRIFLUOROBENZALDEHYDE; 2,4,6-TRIHYDROXYBENZALDEHYDE; 2,4,6-TRIHYDROXYPYRIMIDINE-5-CARBOXALDEHYDE; 2,4,6-TRIIFLUOROPYRIDINE-3-CARBOXALDEHYDE; 2,4,6-TRIMETHYL-3-CYCLOHEXENE-1-CARBOXALDEHYDE; 2,4,6-TRIMETHYLBENZALDEHYDE; 2,4,6-TRIMETHYL-PYRIDINE-3-CARBALDEHYDE; 2,4-DIFLUORO-3-FORMYLBENZONITRILE; 2,4-DIFLUORO-3-HYDROXYBENZALDEHYDE; 2,4-DIFLUORO-3-METHOXYBENZALDEHYDE; 2,4-DIFLUORO-3-METHYLBENZALDEHYDE; 2,4-DIFLUORO-5-METHYLBENZALDEHYDE; 2,4-DIFLUORO-6-HYDROXYBENZALDEHYDE; 2,4-DIFLUORO-6-METHYLBENZALDEHYDE; 2,4-DIFLUOROBENZALDEHYDE; 2,4-DIFLUORONICOTINALDEHYDE; 2,4-DIHYDROXY-3-METHYLBENZALDEHYDE; 2,4-DIHYDROXY-5-METHOXYBENZALDEHYDE; 2,4-DIHYDROXY-6-METHYLBENZALDEHYDE; 2,4-DIHYDROXYBENZALDEHYDE; 2,4-DIHYDROXY-BENZENE-1,3-DICARB-ALDEHYDE; 2,4-DIMETHOXY-5-FORMYLPYRIMIDINE; 2,4-DIMETHOXYBENZALDEHYDE; 2,4-DIMETHOXYNICOTINALDEHYDE; 2,4-DIMETHYL-3-CYCLOHEXENECARBOXALDEHYDE; 2,4-DIMETHYL-3-FLUOROBENZALDEHYDE; 2,4-DIMETHYLBENZALDEHYDE; 2,4-DIMETHYLNICOTINALDEHYDE; 2,4-DIMETHYLPYRIMIDINE-5-CARBALDEHYDE; 2,4-DIOXOTETRAHYDROFURAN-3-CARBALDEHYDE; 2,4-O-ETHYLIDENE-D-ERYTHROSE; 2,4-PYRIDINEDICARBOXALDEHYDE; 2,4-PYRIDINEDICARBOXALDEHYDE, 6-METHYL-; 2,5-ANHYDRO-D-MANNOSE; 2,5-DIFLUORO-3-METHYLBENZALDEHYDE; 2,5-DIFLUORO-4-HYDROXYBENZALDEHYDE; 2,5-DIFLUORO-4-METHOXYBENZALDEHYDE; 2,5-DIFLUORO-4-METHYLBENZALDEHYDE; 2,5-DIFLUORO-6-METHYLBENZALDEHYDE; 2,5-DIFLUOROBENZALDEHYDE; 2,5-DIFLUOROPYRIDINE-3-CARBOXALDEHYDE; 2,5-DIFLUOROPYRIDINE-4-CARBOXALDEHYDE; 2,5-DIHYDRO-1-METHYL-5-OXO-1H-PYRROLE-2-PROPANAL; 2,5-DIHYDRO-5-OXO-2-FURANCARBOXALDEHYDE; 2,5-DIHYDROXY-3-METHOXYBENZENECARBALDEHYDE; 2,5-DIHYDROXYBENZALDEHYDE; 2,5-DIMETHOXY-3-TETRAHYDROFURANCARBOXALDEHYDE; 2,5-DIMETHOXYBENZALDEHYDE; 2,5-DIMETHOXYISONICOTINALDEHYDE; 2,5-DIMETHOXYNICOTINALDEHYDE; 2,5-DIMETHYL-1H-PYRROLE-1-ACETALDEHYDE; 2,5-DIMETHYL-4-METHOXYBENZALDEHYDE; 2,5-DIMETHYLBENZALDEHYDE; 2,5-DIMETHYL-BENZENEPROPANAL; 2,5-DIMETHYLISONICOTINALDEHYDE; 2,5-DIMETHYLPYRIDINE-3-CARBOXALDEHYDE; 2,5-DIMETHYLTEREPHTHALALDEHYDE; 2,5-DIOXO-1-PYRROLIDINEBUTANAL; 2,5-PYRAZINEDICARBOXALDEHYDE; 2,5-PYRIDINEDICARBOXALDEHYDE; 2,6,6-TRIMETHYL-1-CYCLOHEXENE-1-ACETALDEHYDE; 2,6-DIETHYLBENZALDEHYDE; 2,6-DIFLUORO-3-HYDROXYBENZALDEHYDE; 2,6-DIFLUORO-3-METHOXYBENZALDEHYDE; 2,6-DIFLUORO-3-METHYLBENZALDEHYDE; 2,6-DIFLUORO-4-FORMYLBENZONITRILE; 2,6-DIFLUORO-4-HYDROXYBENZALDEHYDE; 2,6-DIFLUORO-4-METHOXYBENZALDEHYDE; 2,6-DIFLUORO-4-METHYLBENZALDEHYDE; 2,6-DIFLUOROBENZALDEHYDE; 2,6-DIFLUOROPYRIDINE-3-CARBOXALDEHYDE; 2,6-DIFLUOROPYRIDINE-4-CARBOXALDEHYDE; 2,6-DIFORMYLPHENOL; 2,6-DIHYDROXY-4-METHYLBENZALDEHYDE; 2,6-DIHYDROXYBENZALDEHYDE; 2,6-DIMETHOXY-3-FORMYLPYRIDINE; 2,6-DIMETHOXYBENZALDEHYDE; 2,6-DIMETHOXYISONICOTINALDEHYDE; 2,6-DIMETHYL-3-HYDROXYBENZALDEHYDE; 2,6-DIMETHYL-3-METHOXYBENZALDEHYDE; 2,6-DIMETHYL-4-FLUOROBENZALDEHYDE; 2,6-DIMETHYL-4-HYDROXYBENZALDEHYDE; 2,6-DIMETHYL-5-HEPTENAL; 2,6-DIMETHYLBENZALDEHYDE; 2,6-DIMETHYL-BENZENEPROPANAL; 2,6-DIMETHYLPHENYLGLYOXAL; 2,6-DIMETHYL-PYRIDINE-3-CARBALDEHYDE; 2,6-DIMETHYLPYRIDINE-4-CARBOXALDEHYDE; 2,6-DIMETHYLPYRIMIDINE-4-CARBALDEHYDE; 2,6-PYRIDINEDICARBOXALDEHYDE; 2,7-NAPHTHYRIDINE-4-CARBALDEHYDE; 2-[(1-METHYL-1H-IMIDAZOL-2-YL)SULFANYL]ACETALDEHYDE; 2-[(1-METHYL-1H-PYRAZOL-4-YL)SULFANYL]ACETALDEHYDE; 2-[(2,2-DIMETHYLPROPYL)(METHYL)AMINO]ACETALDEHYDE; 2-[(2-FLUOROPHENYL)(METHYL)AMINO]ACETALDEHYDE; 2-[(2-FLUOROPHENYL)SULFANYL]ACETALDEHYDE; 2-[(2-HYDROXYETHYL)(METHYL)AMINO]ACETALDEHYDE; 2-[(2-HYDROXYETHYL)(PENTAN-3-YL)AMINO]ACETALDEHYDE; 2-[(2-HYDROXYETHYL)(PROPAN-2-YL)AMINO]ACETALDEHYDE; 2-[(2-HYDROXYETHYL)(PROPYL)AMINO]ACETALDEHYDE; 2-[(2-HYDROXYETHYL)SULFANYL]ACETALDEHYDE; 2-[(2-HYDROXYPROPYL)(METHYL)AMINO]ACETALDEHYDE; 2-[(2-METHOXYETHYL)(2-METHYLPROPYL)AMINO]ACETALDEHYDE; 2-[(2-METHOXYETHYL)(METHYL)AMINO]ACETALDEHYDE; 2-[(2-METHOXYETHYL)SULFANYL]ACETALDEHYDE; 2-[(2-METHYLBUTAN-2-YL)OXY]ACETALDEHYDE; 2-[(2-METHYLPHENYL)SULFANYL]ACETALDEHYDE; 2-[(2-METHYLPROPYL)(PROPAN-2-YL)AMINO]ACETALDEHYDE; 2-[(2-METHYLPROPYL)SULFANYL]ACETALDEHYDE; 2-[(3-FLUOROPHENYL)(METHYL)

AMINO]ACETALDEHYDE; 2-[(3-HYDROXYPROPYL)(PROPAN-2-YL)AMINO]ACETALDEHYDE; 2-[(3-METHOXYPROPYL)(METHYL)AMINO]ACETALDEHYDE; 2-[(3-METHYLCYCLOHEXYL)SULFANYL]ACETALDEHYDE; 2-[(3-METHYLPHENYL)SULFANYL]ACETALDEHYDE; 2-[(4,5-DIMETHYL-4H-1,2,4-TRIAZOL-3-YL)SULFANYL]ACETALDEHYDE; 2-[(4-FLUOROPHENYL)(METHYL)AMINO]ACETALDEHYDE; 2-[(4-FLUOROPHENYL)SULFANYL]ACETALDEHYDE; 2-[(4-HYDROXYPYRIMIDIN-2-YL)SULFANYL]ACETALDEHYDE; 2-[(4-METHYL-1,3-THIAZOL-2-YL)SULFANYL]ACETALDEHYDE; 2-[(4-METHYL-4H-1,2,4-TRIAZOL-3-YL)SULFANYL]ACETALDEHYDE; 2-[(4-METHYLCYCLOHEXYL)OXY]ACETALDEHYDE; 2-[(4-METHYLPENTYL)OXY]ACETALDEHYDE; 2-[(4-METHYLPHENYL)SULFANYL]ACETALDEHYDE; 2-[(4-METHYLPYRIMIDIN-2-YL)SULFANYL]ACETALDEHYDE; 2-[(5-METHYL-1,3,4-OXADIAZOL-2-YL)SULFANYL]ACETALDEHYDE; 2-[(5-METHYL-1,3,4-THIADIAZOL-2-YL)SULFANYL]ACETALDEHYDE; 2-[(5-METHYLPYRIMIDIN-2-YL)SULFANYL]ACETALDEHYDE; 2-[(CYANOMETHYL)(2-OXOETHYL)AMINO]ACETONITRILE; 2-[(CYANOMETHYL)(3-OXOPROPYL)AMINO]ACETONITRILE; 2-[(CYCLOBUTYLMETHYL)(METHYL)AMINO]ACETALDEHYDE; 2-[(CYCLOHEXYLMETHYL)(METHYL)AMINO]ACETALDEHYDE; 2-[(CYCLOPENTYLMETHYL)SULFANYL]ACETALDEHYDE; 2-[(CYCLOPROPYLMETHYL)(METHYL)AMINO]ACETALDEHYDE; 2-[(CYCLOPROPYLMETHYL)(PROPAN-2-YL)AMINO]ACETALDEHYDE; 2-[(CYCLOPROPYLMETHYL)(PROPYL)AMINO]ACETALDEHYDE; 2-[(DIETHYLAMINO)METHYL]-2-METHYLBUTANAL; 2-[(DIMETHYLAMINO)METHYL]-2-ETHYLBUTANAL; 2-[(DIMETHYLAMINO)METHYL]-2-METHYLBUTANAL; 2-[(DIMETHYLAMINO)METHYL]-2-METHYLPENTANAL; 2-[(FURAN-2-YLMETHYL)(METHYL)AMINO]ACETALDEHYDE; 2-[(FURAN-2-YLMETHYL)SULFANYL]ACETALDEHYDE; 2-[(FURAN-3-YLMETHYL)(METHYL)AMINO]ACETALDEHYDE; 2-[(METHYLSULFANYL)METHYL]PYRIMIDINE-4-CARBALDEHYDE; 2-[(METHYLSULFANYL)METHYL]PYRIMIDINE-5-CARBALDEHYDE; 2-[1,2,4]TRIAZOL-1-YL-BENZALDEHYDE; 2-[2-(3-HYDROXYPROPYL)PYRROLIDIN-1-YL]ACETALDEHYDE; 2-[2-(HYDROXYMETHYL)PYRROLIDIN-1-YL]ACETALDEHYDE; 2-[2-(PROPAN-2-YL)-1H-IMIDAZOL-1-YL]ACETALDEHYDE; 2-[2-(PROPAN-2-YLOXY)ETHOXY]ACETALDEHYDE; 2-[2-(PYRIDIN-2-YL)ETHOXY]ACETALDEHYDE; 2-[2-(THIOPHEN-2-YL)ETHOXY]ACETALDEHYDE; 2-[3-(DIMETHYLAMINO)PYRROLIDIN-1-YL]ACETALDEHYDE; 2-[3-(HYDROXYMETHYL)PHENOXY]ACETALDEHYDE; 2-[4-(2-HYDROXYETHYL)PIPERAZIN-1-YL]ACETALDEHYDE; 2-[4-(DIMETHYLAMINO)PIPERIDIN-1-YL]ACETALDEHYDE; 2-[4-(HYDROXYMETHYL)PHENOXY]ACETALDEHYDE; 2-[4-(HYDROXYMETHYL)PIPERIDIN-1-YL]ACETALDEHYDE; 2-[4-(PROPAN-2-YL)PIPERAZIN-1-YL]ACETALDEHYDE; 2-[BENZYL(METHYL)AMINO]ACETALDEHYDE; 2-[BIS(2-HYDROXYETHYL)AMINO]ACETALDEHYDE; 2-[BIS(2-METHYLPROPYL)AMINO]ACETALDEHYDE; 2-[BUTYL(2-HYDROXYETHYL)AMINO]ACETALDEHYDE; 2-[BUTYL(CYCLOPROPYL)AMINO]ACETALDEHYDE; 2-[BUTYL(ETHYL)AMINO]ACETALDEHYDE; 2-[BUTYL(METHYL)AMINO]ACETALDEHYDE; 2-[CYCLOHEPTYL(METHYL)AMINO]ACETALDEHYDE; 2-[CYCLOHEXYL(ETHYL)AMINO]ACETALDEHYDE; 2-[CYCLOHEXYL(METHYL)AMINO]ACETALDEHYDE; 2-[CYCLOPENTYL(2-HYDROXYETHYL)AMINO]ACETALDEHYDE; 2-[CYCLOPENTYL(ETHYL)AMINO]ACETALDEHYDE; 2-[CYCLOPENTYL(METHYL)AMINO]ACETALDEHYDE; 2-[CYCLOPROPYL(2-HYDROXYETHYL)AMINO]ACETALDEHYDE; 2-[CYCLOPROPYL(2-METHOXYETHYL)AMINO]ACETALDEHYDE; 2-[CYCLOPROPYL(2-METHYLPROPYL)AMINO]ACETALDEHYDE; 2-[CYCLOPROPYL(ETHYL)AMINO]ACETALDEHYDE; 2-[CYCLOPROPYL(METHYL)AMINO]ACETALDEHYDE; 2-[CYCLOPROPYL(PROPYL)AMINO]ACETALDEHYDE; 2-[ETHYL(2,2,2-TRIFLUOROETHYL)AMINO]ACETALDEHYDE; 2-[ETHYL(2-ETHYLBUTYL)AMINO]ACETALDEHYDE; 2-[ETHYL(2-HYDROXYETHYL)AMINO]ACETALDEHYDE; 2-[ETHYL(2-METHOXYETHYL)AMINO]ACETALDEHYDE; 2-[ETHYL(2-METHYLPROPYL)AMINO]ACETALDEHYDE; 2-[ETHYL(2-OXOETHYL)AMINO]-N,N-DIMETHYLACETAMIDE; 2-[ETHYL(FURAN-2-YLMETHYL)AMINO]ACETALDEHYDE; 2-[ETHYL(METHYL)AMINO]ACETALDEHYDE; 2-[ETHYL(METHYL)AMINO]BENZALDEHYDE; 2-[ETHYL(PHENYL)AMINO]ACETALDEHYDE; 2-[ETHYL(PROPAN-2-YL)AMINO]ACETALDEHYDE; 2-[ETHYL(PROPYL)AMINO]ACETALDEHYDE; 2-[METHYL(1,3-THIAZOL-4-YLMETHYL)AMINO]ACETALDEHYDE; 2-[METHYL(1-METHYLPIPERIDIN-3-YL)AMINO]ACETALDEHYDE; 2-[METHYL(1-METHYLPIPERIDIN-4-YL)AMINO]ACETALDEHYDE; 2-[METHYL(2,2,2-TRIFLUOROETHYL)AMINO]ACETALDEHYDE; 2-[METHYL(2-METHYLPHENYL)AMINO]ACETALDEHYDE; 2-[METHYL(2-METHYLPROPYL)AMINO]ACETALDEHYDE; 2-[METHYL(3-METHYLBUTYL)AMINO]ACETALDEHYDE; 2-[METHYL(3-METHYLPHENYL)AMINO]ACETALDEHYDE; 2-[METHYL(4-METHYLCYCLOHEXYL)AMINO]ACETALDEHYDE; 2-[METHYL(4-METHYLPHENYL)AMINO]ACETALDEHYDE; 2-[METHYL(PENTAN-3-YL)AMINO]ACETALDEHYDE; 2-[METHYL(PENTYL)AMINO]ACETALDEHYDE; 2-[METHYL(PHENYL)AMINO]ACETALDEHYDE; 2-[METHYL(PROPAN-2-YL)AMINO]ACETALDEHYDE; 2-[METHYL(PROPYL)AMINO]ACETALDEHYDE; 2-[METHYL(PYRIDIN-2-YLMETHYL)AMINO]ACETALDEHYDE; 2-[METHYL(PYRIDIN-3-YLMETHYL)AMINO]ACETALDEHYDE; 2-[METHYL(PYRIDIN-4-YLMETHYL)AMINO]ACETALDEHYDE; 2-[METHYL(THIOPHEN-2-YLMETHYL)AMINO]ACETALDEHYDE; 2-[METHYL(THIOPHEN-3-YLMETHYL)AMINO]ACETALDEHYDE; 2-[PENTYL(PROPAN-2-YL)AMINO]ACETALDEHYDE; 2-[PROPAN-2-YL(PROPYL)AMINO]ACETALDEHYDE; 2-ACETYL-3-PYRIDINECARBOXALDEHYDE; 2-ACETYL-5-OXO-PENTANOIC ACID METHYL ESTER; 2-ACETYLBENZALDEHYDE; 2-ACETYLPYRIDINE-4-CARBALDEHYDE; 2-ALLYL-3-HYDROXYBENZALDEHYDE; 2-ALLYLOXYBENZALDEHYDE; 2-BENZOFURANGLYOXYLALDEHYDE; 2-BENZOFURANPROPANAL; 2-BROMO-2-METHYLPROPIONALDEHYDE; 2-BROMO-3-METHYLBUTYRALDEHYDE; 2-BROMOBUTANAL; 2-BROMOMA-

LONALDEHYDE; 2-BROMO-PROPIONALDEHYDE; 2-BUTOXYACETALDEHYDE; 2-BUTYLPYRIMIDINE-4-CARBALDEHYDE; 2-BUTYL-PYRIMIDINE-5-CARBALDEHYDE; 2-BUTYNAL; 2-CHLORO-2-METHYLPROPANAL; 2-CHLORO-3,4-DIHYDROXYBENZALDEHYDE; 2-CHLORO-3,5-DIMETHYLBENZALDEHYDE; 2-CHLORO-3-CYANOBENZALDEHYDE; 2-CHLORO-3-FLUORO-4-FORMYLPYRIDINE; 2-CHLORO-3-FLUORO-4-HYDROXYBENZALDEHYDE; 2-CHLORO-3-FLUORO-6-HYDROXY-BENZALDEHYDE; 2-CHLORO-3-FLUOROBENZALDEHYDE; 2-CHLORO-3-FLUOROMETHYLBENZALDEHYDE; 2-CHLORO-3-FORMYL-4-PICOLINE; 2-CHLORO-3-FORMYL-6-PICOLINE; 2-CHLORO-3-HYDROXYBENZALDEHYDE; 2-CHLORO-3-HYDROXYISONICOTINALDEHYDE; 2-CHLORO-3-METHOXYBENZALDEHYDE; 2-CHLORO-3-METHOXYPYRIDINE-4-CARBOXALDEHYDE; 2-CHLORO-3-METHYLBENZALDEHYDE; 2-CHLORO-3-METHYLPYRIDINE-4-CARBOXALDEHYDE; 2-CHLORO-3-PHENYLPROPANAL; 2-CHLORO-3-PYRIDINECARBOXALDEHYDE; 2-CHLORO-4,6-DIMETHYLPYRIDINE-3-CARBOXALDEHYDE; 2-CHLORO-4-FLUORO-3-METHYLBENZALDEHYDE; 2-CHLORO-4-FLUOROBENZALDEHYDE; 2-CHLORO-4-FLUORO-PYRIDINE-3-CARBALDEHYDE; 2-CHLORO-4-HYDROXYBENZALDEHYDE; 2-CHLORO-4-HYDROXYNICOTINALDEHYDE; 2-CHLORO-4-METHOXYBENZALDEHYDE; 2-CHLORO-4-METHOXYNICOTINALDEHYDE; 2-CHLORO-4-METHOXYPYRIDINE-5-CARBOXALDEHYDE; 2-CHLORO-4-METHYLBENZALDEHYDE; 2-CHLORO-5-FLUORO-3-FORMYLPYRIDINE; 2-CHLORO-5-FLUORO-4-FORMYLPYRIDINE; 2-CHLORO-5-FLUORO-6-FORMYLPYRIDINE; 2-CHLORO-5-FLUOROBENZALDEHYDE; 2-CHLORO-5-FORMYL-4-PICOLINE; 2-CHLORO-5-FORMYL-NICOTINONITRILE; 2-CHLORO-5-HYDROXY-3-PYRIDINECARBOXALDEHYDE; 2-CHLORO-5-HYDROXYBENZALDEHYDE; 2-CHLORO-5-HYDROXYISONICOTINALDEHYDE; 2-CHLORO-5-METHOXYBENZALDEHYDE; 2-CHLORO-5-METHOXYISONICOTINALDEHYDE; 2-CHLORO-5-METHOXYPYRIDINE-3-CARBOXALDEHYDE; 2-CHLORO-5-METHYLBENZALDEHYDE; 2-CHLORO-5-METHYLPYRIDINE-3-CARBALDEHYDE; 2-CHLORO-5-METHYLPYRIDINE-4-CARBOXALDEHYDE; 2-CHLORO-6-CYANOBENZALDEHYDE; 2-CHLORO-6-CYANOISONICOTINALDEHYDE; 2-CHLORO-6-FLUORO-3-METHYLBENZALDEHYDE; 2-CHLORO-6-FLUOROBENZALDEHYDE; 2-CHLORO-6-FLUOROISONICOTINALDEHYDE; 2-CHLORO-6-FLUORONICOTINALDEHYDE; 2-CHLORO-6-FORMYLBENZONITRILE; 2-CHLORO-6-HYDROXYBENZALDEHYDE; 2-CHLORO-6-HYDROXYISONICOTINALDEHYDE; 2-CHLORO-6-HYDROXYNICOTINALDEHYDE; 2-CHLORO-6-METHOXY-4-PYRIDINECARBOXALDEHYDE; 2-CHLORO-6-METHOXYBENZALDEHYDE; 2-CHLORO-6-METHOXYNICOTINALDEHYDE; 2-CHLORO-6-METHYLPYRIDINE-4-CARBOXALDEHYDE; 2-CHLOROBENZALDEHYDE; 2-CHLOROHEXANAL; 2-CHLOROISONICOTINALDEHYDE; 2-CHLOROISONICOTINALDEHYDE HYDRATE; 2-CHLOROMALONALDEHYDE; 2-CHLOROPHENYLGLYOXAL; 2-CHLOROPROPIONALDEHYDE; 2-CHLORO-PYRIDINE-3,5-DICARBALDEHYDE; 2-CHLOROPYRIMIDINE-4,6-DICARBALDEHYDE; 2-CHLOROPYRIMIDINE-4-CARBALDEHYDE; 2-CHLOROPYRIMIDINE-5-CARBALDEHYDE; 2-CYANO-3-FLUOROBENZALDEHYDE; 2-CYANO-3-HYDROXYBENZALDEHYDE; 2-CYANO-4-FLUOROBENZALDEHYDE; 2-CYANO-4-METHOXYBENZALDEHYDE; 2-CYANO-4-METHYLBENZALDEHYDE; 2-CYANO-5-FLUOROBENZALDEHYDE; 2-CYANO-5-HYDROXYBENZALDEHYDE; 2-CYANO-5-METHOXYBENZALDEHYDE; 2-CYANO-5-METHYLBENZALDEHYDE; 2-CYANO-6-FLUOROBENZALDEHYDE; 2-CYANO-6-HYDROXYBENZALDEHYDE; 2-CYANO-6-METHOXYBENZALDEHYDE; 2-CYANO-6-METHYLBENZALDEHYDE; 2-CYANOBENZALDEHYDE; 2-CYANOPYRIDINE-4-CARBOXALDEHYDE; 2-CYCLOBUTOXYACETALDEHYDE; 2-CYCLOHEXYL PROPANAL; 2-CYCLOHEXYLACETALDEHYDE; 2-CYCLOPROPOXYBENZALDEHYDE; 2-CYCLOPROPYL-2-OXOACETALDEHYDE; 2-CYCLOPROPYL-3-PYRIDINECARBOXALDEHYDE; 2-CYCLOPROPYL-6-METHYLPYRIMIDINE-4-CARBALDEHYDE; 2-CYCLOPROPYLACETALDEHYDE; 2-CYCLOPROPYLBENZALDEHYDE; 2-CYCLOPROPYLETHYNYL-BENZALDEHYDE; 2-CYCLOPROPYLPYRIMIDINE-4-CARBALDEHYDE; 2-CYCLOPROPYLPYRIMIDINE-5-CARBALDEHYDE; 2-DECYNAL; 2-DEOXY-D-GLUCOSE; 2-DEOXY-D-RIBOSE; 2-DEOXY-L-GLUCOSE; 2-DEOXY-L-RIBOSE; 2-DIMETHYLAMINO-1,3-DIOXOHEXANE; 2-DIMETHYLAMINO-5-FORMYLBENZONITRILE; 2-DIMETHYLAMINOMETHYL-BENZALDEHYDE; 2-DIMETHYLAMINO-PYRIMIDINE-5-CARBALDEHYDE; 2-ETHENYLBENZALDEHYDE; 2-ETHOXY-3-METHYLPYRIDINE-5-CARBOXALDEHYDE; 2-ETHOXY-4-FLUOROBENZALDEHYDE; 2-ETHOXY-5-FLUOROBENZALDEHYDE; 2-ETHOXY-5-METHYLBENZALDEHYDE; 2-ETHOXYBENZALDEHYDE; 2-ETHOXYNICOTINALDEHYDE; 2-ETHYL-1,3-DITHIOLANE-2-CARBALDEHYDE; 2-ETHYL-2-([ETHYL(METHYL)AMINO]METHYL)BUTANAL; 2-ETHYL-2,3-DIHYDRO-1H-INDENE-2-CARBALDEHYDE; 2-ETHYL-3-HYDROXYBENZALDEHYDE; 2-ETHYL-3-HYDROXYHEXANAL; 2-ETHYL-3-METHYLBUTANAL; 2-ETHYL-3-PYRIDINECARBOXALDEHYDE; 2-ETHYL-4-HYDROXYBENZALDEHYDE; 2-ETHYL-4-PYRIDINECARBOXALDEHYDE; 2-ETHYL-5-HYDROXYBENZALDEHYDE; 2-ETHYL-5-METHYLCYCLOPENTANAL; 2-ETHYL-6-HYDROXYBENZALDEHYDE; 2-ETHYL-6-METHYL-4-PYRIDINECARBOXALDEHYDE; 2-ETHYL-6-METHYLBENZALDEHYDE; 2-ETHYL-6-METHYLPYRIMIDINE-4-CARBALDEHYDE; 2-ETHYLBENZALDEHYDE; 2-ETHYLBUTYRALDEHYDE; 2-ETHYLHEPTANAL; 2-ETHYLHEXANAL; 2-ETHYLHEXENAL; 2-ETHYLPYRIMIDINE-4-CARBALDEHYDE; 2-ETHYLPYRIMIDINE-5-CARBALDEHYDE; 2-ETHYLSULFANYL-PYRIMIDINE-5-CARBALDEHYDE; 2-ETHYNYL-5-PYRIMIDINECARBOXALDEHYDE; 2-ETHYNYLBENZALDEHYDE; 2-FLUORO-3-(CHLO-

ROMETHYL)BENZALDEHYDE; 2-FLUORO-3-(DIFLUOROMETHYL)BENZALDEHYDE; 2-FLUORO-3,4-DIHYDROXY-BENZALDEHYDE; 2-FLUORO-3-FORMYL-4-PICOLINE; 2-FLUORO-3-FORMYLPHENYLBORONIC ACID; 2-FLUORO-3-FORMYLPYRIDINE; 2-FLUORO-3-HYDROXY-4-METHOXYBENZALDEHYDE; 2-FLUORO-3-HYDROXY-6-METHOXYBENZALDEHYDE; 2-FLUORO-3-HYDROXYBENZALDEHYDE; 2-FLUORO-3-HYDROXYISONICOTINALDEHYDE; 2-FLUORO-3-METHOXY-5-METHYLBENZALDEHYDE; 2-FLUORO-3-METHOXYBENZALDEHYDE; 2-FLUORO-3-METHOXYISONICOTINALDEHYDE; 2-FLUORO-3-METHYL-5-METHOXYBENZALDEHYDE; 2-FLUORO-3-METHYLBENZALDEHYDE; 2-FLUORO-3-METHYL-BENZENEPROPANAL; 2-FLUORO-3-METHYLISONICOTINALDEHYDE; 2-FLUORO-3-NITROBENZALDEHYDE; 2-FLUORO-4-(CHLOROMETHYL)BENZALDEHYDE; 2-FLUORO-4,5-DIHYDROXYBENZALDEHYDE; 2-FLUORO-4-FORMYLBENZONITRILE; 2-FLUORO-4-FORMYLPHENYLBORONIC ACID; 2-FLUORO-4-FORMYLPYRIDINE; 2-FLUORO-4-HYDROXYBENZALDEHYDE; 2-FLUORO-4-MERCAPTOBENZALDEHYDE; 2-FLUORO-4-METHOXYBENZALDEHYDE; 2-FLUORO-4-METHYLBENZALDEHYDE; 2-FLUORO-4-NITROBENZALDEHYDE; 2-FLUORO-5-FORMYL-3-PICOLINE; 2-FLUORO-5-FORMYLBENZONITRILE; 2-FLUORO-5-FORMYLPHENYLBORONIC ACID; 2-FLUORO-5-FORMYLPYRIDINE; 2-FLUORO-5-HYDROXYBENZALDEHYDE; 2-FLUORO-5-HYDROXYISONICOTINALDEHYDE; 2-FLUORO-5-HYDROXYNICOTINALDEHYDE; 2-FLUORO-5-MERCAPTOBENZALDEHYDE; 2-FLUORO-5-METHOXYBENZALDEHYDE; 2-FLUORO-5-METHOXYISONICOTINALDEHYDE; 2-FLUORO-5-METHOXYNICOTINALDEHYDE; 2-FLUORO-5-METHYLBENZALDEHYDE; 2-FLUORO-5-METHYLISONICOTINALDEHYDE; 2-FLUORO-5-METHYLPYRIDINE-3-CARBOXALDEHYDE; 2-FLUORO-5-NITROBENZALDEHYDE; 2-FLUORO-6-FORMYLPYRIDINE; 2-FLUORO-6-HYDROXY-3-METHOXYBENZALDEHYDE; 2-FLUORO-6-HYDROXYBENZALDEHYDE; 2-FLUORO-6-HYDROXYISONICOTINALDEHYDE; 2-FLUORO-6-HYDROXYNICOTINALDEHYDE; 2-FLUORO-6-METHOXYBENZALDEHYDE; 2-FLUORO-6-METHOXYISONICOTINALDEHYDE; 2-FLUORO-6-METHOXYNICOTINALDEHYDE; 2-FLUORO-6-METHYLBENZALDEHYDE; 2-FLUORO-6-METHYLISONICOTINALDEHYDE; 2-FLUORO-6-METHYLNICOTINALDEHYDE; 2-FLUORO-6-NITROBENZALDEHYDE; 2-FLUOROBENZALDEHYDE; 2-FLUORONAPHTHALENE-1-CARBOXALDEHYDE; 2-FLUORONAPHTHALENE-3-CARBOXALDEHYDE; 2-FLUORONAPHTHALENE-4-CARBOXALDEHYDE; 2-FLUORONAPHTHALENE-5-CARBOXALDEHYDE; 2-FLUORONAPHTHALENE-6-CARBOXALDEHYDE; 2-FLUORONAPHTHALENE-7-CARBOXALDEHYDE; 2-FLUOROPHENYLGLYOXAL HYDRATE; 2-FORMYL-1,3-BENZOXAZOLE-6-CARBONITRILE; 2-FORMYL-1,3-BENZOXAZOLE-7-CARBONITRILE; 2-FORMYL-1-PIPERIDINECARBOXYLIC ACID METHYL ESTER; 2-FORMYL-3,4-DIHYDRO-2H-PYRAN; 2-FORMYL-3-METHYL-3H-IMIDAZOLE-4-CARBOXYLIC ACID METHYL ESTER; 2-FORMYL-3-METHYLBUTANENITRILE; 2-FORMYL-3-OXO-BUTYRIC ACID ETHYL ESTER; 2-FORMYL-3-PHENYL-PROPIONITRILE; 2-FORMYL-4-METHYLPENTANENITRILE; 2-FORMYL-4-METHYLPHENYLBORONIC ACID; 2-FORMYL-4-PICOLINE; 2-FORMYL-5,6,7,8-TETRAHYDROQUINAZOLINE; 2-FORMYL-5-HYDROXYBENZONITRILE; 2-FORMYL-5-METHYLPHENYLBORONIC ACID; 2-FORMYL-6-METHOXYBENZONITRILE; 2-FORMYL-6-METHYLBENZONITRILE; 2-FORMYL-6-METHYL-CYCLOPENTAIMIDAZOLE; 2-FORMYL-6-METHYLISONICOTINONITRILE; 2-FORMYL-6-METHYLPYRIDINE-4-BORONIC ACID; 2-FORMYLAZULENE; 2-FORMYL-BENZOYL CHLORIDE; 2-FORMYLBUTANENITRILE; 2-FORMYLNICOTINONITRILE; 2-FORMYLPHENYLBORONIC ACID; 2-FORMYLPROPIONIC ACID ETHYL ESTER; 2-FORMYLPYRIDINE-4-BORONIC ACID; 2-FORMYLPYRIMIDINE-4-CARBONITRILE; 2-FURAN-2-YL-BENZALDEHYDE; 2-FURANBUTANAL; 2-FURANPENTANAL; 2H-1,2,3-TRIAZOLE-4-CARBOXALDEHYDE, 5-[(DIMETHYLAMINO)METHYL]-; 2-HEPTYNAL; 2-HEXYNAL; 2H-PYRAN-4-CARBOXALDEHYDE, 4-FLUOROTETRAHYDRO-; 2H-TETRAZOLE-5-CARBALDEHYDE; 2-HYDROXY-1-NAPHTHALDEHYDE; 2-HYDROXY-3-(METHYLTHIO)BENZALDEHYDE; 2-HYDROXY-3,4-DIMETHYL-BENZALDEHYDE; 2-HYDROXY-3,5-DIMETHYL-BENZALDEHYDE; 2-HYDROXY-3,6-DIMETHYLBENZALDEHYDE; 2-HYDROXY-3-ISOPROPYLBENZALDEHYDE; 2-HYDROXY-3-METHOXY-5-METHYL-BENZALDEHYDE; 2-HYDROXY-3-METHOXYBENZALDEHYDE; 2-HYDROXY-3-METHYLBENZALDEHYDE; 2-HYDROXY-3-METHYLISONICOTINALDEHYDE; 2-HYDROXY-4-(METHYLTHIO)BENZALDEHYDE; 2-HYDROXY-4,5-DIMETHYL-BENZALDEHYDE; 2-HYDROXY-4,6-DIMETHYL-BENZALDEHYDE; 2-HYDROXY-4-ISOPROPYLBENZALDEHYDE; 2-HYDROXY-4-METHOXY-6-METHYLBENZALDEHYDE; 2-HYDROXY-4-METHOXYBENZALDEHYDE; 2-HYDROXY-4-METHYLBENZALDEHYDE; 2-HYDROXY-4-METHYLNICOTINALDEHYDE; 2-HYDROXY-4-NITROBENZALDEHYDE; 2-HYDROXY-4-PYRIDINECARBOXALDEHYDE; 2-HYDROXY-5-(HYDROXYMETHYL)BENZALDEHYDE; 2-HYDROXY-5-(METHYLSULFANYL)BENZALDEHYDE; 2-HYDROXY-5-CHLOROMETHYLBENZALDEHYDE; 2-HYDROXY-5-ISOPROPYL-BENZALDEHYDE; 2-HYDROXY-5-METHOXY-3-METHYL-BENZALDEHYDE; 2-HYDROXY-5-METHOXY-4-METHYL-BENZALDEHYDE; 2-HYDROXY-5-METHOXYBENZALDEHYDE; 2-HYDROXY-5-METHYLBENZALDEHYDE; 2-HYDROXY-5-METHYLISONICOTINALDEHYDE; 2-HYDROXY-5-METHYLISOPHTHALALDEHYDE; 2-HYDROXY-5-METHYLNICOTINALDEHYDE; 2-HYDROXY-5-NITROBENZALDEHYDE; 2-HYDROXY-5-NITRONICOTINALDEHYDE; 2-HYDROXY-5-PROPYL-BENZALDEHYDE; 2-HYDROXY-6-(METHYLTHIO)BENZALDEHYDE; 2-HYDROXY-6-ISOPROPYLBENZALDEHYDE; 2-HYDROXY-6-METHOXYBENZALDEHYDE; 2-HYDROXY-6-METHYLBENZALDEHYDE; 2-HYDROXY-6-METHYLISONICOTINALDEHYDE; 2-HYDROXY-6-

METHYL-PYRIDINE-3-CARBALDEHYDE; 2-HYDROXY-6-METHYLPYRIMIDINE-4-CARBALDEHYDE; 2-HYDROXY-6-NITROBENZALDEHYDE; 2-HYDROXYHEXANEDIAL; 2-HYDROXYNICOTINALDEHYDE; 2-HYDROXYPYRAZINE-6-CARBOXALDEHYDE; 2-HYDROXYPYRIMIDINE-5-CARBALDEHYDE; 2-HYDROXYQUINOLINE-3-CARBALDEHYDE; 2-HYDROXYQUINOLINE-4-CARBOXALDEHYDE; 2-HYDROXYQUINOLINE-5-CARBOXALDEHYDE; 2-HYDROXYQUINOLINE-6-CARBOXALDEHYDE; 2-HYDROXYQUINOLINE-7-CARBOXALDEHYDE; 2-HYDROXYQUINOLINE-8-CARBOXALDEHYDE; 2-HYDROXYTEREPHTHALALDEHYDE; 2-IMIDAZOL-1-YL-BENZALDEHYDE; 2-IMIDAZOL-1-YL-PYRIDINE-3-CARBALDEHYDE; 2-IMIDAZOL-1-YL-PYRIDINE-4-CARBALDEHYDE; 2-ISOPROPOXYBENZALDEHYDE; 2-ISOPROPOXYPYRIDINE-3-CARBALDEHYDE; 2-ISOPROPYL-6-METHYLBENZALDEHYDE; 2-ISOPROPYLBENZALDEHYDE; 2-ISOPROPYLPYRIMIDINE-4-CARBALDEHYDE; 2-ISOPROPYL-PYRIMIDINE-5-CARBALDEHYDE; 2-MERCAPTO-4-METHOXYBENZALDEHYDE; 2-MERCAPTOBENZALDEHYDE; 2-MESITYLACETALDEHYDE; 2-METHOXY-3,5-DIMETHYLBENZALDEHYDE; 2-METHOXY-3-METHYLBENZALDEHYDE; 2-METHOXY-3-METHYLISONICOTINALDEHYDE; 2-METHOXY-3-PYRIDINECARBOXALDEHYDE; 2-METHOXY-4-MERCAPTOBENZALDEHYDE; 2-METHOXY-4-METHYLBENZALDEHYDE; 2-METHOXY-4-METHYLNICOTINALDEHYDE; 2-METHOXY-5-METHYLBENZALDEHYDE; 2-METHOXY-5-METHYLISONICOTINALDEHYDE; 2-METHOXY-5-METHYLNICOTINALDEHYDE; 2-METHOXY-6-METHYL-3-PYRIDINECARBOXALDEHYDE; 2-METHOXY-6-METHYLBENZALDEHYDE; 2-METHOXY-6-METHYLISONICOTINALDEHYDE; 2-METHOXY-6-METHYLPYRIMIDINE-4-CARBALDEHYDE; 2-METHOXY-PENT-4-YNAL; 2-METHOXYPHENYLGLYOXAL; 2-METHOXYPYRAZINE-6-CARBOXALDEHYDE; 2-METHOXYPYRIDINE-4-CARBOXALDEHYDE; 2-METHOXYPYRIMIDINE-4,6-DICARBALDEHYDE; 2-METHOXYPYRIMIDINE-4-CARBALDEHYDE; 2-METHOXYPYRIMIDINE-5-CARBALDEHYDE; 2-METHYL DECANAL; 2-METHYL OCTANAL; 2-METHYL-1-NAPHTHALDEHYDE; 2-METHYL-1-OXOPENTAN-3-YL ETHANETHIOATE; 2-METHYL-1-OXOPENTAN-3-YL ETHANETHIOATE; 2-METHYL-2-([METHYL(PROPAN-2-YL)AMINO]METHYL)BUTANAL; 2-METHYL-2-([METHYL(PROPYL)AMINO]METHYL)BUTANAL; 2-METHYL-2-(PYRROLIDIN-1-YLMETHYL)BUTANAL; 2-METHYL-2,3-DIHYDRO-1-BENZOFURAN-5-CARBALDEHYDE; 2-METHYL-2H-1,2,4-TRIAZOLE-3-CARBALDEHYDE; 2-METHYL-2-METHYLSULFANYL-PROPIONALDEHYDE; 2-METHYL-2-MORPHOLINOPROPANAL; 2-METHYL-2-PHENYLPROPANAL; 2-METHYL-2-PIPERIDINO-PROPANAL; 2-METHYL-3-(1H-PYRROL-1-YL)PROPANAL; 2-METHYL-3-[METHYL(3-OXOPROPYL)AMINO]PROPANENITRILE; 2-METHYL-3-NITROBENZALDEHYDE; 2-METHYL-3-OXO-3-(THIOPHEN-2-YL)PROPANAL; 2-METHYL-3-OXO-BUTANAL; 2-METHYL-3-OXOPROPANENITRILE; 2-METHYL-3-PHENYLPROPANAL; 2-METHYL-3-TOLYLPROPIONALDEHYDE; 2-METHYL-4,5,6,7-TETRAHYDROBENZOFURAN-4-CARBALDEHYDE; 2-METHYL-4,5-DIFLUOROBENZALDEHYDE; 2-METHYL-4-NITROBENZALDEHYDE; 2-METHYL-5-NITROBENZALDEHYDE; 2-METHYL-6-NITROBENZALDEHYDE; 2-METHYL-6-QUINOLINECARBALDEHYDE; 2-METHYLBENZALDEHYDE; 2-METHYLBUTYRALDEHYDE; 2-METHYLCYCLOPROPANE-1-CARBALDEHYDE; 2-METHYLHEPTANAL; 2-METHYLHEXANAL; 2-METHYLISONICOTINAL; 2-METHYLISONICOTINALDEHYDE HYDROCHLORIDE; 2-METHYLNAPHTHALENE-3-CARBOXALDEHYDE; 2-METHYLNAPHTHALENE-4-CARBOXALDEHYDE; 2-METHYLNAPHTHALENE-5-CARBOXALDEHYDE; 2-METHYLNAPHTHALENE-6-CARBOXALDEHYDE; 2-METHYLNAPHTHALENE-8-CARBOXALDEHYDE; 2-METHYLNICOTINALDEHYDE; 2-METHYLNONANAL; 2-METHYL-PENT-4-ENAL; 2-METHYLPYRIMIDINE-4,6-DICARBALDEHYDE; 2-METHYLPYRIMIDINE-4-CARBALDEHYDE; 2-METHYLPYRIMIDINE-5-CARBALDEHYDE; 2-METHYLQUINOLINE-4-CARBOXALDEHYDE; 2-METHYLTHIOACETALDEHYDE; 2-METHYLVALERALDEHYDE; 2-NAPHTHALDEHYDE; 2-NAPHTHALENECARBOXALDEHYDE, 3-HYDROXY-; 2-NAPHTHYLACETALDEHYDE; 2-NITROBENZALDEHYDE; 2-NITRONICOTINALDEHYDE; 2-NONYNAL; 2-OCTYNAL; 2-OXAZOLECARBOXALDEHYDE, 4-METHYL-; 2-OXAZOLECARBOXALDEHYDE, 5-(1,1-DIMETHYLETHYL)-; 2-OXAZOLECARBOXALDEHYDE, 5-ETHYL-; 2-OXO-2-(PIPERIDIN-1-YL)ACETALDEHYDE; 2-OXO-2-(PYRIDIN-2-YL)ACETALDEHYDE; 2-OXO-2-(PYRIDIN-3-YL)ACETALDEHYDE; 2-OXO-2-(PYRIDIN-4-YL)ACETALDEHYDE; 2-OXO-2H-CHROMENE-7-CARBALDEHYDE; 2-OXO-2-O-TOLYLACETALDEHYDE HYDRATE; 2-OXO-3-OXAZOLIDINEPROPANAL; 2-OXO-3-PHENYL-PROPANAL; 2-OXO-5-(PROPAN-2-YL)CYCLOHEXANE-1-CARBALDEHYDE; 2-OXOBUTANALDEHYDE; 2-OXOHEXAHYDRO-2H-CYCLOPENTA[B]FURAN-4-CARBALDEHYDE; 2-PENTYNAL; 2-PHENYL-2H-1,2,3-TRIAZOLE-4-CARBALDEHYDE; 2-PHENYLBUTANAL; 2-PHENYLCYCLOPROPANECARBALDEHYDE; 2-PHENYLMALONDIALDEHYDE; 2-PHENYLPROPIONALDEHYDE; 2-PROPOXYACETALDEHYDE; 2-PROPOXYBENZALDEHYDE; 2-PROPOXY-PYRIDINE-3-CARBALDEHYDE; 2-PROPYL VALERALDEHYDE; 2-PROPYL-4-PYRIDINECARBOXALDEHYDE; 2-PROPYLHEXANAL; 2-PROPYL-PYRIMIDINE-4-CARBALDEHYDE; 2-PROPYL-PYRIMIDINE-5-CARBALDEHYDE; 2-P-TOLYL-CYCLOPROPANECARBALDEHYDE; 2-PYRAZINEBUTANAL; 2-PYRAZINECARBOXALDEHYDE, 3-METHYL-; 2-PYRAZINECARBOXALDEHYDE, 5-METHYL-; 2-PYRIDAZIN-4-YLMALONALDEHYDE; 2-PYRIDIN-4-YLCYCLOPROPANECARBOXALDEHYDE; 2-PYRIDINECARBOXALDEHYDE; 2-PYRIDINECARBOXALDEHYDE, 1-OXIDE; 2-PYRIDINECARBOXALDEHYDE, 3,4-DIMETHYL-; 2-PYRIDINECARBOXALDEHYDE, 3-ETHENYL-; 2-PYRIDINECARBOXALDEHYDE, 4-ETHYL-; 2-PYRIDINECARBOXALDEHYDE, 6-(METHOXYMETHYL)-; 2-PYRIDINECARBOXALDEHYDE,6-(1-METHYLETHOXY)-; 2-PYRIMIDINECARBONITRILE, 5-FORMYL-; 2-PYRIMIDINECARBOXALDEHYDE;

2-PYRIMIDINECARBOXALDEHYDE, 5-METHYL-; 2-QUINOLINECARBOXALDEHYDE; 2-QUINOLINECARBOXALDEHYDE, 1-OXIDE; 2-QUINOXALINECARBALDEHYDE; 2-QUINOXALINECARBALDEHYDE 4-OXIDE; 2-QUINOXALINECARBOXALDEHYDE, 6-METHYL-; 2-TERT-BUTYLBENZALDEHYDE; 2-TERT-BUTYLISONICOTINALDEHYDE; 2-TERT-BUTYLPYRIMIDINE-4-CARBALDEHYDE; 2-TERT-BUTYLPYRIMIDINE-5-CARBALDEHYDE; 2-THIAZOLECARBOXALDEHYDE; 2-THIENYLGLYOXAL; 2-THIOGLYCERALDEHYDE; 2-THIOPHENEBUTANAL; 2-THIOPHENEGLYOXAL HYDRATE; 3-([ETHYL(METHYL)AMINO]METHYL)OXOLANE-3-CARBALDEHYDE; 3-(1,2,4-OXADIAZOL-3-YL)BENZALDEHYDE; 3-(1,3,4-THIADIAZOL-2-YLSULFANYL)PROPANAL; 3-(1,3-THIAZOL-2-YLSULFANYL)PROPANAL; 3-(1,4-OXAZEPAN-4-YL)PROPANAL; 3-(1,4-THIAZEPAN-4-YL)PROPANAL; 3-(1-ETHYL-1H-PYRAZOL-4-YL)-3-OXOPROPANAL; 3-(1H-1,2,4-TRIAZOL-1-YL)BENZALDEHYDE; 3-(1H-1,2,4-TRIAZOL-5-YLSULFANYL)PROPANAL; 3-(1H-IMIDAZOL-1-YL)BENZALDEHYDE; 3-(1H-PYRAZOL-1-YL)BENZALDEHYDE; 3-(1H-PYRAZOL-1-YL)PROPANAL; 3-(1H-PYRAZOL-3-YL)BENZALDEHYDE; 3-(1H-PYRAZOL-4-YL)BENZALDEHYDE; 3-(1H-PYRROL-1-YL)BENZALDEHYDE; 3-(1H-TETRAZOL-5-YL)BENZALDEHYDE; 3-(1-METHYL-1H-IMIDAZOL-4-YL)-PROPIONALDEHYDE; 3-(1-METHYL-1H-PYRAZOL-4-YL)-3-OXOPROPANAL; 3-(1-METHYL-2-OXO-ETHYL)-BENZONITRILE; 3-(2,2,2-TRIFLUOROETHOXY)PROPANAL; 3-(2,2-DIMETHYLMORPHOLIN-4-YL)PROPANAL; 3-(2,2-DIMETHYLPYRROLIDIN-1-YL)PROPANAL; 3-(2,3-DIMETHYLPIPERIDIN-1-YL)PROPANAL; 3-(2,4-DIFLUORO-PHENYL)-PROPIONALDEHYDE; 3-(2,4-DIMETHYL-PHENYL)-PROPIONALDEHYDE; 3-(2,4-DIMETHYLPIPERIDIN-1-YL)PROPANAL; 3-(2,4-DIOXO-1,3-THIAZOLIDIN-3-YL)PROPANAL; 3-(2,5-DIFLUORO-PHENYL)-PROPIONALDEHYDE; 3-(2,5-DIMETHYLFURAN-3-YL)-3-OXOPROPANAL; 3-(2,5-DIMETHYLMORPHOLIN-4-YL)PROPANAL; 3-(2,5-DIOXOPYRROLIDIN-1-YL)-2-METHYLPROPANAL; 3-(2,5-DIOXOPYRROLIDIN-1-YL)PROPANAL; 3-(2,6-DIFLUORO-PHENYL)-PROPIONALDEHYDE; 3-(2,6-DIMETHYLMORPHOLIN-4-YL)PROPANAL; 3-(2,6-DIMETHYLPIPERIDIN-1-YL)PROPANAL; 3-(2,6-DIOXOPIPERIDIN-1-YL)PROPANAL; 3-(2-BUTOXYETHOXY)PROPANAL; 3-(2-CHLORO-PHENYL)-PROPIONALDEHYDE; 3-(2-CHLORO-PYRIMIDIN-5-YL)-PROPIONALDEHYDE; 3-(2-ETHOXYETHOXY)PROPANAL; 3-(2-ETHYLMORPHOLIN-4-YL)PROPANAL; 3-(2-ETHYLPIPERIDIN-1-YL)PROPANAL; 3-(2-ETHYLPYRROLIDIN-1-YL)PROPANAL; 3-(2-FLUOROPHENOXY)PROPANAL; 3-(2-FLUOROPHENYL)-3-OXOPROPANAL; 3-(2-FLUOROPHENYL)-PROPIONALDEHYDE; 3-(2-FORMYLIMIDAZOL-1-YL)-PROPAN-1-OL; 3-(2-FORMYL-IMIDAZOL-1-YL)-PROPIONITRILE; 3-(2-FURYL)-3-OXOPROPANAL; 3-(2-FURYL)BENZALDEHYDE; 3-(2H-TETRAZOL-5-YL)BENZALDEHYDE; 3-(2-HYDROXYETHOXY)BENZALDEHYDE; 3-(2-HYDROXYETHYL)BENZALDEHYDE; 3-(2-HYDROXYMETHYL-PHENYL)-PROPIONALDEHYDE; 3-(2-HYDROXYPHENYL)-3-OXOPROPANAL; 3-(2-HYDROXY-PHENYL)-PROPIONALDEHYDE; 3-(2-METHOXY-PHENYL)-PROPIONALDEHYDE; 3-(2-METHOXYPYRIDIN-4-YL)PROPANAL; 3-(2-METHYL-1,4-OXAZEPAN-4-YL)PROPANAL; 3-(2-METHYLMORPHOLIN-4-YL)PROPANAL; 3-(2-METHYLPHENOXY)PROPANAL; 3-(2-METHYLPHENYL)-3-OXOPROPANAL; 3-(2-METHYLPHENYL)PROPANAL; 3-(2-METHYLPIPERIDIN-1-YL)PROPANAL; 3-(2-METHYLPROPOXY)PROPANAL; 3-(2-METHYLPYRROLIDIN-1-YL)PROPANAL; 3-(2-OXO-1,3-THIAZOLIDIN-3-YL)PROPANAL; 3-(2-OXO-2,3-DIHYDRO-1,3-THIAZOL-3-YL)PROPANAL; 3-(2-OXO-ACETYL)-BENZONITRILE; 3-(2-OXOAZEPAN-1-YL)PROPANAL; 3-(2-OXOETHOXY)BENZALDEHYDE; 3-(2-OXOETHOXY)BENZONITRILE; 3-(2-OXOPIPERIDIN-1-YL)PROPANAL; 3-(2-OXOPYRROLIDIN-1-YL)PROPANAL; 3-(2-PROPEN-1-YL)-BENZALDEHYDE; 3-(3,3-DIMETHYLMORPHOLIN-4-YL)PROPANAL; 3-(3,4-DIFLUORO-PHENYL)-PROPIONALDEHYDE; 3-(3,4-DIHYDROXY-PHENYL)-PROPIONALDEHYDE; 3-(3,5-DIFLUORO-PHENYL)-PROPIONALDEHYDE; 3-(3,5-DIMETHYL-1H-1,2,4-TRIAZOL-1-YL)PROPANAL; 3-(3,5-DIMETHYL-1H-PYRAZOL-1-YL)PROPANAL; 3-(3,5-DIMETHYL-1H-PYRAZOL-1-YL)PROPANALHYDRATE; 3-(3,5-DIMETHYLPIPERIDIN-1-YL)PROPANAL; 3-(3,5-DIOXOMORPHOLIN-4-YL)PROPANAL; 3-(3-ALLYL)-5-HEXEN-1-AL; 3-(3-CHLORO-PHENYL)-PROPIONALDEHYDE; 3-(3-CHLOROPYRIDIN-2-YL)PROPANAL; 3-(3-ETHYLMORPHOLIN-4-YL)PROPANAL; 3-(3-ETHYLPIPERIDIN-1-YL)PROPANAL; 3-(3-FLUORO-4-METHYL-PHENYL)-PROPIONALDEHYDE; 3-(3-FLUOROPHENOXY)PROPANAL; 3-(3-FLUOROPHENYL)-3-OXOPROPANAL; 3-(3-FLUOROPHENYL)PROPANAL; 3-(3-HYDROXY-PHENYL)-PROPIONALDEHYDE; 3-(3-HYDROXYPIPERIDIN-1-YL)PROPANAL; 3-(3-HYDROXY-PROP-1-YNYL)-BENZALDEHYDE; 3-(3-HYDROXYPYRROLIDIN-1-YL)-2,2-DIMETHYLPROPANAL; 3-(3-HYDROXYPYRROLIDIN-1-YL)PROPANAL; 3-(3-METHOXYPHENYL)PROPANAL; 3-(3-METHOXYPROPOXY)PROPANAL; 3-(3-METHYL-2,5-DIOXOIMIDAZOLIDIN-1-YL)PROPANAL; 3-(3-METHYL-2,5-DIOXOPYRROLIDIN-1-YL)PROPANAL; 3-(3-METHYL-2-OXO-1,2-DIHYDROPYRIDIN-1-YL)PROPANAL; 3-(3-METHYL-2-OXOIMIDAZOLIDIN-1-YL)PROPANAL; 3-(3-METHYL-3H-IMIDAZOL-4-YL)-PROPIONALDEHYDE; 3-(3-METHYLBUTOXY)PROPANAL; 3-(3-METHYLMORPHOLIN-4-YL)PROPANAL; 3-(3-METHYLPHENOXY)PROPANAL; 3-(3-METHYLPHENYL)PROPANAL; 3-(3-METHYLPIPERIDIN-1-YL)PROPANAL; 3-(3-METHYLPYRROLIDIN-1-YL)PROPANAL; 3-(3-OXOPROPANOYL)BENZONITRILE; 3-(3-OXO-PROPYL)-BENZONITRILE; 3-(4,4-DIMETHYLPIPERIDIN-1-YL)PROPANAL; 3-(4-CHLORO-PHENYL)-PROPIONALDEHYDE; 3-(4-ETHYL-PHENYL)-PROPIONALDEHYDE; 3-(4-ETHYLPIPERAZIN-1-YL)PROPANAL; 3-(4-ETHYLPIPERIDIN-1-YL)PROPANAL; 3-(4-FLUOROPHENOXY)PROPANAL; 3-(4-FLUOROPHENYL)-3-OXOPROPANAL; 3-(4-FLUOROPHENYL)PROPIONALDEHYDE; 3-(4-HYDROXYMETHYL-PHENYL)-PROPIONALDEHYDE; 3-(4-HYDROXY-PHENYL)-

PROPIONALDEHYDE; 3-(4-HYDROXYPIPERIDIN-1-YL)PROPANAL; 3-(4-METHOXYPHENYL)PROPANAL; 3-(4-METHOXYPIPERIDIN-1-YL)PROPANAL; 3-(4-METHYL-1,4-DIAZEPAN-1-YL)PROPANAL; 3-(4-METHYL-2-OXO-2,3-DIHYDRO-1,3-THIAZOL-3-YL)PROPANAL; 3-(4-METHYL-2-OXOPYRROLIDIN-1-YL)PROPANAL; 3-(4-METHYLPHENOXY)PROPANAL; 3-(4-METHYLPHENYL)-3-OXOPROPANAL; 3-(4-METHYLPHENYL)PROPIONALDEHYDE; 3-(4-METHYLPIPERAZIN-1-YL)PROPANAL; 3-(4-METHYLPIPERIDIN-1-YL)PROPANAL; 3-(4-OXOPIPERIDIN-1-YL)PROPANAL; 3-(5-CHLOROTHIOPHEN-2-YL)PROPANAL; 3-(5-ETHYLTHIOPHEN-2-YL)PROPANAL; 3-(5-METHYL-2-FURYL)BUTYRALDEHYDE; 3-(5-METHYL-2-OXO-1,2-DIHYDROPYRIMIDIN-1-YL)PROPANAL; 3-(5-METHYLFURAN-2-YL)-3-OXOPROPANAL; 3-(5-METHYLTHIEN-2-YL)-3-OXOPROPANAL; 3-(6-CHLORO-PYRIDAZIN-3-YL)-PROPIONALDEHYDE; 3-(ALLYLOXY)BENZALDEHYDE; 3-(AZEPAN-1-YL)PROPANAL; 3-(AZOCAN-1-YL)PROPANAL; 3-(BENZOFURAN-5-YL)PROPANAL; 3-(BENZOFURAN-6-YL)PROPANAL; 3-(BUT-2-YN-1-YLOXY)BENZALDEHYDE; 3-(BUT-3-EN-1-YLOXY)PROPANAL; 3-(BUT-3-YN-1-YLOXY)BENZALDEHYDE; 3-(BUTAN-2-YLOXY)PROPANAL; 3-(BUTAN-2-YLSULFANYL)PROPANAL; 3-(BUTYLSULFANYL)PROPANAL; 3-(CYCLOHEPTYLOXY)PROPANAL; 3-(CYCLOHEXYLMETHOXY)PROPANAL; 3-(CYCLOHEXYLOXY)PROPANAL; 3-(CYCLOHEXYLSULFANYL)PROPANAL; 3-(CYCLOPENTYLOXY)PROPANAL; 3-(CYCLOPENTYLSULFANYL)PROPANAL; 3-(CYCLOPROPYLMETHOXY)PROPANAL; 3-(DIETHYLAMINO)PROPANAL; 3-(DIFLUOROMETHOXY)BENZALDEHYDE; 3-(DIFLUOROMETHOXY)PYRAZINE-2-CARBOXALDEHYDE; 3-(DIMETHYLAMINO)-2-HYDROXYBENZALDEHYDE; 3-(DIMETHYLAMINO)-4-HYDROXYBENZALDEHYDE; 3-(DIMETHYLAMINO)-5-HYDROXYBENZALDEHYDE; 3-(DIMETHYLAMINO)BENZALDEHYDE; 3-(DIMETHYLAMINO)PROPANAL; 3-(DIPROPYLAMINO)PROPANAL; 3-(ETHYLSULFANYL)PROPANAL; 3-(ETHYLTHIO)BUTANAL; 3-(FURAN-2-YL)-2-METHYL-3-OXOPROPANAL; 3-(FURAN-2-YL)PROPANAL; 3-(FURAN-2-YLMETHOXY)PROPANAL; 3-(HEPTYLOXY)PROPANAL; 3-(HEXYLOXY)PROPANAL; 3-(HYDROXYMETHYL)BENZALDEHYDE; 3-(METHOXYMETHOXY)BENZALDEHYDE; 3-(METHYLTHIO)BENZALDEHYDE; 3-(METHYLTHIO)BUTANAL; 3-(METHYLTHIO)HEXANAL; 3-(METHYLTHIO)PROPIONALDEHYDE; 3-(OXAN-2-YLMETHOXY)PROPANAL; 3-(OXAN-4-YL)PROPANAL; 3-(OXAN-4-YLMETHOXY)PROPANAL; 3-(OXAN-4-YLOXY)PROPANAL; 3-(OXAN-4-YLSULFANYL)PROPANAL; 3-(OXOLAN-2-YL)PROPANAL; 3-(OXOLAN-2-YLMETHOXY)PROPANAL; 3-(OXOLAN-3-YLMETHOXY)PROPANAL; 3-(OXOLAN-3-YLOXY)PROPANAL; 3-(PENTYLOXY)PROPANAL; 3-(PHENYLSULFANYL)PROPANAL; 3-(PROP-2-EN-1-YLOXY)PROPANAL; 3-(PROP-2-YNYL)BENZALDEHYDE; 3-(PROPAN-2-YLOXY)PROPANAL; 3-(PROPAN-2-YLSULFANYL)PROPANAL; 3-(PROPYLSULFANYL)PROPANAL; 3-(PYRAZIN-2-YL)BUTANAL; 3-(PYRAZIN-2-YL)PROPANAL; 3-(PYRIDIN-2-YL)PROPANAL; 3-(PYRIDIN-2-YLSULFANYL)PROPANAL; 3-(PYRIDIN-3-YL)PROPANAL; 3-(PYRIMIDIN-2-YL)PROPANAL; 3-(PYRIMIDIN-2-YLSULFANYL)PROPANAL; 3-(PYRIMIDIN-4-YL)PROPANAL; 3-(PYRIMIDIN-5-YL)PROPANAL; 3-(PYRROLIDIN-1-YL)PROPANAL; 3-(TERT-BUTOXY)PROPANAL; 3-(TERT-BUTYLSULFANYL)PROPANAL; 3-(TETRAHYDRO-2H-PYRAN-4-YL)-2,2-DIMETHYLPROPANAL; 3-(TETRAHYDRO-FURAN-3-YL)-PROPIONALDEHYDE; 3-(THIOMORPHOLIN-4-YL)PROPANAL; 3-(THIOPHEN-2-YL)PROPANAL; 3-(THIOPHEN-2-YLMETHOXY)PROPANAL; 3-(THIOPHEN-2-YLSULFANYL)PROPANAL; 3-(THIOPHEN-3-YL)PROPANAL; 3-(TRIFLUOROMETHYL)-1,2,4-OXADIAZOLE-5-CARBALDEHYDE; 3-(TRIFLUOROMETHYL)BENZALDEHYDE; 3-(TRIFLUOROMETHYL)BUTYRALDEHYDE; 3(Z)-NONENAL; 3,3,3-TRIFLUOROPROPANAL; 3,3,3-TRIFLUOROPROPIONALDEHYDE HYDRATE; 3,3,4,4,4-PENTAFLUOROBUTANAL; 3,3-DIMETHOXY-2-(HYDROXYMETHYLENE)PROPIONITRILE SODIUM SALT; 3,3-DIMETHYLBUTYRALDEHYDE; 3,4,5-TRIFLUOROBENZALDEHYDE; 3,4,5-TRIHYDROXYBENZALDEHYDE; 3,4,5-TRIHYDROXYBENZALDEHYDE MONOHYDRATE; 3,4,5-TRIMETHYLBENZALDEHYDE; 3,4-DIFLUORO-2-HYDROXYBENZALDEHYDE; 3,4-DIFLUORO-2-METHYLBENZALDEHYDE; 3,4-DIFLUORO-5-METHOXYBENZALDEHYDE; 3,4-DIFLUORO-5-METHYLBENZALDEHYDE; 3,4-DIFLUOROBENZALDEHYDE; 3,4-DIFLUOROPHENYLGLYOXAL; 3,4-DIHYDRO-1H-2-BENZOPYRAN-1-CARBOXALDEHYDE; 3,4-DIHYDRO-1H-2-BENZOPYRAN-3-CARBOXALDEHYDE; 3,4-DIHYDRO-1H-2-BENZOPYRAN-4-CARBOXALDEHYDE; 3,4-DIHYDRO-1H-2-BENZOPYRAN-5-CARBOXALDEHYDE; 3,4-DIHYDRO-1H-2-BENZOPYRAN-6-CARBOXALDEHYDE; 3,4-DIHYDRO-2H-CHROMENE-4-CARBALDEHYDE; 3,4-DIHYDRO-2H-PYRANO[2,3-B]PYRIDINE-6-CARBALDEHYDE; 3,4-DIHYDROPHENYLGLYOXAL; 3,4-DIHYDROXY PHENYL GLYOXAL; 3,4-DIHYDROXY-5-METHOXYBENZALDEHYDE; 3,4-DIHYDROXYBENZALDEHYDE; 3,4-DIMETHOXYBENZALDEHYDE; 3,4-DIMETHYL-3-CYCLOHEXENYLMETHANAL; 3,4-DIMETHYLBENZALDEHYDE; 3,4-DIMETHYLBENZENEPROPANAL; 3,4-PYRIDINEDICARBOXALDEHYDE; 3,5,5-TRIMETHYLHEXANAL; 3,5,6-TRIMETHYL-2-PYRAZINECARBALDEHYDE; 3,5,6-TRIMETHYL-3-CYCLOHEXENE-1-CARBOXALDEHYDE; 3,5-DIETHYLBENZALDEHYDE; 3,5-DIFLUORO-2-HYDROXYBENZALDEHYDE; 3,5-DIFLUORO-2-METHOXYBENZALDEHYDE; 3,5-DIFLUORO-2-METHYLBENZALDEHYDE; 3,5-DIFLUORO-4-HYDROXYBENZALDEHYDE; 3,5-DIFLUORO-4-METHOXYBENZALDEHYDE; 3,5-DIFLUORO-4-PYRIDINECARBOXALDEHYDE; 3,5-DIFLUOROBENZALDEHYDE; 3,5-DIFLUOROPYRIDINE-2-CARBALDEHYDE; 3,5-DIHYDROXYBENZALDEHYDE; 3,5-DIMETHOXYBENZALDEHYDE; 3,5-DIMETHOXYHEXANAL; 3,5-DIMETHOXYPYRAZINE-2-CARBALDEHYDE; 3,5-DIMETHOXYPYRIDINE-4-CARBOXALDEHYDE; 3,5-DIMETHYL-4-HYDROXYBENZALDEHYDE; 3,5-DIMETHYL-4-METHOXYBENZALDEHYDE; 3,5-DIMETHYLBENZALDEHYDE; 3,5-DIMETHYL-

BENZENEPROPANAL; 3,5-DIMETHYLPYRAZINE-2-CARBALDEHYDE; 3,5-DIMETHYLPYRIDINE-2-CARBOXALDEHYDE; 3,5-DIMETHYLPYRIDINE-4-CARBOXALDEHYDE; 3,6-DIFLUORO-2-HYDROXYBENZALDEHYDE; 3,6-DIFLUORO-2-METHOXYBENZALDEHYDE; 3,6-DIFLUOROPICOLINALDEHYDE; 3,7-DIMETHYL-7-HYDROXYOCTANAL; 3,7-DIMETHYLOCTANAL; 3-[(1-CYCLOPROPYLETHYL)(METHYL)AMINO]PROPANAL; 3-[(1-METHOXYPROPAN-2-YL)(METHYL)AMINO]PROPANAL; 3-[(2,2-DIMETHYLPROPYL)(METHYL)AMINO]PROPANAL; 3-[(2-HYDROXYETHYL)(METHYL)AMINO]-2,2-DIMETHYLPROPANAL; 3-[(2-HYDROXYETHYL)(METHYL)AMINO]PROPANAL; 3-[(2-HYDROXYETHYL)(PROPAN-2-YL)AMINO]PROPANAL; 3-[(2-HYDROXYETHYL)(PROPYL)AMINO]PROPANAL; 3-[(2-HYDROXYETHYL)SULFANYL]PROPANAL; 3-[(2-HYDROXYPROPYL)(METHYL)AMINO]-2,2-DIMETHYLPROPANAL; 3-[(2-HYDROXYPROPYL)(METHYL)AMINO]PROPANAL; 3-[(2-METHOXYETHYL)(2-OXOETHYL)AMINO]PROPANENITRILE; 3-[(2-METHOXYETHYL)(METHYL)AMINO]-2,2-DIMETHYLPROPANAL; 3-[(2-METHOXYETHYL)(METHYL)AMINO]PROPANAL; 3-[(2-METHOXYETHYL)SULFANYL]PROPANAL; 3-[(2-METHYLBUTAN-2-YL)OXY]PROPANAL; 3-[(2-METHYLCYCLOHEXYL)OXY]PROPANAL; 3-[(2-METHYLPROPYL)(2-OXOETHYL)AMINO]PROPANENITRILE; 3-[(2-METHYLPROPYL)(PROPAN-2-YL)AMINO]PROPANAL; 3-[(2-METHYLPROPYL)SULFANYL]PROPANAL; 3-[(2-OXOETHYL)(PROPAN-2-YL)AMINO]PROPANENITRILE; 3-[(3,3-DIMETHYLBUTAN-2-YL)(METHYL)AMINO]PROPANAL; 3-[(3-HYDROXYPROPYL)(PROPAN-2-YL)AMINO]PROPANAL; 3-[(3-METHOXYPROPYL)(METHYL)AMINO]PROPANAL; 3-[(3-METHYLCYCLOHEXYL)OXY]PROPANAL; 3-[(3-OXOPROPYL)(PROPAN-2-YL)AMINO]PROPANENITRILE; 3-[(4-METHYLCYCLOHEXYL)OXY]PROPANAL; 3-[(4-METHYLPENTAN-2-YL)OXY]PROPANAL; 3-[(4-METHYLPENTYL)OXY]PROPANAL; 3-[(5-METHYL-1,3,4-OXADIAZOL-2-YL)SULFANYL]PROPANAL; 3-[(CYCLOBUTYLMETHYL)(METHYL)AMINO]PROPANAL; 3-[(CYCLOPENTYLMETHYL)SULFANYL]PROPANAL; 3-[(CYCLOPROPYLMETHYL)(METHYL)AMINO]-2,2-DIMETHYLPROPANAL; 3-[(CYCLOPROPYLMETHYL)(METHYL)AMINO]PROPANAL; 3-[(CYCLOPROPYLMETHYL)(PROPAN-2-YL)AMINO]PROPANAL; 3-[(CYCLOPROPYLMETHYL)(PROPYL)AMINO]PROPANAL; 3-[(DIMETHYLAMINO)METHYL]BENZALDEHYDE; 3-[(DIMETHYLAMINO)METHYL]OXOLANE-3-CARBALDEHYDE; 3-[(FURAN-2-YLMETHYL)(METHYL)AMINO]PROPANAL; 3-[(FURAN-2-YLMETHYL)SULFANYL]PROPANAL; 3-[(FURAN-3-YLMETHYL)(METHYL)AMINO]PROPANAL; 3-[2-(HYDROXYMETHYL)PIPERIDIN-1-YL]PROPANAL; 3-[2-(HYDROXYMETHYL)PYRROLIDIN-1-YL]PROPANAL; 3-[2-(PROPAN-2-YLOXY)ETHOXY]PROPANAL; 3-[3-(DIMETHYLAMINO)PYRROLIDIN-1-YL]PROPANAL; 3-[3-(HYDROXYMETHYL)PIPERIDIN-1-YL]PROPANAL; 3-[4-(HYDROXYMETHYL)PIPERIDIN-1-YL]PROPANAL; 3-[BIS(2-HYDROXYETHYL)AMINO]PROPANAL; 3-[BUTAN-2-YL(ETHYL)AMINO]PROPANAL; 3-[BUTAN-2-YL(METHYL)AMINO]-2,2-DIMETHYLPROPANAL; 3-[BUTAN-2-YL(METHYL)AMINO]PROPANAL; 3-[BUTYL(2-HYDROXYETHYL)AMINO]PROPANAL; 3-[BUTYL(CYCLOPROPYL)AMINO]PROPANAL; 3-[BUTYL(ETHYL)AMINO]PROPANAL; 3-[BUTYL(METHYL)AMINO]-2,2-DIMETHYLPROPANAL; 3-[BUTYL(METHYL)AMINO]PROPANAL; 3-[CYCLOHEXYL(METHYL)AMINO]PROPANAL; 3-[CYCLOPENTYL(ETHYL)AMINO]PROPANAL; 3-[CYCLOPENTYL(METHYL)AMINO]PROPANAL; 3-[CYCLOPROPYL(2-HYDROXYETHYL)AMINO]PROPANAL; 3-[CYCLOPROPYL(2-METHOXYETHYL)AMINO]PROPANAL; 3-[CYCLOPROPYL(2-METHYLPROPYL)AMINO]PROPANAL; 3-[CYCLOPROPYL(2-OXOETHYL)AMINO]PROPANENITRILE; 3-[CYCLOPROPYL(3-OXOPROPYL)AMINO]PROPANENITRILE; 3-[CYCLOPROPYL(ETHYL)AMINO]-2,2-DIMETHYLPROPANAL; 3-[CYCLOPROPYL(ETHYL)AMINO]PROPANAL; 3-[CYCLOPROPYL(METHYL)AMINO]-2,2-DIMETHYLPROPANAL; 3-[CYCLOPROPYL(METHYL)AMINO]PROPANAL; 3-[CYCLOPROPYL(PROPYL)AMINO]PROPANAL; 3-[ETHYL(1-METHOXYPROPAN-2-YL)AMINO]PROPANAL; 3-[ETHYL(2-HYDROXYETHYL)AMINO]-2,2-DIMETHYLPROPANAL; 3-[ETHYL(2-HYDROXYETHYL)AMINO]PROPANAL; 3-[ETHYL(2-METHOXYETHYL)AMINO]PROPANAL; 3-[ETHYL(2-METHYLPROPYL)AMINO]PROPANAL; 3-[ETHYL(2-OXOETHYL)AMINO]PROPANENITRILE; 3-[ETHYL(3-OXOPROPYL)AMINO]-2-METHYLPROPANENITRILE; 3-[ETHYL(3-OXOPROPYL)AMINO]PROPANENITRILE; 3-[ETHYL(METHYL)AMINO]-2,2-DIMETHYLPROPANAL; 3-[ETHYL(METHYL)AMINO]PROPANAL; 3-[ETHYL(PROPAN-2-YL)AMINO]-2,2-DIMETHYLPROPANAL; 3-[ETHYL(PROPAN-2-YL)AMINO]PROPANAL; 3-[ETHYL(PROPYL)AMINO]-2,2-DIMETHYLPROPANAL; 3-[ETHYL(PROPYL)AMINO]PROPANAL; 3-[METHYL(2,2,2-TRIFLUOROETHYL)AMINO]PROPANAL; 3-[METHYL(2-METHYLBUTYL)AMINO]PROPANAL; 3-[METHYL(2-METHYLPROPYL)AMINO]PROPANAL; 3-[METHYL(2-OXOETHYL)AMINO]BENZONITRILE; 3-[METHYL(2-OXOETHYL)AMINO]BUTANENITRILE; 3-[METHYL(2-OXOETHYL)AMINO]PROPANENITRILE; 3-[METHYL(3-METHYLBUTAN-2-YL)AMINO]PROPANAL; 3-[METHYL(3-METHYLBUTYL)AMINO]PROPANAL; 3-[METHYL(3-OXOPROPYL)AMINO]BUTANENITRILE; 3-[METHYL(3-OXOPROPYL)AMINO]PROPANENITRILE; 3-[METHYL(4-METHYLPENTAN-2-YL)AMINO]PROPANAL; 3-[METHYL(OXAN-4-YL)AMINO]PROPANAL; 3-[METHYL(OXOLAN-2-YLMETHYL)AMINO]PROPANAL; 3-[METHYL(PENTAN-2-YL)AMINO]PROPANAL; 3-[METHYL(PENTAN-3-YL)AMINO]PROPANAL; 3-[METHYL(PENTYL)AMINO]PROPANAL; 3-[METHYL(PHENYL)AMINO]PROPANAL; 3-[METHYL(PROPAN-2-YL)AMINO]PROPANAL; 3-[METHYL(PROPYL)AMINO]PROPANAL; 3-[METHYL(THIOLAN-3-YL)AMINO]PROPANAL; 3-[PROPAN-2-YL(PROPYL)AMINO]PROPANAL; 3-ACETOXYBENZALDEHYDE; 3-ACETYL-4-FLUORO-BENZALDEHYDE; 3-ACETYL-BENZALDEHYDE; 3-ALLYL-4-HYDROXYBENZALDEHYDE; 3-ALLYLSALICYLALDEHYDE; 3-BENZYLOXY-PROPIONALDEHYDE; 3-BUTOXYPROPANAL; 3-BUTYNAL; 3-CHLORO-2-FLUORO-4-HYDROXYBENZALDEHYDE; 3-CHLORO-2-FLUOROBENZALDEHYDE; 3-CHLORO-2-FLUOROPYRIDINE-4-CAR-

BOXALDEHYDE; 3-CHLORO-2-FORMYL-4-PICOLINE; 3-CHLORO-2-HYDROXY-5-FORMYLPYRIDINE; 3-CHLORO-2-HYDROXY-5-METHYL-BENZALDEHYDE; 3-CHLORO-2-HYDROXY-6-METHYL-BENZALDEHYDE; 3-CHLORO-2-HYDROXYBENZALDEHYDE; 3-CHLORO-2-HYDROXYISONICOTINALDEHYDE; 3-CHLORO-2-METHOXYBENZALDEHYDE; 3-CHLORO-2-METHOXYPYRIDINE-6-CARBOXALDEHYDE; 3-CHLORO-2-METHYLBENZALDEHYDE; 3-CHLORO-2-METHYLPYRIDINE-4-CARBOXALDEHYDE; 3-CHLORO-2-METHYLPYRIDINE-5-CARBOXALDEHYDE; 3-CHLORO-2-METHYLPYRIDINE-6-CARBOXALDEHYDE; 3-CHLORO-4,5-DIHYDROXYBENZALDEHYDE; 3-CHLORO-4-CYANOBENZALDEHYDE; 3-CHLORO-4-FLUORO-2-HYDROXYBENZALDEHYDE; 3-CHLORO-4-FLUOROBENZALDEHYDE; 3-CHLORO-4-FORMYL-2-METHOXYPYRIDINE; 3-CHLORO-4-FORMYLBENZONITRILE; 3-CHLORO-4-HYDROXYBENZALDEHYDE; 3-CHLORO-4-METHOXYBENZALDEHYDE; 3-CHLORO-4-METHOXYPYRIDINE-2-CARBOXALDEHYDE; 3-CHLORO-4-METHYLBENZALDEHYDE; 3-CHLORO-5-CYANOBENZALDEHYDE; 3-CHLORO-5-FLUORO-2-HYDROXYBENZALDEHYDE; 3-CHLORO-5-FLUORO-4-HYDROXYBENZALDEHYDE; 3-CHLORO-5-FLUOROBENZALDEHYDE; 3-CHLORO-5-FLUOROISONICOTINALDEHYDE; 3-CHLORO-5-FLUOROPICOLINALDEHYDE; 3-CHLORO-5-FORMYL-2-METHOXYPYRIDINE; 3-CHLORO-5-HYDROXYBENZALDEHYDE; 3-CHLORO-5-HYDROXYPICOLINALDEHYDE; 3-CHLORO-5-METHOXYBENZALDEHYDE; 3-CHLORO-5-METHOXYPYRAZINE-2-CARBALDEHYDE; 3-CHLORO-5-METHOXYPYRIDINE-2-CARBOXALDEHYDE; 3-CHLORO-5-METHOXYPYRIDINE-4-CARBOXALDEHYDE; 3-CHLORO-5-METHYLBENZALDEHYDE; 3-CHLORO-5-METHYLPYRIDINE-2-CARBOXALDEHYDE; 3-CHLORO-5-METHYLPYRIDINE-4-CARBOXALDEHYDE; 3-CHLORO-6-FLUOROPICOLINALDEHYDE; 3-CHLORO-6-HYDROXYPICOLINALDEHYDE; 3-CHLORO-6-METHOXYPICOLINALDEHYDE; 3-CHLORO-6-METHYL-PYRIDINE-2-CARBALDEHYDE; 3-CHLOROBENZALDEHYDE; 3-CHLOROISONICOTINALDEHYDE; 3-CHLOROMETHYL-4-HYDROXY-BENZALDEHYDE; 3-CHLOROPROPANAL; 3-CHLORO-PYRAZINE-2-CARBALDEHYDE; 3-CHLOROPYRIDINE-2-CARBOXALDEHYDE; 3-CINNOLINECARBOXALDEHYDE; 3-CYANO-2-FLUOROBENZALDEHYDE; 3-CYANO-2-HYDROXYBENZALDEHYDE; 3-CYANO-2-METHOXYBENZALDEHYDE; 3-CYANO-2-METHYLBENZALDEHYDE; 3-CYANO-4-HYDROXYBENZALDEHYDE; 3-CYANO-4-METHOXYBENZALDEHYDE; 3-CYANO-5-FLUOROBENZALDEHYDE; 3-CYANO-5-HYDROXYBENZALDEHYDE; 3-CYANO-5-METHOXYBENZALDEHYDE; 3-CYANO-5-METHYLBENZALDEHYDE; 3-CYANOBENZALDEHYDE; 3-CYCLOBUTOXYPROPANAL; 3-CYCLOHEPTYLPROPIONALDEHYDE; 3-CYCLOHEXENE-1-CARBOXALDEHYDE; 3-CYCLOHEXYL-3-OXOPROPANAL; 3-CYCLOHEXYLPROPIONALDEHYDE; 3-CYCLOPENTYL-3-OXOPROPANAL; 3-CYCLOPENTYLPROPANAL; 3-CYCLOPROPOXYBENZALDEHYDE; 3-CYCLOPROPOXYISONICOTINALDEHYDE; 3-CYCLOPROPOXYPICOLINALDEHYDE; 3-CYCLOPROPYL-3-OXOPROPANAL; 3-CYCLOPROPYL-4-FLUOROBENZALDEHYDE; 3-CYCLOPROPYLBENZALDEHYDE; 3-DECYNAL; 3-DEOXYGLUCOSONE; 3-DIETHYLAMINO-2,2-DIMETHYL-PROPIONALDEHYDE; 3-DIMETHYLAMINO-2,2-DIMETHYLPROPIONALDEHYDE; 3-ETHOXY-4-FLUOROBENZALDEHYDE; 3-ETHOXY-4-HYDROXYBENZALDEHYDE; 3-ETHOXY-4-METHYLBENZALDEHYDE; 3-ETHOXY-5-FLUOROBENZALDEHYDE; 3-ETHOXYBENZALDEHYDE; 3-ETHOXYPICOLINALDEHYDE; 3-ETHOXYPROPIONALDEHYDE; 3-ETHOXYSALICYLALDEHYDE; 3-ETHYL-1,2,4-OXADIAZOLE-5-CARBALDEHYDE; 3-ETHYL-1H-INDAZOLE-6-CARBALDEHYDE; 3-ETHYL-2-HYDROXYBENZALDEHYDE; 3-ETHYL-2-PYRAZINECARBOXALDEHYDE; 3-ETHYL-4-FLUOROBENZALDEHYDE; 3-ETHYL-4-FORMYL-BENZONITRILE; 3-ETHYL-4-HYDROXYBENZALDEHYDE; 3-ETHYL-4-METHOXYBENZALDEHYDE; 3-ETHYL-4-PYRIDINECARBOXALDEHYDE; 3-ETHYL-5-HYDROXYBENZALDEHYDE; 3-ETHYLBENZALDEHYDE; 3-ETHYLHEPTANAL; 3-ETHYL-OXETANE-3-CARBALDEHYDE; 3-ETHYNYL-4-METHOXY-BENZALDEHYDE; 3-ETHYNYLBENZALDEHYDE; 3-ETHYNYL-PYRIDINE-4-CARBALDEHYDE; 3-FLUORO-2-FORMYL-4-PICOLINE; 3-FLUORO-2-FORMYL-6-PICOLINE; 3-FLUORO-2-FORMYLPHENYLBORONIC ACID; 3-FLUORO-2-FORMYLPYRIDINE; 3-FLUORO-2-HYDROXY-4-METHYL-BENZALDEHYDE; 3-FLUORO-2-HYDROXY-5-METHYL-BENZALDEHYDE; 3-FLUORO-2-HYDROXY-6-METHOXYBENZALDEHYDE; 3-FLUORO-2-HYDROXY-6-METHYL-BENZALDEHYDE; 3-FLUORO-2-HYDROXYISONICOTINALDEHYDE; 3-FLUORO-2-METHOXYBENZALDEHYDE; 3-FLUORO-2-METHOXYISONICOTINALDEHYDE; 3-FLUORO-2-METHYLBENZALDEHYDE; 3-FLUORO-2-METHYLISONICOTINALDEHYDE; 3-FLUORO-2-NITROBENZALDEHYDE; 3-FLUORO-3-FORMYLOXOLANE; 3-FLUORO-4-FORMYLPHENYLBORONIC ACID; 3-FLUORO-4-HYDROXY-5-METHOXYBENZALDEHYDE; 3-FLUORO-4-HYDROXYBENZALDEHYDE; 3-FLUORO-4-METHOXYBENZALDEHYDE; 3-FLUORO-4-METHYLBENZALDEHYDE; 3-FLUORO-4-NITRO-BENZALDEHYDE; 3-FLUORO-5-(CHLOROMETHYL)BENZALDEHYDE; 3-FLUORO-5-FORMYL-2-METHOXYPYRIDINE; 3-FLUORO-5-FORMYLPHENYLBORONIC ACID; 3-FLUORO-5-FORMYLPYRIDINE; 3-FLUORO-5-HYDROXY-2-PYRIDINECARBOXYLIC ACID; 3-FLUORO-5-HYDROXYBENZALDEHYDE; 3-FLUORO-5-METHOXYBENZALDEHYDE; 3-FLUORO-5-METHOXYPICOLINALDEHYDE; 3-FLUORO-5-METHYLBENZALDEHYDE; 3-FLUORO-5-NITROBENZALDEHYDE; 3-FLUORO-6-FORMYL-2-PICOLINE; 3-FLUORO-6-HYDROXYPYRIDINE-2-CARBOXALDEHYDE; 3-FLUORO-6-METHOXYPICOLINALDEHYDE; 3-FLUOROBENZALDEHYDE; 3-FLUOROISONICOTINALDEHYDE; 3-FLUOROPHENYLGLYOXAL;

3-FLUOROPHENYLGLYOXAL HYDRATE; 3-FLUORO-SALICYLALDEHYDE; 3-FORMYL-1H-INDAZOLE-4-CARBONITRILE; 3-FORMYL-1H-INDAZOLE-6-CARBONITRILE; 3-FORMYL-1H-PYRAZOLE-4-CARBOXYLIC ACID METHYL ESTER; 3-FORMYL-1-PHENYL-1H-PYRAZOLE; 3-FORMYL-2,2-DIMETHYL-CYCLOPROPANECARBOXYLIC ACID ETHYL ESTER; 3-FORMYL-2-PYRIDINECARBONITRILE; 3-FORMYL-4-HYDROXYBENZONITRILE; 3-FORMYL-4-HYDROXYPHENYLBORONIC ACID; 3-FORMYL-4-METHOXYPYRIDINE; 3-FORMYL-4-METHYLPHENYLBORONIC ACID; 3-FORMYL-4-NITROPYRIDINE 1-OXIDE; 3-FORMYL-5-METHYLPHENYLBORONIC ACID; 3-FORMYL-BENZOYL CHLORIDE; 3-FORMYL-CYCLOPENTANECARBONITRILE; 3-FORMYLISONICOTINONITRILE; 3-FORMYLPHENYLBORONIC ACID; 3-FORMYLPYRIDINE-4-BORONIC ACID; 3-FURAN-3-YL-PROPIONALDEHYDE; 3-FURANBUTANAL; 3-FURANPENTANAL; 3-HEPTYNAL; 3-HEXENAL; 3-HEXYNAL; 3-HYDROXY-2-(METHYLTHIO)BENZALDEHYDE; 3-HYDROXY-2,5-DIMETHYLPYRIDINE-4-CARBOXALDEHYDE; 3-HYDROXY-2-ISOPROPYLBENZALDEHYDE; 3-HYDROXY-2-METHOXYBENZALDEHYDE; 3-HYDROXY-2-METHYL-4-PYRIDINECARBOXALDEHYDE; 3-HYDROXY-2-METHYLBENZALDEHYDE; 3-HYDROXY-2-NITROBENZALDEHYDE; 3-HYDROXY-4(HYDROXYMETHYL)-2-METHYL-5-PYRIDINE-CARBOXALDEHYDE; 3-HYDROXY-4-(METHYLTHIO)BENZALDEHYDE; 3-HYDROXY-4-ISOPROPYLBENZALDEHYDE; 3-HYDROXY-4-METHOXYBENZALDEHYDE; 3-HYDROXY-4-METHYL-BENZALDEHYDE; 3-HYDROXY-4-NITROBENZALDEHYDE; 3-HYDROXY-5-(METHYLTHIO)BENZALDEHYDE; 3-HYDROXY-5-ISOPROPYLBENZALDEHYDE; 3-HYDROXY-5-METHOXYBENZALDEHYDE; 3-HYDROXY-5-METHYLBENZALDEHYDE; 3-HYDROXY-5-NITROBENZALDEHYDE; 3-HYDROXY-6-METHOXY-PYRIDINE-2-CARBALDEHYDE; 3-HYDROXY-6-METHYLPYRIDINE-2-CARBOXALDEHYDE; 3-HYDROXYAMINO-BENZALDEHYDE; 3-HYDROXYBENZALDEHYDE; 3-HYDROXY-BENZO[D]ISOXAZOLE-5-CARBALDEHYDE; 3-HYDROXYMETHYL-4-METHOXY-BENZALDEHYDE; 3-HYDROXYNAPHTHALENE-1-CARBOXALDEHYDE; 3-HYDROXYPHENYLGLYOXAL; 3-HYDROXYPHTHALALDEHYDE; 3-HYDROXYPROPANAL; 3-HYDROXYPYRAZINE-2-CARBOXALDEHYDE; 3-HYDROXYPYRIDINE-2-CARBOXALDEHYDE; 3-HYDROXYPYRIDINE-4-CARBOXALDEHYDE; 3-HYDROXYQUINOLINE-2-CARBOXALDEHYDE; 3-HYDROXYQUINOLINE-4-CARBOXALDEHYDE; 3-HYDROXYQUINOLINE-5-CARBOXALDEHYDE; 3-HYDROXYQUINOLINE-6-CARBOXALDEHYDE; 3-HYDROXYQUINOLINE-7-CARBOXALDEHYDE; 3-HYDROXYQUINOLINE-8-CARBOXALDEHYDE; 3-IMIDAZOL-1-YL-PROPIONALDEHYDE; 3-ISOCYANATOBENZALDEHYDE; 3-ISOPROPOXY-BENZALDEHYDE; 3-ISOPROPYL-1,2,4-OXADIAZOLE-5-CARBALDEHYDE; 3-ISOPROPYLBENZALDEHYDE; 3-ISOPROPYLPYRIDINE-2-CARBALDEHYDE; 3-ISOTHIAZOLECARBOXALDEHYDE; 3-ISOTHIAZOLECARBOXALDEHYDE, 4-METHYL-; 3-ISOTHIAZOLECARBOXALDEHYDE, 5-METHYL-; 3-ISOXAZOLECARBOXALDEHYDE, 4-METHYL-; 3-ISOXAZOLECARBOXALDEHYDE, 5-(1-HYDROXY-1-METHYLETHYL)-; 3-MERCAPTO-2-METHYLPENTANAL; 3-MERCAPTOBENZALDEHYDE; 3-METHOXY BUTYRALDEHYDE; 3-METHOXY-2-METHYLBENZALDEHYDE; 3-METHOXY-2-METHYLISONICOTINALDEHYDE; 3-METHOXY-4-METHYLBENZALDEHYDE; 3-METHOXY-4-SULFANYLBENZALDEHYDE; 3-METHOXY-5-METHYLBENZALDEHYDE; 3-METHOXY-5-METHYLPYRAZINE-2-CARBALDEHYDE; 3-METHOXY-6-METHYL-PYRAZINECARBOXALDEHYDE; 3-METHOXYBENZALDEHYDE; 3-METHOXYPHENYLGLYOXAL; 3-METHOXY-PROPIONALDEHYDE; 3-METHOXYPYRAZINE-2-CARBALDEHYDE; 3-METHOXY-PYRIDINE-2-CARBALDEHYDE; 3-METHOXYPYRIDINE-4-CARBOXALDEHYDE; 3-METHYL-[1,2,4]TRIAZINE-5-CARBALDEHYDE; 3-METHYL-1,2,4-OXADIAZOLE-5-CARBALDEHYDE; 3-METHYL-1H-INDAZOLE-5-CARBALDEHYDE; 3-METHYL-1H-PYRAZOLO[3,4-B]PYRIDINE-5-CARBALDEHYDE; 3-METHYL-1-PENTANAL; 3-METHYL-2,3-DIHYDRO-BENZOFURAN-4-CARBALDEHYDE; 3-METHYL-2-NITROBENZALDEHYDE; 3-METHYL-2-PYRIDINECARBOXALDEHYDE; 3-METHYL-2-QUINOXALINECARBALDEHYDE; 3-METHYL-3H-IMIDAZO[4,5-B]PYRIDINE-2-CARBALDEHYDE; 3-METHYL-3H-IMIDAZO[4,5-B]PYRIDINE-6-CARBALDEHYDE; 3-METHYL-3-PHENYLBUTYRALDEHYDE; 3-METHYL-4-NITROBENZALDEHYDE; 3-METHYL-4-NITRO-BUTYRALDEHYDE; 3-METHYL-4-PYRIDINECARBOXALDEHYDE; 3-METHYL-5-NITROBENZALDEHYDE; 3-METHYL-BENZENE-1,2-DICARBOXALDEHYDE; 3-METHYL-HEPTAN-1-AL; 3-METHYLNITROSAMINOPROPIONALDEHYDE; 3-METHYLOCTANAL; 3-METHYLOXETANE-3-CARBALDEHYDE; 3-METHYLPENTANEDIAL; 3-METHYLPYRIDINE-2,5-DICARBALDEHYDE; 3-METHYLQUINOLINE-2-CARBOXALDEHYDE; 3-MORPHOLIN-4-YL-PROPIONALDEHYDE; 3-NITRO-6-PYRIDINECARBOXALDEHYDE; 3-NITROBENZALDEHYDE; 3-NITROISONICOTINALDEHYDE; 3-NITROPROPANAL; 3-NITROPYRIDINE-2-CARBOXALDEHYDE; 3-NITROSALICYLALDEHYDE; 3-NONYNAL; 3-OCTYNAL; 3-OXO-2-(2-THIENYL)PROPANENITRILE; 3-OXO-2-PHENYLPROPANENITRILE; 3-OXO-3-(PYRIDIN-2-YL)PROPANAL; 3-OXO-3-(PYRIDIN-3-YL)PROPANAL; 3-OXO-3-(PYRIDIN-4-YL)PROPANAL; 3-OXO-3-(THIOPHEN-2-YL)PROPANAL; 3-OXO-3-(THIOPHEN-3-YL)PROPANAL; 3-OXO-3-PHENYL-PROPIONALDEHYDE; 3-OXO-BUTANAL; 3-OXOPROPANENITRILE; 3-OXO-PROPIONIC ACID ETHYL ESTER; 3-PENTYNAL; 3-PHENOXYPROPANAL; 3-PHENYL-1,2,4-OXADIAZOLE-5-CARBALDEHYDE; 3-PHENYL-2H-AZIRENE-2-CARBALDEHYDE; 3-PHENYL-4-PENTENAL; 3-PHENYLBUTYRALDEHYDE; 3-PHENYLPROPIONALDEHYDE; 3-PROP-2-YNYLOXY-BENZALDEHYDE; 3-PROPOXYBENZALDEHYDE; 3-PROPOXYPROPANAL; 3-PROPYLBICYCLO(2.2.1)HEPT-5-ENE-2-CARBALDEHYDE; 3-PROPYLENECARBOXYALDEHYDE; 3-PROPYL-SALICYLALDEHYDE; 3-PYRIDAZINECARBOXALDEHYDE, 4-METHYL-; 3-PYRIDAZINECARBOXALDEHYDE, 5-METHYL-; 3-PYRIDIN-4-YL-PROPIONALDEHYDE;

3-PYRIDINECARBOXALDEHYDE; 3-PYRIDINECARBOXALDEHYDE, 1-OXIDE; 3-PYRIDINECARBOXALDEHYDE, 6-(2-HYDROXYETHOXY)-; 3-PYRIDINECARBOXALDEHYDE, 6-ETHYNYL-; 3-PYRIDINECARBOXALDEHYDE, 6-PROPOXY-; 3-QUINOLINECARBOXALDEHYDE; 3-TERT-BUTYL-1,2,4-OXADIAZOLE-5-CARBALDEHYDE; 3-TERT-BUTYLBENZALDEHYDE; 3-TERT-BUTYLDIMETHYLSILYLPROPYNAL; 3-TRIETHYLSILYLPROPYNAL; 3-TRIMETHYLSILYLPROPYNAL; 3-VINYLBENZALDEHYDE; 4-(1,1-DIFLUORO-ETHYL)-BENZALDEHYDE; 4-(1,2,4-OXADIAZOL-3-YL)BENZALDEHYDE; 4-(1,3-DIOXOLAN-2-YL)BUTANAL; 4-(1,3-OXAZOL-4-YL)BENZALDEHYDE; 4-(1-AZIRIDINYL)-BENZALDEHYDE; 4-(1H-1,2,4-TRIAZOL-1-YL)BENZALDEHYDE; 4-(1H-IMIDAZOL-1-YL)BENZALDEHYDE; 4-(1H-PYRAZOL-1-YL)BENZALDEHYDE; 4-(1H-PYRAZOL-3-YL)BENZALDEHYDE; 4-(1H-PYRAZOL-4-YL)BENZALDEHYDE; 4-(1H-PYRROL-1-YL)BENZALDEHYDE; 4-(1H-TETRAZOL-1-YL)-BENZALDEHYDE; 4-(1H-TETRAZOL-5-YL)BENZALDEHYDE; 4-(1-METHYL-2-OXO-PYRROLIDIN-3-YL)-BUTYRALDEHYDE; 4-(1-METHYLETHYL)-3-PYRIDINECARBOXALDEHYDE; 4-(1-METHYLVINYL)BENZALDEHYDE; 4-(2,2,2-TRIFLUOROETHOXY)BUTANAL; 4-(2-FLUOROETHOXY)-BENZALDEHYDE; 4-(2-FURYL)BENZALDEHYDE; 4-(2H-1,2,3-TRIAZOL-2-YL)BENZALDEHYDE; 4-(2H-TETRAZOL-5-YL)BENZALDEHYDE; 4-(2-HYDROXYETHOXY)BENZALDEHYDE; 4-(2-HYDROXYETHYL)BENZALDEHYDE; 4-(2-OXOACETYL)BENZONITRILE; 4-(2-OXOETHOXY)BENZALDEHYDE; 4-(2-OXOETHOXY)BENZONITRILE; 4-(2-PROPEN-1-YL)-3-PYRIDINECARBOXALDEHYDE; 4-(3-BUTEN-1-YL)-5-METHYL-1H-PYRAZOLE-3-CARBOXALDEHYDE; 4-(3-HYDROXYPROP-1-YNYL)BENZALDEHYDE; 4-(3-METHYLBUTOXY)BUTANAL; 4-(3-OXOPROPANOYL)BENZONITRILE; 4-(3-OXO-PROPYL)-BENZONITRILE; 4-(4-HYDROXY-BUT-1-YN-1-YL)BENZALDEHYDE; 4-(BUT-2-YN-1-YLOXY)BENZALDEHYDE; 4-(BUT-3-YN-1-YLOXY)BENZALDEHYDE; 4-(BUTAN-2-YL)-1,3-THIAZOLE-2-CARBALDEHYDE; 4-(CHLOROMETHYL)BENZALDEHYDE; 4-(CHLOROMETHYL)NICOTINALDEHYDE; 4-(DIFLUOROMETHOXY)BENZALDEHYDE; 4-(DIMETHYLAMINO)-2-PYRIDINECARBOXALDEHYDE; 4-(DIMETHYLAMINO)-3-FLUOROBENZALDEHYDE; 4-(DIMETHYLAMINO)-3-HYDROXYBENZALDEHYDE; 4-(DIMETHYLAMINO)-3-METHYLBENZALDEHYDE; 4-(DIMETHYLAMINO)-3-PYRIDINECARBOXALDEHYDE; 4-(DIMETHYLAMINO)BUTANAL; 4-(DIMETHYLAMINO)SALICYLALDEHYDE; 4-(ETHYLTHIO)BENZALDEHYDE; 4-(FLUOROMETHYL)BENZALDEHYDE; 4-(FURAN-2-YL)-4-HYDROXYBUTANAL; 4-(FURAN-2-YL)-4-OXOBUTANAL; 4-(HYDROXY(METHYL)AMINO)BENZALDEHYDE; 4-(HYDROXYMETHYL)-2-PYRIDINECARBOXALDEHYDE; 4-(HYDROXYMETHYL)BENZALDEHYDE; 4-(METHYLSULFINYL)BENZALDEHYDE; 4-(METHYLTHIO)BENZALDEHYDE; 4-(METHYLTHIO)BUTYRALDEHYDE; 4-(OXAZOL-5-YL)BENZALDEHYDE; 4-(PROP-2-YN-1-YLOXY)BENZALDEHYDE; 4-(PROP-2-YNYL)BENZALDEHYDE; 4-(PROPAN-2-YLOXY)BUTANAL; 4-(TRIFLUOROMETHYL)BENZALDEHYDE; 4,4,4-TRIFLUOROBUT-2-YNAL; 4,4,4-TRIFLUOROBUTYRALDEHYDE; 4,4-DIETHOXY-2-BUTYN-1-AL; 4,4-DIFLUOROCYCLOHEXANECARBALDEHYDE; 4,4-DIMETHOXYBUTANAL; 4,4-DIMETHYL-2,6-DIOXOCYCLOHEXANECARBALDEHYDE; 4,4-DIMETHYL-3-OXO-PENTANAL; 4,5,6,7-TETRAHYDRO-1,3-BENZOTHIAZOLE-2-CARBALDEHYDE; 4,5,6,7-TETRAHYDRO-4-BENZOFURANCARBOXALDEHYDE; 4,5,6,7-TETRAHYDRO-4-OXO-5-BENZOFURANCARBOXALDEHYDE; 4,5,6,7-TETRAHYDROBENZO[D]ISOXAZOLE-3-CARBALDEHYDE; 4,5,6,7-TETRAHYDROPYRAZOLO[1,5-A]PYRIDINE-2-CARBALDEHYDE; 4,5-DIFLUORO-2-HYDROXYBENZALDEHYDE; 4,5-DIFLUORO-2-METHOXYBENZALDEHYDE; 4,5-DIFLUORO-3-HYDROXYBENZALDEHYDE; 4,5-DIFLUOROPYRIDINE-2-CARBALDEHYDE; 4,5-DIMETHYL-1,3-THIAZOLE-2-CARBALDEHYDE; 4,5-DIMETHYL-4H-1,2,4-TRIAZOLE-3-CARBALDEHYDE; 4,5-DIMETHYLPYRIDINE-2-CARBALDEHYDE; 4,6,6-TRIMETHYLHEPTANAL; 4,6-DIFLUORO-5-PYRIMIDINE FORMALDEHYDE; 4,6-DIHYDROXY-2-METHYL-PYRIMIDINE-5-CARBALDEHYDE; 4,6-DIHYDROXY-5-FORMYLPYRIMIDINE; 4,6-DIHYDROXY-PYRIDINE-3-CARBALDEHYDE; 4,6-DIMETHOXYPYRIMIDINE-2YL-CARBALDEHYDE; 4,6-DIMETHOXYPYRIMIDINE-5-CARBALDEHYDE; 4,6-DIMETHYL-2-PYRIMIDINECARBOXALDEHYDE; 4,6-DIMETHYL-3-(1H)INDAZOLE CARBOXALDEHYDE; 4,6-DIMETHYL-3-PYRIDINECARBOXALDEHYDE; 4,6-DIMETHYLCYCLOHEX-3-ENECARBALDEHYDE; 4,6-DIMETHYLPYRIDINE-2-CARBALDEHYDE; 4,7-DIMETHYL-1H-INDAZOLE-3-CARBALDEHYDE; 4,8-DIMETHYLNONANAL; 4-[(DIMETHYLAMINO)METHYL]OXANE-4-CARBALDEHYDE; 4-[1,2,3]TRIAZOL-1-YL-BENZALDEHYDE; 4-[ETHYL(METHYL)AMINO]BENZALDEHYDE; 4-[METHYL(2-OXOETHYL)AMINO]BENZONITRILE; 4-ACETOXY-4-METHYL-1-PENTANAL; 4-ACETOXYBENZALDEHYDE; 4-ACETYL-2-PYRIDINECARBOXALDEHYDE; 4-ACETYLBENZALDEHYDE; 4-ALLYLOXYBENZALDEHYDE; 4-BENZOFURANCARBOXALDEHYDE; 4-BROMOBUTYRALDEHYDE; 4-BUTOXYBUTANAL; 4-BUTYLBENZALDEHYDE; 4-BUTYLCYCLOHEXANE-1-CARBALDEHYDE; 4-CARBOXALDEHYDEBENZOCYCLOBUTENE; 4-CHLORO-2,5-DIMETHYLBENZALDEHYDE; 4-CHLORO-2,6-DIMETHYLBENZALDEHYDE; 4-CHLORO-2,6-DIMETHYLPYRIDINE-3-CARBOXALDEHYDE; 4-CHLORO-2-ETHYL-BENZALDEHYDE; 4-CHLORO-2-FLUOROBENZALDEHYDE; 4-CHLORO-2-FLUOROPYRIDINE-3-CARBOXALDEHYDE; 4-CHLORO-2-FORMYLBENZONITRILE; 4-CHLORO-2-HYDROXYBENZALDEHYDE; 4-CHLORO-2-MERCAPTOBENZALDEHYDE; 4-CHLORO-2-METHOXYBENZALDEHYDE; 4-CHLORO-2-METHOXYPYRIDINE-3-CARBALDEHYDE; 4-CHLORO-2-METHOXYPYRIDINE-5-CARBOXALDEHYDE; 4-CHLORO-2-METHYL-5-PYRIMIDINECARBOXALDEHYDE; 4-CHLORO-2-METHYLBENZALDEHYDE; 4-CHLORO-2-METHYL-PYRIDINE-3-CARBALDEHYDE; 4-CHLORO-2-METHYLPYRIDINE-5-CARBOXALDEHYDE; 4-CHLORO-3,5-DIMETHYLBENZALDEHYDE; 4-CHLORO-3-CYANOBENZALDEHYDE; 4-CHLORO-3-ETHYLBENZALDEHYDE; 4-CHLORO-3-FLUOROBENZALDEHYDE; 4-CHLORO-3-FLUO-

ROPICOLINALDEHYDE; 4-CHLORO-3-FORMYLBENZONITRILE; 4-CHLORO-3-HYDROXYBENZALDEHYDE; 4-CHLORO-3-HYDROXYMETHYL-BENZALDEHYDE; 4-CHLORO-3-METHOXYBENZALDEHYDE; 4-CHLORO-3-METHOXYPYRIDINE-2-CARBOXALDEHYDE; 4-CHLORO-3-METHYLBENZALDEHYDE; 4-CHLORO-3-METHYL-PYRIDINE-2-CARBALDEHYDE; 4-CHLORO-5-FLUORO-PYRIDINE-2-CARBALDEHYDE; 4-CHLORO-5-FLUORO-PYRIDINE-3-CARBALDEHYDE; 4-CHLORO-5-HYDROXY-PYRIDINE-2-CARBALDEHYDE; 4-CHLORO-5-HYDROXY-PYRIDINE-3-CARBALDEHYDE; 4-CHLORO-5-METHOXY-PYRIDINE-2-CARBALDEHYDE; 4-CHLORO-5-METHOXYPYRIDINE-3-CARBOXALDEHYDE; 4-CHLORO-5-METHYL-PYRIDINE-2-CARBALDEHYDE; 4-CHLORO-5-METHYL-PYRIDINE-3-CARBALDEHYDE; 4-CHLORO-6-FORMYL-NICOTINONITRILE; 4-CHLORO-6-METHOXY-PYRIDINE-2-CARBALDEHYDE; 4-CHLORO-6-METHOXYPYRIMIDINE-2-CARBALDEHYDE; 4-CHLORO-6-METHYL-PYRIDINE-2-CARBALDEHYDE; 4-CHLOROBENZALDEHYDE; 4-CHLORO-BUTYRALDEHYDE; 4-CHLOROPICOLINALDEHYDE; 4-CHLOROPYRIDINE-2,6-DICARBOXALDEHYDE; 4-CHLOROPYRIDINE-3-CARBOXALDEHYDE; 4-CHLOROPYRIMIDINE-2-CARBALDEHYDE; 4-CHLOROPYRIMIDINE-5-CARBALDEHYDE; 4-CINNOLINECARBOXALDEHYDE; 4-CYANO-2,5-DIFLUOROBENZALDEHYDE; 4-CYANO-2,6-DIFLUOROBENZALDEHYDE; 4-CYANO-2-FLUOROBENZALDEHYDE; 4-CYANO-2-METHOXYBENZALDEHYDE; 4-CYANO-2-METHYLBENZALDEHYDE; 4-CYANO-3-HYDROXYBENZALDEHYDE; 4-CYANO-3-METHOXY-BENZALDEHYDE; 4-CYANO-3-METHYLBENZALDEHYDE; 4-CYANOBENZALDEHYDE; 4-CYANOPYRIDINE-2-CARBOXALDEHYDE; 4-CYCLOHEXYLBUTYRALDEHYDE; 4-CYCLOPENTYL-BENZALDEHYDE; 4-CYCLOPROPOXYBENZALDEHYDE; 4-CYCLOPROPOXYNICOTINALDEHYDE; 4-CYCLOPROPYLPICOLINALDEHYDE; 4-CYCLOPROPYL-2-FLUOROBENZALDEHYDE; 4-CYCLOPROPYLBENZALDEHYDE; 4-DIMETHYLAMINO-2-METHYLBENZALDEHYDE; 4-DIMETHYLAMINOBENZALDEHYDE; 4-DIMETHYLAMINOMETHYL-BENZALDEHYDE; 4-ETHOXY-2-HYDROXY-BENZALDEHYDE; 4-ETHOXY-2-METHYLBENZALDEHYDE; 4-ETHOXY-3-FLUOROBENZALDEHYDE; 4-ETHOXY-3-HYDROXYBENZALDEHYDE; 4-ETHOXY-3-METHYLBENZALDEHYDE; 4-ETHOXY-3-METHYL-PYRIDINE-2-CARBALDEHYDE; 4-ETHOXYBENZALDEHYDE; 4-ETHOXYBUTANAL; 4-ETHOXYNICOTINALDEHYDE; 4-ETHOXYPYRIDINE-2-CARBALDEHYDE; 4-ETHYL-2-HYDROXY-BENZALDEHYDE; 4-ETHYL-2-THIAZOLECARBOXALDEHYDE; 4-ETHYL-3-HYDROXYBENZALDEHYDE; 4-ETHYL-4-FORMYLHEXANENITRILE; 4-ETHYL-4-FORMYL-TETRAHYDROPYRAN; 4-ETHYL-5-METHYL-1,3-THIAZOLE-2-CARBALDEHYDE; 4-ETHYLBENZALDEHYDE; 4-ETHYLOCTANAL; 4-ETHYL-TETRAHYDRO-2H-THIOPYRAN-4-CARBALDEHYDE; 4-ETHYNYLBENZALDEHYDE; 4-ETHYNYL-PYRIDINE-2-CARBALDEHYDE; 4-ETHYNYL-PYRIDINE-3-CARBALDEHYDE; 4-FLUORO-1H-INDAZOLE-3-CARBALDEHYDE; 4-FLUORO-1-NAPHTHALDEHYDE; 4-FLUORO-2-(METHYLTHIO)BENZALDEHYDE; 4-FLUORO-2,3-DIMETHYLBENZALDEHYDE; 4-FLUORO-2-FORMYLPYRIDINE; 4-FLUORO-2-HYDROXYBENZALDEHYDE; 4-FLUORO-2-MERCAPTOBENZALDEHYDE; 4-FLUORO-2-METHOXYBENZALDEHYDE; 4-FLUORO-2-METHYLBENZALDEHYDE; 4-FLUORO-2-METHYL-PYRIDINE-3-CARBALDEHYDE; 4-FLUORO-2-NITROBENZALDEHYDE; 4-FLUORO-3-(CHLOROMETHYL)BENZALDEHYDE; 4-FLUORO-3,5-DIMETHYLBENZALDEHYDE; 4-FLUORO-3-FORMYLPHENYLBORONIC ACID; 4-FLUORO-3-FORMYLPYRIDINE; 4-FLUORO-3-HYDROXYBENZALDEHYDE; 4-FLUORO-3-ISOPROPYLBENZALDEHYDE; 4-FLUORO-3-METHOXYBENZALDEHYDE; 4-FLUORO-3-METHYLBENZALDEHYDE; 4-FLUORO-3-NITROBENZALDEHYDE; 4-FLUORO-4-FORMYLTHIANE; 4-FLUOROBENZALDEHYDE; 4-FLUOROBENZENE-1,2-DICARBOXALDEHYDE; 4-FLUOROBENZO[D]OXAZOLE-2-CARBALDEHYDE; 4-FLUOROBENZOFURAN-7-CARBALDEHYDE; 4-FLUOROBUTYRALDEHYDE; 4-FLUOROPHENYLGLYOXAL HYDRATE; 4-FORMYL-1-PIPERIDINECARBOXYLIC ACID METHYL ESTER; 4-FORMYL-2-METHYLPHENYLBORONIC ACID; 4-FORMYL-3-HYDROXYPHENYLBORONIC ACID; 4-FORMYL-3-METHYLPHENYLBORONIC ACID; 4-FORMYL-4-METHYL-TETRAHYDROPYRAN; 4-FORMYL-4-METHYLTHIANE; 4-FORMYLBENZALDEHYDE-O-METHYL ALDOXIME; 4-FORMYL-BENZENEPROPANAL; 4-FORMYL-BENZOYL CHLORIDE; 4-FORMYL-HEXANOIC ACID METHYL ESTER; 4-FORMYLNICOTINONITRILE; 4-FORMYLPHENYLBORONIC ACID; 4-FORMYLPYRIMIDINE-2-CARBONITRILE; 4-FORMYLTETRAHYDROPYRAN; 4-FORMYL-TETRAHYDRO-PYRAN-4-CARBOXYLIC ACID METHYL ESTER; 4H-CYCLOPENTA[D]THIAZOLE-2-CARBOXALDEHYDE, 5,6-DIHYDRO-; 4-HYDROXY-1H-INDAZOLE-3-CARBALDEHYDE; 4-HYDROXY-1-METHYL-2,5-CYCLOHEXADIENE-1-CARBALDEHYDE; 4-HYDROXY-1-NAPHTHALDEHYDE; 4-HYDROXY-2-(METHYLTHIO)BENZALDEHYDE; 4-HYDROXY-2,5-DIMETHYLBENZALDEHYDE; 4-HYDROXY-2-ISOPROPYLBENZALDEHYDE; 4-HYDROXY-2-METHOXYBENZALDEHYDE; 4-HYDROXY-2-METHYLBENZALDEHYDE; 4-HYDROXY-2-NITROBENZALDEHYDE; 4-HYDROXY-2-QUINOLINECARBALDEHYDE; 4-HYDROXY-3-(METHYLTHIO)BENZALDEHYDE; 4-HYDROXY-3-ISOPROPYLBENZALDEHYDE; 4-HYDROXY-3-METHOXY-5-METHYLBENZENECARBALDEHYDE; 4-HYDROXY-3-METHYLBENZALDEHYDE; 4-HYDROXY-3-NITROBENZALDEHYDE; 4-HYDROXY-4-METHYL-HEX-2-YNAL; 4-HYDROXY-5-BENZOFURANCARBOXALDEHYDE; 4-HYDROXY-5-METHOXY-2-PYRIDINECARBALDEHYDE; 4-HYDROXY-5-METHYL-1,3-DIALDEHYDE; 4-HYDROXY-5-NITRONICOTINALDEHYDE; 4-HYDROXYBENZALDEHYDE; 4-HYDROXYBENZALDEHYDE POTASSIUM SALT; 4-HYDROXY-BICYCLO[2.2.2]OCTANE-1-CARBOXALDEHYDE; 4-HYDROXYINDANE-5-CARBALDEHYDE;

4-HYDROXYISOPHTHALALDEHYDE; 4-HYDROXYNAPHTHALENE-2-CARBOXALDEHYDE; 4-HYDROXYPHENYL GLYOXAL; 4-HYDROXYPHENYLGLYOXAL HYDRATE; 4-HYDROXYPHTHALALDEHYDE; 4-HYDROXY-PYRIDINE-2-CARBALDEHYDE; 4-HYDROXYPYRIDINE-3-CARBOXALDEHYDE; 4-HYDROXY-QUINOLINE-3-CARBALDEHYDE; 4-HYDROXYQUINOLINE-5-CARBOXALDEHYDE; 4-HYDROXYQUINOLINE-6-CARBOXALDEHYDE; 4-HYDROXYQUINOLINE-7-CARBOXALDEHYDE; 4-HYDROXYQUINOLINE-8-CARBOXALDEHYDE; 4-IMIDAZOL-1-YL-BUTYRALDEHYDE; 4-ISOBUTYLBENZALDEHYDE; 4-ISOCYANATOBENZALDEHYDE; 4-ISOPROPOXY-BENZALDEHYDE; 4-ISOPROPYL-1,3-THIAZOLE-2-CARBALDEHYDE; 4-ISOPROPYLBENZALDEHYDE; 4-MERCAPTOBENZALDEHYDE; 4-METHOXY-2,6-DIMETHYLBENZALDEHYDE; 4-METHOXY-2-METHYLBENZALDEHYDE; 4-METHOXY-2-PYRIMIDINECARBOXALDEHYDE; 4-METHOXY-3,5-DIMETHYLPICOLINALDEHYDE; 4-METHOXY-3-METHYLBENZALDEHYDE; 4-METHOXY-3-METHYL-PYRIDINE-2-CARBALDEHYDE; 4-METHOXYBUTANAL; 4-METHOXYISOPHTHALALDEHYDE; 4-METHOXYMETHYLBENZALDEHYDE; 4-METHOXYPHENYLACETALDEHYDE; 4-METHOXYPHTHALALDEHYDE; 4-METHOXYPICOLINALDEHYDE; 4-METHOXYPYRIDINE-2,6-DICARBALDEHYDE; 4-METHYL-1,2,5-OXADIAZOLE-3-CARBOXALDEHYDE; 4-METHYL-1,3-THIAZOLE-2-CARBALDEHYDE; 4-METHYL-1-NAPHTHALDEHYDE; 4-METHYL-2-(PROP-2-YN-1-YLOXY)BENZALDEHYDE; 4-METHYL-2,6-PYRIDINEDICARBOXALDEHYDE; 4-METHYL-2-NITROBENZALDEHYDE; 4-METHYL-2-PYRIMIDINECARBOXALDEHYDE; 4-METHYL-2-THIAZOLECARBOXALDEHYDE 3-OXIDE; 4-METHYL-3-(1H)INDAZOLE CARBOXALDEHYDE; 4-METHYL-3-NITROBENZALDEHYDE; 4-METHYL-3-NITROPICOLINALDEHYDE; 4-METHYL-3-OXOPENTANAL; 4-METHYL-4H-1,2,4-TRIAZOLE-3-CARBALDEHYDE; 4-METHYL-4-NITROVALERALDEHYDE; 4-METHYL-5-OXO-PENTANOIC ACID METHYL ESTER; 4-METHYL-5-THIAZOLEACETALDEHYDE; 4-METHYLHEPTANAL; 4-METHYLHEXANAL; 4-METHYLNICOTINALDEHYDE; 4-METHYLPENTALDEHYDE; 4-METHYLPHENYLGLYOXAL HYDRATE; 4-METHYLPYRIDINE-2,5-DICARBALDEHYDE; 4-METHYLPYRIMIDINE-5-CARBALDEHYDE; 4-METHYQUINOLINE-2-CARBOXALDEHYDE; 4-NITRO-2-FORMYLPYRIDINE N-OXIDE; 4-NITROBENZALDEHYDE; 4-NITRONICOTINALDEHYDE; 4-NITRO-PYRIDINE-2-CARBALDEHYDE; 4-N-PROPOXYBENZALDEHYDE; 4-N-PROPYLBENZALDEHYDE; 4-OXO-4-(3-PYRIDYL)-BUTANAL; 4-OXO-4-(PIPERIDIN-1-YL)BUTANAL; 4-OXO-6,7-DIHYDRO-4H-PYRAZOLO[5,1-C][1,4] OXAZINE-2-CARBALDEHYDE; 4-OXOBUTANOIC ACID METHYL ESTER; 4-OXO-TETRAHYDRO-FURAN-3-CARBOXALDEHYDE; 4-PENTENAL; 4-PHENOXYBUTANAL; 4-PHENYLBUTYRALDEHYDE; 4-PROPYL-1,3-THIAZOLE-2-CARBALDEHYDE; 4-PROPYL-3-PYRIDINECARBOXALDEHYDE; 4-PYRIDAZINECARBOXALDEHYDE, 3-METHYL-; 4-PYRIDAZINECARBOXALDEHYDE, 5-METHYL-; 4-PYRIDAZINECARBOXALDEHYDE, 6-METHYL-; 4-PYRIDIN-2-YLBUTANAL; 4-PYRIDIN-3-YLBUTANAL; 4-PYRIDIN-4-YLBUTANAL; 4-PYRIDINECARBOXALDEHYDE; 4-PYRIDINECARBOXALDEHYDE N-OXIDE; 4-PYRIMIDINECARBOXALDEHYDE, 5-METHYL-; 4-QUINOLINECARBOXALDEHYDE; 4-QUINOLINECARBOXALDEHYDE, 8-HYDROXY-; 4-TERT-BUTYL-1,3-THIAZOLE-2-CARBALDEHYDE; 4-TERT-BUTYLBENZALDEHYDE; 4-TERT-BUTYLCYCLOHEXANE-1-CARBALDEHYDE; 4-TETRAHYDROPYRANYLOXY-BUTANAL; 4-THIAZOLEPROPANAL; 4-VINYL-BENZALDEHYDE; 5-(1,1-DIMETHYL-ETHYL)-3-ISOXAZOLECARBOXALDEHYDE; 5-(1-METHYLETHYL)-2-PYRIDINECARBOXALDEHYDE; 5-(2-FURYL)ISOXAZOLE-3-CARBALDEHYDE; 5-(2-FURYL)PYRIDINE-2-CARBALDEHYDE; 5-(2-METHYL-PROPENYL)-PYRIDINE-2-CARBALDEHYDE; 5-(CHLOROMETHYL)NICOTINALDEHYDE; 5-(CHLOROMETHYL)PICOLINALDEHYDE; 5-(DIFLUOROMETHOXY)PYRAZINE-2-CARBOXALDEHYDE; 5-(DIMETHYLAMINO)-2-PYRIDINECARBOXALDEHYDE; 5-(DIMETHYLAMINO)PYRAZINE-2-CARBALDEHYDE; 5-(DIMETHYLAMINO) SALICYLALDEHYDE; 5-(FURAN-2-YL)PYRIDINE-3-CARBALDEHYDE; 5-(HYDROXYMETHYL)-2-PYRIDINECARBOXALDEHYDE; 5-(METHOXYMETHYL)-4-METHYL-1,3-THIAZOLE-2-CARBALDEHYDE; 5-(METHYLTHIO)-1H-PYRAZOLE-3-CARBALDEHYDE; 5-(PYRIDIN-2-YL)OXAZOLE-2-CARBALDEHYDE; 5-(TRIFLUOROMETHYL)-1,3,4-OXADIAZOLE-2-CARBALDEHYDE; 5-(TRIFLUOROMETHYL)-1H-PYRAZOLE-3-CARBALDEHYDE; 5,5-DIETHOXYPENTANAL; 5,5-DIMETHOXYPENTANAL; 5,5-DIMETHYL-1,3-DIOXANE-2-PROPIONALDEHYDE; 5,5-DIMETHYLHEXANAL; 5,6,7,8-TETRAHYDRO-7-INDOLIZINECARBOXALDEHYDE; 5,6,7,8-TETRAHYDRO-NAPHTHALENE-2-CARBALDEHYDE; 5,6-DIFLUORONICOTINALDEHYDE; 5,6-DIFLUOROPICOLINALDEHYDE; 5,6-DIHYDRO-4H-PYRROLO[1,2-B]PYRAZOLE-2-CARBALDEHYDE; 5,6-DIHYDRO-5-INDOLIZINECARBOXALDEHYDE; 5,6-DIMETHOXYNICOTINALDEHYDE; 5,6-DIMETHOXYPICOLINALDEHYDE; 5,6-DIMETHYLPYRIDINE-2-CARBALDEHYDE; 5,7-DIHYDRO-5-OXO-FURO[3,4-B]PYRIDINE-2-CARBOXALDEHYDE; 5-[(DIMETHYLAMINO)METHYL]ISOXAZOLE-3-CARBALDEHYDE; 5-ACETYL-2-PYRIDINECARBOXALDEHYDE; 5-ACETYL-PYRAZINECARBOXALDEHYDE; 5-BENZOTHIAZOLECARBOXALDEHYDE; 5-CHLORO-2,2-DIMETHYLPENTANAL; 5-CHLORO-2,4-DIHYDROXY-BENZALDEHYDE; 5-CHLORO-2-FLUORO-3-FORMYL-4-PICOLINE; 5-CHLORO-2-FLUOROBENZALDEHYDE; 5-CHLORO-2-FLUOROISONICOTINALDEHYDE; 5-CHLORO-2-FLUOROMETHYLBENZALDEHYDE; 5-CHLORO-2-FLUORONICOTINALDEHYDE; 5-CHLORO-2-FORMYLBENZONITRILE; 5-CHLORO-2-FORMYLPYRIDINE; 5-CHLORO-2-HYDROXY-3-METHYLBENZALDEHYDE; 5-CHLORO-2-HYDROXY-4-METHYL-BENZALDEHYDE; 5-CHLORO-2-HYDROXYISONICOTINALDEHYDE; 5-CHLORO-2-HYDROXYNICOTINALDEHYDE; 5-CHLORO-2-MERCAPTOBENZALDEHYDE; 5-CHLORO-2-METHOXYBENZALDEHYDE; 5-CHLORO-2-METHOXYNICOTINALDEHYDE; 5-CHLORO-2-METHOXY-PYRIDINE-4-CARBALDEHYDE; 5-CHLORO-2-METHYLBENZALDEHYDE;

5-CHLORO-2-METHYL-PYRIDINE-3-CARBALDEHYDE; 5-CHLORO-2-METHYL-PYRIDINE-4-CARBALDEHYDE; 5-CHLORO-3-FLUORO-2-HYDROXYBENZALDEHYDE; 5-CHLORO-3-FLUOROPICOLINALDEHYDE; 5-CHLORO-3-METHOXYPYRAZINE-2-CARBALDEHYDE; 5-CHLORO-3-METHOXYPYRIDINE-2-CARBOXALDEHYDE; 5-CHLORO-3-METHYLPYRIDINE-2-CARBOXALDEHYDE; 5-CHLORO-4-METHOXYPYRIDINE-2-CARBOXALDEHYDE; 5-CHLORO-4-METHOXYPYRIDINE-3-CARBOXALDEHYDE; 5-CHLORO-4-METHYL-PYRIDINE-2-CARBALDEHYDE; 5-CHLORO-4-METHYLPYRIDINE-3-CARBOXALDEHYDE; 5-CHLORO-6-FLUORONICOTINALDEHYDE; 5-CHLORO-6-FLUOROPICOLINALDEHYDE; 5-CHLORO-6-HYDROXYPICOLINALDEHYDE; 5-CHLOROISOPHTHALALDEHYDE; 5-CHLORO-PENTANAL; 5-CHLOROPYRAZINE-2-CARBALDEHYDE; 5-CHLOROPYRIDINE-3-CARBALDEHYDE; 5-CHLOROPYRIMIDINE-2-CARBALDEHYDE; 5-CHLOROPYRIMIDINE-4-CARBOXALDEHYDE; 5-CHLOROSALICYLALDEHYDE; 5-CHLOROTHIAZOLE-2-CARBALDEHYDE; 5-CYANOINDAZOLE-3-CARBOXALDEHYDE; 5-CYANO-2-FLUOROBENZALDEHYDE; 5-CYANO-2-METHOXYBENZALDEHYDE; 5-CYANO-2-METHYLBENZALDEHYDE; 5-CYANOISOPHTHALALDEHYDE; 5-CYCLOPROPOXYNICOTINALDEHYDE; 5-CYCLOPROPOXYPICOLINALDEHYDE; 5-CYCLOPROPYL-1H-PYRAZOLE-3-CARBALDEHYDE; 5-CYCLOPROPYL-2-FLUOROBENZALDEHYDE; 5-CYCLOPROPYL-2-HYDROXYBENZALDEHYDE; 5-CYCLOPROPYLPYRAZINE-2-CARBALDEHYDE; 5-DEOXY-3,4-D1-O-METHYL-D-RIBOSE; 5-DEOXY-3,4-DI-O-METHYL-L-ARABINOSE; 5-DEOXY-D-RIBOSE; 5-DEOXY-L-ARABINOSE; 5-ETHOXY-2-HYDROXY-BENZALDEHYDE; 5-ETHOXYPYRIDINE-2-CARBALDEHYDE; 5-ETHYL-1,3,4-OXADIAZOLE-2-CARBALDEHYDE; 5-ETHYL-1,3-THIAZOLE-2-CARBALDEHYDE; 5-ETHYL-2-HYDROXYBENZENECARBALDEHYDE; 5-ETHYL-2-METHOXYBENZALDEHYDE; 5-ETHYL-2-PYRIDINECARBOXALDEHYDE; 5-ETHYL-3-METHYLBENZALDEHYDE; 5-ETHYL-3-PYRIDINECARBOXALDEHYDE; 5-ETHYLISOXAZOLE-3-CARBALDEHYDE; 5-ETHYNYL-2-METHOXYBENZALDEHYDE; 5-ETHYNYL-2-PYRIDINECARBOXALDEHYDE; 5-ETHYNYLNICOTINALDEHYDE; 5-FLUORO-1H-INDAZOLE-3-CARBALDEHYDE; 5-FLUORO-1-NAPHTHALDEHYDE; 5-FLUORO-2,3-DIHYDROBENZOFURAN-7-CARBOXALDEHYDE; 5-FLUORO-2-FORMYLPHENYLBORONIC ACID; 5-FLUORO-2-FORMYLPYRIDINE; 5-FLUORO-2-HYDROXY-3-METHYLBENZALDEHYDE; 5-FLUORO-2-HYDROXY-4-PYRIDINECARBOXALDEHYDE; 5-FLUORO-2-HYDROXYBENZALDEHYDE; 5-FLUORO-2-HYDROXYNICOTINALDEHYDE; 5-FLUORO-2-MERCAPTOBENZALDEHYDE; 5-FLUORO-2-METHOXYBENZALDEHYDE; 5-FLUORO-2-METHOXYNICOTINALDEHYDE; 5-FLUORO-2-METHYL-3-PYRIDINECARBOXALDEHYDE; 5-FLUORO-2-METHYLBENZALDEHYDE; 5-FLUORO-2-NITROBENZALDEHYDE; 5-FLUORO-4-FORMYL-2-METHOXYPYRIDINE; 5-FLUORO-4-HYDROXYISOPHTHALALDEHYDE; 5-FLUORO-6-HYDROXYNICOTINALDEHYDE; 5-FLUORO-6-HYDROXYPICOLINALDEHYDE; 5-FLUORO-6-METHOXYPICOLINALDEHYDE; 5-FLUORO-6-METHYLNICOTINALDEHYDE; 5-FLUOROBENZO[D]OXAZOLE-2-CARBALDEHYDE; 5-FLUOROISOPHTHALALDEHYDE; 5-FLUORONAPHTHALENE-2-CARBOXALDEHYDE; 5-FLUORO-PYRIMIDINE-2-CARBALDEHYDE; 5-FORMYL-1-INDANONE; 5-FORMYL-2H-PYRAZOLE-3-CARBOXYLIC ACID METHYL ESTER; 5-FORMYL-2-ISOPROXYPYRIDINE; 5-FORMYL-2-METHOXY-4-PICOLINE; 5-FORMYL-2-METHYLBENZONITRILE; 5-FORMYL-2-METHYLPHENYLBORONIC ACID; 5-FORMYLFURO[2,3-B]PYRIDINE; 5-FORMYL-PYRAZINE-2-CARBOXYLIC ACID METHYL ESTER; 5-FORMYLPYRIDINE-2-BORONIC ACID; 5-FORMYLPYRIDINE-2-BORONIC ACIDHYDRATE; 5-FORMYLPYRIDINE-2-CARBONITRILE; 5-FORNYL-3-PYRIDINECARBONITRILE; 5-FURAN-2-YL-[1,2,4]OXADIAZOLE-3-CARBALDEHYDE; 5-FURAN-2-YL-OXAZOLE-2-CARBALDEHYDE; 5-HEXYNAL; 5-HYDROXY-1H-INDAZOLE-3-CARBOXALDEHYDE; 5-HYDROXY-1H-INDAZOLE-4-CARBALDEHYDE; 5-HYDROXY-2-(METHYLTHIO)BENZALDEHYDE; 5-HYDROXY-2-ISOPROPYLBENZALDEHYDE; 5-HYDROXY-2-METHOXYBENZALDEHYDE; 5-HYDROXY-2-METHOXY-PYRIDINE-4-CARBALDEHYDE; 5-HYDROXY-2-METHYLBENZALDEHYDE; 5-HYDROXY-2-METHYL-BENZENEPROPANAL; 5-HYDROXY-2-NITROBENZALDEHYDE; 5-HYDROXY-4,6-DIMETHYL-3-PYRIDINECARBOXALDEHYDE; 5-HYDROXY-4-BENZOFURANCARBOXALDEHYDE; 5-HYDROXY-6-BENZOFURANCARBOXALDEHYDE; 5-HYDROXY-6-METHYL-2-PYRIDINECARBOXALDEHYDE; 5-HYDROXY-6-NITRONICOTINALDEHYDE; 5-HYDROXYNAPHTHALENE-1-CARBOXALDEHYDE; 5-HYDROXYNAPHTHALENE-2-CARBOXALDEHYDE; 5-HYDROXYNICOTINALDEHYDE; 5-HYDROXYPENTANAL; 5-HYDROXYPYRAZINE-2-CARBOXALDEHYDE; 5-HYDROXYPYRIDINE-2-CARBALDEHYDE; 5-HYDROXYPYRIMIDINE-2-CARBOXALDEHYDE; 5-HYDROXYQUINOLINE-2-CARBOXALDEHYDE; 5-HYDROXYQUINOLINE-3-CARBOXALDEHYDE; 5-HYDROXYQUINOLINE-4-CARBOXALDEHYDE; 5-HYDROXYQUINOLINE-6-CARBOXALDEHYDE; 5-HYDROXYQUINOLINE-7-CARBOXALDEHYDE; 5-HYDROXYQUINOLINE-8-CARBOXALDEHYDE; 5-IMIDAZOL-1-YL-PENTANAL; 5-ISOBENZOFURANCARBOXALDEHYDE, 1,3-DIHYDRO-; 5-ISOBUTYL-1H-PYRAZOLE-3-CARBALDEHYDE; 5-ISOBUTYLPYRAZINE-2-CARBALDEHYDE; 5-ISOPROPYL-1,3,4-OXADIAZOLE-2-CARBALDEHYDE; 5-ISOPROPYL-1,3,4-THIADIAZOLE-2-CARBALDEHYDE; 5-ISOPROPYL-3-METHYLBENZALDEHYDE; 5-ISOPROPYLISOXAZOLE-3-CARBALDEHYDE; 5-ISOPROPYLPYRAZINE-2-CARBALDEHYDE; 5-METHANESULFONYLPENTANAL; 5-METHOXY-2-METHYLBENZALDEHYDE; 5-METHOXY-2-PYRIMIDINECARBOXALDEHYDE; 5-METHOXY-3-PYRIDINECARBOXALDEHYDE; 5-METHOXY-6-METHYL-PYRIDINE-2-CARBALDEHYDE; 5-METHOXYISOPHTHALALDEHYDE; 5-METHOXYPENTANAL; 5-METHOXYPYRAZINE-2-CARBALDEHYDE; 5-METHOXYPYRIDINE-2-CARBOXALDEHYDE; 5-METHYL-1,3,4-THIADIAZOLE-2-CARBALDEHYDE; 5-METHYL-1,3-BENZOXAZOLE-

2-CARBALDEHYDE; 5-METHYL-1,3-THIAZOLE-2-CARBALDEHYDE; 5-METHYL-1H-INDAZOLE-3-CARBALDEHYDE; 5-METHYL-1H-PYRAZOLE-3-CARBALDEHYDE; 5-METHYL-2-(PROP-2-YN-1-YLOXY)BENZALDEHYDE; 5-METHYL-2-NITROBENZALDEHYDE; 5-METHYL-3-NITROPICOLINALDEHYDE; 5-METHYL-4-(PROPAN-2-YL)-1,3-THIAZOLE-2-CARBALDEHYDE; 5-METHYLFURAN-2-PROPIONALDEHYDE; 5-METHYLHEXANAL; 5-METHYLISOPHTHALALDEHYDE; 5-METHYLISOXAZOLE-3-CARBOXALDEHYDE; 5-METHYLNICOTINALDEHYDE; 5-METHYL-OXAZOLE-2-CARBALDEHYDE; 5-METHYLPYRIDINE-2-CARBOXALDEHYDE; 5-METHYLQUINOLINE-2-CARBALDEHYDE; 5-NITRO-6-METHYL-2-PYRIDINECARBALDEHYDE; 5-NITRONICOTINALDEHYDE; 5-NORBORNENE-2-CARBOXALDEHYDE; 5-OXO-PENTANOIC ACID METHYL ESTER; 5-OXOPENTYL ACETATE; 5-PHENYL-[1,2,4]OXADIAZOLE-3-CARBALDEHYDE; 5-PHENYL-1,3,4-OXADIAZOLE-2-CARBALDEHYDE; 5-PHENYL-1H-PYRAZOLE-3-CARBALDEHYDE; 5-PHENYLISOXAZOLE-3-CARBALDEHYDE; 5-PHENYL-OXAZOLE-2-CARBALDEHYDE; 5-PHENYLPENTANAL; 5-PYRIDIN-3-YL-OXAZOLE-2-CARBALDEHYDE; 5-QUINAZOLINECARBOXALDEHYDE; 5-TERT-BUTYL-1,3,4-OXADIAZOLE-2-CARBALDEHYDE; 5-TERT-BUTYL-1H-PYRAZOLE-3-CARBALDEHYDE; 6-(1-HYDROXY-1-METHYL-ETHYL)-PYRIDINE-3-CARBALDEHYDE; 6-(1-METHYLETHYL)-2-PYRIDINECARBOXALDEHYDE; 6-(1-METHYLETHYL)-3-PYRIDINECARBOXALDEHYDE; 6-(2-FURYL)NICOTINALDEHYDE; 6-(2-HYDROXYPROPAN-2-YL)PICOLINALDEHYDE; 6-(4H-1,2,4-TRIAZOL-4-YL)PYRIDINE-2-CARBOXALDEHYDE; 6-(CHLOROMETHYL)NICOTINALDEHYDE; 6-(CHLOROMETHYL)PYRIDINE-2-CARBALDEHYDE; 6-(DIMETHYLAMINO)-4-METHYLNICOTINALDEHYDE; 6-(DIMETHYLAMINO)NICOTINALDEHYDE; 6-(FLUOROMETHYL)PYRIDINE-2-CARBALDEHYDE; 6-(FURAN-2-YL)PYRIDINE-2-CARBALDEHYDE; 6-(HYDROXYMETHYL)-3-PYRIDINECARBOXALDEHYDE; 6,6-DIMETHOXYHEXANAL; 6,7-DIHYDRO-4H-PYRAZOLO[5,1-C][1,4]OXAZINE-2-CARBALDEHYDE; 6,7-DIHYDRO-4H-PYRAZOLO[5,1-C][1,4]THIAZINE-2-CARBALDEHYDE; 6,7-DIHYDRO-5H-CYCLOPENTA[C]PYRIDINE-3-CARBOXALDEHYDE; 6,7-DIHYDRO-5H-PYRANO[2,3-D]PYRIMIDINE-2-CARBALDEHYDE; 6,7-DIHYDRO-5H-PYRAZOLO[5,1-B][1,3]OXAZINE-2-CARBALDEHYDE; 6,7-DIMETHYL-1H-INDAZOLE-3-CARBALDEHYDE; 6-[ETHYL(METHYL)AMINO]NICOTINALDEHYDE; 6-ACETYLNICOTINALDEHYDE; 6-ACETYLPYRIDINE-2-CARBALDEHYDE; 6-BENZOTHIAZOLECARBOXALDEHYDE; 6-CHLORO-1,2,4-TRIAZINE-5-CARBALDEHYDE; 6-CHLORO-2-FLUORO-3-METHYLBENZALDEHYDE; 6-CHLORO-2-FLUOROPYRIDINE-3-CARBOXALDEHYDE; 6-CHLORO-2-METHOXY-PYRIDINE-3-CARBALDEHYDE; 6-CHLORO-2-METHYLPYRIMIDINE-4-CARBALDEHYDE; 6-CHLORO-3-FORMYL-2-PICOLINE; 6-CHLORO-3-METHOXYPYRIDINE-2-CARBOXALDEHYDE; 6-CHLORO-3-METHYLPYRIDINE-2-CARBOXALDEHYDE; 6-CHLORO-4-FLUORO-PYRIDINE-2-CARBALDEHYDE; 6-CHLORO-4-FLUORO-PYRIDINE-3-CARBALDEHYDE; 6-CHLORO-4-HYDROXY-PYRIDINE-3-CARBALDEHYDE; 6-CHLORO-4-METHOXY-PYRIDINE-2-CARBALDEHYDE; 6-CHLORO-4-METHYLPICOLINALDEHYDE; 6-CHLORO-5-FLUORONICOTINALDEHYDE; 6-CHLORO-5-FLUOROPICOLINALDEHYDE; 6-CHLORO-5-HYDROXY-3-PYRIDINECARBOXALDEHYDE; 6-CHLORO-5-METHOXYPICOLINALDEHYDE; 6-CHLORO-5-METHOXY-PYRIDINE-3-CARBALDEHYDE; 6-CHLORO-5-METHYLNICOTINALDEHYDE; 6-CHLOROHEXANAL; 6-CHLORONICOTINALDEHYDE; 6-CHLOROPYRAZINE-2-CARBALDEHYDE; 6-CHLOROPYRIDAZINE-3-CARBALDEHYDE; 6-CHLOROPYRIDINE-2-CARBALDEHYDE; 6-CHLOROPYRIMIDINE-4-CARBALDEHYDE; 6-CYANOPYRIDINE-2-CARBOXALDEHYDE; 6-CYCLOPROPYL-2-FORMYLPYRIMIDINE; 6-CYCLOPROPYL-PYRIDINE-3-CARBALDEHYDE; 6-DEOXY-D-GALACTOSE; 6-DEOXY-L-TALOSE; 6-DIMETHYLAMINO-PYRIDINE-2-CARBALDEHYDE; 6-ETHOXY-5-FLUOROPYRIDINE-3-CARBALDEHYDE; 6-ETHOXYNICOTINALDEHYDE; 6-ETHOXYPYRIDINE-2-CARBOXALDEHYDE; 6-ETHYL-3-PYRIDINECARBOXALDEHYDE; 6-ETHYNYLPICOLINALDEHYDE; 6-FLUORO-1H-INDAZOLE-5-CARBALDEHYDE; 6-FLUORO-3-(1H)INDAZOLE CARBOXALDEHYDE; 6-FLUORO-3-FORMYL-2-PICOLINE; 6-FLUORO-5-METHOXYNICOTINALDEHYDE; 6-FLUORO-5-METHYLPYRIDINE-2-CARBALDEHYDE; 6-FLUOROBENZO[D]OXAZOLE-2-CARBALDEHYDE; 6-FORMYL NICOTINONITRILE; 6-FORMYL-2-METHYLPYRIDINE-3-BORONIC ACID; 6-FORMYL-2-PYRIDINE CARBOXYLIC ACID METHYL ESTER; 6-FORMYL-4-METHYLPYRIDINE-3-BORONIC ACID; 6-FORMYLFURO[3,2-C]PYRIDINE; 6-FORMYLPYRIDINE-2-BORONIC ACID; 6-FORMYLPYRIDINE-3-BORONIC ACID; 6-HYDROXY-1H-INDAZOLE-3-CARBOXALDEHYDE; 6-HYDROXY-2-METHYLNICOTINALDEHYDE; 6-HYDROXY-2-METHYLPYRIMIDINE-4-CARBALDEHYDE; 6-HYDROXY-2-NAPHTHALDEHYDE; 6-HYDROXY-5-NITRONICOTINALDEHYDE; 6-HYDROXY-5-QUINOLINECARBOXALDEHYDE; 6-HYDROXYISOQUINOLINE-5-CARBALDEHYDE; 6-HYDROXYMETHYL-2-PYRIDINECARBOXALDEHYDE; 6-HYDROXYNAPHTHALENE-1-CARBOXALDEHYDE; 6-HYDROXYNICOTINALDEHYDE; 6-HYDROXYPYRIDAZINE-3-CARBOXALDEHYDE; 6-HYDROXYPYRIDINE-2-CARBOXALDEHYDE; 6-HYDROXYPYRIMIDINE-4-CARBALDEHYDE; 6-HYDROXYQUINOLINE-2-CARBOXALDEHYDE; 6-HYDROXYQUINOLINE-3-CARBOXALDEHYDE; 6-HYDROXYQUINOLINE-4-CARBOXALDEHYDE; 6-HYDROXYQUINOLINE-7-CARBOXALDEHYDE; 6-HYDROXYQUINOLINE-8-CARBOXALDEHYDE; 6-IMIDAZOL-1-YL-HEXANAL; 6-IMIDAZOL-1-YL-PYRIDINE-2-CARBALDEHYDE; 6-METHOXY-2,6-DIMETHYL HEPTANAL; 6-METHOXY-2-METHYLPYRIDINE-3-CARBOXALDEHYDE; 6-METHOXY-2-PYRIDINECARBOXALDEHYDE; 6-METHOXY-3-METHYLPYRIDINE-2-CARBALDEHYDE; 6-METHOXY-3-PYRIDINECARBOXALDEHYDE; 6-METHOXY-5-METHYLNICOTINALDEHYDE; 6-METHOXY-5-METHYLPYRIDINE-2-CARBALDEHYDE; 6-METHOXYPYRIDAZINE-3-CARBALDE-

HYDE; 6-METHYL-1,3-BENZOXAZOLE-2-CARBALDEHYDE; 6-METHYL-2-(PROPAN-2-YL)PYRIMIDINE-4-CARBALDEHYDE; 6-METHYL-2-PROPYLPYRIMIDINE-4-CARBALDEHYDE; 6-METHYL-2-PYRIDINECARBOXALDEHYDE; 6-METHYL-2-QUINOLINECARBOXALDEHYDE; 6-METHYL-3-(1H)INDAZOLE CARBOXALDEHYDE; 6-METHYL-3-CYCLOHEXENE-1-CARBOXALDEHYDE; 6-METHYL-3-NITROPICOLINALDEHYDE; 6-METHYL-5-QUINOLINECARBALDEHYDE; 6-METHYL-BENZO[1,3]DIOXOLE-5-CARBALDEHYDE; 6-METHYLISOVANILLIN; 6-METHYLNICOTINALDEHYDE; 6-METHYLPYRAZINE-2-CARBOXALDEHYDE; 6-METHYLPYRIDAZINE-3-CARBALDEHYDE; 6-METHYLPYRIMIDINE-4-CARBALDEHYDE; 6-METHYLQUINOLINE-8-CARBOXALDEHYDE; 6-NITROPICOLINALDEHYDE; 6-OXO-HEXANOIC ACID ETHYL ESTER; 6-QUINOLINECARBALDEHYDE; 6-TERT-BUTYL-PYRIDINE-3-CARBALDEHYDE; 7,7-DIMETHOXYHEPTANAL; 7,7-DIMETHYL-2-OXOBICYCLO[2.2.1]HEPTANE-1-CARBALDEHYDE; 7,8-DIHYDRO-5H-PYRANO[4,3-B]PYRIDINE-3-CARBALDEHYDE; 7,8-DIHYDRO-5H-PYRANO[4,3-D]PYRIDINE-4-CARBALDEHYDE; 7,8-DIHYDRO-5H-PYRANO[4,3-D]PYRIMIDINE-2-CARBALDEHYDE; 7,8-DIHYDRO-5H-PYRANO[4,3-D]PYRIMIDINE-4-CARBALDEHYDE; 7-ETHYL-1H-INDAZOLE-5-CARBALDEHYDE; 7-FLUORO-1H-INDAZOLE-3-CARBOXALDEHYDE; 7-FLUORO-1H-INDAZOLE-4-CARBALDEHYDE; 7-FLUOROBENZO[D]OXAZOLE-2-CARBALDEHYDE; 7-FLUORONAPHTHALENE-1-CARBOXALDEHYDE; 7-FORMYL-8-QUINOLINOL; 7-HYDROXY-1,3-BENZODIOXOLE-5-CARBOXALDEHYDE; 7-HYDROXY-3-QUINOLINECARBOXALDEHYDE; 7-HYDROXYISOQUINOLINE-8-CARBALDEHYDE; 7-HYDROXYNAPHTHALENE-1-CARBOXALDEHYDE; 7-HYDROXYNAPHTHALENE-2-CARBOXALDEHYDE; 7-HYDROXYQUINOLINE-2-CARBOXALDEHYDE; 7-HYDROXYQUINOLINE-4-CARBOXALDEHYDE; 7-HYDROXYQUINOLINE-5-CARBOXALDEHYDE; 7-HYDROXYQUINOLINE-6-CARBOXALDEHYDE; 7-HYDROXYQUINOLINE-8-CARBALDEHYDE; 7-METHYL-1H-INDAZOLE-3-CARBALDEHYDE; 7-METHYL-1H-INDAZOLE-5-CARBALDEHYDE; 7-METHYL-2-NAPHTHALDEHYDE; 7-METHYLQUINOLINE-3-CARBALDEHYDE; 7-OXO-HEPTANOIC ACID ETHYL ESTER; 7-OXOHEPTYL ACETATE; 8-HYDROXYNAPHTHALENE-1-CARBOXALDEHYDE; 8-HYDROXYNAPHTHALENE-2-CARBOXALDEHYDE; 8-HYDROXYQUINOLINE-2-CARBOXALDEHYDE; 8-HYDROXYQUINOLINE-3-CARBOXALDEHYDE; 8-HYDROXY-QUINOLINE-5-CARBALDEHYDE; 8-HYDROXYQUINOLINE-6-CARBOXALDEHYDE; 8-METHYLQUINOLINE-5-CARBALDEHYDE; 8-OXOOCTANENITRILE; 8-QUINOLINECARBALDEHYDE; 9-DECENAL; A,A-DIMETHYL-2-PYRIDINEACETALDEHYDE; ACETALDEHYDE; ACETALDEHYDE, (3-METHYLPHENOXY)-; ACETALDEHYDE, 2-NITRO-; ACETALDEHYDE, IODO-; ACETALDEHYDE, PARAMETHYL PHENOXY; ACETIC ACID 2-FORMYL-PHENYL ESTER; ACETIC ACID 3-METHYL-6-OXO-HEX-2-ENYL ESTER; ACETYLOXYACETALDEHYDE; ADIPALDEHYDE; A-FORMYL-2-PYRIDINEACETONITRILE; A-FORMYL-3-PYRIDINEACETONITRILE; A-FORMYL-4-PYRIDINEACETONITRILE; ALDENAL C-11; ALDOL; ALPHA-CYCLOCIRAL; A-METHYL-3-PYRIDINEPROPANAL; A-METHYL-4-PYRIDINEACETALDEHYDE; BENZALDEHYDE; BENZALDEHYDE ON POLYSTYRENE; BENZALDEHYDE-180; BENZENE-1,2,4-TRICARBALDEHYDE; BENZENE-1,3,5-TRICARBALDEHYDE; BENZENEACETALDEHYDE, 2-FLUORO-4-METHOXY-; BENZENEACETALDEHYDE, A,A-DIFLUORO-; BENZENEACETALDEHYDE, A-FLUORO-; BENZENEBUTANAL, 2-METHYL-; BENZENEBUTANAL, 4-FLUORO-; BENZENEBUTANAL, 4-METHYL-; BENZO[B]FURAN-7-CARBALDEHYDE; BENZO[B]THIOPHENE-4-CARBALDEHYDE; BENZO[B]THIOPHENE-7-CARBALDEHYDE; BENZO[D]ISOXAZOLE-5-CARBALDEHYDE; BENZO[D]OXAZOLE-6-CARBALDEHYDE; BENZONITRILE, 4-(2-OXOETHYL)-; BENZONITRILE, 4-FORMYL-3-HYDROXY-; BENZOOXAZOLE-2-CARBALDEHYDE; BENZYLGLYOXYLATE; BENZYLOXYACETALDEHYDE; BETA-CYANOPROPIONALDEHYDE; BETAINE ALDEHYDE; BETAINE ALDEHYDE CHLORIDE; BICYCLO[2,2,1]HEPTANE-2-CARBOXALDEHYDE; BICYCLO[4.2.0]OCTA-1,3,5-TRIENE-7-CARBALDEHYDE; BROMOACETALDEHYDE; BUTANAL, 2,2-DIETHYL-; BUTANAL, 3-METHOXY-3-METHYL-; BUTYL GLYOXYLATE; BUTYLMALONDIALDEHYDE; BUTYRALDEHYDE; BUTYRALDEHYDE,-BTA-BROMO-ALPHA-OXO-; CAMPHOLENIC ALDEHYDE; CHLORAL; CHLOROACETALDEHYDE; CHROMAN-3-CARBALDEHYDE; CHROMAN-6-CARBALDEHYDE; CHROMAN-8-CARBALDEHYDE; CIS-3-HEXENYL OXY-ACETALDEHYDE; CIS-4-DECENAL; CIS-4-HEPTENAL; CIS-6-NONENAL; CIS-7-DECEN-1-AL; CIS-8-UNDECEN-1-AL; CITRONELLAL; COUMARIN-6-CARBOXALDEHYDE; CYCLOBUTANECARBOXALDEHYDE; CYCLOBUTYL(PHENYL)ACETALDEHYDE; CYCLOBUTYLACETALDEHYDE; CYCLOHEPTANECARBALDEHYDE; CYCLOHEXANECARBOXALDEHYDE; CYCLOHEXANONE-4-CARBOXALDEHYDE; CYCLOOCTANECARBALDEHYDE; CYCLOPENTANECARBALDEHYDE; CYCLOPENTYL ACETALDEHYDE; CYCLOPENTYLMALONDIALDEHYDE; CYCLOPROPANECARBOXALDEHYDE; CYCLOPROPANECARBOXALDEHYDE, 2-PHENYL-, (1R,2R)-; CYCLOPROPYLMALONDIALDEHYDE; DECANAL; DIAZOACETALDEHYDE; DICHLOROACETALDEHYDE; DICHLOROACETALDEHYDE HYDRATE; DIMETHYLMALONDIALDEHYDE; DI-N-BUTYLACETALDEHYDE; ETHOXYACETALDEHYDE; ETHYL 1-FORMYLCYCLOBUTANECARBOXYLATE; ETHYL 1-FORMYLCYCLOPENTANECARBOXYLATE; ETHYL 1-FORMYLCYCLOPROPANECARBOXYLATE; ETHYL 2-[(2-OXOETHYL)SULFANYL]ACETATE; ETHYL 2-CHLORO-3-OXOPROPANOATE; ETHYL 2-FORMYL-1-CYCLOPROPANECARBOXYLATE; ETHYL 2-FORMYLBUTANOATE; ETHYL 3-FORMYL-1H-PYRAZOLE-5-CARBOXYLATE; ETHYL 4-OXOBUTANOATE; ETHYL ALLYL FORMYLMETHYLCARBAMATE; ETHYL GLYOXALATE; ETHYL-2-FORMYL-3-OXO-PROPIONATE; ETHYLMALONDIALDEHYDE; FLUOROACETALDEHYDE; FLUOROMALONALDEHYDE; FORMALDEHYDE/GLUTARALDEHYDE; FURO[2,3-C]PYRIDINE-5-CARBALDEHYDE; FURO[3,2-B]PYRIDINE-6-CARBALDEHYDE; GLUTARALDEHYDE; GLUTARALDEHYDEMONOACETAL; GLYCIDALDEHYDE; GLYCOLALDEHYDE; GLYOXAL; GLYOXAL

DIETHYL ACETAL; GLYOXAL DIMETHYL ACETAL; HEPT-6-ENAL; HEPTALDEHYDE; HEX-4-YNAL; HEX-5-ENAL; HEXAHYDRO-4,7-METHANOINDAN-1-CARBOXALDEHYDE; HEXANAL; HEXYL GLYOXYLATE; HYDROXYPIVALDEHYDE; HYDROXYPROPANEDIAL; IMIDAZO[1,2-A]PYRIMIDINE-7-CARBALDEHYDE; IMIDAZO[1,2-B]PYRIDAZINE-6-CARBOXALDEHYDE; IMIDAZO[1,5-A]PYRIDINE-3-CARBALDEHYDE; IMIDAZO[2,1,5-CD]INDOLIZINE-2-CARBOXALDEHYDE; IMIDAZOL-1-YL-ACETALDEHYDE; INDAN-5-CARBALDEHYDE; ISOBUTYRALDEHYDE; ISOPHTHALALDEHYDE; ISOPROPYL GLYOXYLATE; ISOPROPYLMALONDIALDEHYDE; ISOQUINOLINE-1-CARBALDEHYDE; ISOQUINOLINE-3-CARBALDEHYDE; ISOQUINOLINE-4-CARBALDEHYDE; ISOQUINOLINE-5-CARBALDEHYDE; ISOQUINOLINE-6-CARBALDEHYDE; ISOQUINOLINE-7-CARBALDEHYDE; ISOQUINOLINE-8-CARBALDEHYDE; ISOVALERALDEHYDE; ISOXAZOLE-3-CARBALDEHYDE; ISOXAZOLO[4,5-C]PYRIDINE-4-CARBALDEHYDE; MALONDIALDEHYDE; METHOXYACETALDEHYDE; METHYL 2-[(2-OXOETHYL)SULFANYL]ACETATE; METHYL 2-[(3-OXOPROPYL)SULFANYL]ACETATE; METHYL 2-CHLORO-2-FORMYLACETATE; METHYL 2-FORMYLBENZOATE; METHYL 2-FORMYLNICOTINATE; METHYL 2-FORMYLPYRIDINE-4-CARBOXYLATE; METHYL 2-METHYL-3-OXOPROPIONATE; METHYL 3-[(2-OXOETHYL)SULFANYL]PROPANOATE; METHYL 3-FORMYL-2-PYRIDINECARBOXYLATE; METHYL 3-FORMYLBENZOATE; METHYL 3-OXO-PROPANOATE; METHYL 4-FORMYLBENZOATE; METHYL 4-FORMYLPYRIDINE-2-CARBOXYLATE; METHYL 4-FORMYLPYRIMIDINE-2-CARBOXYLATE; METHYL 5-FORMYLNICOTINATE; METHYL 5-FORMYLPICOLINATE; METHYL 5-FORMYLPYRIMIDINE-2-CARBOXYLATE; METHYL 6-FORMYLNICOTINATE; METHYL 6-OXOHEXANOATE; METHYL 7-OXOHEPTANOATE; METHYL DIFORMYLACETATE; METHYL GLYOXYLATE; METHYLMALONDIALDEHYDE; MONO METHOXY PEG ALDEHYDE; MORPHOLIN-4-YL-ACETALDEHYDE; MORPHOLIN-4-YL-ACETALDEHYDE HCL; M-TOLU-ALDEHYDE; N,N-DIMETHYL-2-[METHYL(2-OXOETHYL)AMINO]ACETAMIDE; N,N-DIMETHYL-2-[METHYL(3-OXOPROPYL)AMINO]ACETAMIDE; N-BOC-(METHYLAMINO)ACETALDEHYDE; NITROACETALDEHYDE POTASSIUM SALT; NITROMALONALDEHYDE; NITROMALONALDEHYDE SODIUM SALT; NITROMALONALDEHYDE SODIUM SALT HYDRATE; NON-8-ENAL; NONANAL; O-ANISALDEHYDE; OCT-7-ENAL; OCTANAL; OCTANAL, 8-CHLORO-; OCTANEDIAL; OCTYL OXY-ACETALDEHYDE; O-PHTHALALDEHYDE; OXAZOLE-2-CARBALDEHYDE; OXOPENTANAL(4-); P-ANISALDEHYDE; P-AZIDOBENZALDEHYDE; PENT-4-YNAL; PENTAFLUOROPROPIONALDEHYDE HYDRATE; PENTANAL, 5-BROMO-; PENTANOIC ACID, 5-OXO-, ETHYL ESTER; PHENOXY ACETALDEHYDE; PHENYLACETALDEHYDE; PHENYLETHYL OXYACETALDEHYDE; PHENYLGLYOXAL; PHENYLGLYOXAL MONOHYDRATE; PHENYLPROPARGYL ALDEHYDE; P-HYDROXY PHENYL BUTANONE; PINONALDEHYDE; PIPERONAL; PIPERONYL FORMALDEHYDE; P-METHYLPHENYLACETALDEHYDE; PROPANAL, 3-BROMO-; PROPANOIC ACID, 2-METHYL-3-OXO-, METHYL ESTER, (R)—; PROPANOIC ACID, 2-METHYL-3-OXO-, METHYL ESTER, (S)—; PROPIONALDEHYDE; PROPYLMALONDIALDEHYDE; PROPYNAL; P-TOLUALDEHYDE; PYRAZINE-2,6-DICARBALDEHYDE; PYRAZINE-2-CARBALDEHYDE; PYRAZOLO[1,5-A]PYRIDINE-2-CARBALDEHYDE; PYRIDAZINE-3,6-DICARBALDEHYDE; PYRIDAZINE-3-CARBALDEHYDE; PYRIDAZINE-4-CARBALDEHYDE; PYRIDINE-3,5-DICARBOXALDEHYDE; PYRIDINE-4-ALDEHYDE HYDRATE; PYRIDINIUM, 2-FORMYL-5-HYDROXY-1-PROPYL-, INNER SALT; PYRIDO[2,3-B]PYRAZINE-3-CARBALDEHYDE; PYRIDO[2,3-B]PYRAZINE-6-CARBALDEHYDE; PYRIDO[2,3-B]PYRAZINE-7-CARBOXALDEHYDE; PYRIDO[2,3-E]PYRAZINE-8-CARBALDEHYDE; PYRIDOXAL; PYRIMIDINE-2,4,6-TRICARBALDEHYDE; PYRIMIDINE-2,4-DICARBALDEHYDE; PYRIMIDINE-4,6-DICARBALDEHYDE; PYRIMIDINE-4-CARBOXALDEHYDE; PYRIMIDINE-5-CARBOXALDEHYDE; PYRROLO[1,2-C]PYRIMIDINE-1-CARBOXALDEHYDE; PYRUVIC ALDEHYDE; QUINAZOLINE-2-CARBALDEHYDE; QUINAZOLINE-4-CARBALDEHYDE; QUINAZOLINE-6-CARBALDEHYDE; QUINOLINE-5-CARBALDEHYDE; QUINOLINE-7-CARBALDEHYDE; QUINOXALINE-5-CARBALDEHYDE; QUINOXALINE-6-CARBALDEHYDE; QUINUCLIDINE-2-CARBALDEHYDE; QUINUCLIDINE-3-CARBALDEHYDE; QUINUCLIDINE-4-CARBALDEHYDE; S-2-METHYLBUTANAL; SALICYLALDEHYDE; SALICYLALDEHYDE, SODIUM SALT; SODIUM GLYOXYLATE; SODIUM GLYOXYLATE MONOHYDRATE; SPIROCYCLOHEXYLBUTANE-1,3-DIONE; SUCCINALDEHYDE; TEREPHTHALALDEHYDE; TERT-BUTYL 4-OXOBUTANOATE; TERT-BUTYL 5-OXOPENTANOATE; TERT-BUTYLGLYOXAL; TERT-BUTYLMALONDIALDEHYDE; TETRAHYDRO-2,5-DIMETHOXY-5-METHYLFURAN-3-CARBALDEHYDE; TETRAHYDRO-2-FURANCARBOXALDEHYDE; TETRAHYDRO-2H-PYRAN-2-CARBALDEHYDE; TETRAHYDROFURAN-3-CARBOXALDEHYDE; TETRAHYDRO-PYRAN-3-CARBALDEHYDE; TETRAHYDROPYRAN-4-YLACETALDEHYDE; TETRAHYDRO-THIOPYRAN-3-CARBALDEHYDE; TETRAHYDROTHIOPYRAN-4-CARBALDEHYDE; TRANS-1,4-CYCLOHEXANE DICARBOXALDEHYDE; TRANS-2,2-DIMETHYL-4-HEPTENAL; TRANS-4-DECEN-1-AL; TRANS-4-ETHYL-CYCLOHEXANECARBALDEHYDE; TRANS-4-HEPTENAL; TRIFLUOROACETALDEHYDE; TRIFLUOROACETALDEHYDE HYDRATE; TRIFLUOROPYRUVIC ALDEHYDE; TRIFORMYLMETHANE; TRIMETHYLACETALDEHYDE; TRIPLAL; TRIVERTAL; UNDECANAL; VALERALDEHYDE; VANILLIN; Halogens: (2-BROMO-5-FORMYL-IMIDAZOL-1-YL)-ACETIC ACID METHYL ESTER; (2-CHLORO-3-FORMYL-INDOL-1-YL)-ACETIC ACID METHYL ESTER; (2-CHLORO-5-FORMYL-IMIDAZOL-1-YL)-ACETIC ACID METHYL ESTER; (2E)-2-BROMO-3-(DIMETHYLAMINO)-2-PROPENAL; (2E)-3-(4-BROMOPHENYL)-3-CHLOROACRYLALDEHYDE; (2E)-3-CHLORO-3-(2,4-DIMETHYLPHENYL)-2-METHYLACRYLALDEHYDE; (2Z)-2-CHLORO-2-BUTENAL; (2Z)-3-(4-BROMOPHENYL)-3-CHLOROACRYLALDEHYDE; (4-BROMO-1H-PYRAZOL-1-YL)ACETALDEHYDE; (4-BROMO-3,5-DIMETHYL-1H-PYRAZOL-1-YL)ACETALDEHYDE; (4-CHLORO-1H-PYRAZOL-1-YL)ACETALDEHYDE;

(4-CHLORO-3,5-DIMETHYL-1H-PYRAZOL-1-YL)-ACETALDEHYDE; (4-CHLORO-5-FORMYL-2-OXO-THIAZOL-3-YL)-ACETIC ACID ETHYL ESTER; (4-IODO-1H-PYRAZOL-1-YL)ACETALDEHYDE; (4-IODO-3,5-DIMETHYL-1H-PYRAZOL-1-YL)ACETALDEHYDE; (8-BROMO-3-METHYL-2,6-DIOXO-1,2,3,6-TETRAHYDRO-7H-PURIN-7-YL)ACETALDEHYDE; (E)-3-CHLORO-2-METHYL-3-(2-THENYL) ACROLEIN; (Z)-2-(2-(4-BROMOPHENYL)HYDRAZONO)-2-CHLOROACETALDEHYDE; (Z)-2-BROMO-4-OXO-BUT-2-ENOIC ACID ETHYL ESTER; (Z)-3-CHLORO-2-METHYL-3-(2-THENYL) ACROLEIN; (Z)-3-CHLORO-2-METHYL-3-PHENYL-ACRYLALDEHYDE; (Z)-3-CHLORO-3-(3-CHLOROPHENYL)ACRYLALDEHYDE; (Z)-3-CHLORO-3-(4-FLUOROPHENYL)ACRYLALDEHYDE; (Z)-3-CHLORO-3-(4-METHOXYPHENYL)ACRYLALDEHYDE; (Z)-3-CHLORO-3-(4-NITROPHENYL)ACRYLALDEHYDE; (Z)-3-CHLORO-3-(THIOPHEN-3-YL)ACRYLALDEHYDE; (Z)-3-CHLORO-3-PHENYLACRYLALDEHYDE; (Z)-3-CHLORO-3-P-TOLYLACRYLALDEHYDE; (Z)-3-HYDROXY-2-IODOACROLEIN; (Z)-N-(4-CHLORO-3-ETHYL-5-FORMYLTHIAZOL-2(3H)-YLIDENE)BENZENESULFONAMIDE; 1-(([(4-BROMOTHIOPHEN-2-YL)METHYL](METHYL)AMINO)METHYL)CYCLOHEXANE-1-CARBALDEHYDE; 1-(([(4-BROMOTHIOPHEN-2-YL)METHYL](METHYL)AMINO)METHYL)CYCLOPENTANE-1-CARBALDEHYDE; 1-((6-CHLOROIMIDAZO[1,2-A]PYRIDIN-2-YL)METHYL)PIPERIDINE-2-CARBALDEHYDE; 1-((6-CHLOROIMIDAZO[1,2-A]PYRIDIN-2-YL)METHYL)PIPERIDINE-3-CARBALDEHYDE; 1-((6-CHLOROIMIDAZO[1,2-A]PYRIDIN-2-YL)METHYL)PIPERIDINE-4-CARBALDEHYDE; 1-((BENZYLOXY)METHYL)-4-IODO-1H-IMIDAZOLE-5-CARBALDEHYDE; 1-(2-BROMO-ALLYL)-1H-PYRAZOLE-4-CARBALDEHYDE; 1-(2-BROMOPHENYL)-3,5-DICHLORO-1H-PYRAZOLE-4-CARBOXALDEHYDE; 1-(2-BROMOPHENYL)-3-TERT-BUTYL-5-CHLORO-1H-PYRAZOLE-4-CARBALDEHYDE; 1-(2-BROMOPHENYL)-5-CHLORO-1H-PYRAZOLE-4-CARBOXALDEHYDE; 1-(2-BROMOPHENYL)-5-CHLORO-3-(DIFLUOROMETHYL)-1H-PYRAZOLE-4-CARBALDEHYDE; 1-(2-BROMOPHENYL)-5-CHLORO-3-(METHOXYMETHYL)-1H-PYRAZOLE-4-CARBALDEHYDE; 1-(2-BROMOPHENYL)-5-CHLORO-3-(PROPAN-2-YL)-1H-PYRAZOLE-4-CARBALDEHYDE; 1-(2-BROMOPHENYL)-5-CHLORO-3-ETHYL-1H-PYRAZOLE-4-CARBALDEHYDE; 1-(2-BROMOPHENYL)-5-CHLORO-3-METHYL-1H-PYRAZOLE-4-CARBALDEHYDE; 1-(2-BROMOPHENYL)-5-CHLORO-3-PROPYL-1H-PYRAZOLE-4-CARBALDEHYDE; 1-(2-BROMOPROP-2-EN-1-YL)-3,5-DIMETHYL-1H-PYRAZOLE-4-CARBALDEHYDE; 1-(2-BROMOPROP-2-EN-1-YL)PIPERIDINE-2-CARBALDEHYDE; 1-(2-BROMOPROP-2-EN-1-YL)PIPERIDINE-3-CARBALDEHYDE; 1-(2-BROMOPROP-2-EN-1-YL)PIPERIDINE-4-CARBALDEHYDE; 1-(2-CHLORO-4-FLUOROPHENYL)-3,5-DIBROMO-1H-PYRAZOLE-4-CARBOXALDEHYDE; 1-(2-CHLORO-4-FLUOROPHENYL)-3,5-DICHLORO-1H-PYRAZOLE-4-CARBOXALDEHYDE; 1-(2-CHLORO-5-FLUOROPHENYL)-3,5-DIBROMO-1H-PYRAZOLE-4-CARBOXALDEHYDE; 1-(2-CHLORO-5-FLUOROPHENYL)-3,5-DICHLORO-1H-PYRAZOLE-4-CARBOXALDEHYDE; 1-(2-CHLORO-ALLYL)-1H-PYRAZOLE-4-CARBALDEHYDE; 1-(2-CHLOROPHENYL)-3,5-DIBROMO-1H-PYRAZOLE-4-CARBOXALDEHYDE; 1-(2-CHLOROPHENYL)-3,5-DICHLORO-1H-PYRAZOLE-4-CARBOXALDEHYDE; 1-(2-CHLOROPROP-2-EN-1-YL)-3,5-DIMETHYL-1H-PYRAZOLE-4-CARBALDEHYDE; 1-(2-CHLOROPROP-2-EN-1-YL)PIPERIDINE-2-CARBALDEHYDE; 1-(2-CHLOROPROP-2-EN-1-YL)PIPERIDINE-3-CARBALDEHYDE; 1-(2-CHLOROPROP-2-EN-1-YL)PIPERIDINE-4-CARBALDEHYDE; 1-(3-BROMOPHENYL)-3,5-DICHLORO-1H-PYRAZOLE-4-CARBOXALDEHYDE; 1-(3-BROMOPHENYL)-3-TERT-BUTYL-5-CHLORO-1H-PYRAZOLE-4-CARBALDEHYDE; 1-(3-BROMOPHENYL)-5-CHLORO-1H-PYRAZOLE-4-CARBOXALDEHYDE; 1-(3-BROMOPHENYL)-5-CHLORO-3-(DIFLUOROMETHYL)-1H-PYRAZOLE-4-CARBALDEHYDE; 1-(3-BROMOPHENYL)-5-CHLORO-3-(METHOXYMETHYL)-1H-PYRAZOLE-4-CARBALDEHYDE; 1-(3-BROMOPHENYL)-5-CHLORO-3-(PROPAN-2-YL)-1H-PYRAZOLE-4-CARBALDEHYDE; 1-(3-BROMOPHENYL)-5-CHLORO-3-ETHYL-1H-PYRAZOLE-4-CARBALDEHYDE; 1-(3-BROMOPHENYL)-5-CHLORO-3-METHYL-1H-PYRAZOLE-4-CARBALDEHYDE; 1-(3-BROMOPHENYL)-5-CHLORO-3-PROPYL-1H-PYRAZOLE-4-CARBALDEHYDE; 1-(3-CHLORO-4-FLUOROPHENYL)-3,5-DIBROMO-1H-PYRAZOLE-4-CARBOXALDEHYDE; 1-(3-CHLORO-4-FLUOROPHENYL)-3,5-DICHLORO-1H-PYRAZOLE-4-CARBOXALDEHYDE; 1-(3-CHLOROPHENYL)-3,5-DIBROMO-1H-PYRAZOLE-4-CARBOXALDEHYDE; 1-(3-CHLOROPHENYL)-3,5-DICHLORO-1H-PYRAZOLE-4-CARBOXALDEHYDE; 1-(4-BROMOPHENYL)-3,5-DICHLORO-1H-PYRAZOLE-4-CARBOXALDEHYDE; 1-(4-BROMOPHENYL)-5-CHLORO-1H-PYRAZOLE-4-CARBOXALDEHYDE; 1-(4-BROMOPHENYL)-5-CHLORO-2-(DIMETHYLAMINO)-1H-IMIDAZOLE-4-CARBALDEHYDE; 1-(4-BROMOPHENYL)-5-CHLORO-3-(DIFLUOROMETHYL)-1H-PYRAZOLE-4-CARBALDEHYDE; 1-(4-BROMOPHENYL)-5-CHLORO-3-(METHOXYMETHYL)-1H-PYRAZOLE-4-CARBALDEHYDE; 1-(4-BROMOPHENYL)-5-CHLORO-3-(PROPAN-2-YL)-1H-PYRAZOLE-4-CARBALDEHYDE; 1-(4-BROMOPHENYL)-5-CHLORO-3-ETHYL-1H-PYRAZOLE-4-CARBALDEHYDE; 1-(4-BROMOPHENYL)-5-CHLORO-3-METHYL-1H-PYRAZOLE-4-CARBALDEHYDE; 1-(4-BROMOPHENYL)-5-CHLORO-3-PROPYL-1H-PYRAZOLE-4-CARBALDEHYDE; 1-(4-CHLOROPHENYL)-3,5-DIBROMO-1H-PYRAZOLE-4-CARBOXALDEHYDE; 1-(4-CHLOROPHENYL)-3,5-DICHLORO-1H-PYRAZOLE-4-CARBOXALDEHYDE; 1-(BUTAN-2-YL)-3-TERT-BUTYL-5-CHLORO-1H-PYRAZOLE-4-CARBALDEHYDE; 1-(BUTAN-2-YL)-5-CHLORO-3-(METHOXYMETHYL)-1H-PYRAZOLE-4-CARBALDEHYDE; 1-(BUTAN-2-YL)-5-CHLORO-3-(PROPAN-2-YL)-1H-PYRAZOLE-4-CARBALDEHYDE; 1-(BUTAN-2-YL)-5-CHLORO-3-(TRIFLUOROMETHYL)-1H-PYRAZOLE-4-CARBALDEHYDE; 1-(BUTAN-2-YL)-5-CHLORO-3-CYCLOPROPYL-1H-PYRAZOLE-4-CARBALDEHYDE; 1-(BUTAN-2-YL)-5-CHLORO-3-ETHYL-1H-PYRAZOLE-4-

CARBALDEHYDE; 1-(BUTAN-2-YL)-5-CHLORO-3-METHYL-1H-PYRAZOLE-4-CARBALDEHYDE; 1-(BUTAN-2-YL)-5-CHLORO-3-PHENYL-1H-PYRAZOLE-4-CARBALDEHYDE; 1-(BUTAN-2-YL)-5-CHLORO-3-PROPYL-1H-PYRAZOLE-4-CARBALDEHYDE; 1-(PHENYLSULFONYL)-2-IODO-4-AZAINDOLE-6-CARBOXALDEHYDE; 1-(PHENYLSULFONYL)-2-IODO-7-AZAINDOLE-5-CARBALDEHYDE; 1-(PHENYLSULPHONYL)-2-IODO-7-AZAINDOLE-6-CARBALDEHYDE; 1,3-BIS(2,4-DIFLUOROPHENYL)-5-BROMO-1H-PYRAZOLE-4-CARBOXALDEHYDE; 1,3-BIS(2,5-DIFLUOROPHENYL)-5-BROMO-1H-PYRAZOLE-4-CARBOXALDEHYDE; 1,3-BIS(2-CHLOROPHENYL)-5-BROMO-1H-PYRAZOLE-4-CARBOXALDEHYDE; 1,3-BIS(2-FLUOROPHENYL)-5-BROMO-1H-PYRAZOLE-4-CARBOXALDEHYDE; 1,3-BIS(2-FLUOROPHENYL)-5-CHLORO-1H-PYRAZOLE-4-CARBOXALDEHYDE; 1,3-BIS(3,4-DIFLUOROPHENYL)-5-BROMO-1H-PYRAZOLE-4-CARBOXALDEHYDE; 1,3-BIS(3,5-DIFLUOROPHENYL)-5-BROMO-1H-PYRAZOLE-4-CARBOXALDEHYDE; 1,3-BIS(3-CHLOROPHENYL)-5-BROMO-1H-PYRAZOLE-4-CARBOXALDEHYDE; 1,3-BIS(3-FLUOROPHENYL)-5-CHLORO-1H-PYRAZOLE-4-CARBOXALDEHYDE; 1,3-BIS(4-FLUOROPHENYL)-5-BROMO-1H-PYRAZOLE-4-CARBOXALDEHYDE; 1,3-BIS(4-FLUOROPHENYL)-5-CHLORO-1H-PYRAZOLE-4-CARBOXALDEHYDE; 1,3-DI-TERT-BUTYL-5-CHLORO-1H-PYRAZOLE-4-CARBALDEHYDE; 1-[(3-BROMOTHIOPHEN-2-YL)METHYL]-3,5-DIMETHYL-1H-PYRAZOLE-4-CARBALDEHYDE; 1-[(3-BROMOTHIOPHEN-2-YL)METHYL]PIPERIDINE-2-CARBALDEHYDE; 1-[(3-BROMOTHIOPHEN-2-YL)METHYL]PIPERIDINE-3-CARBALDEHYDE; 1-[(3-BROMOTHIOPHEN-2-YL)METHYL]PIPERIDINE-4-CARBALDEHYDE; 1-[(3-CHLORO-1-BENZOTHIOPHEN-2-YL)METHYL]PIPERIDINE-2-CARBALDEHYDE; 1-[(3-CHLORO-1-BENZOTHIOPHEN-2-YL)METHYL]PIPERIDINE-3-CARBALDEHYDE; 1-[(3-CHLORO-1-BENZOTHIOPHEN-2-YL)METHYL]PIPERIDINE-4-CARBALDEHYDE; 1-[(4-BROMOTHIOPHEN-2-YL)METHYL]-3,5-DIMETHYL-1H-PYRAZOLE-4-CARBALDEHYDE; 1-[(4-BROMOTHIOPHEN-2-YL)METHYL]PIPERIDINE-2-CARBALDEHYDE; 1-[(4-BROMOTHIOPHEN-2-YL)METHYL]PIPERIDINE-3-CARBALDEHYDE; 1-[(4-BROMOTHIOPHEN-2-YL)METHYL]PIPERIDINE-4-CARBALDEHYDE; 1-[(5-CHLORO-1,3-DIMETHYL-1H-PYRAZOL-4-YL)METHYL]PIPERIDINE-2-CARBALDEHYDE; 1-[(5-CHLORO-1,3-DIMETHYL-1H-PYRAZOL-4-YL)METHYL]PIPERIDINE-3-CARBALDEHYDE; 1-[(5-CHLORO-1,3-DIMETHYL-1H-PYRAZOL-4-YL)METHYL]PIPERIDINE-4-CARBALDEHYDE; 1-[(5-CHLORO-1-METHYL-1H-IMIDAZOL-2-YL)METHYL]-3,5-DIMETHYL-1H-PYRAZOLE-4-CARBALDEHYDE; 1-[4-(3-CHLORO-2-THIENYL)-6-METHYL-2-PYRIMIDINYL]-1H-PYRROLE-2-CARBALDEHYDE; 11-CHLORO-13-OXO-8-OXA-1,10-DIAZATRICYCLO[7.4.0.02,7]TRIDECA-2(7),3,5,9,11-PENTAENE-12-CARBALDEHYDE; 11-CHLORO-13-OXO-8-THIA-1,10-DIAZATRICYCLO[7.4.0.02,7]TRIDECA-2(7),3,5,9,11-PENTAENE-12-CARBALDEHYDE; 1-ACETYL-3-CHLORO-1H-INDOLE-2-CARBOXALDEHYDE; 1-ALLYL-2-CHLORO-1H-INDOLE-3-CARBALDEHYDE; 1-BENZYL-2-BROMO-1H-IMIDAZOLE-5-CARBALDEHYDE; 1-BENZYL-2-CHLORO-1H-IMIDAZOLE-5-CARBALDEHYDE; 1-BENZYL-3-TERT-BUTYL-5-CHLORO-1H-PYRAZOLE-4-CARBALDEHYDE; 1-BENZYL-4-IODO-1H-PYRROLE-2-CARBALDEHYDE; 1-BENZYL-5-CHLORO-2,3,6,7-TETRAHYDRO-1H-AZEPINE-4-CARBALDEHYDE HYDROCHLORIDE; 1-BENZYL-5-CHLORO-3-(DIFLUOROMETHYL)-1H-PYRAZOLE-4-CARBALDEHYDE; 1-BENZYL-5-CHLORO-3-(METHOXYMETHYL)-1H-PYRAZOLE-4-CARBALDEHYDE; 1-BENZYL-5-CHLORO-3-(PROPAN-2-YL)-1H-PYRAZOLE-4-CARBALDEHYDE; 1-BENZYL-5-CHLORO-3-(TRIFLUOROMETHYL)-1H-PYRAZOLE-4-CARBALDEHYDE; 1-BENZYL-5-CHLORO-3-ETHYL-1H-PYRAZOLE-4-CARBALDEHYDE; 1-BENZYL-5-CHLORO-3-METHYL-1H-PYRAZOLE-4-CARBALDEHYDE; 1-BENZYL-5-CHLORO-3-PROPYL-1H-PYRAZOLE-4-CARBALDEHYDE; 1-BENZYL-5-CHLORO-6-OXO-1,6-DIHYDRO-3-PYRIDINECARBALDEHYDE; 1-BOC-2-CHLORO-3-FORMYL-INDOLE; 1-BOC-4-CHLORO-5-FORMYL-3,6-DIHYDRO-2H-PYRIDINE; 1-BUTYL-3-TERT-BUTYL-5-CHLORO-1H-PYRAZOLE-4-CARBALDEHYDE; 1-BUTYL-4-CHLORO-3-METHYL-1H-PYRAZOLE-5-CARBALDEHYDE; 1-BUTYL-5-CHLORO-3-(DIFLUOROMETHYL)-1H-PYRAZOLE-4-CARBALDEHYDE; 1-BUTYL-5-CHLORO-3-(METHOXYMETHYL)-1H-PYRAZOLE-4-CARBALDEHYDE; 1-BUTYL-5-CHLORO-3-(PROPAN-2-YL)-1H-PYRAZOLE-4-CARBALDEHYDE; 1-BUTYL-5-CHLORO-3-(TRIFLUOROMETHYL)-1H-PYRAZOLE-4-CARBALDEHYDE; 1-BUTYL-5-CHLORO-3-CYCLOPROPYL-1H-PYRAZOLE-4-CARBALDEHYDE; 1-BUTYL-5-CHLORO-3-ETHYL-1H-PYRAZOLE-4-CARBALDEHYDE; 1-BUTYL-5-CHLORO-3-METHYL-1H-PYRAZOLE-4-CARBALDEHYDE; 1-BUTYL-5-CHLORO-3-PHENYL-1H-PYRAZOLE-4-CARBALDEHYDE; 1-BUTYL-5-CHLORO-3-PROPYL-1H-PYRAZOLE-4-CARBALDEHYDE; 1-BUTYL-6-CHLORO-5-FORMYL-4-METHYL-2-OXO-1,2-DIHYDRO-PYRIDINE-3-CARBONITRILE; 1-CHLORO-2-FORMYL-3-METHYL-BENZO[4,5]IMIDAZO[1,2-A]PYRIDINE-4-CARBONITRILE; 1-CHLORO-3,4-DIHYDRO-2-NAPHTHALENECARBALDEHYDE; 1-CHLORO-5,7-DIMETHYL-3,4-DIHYDRO-NAPHTHALENE-2-CARBALDEHYDE; 1-CHLORO-5-METHOXY-3,4-DIHYDRO-NAPHTHALENE-2-CARBALDEHYDE; 1-CHLORO-6,7-DIMETHOXY-3,4-DIHYDRO-NAPHTHALENE-2-CARBALDEHYDE; 1-CHLORO-6-METHOXY-3,4-DIHYDRO-NAPHTHALENE-2-CARBALDEHYDE; 1-CHLORO-7-METHOXY-3,4-DIHYDRO-NAPHTHALENE-2-CARBALDEHYDE; 1-CHLORO-FORMYL-3H-BENZO[F]CHROMENE; 1H-IMIDAZOLE-4-BROMO-2-CARBOXYALDEHYDE; 1H-INDOLE-1-CARBOXYLIC ACID, 3-BROMO-4-FORMYL-, 1,1-DIMETHYLETHYL ESTER; 1H-INDOLE-1-CARBOXYLIC ACID, 4-FORMYL-3-IODO-, 1,1-DIMETHYLETHYL ESTER; 1H-INDOLE-3-ACETALDEHYDE, 2-IODO-1-(PHENYLSULFONYL)-; 1H-INDOLE-3-ACETALDEHYDE, 2-IODO-1-METHYL-; 1H-INDOLE-3-CARBOXALDEHYDE, 2-CHLORO-5-METHOXY-1,6-DIMETHYL-; 1H-INDOLE-3-CARBOXALDEHYDE, 2-CHLORO-5-METHOXY-6-METHYL-; 1H-INDOLE-3-CARBOXALDEHYDE, 2-IODO-; 1H-INDOLE-3-CARBOXALDEHYDE, 2-IODO-1-(METHOXYMETHYL)-; 1H-INDOLE-3-CARBOXALDEHYDE, 2-IODO-1-METHOXY-; 1H-PYRAZOLE-1-PROPANAL, 4-BROMO-BETA-CYCLOPENTYL-, (BETAR)-; 1H-PYRAZOLO[3,4-C]PYRIDINE-7-CARBOXALDEHYDE, 3-CHLORO-; 1H-PYRROLO[2,3-B]PYRIDINE-3-CARBOXALDEHYDE, 2-CHLORO-; 1-SEC-BUTYL-4-CHLORO-3-METHYL-1H-PYRAZOLE-5-CARBALDEHYDE; 1-SEC-BUTYL-6-CHLORO-5-FORMYL-4-METHYL-2-OXO-1,2-DIHYDRO-PYRIDINE-3-CARBONITRILE; 1-TERT-BUTYL-5-CHLORO-3-(DIFLUOROMETHYL)-1H-PYRAZOLE-4-CARBALDEHYDE; 1-TERT-BUTYL-5-CHLORO-3-(METHOXYMETHYL)-1H-PYRAZOLE-4-CARBALDEHYDE; 1-TERT-BUTYL-5-CHLORO-3-(PROPAN-2-YL)-1H-PYRAZOLE-4-CARBALDEHYDE; 1-TERT-BUTYL-5-CHLORO-3-(TRIFLUOROMETHYL)-1H-PYRAZOLE-4-CARBALDEHYDE; 1-TERT-BUTYL-5-CHLORO-3-CYCLOPROPYL-1H-PYRAZOLE-4-CARBALDEHYDE; 1-TERT-BUTYL-5-CHLORO-3-ETHYL-1H-PYRAZOLE-4-CARBALDEHYDE; 1-TERT-BUTYL-5-CHLORO-3-METHYL-1H-PYRAZOLE-4-CARBALDEHYDE; 1-TERT-BUTYL-5-CHLORO-3-PHENYL-1H-PYRAZOLE-4-CARBALDEHYDE; 1-TERT-BUTYL-5-CHLORO-3-PROPYL-1H-PYRAZOLE-4-CARBALDEHYDE; 2-(([(4-BROMOTHIOPHEN-2-YL)METHYL](METHYL)AMINO)METHYL)-2-ETHYLBUTANAL; 2-(([(4-BROMOTHIOPHEN-2-YL)METHYL](METHYL)AMINO)METHYL)-2-METHYLBUTANAL; 2-(([(4-BROMOTHIOPHEN-2-YL)METHYL](METHYL)AMINO)METHYL)-2-METHYLPENTANAL; 2-([(4-BROMOTHIOPHEN-2-YL)METHYL](METHYL)AMINO)-1,3-THIAZOLE-5-CARBALDEHYDE; 2-([(4-BROMOTHIOPHEN-2-YL)METHYL](METHYL)AMINO)-4-ETHYL-1,3-THIAZOLE-5-CARBALDEHYDE; 2-([(4-BROMOTHIOPHEN-2-YL)METHYL](METHYL)AMINO)-4-METHYL-1,3-THIAZOLE-5-CARBALDEHYDE; 2-([(4-BROMOTHIOPHEN-2-YL)METHYL](METHYL)AMINO)-5-FLUOROBENZALDEHYDE; 2-([(4-BROMOTHIOPHEN-2-YL)METHYL](METHYL)AMINO)ACETALDEHYDE; 2-([(4-BROMOTHIOPHEN-2-YL)METHYL](METHYL)AMINO)BENZALDEHYDE; 2-([5-CHLORO-1-(4-METHYLPHENYL)-6-OXO-1,6-DIHYDROPYRIDAZIN-4-YL]OXY)BENZALDEHYDE; 2-(1-((BENZYLOXY)METHYL)-4-IODO-1H-IMIDAZOL-5-YL)ACETALDEHYDE; 2-(2H-1,3-BENZODIOXOL-5-YL)-6-CHLOROIMIDAZO[1,2-A]PYRIDINE-3-CARBALDEHYDE; 2-(3-BENZYL-5-BROMO-2,6-DIOXO-2,3-DIHYDROPYRIMIDIN-1(6H)-YL)ACETALDEHYDE; 2-(3-BROMO-1H-INDOL-1-YL)ACETALDEHYDE; 2-(3-BROMO-2-METHYL-1H-INDOL-1-YL)ACETALDEHYDE; 2-(3-BROMO-FURAN-2-YL)-4-FORMYL-IMIDAZOLE; 2-(3-BROMOPHENYL)-6-CHLORO-IMIDAZO[1,2-A]PYRIDINE-3-CARBALDEHYDE; 2-(3-BROMO-THIOPHEN-2-YL)-4-FORMYL-1H-IMIDAZOLE; 2-(3-CHLORO-1H-INDOL-1-YL)ACETALDEHYDE; 2-(4,5-DIBROMOFURAN-2-YL)-1,3-THIAZOLE-4-CARBALDEHYDE; 2-(4,5-DIBROMOFURAN-2-YL)-1,3-THIAZOLE-5-CARBALDEHYDE; 2-(4-BROMO-1H-PYRAZOL-1-YL)-5-FLUOROBENZALDEHYDE; 2-(4-BROMO-1H-PYRAZOL-1-YL)-5-NITROBENZALDEHYDE; 2-(4-BROMO-1H-PYRAZOL-1-YL)-6-CHLOROBENZALDEHYDE; 2-(4-BROMO-1H-PYRAZOL-1-YL)BENZALDEHYDE; 2-(4-BROMO-1H-PYRAZOL-1-YL)IMIDAZO[1,2-A]PYRIDINE-3-CARBALDEHYDE; 2-(4-BROMO-1H-PYRAZOL-1-YL)QUINOLINE-3-CARBALDEHYDE; 2-(4-BROMO-3,5-DIMETHYL-1H-PYRAZOL-1-YL)-5-FLUOROBENZALDEHYDE; 2-(4-BROMO-3,5-DIMETHYL-1H-PYRAZOL-1-YL)-5-NITROBENZALDEHYDE; 2-(4-BROMO-3,5-DIMETHYL-1H-PYRAZOL-1-YL)-6-CHLOROBENZALDEHYDE; 2-(4-BROMO-3,5-DIMETHYL-1H-PYRAZOL-1-YL)IMIDAZO[1,2-A]PYRIDINE-3-CARBALDEHYDE; 2-(4-BROMO-3-NITRO-1H-PYRAZOL-1-YL)ACETALDEHYDE; 2-(4-BROMO-FURAN-2-YL)-4-FORMYL-IMIDAZOLE; 2-(4-BROMOPHENYL)-6-CHLOROIMIDAZO[1,2-A]PYRIDINE-3-CARBALDEHYDE; 2-(4-BROMOPHENYL)-7-CHLOROIMIDAZO[1,2-A]PYRIDINE-3-CARBALDEHYDE; 2-(4-BROMOTHIOPHEN-2-YL)-1,3-THIAZOLE-4-CARBALDEHYDE; 2-(4-BROMOTHIOPHEN-2-YL)-1,3-THIAZOLE-5-CARBALDEHYDE; 2-(4-BROMO-THIOPHEN-2-YL)-4-FORMYL-1H-IMIDAZOLE; 2-(4-CHLORO-1H-PYRAZOL-1-YL)-5-FLUOROBENZALDEHYDE; 2-(4-CHLORO-1H-PYRAZOL-1-YL)-5-NITROBENZALDEHYDE; 2-(4-CHLORO-1H-PYRAZOL-1-YL)BENZALDEHYDE; 2-(4-CHLORO-1H-PYRAZOL-1-YL)IMIDAZO[1,2-A]PYRIDINE-3-CARBALDEHYDE; 2-(4-CHLORO-1H-PYRAZOL-1-YL)QUINOLINE-3-CARBALDEHYDE; 2-(4-CHLORO-3,5-DIMETHYL-1H-PYRAZOL-1-YL)-5-FLUOROBENZALDEHYDE; 2-(5-BROMO-1H-PYRAZOL-1-YL)ACETALDEHYDE; 2-(5-BROMO-2,6-DIOXO-3-PHENETHYL-2,3-DIHYDROPYRIMIDIN-1(6H)-YL)ACETALDEHYDE; 2-(5-BROMO-2-OXO-1,2-DIHYDROPYRIDIN-1-YL)ACETALDEHYDE; 2-(5-BROMO-3-ETHYL-2,6-DIOXO-2,3-DIHYDROPYRIMIDIN-1(6H)-YL)ACETALDEHYDE; 2-(5-BROMO-3-METHYL-2,6-DIOXO-2,3-DIHYDROPYRIMIDIN-1(6H)-YL)ACETALDEHYDE; 2-(5-BROMO-3-NITRO-2-OXO-1,2-DIHYDROPYRIDIN-1-YL)ACETALDEHYDE; 2-(5-CHLORO-1H-PYRAZOL-1-YL)ACETALDEHYDE; 2,2'-DIFORMYL-4,4'-DIBROMO-3,3'-BITHIOPHENE; 2,3,3-TRICHLOROPROPENAL; 2,3-DICHLORO-4,4,4-TRIFLUOROBUT-2-ENAL; 2,4-DIBROMOTHIAZOLE-5-CARBOXALDEHYDE; 2,4-DICHLORO-1H-INDOLE-3-CARBALDEHYDE; 2,4-DICHLORO-1-METHYL-1H-IMIDAZOLE-5-CARBALDEHYDE; 2,4-DICHLORO-1-PHENYL-1H-IMIDAZOLE-5-CARBALDEHYDE; 2,4-DICHLORO-5-THIAZOLECARBOXALDEHYDE; 2,5,6-TRICHLORO-1H-INDOLE-3-CARBALDEHYDE; 2,5-DICHLORO-1H-INDOLE-3-CARBALDEHYDE; 2,5-DICHLORO-1-PHENYL-1H-PYRROLE-3,4-DICARBALDEHYDE; 2,6-DICHLORO-1,4-DIDIHYDROPYRIDINE-3,5-DICARBOXYALDEHYDE; 2,6-DICHLORO-1H-INDOLE-3-CARBALDEHYDE; 2,6-DICHLORO-3-FORMYLPYRIDAZINE; 2,6-DICHLORO-IMIDAZO[1,2-A]PYRIDINE-3-CARBOXALDEHYDE; 2,6-DICHLORO-IMIDAZO[2,1-B]THIAZOLE-5-CARBOXALDEHYDE; 2,7-DICHLORO-4-OXO-4H-PYRIDO[1,2-A]PYRIMIDINE-3-CARBALDEHYDE; 2-[(2-BROMOPROP-2-EN-1-YL)OXY]-3,5-DICHLOROBENZALDEHYDE; 2-[(2-BROMOPROP-2-EN-1-YL)OXY]-3-ETHOXYBENZALDEHYDE; 2-[(2-BROMOPROP-2-EN-1-YL)OXY]-3-METHOXYBENZALDEHYDE; 2-[(2-BROMOPROP-2-EN-1-YL)OXY]-4-METHOXYBENZALDEHYDE; 2-[(2-BROMOPROP-2-EN-1-YL)OXY]-4-PROPOXYBENZALDEHYDE; 2-[(2-BROMOPROP-2-EN-1-YL)OXY]-5-CHLOROBENZALDEHYDE; 2-[(2-BROMOPROP-2-EN-1-YL)OXY]-5-METHOXYBENZALDEHYDE; 2-[(2-BROMOPROP-2-EN-1-YL)OXY]-5-

METHYLBENZALDEHYDE; 2-[(2-BROMOPROP-2-EN-1-YL)OXY]-5-NITROBENZALDEHYDE; 2-[(2-BROMOPROP-2-EN-1-YL)OXY]-6-CHLOROBENZALDEHYDE; 2-[(2-BROMOPROP-2-EN-1-YL)OXY]BENZALDEHYDE; 2-[(2-BROMOPROP-2-EN-1-YL)OXY]NAPHTHALENE-1-CARBALDEHYDE; 2-[(2-CHLOROPROP-2-EN-1-YL)OXY]-3-ETHOXYBENZALDEHYDE; 2-[(2-CHLOROPROP-2-EN-1-YL)OXY]-3-METHOXYBENZALDEHYDE; 2-[(2-CHLOROPROP-2-EN-1-YL)OXY]-4-METHOXYBENZALDEHYDE; 2-[(2-CHLOROPROP-2-EN-1-YL)OXY]-4-PROPOXYBENZALDEHYDE; 2-[(2-CHLOROPROP-2-EN-1-YL)OXY]-5-METHOXYBENZALDEHYDE; 2-[(2-CHLOROPROP-2-EN-1-YL)OXY]-5-METHYLBENZALDEHYDE; 2-[(2-CHLOROPROP-2-EN-1-YL)OXY]-5-NITROBENZALDEHYDE; 2-[(2-CHLOROPROP-2-EN-1-YL)OXY]BENZALDEHYDE; 2-[(2-CHLOROPROP-2-EN-1-YL)OXY]NAPHTHALENE-1-CARBALDEHYDE; 2-[(3-BROMOTHIOPHEN-2-YL)METHOXY]-3-ETHOXYBENZALDEHYDE; 2-[(3-BROMOTHIOPHEN-2-YL)METHOXY]-3-METHOXYBENZALDEHYDE; 2-[(3-BROMOTHIOPHEN-2-YL)METHOXY]-4-METHOXYBENZALDEHYDE; 2-[(3-BROMOTHIOPHEN-2-YL)METHOXY]-5-CHLOROBENZALDEHYDE; 2-[(3-BROMOTHIOPHEN-2-YL)METHOXY]-5-METHOXYBENZALDEHYDE; 2-[(3-BROMOTHIOPHEN-2-YL)METHOXY]-5-NITROBENZALDEHYDE; 2-[(3-BROMOTHIOPHEN-2-YL)METHOXY]-6-CHLOROBENZALDEHYDE; 2-[(3-BROMOTHIOPHEN-2-YL)METHOXY]BENZALDEHYDE; 2-[(4-BROMOTHIOPHEN-2-YL)METHOXY]-3-ETHOXYBENZALDEHYDE; 2-[(4-BROMOTHIOPHEN-2-YL)METHOXY]-3-METHOXYBENZALDEHYDE; 2-[(4-BROMOTHIOPHEN-2-YL)METHOXY]-4-METHOXYBENZALDEHYDE; 2-[(4-BROMOTHIOPHEN-2-YL)METHOXY]-5-CHLOROBENZALDEHYDE; 2-[(4-BROMOTHIOPHEN-2-YL)METHOXY]-5-METHOXYBENZALDEHYDE; 2-[(4-BROMOTHIOPHEN-2-YL)METHOXY]-5-NITROBENZALDEHYDE; 2-[(4-BROMOTHIOPHEN-2-YL)METHOXY]-6-CHLOROBENZALDEHYDE; 2-[(4-BROMOTHIOPHEN-2-YL)METHOXY]BENZALDEHYDE; 2-[(5-CHLORO-1-METHYL-1H-IMIDAZOL-2-YL)METHOXY]-3-METHOXYBENZALDEHYDE; 2-[(5-CHLORO-1-METHYL-1H-IMIDAZOL-2-YL)METHOXY]-4-METHOXYBENZALDEHYDE; 2-[(5-CHLORO-1-METHYL-1H-IMIDAZOL-2-YL)METHOXY]-5-METHOXYBENZALDEHYDE; 2-[(5-CHLORO-1-METHYL-1H-IMIDAZOL-2-YL)METHOXY]BENZALDEHYDE; 2-[(5-CHLORO-6-OXO-1-PHENYL-1,6-DIHYDROPYRIDAZIN-4-YL)OXY]BENZALDEHYDE; 2-AMINO-4-CHLORO-1-METHYL-1H-IMIDAZOLE-5-CARBALDEHYDE; 2-AMINO-4-CHLORO-1-PHENYL-1H-IMIDAZOLE-5-CARBALDEHYDE; 2-AMINO-4-CHLORO-3-CYANO-5-FORMYLTHIOPHENE; 2-AMINO-4-CHLORO-6-OXO-1H-PYRIMIDINE-5-CARBALDEHYDE; 2-AMINO-4-CHLOROTHIAZOLE-5-CARBALDEHYDE; 2-AMINO-6-CHLORO-1,4-DIHYDRO-4-OXO-5-PYRIMIDINECARBOXALDEHYDE; 2-AMINO-7-BROMO-[1,2,4]TRIAZOLO[1,5-A]PYRIDINE-5-CARBOXALDEHYDE; 2-AZEPAN-1-YL-4-CHLORO-THIAZOLE-5-CARBALDEHYDE; 2-BIPHENYL-4-YL-6-BROMOIMIDAZO[1,2-A]PYRIDINE-3-CARBALDEHYDE; 2-BIPHENYL-4-YL-6-CHLOROIMIDAZO[1,2-A]PYRIDINE-3-CARBALDEHYDE; 2-BROMO-1H-IMIDAZOLE-5-CARBALDEHYDE; 2-BROMO-1-METHYL-1H-IMIDAZOLE-5-CARBALDEHYDE; 2-BROMO-2-BUTENAL; 2-BROMO-3-DIMETHYLAMINOACROLEIN; 2-BROMO-3-HYDROXY-2-BUTENE-1,4-DIONE; 2-BROMO-3-HYDROXY-PROPENAL; 2-BROMO-3-ISOPROPOXYACRYLALDEHYDE; 2-BROMO-3-METHYLBUT-2-ENAL; 2-BROMO-4-(4-FLUOROPHENYL)-5-NITRO-CYCLOHEX-1-ENECARBALDEHYDE; 2-BROMO-5,5-DIMETHYL-CYCLOHEX-1-ENECARBALDEHYDE; 2-BROMO-CYCLOHEX-1-ENECARBALDEHYDE; 2-BROMO-CYCLOPENT-1-ENECARBALDEHYDE; 2-BROMO-PROPENAL; 2-BUTENAL, 3-CHLORO-4-OXO-4-PHENYL-, (E)-; 2-BUTYL-4-CHLORO-1H-IMIDAZOLE-5-CARBALDEHYDE; 2-BUTYL-5-CHLORO-1H-IMIDAZOLE-4-CARBALDEHYDE; 2-BUTYL-5-IODO-3H-IMIDAZOLE-4-CARBALDEHYDE; 2-CHLORO-1-ETHYL-1H-INDOLE-3-CARBALDEHYDE; 2-CHLORO-1-ETHYL-5-FORMYL-4-METHYL-6-OXO-1,6-DIHYDROPYRIDINE-3-CARBONITRILE; 2-CHLORO-1H-BENZIMIDAZOLE-5-CARBOXALDEHYDE; 2-CHLORO-1H-IMIDAZOLE-5-CARBALDEHYDE; 2-CHLORO-1H-INDOLE-3-CARBALDEHYDE; 2-CHLORO-1H-PYRROLO[2,3-C]PYRIDINE-3-CARBALDEHYDE; 2-CHLORO-1H-PYRROLO[3,2-C]PYRIDINE-3-CARBALDEHYDE; 2-CHLORO-1-METHYL-1H-IMIDAZOLE-5-CARBALDEHYDE; 2-CHLORO-1-METHYL-1H-INDOLE-3,5-DICARBALDEHYDE; 2-CHLORO-1-METHYL-1H-INDOLE-3-CARBALDEHYDE; 2-CHLORO-1-METHYL-1H-PYRROLO[2,3-B]PYRIDINE-3-CARBALDEHYDE; 2-CHLORO-1-METHYL-1H-PYRROLO[2,3-C]PYRIDINE-3-CARBALDEHYDE; 2-CHLORO-1-METHYL-1H-PYRROLO[3,2-B]PYRIDINE-3-CARBALDEHYDE; 2-CHLORO-1-METHYL-1H-PYRROLO[3,2-C]PYRIDINE-3-CARBALDEHYDE; 2-CHLORO-1-METHYL-5-PHENYL-1H-PYRROLE-3,4-DICARBALDEHYDE; 2-CHLORO-1-PHENYL-1H-INDOLE-3-CARBALDEHYDE; 2-CHLORO-1-PHENYL-1H-PYRROLO[2,3-B]PYRIDINE-3-CARBALDEHYDE; 2-CHLORO-3-FORMYL-N,N-DIMETHYL-1H-INDOLE-5-SULFONAMIDE; 2-CHLORO-3-HYDROXY-2-PROPENAL; 2-CHLORO-3-PHENYLPROP-2-ENAL; 2-CHLORO-4-IODO-1H-INDOLE-3-CARBALDEHYDE; 2-CHLORO-4-OXO-4H-PYRIDO[1,2-A]PYRIMIDINE-3-CARBALDEHYDE; 2-CHLORO-5-(MORPHOLIN-4-YLSULFONYL)-1H-INDOLE-3-CARBALDEHYDE; 2-CHLORO-5-(PYRROLIDIN-1-YLSULFONYL)-1H-INDOLE-3-CARBALDEHYDE; 2-CHLORO-5-ETHYLCYCLOHEX-1-ENE-1-CARBALDEHYDE; 2-CHLORO-5-HYDROXY-1H-INDOLE-3-CARBALDEHYDE; 2-CHLORO-5-HYDROXY-6-METHYL-1H-INDOLE-3-CARBALDEHYDE; 2-CHLORO-5-METHOXY-1H-INDOLE-3-CARBALDEHYDE; 2-CHLORO-5-METHOXY-1-METHYL-1H-INDOLE-3-CARBALDEHYDE; 2-CHLORO-5-METHYLCYCLOHEX-1-ENE-1-CARBALDEHYDE; 2-CHLORO-5-PHENYLCYCLOHEX-1-ENE-1-CARBALDEHYDE; 2-CHLORO-6-(4-CHLORO-1H-PYRAZOL-1-YL)BENZALDEHYDE; 2-CHLORO-6-[(2-CHLOROPROP-2-EN-1-YL)OXY]BENZALDEHYDE; 2-CHLORO-6-[(5-CHLORO-1-METHYL-1H-IMIDAZOL-2-YL)METHOXY]BENZALDEHYDE; 2-CHLORO-6-METHYL-4A,8A-

DIHYDRO-3-QUINOLINECARBALDEHYDE; 2-CHLORO-6-METHYL-4-OXO-4H-PYRIDO[1,2-A]PYRIMIDINE-3-CARBALDEHYDE; 2-CHLORO-7-METHYL-4-OXO-4H-PYRIDO[1,2-A]PYRIMIDINE-3-CARBALDEHYDE; 2-CHLORO-8-METHYL-4-OXO-4H-PYRIDO[1,2-A]PYRIMIDINE-3-CARBALDEHYDE; 2-CHLORO-9-METHYL-4-OXO-4H-PYRIDO[1,2-A]PYRIMIDINE-3-CARBALDEHYDE; 2-CHLOROACROLEIN; 2-CHLOROCYCLOHEX-1-ENECARBALDEHYDE; 2-CHLOROCYCLOPENT-1-ENECARBALDEHYDE; 2-CHLORO-IMIDAZO[1,2-A]PYRIDINE-3-CARBALDEHYDE; 2-ETHOXY-4-FORMYLPHENYL 4-CHLORO-1-ETHYLPYRAZOLE-3-CARBOXYLATE; 2-ETHYL-5-CHLORO-1H-IMIDAZOLE-4-CARBALDEHYDE; 2-IODO-4-AZAINDOLE-6-CARBOXALDEHYDE; 3-(([(4-BROMOTHIOPHEN-2-YL)METHYL](METHYL)AMINO)METHYL)OXOLANE-3-CARBALDEHYDE; 3-([(4-BROMOTHIOPHEN-2-YL)METHYL]METHYL)AMINO)-2,2-DIMETHYLPROPANAL; 3-([(4-BROMOTHIOPHEN-2-YL)METHYL](METHYL)AMINO)PROPANAL; 3-([4-BROMO-3,5-BIS(DIFLUOROMETHYL)-1H-PYRAZOL-1-YL]METHYL)-4-METHOXYBENZALDEHYDE; 3-(2-BROMO-4-CHLOROPHENYL)-5-CHLORO-1-METHYL-1H-PYRAZOLE-4-CARBOXALDEHYDE; 3-(2-BROMO-4-FLUOROPHENYL)-5-CHLORO-1-METHYL-1H-PYRAZOLE-4-CARBOXALDEHYDE; 3-(2-BROMO-5-CHLOROPHENYL)-5-CHLORO-1-METHYL-1H-PYRAZOLE-4-CARBOXALDEHYDE; 3-(2-BROMO-5-FLUOROPHENYL)-5-CHLORO-1-METHYL-1H-PYRAZOLE-4-CARBOXALDEHYDE; 3-(2-BROMOPHENYL)-5-CHLORO-1-(1,1-DIMETHYLETHYL)-1H-PYRAZOLE-4-CARBOXALDEHYDE; 3-(2-BROMOPHENYL)-5-CHLORO-1-METHYL-1H-PYRAZOLE-4-CARBOXALDEHYDE; 3-(3-BROMO-1H-INDOL-1-YL)PROPANAL; 3-(3-BROMOPHENYL)-5-CHLORO-1-(1,1-DIMETHYLETHYL)-1H-PYRAZOLE-4-CARBOXALDEHYDE; 3-(3-BROMOPHENYL)-5-CHLORO-1-METHYL-1H-PYRAZOLE-4-CARBOXALDEHYDE; 3-(3-BROMOTHIOPHEN-2-YL)-1-(1-CYCLOPROPYLETHYL)-1H-PYRAZOLE-4-CARBALDEHYDE; 3-(3-BROMOTHIOPHEN-2-YL)-1-(2-METHYLPROPYL)-1H-PYRAZOLE-4-CARBALDEHYDE; 3-(3-BROMOTHIOPHEN-2-YL)-1-(3-METHYLBUTYL)-1H-PYRAZOLE-4-CARBALDEHYDE; 3-(3-BROMOTHIOPHEN-2-YL)-1-(BUTAN-2-YL)-1H-PYRAZOLE-4-CARBALDEHYDE; 3-(3-BROMOTHIOPHEN-2-YL)-1-(PENTAN-3-YL)-1H-PYRAZOLE-4-CARBALDEHYDE; 3-(3-BROMOTHIOPHEN-2-YL)-1-(PROPAN-2-YL)-1H-PYRAZOLE-4-CARBALDEHYDE; 3-(3-BROMOTHIOPHEN-2-YL)-1-(PYRIDIN-2-YL)-1H-PYRAZOLE-4-CARBALDEHYDE; 3-(3-BROMOTHIOPHEN-2-YL)-1-(PYRIDIN-4-YL)-1H-PYRAZOLE-4-CARBALDEHYDE; 3-(3-BROMOTHIOPHEN-2-YL)-1-(PYRIMIDIN-2-YL)-1H-PYRAZOLE-4-CARBALDEHYDE; 3-(3-BROMOTHIOPHEN-2-YL)-1-BUTYL-1H-PYRAZOLE-4-CARBALDEHYDE; 3-(3-BROMOTHIOPHEN-2-YL)-1-CYCLOHEXYL-1H-PYRAZOLE-4-CARBALDEHYDE; 3-(3-BROMOTHIOPHEN-2-YL)-1-CYCLOPENTYL-1H-PYRAZOLE-4-CARBALDEHYDE; 3-(3-BROMOTHIOPHEN-2-YL)-1-ETHYL-1H-PYRAZOLE-4-CARBALDEHYDE; 3-(3-BROMOTHIOPHEN-2-YL)-1H-PYRAZOLE-4-CARBALDEHYDE; 3-(3-BROMOTHIOPHEN-2-YL)-1-METHYL-1H-PYRAZOLE-4-CARBALDEHYDE; 3-(3-BROMOTHIOPHEN-2-YL)-1-PHENYL-1H-PYRAZOLE-4-CARBALDEHYDE; 3-(3-BROMOTHIOPHEN-2-YL)-1-PROPYL-1H-PYRAZOLE-4-CARBALDEHYDE; 3-(3-BROMOTHIOPHEN-2-YL)-1-TERT-BUTYL-1H-PYRAZOLE-4-CARBALDEHYDE; 3-(3-BROMOTHIOPHEN-2-YL)PROPANAL; 3-(3-CHLORO-1H-INDOL-1-YL)PROPANAL; 3-(3-TERT-BUTYL-5-CHLORO-4-FORMYL-1H-PYRAZOL-1-YL)PROPANENITRILE; 3-(4-[(2-CHLOROPROP-2-EN-1-YL)OXY]PHENYL)-1H-PYRAZOLE-4-CARBALDEHYDE; 3-(4-[(2-CHLOROPROP-2-EN-1-YL)OXY]PHENYL)-1-METHYL-1H-PYRAZOLE-4-CARBALDEHYDE; 3-(4-BROMO-2-CHLOROPHENYL)-5-CHLORO-1-METHYL-1H-PYRAZOLE-4-CARBOXALDEHYDE; 3-(4-BROMO-2-FLUOROPHENYL)-5-CHLORO-1-METHYL-1H-PYRAZOLE-4-CARBOXALDEHYDE; 3-(4-BROMO-3-NITRO-1H-PYRAZOL-1-YL)PROPANAL; 3-(4-BROMOPHENYL)-5-CHLORO-1-(1,1-DIMETHYLETHYL)-1H-PYRAZOLE-4-CARBOXALDEHYDE; 3-(4-BROMOPHENYL)-5-CHLORO-1-METHYL-1H-PYRAZOLE-4-CARBOXALDEHYDE; 3-(4-BROMOTHIOPHEN-2-YL)PROPANAL; 3-(4-CHLORO-3-NITRO-PYRAZOL-1-YLMETHYL)-4-METHOXY-BENZALDEHYDE; 3-(4-CHLORO-PYRAZOL-1-YLMETHOXY)-BENZALDEHYDE; 3-(5-BROMO-1H-PYRAZOL-1-YL)PROPANAL; 3-(5-BROMO-2-CHLOROPHENYL)-5-CHLORO-1-METHYL-1H-PYRAZOLE-4-CARBOXALDEHYDE; 3-(5-BROMO-2-FLUOROPHENYL)-5-CHLORO-1-METHYL-1H-PYRAZOLE-4-CARBOXALDEHYDE; 3-(5-BROMO-3-NITRO-2-OXO-1,2-DIHYDROPYRIDIN-1-YL)PROPANAL; 3-(5-CHLORO-1H-PYRAZOL-1-YL)PROPANAL; 3-(5-CHLORO-3-CYCLOPROPYL-4-FORMYL-1H-PYRAZOL-1-YL)PROPANENITRILE; 3-(5-CHLORO-3-ETHYL-4-FORMYL-1H-PYRAZOL-1-YL)BENZONITRILE; 3-(5-CHLORO-3-ETHYL-4-FORMYL-1H-PYRAZOL-1-YL)PROPANENITRILE; 3-(5-CHLORO-4-FORMYL-3-METHYL-1H-PYRAZOL-1-YL)BENZONITRILE; 3-(5-CHLORO-4-FORMYL-3-METHYL-1H-PYRAZOL-1-YL)PROPANENITRILE; 3-(5-CHLORO-4-FORMYL-3-PHENYL-1H-PYRAZOL-1-YL)PROPANENITRILE; 3-(5-CHLORO-4-FORMYL-3-PROPYL-1H-PYRAZOL-1-Yl)BENZONITRILE; 3-(5-CHLORO-4-FORMYL-3-PROPYL-1H-PYRAZOL-1-YL)PROPANENITRILE; 3-(DIMETHYLAMINO)-2-IODOACROLEIN; 3,4-DIBROMO-5-METHYL-2-PYRROLECARBOXALDEHYDE; 3,4-DIBROMOTHIOPHENE-2,5-DICARBOXALDEHYDE; 3,4-DIBROMOTHIOPHENE-2-CARBOXALDEHYDE; 3,4-DICHLORO-2,5-PYRROLEDICARBOXALDEHYDE; 3,5-DIBROMO-1-(2,4-DICHLOROPHENYL)-1H-PYRAZOLE-4-CARBOXALDEHYDE; 3,5-DIBROMO-1-(2,4-DIFLUOROPHENYL)-1H-PYRAZOLE-4-CARBOXALDEHYDE; 3,5-DIBROMO-1-(2,5-DICHLOROPHENYL)-1H-PYRAZOLE-4-CARBOXALDEHYDE; 3,5-DIBROMO-1-(2,5-DIFLUOROPHENYL)-1H-PYRAZOLE-4-CARBOXALDEHYDE; 3,5-DIBROMO-1-(2-FLUOROPHENYL)-1H-PYRAZOLE-4-CARBOXALDEHYDE; 3,5-DIBROMO-1-(2-NITROPHENYL)-1H-PYRAZOLE-4-CARBOXALDEHYDE; 3,5-DIBROMO-1-(3,4-DICHLOROPHENYL)-1H-PYRAZOLE-4-CARBOXALDEHYDE; 3,5-DIBROMO-1-(3,4-

DIFLUOROPHENYL)-1H-PYRAZOLE-4-CARBOXALDEHYDE; 3,5-DIBROMO-1-(3,5-DICHLOROPHENYL)-1H-PYRAZOLE-4-CARBOXALDEHYDE; 3,5-DIBROMO-1-(3,5-DIFLUOROPHENYL)-1H-PYRAZOLE-4-CARBOXALDEHYDE; 3,5-DIBROMO-1-(3-FLUOROPHENYL)-1H-PYRAZOLE-4-CARBOXALDEHYDE; 3,5-DIBROMO-1-(3-NITROPHENYL)-1H-PYRAZOLE-4-CARBOXALDEHYDE; 3,5-DIBROMO-1-(4-FLUOROPHENYL)-1H-PYRAZOLE-4-CARBOXALDEHYDE; 3,5-DIBROMO-1-(4-NITROPHENYL)-1H-PYRAZOLE-4-CARBOXALDEHYDE; 3,5-DIBROMO-1-[2-(TRIFLUOROMETHYL)PHENYL]-1H-PYRAZOLE-4-CARBOXALDEHYDE; 3,5-DIBROMO-1-[3-(TRIFLUOROMETHYL)PHENYL]-1H-PYRAZOLE-4-CARBOXALDEHYDE; 3,5-DIBROMO-1-[4-(TRIFLUOROMETHYL)PHENYL]-1H-PYRAZOLE-4-CARBOXALDEHYDE; 3,5-DIBROMO-1H-PYRAZOLE-4-CARBALDEHYDE; 3,5-DIBROMO-2-THIOPHENECARBOXALDEHYDE; 3,5-DICHLORO-1-(2-(TRIFLUOROMETHYL)PHENYL)-1H-PYRAZOLE-4-CARBOXALDEHYDE; 3,5-DICHLORO-1-(2,4-DICHLOROPHENYL)-1H-PYRAZOLE-4-CARBOXALDEHYDE; 3,5-DICHLORO-1-(2,4-DIFLUOROPHENYL)-1H-PYRAZOLE-4-CARBOXALDEHYDE; 3,5-DICHLORO-1-(2,5-DICHLOROPHENYL)-1H-PYRAZOLE-4-CARBOXALDEHYDE; 3,5-DICHLORO-1-(2,5-DIFLUOROPHENYL)-1H-PYRAZOLE-4-CARBOXALDEHYDE; 3,5-DICHLORO-1-(2-FLUOROPHENYL)-1H-PYRAZOLE-4-CARBOXALDEHYDE; 3,5-DICHLORO-1-(2-NITROPHENYL)-1H-PYRAZOLE-4-CARBOXALDEHYDE; 3,5-DICHLORO-1-(3-(TRIFLUOROMETHYL)PHENYL)-1H-PYRAZOLE-4-CARBOXALDEHYDE; 3,5-DICHLORO-1-(3,4-DICHLOROPHENYL)-1H-PYRAZOLE-4-CARBOXALDEHYDE; 3,5-DICHLORO-1-(3,4-DIFLUOROPHENYL)-1H-PYRAZOLE-4-CARBOXALDEHYDE; 3,5-DICHLORO-1-(3,5-DICHLOROPHENYL)-1H-PYRAZOLE-4-CARBOXALDEHYDE; 3,5-DICHLORO-1-(3,5-DIFLUOROPHENYL)-1H-PYRAZOLE-4-CARBOXALDEHYDE; 3,5-DICHLORO-1-(3-FLUOROPHENYL)-1H-PYRAZOLE-4-CARBOXALDEHYDE; 3,5-DICHLORO-1-(3-NITROPHENYL)-1H-PYRAZOLE-4-CARBOXALDEHYDE; 3,5-DICHLORO-1-(4-(TRIFLUOROMETHYL)PHENYL)-1H-PYRAZOLE-4-CARBOXALDEHYDE; 3,5-DICHLORO-1-(4-FLUOROPHENYL)-1H-PYRAZOLE-4-CARBOXALDEHYDE; 3,5-DICHLORO-1-(4-NITROPHENYL)-1H-PYRAZOLE-4-CARBOXALDEHYDE; 3,5-DICHLORO-1H-PYRROLE-2,4-DICARBALDEHYDE; 3,5-DICHLORO-1-PHENYL-1H-PYRROLE-2,4-DICARBALDEHYDE; 3,5-DICHLORO-2-[(2-CHLOROPROP-2-EN-1-YL)OXY]BENZALDEHYDE; 3,5-DICHLORO-2-[(5-CHLORO-1-METHYL-1H-IMIDAZOL-2-YL)METHOXY]BENZALDEHYDE; 3,5-DICHLORO-2-FURANCARBOXALDEHYDE; 3,5-DIIODO-4-METHYL-2-PYRROLECARBOXALDEHYDE; 3-[(2-BROMOPROP-2-EN-1-YL)OXY]-4-METHOXYBENZALDEHYDE; 3-[(2-BROMOPROP-2-EN-1-YL)OXY]-4-NITROBENZALDEHYDE; 3-[(2-BROMOPROP-2-EN-1-YL)OXY]BENZALDEHYDE; 3-[(2-CHLOROPROP-2-EN-1-YL)OXY]-4-METHOXYBENZALDEHYDE; 3-[(2-CHLOROPROP-2-EN-1-YL)OXY]-4-NITROBENZALDEHYDE; 3-[(2-CHLOROPROP-2-EN-1-YL)OXY]BENZALDEHYDE; 3-[(3-BROMOTHIOPHEN-2-YL)METHOXY]-4-METHOXYBENZALDEHYDE; 3-[(3-BROMOTHIOPHEN-2-YL)METHOXY]-4-NITROBENZALDEHYDE; 3-[(3-BROMOTHIOPHEN-2-YL)METHOXY]BENZALDEHYDE; 3-[(4-BROMO-1H-PYRAZOL-1-YL)METHYL]-4-METHOXYBENZALDEHYDE; 3-[(4-BROMO-3,5-DIMETHYL-1H-PYRAZOL-1-YL)METHYL]-4-METHOXYBENZALDEHYDE; 3-[(4-BROMO-5-METHYL-3-NITRO-1H-PYRAZOL-1-YL)METHYL]-4-METHOXYBENZALDEHYDE; 3-[(4-BROMOTHIOPHEN-2-YL)METHOXY]-4-METHOXYBENZALDEHYDE; 3-[(4-BROMOTHIOPHEN-2-YL)METHOXY]-4-NITROBENZALDEHYDE; 3-[(4-BROMOTHIOPHEN-2-YL)METHOXY]BENZALDEHYDE; 3-[(4-CHLORO-1H-PYRAZOL-1-YL)METHYL]-4-METHOXYBENZALDEHYDE; 3-[(4-CHLORO-3,5-DIMETHYL-1H-PYRAZOL-1-YL)METHYL]-4-METHOXYBENZALDEHYDE; 3-[(4-CHLORO-3-NITRO-1H-PYRAZOL-1-YL)METHOXY]BENZALDEHYDE; 3-[(4-CHLORO-5-METHYL-3-NITRO-1H-PYRAZOL-1-YL)METHYL]-4-METHOXYBENZALDEHYDE; 3-[(4-IODO-3,5-DIMETHYL-1H-PYRAZOL-1-YL)METHYL]-4-METHOXYBENZALDEHYDE; 3-[(5-BROMO-2-OXO-1,2-DIHYDROPYRIDIN-1-YL)METHYL]-4-METHOXYBENZALDEHYDE; 3-[(5-CHLORO-1-METHYL-1H-IMIDAZOL-2-YL)METHOXY]-4-METHOXYBENZALDEHYDE; 3-[(5-CHLORO-1-METHYL-1H-IMIDAZOL-2-YL)METHOXY]BENZALDEHYDE; 3-[2-(3-BROMOTHIOPHEN-2-YL)-2-OXOETHOXY]BENZALDEHYDE; 3-[5-CHLORO-3-(DIFLUOROMETHYL)-4-FORMYL-1H-PYRAZOL-1-YL]BENZONITRILE; 3-[5-CHLORO-4-FORMYL-3-(PROPAN-2-YL)-1H-PYRAZOL-1-YL]BENZONITRILE; 3-[5-CHLORO-4-FORMYL-3-(PROPAN-2-YL)-1H-PYRAZOL-1-YL]PROPANENITRILE; 3-[5-CHLORO-4-FORMYL-3-(TRIFLUOROMETHYL)-1H-PYRAZOL-1-YL]PROPANENITRILE; 3-ALLYL-4-CHLORO-2-OXO-2,3-DIHYDRO-1,3-THIAZOLE-5-CARBALDEHYDE; 3-BENZYL-4-CHLORO-2-OXO-2,3-DIHYDRO-1,3-THIAZOLE-5-CARBALDEHYDE; 3-BENZYLOXYMETHYL-2-BUTYL-5-IODO-3H-IMIDAZOLE-4-CARBALDEHYDE; 3-BROMO INDAZOLE-6-CARBOXALDEHYDE; 3-BROMO-1-(TERT-BUTYLDIMETHYLSILYL)-1H-INDOLE-4-CARBALDEHYDE; 3-BROMO-1H-INDAZOLE-5-CARBALDEHYDE; 3-BROMO-1H-INDOLE-2-CARBALDEHYDE; 3-BROMO-1H-INDOLE-4-CARBALDEHYDE; 3-BROMO-1H-PYRROLO[2,3-B]PYRIDINE-4-CARBALDEHYDE; 3-BROMO-1H-PYRROLO[2,3-B]PYRIDINE-5-CARBALDEHYDE; 3-BROMO-1-METHYL-1H-INDOLE-2-CARBALDEHYDE; 3-BROMO-2-[(2-BROMOPROP-2-EN-1-YL)OXY]BENZALDEHYDE; 3-BROMO-2-[(2-CHLOROPROP-2-EN-1-YL)OXY]BENZALDEHYDE; 3-BROMO-2-[(3-BROMOTHIOPHEN-2-YL)METHOXY]BENZALDEHYDE; 3-BROMO-2-[(4-BROMOTHIOPHEN-2-YL)METHOXY]BENZALDEHYDE; 3-BROMO-2-[(5-CHLORO-1-METHYL-1H-IMIDAZOL-2-YL)METHOXY]

BENZALDEHYDE; 3-BROMO-2-FORMYLFURAN; 3-BROMO-2-FORMYLPYRROLE; 3-BROMO-4-[(2-BROMOPROP-2-EN-1-YL)OXY]-5-ETHOXYBENZALDEHYDE; 3-BROMO-4-[(2-BROMOPROP-2-EN-1-YL)OXY]-5-METHOXYBENZALDEHYDE; 3-BROMO-4-[(2-BROMOPROP-2-EN-1-YL)OXY]BENZALDEHYDE; 3-BROMO-4-[(2-CHLOROPROP-2-EN-1-YL)OXY]-5-ETHOXYBENZALDEHYDE; 3-BROMO-4-[(2-CHLOROPROP-2-EN-1-YL)OXY]-5-METHOXYBENZALDEHYDE; 3-BROMO-4-[(2-CHLOROPROP-2-EN-1-YL)OXY]BENZALDEHYDE; 3-BROMO-4-[(3-BROMOTHIOPHEN-2-YL)METHOXY]BENZALDEHYDE; 3-BROMO-4-[(4-BROMOTHIOPHEN-2-YL)METHOXY]BENZALDEHYDE; 3-BROMO-4-[(5-CHLORO-1-METHYL-1H-IMIDAZOL-2-YL)METHOXY]BENZALDEHYDE; 3-BROMO-4-CHLORO-2-METHYL-1-(4-METHYLPHENYL)-6,7-DIHYDRO-1H-INDOLE-5-CARBALDEHYDE; 3-BROMO-4-FLUORO-6-AZAINDOLE-7-CARBOXALDEHYDE; 3-BROMO-4-FORMYLTHIOPHENE; 3-BROMO-5-FLUORO-1H-INDOLE-2-CARBALDEHYDE; 3-BROMO-5-FLUORO-1-METHYL-1H-INDOLE-2-CARBALDEHYDE; 3-BROMO-5-FORMYLFURAN-2-YLBORONIC ACID; 3-BROMO-5-ISOXAZOLECARBOXALDEHYDE; 3-BROMO-5-METHYL-2-THIOPHENECARBOXALDEHYDE; 3-BROMO-6-AZAINDOLE-7-CARBOXALDEHYDE; 3-BROMO-BENZO[B]THIOPHENE-2-CARBOXALDEHYDE; 3-BROMO-BENZOFURAN-2-CARBALDEHYDE; 3-BROMOIMIDAZO[1,2-A]PYRIDINE-2-CARBALDEHYDE; 3-BROMOIMIDAZO[1,2-A]PYRIDINE-6-CARBALDEHYDE; 3-BROMO-IMIDAZO[1,2-A]PYRIDINE-8-CARBOXALDEHYDE; 3-BROMO-PYRAZOLO[1,5-A]PYRIMIDINE-6-CARBOXALDEHYDE; 3-BROMOTHIOPHENE-2-CARBOXALDEHYDE; 3-CHLORO INDAZOLE-6-CARBOXALDEHYDE; 3-CHLORO-1-BENZOFURAN-2-CARBALDEHYDE; 3-CHLORO-1-BENZOTHIOPHENE-2-CARBALDEHYDE; 3-CHLORO-1-ETHYL-1H-PYRROLE-2-CARBALDEHYDE; 3-CHLORO-1H-INDAZOLE-5-CARBALDEHYDE; 3-CHLORO-1H-INDOLE-2-CARBALDEHYDE; 3-CHLORO-1H-INDOLE-4-CARBALDEHYDE; 3-CHLORO-1H-PYRAZOLO[4,3-C]PYRIDINE-7-CARBALDEHYDE; 3-CHLORO-1H-PYRROLE-2,4-DICARBALDEHYDE; 3-CHLORO-1H-PYRROLE-2-CARBALDEHYDE; 3-CHLORO-1H-PYRROLO[2,3-B]PYRIDINE-4-CARBALDEHYDE; 3-CHLORO-1H-PYRROLO[2,3-B]PYRIDINE-5-CARBALDEHYDE; 3-CHLORO-1-METHYL-1H-INDOLE-2-CARBALDEHYDE; 3-CHLORO-1-METHYL-1H-PYRAZOLE-5-CARBALDEHYDE; 3-CHLORO-1-METHYL-1H-PYRROLE-2-CARBALDEHYDE; 3-CHLORO-2-(4-CHLOROPHENYL)-4,4,4-TRIFLUORBUT-2-ENAL; 3-CHLORO-2-(4-CHLORO-PHENYL)-4,4,4-TRIFLUORO-BUT-2-ENAL; 3-CHLORO-2,3-BIS(4-METHOXYPHENYL)ACRYLALDEHYDE; 3-CHLORO-3-(1,5-DIMETHYL-3-OXO-2-PHENYL-2,3-DIHYDRO-1H-PYRAZOL-4-YL)ACRYLALDEHYDE; 3-CHLORO-3-(2'-FLUORO[1,1-BIPHENYL]-4-YL)-2-METHYLACRYLALDEHYDE; 3-CHLORO-3-(4-CHLOROPHENYL)ACROLEIN; 3-CHLORO-3-(4-NITROPHENYL)ACRYLALDEHYDE; 3-CHLORO-3-(P-CHLOROPHENYL)ACROLEIN; 3-CHLORO-3-PHENYL-PROPENAL; 3-CHLORO-3-TRIFLUOROMETHYL-2-PHENYL-2-PROPENAL; 3-CHLORO-4-[(2-CHLOROPROP-2-EN-1-YL)OXY]-5-METHOXYBENZALDEHYDE; 3-CHLORO-4-[(2-CHLOROPROP-2-EN-1-YL)OXY]BENZALDEHYDE; 3-CHLORO-4-[(5-CHLORO-1-METHYL-1H-IMIDAZOL-2-YL)METHOXY]BENZALDEHYDE; 3-CHLORO-5-FLUORO-1H-INDOLE-2-CARBALDEHYDE; 3-CHLORO-5-METHYL-1H-PYRAZOLE-4-CARBALDEHYDE; 3-CHLORO-5-PHENYL-5H-PYRAZOLO[4,3-C]PYRIDINE-7-CARBALDEHYDE; 3-CHLORO-6-AZAINDOLE-7-CARBOXALDEHYDE; 3-CHLORO-6-METHOXY-1-BENZOFURAN-2-CARBALDEHYDE; 3-CHLORO-6-METHOXY-1H-PYRROLO[2,3-B]PYRIDINE-4-CARBALDEHYDE; 3-CHLOROIMIDAZO[1,2-A]PYRIDINE-2-CARBALDEHYDE; 3-CHLOROTHIOPHENE-2-CARBALDEHYDE; 3-CHLOROTHIOPHENE-4-CARBOXALDEHYDE; 3-FORMYL-4-IODOTHIOPHENE; 3-FORMYLPHENYL 3-CHLORO-1-BENZOTHIOPHENE-2-CARBOXYLATE; 3-FORMYLPHENYL 4-CHLORO-1-ETHYLPYRAZOLE-3-CARBOXYLATE; 3-FORMYLPHENYL 4-IODO-1-METHYL-1H-PYRAZOLE-5-CARBOXYLATE; 3-IODO-1H-INDAZOLE-4-CARBALDEHYDE; 3-IODO-1H-INDAZOLE-5-CARBALDEHYDE; 3-IODO-1H-INDAZOLE-6-CARBALDEHYDE; 3-IODO-1H-INDAZOLE-7-CARBALDEHYDE; 3-IODO-1H-PYRROLO[2,3-B]PYRIDINE-4-CARBALDEHYDE; 3-IODO-1H-PYRROLO[2,3-B]PYRIDINE-5-CARBALDEHYDE; 3-IODO-4,5-DIMETHYLTHIOPHENE-2-CARBALDEHYDE; 3-IODO-6-AZAINDOLE-7-CARBOXALDEHYDE; 3-IODO-6-METHOXY-1H-PYRROLO[2,3-B]PYRIDINE-4-CARBALDEHYDE; 3-IODO-IMIDAZO[1,2-A]PYRIDINE-7-CARBALDEHYDE; 3-IODO-IMIDAZO[1,2-A]PYRIDINE-8-CARBALDEHYDE; 3-IODOTHIOPHENE-2-CARBALDEHYDE; 3-TERT-BUTYL-5-CHLORO-1-(1,1-DIOXO-LAMBDA(6)-THIOLAN-3-YL)-1H-PYRAZOLE-4-CARBALDEHYDE; 3-TERT-BUTYL-5-CHLORO-1-(1-CYCLOPROPYLETHYL)-1H-PYRAZOLE-4-CARBALDEHYDE; 3-TERT-BUTYL-5-CHLORO-1-(2-CHLOROPHENYL)-1H-PYRAZOLE-4-CARBALDEHYDE; 3-TERT-BUTYL-5-CHLORO-1-(2-FLUOROPHENYL)-1H-PYRAZOLE-4-CARBALDEHYDE; 3-TERT-BUTYL-5-CHLORO-1-(2-METHYLPHENYL)-1H-PYRAZOLE-4-CARBALDEHYDE; 3-TERT-BUTYL-5-CHLORO-1-(2-METHYLPROPYL)-1H-PYRAZOLE-4-CARBALDEHYDE; 3-TERT-BUTYL-5-CHLORO-1-(3-CHLOROPHENYL)-1H-PYRAZOLE-4-CARBALDEHYDE; 3-TERT-BUTYL-5-CHLORO-1-(3-FLUOROPHENYL)-1H-PYRAZOLE-4-CARBALDEHYDE; 3-TERT-BUTYL-5-CHLORO-1-(3-METHYLBUTYL)-1H-PYRAZOLE-4-CARBALDEHYDE; 3-TERT-BUTYL-5-CHLORO-1-(3-METHYLPHENYL)-1H-PYRAZOLE-4-CARBALDEHYDE; 3-TERT-BUTYL-5-CHLORO-1-(4-CHLOROPHENYL)-1H-PYRAZOLE-4-CARBALDEHYDE; 3-TERT-BUTYL-5-CHLORO-1-(4-FLUOROPHENYL)-1H-PYRAZOLE-4-CARBALDEHYDE; 3-TERT-BUTYL-5-CHLORO-1-(4-METHYLPHENYL)-1H-PYRAZOLE-4-CARBALDEHYDE; 3-TERT-BUTYL-5-CHLORO-1-(4-METHYLPYRIDIN-2-YL)-1H-PYRAZOLE-4-CARBALDEHYDE; 3-TERT-BUTYL-5-CHLORO-1-(6-CHLOROPYRIDAZIN-3-YL)-1H-PYRAZOLE-4-CARBALDEHYDE; 3-TERT-BUTYL-5-CHLORO-1-(6-METHYLPYRIDAZIN-3-YL)-1H-PYRAZOLE-4-CARBALDEHYDE; 3-TERT-BUTYL-5-CHLORO-1-(6-METHYLPYRIMIDIN-4-YL)-1H-PYRAZOLE-4-CARBALDEHYDE; 3-TERT-BUTYL-5-CHLORO-1-(PENTAN-3-YL)-1H-PYRAZOLE-4-CARBALDEHYDE;

3-TERT-BUTYL-5-CHLORO-1-(PROPAN-2-YL)-1H-PYRAZOLE-4-CARBALDEHYDE; 3-TERT-BUTYL-5-CHLORO-1-(PYRIDIN-2-YL)-1H-PYRAZOLE-4-CARBALDEHYDE; 3-TERT-BUTYL-5-CHLORO-1-(PYRIDIN-4-YL)-1H-PYRAZOLE-4-CARBALDEHYDE; 3-TERT-BUTYL-5-CHLORO-1-(PYRIMIDIN-2-YL)-1H-PYRAZOLE-4-CARBALDEHYDE; 3-TERT-BUTYL-5-CHLORO-1-[2-(DIMETHYLAMINO)ETHYL]-1H-PYRAZOLE-4-CARBALDEHYDE; 3-TERT-BUTYL-5-CHLORO-1-CYCLOHEPTYL-1H-PYRAZOLE-4-CARBALDEHYDE; 3-TERT-BUTYL-5-CHLORO-1-CYCLOHEXYL-1H-PYRAZOLE-4-CARBALDEHYDE; 3-TERT-BUTYL-5-CHLORO-1-CYCLOPENTYL-1H-PYRAZOLE-4-CARBALDEHYDE; 3-TERT-BUTYL-5-CHLORO-1-ETHYL-1H-PYRAZOLE-4-CARBALDEHYDE; 3-TERT-BUTYL-5-CHLORO-1-METHYL-1H-PYRAZOLE-4-CARBALDEHYDE; 3-TERT-BUTYL-5-CHLORO-1-PHENYL-1H-PYRAZOLE-4-CARBALDEHYDE; 3-TERT-BUTYL-5-CHLORO-1-PROPYL-1H-PYRAZOLE-4-CARBALDEHYDE; 4-(([(4-BROMOTHIOPHEN-2-YL)METHYL](METHYL)AMINO)METHYL)OXANE-4-CARBALDEHYDE; 4-([(4-BROMOTHIOPHEN-2-YL)METHYL](METHYL)AMINO)-2-METHYLBENZALDEHYDE; 4-([(4-BROMOTHIOPHEN-2-YL)METHYL](METHYL)AMINO)-3,5-DIFLUOROBENZALDEHYDE; 4-([(4-BROMOTHIOPHEN-2-YL)METHYL](METHYL)AMINO)-3-FLUOROBENZALDEHYDE; 4-([(4-BROMOTHIOPHEN-2-YL)METHYL](METHYL)AMINO)-3-METHYLBENZALDEHYDE; 4-([(4-BROMOTHIOPHEN-2-YL)METHYL](METHYL)AMINO)BENZALDEHYDE; 4-(2-BUTYL-5-FORMYL-4-IODO-IMIDAZOL-1-YLMETHYL)-BENZOIC ACID METHYL ESTER; 4-(3-BROMOTHIEN-2-YL)BENZALDEHYDE; 4-(4-BROMO-1H-PYRAZOL-1-YL)-3-FLUOROBENZALDEHYDE; 4-(4-BROMO-1H-PYRAZOL-1-YL)-3-NITROBENZALDEHYDE; 4-(4-BROMO-1H-PYRAZOL-1-YL)BENZALDEHYDE; 4-(4-BROMO-3,5-DIMETHYL-1H-PYRAZOL-1-YL)-2-METHYLBENZALDEHYDE; 4-(4-BROMO-3,5-DIMETHYL-1H-PYRAZOL-1-YL)-3,5-DIFLUOROBENZALDEHYDE; 4-(4-BROMO-3,5-DIMETHYL-1H-PYRAZOL-1-YL)-3-FLUOROBENZALDEHYDE; 4-(4-BROMO-3,5-DIMETHYL-1H-PYRAZOL-1-YL)-3-METHYLBENZALDEHYDE; 4-(4-CHLORO-1H-PYRAZOL-1-YL)-3-FLUOROBENZALDEHYDE; 4-(4-CHLORO-1H-PYRAZOL-1-YL)-3-NITROBENZALDEHYDE; 4-(4-CHLORO-1H-PYRAZOL-1-YL)BENZALDEHYDE; 4-(4-CHLORO-3,5-DIMETHYL-1H-PYRAZOL-1-YL)-2-METHYLBENZALDEHYDE; 4-(4-CHLORO-3,5-DIMETHYL-1H-PYRAZOL-1-YL)-3-FLUOROBENZALDEHYDE; 4-(4-CHLORO-3,5-DIMETHYL-1H-PYRAZOL-1-YL)-3-METHYLBENZALDEHYDE; 4-(4-CHLORO-3,5-DIMETHYL-1H-PYRAZOL-1-YL)-3-NITROBENZALDEHYDE; 4-(4-CHLORO-PYRAZOL-1-YLMETHYL)-5-METHYL-THIOPHENE-2-CARBALDEHYDE; 4-(4-CHLORO-PYRAZOL-1-YLMETHYL)-THIOPHENE-2-CARBALDEHYDE; 4-(5-CHLORO-3-ETHYL-4-FORMYL-1H-PYRAZOL-1-YL)BENZONITRILE; 4-(5-CHLORO-4-FORMYL-3-METHYL-1H-PYRAZOL-1-YL)BENZONITRILE; 4-(5-CHLORO-4-FORMYL-3-PROPYL-1H-PYRAZOL-1-YL)BENZONITRILE; 4,5-DIBROMO-1H-PYRROLE-2-CARBOXALDEHYDE; 4,5-DIBROMO-1-METHYL-1H-IMIDAZOLE-2-CARBALDEHYDE; 4,5-DIBROMO-2-FURALDEHYDE; 4,5-DIBROMO-3-METHYLTHIOPHENE-2-CARBALDEHYDE; 4,5-DIBROMOTHIOPHENE-2-CARBOXALDEHYDE; 4,5-DICHLORO-3-THIOPHENECARBOXALDEHYDE; 4,6,8-TRICHLORO-3-FORMYLCOUMARIN; 4,6-DICHLORO-2H-1-BENZOTHIINE-3-CARBALDEHYDE; 4,6-DICHLORO-2H-BENZOPYRAN-3-CARBOXALDEHYDE; 4,6-DICHLORO-2-METHYL-2H-1-BENZOTHIINE-3-CARBALDEHYDE; 4,6-DICHLORO-3-FORMYL-7-METHYLCOUMARIN; 4,6-DICHLORO-3-FORMYLCOUMARIN; 4-[(2-BROMOPROP-2-EN-1-YL)OXY]-3,5-DIMETHOXYBENZALDEHYDE; 4-[(2-BROMOPROP-2-EN-1-YL)OXY]-3,5-DIMETHYLBENZALDEHYDE; 4-[(2-BROMOPROP-2-EN-1-YL)OXY]-3-CHLORO-5-METHOXYBENZALDEHYDE; 4-[(2-BROMOPROP-2-EN-1-YL)OXY]-3-CHLOROBENZALDEHYDE; 4-[(2-BROMOPROP-2-EN-1-YL)OXY]-3-ETHOXYBENZALDEHYDE; 4-[(2-BROMOPROP-2-EN-1-YL)OXY]-3-METHOXYBENZALDEHYDE; 4-[(2-BROMOPROP-2-EN-1-YL)OXY]-3-NITROBENZALDEHYDE; 4-[(2-BROMOPROP-2-EN-1-YL)OXY]-5-METHOXY-2-NITROBENZALDEHYDE; 4-[(2-BROMOPROP-2-EN-1-YL)OXY]BENZALDEHYDE; 4-[(2-CHLOROPROP-2-EN-1-YL)OXY]-3,5-DIMETHOXYBENZALDEHYDE; 4-[(2-CHLOROPROP-2-EN-1-YL)OXY]-3,5-DIMETHYLBENZALDEHYDE; 4-[(2-CHLOROPROP-2-EN-1-YL)OXY]-3-ETHOXYBENZALDEHYDE; 4-[(2-CHLOROPROP-2-EN-1-YL)OXY]-3-METHOXYBENZALDEHYDE; 4-[(2-CHLOROPROP-2-EN-1-YL)OXY]-3-NITROBENZALDEHYDE; 4-[(2-CHLOROPROP-2-EN-1-YL)OXY]-5-METHOXY-2-NITROBENZALDEHYDE; 4-[(2-CHLOROPROP-2-EN-1-YL)OXY]BENZALDEHYDE; 4-[(3-BROMOTHIOPHEN-2-YL)METHOXY]-3-CHLORO-5-METHOXYBENZALDEHYDE; 4-[(3-BROMOTHIOPHEN-2-YL)METHOXY]-3-CHLOROBENZALDEHYDE; 4-[(3-BROMOTHIOPHEN-2-YL)METHOXY]-3-ETHOXYBENZALDEHYDE; 4-[(3-BROMOTHIOPHEN-2-YL)METHOXY]-3-METHOXYBENZALDEHYDE; 4-[(3-BROMOTHIOPHEN-2-YL)METHOXY]-3-NITROBENZALDEHYDE; 4-[(3-BROMOTHIOPHEN-2-YL)METHOXY]BENZALDEHYDE; 4-[(4-BROMOTHIOPHEN-2-YL)METHOXY]-3-CHLORO-5-METHOXYBENZALDEHYDE; 4-[(4-BROMOTHIOPHEN-2-YL)METHOXY]-3-CHLOROBENZALDEHYDE; 4-[(4-BROMOTHIOPHEN-2-YL)METHOXY]-3-ETHOXYBENZALDEHYDE; 4-[(4-BROMOTHIOPHEN-2-YL)METHOXY]-3-METHOXYBENZALDEHYDE; 4-[(4-BROMOTHIOPHEN-2-YL)METHOXY]-3-NITROBENZALDEHYDE; 4-[(4-BROMOTHIOPHEN-2-YL)METHOXY]BENZALDEHYDE; 4-[(4-CHLORO-1H-PYRAZOL-1-YL)METHOXY]BENZALDEHYDE; 4-[(4-CHLORO-3-NITRO-1H-PYRAZOL-1-YL)METHOXY]BENZALDEHYDE; 4-[(4-CHLORO-3-NITRO-1H-PYRAZOL-1-YL)METHYL]-3-METHOXYBENZALDEHYDE; 4-[(5-CHLORO-1-METHYL-1H-IMIDAZOL-2-YL)METHOXY]-3,5-DIMETHYLBENZALDEHYDE; 4-[(5-CHLORO-1-METHYL-1H-IMIDAZOL-2-YL)METHOXY]-3-METHOXYBENZALDEHYDE; 4-[(5-CHLORO-1-METHYL-1H-IMIDAZOL-2-YL)METHOXY]BENZALDEHYDE; 4-[2-(3-BROMOTHIOPHEN-2-YL)-

2-OXOETHOXY]-3-CHLOROBENZALDEHYDE; 4-[2-(3-BROMOTHIOPHEN-2-YL)-2-OXOETHOXY]BENZALDEHYDE; 4-[5-CHLORO-3-(DIFLUOROMETHYL)-4-FORMYL-1H-PYRAZOL-1-YL]BENZONITRILE; 4-[5-CHLORO-4-FORMYL-3-(PROPAN-2-YL)-1H-PYRAZOL-1-YL]BENZONITRILE; 4-AMINO-5-CHLORO-1H-PYRAZOLE-3-CARBALDEHYDE; 4-BROMO-1-(4-CHLOROBENZYL)-1H-PYRAZOLE-5-CARBALDEHYDE; 4-BROMO-1-(4-CHLOROPHENYL)-1H-PYRAZOLE-5-CARBOXALDEHYDE; 4-BROMO-1-(4-METHYLBENZYL)-1H-PYRAZOLE-5-CARBOXALDEHYDE; 4-BROMO-1-ETHYL-1H-PYRAZOLE-3-CARBALDEHYDE; 4-BROMO-1H-PYRAZOLE-3-CARBALDEHYDE; 4-BROMO-1H-PYRAZOLE-5-CARBALDEHYDE; 4-BROMO-1H-PYRROLE-2-CARBALDEHYDE; 4-BROMO-1-METHYL-1H-IMIDAZOLE-5-CARBOXALDEHYDE; 4-BROMO-1-METHYL-1H-PYRAZOLE-3-CARBALDEHYDE; 4-BROMO-1-METHYL-1H-PYRAZOLE-5-CARBALDEHYDE; 4-BROMO-1-PROPYL-1H-PYRAZOLE-3-CARBALDEHYDE; 4-BROMO-2-(4-BROMO-1H-PYRAZOL-1-YL)BENZALDEHYDE; 4-BROMO-2-(4-BROMO-3,5-DIMETHYL-1H-PYRAZOL-1-YL)BENZALDEHYDE; 4-BROMO-2-(4-CHLORO-1H-PYRAZOL-1-YL)BENZALDEHYDE; 4-BROMO-2-(4-CHLORO-3,5-DIMETHYL-1H-PYRAZOL-1-YL)BENZALDEHYDE; 4-BROMO-2,3-THIOPHENEDICARBOXALDEHYDE; 4-BROMO-2,5-BIS(ETHYLSULFANYL)-3-THIOPHENECARBALDEHYDE; 4-BROMO-2-CHLORO-1H-INDOLE-3-CARBALDEHYDE; 4-BROMO-2-ETHYL-2H-PYRAZOLE-3-CARBALDEHYDE; 4-BROMO-2-FORMYLTHIAZOLE; 4-BROMO-2-FORMYLTHIOPHEN-3-YLBORONIC ACID; 4-BROMO-2-FURALDEHYDE; 4-BROMO-3,5-DIMETHYL-1H-PYRROLE-2-CARBALDEHYDE; 4-BROMO-3-FORMYL-PYRAZOLO[1,5-A]PYRIDINE-2-CARBOXYLIC ACID ETHYL ESTER; 4-BROMO-3-FORMYLTHIOPHEN-2-YLBORONIC ACID; 4-BROMO-3-METHYL-1H-PYRAZOLE-5-CARBALDEHYDE; 4-BROMO-3-METHYLTHIOPHENE-2-CARBALDEHYDE; 4-BROMO-5-(4-METHYL-PYRIMIDIN-2-YLSULFANYL)-FURAN-2-CARBALDEHYDE; 4-BROMO-5,6-DIHYDRO-2H-PYRAN-3-CARBALDEHYDE; 4-BROMO-5-[(4-CHLOROPHENYL)THIO]-2-FURALDEHYDE; 4-BROMO-5-[(4-METHYLPHENYL)THIO]-2-FURALDEHYDE; 4-BROMO-5-ETHYL-THIOPHENE-2-CARBALDEHYDE; 4-BROMO-5-FORMYL-3,6-DIHYDRO-2H-PYRIDINE-1-CARBOXYLIC ACID BENZYL ESTER; 4-BROMO-5-METHYLTHIOPHENE-2-CARBALDEHYDE; 4-BROMO-5-MORPHOLIN-4-YL-2-FURALDEHYDE; 4-BROMO-5-NITRO-2-THIOPHENECARBOXALDEHYDE; 4-BROMO-5-PROPYLTHIOPHENE-2-CARBALDEHYDE; 4-BROMO-PENT-4-ENAL; 4-BROMOTHIAZOLE-5-CARBALDEHYDE; 4-BROMOTHIOPHENE-2-CARBOXALDEHYDE; 4-CHLORO-1,2-DIHYDRO-2-OXO-3-QUINOLINECARBOXALDEHYDE; 4-CHLORO-1,3-DIMETHYL-1H-PYRAZOLE-5-CARBALDEHYDE; 4-CHLORO-1-ETHYL-1H-IMIDAZOLE-5-CARBALDEHYDE; 4-CHLORO-1-ETHYL-1H-PYRAZOLE-5-CARBOXALDEHYDE; 4-CHLORO-1-ETHYL-3-METHYL-1H-PYRAZOLE-5-CARBALDEHYDE; 4-CHLORO-1-ETHYLPYRAZOLE-3-CARBALDEHYDE; 4-CHLORO-1H-PYRAZOLE-5-CARBALDEHYDE; 4-CHLORO-1-METHYL-1H-PYRAZOLE-3-CARBALDEHYDE; 4-CHLORO-1-METHYL-1H-PYRAZOLE-5-CARBALDEHYDE; 4-CHLORO-1-PROPYL-1H-PYRAZOLE-3-CARBALDEHYDE; 4-CHLORO-2-(1-ACETYL-4-PIPERAZINYL)-5-THIAZOLECARBOXALDEHYDE; 4-CHLORO-2-(1-METHYL-4-PIPERAZINYL)-5-THIAZOLECARBOXALDEHYDE; 4-CHLORO-2-(1-METHYLIMIDAZOLYL-2-THIO)-5-THIAZOLECARBOXALDEHYDE; 4-CHLORO-2-(1-PHENYL-ETHYLAMINO)-THIAZOLE-5-CARBALDEHYDE; 4-CHLORO-2-(1-PIPERIDIN-4-OL)-5-THIAZOLECARBOXALDEHYDE; 4-CHLORO-2-(1-PIPERIDINO)-5-THIAZOLECARBOXALDEHYDE; 4-CHLORO-2-(1-PYRROLIDINO)-5-THIAZOLECARBOXALDEHYDE; 4-CHLORO-2-(2,4-DICHLOROPHENOXY)-5-THIAZOLECARBOXALDEHYDE; 4-CHLORO-2-(2,4-DIFLUOROPHENOXY)-5-THIAZOLECARBOXALDEHYDE; 4-CHLORO-2-(2,6-DIMETHYLPHENYL)-1-METHYL-1H-IMIDAZOLE-5-CARBALDEHYDE; 4-CHLORO-2-(2-BENZOXAZOLYLTHIO)-5-THIAZOLECARBOXALDEHYDE; 4-CHLORO-2-(2-CHLOROPHENOXY)-5-THIAZOLECARBOXALDEHYDE; 4-CHLORO-2-(2-FLUOROPHENOXY)-5-THIAZOLECARBOXALDEHYDE; 4-CHLORO-2-(3,4-DICHLOROPHENOXY)-5-THIAZOLECARBOXALDEHYDE; 4-CHLORO-2-(3,4-DIFLUOROPHENOXY)-5-THIAZOLECARBOXALDEHYDE; 4-CHLORO-2-(3,4-DIHYDRO-1H-ISOQUINOLIN-2-YL)-THIAZOLE-5-CARBALDEHYDE; 4-CHLORO-2-(3,4-DIMETHOXYPHENOXY)-5-THIAZOLECARBOXALDEHYDE; 4-CHLORO-2-(3,4-DIMETHYLPHENOXY)-5-THIAZOLECARBOXALDEHYDE; 4-CHLORO-2-(3-CHLOROPHENOXY)-5-THIAZOLECARBOXALDEHYDE; 4-CHLORO-2-(3-FLUOROPHENOXY)-5-THIAZOLECARBOXALDEHYDE; 4-CHLORO-2-(3-NITROPHENOXY)-5-THIAZOLECARBOXALDEHYDE; 4-CHLORO-2-(4-(TRIFLUOROMETHYL)PHENYL)THIAZOLE-5-CARBALDEHYDE; 4-CHLORO-2-(4-BROMOHENOXY)-5-THIAZOLECARBOXALDEHYDE; 4-CHLORO-2-(4-CARBOMETHOXYL-1-PIPERIDINYL)-5-THIAZOLECARBOXALDEHYDE; 4-CHLORO-2-(4-CHLOROPHENOXY)-5-THIAZOLECARBOXALDEHYDE; 4-CHLORO-2-(4-FLUOROPHENOXY)-5-THIAZOLECARBOXALDEHYDE; 4-CHLORO-2-(4-FLUOROPHENYL)THIAZOLE-5-CARBALDEHYDE; 4-CHLORO-2-(4-METHOXYPHENOXY)-5-THIAZOLECARBOXALDEHYDE; 4-CHLORO-2-(4-METHYLPHENOXY)-5-THIAZOLECARBOXALDEHYDE; 4-CHLORO-2-(4-METHYLPYRIMIDINYL-2-THIO)-5-THIAZOLECARBOXALDEHYDE; 4-CHLORO-2-(4-MORPHOLINO)-5-THIAZOLECARBOXALDEHYDE; 4-CHLORO-2-(4-NITROPHENOXY)-5-THIAZOLECARBOXALDEHYDE; 4-CHLORO-2-(4-OXO-PIPERIDINYL)-5-THIAZOLECARBOXALDEHYDE; 4-CHLORO-2-(4-PHENYL-PIPERAZIN-1-YL)-THIAZOLE-5-CARBALDEHYDE; 4-CHLORO-2-(DIETHYLAMINO)-1,3-THIAZOLE-5-CARBALDEHYDE; 4-CHLORO-2-(DIMETHYLAMINO)-1,3-THIAZOLE-5-CARBALDEHYDE; 4-CHLORO-2-(PHENYLTHIO)-1,3-THIAZOLE-5-CARBALDEHYDE; 4-CHLORO-2-(TERT-BUTYLAMINO)-5-THIAZOLECARBOXALDEHYDE;

4-CHLORO-2-[(2,6-DIETHYLPHENYL)AMINO]-1,3-THIAZOLE-5-CARBALDEHYDE; 4-CHLORO-2-[(2-CHLOROPHENYL)AMINO]-1,3-THIAZOLE-5-CARBALDEHYDE; 4-CHLORO-2-[(2-METHOXYPHENYL)AMINO]-1,3-THIAZOLE-5-CARBALDEHYDE; 4-CHLORO-2-[(2-METHYLPHENYL)AMINO]-1,3-THIAZOLE-5-CARBALDEHYDE; 4-CHLORO-2-[(3-CHLORO-4-METHYLPHENYL)AMINO]-1,3-THIAZOLE-5-CARBALDEHYDE; 4-CHLORO-2-[(4-CHLOROPHENYL)SULFANYL]-1-PHENYL-1H-IMIDAZOLE-5-CARBALDEHYDE; 4-CHLORO-2-[(4-METHOXYPHENYL)AMINO]-1,3-THIAZOLE-5-CARBALDEHYDE; 4-CHLORO-2-[(4-METHYLPHENYL)AMINO]-1,3-THIAZOLE-5-CARBALDEHYDE; 4-CHLORO-2-[(N-METHYL-N'-3-PHENYLPROPYL)AMINO]-5-THIAZOLECARBOXALDEHYDE; 4-CHLORO-2-[2-(TRIFLUOROMETHYL)PHENOXY]-5-THIAZOLECARBOXALDEHYDE; 4-CHLORO-2-[3-(TRIFLUOROMETHYL)PHENOXY]-5-THIAZOLECARBOXALDEHYDE; 4-CHLORO-2-[4-(TRIFLUOROMETHYL)PHENOXY]-5-THIAZOLECARBOXALDEHYDE; 4-CHLORO-2-ETHOXY-1,3-THIAZOLE-5-CARBALDEHYDE; 4-CHLORO-2-FORMYLPHENYL 4-BROMO-1-METHYL-1H-PYRAZOLE-3-CARBOXYLATE; 4-CHLORO-2-FURANCARBOXALDEHYDE; 4-CHLORO-2H-THIOCHROMENE-3-CARBALDEHYDE; 4-CHLORO-2-METHOXY-1,3-THIAZOLE-5-CARBALDEHYDE; 4-CHLORO-2-METHOXY-1-METHYL-1H-IMIDAZOLE-5-CARBALDEHYDE; 4-CHLORO-2-METHYL-1-(3-TRIFLUOROMETHYL-PHENYL)-6,7-DIHYDRO-1H-INDOLE-5-CARBALDEHYDE; 4-CHLORO-2-METHYL-1-(4-METHYLPHENYL)-6,7-DIHYDRO-1H-INDOLE-5-CARBALDEHYDE; 4-CHLORO-2-MORPHOLIN-1YL-THIAZOLE-5-CARBALDEHYDE; 4-CHLORO-2-OXO-2,3-DIHYDROTHIAZOLE-5-CARBALDEHYDE; 4-CHLORO-2-OXO-2H-CHROMENE-3-CARBALDEHYDE; 4-CHLORO-2-OXO-3-PHENYL-2,3-DIHYDRO-1,3-THIAZOLE-5-CARBALDEHYDE; 4-CHLORO-2-OXO-3-PROPYL-2,3-DIHYDRO-1,3-THIAZOLE-5-CARBALDEHYDE; 4-CHLORO-2-PHENOXY-1,3-THIAZOLE-5-CARBALDEHYDE; 4-CHLORO-2-PHENYLAMINO-THIAZOLE-5-CARBALDEHYDE; 4-CHLORO-2-PHENYLTHIAZOLE-5-CARBALDEHYDE; 4-CHLORO-3-(2-CHLOROETHYL)-2-OXO-2,3-DIHYDRO-1,3-THIAZOLE-5-CARBALDEHYDE; 4-CHLORO-3-(3-METHYLPHENYL)-2-OXO-2,3-DIHYDRO-1,3-THIAZOLE-5-CARBALDEHYDE; 4-CHLORO-3-(4-METHYLPHENYL)-2-OXO-2,3-DIHYDRO-1,3-THIAZOLE-5-CARBALDEHYDE; 4-CHLORO-3-ETHYL-2-OXO-2,3-DIHYDRO-1,3-THIAZOLE-5-CARBALDEHYDE; 4-CHLORO-3-FORMYL-2H-BENZO[H]CHROMENE; 4-CHLORO-3-FORMYL-2-THIOPHENEBORONIC ACID; 4-CHLORO-3-FORMYL-6-METHYLCOUMARIN; 4-CHLORO-3-FORMYLPYRAZOLE; 4-CHLORO-3-METHYL-1,6-DIPHENYL-6,7-DIHYDRO-1H-INDAZOLE-5-CARBALDEHYDE; 4-CHLORO-3-METHYL-1H-PYRAZOLE-5-CARBALDEHYDE; 4-CHLORO-3-METHYL-1H-PYRROLE-2-CARBALDEHYDE; 4-CHLORO-3-METHYL-1-PROPYL-1H-PYRAZOLE-5-CARBALDEHYDE; 4-CHLORO-3-METHYL-2-OXO-2,3-DIHYDRO-1,3-THIAZOLE-5-CARBALDEHYDE; 4-CHLORO-5-FORMYL-3,6,6-TRIMETHYL-6,7-DIHYDRO-1H-INDOLE-2-CARBOXYLIC ACID ETHYL ESTER; 4-CHLORO-5-FORMYL-3-METHYL-6,7-DIHYDRO-1H-INDOLE-2-CARBOXYLIC ACID ETHYL ESTER; 4-CHLORO-5-NITRO-2-FURANCARBOXALDEHYDE; 4-CHLORO-6-FLUORO-2H-1-BENZOTHIINE-3-CARBALDEHYDE; 4-CHLORO-6-FLUORO-2H-BENZOPYRAN-3-CARBOXALDEHYDE; 4-CHLORO-6-FLUORO-2-OXO-2H-CHROMENE-3-CARBALDEHYDE; 4-CHLORO-6-METHYL-2H-THIOCHROMENE-3-CARBALDEHYDE; 4-CHLORO-9-METHYL-2,9-DIHYDRO-1H-CARBAZOLE-3-CARBOXALDEHYDE; 4-CHLOROTHIAZOLE-5-CARBOXALDEHYDE; 4-CHLOROTHIOPHENE-2-CARBALDEHYDE; 4-FORMYL-2-METHOXYPHENYL 3-CHLORO-1-BENZOTHIOPHENE-2-CARBOXYLATE; 4-FORMYL-2-METHOXYPHENYL 4-CHLORO-1-ETHYLPYRAZOLE-3-CARBOXYLATE; 4-FORMYLPHENYL 4-BROMO-1-METHYL-1H-PYRAZOLE-3-CARBOXYLATE; 4-FORMYLPHENYL 4-CHLORO-1-ETHYLPYRAZOLE-3-CARBOXYLATE; 4-FORMYLPHENYL 4-IODO-1-METHYL-1H-PYRAZOLE-3-CARBOXYLATE; 4-IODO-1H-IMIDAZOLE-2-CARBALDEHYDE; 4-IODO-1H-PYRROLE-2-CARBALDEHYDE; 4-IODO-1-METHYL-1H-IMIDAZOLE-5-CARBOXALDEHYDE; 4-IODO-2,5-DIMETHYLTHIOPHENE-3-CARBALDEHYDE; 4-IODO-2-THIOPHENECARBALDEHYDE; 5-([(4-BROMOTHIOPHEN-2-YL)METHYL](METHYL)AMINO)-1,3-DIMETHYL-1H-PYRAZOLE-4-CARBALDEHYDE; 5-([(4-BROMOTHIOPHEN-2-YL)METHYL](METHYL)AMINO)FURAN-2-CARBALDEHYDE; 5-(1-CHLOROETHENYL)-1H-PYRROLE-2-CARBOXALDEHYDE; 5-(4-BROMO-1H-PYRAZOL-1-YL)-1,3-DIMETHYL-1H-PYRAZOLE-4-CARBALDEHYDE; 5-(4-BROMO-3,5-BIS-DIFLUOROMETHYL-PYRAZOL-1-YLMETHYL)-FURAN-2-CARBALDEHYDE; 5-(4-BROMO-3-NITRO-PYRAZOL-1-YLMETHYL)-FURAN-2-CARBALDEHYDE; 5-(4-CHLORO-1H-PYRAZOL-1-YL)-1,3-DIMETHYL-1H-PYRAZOLE-4-CARBALDEHYDE; 5-(4-CHLORO-3,5-DIMETHYL-1H-PYRAZOL-1-YL)-1,3-DIMETHYL-1H-PYRAZOLE-4-CARBALDEHYDE; 5-(4-CHLORO-PYRAZOL-1-YLMETHYL)-FURAN-2-CARBALDEHYDE; 5-[(4-CHLORO-3-NITRO-1H-PYRAZOL-1-YL)METHYL]-2-FURALDEHYDE; 5-BROMO-1-(1,1-DIMETHYLETHYL)-3-(2,3,4-TRIFLUOROPHENYL)-1H-PYRAZOLE-4-CARBOXALDEHYDE; 5-BROMO-1-(1,1-DIMETHYLETHYL)-3-(2,6-DIMETHYLPHENYL)-1H-PYRAZOLE-4-CARBOXALDEHYDE; 5-BROMO-1-(1,1-DIMETHYLETHYL)-3-(2-FLUORO-4-NITROPHENYL)-1H-PYRAZOLE-4-CARBOXALDEHYDE; 5-BROMO-1-(1,1-DIMETHYLETHYL)-3-(2-FLUORO-5-NITROPHENYL)-1H-PYRAZOLE-4-CARBOXALDEHYDE; 5-BROMO-1-(1,1-DIMETHYLETHYL)-3-(2-FLUOROPHENYL)-1H-PYRAZOLE-4-CARBOXALDEHYDE; 5-BROMO-1-(1,1-DIMETHYLETHYL)-3-(2-METHOXYPHENYL)-1H-PYRAZOLE-4-CARBOXALDEHYDE; 5-BROMO-1-(1,1-DIMETHYLETHYL)-3-(2-METHYLPHENYL)-1H-PYRAZOLE-4-CARBOXALDEHYDE; 5-BROMO-1-(1,1-DIMETHYLETHYL)-3-(2-NITROPHENYL)-1H-PYRAZOLE-4-CARBOXALDEHYDE; 5-BROMO-1-(1,1-DIMETHYLETHYL)-3-(3,5-DIMETHYLPHENYL)-1H-PYRAZOLE-4-CARBOXALDEHYDE; 5-BROMO-1-(1,1-DIMETHYLETHYL)-3-(3-FLUOROPHENYL)-1H-PYRAZOLE-4-CARBOXALDEHYDE; 5-BROMO-1-(1,1-DIMETHYLETHYL)-3-(3-METHOXYPHENYL)-1H-PYRAZOLE-4-CARBOXALDEHYDE; 5-BROMO-1-(1,

1-DIMETHYLETHYL)-3-(3-METHYLPHENYL)-1H-PYRAZOLE-4-CARBOXALDEHYDE; 5-BROMO-1-(1,1-DIMETHYLETHYL)-3-(3-NITROPHENYL)-1H-PYRAZOLE-4-CARBOXALDEHYDE; 5-BROMO-1-(1,1-DIMETHYLETHYL)-3-(4-ETHYLPHENYL)-1H-PYRAZOLE-4-CARBOXALDEHYDE; 5-BROMO-1-(1,1-DIMETHYLETHYL)-3-(4-FLUORO-3-NITROPHENYL)-1H-PYRAZOLE-4-CARBOXALDEHYDE; 5-BROMO-1-(1,1-DIMETHYLETHYL)-3-(4-FLUOROPHENYL)-1H-PYRAZOLE-4-CARBOXALDEHYDE; 5-BROMO-1-(1,1-DIMETHYLETHYL)-3-(4-METHOXYPHENYL)-1H-PYRAZOLE-4-CARBOXALDEHYDE; 5-BROMO-1-(1,1-DIMETHYLETHYL)-3-(4-METHYLPHENYL)-1H-PYRAZOLE-4-CARBOXALDEHYDE; 5-BROMO-1-(1,1-DIMETHYLETHYL)-3-(4-NITROPHENYL)-1H-PYRAZOLE-4-CARBOXALDEHYDE; 5-BROMO-1-(1,1-DIMETHYLETHYL)-3-(4-PROPYLPHENYL)-1H-PYRAZOLE-4-CARBOXALDEHYDE; 5-BROMO-1-(1,1-DIMETHYLETHYL)-3-[2-(TRIFLUOROMETHYL)PHENYL]-1H-PYRAZOLE-4-CARBOXALDEHYDE; 5-BROMO-1-(1,1-DIMETHYLETHYL)-3-[3-(TRIFLUOROMETHYL)PHENYL]-1H-PYRAZOLE-4-CARBOXALDEHYDE; 5-BROMO-1-(1,1-DIMETHYLETHYL)-3-[4-(1,1-DIMETHYLETHYL)PHENYL]-1H-PYRAZOLE-4-CARBOXALDEHYDE; 5-BROMO-1-(1,1-DIMETHYLETHYL)-3-[4-(1-METHYLETHYL)PHENYL]-1H-PYRAZOLE-4-CARBOXALDEHYDE; 5-BROMO-1-(1,1-DIMETHYLETHYL)-3-[4-(TRIFLUOROMETHYL)PHENYL]-1H-PYRAZOLE-4-CARBOXALDEHYDE; 5-BROMO-1-(1,1-DIMETHYLETHYL)-3-PHENYL-1H-PYRAZOLE-4-CARBOXALDEHYDE; 5-BROMO-1-(2,4-DICHLOROPHENYL)-1H-PYRAZOLE-4-CARBOXALDEHYDE; 5-BROMO-1-(2,4-DICHLOROPHENYL)-3-PHENYL-1H-PYRAZOLE-4-CARBOXALDEHYDE; 5-BROMO-1-(2,4-DIFLUOROPHENYL)-1H-PYRAZOLE-4-CARBOXALDEHYDE; 5-BROMO-1-(2,4-DIFLUOROPHENYL)-3-(2,5-DIFLUOROPHENYL)-1H-PYRAZOLE-4-CARBOXALDEHYDE; 5-BROMO-1-(2,4-DIFLUOROPHENYL)-3-(2,6-DIFLUOROPHENYL)-1H-PYRAZOLE-4-CARBOXALDEHYDE; 5-BROMO-1-(2,4-DIFLUOROPHENYL)-3-(2-FLUOROPHENYL)-1H-PYRAZOLE-4-CARBOXALDEHYDE; 5-BROMO-1-(2,4-DIFLUOROPHENYL)-3-(3,4-DIFLUOROPHENYL)-1H-PYRAZOLE-4-CARBOXALDEHYDE; 5-BROMO-1-(2,4-DIFLUOROPHENYL)-3-(3,5-DIFLUOROPHENYL)-1H-PYRAZOLE-4-CARBOXALDEHYDE; 5-BROMO-1-(2,4-DIFLUOROPHENYL)-3-(3-FLUOROPHENYL)-1H-PYRAZOLE-4-CARBOXALDEHYDE; 5-BROMO-1-(2,4-DIFLUOROPHENYL)-3-(4-FLUOROPHENYL)-1H-PYRAZOLE-4-CARBOXALDEHYDE; 5-BROMO-1-(2,4-DIFLUOROPHENYL)-3-PHENYL-1H-PYRAZOLE-4-CARBOXALDEHYDE; 5-BROMO-1-(2,5-DICHLOROPHENYL)-1H-PYRAZOLE-4-CARBOXALDEHYDE; 5-BROMO-1-(2,5-DICHLOROPHENYL)-3-PHENYL-1H-PYRAZOLE-4-CARBOXALDEHYDE; 5-BROMO-1-(2,5-DIFLUOROPHENYL)-1H-PYRAZOLE-4-CARBOXALDEHYDE; 5-BROMO-1-(2,5-DIFLUOROPHENYL)-3-(2,6-DIFLUOROPHENYL)-1H-PYRAZOLE-4-CARBOXALDEHYDE; 5-BROMO-1-(2,5-DIFLUOROPHENYL)-3-(2-FLUOROPHENYL)-1H-PYRAZOLE-4-CARBOXALDEHYDE; 5-BROMO-1-(2,5-DIFLUOROPHENYL)-3-(3,4-DIFLUOROPHENYL)-1H-PYRAZOLE-4-CARBOXALDEHYDE; 5-BROMO-1-(2,5-DIFLUOROPHENYL)-3-(3,5-DIFLUOROPHENYL)-1H-PYRAZOLE-4-CARBOXALDEHYDE; 5-BROMO-1-(2,5-DIFLUOROPHENYL)-3-(3-FLUOROPHENYL)-1H-PYRAZOLE-4-CARBOXALDEHYDE; 5-BROMO-1-(2,5-DIFLUOROPHENYL)-3-(4-FLUOROPHENYL)-1H-PYRAZOLE-4-CARBOXALDEHYDE; 5-BROMO-1-(2,5-DIFLUOROPHENYL)-3-PHENYL-1H-PYRAZOLE-4-CARBOXALDEHYDE; 5-BROMO-1-(2-BROMOPHENYL)-1H-PYRAZOLE-4-CARBOXALDEHYDE; 5-BROMO-1-(2-CHLORO-4-FLUOROPHENYL)-1H-PYRAZOLE-4-CARBOXALDEHYDE; 5-BROMO-1-(2-CHLORO-5-FLUOROPHENYL)-1H-PYRAZOLE-4-CARBOXALDEHYDE; 5-BROMO-1-(2-CHLORO-6-FLUOROBENZYL)-1,6-DIHYDRO-6-OXOPYRIDINE-3-CARBOXALDEHYDE; 5-BROMO-1-(2-CHLOROPHENYL)-1H-PYRAZOLE-4-CARBOXALDEHYDE; 5-BROMO-1-(2-CHLOROPHENYL)-3-(2,3-DIFLUOROPHENYL)-1H-PYRAZOLE-4-CARBOXALDEHYDE; 5-BROMO-1-(2-CHLOROPHENYL)-3-(2,4-DIFLUOROPHENYL)-1H-PYRAZOLE-4-CARBOXALDEHYDE; 5-BROMO-1-(2-CHLOROPHENYL)-3-(2,5-DIFLUOROPHENYL)-1H-PYRAZOLE-4-CARBOXALDEHYDE; 5-BROMO-1-(2-CHLOROPHENYL)-3-(2,6-DIFLUOROPHENYL)-1H-PYRAZOLE-4-CARBOXALDEHYDE; 5-BROMO-1-(2-CHLOROPHENYL)-3-(2-FLUOROPHENYL)-1H-PYRAZOLE-4-CARBOXALDEHYDE; 5-BROMO-1-(2-CHLOROPHENYL)-3-(3,4-DIFLUOROPHENYL)-1H-PYRAZOLE-4-CARBOXALDEHYDE; 5-BROMO-1-(2-CHLOROPHENYL)-3-(3,5-DIFLUOROPHENYL)-1H-PYRAZOLE-4-CARBOXALDEHYDE; 5-BROMO-1-(2-CHLOROPHENYL)-3-(3-CHLOROPHENYL)-1H-PYRAZOLE-4-CARBOXALDEHYDE; 5-BROMO-1-(2-CHLOROPHENYL)-3-(3-FLUOROPHENYL)-1H-PYRAZOLE-4-CARBOXALDEHYDE; 5-BROMO-1-(2-CHLOROPHENYL)-3-(4-CHLOROPHENYL)-1H-PYRAZOLE-4-CARBOXALDEHYDE; 5-BROMO-1-(2-CHLOROPHENYL)-3-(4-FLUOROPHENYL)-1H-PYRAZOLE-4-CARBOXALDEHYDE; 5-BROMO-1-(2-CHLOROPHENYL)-3-PHENYL-1H-PYRAZOLE-4-CARBOXALDEHYDE; 5-BROMO-1-(2-FLUOROPHENYL)-1H-PYRAZOLE-4-CARBOXALDEHYDE; 5-BROMO-1-(2-FLUOROPHENYL)-3-(2,3,4-TRIFLUOROPHENYL)-1H-PYRAZOLE-4-CARBOXALDEHYDE; 5-BROMO-1-(2-FLUOROPHENYL)-3-(2-NITROPHENYL)-1H-PYRAZOLE-4-CARBOXALDEHYDE; 5-BROMO-1-(2-FLUOROPHENYL)-3-(3-FLUOROPHENYL)-1H-PYRAZOLE-4-CARBOXALDEHYDE; 5-BROMO-1-(2-FLUOROPHENYL)-3-(3-NITROPHENYL)-1H-PYRAZOLE-4-CARBOXALDEHYDE; 5-BROMO-1-(2-FLUOROPHENYL)-3-(4-FLUOROPHENYL)-1H-PYRAZOLE-4-CARBOXALDEHYDE; 5-BROMO-1-(2-FLUOROPHENYL)-3-(4-NITROPHENYL)-1H-PYRAZOLE-4-CARBOXALDEHYDE; 5-BROMO-1-(2-FLUOROPHENYL)-3-PHENYL-1H-PYRAZOLE-4-CARBOXALDEHYDE; 5-BROMO-1-(2-NITROPHENYL)-1H-PYRAZOLE-4-CARBOXALDEHYDE; 5-BROMO-1-(2-NITROPHENYL)-3-PHENYL-1H-PYRAZOLE-4-CARBOXALDEHYDE; 5-BROMO-1-(3,4-DICHLOROBENZYL)-6-OXO-1,6-DIHYDRO-3-PYRIDINECARBALDEHYDE; 5-BROMO-1-(3,4-DICHLOROPHENYL)-1H-PYRAZOLE-4-CARBOXALDEHYDE; 5-BROMO-1-(3,4-DICHLOROPHENYL)-3-PHENYL-1H-PYRAZOLE-4-CARBOXALDEHYDE; 5-BROMO-1-(3,4-

DIFLUOROPHENYL)-1H-PYRAZOLE-4-CARBOXALDEHYDE; 5-BROMO-1-(3,4-DIFLUOROPHENYL)-3-(2-FLUOROPHENYL)-1H-PYRAZOLE-4-CARBOXALDEHYDE; 5-BROMO-1-(3,4-DIFLUOROPHENYL)-3-(3,5-DIFLUOROPHENYL)-1H-PYRAZOLE-4-CARBOXALDEHYDE; 5-BROMO-1-(3,4-DIFLUOROPHENYL)-3-(3-FLUOROPHENYL)-1H-PYRAZOLE-4-CARBOXALDEHYDE; 5-BROMO-1-(3,4-DIFLUOROPHENYL)-3-(4-FLUOROPHENYL)-1H-PYRAZOLE-4-CARBOXALDEHYDE; 5-BROMO-1-(3,4-DIFLUOROPHENYL)-3-PHENYL-1H-PYRAZOLE-4-CARBOXALDEHYDE; 5-BROMO-1-(3,5-DICHLOROPHENYL)-1H-PYRAZOLE-4-CARBOXALDEHYDE; 5-BROMO-1-(3,5-DICHLOROPHENYL)-3-PHENYL-1H-PYRAZOLE-4-CARBOXALDEHYDE; 5-BROMO-1-(3,5-DIFLUOROPHENYL)-1H-PYRAZOLE-4-CARBOXALDEHYDE; 5-BROMO-1-(3,5-DIFLUOROPHENYL)-3-(2-FLUOROPHENYL)-1H-PYRAZOLE-4-CARBOXALDEHYDE; 5-BROMO-1-(3,5-DIFLUOROPHENYL)-3-(3-FLUOROPHENYL)-1H-PYRAZOLE-4-CARBOXALDEHYDE; 5-BROMO-1-(3,5-DIFLUOROPHENYL)-3-(4-FLUOROPHENYL)-1H-PYRAZOLE-4-CARBOXALDEHYDE; 5-BROMO-1-(3,5-DIFLUOROPHENYL)-3-PHENYL-1H-PYRAZOLE-4-CARBOXALDEHYDE; 5-BROMO-1-(3-BROMOPHENYL)-1H-PYRAZOLE-4-CARBOXALDEHYDE; 5-BROMO-1-(3-CHLORO-4-FLUOROPHENYL)-1H-PYRAZOLE-4-CARBOXALDEHYDE; 5-BROMO-1-(3-CHLOROPHENYL)-1H-PYRAZOLE-4-CARBOXALDEHYDE; 5-BROMO-1-(3-CHLOROPHENYL)-3-(2,3-DIFLUOROPHENYL)-1H-PYRAZOLE-4-CARBOXALDEHYDE; 5-BROMO-1-(3-CHLOROPHENYL)-3-(2,4-DIFLUOROPHENYL)-1H-PYRAZOLE-4-CARBOXALDEHYDE; 5-BROMO-1-(3-CHLOROPHENYL)-3-(2,5-DIFLUOROPHENYL)-1H-PYRAZOLE-4-CARBOXALDEHYDE; 5-BROMO-1-(3-CHLOROPHENYL)-3-(2,6-DIFLUOROPHENYL)-1H-PYRAZOLE-4-CARBOXALDEHYDE; 5-BROMO-1-(3-CHLOROPHENYL)-3-(2-FLUOROPHENYL)-1H-PYRAZOLE-4-CARBOXALDEHYDE; 5-BROMO-1-(3-CHLOROPHENYL)-3-(3,4-DIFLUOROPHENYL)-1H-PYRAZOLE-4-CARBOXALDEHYDE; 5-BROMO-1-(3-CHLOROPHENYL)-3-(3,5-DIFLUOROPHENYL)-1H-PYRAZOLE-4-CARBOXALDEHYDE; 5-BROMO-1-(3-CHLOROPHENYL)-3-(3-FLUOROPHENYL)-1H-PYRAZOLE-4-CARBOXALDEHYDE; 5-BROMO-1-(3-CHLOROPHENYL)-3-(4-CHLOROPHENYL)-1H-PYRAZOLE-4-CARBOXALDEHYDE; 5-BROMO-1-(3-CHLOROPHENYL)-3-(4-FLUOROPHENYL)-1H-PYRAZOLE-4-CARBOXALDEHYDE; 5-BROMO-1-(3-CHLOROPHENYL)-3-PHENYL-1H-PYRAZOLE-4-CARBOXALDEHYDE; 5-BROMO-1-(3-FLUOROPHENYL)-1H-PYRAZOLE-4-CARBOXALDEHYDE; 5-BROMO-1-(3-FLUOROPHENYL)-3-(2,3,4-TRIFLUOROPHENYL)-1H-PYRAZOLE-4-CARBOXALDEHYDE; 5-BROMO-1-(3-NITROPHENYL)-1H-PYRAZOLE-4-CARBOXALDEHYDE; 5-BROMO-1-(3-NITROPHENYL)-3-PHENYL-1H-PYRAZOLE-4-CARBOXALDEHYDE; 5-BROMO-1-(4-BROMOPHENYL)-1H-PYRAZOLE-4-CARBOXALDEHYDE; 5-BROMO-1-(4-CHLOROPHENYL)-1H-PYRAZOLE-4-CARBOXALDEHYDE; 5-BROMO-1-(4-CHLOROPHENYL)-3-(2,3-DIFLUOROPHENYL)-1H-PYRAZOLE-4-CARBOXALDEHYDE; 5-BROMO-1-(4-CHLOROPHENYL)-3-(2,4-DIFLUOROPHENYL)-1H-PYRAZOLE-4-CARBOXALDEHYDE; 5-BROMO-1-(4-CHLOROPHENYL)-3-(2,5-DIFLUOROPHENYL)-1H-PYRAZOLE-4-CARBOXALDEHYDE; 5-BROMO-1-(4-CHLOROPHENYL)-3-(2,6-DIFLUOROPHENYL)-1H-PYRAZOLE-4-CARBOXALDEHYDE; 5-BROMO-1-(4-CHLOROPHENYL)-3-(3,4-DIFLUOROPHENYL)-1H-PYRAZOLE-4-CARBOXALDEHYDE; 5-BROMO-1-(4-CHLOROPHENYL)-3-(3,5-DIFLUOROPHENYL)-1H-PYRAZOLE-4-CARBOXALDEHYDE; 5-BROMO-1-(4-FLUOROPHENYL)-1H-PYRAZOLE-4-CARBOXALDEHYDE; 5-BROMO-1-(4-FLUOROPHENYL)-3-(2,3,4-TRIFLUOROPHENYL)-1H-PYRAZOLE-4-CARBOXALDEHYDE; 5-BROMO-1-(4-FLUOROPHENYL)-3-(2-NITROPHENYL)-1H-PYRAZOLE-4-CARBOXALDEHYDE; 5-BROMO-1-(4-FLUOROPHENYL)-3-(3-NITROPHENYL)-1H-PYRAZOLE-4-CARBOXALDEHYDE; 5-BROMO-1-(4-FLUOROPHENYL)-3-(4-NITROPHENYL)-1H-PYRAZOLE-4-CARBOXALDEHYDE; 5-BROMO-1-(4-FLUOROPHENYL)-3-PHENYL-1H-PYRAZOLE-4-CARBOXALDEHYDE; 5-BROMO-1-(4-METHOXYBENZYL)PYRROLE-2-CARBALDEHYDE; 5-BROMO-1-(4-METHYLBENZYL)-6-OXO-1,6-DIHYDRO-3-PYRIDINECARBALDEHYDE; 5-BROMO-1-(4-NITROPHENYL)-1H-PYRAZOLE-4-CARBOXALDEHYDE; 5-BROMO-1-(4-NITROPHENYL)-3-PHENYL-1H-PYRAZOLE-4-CARBOXALDEHYDE; 5-BROMO-1,3-DIMETHYL-1H-PYRAZOLE-4-CARBOXALDEHYDE; 5-BROMO-1,3-DIPHENYL-1H-PYRAZOLE-4-CARBOXALDEHYDE; 5-BROMO-1-[2-(TRIFLUOROMETHYL)PHENYL]-1H-PYRAZOLE-4-CARBOXALDEHYDE; 5-BROMO-1-[3-(TRIFLUOROMETHYL)PHENYL]-1H-PYRAZOLE-4-CARBOXALDEHYDE; 5-BROMO-1-[4-(TRIFLUOROMETHYL)PHENYL]-1H-PYRAZOLE-4-CARBOXALDEHYDE; 5-BROMO-1H-PYRAZOLE-3-CARBALDEHYDE; 5-BROMO-1H-PYRROLE-2-CARBALDEHYDE; 5-BROMO-1H-PYRROLE-3-CARBALDEHYDE; 5-BROMO-1-METHYL-1H-IMIDAZOLE-2-CARBALDEHYDE; 5-BROMO-1-METHYL-1H-PYRAZOLE-4-CARBALDEHYDE; 5-BROMO-1-METHYL-3-(2,3,4-TRIFLUOROPHENYL)-1H-PYRAZOLE-4-CARBOXALDEHYDE; 5-BROMO-1-METHYL-3-(2-METHYLPHENYL)-1H-PYRAZOLE-4-CARBOXALDEHYDE; 5-BROMO-1-METHYL-3-(2-METHYLPROPYL)-1H-PYRAZOLE-4-CARBOXALDEHYDE; 5-BROMO-1-METHYL-3-(2-NITROPHENYL)-1H-PYRAZOLE-4-CARBOXALDEHYDE; 5-BROMO-1-METHYL-3-(3-METHYLPHENYL)-1H-PYRAZOLE-4-CARBOXALDEHYDE; 5-BROMO-1-METHYL-3-(3-NITROPHENYL)-1H-PYRAZOLE-4-CARBOXALDEHYDE; 5-BROMO-1-METHYL-3-(4-METHYLPHENYL)-1H-PYRAZOLE-4-CARBOXALDEHYDE; 5-BROMO-1-METHYL-3-(4-NITROPHENYL)-1H-PYRAZOLE-4-CARBOXALDEHYDE; 5-BROMO-1-METHYL-3-(4-PROPYLPHENYL)-1H-PYRAZOLE-4-CARBOXALDEHYDE; 5-BROMO-1-METHYL-3-[2-(TRIFLUOROMETHYL)PHENYL]-1H-PYRAZOLE-4-CARBOXALDEHYDE; 5-BROMO-1-METHYL-3-[3-(TRIFLUOROMETHYL)PHENYL]-1H-PYRAZOLE-4-CARBOXALDEHYDE; 5-BROMO-1-METHYL-3-[4-(1-METHYLETHYL)PHENYL]-1H-PYRAZOLE-4-CARBOXALDEHYDE; 5-BROMO-1-METHYL-3-[4-

(TRIFLUOROMETHYL)PHENYL]-1H-PYRAZOLE-4-CARBOXALDEHYDE; 5-BROMO-1-METHYL-3-PHENYL-1H-PYRAZOLE-4-CARBOXALDEHYDE; 5-BROMO-1-METHYL-3-PROPYL-1H-PYRAZOLE-4-CARBOXALDEHYDE; 5-BROMO-1-PHENYL-3-(4-PROPYLPHENYL)-1H-PYRAZOLE-4-CARBOXALDEHYDE; 5-BROMO-1-PHENYL-3-[2-(TRIFLUOROMETHYL)PHENYL]-1H-PYRAZOLE-4-CARBOXALDEHYDE; 5-BROMO-1-PHENYL-3-[3-(TRIFLUOROMETHYL)PHENYL]-1H-PYRAZOLE-4-CARBOXALDEHYDE; 5-BROMO-1-PHENYL-3-[4-(TRIFLUOROMETHYL)PHENYL]-1H-PYRAZOLE-4-CARBOXALDEHYDE; 5-BROMO-1-PHENYL-3-PROPYL-1H-PYRAZOLE-4-CARBOXALDEHYDE; 5-BROMO-2-[(2-BROMOPROP-2-EN-1-YL)OXY]BENZALDEHYDE; 5-BROMO-2-[(2-CHLOROPROP-2-EN-1-YL)OXY]BENZALDEHYDE; 5-BROMO-2-[(3-BROMOTHIOPHEN-2-YL)METHOXY]BENZALDEHYDE; 5-BROMO-2-[(4-BROMOTHIOPHEN-2-YL)METHOXY]BENZALDEHYDE; 5-BROMO-2-[(5-CHLORO-1-METHYL-1H-IMIDAZOL-2-YL)METHOXY]BENZALDEHYDE; 5-BROMO-2-CHLORO-1H-INDOLE-3-CARBALDEHYDE; 5-BROMO-2-METHYL-2H-INDAZOLE-3-CARBALDEHYDE; 5-BROMO-2-PHENYLIMIDAZO[1,2-A]PYRIDINE-3-CARBALDEHYDE; 5-BROMO-3-(2,3,4-TRIFLUOROPHENYL)-1-PHENYL-1H-PYRAZOLE-4-CARBOXALDEHYDE; 5-BROMO-3-(2,3-DICHLOROPHENYL)-1-(1,1-DIMETHYLETHYL)-1H-PYRAZOLE-4-CARBOXALDEHYDE; 5-BROMO-3-(2,3-DICHLOROPHENYL)-1-METHYL-1H-PYRAZOLE-4-CARBOXALDEHYDE; 5-BROMO-3-(2,3-DICHLOROPHENYL)-1-PHENYL-1H-PYRAZOLE-4-CARBOXALDEHYDE; 5-BROMO-3-(2,3-DIFLUOROPHENYL)-1-(1,1-DIMETHYLETHYL)-1H-PYRAZOLE-4-CARBOXALDEHYDE; 5-BROMO-3-(2,3-DIFLUOROPHENYL)-1-(2,4-DIFLUOROPHENYL)-1H-PYRAZOLE-4-CARBOXALDEHYDE; 5-BROMO-3-(2,3-DIFLUOROPHENYL)-1-(2,5-DIFLUOROPHENYL)-1H-PYRAZOLE-4-CARBOXALDEHYDE; 5-BROMO-3-(2,3-DIFLUOROPHENYL)-1-(2-FLUOROPHENYL)-1H-PYRAZOLE-4-CARBOXALDEHYDE; 5-BROMO-3-(2,3-DIFLUOROPHENYL)-1-(3,4-DIFLUOROPHENYL)-1H-PYRAZOLE-4-CARBOXALDEHYDE; 5-BROMO-3-(2,3-DIFLUOROPHENYL)-1-(3,5-DIFLUOROPHENYL)-1H-PYRAZOLE-4-CARBOXALDEHYDE; 5-BROMO-3-(2,3-DIFLUOROPHENYL)-1-(3-FLUOROPHENYL)-1H-PYRAZOLE-4-CARBOXALDEHYDE; 5-BROMO-3-(2,3-DIFLUOROPHENYL)-1-(4-FLUOROPHENYL)-1H-PYRAZOLE-4-CARBOXALDEHYDE; 5-BROMO-3-(2,3-DIFLUOROPHENYL)-1-METHYL-1H-PYRAZOLE-4-CARBOXALDEHYDE; 5-BROMO-3-(2,3-DIFLUOROPHENYL)-1-PHENYL-1H-PYRAZOLE-4-CARBOXALDEHYDE; 5-BROMO-3-(2,3-DIMETHOXYPHENYL)-1-(1,1-DIMETHYLETHYL)-1H-PYRAZOLE-4-CARBOXALDEHYDE; 5-BROMO-3-(2,3-DIMETHOXYPHENYL)-1-METHYL-1H-PYRAZOLE-4-CARBOXALDEHYDE; 5-BROMO-3-(2,3-DIMETHOXYPHENYL)-1-PHENYL-1H-PYRAZOLE-4-CARBOXALDEHYDE; 5-BROMO-3-(2,4-DICHLOROPHENYL)-1-(1,1-DIMETHYLETHYL)-1H-PYRAZOLE-4-CARBOXALDEHYDE; 5-BROMO-3-(2,4-DICHLOROPHENYL)-1-METHYL-1H-PYRAZOLE-4-CARBOXALDEHYDE; 5-BROMO-3-(2,4-DICHLOROPHENYL)-1-PHENYL-1H-PYRAZOLE-4-CARBOXALDEHYDE; 5-BROMO-3-(2,4-DIFLUOROPHENYL)-1-(1,1-DIMETHYLETHYL)-1H-PYRAZOLE-4-CARBOXALDEHYDE; 5-BROMO-3-(2,4-DIFLUOROPHENYL)-1-(2,5-DIFLUOROPHENYL)-1H-PYRAZOLE-4-CARBOXALDEHYDE; 5-BROMO-3-(2,4-DIFLUOROPHENYL)-1-(2-FLUOROPHENYL)-1H-PYRAZOLE-4-CARBOXALDEHYDE; 5-BROMO-3-(2,4-DIFLUOROPHENYL)-1-(3,4-DIFLUOROPHENYL)-1H-PYRAZOLE-4-CARBOXALDEHYDE; 5-BROMO-3-(2,4-DIFLUOROPHENYL)-1-(3,5-DIFLUOROPHENYL)-1H-PYRAZOLE-4-CARBOXALDEHYDE; 5-BROMO-3-(2,4-DIFLUOROPHENYL)-1-(3-FLUOROPHENYL)-1H-PYRAZOLE-4-CARBOXALDEHYDE; 5-BROMO-3-(2,4-DIFLUOROPHENYL)-1-(4-FLUOROPHENYL)-1H-PYRAZOLE-4-CARBOXALDEHYDE; 5-BROMO-3-(2,4-DIFLUOROPHENYL)-1-METHYL-1H-PYRAZOLE-4-CARBOXALDEHYDE; 5-BROMO-3-(2,4-DIFLUOROPHENYL)-1-PHENYL-1H-PYRAZOLE-4-CARBOXALDEHYDE; 5-BROMO-3-(2,4-DIMETHOXYPHENYL)-1-(1,1-DIMETHYLETHYL)-1H-PYRAZOLE-4-CARBOXALDEHYDE; 5-BROMO-3-(2,4-DIMETHOXYPHENYL)-1-METHYL-1H-PYRAZOLE-4-CARBOXALDEHYDE; 5-BROMO-3-(2,4-DIMETHOXYPHENYL)-1-PHENYL-1H-PYRAZOLE-4-CARBOXALDEHYDE; 5-BROMO-3-(2,5-DICHLOROPHENYL)-1-(1,1-DIMETHYLETHYL)-1H-PYRAZOLE-4-CARBOXALDEHYDE; 5-BROMO-3-(2,5-DICHLOROPHENYL)-1-METHYL-1H-PYRAZOLE-4-CARBOXALDEHYDE; 5-BROMO-3-(2,5-DICHLOROPHENYL)-1-PHENYL-1H-PYRAZOLE-4-CARBOXALDEHYDE; 5-BROMO-3-(2,5-DIFLUOROPHENYL)-1-(1,1-DIMETHYLETHYL)-1H-PYRAZOLE-4-CARBOXALDEHYDE; 5-BROMO-3-(2,5-DIFLUOROPHENYL)-1-(2-FLUOROPHENYL)-1H-PYRAZOLE-4-CARBOXALDEHYDE; 5-BROMO-3-(2,5-DIFLUOROPHENYL)-1-(3,4-DIFLUOROPHENYL)-1H-PYRAZOLE-4-CARBOXALDEHYDE; 5-BROMO-3-(2,5-DIFLUOROPHENYL)-1-(3,5-DIFLUOROPHENYL)-1H-PYRAZOLE-4-CARBOXALDEHYDE; 5-BROMO-3-(2,5-DIFLUOROPHENYL)-1-(3-FLUOROPHENYL)-1H-PYRAZOLE-4-CARBOXALDEHYDE; 5-BROMO-3-(2,5-DIFLUOROPHENYL)-1-(4-FLUOROPHENYL)-1H-PYRAZOLE-4-CARBOXALDEHYDE; 5-BROMO-3-(2,5-DIFLUOROPHENYL)-1-METHYL-1H-PYRAZOLE-4-CARBOXALDEHYDE; 5-BROMO-3-(2,5-DIFLUOROPHENYL)-1-PHENYL-1H-PYRAZOLE-4-CARBOXALDEHYDE; 5-BROMO-3-(2,5-DIMETHOXYPHENYL)-1-(1,1-DIMETHYLETHYL)-1H-PYRAZOLE-4-CARBOXALDEHYDE; 5-BROMO-3-(2,5-DIMETHOXYPHENYL)-1-METHYL-1H-PYRAZOLE-4-CARBOXALDEHYDE; 5-BROMO-3-(2,5-DIMETHOXYPHENYL)-1-PHENYL-1H-PYRAZOLE-4-CARBOXALDEHYDE; 5-BROMO-3-(2,6-DICHLOROPHENYL)-1-(1,1-DIMETHYLETHYL)-1H-PYRAZOLE-4-CARBOXALDEHYDE; 5-BROMO-3-(2,6-DICHLOROPHENYL)-1-METHYL-1H-PYRAZOLE-4-CARBOXALDEHYDE; 5-BROMO-3-(2,6-DICHLOROPHENYL)-1-PHENYL-1H-PYRAZOLE-4-CARBOXALDEHYDE; 5-BROMO-3-(2,6-DIFLUOROPHENYL)-1-(1,1-DIMETHYLETHYL)-1H-PYRAZOLE-4-CARBOXALDEHYDE; 5-BROMO-3-(2,6-DIFLUOROPHENYL)-1-(2-FLUOROPHENYL)-1H-PYRAZOLE-4-CARBOXALDEHYDE; 5-BROMO-3-(2,6-DIFLUOROPHENYL)-1-(3,4-DIFLUOROPHENYL)-1H-PYRAZOLE-4-CARBOXALDEHYDE; 5-BROMO-3-(2,6-DIFLUOROPHENYL)-1-(3,5-DIFLUOROPHENYL)-1H-PYRAZOLE-4-CARBOXALDEHYDE; 5-BROMO-3-(2,6-DIFLUOROPHENYL)-1-(4-FLUOROPHENYL)-1H-PYRAZOLE-4-CARBOXALDEHYDE; 5-BROMO-3-(2,

6-DIFLUOROPHENYL)-1-METHYL-1H-PYRAZOLE-4-CARBOXALDEHYDE; 5-BROMO-3-(2,6-DIFLUOROPHENYL)-1-PHENYL-1H-PYRAZOLE-4-CARBOXALDEHYDE; 5-BROMO-3-(2,6-DIMETHOXYPHENYL)-1-(1,1-DIMETHYLETHYL)-1H-PYRAZOLE-4-CARBOXALDEHYDE; 5-BROMO-3-(2,6-DIMETHOXYPHENYL)-1-METHYL-1H-PYRAZOLE-4-CARBOXALDEHYDE; 5-BROMO-3-(2,6-DIMETHOXYPHENYL)-1-PHENYL-1H-PYRAZOLE-4-CARBOXALDEHYDE; 5-BROMO-3-(2,6-DIMETHYLPHENYL)-1-PHENYL-1H-PYRAZOLE-4-CARBOXALDEHYDE; 5-BROMO-3-(2-BROMO-4-CHLOROPHENYL)-1-METHYL-1H-PYRAZOLE-4-CARBOXALDEHYDE; 5-BROMO-3-(2-BROMO-4-FLUOROPHENYL)-1-METHYL-1H-PYRAZOLE-4-CARBOXALDEHYDE; 5-BROMO-3-(2-BROMO-5-CHLOROPHENYL)-1-METHYL-1H-PYRAZOLE-4-CARBOXALDEHYDE; 5-BROMO-3-(2-BROMO-5-FLUOROPHENYL)-1-METHYL-1H-PYRAZOLE-4-CARBOXALDEHYDE; 5-BROMO-3-(2-BROMOPHENYL)-1-(1,1-DIMETHYLETHYL)-1H-PYRAZOLE-4-CARBOXALDEHYDE; 5-BROMO-3-(2-BROMOPHENYL)-1-METHYL-1H-PYRAZOLE-4-CARBOXALDEHYDE; 5-BROMO-3-(2-CHLORO-4-FLUOROPHENYL)-1-(1,1-DIMETHYLETHYL)-1H-PYRAZOLE-4-CARBOXALDEHYDE; 5-BROMO-3-(2-CHLORO-4-FLUOROPHENYL)-1-(2-FLUOROPHENYL)-1H-PYRAZOLE-4-CARBOXALDEHYDE; 5-BROMO-3-(2-CHLORO-4-FLUOROPHENYL)-1-(3-FLUOROPHENYL)-1H-PYRAZOLE-4-CARBOXALDEHYDE; 5-BROMO-3-(2-CHLORO-4-FLUOROPHENYL)-1-(4-FLUOROPHENYL)-1H-PYRAZOLE-4-CARBOXALDEHYDE; 5-BROMO-3-(2-CHLORO-4-FLUOROPHENYL)-1-METHYL-1H-PYRAZOLE-4-CARBOXALDEHYDE; 5-BROMO-3-(2-CHLORO-4-FLUOROPHENYL)-1-PHENYL-1H-PYRAZOLE-4-CARBOXALDEHYDE; 5-BROMO-3-(2-CHLORO-4-NITROPHENYL)-1-(1,1-DIMETHYLETHYL)-1H-PYRAZOLE-4-CARBOXALDEHYDE; 5-BROMO-3-(2-CHLORO-4-NITROPHENYL)-1-METHYL-1H-PYRAZOLE-4-CARBOXALDEHYDE; 5-BROMO-3-(2-CHLORO-5-FLUOROPHENYL)-1-(1,1-DIMETHYLETHYL)-1H-PYRAZOLE-4-CARBOXALDEHYDE; 5-BROMO-3-(2-CHLORO-5-FLUOROPHENYL)-1-(2-FLUOROPHENYL)-1H-PYRAZOLE-4-CARBOXALDEHYDE; 5-BROMO-3-(2-CHLORO-5-FLUOROPHENYL)-1-(3-FLUOROPHENYL)-1H-PYRAZOLE-4-CARBOXALDEHYDE; 5-BROMO-3-(2-CHLORO-5-FLUOROPHENYL)-1-(4-FLUOROPHENYL)-1H-PYRAZOLE-4-CARBOXALDEHYDE; 5-BROMO-3-(2-CHLORO-5-FLUOROPHENYL)-1-METHYL-1H-PYRAZOLE-4-CARBOXALDEHYDE; 5-BROMO-3-(2-CHLORO-5-FLUOROPHENYL)-1-PHENYL-1H-PYRAZOLE-4-CARBOXALDEHYDE; 5-BROMO-3-(2-CHLORO-5-NITROPHENYL)-1-(1,1-DIMETHYLETHYL)-1H-PYRAZOLE-4-CARBOXALDEHYDE; 5-BROMO-3-(2-CHLORO-5-NITROPHENYL)-1-METHYL-1H-PYRAZOLE-4-CARBOXALDEHYDE; 5-BROMO-3-(2-CHLORO-6-FLUOROPHENYL)-1-(1,1-DIMETHYLETHYL)-1H-PYRAZOLE-4-CARBOXALDEHYDE; 5-BROMO-3-(2-CHLORO-6-FLUOROPHENYL)-1-(2-FLUOROPHENYL)-1H-PYRAZOLE-4-CARBOXALDEHYDE; 5-BROMO-3-(2-CHLORO-6-FLUOROPHENYL)-1-(3-FLUOROPHENYL)-1H-PYRAZOLE-4-CARBOXALDEHYDE; 5-BROMO-3-(2-CHLORO-6-FLUOROPHENYL)-1-(4-FLUOROPHENYL)-1H-PYRAZOLE-4-CARBOXALDEHYDE; 5-BROMO-3-(2-CHLORO-6-FLUOROPHENYL)-1-METHYL-1H-PYRAZOLE-4-CARBOXALDEHYDE; 5-BROMO-3-(2-CHLORO-6-FLUOROPHENYL)-1-PHENYL-1H-PYRAZOLE-4-CARBOXALDEHYDE; 5-BROMO-3-(2-CHLOROPHENYL)-1-(1,1-DIMETHYLETHYL)-1H-PYRAZOLE-4-CARBOXALDEHYDE; 5-BROMO-3-(2-CHLOROPHENYL)-1-(2,4-DIFLUOROPHENYL)-1H-PYRAZOLE-4-CARBOXALDEHYDE; 5-BROMO-3-(2-CHLOROPHENYL)-1-(2,5-DIFLUOROPHENYL)-1H-PYRAZOLE-4-CARBOXALDEHYDE; 5-BROMO-3-(2-CHLOROPHENYL)-1-(2-FLUOROPHENYL)-1H-PYRAZOLE-4-CARBOXALDEHYDE; 5-BROMO-3-(2-CHLOROPHENYL)-1-(3,4-DIFLUOROPHENYL)-1H-PYRAZOLE-4-CARBOXALDEHYDE; 5-BROMO-3-(2-CHLOROPHENYL)-1-(3,5-DIFLUOROPHENYL)-1H-PYRAZOLE-4-CARBOXALDEHYDE; 5-BROMO-3-(2-CHLOROPHENYL)-1-(3-CHLOROPHENYL)-1H-PYRAZOLE-4-CARBOXALDEHYDE; 5-BROMO-3-(2-CHLOROPHENYL)-1-(4-FLUOROPHENYL)-1H-PYRAZOLE-4-CARBOXALDEHYDE; 5-BROMO-3-(2-CHLOROPHENYL)-1-METHYL-1H-PYRAZOLE-4-CARBOXALDEHYDE; 5-BROMO-3-(2-CHLOROPHENYL)-1-PHENYL-1H-PYRAZOLE-4-CARBOXALDEHYDE; 5-BROMO-3-(2-ETHOXYPHENYL)-1-METHYL-1H-PYRAZOLE-4-CARBOXALDEHYDE; 5-BROMO-3-(2-ETHOXYPHENYL)-1-PHENYL-1H-PYRAZOLE-4-CARBOXALDEHYDE; 5-BROMO-3-(2-FLUORO-4-NITROPHENYL)-1-METHYL-1H-PYRAZOLE-4-CARBOXALDEHYDE; 5-BROMO-3-(2-FLUORO-4-NITROPHENYL)-1-PHENYL-1H-PYRAZOLE-4-CARBOXALDEHYDE; 5-BROMO-3-(2-FLUORO-5-NITROPHENYL)-1-METHYL-1H-PYRAZOLE-4-CARBOXALDEHYDE; 5-BROMO-3-(2-FLUORO-5-NITROPHENYL)-1-PHENYL-1H-PYRAZOLE-4-CARBOXALDEHYDE; 5-BROMO-3-(2-FLUOROPHENYL)-1-(2-NITROPHENYL)-1H-PYRAZOLE-4-CARBOXALDEHYDE; 5-BROMO-3-(2-FLUOROPHENYL)-1-(3-NITROPHENYL)-1H-PYRAZOLE-4-CARBOXALDEHYDE; 5-BROMO-3-(2-FLUOROPHENYL)-1-(4-FLUOROPHENYL)-1H-PYRAZOLE-4-CARBOXALDEHYDE; 5-BROMO-3-(2-FLUOROPHENYL)-1-(4-NITROPHENYL)-1H-PYRAZOLE-4-CARBOXALDEHYDE; 5-BROMO-3-(2-FLUOROPHENYL)-1-METHYL-1H-PYRAZOLE-4-CARBOXALDEHYDE; 5-BROMO-3-(2-FLUOROPHENYL)-1-PHENYL-1H-PYRAZOLE-4-CARBOXALDEHYDE; 5-BROMO-3-(2-METHOXYPHENYL)-1-METHYL-1H-PYRAZOLE-4-CARBOXALDEHYDE; 5-BROMO-3-(2-METHOXYPHENYL)-1-PHENYL-1H-PYRAZOLE-4-CARBOXALDEHYDE; 5-BROMO-3-(2-METHYLPHENYL)-1-PHENYL-1H-PYRAZOLE-4-CARBOXALDEHYDE; 5-BROMO-3-(2-METHYLPROPYL)-1-PHENYL-1H-PYRAZOLE-4-CARBOXALDEHYDE; 5-BROMO-3-(2-NITROPHENYL)-1-PHENYL-1H-PYRAZOLE-4-CARBOXALDEHYDE; 5-BROMO-3-(3,4-DICHLOROPHENYL)-1-(1,1-DIMETHYLETHYL)-1H-PYRAZOLE-4-CARBOXALDEHYDE; 5-BROMO-3-(3,4-DICHLOROPHENYL)-1-METHYL-1H-PYRAZOLE-4-CARBOXALDEHYDE; 5-BROMO-3-(3,4-DICHLOROPHENYL)-1-PHENYL-1H-PYRAZOLE-4-

CARBOXALDEHYDE; 5-BROMO-3-(3,4-DIFLUOROPHENYL)-1-(1,1-DIMETHYLETHYL)-1H-PYRAZOLE-4-CARBOXALDEHYDE; 5-BROMO-3-(3,4-DIFLUOROPHENYL)-1-(2-FLUOROPHENYL)-1H-PYRAZOLE-4-CARBOXALDEHYDE; 5-BROMO-3-(3,4-DIFLUOROPHENYL)-1-(3,5-DIFLUOROPHENYL)-1H-PYRAZOLE-4-CARBOXALDEHYDE; 5-BROMO-3-(3,4-DIFLUOROPHENYL)-1-(3-FLUOROPHENYL)-1H-PYRAZOLE-4-CARBOXALDEHYDE; 5-BROMO-3-(3,4-DIFLUOROPHENYL)-1-(4-FLUOROPHENYL)-1H-PYRAZOLE-4-CARBOXALDEHYDE; 5-BROMO-3-(3,4-DIFLUOROPHENYL)-1-METHYL-1H-PYRAZOLE-4-CARBOXALDEHYDE; 5-BROMO-3-(3,4-DIFLUOROPHENYL)-1-PHENYL-1H-PYRAZOLE-4-CARBOXALDEHYDE; 5-BROMO-3-(3,4-DIMETHOXYPHENYL)-1-(1,1-DIMETHYLETHYL)-1H-PYRAZOLE-4-CARBOXALDEHYDE; 5-BROMO-3-(3,4-DIMETHOXYPHENYL)-1-METHYL-1H-PYRAZOLE-4-CARBOXALDEHYDE; 5-BROMO-3-(3,4-DIMETHOXYPHENYL)-1-PHENYL-1H-PYRAZOLE-4-CARBOXALDEHYDE; 5-BROMO-3-(3,5-DICHLOROPHENYL)-1-(1,1-DIMETHYLETHYL)-1H-PYRAZOLE-4-CARBOXALDEHYDE; 5-BROMO-3-(3,5-DICHLOROPHENYL)-1-METHYL-1H-PYRAZOLE-4-CARBOXALDEHYDE; 5-BROMO-3-(3,5-DICHLOROPHENYL)-1-PHENYL-1H-PYRAZOLE-4-CARBOXALDEHYDE; 5-BROMO-3-(3,5-DIFLUOROPHENYL)-1-(1,1-DIMETHYLETHYL)-1H-PYRAZOLE-4-CARBOXALDEHYDE; 5-BROMO-3-(3,5-DIFLUOROPHENYL)-1-(2-FLUOROPHENYL)-1H-PYRAZOLE-4-CARBOXALDEHYDE; 5-BROMO-3-(3,5-DIFLUOROPHENYL)-1-(3-FLUOROPHENYL)-1H-PYRAZOLE-4-CARBOXALDEHYDE; 5-BROMO-3-(3,5-DIFLUOROPHENYL)-1-(4-FLUOROPHENYL)-1H-PYRAZOLE-4-CARBOXALDEHYDE; 5-BROMO-3-(3,5-DIFLUOROPHENYL)-1-METHYL-1H-PYRAZOLE-4-CARBOXALDEHYDE; 5-BROMO-3-(3,5-DIFLUOROPHENYL)-1-PHENYL-1H-PYRAZOLE-4-CARBOXALDEHYDE; 5-BROMO-3-(3,5-DIMETHOXYPHENYL)-1-(1,1-DIMETHYLETHYL)-1H-PYRAZOLE-4-CARBOXALDEHYDE; 5-BROMO-3-(3,5-DIMETHOXYPHENYL)-1-METHYL-1H-PYRAZOLE-4-CARBOXALDEHYDE; 5-BROMO-3-(3,5-DIMETHOXYPHENYL)-1-PHENYL-1H-PYRAZOLE-4-CARBOXALDEHYDE; 5-BROMO-3-(3,5-DIMETHYLPHENYL)-1-METHYL-1H-PYRAZOLE-4-CARBOXALDEHYDE; 5-BROMO-3-(3,5-DIMETHYLPHENYL)-1-PHENYL-1H-PYRAZOLE-4-CARBOXALDEHYDE; 5-BROMO-3-(3-BROMOPHENYL)-1-(1,1-DIMETHYLETHYL)-1H-PYRAZOLE-4-CARBOXALDEHYDE; 5-BROMO-3-(3-BROMOPHENYL)-1-METHYL-1H-PYRAZOLE-4-CARBOXALDEHYDE; 5-BROMO-3-(3-CHLOROPHENYL)-1-(1,1-DIMETHYLETHYL)-1H-PYRAZOLE-4-CARBOXALDEHYDE; 5-BROMO-3-(3-CHLOROPHENYL)-1-(2,4-DIFLUOROPHENYL)-1H-PYRAZOLE-4-CARBOXALDEHYDE; 5-BROMO-3-(3-CHLOROPHENYL)-1-(2,5-DIFLUOROPHENYL)-1H-PYRAZOLE-4-CARBOXALDEHYDE; 5-BROMO-3-(3-CHLOROPHENYL)-1-(2-FLUOROPHENYL)-1H-PYRAZOLE-4-CARBOXALDEHYDE; 5-BROMO-3-(3-CHLOROPHENYL)-1-(3,4-DIFLUOROPHENYL)-1H-PYRAZOLE-4-CARBOXALDEHYDE; 5-BROMO-3-(3-CHLOROPHENYL)-1-(3,5-DIFLUOROPHENYL)-1H-PYRAZOLE-4-CARBOXALDEHYDE; 5-BROMO-3-(3-CHLOROPHENYL)-1-(4-FLUOROPHENYL)-1H-PYRAZOLE-4-CARBOXALDEHYDE; 5-BROMO-3-(3-CHLOROPHENYL)-1-METHYL-1H-PYRAZOLE-4-CARBOXALDEHYDE; 5-BROMO-3-(3-CHLOROPHENYL)-1-PHENYL-1H-PYRAZOLE-4-CARBOXALDEHYDE; 5-BROMO-3-(3-FLUORO-4-METHOXYPHENYL)-1-METHYL-1H-PYRAZOLE-4-CARBOXALDEHYDE; 5-BROMO-3-(3-FLUORO-4-METHOXYPHENYL)-1-PHENYL-1H-PYRAZOLE-4-CARBOXALDEHYDE; 5-BROMO-3-(3-FLUOROPHENYL)-1-(2-NITROPHENYL)-1H-PYRAZOLE-4-CARBOXALDEHYDE; 5-BROMO-3-(3-FLUOROPHENYL)-1-(3-NITROPHENYL)-1H-PYRAZOLE-4-CARBOXALDEHYDE; 5-BROMO-3-(3-FLUOROPHENYL)-1-(4-FLUOROPHENYL)-1H-PYRAZOLE-4-CARBOXALDEHYDE; 5-BROMO-3-(3-FLUOROPHENYL)-1-(4-NITROPHENYL)-1H-PYRAZOLE-4-CARBOXALDEHYDE; 5-BROMO-3-(3-FLUOROPHENYL)-1-METHYL-1H-PYRAZOLE-4-CARBOXALDEHYDE; 5-BROMO-3-(3-FLUOROPHENYL)-1-PHENYL-1H-PYRAZOLE-4-CARBOXALDEHYDE; 5-BROMO-3-(3-METHOXYPHENYL)-1-METHYL-1H-PYRAZOLE-4-CARBOXALDEHYDE; 5-BROMO-3-(3-METHOXYPHENYL)-1-PHENYL-1H-PYRAZOLE-4-CARBOXALDEHYDE; 5-BROMO-3-(3-METHYLPHENYL)-1-PHENYL-1H-PYRAZOLE-4-CARBOXALDEHYDE; 5-BROMO-3-(3-NITROPHENYL)-1-PHENYL-1H-PYRAZOLE-4-CARBOXALDEHYDE; 5-BROMO-3-(4-BROMO-2-CHLOROPHENYL)-1-METHYL-1H-PYRAZOLE-4-CARBOXALDEHYDE; 5-BROMO-3-(4-BROMO-2-FLUOROPHENYL)-1-METHYL-1H-PYRAZOLE-4-CARBOXALDEHYDE; 5-BROMO-3-(4-BROMOPHENYL)-1-(1,1-DIMETHYLETHYL)-1H-PYRAZOLE-4-CARBOXALDEHYDE; 5-BROMO-3-(4-BROMOPHENYL)-1-METHYL-1H-PYRAZOLE-4-CARBOXALDEHYDE; 5-BROMO-3-(4-CHLORO-3-NITROPHENYL)-1-(1,1-DIMETHYLETHYL)-1H-PYRAZOLE-4-CARBOXALDEHYDE; 5-BROMO-3-(4-CHLORO-3-NITROPHENYL)-1-METHYL-1H-PYRAZOLE-4-CARBOXALDEHYDE; 5-BROMO-3-(4-CHLOROPHENYL)-1-(1,1-DIMETHYLETHYL)-1H-PYRAZOLE-4-CARBOXALDEHYDE; 5-BROMO-3-(4-CHLOROPHENYL)-1-(2,4-DIFLUOROPHENYL)-1H-PYRAZOLE-4-CARBOXALDEHYDE; 5-BROMO-3-(4-CHLOROPHENYL)-1-(2,5-DIFLUOROPHENYL)-1H-PYRAZOLE-4-CARBOXALDEHYDE; 5-BROMO-3-(4-CHLOROPHENYL)-1-(2-FLUOROPHENYL)-1H-PYRAZOLE-4-CARBOXALDEHYDE; 5-BROMO-3-(4-CHLOROPHENYL)-1-(3,4-DIFLUOROPHENYL)-1H-PYRAZOLE-4-CARBOXALDEHYDE; 5-BROMO-3-(4-CHLOROPHENYL)-1-(3,5-DIFLUOROPHENYL)-1H-PYRAZOLE-4-CARBOXALDEHYDE; 5-BROMO-3-(4-CHLOROPHENYL)-1-(4-FLUOROPHENYL)-1H-PYRAZOLE-4-CARBOXALDEHYDE; 5-BROMO-3-(4-CHLOROPHENYL)-1-METHYL-1H-PYRAZOLE-4-CARBOXALDEHYDE; 5-BROMO-3-(4-CHLOROPHENYL)-1-PHENYL-1H-PYRAZOLE-4-CARBOXALDEHYDE; 5-BROMO-3-(4-ETHOXYPHENYL)-1-METHYL-1H-PYRAZOLE-4-CARBOXALDEHYDE; 5-BROMO-3-(4-ETHOXYPHENYL)-1-PHENYL-1H-PYRAZOLE-4-CARBOXALDEHYDE; 5-BROMO-3-(4-ETHYLPHENYL)-1-METHYL-1H-PYRAZOLE-4-CARBOXALDEHYDE; 5-BROMO-3-(4-ETHYLPHENYL)-1-PHENYL-1H-PYRAZOLE-4-CARBOXALDEHYDE; 5-BROMO-3-(4-FLUORO-3-NITROPHENYL)-1-METHYL-1H-PYRAZOLE-4-

CARBOXALDEHYDE; 5-BROMO-3-(4-FLUORO-3-NITROPHENYL)-1-PHENYL-1H-PYRAZOLE-4-CARBOXALDEHYDE; 5-BROMO-3-(4-FLUOROPHENYL)-1-(2-NITROPHENYL)-1H-PYRAZOLE-4-CARBOXALDEHYDE; 5-BROMO-3-(4-FLUOROPHENYL)-1-(3-NITROPHENYL)-1H-PYRAZOLE-4-CARBOXALDEHYDE; 5-BROMO-3-(4-FLUOROPHENYL)-1-(4-NITROPHENYL)-1H-PYRAZOLE-4-CARBOXALDEHYDE; 5-BROMO-3-(4-FLUOROPHENYL)-1-METHYL-1H-PYRAZOLE-4-CARBOXALDEHYDE; 5-BROMO-3-(4-FLUOROPHENYL)-1-PHENYL-1H-PYRAZOLE-4-CARBOXALDEHYDE; 5-BROMO-3-(4-METHOXYPHENYL)-1-METHYL-1H-PYRAZOLE-4-CARBOXALDEHYDE; 5-BROMO-3-(4-METHOXYPHENYL)-1-PHENYL-1H-PYRAZOLE-4-CARBOXALDEHYDE; 5-BROMO-3-(4-METHYLPHENYL)-1-PHENYL-1H-PYRAZOLE-4-CARBOXALDEHYDE; 5-BROMO-3-(4-NITROPHENYL)-1-PHENYL-1H-PYRAZOLE-4-CARBOXALDEHYDE; 5-BROMO-3-(5-BROMO-2-CHLOROPHENYL)-1-METHYL-1H-PYRAZOLE-4-CARBOXALDEHYDE; 5-BROMO-3-(5-BROMO-2-FLUOROPHENYL)-1-METHYL-1H-PYRAZOLE-4-CARBOXALDEHYDE; 5-BROMO-3-[4-(1,1-DIMETHYLETHYL)PHENYL]-1-METHYL-1H-PYRAZOLE-4-CARBOXALDEHYDE; 5-BROMO-3-[4-(1,1-DIMETHYLETHYL)PHENYL]-1-PHENYL-1H-PYRAZOLE-4-CARBOXALDEHYDE; 5-BROMO-3-[4-(1-METHYLETHYL)PHENYL]-1H-PHENYL-1H-PYRAZOLE-4-CARBOXALDEHYDE; 5-BROMO-3-CHLORO-1-BENZOFURAN-2-CARBALDEHYDE; 5-BROMO-3-ETHYL-1-METHYL-1H-PYRAZOLE-4-CARBOXALDEHYDE; 5-BROMO-3-ETHYL-1-PHENYL-1H-PYRAZOLE-4-CARBOXALDEHYDE; 5-BROMO-3-ETHYL-4-METHYL-PYRROLE-2-CARBOXALDEHYDE; 5-BROMO-3-ETHYL-IMIDAZO[1,2-A]PYRIDINE-2-CARBALDEHYDE; 5-BROMO-3-FORMYL-PYRAZOLO[1,5-A]PYRIDINE-2-CARBOXYLIC ACID ETHYL ESTER; 5-BROMO-3H-IMIDAZOLE-4-CARBALDEHYDE; 5-BROMO-3-METHYL-1-PHENYL-1H-PYRAZOLE-4-CARBOXALDEHYDE; 5-BROMO-3-PHENYL-1-[2-(TRIFLUOROMETHYL)PHENYL]-1H-PYRAZOLE-4-CARBOXALDEHYDE; 5-BROMO-3-PHENYL-1-[3-(TRIFLUOROMETHYL)PHENYL]-1H-PYRAZOLE-4-CARBOXALDEHYDE; 5-BROMO-3-PHENYL-1-[4-(TRIFLUOROMETHYL)PHENYL]-1H-PYRAZOLE-4-CARBOXALDEHYDE; 5-BROMO-6-OXO-1,6-DIHYDRO-3-PYRIDINECARBALDEHYDE; 5-BROMOIMIDAZO[1,2-A]PYRIDINE-2-CARBALDEHYDE; 5-CHLORO-1-(1,1-DIMETHYLETHYL)-3-(2,3,4-TRIFLUOROPHENYL)-1H-PYRAZOLE-4-CARBOXALDEHYDE; 5-CHLORO-1-(1,1-DIMETHYLETHYL)-3-(2,6-DIMETHYLPHENYL)-1H-PYRAZOLE-4-CARBOXALDEHYDE; 5-CHLORO-1-(1,1-DIMETHYLETHYL)-3-(2-FLUORO-4-NITROPHENYL)-1H-PYRAZOLE-4-CARBOXALDEHYDE; 5-CHLORO-1-(1,1-DIMETHYLETHYL)-3-(2-FLUORO-5-NITROPHENYL)-1H-PYRAZOLE-4-CARBOXALDEHYDE; 5-CHLORO-1-(1,1-DIMETHYLETHYL)-3-(2-FLUOROPHENYL)-1H-PYRAZOLE-4-CARBOXALDEHYDE; 5-CHLORO-1-(1,1-DIMETHYLETHYL)-3-(2-METHOXYPHENYL)-1H-PYRAZOLE-4-CARBOXALDEHYDE; 5-CHLORO-1-(1,1-DIMETHYLETHYL)-3-(2-METHYLPHENYL)-1H-PYRAZOLE-4-CARBOXALDEHYDE; 5-CHLORO-1-(1,1-DIMETHYLETHYL)-3-(2-NITROPHENYL)-1H-PYRAZOLE-4-CARBOXALDEHYDE; 5-CHLORO-1-(1,1-DIMETHYLETHYL)-3-(3,5-DIMETHYLPHENYL)-1H-PYRAZOLE-4-CARBOXALDEHYDE; 5-CHLORO-1-(1,1-DIMETHYLETHYL)-3-(3-FLUOROPHENYL)-1H-PYRAZOLE-4-CARBOXALDEHYDE; 5-CHLORO-1-(1,1-DIMETHYLETHYL)-3-(3-METHOXYPHENYL)-1H-PYRAZOLE-4-CARBOXALDEHYDE; 5-CHLORO-1-(1,1-DIMETHYLETHYL)-3-(3-METHYLPHENYL)-1H-PYRAZOLE-4-CARBOXALDEHYDE; 5-CHLORO-1-(1,1-DIMETHYLETHYL)-3-(3-NITROPHENYL)-1H-PYRAZOLE-4-CARBOXALDEHYDE; 5-CHLORO-1-(1,1-DIMETHYLETHYL)-3-(4-ETHYLPHENYL)-1H-PYRAZOLE-4-CARBOXALDEHYDE; 5-CHLORO-1-(1,1-DIMETHYLETHYL)-3-(4-FLUORO-3-NITROPHENYL)-1H-PYRAZOLE-4-CARBOXALDEHYDE; 5-CHLORO-1-(1,1-DIMETHYLETHYL)-3-(4-FLUOROPHENYL)-1H-PYRAZOLE-4-CARBOXALDEHYDE; 5-CHLORO-1-(1,1-DIMETHYLETHYL)-3-(4-METHOXYPHENYL)-1H-PYRAZOLE-4-CARBOXALDEHYDE; 5-CHLORO-1-(1,1-DIMETHYLETHYL)-3-(4-METHYLPHENYL)-1H-PYRAZOLE-4-CARBOXALDEHYDE; 5-CHLORO-1-(1,1-DIMETHYLETHYL)-3-(4-NITROPHENYL)-1H-PYRAZOLE-4-CARBOXALDEHYDE; 5-CHLORO-1-(1,1-DIMETHYLETHYL)-3-(4-PROPYLPHENYL)-1H-PYRAZOLE-4-CARBOXALDEHYDE; 5-CHLORO-1-(1,1-DIMETHYLETHYL)-3-[2-(TRIFLUOROMETHYL)PHENYL]-1H-PYRAZOLE-4-CARBOXALDEHYDE; 5-CHLORO-1-(1,1-DIMETHYLETHYL)-3-[3-(TRIFLUOROMETHYL)PHENYL]-1H-PYRAZOLE-4-CARBOXALDEHYDE; 5-CHLORO-1-(1,1-DIMETHYLETHYL)-3-[4-(1,1-DIMETHYLETHYL)PHENYL]-1H-PYRAZOLE-4-CARBOXALDEHYDE; 5-CHLORO-1-(1,1-DIMETHYLETHYL)-3-[4-(1-METHYLETHYL)PHENYL]-1H-PYRAZOLE-4-CARBOXALDEHYDE; 5-CHLORO-1-(1,1-DIMETHYLETHYL)-3-[4-(TRIFLUOROMETHYL)PHENYL]-1H-PYRAZOLE-4-CARBOXALDEHYDE; 5-CHLORO-1-(1,1-DIOXIDOTETRAHYDROTHIEN-3-YL)-3-METHYL-1H-PYRAZOLE-4-CARBALDEHYDE; 5-CHLORO-1-(1,1-DIOXO-1LAMBDA(6)-THIOLAN-3-YL)-3-(PROPAN-2-YL)-1H-PYRAZOLE-4-CARBALDEHYDE; 5-CHLORO-1-(1,1-DIOXO-1LAMBDA(6)-THIOLAN-3-YL)-3-PROPYL-1H-PYRAZOLE-4-CARBALDEHYDE; 5-CHLORO-1-(1,1-DIOXO-LAMBDA(6)-THIOLAN-3-YL)-3-ETHYL-1H-PYRAZOLE-4-CARBALDEHYDE; 5-CHLORO-1-(1-CYCLOPROPYLETHYL)-3-(METHOXYMETHYL)-1H-PYRAZOLE-4-CARBALDEHYDE; 5-CHLORO-1-(1-CYCLOPROPYLETHYL)-3-(PROPAN-2-YL)-1H-PYRAZOLE-4-CARBALDEHYDE; 5-CHLORO-1-(1-CYCLOPROPYLETHYL)-3-(TRIFLUOROMETHYL)-1H-PYRAZOLE-4-CARBALDEHYDE; 5-CHLORO-1-(1-CYCLOPROPYLETHYL)-3-ETHYL-1H-PYRAZOLE-4-CARBALDEHYDE; 5-CHLORO-1-(1-CYCLOPROPYLETHYL)-3-METHYL-1H-PYRAZOLE-4-CARBALDEHYDE; 5-CHLORO-1-(1-CYCLOPROPYLETHYL)-3-PHENYL-1H-PYRAZOLE-4-CARBALDEHYDE; 5-CHLORO-1-(1-CYCLOPROPYLETHYL)-3-PROPYL-1H-PYRAZOLE-4-CARBALDEHYDE; 5-CHLORO-1-(2,4-DICHLOROBENZYL)-6-OXO-1,6-DIHYDRO-3-PYRIDINECARBALDEHYDE; 5-CHLORO-1-(2,4-DICHLOROPHENYL)-1H-PYRAZOLE-4-CARBOXALDEHYDE; 5-CHLORO-1-(2,4-DICHLOROPHENYL)-3-(DIFLUOROMETHYL)-1H-PYRAZOLE-4-CARBALDEHYDE; 5-CHLORO-1-(2,4-

DICHLOROPHENYL)-3-(METHOXYMETHYL)-1H-PYRAZOLE-4-CARBALDEHYDE; 5-CHLORO-1-(2,4-DICHLOROPHENYL)-3-(PROPAN-2-YL)-1H-PYRAZOLE-4-CARBALDEHYDE; 5-CHLORO-1-(2,4-DICHLOROPHENYL)-3-ETHYL-1H-PYRAZOLE-4-CARBALDEHYDE; 5-CHLORO-1-(2,4-DICHLOROPHENYL)-3-METHYL-1H-PYRAZOLE-4-CARBALDEHYDE; 5-CHLORO-1-(2,4-DICHLOROPHENYL)-3-PROPYL-1H-PYRAZOLE-4-CARBALDEHYDE; 5-CHLORO-1-(2,4-DIFLUOROPHENYL)-1H-PYRAZOLE-4-CARBOXALDEHYDE; 5-CHLORO-1-(2,4-DIFLUOROPHENYL)-3-(2-FLUOROPHENYL)-1H-PYRAZOLE-4-CARBOXALDEHYDE; 5-CHLORO-1-(2,4-DIFLUOROPHENYL)-3-(3-FLUOROPHENYL)-1H-PYRAZOLE-4-CARBOXALDEHYDE; 5-CHLORO-1-(2,4-DIFLUOROPHENYL)-3-(4-FLUOROPHENYL)-1H-PYRAZOLE-4-CARBOXALDEHYDE; 5-CHLORO-1-(2,4-DIFLUOROPHENYL)-3-(METHOXYMETHYL)-1H-PYRAZOLE-4-CARBALDEHYDE; 5-CHLORO-1-(2,4-DIFLUOROPHENYL)-3-(PROPAN-2-YL)-1H-PYRAZOLE-4-CARBALDEHYDE; 5-CHLORO-1-(2,4-DIFLUOROPHENYL)-3-ETHYL-1H-PYRAZOLE-4-CARBALDEHYDE; 5-CHLORO-1-(2,4-DIFLUOROPHENYL)-3-METHYL-1H-PYRAZOLE-4-CARBALDEHYDE; 5-CHLORO-1-(2,4-DIFLUOROPHENYL)-3-PHENYL-1H-PYRAZOLE-4-CARBOXALDEHYDE; 5-CHLORO-1-(2,4-DIFLUOROPHENYL)-3-PROPYL-1H-PYRAZOLE-4-CARBALDEHYDE; 5-CHLORO-1-(2,4-DIMETHOXYBENZYL)-3-METHYL-1H-PYRAZOLE-4-CARBALDEHYDE; 5-CHLORO-1-(2,4-DIMETHYLPHENYL)-3-(METHOXYMETHYL)-1H-PYRAZOLE-4-CARBALDEHYDE; 5-CHLORO-1-(2,4-DIMETHYLPHENYL)-3-(PROPAN-2-YL)-1H-PYRAZOLE-4-CARBALDEHYDE; 5-CHLORO-1-(2,4-DIMETHYLPHENYL)-3-ETHYL-1H-PYRAZOLE-4-CARBALDEHYDE; 5-CHLORO-1-(2,4-DIMETHYLPHENYL)-3-METHYL-1H-PYRAZOLE-4-CARBALDEHYDE; 5-CHLORO-1-(2,4-DIMETHYLPHENYL)-3-PROPYL-1H-PYRAZOLE-4-CARBALDEHYDE; 5-CHLORO-1-(2,5-DICHLOROPHENYL)-1H-PYRAZOLE-4-CARBOXALDEHYDE; 5-CHLORO-1-(2,5-DIFLUOROPHENYL)-1H-PYRAZOLE-4-CARBOXALDEHYDE; 5-CHLORO-1-(2,5-DIFLUOROPHENYL)-3-(2-FLUOROPHENYL)-1H-PYRAZOLE-4-CARBOXALDEHYDE; 5-CHLORO-1-(2,5-DIFLUOROPHENYL)-3-(3-FLUOROPHENYL)-1H-PYRAZOLE-4-CARBOXALDEHYDE; 5-CHLORO-1-(2,5-DIFLUOROPHENYL)-3-(4-FLUOROPHENYL)-1H-PYRAZOLE-4-CARBOXALDEHYDE; 5-CHLORO-1-(2,5-DIFLUOROPHENYL)-3-PHENYL-1H-PYRAZOLE-4-CARBOXALDEHYDE; 5-CHLORO-1-(2,5-DIMETHYLPHENYL)-3-(METHOXYMETHYL)-1H-PYRAZOLE-4-CARBALDEHYDE; 5-CHLORO-1-(2,5-DIMETHYLPHENYL)-3-(PROPAN-2-YL)-1H-PYRAZOLE-4-CARBALDEHYDE; 5-CHLORO-1-(2,5-DIMETHYLPHENYL)-3-ETHYL-1H-PYRAZOLE-4-CARBALDEHYDE; 5-CHLORO-1-(2,5-DIMETHYLPHENYL)-3-METHYL-1H-PYRAZOLE-4-CARBALDEHYDE; 5-CHLORO-1-(2,5-DIMETHYLPHENYL)-3-PROPYL-1H-PYRAZOLE-4-CARBALDEHYDE; 5-CHLORO-1-(2-CHLORO-4-FLUOROPHENYL)-1H-PYRAZOLE-4-CARBOXALDEHYDE; 5-CHLORO-1-(2-CHLORO-5-FLUOROPHENYL)-1H-PYRAZOLE-4-CARBOXALDEHYDE; 5-CHLORO-1-(2-CHLORO-6-FLUOROBENZYL)-6-OXO-1,6-DIHYDRO-3-PYRIDINECARBALDEHYDE; 5-CHLORO-1-(2-CHLOROPHENYL)-1H-PYRAZOLE-4-CARBOXALDEHYDE; 5-CHLORO-1-(2-CHLOROPHENYL)-3-(2-FLUOROPHENYL)-1H-PYRAZOLE-4-CARBOXALDEHYDE; 5-CHLORO-1-(2-CHLOROPHENYL)-3-(3-FLUOROPHENYL)-1H-PYRAZOLE-4-CARBOXALDEHYDE; 5-CHLORO-1-(2-CHLOROPHENYL)-3-(4-FLUOROPHENYL)-1H-PYRAZOLE-4-CARBOXALDEHYDE; 5-CHLORO-1-(2-CHLOROPHENYL)-3-(DIFLUOROMETHYL)-1H-PYRAZOLE-4-CARBALDEHYDE; 5-CHLORO-1-(2-CHLOROPHENYL)-3-(METHOXYMETHYL)-1H-PYRAZOLE-4-CARBALDEHYDE; 5-CHLORO-1-(2-CHLOROPHENYL)-3-(PROPAN-2-YL)-1H-PYRAZOLE-4-CARBALDEHYDE; 5-CHLORO-1-(2-CHLOROPHENYL)-3-(TRIFLUOROMETHYL)-1H-PYRAZOLE-4-CARBALDEHYDE; 5-CHLORO-1-(2-CHLOROPHENYL)-3-ETHYL-1H-PYRAZOLE-4-CARBALDEHYDE; 5-CHLORO-1-(2-CHLOROPHENYL)-3-METHYL-1H-PYRAZOLE-4-CARBALDEHYDE; 5-CHLORO-1-(2-CHLOROPHENYL)-3-PHENYL-1H-PYRAZOLE-4-CARBOXALDEHYDE; 5-CHLORO-1-(2-CHLOROPHENYL)-3-PROPYL-1H-PYRAZOLE-4-CARBALDEHYDE; 5-CHLORO-1-(2-FLUOROPHENYL)-1H-PYRAZOLE-4-CARBOXALDEHYDE; CHLORO-1-(2-FLUOROPHENYL)-3-(2-NITROPHENYL)-1H-PYRAZOLE-4-CARBOXALDEHYDE; 5-CHLORO-1-(2-FLUOROPHENYL)-3-(3-FLUOROPHENYL)-1H-PYRAZOLE-4-CARBOXALDEHYDE; 5-CHLORO-1-(2-FLUOROPHENYL)-3-(3-NITROPHENYL)-1H-PYRAZOLE-4-CARBOXALDEHYDE; 5-CHLORO-1-(2-FLUOROPHENYL)-3-(4-FLUOROPHENYL)-1H-PYRAZOLE-4-CARBOXALDEHYDE; 5-CHLORO-1-(2-FLUOROPHENYL)-3-(4-NITROPHENYL)-1H-PYRAZOLE-4-CARBOXALDEHYDE; 5-CHLORO-1-(2-FLUOROPHENYL)-3-(METHOXYMETHYL)-1H-PYRAZOLE-4-CARBALDEHYDE; 5-CHLORO-1-(2-FLUOROPHENYL)-3-(PROPAN-2-YL)-1H-PYRAZOLE-4-CARBALDEHYDE; 5-CHLORO-1-(2-FLUOROPHENYL)-3-(TRIFLUOROMETHYL)-1H-PYRAZOLE-4-CARBALDEHYDE; CHLORO-1-(2-FLUOROPHENYL)-3-METHYL-1H-PYRAZOLE-4-CARBALDEHYDE; 5-CHLORO-1-(2-FLUOROPHENYL)-3-PHENYL-1H-PYRAZOLE-4-CARBOXALDEHYDE; 5-CHLORO-1-(2-FLUOROPHENYL)-3-PROPYL-1H-PYRAZOLE-4-CARBALDEHYDE; 5-CHLORO-1-(2-METHOXYPHENYL)-3-(PROPAN-2-YL)-1H-PYRAZOLE-4-CARBALDEHYDE; 5-CHLORO-1-(2-METHOXYPHENYL)-3-METHYL-1H-PYRAZOLE-4-CARBALDEHYDE; 5-CHLORO-1-(2-METHOXYPHENYL)-3-PROPYL-1H-PYRAZOLE-4-CARBALDEHYDE; 5-CHLORO-1-(2-METHYLPHENYL)-3-(PROPAN-2-YL)-1H-PYRAZOLE-4-CARBALDEHYDE; 5-CHLORO-1-(2-METHYLPHENYL)-3-(TRIFLUOROMETHYL)-1H-PYRAZOLE-4-CARBALDEHYDE; CHLORO-1-(2-METHYLPHENYL)-3-PROPYL-1H-PYRAZOLE-4-CARBALDEHYDE; CHLORO-1-(2-METHYLPROPYL)-3-(PROPAN-2-YL)-1H-PYRAZOLE-4-CARBALDEHYDE; 5-CHLORO-1-(2-METHYLPROPYL)-3-(TRIFLUOROMETHYL)-1H-PYRAZOLE-4-CARBALDEHYDE; 5-CHLORO-1-(2-

METHYLPROPYL)-3-PHENYL-1H-PYRAZOLE-4-CARBALDEHYDE; 5-CHLORO-1-(2-METHYLPROPYL)-3-PROPYL-1H-PYRAZOLE-4-CARBALDEHYDE; 5-CHLORO-1-(2-NITROPHENYL)-1H-PYRAZOLE-4-CARBOXALDEHYDE; 5-CHLORO-1-(2-NITROPHENYL)-3-PHENYL-1H-PYRAZOLE-4-CARBOXALDEHYDE; 5-CHLORO-1-(3,4-DICHLOROPHENYL)-1H-PYRAZOLE-4-CARBOXALDEHYDE; 5-CHLORO-1-(3,4-DICHLOROPHENYL)-3-(DIFLUOROMETHYL)-1H-PYRAZOLE-4-CARBALDEHYDE; 5-CHLORO-1-(3,4-DICHLOROPHENYL)-3-(METHOXYMETHYL)-1H-PYRAZOLE-4-CARBALDEHYDE; CHLORO-1-(3,4-DICHLOROPHENYL)-3-(PROPAN-2-YL)-1H-PYRAZOLE-4-CARBALDEHYDE; 5-CHLORO-1-(3,4-DICHLOROPHENYL)-3-ETHYL-1H-PYRAZOLE-4-CARBALDEHYDE; 5-CHLORO-1-(3,4-DICHLOROPHENYL)-3-METHYL-1H-PYRAZOLE-4-CARBALDEHYDE; 5-CHLORO-1-(3,4-DICHLOROPHENYL)-3-PROPYL-1H-PYRAZOLE-4-CARBALDEHYDE; 5-CHLORO-1-(3,4-DIFLUOROPHENYL)-1H-PYRAZOLE-4-CARBOXALDEHYDE; 5-CHLORO-1-(3,4-DIFLUOROPHENYL)-3-(2-FLUOROPHENYL)-1H-PYRAZOLE-4-CARBOXALDEHYDE; 5-CHLORO-1-(3,4-DIFLUOROPHENYL)-3-(3-FLUOROPHENYL)-1H-PYRAZOLE-4-CARBOXALDEHYDE; 5-CHLORO-1-(3,4-DIFLUOROPHENYL)-3-(4-FLUOROPHENYL)-1H-PYRAZOLE-4-CARBOXALDEHYDE; 5-CHLORO-1-(3,4-DIFLUOROPHENYL)-3-PHENYL-1H-PYRAZOLE-4-CARBOXALDEHYDE; 5-CHLORO-1-(3,5-DICHLOROPHENYL)-1H-PYRAZOLE-4-CARBOXALDEHYDE; 5-CHLORO-1-(3,5-DIFLUOROPHENYL)-1H-PYRAZOLE-4-CARBOXALDEHYDE; 5-CHLORO-1-(3,5-DIFLUOROPHENYL)-3-(2-FLUOROPHENYL)-1H-PYRAZOLE-4-CARBOXALDEHYDE; 5-CHLORO-1-(3,5-DIFLUOROPHENYL)-3-(3-FLUOROPHENYL)-1H-PYRAZOLE-4-CARBOXALDEHYDE; 5-CHLORO-1-(3,5-DIFLUOROPHENYL)-3-(4-FLUOROPHENYL)-1H-PYRAZOLE-4-CARBOXALDEHYDE; 5-CHLORO-1-(3,5-DIFLUOROPHENYL)-3-PHENYL-1H-PYRAZOLE-4-CARBOXALDEHYDE; 5-CHLORO-1-(3,5-DIMETHYLPHENYL)-3-(METHOXYMETHYL)-1H-PYRAZOLE-4-CARBALDEHYDE; 5-CHLORO-1-(3,5-DIMETHYLPHENYL)-3-(PROPAN-2-YL)-1H-PYRAZOLE-4-CARBALDEHYDE; 5-CHLORO-1-(3,5-DIMETHYLPHENYL)-3-ETHYL-1H-PYRAZOLE-4-CARBALDEHYDE; 5-CHLORO-1-(3,5-DIMETHYLPHENYL)-3-METHYL-1H-PYRAZOLE-4-CARBALDEHYDE; 5-CHLORO-1-(3,5-DIMETHYLPHENYL)-3-PROPYL-1H-PYRAZOLE-4-CARBALDEHYDE; 5-CHLORO-1-(3-CHLORO-4-FLUOROPHENYL)-1H-PYRAZOLE-4-CARBOXALDEHYDE; 5-CHLORO-1-(3-CHLORO-4-METHYLPHENYL)-3-(DIFLUOROMETHYL)-1H-PYRAZOLE-4-CARBALDEHYDE; 5-CHLORO-1-(3-CHLORO-4-METHYLPHENYL)-3-(METHOXYMETHYL)-1H-PYRAZOLE-4-CARBALDEHYDE; 5-CHLORO-1-(3-CHLORO-4-METHYLPHENYL)-3-(PROPAN-2-YL)-1H-PYRAZOLE-4-CARBALDEHYDE; 5-CHLORO-1-(3-CHLORO-4-METHYLPHENYL)-3-ETHYL-1H-PYRAZOLE-4-CARBALDEHYDE; 5-CHLORO-1-(3-CHLORO-4-METHYLPHENYL)-3-METHYL-1H-PYRAZOLE-4-CARBALDEHYDE; 5-CHLORO-1-(3-CHLORO-4-METHYLPHENYL)-3-PROPYL-1H-PYRAZOLE-4-CARBALDEHYDE; 5-CHLORO-1-(3-CHLOROPHENYL)-1H-PYRAZOLE-4-CARBOXALDEHYDE; 5-CHLORO-1-(3-CHLOROPHENYL)-3-(2-FLUOROPHENYL)-1H-PYRAZOLE-4-CARBOXALDEHYDE; 5-CHLORO-1-(3-CHLOROPHENYL)-3-(3-FLUOROPHENYL)-1H-PYRAZOLE-4-CARBOXALDEHYDE; 5-CHLORO-1-(3-CHLOROPHENYL)-3-(4-FLUOROPHENYL)-1H-PYRAZOLE-4-CARBOXALDEHYDE; 5-CHLORO-1-(3-CHLOROPHENYL)-3-(DIFLUOROMETHYL)-1H-PYRAZOLE-4-CARBALDEHYDE; 5-CHLORO-1-(3-CHLOROPHENYL)-3-(METHOXYMETHYL)-1H-PYRAZOLE-4-CARBALDEHYDE; 5-CHLORO-1-(3-CHLOROPHENYL)-3-(PROPAN-2-YL)-1H-PYRAZOLE-4-CARBALDEHYDE; 5-CHLORO-1-(3-CHLOROPHENYL)-3-(TRIFLUOROMETHYL)-1H-PYRAZOLE-4-CARBALDEHYDE; 5-CHLORO-1-(3-CHLOROPHENYL)-3-ETHYL-1H-PYRAZOLE-4-CARBALDEHYDE; 5-CHLORO-1-(3-CHLOROPHENYL)-3-METHYL-1H-PYRAZOLE-4-CARBALDEHYDE; 5-CHLORO-1-(3-CHLOROPHENYL)-3-PHENYL-1H-PYRAZOLE-4-CARBOXALDEHYDE; 5-CHLORO-1-(3-CHLOROPHENYL)-3-PROPYL-1H-PYRAZOLE-4-CARBALDEHYDE; 5-CHLORO-1-(3-FLUOROPHENYL)-1H-PYRAZOLE-4-CARBOXALDEHYDE; 5-CHLORO-1-(3-FLUOROPHENYL)-3-(2-NITROPHENYL)-1H-PYRAZOLE-4-CARBOXALDEHYDE; 5-CHLORO-1-(3-FLUOROPHENYL)-3-(3-NITROPHENYL)-1H-PYRAZOLE-4-CARBOXALDEHYDE; 5-CHLORO-1-(3-FLUOROPHENYL)-3-(4-FLUOROPHENYL)-1H-PYRAZOLE-4-CARBOXALDEHYDE; 5-CHLORO-1-(3-FLUOROPHENYL)-3-(4-NITROPHENYL)-1H-PYRAZOLE-4-CARBOXALDEHYDE; 5-CHLORO-1-(3-FLUOROPHENYL)-3-(METHOXYMETHYL)-1H-PYRAZOLE-4-CARBALDEHYDE; 5-CHLORO-1-(3-FLUOROPHENYL)-3-(PROPAN-2-YL)-1H-PYRAZOLE-4-CARBALDEHYDE; 5-CHLORO-1-(3-FLUOROPHENYL)-3-(TRIFLUOROMETHYL)-1H-PYRAZOLE-4-CARBALDEHYDE; 5-CHLORO-1-(3-FLUOROPHENYL)-3-METHYL-1H-PYRAZOLE-4-CARBALDEHYDE; 5-CHLORO-1-(3-FLUOROPHENYL)-3-PHENYL-1H-PYRAZOLE-4-CARBOXALDEHYDE; 5-CHLORO-1-(3-FLUOROPHENYL)-3-PROPYL-1H-PYRAZOLE-4-CARBALDEHYDE; 5-CHLORO-1-(3-METHOXYBENZYL)-3-METHYL-1H-PYRAZOLE-4-CARBALDEHYDE; 5-CHLORO-1-(3-METHYL-1,1-DIOXO-1LAMBDA6-THIOLAN-3-YL)-3-(PROPAN-2-YL)-1H-PYRAZOLE-4-CARBALDEHYDE; 5-CHLORO-1-(3-METHYL-1,1-DIOXO-1LAMBDA6-THIOLAN-3-YL)-3-PROPYL-1H-PYRAZOLE-4-CARBALDEHYDE; 5-CHLORO-1-(3-METHYLBUTYL)-3-(PROPAN-2-YL)-1H-PYRAZOLE-4-CARBALDEHYDE; 5-CHLORO-1-(3-METHYLBUTYL)-3-(TRIFLUOROMETHYL)-1H-PYRAZOLE-4-CARBALDEHYDE; 5-CHLORO-1-(3-METHYLBUTYL)-3-PHENYL-1H-PYRAZOLE-4-CARBALDEHYDE; 5-CHLORO-1-(3-METHYLBUTYL)-3-PROPYL-1H-PYRAZOLE-4-CARBALDEHYDE; 5-CHLORO-1-(3-METHYLPHENYL)-3-(PROPAN-2-YL)-1H-PYRAZOLE-4-CARBALDEHYDE; 5-CHLORO-1-(3-METHYLPHENYL)-3-(TRIFLUOROMETHYL)-1H-PYRAZOLE-4-CARBALDEHYDE; 5-CHLORO-1-(3-METHYLPHENYL)-3-PROPYL-1H-PYRAZOLE-4-CARBALDEHYDE; 5-CHLORO-1-(3-NITROPHENYL)-

1H-PYRAZOLE-4-CARBOXALDEHYDE; 5-CHLORO-1-(3-NITROPHENYL)-3-PHENYL-1H-PYRAZOLE-4-CARBOXALDEHYDE; 5-CHLORO-1-(4,6-DIMETHOXYPYRIMIDIN-2-YL)-3-METHYL-1H-PYRAZOLE-4-CARBALDEHYDE; 5-CHLORO-1-(4,6-DIMETHYLPYRIMIDIN-2-YL)-3-(METHOXYMETHYL)-1H-PYRAZOLE-4-CARBALDEHYDE; 5-CHLORO-1-(4,6-DIMETHYLPYRIMIDIN-2-YL)-3-(PROPAN-2-YL)-1H-PYRAZOLE-4-CARBALDEHYDE; 5-CHLORO-1-(4,6-DIMETHYLPYRIMIDIN-2-YL)-3-ETHYL-1H-PYRAZOLE-4-CARBALDEHYDE; 5-CHLORO-1-(4,6-DIMETHYLPYRIMIDIN-2-YL)-3-METHYL-1H-PYRAZOLE-4-CARBALDEHYDE; 5-CHLORO-1-(4,6-DIMETHYLPYRIMIDIN-2-YL)-3-PROPYL-1H-PYRAZOLE-4-CARBALDEHYDE; 5-CHLORO-1-(4-CHLOROBENZYL)-6-OXO-1,6-DIHYDRO-3-PYRIDINECARBALDEHYDE; 5-CHLORO-1-(4-CHLOROPHENYL)-1H-PYRAZOLE-4-CARBOXALDEHYDE; 5-CHLORO-1-(4-CHLOROPHENYL)-3-(2-FLUOROPHENYL)-1H-PYRAZOLE-4-CARBOXALDEHYDE; 5-CHLORO-1-(4-CHLOROPHENYL)-3-(3-FLUOROPHENYL)-1H-PYRAZOLE-4-CARBOXALDEHYDE; 5-CHLORO-1-(4-CHLOROPHENYL)-3-(4-FLUOROPHENYL)-1H-PYRAZOLE-4-CARBOXALDEHYDE; 5-CHLORO-1-(4-CHLOROPHENYL)-3-(DIFLUOROMETHYL)-1H-PYRAZOLE-4-CARBALDEHYDE; 5-CHLORO-1-(4-CHLOROPHENYL)-3-(METHOXYMETHYL)-1H-PYRAZOLE-4-CARBALDEHYDE; 5-CHLORO-1-(4-CHLOROPHENYL)-3-(PROPAN-2-YL)-1H-PYRAZOLE-4-CARBALDEHYDE; 5-CHLORO-1-(4-CHLOROPHENYL)-3-(TRIFLUOROMETHYL)-1H-PYRAZOLE-4-CARBALDEHYDE; 5-CHLORO-1-(4-CHLOROPHENYL)-3-ETHYL-1H-PYRAZOLE-4-CARBALDEHYDE; 5-CHLORO-1-(4-CHLOROPHENYL)-3-METHYL-1H-PYRAZOLE-4-CARBALDEHYDE; 5-CHLORO-1-(4-CHLOROPHENYL)-3-PHENYL-1H-PYRAZOLE-4-CARBOXALDEHYDE; 5-CHLORO-1-(4-CHLOROPHENYL)-3-PROPYL-1H-PYRAZOLE-4-CARBALDEHYDE; 5-CHLORO-1-(4-FLUOROBENZYL)-6-OXO-1,6-DIHYDRO-3-PYRIDINECARBALDEHYDE; 5-CHLORO-1-(4-FLUOROPHENYL)-1H-PYRAZOLE-4-CARBOXALDEHYDE; 5-CHLORO-1-(4-FLUOROPHENYL)-3-(2-NITROPHENYL)-1H-PYRAZOLE-4-CARBOXALDEHYDE; 5-CHLORO-1-(4-FLUOROPHENYL)-3-(3-NITROPHENYL)-1H-PYRAZOLE-4-CARBOXALDEHYDE; 5-CHLORO-1-(4-FLUOROPHENYL)-3-(4-NITROPHENYL)-1H-PYRAZOLE-4-CARBOXALDEHYDE; 5-CHLORO-1-(4-FLUOROPHENYL)-3-(METHOXYMETHYL)-1H-PYRAZOLE-4-CARBALDEHYDE; 5-CHLORO-1-(4-FLUOROPHENYL)-3-(PROPAN-2-YL)-1H-PYRAZOLE-4-CARBALDEHYDE; 5-CHLORO-1-(4-FLUOROPHENYL)-3-(TRIFLUOROMETHYL)-1H-PYRAZOLE-4-CARBALDEHYDE; 5-CHLORO-1-(4-FLUOROPHENYL)-3-METHYL-1H-PYRAZOLE-4-CARBALDEHYDE; 5-CHLORO-1-(4-FLUOROPHENYL)-3-PHENYL-1H-PYRAZOLE-4-CARBOXALDEHYDE; 5-CHLORO-1-(4-FLUOROPHENYL)-3-PROPYL-1H-PYRAZOLE-4-CARBALDEHYDE; 5-CHLORO-1-(4-METHYLBENZYL)-6-OXO-1,6-DIHYDRO-3-PYRIDINECARBALDEHYDE; 5-CHLORO-1-(4-METHYLPHENYL)-3-(PROPAN-2-YL)-1H-PYRAZOLE-4-CARBALDEHYDE; 5-CHLORO-1-(4-METHYLPHENYL)-3-(TRIFLUOROMETHYL)-1H-PYRAZOLE-4-CARBALDEHYDE; 5-CHLORO-1-(4-METHYLPHENYL)-3-PROPYL-1H-PYRAZOLE-4-CARBALDEHYDE; 5-CHLORO-1-(4-METHYLPYRIDIN-2-YL)-3-(PROPAN-2-YL)-1H-PYRAZOLE-4-CARBALDEHYDE; 5-CHLORO-1-(4-METHYLPYRIDIN-2-YL)-3-(TRIFLUOROMETHYL)-1H-PYRAZOLE-4-CARBALDEHYDE; 5-CHLORO-1-(4-METHYLPYRIDIN-2-YL)-3-PROPYL-1H-PYRAZOLE-4-CARBALDEHYDE; 5-CHLORO-1-(4-NITROPHENYL)-1H-PYRAZOLE-4-CARBOXALDEHYDE; 5-CHLORO-1-(4-NITROPHENYL)-3-PHENYL-1H-PYRAZOLE-4-CARBOXALDEHYDE; 5-CHLORO-1-(6-CHLOROPYRIDAZIN-3-YL)-3-(DIFLUOROMETHYL)-1H-PYRAZOLE-4-CARBALDEHYDE; 5-CHLORO-1-(6-CHLOROPYRIDAZIN-3-YL)-3-(METHOXYMETHYL)-1H-PYRAZOLE-4-CARBALDEHYDE; 5-CHLORO-1-(6-CHLOROPYRIDAZIN-3-YL)-3-(PROPAN-2-YL)-1H-PYRAZOLE-4-CARBALDEHYDE; 5-CHLORO-1-(6-CHLOROPYRIDAZIN-3-YL)-3-(TRIFLUOROMETHYL)-1H-PYRAZOLE-4-CARBALDEHYDE; 5-CHLORO-1-(6-CHLOROPYRIDAZIN-3-YL)-3-ETHYL-1H-PYRAZOLE-4-CARBALDEHYDE; 5-CHLORO-1-(6-CHLOROPYRIDAZIN-3-YL)-3-METHYL-1H-PYRAZOLE-4-CARBALDEHYDE; 5-CHLORO-1-(6-CHLOROPYRIDAZIN-3-YL)-3-PROPYL-1H-PYRAZOLE-4-CARBALDEHYDE; 5-CHLORO-1-(6-METHYLPYRIDAZIN-3-YL)-3-(PROPAN-2-YL)-1H-PYRAZOLE-4-CARBALDEHYDE; 5-CHLORO-1-(6-METHYLPYRIDAZIN-3-YL)-3-(TRIFLUOROMETHYL)-1H-PYRAZOLE-4-CARBALDEHYDE; 5-CHLORO-1-(6-METHYLPYRIDAZIN-3-YL)-3-PROPYL-1H-PYRAZOLE-4-CARBALDEHYDE; 5-CHLORO-1-(6-METHYLPYRIMIDIN-4-YL)-3-(PROPAN-2-YL)-1H-PYRAZOLE-4-CARBALDEHYDE; 5-CHLORO-1-(6-METHYLPYRIMIDIN-4-YL)-3-(TRIFLUOROMETHYL)-1H-PYRAZOLE-4-CARBALDEHYDE; 5-CHLORO-1-(6-METHYLPYRIMIDIN-4-YL)-3-PROPYL-1H-PYRAZOLE-4-CARBALDEHYDE; 5-CHLORO-1-(PENTAN-3-YL)-3-(PROPAN-2-YL)-1H-PYRAZOLE-4-CARBALDEHYDE; 5-CHLORO-1-(PENTAN-3-YL)-3-(TRIFLUOROMETHYL)-1H-PYRAZOLE-4-CARBALDEHYDE; 5-CHLORO-1-(PENTAN-3-YL)-3-PHENYL-1H-PYRAZOLE-4-CARBALDEHYDE; 5-CHLORO-1-(PENTAN-3-YL)-3-PROPYL-1H-PYRAZOLE-4-CARBALDEHYDE; 5-CHLORO-1-(PROPAN-2-YL)-3-(TRIFLUOROMETHYL)-1H-PYRAZOLE-4-CARBALDEHYDE; 5-CHLORO-1-(PROPAN-2-YL)-3-PROPYL-1H-PYRAZOLE-4-CARBALDEHYDE; 5-CHLORO-1-(PYRIDIN-2-YL)-3-(TRIFLUOROMETHYL)-1H-PYRAZOLE-4-CARBALDEHYDE; 5-CHLORO-1-(PYRIDIN-4-YL)-3-(TRIFLUOROMETHYL)-1H-PYRAZOLE-4-CARBALDEHYDE; 5-CHLORO-1-(PYRIMIDIN-2-YL)-3-(TRIFLUOROMETHYL)-1H-PYRAZOLE-4-CARBALDEHYDE; 5-CHLORO-1,3-BIS(PROPAN-2-YL)-1H-PYRAZOLE-4-CARBALDEHYDE; 5-CHLORO-1,3-DIETHYL-1H-PYRAZOLE-4-CARBALDEHYDE; 5-CHLORO-1,3-DIMETHYL-1H-PYRAZOLE-4-CARBALDEHYDE; 5-CHLORO-1,3-DIMETHYL-2,4,7-TRIOXO-8-PHENYL-1,2,3,4,7,8-HEXAHYDROPYRIDO[2,3-D]PYRIMIDINE-6-CARBOXALDEHYDE; 5-CHLORO-1,3-DIPHENYL-

1H-PYRAZOLE-4-CARBALDEHYDE; 5-CHLORO-1,3-DIPROPYL-1H-PYRAZOLE-4-CARBALDEHYDE; 5-CHLORO-1-[(4-METHYLPHENYL)METHYL]-3-(PROPAN-2-YL)-1H-PYRAZOLE-4-CARBALDEHYDE; 5-CHLORO-1-[(4-METHYLPHENYL)METHYL]-3-PROPYL-1H-PYRAZOLE-4-CARBALDEHYDE; 5-CHLORO-1-[2-(DIMETHYLAMINO)ETHYL]-3-(METHOXYMETHYL)-1H-PYRAZOLE-4-CARBALDEHYDE; 5-CHLORO-1-[2-(DIMETHYLAMINO)ETHYL]-3-(PROPAN-2-YL)-1H-PYRAZOLE-4-CARBALDEHYDE; 5-CHLORO-1-[2-(DIMETHYLAMINO)ETHYL]-3-(TRIFLUOROMETHYL)-1H-PYRAZOLE-4-CARBALDEHYDE; 5-CHLORO-1-[2-(DIMETHYLAMINO)ETHYL]-3-ETHYL-1H-PYRAZOLE-4-CARBALDEHYDE; 5-CHLORO-1-[2-(DIMETHYLAMINO)ETHYL]-3-METHYL-1H-PYRAZOLE-4-CARBALDEHYDE; 5-CHLORO-1-[2-(DIMETHYLAMINO)ETHYL]-3-PHENYL-1H-PYRAZOLE-4-CARBALDEHYDE; 5-CHLORO-1-[2-(DIMETHYLAMINO)ETHYL]-3-PROPYL-1H-PYRAZOLE-4-CARBALDEHYDE; 5-CHLORO-1-[2-(TRIFLUOROMETHYL)PHENYL]-1H-PYRAZOLE-4-CARBOXALDEHYDE; 5-CHLORO-1-[3-(TRIFLUOROMETHYL)PHENYL]-1H-PYRAZOLE-4-CARBOXALDEHYDE; 5-CHLORO-1-[4-(TRIFLUOROMETHYL)PHENYL]-1H-PYRAZOLE-4-CARBOXALDEHYDE; 5-CHLORO-1-CYCLOHEPTYL-3-(DIFLUOROMETHYL)-1H-PYRAZOLE-4-CARBALDEHYDE; 5-CHLORO-1-CYCLOHEPTYL-3-(METHOXYMETHYL)-1H-PYRAZOLE-4-CARBALDEHYDE; 5-CHLORO-1-CYCLOHEPTYL-3-(PROPAN-2-YL)-1H-PYRAZOLE-4-CARBALDEHYDE; 5-CHLORO-1-CYCLOHEPTYL-3-(TRIFLUOROMETHYL)-1H-PYRAZOLE-4-CARBALDEHYDE; 5-CHLORO-1-CYCLOHEPTYL-3-ETHYL-1H-PYRAZOLE-4-CARBALDEHYDE; 5-CHLORO-1-CYCLOHEPTYL-3-METHYL-1H-PYRAZOLE-4-CARBALDEHYDE; 5-CHLORO-1-CYCLOHEPTYL-3-PROPYL-1H-PYRAZOLE-4-CARBALDEHYDE; 5-CHLORO-1-CYCLOHEXYL-3-(DIFLUOROMETHYL)-1H-PYRAZOLE-4-CARBALDEHYDE; 5-CHLORO-1-CYCLOHEXYL-3-(METHOXYMETHYL)-1H-PYRAZOLE-4-CARBALDEHYDE; 5-CHLORO-1-CYCLOHEXYL-3-(PROPAN-2-YL)-1H-PYRAZOLE-4-CARBALDEHYDE; 5-CHLORO-1-CYCLOHEXYL-3-(TRIFLUOROMETHYL)-1H-PYRAZOLE-4-CARBALDEHYDE; 5-CHLORO-1-CYCLOHEXYL-3-ETHYL-1H-PYRAZOLE-4-CARBALDEHYDE; 5-CHLORO-1-CYCLOHEXYL-3-METHYL-1H-PYRAZOLE-4-CARBALDEHYDE; 5-CHLORO-1-CYCLOHEXYL-3-PROPYL-1H-PYRAZOLE-4-CARBALDEHYDE; 5-CHLORO-1-CYCLOPENTYL-3-(DIFLUOROMETHYL)-1H-PYRAZOLE-4-CARBALDEHYDE; 5-CHLORO-1-CYCLOPENTYL-3-(METHOXYMETHYL)-1H-PYRAZOLE-4-CARBALDEHYDE; 5-CHLORO-1-CYCLOPENTYL-3-(PROPAN-2-YL)-1H-PYRAZOLE-4-CARBALDEHYDE; 5-CHLORO-1-CYCLOPENTYL-3-(TRIFLUOROMETHYL)-1H-PYRAZOLE-4-CARBALDEHYDE; 5-CHLORO-1-CYCLOPENTYL-3-CYCLOPROPYL-1H-PYRAZOLE-4-CARBALDEHYDE; 5-CHLORO-1-CYCLOPENTYL-3-ETHYL-1H-PYRAZOLE-4-CARBALDEHYDE; 5-CHLORO-1-CYCLOPENTYL-3-METHYL-1H-PYRAZOLE-4-CARBALDEHYDE; 5-CHLORO-1-CYCLOPENTYL-3-PHENYL-1H-PYRAZOLE-4-CARBALDEHYDE; 5-CHLORO-1-CYCLOPENTYL-3-PROPYL-1H-PYRAZOLE-4-CARBALDEHYDE; 5-CHLORO-1-ETHYL-3-(METHOXYMETHYL)-1H-PYRAZOLE-4-CARBALDEHYDE; 5-CHLORO-1-ETHYL-3-(PROPAN-2-YL)-1H-PYRAZOLE-4-CARBALDEHYDE; 5-CHLORO-1-ETHYL-3-(TRIFLUOROMETHYL)-1H-PYRAZOLE-4-CARBALDEHYDE; 5-CHLORO-1-ETHYL-3-METHYL-1H-PYRAZOLE-4-CARBALDEHYDE; 5-CHLORO-1-ETHYL-3-PHENYL-1H-PYRAZOLE-4-CARBALDEHYDE; 5-CHLORO-1-ETHYL-3-PROPYL-1H-PYRAZOLE-4-CARBALDEHYDE; 5-CHLORO-1H-PYRROLE-2,4-DICARBALDEHYDE; 5-CHLORO-1H-PYRROLE-2-CARBALDEHYDE; 5-CHLORO-1-ISOBUTYL-3-METHYL-1H-PYRAZOLE-4-CARBALDEHYDE; 5-CHLORO-1-METHYL-1H-PYRAZOLE-4-CARBALDEHYDE; 5-CHLORO-1-METHYL-1H-PYRROLE-2,4-DICARBALDEHYDE; 5-CHLORO-1-METHYL-1H-PYRROLE-2-CARBALDEHYDE; 5-CHLORO-1-METHYL-3-([(4-METHYLPHENYL)SULFANYL]METHYL)-1H-PYRAZOLE-4-CARBALDEHYDE; 5-CHLORO-1-METHYL-3-(2,3,4-TRIFLUOROPHENYL)-1H-PYRAZOLE-4-CARBOXALDEHYDE; 5-CHLORO-1-METHYL-3-(2-METHYLPHENYL)-1H-PYRAZOLE-4-CARBOXALDEHYDE; 5-CHLORO-1-METHYL-3-(2-METHYLPROPYL)-1H-PYRAZOLE-4-CARBOXALDEHYDE; 5-CHLORO-1-METHYL-3-(2-NITROPHENYL)-1H-PYRAZOLE-4-CARBOXALDEHYDE; 5-CHLORO-1-METHYL-3-(3-METHYLPHENYL)-1H-PYRAZOLE-4-CARBOXALDEHYDE; 5-CHLORO-1-METHYL-3-(3-NITROPHENYL)-1H-PYRAZOLE-4-CARBOXALDEHYDE; 5-CHLORO-1-METHYL-3-(4-METHYLPHENYL)-1H-PYRAZOLE-4-CARBOXALDEHYDE; 5-CHLORO-1-METHYL-3-(4-NITROPHENYL)-1H-PYRAZOLE-4-CARBOXALDEHYDE; 5-CHLORO-1-METHYL-3-(4-PROPYLPHENYL)-1H-PYRAZOLE-4-CARBOXALDEHYDE; 5-CHLORO-1-METHYL-3-(PROPAN-2-YL)-1H-PYRAZOLE-4-CARBALDEHYDE; 5-CHLORO-1-METHYL-3-(TRIFLUOROMETHYL)-1H-PYRAZOLE-4-CARBALDEHYDE; 5-CHLORO-1-METHYL-3-[(PHENYLSULFANYL)METHYL]-1H-PYRAZOLE-4-CARBALDEHYDE; 5-CHLORO-1-METHYL-3-[2-(TRIFLUOROMETHYL)PHENYL]-1H-PYRAZOLE-4-CARBOXALDEHYDE; 5-CHLORO-1-METHYL-3-[3-(TRIFLUOROMETHYL)PHENYL]-1H-PYRAZOLE-4-CARBOXALDEHYDE; 5-CHLORO-1-METHYL-3-[4-(1-METHYLETHYL)PHENYL]-1H-PYRAZOLE-4-CARBOXALDEHYDE; 5-CHLORO-1-METHYL-3-[4-(TRIFLUOROMETHYL)PHENYL]-1H-PYRAZOLE-4-CARBOXALDEHYDE; 5-CHLORO-1-METHYL-3-PHENYL-1H-PYRAZOLE-4-CARBALDEHYDE; 5-CHLORO-1-METHYL-3-PROPYL-1H-PYRAZOLE-4-CARBALDEHYDE; 5-CHLORO-1-PHENYL-3-(2,3,4-TRIFLUOROPHENYL)-1H-PYRAZOLE-4-CARBOXALDEHYDE; 5-CHLORO-1-PHENYL-3-(4-PROPYLPHENYL)-1H-PYRAZOLE-4-CARBOXALDEHYDE; 5-CHLORO-1-PHENYL-3-(PROPAN-2-YL)-1H-PYRAZOLE-4-CARBALDEHYDE; 5-CHLORO-1-PHENYL-3-(TRIFLUOROMETHYL)-1H-PYRAZOLE-4-CARBALDEHYDE; 5-CHLORO-1-PHENYL-3-PROPYL-1H-PYRAZOLE-4-CARBALDEHYDE; 5-CHLORO-1-PROPYL-3-(TRIFLUOROMETHYL)-1H-PYRAZOLE-4-CARBALDEHYDE; 5-CHLORO-2-(DIMETHYLAMINO)-1-(4-FLUOROPHENYL)-1H-IMIDA-

ZOLE-4-CARBALDEHYDE; 5-CHLORO-2-(DIMETHYLAMINO)-1-(4-METHYLPHENYL)-1H-IMIDAZOLE-4-CARBALDEHYDE; 5-CHLORO-2-(DIMETHYLAMINO)-1-PHENYL-1H-IMIDAZOLE-4-CARBALDEHYDE; 5-CHLORO-2-[(2-CHLOROPROP-2-EN-1-YL)OXY]BENZALDEHYDE; 5-CHLORO-2-[(5-CHLORO-1-METHYL-1H-IMIDAZOL-2-YL)METHOXY]BENZALDEHYDE; 5-CHLORO-2-OXO-1,2-DIHYDRO-3-PYRIDINECARBALDEHYDE; 5-CHLORO-2-OXO-3-PHENYL-2,3-DIHYDRO-1H-IMIDAZOLE-4-CARBALDEHYDE; 5-CHLORO-2-PHENYL-1H-IMIDAZOLE-4-CARBALDEHYDE; 5-CHLORO-2-PHENYL-3H-IMIDAZOLE-4-CARBALDEHYDE; 5-CHLORO-2-PHENYLIMIDAZO[1,2-A]PYRIDINE-3-CARBALDEHYDE; 5-CHLORO-3-([(4-CHLOROPHENYL)SULFANYL]METHYL)-1-METHYL-1H-PYRAZOLE-4-CARBALDEHYDE; 5-CHLORO-3-(2,3-DICHLOROPHENYL)-1-(1,1-DIMETHYLETHYL)-1H-PYRAZOLE-4-CARBOXALDEHYDE; 5-CHLORO-3-(2,3-DICHLOROPHENYL)-1-METHYL-1H-PYRAZOLE-4-CARBOXALDEHYDE; 5-CHLORO-3-(2,3-DIFLUOROPHENYL)-1-(1,1-DIMETHYLETHYL)-1H-PYRAZOLE-4-CARBOXALDEHYDE; 5-CHLORO-3-(2,3-DIFLUOROPHENYL)-1-(2-FLUOROPHENYL)-1H-PYRAZOLE-4-CARBOXALDEHYDE; 5-CHLORO-3-(2,3-DIFLUOROPHENYL)-1-(3-FLUOROPHENYL)-1H-PYRAZOLE-4-CARBOXALDEHYDE; 5-CHLORO-3-(2,3-DIFLUOROPHENYL)-1-(4-FLUOROPHENYL)-1H-PYRAZOLE-4-CARBOXALDEHYDE; 5-CHLORO-3-(2,3-DIFLUOROPHENYL)-1-METHYL-1H-PYRAZOLE-4-CARBOXALDEHYDE; 5-CHLORO-3-(2,3-DIFLUOROPHENYL)-1-PHENYL-1H-PYRAZOLE-4-CARBOXALDEHYDE; 5-CHLORO-3-(2,3-DIMETHOXYPHENYL)-1-(1,1-DIMETHYLETHYL)-1H-PYRAZOLE-4-CARBOXALDEHYDE; 5-CHLORO-3-(2,3-DIMETHOXYPHENYL)-1-METHYL-1H-PYRAZOLE-4-CARBOXALDEHYDE; 5-CHLORO-3-(2,3-DIMETHOXYPHENYL)-1-PHENYL-1H-PYRAZOLE-4-CARBOXALDEHYDE; 5-CHLORO-3-(2,4-DICHLOROPHENYL)-1-(1,1-DIMETHYLETHYL)-1H-PYRAZOLE-4-CARBOXALDEHYDE; 5-CHLORO-3-(2,4-DICHLOROPHENYL)-1-METHYL-1H-PYRAZOLE-4-CARBOXALDEHYDE; 5-CHLORO-3-(2,4-DIFLUOROPHENYL)-1-(1,1-DIMETHYLETHYL)-1H-PYRAZOLE-4-CARBOXALDEHYDE; 5-CHLORO-3-(2,4-DIFLUOROPHENYL)-1-(2-FLUOROPHENYL)-1H-PYRAZOLE-4-CARBOXALDEHYDE; 5-CHLORO-3-(2,4-DIFLUOROPHENYL)-1-(3-FLUOROPHENYL)-1H-PYRAZOLE-4-CARBOXALDEHYDE; 5-CHLORO-3-(2,4-DIFLUOROPHENYL)-1-(4-FLUOROPHENYL)-1H-PYRAZOLE-4-CARBOXALDEHYDE; 5-CHLORO-3-(2,4-DIFLUOROPHENYL)-1-METHYL-1H-PYRAZOLE-4-CARBOXALDEHYDE; 5-CHLORO-3-(2,4-DIFLUOROPHENYL)-1-PHENYL-1H-PYRAZOLE-4-CARBOXALDEHYDE; 5-CHLORO-3-(2,4-DIMETHOXYPHENYL)-1-(1,1-DIMETHYLETHYL)-1H-PYRAZOLE-4-CARBOXALDEHYDE; 5-CHLORO-3-(2,4-DIMETHOXYPHENYL)-1-METHYL-1H-PYRAZOLE-4-CARBOXALDEHYDE; 5-CHLORO-3-(2,4-DIMETHOXYPHENYL)-1-PHENYL-1H-PYRAZOLE-4-CARBOXALDEHYDE; 5-CHLORO-3-(2,5-DICHLOROPHENYL)-1-(1,1-DIMETHYLETHYL)-1H-PYRAZOLE-4-CARBOXALDEHYDE; 5-CHLORO-3-(2,5-DICHLOROPHENYL)-1-METHYL-1H-PYRAZOLE-4-CARBOXALDEHYDE; 5-CHLORO-3-(2,5-DIFLUOROPHENYL)-1-(1,1-DIMETHYLETHYL)-1H-PYRAZOLE-4-CARBOXALDEHYDE; 5-CHLORO-3-(2,5-DIFLUOROPHENYL)-1-(2-FLUOROPHENYL)-1H-PYRAZOLE-4-CARBOXALDEHYDE; 5-CHLORO-3-(2,5-DIFLUOROPHENYL)-1-(3-FLUOROPHENYL)-1H-PYRAZOLE-4-CARBOXALDEHYDE; 5-CHLORO-3-(2,5-DIFLUOROPHENYL)-1-(4-FLUOROPHENYL)-1H-PYRAZOLE-4-CARBOXALDEHYDE; 5-CHLORO-3-(2,5-DIFLUOROPHENYL)-1-METHYL-1H-PYRAZOLE-4-CARBOXALDEHYDE; 5-CHLORO-3-(2,5-DIFLUOROPHENYL)-1-PHENYL-1H-PYRAZOLE-4-CARBOXALDEHYDE; 5-CHLORO-3-(2,5-DIMETHOXYPHENYL)-1-(1,1-DIMETHYLETHYL)-1H-PYRAZOLE-4-CARBOXALDEHYDE; 5-CHLORO-3-(2,5-DIMETHOXYPHENYL)-1-METHYL-1H-PYRAZOLE-4-CARBOXALDEHYDE; 5-CHLORO-3-(2,5-DIMETHOXYPHENYL)-1-PHENYL-1H-PYRAZOLE-4-CARBOXALDEHYDE; 5-CHLORO-3-(2,6-DICHLOROPHENYL)-1-(1,1-DIMETHYLETHYL)-1H-PYRAZOLE-4-CARBOXALDEHYDE; 5-CHLORO-3-(2,6-DICHLOROPHENYL)-1-METHYL-1H-PYRAZOLE-4-CARBOXALDEHYDE; 5-CHLORO-3-(2,6-DIFLUOROPHENYL)-1-(1,1-DIMETHYLETHYL)-1H-PYRAZOLE-4-CARBOXALDEHYDE; 5-CHLORO-3-(2,6-DIFLUOROPHENYL)-1-(2-FLUOROPHENYL)-1H-PYRAZOLE-4-CARBOXALDEHYDE; 5-CHLORO-3-(2,6-DIFLUOROPHENYL)-1-(3-FLUOROPHENYL)-1H-PYRAZOLE-4-CARBOXALDEHYDE; 5-CHLORO-3-(2,6-DIFLUOROPHENYL)-1-(4-FLUOROPHENYL)-1H-PYRAZOLE-4-CARBOXALDEHYDE; 5-CHLORO-3-(2,6-DIFLUOROPHENYL)-1-METHYL-1H-PYRAZOLE-4-CARBOXALDEHYDE; 5-CHLORO-3-(2,6-DIFLUOROPHENYL)-1-PHENYL-1H-PYRAZOLE-4-CARBOXALDEHYDE; 5-CHLORO-3-(2,6-DIMETHOXYPHENYL)-1-(1,1-DIMETHYLETHYL)-1H-PYRAZOLE-4-CARBOXALDEHYDE; 5-CHLORO-3-(2,6-DIMETHOXYPHENYL)-1-METHYL-1H-PYRAZOLE-4-CARBOXALDEHYDE; 5-CHLORO-3-(2,6-DIMETHOXYPHENYL)-1-PHENYL-1H-PYRAZOLE-4-CARBOXALDEHYDE; 5-CHLORO-3-(2,6-DIMETHYLPHENYL)-1-PHENYL-1H-PYRAZOLE-4-CARBOXALDEHYDE; 5-CHLORO-3-(2-CHLORO-4-FLUOROPHENYL)-1-(1,1-DIMETHYLETHYL)-1H-PYRAZOLE-4-CARBOXALDEHYDE; 5-CHLORO-3-(2-CHLORO-4-FLUOROPHENYL)-1-METHYL-1H-PYRAZOLE-4-CARBOXALDEHYDE; 5-CHLORO-3-(2-CHLORO-4-FLUOROPHENYL)-1-PHENYL-1H-PYRAZOLE-4-CARBOXALDEHYDE; 5-CHLORO-3-(2-CHLORO-4-NITROPHENYL)-1-(1,1-DIMETHYLETHYL)-1H-PYRAZOLE-4-CARBOXALDEHYDE; 5-CHLORO-3-(2-CHLORO-4-NITROPHENYL)-1-METHYL-1H-PYRAZOLE-4-CARBOXALDEHYDE; 5-CHLORO-3-(2-CHLORO-5-FLUOROPHENYL)-1-(1,1-DIMETHYLETHYL)-1H-PYRAZOLE-4-CARBOXALDEHYDE; 5-CHLORO-3-(2-CHLORO-5-FLUOROPHENYL)-1-METHYL-1H-PYRAZOLE-4-CARBOXALDEHYDE; 5-CHLORO-3-(2-CHLORO-5-FLUOROPHENYL)-1-PHENYL-1H-PYRAZOLE-4-CARBOXALDEHYDE; 5-CHLORO-3-(2-CHLORO-5-NITROPHENYL)-1-(1,1-DIMETHYLETHYL)-1H-PYRAZOLE-4-CARBOXALDEHYDE; 5-CHLORO-3-(2-CHLORO-5-NITROPHENYL)-1-METHYL-1H-PYRAZOLE-4-CARBOXALDEHYDE; 5-CHLORO-3-(2-CHLORO-6-FLUOROPHENYL)-1-(1,1-DIMETHYLETHYL)-1H-PYRAZOLE-4-CARBOXALDEHYDE; 5-CHLORO-3-(2-CHLORO-6-FLUOROPHENYL)-1-METHYL-1H-PYRAZOLE-4-CARBOXALDEHYDE; 5-CHLORO-3-(2-

CHLORO-6-FLUOROPHENYL)-1-PHENYL-1H-PYRAZOLE-4-CARBOXALDEHYDE; 5-CHLORO-3-(2-CHLOROPHENYL)-1-(1,1-DIMETHYLETHYL)-1H-PYRAZOLE-4-CARBOXALDEHYDE; 5-CHLORO-3-(2-CHLOROPHENYL)-1-(2-FLUOROPHENYL)-1H-PYRAZOLE-4-CARBOXALDEHYDE; 5-CHLORO-3-(2-CHLOROPHENYL)-1-(3-FLUOROPHENYL)-1H-PYRAZOLE-4-CARBOXALDEHYDE; 5-CHLORO-3-(2-CHLOROPHENYL)-1-(4-FLUOROPHENYL)-1H-PYRAZOLE-4-CARBOXALDEHYDE; 5-CHLORO-3-(2-CHLOROPHENYL)-1-METHYL-1H-PYRAZOLE-4-CARBOXALDEHYDE; 5-CHLORO-3-(2-CHLOROPHENYL)-1-PHENYL-1H-PYRAZOLE-4-CARBOXALDEHYDE; 5-CHLORO-3-(2-ETHOXYPHENYL)-1-METHYL-1H-PYRAZOLE-4-CARBOXALDEHYDE; 5-CHLORO-3-(2-ETHOXYPHENYL)-1-PHENYL-1H-PYRAZOLE-4-CARBOXALDEHYDE; 5-CHLORO-3-(2-FLUORO-4-NITROPHENYL)-1-METHYL-1H-PYRAZOLE-4-CARBOXALDEHYDE; 5-CHLORO-3-(2-FLUORO-4-NITROPHENYL)-1-PHENYL-1H-PYRAZOLE-4-CARBOXALDEHYDE; 5-CHLORO-3-(2-FLUORO-5-NITROPHENYL)-1-METHYL-1H-PYRAZOLE-4-CARBOXALDEHYDE; 5-CHLORO-3-(2-FLUORO-5-NITROPHENYL)-1-PHENYL-1H-PYRAZOLE-4-CARBOXALDEHYDE; 5-CHLORO-3-(2-FLUOROPHENYL)-1-(2-NITROPHENYL)-1H-PYRAZOLE-4-CARBOXALDEHYDE; 5-CHLORO-3-(2-FLUOROPHENYL)-1-(3-FLUOROPHENYL)-1H-PYRAZOLE-4-CARBOXALDEHYDE; 5-CHLORO-3-(2-FLUOROPHENYL)-1-(3-NITROPHENYL)-1H-PYRAZOLE-4-CARBOXALDEHYDE; 5-CHLORO-3-(2-FLUOROPHENYL)-1-(4-FLUOROPHENYL)-1H-PYRAZOLE-4-CARBOXALDEHYDE; 5-CHLORO-3-(2-FLUOROPHENYL)-1-(4-NITROPHENYL)-1H-PYRAZOLE-4-CARBOXALDEHYDE; 5-CHLORO-3-(2-FLUOROPHENYL)-1-METHYL-1H-PYRAZOLE-4-CARBOXALDEHYDE; 5-CHLORO-3-(2-FLUOROPHENYL)-1-PHENYL-1H-PYRAZOLE-4-CARBOXALDEHYDE; 5-CHLORO-3-(2-METHOXYPHENYL)-1-METHYL-1H-PYRAZOLE-4-CARBOXALDEHYDE; 5-CHLORO-3-(2-METHOXYPHENYL)-1-PHENYL-1H-PYRAZOLE-4-CARBOXALDEHYDE; 5-CHLORO-3-(2-METHYLPHENYL)-1-PHENYL-1H-PYRAZOLE-4-CARBOXALDEHYDE; 5-CHLORO-3-(2-METHYLPROPYL)-1-PHENYL-1H-PYRAZOLE-4-CARBOXALDEHYDE; 5-CHLORO-3-(2-NITROPHENYL)-1-PHENYL-1H-PYRAZOLE-4-CARBOXALDEHYDE; 5-CHLORO-3-(3,4-DICHLOROPHENYL)-1-(1,1-DIMETHYLETHYL)-1H-PYRAZOLE-4-CARBOXALDEHYDE; 5-CHLORO-3-(3,4-DICHLOROPHENYL)-1-METHYL-1H-PYRAZOLE-4-CARBOXALDEHYDE; 5-CHLORO-3-(3,4-DIFLUOROPHENYL)-1-(1,1-DIMETHYLETHYL)-1H-PYRAZOLE-4-CARBOXALDEHYDE; 5-CHLORO-3-(3,4-DIFLUOROPHENYL)-1-(2-FLUOROPHENYL)-1H-PYRAZOLE-4-CARBOXALDEHYDE; 5-CHLORO-3-(3,4-DIFLUOROPHENYL)-1-(3-FLUOROPHENYL)-1H-PYRAZOLE-4-CARBOXALDEHYDE; 5-CHLORO-3-(3,4-DIFLUOROPHENYL)-1-(4-FLUOROPHENYL)-1H-PYRAZOLE-4-CARBOXALDEHYDE; 5-CHLORO-3-(3,4-DIFLUOROPHENYL)-1-METHYL-1H-PYRAZOLE-4-CARBOXALDEHYDE; 5-CHLORO-3-(3,4-DIFLUOROPHENYL)-1-PHENYL-1H-PYRAZOLE-4-CARBOXALDEHYDE; 5-CHLORO-3-(3,4-DIMETHOXYPHENYL)-1-(1,1-DIMETHYLETHYL)-1H-PYRAZOLE-4-CARBOXALDEHYDE; 5-CHLORO-3-(3,4-DIMETHOXYPHENYL)-1-METHYL-1H-PYRAZOLE-4-CARBOXALDEHYDE; 5-CHLORO-3-(3,4-DIMETHOXYPHENYL)-1-PHENYL-1H-PYRAZOLE-4-CARBOXALDEHYDE; 5-CHLORO-3-(3,5-DICHLOROPHENYL)-1-(1,1-DIMETHYLETHYL)-1H-PYRAZOLE-4-CARBOXALDEHYDE; 5-CHLORO-3-(3,5-DICHLOROPHENYL)-1-METHYL-1H-PYRAZOLE-4-CARBOXALDEHYDE; 5-CHLORO-3-(3,5-DIFLUOROPHENYL)-1-(1,1-DIMETHYLETHYL)-1H-PYRAZOLE-4-CARBOXALDEHYDE; 5-CHLORO-3-(3,5-DIFLUOROPHENYL)-1-(2-FLUOROPHENYL)-1H-PYRAZOLE-4-CARBOXALDEHYDE; 5-CHLORO-3-(3,5-DIFLUOROPHENYL)-1-(3-FLUOROPHENYL)-1H-PYRAZOLE-4-CARBOXALDEHYDE; 5-CHLORO-3-(3,5-DIFLUOROPHENYL)-1-(4-FLUOROPHENYL)-1H-PYRAZOLE-4-CARBOXALDEHYDE; 5-CHLORO-3-(3,5-DIFLUOROPHENYL)-1-METHYL-1H-PYRAZOLE-4-CARBOXALDEHYDE; 5-CHLORO-3-(3,5-DIFLUOROPHENYL)-1-PHENYL-1H-PYRAZOLE-4-CARBOXALDEHYDE; 5-CHLORO-3-(3,5-DIMETHOXYPHENYL)-1-(1,1-DIMETHYLETHYL)-1H-PYRAZOLE-4-CARBOXALDEHYDE; 5-CHLORO-3-(3,5-DIMETHOXYPHENYL)-1-METHYL-1H-PYRAZOLE-4-CARBOXALDEHYDE; 5-CHLORO-3-(3,5-DIMETHOXYPHENYL)-1-PHENYL-1H-PYRAZOLE-4-CARBOXALDEHYDE; 5-CHLORO-3-(3,5-DIMETHYLPHENYL)-1-METHYL-1H-PYRAZOLE-4-CARBOXALDEHYDE; 5-CHLORO-3-(3,5-DIMETHYLPHENYL)-1-PHENYL-1H-PYRAZOLE-4-CARBOXALDEHYDE; 5-CHLORO-3-(3-CHLOROPHENYL)-1-(1,1-DIMETHYLETHYL)-1H-PYRAZOLE-4-CARBOXALDEHYDE; 5-CHLORO-3-(3-CHLOROPHENYL)-1-(2-FLUOROPHENYL)-1H-PYRAZOLE-4-CARBOXALDEHYDE; 5-CHLORO-3-(3-CHLOROPHENYL)-1-(3-FLUOROPHENYL)-1H-PYRAZOLE-4-CARBOXALDEHYDE; 5-CHLORO-3-(3-CHLOROPHENYL)-1-(4-FLUOROPHENYL)-1H-PYRAZOLE-4-CARBOXALDEHYDE; 5-CHLORO-3-(3-CHLOROPHENYL)-1-METHYL-1H-PYRAZOLE-4-CARBOXALDEHYDE; 5-CHLORO-3-(3-CHLOROPHENYL)-1-PHENYL-1H-PYRAZOLE-4-CARBOXALDEHYDE; 5-CHLORO-3-(3-FLUORO-4-METHOXYPHENYL)-1-METHYL-1H-PYRAZOLE-4-CARBOXALDEHYDE; 5-CHLORO-3-(3-FLUORO-4-METHOXYPHENYL)-1-PHENYL-1H-PYRAZOLE-4-CARBOXALDEHYDE; 5-CHLORO-3-(3-FLUOROPHENYL)-1-(2-NITROPHENYL)-1H-PYRAZOLE-4-CARBOXALDEHYDE; 5-CHLORO-3-(3-FLUOROPHENYL)-1-(3-NITROPHENYL)-1H-PYRAZOLE-4-CARBOXALDEHYDE; 5-CHLORO-3-(3-FLUOROPHENYL)-1-(4-FLUOROPHENYL)-1H-PYRAZOLE-4-CARBOXALDEHYDE; 5-CHLORO-3-(3-FLUOROPHENYL)-1-(4-NITROPHENYL)-1H-PYRAZOLE-4-CARBOXALDEHYDE; 5-CHLORO-3-(3-FLUOROPHENYL)-1-METHYL-1H-PYRAZOLE-4-CARBOXALDEHYDE; 5-CHLORO-3-(3-FLUOROPHENYL)-1-PHENYL-1H-PYRAZOLE-4-CARBOXALDEHYDE; 5-CHLORO-3-(3-METHOXYPHENYL)-1-METHYL-1H-PYRAZOLE-4-CARBOXALDEHYDE; 5-CHLORO-3-(3-METHOXYPHENYL)-1-PHENYL-1H-PYRAZOLE-4-CARBOXALDEHYDE; 5-CHLORO-3-(3-METHYLPHENYL)-1-PHENYL-1H-PYRAZOLE-4-CARBOXALDEHYDE; 5-CHLORO-3-(3-NITROPHENYL)-1-PHENYL-1H-PYRAZOLE-4-CARBOXALDEHYDE; 5-CHLORO-3-(4-CHLORO-3-

NITROPHENYL)-1-(1,1-DIMETHYLETHYL)-1H-PYRAZOLE-4-CARBOXALDEHYDE; 5-CHLORO-3-(4-CHLORO-3-NITROPHENYL)-1-METHYL-1H-PYRAZOLE-4-CARBOXALDEHYDE; 5-CHLORO-3-(4-CHLOROPHENYL)-1-(1,1-DIMETHYLETHYL)-1H-PYRAZOLE-4-CARBOXALDEHYDE; 5-CHLORO-3-(4-CHLOROPHENYL)-1-(2-FLUOROPHENYL)-1H-PYRAZOLE-4-CARBOXALDEHYDE; 5-CHLORO-3-(4-CHLOROPHENYL)-1-(3-FLUOROPHENYL)-1H-PYRAZOLE-4-CARBOXALDEHYDE; 5-CHLORO-3-(4-CHLOROPHENYL)-1-(4-FLUOROPHENYL)-1H-PYRAZOLE-4-CARBOXALDEHYDE; 5-CHLORO-3-(4-CHLOROPHENYL)-1-METHYL-1H-PYRAZOLE-4-CARBOXALDEHYDE; 5-CHLORO-3-(4-CHLOROPHENYL)-1-PHENYL-1H-PYRAZOLE-4-CARBOXALDEHYDE; 5-CHLORO-3-(4-ETHOXYPHENYL)-1-METHYL-1H-PYRAZOLE-4-CARBOXALDEHYDE; 5-CHLORO-3-(4-ETHOXYPHENYL)-1-PHENYL-1H-PYRAZOLE-4-CARBOXALDEHYDE; 5-CHLORO-3-(4-ETHYLPHENYL)-1-METHYL-1H-PYRAZOLE-4-CARBOXALDEHYDE; 5-CHLORO-3-(4-ETHYLPHENYL)-1-PHENYL-1H-PYRAZOLE-4-CARBOXALDEHYDE; 5-CHLORO-3-(4-FLUORO-3-NITROPHENYL)-1-METHYL-1H-PYRAZOLE-4-CARBOXALDEHYDE; 5-CHLORO-3-(4-FLUORO-3-NITROPHENYL)-1-PHENYL-1H-PYRAZOLE-4-CARBOXALDEHYDE; 5-CHLORO-3-(4-FLUOROPHENYL)-1-(2-NITROPHENYL)-1H-PYRAZOLE-4-CARBOXALDEHYDE; 5-CHLORO-3-(4-FLUOROPHENYL)-1-(3-NITROPHENYL)-1H-PYRAZOLE-4-CARBOXALDEHYDE; 5-CHLORO-3-(4-FLUOROPHENYL)-1-(4-NITROPHENYL)-1H-PYRAZOLE-4-CARBOXALDEHYDE; 5-CHLORO-3-(4-FLUOROPHENYL)-1-METHYL-1H-PYRAZOLE-4-CARBOXALDEHYDE; 5-CHLORO-3-(4-FLUOROPHENYL)-1-PHENYL-1H-PYRAZOLE-4-CARBOXALDEHYDE; 5-CHLORO-3-(4-METHOXYPHENYL)-1-METHYL-1H-PYRAZOLE-4-CARBOXALDEHYDE; 5-CHLORO-3-(4-METHOXYPHENYL)-1-PHENYL-1H-PYRAZOLE-4-CARBOXALDEHYDE; 5-CHLORO-3-(4-METHYLPHENYL)-1-PHENYL-1H-PYRAZOLE-4-CARBOXALDEHYDE; 5-CHLORO-3-(4-NITROPHENYL)-1-PHENYL-1H-PYRAZOLE-4-CARBOXALDEHYDE; 5-CHLORO-3-(DIFLUOROMETHYL)-1-(2,4-DIFLUOROPHENYL)-1H-PYRAZOLE-4-CARBALDEHYDE; 5-CHLORO-3-(DIFLUOROMETHYL)-1-(2,4-DIMETHYLPHENYL)-1H-PYRAZOLE-4-CARBALDEHYDE; 5-CHLORO-3-(DIFLUOROMETHYL)-1-(2,5-DIMETHYLPHENYL)-1H-PYRAZOLE-4-CARBALDEHYDE; 5-CHLORO-3-(DIFLUOROMETHYL)-1-(2-FLUOROPHENYL)-1H-PYRAZOLE-4-CARBALDEHYDE; 5-CHLORO-3-(DIFLUOROMETHYL)-1-(2-METHOXYPHENYL)-1H-PYRAZOLE-4-CARBALDEHYDE; 5-CHLORO-3-(DIFLUOROMETHYL)-1-(2-METHYLPHENYL)-1H-PYRAZOLE-4-CARBALDEHYDE; 5-CHLORO-3-(DIFLUOROMETHYL)-1-(2-METHYLPROPYL)-1H-PYRAZOLE-4-CARBALDEHYDE; 5-CHLORO-3-(DIFLUOROMETHYL)-1-(3,5-DIMETHYLPHENYL)-1H-PYRAZOLE-4-CARBALDEHYDE; 5-CHLORO-3-(DIFLUOROMETHYL)-1-(3-FLUOROPHENYL)-1H-PYRAZOLE-4-CARBALDEHYDE; 5-CHLORO-3-(DIFLUOROMETHYL)-1-(3-METHYLBUTYL)-1H-PYRAZOLE-4-CARBALDEHYDE; 5-CHLORO-3-(DIFLUOROMETHYL)-1-(3-METHYLPHENYL)-1H-PYRAZOLE-4-CARBALDEHYDE; 5-CHLORO-3-(DIFLUOROMETHYL)-1-(4,6-DIMETHYLPYRIMIDIN-2-YL)-1H-PYRAZOLE-4-CARBALDEHYDE; 5-CHLORO-3-(DIFLUOROMETHYL)-1-(4-FLUOROPHENYL)-1H-PYRAZOLE-4-CARBALDEHYDE; 5-CHLORO-3-(DIFLUOROMETHYL)-1-(4-METHYLPHENYL)-1H-PYRAZOLE-4-CARBALDEHYDE; 5-CHLORO-3-(DIFLUOROMETHYL)-1-(4-METHYLPYRIDIN-2-YL)-1H-PYRAZOLE-4-CARBALDEHYDE; 5-CHLORO-3-(DIFLUOROMETHYL)-1-(6-METHYLPYRIDAZIN-3-YL)-1H-PYRAZOLE-4-CARBALDEHYDE; 5-CHLORO-3-(DIFLUOROMETHYL)-1-(6-METHYLPYRIMIDIN-4-YL)-1H-PYRAZOLE-4-CARBALDEHYDE; 5-CHLORO-3-(DIFLUOROMETHYL)-1-(PENTAN-3-YL)-1H-PYRAZOLE-4-CARBALDEHYDE; 5-CHLORO-3-(DIFLUOROMETHYL)-1-(PROPAN-2-YL)-1H-PYRAZOLE-4-CARBALDEHYDE; 5-CHLORO-3-(DIFLUOROMETHYL)-1-(PYRIDIN-2-YL)-1H-PYRAZOLE-4-CARBALDEHYDE; 5-CHLORO-3-(DIFLUOROMETHYL)-1-(PYRIDIN-4-YL)-1H-PYRAZOLE-4-CARBALDEHYDE; 5-CHLORO-3-(DIFLUOROMETHYL)-1-(PYRIMIDIN-2-YL)-1H-PYRAZOLE-4-CARBALDEHYDE; 5-CHLORO-3-(DIFLUOROMETHYL)-1-[(4-METHYLPHENYL)METHYL]-1H-PYRAZOLE-4-CARBALDEHYDE; 5-CHLORO-3-(DIFLUOROMETHYL)-1-[2-(DIMETHYLAMINO)ETHYL]-1H-PYRAZOLE-4-CARBALDEHYDE; 5-CHLORO-3-(DIFLUOROMETHYL)-1-ETHYL-1H-PYRAZOLE-4-CARBALDEHYDE; 5-CHLORO-3-(DIFLUOROMETHYL)-1-METHYL-1H-PYRAZOLE-4-CARBALDEHYDE; 5-CHLORO-3-(DIFLUOROMETHYL)-1-PHENYL-1H-PYRAZOLE-4-CARBALDEHYDE; 5-CHLORO-3-(DIFLUOROMETHYL)-1-PROPYL-1H-PYRAZOLE-4-CARBALDEHYDE; 5-CHLORO-3-(METHOXYMETHYL)-1-(2-METHOXYPHENYL)-1H-PYRAZOLE-4-CARBALDEHYDE; 5-CHLORO-3-(METHOXYMETHYL)-1-(2-METHYLPHENYL)-1H-PYRAZOLE-4-CARBALDEHYDE; 5-CHLORO-3-(METHOXYMETHYL)-1-(2-METHYLPROPYL)-1H-PYRAZOLE-4-CARBALDEHYDE; 5-CHLORO-3-(METHOXYMETHYL)-1-(3-METHYLBUTYL)-1H-PYRAZOLE-4-CARBALDEHYDE; 5-CHLORO-3-(METHOXYMETHYL)-1-(3-METHYLPHENYL)-1H-PYRAZOLE-4-CARBALDEHYDE; 5-CHLORO-3-(METHOXYMETHYL)-1-(4-METHYLPHENYL)-1H-PYRAZOLE-4-CARBALDEHYDE; 5-CHLORO-3-(METHOXYMETHYL)-1-(4-METHYLPYRIDIN-2-YL)-1H-PYRAZOLE-4-CARBALDEHYDE; 5-CHLORO-3-(METHOXYMETHYL)-1-(6-METHYLPYRIDAZIN-3-YL)-1H-PYRAZOLE-4-CARBALDEHYDE; 5-CHLORO-3-(METHOXYMETHYL)-1-(6-METHYLPYRIMIDIN-4-YL)-1H-PYRAZOLE-4-CARBALDEHYDE; 5-CHLORO-3-(METHOXYMETHYL)-1-(PENTAN-3-YL)-1H-PYRAZOLE-4-CARBALDEHYDE; 5-CHLORO-3-(METHOXYMETHYL)-1-(PROPAN-2-YL)-1H-PYRAZOLE-4-CARBALDEHYDE; 5-CHLORO-3-(METHOXYMETHYL)-1-(PYRIDIN-2-YL)-1H-PYRAZOLE-4-CARBALDEHYDE; 5-CHLORO-3-(METHOXYMETHYL)-1-(PYRIDIN-4-YL)-1H-PYRAZOLE-4-CARBALDEHYDE; 5-CHLORO-3-(METHOXYMETHYL)-1-(PYRIMIDIN-2-YL)-1H-PYRAZOLE-4-CARBALDEHYDE; 5-CHLORO-3-(METHOXYMETHYL)-1-[(4-METHYLPHENYL)METHYL]-1H-PYRAZOLE-4-CARBALDEHYDE; 5-CHLORO-3-(METHOXYMETHYL)-1-METHYL-1H-PYRAZOLE-4-CARBALDEHYDE; 5-CHLORO-3-

(METHOXYMETHYL)-1-PHENYL-1H-PYRAZOLE-4-CARBALDEHYDE; 5-CHLORO-3-(METHOXYMETHYL)-1-PROPYL-1H-PYRAZOLE-4-CARBALDEHYDE; 5-CHLORO-3-(PROPAN-2-YL)-1-(PYRIDIN-2-YL)-1H-PYRAZOLE-4-CARBALDEHYDE; 5-CHLORO-3-(PROPAN-2-YL)-1-(PYRIDIN-4-YL)-1H-PYRAZOLE-4-CARBALDEHYDE; 5-CHLORO-3-(PROPAN-2-YL)-1-(PYRIMIDIN-2-YL)-1H-PYRAZOLE-4-CARBALDEHYDE; 5-CHLORO-3-(PROPAN-2-YL)-1-PROPYL-1H-PYRAZOLE-4-CARBALDEHYDE; 5-CHLORO-3-(TRIFLUOROMETHYL)-1H-PYRAZOLE-4-CARBALDEHYDE; 5-CHLORO-3-[2-(DIMETHYLAMINO)-1-FORMYLVINYL]-1-PHENYL-1H-PYRAZOLE-4-CARBOXALDEHYDE; 5-CHLORO-3-[4-(1,1-DIMETHYLETHYL)PHENYL]-1-METHYL-1H-PYRAZOLE-4-CARBOXALDEHYDE; 5-CHLORO-3-[4-(1,1-DIMETHYLETHYL)PHENYL]-1-PHENYL-1H-PYRAZOLE-4-CARBOXALDEHYDE; 5-CHLORO-3-[4-(1-METHYLETHYL)PHENYL]-1-PHENYL-1H-PYRAZOLE-4-CARBOXALDEHYDE; 5-CHLORO-3-CYCLOPROPYL-1-(1-CYCLOPROPYLETHYL)-1H-PYRAZOLE-4-CARBALDEHYDE; 5-CHLORO-3-CYCLOPROPYL-1-(2-METHYLPROPYL)-1H-PYRAZOLE-4-CARBALDEHYDE; 5-CHLORO-3-CYCLOPROPYL-1-(3-METHYLBUTYL)-1H-PYRAZOLE-4-CARBALDEHYDE; 5-CHLORO-3-CYCLOPROPYL-1-(PENTAN-3-YL)-1H-PYRAZOLE-4-CARBALDEHYDE; 5-CHLORO-3-CYCLOPROPYL-1-(PROPAN-2-YL)-1H-PYRAZOLE-4-CARBALDEHYDE; 5-CHLORO-3-CYCLOPROPYL-1-[2-(DIMETHYLAMINO)ETHYL]-1H-PYRAZOLE-4-CARBALDEHYDE; 5-CHLORO-3-CYCLOPROPYL-1-ETHYL-1H-PYRAZOLE-4-CARBALDEHYDE; 5-CHLORO-3-CYCLOPROPYL-1-METHYL-1H-PYRAZOLE-4-CARBALDEHYDE; 5-CHLORO-3-CYCLOPROPYL-1-PROPYL-1H-PYRAZOLE-4-CARBALDEHYDE; 5-CHLORO-3-ETHYL-1-(2,4,6-TRIMETHYLPHENYL)-1H-PYRAZOLE-4-CARBALDEHYDE; 5-CHLORO-3-ETHYL-1-(2-FLUOROPHENYL)-1H-PYRAZOLE-4-CARBALDEHYDE; 5-CHLORO-3-ETHYL-1-(2-METHOXYPHENYL)-1H-PYRAZOLE-4-CARBALDEHYDE; 5-CHLORO-3-ETHYL-1-(2-METHYLPHENYL)-1H-PYRAZOLE-4-CARBALDEHYDE; 5-CHLORO-3-ETHYL-1-(2-METHYLPROPYL)-1H-PYRAZOLE-4-CARBALDEHYDE; 5-CHLORO-3-ETHYL-1-(2-NITROPHENYL)-1H-PYRAZOLE-4-CARBALDEHYDE; 5-CHLORO-3-ETHYL-1-(3-FLUOROPHENYL)-1H-PYRAZOLE-4-CARBALDEHYDE; 5-CHLORO-3-ETHYL-1-(3-METHYL-1,1-DIOXO-1LAMBDA6-THIOLAN-3-YL)-1H-PYRAZOLE-4-CARBALDEHYDE; 5-CHLORO-3-ETHYL-1-(3-METHYLBUTYL)-1H-PYRAZOLE-4-CARBALDEHYDE; 5-CHLORO-3-ETHYL-1-(3-METHYLPHENYL)-1H-PYRAZOLE-4-CARBALDEHYDE; 5-CHLORO-3-ETHYL-1-(3-NITROPHENYL)-1H-PYRAZOLE-4-CARBALDEHYDE; 5-CHLORO-3-ETHYL-1-(4-FLUOROPHENYL)-1H-PYRAZOLE-4-CARBALDEHYDE; 5-CHLORO-3-ETHYL-1-(4-METHYLPHENYL)-1H-PYRAZOLE-4-CARBALDEHYDE; 5-CHLORO-3-ETHYL-1-(4-METHYLPYRIDIN-2-YL)-1H-PYRAZOLE-4-CARBALDEHYDE; 5-CHLORO-3-ETHYL-1-(4-NITROPHENYL)-1H-PYRAZOLE-4-CARBALDEHYDE; 5-CHLORO-3-ETHYL-1-(6-METHYLPYRIDAZIN-3-YL)-1H-PYRAZOLE-4-CARBALDEHYDE; 5-CHLORO-3-ETHYL-1-(6-METHYLPYRIMIDIN-4-YL)-1H-PYRAZOLE-4-CARBALDEHYDE; 5-CHLORO-3-ETHYL-1-(7H-PURIN-6-YL)-1H-PYRAZOLE-4-CARBALDEHYDE; 5-CHLORO-3-ETHYL-1-(PENTAN-3-YL)-1H-PYRAZOLE-4-CARBALDEHYDE; 5-CHLORO-3-ETHYL-1-(PROPAN-2-YL)-1H-PYRAZOLE-4-CARBALDEHYDE; 5-CHLORO-3-ETHYL-1-(PYRIDIN-2-YL)-1H-PYRAZOLE-4-CARBALDEHYDE; 5-CHLORO-3-ETHYL-1-(PYRIDIN-4-YL)-1H-PYRAZOLE-4-CARBALDEHYDE; 5-CHLORO-3-ETHYL-1-(PYRIMIDIN-2-YL)-1H-PYRAZOLE-4-CARBALDEHYDE; 5-CHLORO-3-ETHYL-1-[(4-METHYLPHENYL)METHYL]-1H-PYRAZOLE-4-CARBALDEHYDE; 5-CHLORO-3-ETHYL-1-METHYL-1H-PYRAZOLE-4-CARBALDEHYDE; 5-CHLORO-3-ETHYL-1-PHENYL-1H-PYRAZOLE-4-CARBALDEHYDE; 5-CHLORO-3-ETHYL-1-PROPYL-1H-PYRAZOLE-4-CARBALDEHYDE; 5-CHLORO-3-METHYL-1-(2,4,6-TRIMETHYLPHENYL)-1H-PYRAZOLE-4-CARBALDEHYDE; 5-CHLORO-3-METHYL-1-(2-METHYLPHENYL)-1H-PYRAZOLE-4-CARBALDEHYDE; 5-CHLORO-3-METHYL-1-(2-NITROPHENYL)-1H-PYRAZOLE-4-CARBALDEHYDE; 5-CHLORO-3-METHYL-1-(3-METHYL-1,1-DIOXO-1LAMBDA6-THIOLAN-3-YL)-1H-PYRAZOLE-4-CARBALDEHYDE; 5-CHLORO-3-METHYL-1-(3-METHYLBUTYL)-1H-PYRAZOLE-4-CARBALDEHYDE; 5-CHLORO-3-METHYL-1-(3-METHYLPHENYL)-1H-PYRAZOLE-4-CARBALDEHYDE; 5-CHLORO-3-METHYL-1-(3-NITROPHENYL)-1H-PYRAZOLE-4-CARBALDEHYDE; 5-CHLORO-3-METHYL-1-(4-METHYLBENZYL)-1H-PYRAZOLE-4-CARBALDEHYDE; 5-CHLORO-3-METHYL-1-(4-METHYLPHENYL)-1H-PYRAZOLE-4-CARBALDEHYDE; 5-CHLORO-3-METHYL-1-(4-METHYLPYRIDIN-2-YL)-1H-PYRAZOLE-4-CARBALDEHYDE; 5-CHLORO-3-METHYL-1-(4-NITROPHENYL)-1H-PYRAZOLE-4-CARBALDEHYDE; 5-CHLORO-3-METHYL-1-(6-METHYLPYRIDAZIN-3-YL)-1H-PYRAZOLE-4-CARBALDEHYDE; 5-CHLORO-3-METHYL-1-(6-METHYLPYRIMIDIN-4-YL)-1H-PYRAZOLE-4-CARBALDEHYDE; 5-CHLORO-3-METHYL-1-(7H-PURIN-6-YL)-1H-PYRAZOLE-4-CARBALDEHYDE; 5-CHLORO-3-METHYL-1-(PENTAN-3-YL)-1H-PYRAZOLE-4-CARBALDEHYDE; 5-CHLORO-3-METHYL-1-(PROPAN-2-YL)-1H-PYRAZOLE-4-CARBALDEHYDE; 5-CHLORO-3-METHYL-1-(PYRIDIN-2-YL)-1H-PYRAZOLE-4-CARBALDEHYDE; 5-CHLORO-3-METHYL-1-(PYRIDIN-4-YL)-1H-PYRAZOLE-4-CARBALDEHYDE; 5-CHLORO-3-METHYL-1-(PYRIMIDIN-2-YL)-1H-PYRAZOLE-4-CARBALDEHYDE; 5-CHLORO-3-METHYL-1-[3-(TRIFLUOROMETHYL)PHENYL]-1H-PYRAZOLE-4-CARBALDEHYDE; 5-CHLORO-3-METHYL-1-[5-(TRIFLUOROMETHYL)PYRIDIN-2-YL]-1H-PYRAZOLE-4-CARBALDEHYDE; 5-CHLORO-3-METHYL-1-PHENYL-1H-PYRAZOLE-4-CARBALDEHYDE; 5-CHLORO-3-METHYL-1-PROPYL-1H-PYRAZOLE-4-CARBALDEHYDE; 5-CHLORO-3-PHENYL-1-(PROPAN-2-YL)-1H-PYRAZOLE-4-CARBALDEHYDE; 5-CHLORO-3-PHENYL-1H-PYRAZOLE-4-CARBALDEHYDE; 5-CHLORO-3-PHENYL-1-PROPYL-1H-PYRAZOLE-4-CARBALDEHYDE; 5-CHLORO-3-PROPYL-1-(PYRIDIN-2-YL)-1H-PYRAZOLE-4-CARBALDEHYDE; 5-CHLORO-3-PROPYL-1-(PYRIDIN-4-YL)-1H-PYRA-

ZOLE-4-CARBALDEHYDE; 5-CHLORO-3-PROPYL-1-(PYRIMIDIN-2-YL)-1H-PYRAZOLE-4-CARBALDEHYDE; 5-CHLORO-3-PROPYLIMIDAZO[1,2-A]PYRIDINE-2-CARBALDEHYDE; 5-CHLORO-6-OXO-1,6-DIHYDRO-3-PYRIDINECARBALDEHYDE; 5-CHLOROIMIDAZO[1,2-A]PYRIDINE-3-CARBALDEHYDE; 5-IODO-1H-PYRROLE-2-CARBALDEHYDE; 5-IODO-6-OXO-1,6-DIHYDRO-3-PYRIDINECARBALDEHYDE; 5-TERT-BUTYL-2-CHLORO-3-HYDROXYMETHYLENE-CYCLOHEX-1-ENE CARBOXALDEHYDE; 5-TERT-BUTYL-2-CHLOROCYCLOHEX-1-ENE-1-CARBALDEHYDE; 6-([(4-BROMOTHIOPHEN-2-YL)METHYL](METHYL)AMINO)IMIDAZO[2,1-B][1,3]THIAZOLE-5-CARBALDEHYDE; 6-(4-BROMO-1H-PYRAZOL-1-YL)IMIDAZO[2,1-B][1,3]THIAZOLE-5-CARBALDEHYDE; 6-(4-CHLORO-1H-PYRAZOL-1-YL)IMIDAZO[2,1-B][1,3]THIAZOLE-5-CARBALDEHYDE; 6,8-DIBROMOIMIDAZO[1,2-A]PYRAZINE-3-CARBALDEHYDE; 6,8-DICHLORO-IMIDAZO[1,2-A]PYRIDINE-2-CARBALDEHYDE; 6-[(2-BROMOPROP-2-EN-1-YL)OXY]-2H-1,3-BENZODIOXOLE-5-CARBALDEHYDE; 6-[(2-CHLOROPROP-2-EN-1-YL)OXY]-2H-1,3-BENZODIOXOLE-5-CARBALDEHYDE; 6-[(4-BROMOTHIOPHEN-2-YL)METHOXY]-2H-1,3-BENZODIOXOLE-5-CARBALDEHYDE; 6-BROMO-2-(3,4-DIMETHOXYPHENYL)IMIDAZO[1,2-A]PYRIDINE-3-CARBALDEHYDE; 6-BROMO-2-(3-METHOXYPHENYL)IMIDAZO[1,2-A]PYRIDINE-3-CARBALDEHYDE; 6-BROMO-2-(3-NITROPHENYL)IMIDAZO[1,2-A]PYRIDINE-3-CARBALDEHYDE; 6-BROMO-2-(4-BROMOPHENYL)IMIDAZO[1,2-A]PYRIDINE-3-CARBALDEHYDE; 6-BROMO-2-(4-CHLOROPHENYL)IMIDAZO[1,2-A]PYRIDINE-3-CARBALDEHYDE; 6-BROMO-2-(4-FLUOROPHENYL)-IMIDAZO[1,2-A]-PYRIDINE-3-CARBALDEHYDE; 6-BROMO-2-(4-METHOXYPHENYL)IMIDAZO[1,2-A]PYRIDINE-3-CARBALDEHYDE; 6-BROMO-2-(4-NITROPHENYL)IMIDAZO[1,2-A]PYRIDINE-3-CARBALDEHYDE; 6-BROMO-2-CHLORO-1H-INDOLE-3-CARBALDEHYDE; 6-BROMO-2-METHYL-IMIDAZO[1,2-A]PYRIDINE-3-CARBALDEHYDE; 6-BROMO-2-METHYLPYRAZOLO[1,5-A]PYRIMIDINE-3-CARBALDEHYDE; 6-BROMO-2-PHENYLIMIDAZO[1,2-A]PYRIDINE-3-CARBALDEHYDE; 6-BROMO-2-P-TOLYL-IMIDAZO[1,2-A]PYRIDINE-3-CARBOXALDEHYDE; 6-BROMO-3-FORMYL-PYRAZOLO[1,5-A]PYRIDINE-2-CARBOXYLIC ACID ETHYL ESTER; 6-BROMO-4-CHLORO-3-FORMYL-COUMARIN; 6-BROMO-7-METHYLIMIDAZO[1,2-A]PYRIDINE-3-CARBALDEHYDE; 6-BROMO-8-(DIMETHYLAMINO)IMIDAZO[1,2-A]PYRAZINE-3-CARBALDEHYDE; 6-BROMO-8-FLUOROIMIDAZO[1,2-A]PYRIDINE-3-CARBALDEHYDE; 6-BROMOIMIDAZO[1,2-A]PYRAZINE-3-CARBALDEHYDE; 6-BROMO-IMIDAZO[1,2-A]PYRIDINE-2-CARBALDEHYDE; 6-BROMOIMIDAZO[1,2-A]PYRIDINE-3-CARBALDEHYDE; 6-BROMOIMIDAZO[1,2-A]PYRIMIDINE-3-CARBALDEHYDE; 6-BROMO-IMIDAZO[1,2-B]PYRIDAZINE-2-CARBOXYALDEHYDE; 6-CHLORO-1,3-BIS(2-METHOXYETHYL)-2,4-DIOXO-1,2,3,4-TETRAHYDROPYRIMIDINE-5-CARBALDEHYDE; 6-CHLORO-1,3-DIISOBUTYL-2,4-DIOXO-1,2,3,4-TETRAHYDROPYRIMIDINE-5-CARBALDEHYDE; 6-CHLORO-2-(2,4-DIMETHYLPHENYL)IMIDAZO[1,2-A]PYRIDINE-3-CARBALDEHYDE; 6-CHLORO-2-(2,5-DIMETHYLPHENYL)IMIDAZO[1,2-A]PYRIDINE-3-CARBALDEHYDE; 6-CHLORO-2-(3,4-DIMETHOXYPHENYL)-IMIDAZO[1,2-A]-PYRIDINE-3-CARBALDEHYDE; 6-CHLORO-2-(3,4-DIMETHYLPHENYL)IMIDAZO[1,2-A]PYRIDINE-3-CARBALDEHYDE; 6-CHLORO-2-(3-CHLOROPHENYL)-IMIDAZO[1,2-A]PYRIDINE-3-CARBALDEHYDE; 6-CHLORO-2-(3-FLUOROPHENYL)-IMIDAZO[1,2-A]PYRIDINE-3-CARBALDEHYDE; 6-CHLORO-2-(3-METHOXYPHENYL)-IMIDAZO[1,2-A]-PYRIDINE-3-CARBALDEHYDE; 6-CHLORO-2-(3-NITRO-PHENYL)-IMIDAZO[1,2-A]PYRIDINE-3-CARBALDEHYDE; 6-CHLORO-2-(4-CHLOROPHENYL)IMIDAZO[1,2-A]-PYRIDINE-3-CARBALDEHYDE; 6-CHLORO-2-(4-FLUORO-PHENYL)-IMIDAZO[1,2-A]-PYRIDINE-3-CARBALDEHYDE; 6-CHLORO-2-(4-METHOXY-PHENYL)-IMIDAZO[1,2-A]-PYRIDINE-3-CARBALDEHYDE; 6-CHLORO-2-(4-NITRO-PHENYL)-IMIDAZO[1,2-A]PYRIDINE-3-CARBALDEHYDE; 6-CHLORO-2,3-DIMETHYL-IMIDAZO[2,1-B]THIAZOLE-5-CARBOXALDEHYDE; 6-CHLORO-2-CYCLOBUTYL-IMIDAZO[1,2-B]PYRIDAZINE-3-CARBALDEHYDE; 6-CHLORO-2-CYCLOPROPYL-IMIDAZO[1,2-B]PYRIDAZINE-3-CARBALDEHYDE; 6-CHLORO-2-METHYL-IMIDAZO[1,2-A]PYRIDINE-3-CARBALDEHYDE; 6-CHLORO-2-METHYL-IMIDAZO[2,1-B]THIAZOLE-5-CARBOXALDEHYDE; 6-CHLORO-2-M-TOLYL-IMIDAZO[1,2-A]PYRIDINE-3-CARBALDEHYDE; 6-CHLORO-2-PHENYL-IMIDAZO[1,2-A]PYRIDINE-3-CARBALDEHYDE; 6-CHLORO-2-P-TOLYL-IMIDAZO[1,2-A]PYRIDINE-3-CARBALDEHYDE; 6-CHLORO-3-METHYL-5-PHENYL-5H-ISOXAZOLO[5,4-B]PYRROLO[2,3-E]PYRIDINE-7-CARBALDEHYDE; 6-CHLORO-3-METHYL-IMIDAZO[2,1-B]THIAZOLE-5-CARBOXALDEHYDE; 6-CHLORO-5-FORMYL-1-(2-METHOXY-ETHYL)-4-METHYL-2-OXO-1,2-DIHYDRO-PYRIDINE-3-CARBONITRILE; 6-CHLORO-5-FORMYL-1-(3-METHOXY-PROPYL)-4-METHYL-2-OXO-1,2-DIHYDRO-PYRIDINE-3-CARBONITRILE; 6-CHLORO-5-FORMYL-1,3-DIMETHYLURACIL; 6-CHLORO-5-FORMYL-1,4-DIMETHYL-2-OXO-1,2-DIHYDRO-PYRIDINE-3-CARBONITRILE; 6-CHLORO-5-FORMYL-1-ISOBUTYL-4-METHYL-2-OXO-1,2-DIHYDRO-PYRIDINE-3-CARBONITRILE; 6-CHLORO-5-FORMYL-1-ISOPROPYL-4-METHYL-2-OXO-1,2-DIHYDRO-PYRIDINE-3-CARBONITRILE; 6-CHLORO-5-FORMYL-4-METHYL-1-(3-METHYL-BUTYL)-2-OXO-1,2-DIHYDRO-PYRIDINE-3-CARBONITRILE; 6-CHLORO-5-FORMYL-4-METHYL-2-OXO-1-(TETRAHYDRO-FURAN-2-YLMETHYL)-1,2-DIHYDRO-PYRIDINE-3-CARBONITRILE; 6-CHLORO-5-FORMYL-4-METHYL-2-OXO-1-PROPYL-1,2-DIHYDRO-PYRIDINE-3-CARBONITRILE; 6-CHLORO-IMIDAZO[1,2-A]PYRIDINE-2-CARBALDEHYDE; 6-CHLOROIMIDAZO[1,2-A]PYRIDINE-3-CARBALDEHYDE; 6-CHLOROIMIDAZO[1,2-A]PYRIMIDINE-3-CARBALDEHYDE; 6-CHLORO-IMIDAZO[1,2-B]PYRIDAZINE-2-CARBOXALDEHYDE; 6-CHLOROIMIDAZO[1,2-B]PYRIDAZINE-3-CARBALDEHYDE; 6-CHLOROIMIDAZO[2,1-B]THIAZOLE-5-CARBOXALDEHYDE; 7-BROMO-1-CHLORO-3,4-DIHYDRO-NAPHTHALENE-2-CARBALDEHYDE; 7-BROMO-2-CHLORO-4-OXO-4H-PYRIDO[1,2-A]PYRIMIDINE-3-CARBALDEHYDE; 7-BROMO-2-CHLORO-8-METHYL-4-OXO-4H-PYRIDO[1,2-A]PY-

RIMIDINE-3-CARBALDEHYDE; 7-BROMO-2-METHYL-2H-INDAZOLE-3-CARBALDEHYDE; 7-BROMO-2-METHYL-H-IMIDAZO[1,2-A]PYRIDINE-3-CARBALDEHYDE; 7-BROMO-2-PHENYLIMIDAZO[1,2-A]PYRIDINE-3-CARBALDEHYDE; 7-BROMO-3-FORMYL-PYRAZOLO[1,5-A]PYRIDINE-2-CARBOXYLIC ACID ETHYL ESTER; 7-BROMOIMIDAZO[1,2-A]PYRIDINE-2-CARBALDEHYDE; 7-BROMO-IMIDAZO[1,5-A]PYRIDINE-1-CARBALDEHYDE; 7-CHLORO-2-(4-CHLOROPHENYL)IMIDAZO[1,2-A]PYRIDINE-3-CARBALDEHYDE; 7-CHLORO-2-METHYL-H-IMIDAZO[1,2-A]PYRIDINE-3-CARBALDEHYDE; 7-CHLORO-5-OXO-5H-THIAZOLO[3,2-A]PYRIMIDINE-6-CARBALDEHYDE; 8-BROMO-6-CHLOROIMIDAZO[1,2-A]PYRIDINE-3-CARBALDEHYDE; 8-BROMO-6-METHYLIMIDAZO[1,2-A]PYRIDINE-3-CARBALDEHYDE; 8-BROMOIMIDAZO[1,2-A]PYRIDINE-2-CARBALDEHYDE; 8-CHLORO-6-(TRIFLUOROMETHYL)IMIDAZO[1,2-A]PYRIDINE-2-CARBALDEHYDE; 8-CHLORO-IMIDAZO[1,2-A]PYRIDINE-2-CARBALDEHYDE; ALPHA-BROMO-5-NITRO-2-THIOPHENEACROLEIN; ALPHA-BROMOCINNAMALDEHYDE; ALPHA-BROMOCINNAMALDEHYDE; ALPHA-CHLOROCINNAMALDEHYDE; ETHYL (4-CHLORO-5-FORMYL-2-PHENYL-1H-IMIDAZOL-1-YL)ACETATE; ETHYL 2-(5-CHLORO-4-FORMYL-3-METHYL-1H-PYRAZOL-1-YL)-3,3-BIS(METHYLSULFANYL)ACRYLATE; ETHYL 2-(5-CHLORO-4-FORMYL-3-METHYL-1H-PYRAZOL-1-YL)ACETATE; ETHYL 2-ANILINO-4-CHLORO-5-FORMYL-3-THIOPHENECARBOXYLATE; ETHYL 4-CHLORO-5-FORMYL-2-(METHYLAMINO)-3-THIOPHENECARBOXYLATE; ETHYL 4-CHLORO-5-FORMYL-2-METHYL-3-THIOPHENECARBOXYLATE; ETHYL 4-CHLORO-5-FORMYL-3-(METHYLTHIO)-6,7-DIHYDRO-2-BENZOTHIOPHENE-1-CARBOXYLATE; ETHYL 4-CHLORO-5-FORMYL-3-METHYL-6,7-DIHYDRO-1-BENZOFURAN-2-CARBOXYLATE; ETHYL 4-CHLORO-7-FORMYL-5-METHYLPYRROLO[2,1-F][1,2,4]TRIAZINE-6-CARBOXYLATE; ETHYL 5-CHLORO-4-FORMYL-1-METHYL-1H-PYRAZOLE-3-CARBOXYLATE; ETHYL 5-CHLORO-4-FORMYL-1-PHENYL-1H-PYRAZOLE-3-CARBOXYLATE; ETHYL 6-CHLORO-4-(4-CHLOROPHENYL)-5-FORMYL-2-METHYL-1,4-DIHYDRO-3-PYRIDINECARBOXYLATE; METHYL 4-BROMO-5-FORMYL-2-THIOPHENECARBOXYLATE; METHYL 5-CHLORO-4-FORMYL-1-METHYL-1H-PYRAZOLE-3-CARBOXYLATE; METHYL 5-CHLORO-4-FORMYL-1-PHENYL-1H-PYRAZOLE-3-CARBOXYLATE; N-[(2E)-3-ALLYL-4-CHLORO-5-FORMYL-1,3-THIAZOL-2(3H)-YLIDENE]BENZENESULFONAMIDE; N-[(2E)-3-ALLYL-4-CHLORO-5-FORMYL-1,3-THIAZOL-2(3H)-YLIDENE]THIOPHENE-2-SULFONAMIDE; N-PHENYL-3-FORMYL-4-CHLORO-5-(2-CHLOROETHYL)-6-OXO-1,6-DIHYDROPYRIDINE; TERT-BUTYL 4-FORMYL-3-IODO-1H-INDAZOLE-1-CARBOXYLATE; TERT-BUTYL 5-FORMYL-3-IODO-1H-INDAZOLE-1-CARBOXYLATE; TERT-BUTYL 6-FORMYL-3-IODO-1H-INDAZOLE-1-CARBOXYLATE; TERT-BUTYL 7-FORMYL-3-IODO-1H-INDAZOLE-1-CARBOXYLATE; Primary amine: (2-[(6-FORMYL-2H-1,3-BENZODIOXOL-5-YL)OXY]ACETYL)UREA; (2-AMINO-1H-IMIDAZOL-4-YL)-ACETALDEHYDE HCL; (2-AMINO-6-METHOXY-PHENYL)-ACETALDEHYDE; (2-AMINOPHENYL)CYCLOHEXYL-METHANONE; (2R)-2-AMINO-2-(3-FORMYL-2-HYDROXY-5-METHYLPHENYL)ACETIC ACID; (2R)-2-AMINO-2-(4-[(4-FORMYLPHENYL)METHYL]PHENYL)ACETIC ACID; (2R)-2-AMINO-2-(4-[(4-FORMYLPHENYL)METHYL]PHENYL)PROPANOIC ACID; (2R)-2-AMINO-2-(4-FORMYL(2-PYRIDYL))ACETIC ACID; (2R)-2-AMINO-2-(4-FORMYL(2-PYRIDYL))PROPANOIC ACID; (2R)-2-AMINO-2-(5-FORMYL(2-PYRIDYL))ACETIC ACID; (2R)-2-AMINO-2-(5-FORMYL(2-PYRIDYL))PROPANOIC ACID; (2R)-2-AMINO-2-(5-FORMYL(3-PYRIDYL))ACETIC ACID; (2R)-2-AMINO-2-(5-FORMYL(3-PYRIDYL))PROPANOIC ACID; (2R)-2-AMINO-2-(6-AMINO-5-FORMYL(3-PYRIDYL))ACETIC ACID; (2R)-2-AMINO-2-(6-AMINO-5-FORMYL(3-PYRIDYL))PROPANOIC ACID; (2R)-2-AMINO-2-(6-FORMYL(2-PYRIDYL))ACETIC ACID; (2R)-2-AMINO-2-(6-FORMYL(2-PYRIDYL))PROPANOIC ACID; (2R)-2-AMINO-2-(6-FORMYL(3-PYRIDYL))ACETIC ACID; (2R)-2-AMINO-2-(6-FORMYL(3-PYRIDYL))PROPANOIC ACID; (2R)-2-AMINO-2-(6-FORMYL-3-METHOXY(2-PYRIDYL))ACETIC ACID; (2R)-2-AMINO-2-(6-FORMYL-3-METHOXY(2-PYRIDYL))PROPANOIC ACID; (2S)-1-(3-FORMYL-4-OXO-4H-PYRIDO[1,2-A]PYRIMIDIN-2-YL)PYRROLIDINE-2-CARBOXAMIDE; (2S)-2-AMINO-2-(3-FORMYL-2-HYDROXY-5-METHYLPHENYL)ACETIC ACID; (2S)-2-AMINO-2-(4-[(4-FORMYLPHENYL)METHYL]PHENYL)ACETIC ACID; (2S)-2-AMINO-2-(4-[(4-FORMYLPHENYL)METHYL]PHENYL)PROPANOIC ACID; (2S)-2-AMINO-2-(4-FORMYL(2-PYRIDYL))ACETIC ACID; (2S)-2-AMINO-2-(4-FORMYL(2-PYRIDYL))PROPANOIC ACID; (2S)-2-AMINO-2-(5-FORMYL(2-PYRIDYL))ACETIC ACID; (2S)-2-AMINO-2-(5-FORMYL(2-PYRIDYL))PROPANOIC ACID; (2S)-2-AMINO-2-(5-FORMYL(3-PYRIDYL))ACETIC ACID; (2S)-2-AMINO-2-(5-FORMYL(3-PYRIDYL))PROPANOIC ACID; (2S)-2-AMINO-2-(6-AMINO-5-FORMYL(3-PYRIDYL))ACETIC ACID; (2S)-2-AMINO-2-(6-AMINO-5-FORMYL(3-PYRIDYL))PROPANOIC ACID; (2S)-2-AMINO-2-(6-FORMYL(2-PYRIDYL))ACETIC ACID; (2S)-2-AMINO-2-(6-FORMYL(2-PYRIDYL))PROPANOIC ACID; (2S)-2-AMINO-2-(6-FORMYL(3-PYRIDYL))ACETIC ACID; (2S)-2-AMINO-2-(6-FORMYL(3-PYRIDYL))PROPANOIC ACID; (2S)-2-AMINO-2-(6-FORMYL-3-METHOXY(2-PYRIDYL))ACETIC ACID; (2S)-2-AMINO-2-(6-FORMYL-3-METHOXY(2-PYRIDYL))PROPANOIC ACID; (3-FORMYL-2,5-DIMETHYL-1H-PYRROL-1-YL)UREA; (3R)-3-AMINO-3-(3-FORMYL-2-HYDROXY-5-METHYLPHENYL)PROPANENITRILE; (3R)-3-AMINO-3-(4-FORMYL(2-PYRIDYL))PROPANENITRILE; (3R)-3-AMINO-3-(5-FORMYL(2-PYRIDYL))PROPANENITRILE; (3R)-3-AMINO-3-(5-FORMYL(3-PYRIDYL))PROPANENITRILE; (3R)-3-AMINO-3-(6-AMINO-5-FORMYL(3-PYRIDYL))PROPANENITRILE; (3R)-3-AMINO-3-(6-FORMYL(2-PYRIDYL))PROPANENITRILE; (3R)-3-AMINO-3-(6-FORMYL(3-PYRIDYL))PROPANENITRILE; (3R)-3-AMINO-3-(6-FORMYL-3-METHOXY(2-PYRIDYL))PROPANENITRILE; (3S)-3-AMINO-3-(3-FORMYL-2-HYDROXY-5-METHYLPHENYL)PROPANENITRILE; (3S)-3-AMINO-3-(4-FORMYL(2-PYRIDYL))PROPANENITRILE; (3S)-3-AMINO-3-(5-FORMYL(2-PYRIDYL))PROPANENITRILE; (3S)-3-AMINO-3-(5-FORMYL(3-PYRIDYL))PROPANENITRILE; (3S)-3-AMINO-3-(6-AMINO-5-FORMYL(3-PYRIDYL))PROPANENITRILE; (3S)-3-AMINO-3-(6-FORMYL(2-

PYRIDYL))PROPANENITRILE; (3S)-3-AMINO-3-(6-FORMYL(3-PYRIDYL))PROPANENITRILE; (3S)-3-AMINO-3-(6-FORMYL-3-METHOXY(2-PYRIDYL))PROPANENITRILE; (4-AMINO-PHENYL)-ACETALDEHYDE; (4R)-4-AMINO-4-(3-FORMYL-2-HYDROXY-5-METHYLPHENYL)BUTANOIC ACID; (4S)-4-AMINO-4-(3-FORMYL-2-HYDROXY-5-METHYLPHENYL)BUTANOIC ACID; (5-FORMYLPYRIMIDIN-2-YL)METHANAMINIUM CHLORIDE; (5R)-5-AMINO-5-(3-FORMYL-2-HYDROXY-5-METHYLPHENYL)PENTANOIC ACID; (5S)-5-AMINO-5-(3-FORMYL-2-HYDROXY-5-METHYLPHENYL)PENTANOIC ACID; (E)-3-(5-AMINOFURAN-2-YL)ACRYLALDEHYDE; (S)-4-N-CBZ-AMINO-4-FORMYL BUTYLAMIDE; (Z)-B-AMINOACROLEIN; [2-(2,4-DICHLORO-6-FORMYLPHENOXY)ACETYL]UREA; [2-(2-CHLORO-4-FORMYL-6-METHOXYPHENOXY)ACETYL]UREA; [2-(2-CHLORO-4-FORMYLPHENOXY)ACETYL]UREA; [2-(2-ETHOXY-4-FORMYLPHENOXY)ACETYL]UREA; [2-(2-ETHOXY-6-FORMYLPHENOXY)ACETYL]UREA; [2-(2-FORMYL-4-METHOXYPHENOXY)ACETYL]UREA; [2-(2-FORMYL-4-METHOXYPHENOXY)PROPANOYL]UREA; [2-(2-FORMYL-4-NITROPHENOXY)ACETYL]UREA; [2-(2-FORMYL-5-METHOXYPHENOXY)ACETYL]UREA; [2-(2-FORMYL-5-METHOXYPHENOXY)PROPANOYL]UREA; [2-(2-FORMYL-6-METHOXYPHENOXY)ACETYL]UREA; [2-(2-FORMYL-6-METHOXYPHENOXY)PROPANOYL]UREA; [2-(2-FORMYLPHENOXY)ACETYL]UREA; [2-(2-FORMYLPHENOXY)PROPANOYL]UREA; [2-(2-FORMYLPIPERIDIN-1-YL)ACETYL]UREA; [2-(2-FORMYLPIPERIDIN-1-YL)PROPANOYL]UREA; [2-(3-CHLORO-2-FORMYLPHENOXY)ACETYL]UREA; [2-(3-CHLORO-2-FORMYLPHENOXY)PROPANOYL]UREA; [2-(3-FORMYLPHENOXY)ACETYL]UREA; [2-(3-FORMYLPHENOXY)PROPANOYL]UREA; [2-(3-FORMYLPIPERIDIN-1-YL)ACETYL]UREA; [2-(3-FORMYLPIPERIDIN-1-YL)PROPANOYL]UREA; [2-(4-CHLORO-2-FORMYLPHENOXY)ACETYL]UREA; [2-(4-CHLORO-2-FORMYLPHENOXY)PROPANOYL]UREA; [2-(4-FORMYL-2,6-DIMETHYLPHENOXY)ACETYL]UREA; [2-(4-FORMYL-2,6-DIMETHYLPHENOXY)PROPANOYL]UREA; [2-(4-FORMYL-2-METHOXYPHENOXY)ACETYL]UREA; [2-(4-FORMYL-2-METHOXYPHENOXY)PROPANOYL]UREA; [2-(4-FORMYL-2-NITROPHENOXY)ACETYL]UREA; [2-(4-FORMYLPHENOXY)ACETYL]UREA; [2-(4-FORMYLPHENOXY)PROPANOYL]UREA; [2-(4-FORMYLPIPERIDIN-1-YL)ACETYL]UREA; [2-(4-FORMYLPIPERIDIN-1-YL)PROPANOYL]UREA; [2-(5-FORMYL-2-METHOXYPHENOXY)ACETYL]UREA; [2-(5-FORMYL-2-METHOXYPHENOXY)PROPANOYL]UREA; [2-(5-FORMYL-2-NITROPHENOXY)ACETYL]UREA; [3-(2-FORMYLPIPERIDIN-1-YL)PROPANOYL]UREA; [3-(3-FORMYLPIPERIDIN-1-YL)PROPANOYL]UREA; [3-(4-FORMYLPIPERIDIN-1-YL)PROPANOYL]UREA; 1-(2,6-DIFLUORO-4-FORMYLPHENYL)PIPERIDINE-2-CARBOXAMIDE; 1-(2,6-DIFLUORO-4-FORMYLPHENYL)PIPERIDINE-3-CARBOXAMIDE; 1-(2,6-DIFLUORO-4-FORMYLPHENYL)PIPERIDINE-4-CARBOXAMIDE; 1-(2,6-DIFLUORO-4-FORMYLPHENYL)PYRROLIDINE-2-CARBOXAMIDE; 1-(2-AMINOETHYL)-2-FORMYLIMIDAZOLE HCL; 1-(2-FLUORO-4-FORMYLPHENYL)-6-METHYLPIPERIDINE-3-CARBOXAMIDE; 1-(2-FLUORO-4-FORMYLPHENYL)PIPERIDINE-2-CARBOXAMIDE; 1-(2-FLUORO-4-FORMYLPHENYL)PIPERIDINE-3-CARBOXAMIDE; 1-(2-FLUORO-4-FORMYLPHENYL)PIPERIDINE-4-CARBOXAMIDE; 1-(2-FLUORO-4-FORMYLPHENYL)PYRROLIDINE-2-CARBOXAMIDE; 1-(2-FORMYL-4-NITROPHENYL)PYRROLIDINE-2-CARBOXAMIDE; 1-(2-FORMYLPHENYL)-6-METHYLPIPERIDINE-3-CARBOXAMIDE; 1-(2-FORMYLPHENYL)PIPERIDINE-2-CARBOXAMIDE; 1-(2-FORMYLPHENYL)PIPERIDINE-3-CARBOXAMIDE; 1-(2-FORMYLPHENYL)PIPERIDINE-4-CARBOXAMIDE; 1-(2-FORMYLPHENYL)PYRROLIDINE-2-CARBOXAMIDE; 1-(2-OXOETHYL)PIPERIDINE-3-CARBOXAMIDE; 1-(2-OXOETHYL)PIPERIDINE-4-CARBOXAMIDE; 1-(2-OXOETHYL)PYRROLIDINE-2-CARBOXAMIDE; 1-(3-AMINO-PROPYL)-1H-IMIDAZOLE-2-CARBALDEHYDE HCL; 1-(3-CHLORO-2-FORMYLPHENYL)-6-METHYLPIPERIDINE-3-CARBOXAMIDE; 1-(3-CHLORO-2-FORMYLPHENYL)PIPERIDINE-2-CARBOXAMIDE; 1-(3-CHLORO-2-FORMYLPHENYL)PIPERIDINE-3-CARBOXAMIDE; 1-(3-CHLORO-2-FORMYLPHENYL)PIPERIDINE-4-CARBOXAMIDE; 1-(3-CHLORO-2-FORMYLPHENYL)PYRROLIDINE-2-CARBOXAMIDE; 1-(3-FORMYLIMIDAZO[1,2-A]PYRIDIN-2-YL)PYRROLIDINE-2-CARBOXAMIDE; 1-(3-OXOPROPYL)PIPERIDINE-2-CARBOXAMIDE; 1-(3-OXOPROPYL)PIPERIDINE-3-CARBOXAMIDE; 1-(3-OXOPROPYL)PIPERIDINE-4-CARBOXAMIDE; 1-(3-OXOPROPYL)PYRROLIDINE-2-CARBOXAMIDE; 1-(4-FLUORO-2-FORMYLPHENYL)-6-METHYLPIPERIDINE-3-CARBOXAMIDE; 1-(4-FLUORO-2-FORMYLPHENYL)PIPERIDINE-2-CARBOXAMIDE; 1-(4-FLUORO-2-FORMYLPHENYL)PIPERIDINE-3-CARBOXAMIDE; 1-(4-FLUORO-2-FORMYLPHENYL)PIPERIDINE-4-CARBOXAMIDE; 1-(4-FLUORO-2-FORMYLPHENYL)PYRROLIDINE-2-CARBOXAMIDE; 1-(4-FORMYL-1,3-DIMETHYL-1H-PYRAZOL-5-YL)-6-METHYLPIPERIDINE-3-CARBOXAMIDE; 1-(4-FORMYL-1,3-DIMETHYL-1H-PYRAZOL-5-YL)PIPERIDINE-3-CARBOXAMIDE; 1-(4-FORMYL-1,3-DIMETHYL-1H-PYRAZOL-5-YL)PIPERIDINE-4-CARBOXAMIDE; 1-(4-FORMYL-1,3-DIMETHYL-1H-PYRAZOL-5-YL)PYRROLIDINE-2-CARBOXAMIDE; 1-(4-FORMYL-2-METHYLPHENYL)-6-METHYLPIPERIDINE-3-CARBOXAMIDE; 1-(4-FORMYL-2-METHYLPHENYL)PIPERIDINE-2-CARBOXAMIDE; 1-(4-FORMYL-2-METHYLPHENYL)PIPERIDINE-3-CARBOXAMIDE; 1-(4-FORMYL-2-METHYLPHENYL)PIPERIDINE-4-CARBOXAMIDE; 1-(4-FORMYL-2-METHYLPHENYL)PYRROLIDINE-2-CARBOXAMIDE; 1-(4-FORMYL-2-NITROPHENYL)PYRROLIDINE-2-CARBOXAMIDE; 1-(4-FORMYL-3-METHYLPHENYL)-6-METHYLPIPERIDINE-3-CARBOXAMIDE; 1-(4-FORMYL-3-METHYLPHENYL)PIPERIDINE-2-CARBOXAMIDE; 1-(4-FORMYL-3-METHYLPHENYL)PIPERIDINE-3-CARBOXAMIDE; 1-(4-FORMYL-3-METHYLPHENYL)PIPERIDINE-4-CARBOXAMIDE; 1-(4-FORMYL-3-METHYLPHENYL)PYRROLIDINE-2-CARBOXAMIDE; 1-(4-FORMYLPHENYL)-6-METHYLPIPERIDINE-3-CARBOXAMIDE; 1-(4-FORMYLPHENYL)PIPERIDINE-2-CARBOXAMIDE; 1-(4-FORMYLPHENYL)PIPERIDINE-3-CARBOXAMIDE; 1-(4-FORMYLPHENYL)PIPERIDINE-4-CARBOXAMIDE; 1-(4-FORMYLPHENYL)PYRROLIDINE-2-CAR-

BOXAMIDE; 1-(5-BROMO-2-FORMYLPHENYL)PYRROLIDINE-2-CARBOXAMIDE; 1-(5-FORMYL-2-METHOXYBENZYL)PIPERIDINE-4-CARBOXAMIDE; 1-(5-FORMYLFURAN-2-YL)-6-METHYLPIPERIDINE-3-CARBOXAMIDE; 1-(5-FORMYLFURAN-2-YL)PIPERIDINE-2-CARBOXAMIDE; 1-(5-FORMYLFURAN-2-YL)PIPERIDINE-3-CARBOXAMIDE; 1-(5-FORMYLFURAN-2-YL)PIPERIDINE-4-CARBOXAMIDE; 1-(5-FORMYLFURAN-2-YL)PYRROLIDINE-2-CARBOXAMIDE; 1-(5-FORMYLIMIDAZO[2,1-B][1,3]THIAZOL-6-YL)PIPERIDINE-2-CARBOXAMIDE; 1-(5-FORMYLIMIDAZO[2,1-B][1,3]THIAZOL-6-YL)PIPERIDINE-3-CARBOXAMIDE; 1-(5-FORMYLIMIDAZO[2,1-B][1,3]THIAZOL-6-YL)PIPERIDINE-4-CARBOXAMIDE; 1-(5-FORMYLIMIDAZO[2,1-B][1,3]THIAZOL-6-YL)PYRROLIDINE-2-CARBOXAMIDE; 1-(5-FORMYLPYRIMIDIN-2-YL)ETHANAMINIUM CHLORIDE; 1-[(5-FORMYL-2-METHOXYPHENYL)METHYL]PYRROLIDINE-2-CARBOXAMIDE; 1-AMINO-9,10-DIOXO-9,10-DIHYDRO-2-ANTHRACENECARBALDEHYDE; 1-AMINONAPHTHALENE-2-CARBOXALDEHYDE; 1-AMINONAPHTHALENE-3-CARBOXALDEHYDE; 1-AMINONAPHTHALENE-4-CARBOXALDEHYDE; 1-AMINONAPHTHALENE-5-CARBOXALDEHYDE; 1-AMINONAPHTHALENE-6-CARBOXALDEHYDE; 1-AMINONAPHTHALENE-7-CARBOXALDEHYDE; 1-AMINONAPHTHALENE-8-CARBOXALDEHYDE; 1H-INDOLE-3-CARBOXALDEHYDE, 1-[2-(DIMETHYLAMINO)PROPANAMINE]-2-METHYL-; 1H-PYRROLO[2,3-B]PYRIDINE-5-CARBOXALDEHYDE, 4-AMINO-6,7-DIHYDRO-2,3-DIMETHYL-6-OXO-; 2-((1R)-1,2-DIAMINOETHYL)PYRIDINE-4-CARBALDEHYDE; 2-((1R)-1-AMINO-2,2,2-TRIFLUOROETHYL)PYRIDINE-4-CARBALDEHYDE; 2-((1R)-1-AMINO-2-HYDROXYETHYL)PYRIDINE-4-CARBALDEHYDE; 2-((1R)-1-AMINO-2-METHYLPROPYL)PYRIDINE-4-CARBALDEHYDE; 2-((1R)-1-AMINOBUTYL)PYRIDINE-4-CARBALDEHYDE; 2-((1R)-1-AMINOETHYL)PYRIDINE-4-CARBALDEHYDE; 2-((1R)-1-AMINOPENTYL)PYRIDINE-4-CARBALDEHYDE; 2-((1R)-1-AMINOPROP-2-ENYL)PYRIDINE-4-CARBALDEHYDE; 2-((1R)-1-AMINOPROPYL)PYRIDINE-4-CARBALDEHYDE; 2-((1S)-1,2-DIAMINOETHYL)PYRIDINE-4-CARBALDEHYDE; 2-((1S)-1-AMINO-2,2,2-TRIFLUOROETHYL)PYRIDINE-4-CARBALDEHYDE; 2-((1S)-1-AMINO-2-HYDROXYETHYL)PYRIDINE-4-CARBALDEHYDE; 2-((1S)-1-AMINO-2-METHYLPROPYL)PYRIDINE-4-CARBALDEHYDE; 2-((1S)-1-AMINOBUTYL)PYRIDINE-4-CARBALDEHYDE; 2-((1S)-1-AMINOETHYL)PYRIDINE-4-CARBALDEHYDE; 2-((1S)-1-AMINOPENTYL)PYRIDINE-4-CARBALDEHYDE; 2-((1S)-1-AMINOPROP-2-ENYL)PYRIDINE-4-CARBALDEHYDE; 2-((1S)-1-AMINOPROPYL)PYRIDINE-4-CARBALDEHYDE; 2-((3-FORMYLIMIDAZO[1,2-A]PYRIDIN-2-YL)(METHYL)AMINO)ACETAMIDE; 2-((3-FORMYLIMIDAZO[1,2-A]PYRIDIN-2-YL)(PROPAN-2-YL)AMINO)ACETAMIDE; 2-((5-FORMYLIMIDAZO[2,1-B][1,3]THIAZOL-6-YL)(2-METHYLPROPYL)AMINO)ACETAMIDE; 2-((5-FORMYLIMIDAZO[2,1-B][1,3]THIAZOL-6-YL)(METHYL)AMINO)ACETAMIDE; 2-((5-FORMYLIMIDAZO[2,1-B][1,3]THIAZOL-6-YL)(PROPAN-2-YL)AMINO)ACETAMIDE; 2-([(5-FORMYL-2-METHOXYPHENYL)METHYL](METHYL)AMINO)ACETAMIDE; 2-([(5-FORMYL-2-METHOXYPHENYL)METHYL](PROPAN-2-YL)AMINO)ACETAMIDE; 2-(2,4-DICHLORO-6-FORMYLPHENOXY)ACETAMIDE; 2-(2,4-DICHLORO-6-FORMYLPHENOXY)BUTANAMIDE; 2-(2,4-DICHLORO-6-FORMYLPHENOXY)PROPANAMIDE; 2-(2-AMINO-ETHYL)-1H-IMIDAZOLE-4-CARBALDEHYDE 2HCL; 2-(2-AMINOETHYL)PYRIMIDINE-5-CARBALDEHYDE HYDROCHLORIDE; 2-(2-AMINO-PHENYL)-OXAZOLE-4-CARBALDEHYDE; 2-(2-AMINO-PHENYL)-THIAZOLE-4-CARBALDEHYDE; 2-(2-AMINOPYRIMIDIN-5-YL)BENZALDEHYDE; 2-(2-BROMO-4-FORMYL-6-METHOXYPHENOXY)ACETAMIDE; 2-(2-BROMO-4-FORMYLPHENOXY)ACETAMIDE; 2-(2-BROMO-4-FORMYLPHENOXY)BUTANAMIDE; 2-(2-BROMO-4-FORMYLPHENOXY)PROPANAMIDE; 2-(2-BROMO-6-FORMYLPHENOXY)ACETAMIDE; 2-(2-BROMO-6-FORMYLPHENOXY)BUTANAMIDE; 2-(2-BROMO-6-FORMYLPHENOXY)PROPANAMIDE; 2-(2-CHLORO-4-FORMYL-6-METHOXYPHENOXY)ACETAMIDE; 2-(2-CHLORO-4-FORMYL-6-METHOXYPHENOXY)BUTANAMIDE; 2-(2-CHLORO-4-FORMYL-6-METHOXYPHENOXY)PROPANAMIDE; 2-(2-CHLORO-4-FORMYLPHENOXY)ACETAMIDE; 2-(2-CHLORO-4-FORMYLPHENOXY)BUTANAMIDE; 2-(2-CHLORO-4-FORMYLPHENOXY)PROPANAMIDE; 2-(2-CHLORO-6-ETHOXY-4-FORMYLPHENOXY)ACETAMIDE; 2-(2-ETHOXY-4-FORMYLPHENOXY)ACETAMIDE; 2-(2-ETHOXY-4-FORMYLPHENOXY)BUTANAMIDE; 2-(2-ETHOXY-4-FORMYLPHENOXY)PROPANAMIDE; 2-(2-ETHOXY-6-FORMYLPHENOXY)ACETAMIDE; 2-(2-ETHOXY-6-FORMYLPHENOXY)BUTANAMIDE; 2-(2-ETHOXY-6-FORMYLPHENOXY)PROPANAMIDE; 2-(2-FLUORO-4-FORMYLPHENOXY)BENZAMIDE; 2-(2-FORMYL-4-METHOXYPHENOXY)ACETAMIDE; 2-(2-FORMYL-4-METHOXYPHENOXY)BUTANAMIDE; 2-(2-FORMYL-4-METHOXYPHENOXY)PROPANAMIDE; 2-(2-FORMYL-4-METHYLPHENOXY)ACETAMIDE; 2-(2-FORMYL-4-METHYLPHENOXY)BUTANAMIDE; 2-(2-FORMYL-4-METHYLPHENOXY)PROPANAMIDE; 2-(2-FORMYL-4-NITROPHENOXY)ACETAMIDE; 2-(2-FORMYL-4-NITROPHENOXY)BUTANAMIDE; 2-(2-FORMYL-4-NITROPHENOXY)PROPANAMIDE; 2-(2-FORMYL-5-METHOXYPHENOXY)ACETAMIDE; 2-(2-FORMYL-5-METHOXYPHENOXY)BUTANAMIDE; 2-(2-FORMYL-5-METHOXYPHENOXY)PROPANAMIDE; 2-(2-FORMYL-5-PROPOXYPHENOXY)ACETAMIDE; 2-(2-FORMYL-5-PROPOXYPHENOXY)BUTANAMIDE; 2-(2-FORMYL-5-PROPOXYPHENOXY)PROPANAMIDE; 2-(2-FORMYL-6-METHOXYPHENOXY)ACETAMIDE; 2-(2-FORMYL-6-METHOXYPHENOXY)BUTANAMIDE; 2-(2-FORMYL-6-METHOXYPHENOXY)PROPANAMIDE; 2-(2-FORMYLPHENOXY)ACETAMIDE; 2-(2-FORMYLPHENOXY)BENZAMIDE; 2-(2-FORMYLPHENOXY)BUTANAMIDE; 2-(2-FORMYLPHENOXY)PROPANAMIDE; 2-(2-FORMYLPIPERIDIN-1-YL)-4,6-DIMETHYLPYRIDINE-3-CARBOXAMIDE; 2-(2-FORMYLPIPERIDIN-1-YL)ACETAMIDE; 2-(2-FORMYLPIPERIDIN-1-YL)BUTANAMIDE; 2-(2-FORMYLPIPERIDIN-1-YL)PROPANAMIDE; 2-(2-FORMYLPIPERIDIN-1-YL)PYRIDINE-3-CARBOXAMIDE; 2-(2-OXOETHOXY)BENZAMIDE; 2-(3-AMINO-PHENYL)-OXAZOLE-4-CARBALDEHYDE; 2-(3-AMINO-PHENYL)-THIAZOLE-4-CARBALDEHYDE; 2-(3-AMINOPYRROLIDIN-1-YL)ACETALDEHYDE;

2-(3-CHLORO-2-FORMYLPHENOXY)ACETAMIDE; 2-(3-CHLORO-2-FORMYLPHENOXY)BENZAMIDE; 2-(3-CHLORO-2-FORMYLPHENOXY)BUTANAMIDE; 2-(3-CHLORO-2-FORMYLPHENOXY)PROPANAMIDE; 2-(3-FORMYL-1H-INDOL-1-YL)ACETAMIDE; 2-(3-FORMYL-2,5-DIMETHYL-1H-PYRROL-1-YL)-2-METHYLPROPANAMIDE; 2-(3-FORMYL-2,5-DIMETHYL-1H-PYRROL-1-YL)ACETAMIDE; 2-(3-FORMYL-2,5-DIMETHYL-1H-PYRROL-1-YL)PROPANAMIDE; 2-(3-FORMYL-2-METHYL-INDOL-1-YL)-ACETAMIDE; 2-(3-FORMYL-5-METHOXY-INDOL-1-YL)-ACETAMIDE; 2-(3-FORMYLPHENOXY)ACETAMIDE; 2-(3-FORMYLPHENOXY)BUTANAMIDE; 2-(3-FORMYLPHENOXY)PROPANAMIDE; 2-(3-FORMYLPIPERIDIN-1-YL)-4,6-DIMETHYLPYRIDINE-3-CARBOXAMIDE; 2-(3-FORMYLPIPERIDIN-1-YL)ACETAMIDE; 2-(3-FORMYLPIPERIDIN-1-YL)BUTANAMIDE; 2-(3-FORMYLPIPERIDIN-1-YL)PROPANAMIDE; 2-(3-FORMYLPIPERIDIN-1-YL)PYRIDINE-3-CARBOXAMIDE; 2-(3-OXOPROPOXY)BENZAMIDE; 2-(4-(AMINOMETHYL)PHENYL)-2-OXOACETALDEHYDE; 2-(4-AMINO-BENZOOXAZOL-2-YL)-BENZALDEHYDE; 2-(4-AMINO-PHENYL)-THIAZOLE-4-CARBALDEHYDE; 2-(4-AMINOPIPERIDIN-1-YL)ACETALDEHYDE; 2-(4-BROMO-2-FORMYLPHENOXY)ACETAMIDE; 2-(4-BROMO-2-FORMYLPHENOXY)BUTANAMIDE; 2-(4-BROMO-2-FORMYLPHENOXY)PROPANAMIDE; 2-(4-CHLORO-2-FORMYLPHENOXY)ACETAMIDE; 2-(4-CHLORO-2-FORMYLPHENOXY)BUTANAMIDE; 2-(4-CHLORO-2-FORMYLPHENOXY)PROPANAMIDE; 2-(4-FORMYL-2,6-DIMETHOXYPHENOXY)ACETAMIDE; 2-(4-FORMYL-2,6-DIMETHYLPHENOXY)ACETAMIDE; 2-(4-FORMYL-2,6-DIMETHYLPHENOXY)BUTANAMIDE; 2-(4-FORMYL-2,6-DIMETHYLPHENOXY)PROPANAMIDE; 2-(4-FORMYL-2-METHOXY-5-NITROPHENOXY)ACETAMIDE; 2-(4-FORMYL-2-METHOXY-5-NITROPHENOXY)PROPANAMIDE; 2-(4-FORMYL-2-METHOXYPHENOXY)ACETAMIDE; 2-(4-FORMYL-2-METHOXYPHENOXY)BUTANAMIDE; 2-(4-FORMYL-2-METHOXYPHENOXY)PROPANAMIDE; 2-(4-FORMYL-2-METHYLPHENOXY)BENZAMIDE; 2-(4-FORMYL-2-NITROPHENOXY)ACETAMIDE; 2-(4-FORMYL-2-NITROPHENOXY)BUTANAMIDE; 2-(4-FORMYL-2-NITROPHENOXY)PROPANAMIDE; 2-(4-FORMYL-3,5-DIMETHYL-1H-PYRAZOL-1-YL)ACETAMIDE; 2-(4-FORMYL-3-METHOXYPHENOXY)-ACETAMIDE; 2-(4-FORMYL-3-METHYLPHENOXY)BENZAMIDE; 2-(4-FORMYL-3-PHENYL-1H-PYRAZOL-1-YL)ACETAMIDE; 2-(4-FORMYL-6-METHYLPYRIMIDIN-2-YL)ACETAMIDE; 2-(4-FORMYLPHENOXY)ACETAMIDE; 2-(4-FORMYLPHENOXY)BENZAMIDE; 2-(4-FORMYLPHENOXY)BUTANAMIDE; 2-(4-FORMYLPHENOXY)PROPANAMIDE; 2-(4-FORMYLPIPERIDIN-1-YL)-4,6-DIMETHYLPYRIDINE-3-CARBOXAMIDE; 2-(4-FORMYLPIPERIDIN-1-YL)ACETAMIDE; 2-(4-FORMYLPIPERIDIN-1-YL)BUTANAMIDE; 2-(4-FORMYLPIPERIDIN-1-YL)PROPANAMIDE; 2-(4-FORMYLPIPERIDIN-1-YL)PYRIDINE-3-CARBOXAMIDE; 2-(4-FORMYLPYRIMIDIN-2-YL)ACETAMIDE; 2-(5-AMINO-6-CHLOROPYRIMIDIN-4-YLOXY)-4-METHYLBENZALDEHYDE; 2-(5-AMINO-6-CHLOROPYRIMIDIN-4-YLOXY)-5-METHYLBENZALDEHYDE; 2-(5-AMINO-6-CHLOROPYRIMIDIN-4-YLOXY)BENZALDEHYDE; 2-(5-AMINO-BENZOOXAZOL-2-YL)-BENZALDEHYDE; 2-(5-BROMO-3-FORMYL-1H-INDOL-1-YL)ACETAMIDE; 2-(5-BROMO-4-FORMYL-2-METHOXYPHENOXY)ACETAMIDE; 2-(5-CHLORO-2-ETHOXY-4-FORMYLPHENOXY)ACETAMIDE; 2-(5-CHLORO-4-FORMYL-2-METHOXYPHENOXY)ACETAMIDE; 2-(5-FORMYL-2-METHOXYPHENOXY)-ACETAMIDE; 2-(5-FORMYL-2-METHOXYPHENOXY)BUTANAMIDE; 2-(5-FORMYL-2-METHOXYPHENOXY)PROPANAMIDE; 2-(5-FORMYL-2-NITROPHENOXY)ACETAMIDE; 2-(5-FORMYL-2-NITROPHENOXY)BUTANAMIDE; 2-(5-FORMYL-2-NITROPHENOXY)PROPANAMIDE; 2-(5-FORMYLPYRIMIDIN-2-YL)ACETAMIDE; 2-(6-AMINO-9H-PURIN-9-YL)ACETALDEHYDE; 2-(6-AMINO-BENZOOXAZOL-2-YL)-BENZALDEHYDE; 2-(AMINOMETHYL)-3-CYCLOPROPOXYBENZALDEHYDE; 2-(AMINOMETHYL)-3-CYCLOPROPOXYISONICOTINALDEHYDE; 2-(AMINOMETHYL)-3-HYDROXYBENZALDEHYDE; 2-(AMINOMETHYL)-3-PYRIDINECARBOXALDEHYDE; 2-(AMINOMETHYL)-4-CYCLOPROPOXYBENZALDEHYDE; 2-(AMINOMETHYL)-4-CYCLOPROPOXYNICOTINALDEHYDE; 2-(AMINOMETHYL)-4-HYDROXYBENZALDEHYDE; 2-(AMINOMETHYL)-4-PYRIDINECARBOXALDEHYDE; 2-(AMINOMETHYL)-5-CYCLOPROPOXYBENZALDEHYDE; 2-(AMINOMETHYL)-5-CYCLOPROPOXYISONICOTINALDEHYDE; 2-(AMINOMETHYL)-5-CYCLOPROPOXYNICOTINALDEHYDE; 2-(AMINOMETHYL)-5-HYDROXYBENZALDEHYDE; 2-(AMINOMETHYL)-5-PYRIMIDINECARBOXALDEHYDE; 2-(AMINOMETHYL)-6-CYCLOPROPOXYBENZALDEHYDE; 2-(AMINOMETHYL)-6-HYDROXYBENZALDEHYDE; 2,3-DIAMINOBENZALDEHYDE; 2,3-DIFLUORO-4-AMINO-PHENYLACETALDEHYDE; 2,3-DIFLUORO-6-AMINO-PHENYLACETALDEHYDE; 2,4,6-TRIAMINO-5-PYRIMIDINECARBOXALDEHYDE; 2,4-DIAMINO-5-METHOXYBENZALDEHYDE; 2,4-DIAMINO-6-HYDROXY-5-PYRIMIDINECARBALDEHYDEHYDRATE; 2,4-DIAMINO-6-HYDROXY-PYRIMIDINE-5-CARBALDEHYDE; 2,4-DIAMINO-6-OXO-1,6-DIHYDRO-5-PYRIMIDINECARBALDEHYDE; 2,4-DIAMINO-7H-PYRROLO[2,3-D]PYRIMIDINE-5-CARBALDEHYDE; 2,4-DIAMINOBENZALDEHYDE; 2,4-DIAMINOPTERIDINE-6-CARBALDEHYDE; 2,4-DIAMINOPYRIDO[2,3-D]PYRIMIDINE-6-CARBALDEHYDE; 2,4-DIAMINO-PYRIMIDINE-5-CARBOXALDEHYDE; 2,4-DIAMINOQUINAZOLINE-6-CARBALDEHYDE; 2,4-HEXADIENOIC ACID, 2-AMINO-5-METHYL-6-OXO-, (E,Z)-; 2,6-DIAMINO-1,4-DIHYDRO-4-OXO-5-PYRIMIDINECARBOXALDEHYDE; 2,6-DIAMINO-4-PHENYLPYRIDINE-3,5-DICARBALDEHYDE; 2-[(1-FORMYLNAPHTHALEN-2-YL)OXY]ACETAMIDE; 2-[(1-FORMYLNAPHTHALEN-2-YL)OXY]BUTANAMIDE; 2-[(1-FORMYLNAPHTHALEN-2-YL)OXY]PROPANAMIDE; 2-[(2,6-DIFLUORO-4-FORMYLPHENYL)(2-METHYLPROPYL)AMINO]ACETAMIDE; 2-[(2,6-DIFLUORO-4-FORMYLPHENYL)(METHYL)AMINO]ACETAMIDE; 2-[(2,6-DIFLUORO-4-FORMYLPHENYL)(PROPAN-2-YL)AMINO]ACETAMIDE; 2-[(2-FLUORO-4-FORMYLPHENYL)(2-METHYLPROPYL)AMINO]ACETAMIDE; 2-[(2-FLUORO-4-FORMYLPHENYL)(METHYL)AMINO]ACETAMIDE; 2-[(2-FLUORO-4-FORMYLPHENYL)(PROPAN-2-YL)AMINO]ACETAMIDE; 2-[(2-FORMYL-

4-NITROPHENYL)(METHYL)AMINO]ACETAMIDE; 2-[(2-FORMYL-4-NITROPHENYL)(PROPAN-2-YL)AMINO]ACETAMIDE; 2-[(2-FORMYLPHENYL)(2-METHYLPROPYL)AMINO]ACETAMIDE; 2-[(2-FORMYLPHENYL)(METHYL)AMINO]ACETAMIDE; 2-[(2-FORMYLPHENYL)(PROPAN-2-YL)AMINO]ACETAMIDE; 2-[(2-FORMYLPIPERIDIN-1-YL)METHYL]BENZAMIDE; 2-[(2-METHYLPROPYL)(2-OXOETHYL)AMINO]ACETAMIDE; 2-[(2-METHYLPROPYL)(3-OXOPROPYL)AMINO]ACETAMIDE; 2-[(2-OXOETHYL)(PROPAN-2-YL)AMINO]ACETAMIDE; 2-[(3-CHLORO-2-FORMYLPHENYL)(2-METHYLPROPYL)AMINO]ACETAMIDE; 2-[(3-CHLORO-2-FORMYLPHENYL)(CYCLOPENTYL)AMINO]ACETAMIDE; 2-[(3-CHLORO-2-FORMYLPHENYL)(METHYL)AMINO]ACETAMIDE; 2-[(3-CHLORO-2-FORMYLPHENYL)(PROPAN-2-YL)AMINO]ACETAMIDE; 2-[(3-FORMYLPIPERIDIN-1-YL)METHYL]BENZAMIDE; 2-[(3-FORMYLQUINOLIN-2-YL)(METHYL)AMINO]ACETAMIDE; 2-[(3-OXOPROPYL)(PROPAN-2-YL)AMINO]ACETAMIDE; 2-[(4-FLUORO-2-FORMYLPHENYL)(2-METHYLPROPYL)AMINO]ACETAMIDE; 2-[(4-FLUORO-2-FORMYLPHENYL)(METHYL)AMINO]ACETAMIDE; 2-[(4-FLUORO-2-FORMYLPHENYL)(PROPAN-2-YL)AMINO]ACETAMIDE; 2-[(4-FORMYL-1,3-DIMETHYL-1H-PYRAZOL-5-YL)(2-METHYLPROPYL)AMINO]ACETAMIDE; 2-[(4-FORMYL-1,3-DIMETHYL-1H-PYRAZOL-5-YL)(METHYL)AMINO]ACETAMIDE; 2-[(4-FORMYL-1,3-DIMETHYL-1H-PYRAZOL-5-YL)(PROPAN-2-YL)AMINO]ACETAMIDE; 2-[(4-FORMYL-1,3-DIMETHYL-1H-PYRAZOL-5-YL)OXY]BENZAMIDE; 2-[(4-FORMYL-2-METHYLPHENYL)(2-METHYLPROPYL)AMINO]ACETAMIDE; 2-[(4-FORMYL-2-METHYLPHENYL)(METHYL)AMINO]ACETAMIDE; 2-[(4-FORMYL-2-METHYLPHENYL)(PROPAN-2-YL)AMINO]ACETAMIDE; 2-[(4-FORMYL-2-NITROPHENYL)(METHYL)AMINO]ACETAMIDE; 2-[(4-FORMYL-2-NITROPHENYL)(PROPAN-2-YL)AMINO]ACETAMIDE; 2-[(4-FORMYL-3-METHYLPHENYL)(2-METHYLPROPYL)AMINO]ACETAMIDE; 2-[(4-FORMYL-3-METHYLPHENYL)(METHYL)AMINO]ACETAMIDE; 2-[(4-FORMYL-3-METHYLPHENYL)(PROPAN-2-YL)AMINO]ACETAMIDE; 2-[(4-FORMYLPHENYL)(2-METHYLPROPYL)AMINO]ACETAMIDE; 2-[(4-FORMYLPHENYL)(METHYL)AMINO]ACETAMIDE; 2-[(4-FORMYLPHENYL)(PROPAN-2-YL)AMINO]ACETAMIDE; 2-[(4-FORMYLPIPERIDIN-1-YL)METHYL]BENZAMIDE; 2-[(5-BROMO-2-FORMYLPHENYL)(METHYL)AMINO]ACETAMIDE; 2-[(5-BROMO-2-FORMYLPHENYL)(PROPAN-2-YL)AMINO]ACETAMIDE; 2-[(5-FORMYL-2-FURYL)METHOXY]BENZAMIDE; 2-[(5-FORMYL-2-METHOXYBENZYL)OXY]BENZAMIDE; 2-[(5-FORMYLFURAN-2-YL)(2-METHYLPROPYL)AMINO]ACETAMIDE; 2-[(5-FORMYLFURAN-2-YL)(METHYL)AMINO]ACETAMIDE; 2-[(5-FORMYLFURAN-2-YL)(PROPAN-2-YL)AMINO]ACETAMIDE; 2-[(6-FORMYL-2H-1,3-BENZODIOXOL-5-YL)OXY]ACETAMIDE; 2-[(CARBAMOYLMETHYL)((5-FORMYLIMIDAZO[2,1-B][1,3]THIAZOL-6-YL))AMINO]ACETAMIDE; 2-[(CARBAMOYLMETHYL)(2,6-DIFLUORO-4-FORMYLPHENYL)AMINO]ACETAMIDE; 2-[(CARBAMOYLMETHYL)(2-FLUORO-4-FORMYLPHENYL)AMINO]ACETAMIDE; 2-[(CARBAMOYLMETHYL)(2-FORMYLPHENYL)AMINO]ACETAMIDE; 2-[(CARBAMOYLMETHYL)(2-OXOETHYL)AMINO]ACETAMIDE; 2-[(CARBAMOYLMETHYL)(3-CHLORO-2-FORMYLPHENYL)AMINO]ACETAMIDE; 2-[(CARBAMOYLMETHYL)(3-OXOPROPYL)AMINO]ACETAMIDE; 2-[(CARBAMOYLMETHYL)(4-FLUORO-2-FORMYLPHENYL)AMINO]ACETAMIDE; 2-[(CARBAMOYLMETHYL)(4-FORMYL-1,3-DIMETHYL-1H-PYRAZOL-5-YL)AMINO]ACETAMIDE; 2-[(CARBAMOYLMETHYL)(4-FORMYL-2-METHYLPHENYL)AMINO]ACETAMIDE; 2-[(CARBAMOYLMETHYL)(4-FORMYL-3-METHYLPHENYL)AMINO]ACETAMIDE; 2-[(CARBAMOYLMETHYL)(4-FORMYLPHENYL)AMINO]ACETAMIDE; 2-[1-(2-FLUORO-4-FORMYLPHENYL)PIPERIDIN-4-YL]ACETAMIDE; 2-[1-(2-FORMYLPHENYL)PIPERIDIN-4-YL]ACETAMIDE; 2-[1-(2-OXOETHYL)PIPERIDIN-4-YL]ACETAMIDE; 2-[1-(3-CHLORO-2-FORMYLPHENYL)PIPERIDIN-4-YL]ACETAMIDE; 2-[1-(3-OXOPROPYL)PIPERIDIN-4-YL]ACETAMIDE; 2-[1-(4-FLUORO-2-FORMYLPHENYL)PIPERIDIN-4-YL]ACETAMIDE; 2-[1-(4-FORMYL-1,3-DIMETHYL-1H-PYRAZOL-5-YL)PIPERIDIN-4-YL]ACETAMIDE; 2-[1-(4-FORMYL-2-METHYLPHENYL)PIPERIDIN-4-YL]ACETAMIDE; 2-[1-(4-FORMYL-3-METHYLPHENYL)PIPERIDIN-4-YL]ACETAMIDE; 2-[1-(4-FORMYLPHENYL)PIPERIDIN-4-YL]ACETAMIDE; 2-[1-(5-FORMYLFURAN-2-YL)PIPERIDIN-4-YL]ACETAMIDE; 2-[15N]AMINO-2-DEOXY-D-GLUCOSE HYDROCHLORIDE; 2-[3-(AMINOMETHYL)PYRROLIDIN-1-YL]ACETALDEHYDE; 2-[BUTYL((5-FORMYLIMIDAZO[2,1-B][1,3]THIAZOL-6-YL))AMINO]ACETAMIDE; 2-[BUTYL(2,6-DIFLUORO-4-FORMYLPHENYL)AMINO]ACETAMIDE; 2-[BUTYL(2-FLUORO-4-FORMYLPHENYL)AMINO]ACETAMIDE; 2-[BUTYL(2-FORMYLPHENYL)AMINO]ACETAMIDE; 2-[BUTYL(2-OXOETHYL)AMINO]ACETAMIDE; 2-[BUTYL(3-CHLORO-2-FORMYLPHENYL)AMINO]ACETAMIDE; 2-[BUTYL(3-OXOPROPYL)AMINO]ACETAMIDE; 2-[BUTYL(4-FLUORO-2-FORMYLPHENYL)AMINO]ACETAMIDE; 2-[BUTYL(4-FORMYL-1,3-DIMETHYL-1H-PYRAZOL-5-YL)AMINO]ACETAMIDE; 2-[BUTYL(4-FORMYL-2-METHYLPHENYL)AMINO]ACETAMIDE; 2-[BUTYL(4-FORMYL-3-METHYLPHENYL)AMINO]ACETAMIDE; 2-[BUTYL(4-FORMYLPHENYL)AMINO]ACETAMIDE; 2-[BUTYL(5-FORMYLFURAN-2-YL)AMINO]ACETAMIDE; 2-[CYCLOPENTYL(2-FLUORO-4-FORMYLPHENYL)AMINO]ACETAMIDE; 2-[CYCLOPENTYL(2-FORMYLPHENYL)AMINO]ACETAMIDE; 2-[CYCLOPENTYL(2-OXOETHYL)AMINO]ACETAMIDE; 2-[CYCLOPENTYL(3-OXOPROPYL)AMINO]ACETAMIDE; 2-[CYCLOPENTYL(4-FLUORO-2-FORMYLPHENYL)AMINO]ACETAMIDE; 2-[CYCLOPENTYL(4-FORMYL-1,3-DIMETHYL-1H-PYRAZOL-5-YL)AMINO]ACETAMIDE; 2-[CYCLOPENTYL(4-FORMYL-2-METHYLPHENYL)AMINO]ACETAMIDE; 2-[CYCLOPENTYL(4-FORMYL-3-METHYLPHENYL)AMINO]ACETAMIDE; 2-[CYCLOPENTYL(4-FORMYLPHENYL)AMINO]ACETAMIDE; 2-[CYCLOPENTYL(5-FORMYLFURAN-2-YL)AMINO]ACETAMIDE; 2-[METHYL(2-OXOETHYL)AMINO]ACETAMIDE; 2-[METHYL(3-OXOPROPYL)AMINO]ACETAMIDE; 2-AMINO-1H-IMIDAZOLE-4-CARBALDEHYDE HCL; 2-AMINO-1H-IMIDAZOLE-5-CARBALDEHYDE; 2-AMINO-1-METHYL-1H-IMIDAZOLE-4-CARBALDEHYDE; 2-AMINO-1-

METHYL-1H-INDOLE-3-CARBALDEHYDE; 2-AMINO-1-PROPANAL; 2-AMINO-3-(2-(TRIFLUOROMETHOXY)PHENYL)PYRIDINE-5-CARBOXALDEHYDE; 2-AMINO-3-(2,3-DIFLUOROPHENYL)PYRIDINE-5-CARBOXALDEHYDE; 2-AMINO-3-(3-(TRIFLUOROMETHOXY)PHENYL)PYRIDINE-5-CARBOXALDEHYDE; 2-AMINO-3-(4-(TRIFLUOROMETHOXY)PHENYL)PYRIDINE-5-CARBOXALDEHYDE; 2-AMINO-3-(PERFLUOROPHENYL)PYRIDINE-5-CARBOXALDEHYDE; 2-AMINO-3-(TRIFLUOROMETHOXY)BENZALDEHYDE; 2-AMINO-3-(TRIFLUOROMETHYL)ISONICOTINALDEHYDE; 2-AMINO-3,4,5,6-TETRAHYDROXYHEXANAL HYDROCHLORIDE; 2-AMINO-3,4,5-TRIFLUOROBENZALDEHYDE; 2-AMINO-3,4,6-TRIFLUORO-5-METHYLBENZALDEHYDE; 2-AMINO-3,5-DIBROMOBENZALDEHYDE; 2-AMINO-3,5-DICHLOROBENZALDEHYDE; 2-AMINO-3,5-DIFLUOROBENZALDEHYDE; 2-AMINO-3,6-DIMETHOXYBENZENECARBALDEHYDE; 2-AMINO-3-BROMOBENZALDEHYDE; 2-AMINO-3-CHLOROBENZALDEHYDE; 2-AMINO-3-CYCLOPROPOXYBENZALDEHYDE; 2-AMINO-3-CYCLOPROPOXYISONICOTINALDEHYDE; 2-AMINO-3-FLUOROBENZALDEHYDE; 2-AMINO-3-FORMYL-6,7-DIMETHYLCHROMONE; 2-AMINO-3-FORMYL-6-METHYLCHROMONE; 2-AMINO-3-FORMYLBENZOIC ACID; 2-AMINO-3-FORMYLCHROMONE; 2-AMINO-3-FORMYLPYRIDINE; 2-AMINO-3-HYDROXY-4-METHOXYBENZALDEHYDE; 2-AMINO-3-HYDROXYBENZALDEHYDE; 2-AMINO-3-IODOBENZALDEHYDE; 2-AMINO-3-METHOXYBENZALDEHYDE; 2-AMINO-3-METHYLBENZALDEHYDE; 2-AMINO-3-METHYLISONICOTINALDEHYDE; 2-AMINO-3-NITROBENZALDEHYDE; 2-AMINO-3-PYRIDINECARBOXALDEHYDE HCL; 2-AMINO-4-(TRIFLUOROMETHOXY)BENZALDEHYDE; 2-AMINO-4-(TRIFLUOROMETHYL)BENZALDEHYDE; 2-AMINO-4-(TRIFLUOROMETHYL)NICOTINALDEHYDE; 2-AMINO-4-(TRIFLUOROMETHYL)PYRIMIDINE-5-CARBALDEHYDE; 2-AMINO-4,5-DIMETHOXYBENZALDEHYDE; 2-AMINO-4,6-DICHLOROPYRIMIDINE-5-CARBALDEHYDE; 2-AMINO-4,6-DIFLUOROBENZALDEHYDE; 2-AMINO-4,6-DIPIPERIDINO-5-PYRIMIDINECARBALDEHYDE; 2-AMINO-4-[BENZYL(METHYL)AMINO]-6-CHLORO-5-PYRIMIDINECARBALDEHYDE; 2-AMINO-4-BENZYLOXYBENZALDEHYDE; 2-AMINO-4-BRBOMOPYRIDINE-6-CARBOXALDEHYDE; 2-AMINO-4-BROMOBENZALDEHYDE; 2-AMINO-4-CHLORO-6-METHYL-PYRIMIDINE-5-CARBALDEHYDE; 2-AMINO-4-CHLORO-6-MORPHOLIN-4-YLPYRIMIDINE-5-CARBALDEHYDE; 2-AMINO-4-CHLORO-6-PIPERIDINO-5-PYRIMIDINECARBALDEHYDE; 2-AMINO-4-CHLORO-6-PYRROLIDIN-1-YLPYRIMIDINE-5-CARBALDEHYDE; 2-AMINO-4-CHLOROBENZALDEHYDE; 2-AMINO-4-CHLORO-PYRIDINE-3-CARBALDEHYDE; 2-AMINO-4-CHLOROPYRIMIDINE-5-CARBOXALDEHYDE; 2-AMINO-4-CYCLOPROPOXYBENZALDEHYDE; 2-AMINO-4-CYCLOPROPOXYNICOTINALDEHYDE; 2-AMINO-4-ETHOXYBENZALDEHYDE; 2-AMINO-4-FLUOROBENZALDEHYDE; 2-AMINO-4-HYDROXY-3-METHOXY-BENZALDEHYDE; 2-AMINO-4-HYDROXYBENZALDEHYDE; 2-AMINO-4-HYDROXYPTERIDINE-6-CARBALDEHYDE; 2-AMINO-4-IODOBENZALDEHYDE; 2-AMINO-4-METHOXY-3-PENTYLOXY-BENZALDEHYDE; 2-AMINO-4-METHOXY-6-MORPHOLIN-4-YLPYRIMIDINE-5-CARBALDEHYDE; 2-AMINO-4-METHOXY-6-PYRROLIDIN-1-YLPYRIMIDINE-5-CARBALDEHYDE; 2-AMINO-4-METHOXYBENZALDEHYDE; 2-AMINO-4-METHYL-5-THIAZOLECARBOXALDEHYDE; 2-AMINO-4-METHYLBENZALDEHYDE; 2-AMINO-4-METHYLNICOTINALDEHYDE; 2-AMINO-4-NITRO-5-METHOXYBENZALDEHYDE; 2-AMINO-4-NITROBENZALDEHYDE; 2-AMINO-4-OXOBUTANOIC ACID; 2-AMINO-5-(2-(TRIFLUOROMETHOXY)PHENYL)ISONICOTINALDEHYDE; 2-AMINO-5-(2-(TRIFLUOROMETHOXY)PHENYL)NICOTINALDEHYDE; 2-AMINO-5-(2-(TRIFLUOROMETHYL)PHENYL)ISONICOTINALDEHYDE; 2-AMINO-5-(2-(TRIFLUOROMETHYL)PHENYL)NICOTINALDEHYDE; 2-AMINO-5-(2,3-DIFLUOROPHENYL)ISONICOTINALDEHYDE; 2-AMINO-5-(2,3-DIFLUOROPHENYL)NICOTINALDEHYDE; 2-AMINO-5-(2-FLUOROPHENYL)ISONICOTINALDEHYDE; 2-AMINO-5-(2-FLUOROPHENYL)NICOTINALDEHYDE; 2-AMINO-5-(2-FORMYLPHENYL)ISONICOTINIC ACID; 2-AMINO-5-(2-FORMYLPHENYL)NICOTINIC ACID; 2-AMINO-5-(2-OXOPIPERIDIN-1-YL)-BENZALDEHYDE; 2-AMINO-5-(2-OXOPYRROLIDIN-1-YL)BENZALDEHYDE; 2-AMINO-5-(3-(TRIFLUOROMETHOXY)PHENYL)ISONICOTINALDEHYDE; 2-AMINO-5-(3-(TRIFLUOROMETHOXY)PHENYL)NICOTINALDEHYDE; 2-AMINO-5-(3-(TRIFLUOROMETHYL)PHENYL)ISONICOTINALDEHYDE; 2-AMINO-5-(3-(TRIFLUOROMETHYL)PHENYL)NICOTINALDEHYDE; 2-AMINO-5-(3-FLUOROPHENYL)ISONICOTINALDEHYDE; 2-AMINO-5-(3-FLUOROPHENYL)NICOTINALDEHYDE; 2-AMINO-5-(3-FORMYLPHENYL)ISONICOTINIC ACID; 2-AMINO-5-(3-FORMYLPHENYL)NICOTINIC ACID; 2-AMINO-5-(3-OXO-MORPHOLIN-4-YL)-BENZALDEHYDE; 2-AMINO-5-(4-(TRIFLUOROMETHOXY)PHENYL)ISONICOTINALDEHYDE; 2-AMINO-5-(4-(TRIFLUOROMETHOXY)PHENYL)NICOTINALDEHYDE; 2-AMINO-5-(4-(TRIFLUOROMETHYL)PHENYL)ISONICOTINALDEHYDE; 2-AMINO-5-(4-(TRIFLUOROMETHYL)PHENYL)NICOTINALDEHYDE; 2-AMINO-5-(4-FLUOROPHENYL)ISONICOTINALDEHYDE; 2-AMINO-5-(4-FLUOROPHENYL)NICOTINALDEHYDE; 2-AMINO-5-(4-FORMYLPHENYL)ISONICOTINIC ACID; 2-AMINO-5-(4-FORMYLPHENYL)NICOTINIC ACID; 2-AMINO-5-(PERFLUOROPHENYL)ISONICOTINALDEHYDE; 2-AMINO-5-(PERFLUOROPHENYL)NICOTINALDEHYDE; 2-AMINO-5-(PHENYLETHYNYL)NICOTINALDEHYDE; 2-AMINO-5-(PYRIDIN-3-YL)ISONICOTINALDEHYDE; 2-AMINO-5-(PYRIDIN-3-YL)NICOTINALDEHYDE; 2-AMINO-5-(PYRIDIN-4-YL)ISONICOTINALDEHYDE; 2-AMINO-5-(PYRIDIN-4-YL)NICOTINALDEHYDE; 2-AMINO-5-(TRIFLUOROMETHOXY)BENZALDEHYDE; 2-AMINO-5-(TRIFLUOROMETHYL)ISONICOTINAL-

DEHYDE; 2-AMINO-5-(TRIFLUOROMETHYL)NICOTINALDEHYDE; 2-AMINO-5-BENZYLOXY-4-METHOXYBENZALDEHYDE; 2-AMINO-5-BENZYLOXYBENZALDEHYDE; 2-AMINO-5-BROMOBENZALDEHYDE; 2-AMINO-5-BROMOISONICOTINALDEHYDE; 2-AMINO-5-BROMONICOTINALDEHYDE; 2-AMINO-5-BROMOPYRIMIDINE-4-CARBALDEHYDE; 2-AMINO-5-CHLOROBENZALDEHYDE; 2-AMINO-5-CHLOROBENZALDEHYDE HYDROBROMIDE; 2-AMINO-5-CHLOROBENZALDEHYDE HYDROCHLORIDE; 2-AMINO-5-CHLOROISONICOTINALDEHYDE; 2-AMINO-5-CHLORONICOTINALDEHYDE; 2-AMINO-5-CYCLOPROPOXY-2,3-DIHYDROPYRIDINE-3-CARBALDEHYDE; 2-AMINO-5-CYCLOPROPOXYISONICOTINALDEHYDE; 2-AMINO-5-ETHOXY-4-METHOXYBENZALDEHYDE; 2-AMINO-5-ETHOXYBENZALDEHYDE; 2-AMINO-5-FLUOROBENZALDEHYDE; 2-AMINO-5-FLUOROISONICOTINALDEHYDE; 2-AMINO-5-FLUORO-PYRIDINE-3-CARBALDEHYDE; 2-AMINO-5-FORMYL-4-(TRIFLUOROMETHYL)THIAZOLE; 2-AMINO-5-FORMYLBENZONITRILE; 2-AMINO-5-FORMYLTHIAZOLE; 2-AMINO-5-FORMYLTHIAZOLE HCL; 2-AMINO-5-HYDROXY-4-METHOXYBENZALDEHYDE; 2-AMINO-5-HYDROXYBENZALDEHYDE; 2-AMINO-5-IODOBENZALDEHYDE; 2-AMINO-5-IODOPYRIDINE-3-CARBOXALDEHYDE; 2-AMINO-5-METHOXY-4-(PHENYLMETHOXY)BENZALDEHYDE; 2-AMINO-5-METHOXYBENZALDEHYDE; 2-AMINO-5-METHYLBENZALDEHYDE; 2-AMINO-5-METHYLISONICOTINALDEHYDE; 2-AMINO-5-METHYLNICOTINALDEHYDE; 2-AMINO-5-NITROBENZALDEHYDE; 2-AMINO-5-PHENYLISONICOTINALDEHYDE; 2-AMINO-5-PHENYLNICOTINALDEHYDE; 2-AMINO-5-PYRIMIDINECARBOXYALDEHYDE; 2-AMINO-6-(1-PIPERIDINYL)-3,5-PYRIDINEDICARBALDEHYDE; 2-AMINO-6-(DIMETHYLAMINO)-4-HYDROXYPYRIMIDINE-5-CARBALDEHYDE; 2-AMINO-6-(TRIFLUOROMETHOXY)BENZALDEHYDE; 2-AMINO-6-(TRIFLUOROMETHYL)ISONICOTINALDEHYDE; 2-AMINO-6-(TRIFLUOROMETHYL)NICOTINALDEHYDE; 2-AMINO-6,7-DICHLORO-3-FORMYLCHROMONE; 2-AMINO-6,8-DICHLORO-3-FORMYLCHROMONE; 2-AMINO-6,8-DIMETHYL-4-OXO-4H-CHROMENE-3-CARBALDEHYDE; 2-AMINO-6-BROMO-3-FORMYLCHROMONE; 2-AMINO-6-BROMO-PYRIDINE-3-CARBALDEHYDE; 2-AMINO-6-CHLORO-3-FORMYLCHROMONE; 2-AMINO-6-CHLORO-7-METHYL-3-FORMYL CHROMONE; 2-AMINO-6-CHLOROBENZALDEHYDE; 2-AMINO-6-CHLOROISONICOTINALDEHYDE; 2-AMINO-6-CHLORO-PYRIDINE-3-CARBALDEHYDE; 2-AMINO-6-CYCLOPROPOXYBENZALDEHYDE; 2-AMINO-6-ETHYL-3-FORMYLCHROMONE; 2-AMINO-6-FLUORO-4-OXO-4H-CHROMENE-3-CARBALDEHYDE; 2-AMINO-6-FLUOROBENZALDEHYDE; 2-AMINO-6-HYDROXYBENZALDEHYDE; 2-AMINO-6-IODOBENZALDEHYDE; 2-AMINO-6-ISOPROPYL-4-OXO-4H-BENZOPYRAN-3-CARBOXALDEHYDE; 2-AMINO-6-METHOXY-4-OXO-4H-CHROMENE-3-CARBALDEHYDE; 2-AMINO-6-METHOXYBENZALDEHYDE; 2-AMINO-6-METHYLBENZALDEHYDE; 2-AMINO-6-METHYLISONICOTINALDEHYDE; 2-AMINO-6-METHYL-PYRIDINE-3-CARBALDEHYDE; 2-AMINO-6-METHYLPYRIMIDINE-4-CARBALDEHYDE; 2-AMINO-6-NITROBENZALDEHYDE; 2-AMINO-6-PYRIDINE CARBOXALDEHYDE; 2-AMINO-6-TERT-BUTYL-3-FORMYLCHROMONE; 2-AMINOBENZALDEHYDE; 2-AMINOBENZALDEHYDE HCL; 2-AMINOBENZO[D]THIAZOLE-6-CARBALDEHYDE; 2'-AMINO-BIPHENYL-4-CARBALDEHYDE; 2-AMINONAPHTHALENE-1-CARBOXALDEHYDE; 2-AMINONAPHTHALENE-3-CARBOXALDEHYDE; 2-AMINONAPHTHALENE-4-CARBOXALDEHYDE; 2-AMINONAPHTHALENE-5-CARBOXALDEHYDE; 2-AMINONAPHTHALENE-6-CARBOXALDEHYDE; 2-AMINONAPHTHALENE-7-CARBOXALDEHYDE; 2-AMINONAPHTHALENE-8-CARBOXALDEHYDE; 2-AMINOOXAZOLE-5-CARBALDEHYDE; 2-AMINOPYRIDINE-4-CARBALDEHYDE; 2-AMINOPYRIMIDINE-4-CARBOXALDEHYDE; 2-AMINO-THIAZOLE-4-CARBOXALDEHYDE; 2-AMINOTHIOPHENE-3-CARBOXALDEHYDE; 2-AMINOTHIOPHENE-4-CARBOXALDEHYDE; 2-AMINOTHIOPHENE-5-CARBOXALDEHYDE; 2-CHLORO-3-FORMYL-QUINOLINE-8-CARBOXYLIC ACID AMIDE; 2-CYCLOPROPOXY-3-FORMYLBENZAMIDE; 2-CYCLOPROPOXY-4-FORMYLBENZAMIDE; 2-CYCLOPROPOXY-5-FORMYLBENZAMIDE; 2-CYCLOPROPOXY-6-FORMYLBENZAMIDE; 2-FLUORO-3-AMINOBENZALDEHYDE; 2-FLUORO-6-(2-OXOETHOXY)BENZAMIDE; 2-FLUORO-6-(3-OXOPROPOXY)BENZAMIDE; 2-FORMYL-3-HYDROXYBENZAMIDE; 2-FORMYL-4-HYDROXYBENZAMIDE; 2-FORMYL-5-HYDROXYBENZAMIDE; 2-FORMYL-6-HYDROXYBENZAMIDE; 2-FORMYLBENZYLAMINE; 2-FORMYLBENZYLAMINE HYDROCHLORIDE; 2-NAPHTHALENECARBOXALDEHYDE, 5-AMINO-5,6,7,8-TETRAHYDRO-,(5R)-; 2-THIOPHENECARBOXALDEHYDE, 3-AMINO-5-METHYL-; 3-((1R)-1,2-DIAMINOETHYL)-2-HYDROXY-5-METHYLBENZALDEHYDE; 3-((1R)-1-AMINO-2-(4-PYRIDYL)ETHYL)-2-HYDROXY-5-METHYLBENZALDEHYDE; 3-((1R)-1-AMINO-2,2,2-TRIFLUOROETHYL)-2-HYDROXY-5-METHYLBENZALDEHYDE; 3-((1R)-1-AMINO-2-HYDROXYETHYL)-2-HYDROXY-5-METHYLBENZALDEHYDE; 3-((1R)-1-AMINO-2-METHYLPROPYL)-2-HYDROXY-5-METHYLBENZALDEHYDE; 3-((1R)-1-AMINO-3-HYDROXYPROPYL)-2-HYDROXY-5-METHYLBENZALDEHYDE; 3-((1R)-1-AMINO-4-HYDROXYBUTYL)-2-HYDROXY-5-METHYLBENZALDEHYDE; 3-((1R)-1-AMINO-5-HYDROXYPENTYL)-2-HYDROXY-5-METHYLBENZALDEHYDE; 3-((1R)-1-AMINOBUTYL)-2-HYDROXY-5-METHYLBENZALDEHYDE; 3-((1R)-1-AMINOETHYL)-2-HYDROXY-5-METHYLBENZALDEHYDE; 3-((1R)-1-AMINOPROP-2-ENYL)-2-HYDROXY-5-METHYLBENZALDEHYDE; 3-((1R)-1-AMINOPROPYL)-2-HYDROXY-5-METHYLBENZALDEHYDE; 3-((1R)AMINOCYCLOPROPYLMETHYL)-2-HYDROXY-5-METHYLBENZALDEHYDE; 3-((1R,2R)-1-AMINO-2-HYDROXYPROPYL)-2-HYDROXY-5-METHYLBENZALDEHYDE; 3-((1S)-1,2-DIAMINOETHYL)-2-HYDROXY-5-METHYLBENZALDEHYDE; 3-((1S)-1-AMINO-2-(4-PYRIDYL)ETHYL)-2-HYDROXY-5-METHYLBENZALDEHYDE; 3-((1S)-1-

AMINO-2,2,2-TRIFLUOROETHYL)-2-HYDROXY-5-METHYLBENZALDEHYDE; 3-((1S)-1-AMINO-2-HYDROXYETHYL)-2-HYDROXY-5-METHYLBENZALDEHYDE; 3-((1S)-1-AMINO-2-METHYLPROPYL)-2-HYDROXY-5-METHYLBENZALDEHYDE; 3-((1S)-1-AMINO-3-HYDROXYPROPYL)-2-HYDROXY-5-METHYLBENZALDEHYDE; 3-((1S)-1-AMINO-4-HYDROXYBUTYL)-2-HYDROXY-5-METHYLBENZALDEHYDE; 3-((1S)-1-AMINO-5-HYDROXYPENTYL)-2-HYDROXY-5-METHYLBENZALDEHYDE; 3-((1S)-1-AMINOBUTYL)-2-HYDROXY-5-METHYLBENZALDEHYDE; 3-((1S)-1-AMINOETHYL)-2-HYDROXY-5-METHYLBENZALDEHYDE; 3-((1S)-1-AMINOPROP-2-ENYL)-2-HYDROXY-5-METHYLBENZALDEHYDE; 3-((1S)AMINOCYCLOPROPYLMETHYL)-2-HYDROXY-5-METHYLBENZALDEHYDE; 3-((1S,2R)-1-AMINO-2-HYDROXYPROPYL)-2-HYDROXY-5-METHYLBENZALDEHYDE; 3-([3-(AMINOMETHYL)PYRROLIDIN-1-YL]METHYL)-4-METHOXYBENZALDEHYDE; 3-(2,4-DICHLORO-6-FORMYLPHENOXY)-2-METHYLPROPANAMIDE; 3-(2,4-DICHLORO-6-FORMYLPHENOXY)PROPANAMIDE; 3-(2-AMINOETHYLAMINO)-5-METHYL-1H-PYRAZOLE-4-CARBALDEHYDE; 3-(2-BROMO-4-FORMYLPHENOXY)-2-METHYLPROPANAMIDE; 3-(2-BROMO-4-FORMYLPHENOXY)PROPANAMIDE; 3-(2-BROMO-6-FORMYLPHENOXY)-2-METHYLPROPANAMIDE; 3-(2-BROMO-6-FORMYLPHENOXY)PROPANAMIDE; 3-(2-CHLORO-4-FORMYL-6-METHOXYPHENOXY)-2-METHYLPROPANAMIDE; 3-(2-CHLORO-4-FORMYL-6-METHOXYPHENOXY)PROPANAMIDE; 3-(2-CHLORO-4-FORMYLPHENOXY)-2-METHYLPROPANAMIDE; 3-(2-CHLORO-4-FORMYLPHENOXY)PROPANAMIDE; 3-(2-ETHOXY-4-FORMYLPHENOXY)-2-METHYLPROPANAMIDE; 3-(2-ETHOXY-4-FORMYLPHENOXY)PROPANAMIDE; 3-(2-ETHOXY-6-FORMYLPHENOXY)-2-METHYLPROPANAMIDE; 3-(2-ETHOXY-6-FORMYLPHENOXY)PROPANAMIDE; 3-(2-FORMYL-4-METHOXYPHENOXY)-2-METHYLPROPANAMIDE; 3-(2-FORMYL-4-METHOXYPHENOXY)PROPANAMIDE; 3-(2-FORMYL-4-METHYLPHENOXY)-2-METHYLPROPANAMIDE; 3-(2-FORMYL-4-METHYLPHENOXY)PROPANAMIDE; 3-(2-FORMYL-4-NITROPHENOXY)-2-METHYLPROPANAMIDE; 3-(2-FORMYL-4-NITROPHENOXY)PROPANAMIDE; 3-(2-FORMYL-5-METHOXYPHENOXY)-2-METHYLPROPANAMIDE; 3-(2-FORMYL-5-METHOXYPHENOXY)PROPANAMIDE; 3-(2-FORMYL-5-PROPOXYPHENOXY)-2-METHYLPROPANAMIDE; 3-(2-FORMYL-5-PROPOXYPHENOXY)PROPANAMIDE; 3-(2-FORMYL-6-METHOXYPHENOXY)-2-METHYLPROPANAMIDE; 3-(2-FORMYL-6-METHOXYPHENOXY)PROPANAMIDE; 3-(2-FORMYL-IMIDAZOL-1-YL)-PROPIONAMIDE; 3-(2-FORMYLPHENOXY)-2-METHYLPROPANAMIDE; 3-(2-FORMYLPHENOXY)PROPANAMIDE; 3-(2-FORMYLPIPERIDIN-1-YL)-2-METHYLPROPANAMIDE; 3-(2-FORMYLPIPERIDIN-1-YL)PROPANAMIDE; 3-(2-FORMYLTHIOPHEN-4-YL)-6-AMINOPICOLINIC ACID; 3-(2-OXOETHOXY)BENZAMIDE; 3-(3-AMINO-4-ETHYLPHENYL)PROPANAL; 3-(3-AMINOPIPERIDIN-1-YL)PROPANAL; 3-(3-AMINOPYRROLIDIN-1-YL)PROPANAL; 3-(3-CHLORO-2-FORMYLPHENOXY)-2-METHYLPROPANAMIDE; 3-(3-CHLORO-2-FORMYLPHENOXY)PROPANAMIDE; 3-(3-FORMYL-2,5-DIMETHYL-1H-PYRROL-1-YL)PROPANAMIDE; 3-(3-FORMYL-2-HYDROXYPHENYL)BENZAMIDE; 3-(3-FORMYL-4-HYDROXYPHENYL)BENZAMIDE; 3-(3-FORMYL-INDOL-1-YL)-PROPIONAMIDE; 3-(3-FORMYLPHENOXY)-2-METHYLPROPANAMIDE; 3-(3-FORMYLPHENOXY)PROPANAMIDE; 3-(3-FORMYLPIPERIDIN-1-YL)-2-METHYLPROPANAMIDE; 3-(3-FORMYLPIPERIDIN-1-YL)PROPANAMIDE; 3-(3-OXOPROPOXY)BENZAMIDE; 3-(4-AMINO-IMIDAZOL-1-YL)-PROPIONALDEHYDE 2HCL; 3-(4-AMINOPHENYL)-2-HYDROXYBENZALDEHYDE; 3-(4-AMINOPHENYL)-4-HYDROXYBENZALDEHYDE; 3-(4-AMINOPHENYL)PYRIDINE-4-CARBALDEHYDE; 3-(4-AMINOPIPERIDIN-1-YL)PROPANAL; 3-(4-BROMO-2-FORMYLPHENOXY)-2-METHYLPROPANAMIDE; 3-(4-BROMO-2-FORMYLPHENOXY)PROPANAMIDE; 3-(4-CHLORO-2-FORMYLPHENOXY)-2-METHYLPROPANAMIDE; 3-(4-CHLORO-2-FORMYLPHENOXY)PROPANAMIDE; 3-(4-FORMYL-2,6-DIMETHOXYPHENOXY)-2-METHYLPROPANAMIDE; 3-(4-FORMYL-2,6-DIMETHOXYPHENOXY)PROPANAMIDE; 3-(4-FORMYL-2,6-DIMETHYLPHENOXY)-2-METHYLPROPANAMIDE; 3-(4-FORMYL-2,6-DIMETHYLPHENOXY)PROPANAMIDE; 3-(4-FORMYL-2-METHOXY-5-NITROPHENOXY)PROPANAMIDE; 3-(4-FORMYL-2-METHOXYPHENOXY)-2-METHYLPROPANAMIDE; 3-(4-FORMYL-2-METHOXYPHENOXY)PROPANAMIDE; 3-(4-FORMYL-2-NITROPHENOXY)-2-METHYLPROPANAMIDE; 3-(4-FORMYL-2-NITROPHENOXY)PROPANAMIDE; 3-(4-FORMYL-3,5-DIMETHYL-1H-PYRAZOL-1-YL)-2-METHYLPROPANAMIDE; 3-(4-FORMYL-3,5-DIMETHYL-1H-PYRAZOL-1-YL)PROPANAMIDE; 3-(4-FORMYLPHENOXY)-2-METHYLPROPANAMIDE; 3-(4-FORMYLPHENOXY)PROPANAMIDE; 3-(4-FORMYLPIPERIDIN-1-YL)-2-METHYLPROPANAMIDE; 3-(4-FORMYLPIPERIDIN-1-YL)PROPANAMIDE; 3-(4-FORMYLPYRIDIN-3-YL)BENZAMIDE; 3-(5-AMINO-PYRIDIN-2-YLOXY)BENZALDEHYDE; 3-(5-FORMYL-2-HYDROXYPHENYL)BENZAMIDE; 3-(5-FORMYL-2-METHOXYPHENOXY)-2-METHYLPROPANAMIDE; 3-(5-FORMYL-2-METHOXYPHENOXY)PROPANAMIDE; 3-(5-FORMYL-2-NITROPHENOXY)-2-METHYLPROPANAMIDE; 3-(5-FORMYL-2-NITROPHENOXY)PROPANAMIDE; 3-(5-FORMYL-FURAN-2-YL)-BENZOIC ACID CARBAMOYLMETHYL ESTER; 3-(5-FORMYLPYRIDIN-3-YL)BENZAMIDE; 3-(5-FORMYLTHIOPHEN-2-YL)-6-AMINOPICOLINIC ACID; 3-(AMINOMETHYL)-2-CYCLOPROPOXYBENZALDEHYDE; 3-(AMINOMETHYL)-2-HYDROXYBENZALDEHYDE; 3-(AMINOMETHYL)-4-CYCLOPROPOXYBENZALDEHYDE; 3-(AMINOMETHYL)-4-CYCLOPROPOXYPICOLINALDEHYDE; 3-(AMINOMETHYL)-4-HYDROXYBENZALDEHYDE; 3-(AMINOMETHYL)-5-CYCLOPROPOXYISONICOTINALDEHYDE; 3-(AMINOMETHYL)-5-CYCLOPROPOXYPICOLINALDEHYDE; 3-(AMINOMETHYL)-5-HYDROXYBENZALDEHYDE; 3-[(1-FORMYLNAPHTHALEN-2-YL)OXY]-2-METHYLPROPANAMIDE; 3-[(1-FORMYLNAPHTHALEN-2-YL)OXY]PROPANAMIDE; 3-[(2-FORMYLPIPERIDIN-1-YL)METHYL]BENZAMIDE; 3-[(3-AMINOPIPERIDIN-1-YL)METHYL]-4-

METHOXYBENZALDEHYDE; 3-[(3-AMINOPYRROLIDIN-1-YL)METHYL]-4-METHOXYBENZALDEHYDE; 3-[(3-FORMYLPIPERIDIN-1-YL)METHYL]BENZAMIDE; 3-[(4-AMINOPIPERIDIN-1-YL)METHYL]-4-METHOXYBENZALDEHYDE; 3-[(4-FORMYLPIPERIDIN-1-YL)METHYL]BENZAMIDE; 3-[(6-FORMYL-2H-1,3-BENZODIOXOL-5-YL)OXY]PROPANAMIDE; 3-[3-(AMINOMETHYL)PYRROLIDIN-1-YL]PROPANAL; 3-ALLYL-4-AMINO-2-THIOXO-2,3-DIHYDRO-1,3-THIAZOLE-5-CARBALDEHYDE; 3-AMINO-1H-PYRROLO[2,3-B]PYRIDINE-4-CARBALDEHYDE; 3-AMINO-1-METHYL-1H-PYRAZOLE-4-CARBALDEHYDE; 3-AMINO-2-(TRIFLUOROMETHOXY)BENZALDEHYDE; 3-AMINO-2-(TRIFLUOROMETHYL)ISONICOTINALDEHYDE; 3-AMINO-2,6-DIMETHYLBENZALDEHYDE; 3-AMINO-2-BROMOBENZALDEHYDE; 3-AMINO-2-BROMOPYRIDINE-4-CARBOXALDEHYDE; 3-AMINO-2-BUTENAL; 3-AMINO-2-CHLOROBENZALDEHYDE; 3-AMINO-2-CHLOROPYRIDINE-4-CARBOXALDEHYDE; 3-AMINO-2-CYCLOPROPOXYBENZALDEHYDE; 3-AMINO-2-ETHYLACROLEIN; 3-AMINO-2-HYDROXYBENZALDEHYDE; 3-AMINO-2-IODOBENZALDEHYDE; 3-AMINO-2-IODOPYRIDINE-4-CARBOXALDEHYDE; 3-AMINO-2-ISOPROPYLACROLEIN; 3-AMINO-2-METHOXYBENZALDEHYDE; 3-AMINO-2-METHYLACRYLALDEHYDE; 3-AMINO-2-METHYLBENZALDEHYDE; 3-AMINO-2-METHYLISONICOTINALDEHYDE; 3-AMINO-2-NITROBENZALDEHYDE; 3-AMINO-2-QUINOLINECARBOXALDEHYDE; 3-AMINO-2-QUINOXALINECARBOXALDEHYDE; 3-AMINO-3-DEOXY-D-MANNOSE, HYDROCHLORIDE; 3-AMINO-4-(4-OXOQUINAZOLIN-3(4H)-YL)BENZALDEHYDE; 3-AMINO-4-(TRIFLUOROMETHOXY)BENZALDEHYDE; 3-AMINO-4-BROMOBENZALDEHYDE; 3-AMINO-4-BROMO-BENZALDEHYDE HYDROCHLORIDE; 3-AMINO-4-CHLOROBENZALDEHYDE; 3'-AMINO-4'-CHLORO-BIPHENYL-4-CARBALDEHYDE; 3-AMINO-4-CYCLOPROPOXYBENZALDEHYDE; 3-AMINO-4-CYCLOPROPOXYPICOLINALDEHYDE; 3-AMINO-4-FLUOROBENZALDEHYDE; 3-AMINO-4-HYDROXYBENZALDEHYDE; 3-AMINO-4-IODOBENZALDEHYDE; 3-AMINO-4-METHOXYBENZALDEHYDE; 3-AMINO-4-METHYL-BENZALDEHYDE; 3-AMINO-4-NITROBENZALDEHYDE; 3-AMINO-4-PYRIDINECARBOXYALDEHYDE HYDROCHLORIDE; 3-AMINO-5-(2-FORMYLPHENYL)BENZOIC ACID; 3-AMINO-5-(3-FORMYLPHENYL)BENZOIC ACID; 3-AMINO-5-(4-FORMYLPHENYL)BENZOIC ACID; 3-AMINO-5-(TRIFLUOROMETHOXY)BENZALDEHYDE; 3-AMINO-5-(TRIFLUOROMETHYL)ISONICOTINALDEHYDE; 3-AMINO-5-(TRIFLUOROMETHYL)PICOLINALDEHYDE; 3-AMINO-5,6,7,8-TETRAHYDROTHIENO[2,3-B]QUINOLINE-2-CARBALDEHYDE; 3-AMINO-5-BROMOBENZALDEHYDE; 3-AMINO-5-BROMOBENZOTHIOPHENE-2-CARBOXALDEHYDE; 3-AMINO-5-BROMOPYRAZINE-2-CARBALDEHYDE; 3-AMINO-5-CHLOROBENZALDEHYDE; 3-AMINO-5-CHLOROBENZOTHIOPHENE-2-CARBOXALDEHYDE; 3-AMINO-5-CHLOROPYRAZINE-2-CARBALDEHYDE; 3-AMINO-5-CYCLOPROPOXYBENZALDEHYDE; 3-AMINO-5-CYCLOPROPOXYISONICOTINALDEHYDE; 3-AMINO-5-CYCLOPROPOXYPICOLINALDEHYDE; 3-AMINO-5-FLUOROBENZOTHIOPHENE-2-CARBOXALDEHYDE; 3-AMINO-5-HYDROXYBENZALDEHYDE; 3-AMINO-5-IODOBENZALDEHYDE; 3-AMINO-5-METHOXYBENZALDEHYDE; 3-AMINO-5-METHYL-2-FURANCARBOXALDEHYDE; 3-AMINO-5-METHYLBENZALDEHYDE; 3-AMINO-5-NITROBENZALDEHYDE; 3-AMINO-6,7,8,9-TETRAHYDROBENZALDEHYDE; 3-AMINO-6-BROMOPYRAZINE-2-CARBALDEHYDE; 3-AMINO-6-CHLOROPYRAZINE-2-CARBALDEHYDE; 3-AMINO-6-FORMYL-2-PYRAZINECARBONITRILE; 3-AMINO-6-TRIFLUOROMETHYL-PYRIDINE-2-CARBALDEHYDE; 3-AMINOBENZALDEHYDE; 3-AMINOBENZALDEHYDE HYDROCHLORIDE; 3'-AMINO-BIPHENYL-4-CARBALDEHYDE; 3-AMINOFURAN-2-CARBALDEHYDE; 3-AMINO-IMIDAZO[1,2-A]PYRIDINE-2-CARBOXALDEHYDE; 3-AMINOISONICOTINALDEHYDE; 3-AMINOPYRAZINE-2-CARBALDEHYDE; 3-AMINO-PYRIDINE-2-CARBALDEHYDE; 3-AMINO-PYRIDINE-4-CARBALDEHYDE DIHYDROCHLORIDE; 3-AMINOTHIOPHENE-2-CARBALDEHYDE; 3-AMINOTHIOPHENE-4-CARBOXALDEHYDE; 3-AMINOTHIOPHENE-5-CARBOXALDEHYDE; 3-BROMO-2-FORMYLANILINE; 3-CYCLOHEXYL-4-METHOXY-1-OXO-2-PROPANAMINIUM CHLORIDE; 3-CYCLOPROPOXY-2-FORMYLBENZAMIDE; 3-CYCLOPROPOXY-2-FORMYLISONICOTINAMIDE; 3-CYCLOPROPOXY-4-FORMYLBENZAMIDE; 3-CYCLOPROPOXY-4-FORMYLPICOLINAMIDE; 3-CYCLOPROPOXY-5-FORMYLBENZAMIDE; 3-CYCLOPROPOXY-5-FORMYLISONICOTINAMIDE; 3-CYCLOPROPOXY-5-FORMYLPICOLINAMIDE; 3-CYCLOPROPOXY-6-FORMYLPICOLINAMIDE; 3-FLUORO-4-(4-FORMYLPHENOXY)BENZAMIDE; 3-FLUORO-4-[(2-FORMYLPIPERIDIN-1-YL)METHYL]BENZAMIDE; 3-FLUORO-4-[(3-FORMYLPIPERIDIN-1-YL)METHYL]BENZAMIDE; 3-FLUORO-4-[(4-FORMYLPIPERIDIN-1-YL)METHYL]BENZAMIDE; 3-FORMYL BENZAMIDINE HYDROCHLORIDE; 3-FORMYL-2-HYDROXYBENZAMIDE; 3-FORMYL-4-HYDROXYBENZAMIDE; 3-FORMYL-5-HYDROXYBENZAMIDE; 3-FORMYLBENZAMIDE; 3-FORMYLBENZYLAMINE; 3-FORMYLBENZYLAMINE HYDROCHLORIDE; 3-METHOXY-4-(2-OXOETHOXY)BENZAMIDE; 3-METHOXY-4-(3-OXOPROPOXY)BENZAMIDE; 3-NITRO-4-(2-OXOETHOXY)BENZAMIDE; 3-NITRO-4-(3-OXOPROPOXY)BENZAMIDE; 4-((6-AMINOPYRIDIN-2-YL)OXY)BUTANAL; 4-([4-((1R)-1-AMINO-2-CYCLOPROPYLETHYL)PHENYL]METHYL)BENZALDEHYDE; 4-([4-((1R)-1-AMINO-2-METHYLPROPYL)PHENYL]METHYL)BENZALDEHYDE; 4-([4-((1R)-1-AMINOBUTYL)PHENYL]METHYL)BENZALDEHYDE; 4-([4-((1R)-1-AMINOETHYL)PHENYL]METHYL)BENZALDEHYDE; 4-([4-((1R)-1-AMINOPENTYL)PHENYL]METHYL)BENZALDEHYDE; 4-([4-((1R)-1-AMINOPROPYL)PHENYL]METHYL)BENZALDEHYDE; 4-([4-((1S)-1-AMINO-2-CYCLOPROPYLETHYL)PHENYL]METHYL)BENZALDEHYDE; 4-([4-((1S)-1-AMINO-2-METHYLPROPYL)PHENYL]METHYL)BENZALDEHYDE; 4-([4-((1S)-1-AMINOBUTYL)PHENYL]METHYL)BENZALDEHYDE; 4-([4-((1S)-1-AMINOETHYL)PHENYL]METHYL)BENZALDEHYDE; 4-([4-((1S)-1-AMINOPENTYL)PHENYL]METHYL)BENZALDEHYDE; 4-(2-AMINO-

1H-IMIDAZOL-4-YL)-BUTYRALDEHYDE HCL; 4-(2-AMINOETHYL)BENZALDEHYDE, [ETHYL-2-14C]-; 4-(2-AMINO-IMIDAZOL-1-YL)-BUTYRALDEHYDE HCL; 4-(2-FLUORO-4-FORMYLPHENOXY)BENZAMIDE; 4-(2-FORMYLPHENOXY)BENZAMIDE; 4-(2-FORMYLPIPERIDIN-1-YL)PYRIDINE-2-CARBOXAMIDE; 4-(2-METHOXYETHYLAMINO)-2-(METHYLTHIO)PYRIMIDINE-5-CARBALDEHYDE; 4-(2-OXOETHOXY)BENZAMIDE; 4-(3-AMINOPHENYL)-2-FORMYLPHENOL; 4-(3-CARBAMOYL-4-CHLOROPHENYL)-2-FORMYLPHENOL; 4-(3-CHLORO-2-FORMYLPHENOXY)BENZAMIDE; 4-(3-FORMYL-2,5-DIMETHYL-1H-PYRROL-1-YL)BENZAMIDE; 4-(3-FORMYL-2,5-DIMETHYL-1H-PYRROL-1-YL)BUTANAMIDE; 4-(3-FORMYL-2-HYDROXYPHENYL)BENZAMIDE; 4-(3-FORMYL-4-HYDROXYPHENYL)BENZAMIDE; 4-(3-FORMYLPIPERIDIN-1-YL)PYRIDINE-2-CARBOXAMIDE; 4-(3-OXOPROPOXY)BENZAMIDE; 4-(4-AMINO-BENZOOXAZOL-2-YL)-BENZALDEHYDE; 4-(4-FLUORO-2-FORMYLPHENOXY)BENZAMIDE; 4-(4-FORMYL-2-METHYLPHENOXY)BENZAMIDE; 4-(4-FORMYL-3-METHYLPHENOXY)BENZAMIDE; 4-(4-FORMYLPHENOXY)BENZAMIDE; 4-(4-FORMYLPIPERIDIN-1-YL)PYRIDINE-2-CARBOXAMIDE; 4-(4-FORMYL-PYRIDIN-2-YL)-BENZAMIDE; 4-(4-FORMYLPYRIDIN-3-YL)BENZAMIDE; 4-(5-AMINO-BENZOOXAZOL-2-YL)-BENZALDEHYDE; 4-(5-FORMYL-2-HYDROXYPHENYL)BENZAMIDE; 4-(5-FORMYLFURAN-2-YL)BENZAMIDE; 4-(5-FORMYL-PYRIDIN-3-YL)-BENZAMIDE; 4-(5-FORMYLTHIOPHEN-2-YL)BENZAMIDE; 4-(6-AMINO-BENZOOXAZOL-2-YL)-BENZALDEHYDE; 4-(AMINOMETHYL)-2-CYCLOPROPOXYBENZALDEHYDE; 4-(AMINOMETHYL)-2-HYDROXYBENZALDEHYDE; 4-(AMINOMETHYL)-3-CYCLOPROPOXYBENZALDEHYDE; 4-(AMINOMETHYL)-3-CYCLOPROPOXYPICOLINALDEHYDE; 4-(AMINOMETHYL)-3-HYDROXYBENZALDEHYDE; 4-(AMINOMETHYL)-5-CYCLOPROPOXYNICOTINALDEHYDE; 4-(AMINOMETHYL)-5-CYCLOPROPOXYPICOLINALDEHYDE; 4,5-DIAMINO-2,3-DIFLUOROBENZALDEHYDE; 4,5-DIAMINO-2-BROMOBENZALDEHYDE; 4,5-DIAMINO-2-CHLOROBENZALDEHYDE; 4,5-DIAMINO-2-FLUOROBENZALDEHYDE; 4,6-DIAMINONICOTINALDEHYDE; 4,6-DIAMINOPYRIMIDINE-5-CARBALDEHYDE; 4-[(2-FORMYLPIPERIDIN-1-YL)METHYL]BENZAMIDE; 4-[(3-FORMYLPIPERIDIN-1-YL)METHYL]BENZAMIDE; 4-[(4-FORMYL-1,3-DIMETHYL-1H-PYRAZOL-5-YL)OXY]BENZAMIDE; 4-[(4-FORMYLPIPERIDIN-1-YL)METHYL]BENZAMIDE; 4'-AMINO-[1,1'-BIPHENYL]-3-CARBALDEHYDE; 4-AMINO-1,2-DIHYDRO-2-OXO-5-PYRIMIDINECARBOXALDEHYDE; 4-AMINO-1-BENZYLIMIDAZOLE-5-CARBALDEHYDE; 4-AMINO-1H-PYRROLO[2,3-C]PYRIDINE-3-CARBALDEHYDE; 4-AMINO-1H-PYRROLO[3,2-C]PYRIDINE-2-CARBALDEHYDE; 4-AMINO-1-METHYL-1H-PYRROLE-2-CARBOXALDEHYDE; 4-AMINO-2-(TRIFLUOROMETHOXY)BENZALDEHYDE; 4-AMINO-2-(TRIFLUOROMETHYL)BENZALDEHYDE; 4-AMINO-2,3-DIFLUORO-5-NITROBENZALDEHYDE; 4-AMINO-2,6-DICHLOROPYRIDINE-3-CARBALDEHYDE; 4-AMINO-2,6-DICHLOROPYRIMIDINE-5-CARBOXALDEHYDE; 4-AMINO-2,6-DIFLUOROBENZALDEHYDE; 4-AMINO-2,6-DIHYDROXYPYRIMIDINE-5-CARBALDEHYDE; 4-AMINO-2,6-DIMETHYL-3-PYRIDINECARBOXALDEHYDE; 4-AMINO-2,6-DIMETHYL-5-PYRIMIDINECARBOXALDEHYDE; 4-AMINO-2-BENZYLSULFANYL-PYRIMIDINE-5-CARBALDEHYDE; 4-AMINO-2-BROMO-5-NITROBENZALDEHYDE; 4-AMINO-2-BROMOBENZALDEHYDE; 4-AMINO-2-CHLORO-5-NITROBENZALDEHYDE; 4-AMINO-2-CHLOROBENZALDEHYDE; 4-AMINO-2-CHLORONICOTINALDEHYDE; 4-AMINO-2-CYCLOPROPOXYBENZALDEHYDE; 4-AMINO-2-FLUORO-5-NITROBENZALDEHYDE; 4-AMINO-2-FLUOROBENZALDEHYDE; 4-AMINO-2'-FORMYL[1,1'-BIPHENYL]-3-CARBOXYLIC ACID; 4'-AMINO-2'-HYDROXY-[1,1'-BIPHENYL]-3-CARBALDEHYDE; 4-AMINO-2-HYDROXYBENZALDEHYDE; 4-AMINO-2-IODOBENZALDEHYDE; 4-AMINO-2-MERCAPTOPYRIMIDINE-5-CARBALDEHYDE; 4'-AMINO-2'-METHOXY-[1,1'-BIPHENYL]-3-CARBALDEHYDE; 4-AMINO-2-METHOXY-5-PYRIMIDINECARBOXALDEHYDE; 4-AMINO-2-METHOXYBENZALDEHYDE; 4-AMINO-2-METHOXYNICOTINALDEHYDE; 4-AMINO-2-METHYL-6-(METHYLTHIO)PYRIMIDINE-5-CARBALDEHYDE; 4-AMINO-2-METHYLBENZALDEHYDE; 4-AMINO-2-METHYL-PYRIDINE-3-CARBALDEHYDE; 4-AMINO-2-METHYLPYRIMIDINE-5-CARBALDEHYDE; 4-AMINO-2-METHYLTHIO-PYRIMIDINE-5-CARBALDEHYDE; 4-AMINO-2-NITROBENZALDEHYDE; 4-AMINO-2-PYRROLIDINECARBALDEHYDE; 4-AMINO-3-(TRIFLUOROMETHOXY)BENZALDEHYDE; 4-AMINO-3,5-DIBROMOBENZALDEHYDE; 4-AMINO-3,5-DICHLOROBENZALDEHYDE; 4-AMINO-3,5-DIMETHYLBENZALDEHYDE; 4-AMINO-3-BROMOBENZALDEHYDE; 4-AMINO-3-CHLORO-5-(TRIFLUOROMETHYL)BENZALDEHYDE; 4-AMINO-3-CHLOROBENZALDEHYDE; 4-AMINO-3-CYCLOPROPOXYBENZALDEHYDE; 4-AMINO-3-CYCLOPROPOXYPICOLINALDEHYDE; 4'-AMINO-3'-FLUORO[1,1-BIPHENYL]-2-CARBALDEHYDE; 4'-AMINO-3'-FLUORO[1,1-BIPHENYL]-3-CARBALDEHYDE; 4'-AMINO-3'-FLUORO[1,1-BIPHENYL]-4-CARBALDEHYDE; 4-AMINO-3-FORMYL-BENZOIC ACID METHYL ESTER; 4-AMINO-3-FORMYLPYRIDINE; 4-AMINO-3-HYDROXYBENZALDEHYDE; 4-AMINO-3-IODOBENZALDEHYDE; 4-AMINO-3-METHOXYBENZALDEHYDE; 4-AMINO-3-METHYLBENZALDEHYDE; 4-AMINO-3-NITROBENZALDEHYDE; 4-AMINO-3-PYRIDINECARBOXYALDEHYDE HYDROCHLORIDE; 4-AMINO-4,6-DIDEOXY-D-MANNOSE; 4-AMINO-4'-FORMYL[1,1'-BIPHENYL]-3-CARBOXYLIC ACID; 4-AMINO-5-BROMO-2-CHLOROPYRIDINE-3-CARBALDEHYDE; 4-AMINO-5-CYCLOPROPOXYNICOTINALDEHYDE; 4-AMINO-5-CYCLOPROPOXYPICOLINALDEHYDE; 4-AMINO-5-FORMYL-2-METHOXYPHENYL ACETATE; 4-AMINO-5-IODOPYRIDINE-3-CARBOXALDEHYDE; 4-AMINO-6-(2-OXO-ETHYL)-2-TRIFLUOROMETHYL-QUINOLINE-3-CARBONITRILE; 4-AMINO-6-BROMOPYRIDINE-2-CARBALDEHYDE; 4-AMINO-6-BROMOPYRIDINE-3-CARBALDEHYDE; 4-AMINO-6-CHLORO-2-METHYLSULFANYL-PYRIMIDINE-5-CARBALDEHYDE; 4-AMINO-6-CHLORO-5-PYRIMIDINECARBALDEHYDE; 4-AMINO-6-CHLOROPICOLINALDEHYDE; 4-AMINO-6-CHLOROPYRIDINE-3-CARBALDEHYDE; 4-AMINO-6-FLUORO-3-INDAZOLECARBOXALDEHYDE; 4-AMINO-6-FORMYL-2-TRIFLUOROMETHYL-QUI-

NOLINE-3-CARBONITRILE; 4-AMINOBENZALDEHYDE; 4'-AMINO-BIPHENYL-4-CARBALDEHYDE; 4-AMINOINDOLE-3-CARBOXALDEHYDE; 4-AMINO-N-(4-FORMYL-3-METHYL-PHENYL)-BUTYRAMIDE HYDROCHLORIC ACID; 4-AMINO-PYRIDINE-2-CARBALDEHYDE; 4-AMINO-PYRIDINE-3-CARBALDEHYDE DIHYDROCHLORIDE; 4-AMINO-PYRIDINE-3-CARBALDEHYDE TRIFLUOROACETATE; 4-AMINO-PYRIMIDINE-5-CARBALDEHYDE; 4-AMINOPYRROLO[2,1-F][1,2,4]TRIAZINE-6-CARBALDEHYDE; 4-AMINOPYRROLO[2,1-F][1,2,4]TRIAZINE-7-CARBALDEHYDE; 4-CHLORO-6-AMINO-3-(1H)INDAZOLE CARBOXALDEHYDE; 4-CYCLOPROPOXY-2-FORMYLBENZAMIDE; 4-CYCLOPROPOXY-2-FORMYLNICOTINAMIDE; 4-CYCLOPROPOXY-3-FORMYLBENZAMIDE; 4-CYCLOPROPOXY-3-FORMYLPICOLINAMIDE; 4-CYCLOPROPOXY-5-FORMYLNICOTINAMIDE; 4-CYCLOPROPOXY-5-FORMYLPICOLINAMIDE; 4-CYCLOPROPOXY-6-FORMYLNICOTINAMIDE; 4-CYCLOPROPOXY-6-FORMYLPICOLINAMIDE; 4-FLUORO-3-[(2-FORMYLPIPERIDIN-1-YL)METHYL]BENZAMIDE; 4-FLUORO-3-[(3-FORMYLPIPERIDIN-1-YL)METHYL]BENZAMIDE; 4-FLUORO-3-[(4-FORMYLPIPERIDIN-1-YL)METHYL]BENZAMIDE; 4-FLUORO-3-FORMYLBENZAMIDE; 4-FORMYL BENZAMIDINE HYDROCHLORIDE; 4-FORMYL-1H-PYRAZOLE-1-CARBOTHIOAMIDE; 4-FORMYL-1H-PYRAZOLE-3-CARBOXAMIDE; 4-FORMYL-2H-PYRAZOLE-3-CARBOXYLIC ACID AMIDE; 4-FORMYL-2-HYDROXYBENZAMIDE; 4-FORMYL-3-HYDROXYBENZAMIDE; 4-FORMYLBENZAMIDE; 4-FORMYL-BENZAMIDINE; 4-FORMYLBENZYLAMINE; 4-FORMYLBENZYLAMINE HYDROCHLORIDE; 4-PYRIMIDINECARBOXALDEHYDE, 6-AMINO-2-CYCLOPROPYL-5-FLUORO-; 4-PYRIMIDINECARBOXALDEHYDE, 6-AMINO-5-CHLORO-2-CYCLOPROPYL-; 5-((1R)-1,2-DIAMINOETHYL)-2-AMINOPYRIDINE-3-CARBALDEHYDE; 5-((1R)-1,2-DIAMINOETHYL)PYRIDINE-2-CARBALDEHYDE; 5-((1R)-1,2-DIAMINOETHYL)PYRIDINE-3-CARBALDEHYDE; 5-((1R)-1-AMINO-2,2,2-TRIFLUOROETHYL)-2-AMINOPYRIDINE-3-CARBALDEHYDE; 5-((1R)-1-AMINO-2,2,2-TRIFLUOROETHYL)PYRIDINE-2-CARBALDEHYDE; 5-((1R)-1-AMINO-2,2,2-TRIFLUOROETHYL)PYRIDINE-3-CARBALDEHYDE; 5-((1R)-1-AMINO-2-HYDROXYETHYL)-2-AMINOPYRIDINE-3-CARBALDEHYDE; 5-((1R)-1-AMINO-2-HYDROXYETHYL)PYRIDINE-2-CARBALDEHYDE; 5-((1R)-1-AMINO-2-HYDROXYETHYL)PYRIDINE-3-CARBALDEHYDE; 5-((1R)-1-AMINO-2-HYDROXYISOPROPYL)PYRIDINE-2-CARBALDEHYDE; 5-((1R)-1-AMINO-2-METHYLPROPYL)-2-AMINOPYRIDINE-3-CARBALDEHYDE; 5-((1R)-1-AMINO-2-METHYLPROPYL)PYRIDINE-2-CARBALDEHYDE; 5-((1R)-1-AMINO-2-METHYLPROPYL)PYRIDINE-3-CARBALDEHYDE; 5-((1R)-1-AMINOBUTYL)-2-AMINOPYRIDINE-3-CARBALDEHYDE; 5-((1R)-1-AMINOBUTYL)PYRIDINE-2-CARBALDEHYDE; 5-((1R)-1-AMINOBUTYL)PYRIDINE-3-CARBALDEHYDE; 5-((1R)-1-AMINOETHYL)-2-AMINOPYRIDINE-3-CARBALDEHYDE; 5-((1R)-1-AMINOETHYL)PYRIDINE-2-CARBALDEHYDE; 5-((1R)-1-AMINOETHYL)PYRIDINE-3-CARBALDEHYDE; 5-((1R)-1-AMINOETHYL)THIOPHENE-3-CARBALDEHYDE; 5-((1R)-1-AMINOPENTYL)-2-AMINOPYRIDINE-3-CARBALDEHYDE; 5-((1R)-1-AMINOPENTYL)PYRIDINE-2-CARBALDEHYDE; 5-((1R)-1-AMINOPENTYL)PYRIDINE-3-CARBALDEHYDE; 5-((1R)-1-AMINOPROP-2-ENYL)-2-AMINOPYRIDINE-3-CARBALDEHYDE; 5-((1R)-1-AMINOPROP-2-ENYL)PYRIDINE-2-CARBALDEHYDE; 5-((1R)-1-AMINOPROP-2-ENYL)PYRIDINE-3-CARBALDEHYDE; 5-((1R)-1-AMINOPROPYL)-2-AMINOPYRIDINE-3-CARBALDEHYDE; 5-((1R)-1-AMINOPROPYL)PYRIDINE-2-CARBALDEHYDE; 5-((1R)-1-AMINOPROPYL)PYRIDINE-3-CARBALDEHYDE; 5-((1R)AMINOCYCLOPROPYLMETHYL)PYRIDINE-2-CARBALDEHYDE; 5-((1S)-1,2-DIAMINOETHYL)-2-AMINOPYRIDINE-3-CARBALDEHYDE; 5-((1S)-1,2-DIAMINOETHYL)PYRIDINE-2-CARBALDEHYDE; 5-((1S)-1,2-DIAMINOETHYL)PYRIDINE-3-CARBALDEHYDE; 5-((1S)-1-AMINO-2,2,2-TRIFLUOROETHYL)-2-AMINOPYRIDINE-3-CARBALDEHYDE; 5-((1S)-1-AMINO-2,2,2-TRIFLUOROETHYL)PYRIDINE-2-CARBALDEHYDE; 5-((1S)-1-AMINO-2,2,2-TRIFLUOROETHYL)PYRIDINE-3-CARBALDEHYDE; 5-((1S)-1-AMINO-2-HYDROXYETHYL)-2-AMINOPYRIDINE-3-CARBALDEHYDE; 5-((1S)-1-AMINO-2-HYDROXYETHYL)PYRIDINE-2-CARBALDEHYDE; 5-((1S)-1-AMINO-2-HYDROXYETHYL)PYRIDINE-3-CARBALDEHYDE; 5-((1S)-1-AMINO-2-HYDROXYISOPROPYL)PYRIDINE-2-CARBALDEHYDE; 5-((1S)-1-AMINO-2-METHYLPROPYL)-2-AMINOPYRIDINE-3-CARBALDEHYDE; 5-((1S)-1-AMINO-2-METHYLPROPYL)PYRIDINE-2-CARBALDEHYDE; 5-((1S)-1-AMINO-2-METHYLPROPYL)PYRIDINE-3-CARBALDEHYDE; 5-((1S)-1-AMINOBUTYL)-2-AMINOPYRIDINE-3-CARBALDEHYDE; 5-((1S)-1-AMINOBUTYL)PYRIDINE-2-CARBALDEHYDE; 5-((1S)-1-AMINOBUTYL)PYRIDINE-3-CARBALDEHYDE; 5-((1S)-1-AMINOETHYL)-2-AMINOPYRIDINE-3-CARBALDEHYDE; 5-((1S)-1-AMINOETHYL)PYRIDINE-2-CARBALDEHYDE; 5-((1S)-1-AMINOETHYL)PYRIDINE-3-CARBALDEHYDE; 5-((1S)-1-AMINOETHYL)THIOPHENE-3-CARBALDEHYDE; 5-((1S)-1-AMINOPENTYL)-2-AMINOPYRIDINE-3-CARBALDEHYDE; 5-((1S)-1-AMINOPENTYL)PYRIDINE-2-CARBALDEHYDE; 5-((1S)-1-AMINOPENTYL)PYRIDINE-3-CARBALDEHYDE; 5-((1S)-1-AMINOPROP-2-ENYL)-2-AMINOPYRIDINE-3-CARBALDEHYDE; 5-((1S)-1-AMINOPROP-2-ENYL)PYRIDINE-2-CARBALDEHYDE; 5-((1S)-1-AMINOPROP-2-ENYL)PYRIDINE-3-CARBALDEHYDE; 5-((1S)-1-AMINOPROPYL)-2-AMINOPYRIDINE-3-CARBALDEHYDE; 5-((1S)-1-AMINOPROPYL)PYRIDINE-2-CARBALDEHYDE; 5-((1S)-1-AMINOPROPYL)PYRIDINE-3-CARBALDEHYDE; 5-((1S)AMINOCYCLOPROPYLMETHYL)PYRIDINE-2-CARBALDEHYDE; 5-(2-FORMYLTHIOPHEN-4-YL)-2-AMINOISONICOTINIC ACID; 5-(2-FORMYLTHIOPHEN-4-YL)-2-AMINONICOTINIC ACID; 5-(2-FORMYLTHIOPHEN-4-YL)-3-AMINOBENZOIC ACID; 5-(3-AMINOCARBONYLPHENYL)-2-FORMYLPHENOL; 5-(3-AMINOPHENYL)-2-FORMYLPHENOL; 5-(3-AMINOPHENYL)PENTANAL; 5-(3-CARBAMOYL-4-CHLOROPHENYL)-2-FORMYLPHENOL; 5-(3-FORMYL-PHENYL)-NICOTINAMIDE; 5-(4-AMINOPHENYL)-2-HYDROXYBENZALDEHYDE; 5-(4-AMINOPHENYL)PYRIDINE-3-CARBALDEHYDE; 5-(5-AMINO-4-FORMYL-PYRAZOL-1-YL)-2-METHOXY-BENZONITRILE; 5-(5-FORMYLTHIOPHEN-2-YL)-2-AMINOISONICOTINIC ACID; 5-(5-

FORMYLTHIOPHEN-2-YL)-2-AMINONICOTINIC ACID; 5-(5-FORMYLTHIOPHEN-2-YL)-3-AMINOBENZOIC ACID; 5-(AMINOMETHYL)-2-CYCLOPROPOXYBENZALDEHYDE; 5-(AMINOMETHYL)-2-HYDROXYBENZALDEHYDE; 5-(AMINOMETHYL)-3-CYCLOPROPOXYCYCLOHEXA-1,3-DIENECARBALDEHYDE; 5-(AMINOMETHYL)-3-CYCLOPROPOXYPICOLINALDEHYDE; 5-(AMINOMETHYL)-3-PYRIDINECARBOXALDEHYDE; 5-(AMINOMETHYL)-4-CYCLOPROPOXYNICOTINALDEHYDE; 5-(AMINOMETHYL)-4-CYCLOPROPOXYPICOLINALDEHYDE; 5-AMINO-[1,3,4]THIADIAZOLE-2-CARBALDEHYDE; 5-AMINO-1-BENZYL-1,2,3,6-TETRAHYDROPYRIDINE-4-CARBALDEHYDE; 5-AMINO-1-CYCLOPROPYL-6,7-DIFLUORO-8-METHYL-4-OXO-1,4-DIHYDROQUINOLINE-3-CARBALDEHYDE; 5-AMINO-1H-INDAZOLE-3-CARBOXALDEHYDE; 5-AMINO-1H-PYRAZOLE-3-CARBALDEHYDE; 5-AMINO-1H-PYRROLO[2,3-B]PYRIDINE-3-CARBALDEHYDE; 5-AMINO-1-METHYL-1H-IMIDAZOLE-4-CARBALDEHYDE; 5-AMINO-1-METHYL-1H-PYRAZOLE-4-CARBALDEHYDE; 5-AMINO-2-(4-ETHYLPIPERAZIN-1-YL)BENZALDEHYDE; 5-AMINO-2-(4-METHYLPIPERAZIN-1-YL)BENZALDEHYDE; 5-AMINO-2-(TRIFLUOROMETHOXY)BENZALDEHYDE; 5-AMINO-2,4-DIFLUOROBENZALDEHYDE; 5-AMINO-2-BROMOBENZALDEHYDE; 5-AMINO-2-CHLORO-4-FLUOROBENZALDEHYDE; 5-AMINO-2-CHLOROBENZALDEHYDE; 5-AMINO-2-CHLORO-PYRIDINE-3-CARBALDEHYDE; 5-AMINO-2-CHLORO-PYRIDINE-4-CARBALDEHYDE; 5-AMINO-2-CYCLOPROPOXYBENZALDEHYDE; 5-AMINO-2-FLUOROBENZALDEHYDE; 5-AMINO-2-FLUOROISONICOTINALDEHYDE; 5-AMINO-2-FORMYL-BENZENESULFONIC ACID; 5-AMINO-2-HYDROXYBENZALDEHYDE; 5-AMINO-2-IODOBENZALDEHYDE; 5-AMINO-2-METHOXYBENZALDEHYDE; 5-AMINO-2-METHYL-1H-INDOLE-3-CARBALDEHYDE; 5-AMINO-2-METHYLBENZALDEHYDE; 5-AMINO-2-NITROBENZALDEHYDE; 5-AMINO-2-TRIFLUOROMETHYL-PYRIDINE-3-CARBALDEHYDE; 5-AMINO-2-TRIFLUOROMETHYL-PYRIDINE-4-CARBALDEHYDE; 5-AMINO-3-CYCLOPROPOXYPICOLINALDEHYDE; 5-AMINO-4-BROMO-2-CHLOROBENZALDEHYDE; 5-AMINO-4-BROMO-2-FLUOROBENZALDEHYDE; 5-AMINO-4-BROMO-3-FLUOROBENZALDEHYDE; 5-AMINO-4-CHLORO-PYRIDINE-2-CARBALDEHYDE; 5-AMINO-4-CHLORO-PYRIDINE-3-CARBALDEHYDE; 5-AMINO-4-CYCLOPROPOXYNICOTINALDEHYDE; 5-AMINO-4-CYCLOPROPOXYPICOLINALDEHYDE; 5-AMINO-4-NITROTHIOPHENE-2-CARBALDEHYDE; 5-AMINO-6-CHLORO-PYRIDINE-3-CARBALDEHYDE; 5-AMINOBENZO[B]THIOPHENE-2-CARBALDEHYDE; 5-AMINOINDOLE-3-CARBOXALDEHYDE; 5-AMINOISOPHTHALALDEHYDE; 5-AMINONICOTINALDEHYDE; 5-AMINOPICOLINALDEHYDE; 5-AMINO-PYRAZINE-2-CARBALDEHYDE; 5-AMINO-PYRIMIDINE-2-CARBALDEHYDE; 5-CYCLOPROPOXY-2-FORMYLBENZAMIDE; 5-CYCLOPROPOXY-2-FORMYLISONICOTINAMIDE; 5-CYCLOPROPOXY-2-FORMYLNICOTINAMIDE; 5-CYCLOPROPOXY-3-FORMYLPICOLINAMIDE; 5-CYCLOPROPOXY-4-FORMYLNICOTINAMIDE; 5-CYCLOPROPOXY-4-FORMYLPICOLINAMIDE; 5-CYCLOPROPOXY-6-FORMYLNICOTINAMIDE; 5-CYCLOPROPOXY-6-FORMYLPICOLINAMIDE; 5-FORMYL-1,4-DIMETHYL-1H-PYRROLE-2-CARBOXAMIDE; 5-FORMYL-2-FURANCARBOXAMIDE; 5-FORMYL-2-HYDROXY-BENZAMIDE; 5-FORMYL-2-METHOXY-BENZAMIDE; 5-FORMYL-2-PYRIDINECARBOXAMIDE; 5-FORMYLTHIOPHENE-2-CARBOXAMIDE; 6-((1R)-1,2-DIAMINOETHYL)-5-(PHENYLMETHOXY)PYRIDINE-2-CARBALDEHYDE; 6-((1R)-1,2-DIAMINOETHYL)-5-METHOXYPYRIDINE-2-CARBALDEHYDE; 6-((1R)-1,2-DIAMINOETHYL)PYRIDINE-2-CARBALDEHYDE; 6-((1R)-1,2-DIAMINOETHYL)PYRIDINE-3-CARBALDEHYDE; 6-((1R)-1-AMINO-2,2,2-TRIFLUOROETHYL)-5-METHOXYPYRIDINE-2-CARBALDEHYDE; 6-((1R)-1-AMINO-2,2,2-TRIFLUOROETHYL)PYRIDINE-2-CARBALDEHYDE; 6-((1R)-1-AMINO-2,2,2-TRIFLUOROETHYL)PYRIDINE-3-CARBALDEHYDE; 6-((1R)-1-AMINO-2-HYDROXYETHYL)-5-(PHENYLMETHOXY)PYRIDINE-2-CARBALDEHYDE; 6-((1R)-1-AMINO-2-HYDROXYETHYL)-5-METHOXYPYRIDINE-2-CARBALDEHYDE; 6-((1R)-1-AMINO-2-HYDROXYETHYL)PYRIDINE-2-CARBALDEHYDE; 6-((1R)-1-AMINO-2-HYDROXYETHYL)PYRIDINE-3-CARBALDEHYDE; 6-((1R)-1-AMINO-2-METHYLPROPYL)-5-(PHENYLMETHOXY)PYRIDINE-2-CARBALDEHYDE; 6-((1R)-1-AMINO-2-METHYLPROPYL)-5-METHOXYPYRIDINE-2-CARBALDEHYDE; 6-((1R)-1-AMINO-2-METHYLPROPYL)PYRIDINE-2-CARBALDEHYDE; 6-((1R)-1-AMINO-2-METHYLPROPYL)PYRIDINE-3-CARBALDEHYDE; 6-((1R)-1-AMINOBUTYL)-5-(PHENYLMETHOXY)PYRIDINE-2-CARBALDEHYDE; 6-((1R)-1-AMINOBUTYL)-5-METHOXYPYRIDINE-2-CARBALDEHYDE; 6-((1R)-1-AMINOBUTYL)PYRIDINE-2-CARBALDEHYDE; 6-((1R)-1-AMINOBUTYL)PYRIDINE-3-CARBALDEHYDE; 6-((1R)-1-AMINOETHYL)-5-(PHENYLMETHOXY)PYRIDINE-2-CARBALDEHYDE; 6-((1R)-1-AMINOETHYL)-5-METHOXYPYRIDINE-2-CARBALDEHYDE; 64(1R)-1-AMINOETHYL)PYRIDINE-2-CARBALDEHYDE; 6-((1R)-1-AMINOETHYL)PYRIDINE-3-CARBALDEHYDE; 6-((1R)-1-AMINOPENTYL)-5-(PHENYLMETHOXY)PYRIDINE-2-CARBALDEHYDE; 6-((1R)-1-AMINOPENTYL)-5-METHOXYPYRIDINE-2-CARBALDEHYDE; 6-((1R)-1-AMINOPENTYL)PYRIDINE-2-CARBALDEHYDE; 6-((1R)-1-AMINOPENTYL)PYRIDINE-3-CARBALDEHYDE; 6-((1R)-1-AMINOPROP-2-ENYL)-5-(PHENYLMETHOXY)PYRIDINE-2-CARBALDEHYDE; 6-((1R)-1-AMINOPROP-2-ENYL)-5-METHOXYPYRIDINE-2-CARBALDEHYDE; 6-((1R)-1-AMINOPROP-2-ENYL)PYRIDINE-2-CARBALDEHYDE; 6-((1R)-1-AMINOPROP-2-ENYL)PYRIDINE-3-CARBALDEHYDE; 6-((1R)-1-AMINOPROPYL)-5-(PHENYLMETHOXY)PYRIDINE-2-CARBALDEHYDE; 6-((1R)-1-AMINOPROPYL)-5-METHOXYPYRIDINE-2-CARBALDEHYDE; 6-((1R)-1-AMINOPROPYL)PYRIDINE-2-CARBALDEHYDE; 6-((1R)-1-AMINOPROPYL)PYRIDINE-3-CARBALDEHYDE; 6-((1S)-1,2-DIAMINOETHYL)-5-(PHENYLMETHOXY)PYRIDINE-2-CARBALDEHYDE; 6-((1S)-1,2-DIAMINOETHYL)-5-METHOXYPYRIDINE-2-CARBALDEHYDE; 64(1S)-1,2-DIAMINOETHYL)PYRIDINE-2-CARBALDEHYDE; 6-((1S)-1,2-DIAMINOETHYL)PYRIDINE-3-CARBALDEHYDE; 6-((18)-1-AMINO-2,2,2-TRIFLUORO-

ETHYL)-5-METHOXYPYRIDINE-2-CARBALDEHYDE; 6-((1S)-1-AMINO-2,2,2-TRIFLUOROETHYL)PYRIDINE-2-CARBALDEHYDE; 6-((1S)-1-AMINO-2,2,2-TRIFLUOROETHYL)PYRIDINE-3-CARBALDEHYDE; 6-((1S)-1-AMINO-2-HYDROXYETHYL)-5-(PHENYLMETHOXY)PYRIDINE-2-CARBALDEHYDE; 6-((1S)-1-AMINO-2-HYDROXYETHYL)-5-METHOXYPYRIDINE-2-CARBALDEHYDE; 6-((1S)-1-AMINO-2-HYDROXYETHYL)PYRIDINE-2-CARBALDEHYDE; 6-((1S)-1-AMINO-2-HYDROXYETHYL)PYRIDINE-3-CARBALDEHYDE; 6-((1S)-1-AMINO-2-METHYLPROPYL)-5-(PHENYLMETHOXY)PYRIDINE-2-CARBALDEHYDE; 6-((1S)-1-AMINO-2-METHYLPROPYL)-5-METHOXYPYRIDINE-2-CARBALDEHYDE; 6-((1S)-1-AMINO-2-METHYLPROPYL)PYRIDINE-2-CARBALDEHYDE; 6-((1S)-1-AMINO-2-METHYLPROPYL)PYRIDINE-3-CARBALDEHYDE; 6-((1S)-1-AMINOBUTYL)-5-(PHENYLMETHOXY)PYRIDINE-2-CARBALDEHYDE; 6-((1S)-1-AMINOBUTYL)-5-METHOXYPYRIDINE-2-CARBALDEHYDE; 6-((1S)-1-AMINOBUTYL)PYRIDINE-2-CARBALDEHYDE; 6-((1S)-1-AMINOBUTYL)PYRIDINE-3-CARBALDEHYDE; 6-((1S)-1-AMINOETHYL)-5-(PHENYLMETHOXY)PYRIDINE-2-CARBALDEHYDE; 6-((1S)-1-AMINOETHYL)-5-METHOXYPYRIDINE-2-CARBALDEHYDE; 6-((1S)-1-AMINOETHYL)PYRIDINE-2-CARBALDEHYDE; 6-((1S)-1-AMINOETHYL)PYRIDINE-3-CARBALDEHYDE; 6-((1S)-1-AMINOPENTYL)-5-(PHENYLMETHOXY)PYRIDINE-2-CARBALDEHYDE; 6-((1S)-1-AMINOPENTYL)-5-METHOXYPYRIDINE-2-CARBALDEHYDE; 6-((1S)-1-AMINOPENTYL)PYRIDINE-2-CARBALDEHYDE; 6-((1S)-1-AMINOPENTYL)PYRIDINE-3-CARBALDEHYDE; 6-((1S)-1-AMINOPROP-2-ENYL)-5-(PHENYLMETHOXY)PYRIDINE-2-CARBALDEHYDE; 6-((1S)-1-AMINOPROP-2-ENYL)-5-METHOXYPYRIDINE-2-CARBALDEHYDE; 6-((1S)-1-AMINOPROP-2-ENYL)PYRIDINE-2-CARBALDEHYDE; 6-((1S)-1-AMINOPROP-2-ENYL)PYRIDINE-3-CARBALDEHYDE; 6-((1S)-1-AMINOPROPYL)-5-(PHENYLMETHOXY)PYRIDINE-2-CARBALDEHYDE; 6-((1S)-1-AMINOPROPYL)-5-METHOXYPYRIDINE-2-CARBALDEHYDE; 6-((1S)-1-AMINOPROPYL)PYRIDINE-2-CARBALDEHYDE; 6-((1S)-1-AMINOPROPYL)PYRIDINE-3-CARBALDEHYDE; 6-(3-AMINOPHENYL)-2-FORMYLPHENOL; 6-(3-AMINOPHENYL)HEXANAL; 6-(3-CARBAMOYL-4-CHLOROPHENYL)-2-FORMYLPHENOL; 6-(4-AMINOPHENOXY)PYRIDINE-3-CARBOXALDEHYDE; 6-(AMINOMETHYL)-3-CYCLOPROPOXYPICOLINALDEHYDE; 6-(AMINOMETHYL)-4-CYCLOPROPOXY-1,6-DIHYDROPYRIDINE-2-CARBALDEHYDE; 6-(AMINOMETHYL)-4-CYCLOPROPOXYNICOTINALDEHYDE; 6-(AMINOMETHYL)-5-CYCLOPROPOXYNICOTINALDEHYDE; 6-(AMINOMETHYL)-5-CYCLOPROPOXYPICOLINALDEHYDE; 6-AMINO-(1H)INDAZOLE-3-CARBOXALDEHYDE; 6-AMINO-1-(2-CHLOROPHENYL)-4-OXO-2-THIOXO-1,2,3,4-TETRAHYDRO-5-PYRIMIDINECARBALDEHYDE; 6-AMINO-1-(2-FURYLMETHYL)-2,4-DIOXOTETRAHYDROPYRIMIDINE-5-CARBALDEHYDE; 6-AMINO-1-(2-METHYLPHENYL)-4-OXO-2-THIOXO-1,2,3,4-TETRAHYDRO-5-PYRIMIDINECARBALDEHYDE; 6-AMINO-1-(3-METHOXYPHENYL)-2,4-DIOXO-1,2,3,4-TETRAHYDROPYRIMIDINE-5-CARBALDEHYDE; 6-AMINO-1-(4-CHLOROPHENYL)-2,4-DIOXOTETRAHYDROPYRIMIDINE-5-CARBALDEHYDE; 6-AMINO-1-(4-CHLOROPHENYL)-4-OXO-2-THIOXO-1,2,3,4-TETRAHYDRO-5-PYRIMIDINECARBALDEHYDE; 6-AMINO-1-(4-METHOXYPHENYL)-2,4-DIOXO-1,2,3,4-TETRAHYDROPYRIMIDINE-5-CARBALDEHYDE; 6-AMINO-1-(4-METHOXYPHENYL)-4-OXO-2-THIOXO-1,2,3,4-TETRAHYDRO-5-PYRIMIDINECARBALDEHYDE; 6-AMINO-1-(4-METHYLPHENYL)-4-OXO-2-THIOXO-1,2,3,4-TETRAHYDRO-5-PYRIMIDINECARBALDEHYDE; 6-AMINO-1,3-DIETHYL-5-FORMYLURACIL; 6-AMINO-1,3-DIMETHYL-2,4-DIOXO-1,2,3,4-TETRAHYDROPYRIMIDINE-5-CARBALDEHYDE; 6-AMINO-1-BENZYL-2,4-DIOXOTETRAHYDROPYRIMIDINE-5-CARBALDEHYDE; 6-AMINO-1-BUTYL-5-FORMYL-4-METHYL-2-OXO-1,2-DIHYDRO-PYRIDINE-3-CARBONITRILE; 6-AMINO-1H-PYRROLO[3,2-B]PYRIDINE-3-CARBALDEHYDE; 6-AMINO-1-ISOBUTYL-3-METHYL-2,4-DIOXO-1,2,3,4-TETRAHYDROPYRIMIDINE-5-CARBALDEHYDE; 6-AMINO-1-METHYL-2,4-DIOXO-1,2,3,4-TETRAHYDRO-5-PYRIMIDINECARBALDEHYDE; 6-AMINO-1-SEC-BUTYL-5-FORMYL-4-METHYL-2-OXO-1,2-DIHYDRO-PYRIDINE-3-CARBONITRILE; 6-AMINO-2-(TRIFLUOROMETHYL)NICOTINALDEHYDE; 6-AMINO-2,3,4-TRIFLUOROBENZALDEHYDE; 6-AMINO-2,3-DIFLUOROBENZALDEHYDE; 6-AMINO-2,4-DIOXO-1-(2-PHENYLETHYL)TETRAHYDROPYRIMIDINE-5-CARBALDEHYDE; 6-AMINO-2,4-DIOXO-1-(PYRIDIN-3-YLMETHYL)TETRAHYDROPYRIMIDINE-5-CARBALDEHYDE; 6-AMINO-2,4-DIOXO-1,2,3,4-TETRAHYDRO-PYRIMIDINE-5-CARBALDEHYDE; 6-AMINO-2-BROMO-PYRIDINE-3-CARBALDEHYDE; 6-AMINO-2-METHYLNICOTINALDEHYDE; 6-AMINO-3-(2-(TRIFLUOROMETHOXY)PHENYL)PICOLINALDEHYDE; 6-AMINO-3-(2-(TRIFLUOROMETHYL)PHENYL)PICOLINALDEHYDE; 6-AMINO-3-(2,3-DIFLUOROPHENYL)PICOLINALDEHYDE; 6-AMINO-3-(2-FLUOROPHENYL)PICOLINALDEHYDE; 6-AMINO-3-(2-FORMYLPHENYL)PICOLINIC ACID; 6-AMINO-3-(3-(TRIFLUOROMETHOXY)PHENYL)PICOLINALDEHYDE; 6-AMINO-3-(3-(TRIFLUOROMETHYL)PHENYL)PICOLINALDEHYDE; 6-AMINO-3-(3-FLUOROPHENYL)PICOLINALDEHYDE; 6-AMINO-3-(3-FORMYLPHENYL)PICOLINIC ACID; 6-AMINO-3-(4-(TRIFLUOROMETHOXY)PHENYL)PICOLINALDEHYDE; 6-AMINO-3-(4-(TRIFLUOROMETHYL)PHENYL)PICOLINALDEHYDE; 6-AMINO-3-(4-FLUOROPHENYL)PICOLINALDEHYDE; 6-AMINO-3-(4-FORMYLPHENYL)PICOLINIC ACID; 6-AMINO-3-(PERFLUOROPHENYL)PICOLINALDEHYDE; 6-AMINO-3-(PYRIDIN-3-YL)PICOLINALDEHYDE; 6-AMINO-3-(PYRIDIN-4-YL)PICOLINALDEHYDE; 6-AMINO-3,5-DIBROMOPICOLINALDEHYDE; 6-AMINO-3-BROMO-2,4-DIFLUOROBENZALDEHYDE; 6-AMINO-3-BROMOPICOLINALDEHYDE; 6-AMINO-3-CYCLOPROPOXYCYCLOHEXA-2,4-DIENECARBALDEHYDE; 6-AMINO-3-CYCLOPROPOXYPICOLINALDEHYDE; 6-AMINO-3-PHENYLPICOLINALDEHYDE; 6-AMINO-4-CHLORONICOTINALDEHYDE; 6-AMINO-4-CYCLOPROPOXYNICOTINALDEHYDE; 6-AMINO-4-

CYCLOPROPOXYPICOLINALDEHYDE; 6-AMINO-4-FLUORO-3-(1H)INDAZOLE CARBOXALDEHYDE; 6-AMINO-4-METHYL-3-PYRIDINECARBOXALDEHYD; 6-AMINO-4-OXO-1-PHENYL-2-THIOXO-1,2,3,4-TETRAHYDRO-5-PYRIMIDINECARBALDEHYDE; 6-AMINO-5-(2-(TRIFLUOROMETHYL)PHENYL)NICOTINALDEHYDE; 6-AMINO-5-(2-FLUOROPHENYL)NICOTINALDEHYDE; 6-AMINO-5-(3-(TRIFLUOROMETHYL)PHENYL)NICOTINALDEHYDE; 6-AMINO-5-(3-FLUOROPHENYL)NICOTINALDEHYDE; 6-AMINO-5-(4-(TRIFLUOROMETHYL)PHENYL)NICOTINALDEHYDE; 6-AMINO-5-(4-FLUOROPHENYL)NICOTINALDEHYDE; 6-AMINO-5-(PYRIDIN-3-YL)NICOTINALDEHYDE; 6-AMINO-5-(PYRIDIN-4-YL)NICOTINALDEHYDE; 6-AMINO-5-BROMONICOTINALDEHYDE; 6-AMINO-5-CYCLOPROPOXYNICOTINALDEHYDE; 6-AMINO-5-CYCLOPROPOXYPICOLINALDEHYDE; 6-AMINO-5-FORMYL-1-(2-METHOXY-ETHYL)-4-METHYL-2-OXO-1,2-DIHYDRO-PYRIDINE-3-CARBONITRILE; 6-AMINO-5-FORMYL-1-(3-METHOXY-PROPYL)-4-METHYL-2-OXO-1,2-DIHYDRO-PYRIDINE-3-CARBONITRILE; 6-AMINO-5-FORMYL-1,4-DIMETHYL-2-OXO-1,2-DIHYDROPYRIDINE-3-CARBONITRILE; 6-AMINO-5-FORMYL-1-ISOBUTYL-4-METHYL-2-OXO-1,2-DIHYDRO-PYRIDINE-3-CARBONITRILE; 6-AMINO-5-FORMYL-1-ISOPROPYL-4-METHYL-2-OXO-1,2-DIHYDRO-PYRIDINE-3-CARBONITRILE; 6-AMINO-5-FORMYL-4-METHYL-1-(3-METHYL-BUTYL)-2-OXO-1,2-DIHYDRO-PYRIDINE-3-CARBONITRILE; 6-AMINO-5-FORMYL-4-METHYL-2-OXO-1-(TETRAHYDRO-FURAN-2-YLMETHYL)-1,2-DIHYDRO-PYRIDINE-3-CARBONITRILE; 6-AMINO-5-FORMYL-4-METHYL-2-OXO-1-PROPYL-1,2-DIHYDRO-PYRIDINE-3-CARBONITRILE; 6-AMINO-5-NITRONICOTINALDEHYDE; 6-AMINO-5-NITROPICOLINALDEHYDE; 6-AMINO-5-PHENYLNICOTINALDEHYDE; 6-AMINO-BENZO[1,3]DIOXOLE-5-CARBALDEHYDE; 6-AMINOINDOLE-3-CARBOXALDEHYDE; 6-AMINONICOTINALDEHYDE; 6-AMINOPYRIMIDINE-4-CARBOXALDEHYDE; 6-FORMYLPYRAZOLO[1,5-A]PYRIMIDINE-3-CARBOXAMIDE; 6-METHYL-1-(2-OXOETHYL)PIPERIDINE-3-CARBOXAMIDE; 6-METHYL-1-(3-OXOPROPYL)PIPERIDINE-3-CARBOXAMIDE; 7-AMINO[1,2,4]TRIAZOLO[1,5-A]PYRIMIDINE-6-CARBALDEHYDE; 7-AMINO[1,8]NAPHTHYRIDINE-2-CARBALDEHYDE; 7-AMINO-1H-PYRROLO[3,2-B]PYRIDINE-3-CARBALDEHYDE; 7-AMINO-2-CYCLOPROPYL-5-METHYL-PYRAZOLO[1,5-A]PYRIMIDINE-6-CARBALDEHYDE; 7-AMINO-2-CYCLOPROPYL-PYRAZOLO[1,5-A]PYRIMIDINE-6-CARBALDEHYDE; 7-AMINO-8-METHYLQUINOLINE-3-CARBALDEHYDE; 7-AMINOBENZO[C][1,2,5]THIADIAZOLE-4-CARBALDEHYDE; 7-AMINOINDOLE-3-CARBOXALDEHYDE; 8-AMINOQUINOLINE-7-CARBALDEHYDE; 9-(3-OXOPROP-1-ENYL)ADENINE; ACETALDEHYDE, AMINOBENZOYL-; ADENOSINE, PERIODATE OXIDIZED; ALAHOPCIN; ALPHA-AMINO-BENZENEACETALDEHYDE; BENZALDEHYDE, 3-AMINO-4-HYDROXY-5-METHOXY-; BENZOOXAZOLE-2-CARBALDEHYDE-4-YLAMINE; BENZOOXAZOLE-2-CARBALDEHYDE-5-YLAMINE; BENZOOXAZOLE-2-CARBALDEHYDE-6-YLAMINE; BENZYL (2R)-5-AMINO-4-METHYL-1-OXOPENTAN-2-YLCARBAMATE; CYTOSINE PROPENAL; DAUNOSAMINE; D-GALACTOSAMINE; D-GALACTOSAMINE HYDROCHLORIDE; D-GLUCOSAMINE 6-SULFATE; D-GLUCOSAMINE HYDROCHLORIDE; D-GLUCOSAMINE HYDROCHLORIDE, [1-14C]-; D-GLUCOSAMINE HYDROCHLORIDE, [6-3H]-; D-GLUCOSAMINE SULFATE; DL-CYSTINE-3,3,3',3'-D4; D-LYXOSYLAMINE; D-MANNOSAMINE HYDROCHLORIDE; D-MANNOSAMINE HYDROCHLORIDE, [1-14C]-; EPSILON-PYRROLE-LYSINE; ETHYL 2-AMINO-5-(3-OXOPROP-1-ENYL)-3-FUROATE; ETHYL 2-AMINO-6-FORMYLPYRIMIDINE-4-CARBOXYLATE; FORPHENICINE; GALACTOSAMINE HYDROCHLOR-IDE-D-[1-14C]; GLUCOSAMINE; GLUCOSAMINE HYDROCHLORIDE D-[1-14C]; GLUCOSAMINE HYDROCHLORIDE, D-[14C(U)]; GLUCOSAMINE HYDROCHLORIDE, D-[6-3H]; GLUCURONAMIDE; GUANOSINE PERIODATE OXIDIZED; H-LEU-NHOH ACOH; L-2-AMINOADIPATE 6-SEMIALDEHYDE; L-GLUCOSAMINE; MANNOSAMINE HYDROCHLORIDE D [6-3H]; METHYL (2R)-2-AMINO-2-(3-FORMYL-2-HYDROXY-5-METHYLPHENYL)PROPANOATE; METHYL (2R)-2-AMINO-3-(2-CHLORO-3-FORMYL(4-PYRIDYL))PROPANOATE; METHYL (2R)-2-AMINO-3-(2-FORMYLPHENYL)PROPANOATE; METHYL (2R)-2-AMINO-3-(3-FORMYL(2-PYRIDYL))PROPANOATE; METHYL (2R)-2-AMINO-3-(3-FORMYL-2-HYDROXY-5-METHYLPHENYL)PROPANOATE; METHYL (2R)-2-AMINO-3-(3-FORMYL-2-METHYL(4-HYDROIMIDAZO[1,2-A]PYRIDIN-6-YL))PROPANOATE; METHYL (2R)-2-AMINO-3-(3-FORMYL-4-HYDROXYPHENYL)PROPANOATE; METHYL (2R)-2-AMINO-3-(3-FORMYLPHENYL)PROPANOATE; METHYL (2R)-2-AMINO-3-(4-[(4-FORMYLPHENYL)METHYL]PHENYL)PROPANOATE; METHYL (2R)-2-AMINO-3-(4-FLUORO-3,5-DIFORMYLPHENYL)PROPANOATE; METHYL (2R)-2-AMINO-3-(4-FLUORO-3-FORMYLPHENYL)PROPANOATE; METHYL (2R)-2-AMINO-3-(4-FORMYL(2-PYRIDYL))PROPANOATE; METHYL (2R)-2-AMINO-3-(4-FORMYL(3-PYRIDYL))PROPANOATE; METHYL (2R)-2-AMINO-3-(4-FORMYLPHENYL)PROPANOATE; METHYL (2R)-2-AMINO-3-(5-BROMO-4-FORMYL(3-PYRIDYL))PROPANOATE; METHYL (2R)-2-AMINO-3-(5-FORMYL(2-PYRIDYL))PROPANOATE; METHYL (2R)-2-AMINO-3-(5-FORMYL(3-PYRIDYL))PROPANOATE; METHYL (2R)-2-AMINO-3-(5-FORMYL-6-METHOXY(3-PYRIDYL))PROPANOATE; METHYL (2R)-2-AMINO-3-(6-FORMYL(2-PYRIDYL))PROPANOATE; METHYL (2R)-2-AMINO-3-(6-FORMYL(3-PYRIDYL))PROPANOATE; METHYL (2S)-2-AMINO-2-(3-FORMYL-2-HYDROXY-5-METHYLPHENYL)PROPANOATE; METHYL (2S)-2-AMINO-3-(2-CHLORO-3-FORMYL(4-PYRIDYL))PROPANOATE; METHYL (2S)-2-AMINO-3-(2-FORMYLPHENYL)PROPANOATE; METHYL (2S)-2-AMINO-3-(3-FORMYL(2-PYRIDYL))PROPANOATE; METHYL (2S)-2-AMINO-3-(3-FORMYL-2-HYDROXY-5-METHYLPHENYL)PROPANOATE; METHYL (2S)-2-AMINO-3-(3-FORMYL-2-METHYL(4-HYDROIMIDAZO[1,2-A]PYRIDIN-6-YL))PROPANOATE; METHYL (2S)-2-AMINO-3-(3-FORMYL-4-HYDROXYPHENYL)PROPANOATE; METHYL (2S)-2-AMINO-3-(3-FORMYLPHENYL)PROPANOATE; METHYL (2S)-2-AMINO-3-(4-[(4-FORMYLPHENYL)METHYL]PHENYL)PROPANOATE; METHYL (2S)-2-AMINO-3-(4-FLUORO-3,5-DIFORMYLPHENYL)PROPANOATE; METHYL (2S)-2-AMINO-3-(4-FLUORO-3-FORM-

YLPHENYL)PROPANOATE; METHYL (2S)-2-AMINO-3-(4-FORMYL(2-PYRIDYL))PROPANOATE; METHYL (2S)-2-AMINO-3-(4-FORMYL(3-PYRIDYL))PROPANOATE; METHYL (2S)-2-AMINO-3-(4-FORMYLPHENYL) PROPANOATE; METHYL (2S)-2-AMINO-3-(5-BROMO-4-FORMYL(3-PYRIDYL))PROPANOATE; METHYL (2S)-2-AMINO-3-(5-FORMYL(2-PYRIDYL))PROPANOATE; METHYL (2S)-2-AMINO-3-(5-FORMYL(3-PYRIDYL))PROPANOATE; METHYL (2S)-2-AMINO-3-(5-FORMYL-6-METHOXY(3-PYRIDYL)) PROPANOATE; METHYL (2S)-2-AMINO-3-(6-FORMYL (2-PYRIDYL))PROPANOATE; METHYL (2S)-2-AMINO-3-(6-FORMYL(3-PYRIDYL))PROPANOATE; METHYL (3R)-3-AMINO-3-(3-FORMYL-2-HYDROXY-5-METHYLPHENYL)BUTANOATE; METHYL (3R)-3-AMINO-3-(3-FORMYL-2-HYDROXY-5-METHYLPHENYL)PROPANOATE; METHYL (3R)-3-AMINO-3-(6-FORMYL(3-PYRIDYL))PROPANOATE; METHYL (3S)-3-AMINO-3-(3-FORMYL-2-HYDROXY-5-METHYLPHENYL) BUTANOATE; METHYL (3S)-3-AMINO-3-(3-FORMYL-2-HYDROXY-5-METHYLPHENYL)PROPANOATE; METHYL (3S)-3-AMINO-3-(6-FORMYL(3-PYRIDYL)) PROPANOATE; METHYL (4R)-4-AMINO-4-(3-FORMYL-2-HYDROXY-5-METHYLPHENYL)BUTANOATE; METHYL (4S)-4-AMINO-4-(3-FORMYL-2-HYDROXY-5-METHYLPHENYL)BUTANOATE; METHYL 3-((1R)-1-AMINO-2-HYDROXYETHYL)-5-FORMYL-4-HYDROXYBENZOATE; METHYL 3-((1R)-1-AMINO-3-HYDROXYPROPYL)-5-FORMYL-4-HYDROXYBENZOATE; METHYL 3-((1R)-1-AMINO-4-HYDROXYBUTYL)-5-FORMYL-4-HYDROXYBENZOATE; METHYL 3-((1R)-1-AMINO-5-HYDROXYPENTYL)-5-FORMYL-4-HYDROXYBENZOATE; METHYL 3-((1R)-1-AMINOETHYL)-5-FORMYL-4-HYDROXYBENZOATE; METHYL 3-((1S)-1-AMINO-2-HYDROXYETHYL)-5-FORMYL-4-HYDROXYBENZOATE; METHYL 3-((1S)-1-AMINO-3-HYDROXYPROPYL)-5-FORMYL-4-HYDROXYBENZOATE; METHYL 3-((1S)-1-AMINO-4-HYDROXYBUTYL)-5-FORMYL-4-HYDROXYBENZOATE; METHYL 3-((1S)-1-AMINO-5-HYDROXYPENTYL)-5-FORMYL-4-HYDROXYBENZOATE; METHYL 3-((1S)-1-AMINOETHYL)-5-FORMYL-4-HYDROXYBENZOATE; METHYL 3-AMINO-5-FORMYLBENZOATE; METHYL 4-AMINO-5-FORMYLPYRIDINE-2-CARBOXYLATE; METHYL 5-((1R)-1-AMINO-2-CYANOETHYL)-3-FORMYL-4-HYDROXYBENZOATE; METHYL 5-((1S)-1-AMINO-2-CYANOETHYL)-3-FORMYL-4-HYDROXYBENZOATE; METHYL 6-AMINO-5-FORMYLPYRIDINE-2-CARBOXYLATE; MURAMIC ACID; MURAMIC ACID HYDRATE; P-AMINOETHYL-BENZALDEHYDE HCL; SODIUM, 2-AMINO-4-FORMYL-BENZENESULFONATE; SODIUM, 2-AMINO-5-FORMYL-BENZENESULFONATE; TERT-BUTYL 3-AMINO-4-(4-FORMYLPYRIDIN-3-YL)BENZOATE; TERT-BUTYL 3-AMINO-4-(5-FORMYLPYRIDIN-3-YL)BENZOATE; TERT-BUTYL 5-(AMINOMETHYL)-3-FORMYL-1H-INDOLE-1-CARBOXYLATE; Secondary amine: ((1,3-DIMETHYL-2,6-DIOXO-2,3,6,7-TETRAHYDRO-1H-PURIN-8-YL)THIO) ACETALDEHYDE; (11-OXO-UNDECYL)-CARBAMIC ACID TERT-BUTYL ESTER; (1-FORMYL-CYCLOPROPYL)-CARBAMIC ACID TERT-BUTYL ESTER; (1-FORMYL-VINYL)-CARBAMIC ACID TERT-BUTYL ESTER; (1H-IMIDAZOL-2-YL)-ACETALDEHYDE; (1H-IMIDAZOL-4-YL)-ACETALDEHYDE; (2,4-DIOXO-3,4-DIHYDROPYRIMIDIN-1(2H)-YL)ACETALDEHYDE; (2,6-DIOXO-PIPERIDIN-4-YL)-ACETALDEHYDE; (2-[(6-FORMYL-2H-1,3-BENZODIOXOL-5-YL)OXY] ACETYL)UREA; (2-AMINO-1H-IMIDAZOL-4-YL)-ACETALDEHYDE HCL; (2-CHLORO-4-FORMYL-PHENYL)-CARBAMIC ACID BENZYL ESTER; (2-CHLORO-4-FORMYL-PHENYL)-CARBAMIC ACID TERT-BUTYL ESTER; (2-CHLORO-5-FORMYL-PHENYL)-CARBAMIC ACID BENZYL ESTER; (2-CHLORO-5-FORMYL-PHENYL)-CARBAMIC ACID TERT-BUTYL ESTER; (2-CHLORO-6-FORMYL-PHENYL)-CARBAMIC ACID TERT-BUTYL ESTER; (2E)-2-METHYL-3-(1H-PYRROL-2-YL)-2-PROPENAL; (2E)-3-(1H-INDOL-3-YL)-2-PROPENAL; (2E)-3-(1H-PYRROL-2-YL)-2-PROPENAL; (2E)-3-(1H-PYRROLO[2,3-B] PYRIDIN-3-YL)-2-PROPENAL; (2-FLUORO-4-FORMYL-PHENYL)-CARBAMIC ACID BENZYL ESTER; (2-FLUORO-5-FORMYL-PHENYL)-CARBAMIC ACID BENZYL ESTER; (2-FLUORO-5-FORMYL-PHENYL)-CARBAMIC ACID TERT-BUTYL ESTER; (2-FORMYL-1,4-DIMETHYL-1H-INDOL-5-YL)-CARBAMIC ACID TERT-BUTYL ESTER; (2-FORMYL-1H-PYRROL-3-YL)METHYL ACETATE; (2-FORMYL-3-METHYL-PHENYL)-CARBAMIC ACID BENZYL ESTER; (2-FORMYL-3-METHYL-PHENYL)-CARBAMIC ACID TERT-BUTYL ESTER; (2-FORMYL-4,5-DIMETHOXY-PHENYL)-CARBAMIC ACID TERT-BUTYL ESTER; (2-FORMYL-4-HYDROXY-PHENYL)-CARBAMIC ACID TERT-BUTYL ESTER; (2-FORMYL-4-METHOXY-PHENYL)-CARBAMIC ACID BENZYL ESTER; (2-FORMYL-4-METHOXY-PHENYL)-CARBAMIC ACID TERT-BUTYL ESTER; (2-FORMYL-4-METHYL-PHENYL)-CARBAMIC ACID BENZYL ESTER; (2-FORMYL-4-METHYL-PHENYL)-CARBAMIC ACID TERT-BUTYL ESTER; (2-FORMYL-4-NITRO-PHENYL)-CARBAMIC ACID TERT-BUTYL ESTER; (2-FORMYL-5-METHOXY-PHENYL)-CARBAMIC ACID BENZYL ESTER; (2-FORMYL-5-METHYL-PHENYL)-CARBAMIC ACID BENZYL ESTER; (2-FORMYL-5-METHYL-PHENYL)-CARBAMIC ACID TERT-BUTYL ESTER; (2-FORMYL-6-METHOXY-PHENYL)-CARBAMIC ACID TERT-BUTYL ESTER; (2-FORMYL-6-METHYL-PHENYL)-CARBAMIC ACID BENZYL ESTER; (2-FORMYL-CYCLOHEXYL)-CARBAMIC ACID BENZYL ESTER; (2-FORMYL-PHENYL)-CARBAMIC ACID BENZYL ESTER; (2-FORMYL-PHENYL)-CARBAMIC ACID TERT-BUTYL ESTER; (2-FORMYL-PYRIDIN-3-YL)-CARBAMIC ACID TERT-BUTYL ESTER; (2-FORMYL-PYRIDIN-4-YL)-CARBAMIC ACID TERT-BUTYL ESTER; (2-METHYL-3-OXO-PROPYL)-CARBAMIC ACID BENZYL ESTER; (2-METHYL-3-OXO-PROPYL)-CARBAMIC ACID TERT-BUTYL ESTER; (2-OXO-1-THIOPHEN-3-YL-ETHYL)-CARBAMIC ACID BENZYL ESTER; (2-OXO-1-THIOPHEN-3-YL-ETHYL)-CARBAMIC ACID TERT-BUTYL ESTER; (2-PHENYL-1H-INDOL-3-YL)-ACETALDEHYDE; (2R)-3-HYDROXY-2-([(1R)-2-OXO-1-(6-OXO-1,6-DIHYDRO-9H-PURIN-9-YL)ETHYL]OXY)PROPANAL; (2R,12BS)-2-ETHYL-1,2,6,7,12,12B-HEXAHYDRO-INDOLO[2,3-A] QUINOLIZINE-3-CARBALDEHYDE; (2S)-2-PYRROLIDINECARBOXALDEHYDE; (2Z)-3-(1H-PYRROL-2-YL)-2-PROPENAL; (3-CHLORO-4-FORMYL-PHENYL)-CARBAMIC ACID BENZYL ESTER; (3-CHLORO-4-FORMYL-PHENYL)-CARBAMIC ACID TERT-BUTYL ESTER; (3-CHLORO-5-FORMYL-PHENYL)-CARBAMIC ACID BENZYL ESTER; (3-CHLORO-5-FORMYL-PHENYL)-CARBAMIC ACID TERT-BUTYL ESTER; (3-FLUORO-2-FORMYL-PHENYL)-CARBAMIC ACID TERT-BUTYL ESTER; (3-FLUORO-4-FORMYL-PHENYL)-CARBAMIC ACID BENZYL ESTER; (3-FLUORO-4-FORMYL-PHENYL)-CARBAMIC ACID TERT-BUTYL ESTER; (3-FLUORO-5-FORMYL-PHENYL)-CARBAMIC ACID BENZYL ESTER; (3-FLUORO-5-FORMYL-PHENYL)-CARBAMIC ACID TERT-BUTYL ESTER; (3-FORMYL-1H-INDAZOL-6-YL)-CARBAMIC ACID TERT-BUTYL ESTER; (3-FORMYL-2-METHYL-PHENYL)-CARBAMIC ACID BENZYL ESTER; (3-FORMYL-2-METHYL-PHENYL)-CARBAMIC ACID TERT-BUTYL ESTER; (3-FORMYL-4-METHYL-1H-INDOL-7-YL)-CARBAMIC ACID TERT-BUTYL ESTER; (3-FORMYL-4-METHYL-PHENYL)-CARBAMIC ACID BENZYL ESTER; (3-FORMYL-4-METHYL-PHENYL)-CARBAMIC ACID TERT-BUTYL ESTER; (3-FORMYL-BENZYL)-CARBAMIC ACID BENZYL ESTER; (3-FORMYL-PHENYL)-CARBAMIC ACID BENZYL ESTER; (3-FORMYL-PHENYL)-CARBAMIC ACID TERT-BUTYL ESTER; (3-FORMYL-PYRAZIN-2-YL)-CARBAMIC ACID BENZYL ESTER; (3-FORMYL-PYRAZIN-2-YL)-CARBAMIC ACID TERT-BUTYL ESTER; (3-FORMYL-PYRIDIN-2-YL)-CARBAMIC ACID BENZYL ESTER; (3-FORMYL-PYRIDIN-4-YL)-CARBAMIC ACID BENZYL ESTER; (3-OXO-1-PHENYL-PROPYL)-CARBAMIC ACID BENZYL ESTER; (3-OXO-1-PHENYL-PROPYL)-CARBAMIC ACID TERT-BUTYL ESTER; (3-OXO-3,4-DIHYDRO-2-QUINOXALINYL)(PHENYLHYDRAZONO)ACETALDEHYDE; (3-OXO-PROPYL)-CARBAMIC ACID TERT-BUTYL ESTER; (4,4,8-TRIMETHYL-2-OXO-1,2,3,4-TETRAHYDRO-QUINOLIN-6-YL)-ACETALDEHYDE; (4,5-DIFLUORO-2-FORMYL-PHENYL)-CARBAMIC ACID TERT-BUTYL ESTER; (4-CHLORO-2-FORMYL-PHENYL)-CARBAMIC ACID BENZYL ESTER; (4-CHLORO-3-FORMYL-BENZYL)-CARBAMIC ACID TERT-BUTYL ESTER; (4-CHLORO-6-FORMYL-PYRIDIN-2-YL)-CARBAMIC ACID TERT-BUTYL ESTER; (4-FLUORO-2-FORMYL-PHENYL)-CARBAMIC ACID BENZYL ESTER; (4-FLUORO-3-FORMYL-PHENYL)-CARBAMIC ACID BENZYL ESTER; (4-FLUORO-3-FORMYL-PHENYL)-CARBAMIC ACID TERT-BUTYL ESTER; (4-FORMYL-1H-PYRAZOL-3-YL)-CARBAMIC ACID BENZYL ESTER; (4-FORMYL-1H-PYRAZOL-3-YL)-CARBAMIC ACID TERT-BUTYL ESTER; (4-FORMYL-2-HYDROXY-PHENYL)-CARBAMIC ACID BENZYL ESTER; (4-FORMYL-2-HYDROXY-PHENYL)-CARBAMIC ACID TERT-BUTYL ESTER; (4-FORMYL-2-METHOXY-PHENYL)-CARBAMIC ACID BENZYL ESTER; (4-FORMYL-2-METHOXY-PHENYL)-CARBAMIC ACID TERT-BUTYL ESTER; (4-FORMYL-2-METHYL-PHENYL)-CARBAMIC ACID BENZYL ESTER; (4-FORMYL-2-METHYL-PHENYL)-CARBAMIC ACID TERT-BUTYL ESTER; (4-FORMYL-2-NITRO-PHENYL)-CARBAMIC ACID TERT-BUTYL ESTER; (4-FORMYL-3-NITRO-PHENYL)-CARBAMIC ACID TERT-BUTYL ESTER; (4-FORMYL-BICYCLO[2.2.2]OCT-1-YL)-CARBAMIC ACID BENZYL ESTER; (4-FORMYL-OXAZOL-2-YL)-CARBAMIC ACID TERT-BUTYL ESTER; (4-FORMYL-PHENYL)-CARBAMIC ACID BENZYL ESTER; (4-FORMYL-PHENYL)-CARBAMIC ACID TERT-BUTYL ESTER; (4-FORMYL-PYRIDIN-3-YL)-CARBAMIC ACID BENZYL ESTER; (4-FORMYLTHIAZOL-2-YL)CARBAMIC ACID TERT-BUTYL ESTER; (5-CHLORO-2-FORMYL-PHENYL)-CARBAMIC ACID BENZYL ESTER; (5-CHLORO-2-FORMYL-PHENYL)-CARBAMIC ACID TERT-BUTYL ESTER; (5-FLUORO-2-FORMYL-PHENYL)-CARBAMIC ACID BENZYL ESTER; (5-FLUORO-2-FORMYL-PHENYL)-CARBAMIC ACID TERT-BUTYL ESTER; (5-FORMYL-2,4-DIMETHYL-1H-PYRROL-3-YL)-ACETIC ACID; (5-FORMYL-2H-[1,2,4]TRIAZOL-3-YL)-CARBAMIC ACID BENZYL ESTER; (5-FORMYL-2H-[1,2,4]TRIAZOL-3-YL)-CARBAMIC ACID TERT-BUTYL ESTER; (5-FORMYL-2-HYDROXY-PHENYL)-CARBAMIC ACID TERT-BUTYL ESTER; (5-FORMYL-2-METHOXY-PHENYL)-CARBAMIC ACID BENZYL ESTER; (5-FORMYL-2-METHOXY-PHENYL)-CARBAMIC ACID TERT-BUTYL ESTER; (5-FORMYL-2-METHYL-PYRIDIN-4-YL)-CARBAMIC ACID TERT-BUTYL ESTER; (5-FORMYL-PYRAZIN-2-YL)-CARBAMIC ACID TERT-BUTYL ESTER; (5-FORMYL-PYRIDIN-2-YL)-CARBAMIC ACID BENZYL ESTER; (5-FORMYL-PYRIDIN-3-YL)-CARBAMIC ACID BENZYL ESTER; (5-FORMYL-PYRIDIN-3-YL)-CARBAMIC ACID TERT-BUTYL ESTER; (5-FORMYL-THIAZOL-2-YL)-CARBAMIC ACID BENZYL ESTER; (5-FORMYL-THIAZOL-2-YL)-CARBAMIC ACID TERT-BUTYL ESTER; (5-OXO-PENTYL)-CARBAMIC ACID TERT-BUTYL ESTER; (6-CHLORO-4-FORMYL-PYRIDIN-2-YL)-CARBAMIC ACID TERT-BUTYL ESTER; (6-FORMYL-PYRIDIN-2-YL)-CARBAMIC ACID BENZYL ESTER; (6-FORMYL-PYRIDIN-2-YL)-CARBAMIC ACID TERT-BUTYL ESTER; (6-TRIFLUOROMETHYL)-7-AZAINDOLE-3-CARBOXALDEHYDE; (7-OXO-HEPTYL)-CARBAMIC ACID BENZYL ESTER; (7-OXO-HEPTYL)-CARBAMIC ACID TERT-BUTYL ESTER; (9H-FLUOREN-9-YL)METHYL 2-OXOETHYLCARBAMATE; (E)-3-(1H-INDOL-2-YL)-2-PROPENAL; (R)-(+)-2-(BENZYLCARBONYLAMINO)-3-PHENYLPROPANAL; (R)-(1-ETHYL-3-OXO-PROPYL)-CARBAMIC ACID BENZYL ESTER; (R)-(1-ETHYL-3-OXO-PROPYL)-CARBAMIC ACID TERT-BUTYL ESTER; (R)-(3-OXO-1-PHENYL-PROPYL)-CARBAMIC ACID BENZYL ESTER; (R)-(3-OXO-1-PHENYL-PROPYL)-CARBAMIC ACID TERT-BUTYL ESTER; (R)-[1-(4-CHLORO-PHENYL)-3-OXO-PROPYL]-CARBAMIC ACID TERT-BUTYL ESTER; (R)-[1-(4-METHOXY-PHENYL)-3-OXO-PROPYL]-CARBAMIC ACID TERT-BUTYL ESTER; (R)-2-OXO-IMIDAZOLIDINE-4-CARBALDEHYDE; (R)-5,6-DIOXO-PIPERAZINE-2-CARBALDEHYDE; (R)-BENZYL 1-OXOPROPAN-2-YLCARBAMATE; (R)-N-(1-ETHYL-3-OXO-PROPYL)-ACETAMIDE; (R)—N-(3-OXO-1-PHENYL-PROPYL)-ACETAMIDE; (R)-TERT-BUTYL 1-(5-FORMYLOXAZOL-2-YL)-2-METHYLPROPYLCARBAMATE; (R)-TERT-BUTYL 1-(5-FORMYLOXAZOL-2-YL)BUTYLCARBAMATE; (R)-TERT-BUTYL 1-(5-FORMYLOXAZOL-2-YL)ETHYLCARBAMATE; (R)-TERT-BUTYL 1-OXOPROPAN-2-YLCARBAMATE; (R)-TERT-BUTYL 3-METHYL-1-OXOBUTAN-2-YLCARBAMATE; (S)-(1-ETHYL-3-OXO-PROPYL)-CARBAMIC ACID BENZYL ESTER; (S)-(1-ETHYL-3-OXO-PROPYL)-CARBAMIC ACID TERT-BUTYL ESTER; (S)-[1-(4-CHLORO-PHENYL)-3-OXO-PROPYL]-CARBAMIC ACID TERT-BUTYL ESTER; (S)-[1-(4-METHOXY-PHENYL)-3-OXO-PROPYL]-CARBAMIC ACID TERT-BUTYL ESTER; (S)-2-(1-OXO-1,2,3,4-TETRAHYDROISOQUINOLIN-4-YL)ACETALDEHYDE; (S)-2-PIPERIDINECARBOXALDEHYDE HYDROCHLORIDE; (S)-4-(1-BENZYL-2-HYDROXY- ETHYLAMINO)BENZALDEHYDE; (S)-4-(1-HYDROXYMETHYL-PROPYLAMINO)BENZALDEHYDE; (S)-4-(2-HYDROXY-1-PHENYL-ETHYLAMINO)BENZALDEHYDE; (S)-4-N-CBZ-AMINO-4-FORMYL BUTYLAMIDE; (S)-BENZYL 1-OXOPROPAN-2-YLCARBAMATE; (S)—N-(1-ETHYL-3-OXO-PROPYL)-ACETAMIDE; (S)—N-(2-(2-FORMYL-1-PYRROLIDINYL)-2-OXOETHYL)ACETAMIDE; (S)-TERT-BUTYL 1-(5-FORMYLOXAZOL-2-YL)-2-METHYLPROPYLCARBAMATE; (S)-TERT-BUTYL 1-(5-FORMYLOXAZOL-2-YL)BUTYLCARBAMATE; (S)-TERT-BUTYL 1-(5-FORMYLOXAZOL-2-YL)ETHYLCARBAMATE; (S)-TERT-BUTYL 2-OXO-1-PHENYLETHYLCARBAMATE; (S)-TERT-BUTYL 3-OXO-1-PHENYLPROPYLCARBAMATE; (Z)-2-(3,4-DIHYDROPYRROLO[1,2-A]PYRAZIN-1(2H)-YLIDENE)ACETALDEHYDE; (Z)-2-(PYRROLO[1,2-A]PYRAZIN-1(2H)-YLIDENE)PROPANAL; (Z)-2-METHYL-3-(1H-PYRROL-2-YL)-2-PROPENAL; [1-(2-FORMYL-PHENYL)-AZETIDIN-3-YL]-CARBAMIC ACID TERT-BUTYL ESTER; [1-(3-FORMYL-PHENYL)-AZETIDIN-3-YL]-CARBAMIC ACID TERT-BUTYL ESTER; [1-(3-FORMYL-PHENYL)-PYRROLIDIN-3-YL]-CARBAMIC ACID TERT-BUTYL-ESTER; [1-(4-FORMYL-PHENYL)-AZETIDIN-3-YL]-CARBAMIC ACID TERT-BUTYL ESTER; [1-(4-FORMYL-PHENYL)-PYRROLIDIN-3-YL]-CARBAMIC ACID TERT-BUTYL-ESTER; [2-(2,4-DICHLORO-6-FORMYLPHENOXY)ACETYL]UREA; [2-(2-CHLORO-4-FORMYL-6-METHOXYPHENOXY)ACETYL]UREA; [2-(2-CHLORO-4-FORMYLPHENOXY)ACETYL]UREA; [2-(2-ETHOXY-4-FORMYLPHENOXY)ACETYL]UREA; [2-(2-ETHOXY-6-FORMYLPHENOXY)ACETYL]UREA; [2-(2-FORMYL-4-METHOXYPHENOXY)ACETYL]UREA; [2-(2-FORMYL-4-METHOXYPHENOXY)PROPANOYL]UREA; [2-(2-FORMYL-4-NITROPHENOXY)ACETYL]UREA; [2-(2-FORMYL-5-METHOXYPHENOXY)ACETYL]UREA; [2-(2-FORMYL-5-METHOXYPHENOXY)PROPANOYL]UREA; [2-(2-FORMYL-6-METHOXYPHENOXY)ACETYL]UREA; [2-(2-FORMYL-6-METHOXYPHENOXY)PROPANOYL]UREA; [2-(2-FORMYLPHENOXY)ACETYL]UREA; [2-(2-FORMYLPHENOXY)PROPANOYL]UREA; [2-(2-FORMYL-PHENYL)-1H-IMIDAZOL-4-YL]-ACETIC ACID; [2-(2-FORMYLPIPERIDIN-1-YL)ACETYL]UREA; [2-(2-FORMYLPIPERIDIN-1-YL)PROPANOYL]UREA; [2-(2-OXO-ETHYL)-BENZYL]-CARBAMIC ACID BENZYL ESTER; [2-(3-CHLORO-2-FORMYLPHENOXY)ACETYL]UREA; [2-(3-CHLORO-2-FORMYLPHENOXY)PROPANOYL]UREA; [2-(3-FORMYLPHENOXY)ACETYL]UREA; [2-(3-FORMYLPHENOXY)PROPANOYL]UREA; [2-(3-FORMYL-PHENYL)-1H-IMIDAZOL-4-YL]-ACETIC ACID; [2-(3-FORMYLPIPERIDIN-1-YL)ACETYL]UREA; [2-(3-FORMYLPIPERIDIN-1-YL)PROPANOYL]UREA; [2-(4-CHLORO-2-FORMYLPHENOXY)ACETYL]UREA; [2-(4-CHLORO-2-FORMYLPHENOXY)PROPANOYL]UREA; [2-(4-FORMYL-2,6-DIMETHYLPHENOXY)ACETYL]UREA; [2-(4-FORMYL-2,6-DIMETHYLPHENOXY)PROPANOYL]UREA; [2-(4-FORMYL-2-METHOXYPHENOXY)ACETYL]UREA; [2-(4-FORMYL-2-METHOXYPHENOXY)PROPANOYL]UREA; [2-(4-FORMYL-2-NITROPHENOXY)ACETYL]UREA; [2-(4-FORMYLPHENOXY)ACETYL]UREA; [2-(4-FORMYLPHENOXY)PROPANOYL]UREA; [2-(4-FORMYL-PHENYL)-1H-IMIDAZOL-4-YL]-ACETIC ACID; [2-(4-FORMYLPIPERIDIN-1-YL)ACETYL]UREA; [2-(4-FORMYLPIPERIDIN-1-YL)PROPANOYL]UREA; [2-(5-FORMYL-2-METHOXYPHENOXY)ACETYL]UREA; [2-(5-FORMYL-2-METHOXYPHENOXY)PROPANOYL]UREA; [2-(5-FORMYL-2-NITROPHENOXY)ACETYL]UREA; [2-(5-FORMYL-FURAN-2-YL)-PHENYL]-CARBAMIC ACID TERT-BUTYL ESTER; [2,2-DIMETHYL-1-(2-OXO-ETHYL)-PROPYL]-CARBAMIC ACID TERT-BUTYL ESTER; [2,4'-BI-1H-IMIDAZOLE]-4-CARBOXALDEHYDE; [2,4'-BI-1H-IMIDAZOLE]-5-CARBOXALDEHYDE, 1-METHYL; [2-METHYL-1-(2-OXO-ETHYL)-PROPYL]-CARBAMIC ACID TERT-BUTYL ESTER; [3-(2-FORMYLPIPERIDIN-1-YL)PROPANOYL]UREA; [3-(3-FORMYLPIPERIDIN-1-YL)PROPANOYL]UREA; [3-(4-FORMYLPIPERIDIN-1-YL)PROPANOYL]UREA; [3-(5-FORMYL-FURAN-2-YL)-PHENYL]-CARBAMIC ACID TERT-BUTYL ESTER; [4-(2-OXO-ETHYL)-PHENYL]-CARBAMIC ACID BENZYL ESTER; [4-(2-OXO-ETHYL)-THIAZOL-2-YL]-CARBAMIC ACID BENZYL ESTER; [4-(2-OXO-ETHYL)-THIAZOL-2-YL]-CARBAMIC ACID TERT-BUTYL ESTER; [4-(5-FORMYL-FURAN-2-YL)-PHENYL]-CARBAMIC ACID TERT-BUTYL ESTER; [4-(6-FORMYLPYRIDIN-2-YL)PHENYL]CARBAMIC ACID TERT-BUTYL ESTER; 1-((2R,4S,5R)-4-HYDROXY-5-(HYDROXYMETHYL)TETRAHYDROFURAN-2-YL)-2,4-DIOXO-1,2,3,4-TETRAHYDROPYRIMIDINE-5-CARBALDEHYDE; 14(4-OXO-3H,4H-THIENO[3,2-D]PYRIMIDIN-2-YL)METHYL)-1H-IMIDAZOLE-2-CARBALDEHYDE; 1-((4-OXO-3H,4H-THIENO[3,2-D]PYRIMIDIN-2-YL)METHYL)PIPERIDINE-4-CARBALDEHYDE; 1-(1H-IMIDAZOL-2-YL)-2,5-DIMETHYL-1H-PYRROLE-3-CARBALDEHYDE; 1-(1H-IMIDAZOL-2-YL)-PIPERIDINE-3-CARBALDEHYDE; 1-(1H-IMIDAZOL-2-YL)-PIPERIDINE-4-CARBALDEHYDE HCL; 1-(1-OXO-1,2-DIHYDROISOQUINOLIN-3-YL)PIPERIDINE-4-CARBALDEHYDE; 1-(2,6-DIFLUORO-4-FORMYLPHENYL)-N-METHYLPYRROLIDINE-2-CARBOXAMIDE; 1-(2-BENZYLAMINOETHYL)-2-FORMYLIMIDAZOLE HCL; 1-(2-FLUORO-4-FORMYLPHENYL)-N-METHYLPIPERIDINE-4-CARBOXAMIDE; 1-(2-FORMYLPHENYL)-N-METHYLPIPERIDINE-4-CARBOXAMIDE; 1-(2-PIPERAZIN-1-YLETHYL)-2-FORMYLIMIDAZOLE HCL; 1-(3,5-ANHYDRO-2-DEOXY-BETA-D-THREO-PENTAFURANOSYL)THIMINE; 1-(3-CHLORO-2-FORMYLPHENYL)-N-METHYLPIPERIDINE-4-CARBOXAMIDE; 1-(3-FORMYLPHENYL)PIPERAZINE; 1-(4-ANILINOPHENYL)-1H-PYRROLE-2-CARBALDEHYDE; 1-(4-FLUORO-2-FORMYLPHENYL)-N-METHYLPIPERIDINE-4-CARBOXAMIDE; 1-(4-FORMYL-1,3-DIMETHYL-1H-PYRAZOL-5-YL)-N-METHYLPIPERIDINE-2-CARBOXAMIDE; 1-(4-FORMYL-1,3-DIMETHYL-1H-PYRAZOL-5-YL)-N-METHYLPIPERIDINE-4-CARBOXAMIDE; 1-(4-FORMYL-1H-IMIDAZOL-2-YL)-NAPHTHALEN-2-OL; 1-(4-FORMYL-2-METHYLPHENYL)-N-METHYLPIPERIDINE-2-CARBOXAMIDE; 1-(4-FORMYL-2-METHYLPHENYL)-N-METHYLPIPERIDINE-4-CARBOXAMIDE; 1-(4-FORMYL-2-METHYLPHENYL)-N-METHYLPYRROLIDINE-2-CARBOXAMIDE; 1-(4-FORMYL-3-METHYLPHENYL)-N-METHYLPIPERIDINE-2-CARBOXAMIDE; 1-(4-FORMYL-3-METHYLPHENYL)-N-METHYLPIPERIDINE-4-CARBOXAMIDE; 1-(4-

FORMYL-3-METHYLPHENYL)-N-METHYLPYRROLI-DINE-2-CARBOXAMIDE; 1-(4-FORMYLPHENYL)-N-METHYLPIPERIDINE-4-CARBOXAMIDE; 1-(4-PIPERIDINYL)-1H-1,2,3-TRIAZOLE-4-CARBOXALDEHYDE; 1-(5-FORMYLFURAN-2-YL)-N-METHYLPIPERIDINE-2-CARBOXAMIDE; 1-(5-FORMYLFURAN-2-YL)-N-METHYLPIPERIDINE-4-CARBOXAMIDE; 1-(5-FORMYLFURAN-2-YL)-N-METHYLPYRROLIDINE-2-CARBOXAMIDE; 1-(5-FORMYLIMIDAZO[2,1-B][1,3]THIAZOL-6-YL)-N-METHYLPYRROLIDINE-2-CARBOXAMIDE; 1-(7H-PURIN-6-YL)-1H-PYRAZOLE-4-CARBALDEHYDE; 1-(7H-PURIN-6-YL)PIPERIDINE-2-CARBALDEHYDE; 1-(7H-PURIN-6-YL)PIPERIDINE-3-CARBALDEHYDE; 1-(7H-PURIN-6-YL)PIPERIDINE-4-CARBALDEHYDE; 1-(FURAN-2-CARBONYL)-3-(2-OXO-1-PHENYL-ETHYL)-UREA; 1-(N-BOC-2-AMINOETHYL)-2-FORMYLIMIDAZOLE; 1-(N-BOC-3-AMINOPROPYL)-2-FORMYLIMIDAZOLE; 1-(PIPERIDIN-2-YLMETHYL)-2-FORMYLIMIDAZOLE HCL; 1-(PIPERIDIN-3-YLMETHYL)-2-FORMYLIMIDAZOLE HCL; 1-(PIPERIDIN-4-YL)-2-FORMYLIMIDAZOLE HCL; 1-(PIPERIDIN-4-YLMETHYL)-2-FORMYLIMIDAZOLE HCL; 1-(PYRROLIDIN-3-YLMETHYL)-2-FORMYLIMIDAZOLE HCL; 1',2',3',4',5',6'-HEXAHYDRO-[2,4']BI-PYRIDINYL-5-CARBALDEHYDE; 1,2,3,4-TETRA-HYDRO-1-OXOISOQUINOLINE-6-CARBALDEHYDE; 1,2,3,4-TETRAHYDRO-2-OXO-5-QUINOLINECAR-BOXALDEHYDE; 1,2,3,4-TETRAHYDRO-2-OXO-6-QUINOLINECARBOXALDEHYDE; 1,2,3,4-TETRA-HYDRO-8-QUINOLINECARBOXALDEHYDE; 1,2,3,4-TETRAHYDROCYCLOPENTA[B]INDOLE-5-CARBALDEHYDE; 1,2,3,4-TETRAHYDROISOQUINOLINE-6-CARBALDEHYDE HYDROCHLORIDE; 1,2,3,4-TETRAHYDROISOQUI-NOLINE-7-CARBALDEHYDE HYDROCHLORIDE; 1,2-DIHYDRO-2-OXO-4-PYRIDINECARBOXALDEHYDE; 1,2-DIHYDRO-6,7-DIMETHOXY-2-OXO-3-QUINOLIN-ECARBOXALDEHYDE; 1,2-DIHYDRO-6,7-DIM-ETHYL-2-OXO-3-QUINOLINECARBOXALDEHYDE; 1,2-DIHYDRO-6,8-DIMETHYL-2-OXO-3-QUINOLIN-ECARBOXALDEHYDE; 1,2-DIHYDRO-6-METHYL-2-OXO-3-PYRIDINECARBOXALDEHYDE; 1,2-DI-HYDRO-7,8-DIMETHYL-2-OXO-QUINOLINE-3-CARBOXALDEHYDE; 1,2-DIHYDRO-7-METHYL-2-OXO-3-QUINOLINECARBOXALDEHYDE; 1,2-DIHYDRO-8-METHOXY-2-OXO-3-QUINOLINECARBOXALDEHYDE; 1,2-DIHYDROISOQUINOLINE-4-CARBALDEHYDE; 1,3-DIMETHYL-2,4-DIOXO-6-(PROPYLAMINO)-1,2,3,4-TETRAHYDRO-5-PYRIMIDINECARBALDEHYDE; 1,3-DIMETHYL-2,4-DIOXO-6-[(TETRAHYDRO-2-FURANYLMETHYL)AMINO]-1,2,3,4-TETRAHYDRO-5-PYRIMIDINECARBALDEHYDE; 1,3-DIMETHYL-5-(3-OXOPIPERAZIN-1-YL)-1H-PYRAZOLE-4-CARBALDEHYDE; 1,3-DIMETHYL-5-(5-OXO-1,4-DIAZEPAN-1-YL)-1H-PYRAZOLE-4-CARBALDEHYDE; 1,3-DIMETHYL-6-(METHYLAMINO)-2,4-DIOXO-1,2,3,4-TETRAHYDRO-5-PYRIMIDINECARBALDEHYDE; 1,4,5,6-TETRAHYDRO-4-IMINO-6-OXO-S-TRIAZINE-2-CARBOXALDEHYDE; 1,4-DIHYDRO-3-HYDROXY-2-QUINOXALINECARBOXALDEHYDE; 1,4-DIHYDRO-4-OXO-2-PYRIDINECARBOXALDEHYDE; 1,4-DIHYDRO-5-METHYL-4-OXO-3-PYRIDINECARBOXALDEHYDE; 1,4-DIHYDRO-6-METHYL-4-OXO-3-PYRIDINECARBOXALDEHYDE; 1,4-DIMETHYL-3-FORMYLCARBAZOLE; 1,6-DI-HYDRO-4-METHYL-6-OXO-PYRANO[4,3-B]PYR-ROLE-2-CARBOXALDEHYDE; 1-[(2-OXO-1,3-OXA-ZOLIDIN-5-YL)METHYL]PIPERIDINE-2-CARBALDEHYDE; 1-[(2-OXO-1,3-OXAZOLIDIN-5-YL)METHYL]PIPERIDINE-3-CARBALDEHYDE; 1-[(2-OXO-1,3-OXAZOLIDIN-5-YL)METHYL]PIPERIDINE-4-CARBALDEHYDE; 1-[(4-OXO-3,4-DIHYDROQUINAZOLIN-2-YL)METHYL]-1H-IMIDAZOLE-2-CARBALDEHYDE; 1-[2-(1H-INDOL-3-YL)-ETHYL]-2,5-DIMETHYL-1H-PYRROLE-3-CARBALDEHYDE; 1-[2-(1H-INDOL-3-YL)-ETHYL]-2-FORMYLIMIDAZOLE; 1-[2-(2-FORMYLPHENOXY)PROPANOYL]-3-METHYLUREA; 1-[2-(2-FORMYLPIPERIDIN-1-YL)ACETYL]-3-(2-METHOXYETHYL)UREA; 1-[2-(2-FORMYLPIPERIDIN-1-YL)ACETYL]-3-(2-METHYLPROPYL)UREA; 1-[2-(2-FORMYLPIPERIDIN-1-YL)ACETYL]-3-(PROP-2-EN-1-YL)UREA; 1-[2-(2-FORMYLPIPERIDIN-1-YL)ACETYL]-3-(PROPAN-2-YL)UREA; 1-[2-(2-FORMYLPIPERIDIN-1-YL)ACETYL]-3-METHYLUREA; 1-[2-(3-CHLORO-2-FORMYLPHENOXY)PROPANOYL]-3-METHYLUREA; 1-[2-(3-FORMYLPHENOXY)PROPANOYL]-3-METHY-LUREA; 1-[2-(3-FORMYLPIPERIDIN-1-YL)ACETYL]-3-(2-METHOXYETHYL)UREA; 1-[2-(3-FORMYLPIP-ERIDIN-1-YL)ACETYL]-3-(2-METHYLPROPYL)UREA; 1-[2-(3-FORMYLPIPERIDIN-1-YL)ACETYL]-3-METHYLUREA; 1-[2-(3-FORMYLPIPERIDIN-1-YL)ACETYL]-3-PROPYLUREA; 1-[2-(4,4-DIMETHYL-2,5-DIOXOIMIDAZOLIDIN-1-YL)ETHYL]PIPERIDINE-2-CARBALDEHYDE; 1-[2-(4,4-DIMETHYL-2,5-DIOXOIMIDAZOLIDIN-1-YL)ETHYL]PIPERIDINE-3-CARBALDEHYDE; 1-[2-(4,4-DIMETHYL-2,5-DIOXOIMIDAZOLIDIN-1-YL)ETHYL]PIPERIDINE-4-CARBALDEHYDE; 1-[2-(4-CHLORO-2-FORMYLPHENOXY)PROPANOYL]-3-METHYLUREA; 1-[2-(4-FORMYLPHENOXY)PROPANOYL]-3-METHY-LUREA; 1-[2-(4-FORMYLPIPERIDIN-1-YL)ACETYL]-3-(2-METHOXYETHYL)UREA; 1-[2-(4-FORMYLPIP-ERIDIN-1-YL)ACETYL]-3-(2-METHYLPROPYL)UREA; 1-[2-(4-FORMYLPIPERIDIN-1-YL)ACETYL]-3-(PROP-2-EN-1-YL)UREA; 1-[2-(4-FORMYLPIPERIDIN-1-YL)ACETYL]-3-(PROPAN-2-YL)UREA; 1-[2-(4-FORMYLPIPERIDIN-1-YL)ACETYL]-3-METHYLUREA; 1-[2-(4-FORMYLPIPERIDIN-1-YL)ACETYL]-3-PROPYLUREA; 1-[2-(IMIDAZOL-4-YL)ETHYL]-2-FORMYLIMIDAZOLE; 1-[3-(2-FORMYLPIPERIDIN-1-YL)PROPANOYL]-3-METHYLUREA; 1-[3-(4-FORMYLPIPERIDIN-1-YL)PROPANOYL]-3-METHYLUREA; 1-CYCLOOCTYL-6-METHYL-2,4-DIOXO-1,2,3,4-TETRAHYDROPYRIMIDINE-5-CARBALDEHYDE; 1H-BENZIMIDAZOL-2-YL(METHYLSULFONYL)AC-ETALDEHYDE; 1H-BENZIMIDAZOL-2-YLMALONAL-DEHYDE; 1H-BENZIMIDAZOLE-2-CARBOXALDE-HYDE, 5-CHLORO-; 1H-BENZIMIDAZOLE-2-CARBOXALDEHYDE, 5-IODO-; 1H-BENZIMIDAZOLE-2-CARBOXALDEHYDE, 5-METHYL-; 1H-BENZIMIDAZOLE-2-CARBOXALDE-HYDE, 5-NITRO-; 1H-BENZIMIDAZOLE-2-CARBOX-ALDEHYDE, 5-TRIFLUOROMETHOXY-; 1H-BENZ-IMIDAZOLE-2-CARBOXALDEHYDE, 5-TRIFLUOROMETHYL-; 1H-BENZIMIDAZOLE-5-CARBALDEHYDE; 1H-BENZO[D]IMIDAZOLE-4-CARBALDEHYDE; 1H-BENZO[D]IMIDAZOLE-6-

CARBALDEHYDE; 1H-BENZO[G]INDOLE-3-CARBOXALDEHYDE; 1H-BENZOIMIDAZOLE-2-CARBOXALDEHYDE; 1H-IMIDAZOLE-4-CARBALDEHYDE; 1H-IMIDAZOLE-5-ACETALDEHYDE; 1H-IMIDAZOLE-5-CARBALDEHYDE; 1H-IMIDAZOLE-5-CARBOXALDEHYDE, 4-(1-METHYLETHYL)-; 1H-IMIDAZOLE-5-CARBOXALDEHYDE, 4-ETHYL-; 1H-IMIDAZOLE-5-CARBOXALDEHYDE, 4-PROPYL-; 1H-IMIDAZOLE-5-CARBOXYLIC ACID, 4-FORMYL-, METHYL ESTER; 1H-INDAZOLE-3-CARBOXALDEHYDE, 5-[(CYCLOHEXYLMETHYL)AMINO]-; 1H-INDAZOLE-6-CARBOXAMIDE, 3-FORMYL-N-(4-HYDROXYPHENYL)-; 1H-INDOLE-1-ACETAMIDE, 3-FORMYL-N-2-PROPEN-1-YL-; 1H-INDOLE-1-ACETAMIDE, 3-FORMYL-N-PROPYL-; 1H-INDOLE-1-ACETAMIDE, N-(1,1-DIMETHYLETHYL)-3-FORMYL-; 1H-INDOLE-2,3-DICARBALDEHYDE; 1H-INDOLE-2-CARBALDEHYDE; 1H-INDOLE-2-CARBOXALDEHYDE, 4-METHOXY-; 1H-INDOLE-2-CARBOXYLIC ACID, 3-FORMYL-5-METHOXY-6-METHYL-, ETHYL ESTER; 1H-INDOLE-2-CARBOXYLIC ACID, 5-ETHOXY-3-FORMYL-,ETHYL ESTER; 1H-INDOLE-2-CARBOXYLIC ACID, 3-FORMYL-4-METHYL-,METHYL ESTER; 1H-INDOLE-2-CARBOXYLIC ACID, 3-FORMYL-5,6-DIMETHOXY-,ETHYL ESTER; 1H-INDOLE-2-CARBOXYLIC ACID, 3-FORMYL-5-METHYL-,METHYL ESTER; 1H-INDOLE-2-CARBOXYLIC ACID, 3-FORMYL-6-METHOXY-,ETHYL ESTER; 1H-INDOLE-2-CARBOXYLIC ACID, 3-FORMYL-6-METHYL-,ETHYL ESTER; 1H-INDOLE-2-CARBOXYLIC ACID, 3-FORMYL-7-METHYL-,ETHYL ESTER; 1H-INDOLE-2-CARBOXYLIC ACID, 4-BROMO-3-FORMYL-,ETHYL ESTER; 1H-INDOLE-2-CARBOXYLIC ACID, 4-FLUORO-3-FORMYL-,ETHYL ESTER; 1H-INDOLE-2-CARBOXYLIC ACID, 5-ETHOXY-3-FORMYL-,METHYL ESTER; 1H-INDOLE-2-CARBOXYLIC ACID, 5-FORMYL-,METHYL ESTER; 1H-INDOLE-2-CARBOXYLIC ACID, 6-BROMO-3-FORMYL-, ETHYL ESTER; 1H-INDOLE-2-CARBOXYLIC ACID, 6-BROMO-3-FORMYL-,METHYL ESTER; 1H-INDOLE-2-CARBOXYLIC ACID, 6-CHLORO-3-FORMYL-, METHYL ESTER; 1H-INDOLE-2-CARBOXYLIC ACID, 6-CHLORO-4-FLUORO-3-FORMYL-,ETHYL ESTER; 1H-INDOLE-2-CARBOXYLIC ACID, 6-FLUORO-3-FORMYL-,ETHYL ESTER; 1H-INDOLE-2-CARBOXYLIC ACID, 7-BROMO-3-FORMYL-,ETHYL ESTER; 1H-INDOLE-3-CARBOXALDEHYDE,2-CYCLOPENTYL-5-(TRIFLUOROMETHYL)-; 1H-INDOLE-3-PROPANAL; 1H-INDOLE-3-PROPANOIC ACID, 2-FORMYL-4,5,6,7-TETRAHYDRO-; 1H-INDOLE-4-CARBOXYLIC ACID, 3-FORMYL-, ETHYL ESTER; 1H-INDOLE-5-ACETALDEHYDE; 1H-INDOLE-5-CARBOXALDEHYDE, 2-METHYL-; 1H-INDOLE-5-CARBOXALDEHYDE, RADICAL ION(1+); 1H-PURINE-8-CARBOXALDEHYDE, 2,3,6,9-TETRAHYDRO-2,6-DIOXO-; 1H-PYRROLE-2,3,5-TRICARBOXALDEHYDE; 1H-PYRROLE-2,3-DICARBALDEHYDE; 1H-PYRROLE-2,4-DICARBALDEHYDE; 1H-PYRROLE-2,5-DICARBALDEHYDE; 1H-PYRROLE-2-CARBOXALDEHYDE, 4-(CHLOROACETYL)-3,5-DIMETHYL-; 1H-PYRROLE-2-CARBOXALDEHYDE, 4-FLUORO-3,5-DIMETHYL-; 1H-PYRROLE-2-CARBOXALDEHYDE, 5-(METHYLTHIO)-; 1H-PYRROLE-2-CARBOXYLIC ACID, 4-FORMYL-2,3-DIHYDRO-, METHYL ESTER; 1H-PYRROLE-2-PROPANAL; 1H-PYRROLE-3-CARBALDEHYDE; 1H-PYRROLE-3-CARBOXALDEHYDE, 4-PHENYL-; 1H-PYRROLE-3-PROPANAL; 1H-PYRROLO[2,3-B]PYRIDINE-2-CARBALDEHYDE; 1H-PYRROLO[2,3-B]PYRIDINE-2-CARBOXYLIC ACID, 3-FORMYL-, METHYL ESTER; 1H-PYRROLO[2,3-B]PYRIDINE-3,4-DICARBALDEHYDE; 1H-PYRROLO[2,3-B]PYRIDINE-3-CARBALDEHYDE; 1H-PYRROLO[2,3-B]PYRIDINE-3-CARBOXALDEHYDE, 2-METHYL-; 1H-PYRROLO[2,3-B]PYRIDINE-3-CARBOXALDEHYDE, 4-METHYL-; 1H-PYRROLO[2,3-B]PYRIDINE-3-CARBOXALDEHYDE, 5-CHLORO-2-ETHYL-; 1H-PYRROLO[2,3-B]PYRIDINE-3-CARBOXALDEHYDE, 5-CHLORO-2-METHYL-; 1H-PYRROLO[2,3-B]PYRIDINE-3-CARBOXALDEHYDE, 5-METHOXY-; 1H-PYRROLO[2,3-B]PYRIDINE-3-CARBOXALDEHYDE, 6-BROMO-; 1H-PYRROLO[2,3-B]PYRIDINE-3-CARBOXALDEHYDE, 6-CHLORO-4-METHYL-; 1H-PYRROLO[2,3-B]PYRIDINE-5-CARBALDEHYDE; 1H-PYRROLO[2,3-B]PYRIDINE-5-CARBOXALDEHYDE, 4-(4-FLUOROPHENYL)-6-(1-METHYLETHYL)-; 1H-PYRROLO[2,3-B]PYRIDINE-5-CARBOXALDEHYDE, 4-AMINO-6,7-DIHYDRO-2,3-DIMETHYL-6-OXO-; 1H-PYRROLO[2,3-B]PYRIDINE-5-CARBOXALDEHYDE, 4-CHLORO-3-METHYL; 1H-PYRROLO[2,3-B]PYRIDINE-6-CARBALDEHYDE; 1H-PYRROLO[2,3-C]PYRIDINE-2-CARBALDEHYDE; 1H-PYRROLO[2,3-C]PYRIDINE-5-CARBALDEHYDE; 1H-PYRROLO[3,2-B]PYRIDINE-2-CARBALDEHYDE; 1H-PYRROLO[3,2-B]PYRIDINE-3-CARBALDEHYDE; 1H-PYRROLO[3,2-B]PYRIDINE-5-CARBOXALDEHYDE; 1H-PYRROLO[3,2-B]PYRIDINE-6-CARBALDEHYDE; 1H-PYRROLO[3,2-B]PYRIDINE-7-CARBOXALDEHYDE; 1H-PYRROLO[3,2-C]PYRIDINE-2-CARBALDEHYDE; 1H-PYRROLO[3,2-D]PYRIMIDINE-7-CARBOXALDEHYDE; 1-METHYL-2,4-DIOXO-1,2,3,4-TETRAHYDROPYRIDO[2,3-D]PYRIMIDINE-6-CARBALDEHYDE; 1-METHYL-4-OXO-4,5-DIHYDRO-1H-PYRAZOLO[3,4-D]PYRIMIDINE-3-CARBALDEHYDE; 1-METHYL-4-OXO-4,5-DIHYDRO-1H-PYRROLO[3,2-C]PYRIDINE-2-CARBALDEHYDE; 1-OXO-1,2,3,4-TETRAHYDROISOQUINOLINE-5-CARBALDEHYDE; 1-OXO-1,2-DIHYDROISOQUINOLINE-4-CARBALDEHYDE; 1-OXO-1,2-DIHYDROISOQUINOLINE-5-CARBALDEHYDE; 1-OXO-1,2-DIHYDROISOQUINOLINE-6-CARBALDEHYDE; 1-OXO-1,2-DIHYDROISOQUINOLINE-7-CARBALDEHYDE; 1-OXOISOINDOLINE-4-CARBALDEHYDE; 1-OXOISOINDOLINE-5-CARBALDEHYDE; 2-((2-HYDROXYETHYL)AMINO)-9-ME-4-OXO-4H-PYRIDO(1,2-A)PYRIMIDINE-3-CARBALDEHYDE; 2-((2-METHOXYETHYL)AMINO)-4-OXO-4H-PYRIDO[1,2-A]PYRIMIDINE-3-CARBALDEHYDE; 2-((2R)-2-PIPERIDYL)PYRIDINE-4-CARBALDEHYDE; 2-((2R)AZETIDIN-2-YL)PYRIDINE-4-CARBALDEHYDE; 2-((2R)PYRROLIDIN-2-YL)PYRIDINE-4-CARBALDEHYDE; 2-((2S)-2-PIPERIDYL)PYRIDINE-4-CARBALDEHYDE; 2-((2S)AZETIDIN-2-YL)PYRIDINE-4-CARBALDEHYDE; 2-((2S)PYRROLIDIN-2-YL)PYRIDINE-4-CARBALDEHYDE; 2-((3,4-DIHYDRO-1(2H)-ISOQUINOLINYLIDENE)-ACETALDEHYDE); 2-((3-FORMYLIMIDAZO[1,2-A]PYRIDIN-2-YL)(METHYL)AMINO)-N-METHYLACETAMIDE; 2-((3R)MORPHOLIN-3-YL)PYRIDINE-4-CARBALDEHYDE; 2-((3S)MORPHOLIN-3-YL)PYRIDINE-4-CARBALDEHYDE; 2-((5-FORMYLIMIDAZO[2,1-B][1,3]THIAZOL-6-YL)(METHYL)AMINO)-N-(PROPAN-2-YL)ACET-

AMIDE; 2-((5-FORMYLIMIDAZO[2,1-B][1,3]THIAZOL-6-YL)(METHYL)AMINO)-N-METHYLACETAMIDE; 2-((5-FORMYLIMIDAZO[2,1-B][1,3]THIAZOL-6-YL)(PROPYL)AMINO)-N-METHYLACETAMIDE; 2-((FURAN-2-YLMETHYL)AMINO)-4-OXO-4H-PYRIDO[1,2-A]PYRIMIDINE-3-CARBALDEHYDE; 2-((TETRAHYDROFURAN-2-YLMETHYL)AMINO)PYRIMIDINE-5-CARBALDEHYDE; 2-([(5-FORMYL-2-METHOXYPHENYL)METHYL](METHYL)AMINO)-N-METHYLACETAMIDE; 2-(1,2,3,4-TETRAHYDROISOQUINOLIN-6-YL)ACETALDEHYDE HYDROCHLORIDE; 2-(1,2,3,4-TETRAHYDROISOQUINOLIN-7-YL)ACETALDEHYDE HYDROCHLORIDE; 2-(1-ADAMANTYL)-5-FLUORO-1H-INDOLE-3-CARBALDEHYDE; 2-(1-ADAMANTYL)-5-METHYL-1H-INDOLE-3-CARBALDEHYDE; 2-(1-ETHYL-PENTYL)-1H-IMIDAZOLE-4-CARBALDEHYDE; 2-(1H-BENZOIMIDAZOL-2-YLSULFANYL)-3-PHENYL-PROPENAL; 2-(1H-IMIDAZOL-2-YL)-BENZALDEHYDE; 2-(1H-IMIDAZOL-2-YL)-MALONALDEHYDE; 2-(1H-IMIDAZOL-4-YLMETHYL)-BENZALDEHYDE; 2-(1H-INDOL-3-YL)-2-OXOACETALDEHYDE; 2-(1H-INDOL-3-YL)ACETALDEHYDE; 2-(1H-INDOL-3-YL)PROPANAL; 2-(1H-INDOL-4-YLOXY)-ACETALDEHYDE; 2-(1H-INDOL-5-YL)-BENZALDEHYDE; 2-(1H-PYRROL-2-YL)-4-FORMYL-1H-IMIDAZOLE; 2-(1H-PYRROL-2-YL)OXAZOLE-5-CARBALDEHYDE; 2-(1H-PYRROL-2-YL)PROPANAL; 2-(1H-PYRROL-3-YL)-4-FORMYL-1H-IMIDAZOLE; 2-(1H-PYRROL-3-YL)PROPANAL; 2-(1-METHYL-1H-PYRROL-2-YL)-4-FORMYL-1H-IMIDAZOLE; 2-(1-METHYL-BUTYL)-1H-IMIDAZOLE-4-CARBALDEHYDE; 2-(1-PIPERAZINYL)-3-PYRIDINECARBOXALDEHYDE; 2-(2,3-DICHLORO-PHENYL)-IMIDAZOLE-4-CARBALDEHYDE; 2-(2,3-DIFLUORO-4-METHYL-PHENYL)-4-FORMYLIMIDAZOLE; 2-(2,3-DIFLUOROPHENYL)-4,6-DIMETHYL-1H-INDOLE-3-CARBOXALDEHYDE; 2-(2,3-DIFLUOROPHENYL)-4,7-DIMETHYL-1H-INDOLE-3-CARBOXALDEHYDE; 2-(2,3-DIFLUOROPHENYL)-5-(1-METHYLETHYL)-1H-INDOLE-3-CARBOXALDEHYDE; 2-(2,3-DIFLUOROPHENYL)-5,7-DIMETHYL-1H-INDOLE-3-CARBOXALDEHYDE; 2-(2,3-DIFLUOROPHENYL)-5-FLUORO-1H-INDOLE-3-CARBOXALDEHYDE; 2-(2,3-DIFLUOROPHENYL)-5-METHOXY-1H-INDOLE-3-CARBOXALDEHYDE; 2-(2,3-DIFLUOROPHENYL)-5-METHYL-1H-INDOLE-3-CARBOXALDEHYDE; 2-(2,3-DIFLUOROPHENYL)-6,7-DIMETHYL-1H-INDOLE-3-CARBOXALDEHYDE; 2-(2,3-DIFLUOROPHENYL)-7-FLUORO-1H-INDOLE-3-CARBOXALDEHYDE; 2-(2,3-DIFLUOROPHENYL)-7-FLUORO-5-METHYL-1H-INDOLE-3-CARBOXALDEHYDE; 2-(2,3-DIFLUOROPHENYL)-7-METHOXY-1H-INDOLE-3-CARBOXALDEHYDE; 2-(2,3-DIFLUOROPHENYL)-7-METHYL-1H-INDOLE-3-CARBOXALDEHYDE; DIFLUOROPHENYL)IMIDAZOLE-4-CARBALDEHYDE; 2-(2,3-DIHYDRO-1H-INDOL-5-YL)BENZALDEHYDE; 2-(2,3-DIHYDRO-BENZOFURAN-5-YL)-4-FORMYL-IMIDAZOLE; 2-(2,3-DIMETHOXY-PHENYL)-4-FORMYL-IMIDAZOLE; 2-(2,3-DIMETHYLPHENYL)IMIDAZOLE-4-CARBALDEHYDE; 2-(2,3-DIOXO-2,3-DIHYDRO-1H-INDOL-5-YL)BENZALDEHYDE; 2-(2,4,6-TRIMETHYL-PHENYL)-4-FORMYL-1H-IMIDAZOLE; 2-(2,4-DICHLORO-5-FLUORO-PHENYL)-4-FORMYLIMIDAZOLE; 2-(2,4-DICHLORO-6-FORMYLPHENOXY)-N-(PROP-2-EN-1-YL)ACETAMIDE; 2-(2,4-DICHLORO-6-FORMYLPHENOXY)-N-(PROP-2-YN-1-YL)ACETAMIDE; 2-(2,4-DICHLORO-6-FORMYLPHENOXY)-N-(PROPAN-2-YL)ACETAMIDE; DICHLORO-6-FORMYLPHENOXY)-N-ETHYLACETAMIDE; 2-(2,4-DICHLORO-6-FORMYLPHENOXY)-N-ETHYLPROPANAMIDE; 2-(2,4-DICHLORO-6-FORMYLPHENOXY)-N-METHYLACETAMIDE; 2-(2,4-DICHLORO-6-FORMYLPHENOXY)-N-METHYLPROPANAMIDE; 2-(2,4-DICHLORO-6-FORMYLPHENOXY)-N-PROPYLACETAMIDE; 2-(2,4-DICHLOROPHENYL)-1H-INDOLE-3-CARBALDEHYDE; 2-(2,4-DICHLORO-PHENYL)-IMIDAZOLE-4-CARBALDEHYDE; 2-(2,4-DIFLUOROPHENYL)-4,6-DIMETHYL-1H-INDOLE-3-CARBOXALDEHYDE; 2-(2,4-DIFLUOROPHENYL)-4,7-DIMETHYL-1H-INDOLE-3-CARBOXALDEHYDE; 2-(2,4-DIFLUOROPHENYL)-5-(1-METHYLETHYL)-1H-INDOLE-3-CARBOXALDEHYDE; 2-(2,4-DIFLUOROPHENYL)-5,7-DIMETHYL-1H-INDOLE-3-CARBOXALDEHYDE; 2-(2,4-DIFLUOROPHENYL)-5-FLUORO-1H-INDOLE-3-CARBOXALDEHYDE; 2-(2,4-DIFLUOROPHENYL)-5-METHOXY-1H-INDOLE-3-CARBOXALDEHYDE; 2-(2,4-DIFLUOROPHENYL)-5-METHYL-1H-INDOLE-3-CARBOXALDEHYDE; 2-(2,4-DIFLUOROPHENYL)-6,7-DIMETHYL-1H-INDOLE-3-CARBOXALDEHYDE; 2-(2,4-DIFLUOROPHENYL)-7-FLUORO-1H-INDOLE-3-CARBOXALDEHYDE; 2-(2,4-DIFLUOROPHENYL)-7-FLUORO-5-METHYL-1H-INDOLE-3-CARBOXALDEHYDE; 2-(2,4-DIFLUOROPHENYL)-7-METHOXY-1H-INDOLE-3-CARBOXALDEHYDE; 2-(2,4-DIFLUOROPHENYL)-7-METHYL-1H-INDOLE-3-CARBOXALDEHYDE; 2-(2,4-DIFLUOROPHENYL)IMIDAZOLE-4-CARBALDEHYDE; 2-(2,4-DIMETHOXY-PHENYL)-4-FORMYL-IMIDAZOLE; 2-(2,4-DIMETHYLPHENYL)-1H-INDOLE-3-CARBALDEHYDE; DIMETHYLPHENYL)IMIDAZOLE-4-CARBALDEHYDE; 2-(2,4-DIOXO-1,3-DIAZASPIRO[4.4]NONAN-3-YL)ACETALDEHYDE; 2-(2,4-DIOXO-1,3-DIAZASPIRO[4.5]DECAN-3-YL)ACETALDEHYDE; 2-(2,4-DIOXO-1,3-DIAZASPIRO[4.7]DODECAN-3-YL)ACETALDEHYDE; 2-(2,5-DICHLOROPHENYL)-1H-INDOLE-3-CARBALDEHYDE; 2-(2,5-DICHLORO-PHENYL)-IMIDAZOLE-4-CARBALDEHYDE; 2-(2,5-DIFLUOROPHENYL)-4,6-DIMETHYL-1H-INDOLE-3-CARBOXALDEHYDE; 2-(2,5-DIFLUOROPHENYL)-4,7-DIMETHYL-1H-INDOLE-3-CARBOXALDEHYDE; 2-(2,5-DIFLUOROPHENYL)-5-(1-METHYLETHYL)-1H-INDOLE-3-CARBOXALDEHYDE; 2-(2,5-DIFLUOROPHENYL)-5,7-DIMETHYL-1H-INDOLE-3-CARBOXALDEHYDE; 2-(2,5-DIFLUOROPHENYL)-5-FLUORO-1H-INDOLE-3-CARBOXALDEHYDE; 2-(2,5-DIFLUOROPHENYL)-5-METHOXY-1H-INDOLE-3-CARBOXALDEHYDE; 2-(2,5-DIFLUOROPHENYL)-5-METHYL-1H-INDOLE-3-CARBOXALDEHYDE; 2-(2,5-DIFLUOROPHENYL)-6,7-DIMETHYL-1H-INDOLE-3-CARBOXALDEHYDE; 2-(2,5-DIFLUOROPHENYL)-7-FLUORO-1H-INDOLE-3-CARBOXALDEHYDE; 2-(2,5-DIFLUOROPHENYL)-7-FLUORO-5-METHYL-1H-INDOLE-3-CARBOXALDEHYDE; 2-(2,5-DIFLUOROPHENYL)-7-METHOXY-1H-INDOLE-3-CARBOXALDEHYDE; 2-(2,5-DIFLUOROPHENYL)-7-METHYL-1H-INDOLE-3-CARBOXALDEHYDE; 2-(2,5-DIFLUOROPHENYL)IMIDAZOLE-4-CARBALDEHYDE; 2-(2,5-DIMETHOXYPHENYL)-1H-

INDOLE-3-CARBALDEHYDE; 2-(2,5-DIMETHOXYPHENYL)-4-FORMYL-IMIDAZOLE; 2-(2,5-DIMETHYL-1H-PYRROL-3-YL)-4-FORMYLIMIDAZOLE; 2-(2,5-DIMETHYLPHENYL)-1H-INDOLE-3-CARBALDEHYDE; 2-(2,5-DIMETHYLPHENYL)IMIDAZOLE-4-CARBALDEHYDE; 2-(2,5-DIMETHYLTHIEN-3-YL)-1H-INDOLE-3-CARBALDEHYDE; DIOXOIMIDAZOLIDIN-1-YL)ACETALDEHYDE; 2-(2,6-DICHLORO-PHENYL)-IMIDAZOLE-4-CARBALDEHYDE; 2-(2,6-DIFLUORO-4-METHOXYPHENYL)-4-FORMYLIMIDAZOLE; 2-(2,6-DIFLUOROPHENYL)-4,6-DIMETHYL-1H-INDOLE-3-CARBOXALDEHYDE; 2-(2,6-DIFLUOROPHENYL)-4,7-DIMETHYL-1H-INDOLE-3-CARBOXALDEHYDE; 2-(2,6-DIFLUOROPHENYL)-5-(1-METHYLETHYL)-1H-INDOLE-3-CARBOXALDEHYDE; 2-(2,6-DIFLUOROPHENYL)-5,7-DIMETHYL-1H-INDOLE-3-CARBOXALDEHYDE; 2-(2,6-DIFLUOROPHENYL)-5-FLUORO-1H-INDOLE-3-CARBOXALDEHYDE; 2-(2,6-DIFLUOROPHENYL)-5-METHOXY-1H-INDOLE-3-CARBOXALDEHYDE; 2-(2,6-DIFLUOROPHENYL)-5-METHYL-1H-INDOLE-3-CARBOXALDEHYDE; 2-(2,6-DIFLUOROPHENYL)-6,7-DIMETHYL-1H-INDOLE-3-CARBOXALDEHYDE; 2-(2,6-DIFLUOROPHENYL)-7-FLUORO-1H-INDOLE-3-CARBOXALDEHYDE; 2-(2,6-DIFLUOROPHENYL)-7-FLUORO-5-METHYL-1H-INDOLE-3-CARBOXALDEHYDE; 2-(2,6-DIFLUOROPHENYL)-7-METHOXY-1H-INDOLE-3-CARBOXALDEHYDE; 2-(2,6-DIFLUOROPHENYL)-7-METHYL-1H-INDOLE-3-CARBOXALDEHYDE; 2-(2,6-DIFLUOROPHENYL)IMIDAZOLE-4-CARBALDEHYDE; 2-(2,6-DIMETHOXY-PHENYL)-4-FORMYL-IMIDAZOLE; 2-(2,6-DIMETHYLPHENYL)IMIDAZOLE-4-CARBALDEHYDE; 2-(2-AMINO-ETHYL)-1H-IMIDAZOLE-4-CARBALDEHYDE 2HCL; 2-(2-BROMO-4-FORMYLPHENOXY)-N-(CYANOMETHYL)ACETAMIDE; 2-(2-BROMO-4-FORMYLPHENOXY)-N-(PROP-2-EN-1-YL)ACETAMIDE; 2-(2-BROMO-4-FORMYLPHENOXY)-N-(PROP-2-YN-1-YL)ACETAMIDE; 2-(2-BROMO-4-FORMYLPHENOXY)-N-CYCLOPROPYLACETAMIDE; 2-(2-BROMO-4-FORMYLPHENOXY)-N-ETHYLACETAMIDE; 2-(2-BROMO-4-FORMYLPHENOXY)-N-METHYLACETAMIDE; 2-(2-BROMO-4-FORMYLPHENOXY)-N-METHYLPROPANAMIDE; 2-(2-BROMO-4-METHYL-PHENYL)-4-FORMYL-IMIDAZOLE; 2-(2-BROMO-5-FLUORO-PHENYL)-4-FORMYL-IMIDAZOLE; 2-(2-BROMO-6-FORMYLPHENOXY)-N-(CYANOMETHYL)ACETAMIDE; 2-(2-BROMO-6-FORMYLPHENOXY)-N-(PROP-2-EN-1-YL)ACETAMIDE; 2-(2-BROMO-6-FORMYLPHENOXY)-N-(PROP-2-YN-1-YL)ACETAMIDE; 2-(2-BROMO-6-FORMYLPHENOXY)-N-CYCLOPROPYLACETAMIDE; 2-(2-BROMO-6-FORMYLPHENOXY)-N-ETHYLACETAMIDE; 2-(2-BROMO-6-FORMYLPHENOXY)-N-METHYLACETAMIDE; 2-(2-BROMO-6-FORMYLPHENOXY)-N-METHYLPROPANAMIDE; 2-(2-BROMO-PHENYL)-1H-IMIDAZOLE-4-CARBALDEHYDE; 2-(2-CHLORO-4,5-DIFLUOROPHENYL)-4-FORMYLIMIDAZOLE; 2-(2-CHLORO-4-FLUORO-PHENYL)-4-FORMYL-IMIDAZOLE; 2-(2-CHLORO-4-FLUOROPHENYL)-5-FLUORO-1H-INDOLE-3-CARBOXALDEHYDE; 2-(2-CHLORO-4-FLUOROPHENYL)-5-METHYL-1H-INDOLE-3-CARBOXALDEHYDE; 2-(2-CHLORO-4-FLUOROPHENYL)-7-FLUORO-1H-INDOLE-3-CARBOXALDEHYDE; 2-(2-CHLORO-4-FLUOROPHENYL)-7-METHYL-1H-INDOLE-3-CARBOXALDEHYDE; 2-(2-CHLORO-4-FORMYL-6-METHOXYPHENOXY)-N-(CYANOMETHYL)ACETAMIDE; 2-(2-CHLORO-4-FORMYL-6-METHOXYPHENOXY)-N-(PROP-2-EN-1-YL)ACETAMIDE; 2-(2-CHLORO-4-FORMYL-6-METHOXYPHENOXY)-N-(PROPAN-2-YL)ACETAMIDE; 2-(2-CHLORO-4-FORMYL-6-METHOXYPHENOXY)-N-CYCLOPROPYLACETAMIDE; 2-(2-CHLORO-4-FORMYL-6-METHOXYPHENOXY)-N-ETHYLACETAMIDE; 2-(2-CHLORO-4-FORMYL-6-METHOXYPHENOXY)-N-ETHYLPROPANAMIDE; 2-(2-CHLORO-4-FORMYL-6-METHOXYPHENOXY)-N-METHYLACETAMIDE; 2-(2-CHLORO-4-FORMYL-6-METHOXYPHENOXY)-N-METHYLPROPANAMIDE; 2-(2-CHLORO-4-FORMYL-6-METHOXYPHENOXY)-N-PROP-2-YNYLACETAMIDE; 2-(2-CHLORO-4-FORMYL-6-METHOXYPHENOXY)-N-PROPYLACETAMIDE; 2-(2-CHLORO-4-FORMYLPHENOXY)-N-(2,2,2-TRIFLUOROETHYL)ACETAMIDE; 2-(2-CHLORO-4-FORMYLPHENOXY)-N-(2-CYANOETHYL)ACETAMIDE; 2-(2-CHLORO-4-FORMYLPHENOXY)-N-(2-METHOXYETHYL)ACETAMIDE; 2-(2-CHLORO-4-FORMYLPHENOXY)-N-(2-METHOXYETHYL)PROPANAMIDE; 2-(2-CHLORO-4-FORMYLPHENOXY)-N-(2-METHYLBUTAN-2-YL)ACETAMIDE; 2-(2-CHLORO-4-FORMYLPHENOXY)-N-(2-METHYLPROPYL)ACETAMIDE; 2-(2-CHLORO-4-FORMYLPHENOXY)-N-(3-METHOXYPROPYL)ACETAMIDE; 2-(2-CHLORO-4-FORMYLPHENOXY)-N-(3-METHYLBUTYL)ACETAMIDE; 2-(2-CHLORO-4-FORMYLPHENOXY)-N-(CYANOMETHYL)ACETAMIDE; 2-(2-CHLORO-4-FORMYLPHENOXY)-N-(CYCLOPROPYLMETHYL)ACETAMIDE; 2-(2-CHLORO-4-FORMYLPHENOXY)-N-(PENTAN-3-YL)ACETAMIDE; 2-(2-CHLORO-4-FORMYLPHENOXY)-N-(PROP-2-EN-1-YL)ACETAMIDE; 2-(2-CHLORO-4-FORMYLPHENOXY)-N-(PROP-2-YN-1-YL)ACETAMIDE; 2-(2-CHLORO-4-FORMYLPHENOXY)-N-(PROPAN-2-YL)ACETAMIDE; 2-(2-CHLORO-4-FORMYLPHENOXY)-N-CYCLOPENTYLACETAMIDE; 2-(2-CHLORO-4-FORMYLPHENOXY)-N-CYCLOPROPYLACETAMIDE; 2-(2-CHLORO-4-FORMYLPHENOXY)-N-CYCLOPROPYLPROPANAMIDE; 2-(2-CHLORO-4-FORMYLPHENOXY)-N-ETHYLACETAMIDE; 2-(2-CHLORO-4-FORMYLPHENOXY)-N-ETHYLPROPANAMIDE; 2-(2-CHLORO-4-FORMYLPHENOXY)-N-METHYLACETAMIDE; 2-(2-CHLORO-4-FORMYLPHENOXY)-N-METHYLPROPANAMIDE; 2-(2-CHLORO-4-FORMYLPHENOXY)-N-PHENYLACETAMIDE; 2-(2-CHLORO-4-FORMYLPHENOXY)-N-PROPYLACETAMIDE; 2-(2-CHLORO-4-FORMYLPHENOXY)-N-PROPYLPROPANAMIDE; 2-(2-CHLORO-5-FLUOROPHENYL)-5-FLUORO-1H-INDOLE-3-CARBOXALDEHYDE; 2-(2-CHLORO-5-FLUOROPHENYL)-5-METHYL-1H-INDOLE-3-CARBOXALDEHYDE; 2-(2-CHLORO-5-FLUOROPHENYL)-7-FLUORO-1H-INDOLE-3-CARBOXALDEHYDE; 2-(2-CHLORO-5-FLUOROPHENYL)-7-METHYL-1H-INDOLE-3-CARBOXALDEHYDE; 2-(2-CHLORO-5-NITROPHENYL)-4-FORMYL-IMIDAZOLE; 2-(2-CHLORO-6-FLUORO-PHENYL)-4-FORMYL-IMIDAZOLE; 2-(2-CHLORO-6-FLUOROPHENYL)-5-FLUORO-1H-

INDOLE-3-CARBOXALDEHYDE; 2-(2-CHLORO-6-FLUOROPHENYL)-5-METHYL-1H-INDOLE-3-CARBOXALDEHYDE; 2-(2-CHLORO-6-FLUOROPHENYL)-7-FLUORO-1H-INDOLE-3-CARBOXALDEHYDE; 2-(2-CHLORO-6-FLUOROPHENYL)-7-METHYL-1H-INDOLE-3-CARBOXALDEHYDE; 2-(2-CHLOROANILINO)-4-OXO-4H-PYRIDO(1,2-A)PYRIMIDINE-3-CARBALDEHYDE; 2-(2-CHLORO-PHENYL)-1H-IMIDAZOLE-4-CARBALDEHYDE; 2-(2-CHLOROPHENYL)-4,6-DIFLUORO-1H-INDOLE-3-CARBOXALDEHYDE; 2-(2-CHLOROPHENYL)-4,6-DIMETHYL-1H-INDOLE-3-CARBOXALDEHYDE; 2-(2-CHLOROPHENYL)-4,7-DIFLUORO-1H-INDOLE-3-CARBOXALDEHYDE; 2-(2-CHLOROPHENYL)-4,7-DIMETHYL-1H-INDOLE-3-CARBOXALDEHYDE; 2-(2-CHLOROPHENYL)-5-(1-METHYLETHYL)-1H-INDOLE-3-CARBOXALDEHYDE; 2-(2-CHLOROPHENYL)-5,7-DIFLUORO-1H-INDOLE-3-CARBOXALDEHYDE; 2-(2-CHLOROPHENYL)-5,7-DIMETHYL-1H-INDOLE-3-CARBOXALDEHYDE; 2-(2-CHLOROPHENYL)-5-ETHOXY-1H-INDOLE-3-CARBOXALDEHYDE; 2-(2-CHLOROPHENYL)-5-FLUORO-1H-INDOLE-3-CARBOXALDEHYDE; 2-(2-CHLOROPHENYL)-5-METHOXY-1H-INDOLE-3-CARBOXALDEHYDE; 2-(2-CHLOROPHENYL)-5-METHYL-1H-INDOLE-3-CARBOXALDEHYDE; 2-(2-CHLOROPHENYL)-6,7-DIFLUORO-1H-INDOLE-3-CARBOXALDEHYDE; 2-(2-CHLOROPHENYL)-6,7-DIMETHYL-1H-INDOLE-3-CARBOXALDEHYDE; 2-(2-CHLOROPHENYL)-7-FLUORO-1H-INDOLE-3-CARBOXALDEHYDE; 2-(2-CHLOROPHENYL)-7-FLUORO-5-METHYL-1H-INDOLE-3-CARBOXALDEHYDE; 2-(2-CHLOROPHENYL)-7-METHOXY-1H-INDOLE-3-CARBOXALDEHYDE; 2-(2-CHLOROPHENYL)-7-METHYL-1H-INDOLE-3-CARBOXALDEHYDE; 2-(2-CHLORO-PHENYLAMINO)-PYRIMIDINE-5-CARBALDEHYDE; 2-(2-ETHOXY-4-FORMYLPHENOXY)-N-(PROP-2-EN-1-YL)ACETAMIDE; 2-(2-ETHOXY-4-FORMYLPHENOXY)-N-(PROP-2-YN-1-YL)ACETAMIDE; 2-(2-ETHOXY-4-FORMYLPHENOXY)-N-(PROPAN-2-YL)ACETAMIDE; 2-(2-ETHOXY-4-FORMYLPHENOXY)-N-ETHYLACETAMIDE; 2-(2-ETHOXY-4-FORMYLPHENOXY)-N-ETHYLPROPANAMIDE; 2-(2-ETHOXY-4-FORMYLPHENOXY)-N-METHYLACETAMIDE; 2-(2-ETHOXY-4-FORMYLPHENOXY)-N-METHYLPROPANAMIDE; 2-(2-ETHOXY-4-FORMYLPHENOXY)-N-PHENYLACETAMIDE; 2-(2-ETHOXY-4-FORMYLPHENOXY)-N-PROPYLACETAMIDE; 2-(2-ETHOXY-6-FORMYLPHENOXY)-N-(PROP-2-EN-1-YL)ACETAMIDE; 2-(2-ETHOXY-6-FORMYLPHENOXY)-N-(PROP-2-YN-1-YL)ACETAMIDE; 2-(2-ETHOXY-6-FORMYLPHENOXY)-N-(PROPAN-2-YL)ACETAMIDE; 2-(2-ETHOXY-6-FORMYLPHENOXY)-N-ETHYLACETAMIDE; 2-(2-ETHOXY-6-FORMYLPHENOXY)-N-ETHYLPROPANAMIDE; 2-(2-ETHOXY-6-FORMYLPHENOXY)-N-METHYLACETAMIDE; 2-(2-ETHOXY-6-FORMYLPHENOXY)-N-METHYLPROPANAMIDE; 2-(2-ETHOXY-6-FORMYLPHENOXY)-N-PROPYLACETAMIDE; 2-(2-ETHOXY-PHENYLAMINO)-PYRIMIDINE-5-CARBALDEHYDE; 2-(2-FLUORO-3-METHOXY-PHENYL)-4-FORMYL-IMIDAZOLE; 2-(2-FLUORO-4-METHOXY-PHENYL)-4-FORMYL-IMIDAZOLE; 2-(2-FLUORO-4-NITROPHENYL)-5-METHYL-1H-INDOLE-3-CARBOXALDEHYDE; 2-(2-FLUORO-4-NITROPHENYL)-7-METHYL-1H-INDOLE-3-CARBOXALDEHYDE; 2-(2-FLUORO-5-METHOXY-PHENYL)-4-FORMYL-IMIDAZOLE; 2-(2-FLUORO-5-METHYL-PHENYL)-4-FORMYL-IMIDAZOLE; 2-(2-FLUORO-5-NITRO-PHENYL)-4-FORMYL-IMIDAZOLE; 2-(2-FLUORO-5-NITROPHENYL)-5-METHYL-1H-INDOLE-3-CARBOXALDEHYDE; 2-(2-FLUORO-5-NITROPHENYL)-7-METHYL-1H-INDOLE-3-CARBOXALDEHYDE; 2-(2-FLUORO-6-METHOXY-PHENYL)-4-FORMYL-IMIDAZOLE; 2-(2-FLUOROANILINO)-9-METHYL-4-OXO-4H-PYRIDO(1,2-A)PYRIMIDINE-3-CARBALDEHYDE; 2-(2-FLUORO-PHENYL)-1H-IMIDAZOLE-4-CARBALDEHYDE; 2-(2-FLUOROPHENYL)-5-(1-METHYLETHYL)-1H-INDOLE-3-CARBOXALDEHYDE; 2-(2-FLUOROPHENYL)-5-METHOXY-1H-INDOLE-3-CARBOXALDEHYDE; 2-(2-FLUOROPHENYL)-5-METHYL-1H-INDOLE-3-CARBOXALDEHYDE; 2-(2-FLUOROPHENYL)-5-NITRO-1H-INDOLE-3-CARBOXALDEHYDE; 2-(2-FLUOROPHENYL)-7-METHOXY-1H-INDOLE-3-CARBOXALDEHYDE; 2-(2-FLUOROPHENYL)-7-METHYL-1H-INDOLE-3-CARBOXALDEHYDE; 2-(2-FLUOROPHENYL)-7-METHYL-5-NITRO-1H-INDOLE-3-CARBOXALDEHYDE; 2-(2-FORMYL-1H-IMIDAZOL-1-YL)-N-(2-METHYLPHENYL)ACETAMIDE; 2-(2-FORMYL-1H-IMIDAZOL-1-YL)-N-(3-METHOXYPHENYL)ACETAMIDE; 2-(2-FORMYL-1H-IMIDAZOL-1-YL)-N-(3-METHYLPHENYL)ACETAMIDE; 2-(2-FORMYL-4-METHOXYPHENOXY)-N-(2-FURYLMETHYL)ACETAMIDE; 2-(2-FORMYL-4-METHOXYPHENOXY)-N-(2-METHOXYETHYL)ACETAMIDE; 2-(2-FORMYL-4-METHOXYPHENOXY)-N-(2-METHYLPROPYL)ACETAMIDE; 2-(2-FORMYL-4-METHOXYPHENOXY)-N-(PROP-2-EN-1-YL)ACETAMIDE; 2-(2-FORMYL-4-METHOXYPHENOXY)-N-(PROP-2-EN-1-YL)PROPANAMIDE; 2-(2-FORMYL-4-METHOXYPHENOXY)-N-(PROP-2-YN-1-YL)ACETAMIDE; 2-(2-FORMYL-4-METHOXYPHENOXY)-N-(PROP-2-YN-1-YL)PROPANAMIDE; 2-(2-FORMYL-4-METHOXYPHENOXY)-N-(PROPAN-2-YL)ACETAMIDE; 2-(2-FORMYL-4-METHOXYPHENOXY)-N-(PROPAN-2-YL)PROPANAMIDE; 2-(2-FORMYL-4-METHOXYPHENOXY)-N-(TETRAHYDROFURAN-2-YLMETHYL)ACETAMIDE; 2-(2-FORMYL-4-METHOXYPHENOXY)-N-METHYLACETAMIDE; 2-(2-FORMYL-4-METHOXYPHENOXY)-N-METHYLPROPANAMIDE; 2-(2-FORMYL-4-METHOXYPHENOXY)-N-PROPYLACETAMIDE; 2-(2-FORMYL-4-METHOXYPHENOXY)-N-PROPYLPROPANAMIDE; 2-(2-FORMYL-4-METHYLPHENOXY)-N-METHYLACETAMIDE; 2-(2-FORMYL-4-METHYLPHENOXY)-N-METHYLPROPANAMIDE; 2-(2-FORMYL-4-NITROPHENOXY)-N-(PROP-2-EN-1-YL)ACETAMIDE; 2-(2-FORMYL-4-NITROPHENOXY)-N-(PROP-2-YN-1-YL)ACETAMIDE; 2-(2-FORMYL-4-NITROPHENOXY)-N-(PROPAN-2-YL)ACETAMIDE; 2-(2-FORMYL-4-NITROPHENOXY)-N-METHYLACETAMIDE; 2-(2-FORMYL-4-NITROPHENOXY)-N-METHYLPROPANAMIDE; 2-(2-FORMYL-4-NITROPHENOXY)-N-PROPYLACETAMIDE; 2-(2-

FORMYL-5-METHOXYPHENOXY)-N-(2-METHOXYETHYL)ACETAMIDE; 2-(2-FORMYL-5-METHOXYPHENOXY)-N-(2-METHYLPROPYL) ACETAMIDE; 2-(2-FORMYL-5-METHOXYPHENOXY)-N-(PROP-2-EN-1-YL) ACETAMIDE; 2-(2-FORMYL-5-METHOXYPHENOXY)-N-(PROP-2-EN-1-YL) PROPANAMIDE; 2-(2-FORMYL-5-METHOXYPHENOXY)-N-(PROP-2-YN-1-YL) ACETAMIDE; 2-(2-FORMYL-5-METHOXYPHENOXY)-N-(PROP-2-YN-1-YL) PROPANAMIDE; 2-(2-FORMYL-5-METHOXYPHENOXY)-N-(PROPAN-2-YL) ACETAMIDE; 2-(2-FORMYL-5-METHOXYPHENOXY)-N-(PROPAN-2-YL) PROPANAMIDE; 2-(2-FORMYL-5-METHOXYPHENOXY)-N-METHYLACETAMIDE; 2-(2-FORMYL-5-METHOXYPHENOXY)-N-METHYLPROPANAMIDE; 2-(2-FORMYL-5-METHOXYPHENOXY)-N-PROPYLACETAMIDE; 2-(2-FORMYL-5-METHOXYPHENOXY)-N-PROPYLPROPANAMIDE; 2-(2-FORMYL-5-PROPOXYPHENOXY)-N-(2-METHOXYETHYL) ACETAMIDE; 2-(2-FORMYL-5-PROPOXYPHENOXY)-N-METHYLACETAMIDE; 2-(2-FORMYL-5-PROPOXYPHENOXY)-N-METHYLPROPANAMIDE; 2-(2-FORMYL-6-METHOXYPHENOXY)-N-(2-METHOXYETHYL)ACETAMIDE; 2-(2-FORMYL-6-METHOXYPHENOXY)-N-(2-METHYLPHENYL)ACETAMIDE; 2-(2-FORMYL-6-METHOXYPHENOXY)-N-(2-METHYLPROPYL)ACETAMIDE; 2-(2-FORMYL-6-METHOXYPHENOXY)-N-(PROP-2-EN-1-YL) ACETAMIDE; 2-(2-FORMYL-6-METHOXYPHENOXY)-N-(PROP-2-EN-1-YL) PROPANAMIDE; 2-(2-FORMYL-6-METHOXYPHENOXY)-N-(PROP-2-YN-1-YL) ACETAMIDE; 2-(2-FORMYL-6-METHOXYPHENOXY)-N-(PROP-2-YN-1-YL) PROPANAMIDE; 2-(2-FORMYL-6-METHOXYPHENOXY)-N-(PROPAN-2-YL) ACETAMIDE; 2-(2-FORMYL-6-METHOXYPHENOXY)-N-(PROPAN-2-YL) PROPANAMIDE; 2-(2-FORMYL-6-METHOXYPHENOXY)-N-(TETRAHYDROFURAN-2-YLMETHYL)ACETAMIDE; 2-(2-FORMYL-6-METHOXYPHENOXY)-N-METHYLACETAMIDE; 2-(2-FORMYL-6-METHOXYPHENOXY)-N-METHYLPROPANAMIDE; 2-(2-FORMYL-6-METHOXYPHENOXY)-N-PROPYLACETAMIDE; 2-(2-FORMYL-6-METHOXYPHENOXY)-N-PROPYLPROPANAMIDE; 2-(2-FORMYL-6-METHOXYPHENOXY)-N-P-TOLYL-ACETAMIDE; 2-(2-FORMYLPHENOXY)-N-(1-METHOXYPROPAN-2-YL) ACETAMIDE; 2-(2-FORMYLPHENOXY)-N-(2,2,2-TRIFLUOROETHYL)ACETAMIDE; 2-(2-FORMYLPHENOXY)-N-(2-FURYLMETHYL) ACETAMIDE; 2-(2-FORMYLPHENOXY)-N-(2-METHOXYETHYL)ACETAMIDE; 2-(2-FORMYLPHENOXY)-N-(2-METHOXYETHYL) PROPANAMIDE; 2-(2-FORMYLPHENOXY)-N-(2-METHOXYPHENYL)ACETAMIDE; 2-(2-FORMYLPHENOXY)-N-(2-METHYLBUTAN-2-YL) ACETAMIDE; 2-(2-FORMYLPHENOXY)-N-(2-METHYLBUTAN-2-YL)PROPANAMIDE; 2-(2-FORMYLPHENOXY)-N-(2-METHYLPHENYL) ACETAMIDE; 2-(2-FORMYLPHENOXY)-N-(2-METHYLPROPYL)ACETAMIDE; 2-(2-FORMYLPHENOXY)-N-(2-METHYLPROPYL)PROPANAMIDE; 2-(2-FORMYLPHENOXY)-N-(2-PHENYLETHYL)ACETAMIDE; 2-(2-FORMYLPHENOXY)-N-(3-METHOXYPHENYL)ACETAMIDE; 2-(2-FORMYLPHENOXY)-N-(3-METHOXYPROPYL) ACETAMIDE; 2-(2-FORMYLPHENOXY)-N-(3-METHOXYPROPYL)PROPANAMIDE; 2-(2-FORMYLPHENOXY)-N-(3-METHYLBUTAN-2-YL) ACETAMIDE; 2-(2-FORMYLPHENOXY)-N-(3-METHYLBUTYL)ACETAMIDE; 2-(2-FORMYLPHENOXY)-N-(3-METHYLBUTYL) PROPANAMIDE; 2-(2-FORMYLPHENOXY)-N-(3-METHYLPHENYL)ACETAMIDE; 2-(2-FORMYLPHENOXY)-N-(4-METHYLPHENYL) ACETAMIDE; 2-(2-FORMYLPHENOXY)-N-(OXAN-4-YL)ACETAMIDE; 2-(2-FORMYLPHENOXY)-N-(PENTAN-2-YL)ACETAMIDE; 2-(2-FORMYLPHENOXY)-N-(PENTAN-2-YL) PROPANAMIDE; 2-(2-FORMYLPHENOXY)-N-(PENTAN-3-YL)ACETAMIDE; 2-(2-FORMYLPHENOXY)-N-(PENTAN-3-YL) PROPANAMIDE; 2-(2-FORMYLPHENOXY)-N-(PROP-2-EN-1-YL)ACETAMIDE; 2-(2-FORMYLPHENOXY)-N-(PROP-2-EN-1-YL)PROPANAMIDE; 2-(2-FORMYLPHENOXY)-N-(PROP-2-YN-1-YL) ACETAMIDE; 2-(2-FORMYLPHENOXY)-N-(PROP-2-YN-1-YL)PROPANAMIDE; 2-(2-FORMYLPHENOXY)-N-(PROPAN-2-YL)ACETAMIDE; 2-(2-FORMYLPHENOXY)-N-(PROPAN-2-YL) PROPANAMIDE; 2-(2-FORMYLPHENOXY)-N-(TETRAHYDRO-2-FURANYLMETHYL)ACETAMIDE; 2-(2-FORMYLPHENOXY)-N-METHYLACETAMIDE; 2-(2-FORMYLPHENOXY)-N-METHYLPROPANAMIDE; 2-(2-FORMYLPHENOXY)-N-PENTYLPROPANAMIDE; 2-(2-FORMYLPHENOXY)-N-PHENYLACETAMIDE; 2-(2-FORMYLPHENOXY)-N-PROPYLACETAMIDE; 2-(2-FORMYLPHENOXY)-N-PROPYLPROPANAMIDE; 2-(2-FORMYLPIPERIDIN-1-YL)-N-(1,3-THIAZOL-2-YL)ACETAMIDE; 2-(2-FORMYLPIPERIDIN-1-YL)-N-(1-METHOXYPROPAN-2-YL)ACETAMIDE; 2-(2-FORMYLPIPERIDIN-1-YL)-N-(2,2,2-TRIFLUOROETHYL)ACETAMIDE; 2-(2-FORMYLPIPERIDIN-1-YL)-N-(2-METHOXYETHYL) ACETAMIDE; 2-(2-FORMYLPIPERIDIN-1-YL)-N-(2-METHOXYETHYL)PROPANAMIDE; 2-(2-FORMYLPIPERIDIN-1-YL)-N-(2-METHYL-4-OXOPENTAN-3-YL)ACETAMIDE; 2-(2-FORMYLPIPERIDIN-1-YL)-N-(2-METHYLBUTAN-2-YL)ACETAMIDE; 2-(2-FORMYLPIPERIDIN-1-YL)-N-(2-METHYLBUTAN-2-YL)PROPANAMIDE; 2-(2-FORMYLPIPERIDIN-1-YL)-N-(2-METHYLCYCLOHEXYL)ACETAMIDE; 2-(2-FORMYLPIPERIDIN-1-YL)-N-(2-METHYLPHENYL) ACETAMIDE; 2-(2-FORMYLPIPERIDIN-1-YL)-N-(2-METHYLPROPYL)ACETAMIDE; 2-(2-FORMYLPIPERIDIN-1-YL)-N-(2-METHYLPROPYL) PROPANAMIDE; 2-(2-FORMYLPIPERIDIN-1-YL)-N-(3-METHOXYPROPYL)ACETAMIDE; 2-(2-FORMYLPIPERIDIN-1-YL)-N-(3-METHOXYPROPYL) PROPANAMIDE; 2-(2-FORMYLPIPERIDIN-1-YL)-N-(3-METHYL-1,2-OXAZOL-5-YL)ACETAMIDE; 2-(2-FORMYLPIPERIDIN-1-YL)-N-(3-METHYLBUTAN-2-YL)ACETAMIDE; 2-(2-FORMYLPIPERIDIN-1-YL)-N-(3-METHYLBUTYL)ACETAMIDE; 2-(2-FORMYLPIPERIDIN-1-YL)-N-(3-METHYLBUTYL) PROPANAMIDE; 2-(2-FORMYLPIPERIDIN-1-YL)-N-(3-METHYLPHENYL)ACETAMIDE; 2-(2-

FORMYLPIPERIDIN-1-YL)-N-(4-METHYL-1,3-THIAZOL-2-YL)ACETAMIDE; 2-(2-FORMYLPIPERIDIN-1-YL)-N-(4-METHYLCYCLOHEXYL)ACETAMIDE; 2-(2-FORMYLPIPERIDIN-1-YL)-N-(4-METHYLPHENYL)ACETAMIDE; 2-(2-FORMYLPIPERIDIN-1-YL)-N-(5-METHYL-1,2-OXAZOL-3-YL)ACETAMIDE; 2-(2-FORMYLPIPERIDIN-1-YL)-N-(5-METHYL-1,3,4-OXADIAZOL-2-YL)ACETAMIDE; 2-(2-FORMYLPIPERIDIN-1-YL)-N-(5-METHYLHEXAN-2-YL)ACETAMIDE; 2-(2-FORMYLPIPERIDIN-1-YL)-N-(FURAN-2-YLMETHYL)ACETAMIDE; 2-(2-FORMYLPIPERIDIN-1-YL)-N-(FURAN-2-YLMETHYL)PROPANAMIDE; 2-(2-FORMYLPIPERIDIN-1-YL)-N-(HEPTAN-2-YL)ACETAMIDE; 2-(2-FORMYLPIPERIDIN-1-YL)-N-(OXAN-4-YL)ACETAMIDE; 2-(2-FORMYLPIPERIDIN-1-YL)-N-(OXOLAN-2-YLMETHYL)ACETAMIDE; 2-(2-FORMYLPIPERIDIN-1-YL)-N-(PENTAN-2-YL)ACETAMIDE; 2-(2-FORMYLPIPERIDIN-1-YL)-N-(PENTAN-2-YL)PROPANAMIDE; 2-(2-FORMYLPIPERIDIN-1-YL)-N-(PENTAN-3-YL)ACETAMIDE; 2-(2-FORMYLPIPERIDIN-1-YL)-N-(PENTAN-3-YL)PROPANAMIDE; 2-(2-FORMYLPIPERIDIN-1-YL)-N-(PROP-2-EN-1-YL)ACETAMIDE; 2-(2-FORMYLPIPERIDIN-1-YL)-N-(PROP-2-EN-1-YL)PROPANAMIDE; 2-(2-FORMYLPIPERIDIN-1-YL)-N-(PROP-2-YN-1-YL)ACETAMIDE; 2-(2-FORMYLPIPERIDIN-1-YL)-N-(PROP-2-YN-1-YL)PROPANAMIDE; 2-(2-FORMYLPIPERIDIN-1-YL)-N-(PROPAN-2-YL)ACETAMIDE; 2-(2-FORMYLPIPERIDIN-1-YL)-N-(PROPAN-2-YL)PROPANAMIDE; 2-(2-FORMYLPIPERIDIN-1-YL)-N-(PYRIMIDIN-2-YL)ACETAMIDE; 2-(2-FORMYLPIPERIDIN-1-YL)-N-(THIOPHEN-2-YLMETHYL)ACETAMIDE; 2-(2-FORMYLPIPERIDIN-1-YL)-N-[1-(FURAN-2-YL)ETHYL]ACETAMIDE; 2-(2-FORMYLPIPERIDIN-1-YL)-N-[1-(THIOPHEN-2-YL)ETHYL]ACETAMIDE; 2-(2-FORMYLPIPERIDIN-1-YL)-N-[2-(THIOPHEN-2-YL)ETHYL]ACETAMIDE; 2-(2-FORMYLPIPERIDIN-1-YL)-N-[3-(PROPAN-2-YLOXY)PROPYL]ACETAMIDE; 2-(2-FORMYLPIPERIDIN-1-YL)-N-METHYLACETAMIDE; 2-(2-FORMYLPIPERIDIN-1-YL)-N-METHYLPROPANAMIDE; 2-(2-FORMYLPIPERIDIN-1-YL)-N-PENTYLPROPANAMIDE; 2-(2-FORMYLPIPERIDIN-1-YL)-N-PHENYLACETAMIDE; 2-(2-FORMYLPIPERIDIN-1-YL)-N-PROPYLACETAMIDE; 2-(2-FORMYLPIPERIDIN-1-YL)-N-PROPYLPROPANAMIDE; 2-(2-IODO-PHENYL)-1H-IMIDAZOLE-4-CARBALDEHYDE; 2-(2-METHOXY-5-METHYLPHENYL)-1H-INDOLE-3-CARBALDEHYDE; 2-(2-METHOXY-NAPHTHALEN-1-YL)-4-FORMYLIMIDAZOLE; 2-(2-METHOXY-PHENYL)-1H-IMIDAZOLE-4-CARBALDEHYDE; 2-(2-METHOXY-PHENYLAMINO)-PYRIMIDINE-5-CARBALDEHYDE; 2-(2-METHYLPHENYL)-5-NITRO-1H-INDOLE-3-CARBOXALDEHYDE; 2-(2-METHYLSULFANYL-ETHYL)-4-FORMYLIMIDAZOLE; 2-(2-NAPHTHYL)-1H-INDOLE-3-CARBALDEHYDE; 2-(2-NITRO-PHENYL)-1H-IMIDAZOLE-4-CARBALDEHYDE; 2-(2-OXOPROPYL)-1H-PYRROLE-3-CARBALDEHYDE; 2-(2-PYRIDINYL)-1H-INDOLE-3-CARBALDEHYDE HYDROCHLORIDE; 2-(2-TRIFLUOROMETHOXY-PHENYL)-4-FORMYL-IMIDAZOLE; 2-(2-TRIFLUOROMETHYL-PHENYL)-4-FORMYL-IMIDAZOLE; 2-(3-(TRIFLUOROMETHYL)PHENYL)-1H-IMIDAZOLE-5-CARBALDEHYDE; 2-(3,4-DICHLORO-PHENYL)-IMIDAZOLE-4-CARBALDEHYDE; 2-(3,4-DIFLUOROPHENYL)-4,6-DIMETHYL-1H-INDOLE-3-CARBOXALDEHYDE; 2-(3,4-DIFLUOROPHENYL)-4,7-DIMETHYL-1H-INDOLE-3-CARBOXALDEHYDE; 2-(3,4-DIFLUOROPHENYL)-5-(1-METHYLETHYL)-1H-INDOLE-3-CARBOXALDEHYDE; 2-(3,4-DIFLUOROPHENYL)-5,7-DIMETHYL-1H-INDOLE-3-CARBOXALDEHYDE; 2-(3,4-DIFLUOROPHENYL)-5-FLUORO-1H-INDOLE-3-CARBOXALDEHYDE; 2-(3,4-DIFLUOROPHENYL)-5-METHOXY-1H-INDOLE-3-CARBOXALDEHYDE; 2-(3,4-DIFLUOROPHENYL)-5-METHYL-1H-INDOLE-3-CARBOXALDEHYDE; 2-(3,4-DIFLUOROPHENYL)-6,7-DIMETHYL-1H-INDOLE-3-CARBOXALDEHYDE; 2-(3,4-DIFLUOROPHENYL)-7-FLUORO-1H-INDOLE-3-CARBOXALDEHYDE; 2-(3,4-DIFLUOROPHENYL)-7-FLUORO-5-METHYL-1H-INDOLE-3-CARBOXALDEHYDE; DIFLUOROPHENYL)-7-METHOXY-1H-INDOLE-3-CARBOXALDEHYDE; DIFLUOROPHENYL)-7-METHYL-1H-INDOLE-3-CARBOXALDEHYDE; DIFLUOROPHENYL)IMIDAZOLE-4-CARBALDEHYDE; 2-(3,4-DIMETHOXYPHENYL)-1H-INDOLE-3-CARBALDEHYDE; 2-(3,4-DIMETHOXY-PHENYL)-4-FORMYL-IMIDAZOLE; 2-(3,4-DIMETHYLPHENYL)-1H-INDOLE-3-CARBALDEHYDE; DIMETHYLPHENYL)IMIDAZOLE-4-CARBALDEHYDE; 2-(3,5-DICHLORO-PHENYL)-IMIDAZOLE-4-CARBALDEHYDE; 2-(3,5-DIFLUOROPHENYL)-4,6-DIMETHYL-1H-INDOLE-3-CARBOXALDEHYDE; 2-(3,5-DIFLUOROPHENYL)-4,7-DIMETHYL-1H-INDOLE-3-CARBOXALDEHYDE; 2-(3,5-DIFLUOROPHENYL)-5-(1-METHYLETHYL)-1H-INDOLE-3-CARBOXALDEHYDE; 2-(3,5-DIFLUOROPHENYL)-5,7-DIMETHYL-1H-INDOLE-3-CARBOXALDEHYDE; 2-(3,5-DIFLUOROPHENYL)-5-FLUORO-1H-INDOLE-3-CARBOXALDEHYDE; 2-(3,5-DIFLUOROPHENYL)-5-METHOXY-1H-INDOLE-3-CARBOXALDEHYDE; 2-(3,5-DIFLUOROPHENYL)-5-METHYL-1H-INDOLE-3-CARBOXALDEHYDE; 2-(3,5-DIFLUOROPHENYL)-6,7-DIMETHYL-1H-INDOLE-3-CARBOXALDEHYDE; 2-(3,5-DIFLUOROPHENYL)-7-FLUORO-1H-INDOLE-3-CARBOXALDEHYDE; 2-(3,5-DIFLUOROPHENYL)-7-FLUORO-5-METHYL-1H-INDOLE-3-CARBOXALDEHYDE; 2-(3,5-DIFLUOROPHENYL)-7-METHOXY-1H-INDOLE-3-CARBOXALDEHYDE; 2-(3,5-DIFLUOROPHENYL)-7-METHYL-1H-INDOLE-3-CARBOXALDEHYDE; 2-(3,5-DIFLUOROPHENYL)IMIDAZOLE-4-CARBALDEHYDE; 2-(3,5-DIMETHOXY-PHENYL)-4-FORMYL-1H-IMIDAZOLE; DIMETHYLPHENYL)IMIDAZOLE-4-CARBALDEHYDE; 2-(3-AZETIDINYLOXY)-BENZALDEHYDE; 2-(3-BROMO-4-FLUORO-PHENYL)-4-FORMYL-IMIDAZOLE; 2-(3-BROMO-4-METHOXYPHENYL)-4-FORMYLIMIDAZOLE; 2-(3-BROMO-PHENYL)-1H-IMIDAZOLE-4-CARBALDEHYDE; 2-(3-BROMOPHENYL)-1H-IMIDAZOLE-5-CARBALDEHYDE; 2-(3-CHLORO-2-FLUORO-PHENYL)-4-FORMYL-IMIDAZOLE; 2-(3-CHLORO-2-FORMYLPHENOXY)-N-(2,2,2-TRIFLUOROETHYL)ACETAMIDE; 2-(3-CHLORO-2-FORMYLPHENOXY)-N-(2-CYANOETHYL)ACETAMIDE; 2-(3-CHLORO-2-FORMYLPHENOXY)-N-(2-METHOXYETHYL)ACETAMIDE; 2-(3-CHLORO-2-FORMYLPHENOXY)-N-(2-METHOXYETHYL)PROPANAMIDE; 2-(3-CHLORO-2-FORMYLPHENOXY)-N-(2-METHYLBUTAN-2-YL)ACETAMIDE; 2-(3-CHLORO-2-

FORMYLPHENOXY)-N-(2-METHYLPROPYL)ACETAMIDE; 2-(3-CHLORO-2-FORMYLPHENOXY)-N-(2-METHYLPROPYL)PROPANAMIDE; 2-(3-CHLORO-2-FORMYLPHENOXY)-N-(3-METHOXYPROPYL)ACETAMIDE; 2-(3-CHLORO-2-FORMYLPHENOXY)-N-(3-METHYLBUTYL)ACETAMIDE; 2-(3-CHLORO-2-FORMYLPHENOXY)-N-(CYANOMETHYL)ACETAMIDE; 2-(3-CHLORO-2-FORMYLPHENOXY)-N-(CYCLOPROPYLMETHYL)ACETAMIDE; 2-(3-CHLORO-2-FORMYLPHENOXY)-N-(PENTAN-3-YL)ACETAMIDE; 2-(3-CHLORO-2-FORMYLPHENOXY)-N-(PROP-2-EN-1-YL)ACETAMIDE; 2-(3-CHLORO-2-FORMYLPHENOXY)-N-(PROP-2-EN-1-YL)PROPANAMIDE; 2-(3-CHLORO-2-FORMYLPHENOXY)-N-(PROP-2-YN-1-YL)ACETAMIDE; 2-(3-CHLORO-2-FORMYLPHENOXY)-N-(PROP-2-YN-1-YL)PROPANAMIDE; 2-(3-CHLORO-2-FORMYLPHENOXY)-N-(PROPAN-2-YL)ACETAMIDE; 2-(3-CHLORO-2-FORMYLPHENOXY)-N-(PROPAN-2-YL)PROPANAMIDE; 2-(3-CHLORO-2-FORMYLPHENOXY)-N-CYCLOPENTYLACETAMIDE; 2-(3-CHLORO-2-FORMYLPHENOXY)-N-CYCLOPROPYLACETAMIDE; 2-(3-CHLORO-2-FORMYLPHENOXY)-N-CYCLOPROPYLPROPANAMIDE; 2-(3-CHLORO-2-FORMYLPHENOXY)-N-ETHYLACETAMIDE; 2-(3-CHLORO-2-FORMYLPHENOXY)-N-ETHYLPROPANAMIDE; 2-(3-CHLORO-2-FORMYLPHENOXY)-N-METHYLACETAMIDE; 2-(3-CHLORO-2-FORMYLPHENOXY)-N-METHYLPROPANAMIDE; 2-(3-CHLORO-2-FORMYLPHENOXY)-N-PROPYLACETAMIDE; 2-(3-CHLORO-2-FORMYLPHENOXY)-N-PROPYLPROPANAMIDE; 2-(3-CHLORO-4-FLUOROPHENYL)-4-FORMYLIMIDAZOLE; 2-(3-CHLORO-4-FLUOROPHENYL)-5-FLUORO-1H-INDOLE-3-CARBOXALDEHYDE; 2-(3-CHLORO-4-FLUOROPHENYL)-5-METHYL-1H-INDOLE-3-CARBOXALDEHYDE; 2-(3-CHLORO-4-FLUOROPHENYL)-7-FLUORO-1H-INDOLE-3-CARBOXALDEHYDE; 2-(3-CHLORO-4-FLUOROPHENYL)-7-METHYL-1H-INDOLE-3-CARBOXALDEHYDE; 2-(3-CHLORO-PHENYL)-1H-IMIDAZOLE-4-CARBALDEHYDE; 2-(3-CHLOROPHENYL)-1H-INDOLE-3-CARBOXALDEHYDE; 2-(3-CHLOROPHENYL)-4,6-DIFLUORO-1H-INDOLE-3-CARBOXALDEHYDE; 2-(3-CHLOROPHENYL)-4,6-DIMETHYL-1H-INDOLE-3-CARBOXALDEHYDE; 2-(3-CHLOROPHENYL)-4,7-DIFLUORO-1H-INDOLE-3-CARBOXALDEHYDE; 2-(3-CHLOROPHENYL)-4,7-DIMETHYL-1H-INDOLE-3-CARBOXALDEHYDE; 2-(3-CHLOROPHENYL)-5-(1-METHYLETHYL)-1H-INDOLE-3-CARBOXALDEHYDE; 2-(3-CHLOROPHENYL)-5,7-DIFLUORO-1H-INDOLE-3-CARBOXALDEHYDE; 2-(3-CHLOROPHENYL)-5,7-DIMETHYL-1H-INDOLE-3-CARBOXALDEHYDE; 2-(3-CHLOROPHENYL)-5-ETHOXY-1H-INDOLE-3-CARBOXALDEHYDE; 2-(3-CHLOROPHENYL)-5-FLUORO-1H-INDOLE-3-CARBOXALDEHYDE; 2-(3-CHLOROPHENYL)-5-METHOXY-1H-INDOLE-3-CARBOXALDEHYDE; 2-(3-CHLOROPHENYL)-5-METHYL-1H-INDOLE-3-CARBOXALDEHYDE; 2-(3-CHLOROPHENYL)-6,7-DIFLUORO-1H-INDOLE-3-CARBOXALDEHYDE; 2-(3-CHLOROPHENYL)-6,7-DIMETHYL-1H-INDOLE-3-CARBOXALDEHYDE; 2-(3-CHLOROPHENYL)-7-FLUORO-1H-INDOLE-3-CARBOXALDEHYDE; 2-(3-CHLOROPHENYL)-7-FLUORO-5-METHYL-1H-INDOLE-3-CARBOXALDEHYDE; 2-(3-CHLOROPHENYL)-7-METHOXY-1H-INDOLE-3-CARBOXALDEHYDE; 2-(3-CHLOROPHENYL)-7-METHYL-1H-INDOLE-3-CARBOXALDEHYDE; 2-(3-CHLORO-PHENYLAMINO)-PYRIMIDINE-5-CARBALDEHYDE; 2-(3-FLUORO-2-METHYL-PHENYL)-4-FORMYL-IMIDAZOLE; 2-(3-FLUORO-4-METHOXYPHENYL)-1H-INDOLE-3-CARBALDEHYDE; 2-(3-FLUORO-4-METHOXY-PHENYL)-4-FORMYL-IMIDAZOLE; 2-(3-FLUORO-4-METHYL-PHENYL)-4-FORMYL-IMIDAZOLE; 2-(3-FLUORO-PHENYL)-1H-IMIDAZOLE-4-CARBALDEHYDE; 2-(3-FLUOROPHENYL)-1H-IMIDAZOLE-5-CARBALDEHYDE; 2-(3-FLUOROPHENYL)-5-(1-METHYLETHYL)-1H-INDOLE-3-CARBOXALDEHYDE; 2-(3-FLUOROPHENYL)-5-METHOXY-1H-INDOLE-3-CARBOXALDEHYDE; 2-(3-FLUOROPHENYL)-5-METHYL-1H-INDOLE-3-CARBOXALDEHYDE; 2-(3-FLUOROPHENYL)-5-NITRO-1H-INDOLE-3-CARBOXALDEHYDE; 2-(3-FLUOROPHENYL)-7-METHOXY-1H-INDOLE-3-CARBOXALDEHYDE; 2-(3-FLUOROPHENYL)-7-METHYL-1H-INDOLE-3-CARBOXALDEHYDE; 2-(3-FLUOROPHENYL)-7-METHYL-5-NITRO-1H-INDOLE-3-CARBOXALDEHYDE; 2-(3-FORMYL-1H-INDOL-1-YL)-N-(2-THIENYLMETHYL)ACETAMIDE; 2-(3-FORMYL-1H-PYRROL-2-YL)ACETONITRILE; 2-(3-FORMYL-2,5-DIMETHYL-1H-PYRROL-1-YL)-N-(PROPAN-2-YL)ACETAMIDE; 2-(3-FORMYL-2,5-DIMETHYL-1H-PYRROL-1-YL)-N-METHYLACETAMIDE; 2-(3-FORMYL-2,5-DIMETHYL-1H-PYRROL-1-YL)-N-METHYLPROPANAMIDE; 2-(3-FORMYL-2,5-DIMETHYL-1H-PYRROL-1-YL)-N-PROPYLPROPANAMIDE; 2-(3-FORMYL-2-METHYL-1H-INDOL-1-YL)-N-(3-METHOXYPROPYL)ACETAMIDE; 2-(3-FORMYL-INDOL-1-YL)-N-(2-METHOXY-ETHYL)-ACETAMIDE; 2-(3-FORMYL-INDOL-1-YL)-N-(TETRAHYDRO-FURAN-2-YLMETHYL)-ACETAMIDE; 2-(3-FORMYL-INDOL-1-YL)-N-FURAN-2-YLMETHYL-ACETAMIDE; 2-(3-FORMYL-INDOL-1-YL)-N-ISOPROPYL-ACETAMIDE; 2-(3-FORMYL-INDOL-1-YL)-N-M-TOLYLACETAMIDE; 2-(3-FORMYL-INDOL-1-YL)-N-O-TOLYL-ACETAMIDE; 2-(3-FORMYL-INDOL-1-YL)-N-PHENYL-ACETAMIDE; 2-(3-FORMYL-INDOL-1-YL)-N-P-TOLYLACETAMIDE; 2-(3-FORMYLPHENOXY)-N-(1-METHOXYPROPAN-2-YL)ACETAMIDE; 2-(3-FORMYLPHENOXY)-N-(2,2,2-TRIFLUOROETHYL)ACETAMIDE; 2-(3-FORMYLPHENOXY)-N-(2-METHOXYETHYL)ACETAMIDE; 2-(3-FORMYLPHENOXY)-N-(2-METHOXYETHYL)PROPANAMIDE; 2-(3-FORMYLPHENOXY)-N-(2-METHYLBUTAN-2-YL)ACETAMIDE; 2-(3-FORMYLPHENOXY)-N-(2-METHYLBUTAN-2-YL)PROPANAMIDE; 2-(3-FORMYLPHENOXY)-N-(2-METHYLPHENYL)ACETAMIDE; 2-(3-FORMYLPHENOXY)-N-(2-METHYLPROPYL)ACETAMIDE; 2-(3-FORMYLPHENOXY)-N-(2-METHYLPROPYL)PROPANAMIDE; 2-(3-FORMYLPHENOXY)-N-(3-METHOXYPHENYL)ACETAMIDE; 2-(3-FORMYLPHENOXY)-N-(3-METHOXYPROPYL)ACETAMIDE; 2-(3-FORMYLPHENOXY)-N-(3-METHOXYPROPYL)PROPANAMIDE; 2-(3-FORMYLPHENOXY)-N-(3-METHYLBUTAN-2-YL)ACETAMIDE; 2-(3-

FORMYLPHENOXY)-N-(3-METHYLBUTYL)ACETAMIDE; 2-(3-FORMYLPHENOXY)-N-(3-METHYLBUTYL)PROPANAMIDE; 2-(3-FORMYLPHENOXY)-N-(3-METHYLPHENYL)ACETAMIDE; 2-(3-FORMYLPHENOXY)-N-(4-METHOXYPHENYL)ACETAMIDE; 2-(3-FORMYLPHENOXY)-N-(4-METHYLPHENYL)ACETAMIDE; 2-(3-FORMYLPHENOXY)-N-(OXAN-4-YL)ACETAMIDE; 2-(3-FORMYLPHENOXY)-N-(PENTAN-2-YL)ACETAMIDE; 2-(3-FORMYLPHENOXY)-N-(PENTAN-2-YL)PROPANAMIDE; 2-(3-FORMYLPHENOXY)-N-(PENTAN-3-YL)ACETAMIDE; 2-(3-FORMYLPHENOXY)-N-(PENTAN-3-YL)PROPANAMIDE; 2-(3-FORMYLPHENOXY)-N-(PROP-2-EN-1-YL)ACETAMIDE; 2-(3-FORMYLPHENOXY)-N-(PROP-2-EN-1-YL)PROPANAMIDE; 2-(3-FORMYLPHENOXY)-N-(PROP-2-YN-1-YL)ACETAMIDE; 2-(3-FORMYLPHENOXY)-N-(PROP-2-YN-1-YL)PROPANAMIDE; 2-(3-FORMYLPHENOXY)-N-(PROPAN-2-YL)ACETAMIDE; 2-(3-FORMYLPHENOXY)-N-(PROPAN-2-YL)PROPANAMIDE; 2-(3-FORMYLPHENOXY)-N-MESITYLACETAMIDE; 2-(3-FORMYLPHENOXY)-N-METHYLACETAMIDE; 2-(3-FORMYLPHENOXY)-N-METHYLPROPANAMIDE; 2-(3-FORMYLPHENOXY)-N-PENTYLPROPANAMIDE; 2-(3-FORMYLPHENOXY)-N-PHENYLACETAMIDE; 2-(3-FORMYLPHENOXY)-N-PROPYLACETAMIDE; 2-(3-FORMYLPHENOXY)-N-PROPYLPROPANAMIDE; 2-(3-FORMYLPIPERIDIN-1-YL)-N-(1,3-THIAZOL-2-YL)ACETAMIDE; 2-(3-FORMYLPIPERIDIN-1-YL)-N-(1-METHOXYPROPAN-2-YL)ACETAMIDE; 2-(3-FORMYLPIPERIDIN-1-YL)-N-(2,2,2-TRIFLUOROETHYL)ACETAMIDE; 2-(3-FORMYLPIPERIDIN-1-YL)-N-(2-METHOXYETHYL)ACETAMIDE; 2-(3-FORMYLPIPERIDIN-1-YL)-N-(2-METHOXYETHYL)PROPANAMIDE; 2-(3-FORMYLPIPERIDIN-1-YL)-N-(2-METHYL-4-OXOPENTAN-3-YL)ACETAMIDE; 2-(3-FORMYLPIPERIDIN-1-YL)-N-(2-METHYLBUTAN-2-YL)ACETAMIDE; 2-(3-FORMYLPIPERIDIN-1-YL)-N-(2-METHYLBUTAN-2-YL)PROPANAMIDE; 2-(3-FORMYLPIPERIDIN-1-YL)-N-(2-METHYLCYCLOHEXYL)ACETAMIDE; 2-(3-FORMYLPIPERIDIN-1-YL)-N-(2-METHYLPHENYL)ACETAMIDE; 2-(3-FORMYLPIPERIDIN-1-YL)-N-(2-METHYLPROPYL)ACETAMIDE; 2-(3-FORMYLPIPERIDIN-1-YL)-N-(2-METHYLPROPYL)PROPANAMIDE; 2-(3-FORMYLPIPERIDIN-1-YL)-N-(3-METHOXYPROPYL)ACETAMIDE; 2-(3-FORMYLPIPERIDIN-1-YL)-N-(3-METHOXYPROPYL)PROPANAMIDE; 2-(3-FORMYLPIPERIDIN-1-YL)-N-(3-METHYL-1,2-OXAZOL-5-YL)ACETAMIDE; 2-(3-FORMYLPIPERIDIN-1-YL)-N-(3-METHYLBUTAN-2-YL)ACETAMIDE; 2-(3-FORMYLPIPERIDIN-1-YL)-N-(3-METHYLBUTYL)ACETAMIDE; 2-(3-FORMYLPIPERIDIN-1-YL)-N-(3-METHYLBUTYL)PROPANAMIDE; 2-(3-FORMYLPIPERIDIN-1-YL)-N-(3-METHYLPHENYL)ACETAMIDE; 2-(3-FORMYLPIPERIDIN-1-YL)-N-(4-METHYL-1,3-THIAZOL-2-YL)ACETAMIDE; 2-(3-FORMYLPIPERIDIN-1-YL)-N-(4-METHYLCYCLOHEXYL)ACETAMIDE; 2-(3-FORMYLPIPERIDIN-1-YL)-N-(4-METHYLPHENYL)ACETAMIDE; 2-(3-FORMYLPIPERIDIN-1-YL)-N-(5-METHYL-1,2-OXAZOL-3-YL)ACETAMIDE; 2-(3-FORMYLPIPERIDIN-1-YL)-N-(5-METHYL-1,3,4-OXADIAZOL-2-YL)ACETAMIDE; 2-(3-FORMYLPIPERIDIN-1-YL)-N-(5-METHYLHEXAN-2-YL)ACETAMIDE; 2-(3-FORMYLPIPERIDIN-1-YL)-N-(FURAN-2-YLMETHYL)ACETAMIDE; 2-(3-FORMYLPIPERIDIN-1-YL)-N-(FURAN-2-YLMETHYL)PROPANAMIDE; 2-(3-FORMYLPIPERIDIN-1-YL)-N-(HEPTAN-2-YL)ACETAMIDE; 2-(3-FORMYLPIPERIDIN-1-YL)-N-(OXAN-4-YL)ACETAMIDE; 2-(3-FORMYLPIPERIDIN-1-YL)-N-(OXOLAN-2-YLMETHYL)ACETAMIDE; 2-(3-FORMYLPIPERIDIN-1-YL)-N-(PENTAN-2-YL)ACETAMIDE; 2-(3-FORMYLPIPERIDIN-1-YL)-N-(PENTAN-2-YL)PROPANAMIDE; 2-(3-FORMYLPIPERIDIN-1-YL)-N-(PENTAN-3-YL)ACETAMIDE; 2-(3-FORMYLPIPERIDIN-1-YL)-N-(PENTAN-3-YL)PROPANAMIDE; 2-(3-FORMYLPIPERIDIN-1-YL)-N-(PROP-2-EN-1-YL)ACETAMIDE; 2-(3-FORMYLPIPERIDIN-1-YL)-N-(PROP-2-EN-1-YL)PROPANAMIDE; 2-(3-FORMYLPIPERIDIN-1-YL)-N-(PROP-2-YN-1-YL)ACETAMIDE; 2-(3-FORMYLPIPERIDIN-1-YL)-N-(PROP-2-YN-1-YL)PROPANAMIDE; 2-(3-FORMYLPIPERIDIN-1-YL)-N-(PROPAN-2-YL)ACETAMIDE; 2-(3-FORMYLPIPERIDIN-1-YL)-N-(PROPAN-2-YL)PROPANAMIDE; 2-(3-FORMYLPIPERIDIN-1-YL)-N-(PYRIMIDIN-2-YL)ACETAMIDE; 2-(3-FORMYLPIPERIDIN-1-YL)-N-(THIOPHEN-2-YLMETHYL)ACETAMIDE; 2-(3-FORMYLPIPERIDIN-1-YL)-N-[1-(FURAN-2-YL)ETHYL]ACETAMIDE; 2-(3-FORMYLPIPERIDIN-1-YL)-N-[1-(THIOPHEN-2-YL)ETHYL]ACETAMIDE; 2-(3-FORMYLPIPERIDIN-1-YL)-N-[2-(THIOPHEN-2-YL)ETHYL]ACETAMIDE; 2-(3-FORMYLPIPERIDIN-1-YL)-N-[3-(PROPAN-2-YLOXY)PROPYL]ACETAMIDE; 2-(3-FORMYLPIPERIDIN-1-YL)-N-METHYLACETAMIDE; 2-(3-FORMYLPIPERIDIN-1-YL)-N-METHYLPROPANAMIDE; 2-(3-FORMYLPIPERIDIN-1-YL)-N-PENTYLPROPANAMIDE; 2-(3-FORMYLPIPERIDIN-1-YL)-N-PHENYLACETAMIDE; 2-(3-FORMYLPIPERIDIN-1-YL)-N-PROPYLACETAMIDE; 2-(3-FORMYLPIPERIDIN-1-YL)-N-PROPYLPROPANAMIDE; 2-(3-IODO-PHENYL)-1H-IMIDAZOLE-4-CARBALDEHYDE; 2-(3-METHOXY-PHENYL)-1H-IMIDAZOLE-4-CARBALDEHYDE; 2-(3-METHOXYPHENYL)-1H-IMIDAZOLE-5-CARBALDEHYDE; 2-(3-METHOXY-PHENYLAMINO)-PYRIMIDINE-5-CARBALDEHYDE; 2-(3-METHYLBENZO[B]THIOPHEN-2-YL)$_4$-FORMYLIMIDAZOLE; 2-(3-METHYLPHENYL)-1H-IMIDAZOLE-5-CARBALDEHYDE; 2-(3-METHYLPHENYL)-5-NITRO-1H-INDOLE-3-CARBOXALDEHYDE; 2-(3-METHYLTHIOPHEN-2-YL)-4-FORMYL-1H-IMIDAZOLE; 2-(3-NITRO-PHENYL)-1H-IMIDAZOLE-4-CARBALDEHYDE; 2-(3-OXO-1,2,3,4-TETRAHYDROQUINOXALIN-1-YL)ACETALDEHYDE; 2-(3-OXO-1,2,3,4-TETRAHYDROQUINOXALIN-1-YL)BENZALDEHYDE; 2-(3-OXOPIPERAZIN-1-YL)-1,3-THIAZOLE-5-CARBALDEHYDE; 2-(3-OXOPIPERAZIN-1-YL)ACETALDEHYDE; 2-(3-OXOPIPERAZIN-1-YL)BENZALDEHYDE; 2-(3-OXOPIPERAZIN-1-YL)IMIDAZO[1,2-A]PYRIDINE-3-CARBALDEHYDE; 2-(3-OXOPIPERAZIN-1-YL)QUINOLINE-3-CARBALDEHYDE; 2-(3-PYRIDINYL)-5-(TRIFLUOROMETHYL)-1H-INDOLE-3-CARBOXALDEHYDE; 2-(3-TRIFLUOROMETHOXY-PHENYL)-4-FORMYL-IMIDAZOLE; 2-(3-

TRIFLUOROMETHYL-PHENYL)-4-FORMYL-IMIDAZOLE; 2-(4-(TRIFLUOROMETHYL)PHENYL)-1H-IMIDAZOLE-5-CARBALDEHYDE; DIMETHYL-2,5-DIOXOIMIDAZOLIDIN-1-YL)ACETALDEHYDE; 2-(4,5-DIMETHOXY-2-NITRO-PHENYL)-4-FORMYLIMIDAZOLE; 2-(4,5-DIMETHYL-FURAN-2-YL)-4-FORMYL-1H-IMIDAZOLE; 2-(4-BROMO-2-FLUORO-PHENYL)-4-FORMYL-IMIDAZOLE; 2-(4-BROMO-2-FORMYLPHENOXY)-N-(CYANOMETHYL)ACETAMIDE; 2-(4-BROMO-2-FORMYLPHENOXY)-N-(PROP-2-EN-1-YL)ACETAMIDE; 2-(4-BROMO-2-FORMYLPHENOXY)-N-CYCLOPROPYLACETAMIDE; 2-(4-BROMO-2-FORMYLPHENOXY)-N-ETHYLACETAMIDE; 2-(4-BROMO-2-FORMYLPHENOXY)-N-METHYLACETAMIDE; 2-(4-BROMO-2-FORMYLPHENOXY)-N-METHYLPROPANAMIDE; 2-(4-BROMO-2-FORMYLPHENOXY)-N-PROP-2-YNYLACETAMIDE; 2-(4-BROMO-3-NITRO-PHENYL)-4-FORMYL-IMIDAZOLE; 2-(4-BROMO-PHENYL)-1H-IMIDAZOLE-4-CARBALDEHYDE; 2-(4-BROMOPHENYL)-1H-IMIDAZOLE-5-CARBALDEHYDE; 2-(4-BROMO-PHENYLAMINO)-PYRIMIDINE-5-CARBALDEHYDE; 2-(4-CHLORO-2-FORMYLPHENOXY)-N-(1-METHOXYPROPAN-2-YL)ACETAMIDE; 2-(4-CHLORO-2-FORMYLPHENOXY)-N-(2,2,2-TRIFLUOROETHYL)ACETAMIDE; 2-(4-CHLORO-2-FORMYLPHENOXY)-N-(2-CYANOETHYL)ACETAMIDE; 2-(4-CHLORO-2-FORMYLPHENOXY)-N-(2-METHOXYETHYL)ACETAMIDE; 2-(4-CHLORO-2-FORMYLPHENOXY)-N-(2-METHOXYETHYL)PROPANAMIDE; 2-(4-CHLORO-2-FORMYLPHENOXY)-N-(2-METHYLBUTAN-2-YL)ACETAMIDE; 2-(4-CHLORO-2-FORMYLPHENOXY)-N-(2-METHYLPROPYL)ACETAMIDE; 2-(4-CHLORO-2-FORMYLPHENOXY)-N-(2-METHYLPROPYL)PROPANAMIDE; 2-(4-CHLORO-2-FORMYLPHENOXY)-N-(3-METHOXYPROPYL)ACETAMIDE; 2-(4-CHLORO-2-FORMYLPHENOXY)-N-(3-METHYLBUTAN-2-YL)ACETAMIDE; 2-(4-CHLORO-2-FORMYLPHENOXY)-N-(3-METHYLBUTYL)ACETAMIDE; 2-(4-CHLORO-2-FORMYLPHENOXY)-N-(CYANOMETHYL)ACETAMIDE; 2-(4-CHLORO-2-FORMYLPHENOXY)-N-(CYCLOPROPYLMETHYL)ACETAMIDE; 2-(4-CHLORO-2-FORMYLPHENOXY)-N-(PENTAN-2-YL)ACETAMIDE; 2-(4-CHLORO-2-FORMYLPHENOXY)-N-(PENTAN-3-YL)ACETAMIDE; 2-(4-CHLORO-2-FORMYLPHENOXY)-N-(PROP-2-EN-1-YL)ACETAMIDE; 2-(4-CHLORO-2-FORMYLPHENOXY)-N-(PROP-2-EN-1-YL)PROPANAMIDE; 2-(4-CHLORO-2-FORMYLPHENOXY)-N-(PROP-2-YN-1-YL)ACETAMIDE; 2-(4-CHLORO-2-FORMYLPHENOXY)-N-(PROP-2-YN-1-YL)PROPANAMIDE; 2-(4-CHLORO-2-FORMYLPHENOXY)-N-(PROPAN-2-YL)ACETAMIDE; 2-(4-CHLORO-2-FORMYLPHENOXY)-N-(PROPAN-2-YL)PROPANAMIDE; 2-(4-CHLORO-2-FORMYLPHENOXY)-N-(TETRAHYDROFURAN-2-YLMETHYL)ACETAMIDE; 2-(4-CHLORO-2-FORMYLPHENOXY)-N-CYCLOPENTYLACETAMIDE; 2-(4-CHLORO-2-FORMYLPHENOXY)-N-CYCLOPROPYLACETAMIDE; 2-(4-CHLORO-2-FORMYLPHENOXY)-N-CYCLOPROPYLPROPANAMIDE; 2-(4-CHLORO-2-FORMYLPHENOXY)-N-ETHYLACETAMIDE; 2-(4-CHLORO-2-FORMYLPHENOXY)-N-ETHYLPROPANAMIDE; 2-(4-CHLORO-2-FORMYLPHENOXY)-N-METHYLACETAMIDE; 2-(4-CHLORO-2-FORMYLPHENOXY)-N-METHYLPROPANAMIDE; 2-(4-CHLORO-2-FORMYLPHENOXY)-N-PROPYLACETAMIDE; 2-(4-CHLORO-2-FORMYLPHENOXY)-N-PROPYLPROPANAMIDE; 2-(4-CHLORO-3-FLUORO-PHENYL)-4-FORMYL-IMIDAZOLE; 2-(4-CHLORO-3-NITRO-PHENYL)-4-FORMYL-IMIDAZOLE; 2-(4-CHLORO-PHENYL)-1H-IMIDAZOLE-4-CARBALDEHYDE; 2-(4-CHLOROPHENYL)-1H-IMIDAZOLE-5-CARBALDEHYDE; 2-(4-CHLOROPHENYL)-1H-INDOLE-3-CARBALDEHYDE; 2-(4-CHLOROPHENYL)-4,6-DIFLUORO-1H-INDOLE-3-CARBOXALDEHYDE; 2-(4-CHLOROPHENYL)-4,6-DIMETHYL-1H-INDOLE-3-CARBOXALDEHYDE; 2-(4-CHLOROPHENYL)-4,7-DIFLUORO-1H-INDOLE-3-CARBOXALDEHYDE; 2-(4-CHLOROPHENYL)-4,7-DIMETHYL-1H-INDOLE-3-CARBOXALDEHYDE; 2-(4-CHLOROPHENYL)-5-(1-METHYLETHYL)-1H-INDOLE-3-CARBOXALDEHYDE; 2-(4-CHLOROPHENYL)-5,7-DIFLUORO-1H-INDOLE-3-CARBOXALDEHYDE; 2-(4-CHLOROPHENYL)-5,7-DIMETHYL-1H-INDOLE-3-CARBOXALDEHYDE; 2-(4-CHLOROPHENYL)-5-ETHOXY-1H-INDOLE-3-CARBOXALDEHYDE; 2-(4-CHLOROPHENYL)-5-FLUORO-1H-INDOLE-3-CARBOXALDEHYDE; 2-(4-CHLOROPHENYL)-5-METHOXY-1H-INDOLE-3-CARBOXALDEHYDE; 2-(4-CHLOROPHENYL)-5-METHYL-1H-INDOLE-3-CARBOXALDEHYDE; 2-(4-CHLOROPHENYL)-6,7-DIFLUORO-1H-INDOLE-3-CARBOXALDEHYDE; 2-(4-CHLOROPHENYL)-6,7-DIMETHYL-1H-INDOLE-3-CARBOXALDEHYDE; 2-(4-CHLOROPHENYL)-7-FLUORO-1H-INDOLE-3-CARBOXALDEHYDE; 2-(4-CHLOROPHENYL)-7-FLUORO-5-METHYL-1H-INDOLE-3-CARBOXALDEHYDE; 2-(4-CHLOROPHENYL)-7-METHOXY-1H-INDOLE-3-CARBOXALDEHYDE; 2-(4-CHLOROPHENYL)-7-METHYL-1H-INDOLE-3-CARBOXALDEHYDE; 2-(4-CHLOROPHENYLAMINO)-PYRIMIDINE-5-CARBALDEHYDE; 2-(4-ETHOXYPHENYL)-1H-INDOLE-3-CARBALDEHYDE; 2-(4-ETHOXY-PHENYL)-4-FORMYL-1H-IMIDAZOLE; 2-(4-ETHOXY-PHENYLAMINO)-PYRIMIDINE-5-CARBALDEHYDE; 2-(4-ETHYLPHENYL)-1H-INDOLE-3-CARBALDEHYDE; 2-(4-ETHYL-PHENYL)-4-FORMYL-1H-IMIDAZOLE; 2-(4-ETHYLPHENYL)-5-(1-METHYLETHYL)-1H-INDOLE-3-CARBOXALDEHYDE; 2-(4-ETHYLPHENYL)-5-FLUORO-1H-INDOLE-3-CARBOXALDEHYDE; 2-(4-ETHYLPHENYL)-5-METHOXY-1H-INDOLE-3-CARBOXALDEHYDE; 2-(4-ETHYLPHENYL)-5-METHYL-1H-INDOLE-3-CARBOXALDEHYDE; 2-(4-ETHYLPHENYL)-5-NITRO-1H-INDOLE-3-CARBOXALDEHYDE; 2-(4-ETHYLPHENYL)-7-FLUORO-1H-INDOLE-3-CARBOXALDEHYDE; 2-(4-ETHYLPHENYL)-7-FLUORO-5-METHYL-1H-INDOLE-3-CARBOXALDEHYDE; 2-(4-ETHYLPHENYL)-7-METHOXY-1H-INDOLE-3-CARBOXALDEHYDE; 2-(4-ETHYLPHENYL)-7-METHYL-1H-INDOLE-3-CARBOXALDEHYDE; 2-(4-ETHYL-PHENYLAMINO)-PYRIMIDINE-5-CARBALDEHYDE; 2-(4-FLUORO-3-METHYL-PHENYL)-4-FORMYL-IMIDAZOLE; 2-(4-FLUORO-3-NITRO-PHENYL)-4-FORMYL-IMIDAZOLE; 2-(4-FLUORO-3-NITROPHENYL)-5-METHYL-1H-INDOLE-3-CARBOXALDEHYDE; 2-(4-FLUORO-3-NITROPHENYL)-7-METHYL-1H-INDOLE-3-CARBOXALDEHYDE; 2-(4-FLUOROPHENYL)-1,2-DIHYDROQUINOLINE-4-CARBALDEHYDE; 2-(4-FLUORO-PHENYL)-1H-IMIDAZOLE-4-

CARBALDEHYDE; 2-(4-FLUOROPHENYL)-1H-IMIDAZOLE-5-CARBALDEHYDE; 2-(4-FLUOROPHENYL)-1H-INDOLE-3-CARBALDEHYDE; 2-(4-FLUOROPHENYL)-5-(1-METHYLETHYL)-1H-INDOLE-3-CARBOXALDEHYDE; 2-(4-FLUOROPHENYL)-5-METHOXY-1H-INDOLE-3-CARBOXALDEHYDE; 2-(4-FLUOROPHENYL)-5-METHYL-1H-INDOLE-3-CARBOXALDEHYDE; 2-(4-FLUOROPHENYL)-5-NITRO-1H-INDOLE-3-CARBOXALDEHYDE; 2-(4-FLUOROPHENYL)-7-METHOXY-1H-INDOLE-3-CARBOXALDEHYDE; 2-(4-FLUOROPHENYL)-7-METHYL-1H-INDOLE-3-CARBOXALDEHYDE; 2-(4-FLUOROPHENYL)-7-METHYL-5-NITRO-1H-INDOLE-3-CARBOXALDEHYDE; 2-(4-FORMYL-1H-IMIDAZOL-2-YL)-3-METHOXY-PHENOL; 2-(4-FORMYL-1H-IMIDAZOL-2-YL)-4-METHOXY-PHENOL; 2-(4-FORMYL-1H-IMIDAZOL-2-YL)-4-NITRO-PHENOL; 2-(4-FORMYL-1H-IMIDAZOL-2-YL)-5-METHOXY-PHENOL; 2-(4-FORMYL-1H-IMIDAZOL-2-YL)-6-METHOXY-PHENOL; 2-(4-FORMYL-1H-IMIDAZOL-2-YL)-BENZOIC ACID; 2-(4-FORMYL-1H-IMIDAZOL-2-YL)-BENZONITRILE; 2-(4-FORMYL-1H-IMIDAZOL-2-YL)-PHENOL; 2-(4-FORMYL-2,6-DIMETHOXYPHENOXY)-N-(2-METHOXYETHYL)ACETAMIDE; 2-(4-FORMYL-2,6-DIMETHOXYPHENOXY)-N-METHYLACETAMIDE; 2-(4-FORMYL-2,6-DIMETHYLPHENOXY)-N-(2,2,2-TRIFLUOROETHYL)ACETAMIDE; 2-(4-FORMYL-2,6-DIMETHYLPHENOXY)-N-(2-METHOXYETHYL)ACETAMIDE; 2-(4-FORMYL-2,6-DIMETHYLPHENOXY)-N-(PROP-2-EN-1-YL)ACETAMIDE; 2-(4-FORMYL-2,6-DIMETHYLPHENOXY)-N-(PROP-2-EN-1-YL)PROPANAMIDE; 2-(4-FORMYL-2,6-DIMETHYLPHENOXY)-N-(PROP-2-YN-1-YL)ACETAMIDE; 2-(4-FORMYL-2,6-DIMETHYLPHENOXY)-N-(PROP-2-YN-1-YL)PROPANAMIDE; 2-(4-FORMYL-2,6-DIMETHYLPHENOXY)-N-(PROPAN-2-YL)ACETAMIDE; 2-(4-FORMYL-2,6-DIMETHYLPHENOXY)-N-(PROPAN-2-YL)PROPANAMIDE; 2-(4-FORMYL-2,6-DIMETHYLPHENOXY)-N-(TETRAHYDROFURAN-2-YLMETHYL)ACETAMIDE; 2-(4-FORMYL-2,6-DIMETHYLPHENOXY)-N-ISOBUTYLACETAMIDE; 2-(4-FORMYL-2,6-DIMETHYLPHENOXY)-N-METHYLACETAMIDE; 2-(4-FORMYL-2,6-DIMETHYLPHENOXY)-N-METHYLPROPANAMIDE; 2-(4-FORMYL-2,6-DIMETHYLPHENOXY)-N-PROPYLACETAMIDE; 2-(4-FORMYL-2,6-DIMETHYLPHENOXY)-N-PROPYLPROPANAMIDE; 2-(4-FORMYL-2-METHOXY-5-NITROPHENOXY)-N-METHYLACETAMIDE; 2-(4-FORMYL-2-METHOXY-6-NITROPHENOXY)-N-PROP-2-YNYLACETAMIDE; 2-(4-FORMYL-2-METHOXYPHENOXY)-N-(2-METHOXYETHYL)ACETAMIDE; 2-(4-FORMYL-2-METHOXYPHENOXY)-N-(3-METHYLPHENYL)ACETAMIDE; 2-(4-FORMYL-2-METHOXYPHENOXY)-N-(5-METHYLISOXAZOL-3-YL)ACETAMIDE; 2-(4-FORMYL-2-METHOXYPHENOXY)-N-(PROP-2-EN-1-YL)ACETAMIDE; 2-(4-FORMYL-2-METHOXYPHENOXY)-N-(PROP-2-EN-1-YL)PROPANAMIDE; 2-(4-FORMYL-2-METHOXYPHENOXY)-N-(PROP-2-YN-1-YL)ACETAMIDE; 2-(4-FORMYL-2-METHOXYPHENOXY)-N-(PROP-2-YN-1-YL)PROPANAMIDE; 2-(4-FORMYL-2-METHOXYPHENOXY)-N-(PROPAN-2-YL)ACETAMIDE; 2-(4-FORMYL-2-METHOXYPHENOXY)-N-(PROPAN-2-YL)PROPANAMIDE; 2-(4-FORMYL-2-METHOXYPHENOXY)-N-(TETRAHYDROFURAN-2-YLMETHYL)ACETAMIDE; 2-(4-FORMYL-2-METHOXYPHENOXY)-N-ISOBUTYLACETAMIDE; 2-(4-FORMYL-2-METHOXYPHENOXY)-N-METHYLACETAMIDE; 2-(4-FORMYL-2-METHOXYPHENOXY)-N-METHYLPROPANAMIDE; 2-(4-FORMYL-2-METHOXY-PHENOXY)-N-O-TOLYL-ACETAMIDE; 2-(4-FORMYL-2-METHOXYPHENOXY)-N-PHENYLACETAMIDE; 2-(4-FORMYL-2-METHOXYPHENOXY)-N-PROPYLACETAMIDE; 2-(4-FORMYL-2-METHOXYPHENOXY)-N-PROPYLPROPANAMIDE; 2-(4-FORMYL-2-METHOXY-PHENOXY)-N-P-TOLYL-ACETAMIDE; 2-(4-FORMYL-2-NITROPHENOXY)-N-(PROP-2-EN-1-YL)ACETAMIDE; 2-(4-FORMYL-2-NITROPHENOXY)-N-(PROP-2-YN-1-YL)ACETAMIDE; 2-(4-FORMYL-2-NITROPHENOXY)-N-(PROPAN-2-YL)ACETAMIDE; 2-(4-FORMYL-2-NITROPHENOXY)-N-METHYLACETAMIDE; 2-(4-FORMYL-2-NITROPHENOXY)-N-METHYLPROPANAMIDE; 2-(4-FORMYL-2-NITROPHENOXY)-N-PROPYLACETAMIDE; 2-(4-FORMYL-3,5-DIMETHYL-1H-PYRAZOL-1-YL)-N-(2,2,2-TRIFLUOROETHYL)ACETAMIDE; 2-(4-FORMYL-3,5-DIMETHYL-1H-PYRAZOL-1-YL)-N-(2-METHOXYETHYL)ACETAMIDE; 2-(4-FORMYL-3,5-DIMETHYL-1H-PYRAZOL-1-YL)-N-(2-METHYLBUTAN-2-YL)ACETAMIDE; 2-(4-FORMYL-3,5-DIMETHYL-1H-PYRAZOL-1-YL)-N-(2-METHYLPROPYL)ACETAMIDE; 2-(4-FORMYL-3,5-DIMETHYL-1H-PYRAZOL-1-YL)-N-(3-METHOXYPROPYL)ACETAMIDE; 2-(4-FORMYL-3,5-DIMETHYL-1H-PYRAZOL-1-YL)-N-(3-METHYLBUTYL)ACETAMIDE; 2-(4-FORMYL-3,5-DIMETHYL-1H-PYRAZOL-1-YL)-N-(OXAN-4-YL)ACETAMIDE; 2-(4-FORMYL-3,5-DIMETHYL-1H-PYRAZOL-1-YL)-N-(PENTAN-3-YL)ACETAMIDE; 2-(4-FORMYL-3,5-DIMETHYL-1H-PYRAZOL-1-YL)-N-(PROP-2-EN-1-YL)ACETAMIDE; 2-(4-FORMYL-3,5-DIMETHYL-1H-PYRAZOL-1-YL)-N-(PROP-2-YN-1-YL)ACETAMIDE; 2-(4-FORMYL-3,5-DIMETHYL-1H-PYRAZOL-1-YL)-N-(PROPAN-2-YL)ACETAMIDE; 2-(4-FORMYL-3,5-DIMETHYL-1H-PYRAZOL-1-YL)-N-METHYLACETAMIDE; 2-(4-FORMYL-3,5-DIMETHYL-1H-PYRAZOL-1-YL)-N-PHENYLACETAMIDE; 2-(4-FORMYLIMIDAZOL-2-YL)-4-TRIFLUOROMETHOXYPHENOL; 2-(4-FORMYL-IMIDAZOL-2-YL)-5-METHOXY-4-NITROPHENOL; 2-(4-FORMYLPHENOXY)-N-(1-METHOXYPROPAN-2-YL)ACETAMIDE; 2-(4-FORMYLPHENOXY)-N-(2,2,2-TRIFLUOROETHYL)ACETAMIDE; 2-(4-FORMYLPHENOXY)-N-(2-FURYLMETHYL)ACETAMIDE; 2-(4-FORMYLPHENOXY)-N-(2-METHOXYETHYL)ACETAMIDE; 2-(4-FORMYLPHENOXY)-N-(2-METHOXYETHYL)PROPANAMIDE; 2-(4-FORMYLPHENOXY)-N-(2-METHYLBUTAN-2-YL)ACETAMIDE; 2-(4-FORMYLPHENOXY)-N-(2-METHYLBUTAN-2-YL)PROPANAMIDE; 2-(4-FORMYLPHENOXY)-N-(2-METHYLCYCLOHEXYL)ACETAMIDE; 2-(4-FORMYLPHENOXY)-N-(2-METHYLPHENYL)ACETAMIDE; 2-(4-FORMYLPHENOXY)-N-(2-METHYLPROPYL)PROPANAMIDE; 2-(4-FORMYLPHENOXY)-N-(3-METHOXYPHENYL)ACETAMIDE; 2-(4-FORMYLPHENOXY)-N-(3-METHOXYPROPYL)

ACETAMIDE; 2-(4-FORMYLPHENOXY)-N-(3-METHOXYPROPYL)PROPANAMIDE; 2-(4-FORMYLPHENOXY)-N-(3-METHYLBUTAN-2-YL)ACETAMIDE; 2-(4-FORMYLPHENOXY)-N-(3-METHYLBUTYL)ACETAMIDE; 2-(4-FORMYLPHENOXY)-N-(3-METHYLBUTYL)PROPANAMIDE; 2-(4-FORMYLPHENOXY)-N-(3-METHYLPHENYL)ACETAMIDE; 2-(4-FORMYLPHENOXY)-N-(4-METHOXYPHENYL)ACETAMIDE; 2-(4-FORMYLPHENOXY)-N-(4-METHYLBENZYL)ACETAMIDE; 2-(4-FORMYLPHENOXY)-N-(4-METHYLPHENYL)ACETAMIDE; 2-(4-FORMYLPHENOXY)-N-(OXAN-4-YL)ACETAMIDE; 2-(4-FORMYLPHENOXY)-N-(PENTAN-2-YL)ACETAMIDE; 2-(4-FORMYLPHENOXY)-N-(PENTAN-2-YL)PROPANAMIDE; 2-(4-FORMYLPHENOXY)-N-(PENTAN-3-YL)ACETAMIDE; 2-(4-FORMYLPHENOXY)-N-(PENTAN-3-YL)PROPANAMIDE; 2-(4-FORMYLPHENOXY)-N-(PROP-2-EN-1-YL)ACETAMIDE; 2-(4-FORMYLPHENOXY)-N-(PROP-2-EN-1-YL)PROPANAMIDE; 2-(4-FORMYLPHENOXY)-N-(PROP-2-YN-1-YL)ACETAMIDE; 2-(4-FORMYLPHENOXY)-N-(PROP-2-YN-1-YL)PROPANAMIDE; 2-(4-FORMYLPHENOXY)-N-(PROPAN-2-YL)ACETAMIDE; 2-(4-FORMYLPHENOXY)-N-(PROPAN-2-YL)PROPANAMIDE; 2-(4-FORMYL-PHENOXY)-N-(TETRAHYDRO-FURAN-2-YLMETHYL)-ACETAMIDE; 2-(4-FORMYL-PHENOXY)-N-[2-(1H-IMIDAZOL-4-YL)-ETHYL]-ACETAMIDE; 2-(4-FORMYLPHENOXY)-N-1,3-THIAZOL-2-YLACETAMIDE; 2-(4-FORMYLPHENOXY)-N-2-PYRIDINYLACETAMIDE; 2-(4-FORMYLPHENOXY)-N-ISOBUTYLACETAMIDE; 2-(4-FORMYLPHENOXY)-N-MESITYLACETAMIDE; 2-(4-FORMYLPHENOXY)-N-METHYLACETAMIDE; 2-(4-FORMYLPHENOXY)-N-METHYLPROPANAMIDE; 2-(4-FORMYLPHENOXY)-N-PENTYLACETAMIDE; 2-(4-FORMYLPHENOXY)-N-PENTYLPROPANAMIDE; 2-(4-FORMYLPHENOXY)-N-PHENYLACETAMIDE; 2-(4-FORMYLPHENOXY)-N-PROPYLACETAMIDE; 2-(4-FORMYLPHENOXY)-N-PROPYLPROPANAMIDE; 2-(4-FORMYLPIPERIDIN-1-YL)-N-(1,3-THIAZOL-2-YL)ACETAMIDE; 2-(4-FORMYLPIPERIDIN-1-YL)-N-(1-METHOXYPROPAN-2-YL)ACETAMIDE; 2-(4-FORMYLPIPERIDIN-1-YL)-N-(2,2,2-TRIFLUOROETHYL)ACETAMIDE; 2-(4-FORMYLPIPERIDIN-1-YL)-N-(2-METHOXYETHYL)ACETAMIDE; 2-(4-FORMYLPIPERIDIN-1-YL)-N-(2-METHOXYETHYL)PROPANAMIDE; 2-(4-FORMYLPIPERIDIN-1-YL)-N-(2-METHYL-4-OXOPENTAN-3-YL)ACETAMIDE; 2-(4-FORMYLPIPERIDIN-1-YL)-N-(2-METHYLBUTAN-2-YL)ACETAMIDE; 2-(4-FORMYLPIPERIDIN-1-YL)-N-(2-METHYLBUTAN-2-YL)PROPANAMIDE; 2-(4-FORMYLPIPERIDIN-1-YL)-N-(2-METHYLCYCLOHEXYL)ACETAMIDE; 2-(4-FORMYLPIPERIDIN-1-YL)-N-(2-METHYLPHENYL)ACETAMIDE; 2-(4-FORMYLPIPERIDIN-1-YL)-N-(2-METHYLPROPYL)ACETAMIDE; 2-(4-FORMYLPIPERIDIN-1-YL)-N-(2-METHYLPROPYL)PROPANAMIDE; 2-(4-FORMYLPIPERIDIN-1-YL)-N-(3-METHOXYPROPYL)ACETAMIDE; 2-(4-FORMYLPIPERIDIN-1-YL)-N-(3-METHOXYPROPYL)PROPANAMIDE; 2-(4-FORMYLPIPERIDIN-1-YL)-N-(3-METHYL-1,2-OXAZOL-5-YL)ACETAMIDE; 2-(4-FORMYLPIPERIDIN-1-YL)-N-(3-METHYLBUTAN-2-YL)ACETAMIDE; 2-(4-FORMYLPIPERIDIN-1-YL)-N-(3-METHYLBUTYL)ACETAMIDE; 2-(4-FORMYLPIPERIDIN-1-YL)-N-(3-METHYLBUTYL)PROPANAMIDE; 2-(4-FORMYLPIPERIDIN-1-YL)-N-(3-METHYLPHENYL)ACETAMIDE; 2-(4-FORMYLPIPERIDIN-1-YL)-N-(4-METHYL-1,3-THIAZOL-2-YL)ACETAMIDE; 2-(4-FORMYLPIPERIDIN-1-YL)-N-(4-METHYLCYCLOHEXYL)ACETAMIDE; 2-(4-FORMYLPIPERIDIN-1-YL)-N-(4-METHYLPHENYL)ACETAMIDE; 2-(4-FORMYLPIPERIDIN-1-YL)-N-(5-METHYL-1,2-OXAZOL-3-YL)ACETAMIDE; 2-(4-FORMYLPIPERIDIN-1-YL)-N-(5-METHYL-1,3,4-OXADIAZOL-2-YL)ACETAMIDE; 2-(4-FORMYLPIPERIDIN-1-YL)-N-(5-METHYLHEXAN-2-YL)ACETAMIDE; 2-(4-FORMYLPIPERIDIN-1-YL)-N-(FURAN-2-YLMETHYL)ACETAMIDE; 2-(4-FORMYLPIPERIDIN-1-YL)-N-(FURAN-2-YLMETHYL)PROPANAMIDE; 2-(4-FORMYLPIPERIDIN-1-YL)-N-(HEPTAN-2-YL)ACETAMIDE; 2-(4-FORMYLPIPERIDIN-1-YL)-N-(OXAN-4-YL)ACETAMIDE; 2-(4-FORMYLPIPERIDIN-1-YL)-N-(OXOLAN-2-YLMETHYL)ACETAMIDE; 2-(4-FORMYLPIPERIDIN-1-YL)-N-(PENTAN-2-YL)ACETAMIDE; 2-(4-FORMYLPIPERIDIN-1-YL)-N-(PENTAN-2-YL)PROPANAMIDE; 2-(4-FORMYLPIPERIDIN-1-YL)-N-(PENTAN-3-YL)ACETAMIDE; 2-(4-FORMYLPIPERIDIN-1-YL)-N-(PENTAN-3-YL)PROPANAMIDE; 2-(4-FORMYLPIPERIDIN-1-YL)-N-(PROP-2-EN-1-YL)ACETAMIDE; 2-(4-FORMYLPIPERIDIN-1-YL)-N-(PROP-2-EN-1-YL)PROPANAMIDE; 2-(4-FORMYLPIPERIDIN-1-YL)-N-(PROP-2-YN-1-YL)ACETAMIDE; 2-(4-FORMYLPIPERIDIN-1-YL)-N-(PROP-2-YN-1-YL)PROPANAMIDE; 2-(4-FORMYLPIPERIDIN-1-YL)-N-(PROPAN-2-YL)ACETAMIDE; 2-(4-FORMYLPIPERIDIN-1-YL)-N-(PROPAN-2-YL)PROPANAMIDE; 2-(4-FORMYLPIPERIDIN-1-YL)-N-(PYRIMIDIN-2-YL)ACETAMIDE; 2-(4-FORMYLPIPERIDIN-1-YL)-N-(THIOPHEN-2-YLMETHYL)ACETAMIDE; 2-(4-FORMYLPIPERIDIN-1-YL)-N-[1-(FURAN-2-YL)ETHYL]ACETAMIDE; 2-(4-FORMYLPIPERIDIN-1-YL)-N-[1-(THIOPHEN-2-YL)ETHYL]ACETAMIDE; 2-(4-FORMYLPIPERIDIN-1-YL)-N-[2-(THIOPHEN-2-YL)ETHYL]ACETAMIDE; 2-(4-FORMYLPIPERIDIN-1-YL)-N-[3-(PROPAN-2-YLOXY)PROPYL]ACETAMIDE; 2-(4-FORMYLPIPERIDIN-1-YL)-N-METHYLACETAMIDE; 2-(4-FORMYLPIPERIDIN-1-YL)-N-METHYLPROPANAMIDE; 2-(4-FORMYLPIPERIDIN-1-YL)-N-PENTYLPROPANAMIDE; 2-(4-FORMYLPIPERIDIN-1-YL)-N-PHENYLACETAMIDE; 2-(4-FORMYLPIPERIDIN-1-YL)-N-PROPYLACETAMIDE; 2-(4-FORMYLPIPERIDIN-1-YL)-N-PROPYLPROPANAMIDE; 2-(4H-1,2,4-TRIAZOL-3-YL)-1,3-THIAZOLE-4-CARBALDEHYDE; 2-(4H-1,2,4-TRIAZOL-3-YL)-1,3-THIAZOLE-5-CARBALDEHYDE; 2-(4-HYDROXY-PHENYL)-3H-BENZOIMIDAZOLE-5-CARBALDEHYDE; 2-(4-IODO-PHENYL)-1H-IMIDAZOLE-4-CARBALDEHYDE; 2-(4-ISOPROPOXY-PHENYL)-4-FORMYL-1H-IMIDAZOLE; 2-(4-ISOPROPYLPHENYL)-1H-INDOLE-3-CARBALDEHYDE; 2-(4-ISOPROPYL-PHENYL)-4-FORMYL-IMIDAZOLE; 2-(4-METHOXY-2-NITRO-PHENYL)-4-FORMYL-1H-IMIDAZOLE; 2-(4-METHOXY-3-METHYLPHENYL)-1H-INDOLE-3-

CARBALDEHYDE; 2-(4-METHOXY-NAPHTHALEN-1-YL)-4-FORMYL-IMIDAZOLE; 2-(4-METHOXY-PHENYL)-1H-IMIDAZOLE-4-CARBALDEHYDE; 2-(4-METHOXYPHENYL)-1H-IMIDAZOLE-5-CARBALDEHYDE; 2-(4-METHOXYPHENYL)-1H-INDOLE-3-CARBALDEHYDE; 2-(4-METHOXY-PHENYLAMINO)-PYRIMIDINE-5-CARBALDEHYDE; 2-(4-METHYL-3-NITRO-PHENYL)-4-FORMYL-1H-IMIDAZOLE; 2-(4-METHYLPHENYL)-1H-IMIDAZOLE-5-CARBALDEHYDE; 2-(4-METHYLPHENYL)-1H-INDOLE-3-CARBALDEHYDE; 2-(4-METHYLPHENYL)-5-NITRO-1H-INDOLE-3-CARBOXALDEHYDE; 2-(4-NITRO-PHENYL)-1H-IMIDAZOLE-4-CARBALDEHYDE; 2-(4-TERT-BUTYL-PHENYL)-4-FORMYL-1H-IMIDAZOLE; 2-(4-TRIFLUOROMETHOXY-PHENYL)-4-FORMYL-IMIDAZOLE; 2-(4-TRIFLUOROMETHYL-PHENYL)-4-FORMYL-IMIDAZOLE; 2-(5,6,7,8-TETRAHYDRO-[1,2,4]TRIAZOLO[4,3-A]PYRAZIN-3-YL)-BENZALDEHYDE; 2-(5,6,7,8-TETRAHYDRONAPHTHALEN-2-YL)-1H-INDOLE-3-CARBALDEHYDE; 2-(5-BROMO-2-FLUORO-PHENYL)-4-FORMYL-IMIDAZOLE; 2-(5-BROMO-2-METHOXY-PHENYL)-4-FORMYLIMIDAZOLE; 2-(5-BROMO-FURAN-2-YL)-4-FORMYL-1H-IMIDAZOLE; 2-(5-BROMO-THIOPHEN-2-YL)-4-FORMYL-1H-IMIDAZOLE; 2-(5-CHLORO-FURAN-2-YL)-4-FORMYL-1H-IMIDAZOLE; 2-(5-CHLORO-THIOPHEN-2-YL)-4-FORMYL-1H-IMIDAZOLE; 2-(5-ETHYL-FURAN-2-YL)-4-FORMYL-1H-IMIDAZOLE; 2-(5-ETHYL-THIOPHEN-2-YL)-4-FORMYL-1H-IMIDAZOLE; 2-(5-FLUORO-2,4-DIOXO-1,2,3,4-TETRAHYDROPYRIMIDIN-1-YL)ACETALDEHYDE; 2-(5-FLUORO-2-METHOXY-PHENYL)-4-FORMYL-IMIDAZOLE; 2-(5-FLUORO-2-NITRO-PHENYL)-4-FORMYL-IMIDAZOLE; 2-(5-FORMYL-2-METHOXY-PHENOXY)-N-(2,2,2-TRIFLUOROETHYL)ACETAMIDE; 2-(5-FORMYL-2-METHOXYPHENOXY)-N-(2-METHOXYETHYL)ACETAMIDE; 2-(5-FORMYL-2-METHOXYPHENOXY)-N-(2-METHYLPROPYL)ACETAMIDE; 2-(5-FORMYL-2-METHOXYPHENOXY)-N-(PROP-2-EN-1-YL)ACETAMIDE; 2-(5-FORMYL-2-METHOXYPHENOXY)-N-(PROP-2-EN-1-YL)PROPANAMIDE; 2-(5-FORMYL-2-METHOXYPHENOXY)-N-(PROP-2-YN-1-YL)ACETAMIDE; 2-(5-FORMYL-2-METHOXYPHENOXY)-N-(PROP-2-YN-1-YL)PROPANAMIDE; 2-(5-FORMYL-2-METHOXYPHENOXY)-N-(PROPAN-2-YL)ACETAMIDE; 2-(5-FORMYL-2-METHOXYPHENOXY)-N-(PROPAN-2-YL)PROPANAMIDE; 2-(5-FORMYL-2-METHOXYPHENOXY)-N-METHYLACETAMIDE; 2-(5-FORMYL-2-METHOXYPHENOXY)-N-METHYLPROPANAMIDE; 2-(5-FORMYL-2-METHOXYPHENOXY)-N-PROPYLACETAMIDE; 2-(5-FORMYL-2-METHOXYPHENOXY)-N-PROPYLPROPANAMIDE; 2-(5-FORMYL-2-NITROPHENOXY)-N-(PROP-2-EN-1-YL)ACETAMIDE; 2-(5-FORMYL-2-NITROPHENOXY)-N-(PROP-2-YN-1-YL)ACETAMIDE; 2-(5-FORMYL-2-NITROPHENOXY)-N-(PROPAN-2-YL)ACETAMIDE; 2-(5-FORMYL-2-NITROPHENOXY)-N-METHYLACETAMIDE; 2-(5-FORMYL-2-NITROPHENOXY)-N-METHYLPROPANAMIDE; 2-(5-FORMYL-2-NITROPHENOXY)-N-PROPYLACETAMIDE; 2-(5-HYDROXY-1H-INDOL-3-YL)ACETALDEHYDE; 2-(5-IODO-FURAN-2-YL)-4-FORMYL-IMIDAZOLE; 2-(5-ISOPROPYL-2-METHOXY-PHENYL)-4-FORMYLIMIDAZOLE; 2-(5-METHYL-FURAN-2-YL)-4-FORMYL-1H-IMIDAZOLE; 2-(5-METHYL-THIOPHEN-2-YL)-4-FORMYL-1H-IMIDAZOLE; 2-(5-NITRO-FURAN-2-YL)-4-FORMYL-1H-IMIDAZOLE; 2-(5-NITRO-THIOPHEN-2-YL)-4-FORMYL-1H-IMIDAZOLE; 2-(5-NITRO-THIOPHEN-3-YL)-4-FORMYL-IMIDAZOLE; 2-(5-OXO-1,4-DIAZEPAN-1-YL)-1,3-THIAZOLE-5-CARBALDEHYDE; 2-(5-OXO-1,4-DIAZEPAN-1-YL)ACETALDEHYDE; 2-(5-OXO-1,4-DIAZEPAN-1-YL)BENZALDEHYDE; 2-(5-OXO-1,4-DIAZEPAN-1-YL)IMIDAZO[1,2-A]PYRIDINE-3-CARBALDEHYDE; 2-(6,10-DIMETHYL-2,4-DIOXO-1,3-DIAZASPIRO[4.5]DECAN-3-YL)ACETALDEHYDE; 2-(6-METHOXY-NAPHTHALEN-2-YL)-4-FORMYL-IMIDAZOLE; 2-(8-METHYL-2,4-DIOXO-1,3-DIAZASPIRO[4.5]DECAN-3-YL)ACETALDEHYDE; 2-(9H-PURIN-6-YLSULFANYL)ACETALDEHYDE; 2-(ALLYLAMINO)-4-OXO-4H-PYRIDO[1,2-A]PYRIMIDINE-3-CARBALDEHYDE; 2-(BENZYLAMINO)-4-OXO-4H-PYRIDO[1,2-A]PYRIMIDINE-3-CARBALDEHYDE; 2-(BENZYLAMINO)-9-METHYL-4-OXO-4H-PYRIDO(1,2-A)PYRIMIDINE-3-CARBALDEHYDE; 2-(BENZYLAMINO)NICOTINALDEHYDE; 2-(BENZYLAMINO)PYRIMIDINE-4-CARBALDEHYDE; 2-(BENZYLAMINO)PYRIMIDINE-5-CARBALDEHYDE; 2-(BUTYLAMINO)PYRIMIDINE-5-CARBALDEHYDE; 2-(CYCLOHEXYLAMINO)-BENZALDEHYDE; 2-(DIMETHYLAMINO)-4-OXO-1,4-DIHYDROQUINOLINE-3-CARBALDEHYDE; 2-(ETHYL[(5-FORMYL-2-METHOXYPHENYL)METHYL]AMINO)-N-METHYLACETAMIDE; 2-(ETHYLAMINO)-9-METHYL-4-OXO-4H-PYRIDO(1,2-A)PYRIMIDINE-3-CARBALDEHYDE; 2-(ETHYLAMINO)PYRIMIDINE-4-CARBALDEHYDE; 2-(ETHYLAMINO)PYRIMIDINE-5-CARBALDEHYDE; 2-(HEXYLAMINO)PYRIMIDINE-5-CARBALDEHYDE; 2-(HYDROXYMETHYL)-1H-INDOLE-3-CARBALDEHYDE; 2-(HYDROXYMETHYL)-1H-PYRROLE-3-CARBALDEHYDE; 2-(ISOBUTYLAMINO)PYRIMIDINE-5-CARBALDEHYDE; 2-(ISOPROPYLAMINO)-4-METHYLBENZALDEHYDE; 2-(ISOPROPYLAMINO)PYRIMIDINE-4-CARBALDEHYDE; 2-(ISOPROPYLAMINO)PYRIMIDINE-5-CARBALDEHYDE; 2-(METHYLAMINO)NICOTINALDEHYDE; 2-(METHYLAMINO)PYRIMIDINE-4-CARBOXALDEHYDE; 2-(METHYLTHIO)-4-[(2-METHOXYPHENYL)AMINO]-5-PYRIMIDINECARBOXALDEHYDE; 2-(METHYLTHIO)-5,6,7,8-TETRAHYDROPYRIDO[4,3-D]PYRIMIDINE-4-CARBALDEHYDE; 2-(NAPHTHALEN-1-YLAMINO)-PYRIMIDINE-5-CARBALDEHYDE; 2-(PHENYLAMINO)PYRIMIDINE-4-CARBALDEHYDE; 2-(PIPERAZIN-1-YL)ACETALDEHYDE; 2-(PIPERAZIN-1-YL)PYRIMIDINE-5-CARBALDEHYDE; 2-(PROPYLAMINO)PYRIMIDINE-4-CARBALDEHYDE; 2-(PROPYLAMINO)PYRIMIDINE-5-CARBALDEHYDE; 2-(PYRROLIDIN-2-YL)PYRIMIDINE-4-CARBALDEHYDE; 2-(SEC-BUTYLAMINO)PYRIMIDINE-5-CARBALDEHYDE; 2-(TERT-BUTYLAMINO)PYRIMIDINE-4-CARBALDEHYDE; 2-(TRIFLUOROMETHYL)-1H-BENZO[D]IMIDAZOLE-4-CARBALDEHYDE; 2-(TRIFLUOROMETHYL)-1H-IMIDAZOLE-5-CARBALDEHYDE; 2,2,2-TRIFLUORO-N-(3-FORMYLPHENYL)ACETAMIDE; 2,3,4,5-

TETRAHYDRO-1,4-BENZOXAZEPINE-7-CARBALDEHYDE; 2,3,4,9-TETRAHYDRO-1-H-CARBAZOL-3-CARBALDEHYDE; 2,3,4,9-TETRAHYDRO-1H-CARBAZOLE-8-CARBALDEHYDE; 2,3-DIHYDRO-1H-INDOLE-4-CARBALDEHYDE; 2,3-DIHYDRO-1H-INDOLE-5-CARBALDEHYDE; 2,3-DIHYDRO-1H-INDOLE-6-CARBALDEHYDE; 2,3-DIHYDRO-1H-PYRIDO[3,4-B][1,4]OXAZINE-8-CARBALDEHYDE; 2,3-DIHYDRO-1H-PYRROLO[2,3-B]PYRIDINE-5-CARBALDEHYDE; 2,3-DIHYDRO-2-OXOBENZO[D]OXAZOLE-5-CARBALDEHYDE; 2,3-DIHYDRO-3,3-DIMETHYL-2-OXO-1H-PYRROLO[3,2-C]PYRIDINE-4-CARBALDEHYDE; 2,3-DIHYDRO-4-METHYL-2-OXO-5-THIAZOLECARBOXALDEHYDE; 2,3-DIHYDRO-5-METHOXY-3-PHENYL-2-INDOLECARBOXALDEHYDE; 2,3-DIMETHYL-1H-INDOLE-5-CARBALDEHYDE; 2,3-DIMETHYL-1H-INDOLE-7-CARBALDEHYDE; 2,3-DIMETHYL-1H-PYRROLO[2,3-C]PYRIDINE-7-CARBALDEHYDE; 2,3-DIOXO-3,4-DIHYDRO-2H-BENZO[1,4]OXAZINE-7-CARBALDEHYDE; 2,3-FORMYL PIPERIDINE; 2,4,5-TRIMETHYL-1H-PYRROLE-3-CARBALDEHYDE; 2,4,6-TRIMETHYL-1H-INDOLE-3-CARBALDEHYDE; 2,4,6-TRIOXO-HEXAHYDRO-PYRIMIDINE-5-CARBALDEHYDE; 2,4,7-TRIMETHYL-1H-INDOLE-3-CARBALDEHYDE; 2,4-DIAMINO-6-OXO-1,6-DIHYDRO-5-PYRIMIDINECARBOXALDEHYDE; 2,4-DIAMINO-7H-PYRROLO[2,3-D]PYRIMIDINE-5-CARBALDEHYDE; 2,4-DICHLORO-N-(3-FORMYL-PHENYL)-BENZAMIDE; 2,4-DIFLUORO-6-(4-FORMYL-IMIDAZOL-2-YL)-PHENOL; 2,4-DIHYDROXYMETHYL-3-METHYL PYRROL-5-CARBALDEHYDE; 2,4-DIMETHYL PYRROL-3-CARBALDEHYDE; 2,4-DIMETHYL-3-HYDROXYMETHYL PYRROL-5-CARBALDEHYDE; 2,4-DIMETHYL-5-(5-METHYL-1,3,4-OXADIAZOL-2-YL)-1H-PYRROLE-3-CARBALDEHYDE; 2,4-DIMETHYL-5-(5-PHENYL-1,3,4-OXADIAZOL-2-YL)-1H-PYRROLE-3-CARBALDEHYDE; 2,4-DIMETHYL-5-(5-PROPYL-1,3,4-OXADIAZOL-2-YL)-1H-PYRROLE-3-CARBALDEHYDE; 2,4-DIMETHYL-5-[5-(4-METHYLPHENYL)-1,3,4-OXADIAZOL-2-YL]-1H-PYRROLE-3-CARBALDEHYDE; 2,5,7-TRIMETHYL-1H-INDOLE-3-CARBALDEHYDE; 2,5-DIFORMYL-1H-PYRROLE-3-CARBONITRILE; 2,5-DIMETHYL-1-(2-OXOPIPERIDIN-3-YL)-1H-PYRROLE-3-CARBALDEHYDE; 2,5-DIMETHYL-1H-IMIDAZOLE-4-CARBOXALDEHYDE; 2,5-DIMETHYL-1H-INDOLE-3-CARBALDEHYDE; 2,5-DIMETHYL-1H-PYRROLE-3,4-DICARBALDEHYDE; 2,5-DIMETHYL-1H-PYRROLE-3-CARBALDEHYDE; 2,5-DIMETHYL-4-(3-PHENYL-1,2,4-OXADIAZOL-5-YL)-1H-PYRROLE-3-CARBALDEHYDE; 2,5-DIMETHYL-4-(5-METHYL-1,3,4-OXADIAZOL-2-YL)-1H-PYRROLE-3-CARBALDEHYDE; 2,5-DIMETHYL-4-(5-PHENYL-1,3,4-OXADIAZOL-2-YL)-1H-PYRROLE-3-CARBALDEHYDE; 2,5-DIMETHYL-4-(5-PROPYL-1,3,4-OXADIAZOL-2-YL)-1H-PYRROLE-3-CARBALDEHYDE; 2,5-DIMETHYL-4-[3-(4-METHYLPHENYL)-1,2,4-OXADIAZOL-5-YL]-1H-PYRROLE-3-CARBALDEHYDE; 2,5-DIMETHYL-4-[5-(4-METHYLPHENYL)-1,3,4-OXADIAZOL-2-YL]-1H-PYRROLE-3-CARBALDEHYDE; 2,5-DIOXO-3-PYRROLIDINEACETALDEHYDE; 2,5-DIMETHYL-1H-PYRROLE-3-CARBALDEHYDE; 2,5-DITERT-BUTYL-1H-INDOLE-3-CARBALDEHYDE; 2,6-DIAMINO-1,4-DIHYDRO-4-OXO-5-PYRIMIDINECARBOXALDEHYDE; 2,6-DIMETHYL-1H-INDOLE-3-CARBALDEHYDE; 2,7-DIMETHYL-1H-INDOLE-3-CARBALDEHYDE; 2-[(1-FORMYLNAPHTHALEN-2-YL)OXY]-N-METHYLACETAMIDE; 2-[(1-FORMYLNAPHTHALEN-2-YL)OXY]-N-METHYLPROPANAMIDE; 2-[(2,3-DIMETHYLPHENYL)AMINO]-1,3-THIAZOLE-4-CARBALDEHYDE; 2-[(2,6-DICHLOROPHENYL)AMINO]BENZALDEHYDE; 2-[(2,6-DIFLUORO-4-FORMYLPHENYL)(ETHYL)AMINO]-N-ETHYLACETAMIDE; 2-[(2,6-DIFLUORO-4-FORMYLPHENYL)(ETHYL)AMINO]-N-METHYLACETAMIDE; 2-[(2,6-DIFLUORO-4-FORMYLPHENYL)(METHYL)AMINO]-N-(PROPAN-2-YL)ACETAMIDE; 2-[(2,6-DIFLUORO-4-FORMYLPHENYL)(METHYL)AMINO]-N-ETHYLACETAMIDE; 2-[(2,6-DIFLUORO-4-FORMYLPHENYL)(METHYL)AMINO]-N-METHYLACETAMIDE; 2-[(2,6-DIFLUORO-4-FORMYLPHENYL)(METHYL)AMINO]-N-PROPYLACETAMIDE; 2-[(2,6-DIFLUORO-4-FORMYLPHENYL)(PROPYL)AMINO]-N-METHYLACETAMIDE; 2-[(2-CHLOROPHENYL)AMINO]-BENZALDEHYDE; 2-[(2-FLUORO-4-FORMYLPHENYL)(METHYL)AMINO]-N-(2-METHOXYETHYL)ACETAMIDE; 2-[(2-FLUORO-4-FORMYLPHENYL)(METHYL)AMINO]-N-(PROPAN-2-YL)ACETAMIDE; 2-[(2-FLUORO-4-FORMYLPHENYL)(METHYL)AMINO]-N-METHYLACETAMIDE; 2-[(2-FLUORO-4-FORMYLPHENYL)(METHYL)AMINO]-N-PROPYLACETAMIDE; 2-[(2-FLUORO-4-FORMYLPHENYL)(PROPYL)AMINO]-N-METHYLACETAMIDE; 2-[(2-FORMYL-4-NITROPHENYL)(METHYL)AMINO]-N-METHYLACETAMIDE; 2-[(2-FORMYLPHENYL)(METHYL)AMINO]-N-(2-METHOXYETHYL)ACETAMIDE; 2-[(2-FORMYLPHENYL)(METHYL)AMINO]-N-(PROPAN-2-YL)ACETAMIDE; 2-[(2-FORMYLPHENYL)(METHYL)AMINO]-N-METHYLACETAMIDE; 2-[(2-FORMYLPHENYL)(METHYL)AMINO]-N-PROPYLACETAMIDE; 2-[(2-FORMYLPHENYL)(PROPYL)AMINO]-N-METHYLACETAMIDE; 2-[(2-FURYLMETHYL)AMINO]-7-METHYL-4-OXO-4H-PYRIDO[1,2-A]PYRIMIDINE-3-CARBALDEHYDE; 2-[(2-FURYLMETHYL)AMINO]PYRIMIDINE-5-CARBALDEHYDE; 2-[(2-OXO-1,2,3,4-TETRAHYDROQUINOLIN-6-YL)OXY]ACETALDEHYDE; 2-[(2-OXO-1,3-OXAZOLIDIN-5-YL)METHOXY]BENZALDEHYDE; 2-[(2-OXOAZEPAN-3-YL)OXY]BENZALDEHYDE; 2-[(3-CHLORO-2-FORMYLPHENYL)(ETHYL)AMINO]-N-(PROPAN-2-YL)ACETAMIDE; 2-[(3-CHLORO-2-FORMYLPHENYL)(ETHYL)AMINO]-N-ETHYLACETAMIDE; 2-[(3-CHLORO-2-FORMYLPHENYL)(ETHYL)AMINO]-N-METHYLACETAMIDE; 2-[(3-CHLORO-2-FORMYLPHENYL)(METHYL)AMINO]-N-(2-METHOXYETHYL)ACETAMIDE; 2-[(3-CHLORO-2-FORMYLPHENYL)(METHYL)AMINO]-N-(PROPAN-2-YL)ACETAMIDE; 2-[(3-CHLORO-2-FORMYLPHENYL)(METHYL)AMINO]-N-CYCLOPROPYLACETAMIDE; 2-[(3-CHLORO-2-FORMYLPHENYL)(METHYL)AMINO]-N-ETHYLACETAMIDE; 2-[(3-CHLORO-2-FORMYLPHENYL)(METHYL)AMINO]-N-METHYL-ACETAMIDE; 2-[(3-CHLORO-2-FORMYLPHENYL)(METHYL)AMINO]-N-PROPYLACETAMIDE; 2-[(3-CHLORO-2-FORMYLPHENYL)(PROPYL)AMINO]-N-

METHYLACETAMIDE; 2-[(3-FORMYLQUINOLIN-2-YL)(METHYL)AMINO]-N-METHYLACETAMIDE; 2-[(4-FLUORO-2-FORMYLPHENYL)(METHYL) AMINO]-N-(2-METHOXYETHYL)ACETAMIDE; 2-[(4-FLUORO-2-FORMYLPHENYL)(METHYL)AMINO]-N-(PROPAN-2-YL)ACETAMIDE; 2-[(4-FLUORO-2-FORMYLPHENYL)(METHYL)AMINO]-N-METHYLACETAMIDE; 2-[(4-FLUORO-2-FORMYLPHENYL)(METHYL)AMINO]-N-PROPYLACETAMIDE; 2-[(4-FLUORO-2-FORMYLPHENYL)(PROPYL)AMINO]-N-METHYLACETAMIDE; 2-[(4-FORMYL-1,3-DIMETHYL-1H-PYRAZOL-5-YL)(METHYL)AMINO]-N-(2-METHOXYETHYL)ACETAMIDE; 2-[(4-FORMYL-1,3-DIMETHYL-1H-PYRAZOL-5-YL)(METHYL) AMINO]-N-(PROPAN-2-YL)ACETAMIDE; 2-[(4-FORMYL-1,3-DIMETHYL-1H-PYRAZOL-5-YL) (METHYL)AMINO]-N-METHYLACETAMIDE; 2-[(4-FORMYL-1,3-DIMETHYL-1H-PYRAZOL-5-YL) (METHYL)AMINO]-N-PROPYLACETAMIDE; 2-[(4-FORMYL-1,3-DIMETHYL-1H-PYRAZOL-5-YL) (PROPYL)AMINO]-N-METHYLACETAMIDE; 2-[(4-FORMYL-2-METHYLPHENYL)(METHYL)AMINO]-N-(2-METHOXYETHYL)ACETAMIDE; 2-[(4-FORMYL-2-METHYLPHENYL)(METHYL)AMINO]-N-(PROPAN-2-YL)ACETAMIDE; 2-[(4-FORMYL-2-METHYLPHENYL)(METHYL)AMINO]-N-METHYLACETAMIDE; 2-[(4-FORMYL-2-METHYLPHENYL)(METHYL)AMINO]-N-PROPYLACETAMIDE; 2-[(4-FORMYL-2-METHYLPHENYL)(PROPYL)AMINO]-N-METHYLACETAMIDE; 2-[(4-FORMYL-2-NITROPHENYL)(METHYL)AMINO]-N-METHYLACETAMIDE; 2-[(4-FORMYL-3-METHYLPHENYL)(METHYL)AMINO]-N-(2-METHOXYETHYL)ACETAMIDE; 2-[(4-FORMYL-3-METHYLPHENYL)(METHYL)AMINO]-N-(PROPAN-2-YL)ACETAMIDE; 2-[(4-FORMYL-3-METHYLPHENYL)(METHYL)AMINO]-N-METHYLACETAMIDE; 2-[(4-FORMYL-3-METHYLPHENYL)(METHYL)AMINO]-N-PROPYLACETAMIDE; 2-[(4-FORMYL-3-METHYLPHENYL)(PROPYL)AMINO]-N-METHYLACETAMIDE; 2-[(4-FORMYLPHENYL)(METHYL)AMINO]-N-(2-METHOXYETHYL) ACETAMIDE; 2-[(4-FORMYLPHENYL)(METHYL) AMINO]-N-(PROPAN-2-YL)ACETAMIDE; 2-[(4-FORMYLPHENYL)(METHYL)AMINO]-N-METHYLACETAMIDE; 2-[(4-FORMYLPHENYL) (METHYL)AMINO]-N-PROPYLACETAMIDE; 2-[(4-FORMYLPHENYL)(PROPYL)AMINO]-N-METHYLACETAMIDE; 2-[(4-OXO-6-PROPYL-1,4-DIHYDROPYRIMIDIN-2-YL)SULFANYL] ACETALDEHYDE; 2-[(5-BROMO-2-FORMYLPHENYL)(ETHYL)AMINO]-N-METHYLACETAMIDE; 2-[(5-BROMO-2-FORMYLPHENYL)(METHYL)AMINO]-N-ETHYLACETAMIDE; 2-[(5-BROMO-2-FORMYLPHENYL)(METHYL)AMINO]-N-METHYLACETAMIDE; 2-[(5-FORMYLFURAN-2-YL) (METHYL)AMINO]-N-(2-METHOXYETHYL) ACETAMIDE; 2-[(5-FORMYLFURAN-2-YL)(METHYL) AMINO]-N-(PROPAN-2-YL)ACETAMIDE; 2-[(5-FORMYLFURAN-2-YL)(METHYL)AMINO]-N-METHYLACETAMIDE; 2-[(5-FORMYLFURAN-2-YL) (METHYL)AMINO]-N-PROPYLACETAMIDE; 2-[(5-FORMYLFURAN-2-YL)(PROPYL)AMINO]-N-METHYLACETAMIDE; 2-[(5-METHYL-4H-1,2,4-TRIAZOL-3-YL)SULFANYL]ACETALDEHYDE; 2-[(6-FORMYL-2H-1,3-BENZODIOXOL-5-YL)OXY]-N-(PROP-2-EN-1-YL)ACETAMIDE; 2-[(6-FORMYL-2H-1,3-BENZODIOXOL-5-YL)OXY]-N-(PROP-2-YN-1-YL) ACETAMIDE; 2-[(6-FORMYL-2H-1,3-BENZODIOXOL-5-YL)OXY]-N-(PROPAN-2-YL)ACETAMIDE; 2-[(6-FORMYL-2H-1,3-BENZODIOXOL-5-YL)OXY]-N-METHYLACETAMIDE; 2-[(6-FORMYL-2H-1,3-BENZODIOXOL-5-YL)OXY]-N-PROPYLACETAMIDE; 2-[(6-METHYL-4-OXO-1,4-DIHYDROPYRIMIDIN-2-YL)SULFANYL]ACETALDEHYDE; 2-[(BENZOYLAMINO)METHYL]-4-FORMYLPHENYL ACETATE; 2-[(CYCLOHEXYLAMINO)(PHENYL)METHYLENE] MALONALDEHYDE; 2-[1-(1H-IMIDAZOL-4-YL)-ETHYL]-BENZALDEHYDE; 2-[2-(1H-IMIDAZOL-4-YL)-ETHYL]-BENZALDEHYDE; 2-[2-(1H-IMIDAZOL-4-YL)-VINYL]-BENZALDEHYDE; 2-[2-(2-METHYLIMIDAZOL-4-YL)-ETHYL] BENZALDEHYDE; 2-[2-(2-OXOIMIDAZOLIDIN-1-YL) ETHOXY]BENZALDEHYDE; 2-[3-(2-OXO-PYRROLIDIN-1-YL)-PROPYLAMINO]-PYRIMIDINE-4-CARBALDEHYDE; 2-[4-(1,1-DIMETHYLETHYL) PHENYL]-5-FLUORO-1H-INDOLE-3-CARBOXALDEHYDE; 2-[4-(1,1-DIMETHYLETHYL) PHENYL]-5-METHYL-1H-INDOLE-3-CARBOXALDEHYDE; 2-[4-(1,1-DIMETHYLETHYL) PHENYL]-7-FLUORO-1H-INDOLE-3-CARBOXALDEHYDE; 2-[4-(1,1-DIMETHYLETHYL) PHENYL]-7-METHYL-1H-INDOLE-3-CARBOXALDEHYDE; 2-[4-(PHENYLAMINO) PHENOXY]ACETALDEHYDE; 2-[ETHYL((3-FORMYLIMIDAZO[1,2-A]PYRIDIN-2-YL))AMINO]-N-METHYLACETAMIDE; 2-[ETHYL((5-FORMYLIMIDAZO[2,1-B][1,3]THIAZOL-6-YL)) AMINO]-N-METHYLACETAMIDE; 2-[ETHYL(2-FLUORO-4-FORMYLPHENYL)AMINO]-N-(PROPAN-2-YL)ACETAMIDE; 2-[ETHYL(2-FLUORO-4-FORMYLPHENYL)AMINO]-N-METHYLACETAMIDE; 2-[ETHYL(2-FORMYL-4-NITROPHENYL)AMINO]-N-METHYLACETAMIDE; 2-[ETHYL(2-FORMYLPHENYL)AMINO]-N-(PROPAN-2-YL)ACETAMIDE; 2-[ETHYL(2-FORMYLPHENYL)AMINO]-N-METHYL-ACETAMIDE; 2-[ETHYL(2-OXOETHYL)AMINO]-N-(PROPAN-2-YL)ACETAMIDE; 2-[ETHYL(2-OXOETHYL)AMINO]-N-METHYLACETAMIDE; 2-[ETHYL(3-OXOPROPYL)AMINO]-N-(PROPAN-2-YL) ACETAMIDE; 2-[ETHYL(3-OXOPROPYL)AMINO]-N-METHYLACETAMIDE; 2-[ETHYL(4-FLUORO-2-FORMYLPHENYL)AMINO]-N-(PROPAN-2-YL) ACETAMIDE; 2-[ETHYL(4-FLUORO-2-FORMYLPHENYL)AMINO]-N-METHYLACETAMIDE; 2-[ETHYL(4-FORMYL-1,3-DIMETHYL-1H-PYRAZOL-5-YL)AMINO]-N-(PROPAN-2-YL)ACETAMIDE; 2-[ETHYL(4-FORMYL-1,3-DIMETHYL-1H-PYRAZOL-5-YL)AMINO]-N-METHYLACETAMIDE; 2-[ETHYL(4-FORMYL-2-METHYLPHENYL)AMINO]-N-(PROPAN-2-YL)ACETAMIDE; 2-[ETHYL(4-FORMYL-2-METHYLPHENYL)AMINO]-N-METHYLACETAMIDE; 2-[ETHYL(4-FORMYL-2-NITROPHENYL)AMINO]-N-METHYLACETAMIDE; 2-[ETHYL(4-FORMYL-3-METHYLPHENYL)AMINO]-N-(PROPAN-2-YL)ACETAMIDE; 2-[ETHYL(4-FORMYL-3-METHYLPHENYL) AMINO]-N-METHYLACETAMIDE; 2-[ETHYL(4-FORMYLPHENYL)AMINO]-N-(PROPAN-2-YL) ACETAMIDE; 2-[ETHYL(4-FORMYLPHENYL) AMINO]-N-METHYLACETAMIDE; 2-[ETHYL(5-

FORMYLFURAN-2-YL)AMINO]-N-(PROPAN-2-YL) ACETAMIDE; 2-[ETHYL(5-FORMYLFURAN-2-YL) AMINO]-N-METHYLACETAMIDE; 2-[ETHYL(PIPERIDIN-4-YL)AMINO]ACETALDEHYDE; 2-[METHYL(2-OXOETHYL)AMINO]-N-(PROPAN-2-YL)ACETAMIDE; 2-[METHYL(3-OXOPROPYL)AMINO]-N-(PROPAN-2-YL)ACETAMIDE; 2-[METHYL(3-OXOPROPYL) AMINO]-N-PROPYLACETAMIDE; 2-[METHYL(PIPERIDIN-4-YL)AMINO]ACETALDEHYDE; 2-[PIPERIDIN-4-YL(PROPYL)AMINO]ACETALDEHYDE; 2-ACETAMIDO-2-DEOXY-DEXTRO-GALACTOPYRANOSE HYDRATE; 2-ACETAMIDO-4-HYDROXY-6-PTERIDINECARBOXALDEHYDE; 2-AMINO-1H-IMIDAZOLE-4-CARBALDEHYDE HCL; 2-AMINO-1H-IMIDAZOLE-5-CARBALDEHYDE; 2-ANILINO-7-METHYL-4-OXO-4H-PYRIDO[1,2-A]PYRIMIDINE-3-CARBALDEHYDE; 2-ANILINOPYRIMIDINE-5-CARBALDEHYDE; 2-BENZAMIDOCINNAMALDEHYDE; 2-BENZO[B]THIOPHEN-2-YL-4-FORMYL-IMIDAZOLE; 2-BENZYL-1H-IMIDAZOLE-4-CARBALDEHYDE; 2-BROMO-4-FORMYLPIPERIDINE; 2-BROMO-5H-PYRROLO[2,3-B]PYRAZINE-7-CARBOXALDEHYDE; 2-BUTYL-1H-IMIDAZOLE-4-CARBALDEHYDE; 2-BUTYL-1H-IMIDAZOLE-5-CARBALDEHYDE; 2-CHLORO-5,6,7,8-TETRAHYDROPYRIDO[4,3-D]PYRIMIDINE-4-CARBALDEHYDE; 2-CHLORO-6-(3-OXOPIPERAZIN-1-YL)BENZALDEHYDE; 2-CHLORO-6-(5-OXO-1,4-DIAZEPAN-1-YL)BENZALDEHYDE; 2-CHLORO-6-[(2-OXO-1,3-OXAZOLIDIN-5-YL)METHOXY] BENZALDEHYDE; 2-CHLORO-6-[(2-OXOAZEPAN-3-YL)OXY]BENZALDEHYDE; 2-CHLORO-6-[2-(2-OXOIMIDAZOLIDIN-1-YL)ETHOXY] BENZALDEHYDE; 2-CHLORO-N-(3-FORMYLPHENYL)-BENZAMIDE; 2-CYCLOHEX-3-ENYL-1H-IMIDAZOLE-4-CARBALDEHYDE; 2-CYCLOHEXYL-1H-IMIDAZOLE-4-CARBALDEHYDE; 2-CYCLOHEXYL-4,6-DICHLORO-1H-INDOLE-3-CARBOXALDEHYDE; 2-CYCLOHEXYL-4,6-DIFLUORO-1H-INDOLE-3-CARBOXALDEHYDE; 2-CYCLOHEXYL-4,6-DIMETHYL-1H-INDOLE-3-CARBOXALDEHYDE; 2-CYCLOHEXYL-4,7-DICHLORO-1H-INDOLE-3-CARBOXALDEHYDE; 2-CYCLOHEXYL-4,7-DIFLUORO-1H-INDOLE-3-CARBOXALDEHYDE; 2-CYCLOHEXYL-4,7-DIMETHYL-1H-INDOLE-3-CARBOXALDEHYDE; 2-CYCLOHEXYL-5-(1,1-DIMETHYLETHYL)-1H-INDOLE-3-CARBOXALDEHYDE; 2-CYCLOHEXYL-5-(1-METHYLETHYL)-1H-INDOLE-3-CARBOXALDEHYDE; 2-CYCLOHEXYL-5-(TRIFLUOROMETHYL)-1H-INDOLE-3-CARBOXALDEHYDE; 2-CYCLOHEXYL-5,7-DICHLORO-1H-INDOLE-3-CARBOXALDEHYDE; 2-CYCLOHEXYL-5,7-DIFLUORO-1H-INDOLE-3-CARBOXALDEHYDE; 2-CYCLOHEXYL-5,7-DIMETHYL-1H-INDOLE-3-CARBOXALDEHYDE; 2-CYCLOHEXYL-5-ETHOXY-1H-INDOLE-3-CARBOXALDEHYDE; 2-CYCLOHEXYL-5-METHOXY-1H-INDOLE-3-CARBOXALDEHYDE; 2-CYCLOHEXYL-5-METHYL-1H-INDOLE-3-CARBOXALDEHYDE; 2-CYCLOHEXYL-5-NITRO-1H-INDOLE-3-CARBOXALDEHYDE; 2-CYCLOHEXYL-6,7-DICHLORO-1H-INDOLE-3-CARBOXALDEHYDE; 2-CYCLOHEXYL-6,7-DIFLUORO-1H-INDOLE-3-CARBOXALDEHYDE; 2-CYCLOHEXYL-6,7-DIMETHYL-1H-INDOLE-3-CARBOXALDEHYDE; 2-CYCLOHEXYL-7-(TRIFLUOROMETHYL)-1H-INDOLE-3-CARBOXALDEHYDE; 2-CYCLOHEXYL-7-FLUORO-1H-INDOLE-3-CARBOXALDEHYDE; 2-CYCLOHEXYL-7-FLUORO-5-METHYL-1H-INDOLE-3-CARBOXALDEHYDE; 2-CYCLOHEXYL-7-METHOXY-1H-INDOLE-3-CARBOXALDEHYDE; 2-CYCLOHEXYL-7-METHYL-1H-INDOLE-3-CARBOXALDEHYDE; 2-CYCLOHEXYL-7-METHYL-5-NITRO-1H-INDOLE-3-CARBOXALDEHYDE; 2-CYCLOHEXYLAMINO-PYRIMIDINE-5-CARBALDEHYDE; 2-CYCLOPENTYL-1H-INDOLE-3-CARBALDEHYDE; 2-CYCLOPROPOXY-3-(METHYLAMINO)BENZALDEHYDE; 2-CYCLOPROPOXY-3-FORMYL-N-METHYLBENZAMIDE; 2-CYCLOPROPOXY-4-(METHYLAMINO)BENZALDEHYDE; 2-CYCLOPROPOXY-4-FORMYL-N-METHYLBENZAMIDE; 2-CYCLOPROPOXY-5-(METHYLAMINO)BENZALDEHYDE; 2-CYCLOPROPOXY-5-FORMYL-N-METHYLBENZAMIDE; 2-CYCLOPROPOXY-6-(METHYLAMINO)BENZALDEHYDE; 2-CYCLOPROPOXY-6-FORMYL-N-METHYLBENZAMIDE; 2-CYCLOPROPYL-4,6-DICHLORO-1H-INDOLE-3-CARBOXALDEHYDE; 2-CYCLOPROPYL-4,6-DIFLUORO-1H-INDOLE-3-CARBOXALDEHYDE; 2-CYCLOPROPYL-4,6-DIMETHYL-1H-INDOLE-3-CARBOXALDEHYDE; 2-CYCLOPROPYL-4,7-DICHLORO-1H-INDOLE-3-CARBOXALDEHYDE; 2-CYCLOPROPYL-4,7-DIFLUORO-1H-INDOLE-3-CARBOXALDEHYDE; 2-CYCLOPROPYL-4,7-DIMETHYL-1H-INDOLE-3-CARBOXALDEHYDE; 2-CYCLOPROPYL-5-(1,1-DIMETHYLETHYL)-1H-INDOLE-3-CARBOXALDEHYDE; 2-CYCLOPROPYL-5-(1-METHYLETHYL)-1H-INDOLE-3-CARBOXALDEHYDE; 2-CYCLOPROPYL-5-(TRIFLUOROMETHYL)-1H-INDOLE-3-CARBOXALDEHYDE; 2-CYCLOPROPYL-5,7-DICHLORO-1H-INDOLE-3-CARBOXALDEHYDE; 2-CYCLOPROPYL-5,7-DIFLUORO-1H-INDOLE-3-CARBOXALDEHYDE; 2-CYCLOPROPYL-5,7-DIMETHYL-1H-INDOLE-3-CARBOXALDEHYDE; 2-CYCLOPROPYL-5-ETHOXY-1H-INDOLE-3-CARBOXALDEHYDE; 2-CYCLOPROPYL-5-METHOXY-1H-INDOLE-3-CARBOXALDEHYDE; 2-CYCLOPROPYL-5-METHYL-1H-INDOLE-3-CARBOXALDEHYDE; 2-CYCLOPROPYL-5-NITRO-1H-INDOLE-3-CARBOXALDEHYDE; 2-CYCLOPROPYL-6,7-DICHLORO-1H-INDOLE-3-CARBOXALDEHYDE; 2-CYCLOPROPYL-6,7-DIFLUORO-1H-INDOLE-3-CARBOXALDEHYDE; 2-CYCLOPROPYL-6,7-DIMETHYL-1H-INDOLE-3-CARBOXALDEHYDE; 2-CYCLOPROPYL-7-(TRIFLUOROMETHYL)-1H-INDOLE-3-CARBOXALDEHYDE; 2-CYCLOPROPYL-7-FLUORO-1H-INDOLE-3-CARBOXALDEHYDE; 2-CYCLOPROPYL-7-FLUORO-5-METHYL-1H-INDOLE-3-CARBOXALDEHYDE; 2-CYCLOPROPYL-7-METHOXY-1H-INDOLE-3-CARBOXALDEHYDE; 2-CYCLOPROPYL-7-METHOXY-5-NITRO-1H-INDOLE-3-CARBOXALDEHYDE; 2-CYCLOPROPYL-7-METHYL-1H-INDOLE-3-CARBOXALDEHYDE; 2-CYCLOPROPYLAMINO-PYRIMIDINE-4-CARBALDEHYDE; 2-ETHENYL-1H-INDOLE-3-CARBOXALDEHYDE; 2-ETHYL-1H-IMIDAZOLE-4-CARBALDEHYDE; 2-ETHYL-1H-INDOLE-3-CARBALDEHYDE; 2-ETHYL-1H-PYRROLO[2,3-B]PYRIDINE-3-CARBALDEHYDE; 2-ETHYL-1H-PYRROLO[2,3-B]PYRIDINE-5-CARBALDEHYDE; 2-ETHYL-4-FORMYLIMIDAZOLE; 2-ETHYL-4-METHYL-1H-IMIDAZOLE-5-CARBALDEHYDE;

2-ETHYL-5-METHYL-1H-IMIDAZOLE-4-CARBALDEHYDE; 2-ETHYL-5-OXO-5,6-DIHYDRO-IMIDAZO[1,2-C]PYRIMIDINE-3-CARBALDEHYDE; 2-FLUORO-4-(4-FORMYL-IMIDAZOL-2-YL)-PHENOL; 2-FLUORO-4-(PIPERIDIN-3-YL)BENZALDEHYDE HCL; 2-FLUORO-4-(PIPERIDIN-4-YL)BENZALDEHYDE HYDROCHLORIDE; 2-FLUORO-4-(PYRROLIDIN-3-YL)BENZALDEHYDE HCL; 2-FLUORO-5-(1H-IMIDAZOL-2-YL)-BENZALDEHYDE; 2-FLUORO-5-(4-FORMYL-IMIDAZOL-2-YL)-BENZONITRILE; 2-FLUORO-6-(4-FORMYL-IMIDAZOL-2-YL)-PHENOL; 2-FORMYL-1,4,6,7-TETRAHYDRO-PYRROLO[3,2-C]PYRIDINE-5-CARBOXYLIC ACID TERT-BUTYL ESTER; 2-FORMYL-1H-BENZOIMIDAZOLE-5-CARBOXYLIC ACID METHYL ESTER; 2-FORMYL-1H-IMIDAZOLE-4-CARBONITRILE; 2-FORMYL-1H-IMIDAZOLE-4-CARBOXYLIC ACID; 2-FORMYL-1H-INDOLE-6-CARBONITRILE; 2-FORMYL-1H-PYRROLE-3-CARBONITRILE; 2-FORMYL-3-HYDROXY-N-METHYLBENZAMIDE; 2-FORMYL-3-METHYL-1-OXO-1,5-DIHYDRO-BENZO[4,5]IMIDAZO[1,2-A]PYRIDINE-4-CARBONITRILE; 2-FORMYL-4-(5-BROMOTHIOPHEN-2-YL)IMIDAZOLE; 2-FORMYL-4-(5-CHLOROTHIOPHEN-2-YL)IMIDAZOLE; 2-FORMYL-4-(5-METHYLTHIOPHEN-2-YL)IMIDAZOLE; 2-FORMYL-4,5,6,7-TETRAHYDROTHIENO[3,2-C]PYRIDINE HYDROCHLORIDE; 2-FORMYL-4-[3-(N-METHYLAMINOCARBONYL)PHENYL]PHENOL; 2-FORMYL-4-HYDROXY-N-METHYLBENZAMIDE; 2-FORMYL-4-METHOXY-N-METHYL-BENZAMIDE; 2-FORMYL-5-[3-(N-METHYLAMINOCARBONYL)PHENYL]PHENOL; 2-FORMYL-5-HYDROXY-N-METHYLBENZAMIDE; 2-FORMYL-5-METHOXY-N-METHYL-BENZAMIDE; 2-FORMYL-5-METHYL-1H-IMIDAZO[4,5-C]PIPERIDINE; 2-FORMYL-5-METHYL-1H-PYRROLE-3,4-DICARBONITRILE; 2-FORMYL-6-[3-(N-METHYLAMINOCARBONYL)PHENYL]PHENOL; 2-FORMYL-6H-FURO[2,3-B]PYRROLE-5-CARBOXYLIC ACID; 2-FORMYL-6-HYDROXY-N-METHYLBENZAMIDE; 2-FORMYL-6-METHOXY-1H-INDOLE; 2-FORMYL-7-METHYL-4,5,6,7-TETRAHYDROBENZOIMIDAZOLE; 2-FORMYL-N-ISOPROPYLTHIAZOLE-4-CARBOXAMIDE; 2-FORMYLPIPERIDINE; 2-FORMYLPIPERIDINE HCL; 2-FURAN-2-YL-1H-IMIDAZOLE-4-CARBALDEHYDE; 2-FURAN-3-YL-1H-IMIDAZOLE-4-CARBALDEHYDE; 2-FURANCARBOXALDEHYDE, 5-(1H-INDOL-5-YL)-; 2-HEPTYL-1,4-DIHYDRO-4-OXO-3-QUINOLINECARBOXALDEHYDE; 2-HYDROXY-3-(METHYLAMINO)BENZALDEHYDE; 2-HYDROXY-4-(METHYLAMINO)BENZALDEHYDE; 2-HYDROXY-5-(METHYLAMINO)BENZALDEHYDE; 2-HYDROXY-5-METHYL-3-(PIPERIDIN-3-YL)BENZALDEHYDE; 2-HYDROXY-5-METHYL-3-(PIPERIDIN-4-YL)BENZALDEHYDE; 2-HYDROXY-5-METHYL-3-(PYRROLIDIN-3-YL)BENZALDEHYDE; 2-HYDROXY-6-(METHYLAMINO)BENZALDEHYDE; 2-ISOBUTYL-1H-IMIDAZOLE-4-CARBALDEHYDE; 2-ISOPROPYL-1H-IMIDAZOLE-4-CARBALDEHYDE; 2-MERCAPTO-1H-INDOLE-3-CARBALDEHYDE; 2-METHOXY-1H-IMIDAZOLE-4-CARBALDEHYDE; 2-METHYL-1H-BENZO[D]IMIDAZOLE-4-CARBALDEHYDE; 2-METHYL-1H-IMIDAZOLE-4-CARBALDEHYDE; 2-METHYL-1H-INDOLE-3-ACETALDEHYDE; 2-METHYL-1H-INDOLE-4-CARBALDEHYDE; 2-METHYL-1H-INDOLE-7-CARBALDEHYDE; 2-METHYL-1H-PYRROLE-3-CARBALDEHYDE; 2-METHYL-1H-PYRROLO[2,3-C]PYRIDINE-3-CARBALDEHYDE; 2-METHYL-1H-PYRROLO[3,2-C]PYRIDINE-3-CARBALDEHYDE; 2-METHYL-4-(3-OXOPIPERAZIN-1-YL)BENZALDEHYDE; 2-METHYL-4-(5-OXO-1,4-DIAZEPAN-1-YL)BENZALDEHYDE; 2-METHYL-4-(METHYLAMINO)BENZALDEHYDE; 2-METHYL-4H-FURO[3,2-B]PYRROLE-5-CARBALDEHYDE; 2-METHYL-5,6-DIHYDRO-1H-PYRROLO[2,3-B]PYRIDINE-3-CARBALDEHYDE; 2-METHYL-5-NITRO-1H-INDOLE-3-CARBALDEHYDE; 2-METHYL-5-OXO-5,6-DIHYDRO-IMIDAZO[1,2-C]PYRIMIDINE-3-CARBALDEHYDE; 2-METHYL-9-OXO-4H,9H-PYRAZOLO[3,2-B]QUINAZOLINE-3-CARBALDEHYDE; 2-METHYLAMINO-PYRIMIDINE-5-CARBALDEHYDE; 2-METHYLAMINO-THIAZOLE-5-CARBALDEHYDE; 2-METHYLIMIDAZOLE-5-CARBOXALDEHYDE; 2-METHYLINDOLE-3-CARBOXALDEHYDE; 2-METHYLSULFANYL-3H-IMIDAZOLE-4-CARBALDEHYDE; 2-METHYLSULFANYL-4-PHENYLAMINO-PYRIMIDINE-5-CARBALDEHYDE; 2-METHYLSULFANYL-5-TRIMETHYLSILANYL-1H-IMIDAZOLE-4-CARBALDEHYDE; 2-METHYLTHIO-4-ISOAMYLAMINO-5-PYRIMIDINECARBOXALDEHYDE; 2-MORPHOLINECARBOXALDEHYDE; 2-M-TOLYL-1H-IMIDAZOLE-4-CARBALDEHYDE; 2-M-TOLYLAMINO-PYRIMIDINE-5-CARBALDEHYDE; 2-NAPHTHALEN-1-YL-1H-IMIDAZOLE-4-CARBALDEHYDE; 2-NAPHTHALEN-2-YL-1H-IMIDAZOLE-4-CARBALDEHYDE; 2-N-BOC-AMINO-3-FORMYLPYRIDINE; 2-O-TOLYL-1H-IMIDAZOLE-4-CARBALDEHYDE; 2-O-TOLYLAMINO-PYRIMIDINE-5-CARBALDEHYDE; 2-OXO-1,2,6,7,8,9-HEXAHYDROBENZO[G]QUINOLINE-3-CARBALDEHYDE; 2-OXO-1,2-DIHYDRO-3-PYRIDINECARBALDEHYDE; 2-OXO-1,2-DIHYDRO-QUINOLINE-3-CARBALDEHYDE; 2-OXO-1,2-DIHYDROQUINOLINE-7-CARBALDEHYDE; 2-OXO-2,3-DIHYDRO-1H-IMIDAZOLE-4-CARBALDEHYDE; 2-OXO-2,3-DIHYDRO-1H-PYRIDO[2,3-B][1,4]OXAZINE-7-CARBALDEHYDE; 2-OXO-2,3-DIHYDRO-1H-PYRROLO[2,3-B]PYRIDINE-4-CARBALDEHYDE; 2-OXO-2,3-DIHYDRO-1H-PYRROLO[2,3-B]PYRIDINE-5-CARBALDEHYDE; 2-OXO-2,3-DIHYDRO-1H-PYRROLO[3,2-B]PYRIDINE-6-CARBALDEHYDE; 2-OXO-2,3-DIHYDRO-BENZOOXAZOLE-6-CARBALDEHYDE; 2-OXO-2-PHENYL-ETHYL N-(5-FORMYLPYRIMIDIN-2-YL)GLYCINATE; 2-OXO-4-(PROPYLAMINO)-2H-CHROMENE-3-CARBALDEHYDE; 2-OXO-5-PROPYLINDOLINE-3-CARBALDEHYDE; 2-OXO-IMIDAZOLIDINE-4-CARBALDEHYDE; 2-OXOINDOLINE-3-CARBALDEHYDE; 2-PHENETHYL-1H-IMIDAZOLE-4-CARBALDEHYDE; 2-PHENYL-1H-BENZO[D]IMIDAZOLE-4-CARBALDEHYDE; 2-PHENYL-1H-IMIDAZOLE-4-CARBALDEHYDE; 2-PHENYL-1H-IMIDAZOLE-5-CARBALDEHYDE; 2-PHENYL-1H-PYRROLO[2,3-B]PYRIDINE-3-CARBOXALDEHYDE; 2-PHENYL-1H-PYRROLO[2,3-B]PYRIDINE-4-CARBOXALDEHYDE; 2-PHENYL-1H-PYRROLO[2,3-B]PYRIDINE-5-CARBOXALDEHYDE; 2-PHENYL-1H-PYRROLO[2,3-B]PYRIDINE-6-CARBOXALDEHYDE; 2-PHENYLINDOLE-3-CARBOXALDEHYDE; 2-PIPERAZIN-1-YL-5-TRIFLUOROMETHYLBENZALDEHYDE; 2-PIPERAZIN-1-YL-BENZALDEHYDE; 2-PIPERAZINECARBOXALDEHYDE; 2-PROPENAL, 3-[(4-METHYLPHENYL)AMINO]-2-NITRO-; 2-PROPYL-1H-IMIDAZOLE-4-CARBALDEHYDE; 2-P-

TOLYL-1H-IMIDAZOLE-4-CARBALDEHYDE; 2-P-TOLYLAMINO-PYRIMIDINE-5-CARBALDEHYDE; 2-PYRIDIN-2-YL-1H-IMIDAZOLE-4-CARBALDEHYDE; 2-PYRIDIN-2-YL-1H-INDOLE-3-CARBALDEHYDE; 2-PYRIDIN-3-YL-1H-IMIDAZOLE-4-CARBALDEHYDE; 2-PYRIDIN-3-YL-1H-INDOLE-3-CARBALDEHYDE; 2-PYRIDIN-4-YL-1H-IMIDAZOLE-4-CARBALDEHYDE; 2-PYRIDIN-4-YL-1H-INDOLE-3-CARBALDEHYDE; 2-PYRIDINECARBOXALDEHYDE, 4-[4-(METHYLAMINO)-3-NITROPHENOXY]-; 2-PYRIDONE-6-CARBOXALDEHYDE; 2-PYRROLECARBAMIC ACID, 4-FORMYL-3,5-DIMETHYL-; 2-QUINOLIN-2-YL-1H-IMIDAZOLE-4-CARBALDEHYDE; 2-SEC-BUTYL-1H-IMIDAZOLE-4-CARBALDEHYDE; 2-STYRYL-1H-IMIDAZOLE-4-CARBALDEHYDE; 2-TERT-BUTYL-1H-IMIDAZOLE-4-CARBALDEHYDE; 2-TERT-BUTYL-1H-INDOLE-3-CARBALDEHYDE; 2-TERT-BUTYL-1H-PYRROLO[2,3-B]PYRIDINE-3-CARBALDEHYDE; 2-TERT-BUTYL-3-FORMYL-1H-INDOLE-5-CARBONITRILE; 2-TERT-BUTYL-4-CHLORO-7-METHYL-1H-INDOLE-3-CARBALDEHYDE; 2-TERT-BUTYL-4-FLUORO-7-METHYL-1H-INDOLE-3-CARBALDEHYDE; 2-TERT-BUTYL-5,7-DIFLUORO-1H-INDOLE-3-CARBALDEHYDE; 2-TERT-BUTYL-5-CHLORO-7-METHYL-1H-INDOLE-3-CARBALDEHYDE; 2-TERT-BUTYL-5-ETHYL-1H-INDOLE-3-CARBALDEHYDE; 2-TERT-BUTYL-5-FLUORO-1H-INDOLE-3-CARBALDEHYDE; 2-TERT-BUTYL-5-ISOPROPYL-1H-INDOLE-3-CARBALDEHYDE; 2-TERT-BUTYL-5-PHENYL-1H-INDOLE-3-CARBALDEHYDE; 2-TERT-BUTYL-7-ETHYL-1H-INDOLE-3-CARBALDEHYDE; 2-TERT-BUTYL-7-FLUORO-1H-INDOLE-3-CARBALDEHYDE; 2-TERT-BUTYL-7-METHYL-1H-INDOLE-3-CARBALDEHYDE; 2-THIAZOL-2-YL-1H-IMIDAZOLE-4-CARBALDEHYDE; 2-THIEN-2-YL-1H-INDOLE-3-CARBALDEHYDE; 2-THIOPHEN-2-YL-1H-IMIDAZOLE-4-CARBALDEHYDE; 2-THIOPHEN-3-YL-1H-IMIDAZOLE-4-CARBALDEHYDE; 2-THIOPHENECARBOXALDEHYDE, 5-(1H-INDOL-5-YL)-; 2-THIOXO-1,2-DIHYDROPYRIDINE-3-CARBALDEHYDE; 2-VINYL-1H-IMIDAZOLE-4-CARBALDEHYDE; 3-((2R)(2-PIPERIDYL))-2-HYDROXY-5-METHYLBENZALDEHYDE; 3-((2R)AZETIDIN-2-YL)-2-HYDROXY-5-METHYLBENZALDEHYDE; 3-((2R)PIPERAZIN-2-YL)-2-HYDROXY-5-METHYLBENZALDEHYDE; 3-((2R)PYRROLIDIN-2-YL)-2-HYDROXY-5-METHYLBENZALDEHYDE; 3-((2S)(2-PIPERIDYL))-2-HYDROXY-5-METHYLBENZALDEHYDE; 3-((2S)AZETIDIN-2-YL)-2-HYDROXY-5-METHYLBENZALDEHYDE; 3-((2S)PIPERAZIN-2-YL)-2-HYDROXY-5-METHYLBENZALDEHYDE; 3-((2S)PYRROLIDIN-2-YL)-2-HYDROXY-5-METHYLBENZALDEHYDE; 3-((3R)MORPHOLIN-3-YL)-2-HYDROXY-5-METHYLBENZALDEHYDE; 3-((3S)MORPHOLIN-3-YL)-2-HYDROXY-5-METHYLBENZALDEHYDE; 3-(1,2,3,4-TETRAHYDROISOQUINOLIN-6-YL)PROPANAL HYDROCHLORIDE; 3-(1,2,3,4-TETRAHYDROISOQUINOLIN-7-YL)PROPANAL HYDROCHLORIDE; 3-(1,4-DIAZEPAN-1-YL)PROPANAL; 3-(1H-BENZOIMIDAZOL-2-YLSULFANYL)-3-PHENYL-PROPENAL; 3-(1H-BENZOIMIDAZOL-2-YLSULFANYLMETHYL)-4-METHOXY-BENZALDEHYDE; 3-(1H-IMIDAZOL-2-YL)-BENZALDEHYDE; 3-(1H-IMIDAZOL-2-YL)-PROPIONALDEHYDE; 3-(1H-IMIDAZOL-4-YL)BENZALDEHYDE; 3-(1H-IMIDAZOL-4-YL)PROPIONALDEHYDE; 3-(1H-IMIDAZOL-4-YLMETHYL)-BENZALDEHYDE; 3-(1H-INDOL-5-YL)BENZALDEHYDE; 3-(1-METHYL-1,2,3,6-TETRAHYDROPYRIDIN-4-YL)-1H-INDOLE-5-CARBALDEHYDE; 3-(2,3-DIHYDRO-1H-INDOL-5-YL)BENZALDEHYDE; 3-(2,3-DIOXO-2,3-DIHYDRO-1H-INDOL-5-YL)BENZALDEHYDE; 3-(2,4-DICHLORO-6-FORMYLPHENOXY)-N-ETHYLPROPANAMIDE; 3-(2,4-DICHLORO-6-FORMYLPHENOXY)-N-METHYLPROPANAMIDE; 3-(2,4-DIMETHYL-5-FORMYL-1H-PYRROLE-3-YL)PROPANOIC ACID; 3-(2,4-DIOXO-1,3-DIAZASPIRO[4.4]NONAN-3-YL)PROPANAL; 3-(2,4-DIOXO-1,3-DIAZASPIRO[4.5]DECAN-3-YL)PROPANAL; 3-(2,4-DIOXO-1,3-DIAZASPIRO[4.7]DODECAN-3-YL)PROPANAL; 3-(2,5-DIOXO-4-PROPYLIMIDAZOLIDIN-1-YL)PROPANAL; 3-(2,5-DIOXOIMIDAZOLIDIN-1-YL)PROPANAL; 3-(2-AMINOETHYLAMINO)-5-METHYL-1H-PYRAZOLE-4-CARBALDEHYDE; 3-(2-BROMO-4-FORMYLPHENOXY)-N-METHYLPROPANAMIDE; 3-(2-BROMO-6-FORMYLPHENOXY)-N-METHYLPROPANAMIDE; 3-(2-CHLORO-4-FORMYL-6-METHOXYPHENOXY)-N-ETHYLPROPANAMIDE; 3-(2-CHLORO-4-FORMYL-6-METHOXYPHENOXY)-N-METHYLPROPANAMIDE; 3-(2-CHLORO-4-FORMYLPHENOXY)-N-(PROPAN-2-YL)PROPANAMIDE; 3-(2-CHLORO-4-FORMYLPHENOXY)-N-CYCLOPROPYLPROPANAMIDE; 3-(2-CHLORO-4-FORMYLPHENOXY)-N-ETHYLPROPANAMIDE; 3-(2-CHLORO-4-FORMYLPHENOXY)-N-METHYLPROPANAMIDE; 3-(2-ETHOXY-4-FORMYLPHENOXY)-N-ETHYLPROPANAMIDE; 3-(2-ETHOXY-4-FORMYLPHENOXY)-N-METHYLPROPANAMIDE; 3-(2-ETHOXY-6-FORMYLPHENOXY)-N-ETHYLPROPANAMIDE; 3-(2-ETHOXY-6-FORMYLPHENOXY)-N-METHYLPROPANAMIDE; 3-(2-ETHOXYCARBONYLETHYL)-2,4-DIMETHYL-5-FORMYLPYRROLE; 3-(2-FORMYL-4-METHOXYPHENOXY)-N-(PROPAN-2-YL)PROPANAMIDE; 3-(2-FORMYL-4-METHOXYPHENOXY)-N-METHYLPROPANAMIDE; 3-(2-FORMYL-4-METHYL-1H-PYRROL-3-YL)-PROPIONIC ACID; 3-(2-FORMYL-4-METHYLPHENOXY)-N-METHYLPROPANAMIDE; 3-(2-FORMYL-4-NITROPHENOXY)-N-METHYLPROPANAMIDE; 3-(2-FORMYL-5-METHOXYPHENOXY)-N-(PROPAN-2-YL)PROPANAMIDE; 3-(2-FORMYL-5-METHOXYPHENOXY)-N-METHYLPROPANAMIDE; 3-(2-FORMYL-5-PROPOXYPHENOXY)-N-METHYLPROPANAMIDE; 3-(2-FORMYL-6-METHOXYPHENOXY)-N-(PROPAN-2-YL)PROPANAMIDE; 3-(2-FORMYL-6-METHOXYPHENOXY)-N-METHYLPROPANAMIDE; 3-(2-FORMYLPHENOXY)-N-(PROPAN-2-YL)PROPANAMIDE; 3-(2-FORMYLPHENOXY)-N-METHYLPROPANAMIDE; 3-(2-FORMYLPIPERIDIN-1-YL)-N-(5-METHYL-1,2-OXAZOL-3-YL)PROPANAMIDE; 3-(2-FORMYLPIPERIDIN-1-YL)-N-(PROPAN-2-YL)PROPANAMIDE; 3-(2-FORMYLPIPERIDIN-1-YL)-N-METHYLPROPANAMIDE; 3-(2-FORMYLPIPERIDIN-1-YL)-N-PHENYLPROPANAMIDE; 3-(3-[(METHYLAMINO)METHYL]PIPERIDIN-1-YL)PROPANAL; 3-(3-AZETIDINYLOXY)-BENZALDEHYDE; 3-(3-CHLORO-2-FORMYLPHENOXY)-N-(PROPAN-2-YL)PROPANAMIDE; 3-(3-CHLORO-2-

FORMYLPHENOXY)-N-CYCLOPROPYLPROPANAMIDE; 3-(3-CHLORO-2-FORMYLPHENOXY)-N-ETHYLPROPANAMIDE; 3-(3-CHLORO-2-FORMYLPHENOXY)-N-METHYLPROPANAMIDE; 3-(3-FORMYL-1H-INDOL-5-YL)BENZOIC ACID; 3-(3-FORMYL-1H-INDOL-5-YL)BENZONITRILE; 3-(3-FORMYLPHENOXY)-N-(PROPAN-2-YL)PROPANAMIDE; 3-(3-FORMYLPHENOXY)-N-METHYLPROPANAMIDE; 3-(3-FORMYLPIPERIDIN-1-YL)-N-(5-METHYL-1,2-OXAZOL-3-YL)PROPANAMIDE; 3-(3-FORMYLPIPERIDIN-1-YL)-N-(PROPAN-2-YL)PROPANAMIDE; 3-(3-FORMYLPIPERIDIN-1-YL)-N-METHYLPROPANAMIDE; 3-(3-FORMYLPIPERIDIN-1-YL)-N-PHENYLPROPANAMIDE; 3-(3-OXO-1,2,3,4-TETRAHYDROQUINOXALIN-1-YL)PROPANAL; 3-(3-OXOPIPERAZIN-1-YL)PROPANAL; 3-(4,4-DIMETHYL-2,5-DIOXOIMIDAZOLIDIN-1-YL)PROPANAL; 3-(4-BROMO-2-FORMYLPHENOXY)-N-METHYLPROPANAMIDE; 3-(4-BUTYL-4-METHYL-2,5-DIOXOIMIDAZOLIDIN-1-YL)PROPANAL; 3-(4-CHLORO-2-FORMYLPHENOXY)-N-(PROPAN-2-YL)PROPANAMIDE; 3-(4-CHLORO-2-FORMYLPHENOXY)-N-CYCLOPROPYLPROPANAMIDE; 3-(4-CHLORO-2-FORMYLPHENOXY)-N-ETHYLPROPANAMIDE; 3-(4-CHLORO-2-FORMYLPHENOXY)-N-METHYLPROPANAMIDE; 3-(4-ETHYL-4-METHYL-2,5-DIOXOIMIDAZOLIDIN-1-YL)PROPANAL; 3-(4-FORMYL-1H-IMIDAZOL-2-YL)-4-NITRO-PHENOL; 3-(4-FORMYL-1H-IMIDAZOL-2-YL)-BENZOIC ACID; 3-(4-FORMYL-1H-IMIDAZOL-2-YL)-BENZONITRILE; 3-(4-FORMYL-1H-IMIDAZOL-2-YL)-PHENOL; 3-(4-FORMYL-2,6-DIMETHOXYPHENOXY)-N-METHYLPROPANAMIDE; 3-(4-FORMYL-2,6-DIMETHYLPHENOXY)-N-(PROPAN-2-YL)PROPANAMIDE; 3-(4-FORMYL-2,6-DIMETHYLPHENOXY)-N-METHYLPROPANAMIDE; 3-(4-FORMYL-2-METHOXYPHENOXY)-N-(PROPAN-2-YL)PROPANAMIDE; 3-(4-FORMYL-2-METHOXYPHENOXY)-N-METHYLPROPANAMIDE; 3-(4-FORMYL-2-NITROPHENOXY)-N-METHYLPROPANAMIDE; 3-(4-FORMYL-3,5-DIMETHYL-1H-PYRAZOL-1-YL)-N-(PROPAN-2-YL)PROPANAMIDE; 3-(4-FORMYLPHENOXY)-N-(PROPAN-2-YL)PROPANAMIDE; 3-(4-FORMYLPHENOXY)-N-METHYLPROPANAMIDE; 3-(4-FORMYLPIPERIDIN-1-YL)-N-(5-METHYL-1,2-OXAZOL-3-YL)PROPANAMIDE; 3-(4-FORMYLPIPERIDIN-1-YL)-N-(PROPAN-2-YL)PROPANAMIDE; 3-(4-FORMYLPIPERIDIN-1-YL)-N-METHYLPROPANAMIDE; 3-(4-FORMYLPIPERIDIN-1-YL)-N-PHENYLPROPANAMIDE; 3-(4-PHENYL-1H-IMIDAZOL-2-YL)-BENZALDEHYDE; 3-(5-CHLORO-1H-INDOL-3-YL)PROPANAL; 3-(5-FLUORO-2,4-DIOXO-1,2,3,4-TETRAHYDROPYRIMIDIN-1-YL)PROPANAL; 3-(5-FORMYL-2-METHOXYPHENOXY)-N-(PROPAN-2-YL)PROPANAMIDE; 3-(5-FORMYL-2-METHOXYPHENOXY)-N-METHYLPROPANAMIDE; 3-(5-FORMYL-2-NITROPHENOXY)-N-METHYLPROPANAMIDE; 3-(5-FORMYL-4H-1,2,4-TRIAZOL-3-YL)BENZONITRILE; 3-(5-FORMYL-4-METHYL-1H-PYRROL-3-YL)PROPANENITRILE; 3-(5-OXO-1,4-DIAZEPAN-1-YL)PROPANAL; 3-(5-OXO-PYRROLIDIN-3-YL)-BENZALDEHYDE; 3-(7H-PYRROLO[2,3-D]PYRIMIDIN-4-YL)BENZALDEHYDE; 3-(8-METHYL-2,4-DIOXO-1,3-DIAZASPIRO[4.5]DECAN-3-YL)PROPANAL; 3-(9H-PURIN-6-YLSULFANYL)PROPANAL; 3-(AZETIDIN-3-YL)-2-HYDROXY-5-METHYLBENZALDEHYDE; 3-(BOC-AMIDINO)-BENZALDEHYDE; 3-(CHLOROMETHYL)-2-FORMYL-1-OXO-1,5-DIHYDROPYRIDO[1,2-A]BENZIMIDAZOLE-4-CARBONITRILE; 3-(CYCLOHEXYLAMINO)-2-ISOPROPYL-3-PHENYLACRYLALDEHYDE; 3-(PIPERAZIN-1-YL)PROPANAL; 3,3-DIMETHYL-2-OXO-2,3-DIHYDRO-1H-INDOLE-5-CARBALDEHYDE; 3,4,5,6-TETRAHYDROXY-2-(METHYLAMINO)HEXANAL; 3,4,5-TRIMETHYL-1H-PYRROLE-2-CARBOXALDEHYDE; 3,4-BIS(4-FLUOROPHENYL)-1H-PYRROLE-2-CARBALDEHYDE; 3,4-BIS(TRIFLUOROMETHYL)-1H-PYRROLE-2,5-DICARBALDEHYDE; 3,4-BIS(TRIFLUOROMETHYL)-1H-PYRROLE-2-CARBALDEHYDE; 3,4-DIHYDRO-2,3-DIOXO-2H-BENZO[B][1,4]OXAZINE-6-CARBALDEHYDE; 3,4-DIHYDRO-3-OXO-2H-BENZO[B][1,4]OXAZINE-8-CARBALDEHYDE; 3,4-DIHYDRO-3-OXO-2-QUINOXALINECARBOXALDEHYDE; 3,4-DIMETHYL-1H-PYRROLE-2-CARBOXALDEHYDE; 3,4-DIMETHYL-2,5-PYRROLEDICARBOXALDEHYDE; 3,4-DIMETHYL-5-FORMYLPYRROLE-2-CARBOXYLIC ACID; 3,5-DIBROMO-4-(METHYLAMINO)BENZALDEHYDE; 3,5-DICHLORO-2-[(2-OXO-1,3-OXAZOLIDIN-5-YL)METHOXY]BENZALDEHYDE; 3,5-DICHLORO-4-(METHYLAMINO)BENZALDEHYDE; 3,5-DIFLUORO-4-(3-OXOPIPERAZIN-1-YL)BENZALDEHYDE; 3,5-DIFLUORO-4-(5-OXO-1,4-DIAZEPAN-1-YL)BENZALDEHYDE; 3,5-DIMETHYL-1-(7H-PURIN-6-YL)-1H-PYRAZOLE-4-CARBALDEHYDE; 3,5-DIMETHYL-1H-INDOLE-2-CARBALDEHYDE; 3,5-DIMETHYL-1H-PYRROLE-2-CARBOXALDEHYDE; 3,5-DIMETHYL-4-[(2-OXO-1,3-OXAZOLIDIN-5-YL)METHOXY]BENZALDEHYDE; 3,5-DIMETHYL-4-[(2-OXOAZEPAN-3-YL)OXY]BENZALDEHYDE; 3,5-DIMETHYL-4-[2-(2-OXOIMIDAZOLIDIN-1-YL)ETHOXY]BENZALDEHYDE; 3,5-DIMETHYL-PYRROLE-2,4-DICARBOXALDEHYDE; 3,7-DIMETHYL-1H-INDOLE-2-CARBALDEHYDE; 3,7-DIMETHYL-2,6-DIOXO-2,3,6,7-TETRAHYDRO-1H-PURINE-8-CARBALDEHYDE; 3-[(1-FORMYLNAPHTHALEN-2-YL)OXY]-N-METHYLPROPANAMIDE; 3-[(1R)-1-(METHYLAMINO)ETHYL]-2-HYDROXY-5-METHYLBENZALDEHYDE; 3-[(1S)-1-(METHYLAMINO)ETHYL]-2-HYDROXY-5-METHYLBENZALDEHYDE; 3-[(1S)-2-HYDROXY-1-(METHYLAMINO)ETHYL]-2-HYDROXY-5-METHYLBENZALDEHYDE; 3-[(2,4-DIOXO-1,2,3,4-TETRAHYDROPYRIMIDIN-1-YL)METHYL]-4-METHOXYBENZALDEHYDE; 3-[(2,5-DIOXOIMIDAZOLIDIN-1-YL)METHYL]-4-METHOXYBENZALDEHYDE; 3-[(2-OXO-1,2,3,4-TETRAHYDROQUINOLIN-6-YL)OXY]PROPANAL; 3-[(2-OXO-1,3-OXAZOLIDIN-5-YL)METHOXY]BENZALDEHYDE; 3-[(2-OXOAZEPAN-3-YL)OXY]BENZALDEHYDE; 3-[(4,4-DIMETHYL-2,5-DIOXOIMIDAZOLIDIN-1-YL)METHYL]-4-METHOXYBENZALDEHYDE; 3-[(4-NITROPHENYL)AMINO]-1H-INDOLE-2-CARBALDEHYDE; 3-[(5-METHYL-4H-1,2,4-TRIAZOL-3-YL)SULFANYL]PROPANAL; 3-[(6-FORMYL-2H-1,3-BENZODIOXOL-5-YL)OXY]-N-METHYLPROPANAMIDE; 3-[(BENZYLOXYCARBONYL)AMINO]-1-PROPANAL; 3-[1-(1H-IMIDAZOL-4-YL)-ETHYL]-BENZALDEHYDE; 3-[2-(1H-IMIDAZOL-4-YL)-ETHYL]-BENZAL-

DEHYDE; 3-[2-(1H-IMIDAZOL-4-YL)-VINYL]-BENZ-ALDEHYDE; 3-[2-(2-METHYLIMIDAZOL-4-YL)-ETHYL]-BENZALDEHYDE; 3-[2-(2-OXOIMIDAZOLIDIN-1-YL)ETHOXY]BENZALDEHYDE; 3-[4-(FURAN-2-YL)-4-METHYL-2,5-DIOXOIMIDAZOLIDIN-1-YL]PROPANAL; 3-[4-(PHENYLAMINO)PHENOXY]PROPANAL; 3-[ETHYL(PIPERIDIN-4-YL)AMINO]PROPANAL; 3-[METHYL(PIPERIDIN-4-YL)AMINO]PROPANAL; 3-[PIPERIDIN-4-YL(PROPYL)AMINO]PROPANAL; 3-ACETAMIDOPHENYLGLYOXAL HYDRATE; 3-ACETYL-4-METHYL-1H-PYRROLE-2-CARBALDEHYDE; 3-AMINO-1H-PYRROLO[2,3-B]PYRIDINE-4-CARBALDEHYDE; 3-ANILINO-2-NITROACRYLALDEHYDE; 3-BUTYL-1-[2-(4-FORMYLPIPERIDIN-1-YL)ACETYL]UREA; 3-CHLORO-4-(METHYLAMINO)BENZALDEHYDE; 3-CHLORO-4-[(2-OXO-1,3-OXAZOLIDIN-5-YL)METHOXY]BENZALDEHYDE; 3-CHLORO-4-[2-(2-OXOIMIDAZOLIDIN-1-YL)ETHOXY]BENZALDEHYDE; 3-CHLORO-5-METHOXY-4-[(2-OXO-1,3-OXAZOLIDIN-5-YL)METHOXY]BENZALDEHYDE; 3-CYANO-4-METHYL-7-AZAINDOLE-4-CARBALDEHYDE; 3-CYCLOPROPOXY-2-(METHYLAMINO)BENZALDEHYDE; 3-CYCLOPROPOXY-2-(METHYLAMINO)ISONICOTINALDEHYDE; 3-CYCLOPROPOXY-2-FORMYL-N-METHYLBENZAMIDE; 3-CYCLOPROPOXY-2-FORMYL-N-METHYLISONICOTINAMIDE; 3-CYCLOPROPOXY-4-(METHYLAMINO)BENZALDEHYDE; 3-CYCLOPROPOXY-4-(METHYLAMINO)PICOLINALDEHYDE; 3-CYCLOPROPOXY-4-FORMYL-N-METHYLBENZAMIDE; 3-CYCLOPROPOXY-4-FORMYL-N-METHYLPICOLINAMIDE; 3-CYCLOPROPOXY-5-(METHYLAMINO)CYCLOHEXA-1,3-DIENECARBALDEHYDE; 3-CYCLOPROPOXY-5-(METHYLAMINO)ISONICOTINALDEHYDE; 3-CYCLOPROPOXY-5-(METHYLAMINO)PICOLINALDEHYDE; 3-CYCLOPROPOXY-5-FORMYL-N-METHYLBENZAMIDE; 3-CYCLOPROPOXY-5-FORMYL-N-METHYLISONICOTINAMIDE; 3-CYCLOPROPOXY-5-FORMYL-N-METHYLPICOLINAMIDE; 3-CYCLOPROPOXY-6-(METHYLAMINO)PICOLINALDEHYDE; 3-CYCLOPROPOXY-6-FORMYL-N-METHYLPICOLINAMIDE; 3-CYCLOPROPYL-1-[2-(3-FORMYLPIPERIDIN-1-YL)ACETYL]UREA; 3-CYCLOPROPYL-1-[2-(4-FORMYLPIPERIDIN-1-YL)ACETYL]UREA; 3-DIMETHYLAMINOMETHYL-1H-INDOLE-2-CARBALDEHYDE; 3-ET-5((4-ET-5-FORMYL-3-ME-2H-PYRROL-2-YLIDENE)ME)-4-ME-1H-PYRROLE-2-CARBALDEHYDE; 3-ETHOXY-2-[(2-OXO-1,3-OXAZOLIDIN-5-YL)METHOXY]BENZALDEHYDE; 3-ETHOXY-4-[(2-OXO-1,3-OXAZOLIDIN-5-YL)METHOXY]BENZALDEHYDE; 3-ETHYL-1-[2-(2-FORMYLPHENOXY)PROPANOYL]UREA; 3-ETHYL-1-[2-(2-FORMYLPIPERIDIN-1-YL)PROPANOYL]UREA; 3-ETHYL-1-[2-(3-FORMYLPHENOXY)PROPANOYL]UREA; 3-ETHYL-1-[2-(3-FORMYLPIPERIDIN-1-YL)PROPANOYL]UREA; 3-ETHYL-1-[2-(4-FORMYLPHENOXY)PROPANOYL]UREA; 3-ETHYL-1-[2-(4-FORMYLPIPERIDIN-1-YL)ACETYL]UREA; 3-ETHYL-1H-INDOLE-2-CARBALDEHYDE; 3-ETHYL-4,5-DIMETHYLPYRROLE-2-CARBOXALDEHYDE; 3-ETHYL-4-METHYL-1H-PYRROLE-2,5-DICARBOXALDEHYDE; 3-ETHYL-4-METHYL-1H-PYRROLE-2-CARBOXALDEHYDE; 3-ETHYL-5-METHYL-1H-INDOLE-2-CARBALDEHYDE; 3-ETHYL-5-OXO-5,6-DIHYDRO-IMIDAZO[1,2-C]PYRIMIDINE-2-CARBALDEHYDE; 3-FLUORO-2-(1-PIPERAZINO)-BENZALDEHYDE; 3-FLUORO-2-(1-PIPERAZINO)-BENZALDEHYDE HYDROCHLORIDE; 3-FLUORO-4-(1-PIPERAZINO)-BENZALDEHYDE HYDROCHLORIDE; 3-FLUORO-4-(3-OXOPIPERAZIN-1-YL)BENZALDEHYDE; 3-FLUORO-4-(5-OXO-1,4-DIAZEPAN-1-YL)BENZALDEHYDE; 3-FLUORO-5-(1H-IMIDAZOL-2-YL)-BENZALDEHYDE; 3-FORMALDEHYDE PIPERIDINE; 3-FORMYL-1,6-DIHYDROXYCARBAZOLE; 3-FORMYL-1H-INDOLE-2-CARBONITRILE; 3-FORMYL-1H-INDOLE-2-CARBOXYLIC ACID; 3-FORMYL-1H-INDOLE-4-CARBONITRILE; 3-FORMYL-1H-INDOLE-4-CARBOXYLIC ACID; 3-FORMYL-1H-INDOLE-4-CARBOXYLIC ACID METHYL ESTER; 3-FORMYL-1H-INDOLE-5-CARBOXYLIC ACID ETHYL ESTER; 3-FORMYL-1H-INDOLE-6-CARBONITRILE; 3-FORMYL-1H-INDOLE-6-CARBOXYLIC ACID; 3-FORMYL-1H-INDOLE-6-CARBOXYLIC ACID ETHYL ESTER; 3-FORMYL-1H-INDOLE-7-CARBONITRILE; 3-FORMYL-1H-INDOLE-7-CARBOXYLIC ACID; 3-FORMYL-1H-PYRROLE-2-CARBOXYLIC ACID ETHYL ESTER; 3-FORMYL-1H-PYRROLO[2,3-B]PYRIDINE-4-CARBONITRILE; 3-FORMYL-1H-PYRROLO[2,3-B]PYRIDINE-4-CARBOXYLIC ACID; 3-FORMYL-1H-PYRROLO[2,3-B]PYRIDINE-6-CARBONITRILE; 3-FORMYL-1H-PYRROLO[2,3-C]PYRIDINE-4-CARBONITRILE; 3-FORMYL-1H-PYRROLO[2,3-C]PYRIDINE-4-CARBOXYLIC ACID; 3-FORMYL-1H-PYRROLO[2,3-C]PYRIDINE-7-CARBONITRILE; 3-FORMYL-1H-PYRROLO[2,3-C]PYRIDINE-7-CARBOXYLIC ACID; 3-FORMYL-1H-PYRROLO[3,2-B]PYRIDINE-5-CARBONITRILE; 3-FORMYL-1H-PYRROLO[3,2-B]PYRIDINE-5-CARBOXYLIC ACID; 3-FORMYL-1H-PYRROLO[3,2-B]PYRIDINE-6-CARBONITRILE; 3-FORMYL-1H-PYRROLO[3,2-B]PYRIDINE-7-CARBONITRILE; 3-FORMYL-2-HYDROXY-N-METHYLBENZAMIDE; 3-FORMYL-4(1H)-PYRIDONE; 3-FORMYL-4,6-DIMETHOXY-1H-INDOLE-2-CARBOXYLIC ACID; 3-FORMYL-4,6-DIMETHOXY-1H-INDOLE-2-CARBOXYLIC ACID METHYL ESTER; 3-FORMYL-4-AZAINDOLE-5-CARBOXYLIC ACID METHYL ESTER; 3-FORMYL-4-AZAINDOLE-6-CARBOXYLIC ACID; 3-FORMYL-4-AZAINDOLE-6-CARBOXYLIC ACID METHYL ESTER; 3-FORMYL-4-HYDROXY-N-METHYLBENZAMIDE; 3-FORMYL-4-METHYL-1H-INDOLE-7-CARBONITRILE; 3-FORMYL-4-METHYL-1H-PYRROLO[2,3-B]PYRIDINE-5-CARBOXYLIC ACID; 3-FORMYL-4-METHYL-INDOLE; 3-FORMYL-4-NITRO-7-AZAINDOLE; 3-FORMYL-5,6-DIMETHOXY-1H-INDOLE-2-CARBOXYLIC ACID; 3-FORMYL-5,6-DIMETHOXY-1H-INDOLE-2-CARBOXYLIC ACID METHYL ESTER; 3-FORMYL-5-AZAINDOLE; 3-FORMYL-5-HYDROXY-N-METHYLBENZAMIDE; 3-FORMYL-5-METHOXY-1H-INDOLE-2-CARBOXYLIC ACID; 3-FORMYL-5-METHYL-1H-INDOLE-2-CARBOXYLIC ACID; 3-FORMYL-5-NITRO-1H-INDOLE-2-CARBOXYLIC ACID ETHYL ESTER; 3-FORMYL-6-(TRIFLUOROMETHYL)-1H-INDOLE-5-CARBONITRILE; 3-FORMYL-6-METHOXY-1H-INDOLE-2-CARBOXYLIC ACID; 3-FORMYL-6-METHYL-5-NITRO-7-AZAINDOLE; 3-FORMYL-6-METHYL-7-AZAINDOLE; 3-FORMYLINDOLE-4-BORONIC ACID PINACOL ESTER; 3-FORMYLINDOLE-5-CARBOXYLIC ACID; 3-FORMYLINDOLE-7-CARBOXYLIC ACID ETHYL ESTER;

3-FORMYLINDOLE-7-CARBOXYLIC ACID METHYL ESTER; 3-FORMYL-N,N-DIMETHYL-1H-INDOLE-5-SULFONAMIDE; 3-FORMYL-N-METHYL-BENZ-AMIDE; 3-FORMYLPHENYL PHENYLCARBAMATE; 3H-BENZO[D]IMIDAZOLE-4-CARBALDEHYDE; 3H-IMIDAZO[4,5-B]PYRIDINE-2-CARBOXALDE-HYDE; 3H-IMIDAZO[4,5-B]PYRIDINE-6-CARBALDE-HYDE; 3H-IMIDAZO[4,5-B]PYRIDINE-7-CARBALDE-HYDE; 3-HYDROXY-2-(METHYLAMINO) BENZALDEHYDE; 3-HYDROXY-4-(METHYLAMINO) BENZALDEHYDE; 3-HYDROXY-5-(METHYLAMINO) BENZALDEHYDE; 3-METHOXY-1H-PYRROLE-2-CARBALDEHYDE; 3-METHOXY-2-[(2-OXO-1,3-OXAZOLIDIN-5-YL)METHOXY]BENZALDEHYDE; 3-METHOXY-2-[(2-OXOAZEPAN-3-YL)OXY]BENZ-ALDEHYDE; 3-METHOXY-2-[2-(2-OXOIMIDAZOLI-DIN-1-YL)ETHOXY]BENZALDEHYDE; 3-METHOXY-4-[(2-OXO-1,3-OXAZOLIDIN-5-YL)METHOXY] BENZALDEHYDE; 3-METHOXY-4-[(2-OXOAZEPAN-3-YL)OXY]BENZALDEHYDE; 3-METHOXY-4-[2-(2-OXOIMIDAZOLIDIN-1-YL)ETHOXY] BENZALDEHYDE; 3-METHYL-1H-INDOLE-2-CARBALDEHYDE; 3-METHYL-1H-PYRROLE-2,4-DICARBALDEHYDE; 3-METHYL-1H-PYRROLE-2,5-DICARBALDEHYDE; 3-METHYL-1H-PYRROLE-2-CARBALDEHYDE; 3-METHYL-3-PHENYLAMINO-BUTYRALDEHYDE; 3-METHYL-4-(3-OXOPIPERAZIN-1-YL)BENZALDEHYDE; 3-METHYL-4-(5-OXO-1,4-DIAZEPAN-1-YL)BENZALDEHYDE; 3-METHYL-5-OXO-5,6-DIHYDRO-IMIDAZO[1,2-C]PY-RIMIDINE-2-CARBALDEHYDE; 3-N-BOC-AMINO-4-FORMYL-5-METHOXYPYRIDINE; 3-NITRO-1H-PYR-ROLE-2-CARBALDEHYDE; 3-NITRO-1H-PYRROLO[2,3-B]PYRIDINE-4-CARBALDEHYDE; 3-NITRO-1H-PYRROLO[2,3-B]PYRIDINE-5-CARBALDEHYDE; 3-NITRO-4-(3-OXOPIPERAZIN-1-YL)BENZALDE-HYDE; 3-NITRO-4-(5-OXO-1,4-DIAZEPAN-1-YL)BEN-ZALDEHYDE; 3-NITRO-4-[(2-OXO-1,3-OXAZOLIDIN-5-YL)METHOXY]BENZALDEHYDE; 3-OXO-1,3-DIHYDRO-ISOINDOLE-4-CARBALDEHYDE; 3-OXO-3,4-DIHYDRO-2H-BENZO[1,4]OXAZINE-6-CARBALDEHYDE; 3-OXO-3,4-DIHYDRO-2H-BENZO[B][1,4]OXAZINE-7-CARBALDEHYDE; 3-OXO-3,4-DIHYDRO-2H-PYRIDO[3,2-B][1,4]OXAZINE-6-CARBALDEHYDE; 3-OXO-3,4-DIHYDRO-2H-PYRIDO[3,2-B][1,4]THIAZINE-6-CARBALDEHYDE; 3-OXOISOINDOLINE-5-CARBALDEHYDE; 3-PHE-NYL-1H-INDOLE-2-CARBALDEHYDE; 3-PHENYL-1H-PYRROLO[2,3-B]PYRIDINE-2-CARBOXALDE-HYDE; 3-PHENYL-1H-PYRROLO[2,3-B]PYRIDINE-4-CARBOXALDEHYDE; 3-PHENYL-1H-PYRROLO[2,3-B]PYRIDINE-5-CARBOXALDEHYDE; 3-PHENYL-1H-PYRROLO[2,3-B]PYRIDINE-6-CARBOXALDEHYDE; 3-TERT-BUTYL-1-[2-(4-FORMYLPIPERIDIN-1-YL) ACETYL]UREA; 4-((2,4-DIOXO-1,3-THIAZOLIDIN-5-YLIDENE)METHYL)BENZALDEHYDE; 4-((4-[(1R)-1-(METHYLAMINO)ETHYL]PHENYL)METHYL) BENZALDEHYDE; 4-((4-[(1S)-1-(METHYLAMINO) ETHYL]PHENYL)METHYL)BENZALDEHYDE; 4-((4-[(1S)-2-HYDROXY-1-(METHYLAMINO)ETHYL] PHENYL)METHYL)BENZALDEHYDE; 4-(1,1-DIMETHYLETHYL)-1H-PYRROLE-2-CARBALDEHYDE; 4-(1H-BENZIMIDAZOL-6-YLOXY)-3-CHLORO-BENZALDEHYDE; 4-(1H-BENZIMIDAZOL-6-YLOXY)-BENZALDEHYDE; 4-(1H-BENZOIMIDAZOL-2-YLMETHOXY)-3-METHOXY-BENZALDEHYDE; 4'-(1H-IMIDAZOL-2-YL)-[1,1'-BIPHENYL]-3-CARBOXALDEHYDE; 4-(1H-IMIDAZOL-2-YL)-BENZALDEHYDE; 4-(1H-IMIDAZOL-2-YL)-B-OXO-BENZENEPROPANAL; 4-(1H-IMIDAZOL-2-YL)-BUTYRALDEHYDE; 4-(1H-IMIDAZOL-4-YL)BENZALDEHYDE; 4-(1H-IMIDA-ZOL-4-YL)-BUTYRALDEHYDE; 4-(1H-IMIDAZOL-4-YLMETHYL)-BENZALDEHYDE; 4-(1H-INDOL-3-YL) BUTANAL; 4-(1H-INDOL-4-YL)BENZALDEHYDE; 4-(1H-INDOL-5-YL)BENZALDEHYDE; 4-(2,3-DI-HYDRO-1H-INDOL-5-YL)BENZALDEHYDE; 4-(2,3-DIOXO-2,3-DIHYDRO-1H-INDOL-5-YL)BENZALDE-HYDE; 4-(2,4-DIFLUOROPHENYL)-4-PIPERIDINYLMETHANONE HYDROCHLORIDE; 4-(2-[4-(TRIFLUOROMETHYL)PIPERIDINO]ACETYL)-1H-PYRROLE-2-CARBALDEHYDE; 4-(2-AMINO-1H-IMIDAZOL-4-YL)-BUTYRALDEHYDE HCL; 4-(2-CHLOROACETYL)-1H-PYRROLE-2-CARBALDEHYDE; 4-(2-CHLOROPYRIMIDIN-5-YL)-1H-PYRROLE-2-CARBALDEHYDE; 4-(2-FLUOROPHENYL)-1H-INDOLE-3-CARBALDEHYDE; 4-(2-FORMYLPIPERIDIN-1-YL)-N-METHYLPYRI-DINE-2-CARBOXAMIDE; 4-(2-FORMYLVINYL)-AC-ETANILIDE; 4-(2-HYDROXY-ETHYLAMINO)-BENZ-ALDEHYDE; 4-(2-PIPERIDIN-4-YLETHYL) IMIDAZOLE-2-CARBALDEHYDE; 4-(2-PROPEN-1-YL)-1H-PYRROLE-2-CARBOXALDEHYDE; 4-(2-PYRROLIDIN-1-YLETHYL)IMIDAZOLE-2-CARBALDEHYDE; 4-(3,9-DIAZASPIRO[5.5]UNDEC-3-YL)BENZALDEHYDE; 4-(3-ACETYLAMINOPHENYL)-2-FORMYLPHENOL; 4-(3-AZETIDINYLOXY)-BENZALDEHYDE; 4-(3-BROMOPHENYL)-1H-IMIDAZOLE-2-CARBALDEHYDE; 4-(3-CHLOROPHENYL)-1H-IMIDAZOLE-2-CARBALDEHYDE; 4-(3-FLUOROPHENYL)-1H-IMIDAZOLE-2-CARBALDEHYDE; 4-(3-FLUOROPHENYL)-1H-INDOLE-3-CARBALDEHYDE; 4-(3-FORMYL-1H-INDOL-5-YL)BENZOIC ACID; 4-(3-FORMYL-1H-INDOL-5-YL)BENZONITRILE; 4-(3-FORMYLPIPERIDIN-1-YL)-N-METHYLPYRIDINE-2-CARBOXAMIDE; 4-(3-METHOXYPHENYL)-1H-IMIDAZOLE-2-CARBALDEHYDE; 4-(3-OXO-1,2,3,4-TETRAHYDROQUINOXALIN-1-YL) BENZALDEHYDE; 4-(3-OXO-3,4-DIHYDRO-2H-PYRIDO[3,2-B][1,4]OXAZIN-6-YLOXY)BUTANAL; 4-(3-OXOPIPERAZIN-1-YL)BENZALDEHYDE; 4-(4-BROMOPHENYL)-1H-IMIDAZOLE-2-CARBALDE-HYDE; 4-(4-BROMOPHENYL)-1H-PYRROLE-2-CARB-ALDEHYDE; 4-(4-CHLOROPHENYL)-1H-IMIDAZOLE-2-CARBALDEHYDE; 4-(4-CHLOROPHENYL)-1H-PYRROLE-2-CARBALDEHYDE; 4-(4-DIMETHOXYMETHYLIMIDAZOL-2-YL)-BENZALDEHYDE; 4-(4-FLUORO-PHENYL)-1H-IMIDAZOLE-2-CARBALDEHYDE; 4-(4-FLUOROPHENYL)-1H-INDOLE-3-CARBALDEHYDE; 4-(4-FLUOROPHENYL)-2-THIOXO-2,3-DIHYDRO-1,3-THIAZOLE-5-CARBALDEHYDE; 4-(4-FORMYL-1H-IMIDAZOL-2-YL)-2-NITRO-PHENOL; 4-(4-FORMYL-1H-IMIDAZOL-2-YL)-3-METHOXY-PHENOL; 4-(4-FORMYL-1H-IMIDAZOL-2-YL)-BENZOIC ACID; 4-(4-FORMYL-1H-IMIDAZOL-2-YL)-BENZONITRILE; 4-(4-FORMYL-1H-IMIDAZOL-2-YL)-NAPHTHALEN-1-OL; 4-(4-FORMYL-1H-IMIDAZOL-2-YL)-PHENOL; 4-(4-FORMYLIMIDAZOL-2-YL)-2,6-DIMETHOXY-PHE-NOL; 4-(4-FORMYLIMIDAZOL-2-YL)-2,6-DIMETHYL-PHENOL; 4-(4-FORMYLIMIDAZOL-2-YL)-2-

METHOXY-6-NITROPHENOL; 4-(4-FORMYLIMIDAZOL-2-YL)-2-METHOXY-PHENOL; 4-(4-FORMYLPIPERIDIN-1-YL)-N-METHYLPYRIDINE-2-CARBOXAMIDE; 4-(4-METHOXYPHENYL)-1H-IMIDAZOLE-2-CARBALDEHYDE; 4-(4-METHYL-7-OXO-7,8-DIHYDRO-PYRIDO[2,3-D]PYRIMIDIN-2-YLOXY)BUTYRALDEHYDE; 4-(4-PHENYL-1H-IMIDAZOL-2-YL)-BENZALDEHYDE; 4-(4-PIPERIDINYLOXY)BENZALDEHYDE; 4-(4-PYRIDIN-2-YL-1H-IMIDAZOL-2-YL)-BENZALDEHYDE; 4-(4-PYRIDIN-3-YL-1H-IMIDAZOL-2-YL)-BENZALDEHYDE; 4-(4-PYRIDIN-4-YL-1H-IMIDAZOL-2-YL)-BENZALDEHYDE; 4-(5,6,7,8-TETRAHYDRO-[1,2,4]TRIAZOLO[4,3-A]PYRAZIN-3-YL)-BENZALDEHYDE; 4-(5-ETHYL-1,3,4-OXADIAZOL-2-YL)-2,5-DIMETHYL-1H-PYRROLE-3-CARBALDEHYDE; 4-(5-FLUORO-1H-INDOL-3-YL)BUTANAL; 4-(5-FORMYL-4H-1,2,4-TRIAZOL-3-YL)BENZONITRILE; 4-(5-ISOPROPYL-1,3,4-OXADIAZOL-2-YL)-2,5-DIMETHYL-1H-PYRROLE-3-CARBALDEHYDE; 4-(5-OXO-1,4-DIAZEPAN-1-YL)BENZALDEHYDE; 4-(5-OXO-PYRROLIDIN-3-YL)-BENZALDEHYDE; 4-(7H-PYRROLO[2,3-D]PYRIMIDIN-4-YL)BENZALDEHYDE; 4-(7-OXO-5,6,7,8-TETRAHYDRO-1,8-NAPHTHYRIDIN-2-YLOXY)BUTANAL; 4-(BENZYLAMINO)-2-(METHYLTHIO)PYRIMIDINE-5-CARBALDEHYDE; 4-(BENZYLAMINO)-2-OXO-2H-CHROMENE-3-CARBALDEHYDE; 4-(BENZYLAMINO)-6-CHLORO-5-PYRIMIDINECARBALDEHYDE; 4-(BENZYLOXY)-6-FLUORO-1H-INDOLE-2-CARBALDEHYDE; 4-(BENZYLOXY)-7-FLUORO-1H-INDOLE-2-CARBALDEHYDE; 4-(BOC-AMIDINO)-BENZALDEHYDE; 4-(BUTYLAMINO)-2-OXO-2H-CHROMENE-3-CARBALDEHYDE; 4-(CYCLOBUTYLAMINO)-2-(METHYLTHIO)PYRIMIDINE-5-CARBALDEHYDE; 4-(CYCLOHEPTYLAMINO)-2-(METHYLSULFANYL)-5-PYRIMIDINECARBALDEHYDE; 4-(CYCLOHEXYLAMINO)-3-NITROBENZALDEHYDE; 4-(CYCLOPENTYLAMINO)-2-(METHYLSULFANYL)-5-PYRIMIDINECARBALDEHYDE; 4-(CYCLOPENTYLAMINO)-6-METHYL-2-(METHYLSULFANYL)-5-PYRIMIDINECARBALDEHYDE; 4-(ETHYLAMINO)-2-(METHYLSULFANYL)-5-PYRIMIDINECARBALDEHYDE; 4-(ETHYLAMINO)-2-OXO-2H-CHROMENE-3-CARBALDEHYDE; 4-(ETHYLAMINO)-6-METHYL-2-(METHYLSULFANYL)-5-PYRIMIDINECARBALDEHYDE; 4-(METHYLAMINO)-1H-PYRROLO[2,3-B]PYRIDINE-5-CARBALDEHYDE; 4-(METHYLAMINO)-3-NITROBENZALDEHYDE; 4-(N-BOC-AMINO)CYCLOHEXYLETHANAL; 4-(PIPERIDIN-4-YLOXY)BENZALDEHYDE HYDROCHLORIDE; 4-(PROP-1-YNYL)-1H-PYRROLE-2-CARBALDEHYDE; 4-(PYRIDIN-3-YL)-1H-INDOLE-3-CARBALDEHYDE; 4-(PYRIDIN-4-YL)-1H-INDOLE-3-CARBALDEHYDE; 4-(TRIFLUOROMETHYL)-1H-IMIDAZOLE-2-CARBALDEHYDE; 4-(TRIFLUOROMETHYL)-1H-PYRROLO[2,3-B]PYRIDINE-3-CARBALDEHYDE; 4-(TRIFLUOROMETHYL)-1H-PYRROLO[3,2-C]PYRIDINE-3-CARBALDEHYDE; 4-(TRIFLUOROMETHYL)INDOLE-3-CARBOXALDEHYDE; 4-(TRIMETHYLSILYL)-1H-PYRROLE-2-CARBOXALDEHYDE; 4,4'-DIFORMYLDIPHENYLAMINE; 4,5,6,7,8,9-HEXAHYDRO-1H-CYCLOOCTA[B]PYRROLE-2-CARBALDEHYDE; 4,5,6,7-TETRAFLUOROINDOLE-3-CARBOXALDEHYDE; 4,5,6,7-TETRAHYDRO-1H-INDOLE-2-CARBALDEHYDE; 4,5,6,7-TETRAHYDRO-1H-PYRAZOLO[4,3-C]PYRIDINE-3-CARBALDEHYDE; 4,5,6,7-TETRAHYDRO-2H-ISOINDOLE-1,3-DICARBALDEHYDE; 4,5,6,7-TETRAHYDRO-2H-ISOINDOLE-1-CARBALDEHYDE; 4,5,6,7-TETRAHYDRO-4-OXO-2H-PYRROLO[3,4-C]PYRIDINE-1-CARBOXALDEHYDE; 4,5,6,7-TETRAHYDRO-5-OXO-1H-PYRROLO[2,3-C]PYRIDINE-3-CARBOXALDEHYDE; 4,5,6,7-TETRAHYDRO-7,7-DIMETHYL-1H-INDOLE-2-CARBOXALDEHYDE; 4,5,6,7-TETRAHYDROBENZOIMIDAZOLE-2-CARBALDEHYDE; 4,5,6,7-TETRAHYDROPYRAZOLO[1,5-A]PYRIMIDINE-3-CARBALDEHYDE; 4,5,6,7-TETRAHYDROTHIAZOLO[5,4-C]PYRIDINE-2-CARBALDEHYDE; 4,5,6,7-TETRAHYDROTHIENO[3,2-C]PYRIDINE-2-CARBALDEHYDE; 4,5-DICHLOROINDOLE-3-CARBOXALDEHYDE; 4,5-DIETHYL-1H-IMIDAZOLE-2-CARBALDEHYDE; 4,5-DIFLUOROINDOLE-3-CARBOXALDEHYDE; 4,5-DIHYDRO-4-OXO-3H-PYRROLO[3,2-D]PYRIMIDINE-7-CARBOXALDEHYDE; 4,5-DIHYDRO-4-OXO-FURO[3,2-C]PYRIDINE-2-CARBOXALDEHYDE; 4,5-DIMETHOXY-1H-INDOLE-3-CARBALDEHYDE; 4,5-DIMETHYL-1H-IMIDAZOLE-2-CARBALDEHYDE; 4,5-DIMETHYLPYRROLE-2-CARBOXALDEHYDE; 4,6-DICHLOROINDOLE-3-CARBOXALDEHYDE; 4,6-DIFLUORO-2-(2,3-DIFLUOROPHENYL)-1H-INDOLE-3-CARBOXALDEHYDE; 4,6-DIFLUORO-2-(2,4-DIFLUOROPHENYL)-1H-INDOLE-3-CARBOXALDEHYDE; 4,6-DIFLUORO-2-(2,5-DIFLUOROPHENYL)-1H-INDOLE-3-CARBOXALDEHYDE; 4,6-DIFLUORO-2-(2,6-DIFLUOROPHENYL)-1H-INDOLE-3-CARBOXALDEHYDE; 4,6-DIFLUORO-2-(2-FLUOROPHENYL)-1H-INDOLE-3-CARBOXALDEHYDE; 4,6-DIFLUORO-2-(2-METHYLPHENYL)-1H-INDOLE-3-CARBOXALDEHYDE; 4,6-DIFLUORO-2-(3,4-DIFLUOROPHENYL)-1H-INDOLE-3-CARBOXALDEHYDE; 4,6-DIFLUORO-2-(3,5-DIFLUOROPHENYL)-1H-INDOLE-3-CARBOXALDEHYDE; 4,6-DIFLUORO-2-(3-FLUOROPHENYL)-1H-INDOLE-3-CARBOXALDEHYDE; 4,6-DIFLUORO-2-(3-METHYLPHENYL)-1H-INDOLE-3-CARBOXALDEHYDE; 4,6-DIFLUORO-2-(4-ETHYLPHENYL)-1H-INDOLE-3-CARBOXALDEHYDE; 4,6-DIFLUORO-2-(4-FLUOROPHENYL)-1H-INDOLE-3-CARBOXALDEHYDE; 4,6-DIFLUORO-2-(4-METHYLPHENYL)-1H-INDOLE-3-CARBOXALDEHYDE; 4,6-DIFLUORO-2-[4-(1-METHYLETHYL)PHENYL]-1H-INDOLE-3-CARBOXALDEHYDE; 4,6-DIFLUOROINDOLE-3-CARBOXALDEHYDE; 4,6-DIMETHYL-2-(2-FLUOROPHENYL)-1H-INDOLE-3-CARBOXALDEHYDE; 4,6-DIMETHYL-2-(2-METHYLPHENYL)-1H-INDOLE-3-CARBOXALDEHYDE; 4,6-DIMETHYL-2-(2-NITROPHENYL)-1H-INDOLE-3-CARBOXALDEHYDE; 4,6-DIMETHYL-2-(3-FLUOROPHENYL)-1H-INDOLE-3-CARBOXALDEHYDE; 4,6-DIMETHYL-2-(3-METHYLPHENYL)-1H-INDOLE-3-CARBOXALDEHYDE; 4,6-DIMETHYL-2-(3-NITROPHENYL)-1H-INDOLE-3-CARBOXALDEHYDE; 4,6-DIMETHYL-2-(4-ETHYLPHENYL)-1H-INDOLE-3-CARBOXALDEHYDE;

4,6-DIMETHYL-2-(4-FLUOROPHENYL)-1H-INDOLE-3-CARBOXALDEHYDE; 4,6-DIMETHYL-2-(4-METHYLPHENYL)-1H-INDOLE-3-CARBOXALDEHYDE; 4,6-DIMETHYL-2-(4-NITROPHENYL)-1H-INDOLE-3-CARBOXALDEHYDE; 4,6-DIMETHYL-2-[4-(1-METHYLETHYL)PHENYL]-1H-INDOLE-3-CARBOXALDEHYDE; 4,6-DIMETHYL-3-INDOLE CARBOXALDEHYDE; 4,7-DICHLOROINDOLE-3-CARBOXALDEHYDE; 4,7-DIFLUORO-2-(2,3-DIFLUOROPHENYL)-1H-INDOLE-3-CARBOXALDEHYDE; 4,7-DIFLUORO-2-(2,4-DIFLUOROPHENYL)-1H-INDOLE-3-CARBOXALDEHYDE; 4,7-DIFLUORO-2-(2,5-DIFLUOROPHENYL)-1H-INDOLE-3-CARBOXALDEHYDE; 4,7-DIFLUORO-2-(2,6-DIFLUOROPHENYL)-1H-INDOLE-3-CARBOXALDEHYDE; 4,7-DIFLUORO-2-(2-FLUOROPHENYL)-1H-INDOLE-3-CARBOXALDEHYDE; 4,7-DIFLUORO-2-(2-METHYLPHENYL)-1H-INDOLE-3-CARBOXALDEHYDE; 4,7-DIFLUORO-2-(3,4-DIFLUOROPHENYL)-1H-INDOLE-3-CARBOXALDEHYDE; 4,7-DIFLUORO-2-(3,5-DIFLUOROPHENYL)-1H-INDOLE-3-CARBOXALDEHYDE; 4,7-DIFLUORO-2-(3-FLUOROPHENYL)-1H-INDOLE-3-CARBOXALDEHYDE; 4,7-DIFLUORO-2-(3-METHYLPHENYL)-1H-INDOLE-3-CARBOXALDEHYDE; 4,7-DIFLUORO-2-(4-ETHYLPHENYL)-1H-INDOLE-3-CARBOXALDEHYDE; 4,7-DIFLUORO-2-(4-FLUOROPHENYL)-1H-INDOLE-3-CARBOXALDEHYDE; 4,7-DIFLUORO-2-(4-METHYLPHENYL)-1H-INDOLE-3-CARBOXALDEHYDE; 4,7-DIFLUORO-2-[4-(1-METHYLETHYL)PHENYL]-1H-INDOLE-3-CARBOXALDEHYDE; 4,7-DIFLUOROINDOLE-3-CARBOXALDEHYDE; 4,7-DIMETHOXY-1H-INDOLE-3-CARBALDEHYDE; 4,7-DIMETHYL-2-(2-FLUOROPHENYL)-1H-INDOLE-3-CARBOXALDEHYDE; 4,7-DIMETHYL-2-(2-METHYLPHENYL)-1H-INDOLE-3-CARBOXALDEHYDE; 4,7-DIMETHYL-2-(2-NITROPHENYL)-1H-INDOLE-3-CARBOXALDEHYDE; 4,7-DIMETHYL-2-(3-FLUOROPHENYL)-1H-INDOLE-3-CARBOXALDEHYDE; 4,7-DIMETHYL-2-(3-METHYLPHENYL)-1H-INDOLE-3-CARBOXALDEHYDE; 4,7-DIMETHYL-2-(3-NITROPHENYL)-1H-INDOLE-3-CARBOXALDEHYDE; 4,7-DIMETHYL-2-(4-ETHYLPHENYL)-1H-INDOLE-3-CARBOXALDEHYDE; 4,7-DIMETHYL-2-(4-FLUOROPHENYL)-1H-INDOLE-3-CARBOXALDEHYDE; 4,7-DIMETHYL-2-(4-METHYLPHENYL)-1H-INDOLE-3-CARBOXALDEHYDE; 4,7-DIMETHYL-2-(4-NITROPHENYL)-1H-INDOLE-3-CARBOXALDEHYDE; 4,7-DIMETHYL-2-[4-(1-METHYLETHYL)PHENYL]-1H-INDOLE-3-CARBOXALDEHYDE; 4-[(2,4-DINITROPHENYL)AMINO]BENZALDEHYDE; 4-[(2-IMINO-4-OXO-1,3-THIAZOLIDIN-5-YLIDENE)METHYL]BENZALDEHYDE; 4-[(2-METHOXY)ETHYLAMINO]-2-METHYLTHIO-5-PYRIMIDINECARBOXALDEHYDE; 4-[(2-METHOXYBENZYL)AMINO]-2-(METHYLTHIO)PYRIMIDINE-5-CARBOXALDEHYDE; 4-[(2-OXO-1,3-OXAZOLIDIN-5-YL)METHOXY]BENZALDEHYDE; 4-[(2-OXOAZEPAN-3-YL)OXY]BENZALDEHYDE; 4-[(3-METHOXYBENZYL)AMINO]-2-(METHYLTHIO)PYRIMIDINE-5-CARBOXALDEHYDE; 4-[2-(1H-BENZIMIDAZOL-2-YLTHIO)ETHOXY]BENZALDEHYDE; 4-[2-(1H-IMIDAZOL-4-YL)-ETHYL]-BENZALDEHYDE; 4-[2-(1H-IMIDAZOL-4-YL)-VINYL]BENZALDEHYDE; 4-[2-(2-METHYLIMIDAZOL-4-YL)-ETHYL]-BENZALDEHYDE; 4-[2-(2-OXOIMIDAZOLIDIN-1-YL)ETHOXY]BENZALDEHYDE; 4-[2-HYDROXY-3-[(1-METHYLETHYL)AMINO]PROPOXY]BENZALDEHYDE; 4-[3-(4-FLUOROPHENYL)-1,2,4-OXADIAZOL-5-YL]-2,5-DIMETHYL-1H-PYRROLE-3-CARBALDEHYDE; 4-[3-(4-METHOXYPHENYL)-1,2,4-OXADIAZOL-5-YL]-2,5-DIMETHYL-1H-PYRROLE-3-CARBALDEHYDE; 4-[3-(CYCLOPROPYLAMINOCARBONYL)PHENYL]-2-FORMYLPHENOL; 4-[3-(N-ETHYLAMINOCARBONYL)PHENYL]-2-FORMYLPHENOL; 4-[4-(ETHYLCARBAMOYL)-3-FLUOROPHENYL]-2-FORMYLPHENOL; 4-[5-(4-FLUOROPHENYL)-1,3,4-OXADIAZOL-2-YL]-2,5-DIMETHYL-1H-PYRROLE-3-CARBALDEHYDE; 4-[5-(4-METHOXYPHENYL)-1,3,4-OXADIAZOL-2-YL]-2,5-DIMETHYL-1H-PYRROLE-3-CARBALDEHYDE; 4-[N-(2-PYRIDYLAMINO)ETHOXY]BENZALDEHYDE; 4-ACETAMIDOBENZALDEHYDE; 4-ACETAMIDOPHENYLGLYOXAL HYDRATE; 4-ACETYL-1H-PYRROLE-2-CARBALDEHYDE; 4-ACETYL-3,5-DIMETHYL-PYRROLE-2-CARBOXALDEHYDE; 4-ACETYL-3-METHYL-1H-PYRROLE-2-CARBALDEHYDE; 4-ACETYL-5-FORMYL-3-METHYL-PYRROLE-2-CARBOXYLIC ACID; 4-ACETYL-5-METHYL-PYRROLE-3-CARBOXALDEHYDE; 4-AMINO-1,2-DIHYDRO-2-OXO-5-PYRIMIDINECARBOXALDEHYDE; 4-AMINO-1H-PYRROLO[2,3-C]PYRIDINE-3-CARBALDEHYDE; 4-AMINO-1H-PYRROLO[3,2-C]PYRIDINE-2-CARBALDEHYDE; 4-AMINO-2-PYRROLIDINECARBALDEHYDE; 4-AMINOINDOLE-3-CARBOXALDEHYDE; 4-AMINO-N-(4-FORMYL-3-METHYL-PHENYL)-BUTYRAMIDE HYDROCHLORIC ACID; 4-BENZYLOXYINDOLE-3-CARBOXALDEHYDE; 4-BENZYLOXYMETHYL-1H-INDOLE-3-CARBALDEHYDE; 4-BROMO-1H-PYRROLO[2,3-B]PYRIDINE-3-CARBALDEHYDE; 4-BROMO-1H-PYRROLO[2,3-C]PYRIDINE-3-CARBALDEHYDE; 4-BROMO-1H-PYRROLO[3,2-C]PYRIDINE-3-CARBALDEHYDE; 4-BROMO-2-(3-OXOPIPERAZIN-1-YL)BENZALDEHYDE; 4-BROMO-2-(4-FORMYL-1H-IMIDAZOL-2-YL)-PHENOL; 4-BROMO-2-(5-OXO-1,4-DIAZEPAN-1-YL)BENZALDEHYDE; 4-BROMO-2-(DIMETHYLAMINO)-1H-INDOLE-3-CARBALDEHYDE; 4-BROMO-5-FLUOROINDOLE-3-CARBOXALDEHYDE; 4-BROMO-5-HYDROXYINDOLE-3-CARBOXALDEHYDE; 4-BROMO-5-METHOXYINDOLE-3-CARBOXALDEHYDE; 4-BROMO-6-FLUOROINDOLE-3-CARBOXALDEHYDE; 4-BROMO-6-HYDROXYINDOLE-3-CARBOXALDEHYDE; 4-BROMO-6-METHOXYINDOLE-3-CARBOXALDEHYDE; 4-BROMO-7-CHLORO-1H-PYRROLO[3,2-C]PYRIDINE-3-CARBALDEHYDE; 4-BROMO-7-FLUOROINDOLE-3-CARBOXALDEHYDE; 4-BROMO-7-HYDROXYINDOLE-3-CARBOXALDEHYDE; 4-BROMO-7-METHOXYINDOLE-3-CARBOXALDEHYDE; 4-BROMOINDOLE-3-CARBOXALDEHYDE; 4-BROMO-N-(1-METHYL-3-OXOPROPYL)BENZAMIDE; 4-BUTYL-5-METHYL-1H-IMIDAZOLE-2-CARBALDEHYDE; 4-CARBOXALDEHYDE-N-ISOPROPYLBENZAMIDE; 4-CHLORO-1H-INDOLE-2-CARBALDEHYDE; 4-CHLORO-1H-PYRROLO[2,3-B]PYRIDINE-3-CARBALDEHYDE; 4-CHLORO-1H-PYRROLO[2,3-B]PYRI-

DINE-5-CARBALDEHYDE; 4-CHLORO-1H-PYRROLO[3,2-C]PYRIDINE-3-CARBALDEHYDE; 4-CHLORO-2-(4-FORMYL-IMIDAZOL-2-YL)-PHENOL; 4-CHLORO-2-CYCLOPROPYL-6-(CYCLOPROPYLAMINO)PYRIMIDINE-5-CARBALDEHYDE; 4-CHLORO-2-OXO-3-INDOLINECARBALDEHYDE; 4-CHLORO-5-FLUORO-1H-PYRROLO[2,3-B]PYRIDINE-6-CARBALDEHYDE; 4-CHLORO-5-FLUOROINDOLE-3-CARBOXALDEHYDE; 4-CHLORO-5-HYDROXYINDOLE-3-CARBOXALDEHYDE; 4-CHLORO-5-METHOXYINDOLE-3-CARBOXALDEHYDE; 4-CHLORO-6-FLUOROINDOLE-3-CARBOXALDEHYDE; 4-CHLORO-6-HYDROXYINDOLE-3-CARBOXALDEHYDE; 4-CHLORO-6-METHOXYINDOLE-3-CARBOXALDEHYDE; 4-CHLORO-7-FLUOROINDOLE-3-CARBOXALDEHYDE; 4-CHLORO-7H-PYRROLO[2,3-D]PYRIMIDINE-5-CARBALDEHYDE; 4-CHLORO-7-HYDROXYINDOLE-3-CARBOXALDEHYDE; 4-CHLORO-7-METHOXYINDOLE-3-CARBOXALDEHYDE; 4-CHLOROINDOLE-3-CARBALDEHYDE; 4-CHLORO-N-(1-METHYL-3-OXOPROPYL)BENZAMIDE; 4-CHLORO-N-(3-FORMYL-PHENYL)-BENZAMIDE; 4-CYCLOHEXYL-1H-IMIDAZOLE-2-CARBALDEHYDE; 4-CYCLOHEXYL-5-METHYL-1H-IMIDAZOLE-2-CARBALDEHYDE; 4-CYCLOPROPOXY-2-(METHYLAMINO)BENZALDEHYDE; 4-CYCLOPROPOXY-2-(METHYLAMINO)NICOTINALDEHYDE; 4-CYCLOPROPOXY-2-FORMYL-N-METHYLBENZAMIDE; 4-CYCLOPROPOXY-2-FORMYL-N-METHYLNICOTINAMIDE; 4-CYCLOPROPOXY-3-(METHYLAMINO)BENZALDEHYDE; 4-CYCLOPROPOXY-3-(METHYLAMINO)PICOLINALDEHYDE; 4-CYCLOPROPOXY-3-FORMYL-N-METHYLBENZAMIDE; 4-CYCLOPROPOXY-3-FORMYL-N-METHYLPICOLINAMIDE; 4-CYCLOPROPOXY-5-(METHYLAMINO)NICOTINALDEHYDE; 4-CYCLOPROPOXY-5-(METHYLAMINO)PICOLINALDEHYDE; 4-CYCLOPROPOXY-5-FORMYL-N-METHYLNICOTINAMIDE; 4-CYCLOPROPOXY-5-FORMYL-N-METHYLPICOLINAMIDE; 4-CYCLOPROPOXY-6-(METHYLAMINO)-1,6-DIHYDROPYRIDINE-2-CARBALDEHYDE; 4-CYCLOPROPOXY-6-(METHYLAMINO)NICOTINALDEHYDE; 4-CYCLOPROPOXY-6-ETHYL-1,6-DIHYDROPYRIDINE-2-CARBALDEHYDE; 4-CYCLOPROPOXY-6-FORMYL-N-METHYLNICOTINAMIDE; 4-CYCLOPROPOXY-6-FORMYL-N-METHYLPICOLINAMIDE; 4-CYCLOPROPOXY-6-METHOXY-1,6-DIHYDROPYRIDINE-2-CARBALDEHYDE; 4-CYCLOPROPYL-1H-IMIDAZOLE-2-CARBALDEHYDE; 4-ETHENYL-1H-PYRROLE-2-CARBOXALDEHYDE; 4-ETHOXY-1H-INDOLE-3-CARBALDEHYDE; 4-ETHYL-1H-IMIDAZOLE-2-CARBALDEHYDE; 4-ETHYL-1H-PYRROLE-3-CARBALDEHYDE; 4-ETHYL-3,5-DIMETHYL-1H-PYRROLE-2-CARBALDEHYDE; 4-ETHYL-3-METHYL-1H-PYRROLE-2-CARBALDEHYDE; 4-ETHYL-3-METHYL-5-OXO-3-PYRROLINE-2-CARBOXALDEHYDE; 4-ETHYL-5-FORMYL-3-METHYL-1H-PYRROLE-2-CARBOXYLIC ACID; 4-ETHYL-5-FORMYL-3-METHYL-1H-PYRROLE-2-CARBOXYLIC ACID ETHYL ESTER; 4-ETHYLINDOLE-3-CARBOXALDEHYDE; 4-ETHYNYL-3,5-DIMETHYL-1H-PYRROLE-2-CARBALDEHYDE; 4-ETHYNYL-3-METHYL-1H-PYRROLE-2-CARBALDEHYDE; 4-FLUORO-1H-INDOLE-2-CARBALDEHYDE; 4-FLUORO-1H-INDOLE-3-CARBALDEHYDE; 4-FLUORO-1H-INDOLE-7-CARBALDEHYDE; 4-FLUORO-1H-PYRROLO[2,3-B]PYRIDINE-3-CARBALDEHYDE; 4-FLUORO-1H-PYRROLO[2,3-C]PYRIDINE-3-CARBALDEHYDE; 4-FLUORO-1H-PYRROLO[3,2-C]PYRIDINE-3-CARBALDEHYDE; 4-FLUORO-2-(4-FORMYL-IMIDAZOL-2-YL)-6-METHYLPHENOL; 4-FLUORO-2-(4-FORMYL-IMIDAZOL-2-YL)-PHENOL; 4-FLUORO-5-FORMYL-3-METHYL-1H-PYRROLE-2-CARBOXYLIC ACID; 4-FLUORO-5-HYDROXYINDOLE-3-CARBOXALDEHYDE; 4-FLUORO-5-METHOXYINDOLE-3-CARBOXALDEHYDE; 4-FLUORO-6-HYDROXYINDOLE-3-CARBOXALDEHYDE; 4-FLUORO-6-METHOXYINDOLE-3-CARBOXALDEHYDE; 4-FLUORO-7-HYDROXYINDOLE-3-CARBOXALDEHYDE; 4-FLUORO-7-METHOXYINDOLE-3-CARBOXALDEHYDE; 4-FLUORO-N-(1-METHYL-3-OXOPROPYL)BENZAMIDE; 4-FORMYL-1H-IMIDAZOLE-2-CARBOXYLIC ACID; 4-FORMYL-1H-INDOLE-6-CARBOXYLIC ACID ETHYL ESTER; 4-FORMYL-1H-PYRROLE-2-CARBONITRILE; 4-FORMYL-1H-PYRROLE-2-CARBOTHIOIC ACID O-ETHYL ESTER; 4-FORMYL-1H-PYRROLE-2-CARBOXYLIC ACID; 4-FORMYL-2,5-DIMETHYL-1H-PYRROLE-3-CARBOXYLIC ACID; 4-FORMYL-2-HYDROXY-N-METHYLBENZAMIDE; 4-FORMYL-2-METHOXYPHENYL METHYLCARBAMATE; 4-FORMYL-2-METHOXYPHENYL PHENYLCARBAMATE; 4-FORMYL-3,5-DIMETHYL-1H-PYRROLE-2-CARBOXYLIC ACID; 4-FORMYL-3-HYDROXY-N-METHYLBENZAMIDE; 4-FORMYL-5-METHOXY-N-PHENYLNICOTINAMIDE; 4-FORMYL-5-METHYL-1H-PYRROLE-2-CARBOXYLIC ACID ETHYL ESTER; 4-FORMYL-5-METHYL-1H-PYRROLE-3-CARBOXYLIC ACID METHYL ESTER; 4-FORMYL-7-AZAINDOLE-3-CARBOXYLIC ACID METHYL ESTER; 4-FORMYL-IMIDAZOLE-2-CARBOXYLIC ACID ETHYL ESTER; 4-FORMYL-IMIDAZOLE-2-CARBOXYLIC ACID METHYL ESTER; 4-FORMYL-N-METHYLBENZAMIDE; 4-FORMYL-N-PHENYL-BENZAMIDE; 4-FORMYLPHENYL 2-(2,4-DIOXO-1,3-THIAZOLIDIN-5-YL)ACETATE; 4-FORMYLPHENYL N-PHENYLCARBAMATE; 4-FORMYLPIPERIDINE; 4-FORMYLPIPERIDINE HCL; 4H-FURO[3,2-B]PYRROLE-2-CARBALDEHYDE; 4-HYDROXY-1H-INDOLE-3-CARBALDEHYDE; 4-HYDROXY-1H-PYRROLO[2,3-B]PYRIDINE-3-CARBALDEHYDE; 4-HYDROXY-2-(METHYLAMINO)BENZALDEHYDE; 4-HYDROXY-3-(METHYLAMINO)BENZALDEHYDE; 4-HYDROXY-5-AZAINDOLE-3-CARBALDEHYDE; 4-HYDROXYMETHYL-1H-IMIDAZOLE-2-CARBALDEHYDE HCL; 4-IMIDAZOLIDINEACETALDEHYDE, 4-[(2S)-2,3-DIHYDROXYPROPYL]-A-HYDROXY-2,5-DIOXO-, (AR,4R)-; 4-IMIDAZOLIDINEACETALDEHYDE, A-HYDROXY-2,5-DIOXO-4-(1,2,3-TRIHYDROXYPROPYL)-, [4S-[AS*,4R*(1R*,2S*)]]-; 4-IODO-7-AZAINDOLE-3-CARBALDEHYDE; 4-ISOPROPYL-1H-IMIDAZOLE-2-CARBALDEHYDE; 4-METHOXY-1H-PYRROLO[2,3-B]PYRIDINE-2-CARBALDEHYDE; 4-METHOXY-1H-PYRROLO[2,3-B]PYRIDINE-3-CARBALDEHYDE; 4-METHOXY-1H-PYRROLO[3,2-C]PYRIDINE-3-CARBALDEHYDE; 4-METHOXY-2-[(2-OXO-1,3-OXAZOLIDIN-5-YL)METHOXY]BENZALDEHYDE; 4-METHOXY-2-[(2-OXOAZEPAN-3-YL)OXY]BENZALDEHYDE; 4-METHOXY-2-[2-(2-OXOIMIDAZOLIDIN-1-YL)ETHOXY]BENZALDEHYDE; 4-METHOXY-3-([(5-METHYL-4H-1,2,4-TRIAZOL-3-YL)SULFANYL]METHYL)

BENZALDEHYDE; 4-METHOXY-3-([METHYL(PIPERIDIN-4-YL)AMINO]METHYL)BENZALDEHYDE; 4-METHOXY-3-(PIPERAZIN-1-YLMETHYL)BENZALDEHYDE; 4-METHOXY-3-[(2-OXO-1,3-OXAZOLIDIN-5-YL)METHOXY]BENZALDEHYDE; 4-METHOXY-3-[(2-OXOAZEPAN-3-YL)OXY]BENZALDEHYDE; 4-METHOXY-3-[(3-OXOPIPERAZIN-1-YL)METHYL]BENZALDEHYDE; 4-METHOXY-3-[(5-OXO-1,4-DIAZEPAN-1-YL)METHYL]BENZALDEHYDE; 4-METHOXY-3-[2-(2-OXOIMIDAZOLIDIN-1-YL)ETHOXY]BENZALDEHYDE; 4-METHOXY-5-METHYL-1H-PYRROLE-2-CARBALDEHYDE; 4-METHOXY-7-METHYLINDOLE-3-CARBOXALDEHYDE; 4-METHOXYCARBONYL-7-AZAINDOLE-3-CARBALDEHYDE; 4-METHOXYINDOLE-3-CARBOXALDEHYDE; 4-METHYL-1H-IMIDAZOLE-2-CARBALDEHYDE; 4-METHYL-1H-IMIDAZOLE-5-CARBALDEHYDE; 4-METHYL-1H-PYRROLE-2-CARBALDEHYDE; 4-METHYL-1H-PYRROLE-3-CARBALDEHYDE; 4-METHYL-1H-PYRROLO[2,3-C]PYRIDINE-3-CARBALDEHYDE; 4-METHYL-5,6-DIHYDRO-1H-PYRROLO[2,3-B]PYRIDINE-3-CARBALDEHYDE; 4-METHYL-5-AZAINDOLE-3-CARBOXALDEHYDE; 4-METHYL-5-METHOXY-7-AZAINDOLE-3-CARBALDEHYDE; 4-METHYL-7-NITRO-1H-INDOLE-3-CARBALDEHYDE; 4-METHYLAMINO-2-METHYLSULFANYL-6-(TRIFLUOROMETHYL)PYRIMIDIN-5-CARBALDEHYDE; 4-METHYLAMINO-2-METHYLSULFANYL-PYRIMIDINE-5-CARBALDEHYDE; 4-METHYLINDOLE-2-CARBALDEHYDE; 4-METHYL-INDOLE-6-CARBOXALDEHYDE; 4-N-BOC-AMINO-3-FLUOROBENZALDEHYDE; 4-NITRO-1H-IMIDAZOLE-2-CARBALDEHYDE; 4-NITRO-1H-PYRROLE-2-CARBALDEHYDE; 4-NITRO-1H-PYRROLE-3-CARBALDEHYDE; 4-NITRO-1H-PYRROLO[2,3-C]PYRIDINE-3-CARBALDEHYDE; 4-NITRO-3-[(2-OXO-1,3-OXAZOLIDIN-5-YL)METHOXY]BENZALDEHYDE; 4-NITROINDOLE-3-CARBOXALDEHYDE; 4-OXO-1H-QUINOLINE-3-CARBALDEHYDE; 4-OXO-2-(4-TOLUIDINO)-4H-PYRIDO[1,2-A]PYRIMIDINE-3-CARBOXALDEHYDE; 4-OXO-2,4,6,7-TETRAHYDROPYRANO[3,4-C]PYRROLE-1-CARBALDEHYDE; 4-OXO-3,4-DIHYDROQUINAZOLINE-2-CARBALDEHYDE; 4-OXO-3,4-DIHYDRO-QUINAZOLINE-8-CARBALDEHYDE; 4-OXO-4-(1H-PYRROL-2-YL)BUTANAL; 4-OXO-4,5,6,7-TETRAHYDRO-PYRAZOLO[1,5-A]PYRAZINE-2-CARBALDEHYDE; 4-OXO-5,6,7,8-TETRAHYDRO-4H-1,5,8A-TRIAZA-AZULENE-2-CARBALDEHYDE; 4-PHENETHYL-1H-IMIDAZOLE-2-CARBALDEHYDE; 4-PHENYL-1H-IMIDAZOLE-2-CARBALDEHYDE; 4-PHENYL-1H-PYRROLO[2,3-B]PYRIDINE-2-CARBOXALDEHYDE; 4-PHENYL-1H-PYRROLO[2,3-B]PYRIDINE-3-CARBOXALDEHYDE; 4-PHENYL-1H-PYRROLO[2,3-B]PYRIDINE-5-CARBOXALDEHYDE; 4-PHENYL-1H-PYRROLO[2,3-B]PYRIDINE-6-CARBOXALDEHYDE; 4-PHENYL-4-PIPERIDINECARBOXALDEHYDE; 4-PHENYLAMINOBENZALDEHYDE; 4-PIPERAZIN-1-YL-BENZALDEHYDE; 4-PIPERAZIN-1-YLBENZALDEHYDE HCL; 4-PIPERIDIN-4-YLMETHYLIMIDAZOLE-2-CARBALDEHYDE HCL; 4-PIPERIDINECARBOXYLIC ACID, 4-FORMYL-; 4-PYRIDIN-2-YL-1H-PYRROLE-2-CARBALDEHYDE; 4-STYRYL-1H-IMIDAZOLE-2-CARBALDEHYDE; 4-TERTBUTYLOXYCARBONYL-AMINOPHENYLACETALDEHYDE; 4-THIOPHEN-2-YL-1H-IMIDAZOLE-2-CARBALDEHYDE; 5-((1H-PYRROL-2-YL)METHYL)-1H-PYRROLE-2-CARBALDEHYDE; 5-((2R)-2-PIPERIDYL)PYRIDINE-2-CARBALDEHYDE; 5-((2R)-2-PIPERIDYL)PYRIDINE-3-CARBALDEHYDE; 5-((2R)AZETIDIN-2-YL)PYRIDINE-2-CARBALDEHYDE; 5-((2R)AZETIDIN-2-YL)PYRIDINE-3-CARBALDEHYDE; 5-((2R)PIPERAZIN-2-YL)PYRIDINE-2-CARBALDEHYDE; 5-((2R)PYRROLIDIN-2-YL)PYRIDINE-2-CARBALDEHYDE; 5-((2R)PYRROLIDIN-2-YL)PYRIDINE-3-CARBALDEHYDE; 5-((2S)-2-PIPERIDYL)PYRIDINE-2-CARBALDEHYDE; 5-((2S)-2-PIPERIDYL)PYRIDINE-3-CARBALDEHYDE; 5-((2S)AZETIDIN-2-YL)PYRIDINE-2-CARBALDEHYDE; 5-((2S)AZETIDIN-2-YL)PYRIDINE-3-CARBALDEHYDE; 5-((2S)PIPERAZIN-2-YL)PYRIDINE-2-CARBALDEHYDE; 5-((2S)PYRROLIDIN-2-YL)PYRIDINE-2-CARBALDEHYDE; 5-((2S)PYRROLIDIN-2-YL)PYRIDINE-3-CARBALDEHYDE; 5-((3R)MORPHOLIN-3-YL)PYRIDINE-2-CARBALDEHYDE; 5-((3R)MORPHOLIN-3-YL)PYRIDINE-3-CARBALDEHYDE; 5-((3S)MORPHOLIN-3-YL)PYRIDINE-2-CARBALDEHYDE; 5-((3S)MORPHOLIN-3-YL)PYRIDINE-3-CARBALDEHYDE; 5-(1,1-DIMETHYLETHYL)-2-(2-FLUOROPHENYL)-1H-INDOLE-3-CARBOXALDEHYDE; 5-(1,1-DIMETHYLETHYL)-2-(3-FLUOROPHENYL)-1H-INDOLE-3-CARBOXALDEHYDE; 5-(1,1-DIMETHYLETHYL)-2-(3-METHYLPHENYL)-1H-INDOLE-3-CARBOXALDEHYDE; 5-(1,1-DIMETHYLETHYL)-2-(4-FLUOROPHENYL)-1H-INDOLE-3-CARBOXALDEHYDE; 5-(1,1-DIMETHYLETHYL)-2-(4-METHYLPHENYL)-1H-INDOLE-3-CARBOXALDEHYDE; 5-(1,3-DIOXO-2,3-DIHYDRO-1H-ISOINDOL-5-YL)-2-FURALDEHYDE; 5-(1-BENZOTHIEN-2-YL)-1H-INDOLE-3-CARBALDEHYDE; 5-(1-BENZOTHIEN-3-YL)-1H-INDOLE-3-CARBALDEHYDE; 5-(1H-BENZOIMIDAZOL-2-YLSULFANYL)-FURAN-2-CARBALDEHYDE; 5-(1H-IMIDAZOL-2-YL)-PENTANAL; 5-(1H-IMIDAZOL-4-YL)-PENTANAL; 5-(1H-INDOL-2-YL)-2,4-DIMETHOXYBENZALDEHYDE; 5-(1H-INDOL-2-YL)-3-METHOXY-1H-PYRROLE-2-CARBALDEHYDE; 5-(1-METHYLETHYL)-2-(2-METHYLPHENYL)-1H-INDOLE-3-CARBOXALDEHYDE; 5-(1-METHYLETHYL)-2-(3-METHYLPHENYL)-1H-INDOLE-3-CARBOXALDEHYDE; 5-(1-METHYLETHYL)-2-(4-METHYLPHENYL)-1H-INDOLE-3-CARBOXALDEHYDE; 5-(2,2,6,6-TETRAMETHYL-1,2,3,6-TETRAHYDRO-PYRIDIN-4-YL)-THIOPHENE-2-CARBALDEHYDE; DIHYDRO-1-BENZOFURAN-5-YL)-1H-INDOLE-3-CARBALDEHYDE; 5-(2,3-DIHYDRO-1H-INDOL-5-YL)-2-FURALDEHYDE; 5-(2,3-DIHYDRO-1H-INDOL-5-YL)-2-THIOPHENECARBALDEHYDE; 5-(2,3-DIOXO-2,3-DIHYDRO-1H-INDOL-5-YL)-2-FURALDEHYDE; 5-(2,3-DIOXO-2,3-DIHYDRO-1H-INDOL-5-YL)-2-THIOPHENE CARBALDEHYDE; 5-(2-BROMOPHENYL)-4H-1,2,4-TRIAZOLE-3-CARBALDEHYDE; 5-(2-CHLOROPHENYL)-1H-INDOLE-3-CARBALDEHYDE; 5-(2-FLUOROPHENYL)-1H-INDOLE-3-CARBALDEHYDE; 5-(2-FLUOROPHENYL)-4H-1,2,4-TRIAZOLE-3-CARBALDEHYDE; 5-(2-FURYL)-1H-INDOLE-3-CARBALDEHYDE; 5-(2-METHOXYPHENYL)-1H-INDOLE-3-CARBALDEHYDE; 5-(2-METHOXYPHENYL)-4H-1,2,4-TRIAZOLE-3-CARBALDEHYDE; 5-(2-METHYLPHENYL)-1H-INDOLE-3-CARBALDEHYDE; 5-(2-PROPEN-1-YL)-1H-PYRROLE-2-CARBOXALDE-

HYDE; 5-(2-THIENYL)-1H-INDOLE-3-CARBALDEHYDE; 5-(3-(TRIFLUOROMETHYL)PHENYL)-4H-1,2,4-TRIAZOLE-3-CARBALDEHYDE; 5-(3-ACETYLAMINOPHENYL)-2-FORMYLPHENOL; 5-(3-BROMOPHENYL)-4H-1,2,4-TRIAZOLE-3-CARBALDEHYDE; 5-(3-CHLOROPHENYL)-1H-INDOLE-3-CARBALDEHYDE; 5-(3-CHLOROPHENYL)-1H-PYRROLE-2-CARBALDEHYDE; 5-(3-CHLOROPHENYL)-4H-1,2,4-TRIAZOLE-3-CARBALDEHYDE; 5-(3-FLUOROPHENYL)-1H-INDOLE-3-CARBALDEHYDE; 5-(3-FLUOROPHENYL)-4H-1,2,4-TRIAZOLE-3-CARBALDEHYDE; 5-(3-METHOXYPHENYL)-1H-INDOLE-3-CARBALDEHYDE; 5-(3-METHOXYPHENYL)-4H-1,2,4-TRIAZOLE-3-CARBALDEHYDE; 5-(3-METHYLPHENYL)-1H-INDOLE-3-CARBALDEHYDE; 5-(3-METHYLPHENYL)-4H-1,2,4-TRIAZOLE-3-CARBALDEHYDE; 5-(3-OXO-1,2,3,4-TETRAHYDROQUINOXALIN-1-YL)FURAN-2-CARBALDEHYDE; 5-(3-OXOPIPERAZIN-1-YL)FURAN-2-CARBALDEHYDE; 5-(3-QUINOLINYL)-1H-INDOLE-3-CARBALDEHYDE; 5-(3-THIENYL)-1H-INDOLE-3-CARBALDEHYDE; 5-(4-(TRIFLUOROMETHYL)PHENYL)-4H-1,2,4-TRIAZOLE-3-CARBALDEHYDE; 5-(4,4,5,5-TETRAMETHYL-1,3,2-DIOXABOROLAN-2-YL)-1H-INDOLE-3-CARBALDEHYDE; 5-(4-BROMOPHENYL)-4H-1,2,4-TRIAZOLE-3-CARBALDEHYDE; 5-(4-CHLORO-3-FLUOROPHENYL)-1H-INDOLE-3-CARBALDEHYDE; 5-(4-CHLOROPHENYL)-1H-INDOLE-3-CARBALDEHYDE; 5-(4-CHLOROPHENYL)-4H-1,2,4-TRIAZOLE-3-CARBALDEHYDE; 5-(4-FLUOROPHENYL)-1H-INDOLE-3-CARBALDEHYDE; 5-(4-FLUOROPHENYL)-4H-1,2,4-TRIAZOLE-3-CARBALDEHYDE; 5-(4-FORMYLIMIDAZOL-2-YL)-2-METHOXY-PHENOL; 5-(4H-1,2,4-TRIAZOL-3-YLTHIO)-2-FURALDEHYDE; 5-(4-METHOXYPHENYL)-1H-PYRROLE-2-CARBALDEHYDE; 5-(4-METHOXYPHENYL)-4H-1,2,4-TRIAZOLE-3-CARBALDEHYDE; 5-(4-METHYLPHENYL)-1H-INDOLE-3-CARBALDEHYDE; 5-(4-METHYLPHENYL)-4H-1,2,4-TRIAZOLE-3-CARBALDEHYDE; 5-(4-NITROPHENYL)-4H-1,2,4-TRIAZOLE-3-CARBALDEHYDE; 5-(4-TERT-BUTYLPHENYL)-1H-INDOLE-3-CARBALDEHYDE; 5-(5-ETHYL-1,3,4-OXADIAZOL-2-YL)-2,4-DIMETHYL-1H-PYRROLE-3-CARBALDEHYDE; 5-(5-ISOPROPYL-1,3,4-OXADIAZOL-2-YL)-2,4-DIMETHYL-1H-PYRROLE-3-CARBALDEHYDE; 5-(5-OXO-1,4-DIAZEPAN-1-YL)FURAN-2-CARBALDEHYDE; 5-(5-PYRIMIDINYL)-1H-INDOLE-3-CARBALDEHYDE; 5-(6-METHYL-1H-BENZOIMIDAZOL-2-YLSULFANYL)-FURAN-2-CARBALDEHYDE; 5-(AZETIDIN-3-YL)PICOLINALDEHYDE; 5-(BENZYLOXY)-1H-PYRROLO[3,2-B]PYRIDINE-2-CARBALDEHYDE; 5-(METHYLAMINO)-2-PYRIDINECARBOXALDEHYDE; 5-(N1-PIPERAZINYL)THIOPHENE-2-CARBOXALDEHYDE; 5-(PIPERAZIN-1-YL)FURAN-2-CARBALDEHYDE; 5-(PIPERIDIN-3-YL)PICOLINALDEHYDE; 5-(PIPERIDIN-4-YL)PICOLINALDEHYDE; 5-(PYRIDIN-3-YL)-1H-INDOLE-3-CARBALDEHYDE; 5-(PYRIDIN-4-YL)-1H-INDOLE-3-CARBALDEHYDE; 5-(PYRROLIDIN-3-YL)PICOLINALDEHYDE; 5-(TRIFLUOROMETHOXY)INDOLE-3-CARBOXALDEHYDE; 5-(TRIFLUOROMETHYL)-1H-IMIDAZOLE-2-CARBALDEHYDE; 5-(TRIFLUOROMETHYL)-1H-INDOLE-3-CARBOXALDEHYDE; 5-(TRIFLUOROMETHYL)-1H-PYRROLO[2,3-B]PYRIDINE-3-CARBALDEHYDE; 5-(TRIFLUOROMETHYL)-1H-PYRROLO[2,3-B]PYRIDINE-4-CARBALDEHYDE; 5-(TRIFLUOROMETHYL)-1H-PYRROLO[3,2-B]PYRIDINE-3-CARBALDEHYDE; 5-(TRIFLUOROMETHYL)-4H-1,2,4-TRIAZOLE-3-CARBALDEHYDE; 5-(TRIMETHYLSILYL)-1H-PYRROLE-2-CARBOXALDEHYDE; 5,5'-METHYLENEBIS(1H-PYRROLE-2-CARBALDEHYDE); 5,5'-METHYLENEBIS(3,4-DIMETHYL-1H-PYRROLE-2-CARBALDEHYDE); 5,6,7,8-TETRAHYDRO-[1,2,4]TRIAZOLO[4,3-A]PYRAZINE-3-CARBALDEHYDE; 5,6,7,8-TETRAHYDRO-1,8-NAPHTHYRIDINE-2-CARBALDEHYDE; 5,6,7,8-TETRAHYDRO-7-OXO-PYRIDO[2,3-D]PYRIMIDINE-2-CARBOXALDEHYDE; 5,6,7,8-TETRAHYDRO-IMIDAZO[1,2-A]PYRAZINE-3-CARBALDEHYDE; 5,6,7,8-TETRAHYDROPYRIDO[4,3-D]PYRIMIDINE-2-CARBALDEHYDE; 5,6,7,8-TETRAHYDROPYRIDO[4,3-D]PYRIMIDINE-4-CARBALDEHYDE; 5,6-DICHLORO-1H-BENZOIMIDAZOLE-2-CARBALDEHYDE; 5,6-DICHLORO-1H-INDOLE-2-CARBALDEHYDE; 5,6-DICHLOROINDOLE-3-CARBOXALDEHYDE; 5,6-DIFLUORO-1H-BENZOIMIDAZOLE-2-CARBALDEHYDE; 5,6-DIFLUOROINDOLE-3-CARBOXALDEHYDE; 5,6-DIMETHOXY-1H-INDOLE-3-CARBALDEHYDE; 5,6-DIMETHYL-1H-BENZOIMIDAZOLE-2-CARBALDEHYDE; 5,6-DIOXO-PIPERAZINE-2-CARBALDEHYDE; 5,7-DICHLORO-1H-PYRROLO[2,3-C]PYRIDINE-3-CARBALDEHYDE; 5,7-DICHLORO-INDOLE-3-CARBOXALDEHYDE; 5,7-DIFLUORO-2-(2,3-DIFLUOROPHENYL)-1H-INDOLE-3-CARBOXALDEHYDE; 5,7-DIFLUORO-2-(2,4-DIFLUOROPHENYL)-1H-INDOLE-3-CARBOXALDEHYDE; 5,7-DIFLUORO-2-(2,5-DIFLUOROPHENYL)-1H-INDOLE-3-CARBOXALDEHYDE; 5,7-DIFLUORO-2-(2,6-DIFLUOROPHENYL)-1H-INDOLE-3-CARBOXALDEHYDE; 5,7-DIFLUORO-2-(2-FLUOROPHENYL)-1H-INDOLE-3-CARBOXALDEHYDE; 5,7-DIFLUORO-2-(2-METHYLPHENYL)-1H-INDOLE-3-CARBOXALDEHYDE; 5,7-DIFLUORO-2-(3,4-DIFLUOROPHENYL)-1H-INDOLE-3-CARBOXALDEHYDE; 5,7-DIFLUORO-2-(3,5-DIFLUOROPHENYL)-1H-INDOLE-3-CARBOXALDEHYDE; 5,7-DIFLUORO-2-(3-FLUOROPHENYL)-1H-INDOLE-3-CARBOXALDEHYDE; 5,7-DIFLUORO-2-(3-METHYLPHENYL)-1H-INDOLE-3-CARBOXALDEHYDE; 5,7-DIFLUORO-2-(4-ETHYLPHENYL)-1H-INDOLE-3-CARBOXALDEHYDE; 5,7-DIFLUORO-2-(4-FLUOROPHENYL)-1H-INDOLE-3-CARBOXALDEHYDE; 5,7-DIFLUORO-2-(4-METHYLPHENYL)-1H-INDOLE-3-CARBOXALDEHYDE; 5,7-DIFLUORO-2-[4-(1-METHYLETHYL)PHENYL]-1H-INDOLE-3-CARBOXALDEHYDE; 5,7-DIFLUOROINDOLE-3-CARBOXALDEHYDE; 5,7-DIMETHYL-2-(2-FLUOROPHENYL)-1H-INDOLE-3-CARBOXALDEHYDE; 5,7-DIMETHYL-2-(2-METHYLPHENYL)-1H-INDOLE-3-CARBOXALDEHYDE; 5,7-DIMETHYL-2-(2-NITROPHENYL)-1H-INDOLE-3-CARBOXALDEHYDE;

5,7-DIMETHYL-2-(3-FLUOROPHENYL)-1H-INDOLE-3-CARBOXALDEHYDE; 5,7-DIMETHYL-2-(3-METHYLPHENYL)-1H-INDOLE-3-CARBOXALDEHYDE; 5,7-DIMETHYL-2-(3-NITROPHENYL)-1H-INDOLE-3-CARBOXALDEHYDE; 5,7-DIMETHYL-2-(4-ETHYLPHENYL)-1H-INDOLE-3-CARBOXALDEHYDE; 5,7-DIMETHYL-2-(4-FLUOROPHENYL)-1H-INDOLE-3-CARBOXALDEHYDE; 5,7-DIMETHYL-2-(4-METHYLPHENYL)-1H-INDOLE-3-CARBOXALDEHYDE; 5,7-DIMETHYL-2-(4-NITROPHENYL)-1H-INDOLE-3-CARBOXALDEHYDE; 5,7-DIMETHYL-2-[4-(1-METHYLETHYL)PHENYL]-1H-INDOLE-3-CARBOXALDEHYDE; 5,7-DIMETHYL-2-OXO-1,2-DIHYDRO-3-QUINOLINECARBALDEHYDE; 5,8-DIMETHYL-2-OXO-1,2-DIHYDRO-3-QUINOLINECARBALDEHYDE; 5-[(2,2,6,6-TETRAMETHYL-4-OXO-3-PIPERIDINYLIDENE)METHYL]-2-THIOPHENECARBALDEHYDE; 5-[(4-METHYLPHENYL)SULFANYL]-2-PHENYL-1H-IMIDAZOLE-4-CARBALDEHYDE; 5-[(5-METHYL-1H-BENZIMIDAZOL-2-YL)THIO]-2-FURALDEHYDE; 5-[(7-CHLORO-4-QUINOLINYL)AMINO]-2-HYDROXYBENZALDEHYDE; 5-[3-(1,3-DIOXOLAN-2-YL)PHENYL]-1H-INDOLE-3-CARBALDEHYDE; 5-[3-(CYCLOPROPYLAMINOCARBONYL)PHENYL]-2-FORMYLPHENOL; 5-[3-(N-ETHYLAMINOCARBONYL)PHENYL]-2-FORMYLPHENOL; 5-[3-(TRIFLUOROMETHYL)PHENYL]-1H-INDOLE-3-CARBALDEHYDE; 5-[4-(1,3-DIOXOLAN-2-YL)PHENYL]-1H-INDOLE-3-CARBALDEHYDE; 5-[4-(DIMETHYLAMINO)PHENYL]-1H-INDOLE-3-CARBALDEHYDE; 5-[4-(ETHYLCARBAMOYL)-3-FLUOROPHENYL]-2-FORMYLPHENOL; 5-[4-(METHYLSULFANYL)PHENYL]-1H-INDOLE-3-CARBALDEHYDE; 5-[4-(METHYLSULFONYL)PHENYL]-1H-INDOLE-3-CARBALDEHYDE; 5-[4-(TRIFLUOROMETHYL)PHENYL]-1H-INDOLE-3-CARBALDEHYDE; 5-[5-(4-FLUOROPHENYL)-1,3,4-OXADIAZOL-2-YL]-2,4-DIMETHYL-1H-PYRROLE-3-CARBALDEHYDE; 5-[5-(4-METHOXYPHENYL)-1,3,4-OXADIAZOL-2-YL]-2,4-DIMETHYL-1H-PYRROLE-3-CARBALDEHYDE; 5-ACETYL-1H-IMIDAZOLE-2-CARBALDEHYDE; 5-AMINO-1H-PYRROLO[2,3-B]PYRIDINE-3-CARBALDEHYDE; 5-AMINO-2-METHYL-1H-INDOLE-3-CARBALDEHYDE; 5-AMINOINDOLE-3-CARBOXALDEHYDE; 5-ANILINO-3-PHENYL-4-ISOXAZOLECARBALDEHYDE; 5-BENZOYL-1H-INDOLE-3-CARBALDEHYDE; 5-BENZYLOXY-1H-PYRROLO[2,3-C]PYRIDINE-3-CARBOXALDEHYDE; 5-BENZYLOXYINDOLE-3-CARBOXALDEHYDE; 5-BENZYLOXYMETHYL-1H-INDOLE-3-CARBALDEHYDE; 5-BROMO-1H-INDOLE-2-CARBALDEHYDE; 5-BROMO-1H-PYRROLO[2,3-B]PYRIDINE-3-CARBALDEHYDE; 5-BROMO-1H-PYRROLO[3,2-B]PYRIDINE-3-CARBALDEHYDE; 5-BROMO-2-(2-FLUOROANILINO)BENZALDEHYDE; 5-BROMO-2-(4-FLUOROANILINO)BENZALDEHYDE; 5-BROMO-2-(DIMETHYLAMINO)-1H-INDOLE-3-CARBALDEHYDE; 5-BROMO-2-(METHYLAMINO)NICOTINALDEHYDE; 5-BROMO-2-[(2-FURYLMETHYL)AMINO]BENZALDEHYDE; 5-BROMO-2-CYCLOPROPYL-1H-INDOLE-3-CARBOXALDEHYDE; 5-BROMO-2-CYCLOPROPYL-7-FLUORO-1H-INDOLE-3-CARBOXALDEHYDE; 5-BROMO-2-METHYL-1H-INDOLE-3-CARBALDEHYDE; 5-BROMO-2-OXOINDOLINE-3-CARBALDEHYDE; 5-BROMO-2-TERT-BUTYL-1H-INDOLE-3-CARBALDEHYDE; 5-BROMO-3-FORMYL-1H-INDOLE-2-CARBOXYLIC ACID; 5-BROMO-3-FORMYL-6-METHYL-7-AZAINDOLE; 5-BROMO-3-METHYL-1H-INDOLE-2-CARBALDEHYDE; 5-BROMO-4-FLUOROINDOLE-3-CARBOXALDEHYDE; 5-BROMO-4-HYDROXYINDOLE-3-CARBOXALDEHYDE; 5-BROMO-4-METHOXYINDOLE-3-CARBOXALDEHYDE; 5-BROMO-4-METHYL-1H-PYRROLO[2,3-B]PYRIDINE-3-CARBALDEHYDE; 5-BROMO-5,6-DIHYDRO-1H-PYRROLO[2,3-B]PYRIDINE-3-CARBALDEHYDE; 5-BROMO-6-FLUOROINDOLE-3-CARBOXALDEHYDE; 5-BROMO-6-HYDROXYINDOLE-3-CARBOXALDEHYDE; 5-BROMO-6-METHOXYINDOLE-3-CARBOXALDEHYDE; 5-BROMO-7-FLUOROINDOLE-3-CARBOXALDEHYDE; 5-BROMO-7-HYDROXYINDOLE-3-CARBOXALDEHYDE; 5-BROMO-7-METHOXYINDOLE-3-CARBOXALDEHYDE; 5-BROMO-7-METHYL-1H-INDOLE-3-CARBALDEHYDE; 5-BROMOBENZIMIDAZOLE-2-CARBOXALDEHYDE; 5-BROMOINDOLE-3-CARBOXALDEHYDE; 5-CHLORO-1H-INDOLE-2-CARBALDEHYDE; 5-CHLORO-1H-PYRROLO[2,3-B]PYRIDINE-3-CARBALDEHYDE; 5-CHLORO-1H-PYRROLO[2,3-B]PYRIDINE-4-CARBALDEHYDE; 5-CHLORO-1H-PYRROLO[2,3-B]PYRIDINE-6-CARBALDEHYDE; 5-CHLORO-1H-PYRROLO[2,3-C]PYRIDINE-3-CARBALDEHYDE; 5-CHLORO-1H-PYRROLO[3,2-B]PYRIDINE-3-CARBALDEHYDE; 5-CHLORO-2-(2,3-DIFLUOROPHENYL)-1H-INDOLE-3-CARBOXALDEHYDE; 5-CHLORO-2-(2,4-DIFLUOROPHENYL)-1H-INDOLE-3-CARBOXALDEHYDE; 5-CHLORO-2-(2,5-DIFLUOROPHENYL)-1H-INDOLE-3-CARBOXALDEHYDE; 5-CHLORO-2-(2,5-DIMETHYLANILINO)BENZALDEHYDE; 5-CHLORO-2-(2,6-DIFLUOROPHENYL)-1H-INDOLE-3-CARBOXALDEHYDE; 5-CHLORO-2-(2-CHLOROPHENYL)-1H-INDOLE-3-CARBOXALDEHYDE; 5-CHLORO-2-(2-FLUOROANILINO)BENZALDEHYDE; 5-CHLORO-2-(2-FLUOROPHENYL)-1H-INDOLE-3-CARBOXALDEHYDE; 5-CHLORO-2-(2-METHYLPHENYL)-1H-INDOLE-3-CARBOXALDEHYDE; 5-CHLORO-2-(3,4-DIFLUOROPHENYL)-1H-INDOLE-3-CARBOXALDEHYDE; 5-CHLORO-2-(3,5-DIFLUOROPHENYL)-1H-INDOLE-3-CARBOXALDEHYDE; 5-CHLORO-2-(3-CHLORO-4-METHYLANILINO)BENZALDEHYDE; 5-CHLORO-2-(3-CHLOROANILINO)BENZALDEHYDE; 5-CHLORO-2-(3-CHLOROPHENYL)-1H-INDOLE-3-CARBOXALDEHYDE; 5-CHLORO-2-(3-FLUOROPHENYL)-1H-INDOLE-3-CARBOXALDEHYDE; 5-CHLORO-2-(3-METHYLPHENYL)-1H-INDOLE-3-CARBOXALDEHYDE; 5-CHLORO-2-(4-CHLOROPHENYL)-1H-INDOLE-3-CARBOXALDEHYDE; 5-CHLORO-2-(4-ETHOXYANILINO)BENZALDEHYDE; 5-CHLORO-2-(4-ETHYLPHENYL)-1H-INDOLE-3-CARBOXALDEHYDE; 5-CHLORO-2-(4-FLUOROPHENYL)-1H-INDOLE-3-CARBOXALDEHYDE; 5-CHLORO-2-(4-METHYLPHENYL)-1H-INDOLE-3-CARBOXALDEHYDE; 5-CHLORO-2-(5-CHLORO-2-METHYLANILINO)BENZALDEHYDE; 5-CHLORO-2-

(METHYLAMINO)NICOTINALDEHYDE; 5-CHLORO-2-[(2-OXO-1,3-OXAZOLIDIN-5-YL)METHOXY]BENZALDEHYDE; 5-CHLORO-2-[(2-OXOAZEPAN-3-YL)OXY]BENZALDEHYDE; 5-CHLORO-2-[2-(2-OXOIMIDAZOLIDIN-1-YL)ETHOXY]BENZALDEHYDE; 5-CHLORO-2-[4-(1-METHYLETHYL)PHENYL]-1H-INDOLE-3-CARBOXALDEHYDE; 5-CHLORO-2-CYCLOHEXYL-7-FLUORO-1H-INDOLE-3-CARBOXALDEHYDE; 5-CHLORO-2-CYCLOPROPYL-7-FLUORO-1H-INDOLE-3-CARBOXALDEHYDE; 5-CHLORO-2-METHYL-1H-INDOLE-3-CARBALDEHYDE; 5-CHLORO-2-OXOINDOLINE-3-CARBALDEHYDE; 5-CHLORO-2-PHENYL-1H-INDOLE-3-CARBALDEHYDE; 5-CHLORO-3-ETHYLAMINO-PYRIDINE-2-CARBALDEHYDE; 5-CHLORO-3-FORMYL-1H-INDOLE-2-CARBOXYLIC ACID; 5-CHLORO-3-FORMYL-1H-INDOLE-2-CARBOXYLIC ACID ETHYL ESTER; 5-CHLORO-3-FORMYL-1H-INDOLE-2-CARBOXYLIC ACID METHYL ESTER; 5-CHLORO-3-FORMYL-6-METHYL-7-AZAINDOLE; 5-CHLORO-3-METHYL-1H-INDOLE-2-CARBALDEHYDE; 5-CHLORO-3-METHYLAMINO-PYRIDINE-2-CARBALDEHYDE; 5-CHLORO-4-FLUOROINDOLE-3-CARBOXALDEHYDE; 5-CHLORO-4-HYDROXYINDOLE-3-CARBOXALDEHYDE; 5-CHLORO-4-METHOXYINDOLE-3-CARBOXALDEHYDE; 5-CHLORO-6-FLUORO-1H-BENZOIMIDAZOLE-2-CARBALDEHYDE; 5-CHLORO-6-FLUOROINDOLE-3-CARBOXALDEHYDE; 5-CHLORO-6-HYDROXYINDOLE-3-CARBOXALDEHYDE; 5-CHLORO-6-METHOXYINDOLE-3-CARBOXALDEHYDE; 5-CHLORO-7-FLUORO-2-(2-FLUOROPHENYL)-1H-INDOLE-3-CARBOXALDEHYDE; 5-CHLORO-7-FLUORO-2-(2-METHYLPHENYL)-1H-INDOLE-3-CARBOXALDEHYDE; 5-CHLORO-7-FLUORO-2-(3-FLUOROPHENYL)-1H-INDOLE-3-CARBOXALDEHYDE; 5-CHLORO-7-FLUORO-2-(3-METHYLPHENYL)-1H-INDOLE-3-CARBOXALDEHYDE; 5-CHLORO-7-FLUORO-2-(4-FLUOROPHENYL)-1H-INDOLE-3-CARBOXALDEHYDE; 5-CHLORO-7-FLUORO-2-(4-METHYLPHENYL)-1H-INDOLE-3-CARBOXALDEHYDE; 5-CHLORO-7-FLUOROINDOLE-3-CARBOXALDEHYDE; 5-CHLORO-7-HYDROXYINDOLE-3-CARBOXALDEHYDE; 5-CHLORO-7-METHOXYINDOLE-3-CARBOXALDEHYDE; 5-CHLORO-7-METHYL-1H-INDOLE-3-CARBALDEHYDE; 5-CHLOROINDOLE-3-CARBOXALDEHYDE; 5-CYANO-2,4-DIMETHYL-1H-PYRROLE-3-CARBOXALDEHYDE; 5-CYANOINDOLE-3-CARBOXALDEHYDE; 5-CYCLOPROPOXY-2-(METHYLAMINO)BENZALDEHYDE; 5-CYCLOPROPOXY-2-(METHYLAMINO)ISONICOTINALDEHYDE; 5-CYCLOPROPOXY-2-(METHYLAMINO)NICOTINALDEHYDE; 5-CYCLOPROPOXY-2-FORMYL-N-METHYLBENZAMIDE; 5-CYCLOPROPOXY-2-FORMYL-N-METHYLISONICOTINAMIDE; 5-CYCLOPROPOXY-2-FORMYL-N-METHYLNICOTINAMIDE; 5-CYCLOPROPOXY-3-(METHYLAMINO)PICOLINALDEHYDE; 5-CYCLOPROPOXY-3-FORMYL-N-METHYLPICOLINAMIDE; 5-CYCLOPROPOXY-4-(METHYLAMINO)NICOTINALDEHYDE; 5-CYCLOPROPOXY-4-(METHYLAMINO)PICOLINALDEHYDE; 5-CYCLOPROPOXY-4-FORMYL-N-METHYLNICOTINAMIDE; 5-CYCLOPROPOXY-4-FORMYL-N-METHYLPICOLINAMIDE; 5-CYCLOPROPOXY-6-(METHYLAMINO)NICOTINALDEHYDE; 5-CYCLOPROPOXY-6-(METHYLAMINO)PICOLINALDEHYDE; 5-CYCLOPROPOXY-6-FORMYL-N-METHYLNICOTINAMIDE; 5-CYCLOPROPOXY-6-FORMYL-N-METHYLPICOLINAMIDE; 5-CYCLOPROPYL-1H-INDOLE-3-CARBALDEHYDE; 5'-DEOXYINOSINE DIALDEHYDE; 5-DIETHYLAMINO-2-(4-FORMYLIMIDAZOL-2-YL)-PHENOL; 5-ETHOXY-1H-INDOLE-3-CARBALDEHYDE; 5-ETHOXY-2-(2-FLUOROPHENYL)-1H-INDOLE-3-CARBOXALDEHYDE; 5-ETHOXY-2-(2-METHYLPHENYL)-1H-INDOLE-3-CARBOXALDEHYDE; 5-ETHOXY-2-(3-FLUOROPHENYL)-1H-INDOLE-3-CARBOXALDEHYDE; 5-ETHOXY-2-(3-METHYLPHENYL)-1H-INDOLE-3-CARBOXALDEHYDE; 5-ETHOXY-2-(4-ETHYLPHENYL)-1H-INDOLE-3-CARBOXALDEHYDE; 5-ETHOXY-2-(4-FLUOROPHENYL)-1H-INDOLE-3-CARBOXALDEHYDE; 5-ETHOXY-2-(4-METHYLPHENYL)-1H-INDOLE-3-CARBOXALDEHYDE; 5-ETHOXY-2-OXOINDOLINE-3-CARBALDEHYDE; 5-ETHYL-1H-INDOLE-3-CARBALDEHYDE; 5-ETHYL-2-FORMYL-1H-PYRROLE-3-CARBONITRILE; 5-ETHYL-2-METHYL-1H-INDOLE-3-CARBALDEHYDE; 5-ETHYL-2-OXOINDOLINE-3-CARBALDEHYDE; 5-ETHYL-4H-1,2,4-TRIAZOLE-3-CARBALDEHYDE; 5-ETHYL-4-METHYL-1H-IMIDAZOLE-2-CARBALDEHYDE; 5-ETHYNYL-3,4-DIMETHYL-1H-PYRROLE-2-CARBALDEHYDE; 5-FLUORO-1,2-DIHYDRO-2-OXO-4-PYRIDINECARBOXALDEHYDE; 5-FLUORO-1H-INDOLE-2-CARBALDEHYDE; 5-FLUORO-1H-PYRROLE-2-CARBALDEHYDE; 5-FLUORO-1H-PYRROLO[2,3-B]PYRIDINE-3-CARBALDEHYDE; 5-FLUORO-1H-PYRROLO[2,3-B]PYRIDINE-4-CARBALDEHYDE; 5-FLUORO-1H-PYRROLO[2,3-B]PYRIDINE-6-CARBALDEHYDE; 5-FLUORO-1H-PYRROLO[3,2-B]PYRIDINE-3-CARBALDEHYDE; 5-FLUORO-2-(2,3,4-TRIFLUOROPHENYL)-1H-INDOLE-3-CARBOXALDEHYDE; 5-FLUORO-2-(2,4,5-TRIFLUOROPHENYL)-1H-INDOLE-3-CARBOXALDEHYDE; 5-FLUORO-2-(2-FLUOROPHENYL)-1H-INDOLE-3-CARBOXALDEHYDE; 5-FLUORO-2-(2-METHYLPHENYL)-1H-INDOLE-3-CARBOXALDEHYDE; 5-FLUORO-2-(2-NITROPHENYL)-1H-INDOLE-3-CARBOXALDEHYDE; 5-FLUORO-2-(3-FLUOROPHENYL)-1H-INDOLE-3-CARBOXALDEHYDE; 5-FLUORO-2-(3-METHYLPHENYL)-1H-INDOLE-3-CARBOXALDEHYDE; 5-FLUORO-2-(3-NITROPHENYL)-1H-INDOLE-3-CARBOXALDEHYDE; 5-FLUORO-2-(3-OXOPIPERAZIN-1-YL)BENZALDEHYDE; 5-FLUORO-2-(4-FLUOROPHENYL)-1H-INDOLE-3-CARBOXALDEHYDE; 5-FLUORO-2-(4-FORMYL-IMIDAZOL-2-YL)-PHENOL; 5-FLUORO-2-(4-METHYLPHENYL)-1H-INDOLE-3-CARBOXALDEHYDE; 5-FLUORO-2-(4-NITROPHENYL)-1H-INDOLE-3-CARBOXALDEHYDE; 5-FLUORO-2-(5-OXO-1,4-DIAZEPAN-1-YL)BENZALDEHYDE; 5-FLUORO-2-[4-(1-METHYLETHYL)PHENYL]-1H-INDOLE-3-CARBOXALDEHYDE; 5-FLUORO-2-METHYL-1H-INDOLE-3-CARBALDEHYDE; 5-FLUORO-2-OXOINDOLINE-3-CARBALDEHYDE; 5-FLUORO-3-FORMYL-1H-INDOLE-2-CARBOXYLIC ACID; 5-FLUORO-3-FORMYL-1H-INDOLE-2-CARBOXYLIC ACID ETHYL ESTER; 5-FLUORO-3-FORMYL-1H-INDOLE-2-CARBOXYLIC ACID METHYL ESTER; 5-FLUORO-3-METHYL-1H-INDOLE-2-CARBALDEHYDE; 5-FLUORO-4-HYDROXYIN-

DOLE-3-CARBOXALDEHYDE; 5-FLUORO-4-METHOXYINDOLE-3-CARBOXALDEHYDE; 5-FLUORO-6-HYDROXYINDOLE-3-CARBOXALDEHYDE; 5-FLUORO-6-IODO-1H-PYRROLO[2,3-B]PYRIDINE-4-CARBALDEHYDE; 5-FLUORO-6-METHOXY-INDOLE-3-CARBOXALDEHYDE; 5-FLUORO-7-HYDROXYINDOLE-3-CARBOXALDEHYDE; 5-FLUORO-7-METHOXYINDOLE-3-CARBOXALDEHYDE; 5-FLUORO-7-METHYL-1H-INDOLE-3-CARBALDEHYDE; 5-FLUOROBENZIMIDAZOLE-2-CARBOXALDEHYDE; 5-FLUOROINDOLE-3-CARBOXALDEHYDE; 5-FLUORO-INDOLE-7-CARBOXALDEHYDE; 5-FORMYL-1H-PYRROL-2-YLBORONIC ACID; 5-FORMYL-1H-PYRROLE-2-CARBONITRILE; 5-FORMYL-1H-PYRROLE-2-CARBOXYLIC ACID; 5-FORMYL-1H-PYRROLE-3-CARBONITRILE; 5-FORMYL-2,4-DIMETHYL-1H-PYRROLE-3-CARBOXYLIC ACID; 5-FORMYL-2,4-DIMETHYLPYRROLE-3-PROPIONIC ACID, METHYL ESTER; 5-FORMYL-2-HYDROXY-N-METHYLBENZAMIDE; 5-FORMYL-2-METHYL-1H-PYRROLE-3-CARBOXYLIC ACID METHYL ESTER; 5-FORMYL-3,4-DIMETHYL-1H-PYRROLE-2-CARBONITRILE; 5-FORMYL-3,4-DIMETHYL-1H-PYRROLE-2-CARBOXYLIC ACID ETHYL ESTER; 5-FORMYL-3-METHYL-1H-PYRROLE-2-CARBOXYLIC ACID; 5-FORMYL-4-METHYL-1H-PYRROLE-2-CARBOXYLIC ACID; 5-FORMYL-4-METHYL-1H-PYRROLE-2-CARBOXYLIC ACID ETHYL ESTER; 5-FORMYL-4-METHYL-1H-PYRROLE-2-CARBOXYLIC ACID METHYL ESTER; 5-FORMYL-4-METHYL-1H-PYRROLE-3-CARBOXYLIC ACID; 5-FORMYLIMIDAZOLE-4-CARBOXYLIC ACID METHYL ESTER; 5-FORMYLPYRROLE-2-CARBOXYLIC ACID METHYL ESTER; 5-FORMYLURACIL; 5-FORMYLURIDINE; 5H-PYRIMIDO[5,4-B]INDOLE-8-CARBOXALDEHYDE; 5H-PYRROLO[2,3-B]PYRAZINE-7-CARBOXALDEHYDE; 5-HYDROXY-1H-INDOLE-3-CARBALDEHYDE; 5-HYDROXY-1H-PYRROLO[2,3-B]PYRIDINE-3-CARBALDEHYDE; 5-HYDROXY-2-(METHYLAMINO)BENZALDEHYDE; 5-HYDROXY-2-METHYL-1H-INDOLE-3-CARBALDEHYDE; 5-HYDROXY-4-AZAINDOLE-3-CARBALDEHYDE; 5-HYDROXY-4-METHYL-1H-PYRROLO[2,3-B]PYRIDINE-3-CARBALDEHYDE; 5-IODO-7-AZAINDOLE-3-CARBOXALDEHYDE; 5-ISOPROPYL-2-OXOINDOLINE-3-CARBALDEHYDE; 5-ISOPROPYL-4H-1,2,4-TRIAZOLE-3-CARBALDEHYDE; 5-METHOXY INDOLE-3-CARBOXALDEHYDE, [3-14C]; 5-METHOXY-1H-INDOLE-2-CARBALDEHYDE; 5-METHOXY-1H-INDOLE-4-CARBALDEHYDE; 5-METHOXY-1H-PYRROLE-2-CARBOXALDEHYDE; 5-METHOXY-1H-PYRROLO[2,3-C]PYRIDINE-2-CARBALDEHYDE; 5-METHOXY-1H-PYRROLO[2,3-C]PYRIDINE-3-CARBALDEHYDE; 5-METHOXY-1H-PYRROLO[3,2-B]PYRIDINE-2-CARBALDEHYDE; 5-METHOXY-1H-PYRROLO[3,2-B]PYRIDINE-3-CARBALDEHYDE; 5-METHOXY-2-(2-METHYLPHENYL)-1H-INDOLE-3-CARBOXALDEHYDE; 5-METHOXY-2-(2-NITROPHENYL)-1H-INDOLE-3-CARBOXALDEHYDE; 5-METHOXY-2-(3-METHYLPHENYL)-1H-INDOLE-3-CARBOXALDEHYDE; 5-METHOXY-2-(3-NITROPHENYL)-1H-INDOLE-3-CARBOXALDEHYDE; 5-METHOXY-2-(4-METHYLPHENYL)-1H-INDOLE-3-CARBOXALDEHYDE; 5-METHOXY-2-(4-NITROPHENYL)-1H-INDOLE-3-CARBOXALDEHYDE; 5-METHOXY-2-[(2-OXO-1,3-OXAZOLIDIN-5-YL)METHOXY]BENZALDEHYDE; 5-METHOXY-2-[(2-OXOAZEPAN-3-YL)OXY]BENZALDEHYDE; 5-METHOXY-2-[2-(2-OXOIMIDAZOLIDIN-1-YL)ETHOXY]BENZALDEHYDE; 5-METHOXY-2-[4-(1-METHYLETHYL)PHENYL]-1H-INDOLE-3-CARBOXALDEHYDE; 5-METHOXY-2-METHYL-1H-INDOLE-3-CARBALDEHYDE; 5-METHOXY-2-OXOINDOLINE-3-CARBALDEHYDE; 5-METHOXY-3-METHYL-1H-INDOLE-2-CARBALDEHYDE; 5-METHOXY-4-METHYLINDOLE-3-CARBOXALDEHYDE; 5-METHOXY-5,6-DIHYDRO-1H-PYRROLO[2,3-B]PYRIDINE-3-CARBALDEHYDE; 5-METHOXYBENZIMIDAZOLE-2-CARBOXALDEHYDE; 5-METHOXYINDOLE-3-CARBOXALDEHYDE; 5-METHOXYINDOLE-7-CARBOXALDEHYDE; 5-METHYL-1-(7H-PURIN-6-YL)-1H-PYRAZOLE-4-CARBALDEHYDE; 5-METHYL-1H-BENZOIMIDAZOLE-2-CARBALDEHYDE HYDROCHLORIDE; 5-METHYL-1H-IMIDAZOLE-2-CARBALDEHYDE; 5-METHYL-1H-IMIDAZOLE-4-CARBALDEHYDE; 5-METHYL-1H-INDOLE-2-CARBALDEHYDE; 5-METHYL-1H-INDOLE-7-CARBOXALDEHYDE; 5-METHYL-1H-PYRROLE-2,4-DICARBALDEHYDE; 5-METHYL-1H-PYRROLE-2-CARBALDEHYDE; 5-METHYL-1H-PYRROLO[2,3-B]PYRIDINE-3-CARBALDEHYDE; 5-METHYL-2-(2,3,4-TRIFLUOROPHENYL)-1H-INDOLE-3-CARBOXALDEHYDE; 5-METHYL-2-(2,4,5-TRIFLUOROPHENYL)-1H-INDOLE-3-CARBOXALDEHYDE; 5-METHYL-2-(2-METHYLPHENYL)-1H-INDOLE-3-CARBOXALDEHYDE; 5-METHYL-2-(2-NITROPHENYL)-1H-INDOLE-3-CARBOXALDEHYDE; 5-METHYL-2-(3-METHYLPHENYL)-1H-INDOLE-3-CARBOXALDEHYDE; 5-METHYL-2-(3-NITROPHENYL)-1H-INDOLE-3-CARBOXALDEHYDE; 5-METHYL-2-(4-METHYLPHENYL)-1H-INDOLE-3-CARBOXALDEHYDE; 5-METHYL-2-(4-NITROPHENYL)-1H-INDOLE-3-CARBOXALDEHYDE; 5-METHYL-2-[4-(1-METHYLETHYL)PHENYL]-1H-INDOLE-3-CARBOXALDEHYDE; 5-METHYL-2-OXOINDOLINE-3-CARBALDEHYDE; 5-METHYL-3-(TRIFLUOROMETHYL)-1H-PYRROLE-2-CARBALDEHYDE; 5-METHYL-4-AZAINDOLE-3-CARBALDEHYDE; 5-METHYL-4H-1,2,4-TRIAZOLE-3-CARBALDEHYDE; 5-METHYL-4-NITRO-1H-PYRROLE-2-CARBALDEHYDE; 5-METHYL-4-NITRO-1H-PYRROLE-3-CARBALDEHYDE; 5-METHYL-4-PROPYL-1H-IMIDAZOLE-2-CARBALDEHYDE; 5-METHYLINDOLE-3-CARBOXALDEHYDE; 5-NITRO-1H-IMIDAZOLE-4-CARBALDEHYDE; 5-NITRO-1H-INDOLE-2-CARBALDEHYDE; 5-NITRO-1H-INDOLE-3-CARBALDEHYDE; 5-NITRO-1H-PYRROLE-2-CARBALDEHYDE; 5-NITRO-1H-PYRROLO[2,3-B]PYRIDINE-2-CARBALDEHYDE; 5-NITRO-1H-PYRROLO[2,3-B]PYRIDINE-3-CARBALDEHYDE; 5-NITRO-2-(3-OXOPIPERAZIN-1-YL)BENZALDEHYDE; 5-NITRO-2-(5-OXO-1,4-DIAZEPAN-1-YL)BENZALDEHYDE; 5-NITRO-2-[(2-OXO-1,3-OXAZOLIDIN-5-YL)METHOXY]BENZALDEHYDE; 5-OXO-4,5-DIHYDROPYRAZINE-2-CARBALDEHYDE; 5-PHENYL-1H-INDOLE-3-CARBALDEHYDE; 5-PHENYL-1H-PYRROLO[2,3-B]PYRIDINE-2-CARBALDEHYDE; 5-PHENYL-1H-PYRROLO[2,3-B]PYRIDINE-3-CARBOXALDEHYDE; 5-PHENYL-1H-PYRROLO[2,3-B]PYRIDINE-4-CARBOXALDEHYDE; 5-PHENYL-1H-PYRROLO[2,3-B]PYRIDINE-6-

CARBOXALDEHYDE; 5-PHENYL-4H-1,2,4-TRIAZOLE-3-CARBALDEHYDE; 5-PHENYLPYRROLE-2-CARBOXALDEHYDE; 5-P-TOLYL-1H-PYRROLE-2-CARBALDEHYDE; 5-TERT-BUTYL-1H-IMIDAZOLE-4-CARBALDEHYDE; 5-TERT-BUTYL-2-(2-METHYLPHENYL)-1H-INDOLE-3-CARBALDEHYDE; 5-TERT-BUTYL-2-CYCLOPENTYL-1H-INDOLE-3-CARBALDEHYDE; 5-TERT-BUTYL-4H-1,2,4-TRIAZOLE-3-CARBALDEHYDE; 5-TERT-BUTYL-PYRROLE-2-CARBALDEHYDE; 5-THIEN-2-YL-1H-PYRROLE-2-CARBALDEHYDE; 6-((2R)-2-PIPERIDYL)PYRIDINE-2-CARBALDEHYDE; 6-((2R)-2-PIPERIDYL)PYRIDINE-3-CARBALDEHYDE; 6-((2R)AZETIDIN-2-YL)-5-(PHENYLMETHOXY)PYRIDINE-2-CARBALDEHYDE; 6-((2R)AZETIDIN-2-YL)-5-METHOXYPYRIDINE-2-CARBALDEHYDE; 6-((2R)AZETIDIN-2-YL)PYRIDINE-2-CARBALDEHYDE; 6-((2R)AZETIDIN-2-YL)PYRIDINE-3-CARBALDEHYDE; 6-((2R)PYRROLIDIN-2-YL)PYRIDINE-2-CARBALDEHYDE; 6-((2R)PYRROLIDIN-2-YL)PYRIDINE-3-CARBALDEHYDE; 6-((2S)-2-PIPERIDYL)PYRIDINE-2-CARBALDEHYDE; 6-((2S)-2-PIPERIDYL)PYRIDINE-3-CARBALDEHYDE; 6-((2S)AZETIDIN-2-YL)-5-(PHENYLMETHOXY)PYRIDINE-2-CARBALDEHYDE; 6-((2S)AZETIDIN-2-YL)-5-METHOXYPYRIDINE-2-CARBALDEHYDE; 6-((2S)AZETIDIN-2-YL)PYRIDINE-2-CARBALDEHYDE; 6-((2S)AZETIDIN-2-YL)PYRIDINE-3-CARBALDEHYDE; 6-((2S)PYRROLIDIN-2-YL)PYRIDINE-2-CARBALDEHYDE; 6-((2S)PYRROLIDIN-2-YL)PYRIDINE-3-CARBALDEHYDE; 6-((3R)MORPHOLIN-3-YL)-5-(PHENYLMETHOXY)PYRIDINE-2-CARBALDEHYDE; 6-((3R)MORPHOLIN-3-YL)PYRIDINE-2-CARBALDEHYDE; 6-((3R)MORPHOLIN-3-YL)PYRIDINE-3-CARBALDEHYDE; 6-((3S)MORPHOLIN-3-YL)-5-(PHENYLMETHOXY)PYRIDINE-2-CARBALDEHYDE; 6-((3S)MORPHOLIN-3-YL)PYRIDINE-2-CARBALDEHYDE; 6-((3S)MORPHOLIN-3-YL)PYRIDINE-3-CARBALDEHYDE; 6-(1H-IMIDAZOL-2-YL)-HEXANAL; 6-(1H-IMIDAZOL-4-YL)-HEXANAL; 6-(2-FLUOROPHENYL)-1H-INDOLE-3-CARBALDEHYDE; 6-(2-METHOXYBENZYLAMINO)IMIDAZO[1,2-B]PYRIDAZINE-2-CARBALDEHYDE; 6(3,9-DIAZASPIRO[5.5]UNDEC-3-YL)NICOTINALDEHYDE; 6-(3-ACETYLAMINOPHENYL)-2-FORMYLPHENOL; 6-(3-FLUOROPHENYL)-1H-INDOLE-3-CARBALDEHYDE; 6-(3-OXOPIPERAZIN-1-YL)IMIDAZO[2,1-B][1,3]THIAZOLE-5-CARBALDEHYDE; 6-(4-FLUOROPHENYL)-1H-INDOLE-3-CARBALDEHYDE; 6-(4-FORMYL-1H-IMIDAZOL-2-YL)-NAPHTHALEN-2-OL; 6-(4-FORMYLIMIDAZOL-2-YL)2,3-DIMETHOXYBENZOIC ACID; 6-(5-OXO-1,4-DIAZEPAN-1-YL)IMIDAZO[2,1-B][1,3]THIAZOLE-5-CARBALDEHYDE; 6-(AMINOMETHYL)-4-CYCLOPROPOXY-1,6-DIHYDROPYRIDINE-2-CARBALDEHYDE; 6-(BENZYLAMINO)-5-NITRONICOTINALDEHYDE; 6-(BENZYLAMINO)NICOTINALDEHYDE; 6-(BENZYLOXY)-5-METHYL-1H-INDOLE-3-CARBALDEHYDE; 6-(BUTYLAMINO)NICOTINALDEHYDE; 6-(CYCLOPROPYLAMINO)IMIDAZO[1,2-B]PYRIDAZINE-2-CARBALDEHYDE; 6-(CYCLOPROPYLAMINO)NICOTINALDEHYDE; 6-(ETHYLAMINO)IMIDAZO[1,2-B]PYRIDAZINE-2-CARBALDEHYDE; 6-(ETHYLAMINO)NICOTINALDEHYDE; 6-(ISOPENTYLAMINO)-5-NITRONICOTINALDEHYDE; 6-(ISOPROPYLAMINO)-1,3-DIMETHYL-2,4-DIOXO-1,2,3,4-TETRAHYDRO-5-PYRIMIDINECARBALDEHYDE; 6-(ISOPROPYLAMINO)NICOTINALDEHYDE; 6-(METHYLAMINO)NICOTINALDEHYDE; 6-(PHENYLAMINO)NICOTINALDEHYDE; 6-(PIPERIDIN-4-YLOXY)NICOTINALDEHYDE; 6-(PROPYLAMINO)NICOTINALDEHYDE; 6-(PYRIDIN-3-YL)-1H-INDOLE-3-CARBALDEHYDE; 6-(PYRIDIN-4-YL)-1H-INDOLE-3-CARBALDEHYDE; 6-(PYRROLIDIN-3-YL)NICOTINALDEHYDE; 6-(TERT-BUTYLAMINO)NICOTINALDEHYDE; 6-(TRIFLUOROMETHOXY)-1H-INDOLE-3-CARBALDEHYDE; 6-(TRIFLUOROMETHYL)-1H-IMIDAZO[4,5-B]PYRIDINE-2-CARBALDEHYDE; 6-(TRIFLUOROMETHYL)-1H-PYRROLO[3,2-B]PYRIDINE-3-CARBALDEHYDE; 6-(TRIFLUOROMETHYL)-1H-PYRROLO[3,2-C]PYRIDINE-3-CARBALDEHYDE; 6-(TRIFLUOROMETHYL)INDOLE-3-CARBOXALDEHYDE; 6,7-DICHLOROINDOLE-3-CARBOXALDEHYDE; 6,7-DIETHOXY-2-OXO-1,2-DIHYDROQUINOLINE-3-CARBALDEHYDE; 6,7-DIFLUORO-2-(2,3-DIFLUOROPHENYL)-1H-INDOLE-3-CARBOXALDEHYDE; 6,7-DIFLUORO-2-(2,4-DIFLUOROPHENYL)-1H-INDOLE-3-CARBOXALDEHYDE; 6,7-DIFLUORO-2-(2,5-DIFLUOROPHENYL)-1H-INDOLE-3-CARBOXALDEHYDE; 6,7-DIFLUORO-2-(2,6-DIFLUOROPHENYL)-1H-INDOLE-3-CARBOXALDEHYDE; 6,7-DIFLUORO-2-(2-FLUOROPHENYL)-1H-INDOLE-3-CARBOXALDEHYDE; 6,7-DIFLUORO-2-(2-METHYLPHENYL)-1H-INDOLE-3-CARBOXALDEHYDE; 6,7-DIFLUORO-2-(3,4-DIFLUOROPHENYL)-1H-INDOLE-3-CARBOXALDEHYDE; 6,7-DIFLUORO-2-(3,5-DIFLUOROPHENYL)-1H-INDOLE-3-CARBOXALDEHYDE; 6,7-DIFLUORO-2-(3-FLUOROPHENYL)-1H-INDOLE-3-CARBOXALDEHYDE; 6,7-DIFLUORO-2-(3-METHYLPHENYL)-1H-INDOLE-3-CARBOXALDEHYDE; 6,7-DIFLUORO-2-(4-ETHYLPHENYL)-1H-INDOLE-3-CARBOXALDEHYDE; 6,7-DIFLUORO-2-(4-FLUOROPHENYL)-1H-INDOLE-3-CARBOXALDEHYDE; 6,7-DIFLUORO-2-(4-METHYLPHENYL)-1H-INDOLE-3-CARBOXALDEHYDE; 6,7-DIFLUORO-2-[4-(1-METHYLETHYL)PHENYL]-1H-INDOLE-3-CARBOXALDEHYDE; 6,7-DIFLUOROINDOLE-3-CARBOXALDEHYDE; 6,7-DIMETHYL-2-(2-FLUOROPHENYL)-1H-INDOLE-3-CARBOXALDEHYDE; 6,7-DIMETHYL-2-(2-METHYLPHENYL)-1H-INDOLE-3-CARBOXALDEHYDE; 6,7-DIMETHYL-2-(2-NITROPHENYL)-1H-INDOLE-3-CARBOXALDEHYDE; 6,7-DIMETHYL-2-(3-FLUOROPHENYL)-1H-INDOLE-3-CARBOXALDEHYDE; 6,7-DIMETHYL-2-(3-METHYLPHENYL)-1H-INDOLE-3-CARBOXALDEHYDE; 6,7-DIMETHYL-2-(3-NITROPHENYL)-1H-INDOLE-3-CARBOXALDEHYDE; 6,7-DIMETHYL-2-(4-ETHYLPHENYL)-1H-INDOLE-3-CARBOXALDEHYDE; 6,7-DIMETHYL-2-(4-FLUOROPHENYL)-1H-INDOLE-3-CARBOXALDEHYDE; 6,7-DIMETHYL-2-(4-METHYLPHENYL)-1H-INDOLE-3-CARBOXALDEHYDE; 6,7-DIMETHYL-2-(4-NITROPHENYL)-1H-INDOLE-3-CARBOXALDEHYDE; 6,7-DIMETHYL-2-[4-(1-METHYLETHYL)PHENYL]-1H-INDOLE-3-CARBOXALDEHYDE; 6-[(1-BENZYL-4-PIPERIDYL)AMINO]NICOTINALDEHYDE; 6-[(2-METHOXYETHYL)AMINO]-1,3-DIMETHYL-2,4-DIOXO-1,2,3,4-TETRAHYDRO-5-PYRIMIDINECARBALDEHYDE;

6-[3-(CYCLOPROPYLAMINOCARBONYL)PHENYL]-2-FORMYLPHENOL; 6-[3-(N-ETHYLAMINOCARBONYL)PHENYL]-2-FORMYLPHENOL; 6-[4-(ETHYLCARBAMOYL)-3-FLUOROPHENYL]-2-FORMYLPHENOL; 6-ACETAMIDOHEXANAL; 6-AMINO-1-(2-CHLOROPHENYL)-4-OXO-2-THIOXO-1,2,3,4-TETRAHYDRO-5-PYRIMIDINECARBALDEHYDE; 6-AMINO-1-(2-FURYLMETHYL)-2,4-DIOXO-TETRAHYDROPYRIMIDINE-5-CARBALDEHYDE; 6-AMINO-1-(2-METHYLPHENYL)-4-OXO-2-THIOXO-1,2,3,4-TETRAHYDRO-5-PYRIMIDINECARBALDEHYDE; 6-AMINO-1-(3-METHOXYPHENYL)-2,4-DIOXO-1,2,3,4-TETRAHYDROPYRIMIDINE-5-CARBALDEHYDE; 6-AMINO-1-(4-CHLOROPHENYL)-2,4-DIOXOTETRAHYDROPYRIMIDINE-5-CARBALDEHYDE; 6-AMINO-1-(4-CHLOROPHENYL)-4-OXO-2-THIOXO-1,2,3,4-TETRAHYDRO-5-PYRIMIDINECARBALDEHYDE; 6-AMINO-1-(4-METHOXYPHENYL)-2,4-DIOXO-1,2,3,4-TETRAHYDROPYRIMIDINE-5-CARBALDEHYDE; 6-AMINO-1-(4-METHOXYPHENYL)-4-OXO-2-THIOXO-1,2,3,4-TETRAHYDRO-5-PYRIMIDINECARBALDEHYDE; 6-AMINO-1-(4-METHYLPHENYL)-4-OXO-2-THIOXO-1,2,3,4-TETRAHYDRO-5-PYRIMIDINECARBALDEHYDE; 6-AMINO-1-BENZYL-2,4-DIOXOTETRAHYDROPYRIMIDINE-5-CARBALDEHYDE; 6-AMINO-1H-PYRROLO[3,2-B]PYRIDINE-3-CARBALDEHYDE; 6-AMINO-1-METHYL-2,4-DIOXO-1,2,3,4-TETRAHYDRO-5-PYRIMIDINECARBALDEHYDE; 6-AMINO-2,4-DIOXO-1-(2-PHENYLETHYL)TETRAHYDROPYRIMIDINE-5-CARBALDEHYDE; 6-AMINO-2,4-DIOXO-1-(PYRIDIN-3-YLMETHYL)TETRAHYDROPYRIMIDINE-5-CARBALDEHYDE; 6-AMINO-2,4-DIOXO-1,2,3,4-TETRAHYDRO-PYRIMIDINE-5-CARBALDEHYDE; 6-AMINO-4-OXO-1-PHENYL-2-THIOXO-1,2,3,4-TETRAHYDRO-5-PYRIMIDINECARBALDEHYDE; 6-AMINOINDOLE-3-CARBOXALDEHYDE; 6-AZAINDOLE-3-CARBOXALDEHYDE; 6-BENZOYL-1H-INDOLE-3-CARBALDEHYDE; 6-BENZYLOXYINDOLE-3-CARBOXALDEHYDE; 6-BENZYLOXYMETHYL-1H-INDOLE-3-CARBALDEHYDE; 6-BROMO-1,2-DIHYDRO-2-OXO-3-QUINOLINECARBOXALDEHYDE; 6-BROMO-1H-BENZOIMIDAZOLE-2-CARBALDEHYDE; 6-BROMO-1H-INDOLE-2-CARBALDEHYDE; 6-BROMO-1H-PYRROLO[3,2-B]PYRIDINE-3-CARBALDEHYDE; 6-BROMO-1H-PYRROLO[3,2-C]PYRIDINE-3-CARBALDEHYDE; 6-BROMO-2-(DIMETHYLAMINO)-1H-INDOLE-3-CARBALDEHYDE; 6-BROMO-2-OXO-1,2,3,4-TETRAHYDRO-QUINOLINE-3-CARBALDEHYDE; 6-BROMO-4-FLUOROINDOLE-3-CARBOXALDEHYDE; 6-BROMO-4-HYDROXYINDOLE-3-CARBOXALDEHYDE; 6-BROMO-4-METHOXYINDOLE-3-CARBOXALDEHYDE; 6-BROMO-4-OXO-3,4-DIHYDROQUINAZOLINE-2-CARBALDEHYDE; 6-BROMO-5-FLUOROINDOLE-3-CARBOXALDEHYDE; 6-BROMO-7-FLUOROINDOLE-3-CARBOXALDEHYDE; 6-BROMO-7-HYDROXYINDOLE-3-CARBOXALDEHYDE; 6-BROMO-7-METHOXYINDOLE-3-CARBOXALDEHYDE; 6-BROMOINDOLE-3-CARBOXALDEHYDE; 6-CHLORO-1,2-DIHYDRO-2-OXO-3-QUINOLINECARBOXALDEHYDE; 6-CHLORO-1H-BENZOIMIDAZOLE-2-CARBALDEHYDE; 6-CHLORO-1H-INDOLE-2-CARBALDEHYDE; 6-CHLORO-1H-PYRROLO[2,3-B]PYRIDINE-3-CARBALDEHYDE; 6-CHLORO-1H-PYRROLO[3,2-C]PYRIDINE-3-CARBALDEHYDE; 6-CHLORO-2-CYCLOHEXYL-7-FLUORO-1H-INDOLE-3-CARBOXALDEHYDE; 6-CHLORO-2-CYCLOPROPYL-7-FLUORO-1H-INDOLE-3-CARBOXALDEHYDE; 6-CHLORO-2-METHYL-1H-BENZO[D]IMIDAZOLE-5-CARBALDEHYDE; 6-CHLORO-2-OXO-3-INDOLINECARBALDEHYDE; 6-CHLORO-4-(METHYLAMINO)NICOTINALDEHYDE; 6-CHLORO-4-AZAINDOLE-3-CARBALDEHYDE; 6-CHLORO-4-FLUOROINDOLE-3-CARBOXALDEHYDE; 6-CHLORO-4-HYDROXYINDOLE-3-CARBOXALDEHYDE; 6-CHLORO-4-METHOXYINDOLE-3-CARBOXALDEHYDE; 6-CHLORO-5,6-DIHYDRO-1H-PYRROLO[2,3-B]PYRIDINE-3-CARBALDEHYDE; 6-CHLORO-5-FLUOROINDOLE-3-CARBOXALDEHYDE; 6-CHLORO-5-METHOXY-1H-INDOLE-3-CARBALDEHYDE; 6-CHLORO-7-FLUORO-2-(2-FLUOROPHENYL)-1H-INDOLE-3-CARBOXALDEHYDE; 6-CHLORO-7-FLUORO-2-(2-METHYLPHENYL)-1H-INDOLE-3-CARBOXALDEHYDE; 6-CHLORO-7-FLUORO-2-(3-FLUOROPHENYL)-1H-INDOLE-3-CARBOXALDEHYDE; 6-CHLORO-7-FLUORO-2-(3-METHYLPHENYL)-1H-INDOLE-3-CARBOXALDEHYDE; 6-CHLORO-7-FLUORO-2-(4-FLUOROPHENYL)-1H-INDOLE-3-CARBOXALDEHYDE; 6-CHLORO-7-FLUORO-2-(4-METHYLPHENYL)-1H-INDOLE-3-CARBOXALDEHYDE; 6-CHLORO-7-FLUOROINDOLE-3-CARBOXALDEHYDE; 6-CHLORO-7-HYDROXYINDOLE-3-CARBOXALDEHYDE; 6-CHLORO-7-METHOXYINDOLE-3-CARBOXALDEHYDE; 6-CHLORO-7-METHYL-1H-INDOLE-2-CARBALDEHYDE; 6-CHLOROINDOLE-3-CARBOXALDEHYDE; 6-ETHOXY-2-OXO-1,2-DIHYDRO-QUINOLINE-3-CARBALDEHYDE; 6-ETHOXYINDOLE-3-CARBOXALDEHYDE; 6-ETHYL-1,2-DIHYDRO-2-OXO-3-QUINOLINECARBOXALDEHYDE; 6-ETHYLINDOLE-3-CARBOXALDEHYDE; 6-FLUORO-1H-BENZOIMIDAZOLE-2-CARBALDEHYDE; 6-FLUORO-1H-INDOLE-2-CARBALDEHYDE; 6-FLUORO-1H-PYRROLO[2,3-B]PYRIDINE-3-CARBALDEHYDE; 6-FLUORO-1H-PYRROLO[2,3-B]PYRIDINE-4-CARBALDEHYDE; 6-FLUORO-1H-PYRROLO[3,2-C]PYRIDINE-3-CARBALDEHYDE; 6-FLUORO-2,3,4,9-TETRAHYDRO-1H-CARBAZOLE-3-CARBALDEHYDE; 6-FLUORO-2-OXOINDOLINE-3-CARBALDEHYDE; 6-FLUORO-4,5-DIHYDRO-IMIDAZOL[1,5-A]QUINOXALIN-3-CARBALDEHYDE; 6-FLUORO-4-AZAINDOLE-3-CARBOXALDEHYDE; 6-FLUORO-4-HYDROXY-1H-INDOLE-2-CARBALDEHYDE; 6-FLUORO-4-HYDROXYINDOLE-3-CARBOXALDEHYDE; 6-FLUORO-4-METHOXY-1H-INDOLE-2-CARBALDEHYDE; 6-FLUORO-4-METHOXYINDOLE-3-CARBOXALDEHYDE; 6-FLUORO-7-HYDROXYINDOLE-3-CARBOXALDEHYDE; 6-FLUORO-7-METHOXYINDOLE-3-CARBOXALDEHYDE; 6-FLUORO-7-METHYL-1H-INDOLE-2-CARBALDEHYDE; 6-FLUOROINDOLE-3-CARBOXALDEHYDE; 6-FORMYL-2,3-DIHYDRO-1H-INDOLE HYDROCHLORIDE; 6-FORMYL-2-THIOURACIL; 6-FORMYL-2-THIOURACIL HYDRATE; 6-FORMYL-3-IMINO-4-METHYL-N-PHENYL-3,4-DIHYDRO-2-PYRAZINECARBOXAMIDE; 6-FORMYL-8-FLUORO-2H-1,4-BENZOXAZIN-3(4H)-ONE; 6-FORMYL-N-ISOPROPYL[1,2,4]TRIAZOLO[1,5-A]PYRIMIDINE-2-

CARBOXAMIDE; 6-FORMYL-URACIL MONOHYDRATE; 6H-THIENO[2,3-B]PYRROLE-3-CARBOXALDEHYDE; 6-HYDROXY-1,2,3,4-TETRAHYDROISOQUINOLINE-3-CARBALDEHYDE; 6-HYDROXY-1H-PYRROLO[3,2-C]PYRIDINE-3-CARBALDEHYDE; 6-HYDROXY-2,4-DIOXO-1,2,3,4-TETRAHYDROPYRIMIDINE-5-CARBALDEHYDE; 6-HYDROXY-4-AZAINDOLE-3-CARBALDEHYDE; 6-HYDROXYINDOLE-3-CARBOXALDEHYDE; 6-HYDROXYNICOTINALDEHYDE; 6-IODO-1H-BENZOIMIDAZOLE-2-CARBALDEHYDE; 6-METHOXY-1H-BENZOIMIDAZOLE-2-CARBALDEHYDE; 6-METHOXY-1H-INDOLE-3-CARBALDEHYDE; 6-METHOXY-1H-PYRROLO[2,3-B]PYRIDINE-3-CARBALDEHYDE; 6-METHOXY-1H-PYRROLO[2,3-B]PYRIDINE-4-CARBALDEHYDE; 6-METHOXY-1H-PYRROLO[3,2-B]PYRIDINE-3-CARBALDEHYDE; 6-METHOXY-1H-PYRROLO[3,2-C]PYRIDINE-3-CARBALDEHYDE; 6-METHOXY-2-METHYL-1H-INDOLE-3-CARBALDEHYDE; 6-METHOXY-2-OXO-1,2-DIHYDRO-QUINOLINE-3-CARBALDEHYDE; 6-METHOXY-2-OXOINDOLINE-3-CARBALDEHYDE; 6-METHOXY-9H-PURINE-8-CARBALDEHYDE; 6-METHYL-1H-BENZOIMIDAZOLE-2-CARBALDEHYDE; 6-METHYL-1H-INDOLE-2-CARBALDEHYDE; 6-METHYL-1H-INDOLE-4-CARBALDEHYDE; 6-METHYL-2,4-DIOXO-1,2,3,4-TETRAHYDRO-PYRIMIDINE-5-CARBALDEHYDE; 6-METHYL-2-OXO-1,2-DIHYDROQUINOLIN-3-CARBALDEHYDE; 6-METHYL-2-OXOINDOLINE-3-CARBALDEHYDE; 6-METHYL-5,6-DIHYDRO-1H-PYRROLO[2,3-B]PYRIDINE-3-CARBALDEHYDE; 6-METHYL-5-AZAINDOLE-3-CARBOXALDEHYDE; 6-METHYLINDOLE-3-CARBOXALDEHYDE; 6-NITRO-1H-BENZOIMIDAZOLE-2-CARBALDEHYDE; 6-NITRO-1H-INDOLE-3-CARBALDEHYDE; 6-NITRO-1H-PYRROLO[3,2-B]PYRIDINE-3-CARBALDEHYDE; 6-NITRO-2-METHYL-1H-INDOLE-3-CARBALDEHYDE; 6-OXO-5,6,7,8-TETRAHYDRO-IMIDAZO[1,2-A]PYRAZINE-3-CARBALDEHYDE; 6-OXO-5,6-DIHYDRO-[1,3]DIOXOLO[4,5-G]QUINOLINE-7-CARBALDEHYDE; 6-PHENYL-1H-PYRROLO[2,3-B]PYRIDINE-2-CARBOXALDEHYDE; 6-PHENYL-1H-PYRROLO[2,3-B]PYRIDINE-3-CARBOXALDEHYDE; 6-PHENYL-1H-PYRROLO[2,3-B]PYRIDINE-4-CARBOXALDEHYDE; 6-PHENYL-1H-PYRROLO[2,3-B]PYRIDINE-5-CARBOXALDEHYDE; 6-PIPERAZIN-1-YLNICOTINALDEHYDE; 6-QUINOXALINECARBOXALDEHYDE, 3,4-DIHYDRO-3-OXO-; 6-TRIFLUOROMETHOXY-1H-BENZOIMIDAZOLE-2-CARBALDEHYDE; 6-TRIFLUOROMETHYL-1H-BENZOIMIDAZOLE-2-CARBALDEHYDE; 7-(2-FLUOROPHENYL)-1H-INDOLE-3-CARBALDEHYDE; 7-(3-FLUOROPHENYL)-1H-INDOLE-3-CARBALDEHYDE; 7-(4-FLUOROPHENYL)-1H-INDOLE-3-CARBALDEHYDE; 7-(PYRIDIN-3-YL)-1H-INDOLE-3-CARBALDEHYDE; 7-(PYRIDIN-4-YL)-1H-INDOLE-3-CARBALDEHYDE; 7-(TRIFLUOROMETHYL)-1H-INDOLE-2-CARBALDEHYDE; 7-(TRIFLUOROMETHYL)-1H-PYRROLO[3,2-B]PYRIDINE-3-CARBALDEHYDE; 7-(TRIFLUOROMETHYL)INDOLE-3-CARBOXALDEHYDE; 7-AMINO-1H-PYRROLO[3,2-B]PYRIDINE-3-CARBALDEHYDE; 7-AMINOINDOLE-3-CARBOXALDEHYDE; 7-AZAINDOLE-4-CARBOXALDEHYDE; 7-BENZYLOXYINDOLE-3-CARBALDEHYDE; 7-BENZYLOXYMETHYL-1H-INDOLE-3-CARBALDEHYDE; 7-BROMO-1H-INDOLE-2-CARBALDEHYDE; 7-BROMO-1H-PYRROLO[2,3-C]PYRIDINE-3-CARBALDEHYDE; 7-BROMO-1H-PYRROLO[3,2-B]PYRIDINE-3-CARBALDEHYDE; 7-BROMO-2-CYCLOPROPYL-1H-INDOLE-3-CARBOXALDEHYDE; 7-BROMO-2-CYCLOPROPYL-5-FLUORO-1H-INDOLE-3-CARBOXALDEHYDE; 7-BROMO-3-FORMYL-1H-INDOLE; 7-BROMO-4-CHLORO-1H-PYRROLO[3,2-C]PYRIDINE-3-CARBALDEHYDE; 7-BROMO-4-FLUOROINDOLE-3-CARBOXALDEHYDE; 7-BROMO-4-HYDROXYINDOLE-3-CARBOXALDEHYDE; 7-BROMO-4-METHOXYINDOLE-3-CARBOXALDEHYDE; 7-BROMO-4-METHYL-1H-INDOLE-3-CARBALDEHYDE; 7-BROMO-5-FLUORO-1H-INDOLE-3-CARBALDEHYDE; 7-BROMO-5-HYDROXYINDOLE-3-CARBOXALDEHYDE; 7-BROMO-5-METHOXYINDOLE-3-CARBOXALDEHYDE; 7-BROMO-5-METHYL-1H-INDOLE-2-CARBOXALDEHYDE; 7-BROMO-6-FLUOROINDOLE-3-CARBOXALDEHYDE; 7-BROMO-6-HYDROXYINDOLE-3-CARBOXALDEHYDE; 7-BROMO-6-METHOXYINDOLE-3-CARBOXALDEHYDE; 7-CHLORO-1,2-DIHYDRO-2-OXO-3-QUINOLINECARBOXALDEHYDE; 7-CHLORO-1H-INDOLE-2-CARBALDEHYDE; 7-CHLORO-1H-INDOLE-3-CARBALDEHYDE; 7-CHLORO-1H-INDOLE-4-CARBALDEHYDE; 7-CHLORO-1H-INDOLE-5-CARBALDEHYDE; 7-CHLORO-1H-PYRROLO[2,3-C]PYRIDINE-3-CARBALDEHYDE; 7-CHLORO-1H-PYRROLO[3,2-B]PYRIDINE-3-CARBALDEHYDE; 7-CHLORO-2-(2,3-DIFLUOROPHENYL)-1H-INDOLE-3-CARBOXALDEHYDE; 7-CHLORO-2-(2,4-DIFLUOROPHENYL)-1H-INDOLE-3-CARBOXALDEHYDE; 7-CHLORO-2-(2,5-DIFLUOROPHENYL)-1H-INDOLE-3-CARBOXALDEHYDE; 7-CHLORO-2-(2,6-DIFLUOROPHENYL)-1H-INDOLE-3-CARBOXALDEHYDE; 7-CHLORO-2-(2-CHLOROPHENYL)-1H-INDOLE-3-CARBOXALDEHYDE; 7-CHLORO-2-(2-FLUOROPHENYL)-1H-INDOLE-3-CARBOXALDEHYDE; 7-CHLORO-2-(2-METHYLPHENYL)-1H-INDOLE-3-CARBOXALDEHYDE; 7-CHLORO-2-(3,4-DIFLUOROPHENYL)-1H-INDOLE-3-CARBOXALDEHYDE; 7-CHLORO-2-(3,5-DIFLUOROPHENYL)-1H-INDOLE-3-CARBOXALDEHYDE; 7-CHLORO-2-(3-CHLOROPHENYL)-1H-INDOLE-3-CARBOXALDEHYDE; 7-CHLORO-2-(3-FLUOROPHENYL)-1H-INDOLE-3-CARBOXALDEHYDE; 7-CHLORO-2-(3-METHYLPHENYL)-1H-INDOLE-3-CARBOXALDEHYDE; 7-CHLORO-2-(4-CHLOROPHENYL)-1H-INDOLE-3-CARBOXALDEHYDE; 7-CHLORO-2-(4-ETHYLPHENYL)-1H-INDOLE-3-CARBOXALDEHYDE; 7-CHLORO-2-(4-FLUOROPHENYL)-1H-INDOLE-3-CARBOXALDEHYDE; 7-CHLORO-2-(4-METHYLPHENYL)-1H-INDOLE-3-CARBOXALDEHYDE; 7-CHLORO-2-[4-(1-METHYLETHYL)PHENYL]-1H-INDOLE-3-CARBOXALDEHYDE; 7-CHLORO-2-CYCLOHEXYL-1H-INDOLE-3-CARBOXALDEHYDE; 7-CHLORO-2-CYCLOHEXYL-5-FLUORO-1H-INDOLE-3-CARBOXALDEHYDE; 7-CHLORO-2-CYCLOPROPYL-

1H-INDOLE-3-CARBOXALDEHYDE; 7-CHLORO-2-CYCLOPROPYL-5-FLUORO-1H-INDOLE-3-CARBOXALDEHYDE; 7-CHLORO-2-CYCLOPROPYL-5-NITRO-1H-INDOLE-3-CARBOXALDEHYDE; 7-CHLORO-3,3-DIMETHYL-2,3-DIHYDRO-1H-INDOLE-5-CARBALDEHYDE; 7-CHLORO-3-METHYL-1H-INDOLE-2-CARBALDEHYDE; 7-CHLORO-4-(TRIFLUOROMETHYL)-1H-INDOLE-2-CARBALDEHYDE; 7-CHLORO-4-FLUOROINDOLE-3-CARBOXALDEHYDE; 7-CHLORO-4-HYDROXYINDOLE-3-CARBOXALDEHYDE; 7-CHLORO-4-METHOXYINDOLE-3-CARBOXALDEHYDE; 7-CHLORO-4-METHYL-1H-INDOLE-3-CARBALDEHYDE; 7-CHLORO-5-FLUORO-1H-INDOLE-3-CARBALDEHYDE; 7-CHLORO-5-FLUORO-2-(2-FLUOROPHENYL)-1H-INDOLE-3-CARBOXALDEHYDE; 7-CHLORO-5-FLUORO-2-(2-METHYLPHENYL)-1H-INDOLE-3-CARBOXALDEHYDE; 7-CHLORO-5-FLUORO-2-(3-FLUOROPHENYL)-1H-INDOLE-3-CARBOXALDEHYDE; 7-CHLORO-5-FLUORO-2-(3-METHYLPHENYL)-1H-INDOLE-3-CARBOXALDEHYDE; 7-CHLORO-5-FLUORO-2-(4-FLUOROPHENYL)-1H-INDOLE-3-CARBOXALDEHYDE; 7-CHLORO-5-FLUORO-2-(4-METHYLPHENYL)-1H-INDOLE-3-CARBOXALDEHYDE; 7-CHLORO-5-HYDROXYINDOLE-3-CARBOXALDEHYDE; 7-CHLORO-5-METHOXYINDOLE-3-CARBOXALDEHYDE; 7-CHLORO-5-METHYL-1H-INDOLE-2-CARBOXALDEHYDE; 7-CHLORO-6-FLUOROINDOLE-3-CARBOXALDEHYDE; 7-CHLORO-6-HYDROXYINDOLE-3-CARBOXALDEHYDE; 7-CHLORO-6-METHOXYINDOLE-3-CARBOXALDEHYDE; 7-ETHOXY-1,2-DIHYDRO-2-OXO-3-QUINOLINECARBOXALDEHYDE; 7-ETHOXYINDOLE-3-CARBOXALDEHYDE; 7-ETHYL-1H-INDOLE-3-CARBALDEHYDE; 7-FLUORO-1H-INDOLE-3-CARBALDEHYDE; 7-FLUORO-1H-INDOLE-5-CARBALDEHYDE; 7-FLUORO-1H-PYRROLO[2,3-C]PYRIDINE-3-CARBALDEHYDE; 7-FLUORO-1H-PYRROLO[3,2-C]PYRIDINE-3-CARBALDEHYDE; 7-FLUORO-2-(2,3,4-TRIFLUOROPHENYL)-1H-INDOLE-3-CARBOXALDEHYDE; 7-FLUORO-2-(2,4,5-TRIFLUOROPHENYL)-1H-INDOLE-3-CARBOXALDEHYDE; 7-FLUORO-2-(2-FLUOROPHENYL)-1H-INDOLE-3-CARBOXALDEHYDE; 7-FLUORO-2-(2-FLUOROPHENYL)-5-METHYL-1H-INDOLE-3-CARBOXALDEHYDE; 7-FLUORO-2-(2-METHYLPHENYL)-1H-INDOLE-3-CARBOXALDEHYDE; 7-FLUORO-2-(2-NITROPHENYL)-1H-INDOLE-3-CARBOXALDEHYDE; 7-FLUORO-2-(3-FLUOROPHENYL)-1H-INDOLE-3-CARBOXALDEHYDE; 7-FLUORO-2-(3-FLUOROPHENYL)-5-METHYL-1H-INDOLE-3-CARBOXALDEHYDE; 7-FLUORO-2-(3-METHYLPHENYL)-1H-INDOLE-3-CARBOXALDEHYDE; 7-FLUORO-2-(3-NITROPHENYL)-1H-INDOLE-3-CARBOXALDEHYDE; 7-FLUORO-2-(4-FLUOROPHENYL)-1H-INDOLE-3-CARBOXALDEHYDE; 7-FLUORO-2-(4-FLUOROPHENYL)-5-METHYL-1H-INDOLE-3-CARBOXALDEHYDE; 7-FLUORO-2-(4-METHYLPHENYL)-1H-INDOLE-3-CARBOXALDEHYDE; 7-FLUORO-2-(4-NITROPHENYL)-1H-INDOLE-3-CARBOXALDEHYDE; 7-FLUORO-2-[4-(1-METHYLETHYL)PHENYL]-1H-INDOLE-3-CARBOXALDEHYDE; 7-FLUORO-3,3-DIMETHYL-2,3-DIHYDRO-1H-INDOLE-5-CARBALDEHYDE; 7-FLUORO-3,3-DIMETHYL-2-OXO-2,3-DIHYDRO-1H-INDOLE-5-CARBALDEHYDE; 7-FLUORO-4-HYDROXY-1H-INDOLE-2-CARBALDEHYDE; 7-FLUORO-4-HYDROXYINDOLE-3-CARBOXALDEHYDE; 7-FLUORO-4-METHOXY-1H-INDOLE-2-CARBALDEHYDE; 7-FLUORO-4-METHOXYINDOLE-3-CARBOXALDEHYDE; 7-FLUORO-5-HYDROXYINDOLE-3-CARBOXALDEHYDE; 7-FLUORO-5-METHOXYINDOLE-3-CARBOXALDEHYDE; 7-FLUORO-5-METHYL-2-(2-METHYLPHENYL)-1H-INDOLE-3-CARBOXALDEHYDE; 7-FLUORO-5-METHYL-2-(2-NITROPHENYL)-1H-INDOLE-3-CARBOXALDEHYDE; 7-FLUORO-5-METHYL-2-(3-METHYLPHENYL)-1H-INDOLE-3-CARBOXALDEHYDE; 7-FLUORO-5-METHYL-2-(3-NITROPHENYL)-1H-INDOLE-3-CARBOXALDEHYDE; 7-FLUORO-5-METHYL-2-(4-METHYLPHENYL)-1H-INDOLE-3-CARBOXALDEHYDE; 7-FLUORO-5-METHYL-2-(4-NITROPHENYL)-1H-INDOLE-3-CARBOXALDEHYDE; 7-FLUORO-5-METHYL-2-[4-(1-METHYLETHYL)PHENYL]-1H-INDOLE-3-CARBOXALDEHYDE; 7-FLUORO-6-HYDROXYINDOLE-3-CARBOXALDEHYDE; 7-FLUORO-6-METHOXYINDOLE-3-CARBOXALDEHYDE; 7-FORMYLGRAMINE; 7H-PYRROLO[2,3-D]PYRIMIDINE-5-CARBALDEHYDE; 7-HYDROXY-1H-PYRROLO[2,3-C]PYRIDINE-3-CARBALDEHYDE; 7-HYDROXY-1H-PYRROLO[3,2-B]PYRIDINE-3-CARBALDEHYDE; 7-HYDROXYINDOLE-3-CARBOXALDEHYDE; 7-INDOLINECARBOXALDEHYDE; 7-METHOXY-1H-INDOLE-2-CARBALDEHYDE; 7-METHOXY-1H-PYRROLO[2,3-C]PYRIDINE-3-CARBALDEHYDE; 7-METHOXY-1H-PYRROLO[3,2-B]PYRIDINE-3-CARBALDEHYDE; 7-METHOXY-2-(2-METHYLPHENYL)-1H-INDOLE-3-CARBOXALDEHYDE; 7-METHOXY-2-(2-NITROPHENYL)-1H-INDOLE-3-CARBOXALDEHYDE; 7-METHOXY-2-(3-METHYLPHENYL)-1H-INDOLE-3-CARBOXALDEHYDE; 7-METHOXY-2-(3-NITROPHENYL)-1H-INDOLE-3-CARBOXALDEHYDE; 7-METHOXY-2-(4-METHYLPHENYL)-1H-INDOLE-3-CARBOXALDEHYDE; 7-METHOXY-2-(4-NITROPHENYL)-1H-INDOLE-3-CARBOXALDEHYDE; 7-METHOXY-2-[4-(1-METHYLETHYL)PHENYL]-1H-INDOLE-3-CARBOXALDEHYDE; 7-METHOXY-2-METHYL-1H-INDOLE-3-CARBALDEHYDE; 7-METHOXY-2-OXO-1,2-DIHYDRO-QUINOLINE-3-CARBALDEHYDE; 7-METHOXY-3-INDOLECARBOXALDEHYDE; 7-METHYL-1H-INDOLE-2-CARBALDEHYDE; 7-METHYL-1H-PYRROLO[2,3-C]PYRIDINE-3-CARBALDEHYDE; 7-METHYL-1H-PYRROLO[3,2-B]PYRIDINE-3-CARBALDEHYDE; 7-METHYL-2-(2,3,4-TRIFLUOROPHENYL)-1H-INDOLE-3-CARBOXALDEHYDE; 7-METHYL-2-(2,4,5-TRIFLUOROPHENYL)-1H-INDOLE-3-CARBOXALDEHYDE; 7-METHYL-2-(2-METHYLPHENYL)-1H-INDOLE-3-CARBOXALDEHYDE; 7-METHYL-2-(2-METHYLPHENYL)-5-NITRO-1H-INDOLE-3-CARBOXALDEHYDE; 7-METHYL-2-(2-NITROPHENYL)-1H-INDOLE-3-CARBOXALDEHYDE; 7-METHYL-2-(3-METHYLPHENYL)-1H-INDOLE-3-CARBOXALDEHYDE; 7-METHYL-2-(3-METHYLPHENYL)-5-NITRO-1H-INDOLE-3-CARBOXALDEHYDE; 7-METHYL-2-(3-NITROPHENYL)-1H-INDOLE-3-CARBOXALDEHYDE; 7-METHYL-2-(4-METHYLPHENYL)-1H-INDOLE-3-CARBOXALDEHYDE;

7-METHYL-2-(4-METHYLPHENYL)-5-NITRO-1H-INDOLE-3-CARBOXALDEHYDE; 7-METHYL-2-(4-NITROPHENYL)-1H-INDOLE-3-CARBOXALDEHYDE; 7-METHYL-2-[4-(1-METHYLETHYL)PHENYL]-1H-INDOLE-3-CARBOXALDEHYDE; 7-METHYL-2-PHENYL-1H-INDOLE-3-CARBALDEHYDE; 7-METHYL-4-OXO-2-P-TOLYLAMINO-4H-PYRIDO(1,2-A)PYRIMIDINE-3-CARBALDEHYDE; 7-METHYL-5-AZAINDOLE-3-CARBOXALDEHYDE; 7-METHYLINDOLE-3-CARBOXALDEHYDE; 7-METHYLSULFANYL-2-OXO-1,2-DIHYDRO-QUINOLINE-3-CARBALDEHYDE; 7-NITRO-1H-PYRROLO[3,2-B]PYRIDINE-3-CARBALDEHYDE; 7-NITROINDOLE-3-CARBOXALDEHYDE; 7-OXO-2,3,6,7-TETRAHYDRO-[1,4]DIOXINO[2,3-G]QUINOLINE-8-CARBALDEHYDE; 8-CHLORO-1,2-DIHYDRO-2-OXO-3-QUINOLINECARBOXALDEHYDE; 8-CHLORO-5-METHOXY-2-OXO-1,2-DIHYDRO-QUINOLINE-4-CARBALDEHYDE; 8-ETHYL-1,2-DIHYDRO-2-OXO-3-QUINOLINECARBOXALDEHYDE; 8-METHYL-2-OXO-1,2-DIHYDROQUINOLINE-3-CARBALDEHYDE; 8-METHYL-3-OXO-3,4-DIHYDRO-2H-BENZO[1,4]OXAZINE-6-CARBALDEHYDE; 8-OXO-3,4,8,9-TETRAHYDRO-2H,7H-[1,4]DIOXEPINO[2,3-F]INDOLE-9-CARBALDEHYDE; 9H-CARBAZOLE-2-CARBALDEHYDE; 9H-CARBAZOLE-3-CARBALDEHYDE; 9H-PYRIDO[3,4-B]INDOLE-1-CARBOXALDEHYDE; 9-METHYL-4-OXO-2-(2-PYRIMIDINYLAMINO)-4H-PYRIDO(1,2-A)PYRIMIDINE-3-CARBALDEHYDE; 9-METHYL-4-OXO-2-(4-TOLUIDINO)-4H-PYRIDO(1,2-A)PYRIMIDINE-3-CARBALDEHYDE; ACETAMIDE, N-(2-FORMYL-1H-INDOL-5-YL)-; ACETAMIDE, N-[4-(2-FORMYL-1H-PYRROL-1-YL)PHENYL]-; ACETYL D-MANNOSAMINE N-[MANNOSAMINE-1-14C]; ACETYL-D-GALACTOSAMINE, N-[GALACTOSAMINE-1-14C]; ACETYL-D-GLUCOSAMINE N-[GLUCOSAMINE-6-3H]; ACETYL-D-GLUCOSAMINE, N-[GLUCOSAMINE-1-14C]; ACETYL-D-MANNOSAMINE, N-[MANNOSAMINE-6-3H]; ALAHOPCIN; ALLYL N-(5-FORMYLPYRIMIDIN-2-YL)GLYCINATE; ALORACETAM; AZETIDINE-2-CARBOXALDEHYDE; AZETIDINE-3-CARBOXALDEHYDE; BENZAMIDE, N-(4,6-DIMETHYL-2-PYRIDINYL)-4-FORMYL-; BENZYL (2R)-5-AMINO-4-METHYL-1-OXOPENTAN-2-YLCARBAMATE; BENZYL (4-FORMYL-1H-IMIDAZOL-2-YL)METHYLCARBAMATE; BENZYL (4-FORMYL-6-METHYLPYRIMIDIN-2-YL)METHYLCARBAMATE; BENZYL (4-FORMYLPYRIMIDIN-2-YL)METHYLCARBAMATE; BENZYL (5-FORMYLPYRIMIDIN-2-YL)METHYLCARBAMATE; BENZYL 2-(4-FORMYL-1H-IMIDAZOL-2-YL)ETHYLCARBAMATE; BENZYL 2-(5-FORMYLPYRIMIDIN-2-YL)ETHYLCARBAMATE; BENZYL 2-(FORMYLMETHYL)PHENYLCARBAMATE; BENZYL 2-OXOETHYLCARBAMATE; BENZYL 3-FORMYL-1H-INDOLE-2-CARBOXYLATE; BENZYL 3-FORMYLBICYCLO[2.2.1]HEPT-5-EN-2-YLCARBAMATE; BENZYL 4-ETHYL-5-FORMYL-3-METHYL-2-PYRROLECARBOXYLATE; BENZYL 4-FORMYL-BENZYLCARBAMATE; BENZYL 4-FORMYLPYRIDIN-2-YLCARBAMATE; BENZYL 4-OXOBUTYLCARBAMATE; BENZYL 5-FORMYL-2-HYDROXYPHENYLCARBAMATE; BENZYL 6-FORMYLPYRIDIN-3-YLCARBAMATE; BENZYL CIS-4-FORMYLCYCLOHEXYLCARBAMATE; BENZYL FORMYL(4-HYDROXYPHENYL)METHYLCARBAMATE; BENZYL N-(5-FORMYLPYRIMIDIN-2-YL)GLYCINATE; BENZYL N-[(5-FORMYL-2-THIENYL)METHYL]CARBAMATE; BML-244; BOC-1-AMINO-1-CYCLOPENTANECARBOXALDEHYDE; BOC-ALA-ALDEHYDE; BOC-L-CYSTEINAL; BOC-L-ISOLEUCINAL; BOC-L-METHIONINAL; BOC-L-VALINAL; BUTYL N-(5-FORMYLPYRIMIDIN-2-YL)GLYCINATE; BUTYRAMIDO-MALONALDEHYDIC ACID; CALPAIN INHIBITOR III; CARBAMIC ACID, (1-FORMYLPROPYL)-, 1,1-DIMETHYLETHYL ESTER; CARBAMIC ACID, (2,2-DIMETHYL-3-OXOPROPYL)-, 1,1-DIMETHYLETHYL ESTER; CARBAMIC ACID, (3-OXOPROPYL)-, ETHYL ESTER; CARBAMIC ACID, (3-OXOPROPYL)-, METHYL ESTER; CARBAMIC ACID, (5-OXOPENTYL)-, PHENYLMETHYL ESTER; CARBAMIC ACID, [(1S)-1-FORMYL-2-(PHENYLMETHOXY)ETHYL]-, 1,1-DIMETHYLETHYL ESTER; CARBAMIC ACID, [(1S)-1-FORMYLPROPYL]-, 1,1-DIMETHYLETHYL ESTER; CARBAMIC ACID, N-(1,1-DIMETHYL-2-OXOETHYL)-, PHENYLMETHYL ESTER; CARBAMIC ACID, N-(3-OXOPROPYL)-, 9H-FLUOREN-9-YLMETHYL ESTER; CARBAMIC ACID, N-(4-OXOBUTYL)-, 1,1-DIMETHYLETHYL ESTER; CARBAMIC ACID, N-(6-OXOHEXYL)-, 1,1-DIMETHYLETHYL ESTER; CARBAMIC ACID, N-(6-OXOHEXYL)-, PHENYLMETHYL ESTER; CARBAMIC ACID, N-(8-OXOOCTYL)-, PHENYLMETHYL ESTER; CHROMOGEN I; CIS-N-(4-FORMYL-CYCLOHEXYL)-ACETAMIDE; DIETHYL-[4-(4-FORMYLIMIDAZOL-2-YL)-PHENYL]-AMINE; ETHOXY-N-(2-FORMYL(3-THIENYL))FORMAMIDE; ETHYL (1S,2S)-2-FORMYL-1-(4-METHOXYPHENYL)-3-METHYLBUTYLCARBAMATE; ETHYL (3-FORMYL-1H-INDOL-2-YL)ACETATE; ETHYL 2-(4-FORMYLPHENYL)IMIDAZOLE-4-CARBOXYLATE; ETHYL 2-(ACETYLAMINO)-2-CYANO-3-METHYL-5-OXOPENTANOATE; ETHYL 2-CYANO-3-(5-FORMYL-1H-PYRROL-2-YL)-2-PROPENOATE; ETHYL 3,5-DIMETHYL-4-(3-OXOPROP-1-ENYL)-1H-PYRROLE-2-CARBOXYLATE; ETHYL 3-FORMYL-1H-INDOLE-2-CARBOXYLATE; ETHYL 3-FORMYL-5-METHOXY-1H-INDOLE-2-CARBOXYLATE; ETHYL 3-FORMYL-5-METHYL-1H-INDOLE-2-CARBOXYLATE; ETHYL 3-FORMYL-7-(METHYLSULFANYL)-1H-INDOLE-2-CARBOXYLATE; ETHYL 3-FORMYL-7-NITRO-1H-INDOLE-2-CARBOXYLATE; ETHYL 4,6-DICHLORO-3-FORMYL-1H-INDOLE-2-CARBOXYLATE; ETHYL 4-FORMYL-1H-PYRROLE-2-CARBOXYLATE; ETHYL 4-FORMYL-2,5-DIMETHYL-1H-PYRROLE-3-CARBOXYLATE; ETHYL 4-FORMYL-3,5-DIMETHYL-1H-PYRROLE-2-CARBOXYLATE; ETHYL 4-FORMYL-5-METHYL-1H-PYRROLE-3-CARBOXYLATE; ETHYL 5-(ACETYLAMINO)-4-FORMYL-3-METHYLTHIOPHENE-2-CARBOXYLATE; ETHYL 5-BROMO-3-FORMYL-1H-INDOLE-2-CARBOXYLATE; ETHYL 5-ETHYL-3-FORMYL-1H-INDOLE-2-CARBOXYLATE; ETHYL 5-FORMYL-1H-PYRROLE-2-CARBOXYLATE; ETHYL 5-FORMYL-2,4-DIMETHYL-1H-PYRROLE-3-CARBOXYLATE; ETHYL 5-FORMYL-2-OXO-2,3-DIHYDRO-1H-IMIDAZOLE-4-CARBOXYLATE; ETHYL 5-FORMYLIMIDAZOLE-4-CARBOXYLATE; ETHYL N-(5-FORMYLPYRIMIDIN-2-YL)GLYCINATE; ETHYL N-[2-(2-FORMYLPIPERIDIN-1-YL)ACETYL]CARBAMATE; ETHYL N-[2-(3-FORMYLPIPERIDIN-1-YL)ACETYL]CARBAMATE; ETHYL N-[2-(4-FORMYLPIPERIDIN-1-YL)ACETYL]CARBAMATE; FMOC-ALA-ALDEHYDE; FMOC-D-ALA-ALDEHYDE;

GLUCOSAMIDE HCL; GUANOSINE PERIODATE OXIDIZED; HEXYL N-(5-FORMYLPYRIMIDIN-2-YL)GLYCINATE; IMIDAZOLE-2-CARBOXALDEHYDE; INDOLE-3,4-DICARBOXALDEHYDE; INDOLE-3,5-DICARBOXALDEHYDE; INDOLE-3,6-DICARBOXALDEHYDE; INDOLE-3,7-DICARBOXALDEHYDE; INDOLE-3-CARBOXALDEHYDE; INDOLE-4-CARBOXALDEHYDE; INDOLE-5-CARBOXALDEHYDE; INDOLE-6-CARBOXALDEHYDE; INDOLE-7-CARBOXALDEHYDE; ISOBUTYL N-(5-FORMYLPYRIMIDIN-2-YL)GLYCINATE; ISOINDOLINE-4-CARBALDEHYDE HCL; METHYL 2-FLUORO-4-FORMYLPHENYLCARBAMATE; METHYL 3-((2R)AZETIDIN-2-YL)-5-FORMYL-4-HYDROXYBENZOATE; METHYL 3-((2S)AZETIDIN-2-YL)-5-FORMYL-4-HYDROXYBENZOATE; METHYL 3-(3-FORMYL-1H-INDOL-5-YL)BENZOATE; METHYL 3-(AZETIDIN-3-YL)-5-FORMYL-4-HYDROXYBENZOATE; METHYL 3-[(1R)-1-(METHYLAMINO)ETHYL]-5-FORMYL-4-HYDROXYBENZOATE; METHYL 3-[(1S)-1-(METHYLAMINO)ETHYL]-5-FORMYL-4-HYDROXYBENZOATE; METHYL 3-[(1S)-2-HYDROXY-1-(METHYLAMINO)ETHYL]-5-FORMYL-4-HYDROXYBENZOATE; METHYL 3-FLUORO-4-FORMYLPHENYLCARBAMATE; METHYL 3-FORMYL-1H-INDOLE-2-CARBOXYLATE; METHYL 3-FORMYL-1H-INDOLE-5-CARBOXYLATE; METHYL 3-FORMYL-4-HYDROXY-5-(PIPERIDIN-3-YL)BENZOATE; METHYL 3-FORMYL-4-HYDROXY-5-(PIPERIDIN-4-YL)BENZOATE; METHYL 3-FORMYL-4-HYDROXY-5-(PYRROLIDIN-3-YL)BENZOATE; METHYL 3-FORMYL-4-METHOXY-1H-INDOLE-2-CARBOXYLATE; METHYL 3-FORMYL-5-METHANESULFONYL-1H-INDOLE-2-CARBOXYLATE; METHYL 3-FORMYL-5-METHOXY-1H-INDOLE-2-CARBOXYLATE; METHYL 3-FORMYL-6-METHOXY-1H-INDOLE-2-CARBOXYLATE; METHYL 3-FORMYLINDOLE-6-CARBOXYLATE; METHYL 3-FORMYLPHENYLCARBAMATE; METHYL 4-(3-FORMYL-1H-INDOL-5-YL)BENZOATE; METHYL 4-FORMYL-1H-PYRROLE-2-CARBOXYLATE; METHYL 4-FORMYL-2,5-DIMETHYL-1H-PYRROLE-3-CARBOXYLATE; METHYL 4-FORMYL-3,5-DIMETHYL-1H-PYRROLE-2-CARBOXYLATE; METHYL 4-FORMYLPHENYLCARBAMATE; METHYL 5-(2-FORMYL-1H-PYRROL-1-YL)-4H-1,2,4-TRIAZOLE-3-CARBOXYLATE; METHYL 5-FORMYL-2,4-DIMETHYL-1H-PYRROLE-3-CARBOXYLATE; METHYL 5-FORMYLPYRROLE-3-CARBOXYLATE; METHYL N-(5-FORMYLPYRIMIDIN-2-YL)GLYCINATE; METHYL N-[2-(2-FORMYLPIPERIDIN-1-YL)ACETYL]CARBAMATE; METHYL N-[2-(3-FORMYLPIPERIDIN-1-YL)ACETYL]CARBAMATE; METHYL N-[2-(4-FORMYLPIPERIDIN-1-YL)ACETYL]CARBAMATE; METHYL3-FORMYL-4,5-DIMETHYL-1H-PYRROLE-2-CARBOXYLATE; N-((5-FORMYLFURAN-2-YL)METHYL)ACETAMIDE; N-(1,1-DIMETHYLETHYL)-N'-(3-FORMYL-1H-INDAZOL-4-YL)-UREA; N-(1,1-DIMETHYLETHYL)-N'-(3-FORMYL-1H-INDAZOL-5-YL)-UREA; N-(1,1-DIMETHYLETHYL)-N'-(3-FORMYL-1H-INDAZOL-7-YL)-UREA; N-(11-OXO-UNDECYL)-ACETAMIDE; N-(1-CYCLOPROPYLETHYL)-2-(4-FORMYL-2,6-DIMETHYLPHENOXY)ACETAMIDE; N-(1-METHYL-3-OXOPROPYL)-1-BENZOTHIOPHENE-2-CARBOXAMIDE; N-(1-METHYL-3-OXOPROPYL)BENZAMIDE; N-(2-(DIETHYLAMINO)ETHYL)-5-FORMYL-2,4-DIMETHYL-1H-PYRROLE-3-CARBOXAMIDE; N-(2-(FORMYLMETHYL)BENZYL)ACETAMIDE; N-(2-(FORMYLMETHYL)PHENYOACETAMIDE; N-(2,3-DIMETHYLPHENYL)-2-(2-FORMYLPHENOXY)ACETAMIDE; N-(2,3-DIMETHYLPHENYL)-2-(3-FORMYLPHENOXY)ACETAMIDE; N-(2,3-DIMETHYLPHENYL)-2-(4-FORMYLPHENOXY)ACETAMIDE; N-(2,4-DIMETHYLPHENYL)-2-(2-FORMYLPHENOXY)ACETAMIDE; N-(2,4-DIMETHYLPHENYL)-2-(3-FORMYLPHENOXY)ACETAMIDE; N-(2,4-DIMETHYLPHENYL)-2-(4-FORMYLPHENOXY)ACETAMIDE; N-(2,5-DIMETHYLPHENYL)-2-(2-FORMYLPHENOXY)ACETAMIDE; N-(2,5-DIMETHYLPHENYL)-2-(3-FORMYLPHENOXY)ACETAMIDE; N-(2,5-DIMETHYLPHENYL)-2-(4-FORMYLPHENOXY)ACETAMIDE; N-(2,6-DICHLORO-4-FORMYLPHENYL)ACETAMIDE; N-(2,6-DIMETHYLPHENYL)-2-(3-FORMYLPHENOXY)ACETAMIDE; N-(2-ACETAMIDOETHYL)-2-(2-FORMYLPIPERIDIN-1-YL)ACETAMIDE; N-(2-ACETAMIDOETHYL)-2-(3-FORMYLPIPERIDIN-1-YL)ACETAMIDE; N-(2-ACETAMIDOETHYL)-2-(4-FORMYLPIPERIDIN-1-YL)ACETAMIDE; N-(2-BROMO-5-FORMYLPYRIDIN-3-YL)PIVALAMIDE; N-(2-CHLORO-3-FORMYLPYRIDIN-4-YL)PIVALAMIDE; N-(2-CHLORO-6-FORMYLPYRIDIN-3-YL)PIVALAMIDE; N-(2-CHLOROPHENYL)-2-(2-FORMYLPHENOXY)ACETAMIDE; N-(2-CHLOROPHENYL)-2-(2-FORMYLPIPERIDIN-1-YL)ACETAMIDE; N-(2-CHLOROPHENYL)-2-(3-FORMYLPHENOXY)ACETAMIDE; N-(2-CHLOROPHENYL)-2-(3-FORMYLPIPERIDIN-1-YL)ACETAMIDE; N-(2-CHLOROPHENYL)-2-(4-FORMYLPHENOXY)ACETAMIDE; N-(2-CHLOROPHENYL)-2-(4-FORMYLPIPERIDIN-1-YL)ACETAMIDE; N-(2-CYANO-5-FORMYLPYRIDIN-3-YL)PIVALAMIDE; N-(2-CYANOETHYL)-2-(2-FORMYL-4-METHOXYPHENOXY)ACETAMIDE; N-(2-CYANOETHYL)-2-(2-FORMYL-5-METHOXYPHENOXY)ACETAMIDE; N-(2-CYANOETHYL)-2-(2-FORMYL-6-METHOXYPHENOXY)ACETAMIDE; N-(2-CYANOETHYL)-2-(2-FORMYLPHENOXY)ACETAMIDE; N-(2-CYANOETHYL)-2-(2-FORMYLPIPERIDIN-1-YL)ACETAMIDE; N-(2-CYANOETHYL)-2-(3-FORMYLPHENOXY)ACETAMIDE; N-(2-CYANOETHYL)-2-(3-FORMYLPIPERIDIN-1-YL)ACETAMIDE; N-(2-CYANOETHYL)-2-(4-FORMYL-2,6-DIMETHYLPHENOXY)ACETAMIDE; N-(2-CYANOETHYL)-2-(4-FORMYL-2-METHOXYPHENOXY)ACETAMIDE; N-(2-CYANOETHYL)-2-(4-FORMYL-3,5-DIMETHYL-1H-PYRAZOL-1-YL)ACETAMIDE; N-(2-CYANOETHYL)-2-(4-FORMYLPHENOXY)ACETAMIDE; N-(2-CYANOETHYL)-2-(4-FORMYLPIPERIDIN-1-YL)ACETAMIDE; N-(2-CYANOETHYL)-2-(5-FORMYL-2-METHOXYPHENOXY)ACETAMIDE; N-(2-ETHYLPHENYL)-2-(2-FORMYLPHENOXY)ACETAMIDE; N-(2-ETHYLPHENYL)-2-(3-FORMYLPHENOXY)ACETAMIDE; N-(2-ETHYLPHENYL)-2-(4-FORMYLPHENOXY)ACETAMIDE; N-(2-FLUOROPHENYL)-2-(2-FORMYL-1H-IMIDAZOL-1-YL)ACETAMIDE; N-(2-FLUOROPHENYL)-2-(2-FORMYLPIPERIDIN-1-YL)ACETAMIDE; N-(2-FLUOROPHENYL)-2-(3-FORMYLPIPERIDIN-1-YL)ACETAMIDE; N-(2-FLUOROPHENYL)-2-(4-FORMYLPIPERIDIN-1-YL)

ACETAMIDE; N'-(2-FORMYL-1H-INDOL-3-YL)-N,N-DIMETHYLIMIDOFORMAMIDE; N-(2-FORMYL-3-METHOXYPHENYL)-2,2-DIMETHYLPROPANAMIDE; N-(2-FORMYL-3-METHOXYPYRIDIN-4-YL)PIVALAMIDE; N-(2-FORMYL-4,5-DIMETHOXY-PHENYL)-ACETAMIDE; N-(2-FORMYL-4-METHOXY-PHENYL)-ACETAMIDE; N-(2-FORMYL-4-METHYL-PHENYL)-ACETAMIDE; N-(2-FORMYL-4-NITROPHENYL)ACETAMIDE; N-(2-FORMYL-5,8-DIOXO-5,8-DIHYDROQUINOLIN-7-YL)ACETAMIDE; N'-(2-FORMYL-5-METHOXY-1H-INDOL-3-YL)-N,N-DIMETHYLIMIDOFORMAMIDE; N-(2-FORMYL-5-METHOXY-PHENYL)-ACETAMIDE; N'-(2-FORMYL-5-METHYL-1H-INDOL-3-YL)-N,N-DIMETHYLIMIDOFORMAMIDE; N'-(2-FORMYL-5-METHYL-1H-INDOL-3-YL)-N,N-DIMETHYLIMIDOFORMAMIDE HYDROCHLORIDE; N-(2-FORMYL-5-METHYL-PHENYL)-ACETAMIDE; N'-(2-FORMYL-6-METHYL-1H-INDOL-3-YL)-N,N-DIMETHYLIMIDOFORMAMIDE; N-(2-FORMYL-6-METHYL-PHENYL)-ACETAMIDE; N-(2-FORMYL-FURO[3,2-B]PYRIDIN-7-YL)PIVALAMIDE; N-(2-FORMYLPHENYL)-3-NITROBENZAMIDE; N-(2-FORMYL-PHENYL)-ACETAMIDE; N-(2-FORMYLPHENYL)CYCLOPROPANECARBOXAMIDE; N-(2-FORMYLPHENYL)FORMAMIDE; N-(2-FORMYLQUINOLIN-6-YL)ACETAMIDE; N-(2-METHOXYETHYL)-2-[METHYL(2-OXOETHYL)AMINO]ACETAMIDE; N-(2-METHOXYETHYL)-2-[METHYL(3-OXOPROPYL)AMINO]ACETAMIDE; N-(2-METHYL-3-OXO-PROPYL)-ACETAMIDE; N-(2-OXO-1-THIOPHEN-3-YL-ETHYL)-ACETAMIDE; N-(3,4-DIFLUORO-2-FORMYLPHENYL)PIVALAMIDE; N-(3,4-DIMETHYLPHENYL)-2-(2-FORMYLPHENOXY)ACETAMIDE; N-(3,4-DIMETHYLPHENYL)-2-(3-FORMYLPHENOXY)ACETAMIDE; N-(3,4-DIMETHYLPHENYL)-2-(4-FORMYLPHENOXY)ACETAMIDE; N-(3,5-DIMETHYL-1H-PYRAZOL-4-YL)-2-(2-FORMYLPIPERIDIN-1-YL)ACETAMIDE; N-(3,5-DIMETHYL-1H-PYRAZOL-4-YL)-2-(3-FORMYLPIPERIDIN-1-YL)ACETAMIDE; N-(3,5-DIMETHYL-1H-PYRAZOL-4-YL)-2-(4-FORMYLPIPERIDIN-1-YL)ACETAMIDE; N-(3,5-DIMETHYLPHENYL)-2-(2-FORMYLPHENOXY)ACETAMIDE; N-(3,5-DIMETHYLPHENYL)-2-(3-FORMYLPHENOXY)ACETAMIDE; N-(3-CHLOROPHENYL)-2-(2-FORMYL-1H-IMIDAZOL-1-YL)ACETAMIDE; N-(3-CHLOROPHENYL)-2-(2-FORMYLPIPERIDIN-1-YL)ACETAMIDE; N-(3-CHLOROPHENYL)-2-(3-FORMYLPHENOXY)ACETAMIDE; N-(3-CHLOROPHENYL)-2-(3-FORMYLPIPERIDIN-1-YL)ACETAMIDE; N-(3-CHLOROPHENYL)-2-(4-FORMYLPHENOXY)ACETAMIDE; N-(3-CHLOROPHENYL)-2-(4-FORMYLPIPERIDIN-1-YL)ACETAMIDE; N-(3-CYANOTHIOPHEN-2-YL)-2-(2-FORMYLPIPERIDIN-1-YL)ACETAMIDE; N-(3-CYANOTHIOPHEN-2-YL)-2-(3-FORMYLPIPERIDIN-1-YL)ACETAMIDE; N-(3-CYANOTHIOPHEN-2-YL)-2-(4-FORMYLPIPERIDIN-1-YL)ACETAMIDE; N-(3-DIMETHYLAMINO-PROPYL)-4-FORMYL-BENZAMIDE; N'-(3-ETHYL-5-FORMYL-2,6-DIOXO-1,2,3,6-TETRAHYDRO-PYRIMIDIN-4-YL)-N,N-DIMETHYL-FORMAMIDINE; N-(3-FLUOROPHENYL)-2-(2-FORMYL-1H-IMIDAZOL-1-YL)ACETAMIDE; N-(3-FLUOROPHENYL)-2-(2-FORMYLPIPERIDIN-1-YL)ACETAMIDE; N-(3-FLUOROPHENYL)-2-(3-FORMYLPIPERIDIN-1-YL)ACETAMIDE; N-(3-FLUOROPHENYL)-2-(4-FORMYLPIPERIDIN-1-YL)ACETAMIDE; N-(3'-FORMYL[1,1'-BIPHENYL]-3-YL)ACETAMIDE; N-(3'-FORMYL[1,1'-BIPHENYL]-4-YL)ACETAMIDE; N-(3-FORMYL-2-METHYL-PHENYL)-ACETAMIDE; N-(3-FORMYL-2-PYRIDINYL)-2,2-DIMETHYLPROPANAMIDE; N-(3-FORMYL-4-METHYL-PHENYL)-ACETAMIDE; N-(3-FORMYL-4-PYRIDINYL)-2,2-DIMETHYLPROPANAMIDE; N-(3-FORMYL-5-(TRIFLUOROMETHYL)PYRIDIN-2-YL)PIVALAMIDE; N-(3-FORMYL-5-METHYLPYRIDIN-2-YL)PIVALAMIDE; N-(3-FORMYL-BENZYL)-ACETAMIDE; N-(3-FORMYLPHENYL)-4-METHOXYBENZAMIDE; N-(3-FORMYL-PHENYL)-4-METHYL-BENZAMIDE; N-(3-FORMYL-PYRAZIN-2-YL)-ACETAMIDE; N-(3-FORMYL-PYRIDIN-2-YL)-ACETAMIDE; N-(3-FORMYL-PYRIDIN-4-YL)-ACETAMIDE; N-(3-FORMYLQUINOLIN-7-YL)ACETAMIDE; N-(3-OXO-1-PHENYLPROPYL)ACETAMIDE; N-(4-((5-FORMYL-2-METHOXYBENZYL)OXY)PHENYL)ACETAMIDE; N-(4-(2-OXOACETYL)PHENYL)ACETAMIDE; N-(4-[(2-FORMYLPIPERIDIN-1-YL)METHYL]-1,3-THIAZOL-2-YL)ACETAMIDE; N-(4-[(2-OXOETHYL)SULFANYL]PHENYL)ACETAMIDE; N-(4-[(3-FORMYLPIPERIDIN-1-YL)METHYL]-1,3-THIAZOL-2-YL)ACETAMIDE; N-(4-[(3-OXOPROPYL)SULFANYL]PHENYL)ACETAMIDE; N-(4-[(4-FORMYLPIPERIDIN-1-YL)METHYL]-1,3-THIAZOL-2-YL)ACETAMIDE; N-(4-CHLOROPHENYL)-2-(2-FORMYL-1H-IMIDAZOL-1-YL)ACETAMIDE; N-(4-CHLOROPHENYL)-2-(2-FORMYLPHENOXY)ACETAMIDE; N-(4-CHLOROPHENYL)-2-(2-FORMYLPIPERIDIN-1-YL)ACETAMIDE; N-(4-CHLOROPHENYL)-2-(3-FORMYLPHENOXY)ACETAMIDE; N-(4-CHLOROPHENYL)-2-(3-FORMYLPIPERIDIN-1-YL)ACETAMIDE; N-(4-CHLOROPHENYL)-2-(4-FORMYLPHENOXY)ACETAMIDE; N-(4-CHLOROPHENYL)-2-(4-FORMYLPIPERIDIN-1-YL)ACETAMIDE; N-(4-ETHOXYPHENYL)-2-(2-FORMYLPHENOXY)ACETAMIDE; N-(4-ETHOXYPHENYL)-2-(3-FORMYLPHENOXY)ACETAMIDE; N-(4-ETHOXYPHENYL)-2-(4-FORMYLPHENOXY)ACETAMIDE; N-(4-ETHYLPHENYL)-2-(2-FORMYLPHENOXY)ACETAMIDE; N-(4-ETHYLPHENYL)-2-(3-FORMYLPHENOXY)ACETAMIDE; N-(4-ETHYLPHENYL)-2-(4-FORMYLPHENOXY)ACETAMIDE; N-(4-FLUOROPHENYL)-2-(2-FORMYLPHENOXY)ACETAMIDE; N-(4-FLUOROPHENYL)-2-(2-FORMYLPIPERIDIN-1-YL)ACETAMIDE; N-(4-FLUORO-PHENYL)-2-(3-FORMYL-INDOL-1-YL)-ACETAMIDE; N-(4-FLUOROPHENYL)-2-(3-FORMYLPHENOXY)ACETAMIDE; N-(4-FLUOROPHENYL)-2-(3-FORMYLPIPERIDIN-1-YL)ACETAMIDE; N-(4-FLUOROPHENYL)-2-(4-FORMYLPHENOXY)ACETAMIDE; N-(4-FLUOROPHENYL)-2-(4-FORMYLPIPERIDIN-1-YL)ACETAMIDE; N-(4'-FORMYL[1,1-BIPHENYL]-2-YL)ACETAMIDE; N-(4'-FORMYL[1,1-BIPHENYL]-3-YL)ACETAMIDE; N-(4'-FORMYL[1,1'-BIPHENYL]-4-YL)ACETAMIDE; N-(4-FORMYL-1,3-THIAZOL-2-YL)ACETAMIDE; N-(4-FORMYL-1H-PYRAZOL-3-YL)-ACETAMIDE; N-(4-FORMYL-2-HYDROXY-PHENYL)-ACETAMIDE; N-(4-FORMYL-2-METHOXY-PHENYL)-ACETAMIDE; N-(4-FORMYL-2-METHOXYPYRIDIN-3-YL)PIVALAMIDE; N-(4-FORMYL-2-METHYL-PHENYL)-ACETAMIDE; N-(4-FORMYL-2-

TRIFLUOROMETHOXY-PHENYL)-ACETAMIDE; N-(4-FORMYL-3-METHYLPHENYL)ACETAMIDE; N-(4-FORMYL-3-NITRO-PHENYL)-ACETAMIDE; N-(4-FORMYL-PYRIDIN-2-YL)-ACETAMIDE; N-(4-FORMYL-PYRIDIN-3-YL)-2,2-DIMETHYL-PROPIONAMIDE; N-(4-FORMYLPYRIDIN-3-YL)ACETAMIDE; N'-(5-[(5-FORMYL-1H-PYRROL-3-YL)CARBONYL]-1,3-THIAZOL-2-YL)-N,N-DIMETHYLIMINOFORMAMIDE; N-(5-BROMO-2-FORMYL-QUINOLIN-6-YL)-ACETAMIDE; N-(5-BROMO-2-FORMYL-QUINOLIN-8-YL)-ACETAMIDE; N-(5-BROMO-4-FORMYL-1,3-THIAZOL-2-YL)ACETAMIDE; N'-(5-CHLORO-2-FORMYL-1H-INDOL-3-YL)-N,N-DIMETHYLIMIDOFORMAMIDE; N-(5-CHLORO-3-FORMYLPYRIDIN-2-YL)PIVALAMIDE; N-(5-FLUORO-3-FORMYLPYRIDIN-2-YL)PIVALAMIDE; N-(5-FORMYL-1H-IMIDAZOL-2-YL)-ACETAMIDE; N-(5-FORMYL-2H-[1,2,4]TRIAZOL-3-YL)-ACETAMIDE; N-(5-FORMYL-2-HYDROXYPHENYL)ACETAMIDE; N-(5-FORMYL-2-METHOXY-PHENYL)-ACETAMIDE; N-(5-FORMYL-2-METHYLPHENYL)ACETAMIDE; N-(5-FORMYL-2-THIENYL)ACETAMIDE; N-(5-FORMYL-FURAN-2-YLMETHYL)-BENZAMIDE; N-(5-FORMYL-PYRIDIN-2-YL)-ACETAMIDE; N-(5-FORMYL-PYRIDIN-3-YL)-ACETAMIDE; N-(5-FORMYLPYRIMIDIN-2-YL)GLYCINE; N-(5-FORMYL-THIAZOL-2-YL)-ACETAMIDE; N-(5-OXO-PENTYL)-ACETAMIDE; N-(6-CHLORO-3-FORMYL-PYRIDIN-2-YL)-2,2-DIMETHYL-PROPIONAMIDE; N-(6-FLUORO-3-FORMYLPYRIDIN-2-YL)PIVALAMIDE; N-(6-FORMYL-BENZO[1,3]DIOXOL-5-YL)-ACETAMIDE; N-(6-FORMYL-PYRIDIN-2-YL)-ACETAMIDE; N-(6-FORMYLPYRIDIN-2-YL)PIVALAMIDE; N-(7-FORMYL-[1,8]NAPHTHYRIDIN-2-YL)-ACETAMIDE; N-(BUTAN-2-YL)-2-(2-FORMYL-4-METHOXYPHENOXY)ACETAMIDE; N-(BUTAN-2-YL)-2-(2-FORMYL-5-METHOXYPHENOXY)ACETAMIDE; N-(BUTAN-2-YL)-2-(2-FORMYL-6-METHOXYPHENOXY)ACETAMIDE; N-(BUTAN-2-YL)-2-(2-FORMYLPHENOXY)ACETAMIDE; N-(BUTAN-2-YL)-2-(2-FORMYLPHENOXY)PROPANAMIDE; N-(BUTAN-2-YL)-2-(2-FORMYLPIPERIDIN-1-YL)ACETAMIDE; N-(BUTAN-2-YL)-2-(2-FORMYLPIPERIDIN-1-YL)PROPANAMIDE; N-(BUTAN-2-YL)-2-(3-CHLORO-2-FORMYLPHENOXY)ACETAMIDE; N-(BUTAN-2-YL)-2-(3-CHLORO-2-FORMYLPHENOXY)PROPANAMIDE; N-(BUTAN-2-YL)-2-(3-FORMYLPHENOXY)ACETAMIDE; N-(BUTAN-2-YL)-2-(3-FORMYLPHENOXY)PROPANAMIDE; N-(BUTAN-2-YL)-2-(3-FORMYLPIPERIDIN-1-YL)ACETAMIDE; N-(BUTAN-2-YL)-2-(3-FORMYLPIPERIDIN-1-YL)PROPANAMIDE; N-(BUTAN-2-YL)-2-(4-CHLORO-2-FORMYLPHENOXY)ACETAMIDE; N-(BUTAN-2-YL)-2-(4-CHLORO-2-FORMYLPHENOXY)PROPANAMIDE; N-(BUTAN-2-YL)-2-(4-FORMYL-2,6-DIMETHYLPHENOXY)ACETAMIDE; N-(BUTAN-2-YL)-2-(4-FORMYL-2-METHOXYPHENOXY)ACETAMIDE; N-(BUTAN-2-YL)-2-(4-FORMYL-3,5-DIMETHYL-1H-PYRAZOL-1-YL)ACETAMIDE; N-(BUTAN-2-YL)-2-(4-FORMYLPHENOXY)ACETAMIDE; N-(BUTAN-2-YL)-2-(4-FORMYLPHENOXY)PROPANAMIDE; N-(BUTAN-2-YL)-2-(4-FORMYLPIPERIDIN-1-YL)ACETAMIDE; N-(BUTAN-2-YL)-2-(4-FORMYLPIPERIDIN-1-YL)PROPANAMIDE; N-(BUTAN-2-YL)-2-(5-FORMYL-2-METHOXYPHENOXY)ACETAMIDE; N-(BUTAN-2-YL)-3-(3-FORMYL-2,5-DIMETHYL-1H-PYRROL-1-YL)PROPANAMIDE; N-(CYANOMETHYL)-2-(2,4-DICHLORO-6-FORMYLPHENOXY)ACETAMIDE; N-(CYANOMETHYL)-2-(2-ETHOXY-4-FORMYLPHENOXY)ACETAMIDE; N-(CYANOMETHYL)-2-(2-ETHOXY-6-FORMYLPHENOXY)ACETAMIDE; N-(CYANOMETHYL)-2-(2-FORMYL-4-METHOXYPHENOXY)ACETAMIDE; N-(CYANOMETHYL)-2-(2-FORMYL-4-NITROPHENOXY)ACETAMIDE; N-(CYANOMETHYL)-2-(2-FORMYL-5-METHOXYPHENOXY)ACETAMIDE; N-(CYANOMETHYL)-2-(2-FORMYL-6-METHOXYPHENOXY)ACETAMIDE; N-(CYANOMETHYL)-2-(2-FORMYLPHENOXY)ACETAMIDE; N-(CYANOMETHYL)-2-(2-FORMYLPIPERIDIN-1-YL)ACETAMIDE; N-(CYANOMETHYL)-2-(3-FORMYLPHENOXY)ACETAMIDE; N-(CYANOMETHYL)-2-(3-FORMYLPIPERIDIN-1-YL)ACETAMIDE; N-(CYANOMETHYL)-2-(4-FORMYL-2,6-DIMETHYLPHENOXY)ACETAMIDE; N-(CYANOMETHYL)-2-(4-FORMYL-2-METHOXYPHENOXY)ACETAMIDE; N-(CYANOMETHYL)-2-(4-FORMYL-2-NITROPHENOXY)ACETAMIDE; N-(CYANOMETHYL)-2-(4-FORMYL-3,5-DIMETHYL-1H-PYRAZOL-1-YL)ACETAMIDE; N-(CYANOMETHYL)-2-(4-FORMYLPHENOXY)ACETAMIDE; N-(CYANOMETHYL)-2-(4-FORMYLPIPERIDIN-1-YL)ACETAMIDE; N-(CYANOMETHYL)-2-(5-FORMYL-2-METHOXYPHENOXY)ACETAMIDE; N-(CYANOMETHYL)-2-(5-FORMYL-2-NITROPHENOXY)ACETAMIDE; N-(CYANOMETHYL)-2-[(6-FORMYL-2H-1,3-BENZODIOXOL-5-YL)OXY]ACETAMIDE; N-(CYCLOPROPYLMETHYL)-2-(2-FORMYL-4-METHOXYPHENOXY)ACETAMIDE; N-(CYCLOPROPYLMETHYL)-2-(2-FORMYL-5-METHOXYPHENOXY)ACETAMIDE; N-(CYCLOPROPYLMETHYL)-2-(2-FORMYL-6-METHOXYPHENOXY)ACETAMIDE; N-(CYCLOPROPYLMETHYL)-2-(2-FORMYLPHENOXY)ACETAMIDE; N-(CYCLOPROPYLMETHYL)-2-(2-FORMYLPIPERIDIN-1-YL)ACETAMIDE; N-(CYCLOPROPYLMETHYL)-2-(3-FORMYLPHENOXY)ACETAMIDE; N-(CYCLOPROPYLMETHYL)-2-(3-FORMYLPIPERIDIN-1-YL)ACETAMIDE; N-(CYCLOPROPYLMETHYL)-2-(4-FORMYL-2,6-DIMETHYLPHENOXY)ACETAMIDE; N-(CYCLOPROPYLMETHYL)-2-(4-FORMYL-2-METHOXYPHENOXY)ACETAMIDE; N-(CYCLOPROPYLMETHYL)-2-(4-FORMYL-3,5-DIMETHYL-1H-PYRAZOL-1-YL)ACETAMIDE; N-(CYCLOPROPYLMETHYL)-2-(4-FORMYLPHENOXY)ACETAMIDE; N-(CYCLOPROPYLMETHYL)-2-(4-FORMYLPIPERIDIN-1-YL)ACETAMIDE; N-(CYCLOPROPYLMETHYL)-2-(5-FORMYL-2-METHOXYPHENOXY)ACETAMIDE; N-(TERT-BUTYL)-2-(2-ETHOXY-4-FORMYLPHENOXY)ACETAMIDE; N-(TERT-BUTYL)-2-(4-FORMYL-2,6-DIMETHYLPHENOXY)ACETAMIDE; N-(TERT-BUTYL)-2-(4-FORMYL-2-METHOXYPHENOXY)ACETAMIDE; N-(TERT-BUTYL)-2-(4-FORMYLPHENOXY)ACETAMIDE; N-[2-(2-FORMYLPHENOXY)PHENYL]ACETAMIDE; N-[2-(2-FORMYLPIPERIDIN-1-YL)ETHYL]ACETAMIDE; N-[2-(2-OXOETHOXY)PHENYL]ACETAMIDE; N-[2-(3-FORMYL-2-HYDROXYPHENYL)PHENYL]-2,2-DIMETHYLPROPANAMIDE; N-[2-(3-FORMYL-4-HYDROXYPHENYL)PHENYL]-2,2-DIMETHYLPROPANAMIDE; N-[2-(3-FORMYLPIPERIDIN-1-YL)ETHYL]ACETAMIDE; N-[2-(3-OXOPROPOXY)PHENYL]ACETAMIDE; N-[2-(4-FORMYLPHENOXY)PHENYL]ACETAMIDE; N-[2-(4-

FORMYLPIPERIDIN-1-YL)ETHYL]ACETAMIDE; N-[2-(4-FORMYLPYRIDIN-3-YL)PHENYL]-2,2-DIMETHYL-PROPANAMIDE; N-[2-(5-FORMYL-2-FURYL)PHENYL]ACETAMIDE; N-[2-(5-FORMYL-2-HYDROXYPHENYL)PHENYL]-2,2-DIMETHYLPROPANAMIDE; N-[2-(5-FORMYLPYRIDIN-3-YL)PHENYL]-2,2-DIMETHYLPROPANAMIDE; N-[2-OXO-1-(2-OXO-1,2-DIHYDRO-QUINOLIN-4-YLMETHYL)-ETHYL]-ACETAMIDE; N-[3-(2-OXOETHOXY)PHENYL]ACETAMIDE; N-[3-(3-OXOPROPOXY)PHENYL]ACETAMIDE; N-[3-(5-FORMYL-2-FURYL)PHENYL]ACETAMIDE; N-[3-(BENZYLOXY)-4-FORMYLPHENYL]ACETAMIDE; N-[4-(2-FORMYLPHENOXY)PHENYL]ACETAMIDE; N-[4-(2-OXOETHOXY)PHENYL]ACETAMIDE; N-[4-(2-OXO-ETHYL)-PHENYL]-ACETAMIDE; N-[4-(2-OXO-ETHYL)-THIAZOL-2-YL]-ACETAMIDE; N-[4-(2-OXO-ETHYL)-THIAZOL-2-YL]-FORMAMIDE; N-[4-(3-FORMYL-2,5-DIMETHYL-1H-PYRROL-1-YL)PHENYL]ACETAMIDE; N-[4-(3-OXOPROPOXY)PHENYL]ACETAMIDE; N-[4-(3-OXO-PROPYL)-PHENYL]-ACETAMIDE; N-[4-(5-FORMYL-2-FURYL)PHENYL]ACETAMIDE; N-ACETYL-D-GALACTOSAMINE; N-ACETYL-D-GLUCOSAMINE; N-ACETYL-D-GLUCOSAMINE-2-3H; N-ACETYL-D-MANNOSAMINE; N-ACETYL-D-MANNOSAMINE MONOHYDRATE; N-ACETYLMURAMIC ACID; N-BENZYL-2-(2-FORMYL-6-METHOXYPHENOXY)ACETAMIDE; N-BENZYL-2-(2-FORMYLPHENOXY)ACETAMIDE; N-BENZYL-2-(2-FORMYLPIPERIDIN-1-YL)ACETAMIDE; N-BENZYL-2-(3-FORMYLPHENOXY)ACETAMIDE; N-BENZYL-2-(3-FORMYLPIPERIDIN-1-YL)ACETAMIDE; N-BENZYL-2-(4-FORMYL-2-METHOXYPHENOXY)ACETAMIDE; N-BENZYL-2-(4-FORMYLPIPERIDIN-1-YL)ACETAMIDE; N-BENZYLAMINOACETALDEHYDE; N-BOC-D-PHENYLALANINAL; N-BOC-L-PHENYLALANINAL; N-BUTYL-2-(2-CHLORO-4-FORMYLPHENOXY)ACETAMIDE; N-BUTYL-2-(2-CHLORO-4-FORMYLPHENOXY)PROPANAMIDE; N-BUTYL-2-(2-FORMYL-4-METHOXYPHENOXY)ACETAMIDE; N-BUTYL-2-(2-FORMYL-5-METHOXYPHENOXY)ACETAMIDE; N-BUTYL-2-(2-FORMYL-6-METHOXYPHENOXY)ACETAMIDE; N-BUTYL-2-(2-FORMYLPHENOXY)ACETAMIDE; N-BUTYL-2-(2-FORMYLPHENOXY)PROPANAMIDE; N-BUTYL-2-(2-FORMYLPIPERIDIN-1-YL)ACETAMIDE; N-BUTYL-2-(2-FORMYLPIPERIDIN-1-YL)PROPANAMIDE; N-BUTYL-2-(3-CHLORO-2-FORMYLPHENOXY)ACETAMIDE; N-BUTYL-2-(3-CHLORO-2-FORMYLPHENOXY)PROPANAMIDE; N-BUTYL-2-(3-FORMYLPHENOXY)ACETAMIDE; N-BUTYL-2-(3-FORMYLPHENOXY)PROPANAMIDE; N-BUTYL-2-(3-FORMYLPIPERIDIN-1-YL)ACETAMIDE; N-BUTYL-2-(3-FORMYLPIPERIDIN-1-YL)PROPANAMIDE; N-BUTYL-2-(4-CHLORO-2-FORMYLPHENOXY)ACETAMIDE; N-BUTYL-2-(4-CHLORO-2-FORMYLPHENOXY)PROPANAMIDE; N-BUTYL-2-(4-FORMYL-2,6-DIMETHYLPHENOXY)ACETAMIDE; N-BUTYL-2-(4-FORMYL-2-METHOXYPHENOXY)ACETAMIDE; N-BUTYL-2-(4-FORMYL-3,5-DIMETHYL-1H-PYRAZOL-1-YL)ACETAMIDE; N-BUTYL-2-(4-FORMYLPHENOXY)ACETAMIDE; N-BUTYL-2-(4-FORMYLPHENOXY)PROPANAMIDE; N-BUTYL-2-(4-FORMYLPIPERIDIN-1-YL)ACETAMIDE; N-BUTYL-2-(4-FORMYLPIPERIDIN-1-YL)PROPANAMIDE; N-BUTYL-2-(5-FORMYL-2-METHOXYPHENOXY)ACETAMIDE; N-CYCLOHEPTYL-2-(2-FORMYLPIPERIDIN-1-YL)ACETAMIDE; N-CYCLOHEPTYL-2-(3-FORMYLPIPERIDIN-1-YL)ACETAMIDE; N-CYCLOHEPTYL-2-(4-FORMYLPHENOXY)ACETAMIDE; N-CYCLOHEPTYL-2-(4-FORMYLPIPERIDIN-1-YL)ACETAMIDE; N-CYCLOHEXYL-2-(2-FORMYL-1H-IMIDAZOL-1-YL)ACETAMIDE; N-CYCLOHEXYL-2-(2-FORMYLPHENOXY)ACETAMIDE; N-CYCLOHEXYL-2-(2-FORMYLPIPERIDIN-1-YL)ACETAMIDE; N-CYCLOHEXYL-2-(3-FORMYL-2-METHYL-INDOL-1-YL)-ACETAMIDE; N-CYCLOHEXYL-2-(3-FORMYL-INDOL-1-YL)-ACETAMIDE; N-CYCLOHEXYL-2-(3-FORMYLPHENOXY)ACETAMIDE; N-CYCLOHEXYL-2-(3-FORMYLPIPERIDIN-1-YL)ACETAMIDE; N-CYCLOHEXYL-2-(4-FORMYL-2-METHOXYPHENOXY)ACETAMIDE; N-CYCLOHEXYL-2-(4-FORMYL-3,5-DIMETHYL-1H-PYRAZOL-1-YL)ACETAMIDE; N-CYCLOHEXYL-2-(4-FORMYLPHENOXY)ACETAMIDE; N-CYCLOHEXYL-2-(4-FORMYLPIPERIDIN-1-YL)ACETAMIDE; N-CYCLOHEXYL-3-(2-FORMYLPIPERIDIN-1-YL)PROPANAMIDE; N-CYCLOHEXYL-3-(3-FORMYLPIPERIDIN-1-YL)PROPANAMIDE; N-CYCLOHEXYL-3-(4-FORMYLPIPERIDIN-1-YL)PROPANAMIDE; N-CYCLOPENTYL-2-(2-FORMYL-4-METHOXYPHENOXY)ACETAMIDE; N-CYCLOPENTYL-2-(2-FORMYLPHENOXY)ACETAMIDE; N-CYCLOPENTYL-2-(2-FORMYLPHENOXY)PROPANAMIDE; N-CYCLOPENTYL-2-(2-FORMYLPIPERIDIN-1-YL)ACETAMIDE; N-CYCLOPENTYL-2-(2-FORMYLPIPERIDIN-1-YL)PROPANAMIDE; N-CYCLOPENTYL-2-(3-FORMYL-2-METHYL-INDOL-1-YL)-ACETAMIDE; N-CYCLOPENTYL-2-(3-FORMYL-INDOL-1-YL)-ACETAMIDE; N-CYCLOPENTYL-2-(3-FORMYLPHENOXY)ACETAMIDE; N-CYCLOPENTYL-2-(3-FORMYLPHENOXY)PROPANAMIDE; N-CYCLOPENTYL-2-(3-FORMYLPIPERIDIN-1-YL)ACETAMIDE; N-CYCLOPENTYL-2-(3-FORMYLPIPERIDIN-1-YL)PROPANAMIDE; N-CYCLOPENTYL-2-(4-FORMYL-2,6-DIMETHYLPHENOXY)ACETAMIDE; N-CYCLOPENTYL-2-(4-FORMYL-2-METHOXYPHENOXY)ACETAMIDE; N-CYCLOPENTYL-2-(4-FORMYL-3,5-DIMETHYL-1H-PYRAZOL-1-YL)ACETAMIDE; N-CYCLOPENTYL-2-(4-FORMYLPHENOXY)ACETAMIDE; N-CYCLOPENTYL-2-(4-FORMYLPHENOXY)PROPANAMIDE; N-CYCLOPENTYL-2-(4-FORMYLPIPERIDIN-1-YL)ACETAMIDE; N-CYCLOPENTYL-2-(4-FORMYLPIPERIDIN-1-YL)PROPANAMIDE; N-CYCLOPROPYL-2-((5-FORMYLIMIDAZO[2,1-B][1,3]THIAZOL-6-YL)(METHYL)AMINO)ACETAMIDE; N-CYCLOPROPYL-2-(2,4-DICHLORO-6-FORMYLPHENOXY)ACETAMIDE; N-CYCLOPROPYL-2-(2-ETHOXY-4-FORMYLPHENOXY)ACETAMIDE; N-CYCLOPROPYL-2-(2-ETHOXY-6-FORMYLPHENOXY)ACETAMIDE; N-CYCLOPROPYL-2-(2-FORMYL-4-METHOXYPHENOXY)ACETAMIDE; N-CYCLOPROPYL-2-(2-FORMYL-4-METHOXYPHENOXY)PROPANAMIDE; N-CYCLOPROPYL-2-(2-FORMYL-4-NITROPHENOXY)ACETAMIDE; N-CYCLOPROPYL-2-(2-FORMYL-5-METHOXYPHENOXY)ACETAMIDE; N-CYCLOPROPYL-2-(2-FORMYL-5-METHOXYPHENOXY)PROPANAMIDE; N-CYCLOPROPYL-2-(2-FORMYL-5-PROPOXYPHENOXY)ACETAMIDE; N-CYCLOPROPYL-2-(2-FORMYL-6-METHOXYPHENOXY)ACETAMIDE; N-CYCLOPROPYL-2-(2-FORMYL-6-METHOXYPHE-

NOXY)PROPANAMIDE; N-CYCLOPROPYL-2-(2-FORMYLPHENOXY)ACETAMIDE; N-CYCLOPROPYL-2-(2-FORMYLPHENOXY)PROPANAMIDE; N-CYCLOPROPYL-2-(2-FORMYLPIPERIDIN-1-YL)ACETAMIDE; N-CYCLOPROPYL-2-(2-FORMYLPIPERIDIN-1-YL)PROPANAMIDE; N-CYCLOPROPYL-2-(3-FORMYL-2,5-DIMETHYL-1H-PYRROL-1-YL)ACETAMIDE; N-CYCLOPROPYL-2-(3-FORMYL-2-METHYL-INDOL-1-YL)-ACETAMIDE; N-CYCLOPROPYL-2-(3-FORMYL-INDOL-1-YL)-ACETAMIDE; N-CYCLOPROPYL-2-(3-FORMYLPHENOXY)ACETAMIDE; N-CYCLOPROPYL-2-(3-FORMYLPHENOXY)PROPANAMIDE; N-CYCLOPROPYL-2-(3-FORMYLPIPERIDIN-1-YL)ACETAMIDE; N-CYCLOPROPYL-2-(3-FORMYLPIPERIDIN-1-YL)PROPANAMIDE; N-CYCLOPROPYL-2-(4-FORMYL-2,6-DIMETHOXYPHENOXY)ACETAMIDE; N-CYCLOPROPYL-2-(4-FORMYL-2,6-DIMETHYLPHENOXY)ACETAMIDE; N-CYCLOPROPYL-2-(4-FORMYL-2,6-DIMETHYLPHENOXY)PROPANAMIDE; N-CYCLOPROPYL-2-(4-FORMYL-2-METHOXYPHENOXY)ACETAMIDE; N-CYCLOPROPYL-2-(4-FORMYL-2-METHOXYPHENOXY)PROPANAMIDE; N-CYCLOPROPYL-2-(4-FORMYL-2-NITROPHENOXY)ACETAMIDE; N-CYCLOPROPYL-2-(4-FORMYL-3,5-DIMETHYL-1H-PYRAZOL-1-YL)ACETAMIDE; N-CYCLOPROPYL-2-(4-FORMYLPHENOXY)ACETAMIDE; N-CYCLOPROPYL-2-(4-FORMYLPHENOXY)PROPANAMIDE; N-CYCLOPROPYL-2-(4-FORMYLPIPERIDIN-1-YL)ACETAMIDE; N-CYCLOPROPYL-2-(4-FORMYLPIPERIDIN-1-YL)PROPANAMIDE; N-CYCLOPROPYL-2-(5-FORMYL-2-METHOXYPHENOXY)ACETAMIDE; N-CYCLOPROPYL-2-(5-FORMYL-2-METHOXYPHENOXY)PROPANAMIDE; N-CYCLOPROPYL-2-(5-FORMYL-2-NITROPHENOXY)ACETAMIDE; N-CYCLOPROPYL-2-[(2,6-DIFLUORO-4-FORMYLPHENYL)(METHYL)AMINO]ACETAMIDE; N-CYCLOPROPYL-2-[(2-FLUORO-4-FORMYLPHENYL)(METHYL)AMINO]ACETAMIDE; N-CYCLOPROPYL-2-[(2-FORMYLPHENYL)(METHYL)AMINO]ACETAMIDE; N-CYCLOPROPYL-2-[(4-FLUORO-2-FORMYLPHENYL)(METHYL)AMINO]ACETAMIDE; N-CYCLOPROPYL-2-[(4-FORMYL-1,3-DIMETHYL-1H-PYRAZOL-5-YL)(METHYL)AMINO]ACETAMIDE; N-CYCLOPROPYL-2-[(4-FORMYL-2-METHYLPHENYL)(METHYL)AMINO]ACETAMIDE; N-CYCLOPROPYL-2-[(4-FORMYL-3-METHYLPHENYL)(METHYL)AMINO]ACETAMIDE; N-CYCLOPROPYL-2-[(4-FORMYLPHENYL)(METHYL)AMINO]ACETAMIDE; N-CYCLOPROPYL-2-[(5-FORMYLFURAN-2-YL)(METHYL)AMINO]ACETAMIDE; N-CYCLOPROPYL-2-[(6-FORMYL-2H-1,3-BENZODIOXOL-5-YL)OXY]ACETAMIDE; N-CYCLOPROPYL-2-[METHYL(2-OXOETHYL)AMINO]ACETAMIDE; N-CYCLOPROPYL-2-[METHYL(3-OXOPROPYL)AMINO]ACETAMIDE; N-CYCLOPROPYL-3-(2-FORMYL-4-METHOXYPHENOXY)PROPANAMIDE; N-CYCLOPROPYL-3-(2-FORMYL-5-METHOXYPHENOXY)PROPANAMIDE; N-CYCLOPROPYL-3-(2-FORMYL-6-METHOXYPHENOXY)PROPANAMIDE; N-CYCLOPROPYL-3-(2-FORMYLPHENOXY)PROPANAMIDE; N-CYCLOPROPYL-3-(2-FORMYLPIPERIDIN-1-YL)PROPANAMIDE; N-CYCLOPROPYL-3-(3-FORMYLPHENOXY)PROPANAMIDE; N-CYCLOPROPYL-3-(3-FORMYLPIPERIDIN-1-YL)PROPANAMIDE; N-CYCLOPROPYL-3-(4-FORMYL-2,6-DIMETHYLPHENOXY)PROPANAMIDE; N-CYCLOPROPYL-3-(4-FORMYL-2-METHOXYPHENOXY)PROPANAMIDE; N-CYCLOPROPYL-3-(4-FORMYLPHENOXY)PROPANAMIDE; N-CYCLOPROPYL-3-(4-FORMYLPIPERIDIN-1-YL)PROPANAMIDE; N-CYCLOPROPYL-3-(5-FORMYL-2-METHOXYPHENOXY)PROPANAMIDE; N-CYCLOPROPYL-4-FORMYLBENZAMIDE; N-ETHYL-2-((3-FORMYLIMIDAZO[1,2-A]PYRIDIN-2-YL)(METHYL)AMINO)ACETAMIDE; N-ETHYL-2-((5-FORMYLIMIDAZO[2,1-B][1,3]THIAZOL-6-YL)(METHYL)AMINO)ACETAMIDE; N-ETHYL-2-([(5-FORMYL-2-METHOXYPHENYL)METHYL](METHYL)AMINO)ACETAMIDE; N-ETHYL-2-(2-FORMYL-4-METHOXYPHENOXY)ACETAMIDE; N-ETHYL-2-(2-FORMYL-4-METHOXYPHENOXY)PROPANAMIDE; N-ETHYL-2-(2-FORMYL-4-METHYLPHENOXY)ACETAMIDE; N-ETHYL-2-(2-FORMYL-4-NITROPHENOXY)ACETAMIDE; N-ETHYL-2-(2-FORMYL-4-NITROPHENOXY)PROPANAMIDE; N-ETHYL-2-(2-FORMYL-5-METHOXYPHENOXY)ACETAMIDE; N-ETHYL-2-(2-FORMYL-5-METHOXYPHENOXY)PROPANAMIDE; N-ETHYL-2-(2-FORMYL-5-PROPOXYPHENOXY)ACETAMIDE; N-ETHYL-2-(2-FORMYL-6-METHOXYPHENOXY)ACETAMIDE; N-ETHYL-2-(2-FORMYL-6-METHOXYPHENOXY)PROPANAMIDE; N-ETHYL-2-(2-FORMYLPHENOXY)ACETAMIDE; N-ETHYL-2-(2-FORMYLPHENOXY)PROPANAMIDE; N-ETHYL-2-(2-FORMYLPIPERIDIN-1-YL)ACETAMIDE; N-ETHYL-2-(2-FORMYLPIPERIDIN-1-YL)PROPANAMIDE; N-ETHYL-2-(3-FORMYL-2,5-DIMETHYL-1H-PYRROL-1-YL)ACETAMIDE; N-ETHYL-2-(3-FORMYL-2,5-DIMETHYL-1H-PYRROL-1-YL)PROPANAMIDE; N-ETHYL-2-(3-FORMYLPHENOXY)ACETAMIDE; N-ETHYL-2-(3-FORMYLPHENOXY)PROPANAMIDE; N-ETHYL-2-(3-FORMYLPIPERIDIN-1-YL)ACETAMIDE; N-ETHYL-2-(3-FORMYLPIPERIDIN-1-YL)PROPANAMIDE; N-ETHYL-2-(4-FORMYL-2,6-DIMETHOXYPHENOXY)ACETAMIDE; N-ETHYL-2-(4-FORMYL-2,6-DIMETHYLPHENOXY)ACETAMIDE; N-ETHYL-2-(4-FORMYL-2,6-DIMETHYLPHENOXY)PROPANAMIDE; N-ETHYL-2-(4-FORMYL-2-METHOXY-6-NITROPHENOXY)ACETAMIDE; N-ETHYL-2-(4-FORMYL-2-METHOXYPHENOXY)ACETAMIDE; N-ETHYL-2-(4-FORMYL-2-METHOXYPHENOXY)PROPANAMIDE; N-ETHYL-2-(4-FORMYL-2-NITROPHENOXY)ACETAMIDE; N-ETHYL-2-(4-FORMYL-2-NITROPHENOXY)PROPANAMIDE; N-ETHYL-2-(4-FORMYL-3,5-DIMETHYL-1H-PYRAZOL-1-YL)ACETAMIDE; N-ETHYL-2-(4-FORMYLPHENOXY)ACETAMIDE; N-ETHYL-2-(4-FORMYLPHENOXY)PROPANAMIDE; N-ETHYL-2-(4-FORMYLPIPERIDIN-1-YL)ACETAMIDE; N-ETHYL-2-(4-FORMYLPIPERIDIN-1-YL)PROPANAMIDE; N-ETHYL-2-(5-FORMYL-2-METHOXYPHENOXY)ACETAMIDE; N-ETHYL-2-(5-FORMYL-2-METHOXYPHENOXY)PROPANAMIDE; N-ETHYL-2-(5-FORMYL-2-NITROPHENOXY)ACETAMIDE; N-ETHYL-2-(5-FORMYL-2-NITROPHENOXY)PROPANAMIDE; N-ETHYL-2-[(1-FORMYLNAPHTHALEN-2-YL)OXY]ACETAMIDE; N-ETHYL-2-[(2-FLUORO-4-FORMYLPHENYL)(METHYL)AMINO]ACETAMIDE; N-ETHYL-2-[(2-FORMYL-4-NITROPHENYL)(METHYL)AMINO]ACETAMIDE; N-ETHYL-2-[(2-FORMYLPHENYL)(METHYL)AMINO]ACETAMIDE; N-ETHYL-2-[(4-FLUORO-2-FORMYLPHENYL)

(METHYL)AMINO]ACETAMIDE; N-ETHYL-2-[(4-FORMYL-1,3-DIMETHYL-1H-PYRAZOL-5-YL)(METHYL)AMINO]ACETAMIDE; N-ETHYL-2-[(4-FORMYL-2-METHYLPHENYL)(METHYL)AMINO]ACETAMIDE; N-ETHYL-2-[(4-FORMYL-2-NITROPHENYL)(METHYL)AMINO]ACETAMIDE; N-ETHYL-2-[(4-FORMYL-3-METHYLPHENYL)(METHYL)AMINO]ACETAMIDE; N-ETHYL-2-[(4-FORMYLPHENYL)(METHYL)AMINO]ACETAMIDE; N-ETHYL-2-[(5-FORMYLFURAN-2-YL)(METHYL)AMINO]ACETAMIDE; N-ETHYL-2-[(6-FORMYL-2H-1,3-BENZODIOXOL-5-YL)OXY]ACETAMIDE; N-ETHYL-2-[ETHYL((5-FORMYLIMIDAZO[2,1-B][1,3]THIAZOL-6-YL))AMINO]ACETAMIDE; N-ETHYL-2-[ETHYL(2-FLUORO-4-FORMYLPHENYL)AMINO]ACETAMIDE; N-ETHYL-2-[ETHYL(2-FORMYLPHENYL)AMINO]ACETAMIDE; N-ETHYL-2-[ETHYL(2-OXOETHYL)AMINO]ACETAMIDE; N-ETHYL-2-[ETHYL(3-OXOPROPYL)AMINO]ACETAMIDE; N-ETHYL-2-[ETHYL(4-FLUORO-2-FORMYLPHENYL)AMINO]ACETAMIDE; N-ETHYL-2-[ETHYL(4-FORMYL-1,3-DIMETHYL-1H-PYRAZOL-5-YL)AMINO]ACETAMIDE; N-ETHYL-2-[ETHYL(4-FORMYL-2-METHYLPHENYL)AMINO]ACETAMIDE; N-ETHYL-2-[ETHYL(4-FORMYL-3-METHYLPHENYL)AMINO]ACETAMIDE; N-ETHYL-2-[ETHYL(4-FORMYLPHENYL)AMINO]ACETAMIDE; N-ETHYL-2-[ETHYL(5-FORMYLFURAN-2-YL)AMINO]ACETAMIDE; N-ETHYL-2-[METHYL(2-OXOETHYL)AMINO]ACETAMIDE; N-ETHYL-2-[METHYL(3-OXOPROPYL)AMINO]ACETAMIDE; N-ETHYL-3-(2-FORMYL-4-METHOXYPHENOXY)PROPANAMIDE; N-ETHYL-3-(2-FORMYL-4-NITROPHENOXY)PROPANAMIDE; N-ETHYL-3-(2-FORMYL-5-METHOXYPHENOXY)PROPANAMIDE; N-ETHYL-3-(2-FORMYL-6-METHOXYPHENOXY)PROPANAMIDE; N-ETHYL-3-(2-FORMYLPHENOXY)PROPANAMIDE; N-ETHYL-3-(2-FORMYLPIPERIDIN-1-YL)PROPANAMIDE; N-ETHYL-3-(3-FORMYLPHENOXY)PROPANAMIDE; N-ETHYL-3-(3-FORMYLPIPERIDIN-1-YL)PROPANAMIDE; N-ETHYL-3-(4-FORMYL-2,6-DIMETHYLPHENOXY)PROPANAMIDE; N-ETHYL-3-(4-FORMYL-2-METHOXYPHENOXY)PROPANAMIDE; N-ETHYL-3-(4-FORMYL-2-NITROPHENOXY)PROPANAMIDE; N-ETHYL-3-(4-FORMYLPHENOXY)PROPANAMIDE; N-ETHYL-3-(4-FORMYLPIPERIDIN-1-YL)PROPANAMIDE; N-ETHYL-3-(5-FORMYL-2-METHOXYPHENOXY)PROPANAMIDE; N-ETHYL-3-(5-FORMYL-2-NITROPHENOXY)PROPANAMIDE; N-ETHYL-3-[(6-FORMYL-2H-1,3-BENZODIOXOL-5-YL)OXY]PROPANAMIDE; N-ETHYL-4-(2-FORMYLPIPERIDIN-1-YL)PYRIDINE-2-CARBOXAMIDE; N-ETHYL-4-(3-FORMYLPIPERIDIN-1-YL)PYRIDINE-2-CARBOXAMIDE; N-ETHYL-4-(4-FORMYLPIPERIDIN-1-YL)PYRIDINE-2-CARBOXAMIDE; N-ETHYLGLUCOSAMINE; N-METHYL-1-(2-OXOETHYL)PIPERIDINE-4-CARBOXAMIDE; N-METHYL-1-(3-OXOPROPYL)PIPERIDINE-2-CARBOXAMIDE; N-METHYL-1-(3-OXOPROPYL)PIPERIDINE-4-CARBOXAMIDE; N-METHYL-1-(3-OXOPROPYL)PYRROLIDINE-2-CARBOXAMIDE; N-METHYL-2-[(2-OXOETHYL)(PROPYL)AMINO]ACETAMIDE; N-METHYL-2-[(3-OXOPROPYL)(PROPYL)AMINO]ACETAMIDE; N-METHYL-2-[METHYL(2-OXOETHYL)AMINO]ACETAMIDE; N-METHYL-2-[METHYL(3-OXOPROPYL)AMINO]ACETAMIDE; N-NITROSO-4-METHYLAMINOBENZALDEHYDE; N-OCTYL-D-GLUCOSAMINE; N-PROPANOYL-D-GLUCOSAMINE; N-TERT-BOC-2-(4-FORMYL-2-METHOXYPHENOXY)ETHYLAMINE-D3; N-TERT-BUTYL-2-(2-CHLORO-4-FORMYLPHENOXY)ACETAMIDE; N-TERT-BUTYL-2-(2-CHLORO-4-FORMYLPHENOXY)PROPANAMIDE; N-TERT-BUTYL-2-(2-FORMYL-4-METHOXYPHENOXY)ACETAMIDE; N-TERT-BUTYL-2-(2-FORMYL-5-METHOXYPHENOXY)ACETAMIDE; N-TERT-BUTYL-2-(2-FORMYL-6-METHOXYPHENOXY)ACETAMIDE; N-TERT-BUTYL-2-(2-FORMYLPHENOXY)ACETAMIDE; N-TERT-BUTYL-2-(2-FORMYLPHENOXY)PROPANAMIDE; N-TERT-BUTYL-2-(2-FORMYLPIPERIDIN-1-YL)ACETAMIDE; N-TERT-BUTYL-2-(2-FORMYLPIPERIDIN-1-YL)PROPANAMIDE; N-TERT-BUTYL-2-(3-CHLORO-2-FORMYLPHENOXY)ACETAMIDE; N-TERT-BUTYL-2-(3-CHLORO-2-FORMYLPHENOXY)PROPANAMIDE; N-TERT-BUTYL-2-(3-FORMYLPHENOXY)ACETAMIDE; N-TERT-BUTYL-2-(3-FORMYLPHENOXY)PROPANAMIDE; N-TERT-BUTYL-2-(3-FORMYLPIPERIDIN-1-YL)ACETAMIDE; N-TERT-BUTYL-2-(3-FORMYLPIPERIDIN-1-YL)PROPANAMIDE; N-TERT-BUTYL-2-(4-CHLORO-2-FORMYLPHENOXY)ACETAMIDE; N-TERT-BUTYL-2-(4-CHLORO-2-FORMYLPHENOXY)PROPANAMIDE; N-TERT-BUTYL-2-(4-FORMYL-3,5-DIMETHYL-1H-PYRAZOL-1-YL)ACETAMIDE; N-TERT-BUTYL-2-(4-FORMYLPHENOXY)PROPANAMIDE; N-TERT-BUTYL-2-(4-FORMYLPIPERIDIN-1-YL)ACETAMIDE; N-TERT-BUTYL-2-(4-FORMYLPIPERIDIN-1-YL)PROPANAMIDE; N-TERT-BUTYL-2-(5-FORMYL-2-METHOXYPHENOXY)ACETAMIDE; OROTALALDEHYDE; PHENACETURIC ACID,-ALPHA-FORMYL-ALPHA-METHYL-; PIPERIDINE-3-CARBALDEHYDE; PRINCETON PBMR041959; PROPANAMIDE, N-(2-FORMYLPHENYL)-2,2-DIMETHYL; PROPYL N-(5-FORMYLPYRIMIDIN-2-YL)GLYCINATE; PYRROLE-2-CARBOXALDEHYDE; PYRROLIDINE-2-CARBALDEHYDE; RARECHEM AQ NN 0175; RO 08-2750; T-BUTYL N-(2-OXOETHYL)CABAMATE; TERT-BUTYL (1S,2R)-1-(5-FORMYLOXAZOL-2-YL)-2-METHYLBUTYLCARBAMATE; TERT-BUTYL (1S,2S)-1-(5-FORMYLOXAZOL-2-YL)-2-METHYLBUTYLCARBAMATE; TERT-BUTYL (2S)-1-OXO-3-PHENYLBUTAN-2-YLCARBAMATE; TERT-BUTYL (4-FORMYL-2-METHOXYPYRIDIN-3-YL)CARBAMATE; TERT-BUTYL (4-FORMYL-5-METHYLISOXAZOL-3-YL)CARBAMATE; TERT-BUTYL (5-FORMYL-2-NAPHTHYL)CARBAMATE; TERT-BUTYL (5-FORMYLPYRIDIN-2-YL)CARBAMATE; TERT-BUTYL (6-CHLORO-3-FORMYLPYRIDIN-2-YL)CARBAMATE; TERT-BUTYL (R)-1-FORMYL-3-METHYLBUTYL CARBAMATE; TERT-BUTYL (S)-1-FORMYL-2-(4-HYDROXYPHENYL)ETHYLCARBAMATE; TERT-BUTYL (S)1-FORMYL-3-METHYLBUTYLCARBAMATE; TERT-BUTYL [(1S)-2-CYCLOHEXYL-1-FORMYLETHYL]CARBAMATE; TERT-BUTYL [(1S,3S)-1-FORMYL-3-METHYLPENTYL]CARBAMATE; TERT-BUTYL 1-(FORMYLMETHYL)CYCLOHEXYL CARBAMATE; TERT-BUTYL 1-FORMYL-2-(3-HYDROXYPHENYL)ETHYLCARBAMATE; TERT-BUTYL 1-FORMYLPENTYLCARBAMATE; TERT-BUTYL 1-OXOPROPAN-2-YLCARBAMATE; TERT-BUTYL 2-(5-FORMYLPYRIMIDIN-2-YLAMINO)ACETATE; TERT-BUTYL 2-(FORMYLMETHYL)BENZYLCARBAMATE; TERT-BUTYL 2-(FORMYLMETHYL)PHENYLCARBAMATE; TERT-BUTYL 2,6-DICHLORO-4-FORMYLPHENYL-

CARBAMATE; TERT-BUTYL 2-CHLORO-3-FORMYLPYRIDIN-4-YLCARBAMATE; TERT-BUTYL 2-FLUORO-6-FORMYLPHENYLCARBAMATE; TERT-BUTYL 2-FORMYL-3-METHOXYPHENYLCARBAMATE; TERT-BUTYL 2-FORMYL-4-(TRIFLUOROMETHYL)PHENYLCARBAMATE; TERT-BUTYL 2-FORMYL-4,6-DIMETHYLPHENYLCARBAMATE; TERT-BUTYL 2-FORMYL-5-(TRIFLUOROMETHYL)PHENYLCARBAMATE; TERT-BUTYL 2-FORMYL-5-METHOXYPHENYLCARBAMATE; TERT-BUTYL 2-FORMYL-6-(TRIFLUOROMETHYL)PHENYLCARBAMATE; TERT-BUTYL 2-FORMYL-6,7-DIHYDROTHIAZOLO[5,4-C]PYRIDINE-5(4H)-CARBOXYLATE; TERT-BUTYL 2-FORMYL-6-METHYLPHENYLCARBAMATE; TERT-BUTYL 2-FORMYLFURAN-3-YLCARBAMATE; TERT-BUTYL 2-FORMYLPROPAN-2-YLCARBAMATE; TERT-BUTYL 2-FORMYLQUINOLIN-6-YLCARBAMATE; TERT-BUTYL 2-FORMYLQUINOLIN-8-YLCARBAMATE; TERT-BUTYL 2-METHYL-5-OXOPENT-3-YN-2-YLCARBAMATE; TERT-BUTYL 3-(2-OXOETHYL)PYRIDIN-2-YLCARBAMATE; TERT-BUTYL 3,4,5-TRIFLUORO-2-FORMYLPHENYLCARBAMATE; TERT-BUTYL 3,4-DIFLUORO-2-FORMYLPHENYLCARBAMATE; TERT-BUTYL 3-CHLORO-2-FORMYLPHENYLCARBAMATE; TERT-BUTYL 3-FORMYL-1H-INDOL-4-YLCARBAMATE; TERT-BUTYL 3-FORMYL-5-(TRIFLUOROMETHYL)THIEN-2-YLCARBAMATE; TERT-BUTYL 3-FORMYLBENZYLCARBAMATE; TERT-BUTYL 3-FORMYLPYRIDIN-4-YLCARBAMATE; TERT-BUTYL 3-METHYL-1-OXOBUTAN-2-YLCARBAMATE; TERT-BUTYL 4-(2-OXOETHYL)PYRIDIN-2-YLCARBAMATE; TERT-BUTYL 4-CHLORO-2-FORMYLBENZYLCARBAMATE; TERT-BUTYL 4-CHLORO-2-FORMYLPHENYLCARBAMATE; TERT-BUTYL 4-CHLORO-3-FORMYLPYRIDIN-2-YLCARBAMATE; TERT-BUTYL 4-CHLORO-5-FORMYLPYRIDIN-2-YLCARBAMATE; TERT-BUTYL 4-FLUORO-2-FORMYLPHENYLCARBAMATE; TERT-BUTYL 4-FORMYL-3-(TRIFLUOROMETHYL)PHENYLCARBAMATE; TERT-BUTYL 4-FORMYLBENZO[D]THIAZOL-2-YLCARBAMATE; TERT-BUTYL 4-FORMYLPYRIDIN-2-YLCARBAMATE; TERT-BUTYL 4-FORMYLPYRIDIN-3-YLCARBAMATE; TERT-BUTYL 4-OXOBUT-2-YNYLCARBAMATE; TERT-BUTYL 5-(5-FORMYLOXAZOL-2-YL)-1-METHYL-1H-PYRROL-3-YLCARBAMATE; TERT-BUTYL 5-CHLORO-4-FORMYLPYRIDIN-2-YLCARBAMATE; TERT-BUTYL 5-FLUORO-4-FORMYLPYRIDIN-2-YLCARBAMATE; TERT-BUTYL 5-FORMYL-3,4-DIMETHYL-1H-PYRROLE-2-CARBOXYLATE; TERT-BUTYL 6-(2-OXOETHYL)PYRIDIN-2-YLCARBAMATE; TERT-BUTYL 6-FORMYL-2,3-DIMETHYLPHENYLCARBAMATE; TERT-BUTYL 6-FORMYLPYRIDIN-3-YLCARBAMATE; TERT-BUTYL 6-FORMYLPYRIMIDIN-4-YLCARBAMATE; TERT-BUTYL CIS-4-(2-OXOETHYL)CYCLOHEXYLCARBAMATE; TERT-BUTYL CIS-4-FORMYLCYCLOHEXYLCARBAMATE; TERT-BUTYL FORMYL(4-HYDROXYPHENYL)METHYLCARBAMATE; TERT-BUTYL N-(1-BENZYL-2-OXOETHYL)CARBAMATE; TERT-BUTYL N-(2-FORMYL-1-BENZOFURAN-5-YL)CARBAMATE; TERT-BUTYL N-(4-FORMYLBENZYL)CARBAMATE; TERT-BUTYL TRANS-4-(2-OXOETHYL)CYCLOHEXYLCARBAMATE; TERT-BUTYL TRANS-4-FORMYLCYCLOHEXYLCARBAMATE; TERT-BUTYL(S)-2-(4-FLUOROCYCLOHEXYL)-1-FORMYLETHYLCARBAMATE; THEOPHYLLINEACETIC ALDEHYDE; TRANS-3-(2,4-DIFLUOROPHENYL)PYRROLIDINE-2-CARBALDEHYDE; TRANS-4-(BENZYLOXYCARBONYLAMINO)CYCLOHEXANECARBALDEHYDE; TRANS-BENZYL(-4-FORMYLCYCLOHEXYL)METHYLCARBAMATE; TRANS-TERT-BUTYL (4-FORMYLCYCLOHEXYL)METHYLCARBAMATE; TRIAZOLAL;

List No. 3—Boronic Acids:

(1-([2-(TRIMETHYLSILYL)ETHOXY]METHYL)-1H-IMIDAZOL-4-YL)BORONIC ACID; (1-([2-(TRIMETHYLSILYL)ETHOXY]METHYL)-1H-IMIDAZOL-5-YL)BORONIC ACID; (1-(2-(DIMETHYLAMINO)ETHOXY)-1H-PYRAZOL-4-YL)BORONIC ACID; (1-(3-METHOXYPROPYL)-1H-PYRAZOL-4-YL)BORONIC ACID; (1,2,3,4-TETRAHYDRO-1-OXO-6-ISOQUINOLINYL)-BORONIC ACID; (1,2-DIHYDRO-2-OXO-5-PYRIMIDINYL)-BORONIC ACID; (1,2-DIHYDRO-4,8-DIMETHOXY-2-OXO-3-QUINOLINYL)-BORONIC ACID; (1-[(4-METHYLPHENYL)SULFONYL]-1H-PYRROLO[3,2-B]PYRIDIN-3-YL)BORONIC ACID; (1-[(BENZYLOXY)CARBONYL]-1,2,3,6-TETRAHYDROPYRIDIN-4-YL)BORONIC ACID; (1-[TERT-BUTYL(DIMETHYL)SILYL]-1H-INDOL-3-YL)BORONIC ACID; (1-[TERT-BUTYL(DIMETHYL)SILYL]-1H-PYRROLO[2,3-B]PYRIDIN-5-YL)BORONIC ACID; (10-PHENYLANTHRACEN-9-YL)BORONIC ACID; (1-ACETYL-2,3-DIHYDRO-1H-INDOL-5-YL)BORONIC ACID; (1-BENZYL-1,2,3,6-TETRAHYDROPYRIDIN-4-YL)BORONIC ACID; (1-BENZYLINDAZOL-5-YL)BORONIC ACID; (1-CYCLOPROPYL-1H-PYRAZOL-4-YL)BORONIC ACID; (1-METHYL-1,2,3,6-TETRAHYDROPYRIDIN-4-YL)BORONIC ACID; (1-METHYL-1H-PYRROLO[2,3-B]PYRIDIN-3-YL)BORONIC ACID; (1-METHYLBENZIMIDAZOLE-2-YL)BORONIC ACID; (1-OXO-1,3-DIHYDROISOBENZOFURAN-4-YL)BORONIC ACID; (1-OXO-1,3-DIHYDROISOBENZOFURAN-5-YL)BORONIC ACID; (1-OXO-1,3-DIHYDROISOBENZOFURAN-6-YL)BORONIC ACID; (1-OXO-1,3-DIHYDROISOBENZOFURAN-7-YL)BORONIC ACID; (1-OXO-2-PHENYLISOINDOLIN-4-YL)BORONIC ACID; (1-OXO-2-PHENYLISOINDOLIN-5-YL)BORONIC ACID; (1-OXO-2-PHENYLISOINDOLIN-6-YL)BORONIC ACID; (1-OXO-2-PHENYLISOINDOLIN-7-YL)BORONIC ACID; (1-OXO-2-PROPYLISOINDOLIN-4-YL)BORONIC ACID; (1-OXO-2-PROPYLISOINDOLIN-5-YL)BORONIC ACID; (1-OXO-2-PROPYLISOINDOLIN-6-YL)BORONIC ACID; (1-OXO-2-PROPYLISOINDOLIN-7-YL)BORONIC ACID; (1-OXOISOINDOLIN-7-YL)BORONIC ACID; (1R)-1-(2-THIENYLACETYLAMINO)-1-(3-CARBOXYPHENYL)METHYLBORONIC ACID; (1R,2S)-2-METHYLCYCLOPROPYLBORONIC ACID; (1S)-1,7,7-TRIMETHYLBICYCLO[2.2.1]HEPT-2-EN-2-YLBORONIC ACID; (1S,2S)-2-(CHLOROMETHYL)CYCLOPROPYLBORONIC ACID; (1S,2S)-2-METHYLCYCLOPROPYLBORONIC ACID; (1S,2S)-2-PHENYLCYCLOPROPYLBORONIC ACID; (1S,2S)-2-PROPYLCYCLOPROPYLBORONIC ACID; (1-TRITYL-1H-1,2,3-BENZOTRIAZOL-5-YL)BORONIC ACID; (1-TRITYL-1H-IMIDAZOL-4-YL)BORONIC ACID; (2-([(1,3-DIMETHYL-1H-PYRAZOL-5-YL)SULFANYL]METHYL)PHENYL)BORANEDIOL; (2-([(2,4-DIFLUOROPHENYL)SULFANYL]METHYL)PHENYL)BORANEDIOL; (2-([(2,4-DIMETHYLPHENYL)SULFANYL]METHYL)PHENYL)BORANEDIOL; (2-

([(2,5-DIFLUOROPHENYL)SULFANYL]METHYL) PHENYL)BORANEDIOL; (2-([(2,5-DIMETHYLPHENYL)SULFANYL]METHYL)PHENYL) BORANEDIOL; (2-([(2-CHLOROPHENYL)METHOXY] METHYL)PHENYL)BORANEDIOL; (2-([(2-CHLOROPHENYL)SULFANYL]METHYL)-5-FLUOROPHENYL)BORANEDIOL; (2-([(2E)-3-PHENYLPROP-2-EN-1-YL]OXY)PHENYL) BORANEDIOL; (2-([(2-METHOXYPHENYL) SULFANYL]METHYL)PHENYL)BORANEDIOL; (2-([(3,4-DIFLUOROPHENYL)SULFANYL]METHYL) PHENYL)BORANEDIOL; (2-([(3,4-DIMETHYLPHENYL)SULFANYL]METHYL)PHENYL) BORANEDIOL; (2-([(3-CHLOROPHENYL)SULFANYL] METHYL)-5-FLUOROPHENYL)BORANEDIOL; (2-([(3-CHLOROPHENYL)SULFANYL]METHYL)PHENYL) BORANEDIOL; (2-([(3-METHOXYPHENYL) SULFANYL]METHYL)PHENYL)BORANEDIOL; (2-([(3-METHOXYPROPYL)(METHYL)AMINO] METHYL)PHENYL)BORANEDIOL; (2-([(4,6-DIMETHYLPYRIMIDIN-2-YL)SULFANYL]METHYL) PHENYL)BORANEDIOL; (2-([(4-CHLOROPHENYL) SULFANYL]METHYL)-5-FLUOROPHENYL) BORANEDIOL; (2-([(4-METHOXYPHENYL) SULFANYL]METHYL)PHENYL)BORANEDIOL; (2-([(4-METHYLPYRIMIDIN-2-YL)SULFANYL] METHYL)PHENYL)BORANEDIOL; (2-([(5-METHYL-1, 3,4-OXADIAZOL-2-YL)SULFANYL]METHYL) PHENYL)BORANEDIOL; (2-([(CYCLOBUTYLMETHYL)(METHYL)AMINO] METHYL)-5-FLUOROPHENYL)BORANEDIOL; (2-([(CYCLOBUTYLMETHYL)(METHYL)AMINO] METHYL)PHENYL)BORANEDIOL; (2-([(CYCLOHEXYLMETHYL)(METHYL)AMINO] METHYL)PHENYL)BORANEDIOL; (2-([(CYCLOPROPYLMETHYL)(PROPYL)AMINO] METHYL)-5-FLUOROPHENYL)BORANEDIOL; (2-([3-(1H-IMIDAZOL-1-YL)PROPYL]AMINO)PYRIMIDIN-5-YL)BORONIC ACID; (2-([4-(DIMETHYLAMINO) PIPERIDIN-1-YL]METHYL)PHENYL)BORANEDIOL; (2-([4-(PROPAN-2-YL)PIPERAZIN-1-YL]METHYL) PHENYL)BORANEDIOL; (2-([BENZYL(METHYL) AMINO]METHYL)PHENYL)BORANEDIOL; (2-([BIS (2-METHOXYETHYL)AMINO]METHYL)PHENYL) BORANEDIOL; (2-([BIS(2-METHYLPROPYL)AMINO] METHYL)PHENYL)BORANEDIOL; (2-([BUTYL (CYCLOPROPYL)AMINO]METHYL)-5-FLUOROPHENYL)BORANEDIOL; (2-([CYCLOHEPTYL(METHYL)AMINO]METHYL) PHENYL)BORANEDIOL; (2-([CYCLOHEXYL(ETHYL) AMINO]METHYL)PHENYL)BORANEDIOL; (2-([CYCLOHEXYL(METHYL)AMINO]METHYL)-5-FLUOROPHENYL)BORANEDIOL; (2-([CYCLOPENTYL(ETHYL)AMINO]METHYL)-5-FLUOROPHENYL)BORANEDIOL; (2-([CYCLOPROPYL(2-METHOXYETHYL)AMINO] METHYL)-5-FLUOROPHENYL)BORANEDIOL; (2-([ETHYL(2-ETHYLBUTYL)AMINO]METHYL) PHENYL)BORANEDIOL; (2-([ETHYL(PHENYL) AMINO]METHYL)PHENYL)BORANEDIOL; (2-([METHYL(1-METHYLPIPERIDIN-4-YL)AMINO] METHYL)PHENYL)BORANEDIOL; (2-([METHYL(4-METHYLCYCLOHEXYL)AMINO]METHYL)PHENYL) BORANEDIOL; (2-([METHYL(PYRIDIN-2-YLMETHYL)AMINO]METHYL)PHENYL) BORANEDIOL; (2-([METHYL(PYRIDIN-3-YLMETHYL)AMINO]METHYL)PHENYL) BORANEDIOL; (2-([METHYL(PYRIDIN-4-YLMETHYL)AMINO]METHYL)PHENYL) BORANEDIOL; (2-(2-(DIMETHYLAMINO)ETHOXY) PYRIDIN-4-YL)BORONIC ACID; (2-(2-HYDROXYETHYL)-1-OXOISOINDOLIN-4-YL) BORONIC ACID; (2-(2-HYDROXYETHYL)-1-OXOISOINDOLIN-5-YL)BORONIC ACID; (2-(2-HYDROXYETHYL)-1-OXOISOINDOLIN-6-YL) BORONIC ACID; (2-(2-HYDROXYETHYL)-1-OXOISOINDOLIN-7-YL)BORONIC ACID; (2-(2-METHOXYETHYL)PYRIDIN-4-YL)BORONIC ACID; (2-(3-(DIMETHYLAMINO)PROPYL)PYRIDIN-4-YL) BORONIC ACID; (2-(3-METHOXYPROPYL)PYRIDIN-4-YL)BORONIC ACID; (2-(4-CHLORO-BENZYL)-AMINOPYRIMIDIN-5-YL)BORONIC ACID; (2-(CYANOMETHYL)-1-OXOISOINDOLIN-4-YL) BORONIC ACID; (2-(CYANOMETHYL)-1-OXOISOINDOLIN-5-YL)BORONIC ACID; (2-(CYANOMETHYL)-1-OXOISOINDOLIN-6-YL) BORONIC ACID; (2-(CYANOMETHYL)-1-OXOISOINDOLIN-7-YL)BORONIC ACID; (2-(N-(3,4-DIMETHYLISOXAZOL-5-YL)-N-((2-METHOXYETHOXY)METHYL)SULFAMOYL) PHENYL)BORONIC ACID; (2-(N-(3,4-DIMETHYLISOXAZOL-5-YL)SULFAMOYL)PHENYL) BORONIC ACID; (2-(N-(TERT-BUTYL)SULFAMOYL)-5-ISOBUTYLTHIOPHEN-3-YL)BORONIC ACID; (2,2-DIMETHYL-2,3-DIHYDRO-1-BENZOFURAN-5-YL) BORANEDIOL; (2,3,5,6-TETRACHLOROPHENYL) BORANEDIOL; (2,3-DIFLUORO-4-PROPYLPHENYL)-BORONIC ACID; (2,3-DIMETHOXY-5-METHYLPHENYL)BORONIC ACID; (2,4-DIFLUORO-5-METHYLPHENYL)BORONIC ACID; (2,4-DIMETHYLTHIAZOLE)-5-BORONIC ACID; (2,6-DIETHYLPHENYL)BORONIC ACID; (2,6-DIMETHOXY-4-METHYLPHENYL)BORONIC ACID; (2,6-DIMETHOXY-4-PYRIMIDINYL)-BORONIC ACID; (2,6-DIMETHYL-4-METHOXYPHENYL)BORONIC ACID; (2-[(1-BENZYLPIPERIDIN-4-YL)AMINO]PYRIMIDIN-5-YL)BORONIC ACID; (2-[(1-ETHYL-1H-PYRAZOL-4-YL)METHOXY]-5-FLUOROPHENYL)BORANEDIOL; (2-[(1-ETHYL-1H-PYRAZOL-4-YL) METHOXY]-5-METHYLPHENYL)BORANEDIOL; (2-[(1-ETHYL-1H-PYRAZOL-4-YL)METHOXY]PHENYL) BORANEDIOL; (2-[(1-METHYL-1H-PYRAZOL-4-YL) METHOXY]PHENYL)BORANEDIOL; (2-[(1-PHENYLETHYL)AMINO]PYRIMIDIN-5-YL)BORONIC ACID; (2-[(2,2-DIMETHYLMORPHOLIN-4-YL) METHYL]-5-FLUOROPHENYL)BORANEDIOL; (2-[(2, 3-DIFLUOROPHENYL)METHOXY]PHENYL)BORANEDIOL; (2-[(2,3-DIMETHYLPIPERIDIN-1-YL) METHYL]PHENYL)BORANEDIOL; (2-[(2,4-DIFLUOROPHENYL)METHOXY]PHENYL) BORANEDIOL; (2-[(2,4-DIMETHYLPIPERIDIN-1-YL) METHYL]-5-FLUOROPHENYL)BORANEDIOL; (2-[(2, 5-DIFLUOROPHENYL)METHOXY]PHENYL) BORANEDIOL; (2-[(2,5-DIMETHYLPHENYL) METHOXY]PHENYL)BORANEDIOL; (2-[(2,6-DICHLOROPHENYL)METHOXY]PHENYL) BORANEDIOL; (2-[(2-BUTOXYETHOXY)METHYL]-5-FLUOROPHENYL)BORANEDIOL; (2-[(2-CHLORO-6-FLUOROPHENYL)METHOXY]PHENYL) BORANEDIOL; (2-[(2-CHLOROPHENYL)METHOXY]-5-FLUOROPHENYL)BORANEDIOL; (2-[(2-CHLOROPHENYL)METHOXY]-5-METHYLPHENYL) BORANEDIOL; (2-[(2E)-BUT-2-EN-1-YLOXY]-5-FLUOROPHENYL)BORANEDIOL; (2-[(2E)-BUT-2-EN-

1-YLOXY]-5-METHYLPHENYL)BORANEDIOL; (2-[(2E)-BUT-2-EN-1-YLOXY]NAPHTHALEN-1-YL)BORANEDIOL; (2-[(2E)-BUT-2-EN-1-YLOXY]PHENYL)BORANEDIOL; (2-[(2-FLUOROPHENYL)METHOXY]-5-METHYLPHENYL)BORANEDIOL; (2-[(2-FLUOROPHENYL)METHOXY]PHENYL)BORANEDIOL; (2-[(2-FURYLMETHYL)AMINO]PYRIMIDIN-5-YL)BORONIC ACID; (2-[(2-METHOXYETHYL)AMINO]PYRIMIDIN-5-YL)BORONIC ACID; (2-[(2-METHYLPENTYL)OXY]PHENYL)BORANEDIOL; (2-[(2-METHYLPHENYL)METHOXY]PHENYL)BORANEDIOL; (2-[(2-METHYLPROP-2-EN-1-YL)OXY]NAPHTHALEN-1-YL)BORANEDIOL; (2-[(2-METHYLPROP-2-EN-1-YL)OXY]PHENYL)BORANEDIOL; (2-[(2-PHENYLETHOXY)METHYL]PHENYL)BORANEDIOL; (2-[(2-PHENYLETHYL)AMINO]PYRIMIDIN-5-YL)BORONIC ACID; (2-[(3,3-DIMETHYLMORPHOLIN-4-YL)METHYL]-5-FLUOROPHENYL)BORANEDIOL; (2-[(3,4-DICHLOROPHENYL)METHOXY]PHENYL)BORANEDIOL; (2-[(3,4-DIMETHYLPHENYL)METHOXY]PHENYL)BORANEDIOL; (2-[(3,5-DIMETHYLPHENYL)METHOXY]PHENYL)BORANEDIOL; (2-[(3-CHLOROPHENYL)METHOXY]-5-FLUOROPHENYL)BORANEDIOL; (2-[(3-CHLOROPHENYL)METHOXY]-5-METHYLPHENYL)BORANEDIOL; (2-[(3-FLUOROPHENYL)METHOXY]-5-METHYLPHENYL)BORANEDIOL; (2-[(3-HYDROXYPROPYL)AMINO]PYRIMIDIN-5-YL)BORONIC ACID; (2-[(3-METHOXYPHENYL)METHOXY]PHENYL)BORANEDIOL; (2-[(3-METHYLBUT-2-EN-1-YL)OXY]NAPHTHALEN-1-YL)BORANEDIOL; (2-[(3-METHYLBUT-2-EN-1-YL)OXY]PHENYL)BORANEDIOL; (2-[(3-METHYLPHENYL)METHOXY]PHENYL)BORANEDIOL; (2-[(3-MORPHOLIN-4-YLPROPYL)AMINO]PYRIMIDIN-5-YL)BORONIC ACID; (2-[(3-PHENYLPROP-2-YN-1-YL)OXY]PHENYL)BORANEDIOL; (2-[(4,4-DIMETHYLPIPERIDIN-1-YL)METHYL]-5-FLUOROPHENYL)BORANEDIOL; (2-[(4,4-DIMETHYLPIPERIDIN-1-YL)METHYL]PHENYL)BORANEDIOL; (2-[(4-CHLORO-3,5-DIMETHYL-1H-PYRAZOL-1-YL)METHYL]-5-FLUOROPHENYL)BORANEDIOL; (2-[(4-CHLORO-3,5-DIMETHYL-1H-PYRAZOL-1-YL)METHYL]PHENYL)BORANEDIOL; (2-[(4-CHLOROPHENYL)METHOXY]-5-FLUOROPHENYL)BORANEDIOL; (2-[(4-CHLOROPHENYL)METHOXY]PHENYL)BORANEDIOL; (2-[(4-CYCLOPROPYLPIPERAZIN-1-YL)METHYL]PHENYL)BORANEDIOL; (2-[(4-ETHOXYPIPERIDIN-1-YL)METHYL]PHENYL)BORANEDIOL; (2-[(4-ETHYLPIPERAZIN-1-YL)METHYL]-5-FLUOROPHENYL)BORANEDIOL; (2-[(4-ETHYLPIPERIDIN-1-YL)METHYL]-5-FLUOROPHENYL)BORANEDIOL; (2-[(4-FLUOROPHENYL)METHOXY]-5-METHYLPHENYL)BORANEDIOL; (2-[(4-METHOXYBENZOYL)AMINO]PYRIMIDIN-5-YL)BORONIC ACID; (2-[(4-METHOXYPHENYL)AMINO]PYRIMIDIN-5-YL)BORONIC ACID; (2-[(4-METHYLPHENYL)METHOXY]PHENYL)BORANEDIOL; (2-[(4-METHYLPIPERAZIN-1-YL)METHYL]PHENYL)BORONIC ACID DIHYDROCHLORIDE; (2-[(4-PROPYLPIPERAZIN-1-YL)METHYL]PHENYL)BORANEDIOL; (2-[(4-PROPYLPIPERIDIN-1-YL)METHYL]PHENYL)BORANEDIOL; (2-[(BENZYLOXY)METHYL]-5-FLUOROPHENYL)BORANEDIOL; (2-[(BENZYLSULFANYL)METHYL]-5-FLUOROPHENYL)BORANEDIOL; (2-[(CYCLOHEPTYLOXY)METHYL]-5-FLUOROPHENYL)BORANEDIOL; (2-[(CYCLOHEXYLMETHOXY)METHYL]-5-FLUOROPHENYL)BORANEDIOL; (2-[(CYCLOHEXYLMETHOXY)METHYL]PHENYL)BORANEDIOL; (2-[(CYCLOPENTYLSULFANYL)METHYL]PHENYL)BORANEDIOL; (2-[(DIBUTYLAMINO)METHYL]PHENYL)BORANEDIOL; (2-[(DIISOPROPYLAMINO)CARBONYL]-3-METHOXYPHENYL)BORONIC ACID; (2-[(METHYLAMINO)SULFONYL]PHENYL)BORONIC ACID; (2-[(OCTYLOXY)METHYL]PHENYL)BORANEDIOL; (2-[(OXAN-4-YLMETHOXY)METHYL]PHENYL)BORANEDIOL; (2-[(OXAN-4-YLSULFANYL)METHYL]PHENYL)BORANEDIOL; (2-[(OXOLAN-3-YLOXY)METHYL]PHENYL)BORANEDIOL; (2-[(PYRIDIN-4-YLMETHYL)AMINO]PYRIMIDIN-5-YL)BORONIC ACID; (2-[(TERT-BUTOXYCARBONYL)AMINO]-5-FLUOROPHENYL)BORONIC ACID; (2-[2-(DIETHYLAMINO)ETHOXY]-5-FLUOROPHENYL)BORANEDIOL; (2-[2-(DIETHYLAMINO)ETHOXY]-5-METHYLPHENYL)BORANEDIOL; (2-[2-(DIETHYLAMINO)ETHOXY]PHENYL)BORANEDIOL; (2-[2-(DIMETHYLAMINO)ETHOXY]-5-FLUOROPHENYL)BORANEDIOL; (2-[2-(DIMETHYLAMINO)ETHOXY]-5-METHYLPHENYL)BORANEDIOL; (2-[2-(DIMETHYLAMINO)ETHOXY]NAPHTHALEN-1-YL)BORANEDIOL; (2-[2-(DIMETHYLAMINO)ETHOXY]PHENYL)BORANEDIOL; (2-[2-(MORPHOLIN-4-YL)ETHOXY]PHENYL)BORANEDIOL; (2-[2-(PIPERIDIN-1-YL)ETHOXY]PHENYL)BORANEDIOL; (2-[2-(PYRIDIN-2-YL)ETHOXY]PHENYL)BORANEDIOL; (2-[2-(PYRIDIN-4-YL)ETHOXY]PHENYL)BORANEDIOL; (2-[2-(PYRROLIDIN-1-YL)ETHOXY]PHENYL)BORANEDIOL; (2-[3-(2,2,2-TRIFLUOROETHOXY)PROPOXY]PHENYL)BORANEDIOL; (2-[BENZYL(METHYL)AMINO]PYRIMIDIN-5-YL)BORONIC ACID; (2-ACETYL-1-OXOISOINDOLIN-4-YL)BORONIC ACID; (2-ACETYL-1-OXOISOINDOLIN-5-YL)BORONIC ACID; (2-ACETYL-1-OXOISOINDOLIN-6-YL)BORONIC ACID; (2-ACETYL-1-OXOISOINDOLIN-7-YL)BORONIC ACID; (2-AMINO-4-CARBOXYPHENYL)BORONIC ACID; (2-AMINO-4-CYANO)BENZENEBORONIC ACID, HYDROCHLORIDE; (2-AMINO-4-METHOXYCARBONYLPHENYL)BORONIC ACID HYDROCHLORIDE; (2-AMINOPHENYL)BORONIC ACID HYDROCHLORIDE; (2-ANILINOPYRIMIDIN-5-YL)BORONIC ACID; (2-BENZYLPHENYL)BORANEDIOL; (2-BOC-AMINOMETHYL-5-FLUOROPHENYL)BORONIC ACID; (2-BOC-AMINOPHENYL)BORONIC ACID; (2-BUTOXYNAPHTHALEN-1-YL)BORANEDIOL; (2-CHLORO-3-HYDROXYPHENYL)-BORONIC ACID; (2-CHLORO-5-ISOPROPYLPHENYL)BORONIC ACID; (2-CHLORO-8-METHOXY-3-QUINOLINYL)-BORONIC ACID; (2-CYCLOHEXYLAMINOPYRIMIDIN-5-YL)BORONIC ACID; (2-ETHYL-1-OXOISOINDOLIN-4-YL)BORONIC ACID; (2-ETHYL-1-OXOISOINDOLIN-5-YL)BORONIC ACID; (2-ETHYL-1-OXOISOINDOLIN-6-YL)BORONIC ACID; (2-ETHYL-1-OXOISOINDOLIN-7-YL)BORONIC ACID; (2-ETHYNYLPHENYL)BORONIC ACID; (2-FLUORO-5-([(2-FLUOROPHENYL)SULFANYL]METHYL)PHENYL)BORANEDIOL; (2-FLUORO-5-([(2-METHYLPHENYL)SULFANYL]METHYL)PHENYL)BORANEDIOL; (2-FLUORO-5-([(3-METHOXYPROPYL)(METHYL)AMINO]METHYL)PHENYL)BORANEDIOL; (2-FLUORO-5-([(3-

METHYLPHENYL)SULFANYL]METHYL)PHENYL) BORANEDIOL; (2-FLUORO-5-([(4-FLUOROPHENYL) SULFANYL]METHYL)PHENYL)BORANEDIOL; (2-FLUORO-5-([(4-METHYLCYCLOHEXYL)OXY] METHYL)PHENYL)BORANEDIOL; (2-FLUORO-5-([(4-METHYLPHENYL)SULFANYL]METHYL)PHENYL) BORANEDIOL; (2-FLUORO-5-([(4-METHYLPYRIMIDIN-2-YL)SULFANYL]METHYL) PHENYL)BORANEDIOL; (2-FLUORO-5-([(5-METHYL-1,3,4-OXADIAZOL-2-YL)SULFANYL]METHYL) PHENYL)BORANEDIOL; (2-FLUORO-5-([(5-METHYLPYRIMIDIN-2-YL)SULFANYL]METHYL) PHENYL)BORANEDIOL; (2-FLUORO-5-([METHYL (OXAN-4-YL)AMINO]METHYL)PHENYL) BORANEDIOL; (2-FLUORO-5-([METHYL(PHENYL) AMINO]METHYL)PHENYL)BORANEDIOL; (2-FLUORO-5-[(2,2,3,3-TETRAFLUOROPROPOXY) METHYL]PHENYL)BORANEDIOL; (2-FLUORO-5-[(4-METHOXYPIPERIDIN-1-YL)METHYL]PHENYL)BO-RANEDIOL; (2-FLUORO-5-[(4-METHYL-1,4-DIAZEPAN-1-YL)METHYL]PHENYL)BORANEDIOL; (2-FLUORO-5-[(HEPTYLOXY)METHYL]PHENYL)BO-RANEDIOL; (2-FLUORO-5-[(OXAN-4-YLMETHOXY) METHYL]PHENYL)BORANEDIOL; (2-FLUORO-5-[(OXAN-4-YLSULFANYL)METHYL]PHENYL) BORANEDIOL; (2-ISOPROPOXY-5-TRIFLUOROMETHYLPHENYL)BORONIC ACID; (2-ISOPROPYL-1-OXOISOINDOLIN-4-YL)BORONIC ACID; (2-ISOPROPYL-1-OXOISOINDOLIN-5-YL)BO-RONIC ACID; (2-ISOPROPYL-1-OXOISOINDOLIN-7-YL)BORONIC ACID; (2-ISOPROPYLPYRIMIDIN-5-YL) BORONIC ACID; (2-METHOXY-5-([(3-METHOXYPROPYL)(METHYL)AMINO]METHYL) PHENYL)BORANEDIOL; (2-METHOXY-5-([(4-METHYLPENTYL)OXY]METHYL)PHENYL) BORANEDIOL; (2-METHOXY-5-([(5-METHYL-1,3,4-OXADIAZOL-2-YL)SULFANYL]METHYL)PHENYL) BORANEDIOL; (2-METHOXY-5-([2-(PROPAN-2-YLOXY)ETHOXY]METHYL)PHENYL)BORANEDIOL; (2-METHOXY-5-([METHYL(2,2,2-TRIFLUOROETHYL) AMINO]METHYL)PHENYL)BORANEDIOL; (2-METHOXY-5-([METHYL(3-METHYLBUTYL) AMINO]METHYL)PHENYL)BORANEDIOL; (2-METHOXY-5-([METHYL(PENTAN-3-YL)AMINO] METHYL)PHENYL)BORANEDIOL; (2-METHOXY-5-([METHYL(PENTYL)AMINO]METHYL)PHENYL)BO-RANEDIOL; (2-METHOXY-5-([PROPAN-2-YL (PROPYL)AMINO]METHYL)PHENYL)BORANEDIOL; (2-METHOXY-5-[(4-METHYLPIPERAZIN-1-YL) METHYL]PHENYL)BORANEDIOL; (2-METHOXY-5-[(4-METHYLPIPERIDIN-1-YL)METHYL]PHENYL)BO-RANEDIOL; (2-METHOXY-5-[(OXAN-4-YLOXY) METHYL]PHENYL)BORANEDIOL; (2-METHOXY-5-[(OXAN-4-YLSULFANYL)METHYL]PHENYL) BORANEDIOL; (2-METHOXY-5-[(PHENYLSULFANYL)METHYL]PHENYL) BORANEDIOL; (2-METHOXY-5-[(PYRIDIN-2-YLSULFANYL)METHYL]PHENYL)BORANEDIOL; (2-METHOXY-5-[(PYRIMIDIN-2-YLSULFANYL) METHYL]PHENYL)BORANEDIOL; (2-METHOXY-5-NITROPHENYL)BORONIC ACID; (2-METHOXY-5-PYRIDINYL)BORONIC ACID HYDROCHLORIDE; (2-METHOXY-6-METHYLPHENYL)BORONIC ACID; (2-METHYL-1,3-BENZOXAZOL-6-YL)BORONIC ACID; (2-METHYL-1-OXOISOINDOLIN-4-YL)BO-RONIC ACID; (2-METHYL-1-OXOISOINDOLIN-5-YL) BORONIC ACID; (2-METHYL-1-OXOISOINDOLIN-6-YL)BORONIC ACID; (2-METHYL-1-OXOISOINDOLIN-7-YL)BORONIC ACID; (2-METHYL-2,3-DIHYDRO-1-BENZOFURAN-5-YL)BORANEDIOL; (2-METHYL-3-CARBOXYPHENYL)BORONIC ACID; (2-METHYL-4-CARBOXYPHENYL)BORONIC ACID; (2-METHYL-5-NITROPHENYL)BORONIC ACID; (2-METHYL-5-PHENYL-3-THIENYL)-BORONIC ACID; (2-METHYL-5-QUINOLINYL)BORONIC ACID HYDRATE; (2-METHYLPYRIMIDIN-5-YL)BORONIC ACID; (2-METHYLQUINOLIN-5-YL)BORONIC ACID; (2-METHYLQUINOLIN-8-YL)BORANEDIOL; (2-OXO-2,3-DIHYDRO-1H-INDOL-5-YL)BORONIC ACID; (2-OXO-2,3-DIHYDRO-1H-PYRIDO[2,3-B][1,4] OXAZIN-7-YL)BORONIC ACID; (2-PHENOXYPYRIMI-DIN-5-YL)BORONIC ACID; (2-PIPERAZIN-1-YLPY-RIMIDIN-5-YL)BORONIC ACID; (2-PIPERIDIN-1-YLPYRIMIDIN-5-YL)BORONIC ACID; (2-PROPOXYNAPHTHALEN-1-YL)BORANEDIOL; (2-PROPOXYPYRIMIDIN-5-YL)BORONIC ACID; (2-PYRROLIDIN-1-YLPYRIMIDIN-5-YL)BORONIC ACID; (2-TERT-BUTYLPYRIMIDIN-5-YL)BORONIC ACID; (3-([(2,4-DIFLUOROPHENYL)SULFANYL] METHYL)PHENYL)BORANEDIOL; (3-([(2,4-DIMETH-YLPHENYL)SULFANYL]METHYL)PHENYL)BO-RANEDIOL; (3-([(2,5-DIFLUOROPHENYL) SULFANYL]METHYL)PHENYL)BORANEDIOL; (3-([(2,5-DIMETHYLPHENYL)SULFANYL]METHYL) PHENYL)BORANEDIOL; (3-([(2-CHLOROPHENYL) METHOXY]METHYL)PHENYL)BORANEDIOL; (3-([(2E)-3-PHENYLPROP-2-EN-1-YL]OXY)PHENYL) BORANEDIOL; (3-([(2-METHOXYPHENYL) SULFANYL]METHYL)PHENYL)BORANEDIOL; (3-([(3,4-DIFLUOROPHENYL)SULFANYL]METHYL) PHENYL)BORANEDIOL; (3-([(3,4-DIMETHYLPHENYL)SULFANYL]METHYL)PHENYL) BORANEDIOL; (3-([(3-CHLOROPHENYL)SULFANYL] METHYL)PHENYL)BORANEDIOL; (3-([(3-METHOXYPHENYL)SULFANYL]METHYL)PHENYL) BORANEDIOL; (3-([(3-METHOXYPROPYL)(METHYL) AMINO]METHYL)PHENYL)BORANEDIOL; (3-([(4,6-DIMETHYLPYRIMIDIN-2-YL)SULFANYL]METHYL) PHENYL)BORANEDIOL; (3-([(4-METHOXYPHENYL) SULFANYL]METHYL)PHENYL)BORANEDIOL; (3-([(4-METHYLPYRIMIDIN-2-YL)SULFANYL] METHYL)PHENYL)BORANEDIOL; (3-([(CYCLOBUTYLMETHYL)(METHYL)AMINO] METHYL)-4-METHOXYPHENYL)BORANEDIOL; (3-([CYCLOBUTYLMETHYL)(METHYL)AMINO] METHYL)PHENYL)BORANEDIOL; (3-([CYCLOHEXYLMETHYL)(METHYL)AMINO] METHYL)PHENYL)BORANEDIOL; (3-([4-(DIMETHYLAMINO)PIPERIDIN-1-YL]METHYL) PHENYL)BORANEDIOL; (3-([4-(PROPAN-2-YL) PIPERAZIN-1-YL]METHYL)PHENYL)BORANEDIOL; (3-([BENZYL(METHYL)AMINO]METHYL)PHENYL) BORANEDIOL; (3-([BIS(2-METHOXYETHYL)AMINO] METHYL)PHENYL)BORANEDIOL; (3-([BIS(2-METH-YLPROPYL)AMINO]METHYL)PHENYL) BORANEDIOL; (3-([BUTYL(ETHYL)AMINO] METHYL)-4-METHOXYPHENYL)BORANEDIOL; (3-([CYCLOHEPTYL(METHYL)AMINO]METHYL) PHENYL)BORANEDIOL; (3-([CYCLOHEXYL(ETHYL) AMINO]METHYL)PHENYL)BORANEDIOL; (3-([CYCLOPENTYL(METHYL)AMINO]METHYL)-4-METHOXYPHENYL)BORANEDIOL; (3-([CYCLOPROPYL(PROPYL)AMINO]METHYL)-4-METHOXYPHENYL)BORANEDIOL; (3-([ETHYL(2-

ETHYLBUTYL)AMINO]METHYL)PHENYL)BORANEDIOL; (3-([ETHYL(2-METHOXYETHYL)AMINO]METHYL)-4-METHOXYPHENYL)BORANEDIOL; (3-([ETHYL(2-METHYLPROPYL)AMINO]METHYL)-4-METHOXYPHENYL)BORANEDIOL; (3-([ETHYL(PHENYL)AMINO]METHYL)PHENYL)BORANEDIOL; (3-([METHYL(1-METHYLPIPERIDIN-4-YL)AMINO]METHYL)PHENYL)BORANEDIOL; (3-([METHYL(4-METHYLCYCLOHEXYL)AMINO]METHYL)PHENYL)BORANEDIOL; (3-([METHYL(PYRIDIN-2-YLMETHYL)AMINO]METHYL)PHENYL)BORANEDIOL; (3-([METHYL(PYRIDIN-3-YLMETHYL)AMINO]METHYL)PHENYL)BORANEDIOL; (3-([METHYL(PYRIDIN-4-YLMETHYL)AMINO]METHYL)PHENYL)BORANEDIOL; (3-(2-[(3-METHOXYPROPYL)(METHYL)AMINO]ETHOXY)PHENYL)BORANEDIOL; (3-(2-[(4-METHYLPENTYL)OXY]ETHOXY)PHENYL)BORANEDIOL; (3-(2-[(CYCLOBUTYLMETHYL)(METHYL)AMINO]ETHOXY)PHENYL)BORANEDIOL; (3-(2-[(TERT-BUTOXYCARBONYL)AMINO]ETHYL)PHENYL)BORONIC ACID; (3-(2-[2-(PROPAN-2-YLOXY)ETHOXY]ETHOXY)PHENYL)BORANEDIOL; (3-(2-[BUTYL(ETHYL)AMINO]ETHOXY)PHENYL)BORANEDIOL; (3-(2-[CYCLOPENTYL(METHYL)AMINO]ETHOXY)PHENYL)BORANEDIOL; (3-(2-[CYCLOPROPYL(PROPYL)AMINO]ETHOXY)PHENYL)BORANEDIOL; (3-(2-[ETHYL(2-METHOXYETHYL)AMINO]ETHOXY)PHENYL)BORANEDIOL; (3-(2-[ETHYL(2-METHYLPROPYL)AMINO]ETHOXY)PHENYL)BORANEDIOL; (3-(2-[METHYL(2,2,2-TRIFLUOROETHYL)AMINO]ETHOXY)PHENYL)BORANEDIOL; (3-(2-[METHYL(3-METHYLBUTYL)AMINO]ETHOXY)PHENYL)BORANEDIOL; (3-(2-[METHYL(PENTAN-3-YL)AMINO]ETHOXY)PHENYL)BORANEDIOL; (3-(2-[METHYL(PENTYL)AMINO]ETHOXY)PHENYL)BORANEDIOL; (3-(2-[PROPAN-2-YL(PROPYL)AMINO]ETHOXY)PHENYL)BORANEDIOL; (3-(3-BENZYOXY)PROPOXY)PHENYL BORONIC ACID; (3,4-DIETHOXYPHENYL)BORANEDIOL; (3,4-DIPROPOXYPHENYL)BORANEDIOL; (3,5-DIMETHOXY-D6)-PHENYLBORONIC ACID; (3,5-DIMETHOXYPHENYL)METHANOL-4-BORONIC ACID; (3,5-DIMETHYL-1-PHENYL-1H-PYRAZOL-4-YL)BORANEDIOL; (3,5-DIMETHYL-D6)-PHENYLBORONIC ACID; (3,5-DINITRO-2-METHYLPHENYL)BORONIC ACID; (3,5-DIPHENYLPHENYL)BORONIC ACID; (3,6-DIAMINO-9-ACRIDINYL)-BORONIC ACID; (3-[(1-METHYL-1H-PYRAZOL-4-YL)METHOXY]PHENYL)BORANEDIOL; (3-[(1-METHYLPIPERIDIN-2-YL)METHOXY]PHENYL)BORONIC ACID; (3-[(2,3-DIFLUOROPHENYL)METHOXY]PHENYL)BORANEDIOL; (3-[(2,4-DIFLUOROPHENYL)METHOXY]PHENYL)BORANEDIOL; (3-[(2,5-DIFLUOROPHENYL)METHOXY]PHENYL)BORANEDIOL; (3-[(2,5-DIMETHYLPHENYL)METHOXY]PHENYL)BORANEDIOL; (3-[(2-CHLORO-4-FLUOROPHENYL)METHOXY]PHENYL)BORANEDIOL; (3-[(2-CHLORO-6-FLUOROPHENYL)METHOXY]PHENYL)BORANEDIOL; (3-[(2E)-BUT-2-EN-1-YLOXY]PHENYL)BORANEDIOL; (3-[(2-METHYL-1,4-OXAZEPAN-4-YL)METHYL]PHENYL)BORANEDIOL; (3-[(2-METHYLPENTYL)OXY]PHENYL)BORANEDIOL; (3-[(2-METHYLPHENYL)METHOXY]PHENYL)BORANEDIOL; (3-[(2-METHYLPROP-2-EN-1-YL)OXY]PHENYL)BORANEDIOL; (3-[(2-PHENYLETHOXY)METHYL]PHENYL)BORANEDIOL; (3-[(3,4-DICHLOROPHENYL)METHOXY]PHENYL)BORANEDIOL; (3-[(3,4-DIMETHYLPHENYL)METHOXY]PHENYL)BORANEDIOL; (3-[(3,5-DIMETHYL-1H-1,2,4-TRIAZOL-1-YL)METHYL]-4-METHOXYPHENYL)BORANEDIOL; (3-[(3,5-DIMETHYL-1H-PYRAZOL-1-YL)METHYL]-4-METHOXYPHENYL)BORANEDIOL; (3-[(3,5-DIMETHYLPHENYL)METHOXY]PHENYL)BORANEDIOL; (3-[(3-METHYLBUT-2-EN-1-YL)OXY]PHENYL)BORANEDIOL; (3-[(3-METHYLPHENYL)METHOXY]PHENYL)BORANEDIOL; (3-[(3-PHENYLPROP-2-YN-1-YL)OXY]PHENYL)BORANEDIOL; (3-[(4,4-DIMETHYLPIPERIDIN-1-YL)METHYL]PHENYL)BORANEDIOL; (3-[(4,5-DIMETHYL-1H-IMIDAZOL-1-YL)METHYL]PHENYL)BORANEDIOL; (3-[(4-CHLORO-3,5-DIMETHYL-1H-PYRAZOL-1-YL)METHYL]PHENYL)BORANEDIOL; (3-[(4-CYCLOPROPYLPIPERAZIN-1-YL)METHYL]PHENYL)BORANEDIOL; (3-[(4-ETHOXYPIPERIDIN-1-YL)METHYL]PHENYL)BORANEDIOL; (3-[(4-METHYLPHENYL)METHOXY]PHENYL)BORANEDIOL; (3-[(4-METHYLPIPERAZIN-1-YL)METHYL]PHENYL)BORONIC ACID DIHYDROCHLORIDE; (3-[(4-PROPYLPIPERAZIN-1-YL)METHYL]PHENYL)BORANEDIOL; (3-[(4-PROPYLPIPERIDIN-1-YL)METHYL]PHENYL)BORANEDIOL; (3-[(CYCLOHEXYLMETHOXY)METHYL]PHENYL)BORANEDIOL; (3-[(CYCLOHEXYLOXY)METHYL]-4-METHOXYPHENYL)BORANEDIOL; (3-[(CYCLOHEXYLSULFANYL)METHYL]-4-METHOXYPHENYL)BORANEDIOL; (3-[(CYCLOPENTYLSULFANYL)METHYL]PHENYL)BORANEDIOL; (3-[(DIBUTYLAMINO)METHYL]PHENYL)BORANEDIOL; (3-[(DIPROPYLAMINO)METHYL]-4-METHOXYPHENYL)BORANEDIOL; (3-[(HEXYLOXY)METHYL]-4-METHOXYPHENYL)BORANEDIOL; (3-[(OCTYLOXY)METHYL]PHENYL)BORANEDIOL; (3-[(OXAN-4-YLMETHOXY)METHYL]PHENYL)BORANEDIOL; (3-[(OXAN-4-YLSULFANYL)METHYL]PHENYL)BORANEDIOL; (3-[(OXOLAN-3-YLOXY)METHYL]PHENYL)BORANEDIOL; (3-[(TERT-BUTOXYCARBONYL)AMINO]-5-METHYLISOXAZOL-4-YL)BORONIC ACID; (3-[(TRIMETHYLSILYL)ETHYNYL]PHENYL)BORONIC ACID; (3-[1-(DIMETHYLAMINO)ETHYL]PHENYL)BORONIC ACID; (3-[2-(1,4-OXAZEPAN-4-YL)ETHOXY]PHENYL)BORANEDIOL; (3-[2-(1,4-THIAZEPAN-4-YL)ETHOXY]PHENYL)BORANEDIOL; (3-[2-(3,5-DIMETHYL-1H-1,2,4-TRIAZOL-1-YL)ETHOXY]PHENYL)BORANEDIOL; (3-[2-(3,5-DIMETHYL-1H-PYRAZOL-1-YL)ETHOXY]PHENYL)BORANEDIOL; (3-[2-(4,5-DIMETHYL-1H-IMIDAZOL-1-YL)ETHOXY]PHENYL)BORANEDIOL; (3-[2-(4-METHYLPIPERAZIN-1-YL)ETHOXY]PHENYL)BORANEDIOL; (3-[2-(4-METHYLPIPERIDIN-1-YL)ETHOXY]PHENYL)BORANEDIOL; (3-[2-(AZEPAN-1-YL)ETHOXY]PHENYL)BORANEDIOL; (3-[2-(CYCLOHEXYLOXY)ETHOXY]PHENYL)BORANEDIOL; (3-[2-(CYCLOHEXYLSULFANYL)ETHOXY]PHENYL)BORANEDIOL; (3-[2-(DIETHYLAMINO)ETHOXY]PHENYL)BORANEDIOL; (3-[2-(DIMETHYLAMINO)ETHOXY]PHENYL)BORANEDIOL; (3-[2-(DIPROPYLAMINO)ETHOXY]PHENYL)BORANEDIOL; (3-[2-(HEXYLOXY)ETHOXY

PHENYL)BORANEDIOL; (3-[2-(OXAN-4-YLOXY)ETHOXY]PHENYL)BORANEDIOL; (3-[2-(OXAN-4-YLSULFANYL)ETHOXY]PHENYL)BORANEDIOL; (3-[2-(PHENYLSULFANYL)ETHOXY]PHENYL)BORANEDIOL; (3-[2-(PIPERIDIN-1-YL)ETHOXY]PHENYL)BORANEDIOL; (3-[2-(PYRIDIN-2-YL)ETHOXY]PHENYL)BORANEDIOL; (3-[2-(PYRIDIN-2-YLSULFANYL)ETHOXY]PHENYL)BORANEDIOL; (3-[2-(PYRIDIN-4-YL)ETHOXY]PHENYL)BORANEDIOL; (3-[2-(PYRIMIDIN-2-YLSULFANYL)ETHOXY]PHENYL)BORANEDIOL; (3-[2-(PYRROLIDIN-1-YL)ETHOXY]PHENYL)BORANEDIOL; (3-[3-(2,2,2-TRIFLUOROETHOXY)PROPOXY]PHENYL)BORANEDIOL; (3-[4-(TERT-BUTOXYCARBONYL)PIPERAZIN-1-YL]PHENYL)BORONIC ACID; (3-ACETAMIDO-2-NITRO)BENZENEBORONIC ACID; (3-ACETAMIDOMETHYLPHENYL)BORONIC ACID; (3-ALLYLAMINOCARBONYL)BENZENEBORONIC ACID; (3-AMINO-4-CHLOROPHENYL)BORONIC ACID HYDROCHLORIDE; (3-AMINO-5-METHOXYCARBONYLPHENYL)BORONIC ACID; (3-AMINO-5-NITROPHENYL)BORONIC ACID; (3-AMINO-5-NITROPHENYL)BORONIC ACID HYDROCHLORIDE; (3-AMINOMETHYLPHENYL)BORONIC ACID; (3-AMINOMETHYLPHENYL)BORONIC ACID HYDROCHLORIDE; (3-BENZYLOXYCARBONYL-5-NITROPHENYL)BORONIC ACID; (3-BOC-AMINO-4-METHYLPHENYL)BORONIC ACID; (3-BOC-AMINO-5-NITROPHENYL)BORONIC ACID; (3-BOC-AMINOPHENYL)BORONIC ACID; (3-CARBAMOTHIOYL)BENZENEBORONIC ACID; (3-CHLORO-4-ETHOXYCARBONYL)BENZENEBORONIC ACID; (3-CHLORO-4-METHOXYCARBONYL)BENZENEBORONIC ACID; (3-CHLORO-5-CYANOPHENYL)BORONIC ACID; (3-CYCLOHEXYLPROPYL)BORONIC ACID; (3-ETHOXYCARBONYL-5-NITROPHENYL)BORONIC ACID; (3-ETHYL-1H-INDAZOL-4-YL)BORONIC ACID; (3-FLUORO-4-([(2-FLUOROPHENYL)SULFANYL]METHYL)PHENYL)BORANEDIOL; (3-FLUORO-4-([(2-METHYLPHENYL)SULFANYL]METHYL)PHENYL)BORANEDIOL; (3-FLUORO-4-[[(3-METHOXYPROPYL)(METHYL)AMINO]METHYL]PHENYL)BORANEDIOL; (3-FLUORO-4-([(3-METHYLPHENYL)SULFANYL]METHYL)PHENYL)BORANEDIOL; (3-FLUORO-4-([(4-FLUOROPHENYL)SULFANYL]METHYL)PHENYL)BORANEDIOL; (3-FLUORO-4-([(4-METHYLCYCLOHEXYL)OXY]METHYL)PHENYL)BORANEDIOL; (3-FLUORO-4-([(4-METHYLPHENYL)SULFANYL]METHYL)PHENYL)BORANEDIOL; (3-FLUORO-4-([(4-METHYLPYRIMIDIN-2-YL)SULFANYL]METHYL)PHENYL)BORANEDIOL; (3-FLUORO-4-([(5-METHYL-1,3,4-OXADIAZOL-2-YL)SULFANYL]METHYL)PHENYL)BORANEDIOL; (3-FLUORO-4-([(5-METHYLPYRIMIDIN-2-YL)SULFANYL]METHYL)PHENYL)BORANEDIOL; (3-FLUORO-4-([METHYL(OXAN-4-YL)AMINO]METHYL)PHENYL)BORANEDIOL; (3-FLUORO-4-([METHYL(PHENYL)AMINO]METHYL)PHENYL)BORANEDIOL; (3-FLUORO-4-[(2,2,3,3-TETRAFLUOROPROPOXY)METHYL]PHENYL)BORANEDIOL; (3-FLUORO-4-[4-METHOXYPIPERIDIN-1-YL)METHYL]PHENYL)BORANEDIOL; (3-FLUORO-4-[4-METHYL-1,4-DIAZEPAN-1-YL)METHYL]PHENYL)BORANEDIOL; (3-FLUORO-4-[(HEPTYLOXY)METHYL]PHENYL)BORANEDIOL; (3-FLUORO-4-[(OXAN-4-YLMETHOXY)METHYL]PHENYL)BORANEDIOL; (3-FLUORO-4-[(OXAN-4-YLSULFANYL)METHYL]PHENYL)BORANEDIOL; (3-FLUORO-5-METHOXYCARBONYLPHENYL)BORONIC ACID; (3-FLUORO-5-TRIFLUOROMETHYLPHENYL)BORONIC ACID; (3-FORMYLOXYPHENYL)BORONIC ACID; (3-METHANESULFONYLAMINOMETHYLPHENYL)BORONIC ACID; (3-METHYL-4-[(2-METHYLPROP-2-EN-1-YL)OXY]PHENYL)BORANEDIOL; (3-METHYL-4-[(3-METHYLBUT-2-EN-1-YL)OXY]PHENYL)BORANEDIOL; (3-METHYL-4-CARBOXYPHENYL)BORONIC ACID; (3-METHYL-5-METHOXY-D6)-PHENYLBORONIC ACID; (3-NITRO-4-ISOBUTYLPHENYL)BORONIC ACID; (3-PHENYLAMINOCARBONYLPHENYL)BORONIC ACID; (3-T-BUTYL-5-METHYLPHENYL)BORONIC ACID; (3-TERT-BUTOXYPHENYL)BORONIC ACID; (4-((1-METHYL-1H-IMIDAZOL-4-YL)METHOXY)PHENYL)BORONIC ACID; (4-([(1,3-DIMETHYL-1H-PYRAZOL-5-YL)SULFANYL]METHYL)-3-FLUOROPHENYL)BORANEDIOL; (4-([(2,4-DIFLUOROPHENYL)SULFANYL]METHYL)PHENYL)BORANEDIOL; (4-([(2,4-DIMETHYLPHENYL)SULFANYL]METHYL)PHENYL)BORANEDIOL; (4-([(2,5-DIFLUOROPHENYL)SULFANYL]METHYL)PHENYL)BORANEDIOL; (4-([(2,5-DIMETHYLPHENYL)SULFANYL]METHYL)PHENYL)BORANEDIOL; (4-([(2-CHLOROPHENYL)METHOXY]METHYL)PHENYL)BORANEDIOL; (4-([(2-CHLOROPHENYL)SULFANYL]METHYL)-3-FLUOROPHENYL)BORANEDIOL; (4-([(2-METHOXYPHENYL)SULFANYL]METHYL)PHENYL)BORANEDIOL; (4-([(3,4-DIFLUOROPHENYL)SULFANYL]METHYL)PHENYL)BORANEDIOL; (4-([(3,4-DIMETHYLPHENYL)SULFANYL]METHYL)PHENYL)BORANEDIOL; (4-([(3-CHLOROPHENYL)SULFANYL]METHYL)-3-FLUOROPHENYL)BORANEDIOL; (4-([(3-CHLOROPHENYL)SULFANYL]METHYL)PHENYL)BORANEDIOL; (4-([(3-METHOXYPHENYL)SULFANYL]METHYL)PHENYL)BORANEDIOL; (4-([(3-METHOXYPROPYL)(METHYL)AMINO]METHYL)PHENYL)BORANEDIOL; (4-([(3-METHYLCYCLOHEXYL)SULFANYL]METHYL)PHENYL)BORANEDIOL; (4-([(4,6-DIMETHYLPYRIMIDIN-2-YL)SULFANYL]METHYL)PHENYL)BORANEDIOL; (4-([(4-CHLOROPHENYL)SULFANYL]METHYL)-3-FLUOROPHENYL)BORANEDIOL; (4-([(4-METHOXYPHENYL)SULFANYL]METHYL)PHENYL)BORANEDIOL; (4-([(4-METHYLPYRIMIDIN-2-YL)SULFANYL]METHYL)PHENYL)BORANEDIOL; (4-([(5-METHYL-1,3,4-OXADIAZOL-2-YL)SULFANYL]METHYL)PHENYL)BORANEDIOL; (4-([(CYCLOBUTYLMETHYL)(METHYL)AMINO]METHYL)-3-FLUOROPHENYL)BORANEDIOL; (4-([(CYCLOBUTYLMETHYL)(METHYL)AMINO]METHYL)PHENYL)BORANEDIOL; (4-([(CYCLOHEXYLMETHYL)(METHYL)AMINO]METHYL)PHENYL)BORANEDIOL; (4-([(CYCLOPROPYLMETHYL)(PROPYL)AMINO]METHYL)-3-FLUOROPHENYL)BORANEDIOL; (4-([(TERT-BUTOXYCARBONYL)(METHYL)AMINO]METHYL)PHENYL)BORONIC ACID; (4-([4-(DIMETHYLAMINO)PIPERIDIN-1-YL]METHYL)PHENYL)BORANEDIOL; (4-([4-(PROPAN-2-YL)PIPERAZIN-1-YL]METHYL)PHENYL)BORANEDIOL; (4-([BENZYL(METHYL)AMINO]METHYL)PHENYL)BORANEDIOL; (4-([BIS(2-METHOXYETHYL)AMINO]

METHYL)PHENYL)BORANEDIOL; (4-([BIS(2-METHYLPROPYL)AMINO]METHYL)PHENYL)BORANEDIOL; (4-([BUTYL(CYCLOPROPYL)AMINO]METHYL)-3-FLUOROPHENYL)BORANEDIOL; (4-([CYCLOHEPTYL(METHYL)AMINO]METHYL)PHENYL)BORANEDIOL; (4-([CYCLOHEXYL(ETHYL)AMINO]METHYL)PHENYL)BORANEDIOL; (4-([CYCLOHEXYL(METHYL)AMINO]METHYL)-3-FLUOROPHENYL)BORANEDIOL; (4-([CYCLOPENTYL(ETHYL)AMINO]METHYL)-3-FLUOROPHENYL)BORANEDIOL; (4-([CYCLOPROPYL(2-METHOXYETHYL)AMINO]METHYL)-3-FLUOROPHENYL)BORANEDIOL; (4-([ETHYL(2-ETHYLBUTYL)AMINO]METHYL)PHENYL)BORANEDIOL; (4-([ETHYL(PHENYL)AMINO]METHYL)PHENYL)BORANEDIOL; (4-([METHYL(1-METHYLPIPERIDIN-3-YL)AMINO]METHYL)PHENYL)BORANEDIOL; (4-([METHYL(1-METHYLPIPERIDIN-4-YL)AMINO]METHYL)PHENYL)BORANEDIOL; (4-([METHYL(4-METHYLCYCLOHEXYL)AMINO]METHYL)PHENYL)BORANEDIOL; (4-([METHYL(PYRIDIN-2-YLMETHYL)AMINO]METHYL)PHENYL)BORANEDIOL; (4-([METHYL(PYRIDIN-3-YLMETHYL)AMINO]METHYL)PHENYL)BORANEDIOL; (4-([METHYL(PYRIDIN-4-YLMETHYL)AMINO]METHYL)PHENYL)BORANEDIOL; (4-(2-[(3-METHOXYPROPYL)(METHYL)AMINO]ETHOXY)PHENYL)BORANEDIOL; (4-(2-[(4-METHYLPENTYL)OXY]ETHOXY)PHENYL)BORANEDIOL; (4-(2-[(CYCLOBUTYLMETHYL)(METHYL)AMINO]ETHOXY)PHENYL)BORANEDIOL; (4-(2-[(TERT-BUTOXYCARBONYL)AMINO]ETHYL)PHENYL)BORONIC ACID; (4-(2-[2-(PROPAN-2-YLOXY)ETHOXY]ETHOXY)PHENYL)BORANEDIOL; (4-(2-[BUTYL(ETHYL)AMINO]ETHOXY)PHENYL)BORANEDIOL; (4-(2-[CYCLOPENTYL(METHYL)AMINO]ETHOXY)PHENYL)BORANEDIOL; (4-(2-[CYCLOPROPYL(PROPYL)AMINO]ETHOXY)PHENYL)BORANEDIOL; (4-(2-[ETHYL(2-METHOXYETHYL)AMINO]ETHOXY)PHENYL)BORANEDIOL; (4-(2-[ETHYL(2-METHYLPROPYL)AMINO]ETHOXY)PHENYL)BORANEDIOL; (4-(2-[METHYL(2,2,2-TRIFLUOROETHYL)AMINO]ETHOXY)PHENYL)BORANEDIOL; (4-(2-[METHYL(3-METHYLBUTYL)AMINO]ETHOXY)PHENYL)BORANEDIOL; (4-(2-[METHYL(PENTAN-3-YL)AMINO]ETHOXY)PHENYL)BORANEDIOL; (4-(2-[METHYL(PENTYL)AMINO]ETHOXY)PHENYL)BORANEDIOL; (4-(2-[PROPAN-2-YL(PROPYL)AMINO]ETHOXY)PHENYL)BORANEDIOL; (4-(2-AMINO-2-OXOETHOXY)PHENYL)BORONIC ACID; (4-(2-HYDROXYETHYL)PIPERAZIN-1-YL)(3-BORONOPHENYL)METHANONE, HCL; (4-(2-MORPHOLINO-2-OXOETHOXY)PHENYL)BORONIC ACID; (4-(2-OXO-2-THIOMORPHOLINOETHOXY)PHENYL)BORONIC ACID; (4-(2S)-3-AMINO-2-[(TERT-BUTOXYCARBONYL)AMINO]-3-OXOPROPYLPHENYL)BORONIC ACID; (4-(4-(2-(DIMETHYLAMINO)ACETYL)PIPERAZIN-1-YL)PHENYL)BORONIC ACID; (4-(4-(2-HYDROXYETHYL)PIPERAZIN-1-YL)PHENYL)BORONIC ACID; (4-(4-BENZYLPIPERAZIN-1-YL)PHENYL)BORONIC ACID; (4-(4-ETHYLPIPERAZIN-1-YL)PHENYL)BORONIC ACID; (4-(4-ISOPROPYLPIPERAZIN-1-YL)PHENYL)BORONIC ACID; (4-(4-PROPYLPIPERAZIN-1-YL)PHENYL)BORONIC ACID; (4-(5H,6H,7H,8H-IMIDAZO[1,2-A]PYRAZIN-7-YLMETHYL)PHENYL)BORANEDIOL; (4-[(1-METHYL-1H-PYRAZOL-4-YL)METHOXY]PHENYL)BORANEDIOL; (4-[(1-METHYLPIPERIDIN-2-YL)METHOXY]PHENYL)BORONIC ACID; (4-[(2,2-DIMETHYLMORPHOLIN-4-YL)METHYL]-3-FLUOROPHENYL)BORANEDIOL; (4-[(2,3-DIMETHYLPIPERIDIN-1-YL)METHYL]-3-FLUOROPHENYL)BORANEDIOL; (4-[(2,4-DICHLOROPHENYL)METHOXY]PHENYL)BORANEDIOL; (4-[(2,4-DIFLUOROPHENYL)METHOXY]PHENYL)BORANEDIOL; (4-[(2,5-DIFLUOROPHENYL)METHOXY]PHENYL)BORANEDIOL; (4-[(2,5-DIMETHYLPHENYL)METHOXY]PHENYL)BORANEDIOL; (4-[(2-BUTOXYETHOXY)METHYL]-3-FLUOROPHENYL)BORANEDIOL; (4-[(2-CHLORO-4-FLUOROPHENYL)METHOXY]PHENYL)BORANEDIOL; (4-[(2-CHLORO-6-FLUOROPHENYL)METHOXY]PHENYL)BORANEDIOL; (4-[(2-CHLOROPHENYL)METHOXY]PHENYL)BORANEDIOL; (4-[(2E)-BUT-2-EN-1-YLOXY]PHENYL)BORANEDIOL; (4-[(2-METHYL-1,4-OXAZEPAN-4-YL)METHYL]PHENYL)BORANEDIOL; (4-[(2-METHYLPENTYL)OXY]PHENYL)BORANEDIOL; (4-[(2-METHYLPHENYL)METHOXY]PHENYL)BORANEDIOL; (4-[(2-METHYLPROP-2-EN-1-YL)OXY]PHENYL)BORANEDIOL; (4-[(2-PHENYLETHOXY)METHYL]PHENYL)BORANEDIOL; (4-[(3,3-DIMETHYLMORPHOLIN-4-YL)METHYL]-3-FLUOROPHENYL)BORANEDIOL; (4-[(3,4-DICHLOROPHENYL)METHOXY]PHENYL)BORANEDIOL; (4-[(3,4-DIMETHYLPHENYL)METHOXY]PHENYL)BORANEDIOL; (4-[(3,5-DIMETHYLPHENYL)METHOXY]PHENYL)BORANEDIOL; (4-[(3-METHYLBUT-2-EN-1-YL)OXY]PHENYL)BORANEDIOL; (4-[(3-METHYLPHENYL)METHOXY]PHENYL)BORANEDIOL; (4-[(3-PHENYLPROP-2-YN-1-YL)OXY]PHENYL)BORANEDIOL; (4-[(4,4-DIMETHYLPIPERIDIN-1-YL)METHYL]-3-FLUOROPHENYL)BORANEDIOL; (4-[(4,4-DIMETHYLPIPERIDIN-1-YL)METHYL]PHENYL)BORANEDIOL; (4-[(4,5-DIMETHYL-1H-IMIDAZOL-1-YL)METHYL]-3-FLUOROPHENYL)BORANEDIOL; (4-[(4-CHLORO-3,5-DIMETHYL-1H-PYRAZOL-1-YL)METHYL]-3-FLUOROPHENYL)BORANEDIOL; (4-[(4-CHLORO-3,5-DIMETHYL-1H-PYRAZOL-1-YL)METHYL]PHENYL)BORANEDIOL; (4-[(4-CYCLOPROPYLPIPERAZIN-1-YL)METHYL]PHENYL)BORANEDIOL; (4-[(4-ETHOXYPIPERIDIN-1-YL)METHYL]PHENYL)BORANEDIOL; (4-[(4-ETHYLPIPERAZIN-1-YL)METHYL]-3-FLUOROPHENYL)BORANEDIOL; (4-[(4-ETHYLPIPERIDIN-1-YL)METHYL]-3-FLUOROPHENYL)BORANEDIOL; (4-[(4-METHYLPIPERAZIN-1-YL)METHYL]PHENYL)BORONIC ACID; (4-[(4-PROPYLPIPERAZIN-1-YL)METHYL]PHENYL)BORANEDIOL; (4-[(4-PROPYLPIPERIDIN-1-YL)METHYL]PHENYL)BORANEDIOL; (4-[(BENZYLOXY)METHYL]-3-FLUOROPHENYL)BORANEDIOL; (4-[(BENZYLSULFANYL)METHYL]-3-FLUOROPHENYL)BORANEDIOL; (4-[(CYCLOHEPTYLOXY)METHYL]-3-FLUOROPHENYL)BORANEDIOL; (4-[(CYCLOHEXYLMETHOXY)METHYL]-3-FLUOROPHENYL)BORANEDIOL; (4-[(CYCLOHEXYLMETHOXY)METHYL]PHENYL)

BORANEDIOL; (4-[(CYCLOPENTYLSULFANYL) METHYL]PHENYL)BORANEDIOL; (4-[(DIBUTYLAMINO)METHYL]PHENYL) BORANEDIOL; (4-[(DIMETHYLAMINO)METHYL] PHENYL)BORONIC ACID HYDROCHLORIDE; (4-[(OCTYLOXY)METHYL]PHENYL)BORANEDIOL; (4-[(OXAN-4-YLMETHOXY)METHYL]PHENYL) BORANEDIOL; (4-[(OXAN-4-YLSULFANYL) METHYL]PHENYL)BORANEDIOL; (4-[(OXOLAN-3-YLOXY)METHYL]PHENYL)BORANEDIOL; (4-[(TERT-BUTOXYCARBONYL)AMINO]PYRIDIN-3-YL) BORONIC ACID; (4-[(TRIMETHYLSILYL)ETHYNYL] PHENYL)BORONIC ACID; (4-[[TERT-BUTYL (DIMETHYL)SILYL]OXY]-2-METHOXYPHENYL) BORONIC ACID; (4-[1-(1-PIPERIDINYL)ETHYL] PHENYL)BORONIC ACID; (4-[1-(1-PYRROLIDINYL) ETHYL]PHENYL)BORONIC ACID; (4-[1-(4-MORPHOLINYL)ETHYL]PHENYL)BORONIC ACID; (4-[1-(DIMETHYLAMINO)ETHYL]PHENYL)BORONIC ACID; (4-[2-(1,4-OXAZEPAN-4-YL)ETHOXY]PHENYL)BORANEDIOL; (4-[2-(1,4-THIAZEPAN-4-YL) ETHOXY]PHENYL)BORANEDIOL; (4-[2-(3,5-DIMETHYL-1H-1,2,4-TRIAZOL-1-YL)ETHOXY]PHENYL) BORANEDIOL; (4-[2-(3,5-DIMETHYL-1H-PYRAZOL-1-YL)ETHOXY]PHENYL)BORANEDIOL; (4-[2-(4,5-DIMETHYL-1H-IMIDAZOL-1-YL)ETHOXY]PHENYL) BORANEDIOL; (4-[2-(4-METHYLPIPERAZIN-1-YL) ETHOXY]PHENYL)BORANEDIOL; (4-[2-(4-METHYLPIPERIDIN-1-YL)ETHOXY]PHENYL) BORANEDIOL; (4-[2-(AZEPAN-1-YL)ETHOXY] PHENYL)BORANEDIOL; (4-[2-(CYCLOHEXYLOXY) ETHOXY]PHENYL)BORANEDIOL; (4-[2-(CYCLOHEXYLSULFANYL)ETHOXY]PHENYL) BORANEDIOL; (4-[2-(DIETHYLAMINO)ETHOXY] PHENYL)BORANEDIOL; (4-[2-(DIMETHYLAMINO) ETHOXY]-3-METHYLPHENYL)BORANEDIOL; (4-[2-(DIMETHYLAMINO)ETHOXY]PHENYL) BORANEDIOL; (4-[2-(DIPROPYLAMINO)ETHOXY] PHENYL)BORANEDIOL; (4-[2-(HEXYLOXY) ETHOXY]PHENYL)BORANEDIOL; (4-[2-(MORPHOLIN-4-YL)ETHOXY]PHENYL) BORANEDIOL; (4-[2-(OXAN-4-YLOXY)ETHOXY] PHENYL)BORANEDIOL; (4-[2-(OXAN-4-YLSULFANYL)ETHOXY]PHENYL)BORANEDIOL; (4-[2-(PHENYLSULFANYL)ETHOXY]PHENYL) BORANEDIOL; (4-[2-(PIPERIDIN-1-YL)ETHOXY] PHENYL)BORANEDIOL; (4-[2-(PYRIDIN-2-YL) ETHOXY]PHENYL)BORANEDIOL; (4-[2-(PYRIDIN-2-YLSULFANYL)ETHOXY]PHENYL)BORANEDIOL; (4-[2-(PYRIDIN-4-YL)ETHOXY]PHENYL)BORANEDIOL; (4-[2-(PYRIMIDIN-2-YLSULFANYL)ETHOXY]PHENYL)BORANEDIOL; (4-[2,2':6',2''-TERPYRIDIN]-4'-YLPHENYL)-4'-BORONIC ACID; (4-[3-(2,2,2-TRIFLUOROETHOXY)PROPOXY]PHENYL)BORANEDIOL; (4-[3-(PIPERIDIN-1-YL)PROPOXY]PHENYL)BORANEDIOL; (4-[4-(DIMETHYLAMINO)BUTYL]PHENYL)BORONIC ACID; (4-ACETAMIDOMETHYLPHENYL)BORONIC ACID; (4-ALLYLAMINOCARBONYL) BENZENEBORONIC ACID; (4-AMINO-2-FLUOROPHENYL)BORONIC ACID; (4-AMINOSULFONYLPHENYL)BORONIC ACID; (4-BENZYLOXYCARBONYL-2-NITRO)BENZENEBORONIC ACID; (4-BOC-AMINOPHENYL)BORONIC ACID; (4-BUTOXY-3-METHYLPHENYL)BORANEDIOL; (4-CBZ-AMINOPHENYL)BORONIC ACID; (4-CHLORO-2-ETHOXYCARBONYL)BENZENEBORONIC ACID; (4-CHLORO-2-METHYLTHIAZOLO[4,5-C]PYRIDIN-7-YL)BORONIC ACID; (4-CHLORO-3-HYDROXYPHENYL)BORONIC ACID; (4-CYANO-2-NITROPHENYL)BORONIC ACID; (4-ETHOXY-2-ETHYLPHENYL)BORONIC ACID; (4-ETHOXY-3,5-DIMETHOXYPHENYL)BORONIC ACID; (4-ETHOXY-3-TRIFLUOROMETHYLPHENYL)BORONIC ACID; (4-FLUORO-5-ISOPROPYL-2-METHOXYPHENYL)BORONIC ACID; (4-FLUOROPHENYLAMINOMETHYL)-4-BENZENEBORONIC ACID; (4-FLUOROPHENYLAMINOMETHYLENE)-4-BENZENEBORONIC ACID; (4-HEXYL-2-THIENYL)-BORONIC ACID; (4-HYDROXY-2-METHYL)PHENYLBORONIC ACID; (4-HYDROXY-3-NITROPHENYL)BORONIC ACID; (4-ISOPROPYL-2-METHOXYPHENYL)BORONIC ACID; (4-METHANESULFONYLAMINOMETHYLPHENYL)BORONIC ACID; (4-METHOXY-2,6-DIMETHYLPHENYL)BORONIC ACID HYDRATE; (4-METHOXY-3-[[(3-METHOXYPROPYL)(METHYL) AMINO]METHYL)PHENYL)BORANEDIOL; (4-METHOXY-3-([(4-METHYLPENTYL)OXY] METHYL)PHENYL)BORANEDIOL; (4-METHOXY-3-([(5-METHYL-1,3,4-OXADIAZOL-2-YL)SULFANYL] METHYL)PHENYL)BORANEDIOL; (4-METHOXY-3-([2-(PROPAN-2-YLOXY)ETHOXY]METHYL)PHENYL) BORANEDIOL; (4-METHOXY-3-([METHYL(2,2,2-TRIFLUOROETHYL)AMINO]METHYL)PHENYL) BORANEDIOL; (4-METHOXY-3-([METHYL(3-METHYLBUTYL)AMINO]METHYL)PHENYL) BORANEDIOL; (4-METHOXY-3-([METHYL(PENTAN-3-YL)AMINO]METHYL)PHENYL)BORANEDIOL; (4-METHOXY-3-([METHYL(PENTYL)AMINO] METHYL)PHENYL)BORANEDIOL; (4-METHOXY-3-([PROPAN-2-YL(PROPYL)AMINO]METHYL)PHENYL)BORANEDIOL; (4-METHOXY-3-[(4-METHYLPIPERAZIN-1-YL)METHYL]PHENYL) BORANEDIOL; (4-METHOXY-3-[(4-METHYLPIPERIDIN-1-YL)METHYL]PHENYL) BORANEDIOL; (4-METHOXY-3-[(OXAN-4-YLOXY) METHYL]PHENYL)BORANEDIOL; (4-METHOXY-3-[(OXAN-4-YLSULFANYL)METHYL]PHENYL) BORANEDIOL; (4-METHOXY-3-[(PHENYLSULFANYL)METHYL]PHENYL) BORANEDIOL; (4-METHOXY-3-[(PYRIDIN-2-YLSULFANYL)METHYL]PHENYL)BORANEDIOL; (4-METHOXY-3-[(PYRIMIDIN-2-YLSULFANYL) METHYL]PHENYL)BORANEDIOL; (4-METHOXY-3-TRIFLUOROMETHYLPHENYL)BORONIC ACID; (4-METHOXYCARBONYLMETHYL)PHENYLBORONIC ACID; (4-METHYL-1-NAPHTHALENE)BORONIC ACID; (4-METHYL-2-NITROPHENYL)BORONIC ACID; (4-OXO-1,4-DIHYDROQUINAZOLIN-6-YL)BORONIC ACID; (4-PHENYLAMINOCARBONYLPHENYL)BORONIC ACID; (4-PROPOXY-3-METHYLPHENYL)BORONIC ACID; (4-PYRROLIDIN-1-YLPHENYL)BORONIC ACID; (4-SEC-BUTYLPHENYL)BORONIC ACID; (4-TERT-BUTYL-2-METHOXYPHENYL)BORONIC ACID; (4-THIOMORPHOLINOPHENYL)BORONIC ACID; (5-([(1,3-DIMETHYL-1H-PYRAZOL-5-YL)SULFANYL]METHYL)-2-FLUOROPHENYL)BORANEDIOL; (5-([(2-CHLOROPHENYL)SULFANYL] METHYL)-2-FLUOROPHENYL)BORANEDIOL; (5-([(3-CHLOROPHENYL)SULFANYL]METHYL)-2-FLUOROPHENYL)BORANEDIOL; (5-([(4-CHLOROPHENYL)SULFANYL]METHYL)-2-FLUOROPHENYL)BORANEDIOL; (5-([(CYCLOBUTYLMETHYL)(METHYL)AMINO]

METHYL)-2-FLUOROPHENYL)BORANEDIOL; (5-([(CYCLOBUTYLMETHYL)(METHYL)AMINO]METHYL)-2-METHOXYPHENYL)BORANEDIOL; (5-([(CYCLOPROPYLMETHYL)(PROPYL)AMINO]METHYL)-2-FLUOROPHENYL)BORANEDIOL; (5-([(TERT-BUTOXYCARBONYL)AMINO]METHYL)PYRIDIN-3-YL)BORONIC ACID; (5-([BUTYL(CYCLOPROPYL)AMINO]METHYL)-2-FLUOROPHENYL)BORANEDIOL; (5-([BUTYL(ETHYL)AMINO]METHYL)-2-METHOXYPHENYL)BORANEDIOL; (5-([CYCLOHEXYL(METHYL)AMINO]METHYL)-2-FLUOROPHENYL)BORANEDIOL; (5-([CYCLOPENTYL(ETHYL)AMINO]METHYL)-2-FLUOROPHENYL)BORANEDIOL; (5-([CYCLOPENTYL(METHYL)AMINO]METHYL)-2-METHOXYPHENYL)BORANEDIOL; (5-([CYCLOPROPYL(2-M ETHOXYETHYL)AMINO]METHYL)-2-FLUOROPHENYL)BORANEDIOL; (5-([CYCLOPROPYL(PROPYL)AMINO]METHYL)-2-METHOXYPHENYL)BORANEDIOL; (5-([ETHYL(2-METHOXYETHYL)AMINO]METHYL)-2-METHOXYPHENYL)BORANEDIOL; (5-([ETHYL(2-METHYL)PROPYL)AMINO]METHYL)-2-METHOXYPHENYL)BORANEDIOL; (5-(METHYLTHIO)PYRIDIN-3-YLTHIO)METHYLBORONIC ACID; (5'-(PIPERIDIN-2-YL)-[3,3'-BIPYRIDIN]-5-YL)BORONIC ACID; (5'-(PROP-1-YN-1-YL)[3,3'-BIPYRIDIN]-5-YL)BORONIC ACID; (5,7-DICHLORO-1,2-DIHYDRO-2-OXO-3-QUINOLINYL)-BORONIC ACID; (5-[(2,2-DIMETHYLMORPHOLIN-4-YL)METHYL]-2-FLUOROPHENYL)BORANEDIOL; (5-[(2-BUTOXYETHOXY)METHYL]-2-FLUOROPHENYL)BORANEDIOL; (5-[(3,3-DIMETHYLMORPHOLIN-4-YL)METHYL]-2-FLUOROPHENYL)BORANEDIOL; (5-[(3,5-DIMETHYL-1H-1,2,4-TRIAZOL-1-YL)METHYL]-2-METHOXYPHENYL)BORANEDIOL; (5-[(3,5-DIMETHYL-1H-PYRAZOL-1-YL)METHYL]-2-METHOXYPHENYL)BORANEDIOL; (5-[(4,4-DIMETHYLPIPERIDIN-1-YL)METHYL]-2-FLUOROPHENYL)BORANEDIOL; (5-[(4-ETHYLPIPERAZIN-1-YL)METHYL]-2-FLUOROPHENYL)BORANEDIOL; (5-[(4-ETHYLPIPERIDIN-1-YL)METHYL]-2-FLUOROPHENYL)BORANEDIOL; (5-[(ACETYLAMINO)METHYL]PYRIDIN-3-YL)BORONIC ACID; (5-[(BENZYLOXY)METHYL]-2-FLUOROPHENYL)BORANEDIOL; (5-[(BENZYLSULFANYL)METHYL]-2-FLUOROPHENYL)BORANEDIOL; (5-[(CYCLOHEPTYLOXY)METHYL]-2-FLUOROPHENYL)BORANEDIOL; (5-[(CYCLOHEXYLMETHOXY)METHYL]-2-FLUOROPHENYL)BORANEDIOL; (5-[(CYCLOHEXYLOXY)METHYL]-2-METHOXYPHENYL)BORANEDIOL; (5-[(CYCLOHEXYLSULFANYL)METHYL]-2-METHOXYPHENYL)BORANEDIOL; (5-[(DIPROPYLAMINO)METHYL]-2-METHOXYPHENYL)BORANEDIOL; (5-[(HEXYLOXY)METHYL]-2-METHOXYPHENYL)BORANEDIOL; (5-ACETAMIDO-2-NITRO)BENZENEBORONIC ACID; (5-AMINO-1-NAPHTHALENYL)-BORONIC ACID; (5-AMINO-2-HYDROXYMETHYLPHENYL)BORONIC ACID, HCL, DIHYDRATE; (5-CHLORO-2-[(2,2-DIMETHYLPROPOXY)CARBONYL]PHENYL)BORONIC ACID; (5-CHLORO-2-METHOXYPYRIDIN-4-YL)BORONIC ACID; (5-CHLOROBENZO[B]THIOPHEN-2-YL)BORONIC ACID; (5-FLUORO-2-([(2-FLUOROPHENYL)SULFANYL]METHYL)PHENYL)BORANEDIOL; (5-FLUORO-2-([(2-METHYLPHENYL)SULFANYL]METHYL)PHENYL)BORANEDIOL; (5-FLUORO-2-([(3-METHOXYPROPYL)(METHYL)AMINO]METHYL)PHENYL)BORANEDIOL; (5-FLUORO-2-([(3-METHYLPHENYL)SULFANYL]METHYL)PHENYL)BORANEDIOL; (5-FLUORO-2-([(4-FLUOROPHENYL)SULFANYL]METHYL)PHENYL)BORANEDIOL; (5-FLUORO-2-([(4-METHYLCYCLOHEXYL)OXY]METHYL)PHENYL)BORANEDIOL; (5-FLUORO-2-([(4-METHYLPHENYL)SULFANYL]METHYL)PHENYL)BORANEDIOL; (5-FLUORO-2-([(4-METHYLPYRIMIDIN-2-YL)SULFANYL]METHYL)PHENYL)BORANEDIOL; (5-FLUORO-2-([(5-METHYL-1,3,4-OXADIAZOL-2-YL)SULFANYL]METHYL)PHENYL)BORANEDIOL; (5-FLUORO-2-([(5-METHYLPYRIMIDIN-2-YL)SULFANYL]METHYL)PHENYL)BORANEDIOL; (5-FLUORO-2-([METHYL(OXAN-4-YL)AMINO]METHYL)PHENYL)BORANEDIOL; (5-FLUORO-2-([METHYL(PHENYL)AMINO]METHYL)PHENYL)BORANEDIOL; (5-FLUORO-2-[(1-METHYL-1H-PYRAZOL-4-YL)METHOXY]PHENYL)BORANEDIOL; (5-FLUORO-2-[(2,2,3,3-TETRAFLUOROPROPOXY)METHYL]PHENYL)BORANEDIOL; (5-FLUORO-2-[(2-FLUOROPHENYL)METHOXY]PHENYL)BORANEDIOL; (5-FLUORO-2-[(2-METHYLPROP-2-EN-1-YL)OXY]PHENYL)BORANEDIOL; (5-FLUORO-2-[(3-FLUOROPHENYL)METHOXY]PHENYL)BORANEDIOL; (5-FLUORO-2-[(3-METHYLBUT-2-EN-1-YL)OXY]PHENYL)BORANEDIOL; (5-FLUORO-2-[(4-METHOXYPIPERIDIN-1-YL)METHYL]PHENYL)BORANEDIOL; (5-FLUORO-2-[(4-METHYL-1,4-DIAZEPAN-1-YL)METHYL]PHENYL)BORANEDIOL; (5-FLUORO-2-[(4-METHYLPHENYL)METHOXY]PHENYL)BORANEDIOL; (5-FLUORO-2-[(HEPTYLOXY)METHYL]PHENYL)BORANEDIOL; (5-FLUORO-2-[(OXAN-4-YLMETHOXY)METHYL]PHENYL)BORANEDIOL; (5-FLUORO-2-[(OXAN-4-YLSULFANYL)METHYL]PHENYL)BORANEDIOL; (5-FLUORO-2-[2-(2,2,2-TRIFLUOROETHOXY)ETHOXY]PHENYL)BORANEDIOL; (5-FLUORO-2-[2-(3-METHYLBUTOXY)ETHOXY]PHENYL)BORANEDIOL; (5-FLUORO-2-[2-(MORPHOLIN-4-YL)ETHOXY]PHENYL)BORANEDIOL; (5-FLUORO-2-[2-(PIPERIDIN-1-YL)ETHOXY]PHENYL)BORANEDIOL; (5-FLUORO-2-[2-(PYRIDIN-2-YL)ETHOXY]PHENYL)BORANEDIOL; (5-FLUORO-2-[2-(PYRIDIN-4-YL)ETHOXY]PHENYL)BORANEDIOL; (5-FLUORO-2-[2-(PYRROLIDIN-1-YL)ETHOXY]PHENYL)BORANEDIOL; (5-FLUORO-2-[3-(PYRROLIDIN-1-YL)PROPOXY]PHENYL)BORANEDIOL; (5-FLUORO-2-THIENYL)BORONIC ACID; (5-HYDROXYPYRIDIN-2-YL)BORONIC ACID; (5-ISOPROPYL-1H-INDAZOL-4-YL)BORONIC ACID; (5-METHYL-2-[(1-METHYL-1H-PYRAZOL-4-YL)METHOXY]PHENYL)BORANEDIOL; (5-METHYL-2-[(2-METHYLPENTYL)OXY]PHENYL)BORANEDIOL; (5-METHYL-2-[(2-METHYLPHENYL)METHOXY]PHENYL)BORANEDIOL; (5-METHYL-2-[(2-METHYLPROP-2-EN-1-YL)OXY]PHENYL)BORANEDIOL; (5-METHYL-2-[(3-METHYLBUT-2-EN-1-YL)OXY]PHENYL)BORANEDIOL; (5-METHYL-2-[(3-METHYLPHENYL)METHOXY]PHENYL)BORANEDIOL; (5-METHYL-2-[(4-METHYLPHENYL)METHOXY]PHENYL)BORANEDIOL; (5-METHYL-2-

[2-(2,2,2-TRIFLUOROETHOXY)ETHOXY]PHENYL) BORANEDIOL; (5-METHYL-2-[2-(3-METHYLBUTOXY)ETHOXY]PHENYL)BORANEDIOL; (5-METHYL-2-[2-(MORPHOLIN-4-YL)ETHOXY]PHENYL)BORANEDIOL; (5-METHYL-2-[2-(PIPERIDIN-1-YL)ETHOXY]PHENYL)BORANEDIOL; (5-METHYL-2-[2-(PYRIDIN-2-YL)ETHOXY]PHENYL)BORANEDIOL; (5-METHYL-2-[2-(PYRIDIN-4-YL)ETHOXY]PHENYL) BORANEDIOL; (5-METHYL-2-[2-(PYRROLIDIN-1-YL)ETHOXY]PHENYL)BORANEDIOL; (5-METHYL-2-[3-(PYRROLIDIN-1-YL)PROPOXY]PHENYL) BORANEDIOL; (5-PHENOXY-3-PYRIDINYL) BORONIC ACID; (5-TRIFLUOROMETHYLBENZO[B]THIOPHEN-2-YL)BORONIC ACID; (6-(TERT-BUTOXYCARBONYL)-5,6,7,8-TETRAHYDRO-1,6-NAPHTHYRIDIN-3-YL)BORONIC ACID; (6-AMINOPYRIDIN-3-YL)BORONIC ACID; (6-ETHOXY-5-FLUOROPYRIDIN-3-YL)BORONIC ACID; (7-BUTYL-2-NAPHTHALENYL)BORONIC ACID; (7-CHLORO-1-BENZOTHIOPHEN-2-YL)BORANEDIOL; (7-HEPTYL-2-NAPHTHALENYL)BORONIC ACID; (8-METHOXY-2-METHYL-5-QUINOLINYL)BORONIC ACID TRIHYDRATE; (8-METHOXY-2-METHYLQUINOLIN-5-YL)BORONIC ACID; (8-METHOXY-2-METHYLQUINOLIN-5-YL)BORONIC ACID TRIHYDRATE; (8-METHOXYQUINOLIN-5-YL) BORONIC ACID; (8-METHYL-5-QUINOLINYL)BORONIC ACID HYDRATE; (9-ETHYL-9H-CARBAZOL-3-YL)BORONIC ACID; (9-METHYL-9H-CARBAZOL-3-YL)BORONIC ACID; (E)-(2-(FURAN-2-YL)VINYL) BORONIC ACID; (E)-(2-CYCLOPENTYLETHENYL) BORONIC ACID; (E)-3-((1H-PYRROL-2-YL)METHYLENE)-2-OXOINDOLIN-5-YLBORONIC ACID; (E)-3-(3-ETHOXY-3-OXOPROP-1-ENYL)-2-FLUOROPHENYLBORONIC ACID; (E)-3-(TRIFLUOROMETHYL)STYRYLBORONIC ACID; (E)-3-ACETOXYPROP-1-ENYLBORONIC ACID; (E)-3-METHOXYSTYRYLBORONIC ACID; (E)-3-PHENOXYPROP-1-ENYLBORONIC ACID; (E)-4-(N'-HYDROXYCARBAMIMIDOYL)PHENYLBORONIC ACID; (E)-4-AMINOBUT-2-ENYLBORONIC ACID HYDROCHLORIDE; (E)-5-(2-ETHOXYCARBONYLETHEN-1-YL)-2-FLUOROPHENYLBORONIC ACID; (E)-5-CHLORO-1-PENTENEBORONIC ACID; (E)-BUT-2-EN-2-YLBORONIC ACID; (FURAN-2-YLMETHYL) BORONIC ACID; (M-ACRYLAMIDOPHENYL) BORONIC ACID; (PYRIDIN-2-YLTHIO) METHYLBORONIC ACID; (PYRIDINE-D4)-4-BORONIC ACID; (PYRIMIDINE-2-D1)-5-BORONIC ACID; (S)-4-(2-AMINO-3-TERT-BUTOXY-3-OXOPROPYL)PHENYLBORONIC ACID; (Z)-CYCLOOCTENYLBORONIC ACID; [1-(TERT-BUTOXYCARBONYL)-1H-PYRROLO[2,3-B]PYRIDIN-2-YL]BORONIC ACID; [1,2,4]TRIAZOLO[1,5-A]PYRIDINE-6-BORONIC ACID; [1,2,5]OXADIAZOLO[3,4-B]PYRIDIN-6-YLBORONIC ACID; [1,3]DIOXOLO[4,5-B]PYRIDINE-6-BORONIC ACID; [10-(1-NAPHTHALENYL)-9-ANTHRACENYL] BORONIC ACID; [10-[4-(2-NAPHTHALENYL)PHENYL]-9-ANTHRACENYL]-BORONIC ACID; [2-(([(2-METHYLPHENYL)METHYL]SULFANYL)METHYL) PHENYL]BORANEDIOL; [2-(([(3-METHYLPHENYL) METHYL]SULFANYL)METHYL)PHENYL] BORANEDIOL; [2-((METHYL[(1-METHYL-1H-IMIDAZOL-2-YL)METHYL]AMINO)METHYL) PHENYL]BORANEDIOL; [2-(1,4-DIOXA-8-AZASPIRO[4.5]DEC-8-YL)PYRIMIDIN-5-YL]BORONIC ACID; [2-(1,4-OXAZEPAN-4-YLMETHYL)PHENYL] BORANEDIOL; [2-(1H-INDAZOL-1-YLMETHYL) PHENYL]BORANEDIOL; [2-(1H-PYRAZOL-1-YL) PYRIMIDIN-5-YL]BORONIC ACID; [2-(1H-PYRROL-1-YL)PYRIMIDIN-5-YL]BORONIC ACID; [2-(2,2,2-TRIFLUOROETHOXY)NAPHTHALEN-1-YL] BORANEDIOL; [2-(2,2,2-TRIFLUOROETHOXY) PYRIMIDIN-5-YL]BORONIC ACID; [2-(2,3-DICHLOROPHENOXYMETHYL)PHENYL] BORANEDIOL; [2-(2,3-DIFLUOROPHENOXYMETHYL)PHENYL] BORANEDIOL; [2-(2,3-DIHYDRO-1H-INDOL-1-YLMETHYL)PHENYL]BORANEDIOL; [2-(2,3-DIHYDRO-1H-ISOINDOL-2-YLMETHYL)PHENYL] BORANEDIOL; [2-(2,3-DIMETHYLPHENOXYMETHYL)PHENYL] BORANEDIOL; [2-(2,4-DICHLOROPHENOXYMETHYL)PHENYL] BORANEDIOL; [2-(2,4-DIFLUOROPHENOXYMETHYL)PHENYL] BORANEDIOL; [242,4-DIMETHYLPHENOXYMETHYL)PHENYL] BORANEDIOL; [2-(2,5-DICHLOROPHENOXYMETHYL)PHENYL] BORANEDIOL; [2-(2,5-DIMETHYL-1H-PYRROL-1-YL) PYRIMIDIN-5-YL]BORONIC ACID; [2-(2,5-DIMETHYLPHENOXYMETHYL)PHENYL] BORANEDIOL; [2-(2,6-DICHLOROPHENOXYMETHYL)PHENYL] BORANEDIOL; [2-(2,6-DIMETHYLMORPHOLIN-4-YL)PYRIMIDIN-5-YL]BORONIC ACID; [2-(2,6-DIMETHYLPHENOXYMETHYL)PHENYL] BORANEDIOL; [2-(2-CHLORO-4-FLUOROPHENOXYMETHYL)PHENYL] BORANEDIOL; [2-(2-CHLORO-4-METHYLPHENOXYMETHYL)PHENYL] BORANEDIOL; [2-(2-CHLORO-5-METHYLPHENOXYMETHYL)PHENYL] BORANEDIOL; [2-(2-CHLOROPHENOXYMETHYL)-5-FLUOROPHENYL]BORANEDIOL; [2-(2-ETHOXYETHOXY)-5-FLUOROPHENYL] BORANEDIOL; [2-(2-ETHOXYETHOXY)-5-METHYLPHENYL]BORANEDIOL; [2-(2-ETHOXYETHOXY)NAPHTHALEN-1-YL] BORANEDIOL; [2-(2-ETHYLPHENOXYMETHYL) PHENYL]BORANEDIOL; [2-(2-METHOXYETHOXY)-5-METHYLPHENYL]BORANEDIOL; [2-(2-METHOXYETHOXY)NAPHTHALEN-1-YL] BORANEDIOL; [2-(2-METHOXYPHENOXYMETHYL) PHENYL]BORANEDIOL; [2-(2-METHYLBUTOXY) PHENYL]BORANEDIOL; [2-(2-METHYLPROPOXY) NAPHTHALEN-1-YL]BORANEDIOL; [2-(2-PHENOXYETHOXY)PHENYL]BORANEDIOL; [2-(2-PHENYLETHOXY)PHENYL]BORANEDIOL; [2-(3,4-DICHLOROPHENOXYMETHYL)PHENYL] BORANEDIOL; [243,4-DIFLUOROPHENOXYMETHYL)PHENYL] BORANEDIOL; [2-(3,4-DIMETHYLPHENOXYMETHYL)PHENYL] BORANEDIOL; [243,5-DICHLOROPHENOXYMETHYL)PHENYL] BORANEDIOL; [2-(3,5-DIMETHYL-1H-PYRAZOL-1-YL)-4-METHOXYPHENYL]BORONIC ACID; [2-(3,5-DIMETHYL-1H-PYRAZOL-1-YL)-4-METHOXYPHENYL]BORONIC ACID HYDROCHLORIDE; [2-(3,5-DIMETHYL-1H-PYRAZOL-1-YL)-4-METHYLPHENYL]BORONIC ACID; [2-(3,5-DIMETHYLPHENOXYMETHYL)PHENYL]BO-

RANEDIOL; [2-(3-CHLOROPHENOXYMETHYL)-5-FLUOROPHENYL]BORANEDIOL; [2-(3-ETHYLPHENOXYMETHYL)PHENYL]BORANEDIOL; [2-(3-METHOXYPHENOXYMETHYL)PHENYL]BORANEDIOL; [2-(3-METHOXYPROPOXY)NAPHTHALEN-1-YL]BORANEDIOL; [2-(3-METHYLBUTOXY)NAPHTHALEN-1-YL]BORANEDIOL; [2-(3-METHYLBUTOXY)PHENYL]BORANEDIOL; [2-(3-PHENYLPROPOXY)PHENYL]BORANEDIOL; [2-(4-CHLORO-2-METHYLPHENOXYMETHYL)PHENYL]BORANEDIOL; [2-(4-CHLORO-3-METHYLPHENOXYMETHYL)PHENYL]BORANEDIOL; [2-(4-CHLOROPHENOXYMETHYL)-5-FLUOROPHENYL]BORANEDIOL; [2-(4-ETHYLPHENOXYMETHYL)PHENYL]BORANEDIOL; [2-(4-METHOXYPHENOXYMETHYL)PHENYL]BORANEDIOL; [2-(4-N-BOC-PIPERAZIN-1-YL)PYRIMIDIN-5-YL]BORONIC ACID; [2-(ALLYLAMINO)PYRIMIDIN-5-YL]BORONIC ACID; [2-(AZEPAN-1-YLMETHYL)PHENYL]BORONIC ACID HYDROCHLORIDE; [2-(AZOCAN-1-YLMETHYL)-5-FLUOROPHENYL]BORANEDIOL; [2-(BENZYLAMINO)PYRIMIDIN-5-YL]BORONIC ACID; [2-(BUT-3-EN-2-YLOXY)-5-FLUOROPHENYL]BORANEDIOL; [2-(BUT-3-EN-2-YLOXY)-5-METHYLPHENYL]BORANEDIOL; [2-(BUT-3-EN-2-YLOXY)PHENYL]BORANEDIOL; [2-(BUTAN-2-YLOXY)-5-FLUOROPHENYL]BORANEDIOL; [2-(BUTAN-2-YLOXY)-5-METHYLPHENYL]BORANEDIOL; [2-(BUTAN-2-YLOXY)NAPHTHALEN-1-YL]BORANEDIOL; [2-(BUTAN-2-YLOXY)PHENYL]BORANEDIOL; [2-(CYCLOBUTOXYMETHYL)-5-FLUOROPHENYL]BORANEDIOL; [2-(CYCLOBUTOXYMETHYL)PHENYL]BORANEDIOL; [2-(CYCLOHEXYLMETHOXY)-5-FLUOROPHENYL]BORANEDIOL; [2-(CYCLOHEXYLMETHOXY)-5-METHYLPHENYL]BORANEDIOL; [2-(CYCLOHEXYLMETHOXY)PHENYL]BORANEDIOL; [2-(CYCLOHEXYLOXY)-5-FLUOROPHENYL]BORANEDIOL; [2-(CYCLOHEXYLOXY)-5-METHYLPHENYL]BORANEDIOL; [2-(CYCLOHEXYLOXY)PHENYL]BORANEDIOL; [2-(CYCLOPENTYLMETHOXY)-5-FLUOROPHENYL]BORANEDIOL; [2-(CYCLOPENTYLMETHOXY)-5-METHYLPHENYL]BORANEDIOL; [2-(CYCLOPENTYLOXY)-5-FLUOROPHENYL]BORANEDIOL; [2-(CYCLOPENTYLOXY)-5-METHYLPHENYL]BORANEDIOL; [2-(CYCLOPENTYLOXY)NAPHTHALEN-1-YL]BORANEDIOL; [2-(CYCLOPENTYLOXY)PHENYL]BORANEDIOL; [2-(CYCLOPROPYLMETHOXY)NAPHTHALEN-1-YL]BORANEDIOL; [2-(DIBENZYLAMINO)PYRIMIDIN-5-YL]BORONIC ACID; [2-(DIETHYLAMINO)PYRIMIDIN-5-YL]BORONIC ACID; [2-(DIMETHYLAMINO)PHENYL]BORONIC ACID HYDROCHLORIDE HYDRATE; [2-(E-3-METHOXY-3-OXO-1-PROPEN-1-YL)PHENYL]BORONIC ACID; [2-(HEPTYLOXY)-5-METHYLPHENYL]BORANEDIOL; [2-(HEPTYLOXY)PHENYL]BORANEDIOL; [2-(HEXYLOXY)-5-METHYLPHENYL]BORANEDIOL; [2-(HEXYLOXY)PHENYL]BORANEDIOL; [2-(MORPHOLIN-4-YLMETHYL)PHENYL]BORONIC ACID HYDROCHLORIDE; [2-(NONYLOXY)PHENYL]BORANEDIOL; [2-(OCTAHYDROQUINOLIN-1(2H)-YL)PYRIMIDIN-5-YL]BORONIC ACID; [2-(OCTYLOXY)PHENYL]BORANEDIOL; [2-(OXAN-2-YLMETHOXY)PHENYL]BORANEDIOL; [2-(OXAN-4-YLMETHOXY)PHENYL]BORANEDIOL; [2-(OXOLAN-2-YLMETHOXY)PHENYL]BORANEDIOL; [2-(OXOLAN-3-YLOXY)PHENYL]BORANEDIOL; [2-(PENTYLOXY)NAPHTHALEN-1-YL]BORANEDIOL; [2-(PENTYLOXY)PHENYL]BORANEDIOL; [2-(PIPERIDIN-1-YLMETHYL)PHENYL]BORONIC ACID HYDROCHLORIDE; [2-(PROP-2-EN-1-YLOXY)NAPHTHALEN-1-YL]BORANEDIOL; [2-(PYRIDIN-3-YLMETHOXY)PHENYL]BORANEDIOL; [2-(PYRIMIDIN-2-YLMETHOXY)PHENYL]BORANEDIOL; [2-(PYRROLIDIN-1-YLMETHYL)PHENYL]BORONIC ACID HYDROCHLORIDE; [2-(TRIFLUOROMETHOXY)PYRIMIDIN-5-YL]BORONIC ACID; [2-(TRIFLUOROMETHYL)QUINAZOLIN-4-YL]BORONIC ACID; [2-(TRIFLUOROMETHYL)QUINOLIN-5-YL]BORONIC ACID; [2-(TRIFLUOROMETHYL)QUINOLIN-6-YL]BORONIC ACID; [2,4-BIS(PROPAN-2-YL)PHENYL]BORANEDIOL; [2-[(TERT-BUTOXYCARBONYL)AMINO]PYRIMIDIN-5-YL]BORONIC ACID; [2-[2-(TRIPHENYLMETHYL)-2H-TETRAZOL-5-YL]PHENYL]BORONIC ACID; [2-AMINO-5-(TRIFLUOROMETHYL)PHENYL]BORONIC ACID; [2-FLUORO-3-(METHOXYCARBONYL)PHENYL]BORONIC ACID; [2-FLUORO-3-(TRIFLUOROMETHOXY)PHENYL]BORONIC ACID; [2-FLUORO-5-(1,4-OXAZEPAN-4-YLMETHYL)PHENYL]BORANEDIOL; [2-FLUORO-5-(2-FLUOROPHENOXYMETHYL)PHENYL]BORANEDIOL; [2-FLUORO-5-(2-METHYLPHENOXYMETHYL)PHENYL]BORANEDIOL; [2-FLUORO-5-(3-FLUOROPHENOXYMETHYL)PHENYL]BORANEDIOL; [2-FLUORO-5-(3-METHYLPHENOXYMETHYL)PHENYL]BORANEDIOL; [2-FLUORO-5-(4-FLUOROPHENOXYMETHYL)PHENYL]BORANEDIOL; [2-FLUORO-5-(4-METHYLPHENOXYMETHYL)PHENYL]BORANEDIOL; [2-METHOXY-5-(1,4-OXAZEPAN-4-YLMETHYL)PHENYL]BORANEDIOL; [2-METHOXY-5-(1,4-THIAZEPAN-4-YLMETHYL)PHENYL]BORANEDIOL; [2-METHOXY-5-(PHENOXYMETHYL)PHENYL]BORANEDIOL; [3-(([(2-METHYLPHENYL)METHYL]SULFANYL)METHYL)PHENYL]BORANEDIOL; [3-(([(3-METHYLPHENYL)METHYL]SULFANYL)METHYL)PHENYL]BORANEDIOL; [3-(1,3-DIOXOLAN-2-YL)-2-FLUOROPHENYL]BORONIC ACID; [3-(1,4-OXAZEPAN-4-YLMETHYL)PHENYL]BORANEDIOL; [3-(1H-INDAZOL-1-YLMETHYL)PHENYL]BORANEDIOL; [3-(1H-PYRAZOL-3-YL)PHENYL]BORONIC ACID; [3-(1H-PYRAZOL-5-YL)PHENYL]BORONIC ACID HYDRATE; [3-(1-METHOXYETHYL)PHENYL]BORONIC ACID; [3-(2,3-DICHLOROPHENOXYMETHYL)PHENYL]BORANEDIOL; [3-(2,3-DIFLUOROPHENOXYMETHYL)PHENYL]BORANEDIOL; [3-(2,3-DIHYDRO-1H-INDOL-1-YLMETHYL)PHENYL]BORANEDIOL; [3-(2,3-DIHYDRO-1H-ISOINDOL-2-YLMETHYL)PHENYL]BORANEDIOL; [3-(2,3-DIMETHYLPHENOXYMETHYL)PHENYL]BORANEDIOL; [3-(2,4-DICHLOROPHENOXYMETHYL)PHENYL]BORANEDIOL; [3-(2,4-DIFLUOROPHENOXYMETHYL)PHENYL]BORANEDIOL; [3-(2,4-DIMETHYLPHENOXYMETHYL)PHENYL]BORANEDIOL; [3-(2,5-DICHLOROPHENOXYMETHYL)PHENYL]BORANEDIOL; [3-(2,5-

DIMETHYLPHENOXYMETHYL)PHENYL]BORANEDIOL; [3-(2,6-DICHLOROPHENOXYMETHYL)PHENYL]BORANEDIOL; [3-(2,6-DIMETHYLPHENOXYMETHYL)PHENYL]BORANEDIOL; [3-(2-CARBOXYETHYL)PHENYL]BORONIC ACID; [3-(2-CHLORO-4-FLUOROPHENOXYMETHYL)PHENYL]BORANEDIOL; [3-(2-CHLORO-4-METHYLPHENOXYMETHYL)PHENYL]BORANEDIOL; [3-(2-CHLORO-5-METHYLPHENOXYMETHYL)PHENYL]BORANEDIOL; [3-(2-CYCLOBUTOXYETHOXY)PHENYL]BORANEDIOL; [3-(2-ETHYLPHENOXYMETHYL)PHENYL]BORANEDIOL; [3-(2-METHOXYPHENOXYMETHYL)PHENYL]BORANEDIOL; [3-(2-METHYLBUTOXY)PHENYL]BORANEDIOL; [3-(2-PHENYLETHOXY)PHENYL]BORANEDIOL; [3-(3,4-DICHLOROPHENOXYMETHYL)PHENYL]BORANEDIOL; [3-(3,4-DIFLUOROPHENOXYMETHYL)PHENYL]BORANEDIOL; [3-(3,4-DIMETHYLPHENOXYMETHYL)PHENYL]BORANEDIOL; [3-(3,5-DICHLOROPHENOXYMETHYL)PHENYL]BORANEDIOL; [3-(3,5-DIFLUOROPHENOXYMETHYL)PHENYL]BORANEDIOL; [3-(3,5-DIMETHYLPHENOXYMETHYL)PHENYL]BORANEDIOL; [3-(3-ETHYLPHENOXYMETHYL)PHENYL]BORANEDIOL; [3-(3-HYDROXYPROPYL)PHENYL]BORONIC ACID; [3-(3-METHOXYPHENOXYMETHYL)PHENYL]BORANEDIOL; [3-(3-METHYLBUTOXY)PHENYL]BORANEDIOL; [3-(3-PHENYLPROPOXY)PHENYL]BORANEDIOL; [3-(4-CHLORO-1H-BENZOTHIAZOL-2-YL)PHENYL]-BORONIC ACID; [3-(4-CHLORO-2-METHYLPHENOXYMETHYL)PHENYL]BORANEDIOL; [3-(4-ETHYLPHENOXYMETHYL)PHENYL]BORANEDIOL; [3-(4-METHOXYPHENOXYMETHYL)PHENYL]BORANEDIOL; [3-(AZEPAN-1-YLMETHYL)-4-METHOXYPHENYL]BORANEDIOL; [3-(AZEPAN-1-YLMETHYL)PHENYL]BORONIC ACID HYDROCHLORIDE; [3-(BUT-3-EN-2-YLOXY)PHENYL]BORANEDIOL; [3-(BUTAN-2-YLOXY)PHENYL]BORANEDIOL; [3-(CYCLOBUTOXYMETHYL)-4-METHOXYPHENYL]BORANEDIOL; [3-(CYCLOBUTOXYMETHYL)PHENYL]BORANEDIOL; [3-(CYCLOPENTYLOXY)PHENYL]BORANEDIOL; [3-(E-3-METHOXY-3-OXO-1-PROPEN-1-YL)PHENYL]BORONIC ACID; [3-(HEPTYLOXY)PHENYL]BORANEDIOL; [3-(HEXYLOXY)PHENYL]BORANEDIOL; [3-(ISOBUTYLAMINOCARBONYL)PHENYL]BORONIC ACID; [3-(MORPHOLIN-4-YLMETHYL)PHENYL]BORONIC ACID HYDROCHLORIDE; [3-(N-ISOPROPYLAMINOCARBONYL)PHENYL]BORONIC ACID; [3-(NONYLOXY)PHENYL]BORANEDIOL; [3-(OCTYLOXY)PHENYL]BORANEDIOL; [3-(OXAN-2-YLMETHOXY)PHENYL]BORANEDIOL; [3-(OXOLAN-2-YLMETHOXY)PHENYL]BORANEDIOL; [3-(OXOLAN-3-YLOXY)PHENYL]BORANEDIOL; [3-(PENTYLOXY)PHENYL]BORANEDIOL; [3-(PYRIDIN-3-YLMETHOXY)PHENYL]BORANEDIOL; [3-(PYRIDIN-4-YLMETHOXY)PHENYL]BORANEDIOL; [3-(PYRIMIDIN-2-YLMETHOXY)PHENYL]BORANEDIOL; [3-(PYRROLIDIN-1-YLMETHYL)PHENYL]BORONIC ACID HYDROCHLORIDE; [3,3'-BIPYRIDIN]-5-YLBORONIC ACID; [3-FLUORO-4-(1,4-OXAZEPAN-4-YLMETHYL)PHENYL]BORANEDIOL; [3-FLUORO-4-(2-FLUOROPHENOXYMETHYL)PHENYL]BORANEDIOL; [3-FLUORO-4-(2-METHYLPHENOXYMETHYL)PHENYL]BORANEDIOL; [3-FLUORO-4-(3-FLUOROPHENOXYMETHYL)PHENYL]BORANEDIOL; [3-FLUORO-4-(3-METHYLPHENOXYMETHYL)PHENYL]BORANEDIOL; [3-FLUORO-4-(4-FLUOROPHENOXYMETHYL)PHENYL]BORANEDIOL; [3-FLUORO-4-(4-METHYLPHENOXYMETHYL)PHENYL]BORANEDIOL; [3-METHYL-4-(2,2,2-TRIFLUOROETHOXY)PHENYL]BORANEDIOL; [3-METHYL-4-(2-METHYLBUTOXY)PHENYL]BORANEDIOL; [3-METHYL-4-(2-METHYLPROPOXY)PHENYL]BORANEDIOL; [3-METHYL-4-(3-METHYLBUTOXY)PHENYL]BORANEDIOL; [3-METHYL-4-(OXOLAN-3-YLOXY)PHENYL]BORANEDIOL; [3-METHYL-4-(PENTYLOXY)PHENYL]BORANEDIOL; [3-METHYL-4-(PROP-2-EN-1-YLOXY)PHENYL]BORANEDIOL; [4-(([(2-METHYLPHENYL)METHYL]SULFANYL)METHYL)PHENYL]BORANEDIOL; [4-(([(3-METHYLPHENYL)METHYL]SULFANYL)METHYL)PHENYL]BORANEDIOL; [4-(1'(3'-AMINOPROPYLL)IMIDAZOLE-1-CARBONYL)PHENYL] BORONIC ACID; [4-(1,3,4-OXADIAZOL-2-YL)PHENYL]BORONIC ACID; [4-(1,4-OXAZEPAN-4-YLMETHYL)PHENYL]BORANEDIOL; [4-(1-AMINO-4'-METHYLPIPERAZINE-1-CARBONYL)PHENYL] BORONIC ACID; [4-(1-ETHOXYETHYL)PHENYL]BORONIC ACID; [4-(1-ETHOXYETHYL)PHENYL]BORONIC ACID HYDRATE; [4-(1H-INDAZOL-1-YLMETHYL)PHENYL]BORANEDIOL; [4-(1H-PYRAZOL-1-YL)PHENYL]BORONIC ACID; [4-(1H-PYRAZOL-5-YL)PHENYL]BORONIC ACID; [4-(1-METHOXYETHYL)PHENYL]BORONIC ACID; [4-(2,3-DICHLOROPHENOXYMETHYL)PHENYL]BORANEDIOL; [4-(2,3-DIFLUOROPHENOXYMETHYL)PHENYL]BORANEDIOL; [4-(2,3-DIHYDRO-1H-INDOL-1-YLMETHYL)PHENYL]BORANEDIOL; [4-(2,3-DIHYDRO-1H-ISOINDOL-2-YLMETHYL)PHENYL]BORANEDIOL; [4-(2,3-DIMETHYLPHENOXYMETHYL)PHENYL]BORANEDIOL; [4-(2,4-DICHLOROPHENOXYMETHYL)PHENYL]BORANEDIOL; [4-(2,4-DIFLUOROPHENOXYMETHYL)PHENYL]BORANEDIOL; [4-(2,4-DIMETHYLPHENOXYMETHYL)PHENYL]BORANEDIOL; [4-(2,5-DICHLOROPHENOXYMETHYL)PHENYL]BORANEDIOL; [4-(2,5-DIMETHYLPHENOXYMETHYL)PHENYL]BORANEDIOL; [4-(2,6-DICHLOROPHENOXYMETHYL)PHENYL]BORANEDIOL; [4-(2,6-DIMETHYLPHENOXYMETHYL)PHENYL]BORANEDIOL; [4-(2-CHLORO-4-FLUOROPHENOXYMETHYL)PHENYL]BORANEDIOL; [4-(2-CHLORO-4-METHYLPHENOXYMETHYL)PHENYL]BORANEDIOL; [4-(2-CHLORO-5-METHYLPHENOXYMETHYL)PHENYL]BORANEDIOL; [4-(2-CHLOROPHENOXYMETHYL)-3-FLUOROPHENYL]BORANEDIOL; [4-(2-

CYCLOBUTOXYETHOXY)PHENYL]BORANEDIOL; [4-(2-ETHOXYCARBONYLETHYL)PHENYL]BORONIC ACID; [4-(2-ETHOXYETHOXY)-3-METHYLPHENYL]BORANEDIOL; [4-(2-ETHYLPHENOXYMETHYL)PHENYL]BORANEDIOL; [4-(2-METHOXYETHOXY)-3-METHYLPHENYL]BORANEDIOL; [4-(2-METHOXYPHENOXYMETHYL)PHENYL]BORANEDIOL; [4-(2-METHYLBUTOXY)PHENYL]BORANEDIOL; [4-(2-PHENYL-1H-BENZIMIDAZOL-1-YL)PHENYL]BORONIC ACID; [4-(2-PHENYLETHOXY)PHENYL]BORANEDIOL; [4-(2-PIPERIDIN-1-YLETHYL)PHENYL]BORONIC ACID; [4-(3,4-DICHLOROPHENOXYMETHYL)PHENYL]BORANEDIOL; [4-(3,4-DIFLUOROPHENOXYMETHYL)PHENYL]BORANEDIOL; [4-(3,4-DIMETHYLPHENOXYMETHYL)PHENYL]BORANEDIOL; [4-(3,5-DICHLOROPHENOXYMETHYL)PHENYL]BORANEDIOL; [4-(3,5-DIFLUOROPHENOXYMETHYL)PHENYL]BORANEDIOL; [4-(3,5-DIMETHYL-1H-PYRAZOL-1-YL)PHENYL]BORONIC ACID; [4-(3,5-DIMETHYLPHENOXYMETHYL)PHENYL]BORANEDIOL; [4-(3-CHLOROPHENOXYMETHYL)-3-FLUOROPHENYL]BORANEDIOL; [4-(3-ETHYLPHENOXYMETHYL)PHENYL]BORANEDIOL; [4-(3-METHOXYPHENOXYMETHYL)PHENYL]BORANEDIOL; [4-(3-METHOXYPROPOXY)-3-METHYLPHENYL]BORANEDIOL; [4-(3-PHENYLPROPOXY)PHENYL]BORANEDIOL; [4-(4'-AMINOMORPHOLINE-1-CARBONYL)PHENYL]BORONIC ACID; [4-(4-CHLORO-2-METHYLPHENOXYMETHYL)PHENYL]BORANEDIOL; [4-(4-CHLOROPHENOXYMETHYL)-3-FLUOROPHENYL]BORANEDIOL; [4-(4-ETHYLPHENOXYMETHYL)PHENYL]BORANEDIOL; [4-(4-METHOXYPHENOXYMETHYL)PHENYL]BORANEDIOL; [4-(4-TERT-BUTYLPHENYL)PHENYL]BORANEDIOL; [4-(AZEPAN-1-YLMETHYL)PHENYL]BORONIC ACID; [4-(AZOCAN-1-YLMETHYL)-3-FLUOROPHENYL]BORANEDIOL; [4-(BUT-2-EN-1-YLOXY)-3-METHYLPHENYL]BORANEDIOL; [4-(BUT-3-EN-2-YLOXY)-3-METHYLPHENYL]BORANEDIOL; [4-(BUT-3-EN-2-YLOXY)PHENYL]BORANEDIOL; [4-(BUTAN-2-YLOXY)-3-METHYLPHENYL]BORANEDIOL; [4-(BUTAN-2-YLOXY)PHENYL]BORANEDIOL; [4-(CYCLOBUTOXYMETHYL)-3-FLUOROPHENYL]BORANEDIOL; [4-(CYCLOBUTOXYMETHYL)PHENYL]BORANEDIOL; [4-(CYCLOHEXYLOXY)PHENYL]BORANEDIOL; [4-(CYCLOPENTYLOXY)-3-METHYLPHENYL]BORANEDIOL; [4-(CYCLOPROPYLMETHOXY)-3-METHYLPHENYL]BORANEDIOL; [4-(DIFLUOROMETHOXY)-2-METHOXYPHENYL]BORONIC ACID; [4-(E-3-METHOXY-3-OXO-1-PROPEN-1-YL)PHENYL]BORONIC ACID; [4-(MORPHOLIN-4-YLMETHYL)PHENYL]BORONIC ACID HYDROCHLORIDE; [4-(OXOLAN-2-YLMETHOXY)PHENYL]BORANEDIOL; [4-(OXOLAN-3-YLOXY)PHENYL]BORANEDIOL; [4-(PIPERAZIN-1-YL)PHENYL]BORONIC ACID; [4-(PIPERAZIN-1-YLMETHYL)PHENYL]BORONIC ACID DIHYDROCHLORIDE; [4-(PYRIMIDIN-2-YLMETHOXY)PHENYL]BORANEDIOL; [4-(TRANS-4-N-PROPYLCYCLOHEXYL)PHENYL]BORONIC ACID; [4-(TRIFLUOROMETHYL)PYRIMIDIN-2-YL]BORONIC ACID; [4-(TRIPHENYLSILYL)PHENYL]BORONIC ACID; [4-CHLORO-2-(3,5-DIMETHYL-1H-PYRAZOL-1-YL)PHENYL]BORONIC ACID; [4-FLUORO-3-(HYDROXYMETHYL)PHENYL]BORONIC ACID; [4-METHOXY-2-(1H-PYRAZOL-1-YL)PHENYL]BORONIC ACID; [4-METHOXY-3-(1,4-OXAZEPAN-4-YLMETHYL)PHENYL]BORANEDIOL; [4-METHOXY-3-(1,4-THIAZEPAN-4-YLMETHYL)PHENYL]BORANEDIOL; [4-METHOXY-3-(PHENOXYMETHYL)PHENYL]BORANEDIOL; [4-METHYL-2-(1H-PYRAZOL-1-YL)PHENYL]BORONIC ACID; [4-TRIFLUOROMETHYL-6-[3-(TRIFLUOROMETHYL)PHENYL]PYRIMIDIN-2-YL]BORONIC ACID; [4-TRIFLUOROMETHYL-6-[4-(TRIFLUOROMETHYL)PHENYL]PYRIMIDIN-2-YL]BORONIC ACID; [5-(1,3-DIOXOLAN-2-YL)-2-FLUOROPHENYL]BORONIC ACID; [5-(2-CHLOROPHENOXYMETHYL)-2-FLUOROPHENYL]BORANEDIOL; [5-(3-CHLOROPHENOXYMETHYL)-2-FLUOROPHENYL]BORANEDIOL; [5-(4-CHLOROPHENOXYMETHYL)-2-FLUOROPHENYL]BORANEDIOL; [5-(AZEPAN-1-YLMETHYL)-2-METHOXYPHENYL]BORANEDIOL; [5-(AZOCAN-1-YLMETHYL)-2-FLUOROPHENYL]BORANEDIOL; [5-(BUTYLCARBAMOYL)-2-FLUOROPHENYL]BORONIC ACID; [5-(CYCLOBUTOXYMETHYL)-2-FLUOROPHENYL]BORANEDIOL; [5-(CYCLOBUTOXYMETHYL)-2-METHOXYPHENYL]BORANEDIOL; [5-(DIMETHYLCARBAMOYL)-2-FLUOROPHENYL]BORONIC ACID; [5,6,7,8-TETRAHYDROQUINAZOLIN-2-YL]BORONIC ACID; [5-BENZYLOXY-1-TOSYLINDOL-3-YL]BORONIC ACID; [5-FLUORO-2-(1,4-OXAZEPAN-4-YLMETHYL)PHENYL]BORANEDIOL; [5-FLUORO-2-(2-FLUOROPHENOXYMETHYL)PHENYL]BORANEDIOL; [5-FLUORO-2-(2-METHOXYETHOXY)PHENYL]BORANEDIOL; [5-FLUORO-2-(2-METHYLBUTOXY)PHENYL]BORANEDIOL; [5-FLUORO-2-(2-METHYLPHENOXYMETHYL)PHENYL]BORANEDIOL; [5-FLUORO-2-(2-METHYLPROPOXY)PHENYL]BORANEDIOL; [5-FLUORO-2-(2-PHENYLETHOXY)PHENYL]BORANEDIOL; [5-FLUORO-2-(3-FLUOROPHENOXYMETHYL)PHENYL]BORANEDIOL; [5-FLUORO-2-(3-METHYLBUTOXY)PHENYL]BORANEDIOL; [5-FLUORO-2-(3-METHYLPHENOXYMETHYL)PHENYL]BORANEDIOL; [5-FLUORO-2-(4-FLUOROPHENOXYMETHYL)PHENYL]BORANEDIOL; [5-FLUORO-2-(4-METHYLPHENOXYMETHYL)PHENYL]BORANEDIOL; [5-FLUORO-2-(HEPTYLOXY)PHENYL]BORANEDIOL; [5-FLUORO-2-(HEXYLOXY)PHENYL]BORANEDIOL; [5-FLUORO-2-(OCTYLOXY)PHENYL]BORANEDIOL; [5-FLUORO-2-(OXAN-2-YLMETHOXY)PHENYL]BORANEDIOL; [5-FLUORO-2-(OXAN-4-YLMETHOXY)PHENYL]BORANEDIOL; [5-FLUORO-2-(OXOLAN-2-YLMETHOXY)PHENYL]BORANEDIOL; [5-FLUORO-2-(OXOLAN-3-YLOXY)PHENYL]BORANEDIOL; [5-FLUORO-2-(PENTYLOXY)PHENYL]BORANEDIOL; [5-FLUORO-2-(PROP-2-EN-1-YLOXY)PHENYL]BORANEDIOL; [5-FLUORO-2-(PYRIDIN-2-YLMETHOXY)PHENYL]BORANEDIOL; [5-FLUORO-2-(PYRIDIN-3-YLMETHOXY)PHENYL]BORANEDIOL; [5-FLUORO-2-(PYRIDIN-4-YLMETHOXY)PHENYL]BORANEDIOL; [5-FLUORO-2-(PYRIMIDIN-2-YLMETHOXY)PHENYL]BORANEDIOL; [5-METHYL-2-(2,2,2-TRIFLUOROETHOXY)PHENYL]BORANEDIOL; [5-METHYL-2-(2-METHYLBUTOXY)

PHENYL]BORANEDIOL; [5-METHYL-2-(2-PHENYLETHOXY)PHENYL]BORANEDIOL; [5-METHYL-2-(3-METHYLBUTOXY)PHENYL]BORANEDIOL; [5-METHYL-2-(OCTYLOXY)PHENYL]BORANEDIOL; [5-METHYL-2-(OXAN-2-YLMETHOXY)PHENYL]BORANEDIOL; [5-METHYL-2-(OXAN-4-YLMETHOXY)PHENYL]BORANEDIOL; [5-METHYL-2-(OXOLAN-2-YLMETHOXY)PHENYL]BORANEDIOL; [5-METHYL-2-(OXOLAN-3-YLOXY)PHENYL]BORANEDIOL; [5-METHYL-2-(PENTYLOXY)PHENYL]BORANEDIOL; [5-METHYL-2-(PROP-2-EN-1-YLOXY)PHENYL]BORANEDIOL; [5-METHYL-2-(PYRIDIN-2-YLMETHOXY)PHENYL]BORANEDIOL; [5-METHYL-2-(PYRIDIN-3-YLMETHOXY)PHENYL]BORANEDIOL; [5-METHYL-2-(PYRIDIN-4-YLMETHOXY)PHENYL]BORANEDIOL; [5-METHYL-2-(PYRIMIDIN-2-YLMETHOXY)PHENYL]BORANEDIOL; [6-(1-NAPHTHYL)-4-(TRIFLUOROMETHYL)PYRIMIDIN-2-YL]BORONIC ACID; [6-(2,2,2-TRIFLUOROETHOXY)PYRIDIN-3-YL]BORONIC ACID; [6-(2-METHOXYETHOXY)NAPHTHALEN-2-YL]BORANEDIOL; [6-(2-METHYLBUTOXY)NAPHTHALEN-2-YL]BORANEDIOL; [6-(2-METHYLPROPOXY)NAPHTHALEN-2-YL]BORANEDIOL; [6-(2-NAPHTHYL)-4-(TRIFLUOROMETHYL)PYRIMIDIN-2-YL]BORONIC ACID; [6-(3-METHYLBUTOXY)NAPHTHALEN-2-YL]BORANEDIOL; [6-(4-ETHYLPHENYL)-4-(TRIFLUOROMETHYL)PYRIMIDIN-2-YL]BORONIC ACID; [6-(4-METHYLPIPERAZIN-1-YL)PYRIDIN-3-YL]BORONIC ACID; [6-(M-TOLYL)-4-(TRIFLUOROMETHYL)PYRIMIDIN-2-YL]BORONIC ACID; [6-(O-TOLYL)-4-(TRIFLUOROMETHYL)PYRIMIDIN-2-YL]BORONIC ACID; [6-(P-TOLYL)-4-(TRIFLUOROMETHYL)PYRIMIDIN-2YL]BORONIC ACID; [6-(TERT-BUTYL)-4-(TRIFLUOROMETHYL)PYRIMIDIN-2-YL]BORONIC ACID; [6-(TRIFLUOROMETHOXY)PYRIDIN-3-YL]BORONIC ACID; [6-CYCLOPROPYLPYRIMIDIN-2-YL]BORONIC ACID; [6-METHOXY-1-TOSYLINDOL-3-YL]BORONIC ACID; 1-((2-(TRIMETHYLSILYL)ETHOXY)METHYL)PYRAZOLE-5-BORONIC ACID; 1-([2-(DIHYDROXYBORANYL)-4-FLUOROPHENYL]METHYL)-1,2-DIHYDROPYRIDIN-2-ONE; 1-([2-(DIHYDROXYBORANYL)-4-FLUOROPHENYL]METHYL)-4-METHYL-1,2-DIHYDROPYRIDIN-2-ONE; 1-([2-(DIHYDROXYBORANYL)PHENYL]METHYL)-1,2,3,4-TETRAHYDROPYRIMIDINE-2,4-DIONE; 1-([2-(DIHYDROXYBORANYL)PHENYL]METHYL)-1,2-DIHYDROPYRIDIN-2-ONE; 1-([2-(DIHYDROXYBORANYL)PHENYL]METHYL)-4,6-DIMETHYL-1,2-DIHYDROPYRIMIDIN-2-ONE; 1-([2-(DIHYDROXYBORANYL)PHENYL]METHYL)-4-METHYL-1,2,3,4-TETRAHYDROPYRAZINE-2,3-DIONE; 1-([2-(DIHYDROXYBORANYL)PHENYL]METHYL)-6-METHYL-1,2-DIHYDROPYRIDIN-2-ONE; 1-([3-(DIHYDROXYBORANYL)-4-FLUOROPHENYL]METHYL)-1,2-DIHYDROPYRIDIN-2-ONE; 1-([3-(DIHYDROXYBORANYL)-4-FLUOROPHENYL]METHYL)-1,2-DIHYDROPYRIMIDIN-2-ONE; 1-([3-(DIHYDROXYBORANYL)-4-FLUOROPHENYL]METHYL)-4-METHYL-1,2-DIHYDROPYRIDIN-2-ONE; 1-([3-(DIHYDROXYBORANYL)-4-METHOXYPHENYL]METHYL)-1,2-DIHYDROPYRIMIDIN-2-ONE; 1-([3-(DIHYDROXYBORANYL)PHENYL]METHYL)-1,2,3,4-TETRAHYDROPYRIMIDINE-2,4-DIONE; 1-([3-(DIHYDROXYBORANYL)PHENYL]METHYL)-1,2-DIHYDROPYRIDIN-2-ONE; 1-([3-(DIHYDROXYBORANYL)PHENYL]METHYL)-1,2-DIHYDROPYRIMIDIN-2-ONE; 1-([3-(DIHYDROXYBORANYL)PHENYL]METHYL)-4,6-DIMETHYL-1,2-DIHYDROPYRIMIDIN-2-ONE; 1-([3-(DIHYDROXYBORANYL)PHENYL]METHYL)-4-METHYL-1,2-DIHYDROPYRIDIN-2-ONE; 1-([3-(DIHYDROXYBORANYL)PHENYL]METHYL)-6-METHYL-1,2-DIHYDROPYRIDIN-2-ONE; 1-([4-(DIHYDROXYBORANYL)-2-FLUOROPHENYL]METHYL)-1,2-DIHYDROPYRIDIN-2-ONE; 1-([4-(DIHYDROXYBORANYL)PHENYL]METHYL)-1,2,3,4-TETRAHYDROPYRIMIDINE-2,4-DIONE; 1-([4-(DIHYDROXYBORANYL)PHENYL]METHYL)-1,2-DIHYDROPYRIDIN-2-ONE; 1-([4-(DIHYDROXYBORANYL)PHENYL]METHYL)-4,6-DIMETHYL-1,2-DIHYDROPYRIMIDIN-2-ONE; 1-([4-(DIHYDROXYBORANYL)PHENYL]METHYL)-4-METHYL-1,2-DIHYDROPYRIDIN-2-ONE; 1-([4-(DIHYDROXYBORANYL)PHENYL]METHYL)-6-METHYL-1,2-DIHYDROPYRIDIN-2-ONE; 1-([5-(DIHYDROXYBORANYL)-2-METHOXYPHENYL]METHYL)-1,2-DIHYDROPYRIMIDIN-2-ONE; 1-(1-BOC-PIPERIDINO)PYRAZOLE-4-BORONIC ACID; 1-(1-ETHOXYETHYL)-1H-PYRAZOL-5-YLBORONIC ACID; 1-(2-(DIMETHYLAMINO)ETHYL)-1H-PYRAZOL-4-YLBORONIC ACID; 1-(2-(PYRROLIDIN-1-YL)ETHYL)-1H-PYRAZOL-4-YLBORONIC ACID; 1-(2-(TERT-BUTYLDIMETHYLSILYLOXY)ETHYL)-1H-PYRAZOL-3-YLBORONIC ACID; 1-(2-(TERT-BUTYLDIMETHYLSILYLOXY)ETHYL)-1H-PYRAZOL-4-YLBORONIC ACID; 1-(2,2,2-TRIFLUOROETHYL)-1H-PYRAZOLE-4-BORONIC ACID; 1-(2,2,2-TRIFLUOROETHYL)-1H-PYRAZOLE-5-BORONIC ACID; 1-(2,2-DIETHOXYETHYL)PYRAZOLE-4-BORONIC ACID; 1-(2,2-DIFLUOROETHYL)-PYRROL-2-YLBORONIC ACID; 1-(2,2-DIFLUOROETHYL)-PYRROL-3-YLBORONIC ACID; 1-(2,2-DIMETHYLPROPANOYL)-1H-PYRROL-2-YLBORONIC ACID; 1-(2-[4-(DIHYDROXYBORANYL)PHENOXY]ETHYL)-1,2-DIHYDROPYRIMIDIN-2-ONE; 1-(2-AMINO-2-OXOETHYL)-1H-PYRAZOL-4-YLBORONIC ACID; 1-(2-AMINOETHY)-1H-PYRAZOL-4-YLBORONIC ACID; 1-(2-CHLOROPHENYL)PYRAZOLE-4-BORONIC ACID; 1-(2-HYDROXYETHYL)-1H-PYRAZOL-4-YLBORONIC ACID; 1-(2-METHOXYETHYL)-1H-PYRAZOL-4-YLBORONIC ACID; 1-(2-METHOXYETHYL)-PYRROL-2-YLBORONIC ACID; 1-(2-METHOXYETHYL)-PYRROL-3-YLBORONIC ACID; 1-(3-(DIMETHYLAMINO)PROPYL)-1H-PYRAZOL-4-YLBORONIC ACID; 1-(3,3-DIETHOXYPROPYL)-1H-PYRAZOL-4-YLBORONIC ACID; 1-(3,3-DIETHOXYPROPYL)-1H-PYRAZOL-5-YLBORONIC ACID; 1-(3-CHLOROPHENYL)-1H-PYRAZOL-4-YLBORONIC ACID; 1-(3-CHLOROPHENYL)-1H-PYRAZOLE-3-BORONIC ACID; 1-(3-CHLOROPHENYL)-4-(ETHOXYCARBONYL)-1H-PYRAZOL-5-YLBORONIC ACID; 1-(3-HYDROXYPROPYL)-1H-PYRROL-3-YLBORONIC ACID; 1-(3-METHYLBUTYL)-1H-PYRAZOL-5-YLBORONIC ACID; 1-(3-METHYLBUTYL)-1H-PYRAZOLE-4-BORONIC ACID; 1-(3-PYRIDINYL)-1H-PYRAZOL-4-YLBORONIC ACID; 1-(4-BORONOBENZOYL)PIPERIDINE-4-CARBOXYLIC ACID; 1-(4-BORONOPHENYLSULFONYL)AZETIDINE; 1-(4-CARBOXYBUTYL)INDOLE-5-BORONIC ACID; 1-(4-CHLOROBENZOYL)-1,2,3,6-TETRAHYDROPYRIDIN-4-YLBORONIC ACID; 1-(4-CHLORO-

PHENYL)-4-(ETHOXYCARBONYL)-1H-PYRAZOL-5-YLBORONIC ACID; 1-(4-FLUOROPHENYL)PYRAZOLE-4-BORONIC ACID; 1-(4-PIPERIDINYL)-1H-PYRAZOL-4-YLBORONIC ACID; 1-(4-PYRIDINOMETHYL)PYRAZOLE-4-BORONIC ACID; 1-(4-PYRIDINYL)-1H-PYRAZOL-4-YLBORONIC ACID; 1-(5-METHOXY-5-OXOPENTYL)-1H-PYRAZOL-4-YLBORONIC ACID; 1-(6-CHLOROPYRIMIDIN-4-YL)-1H-PYRAZOL-4-YLBORONIC ACID; 1-(BENZYL)-5-INDOLINEBORONIC ACID; 1-(CYCLOPROPYLMETHYL)-1H-PYRAZOLE-5-BORONIC ACID; 1-(CYCLOPROPYLMETHYL)-PYRROL-2-YLBORONIC ACID; 1-(CYCLOPROPYLMETHYL)-PYRROL-3-YLBORONIC ACID; 1-(DIFLUOROMETHOXY)NAPHTHALENE-2-BORONIC ACID; 1-(DIFLUOROMETHOXY)NAPHTHALENE-3-BORONIC ACID; 1-(DIFLUOROMETHOXY)NAPHTHALENE-4-BORONIC ACID; 1-(DIFLUOROMETHOXY)NAPHTHALENE-5-BORONIC ACID; 1-(DIFLUOROMETHOXY)NAPHTHALENE-6-BORONIC ACID; 1-(DIFLUOROMETHOXY)NAPHTHALENE-7-BORONIC ACID; 1-(DIFLUOROMETHOXY)NAPHTHALENE-8-BORONIC ACID; 1-(DIFLUOROMETHYL)NAPHTHALENE-2-BORONIC ACID; 1-(DIFLUOROMETHYL)NAPHTHALENE-3-BORONIC ACID; 1-(DIFLUOROMETHYL)NAPHTHALENE-4-BORONIC ACID; 1-(DIFLUOROMETHYL)NAPHTHALENE-5-BORONIC ACID; 1-(DIFLUOROMETHYL)NAPHTHALENE-6-BORONIC ACID; 1-(DIFLUOROMETHYL)NAPHTHALENE-7-BORONIC ACID; 1-(DIFLUOROMETHYL)NAPHTHALENE-8-BORONIC ACID; 1-(HYDROXYMETHYL)NAPHTHALENE-2-BORONIC ACID; 1-(METHOXYMETHYL)-2-(PHENYLTHIO)-1H-IMIDAZOL-5-YLBORONIC ACID; 1-(METHYLSULFONYL)-1H-PYRAZOL-4-YLBORONIC ACID; 1-(METHYLSULFONYL)-PYRROL-2-YLBORONIC ACID; 1-(METHYLSULFONYL)-PYRROL-3-YLBORONIC ACID; 1-(N,N-DIMETHYLSULFAMOYL)-1H-PYRAZOL-4-YLBORONIC ACID; 1-(N,N-DIMETHYLSULFAMOYL)-3-(PYRIDIN-2-YL)-1H-PYRAZOL-4-YLBORONIC ACID; 1-(N,N-DIMETHYLSULFAMOYL)-3-(TRIFLUOROMETHYL)-1H-PYRAZOL-4-YLBORONIC ACID; 1-(N,N-DIMETHYLSULFAMOYL)-3-ETHYL-1H-PYRAZOL-4-YLBORONIC ACID; 1-(N,N-DIMETHYLSULFAMOYL)-3-METHYL-1H-PYRAZOL-4-YLBORONIC ACID; 1-(PHENYLSULFONYL)-1H-INDOL-3-YLBORONIC ACID; 1-(PHENYLSULFONYL)-1H-PYRAZOL-4-YLBORONIC ACID; 1-(PHENYLSULFONYL)-1H-PYRROLO[3,2-C]PYRIDINE-2-YLBORONIC ACID; 1-(PHENYLSULFONYL)-2-INDOLEBORONIC ACID; 1-(PHENYLSULFONYL)PYRROLE-2-BORONIC ACID; 1-(PHENYLSULPHONYL)-1H-INDOLE-5-BORONIC ACID; 1-(P-TOLUENESULFONYL)-INDOLE-2-BORONIC ACID; 1-(PYRIDIN-2-YLMETHYL)-1H-PYRAZOL-4-YLBORONIC ACID; 1-(PYRIDIN-3-YLMETHYL)PYRAZOLE-4-BORONIC ACID; 1-(T-BUTOXYCARBONYL)PYRAZOLE-5-BORONIC ACID; 1-(TERT-BUTOXYCARBONYL)-1,2,3,4-TETRAHYDRO-4,4-DIMETHYLQUINOLIN-7-YL-7-BORONIC ACID; 1-(TERT-BUTOXYCARBONYL)-1,2,3,6-TETRAHYDROPYRIDIN-4-YLBORONIC ACID; 1-(TERT-BUTOXYCARBONYL)-1H-INDOL-5-YLBORONIC ACID; 1-(TERT-BUTOXYCARBONYL)-1H-PYRROLO[3,2-C]PYRIDIN-3-YLBORONIC ACID; 1-(TERT-BUTOXYCARBONYL)-2-OXOINDOLIN-5-YLBORONIC ACID; 1'-(TERT-BUTOXYCARBONYL)-2-OXOSPIRO[INDOLINE-3,4'-PIPERIDINE]-5-YLBORONIC ACID; 1-(TERT-BUTOXYCARBONYL)-3,3-DIMETHYLINDOLIN-5-YL-5-BORONIC ACID; 1-(TERT-BUTOXYCARBONYL)-3,3-DIMETHYLINDOLIN-6-YL-6-BORONIC ACID; 1-(TERT-BUTOXYCARBONYL)-3-METHYL-1H-INDOL-2-YLBORONIC ACID; 1-(TERT-BUTOXYCARBONYL)-4-CHLORO-PYRROL-3-YLBORONIC ACID; 1-(TERT-BUTOXYCARBONYL)-4-ISOPROPYL-PYRROL-3-YLBORONIC ACID; 1-(TERT-BUTOXYCARBONYL)-4-METHYL-PYRROL-3-YLBORONIC ACID; 1-(TERT-BUTOXYCARBONYL)-5-((TERT-BUTYLDIMETHYLSILYLOXY)METHYL)-1H-INDOL-2-YLBORONIC ACID; 1-(TERT-BUTOXYCARBONYL)-5-(PENT-4-ENYL)-1H-PYRROL-2-YLBORONIC ACID; 1-(TERT-BUTOXYCARBONYL)-5-(TRIFLUOROMETHOXY)INDOLE-2-BORONIC ACID; 1-(TERT-BUTOXYCARBONYL)-5-(TRIISOPROPYLSILYLOXY)-1H-INDOL-2-YLBORONIC ACID; 1-(TERT-BUTOXYCARBONYL)-5,7-DIMETHOXY-1H-INDOL-3-YLBORONIC ACID; 1-(TERT-BUTOXYCARBONYL)-5-FLUORO-1H-INDOL-3-YLBORONIC ACID; 1-(TERT-BUTOXYCARBONYL)-5-INDOLINEBORONIC ACID; 1-(TERT-BUTOXYCARBONYL)-5-METHOXY-1H-INDOL-2-YLBORONIC ACID; 1-(TERT-BUTOXYCARBONYL)-5-METHOXY-1H-INDOL-3-YLBORONIC ACID; 1-(TERT-BUTOXYCARBONYL)-5-METHOXY-1H-PYRROLO[3,2-B]PYRIDIN-2-YLBORONIC ACID; 1-(TERT-BUTOXYCARBONYL)-5-METHYL-1H-PYRROL-2-YLBORONIC ACID; 1-(TERT-BUTOXYCARBONYL)-6-CHLORO-1H-INDOL-2-YLBORONIC ACID; 1-(TERT-BUTOXYCARBONYL)-6-ETHYL-5-FLUORO-1H-INDOL-2-YLBORONIC ACID; 1-(TERT-BUTOXYCARBONYL)-7-CHLORO-5-METHOXY-1H-INDOL-2-YLBORONIC ACID; 1-(TERT-BUTOXYCARBONYL)-7-METHOXY-1H-INDOL-2-YLBORONIC ACID; 1-(TERT-BUTOXYCARBONYL)-7-METHYL-1H-INDOL-2-YLBORONIC ACID; 1-(TERT-BUTOXYCARBONYL)INDOLE-2-BORONIC ACID; 1-(TERT-BUTOXYCARBONYL)INDOLE-3-BORONIC ACID; 1-(TERT-BUTOXYCARBONYL)INDOLIN-6-YL-6-BORONIC ACID; 1-(TERT-BUTOXYCARBONYL)PYRROLE-2-BORONIC ACID; 1-(TERT-BUTOXYCARBONYLAMINO)NAPHTHALEN-2-YLBORONIC ACID; 1-(TERT-BUTYLDIMETHYLSILYL)-1H-INDOL-5-YLBORONIC ACID; 1-(TERT-BUTYLDIMETHYLSILYL)-1H-INDOL-6-YLBORONIC ACID; 1-(TERT-BUTYLDIMETHYLSILYL)-4-CHLORO-PYRROL-3-YLBORONIC ACID; 1-(TERT-BUTYLDIMETHYLSILYL)-4-ISOPROPYL-PYRROL-3-YLBORONIC ACID; 1-(TERT-BUTYLDIMETHYLSILYL)-4-METHYL-PYRROL-3-YLBORONIC ACID; 1-(TERT-BUTYLDIMETHYLSILYL)-7-CHLORO-1H-INDOL-3-YLBORONIC ACID; 1-(TERT-BUTYLDIMETHYLSILYL)-7-FLUORO-1H-INDOL-3-YLBORONIC ACID; 1-(TERT-BUTYLDIMETHYLSILYL)-PYRROL-3-YLBORONIC ACID; 1-(TETRAHYDRO-2H-PYRAN-2-YL)-1H-INDAZOLE-5-BORONIC ACID; 1-(TETRAHYDRO-2H-PYRAN-2-YL)-1H-PYRAZOL-5-YLBORONIC ACID; 1-(TETRAHYDRO-2H-PYRAN-2-YL)-3-(TRIFLUOROMETHYL)-1H-PYRAZOL-5-YLBORONIC ACID; 1-(TETRAHYDRO-2H-PYRAN-2-YL)PYRAZOLE-4-BORONIC ACID; 1-(TETRAHYDRO-2H-PYRAN-4-YL)VINYLBORONIC ACID; 1-(THIAZOL-2-YLMETHYL)-1H-PYRAZOL-4-YLBORONIC ACID;

1-(TRIFLUOROMETHOXY)NAPHTHALENE-2-BORONIC ACID; 1-(TRIFLUOROMETHOXY)NAPHTHALENE-3-BORONIC ACID; 1-(TRIFLUOROMETHOXY)NAPHTHALENE-4-BORONIC ACID; 1-(TRIFLUOROMETHOXY)NAPHTHALENE-5-BORONIC ACID; 1-(TRIFLUOROMETHOXY)NAPHTHALENE-6-BORONIC ACID; 1-(TRIFLUOROMETHOXY)NAPHTHALENE-7-BORONIC ACID; 1-(TRIFLUOROMETHOXY)NAPHTHALENE-8-BORONIC ACID; 1-(TRIFLUOROMETHYL)NAPHTHALENE-2-BORONIC ACID; 1-(TRIFLUOROMETHYL)NAPHTHALENE-3-BORONIC ACID; 1-(TRIFLUOROMETHYL)NAPHTHALENE-4-BORONIC ACID; 1-(TRIFLUOROMETHYL)NAPHTHALENE-5-BORONIC ACID; 1-(TRIFLUOROMETHYL)NAPHTHALENE-6-BORONIC ACID; 1-(TRIFLUOROMETHYL)NAPHTHALENE-7-BORONIC ACID; 1-(TRIFLUOROMETHYL)NAPHTHALENE-8-BORONIC ACID; 1-(TRIISOPROPYLSILYL)-1H-INDOLE-3-BORONIC ACID; 1-(TRIISOPROPYLSILYL)-1H-PYRAZOL-3-YLBORONIC ACID; 1-(TRIISOPROPYLSILYL)-PYRROL-2-YLBORONIC ACID; 1-(TRIISOPROPYLSILYL)PYRROLE-3-BORONIC ACID; 1-(TRIMETHYLSILYL)-1H-PYRROL-3-YLBORONIC ACID; 1,1-(ETHYLENEDITHIO)-INDANE-5-BORONIC ACID; 1,10-PHENANTHROLIN-2-YLBORONIC ACID; 1,2,2-TRIMETHYL-CYCLOPROPYL BORONIC ACID; 1,2,3,4-TETRAHYDROISOQUINOLIN-6-YL-6-BORONIC ACID HCL; 1,2,3,4-TETRAHYDROISOQUINOLIN-6-YLBORONIC ACID; 1,2,3,4-TETRAHYDROISOQUINOLIN-7-YL-7-BORONIC ACID HYDROCHLORIDE; 1,2,3,6-TETRAHYDROPYRIDIN-4-YLBORONIC ACID HYDROCHLORIDE; 1,2,3,6-TETRAHYDROPYRIDINE-4-YL-BORONIC ACID; 1,2,3-TRIAZOLE-5-BORONIC ACID; 1,2,5,6-TETRAHYDROPYRIDIN-3-YLBORONIC ACID; 1,2-DIHYDRO-NAPHTHALENE-3-BORONIC ACID; 1,2-DIMETHYL-1H-IMIDAZOL-5-YLBORONIC ACID; 1,2-DIMETHYL-1H-INDOLE-7-BORONIC ACID; 1,3,4-THIADIAZOL-2-YLBORONIC ACID; 1,3,4-TRIMETHYL-1H-PYRAZOLE-5-BORONIC ACID; 1,3,5-TRIMETHYL-1H-PYRAZOL-4-YLBORONIC ACID; 1,3,5-TRIMETHYL-1H-PYRAZOLE-4-BORONIC ACID, HYDROCHLORIDE; 1,3-BENZOTHIAZOL-2-YLBORONIC ACID; 1,3-BENZOTHIAZOL-6-YLBORONIC ACID; 1,3-BENZOXAZOLE-5-BORONIC ACID; 1,3-BENZOXAZOLE-6-BORONIC ACID; 1,3-BIS(METHOXYMETHYL)-2,4-DIOXO-1,2,3,4-TETRAHYDROPYRIMIDINE-5-BORONIC ACID; 1,3-DICHLORO-4-METHOXY-BENZENE-2-YLBORONIC ACID; 1,3-DIHYDRO-2-BENZOFURAN-5-YLBORANEDIOL; 1,3-DIHYDRO-2H-PYRROLO[2,3-B]PYRIDIN-2-ONE-4-BORONIC ACID; 1,3-DIMETHYL-1H-INDAZOLE-4-BORONIC ACID; 1,3-DIMETHYL-1H-INDAZOLE-5-BORONIC ACID; 1,3-DIMETHYL-1H-INDAZOLE-6-BORONIC ACID; 1,3-DIMETHYL-1H-INDAZOLE-7-BORONIC ACID; 1,3-DIMETHYL-1H-PYRAZOL-4-YLBORONIC ACID; 1,3-DIMETHYLPYRAZOLE-5-BORONIC ACID; 1,3-DIMETHYLPYRIMIDINE-2,4-DIONE-5-BORONIC ACID; 1,3-OXAZOL-5-YLBORONIC ACID; 1,4-BENZODIOXANE-5-BORONIC ACID; 1,4-BENZODIOXANE-6-BORONIC ACID; 1,4-BENZODIOXIN-2-YLBORONIC ACID; 1,4-DIHYDROQUINAZOLIN-5-YLBORONIC ACID; 1,4-DIMETHOXYNAPHTHALEN-2-YLBORONIC ACID; 1,4-DIMETHYL-1H-INDAZOLE-5-BORONIC ACID; 1,4-DIMETHYL-1H-INDAZOLE-6-BORONIC ACID; 1,4-DIOXA-SPIRO[4,5]DEC-7-EN-8-BORONIC ACID; 1,5-DIMETHYL-1H-INDAZOLE-4-BORONIC ACID; 1,5-DIMETHYL-1H-INDAZOLE-6-BORONIC ACID; 1,5-DIMETHYL-1H-INDOL-2-YLBORONIC ACID; 1,5-DIMETHYLPYRAZOLE-4-BORONIC ACID; 1,5-DIMETHYL-PYRROL-3-YLBORONIC ACID; 1,6-DIMETHYL-1H-INDAZOLE-4-BORONIC ACID; 1,6-DIMETHYL-1H-INDAZOLE-5-BORONIC ACID; 1,7-DIMETHYL-1H-INDAZOLE-4-BORONIC ACID; 1,7-DIMETHYL-1H-INDAZOLE-5-BORONIC ACID; 1,7-NAPHTHYRIDIN-4-YLBORONIC ACID; 1,7-NAPHTHYRIDINE-3-BORONIC ACID; 1,8-NAPHTHALIC ANHYDRIDE-4-BORONIC ACID; 1,8-NAPHTHYRIDIN-2-YLBORONIC ACID; 1,8-NAPHTHYRIDIN-4-YLBORONIC ACID; 1-[1,3]-DIOXOLAN-2-YLMETHYL-1H-PYRAZOLE-4-BORONIC ACID; 1-[5-(DIHYDROXYBORYL)PYRIMIDIN-2-YL]PIPERIDINE-3-CARBOXYLIC ACID; 10-(2-NAPHTHYL)ANTHRACENE-9-BORONIC ACID; 1-ACETYL-1,2,3,6-TETRAHYDROPYRIDIN-4-YLBORONIC ACID; 1-ACETYL-4-CHLORO-PYRROL-3-YLBORONIC ACID; 1-ACETYL-4-ISOPROPYL-PYRROL-3-YLBORONIC ACID; 1-ACETYL-4-METHYL-PYRROL-3-YLBORONIC ACID; 1-ACETYL-PYRROL-3-YLBORONIC ACID; 1-ACETYLPYRROLIDIN-2-YLBORONIC ACID; 1-ALLYL-1H-PYRAZOL-4-YLBORONIC ACID; 1-AMINONAPHTHALENE-2-BORONIC ACID; 1-AMINONAPHTHALENE-3-BORONIC ACID; 1-AMINONAPHTHALENE-4-BORONIC ACID; 1-AMINONAPHTHALENE-6-BORONIC ACID; 1-AMINONAPHTHALENE-7-BORONIC ACID; 1-AMINONAPHTHALENE-8-BORONIC ACID; 1-BENZENESULFONYL-1H-INDOLE-4-BORONIC ACID; 1-BENZENESULFONYL-1H-INDOLE-7-BORONIC ACID; 1-BENZOTHIEN-7-YLBORONIC ACID; 1-BENZYL-1,2,3,4-TETRAHYDRO-6-QUINOLINYLBORONIC ACID; 1-BENZYL-1H-PYRAZOLE-4-BORONIC ACID; 1-BENZYL-4-CHLORO-PYRROL-3-YLBORONIC ACID; 1-BENZYL-4-ISOPROPYL-PYRROL-3-YLBORONIC ACID; 1-BENZYL-4-METHYL-PYRROL-3-YLBORONIC ACID; 1-BENZYL-PIPERIDINE-4-BORONIC ACID; 1-BENZYL-PYRROL-2-YLBORONIC ACID; 1-BENZYL-PYRROL-3-YLBORONIC ACID; 1-BIPHENYLENYLBORONIC ACID; 1-BOC-1,2,3,4-TETRAHYDRO-QUINOLINE-6-BORONIC ACID; 1-BOC-3,5-DIMETHYLPYRAZOLE-4-BORONIC ACID; 1-BOC-3-TRIFLUOROMETHYLPYRAZOLE-5-BORONIC ACID; 1-BOC-5,6-DICHLORO-1H-INDOLE-2-BORONIC ACID; 1-BOC-5-CHLORO-1H-INDOLE-2-BORONIC ACID; 1-BOC-5-CYANO-1H-INDOLE-2-BORONIC ACID; 1-BOC-5-FLUOROINDOLE-2-BORONIC ACID; 1-BOC-5-METHYL-1H-INDOLE-2-BORONIC ACID; 1-BOC-5-TBDMSO-INDOLE-2-BORONIC ACID; 1-BOC-6-CYANOINDOLE-2-BORONIC ACID; 1-BOC-6-METHOXYINDOLE-2-BORONIC ACID; 1-BOC-6-METHYLINDOLE-2-BORONIC ACID; 1-BOC-PIPERIDINE-4-BORONIC ACID; 1-BOC-PYRROLO[2,3-C]PYRIDINE-3-YLBORONIC ACID; 1-BUTENYLBORONIC ACID; 1-CARBOXYLMETHYL-1H-PYRAZOL-4-YLBORONIC ACID; 1-CHLOROISOQUINOLINE-4-BORONIC ACID; 1-CHLORONAPHTHALENE-2-BORONIC ACID; 1-CHLORONAPHTHALENE-3-BORONIC ACID; 1-CHLORONAPHTHALENE-4-BORONIC ACID; 1-CHLORONAPHTHALENE-5-BORONIC ACID; 1-CHLORONAPHTHALENE-6-BORONIC ACID;

1-CHLORONAPHTHALENE-7-BORONIC ACID; 1-CHLORONAPHTHALENE-8-BORONIC ACID; 1-CYCLOHEXEN-1-YL-BORONIC ACID; 1-CYCLOHEXYL-1H-PYRAZOLE-5-BORONIC ACID; 1-CYCLOHEXYL-VINYLBORONIC ACID; 1-CYCLOPENTYL-1H-PYRAZOLE-4-BORONIC ACID; 1-CYCLOPENTYL-PYRROL-3-YLBORONIC ACID; 1-ETHYL-1H-PYRAZOL-5-YLBORONIC ACID; 1-ETHYL-1H-PYRAZOLE-4-BORONIC ACID; 1-ETHYL-3-METHYL-1H-PYRAZOLE-5-BORONIC ACID; 1-ETHYL-3-PHENYL-1H-INDOL-2-YLBORONIC ACID; 1-ETHYL-PYRROL-3-YLBORONIC ACID; 1-FLUORONAPHTHALENE-2-BORONIC ACID; 1-FLUORONAPHTHALENE-3-BORONIC ACID; 1-FLUORONAPHTHALENE-5-BORONIC ACID; 1-FLUORONAPHTHALENE-6-BORONIC ACID; 1-FLUORONAPHTHALENE-7-BORONIC ACID; 1-FLUORONAPHTHALENE-8-BORONIC ACID; 1H-1,2,3-BENZOTRIAZOL-5-YLBORONIC ACID; 1H-1,2,3-BENZOTRIAZOL-6-YLBORONIC ACID; 1H-BENZIMIDAZOL-4-YLBORONIC ACID; 1H-BENZIMIDAZOL-5-YLBORONIC ACID; 1H-BENZIMIDAZOLE-5-BORONIC ACID, HYDROCHLORIDE SALT; 1H-BENZO[D]IMIDAZOL-6-YLBORONIC ACID; 1H-IMIDAZOL-2-YLBORONIC ACID HYDROCHLORIDE; 1H-IMIDAZOL-4-YLBORONIC ACID; 1H-IMIDAZOL-5-YLBORONIC ACID; 1H-INDAZOLE-4-BORONIC ACID; 1H-INDAZOLE-5-BORONIC ACID; 1H-INDAZOLE-5-BORONIC ACID HYDROCHLORIDE; 1H-INDAZOLE-7-BORONIC ACID; 1H-INDENE-2-BORONIC ACID; 1H-INDOL-2-YLBORONIC ACID; 1H-INDOL-4-YLBORONIC ACID HYDROCHLORIDE; 1H-INDOLE-1-CARBOXYLIC ACID, 2-BORONO-4-[[(1,1-DIMETHYLETHYL)DIMETHYLSILYL]OXY]-, 1-(1,1-DIMETHYLETHYL) ESTER; 1H-INDOLE-1-CARBOXYLIC ACID, 2-BORONO-4-METHOXY-, 1-(1,1-DIMETHYLETHYL) ESTER; 1H-INDOLE-1-CARBOXYLIC ACID, 2-BORONO-5-(1-METHYLETHOXY)-, 1-(1,1-DIMETHYLETHYL) ESTER; 1H-INDOLE-1-CARBOXYLIC ACID, 2-BORONO-5-(1-PIPERIDINYL)-, 1-(1,1-DIMETHYLETHYL) ESTER; 1H-INDOLE-1-CARBOXYLIC ACID, 2-BORONO-5-(1-PIPERIDINYLCARBONYL)-, 1-(1,1-DIMETHYLETHYL) ESTER; 1H-INDOLE-1-CARBOXYLIC ACID, 2-BORONO-5-(1-PIPERIDINYLMETHYL)-, 1-(1,1-DIMETHYLETHYL) ESTER; 1H-INDOLE-1-CARBOXYLIC ACID, 2-BORONO-5-(4-METHYL-1-PIPERAZINYL)-, 1-(1,1-DIMETHYLETHYL) ESTER; 1H-INDOLE-1-CARBOXYLIC ACID, 2-BORONO-5-(CYCLOHEXYLAMINO)-, 1-(1,1-DIMETHYLETHYL) ESTER; 1H-INDOLE-1-CARBOXYLIC ACID, 2-BORONO-5-(DIETHYLAMINO)-, 1-(1,1-DIMETHYLETHYL) ESTER; 1H-INDOLE-1-CARBOXYLIC ACID, 2-BORONO-5-(DIMETHYLAMINO)-, 1-(1,1-DIMETHYLETHYL) ESTER; 1H-INDOLE-1-CARBOXYLIC ACID, 2-BORONO-5-(METHYLTHIO)-, 1-(1,1-DIMETHYLETHYL) ESTER; 1H-INDOLE-1-CARBOXYLIC ACID, 2-BORONO-5-[(4,4-DIMETHOXY-1-PIPERIDINYL)METHYL]-, 1-(1,1-DIMETHYLETHYL) ESTER; 1H-INDOLE-1-CARBOXYLIC ACID, 2-BORONO-5-[(4-METHYL-1-PIPERAZINYL)CARBONYL]-, 1-(1,1-DIMETHYLETHYL) ESTER; 1H-INDOLE-1-CARBOXYLIC ACID, 2-BORONO-5-[(4-METHYL-1-PIPERAZINYL)SULFONYL]-, 1-(1,1-DIMETHYLETHYL) ESTER; 1H-INDOLE-1-CARBOXYLIC ACID, 2-BORONO-5-[(DIETHYLAMINO)METHYL]-, 1-(1,1-DIMETHYLETHYL) ESTER; 1H-INDOLE-1-CARBOXYLIC ACID, 2-BORONO-5-[(DIMETHYLAMINO)METHYL]-, 1-(1,1-DIMETHYLETHYL) ESTER; 1H-INDOLE-1-CARBOXYLIC ACID, 2-BORONO-5-[[2-[[(1,1-DIMETHYLETHYL)DIMETHYLSILYL]OXY]ETHYL]AMINO]METHYL]-, 1-(1,1-DIMETHYLETHYL) ESTER; 1H-INDOLE-1-CARBOXYLIC ACID, 2-BORONO-5-[[[3-(DIMETHYLAMINO)-2,2-DIMETHYLPROPYL]AMINO]METHYL]-, 1-(1,1-DIMETHYLETHYL) ESTER; 1H-INDOLE-1-CARBOXYLIC ACID, 2-BORONO-5-[[[DIMETHYL(1-METHYLETHYL)SILYL]OXY]METHYL]-, 1-(1,1-DIMETHYLETHYL) ESTER; 1H-INDOLE-1-CARBOXYLIC ACID, 2-BORONO-5-[[4-(2-HYDROXYETHYL)-1-PIPERAZINYL]METHYL]-, 1-(1,1-DIMETHYLETHYL) ESTER; 1H-INDOLE-1-CARBOXYLIC ACID, 2-BORONO-5-[2-(1-PIPERIDINYL)ETHOXY]-, 1-(1,1-DIMETHYLETHYL) ESTER; 1H-INDOLE-1-CARBOXYLIC ACID, 2-BORONO-5-[2-(4-MORPHOLINYL)ETHOXY]-, 1-(1,1-DIMETHYLETHYL) ESTER; 1H-INDOLE-1-CARBOXYLIC ACID, 2-BORONO-5-[3-(1,3-DIOXOLAN-2-YL)PROPYL]-, 1-(1,1-DIMETHYLETHYL) ESTER; 1H-INDOLE-1-CARBOXYLIC ACID, 2-BORONO-5-[3-(DIMETHYLAMINO)PROPYL]-, 1-(1,1-DIMETHYLETHYL) ESTER; 1H-INDOLE-1-CARBOXYLIC ACID, 2-BORONO-5-HYDROXY-, 1-(1,1-DIMETHYLETHYL) ESTER; 1H-INDOLE-1-CARBOXYLIC ACID, 2-BORONO-5-NITRO-, 1-(1,1-DIMETHYLETHYL) ESTER; 1H-INDOLE-1-CARBOXYLIC ACID, 2-BORONO-6-(TRIFLUOROMETHOXY)-, 1-(1,1-DIMETHYLETHYL) ESTER; 1H-INDOLE-1-CARBOXYLIC ACID, 2-BORONO-6-(TRIFLUOROMETHYL)-, 1-(1,1-DIMETHYLETHYL) ESTER; 1H-INDOLE-1-CARBOXYLIC ACID, 2-BORONO-6-[[(1,1-DIMETHYLETHYL)DIMETHYLSILYL]OXY]-, 1-(1,1-DIMETHYLETHYL) ESTER; 1H-INDOLE-1-CARBOXYLIC ACID, 2-BORONO-6-[[[(1,1-DIMETHYLETHYL)DIMETHYLSILYL]OXY]METHYL]-, 1-(1,1-DIMETHYLETHYL) ESTER; 1H-INDOLE-1-CARBOXYLIC ACID, 2-BORONO-6-ETHOXY-, 1-(1,1-DIMETHYLETHYL) ESTER; 1H-INDOLE-1-CARBOXYLIC ACID, 2-BORONO-6-HYDROXY-, 1-(1,1-DIMETHYLETHYL) ESTER; 1H-INDOLE-1-CARBOXYLIC ACID, 2-BORONO-7-CHLORO-, 1-(1,1-DIMETHYLETHYL) ESTER; 1H-INDOLE-1-CARBOXYLIC ACID, 2-BORONO-7-HYDROXY-, 1-(1,1-DIMETHYLETHYL) ESTER; 1H-INDOLE-1-CARBOXYLIC ACID, 4-[[BIS(1-METHYLETHYL)AMINO]CARBONYL]-2-BORONO-, 1-(1,1-DIMETHYLETHYL) ESTER; 1H-INDOLE-1-CARBOXYLIC ACID, 5-BORONO-2,3-DIHYDRO-7-NITRO-, 1-(1,1-DIMETHYLETHYL) ESTER; 1H-PYRAZOLE-1-BENZYL-4-BORONIC ACID; 1H-PYRAZOLE-3-BORONIC ACID; 1H-PYRAZOLE-3-BORONIC ACID HYDRATE; 1H-PYRAZOLE-4-BORONIC ACID; 1H-PYRAZOLE-4-BORONIC ACID HCL; 1H-PYRAZOLE-5-BORONIC ACID; 1H-PYRAZOLO[3,4-B]PYRIDINE-5-BORONIC ACID; 1H-PYRAZOLO[3,4-C]PYRIDINE-4-BORONIC ACID; 1H-PYRAZOLO[4,3-B]PYRIDINE-6-BORONIC ACID; 1H-PYRAZOLO[4,3-B]PYRIDINE-7-BORONIC ACID; 1H-PYRROLO[2,3-B]PYRIDIN-4-YLBORONIC ACID; 1H-PYRROLO[2,3-B]PYRIDIN-5-YLBORONIC ACID; 1H-PYRROLO[2,3-B]PYRIDINE-2-BORONIC ACID; 1H-PYRROLO[2,3-B]PYRIDINE-3-BORONIC ACID; 1H-PYRROLO[2,3-B]PYRIDINE-6-BORONIC ACID; 1H-PYRROLO[2,3-C]PYRIDINE-3-YLBORONIC ACID; 1H-PYRROLO[3,2-B]PYRIDIN-5-YLBORONIC ACID; 1H-PYRROLO[3,2-B]

PYRIDIN-6-YLBORONIC ACID; 1H-PYRROLO[3,2-B]PYRIDINE-2-BORONIC ACID; 1H-PYRROLO[3,2-B]PYRIDINE-3-BORONIC ACID; 1H-PYRROLO[3,2-B]PYRIDINE-7-BORONIC ACID; 1-HYDROXYL-2-NAPHTHALENEBORONIC ACID; 1-ISOBUTYL-1H-PYRAZOL-5-YLBORONIC ACID; 1-ISOBUTYL-1H-PYRAZOLE-4-BORONIC ACID; 1-ISOPROPYL-1H-PYRAZOL-4-YLBORONIC ACID; 1-ISOPROPYL-1H-PYRAZOLE-5-BORONIC ACID; 1-ISOPROPYL-1H-PYRROL-3-YLBORONIC ACID; 1-ISOPROPYL-3-METHYL-1H-PYRAZOLE-5-BORONIC ACID; 1-ISOPROPYL-PYRROL-2-YLBORONIC ACID; 1-ISOQUINOLYLBORONIC ACID; 1-METHOXYNAPHTHALENE-2-BORONIC ACID; 1-METHOXYNAPHTHALENE-3-BORONIC ACID; 1-METHOXYNAPHTHALENE-5-BORONIC ACID; 1-METHOXYNAPHTHALENE-6-BORONIC ACID; 1-METHOXYNAPHTHALENE-7-BORONIC ACID; 1-METHOXYNAPHTHALENE-8-BORONIC ACID; 1-METHYL-1,2,3-TRIAZOLE-4-BORONIC ACID; 1-METHYL-1H-BENZOIMIDAZOLE-6-BORONIC ACID; 1-METHYL-1H-IMIDAZOL-5-YLBORONIC ACID; 1-METHYL-1H-INDAZOLE-4-BORONIC ACID HYDROCHLORIDE; 1-METHYL-1H-INDAZOLE-5-BORONIC ACID; 1-METHYL-1H-PYRAZOL-3-YLBORONIC ACID; 1-METHYL-1H-PYRAZOL-5-YLBORONIC ACID; 1-METHYL-1H-PYRAZOLE-4-BORONIC ACID; 1-METHYL-1H-PYRAZOLE-4-BORONIC ACID HYDROCHLORIDE; 1-METHYL-1H-PYRROL-2-YL BORONIC ACID; 1-METHYL-1H-PYRROL-3-YLBORONIC ACID; 1-METHYL-2-(TRIPHENYL-METHYL)ISOINDOLE-5-BORONIC ACID; 1-METHYL-2-OXOINDOLIN-6-YLBORONIC ACID; 1-METHYL-3-CYCLOPROPYL-1H-PYRAZOLE-5-BORONIC ACID; 1-METHYL-3-ETHYL-1H-PYRAZOLE-5-BORONIC ACID; 1-METHYL-3-ISOPROPYL-1H-PYRAZOLE-5-BORONIC ACID; 1-METHYL-3-TERT-BUTYL-1H-PYRAZOLE-5-BORONIC ACID; 1-METHYL-3-TRIFLUOROMETHYLPYRAZOLE-5-BORONIC ACID; 1-METHYL-4-CHLORO-1H-PYRAZOLE-5-BORONIC ACID; 1-METHYL-5-PHENYL-PYRROL-3-YLBORONIC ACID; 1-METHYLINDAZOLE-4-BORONIC ACID; 1-METHYLINDAZOLE-6-BORONIC ACID; 1-METHYLINDAZOLE-7-BORONIC ACID; 1-METHYLINDOLE-5-BORONIC ACID; 1-METHYLNAPHTHALENE-2-BORONIC ACID; 1-METHYLNAPHTHALENE-3-BORONIC ACID; 1-METHYLNAPHTHALENE-5-BORONIC ACID; 1-METHYLNAPHTHALENE-6-BORONIC ACID; 1-METHYLNAPHTHALENE-7-BORONIC ACID; 1-METHYLNAPHTHALENE-8-BORONIC ACID; 1-METHYL-PIPERIDINE-4-BORONIC ACID; 1-NAPHTHALENEBORONIC ACID; 1-NAPHTHALENECARBOXYLIC ACID, 5-BORONIC ACID; 1-N-BOC-PYRROLE-3-BORONIC ACID; 1-N-BOC-PYRROLIDIN-2-YLBORONIC ACID; 1-NEOPENTYL-1H-PYRAZOLE-5-BORONIC ACID; 1-NONANEBORONIC ACID; 1-N-THP-PYRAZOL-3-YLBORONIC ACID; 1-PENTEN-YL BORONIC ACID; 1-PENTENYLBORONIC ACID; 1-PHENYL-1H-INDOL-2-YLBORONIC ACID; 1-PHENYL-1H-PYRAZOLE-4-BORONIC ACID; 1-PHENYL-1H-PYRROL-2-YLBORONIC ACID; 1-PHENYL-3,4-DIHYDROPYRROLO[1,2-A]PYRAZIN-6-YLBORONIC ACID; 1-PHENYL-CYCLOPROPYL-1-BORONIC ACID; 1-PHENYL-PYRROL-3-YLBORONIC ACID; 1-PHENYLSULFONYLINDOLE-6-BORONIC ACID; 1-PHENYLVINYLBORONIC ACID; 1-PIPERIDINECARBOXYLIC ACID, 4-(4-BORONOPHENYL)-4-(4-CHLOROPHENYL)-, 1-(1,1-DIMETHYLETHYL) ESTER; 1-PROPYL-1H-PYRAZOL-4-YLBORONIC ACID; 1-PROPYL-1H-PYRAZOL-5-YLBORONIC ACID; 1-P-TOLYL-1H-PYRAZOL-4-YLBORONIC ACID; 1-PYRENEBORONIC ACID; 1-TBDMS-INDOLE-4-BORONIC ACID; 1-TERT-BUTOXYCARBONYL-1H-PYRAZOLE-4-BORONIC ACID; 1-TERT-BUTYL-1H-PYRAZOLE-4-BORONIC ACID; 1-TERT-BUTYL-1H-PYRAZOLE-5-BORONIC ACID; 1-TERT-BUTYL-4-(ETHOXYCARBONYL)-1H-PYRAZOL-5-YLBORONIC ACID; 1-TERT-BUTYLOXYCARBONYL-PYRRAZOLE-3-BORIC ACID; 1-TERT-BUTYRONYCARBONYL-3-BORIC INDAZOLE; 1-TOSYL-1H-PYRROLO[2,3-B]PYRIDIN-3-YLBORONIC ACID; 2-((1-(TERT-BUTOXYCARBONYL)AZEPAN-3-YL)METHYL)PHENYLBORONIC ACID; 2-((1-(TERT-BUTOXYCARBONYL)PIPERIDIN-3-YL)METHYL)PHENYLBORONIC ACID; 2-((1-(TERT-BUTOXYCARBONYL)PYRROLIDIN-3-YL)METHYL)PHENYLBORONIC ACID; 2-((2'-CHLORO-5'-(TRIFLUOROMETHYL)PHENOXY)METHYL)PHENYLBORONIC ACID; 2-((3-(TRIFLUOROMETHYL)PHENOXY)METHYL)PHENYLBORONIC ACID; 2-((3-CYCLOPROPYLUREIDO)METHYL)PHENYLBORONIC ACID; 2-((3-ETHYLUREIDO)METHYL)PHENYLBORONIC ACID; 2-((3-METHYLUREIDO)METHYL)PHENYLBORONIC ACID; 2-((4'-(TRIFLUOROMETHOXY)PHENOXY)METHYL)PHENYLBORONIC ACID; 2-((BENZYLOXY)CARBONYL)-1,2,3,4-TETRAHYDROISOQUINOLIN-6-YL-6-BORONIC ACID; 2-((BENZYLOXYCARBONYLAMINO)METHYL)PHENYLBORONIC ACID; 2-((DIETHYLAMINO)METHYL)PHENYLBORONIC ACID; 2-((DIISOPROPYLAMINO)METHYL)PHENYLBORONIC ACID; 2-((DIMETHYLAMINO)METHYL)-5-NITROPHENYLBORONIC ACID; 2-((DIMETHYLAMINO)METHYL)THIAZOL-5-YLBORONIC ACID; 2-((TERT-BUTOXYCARBONYLAMINO)METHYL)-5-NITROPHENYLBORONIC ACID; 2-((TERT-BUTOXYCARBONYLAMINO)METHYL)PYRIMIDIN-5-YLBORONIC ACID; 2-([2-(DIHYDROXYBORANYL)-4-FLUOROPHENYL]METHYL)-2,3-DIHYDROPYRIDAZIN-3-ONE; 2-([2-(DIHYDROXYBORANYL)PHENYL]METHYL)-2,3-DIHYDROPYRIDAZIN-3-ONE; 2-([2-(DIHYDROXYBORANYL)PHENYL]METHYL)-6-METHYL-2,3-METHYLPYRIDINE-4-BORONIC ACID; 2-(2,4,5-TRICHLOROPHENYL)-3-(TRIFLUOROMETHYL)PYRIDINE-4-BORONIC ACID; 2-(2,4,5-TRICHLOROPHENYL)-4-(TRIFLUOROMETHYL)PYRIDINE-3-BORONIC ACID; 2-(2,4,5-TRICHLOROPHENYL)-5-(TRIFLUOROMETHYL)PYRIDINE-3-BORONIC ACID; 2-(2,4,5-TRICHLOROPHENYL)-5-(TRIFLUOROMETHYL)PYRIDINE-4-BORONIC ACID; 2-(2,4,5-TRICHLOROPHENYL)-6-(TRIFLUOROMETHYL)PYRIDINE-3-BORONIC ACID; 2-(2,4,5-TRICHLOROPHENYL)-6-(TRIFLUOROMETHYL)PYRIDINE-4-BORONIC ACID; 2-(2,4-DICHLOROPHENYLMETHOXY)PHENYLBORONIC ACID; 2-(2,5-DIHYDRO-1H-PYRROL-1-YL)PYRIMIDIN-5-YLBORONIC ACID; 2-(2,5-DIMETHYL-1H-PYRROL-1-YL)PYRIDIN-4-YLBORONIC ACID; 2-(2,5-DIMETHYLPYRROL-1-YL)-5-CHLOROPYRIDINE-4-BORONIC ACID; 2-(2-[3-(DIHYDROXYBORANYL)

PHENOXY]ETHYL)-2,3-DIHYDROPYRIDAZIN-3-ONE; 2-(2-AMINO-2-OXOETHYL)PHENYLBORONIC ACID; 2-(2-BORONOPHENOXYMETHYL)BENZONITRILE; 2-(2-BORONOPHENYL)ACETIC ACID; 2-(2-CARBOXYVINYL)BENZENEBORONIC ACID; 2-(2'-CHLOROBENZYLOXY)PHENYLBORONIC ACID; 2-(2-CHLOROETHYL)-4,5-DIMETHOXYPHENYLBORONIC ACID; 2-(2-CHLOROETHYL)PHENYLBORONIC ACID; 2-(2-CHLOROPHENOXYMETHYL)PHENYLBORONIC ACID; 2-(2-CHLOROPHENYL)PYRIMIDIN-5-YLBORONIC ACID; 2-(2-FLUOROPHENOXY)PHENYLBORONIC ACID; 2-(2-FLUOROPHENYL)PYRIMIDIN-5-YLBORONIC ACID; 2-(2-FURYL)PYRIMIDINE-5-BORONIC ACID; 2-(2H-TETRAZOL-5-YL)-PHENYLBORONIC ACID; 2-(2-HYDROXYETHYL)PHENYLBORONIC ACID; 2-(2'-METHOXYBENZYLOXY)PHENYLBORONIC ACID; 2-(2-METHOXYETHOXY)PHENYLBORONIC ACID; 2-(2-METHOXYPHENYL)PYRIMIDIN-5-YLBORONIC ACID; 2-(2-METHYL-1,3-DIOXOLAN-2-YL)PHENYLBORONIC ACID; 2-(2-METHYLIMIDAZOL-1-YL)PYRIMIDINE-4-BORONIC ACID; 2-(2-METHYLIMIDAZOL-1-YL)PYRIMIDINE-5-BORONIC ACID; 2-(2-METHYLPIPERIDIN-1-YL)THIAZOLE-4-BORONIC ACID; 2-(2-OXOPYRROLIDIN-1-YL)PYRIMIDIN-5-YLBORONIC ACID; 2-(2-PYRIDYL)PYRIMIDINE-5-BORONIC ACID; 2-(2-TERT-BUTYLPHENOXY)PYRIDIN-3-YLBORONIC ACID; 2-(2-THIENYL)PYRIMIDINE-5-BORONIC ACID; 2-(2-TOLYL)PYRIMIDINE-5-BORONIC ACID; 2-(2-TRIFLUOROMETHYL-PHENYL)-ETHENEBORONIC ACID; 2-(3-(TRIFLUOROMETHOXY)PHENYL)-3-(TRIFLUOROMETHYL)PYRIDINE-4-BORONIC ACID; 2-(3-(TRIFLUOROMETHOXY)PHENYL)-4-(TRIFLUOROMETHYL)PYRIDINE-3-BORONIC ACID; 2-(3-(TRIFLUOROMETHOXY)PHENYL)-5-(TRIFLUOROMETHYL)PYRIDINE-3-BORONIC ACID; 2-(3-(TRIFLUOROMETHOXY)PHENYL)-5-(TRIFLUOROMETHYL)PYRIDINE-4-BORONIC ACID; 2-(3-(TRIFLUOROMETHOXY)PHENYL)-6-(TRIFLUOROMETHYL)PYRIDINE-3-BORONIC ACID; 2-(3-(TRIFLUOROMETHOXY)PHENYL)-6-(TRIFLUOROMETHYL)PYRIDINE-4-BORONIC ACID; 2-(3-(TRIFLUOROMETHYL)PHENYL)PYRIMIDIN-5-YLBORONIC ACID; 2-(3,3-DIETHOXYPROPOXY)PHENYLBORONIC ACID; 2-(3-BORONOPHENOXYMETHYL)BENZONITRILE; 2-(3-BORONOPHENYL)-2-METHYL-1,3-DIOXOLANE; 2-(3-BORONOPHENYL)-5-METHYL-1,3,4-OXADIAZOLE; 2-(3-BORONOPHENYL)ACETIC ACID; 2-(3'-CHLOROBENZYLOXY)PHENYLBORONIC ACID; 2-(3-CHLOROPHENOXYMETHYL)PHENYLBORONIC ACID; 2-(3-CHLOROPHENYL)ETHENEBORONIC ACID; 2-(3-CHLOROPHENYL)PYRIMIDIN-5-YLBORONIC ACID; 2-(3-CYANOPHENYLMETHOXY)PHENYLBORONIC ACID; 2-(3'-FLUOROBENZYLOXY)PHENYLBORONIC ACID; 2-(3-FLUOROPHENYL)PYRIMIDIN-5-YLBORONIC ACID; 2-(3-FLUOROPROPOXY)-BENZENEBORONIC ACID; 2-(3-FURYL)PYRIMIDINE-5-BORONIC ACID; 2-(3-HYDROXYPROPOXY)PYRIMIDIN-5-YLBORONIC ACID; 2-(3-HYDROXYPYRROLIDIN-1-YL)PYRIMIDINE-4-BORONIC ACID; 2-(3-METHOXYPHENYL)PYRIMIDIN-5-YLBORONIC ACID; 2-(3-METHOXYPROPOXY)PHENYLBORONIC ACID; 2-(3-METHYL-1H-PYRAZOL-1-YL)PYRIMIDIN-5-YLBORONIC ACID; 2-(3-METHYL-1H-PYRAZOL-1-YL)PYRIMIDINE-4-BORONIC ACID; 2-(3-METHYL-1H-PYRAZOL-1-YL)THIAZOLE-4-BORONIC ACID; 2-(3-METHYLPIPERIDIN-1-YL)THIAZOLE-4-BORONIC ACID; 2-(3-PHENYLBORONIC ACID)-2-METHYL-OXETANE; 2-(3-PYRIDYL)PYRIMIDINE-5-BORONIC ACID; 2-(3-THIENYL)PYRIMIDINE-5-BORONIC ACID; 2-(3-TOLYL)PYRIMIDINE-5-BORONIC ACID; 2-(4-(CYCLOHEXYLOXY)PIPERIDIN-1-YL)PYRIMIDIN-5-YLBORONIC ACID; 2-(4-(T-BUTOXYCARBONYL)PIPERAZIN-1-YL)PYRIDINE-3-BORONIC ACID; 2-(4-(TERT-BUTOXYCARBONYL)PIPERAZIN-1-YL)PYRIDIN-4-YLBORONIC ACID; 2-(4-(TRIFLUOROMETHOXY)PHENYL)-3-(TRIFLUOROMETHYL)PYRIDINE-4-BORONIC ACID; 2-(4-(TRIFLUOROMETHOXY)PHENYL)-4-(TRIFLUOROMETHYL)PYRIDINE-3-BORONIC ACID; 2-(4-(TRIFLUOROMETHOXY)PHENYL)-5-(TRIFLUOROMETHYL)PYRIDINE-3-BORONIC ACID; 2-(4-(TRIFLUOROMETHOXY)PHENYL)-5-(TRIFLUOROMETHYL)PYRIDINE-4-BORONIC ACID; 2-(4-(TRIFLUOROMETHOXY)PHENYL)-6-(TRIFLUOROMETHYL)PYRIDINE-3-BORONIC ACID; 2-(4-(TRIFLUOROMETHOXY)PHENYL)-6-(TRIFLUOROMETHYL)PYRIDINE-4-BORONIC ACID; 2-(4-(TRIFLUOROMETHYL)PHENYL)PYRIMIDIN-5-YLBORONIC ACID; 2-(4-(TRIFLUOROMETHYL)PHENYL)THIAZOL-5-YLBORONIC ACID; 2-(4-ACETYLPIPERAZIN-1-YL)PYRIDIN-4-YLBORONIC ACID; 2-(4-BENZYLOXYPHENYL)PYRIMIDINE-5-BORONIC ACID; 2-(4-BORONOBENZOYL)HYDRAZINECARBOTHIOAMIDE; 2-(4-BORONOBENZOYL)-N-METHYLHYDRAZINECARBOTHIOAMIDE; 2-(4-BORONOPHENOXYMETHYL)BENZONITRILE; 2-(4-BORONOPHENYL)-2-METHYLPROPANENITRILE; 2-(4-BORONOPHENYL)-2-METHYLPROPANOIC ACID; 2-(4-BORONOPHENYL)-5,6-DIHYDRO-4H-1,3-OXAZINE; 2-(4-BORONOPHENYL)ACETIC ACID; 2-(4-CBZ-PIPERAZIN-1-YL)PYRIDINE-5-BORONIC ACID; 2-(4-CHLOROPHENOXYMETHYL)PHENYLBORONIC ACID; 2-(4-CHLOROPHENYL)PYRIMIDIN-5-YLBORONIC ACID; 2-(4-CYANOPHENYLMETHOXY)PHENYLBORONIC ACID; 2-(4-DIHYDROXYBORANE)PHENYL-4-CARBOXY-6-METHYLQUINOLINE; 2-(4-DIHYDROXYBORANE)PHENYL-4-CARBOXYQUINOLINE; 2-(4'-FLUOROBENZYLOXY)PHENYLBORONIC ACID; 2-(4-FLUOROPHENYL)CYCLOPROPYLBORONIC ACID; 2-(4-FLUOROPHENYL)PYRIDIN-4-YLBORONIC ACID; 2-(4-FLUOROPHENYL)PYRIMIDIN-5-YLBORONIC ACID; 2-(4-HYDROXYPIPERIDIN-1-YL)-6-CHLOROPYRIMIDINE-4-BORONIC ACID; 2-(4'-METHOXYBENZYLOXY)PHENYLBORONIC ACID; 2-(4-METHOXYBENZYLOXY)PYRIMIDIN-5-YLBORONIC ACID; 2-(4-METHOXYPHENYL)PYRIDIN-4-YLBORONIC ACID; 2-(4-METHOXYPHENYL)PYRIMIDIN-5-YLBORONIC ACID; 2-(4-METHYL-1H-PYRAZOL-1-YL)PYRIMIDIN-5-YLBORONIC ACID; 2-(4-METHYL-1H-PYRAZOL-1-YL)PYRIMIDINE-4-BORONIC ACID; 2-(4-METHYL-1H-PYRAZOL-1-YL)THIAZOLE-4-BORONIC ACID; 2-(4-METHYLIMIDAZOL-1-YL)PYRIMIDINE-5-BORONIC ACID; 2-(4-METHYLPIPERAZIN-1-YL)PYRIDIN-4-YLBORONIC ACID; 2-(4-METHYLPIPERAZIN-1-YL)PYRIMIDIN-5-YLBORONIC ACID; 2-(4-METHYLPIPERIDIN-1-YL)THIAZOLE-4-BORONIC ACID; 2-(4-NITROPHENYL)ETHENYLBORONIC ACID; 2-(4-PENTYLOXYPHENYL)PYRIMIDINE-5-BORONIC

ACID; 2-(4-PENTYLPHENYL)PYRIMIDINE-5-BORONIC ACID; 2-(4-PYRIDYL)PYRIMIDINE-5-BORONIC ACID; 2-(4-TERT-BUTYLPHENYL)ACETYLENE-1-BORONIC ACID; 2-(4-TOLYL)PYRIMIDINE-5-BORONIC ACID; 2-(5-(3,3,3-TRIFLUOROPROPYL)-1,3,4-OXADIAZOL-2-YL)PHENYLBORONIC ACID; 2-(5-(DIMETHYLAMINO)-1,3,4-OXADIAZOL-2-YL)PHENYLBORONIC ACID; 2-(5-[1,3]DIOXOLAN-2-YL-2,4-DIMETHOXY-PHENYL)-BORONIC ACID; 2-(5-ETHOXY-1,3,4-OXADIAZOL-2-YL)PHENYLBORONIC ACID; 2-(5-ISOBUTYL-1,3,4-OXADIAZOL-2-YL)PHENYLBORONIC ACID; 2-(5-ISOPROPYL-1,3,4-OXADIAZOL-2-YL)PHENYLBORONIC ACID; 2-(5-METHYL-1,3,4-OXADIAZOL-2-YL)-4-(TRIFLUOROMETHYL)PHENYLBORONIC ACID; 2-(5-PROPYL-1,3,4-OXADIAZOL-2-YL)PHENYLBORONIC ACID; 2-(5-PROPYL-1,3,4-THIADIAZOL-2-YL)PHENYLBORONIC ACID; 2-(ALLYLOXY)-5-(TRIFLUOROMETHYL)BENZENEBORONIC ACID; 2-(AMINOMETHYL)-5-FLUOROBENZENEBORONIC ACID HYDROCHLORIDE; 2-(AMINOMETHYL)-5-FLUOROPHENYLBORONIC ACID; 2-(AMINOMETHYL)-5-NITROPHENYLBORONIC ACID; 2-(AMINOMETHYL)PHENYL BORONIC ACID; 2-(AMINOMETHYL)PHENYLBORONIC ACID, HCL; 2-(AMINOMETHYL)THIAZOL-5-YLBORONIC ACID; 2-(AZETIDIN-1-YL)PYRIDIN-4-YLBORONIC ACID; 2-(AZETIDINE-1-CARBONYL)PHENYLBORONIC ACID; 2-(AZIRIDINE-1-CARBONYL)PHENYLBORONIC ACID; 2-(BENZYL(METHYL)AMINO)QUINOLIN-6-YLBORONIC ACID; 2-(BENZYLAMINO)PYRIDIN-4-YLBORONIC ACID; 2-(BENZYLOXY)-3,5-DIFLUOROPHENYLBORONIC ACID; 2-(BENZYLOXY)-3-CHLOROPHENYLBORONIC ACID; 2-(BENZYLOXY)-3-METHYLPHENYLBORONIC ACID; 2-(BENZYLOXY)-4-(DIMETHYLAMINO)PYRIMIDINE-5-BORONIC ACID; 2-(BENZYLOXY)-4-METHOXYPHENYLBORONIC ACID; 2-(BENZYLOXY)-4-METHYLPHENYLBORONIC ACID; 2-(BENZYLOXY)-5-BORONOBENZOIC ACID; 2-(BENZYLOXY)-5-ETHOXYPHENYLBORONIC ACID; 2-(BENZYLOXY)-5-FLUOROPYRIDIN-3-YLBORONIC ACID; 2-(BENZYLOXY)-5-METHOXYPHENYLBORONIC ACID; 2-(BENZYLOXY)-5-TERT-BUTYLPHENYLBORONIC ACID; 2-(BENZYLOXY)NAPHTHALEN-1-YLBORONIC ACID; 2-(BENZYLOXY)PYRIDINE-4-BORONIC ACID; 2-(BENZYLOXY)PYRIMIDIN-5-YLBORONIC ACID; 2-(BENZYLOXYCARBONYLAMINO)ETHYLBORONIC ACID; 2-(BIPHENYL)PHENYLBORONIC ACID; 2-(BOC-AMINO)THIAZOLE-5-BORONIC ACID; 2-(BOC-AMINOMETHYL)PYRIDINE-4-BORONIC ACID; 2-(BUTOXYCARBONYLAMINO)PYRIDIN-3-YLBORONIC ACID; 2-(CHLOROMETHYL)-5-NITROPHENYLBORONIC ACID; 2-(CYANOMETHYL)PHENYLBORONIC ACID; 2-(CYCLOBUTOXY)PYRIMIDINE-5-BORONIC ACID; 2-(CYCLOBUTYL)PYRIMIDINE-5-BORONIC ACID; 2-(CYCLOBUTYLAMINO)THIAZOLE-4-BORONIC ACID; 2-(CYCLOHEXYL)PYRIMIDINE-5-BORONIC ACID; 2-(CYCLOHEXYLAMINO)THIAZOLE-4-BORONIC ACID; 2-(CYCLOHEXYLETHYL)BORONIC ACID; 2-(CYCLOHEXYLOXY)METHYLPHENYLBORONIC ACID; 2-(CYCLOHEXYLOXY)PYRIMIDIN-5-YLBORONIC ACID; 2-(CYCLOPENTOXY)PYRIMIDINE-5-BORONIC ACID; 2-(CYCLOPENTYL)PYRIDINE-4-BORONIC ACID; 2-(CYCLOPENTYL)PYRIMIDINE-5-BORONIC ACID; 2-(CYCLOPENTYLAMINO)THIAZOLE-4-BORONIC ACID; 2-(CYCLOPROPANECARBOXAMIDO)PHENYLBORONIC ACID; 2-(CYCLOPROPYLAMINO)THIAZOLE-4-BORONIC ACID; 2-(CYCLOPROPYLCARBAMOYL)-5-METHYLPYRIDIN-4-YLBORONIC ACID; 2-(CYCLOPROPYLCARBAMOYL)PYRIDIN-4-YLBORONIC ACID; 2-(CYCLOPROPYLMETHOXY)-4-TRIFLUOROMETHYLPHENYLBORONIC ACID; 2-(CYCLOPROPYLMETHOXY)PHENYLBORONIC ACID; 2-(CYCLOPROPYLMETHOXY)PYRIDINE-5-BORONIC ACID; 2-(DICYCLOHEXYLPHOSPHINO)PHENYLBORONIC ACID; 2-(DIETHYLAMINO)THIAZOLE-4-BORONIC ACID; 2-(DIFLUOROMETHOXY)-5-FLUOROPHENYLBORONIC ACID; 2-(DIFLUOROMETHOXY)-6-FLUOROPHENYLBORONIC ACID; 2-(DIFLUOROMETHOXY)-BENZENEBORONIC ACID; 2-(DIFLUOROMETHOXY)NAPHTHALENE-1-BORONIC ACID; 2-(DIFLUOROMETHOXY)NAPHTHALENE-3-BORONIC ACID; 2-(DIFLUOROMETHOXY)NAPHTHALENE-4-BORONIC ACID; 2-(DIFLUOROMETHOXY)NAPHTHALENE-5-BORONIC ACID; 2-(DIFLUOROMETHOXY)NAPHTHALENE-6-BORONIC ACID; 2-(DIFLUOROMETHOXY)NAPHTHALENE-7-BORONIC ACID; 2-(DIFLUOROMETHOXY)NAPHTHALENE-8-BORONIC ACID; 2-(DIFLUOROMETHOXY)PYRAZINE-6-BORONIC ACID; 2-(DIFLUOROMETHYL)-5-FLUOROPHENYLBORONIC ACID; 2-(DIFLUOROMETHYL)NAPHTHALENE-1-BORONIC ACID; 2-(DIFLUOROMETHYL)NAPHTHALENE-3-BORONIC ACID; 2-(DIFLUOROMETHYL)NAPHTHALENE-4-BORONIC ACID; 2-(DIFLUOROMETHYL)NAPHTHALENE-5-BORONIC ACID; 2-(DIFLUOROMETHYL)NAPHTHALENE-6-BORONIC ACID; 2-(DIFLUOROMETHYL)NAPHTHALENE-7-BORONIC ACID; 2-(DIFLUOROMETHYL)NAPHTHALENE-8-BORONIC ACID; 2-(DIHYDROXYBORYL)-3-THIOPHENECARBOXYLIC ACID; 2-(DIHYDROXYBORYL)-4-METHOXYBENZOIC ACID; 2-(DIHYDROXYBORYL)-5-METHOXYBENZOIC ACID; 2-(DIISOPROPYLCARBANOYL) PHENYLBORONIC ACID; 2-(DIMETHYLAMINE)PHENYLBORONIC ACID; 2-(DIMETHYLAMINO)-4,6-DIMETHYLPYRIMIDIN-5-YLBORONIC ACID; 2-(DIMETHYLAMINO)-4-METHOXYPYRIMIDIN-5-YLBORONIC ACID; 2-(DIMETHYLAMINO)-5-METHYLPHENYLBORONIC ACID; 2-(DIMETHYLAMINO)-5-PYRIDINYL BORONIC ACID HYDROCHLORIDE; 2-(DIMETHYLAMINO)-6-OXO-1,6-DIHYDROPYRIMIDIN-5-YLBORONIC ACID; 2-(DIMETHYLAMINO)BENZENEBORONIC ACID HYDROCHLORIDE; 2-(DIMETHYLAMINO)PYRIDINE-3-BORONIC ACID; 2-(DIMETHYLAMINO)PYRIDINE-5-BORONIC ACID HYDRATE; 2-(DIMETHYLAMINO)THIAZOLE-4-BORONIC ACID; 2-(DIMETHYLAMINOCARBONYL)BENZENEBORONIC ACID; 2-(E-CYANOVINYL)PHENYLBORONIC ACID; 2-(ETHOXYCARBONYL)-1H-IMIDAZOL-5-YLBORONIC ACID; 2-(ETHOXYCARBONYL)-1-METHYL-1H-IMIDAZOL-5-YLBORONIC ACID; 2-(ETHOXYCARBONYL)-4-FLUOROPHENYLBORONIC ACID; 2-(ETHOXYCARBONYL)FURAN-3-BORONIC ACID; 2-(ETHOXYCARBONYL)PYRIDINE-4-BORONIC ACID; 2-(ETHOXYCARBONYL)THIOPHEN-3-YLBORONIC ACID; 2-(ETHOXY-D5)-PHENYLBORONIC ACID; 2-(ETHOXY-D5)-PYRIMIDINE-5-BORONIC ACID; 2-(ETHYL-D5)-

PHENYLBORONIC ACID; 2-(ETHYL-D5)-PYRIMIDINE-5-BORONIC ACID; 2-(FURAN-2-YL)PYRIDINE-4-BORONIC ACID; 2-(HYDROXY)PYRIDINE-4-BORONIC ACID; 2-(HYDROXYMETHYL)-6-METHOXYPHENYLBORONIC ACID; 2-(HYDROXYMETHYL)FURAN-3-YLBORONIC ACID; 2-(HYDROXYMETHYL)NAPHTHALENE-1-BORONIC ACID; 2-(HYDROXYMETHYL)PHENYLBORONIC ACID; 2-(HYDROXYMETHYL)THIOPHEN-3-YLBORONIC ACID; 2-(IMIDAZOL-1-YL)PYRIMIDINE-4-BORONIC ACID; 2-(IMIDAZOL-1-YL)PYRIMIDINE-5-BORONIC ACID; 2-(IMIDAZOL-1-YL)THIAZOLE-4-BORONIC ACID; 2-(ISOBUTOXY)PYRIDINE-3-BORONIC ACID; 2-(ISOBUTYLTHIO)-5-(TRIFLUOROMETHYL)PYRIDINE-3-BORONIC ACID; 2-(ISOPROPOXY)PYRIDINE-4-BORONIC ACID; 2-(ISO-PROPOXY-D7)-PHENYLBORONIC ACID; 2-(ISO-PROPOXY-D7)-PYRIMIDINE-5-BORONIC ACID; 2-(ISOPROPYL)PYRIDINE-4-BORONIC ACID; 2-(ISO-PROPYL-D7)-PHENYLBORONIC ACID; 2-(ISO-PROPYL-D7)-PYRIDINE-4-BORONIC ACID; 2-(ISO-PROPYL-D7)-PYRIMIDINE-5-BORONIC ACID; 2-(METHANESULFONYLAMINO)PHENYLBORONIC ACID; 2-(METHOXYCARBONYL)-3-(TRIFLUOROMETHYL)PHENYLBORONIC ACID; 2-(METHOXYCARBONYL)-4-(TRIFLUOROMETHYL)PHENYLBORONIC ACID; 2-(METHOXYCARBONYL)-5-(TRIFLUOROMETHOXY)PHENYLBORONIC ACID; 2-(METHOXYCARBONYL)-5-(TRIFLUOROMETHYL)PHENYLBORONIC ACID; 2-(METHOXYCARBONYL)-5-PHENYLTHIOPHEN-3-YLBORONIC ACID; 2-(METHOXYCARBONYL)PYRIDINE-4-BORONIC ACID; 2-(METHOXYCARBONYL)QUINOLIN-8-YLBORONIC ACID; 2-(METHOXY-D3)-PHENYLBORONIC ACID; 2-(METHOXY-D3)-PYRIDINE-4-BORONIC ACID; 2-(METHOXY-D3)-PYRIMIDINE-5-BORONIC ACID; 2-(METHOXYMETHOXY)-5-METHYLPHENYLBORONIC ACID; 2-(METHOXYMETHOXY)PHENYLBORONIC ACID; 2-(METHYL-13C,D3)PYRIDINE-4-BORONIC ACID; 2-(METHYLAMINO)-6-OXO-1,6-DIHYDROPYRIMIDIN-5-YLBORONIC ACID; 2-(METHYLAMINO)PYRIDIN-4-YLBORONIC ACID; 2-(METHYLAMINO)PYRIMIDIN-5-YLBORONIC ACID; 2-(METHYL-D3)-PHENYLBORONIC ACID; 2-(METHYL-D3)-PYRIDINE-4-BORONIC ACID; 2-(METHYL-D3)-PYRIMIDINE-5-BORONIC ACID; 2-(METHYLSULFINYL)PHENYLBORONIC ACID; 2-(METHYLSULFONAMIDO)PYRIMIDIN-5-YLBORONIC ACID; 2-(METHYLSULFONYL)PHENYLBORONIC ACID; 2-(METHYLSULFONYL)PYRIDINE-5-BORONIC ACID; 2-(METHYLTHIO)PHENYLBORONIC ACID; 2-(METHYLTHIO)PYRIDINE-3-BORONIC ACID; 2-(METHYLTHIO)PYRIMIDINE-5-BORONIC ACID; 2-(METHYLTHIOL-D3)-PHENYLBORONIC ACID; 2-(MORPHOLIN-1-YL)PHENYLBORONIC ACID HCL; 2-(MORPHOLIN-1YL)PYRIMIDIN-5-YLBORONIC ACID HCL; 2-(MORPHOLIN-4-YL)PYRIDINE-4-BORONIC ACID; 2-(MORPHOLIN-4-YLCARBONYL)BENZENEBORONIC ACID; 2-(MORPHOLINO)PHENYLBORONIC ACID; 2-(MORPHOLINOMETHYL)PHENYLBORONIC ACID; 2-(MORPHOLINOMETHYL)PYRID-4-YLBORONIC ACID; 2-(MORPHOLINOSULFONYL)PHENYLBORONIC ACID; 2-(N,N-DIETHYLAMINOCARBONYL)PHENYLBORONIC ACID; 2-(N,N-DIMETHYLAMINO)PYRIDINE-5-BORONIC ACID 2HCL; 2-(N,N-DIMETHYLAMINOMETHYL)PHENYLBORONIC ACID; 2-(N,N-DIMETHYLSULFAMOYL)PYRIDIN-3-YLBORONIC ACID; 2-(N,N-DIMETHYLSULFAMOYLOXY)PHENYLBORONIC ACID; 2-(N,N-DIMETHYLSULPHAMOYL)BENZENEBORONIC ACID; 2-(N,N-METHYLETHYLAMINO)THIAZOLE-4-BORONIC ACID; 2-(NAPHTHALEN-1-YL)PHENYLBORONIC ACID; 2-(NAPHTHALEN-1-YL)PYRIDINE-4-BORONIC ACID; 2-(NAPHTHALEN-2-YL)PHENYLBORONIC ACID; 2-(N-BENZYLSULFAMOYL)-5-METHYLPHENYLBORONIC ACID; 2-(N-BOC-AMINOMETHYL)-4-FLUOROPHENYLBORONIC ACID; 2-(N-ETHYLSULFAMOYL)PHENYLBORONIC ACID; 2-(N-METHYL-N-PHENYL)AMINOMETHYLBENZENEBORONIC ACID; 2-(N-PHENYLAMINOMETHYL)PHENYLBORONIC ACID; 2-(N-PROPOXY-D7)-PYRIMIDINE-5-BORONIC ACID; 2-(N-PROPYL)PYRIMIDINE-5-BORONIC ACID; 2-(N-PROPYL-D7)-PYRIDINE-4-BORONIC ACID; 2-(N-PROPYL-D7)-PYRIDINE-5-BORONIC ACID; 2-(N-PROPYL-D7)-PYRIMIDINE-5-BORONIC ACID; 2-(N-PROPYLSULFAMOYL)PHENYLBORONIC ACID; 2-(N-TERT-BUTYLSULFAMOYL)-5-PROPYLTHIOPHEN-3-YLBORONIC ACID; 2-(PERFLUOROPHENYL)-3-(TRIFLUOROMETHYL)PYRIDINE-4-BORONIC ACID; 2-(PERFLUOROPHENYL)-4-(TRIFLUOROMETHYL)PYRIDINE-3-BORONIC ACID; 2-(PERFLUOROPHENYL)-5-(TRIFLUOROMETHYL)PYRIDINE-3-BORONIC ACID; 2-(PERFLUOROPHENYL)-5-(TRIFLUOROMETHYL)PYRIDINE-4-BORONIC ACID; 2-(PERFLUOROPHENYL)-6-(TRIFLUOROMETHYL)PYRIDINE-3-BORONIC ACID; 2-(PERFLUOROPHENYL)-6-(TRIFLUOROMETHYL)PYRIDINE-4-BORONIC ACID; 2-(PIPERAZIN-1-YL)PYRIDIN-3-YLBORONIC ACID; 2-(PIPERAZIN-1-YL)PYRIDIN-4-YLBORONIC ACID; 2-(PIPERAZIN-1-YL)THIAZOLE-4-BORONIC ACID-HCL; 2-(PIPERAZIN-1-YLMETHYL)PHENYLBORONIC ACID; 2-(PIPERIDIN-1-YL)-6-CHLOROPYRIMIDINE-4-BORONIC ACID; 2-(PIPERIDIN-1-YL)PYRIDIN-4-YLBORONIC ACID; 2-(PIPERIDIN-1-YLMETHYL)PHENYLBORONIC ACID; 2-(PIPERIDIN-1-YLSULFONYL)PHENYLBORONIC ACID; 2-(PIPERIDINO)PHENYLBORONIC ACID HCL; 2-(PROP-1-YNYL)PYRIDIN-4-YLBORONIC ACID; 2-(PROPAN-2-YLOXY)NAPHTHALENE-1-BORONIC ACID; 2-(PYRIDIN-2-YL)PHENYLBORONIC ACID; 2-(PYRIDIN-2-YLMETHOXY)PHENYLBORONIC ACID; 2-(PYRIDIN-4-YLMETHOXY)PHENYLBORONIC ACID; 2-(PYRIDINE-3-YL)PHENYLBORONIC ACID; 2-(PYRIDINE-4-YL)PHENYLBORONIC ACID; 2-(PYRROLIDIN-1-YL)-6-CHLOROPYRIMIDINE-4-BORONIC ACID; 2-(PYRROLIDIN-1-YL)PHENYLBORONIC ACID HYDROCHLORIDE; 2-(PYRROLIDIN-1-YL)PYRIDINE-3-BORONIC ACID; 2-(PYRROLIDINO)PHENYLBORONIC ACID; 2-(PYRROLIDINYLSULFONYL)PHENYLBORONIC ACID; 2-(TERT-BUTOXY)PYRIDINE-4-BORONIC ACID; 2-(TERT-BUTOXYCARBONYL(METHYL)AMINO)PYRIMIDIN-5-YLBORONIC ACID; 2-(TERT-BUTOXYCARBONYL)-1,2,3,4-TETRAHYDROISOQUINOLIN-5-YLBORONIC ACID; 2-(TERT-BUTOXYCARBONYL)-1,2,3,4-TETRAHYDROISOQUINOLIN-6-YL-6-BORONIC ACID; 2-(TERT-BUTOXYCARBONYL)-1,2,3,4-TETRAHYDROISOQUINOLIN-7-YLBORONIC ACID; 2-(TERT-BUTOXYCARBONYL)-1,2,3,4-TETRAHYDROISOQUINOLIN-8-YLBORONIC ACID; 2-(TERT-BUTOXYCARBONYL)-2,3,4,5-TETRAHYDRO-1H-

BENZO[C]AZEPIN-7-YL-7-BORONIC ACID; 2-(TERT-BUTOXYCARBONYL)-2,3,4,5-TETRAHYDRO-1H-BENZO[C]AZEPIN-8-YL-8-BORONIC ACID; 2-(TERT-BUTOXYCARBONYL)-5-(TRIFLUOROMETHYL) PHENYLBORONIC ACID; 2-(TERT-BUTOXYCARBONYL)-5-CHLOROPHENYLBORONIC ACID; 2-(TERT-BUTOXYCARBONYL)-5-METHOXY-PHENYLBORONIC ACID; 2-(TERT-BUTOXYCARBONYL)PHENYLBORONIC ACID; 2-(TERT-BUTOXYCARBONYL)PYRIDIN-3-YLBORONIC ACID; 2-(TERT-BUTOXYCARBONYLAMINO)-3-FLUOROPHENYLBORONIC ACID; 2-(TERT-BUTOXYCARBONYLAMINO)-4-(TRIFLUOROMETHYL)PHENYLBORONIC ACID; 2-(TERT-BUTOXYCARBONYLAMINO)-4-CYANO-PHENYLBORONIC ACID; 2-(TERT-BUTOXYCARBONYLAMINO)-5-CHLOROPYRIDIN-4-YLBORONIC ACID; 2-(TERT-BUTOXYCARBONYLAMINO)-5-METHOXYPHENYLBORONIC ACID; 2-(TERT-BUTOXYCARBONYLAMINO)-6-METHOXYPHENYLBORONIC ACID; 2-(TERT-BUTOXYCARBONYLAMINO)BIPHENYL-3-YLBORONIC ACID; 2-(TERT-BUTOXYCARBONYLAMINO)PYRIDIN-3-YLBORONIC ACID; 2-(TERT-BUTOXYCARBONYLAMINO)-THIOPHENE-3-BORONIC ACID; 2-(TERT-BUTOXYCARBONYLAMINO)-THIOPHENE-4-BORONIC ACID; 2-(TERT-BUTOXYMETHYL)PHENYLBORONIC ACID; 2-(TERT-BUTYL)PYRIDINE-4-BORONIC ACID; 2-(TERT-BUTYLAMINO)SULFONYLPHENYLBORONIC ACID; 2-(TERT-BUTYLCARBAMOYL)-5-ISOBUTYLTHIOPHEN-3-YLBORONIC ACID; 2-(TERT-BUTYLCARBONYLAMINO)-6-CHLOROPHENYLBORONIC ACID; 2-(TERT-BUTYLCARBONYLAMINO)PHENYLBORONIC ACID; 2-(TETRAHYDRO-2H-PYRAN-4-YLOXY)PYRIDIN-4-YLBORONIC ACID; 2-(TETRAHYDRO-FURAN-3-YLOXY)PYRIMIDINE-5-BORONIC ACID; 2-(TETRAHYDROPYRAN-2-YLOXY)PHENYLBORONIC ACID; 2-(TETRAHYDROPYRAN-4-YLOXYMETHY)PHENYLBORONIC ACID; 2-(TETRAZOL-5-YL)PHENYLBORONIC ACID; 2-(THIOMORPHOLINOMETHYL)PHENYLBORONIC ACID; 2-(THIOPHEN-2-YL)PYRIDINE-4-BORONIC ACID; 2-(THIOPHEN-2-YLMETHOXYMETHYL)PHENYLBORONIC ACID; 2-(THIOPHEN-3-YL)PHENYLBORONIC ACID; 2-(TOLYL-D7)-BORONIC ACID; 2-(TRIETHYLSILYL)BENZOTHIOPHENE-7-BORONIC ACID; 2-(TRIFLUOROMETHOXY)NAPHTHALENE-1-BORONIC ACID; 2-(TRIFLUOROMETHOXY)NAPHTHALENE-3-BORONIC ACID; 2-(TRIFLUOROMETHOXY)NAPHTHALENE-4-BORONIC ACID; 2-(TRIFLUOROMETHOXY)NAPHTHALENE-5-BORONIC ACID; 2-(TRIFLUOROMETHOXY)NAPHTHALENE-6-BORONIC ACID; 2-(TRIFLUOROMETHOXY) NAPHTHALENE-7-BORONIC ACID; 2-(TRIFLUOROMETHOXY)NAPHTHALENE-8-BORONIC ACID; 2-(TRIFLUOROMETHOXY)PHENYLBORONIC ACID; 2-(TRIFLUOROMETHOXY)PYRAZINE-6-BORONIC ACID; 2-(TRIFLUOROMETHYL)[1,2,4]TRIAZOLO[1,5-A]PYRIDINE-6-BORONIC ACID; 2-(TRIFLUOROMETHYL)-1H-BENZIMIDAZOLE-5-BORONIC ACID, HYDROCHLORIDE SALT; 2-(TRIFLUOROMETHYL)-1H-INDOL-5-YLBORONIC ACID; 2-(TRIFLUOROMETHYL)-1H-PYRROLO[2,3-B]PYRIDIN-4-YLBORONIC ACID; 2-(TRIFLUOROMETHYL)-3-(2-(TRIFLUOROMETHYL)PHENYL)PYRIDINE-4-BORONIC ACID; 2-(TRIFLUOROMETHYL)-3-(3-(TRIFLUOROMETHYL)PHENYL)PYRIDINE-4-BORONIC ACID; 2-(TRIFLUOROMETHYL)-3-(4-(TRIFLUOROMETHYL)PHENYL)PYRIDINE-4-BORONIC ACID; 2-(TRIFLUOROMETHYL)-3-FLUORO-PHENYLBORONIC ACID; 2-(TRIFLUOROMETHYL)-4-(1,2,4-OXADIAZOL-3-YL)PHENYLBORONIC ACID; 2-(TRIFLUOROMETHYL)-6-(2-(TRIFLUOROMETHYL)PHENYL)PYRIDINE-3-BORONIC ACID; 2-(TRIFLUOROMETHYL)-6-(2-(TRIFLUOROMETHYL)PHENYL)PYRIDINE-4-BORONIC ACID; 2-(TRIFLUOROMETHYL)-6-(3-(TRIFLUOROMETHYL)PHENYL)PYRIDINE-3-BORONIC ACID; 2-(TRIFLUOROMETHYL)-6-(3-(TRIFLUOROMETHYL)PHENYL)PYRIDINE-4-BORONIC ACID; 2-(TRIFLUOROMETHYL)-6-(4-(TRIFLUOROMETHYL)PHENYL)PYRIDINE-3-BORONIC ACID; 2-(TRIFLUOROMETHYL)-6-(4-(TRIFLUOROMETHYL)PHENYL)PYRIDINE-4-BORONIC ACID; 2-(TRIFLUOROMETHYL)-6-NITROPHENYLBORONIC ACID; 2-(TRIFLUOROMETHYL)NAPHTHALENE-1-BORONIC ACID; 2-(TRIFLUOROMETHYL)NAPHTHALENE-3-BORONIC ACID; 2-(TRIFLUOROMETHYL)NAPHTHALENE-4-BORONIC ACID; 2-(TRIFLUOROMETHYL)NAPHTHALENE-5-BORONIC ACID; 2-(TRIFLUOROMETHYL)NAPHTHALENE-6-BORONIC ACID; 2-(TRIFLUOROMETHYL)NAPHTHALENE-7-BORONIC ACID; 2-(TRIFLUOROMETHYL)NAPHTHALENE-8-BORONIC ACID; 2-(TRIFLUOROMETHYL)PHENYLBORONIC ACID; 2-(TRIFLUOROMETHYL)PYRIDINE-3-BORONIC ACID; 2-(TRIFLUOROMETHYL)PYRIDINE-4-BORONIC ACID; 2-(TRIFLUOROMETHYL)PYRIMIDIN-5-YLBORONIC ACID; 2-(TRIFLUOROMETHYLTHIO)-BENZENEBORONIC ACID; 2-(TRIMETHYLSILYL)BENZO[B]THIOPHEN-7-YLBORONIC ACID; 2,1,3-BENZOTHIADIAZOL-4-YL-BORONIC ACID; 2,2,4,4-TETRAFLUORO-4H-BENZO[1,3]DIOXINE-6-BORONIC ACID; 2,2,4,4-TETRAMETHYL-3,4-DIHYDROBENZOTHIOPYRANYL-6-BORONIC ACID; 2,2':6',2"-TERPYRIDINE-4'-BORONIC ACID; 2,2'-BIPYRIDIN-4-YLBORONIC ACID; 2,2'-BITHIOPHENE-5-BORONIC ACID; 2,2-DIFLUOROBENZO[1,3]DIOXOLE-4-BORONIC ACID; 2,2-DIFLUORO-BENZO[1,3]DIOXOLE-5-BORONIC ACID; 2,2-DIMETHYL-2,3-DIHYDRO-1-BENZOFURAN-4-BORONIC ACID; 2,2-DIMETHYL-2,3-DIHYDRO-1-BENZOFURAN-6-BORONIC ACID; 2,2-DIMETHYL-3,4-DIHYDRO-2H-CHROMEN-6-YLBORONIC ACID; 2,2-DIMETHYLETHENYLBORONIC ACID; 2,2-DIMETHYLPROPYL-4'-(TRIFLUOROMETHYL)BENZOATE-2'-BORONIC ACID; 2,2-DIMETHYLPROPYL-4'-METHOXYBENZOATE-2'-BORONIC ACID; 2,2-DIPHENYLVINYLBORONIC ACID; 2,3,4,5,6-PENTAFLUOROBENZENEBORONIC ACID; 2,3,4,5,6-PENTAMETHYLPHENYLBORONIC ACID; 2,3,4,5-TETRAFLUOROPHENYLBORONIC ACID; 2,3,4,6-TETRAFLUOROPHENYLBORONIC ACID; 2,3,4-TRICHLORO-5-NITROPHENYLBORONIC ACID; 2,3,4-TRICHLOROPHENYLBORONIC ACID; 2,3,4-TRIFLUOROPHENYLBORONIC ACID; 2,3,4-TRIMETHOXYPHENYLBORONIC ACID; 2,3,4-TRIS(BENZYLOXY)PHENYLBORONIC ACID; 2,3,5,6-TETRAFLUOROPHENYLBORONIC ACID; 2,3,5,6-TETRAMETHYLPHENYLBORONIC ACID; 2,3,5-

TRICHLOROPHENYLBORONIC ACID; 2,3,5-TRIFLUOROPHENYLBORONIC ACID; 2,3,6-TRICHLOROPHENYLBORONIC ACID; 2,3,6-TRIFLUOROPHENYLBORONIC ACID; 2,3,6-TRIMETHOXYPHENYLBORONIC ACID; 2,3-DICHLORO-4-METHOXYPHENYLBORONIC ACID; 2,3-DICHLORO-6-(TRIFLUOROMETHYL)PHENYL-BORONIC ACID; 2,3-DICHLORO-6-FLUOROPHENYL-BORONIC ACID; 2,3-DICHLOROPHENYLBORONIC ACID; 2,3-DICHLOROPYRIDINE-4-BORONIC ACID; 2,3-DICHLOROPYRIDINE-5-BORONIC ACID; 2,3-DIFLUORO-4-(5-NONYL-1,3-DIOXAN-2-YL)PHENYLBORONIC ACID; 2,3-DIFLUORO-4-(HEPTYLOXY)PHENYLBORONIC ACID; 2,3-DIFLUORO-4-(N-HEXYLOXY)PHENYLBORONIC ACID; 2,3-DIFLUORO-4-BENZYLPHENYLBORONIC ACID; 2,3-DIFLUORO-4-ETHOXYPHENYLBORONIC ACID; 2,3-DIFLUORO-4-ETHYLPHENYLBORONIC ACID; 2,3-DIFLUORO-4'-HEPTYLBIPHENYL-4-BORONIC ACID; 2,3-DIFLUORO-4-HEPTYLPHENYL BORONIC ACID; 2,3-DIFLUORO-4-HEXYLPHENYL BORONIC ACID; 2,3-DIFLUORO-4-HYDROXYPHENYLBORONIC ACID; 2,3-DIFLUORO-4-ISOBUTYLPHENYLBORONIC ACID; 2,3-DIFLUORO-4-METHOXYPHENYLBORONIC ACID; 2,3-DIFLUORO-4-METHYLPHENYLBORONIC ACID; 2,3-DIFLUORO-4-N-BUTYLPHENYLBORONIC ACID; 2,3-DIFLUORO-4'-PENTYLBIPHENYL-4-BORONIC ACID; 2,3-DIFLUORO-4-PENTYLOXYPHENYLBORONIC ACID; 2,3-DIFLUORO-4-PENTYLPHENYL ACID; 2,3-DIFLUORO-5-NITROPHENYLBORONIC ACID; 2,3-DIFLUORO-6-BENZYLOXYPHENYLBORONIC ACID; 2,3-DIFLUORO-6-ETHOXYPHENYLBORONIC ACID; 2,3-DIFLUORO-6-METHOXYPHENYLBORONIC ACID; 2,3-DIFLUOROPHENYLBORONIC ACID; 2,3-DIFLUOROPYRIDINE-4-BORONIC ACID; 2,3-DIHYDRO-1,4-BENZODIOXIN-2-YLBORONIC ACID; 2,3-DIHYDRO-1-BENZOFURAN-7-BORONIC ACID; 2,3-DIHYDRO-1H-INDEN-5-YLBORANEDIOL; 2,3-DIHYDRO-5-FURYLBORONIC ACID; 2,3-DIHYDRO-8-METHOXYBENZO[B][1,4]DIOXIN-5-YL-5-BORONIC ACID; 2,3-DIHYDROBENZOFURAN-5-BORONIC ACID; 2,3-DIHYDROTHIENO[3,4-B][1,4]DIOXIN-5-YLBORONIC ACID; 2,3-DIMETHOXY-1-TERT-BUTYL-PHENYL-5-BORONIC ACID; 2,3-DIMETHOXYPHENYLBORONIC ACID; 2,3-DIMETHOXYPYRIDINE-4-BORONIC ACID; 2,3-DIMETHYL-2H-INDAZOL-6-YLBORONIC ACID; 2,3-DIMETHYL-4-HYDROXYMETHYLPHENYLBORONIC ACID; 2,3-DIMETHYL-4-OXO-3,4-DIHYDROQUINAZOLIN-7-YLBORONIC ACID; 2,3-DIMETHYLANTHRACEN-10-YL-10-BORONIC ACID; 2,3-DIMETHYLBENZO[B]THIOPHENE-7-BORONIC ACID; Z,3'-DIMETHYLBIPHENYL-2-YLBORONIC ACID; 2,3-DIMETHYLINDAZOLE-5-BORONIC ACID; 2,3-DIMETHYLPHENYLBORONIC ACID; 2,3-DIMETHYLPYRIDIN-4-YLBORONIC ACID; 2,3-METHYLENEDIOXYPHENYLBORONIC ACID; 2,4-(DIMETHYL)PYRIMIDINE-5-BORONIC ACID; 2,4,5-TRICHLOROPHENYLBORONIC ACID; 2,4,5-TRIFLUOROPHENYLBORONIC ACID; 2,4,5-TRIMETHYLPHENYLBORONIC ACID; 2,4,6-(TRIMETHYL)PYRIMIDINE-5-BORONIC ACID; 2,4,6-TRICHLOROPHENYLBORONIC ACID; 2,4,6-TRIFLUORO-3-HYDROXYPHENYLBORONIC ACID; 2,4,6-TRIFLUORO-3-METHYLPHENYLBORONIC ACID; 2,4,6-TRIFLUOROPHENYLBORONIC ACID; 2,4,6-TRIISOPROPYLBENZENEBORONIC ACID; 2,4,6-TRIMETHOXYPHENYLBORONIC ACID; 2,4,6-TRIMETHYLPHENYLBORONIC ACID; 2,4,6-TRIMETHYLPYRIDIN-3-YLBORONIC ACID; 2,4,6-TRICHLOROPYRIDINE-3-BORONIC ACID; 2,4-BIS(BENZYLOXY)PHENYLBORONIC ACID; 2,4-BIS(BENZYLOXY)PYRIMIDINE-5-BORONIC ACID; 2,4-BIS(TRIFLUOROMETHYL)PHENYLBORONIC ACID; 2,4-DI(TERT-BUTOXY)PYRIMIDIN-5-YLBORONIC ACID HYDRATE; 2,4-DIAMINOPYRIMIDIN-5-YLBORONIC ACID; 2,4-DIBUTOXYPHENYLBORONIC ACID; 2,4-DICHLORO-3-CYANOPHENYLBORONIC ACID; 2,4-DICHLORO-3-METHOXYPHENYLBORONIC ACID; 2,4-DICHLORO-5-(2-(DIMETHYLAMINO)ETHOXY)PHENYLBORONIC ACID; 2,4-DICHLORO-5-(2-METHOXYETHOXY)PHENYLBORONIC ACID; 2,4-DICHLORO-5-(CYCLOPENTYLOXY)PHENYLBORONIC ACID; 2,4-DICHLORO-5-(CYCLOPROPYLMETHOXY)PHENYLBORONIC ACID; 2,4-DICHLORO-5-(TRIFLUOROMETHOXY)PHENYLBORONIC ACID; 2,4-DICHLORO-5-ETHOXYPHENYLBORONIC ACID; 2,4-DICHLORO-5-HYDROXYPHENYLBORONIC ACID; 2,4-DICHLORO-5-ISOBUTOXYPHENYLBORONIC ACID; 2,4-DICHLORO-5-ISOPROPOXYPHENYLBORONIC ACID; 2,4-DICHLORO-5-METHOXYPHENYLBORONIC ACID; 2,4-DICHLORO-5-NITROPHENYLBORONIC ACID; 2,4-DICHLORO-5-PROPOXYPHENYLBORONIC ACID; 2,4-DICHLORO-6-ETHYLPHENYLBORONIC ACID; 2,4-DICHLORO-6-HYDROXYPHENYLBORONIC ACID; 2,4-DICHLORO-6-METHOXYPHENYLBORONIC ACID; 2,4-DICHLOROPHENYLBORONIC ACID; 2,4-DICHLOROPYRIDINE-3-BORONIC ACID; 2,4-DICHLOROPYRIDINE-5-BORONIC ACID HYDRATE; 2,4-DICHLOROPYRIMIDIN-5-YLBORONIC ACID; 2,4-DIETHOXYPHENYLBORONIC ACID; 2,4-DIETHOXYPYRIMIDIN-5-YLBORONIC ACID; 2,4-DIFLUORO-3-(METHOXYCARBONYL)PHENYLBORONIC ACID; 2,4-DIFLUORO-3-(TRIMETHYLSILYL)PHENYLBORONIC ACID; 2,4-DIFLUORO-3-CYANOPHENYLBORONIC ACID; 2,4-DIFLUORO-5-NITROPHENYLBORONIC ACID; 2,4-DIFLUORO-6-HYDROXYPHENYLBORONIC ACID; 2,4-DIFLUOROPHENYLBORONIC ACID; 2,4-DIFLUOROPYRIDINE-3-BORONIC ACID; 2,4-DIFLUOROPYRIMIDIN-5-YLBORONIC ACID; 2,4-DIHYDROXYPYRIMIDIN-5-YLBORONIC ACID; 2,4-DIISOPROPOXYPYRIMIDIN-5-YLBORONIC ACID; 2,4-DIMETHOXY-6-METHYLPHENYLBORONIC ACID; 2,4-DIMETHOXYPHENYLBORONIC ACID; 2,4-DIMETHOXYPYRIDIN-3-YLBORONIC ACID; 2,4-DIMETHOXYPYRIMIDINE-5-BORONIC ACID; 2,4-DIMETHYL-3-METHOXYBENZENEBORONIC ACID; 2,4-DIMETHYL-6-METHOXYPHENYLBORONIC ACID; 2',4'-DIMETHYLBIPHENYL-2-YLBORONIC ACID; 2,4-DIMETHYLPHENYLBORONIC ACID; 2,4-DIMETHYLPYRIDINE-3-BORONIC ACID; 2,4-DIOXOHEXAHYDROPYRIMIDIN-5-YLBORONIC ACID; 2,4-DIPHENYL-5-PYRIMIDINYLBORONIC ACID; 2,4-DIPROPOXYPHENYLBORONIC ACID; 2,4-DITERT-BUTOXYPYRIMIDIN-5-YLBORONIC ACID; 2,5-BIS(TRIFLUOROMETHYL)BENZENEBORONIC ACID; 2,5-DICHLORO-4-METHOXY-BENZENEBORONIC ACID; 2,5-DICHLORO-4-METHYL-BENZENEBORONIC ACID; 2,5-DICHLOROPHENYLBORONIC ACID; 2,5-DICHLOROPYRIDINE-3-BORONIC ACID;

2,5-DICHLOROPYRIDINE-4-BORONIC ACID; 2,5-DICHLOROTHIOPHENE-3-BORONIC ACID; 2,5-DIFLUORO-4-BENZYLOXYPHENYLBORONIC ACID; 2,5-DIFLUORO-4-ETHOXYPHENYLBORONIC ACID; 2,5-DIFLUORO-4-HYDROXYPHENYLBORONIC ACID; 2,5-DIFLUORO-4-METHOXYPHENYLBORONIC ACID; 2,5-DIFLUORO-6-ETHOXYPHENYLBORONIC ACID; 2,5-DIFLUOROPHENYLBORONIC ACID; 2,5-DIFLUOROPYRIDINE-3-BORONIC ACID; 2,5-DIFLUOROPYRIDINE-4-BORONIC ACID; 2,5-DIMETHOXYPHENYLBORONIC ACID; 2,5-DIMETHOXYPYRIMIDIN-4-YLBORONIC ACID; 2,5-DIMETHYL-4-ETHOXYPHENYLBORONIC ACID; 2,5-DIMETHYL-4-METHOXYPHENYLBORONIC ACID; 2',5'-DIMETHYLBIPHENYL-2-YLBORONIC ACID; 2,5-DIMETHYLPHENYLBORONIC ACID; 2,5-DIMETHYLPYRIDIN-3-YLBORONIC ACID; 2,5-DIMETHYLTHIOPHENE-3-BORONIC ACID; 2,6-BIS(TRIFLUOROMETHYL)PHENYLBORONIC ACID; 2,6-DICHLORO-3-METHYLPHENYLBORONIC ACID; 2,6-DICHLORO-3-NITROPHENYLBORONIC ACID; 2,6-DICHLORO-4-METHYLPHENYLBORONIC ACID; 2,6-DICHLOROBENZYLBORONIC ACID; 2,6-DICHLOROPHENYLBORONIC ACID; 2,6-DICHLOROPYRIDINE-3-BORONIC ACID; 2,6-DICHLOROPYRIDINE-4-BORONIC ACID; 2,6-DICYANOPYRIDINE-4-BORONIC ACID; 2,6-DIETHOXYPYRIDINE-3-BORONIC ACID; 2,6-DIETHYLPYRIDINE-4-BORONIC ACID; 2,6-DIFLUORO-3-(2'-CHLOROBENZYLOXY)PHENYLBORONIC ACID; 2,6-DIFLUORO-3-(2'-FLUOROBENZYLOXY)PHENYLBORONIC ACID; 2,6-DIFLUORO-3-(3',5-DIMETHOXYBENZYLOXY)PHENYLBORONIC ACID; 2,6-DIFLUORO-3-ETHOXYPHENYLBORONIC ACID; 2,6-DIFLUORO-3-HYDROXYPHENYLBORONIC ACID; 2,6-DIFLUORO-3-ISOPROPOXYPHENYLBORONIC ACID; 2,6-DIFLUORO-3-METHOXYPHENYLBORONIC ACID; 2,6-DIFLUORO-3-NITROPHENYLBORONIC ACID; 2,6-DIFLUORO-3-PROPOXYPHENYLBORONIC ACID; 2,6-DIFLUORO-4-(3-FLUOROPHENOXY)PHENYLBORONIC ACID; 2,6-DIFLUORO-4-ETHOXYPHENYLBORONIC ACID; 2,6-DIFLUORO-4-HYDROXYPHENYLBORONIC ACID; 2,6-DIFLUORO-4-METHOXYPHENYLBORONIC ACID; 2,6-DIFLUORO-4-METHYLPHENYLBORONIC ACID; 2,6-DIFLUORO-4-MORPHOLIN-4-YL-PHENYL BORONIC ACID; 2,6-DIFLUOROPHENYLBORONIC ACID; 2,6-DIFLUOROPYRIDINE-3-BORONIC ACID; 2,6-DIFLUOROPYRIDINE-3-BORONIC ACID HYDRATE; 2,6-DIFLUOROPYRIDINE-4-BORONIC ACID; 2,6-DIHYDROXYBENZENEBORONIC ACID; 2,6-DIISOPROPYLPHENYLBORONIC ACID; 2,6-DIMETHOXYPHENYLBORONIC ACID; 2,6-DIMETHOXYPYRIDIN-4-YLBORONIC ACID; 2,6-DIMETHOXYPYRIDINE-3-BORONIC ACID; 2,6-DIMETHYL-4-CHLOROPHENYLBORONIC ACID; 2,6-DIMETHYL-4-ETHOXYPHENYLBORONIC ACID; 2,6-DIMETHYLPHENYLBORONIC ACID; 2,6-DIMETHYLPYRIDINE-3-BORONIC ACID; 2,6-DIMETHYL-PYRIDINE-4-BORONIC ACID; 2,6-DIOXO-1,2,3,6-TETRAHYDROPYRIMIDIN-4-YLBORONIC ACID; 2,6-DIPHENYLPYRIDIN-4-YLBORONIC ACID; 2,6-DIPHENYLPYRIMIDIN-4-YLBORONIC ACID; 2,7-NAPHTHYRIDINE-4-BORONIC ACID; 2-[(1,2',3',4'-TETRAHYDRO-5-NAPHTHYLOXY)METHYL]PHENYLBORONIC ACID; 2-[(1-NAPHTHYLOXY)METHYL]PHENYLBORONIC ACID; 2-[(2,2-DIMETHYLPROPANOYL)AMINO]PYRIDINE-3-BORONIC ACID; 2-[(2',6'-DIISOPROPYLPHENOXY)METHYL]PHENYLBORONIC ACID; 2-[(2-ISOPROPYL-5-METHYLPHENOXY)METHYL]PHENYLBORONIC ACID; 2-[(2-METHYLPHENOXY)METHYL]BENZENEBORONIC ACID; 2-[(3',5'-DIFLUOROPHENOXY)METHYL]PHENYLBORONIC ACID; 2-[(3-DIMETHYLANILINO)METHYL]BENZENEBORONIC ACID; 2-[(4'-(2-METHOXYETHYL)PHENOXY)METHYL]PHENYLBORONIC ACID; 2-[(4'-CHLORO-1-NAPHTHYLOXY)METHYL]PHENYLBORONIC ACID; 2-[(4'-TERT-BUTYL-2'-METHYLPHENOXY)METHYL]PHENYLBORONIC ACID; 2-[2-(4-METHYL-PIPERAZIN-1-YL)-ETHOXY]-PHENYLBORONIC ACID; 2-[2-(4-METHYL-PIPERIDIN-1-YL)-ETHOXY]-PHENYLBORONIC ACID; 2-ACETAMIDO-5-AMINOPHENYLBORONIC ACID; 2-ACETAMIDO-5-CHLOROPHENYLBORONIC ACID; 2-ACETAMIDOBENZO[D]OXAZOL-5-YLBORONIC ACID; 2-ACETAMIDOBENZO[D]OXAZOL-6-YLBORONIC ACID; 2-ACETAMIDOPHENYLBORONIC ACID; 2-ACETAMIDOPYRIDINE-5-BORONIC ACID; 2-ACRYLAMIDOPHENYLBORONIC ACID; 2-ALLYLOXYPHENYLBORONIC ACID; 2-AMINO-3-(TRIFLUOROMETHYL)PYRIDINE-4-BORONIC ACID; 2-AMINO-3-(TRIFLUOROMETHYL)-PYRIDINE-5-BORONIC ACID; 2-AMINO-3,4,5-TRIFLUOROPHENYLBORONIC ACID; 2-AMINO-3,5-DIFLUOROPHENYLBORONIC ACID; 2-AMINO-3-FLUOROPYRIDINE-4-BORONIC ACID; 2-AMINO-3-METHYLPYRIDINE-4-BORONIC ACID; 2-AMINO-4-(2-METHYLPROPYL)PHENYLBORONIC ACID; 2-AMINO-4-(ETHOXYCARBONYL)BENZENEBORONIC ACID HYDROCHLORIDE; 2-AMINO-4-(IMINO(METHOXY)METHYL)PHENYLBORONIC ACID HCL; 2-AMINO-4-(ISOPROPOXYCARBONYL)PHENYLBORONIC ACID, HCL; 2-AMINO-4-(TRIFLUOROMETHYL)PYRIDINE-3-BORONIC ACID; 2-AMINO-4-(TRIFLUOROMETHYL)PYRIMIDIN-5-YLBORONIC ACID; 2-AMINO-4,5-DIFLUOROPHENYLBORONIC ACID; 2-AMINO-4-BORONOBUTANOIC ACID; 2-AMINO-4-CARBOXYBENZENEBORONIC ACID HYDROCHLORIDE; 2-AMINO-4-CHLOROPHENYL BORONIC ACID; 2-AMINO-4-METHOXYCARBONYL PHENYLBORONIC ACID; 2-AMINO-4-METHOXYPYRIMIDIN-5-YLBORONIC ACID; 2-AMINO-4-METHYLPYRIDINE-3-BORONIC ACID; 2-AMINO-4-METHYLPYRIMIDIN-5-YLBORONIC ACID; 2-AMINO-5-(TRIFLUOROMETHYL)PYRIDINE-3-BORONIC ACID; 2-AMINO-5-(TRIFLUOROMETHYL)PYRIDINE-4-BORONIC ACID; 2-AMINO-5-CHLOROPHENYLBORONIC ACID; 2-AMINO-5-CHLORO-PYRIDINE-4-BORONIC ACID; 2-AMINO-5-FLUOROBENZENEBORONIC ACID HYDROCHLORIDE; 2-AMINO-5-FLUOROPHENYLBORONIC ACID; 2-AMINO-5-METHOXYPHENYLBORONIC ACID; 2-AMINO-5-METHYLPYRIDINE-3-BORONIC ACID; 2-AMINO-5-METHYLPYRIDINE-4-BORONIC ACID; 2-AMINO-6-(TRIFLUOROMETHYL)PYRIDINE-3-BORONIC ACID; 2-AMINO-6-(TRIFLUOROMETHYL)PYRIDINE-4-BORONIC ACID; 2-AMINO-6-CHLOROPYRIMIDINE-4-BORONIC ACID; 2-AMINO-6-FLUOROPYRIDIN-3-YLBORONIC ACID; 2-AMINO-6-FLUOROPYRIDIN-4-YLBORONIC ACID; 2-AMINO-6-METHOXYPYRIDINE-3-BORONIC ACID; 2-AMINO-6-METHYL-5-NITROPHENYLBORONIC

ACID; 2-AMINO-6-METHYLPYRIDINE-3-BORONIC ACID; 2-AMINO-6-METHYLPYRIDINE-4-BORONIC ACID; 2-AMINO-6-METHYLPYRIMIDINE-4-BORONIC ACID; 2-AMINOBENZO[D]OXAZOL-5-YLBORONIC ACID; 2-AMINOCARBONYLPHENYLBORONIC ACID; 2-AMINOETHYL BORONIC ACID; 2-AMINOMETHYL-4-FLUOROPHENYLBORONIC ACID, HCL; 2-AMINONAPHTHALENE-1-BORONIC ACID; 2-AMINONAPHTHALENE-3-BORONIC ACID; 2-AMINONAPHTHALENE-4-BORONIC ACID; 2-AMINONAPHTHALENE-5-BORONIC ACID; 2-AMINONAPHTHALENE-6-BORONIC ACID; 2-AMINONAPHTHALENE-7-BORONIC ACID; 2-AMINONAPHTHALENE-8-BORONIC ACID; 2-AMINOPHENYLBORONIC ACID; 2-AMINOPYRIDINE-3-BORONIC ACID; 2-AMINOPYRIDINE-4-BORONIC ACID; 2-AMINOPYRIMIDIN-4-YLBORONIC ACID; 2-AMINOPYRIMIDINE-5-BORONIC ACID; 2-AMINOPYRIMIDINE-5-BORONIC ACID HCL; 2-AMINOQUINAZOLIN-6-YLBORONIC ACID; 2-ANTHRACENYLBORONIC ACID; 2-BENZYL-1,3-DIOXOISOINDOLIN-5-YLBORONIC ACID; 2-BENZYL-1-OXO-1,2-DIHYDROISOQUINOLIN-6-YLBORONIC ACID; 2-BENZYL-2H-INDAZOL-6-YLBORONIC ACID; 2-BENZYLCYCLOPROPYLBORONIC ACID; 2-BENZYLOXY-3-FLUOROPHENYLBORONIC ACID; 2-BENZYLOXY-4-FLUOROPHENYLBORONIC ACID; 2-BENZYLOXY-5-CHLOROPHENYLBORONIC ACID; 2-BENZYLOXY-5-CHLOROPYRIDINE-3-BORONIC ACID; 2-BENZYLOXY-5-FLUOROPHENYLBORONIC ACID; 2-BENZYLOXY-5-METHYLPHENYLBORONIC ACID; 2-BENZYLOXY-5-TRIFLUOROMETHYLPHENYLBORONIC ACID; 2-BENZYLOXY-6-FLUOROPHENYLBORONIC ACID; 2-BENZYLOXYPHENYLBORONIC ACID; 2-BENZYLOXYPYRIDINE-3-BORONIC ACID; 2-BENZYLTHIOPHENYLBORONIC ACID; 2-BIPHENYLBORONIC ACID; 2-BOC-AMINOMETHYLPHENYLBORONIC ACID; 2-BORONO-1-METHYL-1H-INDOLE-5-CARBOXYLIC ACID; 2-BORONO-1-METHYL-1H-INDOLE-6-CARBOXYLIC ACID; 2-BORONO-4,5-DIMETHOXYBENZOIC ACID; 2-BORONO-4-CHLOROBENZOIC ACID; 2-BORONO-5-FLUOROBENZOIC ACID; 2-BORONO-5-TERT-BUTOXYBENZOIC ACID; 2-BORONO-6-(TRIFLUOROMETHYL)BENZOIC ACID; 2-BORONO-6-METHOXYBENZOIC ACID; 2-BORONO-6-METHOXYISONICOTINIC ACID; 2-BORONO-7-METHOXYBENZO[B]THIOPHENE-4-CARBOXYLIC ACID; 2-BORONOBENZENESULFONAMIDE; 2-BORONOBENZO[B]THIOPHENE-5-CARBOXYLIC ACID; 2-BORONOBENZO[B]THIOPHENE-6-CARBOXYLIC ACID; 2-BORONOBENZO[B]THIOPHENE-7-CARBOXYLIC ACID; 2-BUTOXY-3,5-DIMETHYLPHENYLBORONIC ACID; 2-BUTOXY-4-CHLOROPHENYLBORONIC ACID; 2-BUTOXY-4-FLUOROPHENYLBORONIC ACID; 2-BUTOXY-5-CHLOROPHENYLBORONIC ACID; 2-BUTOXY-5-CHLOROPYRIDINE-3-BORONIC ACID; 2-BUTOXY-5-FLUOROPHENYLBORONIC ACID; 2-BUTOXY-5-METHYLPHENYLBORONIC ACID; 2-BUTOXY-6-FLUOROPHENYLBORONIC ACID; 2-BUTOXYPHENYLBORONIC ACID; 2-BUTYLBORONIC ACID; 2-BUTYLTHIO-5-TRIFLUOROMETHYLPYRIDINE-3-BORONIC ACID; 2-CARBAMOYL-4-(TRIFLUOROMETHYL)PHENYLBORONIC ACID; 2-CARBAMOYL-4-FLUOROPHENYLBORONIC ACID; 2-CARBAMOYL-5-CHLOROPHENYLBORONIC ACID; 2-CARBAMOYLTHIAZOL-5-YLBORONIC ACID; 2-CARBOXY-4-CHLOROPHENYLBORONIC ACID; 2-CARBOXY-5-FLUOROPHENYLBORONIC ACID; 2-CARBOXY-6-METHOXYPYRIDINE-3-BORONIC ACID; 2-CARBOXYPHENYLBORONIC ACID; 2-CARBOXYPYRIDINE-4-BORONIC ACID; 2-CARBOXYTHIOPHENE-3-BORONIC ACID; 2-CARBOXYTHIOPHENE-4-BORONIC ACID; 2-CHLORO-1-METHYL-1H-IMIDAZOL-5-YLBORONIC ACID; 2-CHLORO-3-(TRIFLUOROMETHOXY)PHENYLBORONIC ACID; 2-CHLORO-3-(TRIFLUOROMETHYL)PHENYLBORONIC ACID; 2-CHLORO-3-(TRIFLUOROMETHYL)PYRIDINE-4-BORONIC ACID; 2-CHLORO-3,4-DIFLUOROPHENYLBORONIC ACID; 2-CHLORO-3,5-DIFLUOROPHENYLBORONIC ACID; 2-CHLORO-3,6-DIFLUOROPHENYLBORONIC ACID; 2-CHLORO-3-CYANOPHENYLBORONIC ACID; 2-CHLORO-3-CYANOPYRIDINE-4-BORONIC ACID; 2-CHLORO-3-ETHOXY-6-FLUOROPHENYLBORONIC ACID; 2-CHLORO-3-ETHOXYPHENYLBORONIC ACID; 2-CHLORO-3-FLUORO-5-PICOLINE-4-BORONIC ACID; 2-CHLORO-3-FLUOROPHENYLBORONIC ACID; 2-CHLORO-3-FLUOROPYRIDINE-4-BORONIC ACID; 2-CHLORO-3-FLUOROPYRIDINE-4-BORONIC ACID HYDRATE; 2-CHLORO-3-FLUOROPYRIDINE-5-BORONIC ACID; 2-CHLORO-3-HYDROXYPYRIDINE-4-BORONIC ACID; 2-CHLORO-3-METHOXYPHENYLBORONIC ACID; 2-CHLORO-3-METHOXYPYRIDINE-4-BORONIC ACID; 2-CHLORO-3-METHYLPHENYLBORONIC ACID; 2-CHLORO-3-METHYLPYRIDINE-4-BORONIC ACID; 2-CHLORO-3-METHYLPYRIDINE-5-BORONIC ACID; 2-CHLORO-3-PROPOXYPHENYLBORONIC ACID; 2-CHLORO-4-(2-METHOXY-2-OXOETHYL)PHENYLBORONIC ACID; 2-CHLORO-4-(ETHOXYCARBONYL)BENZENEBORONIC ACID; 2-CHLORO-4-(TRIFLUOROMETHYL)PHENYLBORONIC ACID; 2-CHLORO-4-(TRIFLUOROMETHYL)PYRIDINE-3-BORONIC ACID; 2-CHLORO-4,5-DIFLUOROPHENYLBORONIC ACID; 2-CHLORO-4,6-DIFLUOROPHENYLBORONIC ACID; 2-CHLORO-4,6-DIMETHOXYPYRIMIDIN-5-YLBORONIC ACID; 2-CHLORO-4-[((1,1-DIMETHYLETHYL)DIMETHYLSILYL)OXY]PHENYLBORONIC ACID; 2-CHLORO-4-CYANOPHENYLBORONIC ACID; 2-CHLORO-4-CYANOPYRIDIN-3-YLBORONIC ACID; 2-CHLORO-4-ETHOXYPHENYLBORONIC ACID; 2-CHLORO-4-FLUORO-5-(METHOXYCARBONYL)PHENYLBORONIC ACID; 2-CHLORO-4-FLUORO-5-METHOXYPHENYLBORONIC ACID; 2-CHLORO-4-FLUORO-5-METHYLPHENYLBORONIC ACID; 2-CHLORO-4-FLUOROPHENYLBORONIC ACID; 2-CHLORO-4-FLUOROPYRIDINE-3-BORONIC ACID; 2-CHLORO-4-HYDROXYPHENYLBORONIC ACID; 2-CHLORO-4-ISOPROPROXYPHENYLBORONIC ACID; 2-CHLORO-4-METHOXY-5-(METHOXYCARBONYL)PHENYLBORONIC ACID; 2-CHLORO-4-METHOXY-5-METHYL-BENZENEBORONIC ACID; 2-CHLORO-4-METHOXYPHENYLBORONIC ACID; 2-CHLORO-4-METHOXYPYRIDINE-3-BORONIC ACID; 2-CHLORO-4-METHOXYPYRIDINE-5-BORONIC ACID; 2-CHLORO-4-METHYLPHENYLBORONIC ACID; 2-CHLORO-4-METHYLPYRIDINE-3-BORONIC ACID; 2-CHLORO-4-METHYLPYRIDINE-5-BORONIC ACID; 2-CHLORO-4-METHYLPYRIMIDINE-5-BORONIC ACID; 2-CHLORO-4-PHENYLPYRIDINE-3-BORONIC ACID; 2-CHLORO-4-TRIFLUOROMETHOXYPHENYLBO-

RONIC ACID; 2-CHLORO-5-(1,3-DIOXOLAN-2-YL)PYRIDIN-3-YLBORONIC ACID; 2-CHLORO-5-(4-FLUOROPHENYL)THIOPHEN-3-YLBORONIC ACID; 2-CHLORO-5-(ETHOXYCARBONYL)BENZENEBORONIC ACID; 2-CHLORO-5-(ETHYLSULFONYL)PHENYLBORONIC ACID; 2-CHLORO-5-(METHOXYCARBONYL)PHENYLBORONIC ACID; 2-CHLORO-5-(OXAZOL-2-YL)PHENYLBORONIC ACID; 2-CHLORO-5-(THIAZOL-2-YL)PHENYLBORONIC ACID; 2-CHLORO-5-(TRIFLUOROMETHOXY)PHENYLBORONIC ACID; 2-CHLORO-5-(TRIFLUOROMETHYL)PHENYLBORONIC ACID; 2-CHLORO-5-(TRIFLUOROMETHYL)PYRIDINE-3-BORONIC ACID; 2-CHLORO-5-(TRIFLUOROMETHYL)PYRIDINE-4-BORONIC ACID; 2-CHLORO-5-(TRIFLUOROMETHYL)THIOPHENE-3-BORONIC ACID; 2-CHLORO-5-BORONOBENZAMIDE; 2-CHLORO-5-CYANOPHENYLBORONIC ACID; 2-CHLORO-5-CYANOPYRIDINE-3-BORONIC ACID; 2-CHLORO-5-ETHOXYBENZENEBORONIC ACID; 2-CHLORO-5-FLUORO-3-PICOLINE-4-BORONIC ACID; 2-CHLORO-5-FLUORO-6-METHYLPHENYLBORONIC ACID; 2-CHLORO-5-FLUOROPHENYLBORONIC ACID; 2-CHLORO-5-FLUOROPYRIDINE-3-BORONIC ACID; 2-CHLORO-5-FLUOROPYRIDINE-4-BORONIC ACID; 2-CHLORO-5-HYDROXYMETHYLPHENYLBORONIC ACID; 2-CHLORO-5-HYDROXYPHENYLBORONIC ACID; 2-CHLORO-5-HYDROXYPYRIDINE-3-BORONIC ACID; 2-CHLORO-5-HYDROXYPYRIDINE-4-BORONIC ACID; 2-CHLORO-5-ISOBUTOXYPHENYLBORONIC ACID; 2-CHLORO-5-ISOPROPOXYPHENYLBORONIC ACID; 2-CHLORO-5-METHOXY-4-METHYLBENZENEBORONIC ACID; 2-CHLORO-5-METHOXYPHENYLBORONIC ACID; 2-CHLORO-5-METHOXYPYRIDINE-3-BORONIC ACID; 2-CHLORO-5-METHOXYPYRIDINE-4-BORONIC ACID; 2-CHLORO-5-METHOXYPYRIDINE-4-BORONIC ACID, MONOLITHIUM SALT; 2-CHLORO-5-METHYLPHENYLBORONIC ACID; 2-CHLORO-5-METHYLPYRIDINE-3-BORONIC ACID; 2-CHLORO-5-METHYLPYRIDINE-4-BORONIC ACID; 2-CHLORO-5-NITROPHENYLBORONIC ACID; 2-CHLORO-5-PHENYLPYRIDIN-3-YLBORONIC ACID; 2-CHLORO-5-PROPOXYPHENYLBORONIC ACID; 2-CHLORO-6-(1H-PYRAZOL-1-YL)PYRIDINE-3-BORONIC ACID; 2-CHLORO-6-(METHOXYMETHOXY)PHENYLBORONIC ACID; 2-CHLORO-6-(TRIFLUOROMETHOXY)PHENYLBORONIC ACID; 2-CHLORO-6-(TRIFLUOROMETHYL)PHENYLBORONIC ACID; 2-CHLORO-6-(TRIFLUOROMETHYL)PYRIDINE-4-BORONIC ACID; 2-CHLORO-6-CYANOPHENYLBORONIC ACID; 2-CHLORO-6-FLUORO-3-(METHOXYMETHOXY)PHENYLBORONIC ACID; 2-CHLORO-6-FLUORO-3-HYDROXYPHENYLBORONIC ACID; 2-CHLORO-6-FLUORO-3-METHOXYPHENYLBORONIC ACID; 2-CHLORO-6-FLUORO-3-METHYLPHENYLBORONIC ACID; 2-CHLORO-6-FLUORO-5-METHYLPHENYLBORONIC ACID; 2-CHLORO-6-FLUOROPHENYLBORONIC ACID; 2-CHLORO-6-HYDROXYPHENYLBORONIC ACID; 2-CHLORO-6-HYDROXYPYRIDINE-3-BORONIC ACID; 2-CHLORO-6-HYDROXYPYRIDINE-4-BORONIC ACID; 2-CHLORO-6-ISOPROPYLPYRIDINE-3-BORONIC ACID; 2-CHLORO-6-ISOPROPYLPYRIDINE-4-BORONIC ACID; 2-CHLORO-6-METHOXY-4-(METHOXYMETHYL)PHENYLBORONIC ACID; 2-CHLORO-6-METHOXYPHENYLBORONIC ACID; 2-CHLORO-6-METHOXYPYRIDINE-3-BORONIC ACID; 2-CHLORO-6-METHOXYPYRIDINE-4-BORONIC ACID; 2-CHLORO-6-METHYLPHENYLBORONIC ACID; 2-CHLORO-6-METHYLPYRIDINE-3-BORONIC ACID; 2-CHLORO-6-PHENYLPYRIDIN-3-YLBORONIC ACID; 2-CHLOROFURAN-3-YLBORONIC ACID; 2-CHLORONAPHTHALENE-1-BORONIC ACID; 2-CHLORONAPHTHALENE-3-BORONIC ACID; 2-CHLORONAPHTHALENE-4-BORONIC ACID; 2-CHLORONAPHTHALENE-5-BORONIC ACID; 2-CHLORONAPHTHALENE-6-BORONIC ACID; 2-CHLORONAPHTHALENE-7-BORONIC ACID; 2-CHLORONAPHTHALENE-8-BORONIC ACID; 2-CHLOROPHENYLBORONIC ACID; 2-CHLOROPYRIDINE-3-BORONIC ACID; 2-CHLOROPYRIDINE-4-BORONIC ACID; 2-CHLOROPYRIDINE-5-BORONIC ACID; 2-CHLOROPYRIMIDINE-4-BORONIC ACID; 2-CHLOROPYRIMIDINE-5-BORONIC ACID; 2-CHLOROQUINOLINE-3-BORONIC ACID; 2-CHLOROTHIOPHENE-3-BORONIC ACID; 2'-CYANO-2-FLUOROBIPHENYL-3-YLBORONIC ACID; 2-CYANO-3-(TRIFLUOROMETHYL)PHENYLBORONIC ACID; 2-CYANO-3-FLUOROPHENYLBORONIC ACID; 2-CYANO-3-HYDROXYPHENYLBORONIC ACID; 2-CYANO-3-METHOXYPHENYLBORONIC ACID; 2-CYANO-3-METHYLPHENYLBORONIC ACID; 2-CYANO-4-(TRIFLUOROMETHYL)PHENYLBORONIC ACID; 2-CYANO-4-FLUOROPHENYLBORONIC ACID; 2-CYANO-4-HYDROXYPHENYLBORONIC ACID; 2-CYANO-4-METHOXYPHENYLBORONIC ACID; 2-CYANO-4-METHYLPHENYLBORONIC ACID; 2-CYANO-5-(TRIFLUOROMETHYL)PHENYLBORONIC ACID; 2-CYANO-5-FLUOROPHENYLBORONIC ACID; 2-CYANO-5-HYDROXYPHENYLBORONIC ACID; 2-CYANO-5-METHOXYPHENYLBORONIC ACID; 2-CYANO-5-METHYLPHENYLBORONIC ACID; 2-CYANO-6-FLUOROPHENYLBORONIC ACID; 2-CYANO-6-HYDROXYPHENYLBORONIC ACID; 2-CYANO-6-METHOXYPHENYLBORONIC ACID; 2-CYANO-6-METHYLPHENYLBORONIC ACID; 2-CYANO-6-METHYLPYRIMIDINE-4-BORONIC ACID; 2-CYANOMETHOXYPHENYLBORONIC ACID; 2-CYANOPHENYLBORONIC ACID; 2-CYANOPYRIDINE-3-BORONIC ACID; 2-CYANOPYRIDINE-4-BORONIC ACID; 2-CYANOPYRIMIDIN-5-YLBORONIC ACID; 2-CYANOPYRIMIDINE-4-BORONIC ACID; 2-CYANOTHIAZOL-5-YLBORONIC ACID; 2-CYANOTHIOPHEN-3-YLBORONIC ACID; 2-CYCLOBUTYLPHENYLBORONIC ACID; 2-CYCLOHEXYL-CYCLOPROPYL-1-BORONIC ACID; 2-CYCLOHEXYLETHENYLBORONIC ACID; 2-CYCLOHEXYLOXY-5-METHYLPYRIDINE-3-BORONIC ACID; 2-CYCLOPROPOXYPHENYLBORONIC ACID; 2-CYCLOPROPYL-1H-PYRROLO[2,3-B]PYRIDIN-4-YLBORONIC ACID; 2-CYCLOPROPYLPHENYLBORONIC ACID; 2-CYCLOPROPYLPYRIDINE-4-BORONIC ACID; 2-CYCLOPROPYLPYRIMIDIN-5-YLBORONIC ACID; 2-DIFLUOROMETHOXY-3-FLUORO-BENZENEBORONIC ACID; 2-DIFLUOROMETHOXY-3-METHYL-BENZENEBORONIC ACID; 2-DIFLUOROMETHOXY-4-FLUORO-BENZENEBORONIC ACID; 2-DIFLUOROMETHOXY-5-METHYL-BENZENEBORONIC ACID; 2-DIFLUOROMETHOXY-5-TRIFLUOROMETHYL-BENZENEBORONIC ACID; 2-DIFLUOROMETHYL-PHENYLBORONIC ACID; 2-DIMETHYLAMINO-6-

METHOXYPHENYLBORONIC ACID; 2-DIMETHYLAMINOPYRIDINE-4-BORONIC ACID; 2-DIMETHYLAMINOPYRIMIDINYL-5-BORONIC ACID; 2-ETHOXY-1-NAPHTHALENEBORONIC ACID; 2-ETHOXY-3-FLUOROPHENYLBORONIC ACID; 2-ETHOXY-4-FLUOROPHENYLBORONIC ACID; 2-ETHOXY-4-METHYL-5-PYRIDINYLBORONIC ACID; 2-ETHOXY-4-METHYLPYRIDINE-3-BORONIC ACID; 2-ETHOXY-4-TRIFLUOROMETHYLPHENYLBORONIC ACID; 2-ETHOXY-5-(TRIFLUOROMETHOXY)BENZENEBORONIC ACID; 2-ETHOXY-5-FLUOROPHENYLBORONIC ACID; 2-ETHOXY-5-FLUOROPYRIDINE-4-BORONIC ACID; 2-ETHOXY-5-HYDROXYPHENYLBORONIC ACID; 2-ETHOXY-5-METHOXYPHENYLBORONIC ACID; 2-ETHOXY-5-METHYLPHENYLBORONIC ACID; 2-ETHOXY-5-METHYLPYRIDIN-3-YLBORONIC ACID; 2-ETHOXY-5-PYRIDINEBORONIC ACID; 2-ETHOXY-5-TRIFLUOROMETHYLPHENYLBORONIC ACID; 2-ETHOXY-6-FLUOROPHENYLBORONIC ACID; 2-ETHOXY-6-METHYLPYRIDINE-3-BORONIC ACID; 2-ETHOXYCARBONYL-5-FLUOROPHENYLBORONIC ACID; 2-ETHOXYCARBONYLMETHYLPHENYLBORONIC ACID; 2-ETHOXYCARBONYLPHENYLBORONIC ACID; 2-ETHOXYMETHYLPHENYLBORONIC ACID; 2-ETHOXYPHENYLBORONIC ACID; 2-ETHOXYPYRIDINE-3-BORONIC ACID; 2-ETHOXYPYRIDINE-4-BORONIC ACID; 2-ETHOXYPYRIMIDINE-5-BORONIC ACID; 2-ETHOXYQUINOLIN-3-YLBORONIC ACID; 2-ETHOXYQUINOLIN-6-YLBORONIC ACID; 2-ETHYL-3,5-DIMETHYLPHENYLBORONIC ACID; 2-ETHYLBENZOFURAN-3-YLBORONIC ACID; 2-ETHYLPHENYLBORONIC ACID; 2-ETHYLPYRIDINE-3-BORONIC ACID; 2-ETHYLPYRIDINE-4-BORONIC ACID; 2-ETHYLPYRIMIDIN-5-YLBORONIC ACID; 2-ETHYLSULFINYLPHENYLBORONIC ACID; 2-ETHYLSULFONYLPHENYLBORONIC ACID; 2-ETHYLTHIO-5-TRIFLUOROMETHYLPYRIDINE-3-BORONIC ACID; 2-ETHYLTHIOPHENYLBORONIC ACID; 2-ETHYLTHIOPYRIDINE-5-BORONIC ACID; 2-FLUORO-3-(ETHOXYCARBONYL)PHENYLBORONIC ACID; 2-FLUORO-3-(HYDROXYMETHYL)PHENYLBORONIC ACID; 2-FLUORO-3-(N,N-DIMETHYLAMINOCARBONYL)PHENYLBORONIC ACID; 2-FLUORO-3-(PIPERIDIN-1-YLMETHYL)PHENYLBORONIC ACID; 2-FLUORO-3-(TRIFLUOROMETHYL)PHENYLBORONIC ACID; 2-FLUORO-3-(TRIFLUOROMETHYL)PYRIDINE-4-BORONIC ACID; 2-FLUORO-3,4-METHYLENEDIOXYPHENYLBORONIC ACID; 2-FLUORO-3-HYDROXYPHENYLBORONIC ACID; 2-FLUORO-3-HYDROXYPYRIDINE-4-BORONIC ACID; 2-FLUORO-3-ISOBUTOXYPHENYLBORONIC ACID; 2-FLUORO-3-ISOPROPOXYPHENYLBORONIC ACID; 2-FLUORO-3-METHOXYPHENYLBORONIC ACID; 2-FLUORO-3-METHOXYPYRIDINE-4-BORONIC ACID; 2-FLUORO-3-METHOXYPYRIDINE-5-BORONIC ACID; 2-FLUORO-3-METHYLPHENYLBORONIC ACID; 2-FLUORO-3-METHYLPYRIDINE-4-BORONIC ACID; 2-FLUORO-3-METHYLPYRIDINE-5-BORONIC ACID; 2-FLUORO-3-NITROPHENYLBORONIC ACID; 2-FLUORO-4-(1,2,4-OXADIAZOL-3-YL)PHENYLBORONIC ACID; 2-FLUORO-4-(3-(PYRROLIDIN-1-YL)PHENOXY)PHENYLBORONIC ACID; 2-FLUORO-4-(3-FLUOROPHENOXY)PHENYLBORONIC ACID; 2-FLUORO-4-(5-FLUOROPYRIDIN-3-YLOXY)PHENYLBORONIC ACID; 2-FLUORO-4-(6-FLUOROPYRIDIN-3-YLOXY)PHENYLBORONIC ACID; 2-FLUORO-4-(METHOXY-D3)-PHENYLBORONIC ACID; 2-FLUORO-4-(METHYLSULFONYL)PHENYLBORONIC ACID; 2-FLUORO-4-(N-ETHYLAMINOCARBONYL)PHENYLBORONIC ACID; 2-FLUORO-4-(PHENYLAMINO)PHENYLBORONIC ACID; 2-FLUORO-4-(PIPERIDINE-1-CARBONYL)PHENYLBORONIC ACID; 2-FLUORO-4-(PYRIDIN-3-YLOXY)PHENYLBORONIC ACID; 2-FLUORO-4-(TERT-BUTOXYCARBONYLAMINO)PHENYLBORONIC ACID; 2-FLUORO-4-(TETRAHYDRO-2H-PYRAN-4-YLAMINO)PHENYLBORONIC ACID; 2-FLUORO-4-(TRIFLUOROMETHYL)PHENYLBORONIC ACID; 2-FLUORO-4-(TRIFLUOROMETHYL)PYRIDINE-3-BORONIC ACID; 2-FLUORO-4-BIPHENYLYLBORONIC ACID; 2-FLUORO-4-ETHOXYCARBONYLPHENYLBORONIC ACID; 2-FLUORO-4-HYDROXYPHENYLBORONIC ACID; 2-FLUORO-4-ISOPROPOXYPHENYLBORONIC ACID; 2-FLUORO-4-METHOXYCARBONYLPHENYLBORONIC ACID; 2-FLUORO-4-METHOXYPHENYLBORONIC ACID; 2-FLUORO-4-METHYLPHENYLBORONIC ACID; 2-FLUORO-4-METHYLPYRIDINE-3-BORONIC ACID; 2-FLUORO-4-METHYLPYRIDINE-5-BORONIC ACID; 2-FLUORO-4-PHENYLPYRIDIN-3-YLBORONIC ACID; 2-FLUORO-4-PROPOXYPHENYLBORONIC ACID; 2-FLUORO-4-TRIFLUOROMETHOXYPHENYLBORONIC ACID; 2-FLUORO-5-(1,2,4-OXADIAZOL-3-YL)PHENYLBORONIC ACID; 2-FLUORO-5-(1-MORPHOLINOETHYL)PYRIDIN-3-YLBORONIC ACID; 2-FLUORO-5-(4-(METHYLTHIO)BENZYL)PYRIDIN-3-YLBORONIC ACID; 2-FLUORO-5-(HYDRAZINOCARBONYL)BENZENEBORONIC ACID; 2-FLUORO-5-(ISOPROPYLCARBAMOYL)BENZENEBORONIC ACID; 2-FLUORO-5-(METHOXY(METHYL)CARBAMOYL)PHENYLBORONIC ACID; 2-FLUORO-5-(METHOXYCARBAMOYL)BENZENEBORONIC ACID; 2-FLUORO-5-(METHOXYCARBONYL)PHENYLBORONIC ACID; 2-FLUORO-5-(METHOXY-D3)-PHENYLBORONIC ACID; 2-FLUORO-5-(METHYLCARBAMOYL)BENZENEBORONIC ACID; 2-FLUORO-5-(MORPHOLINE-4-CARBONYL)PHENYLBORONIC ACID; 2-FLUORO-5-(MORPHOLINOMETHYL)PYRIDIN-3-YLBORONIC ACID; 2-FLUORO-5-(PHENYLCARBAMOYL)BENZENEBORONIC ACID; 2-FLUORO-5-(PIPERIDIN-1-YLCARBONYL)BENZENEBORONIC ACID; 2-FLUORO-5-(PROPYLCARBAMOYL)BENZENEBORONIC ACID; 2-FLUORO-5-(PYRROLIDINE-1-CARBONYL)PHENYLBORONIC ACID; 2-FLUORO-5-(THIOMORPHOLINOMETHYL)PYRIDIN-3-YLBORONIC ACID; 2-FLUORO-5-(TRIFLUOROMETHOXY)PHENYLBORONIC ACID; 2-FLUORO-5-(TRIFLUOROMETHYL)PHENYLBORONIC ACID; 2-FLUORO-5-(TRIFLUOROMETHYL)PYRIDINE-3-BORONIC ACID; 2-FLUORO-5-(TRIFLUOROMETHYL)PYRIDINE-4-BORONIC ACID; 2-FLUORO-5-HYDROXYMETHYLPHENYLBORONIC ACID; 2-FLUORO-5-HYDROXYPHENYLBORONIC ACID; 2-FLUORO-5-HYDROXYPYRIDINE-3-BORONIC ACID; 2-FLUORO-5-HYDROXYPYRIDINE-4-BORONIC ACID; 2-FLUORO-5-ISOBUTOXYPHENYLBORONIC ACID; 2-FLUORO-5-ISOPROPOXYPHENYLBORONIC ACID; 2-FLUORO-5-ISOPROPYLPHENYLBORONIC ACID; 2-FLUORO-5-METHOXYPHENYLBORONIC ACID; 2-FLUORO-5-METHOXYPYRIDINE-3-BORONIC ACID; 2-FLUORO-

5-METHOXYPYRIDINE-4-BORONIC ACID; 2-FLUORO-5-METHYLPHENYLBORONIC ACID; 2-FLUORO-5-METHYLPYRIDINE-3-BORONIC ACID; 2-FLUORO-5-METHYLPYRIDINE-4-BORONIC ACID; 2-FLUORO-5-NITROPHENYLBORONIC ACID; 2-FLUORO-5-PHENOXYPHENYLBORONIC ACID; 2-FLUORO-5-PROPOXYPHENYLBORONIC ACID; 2-FLUORO-5-VINYLPYRIDIN-3-YLBORONIC ACID; 2-FLUORO-6-(2-METHOXYETHOXY)PYRIDIN-3-YL-BORONIC ACID; 2-FLUORO-6-(HYDROXYMETHYL) PHENYLBORONIC ACID; 2-FLUORO-6-(METHYLTHIOMETHOXY)PHENYLBORONIC ACID; 2-FLUORO-6-(PROP-1-YNYL)PYRIDIN-3-YLBORONIC ACID; 2-FLUORO-6-(TRIFLUOROMETHYL)PHENYLBORONIC ACID; 2-FLUORO-6-(TRIFLUOROMETHYL) PYRIDINE-3-BORONIC ACID; 2-FLUORO-6-(TRIFLUOROMETHYL)PYRIDINE-4-BORONIC ACID; 2-FLUORO-6-HYDROXYPHENYLBORONIC ACID; 2-FLUORO-6-HYDROXYPYRIDINE-3-BORONIC ACID; 2-FLUORO-6-HYDROXYPYRIDINE-4-BORONIC ACID; 2-FLUORO-6-ISOPROPOXYPHENYL-BORONIC ACID; 2-FLUORO-6-METHOXY-3-METHYLPHENYLBORONIC ACID; 2-FLUORO-6-METHOXYPHENYLBORONIC ACID; 2-FLUORO-6-METHOXYPYRIDINE-3-BORONIC ACID; 2-FLUORO-6-METHOXYPYRIDINE-4-BORONIC ACID; 2-FLUORO-6-METHYLPHENYLBORONIC ACID; 2-FLUORO-6-METHYLPYRIDINE-3-BORONIC ACID; 2-FLUORO-6-METHYLPYRIDINE-4-BORONIC ACID; 2-FLUORO-6-MORPHOLINOPYRIDIN-3-YLBORONIC ACID; 2-FLUORO-6-PHENOXYPHENYLBORONIC ACID; 2-FLUORO-6-PHENYLPYRIDINE-3-BORONIC ACID; 2-FLUORO-6-PICOLINE-5-BORONIC ACID; 2-FLUORO-6-PROPOXYPHENYLBORONIC ACID; 2-FLUOROBENZO[B]THIOPHEN-3-YLBORONIC ACID; 2-FLUORONAPHTHALENE-1-BORONIC ACID; 2-FLUORONAPHTHALENE-3-BORONIC ACID; 2-FLUORONAPHTHALENE-4-BORONIC ACID; 2-FLUORONAPHTHALENE-5-BORONIC ACID; 2-FLUORONAPHTHALENE-6-BORONIC ACID; 2-FLUORONAPHTHALENE-7-BORONIC ACID; 2-FLUORONAPHTHALENE-8-BORONIC ACID; 2-FLUOROPHENYLBORONIC ACID; 2-FLUOROPYRIDINE-3-BORONIC ACID; 2-FLUOROPYRIDINE-3-BORONIC ACID HYDRATE; 2-FLUOROPYRIDINE-3-BORONIC ACID TRIHYDRATE; 2-FLUOROPYRIDINE-4-BORONIC ACID; 2-FLUOROPYRIDINE-5-BORONIC ACID; 2-FLUOROPYRIMIDIN-5-YLBORONIC ACID; 2-FLUOROQUINOLINE-3-BORONIC ACID; 2-HEPTYLCYCLOPROPYLBORONIC ACID; 2-HEXYL-CYCLOPROPYL-1-BORONIC ACID; 2-HEXYLTHIOPHENE-3-BORONIC ACID; 2H-ISOQUINOLIN-1-ONE-6-BORONIC ACID; 2H-ISOQUINOLIN-1-ONE-7-BORONIC ACID; 2H-PYRANO[3,2-B]PYRIDIN-7-YLBORONIC ACID; 2-HYDROXY-3-(TRIFLUOROMETHOXY)PHENYLBORONIC ACID; 2-HYDROXY-3-(TRIFLUOROMETHYL)PHENYLBORONIC ACID; 2-HYDROXY-3-(TRIFLUOROMETHYL) PYRIDINE-4-BORONIC ACID; 2-HYDROXY-3-METHYLPHENYLBORONIC ACID; 2-HYDROXY-3-METHYLPYRIDINE-4-BORONIC ACID; 2-HYDROXY-4-(TRIFLUOROMETHOXY)PHENYLBORONIC ACID; 2-HYDROXY-4-(TRIFLUOROMETHYL)PHENYLBORONIC ACID; 2-HYDROXY-4-(TRIFLUOROMETHYL) PYRIDINE-3-BORONIC ACID; 2-HYDROXY-4-METHOXYPHENYLBORONIC ACID; 2-HYDROXY-4-METHYLPHENYLBORONIC ACID; 2-HYDROXY-4-METHYLPYRIDINE-3-BORONIC ACID; 2-HYDROXY-5-(METHOXYCARBONYL)PHENYLBORONIC ACID; 2-HYDROXY-5-(TRIFLUOROMETHOXY)PHENYLBORONIC ACID; 2-HYDROXY-5-(TRIFLUOROMETHYL) PHENYLBORONIC ACID; 2-HYDROXY-5-(TRIFLUOROMETHYL)PYRIDINE-3-BORONIC ACID; 2-HYDROXY-5-(TRIFLUOROMETHYL)PYRIDINE-4-BORONIC ACID; 2-HYDROXY-5-METHOXYPHENYLBORONIC ACID; 2-HYDROXY-5-METHYLPHENYLBORONIC ACID; 2-HYDROXY-5-METHYLPYRIDINE-3-BORONIC ACID; 2-HYDROXY-5-METHYLPYRIDINE-4-BORONIC ACID; 2-HYDROXY-6-(TRIFLUOROMETHOXY)PHENYLBORONIC ACID; 2-HYDROXY-6-(TRIFLUOROMETHYL)PHENYLBORONIC ACID; 2-HYDROXY-6-(TRIFLUOROMETHYL) PYRIDINE-3-BORONIC ACID; 2-HYDROXY-6-(TRIFLUOROMETHYL)PYRIDINE-4-BORONIC ACID; 2-HYDROXY-6-METHOXYPHENYLBORONIC ACID; 2-HYDROXY-6-METHYLPHENYLBORONIC ACID; 2-HYDROXY-6-METHYLPYRIDINE-3-BORONIC ACID; 2-HYDROXY-6-METHYLPYRIDINE-4-BORONIC ACID; 2-HYDROXYL-1-NAPHTHALENEBORONIC ACID; 2-HYDROXYMETHYL-4-METHOXYPHENYLBORONIC ACID; 2-HYDROXYPHENYLBORONIC ACID; 2-HYDROXYPYRAZINE-6-BORONIC ACID; 2-HYDROXYPYRIDIN-3-YLBORONIC ACID; 2-HYDROXYPYRIMIDINE-5-BORONIC ACID; 2-HYDROXYQUINOLIN-3-YLBORONIC ACID; 2-HYDROXYQUINOLINE-4-BORONIC ACID; 2-HYDROXYQUINOLINE-5-BORONIC ACID; 2-HYDROXYQUINOLINE-6-BORONIC ACID; 2-HYDROXYQUINOLINE-7-BORONIC ACID; 2-HYDROXYQUINOLINE-8-BORONIC ACID; 2-ISOBUTOXY-5-METHYLPHENYLBORONIC ACID; 2-ISOBUTOXY-6-METHOXYPHENYLBORONIC ACID; 2-ISOBUTOXYPHENYLBORONIC ACID; 2-ISOPROPOXY-4-(TRIFLUOROMETHYL)PHENYLBORONIC ACID; 2-ISOPROPOXY-5-(TRIFLUOROMETHOXY)PHENYLBORONIC ACID; 2-ISOPROPOXY-5-METHYLPHENYLBORONIC ACID; 2-ISOPROPOXY-6-METHOXYPHENYLBORONIC ACID; 2-ISOPROPOXYPHENYLBORONIC ACID; 2-ISOPROPOXYPYRIDINE-3-BORONIC ACID; 2-ISOPROPOXYPYRIMIDIN-5-YLBORONIC ACID; 2-ISOPROPYL-1H-PYRROLO[2,3-B]PYRIDIN-4-YLBORONIC ACID; 2-ISOPROPYL-6-METHOXYPYRIDIN-3-YLBORONIC ACID; 2-ISOPROPYL-7-METHOXYPYRAZOLO[1,5-A]PYRIDIN-3-YLBORONIC ACID; 2-ISOPROPYLPHENYLBORONIC ACID; 2-ISOPROPYLTHIO-5-TRIFLUOROMETHYLPYRIDINE-3-BORONIC ACID; 2-ISOPROXYPYRIDINE-5-BORONIC ACID; 2-METHOXY-1-NAPHTHALENEBORONIC ACID; 2-METHOXY-3-(TRIFLUOROMETHOXY)PHENYLBORONIC ACID; 2-METHOXY-3-(TRIFLUOROMETHYL)PHENYLBORONIC ACID; 2-METHOXY-3-(TRIFLUOROMETHYL) PYRIDINE-4-BORONIC ACID; 2-METHOXY-3-(TRIMETHYLSILYL)PHENYLBORONIC ACID; 2-METHOXY-3-METHYLPHENYL BORONIC ACID; 2-METHOXY-3-METHYLPYRIDINE-4-BORONIC ACID; 2-METHOXY-4-(METHOXYCARBONYL)PHENYLBORONIC ACID; 2-METHOXY-4-(TRIFLUOROMETHOXY)-PHENYLBORONIC ACID; 2-METHOXY-4-(TRIFLUOROMETHYL)-PHENYLBORONIC ACID; 2-METHOXY-4-(TRIFLUOROMETHYL)PYRIDINE-3-BORONIC ACID; 2-METHOXY-4-METHYLPHENYLBORONIC ACID;

2-METHOXY-4-METHYLPYRIDINE-3-BORONIC ACID; 2-METHOXY-4-METHYL-PYRIDINE-5-BORONIC ACID; 2-METHOXY-4-PHENYLPYRIDINE-3-BORONIC ACID; 2-METHOXY-5-(PYRIDINE-4-YL) PHENYLBORONIC ACID; 2-METHOXY-5-(TRIFLUOROMETHOXY)PHENYLBORONIC ACID; 2-METHOXY-5-(TRIFLUOROMETHYL)PYRIDINE-4-BORONIC ACID; 2-METHOXY-5-METHYLPHENYL-BORONIC ACID; 2-METHOXY-5-METHYLPYRIDINE-3-BORONIC ACID; 2-METHOXY-5-METHYLPYRIDINE-4-BORONIC ACID; 2-METHOXY-5-METHYLTHIOPHEN-3-YLBORONIC ACID; 2-METHOXY-5-PHENYLPYRIDIN-3-YLBORONIC ACID; 2-METHOXY-5-PROPYLPHENYLBORONIC ACID; 2-METHOXY-5-PYRIDINEBORONIC ACID; 2-METHOXY-5-TRIFLUOROMETHYLPHENYLBORONIC ACID; 2-METHOXY-5-TRIFLUOROMETHYLPYRIDINE-3-BORONIC ACID; 2-METHOXY-6-(TRIFLUOROMETHOXY)PHENYLBORONIC ACID; 2-METHOXY-6-(TRIFLUOROMETHYL)PHENYLBORONIC ACID; 2-METHOXY-6-(TRIFLUOROMETHYL)PYRIDINE-3-BORONIC ACID; 2-METHOXY-6-(TRIFLUOROMETHYL)PYRIDINE-4-BORONIC ACID; 2-METHOXY-6-CARBOXYPYRIDINE-4-BORONIC ACID; 2-METHOXY-6-CHLOROPYRIMIDINE-4-BORONIC ACID; 2-METHOXY-6-ISOPROPYLPYRIDINE-3-BORONIC ACID; 2-METHOXY-6-METHYLPYRIDIN-3-YLBORONIC ACID; 2-METHOXY-6-METHYLPYRIDINE-4-BORONIC ACID; 2-METHOXY-6-METHYLTHIOPHENYLBORONIC ACID; 2-METHOXY-6-PHENYLPYRIDINE-3-BORONIC ACID; 2-METHOXYCARBONYL-1,3-BENZOXAZOLE-5-BORONIC ACID; 2-METHOXYCARBONYL-1,3-BENZOXAZOLE-6-BORONIC ACID; 2-METHOXYCARBONYL-3,5-DIFLUOROPHENYLBORONIC ACID; 2-METHOXYCARBONYL-3-FLUOROPHENYLBORONIC ACID; 2-METHOXYCARBONYL-3-METHOXYPHENYLBORONIC ACID; 2-METHOXYCARBONYL-3-METHYLPHENYLBORONIC ACID; 2-METHOXYCARBONYL-4-METHOXYPHENYLBORONIC ACID; 2-METHOXYCARBONYL-4-METHYLPHENYLBORONIC ACID; 2-METHOXYCARBONYLINDOLE-5-BORONIC ACID; 2-METHOXYCARBONYLPHENYLBORONIC ACID; 2-METHOXYMETHOXY-5-(TRIFLUOROMETHYL) PHENYLBORONIC ACID; 2-METHOXYMETHYLPHENYLBORONIC ACID; 2-METHOXYNAPHTHALENE-4-BORONIC ACID; 2-METHOXYNAPHTHALENE-5-BORONIC ACID; 2-METHOXYNAPHTHALENE-7-BORONIC ACID; 2-METHOXYNAPHTHALENE-8-BORONIC ACID; 2-METHOXYPHENYLBORONIC ACID; 2-METHOXYPYRAZINE-6-BORONIC ACID; 2-METHOXYPYRIDINE-3-BORONIC ACID; 2-METHOXYPYRIDINE-3-BORONIC ACID HYDRATE; 2-METHOXYPYRIDINE-3-BORONIC ACID-HCL; 2-METHOXYPYRIDINE-4-BORONIC ACID; 2-METHOXYPYRIDINE-6-BORONIC ACID, HYDROCHLORIDE SALT; 2-METHOXYPYRIMIDINE-4-BORONIC ACID; 2-METHOXYPYRIMIDINE-5-BORONIC ACID; 2-METHOXYQUINOLIN-6-YLBORONIC ACID; 2-METHOXYQUINOLINE-3-BORONIC ACID; 2-METHYL[1,2,4]TRIAZOLO[1,5-A]PYRIDINE-6-BORONIC ACID; 2-METHYL-1-(PHENYLSULFONYL)-1H-PYRROLO[2,3-B]PYRIDIN-4-YLBORONIC ACID; 2-METHYL-1,3-BENZOXAZOLE-5-BORONIC ACID; 2-METHYL-1-[(4-METHYLPHENYL)SULFONYL]-1H-INDOLE-3-BORONIC ACID; 2-METHYL-1H-BENZIMIDAZOLE-5-BORONIC ACID, HYDROCHLORIDE SALT; 2-METHYL-1-OXO-1,2-DIHYDROISOQUINOLIN-6-YLBORONIC ACID; 2-METHYL-2-(4-BORONOPHENYL)PROPYLAMINE, HCL; 2-METHYL-2H-INDAZOLE-6-BORONIC ACID; 2-METHYL-2H-INDAZOLE-7-BORONIC ACID; 2-METHYL-3-(2-(TRIFLUOROMETHOXY)PHENYL)PYRIDINE-4-BORONIC ACID; 2-METHYL-3-(2-(TRIFLUOROMETHYL)PHENYL)PYRIDINE-4-BORONIC ACID; 2-METHYL-3-(2,4,5-TRICHLOROPHENYL)PYRIDINE-4-BORONIC ACID; 2-METHYL-3-(3-(TRIFLUOROMETHOXY)PHENYL) PYRIDINE-4-BORONIC ACID; 2-METHYL-3-(3-(TRIFLUOROMETHYL)PHENYL)PYRIDINE-4-BORONIC ACID; 2-METHYL-3-(4-(TRIFLUOROMETHOXY)PHENYL)PYRIDINE-4-BORONIC ACID; 2-METHYL-3-(4-(TRIFLUOROMETHYL)PHENYL)PYRIDINE-4-BORONIC ACID; 2-METHYL-3-(PERFLUOROPHENYL) PYRIDINE-4-BORONIC ACID; 2-METHYL-3-(TRIFLUOROMETHOXY)PHENYLBORONIC ACID; 2-METHYL-3-(TRIFLUOROMETHYL)PHENYLBORONIC ACID; 2-METHYL-3-NITROPHENYLBORONIC ACID; 2-METHYL-4-(METHOXYMETHOXY)PHENYLBORONIC ACID; 2-METHYL-4-(MORPHOLINOSULFONYL)PHENYLBORONIC ACID; 2-METHYL-4-(N-METHYLSULFAMOYL)PHENYLBORONIC ACID; 2-METHYL-4-(N-PROPYLSULFAMOYL)PHENYLBORONIC ACID; 2-METHYL-4-(PIPERIDIN-1-YLSULFONYL)PHENYLBORONIC ACID; 2-METHYL-4-(PYRROLIDIN-1-YLSULFONYL)PHENYLBORONIC ACID; 2-METHYL-4-(TRIFLUOROMETHOXY)BENZENEBORONIC ACID; 2-METHYL-4-(TRIFLUOROMETHYL)PHENYLBORONIC ACID; 2-METHYL-4-CYANOPHENYLBORONIC ACID; 2-METHYL-4-FLUOROPYRAZOLE-3-BORONIC ACID; 2-METHYL-4-NITROPHENYLBORONIC ACID; 2-METHYL-5-(1,2,4-OXADIAZOL-3-YL)PHENYLBORONIC ACID; 2-METHYL-5-(5-METHYL-1,3,4-OXADIAZOL-2-YL) PHENYLBORONIC ACID; 2-METHYL-5-(5-METHYL-4H-1,2,4-TRIAZOL-3-YL)PHENYLBORONIC ACID; 2-METHYL-5-(N-MORPHOLINYLSULFONYL)PHENYLBORONIC ACID; 2-METHYL-5-(OXAZOL-2-YL) PHENYLBORONIC ACID; 2-METHYL-5-(PIPERIDIN-1-YLSULFONYL)PHENYLBORONIC ACID; 2-METHYL-5-(PYRROLIDIN-1-YLSULFONYL)PHENYLBORONIC ACID; 2-METHYL-5-(THIAZOL-2-YL) PHENYLBORONIC ACID; 2-METHYL-5-(TRIFLUOROMETHOXY)PHENYLBORONIC ACID; 2-METHYL-5-(TRIFLUOROMETHYL)PHENYLBORONIC ACID; 2-METHYL-5-(TRIFLUOROMETHYLSULFONYL) PHENYLBORONIC ACID; 2-METHYL-5-AMINOPYRIDINE-4-BORONIC ACID; 2-METHYL-5-CHLOROPYRIDINE-4-BORONIC ACID; 2-METHYL-5-HYDROXYCABONYL-3-BORONIC ACID; 2-METHYL-5-METHOXYPYRIDINE-4-BORONIC ACID; 2-METHYL-6-(2-(TRIFLUOROMETHOXY)PHENYL) PYRIDINE-3-BORONIC ACID; 2-METHYL-6-(2-(TRIFLUOROMETHOXY)PHENYL)PYRIDINE-4-BORONIC ACID; 2-METHYL-6-(2-(TRIFLUOROMETHYL)PHENYL)PYRIDINE-3-BORONIC ACID; 2-METHYL-6-(2-(TRIFLUOROMETHYL)PHENYL)PYRIDINE-4-BORONIC ACID; 2-METHYL-6-(2,4,5-TRICHLOROPHENYL)PYRIDINE-3-BORONIC ACID; 2-METHYL-6-(2,4,5-TRICHLOROPHENYL)PYRIDINE-4-BORONIC ACID; 2-METHYL-6-(3-(TRIFLUOROMETHOXY)PHENYL)PYRIDINE-3-BORONIC ACID; 2-METHYL-6-(3-(TRIFLUOROMETHOXY)PHE-

NYL)PYRIDINE-4-BORONIC ACID; 2-METHYL-6-(3-(TRIFLUOROMETHYL)PHENYL)PYRIDINE-3-BORONIC ACID; 2-METHYL-6-(3-(TRIFLUOROMETHYL)PHENYL)PYRIDINE-4-BORONIC ACID; 2-METHYL-6-(4-(TRIFLUOROMETHOXY)PHENYL)PYRIDINE-3-BORONIC ACID; 2-METHYL-6-(4-(TRIFLUOROMETHOXY)PHENYL)PYRIDINE-4-BORONIC ACID; 2-METHYL-6-(4-(TRIFLUOROMETHYL)PHENYL)PYRIDINE-3-BORONIC ACID; 2-METHYL-6-(4-(TRIFLUOROMETHYL)PHENYL)PYRIDINE-4-BORONIC ACID; 2-METHYL-6-(PERFLUOROPHENYL)PYRIDINE-3-BORONIC ACID; 2-METHYL-6-(PERFLUOROPHENYL)PYRIDINE-4-BORONIC ACID; 2-METHYL-6-(TRIFLUOROMETHOXY)PHENYLBORONIC ACID; 2-METHYL-6-(TRIFLUOROMETHYL)PHENYLBORONIC ACID; 2-METHYL-6-METHOXYPYRIDINE-3-BORONIC ACID; 2-METHYLBENZO[B]THIOPHEN-3-YLBORONIC ACID; 2-METHYLBENZOTHIAZOLE-4-BORONIC ACID; 2-METHYLBENZOTHIAZOLE-5-BORONIC ACID; 2-METHYLBENZOTHIAZOLE-6-BORONIC ACID; 2-METHYLBENZOTHIAZOLE-7-BORONIC ACID; 2'-METHYLBIPHENYL-2-YLBORONIC ACID; 2-METHYLFURAN-3-BORONIC ACID; 2-METHYLINDAZOLE-4-BORONIC ACID; 2-METHYLINDAZOLE-5-BORONIC ACID; 2-METHYLNAPHTHALENE-1-BORONIC ACID; 2-METHYLNAPHTHALENE-3-BORONIC ACID; 2-METHYLNAPHTHALENE-4-BORONIC ACID; 2-METHYLNAPHTHALENE-5-BORONIC ACID; 2-METHYLNAPHTHALENE-7-BORONIC ACID; 2-METHYLPHENYLBORONIC ACID; 2-METHYLPYRIDINE-3-BORONIC ACID; 2-METHYLPYRIDINE-4-BORONIC ACID; 2-METHYLPYRIMIDIN-4-YLBORONIC ACID; 2-METHYLQUINOLIN-4-YLBORONIC ACID; 2-METHYLQUINOLINE-6-BORONIC ACID; 2-METHYLQUINOLINE-7-BORONIC ACID; 2-METHYLTHIAZOL-5-YLBORONIC ACID; 2-METHYLTHIAZOLE-4-BORONIC ACID; 2-METHYLTHIO-5-TRIFLUOROMETHOXYPHENYLBORONIC ACID; 2-METHYLTHIO-5-TRIFLUOROMETHYLPYRIDINE-3-BORONIC ACID; 2-METHYLTHIO-6-CHLOROPYRIMIDINE-4-BORONIC ACID; 2-METHYLTHIOPHENE-3-BORONIC ACID; 2-METHYLTHIOPYRIDINE-5-BORONIC ACID; 2-MORPHOLINO-6-CHLOROPYRIMIDINE-4-BORONIC ACID; 2-MORPHOLINOPYRIDINE-3-BORONIC ACID; 2-MORPHOLINOPYRIDINE-3-BORONIC ACID-HCL; 2-MORPHOLINOPYRIMIDIN-5-YLBORONIC ACID; 2-MORPHOLINOPYRIMIDINE-4-BORONIC ACID; 2-N,N-DIETHYLSULFAMOYLPHENYLBORONIC ACID; 2-NAPHTHALENEBORONIC ACID; 2-NITRO-5-AMINOPHENYLBORIC ACID; 2-NITRO-5-CARBOXYPHENYLBORONIC ACID; 2-NITROPHENYLBORONIC ACID; 2-NORBORNEN-2-YLBORONIC ACID; 2-OXO-1,2-DIHYDROPYRIDIN-3-YLBORONIC ACID; 2-OXO-1,2-DIHYDROQUINOLIN-3-YLBORONIC ACID; 2-OXO-2,3-DIHYDRO-1H-BENZO[D]IMIDAZOL-5-YLBORONIC ACID; 2-OXO-2,3-DIHYDRO-1H-PYRROLO[2,3-B]PYRIDIN-5-YLBORONIC ACID; 2-OXO-2,3-DIHYDROBENZO[D]OXAZOL-6-YL-BORONIC ACID; 2-PHENOXYPHENYLBORONIC ACID; 2-PHENYL-1H-PYRROLO[2,3-B]PYRIDINE-3-BORONIC ACID; 2-PHENYL-1H-PYRROLO[2,3-B]PYRIDINE-4-BORONIC ACID; 2-PHENYL-1H-PYRROLO[2,3-B]PYRIDINE-5-BORONIC ACID; 2-PHENYL-1H-PYRROLO[2,3-B]PYRIDINE-6-BORONIC ACID; 2-PHENYLCYCLOPROPYLBORONIC ACID; 2-PHENYLFURAN-3-YLBORONIC ACID; 2-PHENYLIMIDAZO[1,2-A]PYRIDIN-6-YLBORONIC ACID; 2-PHENYLOXAZOL-5-YLBORONIC ACID; 2-PHENYLPYRIDIN-4-YLBORONIC ACID; 2-PHENYLPYRIDINE-3-BORONIC ACID; 2-PHENYLPYRIMIDINE-4-BORONIC ACID; 2-PHENYLPYRIMIDINE-5-BORONIC ACID; 2-PHENYLTHIAZOL-5-YLBORONIC ACID; 2-PHENYLTHIOPHEN-3-YLBORONIC ACID; 2-PICOLINE-3-BORONIC ACID HCL; 2-PICOLINE-4-BORONIC ACID HCL; 2-PICOLINE-5-BORONIC ACID HYDRATE; 2-PROPEN-1-YL-BORONIC ACID; 2-PROPOXYPHENYLBORONIC ACID; 2-PROPOXYPYRIDINE-3-BORONIC ACID; 2-PROPYLBENZO[D]OXAZOL-6-YLBORONIC ACID; 2-PROPYLTHIO-5-TRIFLUOROMETHYLPYRIDINE-3-BORONIC ACID; 2-P-TERPHENYLBORONIC ACID; 2-P-TOLYLPYRIDIN-4-YLBORONIC ACID; 2-PYRAZOL-1-YL-PHENYL-BORONIC ACID; 2-PYRIDINEBORONIC ACID; 2-PYRROLIDIN-1-YLPYRIDINE-3-BORONIC ACID HYDROCHLORIDE; 2-PYRROLYLBORONIC ACID; 2-QUINOXALINYLBORONIC ACID; 2-SEC-BUTOXY-5-CHLOROPYRIDIN-3-YLBORONIC ACID; 2-TERT-BUTOXY-PYRIMIDINE-5-BORONIC ACID; 2-TERT-BUTYL-1H-PYRROLO[2,3-B]PYRIDIN-4-YLBORONIC ACID; 2-TRIFLUOROACETYLAMINOPHENYLBORONIC ACID; 2-TRIFLUOROMETHYL-5-PYRIDINEBORIC ACID; 2-TRIFLUOROMETHYL-6-CHLORO-5-PYRIDINEBORIC ACID; 2-TRIPHENYLENYLBORONIC ACID; 2-VINYLPHENYLBORONIC ACID; 3-((1-(TERT-BUTOXYCARBONYL)AZEPAN-3-YL)METHYL)PHENYLBORONIC ACID; 3-((1-(TERT-BUTOXYCARBONYL)PIPERIDIN-3-YL)METHYL)PHENYLBORONIC ACID; 34(1-(TERT-BUTOXYCARBONYL)PYRROLIDIN-3-YL)METHYL)PHENYLBORONIC ACID; 3-((2-(MESITYLSULFONYL)HYDRAZONO)METHYL)PHENYLBORONIC ACID; 3-((2'-CHLORO-5'-(TRIFLUOROMETHYL)PHENOXY)METHYL)PHENYLBORONIC ACID; 3-((4'-(2-METHOXYETHYL)PHENOXY)METHYL)PHENYLBORONIC ACID; 3-((4'-(TRIFLUOROMETHOXY)PHENOXY)METHYL)PHENYLBORONIC ACID; 3-((BUTOXYCARBONYLAMINO)METHYL)PHENYLBORONIC ACID; 3-((DIETHYLCARBAMOYL)OXY)PYRIDINE-4-BORONIC ACID; 3-((DIMETHYLAMINO)METHYL)PHENYLBORONIC ACID; 3-((PHENYLAMINO)METHYL)PHENYLBORONIC ACID; 34(TETRAHYDROFURAN-2-YL)METHYLCARBAMOYL)PHENYLBORONIC ACID; 3-([2-(DIHYDROXYBORANYL)PHENYL]METHYL)-6-METHYL-3,4-DIHYDROPYRIMIDIN-4-ONE; 3-([3-(DIHYDROXYBORANYL)PHENYL]METHYL)-6-METHYL-3,4-DIHYDROPYRIMIDIN-4-ONE; 3-([4-(DIHYDROXYBORANYL)PHENYL]METHYL)-6-METHYL-3,4-DIHYDROPYRIMIDIN-4-ONE; 3-(1-(PYRROLIDIN-1-YL)ETHYL)PHENYLBORONIC ACID; 3-(1-(TERT-BUTOXYCARBONYL)-4-CYANOPIPERIDIN-4-YL)PHENYLBORONIC ACID; 3-(1-(TERT-BUTOXYCARBONYL)AZETIDIN-3-YL)PHENYLBORONIC ACID; 3-(1-(TERT-BUTOXYCARBONYL)PIPERIDIN-3-YL)PHENYLBORONIC ACID; 3-(1-(TERT-BUTOXYCARBONYL)PIPERIDIN-4-YL)PHENYLBORONIC ACID; 3-(1-(TERT-BUTOXYCARBONYL)PIPERIDIN-4-YLOXY)

PHENYLBORONIC ACID; 3-(1-(TERT-BUTOXYCARBONYL)PYRROLIDIN-3-YL)PHENYLBORONIC ACID; 3-(1,1,1-TRIFLUORO-2-METHYLPROPAN-2-YLOXY)-4-(TRIFLUOROMETHYL)PHENYLBORONIC ACID; 3-(1,2,4-OXADIAZOL-3-YL)-4-(TRIFLUOROMETHOXY)PHENYLBORONIC ACID; 3-(1,2,4-OXADIAZOL-3-YL)PHENYLBORONIC ACID; 3-(1,3-DIOXOLAN-2-YL)-5-(TRIFLUOROMETHYL)PHENYLBORONIC ACID; 3-(1-ADAMANTYL)-4-METHOXYPHENYLBORONIC ACID; 3-(1H-1,2,3-TRIAZOL-4-YL)PHENYLBORONIC ACID; 3-(1H-1,2,4-TRIAZOL-3-YL-CARBAMOYL)PHENYLBORONIC ACID; 3-(1H-IMIDAZOL-2-YL)PHENYLBORONIC ACID; 3-(1H-PYRAZOL-4-YL)PHENYLBORONIC ACID; 3-(1H-PYRAZOL-5-YL)PHENYLBORONIC ACID; 3-(1H-PYRROL-1-YL)PHENYLBORONIC ACID; 3-(1H-PYRROLE-1-CARBONYL)PHENYLBORONIC ACID; 3-(1H-TETRAZOL-5-YLCARBAMOYL)BENZENEBORONIC ACID HYDROCHLORIDE; 3-(1-HYDROXYETHYL)PHENYLBORONIC ACID; 3-(1-ISOPROPYLPIPERIDIN-4-YLCARBAMOYL)PHENYLBORONIC ACID; 3-(1-METHYLETHYLSULFONAMIDO)PHENYLBORONIC ACID; 3-(1-PROPYLTHIO)-BENZENEBORONIC ACID; 3-(1-PYRROLIDINO)PHENYLBORONIC ACID HCL; 3-(2-(DIMETHYLAMINO)ETHYLCARBAMOYL)PHENYLBORONIC ACID; 3-(2-(PIPERIDIN-1-YL)ETHYLCARBAMOYL)PHENYLBORONIC ACID; 3-(2-(PIPERIDIN-1-YL)ETHYLCARBAMOYL)PHENYLBORONIC ACID HYDROCHLORIDE; 3-(2-(TRIFLUOROMETHOXY)PHENYL)-2-(TRIFLUOROMETHYL)PYRIDINE-4-BORONIC ACID; 3-(2,2,2-TRICHLOROACETAMIDO)BENZENEBORONIC ACID; 3-(2,2,2-TRIFLUOROACETAMIDO)BENZENEBORONIC ACID; 3-(2,2,2-TRIFLUORO-ETHOXY)-4,5-DIFLUORO-BENZENEBORONIC ACID; 3-(2,2,2-TRIFLUOROETHOXY)PHENYLBORONIC ACID; 3-(2,2,2-TRIFLUOROETHYLTHIO)-BENZENEBORONIC ACID; 3-(2,2-DICYANOVINYL)PHENYLBORONIC ACID; 3-(2,2-DIFLUORO-ETHOXY)-4,5-DIFLUORO-BENZENEBORONIC ACID; 3-(2,2-DIFLUOROETHOXY)PHENYLBORONIC ACID; 3-(2,2-DIFLUOROETHYLTHIO)-BENZENEBORONIC ACID; 3-(2,2-DIMETHOXYETHOXY)PHENYLBORONIC ACID; 3-(2,3-DIFLUOROPHENYL)-2-(TRIFLUOROMETHYL)PYRIDINE-4-BORONIC ACID; 3-(2,3-DIFLUOROPHENYL)-2-METHYLPYRIDINE-4-BORONIC ACID; 3-(2,4,5-TRICHLOROPHENYL)-2-(TRIFLUOROMETHYL)PYRIDINE-4-BORONIC ACID; 3-(2,4-DICHLOROPHENYLMETHOXY)PHENYLBORONIC ACID; 3-(2,5-DIOXOIMIDAZOLIDIN-4-YL)PHENYLBORONIC ACID; 3-(2,6-DICHLOROPHENYLMETHOXY)PHENYLBORONIC ACID; 3-(2-AMINOETHYL)PHENYLBORONIC ACID HYDROCHLORIDE; 3-(2-CARBOXYVINYL)BENZENEBORONIC ACID; 3-(2'-CHLOROBENZYLOXY)PHENYLBORONIC ACID; 3-(2-CHLOROETHYLCARBAMOYL)BENZENEBORONIC ACID; 3-(2-CHLOROPHENOXYMETHYL)PHENYLBORONIC ACID; 3-(2-CYANOETHYLAMINOCARBONYL)PHENYLBORONIC ACID; 3-(2-ETHOXY-2-OXOETHOXY)PHENYLBORONIC ACID; 3-(2-ETHOXYCARBONYLETHYL)PHENYLBORONIC ACID; 3-(2'-FLUOROBENZYLOXY)PHENYLBORONIC ACID; 3-(2H-TETRAZOL-5-YL)-PHENYL-BORONIC ACID; 3-(2-HYDROXYETHYL)PHENYLBORONIC ACID; 3-(2-HYDROXYETHYLAMINO)PYRIDIN-2-YL-BORONIC ACID; 3-(2-HYDROXYETHYLCARBAMOYL)PHENYLBORONIC ACID; 3-(2-HYDROXYPROPAN-2-YL)PYRIDINE-2-BORONIC ACID; 3-(2-METHOXY-2-OXOETHOXY)PHENYLBORONIC ACID; 3-(2-METHOXY-2-OXOETHYL)PHENYLBORONIC ACID; 3-(2'-METHOXYBENZYLOXY)PHENYLBORONIC ACID; 3-(2-METHOXYETHOXY)PHENYLBORONIC ACID; 3-(2-METHOXYETHOXY)THIOPHEN-2-YLBORONIC ACID; 3-(2-METHOXYETHYLAMINOCARBONYL)BENZENEBORONIC ACID; 3-(2-MORPHOLINOETHOXY)PHENYLBORONIC ACID; 3-(2-N,N-DIETHYLAMINOETHYLAMINOCARBONYL)PHENYLBORONIC ACID, HCL; 3-(2-NITRO-4-TRIFLUOROMETHYLPHENOXY)PHENYLBORONIC ACID; 3-(2-NITROETHYL)PHENYLBORONIC ACID; 3-(2-NITROPHENOXY)PHENYLBORONIC ACID; 3-(2-THIAZOLYL)AMINOCARBONYLPHENYLBORONIC ACID; 3-(3-(ETHOXYCARBONYL)PIPERIDINE-1-CARBONYL)PHENYLBORONIC ACID; 3-(3-(METHOXYCARBONYL)PYRROLIDIN-1-YL)PHENYLBORONIC ACID; 3-(3-(TRIFLUOROMETHOXY)PHENYL)-2-(TRIFLUOROMETHYL)PYRIDINE-4-BORONIC ACID; 3-(3'-(TRIFLUOROMETHYL)PHENOXYMETHYL)PHENYLBORONIC ACID; 3-(3,3-DIETHOXYPROPOXY)PHENYLBORONIC ACID; 3-(3,5-DICHLOROPHENYLCARBAMOYL)-4-FLUOROPHENYLBORONIC ACID; 3-(3',5'-DIMETHOXYBENZYLOXY)PHENYLBORONIC ACID; 3-(3,5-DIMETHYL-1H-PYRAZOL-1-YL)PHENYLBORONIC ACID; 3-(3,5-DIMETHYLISOXAZOL-4-YL)PHENYLBORONIC ACID; 3-(3,7-DIMETHYLOCTYLOXY)BENZENEBORONIC ACID; 3-(3-BORONOPHENYL)ACRYLONITRILE; 3-(3-CARBOXYPROPIONYLAMINO)PHENYLBORONIC ACID; 3-(3-CHLORO-4-FLUOROPHENYLCARBAMOYL)-4-FLUOROPHENYLBORONIC ACID; 3-(3'-CHLOROBENZYLOXY)PHENYLBORONIC ACID; 3-(3-CHLOROPHENOXYMETHYL)PHENYLBORONIC ACID; 3-(3-CHLOROPROPYLCARBAMOYL)BENZENEBORONIC ACID; 3-(3-CHLOROPROPYLSULPHONAMIDO)BENZENEBORONIC ACID; 3-(3-ETHOXY-3-OXOPROPYLCARBAMOYL)PHENYLBORONIC ACID; 3-(3-ETHYLTHIOUREIDO)PHENYLBORONIC ACID; 3-(3'-FLUOROBENZYLOXY)PHENYLBORONIC ACID; 3-(3-FLUOROPHENYLCARBAMOYL)PHENYLBORONIC ACID; 3-(3-FLUOROPROPYLOXY)-BENZENEBORONIC ACID; 3-(3-ISOPROPYLTHIOUREIDO)PHENYLBORONIC ACID; 3-(3'-METHOXYBENZYLOXY)PHENYLBORONIC ACID; 3-(3-METHOXYPROPYLCARBAMOYL)PHENYLBORONIC ACID; 3-(3-METHYLTHIOUREIDO)PHENYLBORONIC ACID; 3-(4-(TERT-BUTOXYCARBONYL)PIPERAZINE-1-CARBONYL)PHENYLBORONIC ACID; 3-(4-(TRIFLUOROMETHOXY)PHENYL)-2-(TRIFLUOROMETHYL)PYRIDINE-4-BORONIC ACID; 3-(4-ACETAMIDOPHENYLAMINO)PHENYLBORONIC ACID; 3-(4-ACETYLPIPERAZIN-1-YL)PHENYLBORONIC ACID; 3-(4-AMINOBENZYL)PHENYLBORONIC ACID; 3-(4-AMINOPHENYLAMINO)PHENYLBORONIC ACID; 3-(4-BORONOPHENOXYMETHYL)BENZONITRILE; 3-(4-BORONOPHENYL)CYCLOBUTANONE ETHYLENE KETAL; 3-(4-CARBOETHOXYBUTYL)PHENYLBORONIC ACID; 3-(4-CARBOXYBUTOXY)-2,4,6-TRIFLUOROPHENYLBORONIC ACID; 3-(4'-CHLOROBENZYLOXY)PHENYLBORONIC ACID; 3-(4-CHLOROPHENOXYMETHYL)PHENYLBORONIC ACID; 3-(4-

CYANOPHENYL)AMINOCARBONYLPHENYLBORONIC ACID; 3-(4-CYANOPHENYLMETHOXY)PHENYLBORONIC ACID; 3-(4-CYCLOPROPYLPIPERAZIN-1-YL)PHENYLBORONIC ACID; 3-(4-ETHOXYCARBONYLBUTYLOXY)-2,4,6-TRIFLUOROPHENYLBORONIC ACID; 3-(4-FLUORO-2-NITROPHENOXY)PHENYLBORONIC ACID; 3-(4'-FLUOROBENZYLOXY)PHENYLBORONIC ACID; 3-(4-FLUOROPHENYL)-1H-PYRAZOL-4-YLBORONIC ACID; 3-(4-FLUOROPHENYL)AMINOCARBONYLPHENYLBORONIC ACID; 3-(4'-HEPTYLOXYPHENOXYMETHYL)PHENYLBORONIC ACID; 3-(4-METHOXY)BENZYLOXY-5-(TRIFLUOROMETHYL)BENZENEBORONIC ACID; 3-(4'-METHOXYBENZYLOXY)PHENYLBORONIC ACID; 3-(4-METHYLPIPERAZIN-1-YL)PHENYLBORONIC ACID; 3-(4-METHYLPIPERIDINE-1-CARBONYL)PHENYLBORONIC ACID; 3-(4-NITROPHENOXY)PHENYLBORONIC ACID; 3-(5-(TRIFLUOROMETHYL)PYRIDIN-2-YLOXY)PHENYLBORONIC ACID; 3-(5-METHYL-1,2,4-OXADIAZOL-3-YL)PHENYLBORONIC ACID; 3-(9H-CARBAZOL-9-YL)PHENYLBORONIC ACID; 3-(ACETOXYMETHYL)PHENYLBORONIC ACID; 3-(ALLYLOXY)-4,5-DIFLUOROPHENYLBORONIC ACID; 3-(ALLYLOXYMETHYL)-4-METHOXYPHENYLBORONIC ACID; 3-(ALLYLOXYMETHYL)PHENYLBORONIC ACID; 3-(ALLYLTHIO)BENZENEBORONIC ACID; 3-(AMINOCARBONYL)-4-FLUOROBENZENEBORONIC ACID; 3-(AMINOCARBONYL)-5-FLUOROBENZENEBORONIC ACID; 3-(AMINOMETHYL)-2-FLUOROPHENYLBORONIC ACID, HCL; 3'-(AMINOMETHYL)BIPHENYL-3-YLBORONIC ACID; 3-(AZETIDINE-1-CARBONYL)PHENYLBORONIC ACID; 3-(AZIRIDINE-1-CARBONYL)PHENYLBORONIC ACID; 3-(BENZYL(METHYL)CARBAMOYL)PHENYLBORONIC ACID; 3-(BENZYLAMINO)-5-CHLOROPHENYLBORONIC ACID; 3-(BENZYLAMINO)-5-NITROBENZENEBORONIC ACID HYDROCHLORIDE; 3-(BENZYLCARBAMOYL)-4-FLUOROPHENYLBORONIC ACID; 3-(BENZYLCARBAMOYL)-5-FLUOROBENZENEBORONIC ACID; 3-(BENZYLCARBAMOYL)-5-NITROPHENYLBORONIC ACID; 3-(BENZYLOXY)-2,4-DICHLOROPHENYLBORONIC ACID; 3-(BENZYLOXY)-2,6-DIFLUOROPHENYLBORONIC ACID; 3-(BENZYLOXY)-4-FLUOROPHENYLBORONIC ACID; 3-(BENZYLOXY)-4-METHOXYPHENYLBORONIC ACID; 3-(BENZYLOXY)-4-METHYLPHENYLBORONIC ACID; 3-(BENZYLOXY)-5-CHLOROPHENYLBORONIC ACID; 3-(BENZYLOXY)-5-METHYLPHENYLBORONIC ACID; 3-(BENZYLOXYCARBONYLAMINO)-5-NITROPHENYLBORONIC ACID; 3-(BIS(2-HYDROXYETHYL)AMINO)PYRIDIN-2-YLBORONIC ACID; 3-(BOC-AMINOMETHYL)-PYRIDINE-4-BORONIC ACID; 3-(BUT-3-ENYLOXY)-4-METHOXYPHENYLBORONIC ACID; 3-(BUT-3-ENYLOXY)PHENYLBORONIC ACID; 3-(BUTYLAMINOCARBONYL)PHENYLBORONIC ACID; 3-(BUTYLSULFONAMIDO)PHENYLBORONIC ACID; 3-(CARBOXYMETHOXY)-5-FLUOROBENZENEBORONIC ACID; 3-(CBZ-AMINO)-5-FLUOROPHENYLBORONIC ACID; 3-(CHLOROMETHYL)BENZENEBORONIC ACID; 3-(CYCLOBUTYL)FURAN-2-BORONIC ACID; 3-(CYCLOBUTYL)THIOPHENE-2-BORONIC ACID; 3-(CYCLOBUTYLTHIO)PHENYLBORONIC ACID; 3-(CYCLOHEXYL(METHYL)CARBAMOYL)PHENYLBORONIC ACID; 3-(CYCLOHEXYL)FURAN-2-BORONIC ACID; 3-(CYCLOHEXYL)THIOPHENE-2-BORONIC ACID; 3-(CYCLOHEXYLAMINOCARBONYL)PHENYLBORONIC ACID; 3-(CYCLOHEXYLCARBAMOYL)-4-FLUOROBENZENEBORONIC ACID; 3-(CYCLOHEXYLCARBAMOYL)-5-FLUOROBENZENEBORONIC ACID; 3-(CYCLOHEXYLCARBAMOYL)-5-NITROPHENYLBORONIC ACID; 3-(CYCLOHEXYLMETHOXY)PHENYLBORONIC ACID; 3-(CYCLOHEXYLOXY)METHYLPHENYLBORONIC ACID; 3-(CYCLOHEXYLOXY)PHENYLBORONIC ACID; 3-(CYCLOHEXYLSULFONYL)PHENYLBORONIC ACID; 3-(CYCLOPENTYL)FURAN-2-BORONIC ACID; 3-(CYCLOPENTYL)THIOPHENE-2-BORONIC ACID; 3-(CYCLOPENTYLAMINOCARBONYL)PHENYLBORONIC ACID; 3-(CYCLOPENTYLOXY)-4-METHOXYBENZENEBORONIC ACID; 3-(CYCLOPENTYLOXY)-5-(TRIFLUOROMETHOXY)PHENYLBORONIC ACID; 3-(CYCLOPENTYLOXY)-5-METHYLPHENYLBORONIC ACID; 3-(CYCLOPROPANESULFONAMIDO)PHENYLBORONIC ACID; 3-(CYCLOPROPYL)FURAN-2-BORONIC ACID; 3-(CYCLOPROPYL)THIOPHENE-2-BORONIC ACID; 3-(CYCLOPROPYLAMINO)BENZO[D]ISOXAZOL-5-YLBORONIC ACID; 3-(CYCLOPROPYLAMINOCARBONYL)PHENYLBORONIC ACID; 3-(CYCLOPROPYLCARBAMOYL)-5-NITROPHENYLBORONIC ACID; 3-(CYCLOPROPYLMETHOXY)-5-METHYLPHENYLBORONIC ACID; 3-(CYCLOPROPYLMETHOXY)PHENYLBORONIC ACID; 3-(CYCLOPROPYLMETHYL)THIOPHENYLBORONIC ACID; 3-(CYCLOPROPYLSULFONYL)PHENYLBORONIC ACID; 3-(DANSYLAMINO)PHENYLBORONIC ACID; 3-(DIETHYLCARBAMOYL)-1-METHYL-1H-INDOL-2-YLBORONIC ACID; 3-(DIETHYLCARBAMOYL)-2-FLUOROPHENYLBORONIC ACID; 3-(DIETHYLCARBAMOYL)-4-FLUOROBENZENEBORONIC ACID; 3-(DIETHYLCARBAMOYL)-5-NITROPHENYLBORONIC ACID; 3-(DIETHYLCARBAMOYL)FURAN-2-YLBORONIC ACID; 3-(DIETHYLCARBAMOYL)THIOPHEN-2-YLBORONIC ACID; 3-(DIFLUOROMETHOXY)-2-FLUOROPHENYLBORONIC ACID; 3-(DIFLUOROMETHOXY)-5-FLUOROPHENYLBORONIC ACID; 3-(DIFLUOROMETHOXY)-BENZENEBORONIC ACID; 3-(DIFLUOROMETHOXY)PYRAZINE-2-BORONIC ACID; 3-(DIFLUOROMETHYL)-4-FLUOROPHENYLBORONIC ACID; 3-(DIHYDROXYBORYL)-4-METHOXYPYRIDINIUM; 3-(DIISOPROPYLCARBAMOYL)PHENYLBORONIC ACID; 3-(DIMETHOXYMETHYL)-4-NITROPHENYLBORONIC ACID; 3-(DIMETHYLCARBAMOYL)-4-FLUOROBENZENEBORONIC ACID; 3-(DIMETHYLCARBAMOYL)-5-NITROBENZENEBORONIC ACID; 3-(DIMETHYLCARBAMOYL)PHENYLBORONIC ACID; 3-(DIPROPYLCARBAMOYL)PHENYLBORONIC ACID; 3-(ETHOXYCARBONYL)-5-METHOXYBENZOFURAN-2-YLBORONIC ACID; 3-(ETHOXYCARBONYL)THIOPHEN-2-YLBORONIC ACID; 3-(ETHOXY-D5)-PHENYLBORONIC ACID; 3-(ETHYL(METHYL)CARBAMOYL)PHENYLBORONIC ACID; 3-(ETHYLCARBAMOYL)-4-FLUOROBENZENEBORONIC ACID; 3-(ETHYLCARBAMOYL)-5-NITROPHENYLBORONIC ACID; 3-(ETHYL-D5)-PHENYLBORONIC ACID; 3-(ETHYLSULFONAMIDO)PHENYLBORONIC ACID; 3-(FURFURYLAMINOCARBONYL)PHENYLBORONIC ACID; 3-(HYDROXYIMINO)METHYLPHENYLBORO-

RONIC ACID; 3-(HYDROXYMETHYL)-5-METHYLPHENYLBORONIC ACID; 3-(HYDROXYMETHYL)NAPHTHALENE-1-BORONIC ACID; 3-(HYDROXYMETHYL)NAPHTHALENE-2-BORONIC ACID; 3-(HYDROXYMETHYL)PHENYLBORONIC ACID; 3-(ISOBUTYRAMIDO)BENZENEBORONIC ACID; 3-(ISOPROPOXYCARBONYL)PHENYLBORONIC ACID; 3-(ISO-PROPOXY-D7)-PHENYLBORONIC ACID; 3-(ISO-PROPYL)FURAN-2-BORONIC ACID; 3-(ISO-PROPYL)THIOPHENE-2-BORONIC ACID; 3-(ISO-PROPYL-D7)-PHENYLBORONIC ACID; 3-(METHOXYCARBAMOYL)PHENYLBORONIC ACID; 3-(METHOXYCARBONYL)FURAN-2-BORONIC ACID; 3-(METHOXYCARBONYL)PYRIDINE-2-BORONIC ACID; 3-(METHOXY-D3)-PHENYLBORONIC ACID; 3-(METHOXYMETHOXY)PHENYLBORONIC ACID; 3-(METHYLAMINO)BENZO[D] ISOXAZOL-5-YLBORONIC ACID; 3-(METHYLAMINO)PYRIDIN-2-YLBORONIC ACID; 3-(METHYLCARBAMOYL)-5-NITROPHENYLBORONIC ACID; 3-(METHYL-D3)-5-FLUOROPHENYLBORONIC ACID; 3-(METHYL-D3)-PHENYLBORONIC ACID; 3'-(METHYLSULFONYL)BIPHENYL-3-YLBORONIC ACID; 3-(METHYLSULFONYL)PHENYLBORONIC ACID; 3-(METHYLSULFONYLAMINO)PHENYLBORONIC ACID; 3-(METHYLTHIO)-5-(TRIFLUOROMETHYL)PHENYLBORONIC ACID; 3-(METHYLTHIO)PHENYLBORONIC ACID; 3-(METHYLTHIO)THIOPHEN-2-YL-BORONIC ACID; 3-(METHYLTHIOL-D3)-PHENYLBORONIC ACID; 3-(MORPHOLIN-4-YLSULPHONYL)BENZENEBORONIC ACID; 3-(MORPHOLINE-4-CARBONYL)-5-NITROPHENYLBORONIC ACID; 3-(MORPHOLINE-4-CARBONYL)PHENYLBORONIC ACID; 3-(MORPHOLINO)PHENYLBORONIC ACID; 3-(MORPHOLINOMETHYL)PHENYLBORONIC ACID; 3-(N,N-DIETHYLAMINOCARBONYL)PHENYLBORONIC ACID; 3-(N,N-DIETHYLSULPHAMOYL)BENZENEBORONIC ACID; 3-(N,N-DIMETHYLAMINO)PHENYLBORONIC ACID; 3-(N,N-DIMETHYLSULFAMOYLAMINO)PHENYLBORONIC ACID; 3-(N,N-DIMETHYLSULPHONAMIDO)BENZENEBORONIC ACID; 3-(N,O-DIMETHYLHYDROXYLAMINOCARBONYL)PHENYLBORONIC ACID; 3-(NAPHTHALEN-2-YL)PHENYLBORONIC ACID; 3-(N-BENZYLAMINOCARBONYL)PHENYLBORONIC ACID; 3-(N-BENZYLSULFAMOYL)-4-METHOXYPHENYLBORONIC ACID; 3-(N-BOC-AMINOMETHYL)PHENYLBORONIC ACID; 3-(N-BUTYLCARBAMOYL)-4-FLUOROPHENYLBORONIC ACID; 3-(N-BUTYLCARBAMOYL)-5-NITROPHENYLBORONIC ACID; 3-(N-CYCLOPROPYLSULPHAMOYL)BENZENEBORONIC ACID; 3-(NEOPENTYLOXY)PHENYLBORONIC ACID; 3-(NEOPENTYLOXYSULFONYL)PHENYLBORONIC ACID; 3-(N-ETHYLAMINOCARBONYL)PHENYLBORONIC ACID; 3-(N-ETHYLSULFAMOYL)PHENYLBORONIC ACID; 3-(N-ISOPROPYLAMINOCARBONYL)-5-NITROPHENYLBORONIC ACID; 3-(N-ISOPROPYL-N-(4-METHOXYBENZYL)SULFAMOYL)PHENYLBORONIC ACID; 3-(N-METHYLAMINOCARBONYL)PHENYLBORONIC ACID; 3-(N-PROPYLAMINOCARBONYL)PHENYLBORONIC ACID; 3-(N-T-BUTYL-N-METHYLSULFAMOYL)PHENYLBORONIC ACID; 3-(OXETAN-3-YL)PHENYLBORONIC ACID; 3-(PERFLUOROPHENYL)-2-(TRIFLUOROMETHYL)PYRIDINE-4-BORONIC ACID; 3-(PHENYLAMINO)PHENYLBORONIC ACID; 3-(PHENYLAMINOCARBONYL)-5-NITROPHENYLBORONIC ACID; 3-(PIPERIDIN-1-YL)-4-(TRIFLUOROMETHYL)PHENYLBORONIC ACID; 3-(PIPERIDIN-1-YL)PHENYLBORONIC ACID; 3-(PIPERIDIN-1-YLMETHYL)PHENYLBORONIC ACID; 3-(PIPERIDIN-1-YLMETHYL)PHENYLBORONIC ACID, HCL; 3-(PIPERIDIN-1-YLSULFONYL)PHENYLBORONIC ACID; 3-(PIPERIDINE-1-CARBONYL)PHENYLBORONIC ACID; 3-(PIPERIDINO)PHENYLBORONIC ACID HCL; 3-(PROPOXYCARBONYL)PHENYLBORONIC ACID; 3-(PROPYLCARBAMOYL)-5-NITROPHENYLBORONIC ACID; 3-(PROPYLSULFONAMIDO)PHENYLBORONIC ACID; 3-(P-TOLYLCARBAMOYL)PHENYLBORONIC ACID; 3-(PYRIDIN-2-YL)PHENYL BORONIC ACID; 3-(PYRIDIN-2-YLAMINO)PHENYLBORONIC ACID; 3-(PYRIDIN-2-YLMETHOXY)PHENYLBORONIC ACID; 3-(PYRIDIN-4-YLAMINO)PHENYLBORONIC ACID; 3-(PYRIDINE-3-YL)PHENYLBORONIC ACID; 3-(PYRIDINE-4-YL)PHENYLBORONIC ACID; 3-(PYRROLIDIN-1-YLSULFONYL)PHENYLBORONIC ACID; 3-(PYRROLIDINE-1-CARBONYL)PHENYLBORONIC ACID; 3-(PYRROLIDINO)PHENYLBORONIC ACID; 3-(T-BUTOXYCARBONYLAMINO)-4-CHLOROPHENYLBORONIC ACID; 3-(T-BUTYLCARBAMOYL)-5-NITROPHENYLBORONIC ACID; 3-(T-BUTYLDIMETHYLSILYLOXY)-4-CHLORO-2-FLUOROPHENYLBORONIC ACID; 3-(T-BUTYLDIMETHYLSILYLOXY)-4-METHOXYPHENYLBORONIC ACID; 3-(T-BUTYLDIMETHYLSILYLOXY)PHENYLBORONIC ACID; 3-(T-BUTYLTHIO)PHENYLBORONIC ACID; 3-(TERT-BUTOXYCARBONYL)-2,3,4,5-TETRAHYDRO-1H-BENZO[D]AZEPIN-7-YL-7-BORONIC ACID; 3-(TERT-BUTOXYCARBONYL)PHENYLBORONIC ACID; 3-(TERT-BUTOXYCARBONYLAMINO)-5-(TRIFLUOROMETHYL)PHENYLBORONIC ACID; 3-(TERT-BUTYLAMINOCARBONYL)PHENYLBORONIC ACID; 3-(TERT-BUTYLCARBAMOYL)-4-FLUOROPHENYLBORONIC ACID; 3-(TERT-BUTYLDIMETHYLSILYLOXY)-2,4,6-TRIFLUOROPHENYLBORONIC ACID; 3-(TETRAHYDRO-2H-PYRAN-2-YLOXY)PHENYLBORONIC ACID; 3-(TETRAHYDRO-2H-PYRAN-4-YL)METHOXYPHENYLBORONIC ACID; 3-(TETRAHYDROPYRAN-4-YLOXYMETHY)PHENYLBORONIC ACID; 3-(TETRAZOL-5-YL)PHENYLBORONIC ACID; 3-(THIOMORPHOLIN-4-YLCARBONYL)BENZENEBORONIC ACID; 3-(THIOPHEN-2-YLMETHOXYMETHYL)PHENYLBORONIC ACID; 3-(TOLYL-D7)-BORONIC ACID; 3-(TRANS-4-HYDROXYCYCLOHEXYLCARBAMOYL)PHENYLBORONIC ACID; 3-(TRIFLUOROMETHOXY)PHENYLBORONIC ACID; 3-(TRIFLUOROMETHOXY)PYRAZINE-2-BORONIC ACID; 3-(TRIFLUOROMETHYL)-1-TRITYL-1H-PYRAZOL-4-YLBORONIC ACID; 3-(TRIFLUOROMETHYL)-2-(2-(TRIFLUOROMETHYL)PHENYL)PYRIDINE-4-BORONIC ACID; 3-(TRIFLUOROMETHYL)-2-(3-(TRIFLUOROMETHYL)PHENYL)PYRIDINE-4-BORONIC ACID; 3-(TRIFLUOROMETHYL)-2-(4-(TRIFLUOROMETHYL)PHENYL)PYRIDINE-4-BORONIC ACID; 3-(TRIFLUOROMETHYL)-4-(1,2,4-OXADIAZOL-3-YL)PHENYLBORONIC ACID; 3-(TRIFLUOROMETHYL)-5-(1,2,4-OXADIAZOL-3-YL)PHENYLBORONIC ACID; 3-(TRIFLUOROMETHYL)-5-

(ETHOXY-D5)-PHENYLBORONIC ACID; 3-(TRIFLUOROMETHYL)-5-(ETHYL-D5)-PHENYLBORONIC ACID; 3-(TRIFLUOROMETHYL)-5-(ISO-PROPOXY-D7)-PHENYLBORONIC ACID; 3-(TRIFLUOROMETHYL)-5-(ISO-PROPYL-D7)-PHENYLBORONIC ACID; 3-(TRIFLUOROMETHYL)-5-(METHOXY-D3)-PHENYLBORONIC ACID; 3-(TRIFLUOROMETHYL)-5-(METHYL-D3)-PHENYLBORONIC ACID; 3-(TRIFLUOROMETHYL)-5-METHYL-PHENYLBORONIC ACID; 3-(TRIFLUOROMETHYL)-5-VINYLPHENYLBORONIC ACID; 3-(TRIFLUOROMETHYL)PHENYLBORONIC ACID; 3-(TRIFLUOROMETHYL)PYRIDINE-4-BORONIC ACID; 3-(TRIFLUOROMETHYLTHIO)-BENZENEBORONIC ACID; 3,3-DIMETHYL-1-BUTENYL-BORONIC ACID; 3,3-DIMETHYL-2-OXOINDOLIN-6-YLBORONIC ACID; 3,4-(METHYLENE-D2)-DIOXYPHENYLBORONIC ACID; 3,4,5-TRICHLORO-2-METHYLPHENYLBORONIC ACID; 3,4,5-TRICHLOROPHENYLBORONIC ACID; 3,4,5-TRIFLUOROPHENYLBORONIC ACID; 3,4,5-TRIMETHOXYPHENYLBORONIC ACID; 3,4,5-TRIS(BENZYLOXY)PHENYLBORONIC ACID; 3,4-BIS(2-METHYLBUTYLOXY)BENZENEBORONIC ACID; 3,4-BIS(2-METHYLPROPYLOXY)BENZENEBORONIC ACID; 3,4-BIS(TRIFLUOROMETHYL)PHENYLBORONIC ACID; 3,4-DIAMINOPHENYLBORONIC ACID; 3,4-DICHLORO-2-METHYLPHENYLBORONIC ACID; 3',4'-DICHLORO-4-BIPHENYLBORONIC ACID; 3,4-DICHLORO-5-(TRIFLUOROMETHYL)PHENYLBORONIC ACID; 3,4-DICHLOROPHENYLBORONIC ACID; 3,4-DIFLUORO-2-ISOPROPOXYPHENYLBORONIC ACID; 3,4-DIFLUORO-5-(METHOXYCARBONYL)PHENYLBORONIC ACID; 3,4-DIFLUORO-5-(TRIFLUOROMETHYL)-PHENYLBORONIC ACID; 3,4-DIFLUORO-5-(TRIMETHYLSILYL)PHENYLBORONIC ACID; 3,4-DIFLUORO-5-METHOXYBENZENEBORONIC ACID; 3,4-DIFLUORO-5-NITROPHENYLBORONIC ACID; 3,4-DIFLUOROPHENYLBORONIC ACID; 3,4-DIHYDRO-1H-2-BENZOPYRAN-1-BORONIC ACID; 3,4-DIHYDRO-1H-2-BENZOPYRAN-3-BORONIC ACID; 3,4-DIHYDRO-1H-2-BENZOPYRAN-4-BORONIC ACID; 3,4-DIHYDRO-1H-2-BENZOPYRAN-5-BORONIC ACID; 3,4-DIHYDRO-1H-2-BENZOPYRAN-6-BORONIC ACID; 3,4-DIHYDRO-2H-1,5-BENZODIOXEPIN-6-YLBORONIC ACID; 3,4-DIHYDRO-2H-1,5-BENZODIOXEPIN-7-YLBORONIC ACID; 3,4-DIHYDRO-2H-1-BENZOPYRAN-6-YLBORANEDIOL; 3,4-DIHYDRO-2H-BENZO[B][1,4]OXAZIN-7-YLBORONIC ACID; 3,4-DIHYDRO-2H-PYRAN-6-YLBORONIC ACID; 3,4-DIHYDRO-2H-PYRANO[2,3-B]PYRIDINE-6-BORONIC ACID; 3,4-DIMETHOXYPHENYLBORONIC ACID; 3,4-DIMETHYL-2-OXO-2,3-DIHYDROBENZO[D]OXAZOL-6-YLBORONIC ACID; 3,4-DIMETHYL-5-FLUORO-PHENYLBORONIC ACID; 3',4'-DIMETHYLBIPHENYL-2-YLBORONIC ACID; 3,4-DIMETHYLPHENYLBORONIC ACID; 3,4-METHYLENEDIOXYPHENYLBORONIC ACID; 3,5,5,8,8-PENTAMETHYL-5,6,7,8-TETRAHYDRONAPHTHALEN-2-YLBORONIC ACID; 3,5,5,8,8-PENTAMETHYL-5,8-DIHYDRONAPHTHALEN-2-BORONIC ACID; 3,5-BIS((TERT-BUTYLSILYLOXY)METHYL)PHENYLBORONIC ACID; 3,5-BIS(TERT-BUTYLDIMETHYLSILYLOXY)PHENYLBORONIC ACID; 3,5-BIS(TRIFLUOROMETHYL)BENZYLBORONIC ACID; 3,5-BIS(TRIFLUOROMETHYL)PHENYLBORONIC ACID; 3,5-DIAMINOPHENYL BORONIC ACID; 3,5-DICHLORO-2-FLUOROPYRIDIN-4-YLBORONIC ACID; 3,5-DICHLORO-2-METHOXYPHENYLBORONIC ACID; 3,5-DICHLORO-2-METHYLPHENYLBORONIC ACID; 3,5-DICHLORO-4-CYANOPHENYLBORONIC ACID; 3,5-DICHLORO-4-ETHOXYPHENYLBORONIC ACID; 3,5-DICHLORO-4-METHOXYPHENYLBORONIC ACID; 3,5-DICHLOROPHENYLBORONIC ACID; 3,5-DICHLOROPYRIDINE-2-BORONIC ACID; 3,5-DICHLOROPYRIDINE-4-BORONIC ACID; 3,5-DICHLOROTHIOPHEN-2-YLBORONIC ACID; 3,5-DICYANOPHENYLBORONIC ACID; 3,5-DIFLUORO-2-HYDROXYPHENYLBORONIC ACID; 3,5-DIFLUORO-2-METHOXYPHENYLBORONIC ACID; 3,5-DIFLUORO-2-NITROPHENYLBORONIC ACID; 3,5-DIFLUORO-4-(HYDROXYMETHYL)PHENYLBORONIC ACID; 3,5-DIFLUORO-4-(METHOXYCARBONYL)PHENYLBORONIC ACID; 3,5-DIFLUORO-4-(TRIMETHYLSILYL)PHENYLBORONIC ACID; 3,5-DIFLUORO-4-CHLOROPHENYLBORONIC ACID; 3,5-DIFLUORO-4-DIFLUOROMETHOXY-BENZENEBORONIC ACID; 3,5-DIFLUORO-4-HYDROXYPHENYLBORONIC ACID; 3,5-DIFLUORO-4-METHOXY-PHENYLBORONIC ACID; 3,5-DIFLUOROPHENYLBORONIC ACID; 3,5-DIFLUOROPYRIDINE-4-BORONIC ACID; 3,5-DIFLUOROPYRIDINE-4-BORONIC ACID HYDRATE; 3,5-DIMETHOXYPHENYLBORONIC ACID; 3,5-DIMETHYL-1-(THP)PYRAZOLE-4-BORONIC ACID; 3,5-DIMETHYL-1H-PYRAZOL-4-YLBORONIC ACID HYDROCHLORIDE; 3,5-DIMETHYL-4-(3',5'-DIMETHOXYBENZYLOXY)PHENYLBORONIC ACID; 3,5-DIMETHYL-4-CHLOROPHENYLBORONIC ACID; 3,5-DIMETHYL-4-ETHOXYPHENYLBORONIC ACID; 3,5-DIMETHYL-4-FLUORO-PHENYLBORONIC ACID; 3,5-DIMETHYL-4-ISOPROPOXYPHENYLBORONIC ACID; 3,5-DIMETHYL-4-METHOXYPHENYLBORONIC ACID; 3,5-DIMETHYL-4-PROPOXYPHENYLBORONIC ACID; 3,5-DIMETHYLBENZO[B]THIOPHEN-2-YLBORONIC ACID; 3,5-DIMETHYLISOXAZOLE-4-BORONIC ACID; 3,5-DIMETHYLPHENYLBORONIC ACID; 3,5-DIMETHYLTHIOPHEN-2-YLBORONIC ACID; 3,5-DINITRO-4-METHYLPHENYLBORONIC ACID; 3,5-DINITROPHENYL BORONIC ACID; 3,5-DI-T-BUTYLPHENYLBORONIC ACID; 3,6-DIFLUORO-2-HYDROXYPHENYLBORONIC ACID; 3,6-DIFLUORO-2-METHOXYPHENYLBORONIC ACID; 3,6-DIHYDRO-2H-PYRAN-4-BORONIC ACID; 3,6-DIMETHOXYLPYRIDAZINE-4-BORONIC ACID; 3,6-DIMETHYLPYRAZIN-2-YLBORONIC ACID; 3,6-DIMETHYLPYRIDINE-2-BORONIC ACID; 3-[(1-NAPHTHYLOXY)METHYL]PHENYLBORONIC ACID; 3-[(2-FLUOROPHENYL)CARBAMOYL]BENZENEBORONIC ACID; 3-[(2-ISOPROPYL-5-METHYLPHENOXY)METHYL]PHENYLBORONIC ACID; 3-[(2-MORPHOLIN-4-YLETHYL)CARBAMOYL]BENZENEBORONIC ACID HYDROCHLORIDE; 3-[(2-PYRROLIDIN-1-YLETHYL)CARBAMOYL]BENZENEBORONIC ACID HYDROCHLORIDE; 3-[(3-METHOXY-3-OXOPROPYL)CARBAMOYL]BENZENEBORONIC ACID; 3-[(4'-CHLORO-1-NAPHTHYLOXY)METHYL]PHENYLBORONIC ACID; 3-[(4-CHLORO-3-METHYLPHENOXY)METHYL]PHENYLBORONIC ACID; 3-[(4-CHLOROPHENYL)CARBAMOYL]BENZENEBORONIC ACID; 3-[(4-METHYLPIPERAZIN-1-YL)CARBONYL]BENZENEBORONIC ACID HYDROCHLORIDE; 3-[(4'-

TERT-BUTYL-2'-METHYLPHENOXY)METHYL]PHENYLBORONIC ACID; 3-[(BENZYLOXY)METHYL]PYRIDINE-2-BORONIC ACID; 3-[(E)-2-NITROVINYL]PHENYLBORONIC ACID; 3-[2-(DIHYDROXYBORANYL)PHENOXYMETHYL]PYRIDINE-2-CARBONITRILE; 3-[3-(DIHYDROXYBORANYL)PHENOXYMETHYL]BENZONITRILE; 3-[3-(DIHYDROXYBORANYL)PHENOXYMETHYL]PYRIDINE-2-CARBONITRILE; 3-[4-(DIHYDROXYBORANYL)PHENOXYMETHYL]PYRIDINE-2-CARBONITRILE; 3-[METHOXY(METHYL)CARBAMOYL]-5-NITROPHENYLBORONIC ACID; 3-[N-(4-METHOXYBENZYL)SULFAMOYL]PHENYLBORONIC ACID; 3-[N-CYCLOPROPYL-N-(4-METHOXYBENZYL)SULFAMOYL]PHENYLBORONIC ACID; 3-ACETAMIDO-4-NITROPHENYLBORONIC ACID; 3-ACETAMIDO-5-BORONOBENZOIC ACID; 3-ACETAMIDOBENZO[D]ISOXAZOL-5-YLBORONIC ACID; 3-ACETAMIDOBENZO[D]ISOXAZOL-6-YLBORONIC ACID; 3-ACETAMIDOPHENYLBORONIC ACID; 3-ACETOXY-4-METHOXYPHENYLBORONIC ACID; 3-ALLYLOXYPHENYLBORONIC ACID; 3-AMINO-1H-INDAZOL-6-YLBORONIC ACID; 3-AMINO-2-(METHOXYCARBONYL)PYRIDINE-5-BORONIC ACID; 3-AMINO-2-(TRIFLUOROMETHYL)PYRIDINE-4-BORONIC ACID; 3-AMINO-2-CYANOPYRIDINE-5-BORONIC ACID; 3-AMINO-2-FLUOROPYRIDINE-5-BORONIC ACID; 3-AMINO-2-METHYLPYRIDINE-4-BORONIC ACID; 3-AMINO-2-METHYLPYRIDINE-5-BORONIC ACID; 3-AMINO-3-(2-BORONOPHENYL)PROPANOIC ACID; 3-AMINO-3-(3-BORONOPHENYL)PROPANOIC ACID; 3-AMINO-3-(4-BORONOPHENYL)PROPANOIC ACID; 3-AMINO-4,5-DIFLUOROPHENYLBORONIC ACID; 3-AMINO-4-CHLOROPHENYLBORONIC ACID; 3-AMINO-4-FLUOROPHENYLBORONIC ACID; 3-AMINO-4-FLUOROPHENYLBORONIC ACID HYDROCHLORIDE; 3-AMINO-4-METHOXYPHENYLBORONIC ACID; 3-AMINO-4-METHOXYPHENYLBORONIC ACID HCL; 3-AMINO-4-METHYLPHENYLBORONIC ACID; 3-AMINO-4-METHYLPHENYLBORONIC ACID HYDROCHLORIDE; 3-AMINO-5-(TRIFLUOROMETHYL)PHENYLBORONIC ACID; 3-AMINO-5-CARBOXYLPHENYLBORONIC ACID; 3-AMINO-5-CHLOROPYRIDIN-2-YLBORONIC ACID; 3-AMINO-5-CYANOBENZENEBORONIC ACID HYDROCHLORIDE; 3-AMINO-5-CYANOPHENYLBORONIC ACID; 3-AMINO-5-DIETHYLCARBAMOYLPHENYLBORONIC ACID, HCL; 3-AMINO-5-ETHOXYCARBONYLPHENYLBORONIC ACID; 3-AMINO-5-FLUOROPHENYLBORONIC ACID; 3-AMINO-5-METHOXYCARBONYLPHENYLBORONIC ACID, HCL; 3-AMINO-5-METHOXYPYRIDIN-2-YLBORONIC ACID; 3-AMINO-6,7'[7',8',8'-TRICYANOQUINODIMETHANEPHENYLBORONIC ACID; 3-AMINO-6-METHOXYPYRAZIN-2-YLBORONIC ACID; 3-AMINO-8-HYDROXY-1,10-PHENANTHROLIN-2-YLBORONIC ACID; 3-AMINOCARBONYL-2-FLUOROPHENYLBORONIC ACID; 3-AMINOCARBONYLPHENYLBORONIC ACID; 3-AMINOPHENYLBORONIC ACID; 3-AMINOPHENYLBORONIC ACID HYDROCHLORIDE; 3-AMINOPHENYLBORONIC ACID MONOHYDRATE; 3-AMINOPYRAZIN-2-YLBORONIC ACID; 3-AMINOPYRIDINE-2-BORONIC ACID; 3-AMINOPYRIDINE-4-BORONIC ACID; 3-AMINOPYRIDINE-5-BORONIC ACID; 3-AMINOQUINOLIN-6-YLBORONIC ACID; 3-BENYLOXY-4-CHLORO-PHENYLBORONIC ACID; 3-BENZYLOXY-2-CHLORO-6-FLUOROPHENYLBORONIC ACID; 3-BENZYLOXY-4-CHLORO-2-FLUOROPHENYLBORONIC ACID; 3-BENZYLOXY-5-FLUOROPHENYLBORONIC ACID; 3-BENZYLOXYCARBONYLPHENYLBORONIC ACID; 3-BENZYLOXYPHENYLBORONIC ACID; 3-BIPHENYLBORONIC ACID; 3-BORONO-1H-PYRAZOLE-5-CARBOXYLIC ACID; 3-BORONO-2-METHOXYBENZOIC ACID; 3-BORONO-4-FLUOROBENZOIC ACID ETHYL ESTER; 3-BORONO-4-METHOXYBENZOIC ACID; 3-BORONO-5-CHLOROBENZAMIDE; 3-BORONO-5-METHOXYBENZOIC ACID, 1-METHYL ESTER; 3-BORONO-A,A-DIMETHYL-BENZENEACETIC ACID; 3-BORONOBENZENESULFONAMIDE; 3-BORONOBENZOHYDRAZIDE; 3-BORONOISONICOTINIC ACID; 3-BORONO-N-(2,3-DIMETHYLPHENYL)BENZAMIDE; 3-BORONO-N-(2,4-DIMETHYLPHENYL)BENZAMIDE; 3-BORONO-N-(2,5-DIMETHYLPHENYL)BENZAMIDE; 3-BORONO-N-(2-CHLORO-4-METHYLPHENYL)BENZAMIDE; 3-BUTOXY-2,4,6-TRIFLUOROPHENYLBORONIC ACID; 3-BUTOXY-2,6-DIFLUOROPHENYLBORONIC ACID; 3-BUTOXY-2-CHLOROPHENYLBORONIC ACID; 3-BUTOXY-4-CHLORO-2-FLUOROPHENYLBORONIC ACID; 3-BUTOXY-4-CHLOROPHENYLBORONIC ACID; 3-BUTOXY-4-METHOXYPHENYLBORONIC ACID; 3-BUTOXY-5-CHLOROPHENYLBORONIC ACID; 3-BUTOXY-5-METHOXYPHENYLBORONIC ACID; 3-BUTOXY-5-METHYLPHENYLBORONIC ACID; 3-BUTOXY-5-TRIFLUOROMETHYLPHENYLBORONIC ACID; 3-BUTOXYCARBONYLAMINOPHENYLBORONIC ACID; 3-BUTOXYCARBONYLPHENYLBORONIC ACID; 3-BUTOXYPHENYLBORONIC ACID; 3-CARBAMOYL-5-NITROPHENYLBORONIC ACID; 3'-CARBAMOYLBIPHENYL-3-YLBORONIC ACID; 3-CARBOXY-2,4-DIFLUOROPHENYLBORONIC ACID; 3-CARBOXY-2-FLUOROPHENYLBORONIC ACID; 3-CARBOXY-4,5-DIFLUOROPHENYLBORONIC ACID; 3-CARBOXY-4-CHLOROPHENYLBORONIC ACID; 3-CARBOXY-4-FLUOROPHENYLBORONIC ACID; 3-CARBOXY-4-METHOXYPHENYLBORONIC ACID; 3-CARBOXY-5-CHLOROBENZENEBORONIC ACID; 3-CARBOXY-5-FLUOROPHENYLBORONIC ACID; 3-CARBOXY-5-FLUOROPYRIDINE-4-BORONIC ACID; 3-CARBOXY-5-METHOXYPHENYLBORONIC ACID; 3-CARBOXY-5-METHYLPHENYLBORONIC ACID; 3-CARBOXY-5-NITROPHENYLBORONIC ACID; 3-CARBOXYFURAN-2-BORONIC ACID; 3-CARBOXYMETHYL-6-FLUOROPHENYLBORONIC ACID; 3-CARBOXYPHENYLBORONIC ACID; 3-CHLORO-2-(METHOXYMETHOXY)PHENYLBORONIC ACID; 3-CHLORO-2-(TRIFLUOROMETHOXY)PHENYLBORONIC ACID; 3-CHLORO-2-(TRIFLUOROMETHYL)PYRIDINE-4-BORONIC ACID; 3-CHLORO-2-(TRIMETHYLSILYL)PHENYLBORONIC ACID; 3-CHLORO-2,4-DIFLUOROBENZENEBORONIC ACID; 3-CHLORO-2,5-DIFLUOROPHENYLBORONIC ACID; 3-CHLORO-2,6-DIFLUOROPHENYLBORONIC ACID; 3-CHLORO-2-CYANOPHENYLBORONIC ACID; 3-CHLORO-2-FLUOROPHENYLBORONIC ACID; 3-CHLORO-2-FLUOROPYRIDINE-4-BORONIC ACID; 3-CHLORO-2-HYDROXYMETHYLPHENYLBORONIC ACID; 3-CHLORO-2-HYDROXYPHENYLBORONIC ACID;

3-CHLORO-2-HYDROXYPYRIDINE-4-BORONIC ACID; 3-CHLORO-2-ISOBUTOXYPYRIDINE-5-BORONIC ACID; 3-CHLORO-2-METHOXYPHENYLBORONIC ACID; 3-CHLORO-2-METHOXYPYRIDINE-4-BORONIC ACID; 3-CHLORO-2-METHOXYPYRIDINE-5-BORONIC ACID; 3-CHLORO-2-METHOXYPYRIDINE-6-BORONIC ACID; 3-CHLORO-2-METHYLPHENYLBORONIC ACID; 3-CHLORO-2-METHYLPYRIDINE-4-BORONIC ACID; 3-CHLORO-2-METHYLPYRIDINE-5-BORONIC ACID; 3-CHLORO-2-METHYLPYRIDINE-6-BORONIC ACID; 3-CHLORO-2-MORPHOLINOPYRIDINE-4-BORONIC ACID; 3-CHLORO-4-(2,2,2-TRIFLUOROETHOXY)PHENYLBORONIC ACID; 3-CHLORO-4-(2,2-DIFLUOROETHOXY)PHENYLBORONIC ACID; 3-CHLORO-4-(2'-CHLOROBENZYLOXY)PHENYLBORONIC ACID; 3-CHLORO-4-(2'-FLUOROBENZYLOXY)PHENYLBORONIC ACID; 3-CHLORO-4-(3',5'-DIMETHOXYBENZYLOXY)PHENYLBORONIC ACID; 3-CHLORO-4-(3'-CHLOROBENZYLOXY)PHENYLBORONIC ACID; 3-CHLORO-4-(4'-FLUOROBENZYLOXY)PHENYLBORONIC ACID; 3-CHLORO-4-(CYCLOHEXYLCARBAMOYL)BENZENEBORONIC ACID; 3-CHLORO-4-(CYCLOPENTYLCARBAMOYL)PHENYLBORONIC ACID; 3-CHLORO-4-(CYCLOPENTYLOXY)PHENYLBORONIC ACID; 3-CHLORO-4-(CYCLOPROPYLCARBAMOYL)PHENYLBORONIC ACID; 3-CHLORO-4-(CYCLOPROPYLMETHOXY)PHENYLBORONIC ACID; 3-CHLORO-4-(HYDRAZINOCARBONYL)BENZENEBORONIC ACID; 3-CHLORO-4-(HYDROXYMETHYL)PHENYLBORONIC ACID; 3-CHLORO-4-(MORPHOLINE-4-CARBONYL)BENZENEBORONIC ACID; 3-CHLORO-4-(N,N-DIETHYLCARBAMOYL)PHENYLBORONIC ACID; 3-CHLORO-4-(N,N-DIMETHYLCARBAMOYL)BENZENEBORONIC ACID; 3-CHLORO-4-(N-BENZYLCARBAMOYL)PHENYLBORONIC ACID; 3-CHLORO-4-(N-ETHYLCARBAMOYL)BENZENEBORONIC ACID; 3-CHLORO-4-(N-ISOPROPYLCARBAMOYL)PHENYLBORONIC ACID; 3-CHLORO-4-(N-METHYLCARBAMOYL)BENZENEBORONIC ACID; 3-CHLORO-4-(N-TERT-BUTYLCARBAMOYL)PHENYLBORONIC ACID; 3-CHLORO-4-(PIPERIDINE-1-CARBONYL)PHENYLBORONIC ACID; 3-CHLORO-4-(PYRROLIDINYL-1-CARBONYL)PHENYLBORONIC ACID; 3-CHLORO-4-(TETRAHYDRO-2H-PYRAN-4-YLAMINO)PHENYLBORONIC ACID; 3-CHLORO-4-(TRIFLUOROMETHOXY)PHENYLBORONIC ACID; 3-CHLORO-4-(TRIFLUOROMETHYL)PHENYLBORONIC ACID; 3-CHLORO-4,5-DIFLUOROPHENYLBORONIC ACID; 3-CHLORO-4-CYANOPHENYLBORONIC ACID; 3-CHLORO-4-ETHOXYPHENYLBORONIC ACID; 3-CHLORO-4-FLUORO-5-NITROPHENYLBORONIC ACID; 3-CHLORO-4-FLUOROPHENYLBORONIC ACID; 3-CHLORO-4-HYDROXYPHENYLBORONIC ACID; 3-CHLORO-4-ISOPROPOXYPHENYLBORONIC ACID; 3-CHLORO-4-METHOXY-5-METHYLPHENYLBORONIC ACID; 3-CHLORO-4-METHOXYPHENYLBORONIC ACID; 3-CHLORO-4-METHOXYPYRIDINE-2-BORONIC ACID; 3-CHLORO-4-METHYLPHENYLBORONIC ACID; 3-CHLORO-4-METHYLPYRIDINE-2-BORONIC ACID; 3-CHLORO-4-MORPHOLINOPHENYLBORONIC ACID; 3-CHLORO-4-PROPOXYPHENYLBORONIC ACID; 3-CHLORO-4-PYRIDINEBORONIC ACID; 3-CHLORO-4-PYRIDINEBORONIC ACID HYDRATE; 3-CHLORO-4-PYRIDINEBORONIC ACID PENTAHYDRATE; 3-CHLORO-5-(MORPHOLINE-4-CARBONYL)PHENYLBORONIC ACID; 3-CHLORO-5-(PIPERIDINE-1-CARBONYL)PHENYLBORONIC ACID; 3-CHLORO-5-(TRIFLUOROMETHOXY)PHENYLBORONIC ACID; 3-CHLORO-5-(TRIFLUOROMETHYL)PHENYLBORONIC ACID; 3-CHLORO-5-(TRIFLUOROMETHYL)PYRIDIN-2-YLBORONIC ACID; 3-CHLORO-5-ETHOXYPHENYLBORONIC ACID; 3-CHLORO-5-FLUORO-4-METHYLPHENYLBORONIC ACID; 3-CHLORO-5-FLUOROPHENYLBORONIC ACID; 3-CHLORO-5-FLUOROPYRIDINE-4-BORONIC ACID; 3-CHLORO-5-HYDROXYPYRIDINE-2-BORONIC ACID; 3-CHLORO-5-ISOBUTOXYPHENYLBORONIC ACID; 3-CHLORO-5-METHOXYCARBONYL-PHENYL-BORONIC ACID; 3-CHLORO-5-METHOXYPHENYLBORONIC ACID; 3-CHLORO-5-METHOXYPYRIDINE-2-BORONIC ACID; 3-CHLORO-5-METHOXYPYRIDINE-4-BORONIC ACID; 3-CHLORO-5-METHYLPHENYLBORONIC ACID; 3-CHLORO-5-METHYLPYRIDINE-2-BORONIC ACID; 3-CHLORO-5-METHYLPYRIDINE-4-BORONIC ACID; 3-CHLORO-5-PROPOXYPHENYLBORONIC ACID; 3-CHLORO-5-VINYLPHENYLBORONIC ACID; 3-CHLORO-6-METHOXYPYRIDIN-2-YLBORONIC ACID; 3-CHLORO-6-METHYLPYRIDINE-2-BORONIC ACID; 3'-CHLORO-BIPHENYL-4-BORONIC ACID; 3-CHLOROCARBONYLPHENYLBORONIC ACID; 3-CHLOROPHENYLBORONIC ACID; 3-CHLOROPYRIDINE-2-BORONIC ACID; 3-CHLOROTHIOPHENE-2-BORONIC ACID; 3-CHLOROTHIOPHENE-4-BORONIC ACID; 3-CYANO-2-FLUOROPHENYLBORONIC ACID; 3-CYANO-2-HYDROXYPHENYLBORONIC ACID; 3-CYANO-2-METHOXYPHENYLBORONIC ACID; 3-CYANO-2-METHYLPHENYLBORONIC ACID; 3-CYANO-4-FLUOROPHENYLBORONIC ACID; 3-CYANO-4-HYDROXYPHENYLBORONIC ACID; 3-CYANO-4-ISOPROPOXYPHENYLBORONIC ACID; 3-CYANO-4-METHOXYPHENYLBORONIC ACID; 3-CYANO-4-METHYLPHENYLBORONIC ACID; 3-CYANO-4-PROPOXYPHENYLBORONIC ACID; 3-CYANO-5-(PROP-1-YNYL)PHENYLBORONIC ACID; 3-CYANO-5-(TRIFLUOROMETHYL)PHENYLBORONIC ACID; 3-CYANO-5-FLUOROPHENYLBORONIC ACID; 3-CYANO-5-HYDROXYPHENYLBORONIC ACID; 3-CYANO-5-METHOXYPHENYLBORONIC ACID; 3-CYANO-5-METHYLPHENYLBORONIC ACID; 3-CYANO-5-NITROPHENYLBORONIC ACID; 3'-CYANOBIPHENYL-3-YLBORONIC ACID; 3-CYANOMETHOXYPHENYLBORONIC ACID; 3-CYANOMETHYLPHENYLBORONIC ACID; 3-CYANOPHENYLBORONIC ACID; 3-CYANOPYRAZIN-2-YLBORONIC ACID; 3-CYANOPYRIDINE-2-BORONIC ACID; 3-CYANOPYRIDINE-4-BORONIC ACID; 3-CYANOTHIOPHEN-2-YLBORONIC ACID; 3-CYCLOBUTYLPHENYLBORONIC ACID; 3-CYCLOPROPOXYPHENYLBORONIC ACID; 3-CYCLOPROPYLL-1H-PYRAZOLE-5-BORONIC ACID; 3-CYCLOPROPYLPHENYLBORONIC ACID; 3-CYCLOPROPYLPYRIDIN-4-YLBORONIC ACID; 3-DIFLUOROMETHOXY-4-FLUORO-BENZENEBORONIC ACID; 3-DIFLUOROMETHOXY-4-METHYL-BENZENEBORONIC ACID; 3-DIFLUOROMETHYL-PHENYL-BORONIC ACID; 3-DIMETHYLAMINOPHENYLBORONIC ACID HCL; 3-ETHOXY-2,4,6-TRIFLUOROPHENYLBORONIC ACID; 3-ETHOXY-2-FLUOROPHENYLBORONIC ACID; 3-ETHOXY-4-

FLUOROPHENYLBORONIC ACID; 3-ETHOXY-4-METHOXYPHENYLBORONIC ACID; 3-ETHOXY-5-(TRIFLUOROMETHOXY)PHENYLBORONIC ACID; 3-ETHOXY-5-(TRIFLUOROMETHYL)BENZENEBORONIC ACID; 3-ETHOXY-5-AMINOPYRIDINE-4-BORONIC ACID; 3-ETHOXY-5-FLUOROPHENYLBORONIC ACID; 3-ETHOXY-5-METHYLPHENYLBORONIC ACID; 3-ETHOXY-5-METHYLPYRIDINE-4-BORONIC ACID; 3-ETHOXYCARBONYL-4-FLUOROPHENYLBORONIC ACID; 3-ETHOXYCARBONYLMETHYLPHENYLBORONIC ACID; 3-ETHOXYCARBONYLPHENYLBORONIC ACID; 3-ETHOXYNAPHTHALEN-2-YLBORONIC ACID; 3-ETHOXYPHENYLBORONIC ACID; 3-ETHOXYPYRIDINE-4-BORONIC ACID; 3-ETHYLAMINOPHENYLBORONIC ACID; 3-ETHYLFURAN-2-BORONIC ACID; 3-ETHYLPHENYLBORONIC ACID; 3-ETHYLSULFINYLPHENYLBORONIC ACID; 3-ETHYLSULFONYLPHENYLBORONIC ACID; 3-ETHYLTHIOPHENE-2-BORONIC ACID; 3-ETHYLTHIOPHENYLBORONIC ACID; 3-FLUORO-1H-PYRROLO[2,3-B]PYRIDIN-5-YLBORONIC ACID; 3-FLUORO-1-METHYL-1H-PYRROLE-2-BORONIC ACID; 3-FLUORO-2-(5-PROPYL-1,3,4-OXADIAZOL-2-YL)PHENYLBORONIC ACID; 3-FLUORO-2-(METHYLTHIOMETHOXY)PHENYLBORONIC ACID; 3-FLUORO-2-(TRIFLUOROMETHYL)PYRIDINE-4-BORONIC ACID; 3-FLUORO-2-(TRIMETHYLSILYL)PHENYLBORONIC ACID; 3-FLUORO-2-HYDROXYPHENYLBORONIC ACID; 3-FLUORO-2-HYDROXYPYRIDINE-4-BORONIC ACID; 3-FLUORO-2-METHOXY-5-(METHYLTHIO)BENZENEBORONIC ACID; 3-FLUORO-2-METHOXYPHENYLBORONIC ACID; 3-FLUORO-2-METHOXYPYRIDINE-4-BORONIC ACID; 3-FLUORO-2-METHOXYPYRIDINE-5-BORONIC ACID; 3-FLUORO-2-METHYLPHENYLBORONIC ACID; 3-FLUORO-2-METHYLPYRIDINE-4-BORONIC ACID; 3-FLUORO-2-MORPHOLINOPYRIDINE-4-BORONIC ACID; 3-FLUORO-4-((4-METHOXYBENZYLOXY)CARBAMOYL)PHENYLBORONIC ACID; 3-FLUORO-4-(1,2,4-OXADIAZOL-3-YL)PHENYLBORONIC ACID; 3-FLUORO-4-(2,2,2-TRIFLUOROETHOXY)PHENYLBORONIC ACID; 3-FLUORO-4-(2-HYDROXYETHYLCARBAMOYL)PHENYLBORONIC ACID; 3-FLUORO-4-(4-METHOXYBENZYLTHIO)PHENYLBORONIC ACID; 3-FLUORO-4-(5-METHYL-1,3,4-OXADIAZOL-2-YL)PHENYLBORONIC ACID; 3-FLUORO-4-(ISOPROPYLCARBAMOYL)BENZENEBORONIC ACID; 3-FLUORO-4-(METHOXY(METHYL)CARBAMOYL)PHENYLBORONIC ACID; 3-FLUORO-4-(METHOXYCARBAMOYL)BENZENEBORONIC ACID; 3-FLUORO-4-(METHOXYMETHOXY)PHENYLBORONIC ACID; 3-FLUORO-4-(METHYLCARBAMOYL)BENZENEBORONIC ACID; 3-FLUORO-4-(METHYLSULFONYL)PHENYLBORONIC ACID; 3-FLUORO-4-(METHYLTHIO)PHENYLBORONIC ACID; 3-FLUORO-4-(PHENYLCARBAMOYL)BENZENEBORONIC ACID; 3-FLUORO-4-(PIPERIDIN-1-YLCARBONYL)BENZENEBORONIC ACID; 3-FLUORO-4-(PROPYLCARBAMOYL)BENZENEBORONIC ACID; 3-FLUORO-4-(PYRROLIDINE-1-CARBONYL)PHENYLBORONIC ACID; 3-FLUORO-4-(THIOPHEN-2-YLMETHOXYMETHYL)PHENYLBORONIC ACID; 3-FLUORO-4-(TRIFLUOROMETHOXY)PHENYLBORONIC ACID; 3-FLUORO-4-BIPHENYLBORONIC ACID; 3-FLUORO-4'-HEPTYLBIPHENYL-4-BORONIC ACID; 3-FLUORO-4-HYDRAZINOCARBONYLPHENYLBORONIC ACID; 3-FLUORO-4-HYDROXYPHENYLBORONIC ACID; 3-FLUORO-4-ISOPROPOXYPHENYLBORONIC ACID; 3-FLUORO-4-METHOXY-5-TRIFLUOROMETHYLPHENYLBORONIC ACID; 3-FLUORO-4-METHOXYCARBONYLPHENYLBORONIC ACID; 3-FLUORO-4-METHOXYPHENYLBORONIC ACID; 3-FLUORO-4-METHYLPHENYLBORONIC ACID; 3-FLUORO-4-MORPHOLINOPHENYLBORONIC ACID; 3-FLUORO-4-N-METHYL, N-ETHYLAMIDYL PHENYLBORONIC ACID; 3-FLUORO-4'-PENTYLBIPHENYL-4-BORONIC ACID; 3-FLUORO-4-PROPOXYPHENYLBORONIC ACID; 3-FLUORO-4-TRIFLUOROMETHYL-PHENYLBORONIC ACID; 3-FLUORO-5-(2,2,2-TRIFLUOROETHOXY)BENZENEBORONIC ACID; 3-FLUORO-5-(DIETHYLCARBAMOYL)PHENYLBORONIC ACID; 3-FLUORO-5-(ETHOXY-D5)-PHENYLBORONIC ACID; 3-FLUORO-5-(ETHYL-D5)-PHENYLBORONIC ACID; 3-FLUORO-5-(HYDRAZINECARBONYL)PHENYLBORONIC ACID; 3-FLUORO-5-(ISO-PROPOXY-D7)-PHENYLBORONIC ACID; 3-FLUORO-5-(ISO-PROPYL-D7)-PHENYLBORONIC ACID; 3-FLUORO-5-(METHOXY-D3)-PHENYLBORONIC ACID; 3-FLUORO-5-(METHYLCARBAMOYL)PHENYLBORONIC ACID; 3-FLUORO-5-(MORPHOLIN-4-YLCARBONYL)BENZENEBORONIC ACID; 3-FLUORO-5-(PIPERIDIN-1-YLCARBONYL)BENZENEBORONIC ACID; 3-FLUORO-5-(PROPYLCARBAMOYL)PHENYLBORONIC ACID; 3-FLUORO-5-ETHOXYCARBONYLPHENYLBORONIC ACID; 3-FLUORO-5-HYDROXYPHENYLBORONIC ACID; 3-FLUORO-5-HYDROXYPYRIDINE-2-BORONIC ACID; 3-FLUORO-5-ISOBUTOXYPHENYLBORONIC ACID; 3-FLUORO-5-ISOPROPOXYPHENYLBORONIC ACID; 3-FLUORO-5-METHOXYPHENYLBORONIC ACID; 3-FLUORO-5-METHOXYPYRIDINE-2-BORONIC ACID; 3-FLUORO-5-METHYLPHENYLBORONIC ACID; 3-FLUORO-5-METHYLPYRIDINE-4-BORONIC ACID; 3-FLUORO-5-MORPHOLINOPHENYLBORONIC ACID; 3-FLUORO-5-PYRROLIDINOPHENYLBORONIC ACID; 3-FLUORO-5-VINYLPHENYLBORONIC ACID; 3-FLUOROBENZYLBORONIC ACID; 3'-FLUORO-BIPHENYL-4-BORONIC ACID; 3-FLUOROISOQUINOLIN-7-YLBORONIC ACID; 3-FLUOROPHENYLBORONIC ACID; 3-FLUOROPYRIDINE-2-BORONIC ACID; 3-FLUOROPYRIDINE-4-BORONIC ACID; 3-FLUOROPYRIDINE-4-BORONIC ACID HYDRATE; 3-HEXYLTHIOPHENE-2-BORONIC ACID; 3-HYDROXY-2-(TRIFLUOROMETHOXY)PHENYLBORONIC ACID; 3-HYDROXY-2-(TRIFLUOROMETHYL)PHENYLBORONIC ACID; 3-HYDROXY-2-(TRIFLUOROMETHYL)PYRIDINE-4-BORONIC ACID; 3-HYDROXY-2-METHOXYPHENYLBORONIC ACID; 3-HYDROXY-2-METHYLPHENYLBORONIC ACID; 3-HYDROXY-2-METHYLPYRIDINE-4-BORONIC ACID; 3-HYDROXY-4-(METHOXYCARBONYL)PHENYLBORONIC ACID; 3-HYDROXY-4-(TRIFLUOROMETHOXY)PHENYLBORONIC ACID; 3-HYDROXY-4-(TRIFLUOROMETHYL)PHENYLBORONIC ACID; 3-HYDROXY-4-METHOXYPHENYLBORONIC ACID; 3-HYDROXY-4-METHYLPHENYLBORONIC ACID; 3-HYDROXY-4-MORPHOLINOPHENYLBORONIC ACID; 3-HYDROXY-5-(TRIFLUOROMETHOXY)PHENYLBORONIC ACID; 3-HYDROXY-5-(TRIFLUOROMETHYL)PHENYLBORONIC ACID; 3-HYDROXY-5-METHOXYPHENYLBORONIC

ACID; 3-HYDROXY-5-METHYLPHENYLBORONIC ACID; 3-HYDROXY-5-NITROPHENYLBORONIC ACID; 3-HYDROXYMETHYL-4-(TRIFLUOROMETHOXY)PHENYLBORONIC ACID; 3-HYDROXYMETHYL-4-METHYLPHENYLBORONIC ACID; 3-HYDROXYMETHYLTHIOPHENE-2-BORONIC ACID; 3-HYDROXYNAPHTHALENE-1-BORONIC ACID; 3-HYDROXYNAPHTHALENE-2-BORONIC ACID; 3-HYDROXYPHENYLBORONIC ACID; 3-HYDROXYPYRAZINE-2-BORONIC ACID; 3-HYDROXYPYRIDINE-2-BORONIC ACID; 3-HYDROXYPYRIDINE-4-BORONIC ACID; 3-HYDROXYQUINOLINE-2-BORONIC ACID; 3-HYDROXYQUINOLINE-4-BORONIC ACID; 3-HYDROXYQUINOLINE-5-BORONIC ACID; 3-HYDROXYQUINOLINE-6-BORONIC ACID; 3-HYDROXYQUINOLINE-7-BORONIC ACID; 3-HYDROXYQUINOLINE-8-BORONIC ACID; 3-ISOBUTOXY-4-METHOXYPHENYLBORONIC ACID; 3-ISOBUTOXY-5-(TRIFLUOROMETHOXY)PHENYLBORONIC ACID; 3-ISOBUTOXY-5-METHYLPHENYLBORONIC ACID; 3-ISOBUTOXYPHENYLBORONIC ACID; 3-ISOPROPOXY-2,4,6-TRIFLUOROPHENYLBORONIC ACID; 3-ISOPROPOXY-4-METHOXYPHENYLBORONIC ACID; 3-ISOPROPOXY-5-(TRIFLUOROMETHOXY)PHENYLBORONIC ACID; 3-ISOPROPOXY-5-METHYLPHENYLBORONIC ACID; 3-ISOPROPOXY-5-TRIFLUOROMETHYLPHENYLBORONIC ACID; 3-ISOPROPOXYPHENYLBORONIC ACID; 3-ISOPROPROXY-4-METHYLPHENYLBORONIC ACID; 3-ISOPROPYLPHENYLBORONIC ACID; 3-ISOTHIOCYANOPHENYLBORONIC ACID; 3-MALEIMIDOPHENYL BORONIC ACID; 3-MERCAPTOPHENYLBORONIC ACID; 3-METHACRYLAMIDOPHENYLBORONIC ACID; 3-METHOXY-1-PROPENYLBORONIC ACID; 3-METHOXY-2-(METHOXYMETHOXY)PHENYLBORONIC ACID; 3-METHOXY-2-(TRIFLUOROMETHOXY)PHENYLBORONIC ACID; 3-METHOXY-2-(TRIFLUOROMETHYL)PHENYLBORONIC ACID; 3-METHOXY-2-(TRIFLUOROMETHYL)PYRIDINE-4-BORONIC ACID; 3-METHOXY-2,4,6-TRIFLUOROPHENYLBORONIC ACID; 3-METHOXY-2,5-DIMETHYLPHENYLBORONIC ACID; 3-METHOXY-2-HYDROXYPHENYLBORONIC ACID; 3-METHOXY-2-METHYLPHENYLBORONIC ACID; 3-METHOXY-2-METHYLPYRIDINE-4-BORONIC ACID; 3-METHOXY-3-OXOPROP-1-EN-2-YLBORONIC ACID; 3-METHOXY-4-(1,2,4-OXADIAZOL-3-YL)PHENYLBORONIC ACID; 3-METHOXY-4-(PYRIDIN-3-YLMETHOXY)PHENYLBORONIC ACID; 3-METHOXY-4-(PYRIDIN-4-YLMETHOXY)PHENYLBORONIC ACID; 3-METHOXY-4-(TRIFLUOROMETHOXY)PHENYLBORONIC ACID; 3-METHOXY-4-CARBOXYPHENYLBORONIC ACID; 3-METHOXY-4-METHOXYCARBONYLPHENYLBORONIC ACID; 3-METHOXY-4-METHYLPHENYLBORONIC ACID; 3-METHOXY-4-MORPHOLINOPHENYLBORONIC ACID; 3-METHOXY-5-(TRIFLUOROMETHOXY)PHENYLBORONIC ACID; 3-METHOXY-5-(TRIFLUOROMETHYL)BENZENEBORONIC ACID; 3-METHOXY-5-AMINOPYRIDINE-4-BORONIC ACID; 3-METHOXY-5-METHYLPHENYLBORONIC ACID; 3-METHOXY-5-METHYLPYRIDINE-4-BORONIC ACID; 3-METHOXY-5-PROPOXYPHENYLBORONIC ACID; 3-METHOXY-6-(4-METHOXYPHENYL)PYRIDAZIN-4-YLBORONIC ACID; 3'-METHOXY-BIPHENYL-4-BORONIC ACID; 3-METHOXYCARBONYL-5-METHYLPHENYLBORONIC ACID; 3-METHOXYCARBONYL-5-NITROPHENYLBORONIC ACID; 3-METHOXYCARBONYLPHENYLBORONIC ACID; 3-METHOXYMETHOXY-4-METHYLPHENYLBORONIC ACID; 3-METHOXYMETHYLPHENYLBORONIC ACID; 3-METHOXYNAPHTHALENE-2-BORONIC ACID; 3-METHOXYPHENYLBORONIC ACID; 3-METHOXYPYRAZINE-2-BORONIC ACID; 3-METHOXYPYRIDINE-2-BORONIC ACID; 3-METHOXYPYRIDINE-4-BORONIC ACID; 3-METHOXYPYRIDINE-4-BORONIC ACID HYDRATE; 3-METHOXYTHIOPHENE-2-BORONIC ACID; 3-METHYL-1-(TETRAHYDROPYRAN-2-YL)-1H-INDAZOLE-4-BORONIC ACID; 3-METHYL-1-BUTYLBORONIC ACID; 3-METHYL-1H-INDAZOLE-4-BORONIC ACID; 3-METHYL-1H-INDAZOLE-5-BORONIC ACID; 3-METHYL-1H-INDAZOLE-6-BORONIC ACID; 3-METHYL-1H-INDAZOLE-7-BORONIC ACID; 3-METHYL-1H-PYRAZOL-4-YLBORONIC ACID; 3-METHYL-1-PROPYL-1H-PYRAZOL-5-YLBORONIC ACID; 3-METHYL-2-(2-(TRIFLUOROMETHOXY)PHENYL)PYRIDINE-4-BORONIC ACID; 3-METHYL-2-(2-(TRIFLUOROMETHYL)PHENYL)PYRIDINE-4-BORONIC ACID; 3-METHYL-2-(2,4,5-TRICHLOROPHENYL)PYRIDINE-4-BORONIC ACID; 3-METHYL-2-(3-(TRIFLUOROMETHOXY)PHENYL)PYRIDINE-4-BORONIC ACID; 3-METHYL-2-(3-(TRIFLUOROMETHYL)PHENYL)PYRIDINE-4-BORONIC ACID; 3-METHYL-2-(4-(TRIFLUOROMETHOXY)PHENYL)PYRIDINE-4-BORONIC ACID; 3-METHYL-2-(4-(TRIFLUOROMETHYL)PHENYL)PYRIDINE-4-BORONIC ACID; 3-METHYL-2-(PERFLUOROPHENYL)PYRIDINE-4-BORONIC ACID; 3-METHYL-2-(TRIFLUOROMETHOXY)PHENYLBORONIC ACID; 3-METHYL-2-(TRIFLUOROMETHYL)PHENYLBORONIC ACID; 3-METHYL-2-BUTEN-2-YLBORONIC ACID; 3-METHYL-2-PROPOXYPYRIDINE-5-BORONIC ACID; 3-METHYL-3H-QUINAZOLIN-4-ONE-6-BORONIC ACID; 3-METHYL-4-(1,2,4-OXADIAZOL-3-YL)PHENYLBORONIC ACID; 3-METHYL-4-MORPHOLINOPHENYLBORONIC ACID; 3-METHYL-4-TRIFLUOROMETHOXYPHENYLBORONIC ACID; 3-METHYL-4-TRIFLUOROMETHYLPHENYLBORONIC ACID; 3-METHYL-5-(TRIFLUOROMETHOXY)PHENYLBORONIC ACID; 3-METHYL-5-NITROPYRIDIN-2-YLBORONIC ACID; 3-METHYL-5-PROPOXYPHENYLBORONIC ACID; 3-METHYLBENZO[B]THIOPHENE-2-BORONIC ACID; 3-METHYLBENZOFURAN-2-YLBORONIC ACID; 3'-METHYLBIPHENYL-2-YLBORONIC ACID; 3-METHYLFURAN-2-YLBORONIC ACID; 3-METHYLPHENYLBORONIC ACID; 3-METHYLPYRAZINE-2-BORONIC ACID; 3-METHYLPYRIDINE-2-BORONIC ACID; 3-METHYLPYRIDINE-4-BORONIC ACID; 3-METHYLSULFAMOYLPHENYLBORONIC ACID; 3-METHYLSULFINYLPHENYLBORONIC ACID; 3-METHYLTHIOPHENE-2-BORONIC ACID; 3-MORPHOLINOPHENYLBORONIC ACID HYDROCHLORIDE; 3-MORPHOLINOPYRIDINE-2-BORONIC ACID; 3-N-CYCLOHEXYLSULFAMOYLPHENYLBORONIC ACID; 3-NITRO-5-(PIPERIDIN-1-YLCARBONYL)BENZENEBORONIC ACID; 3-NITRO-5-(PYRROLIDIN-1-YLCARBONYL)BENZENEBORONIC ACID; 3-NITRO-5-(TRIFLUOROMETHYL)BENZENEBORONIC ACID; 3-NITRO-5-VINYLPHENYLBORONIC ACID; 3'-NITRO-BIPHENYL-4-BORONIC ACID; 3-NITROPHENYLBORONIC ACID; 3-NITROPYRIDINE-2-BORONIC

ACID; 3-OXO-2,3-DIHYDROPYRIDAZIN-4-YLBORONIC ACID; 3-OXO-6-(TRIFLUOROMETHYL)ISOINDOLIN-5-YLBORONIC ACID; 3-OXO-6-PHENYLISOINDOLIN-5-YLBORONIC ACID; 3-OXOISOINDOLIN-5-YLBORONIC ACID; 3-PHENOXYPHENYLBORONIC ACID; 3-PHENYL-1H-PYRAZOLE-5-BORONIC ACID; 3-PHENYL-1H-PYRROLO[2,3-B]PYRIDINE-2-BORONIC ACID; 3-PHENYL-1H-PYRROLO[2,3-B]PYRIDINE-4-BORONIC ACID; 3-PHENYL-1H-PYRROLO[2,3-B]PYRIDINE-5-BORONIC ACID; 3-PHENYL-1H-PYRROLO[2,3-B]PYRIDINE-6-BORONIC ACID; 3-PHENYLISOXAZOLE-5-BORONIC ACID; 3-PHENYLPROPYLBORONIC ACID; 3-PHENYLPYRIDINE-2-BORONIC ACID; 3-PHENYLPYRIDINE-4-BORONIC ACID; 3-PHENYLTHIOPHENE-2-BORONIC ACID; 3-PICOLINE-4-BORONIC ACID HCL; 3-PICOLINE-5-BORONIC ACIDHYDRATE; 3-PROPOXY-2,4,6-TRIFLUOROPHENYLBORONIC ACID; 3-PROPOXY-5-(TRIFLUOROMETHOXY)PHENYLBORONIC ACID; 3-PROPOXY-5-TRIFLUOROMETHYLPHENYLBORONIC ACID; 3-PROPOXYPHENYLBORONIC ACID; 3-P-TOLYLISOXAZOL-5-YLBORONIC ACID; 3-PYRAZOL-1-YL-PHENYLBORONIC ACID; 3-PYRIDINECARBOXYLIC ACID-6-BORONIC ACID; 3-PYRROLIDINYLBORONIC ACID; 3-PYRROLIDINYLPYRIDINE-2-BORONIC ACID; 3-PYRROLYLBORONIC ACID; 3-QUINOLINEBORONIC ACID; 3-QUINOLINEBORONIC ACID, HCL; 3-T-BDMSTHIOPHENYLBORONIC ACID; 3-T-BUTOXYCARBOXYPHENYLBORONIC ACID; 3-T-BUTYL-5-CARBOXYPHENYLBORONIC ACID; 3-TERT-BUTOXYMETHYLPHENYLBORONIC ACID; 3-TERT-BUTYL-1H-PYRAZOLE-5-BORONIC ACID; 3-TERT-BUTYLPHENYLBORONIC ACID; 3-TRIFLUOROMETHYLBENZYLBORONIC ACID; 3'-TRIFLUOROMETHYL-BIPHENYL-4-BORONIC ACID; 3-TRIMETHYLSILYLPHENYLBORONIC ACID; 3-VINYLPHENYLBORONIC ACID; 4-((1-(TERT-BUTOXYCARBONYL)AZEPAN-3-YL)METHYL)PHENYLBORONIC ACID; 4-((1-(TERT-BUTOXYCARBONYL)PIPERIDIN-3-YL)METHYL)PHENYLBORONIC ACID; 4-((1-(TERT-BUTOXYCARBONYL)PYRROLIDIN-3-YL)METHYL)PHENYLBORONIC ACID; 4-((1-NAPHTHYLOXY)METHYL)PHENYLBORONIC ACID; 4-((3,3-DIFLUOROPYRROLIDIN-1-YL)METHYL)PHENYLBORONIC ACID; 4-((3,3-DIMETHYLPYRROLIDIN-1-YL)METHYL)PHENYLBORONIC ACID; 4-((3-HYDROXYPYRROLIDIN-1-YL)METHYL)PHENYLBORONIC ACID; 4-((4-(TERT-BUTOXYCARBONYL)PIPERAZIN-1-YL)METHYL)PHENYLBORONIC ACID; 4-((4-(TRIFLUOROMETHYL)PIPERIDIN-1-YL)METHYL)PHENYLBORONIC ACID; 4-((4H-1,2,4-TRIAZOL-3-YL)METHOXY)PHENYLBORONIC ACID; 4-((4H-1,2,4-TRIAZOL-4-YL)CARBAMOYL)PHENYLBORONIC ACID, HCL; 4-((4-METHOXYPIPERIDIN-1-YL)METHYL)PHENYLBORONIC ACID; 4-((BENZYLOXYCARBONYLAMINO)METHYL)PHENYLBORONIC ACID; 4-((DIETHYLAMINO)METHYL)THIOPHEN-2-YLBORONIC ACID; 4-((DIMETHOXYPHOSPHORYL)METHYL)PHENYLBORONIC ACID; 4-((DIMETHYLAMINO)METHYL)PHENYLBORONIC ACID; 4-((DI-TERT-BUTOXYPHOSPHORYL)METHYL)PHENYLBORONIC ACID; 4-((N,N-DIMETHYLSULFAMOYL)METHYL)PHENYLBORONIC ACID; 4-((N-BOC-AMINO)METHYL)PHENYLBORONIC ACID; 4-((N-METHYLACETAMIDO)METHYL)PHENYLBORONIC ACID; 4-((PHENYLAMINO)METHYL)PHENYLBORONIC ACID; 4-((PYRIDIN-4-YLOXY)METHYL)PHENYLBORONIC ACID; 4-((TETRAHYDROFURAN-2-YL)METHYLCARBAMOYL)PHENYLBORONIC ACID; 4-([1,3]DIOXOLAN-2-YLMETHOXY)-PHENYLBORONIC ACID; 4-(1-(BENZYLOXYCARBONYLAMINO)CYCLOPROPYL)PHENYLBORONIC ACID; 4-(1-(HYDROXYMETHYL)CYCLOPROPYL)PHENYLBORONIC ACID; 4-(1-(METHOXYCARBONYL)CYCLOPROPYL)PHENYLBORONIC ACID; 4-(1-(MORPHOLINE-4-CARBONYL)CYCLOPROPYL)PHENYLBORONIC ACID; 4-(1-(TERT-BUTOXYCARBONYL)AZETIDIN-3-YL)PHENYLBORONIC ACID; 4-(1-(TERT-BUTOXYCARBONYL)AZETIDIN-3-YLOXY)PHENYLBORONIC ACID; 4-(1-(TERT-BUTOXYCARBONYL)PIPERIDIN-3-YL)PHENYLBORONIC ACID; 4-(1-(TERT-BUTOXYCARBONYL)PIPERIDIN-4-YL)PHENYLBORONIC ACID; 4-(1-(TERT-BUTOXYCARBONYL)PYRROLIDIN-3-YL)PHENYLBORONIC ACID; 4-(1-(TERT-BUTOXYCARBONYLAMINO)CYCLOPROPYL)PHENYLBORONIC ACID; 4-(1,2,4-OXADIAZOL-3-YL)PHENYLBORONIC ACID; 4-(1,3-DIOXOLAN-2-YL)-2,6-DIFLUOROPHENYLBORONIC ACID; 4-(1,3-DIOXOLAN-2-YL)-2,6-DIMETHOXYPHENYLBORONIC ACID; 4-(1-ALLYL-PIPERIDIN-2-YL)-BENZENEBORONIC ACID; 4-(1-ALLYL-PYRROLIDIN-2YL)BENZENEBORONIC ACID; 4-(1-AMINOCYCLOPROPYL)PHENYLBORONIC ACID HYDROCHLORIDE; 4-(1-AMINOETHYL)PHENYLBORONIC ACID; 4-(1-BENZYL-1H-PYRAZOL-4-YL)-2-FLUOROPHENYLBORONIC ACID; 4-(1-BENZYL-1H-PYRAZOL-4-YL)PHENYLBORONIC ACID; 4-(1-BENZYLPIPERIDIN-4-YL)PHENYLBORONIC ACID; 4(1-BOC-PIPERIDIN-4-YLOXY)-2-METHOXYPHENYLBORONIC ACID; 4(1-BOC-PIPERIDIN-4-YLOXY)-3-METHOXYPHENYLBORONIC ACID; 4-(1-BOC-PIPERIDIN-4-YLOXY)PHENYLBORONIC ACID; 4-(1-BOC-PYRROLIDIN-2-YL)BENZENEBORONIC ACID; 4-(1-BOC-PYRROLIDIN-3-YLOXY)PHENYLBORONIC ACID; 4-(1-CARBAMOYLCYCLOPROPYL)PHENYLBORONIC ACID; 4-(1-CARBOXYCYCLOPROPYL)PHENYLBORONIC ACID; 4-(1-CYANOCYCLOPROPYL)PHENYLBORONIC ACID; 4-(1H-1,2,3-TRIAZOL-4-YL)PHENYLBORONIC ACID; 4-(1H-IMIDAZOL-1-YL)PHENYLBORONIC ACID; 4-(1H-PYRAZOL-1-YLSULFONYL)PHENYLBORONIC ACID; 4-(1H-PYRROL-1-YL)PHENYLBORONIC ACID; 4-(1H-PYRROL-1-YLSULFONYL)PHENYLBORONIC ACID; 4-(1H-TETRAZOL-5-YL)BUTYLBORONIC ACID; 4-(1H-TETRAZOL-5-YLCARBAMOYL)BENZENEBORONIC ACID HYDROCHLORIDE; 4-(1-HYDROXY-1-PHENYL)METHYLPHENYLBORONIC ACID; 4-(1-HYDROXYETHYL)PHENYLBORONIC ACID; 4-(1-METHYL-1H-IMIDAZOL-2-YL)PHENYLBORONIC ACID; 4-(1-PHENYL-1H-BENZO[D]IMIDAZOL-2-YL)PHENYLBORONIC ACID; 4-(1-PYRROLIDINYLMETHYL)PHENYLBORONIC ACID; 4-(2-(1,3-DIOXOISOINDOLIN-2-YL)ETHOXY)PHENYLBORONIC ACID; 4-(2-(1H-IMIDAZOL-1-YL)ETHOXY)PHENYLBORONIC ACID; 4-(2-(1H-PYRAZOL-1-YL)ETHOXY)PHENYLBORONIC ACID; 4-(2-(BENZYLOXYCARBONYLAMINO)ETHYL)PHENYLBORONIC ACID; 4-(2-

(DIETHYLAMINO)ETHYLCARBAMOYL) PHENYLBORONIC ACID, HCL; 4-(2-(DIMETHYLAMINO)-2-OXOETHYL) PHENYLBORONIC ACID; 4-(2-(DIMETHYLAMINO)ETHOXY)-3-METHOXYPHENYLBORONIC ACID; 4-(2-(DIMETHYLAMINO)ETHYLCARBAMOYL)PHENYLBORONIC ACID, HCL; 4-(2-(DIMETHYLAMINO)ETHYLSULFONYL)PHENYLBORONIC ACID; 4-(2-(METHYLAMINO)-2-OXOETHOXY)PHENYLBORONIC ACID; 4-(2-(METHYLAMINO)-2-OXOETHYL)PHENYLBORONIC ACID; 4-(2-(METHYLAMINO)ACETAMIDO)PHENYLBORONIC ACID; 4-(2-(PYRROLIDIN-1-YL)ETHOXY)PHENYLBORONIC ACID; 4-(2-(T-BUTOXYCARBONYLAMINO)ETHYLCARBAMOYL)PHENYLBORONIC ACID; 4-(2,2,2-TRIFLUOROACETAMIDO)NAPHTHALEN-1-YLBORONIC ACID; 4-(2,2,2-TRIFLUOROETHOXY)PHENYLBORONIC ACID; 4-(2,2,2-TRIFLUOROETHYLAMINOCARBONYL)BENZENEBORONIC ACID; 4-(2,2-DIFLUOROETHOXY)PHENYLBORONIC ACID; 4-(2,2-DIMETHOXYETHOXY)PHENYLBORONIC ACID; 4-(2,2-DIMETHYLPROPANOYL)-4H-1,4-BENZOXAZIN-3-YLBORONIC ACID; 4-(2,2-DIPHENYLVINYL)PHENYLBORONIC ACID; 4-(2,4-DIFLUOROPHENOXY)PHENYLBORONIC ACID; 4-(2,4-DIOXOIMIDAZOLIDIN-5-YL)PHENYBORONIC ACID; 4-(2,5-DIMETHYL-1H-PYRROL-1-YL)PHENYLBORONIC ACID; 4-(2,6-DICHLOROPHENYLMETHOXY)PHENYLBORONIC ACID; 4-(2-ACETAMIDOETHOXY)PHENYLBORONIC ACID; 4-(2-ACETAMIDOETHYL)PHENYLBORONIC ACID; 4-(2-AMINOPHENOXY)PHENYLBORONIC ACID, HCL; 4-(2-CARBOXYETHYL)PHENYLBORONIC ACID; 4-(2-CARBOXYVINYL)BENZENEBORONIC ACID; 4-(2'-CHLOROBENZYLOXY)-3,5-DIMETHYLPHENYLBORONIC ACID; 4-(2-CHLOROETHOXY)PHENYLBORONIC ACID; 4-(2-CHLOROETHYLCARBAMOYL)BENZENEBORONIC ACID; 4-(2-CHLOROPHENOXYMETHYL)PHENYLBORONIC ACID; 4-(2-CYANOETHYL)PHENYLBORONIC ACID; 4-(2-CYANOETHYLAMINOCARBONYL)PHENYLBORONIC ACID; 4-(2-CYANOVINYL)PHENYLBORONIC ACID; 4-(2-ETHOXY-2-OXOETHOXY)BENZENEBORONIC ACID; 4-(2-ETHOXY-2-OXOETHYLTHIO)PHENYLBORONIC ACID; 4-(2'-FLUOROBENZYLOXY)PHENYLBORONIC ACID; 4-(2-FLUOROETHOXY)PHENYLBORONIC ACID; 4-(2-FLUOROPHENOXY)PHENYLBORONIC ACID; 4-(2-FLUOROPHENYL)FURAN-2-BORONIC ACID; 4-(2-FLUOROPHENYL)THIOPHENE-2-BORONIC ACID; 4-(2-FURYL)PYRIDINE-2-BORONIC ACID; 4-(2H-TETRAZOL-5-YL)-PHENYLBORONIC ACID; 4-(2-HYDROXYETHOXY)-3-METHOXYPHENYLBORONIC ACID; 4-(2-HYDROXYETHYL)PHENYLBORONIC ACID; 4-(2-HYDROXYETHYLCARBAMOYL)PHENYLBORONIC ACID; 4-(2-HYDROXYPROPAN-2-YL)PYRIDINE-2-BORONIC ACID; 4-(2-HYDROXYPROPAN-2-YL)PYRIDINE-3-BORONIC ACID; 4-(2-METHOXY-2-OXOETHOXY)PHENYLBORONIC ACID; 4-(2-METHOXY-2-OXOETHYL)-2-METHYLPHENYLBORONIC ACID; 4-(2'-METHOXYBENZYLOXY)PHENYLBORONIC ACID; 4-(2-METHOXYCARBONYLETHYL)PHENYLBORONIC ACID; 4-(2-METHOXYETHOXY)PHENYLBORONIC ACID; 4-(2-METHOXYETHYL)PHENYLBORONIC ACID; 4-(2-METHOXYETHYLCARBAMOYL) PHENYLBORONIC ACID; 4-(2-METHOXYPHENYL)FURAN-2-BORONIC ACID; 4-(2-METHOXYPHENYL)THIOPHENE-2-BORONIC ACID; 4-(2-METHYL-1,3-DIOXOLAN-2-YL)PHENYLBORONIC ACID; 4-(2-METHYLTHIAZOL-5-YL)PHENYLBORONIC ACID; 4-(2-MORPHOLINOETHOXY)PHENYLBORONIC ACID, HCL; 4-(2-MORPHOLINOETHYL)PHENYLBORONIC ACID; 4-(2-MORPHOLINOETHYLCARBAMOYL)PHENYLBORONIC ACID; 4-(2-NITRO-4-(TRIFLUOROMETHYL)PHENOXY)PHENYLBORONIC ACID; 4-(2-NITROETHYL)PHENYLBORONIC ACID; 4-(2-NITROPHENOXY)BENZENEBORONIC ACID; 4-(2-O-THP-HYDROXY-ETHYL)-PHENYL-BORONIC ACID; 4-(2-OXO-2-(PROPYLAMINO)ETHYL)PHENYLBORONIC ACID; 4-(2-OXOIMIDAZOLIDIN-1-YL)PHENYLBORONIC ACID; 4-(2-OXOPYRROLIDIN-1-YL)PHENYLBORONIC ACID; 4-(2-OXOTETRAHYDROPYRIMIDIN-1(2H)-YL)PHENYLBORONIC ACID; 4-(2-PYRIDYL)PHENYLBORONIC ACID; 4-(2-TETRAHYDROPYRANYLOXY)PHENYLBORONIC ACID; 4-(2-THIAZOLYL)AMINOCARBONYLPHENYLBORONIC ACID; 4-(2-THIAZOLYL)THIOPHENE-2-BORONIC ACID; 4-(2-THIENYL)PHENYLBORONIC ACID; 4-(2-THIENYL)PYRIDINE-2-BORONIC ACID; 4-(2-TOLYL)FURAN-2-BORONIC ACID; 4-(2-TOLYL)THIOPHENE-2-BORONIC ACID; 4-(3-(2-ACETYLHYDRAZINYL)-3-OXOPROPYL)PHENYLBORONIC ACID; 4-(3-(DIMETHYLAMINO)PHENOXY)PHENYLBORONIC ACID; 4-(3-(ETHOXYCARBONYL)PIPERIDINE-1-CARBONYL)PHENYLBORONIC ACID; 4-(3'-(TRIFLUOROMETHYL)PHENOXYMETHYL)PHENYLBORONIC ACID; 4-(3,3-DIETHOXYPROPOXY)PHENYLBORONIC ACID; 4-(3,4,4-TRIFLUORO-BUT-3-EN-1-YL-OXY)-PHENYLBORONIC ACID; 4-(3,5-DIMETHOXYBENZYLOXY)PHENYLBORONIC ACID; 4-(3,7-DIMETHYLOCTYLOXY)BENZENEBORONIC ACID; 4-(3-CHLOROBENZYLAMINO)PHENYLBORONIC ACID; 4-(3'-CHLOROBENZYLOXY)-3,5-DIMETHYLPHENYLBORONIC ACID; 4-(3-CHLOROBENZYLOXY)PHENYLBORONIC ACID; 4-(3-CHLOROPHENOXY)-3-METHOXYPHENYLBORONIC ACID; 4-(3-CHLOROPHENOXYMETHYL)PHENYLBORONIC ACID; 4-(3-CHLOROPROPYLCARBAMOYL)BENZENEBORONIC ACID; 4-(3-ETHYLUREIDO)-3-METHOXYPHENYLBORONIC ACID; 4-(3-ETHYLUREIDO)PHENYLBORONIC ACID; 4-(3'-FLUOROBENZYLOXY)PHENYLBORONIC ACID; 4-(3-FLUOROPHENOXY)-2-METHYLPHENYLBORONIC ACID; 4-(3-FLUOROPHENOXY)-2-NITROPHENYLBORONIC ACID; 4-(3-FLUOROPHENYL)FURAN-2-BORONIC ACID; 4-(3-FLUOROPHENYL)THIOPHENE-2-BORONIC ACID; 4-(3-FLUOROPHENYLCARBAMOYL)PHENYLBORONIC ACID; 4-(3-FLUORO-PROPOXY)-BENZENEBORONIC ACID; 4-(3-HYDRAZINYL-3-OXOPROPYL)PHENYLBORONIC ACID; 4-(3-HYDROXYPROPYL)PHENYLBORONIC ACID; 4-(3-HYDROXYPROPYLCARBAMOYL)PHENYLBORONIC ACID; 4-(3-ISOPROPYL-2-OXOIMIDAZOLIDIN-1-YL)PHENYLBORONIC ACID; 4-(3-METHOXYPHENYL)FURAN-2-BORONIC ACID; 4-(3-METHOXYPHENYL)THIOPHENE-2-BORONIC ACID; 4-(3-METHOXYPROPOXY)PHENYLBORONIC ACID; 4-(3-METHOXYPROPYLCARBAMOYL)BENZENEBORONIC ACID; 4-(3-METHYL-2-OXOIMIDAZOLIDIN-1-YL)PHENYLBORONIC ACID; 4-(3-

METHYL-2-OXOTETRAHYDROPYRIMIDIN-1(2H)-YL)PHENYLBORONIC ACID; 4-(3-METHYLOXETAN-3-YL)METHOXYPHENYLBORONIC ACID; 4-(3-METHYLTHIOUREIDO)PHENYLBORONIC ACID; 4-(3-PROPYL-1,2,4-OXADIAZOL-5-YL)PHENYLBORONIC ACID; 4-(3-TOLYL)FURAN-2-BORONIC ACID; 4-(3-TOLYL)THIOPHENE-2-BORONIC ACID; 4-(4-(2-HYDROXYETHYL)PIPERAZINE-1-CARBONYL)PHENYLBORONIC ACID; 4-(4'-(2-PENTYLOXY)PHENYL)PHENYLBORONIC ACID; 4-(4-(BENZYLOXY)PHENOXY)PHENYLBORONIC ACID; 4-(4-(DIMETHYLAMINO)PIPERAZIN-1-YL)PHENYLBORONIC ACID; 4-(4-(TERT-BUTOXYCARBONYL)PIPERAZIN-1-YL)PHENYLBORONIC ACID; 4-(4,4,6-TRIMETHYL-1,3-DIOXAN-2-YL)PHENYLBORONIC ACID; 4-(4-BENZYLOXYPHENYL)BENZENEBORONIC ACID; 4-(4-BOC-PIPERAZINE-1-CARBONYL)PHENYLBORONIC ACID; 4-(4-BORONOPHENOXYMETHYL)BENZONITRILE; 4-(4-BUTYLCYCLOHEXYL)PHENYLBORONIC ACID; 4-(4-CHLORO-2-FLUOROBENZYL)PHENYLBORONIC ACID; 4-(4'-CHLOROBENZYLOXY)-3,5-DIMETHYLPHENYLBORONIC ACID; 4-(4'-CHLOROBENZYLOXY)PHENYLBORONIC ACID; 4-(4-CHLOROPHENOXYMETHYL)PHENYLBORONIC ACID; 4-(4-CHLOROPHENYLCARBAMOYL)PHENYLBORONIC ACID; 4-(4-ETHYLCYCLOHEXYL)-2-FLUOROPHENYLBORONIC ACID; 4-(4-ETHYLCYCLOHEXYL)PHENYLBORONIC ACID; 4-(4-FLUORO-2-NITROPHENOXY)PHENYLBORONIC ACID; 4-(4'-FLUOROBENZYLOXY)PHENYLBORONIC ACID; 4-(4-FLUOROPHENYL)FURAN-2-BORONIC ACID; 4-(4-FLUOROPHENYL)PHENYLBORONIC ACID; 4-(4-FLUOROPHENYL)THIOPHENE-2-BORONIC ACID; 4-(4'-ISOPENTYLOXYPHENYL)PHENYLBORONIC ACID; 4-(4'-ISOPROPOXYPHENYL)PHENYLBORONIC ACID; 4-(4'-METHOXYBENZYLOXY)PHENYLBORONIC ACID; 4-(4-METHOXYPHENYL)FURAN-2-BORONIC ACID; 4-(4-METHOXYPHENYL)THIOPHENE-2-BORONIC ACID; 4-(4-METHOXYPIPERIDIN-1-YL)PHENYLBORONIC ACID; 4-(4-METHYLBENZYLOXY)PHENYLBORONIC ACID; 4-(4-METHYLPIPERAZIN-1-YL)PHENYLBORONIC ACID; 4-(4-METHYLPIPERAZINE-1-CARBONYL)PHENYLBORONIC ACID, HCL; 4-(4-METHYL-PIPERAZINESULFONYL)PHENYL BORONIC ACID; 4-(4-METHYLPIPERIDINE-1-CARBONYL)PHENYLBORONIC ACID; 4-(4-NITROPHENOXY)PHENYLBORONIC ACID; 4-(4-PENTYLCYCLOHEXYL)PHENYLBORONIC ACID; 4-(4-PENTYLOXYPHENYL)BENZENEBORONIC ACID; 4-(4-PENTYLPHENYL)BENZENEBORONIC ACID; 4-(4'-PROPOXYPHENYL)PHENYLBORONIC ACID; 4-(4-TOLYL)FURAN-2-BORONIC ACID; 4-(4-TOLYL)THIOPHENE-2-BORONIC ACID; 4-(5-(ETHOXYMETHYL)-1,3,4-OXADIAZOL-2-YL)PHENYLBORONIC ACID; 4-(5-(METHOXYMETHYL)-1,3,4-OXADIAZOL-2-YL)PHENYLBORONIC ACID; 4-(5-(METHYLAMINO)-1,3,4-THIADIAZOL-2-YL)PHENYLBORONIC ACID; 4-(5-AMINO-1,3,4-THIADIAZOL-2-YL)PHENYLBORONIC ACID; 4-(5-BENZYLOXYPYRIMID-2-YL)PHENYLBORONIC ACID; 4-(5-METHYL-1,3,4-OXADIAZOL-2-YL)PHENYLBORONIC ACID; 4-(5-METHYLPYRIDIN-3-YL)PHENYLBORONIC ACID; 4-(5-OXOPYRAZOLIDIN-3-YL)PHENYLBORONIC ACID; 4-(5-PENTYLOXYPYRIMID-2-YL)PHENYLBORONIC ACID; 4-(5-PENTYLOXYTHIEN-2-YL)BENZENEBORONIC ACID; 4-(5-PENTYLPYRIMID-2-YL)PHENYLBORONIC ACID; 4-(5-PENTYLTHIEN-2-YL)BENZENEBORONIC ACID; 4-(5-PROPYL-1,3,4-OXADIAZOL-2-YL)PHENYLBORONIC ACID; 4-(5-TERT-BUTYL-1,3,4-OXADIAZOL-2-YL)PHENYLBORONIC ACID; 4-(6-METHOXYPYRIDIN-3-YL)PHENYLBORONIC ACID; 4-(9H-CARBOZOL-9-YL)PHENYLBORONIC ACID; 4-(9H-FLUOREN-9-YL)PHENYLBORONIC ACID; 4-(ACETAMIDOMETHYL)-3-METHOXYPHENYLBORONIC ACID; 4-(ACETOXYMETHYL)BENZENEBORONIC ACID; 4-(AMINOMETHYL)-3-FLUOROPHENYLBORONIC ACID, HCL; 4-(AMINOMETHYL)BENZENEBORONIC ACID; 4-(AZIRIDINE-1-CARBONYL)PHENYLBORONIC ACID; 4-(BENZYL(ETHYL)CARBAMOYL)PHENYLBORONIC ACID; 4-(BENZYL(METHYL)AMINO)PHENYLBORONIC ACID; 4-(BENZYL(METHYL)CARBAMOYL)PHENYLBORONIC ACID; 4-(BENZYLAMINO)PHENYLBORONIC ACID; 4-(BENZYLCARBAMOYL)-3-FLUOROBENZENEBORONIC ACID; 4-(BENZYLOXY)-2-(TRIFLUOROMETHYL)PHENYLBORONIC ACID; 4-(BENZYLOXY)-2,3-DIFLUOROPHENYLBORONIC ACID; 4-(BENZYLOXY)-2-CHLOROPHENYLBORONIC ACID; 4-(BENZYLOXY)-3-(TRIFLUOROMETHYL)PHENYLBORONIC ACID; 4-(BENZYLOXY)-3,5-DICHLOROPHENYLBORONIC ACID; 4-(BENZYLOXY)-3,5-DIMETHOXYPHENYLBORONIC ACID; 4-(BOC-AMINOMETHYL)PYRIDINE-3-BORONIC ACID; 4-(BUTYLAMINOCARBONYL)PHENYLBORONIC ACID; 4-(BUTYLCARBAMOYL)-3-FLUOROBENZENEBORONIC ACID; 4-(BUTYLSULFINYL)PHENYLBORONIC ACID; 4-(BUTYLSULFONAMIDO)PHENYLBORONIC ACID; 4-(BUTYLSULFONYL)PHENYLBORONIC ACID; 4-(CARBOXYMETHOXY)PHENYLBORONIC ACID; 4-(CYANOMETHYL)BENZENEBORONIC ACID; 4-(CYCLOBUTYL)FURAN-2-BORONIC ACID; 4-(CYCLOBUTYL)THIOPHENE-2-BORONIC ACID; 4-(CYCLOHEXYL(METHYL)CARBAMOYL)PHENYLBORONIC ACID; 4-(CYCLOHEXYL)FURAN-2-BORONIC ACID; 4-(CYCLOHEXYL)THIOPHENE-2-BORONIC ACID; 4-(CYCLOHEXYLAMINO)PHENYLBORONIC ACID; 4-(CYCLOHEXYLAMINOCARBONYL)PHENYLBORONIC ACID; 4-(CYCLOHEXYLCARBAMOYL)-3-FLUOROBENZENEBORONIC ACID; 4-(CYCLOHEXYLMETHOXY)PHENYLBORONIC ACID; 4-(CYCLOHEXYLOXY)METHYLPHENYLBORONIC ACID; 4-(CYCLOHEXYLSULFONYL)PHENYLBORONIC ACID; 4-(CYCLOPENTYL)FURAN-2-BORONIC ACID; 4-(CYCLOPENTYL)THIOPHENE-2-BORONIC ACID; 4-(CYCLOPENTYLAMINOCARBONYL)PHENYLBORONIC ACID; 4-(CYCLOPENTYLCARBAMOYL)-3-FLUOROBENZENEBORONIC ACID; 4-(CYCLOPROPANECARBOXAMIDO)PHENYLBORONIC ACID; 4-(CYCLOPROPANESULFONAMIDO)PHENYLBORONIC ACID; 4-(CYCLOPROPYL)FURAN-2-BORONIC ACID; 4-(CYCLOPROPYL)PYRIDINE-2-BORONIC ACID; 4-(CYCLOPROPYL)THIOPHENE-2-BORONIC ACID; 4-(CYCLOPROPYLAMINO)PHENYLBORONIC ACID; 4-(CYCLOPROPYLAMINOCARBONYL)PHENYLBORONIC ACID; 4-(CYCLOPROPYLMETHOXY)-2-FLUOROPHENYLBORONIC ACID; 4-(CYCLOPROPYLMETHOXY)BENZENEBORONIC ACID; 4-(CYCLOPROPYLMETHYLSULFINYL)PHENYLBO-

RONIC ACID; 4-(CYCLOPROPYLMETHYLSULFONYL)PHENYLBORONIC ACID; 4-(CYCLOPROPYLMETHYLTHIO)PHENYLBORONIC ACID; 4-(CYCLOPROPYLSULFINYL)PHENYLBORONIC ACID; 4-(CYCLOPROPYLSULFONYL)PHENYLBORONIC ACID; 4-(DIBENZYLAMINO)NAPHTHALEN-1-YLBORONIC ACID; 4-(DIBENZYLAMINO)PHENYLBORONIC ACID; 4-(DIETHYLAMINO)PHENYLBORONIC ACID; 4-(DIETHYLCARBAMOYL)-2-METHOXYBENZENEBORONIC ACID; 4-(DIETHYLCARBAMOYL)-3-FLUOROBENZENEBORONIC ACID; 4-(DIFLUOROMETHOXY)-2-FLUOROPHENYLBORONIC ACID; 4-(DIFLUOROMETHOXY)BENZOTHIAZOLE-2-BORONIC ACID; 4-(DIFLUOROMETHOXY)PHENYLBORONIC ACID; 4-(DIFLUOROMETHYL)-3-FLUOROPHENYLBORONIC ACID; 4-(DIHYDROXYBORANYL)-2,3-DIFLUOROBENZOIC ACID; 4-(DIHYDROXYBOROPHENYL)ACETYLENE; 4-(DIHYDROXYBORYL)-2-NITROBENZOIC ACID; 4-(DIHYDROXYBORYL)-3-METHOXYBENZOIC ACID; 4-(DIISOPROPYLCARBAMOYL)-2-ETHOXYPYRIDIN-3-YLBORONIC ACID; 4-(DIISOPROPYLCARBAMOYL)PHENYLBORONIC ACID; 4-(DIISOPROPYLCARBAMOYL)PYRIDIN-3-YLBORONIC ACID; 4-(DIMETHYLAMINO)-2-METHYLPHENYLBORONIC ACID; 4-(DIMETHYLAMINO)PHENYLBORONIC ACID; 4-(DIMETHYLCARBAMOYL)-2-(PROP-1-YNYL)PHENYLBORONIC ACID; 4-(DIMETHYLCARBAMOYL)-2-FLUOROPHENYLBORONIC ACID; 4-(DIMETHYLCARBAMOYL)-3-FLUOROBENZENEBORONIC ACID; 4-(DIPHENYLAMINO)PHENYLBORONIC ACID; 4-(DIPROPYLCARBAMOYL)PHENYLBORONIC ACID; 4-(ETHOXYCARBONYL)-1-(2-NITROPHENYL)-1H-PYRAZOL-5-YLBORONIC ACID; 4-(ETHOXYCARBONYL)-1-(3-FLUOROPHENYL)-1H-PYRAZOL-5-YLBORONIC ACID; 4-(ETHOXYCARBONYL)-1-(4-FLUOROPHENYL)-1H-PYRAZOL-5-YLBORONIC ACID; 4-(ETHOXYCARBONYL)-1-(4-NITROPHENYL)-1H-PYRAZOL-5-YLBORONIC ACID; 4-(ETHOXYCARBONYL)-1-(PYRAZIN-2-YL)-1H-PYRAZOL-5-YLBORONIC ACID; 4-(ETHOXYCARBONYL)-1-(PYRIDIN-2-YL)-1H-PYRAZOL-5-YLBORONIC ACID; 4-(ETHOXYCARBONYL)-1-(PYRIDIN-4-YL)-1H-PYRAZOL-5-YLBORONIC ACID; 4-(ETHOXYCARBONYL)-1-(PYRIMIDIN-2-YL)-1H-PYRAZOL-5-YLBORONIC ACID; 4-(ETHOXYCARBONYL)-2-FURANBORONIC ACID; 4-(ETHOXYCARBONYLDIFLUOROMETHYL)PHENYLBORONIC ACID; 4-(ETHOXY-D5)-PHENYLBORONIC ACID; 4-(ETHOXYMETHOXY)PHENYLBORONIC ACID; 4-(ETHOXYPHENYL-D9)-BORONIC ACID; 4-(ETHYL(METHYL)CARBAMOYL)PHENYLBORONIC ACID; 4-(ETHYLAMINO)-3-(TRIFLUOROMETHYL)PHENYLBORONIC ACID; 4-(ETHYLCARBAMOYL)-3-FLUOROBENZENEBORONIC ACID; 4-(ETHYL-D5)-PHENYLBORONIC ACID; 4-(ETHYLPHENYL-D9)-BORONIC ACID; 4-(ETHYLSULFONAMIDO)PHENYLBORONIC ACID; 4-(ETHYLSULFONYL)PHENYLBORONIC ACID; 4-(FURAN-2-YL)PHENYLBORONIC ACID; 4-(FURFURYLAMINOCARBONYL)PHENYLBORONIC ACID; 4-(HYDROXYIMINO)METHYLPHENYLBORONIC ACID; 4-(HYDROXYMETHYL)-3-(METHYLSULFONYL)PHENYLBORONIC ACID; 4-(HYDROXYMETHYL)NAPHTHALENE-1-BORONIC ACID; 4-(HYDROXYMETHYL)NAPHTHALENE-2-BORONIC ACID; 4-(HYDROXYMETHYL)PHENYLBORONIC ACID; 4-(HYDROXYMETHYL)THIOPHEN-3-YLBORONIC ACID; 4-(ISOBUTYLAMINOCARBONYL)PHENYLBORONIC ACID; 4-(ISOBUTYLSULFINYL)PHENYLBORONIC ACID; 4-(ISOBUTYLSULFONYL)PHENYLBORONIC ACID; 4-(ISOBUTYLTHIO)PHENYLBORONIC ACID; 4-(ISOPENTYLOXY)PHENYLBORONIC ACID; 4-(ISOPENTYLSULFINYL)PHENYLBORONIC ACID; 4-(ISOPENTYLSULFONYL)PHENYLBORONIC ACID; 4-(ISOPENTYLTHIO)PHENYLBORONIC ACID; 4-(ISOPROPOXYCARBONYL)-2-NITROPHENYLBORONIC ACID; 4-(ISOPROPOXYCARBONYLAMINO)PHENYLBORONIC ACID; 4-(ISO-PROPOXY-D7)-PHENYLBORONIC ACID; 4-(ISOPROPYL(METHYL)CARBAMOYL)PHENYLBORONIC ACID; 4-(ISOPROPYL)FURAN-2-BORONIC ACID; 4-(ISO-PROPYL)PYRIDINE-2-BORONIC ACID; 4-(ISO-PROPYL)THIOPHENE-2-BORONIC ACID; 4-(ISOPROPYLAMINO)-3-METHOXYPHENYLBORONIC ACID; 4-(ISOPROPYLAMINO)-5-(METHOXYCARBONYL)THIOPHEN-2-YLBORONIC ACID; 4-(ISOPROPYLAMINO)PHENYLBORONIC ACID; 4-(ISO-PROPYL-D7)-PHENYLBORONIC ACID; 4-(ISOPROPYLPHENYL-D11)-BORONIC ACID; 4-(ISOPROPYLSULFONYLPHENYL)BORONIC ACID; 4-(METHANESULFINYL)BENZENEBORONIC ACID; 4-(METHANESULFONYLAMINO)PHENYLBORONIC ACID; 4-(METHOXYCARBONYL)-1H-INDOL-2-YLBORONIC ACID; 4-(METHOXYCARBONYL)-3-(TRIFLUOROMETHOXY)PHENYLBORONIC ACID; 4-(METHOXYCARBONYL)-3-(TRIFLUOROMETHYL)PHENYLBORONIC ACID; 4'-(METHOXYCARBONYL)BIPHENYL-4-YLBORONIC ACID; 4-(METHOXYCARBONYL)NAPHTHALENE-1-BORONIC ACID; 4-(METHOXYCARBONYL)PYRIDINE-3-BORONIC ACID; 4-(METHOXYCARBONYLAMINO)BENZENEBORONIC ACID; 4-(METHOXY-D3)-PHENYL-BORONIC ACID; 4-(METHOXYMETHOXY)-3,5-DIMETHYLPHENYLBORONIC ACID; 4-(METHOXYMETHOXY)PHENYLBORONIC ACID; 4-(METHOXYMETHOXY)-2,6-DIMETHYLPHENYLBORONIC ACID; 4-(METHOXYMETHYL)PHENYLBORONIC ACID; 4-(METHOXYMETHYLTHIO)PHENYLBORONIC ACID; 4-(METHOXYPHENYL-D7)-BORONIC ACID; 4-(METHYL-D3)-2-(TRIFLUOROMETHYL)PHENYLBORONIC ACID; 4-(METHYL-D3)-PHENYLBORONIC ACID; 4-(METHYLSULFONYL)-2-(TRIFLUOROMETHYL)PHENYLBORONIC ACID; 4-(METHYLSULFONYL)PHENYLBORONIC ACID; 4-(METHYLSULFONYLOXY)PHENYLBORONIC ACID; 4-(METHYLTHIO)-1-(PHENYLSULFONYL)-1H-INDOL-2-YLBORONIC ACID; 4-(METHYLTHIO)-2-(TRIFLUOROMETHYL)PHENYLBORONIC ACID; 4-(METHYLTHIO)PHENYLBORONIC ACID; 4-(METHYLTHIOL-D3)-PHENYLBORONIC ACID; 4-(MORPHOLIN-1-YL)PHENYLBORONIC ACID HCL; 4-(MORPHOLINE-4-CARBONYL)PHENYLBORONIC ACID; 4-(MORPHOLINOMETHYL)PHENYLBORONIC ACID; 4-(MORPHOLINOSULFONYL)PHENYLBORONIC ACID; 4-(N-(1-METHYLPIPERIDIN-4-YL)SULFAMOYL)PHENYLBORONIC ACID; 4-(N-(2-(TBDMSO)ETHYL)SULFAMOYL)PHENYLBORONIC ACID; 4-(N-(3-CHLORO-2-METHYLPHENYL)SULFAMOYL)PHENYLBORONIC ACID; 4-(N-(3-CHLOROPHENYL)

SULFAMOYL)PHENYLBORONIC ACID; 4-(N-(3-CHLOROPROPYL)SULFAMOYL)PHENYLBORONIC ACID; 4-(N-(3-METHYLBUTANOYL)SULFAMOYL) PHENYLBORONIC ACID; 4-(N-(4-FLUORO-3-METHOXYPHENYL)SULFAMOYL)PHENYLBORONIC ACID; 4-(N-(4-HYDROXYCYCLOHEXYL) SULFAMOYL)PHENYLBORONIC ACID; 4-(N-(TERT-BUTOXYCARBONYL)METHYLSULFONAMIDO) PHENYLBORONIC ACID; 4-(N,N-BIS(4-METHOXYBENZYL)SULFAMOYL) PHENYLBORONIC ACID; 4-(N,N-DIETHYLAMINOCARBONYL)PHENYLBORONIC ACID; 4-(N,N-DIETHYLAMINOMETHYL)BENZENEBORONIC ACID; 4-(N,N-DIETHYLSULFAMOYL)-2-METHYLPHENYLBORONIC ACID; 4-(N,N-DIMETHYLAMINOCARBONYL)PHENYLBORONIC ACID; 4-(N,N-DIMETHYLSULFAMOYL)-2-METHYLPHENYLBORONIC ACID; 4-(N,N-DIMETHYLSULFAMOYL)PHENYLBORONIC ACID; 4-(N,O-DIMETHYLHYDROXYLAMINOCARBONYL)PHENYLBORONIC ACID; 4-(N-ACETYLSULFAMOYL)PHENYLBORONIC ACID; 4-(NAPHTHALEN-1-YL)PHENYLBORONIC ACID; 4-(NAPHTHALEN-2-YL)PHENYLBORONIC ACID; 4-(NAPHTHALENE-2-YL)-1-NAPHTHALENE BORONIC ACID; 4-(N-BENZYLAMINOCARBONYL) PHENYLBORONIC ACID; 4-(N-BENZYL-N-(4-METHOXYBENZYL)SULFAMOYL)PHENYLBORONIC ACID; 4-(N-BENZYLSULPHONAMIDO)BENZENEBORONIC ACID; 4-(N-BUTOXYCARBONYL)AMINOPHENYLBORONIC ACID; 4-(N-BUTYL-N-(4-METHOXYBENZYL)SULFAMOYL)PHENYLBORONIC ACID; 4-(N-BUTYLSULPHONAMIDO)BENZENEBORONIC ACID; 4-(N-CYCLOHEXYL-N-(4-METHOXYBENZYL)SULFAMOYL) PHENYLBORONIC ACID; 4-(N-CYCLOHEXYL-N-METHYLSULFAMOYL)PHENYLBORONIC ACID; 4-(N-CYCLOHEXYLSULPHONAMIDO)BENZENEBORONIC ACID; 4-(N-CYCLOPENTYLSULFAMOYL) PHENYLBORONIC ACID; 4-(N-CYCLOPROPYLSULFAMOYL)-2-METHYLPHENYLBORONIC ACID; 4-(N-CYCLOPROPYLSULFAMOYL)PHENYLBORONIC ACID; 4-(NEOPENTYLOXY)PHENYLBORONIC ACID; 4-(NEOPENTYLOXYSULFONYL)PHENYLBORONIC ACID; 4-(N-ETHYLAMINOCARBONYL)PHENYLBORONIC ACID; 4-(N-ETHYLSULFAMOYL)-2-METHYLPHENYLBORONIC ACID; 4-(N-ETHYLSULPHONAMIDO)BENZENEBORONIC ACID; 4-(N'-HYDROXYCARBAMIMIDOYL)BENZENEBORONIC ACID; 4-(N-ISOBUTYRYLSULFAMOYL)PHENYLBORONIC ACID; 4-(N-ISOPROPYLAMINOCARBONYL) PHENYLBORONIC ACID; 4-(N-ISOPROPYL-N-(4-METHOXYBENZYL)SULFAMOYL) PHENYLBORONIC ACID; 4-(N-ISOPROPYLSULFAMOYL)-2-METHYLPHENYLBORONIC ACID; 4-(N-ISOPROPYLSULFAMOYL)PHENYLBORONIC ACID; 4-(N-METHYLAMINOCARBONYL)-2-FLUOROPHENYLBORONIC ACID; 4-(N-METHYLAMINOCARBONYL)PHENYLBORONIC ACID; 4-(N-METHYL-N-(1-METHYLPIPERIDIN-4-YL)SULFAMOYL) PHENYLBORONIC ACID; 4-(N-METHYL-N-(4-METHOXYBENZYL)SULFAMOYL) PHENYLBORONIC ACID; 4-(N-METHYLSULFAMOYLMETHYL)PHENYLBORONIC ACID; 4-(N-NAPHTHALEN-1-YLSULFAMOYL)PHENYLBORONIC ACID; 4-(N-NONYLOXY)BENZENEBORONIC ACID; 4-(N-OCTYL)BENZENEBORONIC ACID; 4-(N-PIPERIDIN-4-YLSULFAMOYL)PHENYLBORONIC ACID; 4-(N-PROPIONYLSULFAMOYL)PHENYLBORONIC ACID; 4-(N-PROPYLAMINOCARBONYL)PHENYLBORONIC ACID; 4-(O-METHYLHYDROXYLAMINOCARBONYL) PHENYLBORONIC ACID; 4-(OXAZOL-5-YL) PHENYLBORONIC ACID; 4-(PENTAN-3-YLOXY) PHENYLBORONIC ACID; 4-(PHENETHYLCARBAMOYL)PHENYLBORONIC ACID; 4-(PHENOXYMETHYL)PHENYLBORONIC ACID; 4-(PIPERIDIN-1-YLMETHYL)PHENYLBORONIC ACID; 4-(PIPERIDIN-1-YLSULFONYL)PHENYLBORONIC ACID; 4-(PIPERIDIN-4-YLSULFONYL) PHENYLBORONIC ACID; 4-(PIPERIDINE-1-CARBONYL)PHENYLBORONIC ACID; 4-(PIPERIDINO)PHENYLBORONIC ACID; 4-(PIPERIDINO)PHENYLBORONIC ACID HCL; 4-(PROP-1-YNYL)PYRIDIN-3-YLBORONIC ACID; 4-(PROP-2-YNYL)PHENYLBORONIC ACID; 4-(PROPYLSULFONYL)PHENYLBORONIC ACID; 4-(PYRIDIN-2-YL-AMINOCARBONYL)BENZENEBORONIC ACID; 4-(PYRIDIN-2-YLMETHOXY)PHENYLBORONIC ACID; 4-(PYRIDIN-2-YLOXY)PHENYLBORONIC ACID; 4-(PYRIDIN-3-YLMETHOXY) PHENYLBORONIC ACID; 4-(PYRIDIN-4-YL)PHENYL BORONIC ACID; 4-(PYRIDIN-4-YLAMINO)PHENYLBORONIC ACID; 4-(PYRIDIN-4-YLMETHOXY)PHENYLBORONIC ACID; 4-(PYRIDIN-4-YLOXY)PHENYLBORONIC ACID; 4-(PYRIDINE-3-YL) PHENYLBORONIC ACID; 4-(PYRROLIDINE-1-CARBONYL)PHENYLBORONIC ACID; 4-(PYRROLIDINO)PHENYLBORONIC ACID HCL; 4-(PYRROLIDINYLSULFONYL)PHENYLBORONIC ACID; 4-(T-BOC-(PHENYL)AMINO)PHENYLBORONIC ACID; 4-(TERT-BUTOXY)PYRIDINE-2-BORONIC ACID; 4-(TERT-BUTOXYCARBONYL)-2,3,4,5-TETRAHYDROBENZO[F][1,4]OXAZEPIN-7-YLBORONIC ACID; 4-(TERT-BUTOXYCARBONYL)-3-METHYLPHENYLBORONIC ACID; 4-(TERT-BUTOXYCARBONYL)PHENYLBORONIC ACID; 4-(TERT-BUTOXYCARBONYLAMINO)-2,6-DIMETHYLPHENYLBORONIC ACID; 4-(TERT-BUTOXYCARBONYL-ISOPROPYLAMINO)-BENZENEBORONIC ACID; 4(TERT-BUTOXYCARBONYL-N-METHYLAMINO)-PHENYLBORONIC ACID; 4-(TERT-BUTYL) PYRIDINE-2-BORONIC ACID; 4-(TERT-BUTYLAMINOCARBONYL)PHENYLBORONIC ACID; 4-(TERT-BUTYLAMINOSULPHONYL)BENZENEBORONIC ACID; 4-(TERT-BUTYLCARBAMOYL)-3-FLUOROBENZENEBORONIC ACID; 4-(TERT-BUTYLDIMETHYLSILYLOXY)-2-(PROP-1-YNYL)PHENYLBORONIC ACID; 4-(TERT-BUTYLDIMETHYLSILYLOXY)-3,5-DICHLOROPHENYLBORONIC ACID; 4-(TERT-BUTYLDIMETHYLSILYLOXY)-3-METHOXYPHENYLBORONIC ACID; 4-(TERT-BUTYLDIMETHYLSILYLOXY)CYCLOHEX-1-ENYLBORONIC ACID; 4-(TERT-BUTYLDIMETHYLSILYLOXY)PHENYLBORONIC ACID; 4-(TERT-BUTYLTHIO)PHENYLBORONIC ACID; 4-(TETRAHYDRO-2H-PYRAN-2-YL) METHOXYPHENYLBORONIC ACID; 4-(TETRAHYDRO-2H-PYRAN-2-YLSULFANYL)PHENYLBORONIC ACID; 4-(TETRAHYDRO-2H-PYRAN-4-YL) METHOXYPHENYLBORONIC ACID; 4-(TETRAHYDROPYRAN-4-YLOXYMETHY)PHENYLBORONIC ACID; 4-(TETRAZOL-5-YL)PHENYL-

BORONIC ACID; 4-(THIAZOL-2-YL)FURAN-2-BORONIC ACID; 4-(THIAZOLINE-3-CARBONYL)PHENYLBORONIC ACID; 4-(THIOMORPHOLIN-4-YLCARBONYL)BENZENEBORONIC ACID; 4-(THIOMORPHOLINYLSULFONYL)PHENYLBORONIC ACID; 4-(THIOPHEN-2-YLCARBAMOYL)PHENYLBORONIC ACID; 4-(TOLYL-D7)-BORONIC ACID; 4-(TRANS-4-BUTYLCYCLOHEXYL)PHENYLBORONIC ACID; 4-(TRANS-4-ETHYLCYCLOHEXYL)PHENYLBORONIC ACID; 4-(TRANS-4-HYDROXYCYCLOHEXYLCARBAMOYL)PHENYLBORONIC ACID; 4-(TRANS-4-PENTYLCYCLOHEXYL)PHENYLBORONIC ACID; 4-(TRIFLUOROMETHOXY)PHENYLBORONIC ACID; 4-(TRIFLUOROMETHYL)-2-(1,2,4-OXADIAZOL-3-YL)PHENYLBORONIC ACID; 4-(TRIFLUOROMETHYL)-2-(2-(TRIFLUOROMETHYL)PHENYL)PYRIDINE-3-BORONIC ACID; 4-(TRIFLUOROMETHYL)-2-(3-(TRIFLUOROMETHYL)PHENYL)PYRIDINE-3-BORONIC ACID; 4-(TRIFLUOROMETHYL)-2-(4-(TRIFLUOROMETHYL)PHENYL)PYRIDINE-3-BORONIC ACID; 4-(TRIFLUOROMETHYL)-2-(TRIMETHYLSILYL)PHENYLBORONIC ACID; 4-(TRIFLUOROMETHYL)-2-FURANBORONIC ACID; 4-(TRIFLUOROMETHYL)-2-THIOPHENEBORONIC ACID; 4'-(TRIFLUOROMETHYL)-4-BIPHENYLBORONIC ACID; 4-(TRIFLUOROMETHYL)CYCLOHEX-1-ENYLBORONIC ACID; 4-(TRIFLUOROMETHYL)PHENYLBORONIC ACID; 4-(TRIFLUOROMETHYL)PYRIDINE-2-BORONIC ACID; 4-(TRIFLUOROMETHYL)PYRIDINE-3-BORONIC ACID; 4-(TRIFLUOROMETHYL)PYRIDINE-3-BORONIC ACID HYDRATE; 4-(TRIFLUOROMETHYL)PYRIMIDINE-5-BORONIC ACID; 4-(TRIFLUOROMETHYLTHIO)-BENZENEBORONIC ACID; 4-(TRIFLUOROVINYLOXYPHENYL) BORONIC ACID; 4-(TRIISOPROPYLSILYLOXY)PHENYL BORONIC ACID; 4-(TRIMETHYLAMMONIUM)METHYLPHENYLBORONIC ACID BROMIDE SALT; 4-(TRIMETHYLAMMONIUM)METHYLPHENYLBORONIC ACID IODIDE SALT; 4-(TRIMETHYLSILYL)THIOPHEN-2-YLBORONIC ACID; 4,4-DIMETHYL-2-OXO-2,4-DIHYDRO-1H-BENZO[D][1,3]OXAZIN-6-YLBORONIC ACID; 4,4-DIMETHYLCYCLOHEXEN-1-YLBORONIC ACID; 4,5,6,7-TETRAHYDRO-3-PYRAZOLO[1,5-A]PYRIDINE BORONIC ACID; 4,5,6,7-TETRAHYDROTHIENO[3,2-C]PYRIDIN-2-YL BORONIC ACID; 4,5-BIS(BENZYLOXY)-2-CHLOROPHENYLBORONIC ACID; 4,5-DICHLORO-2-(2-METHOXYETHOXY)PHENYLBORONIC ACID; 4,5-DICHLORO-2-METHOXYPHENYLBORONIC ACID; 4,5-DICHLOROPYRIDINE-3-BORONIC ACID; 4,5-DICHLOROTHIOPHEN-2-YLBORONIC ACID; 4,5-DIFLUORO-2-ETHOXYPHENYLBORONIC ACID; 4,5-DIFLUORO-2-ISOPROPOXYPHENYLBORONIC ACID; 4,5-DIFLUORO-2-METHOXYPHENYLBORONIC ACID; 4,5-DIFLUORO-2-METHYLPHENYLBORONIC ACID; 4,5-DIFLUORO-2-NITROPHENYLBORONIC ACID; 4,5-DIMETHOXY-2-(METHOXYCARBONYL)PHENYLBORONIC ACID; 4,5-DIMETHYLPYRIDINE-2-BORONIC ACID; 4,5-DIMETHYLPYRIDINE-3-BORONIC ACID; 4,6-DICHLORO-PYRIDINE-2-BORONIC ACID; 4,6-DICHLOROPYRIDINE-3-BORONIC ACID; 4,6-DICHLOROPYRIMIDIN-2-YLBORONIC ACID; 4,6-DIMETHOXYBENZOFURAN-2-YLBORONIC ACID; 4,6-DIMETHOXYPYRIDINE-3-BORONIC ACID; 4,6-DIMETHOXYPYRIMIDIN-5-YLBORONIC ACID; 4,6-DIMETHYLPYRIDINE-2-BORONIC ACID; 4,6-DIMETHYLPYRIDINE-3-BORONIC ACID; 4-[(1,1-DIMETHYLETHOXY)CARBONYL]PHENYLMETHYL)AMINOPHENYLBORONIC ACID; 4-[(2,3-DIFLUOROPHENYL)METHOXY]PHENYLBORONIC ACID; 4-[(2,3-DIMETHYLPHENYL)CARBAMOYL]BENZENEBORONIC ACID; 4-[(2,4-DIMETHYLPHENYL)CARBAMOYL]BENZENEBORONIC ACID; 4-[(2,5-DIMETHYLPHENYL)CARBAMOYL]BENZENEBORONIC ACID; 4-[(2',6'-DIISOPROPYLPHENOXY)METHYL]PHENYLBORONIC ACID; 4-[(2-CHLORO-4-METHYLPHENYL)CARBAMOYL]BENZENEBORONIC ACID; 4-[(2'-CHLORO-5'-(TRIFLUOROMETHYL)PHENOXY)METHYL]PHENYLBORONIC ACID; 4-[(2-FLUOROPHENYL)CARBAMOYL]BENZENEBORONIC ACID; 4-[(2-HYDROXYETHYL)THIO]PHENYLBORONIC ACID; 4-[(2-ISOPROPYL-5-METHYLPHENOXY)METHYL]PHENYLBORONIC ACID; 4-[(2-PIPERIDIN-1-YLETHYL)CARBAMOYL]BENZENEBORONIC ACID HYDROCHLORIDE; 4-[(2-PYRROLIDIN-1-YLETHYL)CARBAMOYL]BENZENEBORONIC ACID HYDROCHLORIDE; 4-[(3-CHLORO-4-METHYLPHENYL)CARBAMOYL]BENZENEBORONIC ACID; 4-[(3-ETHOXY-3-OXOPROPYL)CARBAMOYL]BENZENEBORONIC ACID; 4-[(4'-(2-METHOXYETHYL)PHENOXY)METHYL]PHENYLBORONIC ACID; 4-[(4'-CHLORO-1-NAPHTHYLOXY)METHYL]PHENYLBORONIC ACID; 4-[(4-FLUOROPHENYL)AMINOCARBONYL]BENZENEBORONIC ACID; 4-[(4-METHOXYBENZYL)SULPHAMOYL]BENZENEBORONIC ACID; 4-[(4-TERT-BUTYL-2-METHYLPHENOXY)METHYL]PHENYLBORONIC ACID; 4-[(BENZYLOXY)METHYL]PYRIDINE-2-BORONIC ACID; 4-[(FURAN-2-YLMETHOXY)METHYL]PHENYLBORONIC ACID; 4-[(METHYLSULFONYL)METHYL]PHENYLBORONIC ACID; 4-[(THIEN-2-YLMETHOXY)METHYL]BENZENEBORONIC ACID; 4-[4'-(3-PENTYLOXY)PHENYL]PHENYLBORONIC ACID; 4-[4'-(TRIFLUOROMETHOXY)PHENOXYMETHYL]PHENYLBORONIC ACID; 4-[5-(4-DIMETHYLAMINOPHENYL)OXAZOL-2-YL]PHENYLBORONIC ACID; 4-[N-CYCLOPROPYL-N-(4-METHOXYBENZYL)SULFAMOYL]PHENYLBORONIC ACID; 4-[N-ETHYL-N-(4-METHOXYBENZYL)SULPHAMOYL]BENZENEBORONIC ACID; 4-[TERT-BUTYL(4-METHOXYBENZYL)SULPHAMOYL]BENZENEBORONIC ACID; 4-ACETAMIDO-2-CYANOPHENYLBORONIC ACID; 4-ACETAMIDO-2-METHYLPHENYLBORONIC ACID; 4-ACETAMIDO-3-(TRIFLUOROMETHYL)PHENYLBORONIC ACID; 4-ACETAMIDO-3-CYANOPHENYLBORONIC ACID; 4-ACETAMIDO-3-METHOXYPHENYLBORONIC ACID; 4-ACETAMIDOPHENYLBORONIC ACID; 4-ACETOXY-3-NITROPHENYLBORONIC ACID; 4-ACETOXYBENZENEBORONIC ACID; 4-ALLYLOXY PHENYL BORONIC ACID; 4-AMINO-3-CYANO-2-(TRIFLUOROMETHYL)QUINOLIN-6-YLBORONIC ACID; 4-AMINO-3-FLUOROBENZENEBORONIC ACID, N-CBZ PROTECTED; 4-AMINO-3-FLUOROPHENYLBORONIC ACID; 4-AMINO-3-FLUOROPHENYLBORONIC ACID HYDROCHLORIDE; 4-AMINO-3-NITROPHENYLBORONIC ACID; 4-AMINO-6-METHOXYPYRIDIN-2-YLBORONIC ACID; 4-AMINO-6-METHYLPYRIDINE-3-BORONIC ACID; 4-AMINOBENZYLBORONIC ACID; 4-AMINOCARBO-

NYLPHENYLBORONIC ACID; 4-AMINOMETH-YLPHENYLBORONIC ACID HYDROCHLORIDE; 4-AMINOPHENYLBORONIC ACID; 4-AMINOPHE-NYLBORONIC ACID HYDROCHLORIDE; 4-AMINO-PYRIDIN-3-YLBORONIC ACID; 4-AMINOPYRIDINE-2-BORONIC ACID; 4-BENZAMIDOPHENYLBORONIC ACID; 4-BENZOFURANYL-BORONIC ACID; 4-BEN-ZYLOXY-1H-INDOLE-BORONIC ACID; 4-BENZY-LOXY-1-TERT-BUTOXYCARBONYLINDOLE-2-BO-RONIC ACID; 4-BENZYLOXY-2,5-DIMETHOXYPHENYLBORONIC ACID; 4-BENZYLOXY-2,6-DIFLUOROPHENYLBORONIC ACID; 4-BENZYLOXY-2-DIMETHYLAMINO-PYRIMI-DINE-5-BORONIC ACID; 4-BENZYLOXY-2-FLUORO-PHENYLBORONIC ACID; 4-BENZYLOXY-2-METH-YLPHENYLBORONIC ACID; 4-BENZYLOXY-2-PIPERIDINE-1-YL-PYRIMIDINE-5-BORONIC ACID; 4-BENZYLOXY-3,5-DIFLUOROPHENYLBORONIC ACID; 4-BENZYLOXY-3,5-DIMETHYLPHENYLBO-RONIC ACID; 4-BENZYLOXY-3-CHLORO-5-METH-YLPHENYLBORONIC ACID; 4-BENZYLOXY-3-CHLO-ROPHENYLBORONIC ACID; 4-BENZYLOXY-3-FLUOROPHENYLBORONIC ACID; 4-BENZYLOXY-3-METHOXYBENZENEBORONIC ACID; 4-BENZYLOXY-3-METHYLPHENYLBORONIC ACID; 4'-BENZYLOXYCARBONYLAMINO-BIPHENYL-4-BORONIC ACID; 4-BENZYLOXYCARBONYLPHE-NYLBORONIC ACID; 4-BENZYLOXYPHENYLBO-RONIC ACID; 4-BENZYLTHIOPHENYLBORONIC ACID; 4-BIPHENYLBORONIC ACID; 4'-BORONIC ACID-BIPHENYL-3-CARBOXYLIC ACID METHYL ESTER; 4-BORONO-2-(CYCLOHEXYLOXY)BENZOIC ACID; 4-BORONO-2-(TRIFLUOROMETHYL)BENZOIC ACID; 4-BORONO-2-ISOBUTYLBENZOIC ACID; 4-BORONO-3,5-DIFLUOROBENZOIC ACID; 4-BO-RONO-3-FLUOROTHIOANISOLE; 4-BORONO-5-FLUORO-2-METHOXYBENZOIC ACID; 4-BORONO-BENZENESULFONIC ACID; 4-BORONOBENZOHYDRAZIDE; 4-BORONO-DL-PHE-NYLALANINE; 4-BORONO-DL-PHENYLALANINE B10 ENRICHED; 4-BORONO-D-PHENYLALANINE; 4-BORONO-D-PHENYLALANINE B10 ENRICHED; 4-BORONO-L-PHENYLALANINE; 4-BORONO-L-PHE-NYLALANINE B10 ENRICHED; 4-BORONONICO-TINIC ACID; 4-BORONOPYRIDINE 1-OXIDE; 4-BU-TOXY-2,3,5,6-TETRAFLUOROPHENYLBORONIC ACID; 4-BUTOXY-2-METHYLPHENYLBORONIC ACID; 4-BUTOXY-3,5-DIMETHYLPHENYLBORONIC ACID; 4-BUTOXY-3-CHLOROPHENYLBORONIC ACID; 4-BUTOXY-3-FLUOROPHENYLBORONIC ACID; 4-BUTOXYPHENYLBORONIC ACID; 4'-BUTYL-3-FLUOROBIPHENYL-4-BORONIC ACID; 4'-BUTYL-4-BIPHENYLBORONIC ACID; 4-BUTYLPHENYLBORONIC ACID; 4-BUTYLPYRIMI-DINE-5-BORONIC ACID; 4-BUTYLTHIOPHENYLBO-RONIC ACID; 4-CARBAMOYL-2-FLUOROBENZEN-EBORONIC ACID; 4-CARBAMOYL-3-CHLOROPHENYLBORONIC ACID; 4-CARBAMOYL-3-FLUOROPHENYLBORONIC ACID; 4-CARBOXY-2,6-DICHLOROPHENYLBORONIC ACID; 4-CARBOXY-2-CHLOROPHENYLBORONIC ACID; 4-CARBOXY-2-FLUOROPHENYLBORONIC ACID; 4-CARBOXY-2-NITROPHENYLBORONIC ACID; 4-CARBOXY-3-CHLOROPHENYLBORONIC ACID; 4-CARBOXY-3-FLUOROPHENYLBORONIC ACID; 4-CARBOXY-6-CHLOROPYRIDINE-3-BORONIC ACID; 4-CARBOXYNAPHTHALENE-1-BORONIC ACID; 4-CARBOXYPHENYLBORONIC ACID; 4-CHLORO-1-(2,2-DIFLUOROETHYL)-PYRROL-3-YLBORONIC ACID; 4-CHLORO-1-(2-METHOXYETHYL)-PYRROL-3-YLBORONIC ACID; 4-CHLORO-1-(CYCLOPROPYL-METHYL)-PYRROL-3-YLBORONIC ACID; 4-CHLORO-1-(METHYLSULFONYL)-PYRROL-3-YL-BORONIC ACID; 4-CHLORO-1-(TRIISOPROPYLSI-LYL)-PYRROL-3-YLBORONIC ACID; 4-CHLORO-1-(TRIMETHYLSILYL)-PYRROL-3-YLBORONIC ACID; 4-CHLORO-1-CYCLOPENTYL-PYRROL-3-YLBO-RONIC ACID; 4-CHLORO-1-ETHYL-PYRROL-3-YL-BORONIC ACID; 4-CHLORO-1H-INDOLE-2-BORONIC ACID; 4-CHLORO-1-ISOPROPYL-PYRROL-3-YLBO-RONIC ACID; 4-CHLORO-1-METHYL-1H-INDOL-2-YLBORONIC ACID; 4-CHLORO-1-METHYL-1H-PYR-ROLE-2-BORONIC ACID; 4-CHLORO-1-METHYL-PYRROL-3-YLBORONIC ACID; 4-CHLORO-1-PHENYL-PYRROL-3-YLBORONIC ACID; 4-CHLORO-2-((TETRAHYDRO-2H-PYRAN-2-YL)METHOXY) PHENYLBORONIC ACID; 4-CHLORO-2-(2-METHOXYETHOXY)PHENYLBORONIC ACID; 4-CHLORO-2-(CYCLOPENTYLOXY)PHENYLBO-RONIC ACID; 4-CHLORO-2-(METHOXYMETHYL) PHENYLBORONIC ACID; 4-CHLORO-2-(PIPERIDIN-1-YL)PHENYLBORONIC ACID; 4-CHLORO-2-(TRIFLUOROMETHOXY)PHENYLBORONIC ACID; 4-CHLORO-2-(TRIFLUOROMETHYL)PHENYLBO-RONIC ACID; 4-CHLORO-2,3-DIFLUOROPHENYLBO-RONIC ACID; 4-CHLORO-2,5-DIFLUOROPHENYLBO-RONIC ACID; 4-CHLORO-2,6-DIFLUOROPHENYLBORONIC ACID; 4-CHLORO-2,6-DIMETHOXYPHENYLBORONIC ACID; 4-CHLORO-2,6-DIMETHYLPYRIDINE-3-BORONIC ACID; 4-CHLORO-2-CYANOPHENYLBORONIC ACID; 4-CHLORO-2-ETHOXYPHENYLBORONIC ACID; 4-CHLORO-2-FLUORO-3-(2-METHOXYETHOXY) PHENYLBORONIC ACID; 4-CHLORO-2-FLUORO-3-(METHOXYCARBONYL)PHENYLBORONIC ACID; 4-CHLORO-2-FLUORO-3-ISOPROPOXYPHENYLBO-RONIC ACID; 4-CHLORO-2-FLUORO-3-METHOXY-PHENYLBORONIC ACID; 4-CHLORO-2-FLUORO-3-PROPOXYPHENYLBORONIC ACID; 4-CHLORO-2-FLUORO-5-METHOXYPHENYLBORONIC ACID; 4-CHLORO-2-FLUOROPHENYLBORONIC ACID; 4-CHLORO-2-FURANBORONIC ACID; 4-CHLORO-2-HYDROXY-6-METHYLPHENYLBORONIC ACID; 4-CHLORO-2-HYDROXYPHENYLBORONIC ACID; 4-CHLORO-2-ISOBUTOXYPHENYLBORONIC ACID; 4-CHLORO-2-ISOPROPOXYPHENYLBORONIC ACID; 4-CHLORO-2-METHOXYPHENYLBORONIC ACID; 4-CHLORO-2-METHOXYPYRIDINE-3-BORONIC ACID; 4-CHLORO-2-METHOXYPYRIDINE-5-BO-RONIC ACID; 4-CHLORO-2-METHYLPHENYLBO-RONIC ACID; 4-CHLORO-2-METHYLPYRIDINE-3-BORONIC ACID; 4-CHLORO-2-METHYLPYRIDINE-5-BORONIC ACID; 4-CHLORO-2-PROPOXYPHENYLBORONIC ACID; 4-CHLORO-3-(1,1,1-TRIFLUORO-2-METHYLPROPAN-2-YLOXY) PHENYLBORONIC ACID; 4-CHLORO-3-(2-DIMETHYLAMINOETHOXY)PHENYLBORONIC ACID; 4-CHLORO-3-(2-METHOXYETHOXY)PHENYL-BORONIC ACID; 4-CHLORO-3-(CYCLOHEXYLAMI-NOCARBONYL)PHENYLBORONIC ACID; 4-CHLORO-3-(CYCLOPROPYLCARBAMOYL)PHE-NYLBORONIC ACID; 4-CHLORO-3-(DIMETHYLAMI-NOCARBONYL)PHENYLBORONIC ACID; 4-CHLORO-3-(ETHOXYCARBONYL)PHENYLBO-

RONIC ACID; 4-CHLORO-3-(ETHYLCARBAMOYL)PHENYLBORONIC ACID; 4-CHLORO-3-(ISOPROPYLCARBAMOYL)PHENYLBORONIC ACID; 4-CHLORO-3-(METHOXYCARBONYL)PHENYLBORONIC ACID; 4-CHLORO-3-(N,N-DIETHYLCARBAMOYL)PHENYLBORONIC ACID; 4-CHLORO-3-(N-BUTYLAMINOCARBONYL)PHENYLBORONIC ACID; 4-CHLORO-3-(N-METHYLCARBAMOYL)PHENYLBORONIC ACID; 4-CHLORO-3-(N-MORPHOLINECARBONYL)PHENYLBORONIC ACID; 4-CHLORO-3-(N-PROPYLAMINOCARBONYL)PHENYLBORONIC ACID; 4-CHLORO-3-(PIPERIDINE-1-CARBONYL)PHENYLBORONIC ACID; 4-CHLORO-3-(PYRROLIDINE-1-CARBONYL)PHENYLBORONIC ACID; 4-CHLORO-3-(T-BUTYLCARBAMOYL)PHENYLBORONIC ACID; 4-CHLORO-3-(TRIFLUOROMETHOXY)PHENYLBORONIC ACID; 4-CHLORO-3-(TRIFLUOROMETHYL)PHENYLBORONIC ACID; 4-CHLORO-3-CYANOPHENYLBORONIC ACID; 4-CHLORO-3-ETHOXY-2-FLUOROPHENYLBORONIC ACID; 4-CHLORO-3-ETHOXYPHENYLBORONIC ACID; 4-CHLORO-3-ETHYLPHENYLBORONIC ACID; 4-CHLORO-3-FLUOROPHENYLBORONIC ACID; 4-CHLORO-3-ISOBUTOXYPHENYLBORONIC ACID; 4-CHLORO-3-ISOPROPOXYPHENYLBORONIC ACID; 4-CHLORO-3-METHOXYPHENYLBORONIC ACID; 4-CHLORO-3-METHOXYPYRIDINE-2-BORONIC ACID; 4-CHLORO-3-METHYLPHENYLBORONIC ACID; 4-CHLORO-3-METHYLPYRIDINE-2-BORONIC ACID; 4-CHLORO-3-NITROPHENYLBORONIC ACID; 4-CHLORO-3-PROPOXYPHENYLBORONIC ACID; 4'-CHLORO-4-BIPHENYLBORONIC ACID; 4-CHLORO-5-(METHOXYCARBONYL)THIOPHENE-2-BORONIC ACID; 4-CHLORO-5-METHOXYPYRIDINE-2-BORONIC ACID; 4-CHLORO-5-METHOXYPYRIDINE-3-BORONIC ACID; 4-CHLORO-5-METHYLPYRIDINE-2-BORONIC ACID; 4-CHLORO-5-METHYLPYRIDINE-3-BORONIC ACID; 4-CHLORO-6-(TRIFLUOROMETHYL)PYRIDIN-2-YLBORONIC ACID; 4-CHLORO-6-METHOXYPYRIDIN-2-YLBORONIC ACID; 4-CHLOROCARBONYL-3-FLUOROPHENYLBORONIC ACID; 4-CHLOROCARBONYLPHENYLBORONIC ACID; 4-CHLOROMETHYLPHENYLBORONIC ACID; 4-CHLORO-N-(BOC)-INDOLE-2-BORONIC ACID; 4-CHLOROPHENYLBORONIC ACID; 4-CHLOROPYRIDINE-2-BORONIC ACID; 4-CHLOROPYRIDINE-3-BORONIC ACID; 4-CHLOROPYRIDINE-3-BORONIC ACID, HCL; 4-CHLOROPYRIMIDINE-2-BORONIC ACID; 4-CHLOROPYRIMIDINE-5-BORONIC ACID; 4-CHLORO-PYRROL-3-YLBORONIC ACID; 4-CHLOROQUINOLINE-3-BORONIC ACID; 4-CHLOROTHIOPHEN-2-YLBORONIC ACID; 4-CYANO-1H-INDOL-2-YLBORONIC ACID; 4-CYANO-2,3-DIFLUOROPHENYLBORONIC ACID; 4-CYANO-2,5-DIFLUOROPHENYLBORONIC ACID; 4-CYANO-2,6-DIFLUOROPHENYLBORONIC ACID; 4-CYANO-2-FLUOROPHENYLBORONIC ACID; 4-CYANO-2-HYDROXYPHENYLBORONIC ACID; 4-CYANO-2-METHOXYPHENYLBORONIC ACID; 4-CYANO-2-METHOXYPYRIDIN-3-YLBORONIC ACID; 4-CYANO-2-THIOPHENEBORONIC ACID; 4-CYANO-3-(TRIFLUOROMETHYL)PHENYLBORONIC ACID; 4-CYANO-3,5-DIFLUOROPHENYLBORONIC ACID; 4-CYANO-3-FLUOROPHENYLBORONIC ACID; 4-CYANO-3-HYDROXYPHENYLBORONIC ACID; 4-CYANO-3-METHOXYPHENYLBORONIC ACID; 4-CYANO-3-METHYLBENZO[B]THIOPHEN-2-YLBORONIC ACID; 4-CYANO-3-METHYLPHENYLBORONIC ACID; 4-CYANOBENZO[B]THIOPHEN-2-YLBORONIC ACID; 4-CYANOMETHOXYPHENYLBORONIC ACID; 4-CYANONAPHTHALEN-2-YLBORONIC ACID; 4-CYANOPHENYLBORONIC ACID; 4-CYANOPYRIDINE-2-BORONIC ACID; 4-CYANOPYRIDINE-3-BORONIC ACID; 4-CYANOTHIOPHEN-3-YLBORONIC ACID; 4-CYCLOBUTYL(PHENYL-D4)-BORONIC ACID; 4-CYCLOBUTYLPHENYLBORONIC ACID; 4-CYCLOHEXYLBENZENEBORONIC ACID; 4-CYCLOPENTENYLPHENYLBORONIC ACID; 4-CYCLOPENTOXYPHENYLBORONIC ACID; 4-CYCLOPENTYLPHENYLBORONIC ACID; 4-CYCLOPENTYLPYRIMIDINE-5-BORONIC ACID; 4-CYCLOPROPOXYPHENYLBORONIC ACID; 4-CYCLOPROPYL(PHENYL-D4)-BORONIC ACID; 4-CYCLOPROPYL-BENZENEBORONIC ACID; 4-CYCLOPROPYL-PYRROL-3-YLBORONIC ACID; 4-CYCLOPROPYLTHIOPHENYLBORONIC ACID; 4-DIFLUOROMETHOXY-3-FLUORO-BENZENEBORONIC ACID; 4-DIFLUOROMETHOXY-3-METHYL-BENZENEBORONIC ACID; 4-DIFLUOROMETHOXY-3-TRIFLUOROMETHYL-BENZENEBORONIC ACID; 4-DIFLUOROMETHYL-PHENYLBORONIC ACID; 4-DIMETHYLAMINONAPHTHALENE-1-BORONIC ACID; 4-DIMETHYLAMINOPHENYLBORONIC ACID HYDROCHLORIDE; 4-DIPHENYL-1-NAPHTHALENE BORONIC ACID; 4-ETHOXY-2-(TRIFLUOROMETHOXY)PHENYLBORONIC ACID; 4-ETHOXY-2-(TRIFLUOROMETHYL)PHENYLBORONIC ACID; 4-ETHOXY-2,3,5,6-TETRAFLUOROPHENYLBORONIC ACID; 4-ETHOXY-2-FLUOROPHENYLBORONIC ACID; 4-ETHOXY-2-METHOXYPHENYLBORONIC ACID; 4-ETHOXY-2-METHYLPHENYLBORONIC ACID; 4-ETHOXY-3-FLUOROPHENYLBORONIC ACID; 4-ETHOXY-3-METHYLPHENYLBORONIC ACID; 4-ETHOXYBIPHENYL-4'-BORONIC ACID; 4-ETHOXYCARBONYL-2-NITROPHENYLBORONIC ACID; 4-ETHOXYCARBONYL-3-FLUOROPHENYLBORONIC ACID; 4-ETHOXYCARBONYL-3-METHOXYPHENYLBORONIC ACID; 4-ETHOXYCARBONYLMETHYLPHENYLBORONIC ACID; 4-ETHOXYCARBONYLPHENYLBORONIC ACID; 4-ETHOXYMETHYLPHENYLBORONIC ACID; 4-ETHOXYPHENYLBORONIC ACID; 4-ETHOXYPYRIDINE-3-BORONIC ACID; 4-ETHYL-3,5-DIMETHYLPHENYLBORONIC ACID; 4'-ETHYL-3-FLUOROBIPHENYL-4-BORONIC ACID; 4'-ETHYL-4-BIPHENYLBORONIC ACID; 4-ETHYL-6-(ETHYL(METHYL)AMINO)PYRIDIN-3-YLBORONIC ACID; 4-ETHYLCYCLOHEXEN-1-YLBORONIC ACID; 4-ETHYLFURAN-2-BORONIC ACID; 4-ETHYLPHENYLBORONIC ACID; 4-ETHYLPYRIDINE-3-BORONIC ACID; 4-ETHYL-PYRROL-3-YLBORONIC ACID; 4-ETHYLSULFINYLPHENYLBORONIC ACID; 4-ETHYLTHIOPHEN-2-YLBORONIC ACID; 4-ETHYLTHIOPHENYLBORONIC ACID; 4-ETHYNYL-2-METHYLPYRIDIN-3-YLBORONIC ACID; 4-FLUORO(PHENYL-D4)-BORONIC ACID; 4-FLUORO-1-(TRIISOPROPYLSILYL)-PYRROL-3-YLBORONIC ACID; 4-FLUORO-1H-INDAZOL-6-YLBORONIC ACID; 4-FLUORO-1H-INDOL-3-YLBORONIC ACID; 4-FLUORO-1H-PYRAZOL-5-YLBORONIC ACID; 4-FLUORO-1-METHYL-1H-INDOL-2-YLBORONIC ACID; 4-FLUORO-1-METHYL-1H-PYRROLE-2-BO-

RONIC ACID; 4-FLUORO-2-(1,2,4-OXADIAZOL-3-YL)PHENYLBORONIC ACID; 4-FLUORO-2-(5-PROPYL-1,3,4-OXADIAZOL-2-YL)PHENYLBORONIC ACID; 4-FLUORO-2-(METHYLSULFONYL)PHENYLBORONIC ACID; 4-FLUORO-2-(METHYLTHIO)PHENYLBORONIC ACID; 4-FLUORO-2-(TRIFLUOROMETHYL)PHENYLBORONIC ACID; 4-FLUORO-2,3-DIMETHYLPHENYLBORONIC ACID; 4-FLUORO-2,5-DIMETHYLPHENYLBORONIC ACID; 4-FLUORO-2-FURANBORONIC ACID; 4-FLUORO-2-HYDROXYPHENYLBORONIC ACID; 4-FLUORO-2-ISOPROPOXYPHENYLBORONIC ACID; 4-FLUORO-2-METHOXY-5-METHYLPHENYLBORONIC ACID; 4-FLUORO-2-METHOXYCARBONYLPHENYLBORONIC ACID; 4-FLUORO-2-METHOXYPHENYLBORONIC ACID; 4-FLUORO-2-METHYLPHENYLBORONIC ACID; 4-FLUORO-2-PROPOXYPHENYLBORONIC ACID; 4-FLUORO-2-THIOPHENEBORONIC ACID; 4-FLUORO-3-(2,2,2-TRIFLUOROETHOXY)PHENYLBORONIC ACID; 4-FLUORO-3-(2-CHLORO-PHENYLCARBAMOYL)PHENYLBORONIC ACID; 4-FLUORO-3-(2-HYDROXYETHYLCARBAMOYL)PHENYLBORONIC ACID; 4-FLUORO-3-(ISOPROPYLCARBAMOYL)PHENYLBORONIC ACID; 4-FLUORO-3-(METHOXY(METHYL)CARBAMOYL)PHENYLBORONIC ACID; 4-FLUORO-3-(METHOXYCARBONYL)PHENYLBORONIC ACID; 4-FLUORO-3-(METHYLCARBAMOYL)PHENYLBORONIC ACID; 4-FLUORO-3-(MORPHOLINE-4-CARBONYL)PHENYLBORONIC ACID; 4-FLUORO-3-(N-PROPYLCARBAMOYL)PHENYLBORONIC ACID; 4-FLUORO-3-(PHENYLCARBAMOYL)BENZENEBORONIC ACID; 4-FLUORO-3-(PIPERIDINE-1-CARBONYL)PHENYLBORONIC ACID; 4-FLUORO-3-(PYRROLIDINE-1-CARBONYL)PHENYLBORONIC ACID; 4-FLUORO-3-(TETRAHYDRO-2H-PYRAN-2-YLOXY)PHENYLBORONIC ACID; 4-FLUORO-3-(TETRAZOL-5-YL)PHENYLBORONIC ACID; 4-FLUORO-3-(THIOMORPHOLINOMETHYL)PHENYLBORONIC ACID; 4-FLUORO-3-(TRIFLUOROMETHYL)PHENYLBORONIC ACID; 4-FLUORO-3-(TRIMETHYLSILYL)PHENYLBORONIC ACID; 4-FLUORO-3,5-BIS(TRIMETHYLSILYL)PHENYLBORONIC ACID; 4-FLUORO-3-[(METHOXYAMINO)CARBONYL]BENZENEBORONIC ACID; 4-FLUORO-3-HYDROXYPHENYLBORONIC ACID; 4-FLUORO-3-METHOXYPHENYLBORONIC ACID; 4-FLUORO-3-METHYLPHENYLBORONIC ACID; 4-FLUORO-3-NITROPHENYLBORONIC ACID; 4-FLUOROBENZOFURAN-7-BORONIC ACID; 4-FLUOROBENZYLBORONIC ACID; 4-FLUORONAPHTHALENE-1-BORONIC ACID; 4-FLUOROPHENYLBORONIC ACID; 4-FLUOROPYRIDINE-2-BORONIC ACID; 4-FLUOROPYRIDINE-3-BORONIC ACID; 4-FLUORO-PYRROL-3-YLBORONIC ACID; 4-FLUOROQUINOLINE-3-BORONIC ACID; 4-HEPTYLOXYPHENYLBORONIC ACID; 4-HEXYLOXYPHENYLBORONIC ACID; 4-HEXYLTHIOPHENE-3-BORONIC ACID; 4-HYDROXY-2-(METHOXYCARBONYL)PHENYLBORONIC ACID; 4-HYDROXY-2-(TRIFLUOROMETHOXY)PHENYLBORONIC ACID; 4-HYDROXY-2-(TRIFLUOROMETHYL)PHENYLBORONIC ACID; 4-HYDROXY-2-METHOXYPHENYLBORONIC ACID; 4-HYDROXY-3-(METHOXYCARBONYL)PHENYLBORONIC ACID; 4-HYDROXY-3-(TRIFLUOROMETHOXY)PHENYLBORONIC ACID; 4-HYDROXY-3-(TRIFLUOROMETHYL)PHENYLBORONIC ACID; 4-HYDROXY-3,5-DIMETHYLPHENYLBORONIC ACID; 4-HYDROXY-3-METHOXYPHENYLBORONIC ACID; 4-HYDROXY-3-METHYLBENZENEBORONIC ACID; 4-HYDROXYBENZOTHIAZOLE-2-BORONIC ACID; 4-HYDROXYL-1-NAPHTHALENEBORONIC ACID; 4-HYDROXYMETHYL-2-METHOXYPHENYLBORONIC ACID; 4-HYDROXYMETHYL-3-METHYLPHENYLBORONIC ACID; 4-HYDROXYNAPHTHALENE-2-BORONIC ACID; 4-HYDROXYPHENYLBORONIC ACID; 4-HYDROXYPYRIDINE-2-BORONIC ACID; 4-HYDROXYPYRIDINE-3-BORONIC ACID; 4-HYDROXYQUINOLINE-2-BORONIC ACID; 4-HYDROXYQUINOLINE-3-BORONIC ACID; 4-HYDROXYQUINOLINE-5-BORONIC ACID; 4-HYDROXYQUINOLINE-6-BORONIC ACID; 4-HYDROXYQUINOLINE-7-BORONIC ACID; 4-HYDROXYQUINOLINE-8-BORONIC ACID; 4'-ISOBUTOXYBIPHENYL-4-YLBORONIC ACID; 4-ISOBUTOXYPHENYLBORONIC ACID; 4'-ISOBUTYL-3'-NITROBIPHENYL-4-YLBORONIC ACID; 4-ISOBUTYLPHENYLBORONIC ACID; 4-ISOBUTYRAMIDOBENZENEBORONIC ACID; 4-ISOPROPOXY-2-(TRIFLUOROMETHYL)PHENYLBORONIC ACID; 4-ISOPROPOXY-2,3,5,6-TETRAFLUOROPHENYLBORONIC ACID; 4-ISOPROPOXY-2,6-DIMETHYLPHENYLBORONIC ACID; 4-ISOPROPOXY-2-METHYLPHENYLBORONIC ACID; 4-ISOPROPOXY-3-(TRIFLUOROMETHYL)BENZENEBORONIC ACID; 4-ISOPROPOXY-3-METHYLPHENYLBORONIC ACID; 4-ISOPROPOXYCARBONYLPHENYLBORONIC ACID; 4-ISOPROPOXYPHENYLBORONIC ACID; 4-ISOPROPOXYPHENYLBORONIC ACID HYDRATE; 4-ISOPROPYL-1-(METHYLSULFONYL)-PYRROL-3-YLBORONIC ACID; 4-ISOPROPYL-1-(TRIISOPROPYLSILYL)-PYRROL-3-YLBORONIC ACID; 4-ISOPROPYL-1-(TRIMETHYLSILYL)-PYRROL-3-YLBORONIC ACID; 4-ISOPROPYLPHENYLBORONIC ACID; 4-ISOPROPYLPYRIMIDINE-5-BORONIC ACID; 4-ISOPROPYL-PYRROL-3-YLBORONIC ACID; 4-ISOPROPYLTHIOPHENYLBORONIC ACID; 4-JULOLIDINE BORONIC ACID; 4-MERCAPTOPHENYLBORONIC ACID; 4-METHOXY-1H-INDOL-2-YL-BORONIC ACID; 4-METHOXY-2-(5-PROPYL-1,3,4-OXADIAZOL-2-YL)PHENYLBORONIC ACID; 4-METHOXY-2-(METHOXYMETHOXY)PHENYLBORONIC ACID; 4-METHOXY-2-(TRIFLUOROMETHOXY)PHENYLBORONIC ACID; 4-METHOXY-2-(TRIFLUOROMETHYL)PHENYLBORONIC ACID; 4-METHOXY-2,3,5,6-TETRAFLUOROPHENYLBORONIC ACID; 4-METHOXY-2,3-DIMETHYLPHENYLBORONIC ACID; 4-METHOXY-2-METHYLPHENYLBORONIC ACID; 4-METHOXY-2-NITROPHENYLBORONIC ACID; 4-METHOXY-3-(METHOXYMETHOXY)PHENYLBORONIC ACID; 4-METHOXY-3-(MORPHOLIN-4-YLSULPHONYL)BENZENEBORONIC ACID; 4-METHOXY-3-(N,N-DIETHYLSULFAMOYL)PHENYLBORONIC ACID; 4-METHOXY-3-(PIPERIDIN-1-YLSULPHONYL)BENZENEBORONIC ACID; 4-METHOXY-3-(PYRROLIDIN-1-YLSULPHONYL)BENZENEBORONIC ACID; 4-METHOXY-3-(TRIFLUOROMETHOXY)PHENYLBORONIC ACID; 4-METHOXY-3-METHYLPHENYLBORONIC ACID; 4-METHOXY-3-NITROPHENYLBORONIC ACID; 4-METHOXY-3-PROPOXYPHENYLBORONIC ACID; 4-METHOXY-3-PYRIDINE BORONIC ACID HYDROCHLORIDE;

4-METHOXY-3-PYRIDINEBORONIC ACID; 4'-METHOXY-4-BIPHENYLBORONIC ACID; 4-METHOXY-6-METHYLPYRIDINE-3-BORONIC ACID; 4-METHOXYBENZO[B]THIOPHEN-2-YLBORONIC ACID; 4-METHOXYBENZOTHIAZOLE-2-BORONIC ACID; 4-METHOXYCARBONYL-2-NITROPHENYLBORONIC ACID; 4-METHOXYCARBONYL-3,5-DIMETHYLPHENYLBORONIC ACID; 4-METHOXYCARBONYL-3-METHYLPHENYLBORONIC ACID; 4-METHOXYCARBONYL-3-NITROPHENYLBORONIC ACID; 4-METHOXYCARBONYLPHENYLBORONIC ACID; 4-METHOXYNAPHTHALENE-1-BORONIC ACID; 4-METHOXYPHENYLBORONIC ACID; 4-METHOXYPYRIDINE-2-BORONIC ACID; 4-METHOXYPYRIDINE-3-BORONIC ACID HYDRATE; 4-METHOXYPYRIMIDIN-5-YLBORONIC ACID; 4-METHOXY-QUINOLINE-2-BORONIC ACID; 4-METHYL(PHENYL-D4)-BORONIC ACID; 4-METHYL-1-(METHYLSULFONYL)-PYRROL-3-YL-BORONIC ACID; 4-METHYL-1-(TRIISOPROPYLSILYL)-PYRROL-3-YLBORONIC ACID; 4-METHYL-1-(TRIMETHYLSILYL)-PYRROL-3-YLBORONIC ACID; 4-METHYL-1-CYCLOHEXEN-1-YLBORONIC ACID; 4-METHYL-1H-INDAZOLE-5-BORONIC ACID; 4-METHYL-1H-INDAZOLE-6-BORONIC ACID; 4-METHYL-1H-INDOL-3-YLBORONIC ACID; 4-METHYL-1H-INDOLE-2-BORONIC ACID; 4-METHYL-1-PENTENYLBORONIC ACID; 4-METHYL-1-PHENYL-1H-PYRAZOL-3-YLBORONIC ACID; 4-METHYL-2-(2-(TRIFLUOROMETHOXY)PHENYL)PYRIDINE-3-BORONIC ACID; 4-METHYL-2-(2-(TRIFLUOROMETHYL)PHENYL)PYRIDINE-3-BORONIC ACID; 4-METHYL-2-(2,4,5-TRICHLOROPHENYL)PYRIDINE-3-BORONIC ACID; 4-METHYL-2-(3-(TRIFLUOROMETHOXY)PHENYL)PYRIDINE-3-BORONIC ACID; 4-METHYL-2-(3-(TRIFLUOROMETHYL)PHENYL)PYRIDINE-3-BORONIC ACID; 4-METHYL-2-(4-(TRIFLUOROMETHOXY)PHENYL)PYRIDINE-3-BORONIC ACID; 4-METHYL-2-(4-(TRIFLUOROMETHYL)PHENYL)PYRIDINE-3-BORONIC ACID; 4-METHYL-2-(4-(TRIFLUOROMETHYL)PHENYL)THIAZOL-5-YLBORONIC ACID; 4-METHYL-2-(PERFLUOROPHENYL)PYRIDINE-3-BORONIC ACID; 4-METHYL-2-(TRIFLUOROMETHOXY)PHENYLBORONIC ACID; 4-METHYL-2-(TRIFLUOROMETHYL)PHENYLBORONIC ACID; 4'-METHYL-2,2'-BITHIOPHEN-5-YLBORONIC ACID; 4-METHYL-2-OXO-2,3-DIHYDROBENZO[D]OXAZOL-6-YLBORONIC ACID; 4-METHYL-2-PHENYLTHIAZOL-5-YLBORONIC ACID; 4-METHYL-3-(4-(PYRIDIN-2-YL-METHOXY)BENZAMIDO)PHENYLBORONIC ACID; 4-METHYL-3-(TRIFLUOROMETHOXY)PHENYLBORONIC ACID; 4-METHYL-3-(TRIFLUOROMETHYL)PHENYLBORONIC ACID; 4-METHYL-3,4-DIHYDRO-2H-1,4-BENZOXAZIN-7-YLBORONIC ACID; 4-METHYL-3-NITROPHENYLBORONIC ACID; 4-METHYL-3-THIOPHENEBORONIC ACID; 4'-METHYL-4-BIPHENYLBORONIC ACID; 4-METHYL-6-(1H-PYRAZOL-1-YL)PYRIDIN-3-YLBORONIC ACID; 4-METHYL-6-(1H-PYRROL-1-YL)PYRIDIN-3-YLBORONIC ACID; 4-METHYLFURAN-2-BORONIC ACID; 4-METHYLPHENYLBORONIC ACID; 4-METHYLPYRIDINE-2-BORONIC ACID; 4-METHYLPYRIDINE-3-BORONIC ACID; 4-METHYLPYRIDINE-3-BORONIC ACID, HYDROCHLORIDE; 4-METHYLPYRIMIDINE-5-BORONIC ACID; 4-METHYL-PYRROL-3-YLBORONIC ACID; 4-METHYLTHIOPHENE-2-BORONIC ACID; 4-MORPHOLINOPHENYLBORONIC ACID; 4-MORPHOLINOQUINOLIN-6-YLBORONIC ACID; 4-N-BOC-AMINO-3-FLUOROPHENYLBORONIC ACID; 4-N-BOC-AMINO-3-METHOXY-PHENYLBORONIC ACID; 4-N-BUTOXY-2-FLUOROPHENYLBORONIC ACID; 4-N-HEPTYLPHENYLBORONIC ACID; 4-N-HEXYLPHENYLBORONIC ACID; 4-NITRO-3-(TRIFLUOROMETHYL)PHENYLBORONIC ACID; 4'-NITRO-BIPHENYL-4-BORONIC ACID; 4-NITROPHENYLBORONIC ACID; 4-NITROPYRIDINE-2-BORONIC ACID; 4-N-NONYLBENZENEBORONIC ACID; 4-N-PENTYLPHENYLBORONIC ACID; 4-OCTYLOXYPHENYLBORONIC ACID; 4-OXO-2-THIOXO-1,2,3,4-TETRAHYDROPYRIMIDIN-5-YLBORONIC ACID; 4-PENT-1-YNYLPHENYLBORONIC ACID; 4-PENTENYLBORONIC ACID; 4-PENTYL-2-FLUOROPHENYLBORONIC ACID; 4-PENTYL-3-FLUOROPHENYLBORONIC ACID; 4-PENTYLCYCLOHEX-1-ENYLBORONIC ACID; 4-PENTYLOXY-2-FLUOROPHENYLBORONIC ACID; 4-PENTYLOXY-3-FLUOROPHENYLBORONIC ACID; 4-PENTYLOXYPHENYLBORONIC ACID; 4-PHENOXYPHENYLBORONIC ACID; 4-PHENOXYPYRIDIN-3-YLBORONIC ACID; 4-PHENYL(NAPHTHALENE-1-YL)BORONIC ACID; 4-PHENYL-1H-PYRROLO[2,3-B]PYRIDINE-2-BORONIC ACID; 4-PHENYL-1H-PYRROLO[2,3-B]PYRIDINE-3-BORONIC ACID; 4-PHENYL-1H-PYRROLO[2,3-B]PYRIDINE-5-BORONIC ACID; 4-PHENYL-1H-PYRROLO[2,3-B]PYRIDINE-6-BORONIC ACID; 4-PHENYLFURAN-2-BORONIC ACID; 4-PHENYLPYRIDINE-3-BORONIC ACID; 4-PHENYLPYRIMIDINE-2-BORONIC ACID; 4-PHENYLPYRIMIDINE-5-BORONIC ACID; 4-PHENYL-PYRROL-3-YLBORONIC ACID; 4-PHENYLTHIOPHENE-2-BORONIC ACID; 4-PIVALAMIDOPHENYLBORONIC ACID; 4-PROPOXY-2,3,5,6-TETRAFLUOROPHENYLBORONIC ACID; 4-PROPOXY-2-METHYLPHENYLBORONIC ACID; 4-PROPOXYCARBONYLPHENYLBORONIC ACID; 4-PROPOXYPHENYLBORONIC ACID; 4'-PROPYL-3-FLUOROBIPHENYL-4-BORONIC ACID; 4'-PROPYL-4-BIPHENYLBORONIC ACID; 4-PROPYLCYCLOHEX-1-ENYLBORONIC ACID; 4-PROPYLPHENYLBORONIC ACID; 4-PROPYLPYRIDIN-3-YLBORONIC ACID; 4-PROPYLSULFANYLPHENYLBORONIC ACID; 4-PROPYLTHIOPHEN-2-YLBORONIC ACID; 4-TBDMS-HYDROXYMETHYLPHENYLBORONIC ACID; 4-T-BUTOXYPHENYLBORONIC ACID; 4-T-BUTYLCYCLOHEXEN-1-YLBORONIC ACID; 4-TERT-BUTOXY-2-CHLOROPYRIMIDIN-5-YLBORONIC ACID; 4'-TERT-BUTOXYCARBONYLAMINO-BIPHENYL-4-BORONIC ACID; 4-TERT-BUTOXYCARBOXYPHENYLBORONIC ACID; 4-TERT-BUTOXYMETHYLPHENYLBORONIC ACID; 4-TERT-BUTYL-2-FURANBORONIC ACID; 4-TERT-BUTYL-2-METHYLPHENYLBORONIC ACID; 4-TERT-BUTYL-3-NITROBENZENEBORONIC ACID; 4'-TERT-BUTYLBIPHENYL-2-YLBORONIC ACID; 4-TERT-BUTYLPHENYLBORONIC ACID; 4-TRIFLUOROACETYL AMINOPHENYLBORONIC ACID; 4-TRIFLUOROMETHOXYPHENYL 4-BORONOBENZENESULFONAMIDE; 4-TRIMETHYLSILYLPHENYLBORONIC ACID; 4-VINYLPHENYLBORONIC ACID; 5-((1-PHENYLETHYL)CARBAMOYL)THIOPHEN-2-YLBORONIC ACID; 5-((4-(TERT-BUTOXYCARBONYL)PIPERAZIN-1-YL)METHYL)-2-FLUORO-

PHENYLBORONIC ACID; 5-((BENZYLOXYCARBONYLAMINO)METHYL) THIOPHENE-2-BORONIC ACID; 5-((BOC-AMINO)METHYL)FURAN-2-BORONIC ACID; 5-((CYCLOPENTYLAMINO)METHYL)THIOPHEN-2-YLBORONIC ACID; 5-((CYCLOPROPYLAMINO)METHYL)THIOPHEN-2-YLBORONIC ACID; 5-((DIETHYLAMINO)METHYL)FURAN-2-YLBORONIC ACID; 5-((DIMETHYLAMINO)METHYL)FURAN-2-YLBORONIC ACID; 5-((DIMETHYLAMINO)METHYL)PYRIDIN-3-YLBORONIC ACID; 5-((DIMETHYLAMINO)METHYL)THIOPHEN-2-YLBORONIC ACID; 5-((ETHYLAMINO)METHYL)THIOPHEN-2-YLBORONIC ACID; 5-((ISOPROPYLAMINO)METHYL)THIOPHEN-2-YLBORONIC ACID; 5-((METHYLAMINO)METHYL)FURAN-3-YLBORONIC ACID; 5-((METHYLAMINO)METHYL)THIOPHEN-3-YLBORONIC ACID; 5-((TERT-BUTYLDIMETHYLSILYLOXY)METHYL)-2-FLUOROPYRIDIN-3-YLBORONIC ACID; 5-([TERT-BUTYL(DIMETHYL)SILYL]OXY)PYRIDINE-3-BORONIC ACID; 5-(1-(4-(TERT-BUTOXYCARBONYL)PIPERAZIN-1-YL)ETHYL)-2-FLUOROPYRIDIN-3-YLBORONIC ACID; 5-(1-(TERT-BUTYLDIMETHYLSILYLOXY)-2-METHYLPROPAN-2-YL)-2-FLUOROPYRIDIN-3-YLBORONIC ACID; 5-(1-(TERT-BUTYLDIMETHYLSILYLOXY)PROPAN-2-YL)-2-FLUOROPYRIDIN-3-YLBORONIC ACID; 5-(1,3-DIOXOLAN-2-YL)-2-FLUOROPYRIDIN-3-YLBORONIC ACID; 5-(1,3-DIOXOLAN-2-YL)FURAN-2-YLBORONIC ACID; 5-(1,3-DIOXOLAN-2-YL)PYRIDINE-BORONIC ACID; 5-(1-CYANOCYCLOPROPYL)-2-FLUOROPHENYLBORONIC ACID; 5-(1H-INDOL-4-YL)PYRIDIN-3-YLBORONIC ACID; 5-(1H-PYRAZOL-1-YL)PYRAZINE-2-BORONIC ACID; 5-(1H-PYRIDIN-2-ONE)PYRAZINE-2-BORONIC ACID; 5-(2-(TRIFLUOROMETHYL)PHENYL)PYRIDIN-3-YLBORONIC ACID; 5-(2-FLUOROPHENYL)FURAN-2-BORONIC ACID; 5-(2-FLUOROPHENYL)THIOPHENE-2-BORONIC ACID; 5-(2-FURYL)THIOPHENE-2-BORONIC ACID; 5-(2-HYDROXYPROPAN-2-YL)PYRIDINE-2-BORONIC ACID; 5-(2-HYDROXYPROPAN-2-YL)PYRIDINE-3-BORONIC ACID; 5-(2-METHOXYETHOXY)PYRIDINE-3-BORONIC ACID; 5-(2-METHOXYPHENYL)FURAN-2-BORONIC ACID; 5-(2-METHOXYPHENYL)PYRIDIN-3-YLBORONIC ACID; 5-(2-METHOXYPHENYL)THIOPHENE-2-BORONIC ACID; 5-(2-METHYLIMIDAZOL-1-YL)PYRAZINE-2-BORONIC ACID; 5-(2-METHYLPIPERIDIN-1-YL)PYRAZINE-2-BORONIC ACID; 5-(2-THIAZOLYL)THIOPHENE-2-BORONIC ACID; 5-(2-TOLYL)FURAN-2-BORONIC ACID; 5-(2-TOLYL)THIOPHENE-2-BORONIC ACID; 5-(2-TRIFLUOROMETHYLPHENYL)FURAN-2-BORONIC ACID; 5-(2-TRIFLUOROMETHYLPHENYL)THIOPHENE-2-BORONIC ACID; 5-(3-((TERT-BUTOXYCARBONYL)AMINO)PROPANAMIDO)PYRIDINE-3-BORONIC ACID; 5-(3-(AMINOMETHYL)PHENYL)PYRIDIN-3-YLBORONIC ACID; 5-(3-(METHYLSULFONYL)PHENYL)PYRIDIN-3-YLBORONIC ACID; 5-(3,5-DIMETHYLISOXAZOL-4-YL)BENZO[B]THIOPHEN-2-YLBORONIC ACID; 5-(3,5-DIMETHYLISOXAZOL-4-YL)THIOPHEN-2-YLBORONIC ACID; 5-(3-BORONOPHENYL)PENTANOIC ACID; 5-(3-ETHOXYPHENYL)PYRIDIN-3-YLBORONIC ACID; 5-(3-METHOXYPHENYL)PYRIDIN-2-YLBORONIC ACID; 5-(3-METHYL-1H-PYRAZOL-1-YL)PYRAZINE-2-BORONIC ACID; 5-(3-METHYLPIPERIDIN-1-YL)PYRAZINE-2-BORONIC ACID; 5-(3-MORPHOLINOPHENYL)PYRIDIN-3-YLBORONIC ACID; 5-(3-SULFAMOYLPHENYL)PYRIDIN-3-YLBORONIC ACID; 5-(4-(DIMETHYLAMINO)PHENYL)THIOPHEN-2-YLBORONIC ACID; 5-(4-(METHYLSULFONYL)PHENYL)PYRIMIDIN-2-YLBORONIC ACID; 5-(4-(TRIFLUOROMETHYL)PHENYL)PYRIDIN-3-YLBORONIC ACID; 5-(4,4-DIMETHYL-4,5-DIHYDROOXAZOL-2-YL)PYRIDIN-3-YLBORONIC ACID; 5-(4-CHLOROPHENYL)THIOPHEN-2-YLBORONIC ACID; 5-(4-FLUOROPHENYL)PYRIDIN-3-YLBORONIC ACID; 5-(4-FLUOROPHENYL)THIOPHEN-2-YLBORONIC ACID; 5-(4-METHOXYPHENYL)PYRIDIN-2-YLBORONIC ACID; 5-(4-METHOXYPHENYL)PYRIDIN-3-YLBORONIC ACID; 5-(4-METHOXYPHENYL)THIOPHEN-2-YLBORONIC ACID; 5-(4-METHYL-1H-PYRAZOL-1-YL)PYRAZINE-2-BORONIC ACID; 5-(4-METHYLPHENYL)THIOPHENE-2-BORONIC ACID; 5-(4-METHYLPIPERAZIN-1-YL)PYRAZINE-2-BORONIC ACID; 5-(4-METHYLPIPERAZIN-1-YL)PYRIDIN-3-YLBORONIC ACID; 5-(4-METHYLPIPERIDIN-1-YL)PYRAZINE-2-BORONIC ACID; 5-(4-MORPHOLINOPHENYL)PYRIDIN-3-YLBORONIC ACID; 5-(4-PENTYLOXYPHENYL)THIOPHENE-2-BORONIC ACID; 5-(4-PENTYLPHENYL)THIOPHENE-2-BORONIC ACID; 5-(5-CHLOROPYRIDIN-3-YLOXY)PYRIDIN-3-YLBORONIC ACID; 5-(5-CYCLOPROPYL-1,3,4-OXADIAZOL-2-YL)-2-METHYLPHENYLBORONIC ACID; 5-(AMINOMETHYL)-2-FLUOROPHENYLBORONIC ACID, HCL; 5-(AMINOMETHYL)THIOPHEN-2-YLBORONIC ACID; 5-(BENZO[D]THIAZOL-2-YL)THIOPHENE-2-BORONIC ACID; 5-(BENZYLCARBAMOYL)-2-FLUOROBENZENEBORONIC ACID; 5-(BENZYLOXY)-1H-INDOL-2-YLBORONIC ACID; 5-(BENZYLOXY)-2-(DIETHOXYMETHYL)PHENYLBORONIC ACID; 5-(BENZYLOXY)-2,4-DICHLOROPHENYLBORONIC ACID; 5-(BENZYLOXY)-2-BORONOBENZOIC ACID; 5-(BENZYLOXY)-2-CHLOROPHENYLBORONIC ACID; 5-(BENZYLOXY)-2-FLUOROPHENYLBORONIC ACID; 5-(BENZYLOXY)-2-FLUOROPYRIDIN-3-YLBORONIC ACID; 5-(BENZYLOXY)-2-METHYLPHENYLBORONIC ACID; 5-(BENZYLOXY)PYRIDINE-3-BORONIC ACID-HCL; 5-(BENZYLOXYCARBONYLAMINO)-2-FLUOROPHENYLBORONIC ACID; 5-(BOC-AMINO)PYRIDINE-3-BORONIC ACID; 5-(BOC-AMINOMETHYL)THIOPHENE-2-BORONIC ACID; 5-(CYANOMETHYL)THIOPHEN-3-YLBORONIC ACID; 5-(CYCLOBUTYL)FURAN-2-BORONIC ACID; 5-(CYCLOBUTYL)THIOPHENE-2-BORONIC ACID; 5-(CYCLOHEXYLCARBAMOYL)-2-FLUOROBENZENEBORONIC ACID; 5-(CYCLOPENTOXY)PYRAZINE-2-BORONIC ACID; 5-(CYCLOPROPYL)FURAN-2-BORONIC ACID; 5-(CYCLOPROPYL)THIOPHENE-2-BORONIC ACID; 5-(CYCLOPROPYLCARBAMOYL)-2-FLUOROPHENYLBORONIC ACID; 5-(DIETHOXYMETHYL)FURAN-2-YLBORONIC ACID; 5-(DIETHYLAMINO)PYRAZINE-2-BORONIC ACID; 5-(DIETHYLCARBAMOYL)-2-FLUOROBENZENEBORONIC ACID; 5-(DIETHYLCARBAMOYL)THIOPHEN-2-YLBORONIC ACID; 5-(DIFLUOROMETHOXY)-2-FLUOROPHENYLBORONIC ACID; 5-(DIFLUOROMETHOXY)BENZOTHIAZOLE-2-BO-

RONIC ACID; 5-(DIFLUOROMETHOXY)PYRAZINE-2-BORONIC ACID; 5-(DIHYDROXYBORYL)-2-THIOPHENECARBOXYLIC ACID; 5-(DIMETHOXYMETHYL)FURAN-2-BORONIC ACID; 5-(DIMETHOXYMETHYL)PYRIDINE-3-BORONIC ACID; 5-(DIMETHYLAMINO)-2-METHYLPHENYLBORONIC ACID; 5-(DIMETHYLAMINO)-3-METHYLPYRIDIN-2-YLBORONIC ACID HYDROCHLORIDE; 5-(DIMETHYLAMINO)BENZO[B]THIOPHEN-2-YLBORONIC ACID; 5-(DIMETHYLAMINO)PYRAZINE-2-BORONIC ACID; 5-(DIMETHYLAMINO)PYRIDIN-2-YLBORONIC ACID; 5-(DIMETHYLAMINO)PYRIDIN-3-YLBORONIC ACID; 5-(DIMETHYLAMINO-D6)-PYRIDINE-3-BORONIC ACID; 5-(DIMETHYLCARBAMOYL)-3-FLUOROPHENYLBORONIC ACID; 5-(DIMETHYLCARBAMOYL)PYRIDINE-3-BORONIC ACID; 5-(ETHOXYCARBONYL)-1H-INDOL-2-YLBORONIC ACID; 5-(ETHOXYCARBONYL)-1H-PYRROL-2-YLBORONIC ACID; 5-(ETHOXYCARBONYL)-2-HYDROXYPHENYLBORONIC ACID; 5-(ETHOXYCARBONYL)-2-METHOXYPHENYLBORONIC ACID; 5-(ETHOXYCARBONYL)-3-PYRIDINYL BORONIC ACID; 5-(ETHOXYCARBONYL)-6-METHYLPYRIDINE-3-BORONIC ACID; 5-(ETHOXYCARBONYL)FURAN-2-BORONIC ACID; 5-(ETHOXYCARBONYL)THIOPHENE-2-BORONIC ACID; 5-(ETHOXYCARBONYL)THIOPHENE-3-BORONIC ACID; 5-(ETHOXYMETHYL)PYRIDINE-3-BORONIC ACID; 5-(ETHYLCARBAMOYL)-2-FLUOROBENZENEBORONIC ACID; 5-(ETHYLCARBAMOYL)-3-FLUOROPHENYLBORONIC ACID; 5-(ETHYL-D5)-PYRIDINE-3-BORONIC ACID; 5-(ETHYLTHIO)FURAN-3-YLBORONIC ACID; 5-(FURAN-2-YL)FURAN-2-BORONIC ACID; 5-(HYDROXYMETHYL)-3-PYRIDINYL BORONIC ACID; 5-(HYDROXYMETHYL)FURAN-2-YLBORONIC ACID; 5-(HYDROXYMETHYL)NAPHTHALENE-1-BORONIC ACID; 5-(HYDROXYMETHYL)NAPHTHALENE-2-BORONIC ACID; 5-(HYDROXYMETHYL)PYRIDIN-3-YL-BORONIC ACID HYDROCHLORIDE; 5-(HYDROXYMETHYL)PYRIDINE-2-BORONIC ACID; 5-(IMIDAZOL-1-YL)PYRAZINE-2-BORONIC ACID; 5-(ISOPROPOXY)PYRAZINE-2-BORONIC ACID; 5-(ISO-PROPYL)FURAN-2-BORONIC ACID; 5-(ISO-PROPYL)THIOPHENE-2-BORONIC ACID; 5-(ISO-PROPYL-D7)-PYRIDINE-3-BORONIC ACID; 5-(METHOXY(METHYL)CARBAMOYL)FURAN-2-YLBORONIC ACID; 5-(METHOXYCARBONYL)-1H-PYRAZOL-3-YLBORONIC ACID; 5-(METHOXYCARBONYL)-1H-PYRROL-3-YLBORONIC ACID; 5-(METHOXYCARBONYL)-1-TOSYL-1H-PYRROL-3-YLBORONIC ACID; 5-(METHOXYCARBONYL)-4-METHYLTHIOPHEN-2-YLBORONIC ACID; 5-(METHOXYCARBONYL)-6-(METHYLTHIO)PYRIDIN-3-YLBORONIC ACID; 5-(METHOXYCARBONYL)FURAN-2-BORONIC ACID; 5-(METHOXYCARBONYL)PYRIDINE-2-BORONIC ACID; 5-(METHOXYCARBONYL)PYRIDINE-3-BORONIC ACID; 5-(METHOXYCARBONYL)THIOPHENE-3-BORONIC ACID; 5-(METHOXY-D3)-PYRAZINE-2-BORONIC ACID; 5-(METHOXY-D3)-PYRIDINE-3-BORONIC ACID; 5-(METHOXYMETHOXY)-2-METHYLPHENYLBORONIC ACID; 5-(METHOXYMETHOXY)-2-METHYLPYRIDIN-4-YLBORONIC ACID; 5-(METHOXYMETHYL)-3-PYRIDINYL BORONIC ACID; 5-(METHOXYMETHYL)THIOPHEN-3-YLBORONIC ACID; 5-(METHYL-D3)-PYRIDINE-3-BORONIC ACID; 5-(METHYLSULFANYL)-2-THIENYLBORONIC ACID; 5-(METHYLSULPHONYL)PYRIDINE-3-BORONIC ACID; 5-(METHYLTHIO)PYRAZINE-2-BORONIC ACID; 5-(METHYLTHIO)PYRIDINE-3-BORONIC ACID; 5-(MORPHOLINOMETHYL)THIOPHEN-2-YLBORONIC ACID; 5-(N,N-DIETHYLSULFAMOYL)-2-METHYLPHENYLBORONIC ACID; 5-(N,N-DIMETHYLSULFAMOYL)-2-METHYLPHENYLBORONIC ACID; 5-(N,N-METHYLETHYLAMINO)PYRAZINE-2-BORONIC ACID; 5-(N-PROPOXY)PYRAZINE-2-BORONIC ACID; 5-(N-PROPYL-D7)-PYRIDINE-3-BORONIC ACID; 5-(N-TERT-BUTYLSULFAMOYL)-2-METHYLBENZENEBORONIC ACID; 5-(N-TERT-BUTYLSULFAMOYL)THIOPHEN-2-YLBORONIC ACID; 5-(O-TBDMS)OXYMETHYLFURAN-2-BORONIC ACID; 5-(OXAZOL-5-YL)FURAN-2-YLBORONIC ACID; 5-(OXAZOL-5-YL)THIOPHEN-2-YLBORONIC ACID; 5-(PERFLUOROETHYL)PYRIDIN-3-YLBORONIC ACID; 5-(PIPERIDIN-1-YL)PYRAZINE-2-BORONIC ACID; 5-(PIPERIDIN-2-YL)PYRIDIN-3-YLBORONIC ACID; 5-(PROP-1-YNYL)PYRIDIN-3-YLBORONIC ACID; 5-(PYRIDIN-3-YLOXY)PYRIDINE-3-BORONIC ACID; 5-(PYRROLIDIN-1-YL)PYRAZINE-2-BORONIC ACID; 5-(T-BUTYLDIMETHYLSILYLOXY)-2,3-DIFLUOROPHENYLBORONIC ACID; 5-(T-BUTYLDIMETHYLSILYLOXY)-2-FLUOROPHENYLBORONIC ACID; 5-(T-BUTYLDIMETHYLSILYLOXY)-2-METHOXYPHENYLBORONIC ACID; 5-(TERT-BUTOXY)PYRAZINE-2-BORONIC ACID; 5-(TERT-BUTOXY)PYRIDINE-2-BORONIC ACID; 5-(TERT-BUTOXYCARBONYL)-4,5,6,7-TETRAHYDROTHIENO[3,4-C]PYRIDIN-3-YLBORONIC ACID; 5-(TERT-BUTOXYCARBONYL)-5,6-DIHYDRO-4H-THIENO[3,2-C]PYRROL-2-YLBORONIC ACID; 5-(TERT-BUTOXYCARBONYL)-5,6-DIHYDRO-4H-THIENO[3,4-C]PYRROL-1-YL BORONIC ACID; 5-(TERT-BUTOXYCARBONYLAMINO)-2-(DIMETHYLAMINO)PHENYLBORONIC ACID; 5-(TERT-BUTOXYCARBONYLAMINO)-2-CHLOROPYRIDIN-4-YLBORONIC ACID; 5-(TERT-BUTOXYCARBONYLAMINO)NAPHTHALEN-1-YLBORONIC ACID; 5-(TERT-BUTYL)PYRAZINE-2-BORONIC ACID; 5-(TERT-BUTYLCARBAMOYL)-2-FLUOROBENZENEBORONIC ACID; 5-(TERT-BUTYLCARBAMOYL)-4-METHYLTHIOPHEN-2-YLBORONIC ACID; 5-(TERT-BUTYLCARBAMOYL)PYRIDINE-3-BORONIC ACID; 5-(THIAZOL-2-YL)FURAN-2-BORONIC ACID; 5-(THIOPHEN-2-YL)FURAN-2-BORONIC ACID; 5-(TRIFLUOROMETHOXY)PYRAZINE-2-BORONIC ACID; 5-(TRIFLUOROMETHOXY)PYRIDINE-3-BORONIC ACID; 5-(TRIFLUOROMETHYL)-1H-PYRROL-2-YLBORONIC ACID; 5-(TRIFLUOROMETHYL)-2-(2-(TRIFLUOROMETHYL)PHENYL)PYRIDINE-3-BORONIC ACID; 5-(TRIFLUOROMETHYL)-2-(2-(TRIFLUOROMETHYL)PHENYL)PYRIDINE-4-BORONIC ACID; 5-(TRIFLUOROMETHYL)-2-(3-(TRIFLUOROMETHYL)PHENYL)PYRIDINE-3-BORONIC ACID; 5-(TRIFLUOROMETHYL)-2-(3-(TRIFLUOROMETHYL)PHENYL)PYRIDINE-4-BORONIC ACID; 5-(TRIFLUOROMETHYL)-2-(4-(TRIFLUOROMETHYL)PHENYL)PYRIDINE-3-BORONIC ACID; 5-(TRIFLUOROMETHYL)-2-(4-(TRIFLUOROMETHYL)PHENYL)PYRIDINE-4-

BORONIC ACID; 5-(TRIFLUOROMETHYL)-2-(TRIMETHYLSILYL)PHENYLBORONIC ACID; 5-(TRIFLUOROMETHYL)FURAN-2-BORONIC ACID; 5-(TRIFLUOROMETHYL)PYRIDINE-2-BORONIC ACID; 5-(TRIFLUOROMETHYL)THIOPHENE-2-BORONIC ACID; 5-(TRIFLUOROMETHYL)THIOPHENE-3-BORONIC ACID; 5,5,8,8-TETRAMETHYL-5,6,7,8-TETRAHYDRO-2-NAPHTHALENYLBORONIC ACID; 5,6,7,8-TETRAHYDRO-2-NAPHTHALENYLBORONIC ACID; 5,6,7,8-TETRAHYDROISOQUINOLINE-3-BORONIC ACID; 5,6,7,8-TETRAHYDRONAPHTHALEN-1-YLBORONIC ACID; 5,6,7,8-TETRAHYDROQUINOLINE-2-BORONIC ACID; 5,6-DIFLUOROBENZO[B]THIOPHEN-3-YLBORONIC ACID; 5,6-DIMETHOXY-1H-INDOL-3-YLBORONIC ACID; 5,6-DIMETHOXYPYRAZIN-2-YLBORONIC ACID; 5,6-DIMETHYLPYRIDINE-2-BORONIC ACID; 5,6-DIMETHYLPYRIDINE-3-BORONIC ACID; 5-[(BENZYLOXY)METHYL]PYRIDINE-2-BORONIC ACID; 5-[(TRIMETHYLSILANYL)ETHYNYL]PYRIDINE-3-BORONIC ACID; 5-ACETAMIDO-2-(AMINOMETHYL)PHENYLBORONIC ACID; 5-ACETAMIDO-2-METHYLPHENYLBORONIC ACID; 5-ACRYLAMIDO-2-((DIMETHYLAMINO)METHYL)PHENYLBORONIC ACID; 5-ACRYLAMIDO-2-(AMINOMETHYL)PHENYLBORONIC ACID; 5-ACRYLAMIDO-2-(HYDROXYMETHYL)PHENYLBORONIC ACID; 5-ALLYL-2-METHOXYPHENYLBORONIC ACID; 5-AMINO-2-((TERT-BUTOXYCARBONYLAMINO)METHYL)PHENYLBORONIC ACID; 5-AMINO-2-(HYDROXYMETHYL)BENZENEBORONIC ACID HYDROCHLORIDE; 5-AMINO-2,3-DIFLUOROPHENYLBORONIC ACID; 5-AMINO-2,4-DIFLUOROPHENYLBORONIC ACID; 5-AMINO-2-CHLOROPHENYLBORONIC ACID HYDROCHLORIDE; 5-AMINO-2-CHLOROPYRIDINE-3-BORONIC ACID; 5-AMINO-2-FLUOROPHENYLBORONIC ACID; 5-AMINO-2-FLUOROPHENYLBORONIC ACID HYDROCHLORIDE; 5-AMINO-3-FLUORO-6-(METHOXYCARBONYL)PYRIDIN-2-YLBORONIC ACID; 5-AMINO-6-(2,2,2-TRIFLUOROETHOXY)PYRAZIN-2-YLBORONIC ACID; 5-AMINO-6-(2-METHOXYETHOXY)PYRAZIN-2-YLBORONIC ACID; 5-AMINO-6-(4-(METHOXYCARBONYL)PIPERIDIN-1-YL)PYRAZIN-2-YLBORONIC ACID; 5-AMINO-6-(METHOXYCARBONYL)-3-METHYLPYRIDIN-2-YLBORONIC ACID; 5-AMINO-6-CHLOROPYRIDINE-3-BORONIC ACID; 5-AMINO-6-ETHOXYPYRIDINE-3-BORONIC ACID; 5-AMINO-6-METHOXYPYRAZIN-2-YLBORONIC ACID; 5-AMINO-6-METHOXYPYRIDINE-3-BORONIC ACID; 5-AMINOBENZO[B]THIOPHEN-2-YLBORONIC ACID; 5-AMINOCARBONYLPYRIDINE-2-BORONIC ACID; 5-AMINOPYRAZINE-2-BORONIC ACID; 5-AMINOPYRIDINE-2-BORONIC ACID; 5-AMINOPYRIDINE-3-BORONIC ACID-HCL; 5-AMINOTHIOPHEN-3-YLBORONIC ACID; 5-BENZOTHIOPHENEBORONIC ACID; 5-BENZYLOXY-1-BOC-INDOLE-2-BORONIC ACID; 5-BENZYLOXY-3-PYRIDINYLBORONIC ACID; 5-BORONO-2-(2-HYDROXYPROPAN-2-YL)PYRIDINE 1-OXIDE; 5-BORONO-2,3-DIHYDRO-3-METHYL-1H-PYRROLO[2,3-B]PYRIDINE-1-CARBOXYLIC ACID 1-(1,1-DIMETHYLETHYL) ESTER; 5-BORONO-3-METHYLTHIOPHENE-2-CARBOXYLIC ACID; 5-BORONO-4-CHLORO-2-FLUOROBENZOIC ACID; 5-BORONO-6-FLUOROPICOLINIC ACID; 5-BORONOFURAN-2-CARBOXYLIC ACID; 5-BORONOFURAN-3-CARBOXYLIC ACID; 5-BUTOXY-2,4-DICHLOROPHENYLBORONIC ACID; 5-BUTOXY-2-CHLOROPHENYLBORONIC ACID; 5-BUTOXY-2-FLUOROPHENYLBORONIC ACID; 5-BUTYL-2-(N-TERT-BUTYLSULFAMOYL)THIOPHEN-3-YLBORONIC ACID; 5-BUTYLFURAN-2-YLBORONIC ACID; 5-BUTYLPYRIDIN-2-YLBORONIC ACID; 5-CARBAMOYL-2-CHLOROPHENYLBORONIC ACID; 5-CARBAMOYL-2-FLUOROBENZENEBORONIC ACID; 5-CARBAMOYL-2-HYDROXYPHENYLBORONIC ACID; 5-CARBAMOYLFURAN-3-YLBORONIC ACID; 5-CARBAMOYLTHIOPHEN-2-YLBORONIC ACID; 5-CARBAMOYLTHIOPHEN-3-YLBORONIC ACID; 5-CARBOXY-2-CHLORO-4-METHOXYPHENYLBORONIC ACID; 5-CARBOXY-2-CHLOROPHENYLBORONIC ACID; 5-CARBOXY-2-ETHOXYPHENYLBORONIC ACID; 5-CARBOXY-2-FLUOROPHENYLBORONIC ACID; 5-CARBOXY-2-FLUOROPYRIDINE-3-BORONIC ACID; 5-CARBOXY-6-CHLOROPYRIDINE-3-BORONIC ACID; 5-CARBOXY-6-FLUOROPYRIDINE-3-BORONIC ACID; 5-CARBOXYPYRIDINE-3-BORONIC ACID; 5-CHLORO-1-(TRIISOPROPYLSILYL)-PYRROL-2-YL-BORONIC ACID; 5-CHLORO-1H-INDOL-3-YLBORONIC ACID; 5-CHLORO-1H-INDOLE-2-BORONIC ACID; 5-CHLORO-1-METHYL-1H-INDOL-2-YLBORONIC ACID; 5-CHLORO-1-METHYL-PYRROL-3-YL-BORONIC ACID; 5-CHLORO-2-(ETHOXYCARBONYL)PHENYLBORONIC ACID; 5-CHLORO-2-(METHOXYCARBONYL)PHENYLBORONIC ACID; 5-CHLORO-2-(METHOXYMETHOXY)PHENYLBORONIC ACID; 5-CHLORO-2-(MORPHOLINE-4-CARBONYL)PHENYLBORONIC ACID; 5-CHLORO-2-(PIVALOYLAMINO)PHENYLBORONIC ACID; 5-CHLORO-2-(TRIFLUOROMETHOXY)PHENYLBORONIC ACID; 5-CHLORO-2-(TRIFLUOROMETHYL)PHENYLBORONIC ACID; 5'-CHLORO-2,2'-BITHIOPHEN-5-YLBORONIC ACID; 5-CHLORO-2,3-DIFLUOROPYRIDIN-4-YLBORONIC ACID; 5-CHLORO-2,4-DIFLUOROPHENYLBORONIC ACID; 5-CHLORO-2-CYANOPHENYLBORONIC ACID; 5-CHLORO-2-ETHOXYPHENYLBORONIC ACID; 5-CHLORO-2-ETHOXYPYRIDINE-3-BORONIC ACID; 5-CHLORO-2-FLUORO-3-METHYLPHENYLBORONIC ACID; 5-CHLORO-2-FLUORO-4-METHOXYPHENYLBORONIC ACID; 5-CHLORO-2-FLUORO-4-METHYLPHENYLBORONIC ACID; 5-CHLORO-2-FLUORO-4-PICOLINE-3-BORONIC ACID; 5-CHLORO-2-FLUOROPHENYLBORONIC ACID; 5-CHLORO-2-FLUOROPYRIDINE-3-BORONIC ACID; 5-CHLORO-2-FLUOROPYRIDINE-4-BORONIC ACID; 5-CHLORO-2-HYDROXYPHENYLBORONIC ACID; 5-CHLORO-2-HYDROXYPYRIDINE-4-BORONIC ACID; 5-CHLORO-2-ISOBUTOXYPYRIDINE-3-BORONIC ACID; 5-CHLORO-2-ISOPROPOXYPHENYLBORONIC ACID; 5-CHLORO-2-ISOPROPOXYPYRIDINE-3-BORONIC ACID; 5-CHLORO-2-METHOXYPHENYLBORONIC ACID; 5-CHLORO-2-METHOXYPYRIDINE-3-BORONIC ACID; 5-CHLORO-2-METHYL-3-NITROBENZENEBORONIC ACID; 5-CHLORO-2-METHYL-4-(TRIFLUOROMETHYL)PHENYLBORONIC ACID; 5-CHLORO-2-METHYLPHENYLBORONIC ACID; 5-CHLORO-2-METHYLPYRIDINE-3-BORONIC ACID; 5-CHLORO-2-NITROPHENYLBORONIC ACID; 5-CHLORO-2-PROPOXYPHENYLBORONIC ACID; 5-CHLORO-2-PROPOXYPYRIDIN-4-YLBORONIC ACID; 5-CHLORO-2-PROPOXYPYRIDINE-3-BO-

RONIC ACID; 5-CHLORO-3-METHOXYPYRIDINE-2-BORONIC ACID; 5-CHLORO-3-METHYLBENZO[B]THIOPHEN-2-YLBORONIC ACID; 5-CHLORO-3-METHYLPYRIDIN-2-YLBORONIC ACID; 5-CHLORO-4-METHOXY-2-METHYLPHENYLBORONIC ACID; 5-CHLORO-4-METHOXYPYRIDINE-2-BORONIC ACID; 5-CHLORO-4-METHOXYPYRIDINE-3-BORONIC ACID; 5-CHLORO-4-METHYLPYRIDINE-2-BORONIC ACID; 5-CHLORO-4-METHYLPYRIDINE-3-BORONIC ACID; 5-CHLORO-6-(4-CHLOROPHENYL)PYRIDIN-3-YLBORONIC ACID; 5-CHLORO-6-(4-CHLOROPHENYLAMINO)PYRIDIN-3-YLBORONIC ACID; 5-CHLORO-6-ETHOXYPYRIDINE-3-BORONIC ACID; 5-CHLORO-6-HYDROXYPYRIDIN-3-YLBORONIC ACID; 5-CHLORO-6-ISOPROPOXYPYRIDINE-3-BORONIC ACID; 5-CHLORO-6-OXO-1,6-DIHYDROPYRIDIN-3-YLBORONIC ACID; 5-CHLORO-6-PROPOXYPYRIDINE-3-BORONIC ACID; 5-CHLOROBENZOFURAN-2-YLBORONIC ACID; 5-CHLOROBIPHENYL-3-YLBORONIC ACID; 5-CHLOROPYRAZINE-2-BORONIC ACID; 5-CHLOROPYRIDINE-2-BORONIC ACID; 5-CHLOROPYRIDINE-3-BORONIC ACID; 5-CHLOROPYRIMIDINE-2-BORONIC ACID; 5-CHLOROPYRIMIDINE-4-BORONIC ACID; 5-CHLORO-PYRROL-3-YLBORONIC ACID; 5-CHLOROTHIOPHENE-2-BORONIC ACID; 5-CHLOROTHIOPHENE-3-BORONIC ACID; 5-CYANO-1H-INDOLE-2-BORONIC ACID; 5-CYANO-1-METHYL-1H-PYRROL-2-YLBORONIC ACID; 5-CYANO-2-(METHOXYMETHOXY)PHENYLBORONIC ACID; 5-CYANO-2-(TRIFLUOROMETHOXY)PHENYLBORONIC ACID; 5-CYANO-2-(TRIFLUOROMETHYL)PHENYLBORONIC ACID; 5-CYANO-2-FLUOROPHENYLBORONIC ACID; 5-CYANO-2-HYDROXYPHENYLBORONIC ACID; 5-CYANO-2-HYDROXYPYRIDIN-3-YLBORONIC ACID; 5-CYANO-2-METHOXYPHENYLBORONIC ACID; 5-CYANO-2-METHOXYPYRIDIN-3-YLBORONIC ACID; 5-CYANO-2-METHYLPHENYLBORONIC ACID; 5-CYANO-2-METHYLTHIOPHEN-3-YL-BORONIC ACID; 5-CYANO-2-OXO-1,2-DIHYDROPYRIDIN-3-YLBORONIC ACID; 5-CYANO-3-METHYLPYRIDIN-2-YL-BORONIC ACID; 5-CYANO-3-METHYLTHIOPHENE-2-BORONIC ACID; 5-CYANO-3-PYRIDINYL BORONIC ACID; 5-CYANO-4-METHYLTHIOPHENE-2-BORONIC ACID; 5-CYANO-6-ETHOXYPYRIDINE-3-BORONIC ACID; 5-CYANOBENZOFURAN-2-YLBORONIC ACID; 5-CYANOPYRAZINE-2-BORONIC ACID; 5-CYANOPYRIDIN-2-YL-2-BORONIC ACID; 5-CYANOTHIOPHEN-3-YLBORONIC ACID; 5-CYANOTHIOPHENE-2-BORONIC ACID; 5-CYCLOPROPYLPYRIDIN-3-YLBORONIC ACID; 5-ETHOXY-2-FLUOROPHENYLBORONIC ACID; 5-ETHOXYPYRAZINE-2-BORONIC ACID; 5-ETHOXYPYRIDIN-2-YLBORONIC ACID; 5-ETHOXYPYRIDINE-3-BORONIC ACID; 5-ETHOXYTHIOPHEN-2-YL-BORONIC ACID; 5-ETHYL-1,3,4-THIADIAZOL-2-YLBORONIC ACID; 5-ETHYL-1H-INDAZOL-4-YL BORONIC ACID; 5-ETHYLFURAN-2-BORONIC ACID; 5-ETHYLPYRIDIN-3-YLBORONIC ACID; 5-ETHYLTHIOPHENYLBORONIC ACID; 5-FLUORO-1-(TRIISOPROPYLSILYL)-PYRROL-3-YLBORONIC ACID; 5-FLUORO-1H-INDAZOL-6-YLBORONIC ACID; 5-FLUORO-1H-INDOL-2-YLBORONIC ACID; 5-FLUORO-1-METHYL-1H-INDAZOLE-6-BORONIC ACID; 5-FLUORO-1-METHYL-1H-INDOL-2-YLBORONIC ACID; 5-FLUORO-1-METHYL-PYRROL-3-YL-BORONIC ACID; 5-FLUORO-2-(1,2,4-OXADIAZOL-3-YL)PHENYLBORONIC ACID; 5-FLUORO-2-(4-FLUOROPHENYLMETHOXY)PHENYLBORONIC ACID; 5-FLUORO-2-(5-PROPYL-1,3,4-OXADIAZOL-2-YL)PHENYLBORONIC ACID; 5-FLUORO-2-(METHOXYMETHOXY)PHENYLBORONIC ACID; 5-FLUORO-2-(MORPHOLINOCARBONYL)PHENYLBORONIC ACID; 5-FLUORO-2-(TRIFLUOROETHOXY)PHENYLBORONIC ACID; 5-FLUORO-2-(TRIFLUOROMETHYL)PHENYLBORONIC ACID; 5-FLUORO-2,3-DIMETHOXYPHENYLBORONIC ACID; 5-FLUORO-2-HYDROXYMETHYLPHENYLBORONIC ACID; 5-FLUORO-2-HYDROXYPHENYLBORONIC ACID; 5-FLUORO-2-HYDROXYPYRIDINE-4-BORONIC ACID; 5-FLUORO-2-ISOPROPOXYPHENYLBORONIC ACID; 5-FLUORO-2-ISOPROPOXYPYRIDINE-4-BORONIC ACID; 5-FLUORO-2-METHOXYCARBONYLPHENYLBORONIC ACID; 5-FLUORO-2-METHOXYPHENYLBORONIC ACID; 5-FLUORO-2-METHOXYPYRIDINE-3-BORONIC ACID; 5-FLUORO-2-METHOXYPYRIDINE-4-BORONIC ACID; 5-FLUORO-2-METHYLPHENYLBORONIC ACID; 5-FLUORO-2-METHYLPYRIDINE-4-BORONIC ACID; 5-FLUORO-2-NITROBENZENEBORONIC ACID; 5-FLUORO-2-PROPOXYPHENYLBORONIC ACID; 5-FLUORO-3-METHYLBENZO[B]THIOPHEN-2-YL-BORONIC ACID; 5-FLUORO-3-NITROPYRIDIN-2-YL-BORONIC ACID; 5-FLUORO-4-METHOXYPYRIMIDIN-2-YLBORONIC ACID; 5-FLUORO-6-HYDROXYPYRIDIN-3-YLBORONIC ACID; 5-FLUORO-6-METHYLPYRIDINE-2-BORONIC ACID; 5-FLUOROBENZOFURAN-2-YLBORONIC ACID; 5-FLUOROBENZOTHIOPHENE-2-BORONIC ACID; 5-FLUOROPYRAZINE-2-BORONIC ACID; 5-FLUOROPYRIDINE-2-BORONIC ACID; 5-FLUOROPYRIDINE-3-BORONIC ACID; 5-FLUORO-PYRROL-3-YLBORONIC ACID; 5-FLUOROQUINOLINE-8-BORONIC ACID; 5H-[1,3]DIOXOLO[4,5-F]INDOL-7-YLBORONIC ACID; 5-HEXENYLBORONIC ACID; 5-HEXYLTHIOPHENE-2-BORONIC ACID; 5-HEXYLTHIOPHENE-3-BORONIC ACID; 5-HYDROXY-2-(TRIFLUOROMETHOXY)PHENYLBORONIC ACID; 5-HYDROXY-2-(TRIFLUOROMETHYL)PHENYLBORONIC ACID; 5-HYDROXY-2-METHOXYPHENYLBORONIC ACID; 5-HYDROXY-2-METHYLPHENYLBORONIC ACID; 5-HYDROXYBENZOTHIAZOLE-2-BORONIC ACID; 5-HYDROXYMETHYL-2-METHOXYPHENYLBORONIC ACID; 5-HYDROXYMETHYLTHIOPHENE-2-BORONIC ACID; 5-HYDROXYNAPHTHALENE-1-BORONIC ACID; 5-HYDROXYNAPHTHALENE-2-BORONIC ACID; 5-HYDROXYPYRAZINE-2-BORONIC ACID; 5-HYDROXYPYRIDINE-3-BORONIC ACID; 5-HYDROXYQUINOLINE-2-BORONIC ACID; 5-HYDROXYQUINOLINE-3-BORONIC ACID; 5-HYDROXYQUINOLINE-4-BORONIC ACID; 5-HYDROXYQUINOLINE-6-BORONIC ACID; 5-HYDROXYQUINOLINE-7-BORONIC ACID; 5-HYDROXYQUINOLINE-8-BORONIC ACID; 5-INDOLYLBORONIC ACID; 5-ISOPROPYL-2-METHOXYPHENYLBORONIC ACID; 5-ISOPROPYL-2-METHOXYQUINOLIN-3-YLBORONIC ACID; 5-ISOPROPYLTHIOPHENE-3-BORONIC ACID; 5-METHOXY-1-(PHENYLSULFONYL)-1H-PYRROLO[3,2-B]PYRIDIN-2-YLBORONIC ACID; 5-METHOXY-1-[(4-METHYLPHENYL)SULFONYL]-1H-INDOL-3-YLBORONIC ACID; 5-METHOXY-1H-INDOL-3-YLBORONIC ACID; 5-METHOXY-1H-INDOLE-

2-BORONIC ACID; 5-METHOXY-1H-PYRROLO[3,2-B]PYRIDIN-6-YLBORONIC ACID; 5-METHOXY-1-METHYL-1H-INDOL-3-YLBORONIC ACID; 5-METHOXY-2-(METHOXYMETHOXY)PHENYLBORONIC ACID; 5-METHOXY-2-(TRIFLUOROMETHOXY)PHENYLBORONIC ACID; 5-METHOXY-2-(TRIFLUOROMETHYL)PHENYLBORONIC ACID; 5-METHOXY-2-METHYLPHENYLBORONIC ACID; 5-METHOXYBENZO[B]THIOPHENE-2-BORONIC ACID; 5-METHOXYBENZOFURAN-2-BORONIC ACID; 5-METHOXYBENZOTHIAZOLE-2-BORONIC ACID; 5-METHOXYCARBONYL-1H-INDOLE-2-BORONIC ACID; 5-METHOXYCARBONYL-2-METHYLPHENYLBORONIC ACID; 5-METHOXYFURAN-2-YLBORONIC ACID; 5-METHOXYPYRAZINE-2-BORONIC ACID; 5-METHOXYPYRIDINE-2-BORONIC ACID; 5-METHOXYPYRIDINE-3-BORONIC ACID; 5-METHOXYTHIOPHENE-2-BORONIC ACID; 5-METHYL-1-(TRIISOPROPYLSILYL)-PYRROL-3-YL-BORONIC ACID; 5-METHYL-1-HEXENYLBORONIC ACID; 5-METHYL-1H-INDAZOLE-4-BORONIC ACID; 5-METHYL-1H-INDAZOLE-6-BORONIC ACID; 5-METHYL-1H-INDOL-4-YLBORONIC ACID; 5-METHYL-1H-INDOLE-2-BORONIC ACID; 5-METHYL-1-PHENYL-1H-PYRAZOL-4-YLBORONIC ACID; 5-METHYL-2-(2-(TRIFLUOROMETHOXY)PHENYL)PYRIDINE-3-BORONIC ACID; 5-METHYL-2-(2-(TRIFLUOROMETHOXY)PHENYL)PYRIDINE-4-BORONIC ACID; 5-METHYL-2-(2-(TRIFLUOROMETHYL)PHENYL)PYRIDINE-3-BORONIC ACID; 5-METHYL-2-(2-(TRIFLUOROMETHYL)PHENYL)PYRIDINE-4-BORONIC ACID; 5-METHYL-2-(2,4,5-TRICHLOROPHENYL)PYRIDINE-3-BORONIC ACID; 5-METHYL-2-(2,4,5-TRICHLOROPHENYL)PYRIDINE-4-BORONIC ACID; 5-METHYL-2-(3-(TRIFLUOROMETHOXY)PHENYL)PYRIDINE-3-BORONIC ACID; 5-METHYL-2-(3-(TRIFLUOROMETHOXY)PHENYL)PYRIDINE-4-BORONIC ACID; 5-METHYL-2-(3-(TRIFLUOROMETHYL)PHENYL)PYRIDINE-3-BORONIC ACID; 5-METHYL-2-(3-(TRIFLUOROMETHYL)PHENYL)PYRIDINE-4-BORONIC ACID; 5-METHYL-2-(4-(TRIFLUOROMETHOXY)PHENYL)PYRIDINE-3-BORONIC ACID; 5-METHYL-2-(4-(TRIFLUOROMETHOXY)PHENYL)PYRIDINE-4-BORONIC ACID; 5-METHYL-2-(4-(TRIFLUOROMETHYL)PHENYL)PYRIDINE-3-BORONIC ACID; 5-METHYL-2-(4-(TRIFLUOROMETHYL)PHENYL)PYRIDINE-4-BORONIC ACID; 5-METHYL-2-(METHYLTHIO)PHENYLBORONIC ACID; 5-METHYL-2-(PERFLUOROPHENYL)PYRIDINE-3-BORONIC ACID; 5-METHYL-2-(PERFLUOROPHENYL)PYRIDINE-4-BORONIC ACID; 5-METHYL-2-(TRIFLUOROMETHOXY)PHENYLBORONIC ACID; 5-METHYL-2-(TRIFLUOROMETHYL)PHENYLBORONIC ACID; 5-METHYL-2-OXO-1,2-DIHYDROPYRIDIN-4-YLBORONIC ACID; 5-METHYL-2-PENTYLOXYPYRIDINE-3-BORONIC ACID; 5-METHYL-2-PROPOXYPHENYLBORONIC ACID; 5-METHYL-3-PHENYL-4-ISOXAZOLYLBORONIC ACID; 5-METHYL-5H-PYRROLO[2,3-B]PYRAZIN-3-YLBORONIC ACID; 5-METHYL-6-(METHYL-D3)-PYRIDINE-3-BORONIC ACID; 5-METHYL-6-(METHYLTHIO)PYRIDIN-3-YL-BORONIC ACID; 5-METHYL-6-(MORPHOLIN-4-YL)PYRIDINE-3-BORONIC ACID; 5-METHYL-6-MORPHOLINOPYRIDIN-3-YLBORONIC ACID HYDROCHLORIDE; 5-METHYL-6-THIOMORPHOLINOPYRIDIN-3-YLBORONIC ACID; 5-METHYLBENZO[B]THIOPHEN-3-YLBORONIC ACID; 5-METHYLBENZO[B]THIOPHENE-2-BORONIC ACID; 5-METHYLFURAN-2-BORONIC ACID; 5-METHYLFURAN-3-YLBORONIC ACID; 5-METHYLISOXAZOL-4-YLBORONIC ACID; 5-METHYLPYRAZINE-2-BORONIC ACID; 5-METHYLPYRIDINE-2-BORONIC ACID; 5-METHYLPYRIDINE-3-BORONIC ACID; 5-METHYL-PYRROL-3-YLBORONIC ACID; 5-METHYLTHIOPHENE-2-BORONIC ACID; 5-METHYLTHIOPHENE-3-BORONIC ACID; 5-MORPHOLINOPYRAZINE-2-BORONIC ACID; 5-MORPHOLINOPYRIDIN-2-YLBORONIC ACID; 5-MORPHOLINOPYRIDIN-3-YLBORONIC ACID; 5-NITRO-1H-INDOL-2-YLBORONIC ACID; 5-NITROISOQUINOLINE-8-BORONIC ACID; 5-NITROPYRIDIN-2-YLBORONIC ACID; 5-PENTYLOXYTHIOPHENE-2-BORONIC ACID; 5-PENTYLTHIOPHENE-2-BORONIC ACID; 5-PENTYLTHIOSELENOPHENE-2-BORONIC ACID; 5-PHENYL-1H-PYRROLO[2,3-B]PYRIDINE-2-BORONIC ACID; 5-PHENYL-1H-PYRROLO[2,3-B]PYRIDINE-3-BORONIC ACID; 5-PHENYL-1H-PYRROLO[2,3-B]PYRIDINE-4-BORONIC ACID; 5-PHENYL-1H-PYRROLO[2,3-B]PYRIDINE-6-BORONIC ACID; 5-PHENYL-2-THIENYLBORONIC ACID; 5-PHENYL-3-PYRIDINYL BORONIC ACID; 5-PHENYLFURAN-2-BORONIC ACID; 5-PHENYLPYRIDINE-2-BORONIC ACID; 5-PHENYLPYRIMIDINE-2-BORONIC ACID; 5-PHENYLPYRIMIDINE-4-BORONIC ACID; 5-PHENYL-PYRROL-3-YLBORONIC ACID; 5-PHENYLTHIOPHEN-3-YLBORONIC ACID; 5-PROPOXYBENZOFURAN-2-YLBORONIC ACID; 5-PROPYLPYRIMIDIN-2-YLBORONIC ACID; 5-PROPYLTHIOPHENE-2-BORONIC ACID; 5-SULFAMOYLPYRIDINE-3-BORONIC ACID; 5-SULFAMOYLTHIOPHEN-2-YLBORONIC ACID; 5-TERT-BUTOXYCARBONYLTHIOPHENE-2-BORONIC ACID; 5-TERT-BUTYL-2-CHLOROPHENYLBORONIC ACID; 5-TERT-BUTYL-2-ETHOXYPHENYLBORONIC ACID; 5-TERT-BUTYL-2-FURANBORONIC ACID; 5-TERT-BUTYL-2-METHOXYBENZENEBORONIC ACID; 5-TERT-BUTYLTHIOPHENE-2-BORONIC ACID; 5-TERT-BUTYLTHIOPHENE-3-BORONIC ACID; 5-TRIFLUOROMETHYL-1H-PYRAZOL-3-YLBORONIC ACID; 5-TRIFLUOROMETHYL-1H-PYRAZOL-4-YLBORONIC ACID; 5-TRIFLUOROMETHYLPYRIDINE-3-BORONIC ACID; 5-TRIFLUOROMETHYLQUINOLINE-8-BORONIC ACID; 5-TRIMETHYLSILYLTHIOPHENE-2-BORONIC ACID; 6-(1,4-DIOZA-8-AZASPIRO[4.5]DEC-8-YL)PYRIDINE-3-BORONIC ACID; 6-(1-CYANOCYCLOPROPYL)PYRIDINE-3-BORONIC ACID; 6-(1H-1,2,4-TRIAZOL-1-YL)PYRIDIN-3-YLBORONIC ACID; 6-(1H-IMIDAZOL-2-YL)PYRIDIN-3-YLBORONIC ACID; 6-(1H-PYRIDIN-2-ONE)PYRIDINE-2-BORONIC ACID; 6-(1-METHYL-1H-TETRAZOL-5-YL)PYRIDIN-3-YLBORONIC ACID; 6-(2-(METHOXYMETHOXY)PROPAN-2-YL)PYRIDIN-2-YLBORONIC ACID; 6-(2-(TRIFLUOROMETHOXY)PHENYL)-2-(TRIFLUOROMETHYL)PYRIDINE-3-BORONIC ACID; 6-(2,3-DIFLUOROPHENYL)-2-(TRIFLUOROMETHYL)PYRIDINE-3-BORONIC ACID; 6-(2,3-DIFLUOROPHENYL)-2-METHYLPYRIDINE-3-BORONIC ACID; 6-(2,4,5-TRICHLOROPHENYL)-2-(TRIFLUOROMETHYL)PYRIDINE-3-BORONIC ACID; 6-(2,4-DIMETHYLPHENOXY)PYRIDIN-3-YLBORONIC ACID; 6-(2-CYANOPROPAN-2-YL)PYRIDIN-3-

YLBORONIC ACID; 6-(2-ETHYLIMIDAZOL-1-YL)PYRIDINE-2-BORONIC ACID; 6-(2-FURYL)PYRIDINE-2-BORONIC ACID; 6-(2-HYDROXYPROPAN-2-YL)PYRIDINE-2-BORONIC ACID; 6-(2-HYDROXYPROPAN-2-YL)PYRIDINE-3-BORONIC ACID; 6-(2-METHOXY-2-OXOETHOXY)PYRIDINE-3-BORONIC ACID; 6-(2-METHYL-2H-TETRAZOL-5-YL)PYRIDIN-3-YLBORONIC ACID; 6-(2-METHYLIMIDAZOL-1-YL)PYRIDINE-2-BORONIC ACID; 6-(2-METHYLPHENYL)PYRIDINE-2-BORONIC ACID; 6-(2-METHYLPIPERIDIN-1-YL)PYRIDINE-2-BORONIC ACID; 6-(2-MORPHOLINOETHOXY)PYRIDINE-3-BORONIC ACID; 6-(2-THIENYL)PYRIDINE-2-BORONIC ACID; 6-(3-(TRIFLUOROMETHOXY)PHENYL)-2-(TRIFLUOROMETHYL)PYRIDINE-3-BORONIC ACID; 6-(3-FURAN)PYRIDINE-2-BORONIC ACID; 6-(3-HYDROXYOXETAN-3-YL)PYRIDIN-3-YLBORONIC ACID; 6-(3-HYDROXYPYRROLIDIN-1-YL)PYRIDINE-2-BORONIC ACID; 6-(3-METHYL-1H-PYRAZOL-1-YL)PYRIDINE-2-BORONIC ACID; 6-(3-METHYLPHENYL)PYRIDINE-2-BORONIC ACID; 6-(3-METHYLPIPERIDIN-1-YL)PYRIDINE-2-BORONIC ACID; 6-(3-THIENYL)PYRIDINE-2-BORONIC ACID; 6-(4-(TRIFLUOROMETHOXY)PHENYL)-2-(TRIFLUOROMETHYL)PYRIDINE-3-BORONIC ACID; 6-(4-ACETYLPIPERAZIN-1-YL)PYRIDIN-3-YLBORONIC ACID; 6-(4-CHLOROPHENOXY)PYRIDIN-3-YLBORONIC ACID; 6-(4-FLUOROPHENYL)PYRIDINE-3-BORONIC ACID; 6-(4-HYDROXYPIPERIDIN-1-YL)PYRAZINE-2-BORONIC ACID; 6-(4-METHOXYBENZYLCARBAMOYL)PYRIDINE-3-BORONIC ACID; 6-(4-METHOXYBENZYLOXY)PYRIDIN-3-YLBORONIC ACID; 6-(4-METHOXYPHENOXY)PYRIDIN-3-YLBORONIC ACID; 6-(4-METHYL-1H-PYRAZOL-1-YL)PYRIDINE-2-BORONIC ACID; 6-(4-METHYLPHENOXY)PYRIDIN-3-YLBORONIC ACID; 6-(4-METHYLPHENYL)PYRIDINE-2-BORONIC ACID; 6-(4-METHYLPIPERAZIN-1-YL)PYRIDINE-2-BORONIC ACID; 6-(4-METHYLPIPERIDIN-1-YL)PYRIDINE-2-BORONIC ACID; 6-(4-MORPHOLINYL)-3-PYRIDINYLBORONIC ACID; 6-(4-MORPHOLINYLMETHYL)-3-PYRIDINYL BORONIC ACID; 6-(4-N-BOC-PIPERAZINE-1-YL)-3-PYRIDINYL BORONIC ACID; 6-(5-CHLOROPYRIDIN-3-YLOXY)PYRIDIN-3-YLBORONIC ACID; 6-(5-METHYL-1,3,4-OXADIAZOL-2-YL)PYRIDIN-3-YLBORONIC ACID; 6-(6-CHLOROPYRIDIN-3-YLOXY)PYRIDIN-3-YLBORONIC ACID; 6-(AMINOCARBONYL)PYRIDINE-3-BORONIC ACID; 6-(AZEPAN-1-YL)PYRIDIN-3-YLBORONIC ACID; 6-(BENZYLOXY)-2-NAPHTHYLBORONIC ACID; 6-(BENZYLOXY)-5,6,7,8-TETRAHYDRONAPHTHALEN-2-YLBORONIC ACID; 6-(BOC-METHYLAMINO)PYRIDINE-3-BORONIC ACID; 6-(CYCLOBUTOXY)PYRIDINE-2-BORONIC ACID; 6-(CYCLOBUTYLAMINO)PYRIDINE-2-BORONIC ACID; 6-(CYCLOHEXYL)PYRIDINE-2-BORONIC ACID; 6-(CYCLOHEXYLAMINO)PYRIDINE-2-BORONIC ACID; 6-(CYCLOHEXYLOXY)PYRIDINE-2-BORONIC ACID; 6-(CYCLOPENTOXY)PYRIDINE-2-BORONIC ACID; 6-(CYCLOPENTYL)PYRIDINE-2-BORONIC ACID; 6-(CYCLOPENTYLAMINO)PYRIDINE-2-BORONIC ACID; 6-(CYCLOPROPYLAMINO)PYRIDINE-2-BORONIC ACID; 6-(CYCLOPROPYLMETHOXY)PYRAZIN-2-YL-BORONIC ACID; 6-(DIETHYLAMINO)-4-ETHYLPYRIDIN-3-YLBORONIC ACID; 6-(DIETHYLAMINO)PYRIDINE-2-BORONIC ACID; 6-(DIETHYLAMINO)PYRIDINE-3-BORONIC ACID; 6-(DIFLUOROMETHOXY)BENZOTHIAZOLE-2-BORONIC ACID; 6-(DIMETHOXYMETHYL)PYRIDIN-2-YLBORONIC ACID; 6-(DIMETHYLAMINO)-2-FLUOROPYRIDIN-3-YLBORONIC ACID; 6-(DIMETHYLAMINO)-2-METHYLPYRIDINE-3-BORONIC ACID; 6-(DIMETHYLAMINO)-4-ETHYLPYRIDINE-3-BORONIC ACID; 6-(DIMETHYLAMINO)-4-ISOPROPOXYPYRIDIN-3-YLBORONIC ACID; 6-(DIMETHYLAMINO)-4-METHOXYPYRIDIN-3-YLBORONIC ACID; 6-(DIMETHYLAMINO)-4-METHYLPYRIDINE-3-BORONIC ACID; 6-(DIMETHYLAMINO)-5-METHYLPYRIDIN-3-YLBORONIC ACID; 6-(DIMETHYLAMINO)PYRIDINE-2-BORONIC ACID; 6-(DIMETHYLAMINO)PYRIDINE-3-BORONIC ACID; 6-(DIMETHYLCARBAMOYL)PYRIDINE-3-BORONIC ACID; 6-(ETHANESULFONYL)PYRIDINE-3-BORONIC ACID; 6-(ETHYL(METHYL)AMINO)PYRIDINE-3-BORONIC ACID; 6-(ETHYLAMINO)PYRIDINE-3-BORONIC ACID; 6-(ETHYLCARBAMOYL)PYRIDIN-3-YLBORONIC ACID; 6-(ETHYLTHIO)-5-METHYLPYRIDIN-3-YLBORONIC ACID; 6-(HYDROXYMETHYL)NAPHTHALENE-1-BORONIC ACID; 6-(HYDROXYMETHYL)NAPHTHALENE-2-BORONIC ACID; 6-(HYDROXYMETHYL)PYRIDINE-2-BORONIC ACID; 6-(HYDROXYMETHYL)PYRIDINE-3-BORONIC ACID; 6-(IMIDAZOL-1-YL)PYRIDINE-2-BORONIC ACID; 6-(ISO-PROPOXY)PYRIDINE-2-BORONIC ACID; 6-(ISOPROPYLAMINO)PYRIDINE-3-BORONIC ACID; 6-(ISO-PROPYL-D7)-PYRIDINE-3-BORONIC ACID; 6-(ISOPROPYLTHIO)PYRIDINE-3-BORONIC ACID; 6-(METHOXYCARBONYL)INDOLE-2-BORONIC ACID; 6-(METHOXYCARBONYL)PYRIDINE-2-BORONIC ACID; 6-(METHOXYCARBONYL)PYRIDINE-3-BORONIC ACID; 6-(METHOXYMETHOXY)PYRIDIN-3-YLBORONIC ACID; 6-(METHYLAMINO)PYRIDIN-3-YLBORONIC ACID; 6-(METHYLAMINO)PYRIDIN-3-YLBORONIC ACID HYDROCHLORIDE; 6-(METHYLCARBAMOYL)PYRIDIN-3-YLBORONIC ACID; 6-(METHYL-D3)-PYRIDINE-3-BORONIC ACID; 6-(MORPHOLINOMETHYL)PYRIDIN-3-YLBORONIC ACID; 6-(N,N-METHYLETHYLAMINO)PYRIDINE-2-BORONIC ACID; 6-(NEOPENTYLOXY)PYRIDINE-3-BORONIC ACID; 6-(N-PROPOXY)PYRIDINE-2-BORONIC ACID; 6-(PERFLUOROPHENYL)-2-(TRIFLUOROMETHYL)PYRIDINE-3-BORONIC ACID; 6-(PHENYLTHIO)PYRIDIN-3-YLBORONIC ACID; 6-(PIPERAZIN-1-YL)PYRIDINE-3-BORONIC ACID; 6-(PIPERIDIN-1-YL)PYRAZINE-2-BORONIC ACID; 6-(PIPERIDIN-1-YL)PYRIDIN-3-YLBORONIC ACID; 6-(PIPERIDIN-1-YL)PYRIDINE-2-BORONIC ACID; 6-(PIVALAMIDO)PYRIDINE-3-BORONIC ACID; 6-(PROP-1-YNYL)PYRAZIN-2-YLBORONIC ACID; 6-(PROP-1-YNYL)PYRIMIDIN-4-YLBORONIC ACID; 6-(PROPYLAMINO)PYRIDINE-3-BORONIC ACID; 6-(PYRIDIN-3-YLOXY)PYRIDINE-3-BORONIC ACID; 6-(PYRROL-1-YL)-3-PYRIDINYL BORONIC ACID; 6-(PYRROLIDIN-1-YL)PYRAZINE-2-BORONIC ACID; 6-(PYRROLIDIN-1-YL)PYRIDINE-2-BORONIC ACID; 6-(PYRROLIDIN-1-YL)PYRIDINE-3-BORONIC ACID; 6-(QUINOLIN-3-YL)PYRIDIN-3-YLBORONIC ACID; 6-(TERT-BUTOXY)PYRIDINE-2-BORONIC ACID; 6-(TERT-BUTOXYCARBONYLAMINO)PYRIDIN-3-YLBORONIC ACID; 6-(TERT-BUTOXYMETHYL)PYRIDIN-3-YLBORONIC ACID; 6-(TERT-BUTYL)PYRI-

DINE-2-BORONIC ACID; 6-(TERT-BUTYLDIMETHYLSILYLOXY)-1H-INDOL-2-YLBORONIC ACID; 6-(TETRAHYDRO-2H-PYRAN-2-YLOXY)-2-NAPHTHYLBORONIC ACID; 6-(TETRAHYDRO-2H-PYRAN-4-YLOXY)PYRIDIN-3-YLBORONIC ACID; 6-(TETRAHYDRO-FURAN-3-YLOXY)PYRIDINE-2-BORONIC ACID; 6-(TRIFLUOROMETHYL)-2-(2-(TRIFLUOROMETHYL)PHENYL)PYRIDINE-3-BORONIC ACID; 6-(TRIFLUOROMETHYL)-2-(3-(TRIFLUOROMETHYL)PHENYL)PYRIDINE-3-BORONIC ACID; 6-(TRIFLUOROMETHYL)-2-(4-(TRIFLUOROMETHYL)PHENYL)PYRIDINE-3-BORONIC ACID; 6-(TRIFLUOROMETHYL)PYRIDINE-2-BORONIC ACID; 6,6,6-TRIFLUOROHEXANEBORONIC ACID; 6,7-DIHYDRO-5H-CYCLOPENTA[B]PYRIDINE-2-BORONIC ACID; 6,7-DIMETHOXY-1-METHYL-1H-INDOL-2-YLBORONIC ACID; 6-[(4-CHLOROPHENYL)THIO]PYRIDIN-3-YLBORONIC ACID; 6-[(4-METHYLPHENYL)THIO]PYRIDIN-3-YLBORONIC ACID; 6-[(BENZYLOXY)METHYL]PYRIDINE-2-BORONIC ACID; 6-[(DIETHYLAMINO)CARBONYL]PYRIDINE-3-BORONIC ACID; 6-[4-(TERT-BUTOXYCARBONYL)PIPERAZIN-1-YL]PYRIDINE-2-BORONIC ACID; 6-ACETAMIDO-4-METHYLPYRIDINE-3-BORONIC ACID; 6-ACETAMIDO-5-METHYLPYRIDIN-3-YLBORONIC ACID; 6-ACETOXYNAPHTHALEN-2-YLBORONIC ACID; 6-AMINO-2-(TRIFLUOROMETHYL)PYRIDINE-3-BORONIC ACID; 6-AMINO-2-FLUOROPYRIDIN-3-YLBORONIC ACID; 6-AMINO-2-METHOXYPYRIDINE-3-BORONIC ACID; 6-AMINO-2-METHOXYPYRIDINE-4-BORONIC ACID; 6-AMINO-2-METHYLPYRIDINE-3-BORONIC ACID; 6-AMINO-2-METHYLPYRIMIDIN-4-YLBORONIC ACID; 6-AMINO-4-(TRIFLUOROMETHYL)PYRIDIN-3-YLBORONIC ACID; 6-AMINO-4-CHLOROPYRIDIN-3-YLBORONIC ACID; 6-AMINO-5-FLUOROPYRIDINE-3-BORONIC ACID; 6-AMINO-5-METHOXYPYRIDIN-3-YLBORONIC ACID; 6-AMINO-5-METHYLPYRIDINE-3-BORONIC ACID; 6-AMINO-5-SULFAMOYLPYRIDINE-3-BORONIC ACID; 6-AMINOPYRAZINE-2-BORONIC ACID; 6-AMINOPYRIDAZIN-3-YL-3-BORONIC ACID; 6-AMINOPYRIDINE-2-BORONIC ACID; 6-AMINOPYRIDINE-3-BORONIC ACID-HCL; 6-BENZOXY-5-FLUOROPYRIDINE-3-BORONIC ACID; 6-BENZYLOXY-1-BOC-INDOLE-2-BORONIC ACID; 6-BENZYLOXY-1H-INDOLE-2-BORONIC ACID; 6-BENZYLOXY-2-FLUORO-3-METHYLPHENYLBORONIC ACID; 6-BENZYLOXYPYRIDINE-3-BORONIC ACID; 6-BORONOBENZO[D][1,3]DIOXOLE-5-CARBOXYLIC ACID; 6-BUTOXY-5-CHLOROPYRIDINE-3-BORONIC ACID; 6-BUTOXY-5-METHYLPYRIDINE-3-BORONIC ACID; 6-BUTOXYPYRIDINE-3-BORONIC ACID; 6-CARBOXY-2-NAPHTHALENEBORONIC ACID; 6-CARBOXYPYRIDINE-3-BORONIC ACID; 6-CHLORO-(4-TRIFLUOROMETHYL)PYRIDINE-3-BORONIC ACID; 6-CHLORO(PYRAZINE-D2)-2-BORONIC ACID; 6-CHLORO-1-METHYL-1H-PYRROLO[2,3-B]PYRIDIN-2-YLBORONIC ACID; 6-CHLORO-1-METHYLINDOLE-2-BORONIC ACID; 6-CHLORO-2-(TRIFLUOROMETHYL)PYRIDINE-3-BORONIC ACID; 6'-CHLORO-2,3'-BIPYRIDIN-5-YLBORONIC ACID; 6-CHLORO-2,3-DIFLUOROPHENYLBORONIC ACID; 6-CHLORO-2-FLUORO-3-METHOXYPHENYLBORONIC ACID; 6-CHLORO-2-FLUOROPYRIDINE-3-BORONIC ACID; 6-CHLORO-2-METHOXYPYRIDINE-3-BORONIC ACID; 6-CHLORO-2-METHYLPYRIDINE-3-BORONIC ACID; 6-CHLORO-2-METHYLPYRIMIDINE-4-BORONIC ACID; 6-CHLORO-3-METHOXYPYRIDINE-2-BORONIC ACID; 6-CHLORO-3-METHYLPYRIDINE-2-BORONIC ACID; 6-CHLORO-3-OXOISOINDOLIN-5-YLBORONIC ACID; 6-CHLORO-4-(TRIFLUOROMETHYL)PYRIDINE-2-BORONIC ACID; 6-CHLORO-4-FLUOROPYRIDINE-3-BORONIC ACID; 6-CHLORO-4-METHOXYPYRIDINE-2-BORONIC ACID; 6-CHLORO-4-METHYLPYRIDINE-2-BORONIC ACID; 6-CHLORO-5-METHOXYPYRIDINE-3-BORONIC ACID; 6-CHLOROBENZO[B]THIOPHEN-3-YLBORONIC ACID; 6-CHLOROPYRAZINE-2-BORONIC ACID; 6-CHLOROPYRIDAZIN-3-YL-3-BORONIC ACID; 6-CHLOROPYRIDINE-2-BORONIC ACID; 6-CHLOROPYRIMIDINE-4-BORONIC ACID; 6-CYANO-3-METHYLBENZO[B]THIOPHEN-2-YLBORONIC ACID; 6-CYANO-3-OXOISOINDOLIN-5-YLBORONIC ACID; 6-CYANOBENZO[B]THIOPHEN-2-YLBORONIC ACID; 6-CYANOPYRAZINE-2-BORONIC ACID; 6-CYANOPYRIDIN-3-YLBORONIC ACID; 6-CYANOPYRIDINE-2-BORONIC ACID; 6-CYCLOPROPYLPYRIDIN-3-YLBORONIC ACID; 6-CYCLOPROPYLPYRIDINE-2-BORONIC ACID; 6-ETHOXY-2-METHYLPYRIDINE-3-BORONIC ACID; 6-ETHOXY-2-NAPHTHALENEBORONIC ACID; 6-ETHOXYPYRIDINE-2-BORONIC ACID; 6-ETHYL-1,6-DIHYDROPYRIMIDIN-5-YLBORONIC ACID; 6-ETHYLPYRIDINE-2-BORONIC ACID; 6-FLUORO-1H-INDOLE-2-BORONIC ACID; 6-FLUORO-1-METHYL-1H-INDOL-2-YLBORONIC ACID; 6-FLUORO-2-(2-METHOXYETHOXY)PYRIDIN-3-YLBORONIC ACID; 6-FLUORO-2-(TRIFLUOROMETHYL)PYRIDINE-3-BORONIC ACID; 6-FLUORO-2,3'-BIPYRIDIN-5-YLBORONIC ACID; 6-FLUORO-3-OXOISOINDOLIN-5-YLBORONIC ACID; 6-FLUOROBENZO[B]THIEN-2-YL BORONIC ACID; 6-FLUOROPYRIDAZIN-3-YLBORONIC ACID; 6-FLUOROPYRIDINE-2-BORONIC ACID; 6-FLUOROQUINOLINE-8-BORONIC ACID; 6-HYDROXY-2-(TRIFLUOROMETHYL)PYRIDINE-3-BORONIC ACID; 6-HYDROXY-2-METHYLPYRIDINE-3-BORONIC ACID; 6-HYDROXY-2-NAPHTHALENEBORONIC ACID; 6-HYDROXY-5-(TETRAHYDROPYRAN-2-YL)NAPHTHALENE-2-BORONIC ACID; 6-HYDROXYBENZOTHIAZOLE-2-BORONIC ACID; 6-HYDROXYNAPHTHALENE-1-BORONIC ACID; 6-HYDROXYPYRIDIN-3-YLBORONIC ACID; 6-HYDROXYPYRIDINE-2-BORONIC ACID; 6-HYDROXYQUINOLINE-2-BORONIC ACID; 6-HYDROXYQUINOLINE-3-BORONIC ACID; 6-HYDROXYQUINOLINE-4-BORONIC ACID; 6-HYDROXYQUINOLINE-5-BORONIC ACID; 6-HYDROXYQUINOLINE-7-BORONIC ACID; 6-HYDROXYQUINOLINE-8-BORONIC ACID; 6-INDAZOLYBORONIC ACID; 6-INDAZOLYBORONIC ACID HCL; 6-ISOBUTOXY-5-METHYLPYRIDINE-3-BORONIC ACID; 6-ISOPROPOXYBENZO[B]THIOPHEN-2-YLBORONIC ACID; 6-ISOPROPYL-2-METHYLBENZENEBORONIC ACID; 6-ISO-PROPYLPYRIDINE-2-BORONIC ACID; 6-METHOXY-1,5-NAPHTHYRIDINE-4-BORONIC ACID; 6-METHOXY-1,7-NAPHTHYRIDIN-4-YLBORONIC ACID; 6-METHOXY-1H-INDOL-2-YLBORONIC ACID; 6-METHOXY-1H-INDOL-3-YLBORONIC ACID; 6-METHOXY-2-(TRIFLUOROMETHYL)PYRIDINE-3-

BORONIC ACID; 6-METHOXY-2-ETHYLPYRIDINE-3-BORONIC ACID; 6-METHOXY-2-NAPHTHALENEBORONIC ACID; 6-METHOXY-3-OXOISOINDOLIN-5-YLBORONIC ACID; 6-METHOXY-5-METHYLPYRIDINE-3-BORONIC ACID; 6-METHOXYBENZO[B]THIOPHENE-2-BORONIC ACID; 6-METHOXYBENZOFURAN-2-BORONIC ACID; 6-METHOXYBENZOTHIAZOLE-2-BORONIC ACID; 6-METHOXYPYRIDAZIN-3-YL-3-BORONIC ACID; 6-METHOXYPYRIDINE-2-BORONIC ACID; 6-METHYL-1H-INDAZOLE-4-BORONIC ACID; 6-METHYL-1H-INDAZOLE-5-BORONIC ACID; 6-METHYL-1H-INDOL-3-YLBORONIC ACID; 6-METHYL-1H-INDOLE-2-BORONIC ACID; 6-METHYL-2-(2-(TRIFLUOROMETHOXY)PHENYL)PYRIDINE-3-BORONIC ACID; 6-METHYL-2-(2-(TRIFLUOROMETHYL)PHENYL)PYRIDINE-3-BORONIC ACID; 6-METHYL-2-(2,4,5-TRICHLOROPHENYL)PYRIDINE-3-BORONIC ACID; 6-METHYL-2-(3-(TRIFLUOROMETHOXY)PHENYL)PYRIDINE-3-BORONIC ACID; 6-METHYL-2-(3-(TRIFLUOROMETHYL)PHENYL)PYRIDINE-3-BORONIC ACID; 6-METHYL-2-(4-(TRIFLUOROMETHOXY)PHENYL)PYRIDINE-3-BORONIC ACID; 6-METHYL-2-(4-(TRIFLUOROMETHYL)PHENYL)PYRIDINE-3-BORONIC ACID; 6-METHYL-2-(PERFLUOROPHENYL)PYRIDINE-3-BORONIC ACID; 6-METHYL-2-NAPHTHALENEBORONIC ACID; 6-METHYLBENZO[B]THIEN-2-YL BORONIC ACID; 6-METHYLBENZOFURAN-2-YLBORONIC ACID; 6-METHYLPYRAZINE-2-BORONIC ACID; 6-METHYLPYRIDINE-2-BORONIC ACID; 6-METHYLPYRIDINE-3-BORONIC ACID; 6-METHYLQUINOLINE-8-BORONIC ACID; 6-MORPHOLINOPYRAZINE-2-BORONIC ACID; 6-MORPHOLINOPYRIDINE-2-BORONIC ACID; 6-NITROPYRIDIN-3-YLBORONIC ACID; 6-OXO-1,6-DIHYDROPYRAZIN-2-YLBORONIC ACID; 6-PENTYLNAPTHALENE-2-BORONIC ACID; 6-PENTYLOXYNAPHTHALENE-2-BORONIC ACID; 6-PHENOXYPYRIDIN-3-YLBORONIC ACID; 6-PHENYL-1H-PYRROLO[2,3-B]PYRIDINE-2-BORONIC ACID; 6-PHENYL-1H-PYRROLO[2,3-B]PYRIDINE-3-BORONIC ACID; 6-PHENYL-1H-PYRROLO[2,3-B]PYRIDINE-4-BORONIC ACID; 6-PHENYL-1H-PYRROLO[2,3-B]PYRIDINE-5-BORONIC ACID; 6-PHENYLPYRIDINE-2-BORONIC ACID; 6-PHENYLPYRIDINE-3-BORONIC ACID; 6-PHENYLPYRIMIDINE-4-BORONIC ACID; 6-PROPOXYBENZOFURAN-2-YLBORONIC ACID; 6-PROPOXYPYRIDINE-3-BORONIC ACID; 6-PROPYLPYRIDIN-3-YLBORONIC ACID; 6-QUINAZOLINEBORONIC ACID; 6-QUINOLINYLBORONIC ACID HYDRATE; 6-SEC-BUTYLPYRAZIN-2-YLBORONIC ACID; 6-T-BUTYLDIMETHYLSILYLOXY-2-NAPHTHALENEBORONIC ACID; 6-TERT-BUTYLNAPHTHALEN-2-YLBORONIC ACID; 6-TERT-BUTYLPYRIDIN-3-YLBORONIC ACID; 6-THIOMORPHOLINOPYRIDIN-3-YLBORONIC ACID; 7-(DIFLUOROMETHOXY)BENZOTHIAZOLE-2-BORONIC ACID; 7-(HYDROXYMETHYL)NAPHTHALENE-1-BORONIC ACID; 7-(HYDROXYMETHYL)NAPHTHALENE-2-BORONIC ACID; 7-(TERT-BUTYLDIMETHYLSILYLOXY)-1H-INDOL-2-YLBORONIC ACID; 7-(TRIFLUOROMETHYL)PYRIDO[2,3-D]PYRIMIDIN-4-YLBORONIC ACID; 7-CHLORO-1H-PYRAZOLO[3,4-C]PYRIDINE-4-BORONIC ACID; 7-CHLOROBENZO[B]THIOPHEN-3-YLBORONIC ACID; 7-CHLOROQUINOLINE-4-BORONIC ACID; 7-CYANOBENZO[B]THIOPHEN-2-YLBORONIC ACID; 7-FLUORO-2-METHYLQUINOLINE-8-BORONIC ACID; 7H-PYRROLO[2,3-D]PYRIMIDIN-4-YLBORONIC ACID; 7-HYDROXYBENZOTHIAZOLE-2-BORONIC ACID; 7-HYDROXYNAPHTHALENE-1-BORONIC ACID; 7-HYDROXYNAPHTHALENE-2-BORONIC ACID; 7-HYDROXYQUINOLINE-2-BORONIC ACID; 7-HYDROXYQUINOLINE-3-BORONIC ACID; 7-HYDROXYQUINOLINE-4-BORONIC ACID; 7-HYDROXYQUINOLINE-5-BORONIC ACID; 7-HYDROXYQUINOLINE-6-BORONIC ACID; 7-HYDROXYQUINOLINE-8-BORONIC ACID; 7-METHOXY-1H-INDOL-2-YLBORONIC ACID; 7-METHOXY-1H-INDOL-3-YLBORONIC ACID; 7-METHOXY-2-METHYLQUINOLIN-4-YLBORONIC ACID; 7-METHOXYBENZO[B]THIOPHENE-2-BORONIC ACID; 7-METHOXYBENZOFURAN-2-BORONIC ACID; 7-METHOXYBENZOFURAN-3-YLBORONIC ACID; 7-METHOXYBENZOTHIAZOLE-2-BORONIC ACID; 7-METHOXYQUINOLIN-4-YLBORONIC ACID; 7-METHYL-1-(TRIISOPROPYLSILYL)-1H-INDOL-3-YLBORONIC ACID; 7-METHYL-1H-INDAZOLE-4-BORONIC ACID; 7-METHYL-1H-INDAZOLE-5-BORONIC ACID; 7-METHYL-1H-INDOL-2-YLBORONIC ACID; 7-METHYL-1-NAPHTHALENEBORONIC ACID; 7-METHYLIMIDAZO[1,2-A]PYRIDINE-6-BORONIC ACID; 7-PHENYL-1H-INDOL-2-YLBORONIC ACID; 7-PROPOXYBENZOFURAN-2-YLBORONIC ACID; 8-(HYDROXYMETHYL)NAPHTHALENE-1-BORONIC ACID; 8-(HYDROXYMETHYL)NAPHTHALENE-2-BORONIC ACID; 8-CHLORO-1,7-NAPHTHYRIDINE-3-BORONIC ACID; 8-CHLORO-2-METHYL-1,7-NAPHTHYRIDIN-5-YLBORONIC ACID; 8-FLUORO-2-METHYLQUINOLINE-7-BORONIC ACID; 8-FLUORO-7-HYDROXYQUINOXALIN-6-YLBORONIC ACID; 8-FLUOROQUINOLIN-3-YLBORONIC ACID; 8-FLUOROQUINOLIN-6-YLBORONIC ACID; 8-FLUOROQUINOLINE-7-BORONIC ACID; 8-FLUOROQUINOXALIN-6-YLBORONIC ACID; 8-HYDROXYNAPHTHALENE-1-BORONIC ACID; 8-HYDROXYNAPHTHALENE-2-BORONIC ACID; 8-HYDROXYQUINOLINE-2-BORONIC ACID; 8-HYDROXYQUINOLINE-3-BORONIC ACID; 8-HYDROXYQUINOLINE-4-BORONIC ACID; 8-HYDROXYQUINOLINE-5-BORONIC ACID; 8-HYDROXYQUINOLINE-6-BORONIC ACID; 8-HYDROXYQUINOLINE-7-BORONIC ACID; 8-ISOQUINOLINEBORONIC ACID; 8-METHOXYQUINOLINE-7-BORONIC ACID; 8-METHYL-5-QUINOLINYLBORONIC ACID; 8-OXATRICYCLO[7.4.0.0(2,7)]TRIDECA-1(9),2(7),3,5,10,12-HEXAEN-4-YLBORANEDIOL; 8-TRIFLUOROMETHOXYQUINOLINE-5-BORONIC ACID; 8-TRIFLUOROMETHYLQUINOLINE-6-BORONIC ACID; 9,9-DIETHYLFLUORENE-2-BORONIC ACID; 9,9-DIMETHYL-9H-FLUOREN-2-YL-BORONIC ACID; 9-ACRIDINYL-BORONIC ACID; 9-ANTHRACENEBORONIC ACID; 9H-CARBAZOL-3-YLBORONIC ACID; 9H-FLUOREN-9-YLBORONIC ACID; 9-PHENANTHRENEBORONIC ACID; 9-PHENYLCARBAZOLE-3-BORONIC ACID; ABH; ACENAPHTHENE-5-BORONIC ACID; ACETAMIDOMETHYLBORONIC ACID; ACETYL BOROARGININE TRIFLUOROACETATE; ALLENYLBORONIC ACID; ALPHA-(TRIFLUOROMETHYL)ETHENYL BORONIC ACID; AMINO[4-(DIHYDROXYBORYL)PHENYL]ACETIC ACID; B-(1,6-DIHYDRO-6-OXO-3-PYRIDINYL)-BORONIC

ACID; B-(1-METHYL-1H-INDOL-4-YL)-BORONIC ACID; B-(2'-CHLORO[2,4'-BIPYRIDIN]-4-YL)-BORONIC ACID; B-(3,6-DIHYDRO-1,1-DIOXIDO-2H-THIOPYRAN-4-YL)-BORONIC ACID; B-(3-ETHYNYLPHENYL)-BORONIC ACID; B-(4-AMINO-3-PYRIDINYL)-BORONIC ACID HYDROCHLORIDE; B-(4'-CYANO[1,1'-BIPHENYL]-4-YL)-BORONIC ACID; B-(5-FLUORO-1,6-DIHYDRO-6-OXO-3-PYRIDINYL)-BORONIC ACID; B-(5-METHOXY-1-METHYL-1H-PYRROLO[3,2-B]PYRIDIN-6-YL)-BORONIC ACID; B-(9,10-DIPHENYL-2-ANTHRACENYL)BORONIC ACID; B-[1-(PHENYLSULFONYL)-1H-PYRROLO[2,3-B]PYRIDIN-4-YL]-BORONIC ACID; B-[2-(DIFLUOROMETHYL)-1-(PHENYLSULFONYL)-1H-PYRROLO[2,3-B]PYRIDIN-4-YL]-BORONIC ACID; B-[2,6-DIMETHYL-4-(PHENYLMETHOXY)PHENYL]-BORONIC ACID; B-[3-(1-PROPYN-1-YL)PHENYL]-BORONIC ACID; B-[3,4-BIS[[(1,1-DIMETHYLETHYL)DIMETHYLSILYL]OXY]METHYLPHENYL]-BORONIC ACID; B-[3,5-BIS[(1,1-DIMETHYLETHYL)DIMETHYLSILYL]PHENYL]-BORONIC ACID; B-[4,2':6',4"-TERPYRIDIN]-4'-YL-BORONIC ACID; B-[4-[(TETRAHYDRO-1,1-DIOXIDO-2H-THIOPYRAN-4-YL)AMINO]PHENYL]-BORONIC ACID; B-[4-[[(TETRAHYDRO-1,1-DIOXIDO-2H-THIOPYRAN-4-YL)AMINO]SULFONYL]PHENYL]-BORONIC ACID; B-[4-[BIS(4-METHYLPHENYL)AMINO]PHENYL]-BORONIC ACID; B-[5-(3-METHOXYPHENYL)-3-PYRIDINYL]-BORONIC ACID; B-[5-[(PHENYLSULFONYL)AMINO]-3-PYRIDINYL]BORONIC ACID; B-5H-PYRROLO[3,2-B:4,5-B']DIPYRIDIN-3-YL-BORONIC ACID; B-6-BENZOFURANYL-BORONIC ACID; BEC; BEC AMMONIUM SALT; BEC, HYDROCHLORIDE; BENZAMIDOMETHYLBORONIC ACID; BENZENE-1,4-DIBORONIC ACID MONO-MIDA ESTER; BENZIMIDAZOLE-2-BORONIC ACID; BENZO[B]THIOPHENE-2-BORONIC ACID; BENZO[C][1,2,5]OXADIAZOLE-5-BORONIC ACID; BENZO[D]ISOXAZOL-4-YLBORONIC ACID; BENZO[D]ISOXAZOL-5-YLBORONIC ACID; BENZO[D]ISOXAZOL-6-YLBORONIC ACID; BENZO[D]OXAZOL-7-YLBORONIC ACID; BENZOCYCLOBUTENE-4-BORONIC ACID; BENZOFURAN-2-BORONIC ACID; BENZOFURAN-3-BORONIC ACID; BENZOFURAN-5-BORONIC ACID; BENZOPYRAZINE-6-BORONIC ACID HCL; BENZOTHIOPHENE-3-BORONIC ACID; BENZYLBORONIC ACID; BIPHENYL-2-YLBORONIC ACID HYDRATE; BOC-3-AMINOPYRIDINE-4-BORONIC ACID; BOC-4-AMINO-6-METHYLPYRIDINE-3-BORONIC ACID; BOC-L-PROLINEBORONIC ACID; BORONIC ACID, (2,3,4,5-TETRAHYDRO-3-METHYL-1H-3-BENZAZEPIN-7-YL)-; BORONIC ACID, [2-(1-PIPERIDINYLCARBONYL)PHENYL]-; BORONIC ACID, [2-(1-PYRROLIDINYLCARBONYL)PHENYL]-; BORONIC ACID, [3-(1-METHYLETHYL)-1H-INDAZOL-4-YL]-; BORONIC ACID, [3-(1-NAPHTHALENYL)PHENYL]-; BORONIC ACID, [3-(1-PYRROLIDINYLMETHYL)PHENYL]-, HYDROCHLORIDE, PROPAN-2-OL; BORONIC ACID, [3-(PHENYLMETHYL)PHENYL]-; BORONIC ACID, [4-(1-PIPERIDINYLMETHYL)PHENYL]-, HYDROCHLORIDE; BORONIC ACID, [4-(1-PYRROLIDINYLMETHYL)PHENYL]-, HYDROCHLORIDE; BORONIC ACID, [4-(2-AMINO-3-HYDROXYPROPYL)PHENYL]-; BORONIC ACID, [4-(MERCAPTOMETHYL)PHENYL]-; BORONIC ACID, [4-(PHENYLMETHYL)PHENYL]-; BORONIC ACID, [4-[(2R)-2-AMINO-3-HYDROXYPROPYL]PHENYL]-; BORONIC ACID, [4-[(2S)-2-AMINO-3-HYDROXYPROPYL]PHENYL]-; BORONIC ACID, [4-CHLORO-1-[TRIS(1-METHYLETHYL)SILYL]-1H-PYRROLO[2,3-B]PYRIDIN-5-YL]-; BORONIC ACID, B-(1,2,3,4-TETRAHYDRO-7-ISOQUINOLINYL)-; BORONIC ACID, B-(3-METHOXY-6-PHENYL-4-PYRIDAZINYL)-; BORONIC ACID, B-(5-HYDROXYBENZO[B]THIEN-2-YL)-; BORONIC ACID, B-[2-[1-(TRIPHENYLMETHYL)-1H-TETRAZOL-5-YL]PHENYL]-; BORONIC ACID, B-[3,5-DICHLORO-2-(2,2-DIFLUOROETHOXY)PHENYL]-; BORONIC ACID, B-[3-METHOXY-6-(6-METHOXY-3-PYRIDINYL)-4-PYRIDAZINYL]-; BORONIC ACID, B-[5-(2-METHYLPHENYL)-3-PYRIDINYL]-; BORONIC ACID, B-[5-[(E)-[4-OXO-3-(2-PROPEN-1-YL)-2-THIOXO-5-THIAZOLIDINYLIDENE]METHYL]-2-THIENYL]-; BORONIC ACID, B-[6-(6-FLUORO-3-PYRIDINYL)-3-METHOXY-4-PYRIDAZINYL]-; BORTEZOMIB; BORTEZOMIB-D8; B-PYRIDO[2,3-B]PYRAZIN-7-YL-BORONIC ACID; BUT-1-ENE-4-BORONIC ACID; BZ-PHE-BOROLEU; CARBAZOL-4-YLBORONIC ACID; CARBAZOLE-1-BORONIC ACID; CEP-18770; CHROMABORA II; CHROMAN-8-BORONIC ACID; CIS-1-PROPENE-1-BORONIC ACID; CIS-2-METHYL-CYCLOPROPYL BORONIC ACID; COMBI-BLOCKS BB-2570; CYCLOBUTYLBORONIC ACID; CYCLOHEPTANEBORONIC ACID; CYCLOHEPTEN-1-YLBORONIC ACID; CYCLOHEXYLBORONIC ACID; CYCLOHEXYLMETHYLBORONIC ACID; CYCLOPENTEN-1-YLBORONIC ACID; CYCLOPENTYLBORONIC ACID; CYCLOPROPYLBORONIC ACID; CYCLOPROPYLBORONIC ACID MONOHYDRATE; DIBENZOFURAN-1-BORONIC ACID; DIBENZOFURAN-4-BORONIC ACID; DIBENZOTHIOPHENE-2-BORONIC ACID; DIBENZOTHIOPHENE-4-BORONIC ACID; DITHIENO[3,2-B:2',3'-D]THIOPHENE-2-BORONIC ACID; E-(4-BUTYLPHENYL)ETHENYLBORONIC ACID; E-1-OCTENYLBORONIC ACID; E-HEXEN-1-YLBORONIC ACID; E-PENTADECENE-1-BORONIC ACID; E-PHENYLETHENYLBORONIC ACID; ETHYL (3-BORONOBENZOYLAMINO)ACETATE; ETHYL (4-BORONOBENZOYLAMINO)ACETATE; ETHYL 3-BORONOCINNAMATE; ETHYL 4-BORONOCINNAMATE; ETHYLBORONIC ACID; ETHYL-D5-BORONIC ACID; FERROCENEBORONIC ACID; FLUORANTHENE-3-BORONIC ACID; FLUORENE-2-BORONIC ACID; FURAN-2-BORONIC ACID; FURAN-3-BORONIC ACID; FURO[2,3-C]PYRIDINE-7-BORONIC ACID; FURO[3,2-C]PYRIDINE-4-BORONIC ACID; HEPT-6-ENYLBORONIC ACID; HEPTYLBORONIC ACID; HEX-5-EN-2-YLBORONIC ACID; HEXADECYLBORONIC ACID; H-PYRAZOLO[3,4-B]PYRIDINE-4-BORONIC ACID; IMIDAZO[1,2-A]PYRAZINE-6-BORONIC ACID; IMIDAZO[1,2-A]PYRIDIN-3-YLBORONIC ACID; IMIDAZO[1,2-A]PYRIDIN-8-YLBORONIC ACID; IMIDAZO[1,2-A]PYRIDINE-6-BORONIC ACID; IMIDAZO[1,2-A]PYRIMIDIN-3-YLBORONIC ACID; IMIDAZO[1,2-A]PYRIMIDIN-6-YLBORONIC ACID; IMIDAZO[1,5-A]PYRIDIN-5-YLBORONIC ACID; IMIDAZOLE-2-BORONIC ACID; INDAZOLE-3-BORONIC ACID; INDAZOLE-4-BORONIC ACID HYDROCHLORIDE; INDOLE-3-BORONIC ACID; INDOLE-4-BORONIC ACID; INDOLE-6-BORONIC ACID; INDOLE-7-BORONIC ACID; INDOLIN-6-YLBORONIC ACID; ISOBUTYLBORONIC ACID; ISOINDOLIN-1-ONE-4-BORONIC ACID; ISOIN-

DOLIN-1-ONE-5-BORONIC ACID; ISOPROPYLBORONIC ACID; ISO-PROPYL-D7-BORONIC ACID; ISOQUINOLIN-4-YLBORONIC ACID HYDROCHLORIDE; ISOQUINOLIN-5-YLBORONIC ACID HYDROCHLORIDE; ISOQUINOLIN-6-YLBORONIC ACID HYDROCHLORIDE; ISOQUINOLINE-3-BORONIC ACID; ISOQUINOLINE-4-BORONIC ACID; ISOQUINOLINE-5-BORONIC ACID; ISOQUINOLINE-6-BORONIC ACID; ISOQUINOLINE-7-BORONIC ACID; ISOTHIAZOLE-4-BORONIC ACID; ISOTHIAZOLE-5-BORONIC ACID; ISOXAZOL-3-YLBORONIC ACID; ISOXAZOLE-4-BORONIC ACID; ISOXAZOLE-5-BORONIC ACID; LITHIUM (3-FLUORO-6-METHYLPYRIDIN-2-YL)TRIHYDROXYBORATE; LITHIUM (3-METHYLPYRIDIN-2-YL)TRIHYDROXYBORATE; LITHIUM (4-(1,3-DIOXOLAN-2-YL)PYRIDIN-2-YL)TRIHYDROXYBORATE; LITHIUM (4-METHYLPYRIDIN-2-YL)TRIHYDROXYBORATE; LITHIUM (5-CHLOROPYRIDIN-2-YL)TRIHYDROXYBORATE; LITHIUM (5-CYANOPYRIDIN-2-YL)TRIHYDROXYBORATE; LITHIUM (5-FLUOROPYRIDIN-2-YL)TRIHYDROXYBORATE; LITHIUM (5-METHOXYPYRIDIN-2-YL)TRIHYDROXYBORATE; LITHIUM (6-(1,3-DIOXOLAN-2-YL)PYRIDIN-2-YL)TRIHYDROXYBORATE; LITHIUM (6-METHOXYPYRIDIN-2-YL)TRIHYDROXYBORATE; LITHIUM (PYRAZIN-2-YL)TRIHYDROXYBORATE; LITHIUM (PYRIDIN-2-YL)TRIHYDROXYBORATE; LITHIUM (QUINOLIN-2-YL)TRIHYDROXYBORATE; LITHIUM TRIHYDROXY(4-(TRIFLUOROMETHYL)PYRIDIN-2-YL)BORATE; LITHIUM TRIHYDROXY(5-(TRIFLUOROMETHYL)PYRIDIN-2-YL)BORATE; LITHIUM TRIHYDROXY(6-(TRIFLUOROMETHYL)PYRIDIN-2-YL)BORATE; LITHIUM TRIHYDROXY(6-METHYLPYRIDIN-2-YL)BORATE; LITHIUM TRIHYDROXY(ISOQUINOLIN-1-YL)BORATE; L-PHENYLALANINE, 4-BORONO-, HYDROCHLORIDE; M-AMINOPHENYLBORONIC ACID-AGAROSE; METHYL (4-BORONOBENZOYLAMINO)ACETATE; METHYL 3-(3-BORONOPHENYL)PROPIONATE; METHYL 3-(4-BORONOBENZAMIDO)PROPIONATE; METHYL 3-BORONO-4-METHOXYBENZOATE; METHYL 4-BORONO-3-CHLOROBENZOATE; METHYL 4-BORONOBENZENESULFONAMIDE; METHYL PYRIDINE-2-BORONIC ACID-4-CARBOXYLATE; METHYLBORONIC ACID; METHYL-D3-BORONIC ACID; MLN-2238; N-(2-DIHYDROXYBORYLBENZYL)-N-METHYLM-TOLYLAMINE; N-(2-HYDROXYETHYL) 3-BORONOBENZENESULFONAMIDE; N-(2-HYDROXYETHYL) 4-BORONOBENZENESULFONAMIDE; N-(3,4-DIFLUOROPHENYL) 3-BORONOBENZAMIDE; N-(3-CHLORO-2-METHYLPHENYL) 3-BORONOBENZAMIDE; N-(3-CHLORO-4-FLUOROPHENYL) 3-BORONOBENZAMIDE; N-(4-FLUOROPHENYL) 4-BORONOBENZENESULFONAMIDE; N-(4-METHOXYBENZYL) 4-BORONOBENZAMIDE; N-(4-PHENYLBORONIC)SUCCINAMIC ACID; N-(BOC)-4-FLUOROINDOLE-2-BORONIC ACID; N-(BOC)-6-FLUOROINDOLE-2-BORONIC ACID; N-(BOC)-7-FLUOROINDOLE-2-BORONIC ACID; N-(METHYL-D3)-INDAZOLE-5-BORONIC ACID; N-(METHYL-D3)-INDAZOLE-6-BORONIC ACID; N-(P-TOLUENESULFONYL)INDOLE-3-BORONIC ACID; N-(TERT-BUTOXYCARBONYL)-4-METHYLINDOLE-2-BORONIC ACID; N-(THIAZOLINE-2-YL) 3-BORONOBENZAMIDE; N-(THIAZOLINE-2-YL) 4-BORONOBENZAMIDE; N,N,2-TRIMETHYLANILINE-4-BORONIC ACID; N,N-DIETHYL 4-BORONOBENZENESULFONAMIDE; N-[4-METHOXY-3-(4-METHYLPIPERAZIN-1-YL)-PHENYL]-4-CARBAMIDOBENZENEBORONIC ACID; N-2-TRIFLUOROMETHYLPHENYL 4-BORONOBENZAMIDE; N-BENZYL 3-BORONO-4-METHYLBENZENESULFONAMIDE; N-BENZYL 3-BORONOBENZENESULFONAMIDE; N-BOC-5-(DIETHOXYMETHYL)PYRROLE-2-BORONIC ACID; N-BOC-5-CHLORO-INDOL-3-YL BORONIC ACID; N-BOC-PYRROLIDIN-2-(S)-YLBORONIC ACID; N-BOC-PYRROLIDINYL-3-BORONIC ACID; N-BUTYL 3-BORONOBENZENESULFONAMIDE; N-BUTYLBORONIC ACID; N-CYCLOPROPYL 4-BORONO-2-FLUOROBENZAMIDE; N-DECYLBORONIC ACID; N-DIETHYL 3-BORONO-5-CHLOROBENZAMIDE; N-DIMETHYL 3-BORONO-5-CHLOROBENZAMIDE; N-DODECYLBORONIC ACID; NEOPENTYLBORONIC ACID; N-ETHYL 3-BORONO-5-CHLOROBENZAMIDE; N-ETHYL-5-INDOLE BORONIC ACID; N-HEXYLBORONIC ACID; N-ISOPROPYL 3-BORONOBENZENESULFONAMIDE; N-METHYL 2-BORONO-4-FLUOROBENZAMIDE; N-METHYL 3-BORONO-5-CHLOROBENZAMIDE; N-METHYL-4-PYRIDINEBORONIC ACID IODIDE; N-METHYLINDOLE-2-BORONIC ACID; N-PENTYLBORONIC ACID; N-PROPYLBORONIC ACID; N-PROPYL-D7-BORONIC ACID; N-P-TOLYL 4-BORONOBENZENESULFONAMIDE; N-TETRADECYLBORONIC ACID; N-TRIDECANEBORONIC ACID; N-UNDECANEBORONIC ACID; OCT-7-ENYLBORONIC ACID; OCTADECYLBORONIC ACID; OCTYLBORONIC ACID; OXAZOL-2-YLBORONIC ACID; OXINDOLE-6-BORONIC ACID; P-(4-PROPYLCYCLOHEXYL)PHENYLBORONIC ACID; PERYLENE-3-BORONIC ACID; PHENANTHREN-2-YL-2-BORONIC ACID; PHENANTHREN-3-YL-3-BORONIC ACID; PHENETHYLBORONIC ACID; PHENOXATHIIN-4-BORONIC ACID; PHENYLALANINE, 4-BORONO-, HYDROCHLORIDE; PHENYLBORONIC ACID; PHENYLBORONIC ACID, [RING-14C]-; PHENYL-D5-BORONIC ACID; PIPERIDIN-4-YLBORONIC ACID HYDROCHLORIDE; PIPERIDINE-4-BORONIC ACID; PIVALAMIDOMETHYLBORONIC ACID; PROP-1-EN-2-YL-BORONIC ACID; PROPIONAMIDOMETHYLBORONIC ACID; PYRAZIN-2-YLBORONIC ACID; PYRAZOLE-3-BORONIC ACID, HYDROCHLORIDE; PYRAZOLO[1,5-A]PYRIDIN-3-YLBORONIC ACID; PYRAZOLO[1,5-A]PYRIDIN-5-YLBORONIC ACID; PYRAZOLO[1,5-A]PYRIDIN-7-YLBORONIC ACID; PYRIDAZIN-3-YLBORONIC ACID; PYRIDAZIN-4-YLBORONIC ACID; PYRIDINE-3-BORONIC ACID; PYRIDINE-3-BORONIC ACID HCL; PYRIDINE-4-BORONIC ACID; PYRIDINE-4-BORONIC ACID HYDRATE; PYRIDINE-4-BORONIC ACID HYDROCHLORIDE; PYRIDO[3,4-D]PYRIDAZINE-5-BORONIC ACID; PYRIMIDIN-2-YLBORONIC ACID; PYRIMIDIN-5-YL-5-BORONIC ACID MONOHYDRATE; PYRIMIDINE-4-BORONIC ACID; PYRIMIDINE-5-BORONIC ACID; QUINAZOLIN-4-YLBORONIC ACID; QUINAZOLIN-7-YLBORONIC ACID; QUINOLINE-2-BORONIC ACID; QUINOLINE-4-BORONIC ACID; QUINOLINE-5-BORONIC ACID; QUINOLINE-6-BORONIC ACID; QUINOLINE-6-BORONIC ACID HYDROCHLORIDE; QUINOLINE-7-BORONIC ACID; QUINOLINE-8-BORONIC ACID; QUINOXALINE-6-BORONIC ACID; RACEMIC, TRANS-1-CHLO-

ROMETHYL-CYCLOPROPYL-2-BORONIC ACID; RACEMIC, TRANS-1-PROPYL-CYCLOPROPYL-2-BORONIC ACID; S-(2-BORONOETHYL)-L-CYSTEINE HYDROCHLORIDE; SELENOPHENE-2-BORONIC ACID; SODIUM (TRIHYDROXY)PHENYLBORATE; SODIUM PYRIDINE-3-TRIHYDROXYBORATE; SODIUM THIOPHENE-2-TRIHYDROXYBORATE; SODIUM THIOPHENE-3-TRIHYDROXYBORATE; TALABOSTAT; T-BUTYL 3-BORONOBENZENE-SULFONAMIDE; TERT-BUTYLBORONIC ACID; TETRAHYDROFURAN-3-BORONIC ACID; TETRAHYDROPYRAN-3-BORONIC ACID; TETRAHYDROPYRAN-4-BORONIC ACID; THIANTHRENE-1-BORONIC ACID; THIANTHRENE-2-BORONIC ACID; THIAZOL-5-YLBORONIC ACID; THIAZOLE-2-BORONIC ACID; THIAZOLE-4-BORONIC ACID; THIENO[2,3-B]PYRIDIN-2-YLBORONIC ACID; THIENO[2,3-C]PYRIDINE-7-BORONIC ACID; THIENO[3,2-B]THIOPHENE-2-BORONIC ACID; THIENO[3,2-C]PYRIDIN-2-YL BORONIC ACID; THIENO[3,2-C]PYRIDINE-4-BORONIC ACID; THIOPHENE-2-BORONIC ACID; THIOPHENE-2-CARBOXYLIC ACID METHYL ESTER-5-BORIC ACID; THIOPHENE-3-BORONIC ACID; TRANS-(4-PENTYLCYCLOHEXYL)CYCLOHEX-1-ENYLBORONIC ACID; TRANS-(4-PROPYLCYCLOHEXYL)CYCLOHEX-1-ENYLBORONIC ACID; TRANS-1-PROPEN-1-YLBORONIC ACID; TRANS-2-(3-CHLOROPHENYL)CYCLOPROPANEBORONIC ACID; TRANS-2-(3-FLUOROPHENYL)CYCLOPROPANEBORONIC ACID; TRANS-2-(3-FLUOROPHENYL)VINYLBORONIC ACID; TRANS-2-(3-METHOXYPHENYL)CYCLOPROPANEBORONIC ACID; TRANS-2-(4-BIPHENYL)VINYLBORONIC ACID; TRANS-2-(4-CHLOROPHENYL)VINYLBORONIC ACID; TRANS-2-(4-FLUOROPHENYL)CYCLOPROPANEBORONIC ACID; TRANS-2-(4-FLUOROPHENYL)VINYLBORONIC ACID; TRANS-2-(4-METHOXYPHENYL)VINYLBORONIC ACID; TRANS-2-(4-METHYLPHENYL)CYCLOPROPANEBORONIC ACID; TRANS-2-(4-METHYLPHENYL)VINYLBORONIC ACID; TRANS-2-(6-CHLOROPYRIDIN-3-YL)CYCLOPROPANEBORONIC ACID; TRANS-2-(6-METHOXYPYRIDIN-3-YL)CYCLOPROPANEBORONIC ACID; TRANS-2-(6-METHYLPYRIDIN-3-YL)CYCLOPROPANEBORONIC ACID; TRANS-2-[4-(TRIFLUOROMETHYL)PHENYL]CYCLOPROPANEBORONIC ACID; TRANS-2-[4-(TRIFLUOROMETHYL)PHENYL]VINYLBORONIC ACID; TRANS-2-[6-(TRIFLUOROMETHYL)PYRIDIN-3-YL]CYCLOPROPANEBORONIC ACID; TRANS-2-CHLOROMETHYLVINYLBORONIC ACID; TRANS-2-METHYL-CYCLOPROPYL BORONIC ACID; TRANS-2-PHENYLCYCLOPROPYLBORONIC ACID; TRANS-2-PYRIDIN-3-YLCYCLOPROPANEBORONIC ACID; TRANS-3,3,3-TRIFLUOROPROPENE-1-BORONIC ACID; TRANS-3-PHENYLPROPEN-1-YL-BORONIC ACID; TRANS-4-(BETA-NITROVINYL)BENZENEBORONIC ACID; TRANS-HEPTENYLBORONIC ACID; TRANS-NONENYLBORONIC ACID; TRIMETHYLSILYLETHYNYLBORONIC ACID; URACIL-5-BORONIC ACID; VILDAGLIPTIN-BORONIC ACID; VINYL BORONIC ACID; Z-1-HEXENYLBORONIC ACID

List No. 4—Acids: ((AMINOCARBONYL)AMINO)ACETIC ACID HYDRATE; (−)-(1S,4R)-4-AMINOCYCLOPENT-2-ENECARBOXYLIC ACID; (+)-4-AMINO-2-FLUOROBUTYRIC ACID; (+/−)-2-ACETOXYPROPIONIC ACID; (+/−)-2-AMINO-CYCLOHEXANECARBOXYLIC ACID; (+/−)-CIS-3-METHYL-2-PIPERIDINECARBOXYLIC ACID; (+/−)-THREO-3-METHYLASPARTIC ACID; (+/−)-TRANS-AZETIDINE-2,4-DICARBOXYLIC ACID; (+/−)-TRANS-EPOXYSUCCINIC ACID; (1-AMINO-1H-IMIDAZOL-2-YL)-ACETIC ACID; (1-AMINOCYCLOPENTYL) ACETIC ACID; (1H-[1,2,3]TRIAZOL-4-YL)-ACETIC ACID; (1H-IMIDAZOL-2-YL)-ACETIC ACID; (1H-PYRAZOL-3-YL)-ACETIC ACID; (1H-PYRROL-2-YL)-ACETIC ACID; (1-METHYL-1H-IMIDAZOL-2-YL)-ACETIC ACID; (1-METHYL-1H-IMIDAZOL-4-YL)-ACETIC ACID; (1-METHYL-1H-PYRAZOL-3-YL)ACETIC ACID; (1-METHYL-1H-PYRAZOL-4-YL)-ACETIC ACID; (1-METHYL-1H-PYRAZOL-5-YL)ACETIC ACID; (1-METHYL-1H-PYRROL-3-YL)ACETIC ACID; (1-METHYLHYDRAZINO)ACETIC ACID; (1-METHYLPYRROLIDIN-2-YL)ACETIC ACID; (1R,2R)-(+2-AMINO-1-CYCLOPENTANECARBOXYLIC ACID; (1R,2R)-2-(CHLOROMETHYL)CYCLOPROPANECARBOXYLIC ACID; (1R,2R)-2-AMINOCYCLOHEXANECARBOXYLIC ACID; (1R,2R)-CYCLOBUTANE-1,2-DICARBOXYLIC ACID; (1R,2R,4R)-BICYCLO[2.2.1]HEPT-5-ENE-2-CARBOXYLIC ACID; (1R,2S)-(−)-2-AMINO-CYCLOHEMNECARBOXYLIC ACID; (1R,2S)-2-AMINO-4-METHYLENECYCLOPENTANECARBOXYLIC ACID; (1R,2S)-2-AMINO-CYCLOHEX-3-ENECARBOXYLIC ACID; (1R,2S)-2-AMINO-CYCLOPENTANECARBOXYLIC ACID; (1R,2S)-2-METHYLCYCLOPROPANECARBOXYLIC ACID; (1R,2S)-2-PROPYLCYCLOPROPANECARBOXYLIC ACID; (1R,2S,4R)-BICYCLO[2.2.1]HEPT-5-ENE-2-CARBOXYLIC ACID; (1R,3R)-(3-AMINOCYCLOPENTYL)-ACETIC ACID; (1R,3R)-3-AMINOCYCLOHEXANECARBOXYLIC ACID; (1R,3R)-3-AMINO-CYCLOPENTANE CARBOXYLIC ACID; (1R,3S)-(3-AMINOCYCLOPENTYL)-ACETIC ACID; (1R,3S)-1-AMINO-3-HYDROXYCYCLOPENTANECARBOXYLIC ACID; (1R,3S)-3-AMINO-CYCLOHEXANECARBOXYLIC ACID; (1R,3S)-3-AMINOCYCLOPENTANECARBOXYLIC ACID; (1R,3S,4R)-2-AZABICYCLO[2.2.1]HEPTANE-3-CARBOXYLIC ACID; (1R,3S,4S)-2-AZABICYCLO[2.2.1]HEPTANE-3-CARBOXYLIC ACID; (1R,3S,4S)-3-AMINO-4-FLUOROCYCLOPENTANECARBOXYLIC ACID; (1R,4R)-4-AMINOCYCLOPENT-2-ENECARBOXYLIC ACID; (1R,4S)-4-AMINOCYCLOPENT-2-ENECARBOXYLIC ACID; (1R,4S,5R)-BICYCLO[2.1.1]HEXANE-5-CARBOXYLIC ACID; (1R,4S,5S)-BICYCLO[2.1.1]HEXANE-5-CARBOXYLIC ACID; (1R,5S,6R)-BICYCLO[3.1.1]HEPTANE-6-CARBOXYLIC ACID; (1R,5S,6S)-BICYCLO[3.1.1]HEPTANE-6-CARBOXYLIC ACID; (1R,6R)-6-AMINOCYCLOHEX-3-ENE-1-CARBOXYLIC ACID; (1S)-1-METHYL-2-CYCLOHEXENE-1-CARBOXYLIC ACID; (1S)-3-OXO-CYCLOPENTANEACETIC ACID; (1S,2R)-(−)-2-AMINOCYCLOHEX-3-ENECARBOXYLIC ACID; (1S,2R)-2-(METHOXYCARBONYL)CYCLOPROPANECARBOXYLIC ACID; (1S,2R)-2-AMINO-2-METHYLCYCLOPENTANECARBOXYLIC ACID; (1S,2R)-2-AMINOCYCLOPENTANECARBOXYLIC ACID; (1S,2R)-2-PROPYLCYCLOPROPANECARBOXYLIC ACID; (1S,2S)-2-(HYDROXYMETHYL)CYCLOPROPANECARBOXYLIC ACID; (1S,2S)-2-AMINOCYCLOHEXANECARBOXYLIC ACID; (1S,2S)-2-AMINO-CYCLOPETANECARBOXYLIC ACID; (1S,2S)-3-METHYLENECYCLOPROPANE-1,2-DICARBOXYLIC ACID; (1S,2S)-CYCLOPROPANE-1,2-

DICARBOXYLIC ACID; (1S,2S,5R)-3-AZABICYCLO[3.1.0]HEXANE-2-CARBOXYLIC ACID; (1S,3R)-(3-AMINOCYCLOPENTYL)-ACETIC ACID; (1S,3R)-1-AMINO-3-HYDROXYCYCLOPENTANECARBOXYLIC ACID; (1S,3R)-3-AMINO-CYCLOHEXANECARBOXYLIC ACID; (1S,3R)-3-AMINOCYCLOPENTANECARBOXYLIC ACID; (1S,3R)-3-AMINOMETHYL-CYCLOPENTANECARBOXYLIC ACID; (1S,3S)-(3-AMINOCYCLOPENTYL)-ACETIC ACID; (1S,3S)-3-AMINOCYCLOHEXANECARBOXYLIC ACID; (1S,3S)-3-AMINOCYCLOPENTANECARBOXYLIC ACID; (1S,3S)-3-AMINOMETHYL-CYCLOPENTANECARBOXYLIC ACID; (1S,3S)-3-HYDROXY-CYCLOPENTANECARBOXYLIC ACID; (1S,5R)-2-AZABICYCLO[3.1.0]HEXANE-1-CARBOXYLIC ACID; (1-VINYL-CYCLOBUTYL)-ACETIC ACID; (2-AMINO-1H-IMIDAZOL-4-YL)-ACETIC ACID; (2-AMINO-2-METHYL-PROPOXY)-ACETIC ACID; (2-AMINO-2-OXOETHOXY)ACETIC ACID; (2-AMINO-ETHOXY)-ACETIC ACID; (2E)-((AMINOCARBONOTHIOYL)HYDRAZONO)ACETIC ACID; (2E)-2-(HYDROXYIMINO)HEXANOIC ACID; (2E)-2-[(AMINOCARBONYL)HYDRAZONO]PROPANOIC ACID; (2E)-3-(1H-PYRROL-3-YL)-2-PROPENOIC ACID; (2E)-3-(DIMETHYLCARBAMOYL)PROP-2-ENOIC ACID; (2E)-3-(ETHYLCARBAMOYL)PROP-2-ENOIC ACID; (2E)-3,4-DIMETHYLHEX-2-ENOIC ACID; (2E)-3,4-DIMETHYLPENT-2-ENOIC ACID; (2E)-3,5-DIMETHYLHEX-2-ENOIC ACID; (2E)-3-CYCLOPROPYLBUT-2-ENOIC ACID; (2E)-3-ETHYL-4-METHYLPENT-2-ENOIC ACID; (2E)-3-METHOXY-2-METHYL-2-PROPENOIC ACID; (2E)-4-(DIMETHYLAMINO)BUT-2-ENOIC ACID; (2E,4E)-2-CYANO-2,4-HEXADIENOIC ACID; (2-FURYL)GLYOXYLIC ACID; (2-METHYL-1H-IMIDAZOL-1-YL)ACETIC ACID; (2-METHYL-1H-IMIDAZOL-4-YL)-ACETIC ACID; (2-METHYL-ALLYLOXY)-ACETIC ACID; (2-METHYLAMINO-ETHOXY)-ACETIC ACID; (2-METHYL-CYCLOPENTYL)-ACETIC ACID; (2-OXO-1,3-OXAZOLIDIN-3-YL)ACETIC ACID; (2-OXO-IMIDAZOLIDIN-1-YL)-ACETIC ACID; (2-OXO-PYRROLIDIN-1-YL)-ACETIC ACID; (2-PYRROLIDINYLIDENEAMINO)ACETIC ACID; (2R)-1-FORMYLPYRROLIDINE-2-CARBOXYLIC ACID; (2R)-1-METHYL-2-PIPERIDINECARBOXYLIC ACID; (2R)-2-(ACETYLOXY)-PROPANOIC ACID; (2R)-2-(ISOPROPYLAMINO)PROPANOIC ACID; (2R)-2,5-DIHYDRO-5-OXO-2-FURANACETIC ACID; (2R)-2-AMINO-2-(3-FURYL)ACETIC ACID; (2R)-2-AMINO-2-CYCLOBUTYLPROPANOIC ACID; (2R)-2-AMINO-2-CYCLOPROPYLPROPANOIC ACID; (2R)-2-AMINO-4-METHYLHEXANOIC ACID; (2R)-2-AZIDO-3-HYDROXY-2-METHYL-PROPANOIC ACID; (2R)-2-METHYL-2-PIPERIDINECARBOXYLIC ACID; (2R)-2-PROPANAMIDOPROPANOIC ACID; (2R)-4-AMINO-2-HYDROXY-4-OXOBUTANOIC ACID; (2R)-HYDROXYBUTANEDIOIC ACID 1-METHYL ESTER; (2R)-OXIRANE-2-CARBOXYLIC ACID; (2R,3R)-3-AMINO-2-OXETANECARBOXYLIC ACID; (2R,3S)-3-AMINO-2-OXETANECARBOXYLIC ACID; (2R,3R)-(–)-EPOXYSUCCINIC ACID; (2R,3R)-2-AMINO-3-HYDROXY-4-METHYL-VALERIC ACID; (2R,3R)-2-AMINO-3-HYDROXY-HEXANOIC ACID; (2R,3R)-2-AMINO-3-HYDROXY-PENTANOIC ACID; (2R,3R)-2-AMINO-3-HYDROXY-SUCCINIC ACID; (2R,3R)-2-AMINO-3-METHYLOXYBUTANOIC ACID; (2R,3R)-3-AMINO-2-HYDROXYHEXANOIC ACID; (2R,3R)-3-AMINO-2-METHYL-BUTANOIC ACID; (2R,3R)-3-HYDROXY-D-ISOVALINE; (2R,3R)-3-METHYL-PYRROLINE-2-CARBOXYLIC ACID; (2R,3S)-(+2-AMINO-3-HYDROXY-4-METHYLPENTANOIC ACID; (2R,3S)-2-AMINO-3-HYDROXY-PENTANOIC ACID; (2R,3S)-2-AMINO-3-HYDROXY-SUCCINIC ACID; (2R,3S)-2-AMINO-3-METHYLSUCCINIC ACID; (2R,3S)-3-AMINO-2-HYDROXYHEXANOIC ACID; (2R,3S)-3-AMINO-2-METHYL-BUTANOIC ACID; (2R,3S)-3-HYDROXY-D-ISOVALINE; (2R,4R)-(+)-AZETIDINE-2,4-DICARBOXYLIC ACID; (2R,4R)-4-(METHYLAMINO)PYRROLIDINE-2-CARBOXYLIC ACID; (2R,4R)-4-FLUOROPYRROLIDINE-2-CARBOXYLIC ACID; (2R,4R)-4-METHYL-2-PYROOLIDINE CARBOXYLIC ACID; (2R,4R)-4-METHYLPIPERIDINE-2-CARBOXYLIC ACID; (2R,4S)-4-(METHYLAMINO)PYRROLIDINE-2-CARBOXYLIC ACID; (2R,4S)-4-FLUOROPYRROLIDINE-2-CARBOXYLIC ACID; (2R,4S)-4-HYDROXY-1-METHYLPYRROLIDINE-2-CARBOXYLIC ACID; (2R,4S)-4-HYDROXYPIPERIDINE-2-CARBOXYLIC ACID; (2S)-2-(1H-PYRROL-1-YL)PROPANOIC ACID; (2S)-2-(1H-TETRAZOL-1-YL)PROPANOIC ACID; (2S)-2-(CARBAMOYLAMINO)-3-HYDROXYPROPANOIC ACID; (2S)-2-(CARBAMOYLAMINO)PROPANOIC ACID; (2S)-2,3-DIHYDROXYPROPANOIC ACID; (2S)-2-[(METHOXYCARBONYL)AMINO]PROPANOIC ACID; (2S)-2-[(METHYLCARBAMOYL)AMINO]PROPANOIC ACID; (2S)-2-AMINO-2-(3-FURYL)ACETIC ACID; (2S)-2-AMINO-2,3-DIMETHYLBUTANOIC ACID; (2S)-2-AMINO-2-CYCLOBUTYLPROPANOIC ACID; (2S)-2-AMINO-2-CYCLOPROPYLPROPANOIC ACID; (2S)-2-AMINO-3-(2-METHYLENECYCLOPROPYL)PROPANOIC ACID; (2S)-2-AMINO-4-FLUOROBUTANOIC ACID; (2S)-2-AMINO-4-METHYLHEXANOIC ACID; (2S)-2-AMINO-5-HEXENOIC ACID; (2S)-2-AMINOPENT-4-ENOIC ACID; (2S)-2-BUTOXYPROPANOIC ACID; (2S)-2-METHYL-3-(METHYLSULFANYL)PROPANOIC ACID; (2S)-2-PROPANAMIDOPROPANOIC ACID; (2S)-4-HYDROXYPYRROLIDINE-2-CARBOXYLIC ACID; (2S)-5-HYDROXY-2-PIPERIDINECARBOXYLIC ACID; (2S)-5-METHYLPYRROLIDINE-2-CARBOXYLIC ACID; (2S)AZETIDINE-2-CARBOXYLIC ACID; (2S)-HYDROXYBUTANEDIOIC ACID 1-METHYL ESTER; (2S)-NORBORNANE-2-CARBOXYLIC ACID; (2S)-OXIRANE-2-CARBOXYLIC ACID; (2S)PIPERIDINE-2-CARBOXYLIC ACID; (2S,3S)-3-AMINO-2-OXETANECARBOXYLIC ACID; (2S,3R)-(+)-2-AMINO-3-HYDROXY-4-METHYLPENTANOIC ACID; (2S,3R)-2-AMINO-3-HYDROXY-PENTANOIC ACID; (2S,3R)-2-AMINO-3-METHYLSUCCINIC ACID; (2S,3R)-3-AMINO-2-HYDROXYHEXANOIC ACID; (2S,3R)-3-HYDROXY-L-ISOVALINE; (2S,3S)-(+)-2-AMINO-3-METHYLPENTANOIC-UL-14C ACID HYDROCHLORIDE; (2S,3S)-2-AMINO-3-ETHOXYBUTANOIC ACID; (2S,3S)-2-AMINO-3-HYDROXY-4-METHYL-VALERIC ACID; (2S,3S)-2-AMINO-3-HYDROXY-HEXANOIC ACID; (2S,3S)-2-AMINO-3-HYDROXY-PENTANOIC ACID; (2S,3S)-2-AMINO-3-METHOXYBUTANOIC ACID; (2S,3S)-2-HYDROXY-3-METHYLPENTANOIC ACID; (2S,3S)-3-AMINO-2-HYDROXYHEXANOIC ACID; (2S,3S)-3-HYDROXY-L-ISOVALINE; (2S,3S)-3-METHYLPYRROLIDINE-2-CARBOXYLIC ACID; (2S,3S)-DIAMINOSUCCINIC ACID; (2S,4R)-4-(AMINOMETHYL)PYRROLIDINE-2-CARBOXYLIC ACID; (2S,4R)-4-(HYDROXYMETHYL)

PYRROLIDINE-2-CARBOXYLIC ACID; (2S,4R)-4-(METHYLAMINO)PYRROLIDINE-2-CARBOXYLIC ACID; (2S,4R)-4-AMINOPYRROLIDINE-2-CARBOXYLIC ACID; (2S,4R)-4-CYANOPYRROLIDINE-2-CARBOXYLIC ACID; (2S,4R)-4-FLUOROPYRROLIDINE-2-CARBOXYLIC ACID; (2S,4R)-4-HYDROXY-1-METHYLPYRROLIDINE-2-CARBOXYLIC ACID; (2S,4R)-4-HYDROXYPIPERIDINE-2-CARBOXYLIC ACID; (2S,4S)-(−)-AZETIDINE-2,4-DICARBOXYLIC ACID; (2S,4S)-4-(AMINOMETHYL)PYRROLIDINE-2-CARBOXYLIC ACID; (2S,4S)-4-(METHYLAMINO)PYRROLIDINE-2-CARBOXYLIC ACID; (2S,4S)-4-AMINOPYRROLIDINE-2-CARBOXYLIC ACID; (2S,4S)-4-CYANOPYRROLIDINE-2-CARBOXYLIC ACID; (2S,4S)-4-FLUOROPYRROLIDINE-2-CARBOXYLIC ACID; (2S,4S)-4-HYDROXYPIPERIDINE-2-CARBOXYLIC ACID; (2Z)-3-([AMINO(IMINO)METHYL]SULFANYL)-2-PROPENOIC ACID; (2Z)-3-CYCLOPROPYL-2-PROPENOIC ACID; (2Z)-3-THIOCYANATO-2-PROPENOIC ACID; (2Z,4E)-HEXA-2,4-DIENOIC ACID; (3-AMINO-1H-1,2,4-TRIAZOL-1-YL)ACETIC ACID; (3-AMINO-1H-1,2,4-TRIAZOL-5-YL)ACETIC ACID; (3-AMINOPROPOXY)-ACETIC ACID; (3-AMINOPYRAZOL-1-YL)ACETIC ACID; (3-AMINO-PYRROLIDIN-1-YL)-ACETIC ACID; (3-AMINO-TETRAHYDRO-FURAN-2-YL)-ACETIC ACID; (3-HYDROXY-1H-PYRAZOL-4-YL)ACETIC ACID; (3-HYDROXY-PYRROLIDIN-1-YL)-ACETIC ACID; (3-METHYL)PYRROLIDIN-2-YL ACETIC ACID; (3-METHYL-[1,2,4]OXADIAZOL-5-YL)-ACETIC ACID; (3-METHYL-1H-PYRAZOL-1-YL) ACETIC ACID; (3-METHYL-1H-PYRROL-2-YL)-ACETIC ACID; (3-METHYL-3H-IMIDAZOL-4-YL)-ACETIC ACID; (3-METHYL-4,5-DIHYDRO-1H-PYRAZOL-1-YL)ACETIC ACID; (3-METHYLBUTOXY)ACETIC ACID; (3-OXO-PYRROLIDIN-1-YL)-ACETIC ACID; (3R)-3-(ACETYLAMINO)BUTANOIC ACID; (3R)-3-AMINO-3-HYDROXYPROPANOIC ACID; (3R)-3-AMINO-4-METHYLHEXANOIC ACID; (3R)-3-AMINO-PYRROLIDINE-3-CARBOXYLIC ACID; (3R)-THIOMORPHOLINECARBOXYLIC ACID; (3R,2R)-2,3-DIAMINOBUTYRIC ACID; (3R,4R)-3-AMINO-4-HYDROXYPENTANOIC ACID; (3R,4S)-1-AZABICYCLO[2.2.1]HEPTANE-3-CARBOXYLIC ACID; (3S)-1,3-DIOXANE-2-METHYL-4-CARBOXYLIC ACID; (3S)-1-METHYL-3-PIPERIDINECARBOXYLIC ACID; (3S)-3-(ACETYLAMINO)BUTANOIC ACID; (3S)-3-AMINO-4-METHYLHEXANOIC ACID; (3S)-3-AMINOPYRROLIDINE-3-CARBOXYLIC ACID; (3S,2R)-2,3-DIAMINOBUTYRIC ACID; (3S,2S)-2,3-DIAMINOBUTYRIC ACID; (3S,4S)-4-METHYLPYRROLIDINE-3-CARBOXYLIC ACID; (4,5-DIHYDRO-1H-IMIDAZOL-2-YLAMINO)-ACETIC ACID; (4,5-DIHYDRO-3H-PYRROL-2-YLAMINO)-ACETIC ACID; (4-AMINO-1H-PYRAZOL-1-YL)ACETIC ACID; (4E)-2-AMINOHEX-4-ENOIC ACID; (4-METHYL-[1,2,3]TRIAZOL-1-YL)-ACETIC ACID; (4-METHYL-1H-IMIDAZOL-2-YL)-ACETIC ACID; (4-METHYL-1H-PYRAZOL-1-YL)ACETIC ACID; (4-METHYL-FURAZAN-3-YL)-ACETIC ACID; (4R)-1,3-THIAZINANE-4-CARBOXYLIC ACID; (4R)-2-AMINO-4,5-DIHYDRO-1,3-THIAZOLE-4-CARBOXYLIC ACID; (4R)-3-METHYL-1,3-THIAZOLIDINE-4-CARBOXYLIC ACID; (4S)-1,3-THIAZINANE-4-CARBOXYLIC ACID; (4S)-4-AMINO-D-PROLINE; (4S)-4-METHYLHEPTANOIC ACID; (4S)-4-METHYL-L-PROLINE; (4S)-4-METHYL-NORLEUCINE; (4S,2RS)-2-METHYLTHIAZOLIDINE-4-CARBOXYLIC ACID; (5-AMINO-1H-1,2,4-TRIAZOL-3-YL)ACETIC ACID; (5-AMINO-1H-TETRAZOL-1-YL)ACETIC ACID; (5-AMINO-2H-TETRAZOL-2-YL)ACETIC ACID; (5-AMINO-4H-[1,2,4]TRIAZOL-3-YL)-ACETIC ACID; (5-METHYL-1H-PYRAZOL-3-YL)-ACETIC ACID; (5-METHYL-1H-TETRAZOL-1-YL)ACETIC ACID; (5-METHYL-2H-[1,2,4]TRIAZOL-3-YL)-ACETIC ACID; (5-METHYL-4,5-DIHYDRO-1H-PYRAZOL-1-YL)ACETIC ACID; (5-METHYL-4H-1,2,4-TRIAZOL-3-YL)ACETIC ACID; (5-METHYL-FURAN-2-YL)-ACETIC ACID; (5-METHYL-IMIDAZOL-1-YL)-ACETIC ACID; (5-METHYL-PYRAZOL-1-YL)-ACETIC ACID; (5-OXO-2,5-DIHYDRO-1H-1,2,4-TRIAZOL-3-YL)ACETIC ACID; (5-OXO-2,5-DIHYDRO-1H-PYRAZOL-3-YL)ACETIC ACID; (5-OXO-4,5-DIHYDRO-1H-1,2,4-TRIAZOL-3-YL)ACETIC ACID; (ALLYLSULFINYL)ACETIC ACID; (ALLYLTHIO)ACETIC ACID; (ALPHAR)-ALPHA-HYDROXY-CYCLOPROPANEPROPANOIC ACID; (ALPHAS)-ALPHA-HYDROXY-CYCLOBUTANEPROPANOIC ACID; (ALPHAS)-ALPHA-HYDROXY-CYCLOPROPANEPROPANOIC ACID; (AMIDINOTHIO) ACETIC ACID; (AMINOSULFONYL)ACETIC ACID; (AR)-A-HYDROXY-2-FURANACETIC ACID; (BUTYLTHIO)ACETIC ACID; (BUTYRYLAMINO)ACETIC ACID; (CYCLOBUTYLCARBAMOYL)FORMIC ACID; (CYCLOPENTYLAMINO)ACETIC ACID; (D,L)-2-AMINO-HEPT-6-ENOIC ACID; (DIETHYLAMINO)(OXO)ACETIC ACID; (E)-2-(METHOXYIMINO)ACETIC ACID; (E)-3-(1H-IMIDAZOL-5-YL)-2-PROPENOIC ACID; (E)-3-(1H-PYRROL-1-YL)-2-PROPENOIC ACID; (E)-3-(1H-PYRROL-2-YL)ACRYLIC ACID; (E)-3,4,4-TRIMETHYLPENT-2-ENOIC ACID; (E)-3-CYANO-3-(METHYLIMINO)-2-OXOPROPANOIC ACID; (E)-3-CYCLOBUTYLACRYLIC ACID; (E)-3-CYCLOPENTYLACRYLIC ACID; (E)-3-CYCLOPROPYLACRYLIC ACID; (E)-3-METHOXY-2-BUTENOIC ACID; (E)-4,4-DIMETHYL-2-PENTENOIC ACID; (E)-5-(METHYLTHIO)PENT-2-ENOIC ACID; (E)-5-METHYL-HEX-2-ENOIC ACID; (ETHYLTHIO)ACETIC ACID; (ISOBUTYLAMINO)(OXO)ACETIC ACID; (ISOBUTYLTHIO)ACETIC ACID; (ISOBUTYRYLAMINO)ACETIC ACID; (ISOPROPENYLAMINO)ACETIC ACID; (ISOPROPYLTHIO)ACETIC ACID; (METHYLTHIO)ACETIC ACID; (N'-ACETYL-N-METHYL-HYDRAZINO)-ACETIC ACID; (N-CARBOXYMETHYLHYDRAZINO)-ACETIC ACID; (N-HYDROXYCARBAMIMIDOYL)-ACETIC ACID; (PROP-2-YNYLTHIO)ACETIC ACID; (PROPYLAMINO) ACETIC ACID; (PROPYLTHIO)ACETIC ACID; (PYRROL-3-YL)-ACETIC ACID; (R)-(−)-2-AMINO-2-METHYLBUTANEDIOIC ACID; (R)-(+2-METHYLGLUTARIC ACID; (R)-(−)-5-OXOTETRAHYDROFURAN-2-CARBOXYLIC ACID; (R)-(−)-CITRAMALIC ACID; (R)-(−)-NIPECOTIC ACID; (R)-(+)-2,2-DIMETHYL-1,3-DIOXOLAN-4-CARBOXYLATE; (R)-(+)-2-CHLOROPROPIONIC ACID; (R)-(+)-2-METHOXYPROPIONIC ACID; (R)-(+)-2-TETRAHYDROFUROIC ACID; (R)-(+)-3-CYCLOHEXENECARBOXYLIC ACID; (R)-(+)-3-METHYLSUCCINIC ACID 1-MONOMETHYL ESTER; (R)-(+)-4-OXO-2-AZETIDINECARBOXYLIC ACID; (R)-(+)-METHYLSUCCINIC ACID; (R)-(2-HYDROXYPYRROLIDIN-1-YL)-ACETIC ACID; (R)-(3-AMINO-PYRROLIDIN-1-YL)-ACETIC ACID; (R)-(3-HYDROXYPYRROLIDIN-1-YL)-ACETIC ACID; (R)-1,2,3,6-TETRAHYDROPYRIDINE-2-CARBOXYLIC ACID; (R)-1-AMINO-2,2-DIMETHYLCYCLOPROPAN-

ECARBOXYLIC ACID; (R)-1-METHYLPYRROLIDINE-2-CARBOXYLIC ACID; (R)-2-(PIPERIDIN-2-YL)ACETIC ACID; (R)-2-(PIPERIDIN-3-YL)ACETIC ACID; (R)-2-(PYRROLIDIN-3-YL)ACETIC ACID; (R)-2,2-DIMETHYLCYCLOPROPANECARBOXYLIC ACID; (R)-2,3-DIMETHYLBUTANOIC ACID; (R)-2,5-DIMETHYLHEX-5-ENOIC ACID; (R)-2-AMINO-2-METHYL-4-PENTENOIC ACID; (R)-2-AMINO-2-METHYL-PENTANOIC ACID; (R)-2-AMINO-3-(CARBAMOYLOXY)PROPANOIC ACID; (R)-2-AMINO-3-CYANOPROPANOIC ACID; (R)-2-AMINO-3-HYDROXY-3-METHYLBUTANOIC ACID; (R)-2-AMINO-3-METHOXYLPROPANOIC ACID; (R)-2-AMINO-4-METHOXYBUTYRIC ACID; (R)-2-AMINO-5-METHYLHEXANOIC ACID; (R)-2-AMINO-BUTYRIC ACID HYDROCHLORIDE; (R)-2-AMINOHEPT-6-YNOIC ACID; (R)-2-AMINOHEX-5-YNOIC ACID; (R)-2-AMINOMETHYL-3-METHYL-BUTYRIC ACID; (R)-2-AMINOMETHYL-4-METHYL-PENTANOIC ACID; (R)-2-AMINO-N-METHYL-SUCCINAMIC ACID; (R)-2-CHLORO-3-METHYLBUTYRIC ACID; (R)-2-CHLOROBUTYRIC ACID; (R)-2-HYDROXY-2-METHYLBUTYRIC ACID; (R)-2-HYDROXY-4-METHYLPENTANOIC ACID; (R)-2-HYDROXYBUTYRIC ACID; (R)-2-HYDROXYMETHYLBUTANOIC ACID; (R)-2-HYDROXYMETHYLHEXANOIC ACID; (R)-2-HYDROXYMETHYL-PENTANOIC ACID; (R)-2-HYDROXYMETHYLPROPANOIC ACID; (R)-2-METHYL-4-NITROBUTANOIC ACID; (R)-2-METHYLHEPT-6-ENOIC ACID; (R)-2-METHYLPENTANOIC ACID; (R)-2-METHYLPROLINE; (R)-2-MORPHOLINEACETIC ACID; (R)-2-OXOHEXAHYDROPYRIMIDINE-4-CARBOXYLIC ACID; (R)-2-OXO-IMIDAZOLIDINE-4-CARBOXYLIC ACID; (R)-2-VINYLHEX-5-ENOIC ACID; (R)-2-VINYLHEXANOIC ACID; (R)-2-VINYLPENT-4-ENOIC ACID; (R)-2-VINYLPENTANOIC ACID; (R)-3-(HYDROXYMETHYL)PENT-4-ENOIC ACID; (R)-3,3,3-TRIFLUORO-2-HYDROXYPROPIONIC ACID; (R)-3,4-DIAMINOBUTYRIC ACID; (R)-3,5-DIAMINOPENTANOIC ACID; (R)-3-AMINO-2-(HYDROXYMETHYL)PROPANOIC ACID; (R)-3-AMINO-2-METHYLPROPANOIC ACID-HCL; (R)-3-AMINO-2-METHYL-PROPIONIC ACID; (R)-3-AMINO-3-CYCLOBUTYL-PROPIONIC ACID; (R)-3-AMINO-3-CYCLOPROPYL-PROPIONIC ACID; (R)-3-AMINO-3-METHYLPENTANOIC ACID; (R)-3-AMINO-4-METHYL-PENTANOIC ACID; (R)-3-AMINO-5-METHYL-HEXANOIC ACID; (R)-3-AMINO-BUTANOIC ACID HYDROCHLORIDE SALT; (R)-3-AMINOBUTYRIC ACID; (R)-3-AMINO-HEPT-6-ENOIC ACID; (R)-3-AMINOHEX-5-ENOIC ACID; (R)-3-AMINO-L-PROLINE; (R)-3-AMINO-PENTANOIC ACID; (R)-3-AMINOTETRAHYDRO-2H-PYRAN-3-CARBOXYLIC ACID; (R)-3-AMINOTETRAHYDROFURAN-3-CARBOXYLIC ACID; (R)-3-AMINOTETRAHYDROTHIOPHENE-3-CARBOXYLIC ACID; (R)-3-CHLOROLACTIC ACID; (R)-3-HYDROXYBUTYRIC ACID; (R)-3-METHYLHEPTANOIC ACID; (R)-3-METHYLHEMNOIC ACID; (R)-3-METHYL-PENTANOIC ACID; (R)-4-AMINO-2-HYDROXYBUTYRIC ACID; (R)-4-AMINO-3-HYDROXYBUTANOIC ACID; (R)-4-AMINOHEX-5-ENOIC ACID; (R)-4-OXO-2-PIPERRIDINE CARBOXYLIC ACID; (R)-4-OXOPYRROLIDINE-2-CARBOXYLIC ACID; (R)-5-AMINO-4-HYDROXYPENTANOIC ACID; (R)-5-OXO-PIPERAZINE-2-CARBOXYLIC ACID; (R)-5-OXO-PYRROLIDINE-3-CARBOXYLIC ACID; (R)-6-OXO-PIPERAZINE-2-CARBOXYLIC ACID; (R)-ALPHA-ALLYLALANINE H2O; (R)-ALPHA-ETHYLALANINE H2O; (R)-ALPHA-PROPARGYLALANINE; (R)-AMINOFURAN-2-YL-ACETIC ACID; (R)-HEXAHYDRO-1H-AZEPINE-2-CARBOXYLIC ACID; (R)-ISOSERINE; (R)-MORPHOLIN-3-YL-ACETIC ACID; (R)-MORPHOLINE-2-CARBOXYLIC ACID; (R)-MORPHOLINE-3-CARBOXYLIC ACID; (R)-PIPERAZINE-2-CARBOXYLIC ACID; (R)-PIPERIDINE-2-CARBOXYLIC ACID; (R)-PYRROLIDINE-3-CARBOXYLIC ACID; (R)-TETRAHYDRO-3-FURANCARBOXYLIC ACID; (R)-TRIMETHYLLACTIC ACID; (R,S)-2-AMINO-3-HYDROXY-2-METHYLPROPIONIC ACID HYDRATE; (R,S)-2-AMINO-3-HYDROXY-3-METHYLBUTANOIC ACID; (R,S)-2-AMINOPENT-4-YNOIC ACID HYDROCHLORIDE; (RS)-(TETRAZOL-5-YL)GLYCINE; (S)-(+2-ACETOXYPROPIONIC ACID; (S)-(−)-2-AMINO-2-METHYL-4-PENTENOIC ACID HYDRATE; (S)-(−)-2-CHLOROPROPIONIC ACID; (S)-(−)-2-HYDROXY-3,3-DIMETHYLBUTYRIC ACID; (S)-(−)-2-METHOXYPROPIONIC ACID; (S)-(+3,3,3-TRIFLUORO-2-HYDROXYPROPANOIC ACID; (S)-(−)-3-CYCLOHEXENECARBOXYLIC ACID; (S)-(+4-AMINO-2-HYDROXYBUTYRIC ACID; (S)-(−)-4-OXO-2-AZETIDINECARBOXYLIC ACID; (S)-(−)-METHYLSUCCINIC ACID; (S)-(−)-TETRAHYDRO-2-FUROIC ACID; (S)-(−)-THIOLACTIC ACID; (S)-(+)-2,2-DIMETHYLCYCLOPROPANECARBOXYLIC ACID; (S)-(+)-2-AMINO-2-METHYLBUTANOIC ACID MONOHYDRATE; (S)-(+)-2-AMINO-3-HYDROXY-3-METHYLBUTANOIC ACID; (S)-(+)-2-HYDROXY-3-METHYLBUTYRIC ACID; (S)-(+)-2-METHYLBUTYRIC ACID; (S)-(+)-2-METHYLGLUTARIC ACID; (S)-(+)-5-OXOTETRAHYDROFURAN-2-CARBOXYLIC ACID; (S)-(+)-CITRAMALIC ACID; (S)-(+)-NIPECOTIC ACID; (S)-(+)-SERINE-UL-14C HYDROCHLORIDE; (S)-(+)-VALINE-UL-14C HYDROCHLORIDE; (S)-(2-HYDROXYPYRROLIDIN-1-YL)-ACETIC ACID; (S)-(3-AMINO-PYRROLIDIN-1-YL)-ACETIC ACID; (S)-(3-HYDROXYPYRROLIDIN-1-YL)-ACETIC ACID; (S)-1,2,3,4-TETRAHYDRO-PYRIDINE-2-CARBOXYLIC ACID; (S)-1,4-OXAZEPANE-3-CARBOXYLIC ACID; (S)-1-AMINO-2,2-DIMETHYLCYCLOPROPANECARBOXYLIC ACID; (S)-1-ISOPROPYL-AZETIDINE-2-CARBOXYLIC ACID; (S)-2-(2-PYRROLIDINYL)ACETIC ACID; (S)-2-(PIPERIDIN-2-YL)ACETIC ACID; (S)-2-(PIPERIDIN-3-YL)ACETIC ACID; (S)-2-(PYRROLIDIN-3-YL)ACETIC ACID; (S)-2,2-DIMETHYL-1,3-DIOXOLANE-4-CARBOXYLIC ACID; (S)-2,3-DIMETHYLBUTANOIC ACID; (S)-2,4-DIHYDROXYBUTYRIC ACID; (S)-2,5-DIMETHYLHEX-5-ENOIC ACID; (S)-2-AMINO-2-(MERCAPTOMETHOXY)ACETIC ACID; (S)-2-AMINO-2-FURANACETIC ACID; (S)-2-AMINO-2-METHYL-4-PENTENOIC ACID; (S)-2-AMINO-2-METHYL-PENTANOIC ACID; (S)-2-AMINO-3-METHOXYPROPANOIC ACID; (S)-2-AMINO-4-(METHYLAMINO)-4-OXOBUTANOIC ACID; (S)-2-AMINO-4-CYANOBUTYRIC ACID; (S)-2-AMINO-4-METHOXYBUTYRIC ACID; (S)-2-AMINO-5-METHYLHEXANOIC ACID; (S)-2-AMINO-6-HEPTENOIC ACID; (S)-2-AMINOHEPT-6-YNOIC ACID; (S)-2-AMINOHEX-5-YNOIC ACID; (S)-2-AMINOMETHYL-3-METHYL-BUTYRIC ACID; (S)-2-AMINOMETHYL-4-METHYL-PENTANOIC ACID; (S)-2-

CHLORO-3-METHYLBUTYRIC ACID; (S)-2-CHLORO-N-BUTYRIC ACID; (S)-2-FLUORO-4-METHYLPENTANOIC ACID; (S)-2-HYDROXY-2,3-DIMETHYLBUTANOIC ACID; (S)-2-HYDROXY-2-METHYLBUTYRIC ACID; (S)-2-HYDROXYBUTYRIC ACID; (S)-2-HYDROXYMETHYL-HEXANOIC ACID; (S)-2-HYDROXYMETHYL-PENTANOIC ACID; (S)-2-HYDROXYPENTANOIC ACID; (S)-2-MERCAPTOBUTANOIC ACID; (S)-2-METHYL-1,4,5,6-TETRAHYDROPYRIMIDINE-4-CARBOXYLIC ACID; (S)-2-METHYLHEPT-6-ENOIC ACID; (S)-2-METHYLPENTENOIC ACID; (S)-2-METHYLPIPERIDINE-2-CARBOXYLIC ACID; (S)-2-METHYLSUCCINIC ACID 1-METHYL ESTER; (S)-2-MORPHOLINEACETIC ACID; (S)-2-OXOHEXAHYDROPYRIMIDINE-4-CARBOXYLIC ACID; (S)-2-PIPERIDINONE-6-CARBOXYLIC ACID; (S)-2-PYRROLIDIN-1-YL-PROPIONIC ACID; (S)-2-VINYLHEX-5-ENOIC ACID; (S)-2-VINYLHEXANOIC ACID; (S)-2-VINYLPENT-4-ENOIC ACID; (S)-2-VINYLPENTANOIC ACID; (S)-3-(HYDROXYMETHYL)PENT-4-ENOIC ACID; (S)-3,4-DIAMINOBUTYRIC ACID; (S)-3,5-DIAMINOPENTANOIC ACID; (S)-3-AMINO-2-(HYDROXYMETHYL)PROPANOIC ACID; (S)-3-AMINO-2-METHYLPROPANOIC ACID-HCL; (S)-3-AMINO-2-METHYL-PROPIONIC ACID; (S)-3-AMINO-3-CYCLOBUTYL-PROPIONIC ACID; (S)-3-AMINO-3-CYCLOPROPYL-PROPIONIC ACID; (S)-3-AMINO-3-METHYLPENTANOIC ACID; (S)-3-AMINO-4,4-DIMETHYL-PENTANOIC ACID; (S)-3-AMINO-4-METHYL-PENTANOIC ACID; (S)-3-AMINO-5-METHYL-HEXANOIC ACID; (S)-3-AMINOBUTANOIC ACID; (S)-3-AMINO-HEPT-6-ENOIC ACID; (S)-3-AMINO-HEX-5-ENOIC ACID; (S)-3-AMINO-PENTANOIC ACID; (S)-3-AMINOTETRAHYDRO-2H-PYRAN-3-CARBOXYLIC ACID; (S)-3-AMINOTETRAHYDROFURAN-3-CARBOXYLIC ACID; (S)-3-AMINOTETRAHYDROTHIOPHENE-3-CARBOXYLIC ACID; (S)-3-HYDROXY-2-METHYL-PROPIONIC ACID; (S)-3-HYDROXY-4-METHOXY-4-OXOBUTANOIC ACID; (S)-3-HYDROXYBUTYRIC ACID; (S)-3-METHYLHEPTANOIC ACID; (S)-3-METHYLHEXANOIC ACID; (S)-3-METHYL-PENTANOIC ACID; (S)-4,4-DIMETHYL-PYRROLIDINE-2-CARBOXYLIC ACID; (S)-4,5-DIDEHYDROPIPECOLIC ACID; (S)-4-AMINO-3-HYDROXYBUTANOIC ACID; (S)-4-AMINOHEX-5-ENOIC ACID; (S)-4-METHYL-HEXANOIC ACID; (S)-4-OXO-2-PIPERIDINE CARBOXYLIC ACID; (S)-5-AMINO-4-HYDROXYPENTANOIC ACID; (S)-5-METHYLHEPTANOIC ACID; (S)-5-OXO-PIPERAZINE-2-CARBOXYLIC ACID; (S)-5-OXO-PYRROLIDINE-3-CARBOXYLIC ACID; (S)-6-OXO-PIPERAZINE-2-CARBOXYLIC ACID; (S)-A-AMINO-2-HYDROXYBUTANOIC ACID; (S)-ALPHA-METHYLCYSTEINE; (S)-ALPHA-PROPARGYLALANINE; (S)-AMINO-(1H-IMIDAZOL-2-YL)-ACETIC ACID; (S)-HEXAHYDRO-1H-AZEPINE-2-CARBOXYLIC ACID; (S)-ISOSERINE; (S)-MORPHOLIN-3-YL-ACETIC ACID; (S)-MORPHOLINE-2-CARBOXYLIC ACID; (S)-MORPHOLINE-3-CARBOXYLIC ACID; (S)-OXAZOLIDINE-4-CARBOXYLIC ACID; (S)-PIPERAZINE-2-CARBOXYLIC ACID; (S)-PYRROLIDINE-2-CARBOXYLIC ACID; (S)-TETRAHYDRO-3-FURANCARBOXYLIC ACID; (S)-THIOMORPHOLINE-3-CARBOXYLIC ACID; (SEC-BUTYLAMINO)(OXO) ACETIC ACID; (TERT-BUTYLAMINO)(OXO)ACETIC ACID; (TERT-BUTYLTHIO)ACETIC ACID; (TETRAHYDRO-FURAN-2-YL)-ACETIC ACID; (TETRAHYDRO-FURAN-3-YL)-ACETIC ACID; (TETRAHYDRO-PYRAN-2-YL)-ACETIC ACID; (TETRAHYDRO-PYRAN-4-YLIDENE)-ACETIC ACID; (TRIFLUOROMETHOXY)ACETIC ACID; (TRIMETHYLSILYL)ACETIC ACID; (Z)-3-(1H-PYRROL-2-YL)-2-PROPENOIC ACID; (Z)-3-(2-FURANYL)-2-PROPENOIC ACID; (Z)-3-CYCLOPROPYLBUT-2-ENOIC ACID; (Z)-HEX-2-ENOIC ACID; [(2-AMINO-2-OXO-ETHYL)THIO]ACETIC ACID; [(2-METHOXYETHYL)(METHYL)AMINO]ACETIC ACID; [(2-METHOXYETHYL)CARBAMOYL]FORMIC ACID; [(2-METHYLBUTYL)AMINO]ACETIC ACID; [(2-METHYLCYCLOPROPYL)CARBAMOYL]FORMIC ACID; [(3-METHYLBUTYL)AMINO]ACETIC ACID; [(CYCLOPROPYLMETHYL)THIO]ACETIC ACID; [(PROP-2-EN-1-YL)CARBAMOYL]FORMIC ACID; [(PROP-2-YN-1-YL)CARBAMOYL]FORMIC ACID; [ETHYL(METHYL)AMINO]ACETIC ACID; 1-(2-AMINOETHYL)CYCLOPROPANECARBOXYLIC ACID; 1-(2-PROPYN-1-YL)-1H-PYRROLE-2-CARBOXYLIC ACID; 1-(AMINOMETHYL)CYCLOBUTANE-1-CARBOXYLIC ACID; 1-(AMINOMETHYL)CYCLOPENTANECARBOXYLIC ACID; 1-(AMINOMETHYL)CYCLOPROPANECARBOXYLIC ACID; 1-(CARBOXYMETHYL)PYRIDINIUM; 1-(CHLOROCARBONYL)-CYCLOPROPANECARBOXYLIC ACID; 1-(CYCLOPROPYLMETHYL)CYCLOPROPANECARBOXYLIC ACID; 1-(DIMETHYLAMINO)CYCLOBUTANE-1-CARBOXYLIC ACID; 1-(DIMETHYLAMINO)CYCLOPROPANECARBOXYLIC ACID; 1-(ETHYLAMINO)CYCLOBUTANE-1-CARBOXYLIC ACID; 1-(HYDROXYMETHYL)-1H-PYRAZOLE-3-CARBOXYLIC ACID; 1-(HYDROXYMETHYL)-1H-PYRAZOLE-4-CARBOXYLIC ACID; 1-(HYDROXYMETHYL)-CYCLOPENTANECARBOXYLIC ACID; 1-(HYDROXYMETHYL)CYCLOPROPANECARBOXYLIC ACID; 1-(METHOXYMETHYL)CYCLOBUTANECARBOXYLIC ACID; 1-(METHOXYMETHYL)CYCLOPROPANECARBOXYLIC ACID; 1-(METHYLAMINO)CYCLOBUTANE-1-CARBOXYLIC ACID; 1-(METHYLAMINO)CYCLOPENTANE-1-CARBOXYLIC ACID; 1-(METHYLCARBAMOYL)CYCLOPROPANE-1-CARBOXYLIC ACID; 1,1-CYCLOBUTANEDICARBOXYLIC ACID; 1,1-CYCLOPROPANEDICARBOXYLIC ACID; 1,1-CYCLOPROPANEDICARBOXYLIC ACID MONOMETHYL ESTER; 1,1-DICYCLOPROPANECARBOXYLIC ACID; 1,2,3,6-TETRAHYDRO-PYRIDINE-2-CARBOXYLIC ACID; 1,2,3,6-TETRAHYDRO-PYRIDINE-4-CARBOXYLIC ACID; 1,2,3-THIADIAZOLE-4-CARBOXYLIC ACID; 1,2,3-THIADIAZOLE-5-CARBOXYLIC ACID; 1,2,3-TRIAZOLE-4-CARBOXYLIC ACID; 1,2,4-OXADIAZOLE-3-CARBOXYLIC ACID; 1,2,4-OXADIAZOLE-5-CARBOXYLIC ACID; 1,2,4-TRIAZINE-3-CARBOXYLIC ACID; 1,2,4-TRIAZINE-5-CARBOXYLIC ACID; 1,2,4-TRIAZOLE-1-ACETIC ACID; 1,2,5,6-TETRAHYDROPYRIDINE-3-CARBOXYLIC ACID; 1,2,5-OXADIAZOLE-3-CARBOXYLIC ACID; 1,2,5-OXADIAZOLE-3-CARBOXYLIC ACID, 4-(METHYLAMINO)-; 1,2,5-THIADIAZOLE-3-CARBOXYLIC ACID; 1,2-CYCLOPROPANEDICARBOXYLIC ACID, (1R,2R)-REL-; 1,2-CYCLOPROPANEDICARBOXYLIC ACID, (1R,2S)-REL-; 1,2-DIMETHYL-

1H-IMIDAZOLE-5-CARBOXYLIC ACID; 1,3,4-OXADIAZOLE-2-CARBOXYLIC ACID; 1,3,4-THIADIAZOLE-2-CARBOXYLIC ACID; 1,3,5,7-CYCLOOCTATETRAENECARBOXYLIC ACID; 1,3,5-TRIAZINE-2-CARBOXYLIC ACID; 1,3-ACETONEDICARBOXYLIC ACID; 1,3-DIHYDRO-IMIDAZOL-2-ONE-5-METHYL-4-CARBOXYLIC ACID; 1,3-DIMETHYL-1H-PYRAZOLE-4-CARBOXYLIC ACID; 1,3-DIMETHYL-1H-PYRAZOLE-5-CARBOXYLIC ACID; 1,3-DIMETHYL-1H-PYRROLE-2-CARBOXYLIC ACID; 1,3-DIMETHYL-PYRROLIDINE-3-CARBOXYLIC ACID; 1,3-METHYLENECYCLOBUTANE CARBOXYLIC ACID; 1,3-OXATHIOLANE-2-CARBOXYLIC ACID, 5-OXO-; 1,3-THIAZINANE-4-CARBOXYLIC ACID; 1,3-THIAZOL-4-YLACETIC ACID; 1,4,5,6-TETRAHYDROPYRIDAZINE-3-CARBOXYLIC ACID; 1,4-DIHYDRO-2-METHYLBENZOIC ACID; 1,4-DIHYDRO-4-OXO-2-PYRIDINECARBOXYLIC ACID; 1,4-DIHYDROBENZOIC ACID; 1,4-DIOXANE-2-CARBOXYLIC ACID; 1,4-OXAZEPANE-3-CARBOXYLIC ACID; 1,5-DIMETHYL-1H-1,2,3-TRIAZOLE-4-CARBOXYLIC ACID; 1,5-DIMETHYL-1H-IMIDAZOLE-2-CARBOXYLIC ACID; 1,5-DIMETHYL-1H-PYRAZOLE-3-CARBOXYLIC ACID; 1,5-DIMETHYL-1H-PYRAZOLE-4-CARBOXYLIC ACID; 1,5-DIMETHYL-1H-PYRROLE-2-CARBOXYLIC ACID; 1,6-DIHYDRO-6-OXOPYRIMIDINE-4-CARBOXYLIC ACID; 1-ACETYL-2-AZETIDINECARBOXYLIC ACID; 1-ACETYL-3-AZETIDINECARBOXYLIC ACID; 1-ACETYLCYCLOPROPANECARBOXYLIC ACID; 1-ALLYL-AZETIDINE-2-CARBOXYLIC ACID; 1-ALLYLCYCLOPROPANECARBOXYLIC ACID; 1-AMINO-1H-IMIDAZOLE-2-CARBOXYLIC ACID; 1-AMINO-2,2-DIMETHYLCYCLOPROPANECARBOXYLIC ACID; 1-AMINO-2-ETHENYLCYCLOPROPANECARBOXYLIC ACID; 1-AMINO-2-METHYLCYCLOPENTANECARBOXYLIC ACID; 1-AMINO-2-METHYLENE-CYCLOPROPANECARBOXYLIC ACID; 1-AMINO-3,3-DIMETHYL-CYCLOBUTANECARBOXYLIC ACID; 1-AMINO-3-HYDROXYCYCLOBUTANECARBOXYLIC ACID; 1-AMINO-3-METHYLCYCLOPENTANECARBOXYLIC ACID; 1-AMINOAZETIDINE-2-CARBOXYLIC ACID; 1-AMINOCYCLOBUTANECARBOXYLIC ACID; 1-AMINOCYCLOHEXANECARBOXYLIC ACID; 1-AMINOCYCLOPENT-3-ENECARBOXYLIC ACID; 1-AMINOCYCLOPROPANE-1-CARBOXYLIC ACID; 1-AMINO-CYCLOPROPANE-1-CARBOXYLIC ACID HYDROCHLORIDE; 1-AZABICYCLO[2.2.1]HEPTANE-4-CARBOXYLIC ACID; 1-AZETIDINEACETIC ACID; 1-CARBAMOYL-AZETIDINE-3-CARBOXYLIC ACID; 1-CARBOXYCYCLOPROPANECARBOXAMIDE; 1-CUBANECARBOXYLIC ACID; 1-CYANO-1-CYCLOPROPANECARBOXYLIC ACID; 1-CYANOCYCLOBUTANECARBOXYLIC ACID; 1-CYANOCYCLOPENTANECARBOXYLIC ACID; 1-CYCLOBUTENE-1-CARBOXYLIC ACID; 1-CYCLOHEXENE-1-CARBOXYLIC ACID; 1-CYCLOHEXENYLACETIC ACID; 1-CYCLOPENTENE-1-CARBOXYLIC ACID, 2-AMINO-; 1-CYCLOPENTENECARBOXYLIC ACID; 1-CYCLOPROPYL-2-AZETIDINECARBOXYLIC ACID; 1-ETHYL-1H-1,2,3-TRIAZOLE-4-CARBOXYLIC ACID; 1-ETHYL-1H-IMIDAZOLE-2-CARBOXYLIC ACID; 1-ETHYL-1H-PYRAZOLE-3-CARBOXYLIC ACID; 1-ETHYL-1H-PYRAZOLE-4-CARBOXYLIC ACID; 1-ETHYL-1H-PYRAZOLE-5-CARBOXYLIC ACID; 1-ETHYL-1H-PYRROLE-2-CARBOXYLIC ACID; 1-ETHYL-1H-PYRROLE-3-CARBOXYLIC ACID; 1-ETHYL-4-OXO-2-AZETIDINECARBOXYLIC ACID; 1-ETHYL-AZETIDINE-3-CARBOXYLIC ACID; 1-ETHYLCYCLOBUTANECARBOXYLIC ACID; 1-ETHYLCYCLOPENTANE-1-CARBOXYLIC ACID; 1-ETHYLCYCLOPROPANECARBOXYLIC ACID; 1-ETHYLPYRROLIDINE-2-CARBOXYLIC ACID; 1-ETHYLPYRROLIDINE-3-CARBOXYLIC ACID; 1-FLUOROCYCLOHEXANECARBOXYLIC ACID; 1-FLUORO-CYCLOPROPANECARBOXYLIC ACID; 1-FORMYLPYRROLIDINE-2-CARBOXYLIC ACID; 1-FORMYLPYRROLIDINE-3-CARBOXYLIC ACID; 1H-[1,2,3]TRIAZOLE-4-CARBOXYLIC ACID; 1H-1,2,3-TRIAZOLE-1-ACETIC ACID; 1H-1,2,4-TRIAZOLE-3-CARBOXYLIC ACID; 1H-1,2,4-TRIAZOLE-3-CARBOXYLIC ACID, 5-METHYL-; 1H-1,2,4-TRIAZOLE-3-CARBOXYLIC ACID, 1-AMINO-; 1H-1,2,4-TRIAZOLE-3-CARBOXYLIC ACID, 5-AMINO-2,3-DIHYDRO-; 1H-1,2,4-TRIAZOLE-5-CARBOXYLIC ACID; 1H-IMIDAZOL-1-YL(OXO)ACETIC ACID; 1H-IMIDAZOL-4-YL(OXO)ACETIC ACID; 1H-IMIDAZOLE-1-ACETIC ACID, ALPHA-METHYL-, (R)-; 1H-IMIDAZOLE-1-ACETIC ACID,-ALPHA-FLUORO-; 1H-IMIDAZOLE-2-CARBOXYLIC ACID; 1H-IMIDAZOLE-2-CARBOXYLIC ACID HYDROCHLORIDE; 1H-IMIDAZOLE-2-CARBOXYLIC ACID, 4,5-DIHYDRO-5-OXO-; 1H-IMIDAZOLE-4-CARBOXYLIC ACID; 1H-IMIDAZOLE-5-CARBOXYLIC ACID; 1H-PYRAZOL-1-YLACETIC ACID; 1H-PYRAZOLE-3-CARBOXYLIC ACID; 1H-PYRAZOLE-4-CARBOXYLIC ACID; 1H-PYRAZOLE-4-CARBOXYLIC ACID HYDRATE; 1H-PYRROL-1-YLACETIC ACID; 1H-PYRROLE-2-CARBOXYLIC ACID, 3,4-DIFLUORO-; 1H-TETRAZOLE-1-ACETIC ACID; 1H-TETRAZOLE-5-ACETIC ACID; 1H-TETRAZOLE-5-CARBOXYLIC ACID; 1-HYDROXY-1-CYCLOPROPANECARBOXYLIC ACID; 1-HYDROXY-2-PIPERIDINECARBOXYLIC ACID; 1-HYDROXY-3-METHYLCYCLOPENTANE-1-CARBOXYLIC ACID; 1-HYDROXYCYCLOBUTANECARBOXYLIC ACID; 1-HYDROXYCYCLOHEXANECARBOXYLIC ACID; 1-HYDROXYCYCLOPENTANECARBOXYLIC ACID; 1-ISOPROPYL-AZETIDINE-2-CARBOXYLIC ACID; 1-ISOPROPYLAZETIDINE-3-CARBOXYLIC ACID; 1-METHOXYCYCLOPENTANE-1-CARBOXYLIC ACID; 1-METHYL-1-CYCLOHEXANECARBOXYLIC ACID; 1-METHYL-1H-1,2,3-TRIAZOLE-4-CARBOXYLIC ACID; 1-METHYL-1H-1,2,3-TRIAZOLE-5-CARBOXYLIC ACID; 1-METHYL-1H-1,2,4-TRIAZOLE-3-CARBOXYLIC ACID; 1-METHYL-1H-1,2,4-TRIAZOLE-5-CARBOXYLIC ACID; 1-METHYL-1H-IMIDAZOLE-2-CARBOXYLIC ACID; 1-METHYL-1H-IMIDAZOLE-4-CARBOXYLIC ACID; 1-METHYL-1H-IMIDAZOLE-5-CARBOXYLIC ACID; 1-METHYL-1H-PYRAZOLE-3-CARBOXYLIC ACID; 1-METHYL-1H-PYRAZOLE-4-CARBOXYLIC ACID; 1-METHYL-1H-PYRAZOLE-5-CARBOXYLIC ACID; 1-METHYL-1H-PYRROLE-2-CARBOXYLIC ACID; 1-METHYL-1H-PYRROLE-3-CARBOXYLIC ACID; 1-METHYL-2,5-DIHYDRO-1H-PYRROLE-2-CARBOXYLIC ACID; 1-METHYL-2-CYCLOHEXENE-1-CARBOXYLIC ACID; 1-METHYL-2-IMIDAZOLINE-4-CARBOXYLIC ACID; 1-METHYL-3-AZETIDINECARBOXYLIC ACID; 1-METHYL-3-CYCLOHEXENECARBOXYLIC ACID; 1-METHYL-4-OXO-2-AZETIDINECARBOXYLIC ACID; 1-METHYL-5-OXO-4,5-DIHYDRO-1H-PYRA-

ZOLE-3-CARBOXYLIC ACID; 1-METHYL-5-OXOPYRROLIDINE-2-CARBOXYLIC ACID; 1-METHYL-5-OXO-PYRROLIDINE-3-CARBOXYLIC ACID; 1-METHYLCYCLOBUTANECARBOXYLIC ACID; 1-METHYLCYCLOPENTANECARBOXYLIC ACID; 1-METHYLCYCLOPROPANE-1-CARBOXYLIC ACID; 1-METHYLIMIDAZOLE-2-CARBOXYLIC ACID HYDRATE; 1-METHYLPIPERAZINE-2-CARBOXYLIC ACID; 1-METHYL-PIPERIDINE-2-CARBOXYLIC ACID; 1-METHYLPIPERIDINE-3-CARBOXYLIC ACID; 1-METHYLPIPERIDINE-4-CARBOXYLIC ACID; 1-METHYL-PYRROLE-2-ACETIC ACID; 1-METHYLPYRROLIDINE-2-CARBOXYLIC ACID; 1-METHYLPYRROLIDINE-2-CARBOXYLIC ACID HYDRATE; 1-METHYLPYRROLIDINE-3-CARBOXYLIC ACID; 1-NITRO-3-AZETIDINECARBOXYLIC ACID; 1-PROPYL-AZETIDINE-2-CARBOXYLIC ACID; 1-PROPYLCYCLOBUTANECARBOXYLIC ACID; 1-VINYL-1H-PYRAZOLE-4-CARBOXYLIC ACID; 1-VINYL-1H-PYRROLE-2-CARBOXYLIC ACID; 2-([(2E)-3-CHLOROPROP-2-EN-1-YL]AMINO)ACETIC ACID; 2-([(METHYLCARBAMOYL)METHYL]AMINO)ACETIC ACID; 2-([2-(DIMETHYLAMINO)ETHYL]AMINO) ACETIC ACID; 2-(1-(HYDROXYMETHYL)CYCLOPROPYL)ACETIC ACID; 2-(1,2,4-OXADIAZOL-5-YL) ACETIC ACID; 2-(1,2-OXAZOL-4-YL)ACETIC ACID; 2-(1H-1,2,4-TRIAZOL-1-YL)PROPANOIC ACID; 2-(1H-1,2,4-TRIAZOL-3-YL)ACETIC ACID; 2-(1H-IMIDAZOL-1-YL)PROPANOIC ACID; 2-(1H-PYRAZOL-1-YL)PROPANOIC ACID; 2-(1H-PYRROL-1-YL)PROPANOIC ACID; 2-(1H-PYRROL-2-YL)PROPANOIC ACID; 2-(1-HYDROXYCYCLOBUTYL)ACETIC ACID; 2-(1-HYDROXYCYCLOBUTYL)PROPANOIC ACID; 2-(1-HYDROXYCYCLOPENTYL)ACETIC ACID; 2-(1-METHYL-1H-1,2,4-TRIAZOL-3-YL)ACETIC ACID; 2-(1-METHYL-3-PYRROLIDINYL)ACETIC ACID; 2-(1-METHYLHYDRAZINO)PROPANOIC ACID; 2-(2-AMINOACETAMIDO)ACETIC ACID-15N2; 2-(2-CHLOROETHOXY)ACETIC ACID; 2-(2-CYANOETHYLAMINO)-PROPIONIC ACID; 2-(2-ETHOXYETHOXY)ACETIC ACID; 2-(2H-TETRAZOL-5-YL)ACETIC ACID; 2-(2-HYDROXYETHOXY) ACETIC ACID; 2-(2-HYDROXYETHOXY)BUTANOIC ACID; 2-(2-HYDROXYETHOXY)PROPANOIC ACID; 2-(2-METHOXYETHOXY)ACETIC ACID; 2-(2-METHOXYETHOXY)PROPANOIC ACID; 2-(2-METHYL-1H-IMIDAZOL-5-YL)ACETIC ACID; 2-(2-METHYLENECYCLOPROPYL)ACETIC ACID; 2-(2-METHYLPROPOXY)PROPANOIC ACID; 2-(2-METHYLPROPYL)CYCLOPROPANE-1-CARBOXYLIC ACID; 2-(2-METHYLPYRROLIDIN-1-YL)ACETIC ACID; 2-(3-AMINO-1H-PYRAZOL-5-YL)ACETIC ACID; 2-(3H-IMIDAZOL-4-YL)ACETIC ACID; 2-(3-HYDROXYAZETIDIN-1-YL)ACETIC ACID; 2-(3-HYDROXYAZETIDIN-1-YL)PROPANOIC ACID; 2-(3-HYDROXYOXOLAN-3-YL)ACETIC ACID; 2-(3-HYDROXYPROPOXY)ACETIC ACID; 2-(3-HYDROXYPROPOXY)PROPANOIC ACID; 2-(3-METHOXYPROPOXY)ACETIC ACID; 2-(3-METHYL-1H-PYRROL-1-YL)ACETIC ACID; 2-(3-METHYLPYRROLIDIN-1-YL)ACETIC ACID; 2-(3-OXOCYCLOPENTYL)ACETIC ACID; 2-(3-PYRROLIDINYLIDENE)ACETIC ACID; 2-(4-METHYL)PYRROLIDINYL ACETIC ACID; 2-(5-AMINO-1H-1,2,4-TRIAZOL-1-YL)ACETIC ACID; 2-(5-AMINO-1H-PYRAZOL-1-YL)ACETIC ACID; 2-(5-METHYL-1,3,4-OXADIAZOL-2-YL)ACETIC ACID; 2-(5-METHYL-1H-1,2,4-TRIAZOL-3-YL)ACETIC ACID; 2-(5-METHYLPYRROLIDIN-2-YL)ACETIC ACID; 2-(5-OXO-4,5-DIHYDRO-1H-PYRAZOL-3-YL)ACETIC ACID; 2-(5-OXOPYRROLIDIN-2-YL)ACETIC ACID; 2-(ALLYLAMINO)ACETIC ACID; 2-(ALLYLTHIO)PROPANOIC ACID; 2-(AMINOAMINOCARBONYLAMINO) ACETIC ACID; 2-(AMINOMETHYL)-2-ETHYLBUTANOIC ACID; 2-(AMINOMETHYL)-3-METHYLBUTANOIC ACID; 2-(AMINOMETHYL)-4-METHYLPENTANOIC ACID; 2-(AMINOMETHYL)BUTANOIC ACID; 2-(AMINOMETHYL)CYCLOPROPANECARBOXYLIC ACID; 2-(AMINOMETHYL)PENTANOIC ACID; 2-(AMINOOXY)ACETIC ACID; 2-(AZETIDIN-1-YL)-2-OXOACETIC ACID; 2-(BUT-2-EN-1-YLOXY)ACETIC ACID; 2-(BUT-3-EN-1-YLOXY)ACETIC ACID; 2-(BUT-3-EN-1-YLOXY)PROPANOIC ACID; 2-(BUT-3-EN-2-YLAMINO)ACETIC ACID; 2-(BUT-3-EN-2-YLAMINO)PROPANOIC ACID; 2-(BUT-3-EN-2-YLSULFANYL) ACETIC ACID; 2-(BUT-3-ENAMIDO)ACETIC ACID; 2-(BUT-3-YN-1-YLAMINO)ACETIC ACID; 2-(BUT-3-YN-1-YLAMINO)PROPANOIC ACID; 2-(BUT-3-YN-1-YLSULFANYL)ACETIC ACID; 2-(BUTAN-2-YLAMINO)ACETIC ACID; 2-(BUTAN-2-YLAMINO)PROPANOIC ACID; 2-(BUTAN-2-YLOXY)ACETIC ACID; 2-(BUTAN-2-YLSULFANYL)ACETIC ACID; 2-(BUTYLAMINO)ACETIC ACID; 2-(BUTYLAMINO)PROPANOIC ACID; 2-(CYANOMETHYLTHIO)ACETIC ACID; 2-(CYCLOBUTYLAMINO)ACETIC ACID; 2-(CYCLOBUTYLAMINO)PROPANOIC ACID; 2-(CYCLOBUTYLMETHOXY)-ACETIC ACID; 2-(CYCLOBUTYLMETHYL)ACRYLIC ACID; 2-(CYCLOPENTYLOXY)ACETIC ACID; 2-(CYCLOPROPYLAMINO)-2-METHYLPROPANOIC ACID; 2-(CYCLOPROPYLAMINO)-2-OXOACETIC ACID; 2-(CYCLOPROPYLAMINO)ACETIC ACID; 2-(CYCLOPROPYLAMINO)BUTANOIC ACID; 2-(CYCLOPROPYLAMINO)PROPANOIC ACID; 2-(CYCLOPROPYLCARBAMOYL)ACETIC ACID; 2-(CYCLOPROPYLMETHOXY)-ACETIC ACID; 2-(CYCLOPROPYLMETHOXY)PROPANOIC ACID; 2-(DIETHYLAMINO)PROPANOIC ACID; 2-(DIMETHYLAMINO)-2-METHYLBUTANOIC ACID; 2-(DIMETHYLAMINO)-2-METHYLPROPANOIC ACID; 2-(DIMETHYLAMINO)BUTANOIC ACID; 2-(DIMETHYLAMINO)PENTANOIC ACID; 2-(DIMETHYLAMINO)PROPANOIC ACID; 2-(DIMETHYLCARBAMOYL)ACETIC ACID; 2-(ETHANESULFINYL)ACETIC ACID; 2-(ETHOXYCARBONYLAMINO)ACETIC ACID; 2-(ETHYLAMINO)-2-METHYLBUTANOIC ACID; 2-(ETHYLAMINO)-2-METHYLPROPANOIC ACID; 2-(ETHYLAMINO)-3-METHOXYPROPANOIC ACID; 2-(ETHYLAMINO)-3-METHYLBUTANOIC ACID; 2-(ETHYLAMINO)ACETIC ACID HYDROCHLORIDE; 2-(ETHYLAMINO)BUTANOIC ACID; 2-(ETHYLAMINO)PENTANOIC ACID; 2-(ETHYLAMINO)PROPANOIC ACID; 2-(ETHYLCARBAMOYL)ACETIC ACID; 2-(ETHYLSULFANYL)-2-METHYLPROPANOIC ACID; 2-(ETHYLSULFANYL)BUTANOIC ACID; 2-(ETHYLTHIO)PROPANOIC ACID; 2-(FORMYLOXY)PROPANOIC ACID; 2-(FURAN-2-YL)PROPANOIC ACID; 2-(FURAN-3-YL)-2-HYDROXYACETIC ACID; 2-(HYDROXYMETHYL)-BUTANOIC ACID; 2-(HYDROXYMETHYL)FURAN-3-CARBOXYLIC ACID; 2-(ISOPROPYLIDENEAMINOOXY)PROPIONIC ACID; 2-(ISOPROPYLTHIO)PROPANOIC ACID; 2-(METHOXY(METHYL)AMINO)-2-OXOACETIC

ACID; 2-(METHOXYCARBONYL)CYCLOPROPANE-1-CARBOXYLIC ACID; 2-(METHYLAMINO)-3-(METHYLSULFANYL)PROPANOIC ACID; 2-(METHYLAMINO)BUTANOIC ACID; 2-(METHYLAMINO)HEXANOIC ACID; 2-(METHYLAMINO)PENTANOIC ACID; 2-(METHYLCARBAMOYL)CYCLOPROPANE-1-CARBOXYLIC ACID; 2-(METHYLSULFANYL)BUTANOIC ACID; 2-(METHYLTHIO)PROPANOIC ACID; 2-(N-CYCLOBUTYL-N-METHYLAMINO)ACETIC ACID; 2-(N-ETHYLACETAMIDO)ACETIC ACID; 2-(N-METHYLACETAMIDO)ACETIC ACID; 2-(N-METHYLACETAMIDO)PROPANOIC ACID; 2-(N-METHYLFORMAMIDO)PROPANOIC ACID; 2-(N-METHYLHYDRAZINO)-BUTYRIC ACID; 2-(N-METHYL-N-PROPYLAMINO)ACETIC ACID; 2-(N-METHYLPROP-2-YNAMIDO)ACETIC ACID; 2-(N-PROPYLFORMAMIDO)ACETIC ACID; 2-(OXETAN-3-YLIDENE)ACETIC ACID; 2-(OXOLAN-3-YLAMINO)ACETIC ACID; 2-(OXOLAN-3-YLIDENE)ACETIC ACID; 2-(OXOLAN-3-YLOXY)ACETIC ACID; 2-(PENT-4-ENYLOXY)ACETIC ACID; 2-(PENTAN-2-YLAMINO)ACETIC ACID; 2-(PENTAN-3-YLAMINO)ACETIC ACID; 2-(PENTAN-3-YLOXY)ACETIC ACID; 2-(PENTYLAMINO)ACETIC ACID; 2-(PENTYLOXY)ACETIC ACID; 2-(PROP-2-EN-1-YLAMINO)BUTANOIC ACID; 2-(PROP-2-EN-1-YLAMINO)PROPANOIC ACID; 2-(PROP-2-EN-1-YLOXY)ACETIC ACID; 2-(PROP-2-EN-1-YLOXY)BUTANOIC ACID; 2-(PROP-2-EN-1-YLOXY)PROPANOIC ACID; 2-(PROP-2-YN-1-YLAMINO)ACETIC ACID; 2-(PROP-2-YN-1-YLAMINO)PROPANOIC ACID; 2-(PROP-2-YN-1-YLOXY)ACETIC ACID; 2-(PROP-2-YN-1-YLOXY)BUTANOIC ACID; 2-(PROP-2-YN-1-YLOXY)PROPANOIC ACID; 2-(PROP-2-YN-1-YLSULFANYL)PROPANOIC ACID; 2-(PROP-2-YNAMIDO)ACETIC ACID; 2-(PROP-2-YNAMIDO)PROPANOIC ACID; 2-(PROPAN-2-YL)PENTANOIC ACID; 2-(PROPAN-2-YLAMINO)ACETIC ACID; 2-(PROPAN-2-YLAMINO)BUTANOIC ACID; 2-(PROPAN-2-YLOXY)BUTANOIC ACID; 2-(PROPYLAMINO)BUTANOIC ACID; 2-(PROPYLAMINO)PROPANOIC ACID; 2-(PROPYLCARBAMOYL)ACETIC ACID; 2-(PROPYLSULFANYL)PROPANOIC ACID; 2(S),3(R)-2-AMINO-3-HYDROXYPENT-4-YNOIC ACID; 2(S)-AMINO-4-AZIDO-BUTANOIC ACID; 2-(TERT-BUTOXY)PROPANOIC ACID; 2-(TERT-BUTYLAMINO)ACETIC ACID; 2-(TRIFLUOROMETHYL)ACRYLIC ACID; 2,2,3,3-TETRAMETHYLCYCLOPROPANECARBOXYLIC ACID; 2,2,3-TRIMETHYL-3-BUTENOIC ACID; 2,2,3-TRIMETHYLBUTANOIC ACID; 2,2,3-TRIMETHYLPENTANOIC ACID; 2,2,4-TRIMETHYL-4-PENTENOIC ACID; 2,2,4-TRIMETHYLPENTANOIC ACID; 2,2-BIS(HYDROXYMETHYL)BUTYRIC ACID; 2,2-BIS(HYDROXYMETHYL)PROPIONIC ACID; 2,2-DIAMINO-3-MERCAPTO-PROPIONIC ACID; 2,2-DICHLOROPROPIONIC ACID; 2,2-DICYCLOPROPYLACETIC ACID; 2,2-DIETHYLBUTYRIC ACID; 2,2-DIETHYLCYCLOPROPANECARBOXYLIC ACID; 2,2-DIFLUORO-3-HYDROXYBUTANOIC ACID; 2,2-DIFLUORO-3-METHYLBUTYRIC ACID; 2,2-DIFLUOROBUTYRIC ACID; 2,2-DIFLUOROCYCLOBUTANECARBOXYLIC ACID; 2,2-DIFLUOROCYCLOPROPANECARBOXYLIC ACID; 2,2-DIFLUOROPENT-4-ENOIC ACID; 2,2-DIFLUOROPENTANOIC ACID; 2,2-DIFLUOROPROPIONIC ACID; 2,2-DIMETHYL CYCLOPROPYL CARBOXYLIC ACID; 2,2-DIMETHYL-1,3-DIOXOLANE-4-CARBOXYLIC ACID; 2,2-DIMETHYL-3-(METHYLSULFANYL)PROPANOIC ACID; 2,2-DIMETHYL-3-HYDROXYPROPIONIC ACID; 2,2-DIMETHYL-3-OXOBUTANOIC ACID; 2,2-DIMETHYL-4-OXO-PENTANOIC ACID; 2,2-DIMETHYL-4-PENTENOIC ACID; 2,2-DIMETHYL-5-HEXENOIC ACID; 2,2-DIMETHYL-5-HEXYNOIC ACID; 2,2-DIMETHYLBUT-3-ENOIC ACID; 2,2-DIMETHYL-BUT-3-YNOIC ACID; 2,2-DIMETHYLBUTYRIC ACID; 2,2-DIMETHYL-CYCLOPENTANECARBOXYLIC ACID; 2,2-DIMETHYLHEXANOIC ACID; 2,2-DIMETHYLMALONAMIC ACID; 2,2-DIMETHYL-MALONIC ACID MONOMETHYL ESTER; 2,2-DIMETHYLSUCCINIC ACID; 2,2-DIMETHYLVALERIC ACID; 2,3,3,3-TETRAFLUOROPROPANOIC ACID; 2,3,3-TRIMETHYLBUTANOIC ACID; 2,3,3-TRIMETHYLPROPIONIC ACID; 2,3,4-TRIHYDROXYBUTANOIC ACID; 2,3:4,5-DIEPOXY-HEXANOIC ACID; 2,3-ANHYDRO-4-DEOXYPENTARIC ACID; 2,3-DIAMINOBUTYRIC ACID; 2,3-DIAMINOPROPIONIC ACID; 2,3-DICHLOROPROPIONIC ACID; 2,3'-DIENE-VALPROIC ACID; 2,3-DIENEVALPROIC ACID; 2,3-DIETHYLCYCLOPROP-2-ENE-1-CARBOXYLIC ACID; 2,3-DIHYDRO-2-OXO-4-PYRIDINECARBOXYLIC ACID; 2,3-DIHYDRO-3-OXO-5-1SOTHIAZOLECARBOXAMIDE; 2,3-DIHYDRO-4-METHYL-3-OXO-5-1SOXAZOLECARBOXYLIC ACID; 2,3-DIHYDROXYISOVALERIC ACID; 2,3-DIMERCAPTOPROPIONIC ACID; 2,3-DIMETHYL-2-(METHYLAMINO)BUTANOIC ACID; 2,3-DIMETHYLPENTANOIC ACID; 2,3-DIMETHYLSUCCINIC ACID; 2,3-EPOXYPROPANOIC ACID; 2,4,4-TRIMETHYLPENTANOIC ACID; 2,4,6-OCTATRIENOIC ACID; 2,4-DIAMINO-2-METHYL-BUTYRIC ACID; 2,4-DIAMINO-BUTYRIC ACID; 2,4-DIENE VALPROIC ACID; 2,4-DIMETHYL-2-PENTENOIC ACID; 2,4-DIMETHYL-3-FUROIC ACID; 2,4-DIMETHYLHEXANOIC ACID; 2,4-DIMETHYL-OXAZOLE-5-CARBOXYLIC ACID; 2,4-DIMETHYLPENTANOIC ACID; 2,4-DIMETHYLPYRROLE-3-CARBOXYLIC ACID; 2,5-DIHYDRO-4-METHYL-5-OXO-3-FURANCARBOXYLIC ACID; 2,5-DIHYDRO-5-OXO-2-FURANACETIC ACID; 2,5-DIHYDRO-5-OXO-3-FURANCARBOXYLIC ACID; 2,5-DIHYDRO-FURAN-2-CARBOXYLIC ACID; 2,5-DIMETHYL-1,3-OXAZOLE-4-CARBOXYLIC ACID; 2,5-DIMETHYL-1H-IMIDAZOLE-4-CARBOXYLIC ACID; 2,5-DIMETHYL-3-FUROIC ACID; 2,5-DIMETHYL-HEX-4-ENOIC ACID; 2,5-DIMETHYLHEXANOIC ACID; 2,5-DIMETHYLPYRROLE-3-CARBOXYLIC ACID; 2,5-DIOXO-PYRROLIDINE-3-CARBOXYLIC ACID; 2,6-HEPTADIENOIC ACID; 2-[(1-CARBAMOYLETHYL)AMINO]ACETIC ACID; 2-[(1-CYANOETHYL)(METHYL)AMINO]ACETIC ACID; 2-[(1-CYANOETHYL)SULFANYL]ACETIC ACID; 2-[(1-CYANOPROPYL)AMINO]ACETIC ACID; 2-[(1-CYCLOPROPYLETHYL)AMINO]ACETIC ACID; 2-[(1-HYDROXY-2-METHYLPROPAN-2-YL)AMINO]ACETIC ACID; 2-[(1-HYDROXYBUTAN-2-YL)AMINO]ACETIC ACID; 2-[(1-HYDROXYPROPAN-2-YL)AMINO]ACETIC ACID; 2-[(1-HYDROXYPROPAN-2-YL)AMINO]PROPANOIC ACID; 2-[(1-METHOXYPROPAN-2-YL)AMINO]ACETIC ACID; 2-[(2,2-DIFLUOROETHYL)AMINO]ACETIC ACID; 2-[(2,2-DIMETHYLCYCLOPROPYL)AMINO]ACETIC ACID; 2-[(2,2-DIMETHYLPROPYL)AMINO]ACETIC ACID; 2-[(2-AMINOETHYL)(METHYL)AMINO]ACETIC ACID; 2-[(2-AMINOETHYL)(METHYL)AMINO]PROPANOIC ACID; 2-[(2-AMINOETHYL)AMINO]-2-METHYLPROPANOIC ACID; 2-[(2-AMINOETHYL)

CARBAMOYL]ACETIC ACID; 2-[(2-AMINOETHYL)SULFANYL]ACETIC ACID; 2-[(2-AMINOETHYL)SULFANYL]PROPANOIC ACID; 2-[(2-CARBAMOYLETHYL)AMINO]ACETIC ACID; 2-[(2-CHLOROPROP-2-EN-1-YL)AMINO]ACETIC ACID; 2-[(2-CYANOETHYL)(METHYL)AMINO]ACETIC ACID; 2-[(2E)-BUT-2-EN-1-YL(METHYL)AMINO]ACETIC ACID; 2-[(2E)-BUT-2-EN-1-YLAMINO]PROPANOIC ACID; 2-[(2E)-BUT-2-EN-1-YLSULFANYL]ACETIC ACID; 2-[(2E)-BUT-2-ENAMIDO]ACETIC ACID; 2-[(2-ETHOXYETHYL)AMINO]ACETIC ACID; 2-[(2-HYDROXY-2-METHYLPROPYL)AMINO]ACETIC ACID; 2-[(2-HYDROXYBUTYL)AMINO]ACETIC ACID; 2-[(2-HYDROXYETHYL)(METHYL)AMINO]ACETIC ACID; 2-[(2-HYDROXYETHYL)(METHYL)AMINO]PROPANOIC ACID; 2-[(2-HYDROXYETHYL)AMINO]-2-METHYLPROPANOIC ACID; 2-[(2-HYDROXYETHYL)AMINO]ACETIC ACID; 2-[(2-HYDROXYETHYL)AMINO]PROPANOIC ACID; 2-[(2-HYDROXYETHYL)CARBAMOYL]ACETIC ACID; 2-[(2-HYDROXYETHYL)SULFANYL]ACETIC ACID; 2-[(2-HYDROXYPROPYL)(METHYL)AMINO]ACETIC ACID; 2-[(2-HYDROXYPROPYL)AMINO]ACETIC ACID; 2-[(2-HYDROXYPROPYL)AMINO]PROPANOIC ACID; 2-[(2-METHOXY-2-OXOETHYL)AMINO]ACETIC ACID; 2-[(2-METHOXYACETYL)AMINO]ACETIC ACID; 2-[(2-METHOXYETHYL)AMINO]ACETIC ACID; 2-[(2-METHOXYETHYL)AMINO]PROPANOIC ACID; 2-[(2-METHYLBUTAN-2-YL)AMINO]ACETIC ACID; 2-[(2-METHYLBUTAN-2-YL)OXY]ACETIC ACID; 2-[(2-METHYLCYCLOPROPYL)AMINO]ACETIC ACID; 2-[(2-METHYLCYCLOPROPYL)AMINO]PROPANOIC ACID; 2-[(2-METHYLPROP-2-EN-1-YL)AMINO]ACETIC ACID; 2-[(2-METHYLPROP-2-EN-1-YL)AMINO]PROPANOIC ACID; 2-[(2-METHYLPROP-2-EN-1-YL)SULFANYL]ACETIC ACID; 2-[(2-METHYLPROPYL)AMINO]ACETIC ACID; 2-[(3-AMINOPROPYL)AMINO]ACETIC ACID; 2-[(3-CYANOPROPYL)AMINO]ACETIC ACID; 2-[(3E)-THIOLAN-3-YLIDENE]ACETIC ACID; 2-[(3-HYDROXYPROPYL)(METHYL)AMINO]ACETIC ACID; 2-[(3-HYDROXYPROPYL)AMINO]ACETIC ACID; 2-[(3-HYDROXYPROPYL)AMINO]PROPANOIC ACID; 2-[(3-METHOXYPROPYL)AMINO]ACETIC ACID; 2-[(3-METHYLBUT-2-EN-1-YL)AMINO]ACETIC ACID; 2-[(3-METHYLBUTAN-2-YL)AMINO]ACETIC ACID; 2-[(4-HYDROXYBUTYL)AMINO]ACETIC ACID; 2-[(AMINOCARBONYL)AMINO]-3-HYDROXYPROPANOIC ACID; 2-[(AMINOCARBONYL)AMINO]BUTANOIC ACID; 2-[(AMINOTHIOXOMETHYL)AMINO]ACETIC ACID; 2-[(CARBAMOYLMETHYL)(METHYL)AMINO]ACETIC ACID; 2-[(CARBAMOYLMETHYL)AMINO]ACETIC ACID; 2-[(CARBAMOYLMETHYL)AMINO]PROPANOIC ACID; 2-[(CYANOMETHANE)SULFINYL]ACETIC ACID; 2-[(CYANOMETHYL)(ETHYL)AMINO]ACETIC ACID; 2-[(CYANOMETHYL)(METHYL)AMINO]ACETIC ACID; 2-[(CYANOMETHYL)(METHYL)AMINO]PROPANOIC ACID; 2-[(CYANOMETHYL)AMINO]ACETIC ACID; 2-[(CYANOMETHYL)AMINO]PROPANOIC ACID; 2-[(CYANOMETHYL)CARBAMOYL]ACETIC ACID; 2-[(CYANOMETHYL)SULFANYL]PROPANOIC ACID; 2-[(CYCLOBUTYLMETHYL)AMINO]ACETIC ACID; 2-[(CYCLOPROPYLCARBONYL)AMINO]ACETIC ACID; 2-[(CYCLOPROPYLMETHYL)(METHYL)AMINO]ACETIC ACID; 2-[(CYCLOPROPYLMETHYL)AMINO]ACETIC ACID; 2-[(CYCLOPROPYLMETHYL)AMINO]PROPANOIC ACID; 2-[(ETHYLCARBAMOYL)AMINO]ACETIC ACID; 2-[(METHOXYCARBONYL)(METHYL)AMINO]ACETIC ACID; 2-[(METHOXYCARBONYL)AMINO]ACETIC ACID; 2-[(METHOXYCARBONYL)AMINO]PROPANOIC ACID; 2-[(METHYLCARBAMOYL)AMINO]ACETIC ACID; 2-[(METHYLCARBAMOYL)AMINO]PROPANOIC ACID; 2-[(METHYLCARBAMOYL)METHOXY]ACETIC ACID; 2-[(PROP-2-EN-1-YL)CARBAMOYL]ACETIC ACID; 2-[(PROP-2-YN-1-YL)CARBAMOYL]ACETIC ACID; 2-[(PROPAN-2-YL)AMINO]PROPANOIC ACID; 2-[(PROPAN-2-YL)CARBAMOYL]ACETIC ACID; 2-[1-(MERCAPTOMETHYL)CYCLOPROPYL]ACETIC ACID; 2-[2-(DIAMINOMETHYLIDENE)HYDRAZONO]PROPANOIC ACID; 2-[BUT-2-YN-1-YL(METHYL)AMINO]ACETIC ACID; 2-[BUT-3-YN-1-YL(METHYL)AMINO]ACETIC ACID; 2-[BUTAN-2-YL(METHYL)AMINO]ACETIC ACID; 2-[BUTYL(METHYL)AMINO]ACETIC ACID; 2-[CARBAMOYL(ETHYL)AMINO]ACETIC ACID; 2-[CYCLOPROPYL(ETHYL)AMINO]ACETIC ACID; 2-[CYCLOPROPYL(METHYL)AMINO]ACETIC ACID; 2-[CYCLOPROPYL(METHYL)AMINO]PROPANOIC ACID; 2-[ETHYL(2-HYDROXYETHYL)AMINO]ACETIC ACID; 2-[ETHYL(METHYL)AMINO]-2-METHYLPROPANOIC ACID; 2-[ETHYL(METHYL)AMINO]BUTANOIC ACID; 2-[ETHYL(METHYL)AMINO]PROPANOIC ACID; 2-[ETHYL(METHYL)CARBAMOYL]ACETIC ACID; 2-[ETHYL(PROP-2-EN-1-YL)AMINO]ACETIC ACID; 2-[ETHYL(PROP-2-YN-1-YL)AMINO]ACETIC ACID; 2-[ETHYL(PROPAN-2-YL)AMINO]ACETIC ACID; 2-[ETHYL(PROPYL)AMINO]ACETIC ACID; 2-[METHOXY(METHYL)CARBAMOYL]ACETIC ACID; 2-[METHYL(2-METHYLPROP-2-EN-1-YL)AMINO]ACETIC ACID; 2-[METHYL(2-METHYLPROPYL)AMINO]ACETIC ACID; 2-[METHYL(METHYLCARBAMOYL)AMINO]ACETIC ACID; 2-[METHYL(PROP-2-EN-1-YL)AMINO]ACETIC ACID; 24METHYL(PROP-2-EN-1-YL)AMINO-PROPANOIC ACID; 2-[METHYL(PROP-2-YN-1-YL)AMINO]ACETIC ACID; 2-[METHYL(PROP-2-YN-1-YL)AMINO]PROPANOIC ACID; 2-[METHYL(PROPAN-2-YL)AMINO]PROPANOIC ACID; 2-[METHYL(PROPIONYL)AMINO]ACETIC ACID; 2-[METHYL(PROPYL)AMINO]PROPANOIC ACID; 2-ACETAMIDO-2-METHYLPROPANOIC ACID; 2-ACETAMIDOACRYLIC ACID; 2-ACETAMIDOBUTYRIC ACID; 2-ACETYL-3-OXO-BUTANOIC ACID; 2-ACETYLAMINO-2-HYDROXY-ACETIC ACID; 2-ALLYL-4-PENTENOIC ACID; 2-AMINO-1,3-OXAZOLE-4-CARBOXYLIC ACID; 2-AMINO-1-ETHOXY-CYCLOPROPANECARBOXYLIC ACID; 2-AMINO-1H-IMIDAZOLE-4-CARBOXYLIC ACID; 2-AMINO-2-(1-METHYLCYCLOPROPYL)PROPIONIC ACID; 2-AMINO-2-(OXETAN-3-YL)ACETIC ACID; 2-AMINO-2-CYCLOBUTYLPROPIONIC ACID; 2-AMINO-2-CYCLOPROPYLPROPIONIC ACID; 2-AMINO-2-HYDROXY-ACETIC ACID; 2-AMINO-2-METHYL-3-(METHYLSULFANYL)PROPANOIC ACID; 2-AMINO-2-METHYL-3-METHOXY-PROPANOIC ACID; 2-AMINO-2-METHYL-3-METHYLAMINO-PROPANOIC ACID; 2-AMINO-2-METHYL-4-METHOXY-BUTYRIC ACID; 2-AMINO-2-METHYL-4-PENTENOIC ACID; 2-AMINO-2-METHYL-5-HYDROXY-PENTANOIC ACID; 2-AMINO-2-METHYLBUT-3-YNOIC ACID; 2-AMINO-2-METHYLBUTYRIC ACID;

2-AMINO-2-METHYL-CYCLOPENTANECARBOXYLIC ACID; 2-AMINO-2-METHYLPENTANOIC ACID; 2-AMINO-2-METHYLSUCCINIC ACID; 2-AMINO-3-(DIMETHYLAMINO)-2-METHYLPROPANOIC ACID; 2-AMINO-3-(ETHYLSULFANYL)PROPANOIC ACID; 2-AMINO-3-(METHYLAMINO)PROPANOIC ACID; 2-AMINO-3-[ETHYL(METHYL)AMINO]PROPANOIC ACID; 2-AMINO-3-[METHYLTHIO]BUTYRIC ACID; 2-AMINO-3-BUTENOIC ACID; 2-AMINO-3-CYANOPROPANOIC ACID; 2-AMINO-3-ETHOXY-2-METHYL-PROPANOIC ACID; 2-AMINO-3-ETHOXYPROPANOIC ACID; 2-AMINO-3-ETHYL-PENTANOIC ACID; 2-AMINO-3-FLUOROBUTYRIC ACID; 2-AMINO-3-HYDROXY-2-METHYLBUTANOIC ACID; 2-AMINO-3-HYDROXY-4-METHYL-VALERIC ACID; 2-AMINO-3-HYDROXYBUTANOIC ACID; 2-AMINO-3-METHOXY-2-METHYLPROPANOIC ACID; 2-AMINO-3-METHYLENE-CYCLOBUTANECARBOXYLIC ACID; 2-AMINO-3-METHYL-HEXANOIC ACID; 2-AMINO-3-METHYLPENT-4-ENOIC ACID; 2-AMINO-3-METHYL-PENTANOIC ACID; 2-AMINO-3-PROPOXYPROPANOIC ACID; 2-AMINO-4(5)-IMIDAZOLEACETIC ACID; 2-AMINO-4-(DIMETHYLAMINO)BUTANOIC ACID; 2-AMINO-4,4-DIFLUOROBUTANOIC ACID; 2-AMINO-4-BORONOBUTANOIC ACID; 2-AMINO-4-ETHOXYBUTANOIC ACID; 2-AMINO-4-FLUORO-BUTANOIC ACID; 2-AMINO-4-HEXYNOIC ACID; 2-AMINO-4-METHOXY-2-METHYLBUTANOIC ACID; 2-AMINO-4-METHOXYBUTANOIC ACID; 2-AMINO-4-METHYL-1,3-OXAZOLE-5-CARBOXYLIC ACID; 2-AMINO-4-METHYL-3-PENTENOIC ACID; 2-AMINO-4-METHYLENE-CYCLOBUTANECARBOXYLIC ACID; 2-AMINO-4-METHYLENE-CYCLOPENTANECARBOXYLIC ACID; 2-AMINO-4-METHYL-HEXANOIC ACID; 2-AMINO-4-METHYL-PENT-4-ENOIC ACID; 2-AMINO-4-OXOBUTANOIC ACID; 2-AMINO-4-THIAZOLINIC ACID; 2-AMINO-5-HYDROXYLEVULINIC ACID; 2-AMINO-5-HYDROXYVALERIC ACID; 2-AMINO-5-METHOXYPENTANOIC ACID; 2-AMINO-5-METHYLHEX-4-ENOIC ACID; 2-AMINOBICYCLO[3.1.0]HEXANE-2-CARBOXYLIC ACID; 2-AMINOCYCLOHEX-1-ENECARBOXYLIC ACID; 2-AMINOCYCLOPENTANEACETIC ACID; 2-AMINO-CYCLOPENTANECARBOXYLIC ACID; 2-AMINO-CYCLOPROPANECARBOXYLIC ACID; 2-AMINOHEPTANOIC ACID; 2-AMINOHEX-5-ENOIC ACID; 2-AMINOHEX-5-YNOIC ACID; 2-AMINOISOBUTYRIC ACID; 2-AMINOISOBUTYRIC-15N ACID; 2-AMINOISONICOTINIC ACID; 2-AMINOMETHYL-1H-IMIDAZOLE-4-CARBOXYLIC ACID; 2-AMINONICOTINIC ACID; 2-AMINOOXAZOLE-5-CARBOXYLIC ACID; 2-AMINOPYRIMIDINE-4-CARBOXYLIC ACID; 2-AMINOPYRIMIDINE-5-CARBOXYLIC ACID; 2-AMINOTHIAZOLE-4-CARBOXYLIC ACID; 2-AMINOTHIAZOLE-5-CARBOXYLIC ACID; 2-AMINOTHIOPHENE-3-CARBOXYLIC ACID; 2-AZABICYCLO[2.1.1]HEXANE-1-CARBOXYLIC ACID; 2-AZABICYCLO[2.2.1]HEPTANE-3-CARBOXYLIC ACID; 2-AZETIDINECARBOXYLIC ACID, 3-AMINO-4-OXO-; 2-AZIDO-2-METHYLPROPIONIC ACID; 2-AZIDOACETIC ACID; 2-AZIDOPROPANOIC ACID; 2-BUTOXYACETIC ACID; 2-BUTOXYPROPANOIC ACID; 2-BUTYLCYCLOPROPANECARBOXYLIC ACID; 2-BUTYNOIC ACID; 2-CARBAMOYLCYCLOPROPANE-1-CARBOXYLIC ACID; 2-CARBOXYETHYL ACRYLATE; 2-CARBOXYL MALONIC ACID; 2-CHLORO-1H-IMIDAZOLE-5-CARBOXYLIC ACID; 2-CHLORO-2-FLUORO-CYCLOPROPANECARBONIC ACID; 2-CHLORO-3-FUROIC ACID; 2-CHLORO-3-HYDROXYBUTANOIC ACID; 2-CHLORO-3-METHOXYPROPIONIC ACID; 2-CHLORO-3-METHYLBUTANOIC ACID; 2-CHLORO-ACRYLIC ACID; 2-CHLOROBUTYRIC ACID; 2-CHLOROCYCLOPENT-1-ENE-1-CARBOXYLIC ACID; 2-CHLOROFURAN-4-CARBOXYLIC ACID; 2-CHLOROOXAZOLE-4-CARBOXYLIC ACID; 2-CHLOROPROPIONIC ACID; 2-CHLOROPROPIONIC ACID, [1-14C]; 2-CYANO-2-ETHYLBUTANOIC ACID; 2-CYANO-2-HEXENOIC ACID; 2-CYANO-2-METHYLACETIC ACID; 2-CYANO-2-METHYLPROPANOIC ACID; 2-CYANO-3-METHYL-BUT-2-ENOIC ACID; 2-CYANO-3-METHYLBUTANOIC ACID; 2-CYANO-4-METHYLPENTANOIC ACID; 2-CYANO-4-PYRIDINE CARBOXYLIC ACID; 2-CYANOBENZOIC ACID; 2-CYANOBUTANOIC ACID; 2-CYANO-OXAZOLE-4-CARBOXYLIC ACID; 2-CYANOPYRIDINE-3-CARBOXYLIC ACID; 2-CYANOPYRIMIDINE-5-CARBOXYLIC ACID; 2-CYCLOHEXYLIDENEACETIC ACID; 2-CYCLOPENTANONE CARBOXYLATE; 2-CYCLOPENTENE-1-ACETIC ACID; 2-CYCLOPENTENE-1-CARBOXYLIC ACID; 2-CYCLOPENTENE-1-CARBOXYLIC ACID, 4-AMINO-; 2-CYCLOPENTYL-2-HYDROXYACETIC ACID; 2-CYCLOPENTYLIDENEACETIC ACID; 2-CYCLOPENTYLIDENEPROPANOIC ACID; 2-CYCLOPENTYLPROPANOIC ACID; 2-CYCLOPROPYL-2-(ETHYLAMINO)ACETIC ACID; 2-CYCLOPROPYL-2-(METHYLAMINO)ACETIC ACID; 2-CYCLOPROPYL-2-(METHYLAMINO)PROPANOIC ACID; 2-CYCLOPROPYL-2-FORMAMIDOACETIC ACID; 2-CYCLOPROPYL-2-HYDROXYACETIC ACID; 2-CYCLOPROPYL-2-HYDROXYPROPANOIC ACID; 2-CYCLOPROPYL-2-METHOXYPROPANOIC ACID; 2-CYCLOPROPYL-2-METHYLCYCLOPROPANE-1-CARBOXYLIC ACID; 2-CYCLOPROPYL-2-OXOACETIC ACID; 2-CYCLOPROPYLCYCLOPROPANE-1-CARBOXYLIC ACID; 2-CYCLOPROPYLPROPANOIC ACID; 2-EN-EVALPROIC ACID; 2-ETHOXY-2,2-DIFLUOROACETIC ACID; 2-ETHOXY-2-METHYLBUTANOIC ACID; 2-ETHOXY-2-METHYLPROPANOIC ACID; 2-ETHOXY-2-OXOACETIC ACID; 2-ETHOXY-3-HYDROXYPROPANOIC ACID; 2-ETHOXY-3-METHOXYPROPANOIC ACID; 2-ETHOXY-3-METHYLBUTANOIC ACID; 2-ETHOXY-3-METHYLCYCLOPROPANECARBOXYLIC ACID; 2-ETHOXY-4-HYDROXYBUTANOIC ACID; 2-ETHOXYBUTANOIC ACID; 2-ETHOXYCYCLOPROPANE-1-CARBOXYLIC ACID; 2-ETHOXYPROPANOIC ACID; 2-ETHYL-1,3-OXAZOLE-4-CARBOXYLIC ACID; 2-ETHYL-1H-IMIDAZOLE-4-CARBOXYLIC ACID; 2-ETHYL-2-(METHYLAMINO) BUTANOIC ACID; 2-ETHYL-2-HEXENOIC ACID; 2-ETHYL-2-HEXENOIC ACID, PREDOMINANTLY TRANS; 2-ETHYL-2-HYDROXYBUTYRIC ACID; 2-ETHYL-2-METHOXYBUTANOIC ACID; 2-ETHYL-2-METHYLPENTANOIC ACID; 2-ETHYL-3,3-DIMETHYL-2-OXIRANECARBOXYLIC ACID; 2-ETHYL-3H-IMIDAZOLE-4-CARBOXYLIC ACID; 2-ETHYL-3-HYDROXY-3-METHYLBUTANOIC ACID; 2-ETHYL-3-HYDROXYBUTANOIC ACID; 2-ETHYL-3-HYDROXYPENTANOIC ACID; 2-ETHYL-3-METHYLBUTANOIC ACID; 2-ETHYL-3-METHYLPENTANOIC ACID; 2-ETHYL-4-METHOXYBUTANOIC ACID; 2-ETHYL-4-

METHYLPENTANOIC ACID; 2-ETHYLACRYLIC ACID; 2-ETHYLBUTYRIC ACID; 2-ETHYLCYCLOPROPANE-1-CARBOXYLIC ACID; 2-ETHYLHEXANOIC ACID; 2-ETHYLPENTANOIC ACID; 2-ETHYLPROLINE; 2-ETHYLSUCCINIC ACID; 2-ETHYNYL-BENZOIC ACID; 2-FLUORO-1,3-THIAZOLE-4-CARBOXYLIC ACID; 2-FLUORO-3-METHYLBUTYRIC ACID; 2-FLUORO-3-OXOBUTANOIC ACID; 2-FLUOROACRYLIC ACID; 2-FLUOROBENZOIC ACID; 2-FLUORO-BETA-ALANINE HYDROCHLORIDE; 2-FLUOROISOBUTYRIC ACID; 2-FLUORO-L-PROLINE; 2-FLUORONICOTINIC ACID; 2-FLUOROOXAZOLE-4-CARBOXYLIC ACID; 2-FLUOROPROPIONIC ACID; 2-FLUOROPYRIDINE-4-CARBOXYLIC ACID; 2-FLUORO-THIAZOLE-5-CARBOXYLIC ACID; 2-FORMAMIDO-2-METHYLPROPANOIC ACID; 2-FORMYL-1H-IMIDAZOLE-4-CARBOXYLIC ACID; 2-FORMYLCYCLOPENT-2-ENECARBOXYLIC ACID; 2-FURANACETIC ACID, TETRAHYDRO-5-OXO-; 2-FUROIC ACID; 2-FURYLACETIC ACID; 2-GUANIDINOPROPIONIC ACID; 2-GUANIDINO-PROPIONIC ACID; 2H-1,2,3-TRIAZOLE-2-ACETIC ACID; 2-HEPTENOIC ACID; 2-HEPTYNOIC ACID; 2-HEXYNOIC ACID; 2H-PYRAN-2-ONE-6-CARBOXYLIC ACID; 2H-PYRAZOLE-3-CARBOXYLIC ACID; 2H-PYRROLE-2-CARBOXYLIC ACID, 5-AMINO-3,4-DIHYDRO-4-METHYLENE-, (2S)-; 2H-PYRROLE-2-CARBOXYLIC ACID, 5-AMINO-3,4-DIHYDRO-; 2H-PYRROLE-2-CARBOXYLIC ACID, 5-AMINO-3,4-DIHYDRO-,(2R)-; 2H-TETRAZOL-2-YLACETIC ACID; 2H-TETRAZOLE-5-CARBOXYLIC ACID; 2-HYDRAZINO-3-METHYLBUTANOIC ACID; 2-HYDRAZINOBUTANOIC ACID; 2-HYDRAZINYLACETIC ACID; 2-HYDROXY-1H-IMIDAZOLE-4-CARBOXYLIC ACID; 2-HYDROXY-2,3-DIMETHYLBUTANOIC ACID; 2-HYDROXY-2,4-DIMETHYLPENTANOIC ACID; 2-HYDROXY-2-METHYL-3-OXOBUTANOIC ACID; 2-HYDROXY-2-METHYL-BUT-3-ENOIC ACID; 2-HYDROXY-2-METHYLBUTYRIC ACID; 2-HYDROXY-2-METHYLPENTANOIC ACID; 2-HYDROXY-3,3-DIMETHYLBUTANOIC ACID; 2-HYDROXY-3-BUTENOIC ACID; 2-HYDROXY-3-BUTYNOIC ACID; 2-HYDROXY-3-METHYL-3-BUTEN-1-OIC ACID; 2-HYDROXY-3-METHYLBUTYRIC ACID; 2-HYDROXY-3-METHYLHEXANOIC ACID; 2-HYDROXY-3-METHYLPENTANOIC ACID; 2-HYDROXY-3-NITROPROPANOIC ACID; 2-HYDROXY-3-PYRAZINECARBOXYLIC ACID; 2-HYDROXY-4,4-DIMETHYLPENTANOIC ACID; 2-HYDROXY-4-AMINO BUTANOIC ACID; 2-HYDROXY-4-METHOXY-2-METHYLBUTANOIC ACID; 2-HYDROXY-5-THIAZOLECARBOXYLIC ACID; 2-HYDROXYAMINOBUTYRIC ACID; 2-HYDROXYAMINO-PENTANOIC ACID; 2-HYDROXYCYCLOHEXANECARBOXYLIC ACID; 2-HYDROXYHEPTANOIC ACID; 2-HYDROXYIMINO-BUTYRIC ACID; 2-HYDROXYISOBUTYRIC ACID; 2-HYDROXYISONICOTINIC ACID; 2-HYDROXYNICOTINIC ACID; 2-HYDROXY-PENT-4-ENOIC ACID; 2-HYDROXYPYRIMIDINE-4-CARBOXYLIC ACID; 2-HYDROXYPYRIMIDINE-5-CARBOXYLIC ACID; 2-HYDROXYVALERIC ACID; 2-IMIDAZOLIDONE-4-CARBOXYLIC ACID; 2-ISOBUTOXYACETIC ACID; 2-ISOBUTYLAMINO-PROPIONIC ACID; 2-ISOPROPOXYPROPANOIC ACID; 2-KETOGLUTARIC ACID; 2-MERCAPTO-1H-IMIDAZOLE-5-CARBOXYLIC ACID; 2-MERCAPTOBUTYRIC ACID; 2-MERCAPTOISOBUTYRIC ACID; 2-MERCAPTOPROPIONIC ACID; 2-METHANESULFINYLACETIC ACID; 2-METHANESULFINYLPROPANOIC ACID; 2-METHOXY-2-METHYLBUTANOIC ACID; 2-METHOXY-2-METHYLPENTANOIC ACID; 2-METHOXY-2-METHYLPROPANOIC ACID; 2-METHOXYBUTANOIC ACID; 2-METHOXYCROTONIC ACID; 2-METHOXYPENTANOIC ACID; 2-METHOXYPROPANOIC ACID; 2-METHYL CYCLOBUTANECARBOXYLIC ACID; 2-METHYL-1,3-OXAZOLE-4-CARBOXYLIC ACID; 2-METHYL-1,3-OXAZOLE-5-CARBOXYLIC ACID; 2-METHYL-1,3-THIAZOLE-4-CARBOXYLIC ACID; 2-METHYL-1,3-THIAZOLE-5-CARBOXYLIC ACID; 2-METHYL-1,3-THIAZOLIDINE-4-CARBOXYLIC ACID; 2-METHYL-1,4,5,6-TETRAHYDROPYRIMIDINE-4-CARBOXYLIC ACID; 2-METHYL-1-CYCLOHEXANECARBOXYLIC ACID; 2-METHYL-1H-IMIDAZOLE-4-CARBOXYLIC ACID; 2-METHYL-1H-IMIDAZOLE-4-CARBOXYLIC ACID HYDRATE; 2-METHYL-1H-IMIDAZOLE-5-CARBOXYLIC ACID; 2-METHYL-1H-PYRROLE-3-CARBOXYLIC ACID; 2-METHYL-2-(METHYLAMINO)BUTANOIC ACID; 2-METHYL-2-(METHYLAMINO) PENTANOIC ACID; 2-METHYL-2-(METHYLSULFANYL)BUTANOIC ACID; 2-METHYL-2-(METHYLSULFANYL)PROPANOIC ACID; 2-METHYL-2-(N-METHYLFORMAMIDO)PROPANOIC ACID; 2-METHYL-2-(PROP-2-EN-1-YLAMINO)PROPANOIC ACID; 2-METHYL-2-(PROP-2-EN-1-YLOXY) PROPANOIC ACID; 2-METHYL-2-(PROP-2-YN-1-YLAMINO)PROPANOIC ACID; 2-METHYL-2-(PROPAN-2-YL)CYCLOPROPANE-1-CARBOXYLIC ACID; 2-METHYL-2-(PROPAN-2-YLAMINO)PROPANOIC ACID; 2-METHYL-2-(PROPAN-2-YLOXY) PROPANOIC ACID; 2-METHYL-2-(PROPYLAMINO) PROPANOIC ACID; 2-METHYL-2-ETHYLBUTYRIC ACID; 2-METHYL-2-HEPTENOIC ACID; 2-METHYL-2-HEXENOIC ACID; 2-METHYL-2-PENTENOIC ACID; 2-METHYL-2-PIPERIDINECARBOXYLIC ACID; 2-METHYL-2-PROPOXYPROPANOIC ACID; 2-METHYL-2-PROPYLCYCLOPROPANE-1-CARBOXYLIC ACID; 2-METHYL-2-THIAZOLIDINECARBOXYLIC ACID; 2-METHYL-3-(METHYLAMINO)PROPANOIC ACID; 2-METHYL-3-(METHYLSULFANYL) PROPANOIC ACID; 2-METHYL-3-(PROP-2-EN-1-YLAMINO)PROPANOIC ACID; 2-METHYL-3-(PROP-2-YN-1-YLAMINO)PROPANOIC ACID; 2-METHYL-3-(PROPAN-2-YLAMINO)PROPANOIC ACID; 2-METHYL-3-(PROPYLAMINO)PROPANOIC ACID; 2-METHYL-3-BUTENOIC ACID; 2-METHYL-3-CYCLOHEXENE-1-CARBOXYLIC ACID; 2-METHYL-3-FUROIC ACID; 2-METHYL-3-HYDROXYBUTYRIC ACID; 2-METHYL-3-PENTENOIC ACID; 2-METHYL-4,5-DIHYDRO-FURAN-3-CARBOXYLIC ACID; 2-METHYL-4,5-DIHYDROOXAZOLE-4-CARBOXYLIC ACID; 2-METHYL-4,5-DIHYDROTHIOPHENE-3-CARBOXYLIC ACID; 2-METHYL-4-OXOHEXANOIC ACID; 2-METHYL-4-OXOPENTANOIC ACID; 2-METHYL-4-PENTENOIC ACID; 2-METHYLACETOACETIC ACID; 2-METHYLBUTYRIC ACID; 2-METHYLCYCLOPENTANECARBOXYLIC ACID; 2-METHYLCYCLOPROPANECARBOXYLIC ACID; 2-METHYL-CYSTEINE; 2-METHYL-D-SERINE; 2-METHYLENECYCLOPROPANECARBOXYLIC ACID; 2-METHYLENE-PENTANEDIOIC ACID; 2-METHYLENE-SUCCINIC ACID 1-METHYL ESTER; 2-METHYLGLUTARIC ACID; 2-METHYLHEPTANOIC ACID; 2-METHYLHEXANOIC

ACID; 2-METHYLISONICOTINIC ACID; 2-METHYL-ISOXAZOLE-4-CARBOXYLIC ACID; 2-METHYL-L-SERINE; 2-METHYLNICOTINIC ACID; 2-METHYL-PIPERIDINE-3-CARBOXYLIC ACID; 2-METHYLPROLINE; 2-METHYLPYRIMIDINE-4-CARBOXYLIC ACID; 2-METHYLPYRIMIDINE-5-CARBOXYLIC ACID; 2-METHYLTETRAHYDRO-2H-PYRAN-2-CARBOXYLIC ACID; 2-METHYL-TETRAHYDRO-FURAN-2-CARBOXYLIC ACID; 2-METHYLTHIOPHENE-3-CARBOXYLIC ACID; 2-METHYLVALERIC ACID; 2-MORPHOLINEACETIC ACID; 2-NITROCYCLOPROPANECARBOXYLIC ACID; 2-OCTYNOIC ACID; 2-OXA-BICYCLO[2.1.1]HEXANE-5-CARBOXYLIC ACID; 2-OXA-BICYCLO[3.1.0]HEX-3-ENE-6-CARBOXYLIC ACID; 2-OXABICYCLO[3.1.0]HEXANE-6-CARBOXYLIC ACID; 2-OXABICYCLO[4.1.0]HEPTANE-7-CARBOXYLIC ACID; 2-OXO-1,2-DIHYDROPYRIDINE-3-CARBOXYLIC ACID; 2-OXO-1,2-DIHYDROPYRIDINE-4-CARBOXYLIC ACID; 2-OXO-1,3-OXAZOLIDINE-4-CARBOXYLIC ACID; 2'-OXO-1H-PYRROLE-3-ACETIC ACID; 2-OXO-2-(1H-PYRROL-2-YL)ACETIC ACID; 2-OXO-2,3-DIHYDRO-1H-IMIDAZOLE-4-CARBOXYLIC ACID; 2-OXO-2H-PYRAN-3-CARBOXYLIC ACID; 2-OXO-3H-PYRIMIDINE-4-CARBOXYLIC ACID; 2-OXO-3-OXA-BICYCLO[3.1.0]HEXANE-1-CARBOXYLIC ACID; 2-OXOBUTYRIC ACID; 2-OXOCYCLOHEXANECARBOXYLIC ACID; 2-OXOCYCLOPENTANEACETIC ACID; 2-OXOPENTANOIC ACID; 2-OXO-PIPERIDINE-3-CARBOXYLIC ACID; 2-OXOPIPERIDINE-4-CARBOXYLIC ACID; 2-OXO-PYRROLIDINE-3-CARBOXYLIC ACID; 2-PENTYNOIC ACID; 2-PIPERIDINE ACETIC ACID; 2-PROPOXYACETIC ACID; 2-PROPOXYBUTANOIC ACID; 2-PROPOXYPROPANOIC ACID; 2-PROPYL-3-PENTENOIC ACID; 2-PROPYL-3-PENTYNOIC ACID; 2-PROPYL-4-PENTENOIC ACID; 2-PROPYLACRYLIC ACID; 2-PROPYLCYCLOPROPANE-1-CARBOXYLIC ACID; 2-PYRAZINE ACETIC ACID; 2-PYRAZINECARBOXYLIC ACID; 2-PYRAZINECARBOXYLIC ACID 4-OXIDE; 2-PYRAZINECARBOXYLIC ACID, 5-FLUORO-; 2-PYRIDINECARBOXYLIC ACID, HYDRATE; 2-PYRIDINECARBOXYLIC ACID, 6-AMINO-2,3-DIHYDRO-; 2-PYRIDYLACETIC ACID; 2-PYRIMIDINEACETIC ACID; 2-PYRROLIDIN-1-YLPROPANOIC ACID; 2-PYRROLIDINYL ACETIC ACID; 2R,3R-2-METHYL-PIPERIDINE-3-CARBOXYLIC ACID; 2S,3R-2-METHYL-PIPERIDINE-3-CARBOXYLIC ACID; 2S,3S-2-METHYL-PIPERIDINE-3-CARBOXYLIC ACID; 2-SULFANYL-1H-IMIDAZOLE-4-CARBOXYLIC ACID; 2-SULFANYLCYCLOPENTANE-1-CARBOXYLIC ACID; 2-TETRAHYDROFUROIC ACID; 2-THIABICYCLO[3.1.0]HEX-3-ENE-6-CARBOXYLIC ACID; 2-THIOPHENEACETIC ACID; 2-THIOPHENECARBOXYLIC ACID; 2-THIOPHENECARBOXYLIC ACID, [CARBOXYL-14C]; 2-THIOPHENECARBOXYLIC ACID, 4-FLUORO-; 2-THIOPHENECARBOXYLIC ACID, 5-AMINO-; 3-(1,2,3,4-TETRAAZOL-2-YL)PROPANOIC ACID; 3-(1,2,4-OXADIAZOL-3-YL)PROPANOIC ACID; 3-(1,2,4-OXADIAZOL-5-YL)PROPANOIC ACID; 3-(1,2,5-OXADIAZOL-3-YL)PROPANOIC ACID; 3-(1,3-OXAZOL-2-YL)PROPANOIC ACID; 3-(1H-[1,2,3]TRIAZOL-4-YL)-PROPIONIC ACID; 3-(1H-1,2,3-TRIAZOL-1-YL)PROPANOIC ACID; 3-(1H-1,2,4-TRIAZOL-1-YL)PROPANOIC ACID; 3-(1H-1,2,4-TRIAZOL-3-YL)PROPANOIC ACID; 3-(1H-IMIDAZOL-1-YL)PROPANOIC ACID; 3-(1H-IMIDAZOL-2-YL)-ACRYLIC ACID; 3-(1H-IMIDAZOL-2-YL)-PROPIONIC ACID; 3-(1H-PYRAZOL-1-YL)PROPANOIC ACID; 3-(1H-PYRAZOL-4-YL)-ACRYLIC ACID; 3-(1H-PYRAZOL-4-YL)PROPANOIC ACID; 3-(1H-PYRAZOL-5-YL)PROPANOIC ACID; 3-(1H-PYRROL-1-YL)PROPANOIC ACID; 3-(1H-PYRROL-2-YL)PROPANOIC ACID; 3-(1H-TETRAZOL-1-YL)PROPANOIC ACID; 3-(1H-TETRAZOL-5-YL)PROPANOIC ACID; 3-(1-METHYLCYCLOPROPYL)PROPANOIC ACID; 3-(2-FURYL)ACRYLIC ACID; 3-(2-FURYL)PROP-2-YNOIC ACID; 3-(2-FURYL)PROPANOIC ACID; 3-(2-HYDROXYETHOXY)PROPANOIC ACID; 3-(2-METHOXYETHOXY)PROPANOIC ACID; 3-(2-METHYLPROPOXY)PROPANOIC ACID; 3-(2-PYRIDYL)ACRYLIC ACID; 3-(2-PYRIDYL)PROP-2-YNOIC ACID; 3-(3,3-DIMETHYL-2-OXIRANYLIDENE)-PROPANOIC ACID; 3-(3-FURYL)ACRYLIC ACID; 3-(3-HYDROXYAZETIDIN-1-YL)PROPANOIC ACID; 3-(3-HYDROXYPROPOXY)PROPANOIC ACID; 3-(3-PYRIDYL)ACRYLIC ACID; 3-(4H-1,2,4-TRIAZOL-4-YL)PROPANOIC ACID; 3-(4-PYRIDYL)ACRYLIC ACID; 3-(ACETYLOXY)-2-AMINOPROPANOIC ACID; 3-(ACETYLTHIO)PROPIONIC ACID; 3-(AMINOMETHYL)-OXOLANE-3-CARBOXYLIC ACID; 3-(BUT-2-EN-1-YLOXY)PROPANOIC ACID; 3-(BUT-3-EN-1-YLOXY)PROPANOIC ACID; 3-(BUT-3-EN-2-YLAMINO)PROPANOIC ACID; 3-(BUT-3-YN-1-YLAMINO)PROPANOIC ACID; 3-(BUTAN-2-YLAMINO)PROPANOIC ACID; 3-(BUTAN-2-YLOXY)PROPANOIC ACID; 3-(BUTYLAMINO)PROPANOIC ACID; 3-(CARBAMOYLAMINO)-2-METHYLPROPANOIC ACID; 3-(CARBAMOYLAMINO)BUTANOIC ACID; 3-(CARBOXYMETHYL)-1,2,3-OXADIAZOL-3-IUM-5-OLATE; 3-(CARBOXYMETHYL)-1,3-THIAZOL-3-IUM; 3-(CYCLOBUTYLAMINO)PROPANOIC ACID; 3-(CYCLOPROPYLAMINO)-2-METHYLPROPANOIC ACID; 3-(CYCLOPROPYLAMINO)-2-PROPENOIC ACID; 3-(CYCLOPROPYLAMINO)BUTANOIC ACID; 3-(CYCLOPROPYLMETHOXY)PROPANOIC ACID; 3-(DIETHYLAMINO)PROPANOIC ACID; 3-(DIMETHYLAMINO)-2-(METHYLAMINO)PROPANOIC ACID; 3-(DIMETHYLAMINO)-2-METHYLPROPANOIC ACID; 3-(DIMETHYLAMINO)BUTANOIC ACID; 3-(DIMETHYLAMINO)PENTANOIC ACID; 3-(DIMETHYLAMINO)PROPANOIC ACID; 3-(ETHYLAMINO)-2-METHYLPROPANOIC ACID; 3-(ETHYLAMINO)BUTANOIC ACID; 3-(ETHYLAMINO)PROPANOIC ACID; 3-(ETHYLCARBAMOYL)PROPANOIC ACID; 3-(ETHYLSULFANYL)-2-METHYLPROPANOIC ACID; 3-(ETHYLSULFANYL)BUTANOIC ACID; 3-(ETHYLTHIO)PROPANOIC ACID; 3-(FURAN-3-YL)PROPANOIC ACID; 3-(HYDROXYAMINO)ALANINE-15N; 3-(HYDROXYMETHYL)-1H-PYRAZOLE-5-CARBOXYLIC ACID; 3-(HYDROXYMETHYL)CYCLOBUTANECARBOXYLIC ACID; 3-(HYDROXYMETHYL)-CYCLOPENTANECARBOXYLIC ACID; 3-(HYDROXYMETHYL)FURAN-2-CARBOXYLIC ACID; 3-(IMIDAZOL-4-YL)PROPIONIC ACID; 3-(ISOBUTYLAMINO)PROPANOIC ACID; 3-(ISOPROPYLAMINO)PROPANOIC ACID; 3-(ISOPROPYL-METHYL-AMINO)-PROPIONIC ACID; 3-(ISOPROPYLTHIO)PROPANOIC ACID; 3-(ISOXAZOL-4-YL)PROPANOIC ACID; 3-(METHYLAMINO)-3-OXOPROPANOIC ACID; 3-(METHYLAMINO)BUTANOIC ACID; 3-(METHYLAMINO)OXOLANE-3-CARBOXYLIC ACID; 3-(METHYLAMINO)PROPANOIC ACID HYDROCHLORIDE; 3-(METHYLAMINO)PROPIONIC ACID; 3-(METHYLCARBAMOYL)PROP-2-ENOIC ACID; 3-(METHYL-

SULFANYL)BUTANOIC ACID; 3-(METHYLSULFANYL)PENTANOIC ACID; 3-(N-METHYLAMINO)-L-ALANINE; 3-(N-METHYLFORMAMIDO)PROPANOIC ACID; 3-(N-METHYL-HYDRAZINO)-PROPIONIC ACID; 3-(PROP-2-EN-1-YLAMINO)BUTANOIC ACID; 3-(PROP-2-EN-1-YLAMINO)PROPANOIC ACID; 3-(PROP-2-EN-1-YLSULFANYL)PROPANOIC ACID; 3-(PROP-2-YN-1-YLAMINO)BUTANOIC ACID; 3-(PROP-2-YN-1-YLAMINO)PROPANOIC ACID; 3-(PROP-2-YN-1-YLOXY)PROPANOIC ACID; 3-(PROP-2-YN-1-YLSULFANYL)PROPANOIC ACID; 3-(PROP-2-YNAMIDO)PROPANOIC ACID; 3-(PROPAN-2-YLAMINO)BUTANOIC ACID; 3-(PROPIONYLAMINO)PROPANOIC ACID; 3-(PROPYLAMINO)BUTANOIC ACID; 3-(PROPYLAMINO)PROPANOIC ACID; 3-(PROPYLSULFANYL)PROPANOIC ACID; 3-(PYRROL-3-YL)-PROPIONIC ACID; 3-(TETRAHYDRO-FURAN-2-YL)-PROPIONIC ACID; 3-(TRIMETHYLSILYL)PROPIOLIC ACID; 3,3,3-TRIFLUORO-DL-ALANINE; 3,3,3-TRIFLUOROLACTIC ACID; 3,3,3-TRIFLUOROPROPIONIC ACID; 3,3-DICHLOROACRYLIC ACID; 3,3-DIFLUOROCYCLOBUTANECARBOXYLIC ACID; 3,3-DIFLUOROPROPANOIC ACID; 3,3-DIMETHOXYPROPANOIC ACID; 3,3-DIMETHYL-2-(METHYLAMINO)BUTANOIC ACID; 3,3-DIMETHYL-4-OXOVALERIC ACID; 3,3-DIMETHYL-4-PENTENOIC ACID; 3,3-DIMETHYLACRYLIC ACID; 3,3-DIMETHYLBUTYRIC ACID; 3,3-DIMETHYLCYCLOBUTANECARBOXYLIC ACID; 3,3-DIMETHYLHEXANOIC ACID; 3,3-DIMETHYLPENTANOIC ACID; 3,3-DITHIOPROPIONIC ACID; 3,4,4-TRIMETHYLPENTANOIC ACID; 3,4-DEHYDRO-DL-PROLINE; 3,4-DEHYDRO-D-PROLINE; 3,4-DEHYDRO-L-PROLINE; 3,4-DEHYDRO-L-PROLINE HYDROCHLORIDE; 3,4-DIAMINOBUTYRIC ACID; 3,4-DIHYDRO-2H-PYRAN-2-CARBOXYLIC ACID; 3,4-DIHYDRO-2H-PYRAN-5-CARBOXYLIC ACID; 3,4-DIHYDRO-2H-PYRROLE-2-CARBOXYLIC ACID; 3,4-DIHYDRO-3-OXO-2-PYRAZINECARBOXYLIC ACID; 3,4-DIHYDRO-4-OXO-2-PYRIMIDINECARBOXYLIC ACID; 3,4-DIMETHYL-1H-PYRAZOLE-5-CARBOXYLIC ACID; 3,4-DIMETHYL-1H-PYRROLE-2-CARBOXYLIC ACID; 3,4-DIMETHYLHEXANOIC ACID; 3,4-DIMETHYLISOXAZOLE-5-CARBOXYLIC ACID; 3,4-DIMETHYLPENTANOIC ACID; 3,4-EPOXY-2-HYDROXY-VALERIC ACID; 3,4-METHYLENEDIOXYBUTANOIC ACID; 3,5-DIMETHYL-1H-PYRAZOLE-4-CARBOXYLIC ACID; 3,5-DIMETHYL-1H-PYRROLE-2-CARBOXYLIC ACID; 3,5-DIMETHYL-3H-IMIDAZOLE-4-CARBOXYLIC ACID; 3,5-DIMETHYL-4,5-DIHYDROISOXAZOLE-5-CARBOXYLIC ACID; 3,5-DIMETHYL-FURAN-2-CARBOXYLIC ACID; 3,5-DIMETHYLHEXANOIC ACID; 3,5-DIMETHYLISOXAZOLE-4-CARBOXYLIC ACID; 3,6-DIHYDRO-6-OXO-3-PYRIDAZINECARBOXYLIC ACID; 3-[(1-HYDROXYPROPAN-2-YL)AMINO]PROPANOIC ACID; 3-[(2-AMINOETHYL)(METHYL)AMINO]PROPANOIC ACID; 3-[(2-AMINOETHYL)AMINO]PROPANOIC ACID; 3-[(2-AMINOETHYL)SULFANYL]PROPANOIC ACID; 3-[(2-CYANOETHYL)AMINO]PROPANOIC ACID; 3-[(2E)-BUT-2-EN-1-YLAMINO]PROPANOIC ACID; 3-[(2-HYDROXYETHYL)(METHYL)AMINO]PROPANOIC ACID; 3-[(2-HYDROXYETHYL)AMINO]-2-METHYL-PROPANOIC ACID; 3-[(2-HYDROXYETHYL)AMINO]BUTANOIC ACID; 3-[(2-HYDROXYETHYL)AMINO]PROPANOIC ACID; 3-[(2-HYDROXYPROPYL)AMINO]PROPANOIC ACID; 3-[(2-METHOXYETHYL)AMINO]PROPANOIC ACID; 3-[(2-METHYLCYCLOPROPYL)AMINO]PROPANOIC ACID; 3-[(2-METHYLPROP-2-EN-1-YL)AMINO]PROPANOIC ACID; 3-[(3-AMINOPROPYL)AMINO]PROPANOIC ACID; 3-[(3-HYDROXYPROPYL)AMINO]PROPANOIC ACID; 3-[(CARBAMOYLMETHYL)AMINO]PROPANOIC ACID; 3-[(CYANOMETHYL)(METHYL)AMINO]PROPANOIC ACID; 3-[(CYANOMETHYL)AMINO]PROPANOIC ACID; 3-[(CYANOMETHYL)SULFANYL]PROPANOIC ACID; 3-[(CYCLOPROPYLMETHYL)AMINO]PROPANOIC ACID; 3-[(METHOXYCARBONYL)AMINO]PROPANOIC ACID; 3-[(METHYLCARBAMOYL)AMINO]PROPANOIC ACID; 3-[1,3]DIOXOLAN-2-YL-PROPIONIC ACID; 3-[ACETYL(METHYL)AMINO]PROPANOIC ACID; 3-[CARBAMOYL(METHYL)AMINO]PROPANOIC ACID; 3-[CYCLOPROPYL(METHYL)AMINO]PROPANOIC ACID; 3-[ETHYL(METHYL)AMINO]-2-METHYLPROPANOIC ACID; 3-[ETHYL(METHYL)AMINO]BUTANOIC ACID; 3-[ETHYL(METHYL)AMINO]PROPANOIC ACID; 3-[METHYL(PROP-2-EN-1-YL)AMINO]PROPANOIC ACID; 3-[METHYL(PROP-2-YN-1-YL)AMINO]PROPANOIC ACID; 3-[METHYL(PROPYL)AMINO]PROPANOIC ACID; 3-ACETAMIDO-2-METHYLPROPANOIC ACID; 3-ACETAMIDOBUTANOIC ACID; 3-ACETYLACRYLIC ACID; 3-ALLYLOXYPROPIONIC ACID; 3-AMINO-1,2,4-TRIAZOLE-5-CARBOXYLIC ACID; 3-AMINO-1,2,4-TRIAZOLE-5-CARBOXYLIC ACID HYDRATE; 3-AMINO-1H-PYRAZOLE-5-CARBOXYLIC ACID; 3-AMINO-1H-PYRROLE-2-CARBOXYLIC ACID; 3-AMINO-1-METHYL-1H-PYRAZOLE-5-CARBOXYLIC ACID; 3-AMINO-1-METHYLPYRROLIDINE-3-CARBOXYLIC ACID; 3-AMINO-2-(CYCLOPROPYLMETHYL)PROPANOIC ACID; 3-AMINO-2,2-DIFLUORO-PROPIONIC ACID; 3-AMINO-2,2-DIMETHYL-PROPANOIC ACID; 3-AMINO-2-CYANOBUT-2-ENOIC ACID; 3-AMINO-2-CYANOPROPIONIC ACID; 3-AMINO-2-HYDROXYHEXANOIC ACID; 3-AMINO-2-METHYLPROPANOIC ACID HYDROCHLORIDE; 3-AMINO-2-METHYL-PROPIONIC ACID HYDRATE; 3-AMINO-3,6-DIHYDRO-2H-PYRAN-2-CARBOXYLIC ACID; 3-AMINO-3-CYCLOBUTYL-PROPIONIC ACID; 3-AMINO-3-CYCLOPROPYL-PROPIONIC ACID; 3-AMINO-3-METHYL-BUTYRIC ACID; 3-AMINO-3-METHYLPENTANOIC ACID; 3-AMINO-3-OXOPROPANOIC ACID; 3-AMINO-4-(CARBOXYMETHYL)FURAZANE; 3-AMINO-4-(METHYLTHIO)-BUTANOIC ACID; 3-AMINO-4,4-DIMETHYL-PENTANOIC ACID; 3-AMINO-4-HYDROXYBUTYRIC ACID; 3-AMINO-4-METHYLHEXANOIC ACID; 3-AMINO-4-METHYL-PENT-4-ENOIC ACID; 3-AMINO-4-METHYLPENTANOIC ACID; 3-AMINO-4-OXO-PENTANOIC ACID; 3-AMINO-4-PYRIDAZINECARBOXYLIC ACID; 3-AMINO-4-PYRROLECARBOXYLIC ACID; 3-AMINO-5-ISOXAZOLECARBOXYLIC ACID; 3-AMINO-5-METHYLHEXANOIC ACID; 3-AMINOAZETIDINE-3-CARBOXYLIC ACID; 3-AMINOBENZOIC ACID; 3-AMINOCYCLOBUTANECARBOXYLIC ACID; 3-AMINOCYCLOHEXANECARBOXYLIC ACID; 3-AMINOCYCLOPENTANECARBOXYLIC ACID; 3-AMINOFURAN-2-CARBOXYLIC ACID; 3-AMINOHEPTANOIC ACID; 3-AMINO-HEXANOIC ACID;

3-AMINOISONICOTINIC ACID; 3-AMINOISOTHIAZOLE-4-CARBOXYLIC ACID; 3-AMINO-L-ALANINE HYDROCHLORIDE; 3-AMINOMETHYL-FURAN-2-CARBOXYLIC ACID; 3-AMINOOXETANE-3-CARBOXYLIC ACID; 3-AMINOPENTANE-3-CARBOXYLIC ACID; 3-AMINOPENTANEDIOIC ACID; 3-AMINOPENTANOIC ACID; 3-AMINOPYRAZINE-2-CARBOXYLIC ACID; 3-AMINOPYRAZOLE-4-CARBOXYLIC ACID; 3-AMINOPYRIDINE-2-CARBOXYLIC ACID; 3-AMINOPYRROLIDINE-3-CARBOXYLIC ACID; 3-AMINOTETRAHYDRO-2H-PYRAN-3-CARBOXYLIC ACID; 3-AMINO-TETRAHYDRO-FURAN-2-CARBOXYLIC ACID; 3-AMINOTETRAHYDROFURAN-3-CARBOXYLIC ACID; 3-AMINO-TETRAHYDRO-THIOPHENE-2-CARBOXYLIC ACID; 3-AMINO-TETRAHYDRO-THIOPHENE-3-CARBOXYLIC ACID; 3-AMINOTHIETANE-3-CARBOXYLIC ACID; 3-AMINOTHIOPHENE-2-CARBOXYLIC ACID; 3-AZABICYCLO[3.1.0]HEXANE-2-CARBOXYLIC ACID; 3-AZABICYCLO[3.1.0]HEXANE-2-CARBOXYLIC ACID; 3-AZIDO-2-METHYLPROPANOIC ACID; 3-AZIDO-3-METHYLBUTYRIC ACID; 3-AZIDOBUTANOIC ACID; 3-AZIDOPROPANOIC ACID; 3-BUTOXYPROPANOIC ACID; 3-BUTYNOIC ACID; 3-CARBAMOYL-2,3-DIMETHYLPROP-2-ENOIC ACID; 3-CARBAMOYLPROP-2-ENOIC ACID; 3-CARBOXY-1,1-DIMETHYL-, (E)-2-PROPENYL; 3-CARBOXY-1-METHYLPYRIDINIUM; 3-CHLORO-1H-PYRAZOLE-4-CARBOXYLIC ACID; 3-CHLORO-1H-PYRROLE-2-CARBOXYLIC ACID; 3-CHLORO-2,2-DIMETHYLBUT-3-ENOIC ACID; 3-CHLORO-2,2-DIMETHYLPROPIONIC ACID; 3-CHLORO-2-OXOPROPANOIC ACID; 3-CHLOROBUTYRIC ACID; 3-CHLOROCROTONIC ACID; 3-CHLOROCYCLOBUTANECARBOXYLIC ACID; 3-CHLOROFURAN-2-CARBOXYLIC ACID; 3-CHLOROFURAN-4-CARBOXYLIC ACID; 3-CHLOROISOXAZOLE-5-CARBOXYLIC ACID; 3-CHLORO-L-ALANINE; 3-CHLOROPROPIONIC ACID; 3-CYANOBENZOIC ACID; 3-CYANOISONICOTINIC ACID; 3-CYANOPROPANOIC ACID; 3-CYANOPYRIDINE-2-CARBOXYLIC ACID; 3-CYCLOHEXENE-1-CARBOXYLIC ACID; 3-CYCLOPENT-1-ENYL-ACRYLIC ACID; 3-CYCLOPENTENE-1-CARBOXYLIC ACID; 3-CYCLOPENTYLPROPIONIC ACID; 3-CYCLOPROPYL-2,2-DIMETHYLPROPIONIC ACID; 3-CYCLOPROPYL-2-METHYLPROPIONIC ACID; 3-CYCLOPROPYL-3-HYDROXY-2-METHYLPROPANOIC ACID; 3-CYCLOPROPYL-3-HYDROXYBUTANOIC ACID; 3-CYCLOPROPYL-3-HYDROXYPROPANOIC ACID; 3-CYCLOPROPYL-3-OXO-PROPIONIC ACID; 3-CYCLOPROPYLBUTANOIC ACID; 3-CYCLOPROPYLPROP-2-YNOIC ACID; 3-CYCLOPROPYLPROPIONIC ACID; 3-ETHOXY-2-(METHYLAMINO)PROPANOIC ACID; 3-ETHOXY-2-BUTENOIC ACID; 3-ETHOXYACRYLIC ACID; 3-ETHOXYPROPIONIC ACID; 3-ETHYL CYCLOBUTANECARBOXYLIC ACID; 3-ETHYL-1,2,4-OXADIAZOLE-5-CARBOXYLIC ACID; 3-ETHYL-1H-PYRAZOLE-4-CARBOXYLIC ACID; 3-ETHYL-2-HEXENOIC ACID; 3-ETHYL-2-HYDROXYPENTANOIC ACID; 3-ETHYL-3-HYDROXYPENTANOIC ACID; 3-ETHYL-4,5-DIHYDROISOXAZOLE-5-CARBOXYLIC ACID; 3-ETHYL-4-METHYLPENTANOIC ACID; 3-ETHYLHEXANOIC ACID; 3-ETHYLOXETANE-3-CARBOXYLIC ACID; 3-ETHYLOXOLANE-3-CARBOXYLIC ACID; 3-ETHYLPENT-2-ENOIC ACID; 3-ETHYLPENTANOIC ACID; 3-ETHYLPYRROLIDINE-3-CARBOXYLIC ACID; 3-ETHYNYL-BENZOIC ACID; 3-ETHYNYLPICOLINIC ACID; 3-FLUORO-2,2-DIMETHYLPROPANOIC ACID; 3-FLUORO-2-THIOPHENECARBOXYLIC ACID; 3-FLUOROBENZOIC ACID; 3-FLUOROCYCLOBUTANECARBOXYLIC ACID; 3-FLUORO-DL-ALANINE; 3-FLUORO-DL-NORLEUCINE; 3-FLUORO-DL-VALINE; 3-FLUOROISONICOTINIC ACID; 3-FLUOROPROPANOIC ACID; 3-FLUOROPYRIDINE-2-CARBOXYLIC ACID; 3-FORMAMIDO-2-METHYLPROPANOIC ACID; 3-FORMAMIDOPROPANOIC ACID; 3-FORMYL-2-FUROIC ACID; 3-FUROIC ACID; 3-FURYL(OXO)ACETIC ACID; 3-GUANIDINOPROPIONIC ACID; 3H-1,2,4-TRIAZOLE-3-CARBOXYLIC ACID, 5-AMINO-; 3-HEPTENOIC ACID; 3H-TETRAFLUOROPROPIONIC ACID; 3-HYDROXY-1H-PYRROLE-2-CARBOXYLIC ACID; 3-HYDROXY-1-METHYLPYRROLIDINE-3-CARBOXYLIC ACID; 3-HYDROXY-2-(PROPAN-2-YL)BUTANOIC ACID; 3-HYDROXY-2,2,3-TRIMETHYLBUTANOIC ACID; 3-HYDROXY-2,2-DIMETHYLBUTANOIC ACID; 3-HYDROXY-2,2-DIMETHYLPENTANOIC ACID; 3-HYDROXY-2,3-DIMETHYLBUTANOIC ACID; 3-HYDROXY-2,3-DIMETHYLPENTANOIC ACID; 3-HYDROXY-2,4-DIMETHYLPENTANOIC ACID; 3-HYDROXY-2-METHYLHEXANOIC ACID; 3-HYDROXY-2-METHYLPENTANOIC ACID; 3-HYDROXY-2-METHYLPROPANOIC ACID; 3-HYDROXY-2-OXOPROPANOIC ACID; 3-HYDROXY-3,4-DIMETHYLPENTANOIC ACID; 3-HYDROXY-3-METHYLCYCLOBUTANECARBOXYLIC ACID; 3-HYDROXY-3-METHYL-N-VALERIC ACID; 3-HYDROXY-4,4-DIMETHYLPENTANOIC ACID; 3-HYDROXY-4-METHYLHEXANOIC ACID; 3-HYDROXY-4-METHYLPENTANOIC ACID; 3-HYDROXY-4-PYRIDINECARBOXYLIC ACID; 3-HYDROXY-5-METHYLHEXANOIC ACID; 3-HYDROXYASPARTIC ACID; 3-HYDROXYBENZOIC ACID; 3-HYDROXYBUTYRIC ACID; 3-HYDROXYCYCLOBUTANECARBOXYLIC ACID; 3-HYDROXY-CYCLOPENTANECARBOXYLIC ACID; 3-HYDROXYGLUTARIC ACID; 3-HYDROXYHEXANOIC ACID; 3-HYDROXYISOXAZOLE-5-CARBOXYLIC ACID; 3-HYDROXY-N-METHYLVALINE; 3-HYDROXYOXOLANE-3-CARBOXYLIC ACID; 3-HYDROXYPENT-4-ENOIC ACID; 3-HYDROXYPICOLINIC ACID; 3-HYDROXYPROPIONIC ACID; 3-HYDROXYTETRAHYDRO-3-THIOPHENECARBOXYLIC ACID; 3-HYDROXYTHIOPHENE-2-CARBOXYLIC ACID; 3-ISOPROPOXY-3-OXOPROPANOIC ACID; 3-ISOPROPOXYPROPANOIC ACID; 3-ISOPROPYL-CYCLOBUTANECARBOXYLIC ACID; 3-ISOTHIOUREIDOPROPIONIC ACID; 3-ISOXAZOL-3-YLPROPANOIC ACID; 3-ISOXAZOL-5-YLPROPANOIC ACID; 3-ISOXAZOLEACETIC ACID; 3-ISOXAZOLEACETIC ACID, 5-HYDROXY-; 3-ISOXAZOLECARBOXYLIC ACID; 3-ISOXAZOLIDIN-2-YLPROPANOIC ACID; 3-MERCAPTOISOBUTYRIC ACID; 3-MERCAPTOPROPIONIC ACID; 3-METHANESULFINYLPROPANOIC ACID; 3-METHOXY-1H-PYRAZOLE-4-CARBOXYLIC ACID; 3-METHOXY-2-(METHYLAMINO)PROPANOIC ACID; 3-METHOXY-2,2-DIMETHYLPROPANOIC ACID; 3-METHOXY-2-FUROIC ACID; 3-METHOXY-2-METHYL-2-(METHYLAMINO)PROPANOIC ACID; 3-METHOXY-2-METHYL-3-OXOPROPANOIC ACID; 3-METHOXY-2-METHYLPROPANOIC ACID; 3-METHOXYBUT-2-ENOIC ACID; 3-METHOXYBUTYRIC ACID; 3-METHOXYCYCLOBUTANECARBOXYLIC ACID;

3-METHOXY-ISOXAZOLE-5-CARBOXYLIC ACID; 3-METHOXYPROPIONIC ACID; 3-METHOXYVALINE; 3-METHYL-1,2,4-OXADIAZOLE-5-CARBOXYLIC ACID; 3-METHYL-1-CYCLOHEXANECARBOXYLIC ACID; 3-METHYL-1H-PYRAZOLE-4-CARBOXYLIC ACID; 3-METHYL-1H-PYRAZOLE-5-CARBOXYLIC ACID; 3-METHYL-1H-PYRROLE-2-CARBOXYLIC ACID; 3-METHYL-2-(METHYLAMINO)PENTANOIC ACID; 3-METHYL-2-(METHYLSULFANYL)BUTANOIC ACID; 3-METHYL-2-FUROIC ACID; 3-METHYL-2-HEXENOIC ACID; 3-METHYL-2-OXO-2,3-DIHYDRO-1H-IMIDAZOLE-4-CARBOXYLIC ACID; 3-METHYL-2-OXOBUTYRIC ACID; 3-METHYL-2-OXOVALERIC ACID; 3-METHYL-2-PENTENOIC ACID; 3-METHYL-2-SULFANYLBUTANOIC ACID; 3-METHYL-2-THIOPHENECARBOXYLIC ACID; 3-METHYL-4,5-DIHYDROISOXAZOLE-5-CARBOXYLIC ACID; 3-METHYL-4-ISOXAZOLECARBOXYLIC ACID; 3-METHYL-4-OXO-2-PENTENOIC ACID; 3-METHYL-4-OXOHEXANOIC ACID; 3-METHYL-4-PENTENOIC ACID; 3-METHYL-4-PIPERIDINECARBOXYLIC ACID; 3-METHYL-4-PYRIDAZINECARBOXYLIC ACID; 3-METHYL-4-PYRIDINECARBOXYLIC ACID; 3-METHYL-5,6-DIHYDRO-1,4-DIOXINE-2-CARBOXYLIC ACID; 3-METHYL-5-ISOXAZOLEACETIC ACID; 3-METHYL-5-OXO-4,5-DIHYDRO-1H-PYRAZOLE-4-CARBOXYLIC ACID; 3-METHYL-5-OXO-PYRROLIDINE-2-CARBOXYLIC ACID; 3-METHYLBUT-3-ENOIC ACID; 3-METHYL-CYCLOBUTANEACETIC ACID; 3-METHYLCYCLOBUTYLCARBOXYLIC ACID; 3-METHYLENECYCLOBUTANECARBOXYLIC ACID; 3-METHYLENECYCLOPROPANE-TRANS-1,2-DICARBOXYLIC ACID; 3-METHYLENEPENTANEDIOIC ACID; 3-METHYLGLUTACONIC ACID; 3-METHYLGLUTARIC ACID; 3-METHYLHEPTANOIC ACID; 3-METHYLHEXANOIC ACID; 3-METHYLIDENECYCLOPROPANE-1,2-DICARBOXYLIC ACID; 3-METHYLISOTHIAZOLE-4-CARBOXYLIC ACID; 3-METHYLISOTHIAZOLE-5-CARBOXYLIC ACID; 3-METHYLISOXAZOLE-5-CARBOXYLIC ACID; 3-METHYLOXANE-3-CARBOXYLIC ACID; 3-METHYLOXETANE-3-CARBOXYLIC ACID; 3-METHYL-OXOLANE-3-CARBOXYLIC ACID; 3-METHYL-PENT-2-ENOIC ACID; 3-METHYLPENTANOIC ACID; 3-METHYLPICOLINIC ACID; 3-METHYLPIPERAZINE-2-CARBOXYLIC ACID; 3-METHYL-PIPERIDINE-3-CARBOXYLIC ACID; 3-METHYLPROLINE; 3-METHYLPYRAZINE-2-CARBOXYLIC ACID; 3-METHYL-PYRROLIDINE-3-CARBOXYLIC ACID; 3-METHYLTHIOPROPIONIC ACID; 3-MORPHOLINECARBOXYLIC ACID; 3-NITROPROPIONIC ACID; 3-OCTENOIC ACID; 3-OXABICYCLO[3.1.0]HEXANE-6-CARBOXYLIC ACID; 3-OXALURIC ACID; 3-OXAZOL-5-YL-PROPIONIC ACID; 3-OXO-1-CYCLOHEXANECARBOXYLIC ACID; 3-OXO-2,3-DIHYDROISOXAZOLE-5-CARBOXYLIC ACID; 3-OXO-2,3-DIHYDRO-PYRIDAZINE-4-CARBOXYLIC ACID; 3-OXO-2,3-DIHYDROPYRIDINE-5-CARBOXYLIC ACID; 3-OXOCYCLOBUTANECARBOXYLIC ACID; 3-OXOCYCLOPENT-1-ENECARBOXYLIC ACID; 3-OXOCYCLOPENTANECARBOXYLIC ACID; 3-OXOPENTANOIC ACID; 3-OXO-PIPERAZINE-2-CARBOXYLIC ACID; 3-OXO-PIPERIDINE-2-CARBOXYLIC ACID; 3-OXOPROPANOIC ACID; 3-PENTENOIC ACID; 3-PIPERIDINE ACETIC ACID; 3-PROPOXY-PROPIONIC ACID; 3-PYRIDAZINEACETIC ACID; 3-PYRIDIN-3-YLPROP-2-YNOIC ACID; 3-PYRIDIN-4-YL-PROP-2-YNOIC ACID; 3-PYRIDINECARBOXYLIC ACID, 5-ETHYNYL-; 3-PYRIDINECARBOXYLIC ACID, HYDRATE; 3-PYRIDYLACETIC ACID; 3-PYRROLIDIN-1-YL-PROPIONIC ACID; 3-PYRROLIDIN-2-YL-PROPIONIC ACID; 3-PYRROLIDINEACETIC ACID; 3-PYRROLIDINECARBOXYLIC ACID, 4-AMINO-; 3-SULFANYLPENTANOIC ACID; 3-TERT-BUTOXYPROPIONIC ACID; 3-TERT-BUTYL-DL-ALANINE; 3-THIOLNORVALINE; 3-THIOPHENEACETIC ACID; 3-THIOPHENECARBOXYLIC ACID; 3-THIOPHENECARBOXYLIC ACID, 2-FLUORO-; 3-THIOPHENECARBOXYLIC ACID, 5-AMINO-; 3-TRIMETHYLSILYLPROPIONIC ACID; 3-UREIDOPROPIONIC ACID; 3-VINYLBENZOIC ACID; 4-(1-METHYLCYCLOPROPYL)BUTANOIC ACID; 4-(2-HYDROXYETHOXY)BUTANOIC ACID; 4-(ALLYLOXY)BUTANOIC ACID; 4-(AMINOMETHYL)-1,2,5-OXADIAZOLE-3-CARBOXYLIC ACID; 4-(CYCLOPROPYLAMINO)BUTANOIC ACID; 4-(DIMETHYLAMINO)-3-HYDROXYBUTANOIC ACID; 4-(DIMETHYLAMINO)BUTANOIC ACID; 4-(DIMETHYLAMINO)PENTANOIC ACID; 4-(ETHYLAMINO)BUTANOIC ACID; 4-(ETHYLSULFANYL)BUTANOIC ACID; 4-(HYDROXYMETHYL)FURAN-2-CARBOXYLIC ACID; 4-(ISOPROPYLAMINO)BUTANOIC ACID; 4-(METHYLAMINO)BUTYRIC ACID; 4-(METHYLAMINO)PYRROLIDINE-2-CARBOXYLIC ACID; 4-(METHYLCARBAMOYL)BUTANOIC ACID; 4-(METHYLSULFANYL)BUTANOIC ACID; 4-(METHYLSULFANYL)PENTANOIC ACID; 4-(PROP-2-EN-1-YLAMINO)BUTANOIC ACID; 4-(PROP-2-YN-1-YLAMINO)BUTANOIC ACID; 4-(PROP-2-YN-1-YLOXY)BUTANOIC ACID; 4-(PROPAN-2-YLOXY)BUTANOIC ACID; 4-(PROPYLAMINO)BUTANOIC ACID; 4,4,4-TRIFLUOROBUT-2-YNOIC ACID; 4,4,4-TRIFLUOROBUTYRIC ACID; 4,4,4-TRIFLUOROCROTONIC ACID; 4,4-DIAMINO-3-OXOPENTANOIC ACID; 4,4-DIFLUORO-2-METHYLBUTANOIC ACID; 4,4-DIFLUORO-BUT-2-ENOIC ACID; 4,4-DIFLUOROBUTANOIC ACID; 4,4-DIFLUOROPENTANOIC ACID; 4,4-DIMETHOXY-BUT-2-ENOIC ACID; 4,4-DIMETHOXYBUTANOIC ACID; 4,4-DIMETHYL-2-OXO-PENTANOIC ACID; 4,4-DIMETHYL-3-OXOPENTANOIC ACID; 4,4-DIMETHYLHEXANOIC ACID; 4,4-DIMETHYLPENTANOIC ACID; 4,4-DIMETHYL-PYRROLIDINE-3-CARBOXYLIC ACID; 4,5-DEHYDRO-LEUCINE; 4,5-DIHYDRO-FURAN-3-CARBOXYLIC ACID; 4,5-DIHYDRO-OXAZOLE-4-CARBOXYLIC ACID; 4,5-DIHYDROTHIAZOLE-5-CARBOXYLIC ACID; 4,5-DIMETHYL-1H-IMIDAZOLE-2-CARBOXYLIC ACID; 4,5-DIMETHYL-1H-PYRROLE-2-CARBOXYLIC ACID; 4,5-DIMETHYL-2-FUROIC ACID; 4,5-DIMETHYL-ISOXAZOLE-3-CARBOXYLIC ACID; 4,5-DIOXOVALERIC ACID; 4,5-EPOXY-2-HEXENOIC ACID; 4-[(2-HYDROXYETHYL)AMINO]BUTANOIC ACID; 4-[(CYANOMETHYL)AMINO]BUTANOIC ACID; 4-[ETHYL(METHYL)AMINO]BUTANOIC ACID; 4-ACETAMIDOBUTYRIC ACID; 4-ACETYLBUTYRIC ACID; 4-AMINO-[1,2,5]THIADIAZOLE-3-CARBOXYLIC ACID; 4-AMINO-1,2,5-OXADIAZOLE-3-CARBOXYLIC ACID; 4-AMINO-1-CYCLOHEXENE-1-CARBOXYLIC ACID; 4-AMINO-1H-IMIDAZOLE-2-CARBOXYLIC ACID; 4-AMINO-1H-PYRAZOLE-3-CARBOXYLIC ACID; 4-AMINO-1H-PYRAZOLE-5-CARBOXYLIC ACID; 4-AMINO-1H-

PYRROLE-2-CARBOXYLIC ACID; 4-AMINO-1-METHYL-1H-PYRAZOLE-3-CARBOXYLIC ACID; 4-AMINO-1-METHYL-1H-PYRAZOLE-5-CARBOXYLIC ACID; 4-AMINO-1-METHYL-1H-PYRROLE-2-CARBOXYLIC ACID; 4-AMINO-2,2-DIFLUOROBUTYRIC ACID; 4-AMINO-2,2-DIMETHYL-BUTYRIC ACID; 4-AMINO-2,4-DIMETHYL-PENTANOIC ACID; 4-AMINO-2-HYDROXY-3,3-DIMETHYLBUTANOIC ACID; 4-AMINO-3,3-DIFLUOROBUTANOIC ACID; 4-AMINO-3,3-DIMETHYLBUTANOIC ACID; 4-AMINO-3,4-DIMETHYL-PENTANOIC ACID; 4-AMINO-3-METHYLISOXAZOLE-5-CARBOXYLIC ACID; 4-AMINO-4-METHYLPENTANOIC ACID; 4-AMINO-5-FLUOROPENTANOIC ACID; 4-AMINO-5-IMIDAZOLECARBOXYLIC ACID; 4-AMINO-5-METHYL-1H-PYRAZOLE-3-CARBOXYLIC ACID; 4-AMINO-5-METHYLFURAN-2-CARBOXYLIC ACID; 4-AMINO-5-METHYLHEXANOIC ACID; 4-AMINOBENZOIC ACID; 4-AMINOBUTANOIC ACID HYDROCHLORIDE; 4-AMINOBUTYRIC ACID; 4-AMINOCYCLOHEMNECARBOXYLIC ACID; 4-AMINO-ISOTHIAZOLE-3-CARBOXYLIC ACID; 4-AMINOMETHYL-1H-IMIDAZOLE-2-CARBOXYLIC ACID; 4-AMINONICOTINIC ACID; 4-AMINOPIPERIDINE-3-CARBOXYLIC ACID; 4-AMINOPIPERIDINE-4-CARBOXYLIC ACID; 4-AMINO-PYRIDAZINE-3-CARBOXYLIC ACID; 4-AMINOPYRIDINE-2-CARBOXYLIC ACID; 4-AMINOPYRIMIDINE-2-CARBOXYLIC ACID; 4-AMINOPYRIMIDINE-5-CARBOXYLIC ACID; 4-AMINO-TETRAHYDRO-FURAN-3-CARBOXYLIC ACID; 4-AMINO-TETRAHYDRO-PYRAN-4-CARBOXYLIC ACID; 4-AMINO-TETRAHYDRO-THIOPHENE-3-CARBOXYLIC ACID; 4-AMINOTHIOPHENE-2-CARBOXYLIC ACID; 4-AMINOTHIOPHENE-3-CARBOXYLIC ACID; 4-CARBOXYL BENZOCYCLOBUTENE; 4-CHLORO-1H-PYRAZOLE-3-CARBOXYLIC ACID; 4-CHLORO-1H-PYRAZOLE-5-CARBOXYLIC ACID; 4-CHLORO-1H-PYRROLE-2-CARBOXYLIC ACID; 4-CHLOROBUTYRIC ACID; 4-CHLOROBUTYRIC ACID, [1-14C]; 4-CHLOROFURAN-2-CARBOXYLIC ACID; 4-CYANO-1H-IMIDAZOLE-2-CARBOXYLIC ACID; 4-CYANO-1H-PYRROLE-2-CARBOXYLIC ACID; 4-CYANO-2-PYRIDINECARBOXYLIC ACID; 4-CYANO-3-PYRIDINECARBOXYLIC ACID; 4-CYANOBENZOIC ACID; 4-CYANOBENZOIC ACID, [CYANO-14C]; 4-CYANOBUTANOIC ACID; 4-CYCLOHEPTENE-1-CARBOXYLIC ACID; 4-CYCLOPROPYL-4-HYDROXYBUTANOIC ACID; 4-CYCLOPROPYL-4-OXOBUTYRIC ACID; 4-ETHOXY-2-METHYLBUTANOIC ACID; 4-ETHOXY-4-OXOBUTANOIC ACID; 4-ETHOXYBUTANOIC ACID; 4-ETHOXYPENTANOIC ACID; 4-ETHYLHEXANOIC ACID; 4-ETHYNYL-1H-PYRROLE-2-CARBOXYLIC ACID; 4-ETHYNYL-BENZOIC ACID; 4-FLUORO-2-AZABICYCLO[2.1.1]HEXANE-1-CARBOXYLIC ACID; 4-FLUORO-2-PYRROLIDINECARBOXYLIC ACID; 4-FLUORO-3-METHYL-1H-PYRAZOLE-5-CARBOXYLIC ACID; 4-FLUORO-4-PIPERIDINECARBOXYLIC ACID; 4-FLUOROBENZOIC ACID; 4-FLUOROBUTYRIC ACID; 4-FLUORO-CYCLOHEXANECARBOXYLIC ACID; 4-FLUORO-L-THREONINE; 4-FLUORONICOTINIC ACID; 4-FLUOROPYRIDAZINE-3-CARBOXYLIC ACID; 4-FLUOROPYRIDINE-2-CARBOXYLIC ACID; 4-FLUORO-TETRAHYDRO-2H-PYRAN-4-CARBOXYLIC ACID; 4-FORMAMIDOBUTYRIC ACID; 4-FORMYL-1H-IMIDAZOLE-2-CARBOXYLIC ACID; 4-FORMYL-1H-PYRAZOLE-3-CARBOXYLIC ACID; 4-FORMYL-1H-PYRROLE-2-CARBOXYLIC ACID; 4-GUANIDINOBUTYRIC ACID; 4H-1,2,4-TRIAZOL-4-YLACETIC ACID; 4H-1,2,4-TRIAZOLE-3-CARBOXYLIC ACID; 4-HEXENOIC ACID; 4-HEXYNOIC ACID, 2-AMINO-, (2R)-; 4-HEXYNOIC ACID, 2-AMINO-, (2S)-; 4H-IMIDAZOLE-5-CARBOXYLIC ACID; 4-HYDROXY-2-METHYLHEXANOIC ACID; 4-HYDROXY-2-METHYLPENTANOIC ACID; 4-HYDROXY-2-PYRROLINE-2-CARBOXYLIC ACID; 4-HYDROXY-2-THIOPHENECARBOXYLIC ACID; 4-HYDROXY-3-METHYLHEXANOIC ACID; 4-HYDROXY-3-METHYLPENTANOIC ACID; 4-HYDROXY-4-METHYLPENT-2-YNOIC ACID; 4-HYDROXY-5-METHYLHEXANOIC ACID; 4-HYDROXYBENZOIC ACID; 4-HYDROXYBENZOIC ACID [CARBOXYL-14C]; 4-HYDROXY-BUT-2-ENOIC ACID; 4-HYDROXY-BUT-2-YNOIC ACID; 4-HYDROXYBUTYRIC ACID; 4-HYDROXYBUTYRIC ACID, [2,3-3H]-; 4-HYDROXY-CYCLOHEXANE CARBOXYLIC ACID, [CARBOXYL-14C]; 4-HYDROXYCYCLOHEXANECARBOXYLIC ACID; 4-HYDROXY-DL-PROLINE; 4-HYDROXYFURAZAN-3-CARBOXYLIC ACID; 4-HYDROXYHEPTANOIC ACID; 4-HYDROXYHEXANOIC ACID; 4-HYDROXYIMINO-PENTANOIC ACID; 4-HYDROXYISOLEUCINE; 4-HYDROXY-L-ISOLEUCINE; 4-HYDROXYMETHYL-1H-IMIDAZOLE-2-CARBOXYLIC ACID; 4-HYDROXYMETHYL-PYRROLIDINE-3-CARBOXYLIC ACID; 4-HYDROXYNICOTINIC ACID; 4-HYDROXYOXANE-4-CARBOXYLIC ACID; 4-HYDROXYPENTANOIC ACID; 4-HYDROXYPIPECOLIC ACID; 4-HYDROXYPIPERIDINE-4-CARBOXYLIC ACID; 4-HYDROXYPYRIDAZINE-3-CARBOXYLIC ACID; 4-HYDROXYPYRIDINE-2-CARBOXYLIC ACID; 4-HYDROXYPYRIMIDINE-5-CARBOXYLIC ACID; 4-HYDROXYPYRROLIDINE-2-CARBOXYLIC ACID; 4-HYDROXY-TETRAHYDRO-2-FUROIC ACID; 4-ISOTHIAZOLECARBOXYLIC ACID; 4-MERCAPTO-2-PYRROLIDINECARBOXYLIC ACID; 4-MERCAPTOBUTYRIC ACID; 4-MERCAPTO-PENTANOIC ACID; 4-METHOXY-2-(METHYLAMINO)BUTANOIC ACID; 4-METHOXY-2,2-DIMETHYLBUTANOIC ACID; 4-METHOXY-2-METHYLBUTANOIC ACID; 4-METHOXYBUTANOIC ACID; 4-METHOXYPENTANOIC ACID; 4-METHOXY-PYRROLIDINE-3-CARBOXYLIC ACID; 4-METHYL HYDROGEN L-ASPARTATE; 4-METHYL PYRIDINE-2-CARBOXYLIC ACID, [CARBOXYL-14C]; 4-METHYL-1,2,3-THIADIAZOLE-5-CARBOXYLIC ACID; 4-METHYL-1,2,5-OXADIAZOLE-3-CARBOXYLIC ACID; 4-METHYL-1,3-OXAZOLE-5-CARBOXYLIC ACID; 4-METHYL-1-CYCLOHEXANECARBOXYLIC ACID; 4-METHYL-1H-IMIDAZOLE-2-CARBOXYLIC ACID; 4-METHYL-1H-IMIDAZOLE-2-CARBOXYLIC ACID HYDRATE; 4-METHYL-1H-IMIDAZOLE-5-CARBOXYLIC ACID; 4-METHYL-1H-PYRROLE-3-CARBOXYLIC ACID; 4-METHYL-2,5-CYCLOHEXADIENE-1-CARBOXYLIC ACID; 4-METHYL-2-OXOVALERIC ACID; 4-METHYL-2-PENTENOIC ACID; 4-METHYL-2-PENTYNOIC ACID; 4-METHYL-2-PYRIMIDINECARBOXYLIC ACID; 4-METHYL-2-PYRROLIDINE CARBOXYLIC ACID; 4-METHYL-2-THIOPHENECARBOXYLIC ACID; 4-METHYL-3-FURANCARBOXYLIC ACID; 4-METHYL-3-PENTENOIC ACID; 4-METHYL-3-PYRIDAZINECARBOXYLIC ACID; 4-METHYL-3-

PYRROLIDINECARBOXYLIC ACID; 4-METHYL-4H-1,2,4-TRIAZOLE-3-CARBOXYLIC ACID; 4-METHYL-5-ISOTHIAZOLECARBOXYLIC ACID; 4-METHYL-5-OXO-2,5-DIHYDRO-1H-PYRAZOLE-3-CARBOXYLIC ACID; 4-METHYL-5-OXO-4,5-DIHYDRO-1H-PYRAZOLE-3-CARBOXYLIC ACID; 4-METHYL-5-OXOTETRAHYDRO-3-FURANCARBOXYLIC ACID; 4-METHYL-5-OXY-FURAZAN-3-CARBOXYLIC ACID; 4-METHYLBICYCLO[3.1.0]HEX-2-ENE-6-CARBOXYLIC ACID; 4-METHYLENE-5-OXO-4,5-DIHYDRO-FURAN-3-CARBOXYLIC ACID; 4-METHYLENE-L-PROLINE; 4-METHYLHEPTANOIC ACID; 4-METHYLHEXANOIC ACID; 4-METHYLIDENECYCLOHEXANE-1-CARBOXYLIC ACID; 4-METHYLISOXAZOLE-3-CARBOXYLIC ACID; 4-METHYLISOXAZOLE-5-CARBOXYLIC ACID; 4-METHYLMORPHOLINE-2-CARBOXYLIC ACID; 4-METHYLMORPHOLINE-3-CARBOXYLIC ACID; 4-METHYLNICOTINIC ACID; 4-METHYLOXAZOLE-2-CARBOXYLIC ACID; 4-METHYLPENT-4-ENOIC ACID; 4-METHYLPENTANOIC ACID; 4-METHYLPIPERAZINE-2-CARBOXYLIC ACID; 4-METHYL-PIPERIDINE-2-CARBOXYLIC ACID; 4-METHYLPIPERIDINE-4-CARBOXYLIC ACID; 4-METHYLPYRAZOLE-3-CARBOXYLIC ACID; 4-METHYLPYRIDINE-2-CARBOXYLIC ACID; 4-METHYLPYRIMIDINE-5-CARBOXYLIC ACID; 4-METHYLPYRROLE-2-CARBOXYLIC ACID; 4-METHYLTETRAHYDRO-2H-PYRAN-4-CARBOXYLIC ACID; 4-METHYLTHIAZOLE-2-CARBOXYLIC ACID; 4-METHYLTHIAZOLE-5-CARBOXYLIC ACID; 4-METHYLTHIOPHENE-3-CARBOXYLIC ACID; 4-NITROBUTANOIC ACID; 4-OXAZOLEACETIC ACID; 4-OXAZOLEACETIC ACID, 2-METHYL-; 4-OXAZOLECARBOXYLIC ACID; 4-OXAZOLIDINECARBOXYLIC ACID; 4-OXO-1,4-DIHYDRO-PYRIMIDINE-5-CARBOXYLIC ACID; 4-OXOAZETIDINE-2-CARBOXYLIC ACID; 4-OXOCYCLOHEXANECARBOXYLIC ACID; 4-OXOHEPTANOIC ACID; 4-OXOHEXANOIC ACID; 4-OXOPIPERIDINE-2-CARBOXYLIC ACID; 4-OXO-PIPERIDINE-3-CARBOXYLIC ACID; 4-OXO-PROLINE; 4-OXOPYRROLIDINE-3-CARBOXYLIC ACID; 4-OXOTETRAHYDROFURAN-3-CARBOXYLIC ACID; 4-OXOTETRAHYDROTHIOPHENE-3-CARBOXYLIC ACID; 4-PENTENOIC ACID; 4-PENTYNOIC ACID; 4-PROPOXYBUTANOIC ACID; 4-PYRIDINEACETIC ACID; 4-PYRIDINEACRYLIC ACID; 4-PYRIMIDINEACETIC ACID; 4-PYRIMIDINECARBOXYLIC ACID, 5-HYDROXY-; 4-UREIDO-BUTYRIC ACID; 4-VINYLBENZOIC ACID; 4-YN-VPA; 5-(AMINOMETHYL)-2-FUROIC ACID; 5-(DIMETHYLAMINO)PENTANOIC ACID; 5-(HYDROXYMETHYL)-1H-PYRROLE-2-CARBOXYLIC ACID; 5-(HYDROXYMETHYL)ISOXAZOLE-3-CARBOXYLIC ACID; 5-(HYDROXYMETHYL)OXOLANE-2-CARBOXYLIC ACID; 5-(METHYLAMINO)FURAN-2-CARBOXYLIC ACID; 5-(METHYLSULFANYL)PENTANOIC ACID; 5,5-DIMETHYLHEXANOIC ACID; 5,5-DIMETHYL-PYRROLIDINE-2-CARBOXYLIC ACID; 5,6-DIHYDRO-[1,4]DIOXINE-2-CARBOXYLIC ACID; 5,6-DIHYDRO-1,4-OXATHIINE-2-CARBOXYLIC ACID; 5,6-DIHYDRO-2H-PYRAN-3-CARBOXYLIC ACID; 5,6-DIHYDRO-4H-PYRAN-2-CARBOXYLIC ACID; 5,6-DIHYDRO-5-OXO-2-PYRAZINECARBOXYLIC ACID; 5-ACETYLVALERIC ACID; 5-AMINO CAPROIC ACID; 5-AMINO-1H-[1,2,3]TRIAZOLE-4-CARBOXYLIC ACID; 5-AMINO-1H-1,2,4-TRIAZOLE-3-CARBOXYLIC ACID; 5-AMINO-1H-IMIDAZOLE-4-CARBOXYLIC ACID; 5-AMINO-1H-PYRAZOLE-3-ACETIC ACID; 5-AMINO-1H-PYRAZOLE-3-CARBOXYLIC ACID; 5-AMINO-1H-PYRAZOLE-4-CARBOXYLIC ACID; 5-AMINO-1H-PYRROLE-2-CARBOXYLIC ACID; 5-AMINO-1-METHYL-1H-1,2,3-TRIAZOLE-4-CARBOXYLIC ACID; 5-AMINO-1-METHYL-1H-PYRAZOLE-3-CARBOXYLIC ACID; 5-AMINO-1-METHYL-1H-PYRAZOLE-4-CARBOXYLIC ACID; 5-AMINO-2-PYRAZINECARBOXYLIC ACID; 5-AMINO-2-PYRIDINECARBOXYLIC ACID; 5-AMINO-3-METHYL-1H-PYRAZOLE-4-CARBOXYLIC ACID; 5-AMINO-3-METHYL-ISOXAZOLE-4-CARBOXYLIC ACID; 5-AMINO-3-OXO-2,3-DIHYDRO-1H-PYRAZOLE-4-CARBOXYLIC ACID; 5-AMINO-4,5-DIHYDRO-3H-1,2,4-TRIAZOLE-3-CARBOXYLIC ACID; 5-AMINO-4H-[1,2,4]TRIAZOLE-3-CARBOXYLIC ACID MONOHYDRATE; 5-AMINO-4H-1,2,4-TRIAZOLE-3-CARBOXYLIC ACID; 5-AMINO-5-OXOPENTANOIC ACID; 5-AMINO-FURAN-2-CARBOXYLIC ACID; 5-AMINOLEVULINIC ACID; 5-AMINONICOTINIC ACID; 5-AMINOPENTANOIC ACID HYDRATE; 5-AMINO-PYRIDAZINE-4-CARBOXYLIC ACID; 5-AMINOPYRIMIDINE-2-CARBOXYLIC ACID; 5-AMINO-PYRIMIDINE-4-CARBOXYLIC ACID; 5-AMINOVALERIC ACID; 5-AZASPIRO[2.4]HEPTANE-1-CARBOXYLIC ACID; 5-AZIDO-PENTANOIC ACID; 5-CHLORO-1H-1,2,3-TRIAZOLE-4-CARBOXYLIC ACID; 5-CHLORO-1H-1,2,4-TRIAZOLE-3-CARBOXYLIC ACID; 5-CHLORO-1H-PYRAZOLE-3-CARBOXYLIC ACID; 5-CHLORO-1H-PYRAZOLE-4-CARBOXYLIC ACID; 5-CHLORO-2H-[1,2,4]TRIAZOLE-3-CARBOXYLIC ACID; 5-CHLORO-5-HEXENOIC ACID; 5-CHLOROFURAN-2-CARBOXYLIC ACID; 5-CHLORO-ISOXAZOLE-3-CARBOXYLIC ACID; 5-CHLOROVALERIC ACID; 5-CYANO-1H-PYRROLE-2-CARBOXYLIC ACID; 5-CYANO-2-FURANCARBOXYLIC ACID; 5-CYANO-3-PYRIDINECARBOXYLIC ACID; 5-CYANOPENTANOIC ACID; 5-CYANOPYRIDINE-2-CARBOXYLIC ACID; 5-ETHENYL-2-FURANCARBOXYLIC ACID; 5-ETHENYL-2-PYRIDINECARBOXYLIC ACID; 5-ETHENYL-3-PYRIDINECARBOXYLIC ACID; 5-ETHOXYPENTANOIC ACID; 5-ETHYL-1,2,4-OXADIAZOLE-3-CARBOXYLIC ACID; 5-ETHYL-1,3,4-OXADIAZOLE-2-CARBOXYLIC ACID; 5-ETHYL-1,3-OXAZOLE-4-CARBOXYLIC ACID; 5-ETHYL-1H-1,2,3-TRIAZOLE-4-CARBOXYLIC ACID; 5-ETHYL-1H-PYRAZOLE-3-CARBOXYLIC ACID; 5-ETHYL-1H-PYRAZOLE-4-CARBOXYLIC ACID; 5-ETHYL-4H-1,2,4-TRIAZOLE-3-CARBOXYLIC ACID; 5-ETHYL-FURAN-2-CARBOXYLIC ACID; 5-ETHYL-ISOXAZOLE-3-CARBOXYLIC ACID; 5-ETHYL-ISOXAZOLE-4-CARBOXYLIC ACID; 5-ETHYNYLPICOLINIC ACID; 5-FLUORO-2-THIOPHENECARBOXYLIC ACID; 5-FLUORO-3-THIOPHENECARBOXYLIC ACID; 5-FLUORO-L-PROLINE; 5-FLUORONICOTINIC ACID; 5-FLUOROPIPERIDINE-3-CARBOXYLIC ACID; 5-FLUOROPYRIDINE-2-CARBOXYLIC ACID; 5-FLUOROPYRIMIDINE-2-CARBOXYLIC ACID; 5-FORMYL-1H-PYRROLE-2-CARBOXYLIC ACID; 5-FORMYL-2-FURANCARBOXYLIC ACID; 5-HEXENOIC ACID; 5-HEXYNOIC ACID; 5H-TETRAAZOL-5-YLACETIC ACID; 5-HYDROXY-1,2,4-TRIAZINE-6-CARBOXYLIC ACID; 5-HYDROXY-1H-1,2,4-TRIAZOLE-3-CARBOXYLIC ACID; 5-HYDROXY-1H-PYRAZOLE-3-CARBOX-

YLIC ACID; 5-HYDROXY-1-METHYL-1H-PYRAZOLE-3-CARBOXYLIC ACID; 5-HYDROXY-2-PYRIMIDINECARBOXYLIC ACID; 5-HYDROXY-3-PIPERIDINECARBOXYLIC ACID; 5-HYDROXYFURAN-2-CARBOXYLIC ACID; 5-HYDROXYHEXANOIC ACID; 5-HYDROXY-L-NORVALINE; 5-HYDROXYMETHYL-1H-IMIDAZOLE-4-CARBOXYLIC ACID; 5-HYDROXYMETHYL-2-FURANCARBOXYLIC ACID; 5-HYDROXYNICOTINIC ACID; 5-HYDROXYPENTANOIC ACID; 5-HYDROXYPICOLINIC ACID; 5-HYDROXYPIPERIDINE-2-CARBOXYLIC ACID; 5-HYDROXYPYRAZINE-2-CARBOXYLIC ACID; 5-HYDROXYPYRAZINE-3-CARBOXYLIC ACID; 5-METHOXY-2-FUROIC ACID; 5-METHOXY-2-METHYLPENTANOIC ACID; 5-METHOXY-3-METHYLPENT-2-ENOIC ACID; 5-METHOXY-3-METHYLPENTANOIC ACID; 5-METHOXY-ISOXAZOLE-4-CARBOXYLIC ACID; 5-METHOXYPENTANOIC ACID; 5-METHYL-[1,3,4]OXADIAZOLE-2-CARBOXYLIC ACID; 5-METHYL-1,2,3-OXADIAZOLE-4-CARBOXYLIC ACID; 5-METHYL-1,2,3-THIADIAZOLE-4-CARBOXYLIC ACID; 5-METHYL-1,2,4-OXADIAZOLE-3-CARBOXYLIC ACID; 5-METHYL-1,3,4-THIADIAZOLE-2-CARBOXYLIC ACID; 5-METHYL-1,3-DIOXANE-5-CARBOXYLIC ACID; 5-METHYL-1,3-OXAZOLE-4-CARBOXYLIC ACID; 5-METHYL-1H-1,2,3-TRIAZOLE-4-CARBOXYLIC ACID; 5-METHYL-1H-IMIDAZOLE-2-CARBOXYLIC ACID; 5-METHYL-1H-IMIDAZOLE-4-CARBOXYLIC ACID; 5-METHYL-1H-PYRAZOLE-3-CARBOXYLIC ACID; 5-METHYL-1H-PYRAZOLE-4-CARBOXYLIC ACID; 5-METHYL-1H-PYRROLE-2-CARBOXYLIC ACID; 5-METHYL-1H-PYRROLE-3-CARBOXYLIC ACID; 5-METHYL-2-FUROIC ACID; 5-METHYL-2H-[1,2,4]TRIAZOLE-3-CARBOXYLIC ACID; 5-METHYL-2H-1,2,3-TRIAZOLE-4-CARBOXYLIC ACID; 5-METHYL-2-OXO-2,3-DIHYDRO-OXAZOLE-4-CARBOXYLIC ACID; 5-METHYL-2-PYRAZINECARBOXYLIC ACID; 5-METHYL-2-THIOPHENECARBOXYLIC ACID; 5-METHYL-3,4-DIHYDRO-2H-PYRROLE-2-CARBOXYLIC ACID; 5-METHYL-4H-1,2,4-TRIAZOLE-3-CARBOXYLIC ACID; 5-METHYL-4-HEXENOIC ACID; 5-METHYL-4-OXOHEXANOIC ACID; 5-METHYL-5-HEXENOIC ACID; 5-METHYLFURAN-3-CARBOXYLIC ACID; 5-METHYLHEPT-4-ENOIC ACID; 5-METHYLHEPTANOIC ACID; 5-METHYLHEXANOIC ACID; 5-METHYLISOTHIAZOLE-4-CARBOXYLIC ACID; 5-METHYLISOXAZOLE-3-CARBOXYLIC ACID; 5-METHYLISOXAZOLE-4-CARBOXYLIC ACID; 5-METHYLNICOTINIC ACID; 5-METHYLOXAZOLE-2-CARBOXYLIC ACID; 5-METHYLPICOLINIC ACID; 5-METHYLPROLINE; 5-METHYLPYRIDAZINE-4-CARBOXYLIC ACID; 5-METHYLPYRIMIDINE-2-CARBOXYLIC ACID; 5-METHYLPYRIMIDINE-4-CARBOXYLIC ACID; 5-METHYLTHIAZOLE-2-CARBOXYLIC ACID; 5-METHYLTHIAZOLE-4-CARBOXYLIC ACID; 5-METHYLTHIOPHENE-3-CARBOXYLIC ACID; 5-NORBORNENE-2-CARBOXYLIC ACID; 5-NORBORNENE-2-CARBOXYLIC ACID, PREDOMINANTLY ENDO; 5-OXASPIRO[2.4]HEPTANE-1-CARBOXYLIC ACID; 5-OXO-2,5-DIHYDRO-1H-1,2,4-TRIAZOLE-3-CARBOXYLIC ACID; 5-OXO-2,5-DIHYDRO-1H-PYRAZOLE-3-CARBOXYLIC ACID; 5-OXO-2-HEXENOIC ACID; 5-OXO-4,5-DIHYDRO-1H-[1,2,4]TRIAZOLE-3-CARBOXYLIC ACID; 5-OXO-4,5-DIHYDRO-1H-[1,2,4]TRIAZOLE-3-CARBOXYLIC ACID HYDRATE; 5-OXO-4,5-DIHYDRO-1H-PYRAZOLE-3-CARBOXYLIC ACID; 5-OXO-4,5-DIHYDROPYRAZINE-2-CARBOXYLIC ACID; 5-OXO-CYCLOHEX-1-ENECARBOXYLIC ACID; 5-OXO-HEPTANOIC ACID; 5-OXOPIPERAZINE-2-CARBOXYLIC ACID; 5-OXOPIPERIDINE-2-CARBOXYLIC ACID; 5-OXO-PYRROLIDINE-3-CARBOXYLIC ACID; 5-OXOTETRAHYDROTHIOPHENE-3-CARBOXYLIC ACID; 5-PYRIMIDINEACETIC ACID; 5-SULFANYLFURAN-2-CARBOXYLIC ACID; 5-SULFANYLPENTANOIC ACID; 5-THIAZOLEACETIC ACID; 6-AMINO-[1,2,4]TRIAZINE-5-CARBOXYLIC ACID; 6-AMINO-2,3,4,5-TETRAHYDRO-3-PYRIDINECARBOXYLIC ACID; 6-AMINO-6-OXO-HEXANOIC ACID; 6-AMINOCAPROIC ACID; 6-AMINONICOTINIC ACID; 6-AMINOPYRAZINE-2-CARBOXYLIC ACID; 6-AMINOPYRIDAZINE-3-CARBOXYLIC ACID; 6-AMINOPYRIDINE-2-CARBOXYLIC ACID; 6-AMINO-PYRIMIDINE-4-CARBOXYLIC ACID; 6-CYANONICOTINIC ACID; 6-CYANOPYRIDINE-2-CARBOXYLIC ACID; 6-ETHYNYLNICOTINIC ACID; 6-FLUORONICOTINIC ACID; 6-FLUOROPYRIDINE-2-CARBOXYLIC ACID; 6-HEPTENOIC ACID; 6-HEPTYNOIC ACID; 6-HYDROXYCAPROIC ACID; 6-HYDROXYNICOTINIC ACID; 6-HYDROXYPICOLINIC ACID; 6-HYDROXYPYRIDAZINE-3-CARBOXYLIC ACID; 6-HYDROXYPYRIMIDINE-4-CARBOXYLIC ACID; 6-MERCAPTOHEXANOIC ACID; 6-METHOXYHEXANOIC ACID; 6-METHYL-1,2,3,4-TETRAHYDROPYRIDINE-3-CARBOXYLIC ACID; 6-METHYL-2-PIPERIDINE CARBOXYLIC ACID; 6-METHYL-3,4-DIHYDRO-2H-PYRAN-5-CARBOXYLIC ACID; 6-METHYL-3-PIPERIDINECARBOXYLIC ACID; 6-METHYL-6-HEPTENOIC ACID; 6-METHYLHEPTANOIC ACID; 6-METHYLNICOTINIC ACID; 6-METHYLPICOLINIC ACID; 6-METHYLPYRAZINE-2-CARBOXYLIC ACID; 6-METHYLPYRIDAZINE-3-CARBOXYLIC ACID; 6-METHYLPYRIMIDINE-4-CARBOXYLIC ACID; 6-OXABICYCLO[3.1.0]HEXANE-3-CARBOXYLIC ACID; 6-OXO-1,4,5,6-TETRAHYDROPYRIDAZINE-3-CARBOXYLIC ACID; 6-OXO-1,6-DIHYDROPYRAZINE-2-CARBOXYLIC ACID; 6-OXO-1,6-DIHYDRO-PYRIDAZINE-3-CARBOXYLIC ACID; 6-OXO-1,6-DIHYDROPYRIDAZINE-4-CARBOXYLIC ACID; 6-OXO-1,6-DIHYDROPYRIDINE-2-CARBOXYLIC ACID; 6-OXO-1,6-DIHYDROPYRIDINE-3-CARBOXYLIC ACID; 6-OXO-1,6-DIHYDRO-PYRIMIDINE-5-CARBOXYLIC ACID; 6-OXO-3H-PYRIMIDINE-4-CARBOXYLIC ACID; 6-OXO-HEXAHYDRO-PYRIDAZINE-3-CARBOXYLIC ACID; 6-OXO-PIPERAZINE-2-CARBOXYLIC ACID; 6-OXO-PIPERIDINE-2-CARBOXYLIC ACID; 6-OXOPIPERIDINE-3-CARBOXYLIC ACID; 7-AMINOHEPTANOIC ACID; 7-HYDROXYHEPTANOIC ACID; 7-OCTENOIC ACID; 7-OXA-BICYCLO[2.2.1]HEPT-5-ENE-2-CARBOXYLIC ACID; 7-OXOHEPTANOIC ACID; AC-ALA-OH; AC-D-ALA-OH; ACETAMIDINE ACETATE; ACETATE BUFFER; ACETIC ACID; ACETIC ACID-ACETONITRILE; ACETIC ACID-AMMONIUM ACETATE; ACETOACETIC ACID; ACETONE CARBOXYMETHOXIME; ACETONITRILE WITH AMMONIUM ACETATE; ACETOXYACETIC ACID; ACETYL-D-2-AMINOBUTYRIC ACID; ACETYLENEDICARBOXYLIC ACID; ACETYLPYRUVIC ACID; ACONIC ACID; ACRYLAMIDO BUFFER; ACRYLATE, AMMONIUM; ACRYLIC ACID; ADIPIC ACID; A-FLUORO-B-ALANINE; ALA-GLY; ALANINE-

NH2 ACETATE SALT; ALANOSINE; ALBIZZIIN; ALFA-NITRO ACETIC ACID; ALLO-DL-3-THIOBUTYRINE; ALLO-O-ETHYL-D-THR; ALLYLMALONIC ACID; ALPHA-(METHYLAMINO)ISOBUTYRIC ACID; ALPHA-AMINO-2-CYCLOPENTENYLACETIC ACID; ALPHA-METHYL-D-ALLYLGLYCINE; ALPHA-METHYL-DL-SERINE; ALPHA-METHYL-D-PROPARGYLGLYCINE; ALPHA-METHYL-D-VALINE; ALPHA-METHYL-L-ALLYLGLYCINE; ALPHA-METHYL-L-ASP; ALPHA-METHYL-L-PROLINE; ALPHA-METHYL-L-PROPARGYLGLYCINE; AMINO-(1H-IMIDAZOL-2-YL)-ACETIC ACID; AMINO-(PYRROLIDIN-3-YL)-ACETIC ACID; AMINO-(TETRAHYDRO-FURAN-3-YL)-ACETIC ACID; AMINO-CYCLOPROPYL-ACETIC ACID; AMINO-FURAN-2-YL-ACETIC ACID; AMINO-FURAN-3-YL-ACETIC ACID; AMINOMALONIC ACID; AMINOOXY-ACETIC ACID, HYDROCHLORIDE SALT; AMINO-PYRROL-2-YL-ACETIC ACID; AMMONIUM ACETATE; AMMONIUM ACETATE BUFFER; AMMONIUM BENZOATE; AMMONIUM BIOXALATE MONOHYDRATE; AMMONIUM HYDROGEN MALEATE; AMMONIUM HYDROGEN SUCCINATE; AMMONIUM HYDROGENOXALATE HEMIHYDRATE; AMMONIUM ISOVALERATE; AMMONIUM LACTATE; AMMONIUM OXALATE; AMMONIUM OXALATE MONOHYDRATE; AMMONIUM PROPIONATE; AMMONIUM TRIFLUOROACETATE; ANGELIC ACID; ANTHRANILIC ACID; ATROPIC ACID; AZALEUCINE; AZEPANE-2-CARBOXYLIC ACID; AZEPANE-3-CARBOXYLIC ACID; AZEPANE-4-CARBOXYLIC ACID; AZETIDIN-3-YLACETIC ACID; AZETIDIN-3-YLIDENEACETIC ACID; AZETIDIN-3-YLIDENEACETIC ACID HYDROCHLORIDE; AZETIDINE-2-CARBOXYLIC ACID; AZETIDINE-2-CARBOXYLIC ACID HYDROCHLORIDE; AZETIDINE-3-CARBOXYLIC ACID; AZETIDINE-3-CARBOXYLIC ACID HYDROCHLORIDE; AZIRIDINE-2-CARBOXYLIC ACID; BENZOCYCLOBUTYL-1-CARBOXYLIC ACID; BENZOIC ACID; BENZOIC ACID, 2-ETHENYL-; BENZOIC ACID-12C7; BETA-ALANINE; BETA-ASPARTYL HYDRAZIDE; BETA-CHLORO-DL-ALANINE; BETA-CHLOROLACTIC ACID; BETA-CYANO-L-ALANINE; BETA-FLUOROLACTIC ACID; BETA-HOMOALANINE HYDROCHLORIDE; BETA-HYDROXYISOVALERIC ACID; BETA-HYDROXYLEUCINE; BETA-HYDROXYNORLEUCINE; BETA-HYDROXYNORVALINE; BETA-METHOXYVALINE; BETA-METHYLGUANADINOPROPIONIC ACID; BETA-METHYLLEVULINIC ACID; BETA-N,N-DIMETHYLAMINO-D-ALA; BETA-N,N-DIMETHYLAMINO-L-ALA; BETA-N-ETHANOLAMINO-D-ALA; BETA-N-ETHANOLAMINO-L-ALA; BETA-N-METHYLAMINO-D-ALA; BETA-T-BUTYL-D-ALANINE; BETA-THIOLNORVALINE; BICYCLO[2.2.1]HEPTANE-1-CARBOXYLIC ACID; BICYCLO[2.2.1]HEPTANE-2-CARBOXYLIC ACID; BICYCLO[3.1.0]HEX-2-ENE-6-CARBOXYLIC ACID; BICYCLO[3.1.0]HEXANE-3-CARBOXYLIC ACID; BICYCLO[3.2.0]HEPTANE-3-CARBOXYLIC ACID; BICYCLO[4.1.0]HEPTANE-7-CARBOXYLIC ACID; BICYCLO[4.2.0]OCTA-1(6),2,4-TRIENE-2-CARBOXYLIC ACID; BROMOACETIC ACID; BROMOPROPIOLIC ACID; BUTANOIC ACID, 2-AMINO-3-OXO-; BUTYRAMIDINE HOAC; BUTYRIC ACID; CARBAMIMIDOYL-ACETIC ACID; CARBAMOYL-DL-ALA-OH; CARBOXYMETHYLNITROSOUREA; CHLOROACETIC ACID; CHLORODIFLUOROACETIC ACID; CHLOROFLUOROACETIC ACID; CIS,CIS-MUCONIC ACID; CIS-2-AMINO-1-CYCLOHEXANECARBOXYLIC ACID; CIS-2-AMINO-1-CYCLOPENTANECARBOXYLIC ACID; CIS-2-AMINO-2-METHYL-CYCLOPENTANECARBOXYLIC ACID; CIS-2-AMINO-4-CYCLOHEXENE-1-CARBOXYLIC ACID; CIS-2-AMINO-CYCLOHEX-3-ENECARBOXYLIC ACID; CIS-2-FLUORO-CYCLOPROPANECARBOXYLIC ACID; CIS-2-HYDROXY-1-CYCLOPENTANECARBOXYLIC ACID; CIS-2-METHYLCYCLOPROPANECARBOXYLIC ACID; CIS-3-(1H-IMIDAZOL-4-YL)-2-PROPENOIC ACID; CIS-3-AMINOCYCLOBUTANECARBOXYLIC ACID; CIS-3-AMINOCYCLOHEXANECARBOXYLIC ACID; CIS-3-AMINO-TETRAHYDROPYRAN-4-CARBOXYLIC ACID; CIS-3-CHLOROACRYLIC ACID; CIS-3-CHLOROCYCLOBUTANECARBOXYLIC ACID; CIS-3-FLUOROCYCLOBUTANECARBOXYLIC ACID; CIS-3-HEXENOIC ACID; CIS-3-HYDROXYCYCLOBUTANECARBOXYLIC ACID; CIS-3-HYDROXY-DL-PROLINE; CIS-3-METHYL-2-HEXENOIC ACID; CIS-3-METHYL-CYCLOBUTANEACETIC ACID; CIS-3-METHYLCYCLOBUTANECARBOXYLIC ACID; CIS-4-AMINOCROTONIC ACID; CIS-4-AMINOCYCLOHEXANECARBOXYLIC ACID; CIS-4-HYDROXYCYCLOHEXANECARBOXYLIC ACID; CIS-4-HYDROXY-DL-PROLINE; CIS-4-HYDROXY-D-PROLINE; CIS-4-HYDROXY-L-PROLINE; CIS-4-HYDROXY-TETRAHYDRO-2-FUROIC ACID; CIS-4-MERCAPTO-L-PROLINE; CIS-AZETIDINE-2,4-DICARBOXYLIC ACID; CIS-CYCLOBUTANE-1,2-DICARBOXYLIC ACID; CIS-CYCLOBUTANE-1,3-DICARBOXYLIC ACID; CIS-EPOXYSUCCINIC ACID; CIS-L-3-HYDROXYPROLINE; CITRACONIC ACID; COMANIC ACID; COUMALIC ACID; CREATINE; CROTONIC ACID; CROTYL GLYCINE; CYANO(METHOXYIMINO)ACETIC ACID; CYANO(METHOXYIMINO)ACETIC ACID; CYANOACETIC ACID; CYANOACRYLIC ACID; CYCLOBUTANE-1,1-DICARBOXYLIC ACID MONOAMIDE; CYCLOBUTANE-1,3-DICARBOXYLIC ACID; CYCLOBUTANECARBOXYLIC ACID; CYCLOBUTANEPROPANOIC ACID; CYCLOBUTYL-ACETIC ACID; CYCLOBUTYLIDENEACETIC ACID; CYCLOBUTYL-OXO-ACETIC ACID; CYCLOBUTYLPROPIONIC ACID; CYCLOCREATINE; CYCLOHEPTANECARBOXYLIC ACID; CYCLOHEXANECARBOXYLIC ACID; CYCLOHEXYLACETIC ACID; CYCLOLEUCINE; CYCLOPENTANECARBOXYLIC ACID; CYCLOPENTENYL ACETIC ACID; CYCLOPENTYLACETIC ACID; CYCLOPROPANE-1,2-DICARBOXYLIC ACID; CYCLOPROPANECARBOXYLIC ACID; CYCLOPROPANECARBOXYLIC ACID HYDRAZINE; CYCLOPROPANECARBOXYLIC ACID, 1-AMINO-2-ETHENYL-, (1R,2S)-; CYCLOPROPANECARBOXYLIC ACID, 2-(CHLOROCARBONYL)-, TRANS-; CYCLOPROPYLACETIC ACID; CYCLOPROPYL-HYDROXYIMINO-ACETIC ACID; CYCLOPROPYLIDENE-ACETIC ACID; D(−)-ISOVALINE; D-(+)-MALIC ACID; D,L-2-AMINO-3-(HYDROXY-15N2-AMINO)PROPIONIC ACID; D,L-2-AMINO-3-(HYDROXYAMINO)PROPIONIC ACID; D,L-ALANOSINE; D-2,3-DIAMINOPROPIONIC ACID; D-2,4-DIAMINOBUTYRIC ACID; D-2-AMINO-5-METHYLHEX-4-ENOIC ACID; D-2-AMINOBUTYRIC ACID; D-2-AZIRIDINECARBOXYLIC ACID; D-2-

HYDROXYPENTANEDIOIC ACID; D-3-METHYLASPARTIC ACID; D-3-THIOBUTYRINE; D-3-THIOLNORVALINE; D-6-HYDROXYNORLEUCINE; D-6-OXO-PIPECOLINIC ACID; D-ALA-3-CL; D-ALANINE; D-ALBIZZIIN; D-ALLOISOLEUCINE; D-ALLYLGLYCINE; D-ALPHA-HYDROXYISOVALERIC ACID; D-ASPARAGINE; D-ASPARTIC ACID; D-ASPARTIC ACID BETA-HYDROXAMATE; D-ASPARTIC ACID-BETA-METHYL ESTER; D-AZETIDINE-2-CARBOXYLIC ACID; D-BETA,BETA-DIETHYLALANINE; D-BETA-HOMOSERINE; D-CANALINE; D-CYCLOBUTYLALANINE; D-CYCLOBUTYLGLYCINE; D-CYCLOPENTYLGLYCINE; D-CYCLOPROPYLALANINE; D-CYCLOPROPYLGLYCINE; D-CYSTEINE; D-D-HYDROXYNORVALINE; D-GLUTAMIC ACID; D-GLUTAMINE; D-GLYCERIC ACID; D-HOMOCYSTEINE; D-HOMOSERINE; DICHLOROACETIC ACID; DICHLOROFLUOROACETIC ACID; DIETHYLAMINE ACETATE; DIETHYLAMINO-ACETIC ACID; DIFLUOROACETIC ACID; DIFLUOROMETHYLTHIOACETIC ACID; DIFLUORO-PROPANEDIOIC ACID; DIGLYCOLIC ACID; DIHYDROXYACETIC ACID; DIHYDROXYFUMARIC ACID; DIMETHYLMALONIC ACID; D-ISOASPARAGINE; D-ISOGLUTAMINE; D-ISOLEUCINE; D-ISOTHREONINE; DL-2,3-DIAMINOPROPIONIC ACID HYDROCHLORIDE; DL-2,3-DIAMINOSUCCINIC ACID; DL-2-AMINO-4-PENTENOIC ACID; DL-2-AMINOBUTYRIC ACID; DL-2-FLUORO-3-ALANINE; DL-2-HYDROXY-N-BUTYRIC ACID; DL-2-ISOPROPYLSERINE; DL-3-AMINOBUTYRIC ACID; DL-3-AMINOISOBUTYRIC ACID; DL-3-METHYLASPARTIC ACID; DL-3-THIOBUTYRINE; DL-4-AMINO-2-FLUOROBUTYRIC ACID; DL-4-AMINO-3-HYDROXYBUTYRIC ACID; DL-6-HYDROXYNORLEUCINE; D-LACTIC ACID; DL-ALANINE; DL-ALANYL-GLYCINE; DL-ALLO-ISOLEUCINE; DL-ALLO-THREONINE; DL-ALPHA-HYDROXYCAPROIC ACID; DL-ALPHA-METHYLLEUCINE; DL-ASPARAGINE; DL-ASPARTIC ACID; DL-BETA-HYDROXYNORVALINE; DL-CIS-4-FLUORO-5-PYRROLIDONE-2-CARBOXYLIC ACID; DL-CITRAMALIC ACID; DL-CYCLOBUTYLALANINE; DL-CYCLOBUTYLGLYCINE; DL-CYCLOPENTYLGLYCINE; DL-CYCLOPROPYLALANINE; DL-CYSTEINE; D-LEUCINE; DL-GLUTAMIC ACID; DL-GLUTAMIC ACID ALPHA-AMIDE; DL-GLUTAMINE; DL-GLYCERIC ACID; DL-HOMOCYSTEINE; DL-HOMOLEUCINE; DL-HOMOSERINE; DL-ISOLEUCINE; DL-ISOSERINE; DL-LEUCIC ACID; DL-LEUCINE; DL-LYSINE; DL-MALIC ACID; DL-METHIONINE; DL-METHYLTARTRONIC ACID; DL-NORLEUCINE; DL-NORVALINE; DL-O-METHYLSERINE; DL-ORNITHINE; DL-PENICILLAMINE; DL-PIPECOLINIC ACID; DL-PROLINE; DL-PROPARGYLGLYCINE; DL-PYROGLUTAMIC ACID; DL-SERINE; DL-S-METHYL-CYS-OH; DL-TERT-LEUCINE; DL-THREO-BETA-HYDROXYASPARTIC ACID; DL-THREONINE; DL-TRANS-2,6-DIAMINO-4-HEXENOIC ACID; DL-TRANS-4-FLUORO-5-PYRROLIDONE-2-CARBOXYLIC ACID; DL-TRANS-HYDROXYPROLINE; DL-VALINE; D-LYSINE; D-METHALLYLGLYCINE; D-METHIONINE; D-NORLEUCINE; D-NORVALINE; D-ORNITHINE; D-PENICILLAMINE; D-PROLINE; D-PROPARGYLGLYCINE; D-PYROGLUTAMIC ACID; D-SERINE; D-S-METHYL-CYS-OH; D-TERT-LEUCINE; D-THIAZOLIDINE-4-CARBOXYLIC ACID; D-THREONINE; D-TRANS-4-FLUORO-5-PYRROLIDONE-2-CARBOXYLIC ACID; D-VALINE; D-VINYLGLYCINE; EPOXY METHACRYLATE; ERYTHRO-BETA-HYDROXY-L-ASPARTIC ACID; ERYTHRO-DL-BETA-HYDROXYNORLEUCINE; ERYTHRO-DL-BETA-HYDROXYNORVALINE; ETHOXYACETIC ACID; ETHOXYMETHYLENECYANOACETIC ACID; ETHYL HYDROGEN MALONATE; ETHYLMALONIC ACID; FLUOROACETIC ACID; FOR-D-ALA-OH; FOR-D-VAL-OH; FORMIMINOGLYCINE; FUMARIC ACID; FUMARIC ACID MONOETHYL ESTER; FURAN-3-YL-ACETIC ACID; GABA; GABACULINE; GAMMA-ACETYLENIC GABA; GAMMA-CHLORO-ALPHA-AMINOBUTYRIC ACID; GAMMA-METHYL-L-LEUCINE; GAMMA-METHYLPROLINE; GLUTACONIC ACID; GLUTARIC ACID; GLYCINE; GLYCINE AMIDE ACETATE; GLYCINE HYDROCHLORIDE; GLYCOLIC ACID; GLYCYLDEHYDROALANINE; GLYCYL-DL-ALANINE; GLYCYLGLYCINE; GLYCYL-L-ALANINE; GLYCYL-SARCOSINE; GLY-D-ALA; GLYOXILIC ACID OXIME; GLYOXYLIC ACID; GLYOXYLIC ACID MONOHYDRATE; GLYOXYLIC ACID SEMICARBAZONE; GUANIDINE ACETATE; GUANIDINE OXALATE; HADACIDIN; H-ALPHA-ME-D-LEU-OH; H-ALPHA-ME-DL-VAL-OH; H-ALPHA-ME-LEU-OH; H-ASP-NH2; H-ASP-OME; H-BETA-ALA-GLY-OH; HCL/ACOH; H-D-ALA-GLY-OH; H-D-ALLO-THR-OH; H-D-ASP-OME; H-D-DAP-OH HCL; H-DL-ASP-OME; H-DL-GLU-OH; H-DL-MELEU-OH; H-D-MEALA-OH HCL; H-D-PRA-OH HCL; H-D-SER(AC)-OH; H-D-THR(ME)-OH; HEPT-4-EN-6-YNOIC ACID; HEPT-5-ENOIC ACID; HEPTA-4,6-DIENOIC ACID; HEPTANOIC ACID; HEXA-4,5-DIENOIC ACID; HEXAHYDROPYRIDAZINE-3-CARBOXYLIC ACID; HEXAHYDROPYRIMIDINE-2-CARBOXYLIC ACID; HEXANOIC ACID; H-GLU-2-CHLOROTRITYL RESIN; H-GLY-BETA-ALA-OH; H-L-DAB-OH; H-MEILE-OH; H-MEVAL-OH; H-PRA-OH HCL; HYDANTOIC ACID; HYDRAZINE ACETATE; HYDRAZINE MONOOXALATE; HYDROCHLORIC ACID-PROPIONIC ACID; HYDROXYIMINO-ACETIC ACID; HYDROXYLAMINE ACETATE; HYPOGLYCIN; IMIDAZOL-1-YL-ACETIC ACID; IMIDAZOLE-4-ACETIC ACID; IMINODIACETIC ACID; IMMOBILIZED IMINODIACETIC ACID; ISOBUTYL ACRYLIC ACID; ISOBUTYRIC ACID; ISOCROTONIC ACID; ISONICOTINIC ACID; ISONICOTINIC ACID N-OXIDE; ISONIPECOTIC ACID; ISOPROPOXYACETIC ACID; ISOPROPYLMALONIC ACID; ISOTHIAZOLE-3-CARBOXYLIC ACID; ISOTHIAZOLE-5-CARBOXYLIC ACID; ISOVALERIC ACID; ISOXAZOLE-4-CARBOXYLIC ACID; ISOXAZOLE-5-CARBOXYLIC ACID; ITACONIC ACID; ITACONIC ACID MONOMETHYL ESTER; KETOMALONIC ACID; KETOMALONIC ACID MONOHYDRATE; L-(−)-MALIC ACID; L-(−)-THREO-3-HYDROXYASPARTIC ACID; L-(+)-LACTIC ACID; L-2,3-DIAMINOPROPIONIC ACID; L-2-ACETAMIDOBUTYRIC ACID; L-2-AMINO-5-METHYLHEX-4-ENOIC ACID; L-2-AMINOADIPATE 6-SEMIALDEHYDE; L-2-AMINOBUTYRIC ACID; L-2-AMINOBUTYRIC ACID HYDROCHLORIDE; L-2-AZIRIDINECARBOXYLIC ACID; L-2-METHYLCYSTEINE; L-2-OXOTHIAZOLIDINE-4-CARBOXYLIC ACID; L-3-METHYLASPARTIC ACID; L-3-THIOBUTYRINE; L-3-THIOLNORVALINE; L-6-HYDROXYNORLEUCINE; LACTIC ACID; L-ALANINE; L-ALANINE HYDROCHLORIDE; L-ALLO-ISOLEUCINE; L-ALLO-THREONINE; L-ALLYLGLYCINE; L-ASPARAGINE; L-ASPARTIC ACID; L-ASPARTIC ACID BETA-HYDROXAMATE; L-ASPARTIC ACID-

AGAROSE; L-AZETIDINE-2-CARBOXYLIC ACID; L-AZETIDINE-2-CARBOXYLIC ACID HCL; L-BETA, BETA-DIETHYLALANINE; L-BETA-HOMOALANINE HYDROCHLORIDE; L-BETA-HOMOSERINE; L-BETA-HOMOTHREONINE; L-CANALINE; L-CYCLOBUTYL-ALANINE; L-CYCLOBUTYLGLYCINE; L-CYCLOPENTYLGLYCINE; L-CYCLOPROPYLALANINE; L-CYCLOPROPYLGLYCINE; L-CYSTEINE; LEVULINIC ACID; L-GLUTAMIC ACID; L-GLUTAMINE; L-HOMOCYSTEINE; L-HOMOSERINE; L-HYDROXY-PROLINE; L-ISOGLUTAMINE; L-ISOLEUCINE; L-ISOTHREONINE; L-ISOVALINE; LITHIUM SUCCINATE; L-LEUCIC ACID; L-LEUCINE; L-LYSINE; L-METHIONINE; L-NORLEUCINE; L-NORVALINE; L-ORNITHINE; L-PENICILLAMINE; L-PIPECOLIC ACID; L-PROLINE; L-PROLINE HYDRATE; L-PROPARGYLGLYCINE; L-PYROGLUTAMIC ACID; L-SERINE; L-SERINE [G-3 H]; L-SERINE HYDROCHLORIDE; L-TERT-LEUCINE; L-THIAZOLIDINE-4-CARBOXYLIC ACID; L-THREONIC ACID; L-THREONINE; L-THREONINE-AGAROSE; L-TRANS-4-FLUORO-5-PYRROLIDONE-2-CARBOXYLIC ACID; L-VALINE; L-VINYLGLYCINE; MALEAMIC ACID; MALEIC ACID; MALEIC ACID MONOETHYL ESTER; MALEIC ACID MONOMETHYL ESTER; MALEIC ACID MONOSODIUM SALT; MALONIC ACID; MERCAPTOACETIC ACID; MESACONIC ACID; MESO-2,3-DIAMINOSUCCINIC ACID; MESO-2,3-DIMETHYLSUCCINIC ACID; METHACRYLATE, AMMONIUM; METHACRYLIC ACID; METHANESULFONYLACETIC ACID; METHOXYACETIC ACID; METHOXYCARBONYLOXY-ACETIC ACID; METHYL HYDROGEN GLUTARATE; METHYLMALONIC ACID; METHYLSUCCINIC ACID; MONO-AMMONIUM CITRACONATE; MONOMETHYL AMINOMALONATE; MONOMETHYL FUMARATE; MONOMETHYL MALONATE; MONOMETHYL SUCCINATE; MORPHOLIN-3-YL-ACETIC ACID; MORPHOLIN-4-YL-ACETIC ACID; MORPHOLINE-2-CARBOXYLIC ACID; M-TOLUIC ACID; N-(1-CYANO-1-METHYLETHYL)GLYCINE; N-(2-AMINO-ETHYL)GLYCINE; N-(2CT RESIN)-L-MET-OH; N-(2-CYANOETHYL)-ALANINE; N-(2-CYANOETHYL)GLYCINE; N-(4-AMINOBUTYL)-GLYCINE; N-(TERT-BUTYL)HYDROXYLAMINE ACETATE; N,N-DIMETHYL(2-HYDROXYETHYL)AMMONIUM ACETATE; N,N-DIMETHYLGLYCINE; N,N-DIMETHYLGLYCINE HYDROCHLORIDE; N,N-DIMETHYL-L-ALA-OH; N,N-DIMETHYL-L-VALINE; N,N-DIMETHYLOXAMIC ACID; N,N-DIMETHYLSUCCINAMIC ACID; N,N-DIMETHYLVALINE; N-[(DIMETHYL-AMINO)CARBONYL]GLYCINE; N-ACETYL-BETA-ALANINE; N-ACETYL-DL-ALANINE; N-ACETYL-DL-SERINE; N-ACETYLGLYCINE; N-ACETYL-L-SERINE; N-ALPHA-METHYL-L-2-AMINO PENTANOIC ACID; N-ALPHA-METHYL-L-2-AMINO-CAPROIC ACID; N-ALPHA-METHYL-L-ALANINE HYDROCHLORIDE; N-ALPHA-METHYL-L-THREONINE; N-AMINO-D-PROLINE; N-CARBAMYL-ALPHA-AMINO-ISOBUTYRIC ACID; N-ETHYLGLYCINE; N-ETHYL-L-PROLINE; N-ETHYLMALEAMIC ACID; N-FORMYL CYSTEINE; N-FORMYL-DL-2-AMINO-N-BUTYRIC ACID; N-FORMYL-DL-ALANINE; N-FORMYL-DL-VALINE; N-FORMYLGLYCINE; N-FORMYL-L-ALANINE; N-FORMYL-L-PROLINE; N-FORMYL-L-VALINE; NH2-L-ILE-OH; NH2-L-LEU-OH; NH2-L-PRO-OH; NICOTINIC ACID; NICOTINIC ACID N-OXIDE; NIPECOTIC ACID; N-ISOPROPYL-N-METHYLGLYCINE; NITRAMINOACETIC ACID; N-ME-CIS-HYDROXY-PROLINE; N-ME-DL-VAL-OH; N-METHACRYLOYLGLYCINE; N-METHYL-2-METHYLENE-SUCCINAMIC ACID; N-METHYL-D-ALANINE; N-METHYL-D-ASPARTIC ACID; N-METHYL-D-ISOLEUCINE; N-METHYL-DL-ALANINE; N-METHYL-DL-ASPARTIC ACID; N-METHYL-DL-ISOLEUCINE; N-METHYL-D-PROLINE MONOHYDRATE; N-METHYLHYDROXYLAMINE OXALATE; N-METHYLIMINODIACETIC ACID; N-METHYL-L-ALANINE; N-METHYL-L-ASPARTIC ACID; N-METHYL-L-CYSTEINE; N-METHYL-L-LEUCINE; N-METHYL-L-PROLINE; N-METHYL-L-PROLINE MONOHYDRATE; N-METHYL-L-SERINE; N-METHYLMALEAMIC ACID; N-METHYLSUCCINAMIC ACID; N-NITROSARCOSINE; N-NITROSO-D-PROLINE; N-NITROSO-L-AZETIDINE-2-CARBOXYLIC ACID; N-NITROSO-L-PROLINE; N-NITROSO-N-METHYL-3-AMINOPROPIONIC ACID; N-NITROSO-N-METHYL-4-AMINOBUTYRIC ACID; N-NITROSOSARCOSINE; NORVALINE, 4-OXO-; N-OXALYLGLYCINE; N-PROPIONYLALANINE; N-PROPIONYLGLYCINE; O-(AMINOCARBONYL)SERINE; O-ACETYL-L-SERINE; OCTANOIC ACID; O-METHYLISOUREA ACETATE; O-METHYL-L-THREONINE; O-TBU-(S)-LACTIC ACID; O-TOLUIC ACID; OXALACETIC ACID; OXALIC ACID; OXALIC ACID DIHYDRATE; OXALIC ACID MONO-(N-METHYL)-AMIDE; OXALYL MONOGUANYLHYDRAZIDE; OXALYSINE; OXAMIC ACID; OXAMIC ACID AMMONIUM SALT; OXAZOLE-2-CARBOXYLIC ACID; OXAZOLE-5-CARBOXYLIC ACID; OXETANE-2-CARBOXYLIC ACID; OXETANE-2-CARBOXYLIC ACID AMMONIASALT; OXETANE-3-CARBOXYLIC ACID; OXETIN; OXIRANE-(2S,3S)-DICARBOXYLIC ACID MONOMETHYL ESTER; OXIRANE-2,3-DICARBOXYLIC ACID; OXIRANE-2,3-DICARBOXYLIC ACID MONOMETHYL ESTER; OXO(PROPYLAMINO)ACETIC ACID; OXO-PYRROLIDIN-1-YL-ACETIC ACID; PENT-3-YNOIC ACID; PEROXYMALEIC ACID; PHENYLACETIC ACID; PHENYLPROPIOLIC ACID; PHOSPHONOACETIC ACID; PICOLINIC ACID; PICOLINIC ACID N-OXIDE; PICOLINIC ACID, [3H]-; PIPERAZIN-1-YL-ACETIC ACID; PIPERAZIN-2-YLACETIC ACID; PIPERAZINE-2-CARBOXYLIC ACID; PIPERIDAZINE-3-(R)-CARBOXYLIC ACID; PIPERIDIN-1-YL-ACETIC ACID; PIPERIDIN-4-YLACETIC ACID; PIPERIDIN-4-YLIDENE-ACETIC ACID; PIPERIDINIUM ACETATE; PIVALIC ACID; POTASSIUM BINOXALATE; PROPANEDIOIC ACID MONOPOTASSIUM SALT; PROPANOIC ACID, 2-HYDRAZINO-2-METHYL-; PROPIOLIC ACID; PROPIONIC ACID; PROPYLMALONIC ACID; P-TOLUIC ACID; PYRIDAZIN-4-YLACETIC ACID; PYRIDAZINE-3-CARBOXYLIC ACID; PYRIDAZINE-4-CARBOXYLIC ACID; PYRIDINE 2-CARBOXYLIC ACID, [CARBOXY-14C]; PYRIDINIUM ACETATE; PYRIMIDINE-2-CARBOXYLIC ACID; PYRIMIDINE-4-CARBOXYLIC ACID; PYRIMIDINE-5-CARBOXYLIC ACID; PYRROLE-2-CARBOXYLIC ACID; PYRROLE-3-CARBOXYLIC ACID; PYRROLE-3-CARBOXYLIC ACID HYDRATE; PYRROLIDIN-1-YL-ACETIC ACID; PYRROLIDINE-3-CARBOXYLIC ACID; PYRUVIC ACID; R-2-AMINOBUTYRIC ACID [CARBOXYL-14C]; R-2-AMINOHEPTANOIC ACID; S-2-AMINOBUTYRIC ACID [CARBOXYL-14C]; S-2-AMINOHEPTANOIC ACID; S-2-CHLOROVALERIC ACID; S-ACETYLTHIOACETIC ACID; SALICYLIC ACID; SARCOSINE; SAR-GLY-OH;

S-CYANOCYSTEINE; S-ETHYL-L-CYSTEINE; S-HYPOGLYCINE A; SIGLURE ACID; S-METHYL-L-CYSTEINE; SODIUM ACID OXALATE; SODIUM HYDROGEN FUMARATE; SODIUM HYDROGEN OXALATE; SORBIC ACID; SPIRO[2.2]PENTANE-1-CARBOXYLIC ACID; SPIRO[2.3]HEXANE-1-CARBOXYLIC ACID; SPIRO[2.4]HEPTANE-1-CARBOXYLIC ACID; SQUARAIN-CARBOXYLATE; SUCCINAMIC ACID; SUCCINIC ACID; SUCCINIC ACID MONOSODIUM SALT; SUCCINIC SEMIALDEHYDE; SULFOACETIC ACID; TARTRONIC ACID; TERT-BUTOXY ACETIC ACID; TETRAHYDRO-2H-PYRAN-3-CARBOXYLIC ACID; TETRAHYDRO-2H-PYRAN-3-YLACETIC ACID; TETRAHYDRO-2H-PYRAN-4-CARBOXYLIC ACID; TETRAHYDRO-2H-THIOPYRAN-3-CARBOXYLIC ACID; TETRAHYDRO-3-FUROIC ACID; TETRAHYDRO-5-OXO-2-FURANCARBOXYLIC ACID; TETRAHYDROPYRANYL-4-ACETIC ACID; TETRAHYDROTHIOPHENE-2-CARBOXYLIC ACID; TETRAHYDROTHIOPHENE-3-CARBOXYLIC ACID; TETRAHYDROTHIOPYRAN-4-CARBOXYLIC ACID; THIAZOL-2-YL-ACETIC ACID; THIAZOLE-2-CARBOXYLIC ACID; THIAZOLE-4-CARBOXYLIC ACID; THIAZOLE-5-CARBOXYLIC ACID; THIAZOLIDINE-2-CARBOXYLIC ACID; THIAZOLIDINE-4-CARBOXYLIC ACID; THIOMORPHOLINE-2-CARBOXYLIC ACID; THIOMORPHOLINE-3-CARBOXYLIC ACID; THREO-D-BETA-HYDROXYNORLEUCINE; THREO-DL-BETA-HYDROXYNORLEUCINE; THREO-DL-BETA-HYDROXYNORVALINE; THREO-L-BETA-HYDROXYNORLEUCINE; THREONINE, L-[14C(U)]; TIGLIC ACID; TRANS,TRANS-MUCONIC ACID; TRANS-2,4-PENTADIENOIC ACID; TRANS-2-AMINO-1-CYCLOHEXANECARBOXYLIC ACID; TRANS-2-AMINO-4-CYCLOHEXENE-1-CARBOXYLIC ACID; TRANS-2-AMINO-CYCLOPENTANECARBOXYLIC ACID; TRANS-2-BUTENE-1,4-DICARBOXYLIC ACID; TRANS-2-CHLOROMETHYL-1-CYCLOPROPANECARBOXYLIC ACID; TRANS-2-FLUORO-CYCLOPROPANECARBOXYLIC ACID; TRANS-2-HEXENOIC ACID; TRANS-2-HYDROXYMETHYL-1-CYCLOPROPANECARBOXYLIC ACID; TRANS-2-OCTENOIC ACID; TRANS-2-PENTENOIC ACID; TRANS-3-AMINOCYCLOBUTANECARBOXYLIC ACID; TRANS-3-CHLOROACRYLIC ACID; TRANS-3-CHLOROCYCLOBUTANECARBOXYLIC ACID; TRANS-3-FLUOROCYCLOBUTANECARBOXYLIC ACID; TRANS-3-HEXENOIC ACID; TRANS-3-HYDROXYCYCLOBUTANECARBOXYLIC ACID; TRANS-3-HYDROXYHEPT-4-ENOIC ACID; TRANS-3-HYDROXYHEX-4-ENOIC ACID; TRANS-3-HYDROXY-L-PROLINE; TRANS-3-METHYLCYCLOBUTANEACETIC ACID; TRANS-3-METHYLCYCLOBUTANECARBOXYLIC ACID; TRANS-4-AMINOCROTONIC ACID HYDROCHLORIDE; TRANS-4-AMINOCYCLOHEXANECARBOXYLIC ACID; TRANS-4-HYDROXYCYCLOHEXANECARBOXYLIC ACID; TRANS-4-HYDROXY-D-PROLINE; TRANS-4-HYDROXY-TETRAHYDRO-2-FUROIC ACID; TRANS-4-METHYLCYCLOHEXANECARBOXYLIC ACID; TRANS-CINNAMIC ACID; TRANS-CYCLOBUTANE-1,2-DICARBOXYLIC ACID; TRANS-CYCLOBUTANE-1,3-DICARBOXYLIC ACID; TRIFLUOROACETIC ACID; TRIMETHYLAMMONIUM ACETATE; TRIMETHYLPYRUVIC ACID; UROCANIC ACID; VALERIC ACID; VALPROIC ACID; VIGABATRIN; VINYLACETIC ACID

List No. 5—Carboxylic Acids Aldehydes ((2-FORMYL-3-THIENYL)THIO)ACETIC ACID; ([2-(2-FORMYLPHENOXY)ETHYL]THIO)ACETIC ACID; ([2-(4-FORMYL-2-METHOXYPHENOXY)ETHYL]THIO)ACETIC ACID; ([2-(4-FORMYLPHENOXY)ETHYL]THIO)ACETIC ACID; ([3-(2-FORMYLPHENOXY)PROPYL]THIO)ACETIC ACID; ([3-(4-FORMYLPHENOXY)PROPYL]THIO)ACETIC ACID; ([4-(2-FORMYL-1H-PYRROL-1-YL)PHENYL]THIO)ACETIC ACID; ([4-FORMYL-3-METHYL-1-(4-METHYLBENZYL)-1H-PYRAZOL-5-YL]THIO)ACETIC ACID; (2-BROMO-4-CHLORO-6-FORMYLPHENOXY)ACETIC ACID; (2-BROMO-4-FORMYL-6-METHOXYPHENOXY)ACETIC ACID; (2-BROMO-4-FORMYLPHENOXY)ACETIC ACID; (2-BROMO-6-CHLORO-4-FORMYLPHENOXY)ACETIC ACID; (2-BROMO-6-ETHOXY-4-FORMYLPHENOXY)ACETIC ACID; (2-CHLORO-4-FORMYL-6-METHOXYPHENOXY)ACETIC ACID; (2-CHLORO-4-FORMYLPHENOXY)ACETIC ACID; (2-CHLORO-6-ETHOXY-4-FORMYLPHENOXY)ACETIC ACID; (2E)-2,3-DIBROMO-4-OXOBUT-2-ENOIC ACID; (2-ETHOXY-4-FORMYLPHENOXY)ACETIC ACID; (2-ETHOXY-6-FORMYLPHENOXY)ACETIC ACID; (2-FORMYL-1H-PYRROL-1-YL)(PHENYL)ACETIC ACID; (2-FORMYL-1H-PYRROL-1-YL)ACETIC ACID; (2-FORMYL-6-METHOXY-4-NITROPHENOXY)ACETIC ACID; (2-FORMYL-IMIDAZOL-1-YL)-PHENYL-ACETIC ACID; (2R)-2-AMINO-2-(3-FORMYL-2-HYDROXY-5-METHYLPHENYL)ACETIC ACID; (2R)-2-AMINO-2-(4-[(4-FORMYLPHENYL)METHYL]PHENYL)ACETIC ACID; (2R)-2-AMINO-2-(4-[(4-FORMYLPHENYL)METHYL]PHENYL)PROPANOIC ACID; (2R)-2-AMINO-2-(4-FORMYL(2-PYRIDYL))ACETIC ACID; (2R)-2-AMINO-2-(4-FORMYL(2-PYRIDYL))PROPANOIC ACID; (2R)-2-AMINO-2-(5-FORMYL(2-PYRIDYL))ACETIC ACID; (2R)-2-AMINO-2-(5-FORMYL(2-PYRIDYL))PROPANOIC ACID; (2R)-2-AMINO-2-(5-FORMYL(3-PYRIDYL))ACETIC ACID; (2R)-2-AMINO-2-(5-FORMYL(3-PYRIDYL))PROPANOIC ACID; (2R)-2-AMINO-2-(6-AMINO-5-FORMYL(3-PYRIDYL))ACETIC ACID; (2R)-2-AMINO-2-(6-AMINO-5-FORMYL(3-PYRIDYL))PROPANOIC ACID; (2R)-2-AMINO-2-(6-FORMYL(2-PYRIDYL))ACETIC ACID; (2R)-2-AMINO-2-(6-FORMYL(2-PYRIDYL))PROPANOIC ACID; (2R)-2-AMINO-2-(6-FORMYL(3-PYRIDYL))ACETIC ACID; (2R)-2-AMINO-2-(6-FORMYL(3-PYRIDYL))PROPANOIC ACID; (2R)-2-AMINO-2-(6-FORMYL-3-METHOXY(2-PYRIDYL))ACETIC ACID; (2R)-2-AMINO-2-(6-FORMYL-3-METHOXY(2-PYRIDYL))PROPANOIC ACID; (2RS)-2-(4-FORMYLPHENYL)PROPANOIC ACID; (2S)-2-(2-FORMYL-1H-PYRROL-1-YL)-3-PHENYLPROPANOIC ACID; (2S)-2-(2-FORMYL-1H-PYRROL-1-YL)-4-METHYLPENTANOIC ACID; (2S)-2-(2-FORMYL-1H-PYRROL-1-YL)PROPANOIC ACID; (2S)-2-AMINO-2-(3-FORMYL-2-HYDROXY-5-METHYLPHENYL)ACETIC ACID; (2S)-2-AMINO-2-(4-[(4-FORMYLPHENYL)METHYL]PHENYL)ACETIC ACID; (2S)-2-AMINO-2-(4-[(4-FORMYLPHENYL)METHYL]PHENYL)PROPANOIC ACID; (2S)-2-AMINO-2-(4-FORMYL(2-PYRIDYL))ACETIC ACID; (2S)-2-AMINO-2-(4-FORMYL(2-PYRIDYL))PROPANOIC ACID; (2S)-2-AMINO-2-(5-FORMYL(2-PYRIDYL))ACETIC ACID;

(2S)-2-AMINO-2-(5-FORMYL(2-PYRIDYL))PROPANOIC ACID; (2S)-2-AMINO-2-(5-FORMYL(3-PYRIDYL))ACETIC ACID; (2S)-2-AMINO-2-(5-FORMYL(3-PYRIDYL))PROPANOIC ACID; (2S)-2-AMINO-2-(6-AMINO-5-FORMYL(3-PYRIDYL))ACETIC ACID; (2S)-2-AMINO-2-(6-AMINO-5-FORMYL(3-PYRIDYL))PROPANOIC ACID; (2S)-2-AMINO-2-(6-FORMYL(2-PYRIDYL))ACETIC ACID; (2S)-2-AMINO-2-(6-FORMYL(2-PYRIDYL))PROPANOIC ACID; (2S)-2-AMINO-2-(6-FORMYL(3-PYRIDYL))ACETIC ACID; (2S)-2-AMINO-2-(6-FORMYL(3-PYRIDYL))PROPANOIC ACID; (2S)-2-AMINO-2-(6-FORMYL-3-METHOXY(2-PYRIDYL))ACETIC ACID; (2S)-2-AMINO-2-(6-FORMYL-3-METHOXY(2-PYRIDYL))PROPANOIC ACID; (2S,3R)-2-BENZYL-5-FORMYL-2,3-DIHYDROBENZOFURAN-3-CARBOXYLIC ACID; (2S,3R)-5-FORMYL-2-METHYL-2,3-DIHYDROBENZOFURAN-3-CARBOXYLIC ACID; (2Z)-2,3-DICHLORO-4-OXOBUT-2-ENOIC ACID; (3-FORMYL-2-METHYL-INDOL-1-YL)-ACETIC ACID; (3-FORMYL-4-NITROPHENOXY)ACETIC ACID; (3-FORMYL-5-METHOXY-1H-INDOL-1-YL)ACETIC ACID; (4-BROMO-2-FORMYL-6-METHOXYPHENOXY)ACETIC ACID; (4-BROMO-2-FORMYLPHENOXY)ACETIC ACID; (4-CHLORO-2-FORMYL-6-METHOXYPHENOXY)ACETIC ACID; (4-CHLORO-2-FORMYLPHENOXY)ACETIC ACID; (4-FORMYL-2,6-DIMETHOXYPHENOXY)ACETIC ACID; (4-FORMYL-2-IODO-6-METHOXYPHENOXY)ACETIC ACID; (4-FORMYL-2-IODOPHENOXY)ACETIC ACID; (4-FORMYL-2-METHOXYPHENOXY)ACETIC ACID; (4-FORMYL-3,5-DIMETHOXYPHENOXY)ACETIC ACID; (4-FORMYL-3-METHOXYPHENYL)ACETIC ACID; (4-FORMYL-3-PHENYL-1H-PYRAZOL-1-YL)ACETIC ACID; (4-FORMYL-BENZENESULFONYLAMINO)-ACETIC ACID; (4'-FORMYL-BIPHENYL-2-YL)-ACETIC ACID; (4'-FORMYL-BIPHENYL-3-YL)-ACETIC ACID; (4'-FORMYL-BIPHENYL-4-YL)-ACETIC ACID; (4R)-4-AMINO-4-(3-FORMYL-2-HYDROXY-5-METHYLPHENYL)BUTANOIC ACID; (4S)-4-AMINO-4-(3-FORMYL-2-HYDROXY-5-METHYLPHENYL)BUTANOIC ACID; (5-BROMO-2-ETHOXY-4-FORMYLPHENOXY)ACETIC ACID; (5-BROMO-4-FORMYL-2-METHOXYPHENOXY)ACETIC ACID; (5-CHLORO-2-ETHOXY-4-FORMYLPHENOXY)ACETIC ACID; (5-CHLORO-4-FORMYL-2-METHOXYPHENOXY)ACETIC ACID; (5-FORMYL-2,4-DIMETHYL-1H-PYRROL-3-YL)-ACETIC ACID; (5-FORMYL-2-METHOXYPHENOXY)ACETIC ACID; (5-FORMYL-4-HYDROXY-6-OXO-3-PHENYLPYRIDAZIN-1(6H)-YL)ACETIC ACID; (5-FORMYL-IMIDAZO[2,1-B]THIAZOL-6-YLSULFANYL)-ACETIC ACID; (5R)-5-AMINO-5-(3-FORMYL-2-HYDROXY-5-METHYLPHENYL)PENTANOIC ACID; (5S)-5-AMINO-5-(3-FORMYL-2-HYDROXY-5-METHYLPHENYL)PENTANOIC ACID; (R)-3-((R)-2-((R)-2-ACETAMIDO-3-METHYLBUTANAMIDO)PROPANAMIDO)-4-OXOBUTANOIC ACID; [(2-FORMYL-1-METHYL-1H-INDOL-3-YL)THIO]ACETIC ACID; [(3-ETHOXY-5-FORMYL-2-HYDROXY-BENZYL)-METHYL-AMINO]-ACETIC ACID; [(3-FORMYL-1-METHYL-1H-INDOL-2-YL)THIO]ACETIC ACID; [(3-FORMYL-6-METHOXYQUINOLIN-2-YL)THIO]ACETIC ACID; [(4-FORMYL-2-NITROPHENYL)THIO]ACETIC ACID; [(4-FORMYL-3-METHYL-1-PHENYL-1H-PYRAZOL-5-YL)THIO]ACETIC ACID; [(5-FORMYL-2-HYDROXY-3-METHOXY-BENZYL)-METHYL-AMINO]-ACETIC ACID; [[1-(2-CHLOROBENZYL)-4-FORMYL-3-METHYL-1H-PYRAZOL-5-YL]THIO]ACETIC ACID; [[1-(4-CHLOROBENZYL)-4-FORMYL-3-METHYL-1H-PYRAZOL-5-YL]THIO]ACETIC ACID; [2-(2-FORMYL-PHENYL)-1H-IMIDAZOL-4-YL]-ACETIC ACID; [2-(3-FORMYL-PHENYL)-1H-IMIDAZOL-4-YL]-ACETIC ACID; [2-(4-FORMYL-PHENYL)-1H-IMIDAZOL-4-YL]-ACETIC ACID; [4-(3-FORMYL-2,5-DIMETHYL-1H-PYRROL-1-YL)PHENOXY]ACETIC ACID; [4-FORMYL-3-(4-METHOXYPHENYL)-1H-PYRAZOL-1-YL]ACETIC ACID; [5-(4-FORMYLBENZYLIDENE)-4-OXO-2-THIOXO-1,3-THIAZOLIDIN-3-YL]ACETIC ACID; 1-(2,4-DICHLOROPHENYL)-4-FORMYL-1H-PYRAZOLE-3-CARBOXYLIC ACID; 1-(2,5-DICHLOROPHENYL)-4-FORMYL-1H-PYRAZOLE-3-CARBOXYLIC ACID; 1-(2,5-DIMETHYLBENZYL)-3-FORMYL-1H-INDOLE-2-CARBOXYLIC ACID; 1-(2-BROMOPHENYL)-4-FORMYL-1H-PYRAZOLE-3-CARBOXYLIC ACID; 1-(2-CHLORO-4-FLUOROBENZYL)-3-FORMYL-1H-INDOLE-2-CARBOXYLIC ACID; 1-(2-CHLORO-4-FORMYLPHENOXY)CYCLOHEXANE-1-CARBOXYLIC ACID; 1-(2-CHLORO-4-FORMYLPHENOXY)CYCLOPENTANE-1-CARBOXYLIC ACID; 1-(2-CHLOROPHENYL)-4-FORMYL-1H-PYRAZOLE-3-CARBOXYLIC ACID; 1-(2-FLUOROBENZYL)-3-FORMYL-1H-INDOLE-2-CARBOXYLIC ACID; 1-(2-FLUOROBENZYL)-3-FORMYL-6-METHOXY-1H-INDOLE-2-CARBOXYLIC ACID; 1-(2-FLUOROBENZYL)-3-FORMYL-6-METHYL-1H-INDOLE-2-CARBOXYLIC ACID; 1-(3,4-DIMETHYLPHENYL)-4-FORMYL-1H-PYRAZOLE-3-CARBOXYLIC ACID; 1-(3-BROMOPHENYL)-4-FORMYL-1H-PYRAZOLE-3-CARBOXYLIC ACID; 1-(3-CHLOROBENZYL)-3-FORMYL-1H-INDOLE-2-CARBOXYLIC ACID; 1-(3-CHLOROBENZYL)-4-FORMYL-2,5-DIMETHYL-1H-PYRROLE-3-CARBOXYLIC ACID; 1-(3-CHLOROPHENYL)-4-FORMYL-1H-PYRAZOLE-3-CARBOXYLIC ACID; 1-(3-FORMYL-4-HYDROXY-BENZYL)-PIPERIDINE-4-CARBOXYLIC ACID; 1-(3-FORMYLPHENOXY)-2-METHYLCYCLOHEXANE-1-CARBOXYLIC ACID; 1-(3-FORMYLPHENOXY)-3-METHYLCYCLOHEXANE-1-CARBOXYLIC ACID; 1-(3-FORMYLPHENOXY)-4-METHYLCYCLOHEXANE-1-CARBOXYLIC ACID; 1-(3-FORMYLPHENOXY)CYCLOHEPTANE-1-CARBOXYLIC ACID; 1-(3-FORMYLPHENOXY)CYCLOHEXANE-1-CARBOXYLIC ACID; 1-(3-FORMYLPHENOXY)CYCLOPENTANE-1-CARBOXYLIC ACID; 1-(4-BROMOPHENYL)-4-FORMYL-1H-PYRAZOLE-3-CARBOXYLIC ACID; 1-(4-CHLOROPHENYL)-4-FORMYL-1H-PYRAZOLE-3-CARBOXYLIC ACID; 1-(4-ETHOXYPHENYL)-4-FORMYL-1H-PYRAZOLE-3-CARBOXYLIC ACID; 1-(4-ETHYLPHENYL)-4-FORMYL-1H-PYRAZOLE-3-CARBOXYLIC ACID; 1-(4-FLUOROBENZYL)-3-FORMYL-6-METHOXY-1H-INDOLE-2-CARBOXYLIC ACID; 1-(4-FLUOROBENZYL)-4-FORMYL-2,5-DIMETHYL-1H-PYRROLE-3-CARBOXYLIC ACID; 1-(4-FLUOROPHENYL)-4-FORMYL-1H-PYRAZOLE-3-CARBOXYLIC ACID; 1-(4-FORMYL-2-PHENYL-1,3-THIAZOL-5-YL)PIPERIDINE-4-CARBOXYLIC ACID; 1-(4-FORMYL-BENZENESULFONYL)-PIPERIDINE-4-CARBOXYLIC ACID; 1-(4-FORMYL-BENZENESULFONYL)-PYRROLIDINE-2-CARBOXYLIC ACID; 1-(4-FORMYLPHENOXY)-2-METHYLCYCLOHEXANE-1-CARBOXYLIC ACID; 1-(4-FORMYLPHENOXY)-3-METHYLCYCLO-

HEXANE-1-CARBOXYLIC ACID; 1-(4-FORMYLPHENOXY)-4-METHYLCYCLOHEXANE-1-CARBOXYLIC ACID; 1-(4-FORMYLPHENOXY)CYCLOHEPTANE-1-CARBOXYLIC ACID; 1-(4-FORMYLPHENOXY)CYCLOHEXANE-1-CARBOXYLIC ACID; 1-(4-FORMYLPHENOXY)CYCLOPENTANE-1-CARBOXYLIC ACID; 1-(4-FORMYLPHENYL)-4-PIPERIDINECARBOXYLIC ACID; 1-(5-FORMYL-2-METHOXYBENZYL)-1H-PYRAZOLE-4-CARBOXYLIC ACID; 1,8-NAPHTHALALDEHYDIC ACID; 1-[(5-FORMYL-2-FURYL)METHYL]PYRAZOLE-4-CARBOXYLIC ACID; 1-[2-(3-FORMYLPHENOXY)ETHYL]-1H-1,2,3-TRIAZOLE-4-CARBOXYLIC ACID; 1-[2-(4-FORMYLPHENOXY)ETHYL]-1H-1,2,3-TRIAZOLE-4-CARBOXYLIC ACID; 12-OXO-9(Z)-DODECENOIC ACID; 1-BENZYL-3-FORMYL-1H-INDOLE-2-CARBOXYLIC ACID; 1-BENZYL-3-FORMYL-6-METHOXY-1H-INDOLE-2-CARBOXYLIC ACID; 1-BENZYL-4-FORMYL-2,5-DIMETHYL-1H-PYRROLE-3-CARBOXYLIC ACID; 1-ETHYL-3-FORMYL-1H-INDOLE-2-CARBOXYLIC ACID; 1-ETHYL-3-FORMYL-6-METHOXY-1H-INDOLE-2-CARBOXYLIC ACID; 1H-INDOLE-1-BUTANOIC ACID, 5-BROMO-3-FORMYL-; 1H-INDOLE-1-BUTANOIC ACID, 7-ETHYL-3-FORMYL-; 1H-INDOLE-3-PROPANOIC ACID, 2-FORMYL-4,5,6,7-TETRAHYDRO-; 1H-PYRAZOLE-3-CARBOXYLIC ACID, 5-FORMYL-1-METHYL-; 1H-PYRROLE-1-ACETIC ACID, 3-FORMYL-; 1-PIPERIDINECARBOXYLIC ACID, 2-(2-FORMYLETHYL)-; 2-(2,4-DICHLORO-6-FORMYLPHENOXY)ACETIC ACID; 2-(2,4-DICHLORO-6-FORMYLPHENOXY)PROPANOIC ACID; 2-(2,6-DIBROMO-4-FORMYLPHENOXY)ACETIC ACID; 2-(2,6-DICHLORO-4-FORMYLPHENOXY)PROPANOIC ACID; 2-(2-BROMO-4-FORMYL-6-METHOXYPHENOXY)PROPANOIC ACID; 2-(2-BROMO-4-FORMYLPHENOXY)PROPANOIC ACID; 2-(2-BROMO-6-ETHOXY-4-FORMYLPHENOXY)PROPANOIC ACID; 2-(2-BROMO-6-FORMYLPHENOXY)ACETIC ACID; 2-(2-BROMO-6-FORMYLPHENOXY)PROPANOIC ACID; 2-(2-CHLORO-4-FORMYL-6-METHOXYPHENOXY)PROPANOIC ACID; 2-(2-CHLORO-4-FORMYLPHENOXY)-2,2-DIFLUOROACETIC ACID; 2-(2-CHLORO-4-FORMYLPHENOXY)-2,4-DIMETHYLPENTANOIC ACID; 2-(2-CHLORO-4-FORMYLPHENOXY)-2-CYCLOPROPYLPROPANOIC ACID; 2-(2-CHLORO-4-FORMYLPHENOXY)-2-ETHYLBUTANOIC ACID; 2-(2-CHLORO-4-FORMYLPHENOXY)-2-METHYLBUTANOIC ACID; 2-(2-CHLORO-4-FORMYLPHENOXY)-2-METHYLPENTANOIC ACID; 2-(2-CHLORO-4-FORMYLPHENOXY)-2-METHYLPROPANOIC ACID; 2-(2-CHLORO-4-FORMYLPHENOXY)-3-METHOXY-2-METHYLPROPANOIC ACID; 2-(2-CHLORO-4-FORMYLPHENOXY)-3-METHYLBUTANOIC ACID; 2-(2-CHLORO-4-FORMYLPHENOXY)-4-METHOXY-2-METHYLBUTANOIC ACID; 2-(2-CHLORO-4-FORMYLPHENOXY)BUTANOIC ACID; 2-(2-CHLORO-4-FORMYLPHENOXY)PROPANOIC ACID; 2-(2-CHLORO-4-FORMYLPHENOXYMETHYL)FURAN-3-CARBOXYLIC ACID; 2-(2-CHLORO-6-ETHOXY-4-FORMYLPHENOXY)PROPANOIC ACID; 2-(2-ETHOXY-4-FORMYL-6-NITROPHENOXY)PROPANOIC ACID; 2-(2-ETHOXY-4-FORMYLPHENOXY)PENTANOIC ACID; 2-(2-ETHOXY-4-FORMYLPHENOXY)PROPANOIC ACID; 2-(2-ETHOXY-6-FORMYLPHENOXY)PROPANOIC ACID; 2-(2-FORMYL-1H-PYRROL-1-YL)BENZOIC ACID; 2-(2-FORMYL-4-M ETHOXYPHENOXY)ACETIC ACID; 2-(2-FORMYL-4-METHOXYPHENOXY)PROPANOIC ACID; 2-(2-FORMYL-4-METHYLPHENOXY)ACETIC ACID; 2-(2-FORMYL-4-METHYLPHENOXY)PROPANOIC ACID; 2-(2-FORMYL-4-NITROPHENOXY)PROPANOIC ACID; 2-(2-FORMYL-5-METHOXYPHENOXY)ACETIC ACID; 2-(2-FORMYL-5-METHOXYPHENOXY)PROPANOIC ACID; 2-(2-FORMYL-5-PROPOXYPHENOXY)ACETIC ACID; 2-(2-FORMYL-5-PROPOXYPHENOXY)PROPANOIC ACID; 2-(2-FORMYL-6-METHOXY-4-NITROPHENOXY)PROPANOIC ACID; 2-(2-FORMYL-6-METHOXYPHENOXY)ACETIC ACID; 2-(2-FORMYL-6-METHOXYPHENOXY)PROPANOIC ACID; 2-(2-FORMYL-IMIDAZOL-1-YL)-3-PHENYL-PROPIONIC ACID; 2-(2-FORMYL-IMIDAZOL-1-YLMETHYL)-BENZOIC ACID; 2-(2-FORMYLPHENOXY)PENTANOIC ACID; 2-(2-FORMYLPHENOXY)PROPANOIC ACID; 2-(2-FORMYLPHENYL)-4-NITROBENZOIC ACID; 2-(2-FORMYLPHENYL)-5-METHOXYBENZOIC ACID; 2-(2-FORMYLPHENYL)-5-METHYLBENZOIC ACID; 2-(2-FORMYLPHENYL)-6-METHYLBENZOIC ACID; 2-(2-FORMYLPHENYL)-ISONICOTINIC ACID; 2-(2-FORMYLPHENYL)NICOTINIC ACID; 2-(2-FORMYL-PYRROL-1-YL)-4,5,6,7-TETRAHYDRO-BENZO[B]THIOPHENE-3-CARBOXYLIC ACID; 2-(2-FORMYLTHIOPHEN-4-YL)-4-CHLOROBENZOIC ACID; 2-(2-FORMYLTHIOPHEN-4-YL)-4-FLUOROBENZOIC ACID; 2-(2-FORMYLTHIOPHEN-4-YL)-4-NITROBENZOIC ACID; 2-(2-FORMYLTHIOPHEN-4-YL)-5-FLUOROBENZOIC ACID; 2-(2-FORMYLTHIOPHEN-4-YL)-5-METHOXYBENZOIC ACID; 2-(2-FORMYLTHIOPHEN-4-YL)-5-METHYLBENZOIC ACID; 2-(2-FORMYLTHIOPHEN-4-YL)-6-CHLOROBENZOIC ACID; 2-(2-FORMYLTHIOPHEN-4-YL)-6-FLUOROBENZOIC ACID; 2-(2-FORMYLTHIOPHEN-4-YL)-6-METHYLBENZOIC ACID; 2-(2-FORMYLTHIOPHEN-4-YL)BENZOIC ACID; 2-(2-FORMYLTHIOPHEN-4-YL)ISONICOTINIC ACID; 2-(2-FORMYLTHIOPHEN-4-YL)NICOTINIC ACID; 2-(2-HYDROXYCARBONYL-6-PYRIDYL)MALONDIALDEHYDE; 2-(3-CARBOXYPHENOXY)-4-CHLORO-5-THIAZOLECARBOXALDEHYDE; 2-(3-CHLORO-2-FORMYLPHENOXY)ACETIC ACID; 2-(3-CHLORO-2-FORMYLPHENOXY)PROPANOIC ACID; 2-(3-FORMYL-1H-INDOL-1-YL)BUTANOIC ACID; 2-(3-FORMYL-1H-INDOL-1-YL)PROPANOIC ACID; 2-(3-FORMYL-2,5-DIMETHYL-1H-PYRROL-1-YL)-4,5-DIMETHYL-3-THIOPHENECARBOXYLIC ACID; 2-(3-FORMYL-2,5-DIMETHYL-1H-PYRROL-1-YL)-BENZOIC ACID; 2-(3-FORMYL-2-METHOXYPHENOXY)PROPANOIC ACID; 2-(3-FORMYL-4-HYDROXY-5-METHOXYPHENYL)ACETIC ACID; 2-(3-FORMYLPHENOXY)-2,4-DIMETHYLPENTANOIC ACID; 2-(3-FORMYLPHENOXY)-2,5-DIMETHYLHEXANOIC ACID; 2-(3-FORMYLPHENOXY)-2-METHYLBUTANOIC ACID; 2-(3-FORMYLPHENOXY)-2-METHYLPENTANOIC ACID; 2-(3-FORMYLPHENOXY)-2-METHYLPROPANOIC ACID; 2-(3-FORMYLPHENOXY)-2-PHENYLACETIC ACID; 2-(3-FORMYLPHENOXY)-2-PROPYLPENTANOIC ACID; 2-(3-FORMYLPHENOXY)-3-METHOXY-2-METHYLPROPANOIC ACID; 2-(3-FORMYLPHENOXY)-3-METHYLBUTANOIC ACID; 2-(3-FORMYLPHENOXY)-4-METHOXY-2-METHYLBUTANOIC ACID; 2-(3-FORMYLPHENOXY)BUTANOIC ACID; 2-(3-FORMYLPHENOXY)PROPANOIC ACID; 2-(3-

FORMYLPHENOXYMETHYL)BENZOIC ACID; 2-(3-FORMYLPHENOXYMETHYL)FURAN-3-CARBOXYLIC ACID; 2-(3-FORMYLPHENYL)-4-NITROBENZOIC ACID; 2-(3-FORMYLPHENYL)-5-METHOXYBENZOIC ACID; 2-(3-FORMYLPHENYL)-5-METHYLBENZOIC ACID; 2-(3-FORMYLPHENYL)-6-METHYLBENZOIC ACID; 2-(3-FORMYLPHENYL)ISONICOTINIC ACID; 2-(3-FORMYLPHENYL)NICOTINIC ACID; 2-(3-HYDROXYCARBONYL-2-NITROPHENYL)MALONDIALDEHYDE; 2-(3-HYDROXYCARBONYL-6-PYRIDYL)MALONDIALDEHYDE; 2-(4-BROMO-2-FORMYLPHENOXY)PROPANOIC ACID; 2-(4-CHLORO-2-FORMYL-6-METHOXYPHENOXY)PROPANOIC ACID; 2-(4-CHLORO-2-FORMYLPHENOXY)PROPANOIC ACID; 2-(4-FORMYL-1H-IMIDAZOL-1-YL)ACETIC ACID; 2-(4-FORMYL-1H-IMIDAZOL-2-YL)-BENZOIC ACID; 2-(4-FORMYL-2,6-DIMETHOXYPHENOXY)PROPANOIC ACID; 2-(4-FORMYL-2,6-DIMETHYLPHENOXY)ACETIC ACID; 2-(4-FORMYL-2,6-DIMETHYLPHENOXY)PROPANOIC ACID; 2-(4-FORMYL-2-METHOXY-5-NITROPHENOXY)ACETIC ACID; 2-(4-FORMYL-2-METHOXY-5-NITROPHENOXY)PROPANOIC ACID; 2-(4-FORMYL-2-METHOXY-6-NITROPHENOXY)PROPANOIC ACID; 2-(4-FORMYL-2-METHOXYPHENOXY)PROPANOIC ACID; 2-(4-FORMYL-2-NITROPHENOXY)ACETIC ACID; 2-(4-FORMYL-2-NITROPHENOXY)PROPANOIC ACID; 2-(4-FORMYLPHENOXY)-2,4-DIMETHYLPENTANOIC ACID; 2-(4-FORMYLPHENOXY)-2,5-DIMETHYLHEXANOIC ACID; 2-(4-FORMYLPHENOXY)-2-METHYLBUTANOIC ACID; 2-(4-FORMYLPHENOXY)-2-METHYLPENTANOIC ACID; 2-(4-FORMYLPHENOXY)-2-METHYLPROPANOIC ACID; 2-(4-FORMYLPHENOXY)-2-PHENYLACETIC ACID; 2-(4-FORMYLPHENOXY)-2-PROPYLPENTANOIC ACID; 2-(4-FORMYLPHENOXY)-3-METHOXY-2-METHYLPROPANOIC ACID; 2-(4-FORMYLPHENOXY)-3-METHYLBUTANOIC ACID; 2-(4-FORMYLPHENOXY)-4-METHOXY-2-METHYLBUTANOIC ACID; 2-(4-FORMYLPHENOXY)BUTANOIC ACID; 2-(4-FORMYLPHENOXY)PENTANOIC ACID; 2-(4-FORMYLPHENOXY)PROPANOIC ACID; 2-(4-FORMYLPHENOXYMETHYL)BENZOIC ACID; 2-(4-FORMYLPHENOXYMETHYL)FURAN-3-CARBOXYLIC ACID; 2-(4-FORMYLPHENYL)-4-NITROBENZOIC ACID; 2-(4-FORMYLPHENYL)-5-METHOXYBENZOIC ACID; 2-(4-FORMYLPHENYL)-5-METHYLBENZOIC ACID; 2-(4-FORMYLPHENYL)-6-METHYLBENZOIC ACID; 2-(4-FORMYLPHENYL)ISONICOTINIC ACID; 2-(4-FORMYLPHENYL)NICOTINIC ACID; 2-(4-HYDROXYCARBONYL-2-NITROPHENYL)MALONDIALDEHYDE; 2-(5-(BENZYLOXY)-2-FORMYLPHENOXY)PROPANOIC ACID; 2-(5-FORMYL-1H-BENZIMIDAZOL-1-YL)ACETIC ACID; 2-(5-FORMYL-2-METHOXYPHENOXY)-2-PHENYLACETIC ACID; 2-(5-FORMYL-2-METHOXYPHENOXY)PROPANOIC ACID; 2-(5-FORMYL-2-NITROPHENOXY)ACETIC ACID; 2-(5-FORMYL-2-NITROPHENOXY)PROPANOIC ACID; 2-(5-FORMYLFURAN-2-YL)ACETIC ACID; 2-(5-FORMYL-FURAN-2-YL)-BENZOIC ACID; 2-(5-FORMYLTHIOPHEN-2-YL)-4-CHLOROBENZOIC ACID; 2-(5-FORMYLTHIOPHEN-2-YL)-4-FLUOROBENZOIC ACID; 2-(5-FORMYLTHIOPHEN-2-YL)-4-NITROBENZOIC ACID; 2-(5-FORMYLTHIOPHEN-2-YL)-5-FLUOROBENZOIC ACID; 2-(5-FORMYLTHIOPHEN-2-YL)-5-METHOXYBENZOIC ACID; 2-(5-FORMYLTHIOPHEN-2-YL)-5-METHYLBENZOIC ACID; 2-(5-FORMYLTHIOPHEN-2-YL)-6-CHLOROBENZOIC ACID; 2-(5-FORMYLTHIOPHEN-2-YL)-6-FLUOROBENZOIC ACID; 2-(5-FORMYLTHIOPHEN-2-YL)-6-METHYLBENZOIC ACID; 2-(5-FORMYL-THIOPHEN-2-YL)-BENZOIC ACID; 2-(5-FORMYLTHIOPHEN-2-YL)ISONICOTINIC ACID; 2-(5-FORMYLTHIOPHEN-2-YL)NICOTINIC ACID; 2-(5-HYDROXYCARBONYL-2-NITROPHENYL)MALONDIALDEHYDE; 2-(5-HYDROXYCARBONYL-2-NITROPHENYL)MALONDIALDEHYDE MONOHYDRATE; 2-(5-HYDROXYCARBONYL-6-PYRIDYL)MALONDIALDEHYDE; 2,2-DIFLUORO-2-(3-FORMYLPHENOXY)ACETIC ACID; 2,2-DIFLUORO-2-(4-FORMYLPHENOXY)ACETIC ACID; 2,3-DIBROMO-4-OXO-BUTYRIC ACID; 2,4-DICHLORO-5-FLUORO-3-FORMYL-BENZOIC ACID; 2,4-DIFLUORO-5-FORMYLBENZOIC ACID; 2,4-HEXADIENOIC ACID, 2-AMINO-5-METHYL-6-OXO-, (E,Z)-; 2,6-DIFLUORO-4-FORMYLBENZOIC ACID; 2-[(1-FORMYL-2-NAPHTHYL)OXY]PROPANOIC ACID; 2-[(1-FORMYLNAPHTHALEN-2-YL)OXY]ACETIC ACID; 2-[(4-FORMYL-1,3-DIMETHYL-1H-PYRAZOL-5-YL)SULFANYL] ACETIC ACID; 2-[(5-FORMYL-2-METHOXYBENZYL)THIO]NICOTINIC ACID; 2-[(6-FORMYL-2H-1,3-BENZODIOXOL-5-YL)OXY]ACETIC ACID; 2-[(6-FORMYL-2H-1,3-BENZODIOXOL-5-YL)OXY]PROPANOIC ACID; 2-[2-(3-FORMYL-INDOL-1-YL)-ACETYLAMINO]-BENZOIC ACID; 2-[4-(2-FORMYL-1H-PYRROL-1-YL)PHENOXY]PROPANOIC ACID; 2-[4-(3-FORMYL-2,5-DIMETHYL-1H-1-PYRROLYL)PHENOXY]PROPANOIC ACID; 2-AMINO-3-FORMYL-BENZOIC ACID; 2-AMINO-4-OXOBUTANOIC ACID; 2-AMINO-5-(2-FORMYLPHENYL)ISONICOTINIC ACID; 2-AMINO-5-(2-FORMYLPHENYL)NICOTINIC ACID; 2-AMINO-5-(3-FORMYLPHENYL)ISONICOTINIC ACID; 2-AMINO-5-(3-FORMYLPHENYL)NICOTINIC ACID; 2-AMINO-5-(4-FORMYLPHENYL)ISONICOTINIC ACID; 2-AMINO-5-(4-FORMYLPHENYL)NICOTINIC ACID; 2-BROMO-3-CHLORO-4-OXO-2-BUTENOIC ACID; 2-CARBOXY-3-CHLOROBENZENALDEHYDE; 2-CARBOXYBENZALDEHYDE; 2-CHLORO-4-(2-FORMYLPHENYL)BENZOIC ACID; 2-CHLORO-4-(3-FORMYLPHENYL)BENZOIC ACID; 2-CHLORO-4-(4-FORMYLPHENYL)BENZOIC ACID; 2-CHLORO-4-(5-FORMYL-FURAN-2-YL)-BENZOIC ACID; 2-CHLORO-4-FORMYLBENZOIC ACID; 2-CHLORO-5-(2-FORMYLPHENYL)BENZOIC ACID; 2-CHLORO-5-(2-FORMYLPHENYL)ISONICOTINIC ACID; 2-CHLORO-5-(2-FORMYLPHENYL)NICOTINIC ACID; 2-CHLORO-5-(3-FORMYL-2,5-DIMETHYL-1H-PYRROL-1-YL)BENZOIC ACID; 2-CHLORO-5-(3-FORMYLPHENYL)BENZOIC ACID; 2-CHLORO-5-(3-FORMYLPHENYL)ISONICOTINIC ACID; 2-CHLORO-5-(3-FORMYLPHENYL)NICOTINIC ACID; 2-CHLORO-5-(4-FORMYLPHENYL)BENZOIC ACID; 2-CHLORO-5-(4-FORMYLPHENYL)ISONICOTINIC ACID; 2-CHLORO-5-(4-FORMYLPHENYL)NICOTINIC ACID; 2-CHLORO-5-(5-FORMYL-2-FURYL)BENZOIC ACID; 2-CHLORO-5-FORMYL-BENZOIC ACID; 2-CHLORO-6-FLUORO-3-FORMYL-BENZOIC ACID; 2-CYCLOPROPOXY-3-FORMYLBENZOIC ACID; 2-CYCLOPROPOXY-4-FORMYLBENZOIC ACID; 2-CYCLOPROPOXY-5-FORMYLBENZOIC ACID; 2-CYCLOPROPOXY-6-FORMYLBENZOIC ACID; 2-CYCLOPROPYL-2-(3-FORMYLPHENOXY)PROPANOIC ACID;

2-CYCLOPROPYL-2-(4-FORMYLPHENOXY)PROPANOIC ACID; 2-ETHYL-2-(3-FORMYLPHENOXY)BUTANOIC ACID; 2-ETHYL-2-(4-FORMYLPHENOXY)BUTANOIC ACID; 2-FLUORO-4-(2-FORMYLPHENYL)BENZOIC ACID; 2-FLUORO-4-(3-FORMYL-2-HYDROXYPHENYL)BENZOIC ACID; 2-FLUORO-4-(3-FORMYL-4-HYDROXYPHENYL)BENZOIC ACID; 2-FLUORO-4-(3-FORMYLPHENYL)BENZOIC ACID; 2-FLUORO-4-(4-FORMYLPHENYL)BENZOIC ACID; 2-FLUORO-4-(4-FORMYLPYRIDIN-3-YL)BENZOIC ACID; 2-FLUORO-4-(5-FORMYL-2-HYDROXYPHENYL)BENZOIC ACID; 2-FLUORO-4-(5-FORMYLPYRIDIN-3-YL)BENZOIC ACID; 2-FLUORO-4-FORMYLBENZOIC ACID; 2-FLUORO-5-(2-FORMYLPHENYL)BENZOIC ACID; 2-FLUORO-5-(3-FORMYLPHENYL)BENZOIC ACID; 2-FLUORO-5-(4-FORMYLPHENYL)BENZOIC ACID; 2-FLUORO-5-FORMYLBENZOIC ACID; 2'-FORMYL[1,1'-BIPHENYL]-2-CARBOXYLIC ACID; 2-FORMYL-1H-IMIDAZOLE-4-CARBOXYLIC ACID; 2-FORMYL-1H-PYRROLE-1-PROPANOIC ACID; 2-FORMYL-3-HYDROXYBENZOIC ACID; 2-FORMYL-3-NITRO-BENZOIC ACID; 2-FORMYL-4,5-DIMETHOXY-BENZOIC ACID; 2-FORMYL-4-HYDROXY-3-METHOXYBENZOIC ACID; 2-FORMYL-4-HYDROXYBENZOIC ACID; 2-FORMYL-4-NITROPHENOXYACETIC ACID; 2-FORMYL-5-HYDROXYBENZOIC ACID; 2-FORMYL-5-IODO-BENZOIC ACID; 2-FORMYL-5-METHOXY-BENZOIC ACID; 2-FORMYL-5-NITROBENZOIC ACID; 2-FORMYL-6H-FURO[2,3-B]PYRROLE-5-CARBOXYLIC ACID; 2-FORMYL-6-HYDROXYBENZOIC ACID; 2-FORMYL-6-METHOXYBENZOIC ACID; 2'-FORMYL-BIPHENYL-3-CARBOXYLIC ACID; 2'-FORMYL-BIPHENYL-4-CARBOXYLIC ACID; 2-FORMYLCINNAMIC ACID; 2-FORMYLCYCLOPENT-2-ENECARBOXYLIC ACID; 2-FORMYLPHENOXYACETIC ACID; 2-FORMYLQUINOLINE-6-CARBOXYLIC ACID; 2-FORMYLQUINOLINE-8-CARBOXYLIC ACID; 2-FORMYLTHIOPHENE-3-CARBOXYLIC ACID; 2-HYDROXYISOPHTHALALDEHYDE ACID HYDRATE; 2-NAPHTHALENECARBOXYLIC ACID, 5-FORMYL-4-HYDROXY-6,7-DIMETHOXY-; 2-PYRROLECARBAMIC ACID, 4-FORMYL-3,5-DIMETHYL-; 3-(2,4-DIMETHYL-5-FORMYL-1H-PYRROLE-3-YL)PROPANOIC ACID; 3-(2-CHLORO-4-FORMYL-6-METHOXY-PHENOXYMETHYL)-BENZOIC ACID; 3-(2-CHLORO-4-FORMYLPHENOXY)PROPANOIC ACID; 3-(2-CHLORO-4-FORMYLPHENOXY)THIANE-3-CARBOXYLIC ACID; 3-(2-CHLORO-4-FORMYLPHENOXYMETHYL)FURAN-2-CARBOXYLIC ACID; 3-(2-ETHOXY-4-FORMYLPHENOXY)PROPANOIC ACID; 3-(2-FORMYL-1H-PYRROL-1-YL)-4-METHYL-BENZOIC ACID; 3-(2-FORMYL-1H-PYRROL-1-YL)BENZOIC ACID; 3-(2-FORMYL-4-METHYL-1H-PYRROL-3-YL)-PROPIONIC ACID; 3-(2-FORMYL-IMIDAZOL-1-YL)-PROPIONIC ACID; 3-(2-FORMYL-IMIDAZOL-1-YLMETHYL)-BENZOIC ACID; 3-(2-FORMYLPHENOXY)PROPANOIC ACID; 3-(2-FORMYLPHENYL)-2-METHOXYBENZOIC ACID; 3-(2-FORMYLPHENYL)-2-METHYLBENZOIC ACID; 3-(2-FORMYLPHENYL)-5-HYDROXYBENZOIC ACID; 3-(2-FORMYLPHENYL)-5-METHOXYBENZOIC ACID; 3-(2-FORMYLPHENYL)-5-NITROBENZOIC ACID; 3-(2-FORMYLPHENYL)-5-TRIFLUOROMETHYLBENZOIC ACID; 3-(2-FORMYLPHENYL)ISONICOTINIC ACID; 3-(2-FORMYLPHENYL)PICOLINIC ACID; 3-(2-FORMYLPHENYL)PROPANOIC ACID; 3-(2-FORMYLTHIOPHEN-3-YL)PROPIOLIC ACID; 3-(2-FORMYLTHIOPHEN-4-YL)-2-METHOXYBENZOIC ACID; 3-(2-FORMYLTHIOPHEN-4-YL)-2-METHYLBENZOIC ACID; 3-(2-FORMYLTHIOPHEN-4-YL)-4-CHLOROBENZOIC ACID; 3-(2-FORMYLTHIOPHEN-4-YL)-4-FLUOROBENZOIC ACID; 3-(2-FORMYLTHIOPHEN-4-YL)-5-CHLOROBENZOIC ACID; 3-(2-FORMYLTHIOPHEN-4-YL)-5-FLUOROBENZOIC ACID; 3-(2-FORMYLTHIOPHEN-4-YL)-5-HYDROXYBENZOIC ACID; 3-(2-FORMYLTHIOPHEN-4-YL)-5-METHOXYBENZOIC ACID; 3-(2-FORMYLTHIOPHEN-4-YL)-5-NITROBENZOIC ACID; 3-(2-FORMYLTHIOPHEN-4-YL)-5-TRIFLUOROMETHYLBENZOIC ACID; 3-(2-FORMYLTHIOPHEN-4-YL)-6-AMINOPICOLINIC ACID; 3-(2-FORMYLTHIOPHEN-4-YL)ISONICOTINIC ACID; 3-(2-FORMYLTHIOPHEN-4-YL)PICOLINIC ACID; 3-(3-FORMYL-1H-INDOL-1-YL)PROPANOIC ACID; 3-(3-FORMYL-1H-INDOL-5-YL)BENZOIC ACID; 3-(3-FORMYL-1H-PYRROL-1-YL)PROPANOIC ACID; 3-(3-FORMYL-2,5-DIMETHYL-1H-PYRROL-1-YL)-4-METHYLBENZOIC ACID; 3-(3-FORMYL-2,5-DIMETHYL-PYRROL-1-YL)-2-METHYL-BENZOIC ACID; 3-(3-FORMYL-2,5-DIMETHYL-PYRROL-1-YL)-BENZOIC ACID; 3-(3-FORMYLPHENOXY)PROPANOIC ACID; 3-(3-FORMYLPHENOXY)THIANE-3-CARBOXYLIC ACID; 3-(3-FORMYLPHENOXY)THIOLANE-3-CARBOXYLIC ACID; 3-(3-FORMYLPHENOXYMETHYL)BENZOIC ACID; 3-(3-FORMYLPHENOXYMETHYL)FURAN-2-CARBOXYLIC ACID; 3-(3-FORMYLPHENYL)-2-METHOXYBENZOIC ACID; 3-(3-FORMYLPHENYL)-2-METHYLBENZOIC ACID; 3-(3-FORMYLPHENYL)-5-HYDROXYBENZOIC ACID; 3-(3-FORMYLPHENYL)-5-METHOXYBENZOIC ACID; 3-(3-FORMYLPHENYL)-5-NITROBENZOIC ACID; 3-(3-FORMYLPHENYL)-5-TRIFLUOROMETHYLBENZOIC ACID; 3-(3-FORMYLPHENYL)ISONICOTINIC ACID; 3-(3-FORMYLPHENYL)PICOLINIC ACID; 3-(3-FORMYLPHENYL)PROPANOIC ACID; 3-(3-OXOPROPYL)-BENZOIC ACID; 3-(4-FORMYL-1H-IMIDAZOL-2-YL)-BENZOIC ACID; 3-(4-FORMYL-2-METHOXY-5-NITROPHENOXY)PROPANOIC ACID; 3-(4-FORMYL-2-METHOXYPHENOXY)PROPANOIC ACID; 3-(4-FORMYL-3,5-DIMETHYL-1H-PYRAZOL-1-YL)PROPANOIC ACID; 3-(4-FORMYLPHENOXY)PROPANOIC ACID; 3-(4-FORMYLPHENOXY)THIANE-3-CARBOXYLIC ACID; 3-(4-FORMYLPHENOXY)THIOLANE-3-CARBOXYLIC ACID; 3-(4-FORMYLPHENOXYMETHYL)FURAN-2-CARBOXYLIC ACID; 3-(4-FORMYLPHENYL)-2-METHOXYBENZOIC ACID; 3-(4-FORMYLPHENYL)-2-METHYLBENZOIC ACID; 3-(4-FORMYLPHENYL)-3-METHYLBUTANOIC ACID; 3-(4-FORMYLPHENYL)-5-HYDROXYBENZOIC ACID; 3-(4-FORMYLPHENYL)-5-METHOXYBENZOIC ACID; 3-(4-FORMYLPHENYL)-5-NITROBENZOIC ACID; 3-(4-FORMYLPHENYL)-5-TRIFLUOROMETHYLBENZOIC ACID; 3-(4-FORMYLPHENYL)ISONICOTINIC ACID; 3-(4-FORMYLPHENYL)PICOLINIC ACID; 3-(4-FORMYLPHENYL)PROPANOIC ACID; 3-(5-FORMYL-2-FURYL)BENZOIC ACID; 3-(5-FORMYL-3-THIENYL)BENZOIC ACID; 3-(5-FORMYL-FURAN-2-YL)-2-METHYL-BENZOIC ACID; 3-(5-FORMYL-FURAN-2-YL)-4-METHYL-BENZOIC ACID; 3-(5-FORMYLTHIOPHEN-2-YL)-2-METHOXYBENZOIC

ACID; 3-(5-FORMYLTHIOPHEN-2-YL)-2-METHYL-BENZOIC ACID; 3-(5-FORMYLTHIOPHEN-2-YL)-4-CHLOROBENZOIC ACID; 3-(5-FORMYLTHIOPHEN-2-YL)-4-FLUOROBENZOIC ACID; 3-(5-FORMYLTHIOPHEN-2-YL)-5-CHLOROBENZOIC ACID; 3-(5-FORMYLTHIOPHEN-2-YL)-5-FLUOROBENZOIC ACID; 3-(5-FORMYLTHIOPHEN-2-YL)-5-HYDROXYBENZOIC ACID; 3-(5-FORMYLTHIOPHEN-2-YL)-5-METHOXYBENZOIC ACID; 3-(5-FORMYLTHIOPHEN-2-YL)-5-NITROBENZOIC ACID; 3-(5-FORMYLTHIOPHEN-2-YL)-5-TRIFLUOROMETHYLBENZOIC ACID; 3-(5-FORMYLTHIOPHEN-2-YL)-6-AMINOPICOLINIC ACID; 3-(5-FORMYL-THIOPHEN-2-YL)-BENZOIC ACID; 3-(5-FORMYLTHIOPHEN-2-YL)ISONICOTINIC ACID; 3-(5-FORMYLTHIOPHEN-2-YL)PICOLINIC ACID; 3-(5-FORMYLTHIOPHEN-3-YL)PROPIOLIC ACID; 3-(7-FORMYL-8-HYDROXYQUINOLIN-5-YL)-PROPIONIC ACID; 3,4-DIFORMYL-5-(4-METHOXY-3-NITROPHENYL)PENTANOIC ACID; 3,4-DIMETHYL-5-FORMYLPYRROLE-2-CARBOXYLIC ACID; 3-[(1-FORMYL-2-NAPHTHYL)OXY]PROPANOIC ACID; 3-[(2-CHLORO-6-ETHOXY-4-FORMYLPHENOXY)METHYL]BENZOIC ACID; 3-[(4-FORMYL-2-METHOXYPHENOXY)METHYL]BENZOIC ACID; 3-[(4-FORMYLPHENOXY)METHYL]BENZOIC ACID; 3-[2-(3-FORMYL-INDOL-1-YL)-ACETYLAMINO]-BENZOIC ACID; 3-[4-FORMYL-3-(4-METHOXYPHENYL)-1H-PYRAZOL-1-YL]PROPANOIC ACID; 3-AMINO-5-(2-FORMYLPHENYL)BENZOIC ACID; 3-AMINO-5-(3-FORMYLPHENYL)BENZOIC ACID; 3-AMINO-5-(4-FORMYLPHENYL)BENZOIC ACID; 3-BROMO-2-FORMYL-5-NITRO-BENZOIC ACID; 3-CARBOXYBENZALDEHYDE; 3-CARBOXYLIC ACID-1H-INDAZOLE-4-CARBOXALDEHYDE; 3-CHLORO-2-FORMYL-5-NITRO-BENZOIC ACID; 3-CHLORO-2-FORMYLBENZOIC ACID; 3-CHLORO-5-FORMYLPYRIDINE-2-CARBOXYLIC ACID; 3-CYCLOPROPOXY-2-FORMYLBENZOIC ACID; 3-CYCLOPROPOXY-2-FORMYLISONICOTINIC ACID; 3-CYCLOPROPOXY-4-FORMYLBENZOIC ACID; 3-CYCLOPROPOXY-4-FORMYLPICOLINIC ACID; 3-CYCLOPROPOXY-5-FORMYLBENZOIC ACID; 3-CYCLOPROPOXY-5-FORMYLISONICOTINIC ACID; 3-CYCLOPROPOXY-5-FORMYLPICOLINIC ACID; 3-CYCLOPROPOXY-6-FORMYLPICOLINIC ACID; 3-FLUORO-4-(2-FORMYLPHENYL)BENZOIC ACID; 3-FLUORO-4-(3-FORMYLPHENYL)BENZOIC ACID; 3-FLUORO-4-(4-FORMYLPHENYL)BENZOIC ACID; 3'-FORMYL(1,1'-BIPHENYL)-3-CARBOXYLIC ACID; 3'-FORMYL(1,1'-BIPHENYL)-4-CARBOXYLIC ACID; 3'-FORMYL[1,1-BIPHENYL]-2-CARBOXYLIC ACID; 3-FORMYL-1-(2-METHYLBENZYL)-1H-INDOLE-2-CARBOXYLIC ACID; 3-FORMYL-1-(4-METHOXYBENZYL)-1H-INDOLE-2-CARBOXYLIC ACID; 3-FORMYL-1-(4-VINYLBENZYL)-1H-INDOLE-2-CARBOXYLIC ACID; 3-FORMYL-1H-INDAZOLE-4-CARBOXYLIC ACID; 3-FORMYL-1H-INDAZOLE-5-CARBOXYLIC ACID; 3-FORMYL-1H-INDAZOLE-6-CARBOXYLIC ACID; 3-FORMYL-1H-INDOLE-2-CARBOXYLIC ACID; 3-FORMYL-1H-INDOLE-4-CARBOXYLIC ACID; 3-FORMYL-1H-INDOLE-6-CARBOXYLIC ACID; 3-FORMYL-1H-INDOLE-7-CARBOXYLIC ACID; 3-FORMYL-1H-PYRROLO[2,3-B]PYRIDINE-4-CARBOXYLIC ACID; 3-FORMYL-1H-PYRROLO[2,3-C]PYRIDINE-4-CARBOXYLIC ACID; 3-FORMYL-1H-PYRROLO[2,3-C]PYRIDINE-7-CARBOXYLIC ACID; 3-FORMYL-1H-PYRROLO[3,2-B]PYRIDINE-5-CARBOXYLIC ACID; 3-FORMYL-1-ISOBUTYL-1H-INDOLE-4-CARBOXYLIC ACID; 3-FORMYL-1-METHYL-1H-INDOLE-2-CARBOXYLIC ACID; 3-FORMYL-1-METHYL-1H-INDOLE-4-CARBOXYLIC ACID; 3-FORMYL-1-METHYL-1H-PYRAZOLE-5-CARBOXYLIC ACID; 3-FORMYL-2-FUROIC ACID; 3-FORMYL-2-THIOPHENECARBOXYLIC ACID; 3-FORMYL-4,6-DIMETHOXY-1H-INDOLE-2-CARBOXYLIC ACID; 3-FORMYL-4-AZAINDOLE-6-CARBOXYLIC ACID; 3'-FORMYL-4'-HYDROXY[1,1'-BIPHENYL]-3-CARBOXYLIC ACID; 3'-FORMYL-4-HYDROXY[1,1-BIPHENYL]-3-CARBOXYLIC ACID; 3'-FORMYL-4'-HYDROXY[1,1-BIPHENYL]-4-CARBOXYLIC ACID; 3-FORMYL-4-HYDROXYBENZOIC ACID; 3-FORMYL-4-METHOXY-BENZOIC ACID; 3-FORMYL-4-METHYL-1H-PYRROLO[2,3-B]PYRIDINE-5-CARBOXYLIC ACID; 3-FORMYL-5,6-DIMETHOXY-1H-INDOLE-2-CARBOXYLIC ACID; 3-FORMYL-5-HYDROXYBENZOIC ACID; 3-FORMYL-5-METHOXY-1H-INDOLE-2-CARBOXYLIC ACID; 3-FORMYL-5-METHOXY-BENZOIC ACID; 3-FORMYL-5-METHYL-1H-INDOLE-2-CARBOXYLIC ACID; 3-FORMYL-6-METHOXY-1-(2-METHYLBENZYL)-1H-INDOLE-2-CARBOXYLIC ACID; 3-FORMYL-6-METHOXY-1-(4-METHOXYBENZYL)-1H-INDOLE-2-CARBOXYLIC ACID; 3-FORMYL-6-METHOXY-1-(4-METHYLBENZYL)-1H-INDOLE-2-CARBOXYLIC ACID; 3-FORMYL-6-METHOXY-1-(4-VINYLBENZYL)-1H-INDOLE-2-CARBOXYLIC ACID; 3-FORMYL-6-METHOXY-1H-INDOLE-2-CARBOXYLIC ACID; 3-FORMYL-6-METHOXY-1-METHYL-1H-INDOLE-2-CARBOXYLIC ACID; 3-FORMYLINDOL-1-YL-ACETIC ACID; 3-FORMYLINDOLE-5-CARBOXYLIC ACID; 3-FORMYLPHENOXYACETIC ACID; 3-FORMYLPICOLINIC ACID; 3-FORMYLSALICYLIC ACID; 3-OXO-PROPANOIC ACID; 4-([(4-FORMYL-2-METHOXYPHENOXY)ACETYL]AMINO)BENZOIC ACID; 4-([2-(1,3-BENZOXAZOL-2-YL)-3-OXO-1-PROPENYL]AMINO)-2-HYDROXYBENZOIC ACID; 4-(2,6-DIHYDROXYBENZOYL)-3-FORMYL-5-HYDROXYBENZOIC ACID; 4-(2-BUTYL-5-FORMYL-IMIDAZOL-1-YLMETHYL)-BENZOIC ACID; 4-(2-CARBOXYTHIOPHEN-3-YL)BENZALDEHYDE; 4-(2-CARBOXYTHIOPHENE-4-YL)-2-FORMYLPHENOL; 4-(2-CHLORO-4-FORMYLPHENOXY)BUTANOIC ACID; 4-(2-CHLORO-4-FORMYLPHENOXY)OXANE-4-CARBOXYLIC ACID; 4-(2-CHLORO-4-FORMYLPHENOXY)PENTANOIC ACID; 4-(2-CHLORO-4-FORMYLPHENOXY)THIANE-4-CARBOXYLIC ACID; 4-(2-CHLORO-4-FORMYLPHENOXYMETHYL)-1,3-THIAZOLE-2-CARBOXYLIC ACID; 4-(2-ETHOXY-4-FORMYLPHENOXYMETHYL)BENZOIC ACID; 4-(2-FORMYL-1H-PYRROL-1-YL)-3-METHYL-BENZOIC ACID; 4-(2-FORMYL-1H-PYRROL-1-YL)BENZOIC ACID; 4-(2-FORMYL-IMIDAZOL-1-YL)-BUTYRIC ACID; 4-(2-FORMYL-IMIDAZOL-1-YLMETHYL)-BENZOIC ACID; 4-(2-FORMYLPHENYL)-2-HYDROXYBENZOIC ACID; 4-(2-FORMYLPHENYL)-2-METHOXYBENZOIC ACID; 4-(2-FORMYLPHENYL)-2-NITROBENZOIC ACID; 4-(2-FORMYLPHENYL)-3-HYDROXYBENZOIC ACID; 4-(2-FORMYLPHENYL)-3-METHOXYBENZOIC ACID; 4-(2-FORMYLPHENYL)-3-METHYLBENZOIC ACID; 4-(2-FORMYLPHENYL)NICOTINIC ACID; 4-(2-FORMYLPHENYL)PICOLINIC ACID; 4-(2-FORMYLTHIOPHEN-4-YL)-2-CHLOROBENZOIC ACID; 4-(2-FORMYLTHIOPHEN-4-YL)-2-FLUO-

ROBENZOIC ACID; 4-(2-FORMYLTHIOPHEN-4-YL)-2-HYDROXYBENZOIC ACID; 4-(2-FORMYLTHIOPHEN-4-YL)-2-METHOXYBENZOIC ACID; 4-(2-FORMYLTHIOPHEN-4-YL)-2-NITROBENZOIC ACID; 4-(2-FORMYLTHIOPHEN-4-YL)-3-FLUOROBENZOIC ACID; 4-(2-FORMYLTHIOPHEN-4-YL)-3-HYDROXYBENZOIC ACID; 4-(2-FORMYLTHIOPHEN-4-YL)-3-METHOXYBENZOIC ACID; 4-(2-FORMYLTHIOPHEN-4-YL)-3-METHYLBENZOIC ACID; 4-(2-FORMYLTHIOPHEN-4-YL)NICOTINIC ACID; 4-(2-FORMYLTHIOPHEN-4-YL)PICOLINIC ACID; 4-(2-OXOACETYL)BENZOIC ACID; 4-(3-CARBOXY-4-CHLOROPHENYL)-2-FORMYLPHENOL; 4-(3-CARBOXY-5-FLUOROPHENYL)-2-FORMYLPHENOL; 4-(3-FORMYL-1H-INDOL-5-YL)BENZOIC ACID; 4-(3-FORMYL-2,5-DIMETHYL-1H-PYRROL-1-YL)-BENZENEACETIC ACID; 4-(3-FORMYL-2,5-DIMETHYL-1H-PYRROL-1-YL)BENZENECARBOXYLIC ACID; 4-(3-FORMYL-2,5-DIMETHYL-PYRROL-1-YL)-3-METHYL-BENZOIC ACID; 4-(3-FORMYL-4-NITRO-PHENOXY)-BUTYRIC ACID; 4-(3-FORMYLPHENOXY)BUTANOIC ACID; 4-(3-FORMYLPHENOXY)OXANE-4-CARBOXYLIC ACID; 4-(3-FORMYLPHENOXY)PENTANOIC ACID; 4-(3-FORMYLPHENOXY)THIANE-4-CARBOXYLIC ACID; 4-(3-FORMYLPHENOXYMETHYL)-1,3-THIAZOLE-2-CARBOXYLIC ACID; 4-(3-FORMYLPHENOXYMETHYL)-5-METHYLFURAN-2-CARBOXYLIC ACID; 4-(3-FORMYLPHENOXYMETHYL)BENZOIC ACID; 4-(3-FORMYLPHENYL)-2-HYDROXYBENZOIC ACID; 4-(3-FORMYLPHENYL)-2-METHOXYBENZOIC ACID; 4-(3-FORMYLPHENYL)-2-NITROBENZOIC ACID; 4-(3-FORMYLPHENYL)-3-HYDROXYBENZOIC ACID; 4-(3-FORMYLPHENYL)-3-METHOXYBENZOIC ACID; 4-(3-FORMYLPHENYL)-3-METHYLBENZOIC ACID; 4-(3-FORMYLPHENYL)NICOTINIC ACID; 4-(3-FORMYLPHENYL)PICOLINIC ACID; 4-(3-FORMYL-PYRIDIN-2-YL)-BENZOIC ACID; 4-(3-METHOXY-4-FORMYL)PHENOXYBUTYRIC ACID; 4-(3-OXOPROPYL)-BENZOIC ACID; 4-(4-FORMYL-1H-IMIDAZOL-2-YL)-BENZOIC ACID; 4-(4-FORMYL-2-METHOXYPHENOXY)BUTANOIC ACID; 4-(4-FORMYL-3,5-DIMETHOXYPHENOXY)BUTYRIC ACID; 4-(4-FORMYLPHENOXY)BENZOIC ACID; 4-(4-FORMYLPHENOXY)BUTANOIC ACID; 4-(4-FORMYLPHENOXY)OXANE-4-CARBOXYLIC ACID; 4-(4-FORMYLPHENOXY)PENTANOIC ACID; 4-(4-FORMYLPHENOXY)THIANE-4-CARBOXYLIC ACID; 4-(4-FORMYLPHENOXYMETHYL)-1,3-THIAZOLE-2-CARBOXYLIC ACID; 4-(4-FORMYLPHENOXYMETHYL)-5-METHYLFURAN-2-CARBOXYLIC ACID; 4-(4-FORMYLPHENOXYMETHYL)BENZOIC ACID; 4-(4-FORMYLPHENYL)-2-HYDROXYBENZOIC ACID; 4-(4-FORMYLPHENYL)-2-METHOXYBENZOIC ACID; 4-(4-FORMYLPHENYL)-2-NITROBENZOIC ACID; 4-(4-FORMYLPHENYL)-3-HYDROXYBENZOIC ACID; 4-(4-FORMYLPHENYL)-3-METHOXYBENZOIC ACID; 4-(4-FORMYLPHENYL)-3-METHYLBENZOIC ACID; 4-(4-FORMYLPHENYL)NICOTINIC ACID; 4-(4-FORMYLPHENYL)PICOLINIC ACID; 4-(5-CARBOXY-2-FLUOROPHENYL)-2-FORMYLPHENOL; 4-(5-FORMYL-2-FURYL)BENZOIC ACID; 4-(5-FORMYL-2-FURYL)THIOPHENE-2-CARBOXYLIC ACID; 4-(5-FORMYL-3-THIENYL)BENZOIC ACID; 4-(5-FORMYL-FURAN-2-YL)-2-HYDROXY-BENZOIC ACID; 4-(5-FORMYL-FURAN-2-YL)-3-METHYL-BENZOIC ACID; 4-(5-FORMYLTHIOPHEN-2-YL)-2-CHLOROBENZOIC ACID; 4-(5-FORMYLTHIOPHEN-2-YL)-2-FLUOROBENZOIC ACID; 4-(5-FORMYLTHIOPHEN-2-YL)-2-HYDROXYBENZOIC ACID; 4-(5-FORMYLTHIOPHEN-2-YL)-2-METHOXYBENZOIC ACID; 4-(5-FORMYLTHIOPHEN-2-YL)-2-NITROBENZOIC ACID; 4-(5-FORMYLTHIOPHEN-2-YL)-3-FLUOROBENZOIC ACID; 4-(5-FORMYLTHIOPHEN-2-YL)-3-HYDROXYBENZOIC ACID; 4-(5-FORMYLTHIOPHEN-2-YL)-3-METHOXYBENZOIC ACID; 4-(5-FORMYLTHIOPHEN-2-YL)-3-METHYLBENZOIC ACID; 4-(5-FORMYLTHIOPHEN-2-YL)BENZOIC ACID; 4-(5-FORMYLTHIOPHEN-2-YL)NICOTINIC ACID; 4-(5-FORMYLTHIOPHEN-2-YL)PICOLINIC ACID; 4'-(BENZYLOXY)-3'-FORMYL[1,1-BIPHENYL]-3-CARBOXYLIC ACID; 4'-(BENZYLOXY)-3'-FORMYL[1,1-BIPHENYL]-4-CARBOXYLIC ACID; 4,5-DIOXOVALERIC ACID; 4-[(2,6-DICHLORO-4-FORMYLPHENOXY)METHYL]BENZOIC ACID; 4-[(2-BROMO-4-FORMYLPHENOXY)METHYL]BENZOIC ACID; 4-[(2-CHLORO-4-FORMYL-6-METHOXYPHENOXY)METHYL]BENZOIC ACID; 4-[(2-CHLORO-6-ETHOXY-4-FORMYLPHENOXY)METHYL]BENZOIC ACID; 4-[(2-FORMYL-6-METHOXYPHENOXY)METHYL]BENZOIC ACID; 4-[(2-FORMYLPHENOXY)METHYL]BENZOIC ACID; 4-[(3-FORMYLPHENOXY)METHYL]-5-METHYLISOXAZOLE-3-CARBOXYLIC ACID; 4-[(4-BROMO-2-FORMYLPHENOXY)METHYL]BENZOIC ACID; 4-[(4-FORMYL-2-METHOXYPHENOXY)METHYL]BENZOIC ACID; 4-[(4-FORMYL-3-HYDROXYPHENOXY)METHYL]BENZENECARBOXYLIC ACID; 4-[(4-FORMYLPHENOXY)METHYL]-5-METHYLISOXAZOLE-3-CARBOXYLIC ACID; 4-[(Z)-2-(3-FORMYL-4-HYDROXYPHENYL)DIAZENYL]BENZENECARBOXYLIC ACID; 4-[1-(HYDROXYMETHYLENE)-2-OXOETHYL]-3-NITROBENZOIC ACID; 4-[2-(3-FORMYL-INDOL-1-YL)-ACETYLAMINO]-BENZOIC ACID; 4-[3-(2-CHLOROPHENYL)-4-FORMYL-1H-PYRAZOL-1-YL]BENZOIC ACID; 4-[4-FORMYL-3-(4-METHOXYPHENYL)-1H-PYRAZOL-1-YL]BENZOIC ACID; 4-ACETYL-5-FORMYL-3-METHYL-PYRROLE-2-CARBOXYLIC ACID; 4-AMINO-2'-FORMYL[1,1-BIPHENYL]-3-CARBOXYLIC ACID; 4-AMINO-4'-FORMYL[1,1-BIPHENYL]-3-CARBOXYLIC ACID; 4-AMINO-PYRIDINE-3-CARBALDEHYDE TRIFLUOROACETATE; 4-BROMO-2-FORMYL-5-NITRO-BENZOIC ACID; 4-BROMO-2-FORMYLBENZOIC ACID; 4-BROMO-3-FORMYL-6-INDAZOLECARBOXYLIC ACID; 4-CARBONYLCYCLOHEXANECARBOXYLIC ACID; 4-CARBONYLPHENYLACETIC ACID; 4-CARBOXY-2,6-DIFLUOROBENZALDEHYDE; 4-CARBOXYBENZALDEHYDE; 4-CHLORO-2-(2-FORMYLPHENYL)BENZOIC ACID; 4-CHLORO-2-(3-FORMYLPHENYL)BENZOIC ACID; 4-CHLORO-2-(4-FORMYLPHENYL)BENZOIC ACID; 4-CHLORO-2-FORMYL-5-NITRO-BENZOIC ACID; 4-CHLORO-3-(2-FORMYLPHENYL)BENZOIC ACID; 4-CHLORO-3-(3-FORMYLPHENYL)BENZOIC ACID; 4-CHLORO-3-(4-FORMYLPHENYL)BENZOIC ACID; 4-CHLORO-3-(5-FORMYL-FURAN-2-YL)-BENZOIC ACID; 4-CHLORO-6-CARBOXYLIC ACID-3-(1H)INDAZOLE CARBOXALDEHYDE; 4-CYANO-2-FORMYLBENZOIC ACID; 4-CYCLOPROPOXY-2-FORMYLBENZOIC ACID; 4-CYCLOPROPOXY-2-FORMYLNICOTINIC ACID; 4-CYCLOPROPOXY-3-FORMYLBENZOIC ACID; 4-CYCLOPROPOXY-3-FORMYLPICOLINIC ACID;

ACID; 4-CYCLOPROPOXY-5-FORMYLNICOTINIC ACID; 4-CYCLOPROPOXY-5-FORMYLPICOLINIC ACID; 4-CYCLOPROPOXY-6-FORMYLNICOTINIC ACID; 4-CYCLOPROPOXY-6-FORMYLPICOLINIC ACID; 4-ETHYL-5-FORMYL-3-METHYL-1H-PYRROLE-2-CARBOXYLIC ACID; 4-FLUORO-2-(2-FORMYLPHENYL)BENZOIC ACID; 4-FLUORO-2-(3-FORMYLPHENYL)BENZOIC ACID; 4-FLUORO-2-(4-FORMYLPHENYL)BENZOIC ACID; 4-FLUORO-3-(2-FORMYLPHENYL)BENZOIC ACID; 4-FLUORO-3-(3-FORMYLPHENYL)BENZOIC ACID; 4-FLUORO-3-(4-FORMYLPHENYL)BENZOIC ACID; 4-FLUORO-3-FORMYL-6-INDAZOLECARBOXYLIC ACID; 4-FLUORO-3-FORMYL-BENZOIC ACID; 4-FLUORO-5-FORMYL-3-METHYL-1H-PYRROLE-2-CARBOXYLIC ACID; 4-FORMYL-[1,1-BIPHENYL]-2-CARBOXYLIC ACID; 4-FORMYL-1-(2-METHOXYPHENYL)-2,5-DIMETHYL-1H-PYRROLE-3-CARBOXYLIC ACID; 4-FORMYL-1-(2-METHYLPHENYL)-1H-PYRAZOLE-3-CARBOXYLIC ACID; 4-FORMYL-1-(3-METHOXYPHENYL)-1H-PYRAZOLE-3-CARBOXYLIC ACID; 4-FORMYL-1-(3-METHOXYPHENYL)-2,5-DIMETHYL-1H-PYRROLE-3-CARBOXYLIC ACID; 4-FORMYL-1-(3-METHYLPHENYL)-1H-PYRAZOLE-3-CARBOXYLIC ACID; 4-FORMYL-1-(4-ISOPROPYLPHENYL)-1H-PYRAZOLE-3-CARBOXYLIC ACID; 4-FORMYL-1-(4-METHOXYBENZYL)-2,5-DIMETHYL-1H-PYRROLE-3-CARBOXYLIC ACID; 4-FORMYL-1-(4-METHOXYPHENYL)-1H-PYRAZOLE-3-CARBOXYLIC ACID; 4-FORMYL-1-(4-METHYLPHENYL)-1H-PYRAZOLE-3-CARBOXYLIC ACID; 4-FORMYL-1-(MESITYLMETHYL)-2,5-DIMETHYL-1H-PYRROLE-3-CARBOXYLIC ACID; 4-FORMYL-1,2,5-TRIMETHYL-1H-PYRROLE-3-CARBOXYLIC ACID; 4-FORMYL-1-[3-(TRIFLUOROMETHYL)PHENYL]-1H-PYRAZOLE-3-CARBOXYLIC ACID; 4-FORMYL-1H-IMIDAZOLE-2-CARBOXYLIC ACID; 4-FORMYL-1H-PYRAZOLE-3-CARBOXYLIC ACID; 4-FORMYL-1H-PYRROLE-2-CARBOXYLIC ACID; 4-FORMYL-1-METHYL-1H-PYRROLE-2-CARBOXYLIC ACID; 4-FORMYL-1-METHYL-1H-PYRROLE-3-CARBOXYLIC ACID; 4-FORMYL-1-PHENYL-1H-PYRAZOLE-3-CARBOXYLIC ACID; 4-FORMYL-2,5-DIMETHYL-1-(2-METHYLBENZYL)-1H-PYRROLE-3-CARBOXYLIC ACID; 4-FORMYL-2,5-DIMETHYL-1-(2-METHYLPHENYL)-1H-PYRROLE-3-CARBOXYLIC ACID; 4-FORMYL-2,5-DIMETHYL-1-(3-METHYLBENZYL)-1H-PYRROLE-3-CARBOXYLIC ACID; 4-FORMYL-2,5-DIMETHYL-1-(3-METHYLPHENYL)-1H-PYRROLE-3-CARBOXYLIC ACID; 4-FORMYL-2,5-DIMETHYL-1-(4-METHYLBENZYL)-1H-PYRROLE-3-CARBOXYLIC ACID; 4-FORMYL-2,5-DIMETHYL-1-(4-METHYLPHENYL)-1H-PYRROLE-3-CARBOXYLIC ACID; 4-FORMYL-2,5-DIMETHYL-1H-PYRROLE-3-CARBOXYLIC ACID; 4-FORMYL-2,5-DIMETHYL-1-PHENYL-1H-PYRROLE-3-CARBOXYLIC ACID; 4-FORMYL-2-HYDROXYBENZOIC ACID; 4'-FORMYL-2'ETHYLBIPHENYL-4-CARBOXYLIC ACID; 4-FORMYL-3,5-DIMETHYL-1H-PYRROLE-2-CARBOXYLIC ACID; 4-FORMYL-3-HYDROXYBENZOIC ACID; 4-FORMYL-3-METHOXY-PHENOXYACETIC ACID; 4-FORMYL-3-THIOPHENECARBOXYLIC ACID; 4'-FORMYL-4-HYDROXY[1,1'-BIPHENYL]-3-CARBOXYLIC ACID; 4-FORMYLBICYCLO[2.2.2]OCTANE-1-CARBOXYLIC ACID; 4'-FORMYL-BIPHENYL-2-CARBOXYLIC ACID; 4'-FORMYLBIPHENYL-3-CARBOXYLIC ACID; 4'-FORMYL-BIPHENYL-4-CARBOXYLIC ACID; 4-FORMYLCINNAMIC ACID; 4-FORMYLNAPHTHALENE-1-CARBOXYLIC ACID; 4-FORMYLNICOTINIC ACID; 4-FORMYLPHENOXYACETIC ACID; 4-FORMYLQUINOLINE-6-CARBOXYLIC ACID; 4-FORMYLQUINOLINE-8-CARBOXYLIC ACID; 4-PIPERIDINECARBOXYLIC ACID, 4-FORMYL-; 4-PYRIMIDINECARBOXYLIC ACID, 5-FORMYL-; 5-((3-FORMYL-1H-INDOL-1-YL)METHYL)FURAN-2-CARBOXYLIC ACID; 5-(2-CARBOXYTHIOPHENE-4-YL)-2-FORMYLPHENOL; 5-(2-CHLORO-4-FORMYLPHENOXY)PENTANOIC ACID; 5-(2-CHLORO-4-FORMYLPHENOXYMETHYL)FURAN-2-CARBOXYLIC ACID; 5-(2-CHLORO-4-FORMYLPHENOXYMETHYL)FURAN-3-CARBOXYLIC ACID; 5-(2-CHLORO-4-FORMYLPHENOXYMETHYL)OXOLANE-2-CARBOXYLIC ACID; 5-(2-FORMYL-1H-PYRROL-1-YL)-1-PHENYL-1H-PYRAZOLE-4-CARBOXYLIC ACID; 5-(2-FORMYLPHENYL)-2-FUROIC ACID; 5-(2-FORMYLPHENYL)-2-HYDROXYISONICOTINIC ACID; 5-(2-FORMYLPHENYL)-2-HYDROXYNICOTINIC ACID; 5-(2-FORMYLPHENYL)-2-METHOXYNICOTINIC ACID; 5-(2-FORMYLPHENYL)-2-THIOPHENECARBOXYLIC ACID; 5-(2-FORMYLPHENYL)-6-HYDROXYNICOTINIC ACID; 5-(2-FORMYLPHENYL)NICOTINIC ACID; 5-(2-FORMYLPHENYL)-PICOLINIC ACID; 5-(2-FORMYLTHIOPHEN-4-YL)-2-AMINOISONICOTINIC ACID; 5-(2-FORMYLTHIOPHEN-4-YL)-2-AMINONICOTINIC ACID; 5-(2-FORMYLTHIOPHEN-4-YL)-2-CHLOROBENZOIC ACID; 5-(2-FORMYLTHIOPHEN-4-YL)-2-CHLOROISONICOTINIC ACID; 5-(2-FORMYLTHIOPHEN-4-YL)-2-CHLORONICOTINIC ACID; 5-(2-FORMYLTHIOPHEN-4-YL)-2-FLUOROBENZOIC ACID; 5-(2-FORMYLTHIOPHEN-4-YL)-2-HYDROXYISONICOTINIC ACID; 5-(2-FORMYLTHIOPHEN-4-YL)-2-HYDROXYNICOTINIC ACID; 5-(2-FORMYLTHIOPHEN-4-YL)-2-METHOXYNICOTINIC ACID; 5-(2-FORMYLTHIOPHEN-4-YL)-3-AMINOBENZOIC ACID; 5-(2-FORMYLTHIOPHEN-4-YL)-6-HYDROXYNICOTINIC ACID; 5-(2-FORMYLTHIOPHEN-4-YL)NICOTINIC ACID; 5-(2-FORMYLTHIOPHEN-4-YL)PICOLINIC ACID; 5-(3-ALLYLOXY-4-FORMYLPHENOXY)-PENTANOIC ACID; 5-(3-CARBOXY-4-CHLOROPHENYL)-2-FORMYLPHENOL; 5-(3-CARBOXY-5-FLUOROPHENYL)-2-FORMYLPHENOL; 5-(3-CARBOXYPHENYL)-2-FORMYLPHENOL; 5-(3-FORMYL-1H-INDOL-1-YL)THIOPHENE-2-CARBOXYLIC ACID; 5-(3-FORMYLPHENOXY)PENTANOIC ACID; 5-(3-FORMYLPHENOXYMETHYL)-1,2-OXAZOLE-3-CARBOXYLIC ACID; 5-(3-FORMYLPHENOXYMETHYL)-2-METHYLFURAN-3-CARBOXYLIC ACID; 5-(3-FORMYLPHENOXYMETHYL)-3-METHYLFURAN-2-CARBOXYLIC ACID; 5-(3-FORMYLPHENOXYMETHYL)FURAN-3-CARBOXYLIC ACID; 5-(3-FORMYLPHENOXYMETHYL)OXOLANE-2-CARBOXYLIC ACID; 5-(3-FORMYLPHENYL)-2-FUROIC ACID; 5-(3-FORMYLPHENYL)-2-HYDROXYISONICOTINIC ACID; 5-(3-FORMYLPHENYL)-2-HYDROXYNICOTINIC ACID; 5-(3-FORMYLPHENYL)-2-METHOXYNICOTINIC ACID; 5-(3-FORMYLPHENYL)-6-HYDROXYNICOTINIC ACID; 5-(3-FORMYLPHENYL)NICOTINIC ACID; 5-(3-FORMYLPHENYL)PICOLINIC ACID; 5-(4-CARBOXY-3-FLUOROPHENYL)-2-FORMYLPHENOL; 5-(4-CARBOXYPHENYL)-2-FORMYLPHENOL; 5-(4-

FORMYL-3,5-DIMETHOXYPHENOXY)PENTANOIC ACID; 5-(4-FORMYL-3-HYDROXY-PHENOXY)-PENTANOIC ACID; 5-(4-FORMYLPHENOXY)PENTANOIC ACID; 5-(4-FORMYLPHENOXYMETHYL)-1,2-OXAZOLE-3-CARBOXYLIC ACID; 5-(4-FORMYLPHENOXYMETHYL)-2-METHYLFURAN-3-CARBOXYLIC ACID; 5-(4-FORMYLPHENOXYMETHYL)-3-METHYLFURAN-2-CARBOXYLIC ACID; 5-(4-FORMYLPHENOXYMETHYL)FURAN-3-CARBOXYLIC ACID; 5-(4-FORMYLPHENOXYMETHYL)OXOLANE-2-CARBOXYLIC ACID; 5-(4-FORMYLPHENYL)-2-FUROIC ACID; 5-(4-FORMYLPHENYL)-2-HYDROXYISONICOTINIC ACID; 5-(4-FORMYLPHENYL)-2-HYDROXYNICOTINIC ACID; 5-(4-FORMYLPHENYL)-2-METHOXYNICOTINIC ACID; 5-(4-FORMYLPHENYL)-6-HYDROXYNICOTINIC ACID; 5-(4-FORMYLPHENYL)NICOTINIC ACID; 5-(4-FORMYLPHENYL)-PICOLINIC ACID; 5-(5-CARBOXY-2-FLUOROPHENYL)-2-FORMYLPHENOL; 5-(5-FORMYL-2-FURYL)-2-HYDROXYBENZOIC ACID; 5-(5-FORMYL-2-FURYL)-2-METHYLBENZOIC ACID; 5-(5-FORMYL-2-THIENYL)-2-HYDROXYBENZOIC ACID; 5-(5-FORMYL-FURAN-2-YL)-THIOPHENE-2-CARBOXYLIC ACID; 5-(5-FORMYLPYRIDIN-2-YL)THIOPHENE-2-CARBOXYLIC ACID; 5-(5-FORMYLTHIOPHEN-2-YL)-2-AMINOISONICOTINIC ACID; 5-(5-FORMYLTHIOPHEN-2-YL)-2-AMINONICOTINIC ACID; 5-(5-FORMYLTHIOPHEN-2-YL)-2-CHLOROBENZOIC ACID; 5-(5-FORMYLTHIOPHEN-2-YL)-2-CHLOROISONICOTINIC ACID; 5-(5-FORMYLTHIOPHEN-2-YL)-2-CHLORONICOTINIC ACID; 5-(5-FORMYLTHIOPHEN-2-YL)-2-FLUOROBENZOIC ACID; 5-(5-FORMYLTHIOPHEN-2-YL)-2-HYDROXYISONICOTINIC ACID; 5-(5-FORMYLTHIOPHEN-2-YL)-2-HYDROXYNICOTINIC ACID; 5-(5-FORMYLTHIOPHEN-2-YL)-2-METHOXYNICOTINIC ACID; 5-(5-FORMYLTHIOPHEN-2-YL)-3-AMINOBENZOIC ACID; 5-(5-FORMYLTHIOPHEN-2-YL)-6-HYDROXYNICOTINIC ACID; 5-(5-FORMYL-THIOPHEN-2-YL)-FURAN-2-CARBOXYLIC ACID; 5-(5-FORMYLTHIOPHEN-2-YL)NICOTINIC ACID; 5-(5-FORMYLTHIOPHEN-2-YL)PICOLINIC ACID; 5-(5-FORMYL-THIOPHEN-3-YL)-FURAN-2-CARBOXYLIC ACID; 5-(6-FORMYLPYRIDIN-2-YL)THIOPHENE-2-CARBOXYLIC ACID; 5-[(2-FORMYL-6-METHOXYPHENOXY)METHYL]-2-FUROIC ACID; 5-[(2-FORMYLPHENOXY)METHYL]-2-FUROIC ACID; 5-[(3-FORMYLPHENOXY)METHYL]-2-FUROIC ACID; 5-[(4-FORMYLPHENOXY)METHYL]-2-FUROIC ACID; 5-BROMO-2-FORMYL-BENZOIC ACID; 5-BROMO-3-FORMYL-1H-INDOLE-2-CARBOXYLIC ACID; 5-CARBOXYVANILLIN; 5-CHLORO-2-(3-OXOPROPYL)-BENZOIC ACID; 5-CHLORO-2-FORMYL-BENZOIC ACID; 5-CHLORO-3-(2-FORMYLPHENYL)BENZOIC ACID; 5-CHLORO-3-(3-FORMYLPHENYL)BENZOIC ACID; 5-CHLORO-3-(4-FORMYLPHENYL)BENZOIC ACID; 5-CHLORO-3-FORMYL-1H-INDOLE-2-CARBOXYLIC ACID; 5-CHLORO-4-FORMYL-1-METHYL-1H-PYRROLE-3-CARBOXYLIC ACID; 5-CHLORO-4-FORMYL-1-PHENYL-1H-PYRAZOLE-3-CARBOXYLIC ACID; 5-CYCLOPROPOXY-2-FORMYLBENZOIC ACID; 5-CYCLOPROPOXY-2-FORMYLISONICOTINIC ACID; 5-CYCLOPROPOXY-3-FORMYLNICOTINIC ACID; 5-CYCLOPROPOXY-3-FORMYLPICOLINIC ACID; 5-CYCLOPROPOXY-4-FORMYLNICOTINIC ACID; 5-CYCLOPROPOXY-4-FORMYLPICOLINIC ACID; 5-CYCLOPROPOXY-6-FORMYLNICOTINIC ACID; 5-CYCLOPROPOXY-6-FORMYLPICOLINIC ACID; 5-FLUORO-2-(2-FORMYLPHENYL)BENZOIC ACID; 5-FLUORO-2-(3-FORMYLPHENYL)BENZOIC ACID; 5-FLUORO-2-(4-FORMYLPHENYL)BENZOIC ACID; 5-FLUORO-2-FORMYLBENZOIC ACID; 5-FLUORO-3-(2-FORMYLPHENYL)BENZOIC ACID; 5-FLUORO-3-(3-FORMYLPHENYL)BENZOIC ACID; 5-FLUORO-3-(4-FORMYLPHENYL)BENZOIC ACID; 5-FLUORO-3-FORMYL-1H-INDOLE-2-CARBOXYLIC ACID; 5'-FORMYL-[2,2']BIFURANYL-5-CARBOXYLIC ACID; 5'-FORMYL-[2,2]BITHIOPHENYL-5-CARBOXYLIC ACID; 5'-FORMYL-[2,3']BITHIOPHENYL-5-CARBOXYLIC ACID; 5-FORMYL-1-BENZOFURAN-2-CARBOXYLIC ACID; 5-FORMYL-1H-PYRROLE-2-CARBOXYLIC ACID; 5-FORMYL-1-METHYL-1H-PYRROLE-2-CARBOXYLIC ACID; 5-FORMYL-2,4-DIMETHOXYBENZOIC ACID; 5-FORMYL-2,4-DIMETHYL-1H-PYRROLE-3-CARBOXYLIC ACID; 5-FORMYL-2-FURANCARBOXYLIC ACID; 5-FORMYL-2-METHOXYBENZOIC ACID; 5-FORMYL-2-PYRIDINECARBOXYLIC ACID; 5-FORMYL-2-THIOPHENECARBOXYLIC ACID; 5'-FORMYL-3,3'-BITHIOPHENE-5-CARBOXYLIC ACID; 5-FORMYL-3-METHYL-1H-PYRROLE-2-CARBOXYLIC ACID; 5-FORMYL-4-HYDROXYPICOLINIC ACID; 5-FORMYL-4-METHYL-1H-PYRROLE-2-CARBOXYLIC ACID; 5-FORMYL-4-METHYL-1H-PYRROLE-3-CARBOXYLIC ACID; 5-FORMYL-4-METHYLTHIOPHENE-2-CARBOXYLIC ACID; 5-FORMYL-4-PHENANTHRENECARBOXYLIC ACID; 5-FORMYLNICOTINIC ACID; 5-FORMYLSALICYLIC ACID; 5-FORMYL-THIAZOLE-4-CARBOXYLIC ACID; 5-FORMYLTHIOPHENE-3-CARBOXYLIC ACID; 5-THIAZOLECARBOXYLIC ACID, 2-FORMYL; 6-(2-CARBOXYTHIOPHENE-4-YL)-2-FORMYLPHENOL; 6-(2-FORMYLPHENYL)NICOTINIC ACID; 6-(2-FORMYLPHENYL)PICOLINIC ACID; 6-(2-FORMYLTHIOPHEN-4-YL)NICOTINIC ACID; 6-(2-FORMYLTHIOPHEN-4-YL)PICOLINIC ACID; 6-(3-CARBOXY-4-CHLOROPHENYL)-2-FORMYLPHENOL; 6-(3-CARBOXY-5-FLUOROPHENYL)-2-FORMYLPHENOL; 6-(3-CARBOXYPHENYL)-2-FORMYLPHENOL; 6-(3-FORMYLPHENYL)NICOTINIC ACID; 6-(3-FORMYLPHENYL)PICOLINIC ACID; 6-(4-CARBOXYPHENYL)-2-FORMYLPHENOL; 6-(4-FORMYLIMIDAZOL-2-YL)2,3-DIMETHOXYBENZOIC ACID; 6-(4-FORMYLPHENYL)NICOTINIC ACID; 6-(4-FORMYLPHENYL)PICOLINIC ACID; 6-(5-CARBOXY-2-FLUOROPHENYL)-2-FORMYLPHENOL; 6-(5-FORMYLTHIOPHEN-2-YL)NICOTINIC ACID; 6-(5-FORMYLTHIOPHEN-2-YL)PICOLINIC ACID; 6-AMINO-3-(2-FORMYLPHENYL)PICOLINIC ACID; 6-AMINO-3-(3-FORMYLPHENYL)PICOLINIC ACID; 6-AMINO-3-(4-FORMYLPHENYL)PICOLINIC ACID; 6-BROMO-3-FORMYL-4-INDAZOLECARBOXYLIC ACID; 6-CHLORO-2-(2-FORMYLPHENYL)BENZOIC ACID; 6-CHLORO-2-(3-FORMYLPHENYL)BENZOIC ACID; 6-CHLORO-2-(4-FORMYLPHENYL)BENZOIC ACID; 6-CHLORO-3-CARBOXALDEHYDE-(1H)INDAZOLE-4-CARBOXYLIC ACID; 6-FLUORO-2-(2-FORMYLPHENYL)BENZOIC ACID; 6-FLUORO-2-(3-FORMYLPHENYL)BENZOIC ACID; 6-FLUORO-2-(4-FORMYLPHENYL)BENZOIC ACID; 6-FLUORO-3-FORMYL-4-INDAZOLECARBOXYLIC ACID; 6-FORMYL-2,3-DIMETHOXYBENZOIC ACID; 6-FORMYLPYRIDINE-2-CARBOXYLIC ACID; 7-OXO-

HEPTANOIC ACID; 8-FORMYL-4H-1,3-BENZODIOXINE-6-CARBOXYLIC ACID; 9-OXONONANOIC ACID; AC-VAD-CHO; ALAHOPCIN; BUTYRAMIDO-MALONALDEHYDIC ACID; CHEMDIV-BB BB01-2130; D-(+) GLUCURONIC ACID; D-GLUCURONIC ACID, [6-14C]; EPSILON-PYRROLE-LYSINE; FORPHENICINE; GLYOXYLIC ACID; GLYOXYLIC ACID MONOHYDRATE; L-2-AMINOADIPATE 6-SEMIALDEHYDE; LABOTEST-BB LT00441298; L-IDURONIC ACID, SODIUM SALT; MORPHOLIN-4-YL-ACETALDEHYDE CF3CO2H; MUCOBROMIC ACID; MUCOCHLORIC ACID; MURAMIC ACID; MURAMIC ACID HYDRATE; N-(5-FORMYLPYRIMIDIN-2-YL)GLYCINE; N-(5-FORMYLPYRIMIDIN-2-YL)-N-METHYLGLYCINE; N-ACETYLMURAMIC ACID; PHENACETURIC ACID,-ALPHA-FORMYL-ALPHA-METHYL-; SUCCINIC SEMIALDEHYDE; TRAUMATIN; TUCARESOL; VELARESOL

List No. 6 anilines: Anilines selected from the list of: 2-((5-[3-(DIMETHYLAMINO)PHENYL]-1,3,4-OXADIAZOL-2-YL)SULFANYL)ACETIC ACID; (3-DIMETHYLAMINO-PHENOXY)-ACETIC ACID; 5-OXO-(+/–)-TRANS-4-(2-(N,N-DIMETHYLAMINO)PHENYL)-PYRROLIDINE-2-CARBOXYLIC ACID; 5-OXO-(+/–)-TRANS-4-(3-(N,N-DIMETHYLAMINO)PHENYL)-PYRROLIDINE-2-CARBOXYLIC ACID; (2S,4S)-1-(TERT-BUTOXYCARBONYL)-4-[3-(DIMETHYLAMINO)PHENOXY]-2-PYRROLIDINECARBOXYLIC ACID; 3-[3-(DIMETHYLAMINO)PHENOXY]PROPANOIC ACID; 2-[3-(DIMETHYLAMINO)PHENOXY] PROPANOIC ACID; 2-[3-(DIMETHYLAMINO)PHENOXY]-3-METHYLBUTANOIC ACID; 4-[3-(DIMETHYLAMINO)PHENOXY]BUTANOIC ACID; 2-AMINO-3-[2-(DIMETHYLAMINO)PHENYL]PROPANOIC ACID; 3-[2-(DIMETHYLAMINO)PHENYL]-2-[(TERT-BUTOXY)CARBONYLAMINO]PROPANOIC ACID; (2S,4R)-4-[3-(DIMETHYLAMINO)PHENOXY]-1-[(1-TERT-BUTOXY)CARBONYL]PYRROLIDINE-2-CARBOXYLIC ACID; 2-(2-(DIMETHYLAMINO)PHENYL)ACETIC ACID; 2-(3-(DIMETHYLAMINO)PHENYL)ACETIC ACID; 3-(DIMETHYLAMINO)-BENZENEPROPANOIC ACID; (4S)-4-AMINO-4-[2-(DIMETHYLAMINO)PHENYL]BUTANOIC ACID; (5S)-5-AMINO-5-[2-(DIMETHYLAMINO)PHENYL] PENTANOIC ACID; (5R)-5-AMINO-5-[2-(DIMETHYLAMINO)PHENYL]PENTANOIC ACID; (4R)-4-AMINO-4-[2-(DIMETHYLAMINO)PHENYL]BUTANOIC ACID; 3-[2-(DIMETHYLAMINO)PHENYL]PROP-2-ENOIC ACID; 3-[2-CHLORO-6-(DIMETHYLAMINO)PHENYL]PROP-2-ENOIC ACID; (2E)-3-[4-BROMO-2-(DIMETHYLAMINO)PHENYL]PROP-2-ENOIC ACID; 1-(4-AMINO-2-DIMETHYLAMINOPHENYL)-ACETIC ACID; 2-([2-(DIMETHYLAMINO)PHENYL]SULFAMOYL)ACETIC ACID; 3-([2-(DIMETHYLAMINO)PHENYL]SULFAMOYL) PROPANOIC ACID; 2-([3-CHLORO-2-(DIMETHYLAMINO)PHENYL]SULFAMOYL)ACETIC ACID; 4-([2-(DIMETHYLAMINO)PHENYL]SULFAMOYL)BUTANOIC ACID; 2-((5-[3-(DIMETHYLAMINO)PHENYL]-4H-1,2,4-TRIAZOL-3-YL)SULFANYL)ACETIC ACID; 3-([3-CHLORO-2-(DIMETHYLAMINO)PHENYL]SULFAMOYL) PROPANOIC ACID; (2E)-3-([2-(DIMETHYLAMINO) PHENYL]CARBAMOYL)PROP-2-ENOIC ACID; 2-([2-(DIMETHYLAMINO)PHENYL]CARBAMOYL) CYCLOPROPANE-1-CARBOXYLIC ACID; 2-([3-CHLORO-2-(DIMETHYLAMINO)PHENYL] CARBAMOYL)CYCLOPROPANE-1-CARBOXYLIC ACID; 3-([3-CHLORO-2-(DIMETHYLAMINO)PHENYL]CARBAMOYL)PROPANOIC ACID; 5-([2-(DIMETHYLAMINO)PHENYL]CARBAMOYL)PENTANOIC ACID; (2E)-3-([3-CHLORO-2-(DIMETHYLAMINO) PHENYL]CARBAMOYL)PROP-2-ENOIC ACID; 4-([3-CHLORO-2-(DIMETHYLAMINO)PHENYL]CARBAMOYL)BUTANOIC ACID; 3-([2-(DIMETHYLAMINO) PHENYL]CARBAMOYL)PROPANOIC ACID; 4-([2-(DIMETHYLAMINO)PHENYL]CARBAMOYL) BUTANOIC ACID; 5-[3-(DIMETHYLAMINO) PHENOXY]PENTANOIC ACID; 2-(([3-CHLORO-2-(DIMETHYLAMINO)PHENYL]CARBAMOYL) METHOXY)ACETIC ACID; 2-(([2-(DIMETHYLAMINO) PHENYL]CARBAMOYL)METHOXY)ACETIC ACID; (2S)-2-AMINO-2-[2-(DIMETHYLAMINO)PHENYL] ACETIC ACID; (2R)-2-AMINO-2-[2-(DIMETHYLAMINO)PHENYL]ACETIC ACID; (2S)-2-AMINO-2-[3-(DIMETHYLAMINO)PHENYL]ACETIC ACID; (2R)-2-AMINO-2-[3-(DIMETHYLAMINO)PHENYL]ACETIC ACID; 2-[3-(DIMETHYLAMINO)PHENOXY]BUTANOIC ACID; 3-[3-(DIMETHYLAMINO)PHENOXY]-2-(METHYLAMINO)PROPANOIC ACID; 3-[3-(DIMETHYLAMINO)PHENOXY]-2-(ETHYLAMINO) PROPANOIC ACID; 3-[3-(DIMETHYLAMINO) PHENOXY]-2-(PROPYLAMINO)PROPANOIC ACID; 3-[3-(DIMETHYLAMINO)PHENOXY]-2-(PROPAN-2-YLAMINO)PROPANOIC ACID; 2-(CYCLOPROPYLAMINO)-3-[3-(DIMETHYLAMINO)PHENOXY]PROPANOIC ACID; [5-(3-DIMETHYLAMINO-PHENYL)-4-METHYL-4H-[1,2,4]TRIAZOL-3-YLSULFANYL]-ACETIC ACID; 2-AMINO-3-[3-(DIMETHYLAMINO) PHENOXY]PROPANOIC ACID; 2-([2-(DIMETHYLAMINO)PHENYL]SULFAMOYL) PROPANOIC ACID; 2-([3-CHLORO-2-(DIMETHYLAMINO)PHENYL]SULFAMOYL) PROPANOIC ACID; 2-([2-(DIMETHYLAMINO) PHENYL]CARBAMOYL)ACETIC ACID; 4-[3-(DIMETHYLAMINO)PHENOXY]-2-(ETHYLAMINO) BUTANOIC ACID; 2-[3-(DIMETHYLAMINO) PHENOXY]CYCLOPENTANE-1-CARBOXYLIC ACID; 2-AMINO-4-[3-(DIMETHYLAMINO)PHENOXY]BUTANOIC ACID; 3-[3-(DIMETHYLAMINO)PHENOXY] PENTANOIC ACID; 3-[3-(DIMETHYLAMINO)PHENOXY]-2-ETHOXYPROPANOIC ACID; 4-[3-(DIMETHYLAMINO)PHENOXY]-2-(METHYLAMINO) BUTANOIC ACID; 5-[3-(DIMETHYLAMINO) PHENOXYMETHYL]OXOLANE-2-CARBOXYLIC ACID; 4-[3-(DIMETHYLAMINO)PHENOXY]PENTANOIC ACID; 2-([3-CHLORO-2-(DIMETHYLAMINO) PHENYL]CARBAMOYL)ACETIC ACID; 3-[3-(DIMETHYLAMINO)PHENOXY]-4,4,4-TRIFLUOROBUTANOIC ACID; 4-[3-(DIMETHYLAMINO)PHENOXY]-2-ETHOXYBUTANOIC ACID; 2-[3-(DIMETHYLAMINO) PHENOXY]CYCLOHEXANE-1-CARBOXYLIC ACID; [3-BENZOYL-2-(DIMETHYLAMINO)PHENYL]ACETIC ACID; 4-(2-PYRROLIDIN-1-YL-PHENYLCARBAMOYL)-BUTYRIC ACID; 2-AMINO-3-(2-PYRROLIDINYLPHENYL)PROPANOIC ACID; 2-[(TERT-BUTOXY)CARBONYLAMINO]-3-(2-PYRROLIDINYLPHENYL)PROPANOIC ACID; 1-PHENYLPYRROLIDINE-3-CARBOXYLIC ACID; 1-(3-CHLOROPHENYL)PYRROLIDINE-3-CARBOXYLIC ACID; 1-(3-FLUOROPHENYL)PYRROLIDINE-3-CARBOXYLIC ACID; 1-(3-METHOXYPHENYL)PYRROLIDINE-3-CARBOXYLIC ACID; 1-[3-

(TRIFLUOROMETHYL)PHENYL]PYRROLIDINE-3-CARBOXYLIC ACID; 3-(1-PYRROLIDINYL)-BENZENEPROPANOIC ACID; 2-(1-PYRROLIDINYL)-BENZENEPROPANOIC ACID; (5R)-5-AMINO-5-(2-PYRROLIDINYLPHENYL)PENTANOIC ACID; (5S)-5-AMINO-5-(2-PYRROLIDINYLPHENYL)PENTANOIC ACID; (4R)-4-AMINO-4-(2-PYRROLIDINYLPHENYL)BUTANOIC ACID; (4S)-4-AMINO-4-(2-PYRROLIDINYLPHENYL)BUTANOIC ACID; 3-PYRROLIDINECARBOXYLIC ACID, 1-(2-CHLORO-3-HYDROXYPHENYL)-; (2E)-3-[2-CHLORO-6-(PYRROLIDIN-1-YL)PHENYL]PROP-2-ENOIC ACID; 3-[2-(PYRROLIDIN-1-YL)PHENYL]PROP-2-ENOIC ACID; (2E)-3-[4-BROMO-2-(PYRROLIDIN-1-YL)PHENYL]PROP-2-ENOIC ACID; 3-(([2-(PYRROLIDIN-1-YL)PHENYL]METHYL)AMINO)PROPANOIC ACID; 2-(([2-(PYRROLIDIN-1-YL)PHENYL]METHYL)AMINO)ACETIC ACID; 2-([2-(PYRROLIDIN-1-YL)PHENYL]SULFAMOYL)ACETIC ACID; (2E)-3-([2-(PYRROLIDIN-1-YL)PHENYL]CARBAMOYL)PROP-2-ENOIC ACID; (2E)-3-([3-(PYRROLIDIN-1-YL)PHENYL]CARBAMOYL)PROP-2-ENOIC ACID; 2-([3-(PYRROLIDIN-1-YL)PHENYL]SULFAMOYL)ACETIC ACID; 4-(([2-(PYRROLIDIN-1-YL)PHENYL]METHYL)AMINO)BUTANOIC ACID; 3-([3-(PYRROLIDIN-1-YL)PHENYL]CARBAMOYL)PROPANOIC ACID; 3-([2-(PYRROLIDIN-1-YL)PHENYL]CARBAMOYL)PROPANOIC ACID; 3-[2-CHLORO-6-(3-METHYLPYRROLIDIN-1-YL)PHENYL]DROP-2-ENOIC ACID; 3-[4-BROMO-2-(3-METHYLPYRROLIDIN-1-YL)PHENYL]PROP-2-ENOIC ACID; 3-[2-(3-METHYLPYRROLIDIN-1-YL)PHENYL]PROP-2-ENOIC ACID; (R)-[1-(3,5-BIS-TRIFLUOROMETHYL-PHENYL)-PYRROLIDIN-3-YLOXY]-ACETIC ACID; 4-([3-(PYRROLIDIN-1-YL)PHENYL]CARBAMOYL)BUTANOIC ACID; 5-OXO-1-(2-PYRROLIDIN-1-YL-PHENYL)-PYRROLIDINE-3-CARBOXYLIC ACID; 5-OXO-1-(3-PYRROLIDIN-1-YL-PHENYL)-PYRROLIDINE-3-CARBOXYLIC ACID; 1-(2-METHYL-3-NITROPHENYL)PYRROLIDINE-3-CARBOXYLIC ACID; 1-(3-FLUORO-5-NITROPHENYL)PYRROLIDINE-3-CARBOXYLIC ACID; 1-[2-(TRIFLUOROMETHYL)PHENYL]PYRROLIDINE-3-CARBOXYLIC ACID; 1-(2-NITROPHENYL)PYRROLIDINE-3-CARBOXYLIC ACID; 1-(2-SULFAMOYLPHENYL)PYRROLIDINE-3-CARBOXYLIC ACID; 1-[2-(METHYLSULFAMOYL)PHENYL]PYRROLIDINE-3-CARBOXYLIC ACID; 1-(2-METHYL-5-NITROPHENYL)PYRROLIDINE-3-CARBOXYLIC ACID; 1-(2-CYANOPHENYL)PYRROLIDINE-3-CARBOXYLIC ACID; 1-(3-FLUORO-2-NITROPHENYL)PYRROLIDINE-3-CARBOXYLIC ACID; 1-(2-CARBAMOYL-5-METHYLPHENYL)PYRROLIDINE-3-CARBOXYLIC ACID; 1-(2-CARBAMOYL-3-CHLOROPHENYL)PYRROLIDINE-3-CARBOXYLIC ACID; 1-(3-NITROPHENYL)PYRROLIDINE-3-CARBOXYLIC ACID; 1-(2-CARBAMOYLPHENYL)PYRROLIDINE-3-CARBOXYLIC ACID; 1-(2-CARBAMOYL-5-CHLOROPHENYL)PYRROLIDINE-3-CARBOXYLIC ACID; 2-([2-(PYRROLIDIN-1-YL)PHENYL]CARBAMOYL)ACETIC ACID; 1-(5-FLUORO-2-NITROPHENYL)PYRROLIDINE-3-CARBOXYLIC ACID; 1-(2,3-DIFLUORO-6-NITROPHENYL)PYRROLIDINE-3-CARBOXYLIC ACID; 1-(5-CHLORO-2-CYANOPHENYL)PYRROLIDINE-3-CARBOXYLIC ACID; 2-([3-(PYRROLIDIN-1-YL)PHENYL]CARBAMOYL)ACETIC ACID; 1-(2-CYANO-5-METHYLPHENYL)PYRROLIDINE-3-CARBOXYLIC ACID; 1-(3-CHLORO-2-CYANOPHENYL)PYRROLIDINE-3-CARBOXYLIC ACID N-(2-PIPERIDIN-1-YL-PHENYL)-SUCCINAMIC ACID; 4-(2-PIPERIDIN-1-YL-PHENYLCARBAMOYL)-BUTYRIC ACID; 1-(2-NITROPHENYL)PIPERIDINE-4-CARBOXYLIC ACID; 2-AMINO-2-(1-PHENYLPIPERIDIN-4-YL)ACETIC ACID; TERT-BUTOXYCARBONYLAMINO-(1-PHENYL-PIPERIDIN-4-YL)-ACETIC ACID; [(9H-FLUOREN-9-YLMETHOXYCARBONYLAMINO)]-(1-PHENYL-PIPERIDIN-4-YL)-ACETIC ACID; 2-(4-AMINO-1-(3-METHOXYPHENYL)PIPERIDIN-4-YL)ACETIC ACID; 2-(4-AMINO-1-PHENYLPIPERIDIN-4-YL)ACETIC ACID; 1-(2-NITROPHENYL)PIPERIDINE-3-CARBOXYLIC ACID; 1-[2-(METHYLSULFONYL)PHENYL]PIPERIDINE-3-CARBOXYLIC ACID; 1-[2-(METHYLSULFONYL)PHENYL]PIPERIDINE-4-CARBOXYLIC ACID; 1-(2-CYANOPHENYL)PIPERIDINE-4-CARBOXYLIC ACID; 1-(2-CYANOPHENYL)PIPERIDINE-3-CARBOXYLIC ACID; 1-PHENYL-4-PIPERIDINECARBOXYLIC ACID; 2-AMINO-3-(2-PIPERIDYLPHENYL)PROPANOIC ACID; 2-[(TERT-BUTOXY)CARBONYLAMINO]-3-[2-(4-HYDROXYPIPERIDYL)PHENYL]PROPANOIC ACID; 2-[(TERT-BUTOXY)CARBONYLAMINO]-3-(2-PIPERIDYLPHENYL)PROPANOIC ACID; (S,S)-3-METHYL-1-(2-PIPERIDINOPHENYL)BUTYLAMINE, N-ACETYL-GLUTAMATE SALT; 2-(1-PHENYLPIPERIDIN-4-YLIDENE)ACETIC ACID; (E)-3-(2-(PIPERIDIN-1-YL)PHENYL)ACRYLIC ACID; 2-(1-PHENYLPIPERIDIN-4-YL)ACETIC ACID; 1-[(2-ISOPROPYLSULFONYL-5-TRIFLUOROMETHYL)PHENYL]PIPERIDINE-4-CARBOXYLIC ACID; 1-[(2-ISOPROPYLSULFONYL-5-TRIFLUOROMETHYL)PHENYL]PIPERIDINE-3-CARBOXYLIC ACID; 2-(1-(3-METHOXYPHENYL)PIPERIDIN-4-YLIDENE)ACETIC ACID; 2-(1-(3-METHOXYPHENYL)PIPERIDIN-4-YL)ACETIC ACID; 3-(1-PIPERIDINYL)-BENZENEPROPANOIC ACID; 2-(1-PIPERIDINYL)-BENZENEPROPANOIC ACID; (5R)-5-AMINO-5-(2-PIPERIDYLPHENYL)PENTANOIC ACID; (5S)-5-AMINO-5-(2-PIPERIDYLPHENYL)PENTANOIC ACID; (5R)-5-AMINO-5-[2-(4-HYDROXYPIPERIDYL)PHENYL]PENTANOIC ACID; (5S)-5-AMINO-5-[2-(4-HYDROXYPIPERIDYL)PHENYL]PENTANOIC ACID; 1-(5-BROMO-2-CYANOPHENYL)PIPERIDINE-3-CARBOXYLIC ACID; (S)-1-(5-BROMO-2-CYANOPHENYL)PIPERIDINE-3-CARBOXYLIC ACID; (R)-1-(5-BROMO-2-CYANOPHENYL)PIPERIDINE-3-CARBOXYLIC ACID; 1-(3-BROMO-2-CYANOPHENYL)PIPERIDINE-3-CARBOXYLIC ACID; (S)-1-(3-BROMO-2-CYANOPHENYL)PIPERIDINE-3-CARBOXYLIC ACID; (R)-1-(3-BROMO-2-CYANOPHENYL)PIPERIDINE-3-CARBOXYLIC ACID; 1-(5-CHLORO-2-CYANOPHENYL)PIPERIDINE-3-CARBOXYLIC ACID; (S)-1-(5-CHLORO-2-CYANOPHENYL)PIPERIDINE-3-CARBOXYLIC ACID; (R)-1-(5-CHLORO-2-CYANOPHENYL)PIPERIDINE-3-CARBOXYLIC ACID; 1-(2-CYANO-3-FLUOROPHENYL)PIPERIDINE-4-CARBOXYLIC ACID; 1-(3-CHLORO-2-CYANOPHENYL)PIPERIDINE-4-CARBOXYLIC ACID; 1-(2-CYANO-3-FLUOROPHENYL)PIPERIDINE-3-CARBOXYLIC ACID; (S)-1-(2-CYANO-3-FLUOROPHENYL)PIPERIDINE-3-CARBOXYLIC ACID; (R)-1-(2-CYANO-3-FLUOROPHENYL)PIPERIDINE-3-CARBOXYLIC ACID; (S)-1-(3-CHLORO-2-CYANOPHENYL)PIPERI-

DINE-3-CARBOXYLIC ACID; (R)-1-(3-CHLORO-2-CYANOPHENYL)PIPERIDINE-3-CARBOXYLIC ACID; 1-(5-CHLORO-2-CYANOPHENYL)PIPERIDINE-4-CARBOXYLIC ACID; 1-(5-BROMO-2-CYANOPHENYL)PIPERIDINE-4-CARBOXYLIC ACID; 1-(3-BROMO-2-CYANOPHENYL)PIPERIDINE-4-CARBOXYLIC ACID; 1-(3-CHLORO-2-CYANOPHENYL)PIPERIDINE-3-CARBOXYLIC ACID; 1-(5-CYANO-2-NITROPHENYL)PIPERIDINE-3-CARBOXYLIC ACID; (S)-1-(5-CYANO-2-NITROPHENYL)PIPERIDINE-3-CARBOXYLIC ACID; (5)-1-(2-CYANOPHENYL)PIPERIDINE-3-CARBOXYLIC ACID; (R)-1-(2-CYANOPHENYL)PIPERIDINE-3-CARBOXYLIC ACID; 1-(5-CYANO-2-NITROPHENYL)PIPERIDINE-4-CARBOXYLIC ACID; (S)-1-(2-NITROPHENYL)PIPERIDINE-3-CARBOXYLIC ACID; (R)-1-(2-NITROPHENYL)PIPERIDINE-3-CARBOXYLIC ACID; (R)-1-(5-CYANO-2-NITROPHENYL)PIPERIDINE-3-CARBOXYLIC ACID; (4R)-4-AMINO-4-(2-PIPERIDYLPHENYL)BUTANOIC ACID; (4S)-4-AMINO-4-(2-PIPERIDYLPHENYL)BUTANOIC ACID; (4R)-4-AMINO-4-[2-(4-HYDROXYPIPERIDYL)PHENYL]BUTANOIC ACID; (4S)-4-AMINO-4-[2-(4-HYDROXYPIPERIDYL)PHENYL]BUTANOIC ACID; (2E)-3-[4-BROMO-2-(PIPERIDIN-1-YL)PHENYL]PROP-2-ENOIC ACID; 1-(2-CARBAMOYLPHENYL)PIPERIDINE-3-CARBOXYLIC ACID; 1-(2-CARBAMOYLPHENYL)PIPERIDINE-4-CARBOXYLIC ACID; 1-(5-CHLORO-2-NITROPHENYL)-4-PIPERIDINECARBOXYLIC ACID; (2E)-3-[2-CHLORO-6-(PIPERIDIN-1-YL)PHENYL]PROP-2-ENOIC ACID; (2E)-3-[2-(3-METHYLPIPERIDIN-1-YL)PHENYL]PROP-2-ENOIC ACID; (2E)-3-[2-(4-METHYLPIPERIDIN-1-YL)PHENYL]PROP-2-ENOIC ACID; 1-PHENYL-4-PIPERIDINAMINEACETATE; 1-(3-METHYLPHENYL)-4-PIPERIDINAMINEACETATE; 1-(2-FLUOROPHENYL)-4-PIPERIDINAMINEACETATE; 1-(3-NITROPHENYL)PIPERIDINE-4-CARBOXYLIC ACID; 1-(3-NITROPHENYL)PIPERIDINE-3-CARBOXYLIC ACID; 1-(2-SULFAMOYLPHENYL)PIPERIDINE-4-CARBOXYLIC ACID; (2E)-3-[4-BROMO-2-(3-METHYLPIPERIDIN-1-YL)PHENYL]PROP-2-ENOIC ACID; (2E)-3-[2-(4-METHOXYPIPERIDIN-1-YL)PHENYL]PROP-2-ENOIC ACID; (2E)-3-[2-(3-ETHYLPIPERIDIN-1-YL)PHENYL]PROP-2-ENOIC ACID; (2E)-3-[2-(3,5-DIMETHYLPIPERIDIN-1-YL)PHENYL]PROP-2-ENOIC ACID; (2E)-3-[4-BROMO-2-(4-METHYLPIPERIDIN-1-YL)PHENYL]PROP-2-ENOIC ACID; 1-(2-SULFAMOYLPHENYL)PIPERIDINE-3-CARBOXYLIC ACID; (2E)-3-[2-CHLORO-6-(4-METHYLPIPERIDIN-1-YL)PHENYL]PROP-2-ENOIC ACID; (2E)-3-[2-CHLORO-6-(3-METHYLPIPERIDIN-1-YL)PHENYL]PROP-2-ENOIC ACID; 1-(3-FLUORO-2-NITROPHENYL)PIPERIDINE-4-CARBOXYLIC ACID; 1-(3-FLUORO-2-NITROPHENYL)PIPERIDINE-3-CARBOXYLIC ACID; 1-(3-FLUORO-5-NITROPHENYL)PIPERIDINE-3-CARBOXYLIC ACID; 1-(3-FLUORO-5-NITROPHENYL)PIPERIDINE-4-CARBOXYLIC ACID; 1-(2-AMINO-PHENYL)-PIPERIDINE-4-CARBOXYLIC ACID; 3-[2-(4-ETHYLPIPERIDIN-1-YL)PHENYL]PROP-2-ENOIC ACID; 3-[1-(2-CYANOPHENYL)PIPERIDIN-3-YL]PROPANOIC ACID; 1-[2-(4-METHYL-PIPERIDIN-1-YL)-PHENYL]-5-OXO-PYRROLIDINE-3-CARBOXYLIC ACID; 5-OXO-1-(2-PIPERIDIN-1-YL-PHENYL)-PYRROLIDINE-3-CARBOXYLIC ACID; 1-(2-CARBAMOYL-5-METHYLPHENYL)PIPERIDINE-3-CARBOXYLIC ACID; 2-[1-(3-CHLORO-2-CYANOPHENYL)PIPERIDIN-3-YL]ACETIC ACID; 2-[1-(2-NITROPHENYL)PIPERIDIN-3-YL]ACETIC ACID; 1-(2-CARBAMOYL-5-CHLOROPHENYL)PIPERIDINE-3-CARBOXYLIC ACID; 2-([2-(PIPERIDIN-1-YL)PHENYL]CARBAMOYL)ACETIC ACID; 1-(5-FLUORO-2-NITROPHENYL)PIPERIDINE-4-CARBOXYLIC ACID; 1-(2-CYANO-5-METHYLPHENYL)PIPERIDINE-4-CARBOXYLIC ACID; 1-[2-(TRIFLUOROMETHYL)PHENYL]PIPERIDINE-4-CARBOXYLIC ACID; 2-[1-(2-CYANOPHENYL)PIPERIDIN-3-YL]ACETIC ACID; 2-[1-(2-CYANO-5-METHYLPHENYL)PIPERIDIN-3-YL]ACETIC ACID; 2-[1-(5-CHLORO-2-CYANOPHENYL)PIPERIDIN-3-YL]ACETIC ACID; 3-[2-(4,4-DIMETHYLPIPERIDIN-1-YL)PHENYL]PROP-2-ENOIC ACID; 1-(2-CARBAMOYL-5-METHYLPHENYL)PIPERIDINE-4-CARBOXYLIC ACID; 1-(2-METHYL-3-NITROPHENYL)PIPERIDINE-4-CARBOXYLIC ACID; 1-(2-METHYL-5-NITROPHENYL)PIPERIDINE-3-CARBOXYLIC ACID; 2-[1-(3-NITROPHENYL)PIPERIDIN-3-YL]ACETIC ACID; 1-(2-CYANO-5-METHYLPHENYL)PIPERIDINE-3-CARBOXYLIC ACID; 1-(2-CARBAMOYL-3-CHLOROPHENYL)PIPERIDINE-3-CARBOXYLIC ACID; 2-[1-(2-CARBAMOYLPHENYL)PIPERIDIN-3-YL]ACETIC ACID; 3-[1-(2-CYANOPHENYL)PIPERIDIN-4-YL]PROPANOIC ACID; 1-(5-FLUORO-2-NITROPHENYL)PIPERIDINE-3-CARBOXYLIC ACID; 1-(2-METHYL-3-NITROPHENYL)PIPERIDINE-3-CARBOXYLIC ACID; 1-[2-(TRIFLUOROMETHYL)PHENYL]PIPERIDINE-3-CARBOXYLIC ACID; 1-(2-METHYL-5-NITROPHENYL)PIPERIDINE-4-CARBOXYLIC ACID; 1-(2-CARBAMOYL-3-CHLOROPHENYL)PIPERIDINE-4-CARBOXYLIC ACID; 1-(2-CARBAMOYL-5-CHLOROPHENYL)PIPERIDINE-4-CARBOXYLIC ACID; 1-PHENYL-3-PIPERIDINECARBOXYLIC ACID 3-(HEXAHYDRO-1H-AZEPIN-1-YL)-BENZENEPROPANOIC ACID; 2-(HEXAHYDRO-1H-AZEPIN-1-YL)-BENZENEPROPANOIC ACID; (2E)-3-[2-(AZEPAN-1-YL)PHENYL]PROP-2-ENOIC ACID; (2E)-3-[2-(AZEPAN-1-YL)-4-BROMOPHENYL]PROP-2-ENOIC ACID; (2E)-3-[2-(AZEPAN-1-YL)-6-CHLOROPHENYL]PROP-2-ENOIC ACID

List No. 7—crotonaldehydes: ALL-TRANS-RETINAL; 3-(2-FURYL)ACROLEIN; 2-NITROCINNAMALDEHYDE; CITRAL; TRANS-CINNAMALDEHYDE; 2-METHOXYCINNAMALDEHYDE; 4-DIMETHYLAMINOCINNAMALDEHYDE; CROTONALDEHYDE; 2,4-HEXADIENAL; TRANS,TRANS-2,4-HEPTADIENAL; TRANS,TRANS-2,4-NONADIENAL; TRANS,TRANS-2,4-DECADIENAL; TRANS-2-HEXENAL; TRANS-2-HEPTENAL; TRANS-2-OCTENAL; 4-NITROCINNAMALDEHYDE; TRANS-2-NONENAL; 3,3-DIPHENYLACROLEIN; TRANS-2-PENTENAL; 3-(5-NITRO-2-FURYL)ACROLEIN; 3-METHYL-2-BUTENAL; TRANS,TRANS-5-(4-(DIMETHYLAMINO)PHENYL)-2,4-PENTADIENAL; (2E,4E)-5-(4-NITRO-PHENYL)-PENTA-2,4-DIENAL; TRANS-2-DODECENAL; FEMA 3082; 2,4-OCTADIENAL; TRANS,TRANS-2,4-UNDECADIENAL; TRANS,TRANS-2,4-DODECADIENAL; TRANS-2-DECENAL; TRANS-2-UNDECENAL; 2-TRANS-6-CIS-DODECADIENAL; 4-METHOXYCINNAMALDEHYDE; 3-(THIOPHEN-2-YL)ACRYLALDEHYDE; (4-OXO-2-BUTEN-1-YL)TRIPHENYLPHOSPHONIUM BROMIDE; (1,3,3-TRIMETHYL-1,3-DIHYDRO-INDOL-2-YLIDENE)-ACETALDEHYDE; FARNESAL; TETRABUTYLAMMONIUM GLUTACONALDEHYDE ENOLATE; 3-CHLORO-3-PHENYL-PRO- PENAL; 2-BENZAMIDOCINNAMALDEHYDE; 2-(1,3,3-TRIMETHYLINDOLIN-2-YLIDENE) ACETALDEHYDE; METHYL-(5S,6S)-EPOXY-11-OXO-(7E,9E)-UNDECADIENOATE; 4-HYDROXY-3-METHOXYCINNAMALDEHYDE; TRANS-4-(DIETHYLAMINO)CINNAMALDEHYDE; SINAPINALDEHYDE; 13-CIS-RETINAL; (Z)-3-CHLORO-3-PHENYLACRYLALDEHYDE; (Z)-3-CHLORO-3-(4-FLUOROPHENYL)ACRYLALDEHYDE; (Z)-3-CHLORO-3-(4-METHOXYPHENYL)ACRYLALDEHYDE; 9-CIS-RETINAL; 11-CIS RETINAL; 3-NITROCINNAMALDEHYDE; TRANS-2-TETRADECENAL; 4-CHLOROCINNAMALDEHYDE; BETA-(4-PYRIDYL)ACROLEIN OXALATE; FUMARALDEHYDE MONO(DIMETHYL ACETAL); 3-CHLORO-3-(P-CHLOROPHENYL)ACROLEIN; FUMARALDEHYDIC ACID METHYL ESTER; TRANS, TRANS-2,6-NONADIENAL; (Z)-3,7-DIMETHYLOCTA-2,6-DIENAL; TRANS,TRANSMUCONALDEHYDE; ETHYL TRANS-4-OXO-2-BUTENOATE; DIMETHYL DECADIENAL; 4-ACETOXY-3-METHOXYCINNAMALDEHYDE; DECA-2,4,6,8-TETRAENAL; 3,3-DIMETHYLCYCLOHEXYLIDENEACETALDEHYDE; 11-(2-FURYL)UNDECA-2,4,6,8,10-PENTAENAL; 3-(1-ACETYL-1H-INDOL-3-YL)ACRYLALDEHYDE; ETHYL CITRAL; 4-OXO-3-(3-OXOPROP-1-ENYL)-4H-CHROMEN-6-YL ACETATE; 3-(7-METHYL-4-OXO-4H-CHROMEN-3-YL)ACRYLALDEHYDE; 4-OXO-3-(3-OXOPROP-1-ENYL)-4H-CHROMEN-7-YL ACETATE; 3-(1-OXO-1H-BENZO[F]CHROMEN-2-YL)ACRYLALDEHYDE; 3-(4-TERT-BUTYL-PHENYL)-PROPENAL; LIMONENAL; (2E,4E,6E)-6-(3-ETHYL-1,3-BENZOTHIAZOL-2(3H)-YLIDENE)HEXA-2,4-DIENAL; (E)-3,7-DIMETHYL-4-(3-METHYLBUT-2-EN-1-YL)OCTA-2,6-DIENAL; 3,4,5-TRIMETHOXYCINNAMALDEHYDE; 4-HYDROXYCINNAMALDEHYDE; 4-METHYL-2-PENTENAL; CIS-2-HEXENAL; 3-CHLORO-3-(1,5-DIMETHYL-3-OXO-2-PHENYL-2,3-DIHYDRO-1H-PYRAZOL-4-YL)ACRYLALDEHYDE; 4-KETORETINAL; (E)-4-HYDROXYHEXENAL; 1-(3-OXO-1-PROPENYL)-2-NAPHTHYL ACETATE; 3-BROMOCINNAMALDEHYDE; 2-CHLOROCINNAMALDEHYDE; ETHYL 3,5-DIMETHYL-4-(3-OXOPROP-1-ENYL)-1H-PYRROLE-2-CARBOXYLATE; 2-[(1E)-3-OXOPROP-1-EN-1-YL]PHENYL ACETATE; 3-CHLORO-3-(4-NITROPHENYL)ACRYLALDEHYDE; (2E)-3-(4-BROMOPHENYL)-3-CHLOROACRYLALDEHYDE; 3-CHLORO-3-(4-CHLOROPHENYL)ACROLEIN; 2-HYDROXYCINNAMALDEHYDE; 4-HYDROPEROXY-2-NONENAL; ETHYL 2-AMINO-5-(3-OXOPROP-1-ENYL)-3-FUROATE; 2-HEXENAL; 3-AMINO-2-BUTENAL; 3-(3-PYRIDYL)ACROLEIN; (Z)-3-CHLORO-3-(4-NITROPHENYL)ACRYLALDEHYDE; (5-METHYL-2,4-DIPHENYL-6H-1,3-OXAZIN-6-YLIDENE)ACETALDEHYDE; (2E,4E)-5-(4-FLUOROPHENYL)-2,4-PENTADIENAL; 4-BROMOCINNAMALDEHYDE; AURORA KA-3085; (1-CHLORO-2-FORMYLVINYL)FERROCENE; 4-DIBUTYLAMINOCINNAMALDEHYDE; 4-FLUOROCINNAMALDEHYDE; (E)-3-[3'-(4"-FLUOROPHENYL)-1'-(1"-METHYLETHYL)-1H-INDOL-2"-YL]-2-PROPNAL; (2E)-3-(1H-PYRROL-2-YL)-2-PROPENAL; 4-HYDROXYRETINAL; GRANDLURE; 3-(5-METHYL-2-PHENYL-3-INDOLIZINYL)-3-PHENYLACRYLALDEHYDE; 3-(5-METHYL-2-PHENYL-3-INDOLIZINYL) ACRYLALDEHYDE; 3-(4-[6-(3-OXO-1-PROPENYL) IMIDAZO[1,2-A]PYRIDIN-2-YL]PHENYL) ACRYLALDEHYDE; (2E,4E)-5-(4-CHLOROPHENYL)-2,4-PENTADIENAL; TRAUMATIN; (Z)-3,5-DIMETHYLHEX-2-ENAL; (E)-3,4,8-TRIMETHYLNONA-2,7-DIENAL; (Z)-3,7-DIMETHYL-OCTA-2,7-DIENAL; (2E)-3-(1-BENZYL-1H-1,2,3-TRIAZOL-4-YL) ACRYLALDEHYDE; 4-ISOPROPYLCINNAMALDEHYDE; 2,4,6-TRIMETHYLCINNAMALDEHYDE; (2E)-3-[5-(4-METHYL-3-NITROPHENYL)-2-FURYL]ACRYLALDEHYDE; (2Z)-3-(2-MERCAPTO-1H-BENZIMIDAZOL-1-YL)-3-PHENYLACRYLALDEHYDE; (2E)-3-[5-(3-NITROPHENYL)-2-FURYL]ACRYLALDEHYDE; (2E)-3-[5-(2-CHLOROPHENYL)-2-FURYL] ACRYLALDEHYDE; (2E)-3-[5-(3-CHLORO-4-METHYLPHENYL)-2-FURYL]ACRYLALDEHYDE; (2E)-3-[5-(4-CHLOROPHENYL)-2-FURYL]ACRYLALDEHYDE; 2,6-DIFLUOROCINNAMIC ALDEHYDE; 4-(TRIFLUOROMETHOXY)CINNAMIC ALDEHYDE; 2-CHLORO-4-FLUOROCINNAMALDEHYDE; ALL-TRANS-3-HYDROXYRETINAL; CINNAMALDEHYDE-UL (RING-14C); 3-[(2R,3R)-3-PENTYLOXIRANYL]-2E-PROPENAL; 4-OXO 2-NONENAL-D3; 4-(2-FORMYLVINYL)BENZONITRILE; (+/−)-4-HYDROXY-9,9,9-D3-NON-2E-ENAL; 4-OXO-2-NONENAL; 2-CHLORO-6-FLUOROCINNAMALDEHYDE; 3-CHLOROCINNAMALDEHYDE; 2,3-DIMETHOXYCINNAMALDEHYDE; 2,3-DICHLOROCINNAMALDEHYDE; 2,4-DIFLUOROCINNAMALDEHYDE; 4-PHENYLCINNAMALDEHYDE; 2-FLUOROCINNAMALDEHYDE; 2-PROPENAL, 3-(3-METHYLPHENYL)-,(2E); 3-FLUOROCINNAMALDEHYDE; 2-PROPENAL, 3-(4-METHYLPHENYL)-,(2E); 2-METHYLCINNAMALDEHYDE; 2-PROPENAL, 3-(4-(ACETYLOXY)PHENYL)-,(2E); 4-OXO-2-HEXENAL; 3-(2-HYDROXY-NAPHTHALEN-1-YL)-PROPENAL; (2Z)-3-(4-BROMOPHENYL)-3-CHLOROACRYLALDEHYDE; 3-METHYL-HEX-2-ENAL; (E)-3,6-DIMETHYL-HEPTA-2,5-DIENAL; 3-(NAPHTHALEN-2-YL)ACRYLALDEHYDE; 2-BROMOCINNAMALDEHYDE; (2E,13Z)-OCTADECA-2,13-DIENAL; (2E)-OCTADEC-2-ENAL; 3-(TRIFLUOROMETHYL) CINNAMALDEHYDE; (E)-3-[5-TERT-BUTYLDIMETHYLSILYLOXYMETHYL-2,6-DIISOPROPYL-4-(4-FLUOROPHENYL)-PYRID-3-YL]-PROP-2-ENAL; 3-(9-ANTHRYL)ACROLEIN; (E,E,E)-2,4,6-OCTATRIENAL; 4-(TRIFLUOROMETHYL) CINNAMALDEHYDE; 5-PROP-2-ENAL-1,2:3,4-DI-O-ISOPROPYLIDENE-A-D-GALACTOPYRANOSE; (E)-3-((3AR,6S,6AR)-6-(BENZYLOXY)-TETRAHYDRO-2,2-DIMETHYLFURO[3,2-D][1,3]DIOXOL-5-YL) ACRYLALDEHYDE; (2Z)-3-[(4S)-2,2-DIMETHYL-1,3-DIOXOLAN-4-YL]PROP-2-ENAL; (2Z)-3-[(4R)-2,2-DIMETHYL-1,3-DIOXOLAN-4-YL]PROP-2-ENAL; (2E)-3-[6-(BENZYLOXY)-2,2-DIMETHYLTETRAHYDROFURO[3,4-D][1,3]DIOXOL-4-YL]PROP-2-ENAL; (E)-4-(METHYL-PHENYL-AMINO)-BUT-2-ENAL; 3-METHYL-5-[(2,6,6-TRIMETHYLCYCLOHEX-3,3,7,7,7-D5)-1-ENYL]PENTA-2,4-DIENAL; 3-HYDROXY-RETINAL-D5; 3-(4-AZIDOPHENYL)ACRYLALDEHYDE; (E)-5,9-ANHYDRO-6,7-O-CYCLOHEXYLIDENE-2,3,4,8-TETRADEOXY-8-C-(ETHOXYCARBONYL)METHYL-3-METHYL-D-ALLO-NON-2-ENAL; (E)-3-[2-CYCLOPROPYL-4-(4-FLUOROPHENYL)-3-QUINOLINYL]-2-PROPENAL; 3-(3-METHOXYPHENYL)ACRYLALDEHYDE; 3-(2-(TRIFLUOROMETHYL)PHENYL)ACRYLALDEHYDE; 4,4-DIMETHYLPENT-2-ENAL; (2E,4E)-7-[(4-

METHOXYBENZYL)OXY]-2,4-HEPTADIENAL; (E)-2-HEXADECENAL; (2E,4E)-5-(4-METHOXY-2,3,6-TRIMETHYLPHENYL)-3-METHYLPENTA-2,4-DIENAL; (2E)-3-(5-CHLORO-2-FURYL)ACRYLALDEHYDE; (2E)-3-(5-BROMO-2-FURYL)ACRYLALDEHYDE; 2-(THIETAN-3-YLIDENE)ACETALDEHYDE; 2-(OXETAN-3-YLIDENE)ACETALDEHYDE; 2,4-PENTADIENAL; NONA-2,4,6-TRIENAL; (2Z)-3-(1H-PYRROL-2-YL)-2-PROPENAL; (2E)-3-(3-INDOLIZINYL)-2-PROPENAL; (2E)-3-(1-METHYL-1H-PYRROL-2-YL)-2-PROPENAL; (2E)-3-(1-INDOLIZINYL)-2-PROPENAL; (E)-3-(1-METHYL-5-OXO-2,5-DIHYDRO-1H-PYRROL-3-YL)ACRYLALDEHYDE; (2E)-3-(1H-INDOL-3-YL)-2-PROPENAL; (2E)-3-(1H-PYRROLO[2,3-B]PYRIDIN-3-YL)-2-PROPENAL; (Z)-2-(3,4-DIHYDROPYRROLO[1,2-A]PYRAZIN-1(2H)-YLIDENE)ACETALDEHYDE; (E)-3-(1H-INDOL-2-YL)-2-PROPENAL; (2E)-(3,5,5-TRIMETHYLCYCLOHEX-2-EN-1-YLIDENE)ACETALDEHYDE; 2-BUTENAL, 3-CHLORO-4-OXO-4-PHENYL-, (E)-; 3-(2-PYRIDINYL)-2-PROPENAL; (2E)-3-(2-PYRIDINYL)-2-PROPENAL; (Z)-3-CHLORO-3-(THIOPHEN-3-YL)ACRYLALDEHYDE; (Z)-3-(2,5-DIHYDRO-1-METHYL-5-OXO-1H-PYRROL-3-YL)-2-PROPENAL; 2-((3,4-DIHYDRO-1(2H)-ISOQUINOLINYLIDENE)-ACETALDEHYDE); 2-CYCLOHEPTYLIDENEACETALDEHYDE; (E)-(1-METHYL-2-PIPERIDINYLIDENE)-ACETALDEHYDE; 3-(3-TERT-BUTYL-5-ISOPROPYLPHENYL)BUT-2-ENAL; (Z)-2-BROMO-4-OXO-BUT-2-ENOIC ACID ETHYL ESTER; TRANS,TRANS-5-BROMO-2,4-PENTADIENAL; 3-(5-CHLORO-2-HYDROXY-3-METHOXY-PHENYL)-PROPENAL; 3-(2,3-DICHLORO-6-HYDROXY-5-METHOXY-PHENYL)-PROPENAL; DIBROMO-5-ETHOXY-6-HYDROXY-PHENYL)-PROPENAL; 3-(5-CHLORO-2-HYDROXY-3-NITRO-PHENYL)-PROPENAL; 3-(5-BROMO-2-HYDROXY-3-NITRO-PHENYL)-PROPENAL; 3-(5-BENZYL-3-BROMO-2-HYDROXY-PHENYL)-PROPENAL; 3-(3-BROMO-5-CHLORO-2-HYDROXY-PHENYL)-PROPENAL; 3-(5-BENZYL-2-HYDROXY-3-NITRO-PHENYL)-PROPENAL; 3-(2-HYDROXY-5-NITRO-PHENYL)-PROPENAL; 3-(3,5-DICHLORO-2-HYDROXY-PHENYL)-PROPENAL; 3-(3-BROMO-2-HYDROXY-5-NITRO-PHENYL)-PROPENAL; 3-(5-CHLORO-2-HYDROXY-PHENYL)-PROPENAL; 3-(5-BROMO-2-HYDROXY-PHENYL)-PROPENAL; 3-(3,5-DIBROMO-2-HYDROXY-PHENYL)-PROPENAL; 3-(5-BROMO-2-HYDROXY-3-METHOXY-PHENYL)-PROPENAL; 3-(2-HYDROXY-3-NITRO-PHENYL)-PROPENAL; 3-(5-BENZYL-3-CHLORO-2-HYDROXY-PHENYL)-PROPENAL; 3-(5-BROMO-3-CHLORO-2-HYDROXY-PHENYL)-PROPENAL; 3-(2-HYDROXY-3-METHOXY-5-NITRO-PHENYL)-PROPENAL; 3-(5-BENZYL-2-HYDROXY-PHENYL)-PROPENAL; (E)-3-[2-CYCLOPROPYL-4-(4-FLUOROPHENYL)-3-QUINOLYL]-ACROLEIN; (2E)-3-(2-FURANYL)-2-BUTENAL; (2Z)-3-(3-FURANYL)-2-BUTENAL; (E)-5-(3-OXOPROP-1-ENYL)FURAN-2-CARBALDEHYDE; (E)-3-(5-AMINOFURAN-2-YL)ACRYLALDEHYDE; (2Z)-3-(2-FURANYL)-2-BUTENAL; (2E)-3-(2,5-DIHYDRO-5-OXO-2-FURANYL)-2-PROPENAL; (2E)-3-(4-NITRO-2-FURANYL)-2-PROPENAL; (2Z)-3-(2-FURANYL)-2-PROPENAL; (2E)-3-(3-BENZOFURANYL)-2-PROPENAL; (2E)-3-(5-METHYL-2-FURANYL)-2-PROPENAL; (2E)-3-(2-CHLORO-4-METHOXYPHENYL)-2-PROPENAL; (2E)-3-CYCLOPENTYL-2-PROPENAL; (2Z,4E)-4-(3',4'-DIHYDRO-1'(2'H)-NAPHTHALEN-1'YLIDENE)-3-METHYL-2-BUTENAL; 3-(1H-BENZOIMIDAZOL-2-YLSULFANYL)-3-PHENYL-PROPANAL; (Z)-3-CHLORO-3-P-TOLYLACRYLALDEHYDE; TERT-BUTYL 4-(2-OXOETHYLIDENE)PIPERIDINE-1-CARBOXYLATE; TERT-BUTYL 3-[(1E)-3-OXOPROP-1-ENYL]AZETIDINE-1-CARBOXYLATE; (Z)-3-CHLORO-3-(3-CHLOROPHENYL)ACRYLALDEHYDE; 4-(2-FORMYLVINYL)-ACETANILIDE; N-[4-(4-FLUOROPHENYL)-6-(1-METHYLETHYL)-5-[(1E)-3-OXO-1-PROPEN-1-YL]-2-PYRIMIDINYL]-N-METHYLMETHANESULFONAMIDE; (E)-2-(2-FURANYL)-2-BUTENEDIAL; (E)-2-(5-METHYL-2-FURANYL)-2-BUTENEDIAL; 4-HYDROXY NONENAL ALKYNE; 3-(2-PYRIDINYL)-2-BUTENAL; (2E)-3-(4-PYRIDINYL)-2-PROPENAL; 3-(HEXAHYDRO-1H-AZEPIN-1-YL)-BENZENEPROPANOIC ACID; 2-(HEXAHYDRO-1H-AZEPIN-1-YL)-BENZENEPROPANOIC ACID; (2E)-3-[2-(AZEPAN-1-YL)PHENYL]PROP-2-ENOIC ACID; (2E)-3-[2-(AZEPAN-1-YL)-4-BROMOPHENYL]PROP-2-ENOIC ACID; (2E)-3-[2-(AZEPAN-1-YL)-6-CHLOROPHENYL]PROP-2-ENOIC ACID

List No. 8—Methylketones: CIS-PINONIC ACID; 2-ACETYLBENZOIC ACID; 4-ACETYLBENZOIC ACID; LEVULINIC ACID; 4,6-DIOXOHEPTANOIC ACID; 4-ACETYLBUTYRIC ACID; N-(ACETOACETYL)GLYCINE; DIACETONEAMINE HYDROGEN OXALATE; 5-ACETYLSALICYLIC ACID; 3-ACETYLACRYLIC ACID; 4-ACETYLPHENOXYACETIC ACID; (4-ACETYLPHENYL)ACETIC ACID; 2-PHENYLLEVULINIC ACID; 4-ACETYL-3,5-DIMETHYL-1H-PYRROLE-2-CARBOXYLIC ACID; 5-CARBOXYDEHYDROACETIC ACID; 3,3-DIMETHYL-4-OXOVALERIC ACID; 5-[(4-ACETYLPHENYL)AMINO]-5-OXOPENTANOIC ACID; 3-ACETYLBENZOIC ACID; 5-ACETYLVALERIC ACID; A-ACETYLMANDELIC ACID; ACETOACETIC ACID; 5-ACETYLTHIOPHENE-2-CARBOXYLIC ACID; ACETYLPYRUVIC ACID; 2-(3-ACETYL-2,2-DIMETHYLCYCLOBUTYL)ACETIC ACID; 7-OXOOCTANOIC ACID; 5,7-DIOXOOCTANOIC ACID; N-(ACETOACETYL)ANTHRANILIC ACID; 10-OXOUNDECANOIC ACID; 4-[(2-ACETYL-3-THIENYL)AMINO]-4-OXOBUT-2-ENOIC ACID; 2-([(5-ACETYL-2-METHOXYPHENYL)METHYL]SULFANYL)ACETIC ACID; 2-(([(2-ACETYLPHENYL)CARBAMOYL]METHYL)SULFANYL)ACETIC ACID; 2-(1-ACETYL-2-OXOPROPYL)-5-METHOXYBENZOIC ACID; 2-ACETYLPHENOXY ACETIC ACID; 3-METHYL-4-OXO-2-PENTENOIC ACID; BETA-METHYLLEVULINIC ACID; 2-METHYL-4-OXOPENTANOIC ACID; DIACETONAMINE HYDROGEN OXALATE HYDRATE; 5-[(3-ACETYLPHENYL)AMINO]-5-OXOPENTANOIC ACID; 2-ACETYL-3,6-DIMETHYLBENZOIC ACID; 2-((3-OXO-2-[(1,3-THIAZOL-2-YLAMINO)CARBONYL]-1-BUTENYL)AMINO)ACETIC ACID; 2-(4-ACETYL-2,3-DIHYDRO-5-METHYL-2-OXO-1H-PYRROL-3-YL)ACETIC ACID; 4-(4-ACETYLANILINO)-4-OXO-2-BUTENOIC ACID; 9-OXODEC-2-ENOIC ACID; 2-ACETYLTHIAZOLE-4-CARBOXYLIC ACID; 5-ACETYL-2-AMINO-4-HYDROXYBENZOIC ACID; 5-ACETYL-4-HYDROXY-3-METHOXY-FURAN-2-CARBOXYLIC ACID; 4'-ACETYL-BIPHENYL-4-CARBOXYLIC ACID; 1-(4-ACETYLPHENYL)-4-PIPERIDINECARBOXYLIC ACID; (2-ACETYL-4,5-DIMETHOXYPHENYL)ACETIC ACID; 3-(2-OXOPROPYL)-BENZOIC ACID; 4-(2-OXOPROPYL)

BENZOIC ACID; 2-(1,1-DIMETHYL-2-OXO-PROPYL)-MALONIC ACID; 4-(4-ACETYLANILINO)-4-OXOBUTANOIC ACID; 5-OXO-3-PHENYL-HEXANOIC ACID; 4-(4-ACETYLPHENOXY)BENZOIC ACID; (E)-3-(5-ACETYL-FURAN-2-YL)ACRYLIC ACID; 3-ACETYL-4-HYDROXYBENZOIC ACID; [2-(2-OXO-PROPOXY)PHENOXY]ACETIC ACID; 2-CYANO-3,3-DIMETHYL-4-OXO-PENTANOIC ACID; 4-ACETYL-1-METHYL-1H-PYRROLE-2-CARBOXYLIC ACID; 3-ACETYL-2-OXO-1,2-DIHYDRO-QUINOLINE-4-CARBOXYLIC ACID; 3-ACETYL-4,5-DIMETHYL-1H-PYRROLE-2-CARBOXYLIC ACID; 2-[(4-ACETYLPHENYL)SULFANYL]ACETIC ACID; 2-ISOPROPYL-5-OXOHEXANOIC ACID; 4-KETOVALPROIC ACID; 5-OXO-2-PROPYL-HEXANOIC ACID; 2-ACETYL-3,6-DIFLUOROBENZOIC ACID; 3-ACETYL-2-METHYL-QUINOLINE-4-CARBOXYLIC ACID; 5-ACETYL-2,4-DIMETHYL-1H-PYRROLE-3-CARBOXYLIC ACID; 4-[(3-ACETYLPHENYL)AMINO]-4-OXOBUTANOIC ACID; (2E)-4-[(3-ACETYLPHENYL)AMINO]-4-OXOBUT-2-ENOIC ACID; 4-HYDROXY-2-METHYL-3-(3-OXO-BUTYL)-QUINOLINE-6-CARBOXYLIC ACID; 8-ACETYL-3A,4,5,9B-TETRAHYDRO-3H-CYCLOPENTA[C]QUINOLINE-4-CARBOXYLIC ACID; 3-METHYL-5-(2-OXO-PROPYL)-1-PHENYL-1H-PYRAZOLE-4-CARBOXYLIC ACID; 3-CARBOXY-4-HYDROXYPHENYLACETONE; 4-ACETYL-3,5-DIOXO-1-METHYLCYCLOHEXANECARBOXYLIC ACID; (4-ACETYL-2-METHOXYPHENOXY)ACETIC ACID; 1-(4-ACETYL-PHENYL)-5-METHYL-1H-[1,2,3]TRIAZOLE-4-CARBOXYLIC ACID; 2-ACETYL-1H-INDOLE-3-CARBOXYLIC ACID; 5-ACETYL-2-ACETYLAMINO-4-METHYL-THIOPHENE-3-CARBOXYLIC ACID; 1-(4-ACETYLPHENYL)-5-OXOPYRROLIDINE-3-CARBOXYLIC ACID; 4-(2-ACETYL-3-OXO-1-BUTENYL)BENZENECARBOXYLIC ACID; N-(M-ACETYLPHENYL)ANTHRANILIC ACID; 2-(4-ACETYLPHENOXY)-2-METHYLPROPANOIC ACID; 4-[(2-ACETYLPHENYL)AMINO]-4-OXOBUTANOIC ACID; 3-ACETYLTHIOPHENE-2-CARBOXYLIC ACID; 9-OXODECANOIC ACID; 3-ACETYL-1H-INDOLE-2-CARBOXYLIC ACID; 2-(([(4-ACETYLPHENYL)CARBAMOYL]METHYL)SULFANYL)ACETIC ACID; 2'-ACETYL-2-BIPHENYLCARBOXYLIC ACID; 4-ACETYL-7-METHOXY-1-BENZOFURAN-2-CARBOXYLIC ACID; 2-(3-OXOBUTANAMIDO)PROPANOIC ACID; 4-METHYL-2-(3-OXOBUTANAMIDO)PENTANOIC ACID; 3-(3-OXOBUTANAMIDO)BENZOIC ACID; 4-(3-OXOBUTANAMIDO)BENZOIC ACID; (3-ACETYLPHENOXY)ACETIC ACID; 2-(2-OXOPROPYL)HEXANOIC ACID; 2-(2-OXOPROPYL)BENZOIC ACID; 2-METHYL-3-ACETYLBENZOIC ACID; 4-ACETYL-1H-PYRROLE-2-CARBOXYLIC ACID; 3-(2-HYDROXY-4,4-DIMETHYL-6-OXO-1-CYCLOHEXENYL)-4-OXOPENTANOIC ACID; 3-((4-OXOPENTANOYL)OXY)-2-PHENYLPROPANOIC ACID; MONO-(2-ETHYL-5-OXOHEXYL)-ADIPATE; (S)-2-TERT-BUTOXYCARBONYLAMINO-4-OXO-PENTANOIC ACID; 3-ACETYL-QUINOLINE-4-CARBOXYLIC ACID; 6-ACETYL-7-METHYL-PYRAZOLO[1,5-A]PYRIMIDINE-2-CARBOXYLIC ACID; 6-ACETYL-7-METHYL-PYRAZOLO[1,5-A]PYRIMIDINE-3-CARBOXYLIC ACID; (2-ACETYL-4-METHYLPHENOXY)ACETIC ACID; 4-((5-ACETYL-4-METHYL-1,3-THIAZOL-2-YL)AMINO)-4-OXOBUTANOIC ACID; 3-(2-CARBOXYPHENYL)PENTANE-2,4-DIONE; 4-ACETYL-1-CYCLOPROPYL-2,5-DIMETHYL-1H-PYRROLE-3-CARBOXYLIC ACID; 5-[(4-ACETYLPHENOXY)METHYL]-2-FUROIC ACID; 3-([(5-ACETYL-2-METHOXYPHENYL)METHYL]SULFANYL)PROPANOIC ACID; 1-(3-ACETYLPHENYL)-5-OXO-3-PYRROLIDINECARBOXYLIC ACID; 4-(4-ACETYL-PHENOXY)-BUTYRIC ACID; [(5-ACETYL-3-CYANO-6-METHYLPYRIDIN-2-YL)THIO]ACETIC ACID; 3-(4-ACETYLPHENOXY)PROPANOIC ACID; 3-(3-ACETYL-6-METHYL-4-OXO-4H-PYRAN-2-YLAMINO)-PROPIONIC ACID; 3'-ACETYL-BIPHENYL-2-CARBOXYLIC ACID; (3'-ACETYL-BIPHENYL-3-YL)-ACETIC ACID; 3'-ACETYL-BIPHENYL-3-CARBOXYLIC ACID; 3'-ACETYL-BIPHENYL-4-CARBOXYLIC ACID; (3'-ACETYL-BIPHENYL-4-YL)-ACETIC ACID; 3-METHYL-5-(3-OXOBUTYL)-1-BENZOFURAN-2-CARBOXYLIC ACID; O-(3-OXOBUTYL)-N-PROPYLHYDROXYLAMINE OXALATE SALT; (5-ACETYL-3-THIENYL)ACETIC ACID; 3-(3-ACETYL-BENZENESULFONYLAMINO)-PROPIONIC ACID; 4'-ACETYL-BIPHENYL-3-CARBOXYLIC ACID; (4-ACETYL-PIPERIDIN-1-YL)-ACETIC ACID; 2-[(5-ACETYL-4-METHYL-2-PYRIMIDINYL)SULFANYL]ACETIC ACID; 2,6-DIMETHOXY-4-GLYCOLIC ACID PHENYL ACETONE; (2S)-2-([(3-ACETYLPHENYL)CARBAMOYL]AMINO)PROPANOIC ACID; (2S)-2-([(4-ACETYLPHENYL)CARBAMOYL]AMINO)PROPANOIC ACID; (3-ACETYL-INDOL-1-YL)-ACETIC ACID; 1-(1,2-DIOXOPROPYL)-S-PROLINE; 2-ACETYL-3,4,5,6-TETRAFLUOROBENZOIC ACID; LABOTEST-BB LT03330740; 4-ACETYL-1-BENZYL-PYRROLIDINE-3-CARBOXYLIC ACID; 4-ACETYL-PYRROLIDINE-3-CARBOXYLIC ACID; 2-ACETONICOTINIC ACID; (3-ACETYL-2-METHYL-INDOL-1-YL)-ACETIC ACID; (3-ACETYL-7-ETHYL-INDOL-1-YL)-ACETIC ACID; 6-ACETYL-4-OXO-1,4-DIHYDRO-QUINOLINE-3-CARBOXYLIC ACID; 3-ACETYL-1H-PYRAZOLE-5-CARBOXYLIC ACID; 4-[(4-ACETYLPHENYL)CARBAMOYL]-3-METHYLBUTANOIC ACID; 2-([(4-ACETYLPHENYL)CARBAMOYL]METHOXY)ACETIC ACID; 2-((([(3-ACETYLPHENYL)CARBAMOYL]METHYL)SULFANYL)ACETIC ACID; 2-([(3-ACETYLPHENYL)CARBAMOYL]METHOXY)ACETIC ACID; 3-(4-ACETYL-3,5-DIMETHYL-1H-PYRAZOL-1-YL)BUTANOIC ACID; 3-(3-ACETYL-2,4-DIMETHYL-PYRROL-1-YL)-PROPIONIC ACID; 3-(4-ACETYL-3,5-DIMETHYL-PYRAZOL-1-YL)-PROPIONIC ACID; 3-AMINO-4-OXO-PENTANOIC ACID; 5-ACETYL-6-METHYL-2-OXO-1,2-DIHYDRO-3-PYRIDINECARBOXYLIC ACID; 2-(4-ACETYLPHENOXY)PROPANOIC ACID; 2-([(4-ACETYLPHENYL)SULFONYL]AMINO)PROPANOIC ACID; ([(3-ACETYLPHENYL)SULFONYL]AMINO)ACETIC ACID; (5-ACETYL-2-METHOXYPHENYL)ACETIC ACID; 2-(2-OXOPROPYLTHIO)BENZOIC ACID; 2-[(4-ACETYL-2-FLUOROPHENYL)SULFANYL]ACETIC ACID; ([(4-ACETYLPHENYL)SULFONYL]AMINO)ACETIC ACID; 5-(4-ACETYLPHENYL)-2-FUROIC ACID; 3-([(4-ACETYLPHENYL)SULFONYL]AMINO)PROPANOIC ACID; 2-(4-ACETYLPHENOXY)-2-PHENYLACETIC ACID; L-4-ACETYLPHE; (4-ACETYL-3,5-DIMETHYL-1H-PYRAZOL-1-YL)ACETIC ACID; 3-(4-ACETYL-3,5-DIMETHYL-PYRAZOL-1-YL)-2-METHYL-PROPIONIC ACID; (4-ACETYLANILINO)ACETIC ACID; 5-ACETYL-3-METHYL-1H-INDOLE-2-CARBOXYLIC ACID; 7-ACETYL-4-OXO-1,4-DIHYDRO-QUINOLINE-3-CARBOXYLIC ACID; 2-(2-ACETYL-4-ETHYLPHE-

NOXY)ACETIC ACID; 2'-ACETYLBIPHENYL-3-CARBOXYLIC ACID; 2'-ACETYL[1,1'-BIPHENYL]-4-CARBOXYLIC ACID; 4-(5-ACETYL-2-THIENYL)BENZOIC ACID; 3-(5-ACETYL-2-THIENYL)BENZOIC ACID; 3-(3-ACETYL-INDOL-1-YL)-PROPIONIC ACID; 2-(3-ACETYL-1H-INDOL-1-YL)PROPANOIC ACID; [5-ACETYL-3-(METHOXYCARBONYL)-4-METHYL-1H-PYRROL-2-YL]ACETIC ACID; 4-[5-ACETYL-4-METHYL-1,3-THIAZOL-2-YL)AMINO]BUTANOIC ACID; (S)-2-AMINO-5-OXO-HEXANOIC ACID, HYDROBROMIDE; (2Z)-4-((4-ACETYLPHENYL)AMINO)-3-METHYL-4-OXOBUT-2-ENOIC ACID; 3-(4-ACETYL-5-METHYL-2-FURYL)PROPANOIC ACID; 5-ACETYLTHIOPHENE-3-CARBOXYLIC ACID; 3-(3-ACETYL-2,5-DIMETHYL-PYRROL-1-YLMETHYL)-BENZOIC ACID; 4-(3-ACETYL-2,5-DIMETHYL-PYRROL-1-YLMETHYL)-BENZOIC ACID; (1-(4-ACETYLPHENYL)-2-OXOHYDRAZINO)ACETIC ACID; DL-3-(P-ACETYLPHENYL)-ALANINE; 2-METHYLACETOACETIC ACID; (3AR,4S,9BS)-8-ACETYL-3A,4,5,9B-TETRAHYDRO-3H-CYCLOPENTA[C]QUINOLINE-4-CARBOXYLIC ACID; 2-ACETYL-3-(4-ETHYLPHENYL)BUTANOIC ACID; 3-(4-ACETYL-PHENYL)-2-AMINO-PROPIONIC ACID HYDROCHLORIDE; [(4-ACETYLBENZYL)OXY]ACETIC ACID; 3-ACETYL-5-NITROBENZOIC ACID; 3-ACETYLADAMANTANE-1-CARBOXYLIC ACID; 2-(3-ACETYL-1H-INDOL-1-YL)BUTANOIC ACID; 4-(3-ACETYL-2,5-DIMETHYL-1H-PYRROL-1-YL)BENZOIC ACID; [2-(2-ACETYL-PHENYL)-1H-IMIDAZOL-4-YL]-ACETIC ACID; [2-(3-ACETYL-PHENYL)-1H-IMIDAZOL-4-YL]-ACETIC ACID; [2-(4-ACETYL-PHENYL)-1H-IMIDAZOL-4-YL]-ACETIC ACID; 2-ACETYL-1H-IMIDAZOLE-4-CARBOXYLIC ACID; 5-ACETYL-1H-INDOLE-2-CARBOXYLIC ACID; 7-ACETYL-2-INDOLE CARBOXYLIC ACID; (S)-3-(3-ACETYL-4-HYDROXY-PHENYL)-2-HYDROXY-PROPIONIC ACID; (2S)-3-(3-ACETYL-4-HYDROXYPHENYL)-2-AMINOPROPANOIC ACID; 3-ACETYL-1H-INDOLE-5-CARBOXYLIC ACID; 2-METHYL-6-OXO-HEPTANOIC ACID; (3-ACETYL-2-METHYL-5-PHENYL-1H-PYRROL-1-YL)ACETIC ACID; 5-ACETYL-1H-PYRAZOLE-3-CARBOXYLIC ACID; 4-(2-ACETYL-PHENOXY)-BUTYRIC ACID; 1-(3-ACETYL-PHENYL)-5-METHYL-1H-[1, 2, 3]TRIAZOLE-4-CARBOXYLIC ACID; 1-(3-ACETYL-PHENYL)-5-ISOPROPYL-1H-[1, 2, 3]TRIAZOLE-4-CARBOXYLIC ACID; 1-(3-ACETYL-PHENYL)-5-ETHYL-1H-[1, 2, 3]TRIAZOLE-4-CARBOXYLIC ACID; 1-[(4-ACETYL-1H-PYRROL-2-YL)CARBONYL]PYRROLIDINE-2-CARBOXYLIC ACID; 2-[(4-ACETYL-1-METHYL-1H-PYRROL-2-YL)FORMAMIDO]-3-METHYLBUTANOIC ACID; 6-[(4-ACETYL-1H-PYRROL-2-YL)FORMAMIDO]HEXANOIC ACID; 2-(4-ACETYL-2-METHOXYPHENOXY)PROPANOIC ACID; 2-[(4-ACETYL-1-METHYL-1H-PYRROL-2-YL)FORMAMIDO]PROPANOIC ACID; 2-[4-(3-OXOBUTYL)PHENOXY]PROPANOIC ACID; 3-(3-ACETYLPHENOXY)PROPANOIC ACID; 2-(3-ACETYLPHENOXY)PROPANOIC ACID; 2-[4-(3-OXOBUTYL)PHENOXY]Acetic ACID; 4-[(4-ACETYL-1-METHYL-1H-PYRROL-2-YL)FORMAMIDO]BUTANOIC ACID; 2-[(4-ACETYL-1H-PYRROL-2-YL)FORMAMIDO]-4-METHYLPENTANOIC ACID; 2-[(4-ACETYL-1H-PYRROL-2-YL)FORMAMIDO]-3-METHYLBUTANOIC ACID; 1-[(4-ACETYL-1H-PYRROL-2-YL)CARBONYL]PIPERIDINE-3-CARBOXYLIC ACID; 3-[(4-ACETYL-1H-PYRROL-2-YL)FORMAMIDO]BUTANOIC ACID; 4-[(4-ACETYL-1H-PYRROL-2-YL)FORMAMIDO]BUTANOIC ACID; 3-[(4-ACETYL-1H-PYRROL-2-YL)CARBONYL]-1,3-THIAZOLIDINE-4-CARBOXYLIC ACID; 3-(4-ACETYL-2-METHOXYPHENOXY)PROPANOIC ACID; 1-(4-ACETYL-1H-PYRROLE-2-CARBONYL)PIPERIDINE-2-CARBOXYLIC ACID; 3-[(4-ACETYL-1-METHYL-1H-PYRROL-2-YL)FORMAMIDO]BUTANOIC ACID; 2-(2-ACETYLPHENOXY)-PROPANOIC ACID; 2-[(4-ACETYLBENZENE)(METHYL)SULFONAMIDO]ACETIC ACID; 4'-ACETYL-BIPHENYL-4-ACETIC ACID; 3-[4-(3-OXOBUTYL)PHENOXY]PROPANOIC ACID; 5-(3-ACETYLPHENOXYMETHYL)FURAN-2-CARBOXYLIC ACID; 3-ACETYL-2,6-DIMETHYLISONICOTINIC ACID; 2-ACETYL-3-(4-HYDROXYLPHENYL)-ACRYLIC ACID; 3-ACETYL-1H-PYRROLE-2-CARBOXYLIC ACID; (5-ACETYLTHIEN-2-YL)ACETIC ACID; 5-([(4-ACETYLPHENYL)AMINO]METHYL)-2-FUROIC ACID; 5-([(3-ACETYLPHENYL)AMINO]METHYL)-2-FUROIC ACID; 6-ACETYLPICOLINIC ACID; 5-ACETYL-1H-PYRROLE-2-CARBOXYLIC ACID; 2-(4-ACETYL-2-METHOXYPHENOXY)-3-METHYLBUTANOIC ACID; 4-[4-(3-OXOBUTYL)PHENOXY]BUTANOIC ACID; 4-(3-ACETYLPHENOXY)BUTANOIC ACID; 2-(4-ACETYLPHENOXY)-3-METHYLBUTANOIC ACID; 3-METHYL-2-[4-(3-OXOBUTYL)PHENOXY]BUTANOIC ACID; 2-(3-ACETYLPHENOXY)-3-METHYLBUTANOIC ACID; 2-({[1-(2-AMINO-1,3-THIAZOL-4-YL)-2-OXOPROPYLIDENE]AMINO}OXY)-2-METHYLPROPANOIC ACID; (1S,6R)-6-ACETYL-1-METHYL-3-CYCLOHEXENE-1-CARBOXYLIC ACID; 4-(4-ACETYL-2-METHOXYPHENOXY)BUTANOIC ACID; (2S)-2-([(4-ACETYLPHENYL)SULFONYL]AMINO)PROPANOIC ACID; 2-((1S,3S)-3-ACETYL-2,2-DIMETHYLCYCLOBUTYL)ACETIC ACID; 7-ACETYL-4-HYDROXY-QUINOLINE-3-CARBOXYLIC ACID; 2-ACETYL-3-OXO-BUTANOIC ACID; [1-(4-ACETYL-PHENYL)-PIPERIDIN-4-YL]-ACETIC ACID; 4-ACETYLBENZOIC ACID HYDRATE; 2-([(3-ACETYLPHENYL)CARBAMOYL]AMINO)ACETIC ACID; 2-([(4-ACETYLPHENYL)CARBAMOYL]AMINO)ACETIC ACID; 5-ACETYL-2-PYRIDINECARBOXYLIC ACID; 5-ACETYL-2-HYDROXY-3-METHOXY-BENZOIC ACID; 3-ACETYL-6-AMINO-4-METHYLPICOLINIC ACID; 3-ACETYL-6-AMINO-5-METHYLPICOLINIC ACID; 3-[(3-ACETYLPHENYL)SULFAMOYL]PROPANOIC ACID; 3-[(4-ACETYLPHENYL)SULFAMOYL]PROPANOIC ACID; ETHYL 2-ACETYL-4'-NITROCINNAMATE; N-ACETOACETYLANTHRANILIC ACID HYDRATE; 3-([(4-ACETYLPHENYL)CARBAMOYL]AMINO)PROPANOIC ACID; 3-([(3-ACETYLPHENYL)CARBAMOYL]AMINO)PROPANOIC ACID; 4-([(3-ACETYLPHENYL)CARBAMOYL]AMINO)BUTANOIC ACID; 4-([(4-ACETYLPHENYL)CARBAMOYL]AMINO)BUTANOIC ACID; 5-ACETYL-3-METHYLTHIENO[2,3-B]PYRIDINE-2-CARBOXYLIC ACID; 2-ACETYLISONICOTINIC ACID; (4R)-4-(2-ACETYLPHENYL)-4-AMINOBUTANOIC ACID; (4S)-4-(2-ACETYLPHENYL)-4-AMINOBUTANOIC ACID; (4R)-4-(3-ACETYLPHENYL)-4-AMINOBUTANOIC ACID; (4S)-4-(3-ACETYLPHENYL)-4-AMINOBUTANOIC ACID; 3-ISOXAZOLECARBOXYLIC ACID, 5-ACETYL-; (5R)-5-(2-ACETYLPHENYL)-5-AMINOPENTANOIC ACID; (5S)-5-(2-ACETYLPHENYL)-5-

AMINOPENTANOIC ACID; (5R)-5-(3-ACETYLPHENYL)-5-AMINOPENTANOIC ACID; (5S)-5-(3-ACETYLPHENYL)-5-AMINOPENTANOIC ACID; BENZOIC ACID, 3-ACETYL-2-AMINO-6-METHOXY-; 3-ACETYL-1-BUTYLINDOLE-6-CARBOXYLIC ACID; 2-[(3-ACETYLBENZENE)(METHYL)SULFONAMIDO]ACETIC ACID; 1-ACETYLCYCLOPROPANECARBOXYLIC ACID; 5-(4-ACETYLPHENOXY)PENTANOIC ACID; 5-(3-ACETYLPHENOXY)PENTANOIC ACID; 2-([(5-ACETYL-2-ETHOXYPHENYL)METHYL]SULFANYL)ACETIC ACID; 2-[(4-ACETYL-1H-PYRROL-2-YL)FORMAMIDO]-3-HYDROXYBUTANOIC ACID; 2-[(4-ACETYL-1-METHYL-1H-PYRROL-2-YL)FORMAMIDO]-3-HYDROXYPROPANOIC ACID; 4-[(4-ACETYL-1H-PYRROL-2-YL)-N-METHYLFORMAMIDO]BUTANOIC ACID; 3-([2-(2-ACETYLPHENOXY)ETHYL]SULFANYL)PROPANOIC ACID; 2-([(5-ACETYL-2-METHOXYPHENYL)METHYL]SULFANYL)PROPANOIC ACID; 2-([2-(2-ACETYLPHENOXY)ETHYL]SULFANYL)PROPANOIC ACID; 2-[(3-ACETYLBENZENE)SULFONAMIDO]PROPANOIC ACID; 3-(2-ACETYLPHENOXY)PROPANOIC ACID; 3-[(4-ACETYL-1H-PYRROL-2-YL)FORMAMIDO]PROPANOIC ACID; 3-[(4-ACETYL-1-METHYL-1H-PYRROL-2-YL)FORMAMIDO]PROPANOIC ACID; 2-[(4-ACETYL-1-METHYL-1H-PYRROL-2-YL)-N-METHYLFORMAMIDO]ACETIC ACID; 2-[(4-ACETYL-1H-PYRROL-2-YL)FORMAMIDO]-3-HYDROXYPROPANOIC ACID; 2-([2-(2-ACETYLPHENOXY)ETHYL]SULFANYL)ACETIC ACID; 2-[(3-ACETYLPHENYL)SULFAMOYL]ACETIC ACID; 2-((([(2-METHYL-4-OXOPENTAN-3-YL)CARBAMOYL]METHYL)SULFANYL)PROPANOIC ACID; 4-ACETYL-5-OXO-HEX-2-ENOIC ACID; (S)-3-(3-ACETYL-4-HYDROXY-PHENYL)-2-AMINO-PROPIONIC ACID HYDROCHLORIDE; 2-(2-ACETYL-5-METHOXYPHENYL)ACETIC ACID; N-(((2-ACETYLPHENYL)AMINO)CARBONYL)GLYCINE; N-(((2-ACETYLPHENYL)AMINO)CARBONYL)-BETA-ALANINE; N-(((2-ACETYLPHENYL)AMINO)CARBONYL)-L-ALANINE; BUTANOIC ACID, 2-AMINO-3-OXO-; 2-[(4-ACETYLPHENYL)SULFAMOYL]ACETIC ACID; 2-((([(2-METHYL-4-OXOPENTAN-3-YL)CARBAMOYL]METHYL)SULFANYL)ACETIC ACID; 3-((([(2-METHYL-4-OXOPENTAN-3-YL)CARBAMOYL]METHYL)SULFANYL)PROPANOIC ACID; (2R)-3-(3-ACETYL-4-HYDROXYPHENYL)-2-AMINOPROPANOIC ACID; D-4-ACETYLPHE; AC-THZ-OH; AC-D-THZ-OH; 3'-ACETYL-BIPHENYL-2-ACETIC ACID; 3-[4-(3-OXOBUTYL)PHENOXY]BUTANOIC ACID; 3-(4-ACETYL-2-METHOXYPHENOXY)BUTANOIC ACID; 2-METHYL-3-[4-(3-OXOBUTYL)PHENOXY]PROPANOIC ACID; 3-(4-ACETYL-2-METHOXYPHENOXY)-2-METHYLPROPANOIC ACID; 2-(([(2-ACETYLPHENYL)CARBAMOYL]METHYL)AMINO)ACETIC ACID; 2-([2-(2-ACETYLPHENOXY)ETHYL]AMINO)PROPANOIC ACID; 3-([(5-ACETYL-2-METHOXYPHENYL)METHYL]AMINO)PROPANOIC ACID; 2-(([(4-ACETYLPHENYL)CARBAMOYL]METHYL)AMINO)ACETIC ACID; 3-([2-(2-ACETYLPHENOXY)ETHYL]AMINO)PROPANOIC ACID; 2-([2-(2-ACETYLPHENOXY)ETHYL](METHYL)AMINO)ACETIC ACID; 2-([(5-ACETYL-2-METHOXYPHENYL)METHYL](METHYL)AMINO)ACETIC ACID; 3-[(4-ACETYLPHENYL)SULFANYL]PROPANOIC ACID; 2-[(4-ACETYLPHENYL)SULFANYL]PROPANOIC ACID; 2-([(5-ACETYL-2-METHOXYPHENYL)METHYL]AMINO)PROPANOIC ACID; 2-[4-(3-OXOBUTYL)PHENOXY]BUTANOIC ACID; 2-(3-ACETYLPHENOXY)BUTANOIC ACID; 4-((([(2-METHYL-4-OXOPENTAN-3-YL)CARBAMOYL]METHYL)AMINO)BUTANOIC ACID; 2-(([(3-ACETYLPHENYL)CARBAMOYL]METHYL)AMINO)ACETIC ACID; 2-([(5-ACETYL-2-ETHOXYPHENYL)METHYL]AMINO)ACETIC ACID; 3-[(4-ACETYL-2-FLUOROPHENYL)SULFANYL]PROPANOIC ACID; 2-[(4-ACETYL-2-FLUOROPHENYL)SULFANYL]PROPANOIC ACID; ABAMACHEM ABA-1038178; 3-(3-ACETYL-2-METHYL-5-PHENYL-1H-PYRROL-1-YL)PROPANOIC ACID; 2-(3-ACETYLPHENOXY)-2,2-DIFLUOROACETIC ACID; 2,2-DIFLUORO-2-[4-(3-OXOBUTYL)PHENOXY]ACETIC ACID; 2-(4-ACETYLPHENOXY)-2,2-DIFLUOROACETIC ACID; 2-(4-ACETYL-2-METHOXYPHENOXY)-2,2-DIFLUOROACETIC ACID; 2-((([(2-METHYL-4-OXOPENTAN-3-YL)CARBAMOYL]METHYL)AMINO)ACETIC ACID; 4-ACETYL-5-METHYL-3-PROPYL-1H-PYRROLE-2-CARBOXYLIC ACID; 2-(4-ACETYLPHENOXY)BUTANOIC ACID; 2-([(5-ACETYL-2-ETHOXYPHENYL)METHYL](METHYL)AMINO)ACETIC ACID; FCHGROUP FCH243829; 3-METHYL-2-((([(2-METHYL-4-OXOPENTAN-3-YL)CARBAMOYL]METHYL)AMINO)BUTANOIC ACID; 3-((([(4-ACETYLPHENYL)CARBAMOYL]METHYL)AMINO)PROPANOIC ACID; 2-((([(4-ACETYLPHENYL)CARBAMOYL]METHYL)(METHYL)AMINO)ACETIC ACID; (2-ACETYL-1H-IMIDAZOL-1-YL)ACETIC ACID; 2-([2-(2-ACETYLPHENOXY)ETHYL]AMINO)ACETIC ACID; 2-([(5-ACETYL-2-METHOXYPHENYL)METHYL]AMINO)ACETIC ACID; 4'-ACETYL-2'-METHYLBIPHENYL-4-CARBOXYLIC ACID; 2-(4-ACETYL-2-METHOXYPHENOXY)BUTANOIC ACID; 2-[(4-ACETYLPHENYL)CARBAMOYL]CYCLOPROPANE-1-CARBOXYLIC ACID; 2-[(3-ACETYLPHENYL)CARBAMOYL]CYCLOPROPANE-1-CARBOXYLIC ACID; 3-((([(2-METHYL-4-OXOPENTAN-3-YL)CARBAMOYL]METHYL)AMINO)PROPANOIC ACID; 2-(([(2-METHYL-4-OXOPENTAN-3-YL)CARBAMOYL]METHYL)AMINO)PROPANOIC ACID; 2-[METHYL((([(2-METHYL-4-OXOPENTAN-3-YL)CARBAMOYL]METHYL))AMINO]ACETIC ACID; 2-([(5-ACETYL-2-ETHOXYPHENYL)METHYL]AMINO)PROPANOIC ACID; 4-([2-(2-ACETYLPHENOXY)ETHYL]AMINO)BUTANOIC ACID; 3-((([(2-ACETYLPHENYL)CARBAMOYL]METHYL)AMINO)PROPANOIC ACID; 1-([(2-METHYL-4-OXOPENTAN-3-YL)CARBAMOYL]METHYL)PYRROLIDINE-2-CARBOXYLIC ACID; 1-[(4-ACETYL-1-METHYL-1H-PYRROL-2-YL)CARBONYL]PYRROLIDINE-2-CARBOXYLIC ACID; 3-CARBAMOYL-2-[(4-ACETYL-1H-PYRROL-2-YL)FORMAMIDO]PROPANOIC ACID; 2-CYCLOPROPYL-2-[(4-ACETYL-1H-PYRROL-2-YL)FORMAMIDO]PROPANOIC ACID; 1-[(4-ACETYL-1H-PYRROL-2-YL)CARBONYL]PIPERIDINE-4-CARBOXYLIC ACID; 2-[(4-ACETYLPHENYL)SULFANYL]PYRIDINE-3-CARBOXYLIC ACID; 2-[N-(CYCLOPROPYLMETHYL)(4-ACETYL-1H-PYRROL-2-YL)FORMAMIDO]ACETIC ACID; 2-((([(2-ACETYLPHENYL)CARBAMOYL]METHYL)(METHYL)AMINO)ACETIC ACID; 3-[N-CYCLOPROPYL-1-(4-ACETYL-1H-PYRROL-2-YL)FORMAMIDO]PROPANOIC ACID; 5-[4-(3-OXOBUTYL)PHENOXY]PENTANOIC ACID; 5-(4-ACETYL-2-METHOXYPHENOXY)PENTANOIC ACID; 2-(3-ACETYLPHENOXYMETHYL)FURAN-3-

CARBOXYLIC ACID; 3-(3-ACETYLPHENOXYMETHYL)FURAN-2-CARBOXYLIC ACID; 3-(4-ACETYLPHENOXYMETHYL)FURAN-2-CARBOXYLIC ACID; 2-[(4-ACETYL-1H-PYRROL-2-YL)FORMAMIDO]-3,3-DIMETHYLBUTANOIC ACID; 3-(([(3-ACETYLPHENYL)CARBAMOYL]METHYL)AMINO)PROPANOIC ACID; 3-([(5-ACETYL-2-ETHOXYPHENYL)METHYL]AMINO)PROPANOIC ACID; 2-(([(2-ACETYLPHENYL)CARBAMOYL]METHYL)AMINO)PROPANOIC ACID; 4-([(5-ACETYL-2-METHOXYPHENYL)METHYL]AMINO)BUTANOIC ACID; 5-[(3-ACETYLPHENYL)CARBAMOYL]PENTANOIC ACID; 5-[(4-ACETYLPHENYL)CARBAMOYL]PENTANOIC ACID; 2-[(4-ACETYL-1H-PYRROL-2-YL)FORMAMIDO]-3-METHYLPENTANOIC ACID; 1-[(4-ACETYL-1H-PYRROL-2-YL)CARBONYL]-4-HYDROXYPYRROLIDINE-2-CARBOXYLIC ACID; 1-[(4-ACETYL-1H-PYRROLE-2-)AMIDO]CYCLOPENTANE-1-CARBOXYLIC ACID; 2-(4-ACETYLPHENOXYMETHYL)FURAN-3-CARBOXYLIC ACID; 2-(([(2-METHYL-4-OXOPENTAN-3-YL)CARBAMOYL]METHYL)AMINO)PENTANOIC ACID; 4-[(4-ACETYLPHENYL)SULFANYL]BENZOIC ACID; 2-[(4-ACETYLPHENYL)SULFANYL]BENZOIC ACID; 2-(([(3-ACETYLPHENYL)CARBAMOYL]METHYL)(METHYL)AMINO)ACETIC ACID; 2-[CYCLOPROPYL(([(2-METHYL-4-OXOPENTAN-3-YL)CARBAMOYL]METHYL))AMINO]ACETIC ACID; 2-[(4-ACETYL-1H-PYRROL-2-YL)-N-(PROPAN-2-YL)FORMAMIDO]ACETIC ACID; 2-[N-(BUTAN-2-YL)(4-ACETYL-1H-PYRROL-2-YL)FORMAMIDO]ACETIC ACID; 2-(([(2-METHYL-4-OXOPENTAN-3-YL)CARBAMOYL]METHYL)(PROPAN-2-YL)AMINO)ACETIC ACID; 2-ACETYL-3-HYDROXYTHIOPHENE-5-CARBOXYLIC ACID; 2-(([(4-ACETYLPHENYL)CARBAMOYL]METHYL)AMINO)PROPANOIC ACID; 2-(([(3-ACETYLPHENYL)CARBAMOYL]METHYL)AMINO)PROPANOIC ACID; 5-ACETYL-2-METHOXYBENZOIC ACID; 3-([2-(2-ACETYLPHENOXY)ETHYL](METHYL)AMINO)PROPANOIC ACID; 3-([(5-ACETYL-2-METHOXYPHENYL)METHYL](METHYL)AMINO)PROPANOIC ACID; 2-(3-ACETYL-1H-PYRROL-2-YL)ACETIC ACID; 2,2-DIMETHYL-4-OXO-PENTANOIC ACID; 7-METHYL-8-OXONONANOIC ACID; 4-ACETYL-3-ETHYL-5-METHYL-1H-PYRROLE-2-CARBOXYLIC ACID; 4-ACETYL PHENYLALANINE HYDROCHLORIDE; 1H-BENZIMIDAZOLE-6-CARBOXYLIC ACID, 2-ACETYL-; GLYCINE, N-(1-METHYL-3-OXOBUTYLIDENE)-; 2-ACETYL-ALPHA-AMINO-CYCLOPROPANEACETIC ACID; 3-[METHYL(([(2-METHYL-4-OXOPENTAN-3-YL)CARBAMOYL]METHYL))AMINO]PROPANOIC ACID; 4-(2-ACETYLPHENYL)-4-OXOBUTANOIC ACID; 3-[(4-ACETYL-1H-PYRROL-2-YL)-N-ETHYLFORMAMIDO]PROPANOIC ACID; 3-[(4-ACETYL-1-METHYL-1H-PYRROL-2-YL)-N-ETHYLFORMAMIDO]PROPANOIC ACID; 3-ACETYL-7-BENZOFURANACETIC ACID; 5-OXO-2-HEXENOIC ACID; (2S)-2-[(4-ACETYL-1H-PYRROL-2-YL)FORMAMIDO]-3-METHYLPENTANOIC ACID; 2-[ETHYL([((2-METHYL-4-OXOPENTAN-3-YL)CARBAMOYL]METHYL))AMINO]ACETIC ACID; 3-[ETHYL(([(2-METHYL-4-OXOPENTAN-3-YL)CARBAMOYL]METHYL))AMINO]PROPANOIC ACID; 2-([(5-ACETYL-2-METHOXYPHENYL)METHYL](ETHYL)AMINO)ACETIC ACID; 2-([2-(2-ACETYLPHENOXY)ETHYL](ETHYL)AMINO)ACETIC ACID; 2-(([(2-METHYL-4-OXOPENTAN-3-YL)CARBAMOYL]METHYL)(PROPYL)AMINO)ACETIC ACID; 2-[(4-ACETYL-1H-PYRROL-2-YL)-N-ETHYLFORMAMIDO]ACETIC ACID; 2-[(4-ACETYL-1H-PYRROL-2-YL)FORMAMIDO]-4-HYDROXYBUTANOIC ACID; 2-[(4-ACETYL-1-METHYL-1H-PYRROL-2-YL)FORMAMIDO]-4-HYDROXYBUTANOIC ACID; 4-METHYL-3-(3-OXOBUTANAMIDO)BENZOIC ACID; 3-(3-OXOBUTANAMIDO)-3-(THIOPHEN-2-YL)PROPANOIC ACID; 2-FLUORO-5-(3-OXOBUTANAMIDO)BENZOIC ACID; 4-FLUORO-3-(3-OXOBUTANAMIDO)BENZOIC ACID; 2,4-DIFLUORO-5-(3-OXOBUTANAMIDO)BENZOIC ACID; 2-METHYL-3-(3-OXOBUTANAMIDO)BENZOIC ACID; 3-METHYL-4-(3-OXOBUTANAMIDO)BENZOIC ACID; 2-CHLORO-5-(3-OXOBUTANAMIDO)BENZOIC ACID; 2-[(4-ACETYL-1H-PYRROL-2-YL)FORMAMIDO]-2-METHYLPROPANOIC ACID; 2-[(4-ACETYL-1-METHYL-1H-PYRROL-2-YL)FORMAMIDO]-2-METHYLPROPANOIC ACID; 3-(4-ACETYLPHENYL)-2-BROMOPROPANOIC ACID; 2-PYRIDINECARBOXYLIC ACID, 3-(2-OXOPROPOXY)-; 2-([(4-ACETYLPHENYL)CARBAMOYL]AMINO)-2-METHYLPROPANOIC ACID; 2-([(3-ACETYLPHENYL)CARBAMOYL](METHYL)AMINO)ACETIC ACID; 2-([(3-ACETYLPHENYL)CARBAMOYL]AMINO)PROPANOIC ACID; 2-([(3-ACETYLPHENYL)CARBAMOYL]AMINO)-3-HYDROXYPROPANOIC ACID; 3-([(3-ACETYLPHENYL)CARBAMOYL]AMINO)BUTANOIC ACID; 2-([(3-ACETYLPHENYL)CARBAMOYL]AMINO)BUTANOIC ACID; 3-([(3-ACETYLPHENYL)CARBAMOYL](METHYL)AMINO)PROPANOIC ACID; 2-([(3-ACETYLPHENYL)CARBAMOYL](ETHYL)AMINO)ACETIC ACID; 2-([(3-ACETYLPHENYL)CARBAMOYL]AMINO)-2-METHYLPROPANOIC ACID; 6-[(4-ACETYLPHENYL)SULFANYL]PYRIDINE-3-CARBOXYLIC ACID; 2-([(4-ACETYLPHENYL)CARBAMOYL](METHYL)AMINO)ACETIC ACID; 2-([(4-ACETYLPHENYL)CARBAMOYL]AMINO)-3-HYDROXYPROPANOIC ACID; 3-([(4-ACETYLPHENYL)CARBAMOYL]AMINO)BUTANOIC ACID; 2-([(4-ACETYLPHENYL)CARBAMOYL]AMINO)BUTANOIC ACID; 3-([(4-ACETYLPHENYL)CARBAMOYL](METHYL)AMINO)PROPANOIC ACID; 2-([(4-ACETYLPHENYL)CARBAMOYL](ETHYL)AMINO)ACETIC ACID; 2-[(4-ACETYLPHENYL)SULFANYL]PYRIDINE-4-CARBOXYLIC ACID; 2-(4-ACETYLPHENOXY)-2,4-DIMETHYLPENTANOIC ACID; 2-(4-ACETYLPHENOXY)-2-METHYLPENTANOIC ACID; 2-CYCLOPROPYL-2-(3-ACETYLPHENOXY)PROPANOIC ACID; 2-(3-ACETYLPHENOXY)-2-ETHYLBUTANOIC ACID; 1-(3-ACETYLPHENOXY)CYCLOHEXANE-1-CARBOXYLIC ACID; 1-(4-ACETYLPHENOXY)CYCLOPENTANE-1-CARBOXYLIC ACID; 2-CYCLOPROPYL-2-(4-ACETYLPHENOXY)PROPANOIC ACID; 2-(4-ACETYLPHENOXY)-2-ETHYLBUTANOIC ACID; 1-(4-ACETYLPHENOXY)CYCLOHEXANE-1-CARBOXYLIC ACID; 4-(4-ACETYLPHENOXY)OXANE-4-CARBOXYLIC ACID; 2-(4-ACETYLPHENOXY)-2-METHYLBUTANOIC ACID; 3-(3-ACETYLPHENOXY)THIOLANE-3-CARBOXYLIC ACID; 2-(3-ACETYLPHENOXY)-2,4-DIMETHYLPENTANOIC ACID; 1-(3-ACETYLPHENOXY)CYCLOPENTANE-1-CARBOXYLIC ACID; 4-(3-ACETYLPHE-

NOXY)OXANE-4-CARBOXYLIC ACID; 2-(3-ACETYLPHENOXY)-2-METHYLPENTANOIC ACID; 2-(3-ACETYLPHENOXY)-2-METHYLBUTANOIC ACID; 2-METHYL-2-[4-(3-OXOBUTYL)PHENOXY]PROPANOIC ACID; 2-METHYL-2-[4-(3-OXOBUTYL)PHENOXY]BUTANOIC ACID; 3-(4-ACETYLPHENOXY)THIOLANE-3-CARBOXYLIC ACID; 2-(4-ACETYL-2-METHOXYPHENOXY)-2-METHYLPROPANOIC ACID; 2-(4-ACETYL-2-METHOXYPHENOXY)-2-METHYLBUTANOIC ACID; 2-ACETYL-4-BROMOPHENYLHYDROGENCARBONATE; 3-(2-FURYL)-1-(2-OXOPROPYL)-1H-PYRAZOLE-5-CARBOXYLIC ACID; 3-(2-OXOPROPYL)-3H-IMIDAZO[4,5-B]PYRIDINE-2-CARBOXYLIC ACID; 2-([(4-ACETYLPHENYL)CARBAMOYL]AMINO)PROPANOIC ACID; 4-(METHOXYCARBONYL)-1-(2-OXOPROPYL)-1H-IMIDAZOLE-5-CARBOXYLIC ACID; (2S)-2-([(4-ACETYLPHENYL)CARBAMOYL]AMINO)-3-HYDROXYPROPANOIC ACID; (2S)-2-([(3-ACETYLPHENYL)CARBAMOYL]AMINO)-3-HYDROXYPROPANOIC ACID; 5-ACETYL-1,6-DIMETHYL-2-OXO-1,2-DIHYDROPYRIDINE-3-CARBOXYLIC ACID; 5-ACETYL-1-ETHYL-6-METHYL-2-OXO-1,2-DIHYDROPYRIDINE-3-CARBOXYLIC ACID; 6-ACETYL-5-METHYL-3-OXO-3,4-DIHYDROPYRAZINE-2-CARBOXYLIC ACID; 5-ACETYL-4,6-DIMETHYL-2-OXO-1,2-DIHYDROPYRIDINE-3-CARBOXYLIC ACID; 5-ACETYL-6-METHYL-2-OXO-1-PROPYL-1,2-DIHYDROPYRIDINE-3-CARBOXYLIC ACID; 2-(1-[(4-ACETYL-1H-PYRROL-2-YL)CARBONYL]PYRROLIDIN-2-YL)ACETIC ACID; 4-(3-OXOBUTANAMIDO)BUTANOIC ACID; 2-[(4-ACETYL-2-METHOXYPHENYL)SULFANYL]ACETIC ACID; 2-(3-ACETYLPHENOXY)-2-METHYLPROPANOIC ACID; 2-(ACETYL-METHOXYCARBONYLAMINO)BENZOIC ACID; 5-(2-ACETYLPHENOXYMETHYL)-FURAN-2-CARBOXYLIC ACID; 3-(3-OXOBUTANAMIDO)PROPANOIC ACID; 2-(5-ACETYLFURAN-2-YL)ACETIC ACID; 2-(4-ACETYLPHENOXY)-4-METHOXY-2-METHYLBUTANOIC ACID; 2-(3-ACETYLPHENOXY)-4-METHOXY-2-METHYLBUTANOIC ACID; 5-[2-(3-ACETYL-PHENYL)-PROPYL]-FURAN-2-CARBOXYLIC ACID; 2-[(2-ACETYLNAPHTHALEN-1-YL)OXY]PROPANOIC ACID; 2-(4-ACETYL-3-METHOXYPHENYL)ACETIC ACID; BENZENEACETIC ACID, 3-ACETYL; 4-ACETYL-5-BROMONICOTINIC ACID; 4-ACETYLNICOTINIC ACID; 3-ACETYLISONICOTINIC ACID; 4-(ETHOXYCARBONYL)-3,5-DIMETHYL-1-(2-OXOPROPYL)-1H-PYRROLE-2-CARBOXYLIC ACID; 3-METHYL-2-(3-OXOBUTANAMIDO)BUTANOIC ACID; (2S)-2-(2-ACETYLPHENYL)-2-HYDROXYACETIC ACID; 2-[(3-ACETYLPHENYL)SULFAMOYL]PROPANOIC ACID; 3-ACETYL-2-PYRIDINECARBOXYLIC ACID; 3-ACETYL-5-CHLORO-2-PYRIDINECARBOXYLIC ACID; 2-(2-ACETYL-4-METHYLPHENOXY)PROPANOIC ACID; 2-[(4-ACETYLPHENYL)SULFAMOYL]PROPANOIC ACID; (2R)-2-([(3-ACETYLPHENYL)CARBAMOYL]AMINO)PROPANOIC ACID; (2R)-2-([(4-ACETYLPHENYL)CARBAMOYL]AMINO)PROPANOIC ACID; 3-(4-ACETYLPHENOXY)BENZOIC ACID; 2-(4-ACETYLPHENOXY)BENZOIC ACID; 3-(4-ACETYLPHENOXY)PYRIDINE-2-CARBOXYLIC ACID; 1-(4-ACETYLPHENYL)-3,5-DIMETHYL-1H-PYRAZOLE-4-CARBOXYLIC ACID; 1-(4-ACETYL-2-FLUOROPHENYL)-1H-PYRAZOLE-4-CARBOXYLIC ACID; 1-(4-ACETYLPHENYL)-1H-PYRAZOLE-4-CARBOXYLIC ACID; 2-(2-ACETYL-4-CHLOROPHENOXY)PROPANOIC ACID; 4-ACETYLPYRIMIDINE-5-CARBOXYLIC ACID; 5-ACETYL-2-MERCAPTOBENZOIC ACID; 3-[(6-ACETYL-2-NAPHTHALENYL)AMINO]ALANINE; 5-ACETYLPYRIMIDINE-4-CARBOXYLIC ACID; 5-ACETYL-1-PHENYL-4,5-DIHYDRO-1H-PYRAZOLE-3-CARBOXYLIC ACID; 5-ACETYL-4-METHYL-1H-PYRAZOLE-3-CARBOXYLIC ACID; 2,2-DIMETHYL-3-OXOBUTANOIC ACID; 3-ACETYL-1H-INDOLE-6-CARBOXYLIC ACID; 2-[(4-ACETYLPHENYL)CARBAMOYL]ACETIC ACID; 2-[(3-ACETYLPHENYL)CARBAMOYL]ACETIC ACID; 5-(2-ACETYLPHENYL)-PICOLINIC ACID; 5-(4-ACETYLPHENYL)-PICOLINIC ACID; 5-(3-ACETYLPHENYL)-PICOLINIC ACID; 2-FLUORO-3-OXOBUTANOIC ACID; 2-HYDROXY-2-METHYL-3-OXOBUTANOIC ACID; 5-ACETYL-INDOLE-3-CARBOXYLIC ACID; 2,2-DICHLORO-ACETOACETIC ACID; 5-CHLORO-6-OXO-HEPTANOIC ACID; 4-ACETAMIDO-5-OXO-HEXANOIC ACID; 1-PYRROLIDINECARBOXYLIC ACID, 3-ACETYL-2,4-DIMETHYL-; 1,4-BENZODIOXIN-2-CARBOXYLIC ACID, 2,3-DIHYDRO-6-(2-OXOPROPYL)-; 5-(2-ACETYLPHENYL)-NICOTINIC ACID; 5-(4=ACETYLPHENYL)-NICOTINIC ACID; 4-(4-ACETYL-2-METHOXYPHENOXY)PENTANOIC ACID; 4-(4-ACETYLPHENOXY)PENTANOIC ACID; 5-(5-ACETYLTHIOPHEN-2-YL)-NICOTINIC ACID; 2-(2-ACETYLPHENYL)-ISONICOTINIC ACID; 2-(3-ACETYLPHENYL)-ISONICOTINIC ACID; 2-(4-ACETYLPHENYL)-ISONICOTINIC ACID; 2-([2-(2-ACETYLPHENOXY)ETHYL](METHYL)AMINO)PROPANOIC ACID; 2-METHYL-2-[METHYL((([(2-METHYL-4-OXOPENTAN-3-YL)CARBAMOYL]METHYL))AMINO]PROPANOIC ACID; 2-ACETYL-5-THIAZOLECARBOXYLIC ACID; 2-(4-ACETYLPHENYL)BENZOIC ACID; 5-ACETYL-2-METHYL-NICOTINIC ACID; GLYCINE, N-(4-ACETYL-2-NITROPHENYL)-; BETA-ALANINE, N-(4-ACETYL-2-NITROPHENYL)-; 4-[4-(3-OXOBUTYL)PHENOXY]BUT-2-ENOIC ACID; 2-(2-ACETYL-5-FLUOROPHENOXY)PROPANOIC ACID; 5-(3-ACETYLPHENOXYMETHYL)FURAN-3-CARBOXYLIC ACID; 3-([(3-ACETYLPHENYL)CARBAMOYL]AMINO)-2-METHYLPROPANOIC ACID; 5-(4-ACETYLPHENOXYMETHYL)OXOLANE-2-CARBOXYLIC ACID; 4-(3-ACETYLPHENOXY)PENTANOIC ACID; 3-([(4-ACETYLPHENYL)CARBAMOYL]AMINO)-2-METHYLPROPANOIC ACID; 5-(3-ACETYLPHENOXYMETHYL)OXOLANE-2-CARBOXYLIC ACID; 5-(4-ACETYLPHENOXYMETHYL)FURAN-3-CARBOXYLIC ACID; 2-([(3-ACETYLPHENYL)CARBAMOYL](METHYL)AMINO)PROPANOIC ACID; 2-([(5-ACETYL-2-METHOXYPHENYL)METHYL](METHYL)AMINO)PROPANOIC ACID; 4-[4-(3-OXOBUTYL)PHENOXY]PENTANOIC ACID; 2-(4-ACETYLPHENOXY)-3-METHOXY-2-METHYLPROPANOIC ACID; 2-(3-ACETYLPHENOXY)-3-METHOXY-2-METHYLPROPANOIC ACID; 2-(2-ACETYLPHENYL)-5-FLUOROPYRIDINE-4-CARBOXYLIC ACID; 3-(2-ACETYLPHENYL)PYRIDINE-2-CARBOXYLIC ACID; 4-(2-ACETYLPHENYL)PYRIDINE-2-CARBOXYLIC ACID; 4-(4-ACETYL-2-METHOXYPHENOXY)BUT-2-ENOIC ACID; 2-(2-ACETYLPHENYL)PYRIDINE-3-

CARBOXYLIC ACID; 4-ACETYLTHIOPHENE-2-CARBOXYLIC ACID; 5-(2-ACETYLPHENYL)-2-AMINOPYRIDINE-3-CARBOXYLIC ACID; 3-(2-ACETYLPHENYL)-6-AMINOPYRIDINE-2-CARBOXYLIC ACID; 3-(2-ACETYLPHENYL) PYRIDINE-4-CARBOXYLIC ACID; 6-(2-ACETYLPHENYL)PYRIDINE-3-CARBOXYLIC ACID; 5-(2-ACETYLPHENYL)-2-HYDROXYBENZOIC ACID; 3-(2-ACETYLPHENYL)-4-HYDROXYBENZOIC ACID; 3-(2-ACETYLPHENYL)-5-HYDROXYBENZOIC ACID; 3-(2-ACETYLPHENYL)-2-HYDROXYBENZOIC ACID; (2S)-2-(5-ACETYL-2-CHLORO-6-METHYL(3-PYRIDYL))-2-AMINOPROPANOIC ACID; (2R)-2-(5-ACETYL-2-CHLORO-6-METHYL(3-PYRIDYL))-2-AMINOPROPANOIC ACID; (2S)-2-(5-ACETYL-6-CHLORO(3-PYRIDYL))-2-AMINOPROPANOIC ACID; (2R)-2-(5-ACETYL-6-CHLORO(3-PYRIDYL))-2-AMINOPROPANOIC ACID; (2S)-2-(6-ACETYL(2-PYRIDYL))-2-AMINOPROPANOIC ACID; (2R)-2-(6-ACETYL(2-PYRIDYL))-2-AMINOPROPANOIC ACID; (2R)-2-(6-ACETYL(2-PYRIDYL))-2-AMINOACETIC ACID; (2S)-2-(5-ACETYL-2-CHLORO-6-METHYL(3-PYRIDYL))-2-AMINOACETIC ACID; (2R)-2-(5-ACETYL-2-CHLORO-6-METHYL(3-PYRIDYL))-2-AMINOACETIC ACID; (2S)-2-(5-ACETYL-6-CHLORO(3-PYRIDYL))-2-AMINOACETIC ACID; (2R)-2-(5-ACETYL-6-CHLORO(3-PYRIDYL))-2-AMINOACETIC ACID; (2S)-2-(5-ACETYL(2-PYRIDYL))-2-AMINOPROPANOIC ACID; (2R)-2-(5-ACETYL(2-PYRIDYL))-2-AMINOPROPANOIC ACID; (2S)-2-(5-ACETYL(2-PYRIDYL))-2-AMINOACETIC ACID; (2R)-2-(5-ACETYL(2-PYRIDYL))-2-AMINOACETIC ACID; (2S)-2-(6-ACETYL(2-PYRIDYL))-2-AMINOACETIC ACID; 3-(5-ACETYLTHIOPHEN-3-YL)PROPIOLIC ACID; 3-(2-ACETYLTHIOPHEN-3-YL)PROPIOLIC ACID; 2-(4-ACETYL-5-METHYL-1H-PYRAZOL-1-YL)ACETIC ACID; 5-(4-ACETYLPHENYL)-3-AMINOBENZOIC ACID; 4-(4-ACETYLPHENYL)-3-FLUOROBENZOIC ACID; 5-(3-ACETYLPHENYL)-2-CHLOROBENZOIC ACID; 4-(3-ACETYLPHENYL)-2-CHLOROBENZOIC ACID; 3-(3-ACETYLPHENYL)-5-CHLOROBENZOIC ACID; 2-(3-ACETYLPHENYL)-4-CHLOROBENZOIC ACID; 2-(3-ACETYLPHENYL)-6-CHLOROBENZOIC ACID; 3-(3-ACETYLPHENYL)-4-CHLOROBENZOIC ACID; 2-(4-ACETYLPHENYL)-6-METHYLBENZOIC ACID; 4-(4-ACETYLPHENYL)-3-METHYLBENZOIC ACID; 3-(4-ACETYLPHENYL)-2-METHYLBENZOIC ACID; 2-(4-ACETYLPHENYL)-5-METHYLBENZOIC ACID; 4-(4-ACETYLPHENYL)-3-HYDROXYBENZOIC ACID; 3-(4-ACETYLPHENYL)-5-HYDROXYBENZOIC ACID; 4-(4-ACETYLPHENYL)-2-HYDROXYBENZOIC ACID; 2-(4-ACETYLPHENYL)-4-FLUOROBENZOIC ACID; 2-(4-ACETYLPHENYL)-5-FLUOROBENZOIC ACID; 3-(4-ACETYLPHENYL)-4-FLUOROBENZOIC ACID; 4-(4-ACETYLPHENYL)-2-FLUOROBENZOIC ACID; 5-(4-ACETYLPHENYL)-2-FLUOROBENZOIC ACID; 3-(4-ACETYLPHENYL)-5-FLUOROBENZOIC ACID; 2-(4-ACETYLPHENYL)-6-FLUOROBENZOIC ACID; 4-(4-ACETYLPHENYL)-3-METHOXYBENZOIC ACID; 3-(4-ACETYLPHENYL)-2-METHOXYBENZOIC ACID; 2-(3-ACETYLPHENYL)-6-METHYLBENZOIC ACID; 4-(3-ACETYLPHENYL)-3-METHYLBENZOIC ACID; 3-(3-ACETYLPHENYL)-2-METHYLBENZOIC ACID; 4-(3-ACETYLPHENYL)-2-HYDROXYBENZOIC ACID; 2-(3-ACETYLPHENYL)-4-FLUOROBENZOIC ACID; 2-(3-ACETYLPHENYL)-5-FLUOROBENZOIC ACID; 3-(3-ACETYLPHENYL)-5-FLUOROBENZOIC ACID; 2-(3-ACETYLPHENYL)-6-FLUOROBENZOIC ACID; 4-(3-ACETYLPHENYL)-3-METHOXYBENZOIC ACID; 3-(3-ACETYLPHENYL)-2-METHOXYBENZOIC ACID; 2-(3-ACETYLPHENYL)-5-METHOXYBENZOIC ACID; 3-(3-ACETYLPHENYL)-5-METHOXYBENZOIC ACID; 4-(3-ACETYLPHENYL)-2-METHOXYBENZOIC ACID; 4-(3-ACETYLPHENYL)NICOTINIC ACID; 3-(3-ACETYLPHENYL)-6-AMINOPICOLINIC ACID; 2-(3-ACETYLPHENYL)-5-METHYLBENZOIC ACID; 5-(3-ACETYLPHENYL)-3-AMINOBENZOIC ACID; 4-(3-ACETYLPHENYL)-3-HYDROXYBENZOIC ACID; 3-(3-ACETYLPHENYL)-5-HYDROXYBENZOIC ACID; 3-(3-ACETYLPHENYL)-4-FLUOROBENZOIC ACID; 4-(3-ACETYLPHENYL)-3-FLUOROBENZOIC ACID; 4-(3-ACETYLPHENYL)-2-FLUOROBENZOIC ACID; 5-(3-ACETYLPHENYL)-2-FLUOROBENZOIC ACID; 4-(4-ACETYLPHENYL)NICOTINIC ACID; 3-(4-ACETYLPHENYL)-6-AMINOPICOLINIC ACID; 3-(3-ACETYLPHENYL)ISONICOTINIC ACID; 2-(3-ACETYLPHENYL)NICOTINIC ACID; 5-(3-ACETYLPHENYL)NICOTINIC ACID; 2-(4-ACETYLPHENYL)-5-METHOXYBENZOIC ACID; 3-(4-ACETYLPHENYL)-5-METHOXYBENZOIC ACID; 2-(4-ACETYLPHENYL)-6-CHLOROBENZOIC ACID; 3-(4-ACETYLPHENYL)-4-CHLOROBENZOIC ACID; 4-(4-ACETYLPHENYL)-2-METHOXYBENZOIC ACID; 5-(4-ACETYLPHENYL)-2-CHLOROBENZOIC ACID; 4-(4-ACETYLPHENYL)-2-CHLOROBENZOIC ACID; 3-(4-ACETYLPHENYL)-5-CHLOROBENZOIC ACID; 2-(4-ACETYLPHENYL)-4-CHLOROBENZOIC ACID; 6-(3-ACETYLPHENYL)NICOTINIC ACID; 3-(3-ACETYLPHENYL)PICOLINIC ACID; 4-(3-ACETYLPHENYL)PICOLINIC ACID; 6-(3-ACETYLPHENYL)PICOLINIC ACID; 5-(3-ACETYLPHENYL)-6-HYDROXYNICOTINIC ACID; 5-(3-ACETYLPHENYL)-2-METHOXYNICOTINIC ACID; 4-(4-ACETYLPHENYL)PICOLINIC ACID; 6-(4-ACETYLPHENYL)PICOLINIC ACID; 5-(4-ACETYLPHENYL)-2-AMINOISONICOTINIC ACID; 5-(4-ACETYLPHENYL)-2-AMINONICOTINIC ACID; 5-(4-ACETYLPHENYL)-2-HYDROXYNICOTINIC ACID; 5-(4-ACETYLPHENYL)-2-HYDROXYISONICOTINIC ACID; 5-(4-ACETYLPHENYL)-2-METHOXYNICOTINIC ACID; 5-(3-ACETYLPHENYL)-2-AMINOISONICOTINIC ACID; 5-(3-ACETYLPHENYL)-2-AMINONICOTINIC ACID; 5-(3-ACETYLPHENYL)-2-HYDROXYNICOTINIC ACID; 5-(3-ACETYLPHENYL)-2-HYDROXYISONICOTINIC ACID; 3-(4-ACETYLPHENYL)ISONICOTINIC ACID; 2-(4-ACETYLPHENYL)NICOTINIC ACID; 6-(4-ACETYLPHENYL)NICOTINIC ACID; 3-(4-ACETYLPHENYL)PICOLINIC ACID; 5-(4-ACETYLPHENYL)-6-HYDROXYNICOTINIC ACID; 5-(3-ACETYL-PHENOXY)-FURAN-2-CARBOXYLIC ACID; 5-(4-ACETYL-PHENOXY)-FURAN-2-CARBOXYLIC ACID; 3-ACETYL-4-AZAINDOLE-5-CARBOXYLIC ACID; 3-ACETYL-7-AZAINDOLE-6-CARBOXYLIC ACID; 3-ACETYL-4-AZAINDOLE-7-CARBOXYLIC ACID; 3-ACETYL-4-METHYL-2-PYRROLECARBOXYLIC ACID; 4-ACETYL-5-FORMYL-3-METHYL-PYRROLE-2-CARBOXYLIC ACID; 2-ACETYL-6-NITROBENZOIC ACID; (2-ACETYL-3-HYDROXYPHENOXY)ACETIC ACID; 2,2-DIMETHYL-5-OXOHEXANOIC ACID; 2-BUTYL-5-OXOHEXANOIC ACID; 5-ACETYL-2-FUROIC ACID

List No. 9—Dicarbonyls: FORMYL-2-OXO-2-PHENYLETHYL)SODIUM; (2S)-1-(3-FORMYL-4-OXO-4H-

PYRIDO[1,2-A]PYRIMIDIN-2-YL)PYRROLIDINE-2-CARBOXAMIDE; (5-FORMYL-6-OXO-3-TRIFLUOROMETHYL-6H-PYRIDAZIN-1-YL)-ACETIC ACID ETHYL ESTER; 1-(3,4-DIMETHYLPHENYL)-3-METHYL-5-OXO-3-PYRAZOLIN-4-CARBALDEHYDE; 1,2-DIHYDRO-6-METHYL-2-OXO-3-PYRIDINECARBOXALDEHYDE; 1,3-DIMETHYL-2,4-DIOXO-6-(PROPYLAMINO)-1,2,3,4-TETRAHYDRO-5-PYRIMIDINECARBALDEHYDE; 1,3-DIMETHYL-2,4-DIOXO-6-[(TETRAHYDRO-2-FURANYLMETHYL)AMINO]-1,2,3,4-TETRAHYDRO-5-PYRIMIDINECARBALDEHYDE; 1,3-DIMETHYL-6-(METHYLAMINO)-2,4-DIOXO-1,2,3,4-TETRAHYDRO-5-PYRIMIDINECARBALDEHYDE; 1,4-DIHYDRO-5-METHYL-4-OXO-3-PYRIDINECARBOXALDEHYDE; 1,4-DIHYDRO-6-METHYL-4-OXO-3-PYRIDINECARBOXALDEHYDE; 11-CHLORO-13-OXO-8-OXA-1,10-DIAZATRICYCLO[7.4.0.02,7]TRIDECA-2(7),3,5,9,11-PENTAENE-12-CARBALDEHYDE; 11-CHLORO-13-OXO-8-THIA-1,10-DIAZATRICYCLO[7.4.0.02,7]TRIDECA-2(7),3,5,9,11-PENTAENE-12-CARBALDEHYDE; 1-BENZYL-3-OXOPIPERIDINE-4-CARBALDEHYDE; 1-CYCLOPROPYL-7-FLUORO-8-METHOXY-4-OXO-1,4-DIHYDROQUINOLINE-3-CARBALDEHYDE; 1-CYCLOPROPYL-7-FLUORO-8-METHYL-4-OXO-1,4-DIHYDROQUINOLINE-3-CARBALDEHYDE; 1-ETHOXYCARBONYL-3-FORMYL-4-PIPERIDONE; 1H-PYRROLO[2,3-B]PYRIDINE-5-CARBOXALDEHYDE, 4-AMINO-6,7-DIHYDRO-2,3-DIMETHYL-6-OXO-; 2-((2-METHOXYETHYL)AMINO)-4-OXO-4H-PYRIDO[1,2-A]PYRIMIDINE-3-CARBALDEHYDE; 2-(2-(METHYLTHIO)PYRIMIDIN-4-YL)MALONALDEHYDE; 2-(3-FLUORO-PHENYL)-6-METHOXY-3-OXO-2,3-DIHYDRO-ISOQUINOLINE-4-CARBALDEHYDE; 2-(4-IODOPHENOXY)MALONDIALDEHYDE; 2-(ALLYLAMINO)-4-OXO-4H-PYRIDO[1,2-A]PYRIMIDINE-3-CARBALDEHYDE; 2,2-DIMETHYL-3-OXOHEPT-6-ENAL; 2,2-DIMETHYL-3-OXOHEPTANAL; 2,2-DIMETHYL-3-OXOHEXANAL; 2,2-DIMETHYL-3-OXOOCTANAL; 2,2-DIMETHYL-3-OXOPENTANAL; 2,6-DIAMINO-1,4-DIHYDRO-4-OXO-5-PYRIMIDINECARBOXALDEHYDE; 2,7-DICHLORO-4-OXO-4H-PYRIDO[1,2-A]PYRIMIDINE-3-CARBALDEHYDE; 2-AMINO-6-CHLORO-1,4-DIHYDRO-4-OXO-5-PYRIMIDINECARBOXALDEHYDE; 2-CHLORO-6-METHYL-4-OXO-4H-PYRIDO[1,2-A]PYRIMIDINE-3-CARBALDEHYDE; 2-DIMETHYLAMINO-1,3-DIOXOHEXANE; 2-HEPTYL-1,4-DIHYDRO-4-OXO-3-QUINOLINECARBOXALDEHYDE; 2-IODOMALONALDEHYDE; 2-METHYL-3-(3-NITROPHENYL)-3-OXOPROPANAL; 2-METHYL-3-OXO-3-(THIOPHEN-2-YL)PROPANAL; 2-METHYL-3-OXOBUTANAL; 2-METHYL-5-(MORPHOLIN-4-YL)-3-OXO-2,3-DIHYDROPYRIDAZINE-4-CARBALDEHYDE; 2-OXO-1-[1-(TRIMETHYLSILYL)-2-PROPENYL]CYCLOHEXANECARBALDEHYDE; 2-OXO-5-(PROPAN-2-YL)CYCLOHEXANE-1-CARBALDEHYDE; 2-OXO-5-PROPYLINDOLINE-3-CARBALDEHYDE; 3-(1,1-BIPHENYL-4-YL)-3-OXOPROPANAL; 3-(1,3-BENZODIOXOL-5-YL)-3-OXOPROPANAL; 3-(1,3-BENZOTHIAZOL-2-YL)-3-OXOPROPANAL; 3-(1-BENZOFURAN-2-YL)-3-OXOPROPANAL; 3-(1-ETHYL-1H-PYRAZOL-4-YL)-3-OXOPROPANAL; 3-(1-ETHYL-3,5-DIMETHYL-1H-PYRAZOL-4-YL)-3-OXOPROPANAL; 3-(1-METHYL-1H-1,3-BENZODIAZOL-2-YL)-3-OXOPROPANAL; 3-(1-METHYL-1H-PYRAZOL-4-YL)-3-OXOPROPANAL; 3-(1-NAPHTHYL)-3-OXOPROPANAL; 3-(2,3-DIHYDRO-1,4-BENZODIOXIN-6-YL)-3-OXOPROPANAL; 3-(2,4-DICHLORO-5-FLUOROPHENYL)-3-OXOPROPANAL; DICHLOROPHENYL)-3-OXOPROPANAL; 3-(2,4-DIFLUOROPHENYL)-3-OXOPROPANAL; 3-(2,5-DICHLOROPHENYL)-3-OXOPROPANAL; 3-(2,5-DIFLUOROPHENYL)-3-OXOPROPANAL; 3-(2,5-DIMETHYLFURAN-3-YL)-3-OXOPROPANAL; 3-(2,6-DICHLORO-3-FLUOROPHENYL)-3-OXOPROPANAL; DIFLUOROPHENYL)-3-OXOPROPANAL; 3-(2-BROMOPHENYL)-3-OXOPROPANAL; 3-(2-CHLOROPHENYL)-3-OXOPROPANAL; 3-(2-ETHOXYPHENYL)-3-OXOPROPANAL; 3-(2-FLUOROPHENYL)-3-OXOPROPANAL; 3-(2-FURYL)-3-OXOPROPANAL; 3-(2-METHOXY-5-METHYLPHENYL)-3-OXOPROPANAL; 3-(2-METHYLPHENYL)-3-OXOPROPANAL; 3-(2-NAPHTHYL)-3-OXOPROPANAL; 3-(2-NITROPHENYL)-3-OXOPROPANAL; 3-(3,4-DICHLOROPHENYL)-3-OXOPROPANAL; 3-(3,4-DIFLUOROPHENYL)-3-OXOPROPANAL; 3-(3,4-DIHYDRO-2H-1,5-BENZODIOXEPIN-7-YL)-3-OXOPROPANAL; 3-(3,4-DIMETHOXYPHENYL)-3-OXOPROPANAL; 3-(3,4-DIPROPOXYPHENYL)-3-OXOPROPANAL; 3-(3-BROMOPHENYL)-3-OXOPROPANAL; 3-(3-CHLORO-4-FLUOROPHENYL)-3-OXOPROPANAL; 3-(3-CHLOROPHENYL)-3-OXOPROPANAL; 3-(3-ETHYL-1-BENZOFURAN-2-YL)-3-OXOPROPANAL; 3-(3-FLUOROPHENYL)-3-OXOPROPANAL; 3-(3-NITROPHENYL)-3-OXOPROPANAL; 3-(4-BROMOPHENYL)-3-OXOPROPANAL; 3-(4-ETHOXYPHENYL)-3-OXOPROPANAL; 3-(4-FLUOROPHENYL)-3-OXOPROPANAL; 3-(4-ISOPROPYLPHENYL)-3-OXOPROPANAL; 3-(4-METHYL-3-NITROPHENYL)-3-OXOPROPANAL; 3-(4-METHYLPHENYL)-3-OXOPROPANAL; 3-(4-NITROPHENYL)-3-OXOPROPANAL; 3-(5-BROMO-1-BENZOFURAN-2-YL)-3-OXOPROPANAL; 3-(5-BROMOTHIOPHEN-2-YL)-3-OXOPROPANAL; 3-(5-CHLOROTHIOPHEN-2-YL)-3-OXOPROPANAL; 3-(5-ETHYLTHIOPHEN-2-YL)-3-OXOPROPANAL; 3-(5-METHYLFURAN-2-YL)-3-OXOPROPANAL; 3-(5-METHYLTHIEN-2-YL)-3-OXOPROPANAL; 3-(6-METHOXYNAPHTHALEN-2-YL)-3-OXOPROPANAL; 3-(9H-FLUOREN-2-YL)-3-OXOPROPANAL; 3-(ADAMANTAN-1-YL)-3-OXOPROPANAL; 3-(FURAN-2-YL)-2-METHYL-3-OXOPROPANAL; 3,4-DIHYDRO-3-OXO-2-QUINOXALINECARBOXALDEHYDE; 3-[3,5-BIS(TRIFLUOROMETHYL)PHENYL]-3-OXOPROPANAL; 3-[4-(BENZYLOXY)PHENYL]-3-OXOPROPANAL; 3-[4-(METHYLSULFANYL)PHENYL]-3-OXOPROPANAL; 3-CYCLOHEXYL-3-OXOPROPANAL; 3-CYCLOPENTYL-3-OXOPROPANAL; 3-CYCLOPROPYL-3-OXOPROPANAL; 3-FORMYL-2-(METHYLPHENYLAMINO)CHROMONE; 3-FORMYL-4(1H)-PYRIDONE; 3-MESITYL-3-OXOPROPANAL; 3-OXO-3-(1,3,5-TRIMETHYL-1H-PYRAZOL-4-YL)PROPANAL; 3-OXO-3-(4-PROPOXYPHENYL)PROPANAL; 3-OXO-3-(4-PROPYLPHENYL)PROPANAL; 3-OXO-3-(PYRIDIN-3-YL)PROPANAL; 3-OXO-3-(PYRIDIN-4-YL)PROPANAL; 3-OXO-3-(THIOPHEN-3-YL)PROPANAL; 3-OXO-BUTANAL; 4,5,6,7-TETRAHYDRO-4-OXO-5-BENZOFURANCARBOXALDEHYDE; 4-METHYL-3-OXOPENTANAL; 4-OXO-1H-QUINOLINE-3-CARBALDEHYDE; 4-OXO-6-PHENYL-4H-1-BENZOPYRAN-3-CARBOXALDEHYDE; 4-OXO-TETRAHYDROFURAN-3-CARBOXALDEHYDE;

5-(TERT-BUTYLDIMETHYLSILYLOXY)-2-OXOCYCLOHEXANECARBALDEHYDE; 5,6,7-TRIFLUORO-4-OXO-4H-CHROMENE-3-CARBALDEHYDE; 5-AMINO-1-CYCLOPROPYL-6,7-DIFLUORO-8-METHYL-4-OXO-1,4-DIHYDROQUINOLINE-3-CARBALDEHYDE; 5-BROMO-2-OXOINDOLINE-3-CARBALDEHYDE; 5-CHLORO-2-OXO-1,2-DIHYDRO-3-PYRIDINECARBALDEHYDE; 5-ETHOXY-2-OXOINDOLINE-3-CARBALDEHYDE; 5-ETHYL-2-OXOINDOLINE-3-CARBALDEHYDE; 5-HYDROXY-3-OXO-2,3-DIHYDRO-1-BENZOXEPINE-4-CARBALDEHYDE; 5-ISOPROPYL-2-OXOINDOLINE-3-CARBALDEHYDE; 5-METHYL-2-OXOINDOLINE-3-CARBALDEHYDE; 6-(3-OXOPROPANOYL)PYRIDINE-3-BORONIC ACID; 6-(BROMOMETHYL)-1,3-DIETHYL-2,4-DIOXO-1,2,3,4-TETRAHYDROPYRIMIDINE-5-CARBALDEHYDE; 6-(ISOPROPYLAMINO)-1,3-DIMETHYL-2,4-DIOXO-1,2,3,4-TETRAHYDRO-5-PYRIMIDINECARBALDEHYDE; 6,7-DICHLORO-3-FORMYLCHROMONE; 6-[(2-METHOXYETHYL)AMINO]-1,3-DIMETHYL-2,4-DIOXO-1,2,3,4-TETRAHYDRO-5-PYRIMIDINECARBALDEHYDE; 6-BROMO-2-OXO-1,2,3,4-TETRAHYDRO-QUINOLINE-3-CARBALDEHYDE; 6-CHLORO-1,3-BIS(2-METHOXYETHYL)-2,4-DIOXO-1,2,3,4-TETRAHYDROPYRIMIDINE-5-CARBALDEHYDE; 6-CHLORO-1,3-DIISOBUTYL-2,4-DIOXO-1,2,3,4-TETRAHYDROPYRIMIDINE-5-CARBALDEHYDE; 6-CHLORO-8-NITRO-4-OXO-4H-CHROMENE-3-CARBALDEHYDE; 6-DIMETHYLAMINO-1,3-DIMETHYL-2,4-DIOXO-1,2,3,4-TETRAHYDROPYRIMIDINE-5-CARBOXALDEHYDE; 6-ISOPROPOXY-4-OXO-4H-CHROMENE-3-CARBALDEHYDE; 6-METHYL-8-NITRO-4-OXO-4H-CHROMENE-3-CARBALDEHYDE; 7,8-DIHYDROXY-4-OXO-4H-CHROMENE-3-CARBALDEHYDE; 7-BROMO-2-CHLORO-4-OXO-4H-PYRIDO[1,2-A]PYRIMIDINE-3-CARBALDEHYDE; 7-BROMO-4-OXO-4H-CHROMENE-3-CARBALDEHYDE; 7-CHLORO-5-OXO-5H-THIAZOLO[3,2-A]PYRIMIDINE-6-CARBALDEHYDE; 7-FLUORO-4-OXO-4H-CHROMENE-3-CARBALDEHYDE; 7-HYDROXY-8-METHYL-4-OXO-4H-CHROMENE-3-CARBALDEHYDE; 7-METHYL-4-OXO-4H-CHROMENE-3-CARBALDEHYDE; 7-NITRO-4-OXO-4H-CHROMENE-3-CARBALDEHYDE; 8-BROMO-6-METHYL-4-OXO-4H-CHROMENE-3-CARBALDEHYDE; 8-NITRO-4-OXO-4H-CHROMENE-3-CARBALDEHYDE; 8-OXO-3,4,8,9-TETRAHYDRO-2H,7H-[1,4]DIOXEPINO[2,3-F]INDOLE-9-CARBALDEHYDE; ACETALDEHYDE, AMINOBENZOYL-; ALPHA,ALPHA-DICHLORO-BETA-OXO-BENZENEPROPANAL; ALPHA-CHLORO-BETA-OXO-BENZENEPROPANAL; ALPHA-FLUORO-4-METHYL-BETA-OXO-BENZENEPROPANAL; BUTYLMALONDIALDEHYDE; CYCLOPENTYLMALONDIALDEHYDE; CYCLOPROPYLMALONDIALDEHYDE; DIMETHYLMALONDIALDEHYDE; ETHYLMALONDIALDEHYDE; ISOPROPYLMALONDIALDEHYDE; METHYLMALONDIALDEHYDE; N,N-DIMETHYL-4-(3-OXOPROPANOYOBENZENE-1-SULFONAMIDE; PROPYLMALONDIALDEHYDE; TERT-BUTYLMALONDIALDEHYDE; 4-ANTIPYRINECARBOXALDEHYDE; CHROMONE-3-CARBOXALDEHYDE; 4,4-DIMETHYL-3-OXO-PENTANAL; 5,7-DIMETHYL-3-FORMYLCHROMONE; 6,8-DICHLORO-3-FORMYLCHROMONE; 2,4-DIPHENYL-3-OXOBUTYRALDEHYDE; 6-AMINO-1,3-DIMETHYL-2,4-DIOXO-1,2,3,4-TETRAHYDROPYRIMIDINE-5-CARBALDEHYDE; 6-AMINO-1,3-DIETHYL-5-FORMYLURACIL; 1,3-DIMETHYL-2,4-DIOXO-1,2,3,4-TETRAHYDROPYRIMIDINE-5-CARBALDEHYDE; 6-FLUORO-3-FORMYLCHROMONE; 2-AMINO-6-FLUORO-4-OXO-4H-CHROMENE-3-CARBALDEHYDE; 6-CHLORO-3-FORMYLCHROMONE; 2-AMINO-6-CHLORO-3-FORMYLCHROMONE; 3-FORMYL-6-METHYLCHROMONE; 2-AMINO-3-FORMYL-6-METHYLCHROMONE; AURORA KA-3767; 2-AMINO-6-BROMO-3-FORMYLCHROMONE; 2-AMINO-3-FORMYLCHROMONE; 6-CHLORO-3-FORMYL-7-METHYLCHROMONE; 6-BROMO-3-FORMYLCHROMONE; 3-FORMYL-6-NITROCHROMONE; 5-FORMYLURACIL; 6,7-DIMETHYL-3-FORMYLCHROMONE; 6,8-DIMETHYL-3-FORMYLCHROMONE; 3-FORMYL-6-ISOPROPYLCHROMONE; 6-ETHYL-3-FORMYLCHROMONE; 2-AMINO-3-FORMYL-6,7-DIMETHYLCHROMONE; 2-(2-BENZOXAZOLYL)MALONDIALDEHYDE; 2-(4-PYRIMIDYL)MALONDIALDEHYDE; 2-(4-CHLORO-2-NITROPHENYL)MALONDIALDEHYDE; 2-(3-HYDROXYCARBONYL-2-NITROPHENYL)MALONDIALDEHYDE; 2-(2-NITROPHENYL)MALONDIALDEHYDE; 2-(4-METHOXYPHENYL)MALONDIALDEHYDE; 2-(4-HYDROXYCARBONYL-2-NITROPHENYL)MALONDIALDEHYDE; 2-(4-CHLOROPHENYL)MALONDIALDEHYDE; 2-(4-METHYLPHENYL)MALONDIALDEHYDE; 2-(5-METHOXY-2-NITROPHENYL)MALONDIALDEHYDE MONOHYDRATE; 2-(5-HYDROXYCARBONYL-2-NITROPHENYL)MALONDIALDEHYDE MONOHYDRATE; 2-(4-METHYLSULFONYL-2-NITROPHENYL)MALONDIALDEHYDE; 2-(2-PYRAZINYL)MALONDIALDEHYDE; 2-(2-QUINOXALINYL)MALONDIALDEHYDE; 2-(2-PYRIDYL)MALONDIALDEHYDE; 2-(2-HYDROXYCARBONYL-6-PYRIDYL)MALONDIALDEHYDE; 2-(3-HYDROXYCARBONYL-6-PYRIDYL)MALONDIALDEHYDE; 2-(4-PYRIDYL)MALONDIALDEHYDE; 1,3-DIMETHYL-2,4,6-TRIOXO-HEXAHYDRO-PYRIMIDINE-5-CARBALDEHYDE; 6-HYDROXY-4-OXO-4H-CHROMENE-3-CARBALDEHYDE; 7-HYDROXY-4-OXO-4H-CHROMENE-3-CARBALDEHYDE; 2-BROMOMALONALDEHYDE; 1,2-DIHYDRO-7-METHYL-2-OXO-3-QUINOLINECARBOXALDEHYDE; 7-ETHOXY-1,2-DIHYDRO-2-OXO-3-QUINOLINECARBOXALDEHYDE; 4,4-DIMETHYL-2,6-DIOXOCYCLOHEXANECARBALDEHYDE; 2-AMINO-4-CHLORO-6-OXO-1H-PYRIMIDINE-5-CARBALDEHYDE; 2-OXOINDOLINE-3-CARBALDEHYDE; 2-HYDROXY-4-OXO-4H-PYRIDO[1,2-A]PYRIMIDINE-3-CARBALDEHYDE; 2-OXO-1,2-DIHYDRO-QUINOLINE-3-CARBALDEHYDE; 2-(DIMETHYLAMINO)-4-OXO-1,4-DIHYDROQUINOLINE-3-CARBALDEHYDE; 2-(4-NITRO-1H-PYRAZOL-1-YL)MALONALDEHYDE; 1-METHYL-2-OXOINDOLINE-3-CARBALDEHYDE; 2-OXO-1-PHENYLINDOLINE-3-CARBALDEHYDE; 4-OXO-5-PHENYL-4H-PYRAN-3-CARBOXALDEHYDE; 2-CHLORO-7-METHYL-4-OXO-4H-PYRIDO[1,2-A]PYRIMIDINE-3-CARBALDEHYDE; 2-(BUTYLTHIO)-4-OXO-4H-PYRIDO(1,2-A)PYRIMIDINE-3-CARBALDE-

HYDE; 9-METHYL-4-OXO-2-PIPERIDIN-1-YL-4H-PYRIDO[1,2-A]PYRIMIDINE-3-CARBALDEHYDE; 9-METHYL-2-MORPHOLIN-4-YL-4-OXO-4H-PYRIDO[1,2-A]PYRIMIDINE-3-CARBALDEHYDE; 9-METHYL-2-(4-METHYLPIPERIDIN-1-YL)-4-OXO-4H-PYRIDO[1,2-A]PYRIMIDINE-3-CARBALDEHYDE; 2-(BENZYLTHIO)-4-OXO-4H-PYRIDO(1,2-A)PYRIMIDINE-3-CARBALDEHYDE; 3-OXO-2,5-DIPHENYL-PENT-4-ENAL; 7-METHYL-4-OXO-2-P-TOLYLAMINO-4H-PYRIDO(1,2-A)PYRIMIDINE-3-CARBALDEHYDE; 7-METHYL-4-OXO-2-PIPERIDIN-1-YL-4H-PYRIDO[1,2-A]PYRIMIDINE-3-CARBALDEHYDE; 9-METHYL-2-(METHYLOXY)-4-OXO-4H-PYRIDO[1,2-A]PYRIMIDINE-3-CARBALDEHYDE; 2-(BENZYLAMINO)-9-METHYL-4-OXO-4H-PYRIDO(1,2-A)PYRIMIDINE-3-CARBALDEHYDE; 9-METHYL-4-OXO-2-(4-TOLUIDINO)-4H-PYRIDO(1,2-A)PYRIMIDINE-3-CARBALDEHYDE; 2-DIETHYLAMINO-9-METHYL-4-OXO-4H-PYRIDO[1,2-A]PYRIMIDINE-3-CARBALDEHYDE; 2-CHLORO-8-METHYL-4-OXO-4H-PYRIDO[1,2-A]PYRIMIDINE-3-CARBALDEHYDE; 2-CHLORO-4-OXO-4H-PYRIDO[1,2-A]PYRIMIDINE-3-CARBALDEHYDE; 2-[(CYCLOHEXYLAMINO)(PHENYL)METHYLENE]MALONALDEHYDE; 4-OXO-2-(PHENYLTHIO)-4H-PYRIDO[1,2-A]PYRIMIDINE-3-CARBALDEHYDE; 4-OXO-2-(4-TOLUIDINO)-4H-PYRIDO[1,2-A]PYRIMIDINE-3-CARBOXALDEHYDE; 4-OXO-2-P-TOLYLSULFANYL-4H-PYRIDO[1,2-A]PYRIMIDINE-3-CARBALDEHYDE; 2-(BENZYLAMINO)-4-OXO-4H-PYRIDO[1,2-A]PYRIMIDINE-3-CARBALDEHYDE; MALONDIALDEHYDE; 6-CHLORO-5-FORMYL-1,3-DIMETHYLURACIL; 2-[2-(4-METHOXYPHENYL)HYDRAZONO]-3-OXO-3-(2-THIENYL)PROPANAL; 2-[2-(4-CHLOROPHENYL)HYDRAZONO]-3-OXO-3-(2-THIENYL)PROPANAL; 2-[2-(3-METHYLPHENYL)HYDRAZONO]-3-OXO-3-(2-THIENYL)PROPANAL; 3-OXO-2-(2-PHENYLHYDRAZONO)-3-(2-THIENYL)PROPANAL; 3-(2-FURYL)-3-OXO-2-(2-PHENYLHYDRAZONO)PROPANAL; 2-[2-(4-CHLOROPHENYL)HYDRAZONO]-3-(2-FURYL)-3-OXOPROPANAL; 3-(2-FURYL)-2-[2-(4-METHOXYPHENYL)HYDRAZONO]-3-OXOPROPANAL; 3-(2-FURYL)-2-[2-(3-METHYLPHENYL)HYDRAZONO]-3-OXOPROPANAL; 2-[2-(2,3-DIMETHYLPHENYL)HYDRAZONO]-3-(4-METHYLPHENYL)-3-OXOPROPANAL; 2-[2-(2-CHLOROPHENYL)HYDRAZONO]-3-OXO-3-PHENYLPROPANAL; 2-[2-(4-METHOXYPHENYL)HYDRAZONO]-3-OXO-3-PHENYLPROPANAL; 3-(4-METHOXYPHENYL)-3-OXO-2-(2-PHENYLHYDRAZONO)PROPANAL; 3-OXO-3-PHENYL-2-(2-PHENYLHYDRAZONO)PROPANAL; 2-[2-(4-METHYLPHENYL)HYDRAZONO]-3-OXO-3-(4-PYRIDINYL)PROPANAL; 2-[2-(4-FLUOROPHENYL)HYDRAZONO]-3-OXO-3-(4-PYRIDINYL)PROPANAL; 3-(4-CHLOROPHENYL)-3-OXO-2-(2-PHENYLHYDRAZONO)PROPANAL; 2-[2-(4-CHLOROPHENYL)HYDRAZONO]-3-OXO-3-(4-PYRIDINYL)PROPANAL; 3-OXO-2-(2-PHENYLHYDRAZONO)-3-(4-PYRIDINYL)PROPANAL; 9-METHYL-4-OXO-2-(PHENYLTHIO)-4H-PYRIDO[1,2-A]PYRIMDINE-3-CARBALDEHYDE; 9-METHYL-4-OXO-2-PYRROLIDIN-1-YL-4H-PYRIDO[1,2-A]PYRIMIDINE-3-CARBALDEHYDE; 2-(2,6-DIMETHYL-4-MORPHOLINYL)-4-OXO-4H-PYRIDO(1,2-A)PYRIMIDINE-3-CARBALDEHYDE; 2-(2-CHLOROANILINO)-4-OXO-4H-PYRIDO(1,2-A)PYRIMIDINE-3-CARBALDEHYDE; 4-OXO-2-PYRROLIDIN-1-YL-4H-PYRIDO[1,2-A]PYRIMIDINE-3-CARBALDEHYDE; 2-(4-METHYL-1-PIPERIDINYL)-4-OXO-4H-PYRIDO(1,2-A)PYRIMIDINE-3-CARBALDEHYDE; 4-OXO-2-PIPERIDIN-1-YL-4H-PYRIDO[1,2-A]PYRIMIDINE-3-CARBALDEHYDE; 2-[BENZYL(METHYL)AMINO]-4-OXO-4H-PYRIDO[1,2-A]PYRIMIDINE-3-CARBALDEHYDE; 6-(BROMOMETHYL)-1,3-DIMETHYL-2,4-DIOXO-1,2,3,4-TETRAHYDROPYRIMIDINE-5-CARBALDEHYDE; 2-[(2-FURYLMETHYL)AMINO]-7-METHYL-4-OXO-4H-PYRIDO[1,2-A]PYRIMIDINE-3-CARBALDEHYDE; 6-AMINO-1-METHYL-2,4-DIOXO-1,2,3,4-TETRAHYDRO-5-PYRIMIDINECARBALDEHYDE; 2-(2-FLUOROANILINO)-9-METHYL-4-OXO-4H-PYRIDO(1,2-A)PYRIMIDINE-3-CARBALDEHYDE; 2-ANILINO-7-METHYL-4-OXO-4H-PYRIDO[1,2-A]PYRIMIDINE-3-CARBALDEHYDE; 7-METHYL-2-MORPHOLIN-4-YL-4-OXO-4H-PYRIDO[1,2-A]PYRIMIDINE-3-CARBALDEHYDE; 3-METHYL-5-OXO-1-PHENYL-4,5-DIHYDRO-1H-PYRAZOLE-4-CARBALDEHYDE; 3-OXO-3-(THIOPHEN-2-YL)PROPANAL; 3-FORMYL-4-OXO-4H-CHROMEN-7-YL ACETATE; 2-AMINO-6,8-DICHLORO-3-FORMYLCHROMONE; 2-CHLOROMALONALDEHYDE; 6-METHYL-2,4-DIOXO-1,2,3,4-TETRAHYDRO-PYRIMIDINE-5-CARBALDEHYDE; 5-OXO-2,3-DIHYDRO-1H,5H-PYRIDO[3,2,1-IJ]QUINOLINE-6-CARBALDEHYDE; 4-OXO-1,2-DIHYDRO-4H-PYRROLO[3,2,1-IJ]QUINOLINE-5-CARBALDEHYDE; 2-MORPHOLIN-4-YL-4-OXO-4H-PYRIDO[1,2-A]PYRIMIDINE-3-CARBALDEHYDE; 2-(2-QUINOLYL)MALONDIALDEHYDE; 1-((2R,4S,5R)-4-HYDROXY-5-(HYDROXYMETHYL)TETRAHYDROFURAN-2-YL)-2,4-DIOXO-1,2,3,4-TETRAHYDROPYRIMIDINE-5-CARBALDEHYDE; HYDROXYPROPANEDIAL; 1-CYCLOOCTYL-6-METHYL-2,4-DIOXO-1,2,3,4-TETRAHYDROPYRIMIDINE-5-CARBALDEHYDE; 2-(AZEPAN-1-YL)-9-METHYL-4-OXO-4H-PYRIDO[1,2-A]PYRIMIDINE-3-CARBALDEHYDE; 2-((2-HYDROXYETHYL)AMINO)-9-ME-4-OXO-4H-PYRIDO(1,2-A)PYRIMIDINE-3-CARBALDEHYDE; 2-PYRIDAZIN-4-YLMALONALDEHYDE; 1,2-DIHYDRO-6,8-DIMETHYL-2-OXO-3-QUINOLINECARBOXALDEHYDE; 2-(4-QUINOLYL)MALONDIALDEHYDE SESQUIHYDRATE; 2-[ISOPROPYL(METHYL)AMINO]-4-OXO-4H-PYRIDO[1,2-A]PYRIMIDINE-3-CARBALDEHYDE; METHYL ((3-FORMYL-4-OXO-4H-PYRIDO(1,2-A)PYRIMIDIN-2-YL)THIO)ACETATE; 6-METHYL-2-OXO-1,2-DIHYDROQUINOLIN-3-CARBALDEHYDE; 6-ETHYL-1,2-DIHYDRO-2-OXO-3-QUINOLINECARBOXALDEHYDE; 5,7-DIMETHYL-2-OXO-1,2-DIHYDRO-3-QUINOLINECARBALDEHYDE; 7-METHOXY-2-OXO-1,2-DIHYDRO-QUINOLINE-3-CARBALDEHYDE; 6-METHOXY-2-OXO-1,2-DIHYDRO-QUINOLINE-3-CARBALDEHYDE; 8-METHYL-2-OXO-1,2-DIHYDROQUINOLINE-3-CARBALDEHYDE; 5,8-DIMETHYL-2-OXO-1,2-DIHYDRO-3-QUINOLINECARBALDEHYDE; 1,2-DIHYDRO-7,8-DIMETHYL-2-OXO-QUINOLINE-3-CARBOXALDEHYDE; 6-ETHOXY-2-OXO-1,2-DIHYDRO-QUINOLINE-3-CARBALDEHYDE; 2-(3-FLUORO-PHENYL)-MALONALDEHYDE; 2-(2-METHOXY-PHENYL)-MALONALDEHYDE; 2-(3-METHOXYPHENYL)MALONDIALDEHYDE; 2-(2-CHLOROPHENYL)MALONDIALDEHYDE; 2-(DIMETHYLAMINO)-4-OXO-4H-PYRIDO[1,2-A]PYRIMIDINE-3-CARBALDEHYDE; 2-(4-FLUOROPHENYL)MALONDIALDEHYDE; 2-(3,4-DICHLOROPHE-

NYL)MALONDIALDEHYDE; 2-(3-CHLOROPHENYL) MALONDIALDEHYDE; 2-(2-BROMO-PHENYL)-MALONALDEHYDE; 2-(4-BROMOPHENYL) MALONDIALDEHYDE; 2-(4-NITROPHENYL) MALONDIALDEHYDE; 2-(2,4-DINITROPHENYL) MALONDIALDEHYDE; 2-(3,4-DIMETHYL-PHENYL)-MALONALDEHYDE; 8-ETHYL-1,2-DIHYDRO-2-OXO-3-QUINOLINECARBOXALDEHYDE; 6-OXO-5,6-DIHYDRO-[1,3]DIOXOLO[4,5-G]QUINOLINE-7-CARBALDEHYDE; 8-BROMO-6-CHLORO-3-FORMYLCHROMONE; SODIUM 5-FORMYL-1,3-DIMETHYL-2,6-DIOXO-1,2,3,6-TETRAHYDRO-4-PYRIMIDINOLATE; 2-AMINO-6-CHLORO-7-METHYL-3-FORMYL CHROMONE; 6-METHOXY-4-OXO-4H-CHROMENE-3-CARBALDEHYDE; 1,2-DIHYDRO-6,7-DIMETHYL-2-OXO-3-QUINOLINECARBOXALDEHYDE; 2-(4-ETHYL-PIPERAZIN-1-YL)-4-OXO-4H-PYRIDO[1,2-A]PYRIMIDINE-3-CARBALDEHYDE; 1,3,6-TRIMETHYL-2,4-DIOXO-1,2,3,4-TETRAHYDRO-PYRIMIDINE-5-CARBALDEHYDE; 2-(ETHYLAMINO)-9-METHYL-4-OXO-4H-PYRIDO(1,2-A)PYRIMIDINE-3-CARBALDEHYDE; 9-METHYL-4-OXO-2-(2-PYRIMIDINYLAMINO)-4H-PYRIDO(1,2-A) PYRIMIDINE-3-CARBALDEHYDE; 6-FLUORO-8-NITROCHROMONE-3-CARBOXALDEHYDE; 7-METHYL-2-(4-METHYL-PIPERIDIN-1-YL)-4-OXO-4H-PYRIDO[1,2-A]PYRIMIDINE-3-CARBALDEHYDE; 2-CHLORO-9-METHYL-4-OXO-4H-PYRIDO[1,2-A]PYRIMIDINE-3-CARBALDEHYDE; 7-METHYL-2-(4-METHYL-PIPERAZIN-1-YL)-4-OXO-4H-PYRIDO[1,2-A]PYRIMIDINE-3-CARBALDEHYDE; 4-OXO-2-THIOMORPHOLIN-4-YL-4H-PYRIDO[1,2-A]PYRIMIDINE-3-CARBALDEHYDE; 2-(4-METHYLPIPERAZIN-1-YL)-4-OXO-4H-PYRIDO[1,2-A]PYRIMIDINE-3-CARBALDEHYDE; 7,7-DIMETHYL-2-OXOBICYCLO[2.2.1]HEPTANE-1-CARBALDEHYDE; 9-METHYL-4-OXO-2-THIOMORPHOLIN-4-YL-4H-PYRIDO[1,2-A]PYRIMIDINE-3-CARBALDEHYDE; NITROMALONALDEHYDE; NITROMALONALDEHYDE SODIUM SALT; FLUOROMALONALDEHYDE; 7-CHLORO-3-FORMYLCHROMONE; 2-(4-TRIFLUOROMETHOXYPHENYL)MALONDIALDEHYDE; 2-(4-TRIFLUOROMETHYLPHENYL)MALONDIALDEHYDE; 2-(3-TRIFLUOROMETHYLPHENYL) MALONDIALDEHYDE; 2-AMINO-6-ETHYL-3-FORMYLCHROMONE; 2-AMINO-6-ISOPROPYL-4-OXO-4H-BENZOPYRAN-3-CARBOXALDEHYDE; 2-(3,5-DIFLUOROPHENYL)MALONDIALDEHYDE; 2,3-DIHYDRO-5-METHYL-3-OXO-2-PHENYL-1H-PYRAZOLE-4-CARBOXALDEHYDE; 2-(3-BROMOPHENYL)MALONDIALDEHYDE; 2-(4-ETHOXYPHENYL)MALONDIALDEHYDE; 2-(4-PHENYLPHENYL)MALONDIALDEHYDE; 2-PHENYLMALONDIALDEHYDE; 2-(3-METHYLPHENYL)MALONDIALDEHYDE; 2-(4-CHLOROPHENOXY)MALONDIALDEHYDE; 2-(3-CHLOROPHENOXY)MALONDIALDEHYDE; 2-(3,5-DIMETHYLPIPERIDIN-1-YL)-9-METHYL-4-OXO-4H-PYRIDO[1,2-A]PYRIMIDINE-3-CARBALDEHYDE; 9-METHYL-2-(4-METHYL-PIPERAZIN-1-YL)-4-OXO-4H-PYRIDO[1,2-A]PYRIMIDINE-3-CARBALDEHYDE; (5-FORMYL-4-HYDROXY-6-OXO-3-PHENYLPYRIDAZIN-1(6H)-YL)ACETIC ACID; 5-FORMYLURIDINE; 7-OXO-2,3,6,7-TETRAHYDRO-[1,4]DIOXINO[2,3-G]QUINOLINE-8-CARBALDEHYDE; 4-OXO-4H-BENZO[H]CHROMENE-3-CARBALDEHYDE; 2-FORMYL-3-METHYL-1-OXO-1,5-DIHYDRO-BENZO[4,5]IMIDAZO[1,2-A]PYRIDINE-4-CARBONITRILE; 2-NAPHTHALEN-1-YL-MALONALDEHYDE; 3-(CHLOROMETHYL)-2-FORMYL-1-OXO-1,5-DIHYDROPYRIDO[1,2-A]BENZIMIDAZOLE-4-CARBONITRILE; 6-CHLORO-8-CHLOROMETHYL-4-OXO-4H-CHROMENE-3-CARBALDEHYDE; SPIROCYCLOHEXYLBUTANE-1,3-DIONE; 2-(5-HYDROXYCARBONYL-2-NITROPHENYL)MALONDIALDEHYDE; 2-(2-THIENYLMETHYLENE)MALONALDEHYDE; 2-DIMETHYLAMINO-9-METHYL-4-OXO-4H-PYRIDO[1,2-A]PYRIMIDINE-3-CARBALDEHYDE; 2-((FURAN-2-YLMETHYL)AMINO)-4-OXO-4H-PYRIDO[1,2-A]PYRIMIDINE-3-CARBALDEHYDE; 2-(4-FLUOROPHENOXY)-9-METHYL-4-OXO-4H-PYRIDO[1,2-A]PYRIMIDINE-3-CARBALDEHYDE; 9-METHYL-4-OXO-2-(M-TOLYLOXY)-4H-PYRIDO[1,2-A]PYRIMIDINE-3-CARBALDEHYDE; 2-(AZEPAN-1-YL)-4-OXO-4H-PYRIDO[1,2-A]PYRIMIDINE-3-CARBALDEHYDE; 6-AMINO-1-ISOBUTYL-3-METHYL-2,4-DIOXO-1,2,3,4-TETRAHYDROPYRIMIDINE-5-CARBALDEHYDE; N'-(3-ETHYL-5-FORMYL-2,6-DIOXO-1,2,3,6-TETRAHYDRO-PYRIMIDIN-4-YL)-N,N-DIMETHYL-FORMAMIDINE; 2-AZEPAN-1-YL-7-METHYL-4-OXO-4H-PYRIDO[1,2-A]PYRIMIDINE-3-CARBALDEHYDE; 2-DIETHYLAMINO-4-OXO-4H-PYRIDO[1,2-A]PYRIMIDINE-3-CARBALDEHYDE; 2-DIMETHYLAMINO-7-METHYL-4-OXO-4H-PYRIDO[1,2-A]PYRIMIDINE-3-CARBALDEHYDE; 2-DIETHYLAMINO-7-METHYL-4-OXO-4H-PYRIDO[1,2-A]PYRIMIDINE-3-CARBALDEHYDE; 4-CHLORO-1,2-DIHYDRO-2-OXO-3-QUINOLINECARBOXALDEHYDE; 2,4,6-TRIOXO-HEXAHYDRO-PYRIMIDINE-5-CARBALDEHYDE; 6-AMINO-1-(4-METHYLPHENYL)-4-OXO-2-THIOXO-1,2,3,4-TETRAHYDRO-5-PYRIMIDINECARBALDEHYDE; 6-AMINO-1-(4-METHOXYPHENYL)-4-OXO-2-THIOXO-1,2,3,4-TETRAHYDRO-5-PYRIMIDINECARBALDEHYDE; 6-AMINO-2,4-DIOXO-1,2,3,4-TETRAHYDRO-PYRIMIDINE-5-CARBALDEHYDE; 2-(4-METHOXYPHENOXY)-4-OXO-4H-PYRIDO[1,2-A]PYRIMIDINE-3-CARBALDEHYDE; 2-AMINO-6-METHOXY-4-OXO-4H-CHROMENE-3-CARBALDEHYDE; 2,4-DIOXO-3,4-DIHYDRO-2H-PYRIDO[1,2-A]PYRIMIDINE-3-CARBALDEHYDE; 1-ISOBUTYL-6-METHOXY-2-OXO-1,2-DIHYDRO-QUINOLINE-3-CARBALDEHYDE; 1-BOC-3-FORMYL-4-OXO-PIPERIDINE; 1-METHYL-2-OXO-1,2-DIHYDROQUINOLINE-3-CARBALDEHYDE; 1-ISOBUTYL-2-OXO-1,2-DIHYDRO-QUINOLINE-3-CARBALDEHYDE; 1-(4-METHOXY-BENZYL)-2-OXO-1,2-DIHYDRO-QUINOLINE-3-CARBALDEHYDE; 1-ISOBUTYL-6-METHYL-2-OXO-1,2-DIHYDRO-QUINOLINE-3-CARBALDEHYDE; 3-BENZYLIDENE-2-OXO-CYCLOHEXANECARBALDEHYDE; 4-QUINOLINYLMALONALDEHYDE; 1-(3,5-ANHYDRO-2-DEOXY-BETA-D-THREO-PENTAFURANOSYL) THIMINE; 2-(5-HYDROXYCARBONYL-6-PYRIDYL) MALONDIALDEHYDE; 2-CHLORO-1-ETHYL-5-FORMYL-4-METHYL-6-OXO-1,6-DIHYDROPYRIDINE-3-CARBONITRILE; 2-OXO-1,2,6,7,8,9-HEXAHYDROBENZO[G]QUINOLINE-3-CARBALDEHYDE; 6-METHOXY-1-METHYL-2-OXO-1,2-DIHYDROQUINOLINE-3-CARBALDEHYDE; 6-AMINO-4-OXO-1-PHENYL-2-THIOXO-1,2,3,4-TET-

RAHYDRO-5-PYRIMIDINECARBALDEHYDE; 6-AMINO-1-(2-METHYLPHENYL)-4-OXO-2-THIOXO-1,2,3,4-TETRAHYDRO-5-PYRIMIDINECARBALDEHYDE; 6-AMINO-1-(4-CHLOROPHENYL)-4-OXO-2-THIOXO-1,2,3,4-TETRAHYDRO-5-PYRIMIDINECARBALDEHYDE; 6-AMINO-1-(2-CHLOROPHENYL)-4-OXO-2-THIOXO-1,2,3,4-TETRAHYDRO-5-PYRIMIDINECARBALDEHYDE; 3-FORMYL-8-METHOXYCHROMONE; 3-FORMYL-7-METHOXYCHROMONE; 6-METHOXY-1-OXO-1,2,3,4-TETRAHYDRO-[2]-NAPHTHALDEHYDE; 3-FORMYL-5-METHOXYCHROMONE; 2-(1H-IMIDAZOL-2-YL)-MALONALDEHYDE; 6-AMINO-1-BENZYL-2,4-DIOXOTETRAHYDROPYRIMIDINE-5-CARBALDEHYDE; 6-AMINO-1-(4-CHLOROPHENYL)-2,4-DIOXOTETRAHYDROPYRIMIDINE-5-CARBALDEHYDE; 6-AMINO-1-(4-METHOXYPHENYL)-2,4-DIOXO-1,2,3,4-TETRAHYDROPYRIMIDINE-5-CARBALDEHYDE; 7-CHLORO-3,5-DIOXO-2,3,4,5-TETRAHYDRO-BENZO[B]OXEPINE-4-CARBALDEHYDE; 2-OXO-1,2-DIHYDRO-3-PYRIDINECARBALDEHYDE; 1,2-DIHYDRO-6,7-DIMETHOXY-2-OXO-3-QUINOLINECARBOXALDEHYDE; 6,7-DIETHOXY-2-OXO-1,2-DIHYDROQUINOLINE-3-CARBALDEHYDE; 1-ETHYL-2-OXO-1,2-DIHYDROQUINOLINE-3-CARBALDEHYDE; 6-AMINO-1-(2-FURYLMETHYL)-2,4-DIOXOTETRAHYDROPYRIMIDINE-5-CARBALDEHYDE; 2-(5-CHLORO-1,3-BENZOXAZOL-2-YL)MALONALDEHYDE; 6-AMINO-1-(3-METHOXYPHENYL)-2,4-DIOXO-1,2,3,4-TETRAHYDROPYRIMIDINE-5-CARBALDEHYDE; 6-HYDROXY-2,4-DIOXO-1,2,3,4-TETRAHYDROPYRIMIDINE-5-CARBALDEHYDE; 3-FORMYL-4-OXO-4H-CHROMEN-6-YL ACETATE; 1-OXO-1,2,3,4-TETRAHYDRONAPHTHALENE-2-CARBALDEHYDE; 2,4-DIAMINO-6-OXO-1,6-DIHYDRO-5-PYRIMIDINECARBALDEHYDE; 5-METHOXY-2-OXOINDOLINE-3-CARBALDEHYDE; 6-CHLORO-2-OXO-3-INDOLINECARBALDEHYDE; 6-METHOXY-2-OXOINDOLINE-3-CARBALDEHYDE; 4-CHLORO-2-OXO-3-INDOLINECARBALDEHYDE; 1H-BENZIMIDAZOL-2-YLMALONALDEHYDE; 6-AMINO-2,4-DIOXO-1-(PYRIDIN-3-YLMETHYL)TETRAHYDROPYRIMIDINE-5-CARBALDEHYDE; 7-METHYLSULFANYL-2-OXO-1,2-DIHYDRO-QUINOLINE-3-CARBALDEHYDE; 1-ETHYL-7-METHYL-2-OXO-1,2-DIHYDROQUINOLINE-3-CARBALDEHYDE; 7-METHOXY-1-METHYL-2-OXO-1,2-DIHYDROQUINOLINE-3-CARBALDEHYDE; TRIFORMYLMETHANE; 3-OXO-3-PHENYL-PROPIONALDEHYDE; 2-AMINO-6-TERT-BUTYL-3-FORMYLCHROMONE; 6-AMINO-2,4-DIOXO-1-(2-PHENYLETHYL)TETRAHYDROPYRIMIDINE-5-CARBALDEHYDE; 6-TERT-BUTYL-4-OXO-4H-CHROMENE-3-CARBALDEHYDE; 3-(4-CHLOROPHENYL)-3-OXOPROPANAL; 3-(4-METHOXYPHENYL)-3-OXOPROPANAL; 2-AMINO-6,8-DIMETHYL-4-OXO-4H-CHROMENE-3-CARBALDEHYDE; 2-AMINO-6,7-DICHLORO-3-FORMYLCHROMONE; 3-(5-FLUORO-2-HYDROXYPHENYL)-3-OXOPROPANAL; 3-(2-HYDROXYPHENYL)-3-OXOPROPANAL; 3-(2-HYDROXY-5-METHYLPHENYL)-3-OXOPROPANAL; 3-(5-CHLORO-2-HYDROXYPHENYL)-3-OXOPROPANAL; 3-(5-BROMO-2-HYDROXYPHENYL)-3-OXOPROPANAL; 3-OXO-2-PHENOXY-BUTYRALDEHYDE; 8-CHLORO-1,2-DIHYDRO-2-OXO-3-QUINOLINECARBOXALDEHYDE; 7-CHLORO-1,2-DIHYDRO-2-OXO-3-QUINOLINECARBOXALDEHYDE; 6-CHLORO-1,2-DIHYDRO-2-OXO-3-QUINOLINECARBOXALDEHYDE; 1,2-DIHYDRO-8-METHOXY-2-OXO-3-QUINOLINECARBOXALDEHYDE; 6-BROMO-1,2-DIHYDRO-2-OXO-3-QUINOLINECARBOXALDEHYDE; 1-OXO-1,2,3,4-TETRAHYDRO-2-PHENANTHRENECARBALDEHYDE; 2,2-DIMETHYL-3-OXO-3-PHENYLPROPANAL; NITROMALONALDEHYDE SODIUM SALT HYDRATE; 5-CHLORO-2-OXOINDOLINE-3-CARBALDEHYDE; 5-FLUORO-2-OXOINDOLINE-3-CARBALDEHYDE; 6-FLUORO-2-OXOINDOLINE-3-CARBALDEHYDE; 6-METHYL-2-OXOINDOLINE-3-CARBALDEHYDE; 4-(1H-IMIDAZOL-2-YL)-B-OXO-BENZENEPROPANAL; 3-(2,5-DIMETHOXYPHENYL)-3-OXOPROPANAL; 3-(2,4-DIMETHOXYPHENYL)-3-OXOPROPANAL; 3-OXO-3-[2-(TRIFLUOROMETHYL)PHENYL]PROPANAL; 3-OXO-3-[3-(TRIFLUOROMETHYL)PHENYL]PROPANAL; 3-OXO-3-[4-(TRIFLUOROMETHYL)PHENYL]PROPANAL; 3-(2-METHOXYPHENYL)-3-OXOPROPANAL; 3-(3-METHOXYPHENYL)-3-OXOPROPANAL; 3-(3,4-DIMETHOXYPHENYL)-3-OXOPROPANAL; 3-(4-ETHYLPHENYL)-3-OXOPROPANAL; 3-(4-TERT-BUTYLPHENYL)-3-OXOPROPANAL; 3-[4-(2-METHYLPROPYL)PHENYL]-3-OXOPROPANAL; 3-OXO-3-[4-(PROPAN-2-YLOXY)PHENYL]PROPANAL; 3-OXO-3-(PYRIDIN-2-YL)PROPANAL; 3-(2,4-DIMETHYLPHENYL)-3-OXOPROPANAL; 3-(2,5-DIMETHYLPHENYL)-3-OXOPROPANAL; 3-(3-FLUORO-4-METHOXYPHENYL)-3-OXOPROPANAL; 2-(3-OXOPROPANOYL)BENZONITRILE; 4-(3-OXOPROPANOYL)BENZONITRILE; 3-(3-OXOPROPANOYL)BENZONITRILE; 3-(3-BROMO-4-FLUOROPHENYL)-3-OXOPROPANAL; (2-CHLORO-1-ETHOXY-1,3-DIOXOPROPAN-2-YL)POTASSIUM; 10-OXO-2,3,5,6-TETRAHYDRO-1H,4H,10H-11-OXA-3A-AZA-BENZO[DE]ANTHRACENE-9-CARBALDEHYDE; 1-FORMYL-CYCLOBUTANECARBOXYLIC ACID METHYL ESTER; 1-FORMYL-CYCLOHEXANECARBOXYLIC ACID METHYL ESTER; 1-FORMYL-CYCLOPENTANECARBOXYLIC ACID METHYL ESTER; 1-FORMYL-CYCLOPROPANECARBOXYLIC ACID METHYL ESTER; 1-TERT-BUTYL 4-ETHYL 4-FORMYLPIPERIDINE-1,4-DICARBOXYLATE; 2,3-DIHYDRO-2-OXO-3-FURANCARBOXALDEHYDE; 2,4-DIOXOTETRAHYDROFURAN-3-CARBALDEHYDE; 2,5-DIHYDRO-2-OXO-3-FURANCARBOXALDEHYDE; 2-DIMETHYLAMINO-6-OXO-4-PHENYL-6H-[1,3]OXAZINE-5-CARBALDEHYDE; 2-FORMYL-3-OXO-BUTYRIC ACID ETHYL ESTER; 2-FORMYLPROPIONIC ACID ETHYL ESTER; 2-OXO-2H-CHROMENE-3-CARBALDEHYDE; 2-OXO-4-(PROPYLAMINO)-2H-CHROMENE-3-CARBALDEHYDE; 3-ETHYL-4-FLUOROPHENYL)-3-OXOPROPANOATE; 3-OXOPROPANOIC ACID; 3-OXO-PROPIONIC ACID ETHYL ESTER; 4-(BENZYLAMINO)-2-OXO-2H-CHROMENE-3-CARBALDEHYDE; 4-(BUTYLAMINO)-2-OXO-2H-CHROMENE-3-CARBALDEHYDE; 4-(ETHYLAMINO)-2-OXO-2H-CHROMENE-3-CARBALDEHYDE; 4,6,8-TRICHLORO-3-FORMYLCOUMARIN; 4,6-DICHLORO-3-FORMYL-7-METHYLCOUMARIN; 4,6-DICHLORO-3-FORMYLCOUMARIN; 4-[(4-METHYLPHENYL)SULFANYL]-2-OXO-2H-CHROMENE-3-CARBALDEHYDE; 4-CHLORO-2-OXO-2H-

CHROMENE-3-CARBALDEHYDE; 4-CHLORO-3-FORMYL-6-METHYLCOUMARIN; 4-CHLORO-6-FLUORO-2-OXO-2H-CHROMENE-3-CARBALDEHYDE; 4-FORMYL-TETRAHYDRO-PYRAN-4-CARBOXYLIC ACID METHYL ESTER; 4-HYDROXY-2-OXO-2H-CHROMENE-3-CARBALDEHYDE; 4-HYDROXY-3-FORMYL-6-METHYLCOUMARIN; 4-HYDROXY-5,7-DIMETHYL-2-OXO-2H-CHROMENE-3-CARBALDEHYDE; 4-HYDROXY-6,7-DIMETHYL-2-OXO-2H-CHROMENE-3-CARBALDEHYDE; 4-HYDROXY-6,8-DIMETHYL-2-OXO-2H-CHROMENE-3-CARBALDEHYDE; 4-HYDROXY-6-CHLORO-3-FORMYLCOUMARIN; 4-PIPERIDINECARBOXYLIC ACID, 4-FORMYL-; 5-(ETHOXYCARBONYL)-2-FORMYL-4-METHYL-1H-PYRROLE-3-PROPANOIC ACID METHYL ESTER; 6,8-DICHLORO-3-FORMYLCOUMARIN; 6-BROMO-4-CHLORO-3-FORMYLCOUMARIN; 6-BROMO-4-HYDROXY-2-OXO-2H-CHROMENE-3-CARBALDEHYDE; 6-CHLORO-4-HYDROXY-7-METHYL-2-OXO-2H-CHROMENE-3-CARBALDEHYDE; 6-FLUORO-4-HYDROXY-2-OXO-2H-CHROMENE-3-CARBALDEHYDE; 7-(DIETHYLAMINO)-4-HYDROXY-2-OXOCHROMENE-3-CARBALDEHYDE; 7-DIETHYL-AMINO-3-FORMYLCOUMARIN; 8-METHYL-10-OXO-2,3,5,6-TETRAHYDRO-1H,4H, 10H-11-OXA-3A-AZA-BENZO[DE]ANTHRACENE-9-CARBALDEHYDE; BENZYL 3-OXOPROPANOATE; BUTYRAMIDO-MALONALDEHYDIC ACID; DIETHYL FORMYLSUCCINATE; DIMETHYL 2-FORMYLSUCCINATE; ETHYL 1-FORMYLCYCLOBUTANECARBOXYLATE; ETHYL 1-FORMYLCYCLOHEXANECARBOXYLATE; ETHYL 1-FORMYLCYCLOPENTANECARBOXYLATE; ETHYL 1-FORMYLCYCLOPROPANECARBOXYLATE; ETHYL 2-(4-BROMOPHENYL)-3-OXOPROPANOATE; ETHYL 2-CHLORO-3-OXOPROPANOATE; ETHYL 2-FORMYLBUTANOATE; ETHYL 3-DIMETHYLAMINO-2-FORMYLACRYLATE; ETHYL 3-OXO-2-PHENYLPROPANOATE; MALONALDEHYDIC ACID, N-METHYLACETAMIDO-, ETHYL ESTER; METHYL 2-(2-BROMOPHENYL)-2-FORMYLACETATE; METHYL 2-CHLORO-2-FORMYLACETATE; METHYL 2-METHYL-3-OXOPROPIONATE; METHYL 3-N,N-DIMETHYLAMINO-2-FORMYLACRYLATE; METHYL 3-OXOPROPANOATE; METHYL A-FORMYLPHENYLACETATE; PHENACETURIC ACID,-ALPHA-FORMYL-ALPHA-METHYL-; PROPANOIC ACID, 2-METHYL-3-OXO-, METHYL ESTER, (R)—; PROPANOIC ACID, 2-METHYL-3-OXO-, METHYL ESTER, (S)—; ZINC(II) 2-(CARBOXYMETHYL)-2-FORMYLSUCCINATE;

β-keto-esters: (2-CHLORO-1-ETHOXY-1,3-DIOXOPROPAN-2-YL)POTASSIUM; 10-OXO-2,3,5,6-TETRAHYDRO-1H,4H,10H-11-OXA-3A-AZA-BENZO[DE]ANTHRACENE-9-CARBALDEHYDE; 1-FORMYL-CYCLOBUTANECARBOXYLIC ACID METHYL ESTER; 1-FORMYL-CYCLOHEXANECARBOXYLIC ACID METHYL ESTER; 1-FORMYL-CYCLOPENTANECARBOXYLIC ACID METHYL ESTER; 1-FORMYL-CYCLOPROPANECARBOXYLIC ACID METHYL ESTER; 1-TERT-BUTYL 4-ETHYL 4-FORMYLPIPERIDINE-1,4-DICARBOXYLATE; 2,3-DIHYDRO-2-OXO-3-FURANCARBOXALDEHYDE; 2,4-DIOXOTETRAHYDROFURAN-3-CARBALDEHYDE; 2,5-DIHYDRO-2-OXO-3-FURANCARBOXALDEHYDE; 2-DIMETHYLAMINO-6-OXO-4-PHENYL-6H-[1,3] OXAZINE-5-CARBALDEHYDE; 2-FORMYL-3-OXO-BUTYRIC ACID ETHYL ESTER; 2-FORMYLPROPIONIC ACID ETHYL ESTER; 2-OXO-2H-CHROMENE-3-CARBALDEHYDE; 2-OXO-4-(PROPYLAMINO)-2H-CHROMENE-3-CARBALDEHYDE; 3-ETHYL-4-FLUOROPHENYL-3-OXOPROPANOATE; 3-OXOPROPANOIC ACID; 3-OXO-PROPIONIC ACID ETHYL ESTER; 4-(BENZYLAMINO)-2-OXO-2H-CHROMENE-3-CARBALDEHYDE; 4-(BUTYLAMINO)-2-OXO-2H-CHROMENE-3-CARBALDEHYDE; 4-(ETHYLAMINO)-2-OXO-2H-CHROMENE-3-CARBALDEHYDE; 4,6,8-TRICHLORO-3-FORMYLCOUMARIN; 4,6-DICHLORO-3-FORMYL-7-METHYLCOUMARIN; 4,6-DICHLORO-3-FORMYLCOUMARIN; 4-[(4-METHYLPHENYL)SULFANYL]-2-OXO-2H-CHROMENE-3-CARBALDEHYDE; 4-CHLORO-2-OXO-2H-CHROMENE-3-CARBALDEHYDE; 4-CHLORO-3-FORMYL-6-METHYLCOUMARIN; 4-CHLORO-6-FLUORO-2-OXO-2H-CHROMENE-3-CARBALDEHYDE; 4-FORMYL-TETRAHYDRO-PYRAN-4-CARBOXYLIC ACID METHYL ESTER; 4-HYDROXY-2-OXO-2H-CHROMENE-3-CARBALDEHYDE; 4-HYDROXY-3-FORMYL-6-METHYLCOUMARIN; 4-HYDROXY-5,7-DIMETHYL-2-OXO-2H-CHROMENE-3-CARBALDEHYDE; 4-HYDROXY-6,7-DIMETHYL-2-OXO-2H-CHROMENE-3-CARBALDEHYDE; 4-HYDROXY-6,8-DIMETHYL-2-OXO-2H-CHROMENE-3-CARBALDEHYDE; 4-HYDROXY-6-CHLORO-3-FORMYLCOUMARIN; 4-PIPERIDINECARBOXYLIC ACID, 4-FORMYL-; 5-(ETHOXYCARBONYL)-2-FORMYL-4-METHYL-1H-PYRROLE-3-PROPANOIC ACID METHYL ESTER; 6,8-DICHLORO-3-FORMYLCOUMARIN; 6-BROMO-4-CHLORO-3-FORMYLCOUMARIN; 6-BROMO-4-HYDROXY-2-OXO-2H-CHROMENE-3-CARBALDEHYDE; 6-CHLORO-4-HYDROXY-7-METHYL-2-OXO-2H-CHROMENE-3-CARBALDEHYDE; 6-FLUORO-4-HYDROXY-2-OXO-2H-CHROMENE-3-CARBALDEHYDE; 7-(DIETHYLAMINO)-4-HYDROXY-2-OXOCHROMENE-3-CARBALDEHYDE; 7-DIETHYL-AMINO-3-FORMYLCOUMARIN; 8-METHYL-10-OXO-2,3,5,6-TETRAHYDRO-1H,4H,10H-11-OXA-3A-AZA-BENZO[DE]ANTHRACENE-9-CARBALDEHYDE; BENZYL 3-OXOPROPANOATE; BUTYRAMIDO-MALONALDEHYDIC ACID; DIETHYL FORMYLSUCCINATE; DIMETHYL 2-FORMYLSUCCINATE; ETHYL 1-FORMYLCYCLOBUTANECARBOXYLATE; ETHYL 1-FORMYLCYCLOHEXANECARBOXYLATE; ETHYL 1-FORMYLCYCLOPENTANECARBOXYLATE; ETHYL 1-FORMYLCYCLOPROPANECARBOXYLATE; ETHYL 2-(4-BROMOPHENYL)-3-OXOPROPANOATE; ETHYL 2-CHLORO-3-OXOPROPANOATE; ETHYL 2-FORMYLBUTANOATE; ETHYL 3-DIMETHYLAMINO-2-FORMYLACRYLATE; ETHYL 3-OXO-2-PHENYLPROPANOATE; MALONALDEHYDIC ACID, N-METHYLACETAMIDO-, ETHYL ESTER; METHYL 2-(2-BROMOPHENYL)-2-FORMYLACETATE; METHYL 2-CHLORO-2-FORMYLACETATE; METHYL 2-METHYL-3-OXOPROPIONATE; METHYL 3-N,N-DIMETHYLAMINO-2-FORMYLACRYLATE; METHYL 3-OXOPROPANOATE; METHYL A-FORMYLPHENYLACETATE; PHENACETURIC ACID,-ALPHA-FORMYL-ALPHA-METHYL-; PROPANOIC ACID, 2-METHYL-3-OXO-, METHYL ESTER, (R)—; PRO- PANOIC ACID, 2-METHYL-3-OXO-, METHYL ESTER, (S)—; ZINC(II) 2-(CARBOXYMETHYL)-2-FORMYLSUCCINATE;

β-keto-amides: (2S)-1-(3-FORMYL-4-OXO-4H-PYRIDO[1,2-A]PYRIMIDIN-2-YL)PYRROLIDINE-2-CARBOXAMIDE; (5-FORMYL-4-HYDROXY-6-OXO-3-PHENYLPYRIDAZIN-1(6H)-YL)ACETIC ACID; (5-FORMYL-6-OXO-3-TRIFLUOROMETHYL-6H-PYRIDAZIN-1-YL)-ACETIC ACID ETHYL ESTER; 1-((2R,4S,5R)-4-HYDROXY-5-(HYDROXYMETHYL)TETRAHYDROFURAN-2-YL)-2,4-DIOXO-1,2,3,4-TETRAHYDROPYRIMIDINE-5-CARBALDEHYDE; DIMETHYLPHENYL)-3-METHYL-5-OXO-3-PYRAZOLIN-4-CARBALDEHYDE; 1-(4-METHOXY-BENZYL)-2-OXO-1,2-DIHYDRO-QUINOLINE-3-CARBALDEHYDE; 1,2-DIHYDRO-6,7-DIMETHOXY-2-OXO-3-QUINOLINECARBOXALDEHYDE; 1,2-DIHYDRO-6,7-DIMETHYL-2-OXO-3-QUINOLINECARBOXALDEHYDE; 1,2-DIHYDRO-6,8-DIMETHYL-2-OXO-3-QUINOLINECARBOXALDEHYDE; 1,2-DIHYDRO-6-METHYL-2-OXO-3-PYRIDINECARBOXALDEHYDE; 1,2-DIHYDRO-7,8-DIMETHYL-2-OXO-QUINOLINE-3-CARBOXALDEHYDE; 1,2-DIHYDRO-7-METHYL-2-OXO-3-QUINOLINECARBOXALDEHYDE; 1,2-DIHYDRO-8-METHOXY-2-OXO-3-QUINOLINECARBOXALDEHYDE; 1,3,6-TRIMETHYL-2,4-DIOXO-1,2,3,4-TETRAHYDRO-PYRIMIDINE-5-CARBALDEHYDE; 1,3-DIMETHYL-2,4,6-TRIOXO-HEXAHYDRO-PYRIMIDINE-5-CARBALDEHYDE; 1,3-DIMETHYL-2,4-DIOXO-1,2,3,4-TETRAHYDROPYRIMIDINE-5-CARBALDEHYDE; 1,3-DIMETHYL-2,4-DIOXO-6-(PROPYLAMINO)-1,2,3,4-TETRAHYDRO-5-PYRIMIDINECARBALDEHYDE; 1,3-DIMETHYL-2,4-DIOXO-6-[(TETRAHYDRO-2-FURANYLMETHYL)AMINO]-1,2,3,4-TETRAHYDRO-5-PYRIMIDINECARBALDEHYDE; 1,3-DIMETHYL-6-(METHYLAMINO)-2,4-DIOXO-1,2,3,4-TETRAHYDRO-5-PYRIMIDINECARBALDEHYDE; 11-CHLORO-13-OXO-8-OXA-1,10-DIAZATRICYCLO[7.4.0.02,7]TRIDECA-2(7),3,5,9,11-PENTAENE-12-CARBALDEHYDE; 11-CHLORO-13-OXO-8-THIA-1,10-DIAZATRICYCLO[7.4.0.02,7]TRIDECA-2(7),3,5,9,11-PENTAENE-12-CARBALDEHYDE; 1-CYCLOOCTYL-6-METHYL-2,4-DIOXO-1,2,3,4-TETRAHYDROPYRIMIDINE-5-CARBALDEHYDE; 1-ETHYL-2-OXO-1,2-DIHYDROQUINOLINE-3-CARBALDEHYDE; 1-ETHYL-7-METHYL-2-OXO-1,2-DIHYDROQUINOLINE-3-CARBALDEHYDE; 1H-PYRROLO[2,3-B]PYRIDINE-5-CARBOXALDEHYDE, 4-AMINO-6,7-DIHYDRO-2,3-DIMETHYL-6-OXO-; 1-ISOBUTYL-2-OXO-1,2-DIHYDRO-QUINOLINE-3-CARBALDEHYDE; 1-ISOBUTYL-6-METHOXY-2-OXO-1,2-DIHYDRO-QUINOLINE-3-CARBALDEHYDE; 1-ISOBUTYL-6-METHYL-2-OXO-1,2-DIHYDRO-QUINOLINE-3-CARBALDEHYDE; 1-METHYL-2-OXO-1,2-DIHYDROQUINOLINE-3-CARBALDEHYDE; 1-METHYL-2-OXOINDOLINE-3-CARBALDEHYDE; 2-((2-HYDROXYETHYL)AMINO)-9-ME-4-OXO-4H-PYRIDO(1,2-A)PYRIMIDINE-3-CARBALDEHYDE; 2-((2-METHOXYETHYL)AMINO)-4-OXO-4H-PYRIDO[1,2-A]PYRIMIDINE-3-CARBALDEHYDE; 2-((FURAN-2-YLMETHYL)AMINO)-4-OXO-4H-PYRIDO[1,2-A]PYRIMIDINE-3-CARBALDEHYDE; 2-(2,6-DIMETHYL-4-MORPHOLINYL)-4-OXO-4H-PYRIDO(1,2-A)PYRIMIDINE-3-CARBALDEHYDE; 2-(2-CHLOROANILINO)-4-OXO-4H-PYRIDO(1,2-A)PYRIMIDINE-3-CARBALDEHYDE; 2-(2-FLUOROANILINO)-9-METHYL-4-OXO-4H-PYRIDO(1,2-A)PYRIMIDINE-3-CARBALDEHYDE; 2-(3,5-DIMETHYLPIPERIDIN-1-YL)-9-METHYL-4-OXO-4H-PYRIDO[1,2-A]PYRIMIDINE-3-CARBALDEHYDE; 2-(3-FLUORO-PHENYL)-6-METHOXY-3-OXO-2,3-DIHYDRO-ISOQUINOLINE-4-CARBALDEHYDE; 2-(4-ETHYL-PIPERAZIN-1-YL)-4-OXO-4H-PYRIDO[1,2-A]PYRIMIDINE-3-CARBALDEHYDE; 2-(4-FLUOROPHENOXY)-9-METHYL-4-OXO-4H-PYRIDO[1,2-A]PYRIMIDINE-3-CARBALDEHYDE; 2-(4-METHOXYPHENOXY)-4-OXO-4H-PYRIDO[1,2-A]PYRIMIDINE-3-CARBALDEHYDE; 2-(4-METHYL-1-PIPERIDINYL)-4-OXO-4H-PYRIDO(1,2-A)PYRIMIDINE-3-CARBALDEHYDE; 2-(4-METHYLPIPERAZIN-1-YL)-4-OXO-4H-PYRIDO[1,2-A]PYRIMIDINE-3-CARBALDEHYDE; 2-(ALLYLAMINO)-4-OXO-4H-PYRIDO[1,2-A]PYRIMIDINE-3-CARBALDEHYDE; 2-(AZEPAN-1-YL)-4-OXO-4H-PYRIDO[1,2-A]PYRIMIDINE-3-CARBALDEHYDE; 2-(AZEPAN-1-YL)-9-METHYL-4-OXO-4H-PYRIDO[1,2-A]PYRIMIDINE-3-CARBALDEHYDE; 2-(BENZYLAMINO)-4-OXO-4H-PYRIDO[1,2-A]PYRIMIDINE-3-CARBALDEHYDE; 2-(BENZYLAMINO)-9-METHYL-4-OXO-4H-PYRIDO(1,2-A)PYRIMIDINE-3-CARBALDEHYDE; 2-(BENZYLTHIO)-4-OXO-4H-PYRIDO(1,2-A)PYRIMIDINE-3-CARBALDEHYDE; 2-(BUTYLTHIO)-4-OXO-4H-PYRIDO(1,2-A)PYRIMIDINE-3-CARBALDEHYDE; 2-(DIMETHYLAMINO)-4-OXO-4H-PYRIDO[1,2-A]PYRIMIDINE-3-CARBALDEHYDE; 2-(ETHYLAMINO)-9-METHYL-4-OXO-4H-PYRIDO(1,2-A)PYRIMIDINE-3-CARBALDEHYDE; 2,3-DIHYDRO-5-METHYL-3-OXO-2-PHENYL-1H-PYRAZOLE-4-CARBOXALDEHYDE; 2,4,6-TRIOXO-HEXAHYDRO-PYRIMIDINE-5-CARBALDEHYDE; 2,4-DIAMINO-6-OXO-1,6-DIHYDRO-5-PYRIMIDINECARBALDEHYDE; 2,4-DIOXO-3,4-DIHYDRO-2H-PYRIDO[1,2-A]PYRIMIDINE-3-CARBALDEHYDE; 2,6-DIAMINO-1,4-DIHYDRO-4-OXO-5-PYRIMIDINECARBOXALDEHYDE; 2,7-DICHLORO-4-OXO-4H-PYRIDO[1,2-A]PYRIMIDINE-3-CARBALDEHYDE; 2-[(2-FURYLMETHYL)AMINO]-7-METHYL-4-OXO-4H-PYRIDO[1,2-A]PYRIMIDINE-3-CARBALDEHYDE; 2-[BENZYL(METHYL)AMINO]-4-OXO-4H-PYRIDO[1,2-A]PYRIMIDINE-3-CARBALDEHYDE; 2-[ISOPROPYL(METHYL)AMINO]-4-OXO-4H-PYRIDO[1,2-A]PYRIMIDINE-3-CARBALDEHYDE; 2-AMINO-4-CHLORO-6-OXO-1H-PYRIMIDINE-5-CARBALDEHYDE; 2-AMINO-6-CHLORO-1,4-DIHYDRO-4-OXO-5-PYRIMIDINECARBOXALDEHYDE; 2-ANILINO-7-METHYL-4-OXO-4H-PYRIDO[1,2-A]PYRIMIDINE-3-CARBALDEHYDE; 2-AZEPAN-1-YL-7-METHYL-4-OXO-4H-PYRIDO[1,2-A]PYRIMIDINE-3-CARBALDEHYDE; 2-CHLORO-1-ETHYL-5-FORMYL-4-METHYL-6-OXO-1,6-DIHYDROPYRIDINE-3-CARBONITRILE; 2-CHLORO-4-OXO-4H-PYRIDO[1,2-A]PYRIMIDINE-3-CARBALDEHYDE; 2-CHLORO-6-METHYL-4-OXO-4H-PYRIDO[1,2-A]PYRIMIDINE-3-CARBALDEHYDE; 2-CHLORO-7-METHYL-4-OXO-4H-PYRIDO[1,2-A]PYRIMIDINE-3-CARBALDEHYDE; 2-CHLORO-8-METHYL-4-OXO-4H-PYRIDO[1,2-A]PYRIMIDINE-3-CARBALDEHYDE; 2-CHLORO-9-METHYL-4-OXO-4H-PYRIDO[1,2-A]PYRIMIDINE-3-CARBALDEHYDE; 2-DIETHYLAMINO-4-OXO-4H-PYRIDO[1,2-A]PYRIMIDINE-3-CARBALDEHYDE;

2-DIETHYLAMINO-7-METHYL-4-OXO-4H-PYRIDO[1,2-A]PYRIMIDINE-3-CARBALDEHYDE; 2-DIETHYLAMINO-9-METHYL-4-OXO-4H-PYRIDO[1,2-A]PYRIMIDINE-3-CARBALDEHYDE; 2-DIMETHYLAMINO-7-METHYL-4-OXO-4H-PYRIDO[1,2-A]PYRIMIDINE-3-CARBALDEHYDE; 2-DIMETHYLAMINO-9-METHYL-4-OXO-4H-PYRIDO[1,2-A]PYRIMIDINE-3-CARBALDEHYDE; 2-FORMYL-3-METHYL-1-OXO-1,5-DIHYDRO-BENZO[4,5]IMIDAZO[1,2-A]PYRIDINE-4-CARBONITRILE; 2-HYDROXY-4-OXO-4H-PYRIDO[1,2-A]PYRIMIDINE-3-CARBALDEHYDE; 2-METHYL-5-(MORPHOLIN-4-YL)-3-OXO-2,3-DIHYDROPYRIDAZINE-4-CARBALDEHYDE; 2-MORPHOLIN-4-YL-4-OXO-4H-PYRIDO[1,2-A]PYRIMIDINE-3-CARBALDEHYDE; 2-OXO-1,2,6,7,8,9-HEXAHYDROBENZO[G]QUINOLINE-3-CARBALDEHYDE; 2-OXO-1,2-DIHYDRO-3-PYRIDINECARBALDEHYDE; 2-OXO-1,2-DIHYDROQUINOLINE-3-CARBALDEHYDE; 2-OXO-1-PHENYLINDOLINE-3-CARBALDEHYDE; 2-OXO-5-PROPYLINDOLINE-3-CARBALDEHYDE; 2-OXOINDOLINE-3-CARBALDEHYDE; (CHLOROMETHYL)-2-FORMYL-1-OXO-1,5-DIHYDROPYRIDO[1,2-A]BENZIMIDAZOLE-4-CARBONITRILE; 3,4-DIHYDRO-3-OXO-2-QUINOXALINECARBOXALDEHYDE; 3-METHYL-5-OXO-1-PHENYL-4,5-DIHYDRO-1H-PYRAZOLE-4-CARBALDEHYDE; 4-ANTIPYRINECARBOXALDEHYDE; 4-CHLORO-1,2-DIHYDRO-2-OXO-3-QUINOLINECARBOXALDEHYDE; 4-CHLORO-2-OXO-3-INDOLINECARBALDEHYDE; 4-OXO-1,2-DIHYDRO-4H-PYRROLO[3,2,1-IJ]QUINOLINE-5-CARBALDEHYDE; 4-OXO-2-(4-TOLUIDINO)-4H-PYRIDO[1,2-A]PYRIMIDINE-3-CARBOXALDEHYDE; 4-OXO-2-(PHENYLTHIO)-4H-PYRIDO[1,2-A]PYRIMIDINE-3-CARBALDEHYDE; 4-OXO-2-PIPERIDIN-1-YL-4H-PYRIDO[1,2-A]PYRIMIDINE-3-CARBALDEHYDE; 4-OXO-2-P-TOLYLSULFANYL-4H-PYRIDO[1,2-A]PYRIMIDINE-3-CARBALDEHYDE; 4-OXO-2-PYRROLIDIN-1-YL-4H-PYRIDO[1,2-A]PYRIMIDINE-3-CARBALDEHYDE; 4-OXO-2-THIOMORPHOLIN-4-YL-4H-PYRIDO[1,2-A]PYRIMIDINE-3-CARBALDEHYDE; 5,7-DIMETHYL-2-OXO-1,2-DIHYDRO-3-QUINOLINECARBALDEHYDE; 5,8-DIMETHYL-2-OXO-1,2-DIHYDRO-3-QUINOLINECARBALDEHYDE; 5-BROMO-2-OXOINDOLINE-3-CARBALDEHYDE; 5-CHLORO-2-OXO-1,2-DIHYDRO-3-PYRIDINECARBALDEHYDE; 5-CHLORO-2-OXOINDOLINE-3-CARBALDEHYDE; 5-ETHOXY-2-OXOINDOLINE-3-CARBALDEHYDE; 5-ETHYL-2-OXOINDOLINE-3-CARBALDEHYDE; 5-FLUORO-2-OXOINDOLINE-3-CARBALDEHYDE; 5-FORMYLURACIL; 5-FORMYLURIDINE; 5-ISOPROPYL-2-OXOINDOLINE-3-CARBALDEHYDE; 5-METHOXY-2-OXOINDOLINE-3-CARBALDEHYDE; 5-METHYL-2-OXOINDOLINE-3-CARBALDEHYDE; 5-OXO-2,3-DIHYDRO-1H,5H-PYRIDO[3,2,1-IJ]QUINOLINE-6-CARBALDEHYDE; 6-(BROMOMETHYL)-1,3-DIETHYL-2,4-DIOXO-1,2,3,4-TETRAHYDROPYRIMIDINE-5-CARBALDEHYDE; 6-(BROMOMETHYL)-1,3-DIMETHYL-2,4-DIOXO-1,2,3,4-TETRAHYDROPYRIMIDINE-5-CARBALDEHYDE; 6-(ISOPROPYLAMINO)-1,3-DIMETHYL-2,4-DIOXO-1,2,3,4-TETRAHYDRO-5-PYRIMIDINECARBALDEHYDE; 6,7-DIETHOXY-2-OXO-1,2-DIHYDROQUINOLINE-3-CARBALDEHYDE; 6-[(2-METHOXYETHYL)AMINO]-1,3-DIMETHYL-2,4-DIOXO-1,2,3,4-TETRAHYDRO-5-PYRIMIDINECARBALDEHYDE; 6-AMINO-1-(2-CHLOROPHENYL)-4-OXO-2-THIOXO-1,2,3,4-TETRAHYDRO-5-PYRIMIDINECARBALDEHYDE; 6-AMINO-1-(2-FURYLMETHYL)-2,4-DIOXO-TETRAHYDROPYRIMIDINE-5-CARBALDEHYDE; 6-AMINO-1-(2-METHYLPHENYL)-4-OXO-2-THIOXO-1,2,3,4-TETRAHYDRO-5-PYRIMIDINECARBALDEHYDE; 6-AMINO-1-(3-METHOXYPHENYL)-2,4-DIOXO-1,2,3,4-TETRAHYDROPYRIMIDINE-5-CARBALDEHYDE; 6-AMINO-1-(4-CHLOROPHENYL)-2,4-DIOXOTETRAHYDROPYRIMIDINE-5-CARBALDEHYDE; 6-AMINO-1-(4-CHLOROPHENYL)-4-OXO-2-THIOXO-1,2,3,4-TETRAHYDRO-5-PYRIMIDINECARBALDEHYDE; 6-AMINO-1-(4-METHOXYPHENYL)-2,4-DIOXO-1,2,3,4-TETRAHYDROPYRIMIDINE-5-CARBALDEHYDE; 6-AMINO-1-(4-METHOXYPHENYL)-4-OXO-2-THIOXO-1,2,3,4-TETRAHYDRO-5-PYRIMIDINECARBALDEHYDE; 6-AMINO-1-(4-METHYLPHENYL)-4-OXO-2-THIOXO-1,2,3,4-TETRAHYDRO-5-PYRIMIDINECARBALDEHYDE; 6-AMINO-1,3-DIETHYL-5-FORMYLURACIL; 6-AMINO-1,3-DIMETHYL-2,4-DIOXO-1,2,3,4-TETRAHYDROPYRIMIDINE-5-CARBALDEHYDE; 6-AMINO-1-BENZYL-2,4-DIOXOTETRAHYDROPYRIMIDINE-5-CARBALDEHYDE; 6-AMINO-1-ISOBUTYL-3-METHYL-2,4-DIOXO-1,2,3,4-TETRAHYDROPYRIMIDINE-5-CARBALDEHYDE; 6-AMINO-1-METHYL-2,4-DIOXO-1,2,3,4-TETRAHYDRO-5-PYRIMIDINECARBALDEHYDE; 6-AMINO-2,4-DIOXO-1-(2-PHENYLETHYL)TETRAHYDROPYRIMIDINE-5-CARBALDEHYDE; 6-AMINO-2,4-DIOXO-1-(PYRIDIN-3-YLMETHYL)TETRAHYDROPYRIMIDINE-5-CARBALDEHYDE; 6-AMINO-2,4-DIOXO-1,2,3,4-TETRAHYDRO-PYRIMIDINE-5-CARBALDEHYDE; 6-AMINO-4-OXO-1-PHENYL-2-THIOXO-1,2,3,4-TETRAHYDRO-5-PYRIMIDINECARBALDEHYDE; 6-BROMO-1,2-DIHYDRO-2-OXO-3-QUINOLINECARBOXALDEHYDE; 6-BROMO-2-OXO-1,2,3,4-TETRAHYDRO-QUINOLINE-3-CARBALDEHYDE; 6-CHLORO-1,2-DIHYDRO-2-OXO-3-QUINOLINECARBOXALDEHYDE; 6-CHLORO-1,3-BIS(2-METHOXYETHYL)-2,4-DIOXO-1,2,3,4-TETRAHYDROPYRIMIDINE-5-CARBALDEHYDE; 6-CHLORO-1,3-DIISOBUTYL-2,4-DIOXO-1,2,3,4-TETRAHYDROPYRIMIDINE-5-CARBALDEHYDE; 6-CHLORO-2-OXO-3-INDOLINECARBALDEHYDE; 6-CHLORO-5-FORMYL-1,3-DIMETHYLURACIL; 6-DIMETHYLAMINO-1,3-DIMETHYL-2,4-DIOXO-1,2,3,4-TETRAHYDROPYRIMIDINE-5-CARBOXALDEHYDE; 6-ETHOXY-2-OXO-1,2-DIHYDRO-QUINOLINE-3-CARBALDEHYDE; 6-ETHYL-1,2-DIHYDRO-2-OXO-3-QUINOLINECARBOXALDEHYDE; 6-FLUORO-2-OXOINDOLINE-3-CARBALDEHYDE; 6-HYDROXY-2,4-DIOXO-1,2,3,4-TETRAHYDROPYRIMIDINE-5-CARBALDEHYDE; 6-METHOXY-1-METHYL-2-OXO-1,2-DIHYDROQUINOLINE-3-CARBALDEHYDE; 6-METHOXY-2-OXO-1,2-DIHYDRO-QUINOLINE-3-CARBALDEHYDE; 6-METHOXY-2-OXOINDOLINE-3-CARBALDEHYDE; 6-METHYL-2,4-DIOXO-1,2,3,4-TETRAHYDRO-PYRIMIDINE-5-CARBALDEHYDE; 6-METHYL-2-OXO-1,2-DIHYDROQUINOLIN-3-CARBALDEHYDE; 6-METHYL-2-OXOINDOLINE-3-CARBALDEHYDE; 6-OXO-5,6-DIHYDRO-[1,3]DIOXOLO[4,5-G]QUINOLINE-7-CARBALDEHYDE; 7-BROMO-2-CHLORO-4-OXO-4H-PYRIDO[1,2-A]PYRIMIDINE-3-CARBALDEHYDE; 7-CHLORO-1,2-DIHYDRO-2-OXO-

3-QUINOLINECARBOXALDEHYDE; 7-CHLORO-5-OXO-5H-THIAZOLO[3,2-A]PYRIMIDINE-6-CARBALDEHYDE; 7-ETHOXY-1,2-DIHYDRO-2-OXO-3-QUINOLINECARBOXALDEHYDE; 7-METHOXY-1-METHYL-2-OXO-1,2-DIHYDROQUINOLINE-3-CARBALDEHYDE; 7-METHOXY-2-OXO-1,2-DIHYDRO-QUINOLINE-3-CARBALDEHYDE; 7-METHYL-2-(4-METHYL-PIPERAZIN-1-YL)-4-OXO-4H-PYRIDO[1,2-A]PYRIMIDINE-3-CARBALDEHYDE; 7-METHYL-2-(4-METHYL-PIPERIDIN-1-YL)-4-OXO-4H-PYRIDO[1,2-A]PYRIMIDINE-3-CARBALDEHYDE; 7-METHYL-2-MORPHOLIN-4-YL-4-OXO-4H-PYRIDO[1,2-A]PYRIMIDINE-3-CARBALDEHYDE; 7-METHYL-4-OXO-2-PIPERIDIN-1-YL-4H-PYRIDO[1,2-A]PYRIMIDINE-3-CARBALDEHYDE; 7-METHYL-4-OXO-2-P-TOLYLAMINO-4H-PYRIDO(1,2-A)PYRIMIDINE-3-CARBALDEHYDE; 7-METHYLSULFANYL-2-OXO-1,2-DIHYDRO-QUINOLINE-3-CARBALDEHYDE; 7-OXO-2,3,6,7-TETRAHYDRO-[1,4]DIOXINO[2,3-G]QUINOLINE-8-CARBALDEHYDE; 8-CHLORO-1,2-DIHYDRO-2-OXO-3-QUINOLINECARBOXALDEHYDE; 8-ETHYL-1,2-DIHYDRO-2-OXO-3-QUINOLINECARBOXALDEHYDE; 8-METHYL-2-OXO-1,2-DIHYDRO-QUINOLINE-3-CARBALDEHYDE; 8-OXO-3,4,8,9-TETRAHYDRO-2H,7H-[1,4]DIOXEPINO[2,3-F]INDOLE-9-CARBALDEHYDE; 9-METHYL-2-(4-METHYL-PIPERAZIN-1-YL)-4-OXO-4H-PYRIDO[1,2-A]PYRIMIDINE-3-CARBALDEHYDE; 9-METHYL-2-(4-METHYLPIPERIDIN-1-YL)-4-OXO-4H-PYRIDO[1,2-A]PYRIMIDINE-3-CARBALDEHYDE; 9-METHYL-2-(METHYLOXY)-4-OXO-4H-PYRIDO[1,2-A]PYRIMIDINE-3-CARBALDEHYDE; 9-METHYL-2-MORPHOLIN-4-YL-4-OXO-4H-PYRIDO[1,2-A]PYRIMIDINE-3-CARBALDEHYDE; 9-METHYL-4-OXO-2-(2-PYRIMIDINYLAMINO)-4H-PYRIDO(1,2-A)PYRIMIDINE-3-CARBALDEHYDE; 9-METHYL-4-OXO-2-(4-TOLUIDINO)-4H-PYRIDO(1,2-A)PYRIMIDINE-3-CARBALDEHYDE; 9-METHYL-4-OXO-2-(M-TOLYLOXY)-4H-PYRIDO[1,2-A]PYRIMIDINE-3-CARBALDEHYDE; 9-METHYL-4-OXO-2-(PHENYLTHIO)-4H-PYRIDO[1,2-A]PYRIMIDINE-3-CARBALDEHYDE; 9-METHYL-4-OXO-2-PIPERIDIN-1-YL-4H-PYRIDO[1,2-A]PYRIMIDINE-3-CARBALDEHYDE; 9-METHYL-4-OXO-2-PYRROLIDIN-1-YL-4H-PYRIDO[1,2-A]PYRIMIDINE-3-CARBALDEHYDE; 9-METHYL-4-OXO-2-THIOMORPHOLIN-4-YL-4H-PYRIDO[1,2-A]PYRIMIDINE-3-CARBALDEHYDE; METHYL ((3-FORMYL-4-OXO-4H-PYRIDO(1,2-A)PYRIMIDIN-2-YL)THIO)ACETATE; N'-(3-ETHYL-5-FORMYL-2,6-DIOXO-1,2,3,6-TETRAHYDRO-PYRIMIDIN-4-YL)-N,N-DIMETHYL-FORMAMIDINE; SODIUM 5-FORMYL-1,3-DIMETHYL-2,6-DIOXO-1,2,3,6-TETRAHYDRO-4-PYRIMIDINOLATE

The invention claimed is:

1. A method for the synthesis of a plurality of different bi-functional complexes, each different bi-functional complex comprising a different small molecule part and an identifier oligonucleotide part identifying the different small molecule part, said method comprising the steps of:
  i) providing a plurality of solid supports,
  ii) providing a plurality of different first identifier oligonucleotide tags, each comprising more than one nucleotide and each comprising a chemical reaction site,
  iii) providing a plurality of different first reactive compound building blocks, wherein each different first reactive compound building block is identified by a different first identifier oligonucleotide tag,
  iv) covalently linking each different first identifier oligonucleotide tag to a solid support provided in step i),
  v) reacting in an organic solvent each different first reactive compound building block with the chemical reaction site of its corresponding different first identifier oligonucleotide tag,
  wherein each different first identifier oligonucleotide tag is covalently linked to a different solid support when the first reactive compound building blocks are reacted with the chemical reaction site of their corresponding first identifier oligonucleotide tag,
  wherein said reaction in an organic solvent of the different first reactive compounds building block with their corresponding first identifier oligonucleotide tags generates a plurality of different first intermediate, bi-functional complexes, each linked to a solid support,
  vi) reacting in an organic solvent each different first intermediate bi-functional complex obtained in step v) with a plurality of different second reactive compound building blocks in the absence of corresponding second identifier oligonucleotide tags identifying the second reactive compound building blocks,
  wherein the first intermediate bi-functional complexes are covalently linked to the solid support when the second reactive compound building blocks are reacted with the chemical reaction sites and/or reacted with first intermediate molecule parts of the plurality of different first intermediate bi-functional complexes,
  wherein the reaction of the second reactive compound building blocks and the plurality of different first intermediate bi-functional complex generates a plurality of different second intermediate, bi-functional complexes, each linked to a solid support,
  vii) cleaving the plurality of different second intermediate bi-functional complexes obtained in step vi) from the solid supports, and
  viii) enzymatically ligating in an aqueous medium, each of the plurality of first identifier oligonucleotide tags of the plurality of different second intermediate bi-functional complexes cleaved from the solid supports to a second identifier oligonucleotide tag comprising more than one nucleotide and identifying the second reactive compound building block of the second intermediate bi-functional complex,
  wherein the enzymatic ligation of the first and second identifier oligonucleotide tags generates the plurality of different bi-functional complexes, each comprising the different small molecule part and the identifier oligonucleotide part identifying the different small molecule part.

2. The method of claim 1, wherein the plurality of solid supports provided in step i), the plurality of first identifier oligonucleotide tags provided in step ii) and the plurality of first reactive compound building blocks provided in step iii) are reacted in steps iv) and v) in the same or different reaction compartment(s), thereby generating, in each reaction compartment, a plurality of the same or different first intermediate bi-functional complexes.

3. The method of claim 2, wherein different, optionally protected, first identifier oligonucleotide tags and/or different first reactive compound building blocks are provided in different reaction compartments.

4. The method of claim 2, wherein different first intermediate bi-functional complexes are obtained in different reaction compartments.

5. The method of claim 4, wherein said different first intermediate bi-functional complexes are subsequently mixed into the same reaction compartment.

6. The method of claim 1, wherein the solid supports are linked to first reactive compound building blocks and/or linked to first identifier oligonucleotide tags by a selectively cleavable first linker moiety capable of linking first identifier oligonucleotide tags and/or the first reactive compound building blocks to a solid support, and wherein first reactive compound building blocks are linked to first identifier oligonucleotide tags by a second linker moiety capable of linking first reactive compound building blocks and first identifier oligonucleotide tags.

7. The method of claim 6, wherein the selectively cleavable linker formed between the solid support and the first identifier oligonucleotide tag or the first reactive compound building block is formed by reacting one or more first linker moiety reactive groups with one or more reactive groups of a first identifier oligonucleotide tag and/or one or more reactive groups of a first reactive compound building block.

8. The method of claim 6, wherein the linker formed between the first identifier oligonucleotide tag and the first reactive compound building block is formed by reacting one or more reactive groups of the first identifier oligonucleotide tag and one or more reactive groups of the first reactive compound building block, wherein said reactions form one or more second linker moieties connecting the first identifier oligonucleotide tag and the first reactive compound building block.

9. The method of claim 7, wherein said linker is a covalent linker.

10. The method of claim 8, wherein said linker is a covalent linker.

11. The method of claim 1 comprising the further steps of reacting simultaneously or sequentially the bi-functional complexes with a further plurality of reactive compound building blocks and a further plurality of oligonucleotide tags identifying said further reactive compound building blocks.

12. The method of claim 1, said method comprising the further step of providing a plurality of first and/or second protection groups for protecting reactive groups of reactive compound building blocks or reactive groups of oligonucleotide tags in a first or subsequent reaction cycle.

13. The method of claim 1 comprising the further steps of performing one or more further reaction cycles, wherein, in each reaction cycle, third or further pluralities of intermediate bi-functional complexes are reacted, simultaneously or sequentially, with a plurality of further reactive compound building blocks and a plurality of further oligonucleotide tags identifying said further reactive compound building blocks, wherein, following each further reaction cycle, a plurality of further intermediate bifunctional complexes or bi-functional complexes are generated, each bi-functional complex comprising a different small molecule part and an oligonucleotide identifier part identifying the different small molecule part.

14. The method of claim 1, wherein chemical reaction site(s) of the different bi-functional complexes are reacted one or more times with one or more further reactive compound building blocks and wherein the sites for oligonucleotide tag addition are reacted by an enzyme catalysed reaction with the corresponding oligonucleotide tags identifying said building blocks, wherein the sequence of the oligonucleotide tags of the identifier oligonucleotide part of a final bi-functional complex is used to determine the reactive compound building blocks that have participated in the formation of the small molecule part of the final bi-functional complex.

15. The method of claim 1, wherein a plurality of bi-functional complexes comprise
  a) a small molecule and an oligonucleotide identifier comprising a plurality of oligonucleotide tags identifying reactive compound building blocks having participated in the synthesis of said small molecule,
  b) one or more chemical reaction site(s) comprising one or more reactive groups and
  c) one or more tag addition site(s) for enzymatic addition of an oligonucleotide tag,
  said method comprising the further steps of
    ix) providing a plurality of third reactive compound building blocks each comprising one or more reactive compound building blocks and one or more reactive groups, each third reactive compound building block being capable of reacting with
      a) one or more chemical reaction site(s) of an intermediate bi-functional complex, and/or
      b) one or more reactive groups of a further third reactive compound building block comprising one or more reactive compound building blocks,
      wherein said further third reactive compound building block is provided simultaneously or sequentially in any order with the third reactive compound building block, wherein the third and the further third reactive compound building blocks are identical or different reactive compound building blocks,
    x) providing a plurality of third identifier oligonucleotide tags each capable of hybridising to part of a third identifier oligonucleotide complementary tag, wherein each third identifier oligonucleotide tag identifies a third reactive compound building block and, optionally, a further third reactive compound building block,
    xi) providing a plurality of third identifier oligonucleotide complementary tags each capable of hybridising to at least part of a third identifier oligonucleotide tag provided in step ii) and to at least part of the oligonucleotide identifier of the bi-functional complex,
    xii) reacting each of the third reactive compound building blocks provided in step ix) with a) the one or more chemical reaction site(s) of the bi-functional complexes and/or with b) the one or more reactive groups of a further third reactive compound building block comprising one or more reactive compound building blocks,
      wherein the reaction of complementary reactive groups result in the formation of a covalent bond, and
      wherein one or more reactive group reactions of step xii) result in the formation of one or more covalent bond(s) between the one or more chemical reaction site(s) of the bi-functional complexes and at least one reactive compound building block of at least one reactive compound building block selected from the group consisting of a third reactive compound building block and a further third reactive compound building block,
    xiii) hybridising complementary identifier oligonucleotide tags to the bi-functional complexes and to third identifier oligonucleotide tags,
      wherein method steps xii) and xiii) are simultaneous or sequential in any order,
    xiv) enzymatically ligating the bi-functional complexes and third identifier oligonucleotide tags, thereby generating a further bi-functional complexes,
    xv) dividing the plurality of further bi-functional complexes obtained in step vi) into a plurality of different compartments,
    xvi) providing in each different compartment a plurality of different fourth reactive compound building blocks each comprising one or more reactive compound building blocks and one or more reactive groups capable of reacting with
      a) the one or more chemical reaction site(s) of a further intermediate bi-functional complex obtained in step xiv), and/or
      b) one or more reactive groups of one or more reactive compound building block(s) having reacted in a previous synthesis round, and/or
      c) one or more reactive groups of a further fourth reactive compound building block comprising one or more reactive compound building blocks, wherein said further fourth reactive compound building blocks are provided simultaneously or sequentially in any order with the fourth reactive compound building blocks, wherein the fourth and the further fourth reactive compound building blocks are identical or different reactive compound building blocks, xvii) providing in each different compartment a plurality of fourth identifier oligonucleotide tags each capable of hybridising to part of a fourth identifier oligonucleotide complementary tag, wherein different fourth identifier oligonucleotide tags are provided in each different compartment, and wherein each different fourth identifier oligonucleotide identifies a different fourth reactive compound building block and, optionally, a further fourth reactive compound building block, xviii) providing in each different compartment a plurality of fourth identifier oligonucleotide complementary tags capable of hybridising to part of a third identifier oligonucleotide tag provided in step x) and to part of a fourth identifier oligonucleotide tag provided in step xvii), xix) reacting in each different compartment each of the different fourth reactive compound building blocks provided in step xvi) with a) the one or more chemical reaction site(s) of a further bi-functional complex and/or b) one or more reactive groups of one or more reactive compound building block(s) having reacted in a previous synthesis round and/or c) one or more reactive groups of a further fourth reactive compound building block comprising one or more reactive compound building blocks, wherein said one or more reactions result in the formation of different further bi-functional complexes in each different compartment, wherein the reaction of complementary reactive groups result in the formation of one or more covalent bond(s), and wherein one or more reactive group reactions of step xix) result in
   a) the formation of one or more covalent bond(s) between the one or more chemical reaction site(s) and at least one reactive compound building block of at least one reactive compound building block selected from the group consisting of fourth reactive compound building blocks and further fourth reactive compound building blocks, and/or
   b) the formation of one or more covalent bond(s) between a reactive compound building block having reacted in a previous synthesis round and at least one reactive compound building block of at least one reactive compound building block selected from the group consisting of fourth reactive compound building blocks and further fourth reactive compound building blocks, xx) hybridising complementary oligonucleotide identifier tags to third identifier oligonucleotide tags and fourth identifier oligonucleotide tags in each different compartment, wherein method steps xix) and xx) are simultaneous or sequential in any order, xxi) enzymatically ligating in each different compartment third and fourth identifier oligonucleotide tags in the absence of ligation of third and fourth complementary oligonucleotide tags, and xxii) optionally displacing in each compartment unligated complementary oligonucleotide tags from further bi-functional complexes comprising a molecule and a single stranded oligonucleotide identifier comprising oligonucleotide tags identifying reactive compound building blocks having participated in the synthesis of the molecule.

16. The method of claim 15, wherein steps xv) to xxi) are repeated once or more than once using different reactive compound building blocks and oligonucleotide tags identifying said different reactive compound building blocks.

17. The method of claim 15, wherein different reaction cycles are performed in parallel in different reaction compartments, wherein the same or different bi-functional complexes is/are provided in each of a plurality of separate reaction compartments and subsequently, wherein, in each of said reaction compartments, the third reactive compound building block and optionally also the further third reactive compound building block is/are reacted with the one or more chemical reaction site(s), and wherein, in each of said compartments, a third identifier oligonucleotide tag identifying said one or more reactive compound building block(s) is added enzymatically to the one or more tag addition site(s), said reaction(s) of said reactive compound building block(s) and said addition(s) of said oligonucleotide tag resulting in the formation, in each of said reaction compartments, of different further bi-functional complexes.

18. The method of claim 17, wherein said different bi-functional complexes are mixed, and wherein said mixture of different bi-functional complexes is subsequently divided into a plurality of different reaction compartments.

19. The method of claim 18, wherein a different bi-functional complex is provided in each of said plurality of separate reaction compartments and subsequently, in each of said reaction compartments, the fourth reactive compound building block and optionally also the further fourth reactive compound building block is/are reacted with one or more of a chemical reaction site and one or more reactive group(s) of a third reactive compound building block and/or further third reactive compound building block, and wherein, in each of said compartments, a fourth identifier oligonucleotide tag identifying said one or more reactive compound building block(s) is added enzymatically to the third identifier oligonucleotide tag, said reaction(s) of said reactive compound building block(s) and said addition(s) of said oligonucleotide tag resulting in the formation, in each of said compartments, of further different bi-functional complexes.

20. The method of claim 19, wherein, in each subsequent round of parallel synthesis, the reactive compound building block reaction product of a previous synthesis round reacts with the reactive compound building block in a subsequent synthesis round, and wherein an oligonucleotide tag added in a previous synthesis round acts as a substrate for the enzyme which adds an oligonucleotide tag in a subsequent synthesis round.

* * * * *

SEQUENCE LISTING

```
<160> NUMBER OF SEQ ID NOS: 36

<210> SEQ ID NO 1
<211> LENGTH: 26
<212> TYPE: DNA
<213> ORGANISM: Artificial sequence
<220> FEATURE:
<223> OTHER INFORMATION: Codon B1 encoding building block BB6 (top
      strand)

<400> SEQUENCE: 1
ctgatcgcta aatgtcaatc ggactt                                     26

<210> SEQ ID NO 2
<211> LENGTH: 32
<212> TYPE: DNA
<213> ORGANISM: Artificial sequence
<220> FEATURE:
<223> OTHER INFORMATION: Codon B1 encoding building block BB6 (bottom
      strand)

<400> SEQUENCE: 2
aagtccgatt gacatttagc gatcaggcca at                              32

<210> SEQ ID NO 3
<211> LENGTH: 26
<212> TYPE: DNA
<213> ORGANISM: Artificial sequence
<220> FEATURE:
<223> OTHER INFORMATION: Codon B2 encoding building block BB7 (top
      strand)

<400> SEQUENCE: 3
gatccagcta aatgtcaatc ggactt                                     26

<210> SEQ ID NO 4
<211> LENGTH: 32
```

-continued

```
<212> TYPE: DNA
<213> ORGANISM: Artificial sequence
<220> FEATURE:
<223> OTHER INFORMATION: Codon B2 encoding building block BB7 (bottom
      strand)

<400> SEQUENCE: 4
aagtccgatt gacatttagc tggatcgcca at                                   32

<210> SEQ ID NO 5
<211> LENGTH: 26
<212> TYPE: DNA
<213> ORGANISM: Artificial sequence
<220> FEATURE:
<223> OTHER INFORMATION: Codon B3 encoding building block BB8 (top
      strand)

<400> SEQUENCE: 5
gtagttgcta aatgtcaatc ggactt                                          26

<210> SEQ ID NO 6
<211> LENGTH: 32
<212> TYPE: DNA
<213> ORGANISM: Artificial sequence
<220> FEATURE:
<223> OTHER INFORMATION: Codon B3 encoding building block BB8 (bottom
      strand)

<400> SEQUENCE: 6
aagtccgatt gacatttagc aactacgcca at                                   32

<210> SEQ ID NO 7
<211> LENGTH: 20
<212> TYPE: DNA
<213> ORGANISM: Artificial sequence
<220> FEATURE:
<223> OTHER INFORMATION: Fixed 5' end sequence for encoding tag

<400> SEQUENCE: 7
caagtcacca agaattcatg                                                 20

<210> SEQ ID NO 8
<211> LENGTH: 10
<212> TYPE: DNA
<213> ORGANISM: Artificial sequence
<220> FEATURE:
<223> OTHER INFORMATION: Aset-0001 encoding segment A

<400> SEQUENCE: 8
gatgcttcct                                                            10

<210> SEQ ID NO 9
<211> LENGTH: 10
<212> TYPE: DNA
<213> ORGANISM: Artificial sequence
<220> FEATURE:
<223> OTHER INFORMATION: Aset-0001 encoding segment D

<400> SEQUENCE: 9
cctaggacca                                                            10

<210> SEQ ID NO 10
<211> LENGTH: 10
<212> TYPE: DNA
<213> ORGANISM: Artificial sequence
<220> FEATURE:
<223> OTHER INFORMATION: Aset-0017 encoding segment B
```

```
<400> SEQUENCE: 10
gtgcaacttt                                                          10

<210> SEQ ID NO 11
<211> LENGTH: 10
<212> TYPE: DNA
<213> ORGANISM: Artificial sequence
<220> FEATURE:
<223> OTHER INFORMATION: Aset-0033 encoding segment B

<400> SEQUENCE: 11
gacgaagcac                                                          10

<210> SEQ ID NO 12
<211> LENGTH: 23
<212> TYPE: DNA
<213> ORGANISM: Artificial sequence
<220> FEATURE:
<223> OTHER INFORMATION: Primer

<400> SEQUENCE: 12
caagtcacca agaattcatg tag                                           23

<210> SEQ ID NO 13
<211> LENGTH: 26
<212> TYPE: DNA
<213> ORGANISM: Artificial sequence
<220> FEATURE:
<223> OTHER INFORMATION: Primer

<400> SEQUENCE: 13
caagtcacca agaattcatg tagcac                                        26

<210> SEQ ID NO 14
<211> LENGTH: 26
<212> TYPE: DNA
<213> ORGANISM: Artificial sequence
<220> FEATURE:
<223> OTHER INFORMATION: Primer

<400> SEQUENCE: 14
caagtcacca agaattcatg tagtct                                        26

<210> SEQ ID NO 15
<211> LENGTH: 26
<212> TYPE: DNA
<213> ORGANISM: Artificial sequence
<220> FEATURE:
<223> OTHER INFORMATION: Primer

<400> SEQUENCE: 15
caagtcacca agaattcatg gtaacc                                        26

<210> SEQ ID NO 16
<211> LENGTH: 32
<212> TYPE: DNA
<213> ORGANISM: Artificial sequence
<220> FEATURE:
<223> OTHER INFORMATION: Oligonucleotide tag
<220> FEATURE:
<221> NAME/KEY: misc_feature
<222> LOCATION: (17)..(22)
<223> OTHER INFORMATION: n is a, c, g, or t

<400> SEQUENCE: 16
```
tagcacgatg cttcctnnnn nncctaggac ca                                    32

<210> SEQ ID NO 17
<211> LENGTH: 36
<212> TYPE: DNA
<213> ORGANISM: Artificial sequence
<220> FEATURE:
<223> OTHER INFORMATION: Oligonucleotide tag

<400> SEQUENCE: 17
aggaagcatc gtgctacatg aattcttggt gacttg                                36

<210> SEQ ID NO 18
<211> LENGTH: 32
<212> TYPE: DNA
<213> ORGANISM: Artificial sequence
<220> FEATURE:
<223> OTHER INFORMATION: Oligonucleotide tag
<220> FEATURE:
<221> NAME/KEY: misc_feature
<222> LOCATION: (17)..(22)
<223> OTHER INFORMATION: n is a, c, g, or t

<400> SEQUENCE: 18
tagtctgtgc aactttnnnn nncctaggac ca                                    32

<210> SEQ ID NO 19
<211> LENGTH: 36
<212> TYPE: DNA
<213> ORGANISM: Artificial sequence
<220> FEATURE:
<223> OTHER INFORMATION: Oligonucleotide tag

<400> SEQUENCE: 19
aaagttgcac agactacatg aattcttggt gacttg                                36

<210> SEQ ID NO 20
<211> LENGTH: 32
<212> TYPE: DNA
<213> ORGANISM: Artificial sequence
<220> FEATURE:
<223> OTHER INFORMATION: Oligonucleotide tag
<220> FEATURE:
<221> NAME/KEY: misc_feature
<222> LOCATION: (17)..(22)
<223> OTHER INFORMATION: n is a, c, g, or t

<400> SEQUENCE: 20
gtaaccgacg aagcacnnnn nncctaggac ca                                    32

<210> SEQ ID NO 21
<211> LENGTH: 26
<212> TYPE: DNA
<213> ORGANISM: Artificial sequence
<220> FEATURE:
<223> OTHER INFORMATION: Oligonucleotide tag

<400> SEQUENCE: 21
ggttaccatg aattcttggt gacttg                                           26

<210> SEQ ID NO 22
<211> LENGTH: 32
<212> TYPE: DNA
<213> ORGANISM: Artificial sequence
<220> FEATURE:
<223> OTHER INFORMATION: Oligonucleotide tag

<400> SEQUENCE: 22
gatcgatcga tcgatcgatc gaattcattg gc                                32

<210> SEQ ID NO 23
<211> LENGTH: 32
<212> TYPE: DNA
<213> ORGANISM: Artificial sequence
<220> FEATURE:
<223> OTHER INFORMATION: Oligonucleotide tag

<400> SEQUENCE: 23
gatcgatcga tcgatcgatc ctagtcattg gc                                32

<210> SEQ ID NO 24
<211> LENGTH: 32
<212> TYPE: DNA
<213> ORGANISM: Artificial sequence
<220> FEATURE:
<223> OTHER INFORMATION: Oligonucleotide tag

<400> SEQUENCE: 24
gatcgatcga tcgatcgatc acctgtattg gc                                32

<210> SEQ ID NO 25
<211> LENGTH: 32
<212> TYPE: DNA
<213> ORGANISM: Artificial sequence
<220> FEATURE:
<223> OTHER INFORMATION: Oligonucleotide tag

<400> SEQUENCE: 25
gatcgatcga tcgatcgatc gctagtattg gc                                32

<210> SEQ ID NO 26
<211> LENGTH: 32
<212> TYPE: DNA
<213> ORGANISM: Artificial sequence
<220> FEATURE:
<223> OTHER INFORMATION: Oligonucleotide tag

<400> SEQUENCE: 26
gatccatcga tccatcaatc gaattcattg gc                                32

<210> SEQ ID NO 27
<211> LENGTH: 32
<212> TYPE: DNA
<213> ORGANISM: Artificial sequence
<220> FEATURE:
<223> OTHER INFORMATION: Oligonucleotide tag

<400> SEQUENCE: 27
gatccatcga tccatcaatc ctagtcattg gc                                32

<210> SEQ ID NO 28
<211> LENGTH: 32
<212> TYPE: DNA
<213> ORGANISM: Artificial sequence
<220> FEATURE:
<223> OTHER INFORMATION: Oligonucleotide tag

<400> SEQUENCE: 28
gatccatcga tccatcaatc acctgtattg gc                                32

<210> SEQ ID NO 29
<211> LENGTH: 32
<212> TYPE: DNA

```
<213> ORGANISM: Artificial sequence
<220> FEATURE:
<223> OTHER INFORMATION: Oligonucleotide tag

<400> SEQUENCE: 29
gatccatcga tccatcaatc gctagtattg gc                              32

<210> SEQ ID NO 30
<211> LENGTH: 32
<212> TYPE: DNA
<213> ORGANISM: Artificial sequence
<220> FEATURE:
<223> OTHER INFORMATION: Oligonucleotide tag

<400> SEQUENCE: 30
gatccatcga tccatcaatc tagctaattg gc                              32

<210> SEQ ID NO 31
<211> LENGTH: 27
<212> TYPE: DNA
<213> ORGANISM: Artificial sequence
<220> FEATURE:
<223> OTHER INFORMATION: Oligonucleotide tag
<220> FEATURE:
<221> NAME/KEY: misc_feature
<222> LOCATION: (21)..(27)
<223> OTHER INFORMATION: n is a, c, g, or t

<400> SEQUENCE: 31
caagtcacca agaattcatg nnnnnnn                                    27

<210> SEQ ID NO 32
<211> LENGTH: 20
<212> TYPE: DNA
<213> ORGANISM: Artificial sequence
<220> FEATURE:
<223> OTHER INFORMATION: Antisense oligonucleotide

<400> SEQUENCE: 32
catgaattct tggtgacttg                                            20

<210> SEQ ID NO 33
<211> LENGTH: 12
<212> TYPE: DNA
<213> ORGANISM: Artificial sequence
<220> FEATURE:
<223> OTHER INFORMATION: Oligonucleotide tag

<400> SEQUENCE: 33
caagtcacca ag                                                    12

<210> SEQ ID NO 34
<211> LENGTH: 17
<212> TYPE: DNA
<213> ORGANISM: Artificial sequence
<220> FEATURE:
<223> OTHER INFORMATION: Antisense oligonucleotide

<400> SEQUENCE: 34
caattcttgg tgacttg                                               17

<210> SEQ ID NO 35
<211> LENGTH: 12
<212> TYPE: DNA
<213> ORGANISM: Artificial sequence
<220> FEATURE:
<223> OTHER INFORMATION: Oligonucleotide tag
```

```
<400> SEQUENCE: 35
atgcgagggg gg                                                          12

<210> SEQ ID NO 36
<211> LENGTH: 12
<212> TYPE: DNA
<213> ORGANISM: Artificial sequence
<220> FEATURE:
<223> OTHER INFORMATION: Oligonucleotide tag

<400> SEQUENCE: 36
cccccctcgg ca                                                          12
```